(12) United States Patent
Zhang et al.

(10) Patent No.: US 12,060,347 B2
(45) Date of Patent: Aug. 13, 2024

(54) BICYCLIC HETEROARYL SUBSTITUTED COMPOUNDS

(71) Applicant: BRISTOL-MYERS SQUIBB COMPANY, Princeton, NJ (US)

(72) Inventors: Xiaojun Zhang, Furlong, PA (US); Eldon Scott Priestley, Yardley, PA (US); J. Alex Bates, Hillsborough, NJ (US); Oz Scott Halpern, Robbinsville, NJ (US); Samuel Kaye Reznik, Brookline, MA (US); Jeremy M. Richter, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 647 days.

(21) Appl. No.: 17/123,265

(22) Filed: Dec. 16, 2020

(65) Prior Publication Data

US 2021/0163465 A1  Jun. 3, 2021

Related U.S. Application Data

(63) Continuation of application No. 16/317,248, filed as application No. PCT/US2017/041878 on Jul. 13, 2017, now abandoned.

(Continued)

(51) Int. Cl.
C07D 417/04 (2006.01)
A61P 7/04 (2006.01)
(Continued)

(52) U.S. Cl.
CPC .............. *C07D 417/04* (2013.01); *A61P 7/04* (2018.01); *A61P 9/10* (2018.01); *C07D 403/04* (2013.01);
(Continued)

(58) Field of Classification Search
None
See application file for complete search history.

(56) References Cited

U.S. PATENT DOCUMENTS 6,166,041 A    12/2000  Cavalla et al.
6,313,126 B1 * 11/2001  Mewshaw ............ C07D 401/08
                                                      514/249

(Continued)

FOREIGN PATENT DOCUMENTS

EP    0052016 A1   5/1982
EP    0534443 A1   3/1993
(Continued)

OTHER PUBLICATIONS

Porter. Bioorganic and Medicinal Chemistry Letters, 2009, 19, 397-400 (Year: 2009).*

(Continued)

*Primary Examiner* — Noble E Jarrell
(74) *Attorney, Agent, or Firm* — Mary K. VanAtten

(57) ABSTRACT

Disclosed are compounds of Formula (I) to (VIII):

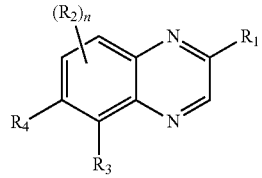

(I)

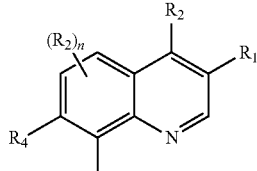

(II)

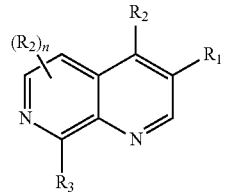

(III)

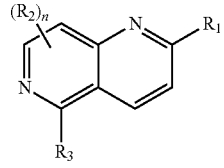

(IV)

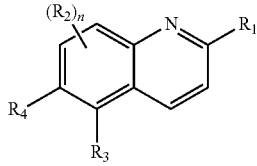

(V)

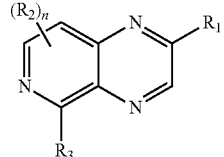

(VI)

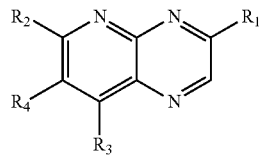

(VII)

(Continued)

-continued

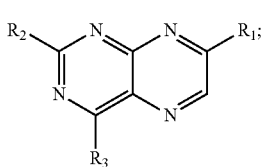

(VIII)

or a stereoisomer, tautomer, pharmaceutically acceptable salt, solvate or prodrug thereof, wherein $R_3$ is a bicyclic heteroaryl group substituted with zero to 3 $R_{3a}$; and $R_1$, $R_2$, $R_{3a}$, $R_4$, and n are defined herein. Also disclosed are methods of using such compounds as PAR4 inhibitors, and pharmaceutical compositions comprising such compounds. These compounds are useful in inhibiting or preventing platelet aggregation, and are useful for the treatment of a thromboembolic disorder or the primary prophylaxis of a thromboembolic disorder.

33 Claims, No Drawings

Related U.S. Application Data

(60) Provisional application No. 62/362,113, filed on Jul. 14, 2016.

(51) Int. Cl.
| | |
|---|---|
| *A61P 9/10* | (2006.01) |
| *C07D 403/04* | (2006.01) |
| *C07D 405/04* | (2006.01) |
| *C07D 405/14* | (2006.01) |
| *C07D 417/14* | (2006.01) |
| *C07D 471/04* | (2006.01) |
| *C07D 487/04* | (2006.01) |
| *C07D 513/04* | (2006.01) |
| *C07D 519/00* | (2006.01) |

(52) U.S. Cl.
CPC ......... *C07D 405/04* (2013.01); *C07D 405/14* (2013.01); *C07D 417/14* (2013.01); *C07D 471/04* (2013.01); *C07D 487/04* (2013.01); *C07D 513/04* (2013.01); *C07D 519/00* (2013.01)

(56) References Cited

U.S. PATENT DOCUMENTS

| | | | |
|---|---|---|---|
| 9,518,064 | B2 | 12/2016 | Martel et al. |
| 9,598,419 | B1 | 3/2017 | Martel et al. |
| 9,617,279 | B1 | 4/2017 | Zhang |
| 9,688,695 | B2 | 6/2017 | Banville et al. |
| 9,862,730 | B2 | 1/2018 | Lawrence et al. |
| 10,047,103 | B2 | 8/2018 | Banville et al. |
| 10,214,544 | B2 | 2/2019 | Banville |
| 10,238,638 | B2 | 3/2019 | Ruediger et al. |
| 10,428,077 | B2 | 10/2019 | Banville et al. |
| 10,517,870 | B2 | 12/2019 | Zhang et al. |
| 2019/0248771 | A1 | 8/2019 | Richter et al. |
| 2019/0300520 | A1 | 10/2019 | Fu et al. |
| 2019/0315774 | A1 | 10/2019 | Zhang et al. |
| 2020/0123160 | A1 | 4/2020 | Banvile et al. |

FOREIGN PATENT DOCUMENTS

| | | |
|---|---|---|
| EP | 1348701 A1 | 10/2003 |
| WO | 199820007 A1 | 5/1998 |
| WO | 2005012288 A1 | 2/2005 |
| WO | 2005113522 A1 | 12/2005 |
| WO | 2006015259 A2 | 2/2006 |
| WO | 2006076529 A1 | 7/2006 |
| WO | 2007149395 A2 | 12/2007 |
| WO | 2008000643 A1 | 1/2008 |
| WO | 2008073451 A2 | 6/2008 |
| WO | 2009073497 A2 | 6/2009 |
| WO | 2009134973 A1 | 11/2009 |
| WO | 2009141386 A1 | 11/2009 |
| WO | 2010011768 A1 | 1/2010 |
| WO | 2010035745 A1 | 4/2010 |
| WO | 2012154888 A1 | 11/2012 |
| WO | 2013130660 A1 | 9/2013 |
| WO | 2013163241 A1 | 10/2013 |
| WO | 2013163279 A1 | 10/2013 |
| WO | 2013163244 A1 | 4/2014 |
| WO | 2016/138199 A1 | 9/2016 |
| WO | 2016134450 A1 | 9/2016 |
| WO | 2016180536 A1 | 11/2016 |
| WO | 2017019828 A1 | 2/2017 |
| WO | 2018/013772 A1 | 1/2018 |
| WO | 2018013770 A1 | 1/2018 |
| WO | 2018013776 A1 | 1/2018 |

OTHER PUBLICATIONS

Meschia. Stroke, 2014, pp. 3754-3832 (Year: 2014).*
Beaulieu, Pierre L. et al., Discovery of the First Thumb Pocket 1 NS5B Polymerase Inhibitor (BILB 1941) with Demonstrated Antiviral Activity in Patients Chronically Infected with Genotype 1 Hepatitis C Virus (HCV), J. Med. Chem., vol. 55, pp. 7650-7666.
Beaulieu, Pierre L. et al., "From benzimidazole to indole-5-carboxamide Thumb Pocket 1 inhibitors of HCV N55B polymerase. Part 1:Indole C-2 SAR and discovery of diamide derivatives with nanomolar potency in cell-based subgenomic replicons", Bioorganic & Medicinal Chemistry Letters, vol. 21, pp. 3658-3663 (2011).
CAS Registered No. 682323-73-5 Registry(STN)[online],May 16, 2004.
CAS Registered No. 686704-00-7 Registry(STN)[online],May 27, 2004.
CAS Registered No. 695808-84-5 Registry(STN)[online],Jun. 18, 2004.
CAS Registered No. 733696-13-4 Registry(STN)[online],Aug. 27, 2004.
CAS Registered No. 752156-37-9 Registry(STN)[online],Sep. 26, 2004.
CAS Registered No. 756430-39-4 Registry(STN)[online],Oct. 3, 2004.
CAS Registered No. 761354-84-1 Registry(STN)[online],Oct. 12, 2004.
CAS Registered No. 772293-06-8 Registry(STN)[online],Oct. 29, 2004.
CAS Registered No. 776248-43-2 Registry(STN)[online],Nov. 8, 2004.
CAS Registered No. 777011-48-0 Registry(STN[online],Nov. 8, 2004.
Laroche, et al., "Direct heteroarylation of 5-bromothiophen-2-ylpyridine and of 8-bromoquinoline via palladium-catalysed C-H bond activation: simpler access to heteroarylated nitrogen-based derivatives", Catalysis Science & Technology, pp. 2072-2080 (2013).
Prakash, et al., "N-Difluoromethylation of Imidazoles and Benzimidazoles Using the Ruppert-Prakash Reagent under Neutral Conditions", Organic Letters, vol. 16, pp. 54-57 (2014).

* cited by examiner

BICYCLIC HETEROARYL SUBSTITUTED COMPOUNDS

CROSS REFERENCE TO RELATED APPLICATIONS

This application is a continuation of U.S. Ser. No. 16/317,248 filed on Jan. 11, 2019, now allowed, which is a 371 International Application of PCT/US2017/041878, filed Jul. 13, 2017, which is entitled to priority pursuant to 35 U.S.C. § 119(e) to U.S. provisional patent application No. 62/362,113, filed Jul. 14, 2016, hereby incorporated by reference in their entireties.

FIELD OF THE INVENTION

The present invention generally relates to bicyclic heteroaryl substituted compounds useful as inhibitors of platelet aggregation. Provided herein are bicyclic heteroaryl substituted compounds, compositions comprising such compounds, and methods of their use. The invention further pertains to pharmaceutical compositions containing at least one compound according to the invention that are useful in preventing or treating thromboembolic disorders.

BACKGROUND OF THE INVENTION

Thromboembolic diseases remain the leading cause of death in developed countries despite the availability of anticoagulants such as warfarin (COUMADIN®), heparin, low molecular weight heparins (LMWH), synthetic pentasaccharides, and antiplatelet agents such as aspirin and clopidogrel (PLAVIX®).

Current anti-platelet therapies have limitations including increased risk of bleeding as well as partial efficacy (relative cardiovascular risk reduction in the 20 to 30% range). Thus, discovering and developing safe and efficacious oral or parenteral antithrombotics for the prevention and treatment of a wide range of thromboembolic disorders remains an important goal.

Alpha-thrombin is the most potent known activator of platelet aggregation and degranulation. Activation of platelets is causally involved in atherothrombotic vascular occlusions. Thrombin activates platelets by cleaving G-protein coupled receptors termed protease activated receptors (PARs). PARs provide their own cryptic ligand present in the N-terminal extracellular domain that is unmasked by proteolytic cleavage, with subsequent intramolecular binding to the receptor to induce signaling (tethered ligand mechanism; Coughlin, S. R., Nature, 407:258-264 (2000)). Synthetic peptides that mimic the sequence of the newly formed N-terminus upon proteolytic activation can induce signaling independent of receptor cleavage. Platelets are a key player in atherothrombotic events. Human platelets express at least two thrombin receptors, commonly referred to as PAR1 and PAR4. Inhibitors of PAR1 have been investigated extensively, and several compounds, including vorapaxar and atopaxar have advanced into late stage clinical trials. Recently, in the TRACER phase III trial in ACS patients, vorapaxar did not significantly reduce cardiovascular events, but significantly increased the risk of major bleeding (Tricoci, P. et al., N. Eng. J. Med., 366(1):20-33 (2012). Thus, there remains a need to discover new antiplatelet agents with increased efficacy and reduced bleeding side effects.

There are several early reports of preclinical studies of PAR4 inhibitors. Lee, F-Y. et al., "Synthesis of 1-Benzyl-3-(5'-hydroxymethyl-2'-furyl)indazole Analogues as Novel Antiplatelet Agents", J. Med. Chem., 44(22):3746-3749 (2001) discloses in the abstract that the compound

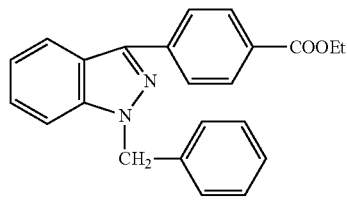

58

"was found to be a selective and potent inhibitor or protease-activated receptor type 4 (PAR4)-dependent platelet activation." Compound 58 is also referred to as YD-3 in Wu, C-C. et al., "Selective Inhibition of Protease-activated Receptor 4-dependent Platelet Activation by YD-3", Thromb. Haemost., 87:1026-1033 (2002). Also, see Chen, H. S. et al., "Synthesis and antiplatelet activity of ethyl 4-(1-benzyl-1H-indazol-3-yl)benzoate (YD-3) derivatives", Bioorg. Med. Chem., 16:1262-1278 (2008).

EP1166785 A1 and EP0667345 disclose various pyrazole derivatives which are useful as inhibitors of platelet aggregation.

The PCT publications WO 2013/163279, WO 2013/163244, and WO 2013/163241 disclose various PAR4 antagonists that are useful as inhibitors of platelet aggregation.

There still remains a need for compounds useful as inhibitors of platelet aggregation.

Applicants have found potent compounds that have activity as PAR4 inhibitors. These compounds are provided to be useful as pharmaceuticals with desirable potency, stability, bioavailability, therapeutic index, and toxicity values that are important to their drugability.

SUMMARY OF THE INVENTION

It has been found that bicyclic heteroaryl substituted compounds in accordance with the present invention are PAR4 antagonists which inhibit platelet aggregation in gamma-thrombin induced platelet aggregation assays.

Accordingly, the present invention provides bicyclic heteroaryl substituted compounds that are PAR4 antagonists and are useful as selective inhibitors of platelet aggregation, including stereoisomers, tautomers, pharmaceutically acceptable salts, solvates, or prodrugs thereof.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for the treatment or prophylaxis of thromboembolic disorders comprising administering to a patient in need of such treatment or prophylaxis a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment or prophylaxis of a thromboembolic disorder.

Other features and advantages of the invention will be apparent from the following detailed description and claims.

DETAILED DESCRIPTION

The first aspect of the present invention provides at least one compound of Formulas (I), (II), (III), (IV), (V), (VI), (VII), or (VIII):

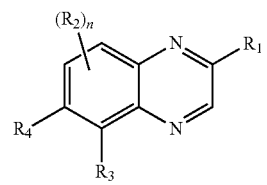
(I)

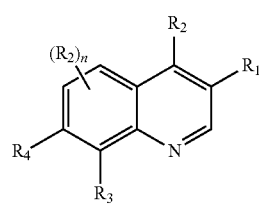
(II)

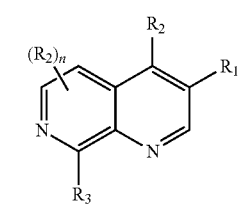
(III)

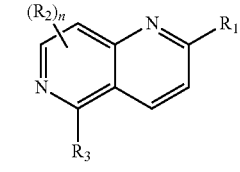
(IV)

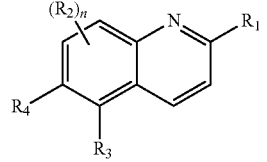
(V)

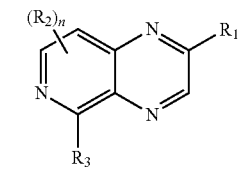
(VI)

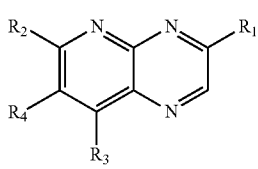
(VII)

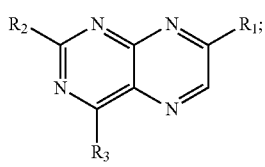
(VIII)

or a salt thereof; wherein:

$R_1$ is F, Cl, —OH, $C_{1-4}$ alkyl, $C_{1-4}$ fluoroalkyl, $C_{2-4}$ alkenyl, $C_{2-4}$ alkynyl, $C_{3-7}$ cycloalkyl, $C_{3-7}$ fluorocycloalkyl, $C_{1-4}$ alkoxy, $C_{1-4}$ fluoroalkoxy, $C_{2-4}$ hydroxyalkoxy, $C_{3-6}$ cycloalkoxy, ($C_{1-3}$ alkoxy)-($C_{1-3}$ alkylene), ($C_{1-3}$ alkoxy)-($C_{1-3}$ fluoroalkylene), ($C_{1-3}$ deuteroalkoxy)-($C_{1-3}$ deuteroalkylene), ($C_{1-3}$ fluoroalkoxy)-($C_{1-3}$ alkylene), ($C_{1-3}$ fluoroalkoxy)-($C_{1-3}$ fluoroalkylene), —$(CH_2)_{1-3}$O(phenyl), —$(CH_2)_{1-3}NR_aR_a$, —C(O)O($C_{1-6}$ alkyl), —C(O)$NR_aR_a$, —C(O)$NR_bR_b$, —$NH_2$, —NH($C_{1-6}$ alkyl), —N($C_{1-6}$ alkyl)$_2$, —NH ($C_{1-6}$ hydroxyalkyl), azetidinyl, pyrrolidinyl, furanyl, pyranyl, piperidinyl, morpholinyl, piperazinyl, —S(O)$_2$($C_{1-3}$alkyl), —S(O)$_2NR_aR_a$, $C_{1-3}$ alkylthio, or $C_{1-3}$ fluoroalkylthio;

$R_2$, at each occurrence, is independently H, F, Cl, Br, —OH, —CN, $C_{1-4}$ alkyl, $C_{1-4}$ fluoroalkyl, $C_{1-4}$ hydroxyalkyl, $C_{1-3}$ aminoalkyl, $C_{2-4}$ alkenyl, $C_{2-4}$ alkynyl, $C_{3-7}$ cycloalkyl, $C_{3-7}$ fluorocycloalkyl, $C_{1-6}$ alkoxy, $C_{1-3}$ fluoroalkoxy, $C_{1-3}$ alkylthio, $C_{1-3}$ fluoroalkylthio, ($C_{1-3}$ alkoxy)-($C_{1-3}$ alkylene), ($C_{1-3}$ fluoroalkoxy)-($C_{1-3}$ alkylene), —C(O)$NH_2$, —C(O)NH($C_{1-6}$ alkyl), —C(O)N($C_{1-6}$ alkyl)$_2$, —C(O)O($C_{1-6}$ alkyl), —C(O)NH($CH_2CH_2O$($C_{1-3}$ alkyl)), —C(O)$NR_bR_b$, —C(O)(piperidinyl), —CH(OH)($C_{3-6}$ cycloalkyl), —CH(OH)(phenyl), —CH(OH)(pyridyl), —S(O)$_2$($C_{1-3}$ alkyl), —S(O)$_2NR_aR_a$, or a cyclic group selected from phenyl, 5- to 6-membered heteroaryl, and 5- to 7-membered heterocyclyl, wherein said cyclic group is substituted with zero to 5 substituents independently selected from F, Cl, hydroxy, $C_{1-3}$ alkyl, $C_{1-3}$ alkoxy, cyclopropyl, and —CN;

$R_3$ is a bicyclic group selected from indolyl, benzofuranyl, benzo[b]thiophenyl, benzo[d]imidazolyl, benzo[d]oxazolyl, benzo[d]thiazolyl, imidazol[1,2-a]pyridinyl, thiazolo[4,5-b]pyridinyl, thiazolo[4,5-c]pyridinyl, thiazolo[5,4-b]pyridinyl, thiazolo[5,4-c]pyridinyl, 4,5,6,7-tetrahydrobenzo[d]thiazolyl, 4,5,6,7-tetrahydrobenzofuranyl, 4,5,6,7-tetrahydrothiazolo[5,4-c]pyridinyl, 5,6,7,8-tetrahydro-4H-cyclohepta[d]thiazolyl, 5,6-dihydro-4H-cyclopenta[d]thiazolyl, indolizinyl, pyrrolo[1,2-a]pyrimidinyl, 6,7-dihydrothiazolo[5,4-c]pyridinyl, 6,7-dihydro-5H-imidazo[2,1-b][1,3]oxazinyl, 4,5,6,7-tetrahydrobenzothiophenyl, furo[3,2-b] pyridinyl, and furo[2,3-b]pyridinyl, each bicyclic group substituted with zero to 3 $R_{3a}$;

$R_{3a}$, at each occurrence, is independently:

(i) F, Cl, —CN, —OH, $C_{1-3}$ alkyl, $C_{1-6}$ fluoroalkyl, $C_{1-6}$ hydroxyalkyl, $C_{1-6}$ hydroxy-deuteroalkyl, $C_{1-6}$ hydroxyfluoroalkyl, $C_{1-6}$ alkoxy, $C_{1-3}$ fluoroalkoxy, $C_{3-6}$ cycloalkyl, $C_{3-6}$ fluorocycloalkyl, 4- to 7-membered heterocyclyl, —CH (OH)R$_y$ wherein R$_y$ is C$_{3-6}$ cycloalkyl, aryl, heteroaryl, or 4- to 7-membered heterocyclyl; (C$_{1-3}$ alkoxy)-(C$_{1-3}$ alkylene), —(CH$_2$)$_{1-3}$NR$_a$R$_a$, —(CH$_2$)$_{1-3}$NHS(O)$_2$(aryl), —O(CH$_2$)$_{1-3}$(aryl), —O(CH$_2$)$_{1-3}$(thiazolyl), —O(CH$_2$)$_{1-3}$(oxazolidinonyl), —O(CH$_2$)$_{1-3}$(amino isoxazolyl), —O(CH$_2$)$_{1-3}$(imidazolyl substituted with phenyl), C$_{1-6}$ hydroxyalkoxy, (C$_{1-3}$ alkoxy)-(C$_{1-6}$ alkoxy), —O(CH$_2$)$_{1-4}$O(aryl), —O(CH$_2$)$_{1-4}$O(CH$_2$)$_{1-3}$(aryl), —O(CH$_2$)$_{1-4}$NR$_a$R$_a$, —O(CH$_2$)$_{1-3}$CHR$_a$NR$_a$(methoxy pyrimidinyl), —O(CH$_2$)$_{1-4}$NHS(O)$_2$(C$_{1-3}$ alkyl), —O(CH$_2$)$_{1-4}$NHS(O)$_2$(aryl), —O(CH$_2$)$_{1-4}$C(O)OH, —O(CH$_2$)$_{1-4}$C(O)O(C$_{1-6}$ alkyl), —O(CH$_2$)$_{1-4}$C(O)NR$_a$(CH$_2$)$_{0-3}$(aryl), —O(CH$_2$)$_{1-4}$C(O)NR$_a$(CH$_2$)$_{0-3}$(heteroaryl), —O(CH$_2$)$_{1-4}$C(O)(morpholinyl), —O(CH$_2$)$_{1-4}$OC(O)O(C$_{1-3}$ alkyl), —O(CH$_2$)$_{1-3}$CHR$_a$OC(O)NR$_a$(CH$_2$)$_{1-4}$C(O)NR$_a$R$_a$, —CH$_2$CHR$_d$OC(O)NR$_a$(heteroaryl), —O(CH$_2$)$_{1-4}$OC(O)NR$_a$(heteroaryl), —O(imidazolyl substituted with aryl), —C(O)OH, —C(O)O(C$_{1-6}$ alkyl), —NR$_a$C(O)(furanyl), —NR$_a$C(O)(pyranyl), —NR$_a$C(O)O(C$_{1-6}$ alkyl), —NR$_a$C(O)O(CH$_2$)$_{1-4}$(aryl), —O(CH$_2$)$_{1-4}$NR$_a$C(O)O(C$_{1-6}$ alkyl), —O(CH$_2$)$_{1-4}$NR$_a$C(O)O(CH$_2$)$_{0-4}$(tetrahydropyranyl), —O(CH$_2$)$_{1-4}$NR$_a$C(O)O(CH$_2$)$_{0-4}$(aryl), —O(CH$_2$)$_{1-4}$NR$_a$C(O)O(CH$_2$)$_{0-4}$(heteroaryl), or —O(CH$_2$)$_{1-4}$NR$_a$C(O)O(CH$_2$)$_{0-4}$(tetrahydrofuranyl), wherein each of said aryl, heteroaryl, and 3- to 6-membered heterocyclyl is substituted with zero to 5 substituents independently selected from F, Cl, —CN, C$_{1-3}$ alkyl, C$_{1-3}$ fluoroalkyl, C$_{1-4}$ hydroxyalkyl, C$_{1-3}$ alkoxy, —OCF$_3$, —OCHF$_2$, —NH$_2$, —NH(C$_{1-6}$ alkyl), —N(C$_{1-6}$ alkyl)$_2$, —C(O)O(C$_{1-3}$ alkyl), C$_{1-3}$ hydroxyalkoxy, phenyl, —CONR$_c$R$_c$, and —S(O)$_2$NR$_c$R$_c$;

(ii) —CH(OH)CR$_h$R$_i$R$_j$ wherein R$_h$ and R$_i$ are independently H, F, C$_{1-4}$ alkyl, C$_{1-4}$ fluoroalkyl, C$_{1-3}$ alkoxy, C$_{1-3}$ fluoroalkoxy, or taken together with the carbon atom to which they are attached, form C$_{3-8}$ cycloalkyl or 4- to 7-membered heterocyclyl ring; and R$_j$ is H, C$_{1-6}$ alkyl, C$_{1-5}$ fluoroalkyl, (C$_{1-3}$ alkoxy)-(C$_{1-3}$ alkylene), C$_{3-8}$ cycloalkyl, C$_{3-8}$ heterocyclyl, aryl, or heteroaryl;

(iii) —O(CH$_2$)$_{1-4}$NR$_a$S(O)$_2$(C$_{1-4}$ alkyl) or —O(CH$_2$)$_{1-4}$NR$_a$S(O)$_2$R$_w$, wherein R$_w$ is aryl or heteroaryl, each substituted with zero to 2 substituents independently selected from F, Cl, cyano, C$_{1-3}$ alkyl, C$_{1-3}$ alkoxy, —OCF$_3$, —OCHF$_2$, and C$_{1-3}$ fluoroalkyl; or (iv) —O(CH$_2$)$_{1-4}$OC(O)NR$_a$R$_x$, —OCH(R$_d$)(CH$_2$)$_{1-3}$OC(O)NR$_a$R$_x$, —OCR$_d$R$_d$(CH$_2$)$_{1-3}$OC(O)NR$_a$R$_x$, —O(CH$_2$)$_{1-3}$CH(R$_d$)OC(O)NR$_a$R$_x$, —O(CH$_2$)$_{1-3}$CR$_d$R$_d$OC(O)NR$_a$R$_x$, —OCH(R$_d$)CH(R$_d$)(CH$_2$)$_{0-2}$OC(O)NR$_a$R$_x$, or —OCR$_d$R$_d$CR$_d$R$_d$(CH$_2$)$_{0-2}$OC(O)NR$_a$R$_x$, wherein R$_x$ is selected from H, C$_{1-4}$ alkyl, C$_{1-4}$ fluoroalkyl, aryl, heteroaryl, and —CH$_2$(heteroaryl), each aryl and heteroaryl substituted with zero to 2 substituents independently selected from F, Cl, Br, —CN, —OH, C$_{1-3}$ alkyl, C$_{1-3}$ fluoroalkyl, C$_{1-6}$ hydroxyalkyl, C$_{1-6}$ hydroxy-deuteroalkyl, C$_{1-6}$ hydroxyalkoxy, C$_{1-6}$ hydroxy-fluoroalkoxy, C$_{1-3}$ alkoxy, —C(O)OH, —(CH$_2$)$_{0-3}$C(O)O(C$_{1-3}$ alkyl), —(CH$_2$)$_{1-3}$OP(O)(OH)$_2$, —CH$_2$(morpholinyl), —C(O)NH$_2$, —C(O)NH(C$_{1-6}$ alkyl), —C(O)N(C$_{1-6}$ alkyl)$_2$, —C(O)NR$_a$(C$_{1-6}$ hydroxyalkyl), —C(O)NR$_b$R$_b$, —S(O)$_2$NR$_a$R$_a$, —NH$_2$, —NH(C$_{1-6}$ alkyl), —NR$_a$(C$_{1-6}$ hydroxyalkyl), —N(C$_{1-6}$ alkyl)$_2$, —NR$_a$C(O)(C$_{1-6}$ alkyl), —NR$_a$C(O)(chloro, fluorophenyl), —NR$_a$S(O)$_2$(C$_{1-3}$ alkyl), —C(O)NR$_a$(CH$_2$)$_{0-1}$(hydroxymethyloxetanyl), —C(O)NR$_a$(CH$_2$)$_{0-1}$(hydroxymethyl C$_{3-6}$ cycloalkyl), —C(O)NR$_a$(CH$_2$)$_{0-1}$(hydroxy C$_{3-6}$ cycloalkyl), —C(O)NHCH$_2$C(CH$_3$)$_2$OP(O)(OH)$_2$, —C(O)(hydroxypiperidinyl), —C(O)(hydroxypyrrolidinyl), —C(O)(hydroxymethylpyrrolidinyl), —C(O)(morpholinyl), —C(O)(hydroxymethylmorpholinyl), pyrrolidinyl, morpholinyl, thiophenyl, methyl triazolyl, and oxazolidinonyl;

R$_4$ is H, F, Cl, or —CH$_3$;

R$_a$, at each occurrence, is independently H, C$_{1-4}$alkyl, or C$_{1-4}$fluoroalkyl;

two R$_b$ along with the nitrogen atom to which they are attached form a 4- to 7-membered heterocyclo ring having 1 to 2 nitrogen atoms and 0-1 oxygen or sulfur atoms;

R$_c$, at each occurrence, is independently C$_{1-3}$ alkyl or C$_{1-3}$ hydroxyalkyl, or two R$_c$ along with the nitrogen atom to which they are attached form a heterocyclyl or bicyclic heterocyclyl;

R$_d$, at each occurrence, is independently C$_{1-6}$ alkyl, C$_{1-4}$ fluoroalkyl, C$_{1-6}$ hydroxyalkyl, (C$_{1-4}$ alkoxy)-(C$_{1-3}$ alkylene), (C$_{1-2}$ fluoroalkoxy)-(C$_{1-2}$ alkylene), (C$_{3-6}$ cycloalkyl)-(C$_{0-2}$ alkylene), aryl(C$_{1-2}$ alkylene), heteroaryl(C$_{1-2}$ alkylene), aryloxy-(C$_{1-2}$ alkylene), arylCH$_2$O—(C$_{1-2}$ alkylene), or heteroaryloxy-(C$_{1-2}$ alkylene); and n is zero, 1, or 2.

One embodiment provides at least one compound of Formulas (I), (II), (III), (IV), (V), (VI), (VII), or (VIII) or a salt thereof, wherein:

R$_1$ is —OH, C$_{1-2}$ alkyl, —CHFCH$_3$, —CH═CH$_2$, C$_{1-3}$ alkoxy, C$_{1-2}$ fluoroalkoxy, —OCH$_2$CH$_2$OH, —CH$_2$O(C$_{1-2}$ alkyl), —CD$_2$OCD$_3$, —CH$_2$OCHF$_2$, —CF$_2$OCH$_3$, —CH$_2$O(phenyl), —CH(CH$_3$)OCH$_3$, —NH(CH$_3$), —N(CH$_3$)$_2$, —CH$_2$N(CH$_3$)$_2$, —C(O)NH$_2$, —C(O)NH(CH$_3$), —C(O)N(CH$_3$)$_2$, —C(O)NH(CH$_2$CH$_2$OH), —C(O)OCH$_3$, —CH(CH$_3$)OCH$_3$, cyclopropyl, furanyl, or —O(cyclopropyl);

R$_2$, at each occurrence, is independently H, F, Cl, —CN, —CH$_3$, —CH$_2$F, —CHF$_2$, —CF$_3$, —OCH$_3$, —CH$_2$OH, —CH$_2$CH$_2$OH, —CH(CH$_3$)OH, —C(CH$_3$)$_2$OH, —CH(OH)CH$_2$OH, —CH$_2$NH$_2$, —C(O)NH$_2$, —C(O)N(CH$_3$)$_2$, —C(O)(piperidinyl), —C(O)OCH$_3$, —C(O)NH(CH$_2$CH$_2$OCH$_3$), —CH(OH)(cyclopropyl), —CH(OH)(phenyl), —CH═CH$_2$, —C(CH$_3$)═CH$_2$, or —C≡CH;

R$_3$ is:

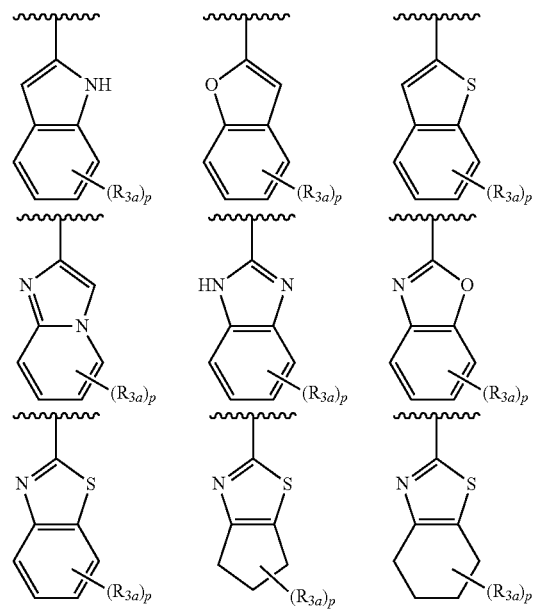

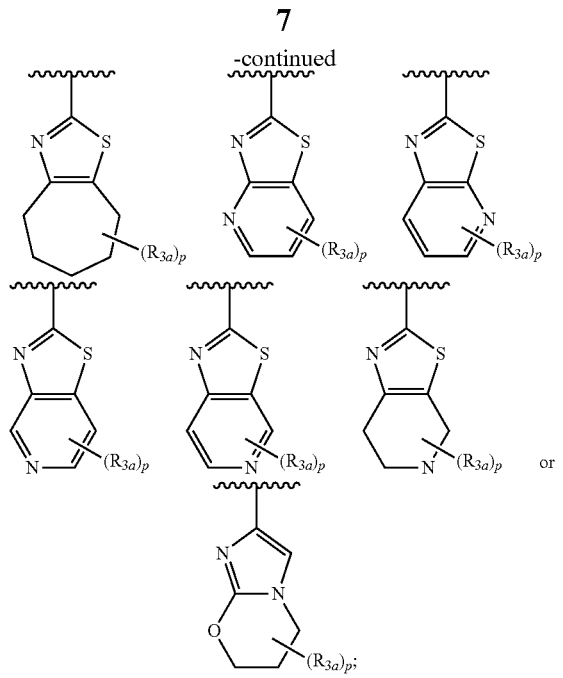

$R_{3a}$, at each occurrence, is independently:

(i) F, Cl, —CN, —OH, —CH₃, —CF₃, —CHFC(CH₃)₃, cyclopropyl, —CH₂OH, —CD₂OH, —CH₂CH₂OH, —CH(OH)CH₃, —C(CH₃)₂OH, —CH(OH)C(CH₃)₃, —CD(OH)C(CH₃)₃, —CH(OH)CF₃, —CH(OH)CH₂CF₃, —CH(OH)(cyclopropyl), —CH(OH)(methylcyclopropyl), —CH(OH)(trifluoromethylcyclopropyl), —CH(OH)(cyclopropyl substituted with phenyl), —CH(OH)(cyclobutyl), —CH(OH)(methoxycyclobutyl), —CH(OH)(ethoxycarbonylcyclobutyl), —CH(OH)(trifluoromethylcyclobutyl), —CH(OH)(hydroxymethylcyclobutyl), —CH(OH)(cyclobutyl substituted with phenyl), —CH(OH)(cyclohexyl), —CH(OH)(methylcyclohexyl), —CH(OH)(phenyl), —CH(OH)(isopropylphenyl), —CH(OH)(trifluoromethylphenyl), —CH(OH)(fluoro, methoxyphenyl), —CH(OH)(pyridinyl), —CH(OH)(thiazolyl), —CH(OH)(tetrahydropyranyl), —CH(OH)(methyltetrahydropyranyl), —CH₂OCH₃, —CH₂N(CH₃)₂, —CH₂NHS(O)₂(phenyl), or —CH(OH)CH₂(phenyl);

(ii) —OCH₃, —OCH₂CH₃, —OCH(CH₃)₂, —OCF₃, —OCHF₂, —OCH₂(phenyl), —OCH₂(thiazolyl), —OCH₂(oxazolidinonyl), —OCH₂(amino isoxazolyl), —OCH₂(imidazolyl substituted with phenyl), —OCH₂CH₂OH, —OCH₂CH(CH₃)OH, —OCH₂CH₂OCH₃, —OCH(CH₃)CH₂OH, —OCH₂CH(OH)CH₃, —OCH(CH₃)CH(OH)CH₃, —OCH₂C(CH₃)₂OH, —OCH₂CH₂O(phenyl), —OCH₂CH₂OCH₂(phenyl), —OCH₂CH₂NH(CH₃), —OCH₂CH(CH₃)NH(methoxy pyrimidinyl), —OCH₂C(O)OH, —OCH₂C(O)OCH₃, —OCH₂C(O)OCH₂CH₃, —OCH₂C(O)OC(CH₃)₃, —OCH₂C(O)NH(phenyl), —OCH₂C(O)NHCH₂(phenyl), —OCH₂C(O)(morpholinyl), —OCH₂CH₂CH₂C(O)NH(pyridinyl), —OCH₂CH₂OC(O)OCH₃, —OCH₂CH(CH₃)OC(O)NHCH₂CH₂C(O)NH₂, —OCH₂CH(CH₂CH₃)OC(O)NH(pyridinyl), —OCH₂CH(CH₂OCH₃)OC(O)NH(pyridinyl), —OCH₂CH(CH₂OC(CH₃)₃)OC(O)NH(pyridinyl), —OCH₂CH(CH₂OCH₂CH(CH₃)₂)OC(O)NH(pyridinyl), —OCH₂CH(CH₂OCH₂(phenyl))OC(O)NH(pyridinyl), —OCH₂CH(CH₂OCH₂CH(CH₃)₂)OC(O)NH(pyrimidinyl), or —OCH₂CH(CH₂OCH₂CH(CH₃)₂)OC(O)NH(methyl pyrimidinyl);

(iii) —C(O)OH, —C(O)OCH₃, or —C(O)OC(CH₃)₃;

(iv) —NHC(O)OCH₃, —NHC(O)OC(CH₃)₃, —NHC(O)OCH₂(phenyl), —NHC(O)OCH₂(tetrahydrofuranyl), or —NHC(O)O(tetrahydropyranyl);

(v) —OCH₂CH₂NHC(O)OCH₃, —OCH₂CH₂NHC(O)O(tetrahydropyranyl), —OCH₂CH₂NHC(O)OCH₂(phenyl), —OCH₂CH₂NHC(O)O(methoxyphenyl), —OCH₂CH₂NHC(O)O(tetrahydrofuranyl), —OCH₂CH₂NHC(O)OCH₂(tetrahydrofuranyl), —OCH₂CH₂NHC(O)NH(pyridinyl), —OCH₂CH₂N(CH₃)C(O)NH(methylpyrimidinyl), or —OCH₂CH(CH₃)OC(O)OCH₂(aminopyridinyl);

(vi) —OCH₂CH₂NHS(O)₂CH₃ or —OCH₂CH₂NHS(O)₂$R_w$ wherein $R_w$ is phenyl or pyridinyl, each substituted with zero to 2 substituents independently selected from F, Cl, and —CH₃; or (vii) —OCH₂CH₂OC(O)NHR_z, —OCH(CH₃)CH₂OC(O)NHR_z, —OCH₂CH(CH₃)OC(O)NHR_z, —OCH(CH₃)CH(CH₃)OC(O)NHR_z, —OCH₂CH(CH—₂O(isobutyl))OC(O)NHR_z, —OCH₂CH(CH₂CH₃)OC(O)NHR_z, —OCH₂CH(CH₂OCH₃)OC(O)NHR_z, or —OCH₂CH(CH₂OCH₂CH(CH₃)₂)OC(O)NHR_z wherein R_z is H, —CH₂CF₃, phenyl, pyrrolyl, pyrazolyl, thiazolyl, isothiazolyl, pyridinyl, pyridazinyl, pyrimidinyl, pyrazinyl, oxadiazolyl, thiadiazolyl, indolyl, pyrrolo[2,3-b]pyridinyl, benzo[d]oxazolonyl, —CH₂(pyrazolyl), —CH₂(imidazolyl), or —CH₂(pyridinyl), each substituted with zero to 2 substituents independently selected from F, Cl, Br, —CN, —OH, —CH₃, —CH₂CH₂CH₃, —CF₃, —CH₂OH, —CD₂OH, —CH(CH₃)OH, —CH₂CH₂OH, —CH₂CH₂CH₂OH, —C(CH₃)₂OH, —CH₂CH(CH₃)OH, —CH₂C(CH₃)₂OH, —CH₂CH₂C(O)OCH₃, —CH₂OP(O)(OH)₂, —CH₂CH₂OP(O)(OH)₂, —CH₂(morpholinyl), —OCH₃, —OCH₂CH₂OH, —OCH₂CH(CH₃)OH, —OCH₂C(CH₃)₂OH, —OCH₂CH₂C(CH₃)₂OH, —OCH(CH₃)CH₂OH, —OCH₂CH(OH)CH₂OH, —OCH₂CF₂OH, —OCH₂CF₂CH₂OH, —C(O)OH, —C(O)OCH₃, —C(O)NH₂, —C(O)NH(CH₃), —C(O)N(CH₃)₂, —C(O)NH(CH₂CH₂OH), —C(O)NH(CH₂CH(CH₃)OH), —C(O)NH(CH₂C(CH₃)₂OH), —C(O)NH(CH₂C(CH₃)₂CH₂OH), —C(O)NH(CH₂CH₂C(CH₃)₂OH), —C(O)N(CH₃)CH₂CH₂OH, —C(O)N(CH₃)CH₂C(CH₃)₂OH, —C(O)NHCH₂(hydroxymethyloxetanyl), —C(O)NH(hydroxymethylcyclobutyl), —C(O)NHCH₂(hydroxycyclobutyl), —C(O)NHCH₂(hydroxymethylcyclobutyl), —C(O)NHCH₂C(CH₃)₂OP(O)(OH)₂, —C(O)(hydroxypiperidinyl), —C(O)(hydroxypyrrolidinyl), —C(O)(hydroxymethylpyrrolidinyl), —C(O)(morpholinyl), —C(O)(hydroxymethylmorpholinyl), —NH₂, —N(CH₃)₂, —NHC(O)CH₃, —NHC(O)(chloro, fluorophenyl), —NH(CH₂C(CH₃)₂OH), —N(CH₃)S(O)₂CH₃, pyrrolidinyl, morpholinyl, thiophenyl, methyl triazolyl, and oxazolidinonyl;

$R_4$ is H, F, or —CH₃; and p is zero, 1, 2, or 3.

One embodiment provides at least one compound of Formulas (I), (II), (III) or (IV) or a salt thereof, wherein $R_1$, $R_2$, $R_3$, $R_4$, and n are defined in the first aspect. Included in this embodiment are compounds in which $R_3$ is:

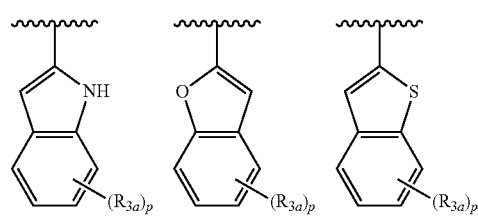

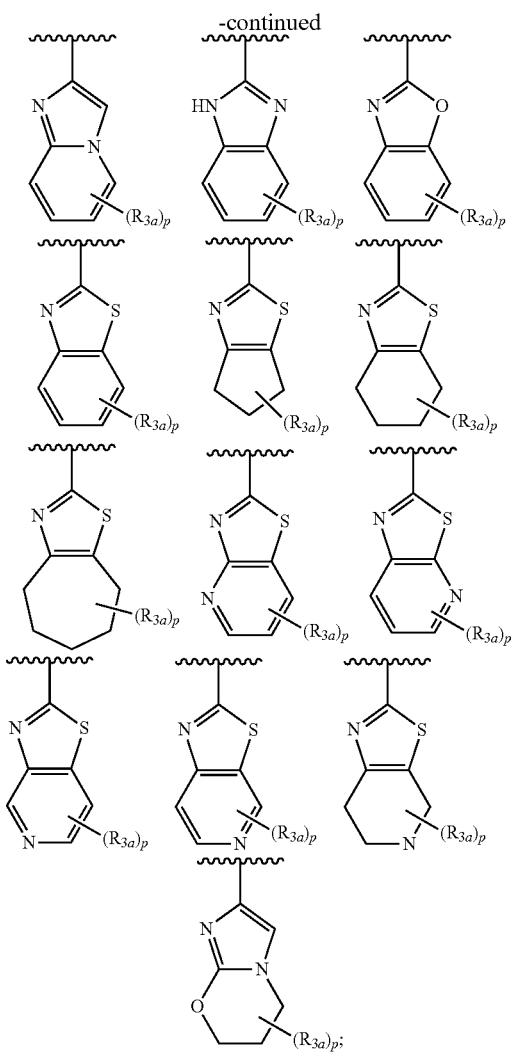

p is zero, 1, 2, or 3; and $R_{3a}$ is defined in the first aspect. Also included in this embodiment are compounds in which $R_4$ is H, F, or —$CH_3$.

One embodiment provides at least one compound of Formulas (I), (II), (III), or (IV) or a salt thereof, wherein $R_1$, $R_2$, $R_3$, $R_4$, and n are defined in the first aspect.

One embodiment provides at least one compound of Formulas (I) or (II) or a salt thereof, wherein $R_1$, $R_2$, $R_3$, $R_4$, and n are defined in the first aspect.

One embodiment provides at least one compound of Formula (I) or a salt thereof, wherein $R_1$, $R_2$, $R_3$, $R_4$, and n are defined in the first aspect.

One embodiment provides at least one compound of Formula (II) or a salt thereof, wherein $R_1$, $R_2$, $R_3$, $R_4$, and n are defined in the first aspect.

One embodiment provides at least one compound of Formula (III) or a salt thereof, wherein $R_1$, $R_2$, $R_3$, and n are defined in the first aspect.

One embodiment provides at least one compound of Formula (IV) or a salt thereof, wherein $R_1$, $R_2$, $R_3$, and n are defined in the first aspect.

One embodiment provides at least one compound of Formula (V) or a salt thereof, wherein $R_1$, $R_2$, $R_3$, $R_4$, and n are defined in the first aspect.

One embodiment provides at least one compound of Formula (VI) or a salt thereof, wherein $R_1$, $R_2$, $R_3$, and n are defined in the first aspect.

One embodiment provides at least one compound of Formula (VII) or a salt thereof, wherein $R_1$, $R_2$, $R_3$, $R_4$, and n are defined in the first aspect.

One embodiment provides at least one compound of Formula (VIII) or a salt thereof, wherein $R_1$, $R_2$, $R_3$, and n are defined in the first aspect.

One embodiment provides at least one compound of Formula (I) or a salt thereof, wherein $R_1$, $R_2$, $R_3$, $R_4$, and n are defined in the first aspect. Included in this embodiment are compounds in which $R_3$ is:

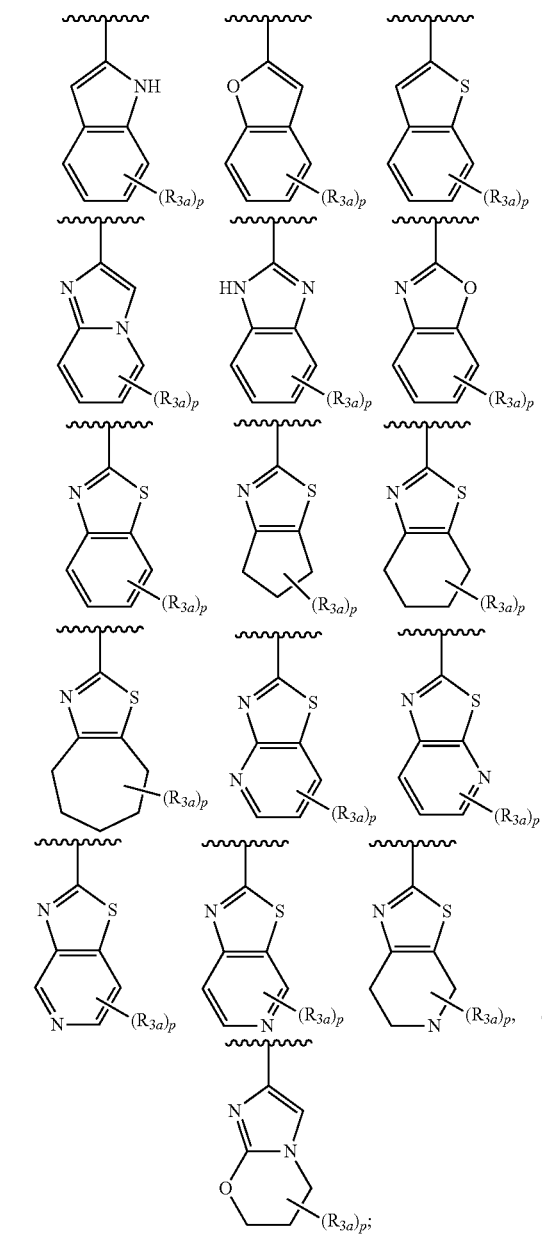

p is zero, 1, 2, or 3; and $R_{3a}$ is defined in the first aspect. Also included in this embodiment are compounds in which $R_4$ is H, F, or —$CH_3$.

One embodiment provides at least one compound of Formulas (I) or (II) or a salt thereof, wherein $R_1$, $R_2$, $R_3$, $R_4$, and n are defined in the first aspect. Included in this embodiment are compounds in which $R_3$ is:

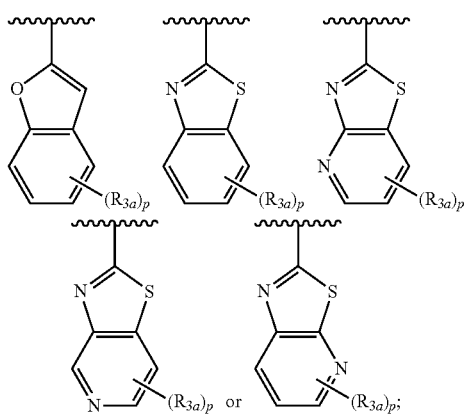

p is zero, 1, 2, or 3; and $R_{3a}$ is defined in the first aspect.

One embodiment provides at least one compound of Formulas (I), (II), (III), (IV), (V), (VI), or (VIII) or a salt thereof, wherein $R_3$ is:

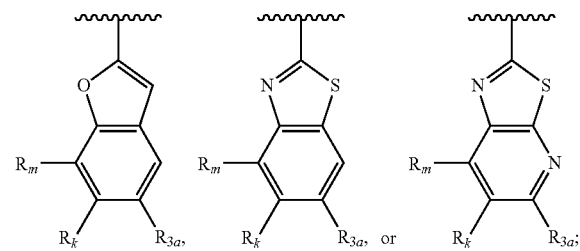

$R_m$ is H or Cl; $R_k$ is H or F; and $R_1$, $R_2$, $R_{3a}$, $R_4$, and n are defined in the first aspect. Included in this embodiment are compounds of Formula (I).

One embodiment provides at least one compound of Formulas (I), (II), (III), (IV), (V), (VI), (VII), or (VIII) or a salt thereof, wherein $R_3$ is:

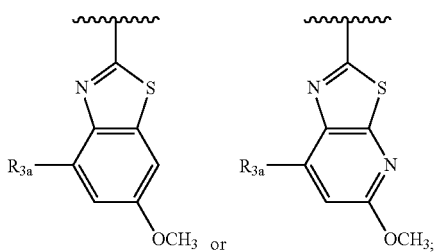

and $R_1$, $R_2$, $R_{3a}$, $R_4$, and n are defined in the first aspect. Included in this embodiment are compounds of Formula (I).

One embodiment provides at least one compound of Formulas (I), (II), (III), (IV), (V), (VI), (VII), or (VIII) or a salt thereof, wherein $R_1$ is —OH, $C_{1-2}$ alkyl, —CHFCH$_3$, —CH═CH$_2$, $C_{1-3}$ alkoxy, $C_{1-2}$ fluoroalkoxy, —OCH$_2$CH$_2$OH, —CH$_2$O($C_{1-2}$ alkyl), —CD$_2$OCD$_3$, —CH$_2$OCHF$_2$, —CF$_2$OCH$_3$, —CH$_2$O(phenyl), —CH(CH$_3$)OCH$_3$, —NH(CH$_3$), —N(CH$_3$)$_2$, —CH$_2$N(CH$_3$)$_2$, —C(O)NH$_2$, —C(O)NH(CH$_3$), —C(O)N(CH$_3$)$_2$, —C(O)NH(CH$_2$CH$_2$OH), —C(O)OCH$_3$, —CH(CH$_3$)OCH$_3$, cyclopropyl, furanyl, or —O(cyclopropyl); and $R_2$, $R_3$, $R_4$, and n are defined in the first aspect. Included in this embodiment are compounds in which $R_1$ is —CH$_2$OCH$_3$, —OCH$_3$, or —OCHF$_2$.

One embodiment provides at least one compound of Formulas (I), (II), (III), (IV), (V), (VI), (VII), or (VIII) or a salt thereof, wherein $R_2$, at each occurrence, is independently H, F, Cl, —CN, —CH$_3$, —CH$_2$F, —CHF$_2$, —CF$_3$, —OCH$_3$, —OCF$_3$, —CH$_2$OH, —CH$_2$CH$_2$OH, —CH(CH$_3$)OH, —C(CH$_3$)$_2$OH, —CH(OH)CH$_2$OH, —CH$_2$NH$_2$, —C(O)NH$_2$, —C(O)N(CH$_3$)$_2$, —C(O)(piperidinyl), —C(O)OCH$_3$, —C(O)NH(CH$_2$CH$_2$OCH$_3$), —CH(OH)(cyclopropyl), —CH(OH)(phenyl), —CH═CH$_2$, —C(CH$_3$)═CH$_2$, or —C≡CH; and $R_1$, $R_3$, $R_4$, and n are defined in the first aspect. Included in this embodiment are compounds in which $R_2$ is F, Cl, —CN, —CH$_3$, or —CH$_2$OH. Also included in this embodiment are compounds in which $R_2$ is —CH$_3$.

One embodiment provides at least one compound of Formula (I), (II), (V), and (VII) or a salt thereof, wherein $R_4$ is H, F, or —CH$_3$; and $R_1$, $R_2$, $R_3$, and n are defined in the first aspect. Included in this embodiment are compounds in which $R_4$ is H and F. Also included in this compounds in which $R_4$ is H.

One embodiment provides at least one compound of Formulas (I), (II), (III), (IV), (V), (VI), (VII), or (VIII) or a salt thereof, wherein $R_{3a}$, at each occurrence, is independently, (i) F, Cl, —CN, —OH, —CH$_3$, —CF$_3$, —CHFC(CH$_3$)$_3$, cyclopropyl, —CH$_2$OH, —CD$_2$OH, —CH$_2$CH$_2$OH, —CH(OH)CH$_3$, —C(CH$_3$)$_2$OH, —CH(OH)C(CH$_3$)$_3$, —CD(OH)C(CH$_3$)$_3$, —CH(OH)CF$_3$, —CH(OH)CH$_2$CF$_3$, —CH(OH)(cyclopropyl), —CH(OH)(methylcyclopropyl), —CH(OH)(trifluoromethylcyclopropyl), —CH(OH)(cyclopropyl substituted with phenyl), —CH(OH)(cyclobutyl), —CH(OH)(methoxycyclobutyl), —CH(OH)(ethoxycarbonylcyclobutyl), —CH(OH)(trifluoromethylcyclobutyl), —CH(OH)(hydroxymethylcyclobutyl), —CH(OH)(cyclobutyl substituted with phenyl), —CH(OH)(cyclohexyl), —CH(OH)(methylcyclohexyl), —CH(OH)(phenyl), —CH(OH)(isopropylphenyl), —CH(OH)(trifluoromethylphenyl), —CH(OH)(fluoro, methoxyphenyl), —CH(OH)(pyridinyl), —CH(OH)(thiazolyl), —CH(OH)(tetrahydropyranyl), —CH(OH)(methyltetrahydropyranyl), —CH$_2$OCH$_3$, —CH$_2$N(CH$_3$)$_2$, —CH$_2$NHS(O)$_2$(phenyl), or —CH(OH)CH$_2$(phenyl); (ii) —OCH$_3$, —OCH$_2$CH$_3$, —OCH(CH$_3$)$_2$, —OCF$_3$, —OCHF$_2$, —OCH$_2$(phenyl), —OCH$_2$(thiazolyl), —OCH$_2$(oxazolidinonyl), —OCH$_2$(amino isoxazolyl), —OCH$_2$(imidazolyl substituted with phenyl), —OCH$_2$CH$_2$OH, —OCH$_2$CH(CH$_3$)OH, —OCH$_2$CH$_2$OCH$_3$, —OCH(CH$_3$)CH$_2$OH, —OCH$_2$CH(OH)CH$_3$, —OCH(CH$_3$)CH(OH)CH$_3$, —OCH$_2$C(CH$_3$)$_2$OH, —OCH$_2$CH$_2$O(phenyl), —OCH$_2$CH$_2$OCH$_2$(phenyl), —OCH$_2$CH$_2$NH(CH$_3$), —OCH$_2$CH(CH$_3$)NH(methoxy pyrimidinyl), —OCH$_2$C(O)OH, —OCH$_2$C(O)OCH$_3$, —OCH$_2$C(O)OCH$_2$CH$_3$, —OCH$_2$C(O)OC(CH$_3$)$_3$, —OCH$_2$C(O)NH(phenyl), —OCH$_2$C(O)NHCH$_2$(phenyl), —OCH$_2$C(O)(morpholinyl), —OCH$_2$CH$_2$CH$_2$C(O)NH(pyridinyl), —OCH$_2$CH$_2$OC(O)OCH$_3$, —OCH$_2$CH(CH$_3$)OC(O)NHCH$_2$CH$_2$C(O)NH$_2$, —OCH$_2$CH(CH$_2$CH$_3$)OC(O)NH(pyridinyl), —OCH$_2$CH(CH$_2$OCH$_3$)OC(O)NH(pyridinyl), —OCH$_2$CH(CH$_2$OC(CH$_3$)$_3$)OC(O)NH(pyridinyl), —OCH$_2$CH(CH$_2$OCH$_2$CH(CH$_3$)$_2$)OC(O)NH(pyridinyl), —OCH$_2$CH(CH$_2$OCH$_2$(phenyl))OC(O)NH(pyridinyl), —OCH$_2$CH(CH$_2$OCH$_2$CH(CH$_3$)$_2$)OC(O)NH(pyrimidinyl), or —OCH$_2$CH(CH$_2$OCH$_2$CH(CH$_3$)$_2$)OC(O)NH(methyl pyrimidinyl); (iii) —C(O)OH, —C(O)OCH$_3$, or —C(O)OC(CH$_3$)$_3$; (iv) —NHC(O)OCH$_3$, —NHC(O)OC(CH$_3$)$_3$, —NHC(O)OCH$_2$(phenyl), —NHC(O)OCH$_2$(tetrahydrofuranyl), or —NHC(O)O(tetrahydropyranyl); (v) —OCH$_2$CH$_2$NHC(O)OCH$_3$, —OCH$_2$CH$_2$NHC(O)O(tetrahydropyranyl), —OCH$_2$CH$_2$NHC(O)OCH$_2$(phenyl), —OCH₂CH₂NHC(O)O(methoxyphenyl), —OCH₂CH₂NHC(O)O(tetrahydrofuranyl), —OCH₂CH₂NHC(O)OCH₂(tetrahydrofuranyl), —OCH₂CH₂NHC(O)NH(pyridinyl), —OCH₂CH₂N(CH₃)C(O)NH(methylpyrimidinyl), or —OCH₂CH(CH₃)OC(O)OCH₂(aminopyridinyl); (vi) —OCH₂CH₂NHS(O)₂CH₃ or —OCH₂CH₂NHS(O)₂R$_w$, wherein R$_w$ is phenyl or pyridinyl, each substituted with zero to 2 substituents independently selected from F, Cl, and —CH₃; or (vii) —OCH₂CH₂OC(O)NHR$_z$, —OCH(CH₃)CH₂OC(O)NHR$_z$, —OCH₂CH(CH₃)OC(O)NHR$_z$, —OCH(CH₃)CH(CH₃)(CH₂)$_{0-2}$OC(O)NHR$_z$, —OCH₂CH(CH—₂O(isobutyl))(CH₂)$_{0-2}$OC(O)NHR$_z$, —OCH₂CH(CH₂CH₃)OC(O)NHR$_z$, —OCH₂CH(CH₂OCH₃)OC(O)NHR$_z$, or —OCH₂CH(CH₂OCH₂CH(CH₃)₂)OC(O)NHR$_z$ wherein R$_z$ is H, —CH₂CF₃, phenyl, pyrrolyl, pyrazolyl, thiazolyl, isothiazolyl, pyridinyl, pyridazinyl, pyrimidinyl, pyrazinyl, oxadiazolyl, thiadiazolyl, indolyl, pyrrolo[2,3-b]pyridinyl, benzo[d]oxazolonyl, —CH₂(pyrazolyl), —CH₂(imidazolyl), or —CH₂(pyridinyl), each substituted with zero to 2 substituents independently selected from F, Cl, Br, —CN, —OH, —CH₃, —CH₂CH₂CH₃, —CF₃, —CH₂OH, —CD₂OH, —CH(CH₃)OH, —CH₂CH₂OH, —CH₂CH₂CH₂OH, —C(CH₃)₂OH, —CH₂CH(CH₃)OH, —CH₂C(CH₃)₂OH, —CH₂CH₂C(O)OCH₃, —CH₂OP(O)(OH)₂, —CH₂CH₂OP(O)(OH)₂, —CH₂(morpholinyl), —OCH₃, —OCH₂CH₂OH, —OCH₂CH(CH₃)OH, —OCH₂C(CH₃)₂OH, —OCH₂CH₂C(CH₃)₂OH, —OCH(CH₃)CH₂OH, —OCH₂CH(OH)CH₂OH, —OCH₂CF₂OH, —OCH₂CF₂CH₂OH, —C(O)OH, —C(O)OCH₃, —C(O)NH₂, —C(O)NH(CH₃), —C(O)N(CH₃)₂, —C(O)NH(CH₂CH₂OH), —C(O)NH(CH₂CH(CH₃)OH), —C(O)NH(CH₂C(CH₃)₂OH), —C(O)NH(CH₂C(CH₃)₂CH₂OH), —C(O)NH(CH₂CH₂C(CH₃)₂OH), —C(O)N(CH₃)CH₂CH₂OH, —C(O)N(CH₃)CH₂C(CH₃)₂OH, —C(O)NHCH₂(hydroxymethyloxetanyl), —C(O)NH(hydroxymethylcyclobutyl), —C(O)NHCH₂(hydroxycyclobutyl), —C(O)NHCH₂(hydroxymethylcyclobutyl), —C(O)NHCH₂C(CH₃)₂OP(O)(OH)₂, —C(O)(hydroxypiperidinyl), —C(O)(hydroxypyrrolidinyl), —C(O)(hydroxymethylpyrrolidinyl), —C(O)(morpholinyl), —C(O)(hydroxymethylmorpholinyl), —NH₂, —N(CH₃)₂, —NHC(O)CH₃, —NHC(O)(chloro, fluorophenyl), —NH(CH₂C(CH₃)₂OH), —N(CH₃)S(O)₂CH₃, pyrrolidinyl, morpholinyl, thiophenyl, methyl triazolyl, and oxazolidinonyl; and R₁, R₂, R₃, R₄, and n are defined in the first aspect.

One embodiment provides at least one compound of Formulas (I), (II), (III), (IV), (V), (VI), (VII), or (VIII) or a salt thereof, wherein R₃ is substituted with one R$_{3a}$ selected from (i) F, Cl, —CN, —OH, —CH₃, —CF₃, —CHFC(CH₃)₃, cyclopropyl, —CH₂OH, —CD₂OH, —CH₂CH₂OH, —CH(OH)CH₃, —C(CH₃)₂OH, —CH(OH)C(CH₃)₃, —CD(OH)C(CH₃)₃, —CH(OH)CF₃, —CH(OH)CH₂CF₃, —CH(OH)(cyclopropyl), —CH(OH)(methylcyclopropyl), —CH(OH)(trifluoromethylcyclopropyl), —CH(OH)(cyclopropyl substituted with phenyl), —CH(OH)(cyclobutyl), —CH(OH)(methoxycyclobutyl), —CH(OH)(ethoxycarbonylcyclobutyl), —CH(OH)(trifluoromethylcyclobutyl), —CH(OH)(hydroxymethylcyclobutyl), —CH(OH)(cyclobutyl substituted with phenyl), —CH(OH)(cyclohexyl), —CH(OH)(methylcyclohexyl), —CH(OH)(phenyl), —CH(OH)(isopropylphenyl), —CH(OH)(trifluoromethylphenyl), —CH(OH)(fluoro, methoxyphenyl), —CH(OH)(pyridinyl), —CH(OH)(thiazolyl), —CH(OH)(tetrahydropyranyl), —CH(OH)(methyltetrahydropyranyl), —CH₂OCH₃, —CH₂N(CH₃)₂, —CH₂NHS(O)₂(phenyl), or —CH(OH)CH₂(phenyl); (ii) —OCH₃, —OCH₂CH₃, —OCH(CH₃)₂, —OCF₃, —OCHF₂, —OCH₂(phenyl), —OCH₂(thiazolyl), —OCH₂(oxazolidinonyl), —OCH₂(amino isoxazolyl), —OCH₂(imidazolyl substituted with phenyl), —OCH₂CH₂OH, —OCH₂CH(CH₃)OH, —OCH₂CH₂OCH₃, —OCH(CH₃)CH₂OH, —OCH₂CH(OH)CH₃, —OCH(CH₃)CH(OH)CH₃, —OCH₂C(CH₃)₂OH, —OCH₂CH₂O(phenyl), —OCH₂CH₂OCH₂(phenyl), —OCH₂CH₂NH(CH₃), —OCH₂CH(CH₃)NH(methoxypyrimidinyl), —OCH₂C(O)OH, —OCH₂C(O)OCH₃, —OCH₂C(O)OCH₂CH₃, —OCH₂C(O)OC(CH₃)₃, —OCH₂C(O)NH(phenyl), —OCH₂C(O)NHCH₂(phenyl), —OCH₂C(O)(morpholinyl), —OCH₂CH₂CH₂C(O)NH(pyridinyl), —OCH₂CH₂OC(O)OCH₃, —OCH₂CH(CH₃)OC(O)NHCH₂CH₂C(O)NH₂, —OCH₂CH(CH₂CH₃)OC(O)NH(pyridinyl), —OCH₂CH(CH₂OCH₃)OC(O)NH(pyridinyl), —OCH₂CH(CH₂OC(CH₃)₃)OC(O)NH(pyridinyl), —OCH₂CH(CH₂OCH₂CH(CH₃)₂)OC(O)NH(pyridinyl), —OCH₂CH(CH₂OCH₂(phenyl))OC(O)NH(pyridinyl), —OCH₂CH(CH₂OCH₂CH(CH₃)₂)OC(O)NH(pyrimidinyl), or —OCH₂CH(CH₂OCH₂CH(CH₃)₂)OC(O)NH(methyl pyrimidinyl); (iii) —C(O)OH, —C(O)OCH₃, or —C(O)OC(CH₃)₃; (iv) —NHC(O)OCH₃, —NHC(O)OC(CH₃)₃, —NHC(O)OCH₂(phenyl), —NHC(O)OCH₂(tetrahydrofuranyl), or —NHC(O)O(tetrahydropyranyl); (v) —OCH₂CH₂NHC(O)OCH₃, —OCH₂CH₂NHC(O)O(tetrahydropyranyl), —OCH₂CH₂NHC(O)OCH₂(phenyl), —OCH₂CH₂NHC(O)O(methoxyphenyl), —OCH₂CH₂NHC(O)O(tetrahydrofuranyl), —OCH₂CH₂NHC(O)OCH₂(tetrahydrofuranyl), —OCH₂CH₂NHC(O)NH(pyridinyl), —OCH₂CH₂N(CH₃)C(O)NH(methylpyrimidinyl), or —OCH₂CH(CH₃)OC(O)OCH₂(aminopyridinyl); (vi) —OCH₂CH₂NHS(O)₂CH₃ or —OCH₂CH₂NHS(O)₂R$_w$, wherein R$_w$ is phenyl or pyridinyl, each substituted with zero to 2 substituents independently selected from F, Cl, and —CH₃; or (vii) —OCH₂CH₂OC(O)NHR$_z$, —OCH(CH₃)CH₂OC(O)NHR$_z$, —OCH₂CH(CH₃)OC(O)NHR$_z$, —OCH(CH₃)CH(CH₃)(CH₂)$_{0-2}$OC(O)NHR$_z$, —OCH₂CH(CH—₂O(isobutyl))(CH₂)$_{0-2}$OC(O)NHR$_z$, —OCH₂CH(CH₂CH₃)OC(O)NHR$_z$, —OCH₂CH(CH₂OCH₃)OC(O)NHR$_z$, or —OCH₂CH(CH₂OCH₂CH(CH₃)₂)OC(O)NHR$_z$ wherein R$_z$ is H, —CH₂CF₃, phenyl, pyrrolyl, pyrazolyl, thiazolyl, isothiazolyl, pyridinyl, pyridazinyl, pyrimidinyl, pyrazinyl, oxadiazolyl, thiadiazolyl, indolyl, pyrrolo[2,3-b]pyridinyl, benzo[d]oxazolonyl, —CH₂(pyrazolyl), —CH₂(imidazolyl), or —CH₂(pyridinyl), each substituted with zero to 2 substituents independently selected from F, Cl, Br, —CN, —OH, —CH₃, —CH₂CH₂CH₃, —CF₃, —CH₂OH, —CD₂OH, —CH(CH₃)OH, —CH₂CH₂OH, —CH₂CH₂CH₂OH, —C(CH₃)₂OH, —CH₂CH(CH₃)OH, —CH₂C(CH₃)₂OH, —CH₂CH₂C(O)OCH₃, —CH₂OP(O)(OH)₂, —CH₂CH₂OP(O)(OH)₂, —CH₂(morpholinyl), —OCH₃, —OCH₂CH₂OH, —OCH₂CH(CH₃)OH, —OCH₂C(CH₃)₂OH, —OCH₂CH₂C(CH₃)₂OH, —OCH(CH₃)CH₂OH, —OCH₂CH(OH)CH₂OH, —OCH₂CF₂OH, —OCH₂CF₂CH₂OH, —C(O)OH, —C(O)OCH₃, —C(O)NH₂, —C(O)NH(CH₃), —C(O)N(CH₃)₂, —C(O)NH(CH₂CH₂OH), —C(O)NH(CH₂CH(CH₃)OH), —C(O)NH(CH₂C(CH₃)₂OH), —C(O)NH(CH₂C(CH₃)₂CH₂OH), —C(O)NH(CH₂CH₂C(CH₃)₂OH), —C(O)N(CH₃)CH₂CH₂OH, —C(O)N(CH₃)CH₂C(CH₃)₂OH, —C(O)NHCH₂(hydroxymethyloxetanyl), —C(O)NH(hydroxymethylcyclobutyl), —C(O)NHCH₂(hydroxycyclobutyl), —C(O)NHCH₂(hydroxymethylcyclobutyl), —C(O)NHCH₂C(CH₃)₂OP(O)(OH)₂, —C(O)(hydroxypiperidinyl), —C(O)(hydroxypyrrolidinyl), —C(O)(hydroxymethylpyrrolidinyl), —C(O)(morpholinyl), —C(O)(hydroxymethylmorpholinyl), —NH$_2$, —N(CH$_3$)$_2$, —NHC(O)CH$_3$, —NHC(O)(chloro, fluorophenyl), —NH(CH$_2$C(CH$_3$)$_2$OH), —N(CH$_3$)S(O)$_2$CH$_3$, pyrrolidinyl, morpholinyl, thiophenyl, methyl triazolyl, and oxazolidinonyl; and zero to 2 R$_{3a}$ independently selected from F, Cl, —CN, —CH$_3$, —CF$_3$, and —OCH$_3$; and R$_1$, R$_2$, R$_3$, R$_4$, and n are defined in the first aspect.

One embodiment provides at least one compound of Formulas (I), (II), (III), (IV), (V), (VI), (VII), or (VIII) or a salt thereof, wherein R$_1$, R$_2$, R$_3$, R$_{3a}$, R$_4$, R$_a$, R$_b$, R$_d$, and n are defined in the first aspect with the proviso that at least one R$_{3a}$ is F, Cl, —CN, —OH, C$_{1-3}$ alkyl, C$_{1-6}$ fluoroalkyl, C$_{1-6}$ hydroxyalkyl, C$_{1-6}$ hydroxy-deuteroalkyl, C$_{1-6}$ hydroxy-fluoroalkyl, C$_{1-6}$ alkoxy, C$_{1-3}$ fluoroalkoxy, C$_{3-6}$ cycloalkyl, C$_{3-6}$ fluorocycloalkyl, 3- to 6-membered heterocyclyl, —CH(OH)R$_y$, wherein R$_y$ is C$_{3-6}$ cycloalkyl, aryl, heteroaryl, or 3- to 6-membered heterocyclyl; (C$_{1-3}$ alkoxy)-(C$_{1-3}$ alkylene), —(CH$_2$)$_{1-3}$NR$_a$R$_a$, —(CH$_2$)$_{1-3}$NHS(O)$_2$(aryl), —O(CH$_2$)$_{1-3}$(aryl), —O(CH$_2$)$_{1-3}$(thiazolyl), —O(CH$_2$)$_{1-3}$(oxazolidinonyl), —O(CH$_2$)$_{1-3}$(amino isoxazolyl), —O(CH$_2$)$_{1-3}$(imidazolyl substituted with phenyl), C$_{1-6}$ hydroxyalkoxy, (C$_{1-3}$ alkoxy)-(C$_{1-6}$ alkoxy), —O(CH$_2$)$_{1-4}$O(aryl), —O(CH$_2$)$_{1-4}$O(CH$_2$)$_{1-3}$(aryl), —O(CH$_2$)$_{1-4}$NR$_a$R$_a$, —O(CH$_2$)$_{1-3}$CHR$_a$R$_a$(methoxy pyrimidinyl), —O(CH$_2$)$_{1-4}$NHS(O)$_2$(C$_{1-3}$ alkyl), —O(CH$_2$)$_{1-4}$NHS(O)$_2$(aryl), —O(CH$_2$)$_{1-4}$C(O)OH, —O(CH$_2$)$_{1-4}$C(O)O(C$_{1-6}$ alkyl), —O(CH$_2$)$_{1-4}$C(O)NR$_a$(CH$_2$)$_{0-3}$(aryl), —O(CH$_2$)$_{1-4}$C(O)NR$_a$(CH$_2$)$_{0-3}$(heteroaryl), —O(CH$_2$)$_{1-4}$C(O)(morpholinyl), —O(CH$_2$)$_{1-4}$OC(O)O(C$_{1-3}$ alkyl), —O(CH$_2$)$_{1-3}$CHR$_a$OC(O)NR$_a$(CH$_2$)$_{1-4}$C(O)NR$_a$R$_a$, —CH$_2$CHR$_d$OC(O)NR$_a$(heteroaryl), —O(CH$_2$)$_{1-4}$OC(O)NR$_a$(heteroaryl), —O(imidazolyl substituted with aryl), —C(O)OH, —C(O)O(C$_{1-6}$ alkyl), —NR$_a$C(O)(furanyl), —NR$_a$C(O)(pyranyl), —NR$_a$C(O)O(C$_{1-6}$ alkyl), —NR$_a$C(O)O(CH$_2$)$_{1-4}$(aryl), —O(CH$_2$)$_{1-4}$NR$_a$C(O)O(C$_{1-6}$ alkyl), —O(CH$_2$)$_{1-4}$NR$_a$C(O)O(CH$_2$)$_{0-4}$(tetrahydropyranyl), —O(CH$_2$)$_{1-4}$NR$_a$C(O)O(CH$_2$)$_{0-4}$(aryl), —O(CH$_2$)$_{1-4}$NR$_a$C(O)O(CH$_2$)$_{0-4}$(heteroaryl), or —O(CH$_2$)$_{1-4}$NR$_a$C(O)O(CH$_2$)$_{0-4}$(tetrahydrofuranyl), wherein each of said aryl, heteroaryl, and 3- to 6-membered heterocyclyl is substituted with zero to 5 substituents independently selected from F, Cl, —CN, C$_{1-3}$ alkyl, C$_{1-3}$ fluoroalkyl, C$_{1-4}$ hydroxyalkyl, C$_{1-3}$ alkoxy, —OCF$_3$, —OCHF$_2$, —NH$_2$, —NH(C$_{1-6}$ alkyl), —N(C$_{1-6}$ alkyl)$_2$, —C(O)O(C$_{1-3}$ alkyl), C$_{1-3}$ hydroxyalkoxy, phenyl, —CONR$_c$R$_c$, and —S(O)$_2$NR$_c$R$_c$.

One embodiment provides at least one compound of Formulas (I), (II), (III), (IV), (V), (VI), (VII), or (VIII) or a salt thereof, wherein R$_1$, R$_2$, R$_3$, R$_{3a}$, R$_4$, R$_a$, R$_b$, R$_d$, and n are defined in the first aspect with the proviso that at least one R$_{3a}$ is —CH(OH)CR$_h$R$_i$R$_j$ wherein R$_h$ and R$_i$ are independently H, F, C$_{1-4}$ alkyl, C$_{1-3}$ alkoxy, or taken together with the carbon atom to which they are attached, form C$_{3-8}$ cycloalkyl or 4- to 7-membered heterocyclyl ring; and is H, C$_{1-6}$ alkyl, C$_{1-5}$ fluoroalkyl, (C$_{1-3}$ alkoxy)-(C$_{1-3}$ alkylene), C$_{3-8}$ cycloalkyl, C$_{3-8}$ heterocyclyl, aryl, or heteroaryl; and p is 1, 2, or 3. Included in this embodiment are compounds of Formulas (I), (II), (III), or (IV).

One embodiment provides at least one compound of Formulas (I), (II), (III), (IV), (V), (VI), (VII), or (VIII) or a salt thereof, wherein R$_1$, R$_2$, R$_3$, R$_{3a}$, R$_4$, R$_a$, R$_b$, R$_d$, and n are defined in the first aspect with the proviso that at least one R$_{3a}$ is —O(CH$_2$)$_{1-4}$NR$_a$S(O)$_2$(C$_{1-3}$ alkyl) or —O(CH$_2$)$_{1-4}$NR$_a$S(O)$_2$R$_w$, wherein R$_w$ is aryl or heteroaryl, each substituted with zero to 2 substituents independently selected from F, Cl, cyano, C$_{1-3}$ alkyl, C$_{1-3}$ alkoxy, —OCF$_3$, —OCHF$_2$, and C$_{1-3}$ fluoroalkyl; and p is 1, 2, or 3. Included in this embodiment are compounds of Formulas (I), (II), (III), or (IV).

One embodiment provides at least one compound of Formulas (I), (II), (III), (IV), (V), (VI), (VII), or (VIII) or a salt thereof, wherein R$_1$, R$_2$, R$_3$, R$_{3a}$, R$_4$, R$_a$, R$_b$, R$_d$, and n are defined in the first aspect with the proviso that at least one R$_{3a}$ is —O(CH$_2$)$_{1-4}$OC(O)NR$_a$R$_x$, —OCH(R$_d$)(CH$_2$)$_{1-3}$OC(O)NR$_a$R$_x$, —OCR$_d$R$_d$(CH$_2$)$_{1-3}$OC(O)NR$_a$R$_x$, —O(CH$_2$)$_{1-3}$CH(R$_d$)OC(O)NR$_a$R$_x$, —O(CH$_2$)$_{1-3}$CR$_d$R$_d$OC(O)NR$_a$R$_x$, —OCH(R$_d$)CH(R$_d$)(CH$_2$)$_{0-2}$OC(O)NR$_a$R$_x$, or —OCR$_d$R$_d$CR$_d$R$_d$(CH$_2$)$_{0-2}$OC(O)NR$_a$R$_x$, wherein R$_x$ is selected from H, C$_{1-4}$ alkyl, C$_{1-4}$ fluoroalkyl, aryl, heteroaryl, and —CH$_2$(heteroaryl), each aryl and heteroaryl substituted with zero to 2 substituents independently selected from F, Cl, Br, —CN, —OH, C$_{1-3}$ alkyl, C$_{1-3}$ fluoroalkyl, C$_{1-6}$ hydroxyalkyl, C$_{1-6}$ hydroxy-deuteroalkyl, C$_{1-6}$ hydroxyalkoxy, C$_{1-6}$ hydroxy-fluoroalkoxy, C$_{1-3}$ alkoxy, —C(O)OH, —(CH$_2$)$_{0-3}$C(O)O(C$_{1-3}$ alkyl), —(CH$_2$)$_{1-3}$OP(O)(OH)$_2$, —CH$_2$(morpholinyl), —C(O)NH$_2$, —C(O)NH(C$_{1-6}$ alkyl), —C(O)N(C$_{1-6}$ alkyl)$_2$, —C(O)NR$_a$(C$_{1-6}$ hydroxyalkyl), —C(O)NR$_b$R$_b$, —S(O)$_2$NR$_a$R$_a$, —NH$_2$, —NH(C$_{1-6}$ alkyl), —NR$_a$(C$_{1-6}$ hydroxyalkyl), —N(C$_{1-6}$ alkyl)$_2$, —NR$_a$C(O)(C$_{1-6}$ alkyl), —NR$_a$C(O)(chloro, fluorophenyl), —NR$_a$S(O)$_2$(C$_{1-3}$ alkyl), —C(O)NR$_a$(CH$_2$)$_{0-1}$(hydroxymethyloxetanyl), —C(O)NR$_a$(CH$_2$)$_{0-1}$ (hydroxymethyl C$_{3-6}$ cycloalkyl), —C(O)NR$_a$(CH$_2$)$_{0-1}$(hydroxy C$_{3-6}$ cycloalkyl), —C(O)NHCH$_2$C(CH$_3$)$_2$OP(O)(OH)$_2$, —C(O)(hydroxypiperidinyl), —C(O)(hydroxypyrrolidinyl), —C(O)(hydroxymethylpyrrolidinyl), —C(O)(morpholinyl), —C(O)(hydroxymethylmorpholinyl), pyrrolidinyl, morpholinyl, thiophenyl, methyl triazolyl, and oxazolidinonyl; and p is 1, 2, or 3. Included in this embodiment are compounds of Formulas (I), (II), (III), or (IV).

One embodiment provides at least one compound of Formulas (I), (II), (III), (IV), (V), (VI), (VII), or (VIII) or a salt thereof, wherein R$_1$, R$_2$, R$_3$, R$_{3a}$, R$_4$, and n are defined in the first aspect with the proviso that at least one R$_{3a}$ is F, Cl, —CN, —OH, —CH$_3$, —CF$_3$, —CHFC(H$_3$)$_3$, cyclopropyl, —CH$_2$OH, —CD$_2$OH, —CH$_2$CH$_2$OH, —CH(OH)CH$_3$, —C(CH$_3$)$_2$OH, —CH(OH)C(CH$_3$)$_3$, —CD(OH)C(CH$_3$)$_3$, —CH(OH)CF$_3$, —CH(OH)CH$_2$CF$_3$, —CH(OH)(cyclopropyl), —CH(OH)(methylcyclopropyl), —CH(OH)(trifluoromethylcyclopropyl), —CH(OH)(cyclopropyl substituted with phenyl), —CH(OH)(cyclobutyl), —CH(OH)(methoxycyclobutyl), —CH(OH)(ethoxycarbonylcyclobutyl), —CH(OH)(trifluoromethylcyclobutyl), —CH(OH)(hydroxymethylcyclobutyl), —CH(OH)(cyclobutyl substituted with phenyl), —CH(OH)(cyclohexyl), —CH(OH)(methylcyclohexyl), —CH(OH)(phenyl), —CH(OH)(isopropylphenyl), —CH(OH)(trifluoromethylphenyl), —CH(OH)(fluoro, methoxyphenyl), —CH(OH)(pyridinyl), —CH(OH)(thiazolyl), —CH(OH)(tetrahydropyranyl), —CH(OH)(methyltetrahydropyranyl), —CH$_2$OCH$_3$, —CH$_2$N(CH$_3$)$_2$, —CH$_2$NHS(O)$_2$(phenyl), or —CH(OH)CH$_2$(phenyl); and p is 1, 2, or 3. Included in this embodiment are compounds of Formulas (I), (II), (III), or (IV).

One embodiment provides at least one compound of Formulas (I), (II), (III), (IV), (V), (VI), (VII), or (VIII) or a salt thereof, wherein R$_1$, R$_2$, R$_3$, R$_{3a}$, R$_4$, and n are defined in the first aspect with the proviso that at least one R$_{3a}$ is —OCH$_3$, —OCH$_2$CH$_3$, —OCH(CH$_3$)$_2$, —OCF$_3$, —OCHF$_2$, —OCH$_2$(phenyl), —OCH$_2$(thiazolyl), —OCH$_2$(oxazolidinonyl), —OCH$_2$(amino isoxazolyl), —OCH$_2$(imidazolyl substituted with phenyl), —OCH$_2$CH$_2$OH, —OCH$_2$CH(CH$_3$)OH, —OCH$_2$CH$_2$OCH$_3$, —OCH(CH$_3$)CH$_2$OH, —OCH$_2$CH(OH)CH$_3$, —OCH(CH$_3$)CH(OH)CH$_3$, —OCH₂C(CH₃)₂OH, —OCH₂CH₂O(phenyl), —OCH₂CH₂OCH₂(phenyl), —OCH₂CH₂NH(CH₃), —OCH₂CH(CH₃)NH(methoxy pyrimidinyl), —OCH₂C(O)OH, —OCH₂C(O)OCH₃, —OCH₂C(O)OCH₂CH₃, —OCH₂C(O)OC(CH₃)₃, —OCH₂C(O)NH(phenyl), —OCH₂C(O)NHCH₂(phenyl), —OCH₂C(O)(morpholinyl), —OCH₂CH₂CH₂C(O)NH(pyridinyl), —OCH₂CH₂OC(O)OCH₃, —OCH₂CH(CH₃)OC(O)NHCH₂CH₂C(O)NH₂, —OCH₂CH(CH₂CH₃)OC(O)NH(pyridinyl), —OCH₂CH(CH₂OCH₃)OC(O)NH(pyridinyl), —OCH₂CH(CH₂OC(CH₃)₃)OC(O)NH(pyridinyl), —OCH₂CH(CH₂OCH₂CH(CH₃)₂)OC(O)NH(pyridinyl), —OCH₂CH(CH₂OCH₂(phenyl))OC(O)NH(pyridinyl), —OCH₂CH(CH₂OCH₂CH(CH₃)₂)OC(O)NH(pyrimidinyl), or —OCH₂CH(CH₂OCH₂CH(CH₃)₂)OC(O)NH(methyl pyrimidinyl); and p is 1, 2, or 3. Included in this embodiment are compounds of Formulas (I), (II), (III), or (IV).

One embodiment provides at least one compound of Formulas (I), (II), (III), (IV), (V), (VI), (VII), or (VIII) or a salt thereof, wherein $R_1$, $R_2$, $R_3$, $R_{3a}$, $R_4$, and n are defined in the first aspect with the proviso that at least one $R_{3a}$ is —C(O)OH, —C(O)OCH₃, or —C(O)OC(CH₃)₃; and p is 1, 2, or 3. Included in this embodiment are compounds of Formulas (I), (II), (III), or (IV).

One embodiment provides at least one compound of Formulas (I), (II), (III), (IV), (V), (VI), (VII), or (VIII) or a salt thereof, wherein $R_1$, $R_2$, $R_3$, $R_{3a}$, $R_4$, and n are defined in the first aspect with the proviso that at least one $R_{3a}$ is —NHC(O)OCH₃, —NHC(O)OC(CH₃)₃, —NHC(O)OCH₂(phenyl), —NHC(O)OCH₂(tetrahydrofuranyl), or —NHC(O)O(tetrahydropyranyl); and p is 1, 2, or 3. Included in this embodiment are compounds of Formulas (I), (II), (III), or (IV).

One embodiment provides at least one compound of Formulas (I), (II), (III), (IV), (V), (VI), (VII), or (VIII) or a salt thereof, wherein $R_1$, $R_2$, $R_3$, $R_{3a}$, $R_4$, and n are defined in the first aspect with the proviso that at least one $R_{3a}$ is —OCH₂CH₂NHC(O)OCH₃, —OCH₂CH₂NHC(O)O(tetrahydropyranyl), —OCH₂CH₂NHC(O)OCH₂(phenyl), —OCH₂CH₂NHC(O)O(methoxyphenyl), —OCH₂CH₂NHC(O)O(tetrahydrofuranyl), —OCH₂CH₂NHC(O)OCH₂(tetrahydrofuranyl), —OCH₂CH₂NHC(O)NH(pyridinyl), —OCH₂CH₂N(CH₃)C(O)NH(methylpyrimidinyl), or —OCH₂CH(CH₃)OC(O)OCH₂(aminopyridinyl); and p is 1, 2, or 3. Included in this embodiment are compounds of Formulas (I), (II), (III), or (IV).

One embodiment provides at least one compound of Formulas (I), (II), (III), (IV), (V), (VI), (VII), or (VIII) or a salt thereof, wherein $R_1$, $R_2$, $R_3$, $R_{3a}$, $R_4$, and n are defined in the first aspect with the proviso that at least one $R_{3a}$ is —OCH₂CH₂NHS(O)₂CH₃ or —OCH₂CH₂NHS(O)₂R_w wherein $R_w$ is phenyl or pyridinyl, each substituted with zero to 2 substituents independently selected from F, Cl, and —CH₃; and p is 1, 2, or 3. Included in this embodiment are compounds of Formulas (I), (II), (III), or (IV).

One embodiment provides at least one compound of Formulas (I), (II), (III), (IV), (V), (VI), (VII), or (VIII) or a salt thereof, wherein $R_1$, $R_2$, $R_3$, $R_{3a}$, $R_4$, and n are defined in the first aspect with the proviso that at least one $R_{3a}$ is —OCH₂CH₂OC(O)NHR_z, —OCH(CH₃)CH₂OC(O)NHR_z, —OCH₂CH(CH₃)OC(O)NHR_z, —OCH(CH₃)CH(CH₃)(CH₂)₀₋₂OC(O)NHR_z, —OCH₂CH(CH—₂O(isobutyl))(CH₂)₀₋₂OC(O)NHR_z, —OCH₂CH(CH₂CH₃)OC(O)NHR_z, —OCH₂CH(CH₂OCH₃)OC(O)NHR_z, or —OCH₂CH(CH₂OCH₂CH(CH₃)₂)OC(O)NHR_z wherein $R_z$ is H, —CH₂CF₃, phenyl, pyrrolyl, pyrazolyl, thiazolyl, isothiazolyl, pyridinyl, pyridazinyl, pyrimidinyl, pyrazinyl, oxadiazolyl, thiadiazolyl, indolyl, pyrrolo[2,3-b]pyridinyl, benzo[d]oxazolonyl, —CH₂(pyrazolyl), —CH₂(imidazolyl), or —CH₂(pyridinyl), each substituted with zero to 2 substituents independently selected from F, Cl, Br, —CN, —OH, —CH₃, —CH₂CH₂CH₃, —CF₃, —CH₂OH, —CD₂OH, —CH(CH₃)OH, —CH₂CH₂OH, —CH₂CH₂CH₂OH, —C(CH₃)₂OH, —CH₂CH(CH₃)OH, —CH₂C(CH₃)₂OH, —CH₂CH₂C(O)OCH₃, —CH₂OP(O)(OH)₂, —CH₂CH₂OP(O)(OH)₂, —CH₂(morpholinyl), —OCH₃, —OCH₂CH₂OH, —OCH₂CH(CH₃)OH, —OCH₂C(CH₃)₂OH, —OCH₂CH₂C(CH₃)₂OH, —OCH(CH₃)CH₂OH, —OCH₂CH(OH)CH₂OH, —OCH₂CF₂OH, —OCH₂CF₂CH₂OH, —C(O)OH, —C(O)OCH₃, —C(O)NH₂, —C(O)NH(CH₃), —C(O)N(CH₃)₂, —C(O)NH(CH₂CH₂OH), —C(O)NH(CH₂CH(CH₃)OH), —C(O)NH(CH₂C(CH₃)₂OH), —C(O)NH(CH₂C(CH₃)₂CH₂OH), —C(O)NH(CH₂CH₂C(CH₃)₂OH), —C(O)N(CH₃)CH₂CH₂OH, —C(O)N(CH₃)CH₂C(CH₃)₂OH, —C(O)NHCH₂(hydroxymethyloxetanyl), —C(O)NH(hydroxymethylcyclobutyl), —C(O)NHCH₂(hydroxycyclobutyl), —C(O)NHCH₂(hydroxymethylcyclobutyl), —C(O)NHC(CH₃)₂OP(O)(OH)₂, —C(O)(hydroxypiperidinyl), —C(O)(hydroxypyrrolidinyl), —C(O)(hydroxymethylpyrrolidinyl), —C(O)(morpholinyl), —C(O)(hydroxymethylmorpholinyl), —NH₂, —N(CH₃)₂, —NHC(O)CH₃, —NHC(O)(chloro, fluorophenyl), —NH(CH₂C(CH₃)₂OH), —N(CH₃)S(O)₂CH₃, pyrrolidinyl, morpholinyl, thiophenyl, methyl triazolyl, and oxazolidinonyl; and p is 1, 2, or 3. Included in this embodiment are compounds of Formulas (I), (II), (III), or (IV).

One embodiment provides at least one compound of Formulas (I), (II), (III), (IV), (V), (VI), (VII), or (VIII) or a salt thereof, wherein $R_3$ is substituted with zero to 1 $R_{3a}$. Included in this embodiment are compounds in which $R_3$ is unsubstituted.

One embodiment provides at least one compound of Formula (I) or a salt thereof, wherein $R_1$ is —OCH₃, —OCHF₂, —OCH₂CH₃, or —CH₂OCH₃; $R_2$, at each occurrence, is independently H, F, Cl, —CN, —CH₃, —OCH₃, or —CH₂OH; and $R_3$ is:

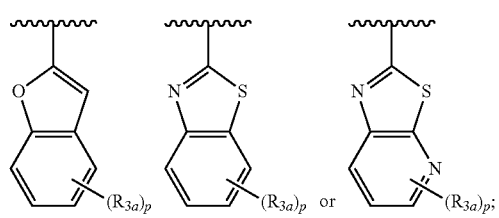

and $R_4$, $R_{3a}$, and p are defined in the first aspect.

One embodiment provides at least one compound of Formula (II) or a salt thereof, wherein $R_1$ is —OH, —OCH₃, —OCH₂CH₃, —OCHF₂, —OCH₂CHF₂, —CH₂OCH₃, or —NH(CH₃); $R_2$, at each occurrence, is independently F, Cl, —CN, —CH₃, —CH₂OH, —CH₂F, —CHF₂, or —OCH₃;

R₃ is:

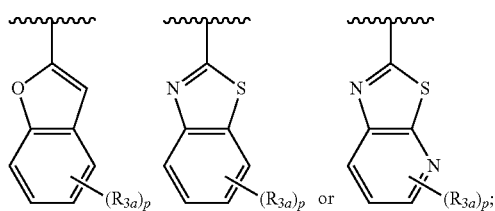

and R$_{3a}$, at each occurrence, is independently F, Cl, —CH$_3$, —OCH$_3$, —CH(OH)(trifluoromethylcyclobutyl), —OCH$_2$CH(CH$_3$)OC(O)NHR$_z$, or —OCH(CH$_3$)CH(CH$_3$)OC(O)NHR$_z$, wherein R$_z$ is pyridinyl, pyrimidinyl, or benzo[d]oxazolonyl, each substituted with zero to 2 substituents independently selected from F, —OH, —CN, —CH$_3$, —CF$_3$, —CH$_2$OH, —CH$_2$CH$_2$OH, —OCH$_2$CH$_2$OH, —OCH$_3$, —CH$_2$CH(CH$_3$)OH, and —OCH$_2$CH$_2$C(CH$_3$)$_2$OH; and R$_4$ and p are defined in the first aspect.

One embodiment provides compounds of Formulas (I), (II), (III), or (IV) or a salt thereof, wherein R$_3$ is indolyl. Included in this embodiment is a compound of Formula (I) selected from 2-(difluoromethoxy)-5-(1H-indol-2-yl)-7-methylquinoxaline (5).

One embodiment provides compounds selected from one of the examples, more preferably, Examples 1 to 837, or stereoisomers, tautomers, pharmaceutically acceptable salts, or solvates thereof.

One embodiment provides compounds of Formulas (I), (II), (III), or (IV) or a salt thereof, wherein R$_3$ is benzofuranyl. Included in this embodiment is a compound of Formulas (I), (II), (III), or (IV) selected from:
5-(benzofuran-2-yl)-2-(difluoromethoxy)-7-methylquinoxaline (1);
2-(difluoromethoxy)-5-(5-methoxybenzofuran-2-yl)-7-methylquinoxaline (2);
2-(difluoromethoxy)-5-(4,5-dimethoxybenzofuran-2-yl)-7-methylquinoxaline (6);
5-(7-chlorobenzofuran-2-yl)-2-methoxy-7-methylquinoxaline (37);
2-((7-chloro-2-(2-methoxy-7-methylquinoxalin-5-yl)benzofuran-5-yl)oxy)ethyl (2-methylpyridin-4-yl)carbamate (38);
N-(2-((7-chloro-2-(2-methoxy-7-methylquinoxalin-5-yl)benzofuran-5-yl)oxy)ethyl)benzenesulfonamide (39);
2-(difluoromethoxy)-5-(7-methoxybenzofuran-2-yl)-7-methylquinoxaline (41);
2-(difluoromethoxy)-5-(4-methoxybenzofuran-2-yl)-7-methylquinoxaline (42);
5-(4-(benzyloxy)benzofuran-2-yl)-2-methoxy-7-methylquinoxaline (43);
5-(5-(benzyloxy) benzofuran-2-yl)-2-(difluoromethoxy)-7-methylquinoxaline (44); methyl 2-(2-(2-(difluoromethoxy)-7-methylquinoxalin-5-yl)benzofuran-5-yloxy)ethylcarbamate (46); tert-butyl 2-(2-(2-(difluoromethoxy)-7-methylquinoxalin-5-yl)benzofuran-5-yloxy) acetate (49);
2-(2-(2-(difluoromethoxy)-7-methylquinoxalin-5-yl)benzofuran-5-yloxy)-N-methylethanamine (54); 2-methoxy-5-(5-methoxybenzofuran-2-yl)-7-methylquinoxaline (56);
5-(6-fluoro-5-methoxybenzofuran-2-yl)-2-methoxy-7-methylquinoxaline (120);
5-(7-chloro-6-fluoro-5-methoxybenzofuran-2-yl)-2-(methoxymethyl)-7-methylquinoxaline (121);
5-(7-chloro-6-fluoro-5-methoxybenzofuran-2-yl)-2-methoxy-7-methylquinoxaline (122);
2-((6-fluoro-2-(2-methoxy-7-methylquinoxalin-5-yl)benzofuran-5-yl)oxy)ethyl (2-methylpyridin-4-yl)carbamate (123);
(8-(7-chloro-6-fluoro-5-methoxybenzofuran-2-yl)-3-methoxyquinoxalin-6-yl)methanol (124); (8-(6-fluoro-5-methoxybenzofuran-2-yl)-3-methoxyquinoxalin-6-yl)methanol (125);
2-((6-fluoro-2-(7-(hydroxymethyl)-2-methoxyquinoxalin-5-yl)benzofuran-5-yl)oxy)ethyl (2-methylpyridin-4-yl)carbamate (126); 5-(benzofuran-2-yl)-7-methyl-2-vinylquinoxaline (131); 5-(benzofuran-2-yl)-2-ethyl-7-methylquinoxaline (132);
5-(benzofuran-2-yl)-2-(difluoromethoxy)-8-methylquinoxaline (133);
5-(benzofuran-2-yl)-2-(furan-3-yl)-7-methylquinoxaline (135);
5-(benzofuran-2-yl)-2-methoxy-7-methylquinoxaline (175); methyl 5-(benzofuran-2-yl)-7-methylquinoxaline-2-carboxylate (176);
5-(benzofuran-2-yl)-2-(1-methoxyethyl)-7-methylquinoxaline (184);
5-(benzofuran-2-yl)-2-(methoxymethyl)-7-methylquinoxaline (195); and
5-(benzofuran-2-yl)-2-ethoxy-7-methylquinoxaline (661).

One embodiment provides compounds of Formulas (I), (II), (III), or (IV) or a salt thereof, wherein R$_3$ is benzo[b]thiophenyl. Included in this embodiment is a compound of Formula (I) selected from
5-(benzo[b]thiophen-2-yl)-2-(difluoromethoxy)-7-methylquinoxaline (40).

One embodiment provides compounds of Formulas (I), (II), (III), or (IV) or a salt thereof, wherein R$_3$ is benzo[d]imidazolyl. Included in this embodiment is a compound of Formula (I) selected from:
5-(1H-benzo[d]imidazol-2-yl)-2-(difluoromethoxy)-7-methylquinoxaline (47); and
2-(difluoromethoxy)-5-(5-methoxy-1H-benzo[d]imidazol-2-yl)-7-methylquinoxaline (50).

One embodiment provides compounds of Formulas (I), (II), (III), or (IV) or a salt thereof, wherein R$_3$ is benzo[d]oxazolyl. Included in this embodiment is a compound of Formula (I) selected from:
2-(2-(difluoromethoxy)-7-methylquinoxalin-5-yl)benzo[d]oxazole (3).

One embodiment provides compounds of Formulas (I), (II), (III), or (IV) or a salt thereof, wherein R$_3$ is benzo[d]thiazolyl. Included in this embodiment is a compound of Formula (I) to (III) selected from:
2-(2-(difluoromethoxy)-7-methylquinoxalin-5-yl)benzo[d]thiazole (4);
6-(benzyloxy)-2-(2-(difluoromethoxy)-7-methylquinoxalin-5-yl)benzo[d]thiazole (7);
4-chloro-2-(2-(difluoromethoxy)-7-methylquinoxalin-5-yl)benzo[d]thiazole (8);
2-(2-(difluoromethoxy)-7-methylquinoxalin-5-yl)-6-methoxy-4-methylbenzo[d]thiazole (10);
2-(2-(difluoromethoxy)-7-methylquinoxalin-5-yl)-7-methoxy-4-methylbenzo[d]thiazole (12);
2-(2-(difluoromethoxy)-7-methylquinoxalin-5-yl)-4,6-difluoro-7-methoxybenzo[d]thiazole (13); tert-butyl (2-(2-(difluoromethoxy)-7-methylquinoxalin-5-yl)benzo[d]thiazol-7-yl) carbamate (14);

2-(2-(difluoromethoxy)-7-methylquinoxalin-5-yl)-7-(thiazol-4-ylmethoxy)benzo[d]thiazole (15); tetrahydrofuran-3-yl (2-((2-(2-(difluoromethoxy)-7-methylquinoxalin-5-yl)benzo[d]thiazol-6-yl)oxy) ethyl)carbamate (16); 2-(2-(difluoromethoxy)-7-methylquinoxalin-5-yl)-7-(2-phenoxyethoxy)benzo[d]thiazole (17); 7-(2-(benzyloxy)ethoxy)-2-(2-(difluoromethoxy)-7-methylquinoxalin-5-yl)benzo[d] thiazole (18); (tetrahydrofuran-2-yl)methyl (2-((2-(2-(difluoromethoxy)-7-methylquinoxalin-5-yl)benzo[d]thiazol-6-yl)oxy)ethyl)carbamate (19); tetrahydro-2H-pyran-4-yl (2-((2-(2-(difluoromethoxy)-7-methylquinoxalin-5-yl)benzo[d]thiazol-6-yl) oxy)ethyl)carbamate (20); tetrahydro-2H-pyran-4-yl (2-(2-(difluoromethoxy)-7-methylquinoxalin-5-yl) benzo[d]thiazol-7-yl)carbamate (21); (tetrahydrofuran-2-yl) methyl (2-(2-(difluoromethoxy)-7-methylquinoxalin-5-yl) benzo[d]thiazol-7-yl)carbamate (22); 4-fluoro-N-(2-((2-(2-methoxy-7-methylquinoxalin-5-yl)-4-methylbenzo[d]thiazol-6-yl)oxy)ethyl)benzenesulfonamide (26); N-(2-((4-chloro-2-(2-methoxy-7-methylquinoxalin-5-yl)benzo[d]thiazol-6-yl)oxy)ethyl) benzenesulfonamide (27); N-(2-((4-chloro-2-(2-methoxy-7-methylquinoxalin-5-yl) benzo[d]thiazol-6-yl)oxy)ethyl)-4-fluorobenzenesulfonamide (28); 4-fluoro-N-(2-((2-(2-(methoxymethyl)-7-methylquinoxalin-5-yl)-4-methylbenzo[d]thiazol-6-yl)oxy)ethyl) benzenesulfonamide (29); N-(2-((2-(2-ethoxy-7-methylquinoxalin-5-yl)-4-methylbenzo[d]thiazol-6-yl)oxy) ethyl)-4-fluorobenzenesulfonamide (30); N-(2-((2-(2-ethyl-7-methylquinoxalin-5-yl)-4-methylbenzo[d]thiazol-6-yl)oxy)ethyl)-4-fluorobenzenesulfonamide (31); methyl 5-(6-(2-(4-fluorophenylsulfonamido)ethoxy)-4-methylbenzo[d]thiazol-2-yl)-7-methylquinoxaline-2-carboxylate (32); N-(2-((2-(2-cyclopropoxy-7-methylquinoxalin-5-yl)-4-methylbenzo[d]thiazol-6-yl)oxy)ethyl)-4-fluorobenzenesulfonamide (33); 4-fluoro-N-(2-((2-(2-(fluoromethoxy)-7-methylquinoxalin-5-yl)-4-methylbenzo[d]thiazol-6-yl) oxy)ethyl)benzenesulfonamide (34); 2-(2-methoxy-7-methylquinoxalin-5-yl)-4-methyl-6-((2-phenyl-1H-imidazol-5-yl)methoxy)benzo[d]thiazole (35); N-benzyl-2-((2-(2-methoxy-7-methylquinoxalin-5-yl)-4-methylbenzo[d]thiazol-6-yl) oxy)acetamide (36); 2-(2-(difluoromethoxy)-7-methylquinoxalin-5-yl)-6-methoxybenzo[d]thiazole (48); 2-(2-(difluoromethoxy)-7-methylquinoxalin-5-yl)-4-methoxybenzo[d]thiazole (51); 2-(2-(difluoromethoxy)-7-methylquinoxalin-5-yl)-4-methylbenzo[d]thiazole (52); 2-(2-(difluoromethoxy)-7-methylquinoxalin-5-yl)-4-fluorobenzo[d]thiazole (53); 2-(2-(difluoromethoxy)-7-methylquinoxalin-5-yl)-4,6-dimethoxybenzo[d]thiazole (55); 2-(2-(difluoromethoxy)-7-methylquinoxalin-5-yl)-7-methoxybenzo[d]thiazole (58); 2-(2-(difluoromethoxy)-7-methylquinoxalin-5-yl)-4-fluoro-6-methoxybenzo[d]thiazole (59); 2-(2-(difluoromethoxy)-7-methylquinoxalin-5-yl)-5-fluorobenzo[d]thiazole (60); methyl 2-(2-(difluoromethoxy)-7-methylquinoxalin-5-yl)benzo[d]thiazole-7-carboxylate (61); N-(2-(2-(2-(difluoromethoxy)-7-methylquinoxalin-5-yl)benzo[d]thiazol-6-yloxy)ethyl) benzenesulfonamide (63); (2-(2-(difluoromethoxy)-7-methylquinoxalin-5-yl)benzo[d] thiazol-7-yl)methanol (64); 2-(2-(difluoromethoxy)-7-methylquinoxalin-5-yl)-7-(methoxymethyl)benzo[d]thiazole (65); N-((2-(2-(difluoromethoxy)-7-methylquinoxalin-5-yl)benzo[d]thiazol-7-yl)methyl)benzenesulfonamide (66); N-(2-(2-(2-(difluoromethoxy)-7-methylquinoxalin-5-yl)-4-fluorobenzo[d]thiazol-6-yloxy) ethyl) benzenesulfonamide (67); 2-(2-(difluoromethoxy)-7-methylquinoxalin-5-yl)-5-methylbenzo[d]thiazole (68); methyl 2-(2-(2-(difluoromethoxy)-7-methylquinoxalin-5-yl)benzo[d]thiazol-7-yloxy)ethylcarbamate (69); methyl 2-(2-(2-(difluoromethoxy)-7-methylquinoxalin-5-yl)-4-methylbenzo[d]thiazol-7-yloxy)ethylcarbamate (70); 2-(2-(difluoromethoxy)-7-methylquinoxalin-5-yl)-6-(thiazol-4-ylmethoxy)benzo[d]thiazole (71); N-(2-(2-(2-methoxy-7-methylquinoxalin-5-yl)benzo[d]thiazol-6-yloxy)ethyl) benzenesulfonamide (72); N-(2-(2-(difluoromethoxy)-7-methylquinoxalin-5-yl)-4-methylbenzo[d]thiazol-6-yloxy) ethyl)benzenesulfonamide (73); 2-(2-(difluoromethoxy)-7-methylquinoxalin-5-yl)benzo[d]thiazol-7-yloxy)ethanol (74); 2-(2-(difluoromethoxy)-7-methylquinoxalin-5-yl)-7-(2-methoxyethoxy)benzo[d]thiazole (75); benzyl 2-(2-(difluoromethoxy)-7-methylquinoxalin-5-yl)benzo[d]thiazol-7-ylcarbamate (76); 2-(2-methoxy-7-methylquinoxalin-5-yl)-6-(2-methoxyethoxy)benzo[d]thiazole (77); 2-(2-methoxy-7-methylquinoxalin-5-yl)-7-(2-methoxyethoxy)benzo[d]thiazole (78); N-(2-(2-(2-methoxy-7-methylquinoxalin-5-yl)-4-methylbenzo[d]thiazol-6-yloxy)ethyl) benzenesulfonamide (79); methyl 2-(2-(difluoromethoxy)-7-methylquinoxalin-5-yl)benzo[d]thiazol-7-ylcarbamate (80); N-(2-(2-(2-(difluoromethoxy)-7-methylquinoxalin-5-yl)-4-methylbenzo[d]thiazol-6-yloxy) ethyl)-4-fluorobenzenesulfonamide (81); 2-(2-(2-(difluoromethoxy)-7-methylquinoxalin-5-yl) benzo[d]thiazol-7-yloxy)-N-phenylacetamide (82); N-(2-(2-(2-(difluoromethoxy)-7-methylquinoxalin-5-yl)-4-methylbenzo[d]thiazol-6-yloxy) ethyl)-4-(trifluoromethyl) benzenesulfonamide (83); N-(2-(2-(2-(difluoromethoxy)-7-methylquinoxalin-5-yl)-4-methylbenzo[d]thiazol-6-yloxy) ethyl)-2,4-difluorobenzenesulfonamide (84); N-(2-(2-(2-(difluoromethoxy)-7-methylquinoxalin-5-yl)-4-methylbenzo[d]thiazol-6-yloxy) ethyl)-3,4-difluorobenzenesulfonamide (85); 4-chloro N-(2-(2-(2-(difluoromethoxy)-7-methylquinoxalin-5-yl)-4-methylbenzo[d]thiazol-6-yloxy)ethyl)benzenesulfonamide (86); N-(2-(2-(2-methoxy-7-methylquinoxalin-5-yl)-4-methylbenzo[d]thiazol-6-yloxy) ethyl)-4-methylbenzenesulfonamide (87); 4-fluoro N-(2-(2-(2-(methoxymethyl)-7-methylquinoxalin-5-yl)-4-methylbenzo[d] thiazol-6-yloxy)ethyl)benzenesulfonamide (89); 4-fluoro N-(2-(2-(2-methoxy-7-methylquinoxalin-5-yl)-4-(trifluoromethyl)benzo[d]thiazol-6-yloxy)ethyl) benzenesulfonamide (90);

N-(2-(2-(2-cyclopropyl-7-methylquinoxalin-5-yl)-4-methylbenzo[d]thiazol-6-yloxy)ethyl)-4-fluorobenzenesulfonamide (91); benzyl 2-(2-(methoxymethyl)-7-methylquinoxalin-5-yl)-4-methylbenzo[d]thiazol-6-yloxy) ethylcarbamate (92);
4-chloro-6-methoxy-2-(2-(methoxymethyl)-7-methylquinoxalin-5-yl)benzo[d]thiazole (93); 5-(5-methoxybenzofuran-2-yl)-2-(methoxymethyl)-7-methylquinoxaline (94);
N-(2-(4-methoxy-2-(2-(methoxymethyl)-7-methylquinoxalin-5-yl)benzo[d] thiazol-6-yloxy)ethyl)benzenesulfonamide (95);
2-fluoro N-(2-(2-(2-(methoxymethyl)-7-methylquinoxalin-5-yl)-4-methylbenzo[d]thiazol-6-yloxy)ethyl) benzenesulfonamide (96);
3-fluoro N-(2-(2-(2-(methoxymethyl)-7-methylquinoxalin-5-yl)-4-methylbenzo[d]thiazol-6-yloxy)ethyl)benzenesulfonamide (97);
N-(2-(4-chloro-2-(2-(methoxymethyl)-7-methylquinoxalin-5-yl)benzo[d]thiazol-6-yloxy) ethyl) methanesulfonamide (98);
N-(2-(4-chloro-2-(2-(methoxymethyl)-7-methylquinoxalin-5-yl)benzo[d]thiazol-6-yloxy) ethyl)benzenesulfonamide (99);
N-(2-(4-chloro-2-(2-(methoxymethyl)-7-methylquinoxalin-5-yl)benzo[d]thiazol-6-yloxy) ethyl)-2-fluorobenzenesulfonamide (100);
N-(2-(4-chloro-2-(2-(methoxymethyl)-7-methylquinoxalin-5-yl)benzo[d]thiazol-6-yloxy) ethyl)-4-fluorobenzenesulfonamide (101);
N-(2-(4-chloro-2-(2-(methoxymethyl)-7-methylquinoxalin-5-yl)benzo[d]thiazol-6-yloxy) ethyl)-3-fluorobenzenesulfonamide (102);
6-methoxy-2-(2-(methoxymethyl)-7-methylquinoxalin-5-yl)benzo[d]thiazole-4-carbonitrile (103);
N-(2-(4-cyclopropyl-2-(2-(methoxymethyl)-7-methylquinoxalin-5-yl)benzo[d]thiazol-6-yloxy)ethyl) benzenesulfonamide (104);
N-(2-(4-cyclopropyl-2-(2-(methoxymethyl)-7-methylquinoxalin-5-yl)benzo[d]thiazol-6-yloxy)ethyl)-4-fluorobenzenesulfonamide (105);
N-(2-(2-(2-(methoxymethyl)-7-methylquinoxalin-5-yl) benzo[d]thiazol-6-yloxy) ethyl)benzenesulfonamide (106);
4-fluoro N-(2-(2-(2-(methoxymethyl)-7-methylquinoxalin-5-yl)benzo[d]thiazol-6-yloxy)ethyl)benzenesulfonamide (107);
4-fluoro N-(2-(2-(2-(1-fluoroethyl)-7-methylquinoxalin-5-yl)-4-methylbenzo[d]thiazol-6-yloxy)ethyl)benzenesulfonamide (108);
N-(2-(4-cyano-2-(2-(methoxymethyl)-7-methylquinoxalin-5-yl)benzo[d]thiazol-6-yloxy)ethyl)-4-fluorobenzenesulfonamide (109);
2-(2-(2-methoxy-7-methylquinoxalin-5-yl)-4-methylbenzo[d]thiazol-6-yloxy)ethyl phenylcarbamate (110); 2-(2-(2-methoxy-7-methylquinoxalin-5-yl)-4-methylbenzo[d]thiazol-6-yloxy)ethyl pyridin-3-ylcarbamate (111);
2-(2-(2-methoxy-7-methylquinoxalin-5-yl)-4-methylbenzo[d]thiazol-6-yloxy)ethyl 6-methoxypyridin-3-ylcarbamate (112);
2-(2-(2-methoxy-7-methylquinoxalin-5-yl)-4-methylbenzo[d]thiazol-6-yloxy)ethyl pyridin-4-ylcarbamate (113);
N-(2-(2-(2-((difluoromethoxy)methyl)-7-methylquinoxalin-5-yl)-4-methylbenzo[d]thiazol-6-yloxy)ethyl)-4-fluorobenzenesulfonamide (114);
2-(2-(2-methoxy-7-methylquinoxalin-5-yl)benzo[d]thiazol-6-yloxy)ethyl 6-methoxypyridin-3-ylcarbamate (115);
2-(2-(2-methoxy-7-methylquinoxalin-5-yl)-4-methylbenzo[d]thiazol-6-yloxy)ethyl 5-cyanopyridin-3-ylcarbamate (116);
2-((2-(2-methoxy-7-methylquinoxalin-5-yl)-4-methylbenzo[d]thiazol-6-yl)oxy)ethyl (6-cyanopyridin-3-yl) carbamate (117);
2-((2-(2-methoxy-7-methylquinoxalin-5-yl)benzo[d]thiazol-6-yl)oxy) ethyl (3-cyanophenyl)carbamate (118);
2-((2-(2-methoxy-7-methylquinoxalin-5-yl)-4-methylbenzo[d]thiazol-6-yl)oxy)ethyl (2-chloropyrimidin-5-yl)carbamate (119);
3-methoxy-8-(6-methoxybenzo[d]thiazol-2-yl)quinoxalin-6-yl)methanol (127);
2-(2-(7-(hydroxymethyl)-2-methoxyquinoxalin-5-yl)-4-methylbenzo[d]thiazol-6-yloxy)ethyl 6-methylpyridin-3-ylcarbamate (128);
2-(2-(7-(hydroxymethyl)-2-methoxyquinoxalin-5-yl)-4-methylbenzo[d]thiazol-6-yloxy)ethyl 2-methylpyridin-4-ylcarbamate (129); methyl
6-methoxy-2-(2-methoxy-7-methylquinoxalin-5-yl)benzo[d]thiazole-4-carboxylate (152);
(6-methoxy-2-(2-methoxy-7-methylquinoxalin-5-yl)benzo[d]thiazol-4-yl)methanol (154);
(6-methoxy-2-(2-(methoxymethyl)-7-methylquinoxalin-5-yl)benzo[d]thiazol-4-yl) methanol (155); 1-(6-methoxy-2-(2-(methoxymethyl)-7-methylquinoxalin-5-yl)benzo[d]thiazol-4-yl) ethanol (156);
2-(6-methoxy-2-(2-(methoxymethyl)-7-methylquinoxalin-5-yl)benzo[d]thiazol-4-yl) propan-2-ol (157);
cyclopropyl(6-methoxy-2-(2-(methoxymethyl)-7-methylquinoxalin-5-yl) benzo[d]thiazol-4-yl)methanol (158);
1-(6-methoxy-2-(2-(methoxymethyl)-7-methylquinoxalin-5-yl)benzo[d]thiazol-4-yl)-N,N-dimethylmethanamine (159);
cyclopropyl(6-methoxy-2-(2-methoxy-7-methylquinoxalin-5-yl)benzo[d]thiazol-4-yl) methanol (160);
(6-methoxy-2-(2-(methoxymethyl)-7-methylquinoxalin-5-yl)benzo[d]thiazol-4-yl) (phenyl)methanol (161);
6-methoxy-2-(2-(methoxymethyl)-7-methylquinoxalin-5-yl)benzo[d]thiazole-4-carboxylic acid (162);
(6-methoxy-2-(2-(methoxymethyl)-7-methylquinoxalin-5-yl)benzo[d]thiazol-4-yl)(phenyl) methanol (163); 1-(6-methoxy-2-(2-(methoxymethyl)-7-methylquinoxalin-5-yl)benzo[d] thiazol-4-yl)-2,2-dimethylpropan-1-ol (164);
cyclohexyl(6-methoxy-2-(2-(methoxymethyl)-7-methylquinoxalin-5-yl)benzo[d]thiazol-4-yl)methanol (165);
cyclobutyl(6-methoxy-2-(2-(methoxymethyl)-7-methylquinoxalin-5-yl)benzo[d]thiazol-4-yl)methanol (166);
(6-methoxy-2-(2-(methoxymethyl)-7-methylquinoxalin-5-yl)benzo [d]thiazol-4-yl)(pyridin-2-yl)methanol (167);
(6-methoxy-2-(2-(methoxymethyl)-7-methylquinoxalin-5-yl)benzo[d]thiazol-4-yl) (pyridin-3-yl)methanol (168);
1-(6-methoxy-2-(2-(methoxymethyl)-7-methylquinoxalin-5-yl)benzo[d]thiazol-4-yl)-2,2-dimethylpropan-1-ol-1-d$_1$ (169);
1-(6-methoxy-2-(2-(methoxymethyl)-7-methylquinoxalin-5-yl)benzo[d]thiazol-4-yl)-2,2-dimethylpropan-1-ol-d$_5$ (170);
2,2,2-trifluoro-1-(6-methoxy-2-(2-(methoxymethyl)-7-methylquinoxalin-5-yl)benzo[d]thiazol-4-yl)ethanol (171);
(6-methoxy-2-(2-(methoxymethyl)-7-methylquinoxalin-5-yl)benzo[d] thiazol-4-yl)(pyridin-4-yl)methanol (172);
3,3,3-trifluoro-1-(6-methoxy-2-(2-(methoxymethyl)-7-methylquinoxalin-5-yl)benzo[d]thiazol-4-yl)propan-1-ol (173);

2,2,2-trifluoro-1-(6-methoxy-2-(2-methoxy-7-methylquinoxalin-5-yl)benzo[d]thiazol-4-yl) ethanol (174);
6-methoxy-2-(2-(methoxymethyl)-7-methylquinoxalin-5-yl)-4-methylbenzo[d]thiazole (183);
2-(2-(difluoro(methoxy)methyl)-7-methylquinoxalin-5-yl)-6-methoxy-4-methylbenzo[d]thiazole (186);
6-methoxy-4-methyl-2-(7-methyl-2-(phenoxymethyl)quinoxalin-5-yl)benzo[d]thiazole (187);
1-(5-(6-methoxy-4-methylbenzo[d]thiazol-2-yl)-7-methylquinoxalin-2-yl)-N,N-dimethyl methanamine (188);
2-(2-(ethoxymethyl)-7-methylquinoxalin-5-yl)-6-methoxy-4-methylbenzo[d]thiazole (189); N-(2-((2-(7-chloro-2-methoxyquinoxalin-5-yl)-4-methylbenzo[d]thiazol-6-yl) oxy) ethyl)-4-fluorobenzenesulfonamide (199); N-(2-((2-(7-chloro-2-(methoxymethyl) quinoxalin-5-yl)-4-methylbenzo[d]thiazol-6-yl)oxy)ethyl)-4-fluorobenzenesulfonamide (200); 2-(7-chloro-2-(methoxymethyl)quinoxalin-5-yl)-6-methoxybenzo[d]thiazole (201);
2-(7-chloro-2-(methoxymethyl)quinoxalin-5-yl)-6-methoxybenzo[d]thiazole (202);
6-methoxy-2-(2-(methoxymethyl)-7-(trifluoromethoxy)quinoxalin-5-yl)-4-methylbenzo[d] thiazole (203); methyl 8-(6-methoxy-4-methylbenzo[d]thiazol-2-yl)-3-(methoxymethyl) quinoxaline-6-carboxylate (204); methyl 8-(6-(2-(4-fluorophenylsulfonamido)ethoxy)-4-methylbenzo[d]thiazol-2-yl)-3-(methoxymethyl)quinoxaline-6-carboxylate (205);
2-(7-fluoro-2-(methoxymethyl)quinoxalin-5-yl)-6-methoxy-4-methylbenzo[d]thiazole (206); 4-fluoro-N-(2-((2-(7-fluoro-2-(methoxymethyl)quinoxalin-5-yl)-4-methylbenzo[d] thiazol-6-yl)oxy)ethyl) benzenesulfonamide (207);
6-methoxy-2-(2-(methoxymethyl)-7-(trifluoromethyl)quinoxalin-5-yl)-4-methylbenzo[d]thiazole (208);
4-fluoro-N-(2-((2-(2-(methoxymethyl)-7-(trifluoromethyl) quinoxalin-5-yl)-4-methylbenzo[d]thiazol-6-yl)oxy) ethyl)benzenesulfonamide (209);
4-chloro-2-(7-chloro-2-(methoxymethyl) quinoxalin-5-yl)-6-methoxybenzo[d]thiazole (210); 3-methoxy-8-(6-methoxy-4-methylbenzo[d] thiazol-2-yl)quinoxaline-6-carbonitrile (211); 4-chloro-6-methoxy-2-(2-(methoxymethyl) quinoxalin-5-yl)benzo[d]thiazole (212); 4-fluoro-N-(2-((2-(2-(methoxymethyl) quinoxalin-5-yl)-4-methylbenzo[d]thiazol-6-yl)oxy) ethyl) benzenesulfonamide (213);
2-(7-chloro-2-methoxyquinoxalin-5-yl)-4,5-difluoro-6-methoxybenzo[d]thiazole (214);
4-chloro-2-(7-chloro-2-methoxyquinoxalin-5-yl)-5-fluoro-6-methoxybenzo[d]thiazole (215); 4-chloro-5-fluoro-6-methoxy-2-(2-methoxy-6,7-dimethylquinoxalin-5-yl) benzo[d] thiazole (216); 8-(4,5-difluoro-6-methoxybenzo [d] thiazol-2-yl)-3-methoxyquinoxaline-6-carbonitrile (217);
(8-(4-chloro-5-fluoro-6-methoxybenzo[d]thiazol-2-yl)-3-methoxyquinoxalin-6-yl)methanol (218); (3-methoxy-8-(6-methoxy-4,5-dimethylbenzo [d]thiazol-2-yl)quinoxalin-6-yl)methanol (219); (8-(4,5-difluoro-6-methoxybenzo[d] thiazol-2-yl)-3-methoxyquinoxalin-6-yl)methanol (220); 8-(5-fluoro-6-methoxybenzo[d]thiazol-2-yl)-3-methoxyquinoxaline-6-carbonitrile (221); (8-(5-fluoro-6-methoxybenzo [d]thiazol-2-yl)-3-methoxyquinoxalin-6-yl)methanol (222);
(8-(4-chloro-5-fluoro-6-methoxybenzo[d]thiazol-2-yl)-5-fluoro-3-methoxyquinoxalin-6-yl)methanol (224);

8-(6-(2-(4-fluorophenylsulfonamido)ethoxy)-4-methylbenzo[d]thiazol-2-yl)-3-(methoxymethyl)quinoxaline-6-carboxamide (225); 8-(6-(2-(4-fluorophenylsulfonamido) ethoxy)-4-methylbenzo[d]thiazol-2-yl)-3-(methoxymethyl)-N,N-dimethylquinoxaline-6-carboxamide (226);
4-fluoro-N-(2-((2-(2-(methoxymethyl)-7-(piperidine-1-carbonyl) quinoxalin-5-yl)-4-methylbenzo[d]thiazol-6-yl)oxy)ethyl)benzenesulfonamide (227);
8-(6-(2-(4-fluorophenylsulfonamido)ethoxy)-4-methylbenzo[d]thiazol-2-yl)-N-(2-methoxyethyl)-3-(methoxymethyl)quinoxaline-6-carboxamide (228);
4-fluoro-N-(2-((2-(2-methoxy-7-vinylquinoxalin-5-yl)-4-methylbenzo[d]thiazol-6-yl)oxy) ethyl) benzenesulfonamide (229);
N-(2-((2-(7-ethynyl-2-methoxyquinoxalin-5-yl)-4-methylbenzo[d]thiazol-6-yl)oxy)ethyl)-4-fluorobenzenesulfonamide (230);
N-(2-((2-(7-cyano-2-methoxyquinoxalin-5-yl)-4-methylbenzo[d]thiazol-6-yl)oxy)ethyl)-4-fluorobenzenesulfonamide (231);
N-(2-((2-(7-cyano-2-(methoxymethyl)quinoxalin-5-yl)-4-methylbenzo[d]thiazol-6-yl) oxy)ethyl)-4-fluorobenzenesulfonamide (232);
8-(6-methoxy-4-methylbenzo[d]thiazol-2-yl)-3-(methoxymethyl)quinoxaline-6-carbonitrile (233);
4-fluoro-N-(2-((2-(2-(methoxymethyl)-7-vinylquinoxalin-5-yl)-4-methylbenzo[d] thiazol-6-yl)oxy)ethyl) benzenesulfonamide (234);
4-fluoro-N-(2-((2-(7-(hydroxymethyl)-2-methoxyquinoxalin-5-yl)-4-methylbenzo[d]thiazol-6-yl)oxy)ethyl) benzenesulfonamide (235);
N-(2-((2-(7-(1,2-dihydroxyethyl)-2-methoxyquinoxalin-5-yl)-4-methylbenzo[d]thiazol-6-yl)oxy) ethyl)-4-fluorobenzenesulfonamide (236);
4-fluoro-N-(2-((2-(7-(2-hydroxyethyl)-2-methoxyquinoxalin-5-yl)-4-methylbenzo[d]thiazol-6-yl)oxy)ethyl)benzenesulfonamide (237);
N-(2-((2-(7-(aminomethyl)-2-methoxyquinoxalin-5-yl)-4-methylbenzo[d]thiazol-6-yl)oxy) ethyl)-4-fluorobenzenesulfonamide (238);
4-fluoro-N-(2-((2-(7-(1-hydroxyethyl)-2-methoxyquinoxalin-5-yl)-4-methylbenzo[d]thiazol-6-yl)oxy)ethyl) benzenesulfonamide (239);
4-fluoro-N-(2-((2-(7-(hydroxy(phenyl)methyl)-2-methoxyquinoxalin-5-yl)-4-methylbenzo[d]thiazol-6-yl)oxy) ethyl)benzenesulfonamide (240);
4-fluoro-N-(2-((2-(2-methoxy-7-(prop-1-en-2-yl)quinoxalin-5-yl)-4-methylbenzo [d]thiazol-6-yl)oxy)ethyl) benzenesulfonamide (241);
4-fluoro-N-(2-((2-(7-(2-hydroxypropan-2-yl)-2-methoxyquinoxalin-5-yl)-4-methylbenzo[d]thiazol-6-yl)oxy) ethyl)benzenesulfonamide (242);
(8-(5-fluoro-6-methoxy-4-methylbenzo[d]thiazol-2-yl)-3-methoxyquinoxalin-6-yl) methanol (243); 1-(8-(5-fluoro-6-methoxy-4-methylbenzo[d] thiazol-2-yl)-3-methoxyquinoxalin-6-yl) ethanol (244);
(8-(5-fluoro-6-methoxy-4-methylbenzo[d] thiazol-2-yl)-3-methoxyquinoxalin-6-yl) (phenyl)methanol (245);
cyclopropyl(8-(5-fluoro-6-methoxy-4-methylbenzo[d]thiazol-2-yl)-3-methoxyquinoxalin-6-yl)methanol (246);
4-fluoro-N-(2-((2-(7-fluoro-2-methylquinoxalin-5-yl)-4-methylbenzo[d]thiazol-6-yl) oxy)ethyl)benzenesulfonamide (247);
(8-(5-fluoro-6-isopropoxybenzo[d]thiazol-2-yl)-3-methoxyquinoxalin-6-yl)methanol (248); N-(2-((2-(7-chloro-2-methoxyquinoxalin-5-yl)-4-methylbenzo[d]thiazol-6-yl) oxy) ethyl)pyridine-3-sulfonamide (249); ethyl 2-((2-(7-chloro-2-methoxyquinoxalin-5-yl)-4-methylbenzo[d]thiazol-6-yl)oxy) acetate (250);
2-((2-(7-chloro-2-methoxyquinoxalin-5-yl)-4-methylbenzo[d]thiazol-6-yl)oxy)acetic acid (251);
2-((2-(7-(hydroxymethyl)-2-methoxyquinoxalin-5-yl)-4-methylbenzo[d]thiazol-6-yl)oxy) ethyl (6-methoxypyridin-3-yl)carbamate (252);
6-methoxy-2-(2-(methoxymethyl)-7-methylquinoxalin-5yl) benzo[d] thiazole (253);
4-fluoro-6-methoxy-2-(2-(methoxymethyl)-7-methylquinoxalin-5-yl) benzo[d]thiazole (254); 6-ethoxy-2-(2-(methoxymethyl)-7-methylquinoxalin-5-yl)benzo[d]thiazole (255);
2-(2-(methoxymethyl)-7-methylquinoxalin-5-yl)benzo[d]thiazole (256);
4,6-difluoro-2-(2-(methoxymethyl)-7-methylquinoxalin-5-yl)benzo[d]thiazole (257);
4,6-dimethoxy-2-(2-(methoxymethyl)-7-methylquinoxalin-5-yl)benzo[d]thiazole (258);
4-methoxy-2-(2-(methoxymethyl)-7-methylquinoxalin-5-yl)benzo[d]thiazole (259);
4-chloro-2-(2-(methoxymethyl)-7-methylquinoxalin-5-yl)benzo[d]thiazole (260);
2-(2-(methoxymethyl)-7-methylquinoxalin-5-yl)-4-methyl-benzo[d]thiazole (261);
2-(2-(methoxymethyl)-7-methylquinoxalin-5-yl)-4-methyl-6-(trifluoromethoxy)benzo[d] thiazole (262);
6-(difluoromethoxy)-2-(2-(methoxymethyl)-7-methylquinoxalin-5-yl)-4-methylbenzo[d]thiazole (263); methyl 2-(2-(methoxymethyl)-7-methylquinoxalin-5-yl)-4-methyl-benzo[d]thiazole-6-carboxylate (264);
4-chloro-7-fluoro-6-methoxy-2-(2-(methoxymethyl)-7-methylquinoxalin-5-yl)benzo[d]thiazole (265);
4-chloro-6-fluoro-2-(2-(methoxymethyl)-7-methylquinoxalin-5-yl)benzo[d]thiazole (266);
4,5-difluoro-6-methoxy-2-(2-(methoxymethyl)-7-methylquinoxalin-5-yl)benzo[d]thiazole (267);
5-chloro-6-methoxy-2-(2-(methoxymethyl)-7-methylquinoxalin-5-yl)benzo[d]thiazole (268); 5,6-difluoro-4-methoxy-2-(2-(methoxymethyl)-7-methylquinoxalin-5-yl)benzo [d]thiazole (269);
6-fluoro-4-methoxy-2-(2-(methoxymethyl)-7-methylquinoxalin-5-yl)benzo[d]thiazole (270);
5-fluoro-4,6-dimethoxy-2-(2-(methoxymethyl)-7-methylquinoxalin-5-yl)benzo[d]thiazole (271); 6-fluoro-2-(2-(methoxymethyl)-7-methylquinoxalin-5-yl)benzo[d]thiazole (272);
4-fluoro-2-(2-(methoxymethyl)-7-methylquinoxalin-5-yl) benzo[d]thiazole (273);
6-chloro-2-(2-(methoxymethyl)-7-methylquinoxalin-5-yl) benzo[d]thiazole (274);
4,6-dichloro-2-(2-(methoxymethyl)-7-methylquinoxalin-5-yl)benzo[d]thiazole (275);
6-methoxy-2-(2-(methoxymethyl)-7-methylquinoxalin-5-yl)-5-methylbenzo[d]thiazole (276);
5-fluoro-6-methoxy-2-(2-(methoxymethyl)-7-methylquinoxalin-5-yl)benzo[d]thiazole (277); 4,5-difluoro-6-methoxy-2-(2-methoxy-7-methylquinoxalin-5-yl)benzo[d]thiazole (278); 6-methoxy-2-(2-methoxy-7-methylquinoxalin-5-yl)-5-methylbenzo[d]thiazole (279); 5-fluoro-6-methoxy-2-(2-methoxy-7-methylquinoxalin-5-yl)benzo[d]thiazole (280); 2-(2-(methoxymethyl)-7-methylquinoxalin-5-yl)-4-methylbenzo[d]thiazol-6-ol (281);
4-chloro-5-fluoro-6-methoxy-2-(2-methoxy-7-methylquinoxalin-5-yl)benzo[d]thiazole (282);
4-chloro-5-fluoro-6-methoxy-2-(2-(methoxymethyl)-7-methylquinoxalin-5-yl)benzo[d]thiazole (283);
6-methoxy-2-(2-(methoxymethyl)-7-methylquinoxalin-5-yl)-4,5-dimethylbenzo[d]thiazole (284); methyl 2-((5-fluoro-2-(2-methoxy-7-methylquinoxalin-5-yl)-4-methylbenzo[d]thiazol-6-yl)oxy)acetate (285); methyl 2-((5-fluoro-2-(2-(methoxymethyl)-7-methylquinoxalin-5-yl)-4-methylbenzo[d]thiazol-6-yl) oxy)acetate (286); methyl 2-((4-chloro-5-fluoro-2-(2-methoxy-7-methylquinoxalin-5-yl) benzo[d]thiazol-6-yl)oxy)acetate (287);
2-((5-fluoro-2-(2-methoxy-7-methylquinoxalin-5-yl)-4-methylbenzo[d]thiazol-6-yl)oxy)ethanol (288);
2-((5-fluoro-2-(2-(methoxymethyl)-7-methylquinoxalin-5-yl)-4-methylbenzo[d]thiazol-6-yl)oxy)ethanol (289);
5-fluoro-2-(2-(methoxymethyl)-7-methylquinoxalin-5-yl)-4-methylbenzo[d] thiazol-6-ol (290); 4-chloro-5-fluoro-2-(2-(methoxymethyl)-7-methylquinoxalin-5-yl) benzo[d]thiazol-6-ol (291); methyl 2-((4-chloro-5-fluoro-2-(2-(methoxymethyl)-7-methylquinoxalin-5-yl)benzo[d]thiazol-6-yl)oxy)acetate (292);
2-((4-chloro-5-fluoro-2-(2-(methoxymethyl)-7-methylquinoxalin-5-yl)benzo[d]thiazol-6-yl)oxy)ethanol (293);
5-fluoro-6-methoxy-2-(2-methoxy-7-methylquinoxalin-5-yl)-4-methylbenzo[d]thiazole (294);
5-fluoro-6-methoxy-2-(2-(methoxymethyl)-7-methylquinoxalin-5-yl)-4-methylbenzo[d]thiazole (295); methyl 2-((2-(2-(methoxymethyl)-7-methylquinoxalin-5-yl)-4,5-dimethylbenzo[d]thiazol-6-yl)oxy)acetate (296);
2-((2-(2-(methoxymethyl)-7-methylquinoxalin-5-yl)-4,5-dimethylbenzo[d]thiazol-6-yl)oxy)ethanol (297);
4-chloro-6-methoxy-2-(2-(methoxymethyl)-7-methylquinoxalin-5-yl)-5-methylbenzo[d]thiazole (298);
4-chloro-6-methoxy-2-(2-methoxy-7-methylquinoxalin-5-yl)-5-methylbenzo[d] thiazole (299);
(6-methoxy-2-(2-(methoxymethyl)-7-methylquinoxalin-5-yl)-5-methylbenzo[d]thiazol-4-yl)methanol (300);
(6-methoxy-2-(2-(methoxymethyl)-7-methylquinoxalin-5-yl)-5-methylbenzo[d]thiazol-4-yl)methanol (301);
2-((5-fluoro-2-(2-methoxy-7-methylquinoxalin-5-yl)-4-methylbenzo[d]thiazol-6-yl)oxy)ethyl (6-fluoropyridin-3-yl)carbamate (302);
2-((5-fluoro-2-(2-(methoxymethyl)-7-methylquinoxalin-5-yl)-4-methylbenzo[d]thiazol-6-yl)oxy)ethyl (6-fluoropyridin-3-yl) carbamate (303);
2-((4-chloro-5-fluoro-2-(2-methoxy-7-methylquinoxalin-5-yl)benzo[d] thiazol-6-yl)oxy)ethyl (6-fluoropyridin-3-yl) carbamate (304);
2-((4-chloro-5-fluoro-2-(2-(methoxymethyl)-7-methylquinoxalin-5-yl)benzo[d]thiazol-6-yl)oxy)ethyl (6-fluoropyridin-3-yl)carbamate (305);
2-(2-(methoxymethyl)-7-methylquinoxalin-5-yl)-4-methyl-benzo[d]thiazol-6-ol (306);
6-(benzyloxy)-2-(2-(methoxymethyl)-7-methylquinoxalin-5-yl)-4-methylbenzo[d]thiazole (307); (2-(2-(methoxymethyl)-7-methylquinoxalin-5-yl)benzo[d]thiazol-6-yl) methanol (308);
6-(methoxymethyl)-2-(2-(methoxymethyl)-7-methylquinoxalin-5-yl)benzo[d]thiazole (309); 6-methoxy-2-(2-(methoxymethyl)-7-methylquinoxalin-5-yl)benzo[d]thiazol-5-ol (310); 5,6-dimethoxy-2-(2-(methoxymethyl)-7-methylquinoxalin-5-yl)benzo[d]thiazole (311); (6-methoxy-2-(2-(methoxymethyl)-7-methylquinoxalin-5-yl)benzo[d]thiazol-5-yl) methanol (312);
6-chloro-5-fluoro-4-methoxy-2-(2-(methoxymethyl)-7-methylquinoxalin-5-yl) benzo[d] thiazole (313);

4-cyclopropyl-5-fluoro-6-methoxy-2-(2-(methoxymethyl)-7-methylquinoxalin-5-yl)benzo [d]thiazole (314);
6-ethoxy-4,5-difluoro-2-(2-methoxy-7-methylquinoxalin-5-yl)benzo[d]thiazole (315); N-(2-((4,5-difluoro-2-(2-methoxy-7-methylquinoxalin-5-yl)benzo[d]thiazol-6-yl) oxy)ethyl)-3-fluorobenzenesulfonamide (316);
N-(2-((4,5-difluoro-2-(2-(methoxymethyl)-7-methylquinoxalin-5-yl)benzo[d] thiazol-6-yl)oxy)ethyl)-3-fluorobenzenesulfonamide (317);
2-((4-chloro-5-fluoro-2-(2-methoxy-7-methylquinoxalin-5-yl)benzo[d]thiazol-6-yl)oxy)ethanol (318);
1-((2-(2-(methoxymethyl)-7-methylquinoxalin-5-yl)-4,5-dimethylbenzo[d]thiazol-6-yl)oxy)-2-methylpropan-2-ol (319);
2-((2-(2-(methoxymethyl)-7-methylquinoxalin-5-yl)-4,5-dimethylbenzo[d]thiazol-6-yl) oxy)ethyl methyl carbonate (320);
2-((2-(2-(methoxymethyl)-7-methylquinoxalin-5-yl)-4,5-dimethylbenzo[d]thiazol-6-yl)oxy) propan-1-ol (racemate) (321);
1-((2-(2-(methoxymethyl)-7-methylquinoxalin-5-yl)-4,5-dimethylbenzo[d]thiazol-6-yl) oxy)propan-2-ol (racemate) (322);
3-((2-(2-(methoxymethyl)-7-methylquinoxalin-5-yl)-4,5-dimethylbenzo[d]thiazol-6-yl)oxy)butan-2-ol (diastereomeric) (323);
2-((4-chloro-5-fluoro-2-(2-methoxy-7-methylquinoxalin-5-yl)benzo[d]thiazol-6-yl)oxy)-1-morpholinoethanone (324);
(6-methoxy-2-(2-methoxy-7-methylquinoxalin-5-yl)-5-methylbenzo[d]thiazol-4-yl) methanol (bis-deuterated) (325); 1-(6-methoxy-2-(2-(methoxymethyl)-7-methylquinoxalin-5-yl)-5-methylbenzo[d]thiazol-4-yl)ethanol (326);
2((4-chloro-2-(2-(methoxymethyl)-7-methylquinoxalin-5-yl)-5-methylbenzo[d]thiazol-6-yl)oxy)ethanol (327);
1-(6-methoxy-2-(2-(methoxymethyl)-7-methylquinoxalin-5-yl)-5-methylbenzo[d]thiazol-4-yl)-2,2-dimethylpropan-1-ol (racemate) (328);
5-fluoro-6-isopropoxy-2-(2-(methoxymethyl)-7-methylquinoxalin-5-yl) benzo[d]thiazole (329); N-(2((4-chloro-5-fluoro-2-(2-methoxy-7-methylquinoxalin-5-yl) benzo[d] thiazol-6-yl)oxy)ethyl)benzenesulfonamide (330);
2((4-chloro-5-fluoro-2-(2-methoxy-7-methylquinoxalin-5-yl)benzo[d]thiazol-6-yl) oxy)ethyl pyridin-3-ylcarbamate (331);
2((4-chloro-5-fluoro-2-(2-methoxy-7-methylquinoxalin-5-yl)benzo[d]thiazol-6-yl)oxy)ethyl (6-methoxypyridin-3-yl)carbamate (332);
2((4-chloro-5-fluoro-2-(2-methoxy-7-methylquinoxalin-5-yl)benzo[d]thiazol-6-yl)oxy)ethyl (2-oxo-2,3-dihydrobenzo[d]oxazol-6-yl)carbamate (333);
2((4-chloro-5-fluoro-2-(2-methoxy-7-methylquinoxalin-5-yl)benzo[d]thiazol-6-yl)oxy)ethyl (2,2,2-trifluoroethyl) carbamate (334);
2((4-chloro-5-fluoro-2-(2-methoxy-7-methylquinoxalin-5-yl)benzo[d]thiazol-6-yl)oxy)ethyl pyridin-4-ylcarbamate (335);
2((4-chloro-5-fluoro-2-(2-methoxy-7-methylquinoxalin-5-yl)benzo[d]thiazol-6-yl)oxy)ethyl (2-methylpyridin-4-yl) carbamate (336);
2((4-chloro-5-fluoro-2-(2-methoxy-7-methylquinoxalin-5-yl)benzo[d]thiazol-6-yl)oxy)ethyl (5-fluoropyridin-3-yl) carbamate (337);
2((4-chloro-5-fluoro-2-(2-methoxy-7-methylquinoxalin-5-yl)benzo[d]thiazol-6-yl)oxy)ethyl (6-(3-methyl-1H-1,2,4-triazol-1-yl)pyridin-3-yl)carbamate (338);
2-((5-fluoro-2-(2-methoxy-7-methylquinoxalin-5-yl) benzo[d]thiazol-6-yl)oxy)ethyl pyridin-3-ylcarbamate (339);
2-((5-fluoro-2-(2-methoxy-7-methylquinoxalin-5-yl)benzo[d]thiazol-6-yl)oxy)ethyl (6-fluoropyridin-3-yl)carbamate (340);
2-((5-fluoro-2-(2-methoxy-7-methylquinoxalin-5-yl)benzo[d]thiazol-6-yl)oxy) ethyl (6-methoxypyridin-3-yl)carbamate (341);
2-((5-fluoro-2-(2-methoxy-7-methylquinoxalin-5-yl)benzo[d]thiazol-6-yl)oxy)ethyl pyridin-4-ylcarbamate (342);
2-((5-fluoro-2-(2-methoxy-7-methylquinoxalin-5-yl)benzo[d]thiazol-6-yl)oxy)ethyl (2-oxo-2,3-dihydrobenzo[d]oxazol-6-yl)carbamate (343);
(R)-2-((5-fluoro-2-(2-methoxy-7-methylquinoxalin-5-yl)benzo[d]thiazol-6-yl)oxy)propyl pyridin-3-ylcarbamate (344);
(S)-2-((5-fluoro-2-(2-methoxy-7-methylquinoxalin-5-yl)benzo[d]thiazol-6-yl)oxy)propyl pyridin-3-ylcarbamate (345); (S)-1-((5-fluoro-2-(2-methoxy-7-methylquinoxalin-5-yl) benzo[d]thiazol-6-yl)oxy)propan-2-ylpyridin-3-ylcarbamate (346);
(R)-1-((5-fluoro-2-(2-methoxy-7-methylquinoxalin-5-yl)benzo[d]thiazol-6-yl)oxy)propan-2-yl pyridin-3-ylcarbamate (347);
(R)-1-((5-fluoro-2-(2-methoxy-7-methylquinoxalin-5-yl)benzo[d] thiazol-6-yl)oxy)propan-2-yl (6-fluoropyridin-3-yl)carbamate (348);
(R)-1-((5-fluoro-2-(2-methoxy-7-methylquinoxalin-5-yl)benzo[d]thiazol-6-yl)oxy)propan-2-yl pyridin-4-ylcarbamate (349);
(R)-1-((5-fluoro-2-(2-methoxy-7-methylquinoxalin-5-yl)benzo[d] thiazol-6-yl)oxy)propan-2-yl (2-oxo-2,3-dihydrobenzo[d]oxazol-6-yl)carbamate (350);
(R)-1-((5-fluoro-2-(2-methoxy-7-methylquinoxalin-5-yl)benzo[d]thiazol-6-yl)oxy) propan-2-yl (6-cyanopyridin-3-yl)carbamate (351);
(R)-1-((5-fluoro-2-(2-methoxy-7-methylquinoxalin-5-yl)benzo[d]thiazol-6-yl)oxy)propan-2-yl (3-amino-3-oxopropyl) carbamate (352);
(R)-1-((5-fluoro-2-(2-methoxy-7-methylquinoxalin-5-yl)benzo[d] thiazol-6-yl)oxy)propan-2-yl pyridazin-4-ylcarbamate (353);
(R)-1-((5-fluoro-2-(2-methoxy-7-methylquinoxalin-5-yl)benzo[d]thiazol-6-yl)oxy)propan-2-yl 1H-pyrrolo[2,3-b]pyridin-5-ylcarbamate (354);
(R)-1-((5-fluoro-2-(2-methoxy-7-methylquinoxalin-5-yl)benzo[d]thiazol-6-yl)oxy)propan-2-yl 1H-indol-5-ylcarbamate (355);
(R)-1-((5-fluoro-2-(2-methoxy-7-methylquinoxalin-5-yl)benzo[d]thiazol-6-yl)oxy)propan-2-yl (1-methyl-1H-indol-5-yl)carbamate (356);
(R)-1-((5-fluoro-2-(2-methoxy-7-methylquinoxalin-5-yl)benzo[d]thiazol-6-yl)oxy)propan-2-yl (2-methylpyrimidin-5-yl)carbamate (357);
2-((4-chloro-5-fluoro-2-(2-methoxy-7-methylquinoxalin-5-yl)benzo[d]thiazol-6-yl)oxy) ethyl carbamate (358);
2-((4-chloro-5-fluoro-2-(2-methoxy-7-methylquinoxalin-5-yl) benzo[d]thiazol-6-yl)oxy)ethyl 1H-pyrrolo[2,3-b]pyridin-5-ylcarbamate (359);
2-((4-chloro-5-fluoro-2-(2-methoxy-7-methylquinoxalin-5-yl)benzo[d]thiazol-6-yl)oxy)ethyl 1H-indol-5-ylcarbamate (360); methyl
5-(((2-((4-chloro-5-fluoro-2-(2-methoxy-7-methylquinoxalin-5-yl)benzo[d]thiazol-6-yl)oxy)ethoxy)carbonyl) amino)picolinate (361);

2-((4-chloro-5-fluoro-2-(2-methoxy-7-methylquinoxalin-5-yl)benzo[d]thiazol-6-yl)oxy)ethyl (2-methylpyrimidin-5-yl)carbamate (362);

2-((4-chloro-5-fluoro-2-(2-methoxy-7-methylquinoxalin-5-yl)benzo[d]thiazol-6-yl)oxy)ethyl (5-methoxy-1,2,4-thiadiazol-3-yl)carbamate (363);

2-((4-chloro-5-fluoro-2-(2-methoxy-7-methylquinoxalin-5-yl)benzo[d]thiazol-6-yl)oxy)ethyl 1H-pyrazol-4-ylcarbamate (364);

2-((4-chloro-5-fluoro-2-(2-methoxy-7-methylquinoxalin-5-yl)benzo[d]thiazol-6-yl)oxy) ethyl (1-methyl-1H-pyrazol-4-yl)carbamate (365);

2-((4-chloro-5-fluoro-2-(2-methoxy-7-methylquinoxalin-5-yl)benzo[d]thiazol-6-yl)oxy)ethyl (5-methyl-1,3,4-oxadiazol-2-yl) carbamate (366);

2-((4-chloro-5-fluoro-2-(2-methoxy-7-methylquinoxalin-5-yl)benzo[d] thiazol-6-yl)oxy)ethyl (1,2-dimethyl-1H-pyrrolo[2,3-b]pyridin-5-yl)carbamate (367);

2-((4-chloro-5-fluoro-2-(2-methoxy-7-methylquinoxalin-5-yl)benzo[d]thiazol-6-yl)oxy) ethyl (pyridin-3-ylmethyl) carbamate (368);

2-((4-chloro-5-fluoro-2-(2-methoxy-7-methylquinoxalin-5-yl)benzo[d]thiazol-6-yl)oxy)ethyl (pyridin-4-ylmethyl) carbamate (369);

(R)-1-((4-chloro-5-fluoro-2-(2-methoxy-7-methylquinoxalin-5-yl)benzo[d]thiazol-6-yl)oxy)propan-2-yl (5-methyl-1,3,4-thiadiazol-2-yl)carbamate (370);

(R)-1-((4-chloro-5-fluoro-2-(2-methoxy-7-methylquinoxalin-5-yl)benzo[d]thiazol-6-yl)oxy)propan-2-yl (6-cyanopyridin-3-yl)carbamate (371);

(R)-1-((4-chloro-5-fluoro-2-(2-methoxy-7-methylquinoxalin-5-yl)benzo[d]thiazol-6-yl)oxy)propan-2-yl pyridin-3-ylcarbamate (372);

(R)-1-((4-chloro-5-fluoro-2-(2-methoxy-7-methylquinoxalin-5-yl)benzo[d]thiazol-6-yl)oxy)propan-2-yl (2-oxo-2,3-dihydrobenzo[d]oxazol-6-yl)carbamate (373);

(R)-1-((4-chloro-5-fluoro-2-(2-methoxy-7-methylquinoxalin-5-yl)benzo[d]thiazol-6-yl)oxy)propan-2-yl (6-(trifluoromethyl)pyridin-3-yl)carbamate (374);

(R)-1-((4-chloro-5-fluoro-2-(2-methoxy-7-methylquinoxalin-5-yl)benzo[d]thiazol-6-yl)oxy)propan-2-yl 3H-pyrrolo [2,3-b]pyridin-5-yl carbamate (375);

(R)-1-((4-chloro-5-fluoro-2-(2-methoxy-7-methylquinoxalin-5-yl)benzo[d]thiazol-6-yl)oxy)propan-2-yl (4-methylpyridin-3-yl) carbamate (376);

(R)-1-((4-chloro-5-fluoro-2-(2-methoxy-7-methylquinoxalin-5-yl) benzo[d]thiazol-6-yl)oxy)propan-2-yl (6-methylpyridin-3-yl)carbamate (377); methyl 4-(((2-((4-chloro-5-fluoro-2-(2-methoxy-7-methylquinoxalin-5-yl)benzo[d]thiazol-6-yl) oxy)ethoxy)carbonyl)amino)-1-methyl-1H-pyrrole-2-carboxylate (378);

1-((5-fluoro-2-(2-methoxy-7-methylquinoxalin-5-yl)benzo[d]thiazol-6-yl)oxy)-3-isobutoxypropan-2-yl pyridin-3-ylcarbamate (379);

1-(benzyloxy)-3-((5-fluoro-2-(2-methoxy-7-methylquinoxalin-5-yl)benzo[d]thiazol-6-yl) oxy)propan-2-yl pyridin-3-ylcarbamate (380);

2-((4-chloro-5-fluoro-2-(2-methoxy-7-methylquinoxalin-5-yl)benzo[d]thiazol-6-yl)oxy)propyl (6-methoxypyridin-3-yl)carbamate (racemate) (381);

(S)-2-((4-chloro-5-fluoro-2-(2-methoxy-7-methylquinoxalin-5-yl)benzo[d]thiazol-6-yl)oxy)propyl (6-methoxypyridin-3-yl)carbamate (382);

2-((4-chloro-5-fluoro-2-(2-methoxy-7-methylquinoxalin-5-yl)benzo[d]thiazol-6-yl)oxy)ethyl (2-chlorothiazol-4-yl)carbamate (383);

2-((4-chloro-5-fluoro-2-(2-methoxy-7-methylquinoxalin-5-yl)benzo[d]thiazol-6-yl)oxy)ethyl thiazol-5-ylcarbamate (384);

(R)-1-((4-chloro-5-fluoro-2-(2-methoxy-7-methylquinoxalin-5-yl)benzo[d]thiazol-6-yl)oxy)propan-2-yl (6-(hydroxymethyl)pyridin-3-yl)carbamate (385);

(2R,3S)-3-((5-fluoro-2-(2-methoxy-7-methylquinoxalin-5-yl)benzo [d]thiazol-6-yl)oxy)butan-2-yl (2-methylpyrimidin-5-yl)carbamate (386);

(2R,3S)-3-((5-fluoro-2-(2-methoxy-7-methylquinoxalin-5-yl)benzo[d]thiazol-6-yl)oxy)butan-2-yl (6-(2-hydroxyethyl)pyridin-3-yl)carbamate (387);

(2R,3S)-3-((5-fluoro-2-(2-methoxy-7-methylquinoxalin-5-yl)benzo[d]thiazol-6-yl)oxy)butan-2-yl (2-(2-hydroxyethoxy) pyridin-4-yl)carbamate (388);

(2R,3S)-3-((2-(2-ethoxy-7-methylquinoxalin-5-yl)-5-fluorobenzo[d]thiazol-6-yl)oxy)butan-2-yl (2-methylpyrimidin-5-yl)carbamate (389);

(2R,3S)-3-((5-fluoro-2-(7-methyl-2-(methylamino)quinoxalin-5-yl)benzo[d]triazol-6-yl)oxy)butan-2-yl (2-methylpyrimidin-5-yl)carbamate (390);

(2R,3S)-3-((5-fluoro-2-(2-methoxy-7-methylquinoxalin-5-yl)benzo[d]thiazol-6-yl)oxy)butan-2-yl (6-carbamoylpyridin-3-yl)carbamate (391);

(2R,3S)-3-((5-fluoro-2-(2-methoxy-7-methylquinoxalin-5-yl)benzo[d]thiazol-6-yl)oxy)butan-2-yl (6-((2-hydroxyethyl) carbamoyl)pyridin-3-yl)carbamate (392);

(2R,3S)-3-((5-fluoro-2-(7-methyl-2-(methylcarbamoyl)quinoxalin-5-yl)benzo[d]thiazol-6-yl)oxy)butan-2-yl (2-methylpyrimidin-5-yl)carbamate (393);

2-((4-chloro-5-fluoro-2-(2-methoxy-7-methylquinoxalin-5-yl)benzo[d]thiazol-6-yl)oxy)ethyl ((1-methyl-1H-imidazol-4-yl)methyl)carbamate (394);

2-((4-chloro-5-fluoro-2-(2-methoxy-7-methylquinoxalin-5-yl)benzo[d]thiazol-6-yl)oxy)ethyl (6-cyanopyridin-3-yl)carbamate (395);

2-((4-chloro-5-fluoro-2-(2-methoxy-7-methylquinoxalin-5-yl)benzo[d]thiazol-6-yl)oxy)ethyl (pyridin-2-ylmethyl) carbamate (396);

2-((4-chloro-5-fluoro-2-(2-methoxy-7-methylquinoxalin-5-yl)benzo[d]thiazol-6-yl)oxy)ethyl ((1-methyl-1H-imidazol-4-yl)methyl)carbamate (397);

2-((4-chloro-5-fluoro-2-(2-methoxy-7-methylquinoxalin-5-yl)benzo[d]thiazol-6-yl)oxy)ethyl ((1-methyl-1H-pyrazol-3-yl)methyl)carbamate (398);

2-((4-chloro-5-fluoro-2-(2-methoxy-7-methylquinoxalin-5-yl)benzo[d]thiazol-6-yl)oxy)ethyl ((1-methyl-1H-pyrazol-4-yl)methyl)carbamate (399);

(R)-1-((4-chloro-5-fluoro-2-(2-methoxy-7-methylquinoxalin-5-yl)benzo[d]thiazol-6-yl)oxy)propan-2-yl (2-cyanopyrimidin-5-yl)carbamate (400);

(R)-1-((4-chloro-5-fluoro-2-(2-methoxy-7-methylquinoxalin-5-yl)benzo[d]thiazol-6-yl)oxy)propan-2-yl (2-chloropyrimidin-5-yl)carbamate (401);

(R)-1-((4-chloro-5-fluoro-2-(2-methoxy-7-methylquinoxalin-5-yl)benzo[d]thiazol-6-yl)oxy)propan-2-yl (6-fluoro-5-methylpyridin-3-yl)carbamate (402);

(R)-1-((4-chloro-5-fluoro-2-(2-methoxy-7-methylquinoxalin-5-yl)benzo[d]thiazol-6-yl)oxy)propan-2-yl (6-bromopyridin-3-yl)carbamate (403);

(2R,3S)-3-((4-chloro-5-fluoro-2-(2-methoxy-7-methylquinoxalin-5-yl)benzo[d]thiazol-6-yl)oxy)butan-2-yl pyridin-3-ylcarbamate (404);

(2R,3S)-3-((5-fluoro-2-(2-methoxy-7-methylquinoxalin-5-yl)benzo[d]thiazol-6-yl)oxy)butan-2-yl (6-methylpyridin-3-yl)carbamate (405);

(2R,3S)-3-((5-fluoro-2-(2-methoxy-7-methylquinoxalin-5-yl)benzo[d]thiazol-6-yl)oxy)butan-2-yl (2-oxo-2,3-dihydrobenzo[d]oxazol-6-yl)carbamate (406);

(2R,3S)-3-((5-fluoro-2-(2-methoxy-7-methylquinoxalin-5-yl)benzo[d]thiazol-6-yl)oxy)butan-2-yl (2-methoxypyrimidin-5-yl)carbamate (407);

(R)-1-((5-fluoro-2-(2-methoxy-7-methylquinoxalin-5-yl)benzo[d]thiazol-6-yl)oxy)propan-2-yl (2-methoxypyrimidin-5-yl)carbamate (408);

(R)-1-((5-fluoro-2-(2-methoxy-7-methylquinoxalin-5-yl)benzo[d]thiazol-6-yl)oxy)propan-2-yl pyrimidin-5-ylcarbamate (409);

(2R,3S)-3-((5-fluoro-2-(2-methoxy-7-methylquinoxalin-5-yl)benzo[d]thiazol-6-yl)oxy)butan-2-yl pyrimidin-5-ylcarbamate (410);

(R)-1-((5-fluoro-2-(2-methoxy-7-methylquinoxalin-5-yl)benzo[d]thiazol-6-yl)oxy)propan-2-yl phenylcarbamate (411);

(2R,3S)-3-((5-fluoro-2-(2-methoxy-7-methylquinoxalin-5-yl)benzo[d]thiazol-6-yl)oxy)butan-2-yl (2-methoxypyridin-4-yl)carbamate (412);

(2R,3S)-3-((5-fluoro-2-(2-methoxy-7-methylquinoxalin-5-yl)benzo[d]thiazol-6-yl)oxy)butan-2-yl pyridazin-4-ylcarbamate (413);

(2R,3S)-3-((5-fluoro-2-(2-methoxy-7-methylquinoxalin-5-yl)benzo[d]thiazol-6-yl)oxy)butan-2-yl (2-propylpyrimidin-5-yl)carbamate (414);

(2R,3S)-3-((5-fluoro-2-(2-methoxy-7-methylquinoxalin-5-yl)benzo[d]thiazol-6-yl)oxy)butan-2-yl (2-(trifluoromethyl)pyrimidin-5-yl)carbamate (415);

(2R,3S)-3-((5-fluoro-2-(2-methoxy-7-methylquinoxalin-5-yl)benzo[d]thiazol-6-yl)oxy)butan-2-yl (6-methylpyridazin-3-yl)carbamate (416);

(2R,3S)-3-((5-fluoro-2-(2-methoxy-7-methylquinoxalin-5-yl)benzo[d]thiazol-6-yl)oxy)butan-2-yl (5-methylpyrazin-2-yl)carbamate (417);

(2R,3S)-3-((5-fluoro-2-(2-methoxy-7-methylquinoxalin-5-yl)benzo[d]thiazol-6-yl)oxy)butan-2-yl (6-methylpyridazin-4-yl)carbamate (418);

(2R,3S)-3-((5-fluoro-2-(2-methoxy-7-methylquinoxalin-5-yl)benzo[d]thiazol-6-yl)oxy)butan-2-yl (5-methylpyridin-3-yl)carbamate (419);

(2R,3S)-3-((5-fluoro-2-(2-methoxy-7-methylquinoxalin-5-yl)benzo[d]thiazol-6-yl)oxy)butan-2-yl (5-methoxypyridin-3-yl)carbamate (420);

(2R,3S)-3-((5-fluoro-2-(2-methoxy-7-methylquinoxalin-5-yl)benzo[d]thiazol-6-yl)oxy)butan-2-yl (5-cyanopyridin-3-yl)carbamate (421);

(2R,3S)-3-((5-fluoro-2-(2-methoxy-7-methylquinoxalin-5-yl)benzo[d]thiazol-6-yl)oxy)butan-2-yl (6-methoxy-5-methylpyridin-3-yl)carbamate (422);

(2R,3S)-3-((5-fluoro-2-(2-methoxy-7-methylquinoxalin-5-yl)benzo[d]thiazol-6-yl)oxy)butan-2-yl pyridin-3-ylcarbamate (423);

2-((5-fluoro-2-(2-methoxy-7-methylquinoxalin-5-yl)benzo[d]thiazol-6-yl)oxy)ethyl (2-methylpyrimidin-5-yl)carbamate (424);

(2R,3S)-3-((4-chloro-5-fluoro-2-(2-methoxy-7-methylquinoxalin-5-yl)benzo[d]thiazol-6-yl)oxy)butan-2-yl (2-methylpyrimidin-5-yl)carbamate (425);

(2R,3S)-3-((5-fluoro-2-(2-methoxy-7-methylquinoxalin-5-yl)benzo[d]thiazol-6-yl)oxy)butan-2-yl (6-(morpholine-4-carbonyl)pyridin-3-yl)carbamate (426);

(R)-1-((4-chloro-5-fluoro-2-(2-methoxy-7-methylquinoxalin-5-yl)benzo[d]thiazol-6-yl)oxy)propan-2-yl (2-carbamoylpyridin-4-yl)carbamate (427);

(R)-1-((4-chloro-5-fluoro-2-(2-methoxy-7-methylquinoxalin-5-yl)benzo[d]thiazol-6-yl)oxy)propan-2-yl (2-(methylcarbamoyl)pyridin-4-yl)carbamate (428);

(R)-1-((5-fluoro-2-(2-methoxy-7-methylquinoxalin-5-yl)benzo[d]thiazol-6-yl)oxy)propan-2-yl (2-carbamoylpyrimidin-5-yl)carbamate (429);

(R)-1-((5-fluoro-2-(2-methoxy-7-methylquinoxalin-5-yl)benzo[d]thiazol-6-yl)oxy)propan-2-yl (2-(methylcarbamoyl)pyrimidin-5-yl)carbamate (430);

(R)-1-((5-fluoro-2-(2-methoxy-7-methylquinoxalin-5-yl)benzo[d]thiazol-6-yl)oxy)propan-2-yl (2-(dimethylcarbamoyl)pyrimidin-5-yl)carbamate (431);

(R)-1-((5-fluoro-2-(2-methoxy-7-methylquinoxalin-5-yl)benzo[d]thiazol-6-yl)oxy)propan-2-yl (6-(methylcarbamoyl)pyridin-3-yl)carbamate (432);

(R)-1-((5-fluoro-2-(2-methoxy-7-methylquinoxalin-5-yl)benzo[d]thiazol-6-yl)oxy)propan-2-yl (6-carbamoylpyridin-3-yl)carbamate (433);

(R)-1-((5-fluoro-2-(2-methoxy-7-methylquinoxalin-5-yl)benzo[d]thiazol-6-yl)oxy)propan-2-yl (6-carbamoylpyridin-3-yl)carbamate (434);

(R)-1-((5-fluoro-2-(2-methoxy-7-methylquinoxalin-5-yl)benzo[d]thiazol-6-yl)oxy)propan-2-yl (6-(morpholine-4-carbonyl)pyridin-3-yl)carbamate (435);

(2R,3S)-3-((5-fluoro-2-(2-methoxy-7-methylquinoxalin-5-yl)benzo[d]thiazol-6-yl)oxy)butan-2-yl (6-(methylcarbamoyl)pyridin-3-yl)carbamate (436);

(2R,3S)-3-((5-fluoro-2-(2-methoxy-7-methylquinoxalin-5-yl)benzo[d]thiazol-6-yl)oxy)butan-2-yl (2-(morpholine-4-carbonyl)pyrimidin-5-yl)carbamate (437);

(2R,3S)-3-((5-fluoro-2-(2-methoxy-7-methylquinoxalin-5-yl)benzo[d]thiazol-6-yl)oxy)butan-2-yl (6-(dimethylcarbamoyl)pyridin-3-yl)carbamate (438);

(2R,3S)-3-((5-fluoro-2-(2-methoxy-7-methylquinoxalin-5-yl)benzo[d]thiazol-6-yl)oxy)butan-2-yl (6-(((R)-2-hydroxypropyl)carbamoyl)pyridin-3-yl)carbamate (439);

(2R,3S)-3-((5-fluoro-2-(2-methoxy-7-methylquinoxalin-5-yl)benzo[d]thiazol-6-yl)oxy)butan-2-yl (2-(methylcarbamoyl)pyrimidin-5-yl)carbamate (440);

(2R,3S)-3-((5-fluoro-2-(2-methoxy-7-methylquinoxalin-5-yl)benzo[d]thiazol-6-yl)oxy)butan-2-yl (6-(((S)-2-hydroxypropyl)carbamoyl)pyridin-3-yl)carbamate (441);

(R)-1-((5-fluoro-2-(2-methoxy-7-methylquinoxalin-5-yl)benzo[d]thiazol-6-yl)oxy)propan-2-yl (2-((2-hydroxyethyl)carbamoyl)pyridin-4-yl)carbamate (442);

(R)-1-((5-fluoro-2-(2-methoxy-7-methylquinoxalin-5-yl)benzo[d]thiazol-6-yl)oxy)propan-2-yl (2-(methylcarbamoyl)pyridin-4-yl)carbamate (443);

(R)-1-((5-fluoro-2-(2-methoxy-7-methylquinoxalin-5-yl)benzo[d]thiazol-6-yl)oxy)propan-2-yl (2-carbamoylpyridin-4-yl)carbamate (444);

(R)-1-((5-fluoro-2-(2-methoxy-7-methylquinoxalin-5-yl)benzo[d]thiazol-6-yl)oxy)propan-2-yl (6-((2-hydroxyethyl)carbamoyl)pyridin-3-yl)carbamate (445);

(2R,3S)-3-((5-fluoro-2-(2-methoxy-7-methylquinoxalin-5-yl)benzo[d]thiazol-6-yl)oxy)butan-2-yl (6-((3-hydroxy-3-methylbutyl)carbamoyl)pyridin-3-yl)carbamate (446);

(R)-1-((5-fluoro-2-(2-methoxy-7-methylquinoxalin-5-yl)benzo[d]thiazol-6-yl)oxy)propan-2-yl (2-(dimethylcarbamoyl)pyridin-4-yl)carbamate (447);

(R)-1-((5-fluoro-2-(2-methoxy-7-methylquinoxalin-5-yl)benzo[d]thiazol-6-yl)oxy)propan-2-yl (6-((2-hydroxy-2-methylpropyl)carbamoyl)pyridin-3-yl)carbamate (448);

(R)-1-((5-fluoro-2-(2-methoxy-7-methylquinoxalin-5-yl)benzo[d]thiazol-6-yl)oxy)propan-2-yl (6-(((R)-2-hydroxypropyl)carbamoyl)pyridin-3-yl)carbamate (449);

(R)-1-((5-fluoro-2-(2-methoxy-7-methylquinoxalin-5-yl)benzo[d]thiazol-6-yl)oxy)propan-2-yl (6-(((S)-2-hydroxypropyl)carbamoyl)pyridin-3-yl)carbamate (450);

(2R,3S)-3-((5-fluoro-2-(2-methoxy-7-methylquinoxalin-5-yl)benzo[d]thiazol-6-yl)oxy)butan-2-yl (2-((2-hydroxyethyl)carbamoyl)pyridin-4-yl)carbamate (451);

(2R,3S)-3-((5-fluoro-2-(2-methoxy-7-methylquinoxalin-5-yl)benzo[d]thiazol-6-yl)oxy)butan-2-yl (2-(((R)-2-hydroxypropyl)carbamoyl)pyridin-4-yl)carbamate (452);

(2R,3S)-3-((5-fluoro-2-(2-methoxy-7-methylquinoxalin-5-yl)benzo[d]thiazol-6-yl)oxy)butan-2-yl (2-carbamoylpyridin-4-yl)carbamate (453);

(2R,3S)-3-((5-fluoro-2-(2-methoxy-7-methylquinoxalin-5-yl)benzo[d]thiazol-6-yl)oxy)butan-2-yl (2-carbamoylpyrimidin-5-yl)carbamate (454);

(2R,3S)-3-((5-fluoro-2-(2-methoxy-7-methylquinoxalin-5-yl)benzo[d]thiazol-6-yl)oxy)butan-2-yl (2-((2-hydroxyethyl)carbamoyl)pyrimidin-5-yl)carbamate (455);

(2R,3S)-3-((5-fluoro-2-(2-methoxy-7-methylquinoxalin-5-yl)benzo[d]thiazol-6-yl)oxy)butan-2-yl (2-((2-hydroxyethyl)carbamoyl)pyrimidin-5-yl)carbamate (456);

(2R,3S)-3-((5-fluoro-2-(2-methoxy-7-methylquinoxalin-5-yl)benzo[d]thiazol-6-yl)oxy)butan-2-yl (2-((2-hydroxy-2-methylpropyl)carbamoyl)pyrimidin-5-yl)carbamate (457);

(2R,3S)-3-((5-fluoro-2-(2-methoxy-7-methylquinoxalin-5-yl)benzo[d]thiazol-6-yl)oxy)butan-2-yl (2-((3-hydroxy-3-methylbutyl)carbamoyl)pyrimidin-5-yl)carbamate (458);

(2R,3S)-3-((5-fluoro-2-(2-methoxy-7-methylquinoxalin-5-yl)benzo[d]thiazol-6-yl)oxy)butan-2-yl (2-((3-hydroxy-3-methylbutyl)carbamoyl)pyridin-4-yl)carbamate (459);

(2R,3S)-3-((5-fluoro-2-(2-methoxy-7-methylquinoxalin-5-yl)benzo[d]thiazol-6-yl)oxy)butan-2-yl (6-((2-hydroxy-2-methylpropyl)carbamoyl)pyridin-3-yl)carbamate (460);

(2R,3S)-3-((5-fluoro-2-(2-methoxy-7-methylquinoxalin-5-yl)benzo[d]thiazol-6-yl)oxy)butan-2-yl (2-(((S)-2-hydroxypropyl)carbamoyl)pyridin-4-yl)carbamate (461);

(2R,3S)-3-((5-fluoro-2-(2-methoxy-7-methylquinoxalin-5-yl)benzo[d]thiazol-6-yl)oxy)butan-2-yl (2-(((S)-2-hydroxypropyl)carbamoyl)pyrimidin-5-yl)carbamate (462);

(2R,3S)-3-((5-fluoro-2-(2-methoxy-7-methylquinoxalin-5-yl)benzo[d]thiazol-6-yl)oxy)butan-2-yl (2-(((1-hydroxycyclobutyl)methyl)carbamoyl)pyrimidin-5-yl)carbamate (463);

(2R,3S)-3-((5-fluoro-2-(2-methoxy-7-methylquinoxalin-5-yl)benzo[d]thiazol-6-yl)oxy)butan-2-yl (6-((3-hydroxy-3-methylbutyl)carbamoyl)pyridin-3-yl)carbamate (464);

(2R,3S)-3-((5-fluoro-2-(2-methoxy-7-methylquinoxalin-5-yl)benzo[d]thiazol-6-yl)oxy)butan-2-yl (2-((2-hydroxy-2-methylpropyl)carbamoyl)pyridin-4-yl)carbamate (465);

(2R,3S)-3-((5-fluoro-2-(2-methoxy-7-methylquinoxalin-5-yl)benzo[d]thiazol-6-yl)oxy)butan-2-yl (2-(methylcarbamoyl)pyridin-4-yl)carbamate (466);

(2R,3S)-3-((5-fluoro-2-(2-methoxy-7-methylquinoxalin-5-yl)benzo[d]thiazol-6-yl)oxy)butan-2-yl (2-(dimethylcarbamoyl)pyridin-4-yl)carbamate (467);

(2R,3S)-3-((5-fluoro-2-(2-methoxy-7-methylquinoxalin-5-yl)benzo[d]thiazol-6-yl)oxy)butan-2-yl (2-(dimethylcarbamoyl)pyrimidin-5-yl)carbamate (468);

(R)-1-((5-fluoro-2-(2-methoxy-7-methylquinoxalin-5-yl)benzo[d]thiazol-6-yl)oxy)propan-2-yl (2-((2-hydroxyethyl)carbamoyl)pyrimidin-5-yl)carbamate (469);

(R)-1-((5-fluoro-2-(2-methoxy-7-methylquinoxalin-5-yl)benzo[d]thiazol-6-yl)oxy)propan-2-yl (6-(((3-(hydroxymethyl)oxetan-3-yl)methyl)carbamoyl)pyridin-3-yl)carbamate (470);

(R)-1-((5-fluoro-2-(2-methoxy-7-methylquinoxalin-5-yl)benzo[d]thiazol-6-yl)oxy)propan-2-yl (6-((2-hydroxyethyl)(methyl)carbamoyl)pyridin-3-yl)carbamate (471);

(R)-1-((5-fluoro-2-(2-methoxy-7-methylquinoxalin-5-yl)benzo[d]thiazol-6-yl)oxy)propan-2-yl (6-((3-hydroxy-2,2-dimethylpropyl)carbamoyl)pyridin-3-yl)carbamate (472);

(R)-1-((5-fluoro-2-(2-methoxy-7-methylquinoxalin-5-yl)benzo[d]thiazol-6-yl)oxy)propan-2-yl (6-(((1-(hydroxymethyl)cyclobutyl)methyl)carbamoyl)pyridin-3-yl)carbamate (473);

(R)-1-((5-fluoro-2-(2-methoxy-7-methylquinoxalin-5-yl)benzo[d]thiazol-6-yl)oxy)propan-2-yl (6-((2-hydroxy-2-methylpropyl)(methyl)carbamoyl)pyridin-3-yl)carbamate (474);

R)-1-((5-fluoro-2-(2-methoxy-7-methylquinoxalin-5-yl)benzo[d]thiazol-6-yl)oxy)propan-2-yl (6-((R)-3-hydroxypyrrolidine-1-carbonyl)pyridin-3-yl)carbamate (475);

(R)-1-((5-fluoro-2-(2-methoxy-7-methylquinoxalin-5-yl)benzo[d]thiazol-6-yl)oxy)propan-2-yl (6-((R)-3-(hydroxymethyl)pyrrolidine-1-carbonyl)pyridin-3-yl)carbamate (476);

(R)-1-((5-fluoro-2-(2-methoxy-7-methylquinoxalin-5-yl)benzo[d]thiazol-6-yl)oxy)propan-2-yl (6-((S)-2-(hydroxymethyl)morpholine-4-carbonyl)pyridin-3-yl)carbamate (477);

(R)-1-((5-fluoro-2-(2-methoxy-7-methylquinoxalin-5-yl)benzo[d]thiazol-6-yl)oxy)propan-2-yl (6-((S)-3-hydroxypyrrolidine-1-carbonyl)pyridin-3-yl)carbamate (478);

(R)-1-((5-fluoro-2-(2-methoxy-7-methylquinoxalin-5-yl)benzo[d]thiazol-6-yl)oxy)propan-2-yl (6-((S)-3-(hydroxymethyl)pyrrolidine-1-carbonyl)pyridin-3-yl)carbamate (479);

(R)-1-((5-fluoro-2-(2-methoxy-7-methylquinoxalin-5-yl)benzo[d]thiazol-6-yl)oxy)propan-2-yl (6-((R)-2-(hydroxymethyl)morpholine-4-carbonyl)pyridin-3-yl)carbamate (480);

(2R,3S)-3-((5-fluoro-2-(2-methoxy-7-methylquinoxalin-5-yl)benzo[d]thiazol-6-yl)oxy)butan-2-yl (6-((S)-3-hydroxypiperidine-1-carbonyl)pyridin-3-yl)carbamate (481);

(2R,3S)-3-((5-fluoro-2-(2-methoxy-7-methylquinoxalin-5-yl)benzo[d]thiazol-6-yl)oxy)butan-2-yl (6-((S)-3-(hydroxymethyl)pyrrolidine-1-carbonyl)pyridin-3-yl)carbamate (482);

(2R,3S)-3-((5-fluoro-2-(2-methoxy-7-methylquinoxalin-5-yl)benzo[d]thiazol-6-yl)oxy)butan-2-yl (6-((R)-3-hydroxypiperidine-1-carbonyl)pyridin-3-yl)carbamate (483);

(R)-1-((5-fluoro-2-(2-methoxy-7-methylquinoxalin-5-yl)benzo[d]thiazol-6-yl)oxy)propan-2-yl (6-((S)-3-hydroxypiperidine-1-carbonyl)pyridin-3-yl)carbamate (484);

(R)-1-((5-fluoro-2-(2-methoxy-7-methylquinoxalin-5-yl)benzo[d]thiazol-6-yl)oxy)propan-2-yl (6-((R)-3-hydroxypiperidine-1-carbonyl)pyridin-3-yl)carbamate (485);

(2R,3S)-3-((2-(2,7-dimethylquinoxalin-5-yl)-5-fluorobenzo[d]thiazol-6-yl)oxy)butan-2-yl (6-((R)-3-(hydroxymethyl)morpholine-4-carbonyl)pyridin-3-yl)carbamate (486);

(2R,3S)-3-((5-fluoro-2-(2-methoxy-7-methylquinoxalin-5-yl)benzo[d]thiazol-6-yl)oxy)butan-2-yl (6-((S)-3-(hydroxymethyl)morpholine-4-carbonyl)pyridin-3-yl)carbamate (487);

(R)-1-((5-fluoro-2-(2-methoxy-7-methylquinoxalin-5-yl)benzo[d]thiazol-6-yl)oxy)propan-2-yl (6-((R)-3-(hydroxymethyl)morpholine-4-carbonyl)pyridin-3-yl)carbamate (488);

(R)-1-((5-fluoro-2-(2-methoxy-7-methylquinoxalin-5-yl)benzo[d]thiazol-6-yl)oxy)propan-2-yl (6-((S)-3-(hydroxymethyl)morpholine-4-carbonyl)pyridin-3-yl)carbamate (489);

(2R,3S)-3-((2-(2-(difluoromethoxy)-7-methylquinoxalin-5-yl)-5-fluorobenzo[d]thiazol-6-yl)oxy)butan-2-yl (2-methylpyrimidin-5-yl)carbamate (490);

(2R,3S)-3-((5-fluoro-2-(7-methyl-2-propoxyquinoxalin-5-yl)benzo[d]thiazol-6-yl)oxy)butan-2-yl (2-methylpyrimidin-5-yl)carbamate (491);

(2R,3S)-3-((5-fluoro-2-(2-isopropoxy-7-methylquinoxalin-5-yl)benzo[d]thiazol-6-yl)oxy) butan-2-yl (2-methylpyrimidin-5-yl)carbamate (492);

(2R,3S)-3-((5-fluoro-2-(2-(2-hydroxyethoxy)-7-methylquinoxalin-5-yl)benzo[d]thiazol-6-yl)oxy)butan-2-yl (2-methylpyrimidin-5-yl)carbamate (493);

(R)-1-((4-chloro-5-fluoro-2-(2-methoxy-7-methylquinoxalin-5-yl)benzo[d]thiazol-6-yl)oxy)propan-2-yl (2-(hydroxymethyl)pyridin-4-yl)carbamate (494);

(R)-1-((5-fluoro-2-(2-methoxy-7-methylquinoxalin-5-yl)benzo[d]thiazol-6-yl)oxy)propan-2-yl (2-(hydroxymethyl)pyridin-4-yl)carbamate (495);

(R)-1-((5-fluoro-2-(2-methoxy-7-methylquinoxalin-5-yl)benzo[d]thiazol-6-yl)oxy)propan-2-yl (2-(hydroxymethyl)pyrimidin-5-yl)carbamate (496);

(R)-1-((5-fluoro-2-(2-methoxy-7-methylquinoxalin-5-yl)benzo[d]thiazol-6-yl)oxy)propan-2-yl (2-(2-hydroxypropan-2-yl)pyrimidin-5-yl)carbamate (497);

(R)-1-((5-fluoro-2-(2-methoxy-7-methylquinoxalin-5-yl)benzo[d]thiazol-6-yl)oxy)propan-2-yl (6-(2-hydroxypropan-2-yl)pyridin-3-yl)carbamate (498);

(2R,3S)-3-((5-fluoro-2-(2-methoxy-7-methylquinoxalin-5-yl)benzo[d]thiazol-6-yl)oxy)butan-2-yl (6-(hydroxymethyl)pyridin-3-yl)carbamate (499);

(2R,3S)-3-((5-fluoro-2-(2-methoxy-7-methylquinoxalin-5-yl)benzo[d]thiazol-6-yl)oxy)butan-2-yl (6-(2-hydroxypropan-2-yl)pyridin-3-yl)carbamate (500);

(2R,3S)-3-((5-fluoro-2-(2-methoxy-7-methylquinoxalin-5-yl)benzo[d]thiazol-6-yl)oxy)butan-2-yl (2-(2-hydroxypropan-2-yl)pyrimidin-5-yl)carbamate (501);

(2R,3S)-3-((5-fluoro-2-(2-methoxy-7-methylquinoxalin-5-yl)benzo[d]thiazol-6-yl)oxy)butan-2-yl (2-(hydroxymethyl)pyrimidin-5-yl)carbamate (502);

4-chloro-2-(2-methoxy-7-methylquinoxalin-5-yl)benzo[d]thiazole (503);

2-(2-methoxy-7-methylquinoxalin-5-yl)benzo[d]thiazole (504);

2-(2-methoxy-7-methylquinoxalin-5-yl)-4-methylbenzo[d]thiazole (505);

4-chloro-6-methoxy-2-(2-methoxy-7-methylquinoxalin-5-yl)benzo[d]thiazole (506);

5-chloro-6-methoxy-2-(2-methoxy-7-methylquinoxalin-5-yl)benzo[d]thiazole (507);

6-methoxy-2-(2-methoxy-7-methylquinoxalin-5-yl)-4-methylbenzo[d]thiazole (509);

6-methoxy-2-(2-methoxy-7-methylquinoxalin-5-yl)-4-methylbenzo[d]thiazole (510);

(2R,3S)-3-((2-(6-chloro-3-methoxyquinolin-8-yl)-5-fluorobenzo[d]thiazol-6-yl)oxy)butan-2-yl (2-(2-hydroxyethoxy)pyrimidin-5-yl)carbamate (512);

(2R,3S)-3-((2-(6-chloro-3-ethoxyquinolin-8-yl)-5-fluorobenzo[d]thiazol-6-yl)oxy)butan-2-yl (2-(2-hydroxyethoxy)pyrimidin-5-yl)carbamate (513);

(2R,3S)-3-((5-fluoro-2-(3-methoxy-6-methylquinolin-8-yl)benzo[d]thiazol-6-yl)oxy)butan-2-yl (2-(2-hydroxyethoxy)pyrimidin-5-yl)carbamate (514);

(2R,3S)-3-((2-(6-chloro-3-(difluoromethoxy)quinolin-8-yl)-5-fluorobenzo[d]thiazol-6-yl) oxy)butan-2-yl (2-(2-hydroxyethoxy)pyrimidin-5-yl)carbamate (515);

1-((5-fluoro-2-(2-methoxy-7-methylquinoxalin-5-yl)benzo[d]thiazol-6-yl)oxy)-3-methoxypropan-2-yl pyridin-3-ylcarbamate (rac) (516);

(R)-1-((5-fluoro-2-(2-methoxy-7-methylquinoxalin-5-yl)benzo[d]thiazol-6-yl)oxy)butan-2-yl pyridin-3-ylcarbamate (517);

4-((4-chloro-5-fluoro-2-(2-methoxy-7-methylquinoxalin-5-yl)benzo[d]thiazol-6-yl)oxy)-N-(pyridin-3-yl)butanamide (518);

1-(2-((4-chloro-5-fluoro-2-(2-methoxy-7-methylquinoxalin-5-yl)benzo[d]thiazol-6-yl)oxy) ethyl)-3-(pyridin-3-yl)urea (519);

1-(2-((4-chloro-5-fluoro-2-(2-methoxy-7-methylquinoxalin-5-yl)benzo[d]thiazol-6-yl)oxy) ethyl)-1-methyl-3-(2-methylpyrimidin-5-yl)urea (520);

(2R,3S)-3-((5-fluoro-2-(2-methoxy-7-methylquinoxalin-5-yl)benzo[d]thiazol-6-yl)oxy) butan-2-yl (6-(morpholinomethyl)pyridin-3-yl)carbamate (521);

(2R,3S)-3-((2-(2-(dimethylamino)-7-methylquinoxalin-5-yl)-5-fluorobenzo[d]thiazol-6-yl) oxy)butan-2-yl (2-methylpyrimidin-5-yl)carbamate (522);

5-((((((2R,3S)-3-((5-fluoro-2-(2-methoxy-7-methylquinoxalin-5-yl)benzo[d]thiazol-6-yl)oxy)butan-2-yl)oxy)carbonyl)amino)picolinic acid, TFA (523);

(2R,3S)-3-((5-fluoro-2-(2-methoxy-7-methylquinoxalin-5-yl)benzo[d]thiazol-6-yl)oxy) butan-2-yl carbamate (524);

1-((5-fluoro-2-(2-methoxy-7-methylquinoxalin-5-yl)benzo[d]thiazol-6-yl)oxy)-3-isobutoxypropan-2-yl (2-methylpyrimidin-5-yl)carbamate (rac) (525);

(2R,3S)-3-((2-(2-ethoxy-7-methylquinoxalin-5-yl)-5-fluorobenzo[d]thiazol-6-yl)oxy)butan-2-yl (6-(2-hydroxyethyl)pyridin-3-yl)carbamate (526);

(2R,3S)-3-((2-(2-ethoxy-7-methylquinoxalin-5-yl)-5-fluorobenzo[d]thiazol-6-yl)oxy)butan-2-yl (6-((2-hydroxy-2-methylpropyl)carbamoyl)pyridin-3-yl)carbamate (527);

(2R,3S)-3-((5-fluoro-2-(2-methoxy-7-methylquinoxalin-5-yl)benzo[d]thiazol-6-yl)oxy)butan-2-yl (2-(hydroxymethyl)pyrimidin-5-yl)carbamate (528);

(2R,3S)-3-((2-(2-ethoxy-7-methylquinoxalin-5-yl)-5-fluorobenzo[d]thiazol-6-yl)oxy)butan-2-yl (2-(hydroxymethyl)pyrimidin-5-yl)carbamate (529);

(R)-1-((5-fluoro-2-(2-methoxy-7-methylquinoxalin-5-yl)benzo[d]thiazol-6-yl)oxy) propan-2-yl (6-((2-methyl-2-(phosphonooxy)propyl)carbamoyl)pyridin-3-yl)carbamate, TFA (530);

(2R,3S)-3-((2-(2-ethoxy-7-methylquinoxalin-5-yl)-5-fluorobenzo[d]thiazol-6-yl)oxy)butan-2-yl (6-(((S)-2-hydroxypropyl)carbamoyl)pyridin-3-yl)carbamate, TFA (531);

(2R,3S)-3-((2-(2-ethoxy-7-methylquinoxalin-5-yl)-5-fluorobenzo[d]thiazol-6-yl)oxy)butan-2-yl (2-((phosphonooxy)methyl)pyrimidin-5-yl)carbamate (532);

(2R,3S)-3-((5-fluoro-2-(2-methoxy-7-methylquinoxalin-5-yl)benzo[d]thiazol-6-yl)oxy)butan-2-yl (5-hydroxypyridin-3-yl)carbamate (533);

(2R,3S)-3-((5-fluoro-2-(2-methoxy-7-methylquinoxalin-5-yl)benzo[d]thiazol-6-yl)oxy) butan-2-yl (5-(2-hydroxyethoxy)pyridin-3-yl)carbamate (534);

(2R,3S)-3-((2-(2-ethoxy-7-methylquinoxalin-5-yl)-5-fluorobenzo[d]thiazol-6-yl)oxy)butan-2-yl (2-((S)-1-hydroxyethyl)pyrimidin-5-yl)carbamate (535);

(2R,3S)-3-((2-(2-ethoxy-7-methylquinoxalin-5-yl)-5-fluorobenzo[d]thiazol-6-yl)oxy) butan-2-yl (2-((R)-1-hydroxyethyl)pyrimidin-5-yl)carbamate (536);

2-((5-fluoro-2-(2-methoxy-7-methylquinoxalin-5-yl)benzo[d]thiazol-6-yl)oxy)ethyl (2-(2-hydroxyethyl)pyrimidin-5-yl)carbamate (537);

(2R,3S)-3-((4-chloro-5-fluoro-2-(2-methoxy-7-methylquinoxalin-5-yl)benzo[d]thiazol-6-yl)oxy)butan-2-yl (2-(2-hydroxyethyl)pyrimidin-5-yl)carbamate (538);

(2R,3S)-3-((2-(6-chloro-3-methoxyquinolin-8-yl)-5-fluorobenzo[d]thiazol-6-yl)oxy)butan-2-yl (2-(hydroxymethyl)pyrimidin-5-yl)carbamate (539);

(2R,3S)-3-((2-(6-chloro-3-methoxyquinolin-8-yl)-5-fluorobenzo[d]thiazol-6-yl)oxy)butan-2-yl (2-((R)-2-hydroxypropoxy)pyrimidin-5-yl)carbamate (540);

(2R,3S)-3-((2-(6-chloro-3-methoxyquinolin-8-yl)-5-fluorobenzo[d]thiazol-6-yl)oxy)butan-2-yl (2-((S)-2-hydroxypropoxy)pyrimidin-5-yl)carbamate (541);

(R)-1-((4-chloro-5-fluoro-2-(2-methoxy-7-methylquinoxalin-5-yl)benzo[d]thiazol-6-yl)oxy)propan-2-yl (6-(2-hydroxyethyl)pyridin-3-yl)carbamate (542);

(R)-1-((5-fluoro-2-(2-methoxy-7-methylquinoxalin-5-yl)benzo[d]thiazol-6-yl)oxy)propan-2-yl (6-(2-hydroxyethyl)pyridin-3-yl)carbamate (543);

(R)-1-((5-fluoro-2-(2-methoxy-7-methylquinoxalin-5-yl)benzo[d]thiazol-6-yl)oxy)propan-2-yl (5-(hydroxymethyl)-6-methylpyridin-3-yl)carbamate (544);

(R)-1-((5-fluoro-2-(2-methoxy-7-methylquinoxalin-5-yl)benzo[d]thiazol-6-yl)oxy)propan-2-yl (2-(2-hydroxyethyl)pyridin-4-yl)carbamate (545);

(R)-1-((5-fluoro-2-(2-methoxy-7-methylquinoxalin-5-yl)benzo[d]thiazol-6-yl)oxy)propan-2-yl (6-(hydroxymethyl)pyridin-3-yl)carbamate (546);

(2R,3S)-3-((5-fluoro-2-(2-methoxy-7-methylquinoxalin-5-yl)benzo[d]thiazol-6-yl)oxy)butan-2-yl (2-(2-hydroxyethyl)pyrimidin-4-yl)carbamate (547);

(2R,3S)-3-((5-fluoro-2-(2-methoxy-7-methylquinoxalin-5-yl)benzo[d]thiazol-6-yl)oxy)butan-2-yl (2-(((R)-1-hydroxypropan-2-yl)oxy)pyridin-4-yl)carbamate (549);

(2R,3S)-3-((5-fluoro-2-(2-methoxy-7-methylquinoxalin-5-yl)benzo[d]thiazol-6-yl)oxy)butan-2-yl (2-((R)-2-hydroxypropoxy)pyridin-4-yl)carbamate (550);

(R)-1-((5-fluoro-2-(2-methoxy-7-methylquinoxalin-5-yl)benzo[d]thiazol-6-yl)oxy)propan-2-yl (2-(2-hydroxyethoxy)pyridin-4-yl)carbamate (552);

(R)-1-((5-fluoro-2-(2-methoxy-7-methylquinoxalin-5-yl)benzo[d]thiazol-6-yl)oxy)propan-2-yl (2-(((R)-1-hydroxypropan-2-yl)oxy)pyrimidin-5-yl)carbamate (553);

(2R,3S)-3-((5-fluoro-2-(2-methoxy-7-methylquinoxalin-5-yl)benzo[d]thiazol-6-yl)oxy)butan-2-yl (2-(((R)-1-hydroxypropan-2-yl)oxy)pyrimidin-5-yl)carbamate (554);

(R)-1-((5-fluoro-2-(2-methoxy-7-methylquinoxalin-5-yl)benzo[d]thiazol-6-yl)oxy)propan-2-yl (2-(2-hydroxyethoxy)pyrimidin-5-yl)carbamate (555);

(2R,3S)-3-((5-fluoro-2-(2-methoxy-7-methylquinoxalin-5-yl)benzo[d]thiazol-6-yl)oxy)butan-2-yl (2-(2-hydroxyethoxy)pyrimidin-5-yl)carbamate (556);

(R)-1-((5-fluoro-2-(2-methoxy-7-methylquinoxalin-5-yl)benzo[d]thiazol-6-yl)oxy)propan-2-yl (6-(2-hydroxy-2-methylpropyl)pyridin-3-yl)carbamate (557);

(R)-1-((5-fluoro-2-(2-methoxy-7-methylquinoxalin-5-yl)benzo[d]thiazol-6-yl)oxy)propan-2-yl (2-(((S)-1-hydroxypropan-2-yl)oxy)pyrimidin-5-yl)carbamate (558);

(2R,3S)-3-((5-fluoro-2-(2-methoxy-7-methylquinoxalin-5-yl)benzo[d]thiazol-6-yl)oxy)butan-2-yl (6-(2-hydroxy-2-methylpropyl)pyridin-3-yl)carbamate (559);

(2R,3S)-3-((5-fluoro-2-(2-methoxy-7-methylquinoxalin-5-yl)benzo[d]thiazol-6-yl)oxy)butan-2-yl (2-(((S)-1-hydroxypropan-2-yl)oxy)pyrimidin-5-yl)carbamate (560);

(2R,3S)-3-((5-fluoro-2-(2-methoxy-7-methylquinoxalin-5-yl)benzo[d]thiazol-6-yl)oxy)butan-2-yl (2-(2-hydroxy-2-methylpropyl)pyridin-4-yl)carbamate (561);

(2R,3S)-3-((5-fluoro-2-(2-methoxy-7-methylquinoxalin-5-yl)benzo[d]thiazol-6-yl)oxy)butan-2-yl (2-(2-hydroxy-2-methylpropoxy)pyridin-4-yl)carbamate (562);

(2R,3S)-3-((5-fluoro-2-(2-methoxy-7-methylquinoxalin-5-yl)benzo[d]thiazol-6-yl)oxy)butan-2-yl (2-(3-hydroxy-3-methylbutoxy)pyridin-4-yl)carbamate (563);

(R)-1-((5-fluoro-2-(2-methoxy-7-methylquinoxalin-5-yl)benzo[d]thiazol-6-yl)oxy)propan-2-yl (2-(2-hydroxyethyl)pyrimidin-5-yl)carbamate (564);

(2R,3S)-3-((5-fluoro-2-(2-methoxy-7-methylquinoxalin-5-yl)benzo[d]thiazol-6-yl)oxy)butan-2-yl (2-(2-hydroxyethyl)pyrimidin-5-yl)carbamate (565);

(2R,3S)-3-((2-(2-ethoxy-7-methylquinoxalin-5-yl)-5-fluorobenzo[d]thiazol-6-yl)oxy)butan-2-yl (2-(2-hydroxyethyl)pyrimidin-5-yl)carbamate (566);

(R)-1-((5-fluoro-2-(2-methoxy-7-methylquinoxalin-5-yl)benzo[d]thiazol-6-yl)oxy)propan-2-yl (2-(3-hydroxy-3-methylbutoxy)pyridin-4-yl)carbamate (567);

(2R,3S)-3-((2-(2-ethoxy-7-methylquinoxalin-5-yl)-5-fluorobenzo[d]thiazol-6-yl)oxy)butan-2-yl (2-(2-hydroxyethoxy)pyrimidin-5-yl)carbamate (568);

(R)-1-((5-fluoro-2-(2-methoxy-7-methylquinoxalin-5-yl)benzo[d]thiazol-6-yl)oxy)propan-2-yl (2-(3-hydroxy-3-methylbutoxy)pyrimidin-5-yl)carbamate (569);

(2R,3S)-3-((5-fluoro-2-(2-methoxy-7-methylquinoxalin-5-yl)benzo[d]thiazol-6-yl)oxy)butan-2-yl (2-(3-hydroxy-3-methylbutoxy)pyrimidin-5-yl)carbamate (570);

(2R,3S)-3-((5-fluoro-2-(2-methoxy-7-methylquinoxalin-5-yl)benzo[d]thiazol-6-yl)oxy)butan-2-yl (6-(2-hydroxyethoxy)pyridin-3-yl)carbamate (571);

(R)-1-((5-fluoro-2-(2-methoxy-7-methylquinoxalin-5-yl)benzo[d]thiazol-6-yl)oxy)propan-2-yl (6-(2-hydroxyethoxy)pyridin-3-yl)carbamate (572);

(2R,3S)-3-((5-fluoro-2-(2-methoxy-7-methylquinoxalin-5-yl)benzo[d]thiazol-6-yl)oxy)butan-2-yl (6-(2,2-difluoro-3-hydroxypropoxy)pyridin-3-yl)carbamate (573);

(R)-1-((5-fluoro-2-(2-methoxy-7-methylquinoxalin-5-yl)benzo[d]thiazol-6-yl)oxy)propan-2-yl (6-(2,2-difluoro-3-hydroxypropoxy)pyridin-3-yl)carbamate (574);

(2R,3S)-3-((5-fluoro-2-(2-methoxy-7-methylquinoxalin-5-yl)benzo[d]thiazol-6-yl)oxy)butan-2-yl (2-(2-hydroxy-2-methylpropoxy)pyrimidin-5-yl)carbamate (575);

(R)-1-((5-fluoro-2-(2-methoxy-7-methylquinoxalin-5-yl)benzo[d]thiazol-6-yl)oxy)propan-2-yl (2-(2-hydroxy-2-methylpropoxy)pyrimidin-5-yl)carbamate (576);

(2R,3S)-3-((5-fluoro-2-(2-methoxy-7-methylquinoxalin-5-yl)benzo[d]thiazol-6-yl)oxy)butan-2-yl (2-(2-hydroxy-2-methylpropyl)pyrimidin-5-yl)carbamate (577);

(2R,3S)-3-((5-fluoro-2-(2-methoxy-7-methylquinoxalin-5-yl)benzo[d]thiazol-6-yl)oxy)butan-2-yl (2-((R)-2-hydroxypropoxy)pyrimidin-5-yl)carbamate (578);

(2R,3S)-3-((2-(6-chloro-3-methoxyquinolin-8-yl)-5-fluorobenzo[d]thiazol-6-yl)oxy)butan-2-yl (2-(2-hydroxyethyl)pyrimidin-5-yl)carbamate (579);

(2R,3S)-3-((2-(2-ethoxy-7-methylquinoxalin-5-yl)-5-fluorobenzo[d]thiazol-6-yl)oxy)butan-2-yl (2-((R)-2-hydroxypropoxy)pyrimidin-5-yl)carbamate (580);

(2R,3S)-3-((5-fluoro-2-(2-methoxy-7-methylquinoxalin-5-yl)benzo[d]thiazol-6-yl)oxy)butan-2-yl (2-((S)-2-hydroxypropoxy)pyrimidin-5-yl)carbamate (581);

(2R,3S)-3-((2-(2-ethoxy-7-methylquinoxalin-5-yl)-5-fluorobenzo[d]thiazol-6-yl)oxy)butan-2-yl (2-((S)-2-hydroxypropoxy)pyrimidin-5-yl)carbamate (582);

(2R,3S)-3-((2-(2-ethoxy-7-methylquinoxalin-5-yl)-5-fluorobenzo[d]thiazol-6-yl)oxy)butan-2-yl (2-((R)-2,3-dihydroxypropoxy)pyrimidin-5-yl)carbamate (583);

(2S,3S)-3-((5-fluoro-2-(2-methoxy-7-methylquinoxalin-5-yl)benzo[d]thiazol-6-yl)oxy)butan-2-yl (2-(2-hydroxyethyl)pyrimidin-5-yl)carbamate (584);

(2R,3S)-3-((5-fluoro-2-(2-methoxy-7-methylquinoxalin-5-yl)benzo[d]thiazol-6-yl)oxy)butan-2-yl (2-((S)-2,3-dihydroxypropoxy)pyrimidin-5-yl)carbamate (585);

(R)-1-((4-chloro-5-fluoro-2-(2-methoxy-7-methylquinoxalin-5-yl)benzo[d]thiazol-6-yl)oxy)propan-2-yl (2-(2-hydroxyethyl)pyrimidin-5-yl)carbamate (586);

(2R,3S)-3-((5-fluoro-2-(2-methoxy-7-methylquinoxalin-5-yl)benzo[d]thiazol-6-yl)oxy)butan-2-yl (2-((R)-2,3-dihydroxypropoxy)pyrimidin-5-yl)carbamate (587);

(2R,3S)-3-((2-(2-ethoxy-7-methylquinoxalin-5-yl)-5-fluorobenzo[d]thiazol-6-yl)oxy)butan-2-yl (2-((S)-2,3-dihydroxypropoxy)pyrimidin-5-yl)carbamate (588);

(R)-1-((4-chloro-5-fluoro-2-(2-methoxy-7-methylquinoxalin-5-yl)benzo[d]thiazol-6-yl)oxy)propan-2-yl (2-methylpyrimidin-5-yl)carbamate (589);

(R)-1-((4-chloro-5-fluoro-2-(2-methoxy-7-methylquinoxalin-5-yl)benzo[d]thiazol-6-yl)oxy)propan-2-yl (2-methylpyridin-3-yl)carbamate (590);

(R)-1-((4-chloro-5-fluoro-2-(2-methoxy-7-methylquinoxalin-5-yl)benzo[d]thiazol-6-yl)oxy)propan-2-yl pyrimidin-5-ylcarbamate (591);

(R)-1-((5-fluoro-2-(2-methoxy-7-methylquinoxalin-5-yl)benzo[d]thiazol-6-yl)oxy)propan-2-yl (6-methylpyridin-3-yl)carbamate (592); methyl 3-(5-(((((2R,3S)-3-((2-(2-ethoxy-7-methylquinoxalin-5-yl)-5-fluorobenzo[d]thiazol-6-yl) oxy)butan-2-yl)oxy)carbonyl)amino)pyrimidin-2-yl)propanoate (593);

(2S,3S)-3-((5-fluoro-2-(2-methoxy-7-methylquinoxalin-5-yl)benzo[d]triazol-6-yl)oxy)butan-2-yl pyridin-3-ylcarbamate (594);

(2S,3S)-3-((5-fluoro-2-(2-methoxy-7-methylquinoxalin-5-yl)benzo[d]triazol-6-yl)oxy)butan-2-yl (2-methylpyrimidin-5-yl)carbamate (595); (R)-(5-aminopyridin-2-yl)methyl (1-((4-chloro-5-fluoro-2-(2-methoxy-7-methylquinoxalin-5-yl)benzo[d]thiazol-6-yl)oxy)propan-2-yl) carbonate (596);

(R)-1-((5-fluoro-2-(2-methoxy-7-methylquinoxalin-5-yl)benzo[d]thiazol-6-yl)oxy)propan-2-yl (2-(dimethylamino)pyrimidin-5-yl)carbamate (597);

(2R,3S)-3-((5-fluoro-2-(2-methoxy-7-methylquinoxalin-5-yl)benzo[d]thiazol-6-yl)oxy)butan-2-yl (2-(dimethylamino)pyrimidin-5-yl)carbamate (598);

(2R,3S)-3-((5-fluoro-2-(2-methoxy-7-methylquinoxalin-5-yl)benzo[d]thiazol-6-yl)oxy)butan-2-yl (6-(dimethylamino)pyridin-3-yl)carbamate (599);

(2R,3S)-3-((5-fluoro-2-(2-methoxy-7-methylquinoxalin-5-yl)benzo[d]thiazol-6-yl)oxy)butan-2-yl (6-(2-oxooxazolidin-3-yl)pyridin-3-yl)carbamate (600);

(2R,3S)-3-((5-fluoro-2-(2-methoxy-7-methylquinoxalin-5-yl)benzo[d]thiazol-6-yl)oxy)butan-2-yl (6-acetamidopyridin-3-yl)carbamate (601);

(2R,3S)-3-((5-fluoro-2-(2-methoxy-7-methylquinoxalin-5-yl)benzo[d]thiazol-6-yl)oxy)butan-2-yl (6-aminopyridin-3-yl)carbamate (602);

(2R,3S)-3-((5-fluoro-2-(2-methoxy-7-methylquinoxalin-5-yl)benzo[d]thiazol-6-yl)oxy)butan-2-yl (6-morpholinopyridin-3-yl)carbamate (603);

(2R,3S)-3-((5-fluoro-2-(2-methoxy-7-methylquinoxalin-5-yl)benzo[d]thiazol-6-yl)oxy)butan-2-yl (2-(3-chloro-4-fluorobenzamido)pyrimidin-5-yl)carbamate (604);

(2R,3S)-3-((5-fluoro-2-(2-methoxy-7-methylquinoxalin-5-yl)benzo[d]thiazol-6-yl)oxy)butan-2-yl (6-(pyrrolidin-1-yl)pyridin-3-yl)carbamate (605);

(2R,3S)-3-((5-fluoro-2-(2-methoxy-7-methylquinoxalin-5-yl)benzo[d]thiazol-6-yl)oxy)butan-2-yl (2-((2-hydroxy-2-methylpropyl)amino)pyrimidin-5-yl)carbamate (606);

(2R,3S)-3-((5-fluoro-2-(2-methoxy-7-methylquinoxalin-5-yl)benzo[d]thiazol-6-yl)oxy)butan-2-yl (2-(N-methylmethylsulfonamido)pyrimidin-5-yl)carbamate (607);

(2R,3S)-3-((5-fluoro-2-(2-methoxy-7-methylquinoxalin-5-yl)benzo[d]thiazol-6-yl)oxy)butan-2-yl (2-morpholinopyrimidin-5-yl)carbamate (608);

(R)-1-((5-fluoro-2-(2-methoxy-7-methylquinoxalin-5-yl)benzo[d]thiazol-6-yl)oxy)propan-2-yl (6-(2-oxooxazolidin-3-yl)pyridin-3-yl)carbamate (609);

(R)-1-((5-fluoro-2-(2-methoxy-7-methylquinoxalin-5-yl)benzo[d]thiazol-6-yl)oxy)propan-2-yl (6-acetamidopyridin-3-yl)carbamate (610);

(R)-1-((5-fluoro-2-(2-methoxy-7-methylquinoxalin-5-yl)benzo[d]thiazol-6-yl)oxy)propan-2-yl (5-(hydroxymethyl)pyridin-3-yl)carbamate (611);

(2S,3S)-3-((5-fluoro-2-(2-methoxy-7-methylquinoxalin-5-yl)benzo[d]thiazol-6-yl)oxy)butan-2-ol (612);

(2R,3S)-3-((2-(2-carbamoyl-7-methylquinoxalin-5-yl)-5-fluorobenzo[d]thiazol-6-yl)oxy) butan-2-yl (2-methylpyrimidin-5-yl)carbamate (613);

(2R,3S)-3-((5-fluoro-2-(7-methyl-2-(methylcarbamoyl)quinoxalin-5-yl)benzo[d]thiazol-6-yl)oxy)butan-2-yl (2-methylpyrimidin-5-yl)carbamate (614);

(2R,3S)-3-((2-(2-(dimethylcarbamoyl)-7-methylquinoxalin-5-yl)-5-fluorobenzo[d]thiazol-6-yl)oxy)butan-2-yl (2-methylpyrimidin-5-yl)carbamate (615);

(2R,3S)-3-((5-fluoro-2-(2-((2-hydroxyethyl)carbamoyl)-7-methylquinoxalin-5-yl)benzo[d]thiazol-6-yl)oxy)butan-2-yl (2-methylpyrimidin-5-yl)carbamate (616);

(2R,3S)-3-((5-fluoro-2-(2-methoxy-7-methylquinoxalin-5-yl)benzo[d]thiazol-6-yl)oxy)butan-2-yl (5-(hydroxymethyl)pyridin-3-yl)carbamate (617);

(2R,3S)-3-((5-fluoro-2-(2-methoxy-7-methylquinoxalin-5-yl)benzo[d]thiazol-6-yl)oxy)butan-2-yl (6-(2-hydroxypropan-2-yl)pyridin-3-yl)carbamate (618);

(2R,3S)-3-((5-fluoro-2-(2-methoxy-7-methylquinoxalin-5-yl)benzo[d]thiazol-6-yl)oxy)butan-2-yl (2-(hydroxymethyl)pyridin-4-yl)carbamate (619);

(2R,3S)-3-((5-fluoro-2-(2-methoxy-7-methylquinoxalin-5-yl)benzo[d]thiazol-6-yl)oxy)butan-2-yl (2-(1-hydroxyethyl)pyrimidin-5-yl)carbamate (620);

2-((4-chloro-5-fluoro-2-(2-methoxy-7-methylquinoxalin-5-yl)benzo[d]thiazol-6-yl)oxy)ethylisothiazol-5-ylcarbamate (621);

(R)-5-(((4-chloro-5-fluoro-2-(2-methoxy-7-methylquinoxalin-5-yl)benzo[d]thiazol-6-yl)oxy)methyl)oxazolidin-2-one (622);

4-(((4-chloro-5-fluoro-2-(2-methoxy-7-methylquinoxalin-5-yl)benzo[d]thiazol-6-yl)oxy) methyl)oxazol-2-amine (623);

(2R,3S)-3-((2-(2-ethoxy-7-methylquinoxalin-5-yl)-5-fluorobenzo[d]thiazol-6-yl)oxy)butan-2-yl (2-(2-(phosphonooxy)ethyl)pyrimidin-5-yl)carbamate (624);
2-(6-chloro-3-(methoxymethyl)quinolin-8-yl)-6-methoxy-4-methylbenzo[d]thiazole (625); 2-(6-chloro-3-methoxyquinolin-8-yl)-6-methoxy-4-methylbenzo[d]thiazole (626);
2-(6-methoxy-2-(2-methoxy-7-methylquinoxalin-5-yl)benzo[d]thiazol-4-yl)propan-2-ol (627);
1-(6-methoxy-2-(2-(methoxymethyl)-7-methylquinoxalin-5-yl)benzo[d]thiazol-4-yl)-2,2-dimethylpropan-1-ol (628);
(6-methoxy-2-(2-methoxy-7-methylquinoxalin-5-yl)benzo[d]thiazol-4-yl) (phenyl)methanol (629);
1-(6-methoxy-2-(2-methoxy-7-methylquinoxalin-5-yl)benzo[d]thiazol-4-yl)-2,2-dimethylpropan-1-ol (630);
1-(6-methoxy-2-(2-methoxy-7-methylquinoxalin-5-yl)benzo[d]thiazol-4-yl)-2-phenylethanol (631);
1-(5-fluoro-6-methoxy-2-(2-methoxy-7-methylquinoxalin-5-yl)benzo[d]thiazol-4-yl)-2,2-dimethylpropan-1-ol (632);
2,2,2-trifluoro-1-(6-methoxy-2-(2-methoxy-7-methylquinoxalin-5-yl)benzo[d]thiazol-4-yl) ethanol (633);
4-(1-fluoro-2,2-dimethylpropyl)-6-methoxy-2-(2-methoxy-7-methylquinoxalin-5-yl)benzo[d]thiazole (634);
4-(benzyloxy)-6-methoxy-2-(2-(methoxymethyl)-7-methylquinoxalin-5-yl)benzo[d]thiazole (635);
1-(2-(7-chloro-2-methoxyquinoxalin-5-yl)-6-methoxybenzo[d]thiazol-4-yl)-2,2-dimethylpropan-1-ol (636);
1-(6-methoxy-2-(2-methoxy-7-methylquinoxalin-5-yl)benzo[d]thiazol-4-yl)-2,2-dimethyl propan-1-ol (637);
2-((4-(1-hydroxy-2,2-dimethylpropyl)-2-(2-methoxy-7-methylquinoxalin-5-yl)benzo[d]thiazol-6-yl)oxy)ethyl (5-cyanopyridin-3-yl)carbamate (638);
8-(4-(1-hydroxy-2,2-dimethylpropyl)-6-methoxybenzo[d]thiazol-2-yl)-3-methoxyquinoxaline-6-carbonitrile (639);
1-(6-ethoxy-2-(2-methoxy-7-methylquinoxalin-5-yl)benzo[d]thiazol-4-yl)-2,2-dimethylpropan-1-ol (640);
2-(6-methoxy-2-(2-methoxy-7-methylquinoxalin-5-yl)benzo[d]thiazol-4-yl)ethanol (641);
(6-methoxy-2-(2-methoxy-7-methylquinoxalin-5-yl)benzo[d]thiazol-4-yl)(3-(trifluoromethyl)phenyl)methanol (642);
(2-isopropylphenyl)(6-methoxy-2-(2-methoxy-7-methylquinoxalin-5-yl)benzo[d]thiazol-4-yl)methanol (643); ethyl
1-(hydroxy(6-methoxy-2-(2-methoxy-7-methylquinoxalin-5-yl)benzo[d]thiazol-4-yl)methyl)cyclobutanecarboxylate (644);
(2R,3S)-3-((2-(6-chloro-3-methoxyquinolin-8-yl)-5-fluorobenzo[d]thiazol-6-yl)oxy)butan-2-yl (2-methylpyrimidin-5-yl)carbamate (645);
(1-(hydroxymethyl)cyclobutyl)(6-methoxy-2-(2-methoxy-7-methylquinoxalin-5-yl) benzo[d]thiazol-4-yl)methanol (646);
(2R,3S)-3-((2-(6-chloro-3-ethylquinolin-8-yl)-5-fluorobenzo[d]thiazol-6-yl)oxy)butan-2-yl (2-methylpyrimidin-5-yl)carbamate (647);
(2R,3S)-3-((5-fluoro-2-(3-methoxy-6-methylquinolin-8-yl)benzo[d]thiazol-6-yl)oxy)butan-2-yl (2-methylpyrimidin-5-yl)carbamate (648);
(2R,3S)-3-((2-(6-chloro-3-ethoxyquinolin-8-yl)-5-fluorobenzo[d]thiazol-6-yl)oxy)butan-2-yl (2-methylpyrimidin-5-yl)carbamate (649);
(2R,3S)-3-((2-(6-chloro-3-(difluoromethoxy)quinolin-8-yl)-5-fluorobenzo[d]thiazol-6-yl) oxy)butan-2-yl (2-methylpyrimidin-5-yl)carbamate (650);
(2R,3S)-3-((2-(6-chloro-3-(2,2-difluoroethoxy)quinolin-8-yl)-5-fluorobenzo[d]thiazol-6-yl)oxy)butan-2-yl (2-methylpyrimidin-5-yl)carbamate (651);
(2R,3S)-3-((2-(6-chloro-3-(methylamino)quinolin-8-yl)-5-fluorobenzo[d]triazol-6-yl)oxy) butan-2-yl (2-methylpyrimidin-5-yl)carbamate (652);
(2R,3S)-3-((2-(6-(difluoromethyl)-3-methoxyquinolin-8-yl)-5-fluorobenzo[d]thiazol-6-yl) oxy)butan-2-yl (2-methylpyrimidin-5-yl)carbamate (653);
(2R,3S)-3-((5-fluoro-2-(6-(fluoromethyl)-3-methoxyquinolin-8-yl)benzo[d]thiazol-6-yl) oxy)butan-2-yl (2-methylpyrimidin-5-yl)carbamate (654);
(2R,3S)-3-((2-(6-cyano-3-methoxyquinolin-8-yl)-5-fluorobenzo[d]thiazol-6-yl)oxy)butan-2-yl (2-methylpyrimidin-5-yl)carbamate (655);
(2-(6-chloro-3-methoxyquinolin-8-yl)-6-methoxybenzo[d]thiazol-4-yl)(1-(trifluoromethyl) cyclobutyl)methanol (656);
(2R,3S)-3-((2-(3,6-dimethoxyquinolin-8-yl)-5-fluorobenzo[d]thiazol-6-yl)oxy)butan-2-yl (2-methylpyrimidin-5-yl)carbamate (657);
2-((4-(1-hydroxy-2,2-dimethylpropyl)-2-(2-methoxy-7-methylquinoxalin-5-yl)benzo[d]thiazol-6-yl)oxy)ethyl pyridin-4-ylcarbamate (658);
(2R,3S)-3-((2-(3-(difluoromethoxy)-6-methylquinolin-8-yl)-5-fluorobenzo[d]thiazol-6-yl) oxy)butan-2-yl (2-methylpyrimidin-5-yl)carbamate (659);
(2R,3S)-3-((2-(3-ethoxy-6-methylquinolin-8-yl)-5-fluorobenzo[d]thiazol-6-yl)oxy)butan-2-yl (2-methylpyrimidin-5-yl)carbamate (660);
5-(benzofuran-2-yl)-2-ethoxy-7-methylquinoxaline (661);
4-methoxyphenyl (2-((2-(2-methoxy-7-methylquinoxalin-5-yl)-7-methylthiazolo[5,4-b] pyridin-5-yl)oxy)ethyl) carbamate (662);
(6-methoxy-2-(2-methoxy-7-methylquinoxalin-5-yl)benzo[d]thiazol-4-yl)(tetrahydro-2H-pyran-4-yl)methanol (663);
(6-methoxy-2-(2-methoxy-7-methylquinoxalin-5-yl)benzo[d]thiazol-4-yl)(tetrahydro-2H-pyran-4-yl)methanol (664);
(6-methoxy-2-(2-methoxy-7-methylquinoxalin-5-yl)benzo[d]thiazol-4-yl)(1-phenylcyclobutyl)methanol (665);
(6-methoxy-2-(2-methoxy-7-methylquinoxalin-5-yl)benzo[d]thiazol-4-yl)(1-methoxycyclobutyl)methanol (666);
(6-methoxy-2-(2-methoxy-7-methylquinoxalin-5-yl)benzo[d]thiazol-4-yl)(1-(trifluoromethyl)cyclopropyl)methanol (667);
(6-methoxy-2-(2-methoxy-7-methylquinoxalin-5-yl)benzo[d]thiazol-4-yl)(1-phenylcyclopropyl)methanol (668);
(6-methoxy-2-(2-methoxy-7-methylquinoxalin-5-yl)benzo[d]thiazol-4-yl)(1-(trifluoromethyl)cyclobutyl)methanol (669);
(6-methoxy-2-(2-methoxy-7-methylquinoxalin-5-yl)benzo[d]thiazol-4-yl)(1-methylcyclopropyl)methanol (671);
(6-methoxy-2-(2-methoxy-7-methylquinoxalin-5-yl)benzo[d]thiazol-4-yl)(1-methylcyclohexyl)methanol (672);
(6-methoxy-2-(2-methoxy-7-methylquinoxalin-5-yl)benzo[d]thiazol-4-yl)(thiazol-2-yl)methanol (673);
(6-methoxy-2-(2-methoxy-7-methylquinoxalin-5-yl)benzo[d]thiazol-4-yl)(4-methyltetrahydro-2H-pyran-4-yl) methanol (674);
(3-fluoro-5-methoxyphenyl)(6-methoxy-2-(2-methoxy-7-methylquinoxalin-5-yl)benzo[d] thiazol-4-yl)methanol (675);
(6-methoxy-2-(2-methoxy-7-methylquinoxalin-5-yl)benzo[d]thiazol-4-yl)(1-methylcyclohexyl)methanol (676);

1-(6-methoxy-2-(2-methoxy-7-methylquinoxalin-5-yl) benzo[d]thiazol-4-yl)ethan-1-ol (677);

(R)-1-((6-fluoro-2-(2-methoxy-7-methylquinoxalin-5-yl) thiazolo[5,4-b]pyridin-5-yl)oxy) propan-2-yl (2-methylpyrimidin-5-yl)carbamate (678);

(R)-1-((6-fluoro-2-(2-methoxy-7-methylquinoxalin-5-yl) thiazolo[5,4-b]pyridin-5-yl)oxy) propan-2-yl (2-methoxypyrimidin-5-yl)carbamate (679);

(R)-1-((6-fluoro-2-(2-methoxy-7-methylquinoxalin-5-yl) thiazolo[5,4-b]pyridin-5-yl)oxy) propan-2-yl pyridin-4-ylcarbamate (680);

(R)-1-((6-fluoro-2-(2-methoxy-7-methylquinoxalin-5-yl) thiazolo[5,4-b]pyridin-5-yl)oxy) propan-2-yl (6-methylpyridin-3-yl)carbamate (681);

(R)-1-((6-fluoro-2-(2-methoxy-7-methylquinoxalin-5-yl) thiazolo[5,4-b]pyridin-5-yl)oxy) propan-2-yl (5-fluoropyridin-3-yl)carbamate (682);

(R)-1-((6-fluoro-2-(2-methoxy-7-methylquinoxalin-5-yl) thiazolo[5,4-b]pyridin-5-yl)oxy) propan-2-yl (2-oxo-2,3-dihydrobenzo[d]oxazol-6-yl)carbamate (683);

(R)-1-((6-fluoro-2-(2-methoxy-7-methylquinoxalin-5-yl) thiazolo[5,4-b]pyridin-5-yl)oxy) propan-2-yl pyridin-3-ylcarbamate (684);

(R)-1-((6-fluoro-2-(2-methoxy-7-methylquinoxalin-5-yl) thiazolo[5,4-b]pyridin-5-yl)oxy) propan-2-yl (2-(2-hydroxyethoxy)pyrimidin-5-yl)carbamate (685);

(R)-1-((6-fluoro-2-(2-methoxy-7-methylquinoxalin-5-yl) thiazolo[5,4-b]pyridin-5-yl)oxy) propan-2-yl (2-(3-hydroxypropyl)pyrimidin-5-yl)carbamate (686);

(R)-1-((6-fluoro-2-(2-methoxy-7-methylquinoxalin-5-yl) thiazolo[5,4-b]pyridin-5-yl)oxy) propan-2-yl (6-(2,2-difluoro-3-hydroxypropoxy)pyridin-3-yl)carbamate (687);

(R)-1-((6-fluoro-2-(2-methoxy-7-methylquinoxalin-5-yl) thiazolo[5,4-b]pyridin-5-yl)oxy) propan-2-yl (2-((R)-2-hydroxypropoxy)pyrimidin-5-yl)carbamate (688); methyl (R)-5-((((1-((6-fluoro-2-(2-methoxy-7-methylquinoxalin-5-yl)thiazolo[5,4-b]pyridin-5-yl) oxy)propan-2-yl)oxy)carbonyl)amino)pyrimidine-2-carboxylate (689); methyl (R)-5-((((1-((6-fluoro-2-(2-methoxy-7-methylquinoxalin-5-yl)thiazolo[5,4-b]pyridin-5-yl) oxy)propan-2-yl)oxy)carbonyl)amino)picolinate (690);

(R)-1-((6-fluoro-2-(2-methoxy-7-methylquinoxalin-5-yl) thiazolo[5,4-b]pyridin-5-yl)oxy) propan-2-yl (6-(2-hydroxyethyl)pyridin-3-yl)carbamate (691);

(R)-1-((6-fluoro-2-(2-methoxy-7-methylquinoxalin-5-yl) thiazolo[5,4-b]pyridin-5-yl)oxy) propan-2-yl (2-(((R)-1-hydroxypropan-2-yl)oxy)pyrimidin-5-yl)carbamate (692);

(R)-1-((6-fluoro-2-(2-methoxy-7-methylquinoxalin-5-yl) thiazolo[5,4-b]pyridin-5-yl)oxy) propan-2-yl (2-(((S)-1-hydroxypropan-2-yl)oxy)pyrimidin-5-yl)carbamate (693);

(R)-1-((6-fluoro-2-(2-methoxy-7-methylquinoxalin-5-yl) thiazolo[5,4-b]pyridin-5-yl)oxy) propan-2-yl (6-(hydroxymethyl)pyridin-3-yl)carbamate (694);

(R)-1-((6-fluoro-2-(2-methoxy-7-methylquinoxalin-5-yl) thiazolo[5,4-b]pyridin-5-yl)oxy) propan-2-yl (6-(2-hydroxypropan-2-yl)pyridin-3-yl)carbamate (695);

(R)-1-((6-fluoro-2-(2-methoxy-7-methylquinoxalin-5-yl) thiazolo[5,4-b]pyridin-5-yl)oxy) propan-2-yl (2-(2-hydroxyethyl)pyridin-4-yl)carbamate (696);

(R)-1-((6-fluoro-2-(2-methoxy-7-methylquinoxalin-5-yl) thiazolo[5,4-b]pyridin-5-yl)oxy) propan-2-yl (2-(2-hydroxyethoxy)pyridin-4-yl)carbamate (697);

(R)-1-((6-fluoro-2-(2-methoxy-7-methylquinoxalin-5-yl) thiazolo[5,4-b]pyridin-5-yl)oxy) propan-2-yl pyridazin-4-ylcarbamate (698);

(R)-1-((6-fluoro-2-(2-methoxy-7-methylquinoxalin-5-yl) thiazolo[5,4-b]pyridin-5-yl)oxy) propan-2-yl (2-(3-hydroxy-3-methylbutoxy)pyridin-4-yl)carbamate (699);

(R)-1-((6-fluoro-2-(2-methoxy-7-methylquinoxalin-5-yl) thiazolo[5,4-b]pyridin-5-yl)oxy) propan-2-yl (6-(2-hydroxyethoxy)pyridin-3-yl)carbamate (700);

(R)-1-((6-fluoro-2-(2-methoxy-7-methylquinoxalin-5-yl) thiazolo[5,4-b]pyridin-5-yl)oxy) propan-2-yl (2-((S)-2-hydroxypropoxy)pyrimidin-5-yl)carbamate (701);

(R)-1-((6-fluoro-2-(2-methoxy-7-methylquinoxalin-5-yl) thiazolo[5,4-b]pyridin-5-yl)oxy) propan-2-yl (2-(3-hydroxy-3-methylbutoxy)pyrimidin-5-yl)carbamate (702);

(2R,3S)-3-((5-fluoro-2-(6-fluoro-3-methoxyquinolin-8-yl) benzo[d]thiazol-6-yl)oxy)butan-2-yl (2-methylpyrimidin-5-yl)carbamate (772);

(2R,3S)-3-((5-fluoro-2-(6-(hydroxymethyl)-3-methoxyquinolin-8-yl)benzo[d]triazol-6-yl) oxy)butan-2-yl (2-methylpyrimidin-5-yl)carbamate (773);

(2R,3S)-3-((2-(6-chloro-3-methoxyquinolin-8-yl)-5-fluorobenzo[d]thiazol-6-yl)oxy)butan-2-yl (5-fluoropyridin-3-yl)carbamate (782);

(2R,3S)-3-((2-(6-chloro-3-methoxyquinolin-8-yl)-5-fluorobenzo[d]thiazol-6-yl)oxy)butan-2-yl (6-(trifluoromethyl)pyridin-3-yl)carbamate (783);

(2R,3S)-3-((2-(6-chloro-3-methoxyquinolin-8-yl)-5-fluorobenzo[d]thiazol-6-yl)oxy)butan-2-yl (6-methoxypyridin-3-yl)carbamate (784);

(2R,3S)-3-((2-(6-chloro-3-methoxyquinolin-8-yl)-5-fluorobenzo[d]thiazol-6-yl)oxy)butan-2-yl (5-methoxypyridin-3-yl)carbamate (785);

(2R,3S)-3-((2-(6-chloro-3-methoxyquinolin-8-yl)-5-fluorobenzo[d]thiazol-6-yl)oxy)butan-2-yl (5-cyanopyridin-3-yl)carbamate (786);

(2R,3S)-3-((2-(6-chloro-3-methoxyquinolin-8-yl)-5-fluorobenzo[d]thiazol-6-yl)oxy)butan-2-yl (5,6-dimethylpyridin-3-yl)carbamate (787);

(2R,3S)-3-((2-(6-chloro-3-methoxyquinolin-8-yl)-5-fluorobenzo[d]thiazol-6-yl)oxy)butan-2-yl pyridin-3-ylcarbamate (788);

(2R,3S)-3-((2-(6-chloro-3-methoxyquinolin-8-yl)-5-fluorobenzo[d]thiazol-6-yl)oxy)butan-2-yl (6-fluoropyridin-3-yl)carbamate (789);

(2R,3S)-3-((2-(6-chloro-3-methoxyquinolin-8-yl)-5-fluorobenzo[d]thiazol-6-yl)oxy)butan-2-yl pyridin-4-ylcarbamate (790);

(2R,3S)-3-((4-chloro-2-(6-chloro-3-methoxyquinolin-8-yl)-5-fluorobenzo[d]thiazol-6-yl) oxy)butan-2-yl (2-(2-hydroxyethoxy)pyrimidin-5-yl)carbamate (795);

(2R,3S)-3-((4-chloro-2-(6-chloro-3-methoxyquinolin-8-yl)-5-fluorobenzo[d]thiazol-6-yl) oxy)butan-2-yl (2-((R)-2-hydroxypropoxy)pyrimidin-5-yl)carbamate (796);

(2R,3S)-3-((4-chloro-2-(6-chloro-3-methoxyquinolin-8-yl)-5-fluorobenzo[d]thiazol-6-yl) oxy)butan-2-yl (6-fluoropyridin-3-yl)carbamate (797);

(2R,3S)-3-((4-chloro-2-(6-chloro-3-methoxyquinolin-8-yl)-5-fluorobenzo[d]thiazol-6-yl) oxy)butan-2-yl pyridin-4-ylcarbamate (798);

(2R,3S)-3-((4-chloro-2-(6-chloro-3-methoxyquinolin-8-yl)-5-fluorobenzo[d]thiazol-6-yl) oxy)butan-2-yl pyridin-3-ylcarbamate (799);

(2R,3S)-3-((4-chloro-2-(6-chloro-3-methoxyquinolin-8-yl)-5-fluorobenzo[d]thiazol-6-yl) oxy)butan-2-yl (5,6-dimethylpyridin-3-yl)carbamate (800);

(2R,3S)-3-((4-chloro-2-(6-chloro-3-methoxyquinolin-8-yl)-5-fluorobenzo[d]thiazol-6-yl) oxy)butan-2-yl (6-methoxypyridin-3-yl)carbamate (801);

(2R,3S)-3-((4-chloro-2-(6-chloro-3-methoxyquinolin-8-yl)-5-fluorobenzo[d]thiazol-6-yl) oxy)butan-2-yl (5-cyanopyridin-3-yl)carbamate (802);

(2R,3S)-3-((4-chloro-2-(6-chloro-3-methoxyquinolin-8-yl)-5-fluorobenzo[d]thiazol-6-yl) oxy)butan-2-yl (5-methoxypyridin-3-yl)carbamate (803);

(2R,3S)-3-((4-chloro-5-fluoro-2-(3-methoxy-6-methylquinolin-8-yl)benzo[d]thiazol-6-yl) oxy)butan-2-yl (5-fluoropyridin-3-yl)carbamate (804);

1-(6-fluoro-2-(2-methoxy-7-methylquinoxalin-5-yl)benzo[d]thiazol-4-yl)-2,2-dimethylpropan-1-ol (806);

6-methoxy-2-(2-methoxy-7-methylquinoxalin-5-yl)-4-(methoxymethyl)benzo[d]thiazole (808);

1-(2-(2-ethoxy-7-methylquinoxalin-5-yl)-6-methoxybenzo[d]thiazol-4-yl)-2,2-dimethylpropan-1-ol (817);

(R)-1-((2-(7-cyano-2-methoxyquinoxalin-5-yl)-5-fluorobenzo[d]thiazol-6-yl)oxy)propan-2-yl (6-cyanopyridin-3-yl)carbamate (818);

(R)-1-((2-(7-cyano-2-methoxyquinoxalin-5-yl)-5-fluorobenzo[d]thiazol-6-yl)oxy)propan-2-yl (2-methylpyrimidin-5-yl)carbamate (819);

(2R,3S)-3-((2-(7-chloro-2-methoxyquinoxalin-5-yl)-5-fluorobenzo[d]thiazol-6-yl)oxy)butan-2-yl (2-methoxypyrimidin-5-yl)carbamate (820);

(2R,3S)-3-((2-(7-chloro-2-methoxyquinoxalin-5-yl)-5-fluorobenzo[d]thiazol-6-yl)oxy)butan-2-yl (6-methoxypyridin-3-yl)carbamate (821);

(2R,3S)-3-((2-(7-chloro-2-methoxyquinoxalin-5-yl)-5-fluorobenzo[d]thiazol-6-yl)oxy)butan-2-yl (6-methylpyridin-3-yl)carbamate (822);

(2R,3S)-3-((2-(7-cyano-2-methoxyquinoxalin-5-yl)-5-fluorobenzo[d]thiazol-6-yl)oxy)butan-2-yl (6-methylpyridin-3-yl)carbamate (823);

(2R,3S)-3-((2-(7-chloro-2-methoxyquinoxalin-5-yl)-5-fluorobenzo[d]thiazol-6-yl)oxy)butan-2-yl (2-methylpyrimidin-5-yl)carbamate (824);

(2R,3S)-3-((2-(7-cyano-2-methoxyquinoxalin-5-yl)-5-fluorobenzo[d]thiazol-6-yl)oxy)butan-2-yl (2-methylpyrimidin-5-yl)carbamate (825);

(2R,3S)-3-((2-(7-chloro-2-methoxyquinoxalin-5-yl)-5-fluorobenzo[d]thiazol-6-yl)oxy)butan-2-yl (5-cyanopyridin-3-yl)carbamate (826);

(2R,3S)-3-((2-(2-(2,2-difluoroethoxy)-7-methylquinoxalin-5-yl)-5-fluorobenzo[d]thiazol-6-yl)oxy)butan-2-yl (2-methylpyrimidin-5-yl)carbamate (827);

(2R,3S)-3-((2-(7-cyano-2-methoxyquinoxalin-5-yl)-5-fluorobenzo[d]thiazol-6-yl)oxy)butan-2-yl (6-cyanopyridin-3-yl)carbamate (828);

(2R,3S)-3-((2-(7-chloro-2-methoxyquinoxalin-5-yl)-5-fluorobenzo[d]thiazol-6-yl)oxy)butan-2-yl (6-cyanopyridin-3-yl)carbamate (829); methyl 5-(((((2R,3S)-3-((2-(7-chloro-2-methoxyquinoxalin-5-yl)-5-fluorobenzo[d]thiazol-6-yl)oxy)butan-2-yl)oxy)carbonyl)amino)picolinate (830);

(2R,3S)-3-((2-(7-chloro-2-methoxyquinoxalin-5-yl)-5-fluorobenzo[d]thiazol-6-yl)oxy)butan-2-yl (6-(hydroxymethyl)pyridin-3-yl)carbamate (831);

(2R,3S)-3-((2-(7-chloro-2-methoxyquinoxalin-5-yl)-5-fluorobenzo[d]thiazol-6-yl)oxy)butan-2-yl (6-(methylcarbamoyl)pyridin-3-yl)carbamate (832);

(2R,3S)-3-((2-(7-chloro-2-methoxyquinoxalin-5-yl)-5-fluorobenzo[d]thiazol-6-yl)oxy) butan-2-yl (6-carbamoylpyridin-3-yl)carbamate (833);

(2R,3S)-3-((2-(7-chloro-2-methoxyquinoxalin-5-yl)-5-fluorobenzo[d]thiazol-6-yl)oxy)butan-2-yl (6-(dimethylcarbamoyl)pyridin-3-yl)carbamate (834);

(2R,3S)-3-((2-(7-chloro-2-methoxyquinoxalin-5-yl)-5-fluorobenzo[d]thiazol-6-yl)oxy)butan-2-yl (6-(2-hydroxy-2-methylpropyl)pyridin-3-yl)carbamate (835);

(2R,3S)-3-((2-(7-chloro-2-methoxyquinoxalin-5-yl)-5-fluorobenzo[d]thiazol-6-yl)oxy)butan-2-yl (6-(2-hydroxyethyl)pyridin-3-yl)carbamate (836); and 2-(7-chloro-2-methoxyquinoxalin-5-yl)-6-methoxy-4-methylbenzo[d]thiazole (837);

One embodiment provides compounds of Formulas (I), (II), (III), or (IV) or a salt thereof, wherein $R_3$ is imidazol[1,2-a]pyridinyl. Included in this embodiment is a compound of Formula (I) selected from:

2-(difluoromethoxy)-5-(imidazo[1,2-a]pyridin-2-yl)-7-methylquinoxaline (45).

One embodiment provides compounds of Formulas (I), (II), (III), or (IV) or a salt thereof, wherein $R_3$ is thiazolo[4,5-b]pyridinyl. Included in this embodiment is a compound of Formula (I) selected from:

2-(2-(difluoromethoxy)-7-methylquinoxalin-5-yl)thiazolo[4,5-b]pyridine (9);

2-(2-(difluoromethoxy)-7-methylquinoxalin-5-yl)-7-methoxythiazolo[4,5-c]pyridine (24);

2-(2-(methoxymethyl)-7-methylquinoxalin-5-yl)thiazolo[4,5-c]pyridine (146); and 2-(2-methoxy-7-methylquinoxalin-5-yl)thiazolo[4,5-c]pyridine (809).

One embodiment provides compounds of Formulas (I), (II), (III), or (IV) or a salt thereof, wherein $R_3$ is thiazolo[5,4-b] pyridinyl. Included in this embodiment is a compound of Formula (I) selected from:

2-(2-(difluoromethoxy)-7-methylquinoxalin-5-yl)-5-methoxythiazolo[5,4-b]pyridine (23);

2-(2-(methoxymethyl)-7-methylquinoxalin-5-yl)thiazolo[5,4-b]pyridine (147);

2-(2-(methoxymethyl)-7-methylquinoxalin-5-yl)thiazolo[5,4-b]pyridine (148);

7-chloro-2-(2-(methoxymethyl)-7-methylquinoxalin-5-yl)thiazolo[5,4-c]pyridine (149);

5-methoxy-2-(2-methoxy-7-methylquinoxalin-5-yl)thiazolo[5,4-b]pyridine (150);

7-chloro-2-(2-methoxy-7-methylquinoxalin-5-yl)thiazolo[5,4-c]pyridine (151);

5-methoxy-2-(2-methoxy-7-methylquinoxalin-5-yl)-7-methylthiazolo[5,4-b]pyridine (179);

6-fluoro-5-methoxy-2-(2-(methoxymethyl)-7-methylquinoxalin-5-yl)thiazolo[5,4-b] pyridine (180);

5-methoxy-2-(2-(methoxymethyl)-7-methylquinoxalin-5-yl)-7-methylthiazolo[5,4-b] pyridine (181);

6-fluoro-5-methoxy-2-(2-methoxy-7-methylquinoxalin-5-yl)thiazolo[5,4-b]pyridine (182); 5-chloro-2-(2-(methoxymethyl)-7-methylquinoxalin-5-yl)-7-methylthiazolo[5,4-b] pyridine (191);

(5-methoxy-2-(2-(methoxymethyl)-7-methylquinoxalin-5-yl)thiazolo[5,4-b]pyridin-7-yl) methanol (192);

4-fluoro-N-(2-((2-(2-(methoxymethyl)-7-methylquinoxalin-5-yl)-7-methylthiazolo[5,4-b] pyridin-5-yl)oxy)ethyl)benzenesulfonamide (193);

4-fluoro-N-(2-((2-(2-methoxy-7-methylquinoxalin-5-yl)-7-methylthiazolo[5,4-b]pyridin-5-yl)oxy)ethyl)benzenesulfonamide (194);

2-((2-(2-methoxy-7-methylquinoxalin-5-yl)-7-methylthiazolo[5,4-b]pyridin-5-yl)oxy)ethyl pyridin-3-ylcarbamate (196);

2-((2-(2-methoxy-7-methylquinoxalin-5-yl)-7-methylthiazolo[5,4-b]pyridin-5-yl)oxy)ethyl (6-cyanopyridin-3-yl)carbamate (197);

2-((6-fluoro-2-(2-methoxy-7-methylquinoxalin-5-yl)thiazolo[5,4-b]pyridin-5-yl)oxy)ethyl (6-cyanopyridin-3-yl)carbamate (198);

(3-methoxy-8-(5-methoxy-7-methylthiazolo[5,4-b]pyridin-2-yl)quinoxalin-6-yl)methanol (223);

(2R,3S)-3-((6-fluoro-2-(2-methoxy-7-methylquinoxalin-5-yl)thiazolo[5,4-b]pyridin-5-yl) oxy)butan-2-yl (2-oxo-2,3-dihydrobenzo[d]oxazol-6-yl)carbamate (708);

(2R,3S)-3-((6-fluoro-2-(2-methoxy-7-methylquinoxalin-5-yl)thiazolo[5,4-b]pyridin-5-yl) oxy)butan-2-yl pyridin-3-ylcarbamate (709);

(2R,3S)-3-((6-fluoro-2-(2-methoxy-7-methylquinoxalin-5-yl)thiazolo[5,4-b]pyridin-5-yl) oxy)butan-2-yl (6-methylpyridin-3-yl)carbamate (710);

(2R,3S)-3-((6-fluoro-2-(2-methoxy-7-methylquinoxalin-5-yl)thiazolo[5,4-b]pyridin-5-yl) oxy)butan-2-yl (2-methoxypyrimidin-5-yl)carbamate (711); methyl 5-(((((2R,3S)-3-((6-fluoro-2-(2-methoxy-7-methylquinoxalin-5-yl)thiazolo[5,4-b]pyridin-5-yl)oxy)butan-2-yl)oxy)carbonyl)amino)pyrimidine-2-carboxylate (712);

(2R,3S)-3-((6-fluoro-2-(2-methoxy-7-methylquinoxalin-5-yl)thiazolo[5,4-b]pyridin-5-yl) oxy)butan-2-yl pyridin-4-ylcarbamate (713);

(2R,3S)-3-((6-fluoro-2-(2-methoxy-7-methylquinoxalin-5-yl)thiazolo[5,4-b]pyridin-5-yl) oxy)butan-2-yl (5-fluoropyridin-3-yl)carbamate (714); methyl 5-(((((2R,3S)-3-((6-fluoro-2-(2-methoxy-7-methylquinoxalin-5-yl)thiazolo[5,4-b]pyridin-5-yl)oxy)butan-2-yl)oxy)carbonyl)amino)picolinate (715);

(2R,3S)-3-((6-fluoro-2-(2-methoxy-7-methylquinoxalin-5-yl)thiazolo[5,4-b]pyridin-5-yl) oxy)butan-2-yl pyrimidin-5-ylcarbamate (716);

(2R,3S)-3-((6-fluoro-2-(2-methoxy-7-methylquinoxalin-5-yl)thiazolo[5,4-b]pyridin-5-yl) oxy)butan-2-yl (2-(2-hydroxyethyl)pyridin-4-yl)carbamate (717);

(2R,3S)-3-((6-fluoro-2-(2-methoxy-7-methylquinoxalin-5-yl)thiazolo[5,4-b]pyridin-5-yl) oxy)butan-2-yl (6-(2-hydroxy-2-methylpropyl)pyridin-3-yl)carbamate (718);

(2R,3S)-3-((6-fluoro-2-(2-methoxy-7-methylquinoxalin-5-yl)thiazolo[5,4-b]pyridin-5-yl) oxy)butan-2-yl (2-(2-hydroxyethoxy)pyridin-4-yl)carbamate (719);

(2R,3S)-3-((6-fluoro-2-(2-methoxy-7-methylquinoxalin-5-yl)thiazolo[5,4-b]pyridin-5-yl) oxy)butan-2-yl (2-(2-hydroxyethyl)pyrimidin-5-yl)carbamate (720);

(2R,3S)-3-((6-fluoro-2-(2-methoxy-7-methylquinoxalin-5-yl)thiazolo[5,4-b]pyridin-5-yl) oxy)butan-2-yl (2-(2-hydroxyethoxy)pyrimidin-5-yl)carbamate (721);

(2R,3S)-3-((6-fluoro-2-(2-methoxy-7-methylquinoxalin-5-yl)thiazolo[5,4-b]pyridin-5-yl) oxy)butan-2-yl (2-(((R)-1-hydroxypropan-2-yl)oxy)pyrimidin-5-yl)carbamate (722);

(2R,3S)-3-((6-fluoro-2-(2-methoxy-7-methylquinoxalin-5-yl)thiazolo[5,4-b]pyridin-5-yl) oxy)butan-2-yl (2-(hydroxymethyl)pyridin-4-yl)carbamate (723);

(2R,3S)-3-((6-fluoro-2-(2-methoxy-7-methylquinoxalin-5-yl)thiazolo[5,4-b]pyridin-5-yl) oxy)butan-2-yl (2-(((S)-1-hydroxypropan-2-yl)oxy)pyrimidin-5-yl)carbamate (724);

(2R,3S)-3-((6-fluoro-2-(2-methoxy-7-methylquinoxalin-5-yl)thiazolo[5,4-b]pyridin-5-yl) oxy)butan-2-yl (6-(2-hydroxyethoxy)pyridin-3-yl)carbamate (725);

(2R,3S)-3-((6-fluoro-2-(2-methoxy-7-methylquinoxalin-5-yl)thiazolo[5,4-b]pyridin-5-yl) oxy)butan-2-yl (6-(2,2-difluoro-3-hydroxypropoxy)pyridin-3-yl)carbamate (726);

(2R,3S)-3-((6-fluoro-2-(2-methoxy-7-methylquinoxalin-5-yl)thiazolo[5,4-b]pyridin-5-yl) oxy)butan-2-yl (2-(3-hydroxy-3-methylbutoxy)pyridin-4-yl)carbamate (727);

(2R,3S)-3-((6-fluoro-2-(2-methoxy-7-methylquinoxalin-5-yl)thiazolo[5,4-b]pyridin-5-yl) oxy)butan-2-yl (2-((S)-2-hydroxypropoxy)pyrimidin-5-yl)carbamate (728);

(2R,3S)-3-((6-fluoro-2-(2-methoxy-7-methylquinoxalin-5-yl)thiazolo[5,4-b]pyridin-5-yl) oxy)butan-2-yl (2-((R)-2-hydroxypropoxy)pyrimidin-5-yl)carbamate (729);

(2R,3S)-3-((6-fluoro-2-(2-methoxy-7-methylquinoxalin-5-yl)thiazolo[5,4-b]pyridin-5-yl) oxy)butan-2-yl (2-(3-hydroxy-3-methylbutoxy)pyrimidin-5-yl)carbamate (730);

(2R,3S)-3-((6-fluoro-2-(2-methoxy-7-methylquinoxalin-5-yl)thiazolo[5,4-b]pyridin-5-yl) oxy)butan-2-yl (2-methylpyrimidin-5-yl)carbamate (731);

(R)-1-((2-(2-methoxy-7-methylquinoxalin-5-yl)-7-methylthiazolo[5,4-b]pyridin-5-yl)oxy) propan-2-yl pyridin-3-ylcarbamate (733);

(R)-1-((2-(2-methoxy-7-methylquinoxalin-5-yl)-7-methylthiazolo[5,4-b]pyridin-5-yl)oxy) propan-2-yl (6-fluoro-5-methylpyridin-3-yl)carbamate (734);

(R)-1-((2-(2-methoxy-7-methylquinoxalin-5-yl)-7-methylthiazolo[5,4-b]pyridin-5-yl)oxy) propan-2-yl (5-cyanopyridin-3-yl)carbamate (735);

(R)-1-((2-(2-methoxy-7-methylquinoxalin-5-yl)-7-methylthiazolo[5,4-b]pyridin-5-yl)oxy) propan-2-yl (2-chloropyrimidin-5-yl)carbamate (736);

(R)-1-((2-(2-methoxy-7-methylquinoxalin-5-yl)-7-methylthiazolo[5,4-b]pyridin-5-yl)oxy) propan-2-yl (2-methylpyrimidin-5-yl)carbamate (737);

(R)-1-((2-(2-methoxy-7-methylquinoxalin-5-yl)-7-methylthiazolo[5,4-b]pyridin-5-yl)oxy) propan-2-yl (2-methoxypyrimidin-5-yl)carbamate (738);

(R)-1-((2-(2-methoxy-7-methylquinoxalin-5-yl)-7-methylthiazolo[5,4-b]pyridin-5-yl)oxy) propan-2-yl pyridin-3-ylcarbamate (740);

(R)-1-((6-fluoro-2-(2-methoxy-7-methylquinoxalin-5-yl)thiazolo[5,4-b]pyridin-5-yl)oxy) propan-2-yl (6-((2-hydroxy-2-methylpropyl)carbamoyl)pyridin-3-yl)carbamate (741);

(R)-1-((6-fluoro-2-(2-methoxy-7-methylquinoxalin-5-yl)thiazolo[5,4-b]pyridin-5-yl)oxy) propan-2-yl (6-(((1-(hydroxymethyl)cyclobutyl)methyl)carbamoyl)pyridin-3-yl)carbamate (742);

(R)-1-((6-fluoro-2-(2-methoxy-7-methylquinoxalin-5-yl)thiazolo[5,4-b]pyridin-5-yl)oxy) propan-2-yl (6-(3-hydroxypiperidine-1-carbonyl)pyridin-3-yl)carbamate (743);

(R)-1-((6-fluoro-2-(2-methoxy-7-methylquinoxalin-5-yl)thiazolo[5,4-b]pyridin-5-yl)oxy) propan-2-yl (6-((S)-3-hydroxypyrrolidine-1-carbonyl)pyridin-3-yl)carbamate (744);

(R)-1-((6-fluoro-2-(2-methoxy-7-methylquinoxalin-5-yl)thiazolo[5,4-b]pyridin-5-yl)oxy) propan-2-yl (6-((R)-3-hydroxypyrrolidine-1-carbonyl)pyridin-3-yl)carbamate (745);

(R)-1-((6-fluoro-2-(2-methoxy-7-methylquinoxalin-5-yl)thiazolo[5,4-b]pyridin-5-yl)oxy) propan-2-yl (6-(4-hydroxypiperidine-1-carbonyl)pyridin-3-yl)carbamate (746);

(R)-1-((6-fluoro-2-(2-methoxy-7-methylquinoxalin-5-yl)thiazolo[5,4-b]pyridin-5-yl)oxy) propan-2-yl (6-(((R)-2-hydroxypropyl)carbamoyl)pyridin-3-yl)carbamate (747);

(R)-1-((6-fluoro-2-(2-methoxy-7-methylquinoxalin-5-yl)thiazolo[5,4-b]pyridin-5-yl)oxy) propan-2-yl (6-(((S)-2-hydroxypropyl)carbamoyl)pyridin-3-yl)carbamate (748);

(R)-1-((6-fluoro-2-(2-methoxy-7-methylquinoxalin-5-yl)thiazolo[5,4-b]pyridin-5-yl)oxy) propan-2-yl (2-carbamoylpyrimidin-5-yl)carbamate (749);

(2R,3S)-3-((6-fluoro-2-(2-methoxy-7-methylquinoxalin-5-yl)thiazolo[5,4-b]pyridin-5-yl) oxy)butan-2-yl (6-(((S)-2-hydroxypropyl)carbamoyl)pyridin-3-yl)carbamate (750);

(2R,3S)-3-((6-fluoro-2-(2-methoxy-7-methylquinoxalin-5-yl)thiazolo[5,4-b]pyridin-5-yl) oxy)butan-2-yl (2-((2-hydroxy-2-methylpropyl)carbamoyl)pyrimidin-5-yl)carbamate (751);

(2R,3S)-3-((6-fluoro-2-(2-methoxy-7-methylquinoxalin-5-yl)thiazolo[5,4-b]pyridin-5-yl) oxy)butan-2-yl (2-(((R)-2-hydroxypropyl)carbamoyl)pyrimidin-5-yl)carbamate (752);

(2R,3S)-3-((6-fluoro-2-(2-methoxy-7-methylquinoxalin-5-yl)thiazolo[5,4-b]pyridin-5-yl) oxy)butan-2-yl (2-(((S)-2-hydroxypropyl)carbamoyl)pyrimidin-5-yl)carbamate (753);

(2R,3S)-3-((6-fluoro-2-(2-methoxy-7-methylquinoxalin-5-yl)thiazolo[5,4-b]pyridin-5-yl) oxy)butan-2-yl (6-carbamoylpyridin-3-yl)carbamate (754);

(2R,3S)-3-((6-fluoro-2-(2-methoxy-7-methylquinoxalin-5-yl)thiazolo[5,4-b]pyridin-5-yl) oxy)butan-2-yl (2-carbamoylpyrimidin-5-yl)carbamate (755);

(2R,3S)-3-((6-fluoro-2-(2-methoxy-7-methylquinoxalin-5-yl)thiazolo[5,4-b]pyridin-5-yl) oxy)butan-2-yl (6-(3-(hydroxymethyl)morpholine-4-carbonyl)pyridin-3-yl)carbamate (756);

(2R,3S)-3-((6-fluoro-2-(2-methoxy-7-methylquinoxalin-5-yl)thiazolo[5,4-b]pyridin-5-yl) oxy)butan-2-yl (6-((S)-3-hydroxypyrrolidine-1-carbonyl)pyridin-3-yl)carbamate (757);

(2R,3S)-3-((6-fluoro-2-(2-methoxy-7-methylquinoxalin-5-yl)thiazolo[5,4-b]pyridin-5-yl) oxy)butan-2-yl (6-(3-hydroxypiperidine-1-carbonyl)pyridin-3-yl)carbamate (758);

(2R,3S)-3-((6-fluoro-2-(2-methoxy-7-methylquinoxalin-5-yl)thiazolo[5,4-b]pyridin-5-yl) oxy)butan-2-yl (6-(4-hydroxypiperidine-1-carbonyl)pyridin-3-yl)carbamate (759);

(2R,3S)-3-((6-fluoro-2-(2-methoxy-7-methylquinoxalin-5-yl)thiazolo[5,4-b]pyridin-5-yl) oxy)butan-2-yl (6-((R)-3-hydroxypyrrolidine-1-carbonyl)pyridin-3-yl)carbamate (760);

(2R,3S)-3-((6-fluoro-2-(2-methoxy-7-methylquinoxalin-5-yl)thiazolo[5,4-b]pyridin-5-yl) oxy)butan-2-yl (6-(((1-(hydroxymethyl)cyclobutyl)methyl)carbamoyl)pyridin-3-yl)carbamate (761);

N-(2-((2-(2-methoxy-7-methylquinoxalin-5-yl)-7-methylthiazolo[5,4-b]pyridin-5-yl)oxy) ethyl)-4-methylbenzenesulfonamide (762);

6-fluoro-5-methoxy-2-(2-(methoxymethyl)-7-methylquinoxalin-5-yl)-7-methylthiazolo[5,4-b]pyridine (763);

(2R,3S)-3-((6-fluoro-2-(2-methoxy-7-methylquinoxalin-5-yl)thiazolo[5,4-b]pyridin-5-yl) oxy)butan-2-yl (2-(hydroxymethyl)pyrimidin-5-yl)carbamate (764);

(2R,3S)-3-((6-fluoro-2-(2-methoxy-7-methylquinoxalin-5-yl)thiazolo[5,4-b]pyridin-5-yl) oxy)butan-2-yl (6-(2-hydroxypropan-2-yl)pyridin-3-yl)carbamate (765);

(2R,3S)-3-((6-fluoro-2-(2-methoxy-7-methylquinoxalin-5-yl)thiazolo[5,4-b]pyridin-5-yl) oxy)butan-2-yl (6-(1-hydroxyethyl)pyridin-3-yl)carbamate (766);

(2R,3S)-3-((6-fluoro-2-(2-methoxy-7-methylquinoxalin-5-yl)thiazolo[5,4-b]pyridin-5-yl) oxy)butan-2-yl (6-(1-hydroxyethyl)pyridin-3-yl)carbamate (767);

(R)-1-((6-fluoro-2-(2-methoxy-7-methylquinoxalin-5-yl)thiazolo[5,4-b]pyridin-5-yl)oxy) propan-2-yl (2-(hydroxymethyl)pyrimidin-5-yl)carbamate (768);

(2R,3S)-3-((2-(6-chloro-3-methoxyquinolin-8-yl)-6-fluorothiazolo[5,4-b]pyridin-5-yl)oxy) butan-2-yl (2-methylpyrimidin-5-yl)carbamate (769);

(R)-1-((2-(6-chloro-3-methoxyquinolin-8-yl)-6-fluorothiazolo[5,4-b]pyridin-5-yl)oxy)propan-2-yl (2-methylpyrimidin-5-yl)carbamate (770);

(2R,3S)-3-((6-fluoro-2-(3-methoxy-6-methylquinolin-8-yl)thiazolo[5,4-b]pyridin-5-yl)oxy)butan-2-yl (2-methylpyrimidin-5-yl)carbamate (771);

(2R,3S)-3-((2-(6-chloro-3-methoxyquinolin-8-yl)-6-fluorothiazolo[5,4-b]pyridin-5-yl)oxy) butan-2-yl (2-(2-hydroxyethoxy)pyrimidin-5-yl)carbamate (774);

(2R,3S)-3-((6-fluoro-2-(3-methoxy-6-methylquinolin-8-yl)thiazolo[5,4-b]pyridin-5-yl)oxy)butan-2-yl (2-(2-hydroxyethoxy)pyrimidin-5-yl)carbamate (775);

(2R,3S)-3-((2-(6-chloro-3-methoxyquinolin-8-yl)-6-fluorothiazolo[5,4-b]pyridin-5-yl) oxy)butan-2-yl (5-fluoropyridin-3-yl)carbamate (776);

(2R,3S)-3-((2-(6-chloro-3-methoxyquinolin-8-yl)-6-fluorothiazolo[5,4-b]pyridin-5-yl)oxy) butan-2-yl (2-oxo-2,3-dihydrobenzo[d]oxazol-6-yl)carbamate (777);

(2R,3S)-3-((2-(6-chloro-3-methoxyquinolin-8-yl)-6-fluorothiazolo[5,4-b]pyridin-5-yl)oxy) butan-2-yl (2-(3-hydroxy-3-methylbutoxy)pyridin-4-yl)carbamate (778);

(2R,3S)-3-((2-(6-chloro-3-methoxyquinolin-8-yl)-6-fluorothiazolo[5,4-b]pyridin-5-yl)oxy) butan-2-yl (6-(2-hydroxyethoxy)pyridin-3-yl)carbamate (779);

(2R,3S)-3-((2-(6-chloro-3-methoxyquinolin-8-yl)-6-fluorothiazolo[5,4-b]pyridin-5-yl)oxy) butan-2-yl (2-(2-hydroxyethoxy)pyridin-4-yl)carbamate (780);

(2R,3S)-3-((2-(6-chloro-3-methoxyquinolin-8-yl)-6-fluorothiazolo[5,4-b]pyridin-5-yl)oxy) butan-2-yl (6-(2-hydroxyethyl)pyridin-3-yl)carbamate (781);

(2R,3S)-3-((6-fluoro-2-(3-methoxy-6-methylquinolin-8-yl)thiazolo[5,4-b]pyridin-5-yl)oxy)butan-2-yl (2-methylpyrimidin-5-yl)carbamate (791);

(2R,3S)-3-((6-fluoro-2-(3-methoxy-6-methylquinolin-8-yl)thiazolo[5,4-b]pyridin-5-yl)oxy)butan-2-yl (2-(hydroxymethyl)pyrimidin-5-yl)carbamate (792);

(2R,3S)-3-((2-(6-chloro-3-methoxyquinolin-8-yl)-6-fluorothiazolo[5,4-b]pyridin-5-yl)oxy) butan-2-yl (2-(hydroxymethyl)pyrimidin-5-yl)carbamate (793);

(R)-1-((2-(6-chloro-3-methoxyquinolin-8-yl)-6-fluorothiazolo[5,4-b]pyridin-5-yl)oxy)propan-2-yl (2-(hydroxymethyl)pyrimidin-5-yl)carbamate (794);

1-(5-methoxy-2-(2-methoxy-7-methylquinoxalin-5-yl)thiazolo[5,4-b]pyridin-7-yl)-2,2-dimethylpropan-1-ol (807);

2-((6-fluoro-2-(2-methoxy-7-methylquinoxalin-5-yl)thiazolo[5,4-b]pyridin-5-yl)oxy)ethyl pyridin-3-ylcarbamate (810);

2-((6-fluoro-2-(2-methoxy-7-methylquinoxalin-5-yl)thiazolo[5,4-b]pyridin-5-yl)oxy) ethyl (6-fluoro-5-methylpyridin-3-yl)carbamate (811);

2-((2-(2-methoxy-7-methylquinoxalin-5-yl)-7-methylthiazolo[5,4-b]pyridin-5-yl)oxy) ethyl (6-(thiophen-2-yl)pyridin-3-yl)carbamate (812);

(R)-1-((2-(2-ethoxy-7-methylquinoxalin-5-yl)-6-fluorothiazolo[5,4-b]pyridin-5-yl)oxy)propan-2-yl (2-methylpyrimidin-5-yl)carbamate (813);

(R)-1-((2-(2-ethoxy-7-methylquinoxalin-5-yl)-6-fluorothiazolo[5,4-b]pyridin-5-yl)oxy)propan-2-yl (2-(2-hydroxyethoxy)pyrimidin-5-yl)carbamate (814);

(R)-1-((2-(2-ethoxy-7-methylquinoxalin-5-yl)-6-fluorothiazolo[5,4-b]pyridin-5-yl)oxy) propan-2-yl (2-((R)-2-hydroxypropoxy)pyrimidin-5-yl)carbamate (815);

(2R,3S)-3-((2-(2-ethoxy-7-methylquinoxalin-5-yl)-6-fluorothiazolo[5,4-b]pyridin-5-yl)oxy)butan-2-yl (2-(hydroxymethyl)pyrimidin-5-yl)carbamate (816); and
1-(2-(2-ethoxy-7-methylquinoxalin-5-yl)-6-methoxybenzo[d]thiazol-4-yl)-2,2-dimethylpropan-1-ol (817).

One embodiment provides compounds of Formulas (I), (II), (III), or (IV) or a salt thereof, wherein $R_3$ is 4,5,6,7-tetrahydrobenzo[d]thiazolyl. Included in this embodiment is a compound of Formula (I) selected from:
2-(2-methoxy-7-methylquinoxalin-5-yl)-4,5,6,7-tetrahydrobenzo[d]thiazol-7-ol (138);
7-methoxy-2-(2-methoxy-7-methylquinoxalin-5-yl)-4,5,6,7-tetrahydrobenzo[d]thiazole (139);
6-methoxy-2-(2-methoxy-7-methylquinoxalin-5-yl)-4,5,6,7-tetrahydrobenzo[d]thiazole (140);
2-(2-methoxy-7-methylquinoxalin-5-yl)-6,6-dimethyl-4,5,6,7-tetrahydrobenzo[d]thiazole (141); 2-(2-(methoxymethyl)-7-methylquinoxalin-5-yl)-4,5,6,7-tetrahydrobenzo[d] thiazol-7-ol (143);
2-(2-(methoxymethyl)-7-methylquinoxalin-5-yl)-4,5,6,7-tetrahydrobenzo[d]thiazole (144);
2-(2-(methoxymethyl)-7-methylquinoxalin-5-yl)-6,6-dimethyl-4,5,6,7-tetrahydrobenzo[d] thiazol-7-ol (145); and
2-(2-(difluoromethoxy)-7-methylquinoxalin-5-yl)-4,5,6,7-tetrahydrobenzo[d]thiazole (178).

One embodiment provides compounds of Formulas (I), (II), (III), or (IV) or a salt thereof, wherein $R_3$ is 4,5,6,7-tetrahydrobenzofuranyl. Included in this embodiment is a compound of Formula (I) selected from: tert-butyl (2-(2-(difluoromethoxy)-7-methylquinoxalin-5-yl)-4,5,6,7-tetrahydrobenzofuran-4-yl) carbamate (25).

One embodiment provides compounds of Formulas (I), (II), (III), or (IV) or a salt thereof, wherein $R_3$ is 6,7-tetrahydrothiazolo[5,4-c]pyridinyl. Included in this embodiment is a compound of Formula (I) selected from: tert-butyl 2-(2-(difluoromethoxy)-7-methylquinoxalin-5-yl)-6,7-dihydrothiazolo[5,4-c]pyridine-5(4H)-carboxylate (11) and methyl
2-(2-(difluoromethoxy)-7-methylquinoxalin-5-yl)-6,7-dihydrothiazolo[5,4-c]pyridine-5(4H)-carboxylate (62).

One embodiment provides compounds of Formulas (I), (II), (III), or (IV) or a salt thereof, wherein $R_3$ is 5,6,7,8-tetrahydro-4H-cyclohepta[d] thiazolyl. Included in this embodiment is a compound of Formula (I) selected from:
2-(2-methoxy-7-methylquinoxalin-5-yl)-5,6,7,8-tetrahydro-4H-cyclohepta[d]thiazole (137).

One embodiment provides compounds of Formulas (I), (II), (III), or (IV) or a salt thereof, wherein $R_3$ is 5,6-dihydro-4H-cyclopenta[d]thiazolyl. Included in this embodiment is a compound of Formula (I) selected from:
2-(2-(difluoromethoxy)-7-methylquinoxalin-5-yl)-5,6-dihydro-4H-cyclopenta[d]thiazole (136); and 2-(2-(2-methoxy-7-methylquinoxalin-5-yl)-5,6-dihydro-4H-cyclopenta[d] thiazol-5-yl) ethanol (142).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.
The term "amino" refers to the group —$NH_2$.
The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to four carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "aminoalkyl" as used herein is intended to include both branched and straight-chain saturated aliphatic hydrocarbon groups substituted with one or more amino groups. For example, "$C_{1-4}$ aminoalkyl" is intended to include $C_1$, $C_2$, $C_3$, and $C_4$ alkyl groups substituted with one or more amino groups. Representative examples of aminoalkyl groups include, but are not limited to, —$CH_2NH_2$, —$CH_2CH_2NH_2$, and —$CH_2CH(NH_2)CH_3$.

The term "hydroxyalkyl" includes both branched and straight-chain saturated alkyl groups substituted with one or more hydroxyl groups. For example, "hydroxyalkyl" includes —$CH_2OH$, —$CH_2CH_2OH$, and $C_{1-4}$ hydroxyalkyl.

The term "hydroxy-deuteroalkyl" includes both branched and straight-chain saturated alkyl groups substituted with one or more hydroxyl groups and one or more deuterium atoms. Representative examples of hydroxy-deuteroalkyl groups include, but are not limited to, —$CD_2OH$ and —$CH(CD_3)_2OH$.

The term "hydroxy-fluoroalkyl" includes both branched and straight-chain saturated alkyl groups substituted with one or more hydroxyl groups and one or more fluorine atoms. Representative examples of hydroxy-fluoroalkyl groups include, but are not limited to, —$CF_2OH$ and —$CF_2CH_2OH$.

As used herein, "alkylene" refers to a bivalent alkyl radical having the general formula —$(CH_2)_n$—, where n is 1 to 10. Non-limiting examples include methylene, dimethylene, trimethylene, tetramethylene, pentamethylene, and hexamethylene. For example, "$C_{1-6}$ alkylene" denotes straight and branched chain alkylene groups with one to six carbon atoms. Further, for example, "$C_{0-4}$ alkylene" denotes a bond and straight and branched chain alkylene groups with one to four carbon atoms.

As used herein, "deuteroalkylene" refers to an alkylene group in which one or more hydrogen atoms have been replaced with deuterium atoms. For example, "$C_{1-6}$ deuteroalkylene" denotes straight and branched chain deuteroalkylene groups with one to six carbon atoms.

As used herein, "fluoroalkylene" refers to an alkylene group substituted with one or more fluorine atoms. For example, "$C_{1-6}$ fluoroalkylene" denotes straight and branched chain fluoroalkylene groups with one to six carbon atoms.

The term "alkenyl" refers to a straight or branched chain hydrocarbon radical containing from 2 to 12 carbon atoms and at least one carbon-carbon double bond. Exemplary such groups include ethenyl or allyl. For example, "$C_{2-6}$ alkenyl" denotes straight and branched chain alkenyl groups with two to six carbon atoms.

The term "alkynyl" refers to a straight or branched chain hydrocarbon radical containing from 2 to 12 carbon atoms and at least one carbon to carbon triple bond. Exemplary such groups include ethynyl. For example, "$C_{2-6}$ alkynyl" denotes straight and branched chain alkynyl groups with two to six carbon atoms.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "fluorocycloalkyl" refers to a cycloalkyl group in which one or more hydrogen atoms are replaced by fluoro group(s).

The term "hydroxycycloalkyl" refers to a cycloalkyl group in which one or more hydrogen atoms are replaced by hydroxyl group(s).

The term "alkoxy," as used herein, refers to an alkyl group attached to the parent molecular moiety through an oxygen atom, for example, methoxy group (—$OCH_3$). For example, "$C_{1-3}$ alkoxy" denotes alkoxy groups with one to three carbon atoms.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "hydroxyalkoxy" represent a hydroxyalkyl group as defined above attached through an oxygen linkage (—O—). For example, "$C_{1-4}$ hydroxyalkoxy" is intended to include $C_1$, $C_2$, $C_3$, and $C_4$ hydroxyalkoxy groups.

The term "hydroxy-fluoroalkoxy" represent a hydroxy-fluoroalkyl group as defined above attached through an oxygen linkage (—O—). For example, "$C_{1-4}$ hydroxy-fluoroalkoxy" is intended to include $C_1$, $C_2$, $C_3$, and $C_4$ hydroxy-fluoroalkoxy groups.

The term "cycloalkoxy," as used herein, refers to a cycloalkyl group attached to the parent molecular moiety through an oxygen atom, for example, cyclopropoxy group (—O(cyclopropyl)).

The term "alkoxyalkoxy" as used herein, refers to an alkoxy group attached through an alkoxy group to the patent molecular moiety. For example, "($C_{1-3}$ alkoxy)-($C_{1-6}$ alkoxy)" denotes a $C_{1-3}$ alkoxy group attached through a $C_{1-6}$ alkoxy group to the parent molecular moiety.

The term "alkoxyalkylene" as used herein, refers to an alkoxy group attached through an alkylene group to the patent molecular moiety. For example, "($C_{1-3}$ alkoxy)-($C_{1-3}$ alkylene)" denotes a $C_{1-3}$ alkoxy group attached through a $C_{1-3}$ alkylene to the parent molecular moiety.

The term "fluoroalkoxyalkylene" as used herein, refers to a fluoroalkoxy group attached through an alkylene group. For example, "($C_{1-2}$ fluoroalkoxy)-($C_{1-2}$ alkylene)" denotes a $C_{1-2}$ fluoroalkoxy group attached through a $C_{1-2}$ alkylene to the parent molecular moiety.

The term "alkoxy-fluoroalkylene" as used herein, refers to an alkoxy group attached through a fluoroalkylene group to the patent molecular moiety. For example, "($C_{1-3}$ alkoxy)-($C_{1-3}$ fluoroalkylene)" denotes a $C_{1-3}$ alkoxy group attached through a $C_{1-3}$ fluoroalkylene to the parent molecular moiety.

The term "deuteroalkoxy-deuteroalkylene" as used herein, refers to a deuteroalkoxy group attached through a deuteroalkylene group to the patent molecular moiety. For example, "($C_{1-3}$ deuteroalkoxy)-($C_{1-3}$ deuteroalkylene)" denotes a $C_{1-3}$ deuteroalkoxy group attached through a $C_{1-3}$ deuteroalkylene to the parent molecular moiety.

The term "alkylthio," as used herein, refers to an alkyl group attached to the parent molecular moiety through a sulfur atom, for example, methylthio group (—$SCH_3$). For example, "$C_{1-3}$ alkylthio" denotes alkylthio groups with one to three carbon atoms.

The term "fluoroalkylthio," as used herein, refers to a fluoroalkyl group attached to the parent molecular moiety through a sulfur atom, for example, trifluoromethylthio group (—SCF$_3$). For example, "C$_{1-3}$ fluoroalkylthio" denotes fluoroalkylthio groups with one to three carbon atoms.

The term "aryl," as used herein, refers to a group of atoms derived from a molecule containing aromatic ring(s) by removing one hydrogen that is bonded to the aromatic ring(s). Representative examples of aryl groups include, but are not limited to, phenyl, naphthyl, indanyl, indenyl, and 1,2,3,4-tetrahydronaphth-5-yl. The aryl ring may be unsubstituted or may contain one or more substituents as valence allows.

The term "benzyl," as used herein, refers to a methyl group in which one of the hydrogen atoms is replaced by a phenyl group. The phenyl ring may be unsubstituted or may contain one or more substituents as valence allows.

The term "aryloxy," as used herein, refers to an aryl group attached through an oxygen group.

The term "phenoxy," as used herein, refers to a phenyl group attached through an oxygen group (—O-phenyl). The phenyl ring may be unsubstituted or may contain one or more substituents as valence allows.

The term "heteroatom" refers to oxygen (O), sulfur (S), and nitrogen (N).

The term "heterocyclo" or "heterocyclyl" may be used interchangeably and refer to non-aromatic 3- to 7-membered monocyclic groups and 6- to 11-membered bicyclic groups, in which at least one of the rings has at least one heteroatom (O, S or N), said heteroatom containing ring preferably having 1 to 3 heteroatoms independently selected from O, S, and/or N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic group may contain only carbon atoms and may be saturated, partially saturated, or unsaturated. The heterocyclo group may be attached at any available nitrogen or carbon atom. The heterocyclo ring may be unsubstituted or may contain one or more substituents as valence allows.

Exemplary monocyclic heterocyclyl groups include oxetanyl, azetidinyl, pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl. Exemplary bicyclic heterocyclo groups include quinuclidinyl.

The term "heteroaryl" refers to substituted and unsubstituted aromatic 5- or 6-membered monocyclic groups and 9- or 10-membered bicyclic groups which have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and tetrahydroquinolinyl.

The term "heteroaryloxy," as used herein, refers to a heteroaryl group attached through an oxygen group to the patent molecular moiety.

The term "arylalkylene" refers to an aryl group attached through an alkylene group to the patent molecular moiety. For example, "aryl(C$_{1-2}$ alkylene)" refers to an aryl group attached through a C$_{1-2}$ alkylene to the parent molecular moiety.

The term "heteroarylalkylene" refers to a heteroaryl group attached through an alkylene group to the patent molecular moiety. For example, "heteroaryl(C$_{1-2}$ alkylene)" refers to a heteroaryl group attached through a C$_{1-2}$ alkylene to the parent molecular moiety.

The term "aryloxyalkylene" refers to an aryloxy group attached through an alkylene group to the patent molecular moiety. For example, "aryloxy-(C$_{1-2}$ alkylene)" refers to an aryloxy group attached through a C$_{1-2}$ alkylene to the parent molecular moiety.

The term "heteroaryloxyalkylene" refers to a heteroaryloxy group attached through an alkylene group to the patent molecular moiety. For example, "heteroaryloxy-(C$_{1-2}$ alkylene)" refers to a heteroaryloxy group attached through a C$_{1-2}$ alkylene to the parent molecular moiety.

The compounds of the present invention can be provided as amorphous solids or crystalline solids. Lyophilization can be employed to provide the compounds as amorphous solids.

It should further be understood that solvates (e.g., hydrates) of the Compounds of the invention are also within the scope of the present invention. The term "solvate" means a physical association of a compound of Formulas (I) to (VIII) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

In addition, compounds of Formulas (I) to (VIII), subsequent to their preparation, can be isolated and purified to obtain a composition containing an amount by weight equal to or greater than 99% of a compound of Formulas (I) to (VIII) ("substantially pure"), which is then used or formulated as described herein. Such "substantially pure" compounds of Formulas (I) to (VIII) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Biology

The term "PAR4 antagonist" denotes an inhibitor of platelet aggregation which binds PAR4 and inhibits PAR4 cleavage and/or signaling. Typically, PAR4 activity is reduced in a dose dependent manner by at least 10%, 20%, 30%, 40%, 50%, 60%, 70%, 80%, 90%, or 100% compared to such activity in a control cell. The control cell is a cell that has not been treated with the compound. PAR4 activity is determined by any standard method in the art, including those described herein (for example calcium mobilization in PAR4 expressing cells, platelet aggregation, platelet activation assays measuring e.g., calcium mobilization, P-selectin or CD40L release, or thrombosis and hemostasis models). In certain embodiments, platelet activation is measured by changes in the platelet cytoplasm, by changes of the platelet membrane, by changes in the levels of analytes released by platelets, by the changes in the morphology of the platelet, by the ability of platelets to form thrombi or platelet aggregates in flowing or stirred whole blood, by the ability of platelets to adhere to a static surface which is derivatized with relevant ligands (e.g., von Willebrand Factor, collagen, fibrinogen, other extracellular matrix proteins, synthetic fragments of any of the proteins, or any combination thereof), by changes in the shape of the platelets, or any combinations thereof. In one embodiment, platelet activation is measured by changes in the levels of one or more analytes released by platelets. For example, the one or more analytes released by platelets can be P-selectin (CD62p), CD63, ATP, or any combination thereof. In a particular embodiment, platelet activation is measured by the level of binding of fibrinogen or GPIIbIIIa antibodies to platelets. In other embodiments, platelet activation is measured by the degree of phosphorylation of vasodilator-stimulated phosphoprotein (VASP) upon platelet activation. In yet other embodiments, platelet activation is measured by the level of platelet-leukocyte aggregates. In certain embodiments, platelet activation is measured by proteomics profiling. The term "PAR4 antagonist" also includes a compound that inhibits both PAR1 and PAR4.

Preferably, compounds of the invention have IC$_{50}$s in the PAR4 FLIPR Assay (described hereinafter) of about 10 μM, preferably 1 μM or less, more preferably 100 nM or less, and even more preferably 10 nM or less. PAR4 FLIPR assay data for compounds of the present invention is presented in the Table.

In some embodiments, the present invention provides a pharmaceutical composition, which includes a pharmaceutically acceptable carrier and a therapeutically effective amount of a compound of Formula I-VIII, preferably, a compound selected from one of the examples, more preferably, Examples 1 to 837, or stereoisomers, tautomers, pharmaceutically acceptable salts, or solvates thereof, alone or in combination with another therapeutic agent.

In some embodiments, the present invention provides a pharmaceutical composition which further includes another therapeutic agent(s). In a preferred embodiment, the present invention provides a pharmaceutical composition, wherein the additional therapeutic agent(s) are an anti-platelet agent or a combination thereof. Preferably, the anti-platelet agent(s) are P2Y12 antagonists and/or aspirin. Preferably, the P2Y12 antagonists are clopidogrel, ticagrelor, or prasugrel. In another preferred embodiment, the present invention provides a pharmaceutical composition, wherein the additional therapeutic agent(s) are an anticoagulant or a combination thereof. Preferably, the anticoagulant agent(s) are a FXa inhibitor, a thrombin inhibitor, or a FXIa inhibitor. Preferably, the FXa inhibitors are apixaban, rivaroxaban, edoxaban, or betrixaban. Preferably, the thrombin inhibitor is dabigatran.

It is desirable to find compounds with advantageous and improved characteristics compared with known anti-platelet agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; (h) improved therapeutic index with less propensity for bleeding; and (h) factors that improve manufacturing costs or feasibility.

As used herein, the term "patient" encompasses all mammalian species.

As used herein, the term "subject" refers to any human or nonhuman organism that could potentially benefit from treatment with a PAR4 antagonist. Exemplary subjects include human beings of any age with risk factors for cardiovascular disease, or patients that have already experienced one episode of cardiovascular disease. Common risk factors include, but are not limited to, age, male sex, hypertension, smoking or smoking history, elevation of triglycerides, elevation of total cholesterol or LDL cholesterol.

In some embodiments, the subject is a species having a dual PAR1/PAR4 platelet receptor repertoire. As used herein, the term "dual PAR1/PAR4 platelet receptor repertoire" means that a subject expresses PAR1 and PAR4 in platelets or their precursors. Exemplary subjects having a dual PAR1/PAR4 platelet receptor repertoire include human beings, non-human primates, and guinea pigs.

In other embodiments, the subject is a species having a dual PAR3/PAR4 platelet receptor repertoire. As used herein, the term "dual PAR3/PAR4 platelet receptor repertoire" means that a subject expresses PAR3 and PAR4 in platelets or their precursors. Exemplary subjects having a dual PAR3/PAR4 platelet receptor repertoire include rodents and rabbits.

As used herein, "treating" or "treatment" cover the treatment of a disease-state in a mammal, particularly in a human, and include: (a) inhibiting the disease-state, i.e., arresting its development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit and/or antagonize PAR4 and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi) within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid internal, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, atrial fibrillation is frequently associated with thromboembolic disorders. Risk factors for atrial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population. (Levitan, N. et al., *Medicine* (Baltimore), 78(5):285-291 (1999); Levine M. et al., *N. Engl. J Med.,* 334(11):677-681 (1996); Blom, J. W. et al., *JAMA,* 293(6):715-722 (2005).) Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and antiangiogenic drugs. Thus, it is common clinical practice to dose patients having advanced tumors with heparin or low molecular heparin to prevent thromboembolic disorders. A number of low molecular weight heparin preparations have been approved by the FDA for these indications.

The term "pharmaceutical composition," as used herein, means any composition, which contains at least one therapeutically or biologically active agent and is suitable for administration to the patient. Any of these formulations can be prepared by well-known and accepted methods of the art. See, for example, Gennaro, A. R., ed., *Remington: The Science and Practice of Pharmacy,* 20th Edition, Mack Publishing Co., Easton, Pa. (2000).

The invention includes administering to a subject a pharmaceutical composition that includes a compound that binds to PAR4 and inhibits PAR4 cleavage and/or signaling (referred to herein as a "PAR4 antagonist" or "therapeutic compound").

The pharmaceutical composition is administered using methods known in the art. Preferably, the compound is administered orally, rectally, nasally, by inhalation, topically or parenterally, e.g., subcutaneously, intraperitoneally, intramuscularly, and intravenously. The compound is optionally formulated as a component of a cocktail of therapeutic drugs to treat a thromboembolic disorder. In one embodiment, the pharmaceutical composition is administered orally.

The therapeutic compounds described herein are formulated into pharmaceutical compositions utilizing conventional methods. For example, a PAR4 antagonist is formulated in a capsule or a tablet for oral administration. Capsules may contain any standard pharmaceutically acceptable materials such as gelatin or cellulose. Tablets may be formulated in accordance with conventional procedures by compressing mixtures of a therapeutic compound with a solid carrier and a lubricant. Examples of solid carriers include starch and sugar bentonite. The compound is administered in the form of a hard shell tablet or a capsule containing a binder, e.g., lactose or mannitol, a conventional filler, and a tableting agent. Other formulations include an ointment, suppository, paste, spray, patch, cream, gel, resorbable sponge, or foam. Such formulations are produced using methods well known in the art. The compositions of the invention are also useful for parenteral administration, such as intravenous, subcutaneous, intramuscular, and intraperitoneal. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

The preferred dose of the PAR4 antagonist is a biologically active dose. A biologically active dose is a dose that will inhibit cleavage and/or signaling of PAR4 and have an anti-thrombotic effect. Desirably, the PAR4 antagonist has the ability to reduce the activity of PAR4 by at least 5%, 10%, 20%, 30%, 40%, 50%, 60%, 70%, 80%, 90%, 100%, or more than 100% below untreated control levels. The levels of PAR4 in platelets is measured by any method known in the art, including, for example, receptor binding assay, platelet aggregation, platelet activation assays (e.g., p-selectin expression by FACS), Western blot or ELISA analysis using PAR4 cleavage sensitive antibodies. Alternatively, the biological activity of PAR4 is measured by assessing cellular signaling elicited by PAR4 (e.g., calcium mobilization or other second messenger assays).

In some embodiments, a therapeutically effective amount of a PAR4 compound is preferably from about less than 100 mg/kg, 50 mg/kg, 10 mg/kg, 5 mg/kg, 1 mg/kg, or less than 1 mg/kg. In a more preferred embodiment, the therapeutically effective amount of the PAR4 compound is less than 5 mg/kg. In a most preferred embodiment, the therapeutically effective amount of the PAR4 compound is less than 1 mg/kg. Effective doses vary, as recognized by those skilled in the art, depending on route of administration and excipient usage.

The activity of the PAR4 antagonists of the present invention can be measured in a variety of in vitro assays. Exemplary assays are shown below.

The Fluorometric Imaging Plate Reader (FLIPR) assay is an exemplary in vitro assay for measuring the activity of the PAR4 antagonists of the present invention. In this assay, intracellular calcium mobilization is induced in PAR4 expressing cells by a PAR4 agonist and calcium mobilization is monitored.

AYPGKF is a known PAR4 agonist. An alternative PAR4 agonist is H-Ala-Phe(4-F)-Pro-Gly-Trp-Leu-Val-Lys-Asn-Gly-NH$_2$. As shown in Example B of WO2013/163279, H-Ala-Phe(4-F)-Pro-Gly-Trp-Leu-Val-Lys-Asn-Gly-NH$_2$ was validated as a PAR4 agonist in the FLIPR assay. A side-by-side comparison of the IC$_{50}$ values of ~180 compounds were performed using AYPGKF versus H-Ala-Phe(4-F)-Pro-Gly-Trp-Leu-Val-Lys-Asn-Gly-NH$_2$. The results demonstrated a strong correlation between the two assays. Additionally, H-Ala-Phe(4-F)-Pro-Gly-Trp-Leu-Val-Lys-Asn-Gly-NH$_2$ has improved agonist activity as compared to AYPGKF with an $EC_{50}$ that is 10 fold lower than the $EC_{50}$ for AYPGKF in the FLIPR assay. H-Ala-Phe(4-F)-Pro-Gly-Trp-Leu-Val-Lys-Asn-Gly-$NH_2$ can be synthesized using methods well known to those of skill in the art.

The FLIPR assay can also be used as a counterscreen to test agonist activity or PAR1 antagonist activity in a cell line that expresses both PAR1 and PAR4. The PAR1 antagonist activity can be tested by the ability of the compound to inhibit calcium mobilization induced by the PAR1 agonist peptide SFLLRN or other PAR1 agonist peptides.

The compounds of the current invention can be tested in vitro for their ability to inhibit platelet aggregation induced by gamma-thrombin as shown below. Gamma-thrombin, a proteolytic product of alpha-thrombin which no longer interacts with PAR1, selectively cleaves and activates PAR4 (Soslau, G. et al., "Unique pathway of thrombin-induced platelet aggregation mediated by glycoprotein Ib", *J. Biol. Chem.*, 276:21173-21183 (2001)). Platelet aggregation can be monitored in a 96-well microplate aggregation assay format or using standard platelet aggregometer. The aggregation assay can also be employed to test the selectivity of the compound for inhibiting platelet aggregation induced by PAR4 agonist peptides, PAR1 agonist peptide, ADP, or thromboxane analogue U46619.

The compounds of the current invention can be tested in vitro for their ability to inhibit platelet aggregation induced by alpha-thrombin as shown below. Alpha-thrombin activates both PAR1 and PAR4. The ability of a selective PAR4 antagonist of the present invention to inhibit platelet aggregation can be measured using a standard optical aggregometer.

The compounds of the current invention can be tested in vitro for their ability to inhibit platelet aggregation induced by tissue factor as shown below. The conditions in this assay mimic the physiological events during thrombus formation. In this assay, platelet aggregation in human platelet rich plasma (PRP) is initiated by the addition of tissue factor and $CaCl_2$. Tissue factor, the initiator of the extrinsic coagulation cascade, is highly elevated in human atherosclerotic plaque. Exposure of blood to tissue factor at the atherosclerotic site triggers a robust generation of thrombin and induces the formation of obstructive thrombi.

The activity of the PAR4 antagonists of the present invention can also be measured in a variety of in vivo assays. Exemplary mammals that can provide models of thrombosis and hemostasis to test the effectiveness of the PAR4 antagonists of the present invention as antithrombotic agents include, but are not limited to, guinea pigs and primates. Relevant efficacy models include, but are not limited to, electrically-induced carotid arterial thrombosis, $FeCl_3$-induced carotid artery thrombosis and arteriovenous-shunt thrombosis. Models of kidney bleeding time, renal bleeding time and other bleeding time measurements can be used to assess the bleeding risk of the antithrombotic agents described in the current invention.

Assays

Materials
1) PAR1 and PAR4 Agonist Peptides

SFFLRR is a known high affinity PAR1 selective agonist peptide. (Reference: Seiler, S. M., "Thrombin receptor antagonists", *Seminars in Thrombosis and Hemostasis*, 22(3):223-232 (1996).) The PAR4 agonist peptides AYPGKF and H-Ala-Phe(4-F)-Pro-Gly-Trp-Leu-Val-Lys-Asn-Gly-$NH_2$ were synthesized. H-Ala-Phe(4-F)-Pro-Gly-Trp-Leu-Val-Lys-Asn-Gly-$NH_2$ showed improved PAR4 agonist activity over AYPGKF in the FLIPR assay ($EC_{50}$ value of 8 µM for H-Ala-Phe(4-F)-Pro-Gly-Trp-Leu-Val-Lys-Asn-Gly-$NH_2$ and 60 µM for AYPGKF) and in washed platelet aggregation assay ($EC_{50}$ value of 0.9 µM for H-Ala-Phe(4-F)-Pro-Gly-Trp-Leu-Val-Lys-Asn-Gly-$NH_2$ and 12 µM for AYPGKF).

2) PAR4 Expressing Cells

HEK293 cells stably expressing PAR4 were generated by a standard method of transfection of human PAR4 (F2R23) cDNA expression vector and selected based on PAR4 protein expression or mRNA expression. Those cells demonstrated functional responses to PAR4 agonist peptide-induced intracellular calcium elevation using FLIPR® (Fluorometric Imaging Plate Reader; Molecular Devices Corp.). These cells also express endogenous PAR1 and can elicit calcium signal upon stimulation with PAR1 agonist peptide. Therefore, the same cells were also used to determine selectivity against PAR1 and agonist activity for both receptors. Cells from HEK293 PAR4 Clone 1.2A (BMS Arctic ID 383940) were propagated and used for calcium mobilization studies.

3) Preparation of Platelet Rich Plasma (PRP)

Human blood was collected in 3.8% sodium citrate at a ratio of 1 ml per 9 ml blood and centrifuged in a Sorvall® RT6000B centrifuge at 900 revolution per minute (rpm) at room temperature (RT) for 15 minutes. PRP was collected and used for aggregation assay. Refludan (Berlex Labs, Wayne, NJ), a recombinant hirudin, at a final concentration of 1 unit/mL was added to the sample to selectively prevent PAR1 activation induced by residual alpha-thrombin contamination. The remaining blood sample was centrifuged at 2500 rpm at room temperature for 5 minutes to collect platelet-poor plasma (PPP).

4) Preparation of Washed Platelets (WP)

Human blood was collected in ACD (85 mM tri-sodium citrate, 78 mM citric acid, 110 mM D-glucose, pH 4.4) at a ratio of 1.4 ml per 10 ml blood. PRP was isolated by centrifugation at 170 g for 14 minutes and platelets were further pelleted by centrifugation at 1300 g for 6 minutes. Platelets were washed once with 10 ml ACD containing 1 mg/ml bovine serum albumin. Platelets were resuspended at ~$2.5 \times 10^8$/ml in Tyrode's Buffer (137 mM NaCl, 2 mM KCl, 1.0 mM $MgCl_2$, 1 mM $CaCl_2$, 5 mM glucose, 20 mM HEPES pH 7.4).

FLIPR Assay in PAR4-Expressing HEK293 Cells

FLIPR-based calcium mobilization assay in HEK293 cells was used to measure PAR4 antagonism, agonism, and selectivity against PAR1. The activity of the PAR4 antagonists of the present invention were tested in PAR4 expressing cells by monitoring H-Ala-Phe(4-F)-Pro-Gly-Trp-Leu-Val-Lys-Asn-Gly-$NH_2$-induced intracellular calcium mobilization. Counter screens for agonist activity and PAR1 antagonist activity were also performed. Briefly, PAR1/PAR4-expressing HEK293 cells were grown in DMEM (Life Technology, Grand Island, NY) containing 10% heat-inactivated FBS, 1% Penicillin-Streptomycin, 10 µg/mL blasticidin, and 100 µg/mL Zeocin at 37° C. with 5% $CO_2$. Cells were plated overnight prior to the experiment in a black 384-well Purecoat Amine clear bottom plate (Becton Dickinson Biosciences, San Jose, CA) at 10,000 cells/well in 30 µL growth medium and incubated in a humidified chamber at 37° C. with 5% $CO_2$ overnight. Prior to compound addition, the cell medium was replaced with 40 µL of 1× calcium and magnesium-containing Hank's Balanced Saline Solution (HBSS) (with 20 mM HEPES) and 1:1000 diluted fluorescent calcium indicator (Codex Biosolutions, Gaithersburg, MD). After a 30 minute incubation period at 37° C. and a further 30 minute incubation and equilibration period at room temperature, 20 µL test compound (diluted in 1×HBSS buffer) was added at various concentrations at 0.17% dimethyl sulfoxide (DMSO) final concentration. Changes in fluorescence intensity were measured using a Functional Drug Screening System (FDSS, Hamamatsu, Japan) to determine agonist activities. The cells were then incubated for 30 minutes at room temperature followed by addition of 20 µL of agonist peptide for antagonist activity measurement. The PAR4 agonist peptide (H-Ala-Phe(4-F)-Pro-Gly-Trp-Leu-Val-Lys-Asn-Gly-NH$_2$) and the PAR1 agonist peptide (SFFLRR) were routinely tested to ensure a proper response at the EC$_{50}$ value in the assay (~5 µM for PAR4 agonist peptide and ~2 µM for PAR1 agonist peptide). Compound potency was derived from 11-point concentration-response curves.

Gamma Thrombin Induced Platelet Aggregation Assays

The ability of the compounds of the current invention to inhibit platelet aggregation induced by gamma-thrombin was tested in a 96-well microplate aggregation assay format. Briefly, 90 µL of PRP or washed platelets were pre-incubated for 5 minutes at 37° C. with 3-fold serially diluted test compound, which was prepared as a 100-fold stock solution in dimethyl sulfoxide (DMSO). Aggregation was initiated by addition of 10 µL of gamma-thrombin (Haematologic Technologies, Inc. Essex Junction, VT) at 50-100 nM final concentration, which was titrated daily to achieve 80% platelet aggregation. The plate was then placed into a SpectraMax® Plus Plate Reader (Molecular Devices) at 37° C. Platelet aggregation was monitored at a wavelength of 405 nm using a kinetic analysis mode. Prior to the first data collection time point, the plate was shaken for 10 seconds to allow thorough mixing. Data was subsequently collected every 10 seconds for up to 7 minutes total. Data was collected using SoftMax® 5.4.1 software and exported to Microsoft Excel for analysis. The optical density (OD) values at the time point that achieved 75% platelet activation by agonist alone were used for analysis. The OD value from a PRP sample without any treatment served as ODmaximum, and the OD value from a PPP sample containing no platelets served as the ODminimum. Inhibition of platelet aggregation (IPA) was calculated based on the formula: % IPA=(100−100*[ODcompound−ODminimum]/[ODmaximum−ODminimum]). The IC$_{50}$ value of the test compound was calculated by fitting the % IPA values to the one-site concentration response equation: Y=A+(B−A)/{1+(C/X)^D}, using XLfit for 32 bit Excel® Version 2 Build 30 (ID Business Solutions Limited).

The aggregation assays were also employed to test the selectivity of the compound against other platelet receptors by using SFFLRR for PAR$_1$, collagen (Chrono-Log, Havertown, PA) for collagen receptors, ADP for P2Y1 and P2Y12 and U46619 (Cayman Chemical, Ann Arbor, MI) for thromboxane receptors.

Alpha-Thrombin Induced Platelet Aggregation Assays

The ability of PAR4 antagonists to inhibit platelet aggregation induced by alpha-thrombin can be tested using human washed platelets. The antagonists are pre-incubated with washed platelets for 20 min. Aggregation is initiated by addition of 1.5 nM alpha-thrombin (Haematologic Technologies, Essex Junction, VT) to 300 µl of washed platelets at stirring speed of 1000 rpm. Platelet aggregation is monitored using an Optical Aggregometer (Chrono-Log, Havertown, PA) and the area under the curve (AUC) at 6 min was measured. IC$_{50}$ values are calculated using vehicle control as 0% inhibition.

Tissue Factor-Induced Platelet Aggregation Assay

The ability of PAR1 or PAR4 antagonists to inhibit platelet aggregation induced by endogenous thrombin can be tested in a tissue factor driven aggregation assay. Aggregation is initiated by addition of CaCl$_2$ and recombinant human tissue factor, which results in the generation of thrombin through activation of the coagulation pathway in the plasma. Anticoagulant agents such as corn trypsin inhibitor (Haematologic Technologies, Essex Junction, VT) at 50 µg/ml and PEFABLOC® FG (Centerchem, Norwalk, CT) are also added to the sample to prevent fibrin clot formation during the time of the study. Platelet aggregation is monitored using standard instrumentation including optical aggregometer or impedance aggregometer.

The following table sets out the results obtained employing various compounds of the invention tested in the PAR4 FLIPR assay.

TABLE

| Ex. No. | PAR4 FLIPR assay (IC50, nM) |
| --- | --- |
| 1 | 29 |
| 2 | 11 |
| 3 | 240 |
| 4 | 17 |
| 5 | 880 |
| 6 | 130 |
| 7 | 800 |
| 8 | 8.1 |
| 9 | 220 |
| 10 | 2.2 |
| 11 | 1700 |
| 12 | 2.0 |
| 13 | 3.5 |
| 14 | 6.8 |
| 15 | 38 |
| 16 | 80 |
| 17 | 13 |
| 18 | 98 |
| 19 | 41 |
| 20 | 30 |
| 21 | 3.3 |
| 22 | 1.8 |
| 23 | 5.3 |
| 24 | 2.0 |
| 25 | 130 |
| 26 | 3.3 |
| 27 | 5.4 |
| 28 | 3.0 |
| 29 | 1.4 |
| 30 | 4.7 |
| 31 | 240 |
| 32 | 3.0 |
| 33 | 120 |
| 34 | 1.6 |
| 35 | 54 |
| 36 | 7.7 |
| 37 | 22 |
| 38 | 2.1 |
| 39 | 10 |
| 40 | 36 |
| 41 | 400 |
| 42 | 5.2 |
| 43 | 170 |
| 44 | 220 |

TABLE-continued

| Ex. No. | PAR4 FLIPR assay (IC50, nM) |
|---|---|
| 45 | 99 |
| 46 | 17 |
| 47 | 34 |
| 48 | 2.1 |
| 49 | 9.7 |
| 50 | 92 |
| 51 | 180 |
| 52 | 4.7 |
| 53 | 9.8 |
| 54 | 94 |
| 55 | 14 |
| 56 | 4.7 |
| 58 | 3.0 |
| 59 | 5.0 |
| 60 | 19 |
| 61 | 43 |
| 62 | 100 |
| 63 | 2.9 |
| 64 | 7.4 |
| 65 | 31 |
| 66 | 28 |
| 67 | 2.9 |
| 68 | 120 |
| 69 | 36 |
| 70 | 34 |
| 71 | 160 |
| 72 | 1.0 |
| 73 | 2.3 |
| 74 | 9.3 |
| 75 | 14 |
| 76 | 2.1 |
| 77 | 130 |
| 78 | 39 |
| 79 | 2.2 |
| 80 | 21 |
| 81 | 1.5 |
| 82 | 280 |
| 83 | 11 |
| 84 | 2.5 |
| 85 | 8.5 |
| 86 | 7.2 |
| 87 | 2.0 |
| 89 | 1.4 |
| 90 | 84 |
| 91 | 62 |
| 92 | 2.0 |
| 93 | 0.3 |
| 94 | 1.4 |
| 95 | 0.8 |
| 96 | 1.1 |
| 97 | 1.7 |
| 98 | 0.3 |
| 99 | 0.6 |
| 100 | 0.5 |
| 101 | 0.2 |
| 102 | 0.9 |
| 103 | 2.5 |
| 104 | 1.7 |
| 105 | 8.1 |
| 106 | 1.6 |
| 107 | 2.8 |
| 108 | 1100 |
| 109 | 8.3 |
| 110 | 12 |
| 111 | 1.1 |
| 112 | 2.0 |
| 113 | 3.0 |
| 114 | 1600 |
| 115 | 1.3 |
| 116 | 1.4 |
| 117 | 0.5 |
| 118 | 2.2 |
| 119 | 16 |
| 120 | 28 |
| 121 | 0.7 |
| 122 | 3.9 |
| 123 | 1.5 |
| 124 | 1.8 |
| 125 | 2.0 |
| 126 | 1.2 |
| 127 | 8.3 |
| 128 | 2.2 |
| 129 | 3.2 |
| 130 | 460 |
| 131 | 890 |
| 132 | 59 |
| 133 | 570 |
| 134 | 120 |
| 135 | 2200 |
| 136 | 29 |
| 137 | 29 |
| 138 | 33 |
| 139 | 3.9 |
| 140 | 21 |
| 141 | 80 |
| 142 | 5.6 |
| 143 | 36 |
| 144 | 0.3 |
| 145 | 4.5 |
| 146 | 7.0 |
| 147 | 1.7 |
| 148 | 48 |
| 149 | 4.2 |
| 150 | 94 |
| 151 | 2000 |
| 152 | 38 |
| 153 | 16 |
| 154 | 3.8 |
| 155 | 0.8 |
| 156 | 1.4 |
| 157 | 31 |
| 158 | 0.7 |
| 159 | 25 |
| 160 | 1.2 |
| 161 | 0.7 |
| 162 | 270 |
| 163 | 0.5 |
| 164 | 0.5 |
| 165 | 1.2 |
| 166 | 2.8 |
| 167 | 4.5 |
| 168 | 2.0 |
| 169 | 0.4 |
| 170 | 0.3 |
| 171 | 0.6 |
| 172 | 1.7 |
| 173 | 2.7 |
| 174 | 3.0 |
| 175 | 23 |
| 176 | 980 |
| 177 | 190 |
| 178 | 13 |
| 179 | 18 |
| 180 | 2.7 |
| 181 | 1.2 |
| 182 | 22 |
| 183 | 0.6 |
| 184 | 2300 |
| 185 | 6.5 |
| 186 | 17 |
| 187 | 390 |
| 188 | 580 |
| 189 | 140 |
| 190 | 1700 |
| 191 | 6.4 |
| 192 | 2.8 |
| 193 | 1.2 |
| 194 | 2.5 |
| 195 | 32 |
| 196 | 2.3 |
| 197 | 1.3 |
| 198 | 0.6 |
| 199 | 2.5 |
| 200 | 1.6 |
| 201 | 1.3 |
| 202 | 0.9 |

TABLE-continued

| Ex. No. | PAR4 FLIPR assay (IC50, nM) |
|---|---|
| 203 | 4.1 |
| 204 | 3.1 |
| 205 | 51 |
| 206 | 0.7 |
| 207 | 0.9 |
| 208 | 1.1 |
| 209 | 1.1 |
| 210 | 0.3 |
| 211 | 21 |
| 212 | 2.4 |
| 213 | 5.8 |
| 214 | 4.3 |
| 215 | 2.9 |
| 216 | 160 |
| 217 | 18 |
| 218 | 2.5 |
| 219 | 5.5 |
| 220 | 2.6 |
| 221 | 21 |
| 222 | 1.0 |
| 223 | 10 |
| 224 | 15 |
| 225 | 54 |
| 226 | 140 |
| 227 | 160 |
| 228 | 890 |
| 229 | 3.9 |
| 230 | 2.2 |
| 231 | 1.0 |
| 232 | 0.7 |
| 233 | 0.4 |
| 234 | 1.4 |
| 235 | 2.2 |
| 236 | 140 |
| 237 | 170 |
| 238 | 1300 |
| 239 | 7.9 |
| 240 | 72 |
| 241 | 5.4 |
| 242 | 120 |
| 243 | 1.2 |
| 244 | 2.0 |
| 245 | 92 |
| 246 | 140 |
| 247 | 19 |
| 248 | 19 |
| 249 | 6.9 |
| 250 | 31 |
| 251 | 17 |
| 252 | 0.5 |
| 253 | 0.6 |
| 254 | 1.5 |
| 255 | 0.8 |
| 256 | 1.2 |
| 257 | 2.1 |
| 258 | 2.8 |
| 259 | 14 |
| 260 | 4.8 |
| 261 | 1.2 |
| 262 | 0.8 |
| 263 | 0.8 |
| 264 | 8.3 |
| 265 | 6.8 |
| 266 | 2.2 |
| 267 | 0.8 |
| 268 | 0.9 |
| 269 | 3.6 |
| 270 | 17 |
| 271 | 1.5 |
| 272 | 3.2 |
| 273 | 4.3 |
| 274 | 5.7 |
| 275 | 0.9 |
| 276 | 1.2 |
| 277 | 9.0 |
| 278 | 4.6 |
| 279 | 18 |
| 280 | 4.3 |
| 281 | 3.6 |
| 282 | 1.1 |
| 283 | 1.9 |
| 284 | 5.9 |
| 285 | 16 |
| 286 | 0.5 |
| 287 | 8.5 |
| 288 | 8.6 |
| 289 | 1.3 |
| 290 | 6.0 |
| 291 | 11 |
| 292 | 0.8 |
| 293 | 1.0 |
| 294 | 5.2 |
| 295 | 0.7 |
| 296 | 1.2 |
| 297 | 5.7 |
| 298 | 2.1 |
| 299 | 10 |
| 300 | 0.9 |
| 301 | 15 |
| 302 | 3.2 |
| 303 | 0.9 |
| 304 | 2.3 |
| 305 | 1.0 |
| 306 | 1.0 |
| 307 | 0.9 |
| 308 | 3.6 |
| 309 | 3.3 |
| 310 | 9.1 |
| 311 | 93 |
| 312 | 6.7 |
| 313 | 2.9 |
| 314 | 10 |
| 315 | 3.3 |
| 316 | 4.9 |
| 317 | 4.5 |
| 318 | 7.8 |
| 319 | 7.3 |
| 320 | 3.4 |
| 321 | 3.1 |
| 322 | 5.1 |
| 323 | 15 |
| 324 | 42 |
| 325 | 0.7 |
| 326 | 1.1 |
| 327 | 5.2 |
| 328 | 1.4 |
| 329 | 1.1 |
| 330 | 57 |
| 331 | 9.2 |
| 332 | 2.4 |
| 333 | 1.7 |
| 334 | 29 |
| 335 | 2.5 |
| 336 | 5.5 |
| 337 | 0.7 |
| 338 | 2.0 |
| 339 | 1.6 |
| 340 | 1.5 |
| 341 | 15 |
| 342 | 11 |
| 343 | 0.7 |
| 344 | 11 |
| 345 | 0.6 |
| 346 | 3.7 |
| 347 | 0.8 |
| 348 | 4.4 |
| 349 | 2.7 |
| 350 | 2.8 |
| 351 | 2.7 |
| 352 | 390 |
| 353 | 22 |
| 354 | 1.2 |
| 355 | 17 |
| 356 | 2.1 |
| 357 | 6.7 |
| 358 | 270 |

| Ex. No. | PAR4 FLIPR assay (IC50, nM) |
|---|---|
| 359 | 170 |
| 360 | 160 |
| 361 | 5.5 |
| 362 | 4.1 |
| 363 | 1700 |
| 364 | 19 |
| 365 | 2.5 |
| 366 | 550 |
| 367 | 12 |
| 369 | 13 |
| 370 | 5.8 |
| 371 | 1.8 |
| 372 | 1.3 |
| 373 | 0.9 |
| 374 | 110 |
| 375 | 1.7 |
| 376 | 72 |
| 377 | 4.3 |
| 378 | 8.7 |
| 379 | 1.7 |
| 380 | 2.3 |
| 381 | 1.4 |
| 382 | 1.3 |
| 383 | 590 |
| 384 | 18 |
| 385 | 2.3 |
| 386 | 7.8 |
| 387 | 1.5 |
| 388 | 0.7 |
| 389 | 0.4 |
| 390 | 3.6 |
| 391 | 2.0 |
| 392 | 3.1 |
| 393 | 30 |
| 394 | 130 |
| 395 | 5.8 |
| 396 | 4.6 |
| 397 | 210 |
| 398 | 8.6 |
| 399 | 3.9 |
| 400 | 2.0 |
| 401 | 2.7 |
| 402 | 3.7 |
| 403 | 1.7 |
| 404 | 2.2 |
| 405 | 1.9 |
| 406 | 3.5 |
| 407 | 0.9 |
| 408 | 3.2 |
| 409 | 0.4 |
| 410 | 0.3 |
| 411 | 4.4 |
| 412 | 0.3 |
| 413 | 3.4 |
| 414 | 7.0 |
| 415 | 3.1 |
| 416 | 32 |
| 417 | 11 |
| 418 | 1.3 |
| 419 | 2.0 |
| 420 | 2.2 |
| 421 | 1.8 |
| 422 | 2.2 |
| 423 | 4.2 |
| 426 | 5.4 |
| 427 | 7.6 |
| 428 | 5.9 |
| 429 | 0.5 |
| 430 | 0.9 |
| 431 | 1.1 |
| 432 | 0.4 |
| 433 | 0.6 |
| 434 | 1.4 |
| 435 | 0.9 |
| 436 | 1.5 |
| 437 | 4.9 |
| 438 | 1.9 |
| 439 | 0.9 |
| 440 | 0.8 |
| 441 | 0.9 |
| 442 | 0.8 |
| 443 | 0.6 |
| 444 | 0.8 |
| 445 | 3.2 |
| 446 | 2.3 |
| 447 | 21 |
| 448 | 2.1 |
| 449 | 0.3 |
| 450 | 0.5 |
| 451 | 0.7 |
| 452 | 0.4 |
| 453 | 0.6 |
| 454 | 1.3 |
| 455 | 0.8 |
| 456 | 0.7 |
| 457 | 0.4 |
| 458 | 0.5 |
| 459 | 0.9 |
| 460 | 0.9 |
| 461 | 0.4 |
| 462 | 0.2 |
| 463 | 0.7 |
| 464 | 1.5 |
| 465 | 1.4 |
| 466 | 0.7 |
| 467 | 1.9 |
| 468 | 0.8 |
| 470 | 2.2 |
| 471 | 5.2 |
| 472 | 4.6 |
| 473 | 3.4 |
| 474 | 11 |
| 475 | 4.8 |
| 476 | 10 |
| 477 | 3.0 |
| 478 | 9.1 |
| 479 | 1.4 |
| 480 | 3.4 |
| 481 | 0.6 |
| 482 | 0.6 |
| 483 | 0.8 |
| 484 | 1.0 |
| 485 | 1.6 |
| 486 | 1.5 |
| 487 | 1.3 |
| 488 | 14 |
| 489 | 9.1 |
| 490 | 5.1 |
| 491 | 0.4 |
| 492 | 7.4 |
| 493 | 21 |
| 494 | 1.8 |
| 495 | 15 |
| 496 | 1.9 |
| 497 | 1.3 |
| 498 | 1.3 |
| 499 | 4.4 |
| 500 | 3.8 |
| 501 | 4.0 |
| 502 | 1.7 |
| 512 | 1.2 |
| 513 | 1.1 |
| 514 | 1.9 |
| 515 | 2.6 |
| 516 | 2.0 |
| 517 | 1.1 |
| 518 | 13 |
| 519 | 16 |
| 520 | 77 |
| 521 | 24 |
| 522 | 20 |
| 523 | 2.6 |
| 524 | 84 |
| 525 | 2.3 |
| 526 | 2.0 |
| 527 | 1.4 |

| Ex. No. | PAR4 FLIPR assay (IC50, nM) |
|---|---|
| 528 | 5.0 |
| 529 | 0.9 |
| 530 | 1.8 |
| 531 | 0.7 |
| 532 | 1.7 |
| 533 | 0.7 |
| 534 | 0.9 |
| 535 | 5.2 |
| 536 | 4.9 |
| 539 | 6.5 |
| 540 | 3.0 |
| 541 | 3.4 |
| 542 | 1.6 |
| 543 | 1.3 |
| 544 | 34 |
| 545 | 1.5 |
| 546 | 14 |
| 547 | 5.2 |
| 549 | 1.0 |
| 550 | 0.4 |
| 552 | 0.7 |
| 553 | 1.2 |
| 554 | 0.7 |
| 555 | 1.1 |
| 556 | 0.7 |
| 557 | 0.7 |
| 558 | 1.5 |
| 559 | 0.9 |
| 560 | 1.4 |
| 561 | 53 |
| 562 | 1.6 |
| 563 | 2.8 |
| 564 | 3.7 |
| 565 | 3.0 |
| 566 | 1.8 |
| 567 | 5.9 |
| 568 | 2.4 |
| 569 | 8.2 |
| 570 | 6.6 |
| 571 | 1.0 |
| 572 | 0.9 |
| 573 | 1.6 |
| 574 | 2.0 |
| 575 | 0.6 |
| 576 | 1.2 |
| 577 | 1.0 |
| 578 | 5.8 |
| 579 | 3.3 |
| 580 | 1.1 |
| 581 | 4.1 |
| 582 | 5.3 |
| 589 | 0.8 |
| 590 | 25 |
| 591 | 7.0 |
| 592 | 0.7 |
| 596 | 130 |
| 597 | 15 |
| 598 | 3.7 |
| 599 | 5.6 |
| 600 | 2.4 |
| 601 | 3.5 |
| 602 | 6.4 |
| 603 | 2.1 |
| 604 | 17 |
| 605 | 0.7 |
| 606 | 0.4 |
| 607 | 0.2 |
| 608 | 0.5 |
| 609 | 1.9 |
| 610 | 4.3 |
| 611 | 2.1 |
| 613 | 65 |
| 614 | 30 |
| 615 | 870 |
| 616 | 4200 |
| 618 | 3.8 |
| 621 | 8.0 |
| 622 | 350 |
| 623 | 320 |
| 624 | 0.7 |
| 625 | 1.8 |
| 626 | 7.2 |
| 627 | 1400 |
| 628 | 1.4 |
| 629 | 2.2 |
| 630 | 1.4 |
| 631 | 5.3 |
| 632 | 10 |
| 633 | 2.6 |
| 634 | 44 |
| 635 | 10 |
| 636 | 3.0 |
| 637 | 2.1 |
| 638 | 2.7 |
| 639 | 1.4 |
| 640 | 8.0 |
| 641 | 250 |
| 642 | 4.6 |
| 643 | 5.3 |
| 644 | 21 |
| 645 | 4.9 |
| 646 | 3.8 |
| 647 | 19 |
| 648 | 3.0 |
| 649 | 7.4 |
| 650 | 5.6 |
| 651 | 4.3 |
| 652 | 11 |
| 653 | 0.83 |
| 654 | 1.0 |
| 655 | 1.1 |
| 656 | 2.4 |
| 657 | 1.1 |
| 658 | 3.0 |
| 659 | 2.1 |
| 660 | 2.0 |
| 661 | 55 |
| 662 | 77 |
| 663 | 7.0 |
| 664 | 0.9 |
| 665 | 1.7 |
| 666 | 1.1 |
| 667 | 5.6 |
| 668 | 7.3 |
| 669 | 2.3 |
| 671 | 1.9 |
| 672 | 1.9 |
| 673 | 39 |
| 674 | 20 |
| 675 | 10 |
| 676 | 3.2 |
| 677 | 3.8 |
| 678 | 1.0 |
| 679 | 2.5 |
| 680 | 0.8 |
| 681 | 0.4 |
| 682 | 0.9 |
| 683 | 0.7 |
| 684 | 0.7 |
| 685 | 1.7 |
| 686 | 9.9 |
| 687 | 0.9 |
| 688 | 4.5 |
| 689 | 0.3 |
| 690 | 0.3 |
| 691 | 0.9 |
| 692 | 1.8 |
| 693 | 1.3 |
| 694 | 2.1 |
| 695 | 1.0 |
| 696 | 2.6 |
| 697 | 2.9 |
| 698 | 17 |
| 699 | 1.1 |
| 700 | 0.9 |
| 701 | 2.7 |

TABLE-continued

| Ex. No. | PAR4 FLIPR assay (IC50, nM) |
|---|---|
| 702 | 4.3 |
| 708 | 2.6 |
| 709 | 0.4 |
| 710 | 1.8 |
| 711 | 2.4 |
| 712 | 3.2 |
| 713 | 1.8 |
| 714 | 1.2 |
| 715 | 0.9 |
| 716 | 2.0 |
| 717 | 1.6 |
| 718 | 1.7 |
| 719 | 1.7 |
| 720 | 3.2 |
| 721 | 2.6 |
| 722 | 1.4 |
| 723 | 2.4 |
| 724 | 2.1 |
| 725 | 0.8 |
| 726 | 1.2 |
| 727 | 1.7 |
| 728 | 2.4 |
| 729 | 2.8 |
| 730 | 13 |
| 731 | 0.9 |
| 733 | 1.1 |
| 734 | 1.0 |
| 735 | 1.1 |
| 736 | 5.3 |
| 737 | 8.1 |
| 738 | 10 |
| 740 | 0.9 |
| 741 | 2.1 |
| 747 | 2.4 |
| 748 | 2.9 |
| 749 | 4.3 |
| 750 | 1.1 |
| 751 | 4.7 |
| 752 | 14 |
| 753 | 12 |
| 754 | 0.3 |
| 755 | 0.3 |
| 762 | 1.4 |
| 763 | 4.0 |
| 764 | 1.7 |
| 765 | 0.8 |
| 766 | 2.9 |
| 767 | 3.4 |
| 768 | 10 |
| 769 | 3.2 |
| 770 | 1.9 |
| 771 | 6.3 |
| 772 | 1.5 |
| 773 | 11 |
| 774 | 1.2 |
| 775 | 0.8 |
| 776 | 2.5 |
| 777 | 8.6 |
| 778 | 3.4 |
| 779 | 3.3 |
| 780 | 5.0 |
| 781 | 6.0 |
| 782 | 2.7 |
| 783 | 4.2 |
| 784 | 2.8 |
| 785 | 3.5 |
| 786 | 2.2 |
| 787 | 2.9 |
| 788 | 3.1 |
| 789 | 2.4 |
| 790 | 4.4 |
| 791 | 2.3 |
| 792 | 11 |
| 793 | 24 |
| 794 | 10 |
| 795 | 0.8 |
| 796 | 1.3 |
| 797 | 3.1 |
| 798 | 2.5 |
| 799 | 2.9 |
| 800 | 2.5 |
| 801 | 2.6 |
| 802 | 2.0 |
| 803 | 3.5 |
| 804 | 2.8 |
| 806 | 6.6 |
| 807 | 2.6 |
| 808 | 2.0 |
| 809 | 54 |
| 810 | 6.9 |
| 811 | 1.5 |
| 812 | 7.0 |
| 813 | 1.0 |
| 814 | 7.2 |
| 815 | 6.4 |
| 816 | 10 |
| 817 | 3.6 |
| 818 | 1.8 |
| 819 | 1.2 |
| 820 | 1.7 |
| 821 | 4.6 |
| 822 | 1.6 |
| 823 | 5.1 |
| 824 | 1.5 |
| 825 | 8.0 |
| 826 | 1.9 |
| 827 | 6.2 |
| 828 | 0.7 |
| 829 | 0.6 |
| 830 | 1.6 |
| 831 | 2.2 |
| 832 | 2.5 |
| 833 | 1.6 |
| 834 | 3.0 |
| 835 | 0.5 |
| 836 | 1.2 |
| 837 | 17 |

Methods of Preparation

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reaction mixtures are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Wuts et al. (*Greene's Protective Groups In Organic Synthesis,* 4th Edition, Wiley-Interscience (2006).

Compounds of Formula I of this invention can be obtained by palladium catalyzed cross coupling of aryl halides of Formula Ia with organometallic species $R_3$-M as shown in Scheme 1.

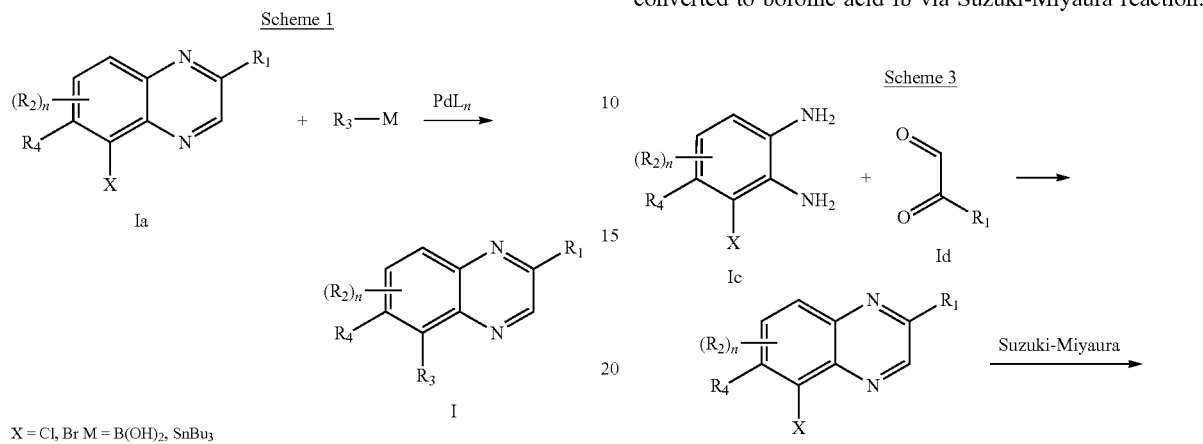

Alternatively, compounds of Formula I can also be prepared from palladium catalyzed cross coupling of arylboronic acids of Formula Ib with halides $R_3$-X shown in Scheme 2.

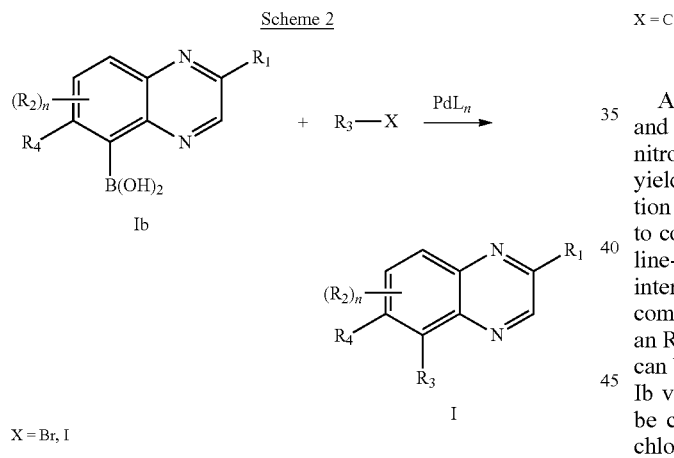

One way to prepare the quinoxalines of Formula Ia and Ib is through the condensation reaction of the diamine Ic with ketoaldehyde Id, as shown in Scheme 3. In general, the condensation will give two regioisomers that may be separated by chromatography. Structure of Formula Ia can be converted to boronic acid Ib via Suzuki-Miyaura reaction.

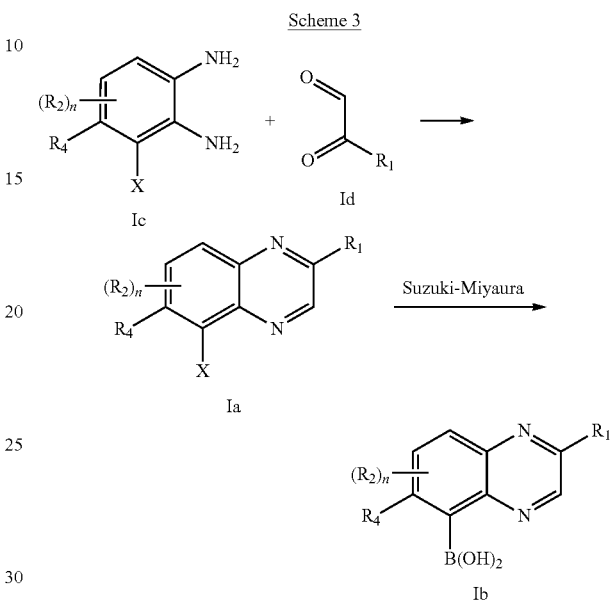

A regio specific synthesis of quinoxalines of Formula Ia and Ib is shown in Scheme 4. A properly protected ortho-nitro aniline Ie is alkylated with methyl bromoacetate to yield compound If. Deprotection of compound If and reduction of compound Ig should initiate cyclization to give rise to compound Ih. Compound Ih can be oxidized to quinoxaline-2-one of Formula Ii, which can be converted to the intermediate Ij with oxophosphorus halides. The halides in compound Ij can be displaced with a nucleophile containing an $R_1$ group to compound Ia, and compounds of Formula Ia can be converted to corresponding boronic acids of Formula Ib via Suzuki-Miyaura reaction. Intermediate Ii could also be converted to Ik by condensation reaction with sodium chlorodifluoroacetate in the presence of a base such as $K_2CO_3$. The difluoroalkoxy maybe displaced with a nucleophile containing an $R_1$ group to compound Ia.

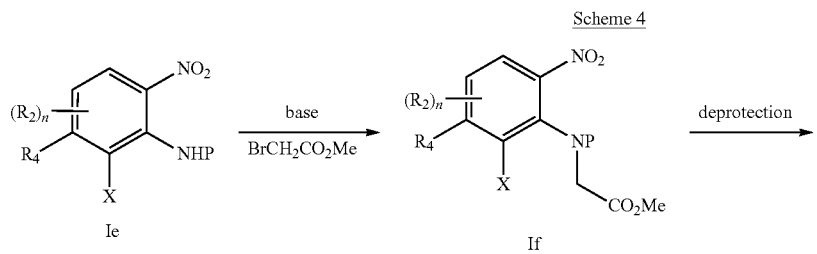

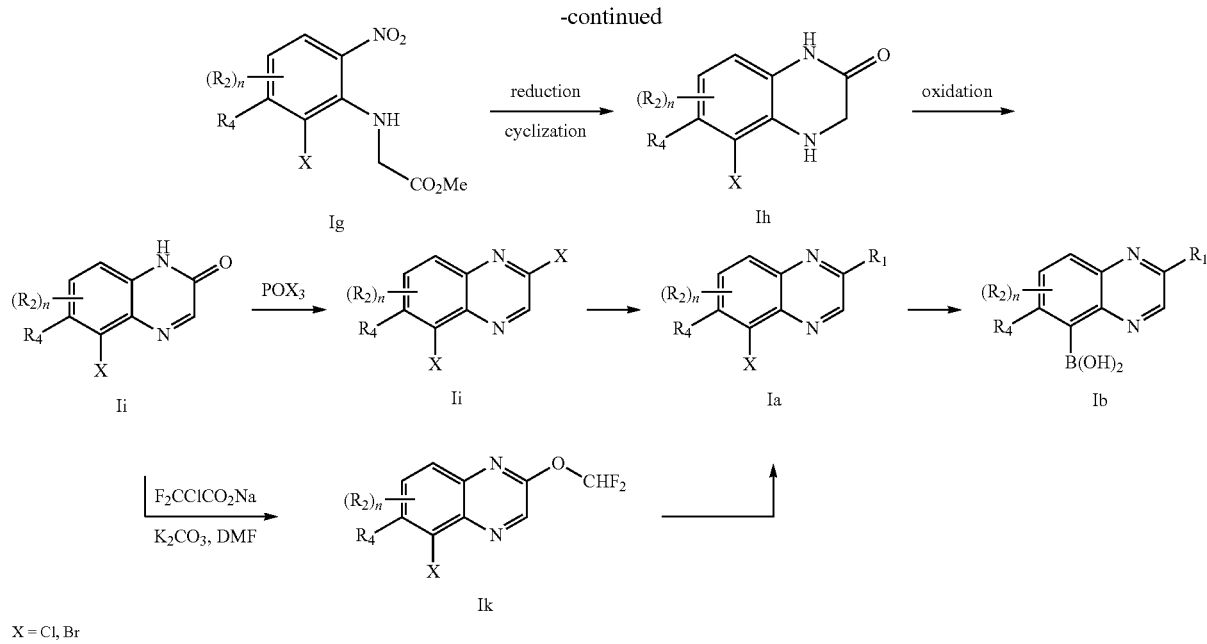

X = Cl, Br

Compounds of Formula II of this invention can be obtained as shown in Scheme 5. Compound IIa can be condensed with dicarbonyl IIb to give compound IIc. Acid catalyzed cyclization provides the key bromide IId. Palladium catalyzed cross coupling reaction with an appropriate boronic acid furnishes compound II.

Scheme 5

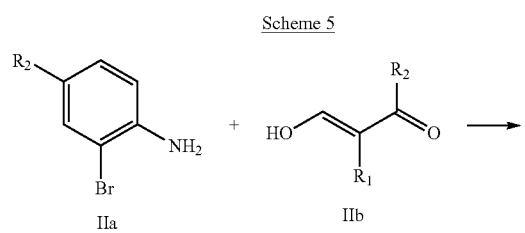

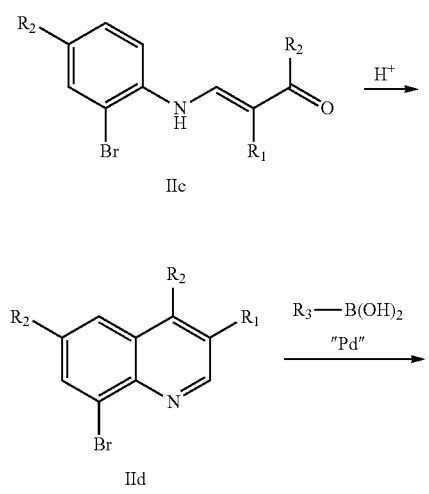

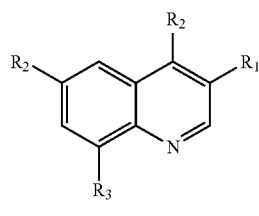

II

Compounds of Formula III of this invention can be obtained as shown in Scheme 6. Compound IIIa can be condensed with dimethylacetal IIIb to give compound IIIc. Acid catalyzed cyclization and triflate formation provides the key coupling partner IIId. Palladium catalyzed cross coupling reaction with an appropriate boronic acid furnishes the compound of Formula III Scheme 6

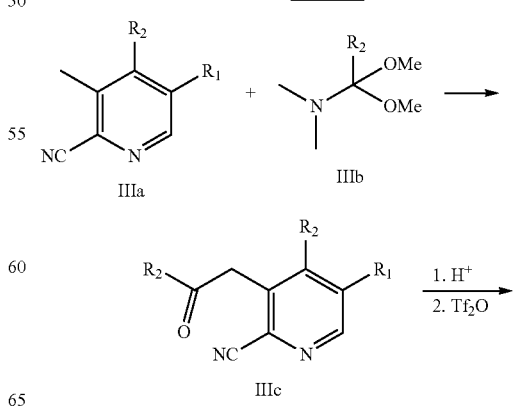

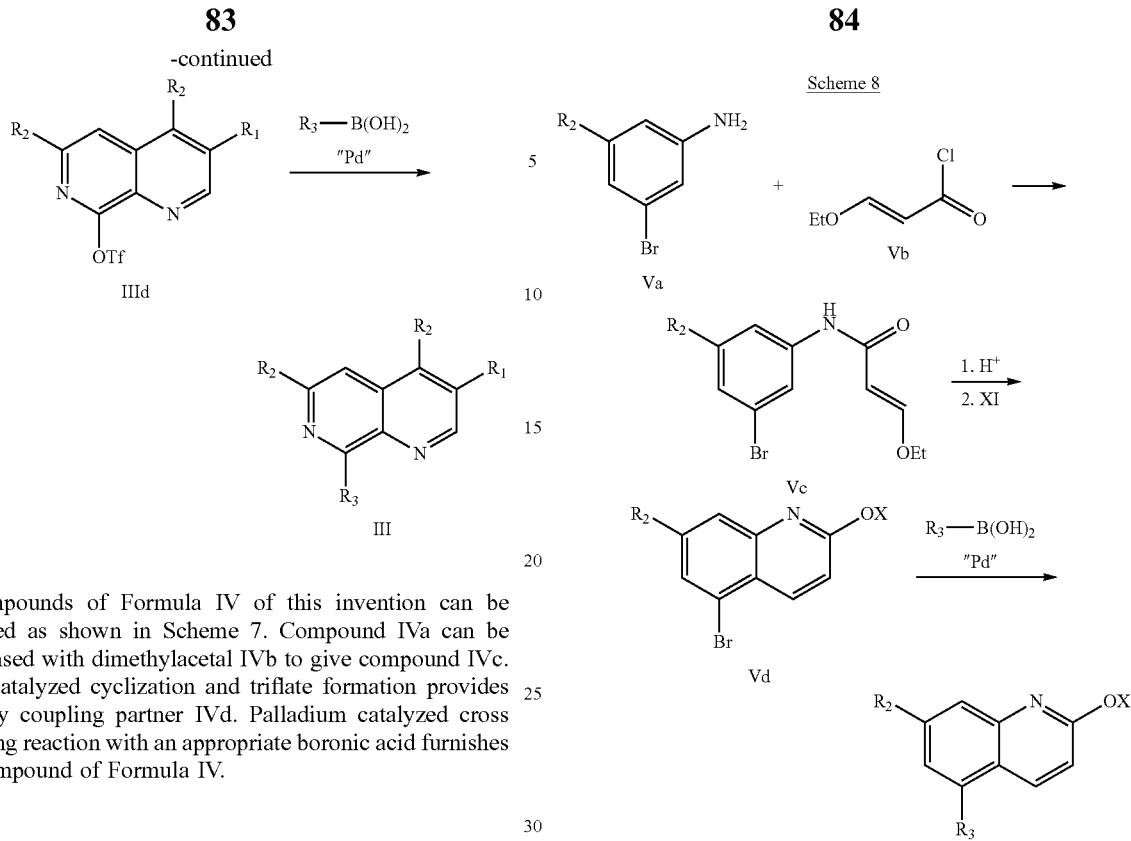

Compounds of Formula IV of this invention can be obtained as shown in Scheme 7. Compound IVa can be condensed with dimethylacetal IVb to give compound IVc. Acid catalyzed cyclization and triflate formation provides the key coupling partner IVd. Palladium catalyzed cross coupling reaction with an appropriate boronic acid furnishes the compound of Formula IV.

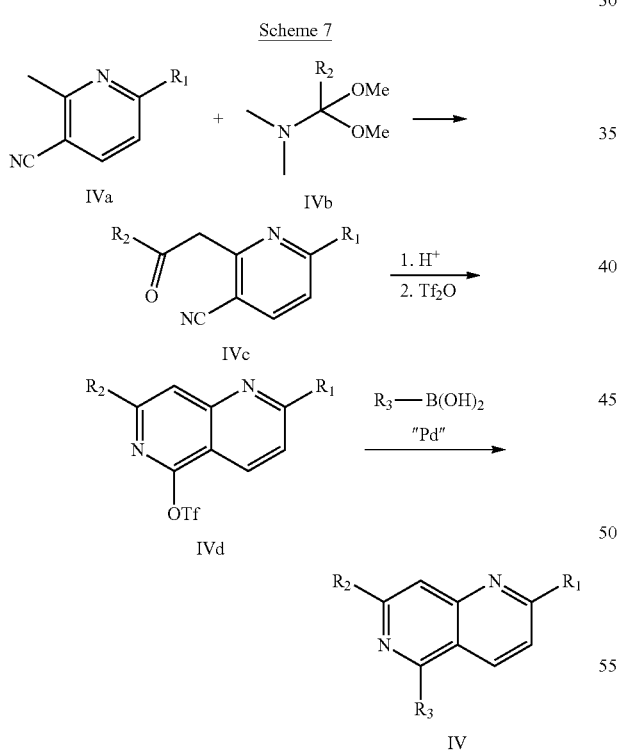

Compounds of Formula V of this invention can be obtained as shown in Scheme 8. Compound Va can be condensed with acid chloride Vb to give compound Vc. Acid catalyzed cyclization and carbonyl alkylation provides the key bromide Vd. Palladium catalyzed cross coupling reaction with an appropriate boronic acid furnishes the compound of Formula V.

Compounds of Formula VI of this invention can be obtained as shown in Scheme 9. Compound VIa can be condensed with dicarbonyl compound VIb to give compound VIc. Palladium catalyzed cross coupling reaction with an appropriate boronic acid furnishes the compound of Formula VI.

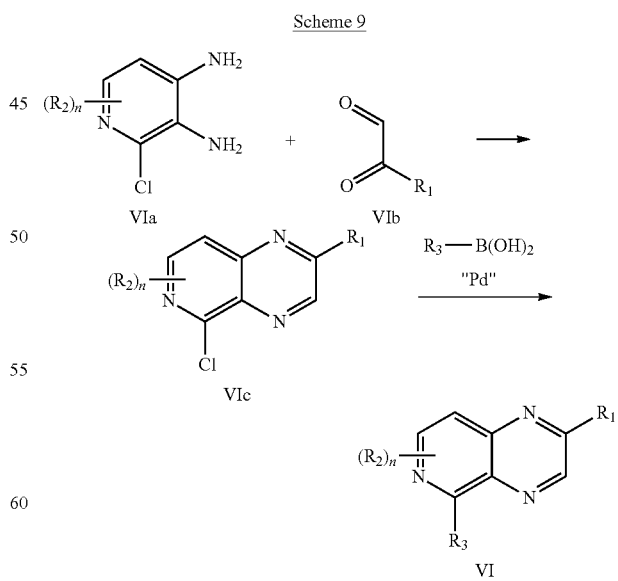

In this invention, compounds of Formula VII can be obtained through the synthetic route shown in Scheme 10. Beginning with aryl chloride VIIa, palladium catalyzed cross coupling of various boronic acids or stannanes yields substituted anilines of structure VIIb. Nitration of compound VIIb and reduction of compound VIIc allows access to compounds of Formula VIId. Base mediated condensation of dianiline VIId with substituted bromo-ketones provides heterocycles of Formula VIIe. A final palladium-catalyzed cross coupling with aryl boronic acids or stannanes then furnishes the compounds of Formula VII.

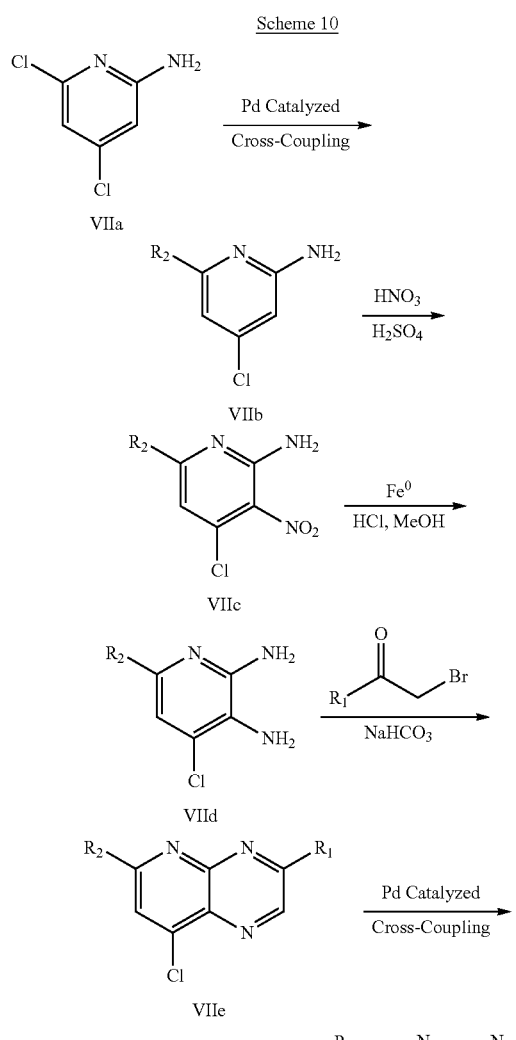

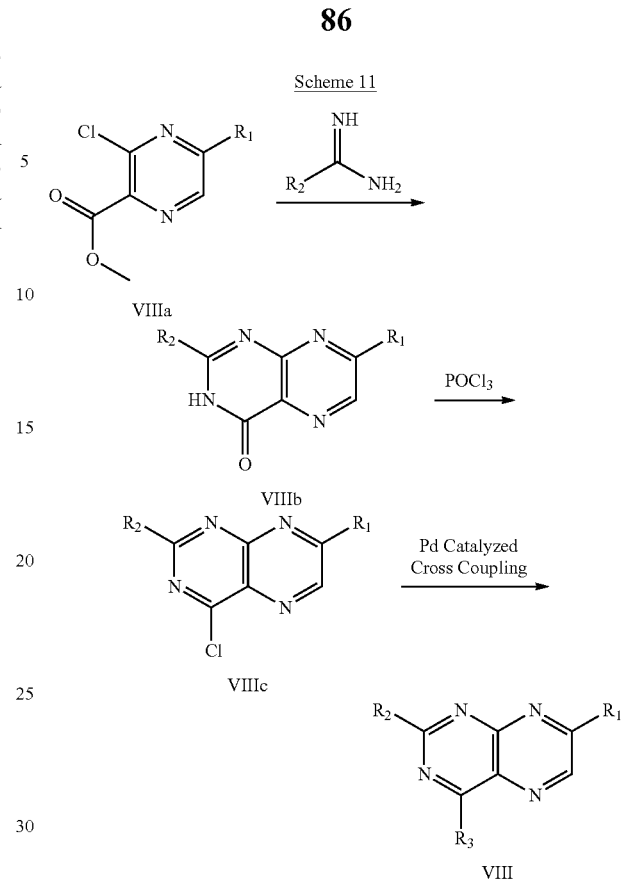

Compounds of Formula VIII of this invention can be obtained by palladium catalyzed cross coupling of aryl boronic acids or stannanes with aryl chloride VIIIc as shown in Scheme 11. Compound VIIIa can be condensed with amidines to give compound VIIIb. Phosphorous oxychloride conversion of compound VIIIb to aryl chloride VIIIc followed by palladium-catalyzed cross coupling with aryl boronic acids or stannanes furnishes the compound of Formula VIII.

A synthesis of 2-halo benzothiazole XXI is shown in Scheme 12. Beginning with the appropriately substituted aniline XIX, the 2-amino benzothiazole XX is formed via addition and oxidative cyclization of a thiocyanate. Subsequent Sandmeyer chemistry is employed to generate the desired 2-halo benzothiazole XXI. With XXI in hand, various compounds of Formula I with structure XXIIa are prepared with boronic acid Ib via Suzuki cross-coupling. Intermediates for preparation of compounds of Formulas I-VIII containing bicyclic $R_3$ groups other than benzothiazole are commercially available or can be prepared by one skilled in the art, and can be incorporated into compounds of Formulas I-VIII via cross coupling chemistry as shown in Scheme 12.

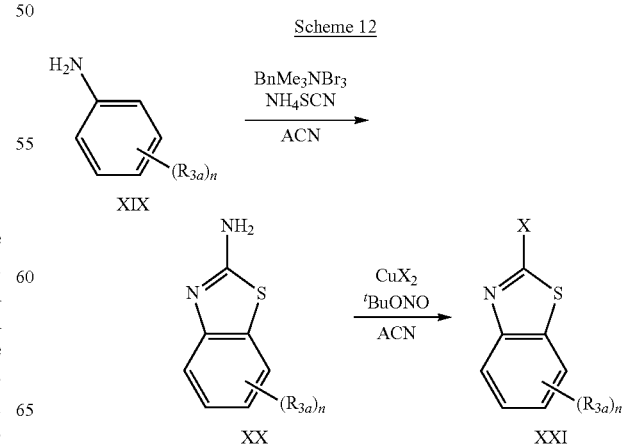

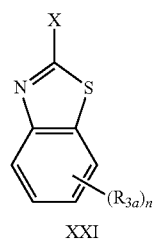

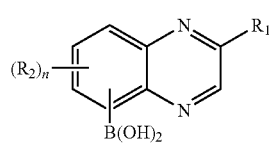

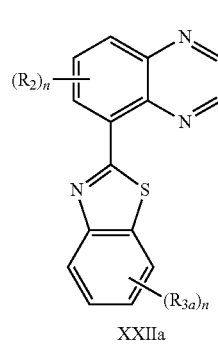

When compounds of structure XXIIb are used as a starting material, several compounds of Formula I with structure XXIII are prepared through either alkylation or Mitsunobu chemistry as shown in Scheme 13. Compounds XXIVa are accessed via epoxide opening of a variety of mono-substituted epoxides, and compounds XXIVb are accessed through the opening of di-substituted cyclic sulfates.

Scheme 13

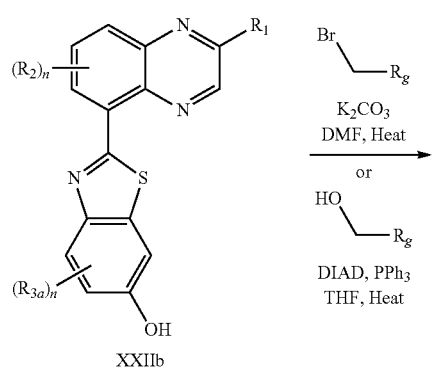

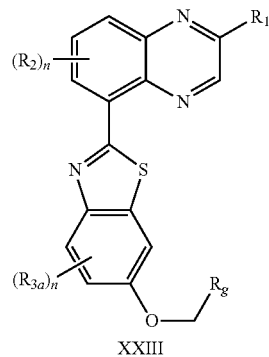

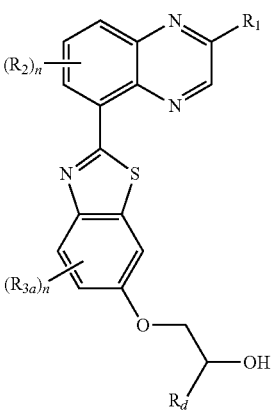

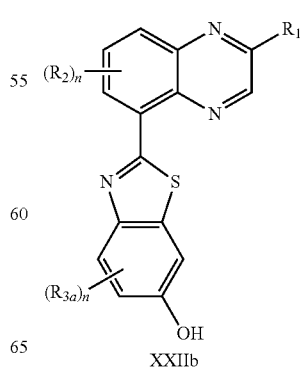

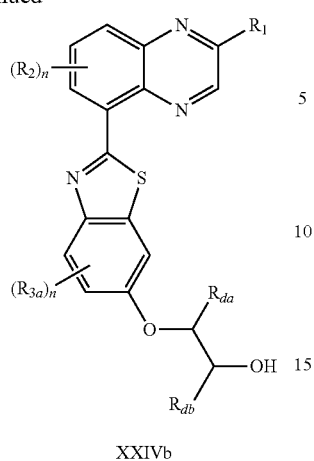

XXIVb

Substitution at the 4-position of the benzothiazole R₃ group can be accomplished from intermediates XXVa and XXVb as shown in Scheme 14. Lithiation of XXVa followed by its addition to a variety of aldehydes provides XXVI, as does Grignard addition to benzaldehyde XXVb. XXVI is then coupled to Ib as described above to provide compounds of Formula I with structure XXVII.

Scheme 14

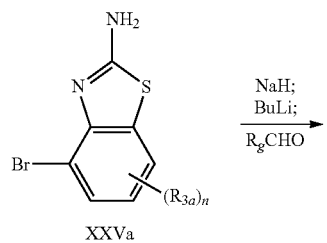

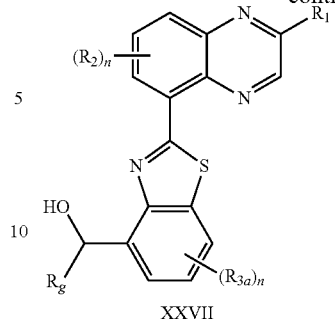

XXVII

Many compounds derived from the core structures depicted above can be either acylated or sulfonylated using the strategy shown in Scheme 15. Thus, chloroformate XXIX is synthesized from compounds with formulas analogous to XXVIII using phosgene. These chloroformates are then reacted with a variety of nucleophiles to generate compounds of structure XXX. Compounds of structure XXXII are synthesized from amines such as XXXI using sulfonyl chloride reagents.

Scheme 15

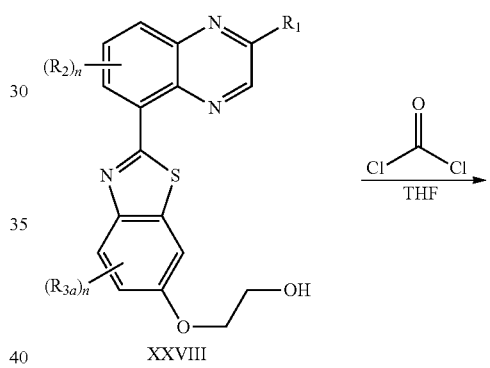

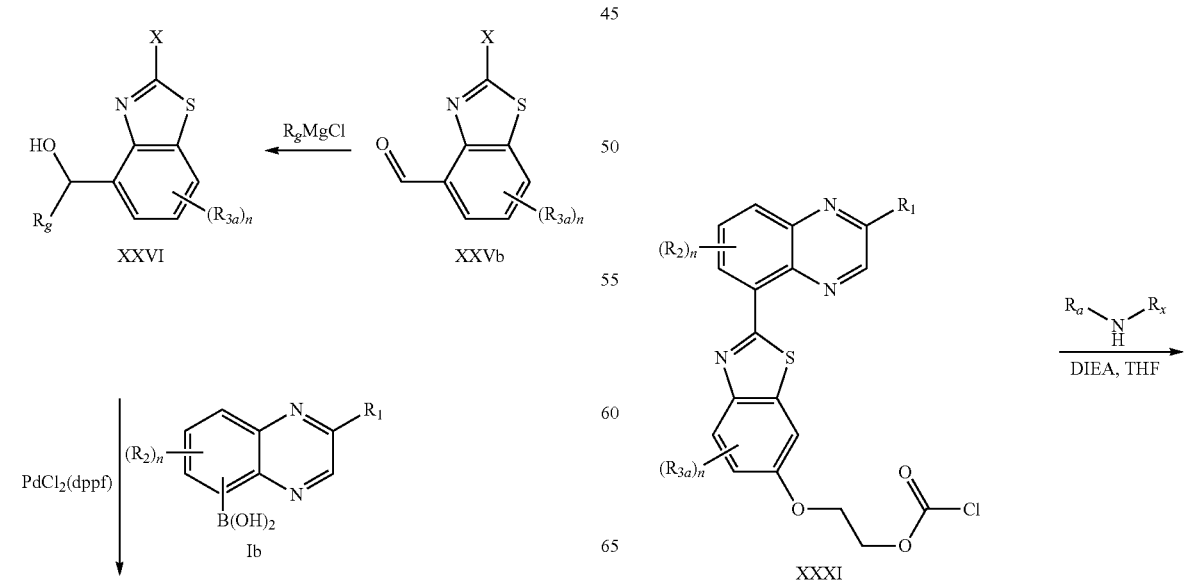

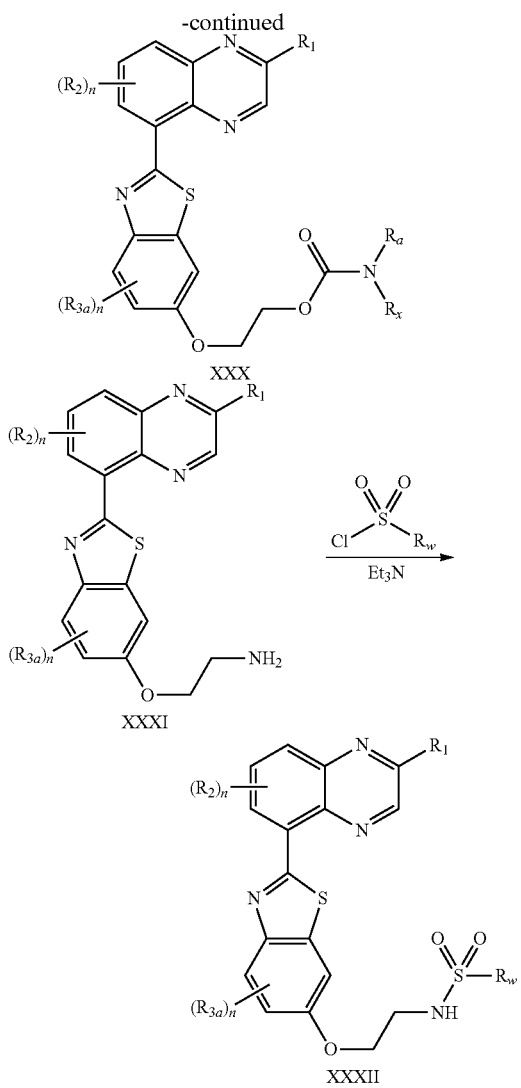

General Methods

The following methods were used in the exemplified Examples, except where noted otherwise.

Products were analyzed by reverse phase analytical HPLC carried out on a Shimadzu Analytical HPLC system running Discovery VP software using one of the following methods:

Method A: PHENOMENEX® Luna C18 column (4.6×50 mm or 4.6×75 mm) eluted at 4 mL/min with 2, 4 or 8 min gradient from 100% A to 100% B (A: 10% methanol, 89.9% water, 0.1% TFA; B: 10% water, 89.9% methanol, 0.1% TFA, UV 220 nm).

Method B: PHENOMENEX® Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm).

Method C: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $H_3PO_4$; B: 10% water, 89.9% methanol, 0.1% $H_3PO_4$, UV 220 nm).

Method D: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $NH_4OAc$; B: 10% water, 89.9% methanol, 0.1% $NH_4OAc$, UV 220 nm).

Method E: BEH C18 2.1×50 mm; A: water+0.05% TFA; B: acetonitrile+0.05% TFA; wavelength 220 nm; flow rate 0.8 mL/min; 0% B to 100% B in 1 minute, gradient time 1.5 min.

Method F: BEH C18 2.1×50 mm; A: water+0.05% TFA; B: acetonitrile+0.05% TFA; wavelength 220 nm; flow rate 0.8 mL/min; 0% B to 50% B in 1 minute, gradient time 1.5 min.

Method G: BEH C18 2.1×50 mm; A: water+0.05% TFA; B: acetonitrile+0.05% TFA; wavelength 220 nm; flow rate 0.8 mL/min; 50% B to 100% B in 1 minute, gradient time 1.5 min.

Reverse phase preparative HPLC was carried out using a Shimadzu Preparative HPLC system running Discovery VP software using one of the following methods.

Method A: PHENOMENEX® Axia Luna 5 μM C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm).

Method B: YMC Sunfire 5 μM C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm).

Method C: XBridge C18, 19×200 mm column, 5-μm particles; Mobile Phase A: 5:95 acetonitrile: water with 0.1% trifluoroacetic acid; Mobile Phase B: 95:5 acetonitrile: water with 0.1% trifluoroacetic acid; Flow: 20 mL/min.

Method D: Waters XBridge C18, 19×100 mm column, 5-μm particles; Mobile Phase A: 5:95 acetonitrile: water with 10-mM ammonium acetate; Mobile Phase B: 95:5 acetonitrile: water with 10-mM ammonium acetate; Flow: 20 mL/min.

Method E: PHENOMENEX® Luna 5 μM C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm).

Method F: PHENOMENEX® Luna 5 μM C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm).

Method G: Waters XBridge C18, 19×200 mm, 5-μm particles; Mobile Phase A: 5:95 acetonitrile:water with 0.1% formic acid; Mobile Phase B: 95:5 acetonitrile:water with 0.1% formic acid; Flow: 20 mL/min.

LCMS chromatograms were obtained on a Shimadzu HPLC system running Discovery VP software, coupled with a Waters ZQ mass spectrometer running MassLynx version 3.5 software using:

Method A: A linear gradient using solvent A (10% acetonitrile, 90% water, 0.1% of TFA) and solvent B (90% acetonitrile, 10% water, 0.1% of TFA); 0-100% of solvent B over 2 min and then 100% of solvent B over 1 min. Column: PHENOMENEX® Luna 3u C18(2) (2.0×30 mm). Flow rate was 5 ml/min. And UV detection was set to 220 nm. The LC column was maintained at room temperature.

Method B: A linear gradient using solvent A (10% methanol, 90% water, 0.1% of TFA) and solvent B (90% methanol, 10% water, 0.1% of TFA); 0-100% of solvent B over 4 min and then 100% of solvent B over 1 min. Column: PHENOMENEX® Luna 5u C18 (4.5×30 mm). Flow rate was 4 ml/min. And UV detection was set to 220 nm. The LC column was maintained at room temperature.

Method C: A linear gradient using solvent A (10% methanol, 90% water, 0.1% of TFA) and solvent B (90% methanol, 10% water, 0.1% of TFA); 0-100% of solvent B over 2 min and then 100% of solvent B over 1 min. Column: PHENOMENEX® Luna 3u C18(2) (2.0×30 mm). Flow rate was 1 ml/min. And UV detection was set to 220 nm. The LC column was maintained at room temperature.

Method D: A linear gradient using solvent A (10% methanol, 90% water, 0.1% of TFA) and solvent B (90% methanol, 10% water, 0.1% of TFA); 0-100% of solvent B over 2 min and then 100% of solvent B over 1 min. Column: PHENOMENEX® Luna 3u C18(2) (4.5×30 mm). Flow rate was 5 ml/min. And UV detection was set to 220 nm. The LC column was maintained at room temperature.

Method E: 30-95% acetonitrile in water with 0.1% TFA in 8 min run, Waters Xbridge 4.6×50 mm 5 um C18, flow rate 1.2 mL/min and UV detection was set to 220 nm. The LC column was maintained at room temperature.

Method F: 10-95% methanol in water, 0.1% TFA in a 10 min run, PHENOMENEX® Onyx Monolithic 4.6×100 mm 5 um C18, flow rate 2.0 mL/mL and UV detection was set to 220 nm. The LC column was maintained at room temperature.

Method G: 5-95% acetonitrile in water, 10 mM of modifier in 6 min run, Waters Xbridge 2.1×50 mm 5 um C18, flow rate 1.0 mL/min and UV detection was set to 220 nm. The LC column was maintained at room temperature.

Method H: BEH C18 2.1×50 mm; A: water+0.05% TFA; B: acetonitrile+0.05% TFA; wavelength 220 nm; flow rate 0.8 mL/min; gradient time 1.5 min; 2 to 98% B.

Method I: BEH C18 2.1×50 mm; A: water+0.05% TFA; B: acetonitrile+0.05% TFA; wavelength 220 nm; flow rate 0.8 mL/min; gradient time 1.5 min; 2 to 52% B.

Method J: BEH C18 2.1×50 mm; A: water+0.05% TFA; B: acetonitrile+0.05% TFA; wavelength 220 nm; flow rate 0.8 mL/min; gradient time 1.5 min; 48 to 98% B.

Method K: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm.

Method L: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.11 mL/min; Detection: UV at 220 nm.

In addition, the following orthogonal HPLC conditions were used to check the purity of the compounds:

Method A: Two analytical LC/MS injections were used to determine the final purity. Injection 1 condition: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Sunfire C18 3.5 um (4.6×150 mm). Flow rate was 2 ml/min. And UV detection was set to 220 nm. The LC column was maintained at room temperature. Injection 2 conditions: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Xbridge Phenyl 3.5 um (4.6×150 mm). Flow rate was 2 ml/min. And UV detection was set to 220 nm. The LC column was maintained at room temperature.

Method B: Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.11 mL/min; Detection: UV at 220 nm.

General Procedures

The following procedures were used during the synthesis of the Examples and Intermediates where indicated below.

Procedure A: 5-bromo-2-chloropyrimidine (1.0 equiv.) was solvated in DMF (0.2 M) along with the appropriate diol (2.0 equiv.). 60% sodium hydride in mineral oil (3.0 equiv.) was added to the reaction mixture portion-wise at 0° C., then the reaction mixture allowed to warm to room temperature and stirred for 30 minutes. The reaction mixture was then quenched with saturated ammonium chloride and diluted with EtOAc. The organic layer was washed with 10% aqueous LiCl solution (3×), brine (1×), dried with sodium sulfate, filtered and concentrated. The resulting residue was dissolved in methylene chloride before being purified by silica gel chromatography to provide the desired material.

Procedure B: To a vial containing the appropriate 5-bromopyrimidine (1.0 equiv.), palladium(II) acetate (0.1 equiv.), BINAP (0.2 equiv.), cesium carbonate (1.2 equiv.) and diphenylmethanimine (1.1 equiv.) was added toluene (0.5 M). The vial was sealed, evacuated and backfilled with Ar 3×, and the reaction mixture was heated to 105° C. for 18 hours. The reaction mixture was then diluted with EtOAc and washed with 1M aqueous NaOH (1×) and brine (1×). The organic layer was dried with sodium sulfate, filtered and concentrated. The resulting residue was dissolved in methylene chloride before being purified by silica gel chromatography to provide the desired material.

Procedure C: The 4-((diphenylmethylene)amino)pyrimidine intermediate (1.0 equiv.) was dissolved in 1:1 MeOH/THF (0.06M). 1M aqueous HCl (2.5 equiv.) was added to the reaction mixture at room temperature. The reaction mixture was allowed to stir at room temperature for 1 hour then diluted with water and extracted with 5:1 EtOAc/Hexanes (3×). The aqueous phase was concentrated and azeotroped with toluene 3× to yield the desired 4-aminopyrimidine which was brought forward without further purification.

Procedure D: 4-bromo-2-fluoropyridine (1.0 equiv.) was dissolved in DMF (1.1 M) along with the appropriate diol (1.5 equiv.). 60% sodium hydride in mineral oil (2.0 equiv.) was added to the reaction mixture portion-wise at 0° C. and the reaction mixture was allowed to warm to room temperature and stirred at room temperature for 4 hours. The reaction mixture was then quenched with saturated ammonium chloride solution and extracted with EtOAc (3×). The organic layer was washed with brine, dried with sodium sulfate, filtered and concentrated. The resulting residue was dissolved in methylene chloride before being purified by silica gel chromatography to provide the desired material.

Procedure E: N1,N2-dimethylethane-1,2-diamine (1.0 equiv.), 2,2,2-trifluoroacetamide (2.0 equiv.), copper(I) iodide (0.2 equiv.), potassium carbonate (2.0 equiv.) and the 4-boromo-2-alkoxypyridine intermediate (1.0 equiv.) were dissolved in dioxane (0.6 M) in a sealed vial. The vial was evacuated and backfilled with Ar 3× then the reaction mixture was stirred at 75° C. for 2 hours. 3 mL of 1:1 MeOH/H$_2$O was added to the mixture which was stirred at room temperature for 2 h then at 40° C. for 1 h. The reaction mixture was then diluted with water and extracted with EtOAc (3×). The combined organic layer was washed with brine, dried with sodium sulfate, filtered and concentrated. The resulting residue was dissolved in a small amount of methylene chloride before being purified by silica gel chromatography to provide the desired material.

Procedure F: The ester (1.0 equiv.) was dissolved in THF (0.2 M) and the solution was cooled to −78° C. 1M DIBAL-H in toluene (3.0 equiv.) was added to the mixture which was allowed to warm to room temperature and stirred at room temperature for 30 minutes. The reaction mixture was then quenched saturated Rochelle's salt and allowed to stir for 18 h at room temperature. The mixture was then diluted with water and extracted with EtOAc (3×). The combined organic layer was washed with brine (1×), dried with sodium sulfate, filtered and concentrated yield the desired product.

Procedure G: The ester (1.0 equiv.) was dissolved in THF (0.2 M) and cooled to −78° C. To the cooled reaction mixture was added 1M DIBAL-H in toluene (3.0 equiv.) and the reaction mixture was allowed to stir at −78° C. for 1 hour. The reaction mixture was then quenched saturated Rochelle's salt and allowed to stir for 2 h at room temperature. The mixture was then diluted with water and extracted with EtOAc (3×). The combined organic layer was washed with brine (1×), dried with sodium sulfate, filtered and concentrated. The resulting aldehyde intermediate was then re-subjected to the conditions described above to ultimately yield the desired alcohol product.

Procedure H: To the ester (1.0 equiv.) dissolved in THF (0.06 M) at −78° C. was added methylmagnesium bromide (10.0 equiv.). The reaction mixture was allowed to warm to room temperature and stirred for 30 minutes at room temperature. The reaction mixture was then quenched with saturated ammonium chloride, diluted with water and extracted with EtOAc (3×). The combined organic layer was washed with brine (1×), dried with sodium sulfate, filtered and concentrated. The resulting residue was purified by reverse phase preparative HPLC to yield the desired product.

Procedure I: The alcohol (1.0 equiv.), imidazole (2.2 equiv.) and TBS-Cl (2.0 equiv.) were dissolved in THF or DCM (0.1 M). The reaction mixture was allowed to stir at room temperature for 18 h. The reaction mixture was then diluted with 1.5 M dipotassium phosphate solution and extracted with EtOAc (3×). The combined organic layer was washed with brine (1×), dried with sodium sulfate, filtered and concentrated. The resulting residue was dissolved in a small amount of methylene chloride and purified by silica gel chromatography to yield the desired product.

Procedure J: The silyl protected intermediate (1.0 equiv.) was dissolved in a mixture of 20:1 MeOH/concentrated aqueous HCl (0.01 M), and the reaction mixture was stirred at room temperature. The reaction was monitored by LCMS, and after completion of the reaction (10 min-12 hours) the reaction mixture was concentrated, dissolved in DMF and purified by preparative HPLC to yield the desired example.

Procedure K: The acetonide intermediate (1.0 equiv.) was dissolved in a mixture of 4:3:2 THF/MeOH/concentrated aqueous HCl (0.01 M), and the solution was stirred at room temperature. The resulting mixture was monitored by LCMS, and after completion of the reaction (10 min-12 hours) the mixture was diluted with EtOAc, washed with 1.5 M K$_2$HPO$_4$, dried over sodium sulfate, filtered, concentrated, dissolved in DMF and purified by preparative HPLC to yield the desired example.

EXAMPLES

The invention is further defined in the following Examples. It should be understood that the Examples are given by the way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather is defined by the claims appended hereto.

Abbreviations

AcOH acetic acid
ACN acetonitrile
BINAP 2,2'-bis(diphenylphosphino)-1,1'-binaphthylene
Boc tert-butoxycarbonyl
BOC$_2$O di(tert-butoxycarbonyl) ether
BuLi butyl lithium
DCE dichloroethane
DCM dichloromethane
DIAD diisopropyl azodicarboxylate
DIBAL-H diisobutylaluminium hydride
DIEA diisopropylethylamine
DMAP dimethylaminopyridine
DMF dimethylformamide
DMSO dimethylsulfoxide
EtOAc ethyl acetate
EtOH ethanol
HOBt hydroxybenzotriazole
mCPBA 3-chloroperbenzoic acid
MeCN acetonitrile
MeOH methanol
NH$_4$OAc ammonium acetate
NMP N-methylpyrrolidinone
PdCl$_2$(dppf)-CH$_2$Cl$_2$ [1,1'-bis(diphenylphosphino)ferrocene]dichloropalladium(II), dichloromethane adduct
Pd(OAc)$_2$ palladium acetate
Pd(Ph$_3$P)$_4$ tetrakis(triphenylphosphine)palladium
TBAF tetrabutylammonium fluoride
TBDMS-Cl tert-butyldimethylsilyl chloride
TEA triethylamine
TFA trifluoroacetate
THF tetrahydrofuran
HPLC high pressure liquid chromatography
MS mass spectrometry
g gram(s)
h or hr hour(s)
min. minute(s)
mL milliliter(s)
mmol millimole(s)
RT retention time

Intermediate I-1

2-(difluoromethoxy)-7-methyl-5-(4,4,5,5-tetramethyl-1,3,2-dioxaborolan-2-yl) quinoxaline

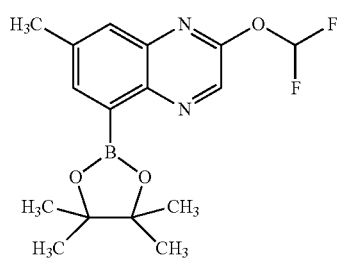

(I-1)

Intermediate I-1A: tert-butyl N-(2-bromo-4-methyl-6-nitrophenyl)-N-[(tert-butoxy) carbonyl]carbamate

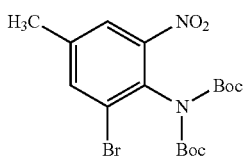

(I-1A)

To a solution of 2-bromo-4-methyl-6-nitroaniline (9.6 g, 41.6 mmol) in THF (60 mL) was added DMAP (0.508 g, 4.16 mmol), followed by BOC$_2$O (22.67 g, 104 mmol) as a solid. The mixture was stirred at room temperature overnight. Solvent was removed by vacuum. The crude product was dissolved in a small amount of chloroform and charged to a 120 g silica gel cartridge (2 separate columns) which was eluted with 5% EtOAc in hexanes for 4 min., then a 12 min gradient from 5% to 30% EtOAc in hexanes. The desired fractions were combined and concentrated to give Intermediate I-1A (17.12 g, 39.7 mmol, 96% yield) as a white solid. $^1$H NMR (500 MHz, chloroform-d) δ 7.80-7.79 (m, 1H), 7.73 (dd, J=1.9, 0.8 Hz, 1H), 2.48 (s, 3H), 1.42 (s, 18H); LC-MS: method A, RT=1.90 min, MS (ESI) m/z: 230.0 and 232.0 (M−2 Boc)$^+$.

Intermediate I-1B: tert-butyl (2-bromo-4-methyl-6-nitrophenyl)carbamate

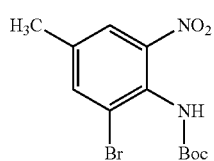

(I-1B)

To a solution of Intermediate I-1A (17.1 g, 39.6 mmol) in dichloromethane (60 mL) was added TFA (6.11 mL, 79 mmol) and the mixture was stirred at room temperature for 1.0 h. The reaction mixture was quenched by addition of saturated sodium bicarbonate, extracted with dichloromethane (3×), dried over sodium sulfate. After evaporation of solvent, Intermediate I-1B was obtained as a yellow solid (12.88 g, 88% yield): $^1$H NMR (500 MHz, chloroform-d) δ 7.71 (d, J=1.1 Hz, 1H), 7.68 (dd, J=1.9, 0.8 Hz, 1H), 2.42 (s, 3H), 1.51 (s, 9H); LC-MS: method A, RT=1.53 min, MS (ESI) m/z: 231.0 and 233.0 (M−Boc)$^+$.

Intermediate I-1C: methyl 2-((2-bromo-4-methyl-6-nitrophenyl)(tert-butoxycarbonyl) amino)acetate

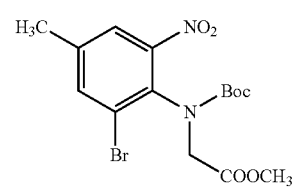

(I-1C)

Intermediate I-1B (12 g, 26.3 mmol) was dissolved in DMF (80 mL), cooled with a water bath. Cs$_2$CO$_3$ (25.8 g, 79 mmol) was added. The dark brown solution was stirred at room temperature for 10 min, then methyl 2-bromoacetate (4.37 mL, 47.6 mmol) was added dropwise. After addition of methyl bromoacetate, the brown color faded to yellow. The mixture was stirred at room temperature for 1.0 h, diluted with EtOAc, quenched with water. The organic layer was collected, washed with brine, dried over sodium sulfate. After evaporation of solvent, the crude product was dissolved in a small amount of chloroform and charged to a 330 g silica gel cartridge which was eluted with 5% EtOAc in hexanes for 5 min., then a 12 min gradient from 5% to 50% EtOAc in hexanes. The desired fractions were combined and concentrated to give Intermediate I-1C (15.2 g, 37.7 mmol, 95% yield) as an yellow oil. $^1$H NMR (500 MHz, chloroform-d) indicated a mixture of rotamers: δ 7.75-7.67 (m, 2H), 4.61-3.97 (m, 2H), 3.76 and 3.69 (s, 3H), 2.48 and 2.43 (s, 3H), 1.55 and 1.37 (s, 9H); LC-MS: method A, RT=1.70 min, MS (ESI) m/z: 303.0 and 305.0 (M−Boc)$^+$.

Intermediate I-1D: methyl 2-((2-bromo-4-methyl-6-nitrophenyl)amino)acetate

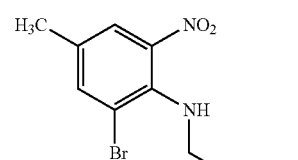

(I-1D)

To Intermediate I-1C (15.2 g, 37.7 mmol) was added 4.0 N HCl in dioxane (47.1 ml, 188 mmol) and the mixture was stirred at room temperature overnight. Solvent was removed under vacuum, chased with EtOAc (2×) to give Intermediate I-1D (13.6 g, 40.1 mmol, 106% yield) as a yellow solid. $^1$H NMR (500 MHz, methanol-d$_4$) δ 7.88 (dd, J=1.9, 0.6 Hz, 1H), 7.80 (dd, J=1.9, 0.6 Hz, 1H), 4.47 (d, J=17.3 Hz, 1H), 4.08 (d, J=17.1 Hz, 1H), 3.69 (s, 3H), 2.46 (s, 3H); LC-MS: Method A, RT=1.94 min, MS (ESI) m/z: 303.1 and 305.1 (M+H)$^+$.

Intermediate I-1E:
5-bromo-7-methyl-3,4-dihydroquinoxalin-2(1H)-one

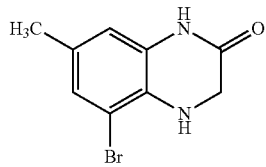

To a solution of Intermediate I-1D (13.6 g, 40.1 mmol) in MeOH (100 mL) in a 1 L flask cooled with water bath was added concentrated HCl (13.35 mL, 160 mmol), followed by tin(II) chloride dihydrate (36.1 g, 160 mmol). The mixture was stirred at 68° C. for 2.5 h. MeOH was removed by vacuum. The crude was partitioned in water (100 mL)/EtOAc (200 mL), and the pH was adjusted to neutral with 4.0 N NaOH (ca 90 mL). The white precipitate formed was very fine particle that was very hard to remove by filtration. The mixture was transferred to a separatory funnel. The organic layer was collected. The aqueous was further extracted (2×200 mL) with EtOAc. The combined organic layer was washed with water (2×) and brine (2×), dried over sodium sulfate. After evaporation of solvent, Intermediate I-1E (8.36 g, 34.7 mmol, 87% yield) was obtained as a pale yellow solid. $^1$H NMR (500 MHz, DMSO-$d_6$) δ 10.37 (s, 1H), 6.87 (dd, J=1.8, 0.7 Hz, 1H), 6.56 (dd, J=1.1, 0.6 Hz, 1H), 5.46 (s, 1H), 3.76 (d, J=2.2 Hz, 2H), 2.14 (s, 3H); LC-MS: method A, RT=1.66 min, MS (ESI) m/z: 241.0 and 243.0 (M+H)$^+$.

Intermediate I-1F: 5-bromo-7-methylquinoxalin-2-ol

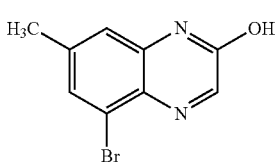

To a suspension of Intermediate I-1E (6.7 g, 27.8 mmol) in MeOH (50 mL) in a 1 L flask was added 30% hydrogen peroxide (28.4 mL, 278 mmol), followed by 4.0 N NaOH (20.84 mL, 83 mmol). The mixture was stirred at room temperature for 5 min, then gently heated at 60° C. After 15 min heating, the reaction mixture turned strongly exothermic, suggesting an initiation of the reaction mixture. The heating bath was removed and stirring continued for 30 min until the mixture turned completely clear. After cooling to room temperature with a water bath, MeOH was removed by vacuum. The mixture was then neutralized with 2.0 N HCl (to pH 2-3) and ice cooling. The precipitate formed was collected by filtration, washed with water, dried under vacuum in the air for 1.0 h and then at vacuum at 60° C. for 2.0 h, and under high vacuum to give Intermediate I-1F (6.55 g, 27.4 mmol, 99% yield) as an off-white solid. $^1$H NMR (500 MHz, DMSO-$d_6$) δ 12.52 (br. s., 1H), 8.17 (s, 1H), 7.49 (d, J=1.1 Hz, 1H), 7.08 (s, 1H), 2.40 (s, 3H); LC-MS: method A, RT=1.62 min, MS (ESI) m/z: 239.0 and 241.0 (M+H)$^+$.

Intermediate I-1G: 5-bromo-2-(difluoromethoxy)-7-methylquinoxaline

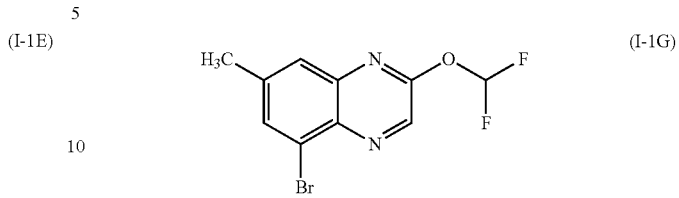

A mixture of Intermediate I-1F (7.4 g, 26.9 mmol) and potassium carbonate (18.56 g, 134 mmol) in DMF (120 mL) was heated at 100° C. for 5 min. Sodium 2-chloro-2,2-difluoroacetate (16.40 g, 107.6 mmol) was added in one portion, and the mixture was stirred at 100° C. for 10 min. The mixture turned from yellow slurry to brown. The mixture was cooled to room temperature, diluted with EtOAc and water, extracted with EtOAc (3×). The combined organic layer was washed with brine, dried over sodium sulfate. After evaporation of solvent, the crude product was dissolved in a small amount of chloroform/toluene and purified with a 330 g ISCO column eluted with 5% dichloromethane in hexanes for 3 min, then 5-70% DCM/hexanes for 40 min (12 min gradient time). The desired fractions were combined, concentrated to give Intermediate I-1G (6.0 g, 20.76 mmol, 77% yield) as a slightly yellow solid. $^1$H NMR (500 MHz, chloroform-d) δ 8.64 (s, 1H), 7.89 (d, J=1.7 Hz, 1H), 7.68 (dd, J=1.8, 1.0 Hz, 1H), 7.63 (t, $J_{HF}$=71.80 Hz, 1H), 2.59 (s, 3H); $^{19}$F NMR (471 MHz, chloroform-d) δ −89.82 (s, 2F); LC-MS: method A, RT=2.09 min, MS (ESI) m/z: 289.0 and 291.0 (M+H)$^+$.

Intermediate I-1

A mixture of Intermediate I-1G (1.04 g, 3.60 mmol), 4,4,4',4',5,5,5',5'-octamethyl-2,2'-bi(1,3,2-dioxaborolane) (1.370 g, 5.40 mmol), potassium acetate (0.883 g, 8.99 mmol) and [1,1'-bis(diphenylphosphino)ferrocene]dichloropalladium (II) complex with dichloromethane (1:1) (0.147 g, 0.180 mmol) in dioxane (14 mL) was degassed by bubbling argon for 10 min. The reaction mixture vial was sealed and heated in microwave reactor at 135° C. for 30 min. The mixture was diluted with EtOAc/water, insoluble material was removed by filtration. The filtrate was extracted with EtOAc, washed with brine and dried over sodium sulfate. After evaporation of solvent, the crude product was dissolved in a small amount of toluene and charged to a 40 g silica gel cartridge which was eluted with 5% EtOAc in hexanes for 2 min., then a 18 min gradient from 5% to 75% EtOAc in hexanes. The desired fractions were concentrated and lyophilized to give Intermediate I-1 (0.93 g, 72% yield) as a pale solid. $^1$H NMR was complicated by the presence of two sets of signals. $^{19}$F NMR indicated a single compound. $^{19}$F NMR (471 MHz, chloroform-d) δ −89.64 (s., 2F). LC-MS: method A, RT=2.01 min, MS (ESI) m/z: 225.0 (boronic acid)$^+$.

Intermediate I-2

2-(methoxymethyl)-7-methyl-5-(4,4,5,5-tetramethyl-1,3,2-dioxaborolan-2-yl)quinoxaline

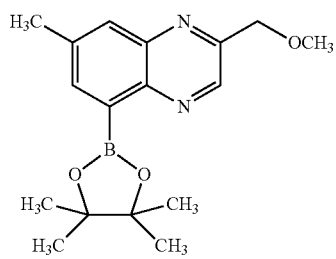
(I-2)

Intermediate I-2A: 1-diazo-3-methoxypropan-2-one

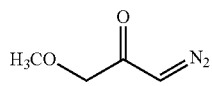
(I-2A)

To 2-methoxyacetyl chloride (2.4 g, 22.12 mmol) in MeCN (40 mL) cooled with ice-bath was added (diazomethyl)trimethylsilane 2.0 M in diethyl ether (19.35 mL, 38.7 mmol). The mixture was allowed to stir at room temperature overnight. Solvent was removed under reduced pressure. The crude product was purified by flash chromatography (loading in chloroform, 0% to 50% EtOAc in hexane over 18 min using a 40 g silica gel cartridge). The desired fractions were combined and concentrated (bath temp below 35° C.) to yield Intermediate I-2A (1.82 g, 15.95 mmol, 72.1% yield) as a yellow liquid. $^1$H NMR (500 MHz, chloroform-d) δ 5.73 (br. s., 1H), 3.97 (br. s., 2H), 3.43 (s, 3H); LC-MS: method A, RT=0.43 min, MS (ESI) m/z: 137.0 (M+Na)$^+$.

Intermediate I-2B: 1-bromo-3-methoxypropan-2-one

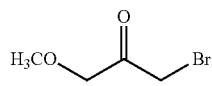
(I-2B)

To Intermediate I-2A (1.6 g, 14.02 mmol) in diethyl ether (20 mL) at 0° C. was added aqueous HBr 48% (2.380 mL, 21.03 mmol) dropwise. After stirring at 0° C. for 5 min and at room temperature for 10 min, the reaction mixture was diluted with EtOAc, washed with water, saturated sodium bicarbonate (2×) and brine. The organic layer was dried over sodium sulfate, concentrated (keep bath temp below 30° C.) to give Intermediate I-2B (1.5 g, 8.98 mmol, 64.1% yield) as a slightly yellow liquid. $^1$H NMR indicated >92% purity. The compound was used immediately for the next step without further purification. $^1$H NMR (500 MHz, chloroform-d) δ 4.24 (s, 2H), 4.03 (s, 2H), 3.45 (s, 3H), consistent with literature report (*J. Org. Chem.* 1981, 217).

Intermediate I-2C: tert-butyl (2-bromo-4-methyl-6-nitrophenyl)(3-methoxy-2-oxopropyl)carbamate

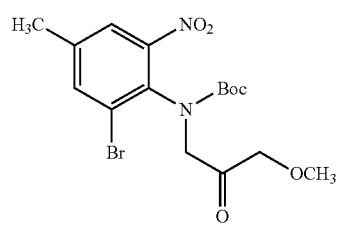
(I-2C)

To Intermediate I-1B (1.98 g, 5.98 mmol) in DMF (20 mL) at 0° C. was added Cs$_2$CO$_3$ (3.41 g, 10.46 mmol). The brown solution was stirred at 0° C. for 10 min, followed by addition of Intermediate I-2B (1.498 g, 8.97 mmol) in acetonitrile (5.0 mL). The brown solution turned yellow. The mixture was stirred at 0° C. for 15 min., diluted with EtOAc, washed with water, brine, dried over sodium sulfate and concentrated. The crude product was purified by flash chromatography (loading in chloroform, 0% to 60% EtOAc in hexane over 18 min using a 80 g silica gel cartridge). The desired fractions were combined and concentrated to yield Intermediate I-2C (2.4 g, 5.75 mmol, 96% yield) as a yellow oil. $^1$H NMR indicated presence of two rotamers. $^1$H NMR (500 MHz, chloroform-d) δ 7.70-7.65 (m, 2H), 4.55 (d, J=17.9 Hz, 1H), 4.18 (d, J=17.9 Hz, 1H), 4.32 and 4.14 (d, J=1.4 Hz, 2H), 3.44 and 3.40 (s, 3H), 2.45 and 2.40 (s, 3H), 1.49 and 1.35 (s, 9H); LC-MS: method A, RT=1.89 min, MS (ESI) m/z: 317 and 319 (M–Boc)$^+$.

Intermediate I-2D 6-bromo-3-hydroxy-3-(methoxymethyl)-8-methyl-1-oxo-1,3,4,5-tetrahydrobenzo[c][1,2,5]oxadiazepin-1-ium

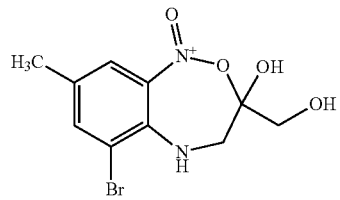
(I-2D)

To Intermediate I-2C (1.67 g, 4.00 mmol) in ethyl acetate (10 mL) was added 4.0 N HCl in dioxane (10.01 mL, 40.0 mmol) and the mixture was stirred at room temperature for 20 min. Solvent was removed under vacuum, chased with EtOAc once to give Intermediate I-2D (1.25 g, 99%) as a yellow oil. $^1$H NMR (400 MHz, chloroform-d) δ 7.75-7.66 (m, 2H), 4.13-3.98 (m, 1H), 3.78-3.56 (m, 3H), 3.50 and 3.44 (m, 3H), 2.39 (s, 3H); LC-MS: method A, RT=1.47 min, MS (ESI) m/z: 317.0 and 319.0 (M+H)$^+$.

Intermediate I-2E:
5-bromo-2-(methoxymethyl)-7-methylquinoxaline

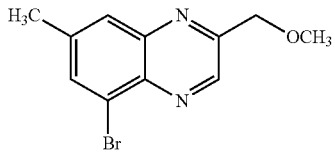

(I-2E)

Intermediate I-2D (1.25 g, 3.9 mmol) was dissolved in THF (30 mL). Concentrated HCl (0.986 mL, 12.01 mmol) was added, followed by tin(II) chloride dihydrate (3.61 g, 16.01 mmol). The mixture was placed and stirred in an oil bath pre-heated at 40° C. for 4.0 h. The reaction mixture was diluted with EtOAc/water, The organic phase was neutralized with saturated sodium bicarbonate and stirred at room temperature for 15 min, the precipitate was removed by filtration with a pad of wet celite. The filtrate was collected. The organic layer was washed with brine, dried over sodium sulfate and concentrated. The crude product was purified by flash chromatography (loading in chloroform, 0% to 60% EtOAc in hexane over 20 min using a 120 g silica gel cartridge). The desired fractions were combined and concentrated to yield Intermediate I-2D (0.57 g, 1.920 mmol, 48.0% yield) as a brown solid: $^1$H NMR (400 MHz, chloroform-d) δ 9.03 (s, 1H), 7.95 (d, J=1.5 Hz, 1H), 7.84 (dd, J=1.8, 1.1 Hz, 1H), 4.84 (s, 2H), 3.56 (s, 3H), 2.60 (s, 3H); Intermediate I-2D was contaminated with ca 10% of a side product 5-bromo-2,7-dimethylquinoxaline.

Intermediate I-2

A mixture of Intermediate I-2E (900 mg, 3.37 mmol), 4,4,4',4',5,5,5',5'-octamethyl-2,2'-bi(1,3,2-dioxaborolane) (1369 mg, 5.39 mmol), potassium acetate (661 mg, 6.74 mmol) and [1,1'-bis(diphenylphosphino)ferrocene]dichloropalladium (II) complex with dichloromethane (1:1) (110 mg, 0.135 mmol) in dioxane (15 mL) was degassed by bubbling argon for 10 min. The reaction vial was sealed and heated in microwave reactor at 130° C. for 30 min. The mixture was diluted with EtOAc/water, insoluble material was removed by filtration. The filtrate was extracted with EtOAc, washed with brine and dried over sodium sulfate, concentrated. The crude product was purified by flash chromatography (loading in chloroform, 0% to 20% dichloromethane in MeOH over 15 min using a 40 g silica gel cartridge). The desired fractions were combined and concentrated and further purified by prep HPLC (method A, 10-80% B in 8 mins; with a flow rate of 40 mL/min). The desired fractions were placed in a SpeedVac overnight to remove solvent. The material was dissolved in EtOAc, washed with diluted saturated sodium bicarbonate (to remove TFA), brine, dried over sodium sulfate, concentrated and lyophilized to give Intermediate I-2 (360 mg, 1.550 mmol, 46% yield) as a slightly colored solid. LC-MS: method A, RT=1.73 min, MS (ESI) m/z: 233.1 boronic acid (M+H)$^+$.

Intermediate I-3

2-bromo-6-methoxy-4-methylbenzo[d]thiazole

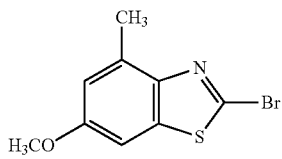

(I-3)

Intermediate I-3A: 6-methoxy-4-methylbenzo[d]thiazol-2-amine

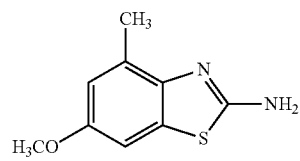

(I-3A)

To 4-methoxy-2-methylaniline (209 mg, 1.524 mmol) in acetonitrile (8 mL) was added ammonium thiocyanate (174 mg, 2.285 mmol). The mixture was stirred at room temperature for 10 min. Then it was cooled with tap water, and benzyltrimethylammonium tribromide (594 mg, 1.524 mmol) in acetonitrile (3.0 mL) was added dropwise. The mixture was then stirred at room temperature overnight. HPLC and LCMS indicated a clean reaction. The mixture was diluted with EtOAc/saturated sodium bicarbonate. The organic layer was collected, washed with brine, dried over sodium sulfate. After evaporation of solvent, the crude product was dissolved in a small amount of chloroform/MeOH, and charged to a 24 g silica gel cartridge which was eluted with 5% EtOAc in hexanes for 3 min., then a 12 min gradient from 5% to 50% EtOAc in hexanes. The desired fractions were combined and concentrated to give Intermediate I-3A (240 mg, 1.235 mmol, 81% yield) as a pale solid. $^1$H NMR (500 MHz, methanol-$d_4$) δ 7.03 (d, J=2.5 Hz, 1H), 6.71 (d, J=1.9 Hz, 1H), 3.79 (s, 3H), 2.46 (s, 3H); LC-MS: method A, RT=1.22 min, MS (ESI) m/z: 195.0 (M+H)$^+$.

Intermediate I-3 t-Butyl nitrite (0.969 mL, 8.15 mmol) was added to copper(II) bromide (1820 mg, 8.15 mmol) in dry acetonitrile (20 mL) under argon. The mixture was stirred at room temperature for 10 min. A suspension of Intermediate I-3A (931 mg, 4.79 mmol) in acetonitrile (30 mL) was added dropwise. The reaction mixture was stirred at room temperature for 1.0 h. LCMS indicated a clean reaction. Acetonitrile was removed under vacuum, the reaction mixture was diluted with EtOAc (30 mL) and 20 mL of 0.5M HCl (aqueous). After separation, organic layer was washed with 0.5 N HCl (20 mL×2), saturated sodium bicarbonate (15 mL), brine (15 mL) and dried over sodium sulfate. After evaporation of the solvent, the crude product was purified by ISCO (80 g silica gel column, 20% EtOAc/hexanes). Removing solvent gave Intermediate I-3 as white solid (1.13 g, 91%). $^1$H NMR (400 MHz, methanol-$d_4$) δ 7.29 (d, J=2.5

Hz, 1H), 6.95-6.87 (m, 1H), 3.84 (s, 3H), 2.60 (s, 3H); LC-MS: (BEH C18 2.1×50 mm; A: 10% MeCN-90% H$_2$O −0.1% TFA; B: 90% MeCN −10% H$_2$O −0.1% TFA; wavelength 220/254 nm; flow rate 5 mL/min; gradient time 2 min; 2 to 98% B) 1.11 min, [M+1]$^+$=258.0, 260.0;

Intermediate I-4

2-((2-(2-(difluoromethoxy)-7-methylquinoxalin-5-yl)benzo[d]thiazol-6-yl)oxy)ethanamine

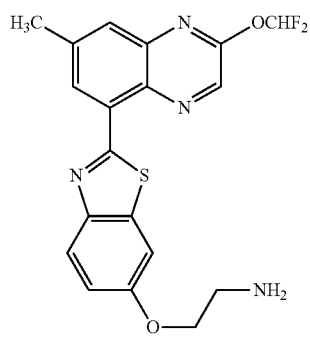

(I-4)

Intermediate I-4A: 2-chlorobenzo[d]thiazol-6-ol

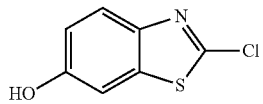

(I-4A)

Aluminum chloride (3.07 g, 22.99 mmol) was added to a solution of 2-chloro-6-methoxybenzo[d]thiazole (1.53 g, 7.66 mmol) in toluene (50 mL). The mixture was heated at 110° C. for 1.5 h. TLC indicated a complete conversion of starting material. The reaction mixture was cooled to room temperature, quenched with ice-cold 1.0 N HCl (50 mL), stirred at room temperature for 30 min. The precipitate was collected by filtration, washed with water (3×), saturated sodium bicarbonate (3×), water (3×) and air-dried for 1.0 h under vacuum. It was further dried under high vacuum overnight to give Intermediate I-4A (1.18 g, 6.36 mmol, 83% yield) as a pale brown solid. $^1$H NMR (500 MHz, chloroform-d) δ 7.82 (d, J=8.8 Hz, 1H), 7.24 (d, J=2.5 Hz, 1H), 7.03 (dd, J=8.8, 2.5 Hz, 1H), 5.53 (s, 1H); LC-MS: method A, RT=1.62 min, MS (ESI) m/z: 186.0 and 188.0 (M+H)$^+$.

Intermediate I-4B: 6-((tert-butyldimethylsilyl)oxy)-2-chlorobenzo[d]thiazole

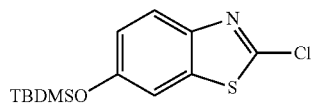

(I-4B)

To a stirred solution of Intermediate I-4A (1.15 g, 6.20 mmol) in DMF (20 mL) was added TBDMS-Cl (1.307 g, 8.67 mmol) and imidazole (0.738 g, 10.84 mmol). After stirring at room temperature for 1.0 h, the reaction mixture was partitioned between EtOAc/water. The organic layer was washed with brine and dried over sodium sulfate. After evaporation of solvent, the crude product was dissolved in a small amount of chloroform and charged to a 24 g silica gel cartridge which was eluted with hexanes for 3 min., then a 15 min gradient from 0% to 15% EtOAc in hexanes. The desired fractions were combined and concentrated to give Intermediate I-4B (1.78 g, 5.94 mmol, 96% yield) as a clear brownish oil. $^1$H NMR (500 MHz, chloroform-d) δ 7.81 (d, J=8.8 Hz, 1H), 7.22 (d, J=2.2 Hz, 1H), 7.01 (dd, J=8.8, 2.5 Hz, 1H), 1.04 (s, 9H), 0.26 (s, 6H); LC-MS: Method A, 50 to 100% B. RT=2.34 min, MS (ESI) m/z: 300.0 and 302.0 (M+H)$^+$.

Intermediate I-4C 6-((tert-butyldimethyl silyl)oxy)-2-(2-(difluoromethoxy)-7-methylquinoxalin-5-yl)benzo[d]thiazole

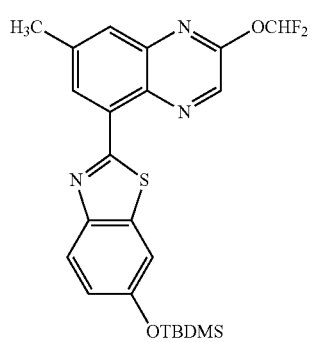

(I-4C)

To Intermediate I-1 (1.45 g, 4.31 mmol), Intermediate I-4B (1.488 g, 4.96 mmol) and [1,1'-bis(diphenylphosphino)ferrocene]dichloropalladium (II) complex with dichloromethane (1:1) (0.176 g, 0.216 mmol) was added toluene (9 mL) and EtOH (3 mL). The mixture was sonicated for 1 min, and flushed with argon. To this was added sodium carbonate, 2M (4.53 mL, 9.06 mmol). The reaction mixture was heated in a microwave at 130° C. for 80 min. HPLC and LCMS indicated a clean reaction. To the reaction mixture was added EtOAc/water. The organic layers were collected, dried over sodium sulfate. After evaporation of solvent, the crude product was dissolved in a small amount of toluene/chloroform and charged to a 80 g silica gel cartridge which was eluted with 5% dichloromethane in hexanes for 3 min., then a 18 min gradient from 5% to 75% dichloromethane in hexanes (flow rate 50 mL/min). The desired fractions were combined and concentrated to give Intermediate I-4C (1.65 g, 3.48 mmol, 81% yield) as a bright yellow solid. $^1$H NMR (500 MHz, chloroform-d) δ 8.76 (d, J=1.9 Hz, 1H), 8.71 (s, 1H), 8.01 (d, J=8.8 Hz, 1H), 7.80 (dd, J=1.8, 1.0 Hz, 1H), 7.68 (t, J$_{HF}$=71.80 Hz, 1H), 7.41 (d, J=2.2 Hz, 1H), 7.07 (dd, J=8.7, 2.3 Hz, 1H), 2.70 (s, 3H), 1.07-1.05 (m, 9H), 0.30-0.28 (m, 6H); $^{19}$F NMR (471 MHz, chloroform-d) δ −89.74 (s, 2F); LC-MS: method A, RT=2.89 min, MS (ESI) m/z: 474.1 (M+H)$^+$.

Intermediate I-4D: 2-(2-(difluoromethoxy)-7-methylquinoxalin-5-yl)benzo[d]thiazol-6-ol

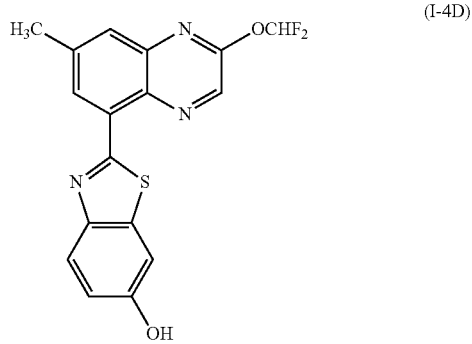 [SMILES: Cc1cc(-c2nc3ccc(O)cc3s2)c2ncc(OC(F)F)nc2c1]

(I-4D)

To a solution of Intermediate I-4C (1.65 g, 3.48 mmol) in THF (15 mL) at room temperature was added acetic acid (0.439 mL, 7.66 mmol), followed by addition of 1.0 N TBAF in THF (4.53 mL, 4.53 mmol) dropwise. The mixture was stirred at room temperature for 40 min. HPLC and LCMS indicated a completion of reaction. The mixture was diluted with EtOAc, washed with water, saturated sodium bicarbonate (2×), brine, and dried over sodium sulfate. After evaporation of the solvent, the crude product was triturated with EtOAc/hexanes (1:4). The precipitate was collected by filtration to give Intermediate I-4D (1.13 g) of the desired product. $^1$H NMR (500 MHz, chloroform-d) δ 8.58 (d, J=1.9 Hz, 1H), 8.53 (s, 1H), 7.76 (d, J=8.8 Hz, 1H), 7.63 (s, 1H), 7.22 (d, J=2.5 Hz, 1H), 7.50 (t, $J_{HF}$=71.80 Hz, 1H), 6.98 (s, 1H), 6.88 (dd, J=8.8, 2.5 Hz, 1H), 2.52 (s, 3H); $^{19}$F NMR (471 MHz, chloroform-d) δ −89.75 (s, 2F); LC-MS: method A, RT=2.24 min, MS (ESI) m/z: 360.0 (M+H)$^+$.

Intermediate I-4E: tert-butyl (2-((2-(2-(difluoromethoxy)-7-methylquinoxalin-5-yl)benzo[d]thiazol-6-yl)oxy)ethyl)carbamate

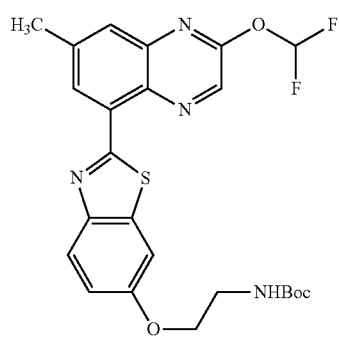

(I-4E)

A solution of tert-butyl (2-hydroxyethyl)carbamate (1.252 g, 7.76 mmol) and DIAD (1.510 mL, 7.76 mmol) in THF (6 mL) was added to a mixture of Intermediate I-4D (0.93 g, 2.59 mmol) and triphenylphosphine (1.358 g, 5.18 mmol) in THF (10 mL) heated at 70° C. dropwise with a syringe pump in 3 h. At the end of addition, HPLC and LCMS indicated a complete conversion of starting material to the product. The mixture was diluted with EtOAc, washed with saturated sodium bicarbonate (2×), brine. The organic layers were collected, dried over sodium sulfate. After evaporation of solvent, the crude product was dissolved in a small amount of chloroform and charged to a 80 g silica gel cartridge which was eluted with dichloromethane for 5 min., then a 18 min gradient from 0% to 25% EtOAc in dichloromethane, flow rate 60 mL/min. The desired fractions were combined and purified with a second ISCO (80 g) column, to give Intermediate I-4E (1.0 g, 1.990 mmol, 77% yield) as a yellow solid. $^1$H NMR (500 MHz, chloroform-d) δ 8.80 (d, J=1.7 Hz, 1H), 8.71 (s, 1H), 8.06 (d, J=8.8 Hz, 1H), 7.81 (dd, J=1.8, 1.0 Hz, 1H), 7.68 (t, $J_{HF}$=71.68 Hz, 1H), 7.43 (d, J=2.5 Hz, 1H), 7.15 (dd, 2.5 Hz, 1H), 4.19-4.12 (m, 2H), 3.63 (d, J=5.0 Hz, 2H), 2.71 (s, 3H), 1.53-1.48 (s, 9H); $^{19}$F NMR (471 MHz, chloroform-d) δ −89.75 (s, 2F); LC-MS: Method A, 50 to 100% B. RT=2.20 min, MS (ESI) m/z: 503.0 (M+H)$^+$.

Intermediate I-4

Intermediate I-4E (1.2 g, 2.388 mmol) was added 4.0 N HCl in dioxane (41.8 ml, 167 mmol), followed by addition of EtOAc (10 mL) to rinse the solid residue on the flask wall. The mixture was left stirring at room temperature overnight. HPLC and LCMS indicated a clean reaction. Solvent was removed, chased twice with EtOAc, once with MeOH, and then dried under high vacuum over the weekend to give Intermediate I-4 (1.0 g, 2.279 mmol, 95% yield) as a bright yellow solid. $^1$H NMR (500 MHz, methanol-$d_4$) δ 8.75 (d, J=1.7 Hz, 1H), 8.73 (s, 1H), 8.11 (d, J=8.8 Hz, 1H), 7.91-7.89 (m, 1H), 7.69 (t, $J_{HF}$=71.53 Hz, 1H), 7.63 (d, J=2.5 Hz, 1H), 7.29 (dd, J=8.9, 2.3 Hz, 1H), 4.38 (t, J=5.0 Hz, 2H), 3.42 (t, J=4.5 Hz, 2H), 2.71 (s, 3H); LC-MS: method A, RT=1.90 min, MS (ESI) m/z: 403.0 (M+H)$^+$.

Intermediate I-5

N-(2-((2-bromo-4-methylbenzo[d]thiazol-6-yl)oxy)ethyl)-4-fluorobenzenesulfonamide

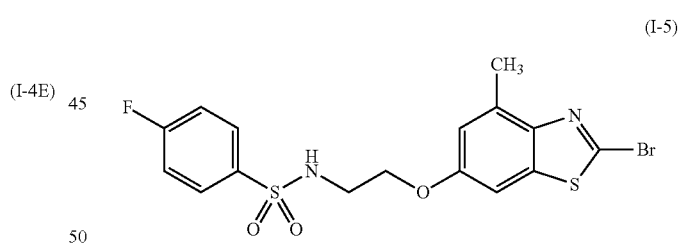

(I-5)

Intermediate I-5A: tert-butyl (2-(3-methyl-4-nitrophenoxy)ethyl)carbamate

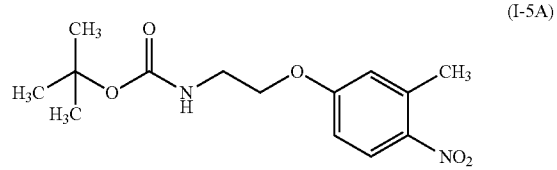 [SMILES: Cc1cc(OCCNC(=O)OC(C)(C)C)ccc1[N+](=O)[O-]]

(I-5A)

In a round bottom flask, tert-butyl (2-hydroxyethyl)carbamate (3.0 g, 18.61 mmol) was dissolved in DMF (20 mL)

and mixed with 4-fluoro-2-methyl-1-nitrobenzene (2.89 g, 18.61 mmol). $K_2CO_3$ (7.72 g, 55.8 mmol) was added. Then the mixture was stirred at 100° C. overnight. On the next day, the reaction mixture was poured into ice water (50 mL) and was extracted with EtOAc (50 mL×2). The combined organic phases were washed with brine, dried over $Na_2SO_4$, filtered, and concentrated to give a crude product that was purified by flash chromatography (80 g silica gel column, eluted with 0-100% EtOAc/Hexane gradient). Collecting desired fractions and removing solvent gave the desired product as a yellow oil. (2.44 g, 8.2 mmol, 44.2%). $^1$H NMR (400 MHz, chloroform-d): δ 8.19-7.94 (m, 1H), 6.91-6.70 (m, 2H), 4.95 (br s, 1H), 4.14-4.05 (m, 2H), 3.56 (q, J=5.3 Hz, 2H), 2.64 (s, 3H), 1.46 (s, 9H); LC-MS: method H, RT=1.13 min, MS (ESI) m/z: 241.1 ([M+H—$(CH_3)_3C$]$^+$).

Intermediate I-5B: tert-butyl (2-(4-amino-3-methylphenoxy)ethyl)carbamate

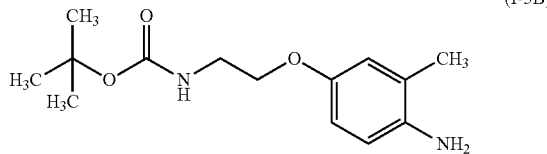

(I-5B)

Intermediate I-5A (3.94 g, 13.30 mmol) was dissolved in MeOH (50 mL) and mixed with wet Pd—C (0.708 g, 0.665 mmol). After applying vacuum and refilling with $H_2$ 3×, the mixture was treated with 1 atm $H_2$ for 4 h. The resulting mixture was filtered over celite and washed with a small amount of MeOH several times. Solvent was removed in vacuo to give Intermediate I-5B as yellow oil. (3.28 g, 93%). $^1$H NMR (500 MHz, CHLOROFORM-d) δ 6.67 (s, 1H), 6.62 (d, J=1.7 Hz, 2H), 5.00 (br. s., 1H), 3.95 (t, J=5.1 Hz, 2H), 3.49 (d, J=5.0 Hz, 2H), 3.37 (br. s., 2H), 2.16 (d, J=0.6 Hz, 3H), 1.46 (s, 9H); LC-MS: method H, RT=0.79 min, MS (ESI) m/z: 267.3).

Intermediate I-5C: tert-butyl (2-((2-amino-4-methyl-benzo[d]thiazol-6-yl)oxy)ethyl) carbamate

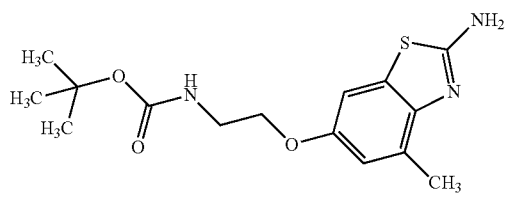

(I-5C)

To Intermediate I-5B (3.28 g, 12.3 mmol) in acetonitrile (30 mL) was added ammonium thiocyanate (1.406 g, 18.5 mmol). The mixture was stirred at room temperature for 10 min, cooled in an ice water bath, and benzyltrimethylammonium tribromide (4.80 g, 12.3 mmol) in acetonitrile (20 mL) was added dropwise. The mixture was stirred at room temperature for 2 h, and then diluted with EtOAc/saturated sodium bicarbonate (100 mL/30 mL). The layers were separated, and the aqueous phase was extracted with EtOAc (30 mL×2). Then organic phases were combined, washed with saturated $NaHCO_3$ (aqueous, 30 mL) and brine (30 mL), dried over $Na_2SO_4$, filtered, and concentrated on a rotary evaporator to give Intermediate I-5C (3.972 g, 12.3 mmol, 100%) as a brown solid. The crude product was used in the next step without further purification. $^1$H NMR (400 MHz, chloroform-d): δ 6.97 (d, J=2.4 Hz, 1H), 6.75 (s, 1H), 5.13 (br s, 2H), 5.00 (br s, 1H), 4.02 (t, J=5.1 Hz, 2H), 3.53 (d, J=4.8 Hz, 2H), 2.53 (d, J=0.4 Hz, 3H), 1.46 (s, 9H); LC-MS: method H, RT=1.04 min, MS (ESI) m/z: 324.2.

Intermediate I-5D: tert-butyl (2-((2-bromo-4-methylbenzo[d]thiazol-6-yl)oxy)ethyl) carbamate

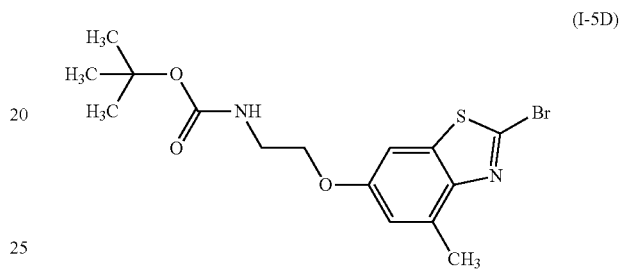

(I-5D)

In a round bottom flask charged with a stirring bar, copper (II) bromide (441 mg, 1.976 mmol), and dry acetonitrile (5 mL) under argon, tert-butyl nitrite (204 mg, 1.976 mmol) was added. The mixture was stirred at room temperature for 10 min. A suspension of Intermediate I-5C (376 mg, 1.163 mmol) in dry acetonitrile (5 mL) was added dropwise. The reaction mixture was stirred at room temperature for 1.0 h, and the acetonitrile was removed under vacuum. The reaction mixture was diluted with EtOAc (50 mL) and 40 mL of 0.5M HCl (aqueous). After separation, the organic layer was washed with 0.5 N HCl (aqueous, 30 mL×2), saturated sodium bicarbonate (aqueous, 30 mL), brine (20 mL), dried over sodium sulfate, filtered, and concentrated on a rotary evaporator. The residue was purified by flash chromatography (40 g silica gel column, 0-50% EtOAc/hexane) to give the desired product as a colorless oil (340 mg, 1.50 mmol, 76%). $^1$H NMR (400 MHz, chloroform-d) δ 7.08 (d, J=2.2 Hz, 1H), 6.88 (d, J=1.5 Hz, 1H), 4.98 (br s, 1H), 4.06 (t, J=5.1 Hz, 2H), 3.56 (d, J=5.1 Hz, 2H), 2.67 (s, 3H), 1.46 (s, 9H); LC-MS: method H, RT=1.37 min, MS (ESI) m/z: 387.0, 389.0.

Intermediate I-5E: tert 2-((2-bromo-4-methylbenzo[d]thiazol-6-yl)oxy)ethanamine

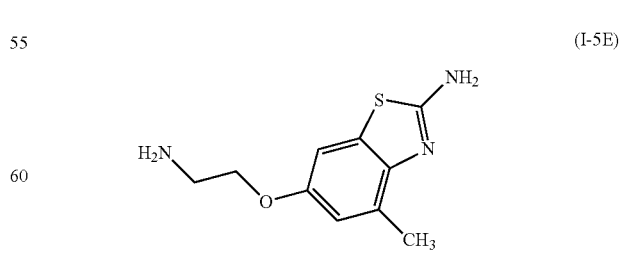

(I-5E)

In a round bottom flask charged with a stirring bar, Intermediate I-5D (940 mg, 2.43 mmol) was dissolved in DCM (4 mL) and treated with TFA (2 ml, 26.0 mmol) at room temperature for 1 hour. Solvent and extra TFA were removed on a rotary evaporator and the residue was dissolved in 30 mL of DCM and was washed with 20 mL of saturated NaHCO$_3$, 20 mL of brine, and dried over Na$_2$SO$_4$. Removing solvent gave the crude product used without purification in the next step. (657 mg, 2.28 mmol, 94%) LC-MS: method H, RT=0.85 min, MS (ESI) m/z: 87.0, 289.0.

Intermediate I-5

Intermediate I-5E (534 mg, 1.86 mmol) was dissolved in a mixture of THF (5 mL) and DIEA (1.30 mL, 7.45 mmol). 4-Fluorobenzene-1-sulfonyl chloride (362 mg, 1.862 mmol) in THF (5 mL) was added dropwise, and the mixture was stirred at room temperature for 30 minutes. Solvent was removed on a rotary evaporator and the residue was purified by flash chromatography (40 g silica gel column, 0-100% EtOAc/hexane gradient) to give the title compound as a white solid (666 mg, 1.49 mmol, 80%). $^1$H NMR (400 MHz, chloroform-d) δ 7.96-7.87 (m, 2H), 7.23-7.14 (m, 2H), 6.99 (d, J=2.2 Hz, 1H), 6.79-6.76 (m, 1H), 4.05 (t, J=5.1 Hz, 2H), 3.46-3.36 (m, 2H), 2.66 (s, 3H); LC-MS: method H, RT=1.37 min, MS (ESI) m/z: 444.9 and 446.9.

Intermediate I-9

(2-methoxy-7-methylquinoxalin-5-yl)boronic acid

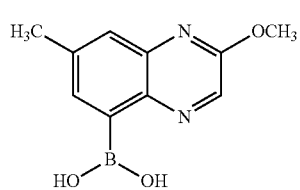

(I-9)

Intermediate I-9A:
5-bromo-2-methoxy-7-methylquinoxaline

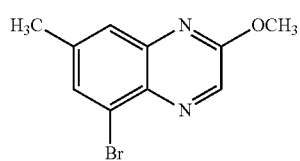

(I-9A)

To Intermediate I-1G (3.13 g, 10.83 mmol) dissolved in THF (20 mL) and MeOH (15 mL) at room temperature was added 4.3 M sodium methoxide in MeOH (7.55 mL, 32.5 mmol). The reaction mixture was stirred at room temperature overnight. Methanol was removed under vacuum. The reaction mixture was diluted with EtOAc, quenched with 0.5 N HCl (30.0 mL). The organic layer was washed with saturated sodium bicarbonate, brine, dried and concentrated to give Intermediate I-9A (2.7 g, 10.67 mmol, 99% yield) as a slightly yellow solid. $^1$H NMR (500 MHz, chloroform-d) δ 8.48 (s, 1H), 7.72 (d, J=1.7 Hz, 1H), 7.60 (dd, J=1.8, 1.0 Hz, 1H), 4.10 (s, 3H), 2.53 (s, 3H); LC-MS: Method A, 30 to 100% B. RT=1.71 min, MS (ESI) m/z: 253.0 and 255.0 (M+H)$^+$.

Intermediate I-9

A mixture of Intermediate I-9A (700 mg, 2.77 mmol), 4,4,4',4',5,5,5',5'-octamethyl-2,2'-bi(1,3,2-dioxaborolane) (1053 mg, 4.15 mmol), potassium acetate (679 mg, 6.91 mmol) and [1,1'-bis(diphenylphosphino)ferrocene]dichloropalladium (II) complex with dichloromethane (1:1) (113 mg, 0.138 mmol) in dioxane (14 mL) was degassed by bubbling argon for 5 min. It was then heated at 130° C. for 40 min. The reaction mixture was mixed with EtOAc/water and stirred at room temperature for 15 min. The insoluble material was removed by filtration through a pad of wet celite. The organic layer was washed with brine, dried over sodium sulfate and concentrated. The crude product was purified by flash chromatography (loading in chloroform, 5% to 100% EtOAc in hexane over 15 min using a 80 g silica gel cartridge). The desired fractions were combined, concentrated and lyophilized to yield to yield Intermediate I-9 (362 mg, 1.659 mmol, 60% yield) as a solid. $^1$H NMR (500 MHz, methanol-d$_4$) δ 8.41 (s, 1H), 7.69 (br. s., 1H), 7.49 (br. s., 1H), 4.10 (s, 3H), 2.56 (s, 3H). LC-MS: method H, RT=0.83 min, MS (ESI) m/z: 219.1 (M+H)$^+$.

Intermediate I-12

2-methoxy-7-methylquinoxaline-5-carbothioamide

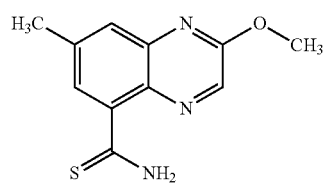

(I-12)

Intermediate I-12A:
2-methoxy-7-methylquinoxaline-5-carbonitrile

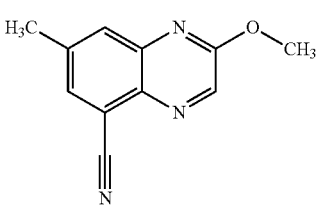

(I-12A)

Intermediate I-9A (0.458 g, 1.810 mmol) and copper(I) cyanide (0.600 g, 6.70 mmol) were dissolved in DMF (18.10 mL) and heated to reflux for 20 hours. The reaction mixture was cooled to ambient temperature. The reaction mixture was diluted with saturated NaHCO$_3$ and extracted with EtOAc. The organic layer was further washed with water then brine, dried (Na$_2$SO$_4$), filtered, and concentrated in vacuo. The crude material was purified by column chromatography (ISCO, 12 g silica gel column, 17 minute gradient from 0 to 100% EtOAc in hexanes) to give Intermediate I-12A (247 mg, 1.24 mmol, 68.5%) as a white solid: $^1$H NMR (400 MHz, CHLOROFORM-d) δ 8.55 (s, 1H), 7.86 (d, J=0.8 Hz, 1H), 7.78 (s, 1H), 4.11 (s, 3H), 2.58 (s, 3H); LC-MS: Method H, RT=0.92 min, MS (ESI) m/z: 200.1 (M+H)$^+$.

Intermediate I-12

Intermediate I-12A (0.247 g, 1.240 mmol), sodium hydrosulfide (1.043 g, 18.60 mmol), and magnesium chloride (1.771 g, 18.60 mmol) were dissolved in DMF (12.40 mL) and stirred for 18 hours. The reaction mixture was diluted with water, which formed copious amounts of precipitates. The reaction mixture was extracted thrice with EtOAc. The combined organic layers were washed with brine, dried (Na$_2$SO$_4$), filtered, and concentrated in vacuo. The solid was sonicated with DCM then filtered. The resulting solution was concentrated in vacuo to give Intermediate I-12 (111 mg, 0.476 mmol, 38.4%) as an orange solid: $^1$H NMR (400 MHz, CHLOROFORM-d) δ 11.86 (br. s., 1H), 9.04 (d, J=2.0 Hz, 1H), 8.40 (s, 1H), 8.32 (br. s., 1H), 7.82 (dd, J=1.9, 0.9 Hz, 1H), 4.11 (s, 3H), 2.61 (s, 3H); LC-MS: Method H, RT=0.88 min, MS (ESI) m/z: 234.0 (M+H)$^+$.

Intermediate I-14

5-iodo-7-methylquinoxalin-2(1H)-one

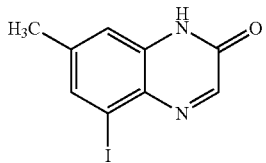

(I-14)

Intermediate I-14A: 2-iodo-4-methyl-6-nitroaniline

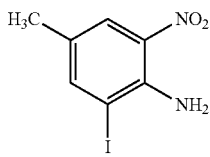

(I-14A)

Iodine (4.59 g, 18.07 mmol) was dissolved in EtOH (65.7 mL). Next, 4-methyl-2-nitroaniline (2.5 g, 16.43 mmol) and then silver sulfate (5.64 g, 18.07 mmol) were added and the reaction mixture was allowed to stir for 18 hours. The reaction mixture was diluted with EtOAc, filtered through a sintered glass funnel, and concentrated in vacuo. The crude material was redissolved in EtOAc and washed with saturated Na$_2$S$_2$O$_3$, saturated NaHCO$_3$, then brine, dried (Na$_2$SO$_4$), filtered, and concentrated in vacuo to give Intermediate I-14A (4.65 g, 16.72 mmol, 100%) as an orange solid: $^1$H NMR (400 MHz, CHLOROFORM-d) δ 7.97 (d, J=1.0 Hz, 1H), 7.78 (d, J=2.0 Hz, 1H), 6.49 (br. s., 2H), 2.26 (s, 3H); LC-MS: Method H, RT=0.98 min, MS (ESI) m/z: 279.0 (M+H)$^+$.

Intermediate I-14B: bis-tert-butyl (2-iodo-4-methyl-6-nitroaniline)bis carbamate

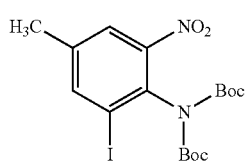

(I-14B)

Intermediate I-14A (4.65 g, 16.72 mmol), DMAP (0.204 g, 1.672 mmol), and Boc$_2$O (9.71 mL, 41.8 mmol) were dissolved in THF (27.9 mL) and stirred for 18 hours. The reaction mixture was diluted with water and extracted with EtOAc. The organic layer was washed with brine, dried (Na$_2$SO$_4$), filtered, and concentrated in vacuo. The crude material was purified by column chromatography (ISCO, 220 g silica gel column, 50 minute gradient from 0 to 100% EtOAc in hexanes), to give Intermediate I-14B (5.4 g, 11.29 mmol, 67.5%) as a light yellow solid: $^1$H NMR (400 MHz, CHLOROFORM-d) δ 7.94 (s, 1H), 7.78 (s, 1H), 2.43 (s, 3H), 1.40 (s, 18H); LC-MS: Method H, RT=1.10 min, MS (ESI) m/z: (bis-deboc mass observed) 278.9 (M+H)$^+$.

Intermediate I-14C: methyl 2-((tert-butoxycarbonyl) (2-iodo-4-methyl-6-nitrophenyl)amino)acetate

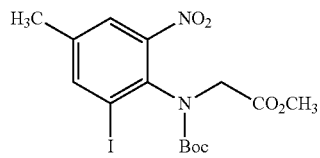

(I-14C)

Intermediate I-14B (5.4 g, 11.29 mmol) was dissolved in DCM (18.82 mL) and TFA (1.740 mL, 22.58 mmol) and stirred for 30 minutes. The reaction mixture was diluted with DCM, quenched with saturated NaHCO$_3$, washed with brine, dried (Na$_2$SO$_4$), filtered, and concentrated in vacuo. The crude material was dissolved in DMF (18.82 mL). Cs$_2$CO$_3$ (9.20 g, 28.2 mmol) was added and stirred for 15 minutes. The reaction mixture turned deep red. Methyl bromoacetate (1.249 mL, 13.55 mmol) was added and the reaction mixture was allowed to stir 24 hours. The reaction mixture turned from deep red to yellow. The reaction mixture was diluted with EtOAc, washed with water, then brine, dried (Na$_2$SO$_4$), filtered, and concentrated in vacuo. The crude material was purified by column chromatography (ISCO, 220 g silica gel column, 50 minute gradient from 0 to 100% EtOAc in hexanes) to give Intermediate I-14C (3.51 g, 7.80 mmol, 69.1%) as an orange solid: LC-MS: Method H, RT=1.00 min, MS (ESI) m/z: (deboc mass observed) 350.9 (M+H)$^+$.

Intermediate I-14D: methyl 2-((2-iodo-4-methyl-6-nitrophenyl)amino)acetate

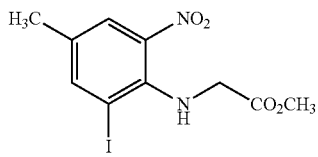

(I-14D)

Intermediate I-14C (3.51 g, 7.80 mmol) was dissolved in HCl in dioxane (4 M, 9.75 mL, 39.0 mmol) and stirred for 1 hour. The reaction mixture was concentrated in vacuo to give Intermediate I-14D, which was used directly in the subsequent step without purification: LC-MS: Method H, RT=0.79 min, MS (ESI) m/z: 350.9 (M+H)$^+$.

Intermediate I-14E: 5-iodo-7-methyl-3,4-dihydroquinoxalin-2(1H)-one

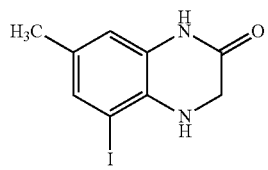

(I-14E)

Intermediate I-14D (2.73 g, 7.80 mmol) was dissolved in MeOH (28.4 mL). HCl (2.60 mL, 31.2 mmol) then tin(II) chloride dihydrate (7.04 g, 31.2 mmol) were added and the reaction mixture was heated to 65° C. for 3.5 hours. The reaction mixture was cooled to ambient temperature, neutralized with 10 N NaOH and diluted with brine then EtOAc. Vigorous stirring was allowed for 15 minutes. The mixture was filtered through celite and concentrated in vacuo to give Intermediate I-14E (1.77 g, 6.14 mmol, 79.0%) as an orange solid: $^1$H NMR (400 MHz, CHLOROFORM-d) δ 7.57 (br. s., 1H), 7.17 (s, 1H), 6.48 (s, 1H), 4.17 (br. s., 1H), 4.02 (d, J=1.8 Hz, 2H), 2.21 (s, 3H); LC-MS: Method H, RT=0.82 min, MS (ESI) m/z: 289.0 (M+H)$^+$.

Intermediate I-14

Intermediate I-14E (1.7696 g, 6.14 mmol) was suspended in MeOH (17.86 mL). 1 N NaOH (18.43 mL, 18.43 mmol) then H$_2$O$_2$ (30%) (3.23 mL, 36.9 mmol) were added and the reaction mixture stirred 24 hours. More H$_2$O$_2$ (3.23 mL, 36.9 mmol) was added and the reaction mixture was stirred for 24 hours. More H$_2$O$_2$ (3.23 mL, 36.9 mmol) was added and the reaction mixture was stirred for 24 hours. The reaction mixture was diluted with ca 50 mL of water then about 50 mL of brine. The mixture was evaporated under a nitrogen stream to remove MeOH. The aqueous material was extracted thrice with EtOAc. During the extractions, an off-white solid precipitated. This precipitate was collected by suction filtration to give Intermediate I-14 (1.35 g, 4.72 mmol, 77.0%): $^1$H NMR (400 MHz, DMSO-d$_6$) δ 12.44 (br. s., 1H), 8.11 (s, 1H), 7.72 (d, J=1.5 Hz, 1H), 7.09 (s, 1H), 2.37 (s, 3H); LC-MS: Method H, RT=0.80 min, MS (ESI) m/z: 287.0 (M+H)$^+$.

Intermediate I-15

(2-(ethoxycarbonyl)-7-methylquinoxalin-5-yl)boronic acid

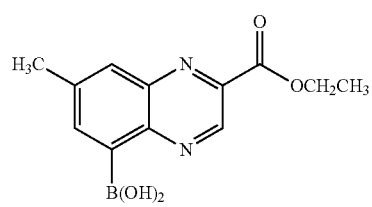

(I-15)

Intermediate I-15A: 3-bromo-5-methylbenzene-1,2-diamine

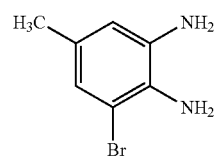

(I-15A)

2-bromo-4-methyl-6-nitroaniline (5.00 g, 21.64 mmol) was dissolved in MeOH (148 mL) and THF (18.50 mL). Ammonium chloride (23.15 g, 433 mmol) then zinc (14.15 g, 216 mmol) were added and the reaction mixture was heated to 40° C. for 1 h. The reaction mixture was cooled to ambient temperature, concentrated in vacuo, re-dissolved in EtOAc and saturated Na$_2$CO$_3$, and stirred vigorously for 10 minutes. The mixture was filtered through a sintered glass funnel and washed with more EtOAc. The organic layer was further washed twice with water, washed with brine, dried with sodium sulfate, filtered, and concentrated in vacuo to yield Intermediate I-15A (4.35 g, 21.63 mmol, 100% yield). $^1$H NMR (400 MHz, CHLOROFORM-d) δ 6.81 (s, 1H), 6.48 (s, 1H), 3.66 (br. s., 2H), 3.46 (br. s., 2H), 2.19 (s, 3H). LC-MS: method H, RT=0.93 min, MS (ESI) m/z: 201.0 (M+H)$^+$.

Intermediate I-15B: ethyl 5-bromo-7-methylquinoxaline-2-carboxylate

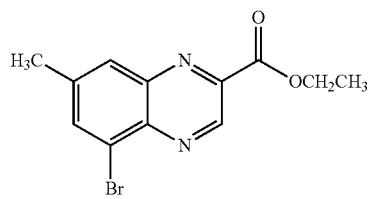

(I-15B)

Intermediate I-15A (4.35 g, 21.63 mmol) and ethyl 3-bromo-2-oxopropanoate (3.63 mL, 26.0 mmol) were dissolved in NMP (72.1 mL) and allowed to stir at room temperature for 18 h open to air. The reaction mixture was diluted with water and EtOAc. The layers were separated and the aqueous layer was back extracted with EtOAc (×3). The combined organic layer was washed with brine, dried with sodium sulfate, and concentrated under reduced pressure. The reaction mixture was purified by ISCO column using 0-40% EtOAc in hexanes on a 220 g column to yield a mixture of regioisomers. The reaction mixture was purified by SFC on a Chiralcel OD-H, 30×250 mm, 5 micron column using 20% IPA/80% $CO_2$ with 85 mL/min, 100 Bar, 40° C. to yield Intermediate I-15B (0.936 g, 3.17 mmol, 14.66% yield) as a yellow solid. $^1$H NMR (400 MHz, CHLOROFORM-d) δ 9.48 (s, 1H), 8.01 (s, 1H), 7.99 (s, 1H), 4.53 (q, J=7.0 Hz, 2H), 2.55 (s, 3H), 1.44 (t, J=7.2 Hz, 3H). LC-MS: method H, RT=1.15 min, MS (ESI) m/z: 295.1 (M+H)$^+$.

Intermediate I-15

A mixture of Intermediate I-15B (0.100 g, 0.339 mmol), 4,4,4',4',5,5,5',5'-octamethyl-2,2'-bi(1,3,2-dioxaborolane) (0.129 g, 0.508 mmol), potassium acetate (0.083 g, 0.847 mmol) in dioxane (3.39 mL) were degassed by bubbling argon for 5 min. $PdCl_2$(dppf)-$CH_2Cl$ adduct (0.014 g, 0.017 mmol) was added and the mixture was sealed and heated in microwave at 130° C. for 30 min. The reaction mixture was diluted with water and EtOAc. The layers were separated and the organic layer was washed with brine, dried with sodium sulfate, and concentrated under reduced pressure to yield a brown oil. The reaction mixture was purified on Prep HPLC using Method A to yield Intermediate I-15 (0.027 g, 0.104 mmol, 30.6% yield) as an off white solid. LC-MS: method H, RT=1.15 min, MS (ESI) m/z: 261.2 (M+H)$^+$.

Intermediate I-16

(2-bromo-5-methoxy-7-methylthiazolo[5,4-b]pyridine

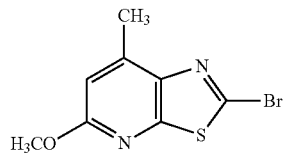

(I-16)

Intermediate I-16A:
1-(6-methoxy-4-methylpyridin-3-yl)thiourea

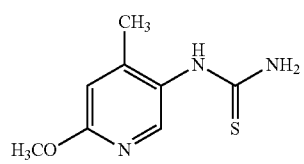

(I-16A)

To a solution of 6-methoxy-4-methylpyridin-3-amine (0.150 g, 1.086 mmol) in acetone (1 mL) was added dropwise benzoyl isothiocyanate (0.161 mL, 1.194 mmol). The reaction mixture was allowed to stir at room temperature for 2.5 h. The reaction mixture was concentrated under reduced pressure and re-dissolved in tetrahydrofuran (1 mL). To this solution was added sodium methoxide (0.5 M in MeOH) (3.26 mL, 1.628 mmol), and the reaction mixture was allowed to stir at room temperature for 30 min. The reaction mixture was diluted with water and EtOAc. The layers were separated and the organic layer was washed with brine, dried with sodium sulfate, and concentrated under reduced pressure. The reaction mixture was triturated with $Et_2O$ and filtered. The solid was collected to yield Intermediate I-16A (0.148 g, 0.750 mmol, 69.1% yield) as a brown solid. $^1$H NMR (400 MHz, CHLOROFORM-d) δ 8.04 (s, 1H), 7.54 (br. s., 1H), 6.69 (s, 1H), 6.51-5.18 (m, 2H), 3.93 (s, 3H), 2.28 (s, 3H). LC-MS: method H, RT=0.93 min, MS (ESI) m/z: 198.1 (M+H)$^+$.

Intermediate I-16B: 5-methoxy-7-methylthiazolo[5,4-b]pyridin-2-amine

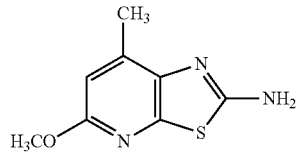

(I-16B)

To a solution of Intermediate I-16A (0.146 g, 0.740 mmol) in tetrahydrofuran (1 mL) was added benzyltrimethylammonium tribromide (0.289 g, 0.740 mmol). The reaction mixture was allowed to stir at room temperature for 2 hours. The reaction mixture was diluted with water and EtOAc. The layers were separated and the organic layer was washed with saturated aqueous $NaHCO_3$, washed with brine, dried with sodium sulfate, and concentrated under reduced pressure. The reaction mixture was purified on ISCO using 0-100% EtOAc in hexanes gradient on a 24 g column to yield Intermediate I-16B (0.035 g, 0.179 mmol, 24.22% yield) as a white solid. $^1$H NMR (400 MHz, CHLOROFORM-d) δ 6.53 (d, J=0.7 Hz, 1H), 5.00 (br. s., 2H), 3.91 (s, 3H), 2.49 (d, J=0.9 Hz, 3H). LC-MS: method H, RT=0.93 min, MS (ESI) m/z: 196.1 (M+H)$^+$.

Intermediate I-16

Copper (II) bromide (0.068 g, 0.305 mmol) and t-butyl nitrite (0.036 mL, 0.305 mmol) were dissolved in MeCN (0.717 mL) and allowed to stir 10 minutes. Intermediate I-16B (0.035 g, 0.179 mmol) was dissolved in MeCN (1.076 mL) and the copper solution was added. The reaction mixture was allowed to stir at room temperature for 2 h. The reaction mixture was diluted with EtOAc, washed with 1 N HCl, saturated aqueous $NaHCO_3$, washed with brine, dried with sodium sulfate, filtered, and concentrated in vacuo to yield Intermediate I-16 (0.030 g, 0.116 mmol, 64.6% yield). $^1$H NMR (400 MHz, CHLOROFORM-d) δ 6.64 (d, J=1.1 Hz, 1H), 3.96 (s, 3H), 2.62 (d, J=0.9 Hz, 3H). LC-MS: method H, RT=0.93 min, MS (ESI) m/z: 359.1 (M+H)$^+$.

Intermediate I-17

2-bromo-6-fluoro-5-methoxythiazolo[5,4-b]pyridine

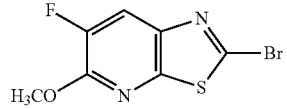

(I-17)

Intermediate I-17A: N-((5-fluoro-6-methoxypyridin-3-yl)carbamothioyl)benzamide

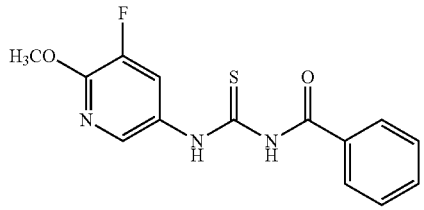

(I-17A)

To a solution of 5-fluoro-6-methoxypyridin-3-amine (0.100 g, 0.704 mmol) in acetone (1 mL) was added dropwise benzoyl isothiocyanate (0.104 mL, 0.774 mmol). The reaction mixture was allowed to stir at room temperature for 3 h. The reaction mixture was diluted with water and EtOAc. The layers were separated and the organic layer was washed with brine, dried with sodium sulfate, and concentrated under reduced pressure to yield Intermediate I-17A (0.215 g, 0.704 mmol, 100% yield): $^1$H NMR (400 MHz, CHLOROFORM-d) δ 12.48 (br. s., 1H), 9.12 (br. s., 1H), 8.06 (d, J=2.0 Hz, 1H), 8.01 (dd, J=10.8, 2.2 Hz, 1H), 7.91 (d, J=1.1 Hz, 1H), 7.89 (d, J=1.5 Hz, 1H), 7.71-7.65 (m, 1H), 7.60-7.54 (m, 2H), 4.06 (s, 3H). LC-MS: method H, RT=1.18 min, MS (ESI) m/z: 306.1 (M+H)$^+$.

Intermediate I-17B: 1-(5-fluoro-6-methoxypyridin-3-yl)thiourea

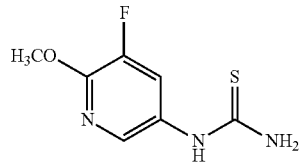

(I-17B)

To a solution of Intermediate I-17A (0.215 g, 0.704 mmol) in tetrahydrofuran (1 mL) was added dropwise sodium methoxide (0.5 M in MeOH) (2.112 mL, 1.056 mmol). The reaction mixture was allowed to stir at room temperature for 18 h. The reaction mixture was diluted with water and EtOAc. The layers were separated and the organic layer was washed with brine, dried with sodium sulfate, and concentrated under reduced pressure. The residue was triturated with Et$_2$O, and the solid was collected to yield Intermediate I-17B (0.09 g, 0.447 mmol, 63.5% yield) as a pale yellow solid. LC-MS: method H, RT=0.81 min, MS (ESI) m/z: 202.1 (M+H)$^+$. $^1$H NMR (400 MHz, CHLOROFORM-d) δ 7.86 (d, J=2.2 Hz, 1H), 7.63 (br. s., 2H), 7.32 (s, 1H), 4.03 (s, 3H).

Intermediate I-17C: 6-fluoro-5-methoxythiazolo[5,4-b]pyridin-2-amine

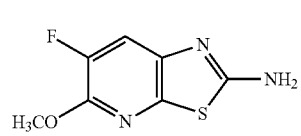

(I-17C)

To a solution of Intermediate I-17B (0.078 g, 0.338 mmol) in tetrahydrofuran (1 mL) was added benzyltrimethylammonium tribromide (0.151 g, 0.388 mmol). The reaction mixture was allowed to stir at room temperature for 2 hours. The reaction mixture was diluted with water and EtOAc. The layers were separated and the organic layer was washed with saturated aqueous NaHCO$_3$, washed with brine, dried with sodium sulfate, and concentrated under reduced pressure. The reaction mixture was purified on Prep HPLC using Method A to yield Intermediate I-17C (0.028 g, 0.141 mmol, 36.3% yield) as a white solid. $^1$H NMR (400 MHz, CHLOROFORM-d) δ 7.87 (br. s., 2H), 7.59 (d, J=9.7 Hz, 1H), 4.05 (s, 3H) LC-MS: method H, RT=0.84 min, MS (ESI) m/z: 200.1 (M+H)$^+$.

Intermediate I-17

Copper (II) bromide (0.055 g, 0.247 mmol) and t-butyl nitrite (0.029 mL, 0.247 mmol) were dissolved in MeCN (0.582 mL) and allowed to stir 10 minutes. Intermediate I-17C (0.029 g, 0.146 mmol) was dissolved in MeCN (0.873 mL) and the copper solution was added. The reaction mixture was diluted with EtOAc, washed with 1 N HCl, saturated aqueous NaHCO$_3$, then brine, dried with sodium sulfate, filtered, and concentrated in vacuo to yield Intermediate I-17 (0.035 g, 0.133 mmol, 91% yield). $^1$H NMR (400 MHz, CHLOROFORM-d) δ 7.86 (d, J=9.9 Hz, 1H), 4.09 (s, 3H). LC-MS: method H, RT=1.23 min, MS (ESI) m/z: 263.0 (M+H)$^+$.

Intermediate I-20

2-bromo-6-methoxybenzo[d]thiazole-4-carbaldehyde

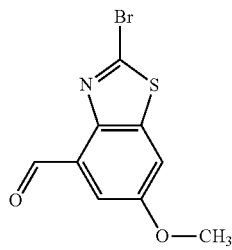

(I-20)

Intermediate I-20A: Methyl 2-amino-5-methoxybenzoate

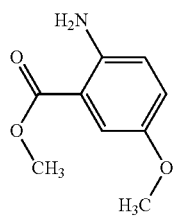

(I-20A)

2-amino-5-methoxybenzoic acid (250 mg, 1.496 mmol) was dissolved in MeOH (7478 µL). Thionyl chloride (327 µL, 4.49 mmol) was added and the reaction mixture was heated to reflux for 3 days. The reaction mixture was concentrated in vacuo. The crude material was dissolved in EtOAc and washed with 1 N NaOH, then water, then brine, dried (Na$_2$SO$_4$), filtered, and concentrated in vacuo to give Intermediate I-20A (190 mg, 1.049 mmol, 70.1%) as a brown oil: $^1$H NMR (400 MHz, CHLOROFORM-d) δ 7.38 (d, J=3.1 Hz, 1H), 6.98 (dd, J=9.0, 3.1 Hz, 1H), 6.66 (d, J=8.8 Hz, 1H), 5.43 (br. s., 2H), 3.90 (s, 3H), 3.79 (s, 3H); LC-MS: Method H, RT=0.89 min, MS (ESI) m/z: 182.1 (M+H)$^+$.

Intermediate I-20B: Methyl 2-amino-6-methoxy-benzo[d]thiazole-4-carboxylate

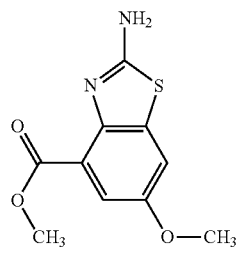

(I-20B)

Intermediate I-20A (190 mg, 1.049 mmol) was dissolved in MeCN (5243 μL). Ammonium thiocyanate (120 mg, 1.573 mmol) was added, followed by benzyltrimethylammonium tribromide (409 mg, 1.049 mmol). After 4 hours, the reaction mixture was diluted with EtOAc, washed with saturated NaHCO$_3$, then brine, dried (Na$_2$SO$_4$), filtered, and concentrated in vacuo. The crude material was purified by column chromatography (ISCO, 12 g silica gel column, 17 minute gradient from 0 to 100% EtOAc in hexanes) to give Intermediate I-20B (100 mg, 0.42 mmol, 40%) as a brown solid: $^1$H NMR (400 MHz, CHLOROFORM-d) δ 7.51 (d, J=2.6 Hz, 1H), 7.35 (d, J=2.6 Hz, 1H), 5.89 (br. s., 2H), 3.99 (s, 3H), 3.88 (s, 3H); LC-MS: Method H, RT=0.82 min, MS (ESI) m/z: 239.1 (M+H)$^+$.

Intermediate I-20C: Methyl 2-bromo-6-methoxy-benzo[d]thiazole-4-carboxylate

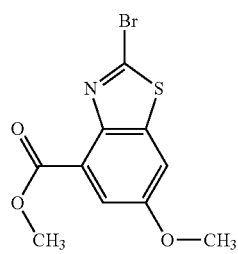

(I-20C)

Copper(II) bromide (159 mg, 0.713 mmol) and t-butyl nitrite (85 μL, 0.713 mmol) were dissolved in MeCN (1679 μL) and allowed to stir 10 minutes. Intermediate I-20B (100 mg, 0.420 mmol) was dissolved in MeCN (2518 μL) and the copper solution was added. After 2 hours, the reaction mixture was diluted with EtOAc, washed with 1 N HCl, saturated NaHCO$_3$, then brine, dried (Na$_2$SO$_4$), filtered, and concentrated in vacuo to give Intermediate I-20C (100.6 mg, 0.333 mmol, 79%) as a red solid: $^1$H NMR (400 MHz, CHLOROFORM-d) δ 7.68 (d, J=2.6 Hz, 1H), 7.46 (d, J=2.6 Hz, 1H), 4.05 (s, 3H), 3.93 (s, 3H); LC-MS: Method H, The compound did not ionize.

Intermediate I-20D: (2-bromo-6-methoxybenzo[d]thiazol-4-yl)methanol

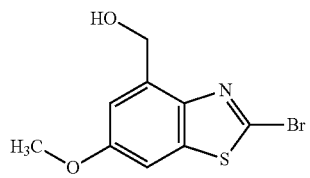

(I-20D)

Intermediate I-20C (93.5 mg, 0.309 mmol) was dissolved in toluene (2063 μL) and THF (1032 μL) and cooled to −78° C. DIBAL-H (681 μL, 0.681 mmol) was added and the reaction mixture was warmed to ambient temperature for 1 hour. The reaction was quenched with 1 N HCl (1 mL), diluted with EtOAc, filtered through celite, and concentrated in vacuo. The crude material was purified by column chromatography (ISCO, 12 g silica gel column, 17 minute gradient from 0 to 100% EtOAc in hexanes) to give Intermediate I-20D (28.1 mg, 0.103 mmol, 33%) as an off-white solid: $^1$H NMR (400 MHz, CHLOROFORM-d) δ 7.17 (d, J=2.6 Hz, 1H), 7.04 (d, J=2.6 Hz, 1H), 5.05 (d, J=6.6 Hz, 2H), 3.87 (s, 3H), 3.00 (t, J=6.5 Hz, 1H); LC-MS: Method H, RT=1.06 min, MS (ESI) m/z: 274/276 (M+H)$^+$.

Intermediate I-20

Intermediate I-20D (188.8 mg, 0.689 mmol) was dissolved in CHCl$_3$ (4591 μL). Manganese dioxide (359 mg, 4.13 mmol) was added and the reaction mixture was allowed to stir for 24 hours. More manganese dioxide (359 mg, 4.13 mmol) was added and the reaction mixture was allowed to stir for 3 days. The reaction mixture was filtered through celite and concentrated in vacuo. The crude material was purified by column chromatography (ISCO, 12 g silica gel column, 17 minute gradient from 0 to 100% EtOAc in hexanes) to give Intermediate I-20 (136.3 mg, 0.501 mmol, 72.7%) as a white solid: $^1$H NMR (400 MHz, CHLOROFORM-d) δ 10.90-10.84 (m, 1H), 7.63-7.59 (m, 1H), 7.57-7.51 (m, 1H), 3.93 (s, 3H); LC-MS: Method H, RT=1.17 min, MS (ESI) m/z: 272/274 (M+H)$^+$.

Intermediate I-22

4-bromo-6-methoxybenzo[d]thiazol-2-amine

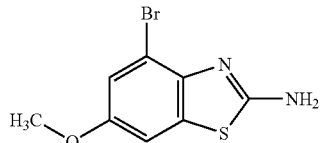

(I-22)

2-Bromo-4-methoxyaniline (10 g, 49.5 mmol) was dissolved in MeCN (247 mL). Ammonium thiocyanate (5.65 g, 74.2 mmol) was added, followed by benzyltrimethylammonium tribromide (19.3 g, 49.5 mmol). After stirring for 2 days, the reaction mixture was diluted with saturated NaHCO$_3$ and the resulting solid was collected by suction filtration. The solid was washed with water to give Intermediate I-22 (10.75 g, 41.5 mmol, 84% yield) as a light brown solid: $^1$H NMR (400 MHz, CHLOROFORM-d) δ 7.19 (d, J=2.4 Hz, 1H), 7.06 (d, J=2.4 Hz, 1H), 3.78 (s, 3H); LC-MS: Method H, RT=0.70 min, MS (ESI) m/z: 259/261 (M+H)$^+$.

Intermediate I-25

2-(methoxymethyl)-7-methyl-5-(4,4,5,5-tetramethyl-1,3,2-dioxaborolan-2-yl) quinoxaline, D$_5$

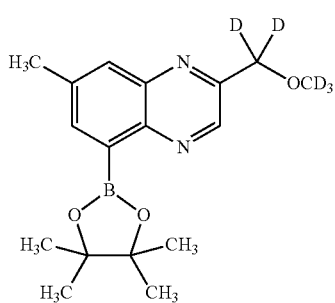

(I-25)

Intermediate I-25A:
(5-bromo-7-methylquinoxalin-2-yl)methanol

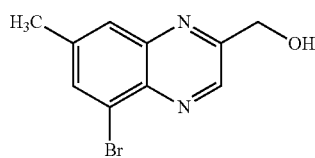

(I-25A)

NaBH$_4$ (135 mg, 3.56 mmol) and calcium chloride (197 mg, 1.779 mmol) were dissolved in THF (5270 µl). A solution of Intermediate I-15B (500 mg, 1.779 mmol) in THF (1318 µl) was added dropwise, and the reaction mixture was allowed to stir at room temperature for 18 h. The reaction mixture was diluted with EtOAc, washed with water, washed with brine, dried with sodium sulfate, filtered, and concentrated under reduced pressure. The crude material was purified by column chromatography (ISCO, 40 g silica gel column, 19 minute gradient from 0 to 100% EtOAc in hexanes) to yield Intermediate I-25A (0.263 g, 1.04 mmol, 58%) as a yellow solid. $^1$H NMR (500 MHz, CHLOROFORM-d) δ 8.85 (s, 1H), 7.92 (d, J=1.7 Hz, 1H), 7.79 (dd, J=1.7, 1.1 Hz, 1H), 5.04 (s, 2H), 3.73 (br. s., 1H), 2.58 (s, 3H). LC-MS: method H, RT=0.93 min, MS (ESI) m/z: 253.1 (M+H)$^+$.

Intermediate I-25B:
(5-bromo-7-methylquinoxalin-2-yl)methyl methanesulfonate

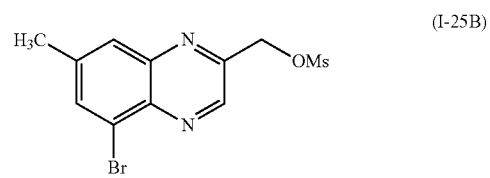 [SMILES: Cc1cc(Br)c2ncc(COS(C)(=O)=O)nc2c1]

(I-25B)

Intermediate I-25A (262.5 mg, 1.037 mmol) and TEA (0.434 mL, 3.11 mmol) were dissolved in DCM (20 mL) and methanesulfonic anhydride (217 mg, 1.245 mmol) was added. The reaction mixture was stirred at room temperature for 1 h. The reaction mixture was diluted with DCM and washed with saturated NaHCO$_3$, dried with sodium sulfate, filtered, and concentrated in vacuo to yield Intermediate I-25B (0.343 g, 1.04 mmol, 100%) as an orange solid. The material will be used crude in the next step. LC-MS: method H, RT=1.00 min, MS (ESI) m/z: 331.0 (M+H)$^+$.

Intermediate I-25C:
5-bromo-2-(methoxymethyl)-7-methylquinoxaline, d$_5$

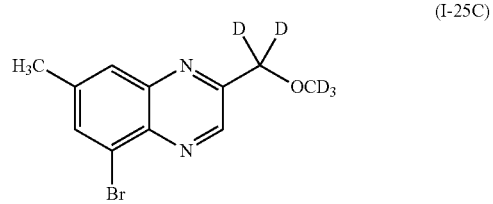

(I-25C)

CD$_3$ONa was prepared by dissolving sodium metal (60 mg, 2.500 mmol) in CD$_3$OD (0.405 mL, 10 mmol) for 30 minutes. Intermediate I-25B (207 mg, 0.625 mmol) was dissolved in THF (12 mL). CD$_3$ONa (71.3 mg, 1.250 mmol) was added, and the reaction mixture was allowed to stir at room temperature for 18 h. The reaction mixture was partially concentrated in vacuo to remove THF, diluted with EtOAc and washed with water, washed with brine, dried with sodium sulfate, filtered, and concentrated in vacuo to yield Intermediate I-25C (0.118 g, 0.432 mmol, 69% yield). $^1$H NMR (400 MHz, CHLOROFORM-d) δ 9.01 (s, 1H), 7.93 (d, J=1.5 Hz, 1H), 7.82 (dd, J=1.8, 0.9 Hz, 1H), 2.58 (s, 3H). LC-MS: method H, RT=0.90 min, MS (ESI) m/z: 272.1 (M+H)$^+$.

Intermediate I-25

Intermediate I-25C (117.6 mg, 0.432 mmol), bis(pinacolato)diboron (165 mg, 0.648 mmol), and potassium acetate (106 mg, 1.080 mmol) were dissolved in dioxane (4321 µl) and degassed for 5 minutes by bubbling with argon. PdCl$_2$(dppf)-CH$_2$Cl$_2$ adduct (28.2 mg, 0.035 mmol) was added and the reaction mixture was degassed for an additional 10 minutes. The reaction mixture was heated to 130° C. in the microwave for 45 minutes. The reaction mixture was diluted with EtOAc and water and filtered. The reaction mixture was further extracted twice with EtOAc. The combined organic layers were washed with brine, dried with sodium sulfate, filtered, and concentrated in vacuo to yield Intermediate I-25 (0.097 g, 0.302 mmol, 70% yield). LC-MS: method H, RT=0.75 min, MS (ESI) m/z: 238.2 (M+H)$^+$. Observed the mass of the boronic acid in LC/MS.

Intermediate I-26

(R)-(2-chloro-4-methyl-7,8-dihydro-[1,4]dioxino[2',3':3,4]benzo[1,2-d]thiazol-7-yl)methyl acetate

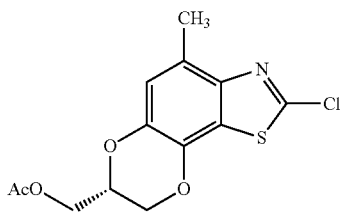

(I-26)

Intermediate I-26A: (R)-5-methyl-2-(oxiran-2-ylmethoxy)benzaldehyde

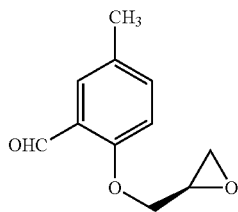

(I-26A)

To a solution of 2-hydroxy-5-methylbenzaldehyde (5 g, 36.7 mmol) in DMF (80 mL) was added (R)-oxiran-2-ylmethyl 3-nitrobenzenesulfonate (10.47 g, 40.4 mmol) and Cs$_2$CO$_3$ (35.9 g, 110 mmol). The mixture was stirred at room temperature overnight. LCMS indicated a completion of the reaction mixture. The mixture was diluted with EtOAc and water, extracted with EtOAc. The combined organic layer was washed with brine, dried over MgSO$_4$ and concentrated. The crude sample was purified with a 120 g ISCO column eluted with 0-100% EtOAc/hexanes for 40 min. The desired fractions were collected and concentrated to give Intermediate I-26A (7 g, 36.4 mmol, 99% yield) as a colorless oil. $^1$H NMR (400 MHz, chloroform-d) δ 10.50 (s, 1H), 7.65 (d, J=2.2 Hz, 1H), 7.35 (ddd, J=8.6, 2.4, 0.7 Hz, 1H), 6.90 (d, J=8.6 Hz, 1H), 4.36 (dd, J=11.1, 3.0 Hz, 1H), 4.05 (dd, J=11.1, 5.6 Hz, 1H), 3.40 (ddt, J=5.6, 4.1, 2.8 Hz, 1H), 2.94 (dd, J=4.7, 4.1 Hz, 1H), 2.80 (dd, J=4.8, 2.6 Hz, 1H), 2.32 (s, 3H); LC-MS: method C, RT=1.59 min, MS (ESI) m/z: 193.0 (M+H)$^+$.

Intermediate I-26B: (S)-(7-methyl-2,3-dihydrobenzo[b][1,4]dioxin-2-yl)methanol

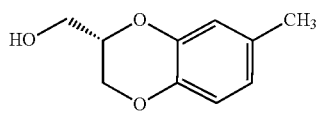

(I-26B)

To a stirred solution of Intermediate I-26A (7 g, 36.4 mmol) in dichloromethane (100 mL) cooled with an ice bath was added mCPBA (12.36 g, 53.7 mmol). Next, trifluoroacetic acid (2.81 mL, 36.4 mmol) in dichloromethane (10 mL) was added dropwise. Ice bath was removed and the mixture was stirred at room temperature for 1.0 h. TLC and LCMS indicated no starting material remaining. The reaction mixture was quenched by addition of saturated sodium bicarbonate, followed by 10% sodium thiosulfite (20.0 mL), extracted with dichloromethane. The organic layers were collected, washed with saturated sodium bicarbonate, brine and dried over sodium sulfate. After evaporation of solvent, the crude product was dissolved in MeOH (100 mL), and K$_2$CO$_3$ (15.10 g, 109 mmol) was added. The mixture was stirred overnight at room temperature. The reaction mixture was diluted with EtOAc and water, extracted with EtOAc, the combined organic layer was washed with brine, dried over MgSO$_4$ and concentrated. The crude sample was purified with a 120 g ISCO column eluted with 0-100% EtOAc/hexanes for 40 min. The desired fractions were combined and concentrated to give Intermediate I-26B (4.65 g, 25.8 mmol, 70.9% yield). $^1$H NMR (400 MHz, chloroform-d) δ 6.78 (d, J=8.1 Hz, 1H), 6.73 (d, J=1.3 Hz, 1H), 6.69-6.63 (m, 1H), 4.33-4.21 (m, 2H), 4.15-4.05 (m, 1H), 3.96-3.76 (m, 2H), 2.26 (s, 3H). LC-MS: method C, RT=1.55 min, MS (ESI) m/z: 209.0 (M+H)$^+$.

Intermediate I-26C: (R)-(7-methyl-2,3-dihydrobenzo[b][1,4]dioxin-2-yl)methyl acetate

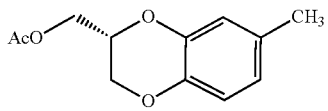

(I-26C)

To a solution of Intermediate I-26B (4.6 g, 25.5 mmol) in THF (100 mL) at 0° C. was added TEA (8.89 mL, 63.8 mmol), followed by acetyl chloride in DCM (31.9 mL, 31.9 mmol) dropwise. The mixture was stirred at 0° C. for 10 min, and at room temperature for 1.0 h. The mixture was diluted with EtOAc, washed with water. The organic layer was washed with 0.5 N HCl, saturated sodium bicarbonate, brine and dried over sodium sulfate. After evaporation of solvent, Intermediate I-26C (5.3 g, 23.85 mmol, 93% yield) was obtained as a yellow oil. It was used for the next step without further purification. $^1$H NMR (400 MHz, chloroform-d) δ 6.76 (d, J=8.1 Hz, 1H), 6.72 (d, J=1.3 Hz, 1H), 6.68-6.61 (m, 1H), 4.40-4.33 (m, 1H), 4.30 (dd, J=5.1, 4.4 Hz, 2H), 4.25 (dd, J=11.3, 2.3 Hz, 1H), 4.03 (dd, J=11.4, 6.8 Hz, 1H), 2.25 (s, 3H), 2.11 (s, 3H). LC-MS: method C, RT=1.92 min, MS (ESI) m/z: 245.0 (M+H)$^+$.

Intermediate I-26D: (R)-(7-methyl-6-nitro-2,3-dihydrobenzo[b][1,4]dioxin-2-yl)methyl acetate

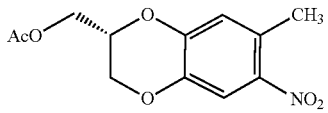

(I-26D)

To a solution of Intermediate I-26C (4.15 g, 18.67 mmol) in acetic acid (40 mL) cooled at 0° C. with an ice-bath was added fuming nitric acid (4.36 mL, 93 mmol) dropwise. The mixture was stirred at 0° C. for 1 h, then at room temperature for 30 min. TLC (PMA stain) indicated a completion of the reaction. It was quenched with ice water. The aqueous was removed and the organic layer was washed with saturated sodium bicarbonate (3×), brine and dried over sodium sulfate. After evaporation of solvent, Intermediate I-26D (4.6 g, 17.21 mmol, 92% yield) was obtained as an off-white solid which was used for the next step without further purification. $^1$H NMR (400 MHz, chloroform-d) δ 7.71 (s, 1H), 6.83 (s, 1H), 4.54-4.45 (m, 1H), 4.39-4.28 (m, 3H), 4.09 (dd, J=11.9, 7.0 Hz, 1H), 2.55 (d, J=0.4 Hz, 3H), 2.13 (s, 3H). LC-MS: method C, RT=1.90 min, MS (ESI) m/z: 290.0 (M+H)$^+$.

Intermediate I-26E: (R)-(6-amino-7-methyl-2,3-dihydrobenzo[b][1,4]dioxin-2-yl)methyl acetate

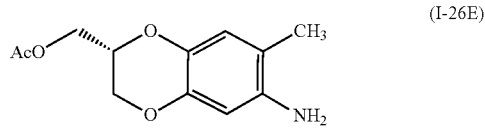 [SMILES: CC(=O)OC[C@H]1COc2cc(N)c(C)cc2O1]

(I-26E)

To a solution of Intermediate I-26D (5.3 g, 19.83 mmol) in MeOH (80 mL) and THF (80 mL) cooled with an ice bath was added ammonium chloride (16.97 g, 317 mmol) and zinc dust (10.37 g, 159 mmol). The mixture was stirred at 0° C. for 30 min, and at room temperature for 1.0 h. MeOH and THF were removed under vacuum. The residue was diluted with EtOAc/saturated sodium bicarbonate and stirred at room temperature for 3 min. The mixture was filtered through a pad of wet celite to remove insoluble material. The filtrate was collected, organic layer was washed with brine, dried over sodium sulfate, concentrated to give Intermediate I-26E (4.7 g, 19.81 mmol, 100% yield) as off-white solid. $^1$H NMR (400 MHz, chloroform-d) δ 6.63 (s, 1H), 6.25 (s, 1H), 4.38-4.20 (m, 4H), 4.06-3.95 (m, 1H), 3.35 (br. s., 2H), 2.11 (s, 3H), 2.09 (s, 3H). LC-MS: method C, RT=1.14 min, MS (ESI) m/z: 238.0 (M+H)$^+$.

Intermediate I-26F (R)-(2-amino-4-methyl-7,8-dihydro-[1,4]dioxino[2',3':3,4]benzo[1,2-d]thiazol-7-yl)methyl acetate

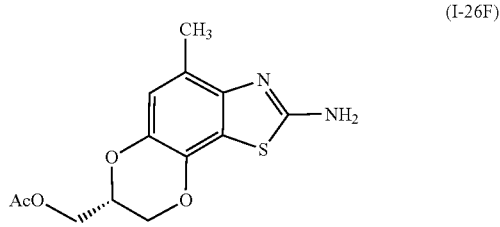 [SMILES: CC(=O)OC[C@H]1COc2c(cc(C)c3nc(N)sc23)O1]

(I-26F)

To Intermediate I-26E (4.7 g, 19.81 mmol) dissolved in acetonitrile (120 mL) was added ammonium thiocyanate (2.262 g, 29.7 mmol). The mixture was stirred at room temperature for 10 min. Benzyltrimethylammonium tribromide (8.11 g, 20.80 mmol) in acetonitrile (20 mL) was added dropwise (5 min). The reaction mixture was stirred at room temperature overnight, diluted with EtOAc/THF/saturated sodium bicarbonate. The insoluble material was removed by filtration. The organic layer of the filtrate was collected, washed with brine, dried over sodium sulfate. After evaporation of solvent, Intermediate I-26F (5.8 g, 19.71 mmol, 99% yield) was obtained as a yellow solid. $^1$H NMR (400 MHz, chloroform-d) δ 6.73 (d, J=0.7 Hz, 1H), 5.10 (s, 2H), 4.47-4.28 (m, 4H), 4.14 (dd, J=11.3, 6.9 Hz, 1H), 2.45 (d, J=0.7 Hz, 3H), 2.12 (s, 3H). LC-MS: method C, RT=1.46 min, MS (ESI) m/z: 295.0 (M+H)$^+$.

Intermediate I-26

To a suspension of Intermediate I-26F (5.8 g, 19.71 mmol) in dry acetonitrile (80 mL) was added copper (II) chloride (4.5 g, 33.5 mmol), followed by tert-butyl nitrite (4.56 mL, 34.5 mmol) dropwise. The reaction mixture was stirred at room temperature for 2 h. LCMS indicated a completion of the reaction. Acetonitrile was removed under vacuum, the reaction mixture was diluted with EtOAc, quenched with 1.0 N HCl. The organic layer was collected, washed with 0.5 N HCl (2×), saturated sodium bicarbonate, brine and dried over sodium sulfate. After evaporation of solvent, the crude product was purified with a 220 g ISCO column eluted with 0% to 70% EtOAc in hexanes over 60 min. The desired fraction was collected and concentrated to yield Intermediate I-26 (3.9 g, 12.43 mmol, 63.1% yield) as an off-white solid. $^1$H NMR (400 MHz, chloroform-d) δ 6.89 (d, J=0.7 Hz, 1H), 4.55-4.28 (m, 4H), 4.18 (dd, J=11.4, 7.0 Hz, 1H), 2.59 (s, 3H), 2.13 (s, 3H). LC-MS: method C, RT=2.18 min, MS (ESI) m/z: 314.0 (M+H)$^+$.

Intermediate I-27

7-((tert-butyl dimethyl silyloxy)methyl)-2-methoxy-5-(4,4,5,5-tetramethyl-1,3,2-dioxaborolan-2-yl)quinoxaline

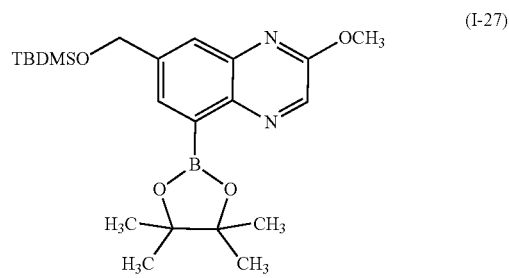 [SMILES: COc1cnc2c(B3OC(C)(C)C(C)(C)O3)cc(CO[Si](C)(C)C(C)(C)C)cc2n1]

(I-27)

Intermediate I-27A:
8-bromo-3-methoxyquinoxaline-6-carbaldehyde

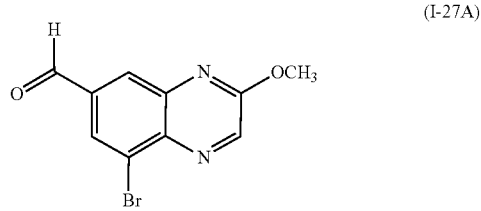 [SMILES: COc1cnc2c(Br)cc(C=O)cc2n1]

(I-27A)

To a solution of Intermediate I-9A (1 g, 3.95 mmol) in CCl$_4$ (20 mL) was added NBS (1.547 g, 8.69 mmol) and benzoic peroxide (0.115 g, 0.474 mmol). The mixture was heated at reflux (95° C. oil bath) for 3 h. TLC and LCMS indicated a completion of the reaction. The mixture was cooled to room temperature and filtered. The filtrate was concentrated to a yellow solid. The crude sample was dissolved in THF (10 ml) and silver nitrate (6.71 g, 39.5 mmol) in water (10 ml) was added. The mixture was stirred at 95° C. for 1 h. LCMS indicated a completion of the reaction. The mixture was cooled to room temperature and poured to 60 ml of water. The mixture was filtered and the filter cake was washed with CHCl$_3$ for 3 times. The combined filtrate was extracted with CHCl$_3$ and the organic layer was combined, washed with NaHCO$_3$ and brine dried over MgSO$_4$ and concentrated to Intermediate I-27A (1 g, 3.74 mmol, 95% yield). The crude sample was used for next step without purification. LC-MS: method C, RT=1.84 min, MS (ESI) m/z: 267 and 269 (M+H)$^+$.

Intermediate I-27B:
(8-bromo-3-methoxyquinoxalin-6-yl)methanol

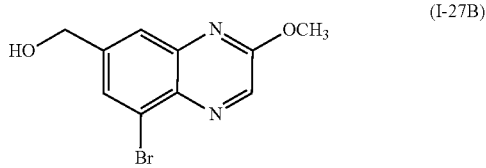 [SMILES: COc1cnc2c(Br)cc(CO)cc2n1]

Intermediate I-27A (1.055 g, 3.95 mmol) suspended in THF (10 mL) and MeOH (10 mL) was treated with NaBH$_4$ (0.149 g, 3.95 mmol) at room temperature for 15 min. The reaction mixture turned to a clear solution. LCMS indicated a completion of the reaction. Saturated NH$_4$Cl was added to quench the reaction. After stirring at room temperature for 10 min, it was diluted with EtOAc and water. The organic layer was washed with brine, dried over MgSO$_4$ and concentrated. The crude product was purified with a 120 g ISCO column eluted with 0-100% EtOAc in hexanes. The desired fraction was collected and concentrated to give Intermediate I-27B (380 mg, 1.412 mmol, 35.7% yield). $^1$H NMR (400 MHz, chloroform-d) δ 8.54 (s, 1H), 8.01-7.77 (m, 2H), 4.90 (s, 2H), 4.13 (s, 3H). LC-MS: method C, RT=1.64 min, MS (ESI) (m/z) 269 and 271 (M+H)$^+$.

Intermediate I-27C 5-bromo-7-((tert-butyldimethylsilyloxy)methyl)-2-methoxyquinoxaline

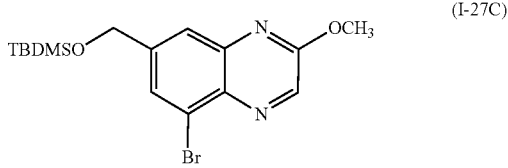 [SMILES: COc1cnc2c(Br)cc(CO[Si](C)(C)C(C)(C)C)cc2n1]

To a stirred solution of Intermediate I-27B (380 mg, 1.412 mmol) in DMF (5 mL) was added TBDMS-Cl (319 mg, 2.118 mmol) and imidazole (173 mg, 2.54 mmol). The reaction mixture was stirred at room temperature for 1.0 h. TLC and LCMS indicated a clean reaction. The mixture was partitioned between EtOAc/water. The organic layer was washed with water, brine, dried over sodium sulfate. After evaporation of solvent, the crude product was dissolved in a small amount of chloroform and charged to a 40 g silica gel cartridge which was eluted with hexanes for 3 min., then a 20 min gradient from 0% to 15% EtOAc in hexanes. The desired fractions were combined and concentrated to give Intermediate I-27C (480 mg, 1.252 mmol, 89% yield) as a white solid. LC-MS: method C, RT=2.74 min, MS (ESI) (m/z) 383 and 385 (M+H)$^+$.

Intermediate I-27

A mixture of Intermediate I-27C (100 mg, 0.261 mmol), 4,4,4',4',5,5,5',5'-octamethyl-2,2'-bi(1,3,2-dioxaborolane) (99 mg, 0.391 mmol), potassium acetate (64.0 mg, 0.652 mmol) in dioxane (2 mL) was degassed with argon for 5 min, then [1,1'-bis(diphenylphosphino)ferrocene]dichloropalladium (II) complex with dichloromethane (1:1) (10.65 mg, 0.013 mmol) was added. The mixture was sealed and heated in microwave reactor at 130° C. for 30 min. LCMS indicated a clean reaction. The mixture was diluted with EtOAc/water, insoluble material was removed by filtration. The filtrate was extracted with EtOAc, washed with brine, dried over sodium sulfate. After evaporation of solvent, the crude product was dissolved in a small amount of toluene and charged to a 40 g silica gel cartridge which was eluted with 5% EtOAc in hexanes for 2 min., then a 18 min gradient from 5% to 75% EtOAc in hexanes. The desired fractions were combined, concentrated and lyophilized to give Intermediate I-27 (105 mg, 0.244 mmol, 94% yield) as a pale solid. $^1$H NMR (400 MHz, chloroform-d) δ 8.39 (s, 1H), 8.12 (d, J=2.0 Hz, 1H), 7.96 (dt, J=2.0, 1.0 Hz, 1H), 4.96 (s, 2H), 4.13 (s, 3H), 1.45 (s, 12H), 1.00 (s, 9H), 0.16 (s, 6H). LC-MS: method C, RT=2.73 min, MS (ESI) (m/z) 349 (M+H)$^+$ (boronic acid).

Intermediate I-28

7-chloro-2-methoxy-5-(4,4,5,5-tetramethyl-1,3,2-dioxaborolan-2-yl)quinoxaline

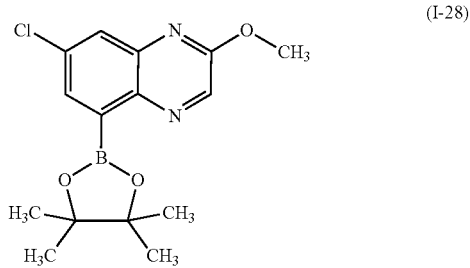 [SMILES: COc1cnc2c(B3OC(C)(C)C(C)(C)O3)cc(Cl)cc2n1]

Intermediate I-28A: 2-bromo-4-chloro-6-nitroaniline

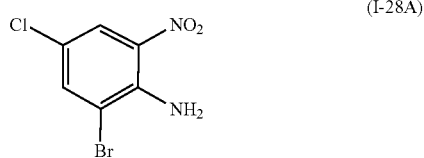 [SMILES: Nc1c(Br)cc(Cl)cc1[N+](=O)[O-]]

A solution of 4-chloro-2-nitroaniline (10 g, 57.9 mmol) in acetic acid (50 mL) was cooled to 0° C. with an ice bath. Bromine (3.28 mL, 63.7 mmol) was added dropwise, and the mixture was stirred at room temperature for 1 hr, and then poured into ice water. The precipitated solid was filtered and was washed with water several times. The filter cake was re-dissolved in EtOAc, dried over sodium sulfate, filtered and concentrated in vacuo to give the title compound as a yellow solid (14.66 g, 100%). $^1$H NMR (400 MHz, DMSO-d$_6$) δ 8.08 (d, J=2.4 Hz, 1H), 8.02 (d, J=2.6 Hz, 1H), 7.27 (br s, 2H); LC-MS: method H, RT=1.15 min, MS (ESI) m/z: 250.9 and 252.9 (M+H)$^+$.

Intermediate I-28B: tert-butyl N-(2-bromo-4-chloro-6-nitrophenyl)-N-[(tert-butoxy)carbonyl]carbamate

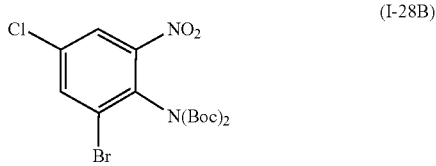

In a round bottom flask charged with a stirring bar, Intermediate I-28A (5 g, 19.88 mmol) was dissolved in THF (30 mL). DMAP (0.243 g, 1.988 mmol) was added, followed by di-tert-butyl dicarbonate (11.54 mL, 49.7 mmol). The reaction mixture was stirred at room temperature for 1 hour, and then solvent was removed on a rotary evaporator. The residue was purified by flash chromatography (120 g silica gel column eluted with 0-100% EtOAc/Hexane) to give the title compound as a white solid (8.2 g, 18.1 mmol, 91%). $^1$H NMR (400 MHz, chloroform-d): 7.97 (d, J=2.4 Hz, 1H), 7.90 (d, J=2.4 Hz, 1H), 1.42 (s, 18H); LC-MS: method H, RT=1.04 min, MS (ESI) m/z: 250.9 and 252.9 (M+H–2Boc)$^+$.

Intermediate I-28C: tert-butyl (2-bromo-4-chloro-6-nitrophenyl)carbamate

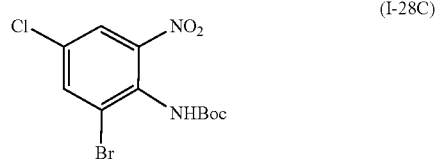 [SMILES: CC(C)(C)OC(=O)Nc1c(Br)cc(Cl)cc1[N+](=O)[O-]]

To a solution of Intermediate I-28B (8.2 g, 18.15 mmol) in DCM (50 mL) was added TFA (2.80 mL, 36.3 mmol) and the mixture was stirred at room temperature for 1 hour. Saturated NaHCO$_3$ (aqueous 30 mL) was added to the mixture. After stirring at room temperature for 10 minutes, the layers were separated and the aqueous layer was extracted by DCM (30 mL×2). The combined organic solution was washed with brine, dried over Na$_2$SO$_4$ and concentrated to give the title compound as a yellow solid (6.32 g, 18.0 mmol, 99%). $^1$H NMR (400 MHz, DMSO-d$_6$) δ 9.45 (br s, 1H), 8.24 (d, J=2.4 Hz, 1H), 8.12 (d, J=2.4 Hz, 1H), 1.43 (br s, 9H); LC-MS: method H, RT=0.82 min, MS (ESI) m/z: 250.9 and 252.9 (M+H–Boc)$^+$.

Intermediate I-28D: methyl 2-((2-bromo-4-methyl-6-nitrophenyl)amino)acetate

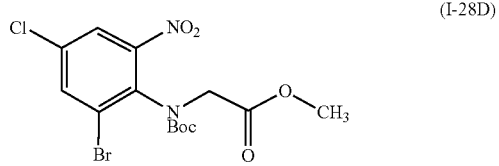 [SMILES: COC(=O)CN(C(=O)OC(C)(C)C)c1c(Br)cc(Cl)cc1[N+](=O)[O-]]

To a solution of Intermediate I-28C (6.32 g, 18.0 mmol) in DMF (30 mL) was added Cs$_2$CO$_3$ (14.64 g, 44.9 mmol. Methyl 2-bromoacetate (5.50 g, 36.0 mmol) was added dropwise and the mixture was stirred at room temperature for 30 minutes. The reaction mixture was diluted with 100 mL of EtOAc and 50 mL of water. After separation, the aqueous layer was extracted by EtOAc (50 mL), and the combined organic layers were washed with brine and concentrated. The residue was purified by flash chromatography (120 g silica gel column, eluted with 0-50% EtOAc/Hex) to give the title compound (7.55 g, 17.8 mmol, 99%) as a yellow oil. $^1$H NMR (400 MHz, chloroform-d) δ 7.92-7.81 (m, 2H), 4.58 (d, J=17.6 Hz, 1H), 3.99 (d, J=17.4 Hz, 1H), 3.69 (s, 3H), 1.38 (s, 9H); LC-MS: method H, RT=1.23 min, MS (ESI) m/z: 366.9 and 368.9 (M+H–56)$^+$.

Intermediate I-28E: methyl 2-((2-bromo-4-chloro-6-nitrophenyl)amino)acetate, TFA Salt

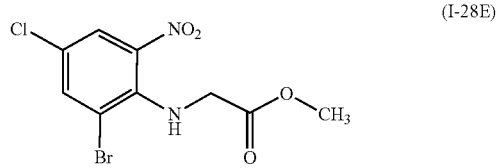 [SMILES: COC(=O)CNc1c(Br)cc(Cl)cc1[N+](=O)[O-]]

Intermediate I-28D (5.6 g, 13.22 mmol) was dissolved in DCM (30 mL) and was treated with TFA (10.18 mL, 132 mmol) at room temperature overnight. On the next day, the solvent was removed and the crude product was used in the next step without purification. LC-MS: method H, RT=1.22 min, MS (ESI) m/z: 323.0 and 324.9 (M+H)$^+$.

Intermediate I-28F: 5-bromo-7-chloro-3,4-dihydroquinoxalin-2(1H)-one

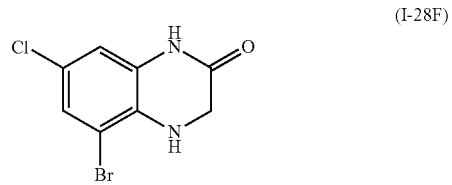 [SMILES: O=C1CNc2c(Br)cc(Cl)cc2N1]

In a round bottom flask charged with a stirring bar, Intermediate I-28E (6.0 g, 18.55 mmol) was dissolved in MeOH (60 mL), and concentrated HCl (4.64 mL, 55.6 mmol) was added, followed by SnCl$_2$ (14.07 g, 74.2 mmol). The reaction mixture was stirred at 60° C. overnight. On the next day, after cooling to room temperature, another 2 equivalents of SnCl$_2$ was added to the reaction mixture. After 2 h at 60° C., the reaction mixture was cooled to room temperature; the precipitate was filtered, washed with small amount of MeOH, and dried to give a white solid as desired product. The filtrate was concentrated on a rotary evaporator and then partitioned between 150 mL of EtOAc and 30 mL of water. Next, 4M NaOH (aqueous) was added to adjust the pH to 12. The solid was filtered on a Celite pad and the filter cake was washed with EtOAc. The layers were separated and the aqueous phase was extracted twice with EtOAc. The combined organic phases were washed with saturated NaHCO$_3$ (aqueous), brine, dried over Na$_2$SO$_4$, filtered, and concentrated in vacuo to give additional product. Combining material gave 5-bromo-7-chloro-3,4-dihydroquinoxalin-2 (1H)-one (3.55 g, 13.58 mmol, 73.2% yield) as a white solid. $^1$H NMR (400 MHz, DMSO-d$_6$) δ 10.53 (s, 1H), 7.12 (d, J=2.2 Hz, 1H), 6.85-6.66 (m, 1H), 5.83 (s, 1H), 3.82 (d, J=2.0 Hz, 2H); LC-MS: method H, RT=1.02 min, MS (ESI) m/z: 261.0 and 263.0 (M+H)$^+$.

Intermediate I-28G:
5-bromo-7-chloroquinoxalin-2-ol

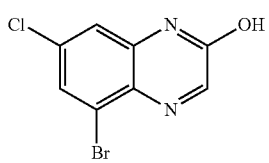

In 1 L round bottom flask charged with a stirring bar, Intermediate I-28F (3.84 g, 14.7 mmol) was suspended in MeOH (50 mL), and H$_2$O$_2$ (15.00 mL, 147 mmol, 30% in water) was added, followed by 4N NaOH (11.01 mL, 44.1 mmol). The mixture was stirred at room temperature for 5 minutes, and then heated at 60° C. for 15 minutes. Heating was removed and the reaction mixture was stirred at room temperature over the weekend. Another 5 mL of H$_2$O$_2$ was added and the mixture was stirred at room temperature for 2 h. The reaction mixture was concentrated on a rotary evaporator. The residual mixture was cooled in an ice bath, and 6 N HCl was added to adjust the pH value to 2-3, followed by 200 mL of EtOAc. After shaking and separation, the aqueous layer was extracted with EtOAc (50 mL×2). The combined organic phases were combined and dried over Na$_2$SO$_4$. Removing solvent in vacuo gave the title compound as a brown solid. (2.51 g, 9.70 mmol, 66%). $^1$H NMR (400 MHz, DMSO-d$_6$): δ 12.63 (br s, 1H), 8.23 (s, 1H), 7.73 (d, J=2.0 Hz, 1H), 7.31 (d, J=2.0 Hz, 1H); LC-MS: method H, RT=1.01 min, MS (ESI) m/z: 258.9 and 260.9 (M+H)$^+$.

Intermediate I-28H:
5-bromo-7-chloro-2-methoxyquinoxaline

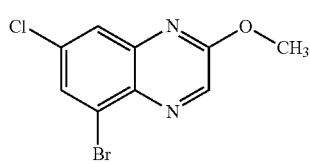

In a round bottom flask charged with a stirring bar, Intermediate I-28G (1.60 g, 6.17 mmol) was suspended in POCl$_3$ (10 mL, 107 mmol), and the mixture was refluxed for 2 h. Excess POCl$_3$ was removed on a rotary evaporator and the residue was dried in vacuo for 30 minutes to give a brown solid. This brown solid was suspended in MeOH (30 mL), and anhydrous K$_2$CO$_3$ (1.704 g, 12.33 mmol) was added. The mixture was stirred at room temperature for 10 minutes, and then refluxed for 2 h. After cooling to room temperature, the solvent was removed on a rotary evaporator. The residue was dissolved in 100 ml of EtOAc, washed with water, brine, dried over Na$_2$SO$_4$, filtered, and concentrated to give the crude product. The crude product was purified by flash chromatography (80 g silica gel column, 0-50% EtOAc/Hexane) to give Intermediate I-28H (1.02 g, 3.73 mmol, 60.5% yield) as a yellow solid. $^1$H NMR (400 MHz, chloroform-d): δ 8.53 (s, 1H), 7.87-7.83 (m, 2H), 4.12 (s, 3H); LC-MS: method J, RT=0.96 min, MS (ESI) m/z: 273.0 and 275.0 (M+H)$^+$.

Intermediate I-28

In a microwave vial charged with a stirring bar, Intermediate I-28H (330 mg, 1.207 mmol), 4,4,4',4',5,5,5',5'-octamethyl-2,2'-bi(1,3,2-dioxaborolane) (460 mg, 1.810 mmol), potassium acetate (296 mg, 3.02 mmol) were mixed with 1,4-dioxane (10 mL). After degassing with bubbling N$_2$ for 10 minutes, PdCl$_2$(dppf)-CH$_2$Cl$_2$ adduct (49.3 mg, 0.060 mmol) was added. The vial was sealed and was heated by microwave to 120° C. for 60 minutes. After cooling to room temperature, the reaction mixture was diluted by adding 40 mL of EtOAc and 30 mL of water. After separation, the aqueous layer was extracted with EtOAc (20 mL×2). The combined organic layers were dried over Na$_2$SO$_4$ and concentrated on a rotary evaporator. The residue was purified by flash chromatography (40 g silica gel column, 0-100% EtOAc/hexane gradient in 10 minutes, 100% EtOAc for 10 minutes) to give Intermediate I-28 as a yellow solid. (293 mg, 76%). $^1$H NMR (400 MHz, chloroform-d): 8.53 (s, 1H), 7.92-7.85 (m, 2H), 4.08 (s, 3H), 1.45 (s, 12H); LC-MS: method H, RT=1.09 min, MS (ESI) m/z: 239.1 (M+H−82)$^+$.

Intermediate I-29

7-chloro-2-(methoxymethyl)-5-(4,4,5,5-tetramethyl-1,3,2-dioxaborolan-2-yl)quinoxaline

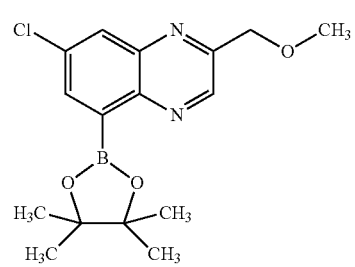

Intermediate I-29A: tert-butyl (2-bromo-4-chloro-6-nitrophenyl)(3-methoxy-2-oxopropyl)carbamate

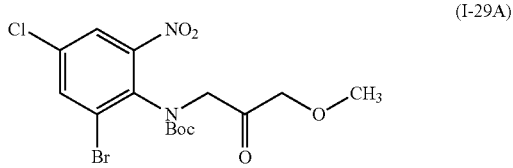 [SMILES: COCC(=O)CN(C(=O)OC(C)(C)C)c1c(Br)cc(Cl)cc1[N+](=O)[O-]]

(I-29A)

To Intermediate I-28C (2.0 g, 5.69 mmol) in DMF (20 mL) at 0° C. was added cesium carbonate (3.24 g, 9.96 mmol). The brown solution was stirred at 0° C. for 10 min, followed by addition of Intermediate I-2B (1.140 g, 6.83 mmol) in DMF (5.0 mL). The brown solution turned yellow. The mixture was stirred at 0° C. for 15 min. The mixture was diluted with EtOAc, washed with water, brine, dried over sodium sulfate and concentrated. The crude product was purified by flash chromatography (80 g silica gel column, 0% to 60% EtOAc/hexane over 18 min) to yield the desired product (2.01 g, 81%) as a yellow oil. $^1$H NMR (400 MHz, chloroform-d): δ 7.95-7.80 (m, 2H), 4.65 (d, J=18.3 Hz, 1H), 4.22 (d, J=18.0 Hz, 1H), 4.09 (s, 2H), 3.42 (s, 3H), 1.37 (s, 9H); LC-MS: method H, RT=1.20 min, MS (ESI) m/z: 383.0 (M+H−54)$^+$.

Intermediate I-29B:
5-bromo-7-chloro-2-(methoxymethyl)quinoxaline

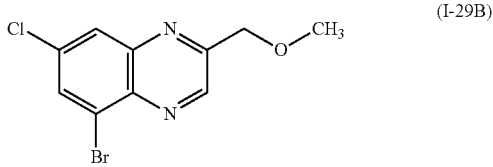

(I-29B)

To Intermediate I-29A (2.0 g, 4.57 mmol) in ethyl acetate (10 mL) was added HCl in 1,4-dioxane (11.42 mL, 45.7 mmol) and the mixture was stirred at room temperature for 20 min. LCMS indicated a clean reaction. Solvent was removed under vacuum, and chased with EtOAc once to give the deprotected intermediate as yellow oil. The deprotected intermediate was dissolved in THF (40 mL). Concentrated HCl (aqueous) (1.142 mL, 13.71 mmol) was added, followed by SnCl$_2$ (3.47 g, 18.28 mmol). The mixture was stirred in an oil bath at 40° C. for 4.0 h. After cooling to room temperature, the reaction mixture was diluted with EtOAc (100 mL)/water (50 mL). The organic phase was neutralized with saturated sodium bicarbonate, stirred at room temperature for 15 min, and the precipitate was removed by filtration with a pad of wet Celite. The organic solution was washed with brine, dried over sodium sulfate and concentrated. The crude product was purified by flash chromatography (loading in chloroform, 0% to 40% EtOAc in hexane over 20 min using an 80 g silica gel cartridge) to yield a brown solid (0.48 g, 36.5%). $^1$H NMR (400 MHz, chloroform-d) δ 9.07 (s, 1H), 8.06 (s, 2H), 4.83 (s, 2H), 3.56 (s, 3H); LC-MS: method J, RT=1.20 min, MS (ESI) m/z: 287.1, 289.0 (M+H)$^+$.

Intermediate I-29

In a microwave vial charged with a stirring bar, Intermediate I-29B (475 mg, 1.652 mmol), 4,4,4',4',5,5,5',5'-octamethyl-2,2'-bi(1,3,2-dioxaborolane) (629 mg, 2.478 mmol) and potassium acetate (405 mg, 4.13 mmol) were mixed in 1,4-dioxane (10 mL). After degassing with bubbling N$_2$ for 10 minutes, Pd(dppf)$_2$Cl$_2$·CH$_2$Cl$_2$ (67.5 mg, 0.083 mmol) was added. The vial was sealed and was irradiated in the microwave at 120° C. for 60 minutes. Solvent was removed and the residue was purified by flash chromatography (24 g silica gel column, 0-100% EtOAc/Hexane) to give Intermediate I-29 (432 mg, 76%) as an off-white solid. $^1$H NMR (400 MHz, chloroform-d) δ 9.07 (s, 1H), 8.12 (d, J=2.4 Hz, 1H), 8.08 (d, J=2.2 Hz, 1H), 4.78 (s, 2H), 3.51 (s, 3H), 1.24 (s, 12H); LC-MS: method J, RT=1.20 min, MS (ESI) m/z: 253.0 (M+H−82)$^+$.

Intermediate I-30 to Intermediate I-34

Intermediate I-30 to Intermediate I-34 were synthesized by following the general procedures described in Intermediate I-28 and I-29.

| Intermediate | Structure | LCMS [M + H]$^+$ m/z | LCMS RT(Min)/ Method | NMR |
|---|---|---|---|---|
| I-30 | ![structure] | 237.1* | 1.00/H | |

-continued

| Intermediate | Structure | LCMS [M + H]+ m/z | LCMS RT(Min)/ Method | NMR |
|---|---|---|---|---|
| I-31 | 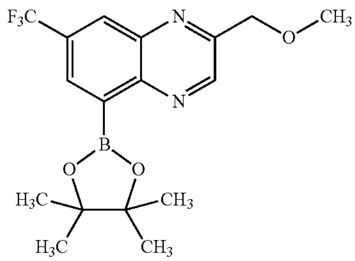 [SMILES: COCc1cnc2c(B3OC(C)(C)C(C)(C)O3)cc(C(F)(F)F)cc2n1] | 287.2* | 0.61/J | |
| I-32 | 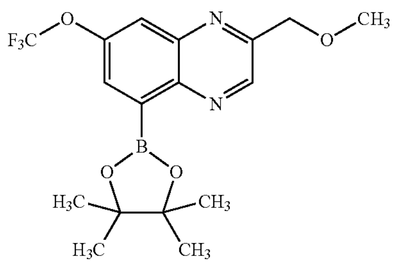 [SMILES: COCc1cnc2c(B3OC(C)(C)C(C)(C)O3)cc(OC(F)(F)F)cc2n1] | 303.2* | 0.73/J | |
| I-33 | 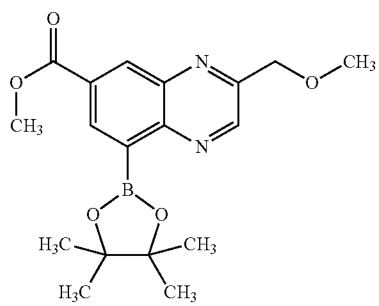 [SMILES: COCc1cnc2c(B3OC(C)(C)C(C)(C)O3)cc(C(=O)OC)cc2n1] | 277.1* | 0.92/J | |
| I-34 | 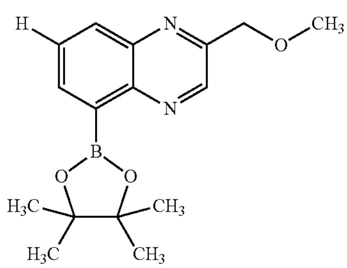 | 219.1* | 0.86/H | |

*(M + H)+ of boronic acid

Intermediate I-35

(7-(hydroxymethyl)-2-methoxyquinoxalin-5-yl)boronic acid

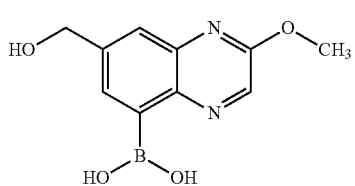

(I-35)

Intermediate I-35A: 4-bromo-2-chloro-6-nitroaniline

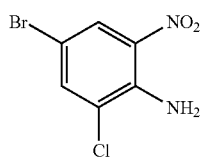

(I-35A)

A mixture of 4-bromo-2-nitroaniline (10.82 g, 49.9 mmol) and NCS (8.32 g, 62.3 mmol) in DMF (100 mL) was heated to 100° C. for 1 h. After cooling to room temperature, the solution was poured into ice water. The yellow precipitate was collected by filtration and was washed with water. The solid was dissolved in dichloromethane (100 mL) and the organic phase was washed with water and brine, dried (Na₂SO₄), filtered, and concentrated to yield the title compound (11.54 g, 45.9 mmol, 92% yield) as a yellow solid. $^1$H NMR (400 MHz, chloroform-d) δ 8.26 (d, J=2.2 Hz, 1H), 7.67 (d, J=2.2 Hz, 1H), 6.57 (br s, 2H).

Intermediate I-35B: tert-butyl N-(4-bromo-2-chloro-6-nitrophenyl)-N-[(tert-butoxy)carbonyl]carbamate

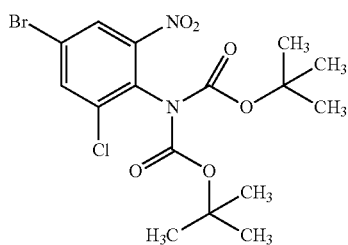

Intermediate I-35B (11.75 g, 87%) was made as a yellow solid from Intermediate I-35A (7.52 g, 29.9 mmol) via the same procedure as Intermediate I-28B. $^1$H NMR (400 MHz, chloroform-d) δ 8.08 (d, J=2.2 Hz, 1H), 7.89 (d, J=2.2 Hz, 1H), 1.42 (s, 18H).

Intermediate I-35C: tert-butyl (4-bromo-2-chloro-6-nitrophenyl)carbamate

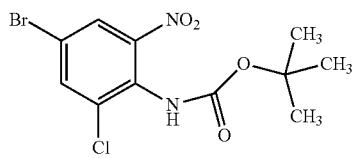

Intermediate I-35C (5.2 g, 14.8 mmol, 98%) was made as a brown waxy solid from Intermediate I-35B (6.8 g, 15.0 mmol) via the same procedure as Intermediate I-28C. $^1$H NMR (400 MHz, chloroform-d) δ 8.00 (d, J=2.2 Hz, 1H), 7.81 (d, J=2.2 Hz, 1H), 6.92 (br s, 1H), 1.50 (s, 9H)

Intermediate I-35D: methyl 2-((4-bromo-2-chloro-6-nitrophenyl)(tert-butoxycarbonyl)amino)acetate

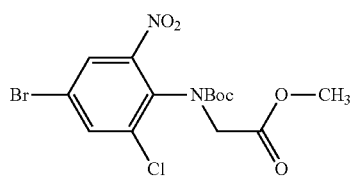

Intermediate I-35D (5.4 g, 12.8 mmol, 87%) was made as a yellow oil from Intermediate I-35C (5.2 g, 14.8 mmol) via the same procedure as Intermediate I-28D. $^1$H NMR (400 MHz, chloroform-d) δ 7.99 (d, J=2.2 Hz, 1H), 7.88-7.85 (m, 1H), 4.49 (d, J=17.4 Hz, 1H), 4.07 (d, J=17.4 Hz, 1H), 3.71-3.67 (m, 3H), 1.37 (s, 9H); LC-MS: method H, RT=1.04 min, MS (ESI) m/z: 323.0 and 325.0 (M+H−100)⁺.

Intermediate I-35E: methyl 2-((4-bromo-2-chloro-6-nitrophenyl)amino)acetate

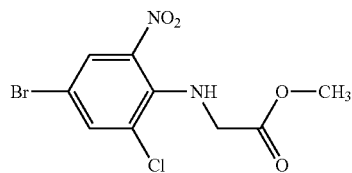

Intermediate I-35E (4.15 g, 12.8 mmol, 100%) was made as a brown oil from Intermediate I-35D (5.44 g, 12.8 mmol) via the same procedure as Intermediate I-28E. LC-MS: method H, RT=1.0 min, MS (ESI) m/z: 323.1 and 325.0 (M+H)⁺.

Intermediate I-35F: 7-bromo-5-chloro-3,4-dihydroquinoxalin-2(1H)-one

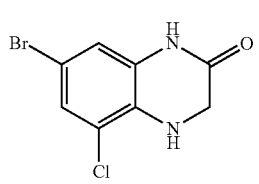

Intermediate I-35F (3.02 g, 11.55 mmol, 73%) was made as a white solid from Intermediate I-35E (5.1 g, 15.8 mmol) via the same procedure as Intermediate I-28F. $^1$H NMR (400 MHz, DMSO-d₆) δ 10.54 (s, 1H), 7.10 (d, J=2.0 Hz, 1H), 6.83 (d, J=2.2 Hz, 1H), 6.02 (s, 1H), 3.82 (d, J=1.8 Hz, 2H); LC-MS: method H, RT=0.84 min, MS (ESI) m/z: 261.0 and 263.0 (M+H)⁺.

Intermediate I-35G: 7-bromo-5-chloroquinoxalin-2(1H)-one

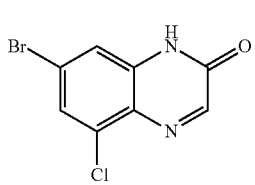

Intermediate I-35G (3.40 g, 13.10 mmol, 70%) was made as an off-white solid from Intermediate I-35F (4.85 g, 18.5 mmol) via the same procedure as Intermediate I-28G. $^1$H NMR (400 MHz, DMSO-d₆) δ 7.76 (s, 1H), 7.21 (d, J=2.2 Hz, 1H), 7.11 (d, J=2.2 Hz, 1H); LC-MS: method H, RT=1.08 min, MS (ESI) m/z: 259.1 and 261.1 (M+H)⁺.

Intermediate I-35H:
7-bromo-5-chloro-2-methoxyquinoxaline

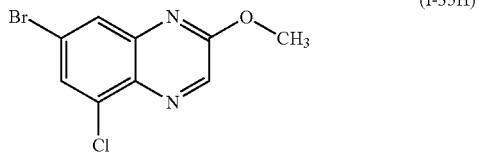

(I-35H)

Intermediate I-35H (2.13 g, 7.79 mmol, 86%) was made as a yellow solid from Intermediate I-35G (2.34 g, 9.02 mmol) via the same procedure as Intermediate I-28H. $^1$H NMR (400 MHz, chloroform-d) δ 8.55 (s, 1H), 7.98 (d, J=2.2 Hz, 1H), 7.80 (d, J=2.0 Hz, 1H), 4.12 (s, 3H); LC-MS: method H, RT=1.07 min, MS (ESI) m/z: 273.1 and 275.1 (M+H)$^+$.

Intermediate I-35I:
5-chloro-2-methoxy-7-vinylquinoxaline

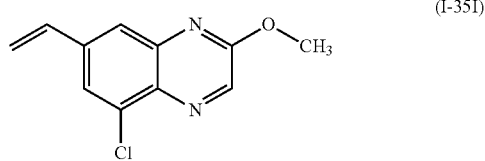

(I-35I)

To a vial charged with a stirring bar was added Intermediate I-35H (0.7 g, 2.56 mmol), potassium vinyltrifluoroborate (0.377 g, 2.82 mmol), cesium carbonate (1.668 g, 5.12 mmol), (s)-2,2'-bis(diphenylphosphino)-1,1'-binaphthalene (0.159 g, 0.256 mmol) and diacetoxypalladium (0.029 g, 0.128 mmol). After applying vacuum and refilling with N$_2$ 3 times, DMF (10 mL) was added and N$_2$ was bubbled through the solution for 10 minutes. The vial was sealed, stirred at room temperature for 10 minutes, and then heated at 80° C. for 3 h. After cooling to room temperature, the reaction mixture was diluted with 60 mL of EtOAc, washed with water and brine, dried over Na$_2$SO$_4$, filtered and concentrated. The crude product was purified by flash chromatography (0-50% EtOAc/Hexane in 12 minutes, 50-100% EtOAc/hexane in 6 minutes, 40 g silica gel column) to give the title compound (470 mg, 2.130 mmol, 83% yield) as an off-white solid. $^1$H NMR (400 MHz, chloroform-d) δ 8.51 (s, 1H), 7.79 (d, J=2.0 Hz, 1H), 7.73 (d, J=1.8 Hz, 1H), 6.83 (dd, J=17.5, 10.9 Hz, 1H), 5.96 (d, J=17.4 Hz, 1H), 5.48 (d, J=11.0 Hz, 1H), 4.12 (s, 3H); LC-MS: method H, RT=1.02 min, MS (ESI) m/z: 221.1.

Intermediate I-35J:
8-chloro-3-methoxyquinoxaline-6-carbaldehyde

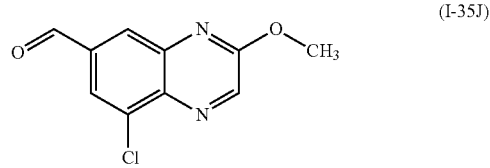

(I-35J)

In a round bottom flask charged with a stirring bar, Intermediate I-35I (470 mg, 2.130 mmol) was dissolved in THF (20 mL)/water (6 mL), and treated with sodium periodate (1367 mg, 6.39 mmol) and osmium tetroxide (4% by wt. in water) (0.271 mL, 0.043 mmol). The mixture was stirred at room temperature for 4 h, and then reaction mixture was diluted by adding 40 mL of EtOAc and 20 mL of water. The organic phase was washed with saturated Na$_2$S$_2$O$_3$ (aqueous, 3×) and brine, dried over Na$_2$SO$_4$, and filtered. The filtrate was concentrated on a rotary evaporator to give the title compound (457 mg, 2.053 mmol, 96% yield) as a yellow solid. $^1$H NMR (400 MHz, chloroform-d) δ 10.17 (s, 1H), 8.67 (s, 1H), 8.27 (d, J=1.8 Hz, 1H), 8.16 (d, J=1.8 Hz, 1H), 4.17 (s, 3H); LC-MS: method H, RT=0.88 min, MS (ESI) m/z: 223.2.

Intermediate I-35K:
(8-chloro-3-methoxyquinoxalin-6-yl)methanol

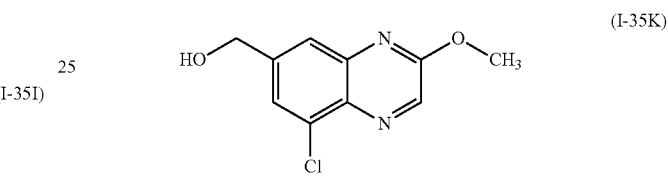

(I-35K)

In a round bottom flask charged with a stirring bar, Intermediate I-35J (421 mg, 1.89 mmol) was dissolved in toluene (10 mL) and mixed with sodium triacetoxyborohydride (882 mg, 4.16 mmol). The mixture was stirred at 60° C. for 4 h. After cooling to room temperature, the solvent was removed on a rotary evaporator. The residue was dissolved in 30 mL of EtOAc and 20 mL of water. The organic phase was washed with brine, dried over Na$_2$SO$_4$, filtered and concentrated on a rotary evaporator to give the title compound (0.415 g, 1.847 mmol, 98% yield) as an off-white solid. $^1$H NMR (400 MHz, chloroform-d) δ 8.55 (s, 1H), 7.79-7.75 (m, 1H), 7.70 (d, J=1.8 Hz, 1H), 4.89 (s, 2H), 4.12 (s, 3H), 1.94 (br s, 1H); LC-MS: method H, RT=0.75 min, MS (ESI) m/z: 225.2.

Intermediate I-35

A microwave tube was charged with Pd$_2$(dba)$_3$ (48.9 mg, 0.053 mmol), X-Phos (102 mg, 0.214 mmol), 4,4,4',4',5,5,5',5'-octamethyl-2,2'-bi(1,3,2-dioxaborolane) (814 mg, 3.21 mmol), and potassium acetate (315 mg, 3.21 mmol). The tube was capped and then evacuated and backfilled with argon 3 times. Intermediate I-35K (240 mg, 1.068 mmol) in 1,4-dioxane (10 mL) was added via syringe, followed by flushing the reaction mixture with N$_2$ for 10 minutes. The reaction mixture was heated at 110° C. in a microwave reactor for 30 minutes. After cooling to room temperature, the reaction mixture was concentrated in vacuo and the residue was purified by flash chromatography (40 g silica gel, 0-100% EtOAc, then 0-10% MeOH/DCM) to give Intermediate I-35 (121 mg, 0.517 mmol, 48.4% yield) as a grey solid. LC-MS: method H, RT=0.75 min, MS (ESI) m/z: 235.2.

Intermediate I-36

2-methoxy-6,7-dimethyl-5-(4,4,5,5-tetramethyl-1,3,2-dioxaborolan-2-yl)quinoxaline

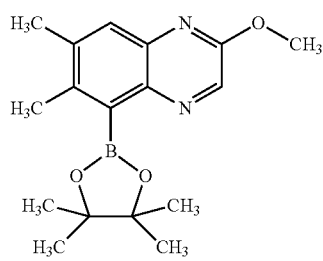

Intermediate I-36A:
2-bromo-3,4-dimethyl-6-nitroaniline

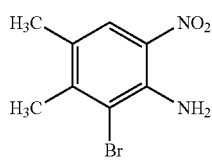
(I-36A)

From commercially available 4,5-dimethyl-2-nitroaniline (5.76 g, 34.7 mmol), Intermediate I-36A was prepared as a yellow solid (7.78 g, 31.7 g, 114%) via the same procedure as Intermediate I-28A. $^1$H NMR (400 MHz, DMSO-$d_6$) δ 7.90 (s, 1H), 7.11 (br s, 2H), 2.38 (s, 3H), 2.26 (s, 3H); LC-MS: method H, RT=1.22 min, MS (ESI) m/z: 245.1 and 247.0 (M+H)$^+$.

Intermediate I-36B: t-butyl N-(2-bromo-3,4-dimethyl-6-nitrophenyl)-N-[(tert-butoxy)carbonyl]carbamate

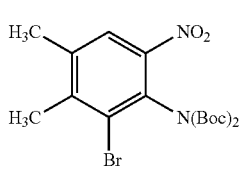
(I-36B)

Intermediate I-36B (9.2 g, 19.2 mmol, 65.1%) was made as a yellow solid from Intermediate I-36A (7.78 g, 20.66 mmol) via the same procedure as Intermediate I-28B. $^1$H NMR (400 MHz, chloroform-d) δ 7.83 (s, 1H), 2.51 (s, 3H), 2.46 (s, 3H), 1.41 (s, 18H); LC-MS: method J, RT=1.03 min, MS (ESI) m/z: 445.1 and 447.0 (M+H)$^+$.

Intermediate I-36C: tert-butyl (2-bromo-3,4-dimethyl-6-nitrophenyl)carbamate

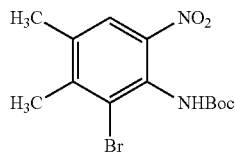
(I-36C)

Intermediate I-36C (6.6 g, 19.1 mmol, 93%) was made as a yellow solid from Intermediate I-36B (9.2 g, 1.30 mmol) via the same procedure as Intermediate I-28C. $^1$H NMR (400 MHz, DMSO-$d_6$) δ 9.18 (br s, 1H), 7.80 (s, 1H), 2.42 (s, 3H), 2.39 (s, 3H), 1.50-1.22 (m, 9H); LC-MS: method J, RT=0.88 min, MS (ESI) m/z: 245.0 and 247.0 (M+H−100)$^+$.

Intermediate I-36D: methyl 2-((2-bromo-3,4-dimethyl-6-nitrophenyl)(tert-butoxycarbonyl)amino)acetate

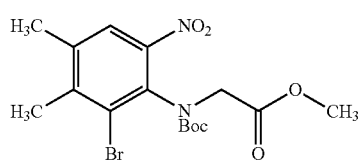
(I-36D)

Intermediate I-36D (3.21 g, 7.69 mmol, 87%) was made as an orange oil from Intermediate I-36C (3.05 g, 8.84 mmol) via the same procedure as Intermediate I-28D. LC-MS: method H, RT=1.27 min, MS (ESI) m/z: 317.0 and 319.1 (M+H−100)$^+$.

Intermediate I-36E: methyl 2-((2-bromo-3,4-dimethyl-6-nitrophenyl)amino)acetate

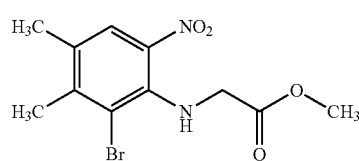
(I-36E)

Intermediate I-36E (2.43 g, 7.67 mmol, 100%) was made as a brown solid from Intermediate I-36D (3.2 g, 7.67 mmol) via the same procedure as Intermediate I-28E. LC-MS: method H, RT=1.22 min, MS (ESI) m/z: 317.0 and 319.0 (M+H)$^+$.

Intermediate I-36F: 5-bromo-6,7-dimethyl-3,4-dihydroquinoxalin-2(1H)-one

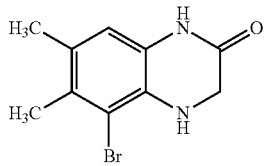

(I-36F)

Intermediate I-36F (1.69 g, 6.62 mmol, 86%) was made as a white solid from Intermediate I-36E (2.43 g, 7.67 mmol) via the same procedure as Intermediate I-28F. LC-MS: method H, RT=1.04 min, MS (ESI) m/z: 255.1 and 257.0 (M+H)+.

Intermediate I-36G: 5-bromo-6,7-dimethylquinoxalin-2(1H)-one

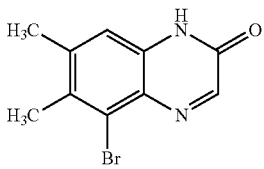

(I-36G)

Intermediate I-36G (1.12 g, 4.43 mmol, 86%) was made as a white solid from Intermediate I-36F (1.26 g, 4.94 mmol) via the same procedure as Intermediate I-28G. LC-MS: method H, RT=1.03 min, MS (ESI) m/z: 253.0 and 255.1 (M+H)+.

Intermediate I-36H: 5-bromo-2-methoxy-6,7-dimethylquinoxaline

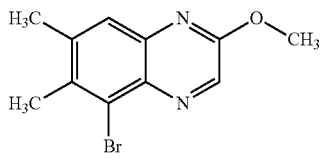

(I-36H)

Intermediate I-36H (0.79 g, 2.97 mmol, 67.2%) was made as a white solid from Intermediate I-36G (1.12 g, 4.43 mmol) via the same procedure as Intermediate I-28H. $^1$H NMR (400 MHz, chloroform-d) δ 8.48 (s, 1H), 7.61 (s, 1H), 4.10 (s, 3H), 2.61 (s, 3H), 2.53 (s, 3H); LC-MS: method H, RT=1.19 min, MS (ESI) m/z: 267.0 and 268.8 (M+H)+.

Intermediate I-36

Intermediate I-36 (0.50 g, 2.14 mmol, 72.5%) was made as a brown solid from Intermediate I-36H (0.79 g, 2.96 mmol) via the same procedure as Intermediate I-28I. LC-MS: method H, RT=0.96 min, MS (ESI) m/z: 232.9 (M+H−82)+.

Intermediate I-37

2(5-fluoro-3-methoxy-8-(4,4,5,5-tetramethyl-1,3,2-dioxaborolan-2-yl)quinoxalin-6-yl) methanol

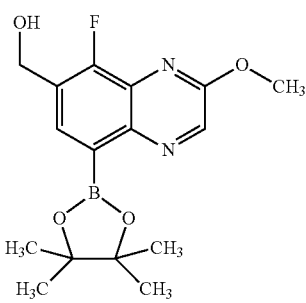

(I-37)

Intermediate I-37A: 4-bromo-6-chloro-3-fluoro-2-nitroaniline

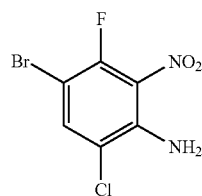

(I-37A)

A mixture of 4-bromo-3-fluoro-2-nitroaniline (1.0 g, 4.26 mmol), NCS (0.710 g, 5.32 mmol) in DMF (10 mL) was heated to 100° C. for 1 h. After cooling to room temperature, the reaction mixture was diluted by adding 40 mL of DCM and 30 mL of water. After shaking and separation, aqueous layer was extracted with DCM (20 mL×2). Then organic phases were combined and washed with brine, dried over Na$_2$SO$_4$, filtered concentrated on a rotary evaporator, dried on a high vacuum pump to give 4-bromo-6-chloro-3-fluoro-2-nitroaniline (1.22 g, 4.53 mmol, 106% yield) as brown oil. $^1$H NMR (400 MHz, chloroform-d) δ 7.64 (d, J=6.4 Hz, 1H), 6.02 (br s, 2H); $^{19}$F NMR (376 MHz, chloroform-d) δ −109.56 (s, 1F)

Intermediate I-37B: t-butyl N-(4-bromo-6-chloro-3-fluoro-2-nitrophenyl)-N-[(tert-butoxy)carbonyl]carbamate

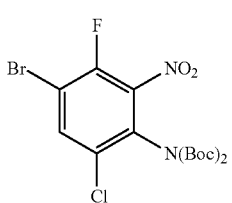

(I-37B)

Intermediate I-37A (1.22 g, 4.53 mmol) was dissolved in THF (10 mL) and mixed with di-tert-butyl dicarbonate (1.976 g, 9.06 mmol) at room temperature, DMAP (0.055 g, 0.453 mmol) was added. The mixture was stirred at room temperature overnight. the next day, solvent was removed on a rotary evaporator and residue was purified by flash chromatography for purification (40 g silica gel column, 0-50% EtOAc/Hexane gradient) to give the title compound (1.141 g, 2.429 mmol, 53.7% yield) as a white solid. $^1$H NMR (400 MHz, chloroform-d) δ 7.86 (d, J=6.4 Hz, 1H), 1.43 (s, 18H); $^{19}$F NMR (376 MHz, chloroform-d) δ −114.28 (s, 1F).

Intermediate I-37C: tert-butyl (4-bromo-6-chloro-3-fluoro-2-nitrophenyl)carbamate

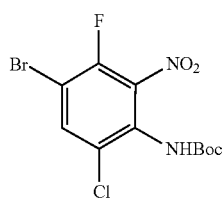

(I-37C)

Intermediate I-37C (0.85 g, 2.3 mmol, 95%) was made as a yellow solid from Intermediate I-37B (9.2 g, 1.30 mmol) via the same procedure as Intermediate I-28C. $^1$H NMR (400 MHz, chloroform-d) δ 7.82 (d, J=6.4 Hz, 1H), 6.61 (br s, 1H), 1.50 (s, 9H); $^{19}$F NMR (376 MHz, chloroform-d) δ −112.58 (br s, 1F).

Intermediate I-37D: methyl 2-((4-bromo-6-chloro-3-fluoro-2-nitrophenyl)(tert-butoxycarbonyl)amino)acetate

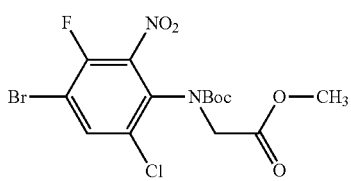

(I-37D)

Intermediate I-37D (0.68 g, 1.55 mmol, 68%) was made as a colorless oil from Intermediate I-37C (0.85 g, 2.30 mmol) via the same procedure as Intermediate I-28D. $^1$H NMR (400 MHz, chloroform-d) δ 7.85 (d, J=6.4 Hz, 1H), 4.44 (d, J=17.4 Hz, 1H), 3.96-3.89 (m, 1H), 3.74 (s, 3H), 1.40 (s, 9H); $^{19}$F NMR (376 MHz, chloroform-d) δ −114.08 (s, 1F); LC-MS: method H, RT=1.05 min, MS (ESI) m/z: 341.1 and 343.0 (M+H−100)$^+$.

Intermediate I-37E: methyl 2-((4-bromo-6-chloro-3-fluoro-2-nitrophenyl)amino)acetate

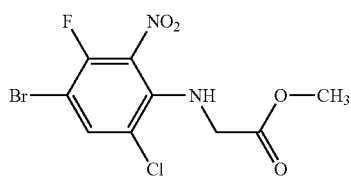

(I-37E)

Intermediate I-37E (0.53 g, 1.55 mmol, 100%) was made as brown oil from Intermediate I-37D (0.68 g, 1.55 mmol) via the same procedure as Intermediate I-28E. LC-MS: method H, RT=1.01 min, MS (ESI) m/z: 341.1 and 343.0 (M+H)$^+$.

Intermediate I-37F: 7-bromo-5-chloro-8-fluoro-3,4-dihydroquinoxalin-2(1H)-one

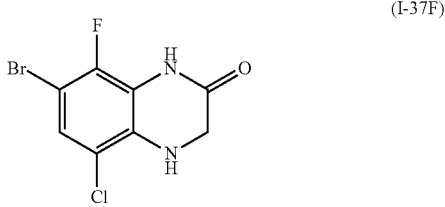 [SMILES: O=C1CNc2c(Cl)cc(Br)c(F)c2N1]

(I-37F)

Intermediate I-37F (0.34 g, 1.22 mmol, 79%) was made as a yellow oil from Intermediate I-37E (0.53 g, 1.55 mmol) via the same procedure as Intermediate I-28F. $^1$H NMR (400 MHz, Acetone) δ 9.51 (br s, 1H), 7.17 (d, J=6.4 Hz, 1H), 5.72 (br s, 1H), 4.05-3.97 (m, 2H); $^{19}$F NMR (376 MHz, Acetone) δ 47.90 (br s, 1F); LC-MS: method I, RT=1.17 min, MS (ESI) m/z: 279.0 and 281.1 (M+H)$^+$.

Intermediate I-37G: 7-bromo-5-chloro-8-fluoroquinoxalin-2(1H)-one

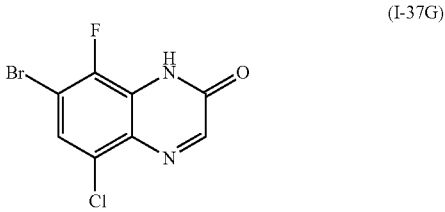 [SMILES: O=c1cnc2c(Cl)cc(Br)c(F)c2[nH]1]

(I-37G)

Intermediate I-37G (0.31 g, 1.10 mmol, 90%) was made as a yellow solid from Intermediate I-37F (0.34 g, 1.22 mmol) via the same procedure as Intermediate I-28G. LC-MS: method H, RT=0.77 min, MS (ESI) m/z: 277.0 and 279.0 (M+H)$^+$.

Intermediate I-37H: 7-bromo-5-chloro-8-fluoro-2-methoxyquinoxaline

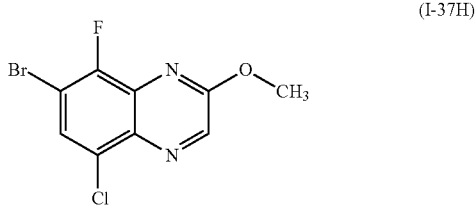

(I-37H)

Intermediate I-37G (306 mg, 1.103 mmol) was treated with POCl$_3$ (3 mL, 32.2 mmol) and heated to refluxing for 1 hour. After cooling to room temperature, extra POCl$_3$ was removed on a rotary evaporator and the residue was dried on HVAC for 1 hour. Then the material was dissolved in anhydrous MeOH (10 mL) and K$_2$CO$_3$ (517 mg, 3.74 mmol) was added. After stirring at room temperature for 10 minutes, the mixture was refluxed for 2 h. Then reaction mixture was cooled to room temperature. Most of MeOH was removed on a rotary evaporator and residue was dissolved in 30 mL of EtOAc and 15 mL of H$_2$O. After separation, organic phase was washed with brine, dried over Na$_2$SO$_4$, filtered and concentrated on a rotary evaporator. The residue was purified by flash chromatography column (40 g silica gel, 0-100% EtOAc/Hexane gradient). Removing solvent gave 7-bromo-5-chloro-8-fluoro-2-methoxyquinoxaline (85 mg, 0.292 mmol, 26.4% yield) as a yellow solid. $^1$H NMR (400 MHz, chloroform-d) δ 8.60 (s, 1H), 7.82 (d, J=6.2 Hz, 1H), 4.18 (s, 3H); $^{19}$F NMR (376 MHz, chloroform-d) δ −119.01 (s, 1F); LC-MS: method H, RT=1.05 min, MS (ESI) m/z: 291.0 and 293.1 (M+H)$^+$.

Intermediate I-37I:
5-chloro-8-fluoro-2-methoxy-7-vinylquinoxaline

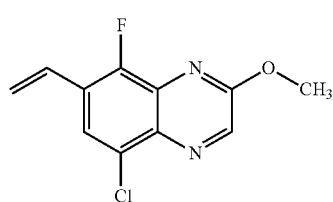

(I-37I)

To a vial charged with a stirring bar was added Intermediate I-37H (83 mg, 0.285 mmol), potassium trifluoro(vinyl)borate (36.2 mg, 0.270 mmol), cesium carbonate (186 mg, 0.569 mmol), (s)-2,2'-bis(diphenylphosphino)-1,1'-binaphthalene (35.5 mg, 0.057 mmol) and Pd(OAc)$_2$ (6.39 mg, 0.028 mmol). After applying vacuum and refilling with N$_2$ 3 times, DMF (1.0 mL) was added and the mixture was degassed with bubbling N$_2$ for 10 minutes. The vial was sealed and the reaction mixture was stirred at room temperature for 10 minutes, then heated at 120° C. for 2 h. After cooling to room temperature, the reaction mixture was diluted by adding 20 mL of EtOAc and washed with water and brine, dried over Na$_2$SO$_4$ and filtered. Removing solvent gave crude product that was purified by flash chromatography (24 g silica gel column, 0-100% EtOAc/Hexane gradient in 10 minutes). Removing solvent gave 5-chloro-8-fluoro-2-methoxy-7-vinylquinoxaline (43 mg, 0.180 mmol, 63.3% yield) as a yellow solid. LC-MS: method H, RT=1.05 min, MS (ESI) m/z: 239.0 (M+H)$^+$.

Intermediate I-37J: 8-chloro-5-fluoro-3-methoxyquinoxaline-6-carbaldehyde

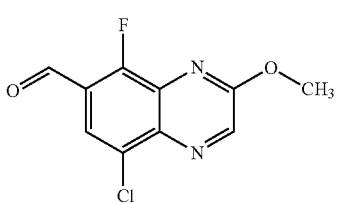

(I-37J)

Intermediate I-37I (43 mg, 0.180 mmol) was dissolved in THF (3 mL))/water (1 mL). Sodium periodate (116 mg, 0.541 mmol) was added, followed by osmium tetroxide (0.023 mL, 3.60 μmol). The mixture was stirred at room temperature for 6 h. Then the reaction mixture was diluted by adding 30 mL of EtOAc and 20 mL of water. After separation, organic phase was washed with saturated Na$_2$S$_2$O$_3$ (aqueous) 3 times, brine, dried over Na$_2$SO$_4$ and filtered. Concentration on a rotary evaporator gave 8-chloro-5-fluoro-3-methoxyquinoxaline-6-carbaldehyde (32 mg, 0.133 mmol, 73.8% yield) as light yellow solid. $^1$H NMR (400 MHz, chloroform-d) δ 10.58 (s, 1H), 8.70 (s, 1H), 8.07 (d, J=5.9 Hz, 1H), 4.22 (s, 3H); LC-MS: method H, RT=0.90 min, MS (ESI) m/z: 241.0 (M+H)$^+$.

Intermediate I-37K: (8-chloro-5-fluoro-3-methoxyquinoxalin-6-yl)methanol

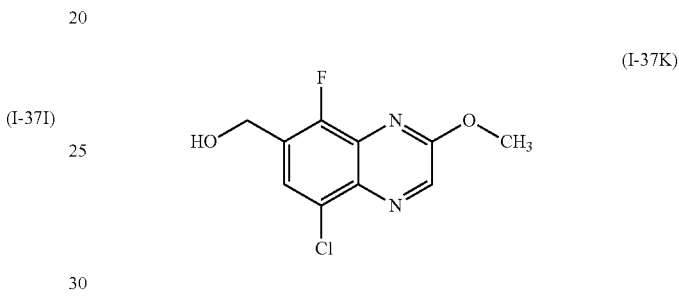

(I-37K)

Intermediate I-37J (32 mg, 0.133 mmol) was dissolved in toluene (1 mL) and mixed with sodium triacetoxyborohydride (62.0 mg, 0.293 mmol). The mixture was stirred at 60° C. for 4 hour. Then reaction mixture was cooled to room temperature, solvent was removed on a rotary evaporator. The residue was dissolved in 20 mL of EtOAc and 10 mL of water. After separation, organic phase was washed with brine, passed over Na$_2$SO$_4$, concentrated on a rotary evaporator to give (8-chloro-5-fluoro-3-methoxyquinoxalin-6-yl)methanol (26 mg, 0.107 mmol, 81% yield) as a solid. $^1$H NMR (400 MHz, chloroform-d) δ 8.58 (s, 1H), 7.80 (d, J=6.2 Hz, 1H), 4.97 (d, J=4.4 Hz, 2H), 4.17 (s, 3H), 2.10-2.03 (m, 1H); LC-MS: method H, RT=0.75 min, MS (ESI) m/z: 243.0 (M+H)$^+$.

Intermediate I-37

In a microwave tube was charged with Pd$_2$(dba)$_3$ (4.91 mg, 5.36 μmol), XPhos (10.22 mg, 0.021 mmol), 4,4,4',4',5,5,5',5'-octamethyl-2,2'-bi(1,3,2-dioxaborolane) (82 mg, 0.321 mmol) and potassium acetate (31.5 mg, 0.321 mmol). The microwave tube was capped, evacuated and backfilled with argon (this sequence was carried out two times). Intermediate I-37J (26 mg, 0.107 mmol) in 1,4-dioxane (1 ml) was added via syringe, followed by flushing the reaction mixture with N$_2$ for 10 minutes. The microwave tube was sealed and the reaction mixture was heated at 130° C. in a microwave reactor for 30 minutes. After cooling to room temperature, the reaction mixture was removed. The crude material Intermediate I-37 was used without purification in the next step. LC-MS: method H, RT=0.65 min, MS (ESI) m/z: 253.1 (M+H)$^+$.

Intermediate I-38

3-methoxy-8-(4,4,5,5-tetramethyl-1,3,2-dioxaborolan-2-yl)quinoxaline-6-carbonitrile

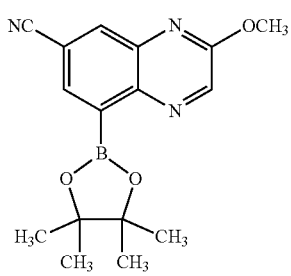
(I-38)

Intermediate I-38A: 8-bromo-3-oxo-1,2,3,4-tetrahydroquinoxaline-6-carbonitrile

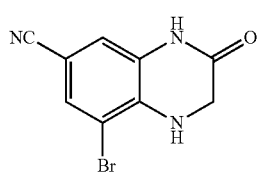
(I-38A)

Intermediate I-38A was synthesized from 4-amino-3-nitrobenzonitrile via the route described for Intermediate I-28. LC-MS: method I, RT=0.94 min, MS (ESI) m/z: 252.0 and 253.9 (M+H)$^+$.

Intermediate I-38B: 8-bromo-3-oxo-3,4-dihydroquinoxaline-6-carbonitrile

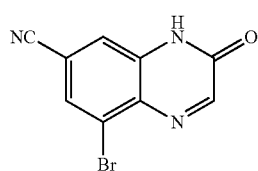
(I-38B)

In a round bottom flask charged with a stirring bar, Intermediate I-38A (394 mg, 1.563 mmol) was suspended in DMF (10 mL), and manganese dioxide (1359 mg, 15.63 mmol) was added. The mixture was stirred at room temperature for 60 minutes. LCMS showed starting material remained. Another 10 equivalents of manganese dioxide (1359 mg, 15.63 mmol) was added, and the mixture was stirred at room temperature overnight. The next day, the solid was filtered and solvent was removed on a rotary evaporator and dried on HVAC to give the title compound (100 mg, 0.400 mmol, 25.6% yield) as a yellow solid. $^1$H NMR (400 MHz, DMSO-d$_6$) δ 8.32 (s, 1H), 7.95 (d, J=2.6 Hz, 1H), 7.65 (s, 1H); LC-MS: method A, RT=2.42 min, MS (ESI) m/z: 248.0 and 250.0 (M+H)$^+$.

Intermediate I-38 was synthesized in two steps from Intermediate I-38B via the route described in Intermediate I-28. LC-MS: method A, RT=0.97 min, MS (ESI) m/z: 230.1 (M+H)$^+$ of boronic acid.

Intermediate I-39

Ethyl 2-((2-bromo-4-methylbenzo[d]thiazol-6-yl)oxy)acetate

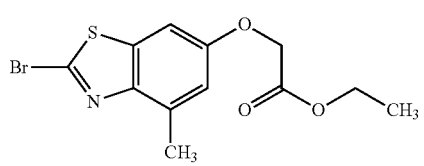
(I-39)

Intermediate I-39 was made from Intermediate I-40 following the procedure described in I-49. $^1$H NMR (400 MHz, chloroform-d) δ 7.08 (d, J=2.2 Hz, 1H), 6.95-6.92 (m, 1H), 4.66 (s, 2H), 4.29 (q, J=7.3 Hz, 2H), 2.67 (s, 3H), 1.31 (t, J=7.2 Hz, 3H; LC-MS: method H, RT=1.37 min, MS (ESI) m/z: 330.0 and 332.0.

Intermediate I-40

2-bromo-4-methylbenzo[d]thiazol-6-ol

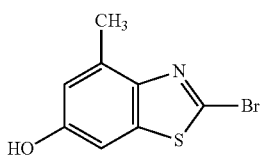
(I-40)

Intermediate I-3 (100 mg, 0.387 mmol) was solvated in DCM (3.87 mL) and cooled to 0° C. Boron tribromide (1.0 M in Hexanes) (0.415 mL, 0.415 mmol) was slowly added dropwise. After 1 h of stirring, the reaction mixture was allowed to thaw to room temperature. Once at room temperature, the reaction mixture was recooled to 0° C. and quenched with saturated NH$_4$Cl. The resulting mixture was extracted twice with DCM and the organic phase was dried over MgSO$_4$, filtered and concentrated. The crude product was purified by ISCO (12 g, 0-30% EtOAc/Hexanes, 18 min. Product at 18%) to give clean Intermediate I-40 (54 mg, 0.221 mmol, 57.1% yield) as a white solid. LC-MS: Method H, RT=1.10 min, MS (ESI) m/z: 244.0, 246.0 (M+H)$^+$. $^1$H NMR (400 MHz, METHANOL-d$_4$) δ 7.06 (d, J=2.2 Hz, 1H), 6.79 (s, 1H), 2.57 (s, 1H).

Intermediate I-41

2-bromo-4,5-difluoro-6-methoxybenzo[d]thiazole

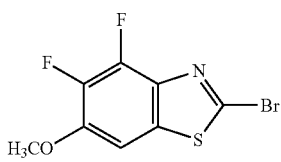
(I-41)

Intermediate I-41A: 2,3-difluoro-4-methoxyaniline

(I-41A)

Degussa grade Pd/C (1.125 g, 1.058 mmol) was added to a 250 mL round bottom flask previously purged with argon. The Pd was carefully wetted with a few milliliters of MeOH before the full amount of solvent (42.3 ml) was added. The head space of the flask was evacuated until the solvent began to slightly bubble and then back-filled 3× with $N_2$. 2,3-difluoro-1-methoxy-4-nitrobenzene (2.0 g, 10.58 mmol) was added to the black suspension, and a balloon of $H_2$ gas was attached. The heterogeneous mixture was sparged with $H_2$ for 30 min, before being allowed to stir under an atmosphere of $H_2$ for an additional 4 h. The reaction mixture was then filtered over celite to remove Pd/C. The celite was rinsed with EtOAc, and the filtrate was concentrated to afford Intermediate I-41A (1.63 g, 10.24 mmol, 97% yield) as a purple solid. LC-MS: Method H, RT=0.83 min, MS (ESI) m/z: 160.1 (M+H)+. 1H NMR (400 MHz, CHLOROFORM-d) δ 6.59 (td, J=8.6, 2.2 Hz, 1H), 6.49-6.43 (m, 1H), 3.83 (s, 3H), 3.51 (br. s., 2H).

Intermediate I-41B: 4,5-difluoro-6-methoxybenzo[d]thiazol-2-amine

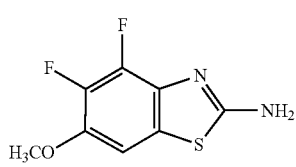
(I-41-B)

To a solution of Intermediate I-41A (1.63 g, 10.24 mmol) in acetonitrile (51.2 ml) was added ammonium thiocyanate (1.014 g, 13.32 mmol). The mixture was stirred at room temperature for 10 min followed by the addition of benzyltrimethylammonium tribromide (4.39 g, 11.27 mmol). After 16 h, the reaction mixture was concentrated down and retaken in DCM. The organic phase was washed with saturated $NaHCO_3$, concentrated and purified by ISCO (120 g, 0-100% EtOAc/Hexanes, 16 min. Product from 55%-100%) to afford Intermediate I-41B (398 mg, 1.843 mmol, 18% yield). LC-MS: Method H, RT=0.93 min, MS (ESI) m/z: 217.2 (M+H)+. 1H NMR (400 MHz, CHLOROFORM-d) δ 6.96 (dd, J=6.9, 2.1 Hz, 1H), 5.19 (br. s., 2H), 3.92 (s, 3H).

Intermediate I-41

To a solution of copper (II) bromide (289 mg, 1.295 mmol) and Intermediate I-41B (280 mg, 1.295 mmol) in acetonitrile (10 mL) was added t-Butyl nitrite (0.222 mL, 1.684 mmol) at room temperature. After 30 min, the crude mixture was diluted with EtOAc and washed with 1 M HCl. The organic phase was dried over $MgSO_4$, filtered, concentrated and purified by ISCO flash chromatography (0-20% EtOAc/Hex, 19 min, 40 g silica gel cartridge. Product from 12% to 20%) to afford Intermediate I-41 (271 mg, 0.968 mmol, 74.7% yield) as an off-white solid. LC-MS: Method H, RT=1.21 min, MS (ESI) m/z: 280.1, 282.0 (M+H)+. 1H NMR (400 MHz, CHLOROFORM-d) δ 7.11 (dd, J=6.6, 2.0 Hz, 1H), 3.98 (s, 3H).

Intermediate I-42

2-bromo-4,5-difluorobenzo[d]thiazol-6-ol

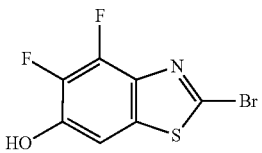
(I-42)

A solution of Intermediate I-41 (220 mg, 0.785 mmol) solvated in DCM (20 ml) was cooled to 0° C. A solution of $BBr_3$ (1.0 M hexanes) (1.571 ml, 1.571 mmol) was then added dropwise. After 5 min, the mixture was allowed to thaw to room temperature. After an additional 18 h, the reaction mixture was quenched with 1 M HCl (20.0 mL) and stirred vigorously for 20 min to fully cleave the boronate complex. The mixture was diluted with EtOAc and extracted. The organic phase was dried over $MgSO_4$, filtered and concentrated to give Intermediate I-42 (208 mg, 0.785 mmol, 100% yield) which was taken forward without further purification. LC-MS: Method H, RT=1.08 min, MS (ESI) m/z: 266.0, 268.0 (M+H)+. 1H NMR (400 MHz, METHANOL-d4) δ 7.24 (dd, J=7.2, 2.1 Hz, 1H).

Intermediate I-43

2-bromo-4-chloro-5-fluoro-6-methoxybenzo[d]thiazole

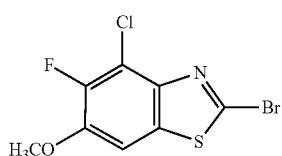
(I-43)

Intermediate I-43A:
2-chloro-3-fluoro-4-methoxy-1-nitrobenzene

(I-43A)

To a 0° C. solution of 1-chloro-2-fluoro-3-methoxybenzene (1.606 g, 10 mmol) in acetic acid (5.00 ml) was added fuming nitric acid (0.933 ml, 20.00 mmol) followed by the dropwise addition of sulfuric acid (2.132 ml, 40.0 mmol). After 30 min, the reaction mixture was poured into water and diluted with ethyl acetate. The organic phase was separated and washed 2× with saturated NaHCO$_3$ followed by a final brine wash. The organic solution was then dried over MgSO$_4$, filtered, concentrated and purify by ISCO (120 g, 10-50% EtOAc/Hexanes, 25 min. Desired regioisomer eluted second) affording Intermediate I-43A (1.10 g, 5.35 mmol, 53% yield) as a yellow solid. LC-MS: Method H, RT=1.13 min, MS (ESI) m/z: No Ionization Observed (M+H)$^+$. $^1$H NMR (400 MHz, CHLOROFORM-d) δ 7.89 (dd, J=9.2, 2.2 Hz, 1H), 6.95 (dd, J=9.4, 7.6 Hz, 1H), 4.00 (s, 3H). Regiochemistry confirmed through NMR analysis of both regioisomeric products.

Intermediate I-43B:
2-chloro-3-fluoro-4-methoxyaniline

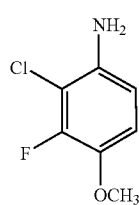

(I-43B)

To a solution of Intermediate I-43A (1.10 g, 5.35 mmol) in MeOH (26.7 mL, 0.2 M) was added NH$_4$Cl (5.72 g, 107 mmol) and zinc dust (3.50 g, 53.5 mmol). The resulting mixture was allowed to stir at room temperature overnight. After 14 h, the MeOH solvent was removed in vacuo. The resulting residue was diluted with EtOAc and saturated sodium bicarbonate (0.2 M of each) and stirred vigorously for 1 hr and then filtered over celite. The organic layer was then separated, washed with brine, dried over MgSO$_4$, filtered and concentrated to give Intermediate I-43B (710 mg, 4.04 mmol, 76% yield) as a dark brown solid. This material was taken on without further purification. LC-MS: Method H, RT=0.95 min, MS (ESI) m/z: 176.1, 178.1 (M+H)$^+$. $^1$H NMR (400 MHz, CHLOROFORM-d) δ 6.76 (t, J=8.7 Hz, 1H), 6.49 (dd, J=9.0, 2.2 Hz, 1H), 3.86 (br. s, 2H), 3.82 (s, 3H).

Intermediate I-43C: 4-chloro-5-fluoro-6-methoxy-benzo[d]thiazol-2-amine

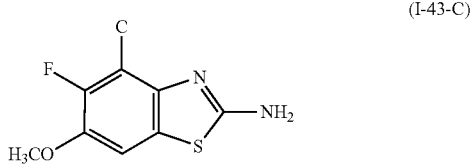

(I-43-C)

To a solution of Intermediate I-43B (820 mg, 3.74 mmol) in acetonitrile (18.700 mL) was added ammonium thiocyanate (370 mg, 4.86 mmol). The mixture was stirred at room temperature for 10 min and then benzyltrimethylammonium tribromide (1457 mg, 3.74 mmol) was added. The resulting heterogeneous mixture was stirred vigorously overnight. After 16 h, the reaction mixture was concentrated and retaken in 30 mL saturated NaHCO$_3$. This suspension was stirred vigorously and then filtered. The collected solid was washed with water and transferred to a new flask using acetone. This solution was concentrated in vacuo to afford Intermediate I-43C (863 mg, 3.67 mmol, 99% yield) as a yellow solid. This material was taken on without further purification. LC-MS: Method H, RT=0.95 min, MS (ESI) m/z: 233.1, 235.1 (M+H)$^+$. $^1$H NMR (400 MHz, METHANOL-d$_4$) δ 7.34 (d, J=7.5 Hz, 1H), 3.88 (s, 3H).

Intermediate I-43

To a solution of copper (II) bromide (835 mg, 3.74 mmol) and Intermediate I-43C (870 mg, 3.74 mmol) in acetonitrile (18.700 mL) was added t-butyl nitrite (0.642 mL, 4.86 mmol) at room temperature. After 30 min, the reaction mixture was diluted with EtOAc and washed with 1 M HCl followed by 1 M K$_2$HPO$_4$, then brine. The organic phase was concentrated and purified by ISCO flash chromatography (0-20% EtOAc/Hex over 30 min, 120 g silica gel cartridge-product at 10%) to afford Intermediate I-43 (723 mg, 2.267 mmol, 60.6% yield) as a yellow solid. LC-MS: Method H, RT=1.23 min, MS (ESI) m/z: 295.9, 297.9, 299.9 (M+H)$^+$. $^1$H NMR (400 MHz, CHLOROFORM-d) δ 7.23 (d, J=7.3 Hz, 1H), 3.96 (s, 3H).

Intermediate I-44

2-bromo-4-chloro-5-fluorobenzo[d]thiazol-6-ol

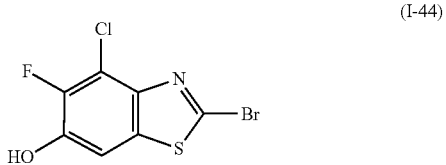 [SMILES: Oc1cc2sc(Br)nc2c(Cl)c1F]

(I-44)

To a solution of Intermediate I-43 (72 mg, 0.243 mmol) in toluene (2428 µl) was added AlCl$_3$ (97 mg, 0.728 mmol) and the mixture was heated to reflux. After 2 h, the solution was allowed to cool to room temperature, and the resulting mixture was diluted with 1 M HCl followed by EtOAc. The organic phase was separated, dried over MgSO$_4$, filtered and concentrated to give Intermediate I-44 (38 mg, 0.135 mmol, 55.4% yield) as a brown solid. The isolated material was taken on without further purification. LC-MS: Method H, RT=1.10 min, MS (ESI) m/z: 281.9, 284.0, 285.9 (M+H)+. 1H NMR (400 MHz, METHANOL-d4) δ 7.39 (d, J=7.7 Hz, 1H).

Intermediate I-45

2-bromo-5-fluoro-6-methoxy-4-methylbenzo[d]thiazole

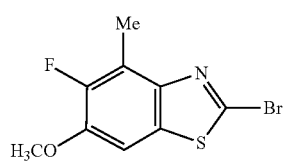

Intermediate I-45A: 1-chloro-3-fluoro-2-methoxy-4-methyl-5-nitrobenzene

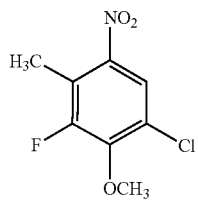

A solution of 1-chloro-3-fluoro-2-methoxy-4-methylbenzene (1 g, 5.73 mmol) in acetic acid (2.86 ml) was cooled to 0° C. To this cooled solution was added fuming nitric acid (0.535 ml, 11.45 mmol) followed by sulfuric acid (1.221 ml, 22.91 mmol) dropwise. After 30 min, the reaction mixture was poured into ice water and extracted with ethyl acetate. The organic phase was washed with 1 M K2HPO4 and then concentrated in vacuo to give Intermediate I-45A (1.26 g, 5.16 mmol, 90% yield) as a dark orange oil. This material was taken forward without further purification. LC-MS: Method H, RT=1.22 min, MS (ESI) m/z: None Observed (M+H)+. 1H NMR (400 MHz, CHLOROFORM-d) δ 7.91 (d, J=2.2 Hz, 1H), 4.08 (d, J=2.4 Hz, 3H), 2.50 (d, J=2.9 Hz, 3H).

Intermediate I-45B: 5-chloro-3-fluoro-4-methoxy-2-methylaniline

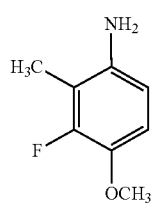

A 250 mL round bottom flask containing Intermediate I-45A (1.26 g, 5.74 mmol) was evacuated and back-filled with N2. Degussa grade Pd/C (0.611 g, 0.574 mmol) was then added to the orange oil. This mixture was carefully wet with a few mL of MeOH before the full solvent volume (28.7 ml) was added. The head space of the flask was evacuated until the solvent began to slightly bubble and then back-filled with N2. A balloon of hydrogen gas was attached and the mixture was sparged with H2 for about 15 minutes through a vent needle. The vent was removed and the reaction mixture was stirred vigorously under an atmosphere of H2 overnight. After 14 h, the reaction mixture was filtered over Celite and rinsed with EtOAc to afford Intermediate I-45B (890 mg, 5.74 mmol, 100% yield) as a tan solid. This material was taken on to the next reaction without further purification. LC-MS: Method H, RT=0.71 min, MS (ESI) m/z: 156.0 (M+H)+. 1H NMR (400 MHz, METHANOL-d4) δ 7.18-6.95 (m, 2H), 3.88 (s, 3H), 2.27 (d, J=2.4 Hz, 3H).

Intermediate I-45C: 5-fluoro-6-methoxy-4-methylbenzo[d]thiazol-2-amine

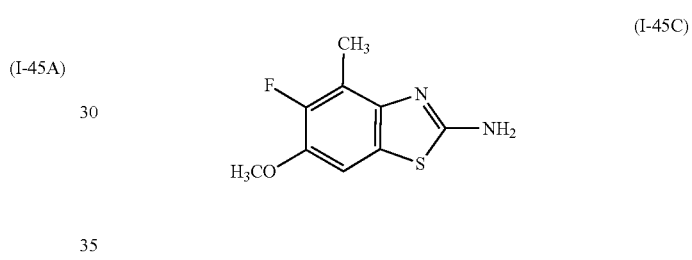

To a solution of Intermediate I-45B (1.03 g, 6.64 mmol) in acetonitrile (33.2 ml) was added ammonium thiocyanate (0.657 g, 8.63 mmol) followed by benzyltrimethylammonium tribromide (2.59 g, 6.64 mmol). The resulting mixture was stirred vigorously for 4 h before being diluted with saturated NaHCO3 and extracted 2× with DCM. The organic phase was dried over MgSO4, filtered and concentrated in vacuo to afford Intermediate I-45C (920 mg, 4.33 mmol, 65.3% yield). This material was taken on without further purification. LC-MS: Method H, RT=0.84 min, MS (ESI) m/z: 213.1 (M+H)+. 1H NMR (400 MHz, DMSO-d6) δ 7.39 (br. s., 2H), 7.35 (d, J=8.1 Hz, 1H), 3.80 (s, 3H), 2.33 (d, J=2.2 Hz, 3H).

Intermediate I-45

To a heterogeneous solution of Intermediate I-45C (920 mg, 4.33 mmol) in acetonitrile (43.3 ml) was added copper (II) bromide (0.968 g, 4.33 mmol) followed by t-butyl nitrite (0.745 ml, 5.64 mmol). After 30 min, the reaction mixture was diluted with 1 M HCl and extracted 2× with EtOAc. The organic phase was dried over MgSO4, filtered over celite, concentrated and purified by ISCO (120 g, 0-10% EtOAc/Hexanes, 35 min. Product at 4%) to afford Intermediate I-45 (750 mg, 2.72 mmol, 62.7% yield) as a beige solid. LC-MS: Method H, RT=1.28 min, MS (ESI) m/z: 276.0, 278.0 (M+H)+. 1H NMR (400 MHz, CHLOROFORM-d) δ 7.15 (d, J=7.5 Hz, 1H), 3.93 (s, 3H), 2.61 (dd, J=2.4, 0.4 Hz, 3H).

Intermediate I-46

2-bromo-5-fluoro-4-methylbenzo[d]thiazol-6-ol

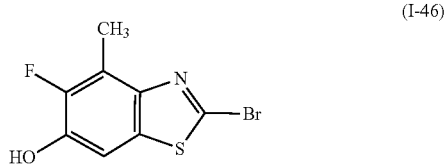

(I-46)

To a solution of Intermediate I-45 (155 mg, 0.561 mmol) in toluene (2807 μl) was added AlCl₃ (225 mg, 1.684 mmol). The mixture was heated to 90° C. for 30 min and then allowed to cool room temperature. The resulting mixture was diluted with EtOAc and washed 2× with 1 M HCl followed by Brine. The organic phase was dried over MgSO₄, filtered and concentrated in vacuo to afford Intermediate I-46 (123 mg, 0.399 mmol, 71.1% yield) as a brown solid. This material was taken on without further purification. LC-MS: Method H, RT=1.11 min, MS (ESI) m/z: 262.0, 264.0 (M+H)⁺. ¹H NMR (400 MHz, METHANOL-d₄) δ 7.23 (dd, J=7.9, 0.4 Hz, 1H), 2.54 (dd, J=2.4, 0.4 Hz, 3H).

Intermediate I-47

2-bromo-6-methoxy-4,5-dimethylbenzo[d]thiazole

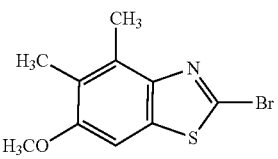

(I-47)

Intermediate I-47A: 4-methoxy-2,3-dimethylaniline

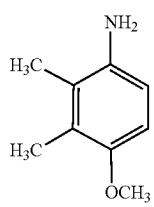

(I-47A)

A 250 mL round bottom flask containing 1-methoxy-2,3-dimethyl-4-nitrobenzene (1 g, 5.52 mmol) was evacuated and back-filled with N₂. The flask was then charged with Degussa grade Pd/C (0.587 g, 0.552 mmol). This mixture was carefully wet with a few milliliters of MeOH before the full solvent volume (27.6 ml) was added. The head space of the flask was evacuated until the solvent began to slightly bubble and then back-filled with N₂. A balloon of hydrogen gas was attached and the mixture was sparged with H₂ for about 15 minutes through a vent needle. The vent was removed and the reaction mixture was stirred vigorously under an atmosphere of H₂ overnight. After 14 h, the reaction mixture was filtered over celite and rinsed with EtOAc to afford Intermediate I-47B (820 mg, 5.42 mmol, 98% yield) as a dark brown solid. This material was taken on to the next reaction without further purification. LC-MS: Method H, RT=0.71 min, MS (ESI) m/z: 152.1 (M+H)⁺. ¹H NMR (400 MHz, CHLOROFORM-d) δ 6.66-6.47 (m, 2H), 3.75 (s, 3H), 3.34 (br. s., 2H), 2.17 (s, 3H), 2.10 (s, 3H).

Intermediate I-47B: 6-methoxy-4,5-dimethylbenzo[d]thiazol-2-amine

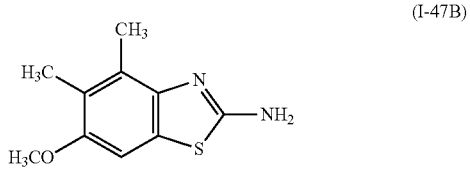

(I-47B)

To a solution of Intermediate I-47A (100 mg, 0.661 mmol) in acetonitrile (18.700 mL) was added ammonium thiocyanate (370 mg, 4.86 mmol). The mixture was stirred at room temperature for 10 min and then benzyltrimethylammonium tribromide (1457 mg, 3.74 mmol) was added. After 2 h of vigorous stirring, the reaction mixture was concentrated and retaken in 5 mL saturated NaHCO₃. This suspension was stirred vigorously and then filtered. The collected solid was washed with water and transferred to a new flask using acetone. This solution was concentrated in vacuo to afford Intermediate I-47B (136 mg, 0.654 mmol, 99% yield) as a tan solid. This material was taken on without further purification. LC-MS: Method H, RT=0.88 min, MS (ESI) m/z: 209.2 (M+H)⁺. ¹H NMR (400 MHz, METHANOL-d₄) δ 7.03 (s, 1H), 3.79 (s, 3H), 2.42 (s, 3H), 2.17 (s, 3H).

Intermediate I-47

To a heterogeneous solution of crude Intermediate I-47B (136 mg, 0.65 mmol) in acetonitrile (6600 μl) was added copper (II) bromide (145 mg, 0.65 mmol) followed by t-butyl nitrite (113 μl, 0.858 mmol). After 30 min, the reaction mixture was diluted with 1 M HCl and EtOAc. The organic phase was dried over MgSO₄, filtered, concentrated and purified by ISCO (24 g, 0-20% EtOAc/Hexanes, 25 min. Product at 5%) to afford Intermediate I-47 (45 mg, 0.165 mmol, 25.05% yield) as a beige solid. LC-MS: Method H, RT=1.34 min, MS (ESI) m/z: 272.1, 274.1 (M+H)⁺. ¹H NMR (400 MHz, CHLOROFORM-d) δ 7.05 (s, 1H), 3.87 (s, 3H), 2.64 (s, 3H), 2.25 (s, 3H).

Intermediate I-48

2-bromo-4,5-dimethylbenzo[d]thiazol-6-ol

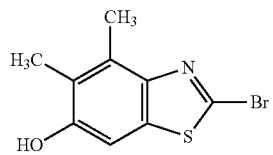

(I-48)

To a solution of Intermediate I-47 (600 mg, 2.205 mmol) in toluene (22.000 mL) was added AlCl₃ (588 mg, 4.41 mmol). The mixture was heated to 90° C. under an atmosphere of N₂ for 1 h. The solution was then cooled to room temperature and 22 mL of 1 M HCl was added. The resulting mixture was stirred vigorously at room temperature for 1 h. The solution was then filtered to collect the off-white solid which had precipitated out of the mixture. These solids were washed with water, retaken in toluene and concentrated in vacuo to afford Intermediate I-48 (350 mg, 2.205 mmol, 61.5% yield), which was taken on without further purification. LC-MS: Method H, RT=1.17 min, MS (ESI) m/z: 258.0, 260.0 (M+H)⁺. ¹H NMR (400 MHz, METHANOL-d₄) δ 7.06 (s, 1H), 2.57 (s, 3H), 2.24 (s, 3H).

Intermediate I-49 methyl 2-((2-bromo-4,5-dimethylbenzo[d]thiazol-6-yl)oxy)acetate

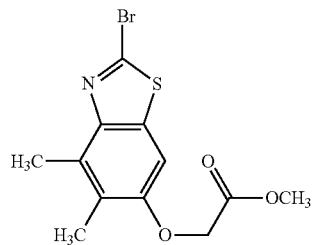

(I-49)

To a solution of Intermediate I-48 (240 mg, 0.930 mmol) solvated in DMF (9297 µl) was added methyl 2-bromoacetate (132 µl, 1.395 mmol) followed by K₂CO₃ (257 mg, 1.859 mmol). The resulting mixture was stirred vigorously at room temperature for 30 min, before being diluted EtOAc, filtered over celite, concentrated and purified by ISCO (40 g, 0-30% EtOAc/Hexanes, 19 min. Product at 15%) to afford Intermediate I-49 (268 mg, 0.812 mmol, 87% yield) as a light pink solid. LC-MS: Method H, RT=1.29 min, MS (ESI) m/z: 333.0, 332.0 (M+H)⁺. ¹H NMR (400 MHz, CHLOROFORM-d) δ 6.96 (s, 1H), 4.69 (s, 2H), 3.82 (s, 3H), 2.65 (s, 3H), 2.33 (s, 3H).

Intermediate I-50 methyl 2-((2-bromo-4,5-dimethylbenzo[d]thiazol-6-yl)oxy)propanoate (racemate)

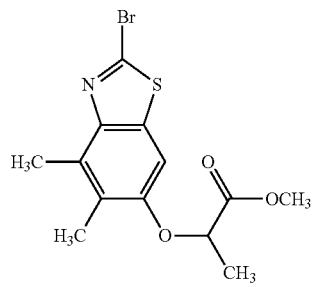

(I-50)

To a solution of Intermediate I-48 (30 mg, 0.116 mmol) solvated in DMF (1162 µl) was added methyl 2-bromopropanoate (38.9 µl, 0.349 mmol) followed by K₂CO₃ (48.2 mg, 0.349 mmol). The mixture was stirred vigorously for 1.5 h before being diluted with EtOAc, filtered over celite, concentrated and purified by ISCO (12 g, 0-30% EtOAc/Hexanes, 16 min. Product at 15%) to afford Intermediate I-50 (rac) (37 mg, 0.107 mmol, 92% yield) as a light pink solid. LC-MS: Method H, RT=1.31 min, MS (ESI) m/z: 344.1, 346.1 (M+H)⁺. ¹H NMR (400 MHz, CHLOROFORM-d) δ 6.93 (s, 1H), 4.76 (q, J=6.8 Hz, 1H), 3.76 (s, 3H), 2.64 (s, 3H), 2.31 (s, 3H), 1.67 (d, J=6.6 Hz, 3H).

Intermediate I-51

2-((2-bromo-4,5-dimethylbenzo[d]thiazol-6-yl)oxy)ethanol

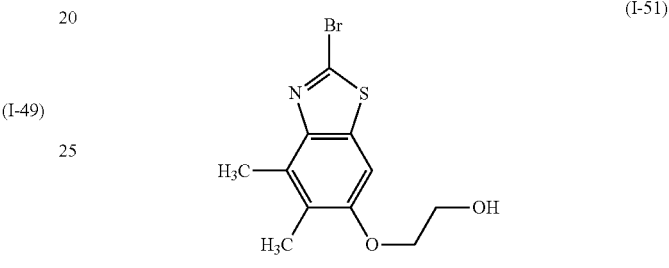

(I-51)

A solution of Intermediate I-49 (170 mg, 0.515 mmol) in toluene (3432 µl) and THF (1716 µl) was cooled to −78° C. under an atmosphere of N₂. To this cold solution was added DIBAL-H (1 M in Toluene) (1.13 mL, 1.13 mmol) dropwise. After 5 min of stirring, the reaction mixture was allowed to thaw to room temperature. Once this solution reached room temperature, 5 mL of 1 M HCl was added. The resulting slurry was stirred vigorously for 1 hr to fully cleave the aluminate complexes. The mixture was then diluted with EtOAc, extracted, washed with brine, dried over MgSO₄, filtered and concentrated. The crude product was purified by ISCO (40 g, 0-100% EtOAc/Hexanes, 19 min. Product at 47%) to afford 2-((2-bromo-4,5-dimethylbenzo[d]thiazol-6-yl)oxy) ethanol (156 mg, 0.516 mmol, 100% yield) as an off-white, amorphous solid. LC-MS: Method H, RT=1.19 min, MS (ESI) m/z: 302.1, 304.1 (M+H)⁺. ¹H NMR (400 MHz, CHLOROFORM-d) δ 7.08 (s, 1H), 4.15-4.09 (m, 2H), 4.06-3.99 (m, 2H), 2.65 (s, 3H), 2.29 (s, 3H), 1.94 (t, J=6.3 Hz, 1H).

Intermediate I-52

Methyl 2-((2-bromo-5-fluoro-4-methylbenzo[d]thiazol-6-yl)oxy)acetate

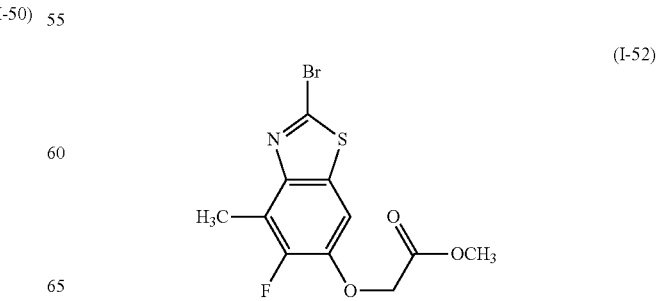

(I-52)

To a solution of Intermediate I-46 (105 mg, 0.341 mmol) solvated in DMF (3405 μl) was added methyl 2-bromoacetate (48.4 μl, 0.511 mmol) followed by K₂CO₃ (94 mg, 0.681 mmol). The reaction mixture was stirred vigorously at room temperature for 1 h before being diluted with EtOAc, filtered over celite and concentrated. The crude material was purified by ISCO (24 g, 0-50% EtOAc/Hexanes, 20 min. Product at 18%) to afford Intermediate I-52 (81 mg, 0.242 mmol, 71% yield) as a pink solid. LC-MS: Method H, RT=1.20 min, MS (ESI) m/z: 334.0, 336.0 (M+H)⁺. ¹H NMR (400 MHz, CHLOROFORM-d) δ 7.15 (d, J=7.5 Hz, 1H), 4.74 (s, 2H), 3.82 (s, 3H), 2.62 (dd, J=2.4, 0.4 Hz, 3H).

Intermediate I-53

2-((2-bromo-5-fluoro-4-methylbenzo[d]thiazol-6-yl)oxy)ethanol

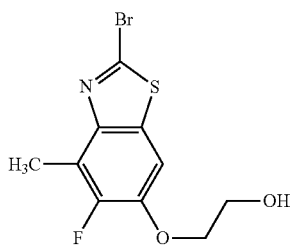

(I-53)

This intermediate was prepared in a manner analogous to Intermediate I-51. Thus, Intermediate I-52 was reacted to afford Intermediate I-53 (82% yield) as an off-white, amorphous solid. LC-MS: Method H, RT=1.09 min, MS (ESI) m/z: 306.0, 308.0 (M+H)⁺. ¹H NMR (400 MHz, CHLOROFORM-d) δ 7.19 (d, J=7.5 Hz, 1H), 4.20-4.15 (m, 2H), 4.02 (dt, J=6.2, 4.5 Hz, 2H), 2.61 (d, J=2.4 Hz, 3H), 2.08 (t, J=6.4 Hz, 1H).

Intermediate I-54

(2-bromo-6-methoxy-5-methylbenzo[d]thiazol-4-yl)methanol

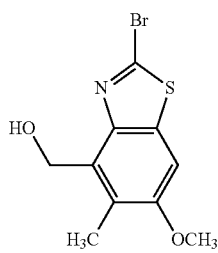

(I-54)

Intermediate I-54A: methyl 3-methoxy-2-methyl-6-nitrobenzoate

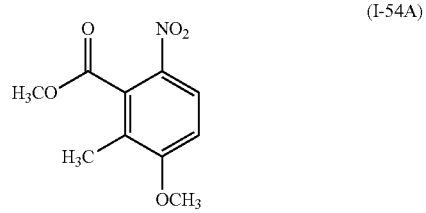 [SMILES: COC(=O)c1c([N+](=O)[O-])ccc(OC)c1C]

(I-54A)

This intermediate was prepared in a manner analogous to Intermediate I-43A. Thus, methyl 3-methoxy-2-methylbenzoate was reacted to afford Intermediate I-54A (56% yield) as the major regioisomer isolated from the reaction mixture (second eluting on silica gel). LC-MS: Method H, RT=1.20 min, MS (ESI) m/z: None Observed (M+H)⁺. ¹H NMR (400 MHz, CHLOROFORM-d) δ 8.13 (d, J=9.0 Hz, 1H), 6.92 (d, J=9.2 Hz, 1H), 3.97 (s, 3H), 3.95 (s, 3H), 2.20 (s, 3H).

Intermediate I-54B: methyl 6-amino-3-methoxy-2-methylbenzoate

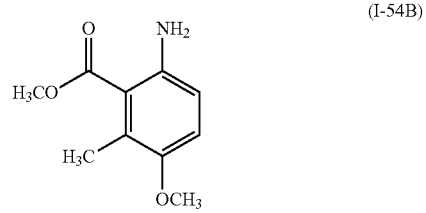

(I-54B)

This intermediate was prepared in a manner analogous to Intermediate I-47A. Thus, Intermediate I-54A was reacted to afford Intermediate I-54B (100% yield) as a brown oil. LC-MS: Method H, RT=0.60 min, MS (ESI) m/z: 196.0 (M+H)⁺. ¹H NMR (400 MHz, CHLOROFORM-d) δ 6.82 (d, J=8.8 Hz, 1H), 6.53 (dd, J=8.7, 0.6 Hz, 1H), 4.38 (br. s., 2H), 3.90 (s, 3H), 3.75 (s, 3H), 2.26 (s, 3H).

Intermediate I-54C: methyl 2-amino-6-methoxy-5-methylbenzo[d]thiazole-4-carboxylate

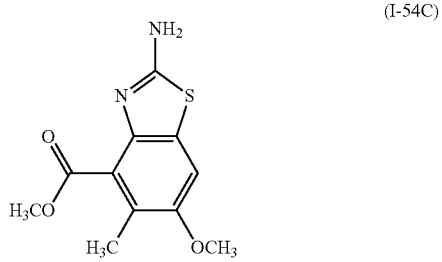 [SMILES: COC(=O)c1c(C)c(OC)cc2sc(N)nc12]

(I-54C)

This intermediate was prepared in a manner analogous to Intermediate I-47B. Thus, Intermediate I-54B was reacted to afford Intermediate I-54C (60% yield) as a brown solid. LC-MS: Method H, RT=0.66 min, MS (ESI) m/z: 252.9

(M+H)⁺. ¹H NMR (400 MHz, METHANOL-d₄) δ 7.29 (s, 1H), 3.93 (s, 3H), 3.84 (s, 3H), 2.17 (s, 3H).

Intermediate I-54D: methyl 2-bromo-6-methoxy-5-methylbenzo[d]thiazole-4-carboxylate

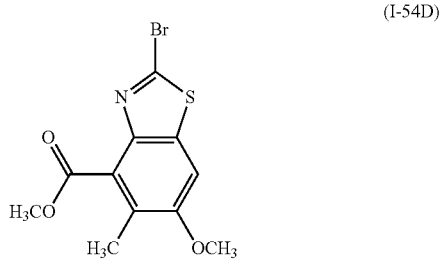 [SMILES: COC(=O)c1c(C)c(OC)cc2sc(Br)nc12]

(I-54D)

This intermediate was prepared in a manner analogous to Intermediate I-47. Thus, Intermediate I-54C was reacted to afford Intermediate I-54D (70% yield) as a bright yellow solid. LC-MS: Method H, RT=0.99 min, MS (ESI) m/z: 315.7, 317.7 (M+H)⁺. ¹H NMR (400 MHz, CHLOROFORM-d) δ 7.22 (s, 1H), 4.03 (s, 3H), 3.90 (s, 3H), 2.29 (s, 3H).

Intermediate I-54

A solution of Intermediate I-54D (390 mg, 1.234 mmol) in toluene (8223 µl) and THF (4112 µl) was cooled to −78° C. under an atmosphere of N₂. To this cooled solution was added DIBAL-H (1 M in toluene) (2714 µl, 2.71 mmol) dropwise. After 5 min of stirring, the mixture was allowed to thaw to room temperature. Once at room temperature, the reaction was quenched with 12 mL 1 M HCl and stirred vigorously for 30 min to fully cleave any aluminate complexes. The mixture was then diluted with EtOAc, extracted, washed with brine, dried over MgSO₄, filtered and concentrated. The crude product was purified by ISCO (80 g, 0-100% EtOAc/Hexanes, 33 min. SM peak recovered at 20%, Product peak) to afford Intermediate I-54 (213 mg, 0.739 mmol, 59.9% yield) as white powder. LC-MS: Method H, RT=0.88 min, MS (ESI) m/z: 287.8, 289.8 (M+H)⁺. ¹H NMR (400 MHz, CHLOROFORM-d) δ 7.14 (s, 1H), 5.14 (d, J=6.4 Hz, 2H), 3.89 (s, 3H), 3.42 (t, J=6.3 Hz, 1H), 2.33 (s, 3H).

Intermediate I-55

2-bromo-6-methoxy-5-methylbenzo[d]thiazole-4-carbaldehyde

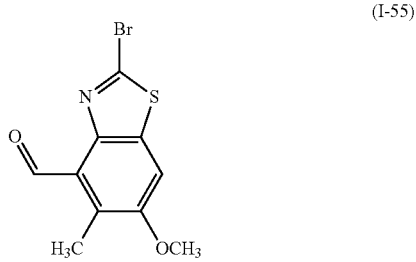

(I-55)

To a solution of Intermediate I-54 (80 mg, 0.278 mmol) in DCE (2776 µl) was added manganese(IV) oxide (241 mg, 2.78 mmol). The solution was heated to reflux under an atmosphere of N₂ for 4 h. The reaction mixture was allowed to cool to room temperature before being filtered over celite and washed with EtOAc. The filtrate was concentrate in vacuo to afford Intermediate I-55 (61 mg, 0.213 mmol, 77% yield) as an off-white solid. This material was taken on without further purification. LC-MS: Method H, RT=1.04 min, MS (ESI) m/z: 285.7, 287.7 (M+H)⁺. ¹H NMR (400 MHz, CHLOROFORM-d) δ 11.12 (s, 1H), 7.42 (s, 1H), 3.93 (s, 3H), 2.63 (s, 3H).

Intermediate I-56

2-bromo-4-chloro-6-methoxy-5-methylbenzo[d]thiazole

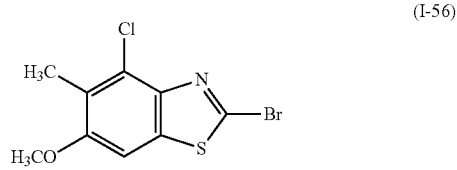

(I-56)

Intermediate I-56A: 2-chloro-4-methoxy-3-methyl-1-nitrobenzene

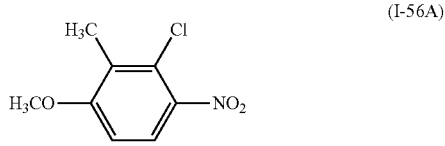

(I-56A)

This intermediate was prepared in a manner analogous to Intermediate I-43A. Thus 1-chloro-3-methoxy-2-methylbenzene was reacted to afford Intermediate I-56A (52% yield) as the major regioisomer isolated from the reaction mixture (second eluting on silica gel). LC-MS: Method H, RT=0.85 min, MS (ESI) m/z: None Observed (M+H)⁺. ¹H NMR (400 MHz, CHLOROFORM-d) δ 7.80 (d, J=8.8 Hz, 1H), 6.80 (d, J=9.0 Hz, 1H), 3.93 (s, 3H), 2.34 (s, 3H).

Intermediate I-56B: 2-chloro-4-methoxy-3-methylaniline

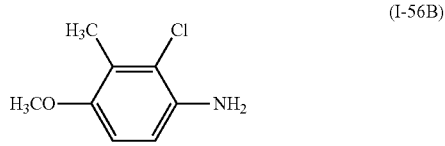

(I-56B)

This intermediate was prepared in a manner analogous to Intermediate I-43B. Thus, Intermediate I-56A was reacted to afford Intermediate I-56B (42% yield) as a purple oil. LC-MS: Method H, RT=0.91 min, MS (ESI) m/z: 172.1, 174.1 (M+H)+. 1H NMR (400 MHz, CHLOROFORM-d) δ 6.68-6.58 (m, 2H), 3.77 (br. s., 2H), 3.76 (s, 3H), 2.27 (s, 3H).

Intermediate I-56C: 4-chloro-6-methoxy-5-methyl-benzo[d]thiazol-2-amine

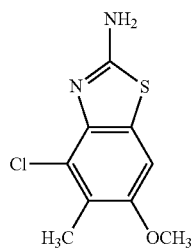
(I-56C)

This intermediate was prepared in a manner analogous to Intermediate I-43C. Thus, Intermediate I-56B was reacted to afford Intermediate I-56C (81% yield) as a purple oil. LC-MS: Method H, RT=1.06 min, MS (ESI) m/z: 229.1, 231.1 (M+H)+. 1H NMR (400 MHz, DMSO-d6) δ 7.50 (s, 1H), 7.34 (s, 1H), 3.79 (s, 3H), 2.24 (s, 3H).

Intermediate I-56

This intermediate was prepared in a manner analogous to Intermediate I-43. Thus, Intermediate I-56C was reacted to afford Intermediate I-56 (51% yield) as a beige solid. LC-MS: Method H, RT=1.36 min, MS (ESI) m/z: 292.0, 294.0, 295.9 (M+H)+. 1H NMR (400 MHz, DMSO-d6) δ 7.50 (s, 1H), 7.34 (s, 1H), 3.79 (s, 3H), 2.24 (s, 3H).

Intermediate I-57 methyl 2-((2-bromo-4-chloro-5-fluorobenzo[d]thiazol-6-yl)oxy)acetate

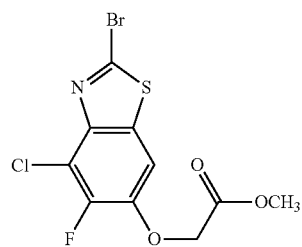
(I-57)

Intermediate I-57A: 2-amino-4-chloro-5-fluorobenzo[d]thiazol-6-ol, hydrobromide

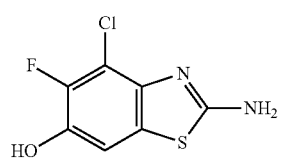
(I-57A)

A suspension of Intermediate I-43C (100 mg, 0.430 mmol) in acetic acid (2 mL) and HBr (48% in water) (2 mL, 17.68 mmol) was heated to 125° C. After 3 h of heating, the mixture was cooled to room temperature and concentrated in vacuo to give Intermediate I-57A (116 mg, 0.387 mmol, 90% yield) as its HBr salt. LC-MS: Method H, RT=0.80 min, MS (ESI) m/z: 218.9, 220.8 (M+H)+. 1H NMR (400 MHz, METHANOL-d4) δ 7.36 (d, J=7.3 Hz, 1H).

Intermediate I-57B: methyl 2-((2-amino-4-chloro-5-fluorobenzo[d]thiazol-6-yl)oxy) acetate

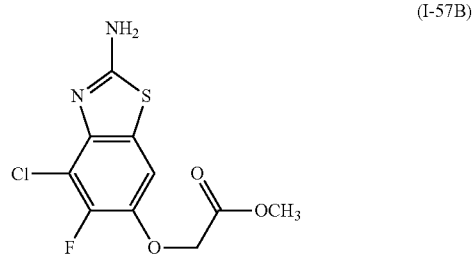 [SMILES: COC(=O)COc1cc2sc(N)nc2c(Cl)c1F]
(I-57B)

To a solution of Intermediate I-57A (129 mg, 0.431 mmol) in DMF (5 mL) was added Cs2CO3 (631 mg, 1.938 mmol) followed by methyl bromoacetate (0.044 mL, 0.474 mmol). The reaction mixture was stirred vigorously for 30 min before being quenched with AcOH (0.247 mL, 4.31 mmol) followed by 5 mL deionized water. This solution was diluted with DCM and extracted 3×. The organic phase was concentrated and the crude residue was purified by ISCO (40 g, 0-10% DCM/MeOH, 17 min. Product at 5%) to afford Intermediate I-57B (135 mg, 0.418 mmol, 97% yield). LC-MS: Method H, RT=0.90 min, MS (ESI) m/z: 290.8, 292.7 (M+H)+. 1H NMR (400 MHz, METHANOL-d4) δ 7.33 (d, J=7.5 Hz, 1H), 4.77 (s, 2H), 3.78 (s, 3H).

Intermediate I-57C: methyl 2-((2-amino-4-chloro-5-fluorobenzo[d]thiazol-6-yl)oxy) acetate

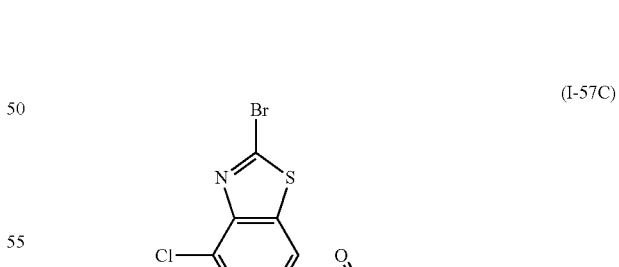
(I-57C)

This intermediate was prepared in a manner analogous to Intermediate I-43. Thus, Intermediate I-57B was reacted to afford Intermediate I-57C (57% yield) as a beige solid. LC-MS: Method H, RT=1.00 min, MS (ESI) m/z: 353.9, 356.0, 357.9 (M+H)+. 1H NMR (400 MHz, CHLOROFORM-d) δ 7.25 (d, 1H-buried under CDCl3), 4.77 (s, 2H), 3.82 (s, 3H).

Intermediate I-58

2-((4-chloro-5-fluoro-2-(2-methoxy-7-methylquinoxalin-5-yl)benzo[d]thiazol-6-yl)oxy)acetic acid

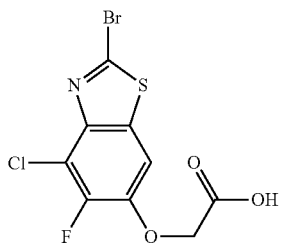

(I-58)

To a mixture of Intermediate I-57 (88 mg, 0.248 mmol) in THF (3.5 mL) and water (1.0 mL) was added LiOH monohydrate (51.2 mg, 1.241 mmol). After 30 min the reaction mixture was diluted with EtOAc and washed with 1 M HCl. The organic phase was concentrated to afford Intermediate I-58 (88 mg, 0.258 mmol, 104% yield) as a beige solid. This material was taken forward without further purification. LC-MS: Method H, RT=0.88 min, MS (ESI) m/z: 340.0, 342.0, 344.0 (M+H)$^+$. $^1$H NMR (400 MHz, METHANOL-d$_4$) δ 7.62 (d, J=7.5 Hz, 1H), 4.83 (s, 2H).

Intermediate I-59

2-((2-bromo-4-chloro-5-fluorobenzo[d]thiazol-6-yl)oxy)ethanol


(I-59)

This intermediate was prepared in a manner analogous to Intermediate I-51. Intermediate I-57 was reacted to afford Intermediate I-59 (77% yield) as a yellow solid. LC-MS: Method H, RT=1.07 min, MS (ESI) m/z: 326.0, 327.9, 329.9 (M+H)$^+$. $^1$H NMR (400 MHz, METHANOL-d$_4$) δ 7.68 (d, J=7.3 Hz, 1H), 4.25-4.15 (m, 2H), 4.00-3.89 (m, 2H).

Intermediate I-60

2-bromo-5-fluorobenzo[d]thiazol-6-ol

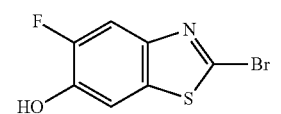

(I-60)

A solution of Intermediate 277B (502 mg, 1.915 mmol) in CH$_2$Cl$_2$ (10 mL) was cooled to 0° C. To this mixture was slowly added BBr$_3$ (1 M in Hexanes) (5.75 mL, 5.75 mmol) over 5 minutes. After this addition, the reaction mixture was allowed to thaw to room temperature overnight. After 16 h, the reaction mixture was poured into ice. The mixture was diluted with 30 mL of EtOAc and stirred vigorously for 10 min. The organic phase was separated and the aqueous phase was washed 2× with EtOAc. The combined organic phase was dried over MgSO$_4$, filtered and concentrated in vacuo to afford Intermediate I-60 (468 mg, 1.887 mmol, 98% yield) as an off-white solid. LC-MS: Method H, RT=0.85 min, MS (ESI) m/z: 248.0, 249.9 (M+H)$^+$. $^1$H NMR (400 MHz, DMSO-d$_6$) δ 10.48 (s, 1H), 7.84 (d, J=11.4 Hz, 1H), 7.62 (d, J=8.4 Hz, 1H). $^{19}$F NMR (376 MHz, DMSO-d$_6$) δ −135.05 (s, 1F).

Intermediate I-61

2-((2-bromo-5-fluorobenzo[d]thiazol-6-yl)oxy)ethanol

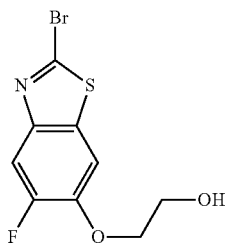

(I-61)

Intermediate I-61A: methyl 2-((2-bromo-5-fluorobenzo[d]thiazol-6-yl)oxy)acetate

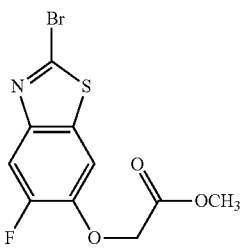

(I-61A)

This intermediate was prepared in a manner analogous to Intermediate I-52. Thus, Intermediate I-60 was reacted to afford Intermediate I-61A (96% yield) as a white solid. LC-MS: Method H, RT=0.92 min, MS (ESI) m/z: 320.1, 322.1 (M+H)$^+$. $^1$H NMR (400 MHz, CHLOROFORM-d) δ 7.72 (d, J=11.0 Hz, 1H), 7.33 (d, J=7.7 Hz, 1H), 4.76 (s, 2H), 3.82 (s, 3H).

Intermediate I-61

This intermediate was prepared in a manner analogous to Intermediate I-51. Thus, Intermediate I-61A was reacted to afford Intermediate I-61 (98% yield) as an off-white, amorphous solid. LC-MS: Method H, RT=0.81 min, MS (ESI)

m/z: 292.1, 294.1 (M+H)+. 1H NMR (400 MHz, CHLOROFORM-d) δ 7.70 (d, J=11.0 Hz, 1H), 7.36 (d, J=7.7 Hz, 1H), 4.22-4.17 (m, 2H), 4.04 (dt, J=6.2, 4.5 Hz, 2H), 2.10-2.04 (m, 1H).

Intermediate I-62

2-((2-bromo-5-fluoro-4-methylbenzo[d]thiazol-6-yl)oxy)ethyl (6-fluoropyridin-3-yl) carbamate

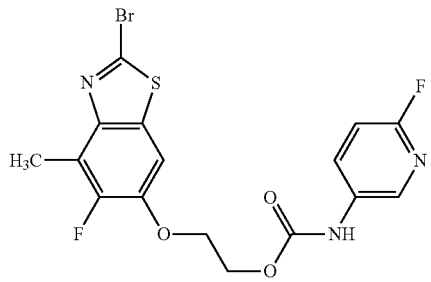

(I-62)

To a solution of Intermediate I-53 (22 mg, 0.072 mmol) in THF (1.5 mL) was added DIEA (0.065 mL, 0.370 mmol) followed by a solution of phosgene (15% by wt. in toluene) (0.253 mL, 0.359 mmol) at room temperature. After 2 h of stirring, the crude chlorofomate intermediate was concentrated to remove excess phosgene and retaken in THF (1 mL). Another batch of DIEA (0.065 mL, 0.370 mmol) was added followed by 6-fluoropyridin-3-amine (24.90 mg, 0.222 mmol). After 15 min, the crude reaction mixture was concentrated and purified by ISCO (12 g, 0-70% EtOAc/Hexanes, 16 min. Product at 35%) to afford Intermediate I-62 (28 mg, 0.070 mmol, 95% yield) as an off-white solid. LC-MS: Method H, RT=1.21 min, MS (ESI) m/z: 443.1, 445.2 (M+H)+. 1H NMR (400 MHz, THF) δ 9.10 (br. s., 1H), 8.07 (br. s., 1H), 8.02-7.91 (m, 1H), 7.40 (t, J=7.7 Hz, 1H), 6.80 (dd, 3.5 Hz, 1H), 4.46-4.38 (m, 2H), 4.26-4.18 (m, 2H), 2.44 (dd, 2.5 Hz, 3H).

Intermediate I-63

2-((2-bromo-4-chloro-5-fluorobenzo[d]thiazol-6-yl)oxy)ethyl (6-fluoropyridin-3-yl) carbamate

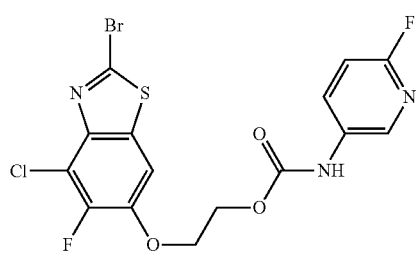

(I-63)

This intermediate was prepared in a manner analogous to Intermediate I-62. Thus, Intermediate I-59 was reacted to afford Intermediate I-63 (90% yield) as an off-white solid. LC-MS: Method H, RT=1.18 min, MS (ESI) m/z: 464.0, 466.0, 468.0 (M+H)+. 1H NMR (400 MHz, THF) δ 9.22 (br. s., 1H), 8.19 (br. s., 1H), 8.12-8.02 (m, 1H), 7.70 (d, J=7.3 Hz, 1H), 6.92 (dd, 3.5 Hz, 1H), 4.56-4.53 (m, 2H), 4.41-4.37 (m, 2H).

Intermediate I-64

5-fluoro-2-(2-methoxy-7-methylquinoxalin-5-yl)benzo[d]thiazol-6-ol

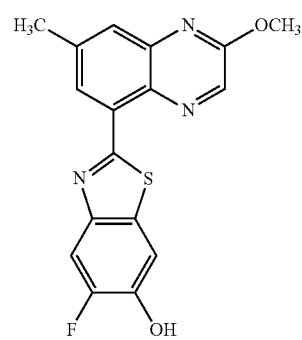

(I-64)

Intermediate I-64A 2-(2-(difluoromethoxy)-7-methylquinoxalin-5-yl)-5-fluorobenzo[d]thiazol-6-ol

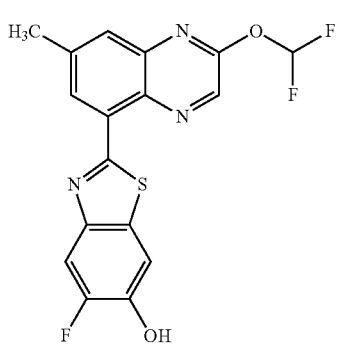

(I-64A)

A microwave vial was charged with Intermediate I-1 (106 mg, 0.314 mmol), Intermediate I-60 (65 mg, 0.262 mmol) and [1,1′-bis(diphenylphosphino)ferrocene] dichloropalladium (II) complex with dichloromethane (1:1) (17.12 mg, 0.021 mmol). A solvent mixture of toluene (1638 μl), EtOH (546 μl) and 2.0 M Na2CO3 (197 μl, 0.393 mmol) was then added, and the resulting solution was sparged with argon for 10 min before being sealed and then heated in the microwave at 130° C. for 30 min. The crude reaction mixture was diluted with EtOAc and filtered over celite before being concentrated and purified by ISCO (24 g, 0-100% EtOAc/Hexanes, 16 min. Product at 35%.) to afford Intermediate I-64A (95 mg, 0.252 mmol, 96% yield) as a dark yellow solid. LC-MS: Method H, RT=1.06 min, MS (ESI) m/z: 378.2 (M+H)+. 1H NMR (400 MHz, CHLOROFORM-d) δ 8.76 (d, J=2.0 Hz, 1H), 8.69 (s, 1H), 7.84 (d, J=10.8 Hz, 1H), 7.80 (s, 1H), 7.66 (t, J=71.8 Hz, 1H), 7.55 (d, J=8.4 Hz, 1H), 5.30 (d, J=5.1 Hz, 1H), 2.68 (s, 3H).

Intermediate I-64

To a solution of Intermediate I-64A (20 mg, 0.053 mmol) in THF (1 mL) was added a 0.5 M NaOMe solution in MeOH (0.530 mL, 0.265 mmol). After 1 h, the reaction mixture was diluted with EtOAc and quenched with 1.0 N HCl. The organic phase was extracted, dried over MgSO$_4$, filtered and concentrated in vacuo to afford Intermediate I-64 (18 mg, 0.053 mmol, 99% yield) as a yellow solid. This material was taken on without further purification. LC-MS: Method H, RT=1.08 min, MS (ESI) m/z: 342.2 (M+H)$^+$. $^1$H NMR (400 MHz, THF) δ 8.95 (br. s., 1H), 8.70 (d, J=1.3 Hz, 1H), 8.54 (s, 1H), 7.80-7.67 (m, 2H), 7.46 (d, J=8.6 Hz, 1H), 4.10 (s, 3H), 2.63 (s, 3H).

Intermediate I-65

4-chloro-5-fluoro-2-(2-methoxy-7-methylquinoxalin-5-yl)benzo[d]thiazol-6-ol

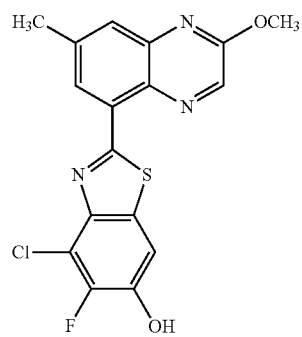

(I-65)

Intermediate I-65A 4-chloro-2-(2-(difluoromethoxy)-7-methylquinoxalin-5-yl)-5-fluorobenzo[d]thiazol-6-ol

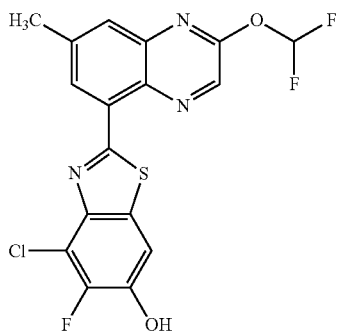

(I-65A)

This intermediate was prepared in a manner analogous to Intermediate I-64A. Thus, Intermediate I-1 was reacted with Intermediate I-44 to afford Intermediate I-65A (81% yield) as a bright yellow solid. LC-MS: Method H, RT=1.15 min, MS (ESI) m/z: 412.0, 414.1 (M+H)$^+$. $^1$H NMR (400 MHz, DMSO-d$_6$) δ 8.94-9.01 (m, 1H), 8.69-8.78 (m, 1H), 7.72-8.10 (m, 2H), 7.64-7.70 (m, 1H), 2.70 (s, 3H).

Intermediate I-65

This intermediate was prepared in a manner analogous to Intermediate I-64. Thus, Intermediate I-65A was reacted to afford Intermediate I-65 (100% yield) as a dark orange solid. LC-MS: Method H, RT=1.36 min, MS (ESI) m/z: 376.0, 378.1 (M+H)$^+$. $^1$H NMR (400 MHz, DMSO-d$_6$) δ 8.94-9.01 (m, 1H), 8.69-8.78 (m, 1H), 7.72-8.10 (m, 2H), 7.64-7.70 (m, 1H), 2.70 (s, 3H).

Intermediate I-66

2-((5-fluoro-2-(2-methoxy-7-methylquinoxalin-5-yl)benzo[d]thiazol-6-yl)oxy)ethanol

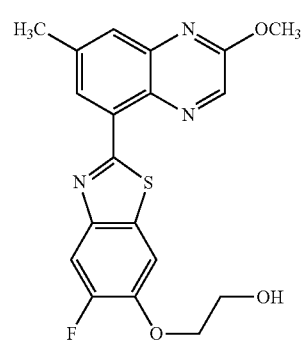

(I-66)

Intermediate I-66A 2-((2-(2-(difluoromethoxy)-7-methylquinoxalin-5-yl)-5-fluorobenzo[d]thiazol-6-yl)oxy)ethanol

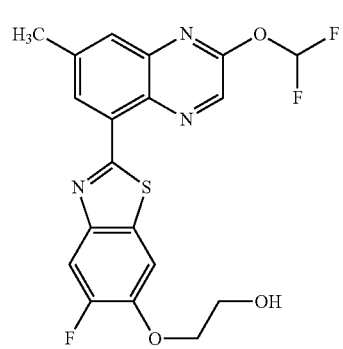

(I-66A)

This intermediate was prepared in a manner analogous to Intermediate I-64A. Thus, Intermediate I-1 was reacted with Intermediate I-61 to afford Intermediate I-66A (75% yield) as a yellow solid. LC-MS: Method H, RT=1.07 min, MS (ESI) m/z: 422.2 (M+H)$^+$. $^1$H NMR (400 MHz, CHLOROFORM-d) δ 8.76 (d, J=1.8 Hz, 1H), 8.69 (s, 1H), 7.84 (d, J=11.4 Hz, 1H), 7.80 (dd, J=1.8, 0.9 Hz, 1H), 7.66 (t, J=71.8 Hz, 1H), 7.50 (d, J=7.7 Hz, 1H), 4.29-4.23 (m, 2H), 4.10-4.03 (m, 2H), 2.69 (s, 3H), 2.14 (t, J=6.4 Hz, 1H).

Intermediate I-66

This intermediate was prepared in a manner analogous to Intermediate I-64. Intermediate I-66A was reacted to afford Intermediate I-66 (43% yield) as a dark orange solid. LC-MS: Method H, RT=1.08 min, MS (ESI) m/z: 386.1 (M+H)+. ¹H NMR (400 MHz, THF) δ 8.71 (d, J=1.8 Hz, 1H), 8.55 (s, 1H), 7.77-7.73 (m, 2H), 7.71 (d, J=8.1 Hz, 1H), 4.22-4.16 (m, 2H), 4.10 (s, 3H), 3.93-3.85 (m, 2H), 2.64 (s, 3H).

Intermediate I-67

(R)-1-((5-fluoro-2-(2-methoxy-7-methylquinoxalin-5-yl)benzo[d]thiazol-6-yl)oxy)propan-2-ol

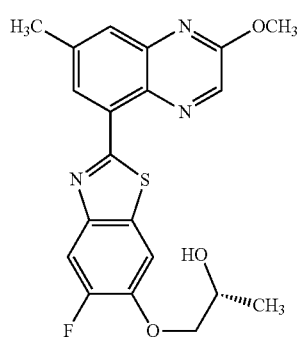

(I-67)

To a suspension of Intermediate I-64 (30 mg, 0.088 mmol) neat in (R)-2-methyloxirane (1 mL, 14.29 mmol) was added tetrabutylammonium bromide (56.7 mg, 0.176 mmol) followed by K₂CO₃ (36.4 mg, 0.264 mmol). The reaction vessel was sealed, heated to 65° C. and stirred vigorously for 4 h. The reaction mixture was then cooled to room temperature and quenched with a few drops of AcOH. The resulting mixture was concentrated and purified by ISCO (12 g, 0-70% EtOAc/Hexanes, 16 min. Product at 38%) to afford Intermediate I-67 (27 mg, 0.068 mmol, 77% yield) as a bright yellow solid. LC-MS: Method H, RT=1.16 min, MS (ESI) m/z: 400.1 (M+H)+. ¹H NMR (400 MHz, THF) δ 8.70 (d, J=1.8 Hz, 1H), 8.56 (s, 1H), 7.78-7.73 (m, 2H), 7.71 (d, J=8.1 Hz, 1H), 4.10 (s, 3H), 4.16-4.07 (m, 1H), 4.07-4.00 (m, 1H), 4.00-3.92 (m, 1H), 2.64 (s, 3H), 2.55 (br. s, 1H), 1.26 (d, J=6.4 Hz, 3H).

Intermediate I-68

(S)-1-((5-fluoro-2-(2-methoxy-7-methylquinoxalin-5-yl)benzo[d]thiazol-6-yl)oxy)propan-2-ol

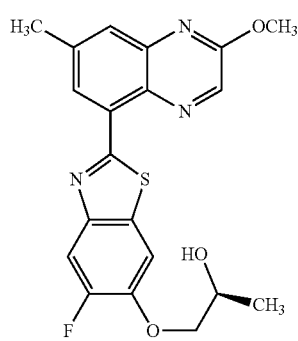

(I-68)

This intermediate was prepared in a manner analogous to Intermediate I-67. Intermediate I-64 was reacted with (S)-2-methyloxirane to afford Intermediate I-68 (73% yield) as a bright yellow solid. LC-MS: Method H, RT=1.07 min, MS (ESI) m/z: 422.2 (M+H)+. ¹H NMR (400 MHz, CHLOROFORM-d) δ 8.76 (d, J=1.8 Hz, 1H), 8.69 (s, 1H), 7.84 (d, J=11.4 Hz, 1H), 7.80 (dd, J=1.8, 0.9 Hz, 1H), 7.66 (t, J=71.8 Hz, 1H), 7.50 (d, J=7.7 Hz, 1H), 4.29-4.23 (m, 2H), 4.10-4.03 (m, 2H), 3.79 (s, 3H), 2.14 (t, J=6.4 Hz, 1H).

Intermediate I-69

(R)-1-((4-chloro-5-fluoro-2-(2-methoxy-7-methylquinoxalin-5-yl)benzo[d]thiazol-6-yl)oxy)propan-2-ol

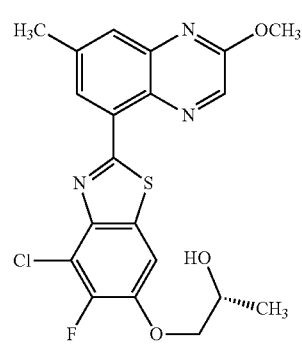

(I-69)

This intermediate was prepared in a manner analogous to Intermediate I-67. Thus, Intermediate I-65 was reacted with (R)-2-methyloxirane to afford Intermediate I-69 (74% yield) as a bright yellow solid. LC-MS: Method H, RT=1.20 min, MS (ESI) m/z: 434.1 (M+H)+. ¹H NMR (400 MHz, DMSO-d₆) δ 8.78 (s, 1H), 8.62 (d, J=2.0 Hz, 1H), 8.01 (d, J=7.7 Hz, 1H), 7.88 (s, 1H), 5.00 (d, J=4.2 Hz, 1H), 4.10 (s, 3H), 4.10-4.00 (m, 3H), 2.67 (s, 3H), 1.22 (d, J=5.9 Hz, 3H).

Intermediate I-70

(S)-2-((5-fluoro-2-(2-methoxy-7-methylquinoxalin-5-yl)benzo[d]thiazol-6-yl)oxy)propan-1-ol

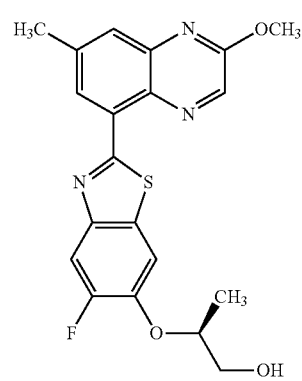

(I-70)

Intermediate I-70A (S)-6-((1-((tert-butyldimethylsilyl)oxy)propan-2-yl)oxy)-5-fluoro-2-(2-methoxy-7-methyl quinoxalin-5-yl)benzo[d]thiazole

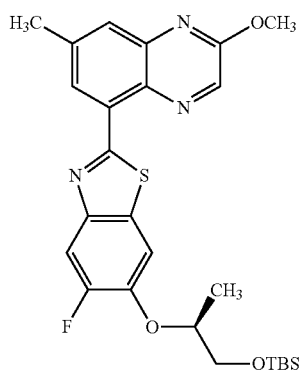

(I-70A)

A solution of Intermediate I-64 (30 mg, 0.088 mmol) and triphenylphosphine (92 mg, 0.352 mmol) in THF (1.0 mL) was heated to 65° C. To this mixture was added a solution of (R)-1-((tert-butyldimethylsilyl)oxy)propan-2-ol (84 mg, 0.439 mmol) mixed with DIAD (0.085 mL, 0.439 mmol) in THF (1.0 mL) dropwise over 1 h via syringe pump. At the end of addition, the crude mixture was allowed to cool to room temperature then was concentrated and purified by ISCO (12 g, 0-10% EtOAc/Hexanes, 16 min. Product at 7%) to afford Intermediate I-70A (31 mg, 0.060 mmol, 68.7% yield) as a yellow oil. LC-MS: Method H, RT=1.56 min, MS (ESI) m/z: 514.3 (M+H)$^+$. $^1$H NMR (400 MHz, CHLOROFORM-d) δ 8.61 (d, J=2.0 Hz, 1H), 8.55 (s, 1H), 7.80 (d, J=11.2 Hz, 1H), 7.75 (d, J=0.7 Hz, 1H), 7.56 (d, J=7.7 Hz, 1H), 4.52 (sxt, J=5.9 Hz, 1H), 4.13 (s, 3H), 3.89 (dd, J=10.7, 5.8 Hz, 1H), 3.75 (dd, J=10.7, 5.0 Hz, 1H), 2.65 (s, 3H), 1.39 (d, J=6.2 Hz, 3H), 0.89 (s, 9H), 0.09 (s, 3H), 0.06 (s, 3H).

Intermediate I-70

To a solution of Intermediate I-70A (20 mg, 0.039 mmol) in THF (0.8 mL) and methanol (0.2 mL) was added several drops of concentrated HCl (12.1M, 0.016 mL, 0.195 mmol). After stirring for 5 min at room temperature, the reaction mixture was quenched with saturated NaHCO$_3$. This solution was then diluted with DCM and extracted. The organic phase was dried over MgSO$_4$, filtered and concentrated in vacuo to afford Intermediate I-70 (15 mg, 0.039 mmol, 100% yield), which was taken on without further purification. LC-MS(ESI) m/z: 400.2 (M+H)$^+$. RT=1.11 min (1 min gradient, ACN/water/TFA). $^1$H NMR (500 MHz, DMSO-d$_6$) δ 8.72 (s, 1H), 8.57 (d, J=1.7 Hz, 1H), 7.99 (d, J=8.3 Hz, 1H), 7.94 (d, J=11.6 Hz, 1H), 7.82 (d, J=0.8 Hz, 1H), 4.96 (t, J=5.6 Hz, 1H), 4.63-4.55 (m, 1H), 4.08 (s, 3H), 3.68-3.61 (m, 1H), 3.61-3.55 (m, 1H), 2.63 (s, 3H), 2.51 (dt, J=3.5, 1.7 Hz, 8H), 1.30 (d, J=6.1 Hz, 3H).

Intermediate I-71

(R)-2-((5-fluoro-2-(2-methoxy-7-methylquinoxalin-5-yl)benzo[d]thiazol-6-yl)oxy)propan-1-ol

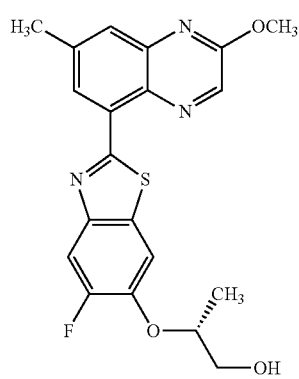

(I-71)

Intermediate I-71A (R)-6-((1-((tert-butyldimethylsilyl)oxy)propan-2-yl)oxy)-5-fluoro-2-(2-methoxy-7-methyl quinoxalin-5-yl)benzo[d]thiazole This intermediate was prepared in a manner analogous to Intermediate I-70A. Intermediate I-64 was reacted with (S)-1-((tert-butyldimethylsilyl)oxy)propan-2-ol to afford Intermediate I-71A (61% yield) as a yellow oil. LC-MS: Method H, RT=1.56 min, MS (ESI) m/z: 514.3 (M+H)$^+$. $^1$H NMR (400 MHz, CHLOROFORM-d) δ 8.61 (d, J=2.0 Hz, 1H), 8.55 (s, 1H), 7.80 (d, J=11.2 Hz, 1H), 7.75 (d, J=0.7 Hz, 1H), 7.56 (d, J=7.7 Hz, 1H), 4.52 (sxt, J=5.9 Hz, 1H), 4.13 (s, 3H), 3.89 (dd, J=10.7, 5.8 Hz, 1H), 3.75 (dd, J=10.7, 5.0 Hz, 1H), 2.65 (s, 3H), 1.39 (d, J=6.2 Hz, 3H), 0.89 (s, 9H), 0.09 (s, 3H), 0.06 (s, 3H).

Intermediate I-71

This intermediate was prepared in a manner analogous to Intermediate I-70. Thus, Intermediate I-71A was reacted to afford Intermediate I-71 (94% yield). LC-MS(ESI) m/z: 400.2 (M+H)$^+$. RT=1.11 min (1 min gradient, ACN/water/TFA). $^1$H NMR (500 MHz, DMSO-d$_6$) δ 8.72 (s, 1H), 8.57

(d, J=1.7 Hz, 1H), 7.99 (d, J=8.3 Hz, 1H), 7.94 (d, J=11.6 Hz, 1H), 7.82 (d, J=0.8 Hz, 1H), 4.96 (t, J=5.6 Hz, 1H), 4.63-4.55 (m, 1H), 4.08 (s, 3H), 3.68-3.61 (m, 1H), 3.61-3.55 (m, 1H), 2.63 (s, 3H), 2.51 (dt, J=3.5, 1.7 Hz, 8H), 1.30 (d, J=6.1 Hz, 3H).

Intermediate I-72

(2R,3S)-3-((5-fluoro-2-(2-methoxy-7-methylquinoxalin-5-yl)benzo[d]thiazol-6-yl)oxy)butan-2-ol

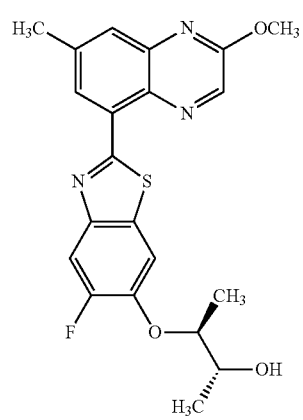

Intermediate I-72A: (2R,3S)-3-((2-bromo-5-fluorobenzo[d]thiazol-6-yl)oxy)butan-2-ol

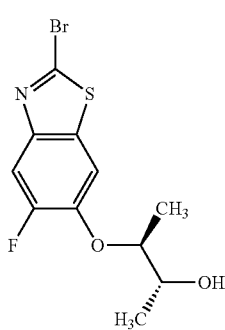

To a solution of Intermediate I-60 (1.0 g, 4.03 mmol) in THF (26.9 ml) was added (4R,5R)-4,5-dimethyl-1,3,2-dioxathiolane 2,2-dioxide (0.736 g, 4.84 mmol) followed by potassium carbonate (0.669 g, 4.84 mmol). The reaction mixture was sealed and heated to 65° C. for 16 h. The reaction mixture was cooled to 0° C. and concentrated sulfuric acid (0.430 ml, 8.06 mmol) was added (caution: significant bubbling observed) followed by water (0.218 ml, 12.09 mmol). The reaction mixture was allowed to thaw to room temperature for 10 min before being quenched with 1.5 M K$_2$HPO$_4$, extracted with EtOAc, washed with brine, dried over MgSO$_4$, filtered over celite and concentrated down to afford Intermediate I-72A (1.29 g, 4.03 mmol) as beige solid. The crude material was taken on without further purification. LC-MS: Method H, RT=0.96 min, MS (ESI) m/z: 319.9, 321.9 (M+H)$^+$. $^1$H NMR (400 MHz, DMSO-d$_6$) δ 7.96 (d, J=8.1 Hz, 1H), 7.89 (d, J=11.4 Hz, 1H), 4.86 (d, J=5.3 Hz, 1H), 4.35-4.25 (m, 1H), 3.84-3.73 (m, 1H), 1.26 (d, J=6.4 Hz, 3H), 1.15 (d, J=6.4 Hz, 3H). $^{19}$F NMR (376 MHz, DMSO-d$_6$) δ −132.96.

Intermediate I-72B (2R,3S)-3-((2-(2-(difluoromethoxy)-7-methylquinoxalin-5-yl)-5-fluorobenzo[d]thiazol-6-yl)oxy)butan-2-ol

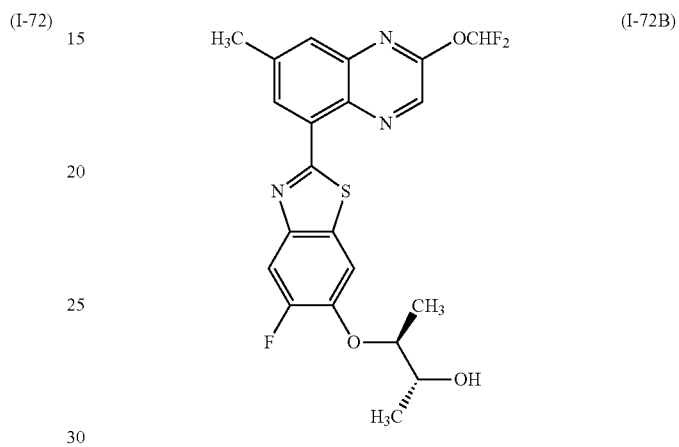

To a 250 mL round bottom flask charged with Intermediate I-1 (787 mg, 2.342 mmol) and Intermediate I-72A (750 mg, 2.342 mmol) was added toluene (8784 μl) and EtOH (2928 μl) followed by a 2M solution of sodium carbonate (1757 μl 3.51 mmol). The mixture was stirred vigorously and sparged with argon for 10 minutes. [1,1'-Bis(diphenylphosphino)ferrocene]dichloropalladium (II) complex with dichloromethane (1:1) (191 mg, 0.234 mmol) was then added and the mixture was sparged with argon for an additional 5 min. The reaction mixture was heated to reflux under an atmosphere of argon. After 2 h of heating, the reaction mixture was diluted with EtOAc and filtered through celite before being concentrated, dry loaded onto celite and purified by ISCO (120 g, 0-100% DCM/EtOAc, Product at 25%) to afford Intermediate I-72B (470 mg, 1.046 mmol, 44.6% yield) as a bright yellow solid. LC-MS: Method H, RT=1.19 min, MS (ESI) m/z: 450.9 (M+H)$^+$. $^1$H NMR (400 MHz, CHLOROFORM-d) δ 8.76 (d, J=2.0 Hz, 1H), 8.69 (s, 1H), 7.83 (d, J=11.4 Hz, 1H), 7.80 (dd, J=1.9, 1.0 Hz, 1H), 7.66 (t, J=71.8 Hz, 1H), 7.54 (d, J=7.7 Hz, 1H), 4.40 (qd, J=6.3, 3.3 Hz, 1H), 4.18-4.06 (m, 1H), 2.69 (s, 3H), 2.14 (d, J=4.8 Hz, 1H), 1.38 (d, J=6.4 Hz, 3H), 1.30 (d, J=6.6 Hz, 3H). $^{19}$F NMR (376 MHz, CHLOROFORM-d) δ −89.77, −132.68.

Intermediate I-72

Intermediate I-72B (470 mg, 1.046 mmol) was co-evaporated with toluene to removed adventitious water. The crude solid was retake in THF (20.900 mL) and a 0.5 M solution sodium methoxide in MeOH (20.91 mL, 10.46 mmol) was added causing the solution to turn dark red. The reaction mixture was quenched after 30 min with 1.0 N HCl (21 mL) causing the solution to return to a bright yellow color. The reaction mixture was diluted with 150 mL EtOAc, extracted and washed with brine. The organic phase was dried over

Intermediate I-73

(2R,3S)-3-((2-(2-(difluoromethoxy)-7-methylquinoxalin-5-yl)-5-fluorobenzo[d]thiazol-6-yl)oxy)butan-2-yl (2-methylpyrimidin-5-yl)carbamate

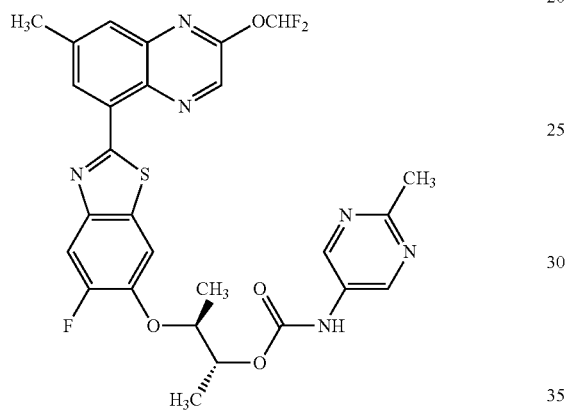

(I-73)

Intermediate I-74

Methyl 5-(((((2R,3S)-3-((5-fluoro-2-(2-methoxy-7-methylquinoxalin-5-yl)benzo[d]thiazol-6-yl)oxy)butan-2-yl)oxy)carbonyl)amino)picolinate

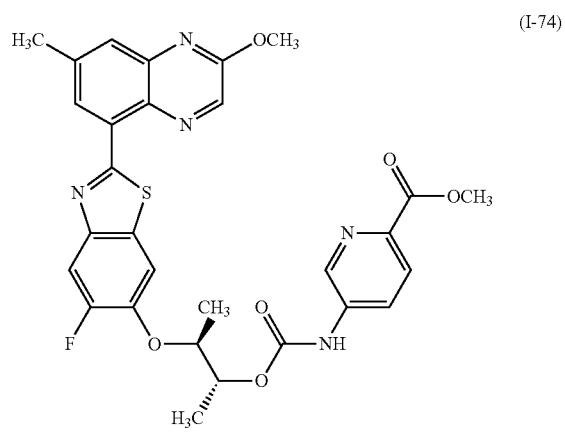 [SMILES: COC(=O)c1ccc(NC(=O)O[C@H](C)[C@H](C)Oc2cc3sc(-c4cc(C)cc5nc(OC)cnc45)nc3cc2F)cn1]

(I-74)

To a solution of Intermediate I-72B (170 mg, 0.332 mmol) in THF (6.5 mL) was added a 15% phosgene solution in toluene (2354 μl, 3.34 mmol). The resulting slurry was allowed to stir at room temperature for 16 h before being concentrated down to the crude chloroformate intermediate. This crude residue was retaken in THF (6.5 mL) and 2-methylpyrimidin-5-amine (39.9 mg, 0.365 mmol) followed by pyridine (0.134 mL, 1.660 mmol) were added to the reaction mixture. After 10 min, the reaction mixture was concentrated and purified by ISCO (40 g, 0-100% EtOAc/Hex, Product at 85%) to afford Intermediate I-73 (182 mg, 0.311 mmol, 94% yield) as a yellow solid. LC-MS: Method H, RT=1.17 min, MS (ESI) m/z: 585.2 (M+H)+. $^1$H NMR (400 MHz, CHLOROFORM-d) δ 8.76 (d, J=2.0 Hz, 1H), 8.72 (br. s., 2H), 8.69 (s, 1H), 7.86-7.78 (m, 2H), 7.66 (t, J=71.8 Hz, 1H), 7.53 (d, J=7.9 Hz, 1H), 6.49 (br. s., 1H), 5.21-5.12 (m, 1H), 4.63 (dd, J=6.4, 3.3 Hz, 1H), 2.69 (s, 3H), 2.68 (s, 3H), 1.47 (d, J=6.6 Hz, 3H), 1.44 (d, J=6.4 Hz, 3H). $^{19}$F NMR (376 MHz, CHLOROFORM-d) δ −89.78 (s, 3F), −132.17 (s, 1F)

To a solution of Intermediate I-72 (30 mg, 0.073 mmol) in THF (1.5 mL) was added a 15% phosgene solution in toluene (512 μl, 0.726 mmol). The resulting slurry was allowed to stir at room temperature for 16 h before being concentrated down to the crude chloroformate intermediate. This crude residue was retaken in THF (1.5 mL) and methyl 5-aminopicolinate (13.25 mg, 0.087 mmol) was added followed by pyridine (0.059 mL, 0.726 mmol). After 10 min, the reaction mixture was concentrated and loaded directly onto an ISCO column (12 g, 0-60%, DCM/EtOAc, Product at 28%) to afford Intermediate I-74 (40 mg, 0.068 mmol, 93% yield) as a light yellow solid. LC-MS: Method H, RT=1.26 min, MS (ESI) m/z: 592.1 (M+H)+. $^1$H NMR (400 MHz, CHLOROFORM-d) δ 8.64-8.59 (m, 1H), 8.57 (d, J=1.8 Hz, 1H), 8.55 (d, J=2.6 Hz, 1H), 8.51 (s, 1H), 8.18-8.11 (m, 1H), 8.10-8.06 (m, 1H), 7.79 (d, J=11.2 Hz, 1H), 7.74 (d, J=0.9 Hz, 1H), 7.50 (d, J=7.7 Hz, 1H), 7.18 (s, 1H), 5.16 (qd, J=6.5, 3.1 Hz, 1H), 4.65-4.57 (m, 1H), 4.12 (s, 3H), 3.95 (s, 3H), 2.63 (s, 3H), 1.46 (d, J=6.6 Hz, 3H), 1.42 (d, J=6.4 Hz, 3H).

Intermediate I-75

Methyl 5-(((((2R,3S)-3-((5-fluoro-2-(2-methoxy-7-methylquinoxalin-5-yl)benzo[d]thiazol-6-yl)oxy)butan-2-yl)oxy)carbonyl)amino)picolinate

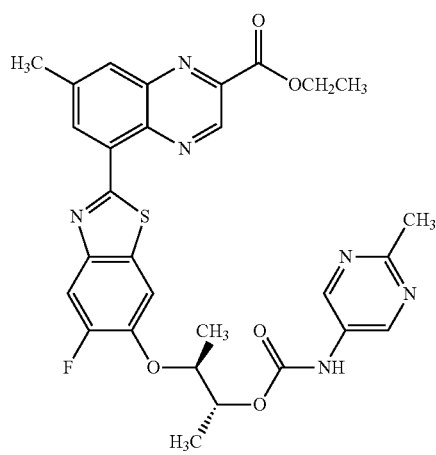

(I-75)

Intermediate I-75A: (ethyl 5-(5-fluoro-6-(((2S,3R)-3-hydroxybutan-2-yl)oxy) benzo[d]thiazol-2-yl)-7-methylquinoxaline-2-carboxylate

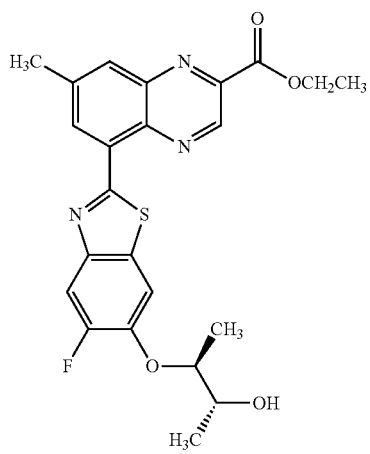

(I-75A)

This intermediate was prepared in a manner analogous to Intermediate I-70A. Thus, Intermediate I-72A was reacted with Intermediate I-15 and purified by ISCO (0-100% EtOAc/Hex, Product at 60%) to afford Intermediate I-75A (79% yield) as a dark yellow solid. LC-MS: Method H, RT=1.17 min, MS (ESI) m/z: 456.1 (M+H)⁺. $^1$H NMR (400 MHz, CHLOROFORM-d) δ 9.62 (s, 1H), 8.99 (d, J=2.0 Hz, 1H), 8.20 (s, 1H), 7.84 (d, J=11.2 Hz, 1H), 7.56 (d, J=7.9 Hz, 1H), 4.67-4.58 (m, 2H), 4.47-4.36 (m, 1H), 4.17-4.08 (m, 1H), 2.74 (s, 3H), 2.14 (d, J=4.6 Hz, 1H), 1.56-1.53 (m, 3H), 1.38 (d, J=6.4 Hz, 3H), 1.30 (d, J=6.6 Hz, 3H).

Intermediate I-75

This intermediate was prepared in a manner analogous to Intermediate I-73. Thus Intermediate I-75A was reacted to afford Intermediate I-75 (50% yield) as a yellow solid. LC-MS: Method H, RT=1.08 min, MS (ESI) m/z: 591.8 (M+H)⁺. $^1$H NMR (500 MHz, DMSO-d$_6$) δ 9.97 (br. s., 1H), 9.46 (s, 1H), 8.85 (br. s., 1H), 8.73 (br. s., 2H), 8.18 (br. s., 1H), 8.05 (d, J=7.6 Hz, 1H), 7.94 (d, J=11.6 Hz, 1H), 5.12 (br. s., 1H), 4.84 (br. s., 1H), 4.49 (d, J=6.7 Hz, 2H), 2.69 (br. s., 3H), 2.56 (s, 3H), 1.56-1.34 (m, 9H).

Intermediate I-76

(2R,3S)-3-((2-bromo-5-fluorobenzo[d]thiazol-6-yl)oxy)butan-2-ol

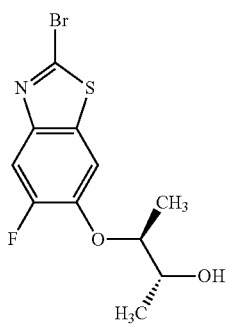

(I-76)

Intermediate I-76A: (4R,5R)-4,5-dimethyl-1,3,2-dioxathiolane 2-oxide

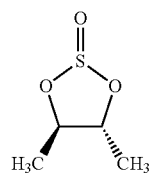

(I-76A)

To a solution of thionyl chloride (5.37 ml, 73.5 mmol) in DCM (235 ml) was added (2R,3R)-butane-2,3iol (5.37 ml, 58.8 mmol). The reaction mixture immediately became opaque and bubbled. Over time, the solution became clear once again. After 30 min, the reaction mixture was carefully concentrated [Note: This product is volatile]. Intermediate I-76A (8.01 g, 58.8 mmol, 100% yield) was isolated as a light tan oil mixed with some residual DCM. The product was taken on to the subsequent sulfur oxidation without purification. $^1$H NMR (400 MHz, CDCl$_3$) δ 4.68 (dq, J=9.0, 6.2 Hz, 1H), 4.11 (dq, J=8.9, 6.3 Hz, 1H), 1.57 (d, J=6.2 Hz, 3H), 1.48 (d, J=6.2 Hz, 3H).

Intermediate I-76B:
(4R,5R)-4,5-dimethyl-1,3,2-dioxathiolane 2,2-dioxide

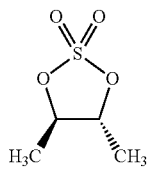

(I-76B)

A solution of Intermediate I-76A in CCl₄ (73.4 ml), acetonitrile (73.4 ml) and H₂O (147 ml) was cooled to 0° C. Sodium periodate (18.85 g, 88 mmol) was added to the mixture followed by ruthenium(III) chloride (0.244 g, 1.175 mmol). The resulting mixture was stirred at 0° C. for 1 h, over which time it took on a reddish-brown hue. The reaction mixture was then diluted with 200 mL DI H₂O and extracted with 500 mL EtOAc. The organic phase was washed with brine, dried over MgSO₄, and filtered over a pad of silica gel. This organic solution was concentrated down to a black oil and retaken in DCM. This DCM solution was filtered over a second pad of silica gel which removed more of the ruthenium impurities. The resulting solution was concentrated to afford Intermediate I-76B (7.6 g, 49.9 mmol, 85% yield) as a brown tinged oil. [Note: This material can be stored as a frozen solid at −20° C.]. ¹H NMR (400 MHz, CHLOROFORM-d) δ 4.75-4.63 (m, 2H), 1.58-1.52 (m, 6H).

Intermediate I-76

To a solution of Intermediate I-60 (2.65 g, 10.68 mmol) in THF (42.7 ml) was added Intermediate I-76B followed by potassium carbonate (2.215 g, 16.02 mmol). A reflux condenser was attached, and the reaction mixture was heated to reflux (65° C.) overnight. After 15 h of refluxing, the solution was cooled to 0° C. Cleavage of the resulting sulfate intermediate was affected by the addition of concentrated sulfuric acid (1.708 ml, 32.0 mmol) followed by water (0.962 ml, 53.4 mmol) [Note: vigorous bubbling observed]. The reaction mixture was allowed to thaw to room temperature and stirred vigorously for 1 h. The reaction mixture was then quenched with 100 mL of a 1.5 M K₂HPO₄ solution, extracted with 300 mL EtOAc, washed with brine, dried over MgSO₄, filtered and concentrated to afford a beige solid. This solid was dry loaded onto Celite and purified by ISCO (220 g, 0-50% EtOAc/DCM, 36 min. Product at 15%) to afford Intermediate I-76 (3.1 g, 9.68 mmol, 91% yield, 99% ee) as an off-white solid. LC-MS: Method H, RT=0.78 min, MS (ESI) m/z: 399.9, 401.9 (M+H)⁺—Sulfate Intermediate. LC-MS: Method H, RT=0.93 min, MS (ESI) m/z: 320.0, 322.0 (M+H)⁺—Desired Alcohol. Chiral HPLC: Chiral AD 10 micron 4.6×250 mm, Solvent A (heptane), Solvent B (1:1 MeOH/EtOH). Isocratic gradient at 16% B, product retention time 6.0 min. ¹H NMR (400 MHz, DMSO-d₆) δ 7.98 (d, J=8.4 Hz, 1H), 7.91 (d, J=11.7 Hz, 1H), 4.90 (d, J=5.3 Hz, 1H), 4.35-4.26 (m, 1H), 3.85-3.73 (m, 1H), 1.27 (d, J=6.2 Hz, 3H), 1.16 (d, J=6.4 Hz, 3H). ¹⁹F NMR (376 MHz, DMSO-d₆) δ −132.96 (s, 1F).

Intermediate I-77

(2R,3S)-3-((2-bromo-4-chloro-5-fluorobenzo[d]thiazol-6-yl)oxy)butan-2-ol

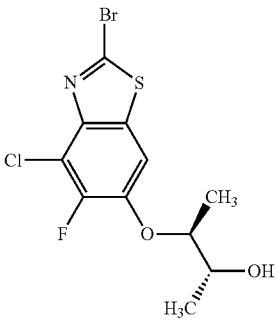

(I-77)

This intermediate was prepared in a manner analogous to Intermediate I-76. Thus, Intermediate I-44 was reacted with Intermediate I-76A to afford Intermediate I-77 (58% yield) as an off-white solid. LC-MS: Method H, RT=1.00 min, MS (ESI) m/z: 353.9, 355.9, 358.0 (M+H)⁺. ¹H NMR (400 MHz, CDCl₃) δ 7.34 (d, J=7.0 Hz, 1H), 4.38 (dd, J=6.3, 3.4 Hz, 1H), 4.16-4.03 (m, 1H), 2.01 (d, J=4.8 Hz, 1H), 1.37 (d, J=6.4 Hz, 3H), 1.31 (d, J=6.6 Hz, 3H).

Intermediate I-78

(2R,3S)-3-((2-(2-(difluoromethoxy)-7-methylquinoxalin-5-yl)-5-fluorobenzo[d]thiazol-6-yl)oxy)butan-2-ol

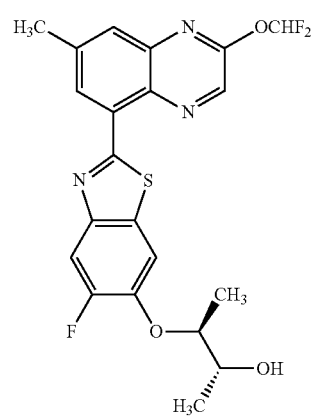

(I-78)

To a flask charged with Intermediate I-1 (254 mg, 0.756 mmol) and Intermediate I-76 (220 mg, 0.687 mmol) was added toluene (2577 µl) and EtOH (859 µl) followed by a 2 M aqueous solution of sodium carbonate (515 µl, 1.031 mmol). The mixture was stirred vigorously and sparged with argon for 10 minutes. [1,1'-Bis(diphenylphosphino) ferrocene]dichloropalladium (II) complex with dichloromethane (1:1) (56.1 mg, 0.069 mmol) was then added and the mixture was sparged with argon for an additional 5 min. The flask was then heated to reflux under an atmosphere of argon. After 2 h of refluxing, the reaction mixture was diluted with EtOAc, filtered over Celite and concentrated. The crude residue was dry-loaded onto Celite and purified by ISCO (80 g, 0-70% DCM/EtOAc, product at 20%) to afford Intermediate I-78 (260 mg, 0.578 mmol, 84% yield) as a bright yellow foaming solid. LC-MS: Method H, RT=1.14 min, MS (ESI) m/z: 450.1 (M+H)⁺. ¹H NMR (400 MHz, CDCl₃) δ 8.76 (d, J=2.0 Hz, 1H), 8.69 (s, 1H), 7.83 (d, J=11.4 Hz, 1H), 7.80 (dd, J=1.9, 1.0 Hz, 1H), 7.66 (t, J=71.8 Hz, 1H), 7.54 (d, J=7.7 Hz, 1H), 4.40 (qd, J=6.3, 3.3 Hz, 1H), 4.18-4.06 (m, 1H), 2.69 (s, 3H), 2.14 (d, J=4.8 Hz, 1H), 1.38 (d, J=6.4 Hz, 3H), 1.30 (d, J=6.6 Hz, 3H). ¹⁹F NMR (376 MHz, CDCl₃) δ −89.77 (s, 2F), −132.68 (s,1F).

Intermediate I-79

(2R,3S)-3-((5-fluoro-2-(2-methoxy-7-methylquinoxalin-5-yl)benzo[d]thiazol-6-yl)oxy) butan-2-ol

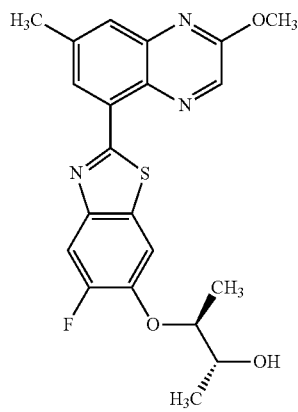

(I-79)

The starting material Intermediate I-78 (0.91 g, 2.025 mmol) was co-evaporated with toluene to remove any adventitious water. The dried solid was retaken in THF (40.5 ml) and a 0.5 M solution of sodium methoxide in methanol (40.5 ml, 20.25 mmol) was added. After 1 h of stirring, the reaction mixture was quenched with 1.0 N HCl (41 mL). The mixture was then diluted with 500 mL EtOAc and washed with 150 mL Brine. The organic phase was dried over MgSO₄, filtered, and concentrated onto Celite for dry-load purification by ISCO (80 g, 0-100% DCM/EtOAc) to give Intermediate I-79 (0.73 g, 1.766 mmol, 87% yield) as a yellow foamy solid. LC-MS: Method H, RT=1.25 min, MS (ESI) m/z: 414.1 (M+H)⁺. ¹H NMR (400 MHz, DMSO-d₆) δ 8.74 (s, 1H), 8.58 (d, J=1.8 Hz, 1H), 7.99 (d, J=8.4 Hz, 1H), 7.95 (d, J=11.7 Hz, 1H), 7.83 (d, J=0.7 Hz, 1H), 4.91 (d, J=5.1 Hz, 1H), 4.38 (quin, J=5.8 Hz, 1H), 4.09 (s, 3H), 3.87-3.77 (m, 1H), 2.63 (s, 3H), 1.31 (d, J=6.2 Hz, 3H), 1.19 (d, J=6.2 Hz, 3H)

Intermediate I-80

(2R,3S)-3-((2-(2-ethoxy-7-methylquinoxalin-5-yl)-5-fluorobenzo[d]thiazol-6-yl)oxy) butan-2-ol

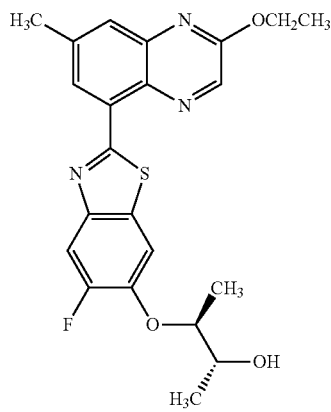

(I-80)

To a solution of Intermediate I-78 (370 mg, 0.823 mmol) in THF (6174 μl) was added ethanol (2058 μl) followed by the portion-wise addition of sodium hydride (329 mg, 8.23 mmol). After 10 minutes of stirring, the reaction mixture was quenched with saturated NH₄Cl (~2 mL), and the resulting mixture was concentrated onto Celite for dry loading and purified by ISCO (80 g, 0-70% DCM/EtOAc, 33 min, product at 20%) to afford Intermediate I-80 (320 mg, 0.749 mmol, 91% yield) as a bright yellow solid. LC-MS: Method H, RT=1.48 min, MS (ESI) m/z: 428.1 (M+H)⁺. ¹H NMR (400 MHz, DMSO-d₆) δ 8.72 (s, 1H), 8.58 (d, J=2.0 Hz, 1H), 7.99 (d, J=8.1 Hz, 1H), 7.95 (d, J=11.7 Hz, 1H), 7.81 (s, 1H), 4.91 (d, J=5.3 Hz, 1H), 4.54 (q, J=7.0 Hz, 2H), 4.37 (quin, J=5.8 Hz, 1H), 3.87-3.78 (m, 1H), 2.63 (s, 3H), 1.45 (t, J=7.0 Hz, 3H), 1.31 (d, J=6.2 Hz, 3H), 1.19 (d, J=6.4 Hz, 3H).

Intermediate I-81

(2R,3S)-3-((4-chloro-5-fluoro-2-(2-methoxy-7-methylquinoxalin-5-yl) benzo[d]thiazol-6-yl)oxy)butan-2-ol

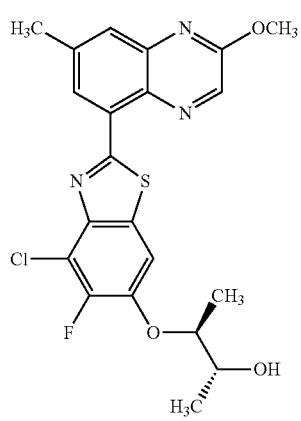

(I-81)

This intermediate was prepared in a manner analogous to Intermediate I-78. Thus, Intermediate I-9 was reacted with Intermediate I-77 to afford Intermediate I-81 (25% yield) as a yellow solid. LC-MS: Method H, RT=1.29 min, MS (ESI) m/z: 447.9, 449.8 (M+H)⁺. ¹H NMR (400 MHz, CDCl₃) δ 8.71 (d, J=1.8 Hz, 1H), 8.50 (s, 1H), 7.75 (d, J=0.9 Hz, 1H), 7.41 (d, J=7.0 Hz, 1H), 4.43-4.33 (m, 1H), 4.15-4.06 (m, 4H), 2.65 (s, 3H), 2.15 (d, J=4.2 Hz, 1H), 1.37 (d, J=6.4 Hz, 3H), 1.30 (d, J=6.6 Hz, 3H).

Intermediate I-82

(R)-methyl 5-((((1-((5-fluoro-2-(2-methoxy-7-methylquinoxalin-5-yl) benzo[d]thiazol-6-yl)oxy)propan-2-yl)oxy)carbonyl)amino)picolinate

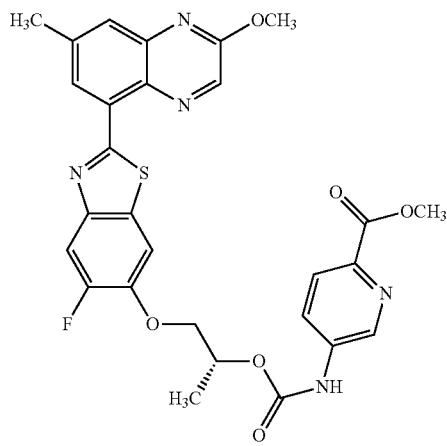

(I-82)

To a solution Intermediate I-67 (194 mg, 0.486 mmol) in THF (9714 μl) was added a 15% phosgene solution in toluene (3425 μl, 4.86 mmol). The resulting slurry was allowed to stir overnight before being concentrated down to a crude yellow residue. This intermediate chloroformate was retaken in THF (9714 μl) and added dropwise to a premixed solution of methyl 5-aminopicolinate (217 mg, 1.429 mmol) and pyridine (385 μl, 4.76 mmol) in THF (9526 μl). After 10 min of stirring, the reaction mixture was concentrated and loaded directly onto an ISCO cartridge for purification (40 g, 0-100% EtOAc/DCM, product at 35%) to afford Intermediate I-82 (250 mg, 0.433 mmol, 91% yield) as a yellow solid. LC-MS: Method H, RT=1.24 min, MS (ESI) m/z: 578.2 (M+H)⁺. ¹H NMR (400 MHz, DMSO-d₆) δ 10.40 (s, 1H), 8.78-8.72 (m, 2H), 8.58 (d, J=1.8 Hz, 1H), 8.12-7.94 (m, 4H), 7.84 (s, 1H), 5.30 (td, J=6.2, 3.2 Hz, 1H), 4.47-4.36 (m, 1H), 4.35-4.24 (m, 1H), 4.09 (s, 3H), 3.84 (s, 3H), 2.64 (s, 3H), 1.45 (d, J=6.6 Hz, 3H).

Intermediate I-83

(R)-methyl 4-((((1-((5-fluoro-2-(2-methoxy-7-methylquinoxalin-5-yl)benzo[d]thiazol-6-yl)oxy)propan-2-yl)oxy)carbonyl)amino)picolinate

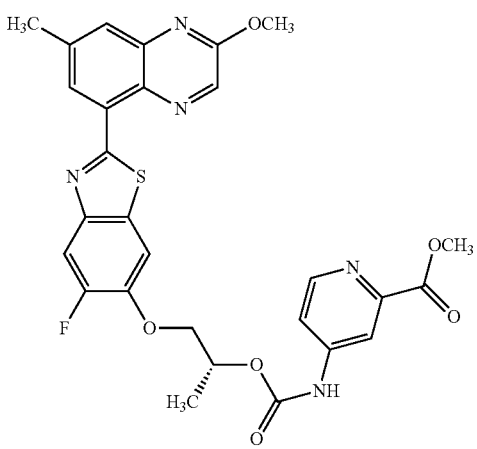

(I-83)

This intermediate was prepared in a manner analogous to Intermediate I-82. Thus, Intermediate I-67 was reacted with methyl 4-aminopicolinate to afford Intermediate I-83 (59% yield) as a yellow solid. LC-MS: Method H, RT=1.33 min, MS (ESI) m/z: 578.2 (M+H)⁺. ¹H NMR (400 MHz, CDCl₃) δ 8.63-8.57 (m, 2H), 8.53 (s, 1H), 8.02 (d, J=2.0 Hz, 1H), 7.81 (d, J=11.4 Hz, 1H), 7.78-7.70 (m, 2H), 7.47 (d, J=7.7 Hz, 1H), 7.14 (s, 1H), 5.43-5.33 (m, 1H), 4.30-4.17 (m, 2H), 4.12 (s, 3H), 3.98 (s, 3H), 2.64 (s, 3H), 1.51 (d, J=6.4 Hz, 3H).

Intermediate I-84

(R)-methyl 5-((((1-((5-fluoro-2-(2-methoxy-7-methylquinoxalin-5-yl)benzo[d]thiazol-6-yl)oxy)propan-2-yl)oxy)carbonyl)amino)pyrimidine-2-carboxylate

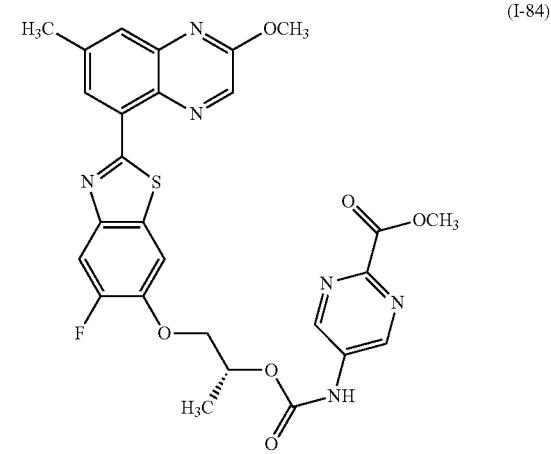 [SMILES: COC(=O)c1ccc(NC(=O)O[C@H](C)COc2cc3sc(-c4cc(C)cc5nc(OC)cnc45)nc3cc2F)cn1]

(I-84)

This intermediate was prepared in a manner analogous to Intermediate I-82. Thus, Intermediate I-67 was reacted with Intermediate I-107 to afford Intermediate I-84 (66% yield) as a yellow solid. LC-MS: Method H, RT=1.14 min, MS (ESI) m/z: 579.0 (M+H)⁺. ¹H NMR (400 MHz, DMSO-d₆) δ 10.57 (br. s., 1H), 9.01 (s, 2H), 8.76 (s, 1H), 8.59 (d, J=2.0

Hz, 1H), 8.03 (d, J=8.4 Hz, 1H), 7.99 (d, J=11.7 Hz, 1H), 7.85 (dd, J=1.9, 1.0 Hz, 1H), 5.31 (td, J=6.2, 3.2 Hz, 1H), 4.45-4.38 (m, 1H), 4.35-4.27 (m, 1H), 4.10 (s, 3H), 3.87 (s, 3H), 2.64 (s, 3H), 1.45 (d, J=6.6 Hz, 3H)

Intermediate I-85

Methyl 4-(((((2R,3S)-3-((5-fluoro-2-(2-methoxy-7-methylquinoxalin-5-yl) benzo[d]thiazol-6-yl)oxy) butan-2-yl)oxy)carbonyl)amino)picolinate (I-85)

This intermediate was prepared in a manner analogous to Intermediate I-82. Thus, Intermediate I-79 was reacted with methyl 4-aminopicolinate to afford Intermediate I-85 (46% yield) as a yellow solid. LC-MS: Method H, RT=1.10 min, MS (ESI) m/z: 592.1 (M+H)+. 1H NMR (400 MHz, CDCl3) δ 8.58 (d, J=1.8 Hz, 1H), 8.56 (d, J=5.5 Hz, 1H), 8.51 (s, 1H), 7.99 (d, J=2.0 Hz, 1H), 7.80 (d, J=11.4 Hz, 1H), 7.75 (d, J=0.9 Hz, 1H), 7.69 (dd, J=5.6, 2.1 Hz, 1H), 7.51 (d, J=7.7 Hz, 1H), 7.12 (s, 1H), 5.16 (qd, J=6.5, 3.0 Hz, 1H), 4.67-4.56 (m, 1H), 4.12 (s, 3H), 3.95 (s, 3H), 2.64 (s, 3H), 1.47 (d, J=6.6 Hz, 3H), 1.43 (d, J=6.4 Hz, 3H).

Intermediate I-86

Methyl 5-(((((2R,3S)-3-((5-fluoro-2-(2-methoxy-7-methylquinoxalin-5-yl) benzo[d]thiazol-6-yl)oxy) butan-2-yl)oxy)carbonyl)amino)pyrimidine-2-carboxylate (I-86)

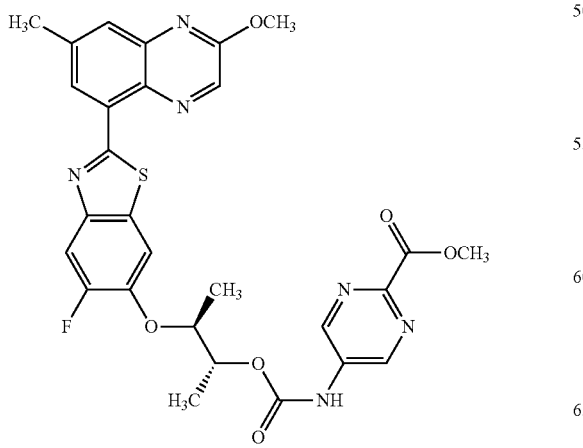

This intermediate was prepared in a manner analogous to Intermediate I-82. Thus, Intermediate I-67 was reacted with Intermediate I-107 to afford Intermediate I-86 (66% yield) as a yellow solid. LC-MS: Method H, RT=1.19 min, MS (ESI) m/z: 593.1 (M+H)+. 1H NMR (400 MHz, CDCl3) δ 9.03 (s, 2H), 8.62 (br. s., 1H), 8.57 (d, J=1.8 Hz, 1H), 8.51 (s, 1H), 7.78 (d, J=11.4 Hz, 1H), 7.76-7.73 (m, 1H), 7.49 (d, J=7.7 Hz, 1H), 5.17 (qd, J=6.5, 3.1 Hz, 1H), 4.62 (qd, J=6.4, 2.9 Hz, 1H), 4.12 (s, 3H), 4.02 (s, 3H), 2.64 (s, 3H), 1.47 (d, J=6.6 Hz, 3H), 1.41 (d, J=6.4 Hz, 3H).

Intermediate I-87

(R)-methyl 4-(((((1-((4-chloro-5-fluoro-2-(2-methoxy-7-methylquinoxalin-5-yl)benzo[d]thiazol-6-yl)oxy)propan-2-yl)oxy)carbonyl)amino)picolinate (I-87)

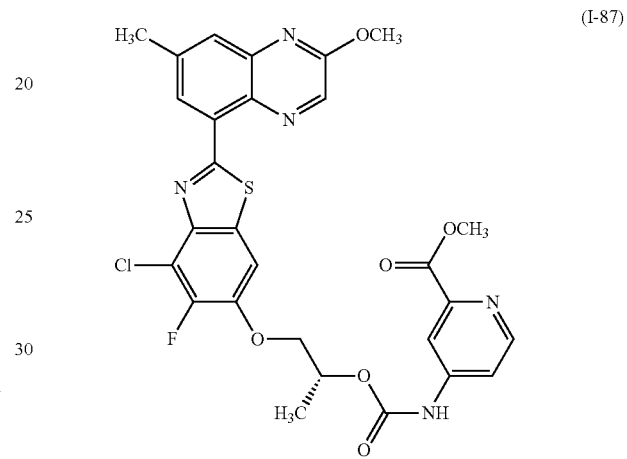

This intermediate was prepared in a manner analogous to Intermediate I-82. Thus, Intermediate I-69 was reacted with methyl 4-aminopicolinate to afford Intermediate I-87 (58% yield) as a yellow solid. LC-MS: Method H, RT=1.12 min, MS (ESI) m/z: 612.2, 614.1 (M+H)+. 1H NMR (400 MHz, CDCl3) δ 8.76 (d, J=1.5 Hz, 1H), 8.64 (d, J=5.5 Hz, 1H), 8.55 (s, 1H), 8.04 (d, J=2.0 Hz, 1H), 7.80 (dd, J=2.0, 0.9 Hz, 1H), 7.75 (dd, 2.2 Hz, 1H), 7.43 (d, J=7.3 Hz, 1H), 7.01 (s, 1H), 5.46-5.35 (m, 1H), 4.35-4.20 (m, 2H), 4.16 (s, 3H), 4.02 (s, 3H), 2.69 (s, 3H), 1.55 (d, J=6.6 Hz, 3H).

Intermediate I-88

(2R,3S)-3-((2-chloro-5-fluorobenzo[d]thiazol-6-yl)oxy)butan-2-yl (2-(2-hydroxyethoxy)pyrimidin-5-yl) carbamate (I-88)

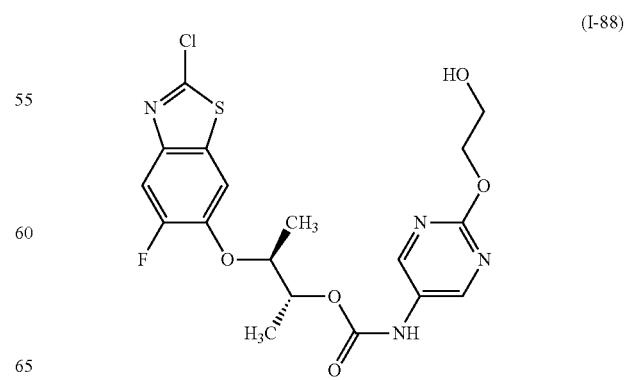

Intermediate I-88A: (2R,3S)-3-((2-chloro-5-fluorobenzo[d]thiazol-6-yl)oxy)butan-2-yl carbonochloridate

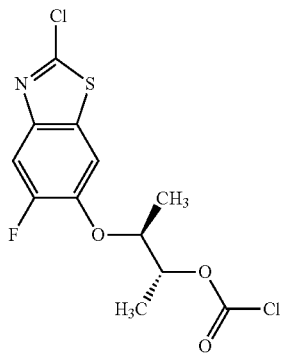

(I-88A)

To a solution Intermediate I-72A (780 mg, 2.436 mmol) in THF (24.4 mL, 0.1 M) was added 15% phosgene in toluene (8.59 mL, 12.18 mmol). The resulting slurry was allowed to stir at room temperature. After t=5 h, the resulting mixture was concentrated to remove the excess phosgene and afford Intermediate I-88A (824 mg, 2.436 mmol) as a yellow solid. Quantitative yield was assumed, and this material was telescope into the next reaction without purification. LC-MS: Method H, RT=1.14 min, MS (ESI) m/z: 338.0, 339.9 (M+H)$^+$.

Intermediate I-88B: (2R,3S)-3-((2-chloro-5-fluorobenzo[d]thiazol-6-yl)oxy)butan-2-yl (2-(2-((tert-butyldimethylsilyl)oxy)ethoxy)pyrimidin-5-yl)carbamate

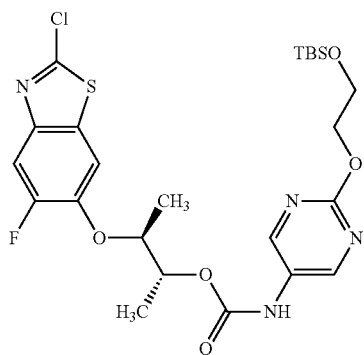

(I-88B)

To a solution of Intermediate I-97 (784 mg, 2.91 mmol) and pyridine (1.961 mL, 24.25 mmol) in DCM (48.5 mL, 0.05 M) was added crude Intermediate I-88A (820 mg, 2.425 mmol) dropwise from its own solution of DCM (48.500 mL). [Note: Addition funnel was used to add solution over 10 min]. Following the reagent addition, the reaction mixture was concentrated down to remove excess pyridine and purified by ISCO (0-100% EtOAc/Hex, product at 35%) to afford Intermediate I-88B (1.10 g, 1.63 mmol, 67% yield) as an off-white solid. LC-MS: Method H, RT=1.29 min, MS (ESI) m/z: 571.0, 573.0 (M+H)$^+$. $^1$H NMR (400 MHz, CDCl$_3$) δ 8.67-8.49 (m, 2H), 7.66 (dd, J=11.0, 3.5 Hz, 1H), 7.41-7.34 (m, 1H), 5.12 (dd, J=6.5, 3.0 Hz, 1H), 4.55 (dd, J=6.3, 3.0 Hz, 1H), 4.45-4.39 (m, 2H), 3.98 (t, J=5.5 Hz, 2H), 1.34 (d, J=6.4 Hz, 3H), 1.28 (d, J=6.6 Hz, 3H), 0.92-0.86 (m, 9H), 0.08 (s, 6H).

Intermediate I-88

To a solution of Intermediate I-88B (95 mg, 0.166 mmol) in THF (3327 µl) was added 1 M HCl (832 µl, 0.832 mmol) at room temperature (12 pm). After 1.5 h, the reaction was quenched with saturated NaHCO$_3$, diluted with EtOAc, extracted, dried over MgSO$_4$, filtered, concentrated, and purified by ISCO (12 g, 0-100% EtOAc/DCM, product at 85%) to afford Intermediate I-88 (50 mg, 0.109 mmol, 65.8% yield) as a colorless oil. LC-MS: Method H, RT=0.91 min, MS (ESI) m/z: 456.9, 458.9 (M+H)$^+$. $^1$H NMR (400 MHz, CDCl$_3$) δ 8.61 (br. s., 2H), 7.64 (d, J=11.0 Hz, 1H), 7.43-7.32 (m, 1H), 7.00 (br. s., 1H), 5.12 (qd, J=6.5, 3.0 Hz, 1H), 4.56 (qd, J=6.4, 3.1 Hz, 1H), 4.51-4.44 (m, 2H), 4.23 (t, J=6.3 Hz, 1H), 3.98 (m, 2H), 1.43 (d, J=6.4 Hz, 3H), 1.39 (d, J=6.4 Hz, 3H).

Intermediate I-89 methyl 5-(((((2R,3S)-3-((2-(2-ethoxy-7-methylquinoxalin-5-yl)-5-fluorobenzo[d]thiazol-6-yl)oxy)butan-2-yl)oxy)carbonyl)amino)picolinate

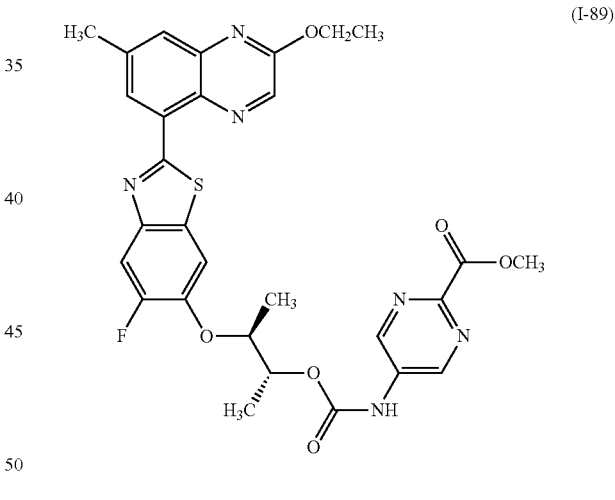

(I-89)

This intermediate was prepared in a manner analogous to Intermediate I-82. Thus, Intermediate I-80 was reacted with methyl 5-aminopicolinate and purified by ISCO (0-100% EtOAc/DCM, product at 35%) to afford Intermediate I-89 (76% yield) as a yellow solid. LC-MS: Method H, RT=1.31 min, MS (ESI) m/z: 606.2 (M+H)$^+$. $^1$H NMR (400 MHz, CDCl$_3$) δ 8.55 (s, 2H), 8.47 (s, 1H), 8.20-8.11 (m, 1H), 8.10-8.05 (m, 1H), 7.78 (d, J=11.4 Hz, 1H), 7.70 (dd, J=2.0, 0.9 Hz, 1H), 7.49 (d, J=7.9 Hz, 1H), 7.24 (s, 1H), 5.16 (qd, J=6.5, 3.0 Hz, 1H), 4.65-4.58 (m, 1H), 4.55 (q, J=7.0 Hz, 2H), 3.95 (s, 3H), 2.62 (s, 3H), 1.49 (t, J=7.0 Hz, 3H), 1.46 (d, J=6.6 Hz, 3H), 1.41 (d, J=6.4 Hz, 3H).

Intermediate I-90 methyl 5-(((((2R,3S)-3-((2-(2-ethoxy-7-methylquinoxalin-5-yl)-5-fluorobenzo[d]thiazol-6-yl)oxy)butan-2-yl)oxy)carbonyl)amino)pyrimidine-2-carboxylate

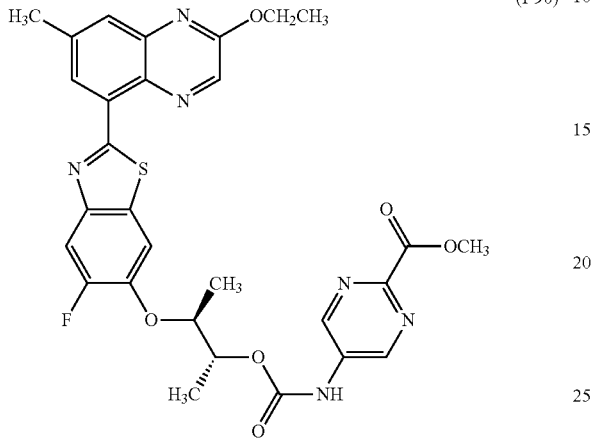

(I-90)

This intermediate was prepared in a manner analogous to Intermediate I-82. Thus, Intermediate I-80 was reacted with Intermediate I-107 and purified by ISCO (0-80% EtOAc/DCM, product at 40%) to afford Intermediate I-90 (81% yield) as a yellow solid. LC-MS: Method H, RT=1.24 min, MS (ESI) m/z: 607.1 (M+H)$^+$. $^1$H NMR (400 MHz, CDCl$_3$) δ 9.04 (s, 2H), 8.53 (d, J=2.0 Hz, 1H), 8.47 (s, 1H), 7.77 (d, J=11.2 Hz, 1H), 7.70 (dd, J=1.8, 0.9 Hz, 1H), 7.48 (d, J=7.9 Hz, 1H), 7.45 (s, 1H), 5.17 (qd, J=6.5, 2.9 Hz, 1H), 4.65-4.58 (m, 1H), 4.58-4.51 (m, 2H), 4.02 (s, 3H), 2.62 (s, 3H), 1.49 (t, J=7.0 Hz, 3H), 1.46 (d, J=6.6 Hz, 3H), 1.40 (d, J=6.6 Hz, 3H). $^{19}$F NMR (376 MHz, CDCl$_3$) δ −132.68 (s, 1F).

Intermediate I-91

(2R,3S)-3-((2-(6-chloro-3-methoxyquinolin-8-yl)-5-fluorobenzo[d]thiazol-6-yl)oxy)butan

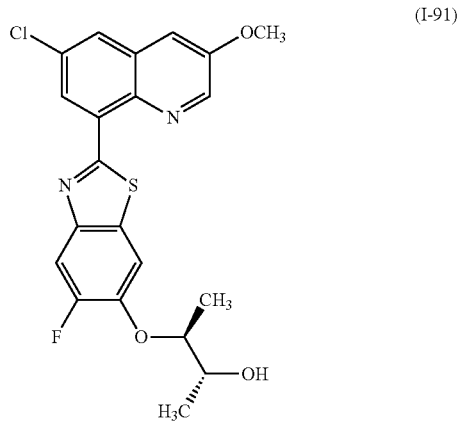 [SMILES: COc1cnc2c(-c3nc4cc(F)c(O[C@@H](C)[C@@H](C)O)cc4s3)cc(Cl)cc2c1]

(I-91)

This intermediate was prepared in a manner analogous to Intermediate I-78. Thus, Intermediate I-72A was reacted with Intermediate I-121 and purified by ISCO (0-70% EtOAc/DCM, product at 30%) to afford I-91 (55% yield) as a yellow solid. LC-MS: Method H, RT=1.16 min, MS (ESI) m/z: 433.0, 435.0 (M+H)$^+$. $^1$H NMR (400 MHz, DMSO-d$_6$) δ 8.90 (d, J=3.1 Hz, 1H), 8.65 (d, J=2.4 Hz, 1H), 8.21 (d, J=2.4 Hz, 1H), 8.03-7.94 (m, 3H), 4.89 (d, J=5.1 Hz, 1H), 4.43-4.34 (m, 1H), 4.01 (s, 3H), 3.88-3.77 (m, 1H), 1.32 (d, J=6.2 Hz, 3H), 1.20 (d, J=6.2 Hz, 3H) $^{19}$F NMR (376 MHz, DMSO-d$_6$) δ −133.13 (s, 1F).

Intermediate I-92

1-(5-aminopyridin-2-yl)-2-methylpropan-2-ol

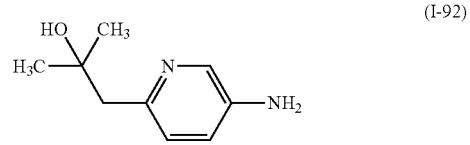

(I-92)

Intermediate I-92A: 1-(5-bromopyridin-2-yl)-2-methylpropan-2-ol

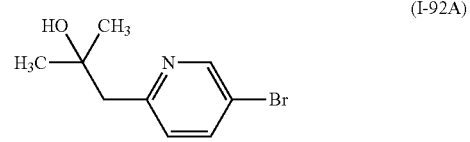

(I-92A)

5-bromo-2-methylpyridine (0.7 g, 4.07 mmol) was dissolved in anhydrous THF (20 mL). The solution was cooled to −78° C. and 2M LDA in THF (2.442 mL, 4.88 mmol) was added dropwise. The reaction mixture was stirred for 20 minutes at −78° C. then freshly distilled acetone (1.046 mL, 14.24 mmol) was added and the reaction mixture continued to stir for 20 minutes at −78° C. The reaction mixture was then quenched with saturated ammonium chloride and extracted with EtOAc (3×). The combined organic layer was washed with brine (1×), dried with sodium sulfate, filtered and concentrated. The resulting residue was dissolved in a small amount of methylene chloride before being charged to a 24 g silica gel cartridge which was eluted with a 15 min gradient from 0-100% EtOAc in hexane, The desired fractions were collected and concentrated to yield Intermediate I-92A (0.432 g, 1.877 mmol, 46.1% yield). LC-MS: Method H, MS (ESI) m/z: 232.0 (M+H)$^+$. $^1$H NMR (400 MHz, CDCl$_3$) δ 8.61 (d, J=2.2 Hz, 1H), 7.79 (dd, J=8.1, 2.4 Hz, 1H), 7.08 (d, J=8.4 Hz, 1H), 2.91 (s, 2H), 1.28-1.17 (m, 6H).

Intermediate I-92

To a solution of Intermediate I-92A (432 mg, 1.877 mmol) dissolved in DMSO (5 mL) was added L-proline (86 mg, 0.751 mmol), ammonium hydroxide (0.146 mL, 3.75 mmol), potassium carbonate (519 mg, 3.75 mmol) and copper(I) iodide (71.5 mg, 0.375 mmol). The reaction vessel was evacuated and backfilled with Ar 3× then stirred at 90° C. for 18 h. The reaction mixture was then diluted with water and extracted with EtOAc (3×). The combined organic layer was washed with brine, dried with sodium sulfate, filtered and concentrated. The resulting residue was dissolved in methylene chloride before being charged to a 24 g silica gel cartridge which was eluted with a 15 min gradient from 0-30% MeOH in methylene chloride. The desired fractions were collected and concentrated to yield Intermediate I-92 (47 mg, 0.283 mmol, 15% yield), as a white solid. LC-MS: Method H, MS (ESI) m/z: 167.1 (M+H)+. $^1$H NMR (400 MHz, CDCl$_3$) δ 8.04 (d, J=2.6 Hz, 1H), 7.00-6.96 (m, 1H), 6.95-6.90 (m, 1H), 2.81 (s, 2H), 1.22 (s, 6H).

Intermediate I-93

6-(2-((tert-butyldimethyl silyl)oxy)ethyl)pyridin-3-amine

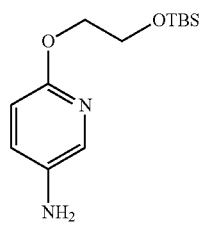

(I-93)

Intermediate I-93A:
2-((5-nitropyridin-2-yl)oxy)ethanol

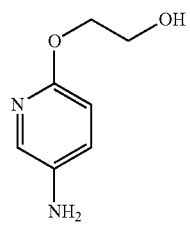

(I-93A)

Ethylene glycol (0.883 mL, 15.84 mmol) was dissolved in DMF (10 mL) at 0° C. Sodium hydride (253 mg, 6.33 mmol, 60% in mineral oil) was added to the reaction mixture portion wise and the reaction mixture was stirred for 10 minutes at 0° C. 2-fluoro-5-nitropyridine (450 mg, 3.17 mmol) dissolved in 1 mL of DMF was then added to the reaction mixture which was allowed to stir for 15 minutes at room temperature. The mixture was then quenched with saturated ammonium chloride and extracted with EtOAc (1×). The organic layer was then washed with 10% aqueous LiCl (3×), brine (1×), dried with sodium sulfate, filtered and concentrated to yield Intermediate I-93A, (530 mg, 2.88 mmol, 91% yield), as a clear oil which was brought forward without further purification. LC-MS: Method H, MS (ESI) m/z: 185.1 (M+H)+. $^1$H NMR (400 MHz, CDCl$_3$) δ 9.09 (d, J=2.9 Hz, 1H), 8.41 (dd, J=9.0, 2.9 Hz, 1H), 6.92 (dd, 0.4 Hz, 1H), 4.65-4.54 (m, 2H), 4.09-3.96 (m, 2H), 2.32 (t, J=5.9 Hz, 1H).

Intermediate I-93B: 2-(2-((tert-butyldimethylsilyl)oxy)ethoxy)-5-nitropyridine

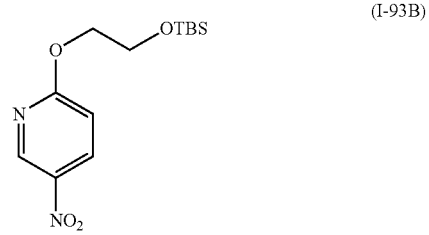 [SMILES: CC(C)(C)[Si](C)(C)OCCOc1ccc([N+](=O)[O-])cn1]

(I-93B)

Intermediate I-93A (530 mg, 2.88 mmol) was dissolved in dichloromethane (20 mL) along with TEA (0.521 mL, 3.74 mmol) and DMAP (70.3 mg, 0.576 mmol). TBS-Cl (521 mg, 3.45 mmol) was added to the reaction mixture which was allowed to stir at room temperature for 18 h. The reaction mixture was then quenched with saturated aqueous sodium bicarbonate and extracted with DCM (2×). The organic layer was washed with brine (1×), dried with sodium sulfate, filtered and concentrated. The resulting residue was dissolved in methylene chloride before being charged to a 40 g silica gel cartridge which was eluted with a 15 min gradient from 0-100% EtOAc in hexane. The desired fractions were collected and concentrated to yield Intermediate I-93B, (700 mg, 2.346 mmol, 82% yield), as a clear oil. LC-MS: Method H, RT=1.25 min, MS (ESI) m/z: 299.2 (M+H)+. $^1$H NMR (400 MHz, CDCl$_3$) δ 8.98 (d, J=2.4 Hz, 1H), 8.27 (dd, J=9.0, 2.9 Hz, 1H), 6.80-6.72 (m, 1H), 4.47-4.35 (m, 2H), 3.90 (dd, 4.5 Hz, 2H), 0.84-0.73 (m, 9H), 0.03-0.01 (m, 6H).

Intermediate I-93

Intermediate I-93B (700 mg, 2.346 mmol) was dissolved in ethyl acetate (10 mL). Pd—C (125 mg, 0.117 mmol, 10% by wt.) was added to the reaction mixture which was evacuated and backfilled with 1 atm of hydrogen 3× and stirred under 1 atm of hydrogen at room temperature for 3 h. The reaction mixture was then filtered through a pad of celite and the filtrate was concentrated to yield Intermediate I-93, (561 mg, 2.090 mmol, 89% yield), as a yellow oil. The product was brought forward without further purification. LC-MS: Method H, MS (ESI) m/z: 289.2 (M+H)+. $^1$H NMR (400 MHz, CDCl$_3$) δ 7.59-7.53 (m, 1H), 7.01-6.86 (m, 1H), 6.58-6.47 (m, 1H), 4.27-4.14 (m, 2H), 3.96-3.80 (m, 2H), 3.37-3.11 (m, 2H), 0.86-0.77 (m, 10H), 0.00 (s, 6H).

Intermediate I-94

2-(2-((tert-butyldimethylsilyl)oxy)ethyl)pyridin-4-amine

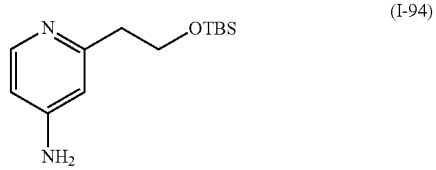 [SMILES: CC(C)(C)[Si](C)(C)OCCc1cc(N)ccn1]

(I-94)

Intermediate I-94A: 2-(4-bromopyridin-2-yl)ethanol

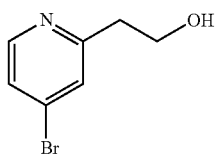

4-bromo-2-methylpyridine (2.5 g, 14.53 mmol) was dissolved in anhydrous THF (50 mL) at −78° C. LDA (25.4 mL, 50.9 mmol) was added to the reaction mixture which was allowed to stir at −78° C. for 30 minutes. Anhydrous DMF (3.38 mL, 43.6 mmol) was then added to the reaction mixture which continued to stir at −78° C. for an additional 45 minutes. A mixture of acetic acid (3.33 mL, 58.1 mmol)/MeOH (10 mL) was then added to the mixture at −78° C. followed by sodium borohydride (0.550 g, 14.53 mmol). The reaction mixture was then allowed to warm to room temperature and was stirred for 1 h then quenched with 10% aqueous citric acid solution at room temperature and stirred for an additional 10 minutes. The reaction mixture was extracted with EtOAc (3×). The organic layer was washed with brine (1×), dried with sodium sulfate, filtered and concentrated to yield Intermediate I-94A which was brought forward without further purification. LC-MS: Method H, MS (ESI) m/z: 201.9 (M+H)$^+$. $^1$H NMR (400 MHz, DMSO-$d_6$) δ 8.37 (d, J=5.3 Hz, 1H), 7.58 (d, J=1.8 Hz, 1H), 7.49 (dd, J=5.4, 1.9 Hz, 1H), 3.78-3.70 (m, 1H), 2.89-2.86 (m, 2H), 2.28 (d, J=5.5 Hz, 1H).

Intermediate I-94B: 2-(4-bromopyridin-2-yl)ethyl acetate

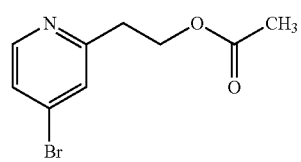

Intermediate I-94A (2.9 g, 14.35 mmol) was dissolved in THF (50 mL). Acetic anhydride (4.06 mL, 43.1 mmol) was added to the reaction mixture followed by DMAP (0.351 g, 2.87 mmol) and pyridine (3.48 mL, 43.1 mmol). The mixture was stirred at room temperature for 2 hours then diluted with EtOAc and 1.5M potassium diphosphate solution and extracted with EtOAc (3×). The organic layer was washed with brine (1×), dried with sodium sulfate, filtered and concentrated. The resulting residue was dissolved in methylene chloride before being charged to an 80 g silica gel cartridge which was eluted with a 30 min gradient from 0-80% EtOAc in hexane. The desired fractions were collected and concentrated to yield Intermediate I-94B (0.98 g, 4.01 mmol, 28.0% yield) as a yellow oil. LC-MS: Method H, MS (ESI) m/z: 246.0 (M+H)$^+$. $^1$H NMR (400 MHz, CDCl$_3$) δ 8.40 (d, J=5.5 Hz, 1H), 7.41 (d, J=1.8 Hz, 1H), 7.36 (dd, J=5.3, 1.8 Hz, 1H), 4.48 (t, J=6.6 Hz, 2H), 3.11 (t, J=6.6 Hz, 2H), 2.08-1.99 (m, 3H).

Intermediate I-94

Intermediate I-94B (282 mg, 3.20 mmol), 2,2,2-trifluoroacetamide (722 mg, 6.39 mmol), 2-(4-bromopyridin-2-yl) ethyl acetate (780 mg, 3.20 mmol), 3 Å molecular sieves (250 mg, 3.20 mmol), copper(I) iodide (122 mg, 0.639 mmol) and potassium carbonate (883 mg, 6.39 mmol) were dissolved in dioxane (1 mL). The reaction vessel was evacuated and backfilled with Ar 3× then heated to 75° C. for 4 h. 5 mL of MeOH was then added to the reaction mixture which was allowed to stir for 30 minutes at room temperature. The reaction mixture was then filtered through celite and the filtrate was concentrated. The resulting residue was dissolved in THF (30 mL). 1M aqueous LiOH (12.05 mL, 12.05 mmol) was added to the mixture which was allowed to stir at room temperature for 18 h. The reaction mixture was then concentrated to dryness, redissolved in THF (30 mL) and filtered through a pad of celite. The celite pad was washed with excess THF. To the THF solution (~50 mL) was added TBS-Cl (3028 mg, 20.09 mmol) and imidazole (1368 mg, 20.09 mmol). The reaction mixture was stirred at room temperature for 1 hour then filtered through a pad of celite and the filtrate was concentrated. The resulting residue was dissolved in methylene chloride before being charged to an 80 g silica gel cartridge which was eluted with a 30 min gradient from 0-25% MeOH in methylene chloride. The fractions containing desired product were concentrated and the resulting isolate was repurified on an 80 g column using 1M NH$_3$ MeOH/DCM (0-20%, 30 min gradient). Fractions containing the desired product were concentrated to yield Intermediate I-94 (293 mg, 1.16 mmol, 29% yield). LC-MS: Method H, MS (ESI) m/z: 253.2 (M+H)$^+$. $^1$H NMR (400 MHz, CDCl$_3$) δ 8.20 (d, J=5.7 Hz, 1H), 6.51 (d, J=2.2 Hz, 1H), 6.44 (dd, J=5.6, 2.3 Hz, 1H), 4.35-4.11 (m, 2H), 3.97 (t, J=6.6 Hz, 2H), 2.91 (t, J=6.5 Hz, 2H), 0.88 (s, 9H), 0.00 (s, 6H).

Intermediate I-95

1-(4-aminopyridin-2-yl)-2-methylpropan-2-ol

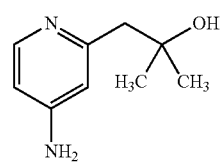

Intermediate I-95A: 1-(4-bromopyridin-2-yl)-2-methylpropan-2-ol

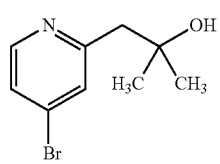

To a stirred solution of 4-bromo-2-methylpyridine (0.7 g, 4.07 mmol) in anhydrous THF (20 mL) at −78° C. was added 2M LDA in THF (2.442 mL, 4.88 mmol) dropwise. The reaction mixture was stirred for 20 minutes at −78° C. Freshly distilled acetone (1.046 mL, 14.24 mmol) was then added to the reaction mixture which stirred for an additional 20 minutes at −78° C. The reaction mixture was then quenched with saturated ammonium chloride and was allowed to warm to room temperature. The reaction mixture was then diluted with water and extracted with EtOAc (3×). The organic layer was washed with brine (1×), dried with sodium sulfate, filtered and concentrated. The resulting residue was dissolved in methylene chloride before being charged to a 24 g silica gel cartridge which was eluted with a 15 min gradient from 0-100% EtOAc in hexane. The desired fractions were collected and concentrated to yield Intermediate I-95A (0.588 g, 2.56 mmol, 62.8% yield). LC-MS: Method H, MS (ESI) m/z: 232.0 (M+H)$^+$. $^1$H NMR (400 MHz, CDCl$_3$) δ 8.36 (d, J=5.3 Hz, 1H), 7.42-7.34 (m, 2H), 5.35-5.01 (m, 1H), 2.92 (s, 2H), 1.25 (s, 6H).

Intermediate I-95

Intermediate I-95A (588 mg, 2.56 mmol) was dissolved in DMSO (5 mL) along with L-proline (118 mg, 1.022 mmol), ammonium hydroxide (0.199 mL, 5.11 mmol), potassium carbonate (706 mg, 5.11 mmol) and copper(I) iodide (97 mg, 0.511 mmol). The reaction mixture was evacuated and backfilled with argon three times before being sealed and heated to 90° C. for 5 hours. The reaction mixture was then filtered through celite, washed with MeOH and the filtrate was concentrated. The resulting residue was dissolved in methylene chloride before being charged to a 24 g silica gel cartridge which was eluted with a 15 min gradient from 0-30% MeOH in methylene chloride. Fractions containing desired product were concentrated and repurified by Prep HPLC using Method A to yield Intermediate I-95 (28 mg, 0.168 mmol, 7% yield). LC-MS: Method H, MS (ESI) m/z: 167.0 (M+H)$^+$. $^1$H NMR (400 MHz, MeOH-d$_4$) δ 7.94 (d, J=7.0 Hz, 1H), 6.76 (dd, J=6.9, 2.3 Hz, 1H), 6.74-6.68 (m, 1H), 2.84 (s, 2H), 1.28 (s, 6H).

Intermediate I-96

1-((4-aminopyridin-2-yl)oxy)-2-methylpropan-2-ol

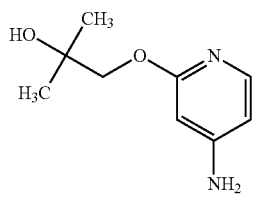
(I-96)

Intermediate I-96A: 1-((4-bromopyridin-2-yl)oxy)-2-methylpropan-2-ol

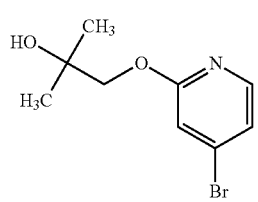
(I-96A)

This intermediate was prepared according to Procedure D from 2-methylpropane-1,2-diol. Intermediate I-96A was afforded in 52% yield after column chromatography. LC-MS: Method H, MS (ESI) m/z: 247.9 (M+H)$^+$. $^1$H NMR (400 MHz, CDCl$_3$) δ 7.98 (d, J=5.5 Hz, 1H), 7.08 (dd, J=5.5, 1.5 Hz, 1H), 7.05 (d, J=1.3 Hz, 1H), 4.23 (s, 2H), 3.01 (s, 1H), 1.34 (s, 6H).

Intermediate I-96

This intermediate was prepared from Intermediate I-96A according to Procedure E. Intermediate I-96 was afforded in 66% yield. LC-MS: Method H, MS (ESI) m/z: 183.1 (M+H)$^+$. $^1$H NMR (400 MHz, DMSO-d$_6$) δ 7.72-7.38 (m, 1H), 6.24-6.15 (m, 1H), 6.14-5.95 (m, 2H), 5.91-5.80 (m, 1H), 3.91 (s, 2H), 1.15 (s, 6H).

Intermediate I-97

2-(2-((tert-butyl dimethyl silyl)oxy)ethoxy)pyrimidin-5-amine

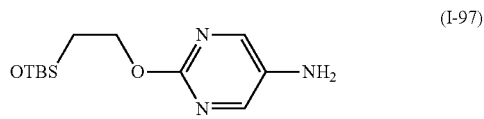
(I-97)

Intermediate I-97A:
2-((5-nitropyrimidin-2-yl)oxy)ethanol

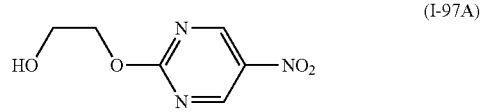 [SMILES: O=[N+]([O-])c1cnc(OCCO)nc1]
(I-97A)

2-chloro-5-nitropyrimidine (1 g, 6.27 mmol) was mixed with ethylene glycol (8 ml, 143 mmol) and DIEA (3.28 ml, 18.81 mmol) was added. The mixture was stirred at 80° C. for 20 minutes and was then poured into 30 mL of ice water. 40 mL of EtOAc was added to the mixture followed by 20 mL of 1N aqueous HCl. EtOAc (30 mL×3) was used to extract the aqueous layer. The combined organic layer was washed with brine, dried with sodium sulfate, filtered and concentrated to give Intermediate I-97A in quantitative yield as a yellow oil. The product was brought forward without further purification. $^1$H NMR (400 MHz, CDCl$_3$) δ 9.33 (s, 2H), 4.73-4.51 (m, 2H), 4.08-3.96 (m, 2H), 2.41 (br. s, 1H).

Intermediate I-97B: 2-(2-((tert-butyldimethylsilyl)oxy)ethoxy)-5-nitropyrimidine

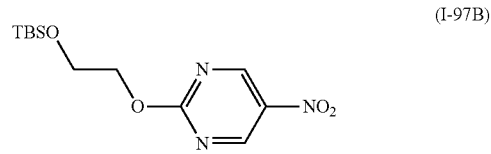 [SMILES: CC(C)(C)[Si](C)(C)OCCOc1ncc([N+](=O)[O-])cn1]
(I-97B)

Intermediate I-97A, (1.23 g, 6.64 mmol), was mixed with tert-butylchlorodimethylsilane (2.003 g, 13.29 mmol) in DCM (20 ml). Imidazole (0.905 g, 13.29 mmol) was added to the reaction mixture and the reaction mixture stirred at room temperature for 30 minutes. The solid was filtered off and the filter cake was washed with a small amount of DCM. The filtrate was mixed with 30 g of silica gel, evaporated to dryness and loaded on CombiFlash (80 g column, 0-50% EtOAc/Hexane) for purification. The fractions containing desired product were collected and concentrated to give Intermediate I-97B, (1.73 g, 5.78 mmol, 87% yield), as a light yellow solid. LC-MS: Method H, MS (ESI) m/z: 300.0 (M+H)$^+$. $^1$H NMR (400 MHz, CDCl$_3$) δ ppm 9.30 (2H, s), 4.61 (2H, dd, J=5.50, 4.62 Hz), 4.02 (2H, dd, J=5.61, 4.73 Hz), 0.88 (9H, s), 0.09 (6H, s).

Intermediate I-97

Intermediate I-97B, (1.73 g, 5.78 mmol), was dissolved in THF (40 ml). Wet Pd—C (0.307 g, 0.289 mmol, 10% by wt.) was then added to the solution. The mixture was then evacuated and backfilled with hydrogen 3×, and the mixture was stirred under 1 atm H$_2$ for 7 hours at room temperature. The catalyst was filtered off over a pad of celite which was washed with a small amount of EtOAc. The filtrate was concentrated to yield Intermediate I-97, (1.53 g, 5.68 mmol, 98% yield), as a gray solid. LC-MS: Method H, MS (ESI) m/z: 270.1 (M+H)$^+$. $^1$H NMR (400 MHz, CDCl$_3$) δ ppm 8.05 (2H, s), 4.35 (2H, t, J=5.50 Hz), 3.97 (2H, t, J=5.61 Hz), 1.69 (2H, d, J=5.06 Hz), 0.89 (9H, s), 0.08 (6H, s).

Intermediate I-98

2-(2-((tert-butyldiphenylsilyl)oxy)ethyl)pyrimidin-5-amine

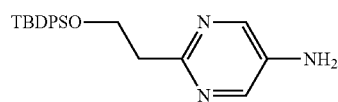
(I-98)

Intermediate I-98A: 3-hydroxypropanimidamide, HCl

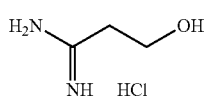
(I-98A)

To a mixture of MeOH (5 mL, 124 mmol)/toluene (30.1 mL) at 0° C. was added acetyl chloride (3.00 mL, 42.2 mmol) slowly over 10 minutes. The reaction mixture was allowed to stir at 0° C. for 10 minutes then at room temperature for 10 minutes. The reaction mixture was cooled to 0° C. and 3-hydroxypropanenitrile (1.5 g, 21.10 mmol) dissolved in 5 mL of toluene added and the reaction mixture was allowed to stir at room temperature for 18 h. The reaction mixture was cooled to 0° C. and 7N ammonia in MeOH (15.07 mL, 106 mmol) was added carefully over 5 minutes. The reaction mixture was then allowed to warm to room temperature and stirred for 18 h at room temperature. The mixture was then filtered through celite and the filter cake washed with 2:1 toluene/MeOH. The filtrate was concentrated to yield Intermediate I-98A in quantitative yield. The product was brought forward without further purification. $^1$H NMR (400 MHz, DMSO-d$_6$) δ 3.70 (t, J=5.9 Hz, 2H), 2.77 (t, J=5.9 Hz, 2H).

Intermediate I-98B: methyl 2-(2-hydroxyethyl)pyrimidine-5-carboxylate

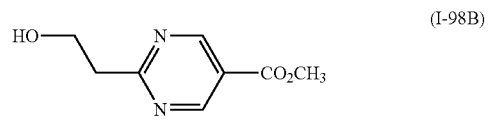 [SMILES: COC(=O)c1cnc(CCO)nc1]
(I-98B)

Intermediate I-98A (8.9 g, 71.4 mmol) was dissolved in DMF (200 ml). While the solution stirred at room temperature, sodium (Z)-2-(dimethoxymethyl)-3-methoxy-3-oxo-prop-1-en-1-olate (16.5 g, 83 mmol) was added in portionwise and the reaction mixture was stirred at room temperature for 18 h. The reaction mixture was then concentrated under reduced pressure and heat. The resulting residue was then suspended in 10:1 DCM:MeOH mixture and run through a pad of silica gel/celite which was washed with 500 mL of additional 10:1 DCM/MeOH solution. The filtrate was concentrated to yield Intermediate I-98B (10.5 g, 57.6 mmol, 81% yield), as a red oil. The product was brought forward without further purification. LC-MS: Method H, MS (ESI) m/z: 183.0 (M+H)$^+$. $^1$H NMR (400 MHz, DMSO-d$_6$) δ 9.16 (s, 2H), 4.69 (t, J=5.4 Hz, 1H), 4.03-3.79 (m, 5H), 3.12 (t, J=6.6 Hz, 2H).

Intermediate I-98C: methyl 2-(2-((tert-butyldiphenylsilyl)oxy)ethyl)pyrimidine-5-carboxylate

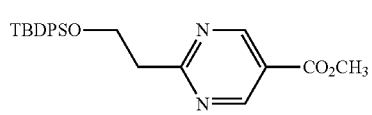
(I-98C)

To the solution of Intermediate I-98B (4 g, 21.96 mmol) in THF (80 mL) was added DMAP (0.134 g, 1.098 mmol), TEA (7.65 mL, 54.9 mmol) and TBDPS-Cl (8.46 mL, 32.9 mmol). The reaction mixture was stirred for 18 h at room temperature. 5 mL of methanol was then added and the reaction mixture stirred for 10 minutes at room temperature followed by evaporation under reduced pressure. The crude product was purified by silica gel chromatography on a 120 g silica column using petroleumether, chloroform and EtOAc as eluent. First an eluent of 0-100% chloroform in petroleum ether was used followed by an eluent of 0-100% EtOAc in chloroform. Fractions containing desired product were collected and concentrated to yield Intermediate I-98C (7.5 g, 17.9 mmol, 82% yield), as a colorless oil. LC-MS: Method H, MS (ESI) m/z: 421.2 (M+H)$^+$. $^1$H NMR (400 MHz, CDCl$_3$) δ 9.16 (s, 2H), 7.73-7.28 (m, 10H), 4.22 (t, J=6.4 Hz, 2H), 3.97 (s, 4H), 3.30 (t, J=6.4 Hz, 2H), 0.98-0.94 (m, 9H).

Intermediate I-98D: 2-(2-((tert-butyldiphenylsilyl)oxy)ethyl)pyrimidine-5-carboxylic acid

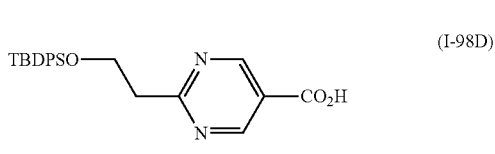
(I-98D)

Intermediate I-98C (2.14 g, 5.09 mmol) was dissolved in THF (60 mL). 1M aqueous LiOH (15.26 mL, 15.26 mmol) was added and the reaction mixture was allowed to stir at room temperature for 1 hour. The majority of the THF was concentrated under reduced pressure and the reaction mixture was acidified with 10% citric acid to pH 4-5 then extracted 3× with EtOAc. The combined organic layer was washed with brine, dried with sodium sulfate, filtered and concentrated to yield Intermediate I-98D, (2.07 g, 5.09 mmol, 100% yield), as a clear glass. LC-MS: Method H, MS (ESI) m/z: 407.2 (M+H)$^+$. $^1$H NMR (400 MHz, DMSO-$d_6$) δ 9.13 (s, 2H), 7.76-7.23 (m, 10H), 4.19 (t, J=6.3 Hz, 2H), 3.25 (t, J=6.3 Hz, 2H), 0.90 (s, 9H).

Intermediate I-98

Intermediate I-98D (5.5 g, 13.53 mmol) was dissolved in THF (350 mL). TEA (9.43 mL, 67.6 mmol) was added to the mixture followed by diphenyl phosphorazidate (9.31 g, 33.8 mmol) at room temperature. The reaction mixture was heated to 65° C. under a reflux condenser for 22 hours. The reaction mixture was then allowed to cool to room temperature and water (175 mL) was added. The mixture was stirred at room temperature for 2 hours and 15 minutes. The majority of THF was evaporated off under reduced pressure and the mixture was then diluted with water and a small amount of brine and extracted 3× with a total of ~500 mL of EtOAc. The organic layer was washed with brine, dried with sodium sulfate, filtered and concentrated. The resulting residue was dissolved in methylene chloride before being charged to a 330 g column which was eluted with a gradient from 0-20% MeOH/DCM. Fractions containing desired product were collected and concentrated to yield Intermediate I-98, (1.135 g, 3.01 mmol, 22% yield), as an orange oil. LC-MS: Method H, MS (ESI) m/z: 378.2. (M+H)$^+$. $^1$H NMR (500 MHz, DMSO-$d_6$) δ 8.04 (s, 2H), 7.59-7.53 (m, 4H), 7.47-7.31 (m, 6H), 5.76 (s, 2H), 4.02 (t, J=6.7 Hz, 2H), 2.97 (t, J=6.7 Hz, 2H), 0.92 (s, 9H).

Intermediate I-99

6-(3-((tert-butyldimethylsilyl)oxy)-2,2-difluoropropoxy)pyridin-3-amine

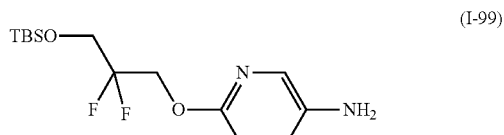
(I-99)

Intermediate I-99A: 2,2-difluoro-3-((5-nitropyridin-2-yl)oxy)propan-1-ol

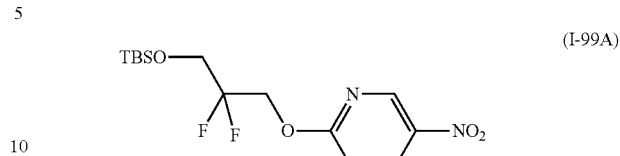
(I-99A)

2,2-difluoropropane-1,3-diol (394 mg, 3.52 mmol) was dissolved in DMF (10 mL). Sodium hydride (77 mg, 1.934 mmol, 60% by wt.) was added to the mixture at 0° C. and the reaction mixture was stirred at 0° C. for 10 minutes. 2-fluoro-5-nitropyridine (250 mg, 1.758 mmol) dissolved in 1 mL of DMF was then added to the reaction mixture which was allowed to stir at room temperature for 1 hour. The mixture was then quenched with saturated ammonium chloride and diluted with EtOAc. The organic layer was washed with 10% aqueous LiCl (3×), and brine (1×), dried with sodium sulfate, filtered and concentrated to yield 2,2-difluoro-3-((5-nitropyridin-2-yl)oxy)propane as a yellow oil. To the crude intermediate dissolved in DCM (9 mL) was added TEA (1137 µl, 8.16 mmol) and DMAP (39.9 mg, 0.326 mmol) followed by TBS-Cl (738 mg, 4.89 mmol). The reaction mixture stirred for 18 h at room temperature. 5 mL of MeOH was then added to the reaction mixture which was allowed to stir for 10 minutes at room temperature. The reaction mixture was then quenched with saturated sodium bicarbonate and extracted DCM (3×). The organic layer was washed with brine (1×), dried with sodium sulfate, filtered and concentrated. The resulting residue was dissolved in a small amount of methylene chloride and charged to a 40 g silica gel cartridge which was eluted with a 15 min gradient from 0-100% EtOAc in hexane. Fractions containing desired product were concentrated to yield Intermediate I-99A (204 mg, 0.586 mmol, 36% yield) as a clear oil. LC-MS: Method H, MS (ESI) m/z: 349.2 (M+H)$^+$. $^1$H NMR (400 MHz, CDCl$_3$) δ 9.01 (dd, J=2.9, 0.4 Hz, 1H), 8.34 (dd, J=9.1, 2.8 Hz, 1H), 6.86 (dd, J=9.0, 0.4 Hz, 1H), 4.66 (t, J=12.4 Hz, 2H), 3.85 (t, J=12.2 Hz, 2H), 0.81-0.78 (m, 9H), 0.00 (s, 6H).

Intermediate I-99

Intermediate I-99A (204 mg, 0.586 mmol) was dissolved in EtOAc (10 mL). Pd—C (18.69 mg, 0.176 mmol, 10% by wt.) was added to the solution and the flask was evacuated and backfilled with 1 atm of hydrogen 3×. The reaction mixture was stirred under 1 atm of hydrogen for 18 h and then filtered through celite and the celite pad washed with excess EtOAc. The filtrate was concentrated to yield Intermediate I-99 in quantitative yield as a green oil. The product was brought forward without further purification. LC-MS: Method H, MS (ESI) m/z: 319. (M+H)$^+$. $^1$H NMR (400 MHz, CDCl$_3$) δ 7.60-7.54 (m, 1H), 7.02-6.95 (m, 1H), 6.63-6.50 (m, 1H), 4.45 (t, J=12.5 Hz, 2H), 3.86 (t, J=12.4 Hz, 2H), 0.81 (s, 9H), 0.00 (s, 6H).

Intermediate I-100

4-((5-aminopyrimidin-2-yl)oxy)-2-methylbutan-2-ol, HCl

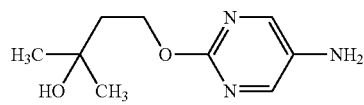
(I-100)

Intermediate I-100A: 4-((5-bromopyrimidin-2-yl)oxy)-2-methylbutan-2-ol

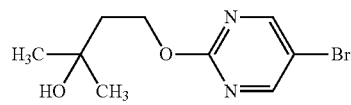
(I-100A)

This intermediate was prepared according to Procedure A from 3-methylbutane-1,3-diol. Intermediate I-100A was afforded in 68% yield after silica gel chromatography. LC-MS: Method H, MS (ESI) m/z: 263.0. $^1$H NMR (400 MHz, CDCl$_3$) δ 8.55 (s, 2H), 4.56 (t, J=6.8 Hz, 2H), 2.05 (t, J=6.8 Hz, 2H), 1.34 (s, 6H).

Intermediate I-100B 4-((5-((diphenylmethylene)amino)pyrimidin-2-yl)oxy)-2-methylbutan-2-ol

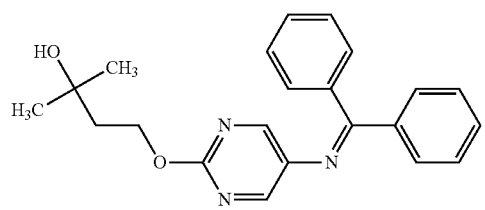
(I-100B)

This intermediate was prepared according to Procedure B from Intermediate I-100A. Intermediate I-100B was afforded in 81% yield after silica gel chromatography. LC-MS: Method H, MS (ESI) m/z: 362.1.

Intermediate I-100

Intermediate I-100 was afforded from Intermediate I-100B in 77% yield according to Procedure C. LC-MS: Method H, MS (ESI) m/z: 198.1.

Intermediate I-101

2-(2-methyl-2-((triethylsilyl)oxy)propoxy)pyrimidin-5-amine

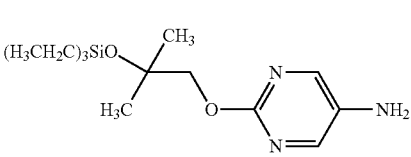
(I-101)

Intermediate I-101A: 1-((5-bromopyrimidin-2-yl)oxy)-2-methylpropan-2-ol

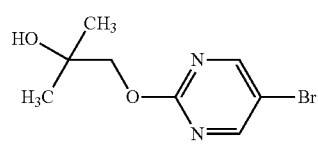
(I-101A)

This intermediate was prepared according to Procedure A from 2-methylpropane-1,2-diol. Intermediate I-101A was afforded in 29% yield after silica gel chromatography. LC-MS: Method H, MS (ESI) m/z: 249.0. $^1$H NMR (400 MHz, CDCl$_3$) δ 8.57 (s, 2H), 4.25 (s, 2H), 1.38 (s, 6H).

Intermediate I-101B 1-((5-((diphenylmethylene)amino)pyrimidin-2-yl)oxy)-2-methylpropan-2-ol

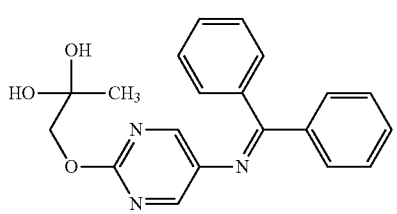
(I-101B)

This intermediate was prepared according to Procedure B from Intermediate I-101A. Intermediate I-101B was afforded in 58% yield after silica gel chromatography. LC-MS: Method H, MS (ESI) m/z: 348.2. $^1$H NMR (400 MHz, CDCl$_3$) δ 7.99 (s, 2H), 7.81-7.67 (m, 2H), 7.58-7.35 (m, 6H), 7.19-7.02 (m, 2H), 4.17 (s, 2H), 1.34 (s, 6H).

Intermediate I-101

Intermediate I-101B (152 mg, 0.438 mmol) was dissolved in MeOH (5 mL)/THF (5.00 mL). 1M HCl (1.0 mL, 1.0 mmol) was added to the reaction mixture and the reaction mixture was stirred for 30 minutes at room temperature. The mixture was then concentrated under reduced pressure and azeotroped with toluene 3×. The resulting residue was dissolved in anhydrous DCM (5 mL) along with Hunig's Base (0.534 mL, 3.06 mmol). The reaction mixture was then cooled to 0° C. and triethylsilyl trifluoromethanesulfonate (347 mg, 1.311 mmol) was added dropwise and the reaction mixture was allowed to stir at 0° C. for 30 minutes and then at room temperature for 30 minutes. The mixture was then quenched with saturated sodium bicarbonate and extracted with DCM (3×). The organic layer was washed with brine (1×), dried with sodium sulfate, filtered and concentrated. The resulting residue was dissolved in methylene chloride before being charged to a 24 g silica gel cartridge which was eluted with a 15 min gradient from 0-25% MeOH in methylene chloride. The desired fractions were collected and concentrated to yield Intermediate I-101 (42 mg, 0.141 mmol, 32.3% yield). LC-MS: Method H, MS (ESI) m/z: 298.2. $^1$H NMR (400 MHz, CDCl$_3$) δ 8.07 (s, 2H), 4.08 (s, 2H), 1.38 (s, 6H), 0.98-0.93 (m, 6H), 0.67-0.57 (m, 9H).

Intermediate I-102

1-(5-aminopyrimidin-2-yl)-2-methylpropan-2-ol

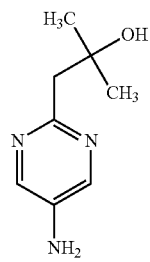

(I-102)

Intermediate I-102A:
3-hydroxy-3-methylbutanimidamide, HCl

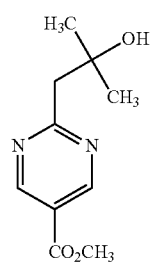

(I-102A)

This intermediate was synthesized from 3-hydroxy-3-methylbutanenitrile using the method described to synthesize Intermediate I-98A. Intermediate I-102A was afforded in quantitative yield. $^1$H NMR (400 MHz, DMSO-d$_6$) δ 2.54 (s, 2H), 1.36-1.00 (m, 6H).

Intermediate I-102B: methyl 2-(2-hydroxy-2-methylpropyl)pyrimidine-5-carboxylate

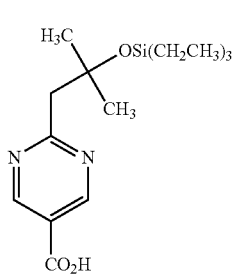

(I-102B)

This intermediate was synthesized from I-102A using the procedure described for Intermediate I-98B. Intermediate I-102B was afforded in 58% yield after chromatography. LC-MS: Method H, MS (ESI) m/z: 211.0 (M+H)$^+$. $^1$H NMR (400 MHz, DMSO-d$_6$) δ 9.18 (s, 2H), 4.70 (s, 1H), 3.91 (s, 3H), 3.09 (s, 2H), 1.17 (s, 6H).

Intermediate I-102C: methyl 2-(2-methyl-2-((triethylsilyl)oxy)propyl)pyrimidine-5-carboxylate

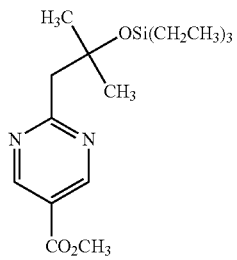

(I-102C)

To a solution of Intermediate I-102B (0.7 g, 3.33 mmol) and 2,6-lutidine (0.776 ml, 6.66 mmol) in DCM (16.65 ml) was added triethylsilyl trifluoromethanesulfonate (1.408 g, 5.33 mmol) dropwise at 0° C. The reaction mixture was allowed to stir at 0° C. for 30 minutes. The reaction mixture was quenched with saturated sodium bicarbonate and extracted with DCM (3×). The combined organic layer was washed with brine, dried with sodium sulfate, filtered and concentrated. The resulting residue was dissolved in a small amount of methylene chloride and charged to a 40 g silica gel cartridge which was eluted with a 15 min gradient from 0-100% EtOAc in hexane. Fractions containing the desired product were concentrated to yield Intermediate I-102C (0.629 g, 1.938 mmol, 58% yield) as a clear oil. LC-MS: Method H, MS (ESI) m/z: 325.3 (M+H)$^+$. $^1$H NMR (400 MHz, CDCl$_3$) δ 9.22 (s, 2H), 4.00 (s, 3H), 3.24 (s, 2H), 1.37 (s, 6H), 0.94-0.81 (m, 9H), 0.56 (q, J=8.1 Hz, 7H).

Intermediate I-102D: 2-(2-methyl-2-((triethylsilyl)oxy)propyl)pyrimidine-5-carboxylic acid (I-102D)

Intermediate I-102C (0.629 g, 1.938 mmol) was dissolved in THF (20 mL). 1M aqueous LiOH (5.82 mL, 5.82 mmol) was added to the reaction mixture which was allowed to stir at room temperature for 1 hour. Most of the THF was evaporated off and the reaction mixture was acidified to pH 4-5 with 10% citric acid and extracted with EtOAc (3×). The combined organic layer was washed with brine, filtered and concentrated to yield Intermediate I-102D (0.6 g, 1.623 mmol, 84% yield) as a clear glass. LC-MS: Method H, MS (ESI) m/z: 311.2 (M+H)$^+$. $^1$H NMR (400 MHz, DMSO-d$_6$) δ 9.14 (s, 2H), 3.13 (s, 2H), 1.31 (s, 6H), 0.84 (t, J=7.9 Hz, 9H), 0.53-0.40 (m, 6H).

Intermediate I-102

This intermediate was synthesized from I-102D according to the procedure described for conversion of Intermediate I-98D to Intermediate I-98. Intermediate I-102 was afforded in 78% yield after chromatography. LC-MS: Method H, MS (ESI) m/z: 168.1 (M+H)$^+$. $^1$H NMR (400 MHz, MeOH-d$_4$) δ 8.16 (s, 2H), 2.94 (s, 2H), 1.22 (s, 6H).

Intermediate I-103

(R)-2-(2-((tert-butyldimethylsilyl)oxy)propoxy)pyrimidin-5-amine

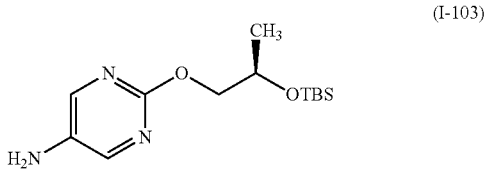 [SMILES: C[C@H](COc1ncc(N)cn1)O[Si](C)(C)C(C)(C)C]

This intermediate was prepared from (R)-ethyl 2-hydroxypropanoate in the same manner as described for Intermediate I-104 below. LC-MS: Method H, MS (ESI) m/z: 284.2 (M+H)$^+$. $^1$H NMR (400 MHz, CDCl$_3$) δ 7.97 (s, 2H), 4.20-4.06 (m, 2H), 4.01-3.93 (m, 1H), 3.29 (br. s., 2H), 1.17 (d, J=6.2 Hz, 3H), 0.81 (s, 9H), 0.01 (d, J=6.2 Hz, 6H). MS (ESI) m/z: 284.2 (M+H)$^+$.

Intermediate I-104

(S)-2-(2-((tert-butyldimethylsilyl)oxy)propoxy)pyrimidin-5-amine

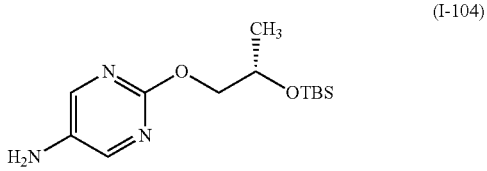 [SMILES: C[C@@H](COc1ncc(N)cn1)O[Si](C)(C)C(C)(C)C]

Intermediate I-104A: (S)-ethyl 2-((tert-butyldimethylsilyl)oxy)propanoate

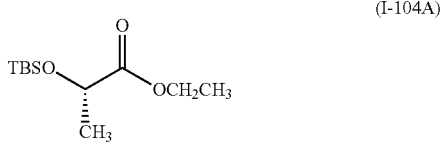

(S)-ethyl 2-hydroxypropanoate (1.50 g, 12.70 mmol) was reacted according to Procedure I using DCM as a solvent to afford Intermediate I-104A (2.3 g, 9.90 mmol, 78% yield) as a clear oil. $^1$H NMR (400 MHz, CDCl$_3$) δ 4.35-4.28 (m, 1H), 4.18 (t, J=7.5 Hz, 2H), 1.40 (d, J=6.8 Hz, 3H), 1.28 (t, J=7.2 Hz, 3H), 0.91 (s, 9H), 0.10 (s, 3H), 0.07 (s, 3H).

Intermediate I-104B: (S)-2-((tert-butyldimethylsilyl)oxy)propan-1-ol

Intermediate I-104A (2.2 g, 9.47 mmol) was dissolved in THF (100 ml) and the solution was cooled to −78° C. To the reaction mixture was added DIBAL-H (23.67 ml, 23.67 mmol) and the reaction mixture was allowed to warm to room temperature and stirred for 3 h at room temperature before being quenched with saturated Rochelle's salt. The quenched reaction mixture was stirred for 18 h at room temperature and then extracted with EtOAc (3×). The combined organic layer was washed with brine, dried with sodium sulfate, filtered and concentrated under reduced pressure to yield Intermediate I-104B in quantitative yield. $^1$H NMR (400 MHz, CDCl$_3$) δ 3.87-3.77 (m, J=2.6 Hz, 1H), 3.46-3.37 (m, 1H), 3.32-3.21 (m, 1H), 1.03 (d, J=6.4 Hz, 3H), 0.82 (s, 9H), 0.00 (s, 6H).

Intermediate I-104C: (S)-5-bromo-2-(2-((tert-butyldimethylsilyl)oxy)propoxy)pyrimidine

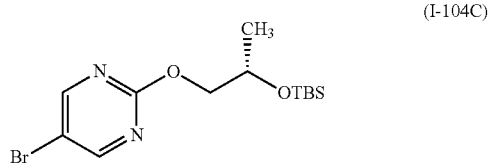 [SMILES: C[C@@H](COc1ncc(Br)cn1)O[Si](C)(C)C(C)(C)C]

Triphenylphosphine (2.88 g, 10.98 mmol) was dissolved in THF (143 ml) and the solution was cooled to 0° C. DIAD (1.941 ml, 9.98 mmol) was added and reaction mixture was allowed to stir for 5 minutes at 0° C. Intermediate I-104B (1.9 g, 9.98 mmol) was added to the reaction mixture and the reaction mixture was allowed to stir for 10 minutes at 0° C. 5-bromopyrimidin-2-ol (1.5 g, 8.57 mmol) was then added to the reaction mixture which was allowed to warm to room temperature slowly and stirred for 72 hours at room temperature. The reaction mixture was then diluted with water and extracted with EtOAc (3×). The combined organic layer was washed with brine (1×), dried with sodium sulfate, filtered and concentrated. The resulting residue was dissolved in a small amount of methylene chloride before being charged to an 80 g silica gel cartridge which was eluted with a 30 min gradient from 0-100% EtOAc in hexane. Fractions containing desired product were collected and concentrated to yield Intermediate I-104C (1.9 g, 5.47 mmol, 55% yield). $^1$H NMR (400 MHz, CDCl$_3$) δ 8.52 (s, 2H), 4.34-4.26 (m, 1H), 4.18 (s, 1H), 4.15-4.05 (m, 1H), 1.24 (d, J=6.2 Hz, 3H), 0.87 (s, 9H), 0.07 (d, J=8.1 Hz, 5H). LC-MS: Method H, MS (ESI) m/z: 349.1 (M+H)$^+$.

Intermediate I-104D (S)-2-(2-((tert-butyldimethylsilyl)oxy)propoxy)-N-(diphenylmethylene)pyrimidin-5-amine

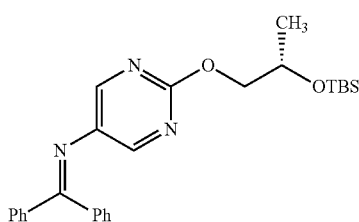
(I-104D)

This intermediate was synthesized from Intermediate I-104C using Procedure B. Intermediate I-104D was afforded in 78% yield after chromatography. LC-MS: Method H, MS (ESI) m/z: 448.2 (M+H)$^+$. $^1$H NMR (400 MHz, CDCl$_3$) δ 7.95 (s, 2H), 7.78-7.71 (m, 2H), 7.53-7.30 (m, 6H), 7.16-7.06 (m, 2H), 4.31-4.11 (m, 2H), 4.08-4.01 (m, 1H), 1.22 (d, J=5.9 Hz, 3H), 0.87 (s, 9H), 0.05 (d, J=9.9 Hz, 6H).

Intermediate I-104

Intermediate I-104D (1.9 g, 4.24 mmol) was dissolved in 90:10:0.1 MeOH/water/TFA (14 ml) and the solution stirred for 15 minutes at room temperature then basified with 1.5 M dipotassium phosphate solution and extracted with EtOAc (3×). The combined organic layer was washed with brine (1×), dried with sodium sulfate, filtered and concentrated. The resulting residue was dissolved in methylene chloride and charged to an 80 g silica gel cartridge which was eluted with a 30 min gradient from 0-15% MeOH in methylene chloride. Fractions containing the desired product were concentrated to yield Intermediate I-104 (210 mg, 0.741 mmol, 17% yield). LC-MS: RT=1.01 min, LC-MS: Method H, MS (ESI) m/z: 284.2 (M+H)$^+$. $^1$H NMR (400 MHz, DMSO-d$_6$) δ 7.92 (s, 2H), 4.93 (s, 2H), 4.16-3.83 (m, J=7.4, 5.6 Hz, 3H), 1.12 (d, J=6.2 Hz, 3H).

Intermediate I-105

(S)-2-((1-((tert-butyldimethylsilyl)oxy)propan-2-yl)oxy)pyrimidin-5-amine

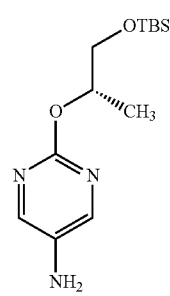
(I-105)

This intermediate was prepared from (S)-propane-1,2-diol using the same reaction sequence as described for Intermediate I-106 below. LC-MS: Method H, MS (ESI) m/z: 284.2 (M+H)$^+$. $^1$H NMR (400 MHz, CDCl$_3$) δ 7.97 (s, 2H), 5.04 (d, J=6.2 Hz, 1H), 3.78 (dd, J=10.3, 5.5 Hz, 1H), 3.60 (dd, J=10.3, 5.7 Hz, 1H), 1.28 (d, J=6.4 Hz, 3H), 0.83 (s, 9H), 0.00 (s, 3H), −0.03 (s, 3H).

Intermediate I-106

(R)-2-((1-((tert-butyldimethylsilyl)oxy)propan-2-yl)oxy)pyrimidin-5-amine

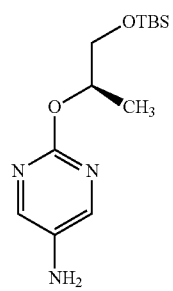
(I-106)

Intermediate I-106A: (R)-2-((5-nitropyrimidin-2-yl)oxy)propan-1-ol, (R)-1-((5-nitropyrimidin-2-yl)oxy)propan-2-ol

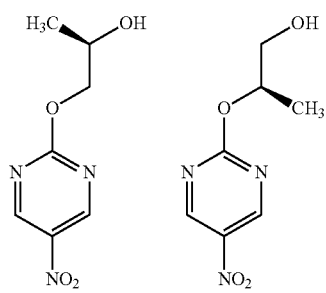
(I-106A)

To a vial containing 2-chloro-5-nitropyrimidine (300 mg, 1.9 mmol) was added DMF (3 mL) followed by (R)-propane-1,2-diol (0.5 mL, 6.81 mmol). Potassium carbonate (520 mg, 3.76 mmol) was then added to the reaction mixture which was allowed to stir vigorously at 65° C. for 1 h. The reaction mixture was then quenched with acetic acid (0.323 mL, 5.64 mmol), diluted with EtOAc and filtered over a pad of silica gel. The filtrate was concentrated before being purified by ISCO (40 g Gold Column, 0-100% EtOAc/Hex) to afford Intermediate I-106A as a mixture of regioisomers (64 mg, 0.32 mmol, 17% yield). LC-MS: Method H, MS (ESI) m/z: 199.6 (M+H)$^+$.

Intermediate I-106B (R)-2-((1-((tert-butyldimethylsilyl)oxy)propan-2-yl)oxy)-5-nitropyrimidine

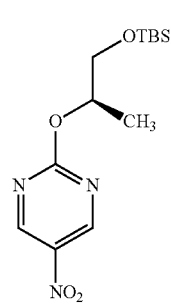
(I-106B)

Intermediate I-106A (64.0 mg, 0.321 mmol) was dissolved in THF (5 mL) along with TEA (0.224 mL, 1.607 mmol) and DMAP (7.85 mg, 0.064 mmol). TBS-Cl (242 mg, 1.607 mmol) was added to the reaction mixture which was allowed to stir for 18 h at room temperature. The reaction mixture was then concentrated and the resulting residue was dissolved in a small amount of methylene chloride and charged to a 24 g silica gel cartridge which was eluted with a 15 min gradient from 0-100% EtOAc in hexane. Fractions containing the desired product concentrated to yield Intermediate I-106B (67 mg, 0.214 mmol, 66.5% yield). LC-MS: Method H, MS (ESI) m/z: 314.1 (M+H)$^+$. $^1$H NMR (400 MHz, CDCl$_3$) δ 9.22 (s, 2H), 5.38 (d, J=4.8 Hz, 1H), 3.83-3.64 (m, 2H), 0.80-0.77 (m, 9H), 0.00 (s, 3H), −0.03 (s, 3H). MS (ESI) m/z 314.1 (M+H).

Intermediate I-106

Intermediate I-106B (67 mg, 0.214 mmol) was dissolved in EtOAc (10 mL). Wet Pd—C (22.75 mg, 0.021 mmol, 10% by wt.) was added to the reaction mixture which was allowed to stir under 1 atm of hydrogen for 6 hours at room temperature. The reaction mixture was then filtered through celite. The filtrate was concentrated to yield Intermediate I-106 (55 mg, 0.194 mmol, 91% yield). The product was brought forward without further purification. LC-MS: Method H, MS (ESI) m/z: 284.2 (M+H)$^+$. $^1$H NMR (400 MHz, CDCl$_3$) δ 7.97 (s, 2H), 5.11-4.82 (m, 1H), 3.80-3.73 (m, 1H), 3.64-3.52 (m, 1H), 3.28 (br. s., 2H), 1.28 (d, J=6.2 Hz, 3H), 0.83-0.77 (m, 9H), 0.00 (s, 3H), −0.03 (s, 3H).

Intermediate I-107

Methyl 5-aminopyrimidine-2-carboxylate

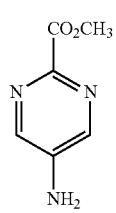
(I-107)

Intermediate I-107A: methyl 5-((diphenylmethylene)amino)pyrimidine-2-carboxylate

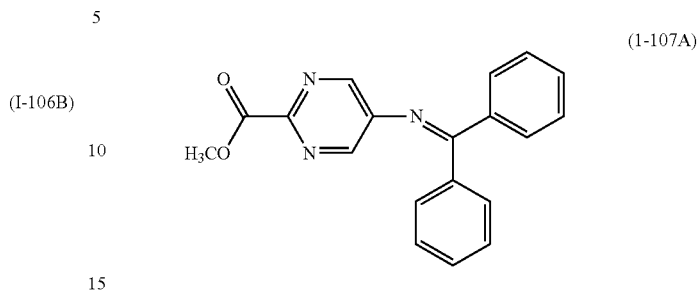
(I-107A)

5-bromopyrimidine-2-carboxylate was reacted according to Procedure B to afford Intermediate I-107A (3.1 g, 9.77 mmol, 70.7% yield) as a yellow solid. LC-MS: Method H, MS (ESI) m/z: 318.1 (M+H)$^+$. $^1$H NMR (500 MHz, CDCl$_3$) δ 8.33 (s, 2H), 7.82 (d, J=6.3 Hz, 2H), 7.72-7.32 (m, 6H), 7.13 (br. s., 2H), 4.04 (s, 3H).

Intermediate I-107

Intermediate I-107A (0.2 g, 0.630 mmol) was solvated in a mixture of THF (5 ml) and MeOH (5.00 ml). To this solution was added 1M aqueous HCl (1.576 ml, 1.576 mmol). After 30 minutes of stirring at room temperature the reaction mixture was diluted with water and the aqueous phase was washed with 4:1 EtOAc/Hexanes (3×) then concentrated to afford the aminopyrimidine HCl salt intermediate. This crude intermediate was dissolved in MeOH and run through solid supported HCO$_3^-$ cartridge (PL-HCO3 MP SCE) to form the free base. The cartridge was washed with MeOH and the resulting solution was concentrated to yield Intermediate I-107 (0.065 g, 0.42 mmol, 67% yield). LC-MS: Method H, MS (ESI) m/z: 154.1 (M+H)$^+$. $^1$H NMR (400 MHz, DMSO-d$_6$) δ 8.16 (s, 2H), 6.38 (s, 2H), 3.80 (s, 3H).

Intermediate I-108

4-((4-aminopyridin-2-yl)oxy)-2-methylbutan-2-ol

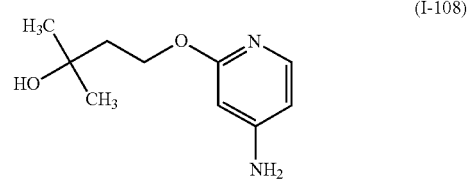
(I-108)

Intermediate I-108A: 4-((4-bromopyridin-2-yl)oxy)-2-methylbutan-2-ol

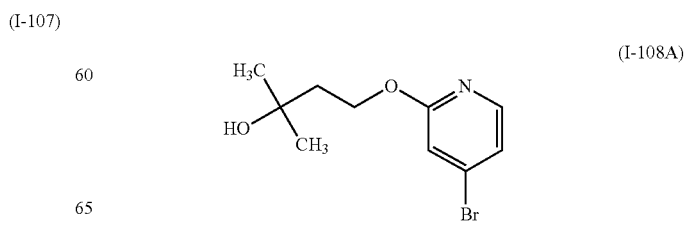
(I-108A)

This intermediate was prepared according to Procedure D from 3-methylbutane-1,3-diol. Intermediate I-108A was afforded in 80% yield after chromatography. LC-MS: Method H, MS (ESI) m/z: 261.9. (M+H)⁺. ¹H NMR (400 MHz, CDCl₃) δ 8.00 (d, J=5.5 Hz, 1H), 7.05 (dd, J=5.5, 1.8 Hz, 1H), 6.96 (d, J=1.5 Hz, 1H), 4.52 (t, J=6.5 Hz, 2H), 2.00 (t, J=6.5 Hz, 2H), 1.32 (s, 6H).

Intermediate I-108

Intermediate I-108 was prepared from Intermediate I-108A according to Procedure E. Intermediate I-108 was afforded in 61% yield after chromatography. LC-MS: Method H, MS (ESI) m/z: 197.0. ¹H NMR (400 MHz, DMSO-d₆) δ 7.60 (d, J=5.7 Hz, 1H), 6.14 (dd, J=5.7, 2.0 Hz, 1H), 5.89 (s, 2H), 5.77 (d, J=1.8 Hz, 1H), 4.33 (s, 1H), 4.21 (t, J=7.4 Hz, 2H), 1.76 (t, J=7.4 Hz, 2H), 1.13 (s, 6H).

Intermediate I-109

6-(2-((tert-butyldimethyl silyl)oxy)ethyl)pyridin-3-amine

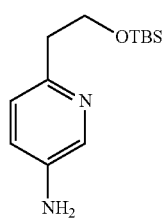

(I-109)

Intermediate I-109A: methyl 2-(5-nitropyridin-2-yl)acetate

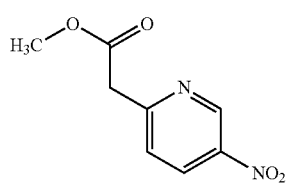

(I-109A)

Tert-butyl methyl malonate (2.64 g, 15.14 mmol) was dissolved in THF (50 mL). Sodium hydride (0.605 g, 15.14 mmol) was added portion-wise at 0° C. and the reaction mixture was allowed to stir for 15 min at room temperature. 2-chloro-5-nitropyridine (2.0 g, 12.61 mmol) dissolved in 10 mL of THF was then added to the mixture and the mixture was allowed to stir for 4 hours at room temperature before being quenched with saturated aqueous ammonium chloride and extracted with EtOAc (3×). The combined organic layer was washed with brine, dried with sodium sulfate, filtered and concentrated. The resulting residue was dissolved in 30 mL of 2:1 DCM/TFA and stirred for 1.5 hours. The reaction mixture was then diluted with 1.5 M potassium phosphate solution and extracted with EtOAc (3×). The combined organic layer was washed with brine, dried with sodium sulfate, filtered and concentrated. The resulting residue was dissolved in methylene chloride before being charged to an 80 g silica gel cartridge which was eluted with a 30 min gradient from 0-100% EtOAc in hexane. Fractions containing the desired product were concentrated to yield Intermediate I-109A (1.06 g, 5.40 mmol, 42.8% yield), as a yellow oil. LC-MS: Method H, MS (ESI) m/z: 197.0 (M+H)⁺. ¹H NMR (400 MHz, CDCl₃) δ 9.41 (d, J=2.6 Hz, 1H), 8.49 (dd, J=8.6, 2.6 Hz, 1H), 7.56 (d, J=8.6 Hz, 1H), 4.02 (s, 2H), 3.78 (s, 3H).

Intermediate I-109B: 2-(5-nitropyridin-2-yl)ethanol

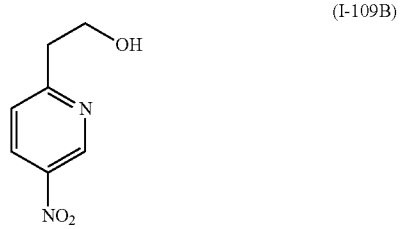

(I-109B)

This intermediate was prepared from Intermediate I-109A using Procedure F. Intermediate I-109B was afforded in quantitative yield and was brought forward without purification. LC-MS: Method H, MS (ESI) m/z: 169.0 (M+H)⁺. ¹H NMR (400 MHz, MeOH-d₄) δ 9.30 (d, J=2.6 Hz, 1H), 8.51 (dd, J=8.6, 2.6 Hz, 1H), 7.64-7.49 (m, 1H), 3.96 (t, J=6.3 Hz, 2H), 3.12 (t, J=6.4 Hz, 2H).

Intermediate I-109C: 2-(2-((tert-butyldimethylsilyl)oxy)ethyl)-5-nitropyridine

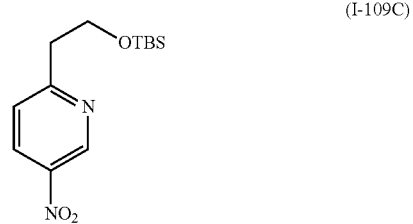 [SMILES: CC(C)(C)[Si](C)(C)OCCc1ccc(N)cn1]

(I-109C)

Intermediate I-109B was reacted according to Procedure I using THF as a solvent to afford Intermediate I-109C (0.150 g, 0.531 mmol, 89% yield) as a yellow oil. LC-MS: Method H, MS (ESI) m/z: 283.1 (M+H)⁺. ¹H NMR (400 MHz, CDCl₃) δ 9.27 (d, J=2.6 Hz, 1H), 8.28 (dd, J=8.6, 2.6 Hz, 1H), 7.32 (d, J=8.6 Hz, 1H), 3.92 (t, J=6.2 Hz, 2H), 3.01 (t, J=6.2 Hz, 2H), 0.81 (s, 9H), 0.00 (s, 6H).

Intermediate I-109

Intermediate I-109C (0.150 g, 0.531 mmol) was dissolved in ethanol (5.3 ml) and Pd—C (0.113 g, 0.106 mmol, 10% by wt.) was added to the solution followed by ammonium formate (0.167 g, 2.66 mmol). The reaction mixture was allowed to stir at reflux for 3 hours and was then filtered over celite and concentrated under reduced pressure to yield Intermediate I-109 (0.075 g, 0.297 mmol, 56% yield). LC-MS: Method H, MS (ESI) m/z: 253.1 (M+H)⁺. ¹H NMR (400 MHz, CDCl₃) δ 8.08 (d, J=2.6 Hz, 1H), 7.02 (s, 1H), 6.99-6.94 (m, 1H), 3.94 (t, J=6.7 Hz, 2H), 3.69-3.54 (m, 2H), 2.92 (s, 2H), 0.89 (s, 9H), 0.00 (s, 6H).

Intermediate I-110

2-(2-((tert-butyldimethylsilyl)oxy)ethoxy)pyridin-4-amine

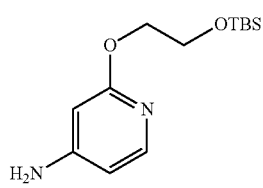
(I-110)

Intermediate I-110A:
2-((4-bromopyridin-2-yl)oxy)ethanol

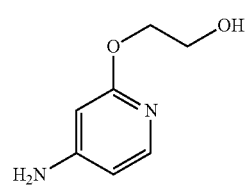
(I-110A)

This intermediate was prepared according to Procedure D from ethane-1,2-diol. Intermediate I-110A was afforded in 78% yield after chromatography. LC-MS: Method H, MS (ESI) m/z: 219.9 (M+H)+. $^1$H NMR (400 MHz, CDCl$_3$) δ 7.98 (d, J=5.5 Hz, 1H), 7.09 (dd, 1.5 Hz, 1H), 7.04 (d, J=1.5 Hz, 1H), 4.51-4.47 (m, 2H), 4.01-3.87 (m, 2H), 3.16 (s, 1H).

Intermediate I-110

Intermediate I-110A was reacted according to Procedure E to afford the 4-aminopyridine intermediate which was brought forward without further purification. To a solution of the crude 4-aminopyridine intermediate (205 mg, 1.330 mmol) dissolved in THF (5 mL) was added DMAP (32.5 mg, 0.266 mmol) and TEA (0.927 mL, 6.65 mmol) followed by TBS-Cl (1002 mg, 6.65 mmol) and the mixture was allowed to stir for 18 h at room temperature. The mixture was then filtered through celite and the filtrate was concentrated. The resulting residue was dissolved in methylene chloride before being charged to a 24 g silica gel cartridge which was eluted with a 15 min gradient from 0-25% 2M NH$_3$/MeOH in methylene chloride. The fractions containing desired product were extracted with saturated sodium bicarbonate (3×) to remove triethyl amine hydrochloride, washed with brine (1×), dried with sodium sulfate, filtered and concentrated to yield Intermediate I-110 (70 mg, 0.261 mmol, 20% yield), as a clear oil. LC-MS: Method H, MS (ESI) m/z: 269.4 (M+H)+. $^1$H NMR (400 MHz, CDCl$_3$) δ 7.89-7.58 (m, 1H), 6.27-6.08 (m, 1H), 6.02-5.63 (m, 1H), 4.28-4.18 (m, 2H), 3.91-3.80 (m, 2H), 0.82 (s, 9H), 0.00 (s, 6H).

Intermediate I-111

(R)-2-(2-((tert-butyldimethylsilyl)oxy)propoxy)pyridin-4-amine, (R)-2-((1-((tert-butyldimethylsilyl)oxy)propan-2-yl)oxy)pyridin-4-amine (Regioisomeric Mixture)

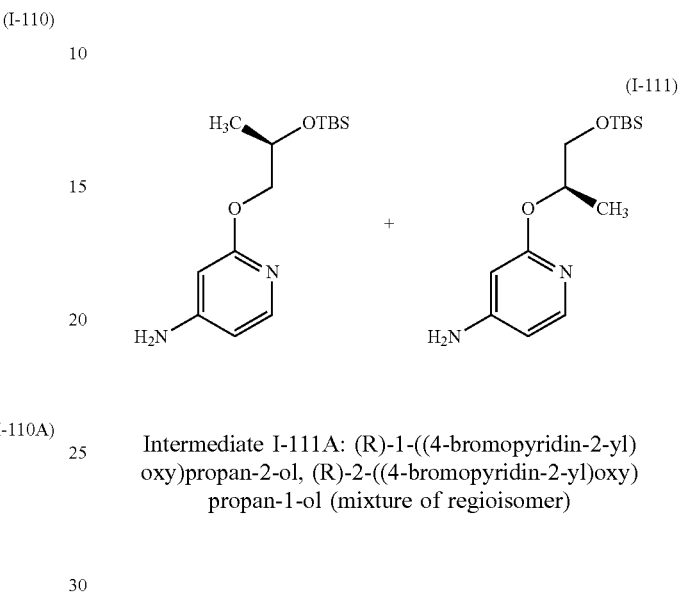
(I-111)

Intermediate I-111A: (R)-1-((4-bromopyridin-2-yl)oxy)propan-2-ol, (R)-2-((4-bromopyridin-2-yl)oxy)propan-1-ol (mixture of regioisomer)

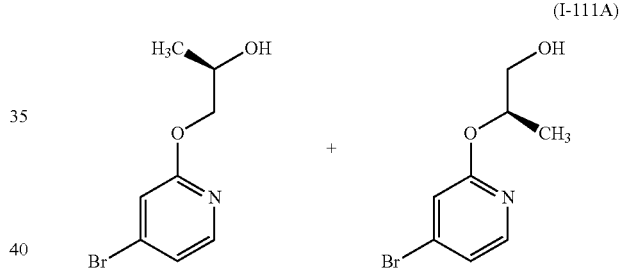
(I-111A)

This intermediate was prepared from (R)-propane-1,2-diol using Procedure D. Intermediate I-111A was afforded as mixture of regioisomers in quantitative yield. LC-MS: Method H, MS (ESI) m/z: 233.9 (M+H)+.

Intermediate I-111

Intermediate I-111A was reacted according to Procedure E to afford the 4-aminopyridine intermediates as a mixture of regioisomers. To the crude mixture of 4-aminopyridine regioisomers (302 mg, 1.8 mmol) dissolved in THF (5 mL) was added DMAP (43.9 mg, 0.359 mmol) and TEA (1.251 mL, 8.98 mmol) followed by TBS-Cl (1353 mg, 8.98 mmol) and the reaction mixture was allowed to stir at room temperature for 18 h. The reaction mixture was then filtered through celite and the filtrate was concentrated. The resulting residue was dissolved in methylene chloride before being charged to a 24 g silica gel cartridge which was eluted with a 15 min gradient from 0-25% 2M NH$_3$/MeOH in methylene chloride. Fractions containing the desired product were concentrated to yield Intermediate I-111 as a mixture (327 mg, 1.2 mmol, 65% yield). LC-MS: Method H, MS (ESI) m/z: 283.0 (M+H)+.

Intermediate I-112

5-(((tert-butyldimethylsilyl)oxy)methyl)-6-methylpyridin-3-amine

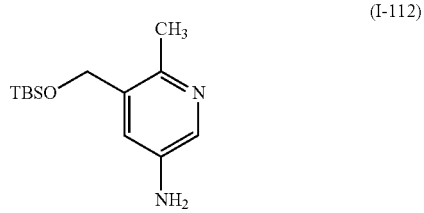 [SMILES: Cc1ncc(N)cc1CO[Si](C)(C)C(C)(C)C]
(I-112)

Intermediate I-112A: ethyl 5-((tert-butoxycarbonyl)amino)-2-methylnicotinate

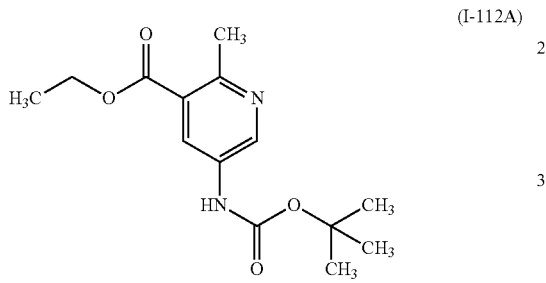
(I-112A)

Tert-butyl carbamate (605 mg, 5.16 mmol), ethyl 5-bromo-2-methylnicotinate (420 mg, 1.72 mmol), xanthphos (100 mg, 0.172 mmol), Pd$_2$(dba)$_3$ (158 mg, 0.172 mmol), cesium carbonate (1121 mg, 3.44 mmol) and tert-butyl carbamate (605 mg, 5.16 mmol) were dissolved in dioxane (10 mL) in a pressure rated vial and evacuated and backfilled with Ar 3×. The reaction mixture was then heated at 85° C. for 18 h. The reaction mixture was then filtered through celite and the filtrate was concentrated. The resulting residue was dissolved in a small amount of methylene chloride before being charged to a 4 g silica gel cartridge which was eluted with a 15 min gradient from 0-100% EtOAc in hexane. Fractions containing the desired product were concentrated to yield Intermediate I-112A in quantitative yield. $^1$H NMR (400 MHz, CDCl$_3$) δ 8.44 (d, J=2.6 Hz, 1H), 8.32-8.24 (m, 1H), 6.49-6.31 (m, 1H), 4.31 (q, J=7.3 Hz, 2H), 1.46 (s, 9H), 1.33 (t, J=7.2 Hz, 3H).

Intermediate I-112

Intermediate I-112A (555 mg, 1.4 mmol) was dissolved in DCM (10 mL)/TFA (2.5 mL) and the solution was stirred for 30 minutes at room temperature. The reaction mixture was then concentrated to yield the deprotected aminopyridine intermediate. This crude intermediate was dissolved in THF (20 mL) at 0° C. under Ar. 1M LAH in THF (12.94 mL, 12.94 mmol) was added dropwise to the reaction mixture and the reaction mixture was allowed to stir at room temperature for 1.5 hours. The reaction mixture was then cooled to 0° C. and quenched with 0.5 mL of water, 1 mL of 3N NaOH and then 5 mL of water. Magnesium sulfate was added to the quenched mixture, which stirred for 10 minutes before being filtered through celite and concentrated to yield the alcohol intermediate. To the crude alcohol dissolved in DCM (10 mL) was added imidazole (308 mg, 4.53 mmol) followed by TBS-Cl (634 mg, 4.21 mmol). The reaction mixture was stirred at room temperature for 1 hour and was then concentrated to dryness. The resulting residue was dissolved in a small amount of methylene chloride before being charged to a 12 g silica gel cartridge which was eluted with a 15 min gradient from 0-100% EtOAc in hexane. Fractions containing desired product were concentrated to yield Intermediate I-112 (22 mg, 0.087 mmol, 3% yield). LC-MS: Method H, MS (ESI) m/z: 253.2 (M+H)$^+$.

Intermediate I-113

(R)-2-((2,2-dimethyl-1,3-dioxolan-4-yl)methoxy)pyrimidin-5-amine

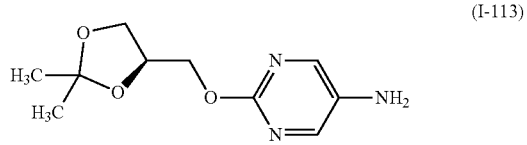 [SMILES: CC1(C)OC[C@@H](COc2ncc(N)cn2)O1]
(I-113)

Intermediate I-113A: (R)-5-bromo-2-((2,2-dimethyl-1,3-dioxolan-4-yl)methoxy) pyrimidine

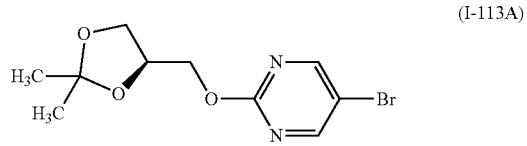 [SMILES: CC1(C)OC[C@@H](COc2ncc(Br)cn2)O1]
(I-113A)

(R)-(2,2-dimethyl-1,3-dioxolan-4-yl)methanol (189 mg, 1.429 mmol) was reacted with 5-bromopyrimidin-2-ol (250 mg, 1.429 mmol) according to the procedure described for Intermediate I-104C. After silica gel chromatography, Intermediate I-113A (315 mg, 1.089 mmol, 76% yield) was yielded as a colorless oil. LC-MS: Method H, MS (ESI) m/z: 290.1 (M+H)$^+$. $^1$H NMR (400 MHz, CDCl$_3$) δ 8.53 (s, 1H), 4.54-4.46 (m, 1H), 4.46-4.40 (m, 1H), 4.38-4.31 (m, 1H), 4.15 (dd, J=8.6, 6.4 Hz, 1H), 3.93 (dd, 5.6 Hz, 1H), 1.45 (s, 3H), 1.38 (s, 3H).

Intermediate I-113B (R)-2-((2,2-dimethyl-1,3-dioxolan-4-yl)methoxy)-N-(diphenylmethylene)pyrimidin-5-amine

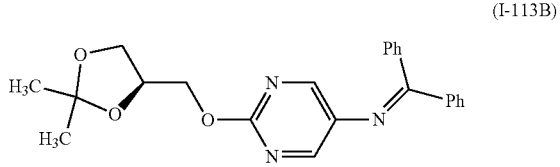 [SMILES: CC1(C)OC[C@@H](COc2ncc(N=C(c3ccccc3)c3ccccc3)cn2)O1]
(I-113B)

Intermediate I-113A ((315 mg, 1.089 mmol) was reacted according to Procedure B to afford Intermediate I-113B, (300 mg, 1.089 mmol, 71% yield). LC-MS: Method H, MS (ESI) m/z: 390.1 (M+H)+. 1H NMR (400 MHz, CDCl3) δ 7.95 (s, 1H), 7.79-7.72 (m, 1H), 7.53-7.47 (m, 1H), 7.45-7.39 (m, 2H), 7.38-7.31 (m, 3H), 7.16-7.09 (m, 2H), 4.50-4.42 (m, 1H), 4.38-4.31 (m, 1H), 4.29-4.23 (m, 1H), 4.15-4.08 (m, 1H), 3.91 (dd, J=8.6, 5.7 Hz, 1H), 1.45-1.41 (m, 3H), 1.39-1.35 (m, 3H).

Intermediate I-113

Intermediate I-113B (300 mg, 0.770 mmol) was solvated in MeOH with 0.1% TFA (8 mL) and the solution was stirred vigorously. After 30 min of stirring, the reaction mixture was passed through a PL-HCO3 ion exchange cartridge and washed with MeOH to remove the TFA. The resulting solution was concentrated and azeotroped with toluene to afford a 1:1 mixture of Intermediate I-113 and benzophenone (115 mg, 0.631 mmol, 82% yield). The intermediate was brought forward without further purification. LC-MS: Method H, MS (ESI) m/z: 226.1 (M+H)+. 1H NMR (400 MHz, CDCl3) δ 8.03 (s, 1H), 4.55-4.44 (m, 1H), 4.41-4.33 (m, 1H), 4.30-4.21 (m, 1H), 4.15 (dd, J=8.6, 6.2 Hz, 1H), 3.93 (dd, J=8.5, 5.8 Hz, 1H), 1.45 (s, 3H), 1.38 (s, 3H).

Intermediate I-114

(S)-2-((2,2-dimethyl-1,3-dioxolan-4-yl)methoxy)pyrimidin-5-amine

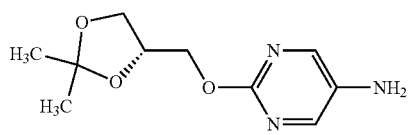
(I-114)

Intermediate I-114 was prepared using the same reaction sequence as described for I-113. LC-MS: Method H, MS (ESI) m/z: 226.2 (M+H)+. 1H NMR (400 MHz, CDCl3) δ 8.03 (s, 1H), 4.55-4.44 (m, 1H), 4.41-4.33 (m, 1H), 4.30-4.21 (m, 1H), 4.15 (dd, J=8.6, 6.2 Hz, 1H), 3.93 (dd, J=8.5, 5.8 Hz, 1H), 1.45 (s, 3H), 1.38 (s, 3H).

Intermediate I-115

N2,N2-dimethylpyrimidine-2,5-diamine, 2 HCl

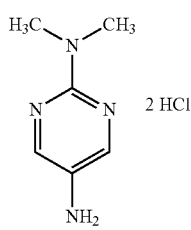
(I-115)

Intermediate I-115A: N5-(diphenylmethylene)-N2,N2-dimethylpyrimidine-2,5-diamine

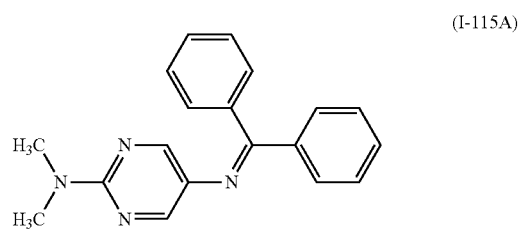 [SMILES: CN(C)c1ncc(N=C(c2ccccc2)c2ccccc2)cn1]
(I-115A)

5-bromo-N,N-dimethylpyrimidin-2-amine (200 mg, 1.0 mmol) was reacted according to Procedure B to afford Intermediate I-115A, (70 mg, 0.23 mmol, 24% yield) after chromatography. LC-MS: Method H, MS (ESI) m/z: 303.2 (M+H)+.

Intermediate I-115

Intermediate I-115A was reacted according to Procedure C to afford Intermediate I-115 in quantitative yield. This intermediate was brought forward without further purification. LC-MS: Method H, MS (ESI) m/z: 138.9 (M+H)+.

Intermediate I-116

N-(5-aminopyrimidin-2-yl)-N-methylmethanesulfonamide

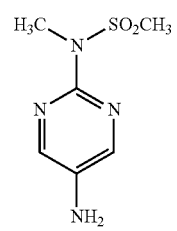
(I-116)

Intermediate I-116A: N-(5-bromopyrimidin-2-yl)-N-methylmethanesulfonamide

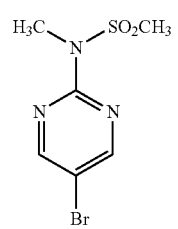
(I-116A)

To a solution of 5-bromo-N-methylpyrimidin-2-amine (2.55 g, 13.56 mmol) in DMF (30 mL) at 0° C. was added NaH (0.705 g, 17.63 mmol) portion-wise. The mixture was stirred for 30 min at 0° C. Methanesulfonyl chloride (1.864 g, 16.27 mmol) was then added dropwise. The mixture was warmed to room temperature and stirred for an additional 2 h at room temperature. The reaction mixture was then quenched with water (10 mL) at 0° C. and then extracted with EtOAc (3×30 mL). The combined organic layer was washed with brine (30 mL), dried over MgSO$_4$, filtered, and concentrated. This resulting residue was dissolved in a small amount of methylene chloride before being charged to an 80 g column which was eluted with 1% MeOH in DCM. Fractions containing the desired product were concentrated to yield Intermediate I-116A (1.26 g, 35% yield). LC-MS: Method H, MS (ESI) m/z: 268.0 (M+H)$^+$.

Intermediate I-116

Intermediate I-116A was reacted according to Procedure B to provide to the desired imine intermediate after silica gel chromatography. This imine intermediate was reacted according to Procedure C to afford the desired product which was brought forward without further purification. LC-MS: Method H, MS (ESI) m/z: 203.0 (M+H)$^+$.

Intermediate I-117 methyl 3-(5-aminopyrimidin-2-yl)propanoate

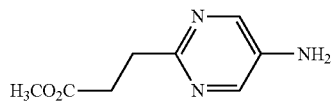

(I-117)

Intermediate I-117A: 5-((diphenylmethylene)amino)pyrimidine-2-carbaldehyde

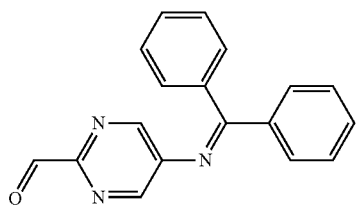

(I-117A)

Intermediate I-107A (1.1 g, 3.47 mmol) was dissolved in THF (50 ml) and the mixture was cooled to −78° C. DIBAL-H (10.40 ml, 10.40 mmol) was added to the mixture which was allowed to stir for 1 hour at −78° C. The reaction mixture was then quenched with saturated Rochelle's salt at −78° C. and the resulting slurry was allowed to stir overnight under a stream of Ar. The mixture was then extracted with EtOAc (3×) and the combined organic layer was washed with brine, dried with sodium sulfate, filtered through celite and concentrated to yield Intermediate I-117A in quantitative yield. LC-MS: Method H, MS (ESI) m/z: 154.1 (M+H)$^+$. $^1$H NMR (400 MHz, DMSO-d$_6$) δ 8.17 (s, 2H), 3.80 (s, 3H).

Intermediate I-117B: (E)-methyl 3-(5-((diphenylmethylene)amino)pyrimidin-2-yl)acrylate

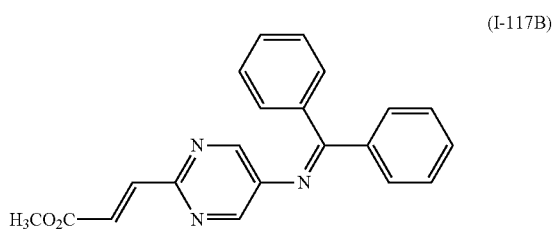 [SMILES: COC(=O)/C=C/c1ncc(N=C(c2ccccc2)c2ccccc2)cn1]

(I-117B)

Methyl 2-(dimethoxyphosphoryl)acetate (0.190 g, 1.044 mmol) was dissolved in THF (10 mL). 60% sodium hydride in mineral oil (0.042 g, 1.044 mmol) was added to the solution at 0° C. and the solution was allowed to stir at 0° C. for 20 minutes. Intermediate I-117A (0.25 g, 0.870 mmol) dissolved in 2 mL of THF was then added to the reaction mixture at 0° C. which was then allowed to warm to room temperature and stir for 5 minutes. The reaction mixture was then quenched with saturated ammonium chloride and extracted with EtOAc (3×). The combined organic layer was washed with brine, dried with sodium sulfate, filtered and concentrated. The resulting residue was dissolved in a small amount of methylene chloride and charged to a 24 g silica gel cartridge which was eluted with a 15 min gradient from 0-100% EtOAc in hexane. Fractions containing desired product were collected and concentrated to yield Intermediate I-117B (250 mg, 0.728 mmol, 84% yield) as a yellow solid. LC-MS: Method H, MS (ESI) m/z: 344.2 (M+H)$^+$. $^1$H NMR (400 MHz, CDCl$_3$) δ 8.18 (s, 2H), 7.84-7.71 (m, 3H), 7.60 (d, J=15.8 Hz, 1H), 7.55-7.29 (m, 8H), 7.17-7.09 (m, 3H), 7.02 (d, J=15.6 Hz, 1H), 3.80 (s, 3H).

Intermediate I-117

Intermediate I-117B (170 mg, 0.495 mmol) was dissolved in MeOH (10 mL)/water (0.5 mL). TFA (0.038 mL, 0.495 mmol) was added to the solution which was allowed to stir at room temperature for 2.5 h. The reaction mixture was concentrated. The resulting free aniline intermediate was then dissolved in ethanol (10 mL)/ethyl acetate (10 mL) and Hunig's Base (0.432 mL, 2.473 mmol) was added to the solution. Wet Pd—C (25 mg, 0.235 mmol, 10% by wt.) was then added to the reaction mixture which was evacuated and backfilled with 1 atm of hydrogen 3×. The reaction mixture was allowed to stir for 1 h under 1 atm of hydrogen at room temperature. The mixture was then filtered through a pad of celite, concentrated and the resulting residue was dissolved in methylene chloride and charged to a 12 g silica gel cartridge which was eluted with a 15 min gradient from 0-20% MeOH in methylene chloride. Fractions containing the desired product were collected and concentrated to yield Intermediate I-117 (30 mg, 0.166 mmol, 34% yield). LC-MS: Method H, MS (ESI) m/z: 182.1 (M+H)$^+$. $^1$H NMR (400 MHz, CDCl$_3$) δ 8.17 (s, 2H), 3.70 (s, 3H), 3.60 (br. s., 2H), 3.22 (t, J=7.4 Hz, 2H), 2.86 (t, J=7.4 Hz, 2H).

Intermediate I-118 methyl 5-(((((2R,3S)-3-((5-fluoro-2-(2-methoxy-7-methylquinoxalin-5-yl)benzo[d]thiazol-6-yl)oxy)butan-2-yl)oxy)carbonyl)amino)nicotinate

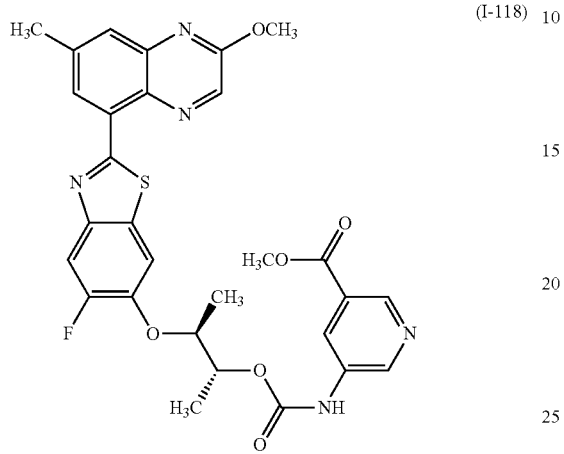

Intermediate I-118 was prepared from Intermediate I-72 and methyl 5-aminonicotinate according to the procedure described in the table of carbamate examples below. LC-MS: Method H, MS (ESI) m/z: 593.0 (M+H)$^+$.

Intermediate I-119

5-(((tert-butyldimethylsilyl)oxy)methyl)pyridin-3-amine

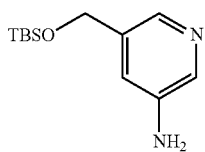

Methyl 5-aminonicotinate (250 mg, 1.643 mmol) was dissolved in THF (20 mL) at 0° C. LAH (6.57 mL, 6.57 mmol, 1 M in THF) was added dropwise to the solution over 2 minutes. The reaction mixture was then allowed to warm to room temperature and stirred at room temperature for 1.5 hours. The reaction mixture was then quenched water at 0° C. (1 mL), followed by addition of 1M NaOH (2 mL) and an additional 4 mL of water. The quenched reaction mixture was stirred for 10 minutes at room temperature then magnesium sulfate was added. The mixture was filtered through celite and the filtrate was concentrated to yield the intermediate alcohol. This crude alcohol intermediate was reacted according to Procedure I to yield Intermediate I-119 (251 mg, 1.05 mmol, 65% yield) after silica chromatography. LC-MS: Method H, MS (ESI) m/z: 239.2 (M+H)$^+$.

Intermediate I-120

(2R,3S)-3-((5-fluoro-2-(2-methoxy-7-methylquinoxalin-5-yl)benzo[d]thiazol-6-yl) oxy)butan-2-yl (2-formylpyrimidin-5-yl)carbamate

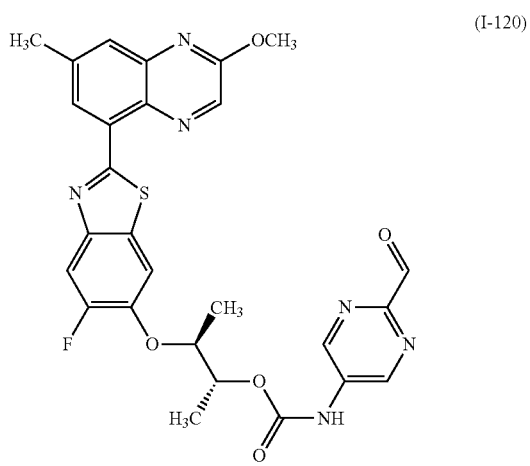 [SMILES: COc1cnc2c(-c3nc4cc(F)c(O[C@@H](C)[C@@H](C)OC(=O)Nc5cnc(C=O)nc5)cc4s3)cc(C)cc2n1]

Intermediate I-86 (16 mg, 0.027 mmol) was dissolved in THF (5 mL) and cooled –78° C. DIBAL-H (0.135 mL, 0.135 mmol) was added to the reaction mixture dropwise which was then allowed to stir at –78° C. for 1 hour. The mixture was then quenched with saturated Rochelle's salt and stirred for 30 min. at room temperature. The resulting mixture was extracted with EtOAc (3×) and the combined organic layer was washed with brine, dried with sodium sulfate, filtered and concentrated to yield Intermediate I-120 (5 mg, 8.89 μmol, 32.9% yield). The product was brought forward without further purification. LC-MS: Method H, MS (ESI) m/z: 562.9 (M+H)$^+$. $^1$H NMR (400 MHz, CDCl$_3$) δ 9.92 (s, 1H), 8.99 (s, 2H), 8.53-8.28 (m, 2H), 7.77-7.60 (m, 2H), 7.42 (d, J=7.7 Hz, 1H), 6.91 (s, 1H), 5.17-5.05 (m, 1H), 4.66-4.46 (m, 1H), 4.13-3.83 (m, 3H), 2.56 (s, 3H), 1.47-1.39 (m, 3H), 1.35-1.33 (m, 3H).

Intermediate I-121

6-chloro-3-methoxy-8-(4,4,5,5-tetramethyl-1,3,2-dioxaborolan-2-yl)quinoline

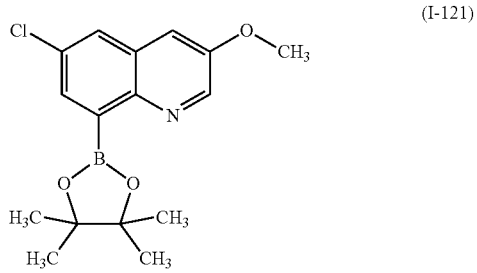 [SMILES: COc1cnc2c(B3OC(C)(C)C(C)(C)O3)cc(Cl)cc2c1]

Intermediate I-121A:
8-bromo-6-chloro-3-methoxyquinoline

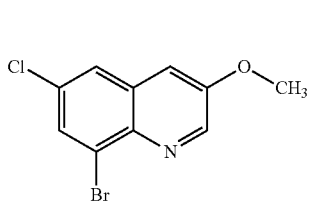

(I-121A)

Intermediate I-122 (2 g, 6.78 mmol), potassium carbonate (2.81 g, 20.3 mmol), and methyl iodide (0.848 mL, 13.6 mmol) were dissolved in acetone (67.8 mL) and heated to 50° C. in a sealed tube. After heating overnight, the reaction mixture was diluted with EtOAc, washed with water, then brine, dried (Na$_2$SO$_4$), filtered, and concentrated in vacuo to give I-121A (2.04 g, 7.48 mmol) as a yellow solid: $^1$H NMR (400 MHz, CDCl$_3$) δ 8.76 (d, J=2.6 Hz, 1H), 7.86 (d, J=2.2 Hz, 1H), 7.70 (d, J=2.2 Hz, 1H), 7.29 (d, J=2.9 Hz, 1H), 3.97 (s, 3H); LC-MS: Method H, RT=1.07 min, MS (ESI) m/z: 272/274 (M+H)$^+$.

Intermediate I-121

Intermediate I-121A (1 g, 3.67 mmol), bispinacolatodiboron (1.86 g, 7.34 mmol), potassium acetate (0.900 g, 9.17 mmol), and PdCl$_2$(dppf)-CH$_2$Cl$_2$ adduct (0.240 g, 0.294 mmol) were stored on HIVAC for 15 minutes then were dissolved in dry 1,4-dioxane (18.4 mL) and degassed for 15 minutes by bubbling with argon. The reaction mixture was heated to 130° C. in the microwave for 40 minutes. The reaction mixture was diluted with EtOAc and washed with water then brine, dried (Na$_2$SO$_4$), filtered, and concentrated in vacuo. The crude material was purified by column chromatography (ISCO, 80 g silica gel column, 29 minute gradient from 0 to 100% EtOAc in DCM, followed by 0 to 20% MeOH in DCM) to give Intermediate I-121 (368 mg, 1.15 mmol, 31.4%) as a brown solid: LC-MS: Method H, RT=0.81 min, MS (ESI) m/z: 237.9 (boronic acid mass observed, M+H)$^+$.

Intermediate I-122

8-bromo-6-chloroquinolin-3-ol, HCl

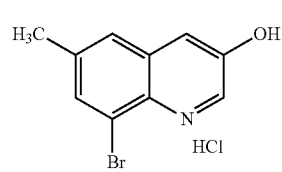

(I-122)

Intermediate I-122A:
3-(benzyloxy)-8-bromo-6-chloroquinoline

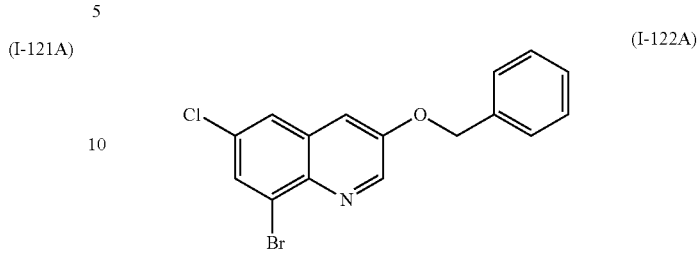

(I-122A)

Intermediate I-123 (5 g, 21.32 mmol), 2-(benzyloxy)acetaldehyde (3.20 g, 21.3 mmol), and sodium methoxide solution (0.5 M in MeOH, 46.9 mL, 23.5 mmol) were dissolved in MeOH (42.6 mL) and heated to reflux. After heating overnight, the reaction mixture was diluted with saturated NH$_4$Cl, partially concentrated in vacuo and diluted with EtOAc. The layers were separated and the organic layer was washed with brine, dried (Na$_2$SO$_4$), filtered, and concentrated in vacuo. The crude material was purified by column chromatography (ISCO, 330 g silica gel column, 30 minute gradient from 0 to 17% EtOAc in hexanes) to give Intermediate I-122A (4.97 g, 14.3 mmol, 67%) as a yellow solid: $^1$H NMR (500 MHz, CDCl$_3$) δ 8.85 (d, J=2.8 Hz, 1H), 7.89 (d, J=1.9 Hz, 1H), 7.69 (d, J=2.2 Hz, 1H), 7.52-7.48 (m, 2H), 7.48-7.43 (m, 2H), 7.43-7.38 (m, 1H), 7.37 (d, J=2.8 Hz, 1H), 5.24 (s, 2H); LC-MS: Method H, RT=1.46 min, MS (ESI) m/z: 348/350 (M+H)$^+$.

Intermediate I-122

Intermediate I-122A (4.87 g, 14 mmol) and pentamethylbenzene (14.5 g, 98 mmol) were dissolved in DCM (279 mL) and cooled to −78° C. Boron trichloride (1 M in heptane, 36.3 mL, 36.3 mmol) was then added and the reaction mixture was allowed to slowly warm to ambient temperature. After stirring overnight, the reaction mixture was diluted with hexanes and 1 N HCl and allowed to stir for 1 hour. The resulting solid was collected by suction filtration, rinsing with water and hexanes to give Intermediate I-122 (3.39 g, 11.5 mmol, 82%) as an off-white solid: $^1$H NMR (400 MHz, MeOH$_4$) δ 8.59 (d, J=2.6 Hz, 1H), 7.84 (d, J=2.2 Hz, 1H), 7.80 (d, J=2.0 Hz, 1H), 7.47 (d, J=2.6 Hz, 1H); LC-MS: Method H, RT=0.92 min, MS (ESI) m/z: 258/260 (M+H)$^+$.

Intermediate I-123

2-amino-3-bromo-5-chlorobenzaldehyde

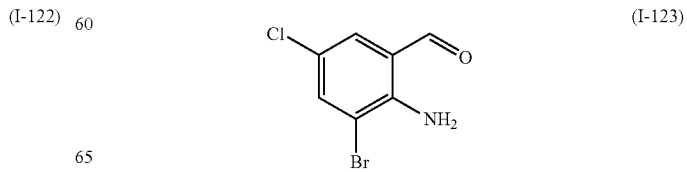

(I-123)

Intermediate I-123A: methyl 2-amino-3-bromo-5-chlorobenzoate

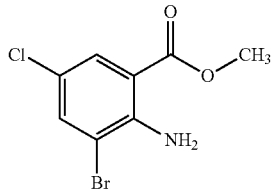

(I-123A)

Methyl 2-amino-5-chlorobenzoate (18.1 g, 97 mmol) and NBS (17.3 g, 97 mmol) were dissolved in AcOH (195 mL) and heated to 120° C. After 1.5 hours, the reaction mixture was cooled to ambient temperature and diluted with EtOAc. The reaction was then quenched with vigorous stirring with saturated NaHCO$_3$. The layers were separated and the organic layer further washed with brine, dried (Na$_2$SO$_4$), filtered, and concentrated in vacuo to give Intermediate I-123A (25.7 g, 97 mmol, 100%) as a yellow solid: $^1$H NMR (400 MHz, CDCl$_3$) δ 7.87 (d, J=2.4 Hz, 1H), 7.59 (d, J=2.4 Hz, 1H), 6.36 (br. s., 2H), 3.92 (s, 3H); LC-MS: Method H, RT=1.20 min, MS (ESI) m/z: 264/266 (M+H)$^+$.

Intermediate I-123B: (2-amino-3-bromo-5-chlorophenyl)methanol

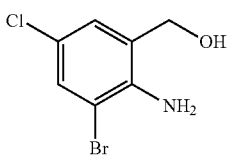

(I-123B)

Intermediate I-123A (25.7 g, 97 mmol) was dissolved in THF (324 mL). Lithium borohydride (4.23 g, 194 mmol) was added and the reaction mixture was heated to 50° C. After 2 hours, the reaction mixture was diluted with water and stirred for 30 minutes. All of the lithium borohydride had not dissolved, so concentrated HCl was added carefully to speed up the quenching process. The reaction mixture was then extracted thrice with EtOAc. The combined organic layers were washed with brine, dried (Na$_2$SO$_4$), filtered, and concentrated in vacuo to give Intermediate I-123B (23.9 g, 101 mmol, 100%) as a white solid: $^1$H NMR (400 MHz, CDCl$_3$) δ 7.43 (d, J=2.4 Hz, 1H), 7.05 (d, J=2.4 Hz, 1H), 4.72 (br. s., 2H), 4.68 (d, J=5.9 Hz, 2H), 1.63 (t, J=5.8 Hz, 1H); LC-MS: Method H, RT=1.11 min, MS (ESI) m/z: 236/238 (M+H)$^+$.

Intermediate I-123

Intermediate I-123B (23.9 g, 101 mmol) was dissolved in CHCl$_3$ (674 mL). Manganese dioxide (17.6 g, 202 mmol) was added and the reaction mixture was heated to 40° C. After heating for 2 days, more manganese dioxide (17.6 g, 202 mmol) was added and heating was continued. After heating overnight, the reaction mixture was filtered through celite and concentrated in vacuo to give Intermediate I-123 (22 g, 94 mmol, 93%) as a yellow solid: $^1$H NMR (400 MHz, CDCl$_3$) δ 9.79 (s, 1H), 7.64 (d, J=2.4 Hz, 1H), 7.49 (d, J=2.4 Hz, 1H), 6.70 (br. s., 2H); LC-MS: Method H, RT=1.27 min, compound did not ionize.

Intermediate I-124

3-methoxy-6-methyl-8-(4,4,5,5-tetramethyl-1,3,2-dioxaborolan-2-yl)quinoline

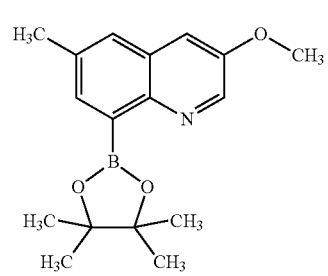

(I-124)

Intermediate I-125 (183 mg, 0.726 mmol), bispinacolatodiboron (369 mg, 1.45 mmol), potassium acetate (178 mg, 1.82 mmol), and PdCl$_2$(dppf)-CH$_2$Cl$_2$ adduct (47.4 mg, 0.058 mmol) were stored on HIVAC for 15 minutes then were dissolved in dry 1,4-dioxane (7.26 mL) and degassed for 15 minutes by bubbling with argon. The reaction mixture was heated to 130° C. in the microwave for 40 minutes. The reaction mixture was diluted with EtOAc and washed with water then brine, dried (Na$_2$SO$_4$), filtered, and concentrated in vacuo. The crude material was purified by column chromatography (ISCO, 24 g silica gel column, 19 minute gradient from 0 to 100% EtOAc in DCM then 0 to 20% MeOH in DCM) to give Intermediate I-124 (108 mg, 0.36 mmol, 50%) as a brown solid: LC-MS: Method H, RT=0.80 min, MS (ESI) m/z: 218.0 (boronic acid observed, M+H)$^+$.

Intermediate I-125

8-bromo-3-methoxy-6-methylquinoline

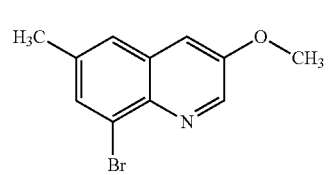

(I-125)

Intermediate I-125A: methyl 2-amino-3-bromo-5-methylbenzoate

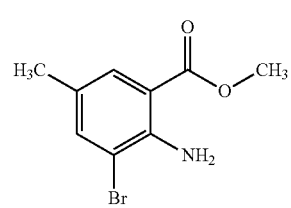

(I-125A)

2-Amino-3-bromo-5-methylbenzoic acid (3.8 g, 16.5 mmol) was dissolved in MeOH (33.0 mL). Thionyl chloride (3.62 mL, 49.6 mmol) was added carefully dropwise and the reaction mixture was heated to 65° C. After stirring for 8 days, the reaction mixture was concentrated in vacuo. The crude material was redissolved in EtOAc, washed with 1 N NaOH, water, then brine, dried ($Na_2SO_4$), filtered, and concentrated in vacuo to give Intermediate I-125A (3.38 g, 13.9 mmol, 84%) as an orange oil: $^1$H NMR (400 MHz, $CDCl_3$) δ 7.66 (d, J=1.1 Hz, 1H), 7.43 (d, J=1.8 Hz, 1H), 6.14 (br. s., 2H), 3.88 (s, 3H), 2.22 (s, 3H); LC-MS: Method H, RT=1.18 min, MS (ESI) m/z: 244/246 $(M+H)^+$.

Intermediate I-125B:
(2-amino-3-bromo-5-methylphenyl)methanol

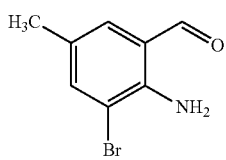

(I-125B)

Intermediate I-125A (3.38 g, 13.8 mmol) was dissolved in THF (46.2 mL). Lithium borohydride (0.603 g, 27.7 mmol) was added and the reaction mixture was heated to 50° C. After 1 hour, the reaction mixture was diluted with water and stirred for 30 minutes. All of the lithium borohydride had not dissolved, so concentrated HCl was added carefully to speed up the quenching process. The reaction mixture was then extracted thrice with EtOAc. The combined organic layers were washed with brine, dried ($Na_2SO_4$), filtered, and concentrated in vacuo to give Intermediate I-125B (2.85 g, 13.2 mmol, 95%) as a white solid: $^1$H NMR (400 MHz, $CDCl_3$) δ 7.23 (d, J=1.1 Hz, 1H), 6.84 (d, J=1.3 Hz, 1H), 4.65 (s, 2H), 4.53 (br. s., 2H), 2.22 (s, 3H); LC-MS: Method H, RT=1.00 min, MS (ESI) m/z: 216/218 $(M+H)^+$.

Intermediate I-125C:
2-amino-3-bromo-5-methylbenzaldehyde

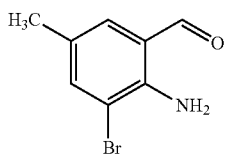

(I-125C)

Intermediate I-125B (2.85 g, 13.2 mmol) was dissolved in $CHCl_3$ (88 mL). Manganese dioxide (6.88 g, 79 mmol) was added and the reaction mixture was heated to 40° C. After heating overnight, the reaction mixture was filtered through celite and concentrated in vacuo to give Intermediate I-125C (2.72 g, 12.7 mmol, 96%) as a yellow solid: $^1$H NMR (400 MHz, $CDCl_3$) δ 9.78 (s, 1H), 7.47 (d, J=1.5 Hz, 1H), 7.28-7.26 (m, 1H), 6.49 (br. s., 2H), 2.28 (s, 3H); LC-MS: Method H, RT=1.26 min, MS (ESI) m/z: 214/216 $(M+H)^+$.

Intermediate I-125D:
3-(benzyloxy)-8-bromo-6-methylquinoline

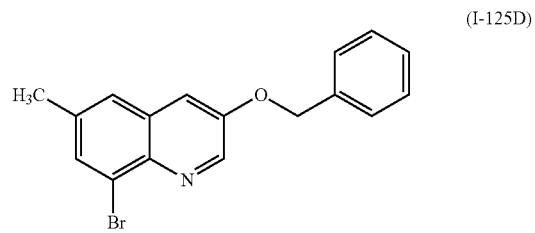 [SMILES: Cc1cc(Br)c2ncc(OCc3ccccc3)cc2c1]

(I-125D)

Intermediate I-125C (2.72 g, 12.7 mmol), 2-(benzyloxy)acetaldehyde (1.91 g, 12.7 mmol), and sodium methoxide (0.5 M in MeOH, 28.0 mL, 13.98 mmol) were dissolved in MeOH (50.8 mL) and heated to reflux. After heating overnight, the reaction mixture was diluted with saturated $NH_4Cl$, partially concentrated in vacuo and diluted with EtOAc. The layers were separated and the organic layer was washed with brine, dried ($Na_2SO_4$), filtered, and concentrated in vacuo. The crude material was purified by column chromatography (ISCO, 220 g silica gel column, 41 minute gradient from 0 to 40% EtOAc in hexanes) to give Intermediate I-125D (1.86 g, 5.67 mmol, 45%) as a yellow solid: $^1$H NMR (400 MHz, $CDCl_3$) δ 8.79 (d, J=2.9 Hz, 1H), 7.74 (d, J=1.5 Hz, 1H), 7.51-7.46 (m, 2H), 7.45-7.40 (m, 3H), 7.39-7.33 (m, 2H), 5.20 (s, 2H), 2.49 (s, 3H); LC-MS: Method H, RT=1.22 min, MS (ESI) m/z: 328/330 $(M+H)^+$.

Intermediate I-125E:
8-bromo-6-methylquinolin-3-ol

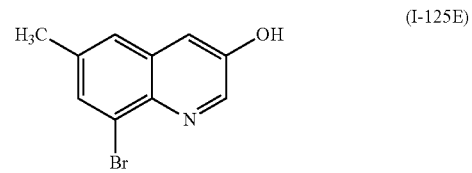

(I-125E)

Intermediate I-125D (1.86 g, 5.67 mmol) and pentamethylbenzene (5.88 g, 39.7 mmol) were dissolved in DCM (113 mL) and cooled to −78° C. Boron trichloride (1 M in heptane, 14.7 mL, 14.7 mmol) was added and the reaction mixture was allowed to warm slowly to ambient temperature. After stirring overnight, the reaction mixture was diluted with hexanes and 1 N HCl and allowed to stir for 1 hour. The aqueous layer still contained product by LCMS. The aqueous layer was neutralized with NaOH until approximately pH 7 and copious amounts of precipitates were formed. The precipitate was collected by suction filtration to give I-125E (829 mg, 3.48 mmol, 62%) as an off-white solid: $^1$H NMR (400 MHz, $MeOH_4$) δ 8.50 (d, J=2.6 Hz, 1H), 7.72 (s, 1H), 7.51 (s, 1H), 7.43 (d, J=1.8 Hz, 1H), 2.47 (s, 3H); LC-MS: Method H, RT=0.82 min, MS (ESI) m/z: 238/240 $(M+H)^+$.

Intermediate I-125

Intermediate I-125E (200 mg, 0.728 mmol), $K_2CO_3$ (302 mg, 2.18 mmol), and methyl iodide (91 μl 1.46 mmol) were dissolved in acetone (7.29 mL) and heated to 50° C. in a sealed tube. After heating overnight, the reaction mixture was diluted with EtOAc, washed with water, then brine, dried (Na$_2$SO$_4$), filtered, and concentrated in vacuo to give Intermediate I-125 (207 mg, 0.82 mmol, 100%) as a yellow solid: $^1$H NMR (400 MHz, CDCl$_3$) δ 8.71 (d, J=2.9 Hz, 1H), 7.74 (d, J=1.8 Hz, 1H), 7.46 (s, 1H), 7.29 (d, J=2.9 Hz, 1H), 3.95 (s, 3H), 2.50 (s, 3H); LC-MS: Method H, RT=1.06 min, MS (ESI) m/z: 252/254 (M+H)$^+$.

Intermediate I-126

6-chloro-3-ethoxy-8-(4,4,5,5-tetramethyl-1,3,2-dioxaborolan-2-yl)quinoline

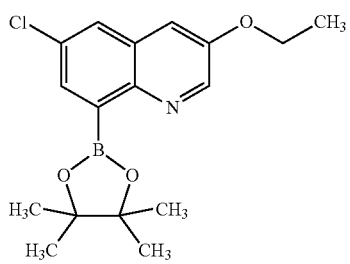

Intermediate I-126A:
8-bromo-6-chloro-3-ethoxyquinoline

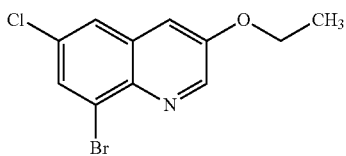

Intermediate I-122 (300 mg, 1.02 mmol), K$_2$CO$_3$ (422 mg, 3.05 mmol), and iodoethane (163 μL, 2.03 mmol) were dissolved in Acetone (10 mL) and heated to 50° C. in a sealed tube. After heating overnight, the reaction mixture was diluted with EtOAc, washed with water, then brine, dried (Na$_2$SO$_4$), filtered, and concentrated in vacuo to give Intermediate I-126A (319 mg, 1.11 mmol, 100%) as a light yellow solid: $^1$H NMR (400 MHz, CDCl$_3$) δ 8.74 (d, J=2.6 Hz, 1H), 7.85 (d, J=2.2 Hz, 1H), 7.67 (d, J=2.2 Hz, 1H), 7.28-7.24 (m, 1H), 4.17 (q, J=6.9 Hz, 2H), 1.52 (t, J=7.0 Hz, 3H); LC-MS: Method H, RT=1.22 min, MS (ESI) m/z: 286/288 (M+H)$^+$.

Intermediate I-126

Intermediate I-126A (319 mg, 1.11 mmol), bispinacolatodiboron (565 mg, 2.23 mmol), potassium acetate (273 mg, 2.78 mmol), and PdCl$_2$(dppf)-CH$_2$Cl$_2$ adduct (72.7 mg, 0.089 mmol) were stored on HIVAC for 15 minutes then were dissolved in dry 1,4-dioxane (5.67 mL) and degassed for 15 minutes by bubbling with argon. The reaction mixture was heated to 130° C. in the microwave for 40 minutes. The reaction mixture was diluted with EtOAc and washed with water then brine, dried (Na$_2$SO$_4$), filtered, and concentrated in vacuo. The crude material was purified by column chromatography (ISCO, 80 g silica gel column, 29 minute gradient from 0 to 100% EtOAc in DCM, followed by 0 to 20% MeOH in DCM) to give Intermediate I-126 (114 mg, 0.343 mmol, 31%) as a brown solid: LC-MS: Method H, RT=0.88 min, MS (ESI) m/z: 251.9 (boronic acid mass observed, M+H)$^+$.

Intermediate I-127

6-chloro-3-(difluoromethoxy)-8-(4,4,5,5-tetramethyl-1,3,2-dioxaborolan-2-yl)quinoline

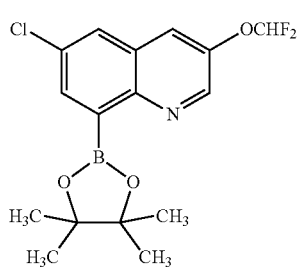

Intermediate I-127A:
8-bromo-6-chloro-3-(difluoromethoxy)quinoline

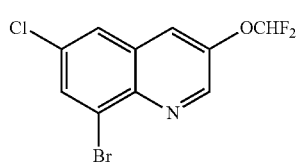

Intermediate I-122 (0.5 g, 1.7 mmol) and K$_2$CO$_3$ (1.17 g, 8.48 mmol) were suspended in DMF (17 mL) and heated to 100° C. Sodium 2-chloro-2,2-difluoroacetate (1.03 g, 6.78 mmol) was then added. After heating for 1 hour, the reaction mixture was cooled to ambient temperature, diluted with water, and extracted thrice with EtOAc. The combined organic extracts were washed with brine, dried (Na$_2$SO$_4$), filtered, and concentrated in vacuo. The crude material was purified by column chromatography (ISCO, 12 g silica gel column, 17 minute gradient from 0 to 50% EtOAc in hexanes) to give Intermediate I-127A (342 mg, 1.11 mmol, 66%) as a light yellow solid: $^1$H NMR (400 MHz, CDCl$_3$) δ 8.87 (d, J=2.6 Hz, 1H), 8.02 (d, J=2.0 Hz, 1H), 7.80 (d, J=2.4 Hz, 1H), 7.78 (d, J=2.0 Hz, 1H), 6.88-6.49 (m, 1H); LC-MS: Method H, RT=1.09 min, MS (ESI) m/z: 308/310 (M+H)$^+$.

Intermediate I-127

Intermediate I-127A (340 mg, 1.1 mmol), bispinacolatodiboron (560 mg, 2.2 mmol), potassium acetate (270 mg, 2.76 mmol), and PdCl$_2$(dppf)-CH$_2$Cl$_2$ adduct (72.0 mg, 0.088 mmol) were stored on HIVAC for 15 minutes then were dissolved in dry 1,4-dioxane (5.51 mL) and degassed for 15 minutes by bubbling with argon. The reaction mixture was heated to 130° C. in the microwave for 40 minutes. The reaction mixture was diluted with EtOAc and washed with water then brine, dried (Na$_2$SO$_4$), filtered, and concentrated in vacuo. The crude material was purified by column chromatography (ISCO, 80 g silica gel column, 29 minute gradient from 0 to 100% EtOAc in DCM, followed by 0 to 20% MeOH in DCM) to give Intermediate I-127 (175 mg, 0.492 mmol, 45%) as a brown solid: LC-MS: Method H, RT=0.93 min, MS (ESI) m/z: 274.1 (boronic acid mass observed, M+H)$^+$.

Intermediate I-128

6-(difluoromethyl)-3-methoxy-8-(4,4,5,5-tetramethyl-1,3,2-dioxaborolan-2-yl)quinoline

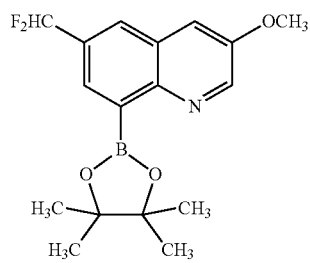
(I-128)

Intermediate I-128A:
8-bromo-3-methoxyquinoline-6-carbaldehyde

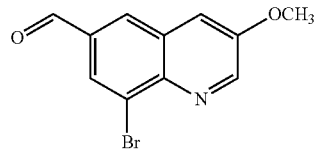
(I-128A)

Intermediate I-125 (152 mg, 0.602 mmol) and selenium dioxide (401 mg, 3.61 mmol) were suspended in 1,4-dioxane (3.01 mL) and heated to 180° C. in the microwave for 8 hours. The reaction mixture was filtered and concentrated in vacuo. The solids were then suspended in DCM and the insoluble material removed by suction filtration to give Intermediate I-128A (170 mg, 0.639 mmol, 100%) as a white solid: $^1$H NMR (400 MHz, CDCl$_3$) δ 10.15 (s, 1H), 8.93 (d, J=2.9 Hz, 1H), 8.39 (d, J=1.8 Hz, 1H), 8.25 (d, J=1.5 Hz, 1H), 7.56 (d, J=2.9 Hz, 1H), 4.04 (s, 3H); LC-MS: Method H, RT=0.89 min, MS (ESI) m/z: 266/268 (M+H)$^+$.

Intermediate I-128B:
8-bromo-6-(difluoromethyl)-3-methoxyquinoline

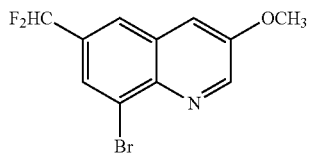
(I-128B)

Intermediate I-128A (50 mg, 0.188 mmol) and deoxofluor (104 μl, 0.564 mmol) were dissolved in DCM (940 After stirring overnight, the reaction mixture was diluted carefully with water then extracted thrice with DCM. The combined organic layers were washed with saturated NaHCO$_3$ then brine, dried (Na$_2$SO$_4$), filtered, and concentrated in vacuo. The crude material was purified by column chromatography (ISCO, 12 g silica gel column, 17 minute gradient from 0 to 100% EtOAc in hexanes) to give Intermediate I-128B (37 mg, 0.129 mmol, 68%) as a white solid: $^1$H NMR (400 MHz, CDCl$_3$) δ 8.88 (d, J=2.9 Hz, 1H), 8.03 (d, J=1.5 Hz, 1H), 7.89 (d, J=1.3 Hz, 1H), 7.46 (d, J=2.9 Hz, 1H), 6.96-6.64 (t, J=56 Hz, 1H), 4.02 (s, 1H); LC-MS: Method H, RT=0.98 min, MS (ESI) m/z: 288/290 (M+H)$^+$.

Intermediate I-128

Intermediate I-128B (37 mg, 0.128 mmol), bispinacolatodiboron (65.2 mg, 0.257 mmol), potassium acetate (31.5 mg, 0.321 mmol), and PdCl$_2$(dppf)-CH$_2$Cl$_2$ adduct (8.39 mg, 10.3 μmol) were stored on HIVAC for 15 minutes then were dissolved in dry 1,4-dioxane (642 μL) and degassed for 15 minutes by bubbling with argon. The reaction mixture was heated to 130° C. in the microwave for 40 minutes. The reaction mixture was diluted with EtOAc and washed with water then brine, dried (Na$_2$SO$_4$), filtered, and concentrated in vacuo to give Intermediate I-128. The crude material was used directly in the subsequent step: LC-MS: Method H, RT=0.80 min, MS (ESI) m/z: 254.1 (boronic acid mass observed, M+H)$^+$.

Intermediate I-129

6-(fluoromethyl)-3-methoxy-8-(4,4,5,5-tetramethyl-1,3,2-dioxaborolan-2-yl)quinoline

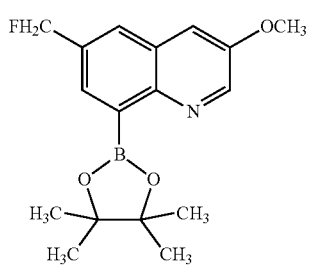
(I-129)

Intermediate I-129A:
(8-bromo-3-methoxyquinolin-6-yl)methanol

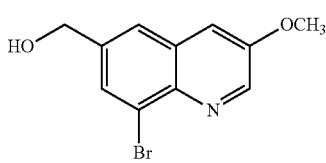
(I-129A)

Intermediate I-128A (50 mg, 0.188 mmol) was dissolved in MeOH (1.88 mL) and cooled to 0° C. Sodium borohydride (14.2 mg, 0.376 mmol) was then added. After 1 hour, the reaction mixture was diluted with EtOAc, washed with water, then brine, dried (Na$_2$SO$_4$), filtered, and concentrated in vacuo to give Intermediate I-129A (38.6 mg, 0.144 mmol, 77%) as a white solid: $^1$H NMR (400 MHz, CDCl$_3$) δ 8.79 (d, J=2.9 Hz, 1H), 7.92 (d, J=1.8 Hz, 1H), 7.72 (s, 1H), 7.40 (d, J=2.9 Hz, 1H), 4.89 (d, J=5.1 Hz, 2H), 4.00 (s, 3H), 1.89 (t, J=5.6 Hz, 1H); LC-MS: Method H, RT=0.73 min, MS (ESI) m/z: 268/270 (M+H)$^+$.

Intermediate I-129B:
8-bromo-6-(fluoromethyl)-3-methoxyquinoline

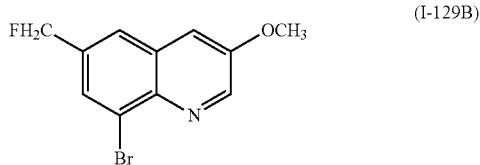

Intermediate I-129A (38 mg, 0.142 mmol) and Deoxofluor (78 μL, 0.425 mmol) were dissolved in DCM (709 μL). After stirring overnight, the reaction mixture was diluted carefully with water then extracted thrice with DCM. The combined organic layers were washed with saturated NaHCO$_3$ then brine, dried (Na$_2$SO$_4$), filtered, and concentrated in vacuo. The crude material was purified by column chromatography (ISCO, 12 g silica gel column, 17 minute gradient from 0 to 100% EtOAc in hexanes) to give Intermediate I-129B (29 mg, 0.109 mmol, 77%) as a white solid: $^1$H NMR (400 MHz, CDCl$_3$) δ 8.83 (d, J=2.9 Hz, 1H), 7.91 (s, 1H), 7.73 (s, 1H), 7.41 (d, J=2.6 Hz, 1H), 5.62-5.48 (t, J=48 Hz, 2H), 4.00 (s, 3H); LC-MS: Method H, RT=0.94 min, MS (ESI) m/z: 270/272 (M+H)$^+$.

Intermediate I-129

Intermediate I-129B (29 mg, 0.107 mmol), bispinacolatodiboron (54.5 mg, 0.215 mmol), potassium acetate (26.3 mg, 0.268 mmol), and PdCl$_2$(dppf)-CH$_2$Cl$_2$ adduct (7.01 mg, 8.59 μmol) were stored on HIVAC for 15 minutes then were dissolved in dry 1,4-dioxane (537 μL) and degassed for 15 minutes by bubbling with argon. The reaction mixture was heated to 130° C. in the microwave for 40 minutes. The reaction mixture was diluted with EtOAc and washed with water then brine, dried (Na$_2$SO$_4$), filtered, and concentrated in vacuo to give Intermediate I-129, which was used directly for the subsequent step: LC-MS: Method H, RT=0.68 min, MS (ESI) m/z: 236.1 (boronic acid mass observed, M+H)$^+$ Intermediate I-130

(2R,3S)-3-((2-chloro-5-fluorobenzo[d]thiazol-6-yl)oxy)butan-2-yl (2-methylpyrimidin-5-yl)carbamate

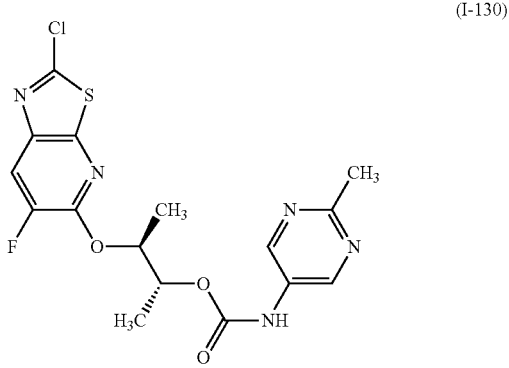 [SMILES: Cc1ncc(NC(=O)O[C@H](C)[C@H](C)Oc2nc3sc(Cl)nc3cc2F)cn1]

Intermediate I-72A (300 mg, 0.937 mmol) was dissolved in THF (18.7 mL). Phosgene solution (15% in toluene, 7.14 mL, 9.37 mmol) was then added. After stirring overnight, the reaction mixture was concentrated in vacuo and stored on HIVAC for 3 hours. The reaction mixture was dissolved in THF (18.7 mL). 2-Methylpyrimidin-5-amine (123 mg, 1.12 mmol) and pyridine (758 μl 9.37 mmol) were added. After 1 hour, the reaction mixture was concentrated in vacuo and purified by column chromatography (ISCO, 24 g silica gel column, 19 minute gradient from 0 to 100% EtOAc in hexanes) to give Intermediate I-130 (327 mg, 0.796 mmol, 85%) as a white solid: $^1$H NMR (400 MHz, CDCl$_3$) δ 8.72 (br. s., 2H), 7.66 (d, J=11.0 Hz, 1H), 7.36 (d, J=7.7 Hz, 1H), 6.55 (br. s., 1H), 5.14 (dd, J=6.5, 3.0 Hz, 1H), 4.60-4.49 (m, 1H), 2.71 (s, 3H), 1.44 (d, J=6.6 Hz, 3H), 1.40 (d, J=6.4 Hz, 3H); LC-MS: Method H, RT=0.95 min, MS (ESI) m/z: 411.0 (M+H)$^+$.

Intermediate I-131

(R)-1-((2-chloro-6-fluorothiazolo[5,4-b]pyridin-5-yl)oxy)propan-2-ol

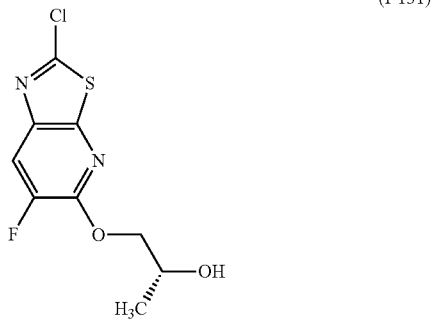

Intermediate I-131A: 6-fluoro-5-methoxythiazolo[5,4-b]pyridin-2-amine

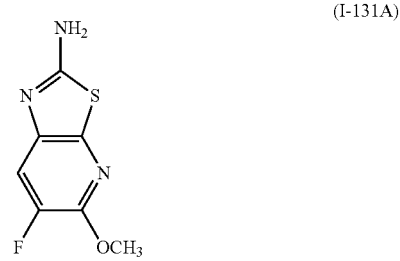 [SMILES: COc1nc2sc(N)nc2cc1F]

Potassium thiocyanate (0.738 g, 7.59 mmol) was dissolved in acetic acid (5 mL) and cooled to 0° C. 5-fluoro-6-methoxypyridin-3-amine (1.079 g, 7.59 mmol) was dissolved in acetic acid (1.667 mL) and added dropwise. Bromine (0.782 mL, 15.18 mmol) was dissolved in acetic acid (1.667 mL) and added dropwise to the reaction. The reaction mixture was allowed to warm to room temperature and stir overnight. The reaction mixture was concentrated under reduced pressure. The resultant residue was diluted with water and neutralized with 1 N NaOH. The aqueous solution was extracted with EtOAc×3. The combined organic layer was washed with brine, dried with sodium sulfate, and concentrated under reduced pressure to yield Intermediate I-131A (1.496 g, 7.51 mmol, 99% yield). $^1$H NMR (400 MHz, CDCl$_3$) δ 7.49 (d, J=10.6 Hz, 1H), 5.14 (br. s., 2H), 4.03 (s, 3H). LC-MS: method H, RT=0.65 min, MS (ESI) m/z: 200.0 (M+H)$^+$.

Intermediate I-131B: 2-amino-6-fluorothiazolo[5,4-b]pyridin-5-ol, 2 hydrobromide

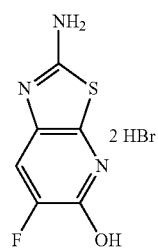

(I-131B)

Intermediate I-131A (0.500 g, 2.510 mmol) was dissolved in a solution of HBr in acetic acid (1.704 mL, 15.06 mmol, 33% by wt.) and the reaction mixture was stirred at 130° C. for 3 h. The reaction mixture was concentrated under reduced pressure to yield Intermediate I-131B (0.88 g, 2.54 mmol, 101% yield) as a tan solid. $^1$H NMR (400 MHz, MeOH$_4$) δ 7.66 (d, J=9.7 Hz, 1H) LC-MS: method H, RT=0.45 min, MS (ESI) m/z: 186.1 (M+H)$^+$.

Intermediate I-131C (R)-1-((2-amino-6-fluorothiazolo[5,4-b]pyridin-5-yl)oxy)propan-2-ol

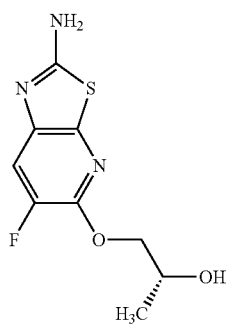

(I-131C)

To a solution of Intermediate I-131B (1.00 g, 2.88 mmol) in tetrahydrofuran (23.05 ml) was added (R)-4-methyl-1,3,2-dioxathiolane 2,2-dioxide (0.478 g, 3.46 mmol) followed by potassium carbonate (1.195 g, 8.65 mmol). The reaction mixture was stirred vigorously at 60° C. for 3 h then at room temperature for 48 hours. Sulfuric acid (0.768 ml, 14.41 mmol) followed by water (0.156 ml, 8.65 mmol) were added slowly to the reaction. The reaction mixture was allowed to stir at room temperature for 1 h. The reaction mixture was diluted with 1 N NaOH and EtOAc. The layers were separated and the organic layer was washed with brine, dried with sodium sulfate, and concentrated under reduced pressure to yield Intermediate I-131C (0.284 g, 1.167 mmol, 40.5% yield) as a yellow solid. $^1$H NMR (400 MHz, CDCl$_3$) δ 7.51 (d, J=10.6 Hz, 1H), 5.09 (br. s., 2H), 4.40 (d, J=7.9 Hz, 1H), 4.23 (d, J=6.6 Hz, 2H), 2.58 (d, J=2.9 Hz, 1H), 1.30 (d, J=5.9 Hz, 3H). LC-MS: method H, RT=0.59 min, MS (ESI) m/z: 244.1 (M+H)$^+$.

Intermediate I-131

Copper(II) chloride (0.658 g, 4.89 mmol) and t-butyl nitrite (0.582 ml, 4.89 mmol) were dissolved in MeCN (11.51 ml) and allowed to stir 10 minutes. Intermediate I-131C (0.700 g, 2.88 mmol) was dissolved in MeCN (17.27 ml) and the copper solution was added. The reaction mixture was stirred for 2.5 hours at 60° C. The reaction mixture was diluted with EtOAc, then brine, dried (Na$_2$SO$_4$), filtered, and concentrated in vacuo. Purified on ISCO using a 12 g column with 0-100% gradient of EtOAc in hexanes to Intermediate I-131 (0.698 g, 2.66 mmol, 92% yield). $^1$H NMR (400 MHz, CDCl$_3$) δ 7.79 (d, J=9.9 Hz, 1H), 4.45-4.34 (m, 1H), 4.26-4.19 (m, 2H), 3.86-3.71 (m, 1H), 2.25 (d, J=3.5 Hz, 1H), 1.39-1.24 (m, 3H). LC-MS: method H, RT=0.88 min, MS (ESI) m/z: 263.0 (M+H)$^+$.

Intermediate I-132

(R)-1-((6-fluoro-2-(2-methoxy-7-methylquinoxalin-5-yl)thiazolo[5,4-b]pyridin-5-yl)oxy) propan-2-yl carbonochloridate

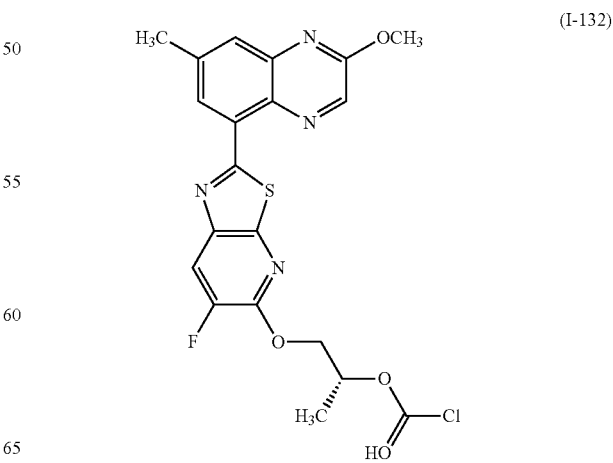

(I-132)

Intermediate I-132A: (R)-1-((6-fluoro-2-(2-methoxy-7-methylquinoxalin-5-yl) thiazolo[5,4-b]pyridin-5-yl)oxy)propan-2-ol

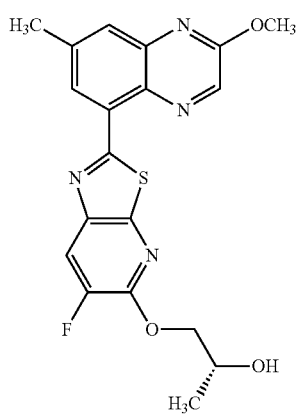

(I-132A)

Intermediate I-9 (0.343 g, 1.142 mmol) and Intermediate I-131 (0.300 g, 1.142 mmol) were dissolved in DMF (11.42 ml). PdCl$_2$(dppf)-CH$_2$Cl$_2$ adduct (0.056 g, 0.069 mmol) was added, and the reaction degassed by bubbling with argon for 15 minutes. Na$_2$CO$_3$, 3 M aqueous solution (0.381 ml, 1.142 mmol) was added and the reaction degassed for 5 minutes, then sealed and heated to 90° C. in the microwave for 30 minutes. The reaction mixture was purified on ISCO using a 24 g column eluting with 0-100% EtOAc in hexanes to yield Intermediate I-132A (0.223 g, 0.557 mmol, 48.8% yield) as a yellow solid. $^1$H NMR (400 MHz, CDCl$_3$) δ 8.56 (d, J=12.5 Hz, 1H), 8.01 (d, J=10.1 Hz, 1H), 7.78 (br. s., 1H), 7.33-7.28 (m, 1H), 4.55 (d, J=11.2 Hz, 1H), 4.38 (br. s., 2H), 4.13 (s, 4H), 2.65 (br. s., 3H), 1.35 (d, J=5.9 Hz, 3H). LC-MS: method H, RT=1.25 min, MS (ESI) m/z: 401.1 (M+H)$^+$.

Intermediate I-132

To a solution of (R)-1-((6-fluoro-2-(2-methoxy-7-methylquinoxalin-5-yl)thiazolo [5,4-b]pyridin-5-yl)oxy)propan-2-ol (0.098 g, 0.245 mmol) in THF (3 mL) at room temperature was added 15% phosgene in toluene (0.863 mL, 1.224 mmol) and the mixture was stirred at room temperature for 1 h. Solvent was completely removed and the sample was under vacuum overnight to give Intermediate I-132 (0.113 g, 0.244 mmol, 100% yield) as a yellow solid. This intermediate was used without further purification in the next step. LC-MS: method H, RT=1.37 min, MS (ESI) m/z: 463.0 (M+H)$^+$.

Intermediate I-133

(2R,3S)-3-((2-chloro-6-fluorothiazolo[5,4-b]pyridin-5-yl)oxy)butan-2-ol

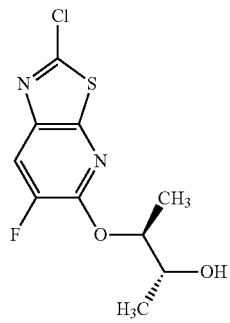

(I-133)

Intermediate I-133A: (2R,3S)-3-((2-amino-6-fluoro-thiazolo[5,4-b]pyridin-5-yl)oxy) butan-2-ol

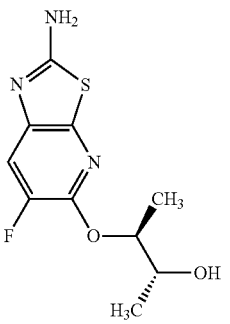

(I-133A)

To a solution of Intermediate I-131B (150 mg, 0.432 mmol) in DMF (1729 µl) was added (4R,5R)-4,5-dimethyl-1,3,2-dioxathiolane 2,2-dioxide (79 mg, 0.519 mmol) followed by potassium carbonate (179 mg, 1.297 mmol). The reaction mixture was stirred vigorously at 60° C. for 3 h and then allowed to stir at room temperature for 48 h. The reaction mixture was then diluted with EtOAc and filtered. The resulting solution was concentrated under reduced pressure to yield a dark oil. This residue was dissolved in THF (1729 µl) and sulfuric acid (69.1 µl, 1.297 mmol) followed by water (23.36 µl, 1.297 mmol). This reaction mixture was allowed to stir at room temperature for 1 hour before being diluted with 1 N NaOH and EtOAc. The layers were separated and the organic layer was washed with brine, dried with sodium sulfate, and concentrated under reduced pressure to yield Intermediate I-133A (0.11 g, 0.428 mmol, 99% yield) as a yellow solid. $^1$H NMR (400 MHz, MeOH$_4$) δ 7.42 (d, J=11.0 Hz, 1H), 5.12-5.02 (m, 1H), 3.96-3.88 (m, 1H), 1.33 (d, J=6.4 Hz, 3H), 1.24 (d, J=6.6 Hz, 3H). LC-MS: method H, RT=0.63 min, MS (ESI) m/z: 258.0 (M+H)$^+$.

Intermediate I-133

Copper(II) chloride (0.588 g, 4.37 mmol) and t-butyl nitrite (0.589 ml, 4.96 mmol) were dissolved in MeCN (11.66 ml) and allowed to stir 10 minutes. Intermediate I-133A (0.750 g, 2.92 mmol) was dissolved in MeCN (17.49 ml) and the copper solution was added. The reaction mixture was stirred for 1.5 h at 60° C. The reaction mixture was diluted with EtOAc, then brine, dried (Na$_2$SO$_4$), filtered, and concentrated in vacuo. Purified on ISCO using a 40 g column with 0-100% gradient of EtOAc in hexanes to yield Intermediate I-133 (0.722 g, 2.61 mmol, 90% yield). $^1$H NMR (400 MHz, CDCl$_3$) δ 7.87 (d, J=9.9 Hz, 1H), 5.31 (dd, J=6.4, 3.1 Hz, 1H), 4.12 (ddd, J=6.4, 4.7, 3.2 Hz, 1H), 2.14 (d, J=4.6 Hz, 1H), 1.42 (d, J=6.4 Hz, 3H), 1.31 (d, J=6.4 Hz, 3H). LC-MS: method H, RT=0.95, MS (ESI) m/z: 277.1 (M+H)$^+$.

Intermediate I-134

(2R,3S)-3-((6-fluoro-2-(2-methoxy-7-methylquinoxalin-5-yl)thiazolo[5,4-b]pyridin-5-yl) oxy)butan-2-yl carbonochloridate

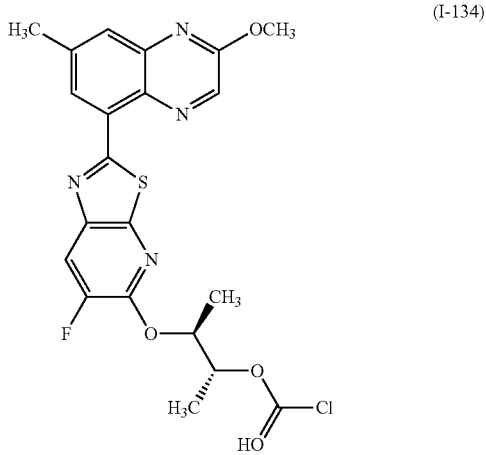 [SMILES: COc1cnc2c(-c3nc4cc(F)c(O[C@@H](C)[C@@H](C)OC(=O)Cl)nc4s3)cc(C)cc2n1]

(I-134)

Intermediate I-134A: (2R,3S)-3-((6-fluoro-2-(2-methoxy-7-methylquinoxalin-5-yl) thiazolo[5,4-b]pyridin-5-yl)oxy)butan-2-ol

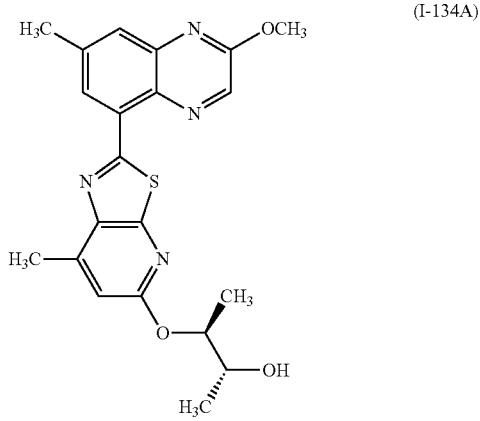 [SMILES: COc1cnc2c(-c3nc4c(C)cc(O[C@@H](C)[C@@H](C)O)nc4s3)cc(C)cc2n1]

(I-134A)

Intermediate I-9 (0.067 g, 0.224 mmol) and Intermediate I-133 (0.062 g, 0.224 mmol) were dissolved in DMF (2.241 ml). PdCl$_2$(dppf)-CH$_2$Cl$_2$ adduct (10.98 mg, 0.013 mmol) was added and the reaction degassed by bubbling with argon for 15 minutes. Na$_2$CO$_3$, 3 M aqueous solution (0.075 ml, 0.224 mmol) was added and the reaction degassed for 5 minutes, then sealed and heated to 90° C. in the microwave for 30 minutes. Purified on ISCO using a 40 g column eluting with 0-100% EtOAc in hexanes to yield Intermediate I-134A (0.090 g, 0.219 mmol, 95%) as a yellow solid. $^1$H NMR (400 MHz, CDCl$_3$) δ 8.57 (d, J=1.8 Hz, 1H), 8.54 (s, 1H), 7.99 (d, J=10.1 Hz, 1H), 7.77 (s, 1H), 5.37 (dd, J=6.4, 2.9 Hz, 1H), 4.13 (s, 3H), 2.65 (s, 3H), 2.46 (d, J=4.8 Hz, 1H), 1.43 (d, J=6.4 Hz, 3H), 1.39 (d, J=6.4 Hz, 1H), 1.30 (d, J=6.6 Hz, 5H). LC-MS: method H, RT=1.24 min, MS (ESI) m/z: 415.1 (M+H)$^+$.

Intermediate I-134

To a solution of Intermediate I-134A (0.045 g, 0.109 mmol) in THF (3 mL) at room temperature was added 15% phosgene solution in toluene (0.383 mL, 0.543 mmol) and the mixture was stirred room temperature overnight. Solvent was completely removed to yield Intermediate I-134 (0.052 g, 0.098 mmol, 90% yield) as a yellow solid. Used without further purification in the next step. LC-MS: method H, RT=1.46 min, MS (ESI) m/z: 477.0 (M+H)$^+$.

Intermediate I-135

(2R,3S)-3-((2-chloro-6-fluorothiazolo[5,4-b]pyridin-5-yl)oxy)butan-2-yl (2-methylpyrimidin-5-yl)carbamate

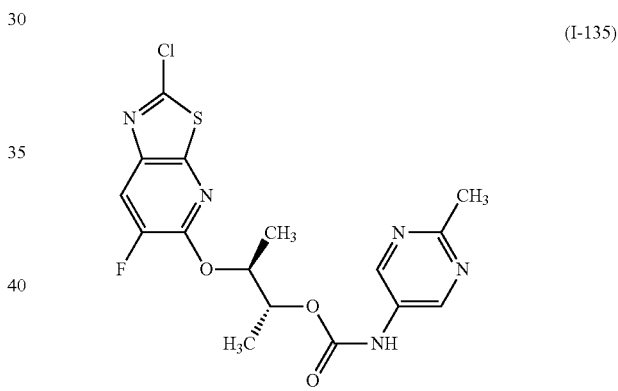

(I-135)

Intermediate I-135A: (2R,3S)-3-((2-chloro-6-fluorothiazolo[5,4-b]pyridin-5-yl)oxy) butan-2-yl carbonochloridate

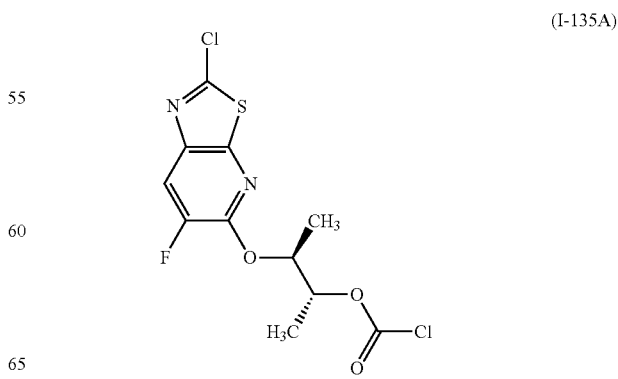

(I-135A)

To a solution of Intermediate I-133 (0.030 g, 0.108 mmol) in THF (3 mL) at room temperature was added 15% phosgene solution in toluene (0.382 mL, 0.542 mmol), and the mixture was stirred at room temperature overnight. Solvent was completely removed to give Intermediate I-135A (0.035 g, 0.103 mmol, 95% yield) as a yellow solid. Used without further purification in the next step. LC-MS: method H, RT=1.46 min, MS (ESI) m/z: 340.0 (M+H)⁺.

Intermediate I-135

2-Methylpyrimidin-5-amine (0.023 g, 0.206 mmol) and pyridine (0.083 mL, 1.032 mmol) were dissolved in DCM (2 mL) To this solution was added Intermediate I-135A (0.035 g, 0.103 mmol) as a solution in DCM (1 mL). The reaction mixture was allowed to stir for 1 h. The reaction mixture was concentrated under reduced pressure to yield Intermediate I-135 (0.040 g, 0.097 mmol, 94%). LC-MS: method H, RT=1.09 min, MS (ESI) m/z: 412.0 (M+H)⁺.

Intermediate I-136

6-fluoro-3-methoxy-8-(4,4,5,5-tetramethyl-1,3,2-dioxaborolan-2-yl)quinoline

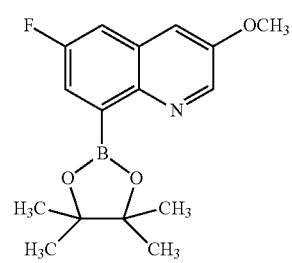

(I-136)

Intermediate I-136A:
(2-amino-3-bromo-5-fluorophenyl)methanol

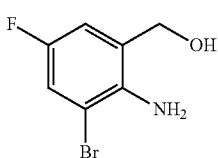

(I-136A)

Methyl 2-amino-3-bromo-5-fluorobenzoate (0.910 g, 3.67 mmol) was dissolved in THF (12.23 ml). LiBH₄ (0.160 g, 7.34 mmol) was added and the reaction mixture was heated to 50° C. for 2 hours. The reaction mixture was diluted with water and stirred for 30 minutes. The reaction mixture was then extracted thrice with EtOAc. The combined organic layers were washed with brine, dried (Na₂SO₄), filtered, and concentrated in vacuo to yield Intermediate I-136A (0.799 g, 3.63 mmol, 99% yield) as a white solid. ¹H NMR (400 MHz, CDCl₃) δ 7.20 (dd, J=7.7, 2.9 Hz, 1H), 6.86 (dd, J=8.4, 2.9 Hz, 1H), 4.68 (s, 2H), 4.52 (d, J=12.8 Hz, 2H), 1.89-1.69 (m, 1H). LC-MS: method H, RT=0.94 min, MS (ESI) m/z: 219.9 (M+H)⁺.

Intermediate I-136B:
2-amino-3-bromo-5-fluorobenzaldehyde

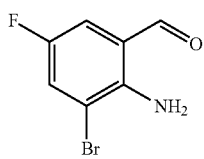

(I-136B)

Intermediate I-136A (0.799 g, 3.63 mmol) was dissolved in CHCl₃ (24.21 ml). Manganese dioxide (1.263 g, 14.52 mmol) was added and the reaction mixture was heated to 40° C. overnight. The reaction mixture was filtered through celite and concentrated in vacuo to yield Intermediate I-136B (0.750 g, 3.44 mmol, 95%). ¹H NMR (400 MHz, CDCl₃) δ 9.80 (s, 1H), 7.48 (dd, J=7.5, 2.9 Hz, 1H), 7.25 (dd, J=7.9, 2.9 Hz, 1H), 6.55 (br. s., 2H).

Intermediate I-136C:
3-(benzyloxy)-8-bromo-6-fluoroquinoline

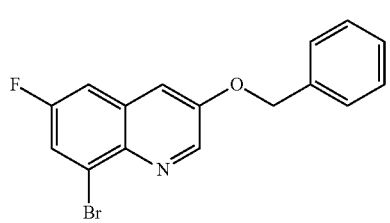

(I-136C)

Intermediate I-136B (0.800 g, 3.67 mmol), 2-(benzyloxy)acetaldehyde (0.551 g, 3.67 mmol), and sodium methoxide (8.07 ml, 4.04 mmol) were dissolved in MeOH (7.34 ml) and heated to reflux overnight. The reaction mixture was diluted with saturated NH₄Cl, partially concentrated in vacuo and diluted with EtOAc. The layers were separated and the organic layer was washed with brine, dried (Na₂SO₄), filtered, and concentrated in vacuo. Purified on ISCO using 80 g column eluting with 0-60% gradient of EtOAc in hexanes to yield Intermediate I-136C (0.363 g, 1.093 mmol, 30%). ¹H NMR (500 MHz, CDCl₃) δ 8.83 (d, J=2.5 Hz, 1H), 7.72 (dd, J=8.1, 2.6 Hz, 1H), 7.52-7.49 (m, 2H), 7.45 (t, J=7.3 Hz, 2H), 7.41 (d, J=2.8 Hz, 2H), 7.34 (dd, J=8.7, 2.6 Hz, 1H), 5.24 (s, 2H). LC-MS: method H, RT=1.38 min, MS (ESI) m/z: 331.9 (M+H)⁺.

Intermediate I-136D: 8-bromo-6-fluoroquinolin-3-ol

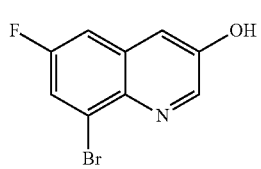

(I-136D)

Intermediate I-136C (0.363 g, 1.093 mmol) and pentamethylbenzene (1.134 g, 7.65 mmol) were dissolved in DCM (21.86 ml) and cooled to −78° C. Boron trichloride (1 M in heptane) (2.84 ml, 2.84 mmol) was added and the reaction mixture was allowed to warm to room temperature overnight. The reaction mixture was diluted with hexanes and 1 N HCl and allowed to stir for 1 hour. The resulting solid was collected by suction filtration, washing with water and hexanes to yield Intermediate I-136D (0.176 g, 0.727 mmol, 66.5% yield): $^1$H NMR (400 MHz, MeOH$_4$) δ 8.53 (d, J=2.9 Hz, 1H), 7.68 (dd, J=8.4, 2.6 Hz, 1H), 7.49-7.37 (m, 2H). LC-MS: method H, RT=1.12 min, MS (ESI) m/z: 241.9 (M+H)$^+$.

Intermediate I-136E:
8-bromo-6-fluoro-3-methoxyquinoline

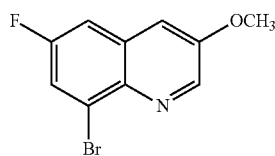

(I-136E)

Intermediate I-136D (0.095 g, 0.341 mmol), K$_2$CO$_3$ (0.141 g, 1.023 mmol), and methyl iodide (0.043 ml, 0.682 mmol) were dissolved in acetone (3.41 ml) and heated to 50° C. in a sealed tube overnight. The reaction mixture was diluted with EtOAc, washed with water, then brine, dried (Na$_2$SO$_4$), filtered, and concentrated in vacuo to yield Intermediate I-136E (0.060 g, 0.234 mmol, 68.7% yield). $^1$H NMR (400 MHz, CDCl$_3$) δ 8.76 (dd, J=2.8, 0.6 Hz, 1H), 7.72 (dd, J=8.0, 2.8 Hz, 1H), 7.37 (dd, J=8.8, 2.6 Hz, 1H), 7.35 (d, J=2.6 Hz, 1H), 4.00 (s, 3H). LC-MS: method H, RT=1.31 min, MS (ESI) m/z: 255.8 (M+H)$^+$.

Intermediate I-136

Intermediate I-136E (0.087 g, 0.340 mmol), BISPIN (0.173 g, 0.679 mmol), potassium acetate (0.083 g, 0.849 mmol), and PdCl$_2$(dppf)-CH$_2$Cl$_2$ adduct (0.022 g, 0.027 mmol) were stored on HIVAC for 15 minutes then were dissolved in 1,4-dioxane (3 ml) and degassed for 15 minutes by bubbling with argon. The reaction mixture was heated to 130° C. in the microwave for 40 minutes. The reaction mixture was diluted with EtOAc and washed with water then brine, dried (Na$_2$SO$_4$), filtered, and concentrated in vacuo to yield Intermediate I-136 (0.103 g, 0.170 mmol, 50%). This material was dissolved in DMF to make a stock solution of 10 mg per mL and used without further purification. LC-MS: method H, RT=1.10 min, MS (ESI) m/z: 221.9 (M+H)$^+$. See the mass of the boronic acid in the LC/MS.

Intermediate I-137

(2R,3S)-3-((2-chloro-6-fluorothiazolo[5,4-b]pyridin-5-yl)oxy)butan-2-yl (2-(2-((tert-butyldimethylsilyl)oxy)ethoxy)pyrimidin-5-yl)carbamate

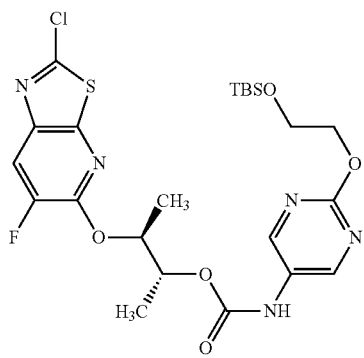

(I-137)

Intermediate I-137A: (2R,3S)-3-((2-chloro-6-fluorothiazolo[5,4-b]pyridin-5-yl)oxy) butan-2-yl carbonochloridate

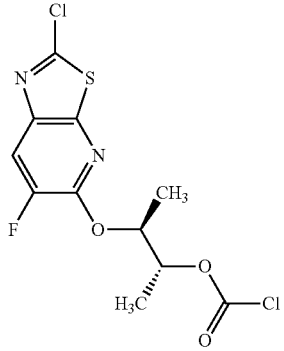

(I-137A)

To a solution of Intermediate I-133 (0.100 g, 0.361 mmol) in THF (5 mL) at room temperature was added 15% phosgene solution in toluene (1.274 mL, 1.807 mmol) and the mixture was stirred at room temperature overnight. Solvent was completely removed to give Intermediate I-137A (0.125 g, 0.369 mmol, 102% yield) as a yellow solid. LC-MS: method H, RT=1.20 min, MS (ESI) m/z: 338.9 (M+H)$^+$.

Intermediate I-137

2-(2-((tert-Butyldimethylsilyl)oxy)ethoxy)pyrimidin-5-amine (0.199 g, 0.737 mmol) and pyridine (0.298 mL, 3.69 mmol) were dissolved in DCM (2 mL) To this solution was added Intermediate I-137A (0.125 g, 0.369 mmol) as a solution in DCM (1 mL). The reaction mixture was allowed to stir for 1 h. The reaction mixture was concentrated under reduced pressure to yield Intermediate I-137 (0.130 g, 0.227 mmol, 62%). $^1$H NMR (400 MHz, CDCl$_3$) δ 8.48 (br. s., 2H), 7.76 (d, J=9.7 Hz, 1H), 5.45 (dd, J=6.6, 2.9 Hz, 1H), 5.12 (dd, J=6.6, 2.9 Hz, 1H), 4.33 (t, J=5.5 Hz, 2H), 3.90 (t, J=5.4 Hz, 2H), 1.34 (d, J=6.6 Hz, 6H), 0.81 (s, 9H), 0.00 (s, 6H). LC-MS: method H, RT=1.20 min, MS (ESI) m/z: 572.1 (M+H)$^+$.

Intermediate I-138

(R)-1-((2-(2-methoxy-7-methylquinoxalin-5-yl)-7-methylthiazolo[5,4-b]pyridin-5-yl) oxy)propan-2-yl carbonochloridate

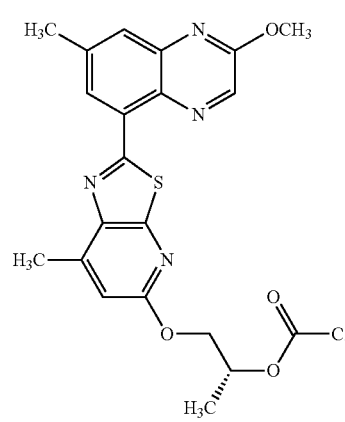

(I-138)

Intermediate I-138A: 2-amino-7-methylthiazolo[5,4-b]pyridin-5-ol, 2 hydrobromide

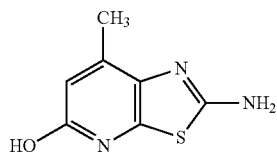

(I-138A)

Intermediate I-16B (0.500 g, 2.56 mmol) was dissolved in HBr in acetic acid (1.738 mL, 15.37 mmol, 33% by wt.), and the reaction mixture was stirred at 130° C. for 3 h. The reaction mixture was concentrated under reduced pressure to yield Intermediate I-138A (0.636, 1.854 mmol, 72.4% yield) as a tan solid. $^1$H NMR (400 MHz, CDCl$_3$) δ 6.66 (d, J=0.9 Hz, 1H), 2.48 (d, J=0.7 Hz, 3H). LC-MS: method H, RT=0.46 min, MS (ESI) m/z: 182.1 (M+H)$^+$.

Intermediate I-138B: (R)-5-(2-((tert-butyldiphenylsilyl)oxy)propoxy)-7-methylthiazolo [5,4-b]pyridin-2-amine

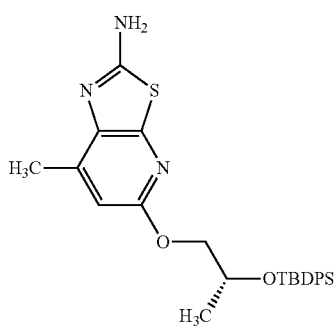

(I-138B)

Intermediate I-138A (0.500 g, 1.458 mmol) was dissolved in DMF (14.58 ml) and Cs$_2$CO$_3$ (2.85 g, 8.75 mmol) was added followed by (R)-tert-Butyl((1-iodopropan-2-yl) oxy) diphenylsilane (0.619 g, 1.458 mmol). The reaction mixture was stirred at room temperature for 3 h. The reaction mixture was then heated to 40° C. and allow to stir overnight. The reaction mixture was diluted with water and EtOAc. The layers were separated and the organic layer was washed with brine, dried with sodium sulfate, and concentrated under reduced pressure. The resulting residue was purified on ISCO using 40 g column eluting with 0-100% EtOAc in hexanes to yield Intermediate I-138B (0.324 g, 0.678 mmol, 46.5% yield) as a yellow solid. $^1$H NMR (400 MHz, CDCl$_3$) δ 7.69 (ddd, J=8.0, 4.1, 1.5 Hz, 4H), 7.42-7.28 (m, 6H), 6.32 (d, J=0.7 Hz, 1H), 4.97 (s, 2H), 4.26-4.18 (m, 2H), 4.16-4.09 (m, 5H), 2.45 (d, J=0.7 Hz, 3H), 1.15 (d, J=6.2 Hz, 3H), 1.06 (s, 9H). LC-MS: method H, RT=1.24 min, MS (ESI) m/z: 478.3 (M+H)$^+$.

Intermediate I-138C (R)-5-(2-((tert-butyldiphenylsilyl)oxy)propoxy)-2-chloro-7-methylthiazolo[5,4-b]pyridine

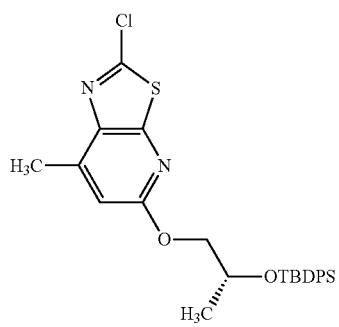

(I-138C)

Copper(II) chloride (0.155 g, 1.153 mmol) and t-butyl nitrite (0.137 ml, 1.153 mmol) were dissolved in MeCN (2.71 ml) and allowed to stir 10 minutes. Intermediate I-138B (0.324 g, 0.678 mmol) was dissolved in MeCN (4.07 ml) and the copper solution was added. The reaction mixture was stirred for 2.5 h at 60° C. The reaction mixture was diluted with EtOAc, washed with 1 N HCl, saturated NaHCO$_3$, then brine, dried (Na$_2$SO$_4$), filtered, and concentrated in vacuo. Purified on ISCO using a 24 g column with 0-100% gradient of EtOAc in hexanes to yield Intermediate I-138C (0.222 g, 0.447 mmol, 65.8% yield) as a yellow solid. $^1$H NMR (400 MHz, CDCl$_3$) δ 7.71-7.64 (m, 4H), 7.44-7.28 (m, 6H), 6.42 (s, 1H), 4.34-4.09 (m, 3H), 2.56 (d, J=0.7 Hz, 3H), 1.18 (d, J=5.9 Hz, 3H), 1.06 (s, 9H). LC-MS: method H, RT=1.71 min, MS (ESI) m/z: 497.2 (M+H)$^+$.

Intermediate I-138D (R)-5-(2-((tert-butyldiphenyl silyl)oxy)propoxy)-2-(2-methoxy-7-methylquinoxalin-5-yl)-7-methylthiazolo[5,4-b]pyridine

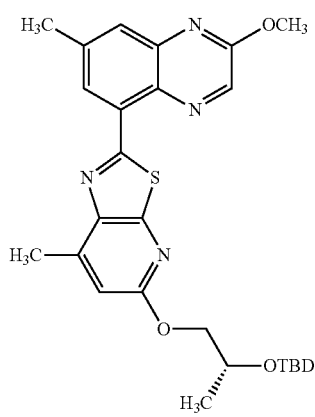

(I-138D)

Intermediate I-9 (0.052 g, 0.173 mmol) and Intermediate I-138C (0.086 g, 0.173 mmol) were dissolved in DMF (1.730 ml). PdCl$_2$(dppf)-CH$_2$Cl$_2$ adduct (8.48 mg, 10.38 μmol) was added and the reaction degassed by bubbling with argon for 15 minutes. Na₂CO₃, 3 M aqueous solution (0.100 ml, 0.300 mmol) was added and the reaction degassed for 5 minutes, then sealed and heated to 90° C. in the microwave for 30 minutes. The reaction mixture was filtered and purified on ISCO using 0-100% EtOAc in hexanes on a 24 g column to yield Intermediate I-138D (0.055 g, 0.087 mmol, 50.1% yield) as a yellow solid. ¹H NMR (400 MHz, CDCl₃) δ 8.59 (d, J=2.0 Hz, 1H), 8.54 (s, 1H), 7.71-7.69 (m, 4H), 7.41-7.30 (m, 7H), 6.47 (d, J=0.9 Hz, 1H), 4.40-4.24 (m, 4H), 4.12 (s, 3H), 2.74 (d, J=0.9 Hz, 3H), 2.66 (s, 3H), 1.19 (d, J=5.9 Hz, 3H), 1.08 (s, 9H). LC-MS: method H, RT=1.15 min, Compound does not ionize.

Intermediate I-138E (R)-1-((2-(2-methoxy-7-methylquinoxalin-5-yl)-7-methylthiazolo[5,4-b] pyridin-5-yl)oxy) propan-2-ol

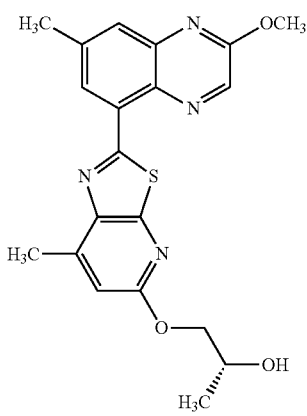

(I-138E)

Intermediate I-138D (0.055 g, 0.087 mmol) was dissolved in THF (0.866 ml) and TBAF (0.104 ml, 0.104 mmol) was added. The reaction mixture was allowed to stir at room temperature for 1 h and concentrated under reduced pressure. Purified on ISCO using 0-100% EtOAc in hexanes gradient on a 12 g column to yield Intermediate I-138E (0.027 g, 0.068 mmol, 79% yield) as a yellow solid. ¹H NMR (400 MHz, CDCl₃) δ 8.60 (d, J=1.8 Hz, 1H), 8.54 (s, 1H), 7.75 (s, 1H), 6.75 (d, J=0.9 Hz, 1H), 4.56-4.19 (m, 4H), 4.12 (s, 3H), 3.49 (d, J=5.5 Hz, 1H), 2.95 (s, 1H), 2.80 (d, J=0.9 Hz, 3H), 2.66 (s, 3H), 1.31 (d, J=6.2 Hz, 3H). LC-MS: method H, RT=1.26 min, MS (ESI) m/z: 397.2 (M+H)⁺.

Intermediate I-138

To a solution of Intermediate I-138E (0.027 g, 0.068 mmol) in THF (3 mL) at room temperature was added 15% phosgene solution in toluene (0.240 mL, 0.341 mmol) and the mixture was stirred at room temperature for 1 h. Solvent was completely removed and the sample was under vacuum overnight to give Intermediate I-138 (0.030 g, 0.065 mmol, 96% yield) as a yellow solid. Used without any purification. LC-MS: method H, RT=1.43 min, MS (ESI) m/z: 459.1 (M+H)⁺.

Intermediate I-139

(R)-1-((2-chloro-6-fluorothiazolo[5,4-b]pyridin-5-yl)oxy)propan-2-yl (2-methylpyrimidin-5-yl)carbamate

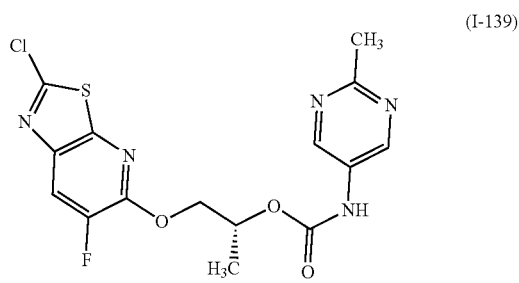 [SMILES: Cc1ncc(NC(=O)O[C@H](C)COc2nc3sc(Cl)nc3cc2F)cn1]

(I-139)

Intermediate I-139A (2R,3S)-3-((2-chloro-6-fluorothiazolo[5,4-b]pyridin-5-yl)oxy)butan-2-yl carbonochloridate

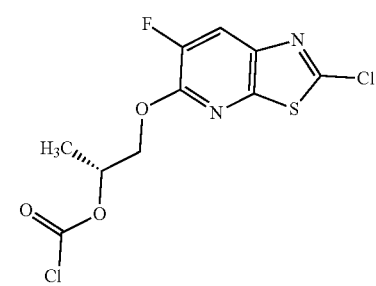

(I-139A)

To a solution of Intermediate I-131 (0.030 g, 0.114 mmol) in THF (3 mL) at room temperature was added 15% phosgene solution in toluene (0.403 mL, 0.571 mmol), and the mixture was stirred at room temperature overnight. Solvent was completely removed to give Intermediate I-139A (0.035 g, 0.108 mmol, 95% yield) as a yellow solid. Used without further purification in the next step. LC-MS: method H, RT=1.22 min, MS (ESI) m/z: 325.0 (M+H)⁺.

Intermediate I-139

2-Methylpyrimidin-5-amine (0.023 g, 0.215 mmol) and pyridine (0.083 mL, 1.032 mmol) were dissolved in DCM (2 mL) To this solution was added Intermediate I-139A (0.035 g, 0.108 mmol) as a solution in DCM (1 mL). The reaction mixture was allowed to stir for 1 h. The reaction mixture was concentrated under reduced pressure to yield Intermediate I-139 (0.038 g, 0.096 mmol, 89%). LC-MS: method H, RT=1.04 min, MS (ESI) m/z: 398.0 (M+H)⁺.

Intermediate I-140

(3-Methoxy-8-(4,4,5,5-tetramethyl-1,3,2-dioxaborolan-2-yl)quinolin-6-yl)methanol

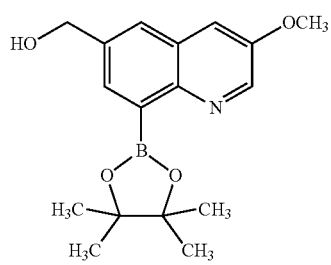

(I-140)

Intermediate I-140A:
8-Bromo-3-methoxyquinoline-6-carbaldehyde

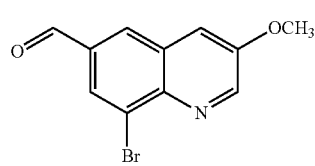

(I-140A)

A mixture of Intermediate I-125 (0.050 g, 0.198 mmol) and selenium dioxide (0.132 g, 1.190 mmol) in dioxane (3.0 mL) was heated in a microwave at 180° C. for 9 hours. The insoluble material was removed by filtration and washed with EtOAc. The crude product was purified by flash chromatography (loading in chloroform, 0% to 100% EtOAc in hexane using a 12 g silica gel cartridge). The desired fractions were combined and concentrated to yield Intermediate I-140A (0.051 g, 0.163 mmol, 82% yield) as a white solid. Contains 15% starting material. Will be used without further purification. LC-MS: method H, RT=0.83 min, MS (ESI) m/z: 267.9 (M+H)$^+$.

Intermediate I-140B:
(8-Bromo-3-methoxyquinolin-6-yl)methanol

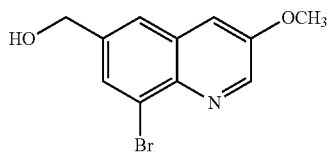

(I-140B)

Intermediate I-140A (0.0502 g, 0.189 mmol) was dissolved in THF (1.887 ml) and sodium borohydride (7.14 mg, 0.189 mmol) was added in one portion. The reaction mixture was allowed to stir at room temperature for 3 h. The reaction mixture was diluted with water and EtOAc. The layers were separated and the organic layer was washed with water, washed with brine, dried with sodium sulfate, and concentrated under reduced pressure to yield Intermediate I-140B (0.048 g, 0.179 mmol, 95% yield) as a white solid. $^1$H NMR (400 MHz, CDCl$_3$) δ 8.79 (d, J=2.9 Hz, 1H), 7.92 (d, J=1.8 Hz, 1H), 7.72 (s, 1H), 7.40 (d, J=2.9 Hz, 1H), 4.89 (d, J=5.1 Hz, 2H), 4.00 (s, 3H), 1.91 (s, 1H). LC-MS: method H, RT=0.69 min, MS (ESI) m/z: 269.9 (M+H)$^+$.

Intermediate I-140

Intermediate I-140B (0.0524 g, 0.195 mmol), BISPIN (0.099 g, 0.391 mmol), potassium acetate (0.048 g, 0.489 mmol), and PdCl$_2$(dppf)-CH$_2$Cl$_2$ adduct (0.013 g, 0.016 mmol) were stored on HIVAC for 15 minutes then were dissolved in 1,4-dioxane (3 ml) (sure sealed bottle) and degassed for 15 minutes by bubbling with argon. The reaction mixture was heated to 130° C. in the microwave for 40 minutes (fixed hold time off). The reaction mixture was diluted with EtOAc and washed with water then brine, dried (Na$_2$SO$_4$), filtered, and concentrated in vacuo. The residue was dissolved in dioxanes to provide a 10 mg/mL stock solution of the above boronic ester. Used without further purification. See mass of boronic acid in the LC/MS LC-MS: method H, RT=0.50 min, MS (ESI) m/z: 234.0 (M+H)$^+$.

Intermediate I-141

Methyl 5-(((((2R,3S)-3-((2-chloro-6-fluorothiazolo[5,4-b]pyridin-5-yl)oxy)butan-2-yl) oxy)carbonyl)amino)pyrimidine-2-carboxylate

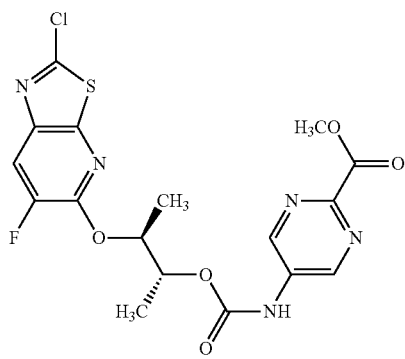

(I-141)

Intermediate I-141A: (2R,3S)-3-((2-chloro-6-fluorothiazolo[5,4-b]pyridin-5-yl)oxy) butan-2-yl carbonochloridate

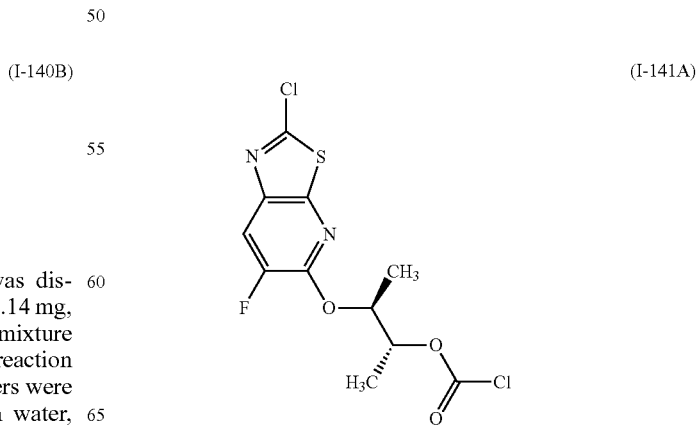

(I-141A)

To a solution of Intermediate I-133 (0.058 g, 0.210 mmol) in THF (5 mL) at room temperature was added 15% phosgene in toluene (0.739 mL, 1.048 mmol) and the mixture was stirred at room temperature overnight. The solvent was completely removed to give Intermediate I-141A (0.071 g, 0.209 mmol, 100% yield) as a yellow solid. LC-MS: method H, RT=1.22 min, MS (ESI) m/z: 339.1 (M+H)$^+$.

Intermediate I-141

Methyl 5-aminopyrimidine-2-carboxylate (0.065 g, 0.425 mmol) and pyridine (0.172 mL, 2.123 mmol) were dissolved in DCM (2 mL). To this solution was added Intermediate I-141A (0.072 g, 0.212 mmol) as a solution in DCM (1 mL). The reaction mixture was allowed to stir for 1 h. The reaction mixture was concentrated under reduced pressure. Purified on ISCO using 0-100% EtOAc in hexanes to yield Intermediate I-141 (0.066 g, 0.145 mmol, 68.2% yield) as a white solid. $^1$H NMR (400 MHz, CDCl$_3$) δ 9.04 (s, 2H), 7.87 (d, J=9.7 Hz, 1H), 6.94 (s, 1H), 5.56 (dd, J=6.5, 2.8 Hz, 1H), 5.38-5.17 (m, 1H), 4.09 (s, 3H), 1.47 (d, J=6.4 Hz, 6H). LC-MS: method H, RT=0.93 min, MS (ESI) m/z: 456.0 (M+H)$^+$.

Intermediate I-142

(R)-methyl 5-((((1-((2-chloro-6-fluorothiazolo[5,4-b]pyridin-5-yl)oxy)propan-2-yl)oxy) carbonyl) amino)pyrimidine-2-carboxylate

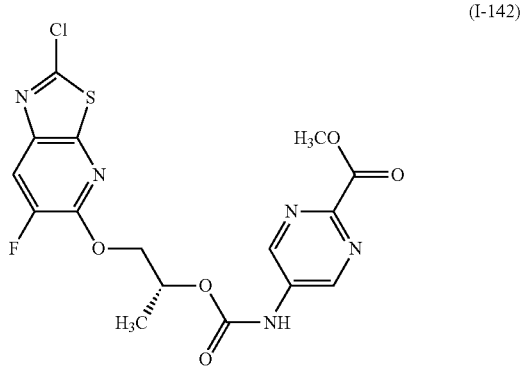 [SMILES: COC(=O)c1ncc(NC(=O)O[C@H](C)COc2nc3sc(Cl)nc3cc2F)cn1]

(I-142)

Intermediate I-142A: (R)-1-((2-chloro-6-fluorothiazolo[5,4-b]pyridin-5-yl)oxy) propan-2-yl carbonochloridate

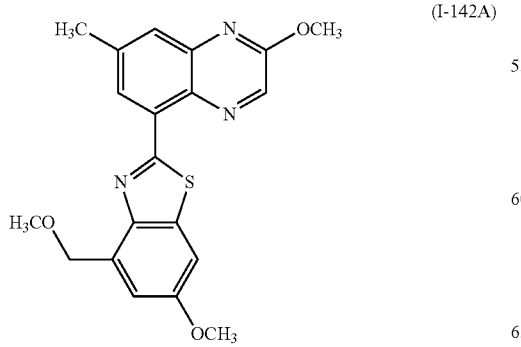

(I-142A)

To a solution of Intermediate I-131 (0.058 g, 0.210 mmol) in THF (5 mL) at room temperature was added 15% phosgene in toluene (0.739 mL, 1.048 mmol) and the mixture was stirred at room temperature overnight. The solvent was completely removed to give Intermediate I-142A (0.072 g, 0.221 mmol, 100% yield) as a yellow solid. LC-MS: method H, RT=1.17 min, MS (ESI) m/z: 325.1 (M+H)$^+$.

Intermediate I-142

Methyl 5-aminopyrimidine-2-carboxylate (0.068 g, 0.443 mmol) and pyridine (0.179 mL, 2.214 mmol) were dissolved in DCM (2 mL). To this solution was added Intermediate I-142A (0.072 g, 0.221 mmol) as a solution in DCM (1 mL). The reaction mixture was allowed to stir for 1 h. The reaction mixture was concentrated under reduced pressure. Purified on ISCO using 0-100% EtOAc in hexanes to yield I-142 (0.87 g, 0.197 mmol, 89% yield) as a white solid. $^1$H NMR (400 MHz, CDCl$_3$) δ 9.06 (s, 2H), 7.89 (d, J=9.9 Hz, 1H), 6.98 (s, 1H), 5.42 (d, J=3.3 Hz, 1H), 4.72 (dd, J=11.9, 3.1 Hz, 1H), 4.48 (dd, J=11.9, 6.6 Hz, 1H), 4.09 (s, 3H), 1.51 (d, J=6.6 Hz, 3H). LC-MS: method H, RT=0.88 min, MS (ESI) m/z: 442.0 (M+H)$^+$.

Intermediate I-143

(2R,3S)-3-((4-chloro-2-(6-chloro-3-methoxyquinolin-8-yl)-5-fluorobenzo[d]thiazol-6-yl) oxy)butan-2-yl carbonochloridate

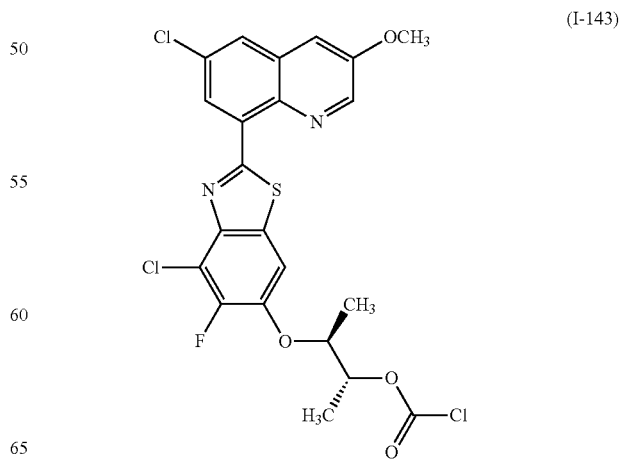

(I-143)

Intermediate I-143A: (2R,3S)-3-((2-bromo-4-chloro-5-fluorobenzo[d]thiazol-6-yl)oxy) butan-2-ol

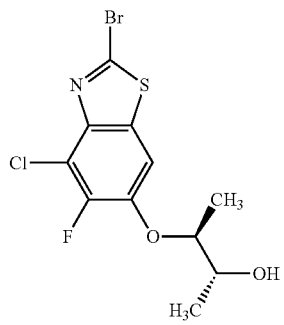
(I-143A)

To a solution of Intermediate I-44 (0.200 g, 0.708 mmol) in THF (2.83 ml) was added (4R,5R)-4,5-dimethyl-1,3,2-dioxathiolane 2,2-dioxide (0.140 g, 0.920 mmol) followed by potassium carbonate (0.147 g, 1.062 mmol). The reaction vial was sealed and heated to 65° C. overnight. The crude mixture was cooled to 0° C. and concentrated sulfuric acid (0.113 ml, 2.124 mmol) was added followed by water (0.064 ml, 3.54 mmol). The reaction mixture was allowed to thaw to room temperature, and stirred for 20 min. The reaction mixture was quenched with 20 mL 1.5 M $K_2HPO_4$, extracted with 100 mL EtOAc, washed with brine, dried over $MgSO_4$, filtered and concentrated to afford a beige solid that was dry loaded onto celite and purified by ISCO (40 g, 0-50% DCM/EtOAc) to afford Intermediate I-143A (0.145 g, 0.409 mmol, 57.8% yield) as an off white solid. $^1$H NMR (400 MHz, CDCl$_3$) δ 7.34 (d, J=7.0 Hz, 1H), 4.38 (dd, 3.4 Hz, 1H), 4.16-4.03 (m, 1H), 2.01 (d, J=4.8 Hz, 1H), 1.37 (d, J=6.4 Hz, 3H), 1.31 (d, J=6.6 Hz, 3H). LC-MS: method H, RT=0.82 min, MS (ESI) m/z: 353.9 (M+H)$^+$.

Intermediate I-143B (2R,3S)-3-((4-chloro-2-(6-chloro-3-methoxyquinolin-8-yl)-5-fluorobenzo[d]thiazol-6-yl) oxy)butan-2-ol

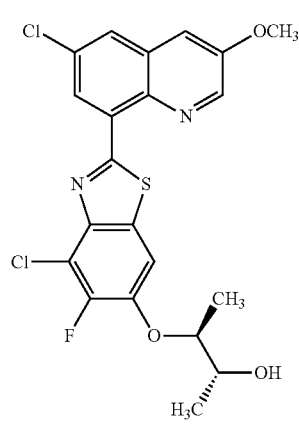
(I-143B)

Intermediate I-121 (149 mg, 0.467 mmol), Intermediate I-143A (145 mg, 0.467 mmol) and PdCl$_2$(dppf) (20.52 mg, 0.028 mmol) were dissolved in dioxane (8.523 mL) and Na$_2$CO$_3$ (2.104 mL, 4.21 mmol, 2 M) and heated to 100° C. in an oil bath for 1 hour. The reaction mixture was cooled to ambient temperature, diluted with EtOAc, washed with water, then brine, dried (Na$_2$SO$_4$), filtered, and concentrated in vacuo. Purified on ISCO using 0-100% EtOAc in DCM on a 24 g column to yield Intermediate I-143B (0.022 g, 0.047 mmol, 10.07% yield): LC-MS: method H, RT=1.40 min, MS (ESI) m/z: 466.8 (M+H)$^+$.

Intermediate I-143

To a solution of Intermediate I-143B (0.022 g, 0.047 mmol) in THF (5 mL) at room temperature was added 15% phosgene in toluene (0.166 mL, 0.235 mmol) and the mixture was stirred at room temperature overnight. Solvent was completely removed to give Intermediate I-143 (0.025 g, 0.047 mmol, 100% yield) as a yellow solid. LC-MS: method H, RT=1.41 min, MS (ESI) m/z: 530.8 (M+H)$^+$.

Intermediate I-144

2-ethoxy-7-methyl-5-(4,4,5,5-tetramethyl-1,3,2-dioxaborolan-2-yl)quinoxaline

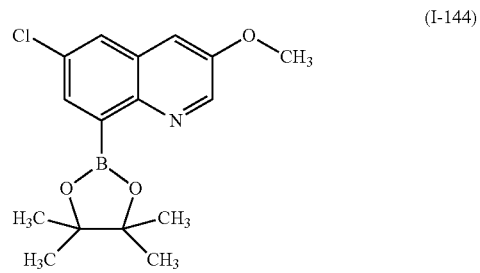 [SMILES: COc1cnc2c(B3OC(C)(C)C(C)(C)O3)cc(Cl)cc2c1]
(I-144)

Intermediate I-144A:
5-bromo-2-ethoxy-7-methylquinoxaline

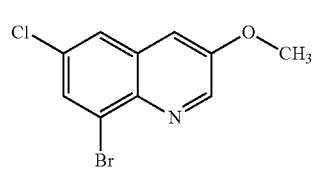
(I-144A)

Intermediate I-1G (372 mg, 1.287 mmol) was suspended in EtOH (10 mL) and was mixed with 21% sodium ethoxide in ethanol (2 mL, 5.36 mmol). Mixture was stirred at 40° C. for 1 hour. The solvent was removed on rotavapor and residue was dissolved in 20 mL of EtOAc and 15 mL of water. The layers were separated and the aqueous layer was extracted with EtOAc (10 mL×2). The combined organic layer was washed with brine, dried over Na$_2$SO$_4$, filtered and concentrated. Crude product was loaded on ISCO (24 g column, 0-50% EtOAC/Hexane gradient) to yield Intermediate I-144A (292 mg, 1.093 mmol, 85% yield) as white solid. $^1$H NMR (400 MHz, DMSO-d$_6$) δ 8.58 (s, 1H), 7.85 (d, J=1.5 Hz, 1H), 7.65 (s, 1H), 4.50 (q, J=7.0 Hz, 2H), 2.50

(s, 3H), 1.42 (t, J=7.0 Hz, 3H) LC-MS: method H, RT=1.14 min, MS (ESI) m/z: 269.1 (M+H)⁺.

Intermediate I-144

In a sealed tube, Intermediate I-144A (290 mg, 1.086 mmol), 4,4,4',4',5,5,5',5'-octamethyl-2,2'-bi(1,3,2-dioxaborolane) (551 mg, 2.171 mmol), potassium acetate (213 mg, 2.171 mmol) were mixed in 1,4-dioxane (5 mL). After degassing with bubbling $N_2$ for 10 minutes, Pd(dppf)Cl$_2$ CH$_2$Cl$_2$ adduct (44.3 mg, 0.054 mmol) was added. The vial was sealed and was heated at 120° C. for 60 minutes. The reaction mixture was cooled room temperature and loaded on celite. Purified on ISCO (40 g column, 0-50% EtOAc/Hexane in 18 minutes) to yield I-144 (0.311 g, 0.990 mmol, 91% yield). ¹H NMR (400 MHz, DMSO-d$_6$) δ 8.53 (s, 1H), 7.91 (s, 1H), 7.68 (s, 1H), 4.47 (q, J=7.2 Hz, 2H), 3.26 (br. s., 3H), 1.41 (t, J=7.0 Hz, 3H), 1.34 (s, 12H). LC-MS: method H, RT=0.94 min, MS (ESI) m/z: 233.0 (M+H)⁺. See mass of boronic acid.

Example 1

5-(benzofuran-2-yl)-2-(difluoromethoxy)-7-methylquinoxaline

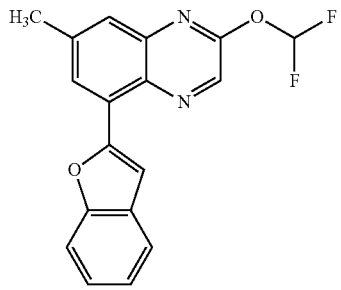

(1)

A mixture of Intermediate I-1G (40 mg, 0.138 mmol), benzofuran-2-ylboronic acid (28.0 mg, 0.173 mmol) and [1,1'-bis(diphenylphosphino)ferrocene] dichloropalladium (II) complex with dichloromethane (1:1) (6.78 mg, 8.30 μmol) in toluene (1.8 mL) and EtOH (0.600 mL) was degassed with argon for 2.0 min. To this solution was added sodium carbonate (2M, 0.121 mL, 0.242 mmol). The mixture was heated in a microwave reactor at 100° C. for 30 min. The reaction mixture was diluted with EtOAc/water. The organic layer was collected, dried over sodium sulfate. The crude residue was dissolved in DMSO/acetonitrile (6 mL/6 mL), purified using a preparative HPLC (method A, 70-100% B in 10 min, flow rate of 40 mL/min). The desired fractions were placed in a SpeedVac overnight to remove solvent, then lyophilized to give Example 1 (28 mg, 0.085 mmol, 61.4% yield) as yellow lyophilate. ¹H NMR (500 MHz, DMSO-d$_6$) δ 8.87 (s, 1H), 8.27 (d, J=1.9 Hz, 1H), 8.13 (d, J=0.8 Hz, 1H), 7.85 (t, $J_{HF}$=71.85 Hz, 1H), 7.79 (dd, J=7.7, 0.6 Hz, 1H), 7.75 (dd, J=1.8, 1.0 Hz, 1H), 7.68 (dd, J=8.3, 0.8 Hz, 1H), 7.41 (ddd, J=8.3, 7.2, 1.1 Hz, 1H), 7.34-7.30 (m, 1H), 2.66 (s, 3H); ¹⁹F NMR (471 MHz, DMSO-d$_6$) δ −88.42 (s, 2F); LC-MS: Method A, 50 to 100% B. RT=2.32 min, MS (ESI) m/z: 327.1 (M+H)⁺. Analytical HPLC (low pH, 254 nM): Sunfire, RT=12.62 min, 100% purity; XBridge, RT=8.29 min, 99% purity.

Example 2

2-(difluoromethoxy)-5-(5-methoxybenzofuran-2-yl)-7-methylquinoxaline

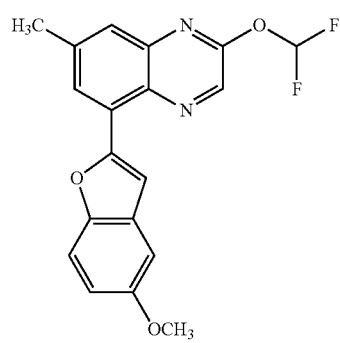

(2)

Intermediate 2A: (5-methoxybenzofuran-2-yl)boronic acid

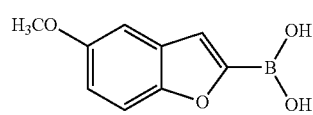

(2A)

To 5-methoxybenzofuran (188 mg, 1.269 mmol) in THF (4.0 mL) at −78° C. was added 1.6 N n-BuLi in hexanes (1.190 mL, 1.903 mmol) dropwise. The solution became slightly yellow. The reaction mixture was stirred at −78° C. for 20 min, followed by addition of triisopropyl borate (0.737 mL, 3.17 mmol). After 30 min stirring at −78° C., the cooling bath was removed and the stirring was continued at room temperature for 1.5 h. The reaction mixture was diluted with EtOAc, quenched with 3.0 mL of 1.0 N HCl. After stirring at room temperature for 25 min, the organic layer was collected, washed with brine and dried over sodium sulfate. After evaporation of solvent, the crude product was dissolved in a small amount of chloroform/a drop of MeOH and charged to a 4 g silica gel cartridge which was eluted with hexanes for 2 min., then a 10 min gradient from 0% to 60%. The desired fractions were combined, concentrated and lyophilized to give Intermediate 2A (170 mg, 0.886 mmol, 69.8% yield) as a white solid. ¹H NMR (500 MHz, methanol-d$_4$) δ 7.41 (d, J=9.1 Hz, 1H), 7.30 (s, 1H), 7.14 (d, J=2.5 Hz, 1H), 6.96 (dd, J=8.9, 2.6 Hz, 1H), 3.84 (s, 3H); LC-MS: method A, RT=1.45 min, MS (ESI) m/z: 149.0 (M-B(OH)$_2$)⁺.

Example 2

A mixture of Intermediate I-1G (22 mg, 0.076 mmol), Intermediate 2A (18.26 mg, 0.095 mmol) and [1,1'-bis(diphenylphosphino)ferrocene]dichloropalladium (II) complex with dichloromethane (1:1) (4.97 mg, 6.09 μmol) in toluene (1.5 mL) and EtOH (0.5 mL) was degassed with argon for 2.0 min. To this solution was added sodium carbonate (2M, 0.067 mL, 0.133 mmol). The reaction mixture was heated in a microwave reactor at 100° C. for 30 min, then diluted with EtOAc/water. The organic layer was collected, dried over sodium sulfate. After evaporation of solvent, the crude residue was dissolved in DMSO/MeOH (6 mL/4 mL), purified using a preparative HPLC (method A, 70-100% B in 10 min, flow rate of 40 mL/min). The desired fractions were placed in a SpeedVac overnight to remove solvent, then lyophilized to give Example 2 (15 mg, 0.042 mmol, 54.8% yield) as yellow lyophilate. $^1$H NMR (500 MHz, DMSO-$d_6$) δ 8.90 (s, 1H), 8.21 (d, J=1.4 Hz, 1H), 8.05 (s, 1H), 7.88 (t, $J_{HF}$=71.53 Hz, 1H), 7.75 (s, 1H), 7.58 (d, J=8.8 Hz, 1H), 7.30 (d, J=2.8 Hz, 1H), 6.98 (dd, J=8.9, 2.6 Hz, 1H), 3.82 (s, 3H), 2.63 (s, 3H); $^{19}$F NMR (471 MHz, DMSO-$d_6$) δ −87.80 (s, 2F); LC-MS: Method A, 50 to 100% B. RT=2.27 min, MS (ESI) m/z: 357.0 (M+H)$^+$. Analytical HPLC (low pH, 254 nM): Sunfire, RT=12.92 min, 99% purity; XBridge, RT=9.70 min, 99% purity.

Example 3

2-(2-(difluoromethoxy)-7-methylquinoxalin-5-yl)benzo[d]oxazole

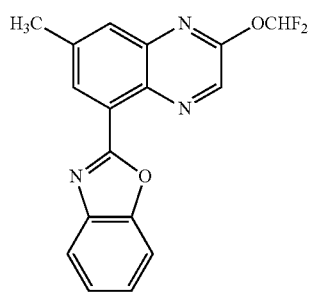

(3)

Intermediate 3A: 2-iodobenzo[d]oxazole

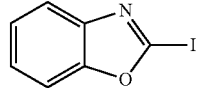

(3A)

To magnesium bromide (52 mg, 0.282 mmol) in THF (0.5 mL) cooled at −10° C. was added 1.6 N n-BuLi in hexanes (0.530 mL, 0.847 mmol) dropwise. The reaction mixture was stirred between −10° C. and 0° C. for 1.0 h. Benzo[d]oxazole (101 mg, 0.847 mmol) in THF (0.5 mL) was added, and the brown mixture was stirred at room temperature for 2.0 h. Iodine (79 mg, 0.311 mmol) in THF (0.5 mL) was added, and the reaction mixture was stirred at room temperature for 18 h. The mixture was diluted with EtOAc, quenched with 10% Na$_2$S$_2$O$_3$. The organic layer was washed with water, brine and dried over sodium sulfate. After evaporation of solvent, the crude product was dissolved in a small amount of chloroform and charged to a 12 g silica gel cartridge which was eluted with hexanes for 3 min., then a 15 min gradient from 0% to 30%. The desired fractions were combined and concentrated to give Intermediate 3A (47 mg, 0.192 mmol, 67.9% yield) as a solid. $^1$H NMR (400 MHz, chloroform-d) δ 7.67-7.60 (m, 1H), 7.50-7.44 (m, 1H), 7.28-7.20 (m, 2H); LC-MS: method A, RT=1.73 min, MS (ESI) m/z: 246.0 (M+H)$^+$.

Example 3

To Intermediate I-1 (31 mg, 0.092 mmol), Intermediate 3A (29.4 mg, 0.120 mmol) and [1,1'-bis(diphenylphosphino)ferrocene]dichloropalladium (II) complex with dichloromethane (1:1) (6.03 mg, 7.38 μmol) was added toluene (0.9 mL) and EtOH (0.3 mL). The mixture was sonicated for 1 min, and flushed with argon. To this was added sodium carbonate (2M, 0.101 mL, 0.203 mmol). The reaction mixture was heated in a microwave reactor at 110° C. for 30 min. HPLC and LCMS indicated a completion of the reaction. To the reaction mixture was added EtOAc/water. The organic layer was collected, dried over sodium sulfate. After evaporation of solvent, the crude residue was purified using a preparative HPLC (method A, 40-100% B in 10 min, flow rate of 40 mL/min). The desired fractions were placed in a SpeedVac overnight to remove solvent, then lyophilized to give Example 3 (27 mg, 0.082 mmol, 89% yield) as a white lyophilate. $^1$H NMR (500 MHz, acetonitrile-$d_3$) 8.74 (br. s., 1H), 8.32 (d, J=1.9 Hz, 1H), 7.93 (br. s., 1H), 7.89-7.85 (m, 1H), 7.76 (d, J=7.2 Hz, 1H), 7.71 (t, $J_{HF}$=71.53 Hz, 1H), 7.53-7.45 (m, 2H), 2.69 (s, 3H); $^{19}$F NMR (471 MHz, acetonitrile-$d_3$) δ −90.12 (s, 2F); LC-MS: Method A, 40 to 100% B. RT=1.81 min, MS (ESI) m/z: 328.0 (M+H)$^+$. Analytical HPLC (low pH, 254 nM): Sunfire, RT=9.41 min, 99% purity; XBridge, RT=7.19 min, 99% purity.

Example 4

2-(2-(difluoromethoxy)-7-methylquinoxalin-5-yl)benzo[d]thiazole

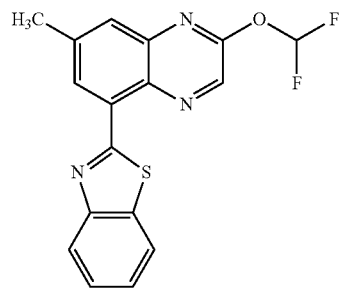

(4)

To a microwave reaction tube was charged dichlorobis(chloro-di-tert-butylphosphine)palladium (1.118 mg, 2.076 μmol), Cu(Xantphos)I (6.39 mg, 8.30 μmol), cesium carbonate (85 mg, 0.259 mmol), benzo[d]thiazole (0.017 mL, 0.156 mmol) and Intermediate I-1G (30 mg, 0.104 mmol). Toluene (1.0 mL) was added and the reaction mixture was sealed and heated at 100° C. The mixture was diluted with EtOAc/water, the organic layer was collected, dried over sodium sulfate. The crude residue was purified using a preparative HPLC (method A, 60-100% B in 10 min, flow rate of 40 mL/min). The desired fractions were placed in a SpeedVac overnight to remove solvent, then lyophilized to give Example 4 (2.2 mg, 6.34 μmol, 6.11% yield) as a white lyophilate. $^1$H NMR (500 MHz, acetonitrile-$d_3$) δ 8.84 (d, J=1.7 Hz, 1H), 8.78 (s, 1H), 8.15-8.11 (m, 2H), 7.87 (dd, J=1.8, 1.0 Hz, 1H), 7.72 (t, $J_{HF}$=71.82 Hz, 1H), 7.59 (ddd, J=8.2, 7.1, 1.2 Hz, 1H), 7.50 (td, J=7.6, 1.1 Hz, 1H), 2.72 (s, 3H); $^{19}$F NMR (471 MHz, acetonitrile-$d_3$) δ −90.06 (s, 2F); LC-MS: Method H, 50 to 100% B. RT=1.93 min, MS (ESI)

m/z: 344.2 (M+H)⁺. Analytical HPLC (low pH, 254 nM): Sunfire, RT=12.49 min, 100% purity; XBridge, RT=9.38 min, 99% purity.

Example 5

2-(difluoromethoxy)-5-(1H-indol-2-yl)-7-methylquinoxaline

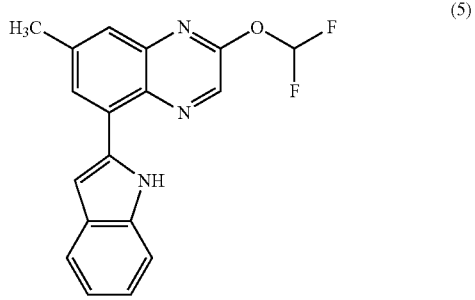 [SMILES: Cc1cc(-c2cc3ccccc3[nH]2)c2ncc(OC(F)F)nc2c1]
(5)

Intermediate 5A: tert-butyl 2-(tributylstannyl)-1H-indole-1-carboxylate

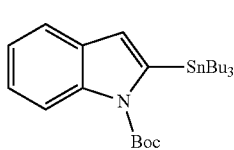
(5A)

To diisopropylamine (0.984 mL, 6.90 mmol) in THF (12 mL) at −78° C. was added 1.6 N n-BuLi in hexanes (4.32 mL, 6.90 mmol). The reaction mixture was stirred at −78° C. for 0.5 h. Next, tert-butyl 1H-indole-1-carboxylate (0.935 mL, 4.60 mmol) was added, and the reaction mixture was stirred at −78° C. for 0.5 h. Tributyltin chloride (1.489 mL, 5.52 mmol) was added, and the reaction mixture was stirred at −78° C. for 0.5 h, then at room temperature for 1.5 h. The reaction mixture was diluted with EtOAc, quenched with saturated ammonium chloride. The organic layer was washed with brine, dried over sodium sulfate. After evaporation of solvent, the crude product was dissolved in a small amount of chloroform and charged to a 40 g silica gel cartridge which was eluted with hexanes for 3 min., then a 18 min gradient from 0% to 30%. The desired fractions were combined and concentrated to give Intermediate 5A (2.1 g, 4.15 mmol, 90% yield) as clear oil. ¹H NMR (500 MHz, chloroform-d) δ 7.98-7.94 (m, 1H), 7.54-7.50 (m, 1H), 7.26-7.15 (m, 2H), 6.74-6.69 (m, 1H), 1.71 (s, 9H), 1.58-1.49 (m, 7H), 1.33 (sxt, J=7.3 Hz, 6H), 1.11-1.06 (m, 5H), 0.89 (t, J=7.4 Hz, 9H); LC-MS: Method A, 60 to 100% B. RT=1.86 min, MS (ESI) m/z: not observed.

Example 5

A solution of Intermediate 5A (65.7 mg, 0.130 mmol) and Intermediate I-1G (30 mg, 0.104 mmol) in toluene (1.2 mL) was degassed with argon for 3 min. Tetrakis(triphenylphosphine)palladium(0) (6.00 mg, 5.19 µmol) was added. The reaction mixture was sealed and heated in a microwave reactor at 125° C. for 30 min. HPLC and LCMS indicated only 15% conversion. Then another portion of Intermediate 5A (65.7 mg, 0.130 mmol) and tetrakis(triphenylphosphine)palladium(0) (6.00 mg, 5.19 µmol) were added, and the reaction mixture was heated at 125° C. for another 1.0 h. Toluene was removed under vacuum. 4.0 N HCl in dioxane (2.076 mL, 8.30 mmol) was added and the reaction mixture was stirred at room temperature overnight. Solvent was removed in vacuum. The crude residue was purified using a preparative HPLC (method A, 50-100% B in 10 min, flow rate of 40 mL/min). The desired fractions were placed in a SpeedVac overnight to remove solvent, then lyophilized to give Example 5 (5.0 mg, 0.014 mmol, 13.92% yield) as yellow lyophilate. ¹H NMR (500 MHz, acetonitrile-d₃) δ 8.72 (s, 1H), 8.26 (d, J=1.7 Hz, 1H), 7.71 (t, J_HF=71.82 Hz, 1H), 7.68 (d, J=8.0 Hz, 1H), 7.65 (d, J=0.8 Hz, 1H), 7.61 (dd, J=8.3, 0.8 Hz, 1H), 7.30-7.28 (m, 1H), 7.23 (ddd, J=8.1, 7.0, 1.1 Hz, 1H), 7.12 (td, J=7.5, 1.0 Hz, 1H), 2.65 (s, 3H); ¹⁹F NMR (471 MHz, acetonitrile-d₃) δ −90.04 (s, 2F); LC-MS: Method H, 0 to 100% B. RT=1.88 min, MS (ESI) m/z: 326.3 (M+H)⁺. Analytical HPLC (method A): Sunfire, RT=11.54 min, 99% purity; XBridge, RT=9.21 min, 90% purity.

Example 6

2-(difluoromethoxy)-5-(4,5-dimethoxybenzofuran-2-yl)-7-methylquinoxaline

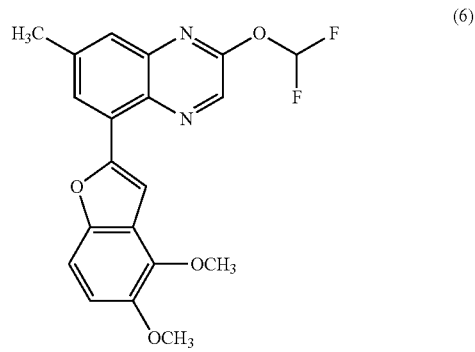 [SMILES: COc1ccc2oc(-c3cc(C)cc4nc(OC(F)F)cnc34)cc2c1OC]
(6)

Intermediate 6A: 5-(hydroxymethylene)-6,7-dihydrobenzofuran-4(5H)-one

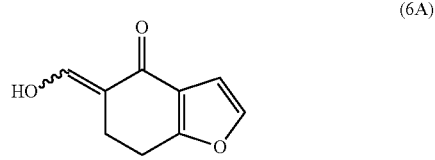 [SMILES: O=C1C(=CO)CCc2occc21]
(6A)

To sodium hydride (1.175 g, 29.4 mmol) and potassium hydride (0.098 g, 0.734 mmol) in THF (25 mL) at 0° C. was added ethyl formate (2.99 mL, 36.7 mmol), followed by addition of 6,7-dihydrobenzofuran-4(5H)-one (1.0 g, 7.34 mmol) in THF (5.0 mL) dropwise. The reaction mixture was stirred at room temperature for 1.0 h and heated at 50° C. for 1.5 h. HPLC and LCMS indicated a completion of reaction. The mixture was diluted with EtOAc, cooled to 0° C., quenched with 3.0 mL MeOH/water, pH was adjusted to 7 with 1.0 N HCl. The organic layer was collected, washed with brine, dried over sodium sulfate. After evaporation of solvent, Intermediate 6A (1.36 g, 8.28 mmol, 113% yield) was obtained as yellow liquid. It was used for the next step without further purification. $^1$H NMR indicated a mixture of the keto and enol form in a ratio of 1:7. $^1$HNMR of the enol form: (500 MHz, chloroform-d) δ 7.39-7.36 (m, 1H), 7.31-7.26 (m, 1H), 6.74 (d, J=2.2 Hz, 1H), 2.93-2.87 (m, 2H), 2.68 (td, J=7.0, 0.8 Hz, 2H); LC-MS: method A, RT=1.19 and 1.35 min, MS (ESI) m/z: 165.0 (M+H)$^+$.

Intermediate 6B:
4-hydroxybenzofuran-5-carbaldehyde

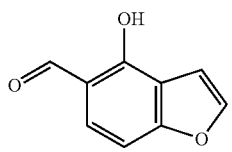

(6B)

To a suspension of DDQ (2.074 g, 9.14 mmol) in dioxane (6.0 mL) was added Intermediate 6A (1.2 g, 7.31 mmol) in dioxane (7.0 mL) dropwise. The reaction mixture was stirred at room temperature for 2.0 h. TLC indicated a completion of the reaction. It was diluted with EtOAc, stirred for 15 min. The precipitate was filtered and the filtrate was concentrated. The crude was triturated with chloroform and the precipitate was removed by filtration. The filtrate was concentrated, dissolved in a small amount of chloroform and charged to a 80 g silica gel cartridge which was eluted with hexanes for 3 min., then a 15 min gradient from 0% to 40%. The desired fractions were combined and concentrated to give Intermediate 6B (0.66 g, 4.07 mmol, 55.7% yield) as a slightly brown solid. $^1$H NMR (500 MHz, chloroform-d) δ 12.01 (s, 1H), 9.94 (s, 1H), 7.63 (d, J=2.2 Hz, 1H), 7.48 (d, J=8.5 Hz, 1H), 7.18 (dd, J=8.7, 1.0 Hz, 1H), 7.03 (dd, J=2.2, 0.8 Hz, 1H); LC-MS: method A, RT=1.65 min, MS (ESI) m/z: 163.0 (M+H)$^+$.

Intermediate 6C:
4-methoxybenzofuran-5-carbaldehyde

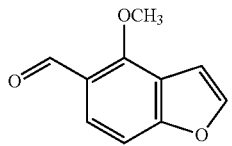

(6C)

To Intermediate 6B (0.66 g, 4.07 mmol) in DMF (6.0 mL) was added potassium carbonate (1.547 g, 11.19 mmol), followed by iodomethane (0.445 mL, 7.12 mmol). The mixture was allowed to stir at room temperature overnight. The reaction mixture was diluted with EtOAc/water. The organic layer was collected, washed with brine, dried over sodium sulfate. After evaporation of solvent, Intermediate 6C (0.68 g, 3.86 mmol, 95% yield) was obtained as a white solid. It was used for the next step without further purification. $^1$H NMR (500 MHz, chloroform-d) δ 10.51 (d, J=0.8 Hz, 1H), 7.85 (d, J=8.5 Hz, 1H), 7.66 (d, J=2.2 Hz, 1H), 7.28-7.24 (m, 1H), 7.08 (dd, J=2.2, 0.8 Hz, 1H), 4.29 (s, 3H); LC-MS: method A, RT=1.62 min, MS (ESI) m/z: 177.0 (M+H)$^+$.

Intermediate 6D: 4-methoxybenzofuran-5-yl formate

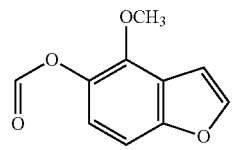

(6D)

To a stirred solution of Intermediate 6C (0.31 g, 1.760 mmol) in dichloromethane (4.0 mL) was added mCPBA (0.557 g, 2.420 mmol). Trifluoroacetic acid (0.136 mL, 1.760 mmol) in dichloromethane (2.0 mL) was added. The reaction mixture was stirred at room temperature for 2.0 h. Sodium thiosulfite (10%, 1.0 mL) was added to quench the reaction. Solvent was removed under vacuum. The residue was partitioned between EtOAc/saturated sodium bicarbonate. The organic layer was collected, washed with saturated sodium bicarbonate, brine and dried over sodium sulfate. After evaporation of solvent, Intermediate 6D (0.34 g, 1.769 mmol, 101% yield) was obtained as brown oil that was used for next step without further purification. LC-MS: method A, RT=1.53 min, MS (ESI) m/z: 215.0 (M+Na)$^+$.

Intermediate 6E: 4-methoxybenzofuran-5-ol

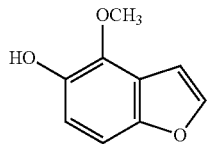

(6E)

To Intermediate 6D (0.34 g, 1.769 mmol) in MeOH (5.0 mL) was added potassium carbonate (0.428 g, 3.10 mmol). The mixture was allowed to stir at room temperature for 20 min. MeOH was removed under vacuum. The residue was partitioned between EtOAc/water. The organic layer was collected, washed with brine, dried over sodium sulfate. After evaporation of solvent, the crude product was dissolved in a small amount of chloroform and charged to a 12 g silica gel cartridge which was eluted with hexanes for 2 min., then a 15 min gradient from 0% to 40%. The desired fractions were combined and concentrated to give Intermediate 6E (0.22 g, 1.340 mmol, 76% yield) as viscous oil. $^1$H NMR (500 MHz, chloroform-d) δ 7.57 (d, J=2.2 Hz, 1H), 7.13 (dd, J=8.7, 1.0 Hz, 1H), 6.96 (d, J=8.8 Hz, 1H), 6.88 (dd, J=2.2, 0.8 Hz, 1H), 4.13 (s, 3H); LC-MS: method A, RT=1.40 min, MS (ESI) m/z: 187.0 (M+Na)$^+$.

Intermediate 6F:
4-methoxy-5-(methoxymethoxy)benzofuran

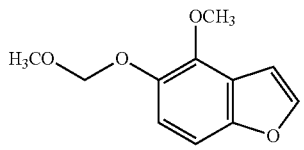
(6F)

To Intermediate 6E (0.21 g, 1.279 mmol) in DMF (4.0 mL) at 0° C. was added sodium hydride (0.070 g, 1.759 mmol, 60% in mineral). The reaction mixture was stirred at 0° C. for 5 min, and at room temperature for 10 min. The mixture turned to deep blue color. Chloromethyl methyl ether (0.136 mL, 1.791 mmol) was added slowly, and the reaction mixture was stirred at room temperature for 30 min. HPLC and TLC indicated a completion of the reaction. The mixture was diluted with EtOAc, washed with water, brine. The organic layer was dried over sodium sulfate. After evaporation of solvent, the crude product was dissolved in a small amount of chloroform and charged to a 12 g silica gel cartridge which was eluted with hexanes for 3 min., then a 12 min gradient from 0% to 30%. The desired fractions were combined and concentrated to give Intermediate 6F (0.24 g, 1.153 mmol, 90% yield). $^1$H NMR (500 MHz, chloroform-d) δ 7.56 (d, J=2.2 Hz, 1H), 7.18-7.13 (m, 2H), 6.91 (dd, J=2.2, 0.6 Hz, 1H), 5.21 (s, 2H), 4.10 (s, 3H), 3.59 (s, 3H); LC-MS: method A, RT=1.70 min, MS (ESI) m/z: 231.0 (M+H)$^+$.

Intermediate 6G: (4-methoxy-5-(methoxymethoxy)benzofuran-2-yl)boronic acid

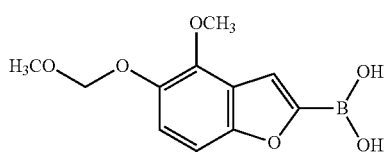
(6G)

To Intermediate 6F (0.236 g, 1.133 mmol) in THF (4.0 mL) at −78° C. was added 1.6 N n-BuLi in hexanes (1.240 mL, 1.984 mmol) dropwise. The reaction mixture was stirred at −78° C. for 30 min, followed by addition of triisopropyl borate (0.790 mL, 3.40 mmol). The reaction mixture was stirred for 30 min, and the cooling bath was removed to allow warm up to room temperature for 1.0 h. TLC and HPLC indicated a completion of the reaction. The reaction mixture was diluted with EtOAc and quenched with 4.0 mL of 0.5 N HCl. After stirring at room temperature for 10 min, the organic layer was collected, washed with brine and dried over sodium sulfate. After evaporation of solvent, the crude product was dissolved in a small amount of chloroform and charged to a 4 g silica gel cartridge which was eluted with 5% for 2 min., then a 5 min gradient from 5% to 85%. The desired fractions were combined, concentrated and lyophilized to give Intermediate 6G (0.23 g, 0.913 mmol, 81% yield) as a white solid. $^1$H NMR (400 MHz, methanol-d$_4$) δ 7.39 (s, 1H), 7.06 (s, 2H), 5.06 (s, 2H), 4.72 (br. s., 1H), 3.98 (s, 3H), 3.46 (s, 3H); LC-MS: method A, RT=1.42 min, MS (ESI) m/z: 177.0.

Intermediate 6H 2-(difluoromethoxy)-5-(4-methoxy-5-(methoxymethoxy)benzofuran-2-yl)-7-methylquinoxaline

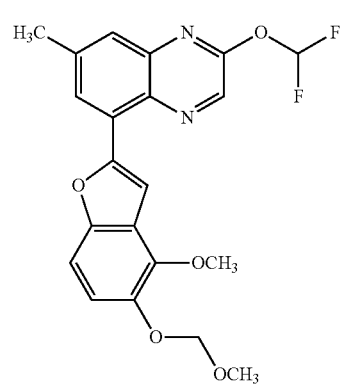
(6H)

A mixture of Intermediate I-1G (30 mg, 0.104 mmol), Intermediate 6G (32.7 mg, 0.130 mmol) and [1,1'-bis(diphenylphosphino)ferrocene]dichloropalladium (II) complex with dichloromethane (1:1) (5.93 mg, 7.26 μmol) in toluene (1.8 mL) and EtOH (0.600 mL) was degassed with argon for 2.0 min. To this solution was added sodium carbonate (2M, 0.104 mL, 0.208 mmol). The mixture was heated in a microwave reactor at 100° C. for 30 min, at which time HPLC and LCMS indicated a completion of the reaction. The reaction mixture was diluted with EtOAc/water. The organic layer was collected, dried over sodium sulfate. The crude residue was dissolved in DMSO/acetonitrile (2 mL/3 mL), purified using a preparative HPLC (method A, 50-100% B in 10 min; RT=9.5 min). The desired fractions were placed in a SpeedVac overnight to remove solvent, then lyophilized to give Intermediate 6H (26 mg, 0.060 mmol, 57.8% yield) as yellow lyophilate. $^1$H NMR (500 MHz, acetonitrile-d$_3$) δ 8.75 (s, 1H), 8.27 (d, J=1.9 Hz, 1H), 8.25 (d, J=0.8 Hz, 1H), 7.72 (dd, J=1.9, 1.1 Hz, 1H), 7.71 (t, J$_{HF}$=71.80 Hz, 1H), 7.29-7.25 (m, 1H), 7.22-7.19 (m, 1H), 5.20 (s, 2H), 4.14 (s, 3H), 3.55 (s, 3H), 2.67 (s, 3H); $^{19}$F NMR (471 MHz, acetonitrile-d$_3$) δ −90.01 (s, 2F); LC-MS: Method A, 50 to 100% B. RT=2.19 min, MS (ESI) m/z: 417.1 (M+H)$^+$. Analytical HPLC (method A): Sunfire, RT=12.38 min, 99% purity; XBridge, RT=9.66 min, 94% purity.

Intermediate 6I 2-(2-(difluoromethoxy)-7-methylquinoxalin-5-yl)-4-methoxybenzofuran-5-ol

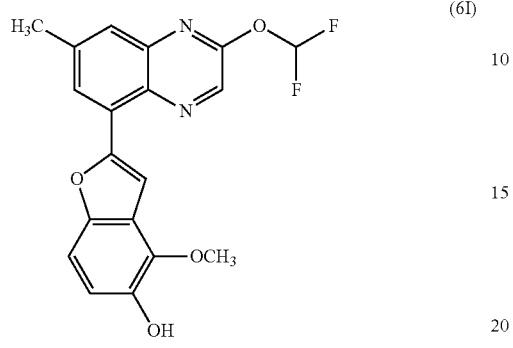

(6I)

To Intermediate 6H (16 mg, 0.038 mmol) in THF (1.5 mL) and MeOH (0.5 mL) was added 6.0 N HCl (0.640 mL, 3.84 mmol). The reaction mixture was stirred at 60° C. for 1.0 h. HPLC indicated a completion of the reaction. It was diluted with EtOAc, washed with water, brine. The organic layer was collected, dried over sodium sulfate. After evaporation of solvent, Intermediate 6I (13 mg, 0.035 mmol, 91% yield) was obtained as a brown solid that was used for next step without further purification. $^1$H NMR (500 MHz, acetonitrile-d$_3$) δ 8.72 (s, 1H), 8.21 (d, J=5.0 Hz, 2H), 7.69 (t, J$_{HF}$=71.53 Hz, 1H), 7.68 (br. s., 1H), 7.18 (d, J=8.5 Hz, 1H), 6.94 (d, J=8.5 Hz, 1H), 6.53 (br. s., 1H), 4.14 (s, 3H), 2.65 (s, 3H); $^{19}$F NMR (471 MHz, acetonitrile-d$_3$) δ −89.92 (br. s., 2F); LC-MS: method A, RT=1.86 min, MS (ESI) m/z: 373.0 (M+H)$^+$.

Example 6

To a stirred solution of Intermediate 6I (13 mg, 0.035 mmol) and cesium carbonate (28.4 mg, 0.087 mmol) in DMF (0.8 mL) at room temperature was added methyl iodide (3.82 μl, 0.061 mmol) in acetonitrile (0.03 mL). The reaction mixture was stirred at room temperature for 1.0 h. HPLC and LCMS indicated a completion of the reaction. The mixture was diluted with EtOAc, quenched with 0.2 N HCl (2.0 mL). The organic layer was collected, dried over sodium sulfate. After evaporation of solvent, the crude was purified using a preparative HPLC (method A, 60-100% B in 10 min; RT=8.5 min). The desired fractions were placed in a SpeedVac overnight to remove solvent, then lyophilized to give Example 6 (9.5 mg, 0.024 mmol, 68.3% yield) as yellow lyophilate. $^1$H NMR (500 MHz, acetonitrile-d$_3$) δ 8.74 (s, 1H), 8.24 (d, J=1.7 Hz, 1H), 8.19 (s, 1H), 7.71 (t, J$_{HF}$=71.80 Hz, 1H), 7.70 (s, 1H), 7.27 (d, J=8.8 Hz, 1H), 7.12 (d, J=8.8 Hz, 1H), 4.09 (s, 3H), 3.91 (s, 3H), 2.66 (s, 3H); $^{19}$F NMR (471 MHz, acetonitrile-d$_3$) δ −90.01 (s, 2F); LC-MS: Method A, 50 to 100% B. RT=2.15 min, MS (ESI) m/z: 387.0 (M+H)$^+$. Analytical HPLC (method A): Sunfire, RT=12.88 min, 100% purity; XBridge, RT=10.21 min, 96% purity.

Example 7

6-(benzyloxy)-2-(2-(difluoromethoxy)-7-methylquinoxalin-5-yl)benzo[d]thiazole

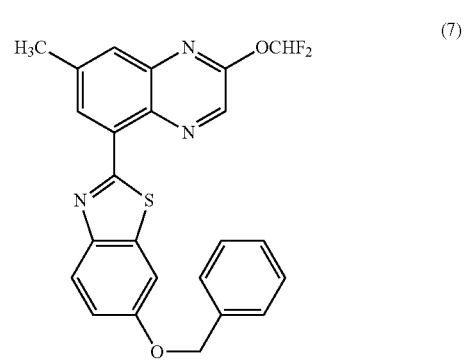 [SMILES: Cc1cc(-c2nc3ccc(OCc4ccccc4)cc3s2)c2ncc(OC(F)F)nc2c1]

(7)

To a stirred solution of Intermediate I-4D (10 mg, 0.028 mmol) and cesium carbonate (22.67 mg, 0.070 mmol) in DMF (0.6 mL) at room temperature was added benzyl bromide (5.79 μL, 0.049 mmol) in acetonitrile (0.03 mL). The reaction mixture was stirred at room temperature for 3 h. HPLC and LCMS indicated a completion of the reaction. The mixture was diluted with EtOAc, quenched with 0.2 N HCl (2.0 mL). The organic layer was collected, dried over sodium sulfate. After evaporation of solvent, the crude was purified via preparative LC/MS (method D), 55-95% B over 10 minutes. Fractions containing the desired product were combined and dried via centrifugal evaporation to yield Example 7 (12.1 mg). $^1$H NMR (500 MHz, DMSO-d$_6$) δ 8.96 (s, 1H), 8.73 (d, J=1.4 Hz, 1H), 8.05-8.02 (m, 1H), 7.90 (d, J=5.8 Hz, 1H), 7.89 (t, J$_{HF}$=71.53 Hz, 1H), 7.85 (d, J=2.5 Hz, 1H), 7.53 (d, J=7.4 Hz, 2H), 7.43 (t, J=7.4 Hz, 2H), 7.39-7.35 (m, 1H), 7.26 (dd, 2.5 Hz, 1H), 5.23 (s, 2H), 2.67 (s, 3H); LC-MS: Method A, 0 to 100% B. RT=3.33 min, MS (ESI) m/z: 450.0 (M+H)$^+$. Analytical HPLC purity (method B): 100%.

Example 8

4-chloro-2-(2-(difluoromethoxy)-7-methylquinoxalin-5-yl)benzo[d]thiazole

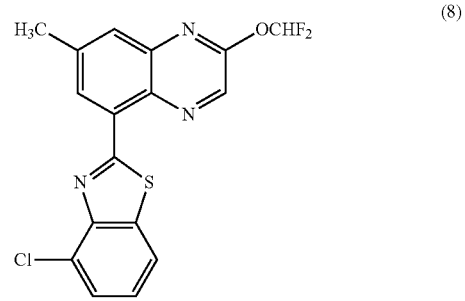 [SMILES: Cc1cc(-c2nc3c(Cl)cccc3s2)c2ncc(OC(F)F)nc2c1]

(8)

Intermediate 8A: 4-chloro-2-iodobenzo[d]thiazole

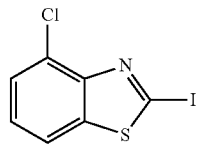

(8A)

To a suspension of 4-chlorobenzo[d]thiazol-2-amine (0.66 g, 3.57 mmol) and p-TSA monohydrate (2.040 g, 10.72 mmol) in acetonitrile (16 mL) at 10° C. (cooled with ice water) was added dropwise a solution of sodium nitrite (0.493 g, 7.15 mmol) and potassium iodide (1.483 g, 8.94 mmol) in water (4 mL) over a period of 25 min. The reaction mixture was stirred at 10° C. for 10 min, and allowed to warm up to room temperature and stirred over the weekend. To the reaction mixture was added sodium bicarbonate (pH to 9.0), water and EtOAc. The organic layer was collected, washed with water, saturated $Na_2S_2O_3$, water, brine and dried over sodium sulfate. After evaporation of solvent, the crude product was dissolved in a small amount of chloroform/toluene/MeOH and charged to a 40 silica gel cartridge which was eluted with hexanes for 3 min., then a 18 min gradient from 0% to 30%. The desired fractions were combined and concentrated to give Intermediate 8A (0.571 g, 1.932 mmol, 54.1% yield) as a white solid. $^1$H NMR (500 MHz, chloroform-d) δ 7.77 (dd, J=8.1, 1.0 Hz, 1H), 7.49 (dd, J=7.8, 1.0 Hz, 1H), 7.38-7.33 (m, 1H); LC-MS: method A, RT=1.94 min, MS (ESI) m/z: 296.0 and 298.0 (M+H)$^+$.

Example 8

To Intermediate I-1 (16 mg, 0.048 mmol), Intermediate 8A (20 mg, 0.067 mmol) and [1,1'-bis(diphenylphosphino)ferrocene]dichloropalladium (II) complex with dichloromethane (1:1) (3.0 mg, 3.67 μmol) was added toluene (1.2 mL) and EtOH (0.4 mL). The mixture was sonicated for 1 min, and flushed with argon. To this was added sodium carbonate (2M, 0.052 mL, 0.105 mmol). The reaction mixture was heated in a microwave reactor at 110° C. for 30 min. HPLC and LCMS indicated a completion of the reaction. To the reaction mixture was added EtOAc/water. The organic layer was collected, dried over sodium sulfate. After evaporation of solvent, the crude material was purified via preparative LC/MS (method D, 55-90% B over 10 minutes). Fractions containing the desired product were combined and dried via centrifugal evaporation to yield the Example 8 (4.2 mg). $^1$H NMR (500 MHz, DMSO-$d_6$) δ 8.99 (s, 1H), 8.79 (d, J=1.4 Hz, 1H), 8.19 (d, J=8.0 Hz, 1H), 7.97 (s, 1H), 7.90 (t, $J_{HF}$=71.53 Hz, 1H), 7.68 (d, J=7.7 Hz, 1H), 7.49 (t, J=7.8 Hz, 1H), 2.71 (s, 3H); LC-MS: Method H, 0 to 100% B. RT=3.66 min, MS (ESI) m/z: 378.0 (M+H)$^+$. Analytical HPLC purity (method B): 100%.

Example 9

2-(2-(difluoromethoxy)-7-methylquinoxalin-5-yl)thiazolo[4,5-b]pyridine

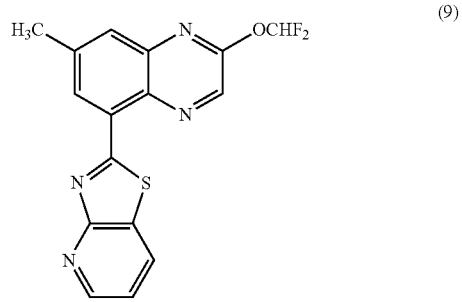

(9)

Intermediate 9A: 2-chlorothiazolo[4,5-b]pyridine

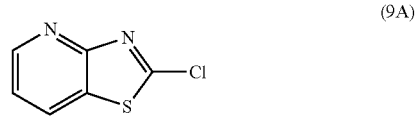

(9A)

To a slurry of thiazolo[4,5-b]pyridine-2-thiol (343 mg, 2.039 mmol) in dichloromethane (0.5 mL) was added sulfuryl chloride (3.32 mL, 40.8 mmol). The suspension was stirred at 50° C. for 2.0 h, and at room temperature overnight. To the yellow suspension was added ice water, stirred at room temperature for 15 min to decompose the excess sulfuryl chloride. EtOAc and 4.0 N NaOH were added to adjust the pH to 10-12. The organic layer was collected, washed with brine, dried over sodium sulfate. After evaporation of solvent, the crude product was dissolved in a small amount of chloroform and charged to a 12 g silica gel cartridge which was eluted with 5% for 3 min., then a 12 min gradient from 5% to 60%. The desired fractions were combined and concentrated to give Intermediate 9A (265 mg, 1.553 mmol, 76% yield) as a white solid. $^1$H NMR (500 MHz, chloroform-d) δ 8.76 (dd, J=5.0, 1.7 Hz, 1H), 8.19 (dd, J=8.0, 1.7 Hz, 1H), 7.39 (dd, J=8.0, 4.7 Hz, 1H); LC-MS: method A, RT=1.22 min, MS (ESI) m/z: 171 and 173 (M+H)$^+$.

Example 9

To Intermediate I-1 (17 mg, 0.051 mmol), Intermediate 9A (11.22 mg, 0.066 mmol) and [1,1'-bis(diphenylphosphino)ferrocene]dichloropalladium (II) complex with dichloromethane (1:1) (3.30 mg, 4.05 μmol) was added toluene (0.9 mL) and EtOH (0.3 mL). The mixture was sonicated for 1 min, and flushed with argon. To this was added sodium carbonate (2M, 0.056 mL, 0.111 mmol). The reaction mixture was heated in a microwave reactor at 130° C. for 30 min. HPLC and LCMS indicated a completion of the reaction. To the reaction mixture was added EtOAc/water. The mixture was stirred at room temperature for 15 min. The organic layer was collected. After evaporation of solvent, the crude material was purified via preparative LC/MS (method D, 40-90% B over 10 minutes) to yield the Example 9 (11.2 mg). $^1$H NMR (500 MHz, methanol-d$_4$) δ 8.93 (d, J=1.7 Hz, 1H), 8.73 (s, 1H), 8.72 (dd, J=4.7, 1.4 Hz, 1H), 8.47 (dd, J=8.0, 1.4 Hz, 1H), 7.89 (s, 1H), 7.71 (t, J$_{HF}$=71.53 Hz, 1H), 7.61 (s, 1H), 7.44 (dd, J=8.0, 4.7 Hz, 1H), 2.71 (s, 3H); LC-MS: Method H, 0 to 100% B. RT=2.59 min, MS (ESI) m/z: 345.0 (M+H)$^+$. Analytical HPLC purity (method B): 95%.

Example 10

2-(2-(difluoromethoxy)-7-methylquinoxalin-5-yl)-6-methoxy-4-methylbenzo[d]thiazole

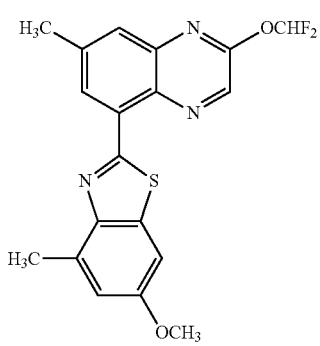

(10)

To Intermediate I-1 (25 mg, 0.074 mmol), Intermediate I-3 (24 mg, 0.093 mmol) and [1,1'-bis(diphenylphosphino)ferrocene]dichloropalladium (II) complex with dichloromethane (1:1) (4.86 mg, 5.95 μmol) was added toluene (1.2 mL) and EtOH (0.4 mL). The mixture was sonicated for 1 min, and flushed with argon. To this was added sodium carbonate (2M, 0.082 mL, 0.164 mmol). The reaction mixture was heated in a microwave reactor at 110° C. for 30 min. HPLC and LCMS indicated a completion of the reaction. EtOAc/brine was added to the mixture. The organic layer was collected, dried over sodium sulfate. After evaporation of solvent, the crude was dissolved in DMF (3.5 mL) and was purified via preparative LC/MS (method D, 60-100% B over 10 minutes) to yield Example 10 (15 mg). $^1$H NMR (500 MHz, DMSO-d$_6$) δ 8.96 (s, 1H), 8.73 (s, 1H), 7.89 (s, 1H), 7.87 (t, J$_{HF}$=71.89 Hz, 1H), 7.55 (d, J=1.9 Hz, 1H), 7.02 (s, 1H), 3.86 (s, 3H), 2.75 (s, 3H), 2.68 (s, 3H); LC-MS: method A, RT=2.66 min, MS (ESI) m/z: 388.0 (M+H)$^+$. Analytical HPLC purity (method B): 100%.

Example 11 tert-butyl 2-(2-(difluoromethoxy)-7-methylquinoxalin-5-yl)-6,7-dihydrothiazolo[5,4-c]pyridine-5(4H)-carboxylate

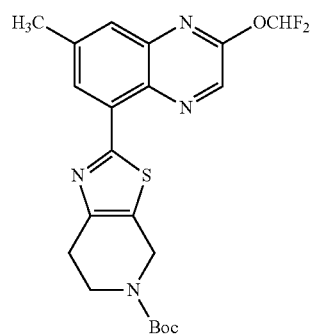

(11)

Intermediate 11A: tert-butyl 2-bromo-6,7-dihydrothiazolo[5,4-c]pyridine-5(4H)-carboxylate

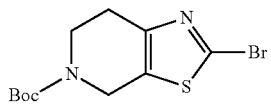

(11A)

tert-Butyl nitrite (0.181 mL, 1.371 mmol) was added to copper (II) bromide (297 mg, 1.332 mmol) in dry acetonitrile (3.0 mL) under argon. The reaction mixture was stirred at room temperature for 10 min. A suspension of tert-butyl 2-amino-6,7-dihydrothiazolo[5,4-c]pyridine-5(4H)-carboxylate (200 mg, 0.783 mmol) in dry acetonitrile (4.0 mL) was added dropwise. The reaction mixture was stirred at room temperature for 1.0 h. Acetonitrile was removed under vacuum, the reaction mixture was diluted with EtOAc, quenched with 1.0 N HCl. The organic layer was collected, washed with 0.5 N HCl (2×), saturated sodium bicarbonate, brine and dried over sodium sulfate. After evaporation of solvent, the crude product was dissolved in a small amount of chloroform and charged to a 12 g silica gel cartridge which was eluted with hexanes for 2 min., then a 12 min gradient from 0% to 50%. The desired fractions were combined, concentrated and lyophilized to give Intermediate 11A (85 mg, 0.266 mmol, 34.0% yield) as a white solid. $^1$H NMR (500 MHz, acetonitrile-d$_3$) δ 4.56 (t, J=1.8 Hz, 2H), 3.70 (t, J=5.8 Hz, 2H), 2.81-2.76 (m, 2H), 1.47 (s, 9H); LC-MS: method A, RT=1.86 min, MS (ESI) m/z: 319.0 and 321.0 (M+H)$^+$.

Example 11

To Intermediate I-1 (30 mg, 0.089 mmol), Intermediate 11A (34.2 mg, 0.107 mmol) and [1,1'-bis(diphenylphosphino)ferrocene]dichloropalladium (II) complex with dichloromethane (1:1) (5.83 mg, 7.14 μmol) was added toluene (2.1 mL) and EtOH (0.7 mL). The mixture was sonicated for 1 min, and flushed with argon. To this was added sodium carbonate (2M, 0.098 mL, 0.196 mmol). The reaction mixture was heated in a microwave reactor at 120° C. for 30 min. HPLC and LCMS indicated a completion of the reaction. To the reaction mixture was added EtOAc/ water. The organic layer was collected, dried over sodium sulfate. After evaporation of solvent, the crude product was purified via a prep LC/MS (method D) to give Example 11 (23.4 mg, 0.052 mmol, 57.9% yield): $^1$H NMR (500 MHz, methanol-d$_4$) δ 8.66 (s, 1H), 8.49 (d, J=1.7 Hz, 1H), 7.76 (d, J=0.8 Hz, 1H), 7.69 (t, J$_{HF}$=71.80 Hz, 1H), 4.76 (s, 2H), 3.83 (t, J=5.8 Hz, 2H), 2.99 (t, J=5.6 Hz, 2H), 2.65 (s, 3H), 1.51 (s, 9H); LC-MS: method A, RT=2.51 min, MS (ESI) m/z: 449.0 (M+H)$^+$. Analytical HPLC purity (method B): 99%.

Example 12

2-(2-(difluoromethoxy)-7-methylquinoxalin-5-yl)-7-methoxy-4-methylbenzo[d]thiazole

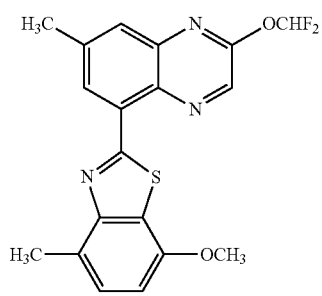

(12)

Intermediate 12A: N-((5-methoxy-2-methylphenyl)carbamothioyl)benzamide

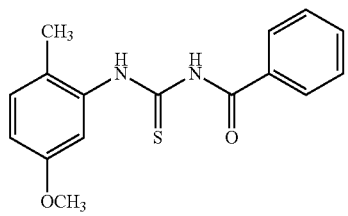

(12A)

To a solution of 5-methoxy-2-methylaniline (1.47 g, 10.72 mmol) in acetone was added dropwise benzoyl isothiocyanate (1.924 g, 11.79 mmol). The reaction mixture was stirred at room temperature for 30 min. HPLC and LCMS indicated a completion of the reaction. Acetone was removed under vacuum. The crude was triturated with EtOAc/hexanes (1:4). The precipitate was collected by filtration, dried under vacuum to give Intermediate 12A (3.1 g, 10.32 mmol, 96% yield) as a green solid. $^1$H NMR (500 MHz, chloroform-d) δ 12.33 (br. s., 1H), 9.14 (br. s., 1H), 7.96-7.92 (m, 2H), 7.71-7.67 (m, 1H), 7.61-7.56 (m, 3H), 7.21 (d, J=8.5 Hz, 1H), 6.83 (dd, J=8.4, 2.6 Hz, 1H), 3.84 (s, 3H), 2.33 (s, 3H); LC-MS: method A, RT=2.11 min, MS (ESI) m/z: 301(M+H)$^+$.

Intermediate 12B: 1-(5-methoxy-2-methylphenyl)thiourea

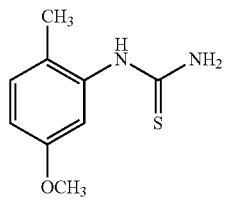

(12B)

To a solution of Intermediate 12A (3.1 g, 10.32 mmol) in THF (20 mL) and MeOH (10 mL) heated at 70° C. was added 4.0 N NaOH (7.74 mL, 31.0 mmol). The reaction mixture was stirred at 70° C. for 2.0 h. HPLC and TLC indicated a completion of the reaction. The mixture was then left stirring at room temperature overnight. THF and MeOH were removed under vacuum. The crude product was then suspended in water. The precipitate was collected by filtration, washed with water and dried in the air under vacuum and then dried under high vacuum to give Intermediate 12B (1.6 g, 8.15 mmol, 79% yield) as a solid. $^1$H NMR (500 MHz, DMSO-d$_6$) δ 9.19 (s, 1H), 7.14 (d, J=8.5 Hz, 1H), 6.83 (d, J=2.2 Hz, 1H), 6.76 (dd, J=8.3, 2.8 Hz, 1H), 3.31 (s, 3H), 2.11 (s, 3H); LC-MS: method A, RT=1.16 min, MS (ESI) m/z: 197.0 (M+H)$^+$.

Intermediate 12C: 7-methoxy-4-methylbenzo[d]thiazol-2-amine

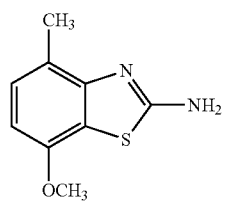

(12C)

To a suspension of Intermediate 12B (1.43 g, 7.29 mmol) in AcOH (20 mL) at room temperature was added benzyltrimethylammonium tribromide (2.84 g, 7.29 mmol) in acetonitrile (15 mL) dropwise (15 min). The reaction mixture was stirred at room temperature overnight. HPLC and LCMS indicated a completion of the reaction. Most of the solvent was removed under vacuum. The mixture was diluted with EtOAc, and the pH was adjusted to 8 with 1.0 N NaOH. The insoluble material was removed by filtration. The organic layer of the filtrate was collected, washed with saturated sodium bicarbonate, brine, dried over sodium sulfate. After evaporation of solvent, Intermediate 12C (1.42 g, 7.31 mmol, 100% yield) was obtained as a solid. $^1$HNMR and HPLC indicated >90% purity. It was used for the next step without further purification. $^1$H NMR (500 MHz, chloroform-d) δ 7.09 (dd, J=8.1, 0.7 Hz, 1H), 6.60 (d, J=8.3 Hz, 1H), 3.93 (s, 3H), 2.51 (s, 3H); LC-MS: method A, RT=1.28 min, MS (ESI) m/z: 195.0 (M+H)$^+$.

Intermediate 12D: 2-bromo-7-methoxy-4-methyl-benzo[d]thiazole

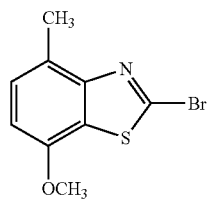

(12D)

Tert-butyl nitrite (0.225 mL, 1.699 mmol) was added to a solution of copper (II) bromide (354 mg, 1.586 mmol) in acetonitrile (5.0 mL). The reaction mixture was stirred at room temperature for 10 min, followed by addition of Intermediate 12C (220 mg, 1.133 mmol) in acetonitrile (3.0 mL). The reaction mixture was stirred at room temperature 1.0 h. HPLC and LCMS indicated a complete conversion of starting material to the desired mono-bromo and undesired di-bromo product. Acetonitrile was removed under vacuum, the reaction mixture was diluted with EtOAc, quenched with 1.0 N HCl. The organic layer was collected, washed with 0.5 N HCl (2×), saturated sodium bicarbonate, brine and dried over sodium sulfate. After evaporation of solvent, the crude product was dissolved in a small amount of chloroform and charged to a 40 g silica gel cartridge which was eluted with hexanes for 2 min., then a 18 min gradient from 0% to 20%. TLC indicated the two products were not separated by ISCO column. The crude residue was then purified using a preparative HPLC (method A, 50-100% B in 10 min., RT=7.0 min). The desired fractions were placed in a SpeedVac overnight to remove solvent, then lyophilized to give Intermediate 12D (120 mg, 0.465 mmol, 41.0% yield). $^1$H NMR (500 MHz, chloroform-d) δ 7.22 (dd, J=8.0, 0.8 Hz, 1H), 6.78 (d, J=8.0 Hz, 1H), 3.97 (s, 3H), 2.65 (d, J=0.8 Hz, 3H); LC-MS: method A, RT=2.17 min, MS (ESI) m/z: 258.0 and 260.0 (M+H)$^+$.

Example 12

To Intermediate I-1 (20 mg, 0.059 mmol), Intermediate 12D (19.97 mg, 0.077 mmol) and [1,1'-bis(diphenylphosphino)ferrocene]dichloropalladium (II) complex with dichloromethane (1:1) (3.89 mg, 4.76 µmol) was added toluene (1.5 mL) and EtOH (0.5 mL). The mixture was sonicated for 1 min, and flushed with argon. To this was added sodium carbonate (2M, 0.074 mL, 0.149 mmol). The reaction mixture was heated in a microwave reactor at 125° C. for 30 min. HPLC and LCMS indicated a completion of the reaction. To the reaction mixture was added EtOAc/water. The organic layer was collected, dried over sodium sulfate. After evaporation of solvent, the crude was dissolved in DMF (4.0 mL) and purified via preparative LC/MS (method D, 60-100% B over 25 minutes). Fractions containing the desired product were combined and dried via centrifugal evaporation to yield Example 12 (2.5 mg). $^1$H NMR (500 MHz, DMSO-d$_6$) δ 9.03 (s, 1H), 8.81 (d, J=1.9 Hz, 1H), 7.94 (s, 1H), 7.90 (t, J$_{HF}$=71.53 Hz, 1H), 7.33 (d, J=8.0 Hz, 1H), 6.98 (d, J=8.0 Hz, 1H), 3.99 (s, 3H), 2.73 (s, 3H), 2.70 (s, 3H); LC-MS: method A, RT=2.77 min, MS (ESI) m/z: 388.0 (M+H)$^+$.

Example 13

2-(2-(difluoromethoxy)-7-methylquinoxalin-5-yl)-4,6-difluoro-7-methoxybenzo[d]thiazole

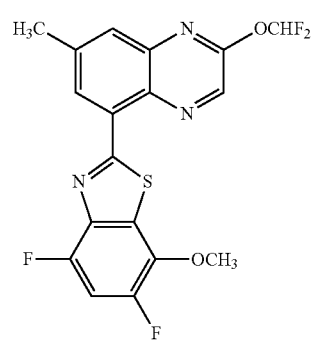

(13)

Intermediate 13A: 4,6-difluoro-7-methoxybenzo[d]thiazol-2-amine

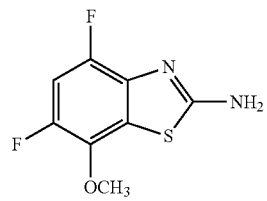

(13A)

To 2,4-difluoro-5-methoxyaniline (270 mg, 1.697 mmol) in acetonitrile (6 mL) was added ammonium thiocyanate (194 mg, 2.55 mmol). The reaction mixture was stirred at room temperature for 10 min. Then benzyltrimethylammonium tribromide (662 mg, 1.697 mmol) in acetonitrile (3.0 mL) was added dropwise (10 min). The mixture was then stirred at room temperature overnight. HPLC and LCMS indicated a completion of the reaction. The mixture was diluted with EtOAc/saturated sodium bicarbonate. The organic layer was collected, washed with brine, dried over sodium sulfate. After evaporation of solvent, the crude product was dissolved in a small amount of chloroform/MeOH, and charged to a 12 g silica gel cartridge which was eluted with 5% for 3 min., then a 12 min gradient from 5% to 75%. The desired fractions were combined and concentrated to give Intermediate 13A (240 mg, 1.110 mmol, 65.4% yield) as a pale solid. $^1$H NMR (500 MHz, methanol-d$_4$) δ 6.98 (dd, J=12.1, 10.5 Hz, 1H), 3.99 (d, J=1.7 Hz, 3H); $^{19}$F NMR (471 MHz, methanol-d$_4$) δ -132.46 (s, 1F), -139.29 (s, 1F); LC-MS: method A, RT=1.54 min, MS (ESI) m/z: 217.0 (M+H)$^+$.

Intermediate 13B: 2-chloro-4,6-difluoro-7-methoxy-benzo[d]thiazole

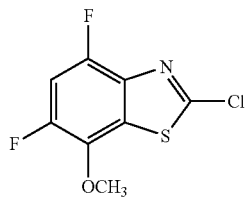

(13B)

To a solution of copper (II) chloride (82 mg, 0.611 mmol) in acetonitrile (6.0 mL) at 40° C. was added tert-butyl nitrite (0.087 mL, 0.661 mmol), followed by Intermediate 13A (110 mg, 0.509 mmol) as a solid. The reaction mixture was stirred at 40° C. for 1.0 h, and left stirring at room temperature overnight. It was diluted with EtOAc, washed with 0.5 HCl, saturated sodium bicarbonate and brine. After evaporation of solvent, Intermediate 13B (12 mg, 0.051 mmol, 10.01% yield) was obtained as yellow solid. $^1$H NMR (500 MHz, chloroform-d) δ 7.07 (dd, J=12.1, 9.6 Hz, 1H), 4.10 (d, J=2.2 Hz, 3H); $^{19}$F NMR (471 MHz, chloroform-d) δ -125.09 (s, 1F), -130.33 (s, 1F); LC-MS: method A, RT=2.01 min, MS (ESI) m/z: 236.0 and 238.0 (M+H)$^+$.

Example 13

To Intermediate I-1 (12 mg, 0.036 mmol), Intermediate 13B (11.36 mg, 0.048 mmol) and [1,1'-bis(diphenylphosphino)ferrocene]dichloropalladium (II) complex with dichloromethane (1:1) (2.332 mg, 2.86 µmol) was added toluene (1.5 mL) and EtOH (0.5 mL). The mixture was sonicated for 1 min, and flushed with argon. To this was added sodium carbonate (2M, 0.045 mL, 0.089 mmol). The reaction mixture was heated in a microwave reactor at 125° C. for 30 min. HPLC and LCMS indicated a completion of the reaction. To the reaction mixture was added EtOAc/water. The organic layer was collected, dried over sodium sulfate. After evaporation of solvent, the crude residue was purified using a preparative HPLC (method A, 70-100% B in 10 min; RT=9.0 min). The desired fractions were placed in a SpeedVac overnight to remove solvent, then lyophilized to give Intermediate 13 (2.0 mg, 4.84 µmol, 13.55% yield). $^1$H NMR (500 MHz, acetonitrile-d$_3$) δ 8.84 (d, J=1.7 Hz, 1H), 8.82 (s, 1H), 7.91 (dd, J=1.9, 0.8 Hz, 1H), 7.73 (t, J$_{HF}$=71.80 Hz, 1H), 7.27 (dd, J=12.0, 10.3 Hz, 1H), 4.15 (d, J=1.7 Hz, 3H), 2.73 (s, 3H); $^{19}$F NMR (471 MHz, acetonitrile-d$_3$) δ -89.97 (s, 2F), -127.74 (s, 1F), -133.31 (s, 1F); LC-MS: Method A, 50 to 100% B. RT=2.30 min, MS (ESI) m/z: 410.0 (M+H)$^+$. Analytical HPLC (method A): Sunfire, RT=13.23 min, 99% purity; XBridge, RT=8.56 min, 99% purity.

Example 14 tert-butyl (2-(2-(difluoromethoxy)-7-methylquinoxalin-5-yl)benzo[d]thiazol-7-yl) carbamate

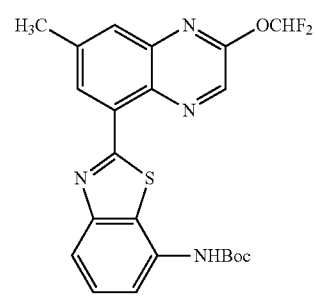

(14)

Intermediate 14A: methyl 2-bromobenzo[d]thiazole-7-carboxylate

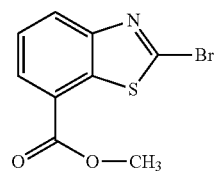

(14A)

Tert-butyl nitrite (1.111 mL, 8.40 mmol) was added to copper (II) bromide (1.770 g, 7.92 mmol) in dry acetonitrile (15 mL) under argon. The reaction mixture was stirred at room temperature for 10 min. A suspension of methyl 2-aminobenzo[d]thiazole-7-carboxylate (1.0 g, 4.80 mmol) in dry acetonitrile (15 mL) was added dropwise. The reaction mixture was stirred at room temperature for 1.5 h, then at 50° C. for 45 min. HPLC and LCMS indicated a completion of the reaction. Acetonitrile was removed under vacuum, the reaction mixture was diluted with EtOAc, quenched with 1.0 N HCl. The organic layer was collected, washed with 0.5 N HCl (2×), saturated sodium bicarbonate, brine and dried over sodium sulfate. After evaporation of solvent, Intermediate 14A (1.2 g, 4.41 mmol, 92% yield) was obtained as a brown solid. It was used for next step without further purification. $^1$H NMR (500 MHz, chloroform-d) δ 8.19 (dd, J=8.0, 1.1 Hz, 1H), 8.13 (dd, J=7.7, 1.1 Hz, 1H), 7.58 (t, J=7.8 Hz, 1H), 4.05 (s, 3H); LC-MS: method A, RT=2.02 min, MS (ESI) m/z: 272.0 274.0 (M+H)$^+$.

Intermediate 14B: 2-bromobenzo[d]thiazole-7-carboxylic acid

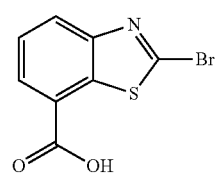

(14B)

To a solution of Intermediate 14A (0.64 g, 2.352 mmol) in THF (12 mL) was added lithium hydroxide monohydrate (0.296 g, 7.06 mmol) dissolved in water (4.0 mL). The reaction mixture was stirred at room temperature for 2.5 h. HPLC indicated a completion of the reaction. The mixture was diluted with EtOAc, quenched with 0.5N HCl (20 mL). The organic layer was collected, washed with brine, dried over sodium sulfate. After evaporation of solvent, Intermediate 14B (0.60 g, 2.325 mmol, 99% yield) was obtained as a yellow solid. It was used for next step without further purification. $^1$H NMR (500 MHz, DMSO-d$_6$) δ 8.28 (dd, J=8.3, 1.1 Hz, 1H), 8.12 (dd, J=7.7, 1.1 Hz, 1H), 7.71 (t, J=7.8 Hz, 1H); LC-MS: method A, RT=1.76 min, MS (ESI) m/z: 258.0 and 260.0 (M+H)$^+$.

Intermediate 14C: tert-butyl (2-bromobenzo[d]thiazol-7-yl)carbamate

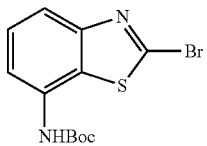

(14C)

To a suspension of Intermediate 14B (80 mg, 0.310 mmol) in THF (2.0 mL) was added TEA (0.065 mL, 0.465 mmol). The mixture turned to a clear solution. To this solution was added trimethylsilyl azide (0.045 mL, 0.341 mmol) and T$_3$P 50% wt in EtOAc (0.203 mL, 0.341 mmol). The reaction mixture was stirred at room temperature for 5 min, then tert-butanol (0.039 mL, 0.403 mmol) was added. The mixture was heated at 80° C. for 2.0 h. Another 2.0 equivalents of triethylamine and 3 equivalents of t-BuOH were added, and the mixture was heated at 80° C. for 8.0 h. The reaction mixture was diluted with EtOAc, washed with 0.5 N HCl, brine. The organic layer was dried over sodium sulfate. After evaporation of solvent, the crude product was dissolved in a small amount of chloroform and charged to a 12 g silica gel cartridge which was eluted with hexanes for 2 min., then a 15 min gradient from 0% to 30%. The desired fractions were combined and concentrated to give Intermediate 14C (36 mg, 0.109 mmol, 35.3% yield): a white solid. $^1$H NMR (500 MHz, chloroform-d) δ 7.79 (dd, J=7.8, 1.2 Hz, 1H), 7.51-7.43 (m, 2H), 6.48 (br. s., 1H), 1.58 (s, 9H); LC-MS: method A, RT=1.99 min, MS (ESI) m/z: 329.0 and 331.0 (M+H)$^+$.

Example 14

To Intermediate I-1 (28 mg, 0.083 mmol), Intermediate 14C (32.9 mg, 0.100 mmol) and [1,1'-bis(diphenylphosphino)ferrocene]dichloropalladium (II) complex with dichloromethane (1:1) (5.44 mg, 6.66 µmol) was added toluene (1.5 mL) and EtOH (0.5 mL). The mixture was sonicated for 1 min, and flushed with argon. To this was added sodium carbonate (2M, 0.104 mL, 0.208 mmol). The reaction mixture was heated in a microwave reactor at 130° C. for 35 min. The mixture was diluted with EtOAc, washed with brine. The organic layer was dried over sodium sulfate. After evaporation of solvent, the crude product was dissolved in a small amount of chloroform and charged to a g silica gel cartridge which was eluted with hexanes for 2 min., then a 10 min gradient from 0% to 30%. The desired fractions were combined and concentrated to give 20 mg of the crude product. This crude product was further purified by prep HPLC. The crude residue was purified using a preparative HPLC (method A, 60-100% B in 10 min; RT=8.5 min). The desired fractions were placed in a SpeedVac overnight to remove solvent, then lyophilized to give Example 14 (11 mg, 28% yield). $^1$H NMR (500 MHz, chloroform-d) δ 8.78 (d, J=1.7 Hz, 1H), 8.72 (s, 1H), 7.98 (d, J=8.3 Hz, 1H), 7.88 (dd, J=1.8, 1.0 Hz, 1H), 7.69 (t, J$_{HF}$=71.53 Hz, 1H), 7.56 (t, J=8.0 Hz, 1H), 2.71 (s, 3H), 1.62 (s, 9H); LC-MS: Method A, 50 to 100% B. RT=2.00 min, MS (ESI) m/z: 459.0 (M+H)$^+$. Analytical HPLC (method A): Sunfire, RT=11.9 min, 100% purity; XBridge, RT=7.46 min, 97% purity.

Example 15

2-(2-(difluoromethoxy)-7-methylquinoxalin-5-yl)-7-(thiazol-4-ylmethoxy)benzo[d]thiazole

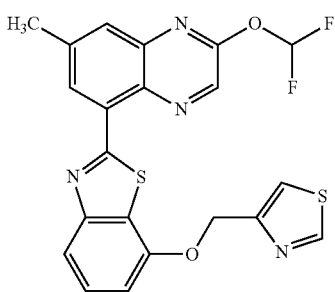

(15)

Intermediate 15A: 2-bromo-3-methoxyaniline

(15A)

To a suspension of 2-bromo-1-methoxy-3-nitrobenzene (3.90 g, 16.81 mmol) and iron powder (2.82 g, 50.4 mmol) in EtOH (50 mL) was added concentrated HCl (3.08 mL, 37.0 mmol). The mixture was heated at 85° C. for 2.0 h. HPLC indicated a completion of the reaction. After cooled to room temperature, the solvent was removed under vacuum. The residue was suspended in EtOAc and saturated sodium bicarbonate. The insoluble material was removed by filtration through a pad of wet celite. The organic layer of the filtrate was collected, washed with brine, dried over sodium sulfate. After evaporation of solvent, Intermediate 15A (3.25 g, 16.09 mmol, 96% yield) was obtained as brown oil. It was used for the next step without further purification. $^1$H NMR (500 MHz, chloroform-d) δ 7.08 (t, J=8.1 Hz, 1H), 6.45 (dd, J=8.0, 1.4 Hz, 1H), 6.34 (dd, J=8.3, 1.1 Hz, 1H), 3.89 (s, 2H); LC-MS: method A, RT=1.21 min, MS (ESI) m/z: 202.0 and 204.0 (M+H)$^+$.

Intermediate 15B: 7-methoxybenzo[d]thiazole-2-thiol

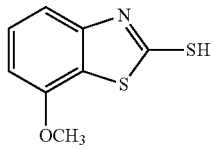

A solution of Intermediate 15A (3.25 g, 16.09 mmol) and potassium O-ethyl carbonodithioate (6.45 g, 40.2 mmol) in DMF (20 mL) was heated at 135° C. under argon for 6.0 h. HPLC and LCMS indicated a completion of the reaction. The mixture was cooled to room temperature, diluted with 20 mL water, followed by addition of 30 mL 1.0 N HCl. The precipitate formed was collected by filtration, washed with water, dried under vacuum and then chased with toluene (3×) to yield Intermediate 15B (3.1 g, 15.71 mmol, 98% yield) as a brown solid. It was used for the next step without further purification. $^1$H NMR (500 MHz, DMSO-$d_6$) δ 13.77 (br. s., 1H), 7.38 (t, J=8.1 Hz, 1H), 6.94 (t, J=8.1 Hz, 2H), 3.91 (s, 3H); LC-MS: method A, RT=1.63 min, MS (ESI) m/z: 198.0(M+H)$^+$.

Intermediate 15C: 7-methoxy-2-(methylthio)benzo[d]thiazole

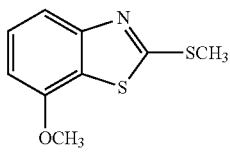

To a solution of Intermediate 15B (2.01 g, 10.19 mmol) in DMF (40 mL) at room temperature was added potassium carbonate (3.52 g, 25.5 mmol). After stirring at room temperature for 10 min, iodomethane (0.796 mL, 12.74 mmol) was added. The reaction mixture was stirred at room temperature for 20 min, at which time HPLC indicated a completion of the reaction. It was diluted with EtOAc, washed with water, brine and dried over sodium sulfate. After evaporation of solvent, Intermediate 15C (2.2 g, 10.41 mmol, 102% yield) was obtained as a brown solid. It was used for the next step without purification. $^1$H NMR (500 MHz, chloroform-d) δ 7.53 (dd, J=8.0, 0.8 Hz, 1H), 7.39 (t, J=8.1 Hz, 1H), 6.79 (dd, J=8.0, 0.6 Hz, 1H), 3.99 (s, 3H), 2.82 (s, 3H); LC-MS: method A, RT=2.00 min, MS (ESI) m/z: 212.0 (M+H)$^+$.

Intermediate 15D: 7-methoxy-2-(methylsulfonyl)benzo[d]thiazole

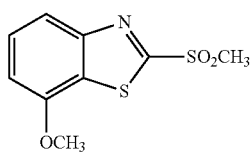

To a solution of Intermediate 15C (2.2 g, 10.41 mmol) dissolved in MeOH (100 mL) was added dropwise a solution of OXONE (19.20 g, 31.2 mmol) suspended in water (100 mL). The reaction mixture was stirred at room temperature over the weekend. HPLC and TLC indicated a completion of the reaction. The reaction was quenched by addition of dimethyl sulfide (4.62 mL, 62.5 mmol). After stirring at room temperature for 45 min, methanol was removed under vacuum. The mixture was diluted with EtOAc/water. The insoluble material was removed by filtration. The filtrate was collected. The organic layer was washed with water (2×), saturated sodium bicarbonate, brine and dried over sodium sulfate. After evaporation of solvent, Intermediate 15D (2.5 g, 10.28 mmol, 99% yield) was obtained as a pale solid. $^1$H NMR (500 MHz, chloroform-d) δ 7.83 (dd, J=8.3, 0.8 Hz, 1H), 7.59 (t, J=8.1 Hz, 1H), 7.01 (d, J=8.0 Hz, 1H), 4.05 (s, 3H), 3.42 (s, 3H); LC-MS: method A, RT=1.55 min, MS (ESI) m/z: 243.9 (M+H)$^+$.

Intermediate 15E: 2-hydrazinyl-7-methoxybenzo[d]thiazole

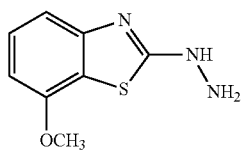

To a suspension of Intermediate 15D (2.5 g, 10.28 mmol) in EtOH (15 mL) was added hydrazine monohydrate (15.55 mL, 308 mmol). The mixture was sonicated for 2 min, heated in oil bath at 100° C. for 1.0 h. HPLC and LCMS indicated a completion of the reaction. Solvent was removed under vacuum. The crude was redissolved in MeOH, and MeOH was removed under vacuum. To the crude was then added ice-cold water (6.0 mL). The precipitate formed was collected by filtration, washed with water, dried over air for 30 min and then at high vacuum over night to give Intermediate 15E (1.67 g, 8.55 mmol, 83% yield) as a pale yellow solid. $^1$H NMR (500 MHz, DMSO-$d_6$) δ 8.97 (s, 1H), 7.17 (t, J=8.0 Hz, 1H), 6.97 (dd, J=8.0, 0.8 Hz, 1H), 6.64 (dd, J=8.3, 0.6 Hz, 1H), 5.01 (s, 2H), 3.32 (s, 3H); LC-MS: method A, 0 to 100% B. RT=1.15 min, MS (ESI) m/z: 196.0 (M+H)$^+$.

Intermediate 15F: 2-chloro-7-methoxybenzo[d]thiazole

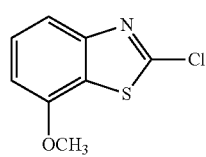

To Intermediate 15E (1.6 g, 8.19 mmol) suspended in dichloromethane (8.0 mL) in a round-bottom flask was added thionyl chloride (8.37 mL, 115 mmol) slowly. The reaction mixture was heated in a pre-heated oil bath at 55° C. for 30 min. HPLC indicated a completion of the reaction.

Thionyl chloride was removed under vacuum, chased with EtOAc once to give a yellow solid. The solid was dissolved in EtOAc, washed with saturated sodium bicarbonate, brine, dried over sodium sulfate. After evaporation of solvent, Intermediate 15F (1.6 g, 8.01 mmol, 98% yield) was obtained as yellow solid. It was used for the next step without further purification. $^1$H NMR (400 MHz, chloroform-d) δ 7.53-7.48 (m, 1H), 7.36 (t, J=8.2 Hz, 1H), 6.79 (d, J=8.2 Hz, 1H), 3.91 (s, 3H); LC-MS: method A, RT=1.98 min, MS (ESI) m/z: 199.9 201.9 (M+H)$^+$.

Intermediate 15G: 2-chlorobenzo[d]thiazol-7-ol

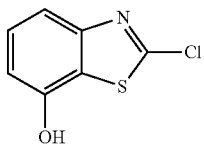

(15G)

Aluminum chloride (2.67 g, 20.03 mmol) was added to a solution of Intermediate 15F (1.6 g, 8.01 mmol) in toluene (40 mL). The mixture was heated at 85° C. for 1.5 h. HPLC indicated a complete conversion of starting material. The reaction mixture was cooled to room temperature, quenched with ice-cold 1.0 N HCl (30 mL) and EtOAc (50 mL), and stirred at room temperature for 30 min. The organic layer was collected, washed with water, saturated sodium bicarbonate, brine and dried over sodium sulfate. After evaporation of solvent, the crude product was triturated with EtOAc/hexanes (1:3). The precipitate was collected to give Intermediate 15G (1.3 g). The filtrate was concentrated, dissolved in a small amount of chloroform and charged to a 12 g silica gel cartridge which was eluted with 5% for 2 min., then a 12 min gradient from 5% to 50%. The desired fractions were combined and concentrated to give additional product (96 mg). LC-MS: method A, RT=1.66 min, MS (ESI) m/z: 186.0 and 188.0 (M+H)$^+$.

Intermediate 15H: 7-((tert-butyldimethylsilyl)oxy)-2-chlorobenzo[d]thiazole

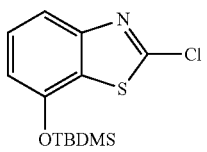

(15H)

To a stirred solution of Intermediate 15G (1.39 g, 7.49 mmol) in DMF (20 mL) was added TBDMS-Cl (1.467 g, 9.73 mmol) and imidazole (0.892 g, 13.10 mmol). The reaction mixture was left stirring at room temperature for 1.0 h. The mixture was partitioned between EtOAc/water. The organic layer was washed with brine and dried over sodium sulfate. After evaporation of solvent, the crude product was dissolved in a small amount of chloroform and charged to a 40 g silica gel cartridge which was eluted with hexanes for 3 min., then a Intermediate 15 min gradient from 0% to 15%. The desired fractions were combined and concentrated to give Intermediate 15H (2.14 g, 7.14 mmol, 95% yield) as brown oil. $^1$H NMR (500 MHz, chloroform-d) δ 7.60 (dd, J=8.3, 0.8 Hz, 1H), 7.37 (t, J=8.1 Hz, 1H), 6.85 (dd, J=8.0, 0.8 Hz, 1H), 1.07 (s, 9H), 0.29 (s, 6H); LC-MS: Method A, 50 to 100% B. RT=2.38 min, MS (ESI) m/z: 300.0 and 302.0 (M+H)$^+$.

Intermediate 15I 7-((tert-butyldimethylsilyl)oxy)-2-(2-(difluoromethoxy)-7-methylquinoxalin-5-yl)benzo[d]thiazole

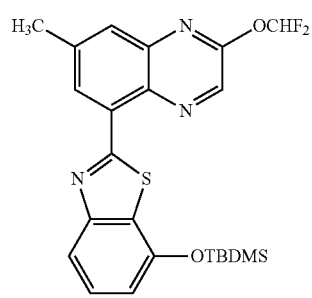

(15I)

To Intermediate I-1 (1.05 g, 3.12 mmol), Intermediate 15H (1.077 g, 3.59 mmol) and [1,1'-bis(diphenylphosphino)ferrocene]dichloropalladium (II) complex with dichloromethane (1:1) (0.128 g, 0.156 mmol) was added toluene (9 mL), EtOH (3 mL) and sodium carbonate (2M, 3.12 mL, 6.25 mmol). The mixture was degassed with argon for 5 min. The reaction mixture was heated in a microwave reactor at 135° C. for 70 min. HPLC indicated completion of reaction. To the reaction mixture was added EtOAc/water/brine. The insoluble was removed by filtration with a pad of celite. The organic layer was collected, washed with brine, dried over sodium sulfate. After evaporation of solvent, the crude product was dissolved in a small amount of toluene/chloroform and charged to a 80 g silica gel cartridge which was eluted with hexanes for 3 min., then a 20 min gradient from 0% to 75%. The desired fractions were combined and concentrated to give Intermediate 15I (0.98 g, 2.069 mmol, 66.2% yield) as a bright yellow solid. $^1$H NMR (500 MHz, chloroform-d) δ 8.81 (d, J=1.9 Hz, 1H), 8.76 (s, 1H), 7.83-7.80 (m, 2H), 7.68 (t, J$_{HF}$=71.80 Hz, 1H), 7.42 (t, J=8.0 Hz, 1H), 6.86 (dd, J=7.8, 0.7 Hz, 1H), 2.71 (s, 3H), 1.13 (s, 9H), 0.35 (s, 6H); $^{19}$F NMR (471 MHz, chloroform-d) δ −89.74 (s, 2F); LC-MS: Method A, 80 to 100% B. RT=2.41 min, MS (ESI) m/z: 474.0 (M+H)$^+$.

Intermediate 15J: 2-(2-(difluoromethoxy)-7-methylquinoxalin-5-yl)benzo[d]thiazol-7-ol

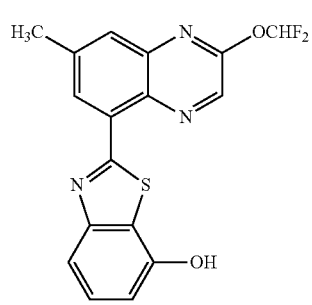

(15J)

To a solution of Intermediate 151 (1.96 g, 4.14 mmol) in THF (15 mL) at room temperature was added acetic acid (0.521 mL, 9.10 mmol), followed by addition of 1.0 N TBAF in THF (4.97 mL, 4.97 mmol) dropwise. The reaction mixture was stirred at room temperature for 20 min, at which time HPLC and LCMS indicated a completion of the reaction. The mixture was diluted with EtOAc, washed with water, saturated sodium bicarbonate (2×), brine, and dried over sodium sulfate. After evaporation of the solvent, the crude product was triturated with EtOAc/hexanes (1:4). The precipitate was collected by filtration to give Intermediate 15J (1.40 g, 3.893 mmol, 94.0% yield). The filtrate was further concentrated and purified with a 12 g ISCO column eluting with 5%-50% EtOAc in hexanes over 12 min. to give additional product (60 mg). $^1$H NMR (500 MHz, methanol-d$_4$) δ 8.78 (s, 1H), 8.72 (d, J=1.9 Hz, 1H), 7.87 (s, 1H), 7.79 (t, $J_{HF}$=71.80 Hz, 1H), 7.60 (dd, J=8.3, 0.6 Hz, 1H), 7.38 (t, J=8.0 Hz, 1H), 6.84 (dd, J=7.7, 0.6 Hz, 1H), 2.70 (s, 3H); $^{19}$F NMR (471 MHz, methanol-d$_4$) δ −91.07 (s, 2F); LC-MS: Method A, 50 to 100% B. RT=1.68 min, MS (ESI) m/z: 360.0 (M+H)$^+$.

Example 15

A solution of 4-hydroxymethyl thiazole (24.03 mg, 0.209 mmol) and DIAD (0.041 mL, 0.209 mmol) in THF (1.0 mL) was added dropwise to a mixture of Intermediate 15J (25 mg, 0.070 mmol) and triphenylphosphine (36.5 mg, 0.139 mmol) in THF (0.5 mL) heated at 65° C. At the end of addition, HPLC and LCMS indicated a complete conversion of starting material to the product. Solvent was removed under vacuum and the crude was dissolved in DMSO/acetonitrile (2 mL/1 mL), filtered and purified by prep HPLC (method A, 65-100% B in 10 min; RT=7.2 min). The desired fractions were placed in a SpeedVac overnight to remove solvent, then lyophilized to give Example 15 (10 mg, 0.022 mmol, 31.2% yield) as yellow lyophilate. $^1$H NMR (500 MHz, chloroform-d) δ 8.94 (d, J=2.2 Hz, 1H), 8.85 (d, J=1.7 Hz, 1H), 8.74 (s, 1H), 7.86-7.82 (m, 2H), 7.69 (t, $J_{HF}$=71.53 Hz, 1H), 7.59-7.56 (m, 1H), 7.49 (t, J=8.0 Hz, 1H), 7.00 (d, J=7.7 Hz, 1H), 5.57 (d, J=0.6 Hz, 2H), 2.71 (s, 3H); $^{19}$F NMR (471 MHz, chloroform-d) δ −89.74 (s, 2F); LC-MS: Method A, 50 to 100% B. RT=1.94 min, MS (ESI) m/z: 457.0 (M+H)$^+$. Analytical HPLC (method A): Sunfire, RT=11.07 min, 99% purity; XBridge, RT=7.14 min, 99% purity.

Example 16 tetrahydrofuran-3-yl (2-((2-(2-(difluoromethoxy)-7-methylquinoxalin-5-yl)benzo[d]thiazol-6-yl)oxy)ethyl)carbamate

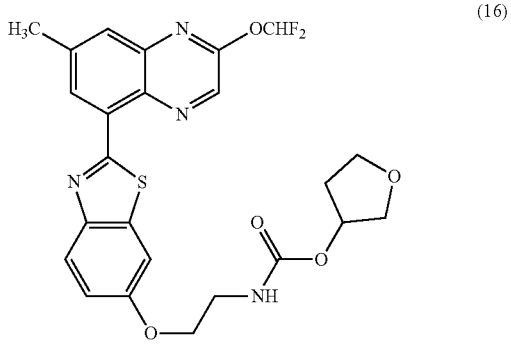 [SMILES: Cc1cc(-c2nc3ccc(OCCNC(=O)OC4CCOC4)cc3s2)c2ncc(OC(F)F)nc2c1]

(16)

To a stirred solution of THF-3-ol (8.21 mg, 0.093 mmol) in dichloromethane (0.6 mL) was added 20% phosgene in toluene (0.078 mL, 0.149 mmol). The reaction mixture was stirred at room temperature for 1.5 h. Solvent was removed under vacuum. The chloroformate obtained was dissolved in dichloromethane (0.5 mL) and added to a solution of Intermediate I-4 (15 mg, 0.037 mmol) and TEA (0.026 mL, 0.186 mmol) in dichloromethane (0.6 mL). The reaction mixture was stirred at room temperature for 30 min. Solvent was removed under vacuum. The crude was dissolved in acetonitrile/DMSO (1 mL/0.5 mL) and was purified by prep HPLC (method A, 60-100% B in 10 min; RT=6 min). The desired fractions were placed in a SpeedVac overnight to remove solvent, then lyophilized to give Example 16 (3.0 mg, 5.69 μmol, 15.27% yield). $^1$H NMR (500 MHz, chloroform-d) δ 8.76 (d, J=1.9 Hz, 1H), 8.71 (s, 1H), 8.09 (d, J=8.8 Hz, 1H), 7.84 (dd, J=1.9, 0.8 Hz, 1H), 7.68 (t, $J_{HF}$=71.53 Hz, 1H), 7.43 (d, J=2.5 Hz, 1H), 7.17 (dd, J=9.1, 2.5 Hz, 1H), 5.35-5.24 (m, 2H), 4.18 (t, J=5.0 Hz, 2H), 3.99-3.86 (m, 3H), 3.69 (q, J=5.0 Hz, 2H), 2.71 (s, 3H), 2.20 (dd, J=14.2, 6.2 Hz, 1H), 2.11-2.04 (m, 1H); $^{19}$F NMR (471 MHz, chloroform-d) δ −89.77 (s, 2F); LC-MS: method A, RT=2.31 min, MS (ESI) m/z: 517.0 (M+H)$^+$. Analytical HPLC (method A): Sunfire, RT=8.80 min, 98% purity; XBridge, RT=5.64 min, 98% purity.

Example 17

2-(2-(difluoromethoxy)-7-methylquinoxalin-5-yl)-7-(2-phenoxyethoxy)benzo[d]thiazole

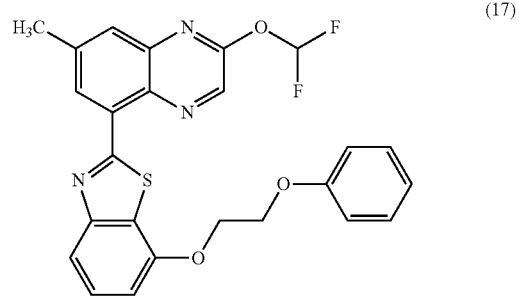 [SMILES: Cc1cc(-c2nc3cccc(OCCOc4ccccc4)c3s2)c2ncc(OC(F)F)nc2c1]

(17)

A solution of 2-phenoxyethanol (20.76 mg, 0.150 mmol) and DIAD (0.029 mL, 0.150 mmol) in THF (1.0 mL) was added dropwise to a mixture of Intermediate 15J (18 mg, 0.050 mmol) and triphenylphosphine (26.3 mg, 0.100 mmol) in THF (0.5 mL) heated at 65° C. At the end of addition, HPLC and LCMS indicated a complete conversion of starting material to the product. Solvent was removed under vacuum and the crude was dissolved in DMSO/acetonitrile (1 mL/1 mL), filtered and purified by prep HPLC (method A, 80-100% B in 10 min; RT=8 min). The desired fractions were placed in a SpeedVac overnight to remove solvent, then lyophilized to give Example 17 (13 mg, 0.026 mmol, 52.5% yield) as yellow lyophilate. $^1$H NMR (500 MHz, methanol-d$_4$) δ 8.66 (d, J=1.7 Hz, 1H), 8.62 (s, 1H), 7.73 (s, 1H), 7.69 (d, J=8.3 Hz, 1H), 7.57 (t, $J_{HF}$=71.80 Hz, 1H), 7.39 (t, J=8.1 Hz, 1H), 7.24 (t, J=8.0 Hz, 2H), 6.95-6.89 (m, 3H), 6.85 (d, J=8.0 Hz, 1H), 4.51-4.47 (m, 2H), 4.41-4.36 (m, 2H), 2.59 (s, 3H); $^{19}$F NMR (471 MHz, methanol-d$_4$) δ −93.93 (s, 2F); LC-MS: Method A, 50 to 100% B. RT=2.35 min, MS (ESI) m/z: 480.0 (M+H)$^+$. Analytical HPLC (method A): Sunfire, RT=5.27 min, 97% purity; XBridge, RT=2.99 min, 97% purity.

Example 18

7-(2-(benzyloxy)ethoxy)-2-(2-(difluoromethoxy)-7-methylquinoxalin-5-yl) benzo[d]thiazole

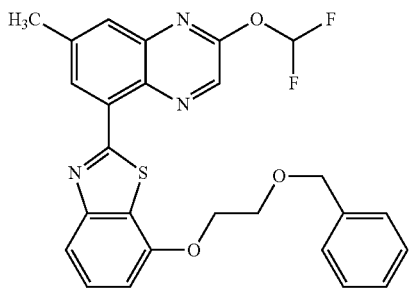

A solution of 2-(benzyloxy)ethanol (22.87 mg, 0.150 mmol) and DIAD (0.029 mL, 0.150 mmol) in THF (1.0 mL) was added dropwise to a mixture of Intermediate 15J (18 mg, 0.050 mmol) and triphenylphosphine (26.3 mg, 0.100 mmol) in THF (0.5 mL) heated at 65° C. At the end of addition, HPLC and LCMS indicated a complete conversion of starting material to the product. Solvent was removed under vacuum and the crude was dissolved in DMSO/acetonitrile (1 mL/1 mL), filtered and purified by prep HPLC (method A, 65-100% B in 10 min; RT=7.2 min). The desired fractions were placed in a SpeedVac overnight to remove solvent, then lyophilized to give Example 18 (5.0 mg, 9.83 μmol, 19.62% yield) as yellow lyophilate. $^1$H NMR (500 MHz, chloroform-d) δ 8.87 (d, J=1.9 Hz, 1H), 8.74 (s, 1H), 7.84 (dd, J=2.2, 1.1 Hz, 1H), 7.82 (d, J=8.0 Hz, 1H), 7.69 (t, $J_{HF}$=71.80 Hz, 1H), 7.50-7.45 (m, 3H), 7.44-7.39 (m, 2H), 7.36-7.32 (m, 1H), 6.90 (d, J=8.0 Hz, 1H), 4.75 (s, 2H), 4.47-4.42 (m, 2H), 4.03-3.98 (m, 2H), 2.72 (s, 3H); $^{19}$F NMR (471 MHz, chloroform-d) δ −89.74 (s, 2F); LC-MS: Method A, 50 to 100% B. RT=2.33 min, MS (ESI) m/z: 494.0 (M+H)$^+$. Analytical HPLC (method A): Sunfire, RT=5.58 min, 96% purity; XBridge, RT=3.01 min, 98% purity.

Example 19

(Tetrahydrofuran-2-yl)methyl (2-((2-(2-(difluoromethoxy)-7-methylquinoxalin-5-yl) benzo[d]thiazol-6-yl)oxy)ethyl)carbamate

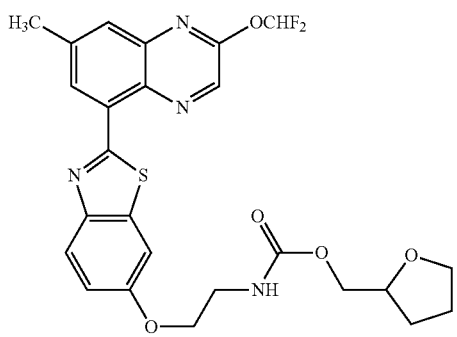

To a solution of (THF-2-yl)methanol (0.194 mL, 1.997 mmol) in dichloromethane (2.0 mL) was added phosgene, 20% in toluene (3.15 mL, 5.99 mmol). The reaction mixture was stirred at room temperature for 18 h. Solvent was removed under vacuum to give the chloroformate (0.32 g, 1.944 mmol, 97% yield) as a colorless liquid that was used for the next step without further purification.

To a solution of Intermediate I-4 (15 mg, 0.037 mmol) in dichloromethane (0.5 mL) was added DIEA (0.052 mL, 0.298 mmol). After stirring at room temperature for 5 min, the chloroformate obtained above (18.40 mg, 0.112 mmol) was added. The reaction mixture was stirred at room temperature for 15 min. HPLC and LCMS indicated a completion of the reaction. Solvent was removed under vacuum. The crude was dissolved in acetonitrile/DMSO (1 mL/1.0 mL) and was purified by prep HPLC (method A, 60-100% B in 10 min; RT=6.5 min). The desired fractions were placed in a SpeedVac overnight to remove solvent, then lyophilized to give Example 19 (14 mg, 0.026 mmol, 68.7% yield) as yellow lyophilate. $^1$H NMR (500 MHz, chloroform-d) δ 8.73 (d, J=1.9 Hz, 1H), 8.67 (s, 1H), 8.09 (d, J=9.1 Hz, 1H), 7.82 (dd, J=1.9, 1.1 Hz, 1H), 7.67 (t, $J_{HF}$=71.80 Hz, 1H), 7.39 (d, J=1.9 Hz, 1H), 7.16 (dd, J=8.9, 2.3 Hz, 1H), 5.40 (br. s., 1H), 4.25 (dd, J=11.3, 3.0 Hz, 1H), 4.19-4.15 (m, 3H), 4.03 (dd, J=11.1, 7.6 Hz, 1H), 3.96-3.90 (m, 1H), 3.88-3.82 (m, 1H), 3.69 (q, J=5.4 Hz, 2H), 2.69 (s, 3H), 2.07-2.00 (m, 1H), 1.99-1.91 (m, 2H); $^{19}$F NMR (471 MHz, chloroform-d) δ −89.77 (s, 2F); LC-MS: Method A, 50 to 100% B. RT=1.88 min, MS (ESI) m/z: 531.0 (M+H)$^+$. Analytical HPLC (method A): Sunfire, RT=4.06 min, 97% purity; XBridge, RT=3.02 min, 97% purity.

Example 20 tetrahydro-2H-pyran-4-yl (2-((2-(2-(difluoromethoxy)-7-methylquinoxalin-5-yl)benzo[d]thiazol-6-yl)oxy)ethyl)carbamate

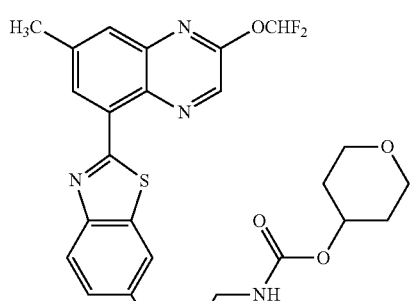

To a solution of tetrahydro-2H-pyran-4-ol (0.196 mL, 2.056 mmol) and in dichloromethane (2.0 mL) was added phosgene, 20% in toluene (3.25 mL, 6.17 mmol). The reaction mixture was stirred at room temperature for 18 h. Solvent was removed under vacuum to give the chloroformate (0.33 g, 2.005 mmol, 98% yield) as a colorless liquid that was used for the next step without further purification.

To a solution of Intermediate I-4 (15 mg, 0.037 mmol) in dichloromethane (0.5 mL) was added DIEA (0.052 mL, 0.298 mmol). After stirring at room temperature for 5 min, the chloroformate (18.40 mg, 0.112 mmol) was added. The reaction mixture was stirred at room temperature for 15 min. HPLC and LCMS indicated a completion of the reaction. Solvent was removed under vacuum. The crude was dissolved in acetonitrile/DMSO (1 mL/1.0 mL) and was purified by prep HPLC (method A, 60-100% B in 10 min; RT=6.5 min). The desired fractions were placed in a SpeedVac overnight to remove solvent, then lyophilized to give Example 20 (4.0 mg, 7.39 μmol, 19.82% yield) as yellow lyophilate. $^1$H NMR (500 MHz, chloroform-d) δ 8.78 (d, J=1.7 Hz, 1H), 8.71 (s, 1H), 8.11 (d, J=9.1 Hz, 1H), 7.84 (dd, J=1.8, 1.0 Hz, 1H), 7.67 (t, $J_{HF}$=71.80 Hz, 1H), 7.44 (d, J=2.5 Hz, 1H), 7.19 (dd, J=8.8, 2.5 Hz, 1H), 5.24 (br. s., 1H), 4.91 (br. s., 1H), 4.19 (t, J=5.1 Hz, 3H), 3.99-3.93 (m, 4H), 3.70 (q, J=5.3 Hz, 3H), 3.58 (t, J=9.5 Hz, 3H), 2.71 (s, 3H), 1.98 (d, J=10.7 Hz, 2H), 1.76-1.68 (m, 2H); $^{19}$F NMR (471 MHz, chloroform-d) δ -89.78 (s, 2F); LC-MS: Method A, 50 to 100% B. RT=1.86 min, MS (ESI) m/z: 531.0 (M+H)$^+$. Analytical HPLC (method A): Sunfire, RT=4.09 min, 97% purity; XBridge, RT=3.04 min, 98% purity.

Example 21 tetrahydro-2H-pyran-4-yl (2-(2-(difluoromethoxy)-7-methylquinoxalin-5-yl) benzo[d]thiazol-7-yl)carbamate

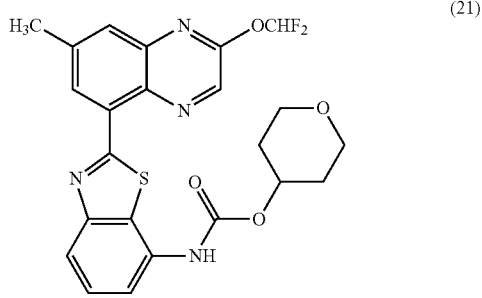 [SMILES: Cc1cc(-c2nc3cccc(NC(=O)OC4CCOCC4)c3s2)c2ncc(OC(F)F)nc2c1]

(21)

Intermediate 21A 2-(2-(difluoromethoxy)-7-methylquinoxalin-5-yl)benzo[d]thiazol-7-amine

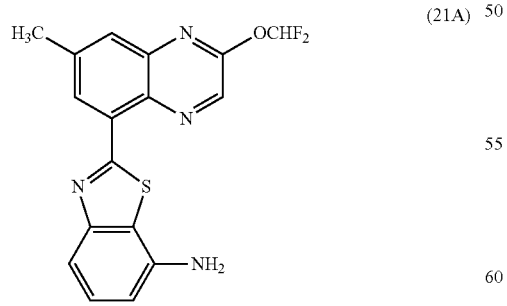

(21A)

To a suspension of Example 14 (90 mg, 0.196 mmol) in ethyl acetate (1.0 mL) and MeOH (1.0 mL) was added 4.0 N HCl in dioxane (2.454 mL, 9.82 mmol). The reaction mixture was stirred at room temperature overnight. After evaporation of solvent, the crude residue was purified using a preparative HPLC (method A, 50-100% B in 10 min; RT=6 min). The desired fractions were placed in a SpeedVac overnight to remove solvent. TFA was removed by redissolving in EtOAc and washing with saturated sodium bicarbonate. After evaporation of solvent and lyophilization, Intermediate 21A (47 mg, 0.125 mmol, 63.5% yield) was obtained as yellow lyophilate. $^1$H NMR (500 MHz, chloroform-d) δ 8.84 (s, 1H), 8.70 (s, 1H), 7.81 (s, 1H), 7.66 (t, $J_{HF}$=71.80 Hz, 1H), 7.64 (d, J=8.0 Hz, 1H), 7.36 (t, J=7.8 Hz, 1H), 6.75 (d, J=7.7 Hz, 1H), 2.69 (s, 3H); LC-MS: Method A, 40 to 100% B. RT=1.60 min, MS (ESI) m/z: 359.0 (M+H)$^+$. Analytical HPLC (method A): Sunfire, RT=5.54 min, 95% purity; XBridge, RT=4.54 min, 95% purity.

Example 21

To a solution of Intermediate 21A (15 mg, 0.042 mmol) in THF (0.8 mL) was added TEA (0.035 mL, 0.251 mmol). After stirring at room temperature for 2 min, the chloroformate prepared in Example 20 (20.67 mg, 0.126 mmol) was added. The reaction mixture was stirred at 50° C. for 1.0 h. HPLC and LCMS indicated a completion of the reaction. The reaction mixture was quenched with 1.0 N HCl (0.25 mL). Solvent was removed under vacuum. The crude was purified via preparative LC/MS (method D, 40-75% B over 10 minutes). Fractions containing the desired product were combined and dried via centrifugal evaporation to give Example 21 (8 mg). $^1$H NMR (500 MHz, methanol-d$_4$) δ 8.72 (s, 2H), 7.92 (d, J=8.5 Hz, 1H), 7.85 (d, J=1.9 Hz, 1H), 7.71 (t, $J_{HF}$=71.53 Hz, 1H), 7.58-7.53 (m, 1H), 7.53-7.48 (m, 1H), 5.01 (dt, J=8.4, 4.3 Hz, 1H), 4.25 (s, 2H), 3.98 (br. s., 2H), 3.66-3.59 (m, 1H), 2.69 (s, 3H), 2.08 (dd, J=9.1, 4.1 Hz, 1H), 1.83 (ddt, J=13.2, 8.8, 4.3 Hz, 1H); LC-MS: method A, RT=2.18 min, MS (ESI) m/z: 487.2 (M+H)$^+$. Analytical HPLC purity (method B): 100%.

Example 22

(Tetrahydrofuran-2-yl)methyl (2-(2-(difluoromethoxy)-7-methylquinoxalin-5-yl)benzo[d]thiazol-7-yl)carbamate

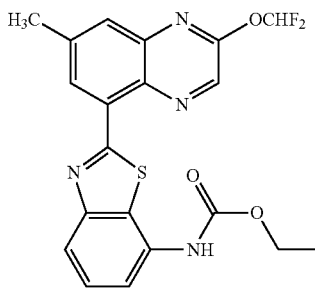

(22)

To a solution of Intermediate 21A (15 mg, 0.042 mmol) in THF (0.5 mL) was added TEA (0.035 mL, 0.251 mmol). After stirring at room temperature for 2 min, the chloroformate prepared in Example 19 (15.16 mg, 0.092 mmol) was added. The reaction mixture was stirred at room temperature for 45 min. The reaction mixture was quenched with 1.0 N HCl (0.25 mL). Solvent was removed under vacuum. The crude was purified via preparative LC/MS (method D, 40-75% B over 13 minutes). Fractions containing the desired product were combined and dried via centrifugal evaporation to yield Example 22 (9 mg). ¹H NMR (500 MHz, methanol-d₄) δ 8.73 (d, J=1.9 Hz, 1H), 8.71 (s, 1H), 7.91 (d, J=8.0 Hz, 1H), 7.85 (s, 1H), 7.71 (t, $J_{HF}$=71.53 Hz, 1H), 7.57 (d, J=10.7 Hz, 1H), 7.53-7.48 (m, 1H), 4.31 (dd, J=11.3, 3.3 Hz, 1H), 4.28-4.22 (m, 1H), 4.17-4.11 (m, 1H), 3.94 (br. s., 1H), 3.86 (d, J=7.2 Hz, 1H), 2.69 (s, 3H), 2.10 (dd, J=12.1, 5.8 Hz, 1H), 1.98 (d, J=7.2 Hz, 2H), 1.78-1.69 (m, 1H); LC-MS: method A, RT=2.18 min, MS (ESI) m/z: 487.3(M+H)⁺. Analytical HPLC purity (method B): 100%.

Example 23

2-(2-(difluoromethoxy)-7-methylquinoxalin-5-yl)-5-methoxythiazolo[5,4-b]pyridine

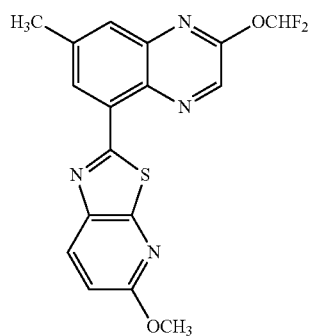
(23)

Intermediate 23A:
5-methoxythiazolo[5,4-b]pyridin-2-amine

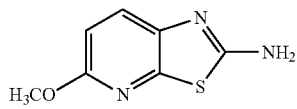
(23A)

To 6-methoxypyridin-3-amine (636 mg, 5.12 mmol) in acetonitrile (14 mL) was added ammonium thiocyanate (585 mg, 7.68 mmol). The reaction mixture was stirred at room temperature for 10 min. Then benzyltrimethylammonium tribromide (1998 mg, 5.12 mmol) in acetonitrile (5.0 mL) was added dropwise (10 min). The mixture was then stirred at room temperature overnight. HPLC and LCMS indicated a single major peak with the desired mass. The mixture was diluted with EtOAc/saturated sodium bicarbonate. The organic layer was collected, washed with saturated sodium bicarbonate, brine, dried over sodium sulfate. After evaporation of solvent, Intermediate 23A (900 mg, 4.97 mmol, 97% yield) was obtained as a brown solid. ¹H NMR indicated >90% purity. It was used for the next step without further purification. ¹H NMR (500 MHz, DMSO-d₆) δ 7.61 (d, J=8.5 Hz, 1H), 7.41 (s, 2H), 6.69 (d, J=8.5 Hz, 1H), 3.83 (s, 3H); LC-MS: method A, RT=1.08 min, MS (ESI) m/z: 181.9 (M+H)⁺.

Intermediate 23B:
2-bromo-5-methoxythiazolo[5,4-b]pyridine

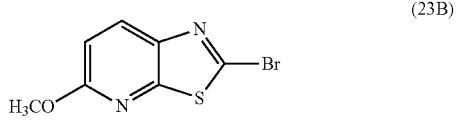 [SMILES: COc1ccc2nc(Br)sc2n1]
(23B)

Tert-butyl nitrite (0.175 mL, 1.324 mmol) was added to copper (II) bromide (266 mg, 1.192 mmol) in dry acetonitrile (5 mL) under argon. The reaction mixture was stirred at room temperature for 10 min. Intermediate 23A (160 mg, 0.883 mmol) was added. The reaction mixture was stirred at room temperature for 4.0 h. HPLC and LCMS indicated a completion of the reaction. Acetonitrile was removed under vacuum, the reaction mixture was diluted with EtOAc, quenched with 0.5N HCl. After stirring at room temperature for 10 min, some insoluble impurity was removed by filtration through a pad of wet celite. The organic layer of the filtrate was collected, washed with saturated sodium bicarbonate, brine and dried over sodium sulfate. The crude product was purified by flash chromatography (loading in chloroform, 0% to 30% EtOAc in hexane over 15 min using a 12 g silica gel cartridge). The desired fractions were combined and concentrated to yield Intermediate 23B (194 mg, 0.792 mmol, 90% yield) as yellow solid. ¹H NMR (500 MHz, chloroform-d) δ 8.08 (d, J=8.8 Hz, 1H), 6.86 (d, J=8.8 Hz, 1H), 4.02 (s, 3H); LC-MS: method A, RT=1.92 min, MS (ESI) m/z: 244.8 and 246.8 (M+H)⁺.

Example 23

To Intermediate I-1 (25 mg, 0.074 mmol), Intermediate 23B (22.79 mg, 0.093 mmol) and [1,1'-bis(diphenylphosphino)ferrocene]dichloropalladium (II) complex with dichloromethane (1:1) (3.04 mg, 3.72 μmol) was added toluene (1.5 mL) and EtOH (0.5 mL). The mixture was sonicated for 1 min, and flushed with argon. To this was added sodium carbonate (2M, 0.082 mL, 0.164 mmol). The reaction mixture was heated in a microwave reactor at 130° C. for 30 min. After cooled to room temperature, it was diluted with EtOAc, washed with saturated sodium bicarbonate, brine. The organic layer was dried over sodium sulfate, concentrated and purified via preparative LC/MS (method D, 50-90% B over 10 minutes, then a 5-minute hold at 100% B). Fractions containing the desired product were combined and dried via centrifugal evaporation to yield Example 23 (8.0 mg). ¹H NMR (500 MHz, DMSO-d₆) δ 8.98 (s, 1H), 8.71 (s, 1H), 8.40 (d, J=8.8 Hz, 1H), 7.93 (s, 1H), 7.89 (t, $J_{HF}$=71.25 Hz, 1H), 7.06 (d, J=9.1 Hz, 1H), 4.01 (s, 3H), 2.68 (s, 3H); LC-MS: method A, RT=2.39 min, MS (ESI) m/z: 375.0 (M+H)⁺. Analytical HPLC purity (method B): 100%.

Example 24

2-(2-(difluoromethoxy)-7-methylquinoxalin-5-yl)-7-methoxythiazolo[4,5-c]pyridine

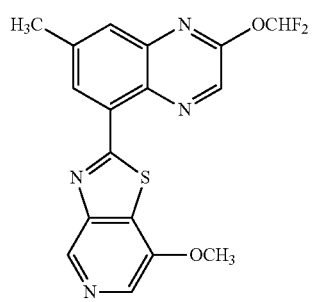

Intermediate 24A:
7-methoxythiazolo[4,5-c]pyridine-2-thiol

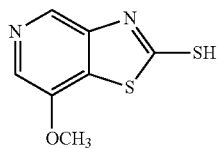

A solution of 4-chloro-5-methoxypyridin-3-amine (0.25 g, 1.576 mmol) and potassium O-ethyl carbonodithioate (0.695 g, 4.34 mmol) in DMF (2) was heated at 135° C. under argon for 3.0 h. HPLC and LCMS indicated a completion of the reaction. The mixture was cooled to room temperature, diluted with 2.0 mL water, followed by addition of 10 mL 1.0 N HCl. The precipitated formed was stirred at room temperature for 15 min, then collected by filtration, washed with water, dried under vacuum and then lyophilized to give Intermediate 24A (0.27 g, 1.362 mmol, 86% yield) as a brown solid. It was used for the next step without further purification. $^1$H NMR (500 MHz, DMSO-$d_6$) δ 8.24 (s, 1H), 8.23 (s, 1H), 4.02 (s, 3H); LC-MS: method A, RT=1.20 min, MS (ESI) m/z: 198.9 (M+H)$^+$.

Intermediate 24B: 2-chloro-7-methoxythiazolo[4,5-c]pyridine

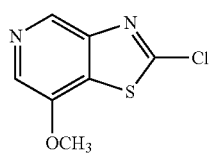

To a slurry of Intermediate 24A (60 mg, 0.303 mmol) in dichloromethane (0.3 mL) was added sulfuryl chloride (0.492 mL, 6.05 mmol). The suspension was stirred at room temperature overnight. To the yellow suspension was added ice/water, stirred at room temperature for 15 min to decompose the excess sulfuryl chloride (exothermic!). EtOAc and 4.0 N NaOH were added to adjust the pH to 10-12. The organic layer was collected, washed with brine, dried over sodium sulfate. After evaporation of solvent, the crude product was dissolved in a small amount of chloroform and charged to a 4 g silica gel cartridge which was eluted with 5% EtOAc in hexanes for 2 min., then a 10 min gradient from 5% to 60%. The desired fractions were combined and concentrated to give Intermediate 24B (40 mg, 0.199 mmol, 65.9% yield) as a white solid. $^1$H NMR (500 MHz, chloroform-d) δ 8.95 (s, 1H), 8.24 (s, 1H), 4.11 (s, 3H); LC-MS: method A, RT=1.21 min, MS (ESI) m/z: 200.9 and 202.9 (M+H)$^+$.

Example 24

To Intermediate I-1 (30 mg, 0.089 mmol), Intermediate 24B (22.38 mg, 0.112 mmol) and [1,1'-bis(diphenylphosphino)ferrocene]dichloropalladium (II) complex with dichloromethane (1:1) (3.64 mg, 4.46 µmol) was added toluene (1.5 mL) and EtOH (0.5 mL). The mixture was sonicated for 1 min, and flushed with argon. To this was added sodium carbonate (2M, 0.098 mL, 0.196 mmol). The reaction mixture was heated in a microwave reactor at 130° C. for 30 min. After cooled to room temperature, it was diluted with EtOAc, washed with saturated sodium bicarbonate, brine. The organic layer was dried over sodium sulfate, concentrated and purified via preparative LC/MS (method D, 35-80% B over 10 minutes, then a After a five-minute hold at 100% B). Fractions containing the desired product were combined and dried via centrifugal evaporation to yield Example 24 (4.1 mg). $^1$H NMR (400 MHz, acetonitrile-$d_3$) δ 9.23 (s, 1H), 8.91 (s, 1H), 8.86 (s, 1H), 8.32 (s, 1H), 8.00 (s, 1H), 7.73 (t, $J_{HF}$=71.50 Hz, 1H), 4.24 (s, 3H); $^{19}$F NMR (376 MHz, acetonitrile-$d_3$) δ -77.11 (br. s., 3F, TFA), -90.66 (s, 2F); LC-MS: method A, RT=1.95 min, MS (ESI) m/z: 374.9 (M+H)$^+$. Analytical HPLC purity (method B): 91%.

Example 25 tert-butyl (2-(2-(difluoromethoxy)-7-methylquinoxalin-5-yl)-4,5,6,7-tetrahydrobenzofuran-4-yl)carbamate

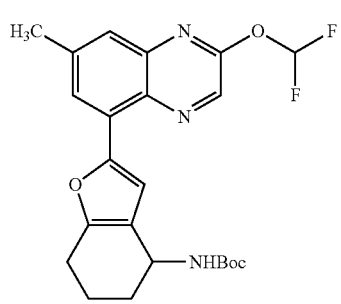

Intermediate 25A: 4,5,6,7-tetrahydrobenzofuran-4-ol

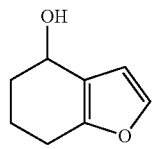
(25A)

To a solution of 6,7-dihydrobenzofuran-4(5H)-one (4.94 g, 36.3 mmol) in MeOH (110 mL) at 0° C. was added NaBH$_4$ (1.579 g, 41.7 mmol) in 3 portions. The reaction mixture was stirred at 0° C. for 2.0 h. TLC indicated a completion of the reaction. MeOH was removed under reduced pressure. To the residue was added EtOAc, water. The pH was adjusted to 7 with saturated ammonium chloride/0.5 N HCl. The organic layer was collected, washed with brine, dried over sodium sulfate. After evaporation of solvent, Intermediate 25A (4.96 g, 35.9 mmol, 99% yield) was obtained as a clear oil. $^1$H NMR (500 MHz, chloroform-d) δ 7.29-7.26 (d, J=1.77 Hz, 1H), 6.41 (d, J=1.77 Hz, 1H), 4.77-4.71 (m, 1H), 2.69-2.61 (m, 1H), 2.59-2.50 (m, 1H), 2.04-1.89 (m, 2H), 1.87-1.75 (m, 2H), 1.64 (br. s., 1H); LC-MS: method A, RT=1.24 min, MS (ESI) m/z: No (M+H)$^+$.

Intermediate 25B: tert-butyldimethyl((4,5,6,7-tetrahydrobenzofuran-4-yl)oxy)silane

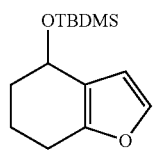
(25B)

To a solution of Intermediate 25A (4.96 g, 35.9 mmol) in DMF (60 mL) was added imidazole (3.67 g, 53.8 mmol) and TBDMS-Cl (6.76 g, 44.9 mmol). The reaction mixture was stirred at room temperature for 1.5 h. TLC and HPLC indicated a completion of the reaction. The reaction mixture was diluted with EtOAc and quenched with water. The organic layer was collected, washed with brine, dried over sodium sulfate and concentrated in vacuum. The crude product was purified by flash chromatography (loading in chloroform, 0% to 10% EtOAc in hexane over 20 min using a 120 g silica gel cartridge). The desired fractions were combined and concentrated to yield Intermediate 25B (8.34 g, 33.0 mmol, 92% yield) as a clear oil. $^1$H NMR (500 MHz, chloroform-d) δ 7.27-7.25 (m, 1H), 6.33 (d, J=1.9 Hz, 1H), 4.79-4.75 (m, 1H), 2.68-2.61 (m, 1H), 2.57-2.50 (m, 1H), 2.10-2.02 (m, 1H), 1.95-1.89 (m, 1H), 1.81-1.68 (m, 2H), 0.95 (s, 9H), 0.16 (s, 3H), 0.15 (s, 3H); LC-MS: Method A, 40 to 100% B. RT=2.30 min, MS (ESI) m/z: No (M+H)$^+$.

Intermediate 25C: tert-butyl((2-iodo-4,5,6,7-tetrahydrobenzofuran-4-yl)oxy) dimethylsilane

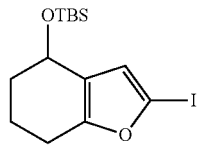
(25C)

To Intermediate 25B (300 mg, 1.188 mmol) in THF (4.0 mL) at −78° C. was added 1.6 N n-BuLi in hexanes (1.114 mL, 1.783 mmol). The mixture was warmed up to 0° C. with an ice bath and stirred for 20 min. The mixture was cooled to −78° C. with dry ice/acetone bath, and iodine (362 mg, 1.426 mmol) in 1 ml THF was added slowly, The reaction mixture was stirred at −78° C. for 10 min, then at 0° C. for 30 min. The reaction mixture was diluted with EtOAc, quenched with saturated ammonium chloride. The organic layer was washed with 10% Na$_2$S$_2$O$_3$, brine, dried over sodium sulfate. After evaporation of solvent, Intermediate 25C (414 mg, 0.996 mmol, 84% yield) was obtained as a brown oil. $^1$H NMR indicated >90% purity. It was used for next step without further purification. $^1$H NMR (500 MHz, chloroform-d) δ 6.47 (s, 1H), 4.74-4.70 (m, 1H), 2.71-2.65 (m, 1H), 2.61-2.54 (m, 1H), 2.06-1.99 (m, 1H), 1.92-1.86 (m, 1H), 1.77-1.64 (m, 2H), 0.95 (s, 9H), 0.15 (s, 3H), 0.14 (s, 3H); LC-MS: Method A, 80 to 100% B. RT=1.76 min, MS (ESI) m/z: No (M+H)$^+$.

Intermediate 25D 5-(4-((tert-butyldimethylsilyl)oxy)-4,5,6,7-tetrahydrobenzofuran-2-yl)-2-(difluoromethoxy)-7-methylquinoxaline

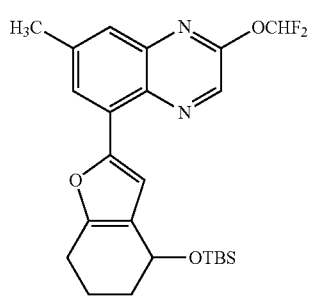
(25D)

To Intermediate 25C (410 mg, 1.084 mmol) and Intermediate I-1 (335 mg, 0.997 mmol) was added toluene (3 mL) and EtOH (1 mL). The reaction mixture was stirred at room temperature until solids are dissolved then [1,1′-bis(diphenylphosphino)ferrocene] dichloropalladium (II) complex with dichloromethane (1:1) (35.4 mg, 0.043 mmol) was added. The flask was degassed and flushed with argon. Finally sodium carbonate (2M, 1.084 mL, 2.167 mmol) was added dropwise. The reaction vessel was sealed and bubbled with argon for 5 min, then put in microwave reactor at 130° C. for 30 min. To the reaction mixture was added EtOAc/water, stirred at room temperature for 10 min. The insoluble material was removed by filtration. The filtrate was extracted with EtOAc, washed with brine and concentrated. The crude product was purified by flash chromatography (loading in chloroform, 0% to 15% EtOAc in hexane over 15 min using a 40 g silica gel cartridge). The desired fractions were combined and concentrated to yield Intermediate 25D (320 mg, 0.591 mmol, 54.5% yield): LC-MS: Method A, 80 to 100% B. RT=2.74 min, MS (ESI) m/z: 461.22 (M+H)+.

Intermediate 25E 2-(2-(difluoromethoxy)-7-methylquinoxalin-5-yl)-4,5,6,7-tetrahydrobenzofuran-4-ol

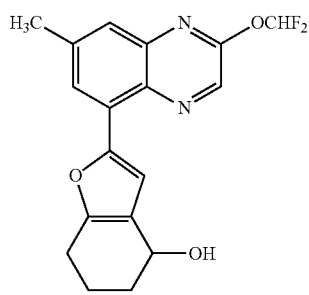

(25E)

To a solution of Intermediate 25D (320 mg, 0.695 mmol) in THF (2.0 mL) at room temperature was added 1.0 N TBAF in THF (0.834 mL, 0.834 mmol). The reaction mixture was stirred at room temperature for 4.0 h. HPLC indicated a completion of reaction. The mixture was diluted with EtOAc, washed with saturated sodium bicarbonate, brine, dried over sodium sulfate and concentrated. The crude product was purified by flash chromatography (loading in chloroform, 0% to 30% EtOAc in hexane over 12 min using a 12 g silica gel cartridge). The desired fractions were combined and concentrated to yield Intermediate 25E (80 mg, 0.226 mmol, 32.6% yield). $^1$H NMR (500 MHz, methanol-$d_4$) δ 8.57 (s, 1H), 7.97 (d, J=1.7 Hz, 1H), 7.67 (t, $J_{HF}$=71.28 Hz, 1H), 7.67 (s, 1H), 7.53 (s, 1H), 4.78 (t, J=4.7 Hz, 1H), 2.81-2.74 (m, 1H), 2.72-2.64 (m, 1H), 2.59 (s, 3H), 2.14-2.07 (m, 1H), 2.02-1.95 (m, 1H), 1.91-1.77 (m, 2H); LC-MS: method A, RT=2.13 min, MS (ESI) m/z: 347.3 (M+H)+.

Intermediate 25F: tert-butyl

N-[(tert-butoxy)carbonyl]-N-{2-[2-(difluoromethoxy)-7-methylquinoxalin-5-yl]-4,5,6,7-tetrahydro-1-benzofuran-4-yl}carbamate

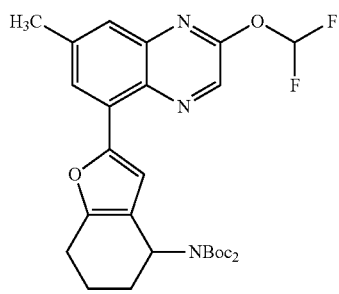

(25F)

A solution of Intermediate 25E (74 mg, 0.214 mmol) and DIAD (0.091 mL, 0.470 mmol) in THF (2.0 mL) was added dropwise to a mixture of di-tert-butyl iminodicarboxylate (81 mg, 0.374 mmol) and triphenylphosphine (112 mg, 0.427 mmol) in THF (1.0 mL) heated at 50° C. At the end of addition, HPLC and LCMS indicated a complete conversion of starting material to the product. After evaporation of solvent, the crude product was purified by flash chromatography (loading in chloroform, 0% to 30% EtOAc in hexanes over 18 min using a 12 g silica gel cartridge). The desired fractions were combined and concentrated to yield Intermediate 25F (12 mg, 0.022 mmol, 10.29% yield) as yellow solid. $^1$H NMR (500 MHz, chloroform-d) δ 8.58 (s, 1H), 7.98 (d, J=1.7 Hz, 1H), 7.65 (t, $J_{HF}$=71.80 Hz, 1H), 7.56 (s, 1H), 7.52 (dd, J=1.8, 1.0 Hz, 1H), 5.41-5.35 (m, 1H), 2.77-2.73 (m, 2H), 2.60 (s, 3H), 2.20-2.11 (m, 4H), 1.47-1.44 (s, 18H); LC-MS: Method A, 50 to 100% B. RT=2.47 min, MS (ESI) m/z: 446.2 (M−Boc)+.

Example 25

To Intermediate 25F (12 mg, 0.022 mmol) was added dichloromethane (1.0 mL) containing TFA (3.39 μl, 0.044 mmol). The solution was aged at room temperature overnight. Solvent was removed under vacuum. The crude material was purified via preparative LCMS (method D,55-95% B over 10 minutes, then a 5-minute hold at 100% B). Fractions containing the desired product were combined and dried via centrifugal evaporation to yield Example 25 (5.3 mg). $^1$H NMR (500 MHz, methanol-$d_4$) δ 8.56 (s, 1H), 7.96 (s, 1H), 7.66 (t, $J_{HF}$=72.80 Hz, 1H), 7.56-7.52 (m, 2H), 4.70 (br. s., 1H), 2.75-2.68 (m, 2H), 2.58 (s, 3H), 2.03 (d, J=9.4 Hz, 2H), 1.94-1.87 (m, 1H), 1.74 (dd, J=10.2, 6.3 Hz, 1H); LC-MS: method A, RT=2.59 min, MS (ESI) m/z: 468.3 (M+Na)+. Analytical HPLC purity (method B): 100%.

Example 26

4-fluoro-N-(2-((2-(2-methoxy-7-methylquinoxalin-5-yl)-4-methylbenzo[d]thiazol-6-yl)oxy)ethyl)benzenesulfonamide

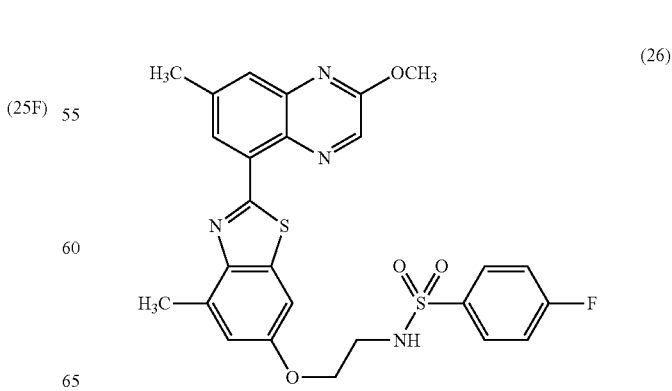

(26)

Intermediate 26A: 2-chloro-6-methoxy-4-methyl-benzo[d]thiazole

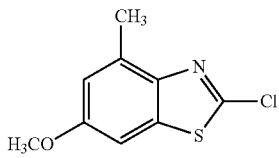

(26A)

To a solution of copper (II) chloride (1.661 g, 12.35 mmol) in acetonitrile (8 mL) at 40° C. was added tert-butyl nitrite (1.769 mL, 13.38 mmol), followed by Intermediate I-3A (2 g, 10.30 mmol) as a solid. The mixture was stirring at 40° C. for 2.0 h. HPLC and LCMS indicated a complete conversion of starting material. The mixture was diluted with EtOAc, washed with 0.5 HCl, saturated sodium bicarbonate and brine. After evaporation of solvent, Intermediate 26A (2.4 g, 11.23 mmol, 99% yield) was obtained as a brown solid. $^1$HNMR indicated >95% purity. $^1$H NMR (500 MHz, chloroform-d) δ 7.07 (d, J=2.5 Hz, 1H), 6.93-6.77 (m, 1H), 3.85 (s, 3H), 2.66 (s, 3H); LC-MS: method B, 0 to 100% B), retention time: 2.08 min, [M+1]$^+$=213.9

Intermediate 26B: 2-chloro-4-methylbenzo[d]thiazol-6-ol

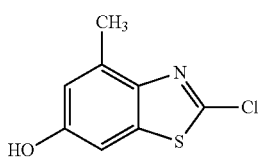

(26B)

Aluminum chloride (4.49 g, 33.7 mmol) was added to a solution of Intermediate 26A (2.4 g, 11.23 mmol) in toluene (50 mL). The mixture was heated at 110° C. for 1.5 h. TLC indicated a complete conversion of starting material. The reaction mixture was cooled to room temperature, quenched with ice-cold 1.0 N HCl (50 mL), stirred at room temperature for 30 min. The precipitate was collected by filtration, washed with water (3×), saturated sodium bicarbonate (3×), water (3×) and air-dried for 1.0 h under vacuum. It was further dried under high vacuum overnight to give Intermediate 26B as a brown solid (1.9 g). $^1$H NMR (400 MHz, methanol-d$_4$) δ 7.06 (d, J=2.3 Hz, 1H), 6.82 (s, 1H), 2.57 (s, 3H). LC-MS: Method A, 50 to 100% B. RT=1.72 min, MS (ESI) m/z: 200.0 and 202.0 (M+H)$^+$.

Intermediate 26C: 6-((tert-butyldimethylsilyl)oxy)-2-chloro-4-methylbenzo[d]thiazole

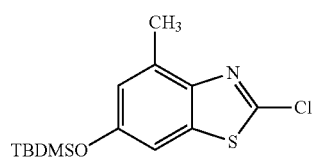

(26C)

To a stirred solution of Intermediate 26B (2.2 g, 11.02 mmol) in DMF (50 mL) was added TBDMS-Cl (2.325 g, 15.43 mmol) and imidazole (1.313 g, 19.28 mmol). The reaction mixture was left stirring at room temperature for 1.0 h. HPLC and TLC indicated a completion of the reaction. The mixture was partitioned between EtOAc/water. The organic layer was washed with brine and dried over sodium sulfate. After evaporation of solvent, the crude product was dissolved in a small amount of chloroform and charged to a 120 g ISCO column which was eluted with hexanes for 3 min., then a 30 min gradient from 0% to 50% EtOAc in hexanes. The desired fractions were combined and concentrated to give Intermediate 26C (1.57 g, 5.00 mmol, 45.4% yield) as an orange solid. $^1$HNMR (400 MHz, chloroform-d) δ 7.09-6.94 (m, 1H), 6.81 (dd, J=2.5, 0.8 Hz, 1H), 2.64 (s, 3H), 1.01 (s, 9H), 0.23 (s, 6H). LC-MS: Method A, 50 to 100% B. RT=2.72 min, MS (ESI) m/z: 314.0 and 316.0.0 (M+H)$^+$.

Intermediate 26D 6-((tert-butyldimethyl silyl)oxy)-2-(2-(difluoromethoxy)-7-methylquinoxalin-5-yl)-4-methyl-benzo[d]thiazole

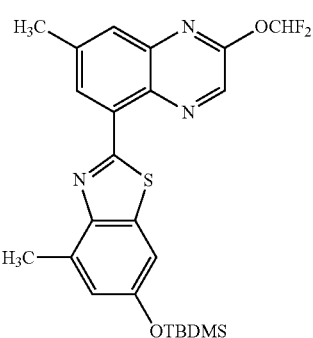

(26D)

To Intermediate I-1 (310 mg, 0.922 mmol), Intermediate 26C (333 mg, 1.061 mmol) and [1,1'-bis(diphenylphosphino)ferrocene]dichloropalladium (II) complex with dichloromethane (1:1) (37.7 mg, 0.046 mmol) was added toluene (3 mL), EtOH (1 mL) and sodium carbonate (2M, 0.922 mL, 1.844 mmol). The mixture was degassed with argon for 5 min. The reaction mixture was heated in a microwave reactor at 135° C. for 40 min. To the reaction mixture was added EtOAc/water/brine. The insoluble was removed by filtration with a pad of celite. The organic layer was collected, washed with brine, dried over sodium sulfate. After evaporation of solvent, the crude product was dissolved in a small amount of chloroform and charged to a 12 g ISCO column which was eluted with hexanes for 3 min., then a 20 min gradient from 0% to 75% EtOAc in hexanes. The desired fractions were combined and concentrated to yield Intermediate 26D (450 mg, 0.923 mmol, 100% yield) as a bright yellow solid. LC-MS: Method A, 50 to 100% B. RT=2.72 min, MS (ESI) m/z: 488.0 (M+H)$^+$.

Intermediate 26E 2-(2-(difluoromethoxy)-7-methylquinoxalin-5-yl)-4-methylbenzo[d]thiazol-6-ol

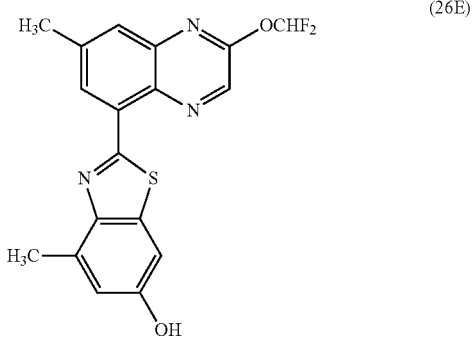 [SMILES: Cc1cc(-c2nc3c(C)cc(O)cc3s2)c2ncc(OC(F)F)nc2c1]

(26E)

To a solution of Intermediate 26D (450 mg, 0.923 mmol) in THF (5 mL) at room temperature was added acetic acid (0.116 mL, 2.030 mmol), followed by addition of 1.0 N TBAF in THF (1.107 mL, 1.107 mmol) dropwise. The reaction mixture was stirred at room temperature for 30 min. LCMS indicated a completion of reaction. The mixture was diluted with EtOAc, washed with water, saturated sodium bicarbonate (2×), brine, and dried over sodium sulfate. After evaporation of the solvent, the crude product was purified with a 12 g ISCO column eluting from 5% EtOAc to 50% EtOAc in hexanes to give Intermediate 26E (290 mg, 0.777 mmol, 84% yield). $^1$H NMR (500 MHz, acetonitrile-d$_3$) δ 8.81 (d, J=1.9 Hz, 1H), 8.74 (s, 1H), 7.80 (dd, J=1.8, 1.0 Hz, 1H), 7.89-7.51 (m, 1H), 7.28 (d, J=1.9 Hz, 1H), 6.88 (dd, J=2.5, 0.8 Hz, 1H), 2.76 (s, 3H), 2.69 (s, 3H). LC-MS: Method A, 50 to 100% B. RT=1.44 min, MS (ESI) m/z: 373.9 (M+H)$^+$.

Intermediate 26F 2-((2-(2-(difluoromethoxy)-7-methylquinoxalin-5-yl)-4-methylbenzo[d]thiazol-6-yl)oxy) ethanamine hydrochloride

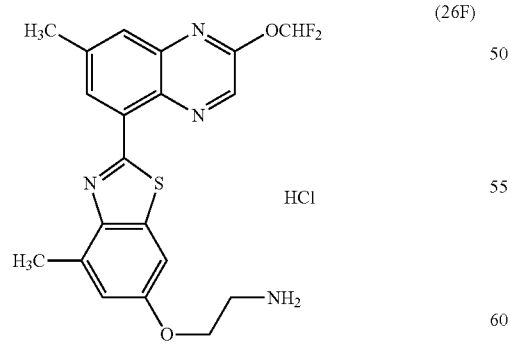

(26F)

A solution of DIAD (0.391 mL, 2.009 mmol) was added to a mixture of Intermediate 26E (250 mg, 0.670 mmol). Tert-butyl (2-hydroxyethyl)carbamate (108 mg, 0.670 mmol) and triphenylphosphine (351 mg, 1.339 mmol) in toluene (5 mL) was added dropwise. The reaction mixture was heated 110° C. for 30 min. The mixture was concentrated and dissolved in 1 ml of DCM and purified by 40 g ISCO column eluted with 0-70% EtOAc in hexanes for 20 min. The desired fraction was concentrated. The sample was redissolved in 5 ml of DCM and 4N HCl/dioxane (8.37 mL, 33.5 mmol) was added. The reaction mixture was stirred at room temperature for 3 h. Solvent was removed under vacuum to give Intermediate 26F (250 mg, 0.552 mmol, 82% yield) as a solid. $^1$H NMR (400 MHz, chloroform-d) δ 8.65 (d, J=1.8 Hz, 1H), 8.52 (s, 1H), 7.62 (d, J=0.8 Hz, 1H), 7.54 (t, $J_{HF}$=72 Hz, 1H), 7.13 (d, J=2.0 Hz, 1H), 6.86 (d, J=1.5 Hz, 1H), 5.02-4.95 (m, 2H), 3.98 (t, J=5.1 Hz, 2H), 2.72 (s, 4H), 2.58 (s, 4H); LC-MS: Method A, 50 to 100% B. RT=2.12 min, MS (ESI) m/z: 416.9 (M+H)$^+$.

Example 26

To a solution of Intermediate 26F (15 mg, 0.033 mmol) and DIEA (0.058 mL, 0.331 mmol) in DMF (1 mL) was added a solution of 4-fluorobenzene-1-sulfonyl chloride (7.73 mg, 0.040 mmol) in 0.2 ml of DCM. The reaction mixture was stirred at room temperature for 1 h, diluted with EtOAc and water, extracted with EtOAc. The combined organic layer was washed with brine, dried with MgSO$_4$ and concentrated. The crude sample was dissolved in 1 ml of MeOH and sodium methoxide (0.199 mL, 0.099 mmol) was added. The reaction mixture was stirred at room temperature for 1 h. The crude material was purified via preparative LC/MS (method C, 45-85% B over 20 minutes, then a 5-minute hold at 100% B). Fractions containing the desired product were combined and dried via centrifugal evaporation to yield Example 26 (7.0 mg). $^1$H NMR (500 MHz, DMSO-d$_6$) δ 8.72 (s, 1H), 8.58 (s, 1H), 7.91 (dd, J=8.3, 5.5 Hz, 2H), 7.81 (s, 1H), 7.46-7.41 (m, 3H), 6.86 (s, 1H), 4.09 (s, 3H), 4.06 (t, J=5.2 Hz, 2H), 3.23 (t, J=5.2 Hz, 2H), 2.73 (s, 3H), 2.64 (s, 3H); LC-MS: method A, RT=2.360 min, MS (ESI) m/z: 539.2 (M+H)$^+$. Analytical HPLC purity (method B): 100%.

Example 27

N-(2-((4-chloro-2-(2-methoxy-7-methylquinoxalin-5-yl)benzo[d]thiazol-6-yl)oxy)ethyl)benzenesulfonamide

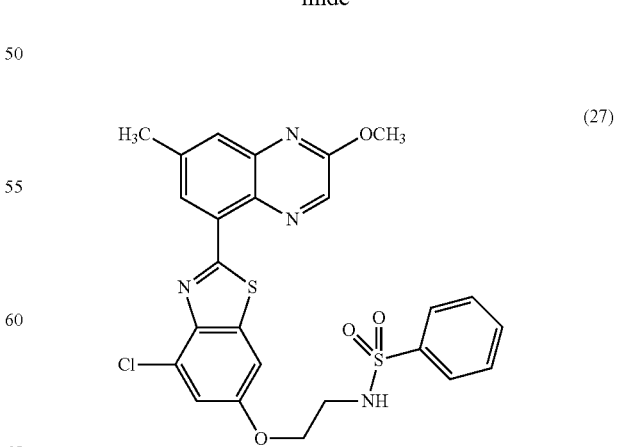

(27)

Intermediate 27A: tert-butyl (2-(3-chloro-4-nitrophenoxy)ethyl)carbamate

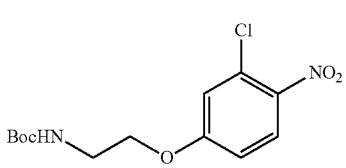

(27A)

To a solution of tert-butyl (2-hydroxyethyl)carbamate (918 mg, 5.70 mmol) in THF (8 mL) was added 0.5 M potassium bis(trimethylsilyl)amide in toluene (12.53 mL, 6.27 mmol). The reaction mixture was stirred at room temperature for 20 min. 2-Chloro-4-fluoro-1-nitrobenzene (500 mg, 2.85 mmol) was added and the reaction mixture was stirred at room temperature for 0.5 h, then at 55° C. for 1.5 h. The mixture was diluted with EtOAc, quenched with saturated ammonium chloride. The organic layer was washed with saturated sodium bicarbonate, brine, dried over sodium sulfate and concentrated. The crude product was purified by flash chromatography (loading in chloroform, 0% to 45% EtOAc in hexane over 15 min using a 40 g silica gel cartridge). The desired fractions were combined and concentrated to yield Intermediate 27A (425 mg, 1.342 mmol, 47.1% yield) as yellow liquid. $^1$H NMR (500 MHz, chloroform-d) δ 8.04-8.00 (d, J=9.1 Hz, 1H), 7.05 (d, J=2.8 Hz, 1H), 6.90 (dd, 2.5 Hz, 1H), 4.14-4.10 (m, 2H), 3.58 (q, J=5.3 Hz, 2H), 1.50 (s, 9H); LC-MS: method A, RT=1.97 min, MS (ESI) m/z: 261.1 and 263.1 (M−t−Bu)$^+$.

Intermediate 27B: tert-butyl (2-(4-amino-3-chlorophenoxy)ethyl)carbamate

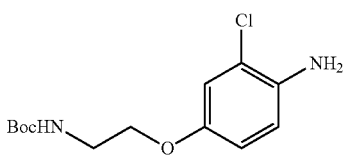

(27B)

To a solution of Intermediate 27A (0.42 g, 1.326 mmol) in MeOH (10 mL) was added ammonium chloride (1.135 g, 21.22 mmol) and zinc dust (0.694 g, 10.61 mmol). The reaction mixture was stirred at room temperature for 30 min. HPLC and LCMS indicated a completion of the reaction. MeOH was removed under vacuum. The residue was diluted with EtOAc/saturated sodium bicarbonate and stirred at room temperature for 10 min. The mixture was filtered to remove insoluble material. The filtrate was collected, organic layer was washed with brine, dried over sodium sulfate, concentrated to give Intermediate 27B (380 mg, 1.325 mmol, 100% yield) as oil. $^1$H NMR (500 MHz, chloroform-d) δ 6.87 (d, J=2.5 Hz, 1H), 6.75-6.68 (m, 2H), 4.98 (br. s., 1H), 3.95 (t, J=5.2 Hz, 2H), 3.51 (t, J=5.0 Hz, 2H), 1.48 (s, 9H); LC-MS: method A, RT=1.47 min, MS (ESI) m/z: 187.1 and 189.1 (M−Boc)$^+$.

Intermediate 27C: tert-butyl (2-((2-amino-4-chlorobenzo[d]thiazol-6-yl)oxy)ethyl) carbamate

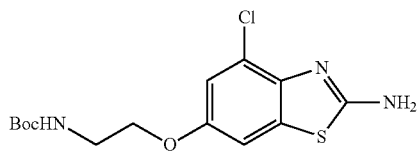

(27C)

To Intermediate 27B (465 mg, 1.622 mmol) in acetonitrile (5.0 mL) was added ammonium thiocyanate (216 mg, 2.84 mmol). The reaction mixture was stirred at room temperature for 10 min. Benzyltrimethylammonium tribromide (854 mg, 2.189 mmol) in acetonitrile (2.0 mL) was added dropwise (5 min). The reaction mixture was stirred at room temperature for 30 min. HPLC and LCMS indicated ca 30% starting material present. Then another portion of ammonium thiocyanate (211 mg, 2.77 mmol) and benzyltrimethylammonium tribromide (415 mg, 1.06 mmol) were added. The reaction mixture was left stirring at room temperature overnight. Acetonitrile was removed under vacuum. The mixture was diluted with EtOAc, THF/saturated sodium bicarbonate. The insoluble material was removed by filtration. The organic layer of the filtrate was collected, washed with brine, dried over sodium sulfate and concentrated to give Intermediate 27C (460 mg, 1.204 mmol, 74.3% yield) as yellow solid that was used for the next step without further purification. $^1$H NMR (500 MHz, DMSO-d$_6$) δ 7.59 (s, 2H), 7.30 (d, J=2.5 Hz, 1H), 7.01-6.96 (m, 1H), 6.92 (d, J=2.5 Hz, 1H), 3.95 (t, J=5.8 Hz, 2H), 3.27 (q, J=5.5 Hz, 2H), 1.39 (s, 9H); LC-MS: method A, RT=1.67 min, MS (ESI) m/z: 344.1 (M+H)$^+$.

Intermediate 27D: tert-butyl (2-((2-bromo-4-chlorobenzo[d]thiazol-6-yl)oxy)ethyl) carbamate

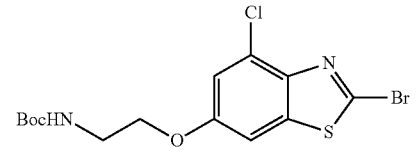

(27D)

Tert-butyl nitrite (0.249 mL, 1.885 mmol) was added to copper (II) bromide (421 mg, 1.885 mmol) in acetonitrile (6 mL) under argon. The reaction mixture was stirred at room temperature for 10 min. Intermediate 27C (405 mg, 1.178 mmol) suspended in acetonitrile (6 mL) was added dropwise. The reaction mixture was stirred at room temperature for 20 min. HPLC and LCMS indicated a completion of the reaction. The reaction mixture was diluted with EtOAc, quenched with 0.5N HCl. After stirring at room temperature for 10 min, the organic layer of the filtrate was collected, washed with 0.5 N HCl, saturated sodium bicarbonate, brine, dried over sodium sulfate and concentrated. The crude product was purified by flash chromatography (loading in chloroform, 0% to 35% EtOAc in hexane over 18 min using a 24 g silica gel cartridge). The desired fractions were combined and concentrated to yield Intermediate 27D (411 mg, 1.008 mmol, 86% yield) as a semisolid which was lyophilized to a solid. ¹H NMR (500 MHz, chloroform-d) δ 7.18 (d, J=2.2 Hz, 1H), 7.14 (d, J=2.2 Hz, 1H), 4.98 (br. s., 1H), 4.09 (t, J=5.1 Hz, 2H), 3.58 (q, J=5.0 Hz, 2H), 1.48 (s, 9H); LC-MS: method A, RT=1.72 min, MS (ESI) m/z: 407.0 and 409.0 (M+H)⁺.

Intermediate 27E: tert-butyl (2-((4-chloro-2-(2-(difluoromethoxy)-7-methylquinoxalin-5-yl)benzo[d]thiazol-6-yl)oxy) ethyl)carbamate

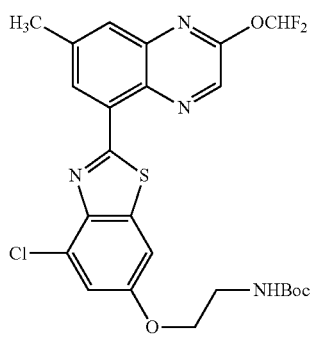

(27E)

To Intermediate 27D (358 mg, 0.878 mmol) and Intermediate I-1 (295 mg, 0.878 mmol) was added toluene (6 mL) and EtOH (2 mL). The reaction mixture was stirred at room temperature until solids are dissolved then [1,1'-bis(diphenylphosphino)ferrocene] dichloropalladium (II) complex with dichloromethane (1:1) (35.9 mg, 0.044 mmol) was added. The flask was degassed and flushed with argon. Sodium carbonate (2M, 0.878 mL, 1.756 mmol) was added dropwise. The reaction vessel was sealed and bubbled with argon for 5 min, then put in microwave reactor at 120° C. for 35 min. HPLC and TLC indicated a completion of the reaction. To the reaction mixture was added EtOAc/water, stirred at room temperature for 10 min. The insoluble material was removed by filtration. The filtrate was extracted with EtOAc, washed with brine and concentrated. The crude product was purified by flash chromatography (loading in chloroform, 0% to 35% EtOAc in hexanes over 15 min using a 24 g silica gel cartridge). The desired fractions were combined and concentrated to yield Intermediate 27E (421 mg, 0.784 mmol, 89% yield) as yellow solid. ¹H NMR (400 MHz, acetonitrile-d₃) δ 8.77 (d, J=1.5 Hz, 1H), 8.72 (s, 1H), 7.82 (dd, J=1.9, 1.0 Hz, 1H), 7.71 (t, J$_{HF}$=71.53 Hz, 1H), 7.50 (d, J=2.4 Hz, 1H), 7.23 (d, J=2.4 Hz, 1H), 4.12 (t, J=5.5 Hz, 2H), 3.49 (q, J=5.6 Hz, 2H), 2.71 (s, 3H), 1.45 (s, 9H); ¹⁹F NMR (376 MHz, acetonitrile-d₃) δ −90.04 (s, 2F); LC-MS: Method A, 40 to 100% B. RT=2.44 min, MS (ESI) m/z: 537.2 (M+H)⁺.

Intermediate 27F: tert-butyl (2-((4-chloro-2-(2-methoxy-7-methylquinoxalin-5-yl) benzo[d]thiazol-6-yl)oxy)ethyl)carbamate

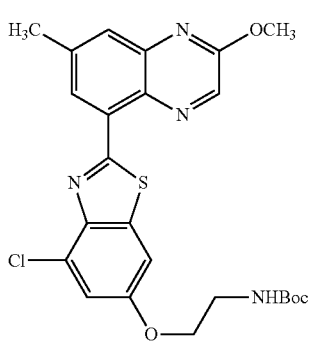

(27F)

To Intermediate 27E (400 mg, 0.745 mmol) in DMF (5.0 mL) was added 0.5 N NaOMe in MeOH (3.28 mL, 1.639 mmol). The reaction mixture was stirred at room temperature for 40 min, diluted with THF (3.0 mL) and EtOAc (10 mL) and quenched with 1.0 N HCl (1.862 mL, 1.862 mmol). THF (50 mL) was added followed with brine. The mixture turned to a clean solution. The organic layer was washed with brine, dried over sodium sulfate and concentrated to give Intermediate 27F (370 mg, 0.739 mmol, 99% yield) as yellow solid. ¹H NMR (500 MHz, DMSO-d₆) δ 8.72 (s, 1H), 8.57 (d, J=1.9 Hz, 1H), 7.84 (dd, J=1.8, 1.0 Hz, 1H), 7.72 (d, J=2.5 Hz, 1H), 7.29 (d, J=2.5 Hz, 1H), 4.10 (t, J=5.78 Hz, 2H), 4.09 (s, 3H), 3.38-3.34 (m, 2H), 2.65 (s, 3H), 1.40 (s, 9H); LC-MS: Method A, 40 to 100% B. RT=2.44 min, MS (ESI) m/z: 501.2 and 503.2 (M+H)⁺.

Intermediate 27G 2-((4-chloro-2-(2-methoxy-7-methylquinoxalin-5-yl)benzo[d]thiazol-6-yl)oxy)ethanamine hydrochloride

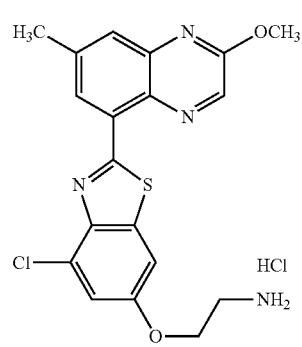

(27G)

To Intermediate 27F (0.32 g, 0.639 mmol) was added 4.0 N HCl in dioxane (15.97 mL, 63.9 mmol), followed by MeOH (8.0 mL). The reaction mixture was stirred at 45° C. for 15 min, and then at room temperature for 30 min. HPLC indicated a completion of reaction. Solvent was removed under vacuum. The crude was partitioned between EtOAc/saturated sodium bicarbonate. The organic layer was washed with brine, dried over sodium sulfate, concentrated and lyophilized to give Intermediate 27G (50 mg, 0.114 mmol, 17.90% yield). ¹H NMR (400 MHz, methanol-d₄) δ 8.19 (d, J=1.8 Hz, 1H), 8.05 (s, 1H), 7.31 (s, 1H), 7.26 (d, J=2.4 Hz, 1H), 7.12 (d, J=2.2 Hz, 1H), 4.27 (t, J=5.0 Hz, 2H), 3.94 (s, 3H), 3.44 (t, J=5.0 Hz, 2H), 2.44 (s, 3H); LC-MS: method A, RT=1.99 min, MS (ESI) m/z: 401.1 and 403.1 (M+H)⁺.

Example 27

To Intermediate 27G (24 mg, 0.055 mmol) in DMF (0.8 mL) was added DIEA (0.058 mL, 0.329 mmol). After stirring at room temperature for 2 min, benzenesulfonyl chloride (10.61 µL, 0.082 mmol) was added and the reaction mixture was stirred at room temperature for 20 min. The reaction mixture was quenched with MeOH (1.0 mL). The crude material was purified via preparative LC/MS (method C, 40-85% B over 20 minutes, then a 5-minute hold at 100% B). Fractions containing the desired product were combined and dried via centrifugal evaporation to yield Example 27 (6.4 mg, 22% yield). ¹HNMR (500 MHz, DMSO-d₆) δ 8.73 (s, 1H), 8.57 (d, J=1.7 Hz, 1H), 7.87-7.85 (m, 1H), 7.85-7.83 (m, 2H), 7.64-7.58 (m, 4H), 7.15 (d, J=2.2 Hz, 1H), 4.11-4.07 (m, 5H), 3.22 (br. s., 2H), 2.65 (s, 3H); LC-MS: method A, RT=2.55 min, MS (ESI) m/z: 541.0 (M+H)⁺. Analytical HPLC purity (method B): 100%.

Example 28

N-(2-((4-chloro-2-(2-methoxy-7-methylquinoxalin-5-yl)benzo[d]thiazol-6-yl)oxy)ethyl)-4-fluorobenzenesulfonamide

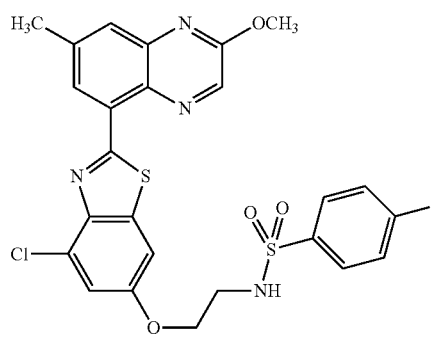

(28)

To Intermediate 27G (30 mg, 0.069 mmol) in DMF (0.8 mL) was added DIEA (0.060 mL, 0.343 mmol). After stirring at room temperature for 4 min, 4-fluorobenzenesulfonyl chloride (14.68 mg, 0.075 mmol) was added and the reaction mixture was stirred at room temperature for 30 min. The reaction was quenched with MeOH (1.0 mL) and purified via preparative LC/MS (method C, 45-85% B over 20 minutes, then a 5-minute hold at 100% B). Fractions containing the desired product were combined and dried via centrifugal evaporation to yield Example 28 (8.9 mg, 22% yield). ¹H NMR (500 MHz, DMSO-d₆) δ 8.73 (s, 1H), 8.57 (d, J=1.7 Hz, 1H), 7.97-7.89 (m, 3H), 7.84 (s, 1H), 7.64 (d, J=2.2 Hz, 1H), 7.45-7.40 (m, 2H), 7.14 (d, J=2.2 Hz, 1H), 4.11-4.07 (m, 5H), 3.24 (t, J=5.2 Hz, 2H), 2.65 (s, 3H); LC-MS: method A, RT=2.50 min, MS (ESI) m/z: 559.0 and 561.0 (M+H)⁺. Analytical HPLC purity (method B): 100%.

Example 29

4-fluoro-N-(2-((2-(2-(methoxymethyl)-7-methylquinoxalin-5-yl)-4-methylbenzo[d]thiazol-6-yl)oxy)ethyl)benzenesulfonamide

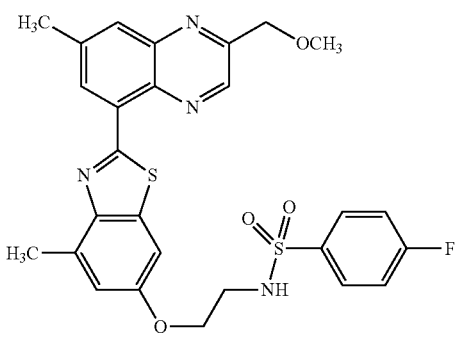

(29)

To Intermediate I-2 (41 mg, 0.177 mmol), Intermediate I-5 (79 mg, 0.177 mmol) and [1,1'-bis(diphenylphosphino)ferrocene]dichloropalladium (II) complex with dichloromethane (1:1) (7.21 mg, 8.83 µmol) was added toluene (1.5 mL) and EtOH (0.5 mL). The mixture was sonicated for 1 min, and flushed with argon. To this was added sodium carbonate (2M, 0.177 mL, 0.353 mmol). The reaction mixture was heated in a microwave reactor at 130° C. for 30 min. HPLC and LCMS indicated a completion of the reaction. To the reaction mixture was added EtOAc/water. The organic layer was collected, dried over sodium sulfate, concentrated. The crude residue was dissolved in DMSO/MeOH (3.5 mL each), purified using a preparative HPLC (method A, 65-100% B in 10 min; then 100% B in 2 min, RT=7.2 min). The desired fractions were placed in a Speed-Vac overnight to remove solvent, then lyophilized to give Example 29 (59 mg, 0.106 mmol, 59.8% yield). ¹H NMR (400 MHz, acetonitrile-d₃) δ 9.05 (s, 1H), 8.88 (s, 1H), 7.98-7.89 (m, 3H), 7.26 (td, J=8.7, 1.8 Hz, 3H), 6.85 (s, 1H), 5.95 (br. s., 1H), 4.82 (s, 2H), 4.07 (t, J=4.6 Hz, 2H), 3.56 (s, 3H), 3.39-3.31 (m, 2H), 2.80 (s, 3H), 2.72 (s, 3H); ¹⁹F NMR (471 MHz, acetonitrile-d₃) δ –107.47 (s, 1F); LC-MS: method A, RT=2.32 min, MS (ESI) m/z: 553.1 (M+H)⁺. Analytical HPLC (method A): Sunfire, RT=10.81 min, 99% purity; XBridge, RT=6.64 min, 99% purity.

Example 30

N-(2-((2-(2-ethoxy-7-methylquinoxalin-5-yl)-4-methylbenzo[d]thiazol-6-yl)oxy)ethyl)-4-fluorobenzenesulfonamide

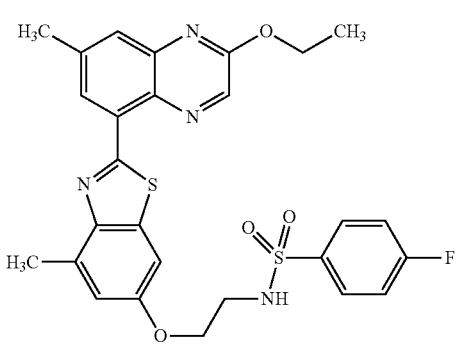

(30)

Intermediate 30A

N-(2-((2-(2-(difluoromethoxy)-7-methylquinoxalin-5-yl)-4-methylbenzo[d]thiazol-6-yl)oxy)ethyl)-4-fluorobenzenesulfonamide

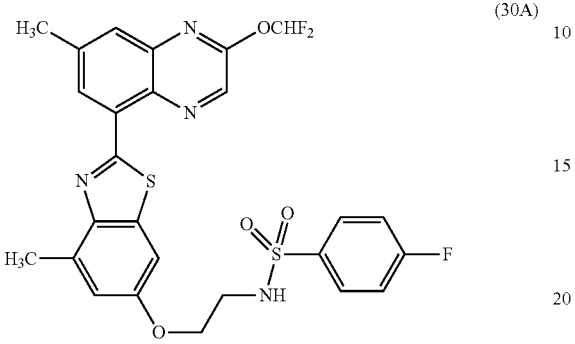
(30A)

To Intermediate I-1 (40 mg, 0.119 mmol), Intermediate I-5 (48.2 mg, 0.108 mmol) and [1,1'-bis(diphenylphosphino)ferrocene]dichloropalladium (II) complex with dichloromethane (1:1) (7.07 mg, 8.65 μmol) was added toluene (1.5 mL) and EtOH (0.5 mL). The mixture was sonicated for 1 min, and flushed with argon. To this was added sodium carbonate (2M, 0.119 mL, 0.238 mmol). The reaction mixture was heated in a microwave reactor at 130° C. for 30 min. HPLC and LCMS indicated a completion of the reaction. To the reaction mixture was added EtOAc/water. The organic layer was collected, dried over sodium sulfate, concentrated. The crude product was purified by flash chromatography (loading in chloroform, 0% to 75% EtOAc in hexane over 20 min using a 12 g silica gel cartridge). The desired fractions were combined and concentrated to yield Intermediate 30A (50 mg, 0.087 mmol, 80% yield) as yellow solid. LC-MS: method A, RT=2.71 min, MS (ESI) m/z: 575.1 (M+H)$^+$.

Example 30

To Intermediate 30A (14 mg, 0.024 mmol) dissolved in EtOH (0.5 mL) and THF (0.4 mL) was added sodiumethoxide in ethanol (0.027 mL, 0.073 mmol) (21% by weight). The reaction mixture was stirred at room temperature for 15 min., another portion of sodiumethoxide in ethanol (0.027 mL, 0.073 mmol) was added. The mixture was left stirring at room temperature overnight. LCMS indicated a completion of the reaction. Solvent was removed and the residue was dissolved in DMSO/MEOH (1:1) and purified via preparative LC/MS (method D, 65-100% B over 10 minutes, then a 5-minute hold at 100% B). Fractions containing the desired product were combined and dried via centrifugal evaporation to yield Example 30 (11.3 mg). $^1$H NMR (500 MHz, DMSO-d$_6$) δ 8.69 (s, 1H), 8.58 (d, J=1.1 Hz, 1H), 7.91 (dd, 5.5 Hz, 2H), 7.78 (s, 1H), 7.46-7.41 (m, 3H), 6.86 (s, 1H), 4.54 (q, J=7.1 Hz, 2H), 4.05 (t, J=5.2 Hz, 2H), 3.23 (t, J=5.2 Hz, 2H), 2.73 (s, 3H), 2.64 (s, 3H), 1.45 (t, J=7.2 Hz, 3H); LC-MS: method A, RT=2.48 min, MS (ESI) m/z: 553.3 (M+H)$^+$. Analytical HPLC purity (method B): 100%.

Example 31

N-(2-((2-(2-ethyl-7-methylquinoxalin-5-yl)-4-methylbenzo[d]thiazol-6-yl)oxy)ethyl)-4-fluorobenzenesulfonamide

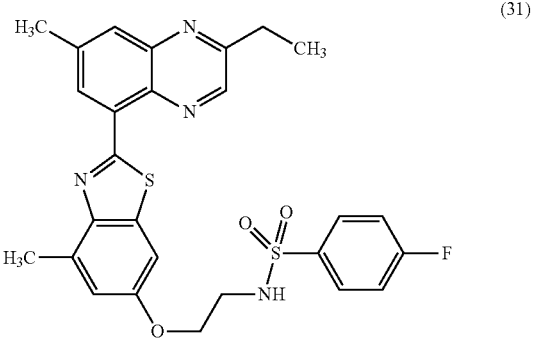 [SMILES: CCc1cnc2c(-c3nc4c(C)cc(OCCNS(=O)(=O)c5ccc(F)cc5)cc4s3)cc(C)cc2n1]
(31)

Intermediate 31A: tert-butyl (2-bromo-4-methyl-6-nitrophenyl)(2-oxobutyl)carbamate

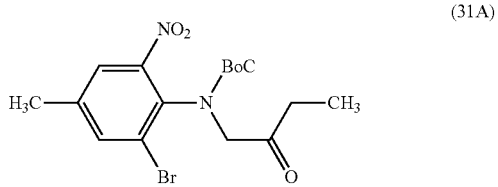
(31A)

To Intermediate I-1B (1.28 g, 3.87 mmol) in DMF (15 mL) at room temperature was added Cs$_2$CO$_3$ (2.204 g, 6.76 mmol). The brown solution was stirred at room temperature for 5 min, followed by addition of 1-bromobutan-2-one (0.592 mL, 5.80 mmol) in acetonitrile (0.4 mL). The brown solution turned yellow. The reaction mixture was stirred at room temperature for 15 min. TLC indicated a completion of the reaction The mixture was diluted with EtOAc, washed with water, brine, dried over sodium sulfate and concentrated. The crude product was purified by flash chromatography (loading in chloroform, 0% to 40% EtOAc in hexane over 10 min using a 40 g silica gel cartridge). The desired fractions were combined and concentrated to yield Intermediate 31A (1.5 g, 3.74 mmol, 97% yield) as yellow liquid. $^1$H NMR (400 MHz, chloroform-d) indicated presence of two rotamers. δ 7.73-7.67 (m, 2H), 4.51-4.05 (m, 2H), 2.57-2.49 (m, 2H), 2.47 and 2.42 (s, 3H), 1.53 and 1.37 (s, 9H), 1.18 and 1.13 (t, J=7.26 Hz, 3H); LC-MS: method A, RT=1.99 min, MS (ESI) m/z: 310.0 and 303.0 (M–Boc)$^+$.

Intermediate 31B:
5-bromo-2-ethyl-7-methylquinoxaline

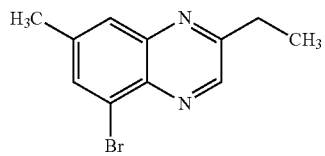

(31B)

To Intermediate 31A (1.55 g, 3.86 mmol) in ethyl acetate (8 mL) was added 4.0 N HCl in dioxane (11.59 mL, 46.4 mmol) and the reaction mixture was stirred at room temperature for 45 min. HPLC indicated a completion of the reaction. Solvent was removed under vacuum to give the deprotected intermediate as yellow oil. The deprotected intermediate was dissolved in THF (20 mL). Tin (II) chloride dihydrate (2.88 g, 12.75 mmol) was added, followed by concentrated HCl (0.476 mL, 5.79 mmol). The mixture was placed and stirred in oil bath pre-heated at 45° C. for 1.0 h. HPLC and LCMS indicated a completion of the reaction. The reaction mixture was diluted with EtOAc/water and neutralized with saturated sodium bicarbonate. The reaction mixture was stirred at room temperature for 15 min, the precipitate was removed by a separatory funnel. The organic layer was washed with saturated sodium bicarbonate, brine, dried over sodium sulfate and concentrated to give Intermediate 31B (0.93 g, 3.70 mmol, 96% yield) as a light yellow solid. $^1$H NMR (400 MHz, chloroform-d) δ 8.70 (s, 1H), 7.80 (d, J=1.8 Hz, 1H), 7.72 (dd, J=1.8, 0.9 Hz, 1H), 2.99 (q, J=7.7 Hz, 2H), 2.50 (s, 3H), 1.36 (t, J=7.6 Hz, 3H); LC-MS: method A, RT=1.93 min, MS (ESI) m/z: 251.1 and 253.1 (M+H)$^+$.

Intermediate 31C:
(2-ethyl-7-methylquinoxalin-5-yl)boronic acid

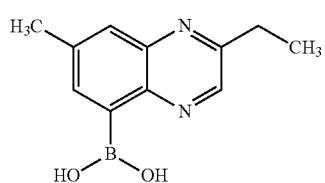

(31C)

A mixture of Intermediate 31B (129 mg, 0.514 mmol), 4,4,4',4',5,5,5',5'-octamethyl-2,2'-bi(1,3,2-dioxaborolane) (261 mg, 1.027 mmol), potassium acetate (101 mg, 1.027 mmol) and [1,1'-bis(diphenylphosphino)ferrocene]dichloropalladium (II) complex with dichloromethane (1:1) (16.78 mg, 0.021 mmol) in dioxane (3.0 mL) was degassed by bubbling argon for 10 min. The reaction vial was sealed and heated in microwave reactor at 130° C. for 30 min. LCMS indicated complete conversion of starting material. The mixture was diluted with EtOAc/water, insoluble material was removed by filtration. The filtrate was extracted with EtOAc, washed with brine and dried over sodium sulfate.

The crude residue was dissolved in MeOH/DMSO (1:1) and purified using a preparative HPLC (method A, 20-100% B in 10 min; then 100% B in 2 min; RT=3.5 min). The desired fractions were placed in a SpeedVac overnight to remove solvent, then lyophilized to give Intermediate 31C (50 mg, 0.231 mmol, 45.1% yield) as a solid. $^1$HNMR in CDCl$_3$ suggested presence of isomeric forms. HPLC and LCMS indicated a single peak. LC-MS: method A, RT=1.86 min, MS (ESI) m/z: 217.0 (M+H)$^+$.

Example 31

To Intermediate 31C (8.73 mg, 0.040 mmol), Intermediate I-5 (18 mg, 0.040 mmol) and [1,1'-bis(diphenylphosphino)ferrocene]dichloropalladium (II) complex with dichloromethane (1:1) (2.64 mg, 3.23 µmol) was added toluene (0.9 mL) and EtOH (0.3 mL). The mixture was sonicated for 1 min, and flushed with argon. To this was added sodium carbonate (2M, 0.040 mL, 0.081 mmol). The reaction mixture was heated in a microwave reactor at 120° C. for 30 min. HPLC and LCMS indicated a completion of the reaction. To the reaction mixture was added EtOAc/water. The organic layer was collected, dried over sodium sulfate, concentrated. The crude product was purified via preparative LC/MS (method D, 60-100% B over 10 minutes, then a 5-minute hold at 100% B). Fractions containing the desired product were combined and dried via centrifugal evaporation to yield Example 31 (15.2 mg). $^1$H NMR (500 MHz, DMSO-d$_6$) δ 9.02 (s, 1H), 8.75 (s, 1H), 8.04 (br. s., 1H), 7.99 (s, 1H), 7.91 (dd, J=8.7, 5.4 Hz, 2H), 7.47-7.41 (m, 3H), 6.87 (s, 1H), 4.06 (t, J=5.1 Hz, 2H), 3.23 (t, J=5.1 Hz, 2H), 3.09 (q, J=7.7 Hz, 2H), 2.74 (s, 3H), 2.68 (s, 3H), 1.40 (t, J=7.6 Hz, 3H); LC-MS: method A, RT=2.59 min, MS (ESI) m/z: 537.3 (M+H)$^+$. Analytical HPLC purity (method B): 100%.

Example 32 methyl 5-(6-(2-(4-fluorophenylsulfonamido)ethoxy)-4-methylbenzo[d]thiazol-2-yl)-7-methylquinoxaline-2-carboxylate

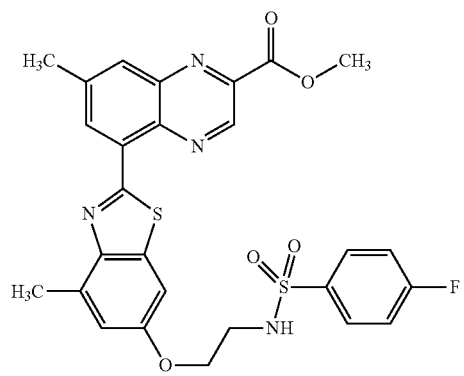

(32)

Intermediate 32A: (2-(methoxycarbonyl)-7-methylquinoxalin-5-yl)boronic acid

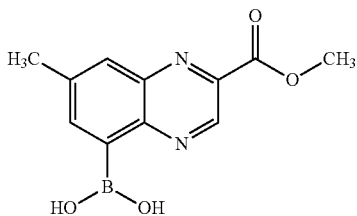

(32A)

A mixture of methyl 5-bromo-7-methylquinoxaline-2-carboxylate (103 mg, 0.366 mmol), 4,4,4',4',5,5,5',5'-octamethyl-2,2'-bi(1,3,2-dioxaborolane) (205 mg, 0.806 mmol), potassium acetate (90 mg, 0.916 mmol) and [1,1'-bis(diphenylphosphino)ferrocene] dichloropalladium (II) complex with dichloromethane (1:1) (11.97 mg, 0.015 mmol) in dioxane (3.0 mL) was degassed by bubbling argon for 10 min. The reaction vial was sealed and heated in microwave reactor at 130° C. for 30 min. LCMS indicated complete conversion of starting material. The mixture was diluted with EtOAc/water, insoluble material was removed by filtration. The filtrate was extracted with EtOAc, washed with brine and dried over sodium sulfate. The crude residue was dissolved in MeOH/DMSO (1:1) and purified using a preparative HPLC (method A, 30-100% B in 10 min; then 100% B in 2 min; RT=3.5 min). The desired fractions were placed in a SpeedVac overnight to remove solvent, then lyophilized to give Intermediate 32A (46 mg, 0.187 mmol, 51.0% yield) as a white solid. $^1$H NMR (400 MHz, methanol-$d_4$) δ 9.43 (s, 1H), 8.30 (br. s., 1H), 8.07 (br. s., 1H), 4.11 (s, 3H), 2.64 (s, 3H); LC-MS: method A, RT=1.64 min, MS (ESI) m/z: 247.1 boronic acid (M+H)$^+$.

Intermediate 32B 5-(6-(2-(4-fluorophenylsulfonamido)ethoxy)-4-methylbenzo[d]thiazol-2-yl)-7-methylquinoxaline-2-carboxylic acid

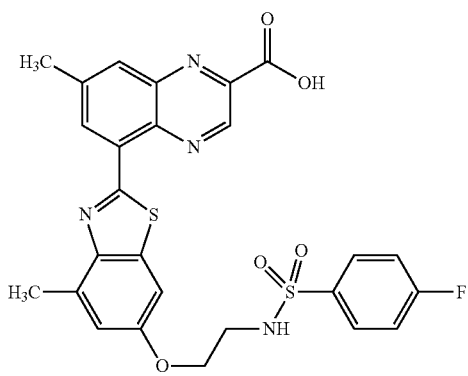

(32B)

To Intermediate 32A (24 mg, 0.098 mmol), Intermediate I-5 (43.4 mg, 0.098 mmol) and [1,1'-bis(diphenylphosphino)ferrocene]dichloropalladium (II) complex with dichloromethane (1:1) (3.98 mg, 4.88 μmol) was added toluene (1.5 mL) and MeOH (0.5 mL). The mixture was sonicated for 1 min, and flushed with argon. To this was added sodium carbonate (2M, 0.098 mL, 0.195 mmol). The reaction mixture was heated in a microwave reactor at 120° C. for 30 min. LCMS indicated a completion of the reaction to the acid. The mixture was diluted with EtOAc/THF (40 Ml/20 mL), acidified with 0.5 N HCl. The organic layer was washed with brine, dried over sodium sulfate and concentrated, purified via preparative LC/MS (method D, 15-55% B over 20 minutes, then a 5-minute hold at 100% B). Fractions containing the desired product were combined and dried via centrifugal evaporation to yield Intermediate 32B (38.5 mg). $^1$H NMR (500 MHz, DMSO-$d_6$) δ 9.49 (s, 1H), 8.91 (s, 1H), 8.16 (br. s., 1H), 8.05 (t, J=5.2 Hz, 1H), 7.98-7.89 (m, 3H), 7.48-7.41 (m, 2H), 6.87 (d, J=1.1 Hz, 1H), 4.07 (t, J=5.2 Hz, 2H), 3.25-3.21 (m, 2H), 2.74 (s, 3H), 2.73 (s, 3H); LC-MS: method A, RT=2.04 min, MS (ESI) m/z: 553.2 (M+H)$^+$.

Example 32

To a suspension of Intermediate 32B (28 mg, 0.051 mmol) in CH$_2$Cl$_2$ (2.0 mL) and MeOH (0.5 mL) at room temperature was added (diazomethyl)trimethylsilane 2.0 M in diethyl ether (0.076 mL, 0.152 mmol). The suspension turned clear. The reaction mixture was stirred at room temperature for 1.0 h. HPLC and LCMS indicated a completion of the reaction. Solvent was removed under vacuum. The crude was purified via preparative LC/MS (method D, 50-90% B over 10 minutes, then a 5-minute hold at 100% B). Fractions containing the desired product were combined and dried via centrifugal evaporation to yield Example 32 (16.4 mg). $^1$H NMR (500 MHz, DMSO-$d_6$) δ 9.50 (s, 1H), 8.92 (d, J=1.1 Hz, 1H), 8.18 (s, 1H), 7.92 (dd, J=8.5, 5.2 Hz, 2H), 7.48-7.45 (m, 2H), 7.45-7.42 (m, 2H), 6.87 (s, 1H), 4.07 (t, J=5.4 Hz, 2H), 4.04 (s, 3H), 3.24 (br. s., 2H), 2.74 (s, 3H), 2.73 (s, 3H); LC-MS: method A, RT=2.28 min, MS (ESI) m/z: 567.2 (M+H)$^+$. Analytical HPLC purity (method B): 100%.

Example 33

N-(2-((2-(2-cyclopropoxy-7-methylquinoxalin-5-yl)-4-methylbenzo[d]thiazol-6-yl)oxy)ethyl)-4-fluorobenzenesulfonamide

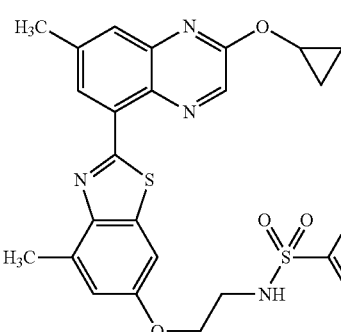

(33)

Intermediate 33A: cyclopropanol

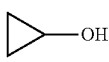
(33A)

To a solution of cyclopropylboronic acid (0.65 g, 7.57 mmol) in 10% NaOH (5.0 mL) at 0° C. was added a solution of 30% hydrogen peroxide (21.44 mL, 189 mmol) dropwise. The reaction mixture was stirred at 0° C. for 1.5 h. The reaction mixture was diluted with diethyl ether, quenched with saturated NaHSO$_3$ (15 mL) at 0° C. After stirring for 15 min, the organic layer was collected, washed with brine, dried over sodium sulfate and concentrated at 0° C. to give Intermediate 33A (0.16 g, 2.75 mmol, 36.4% yield) as colorless liquid. It was used for the next step without further purification. $^1$H NMR (400 MHz, chloroform-d) δ 3.62-3.41 (m, 1H), 0.69-0.40 (m, 4H).

Example 33

To 60% sodium hydride (15.66 mg, 0.392 mmol) was added Intermediate 33A (37.9 mg, 0.653 mmol) in DMF (0.5 mL). The reaction mixture was stirred at room temperature for 15 min. A solution of Intermediate 30A (15 mg, 0.026 mmol) in DMF (1.0 mL) was added. The reaction mixture was stirred at room temperature for 25 min. LCMS indicated a completion of the reaction. The reaction mixture was diluted with EtOAc, quenched with 0.5 N HCl. The organic layer was collected, washed with brine, dried over sodium sulfate and concentrated. The crude was dissolved in DMF/acetonitrile (1:1, 2.2 mL) and purified via preparative LC/MS (method D, 60-100% B over 10 minutes, then a 5-minute hold at 100% B). Fractions containing the desired product were combined and dried via centrifugal evaporation to yield Example 33 (8.6 mg). $^1$H NMR (500 MHz, DMSO-d$_6$) δ 8.67 (s, 1H), 8.59 (s, 1H), 7.90 (dd, J=8.5, 5.2 Hz, 2H), 7.83 (s, 1H), 7.45-7.40 (m, 3H), 6.85 (s, 1H), 4.53-4.49 (m, 1H), 4.05 (t, J=5.4 Hz, 2H), 3.22 (t, J=5.2 Hz, 2H), 2.73 (s, 3H), 2.64 (s, 3H), 0.93-0.88 (m, 2H), 0.87-0.82 (m, 2H); LC-MS: method A, RT=2.67 min, MS (ESI) m/z: 565.1(M+H)$^+$. Analytical HPLC purity (method B): 100%.

Example 34

4-fluoro-N-(2-((2-(2-(fluoromethoxy)-7-methylquinoxalin-5-yl)-4-methylbenzo[d]thiazol-6-yl)oxy)ethyl)benzenesulfonamide

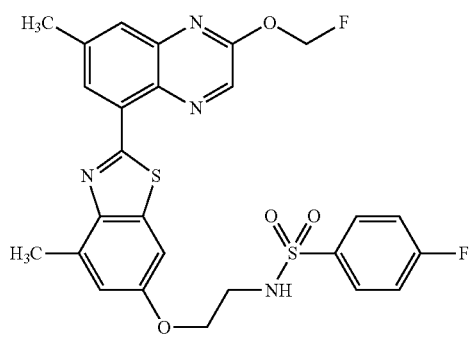
(34)

Intermediate 34A: methyl 2-((5-bromo-7-methylquinoxalin-2-yl)oxy)acetate

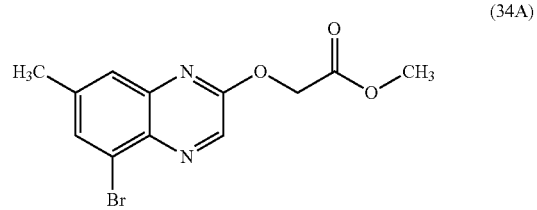
(34A)

To sodium hydride, 60% (411 mg, 10.27 mmol) in DMF (15 mL) cooled with a water bath was added methyl 2-hydroxyacetate (0.959 mL, 12.45 mmol). The reaction mixture was stirred for 20 min. A solution of Intermediate I-1G (900 mg, 3.11 mmol) in DMF (5 mL) was added at room temperature. The reaction mixture was stirred at room temperature for 0.5 h. HPLC indicated a completion of the reaction. The reaction mixture was diluted with EtOAc, quenched with 0.5 N HCl. The organic layer was washed with brine, dried over sodium sulfate and concentrated. The crude product was purified by flash chromatography (loading in chloroform, 0% to 30% EtOAc in hexane over 12 min using a 40 g silica gel cartridge). The desired fractions were combined and concentrated to yield Intermediate 34A (811 mg, 2.61 mmol, 84% yield) as a white solid. $^1$H NMR (400 MHz, chloroform-d) δ 8.51 (s, 1H), 7.63 (d, J=1.5 Hz, 1H), 7.44 (dd, 0.9 Hz, 1H), 4.97 (s, 2H), 3.71 (s, 3H), 2.41 (s, 3H); LC-MS: method A, RT=1.97 min, MS (ESI) m/z: 311.0 and 313.0 (M+H)$^+$.

Intermediate 34B: 2-((5-bromo-7-methylquinoxalin-2-yl)oxy)acetic acid

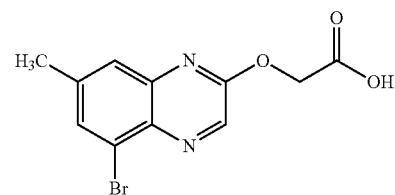
(34B)

To Intermediate 34A (811 mg, 2.61 mmol) dissolved in THF (16 mL) at room temperature was added 1.0 N NaOH (4.56 mL, 4.56 mmol). The reaction mixture was stirred at room temperature for 15 min. HPLC and LCMS indicated a completion of the reaction. The mixture was diluted with EtOAc/water, quenched with 1.0 N HCl (4.95 mL, 4.95 mmol). The organic layer was collected, washed with brine, dried over sodium sulfate and concentrated to give Intermediate 34B (730 mg, 2.457 mmol, 94% yield) as a white solid. $^1$H NMR (400 MHz, chloroform-d) δ 8.63 (s, 1H), 7.77 (d, J=1.5 Hz, 1H), 7.58 (dd, J=1.5, 0.9 Hz, 1H), 5.12 (s, 2H), 2.53 (s, 3H); LC-MS: method A, RT=1.81 min, MS (ESI) m/z: 297.0 and 299.0 (M+H)$^+$.

Intermediate 34C:
5-bromo-2-(fluoromethoxy)-7-methylquinoxaline

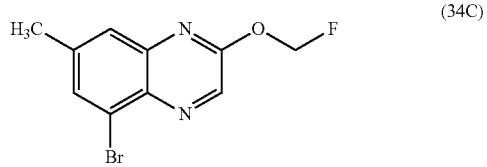

To a suspension of Intermediate 34B (400 mg, 1.346 mmol) in dichloromethane (30 mL) at room temperature was added xenon difluoride (251 mg, 1.481 mmol). The reaction mixture was stirred at room temperature for 4.0 h, followed by addition of another portion of xenon difluoride (251 mg, 1.481 mmol). The reaction mixture was left stirring at room temperature overnight. The suspension turned to a clear solution at this point. A third portion of xenon difluoride (387 mg, 2.289 mmol) was added and the reaction mixture was stirred at room temperature for 4.0 h. The reaction was quenched by addition of saturated sodium bicarbonate, extracted with dichloromethane, dried over sodium sulfate and concentrated. The crude product was purified by flash chromatography (loading in chloroform, 0% to 30% EtOAc in hexane over 15 min using a 24 g silica gel cartridge). The desired fractions were combined and concentrated to yield Intermediate 34C (55 mg, 0.203 mmol, 15.07% yield) as a white solid. $^1$H NMR (400 MHz, chloroform-d) δ 8.60 (s, 1H), 7.82 (d, J=1.5 Hz, 1H), 7.68 (dd, J=1.7, 1.0 Hz, 1H), 6.28 and 6.16 (d, $J_{HF}$=51.28 Hz, 2H), 2.56 (s, 3H); $^{19}$F NMR (376 MHz, chloroform-d) δ −157.89 (s, 1F); LC-MS: method A, RT=1.97 min, MS (ESI) m/z: 271.0 and 273.0 (M+H)$^+$.

Intermediate 34D:
(2-(fluoromethoxy)-7-methylquinoxalin-5-yl)boronic acid

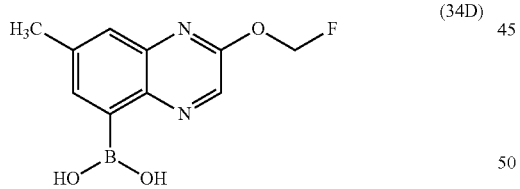

A mixture of Intermediate 34C (48 mg, 0.177 mmol), 4,4,4',4',5,5,5',5'-octamethyl-2,2'-bi(1,3,2-dioxaborolane) (71.9 mg, 0.283 mmol), potassium acetate (34.8 mg, 0.354 mmol) and [1,1'-bis(diphenylphosphino)ferrocene]dichloropalladium (II) complex with dichloromethane (1:1) (5.78 mg, 7.08 µmol) in dioxane (2.0 mL) was degassed by bubbling argon for 5 min. The reaction mixture was heated in a microwave reactor at 120° C. for 30 min. HPLC and LCMS indicated complete conversion of starting material. The mixture was diluted with EtOAc, washed with brine. The organic layer was dried over sodium sulfate. The crude residue was purified using a preparative HPLC (method A, 30-100% B in 10 min; then 100% B in 2 min). The desired fractions were placed in a SpeedVac overnight to remove solvent, then lyophilized to give Intermediate 34D (20 mg, 0.085 mmol, 47.9% yield) as a white solid. $^1$H NMR (400 MHz, methanol-d$_4$) δ 8.48 (s, 1H), 8.02 (br. s., 1H), 7.75 (br. s., 1H), 6.24 and 6.14 (d, $J_{HF}$=51.50 Hz, 1H), 2.56 (s, 3H); $^{19}$F NMR (376 MHz, methanol-d$_4$) δ −158.05 (br. s., 1F); LC-MS: method A, RT=1.87 min, MS (ESI) m/z: 237.0 (M+H)$^+$.

Example 34

To Intermediate 34D (9.54 mg, 0.040 mmol), Intermediate I-5 (18 mg, 0.040 mmol) and [1,1'-bis(diphenylphosphino)ferrocene]dichloropalladium (II) complex with dichloromethane (1:1) (2.64 mg, 3.23 µmol) was added toluene (0.9 mL) and EtOH (0.3 mL). The mixture was sonicated for 1 min, and flushed with argon. To this was added sodium carbonate (2M, 0.040 mL, 0.081 mmol). The reaction mixture was heated in a microwave reactor at 130° C. for 30 min. HPLC and LCMS indicated a completion of the reaction. To the reaction mixture was added EtOAc/water. The organic layer was collected, dried over sodium sulfate, concentrated. The crude product was purified via preparative LC/MS (method G, 60-100% B over 20 minutes, then a 5-minute hold at 100% B). Fractions containing the desired product were combined and dried via centrifugal evaporation to yield Example 34 (19.9 mg). $^1$H NMR (500 MHz, DMSO-d$_6$) δ 8.88 (s, 1H), 8.68 (s, 1H), 7.98-7.87 (m, 3H), 7.48-7.41 (m, 3H), 6.87 (s, 1H), 6.37 and 6.23 (d, $J_{HF}$=51.44 Hz, 2H), 4.06 (t, J=5.1 Hz, 2H), 3.24 (t, J=5.1 Hz, 2H), 2.74 (s, 3H), 2.67 (s, 3H); LC-MS: method A, RT=2.52 min, MS (ESI) m/z: 557.1 (M+H)$^+$. Analytical HPLC purity (method B): 100%.

Example 35

2-(2-methoxy-7-methylquinoxalin-5-yl)-4-methyl-6-((2-phenyl-1H-imidazol-5-yl)methoxy)benzo[d]thiazole

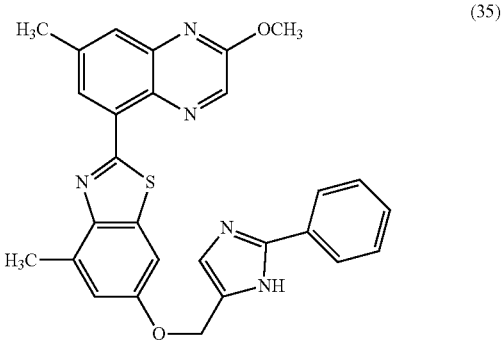 [SMILES: COc1cnc2c(-c3nc4c(C)cc(OCc5cnc(-c6ccccc6)[nH]5)cc4s3)cc(C)cc2n1]

Intermediate 35A:
5-(chloromethyl)-2-phenyl-1H-imidazole hydrochloride

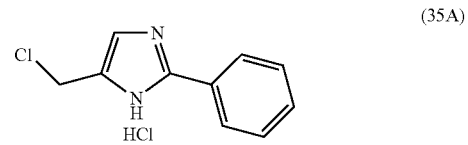 [SMILES: ClCc1cnc(-c2ccccc2)[nH]1 ; Cl]

To (2-phenyl-1H-imidazol-5-yl)methanol (0.216 g, 1.240 mmol) at room temperature was added thionyl chloride (0.453 ml, 6.20 mmol). The reaction mixture was stirred at room temperature for 10 min, and then at 65° C. for 2.0 h. The reaction mixture was diluted with chloroform (5.0 mL) and the resulting solution was evaporated. Additional co-evaporation with chloroform gave Intermediate 35A (0.28 g, 1.222 mmol, 99% yield) as a brown solid. ¹H NMR (400 MHz, DMSO-d₆) δ 8.21-8.15 (m, 2H), 7.83 (s, 1H), 7.67-7.62 (m, 3H), 4.93 (s, 2H).

Intermediate 35B: 2-(2-methoxy-7-methylquinoxalin-5-yl)-4-methylbenzo[d]thiazol-6-ol

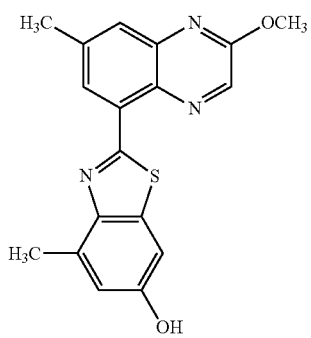

(35B)

To Intermediate 26D (561 mg, 1.150 mmol) dissolved in THF (4.0 mL) at room temperature was added 5.4 M sodium methoxide in MeOH (0.746 mL, 4.03 mmol). The reaction mixture turned deep red. The reaction mixture was stirred at room temperature for 20 min. HPLC and LCMS indicated a completion of the reaction. The reaction mixture was diluted with EtOAc, quenched with 1.0 N HCl (2.88 mL, 2.88 mmol). The organic layer was washed with brine, dried and concentrated to give Intermediate 35B (300 mg, 0.889 mmol, 77% yield) as yellow solid. ¹H NMR (400 MHz, chloroform-d) δ 8.47 (d, J=1.5 Hz, 1H), 8.43 (s, 1H), 7.63 (s, 1H), 7.09 (d, J=2.2 Hz, 1H), 6.75 (d, J=2.0 Hz, 1H), 3.73 (s, 3H), 2.69 (s, 3H), 2.55 (s, 3H); LC-MS: Method A, 50 to 100% B. RT=2.45 min, MS (ESI) m/z: 338.1 (M+H)⁺.

Example 35

To a stirred solution of Intermediate 35B (25 mg, 0.074 mmol) and cesium carbonate (97 mg, 0.296 mmol) in DMF (0.8 mL) at room temperature was added a solution of Intermediate 35A (37.3 mg, 0.163 mmol) in DMF (0.8 mL) dropwise. The reaction mixture was stirred at room temperature for 0.5 h, then another portion of Intermediate 35A (37.3 mg, 0.163 mmol) in DMF (0.8 mL) was added. The reaction mixture was stirred at room temperature for 1.0 h, diluted with EtOAc, quenched with ammonium chloride. The organic layer was collected, washed with brine, dried over sodium sulfate and concentrated. The crude material was purified via preparative LC/MS (method D, 50-90% B over 20 minutes, then a 5-minute hold at 100% B). Fractions containing the desired product were combined and dried via centrifugal evaporation to yield Example 35 (6.1 mg). ¹H NMR (500 MHz, DMSO-d₆) δ 8.75 (br. s., 1H), 8.61 (br. s., 1H), 8.02 (d, J=6.9 Hz, 2H), 7.84 (br. s., 2H), 7.74 (br. s., 1H), 7.61 (d, J=7.4 Hz, 3H), 7.12 (br. s., 1H), 5.26 (br. s., 2H), 4.09 (br. s., 3H), 2.77 (br. s., 3H), 2.66 (br. s., 3H); LC-MS: method A, RT=2.54 min, MS (ESI) m/z: 494.2 (M+H)⁺. Analytical HPLC purity (method B): 98%.

Example 36

N-benzyl-2-((2-(2-methoxy-7-methylquinoxalin-5-yl)-4-methylbenzo[d]thiazol-6-yl) oxy)acetamide

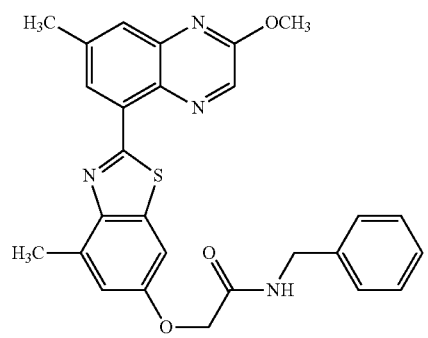

(36)

Intermediate 36A: methyl 2-((2-(2-methoxy-7-methylquinoxalin-5-yl)-4-methylbenzo[d]thiazol-6-yl) oxy)acetate

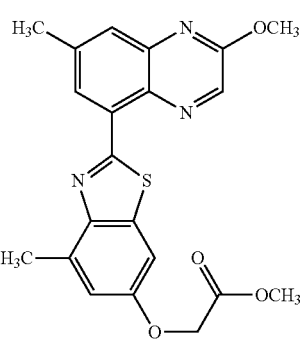

(36A)

To a suspension of Intermediate 35B (240 mg, 0.711 mmol) in DMF (10 mL) was added THF (2.0 mL) and cesium carbonate (695 mg, 2.134 mmol). The solution turned from yellow to brown. Methyl bromoacetate (0.328 mL, 3.56 mmol) was added dropwise. The reaction mixture was stirred at room temperature for 20 min, then at 50° C. for 2.0 h. HPLC and LCMS indicated a completion of the reaction. The reaction mixture was diluted with EtOAc/THF and water. The product could not dissolve at this stage. The organic suspension was separated from aqueous solution, concentrated to remove solvent and water. The crude was triturated with a mixture of acetonitrile and water. The solid was collected by filtration, washed with acetonitrile and dried to give Intermediate 36A (280 mg, 0.684 mmol, 96% yield) as yellow solid. ¹HNMR was not taken due to very poor solubility in DMSO-d₆. LC-MS: method A, RT=1.17 min, MS (ESI) m/z: 410.0 (M+H)⁺.

Intermediate 36B 2-((2-(2-methoxy-7-methylquinoxalin-5-yl)-4-methylbenzo[d]thiazol-6-yl)oxy)acetic acid

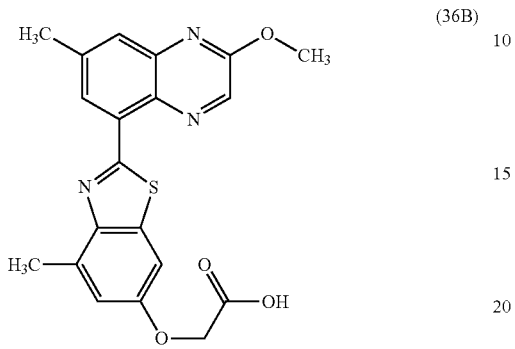
(36B)

To a suspension of Intermediate 36A (44 mg, 0.107 mmol) in THF (2.0 mL) and MeOH (0.5 mL) at room temperature was added 1.0 N NaOH (0.537 mL, 0.537 mmol). The suspension was stirred at room temperature for 2.0 h with occasional sonicating (3×) for 1 min. HPLC and LCMS indicated a complete of reaction. To the reaction mixture was added 1.0 N HCl (0.537 mL, 0.537 mmol), followed by addition of EtOAc/water. The organic layer was washed with brine and dried over sodium sulfate and concentrated. The crude was lyophilized to give Intermediate 36B (42 mg, 0.102 mmol, 95% yield) as a light yellow lyophilate. $^1$H NMR (500 MHz, methanol-$d_4$) δ 8.57 (d, J=1.9 Hz, 1H), 8.52 (s, 1H), 7.73 (dd, J=1.9, 0.8 Hz, 1H), 7.25 (d, J=2.5 Hz, 1H), 6.98 (dd, J=2.5, 0.8 Hz, 1H), 4.68 (s, 2H), 4.11 (s, 3H), 2.80 (s, 3H), 2.64 (s, 3H); LC-MS: method A, RT=1.06 min, MS (ESI) m/z: 396.0 (M+H)$^+$. Analytical HPLC purity (method B): 96%.

Example 36

To a suspension of Intermediate 36B (12.5 mg, 0.032 mmol) and phenylmethanamine (0.014 mL, 0.126 mmol) in DMF (1.0 mL) was added DIEA (0.044 mL, 0.253 mmol), followed by T$_3$P 50% wt in EtOAc (0.075 mL, 0.126 mmol). The reaction mixture was stirred at room temperature for 1.0 h. HPLC and LCMS indicated a completion of the reaction. The reaction was quenched by addition of 0.1% TFA in MeOH/water. The crude material was purified via preparative LC/MS (method D, 60-100% B over 15 minutes, then a 10-minute hold at 100% B). Fractions containing the desired product were combined and dried via centrifugal evaporation to yield Example 36 (9.8 mg). $^1$H NMR (500 MHz, DMSO-$d_6$) δ 8.75 (s, 1H), 8.72 (t, J=6.2 Hz, 1H), 8.62 (d, J=1.7 Hz, 1H), 7.84 (d, J=0.8 Hz, 1H), 7.55 (d, J=2.2 Hz, 1H), 7.33-7.22 (m, 5H), 7.11 (d, J=1.7 Hz, 1H), 4.67 (s, 2H), 4.39 (d, J=6.1 Hz, 2H), 4.10 (s, 3H), 2.77 (s, 3H), 2.66 (s, 3H); LC-MS: method A, RT=2.55 min, MS (ESI) m/z: 485.2 (M+H)$^+$. Analytical HPLC purity (method B): 95%.

Example 37

5-(7-chlorobenzofuran-2-yl)-2-methoxy-7-methylquinoxaline

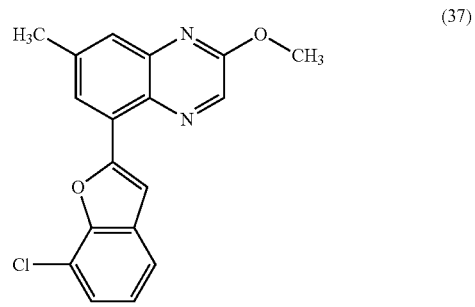 [SMILES: COc1cnc2c(-c3cc4cccc(Cl)c4o3)cc(C)cc2n1]
(37)

Intermediate 37A: 7-chloro-2-iodobenzofuran

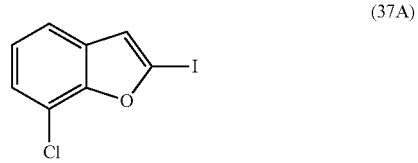 [SMILES: Clc1cccc2cc(I)oc12]
(37A)

To diisopropylamine (0.280 mL, 1.966 mmol) in THF (4.0 mL) at −78° C. was added 1.6 N n-BuLi in hexanes (1.229 mL, 1.966 mmol). The reaction mixture was stirred at −78° C. for 0.5 h. 7-Chlorobenzofuran (200 mg, 1.311 mmol) in THF (1.0 mL) was added, The reaction mixture was stirred at −78° C. for 0.5 h. Iodine (665 mg, 2.62 mmol) in THF (1.0 mL) was added dropwise until the brown color persisted (ca 1.3 eq.) The reaction mixture was stirred at −78° C. for 0.5 h, then at room temperature for 0.5 h. The reaction mixture was diluted with EtOAc, quenched with saturated ammonium chloride (5.0 mL) and 10% Na$_2$S$_2$O$_3$ (5.0 mL). After stirring at room temperature for 10 min, the organic layer was washed with brine, dried over sodium sulfate. After evaporation of solvent, the crude product Intermediate 37A (360 mg, 1.189 mmol, 91% yield) was obtained as a slightly brown oil. It was used for the next step without further purification. $^1$H NMR (400 MHz, chloroform-d) δ 7.40 (dd, J=7.7, 1.3 Hz, 1H), 7.24-7.20 (m, 1H), 7.17-7.11 (m, 1H), 6.99 (s, 1H). LC-MS: method H, 2 to 98% B. RT=1.07 min, MS (ESI) m/z: MW not observed (M+H)$^+$.

Intermediate 37B: 5-(7-chlorobenzofuran-2-yl)-2-(difluoromethoxy)-7-methylquinoxaline

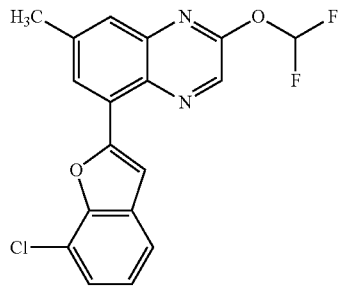

(37B)

To Intermediate I-1 (45.6 mg, 0.180 mmol), Intermediate 37A (50.0 mg, 0.180 mmol) and [1,1'-bis(diphenylphosphino)ferrocene]dichloropalladium (II) complex with dichloromethane (1:1) (5.87 mg, 7.18 µmol) was added toluene (1.5 mL) and EtOH (0.5 mL). The mixture was sonicated for 1 min, and flushed with argon. To this was added sodium carbonate (2M, 0.157 mL, 0.314 mmol). The reaction mixture was heated in a microwave reactor at 120° C. for 30 min. HPLC and LCMS indicated a completion of the reaction. The crude reaction mixture was diluted with EtOAc/water. The insoluble material was removed by filtration. The organic layer was washed with brine, dried over sodium sulfate and concentrated to give Intermediate 37B (64 mg, 0.177 mmol, 99% yield) as a brown solid. $^1$H NMR (500 MHz, DMSO-d$_6$) δ 8.93 (s, 1H), 8.24 (d, J=1.9 Hz, 1H), 8.20 (s, 1H), 7.90 (t, J$_{HF}$=71.53 Hz, 1H), 7.83-7.81 (m, 1H), 7.79 (dd, J=7.8, 1.0 Hz, 1H), 7.51 (dd, J=7.8, 1.0 Hz, 1H), 7.34 (t, J=7.7 Hz, 1H), 2.67 (s, 3H); LC-MS: method H, RT=2.70 min, MS (ESI) m/z: 361.0 (M+H)$^+$.

Example 37

To Intermediate 37B (35 mg, 0.097 mmol) dissolved in THF (1.5 mL) and MeOH (1.5 mL) at room temperature was added 4.3 M sodium methoxide in MeOH (0.090 mL, 0.388 mmol). The reaction mixture was stirred at room temperature for 1.0 h. LCMS indicated ca 60% conversion. Then another portion of 4.3 M sodium methoxide in MeOH (0.090 mL, 0.388 mmol) was added and the reaction was continued at room temperature for 2.0 h. LCMS indicated a completion of the reaction. Methanol was removed under vacuum. The reaction mixture was diluted with EtOAc, quenched with 0.5 N HCl (2.0 mL). The organic layer was washed with saturated sodium bicarbonate, brine, dried and concentrated. The crude material was purified via preparative LC/MS (method D, 65-100% B over 20 minutes, then a 8-minute hold at 100% B). Fractions containing the desired product were combined and dried via centrifugal evaporation to yield Example 37 (16.0 mg). $^1$H NMR (500 MHz, DMSO-d$_6$) δ 8.70 (s, 1H), 8.17 (s, 1H), 8.10 (d, J=1.7 Hz, 1H), 7.77 (dd, J=7.8, 1.0 Hz, 1H), 7.74 (d, J=0.8 Hz, 1H), 7.49 (dd, J=7.8, 1.0 Hz, 1H), 7.33 (t, J=7.7 Hz, 1H), 4.09 (s, 3H), 2.64 (s, 3H); LC-MS: method H, RT=2.76 min, MS (ESI) m/z: 325.1 and 327.1 (M+H)$^+$. Analytical HPLC purity (method B): 95%.

Example 38

2-((7-chloro-2-(2-methoxy-7-methylquinoxalin-5-yl)benzofuran-5-yl)oxy)ethyl (2-methylpyridin-4-yl) carbamate

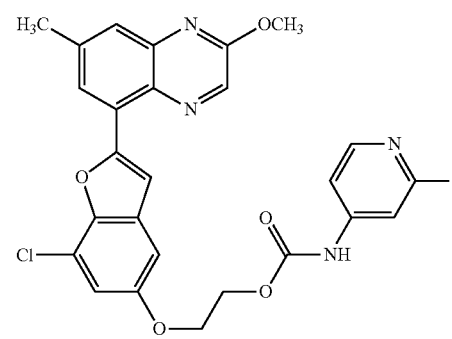

(38)

Intermediate 38A:
2-chloro-1-(2,2-diethoxyethoxy)-4-methoxybenzene

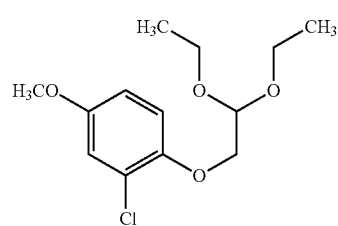

(38A)

To a suspension of sodium hydride (60%) (0.189 g, 4.73 mmol) in DMF (5.0 mL) was added 2-chloro-4-methoxyphenol (0.5 g, 3.15 mmol) dissolved in DMF (3.0 mL) at room temperature. After hydrogen evolution was ceased (20 min at 40° C. oil bath), 2-bromo-1,1-diethoxyethane (0.593 mL, 3.94 mmol) was added. The reaction mixture was heated at 160° C. for 18 h. After cooled to room temperature, the reaction mixture was diluted with EtOAc/water. The organic layer was washed with saturated sodium bicarbonate, brine, dried over sodium sulfate and concentrated to give Intermediate 38A (0.95 g, 3.46 mmol, 110% yield) as a light yellow oil. It was used for the next step without further purification. $^1$H NMR (400 MHz, chloroform-d) δ 6.93 (d, J=3.1 Hz, 1H), 6.90 (d, J=9.0 Hz, 1H), 6.73 (dd, J=8.9, 3.0 Hz, 1H), 4.84 (t, J=5.2 Hz, 1H), 4.00 (d, J=5.3 Hz, 2H), 3.83-3.76 (m, 2H), 3.75 (s, 3H), 3.71-3.64 (m, 2H), 1.27-1.22 (t, J=7.04 Hz, 6H). LC-MS: method H, 2 to 98% B. RT=1.02 min, MS (ESI) m/z: 297.0 (M+Na)$^+$.

Intermediate 38B: 7-chloro-5-methoxybenzofuran

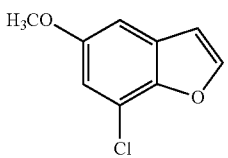

(38B)

A mixture of Amberlyst-15 (1.2 g, 2.91 mmol) in chlorobenzene (100 mL) was heated at reflux (oil bath temperature 165° C.) to remove water by azeotropic distillation. Distillate was removed until the volume remaining in the flask was about 80 mL. To this mixture was then added dropwise over 1.0 h a solution of Intermediate 38A (0.8 g, 2.91 mmol) in chlorobenzene (9.0 mL). The reaction mixture was stirred at reflux with constant water removal for another 2.0 h. After cooled to room temperature, the Amberlyst-15 was removed by filtration. The filtrated was concentrated under vacuum, and loaded directly to ISCO column for purification. The crude product was purified by flash chromatography (loading in chloroform, 0% to 30% EtOAc in hexane over 15 min using a 24 g silica gel cartridge). The desired fractions were combined and concentrated to yield Intermediate 38B (0.32 g, 1.752 mmol, 60.2% yield) as a light yellow oil. $^1$H NMR (400 MHz, chloroform-d) δ 7.64 (d, J=2.2 Hz, 1H), 6.97-6.93 (m, 2H), 6.73 (d, J=2.2 Hz, 1H), 3.83 (s, 3H); LC-MS: method H, 2 to 98% B. RT=0.94 min, MS (ESI) m/z: 183.0 (M+H)$^+$.

Intermediate 38C: 7-chlorobenzofuran-5-ol

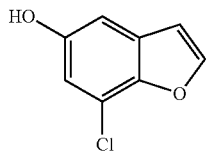

(38C)

To Intermediate 38B (0.32 g, 1.752 mmol) and tetrabutylammonium iodide (0.680 g, 1.840 mmol) in dichloromethane (4 mL) at −78° C. was added 1.0 M boron trichloride in heptane (4.12 ml, 4.12 mmol) dropwise. The reaction mixture was stirred at −78° C. for 45 min. Then the cooling bath was removed and the reaction mixture was stirred at room temperature for 3.0 h. HPLC and TLC indicated a completion of the reaction. The mixture was poured into saturated sodium bicarbonate and ice, stirred for 20 min, extracted with EtOAc. The organic layer was collected, washed with 10% $Na_2S_2O_3$, water, brine and dried over sodium sulfate. After evaporation of solvent, the crude product was dissolved in a small amount of chloroform and charged to a 12 g silica gel cartridge which was eluted with hexanes for 1 min., then a 15 min gradient from 0% to 50% EtOAc in hexanes. The desired fractions were combined and concentrated to give Intermediate 38C (0.29 g, 1.720 mmol, 98% yield) as a slightly brown solid. $^1$H NMR (400 MHz, chloroform-d) δ 7.64 (d, J=2.0 Hz, 1H), 6.92 (d, J=2.4 Hz, 1H), 6.88 (d, J=2.4 Hz, 1H), 6.71 (d, J=2.2 Hz, 1H).

Intermediate 38D: tert-butyl((7-chlorobenzofuran-5-yl)oxy)dimethylsilane

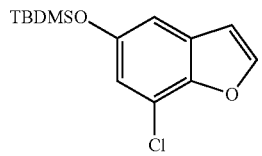

(38D)

To a stirred solution of Intermediate 38C (0.30 g, 1.780 mmol) in DMF (4.0 mL) was added TBDMS-Cl (0.402 g, 2.67 mmol) and imidazole (0.218 g, 3.20 mmol). The reaction mixture was stirred at room temperature for 1.5 h. HPLC and TLC indicated a completion of the reaction. The mixture was partitioned between EtOAc/water. The organic layer was washed with water, brine and dried over sodium sulfate. After evaporation of solvent, the crude product was dissolved in a small amount of chloroform and charged to a 12 g silica gel cartridge which was eluted with hexanes for 3 min., then a 15 min gradient from 0% to 15%. The desired fractions were combined and concentrated to give Intermediate 38D (0.4 g, 1.414 mmol, 79% yield) as a clear oil. $^1$H NMR (400 MHz, chloroform-d) δ 7.64 (d, J=2.2 Hz, 1H), 6.93 (d, J=2.2 Hz, 1H), 6.86 (d, J=2.2 Hz, 1H), 6.72 (d, J=2.2 Hz, 1H), 1.01 (s, 9H), 0.22 (s, 6H); LC-MS: method H, 2 to 98% B. RT=0.96 min, MS (ESI) m/z: MS not observed (M+H)$^+$.

Intermediate 38E: tert-butyl((7-chloro-2-iodobenzofuran-5-yl)oxy)dimethylsilane

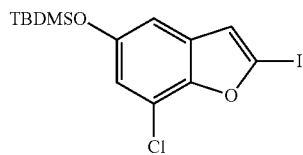

(38E)

To diisopropylamine (0.302 mL, 2.121 mmol) in THF (4.0 mL) at −78° C. was added 1.6 N n-BuLi in hexanes (1.326 mL, 2.121 mmol). The reaction mixture was stirred at −78° C. for 20 min. Intermediate 38D (0.4 g, 1.414 mmol) in THF (1.0 mL) was added dropwise, The reaction mixture was stirred at −78° C. for 0.5 h. Iodine (0.610 g, 2.404 mmol) in THF (1.0 mL) was added dropwise until the brown color persisted (ca 1.2 eq), and the reaction mixture was stirred at −78° C. for 0.5 h, then at room temperature for 0.5 h. The reaction mixture was diluted with EtOAc, quenched with saturated ammonium chloride (5.0 mL) and 10% $Na_2S_2O_3$ (5.0 mL). After stirring at room temperature for 10 min, the organic layer was washed with brine, dried over sodium sulfate. After evaporation of solvent, Intermediate 38E (0.51 g, 1.148 mmol, 81% yield) was obtained as a slightly brown oil. It was used for the next step without further purification. $^1$H NMR (400 MHz, chloroform-d) δ 6.89 (s, 1H), 6.84 (d, J=2.2 Hz, 1H), 6.78 (d, J=2.2 Hz, 1H), 1.00 (s, 9H), 0.21 (s, 6H). LC-MS: method H, 2 to 98% B. RT=1.36 min, MS (ESI) m/z: no desired MS observed (M+H)$^+$.

Intermediate 38F 5-(5-((tert-butyldimethylsilyl)oxy)-7-chlorobenzofuran-2-yl)-2-(difluoromethoxy)-7-methylquinoxaline

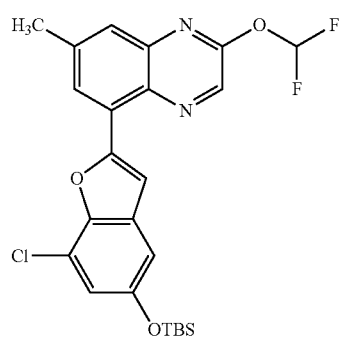

(38F)

To Intermediate I-1 (0.311 g, 1.223 mmol), Intermediate 38E (0.5 g, 1.223 mmol) and [1,1'-bis(diphenylphosphino)ferrocene]dichloropalladium (II) complex with dichloromethane (1:1) (0.040 g, 0.049 mmol) was added toluene (4.5 mL) and EtOH (1.5 mL). The mixture was sonicated for 1 min, and flushed with argon. To this was added sodium carbonate (2M, 1.070 mL, 2.141 mmol). The reaction mixture was heated in a microwave reactor at 120° C. for 30 min. HPLC and LCMS indicated a completion of the reaction. The crude reaction mixture was directly loaded on an ISCO column for purification. The crude product was purified by flash chromatography (loading in chloroform, 0% to 25% EtOAc in hexane over 15 min using a 24 g silica gel cartridge). The desired fractions were combined and concentrated to yield Intermediate 38F (0.36 g, 0.733 mmol, 59.9% yield) as an yellow solid. $^1$H NMR (400 MHz, chloroform-d) δ 8.63 (s, 1H), 8.27 (d, J=1.8 Hz, 1H), 8.02 (s, 1H), 7.66 (dd, J=1.8, 0.9 Hz, 1H), 7.65 (t, $J_{HF}$=71.75 Hz, 1H), 6.99 (d, J=2.2 Hz, 1H), 6.88 (d, J=2.2 Hz, 1H), 2.66 (s, 3H), 1.02 (s, 9H), 0.23 (s, 6H); $^{19}$F NMR (376 MHz, chloroform-d) δ −89.72 (s, 1F); LC-MS: method H, 2 to 98% B. RT=1.51 min, MS (ESI) m/z: 491.1 and 493.1 (M+H)$^+$.

Intermediate 38G: 7-chloro-2-(2-methoxy-7-methylquinoxalin-5-yl)benzofuran-5-ol

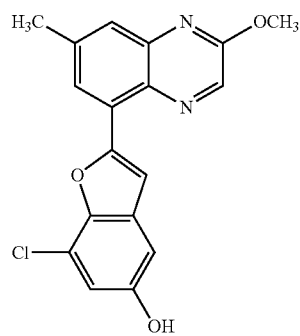

(38G)

To Intermediate 38F (0.36 g, 0.733 mmol) dissolved in THF (3.0 mL) and MeOH (3.0 mL) at room temperature was added 4.3 M sodium methoxide in MeOH (0.767 mL, 3.30 mmol). The reaction mixture was stirred at room temperature for 4.0 h. HPLC and LCMS indicated a completion of the reaction. The reaction mixture was quenched with 1.0 N HCl (2.93 mL, 2.93 mmol), diluted with EtOAc. The organic layer was washed with brine, dried and concentrated to give Intermediate 38G (0.26 g, 0.687 mmol, 94% yield) as yellow solid. This was used for the next step without further purification. $^1$H NMR (400 MHz, chloroform-d) δ 8.43 (s, 1H), 8.08 (d, J=1.8 Hz, 1H), 7.90 (s, 1H), 7.57 (d, J=0.9 Hz, 1H), 6.90 (d, J=2.2 Hz, 1H), 6.84-6.80 (m, 1H), 4.05 (s, 3H), 2.56 (s, 3H); LC-MS: method H, 2 to 98% B. RT=1.14 min, MS (ESI) m/z: 341.0 and 343.0 (M+H)$^+$.

Intermediate 38H 2-((7-chloro-2-(2-methoxy-7-methylquinoxalin-5-yl)benzofuran-5-yl)oxy)ethanol

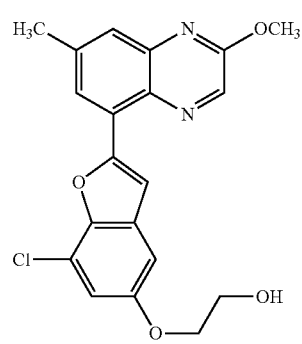

(38H)

To a suspension of Intermediate 38G (145 mg, 0.426 mmol) in DMF (3.0 mL) and THF (2.0 mL) was added cesium carbonate (277 mg, 0.851 mmol). The reaction mixture was stirred at room temperature for 20 min. Then 2-bromoethyl acetate (0.063 mL, 0.574 mmol) in THF (0.5 mL) was added dropwise. The reaction mixture was stirred at room temperature for 30 min, then at 65° C. for 1.5 h. HPLC and LCMS indicated completion of reaction. After cooled to room temperature, the reaction mixture was diluted with EtOAc and water, extracted with EtOAc (6×). The combined organic layer was washed with brine and dried with sodium sulfate and concentrated to give yellow solid as the acetate. The crude acetate was suspended in a mixture of THF (3.0 mL) and MeOH (0.8 mL). To this suspension was added 1.0 N NaOH (0.851 mL, 0.851 mmol). The reaction mixture was stirred at room temperature for 30 min. The suspension turned to a clear brown solution. HPLC and LCMS indicated a clean conversion of the ester to acid. The reaction was quenched with 1.0 N HCl (0.638 mL, 0.638 mmol) diluted in 1.0 mL of water, extracted with EtOAc, washed with saturated sodium bicarbonate, brine, dried over sodium sulfate and concentrated. The crude product was purified by flash chromatography (loading in chloroform, 10% to 60% EtOAc in hexane over 10 min using a 12 g silica gel cartridge). The desired fractions were combined and concentrated to yield Intermediate 38H (110 mg, 0.286 mmol, 67.2% yield) as a lightly yellow solid. $^1$H NMR (400 MHz, DMSO-d$_6$) δ 8.67 (s, 1H), 8.07 (s, 1H), 8.04 (d, J=1.8 Hz, 1H), 7.70 (dd, J=1.8, 0.9 Hz, 1H), 7.29 (d, J=2.4 Hz, 1H), 7.10 (d, J=2.2 Hz, 1H), 4.90 (t, J=5.5 Hz, 1H), 4.07 (s, 3H), 4.06 (m, 2H), 3.78-3.74 (m, 2H), 2.61 (s, 3H); LC-MS: method H, 2 to 98% B. RT=1.14 min, MS (ESI) m/z: 385.0 and 387.0 (M+H).

Intermediate 38I

2-{[7-chloro-2-(2-methoxy-7-methylquinoxalin-5-yl)-1-benzofuran-5-yl]oxy}ethyl chloroformate

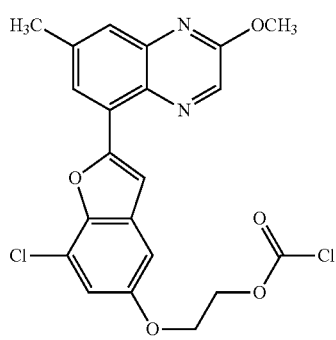

To a solution Intermediate 38H (100 mg, 0.260 mmol) in THF (3.0 mL) at room temperature was added 15% phosgene in toluene (0.733 mL, 1.039 mmol). The reaction mixture was left stirring at room temperature overnight. HPLC and LCMS indicated the reaction was complete. Solvent was completely removed under high vacuum to give Intermediate 38I (116 mg, 0.259 mmol, 100% yield) as a slightly yellow solid. It was used for the next step without purification. LC-MS: method H, 2 to 98% B. RT=1.30 min, MS (ESI) m/z: 447.1 (M+H)⁺.

Example 38

To a solution of 2-methylpyridin-4-amine (19.34 mg, 0.179 mmol) in DCM (0.8 mL) was added DIEA (0.062 mL, 0.358 mmol), followed by addition of Intermediate 38I (16 mg, 0.036 mmol) in THF (0.8 mL). The reaction mixture was stirred at room temperature for 1.0 h. HPLC and LCMS indicated a completion of reaction. The reaction was quenched by addition of a small amount of MeOH/water/ 0.1% TFA. Solvent was removed under vacuum. The crude material was purified via preparative LC/MS (method D, 50-90% B over 18 minutes, then a 5-minute hold at 100% B). Fractions containing the desired product were combined and dried via centrifugal evaporation to yield Example 38 (10 mg). ¹H NMR (500 MHz, DMSO-d₆) δ 10.37 (br. s., 1H), 8.68 (s, 1H), 8.29 (d, J=5.5 Hz, 1H), 8.08 (s, 1H), 8.05 (s, 1H), 7.72 (s, 1H), 7.39-7.32 (m, 3H), 7.16 (d, J=1.9 Hz, 1H), 4.51 (d, J=4.4 Hz, 2H), 4.34 (d, J=3.9 Hz, 2H), 4.07 (s, 3H), 2.62 (s, 3H), 2.42 (s, 3H); LC-MS: method H, RT=2.16 min, MS (ESI) m/z: 519.2 (M+H)⁺. Analytical HPLC purity (method B): 99%.

Example 39

N-(2-((7-chloro-2-(2-methoxy-7-methylquinoxalin-5-yl)benzofuran-5-yl)oxy)ethyl)benzenesulfonamide

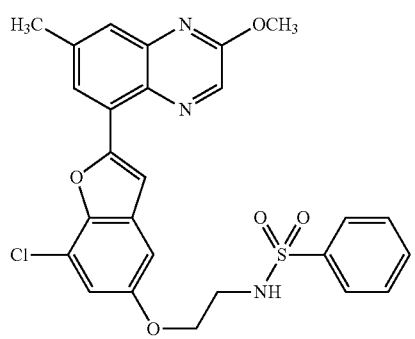

Intermediate 39A: tert-butyl (2-((7-chloro-2-(2-methoxy-7-methylquinoxalin-5-yl) benzofuran-5-yl) oxy)ethyl)carbamate

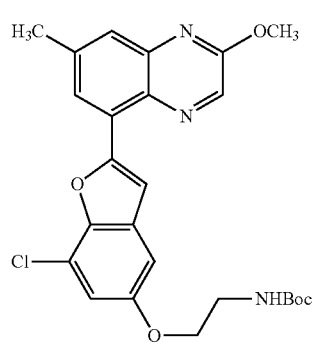

A solution of tert-butyl (2-hydroxyethyl)carbamate (85 mg, 0.528 mmol) and DIAD (0.123 mL, 0.634 mmol) in THF (1.0 mL) was added dropwise to a mixture of Intermediate 38G (72 mg, 0.211 mmol) and triphenylphosphine (163 mg, 0.623 mmol) in THF (2.0 mL) heated at 70° C. The reaction mixture was stirred at 70° C. for 15 min, at which time HPLC and LCMS indicated a completion of the reaction. Solvent was removed under vacuum. The crude product was purified by flash chromatography (loading in chloroform, 5% to 45% EtOAc in hexane over 15 min using a 12 g silica gel cartridge). The desired fractions were combined and concentrated to yield Intermediate 39A (80 mg, 0.152 mmol, 72.0% yield) as a pale yellow solid. ¹H NMR (400 MHz, DMSO-d₆) δ 8.63 (s, 1H), 8.05 (s, 1H), 8.04 (d, J=1.8 Hz, 1H), 7.68 (s, 1H), 7.25 (d, J=2.4 Hz, 1H), 7.06 (d, J=2.2 Hz, 1H), 4.03-4.00 (m, 2H), 3.34 (t, J=5.6 Hz, 2H), 2.60 (s, 3H), 1.40 (s, 9H); LC-MS: method H, 2 to 98% B. RT=1.29 min, MS (ESI) m/z: 484.1 (M+H)⁺.

Intermediate 39B 2-((7-chloro-2-(2-methoxy-7-methylquinoxalin-5-yl)benzofuran-5-yl)oxy)ethanamine

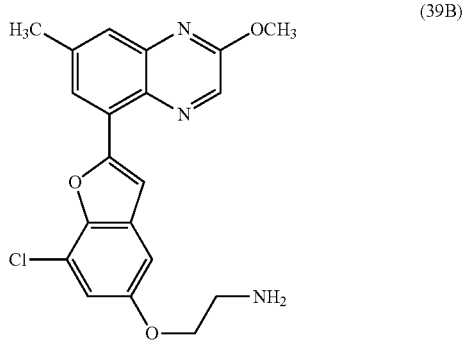 [SMILES: COc1cnc2c(-c3cc4cc(OCCN)cc(Cl)c4o3)cc(C)cc2n1]

(39B)

To Intermediate 39A (80 mg, 0.165 mmol) in DCM (2 mL) was added 2,6-lutidine (0.077 mL, 0.661 mmol) followed by TMS-OTf (0.119 mL, 0.661 mmol). The reaction mixture was stirred at room temperature for 1 h. The mixture was diluted with EtOAc and NaHCO₃ and extracted with EtOAc. The combined organic layer was washed with brine and concentrated. The residual was treated with 1.0 ml of MeOH, stirred at room temperature for 15 min, and concentrated to give Intermediate 39B (60 mg) as yellow solid. the crude sample was used for next step without purification.

Example 39

To a suspension of Intermediate 39B (18 mg, 0.047 mmol) in DMF (1.0 mL) and THF (1.0 mL) was added DIEA (0.066 mL, 0.375 mmol), followed by benzenesulfonyl chloride (8.27 µl, 0.064 mmol). The reaction mixture was stirred at room temperature for 2.0 h. Solvent was removed and the crude was purified via preparative LC/MS (method D, 55-95% B over 10 minutes, then a 7-minute hold at 100% B). Fractions containing the desired product were combined and dried via centrifugal evaporation to yield 39 (22.8 mg). ¹H NMR (500 MHz, chloroform-d) δ 8.51 (s, 1H), 8.16 (s, 1H), 8.02 (s, 1H), 7.91 (d, J=7.7 Hz, 2H), 7.65 (s, 1H), 7.62-7.57 (m, 1H), 7.55-7.50 (m, 2H), 6.91 (d, J=1.9 Hz, 1H), 6.83 (d, J=2.2 Hz, 1H), 4.99 (t, J=6.1 Hz, 1H), 4.12 (s, 3H), 4.03 (t, J=5.1 Hz, 2H), 3.42 (q, J=5.5 Hz, 2H), 2.63 (s, 3H); LC-MS: method H. RT=2.66 min, MS (ESI) m/z: 524.2 (M+H)⁺. Analytical HPLC purity (method B):100%.

Example 40

5-(benzo[b]thiophen-2-yl)-2-(difluoromethoxy)-7-methylquinoxaline

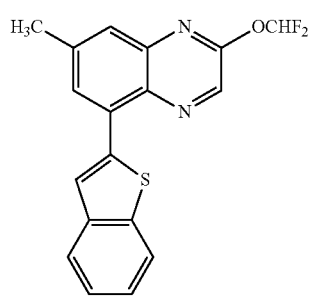

(40)

To a solution of benzo[b]thiophen-2-yltributylstannane (35.1 mg, 0.083 mmol) and Intermediate I-1G (20 mg, 0.069 mmol) in 1,4-dioxane (1 mL) was added Pd(Ph₃P)₄ (9.59 mg, 8.30 µmol). The mixture was heated at 150° C. for 1 h in a microwave reactor. LCMS indicated a completion of the reaction. The mixture was diluted with acetonitrile and filtered. The filtrate was concentrated and purified by a preparative HPLC (method A, 65-100% B in 8 min.). The desired fractions were collected, dried and lyophilized to give 40 (18 mg, 0.050 mmol, 72.2% yield). ¹H NMR (400 MHz, chloroform-d) δ 8.66 (s, 1H), 8.07 (s, 1H), 8.00-7.46 (m, 5H), 7.45-7.32 (m, 2H), 2.64 (s, 3H). ¹⁹F NMR (376 MHz, chloroform-d) δ -90.43 (s, 2F). LC-MS: method B, RT=2.55 min, MS (ESI) m/z: 343.0 (M+H)⁺. Analytical HPLC purity (method A): 99%.

Example 41

2-(difluoromethoxy)-5-(7-methoxybenzofuran-2-yl)-7-methylquinoxaline

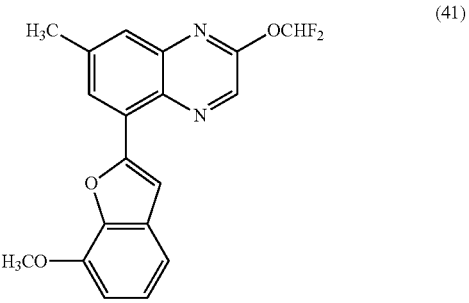 [SMILES: COc1cccc2cc(-c3cc(C)cc4nc(OC(F)F)cnc34)oc12]

(41)

To (7-methoxybenzofuran-2-yl)boronic acid (13.28 mg, 0.069 mmol) and Intermediate I-1G was added toluene (0.75 mL) and EtOH (0.25 mL). The reaction mixture was stirred at room temperature until solids are dissolved, then [1,1'-bis(diphenylphosphino)ferrocene] dichloropalladium (II) complex with dichloromethane (1:1) (6.78 mg, 8.30 µmol) was added. The flask was degassed and flushed with argon. Finally sodium carbonate 2M (0.069 mL, 0.138 mmol) was added dropwise. The reaction vessel was sealed and bubbled with argon for 5 min, then placed in microwave reactor at 140° C. for 30 min. The reaction mixture was cooled to room temperature, diluted with EtOAc and water, extracted with EtOAc (3×). The combined organic layer was washed with brine, dried with MgSO₄ and concentrated. The crude sample was purified by 12 g ISCO column eluted with 0-70% EtOAc in hexane for 15 min. The desired fraction was collected, dried and purified by preparative HPLC (method A, 30-100% B in 10 min.) to give Example 41 (8 mg, 0.022 mmol, 31.5% yield). ¹H NMR (400 MHz, chloroform-d) δ 8.66 (s, 1H), 8.34 (d, J=1.8 Hz, 1H), 8.10 (s, 1H), 7.91-7.47 (m, 2H), 7.29 (s, 1H), 7.23-7.17 (m, 1H), 6.88 (d, J=7.8 Hz, 1H), 4.10 (s, 3H), 2.65 (s, 3H). ¹⁹F NMR (376 MHz, chloroform-d) -90.12 (s, 2F). LC-MS: method B, RT=2.53 min, MS (ESI) m/z: 357.0 (M+H)⁺. Analytical HPLC purity (method A): 98%.

Example 42

2-(difluoromethoxy)-5-(4-methoxybenzofuran-2-yl)-7-methylquinoxaline

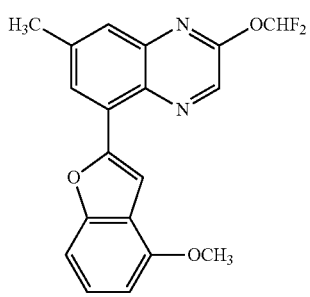
(42)

Intermediate 42A: (benzofuran-4-yloxy)(tert-butyl)dimethylsilane

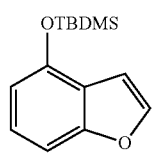
(42A)

To a solution of benzofuran-4-ol (200 mg, 1.491 mmol) in DMF (5 mL) was added TBDMS-Cl (337 mg, 2.237 mmol) and imidazole (203 mg, 2.98 mmol). The mixture was stirred at room temperature for 2 h. LCMS indicated a completion of the reaction. The mixture was diluted by EtOAc and water, extracted with EtOAc, the combined organic layer was washed with brine, dried with MgSO$_4$ and concentrated. The crude sample was purified with a 12 g ISCO column eluted with 0-50% EtOAc/Hex, the desired fraction was collected to give Intermediate 42A (270 mg, 1.087 mmol, 72.9% yield). $^1$H NMR (400 MHz, chloroform-d) δ 7.53 (d, J=2.3 Hz, 1H), 7.18-7.10 (m, 2H), 6.79 (d, J=1.8 Hz, 1H), 6.72-6.60 (m, 1H), 1.06 (s, 10H), 0.31-0.18 (m, 6H). LC-MS: method B, RT=2.55 min, MS (ESI) m/z: 249 (M+H)$^+$.

Intermediate 42B: 4-(tert-butyldimethylsilyloxy)benzofuran-2-ylboronic acid

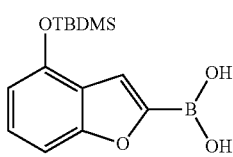
(42B)

To a solution of Intermediate 42A (270 mg, 1.087 mmol) in THF (4 mL) was added n-BuLi (0.815 mL, 1.304 mmol) at −78° C. After 30 min stirring, trimethyl borate (0.243 mL, 2.174 mmol) was added, and the reaction mixture was slowly warmed up to room temperature over 1 h. HCl (5.43 mL, 5.43 mmol) was added and the mixture was stirred at room temperature for 30 min. The mixture was diluted with EtOAc and water, extracted with EtOAc and the combined organic layer was washed with brine, dried with MgSO$_4$ and concentrated. The crude sample was purified with a 12 g ISCO column eluted with 0-70% EtOAc/Hex. The desired fraction was collected to give Intermediate 42B (190 mg, 0.650 mmol, 59.8% yield). LC-MS: method C, RT=2.35 min, MS (ESI) m/z: 293 (M+H)$^+$.

Intermediate 42C

5-(4-(tert-butyldimethylsilyloxy)benzofuran-2-yl)-2-(difluoromethoxy)-7-methylquinoxaline

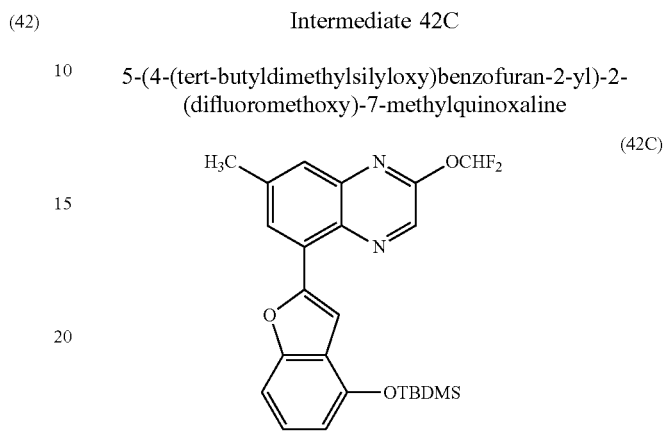
(42C)

To Intermediate I-1 (50 mg, 0.173 mmol) and Intermediate 42B (60.7 mg, 0.208 mmol) was added toluene (0.75 mL) and EtOH (0.25 mL). The reaction mixture was stirred at room temperature until solids are dissolved, then [1,1'-bis(diphenylphosphino) ferrocene]dichloropalladium (II) complex with dichloromethane (1:1) (16.95 mg, 0.021 mmol) was added. The flask was degassed and flushed with argon. Finally sodium carbonate (0.173 mL, 2M, 0.346 mmol) was added dropwise. The reaction vessel was sealed and bubbled with argon for 5 min, then placed in microwave reactor at 120° C. for 30 min. LCMS indicated a completion of the reaction. The reaction mixture was cooled to room temperature and was diluted with EtOAc and water, extracted with EtOAc (3×), the combined organic layer was washed with brine, dried with MgSO$_4$ and concentrated. The crude sample was purified with a 12 g ISCO column eluted with 0-70% EtOAc in hexanes for 15 min. The desired fraction was collected to give Intermediate 42C (79 mg, 0.173 mmol, 100% yield). $^1$H NMR (400 MHz, chloroform-d) δ 8.66 (s, 1H), 8.23 (d, J=1.8 Hz, 1H), 8.09 (s, 1H), 7.88-7.47 (m, 2H), 7.23-7.18 (m, 2H), 6.69 (dd, J=6.3, 2.3 Hz, 1H), 2.65 (s, 3H), 1.12-1.09 (m, 9H), 0.29 (s, 6H). $^{19}$F NMR (376 MHz, acetonitrile-d$_3$) δ −90.43 (s, 2F). LC-MS: method C, RT=2.68 min.

Intermediate 42D: 2-(2-(difluoromethoxy)-7-methylquinoxalin-5-yl)benzofuran-4-ol

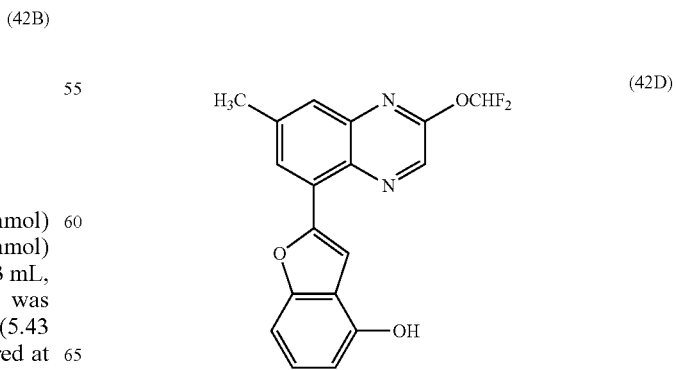
(42D)

To a solution of Intermediate 42C (76 mg, 0.166 mmol) in MeOH (1 mL) and THF was added HCl (0.277 mL, 12M, 3.33 mmol). The mixture was stirred at room temperature for 1 h. LCMS indicated a completion of the reaction. The mixture was diluted with EtOAc and saturated NaHCO$_3$, extracted with EtOAc, the combined organic layer was washed with brine, dried with MgSO$_4$ and concentrated. Intermediate 42D (50 mg, 0.142 mmol, 85% yield) was obtained and used for next step without purification. $^1$H NMR (400 MHz, chloroform-d) δ 8.65 (s, 1H), 8.25 (d, J=1.8 Hz, 1H), 8.20 (s, 1H), 7.87-7.47 (m, 2H), 7.23-7.18 (m, 2H), 6.72-6.65 (m, 1H), 2.66 (s, 3H). $^{19}$F NMR (376 MHz, chloroform-d) −90.12 (s, 2F). LC-MS: method B, RT=4.44 min, MS (ESI) m/z: 343.1 (M+H)$^+$.

Example 42

To a solution of Intermediate 42D (10 mg, 0.029 mmol) in acetonitrile (1 mL) was added Cs$_2$CO$_3$ (28.6 mg, 0.088 mmol) and MeI (1.827 μL, 0.029 mmol). The mixture was stirred at 45° C. for 1 h. The mixture was diluted with 1 ml of DMSO and 1 ml of acetonitrile, filtered and purified with a preparative HPLC (method A, 65-100% B in 8 min.). The desired fractions were placed in a SpeedVac overnight to remove solvent, then lyophilized to give Example 42 (5.6 mg, 0.015 mmol, 52.7% yield). $^1$H NMR (chloroform-d, 400 MHz): δ=8.65 (s, 1H), 8.25 (s, 1H), 8.20 (s, 1H), 7.46-7.86 (m, 2H), 7.28-7.32 (m, 1H), 7.19-7.23 (m, 1H), 6.71 (d, J=7.8 Hz, 1H), 4.02 (s, 3H), 2.65 ppm (s, 3H). $^{19}$F NMR (chloroform-d, 400 MHz) −90.12 (s, 2F). LC-MS: method B, RT=4.56 min, MS (ESI) m/z: 357.1 (M+H)$^+$. Analytical HPLC purity (method A): 98%.

Example 43

5-(4-(benzyloxy)benzofuran-2-yl)-2-methoxy-7-methylquinoxaline

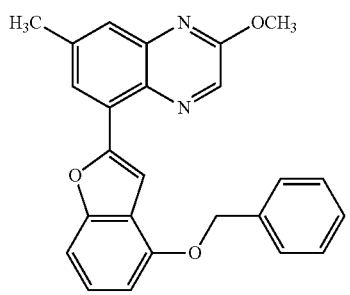

(43)

To a solution of Intermediate 42D (10 mg, 0.029 mmol) in acetonitrile (1 mL) was added Cs$_2$CO$_3$ (28.6 mg, 0.088 mmol) and benzyl bromide (3.47 μl, 0.029 mmol). The mixture was stirred at 45° C. for 1 h. The mixture was diluted with 1.0 ml of MeOH and water, extracted with EtOAc. The combined organic layer was washed with brine, dried with MgSO$_4$ and concentrated. The mixture was purified with preparative HPLC (method A, 65-100% B in 6 min.). The desired fractions were placed in a SpeedVac overnight to remove solvent, then lyophilized to give 43 (2.5 mg, 5.86 μmol, 20.07% yield). $^1$H NMR (chloroform-d, 400 MHz): δ=8.53 (s, 1H), 8.19 (s, 1H), 8.12 (d, J=1.8 Hz, 1H), 7.62 (s, 1H), 7.49-7.57 (m, 2H), 7.40-7.47 (m, 2H), 7.33-7.39 (m, 1H), 7.21-7.25 (m, 2H), 6.72-6.80 (m, 1H), 5.28 (s, 2H), 4.12 (s, 3H), 2.63 ppm (s, 3H). LC-MS: method C, RT=3.25 min, MS (ESI) m/z: 397.1 (M+H)$^+$. Analytical HPLC purity (method A): 93.0%.

Example 44

5-(5-(benzyloxy)benzofuran-2-yl)-2-(difluoromethoxy)-7-methylquinoxaline

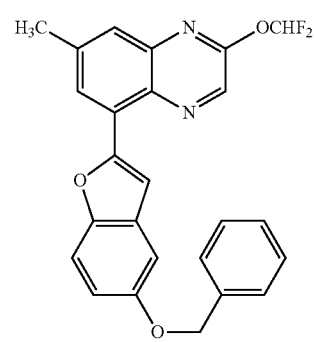

(44)

Intermediate 44A: benzofuran-5-ol

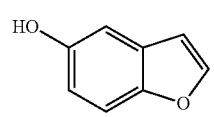

(44A)

To an ice-cooled solution of 5-methoxybenzofuran (0.71 g, 4.79 mmol) in dichloromethane (8.0 mL) was added 1.0 M boron tribromide in dichloromethane (4.79 mL, 4.79 mmol). The mixture was stirred at 0° C. for 1.0 h. HPLC indicated ca 30-40% starting material still remaining. Then another portion of 1.0 M boron tribromide in dichloromethane (4.79 mL, 4.79 mmol) was added and the mixture was stirred from 0° C. to room temperature over an hour. HPLC indicated a complete conversion of starting material. The mixture was poured into ice water, stirred for 15 min, extracted with dichloromethane. The organic layer was dried over sodium sulfate. After evaporation of solvent, Intermediate 44A (0.33 g, 2.460 mmol, 51.3% yield) was obtained as slightly brown oil. It was used for the next step without further purification. $^1$H NMR (500 MHz, chloroform-d) δ 7.60 (d, J=2.2 Hz, 1H), 7.36 (d, J=8.8 Hz, 1H), 7.02 (d, J=2.5 Hz, 1H), 6.82 (dd, J=8.8, 2.8 Hz, 1H), 6.69-6.67 (m, 1H), 4.78 (s, 1H); LC-MS: Method A, 50 to 100% B. RT=2.32 min, MS (ESI) m/z: no (M+H)$^+$.

Intermediate 44B: (benzofuran-5-yloxy)(tert-butyl)dimethylsilane

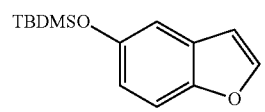

(44B)

To a stirred solution of Intermediate 44A (0.33 g, 2.460 mmol) in DMF (8.0 mL) was added TBDMS-Cl (0.519 g, 3.44 mmol) and imidazole (0.285 g, 4.18 mmol). The reaction mixture was left stirring at room temperature for 2.0 h. The mixture was partitioned between EtOAc/water. The organic layer was washed with brine, dried over sodium sulfate. After evaporation of solvent, the crude product was dissolved in a small amount of chloroform and charged to a 24 g silica gel cartridge which was eluted with hexanes for 3 min., then a 15 min gradient from 0% to 20% EtOAc in hexanes. The desired fractions were combined and concentrated to give Intermediate 44B (0.48 g, 1.932 mmol, 79% yield) as a clear oil. $^1$H NMR (500 MHz, chloroform-d) δ 7.60 (d, J=1.9 Hz, 1H), 7.36 (d, J=8.8 Hz, 1H), 7.04 (d, J=2.5 Hz, 1H), 6.83 (dd, J=8.7, 2.3 Hz, 1H), 6.70-6.69 (m, 1H), 1.03 (s, 9H), 0.23 (s, 6H); LC-MS: Method A, 50 to 100% B. RT=2.19 min, MS (ESI) m/z: 249 (M+H)$^+$.

Intermediate 44C: 5-(tert-butyldimethylsilyloxy)benzofuran-2-ylboronic acid

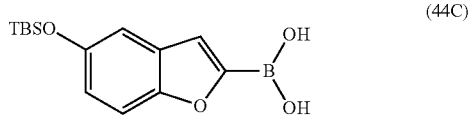 [SMILES: CC(C)(C)[Si](C)(C)Oc1ccc2oc(B(O)O)cc2c1]

To Intermediate 44B (0.48 g, 1.932 mmol) in THF (7.0 mL) at −78° C. was added 1.6 N n-BuLi in hexanes (1.993 mL, 3.19 mmol) dropwise. The solution turned to brown. The mixture was stirred at −78° C. for 10 min, followed by addition of triisopropyl borate (1.346 mL, 5.80 mmol). The mixture was stirred for 20 min, and the cooling bath was removed to allow warm up to room temperature over 0.5 h. It was diluted with EtOAc, quenched with 20 mL of 0.5 N HCl. After stirring at room temperature for 10 min, the organic layer was collected, washed with brine, dried over sodium sulfate. After evaporation of solvent, the crude product was dissolved in a small amount of chloroform and charged to a 12 g silica gel cartridge which was eluted with hexanes for 3 min., then a 12 min gradient from 0% to 60% EtOAc in hexanes. The desired fractions were combined, concentrated and lyophilized to give Intermediate 44C (0.416 g, 1.424 mmol, 73.7% yield) as a white solid. $^1$H NMR (500 MHz, methanol-d$_4$) δ 7.39 (d, J=8.8 Hz, 1H), 7.28 (s, 1H), 7.07 (d, J=2.5 Hz, 1H), 6.88 (dd, J=8.8, 2.5 Hz, 1H), 1.03 (s, 9H), 0.22 (s, 6H); LC-MS: Method A, 0 to 100% B. RT=2.30 min, MS (ESI) m/z: 293.1 (M+H)$^+$.

Intermediate 44D: 2-(2-(difluoromethoxy)-7-methylquinoxalin-5-yl)benzofuran-5-ol

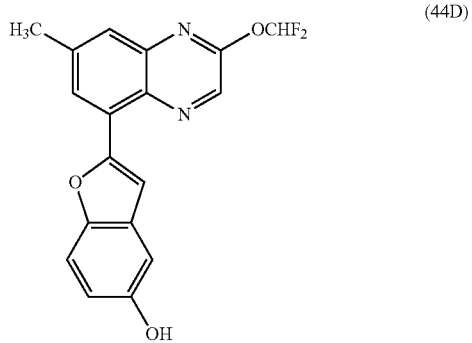 [SMILES: Cc1cc(-c2cc3cc(O)ccc3o2)c2ncc(OC(F)F)nc2c1]

A mixture of Intermediate I-1G (324 mg, 1.122 mmol), Intermediate 44C (410 mg, 1.403 mmol) and [1,1'-bis(diphenylphosphino)ferrocene]dichloropalladium (II) complex with dichloromethane (1:1) (36.7 mg, 0.045 mmol) in toluene (6 mL) and EtOH (2.000 mL) was degassed with argon for 2.0 min. To this solution was added sodium carbonate (2.0 M, 0.982 mL, 1.964 mmol). The mixture was then heated in an oil bath at 85° C. overnight. The crude reaction mixture was diluted with EtOAc/water. The organic layer was collected, dried over sodium sulfate. After evaporation of solvent, the crude product was obtained as brown oil that solidified when treated with MeOH. It was used for the next step without further purification.

To the crude product obtained above (0.55 g, 1.205 mmol) in MeOH (4.0 mL) and THF (4.00 mL) was added 12 N HCl (1.004 mL, 12.05 mmol). The mixture was stirred at room temperature for 30 min. TLC indicated ca 40% starting material remaining. Another portion of 12 N HCl (1.004 mL, 12.05 mmol) was added. The reaction was continued at room temperature for 1.5 h. TLC indicated a clean reaction. Methanol was removed under vacuum, the crude was diluted with EtOAc, washed with water and brine. The organic layer was collected, dried over sodium sulfate. After evaporation of solvent, the crude product was dissolved in a small amount of chloroform/THF and charged to a 12 g silica gel cartridge which was eluted with hexanes for 3 min., then a 10 min gradient from 0% to 60% EtOAc in hexanes. The desired fractions were combined and concentrated to give Intermediate 44D (0.423 g, 1.236 mmol, 103% yield) as a yellow solid. $^1$H NMR (500 MHz, DMSO-d$_6$) δ 9.26 (s, 1H), 8.90 (s, 1H), 8.21 (d, J=1.7 Hz, 1H), 7.99 (d, J=0.8 Hz, 1H), 7.89 (t, J$_{HF}$=71.53 Hz, 1H), 7.75 (dd, J=1.9, 1.1 Hz, 1H), 7.47 (d, J=8.8 Hz, 1H), 7.08 (d, J=2.5 Hz, 1H), 6.84 (dd, J=8.8, 2.5 Hz, 1H), 2.63 (s, 3H); $^{19}$F NMR (471 MHz, DMSO-d$_6$) δ −87.80 (s, 2F); LC-MS: Method A, 0 to 100% B. RT=2.30 min, MS (ESI) m/z: 343.0 (M+H)$^+$.

Example 44

To a solution of Intermediate 44D (20 mg, 0.058 mmol) in acetonitrile (1 mL) was added Cs$_2$CO$_3$ (57.1 mg, 0.175 mmol) and (bromomethyl)benzene (100 mg, 0.584 mmol). The mixture was stirred at 45° C. for 1 h. The mixture was diluted with 1 ml of DMSO and 1 ml of acetonitrile and filtered. The filtrate was purified with a preparative HPLC (method A, 65-100% B in 8 min.). The desired fractions were placed in a SpeedVac overnight to remove solvent, then lyophilized to give Example 44 (17 mg, 0.037 mmol, 63.9% yield). $^1$H NMR (400 MHz, chloroform-d) δ 8.63 (s, 1H), 8.22 (s, 1H), 8.01 (s, 1H), 7.66-7.34 (m, 8H), 7.20 (d, J=2.2 Hz, 1H), 7.07-7.02 (m, 1H), 5.14 (s, 2H), 2.64 (s, 3H). $^{19}$F NMR (chloroform-d, 400 MHz):) −90.12 (s, 2F). LC-MS: method C, RT=2.84 min, MS (ESI) m/z: 433.0 (M+H)$^+$. Analytical HPLC purity (method A): 100%.

Example 45

2-(difluoromethoxy)-5-(imidazo[1,2-a]pyridin-2-yl)-7-methylquinoxaline

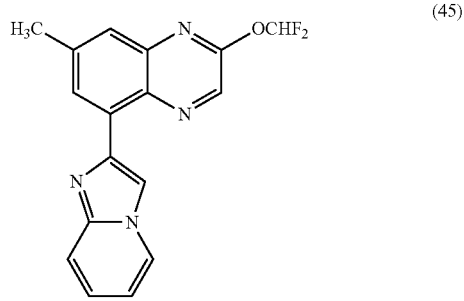 [SMILES: Cc1cc(-c2cn3ccccc3n2)c2ncc(OC(F)F)nc2c1]

(45)

To 2-bromoimidazo[1,2-a]pyridine (17.58 mg, 0.089 mmol) and Intermediate I-1 (20 mg, 0.059 mmol) was added toluene (0.75 mL) and EtOH (0.25 mL). The reaction mixture was stirred at room temperature until solids are dissolved, then [1,1'-bis(diphenylphosphino)ferrocene] dichloropalladium (II) complex with dichloromethane (1:1) (5.83 mg, 7.14 µmol) was added. The flask was degassed and flushed with argon. Finally sodium carbonate (0.059 mL, 2M, 0.119 mmol) was added dropwise. The reaction vessel was sealed and bubbled with argon for 5 min, then placed in microwave reactor at 120° C. for 30 min. The reaction mixture was cooled to room temperature and was diluted with EtOAc and water, extracted with EtOAc (3×). The combined organic layer was washed with brine, dried with MgSO$_4$ and concentrated. The crude sample was purified with a preparative HPLC (method A, 30-100% B in 10 min.). The desired fractions were placed in a SpeedVac overnight to remove solvent, then lyophilized to give Example 45 (6.5 mg, 0.019 mmol, 32.1% yield). $^1$H NMR (400 MHz, acetonitrile-d$_3$) δ 8.90 (br. s., 1H), 8.71 (br. s., 1H), 8.58 (d, J=6.8 Hz, 1H), 8.43 (s, 1H), 8.03 (br. s., 1H), 7.50 (s, 2H), 7.31 (t, J=6.8 Hz, 1H), 2.63 (s, 3H). $^{19}$F NMR (376 MHz, acetonitrile-d$_3$) δ −90.60 (br. s., 2F). LC-MS: method C, RT=1.66 min, MS (ESI) m/z: 327.0 (M+H)$^+$. Analytical HPLC purity (method A): 99%.

Example 46

Methyl 2-(2-(2-(difluoromethoxy)-7-methylquinoxalin-5-yl)benzofuran-5-yloxy)ethylcarbamate

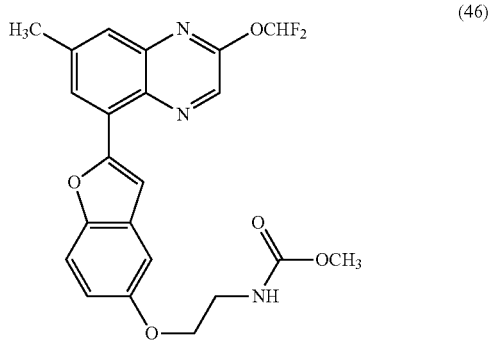 [SMILES: COC(=O)NCCOc1ccc2oc(-c3cc(C)cc4nc(OC(F)F)cnc34)cc2c1]

(46)

Intermediate 46A: tert-butyl 2-(2-(2-(difluoromethoxy)-7-methylquinoxalin-5-yl)benzofuran-5-yloxy)ethylcarbamate

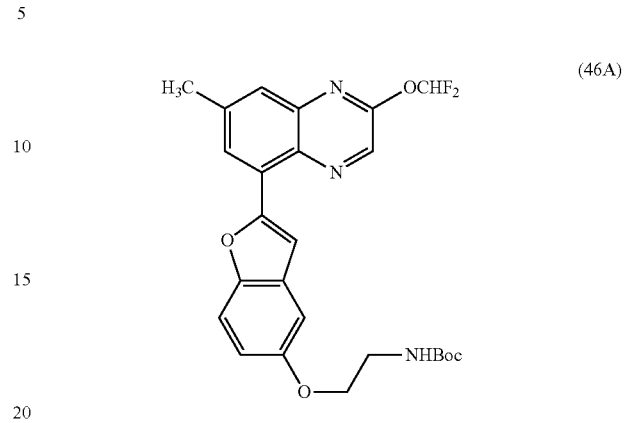

(46A)

To a solution of triphenylphosphine (53.6 mg, 0.205 mmol) in THF (1.0 mL) at 0° C., was added DIAD (0.040 mL, 0.205 mmol) dropwise. The mixture was stirred at 0° C. for 10 min. A solution of Intermediate 44D (35 mg, 0.102 mmol) and tert-butyl (2-hydroxyethyl)carbamate (33.0 mg, 0.205 mmol) in THF (1.0 mL) was added dropwise. The mixture was stirred at 0° C. to room temperature for 30 min, then heated up to 55° C. overnight. After evaporation of solvent, the crude was dissolved in DMSO/acetonitrile (1.5 mL/1.5 mL) and purified using a preparative HPLC (method A, 30-100% B in 10 min.). The desired fractions were placed in a SpeedVac overnight to remove solvent, then lyophilized to give Intermediate 46A (18 mg, 0.037 mmol, 36.3% yield) as a yellow lyophilate. $^1$H NMR (chloroform-d, 400 MHz): δ=8.65 (s, 1H), 8.25 (s, 1H), 8.04 (s, 1H), 7.40-7.91 (m, 3H), 7.13 (d, J=2.5 Hz, 1H), 6.90-7.03 (m, 1H), 5.05 (br. s., 1H), 4.02-4.20 (m, 2H), 3.59 (br. s., 2H), 2.66 (s, 3H), 1.48 ppm (s, 9H). $^{19}$F NMR (chloroform-d, 376 MHz): δ=−90.15 ppm (s, 2F). LC-MS: method B, RT=2.58 min, MS (ESI) m/z: 486.1 (M+H)$^+$.

Intermediate 46B 2-(2-(2-(difluoromethoxy)-7-methylquinoxalin-5-yl)benzofuran-5-yloxy)ethanamine

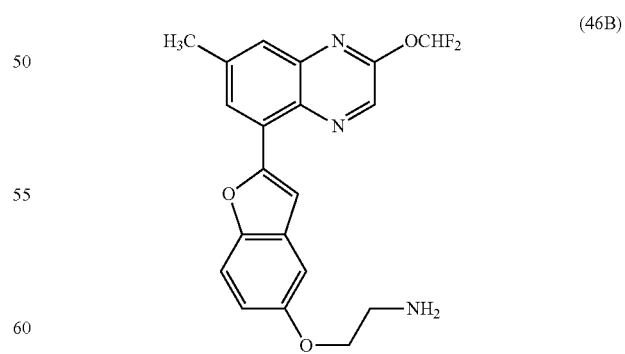

(46B)

To a solution of Intermediate 46A (13 mg, 0.027 mmol) in DCM (2 mL) was added TFA (0.206 mL, 2.68 mmol) and the mixture was stirred at room temperature overnight. Solvent was removed. The residual was purified with a preparative HPLC (method A, 30-100% B in 10 min.). The desired fractions were placed in a SpeedVac overnight to remove solvent, then lyophilized to give Intermediate 46B (8 mg, 0.020 mmol, 75% yield). $^1$H NMR (acetonitrile-d$_3$, 400 MHz): δ=8.71 (s, 1H), 8.25 (s, 1H), 8.06 (s, 1H), 7.49-7.89 (m, 3H), 7.27 (d, J=2.5 Hz, 1H), 7.03 (dd, J=8.8, 2.5 Hz, 1H), 4.27 (t, J=4.8 Hz, 2H), 3.40 (t, J=4.9 Hz, 2H), 2.65 ppm (s, 3H). $^{19}$F NMR (acetonitrile-d$_3$, 376 MHz): δ=−76.15 (br. s., 3F), −90.48 ppm (s, 2F). LC-MS: method C, RT=2.02 min, MS (ESI) m/z: 386.0 (M+H)$^+$. Analytical HPLC purity (method A): 98%.

Example 46

To a suspension of Intermediate 46B (6.5 mg, 0.013 mmol) in DCM (1 mL) was added Et$_3$N (9.07 μL, 0.065 mmol) followed by methyl chloroformate (2.016 μL, 0.026 mmol). The mixture was stirred at room temperature for 1 h. Solvent was removed and the residual was purified with a preparative HPLC (method A, 50-100% B in 8 min.). The desired fractions were placed in a SpeedVac overnight to remove solvent, then lyophilized to give Example 46 (4.0 mg, 8.75 μmol, 67.2% yield). $^1$H NMR (acetonitrile-d$_3$, 400 MHz): δ=8.71 (s, 1H), 8.25 (d, J=1.8 Hz, 1H), 8.04 (s, 1H), 7.44-7.91 (m, 3H), 7.23 (d, J=2.5 Hz, 1H), 6.98 (dd, J=8.8, 2.5 Hz, 1H), 4.08 (t, J=5.6 Hz, 2H), 3.61 (s, 3H), 3.50 (q, J=5.7 Hz, 2H), 2.64 ppm (s, 3H). $^{19}$F NMR (acetonitrile-d$_3$, 376 MHz): δ=−90.47 ppm (s, 2F). LC-MS: method C, RT=2.42 min, MS (ESI) m/z: 444.1 (M+H)$^+$. Analytical HPLC purity (method A): 98%.

Example 47

5-(1H-benzo[d]imidazol-2-yl)-2-(difluoromethoxy)-7-methylquinoxaline

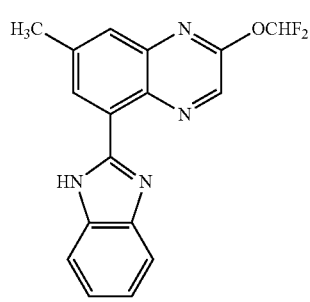

(47)

To 2-chloro-1H-benzo[d]imidazole (10.89 mg, 0.071 mmol) and Intermediate I-1 (20 mg, 0.059 mmol) was added toluene (0.75 mL) and EtOH (0.25 mL). The mixture was stirred at room temperature until solids are dissolved, then [1,1'-bis(diphenylphosphino)ferrocene] dichloropalladium (II) complex with dichloromethane (1:1) (5.83 mg, 7.14 μmol) was added. The flask was degassed and flushed with argon. Finally sodium carbonate (0.045 mL, 2M, 0.089 mmol) was added dropwise. The reaction vessel was sealed and bubbled with argon for 5 min, then placed in microwave reactor at 120° C. for 30 min, then at 140° C. for 20 min. The reaction mixture was cooled to room temperature and was diluted with EtOAc and water, extracted with EtOAc (3×). The combined organic layer was washed with brine, dried with MgSO$_4$ and concentrated. The crude sample was purified with a preparative HPLC (method A, 20-100% B in 8 min.). The desired fractions were placed in a SpeedVac overnight to remove solvent, then lyophilized to give Example 47 (10 mg, 0.030 mmol, 50.5% yield). $^1$H NMR (acetonitrile-d$_3$, 400 MHz): δ=8.85 (d, J=1.5 Hz, 1H), 8.79 (br. s., 1H), 7.46-7.93 (m, 6H), 2.66 ppm (s, 3H). $^{19}$F NMR (376 MHz, acetonitrile-d$_3$) δ −90.69 (s, 2F). LC-MS: method C, RT=1.71 min, MS (ESI) m/z: 327.1 (M+H)$^+$. Analytical HPLC purity (method A): 98%.

Example 48

2-(2-(difluoromethoxy)-7-methylquinoxalin-5-yl)-6-methoxybenzo[d]thiazole

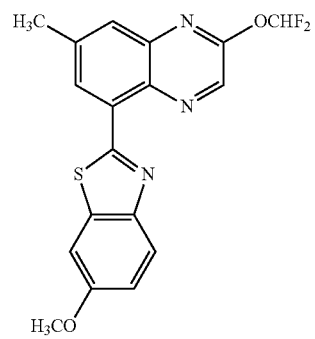

(48)

To 2-chloro-6-methoxybenzo[d]thiazole (14.26 mg, 0.071 mmol) and Intermediate I-1 (20 mg, 0.059 mmol) was added toluene (0.75 mL) and EtOH (0.25 mL). The mixture was stirred at room temperature until solids are dissolved, then [1,1'-bis(diphenylphosphino)ferrocene]dichloropalladium (II) complex with dichloromethane (1:1) (5.83 mg, 7.14 μmol) was added. The flask was degassed and flushed with argon. Finally sodium carbonate (0.045 mL, 2M, 0.089 mmol) was added dropwise. The reaction vessel was sealed and bubbled with argon for 5 min, then placed in microwave reactor at 120° C. for 30 min. The reaction mixture was cooled to room temperature and was diluted with EtOAc and water, extracted with EtOAc (3×). The combined organic layer was washed with brine, dried with MgSO$_4$ and concentrated. The crude sample was purified with a preparative HPLC (method A, 65-100% B in 8 min.). The desired fractions were placed in a SpeedVac overnight to remove solvent, then lyophilized to give Example 48 (12.5 mg, 0.033 mmol, 55.1% yield). $^1$H NMR (acetonitrile-d$_3$, 400 MHz): δ=8.70-8.83 (m, 2H), 7.95-8.04 (m, 1H), 7.48-7.90 (m, 3H), 7.12-7.21 (m, 1H), 3.90 (s, 3H), 2.69 ppm (s, 3H). $^{19}$F NMR (acetonitrile-d$_3$, 400 MHz):) −90.12 (s, 2F). LC-MS: method C, RT=2.50 min, MS (ESI) m/z: 374.0 (M+H)$^+$. Analytical HPLC purity (method A): 98%.

Example 49 tert-butyl 2-(2-(2-(difluoromethoxy)-7-methylquinoxalin-5-yl)benzofuran-5-yloxy) acetate

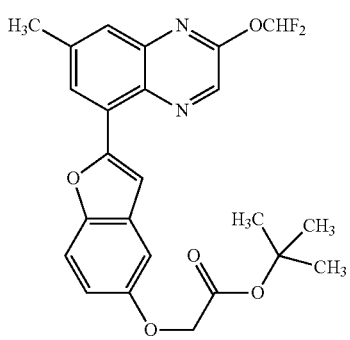

(49)

To a solution of Intermediate 44D (20 mg, 0.058 mmol) in DMF (1 mL) was added Cs$_2$CO$_3$ (57.1 mg, 0.175 mmol) and tert-butyl 2-bromoacetate (57.0 mg, 0.292 mmol). The mixture was stirred at 100° C. for 2 h. The mixture was diluted with 1 ml of DMSO and 1 ml of acetonitrile, filtered. The filtrate was purified with a preparative HPLC (method A, 65-100% B in 6 min.). The desired fractions were placed in a SpeedVac overnight to remove solvent, then lyophilized to give Example 49 (20 mg, 0.043 mmol, 73.5% yield). $^1$H NMR (chloroform-d, 400 MHz): δ=8.64 (s, 1H), 8.23 (d, J=1.5 Hz, 1H), 8.02 (s, 1H), 7.42-7.86 (m, 3H), 7.12 (d, J=2.5 Hz, 1H), 7.01 (dd, 2.5 Hz, 1H), 4.59 (s, 2H), 2.65 (s, 3H), 1.50-1.56 ppm (m, 9H). $^{19}$F NMR (chloroform-d, 376 MHz): δ=−90.15 ppm (s, 2F). LC-MS: method C, RT=2.61 min, MS (ESI) m/z: 457.1 (M+H)$^+$. Analytical HPLC purity (method A): 100%.

Example 50

2-(difluoromethoxy)-5-(5-methoxy-1H-benzo[d]imidazol-2-yl)-7-methylquinoxaline

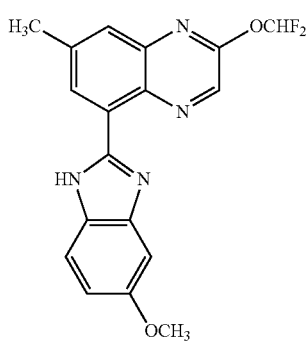

(50)

To 2-chloro-5-methoxy-1H-benzo[d]imidazole (13.04 mg, 0.071 mmol) and Intermediate I-1 (20 mg, 0.059 mmol) was added toluene (0.75 mL) and EtOH (0.25 mL). The reaction mixture was stirred at room temperature until solids are dissolved, then [1,1'-Bis(diphenylphosphino)ferrocene] dichloropalladium (II) complex with dichloromethane (1:1) (5.83 mg, 7.14 μmol) was added. The flask was degassed and flushed with argon. Finally sodium carbonate (0.059 mL, 2M, 0.119 mmol) was added dropwise. The reaction vessel was sealed and bubbled with argon for 5 min, then placed in microwave reactor at 140° C. for 30 min. The reaction mixture was cooled to room temperature and was diluted with EtOAc and water, extracted with EtOAc (3×). The combined organic layer was washed with brine, dried with MgSO$_4$ and concentrated. The crude sample was purified with a preparative HPLC (method A, 30-100% B in 8 min.). The desired fractions were placed in a SpeedVac overnight to remove solvent, then lyophilized to give Example 50 (6 mg, 0.016 mmol, 27.5% yield). $^1$H NMR (acetonitrile-d$_3$, 400 MHz): δ=8.77 (br. s., 2H), 7.70 (s, 3H), 7.27-7.39 (m, 1H), 7.05-7.18 (m, 1H), 3.90 (s, 3H), 2.65 ppm (s, 3H). $^{19}$F NMR (acetonitrile-d$_3$, 376 MHz): δ=−76.64 (br. s., 3F), −90.69 ppm (s, 2F). LC-MS: method C, RT=1.78 min, MS (ESI) m/z: 357.0 (M+H)$^+$. Analytical HPLC purity (method A): 98%

Example 51

2-(2-(difluoromethoxy)-7-methylquinoxalin-5-yl)-4-methoxybenzo[d]thiazole

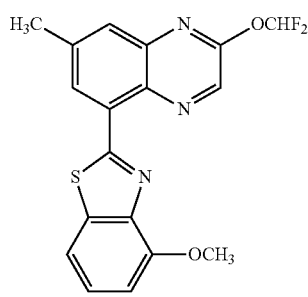

(51)

Intermediate 51A: 2-bromo-4-methoxybenzo[d]thiazole

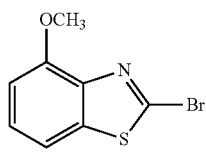

(51A)

To a suspension of 4-methoxybenzo[d]thiazol-2-amine (2.5 g, 13.87 mmol) and p-TSA monohydrate (7.92 g, 41.6 mmol) in acetonitrile (80 mL) at 10° C. (cooled with ice water) was added dropwise a solution of sodium nitrite (1.914 g, 27.7 mmol) and potassium bromide (4.13 g, 34.7 mmol) in water (5 ml) over a period of 25 min. The reaction mixture was stirred at 10° C. for 10 min, and allowed to warm up to room temperature and stirred for 2.0 h. HPLC indicated a completion of reaction. To the reaction mixture was added sodium bicarbonate (pH to 9.0), water and EtOAc. The organic layer was collected, washed with water, saturated Na$_2$S$_2$O$_3$, water, brine, dried over sodium sulfate. After evaporation of solvent, the crude product was dissolved in a small amount of chloroform and charged to a 120 g silica gel cartridge which was eluted with hexanes for 4 min., then an 18 min gradient from 0% to 40% EtOAc in hexanes. The desired fractions were combined and concentrated to give Intermediate 51A (2.51 g, 10.28 mmol, 74.1% yield) as a slightly yellow solid. $^1$H NMR (500 MHz, chloroform-d) δ 7.40-7.37 (m, 2H), 6.92 (dd, 2.5 Hz, 1H), 4.06 (s, 3H); LC-MS: method A, RT=1.79 min, MS (ESI) m/z: 244.0 and 246.0 (M+H)$^+$.

Example 51

To Intermediate 51A (10 mg, 0.041 mmol) and Intermediate I-1 (20.66 mg, 0.061 mmol) was added toluene (0.75 mL) and EtOH (0.25 mL). The mixture was stirred at room temperature until solids are dissolved, then [1,1'-bis(diphenylphosphino)ferrocene] dichloropalladium (II) complex with dichloromethane (1:1) (4.01 mg, 4.92 μmol) was added. The flask was degassed and flushed with argon. Finally sodium carbonate (0.031 mL, 2M, 0.061 mmol) was added dropwise. The reaction vessel was sealed and bubbled with argon for 5 min, then placed in microwave reactor at 120° C. for 30 min. LCMS indicated a completion of the reaction. The reaction mixture was cooled to room temperature and was diluted with EtOAc and water, extracted with EtOAc (3×). The combined organic layer was washed with brine, dried with MgSO$_4$ and concentrated. The crude sample was purified with a preparative HPLC (method A, 50-100% B in 8 min.). The desired fractions were placed in a SpeedVac overnight to remove solvent, then lyophilized to give Example 51 (2.5 mg, 6.43 μmol, 15.69% yield). $^1$H NMR (400 MHz, chloroform-d) δ 8.93 (d, J=1.65 Hz, 1H), 8.71 (s, 1H), 7.80 (s, 1H), 7.58 (d, J=8.25 Hz, 1H), 7.47-7.86 (m, 1H), 7.39 (t, J=7.97 Hz, 1H), 6.96 (d, J=7.70 Hz, 1H), 4.13 (s, 3H), 2.68 (s, 3H). $^{19}$F NMR (376 MHz, chloroform-d) δ −89.62 (s, 2F). LC-MS: method C, RT=2.45 min, MS (ESI) m/z: 374.0 (M+H)$^+$. Analytical HPLC purity (method A): 97%.

Example 52

2-(2-(difluoromethoxy)-7-methylquinoxalin-5-yl)-4-methylbenzo[d]thiazole

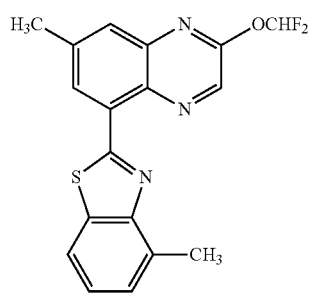

(52)

Intermediate 52A:
2-bromo-4-methylbenzo[d]thiazole

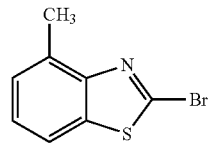

(52A)

To a white suspension of 4-methylbenzo[d]thiazol-2-amine (0.5 g, 3.04 mmol) and p-TSA monohydrate (1.737 g, 9.13 mmol) in acetonitrile (20 mL) at 10° C. (cooled with ice water) was added dropwise a solution of sodium nitrite (0.420 g, 6.09 mmol) and potassium bromide (0.906 g, 7.61 mmol) in water (5 mL) over a period of 25 min. The reaction mixture was stirred at 10° C. for 10 min, and allowed to warm up to room temperature and stirred for 1.0 h. To the reaction mixture was added sodium bicarbonate (pH to 9.0), water and EtOAc. The organic layer was collected, washed with water, saturated Na$_2$S$_2$O$_3$, water, brine, dried over sodium sulfate. After evaporation of solvent, the crude product was dissolved in a small amount of chloroform and charged to a 40 g ISCO column which was eluted with hexanes for 2 min., then a 20 min gradient from 0% to 40% EtOAc in hexanes. The desired fractions were combined and concentrated to give Intermediate 52A (640 mg, 2.81 mmol, 92% yield) as a yellow solid. $^1$H NMR (400 MHz, chloroform-d) δ 7.62 (td, J=0.69, 7.71 Hz, 1H), 7.21-7.34 (m, 3H), 2.71 (s, 3H). LC-MS: method C, RT=2.11 min, MS (ESI) m/z: 227.0 and 229.0 (M+H)$^+$.

Example 52

To Intermediate 52A (17 mg, 0.074 mmol) and Intermediate I-1 (30 mg, 0.089 mmol) was added toluene (0.75 mL) and EtOH (0.25 mL). The mixture was stirred at room temperature until solids are dissolved, then [1,1'-bis(diphenylphosphino)ferrocene] dichloropalladium (II) complex with dichloromethane (1:1) (7.29 mg, 8.92 μmol) was added. The flask was degassed and flushed with argon. Finally sodium carbonate (0.056 mL, 2M, 0.112 mmol) was added dropwise. The reaction vessel was sealed and bubbled with argon for 5 min, then placed in microwave reactor at 120° C. for 30 min. The reaction mixture was cooled to room temperature and was diluted with EtOAc and water, extracted with EtOAc (3×). The combined organic layer was washed with brine, dried with MgSO$_4$ and concentrated. The crude sample was purified with a preparative HPLC (method A, 65-100% B in 8 min.). The desired fractions were placed in a SpeedVac overnight to remove solvent, then lyophilized to give Example 52 (11.5 mg, 0.031 mmol, 41.5% yield). $^1$H NMR (400 MHz, chloroform-d) δ 8.86 (d, J=1.52 Hz, 1H), 8.71 (s, 1H), 7.47-7.90 (m, 3H), 7.30-7.36 (m, 2H), 2.90 (s, 3H), 2.72 (s, 3H). $^{19}$F NMR (400 MHz, chloroform-d) δ −90.12 (s, 2F). LC-MS: method C, RT=2.68 min, MS (ESI) m/z: 358.0 (M+H)$^+$. Analytical HPLC purity (method A): 98%.

Example 53

2-(2-(difluoromethoxy)-7-methylquinoxalin-5-yl)-4-fluorobenzo[d]thiazole

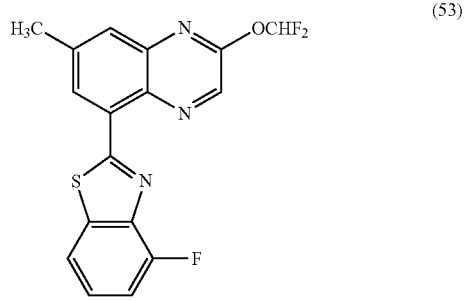 [SMILES: Cc1cc(-c2nc3c(F)cccc3s2)c2ncc(OC(F)F)nc2c1]

(53)

Intermediate 53A:
2-bromo-4-fluorobenzo[d]thiazole

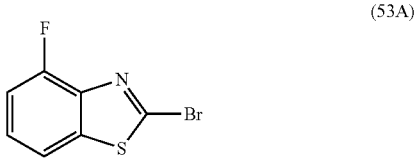 [SMILES: Fc1cccc2sc(Br)nc12]

(53A)

To a suspension of 4-fluorobenzo[d]thiazol-2-amine (0.52 g, 3.09 mmol) and p-TSA monohydrate (1.764 g, 9.28 mmol) in acetonitrile (20 mL) at 10° C. (cooled with ice water) was added dropwise a solution of sodium nitrite (0.427 g, 6.18 mmol) and potassium bromide (0.920 g, 7.73 mmol) in water (5 mL) over a period of 25 min. The reaction mixture was stirred at 10° C. for 10 min, and allowed to warm up to room temperature and stirred for 1.0 h. To the reaction mixture was added sodium bicarbonate (pH to 9.0), water and EtOAc. The organic layer was collected, washed with water, saturated $Na_2S_2O_3$, water, brine, dried over sodium sulfate. After evaporation of solvent, the crude product was dissolved in a small amount of chloroform and charged to a 40 g ISCO column which was eluted with hexanes for 2 min., then a 20 min gradient from 0% to 40% EtOAc in hexanes. The desired fractions were combined and concentrated to give Intermediate 53A (640 mg, 2.76 mmol, 89% yield) as a yellow solid. $^1$H NMR (400 MHz, chloroform-d) δ 7.59 (dd, J=0.76, 8.08 Hz, 1H), 7.40 (dt, J=4.55, 8.08 Hz, 1H), 7.20 (ddd, J=1.01, 8.08, 10.11 Hz, 1H). LC-MS: method C, RT=1.84 min, MS (ESI) m/z: 231.9 and 233.9 (M+H)$^+$.

Example 53

To Intermediate 53A (17.26 mg, 0.074 mmol) and Intermediate I-1 (30 mg, 0.089 mmol) was added toluene (0.75 mL) and EtOH (0.25 mL). The mixture was stirred at room temperature until solids are dissolved, then [1,1'-bis(diphenylphosphino)ferrocene] dichloropalladium (II) complex with dichloromethane (1:1) (7.29 mg, 8.92 μmol) was added. The flask was degassed and flushed with argon. Finally sodium carbonate (0.056 mL, 2M, 0.112 mmol) was added dropwise. The reaction vessel was sealed and bubbled with argon for 5 min, then placed in microwave reactor at 120° C. for 30 min. The reaction mixture was cooled to room temperature and was diluted with EtOAc and water, extracted with EtOAc (3×). The combined organic layer was washed with brine, dried with $MgSO_4$ and concentrated. The crude sample was purified with a preparative HPLC (method A, 50-100% B in 6 min.). The desired fractions were placed in a SpeedVac overnight to remove solvent, then lyophilized to give Example 53 (15.0 mg, 0.039 mmol, 53.0% yield). $^1$H NMR (400 MHz, chloroform-d) δ 8.92 (d, J=1.77 Hz, 1H), 8.71 (s, 1H), 7.84 (dd, J=0.88, 1.89 Hz, 1H), 7.76 (dd, J=0.88, 7.96 Hz, 1H), 7.48-7.87 (m, 1H), 7.39 (dt, J=4.67, 8.02 Hz, 1H), 7.23 (ddd, J=1.01, 7.96, 10.48 Hz, 1H), 2.71 (s, 3H). $^{19}$F NMR (400 MHz, chloroform-d) −90.12 (s, 2F). LC-MS: method C, RT=2.53 min, MS (ESI) m/z: 362.0 (M+H)$^+$. Analytical HPLC purity (method A): 96%.

Example 54

2-(2-(2-(difluoromethoxy)-7-methylquinoxalin-5-yl)benzofuran-5-yloxy)-N-methylethanamine

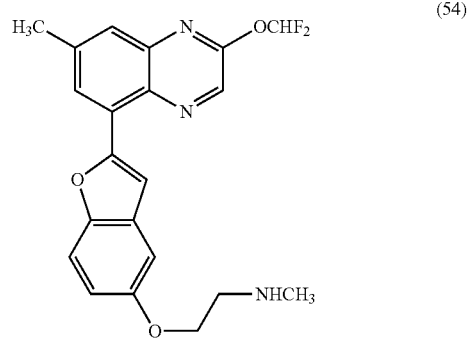

(54)

Intermediate 54A: tert-butyl 2-(2-(2-(difluoromethoxy)-7-methylquinoxalin-5-yl)benzofuran-5-yloxy)ethyl(methyl)carbamate

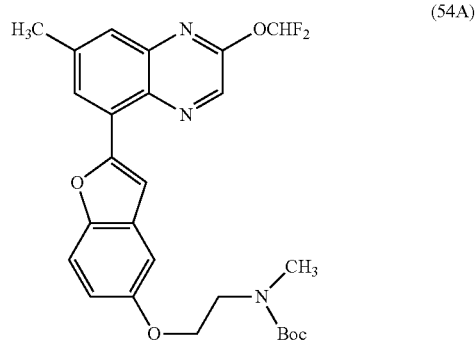

(54A)

A solution of tert-butyl (2-hydroxyethyl)(methyl)carbamate (41.0 mg, 0.234 mmol) and DIAD (0.057 mL, 0.292 mmol) in THF (1.0 mL) was added to a mixture of Intermediate 44D (20 mg, 0.058 mmol) and triphenylphosphine (30.7 mg, 0.117 mmol) in THF (2 mL) at 80° C. using a syringe pump over 4 h. The mixture was stirred at 80° C. for 1 h. Solvent was removed, the residual was dissolved in 1 ml of DMF. The crude material was purified via preparative LC/MS (method D, 65-85% B over 10 min., then an 8-min hold at 100% B). Fractions containing the desired product were combined and dried via centrifugal evaporation to give Intermediate 54A (14.8 mg, 0.028 mmol, 47.2% yield). $^1$H NMR (500 MHz, methanol-d$_4$) δ 8.61 (s, 1H), 8.18 (d, J=1.38 Hz, 1H), 7.97 (s, 1H), 7.62 (s, 1H), 7.49-7.83 (m, 1H), 7.42 (d, J=8.80 Hz, 1H), 7.11 (d, J=2.48 Hz, 1H), 6.92 (dd, J=2.48, 8.80 Hz, 1H), 4.15 (t, J=5.50 Hz, 2H), 3.63 (t, J=5.23 Hz, 2H), 2.99 (s, 3H), 2.61 (s, 3H), 1.45 (s, 9H). LC-MS: method C, RT=2.69 min, MS (ESI) m/z: 500.2 (M+H)$^+$.

Example 54

To a solution of Intermediate 54A (9 mg, 0.018 mmol) in DCM (1 mL) was added TFA (1 ml). The mixture was stirred at room temperature for 1 h. Solvent was removed and the crude sample was purified with preparative HPLC (method A, 30-100% B in 6 min.). The desired fractions were placed in a SpeedVac overnight to remove solvent, then lyophilized to give Example 54 (7 mg, 0.013 mmol, 74.9% yield). $^1$H NMR (400 MHz, methanol-d$_4$) δ 8.68 (s, 1H), 8.23 (d, J=1.77 Hz, 1H), 8.06 (s, 1H), 7.70 (s, 1H), 7.56-7.97 (m, 1H), 7.52 (d, J=8.84 Hz, 1H), 7.29 (d, J=2.53 Hz, 1H), 7.07 (dd, J=2.65, 8.97 Hz, 1H), 4.28-4.38 (m, 2H), 3.45-3.58 (m, 2H), 2.83 (s, 3H), 2.64 (s, 3H). $^{19}$F NMR (376 MHz, methanol-d$_3$) δ −76.92 (br. s., 3F), −95.23-88.19 (m, 2F). LC-MS: method C, RT=2.02 min, MS (ESI) m/z: 400.0 (M+H)$^+$. Analytical HPLC purity (method A): 99%

Example 55

2-(2-(difluoromethoxy)-7-methylquinoxalin-5-yl)-4,6-dimethoxybenzo[d]thiazole

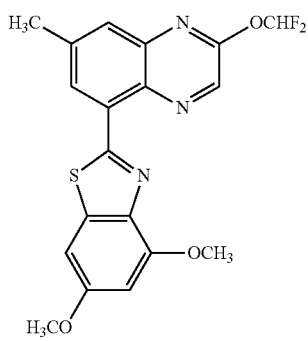

(55)

Intermediate 55A: 2,7-dibromo-4,6-dimethoxybenzo[d]thiazole

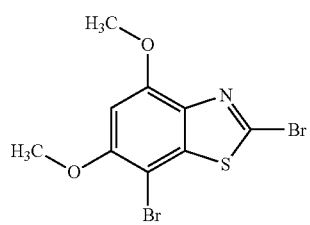

(55A)

To a mixture of 4,6-dimethoxybenzo[d]thiazol-2-amine (0.5 g, 2.378 mmol) and p-TSA monohydrate (1.357 g, 7.13 mmol) in acetonitrile (20 mL) at 10° C. (cooled with ice water) was added dropwise a solution of sodium nitrite (0.328 g, 4.76 mmol) and potassium bromide (0.707 g, 5.95 mmol) in water (5 mL) over a period of 25 min. The reaction mixture was stirred at 10° C. for 10 min, and allowed to warm up to room temperature and stirred for 1.0 h. The mixture was turned to a clear brown solution. To the reaction mixture was added sodium bicarbonate (pH to 9.0), water and EtOAc. The organic layer was collected, washed with water, saturated Na$_2$S$_2$O$_3$, water, brine, dried over sodium sulfate. After evaporation of solvent, the crude product was dissolved in a small amount of chloroform and charged to a 40 g ISCO column which was eluted with hexanes for 2 min., then a 20 min gradient from 0% to 40% EtOAc in hexanes. The desired fraction was collected and concentrated to Intermediate 55A (110 mg, 13% yield). $^1$H NMR (400 MHz, chloroform-d) δ 6.60 (s, 1H), 4.06 (s, 3H), 3.98 (s, 3H). LC-MS: method C, RT=2.18 min, MS (ESI) m/z: 351 353 and 355 (M+H)$^+$.

Intermediate 55B 7-bromo-2-(2-(difluoromethoxy)-7-methylquinoxalin-5-yl)-4,6-dimethoxybenzo[d]thiazole

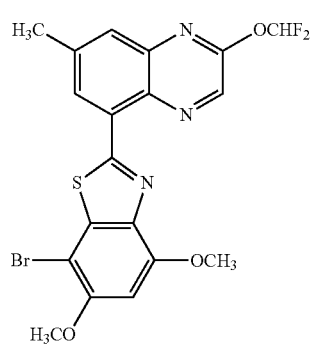

(55B)

To Intermediate 55A (26 mg, 0.074 mmol) and Intermediate I-1 (30 mg, 0.088 mmol) was added toluene (0.75 mL) and EtOH (0.25 mL). The mixture was stirred at room temperature until solids are dissolved, then [1,1'-bis(diphenylphosphino) ferrocene] dichloropalladium (II) complex with dichloromethane (1:1) (4.81 mg, 5.89 µmol) was added. The flask was degassed and flushed with argon. Finally sodium carbonate (0.055 mL, 2M, 0.110 mmol) was added dropwise. The reaction vessel was sealed and bubbled with argon for 5 min, then placed in microwave reactor at 100° C. for 2 h. The reaction mixture was cooled to room temperature and was diluted with EtOAc and water, extracted with EtOAc (3x). The combined organic layer was washed with brine, dried with MgSO$_4$ and concentrated. The crude sample was purified with a preparative HPLC (method A, 70-100% B in 6 min.). The desired fractions were placed in a SpeedVac overnight to remove solvent, then lyophilized to give Intermediate 55B (8 mg, 0.016 mmol, 22.07% yield). $^1$H NMR (400 MHz, chloroform-d) δ 8.85 (d, J=1.77 Hz, 1H), 8.73 (s, 1H), 7.79 (dd, J=0.88, 1.90 Hz, 1H), 7.47-7.89 (m, 1H), 6.68 (s, 1H), 4.15 (s, 3H), 4.04 (s, 3H), 2.67 (s, 3H).

$^{19}$F NMR (400 MHz, chloroform-d) −90.12 (s, 2F). LC-MS: method C, RT=2.56 min, MS (ESI) m/z: 481.9 and 484.0 (M+H)$^+$.

Example 55

To a solution of Intermediate 55B (6 mg, 0.012 mmol) in ethyl acetate (5 ml) was added Pd/C (5 mg) and TEA (10.40 μl, 0.075 mmol) and the mixture was stirred under a hydrogen balloon at 50° C. for 2 h. The reaction mixture was cooled to room temperature and filtered. The filtrate was concentrated. The crude material was purified via preparative LC/MS (method D, 45-90% B over 10 min., then a 10-min hold at 100% B). Fractions containing the desired product were combined and dried via centrifugal evaporation to Example 55 (0.2 mg, 0.496 μmol, 3.99% yield). $^1$H NMR (500 MHz, methanol-d$_4$) δ 8.76 (d, J=1.65 Hz, 1H), 8.67 (s, 1H), 7.77 (d, J=0.83 Hz, 1H), 7.48-7.85 (m, 1H), 7.03 (s, 1H), 6.59 (d, J=2.20 Hz, 1H), 4.05 (s, 3H), 3.89 (s, 3H). LC-MS: method C, RT=2.46 min, MS (ESI) m/z: 404 (M+H)$^+$. Analytical HPLC purity (method A): 100%.

Example 56

2-methoxy-5-(5-methoxybenzofuran-2-yl)-7-methylquinoxaline

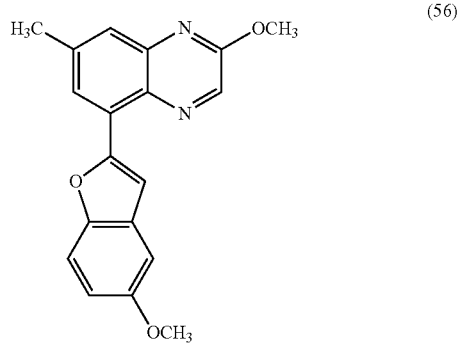 [SMILES: COc1ccc2oc(-c3cc(C)cc4nc(OC)cnc34)cc2c1]

Intermediate 56A:
5-methoxybenzofuran-2-ylboronic acid

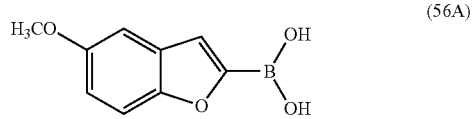 [SMILES: COc1ccc2oc(B(O)O)cc2c1]

To 5-methoxybenzofuran (188 mg, 1.269 mmol) in THF (4.0 mL) at −78° C. was added 1.6 N n-BuLi in hexanes (1.190 mL, 1.903 mmol) dropwise. The solution turned to slightly yellow. The mixture was stirred at −78° C. for 20 min, followed by addition of triisopropyl borate (0.737 mL, 3.17 mmol). The mixture was stirred for 30 min, and the cooling bath was removed to allow warm up to room temperature over 1.5 h. It was diluted with EtOAc, quenched with 3.0 mL of 1.0 N HCl. After stirring at room temperature for 25 min, the organic layer was collected, washed with brine, dried over sodium sulfate. After evaporation of solvent, the crude product was dissolved in a small amount of chloroform with a drop of MeOH, and charged to a 4 g silica gel cartridge which was eluted with hexanes for 2 min., then a 10 min gradient from 0% to 60% EtOAc in hexanes. The desired fractions were combined, concentrated and lyophilized to give Intermediate 56A (170 mg, 0.886 mmol, 69.8% yield) as a white solid. $^1$H NMR (500 MHz, methanol-d$_4$) δ 7.41 (d, J=9.1 Hz, 1H), 7.30 (s, 1H), 7.14 (d, J=2.5 Hz, 1H), 6.96 (dd, J=8.9, 2.6 Hz, 1H), 3.84 (s, 3H); LC-MS: method A, RT=1.45 min, MS (ESI) m/z: 149.0 (M-B(OH)$_2$)$^+$.

Example 56

To Intermediate I-9A (20 mg, 0.079 mmol) and Intermediate 56A (20.48 mg, 0.107 mmol) was added toluene (0.75 mL) and EtOH (0.250 mL). The reaction mixture was stirred at room temperature until solids are dissolved, then [1,1'-bis(diphenylphosphino)ferrocene] dichloropalladium(II) complex with dichloromethane (1:1) (5.16 mg, 6.32 μmol) was added. The flask was degassed and flushed with argon. Finally sodium carbonate (0.079 mL, 2M, 0.158 mmol) was added dropwise. The reaction vessel was sealed and bubbled with argon for 5 min, then placed in microwave reactor at 120° C. for 30 min. The reaction mixture was cooled to room temperature and was diluted with EtOAc and water, extracted with EtOAc (3×). The combined organic layer was washed with brine, dried with MgSO$_4$ and concentrated. The crude material was purified via preparative LC/MS (method D, 55-90% B over 10 min., then a 10-min hold at 100% B). Fractions containing the desired product were combined and dried via centrifugal evaporation to yield Example 56 (13.7 mg, 0.043 mmol, 54.1% yield). $^1$H NMR (500 MHz, methanol-d$_4$) δ 8.47 (s, 1H), 8.06 (d, J=1.93 Hz, 1H), 7.94 (d, J=0.83 Hz, 1H), 7.56-7.65 (m, 2H), 7.41 (d, J=9.08 Hz, 1H), 7.11 (d, J=2.48 Hz, 1H), 6.90 (dd, J=2.48, 8.80 Hz, 1H), 4.09 (s, 3H), 3.85 (s, 3H), 2.59 (s, 3H). LC-MS: method C, RT=2.63 min, MS (ESI) m/z: 321 (M+H)$^+$. Analytical HPLC purity (method B): 100%.

Example 58

2-(2-(difluoromethoxy)-7-methylquinoxalin-5-yl)-7-methoxybenzo[d]thiazole

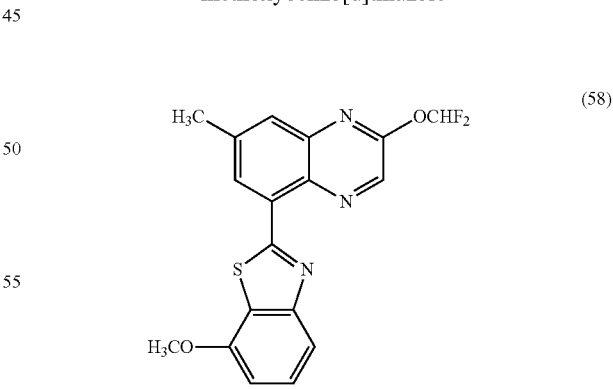

To Intermediate 15F (15 mg, 0.075 mmol) and Intermediate I-1 (30.3 mg, 0.090 mmol) was added toluene (0.75 mL) and EtOH (0.25 mL). The mixture was stirred at room temperature until solids are dissolved, then [1,1'-bis(diphenylphosphino)ferrocene] dichloropalladium (II) complex with dichloromethane (1:1) (7.36 mg, 9.02 μmol) was added. The flask was degassed and flushed with argon. Finally sodium carbonate (0.056 mL, 2M, 0.113 mmol) was added dropwise. The reaction vessel was sealed and bubbled with argon for 5 min, then placed in microwave reactor at 120° C. for 30 min. The reaction mixture was cooled to room temperature and was diluted with EtOAc and water, extracted with EtOAc (3×). The combined organic layer was washed with brine, dried with MgSO₄ and concentrated. The crude sample was purified with a preparative HPLC (method A, 65-100% B in 8 min.). The desired fractions were placed in a SpeedVac overnight to remove solvent, then lyophilized to give Example 58 (10.5 mg, 0.028 mmol, 37.1% yield). $^1$H NMR (400 MHz, chloroform-d) δ 8.84 (d, J=1.52 Hz, 1H), 8.72 (s, 1H), 7.81-7.83 (m, 1H), 7.79 (dd, J=0.63, 8.21 Hz, 1H), 7.45-7.87 (m, 2H), 6.88 (d, J=7.83 Hz, 1H), 4.07 (s, 3H), 2.70 (s, 3H). $^{19}$F NMR (400 MHz, chloroform-d) −90.12 (s, 2F). LC-MS: method C, RT=2.50 min, MS (ESI) m/z: 374.0 (M+H)⁺. Analytical HPLC purity (method A): 99%.

Example 59

2-(2-(difluoromethoxy)-7-methylquinoxalin-5-yl)-4-fluoro-6-methoxybenzo[d]thiazole

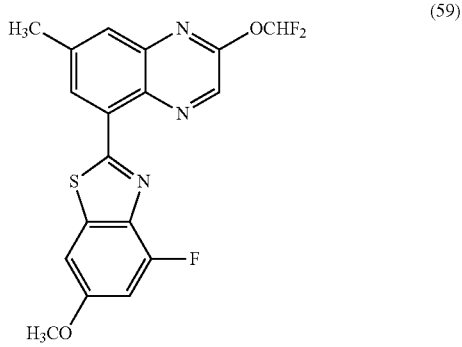 [SMILES: COc1cc(F)c2nc(-c3cc(C)cc4nc(OC(F)F)cnc34)sc2c1]

(59)

Intermediate 59A: 4-fluoro-6-methoxybenzo[d]thiazol-2-amine

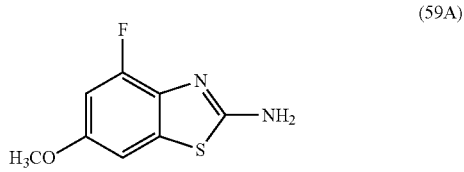 [SMILES: COc1cc(F)c2nc(N)sc2c1]

(59A)

To 2-fluoro-4-methoxyaniline (636 mg, 4.51 mmol) in acetonitrile (14 mL) was added ammonium thiocyanate (515 mg, 6.76 mmol). The mixture was stirred at room temperature for 10 min. Then it was cooled with tape water, and benzyltrimethylammonium tribromide (1757 mg, 4.51 mmol) in acetonitrile (5.0 mL) was added dropwise (10 min). The mixture was then stirred at room temperature overnight. The mixture was diluted with EtOAc/saturated sodium bicarbonate. The organic layer was collected, washed with brine, dried over sodium sulfate. After evaporation of solvent, the crude product was dissolved in a small amount of chloroform/a small amount of MeOH and charged to a 40 g silica gel cartridge which was eluted with 5% EtOAc in hexanes for 3 min., then a 12 min gradient from 5% to 75% EtOAc in hexanes. The desired fractions were combined and concentrated to give Intermediate 59A (0.65 g, 3.28 mmol, 72.8% yield) as a pale solid. $^1$H NMR (500 MHz, DMSO-d₆) δ 6.84 (d, J=1.7 Hz, 1H), 6.75 (br. s., 2H), 6.55 (dd, J=12.1, 2.2 Hz, 1H), 3.74-3.72 (m, 3H); $^{19}$F NMR (471 MHz, DMSO-d₆) δ −124.96 (s, 1F); LC-MS: method A, RT=1.17 min, MS (ESI) m/z: 199.0 (M+H).

Intermediate 59B: 2-bromo-4-fluoro-6-methoxybenzo[d]thiazole

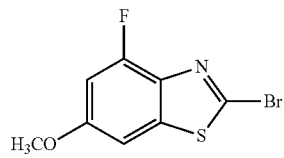

(59B)

To a suspension of Intermediate 59A (0.32 g, 1.614 mmol) in acetonitrile (15 mL) was added p-TSA monohydrate (0.983 g, 5.17 mmol). The salt formed was stirred at room temperature for 15 min, and at 10° C. (cooled with ice water) for 5 min, followed by dropwise addition of a solution of sodium nitrite (0.223 g, 3.23 mmol) and potassium bromide (0.480 g, 4.04 mmol) in water (5 mL) over a period of 2 min. The reaction mixture was stirred at from 10° C. to room temperature overnight. The reaction was quenched with saturated sodium bicarbonate. The insoluble material was removed by filtration. The filtrate was extracted with EtOAc. The organic layer was washed with brine, dried over sodium sulfate. After evaporation of solvent, the crude product was dissolved in a small amount of chloroform and charged to a 12 g silica gel cartridge which was eluted with hexanes for 2 min., then a 15 min gradient from 0% to 30% EtOAc in hexanes. The desired fractions were combined and concentrated to give Intermediate 59B (0.15 g, 0.572 mmol, 35.5% yield) as a pale yellow solid. $^1$H NMR (500 MHz, chloroform-d) δ 7.07 (dd, J=2.2, 0.8 Hz, 1H), 6.84 (dd, J=11.6, 2.2 Hz, 1H), 3.89 (s, 3H); $^{19}$F NMR (471 MHz, chloroform-d) δ −119.63 (s, 1F); LC-MS: method A, RT=1.87 min, MS (ESI) m/z: 262.0 and 264.0 (M+H)⁺.

Example 59

To Intermediate 59B (15 mg, 0.057 mmol) and Intermediate I-1 (23.08 mg, 0.069 mmol) was added toluene (0.75 mL) and EtOH (0.25 mL). The mixture was stirred at room temperature until solids are dissolved, then [1,1'-bis(diphenylphosphino)ferrocene] dichloropalladium (II) complex with dichloromethane (1:1) (5.61 mg, 6.87 μmol) was added. The flask was degassed and flushed with argon. Finally sodium carbonate (0.043 mL, 2M, 0.086 mmol) was added dropwise. The reaction vessel was sealed and bubbled with argon for 5 min, then placed in microwave reactor at 120° C. for 40 min. The reaction mixture was cooled to room temperature and was diluted with EtOAc and water, extracted with EtOAc (3×). The combined organic layer was washed with brine, dried with MgSO₄ and concentrated. The crude sample was purified with a preparative HPLC (method A, 60-100% B in 8 min.). The desired fractions were placed in a SpeedVac overnight to remove solvent, then lyophilized to give Example 59 (8.5 mg, 0.022 mmol, 37.9% yield). $^1$H NMR (400 MHz, chloroform-d) δ 8.86 (d, J=1.52 Hz, 1H), 8.70 (s, 1H), 7.81 (d, J=0.76 Hz, 1H), 7.45-7.97 (m, 1H), 7.22 (d, J=2.27 Hz, 1H), 6.88 (dd, J=2.15, 11.75 Hz, 1H), 3.92 (s, 3H), 2.69 (s, 3H). $^{19}$F NMR (376 MHz, chloroform-d) δ −90.22 (s, 2F), −121.48 (br. s., 1F). LC-MS: method C, RT=2.53 min, MS (ESI) m/z: 391.9 (M+H)$^+$. Analytical HPLC purity (method A): 100%.

Example 60

2-(2-(difluoromethoxy)-7-methylquinoxalin-5-yl)-5-fluorobenzo[d]thiazole

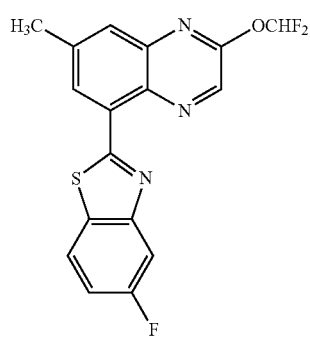

(60)

To 2-chloro-5-fluorobenzo[d]thiazole (15 mg, 0.080 mmol) and Intermediate I-1 (32.2 mg, 0.096 mmol) was added toluene (0.75 mL) and EtOH (0.25 mL). The mixture was stirred at room temperature until solids are dissolved, then [1,1'-bis(diphenylphosphino)ferrocene] dichloropalladium (II) complex with dichloromethane (1:1) (7.83 mg, 9.59 μmol) was added. The flask was degassed and flushed with Ar. Finally sodium carbonate (2M, 0.12 mL, 0.24 mmol) was added dropwise. The reaction vessel was sealed and bubbled with argon for 5 min, then placed in microwave reactor at 120° C. for 40 min. The reaction mixture was cooled to room temperature and was diluted with EtOAc and water, extracted with EtOAc (3×). The combined organic layer was washed with brine, dried with MgSO$_4$ and concentrated. The crude material was purified via preparative LC/MS (method D, 60-100% B over 10 min., then a 5-min hold at 100% B). Fractions containing the desired product were combined and dried via centrifugal evaporation to yield Example 60 (18.8 mg, 0.052 mmol, 65.1% yield). $^1$H NMR (500 MHz, DMSO-d$_6$) δ 8.96 (s, 1H), 8.75 (d, J=1.65 Hz, 1H), 8.15 (dd, J=4.81, 8.94 Hz, 1H), 8.09 (dd, J=2.48, 8.53 Hz, 1H), 7.93 (s, 1H), 7.73-8.04 (m, 1H), 7.44 (dt, J=2.75, 9.08 Hz, 1H), 2.67 (s, 3H). LC-MS: method C, a=2.54 min, MS (ESI) m/z: 361.9 (M+H)$^+$. Analytical HPLC purity (method A): 100%.

Example 61

Methyl 2-(2-(difluoromethoxy)-7-methylquinoxalin-5-yl)benzo[d]thiazole-7-carboxylate

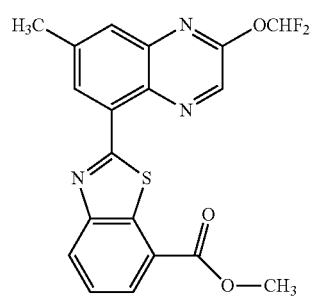

(61)

Intermediate 61A: methyl 2-bromobenzo[d]thiazole-7-carboxylate

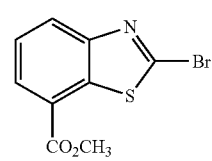

(61A)

tert-Butyl nitrite (1.111 mL, 8.40 mmol) was added to copper (II) bromide (1.770 g, 7.92 mmol) in dry acetonitrile (15 mL) under argon. The mixture was stirred at room temperature for 10 min. A suspension of methyl 2-amino-benzo[d]thiazole-7-carboxylate (1.0 g, 4.80 mmol) in dry acetonitrile (15 mL) was added dropwise. The reaction mixture was stirred at room temperature for 1.5 h. The mixture was heated at 50° C. for 45 min. Acetonitrile was removed under vacuum, the reaction mixture was diluted with EtOAc, quenched with 1.0 N HCl. The organic layer was collected, washed with 0.5 N HCl (2×), saturated sodium bicarbonate, brine, dried over sodium sulfate. After evaporation of solvent, Intermediate 61A (1.2 g, 4.41 mmol, 92% yield) was obtained as brown solid. It was used for next step without further purification. $^1$H NMR (500 MHz, chloroform-d) δ 8.19 (dd, J=8.0, 1.1 Hz, 1H), 8.13 (dd, J=7.7, 1.1 Hz, 1H), 7.58 (t, J=7.8 Hz, 1H), 4.05 (s, 3H); LC-MS: method A, RT=2.02 min, MS (ESI) m/z: 272.0 274.0 (M+H)$^+$.

Example 61

To Intermediate I-1 (30 mg, 0.089 mmol), Intermediate 61A (31.6 mg, 0.116 mmol) and [1,1'-bis(diphenylphosphino)ferrocene]dichloropalladium (II) complex with dichloromethane (1:1) (5.83 mg, 7.14 μmol) was added toluene (1.5 mL) and EtOH (0.5 mL). The mixture was sonicated for 1 min, and flushed with argon. To this was added sodium carbonate (0.098 mL, 2M, 0.196 mmol). The reaction mixture was heated in a microwave reactor at 120° C. for 30 min. To the reaction mixture was added EtOAc/water. The organic layers were collected, dried over sodium sulfate. After evaporation of solvent, the crude product was purified via preparative LC/MS (method D, 55-95% B over 10 min., then a 5-min hold at 100% B). Fractions containing the desired product were combined and dried via centrifugal evaporation to yield Example 61 (2.9 mg, 7.08 μmol, 7.93%). ¹H NMR (500 MHz, Methanol-d₄) δ 8.73 (s, 1H), 8.71 (d, J=1.65 Hz, 1H), 8.30 (dd, J=0.83, 7.98 Hz, 1H), 8.15 (dd, J=0.83, 7.43 Hz, 1H), 7.84 (s, 1H), 7.61 (t, J=7.70 Hz, 1H), 7.52-7.82 (m, 1H), 4.05 (s, 3H), 2.68 (s, 3H). LC-MS: method C, RT=2.41 min, MS (ESI) m/z: 402.10 (M+H)⁺. Analytical HPLC purity (method B): 98%

Example 62

Methyl 2-(2-(difluoromethoxy)-7-methylquinoxalin-5-yl)-6,7-dihydrothiazolo[5,4-c]pyridine-5(4H)-carboxylate

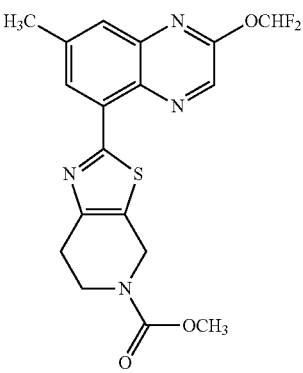

(62)

Intermediate 62A 2-(2-(difluoromethoxy)-7-methylquinoxalin-5-yl)-4,5,6,7-tetrahydrothiazolo[5,4-c]pyridine

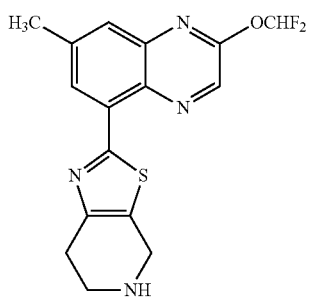

(62A)

To Example 11 (19 mg, 0.042 mmol) was added 4.0 N HCl in dioxane (1059 μl, 4.24 mmol). The mixture was aged at room temperature for 2.0 h. Solvent was removed and the product was lyophilized overnight to give Intermediate 62A (14 mg, 0.034 mmol, 81% yield). ¹H NMR (500 MHz, methanol-d₄) δ 8.65 (s, 1H), 8.61 (s, 1H), 7.82 (s, 1H), 7.65 (t, $J_{HF}$=71.53 Hz, 1H), 4.56 (br. s., 2H), 3.77-3.73 (m, 2H), 3.72-3.68 (m, 2H), 2.66 (s, 3H); ¹⁹F NMR (471 MHz, methanol-d₄) δ -90.23 (s, 2F); LC-MS: method A, RT=1.70 min, MS (ESI) m/z: 349.0 (M+H)⁺.

Example 62

To a solution of Intermediate 62A (9 mg, 0.026 mmol) and DIEA (0.023 mL, 0.129 mmol) in DCM (1 mL) was added a solution of methyl chloroformate (4.00 μl, 0.052 mmol) in DCM (1 mL). The mixture was stirred at room temperature for 1.0 h. The reaction mixture was diluted with EtOAc and water, extracted with EtOAc. The combined organic layer was washed with brine, dried with MgSO₄ and concentrated. The crude was purified with a preparative HPLC (method A, 60-100% B in 6 min.). The desired fractions were placed in a SpeedVac overnight to remove solvent, then lyophilized to give Example 62 (8 mg, 0.018 mmol, 68.6% yield). ¹H NMR (400 MHz, chloroform-d) δ 8.63 (s, 1H), 8.55 (s, 1H), 7.74 (s, 1H), 7.40-7.97 (m, 1H), 4.82 (br. s., 2H), 3.88 (br. s., 2H), 3.79 (s, 3H), 3.05 (br. s., 2H), 2.64 (s, 3H). ¹⁹F NMR (376 MHz, chloroform-d) δ -90.20 (s, 2F). LC-MS: method C, RT=2.43 min, MS (ESI) m/z: 406.9 (M+H)⁺. Analytical HPLC purity (method A): 92%.

Example 63

N-(2-(2-(2-(difluoromethoxy)-7-methylquinoxalin-5-yl)benzo[d]thiazol-6-yloxy)ethyl) benzenesulfonamide

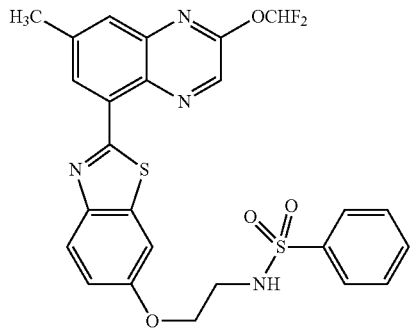

(63)

To a solution of Intermediate I-4 (12 mg, 0.027 mmol) and DIEA (23.88 μl, 0.137 mmol) in DCM (2 ml) was added a solution of benzenesulfonyl chloride (9.66 mg, 0.055 mmol) in 0.2 ml of DCM. The mixture was stirred at room temperature for 1 h. The reaction mixture was diluted with EtOAc and water, extracted with EtOAc. The combined organic layer was washed with brine, dried with MgSO₄ and concentrated. The crude sample was purified with a preparative HPLC (method A, 50-100% B in 6 min.). The desired fractions were placed in a SpeedVac overnight to remove solvent, then lyophilized to give Example 63 (10 mg, 0.018 mmol, 64.7% yield). ¹H NMR (400 MHz, acetonitrile-d₃) δ 8.90-8.58 (m, 2H), 7.95 (d, J=8.8 Hz, 1H), 7.90-7.50 (m, 7H), 7.05 (dd, J=8.8, 2.5 Hz, 1H), 5.97 (br. s., 1H), 4.06 (t, J=5.3 Hz, 2H), 3.33 (q, J=5.6 Hz, 2H), 2.68 (s, 3H). ¹⁹F NMR (376 MHz, acetonitrile-d₃) δ -90.50 (s, 2F). LC-MS: method C, RT=2.39 min, MS (ESI) m/z: 543.0 (M+H)⁺. Analytical HPLC purity (method A): 96%.

Example 64

(2-(2-(difluoromethoxy)-7-methylquinoxalin-5-yl)benzo[d]thiazol-7-yl)methanol

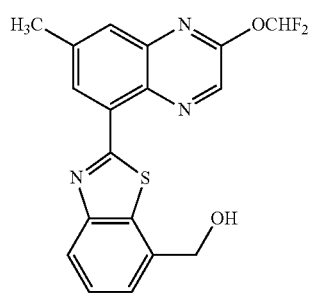

(64)

Intermediate 64A:
(2-bromobenzo[d]thiazol-7-yl)methanol

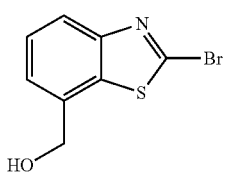

(64A)

To a solution of Intermediate 61A (0.53 g, 1.948 mmol) in THF (10 mL) at 0° C. was added 1.0 M Super-H in THF (4.28 mL, 4.28 mmol) dropwise. The mixture was stirred at 0° C. for 1.0 h. The reaction mixture was diluted with EtOAc, quenched with saturated ammonium chloride at 0° C., and then with a few drops of 1.0 N HCl. The organic layer was washed with brine, dried over sodium sulfate. After evaporation of solvent, the crude product was dissolved in a small amount of chloroform and was purified with 40 g ISCO column eluted with hexanes for 3 min, then an 18 min gradient from 0 to 100% EtOAc in hexanes. The desired fractions were combined and concentrated to give Intermediate 64A (380 mg, 1.557 mmol, 80% yield) as a light yellow solid. $^1$H NMR (400 MHz, Methanol-d$_4$) δ 7.80 (d, J=8.08 Hz, 1H), 7.44 (t, J=7.71 Hz, 1H), 7.31 (d, J=7.33 Hz, 1H), 4.83 (s, 2H). LC-MS: method C, RT=1.58 min, MS (ESI) m/z: 243 and 245 (M+H)$^+$.

Example 64

To Intermediate I-1 (106 mg, 0.315 mmol), Intermediate 64A (100 mg, 0.410 mmol) and [1,1'-bis(diphenylphosphino)ferrocene]dichloropalladium (II) complex with dichloromethane (1:1) (20.59 mg, 0.025 mmol) was added toluene (7.5 mL) and EtOH (2.500 mL). The mixture was sonicated for 1 min, and flushed with argon. To this was added sodium carbonate (0.315 mL, 2M, 0.630 mmol). The reaction mixture was heated in a microwave reactor at 120° C. for 30 min. The reaction mixture was diluted with EtOAc and water, extracted with EtOAc (3×). The combined organic layer was washed with brine, dried with MgSO$_4$ and concentrated. The crude sample was purified 12 g ISCO column eluted with 0-100% EtOAc in hexanes for 15 min., followed by a preparative HPLC (method A, 30-100% B in 8 min.). The desired fractions were placed in a SpeedVac overnight to remove solvent, then lyophilized to give Example 64 (88 mg, 0.261 mmol, 83% yield). $^1$H NMR (500 MHz, methanol-d$_4$) δ 8.76 (s, 1H), 8.02 (d, J=8.25 Hz, 1H), 7.88 (dd, J=1.10, 1.93 Hz, 1H), 7.62-7.94 (m, 1H), 7.50-7.58 (m, 1H), 7.43 (dd, J=0.96, 7.29 Hz, 1H), 4.94 (s, 2H), 2.69 (s, 3H). $^{19}$F NMR (376 MHz, methanol-d$_4$) δ −91.06 (s, 2F). LC-MS: method C, RT=2.24 min, MS (ESI) m/z: 373.9 (M+H)$^+$. Analytical HPLC purity (method A): 98%.

Example 65

2-(2-(difluoromethoxy)-7-methylquinoxalin-5-yl)-7-(methoxymethyl)benzo[d]thiazole

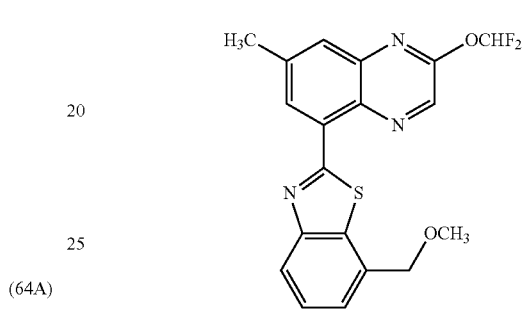

(65)

To a suspension of Example 64 (18 mg, 0.048 mmol) in THF (1 mL) was added NaH (3.86 mg, 0.096 mmol) and the mixture was stirred at room temperature for 30 min Then MeI (0.090 mL, 1.446 mmol) was added. The mixture was heated up to 50° C. for 2 h. The mixture was diluted with EtOAc and water, extracted with EtOAc. The combined organic layer was washed with brine, dried with MgSO$_4$ and concentrated. The crude was purified with a preparative HPLC (method A, 50-100% B in 6 min.). The desired fractions were placed in a SpeedVac overnight to remove solvent, then lyophilized to give Example 65 (2 mg, 5.06 μmol, 10.49% yield). $^1$H NMR (400 MHz, chloroform-d) δ 8.82 (d, J=2.02 Hz, 1H), 8.75 (s, 1H), 8.13 (d, J=8.08 Hz, 1H), 7.84 (s, 1H), 7.48-7.88 (m, 2H), 7.39 (d, J=7.33 Hz, 1H), 4.84 (s, 2H), 3.49 (s, 3H), 2.70 (s, 3H). $^{19}$F NMR (376 MHz, chloroform-d) δ −90.20 (s, 2F). LC-MS: method C, RT=2.45 min, MS (ESI) m/z: 387.9 (M+H)$^+$. Analytical HPLC purity (method A): 99%.

Example 66

N-((2-(2-(difluoromethoxy)-7-methylquinoxalin-5-yl)benzo[d]thiazol-7-yl)methyl)benzenesulfonamide

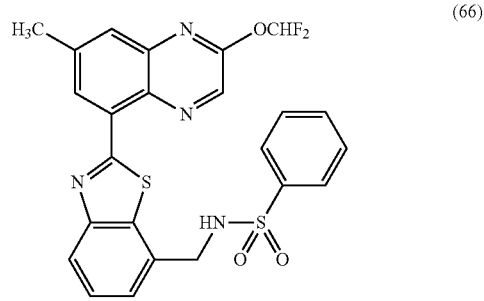 [SMILES: Cc1cc(-c2nc3cccc(CNS(=O)(=O)c4ccccc4)c3s2)c2ncc(OC(F)F)nc2c1]

(66)

Intermediate 66A: tert-butyl N-[(2-bromo-1,3-benzothiazol-7-yl)methyl]-N-[(tert-butoxy)carbonyl]carbamate

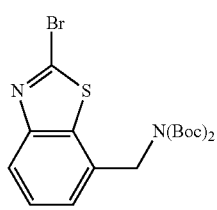

(66A)

A solution of DIAD (0.134 mL, 0.688 mmol) in THF (2 mL) was added to a solution of di-tert-butyl iminodicarboxylate (150 mg, 0.688 mmol), Intermediate 64A (56 mg, 0.229 mmol) and triphenylphosphine (181 mg, 0.688 mmol) in THF (2 mL). The mixture was stirred at room temperature for 1 h, diluted with DCM and saturated NaHCO$_3$, extracted with DCM, the combined organic layer was washed with brine, dried MgSO$_4$ and concentrated. The crude sample was purified with 40 g ISCO column eluted with 0-100% DCM/Hex for 20 min, the desired fraction was collected to give Intermediate 66A (55 mg, 0.124 mmol, 54.1% yield) as a yellow solid. $^1$H NMR (500 MHz, chloroform-d) δ 7.90 (d, J=7.98 Hz, 1H), 7.45 (t, J=7.84 Hz, 1H), 7.30 (dd, J=0.83, 7.43 Hz, 1H), 4.98 (s, 2H), 1.41-1.46 (m, 18H). LC-MS: method C, RT=2.37 min, MS (ESI) m/z: 908.9 [2M+23]$^+$.

Intermediate 66B: tert-butyl N-[(tert-butoxy)carbonyl]-N-({2-[2-(difluoromethoxy)-7-methylquinoxalin-5-yl]-1,3-benzothiazol-7-yl}methyl)carbamate

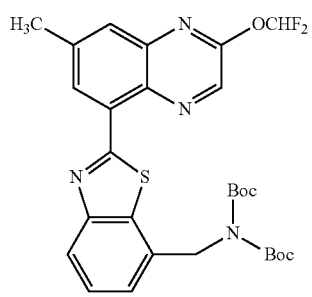

(66B)

To Intermediate I-1 (37.9 mg, 0.113 mmol), Intermediate 66A (50 mg, 0.113 mmol) and [1,1'-bis(diphenylphosphino)ferrocene]dichloropalladium (II) complex with dichloromethane (1:1) (7.37 mg, 9.02 μmol) was added toluene (7.5 mL) and EtOH (2.500 mL). The mixture was sonicated for 1 min, and flushed with argon. To this was added sodium carbonate (0.113 mL, 2M, 0.226 mmol). The reaction mixture was heated in a microwave reactor at 120° C. for 30 min. The reaction mixture was diluted with EtOAc and water, extracted with EtOAc. The combined organic layer was washed with brine, dried with MgSO$_4$ and concentrated. The crude sample was purified with a preparative HPLC (method A, 70-100% B in 6 min.). The desired fractions were placed in a SpeedVac overnight to remove solvent, then lyophilized to give Intermediate 66B (21 mg, 0.035 mmol, 30.9% yield). $^1$H NMR (500 MHz, methanol-d$_4$) δ 8.76 (s, 1H), 8.02 (d, J=8.25 Hz, 1H), 7.88 (dd, J=1.10, 1.93 Hz, 1H), 7.62-7.94 (m, 1H), 7.50-7.58 (m, 1H), 7.43 (dd, J=0.96, 7.29 Hz, 1H), 4.94 (s, 2H), 2.69 (s, 3H). $^{19}$F NMR (376 MHz, methanol-d) δ -90.20 (s, 2F). LC-MS: method C, RT=2.62 min, MS (ESI) m/z: 573.2 (M+H)$^+$.

Intermediate 66C: tert-butyl (2-(2-(difluoromethoxy)-7-methylquinoxalin-5-yl) benzo[d]thiazol-7-yl)methylcarbamate

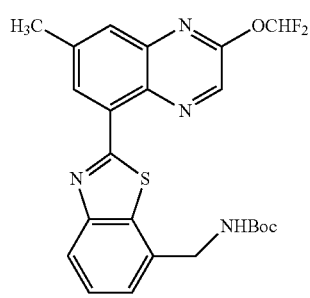

(66C)

To a solution of Intermediate 66B (17 mg, 0.030 mmol) in DCM (1 mL) was added TFA (0.023 mL, 0.297 mmol). The mixture was stirred at room temperature for 15 min, diluted with EtOAc and water, extracted with EtOAc. The combined organic layer was washed with NaHCO$_3$ and brine, dried with MgSO$_4$ and concentrated. The crude sample was purified with a preparative HPLC (method A, 70-100% B in 6 min.). The desired fractions were placed in a SpeedVac overnight to remove solvent, then lyophilized to give Intermediate 66C (13 mg, 0.027 mmol, 92% yield). $^1$H NMR (400 MHz, chloroform-d) δ 8.83 (d, J=1.8 Hz, 1H), 8.70 (s, 1H), 8.10 (d, J=7.8 Hz, 1H), 7.84 (d, J=1.0 Hz, 1H), 7.87-7.48 (m, 3H), 7.37 (d, J=6.8 Hz, 1H), 2.70 (s, 3H), 1.52 (s, 9H). $^{19}$F NMR (376 MHz, chloroform-d) δ -90.20 (s, 2F). LC-MS: method C, RT=2.44 min, MS (ESI) m/z: 472.9 (M+H)$^+$.

Intermediate 66D (2-(2-(difluoromethoxy)-7-methylquinoxalin-5-yl)benzo[d]thiazol-7-yl)methanamine

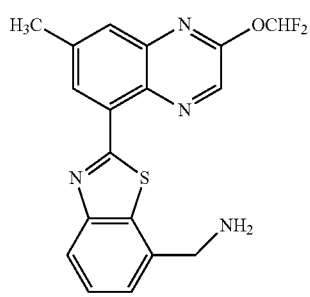

(66D)

To a solution of Intermediate 66C (11 mg, 0.022 mmol, 94% yield) in DCM was added TFA (359 μl 4.66 mmol) and the mixture was stirred at room temperature for 15 min. The crude was purified with a preparative HPLC (method A, 30-100% B in 6 min.). The desired fractions were placed in a SpeedVac overnight to remove solvent, then lyophilized to give Intermediate 66D (11 mg, 0.022 mmol, 94% yield). $^1$H NMR (400 MHz, methanol-$d_4$) δ 8.80 (d, J=1.8 Hz, 1H), 8.71 (s, 1H), 8.16 (d, J=8.1 Hz, 1H), 7.92-7.59 (m, 3H), 7.52-7.44 (m, 1H), 4.44 (s, 2H), 2.70 (s, 3H). $^{19}$F NMR (376 MHz, methanol-$d_4$) δ −78.07 (s, 3F), −92.13 (s, 2F). LC-MS: method C, RT=1.91 min, MS (ESI) m/z: 372.9 (M+H)$^+$.

Example 66

To a solution of Intermediate 66D (8 mg, 0.016 mmol) and DIEA (0.014 mL, 0.082 mmol) in DCM (1 mL) was added a solution of benzenesulfonyl chloride (5.81 mg, 0.033 mmol) in 0.2 ml of DCM. The mixture was stirred at room temperature for 1.0 h. Solvent was removed, the residual was purified with a preparative HPLC (method A, 50-100% B in 6 min.). The desired fractions were placed in a SpeedVac overnight to remove solvent, then lyophilized to give Example 66 (3 mg, 5.21 μmol, 31.7% yield). $^1$H NMR (400 MHz, chloroform-d) δ 8.76 (d, J=1.8 Hz, 1H), 8.73 (s, 1H), 8.06 (d, J=8.1 Hz, 1H), 7.92-7.84 (m, 3H), 7.70-7.30 (m, 6H), 4.93 (d, J=5.8 Hz, 1H), 4.56 (d, J=5.8 Hz, 2H), 2.70 (s, 3H). $^{19}$F NMR (376 MHz, chloroform-d) δ −90.22 (s, 2F). LC-MS: method C, RT=2.30 min, MS (ESI) m/z: 513.1 (M+H)$^+$. Analytical HPLC purity (method A): 90%

Example 67

N-(2-(2-(2-(difluoromethoxy)-7-methylquinoxalin-5-yl)-4-fluorobenzo[d]thiazol-6-yloxy)ethyl)benzenesulfonamide

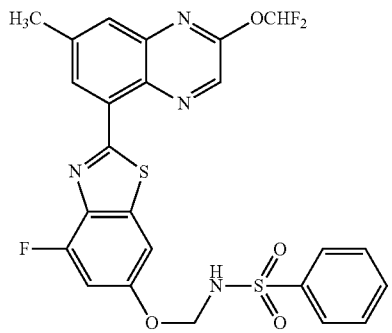

(67)

Intermediate 67A:
2-bromo-4-fluorobenzo[d]thiazol-6-ol

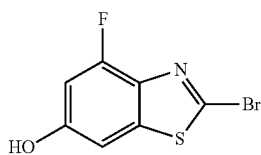

(67A)

Aluminum chloride (308 mg, 2.308 mmol) was added to a solution of Intermediate 59B (220 mg, 0.839 mmol) in toluene (4 mL). The mixture was heated at 85° C. for 1.5 h. The reaction mixture was cooled to room temperature, quenched with ice-cold 1.0 N HCl (10 mL) and EtOAc (10 mL), and stirred at room temperature for 30 min. The organic layer was collected, washed with water, saturated sodium bicarbonate, brine, dried over sodium sulfate. After evaporation of solvent, the crude product was dissolved in a small amount of chloroform and charged to a 12 g silica gel cartridge which was eluted with hexanes for 5 min., then an 18 min gradient from 0% to 40% EtOAc in hexanes. The desired fractions were combined and concentrated to give Intermediate 67A (45 mg, 0.181 mmol, 21.61% yield) as brown solid. $^1$H NMR (400 MHz, methanol-$d_4$) δ 6.98 (dd, J=2.3, 0.8 Hz, 1H), 6.71 (dd, J=11.9, 2.3 Hz, 1H). LC-MS: method C, RT=1.72 min, MS (ESI) m/z: 247 and 249 (M+H)$^+$.

Intermediate 67B: tert-butyl 2-(2-bromo-4-fluorobenzo[d]thiazol-6-yloxy)ethylcarbamate

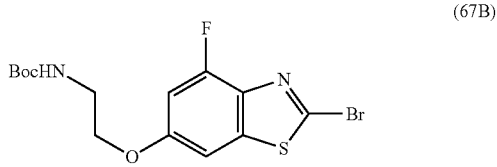 [SMILES: CC(C)(C)OC(=O)NCCOc1cc(F)c2nc(Br)sc2c1]

(67B)

A solution of DIAD (0.088 mL, 0.453 mmol) and tert-butyl (2-hydroxyethyl) carbamate (0.070 mL, 0.453 mmol) in THF (1 mL) was added to a solution of Intermediate 67A (45 mg, 0.181 mmol) and triphenylphosphine (71.4 mg, 0.272 mmol) in THF (2 mL) at 80° C. using syringe pump over 2 h. The mixture was concentrated and redissolved in 1 ml of DCM and was purified with a 12 g ISCO column eluted with 0-70% EtOAc in hexanes for 15 min, the desired fraction was collected to give Intermediate 67B (30 mg, 0.077 mmol, 42.3% yield). $^1$H NMR (400 MHz, chloroform-d) δ 7.05 (d, J=1.8 Hz, 1H), 6.82 (dd, J=11.4, 2.3 Hz, 1H), 5.13-4.95 (m, 1H), 4.07 (t, J=5.1 Hz, 2H), 3.62-3.48 (m, 2H), 1.48-1.42 (m, 9H). LC-MS: method C, RT=2.14 min, MS (ESI) m/z: 391 and 393 (M+H)$^+$.

Intermediate 67C: tert-butyl 2-(2-(2-(difluoromethoxy)-7-methylquinoxalin-5-yl)-4-fluorobenzo[d]thiazol-6-yloxy)ethylcarbamate

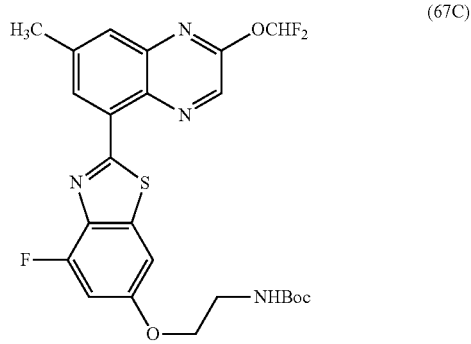 [SMILES: Cc1cc(-c2nc3c(F)cc(OCCNC(=O)OC(C)(C)C)cc3s2)c2ncc(OC(F)F)nc2c1]

(67C)

To Intermediate I-1 (23 mg, 0.068 mmol), Intermediate 67B (29.4 mg, 0.075 mmol) and [1,1'-bis(diphenylphosphino)ferrocene]dichloropalladium (II) complex with dichloromethane (1:1) (4.47 mg, 5.47 μmol) was added toluene (0.75 mL) and EtOH (0.250 mL). The mixture was sonicated for 1 min, and flushed with argon. To this was added sodium carbonate (0.068 mL, 2M, 0.137 mmol). The reaction mixture was heated in a microwave reactor at 100° C. for 30 min. To the reaction mixture was added EtOAc/water. The organic layers were collected, dried over sodium sulfate. The crude residue was purified with a 12 g ISCO column eluted with 0-70% EtOAc in hexanes for 15 min. The desired fraction was concentrated and further purified with a preparative HPLC (method A, 70-100% B in 6 min.). The desired fractions were placed in a SpeedVac overnight to remove solvent, then lyophilized to give Intermediate 67C (30 mg, 0.054 mmol, 79% yield). $^1$H NMR (400 MHz, chloroform-d) δ 8.85 (d, J=1.8 Hz, 1H), 8.69 (s, 1H), 7.81 (dd, J=1.9, 0.9 Hz, 1H), 7.95-7.41 (m, 1H), 7.21 (d, J=2.0 Hz, 1H), 6.88 (dd, J=11.6, 2.3 Hz, 1H), 4.13 (t, J=5.1 Hz, 2H), 3.60 (br. s., 2H), 2.69 (s, 3H), 1.48 (s, 9H). $^{19}$F NMR (376 MHz, chloroform-d) δ −90.55 (s, 2F), −123.30 (br. s., 1F). LC-MS: method C, RT=2.47 min, MS (ESI) m/z: 521.2 (M+H)$^+$.

Intermediate 67D 2-(2-(2-(difluoromethoxy)-7-methylquinoxalin-5-yl)-4-fluorobenzo[d]thiazol-6-yloxy)ethanamine

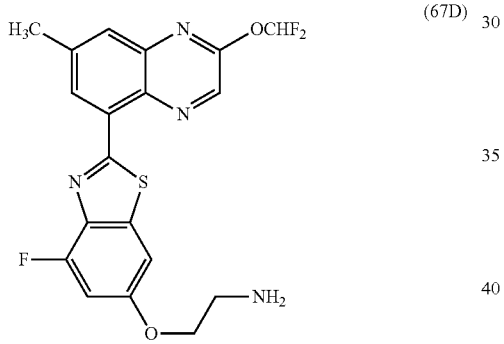

To a solution of Intermediate 67C (25 mg, 0.048 mmol) in DCM (1 mL) was added TFA (0.920 mL, 11.94 mmol). The mixture was stirred at room temperature for 1 h. Solvent was removed, the residual was purified with a preparative HPLC (method A, 30-100% B in 6 min.). The desired fractions were placed in a SpeedVac overnight to remove solvent, then lyophilized to give Intermediate 67D (22 mg, 0.040 mmol, 84% yield). $^1$H NMR (400 MHz, methanol-d$_4$) δ 8.78 (d, J=2.0 Hz, 1H), 8.74 (s, 1H), 7.87 (d, J=1.0 Hz, 1H), 8.00-7.55 (m, 1H), 7.48 (d, J=2.3 Hz, 1H), 7.04 (dd, J=11.9, 2.3 Hz, 1H), 4.43-4.30 (m, 2H), 3.52-3.41 (m, 2H), 2.69 (s, 3H). $^{19}$F NMR (376 MHz, methanol-d$_4$) δ −77.57 (br. s., 3F), −84.34-98.20 (s 2F), −123.30 (br. s., 1F). LC-MS: method C, RT=2.03 min, MS (ESI) m/z: 421.2 (M+H)$^+$.

Example 67

To a solution of Intermediate 67D (15 mg, 0.028 mmol) and DIEA (49.0 μl, 0.281 mmol) in DCM was added a solution of benzenesulfonyl chloride (7.20 μl, 0.056 mmol) in 0.2 ml of DCM. The mixture was stirred at room temperature for 1.0 h. The reaction mixture was diluted with EtOAc and water, extracted with EtOAc. The combined organic layer was washed with brine, dried with MgSO$_4$ and concentrated. The crude sample was purified with a preparative HPLC (method A, 50-100% B in 6 min.). The desired fractions were placed in a SpeedVac overnight to remove solvent, then lyophilized to give Example 67 (4 mg, 6.64 μmol, 23.64% yield). $^1$H NMR (400 MHz, chloroform-d) δ 8.86 (d, J=1.8 Hz, 1H), 8.69 (s, 1H), 7.98-7.90 (m, 2H), 7.81 (s, 1H), 7.64-7.50 (m, 3H), 7.87-7.43 (m, 1H), 7.10 (d, J=2.3 Hz, 1H), 6.77 (dd, J=11.5, 2.1 Hz, 1H), 4.96 (t, J=5.9 Hz, 1H), 4.10 (t, J=5.1 Hz, 2H), 3.47 (q, J=5.3 Hz, 2H), 2.69 (s, 3H). $^{19}$F NMR (376 MHz, chloroform-d) δ −90.22 (s, 2F), −120.80 (br. s., 1F). LC-MS: method C, RT=2.40 min, MS (ESI) m/z: 560.9 (M+H)$^+$. Analytical HPLC purity (method A): 95%.

Example 68

2-(2-(difluoromethoxy)-7-methylquinoxalin-5-yl)-5-methylbenzo[d]thiazole

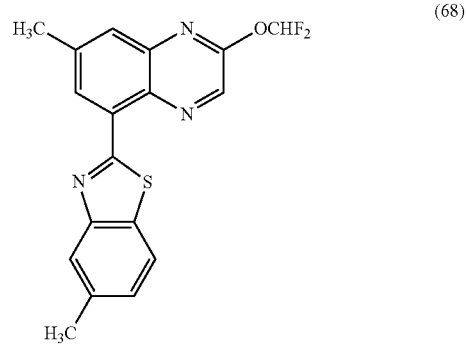 [SMILES: Cc1ccc2sc(-c3cc(C)cc4nc(OC(F)F)cnc34)nc2c1]

To Intermediate I-1 (20 mg, 0.059 mmol), 2-chloro-5-methylbenzo[d]thiazole (14.21 mg, 0.077 mmol) and [1,1'-bis(diphenylphosphino)ferrocene]dichloropalladium (II) complex with dichloromethane (1:1) (3.89 mg, 4.76 μmol) was added toluene (1.5 mL) and EtOH (0.5 mL). The mixture was sonicated for 1 min, and flushed with argon. To this was added sodium carbonate (0.065 mL, 2M, 0.131 mmol). The reaction mixture was heated in a microwave reactor at 100° C. for 30 min. To the reaction mixture was added EtOAc/water. The organic layers were collected, dried over sodium sulfate. After evaporation of solvent, the crude was purified with a preparative HPLC (method A, 50-100% B in 6 min.). The desired fractions were placed in a SpeedVac overnight to remove solvent, then lyophilized to give Example 68 (11 mg, 0.030 mmol, 50.7% yield). $^1$H NMR (400 MHz, chloroform-d) δ 8.81 (d, J=2.0 Hz, 1H), 8.71 (s, 1H), 7.97 (s, 1H), 7.87 (d, J=8.1 Hz, 1H), 7.82 (dd, J=1.9, 0.9 Hz, 1H), 7.85-7.48 (m, 1H), 7.28 (br. s., 1H), 2.70 (s, 3H), 2.56 (s, 3H). $^{19}$F NMR (376 MHz, chloroform-d) δ −90.20 (s, 2F). LC-MS: method C, RT=2.57 min, MS (ESI) m/z: 357.9 (M+H)$^+$. Analytical HPLC purity (method A): 98%.

Example 69

Methyl 2-(2-(2-(difluoromethoxy)-7-methylquinoxalin-5-yl)benzo[d]thiazol-7-yloxy)ethylcarbamate

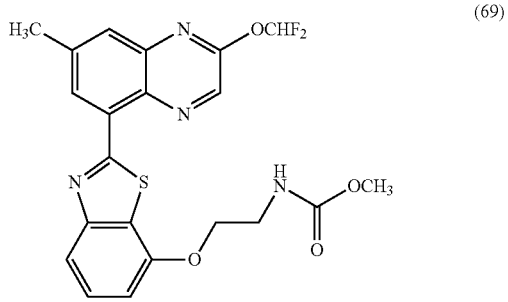 [SMILES: COC(=O)NCCOc1cccc2nc(-c3cc(C)cc4nc(OC(F)F)cnc34)sc12]

(69)

Intermediate 69A: 2-chlorobenzo[d]thiazol-7-ol

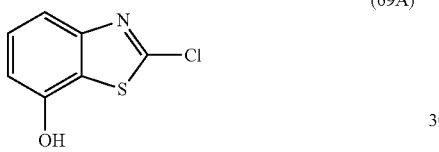

(69A)

Aluminum chloride (184 mg, 1.377 mmol) was added to a solution of 2-chloro-7-methoxybenzo[d]thiazole (100 mg, 0.501 mmol) in toluene (2 mL). The mixture was heated at 85° C. for 1.5 h. HPLC indicated a complete conversion of starting material. The reaction mixture was cooled to room temperature, quenched with ice-cold 1.0 N HCl (50 mL) and EtOAc (50 mL), and stirred at room temperature for 30 min. The organic layer was collected, washed with water, saturated sodium bicarbonate, brine, dried over sodium sulfate. After evaporation of solvent, the crude product was dissolved in a small amount of chloroform and charged to a 12 g silica gel cartridge which was eluted with hexanes for 5 min., then a 10 min gradient from 0% to 40% EtOAc in hexanes. The desired fractions were combined and concentrated to give Intermediate 69A (85 mg, 0.458 mmol, 91% yield) as brown solid. $^1$H NMR (400 MHz, methanol-$d_4$) δ 7.47-7.36 (m, 1H), 7.35-7.24 (m, 1H), 6.82 (d, J=8.1 Hz, 1H). LC-MS: method C, RT=1.72 min, MS (ESI) m/z: 185.8 (M+H)$^+$.

Intermediate 69B: tert-butyl 2-(2-chlorobenzo[d]thiazol-7-yloxy)ethylcarbamate

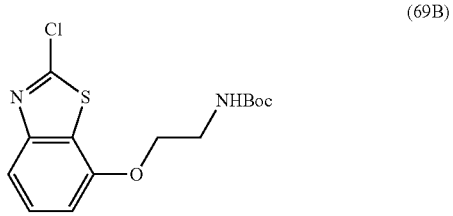 [SMILES: CC(C)(C)OC(=O)NCCOc1cccc2nc(Cl)sc12]

(69B)

A solution of DIAD (0.223 mL, 1.145 mmol) and tert-butyl (2-hydroxyethyl) carbamate (0.177 mL, 1.145 mmol) in THF (1 mL) was added to a solution of Intermediate 69A (85 mg, 0.458 mmol) and triphenylphosphine (180 mg, 0.687 mmol) in THF (2 mL) at 80° C. using syringe pump over 3 h. LCMS indicated a completion of the reaction. The mixture was diluted with EtOAc and saturated NaHCO$_3$, extracted with EtOAc, the combined organic layer was washed with brine, dried with MgSO$_4$ and concentrated. The crude was purified with a 12 g ISCO column eluted with 0-70% EtOAc in hexanes for 15 min, the desired fraction was collected to give Intermediate 69B (125 mg, 0.380 mmol, 83% yield). $^1$H NMR (400 MHz, chloroform-d) δ 7.58 (dd, 0.6 Hz, 1H), 7.41 (t, J=8.1 Hz, 1H), 6.86 (d, J=8.1 Hz, 1H), 4.21 (t, J=5.2 Hz, 2H), 3.60 (q, J=5.3 Hz, 2H), 1.51-1.44 (m, 9H). LC-MS: method C, RT=2.17 min, MS (ESI) m/z: 329. (M+H)$^+$.

Intermediate 69C: tert-butyl 2-(2-(2-(difluoromethoxy)-7-methylquinoxalin-5-yl)benzo[d]thiazol-7-yloxy)ethylcarbamate

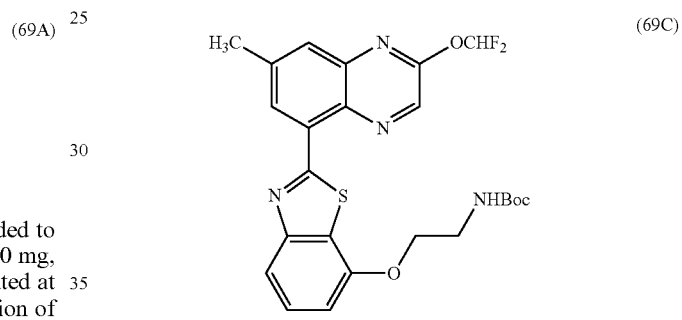

(69C)

To Intermediate I-1 (29 mg, 0.086 mmol), Intermediate 69B (32.6 mg, 0.099 mmol) and [1,1'-bis(diphenylphosphino)ferrocene]dichloropalladium (II) complex with dichloromethane (1:1) (5.64 mg, 6.90 μmol) was added toluene (0.75 mL) and EtOH (0.250 mL). The mixture was sonicated for 1 min, and flushed with argon. To this was added sodium carbonate (0.086 mL, 2M, 0.173 mmol). The reaction mixture was heated in a microwave reactor at 100° C. for 30 min. To the reaction was added EtOAc/water, extracted with EtOAc. The combined organic layer was washed with brine, dried with MgSO$_4$ and concentrated. The crude sample was purified with a 12 g ISCO column eluted with 0-50% EtOAc in hexane for 15 min. The desired fraction was collected and concentrated to give Intermediate 69C (35 mg, 0.068 mmol, 79% yield). $^1$H NMR (400 MHz, acetonitrile-$d_3$) δ 8.79 (s, 1H), 8.77 (d, J=1.8 Hz, 1H), 7.80 (dd, J=1.9, 0.9 Hz, 1H), 7.67-7.62 (m, 1H), 7.97-7.56 (m, 1H), 7.41 (t, J=8.1 Hz, 1H), 6.96 (d, J=8.1 Hz, 1H), 4.25 (t, J=5.7 Hz, 2H), 3.53 (q, J=5.8 Hz, 2H), 2.66 (d, J=13.6 Hz, 1H), 2.63 (s, 3H), 1.33 (s, 9H). $^{19}$F NMR (376 MHz, acetonitrile-$d_3$) δ -90.55 (s, 2F). LC-MS: method C, RT=2.49 min, MS (ESI) m/z: 503.0 (M+H)$^+$.

Intermediate 69D 2-(2-(2-(difluoromethoxy)-7-methylquinoxalin-5-yl)benzo[d]thiazol-7-yloxy)ethanamine

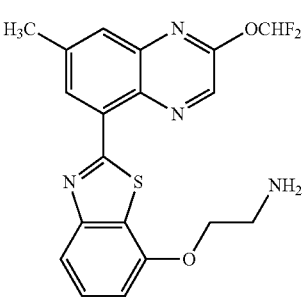
(69D)

To a solution of Intermediate 69C (30 mg, 0.060 mmol) in DCM (1 mL) was added TFA (0.920 mL, 11.94 mmol). The mixture was stirred at room temperature for 1 h. Solvent was removed, the residual was purified with a preparative HPLC (method A, 30-100% B in 6 min.). The desired fractions were placed in a SpeedVac overnight to remove solvent, then lyophilized to give Intermediate 69D (30 mg, 0.058 mmol, 96% yield). $^1$H NMR (400 MHz, methanol-$d_4$) δ 8.79 (d, J=1.8 Hz, 1H), 8.73 (s, 1H), 7.90 (d, J=0.8 Hz, 1H), 7.79 (s, 1H), 7.99-7.60 (m, 1H), 7.53 (t, J=8.1 Hz, 1H), 7.06 (d, J=8.1 Hz, 1H), 4.56-4.42 (m, 2H), 3.52 (t, J=4.9 Hz, 2H), 2.70 (s, 3H). $^{19}$F NMR (376 MHz, methanol-$d_4$) δ −77.64 (br. s., 3F), −91.57 (br. s., 2F). LC-MS: method C, RT=1.96 min, MS (ESI) m/z: 402.9 (M+H)$^+$.

Example 69

To a solution of Intermediate 69D (10 mg, 0.019 mmol) and DIEA (0.017 mL, 0.097 mmol) in DCM (1 mL) was added a solution of methyl chloroformate (3.00 μl 0.039 mmol) in DCM. The mixture was stirred at room temperature for 1 hour. The reaction mixture was diluted with EtOAc and water, and then extracted with EtOAc. The combined organic layer was washed with brine, dried with MgSO$_4$ and concentrated. The crude sample was purified with a preparative HPLC (method A, 60-100% B in 6 min.). The desired fractions were placed in a SpeedVac overnight to remove solvent, then lyophilized to give Example 69 (5.5 mg, 0.011 mmol, 58.6% yield). $^1$H NMR (400 MHz, acetonitrile-$d_3$) δ 8.84-8.81 (m, 1H), 8.79 (s, 1H), 7.90-7.46 (m, 5H), 6.99 (d, J=7.8 Hz, 1H), 4.29 (t, J=5.4 Hz, 2H), 3.65-3.56 (m, 6H), 2.70 (s, 3H). $^{19}$F NMR (376 MHz, acetonitrile-$d_3$) δ −86.49-95.62 (m, 2F). LC-MS: method C, RT=2.36 min, MS (ESI) m/z: 461.0 (M+H)$^+$. Analytical HPLC purity (method A): 95%.

Example 70

Methyl 2-(2-(2-(difluoromethoxy)-7-methylquinoxalin-5-yl)-4-methylbenzo[d]thiazol-7-yloxy)ethylcarbamate

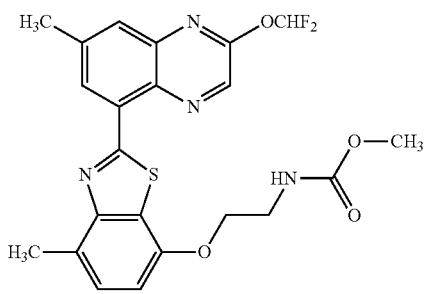
(70)

Intermediate 70A: 2-chloro-7-methoxy-4-methylbenzo[d]thiazole

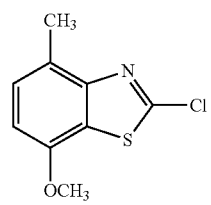
(70A)

To a solution of copper (II) chloride (1.030 g, 7.66 mmol) in acetonitrile (60 mL) at 40° C. was added tert-butyl nitrite (1.097 mL, 8.30 mmol), followed by Intermediate 12C (1.24 g, 6.38 mmol) as a solid. The mixture was stirred at 40° C. for 1.0 h, diluted with EtOAc, washed with 1.0 N HCl, water and brine. After evaporation of solvent, the crude product was dissolved in a small amount of chloroform and charged to a 40 g silica gel cartridge which was eluted with 5% dichloromethane in hexanes for 2 min., then a 12 min gradient from 5% to 50% dichloromethane in hexanes. The desired fractions were combined and concentrated to give Intermediate 70A (1.2 g, 5.62 mmol, 88% yield) as a slightly yellow solid.

Intermediate 70B: 2-chloro-4-methylbenzo[d]thiazol-7-ol

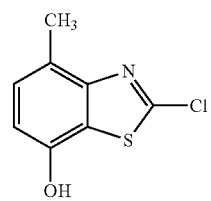
(70B)

Aluminum chloride (369 mg, 2.77 mmol) was added to a solution of Intermediate 70A (215 mg, 1.006 mmol) in toluene (4 mL). The mixture was heated at 85° C. for 1.5 h. The reaction mixture was cooled to room temperature, quenched with ice-cold 1.0 N HCl (50 mL) and EtOAc (50 mL), and stirred at room temperature for 30 min. The organic layer was collected, washed with water, saturated sodium bicarbonate, brine, dried over sodium sulfate. After evaporation of solvent, the crude product was dissolved in a small amount of chloroform and charged to a 40 g silica gel cartridge which was eluted with hexanes for 5 min., then an 18 min gradient from 0% to 40% EtOAc in hexanes. The desired fractions were combined and concentrated to give Intermediate 70B (105 mg, 0.526 mmol, 52.3% yield) as brown solid. $^1$H NMR (400 MHz, Methanol-$d_4$) δ 6.98 (dd, J=2.3, 0.8 Hz, 1H), 6.71 (dd, J=11.9, 2.3 Hz, 1H). LC-MS: method C, RT=2.20 min, MS (ESI) m/z: 547.2 (M+H)$^+$. LC-MS: method C, RT=1.87 min, MS (ESI) m/z: 199.8 (M+H)$^+$.

Intermediate 70C: tert-butyl 2-(2-chloro-4-methyl-benzo[d]thiazol-7-yloxy) ethylcarbamate

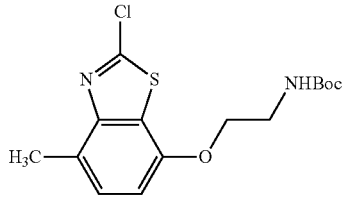

(70C)

A solution of DIAD (0.243 mL, 1.252 mmol) and Intermediate 70B (100 mg, 0.501 mmol) in THF (1 mL) was added to a solution of tert-butyl (2-hydroxyethyl) carbamate (0.194 mL, 1.252 mmol) and triphenylphosphine (197 mg, 0.751 mmol) in THF (2 mL) at 80° C. using a syringe pump for 2 h. The mixture was diluted with dichloromethane and saturated NaHCO$_3$, extracted with dichloromethane, the combined organic layer was washed with brine, dried with MgSO$_4$ and concentrated. The crude sample was purified with 40 g ISCO column eluted with 0-100% EtOAc in hexanes for 20 min, the desired fraction was collected to give Intermediate 70C (170 mg, 0.496 mmol, 99% yield) as a yellow solid. $^1$H NMR (400 MHz, chloroform-d) δ 7.17 (dd, J=8.2, 0.9 Hz, 1H), 6.74 (d, J=8.3 Hz, 1H), 5.09-4.94 (m, 1H), 4.23-4.14 (m, 2H), 3.57 (q, J=5.1 Hz, 2H), 2.60 (d, J=0.5 Hz, 3H), 1.55-1.42 (m, 9H). LC-MS: method C, RT=2.26 min, MS (ESI) m/z: 342.9 (M+H)$^+$.

Intermediate 70D: tert-butyl 2-(2-(2-(difluoromethoxy)-7-methylquinoxalin-5-yl)-4-methylbenzo[d]thiazol-7-yloxy)ethylcarbamate

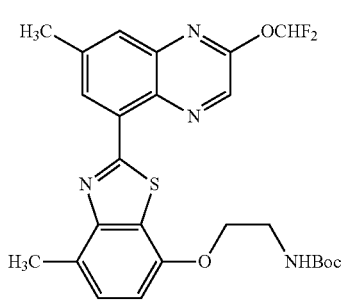

(70D)

To Intermediate I-1 (33.9 mg, 0.101 mmol), Intermediate 70C (45 mg, 0.131 mmol) and [1,1'-bis(diphenylphosphino)ferrocene]dichloropalladium (II) complex with dichloromethane (1:1) (6.60 mg, 8.08 μmol) was added toluene (1.5 mL) and EtOH (0.5 mL). The mixture was sonicated for 1 min, and flushed with argon. To this was added sodium carbonate (0.111 mL, 2M, 0.222 mmol). The reaction mixture was heated in a microwave reactor at 100° C. for 30 min. To the reaction mixture was added EtOAc/water. The organic layers were collected, dried over sodium sulfate. After evaporation of solvent, the crude product was purified with a 12 g ISCO column eluted with 0-70% EtOAc in hexanes for 15 min. The desired fraction was collected to give Intermediate 70D (46 mg, 0.087 mmol, 86% yield) was obtained as a yellow solid. $^1$H NMR (400 MHz, chloroform-d) δ 8.87 (d, J=1.5 Hz, 1H), 8.74 (s, 1H), 7.81 (dd, 1.0 Hz, 1H), 7.94-7.46 (m, 1H), 7.23 (dd, J=8.0, 0.9 Hz, 1H), 6.77 (d, J=8.1 Hz, 1H), 4.25 (t, J=4.9 Hz, 2H), 3.67 (d, J=4.8 Hz, 2H), 2.81 (s, 3H), 2.71 (s, 3H), 1.48 (s, 9H). $^{19}$F NMR (376 MHz, chloroform-d) δ −90.17 (s, 2F). LC-MS: method C, RT=2.63 min, MS (ESI) m/z: 517.0 (M+H)$^+$.

Intermediate 70E 2-(2-(2-(difluoromethoxy)-7-methylquinoxalin-5-yl)-4-methylbenzo[d]thiazol-7-yloxy)ethanamine

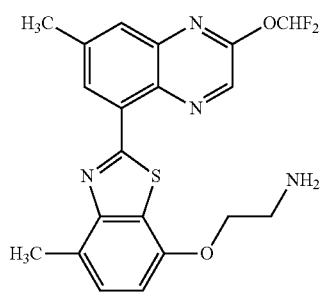

(70E)

To a solution of Intermediate 70D (40 mg, 0.077 mmol) in DCM (1 mL) was added TFA (0.597 mL, 7.74 mmol). The mixture was stirred at room temperature for 1 h. Solvent was removed, the residual was purified with a preparative HPLC (method A, 30-100% B in 6 min.). The desired fractions were placed in a SpeedVac overnight to remove solvent, then lyophilized to Intermediate 70E (35 mg, 0.065 mmol, 84% yield). $^1$H NMR (400 MHz, Methanol-$d_4$) δ 8.85 (s, 1H), 8.71 (s, 1H), 7.87 (s, 1H), 8.01-7.54 (m, 1H), 7.29 (d, J=8.1 Hz, 1H), 6.91 (d, J=8.1 Hz, 1H), 4.45 (t, J=4.9 Hz, 2H), 3.48 (t, J=4.9 Hz, 2H), 2.78 (s, 3H), 2.71 (s, 3H). $^{19}$F NMR (376 MHz, Methanol-$d_4$) δ −78.76 (br. s., 3F), −92.71 (s, 2F). LC-MS: method C, RT=2.10 min, MS (ESI) m/z: 416.9 (M+H)$^+$.

Example 70

To a solution of Intermediate 70E (10 mg, 0.019 mmol) and DIEA (0.016 mL, 0.094 mmol) in DCM (1 mL) was added a solution of methyl chloroformate (2.92 μl 0.038 mmol) in DCM. The mixture was stirred at room temperature for 1 h. The reaction mixture was diluted with EtOAc and water, extracted with EtOAc. The combined organic layer was washed with brine, dried with MgSO$_4$ and concentrated. The crude was purified with a preparative HPLC (method A, 60-100% B in 6 min.). The desired fractions were placed in a SpeedVac overnight to remove solvent, then lyophilized to give Example 70 (5.5 mg, 0.019 mmol, 59% yield). $^1$H NMR (400 MHz, DMSO-$d_6$) δ 9.00 (s, 1H), 8.80 (d, J=1.8 Hz, 1H), 7.93 (s, 1H), 8.11-7.68 (m, 1H), 7.42 (br. s., 1H), 7.30 (d, J=7.8 Hz, 1H), 6.98 (d, J=8.1 Hz, 1H), 4.22 (t, J=5.6 Hz, 2H), 3.50-3.38 (m, 5H), 2.71 (s, 3H), 2.69 (s, 3H). $^{19}$F NMR (376 MHz, DMSO-$d_6$) δ −88.27 (s, 2F). LC-MS: method C, RT=2.49 min, MS (ESI) m/z: 475.0 (M+H)$^+$. Analytical HPLC purity (method A): 96%.

Example 71

2-(2-(difluoromethoxy)-7-methylquinoxalin-5-yl)-6-(thiazol-4-ylmethoxy) benzo[d]thiazole

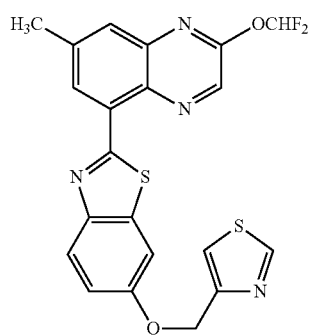
(71)

Intermediate 71A: 2-chlorobenzo[d]thiazol-6-ol

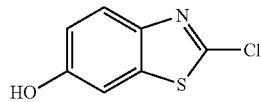
(71A)

Aluminum chloride (6.01 g, 45.1 mmol) was added to a solution of 2-chloro-6-methoxybenzo[d]thiazole (3 g, 15.03 mmol) in toluene (80 mL). The mixture was heated at 110° C. for 1.5 h. TLC indicated a complete conversion of starting material. The reaction mixture was cooled to room temperature, quenched with ice-cold 1.0 N HCl (50 mL), stirred at room temperature for 30 min. The precipitate was collected by filtration, washed with water (3×), saturated sodium bicarbonate (3×), water (3×) and air-dried for 1.0 h under vacuum. It was further dried under high vacuum overnight to give Intermediate 71A (2.6 g, 14.01 mmol, 93% yield) as a pale gray solid. The crude sample was used for the next step without further purification. $^1$H NMR (400 MHz, Methanol-$d_4$) δ 7.70 (d, J=8.8 Hz, 1H), 7.25 (s, 1H), 7.00 (dd, 1.5 Hz, 1H). LC-MS: method C, RT=1.65 min, MS (ESI) m/z: 185.8 (M+H)$^+$.

Intermediate 71B: 6-(tert-butyldimethylsilyloxy)-2-chlorobenzo[d]thiazole

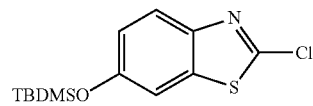
(71B)

To a stirred solution of Intermediate 71A (2.6 g, 14.01 mmol) in DMF (50 mL) was added TBDMS-Cl (2.96 g, 19.61 mmol) and imidazole (1.669 g, 24.51 mmol). The reaction mixture was left stirring at room temperature for 1.0 h. The mixture was diluted with EtOAc/water and extracted with EtOAc. The combined organic layer was washed with brine, dried over sodium sulfate. After evaporation of solvent, the crude product was dissolved in a small amount of chloroform and charged to a 120 g ISCO column which was eluted with hexanes for 3 min., then a 30 min gradient from 0% to 50% EtOAc in hexanes. The desired fractions were combined and concentrated to give Intermediate 71B (3 g, 10.00 mmol, 71.4% yield) as clear orange oil. $^1$H NMR (400 MHz, chloroform-d) δ 7.80 (s, 1H), 7.21 (s, 1H), 7.03-6.94 (m, 1H), 1.01 (s, 9H), 0.24 (s, 6H). LC-MS: method C, RT=2.57 min, MS (ESI) m/z: 300 (M+H)$^+$.

Intermediate 71C 6-(tert-butyldimethylsilyloxy)-2-(2-(difluoromethoxy)-7-methylquinoxalin-5-yl)benzo[d]thiazole

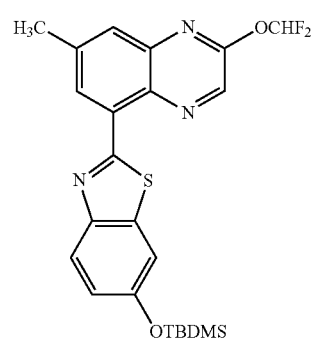
(71C)

To Intermediate I-1 (1 g, 3.94 mmol), Intermediate 71B (1.358 g, 4.53 mmol) and [1,1'-bis(diphenylphosphino)ferrocene]dichloropalladium (II) complex with dichloromethane (1:1) (0.161 g, 0.197 mmol) was added toluene (9 mL), EtOH (3 mL) and sodium carbonate (3.94 mL, 2 M, 7.87 mmol). The mixture was degassed with argon for 5 min. The reaction mixture was heated in a microwave reactor at 135° C. for 30 min. To the reaction mixture was added EtOAc/water/brine. The insoluble was removed by filtration with a pad of celite. The organic layers were collected, washed with brine, dried over sodium sulfate. After evaporation of solvent, the crude product was dissolved in a small amount of toluene/chloroform and charged to a 120 g silica gel cartridge which was eluted with hexanes for 3 min., then a 20 min gradient from 0% to 75% dichloromethane in hexanes (flow rate 65 mL/min). The desired fractions were combined and concentrated to give Intermediate 71C (1.6 g, 2.70 mmol, 68.6% yield) as a bright yellow solid. $^1$H NMR (400 MHz, chloroform-d) δ 8.75 (d, J=1.8 Hz, 1H), 8.69 (s, 1H), 8.03-7.98 (m, 1H), 7.81-7.78 (m, 1H), 7.86-7.49 (m, 1H), 7.40 (d, J=2.5 Hz, 1H), 7.06 (dd, J=8.7, 2.4 Hz, 1H), 2.69 (s, 3H), 1.04 (s, 9H), 0.27 (s, 6H). LC-MS: method C, gradient time 1 min, RT=2.30 min, MS (ESI) m/z: 473.9 (M+H)$^+$.

Intermediate 71D: 2-(2-(difluoromethoxy)-7-methylquinoxalin-5-yl)benzo[d]thiazol-6-ol

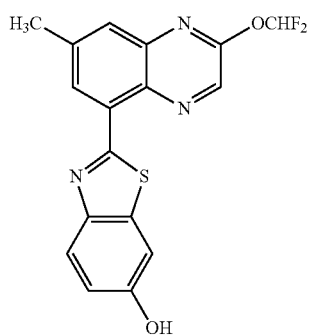

(71D)

To a solution of Intermediate 71C (1.75 g, 3.70 mmol) in THF (15 mL) at room temperature was added acetic acid (0.465 mL, 8.13 mmol), followed by addition of 1.0 N TBAF in THF (4.43 mL, 4.43 mmol) dropwise. The mixture was stirred at room temperature for 20 min. The mixture was diluted with EtOAc, washed with water, saturated sodium bicarbonate (2×), brine, and dried over sodium sulfate. After evaporation of the solvent, the crude product was triturated with EtOAc in hexanes (1:4). The precipitate was collected by filtration to give Intermediate 71D (1 g, 2.78 mmol, 75% yield) as a yellow solid. $^1$H NMR (400 MHz, Methanol-d$_4$) δ 8.70 (s, 1H), 8.64 (d, J=2.0 Hz, 1H), 7.96 (s, 1H), 7.93-7.53 (m, 3H), 7.34 (d, J=2.3 Hz, 1H), 7.03 (dd, 2.5 Hz, 1H), 2.67 (s, 3H). LC-MS: method C, gradient time 1 min, RT=1.45 min, MS (ESI) m/z: 359.9 (M+H)$^+$.

Example 71

A solution of DIAD (0.019 mL, 0.100 mmol) in toluene (0.5 mL) was added to a mixture of Intermediate 71D (12 mg, 0.033 mmol), thiazol-4-ylmethanol (11.54 mg, 0.100 mmol) and triphenylphosphine (17.52 mg, 0.067 mmol) in toluene (2 mL) at 110° C. on 5 portions (0.4 ml each for 30 min). The mixture turned to a clear solution and was stirred at 110° C. for 30 min. The mixture was concentrated and purified with a preparative HPLC (method A, 70-100% B in 6 min.). The desired fractions were placed in a SpeedVac overnight to remove solvent, then lyophilized to give Example 71 (5 mg, 9.86 μmol, 29.5% yield). $^1$H NMR (400 MHz, acetonitrile-d$_3$) δ 8.95 (d, J=2.0 Hz, 1H), 8.78-8.73 (m, 2H), 7.99 (d, J=8.8 Hz, 1H), 7.81 (dd, J=1.9, 0.9 Hz, 1H), 7.71 (d, J=2.5 Hz, 1H), 7.63 (d, J=2.0 Hz, 1H), 7.89-7.48 (m, 1H), 7.24 (dd, J=9.1, 2.5 Hz, 1H), 5.35 (s, 2H), 2.68 (s, 3H). $^{19}$F NMR (376 MHz, acetonitrile-d$_3$) δ −90.50 (s, 2F). LC-MS: method C, RT=2.38 min, MS (ESI) m/z: 456.9 (M+H)$^+$. Analytical HPLC purity (method A): 90%.

Example 72

N-(2-(2-(2-methoxy-7-methylquinoxalin-5-yl)benzo[d]thiazol-6-yloxy)ethyl)benzenesulfonamide

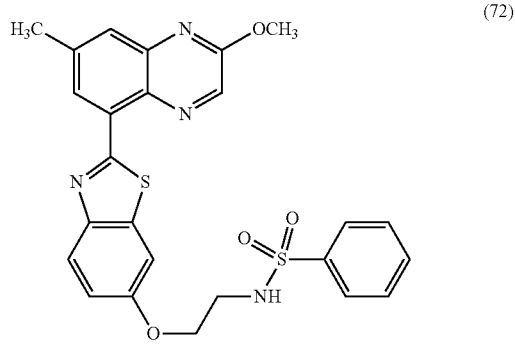 [SMILES: COc1cnc2c(-c3nc4ccc(OCCNS(=O)(=O)c5ccccc5)cc4s3)cc(C)cc2n1]

(72)

To a solution of Example 63 (6.9 mg, 0.013 mmol) in THF (0.5 mL) was added sodium methoxide (0.076 mL, 0.038 mmol). The mixture was stirred at room temperature for 1 h. The reaction mixture was diluted with EtOAc and water, extracted with EtOAc. The combined organic layer was washed with brine, dried with MgSO$_4$ and concentrated. The crude sample was purified with a preparative HPLC (method A, 60-100% B in 6 min.). The desired fractions were placed in a SpeedVac overnight to remove solvent, then lyophilized to give Example 72 (4 mg, 7.11 μmol, 55.9% yield). $^1$H NMR (400 MHz, chloroform-d) δ 8.61 (d, J=2.0 Hz, 1H), 8.56 (s, 1H), 8.02 (d, J=8.8 Hz, 1H), 7.95-7.89 (m, 2H), 7.78 (dd, J=1.9, 0.9 Hz, 1H), 7.61-7.56 (m, 1H), 7.55-7.49 (m, 2H), 7.30 (d, J=2.5 Hz, 1H), 7.03 (dd, J=8.8, 2.5 Hz, 1H), 5.00 (t, J=5.9 Hz, 1H), 4.14 (s, 3H), 4.10 (t, J=5.1 Hz, 2H), 3.47 (q, J=5.7 Hz, 2H), 2.66 (s, 3H). LC-MS: method C, RT=2.37 min, MS (ESI) m/z: 507.0 (M+H)$^+$. Analytical HPLC purity (method A): 95%.

Example 73

N-(2-(2-(2-(difluoromethoxy)-7-methylquinoxalin-5-yl)-4-methylbenzo[d]thiazol-6-yloxy) ethyl)benzenesulfonamide

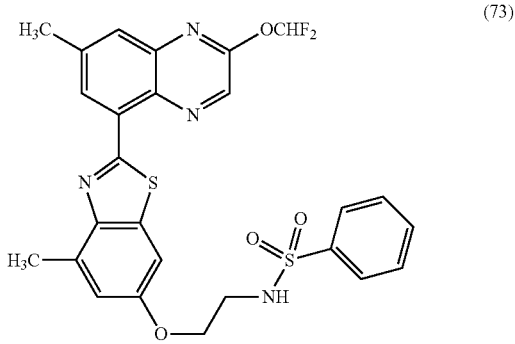 [SMILES: COc1cnc2c(-c3nc4c(C)cc(OCCNS(=O)(=O)c5ccccc5)cc4s3)cc(C)cc2n1]

(73)

To a solution of Intermediate 26F (28 mg, 0.054 mmol) in DCM (1 mL) was added DIEA (0.095 ml, 0.542 mmol) and benzenesulfonyl chloride (19.15 mg, 0.108 mmol). The mixture was stirred at room temperature for 1 hour. Solvent

Example 74

2-(2-(2-(difluoromethoxy)-7-methylquinoxalin-5-yl)benzo[d]thiazol-7-yloxy)ethanol

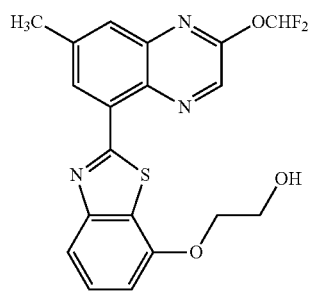

(74)

A solution of DIAD (0.041 mL, 0.209 mmol) in toluene (0.5 mL) was added to a mixture of Intermediate 15J (25 mg, 0.070 mmol), 2-((tetrahydro-2H-pyran-2-yl)oxy)ethanol (20.34 mg, 0.139 mmol) and triphenylphosphine (36.5 mg, 0.139 mmol) in toluene (2 mL) at 110° C. on 5 portion of 0.4 ml each for 30 min. The mixture turned to a clean solution and was stirred at 110° C. for 30 min. The mixture was concentrated and the residual was dissolved in 1 ml of DCM and treated with 12N HCl (0.290 mL, 3.48 mmol) and the mixture was stirred at room temperature for 1 h. The mixture was concentrated and purified with a preparative HPLC (method A, 50-100% B in 6 min.). The desired fractions were placed in a SpeedVac overnight to remove solvent, then lyophilized to give Example 74 (11.5 mg, 0.027 mmol, 38.5% yield). $^1$H NMR (400 MHz, acetonitrile-d$_3$) δ 8.81 (d, J=2.0 Hz, 1H), 8.78 (s, 1H), 7.84 (dd, J=1.9, 0.9 Hz, 1H), 7.90-7.46 (m, 3H), 6.99 (d, J=7.8 Hz, 1H), 4.33-4.25 (m, 2H), 3.99-3.92 (m, 2H), 2.69 (s, 3H). $^{19}$F NMR (376 MHz, acetonitrile-d$_3$) δ −90.50 (s, 2F). LC-MS: method C, RT=2.33 min, MS (ESI) m/z: 403.9 (M+H)$^+$. Analytical HPLC purity (method A): 94%

Example 75

2-(2-(difluoromethoxy)-7-methylquinoxalin-5-yl)-7-(2-methoxyethoxy)benzo[d]thiazole

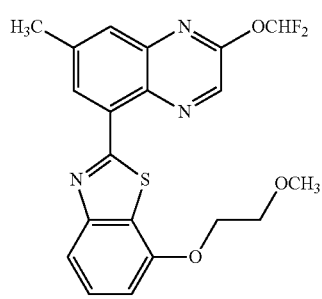

(75)

A solution of DIAD (0.016 mL, 0.083 mmol) in toluene (0.5 mL) was added to a mixture of Intermediate 15J (10 mg, 0.028 mmol), 2-methoxyethanol (4.24 mg, 0.056 mmol) and triphenylphosphine (14.60 mg, 0.056 mmol) in toluene (2 mL) at 110° C. on 5 portion of 0.4 ml each for 30 min. The mixture turned to a clean solution and was stirred at 110° C. for 30 min. The mixture was concentrated and redissolved in 1 ml of DMF and was purified with a preparative HPLC (method A, 60-100% B in 6 min.). The desired fractions were placed in a SpeedVac overnight to remove solvent, then lyophilized to give Example 75 (10 mg, 0.023 mmol, 82% yield). $^1$H NMR (400 MHz, acetonitrile-d$_3$) δ 8.81 (d, J=2.0 Hz, 1H), 8.79 (s, 1H), 7.84 (d, J=0.8 Hz, 1H), 7.90-7.43 (m, 3H), 6.99 (d, J=7.8 Hz, 1H), 4.44-4.25 (m, 2H), 3.87-3.80 (m, 2H), 3.44 (s, 3H), 2.69 (s, 3H) $^{19}$F NMR (376 MHz, acetonitrile-d$_3$) δ −90.22 (s, 2F). LC-MS: method C, RT=2.46 min, MS (ESI) m/z: 418.0 (M+H)$^+$. Analytical HPLC purity (method A): 99%.

Example 76 benzyl 2-(2-(difluoromethoxy)-7-methylquinoxalin-5-yl)benzo[d]thiazol-7-ylcarbamate

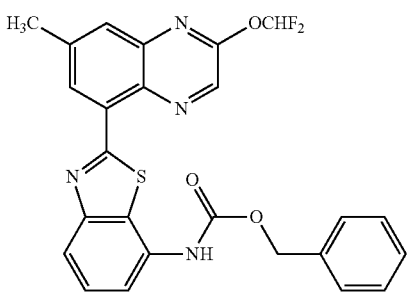

(76)

To a solution of Intermediate 21A (15 mg, 0.042 mmol) in DCM (1 mL) was added DIEA (0.044 mL, 0.251 mmol). After stirring at room temperature for 2 min, benzyl carbonochloridate (0.013 mL, 0.092 mmol) was added. The mixture was heated up to 60° C. for 2 h. The mixture was concentrated and redissolved in 1 ml of DMF and was purified with a preparative HPLC (method A, 50-100% B in 6 min.). The desired fractions were placed in a SpeedVac overnight to remove solvent, then lyophilized to give Example 76 (5 mg, 9.95 μmol, 23.77% yield). ¹H NMR (400 MHz, acetonitrile-d₃) δ 8.80 (d, J=1.8 Hz, 1H), 8.73 (s, 1H), 7.89 (dd, J=8.1, 0.8 Hz, 1H), 7.83 (s, 1H), 7.75 (br. s., 1H), 7.60 (d, J=7.8 Hz, 1H), 7.86-7.51 (m, 1H), 7.48-7.44 (m, 2H), 7.43-7.33 (m, 3H), 5.25 (s, 2H), 2.68 (s, 3H). ¹⁹F NMR (376 MHz, acetonitrile-d₃) δ −90.22 (s, 2F). LC-MS: method C, RT=2.41 min, MS (ESI) m/z: 492.9 (M+H)⁺. Analytical HPLC purity (method A): 98%.

Example 77

2-(2-methoxy-7-methylquinoxalin-5-yl)-6-(2-methoxyethoxy)benzo[d]thiazole

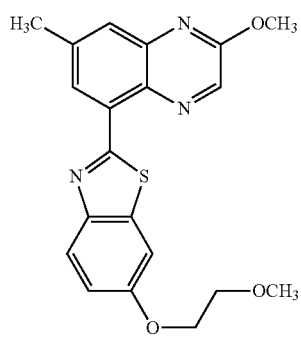

(77)

Intermediate 77A 2-(2-(difluoromethoxy)-7-methylquinoxalin-5-yl)-6-(2-methoxyethoxy)benzo[d]thiazole

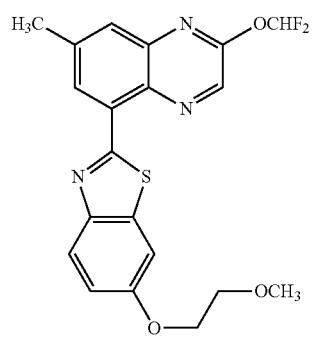

(77A)

A solution of DIAD (0.016 mL, 0.083 mmol) in toluene (0.5 mL) was added to a mixture of Intermediate 71D (10 mg, 0.028 mmol), 2-methoxyethanol (4.24 mg, 0.056 mmol) and triphenylphosphine (14.60 mg, 0.056 mmol) in toluene (2 mL) at 110° C. on 5 portion of 0.4 ml each for 30 min and then was stirred at 110° C. for 30 min. The mixture was concentrated and redissolved in 1 ml of DMF and was purified with a preparative HPLC (method A, 60-100% B in 6 min.). The desired fractions were placed in a SpeedVac overnight to remove solvent, then lyophilized to give Intermediate 77A (10 mg, 0.023 mmol, 82% yield). ¹H NMR (400 MHz, acetonitrile-d₃) δ 8.75 (d, J=1.8 Hz, 1H), 8.74 (s, 1H), 7.98 (d, J=8.8 Hz, 1H), 7.81 (dd, J=1.9, 0.9 Hz, 1H), 7.60 (d, J=2.5 Hz, 1H), 7.88-7.50 (m, 1H), 7.16 (dd, J=8.8, 2.5 Hz, 1H), 4.27-4.08 (m, 2H), 3.82-3.67 (m, 2H), 3.40 (s, 3H), 2.68 (s, 3H). ¹⁹F NMR (376 MHz, acetonitrile-d₃) δ −90.22 (s, 2F). LC-MS: method C, RT=2.47 min, MS (ESI) m/z: 418.1 (M+H)⁺. Analytical HPLC purity (method A): 95%.

Example 77

To a solution of Intermediate 77A (5 mg, 0.012 mmol) in THF (0.5 mL) was added sodium methoxide (0.072 mL, 0.036 mmol). The mixture was stirred at room temperature for 1 h. The reaction was quenched by 1 drop of water and concentrated. The residual was purified via preparative LC/MS (method C, 50-90% B over 10 min., then a 5-min hold at 100% B). Fractions containing the desired product were combined and dried via centrifugal evaporation to Example 77 (3.0 mg, 7.79 μmol, 65.0% yield). ¹H NMR (500 MHz, methanol-d₄) δ 8.51 (s, 1H), 8.47 (d, J=1.9 Hz, 1H), 7.95 (d, J=9.1 Hz, 1H), 7.74 (d, J=0.8 Hz, 1H), 7.47 (s, 1H), 7.15 (dd, J=8.8, 2.5 Hz, 1H), 4.24-4.18 (m, 2H), 4.11 (s, 3H), 3.85-3.78 (m, 2H), 2.63 (s, 3H). LC-MS: method C, RT=2.41 min, MS (ESI) m/z: 382.15 (M+H)⁺. Analytical HPLC purity (method B): 99%.

Example 78

2-(2-methoxy-7-methylquinoxalin-5-yl)-7-(2-methoxyethoxy)benzo[d]thiazole

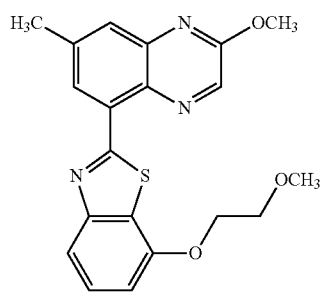

(78)

To a solution of Example 75 (8.5 mg, 0.020 mmol) in THF (0.5 mL) was added sodium methoxide (0.122 mL, 0.061 mmol). The mixture was stirred at room temperature for 1 h. The reaction was quenched by 1 drop of water solvent was removed, the residual was purified via preparative LC/MS (method C, 50-90% B over 10 min., then a 5-min hold at 100% B). Fractions containing the desired product were combined and dried via centrifugal evaporation to Example 78 (6.6 mg, 0.017 mmol, 85% yield). ¹H NMR (500 MHz, methanol-d₄) δ 8.55 (s, 1H), 8.53 (d, J=1.9 Hz, 1H), 7.76 (s, 1H), 7.70 (d, J=8.0 Hz, 1H), 7.43 (t, J=8.1 Hz, 1H), 6.90 (d, J=7.7 Hz, 1H), 4.41-4.32 (m, 2H), 4.11 (s, 3H), 3.88 (dd, J=5.4, 3.7 Hz, 2H), 3.50 (s, 3H), 2.63 (s, 3H). LC-MS: method C, RT=2.41 min, MS (ESI) m/z: 382.15 (M+H)⁺. Analytical HPLC purity (method B): 100%.

Example 79

N-(2-(2-(2-methoxy-7-methylquinoxalin-5-yl)-4-methylbenzo[d]thiazol-6-yloxy)ethyl) benzenesulfonamide

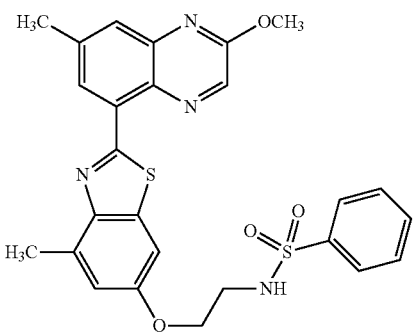

(79)

Intermediate 79A

N-(2-(2-(2-(difluoromethoxy)-7-methylquinoxalin-5-yl)-4-methylbenzo[d]thiazol-6-yloxy) ethyl)-2,2,2-trifluoro-N-(phenylsulfonyl)acetamide

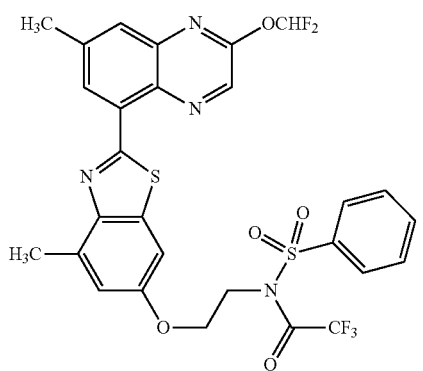

(79A)

To a solution of Intermediate 26F (28 mg, 0.054 mmol) in DCM (1 ml) was added TFA (0.418 ml, 5.42 mmol) and the mixture was stirred at room temperature for 1 hour. Solvent was removed and the sample was under vacuum overnight. The residual was dissolved in DCM (1 ml) then DIEA (0.095 ml, 0.542 mmol) and benzenesulfonyl chloride (19.15 mg, 0.108 mmol) was added. The mixture was stirred at room temperature for 1 hour. Solvent was removed under vacuum and the residual was purified with a preparative HPLC (method A, 70-100% B in 6 min.). The desired fractions were lyophilized in a SpeedVac overnight to remove solvent, then lyophilized to give Intermediate 79A (8 mg, 0.012 mmol, 22.62% yield). LC-MS: method C, RT=2.68 min, MS (ESI) m/z: 653 (M+H)+.

Example 79

To a solution of Intermediate 79A (8 mg, 0.012 mmol) in THF (0.5 mL) was added sodium methoxide (0.074 mL, 0.037 mmol). The mixture was stirred at room temperature for 1 h. The reaction was quenched by 1 drop of water and concentrated. The residual was diluted with 1 ml of DMF and was purified via preparative LC/MS (method C, 55-90% B over 20 min., then a 10-min hold at 90% B). Fractions containing the desired product were combined and dried via centrifugal evaporation to Example 79 (3.9 mg, 7.49 µmol, 61.1% yield). $^1$H NMR (500 MHz, methanol-$d_4$) δ 8.55 (d, J=1.7 Hz, 1H), 8.51 (s, 1H), 7.88 (s, 1H), 7.87-7.85 (m, 1H), 7.73 (s, 1H), 7.54 (d, J=7.2 Hz, 1H), 7.51-7.46 (m, 2H), 7.13 (d, J=2.2 Hz, 1H), 6.80 (d, J=1.7 Hz, 1H), 4.10 (s, 3H), 4.03 (t, J=5.5 Hz, 2H), 3.34 (t, J=5.5 Hz, 2H), 2.75 (s, 3H), 2.64 (s, 3H). LC-MS: method C, RT=2.48 min, MS (ESI) m/z: 521.0 (M+H)+. Analytical HPLC purity (method B): 100%.

Example 80

Methyl 2-(2-(difluoromethoxy)-7-methylquinoxalin-5-yl)benzo[d]thiazol-7-ylcarbamate

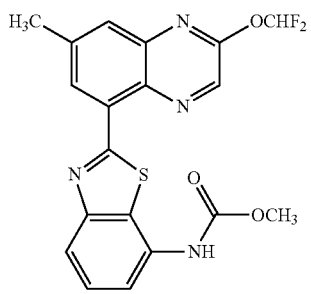

(80)

To a solution of Intermediate 21A (6 mg, 0.017 mmol) in DCM (1 mL) was added DIEA (0.058 mL, 0.335 mmol). After stirring at room temperature for 2 min, methyl chloroformate (18.99 mg, 0.201 mmol) was added to the solution and the mixture was stirred at 60° C. for 3 h. Solvent was removed, the residual was dissolved in 1 ml of DMF and purified via preparative LC/MS (method C, 35-70% B over 10 min., then a 5-min hold at 100% B). Fractions containing the desired product were combined and dried via centrifugal evaporation to afford Example 80 (3.6 mg, 8.30 µmol, 49.6% yield). $^1$H NMR (500 MHz, methanol-$d_4$) δ 8.72-8.68 (m, 2H), 7.88 (d, J=8.8 Hz, 1H), 7.84-7.52 (m, 3H), 7.51-7.45 (m, 1H), 3.82 (s, 3H), 2.67 (s, 3H). LC-MS: method C, RT=2.24 min, MS (ESI) m/z: 416.9 (M+H)+. Analytical HPLC purity (method B): 96%

Example 81

N-(2-(2-(2-(difluoromethoxy)-7-methylquinoxalin-5-yl)-4-methylbenzo[d]thiazol-6-yloxy)ethyl)-4-fluorobenzenesulfonamide

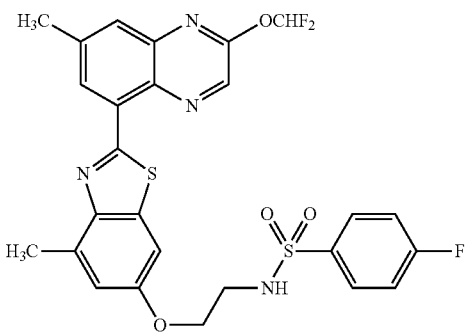
(81)

To a solution of Intermediate 26F (10 mg, 0.022 mmol) and DIEA (0.039 mL, 0.221 mmol) in DCM (1 mL) was added a solution of 4-fluorobenzene-1-sulfonyl chloride (8.59 mg, 0.044 mmol) in 0.2 ml of DCM. The mixture was stirred at room temperature for 1 h. Solvent was removed under vacuum and the residual was purified via preparative LC/MS (method C, 45-85% B over 10 min., then a 7-min hold at 100% B). Fractions containing the desired product were combined and dried via centrifugal evaporation to Example 81 (4.4 mg, 7.66 µmol, 34.7% yield). $^1$H NMR (500 MHz, methanol-$d_4$) δ 8.71 (d, J=1.9 Hz, 1H), 8.67 (s, 1H), 7.93-7.88 (m, 2H), 7.78 (dd, 1.0 Hz, 1H), 7.83-7.51 (m, 1H), 7.23-7.12 (m, 3H), 6.80 (dd, J=2.5, 0.8 Hz, 1H), 4.05 (t, J=5.5 Hz, 2H), 3.35 (t, J=5.5 Hz, 2H), 2.76 (s, 3H), 2.67 (s, 3H). LC-MS: method C, RT=2.50 min, MS (ESI) m/z: 575.1 (M+H)$^+$. Analytical HPLC purity (method B): 100%.

Example 82

2-(2-(2-(difluoromethoxy)-7-methylquinoxalin-5-yl)benzo[d]thiazol-7-yloxy)-N-phenylacetamide

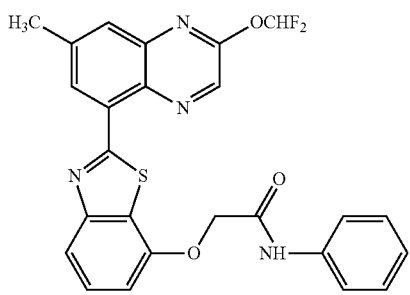
(82)

Intermediate 82A: tert-butyl 2-((2-(2-(difluoromethoxy)-7-methylquinoxalin-5-yl)benzo[d]thiazol-7-yl)oxy)acetate

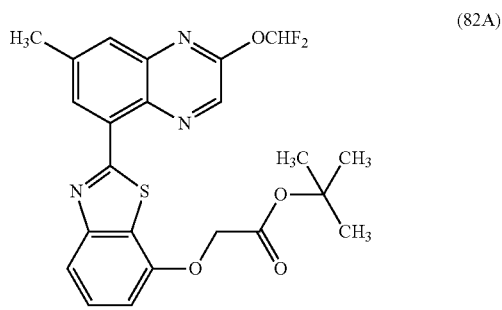 [SMILES: Cc1cc(-c2nc3cccc(OCC(=O)OC(C)(C)C)c3s2)c2ncc(OC(F)F)nc2c1]
(82A)

To a solution of Intermediate 15J (20 mg, 0.056 mmol) in DMF (1 mL) was added butyl 2-bromoacetate (0.041 mL, 0.278 mmol) and NaH (4.45 mg, 0.111 mmol). The mixture was stirred at room temperature for 30 min, diluted with EtOAc and water, extracted with EtOAc. The combined organic layer was washed with brine, dried with MgSO$_4$ and concentrated. The crude sample was purified with a 12 g ISCO column eluted with 0-50% EtOAc in hexanes for 15 min. The desired fraction was collected to give Intermediate 82A (25 mg, 0.053 mmol, 95% yield) as a yellow solid. $^1$H NMR (500 MHz, Methanol-$d_4$) δ 8.71 (s, 2H), 7.87-7.66 (m, 3H), 7.44 (t, J=8.0 Hz, 1H), 6.79 (d, J=8.0 Hz, 1H), 4.78 (s, 2H), 2.68 (s, 3H), 1.48 (s, 9H). LC-MS: method C, RT=2.54 min, MS (ESI) m/z: 474 (M+H)$^+$.

Intermediate 82B 2-(2-(2-(difluoromethoxy)-7-methylquinoxalin-5-yl)benzo[d]thiazol-7-yloxy)acetic acid

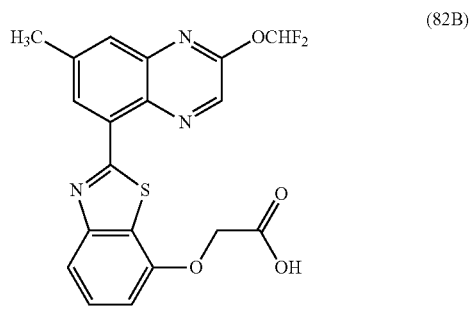 [SMILES: Cc1cc(-c2nc3cccc(OCC(=O)O)c3s2)c2ncc(OC(F)F)nc2c1]
(82B)

To a solution of Intermediate 82A (16 mg, 0.034 mmol) in DCM (1 mL) was added TFA (0.260 mL, 3.38 mmol). The mixture was stirred at room temperature overnight, Solvent was removed, the residual was dissolved in 1 ml of DMF and was purified via preparative LC/MS (method D, 10-45% B over 10 min., then a 5-min hold at 100% B). Fractions containing the desired product were combined and dried via centrifugal evaporation to give Intermediate 82B (14 mg, 0.034 mmol, 99% yield). LC-MS: method C, RT=2.25 min, MS (ESI) m/z: 418(M+H)$^+$.

Example 82

To a solution of Intermediate 82B (6.5 mg, 0.016 mmol) in CH$_2$Cl$_2$ (1 mL) was added DIEA (27.2 µL, 0.156 mmol)

and 1-propanephosphonic acid cyclic anhydride, (T3P) (180 μL, 50 wt % solution in ethyl acetate, 0.047 mmol) was added aniline (5.80, 0.062 mmol). The reaction mixture was stirred at room temperature for 2 h. Solvent was removed, the residual was dissolved in 1 ml of DMF and was purified via preparative LC/MS (method C, 50-90% B over 10 min., then a 7-min hold at 100% B). Fractions containing the desired product were combined and dried via centrifugal evaporation to afford Example 82 (5.0 mg, 10.15 μmol, 65.2% yield). $^1$H NMR (500 MHz, DMSO-d$_6$) δ 9.49 (s, 1H), 8.23 (s, 1H), 7.99 (d, J=1.7 Hz, 1H), 7.36-6.91 (m, 2H), 6.82 (d, J=7.7 Hz, 2H), 6.71 (t, J=8.0 Hz, 1H), 6.52 (t, J=8.0 Hz, 2H), 6.27 (s, 1H), 6.20 (d, J=7.7 Hz, 1H), 1.87 (s, 3H), 1.73-1.57 (m, 3H). LC-MS: method C, RT=2.46 min, MS (ESI) m/z: 493.1 (M+H)$^+$. Analytical HPLC purity (method B): 100%.

Example 83

N-(2-(2-(2-(difluoromethoxy)-7-methylquinoxalin-5-yl)-4-methylbenzo[d]thiazol-6-yloxy) ethyl)-4-(trifluoromethyl)benzenesulfonamide

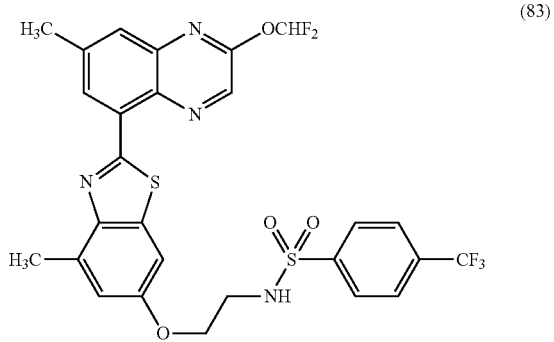 [SMILES: Cc1cc(-c2nc3c(C)cc(OCCNS(=O)(=O)c4ccc(C(F)(F)F)cc4)cc3s2)c2ncc(OC(F)F)nc2c1]

(83)

To a solution of Intermediate 26F (15 mg, 0.033 mmol) and DIEA (0.058 mL, 0.331 mmol) in DCM (1 mL) was added a solution of 4-(trifluoromethyl)benzene-1-sulfonyl chloride (12.15 mg, 0.050 mmol) in 0.2 ml of DCM. The mixture was stirred at room temperature for 1 h. Solvent was removed, the residual was purified via preparative LC/MS (method C, 55-95% B over 10 min., then a 5-min hold at 100% B). Fractions containing the desired product were combined and dried via centrifugal evaporation to give Example 83 (6.2 mg, 9.93 μmol, 30.0% yield). $^1$H NMR (500 MHz, DMSO-d$_6$) δ 8.13 (s, 1H), 7.97-7.84 (m, 1H), 7.51-7.41 (m, 1H), 7.26-7.22 (m, 2H), 7.17-7.12 (m, 2H), 7.21-6.91 (m, 2H), 6.69-6.46 (m, 1H), 6.02-5.83 (m, 1H), 3.26-3.18 (m, 2H), 2.50 (s, 2H), 1.89 (s, 3H), 1.86 (s, 3H). LC-MS: method C, RT=2.54 min, MS (ESI) m/z: 625.1(M+H)$^+$. Analytical HPLC purity (method B): 99%.

Example 84

N-(2-(2-(2-(difluoromethoxy)-7-methylquinoxalin-5-yl)-4-methylbenzo[d]thiazol-6-yloxy) ethyl)-2,4-difluorobenzenesulfonamide

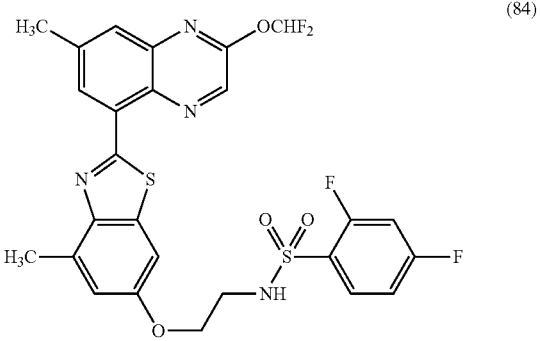 [SMILES: Cc1cc(-c2nc3c(C)cc(OCCNS(=O)(=O)c4ccc(F)cc4F)cc3s2)c2ncc(OC(F)F)nc2c1]

(84)

To a solution of Intermediate 26F (15 mg, 0.033 mmol) and DIEA (0.058 mL, 0.331 mmol) in DMF (1 mL) was added a solution of 2,4-difluorobenzene-1-sulfonyl chloride (10.56 mg, 0.050 mmol) in 0.2 ml of DCM. The mixture was stirred at room temperature for 1 h. Solvent was removed, the residual was purified via preparative LC/MS (method C: 0-100% B over 10 min., then a 5-min hold at 100% B). Fractions containing the desired product were combined and dried via centrifugal evaporation to give Example 84 (7.8 mg, 0.013 mmol, 39.7% yield). $^1$H NMR (500 MHz, Methanol-d$_4$) δ 8.72 (s, 1H), 8.69 (s, 1H), 7.92 (d, J=6.1 Hz, 1H), 7.79 (s, 1H), 7.84-7.52 (m, 1H), 7.15 (s, 1H), 7.01 (s, 1H), 6.96-6.88 (m, 1H), 6.75 (s, 1H), 4.07-4.03 (m, 2H), 3.73 (s, 3H), 3.46 (t, J=5.4 Hz, 2H). LC-MS: method C, RT=2.45 min, MS (ESI) m/z: 593.1 (M+H)$^+$. Analytical HPLC purity (method B): 100%.

Example 85

N-(2-(2-(2-(difluoromethoxy)-7-methylquinoxalin-5-yl)-4-methylbenzo[d]thiazol-6-yloxy) ethyl)-3,4-difluorobenzenesulfonamide

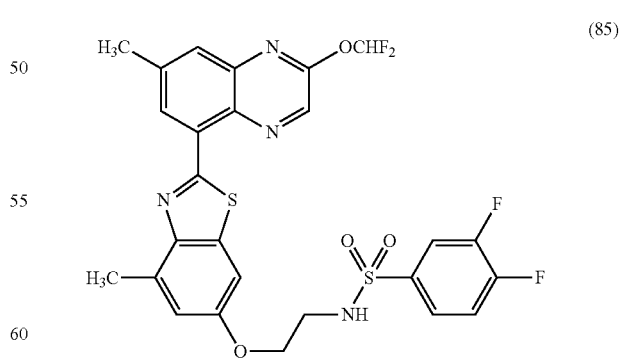

(85)

To a solution of Intermediate 26F (15 mg, 0.033 mmol) and DIEA (0.058 mL, 0.331 mmol) in DMF (1 mL) was added a solution of 3,4-difluorobenzene-1-sulfonyl chloride (10.56 mg, 0.050 mmol) in 0.2 ml of DCM. The mixture was stirred at room temperature for 2 h. Solvent was removed, Example 86

4-chloro N-(2-(2-(2-(difluoromethoxy)-7-methylquinoxalin-5-yl)-4-methylbenzo[d]thiazol-6-yloxy)ethyl)benzenesulfonamide

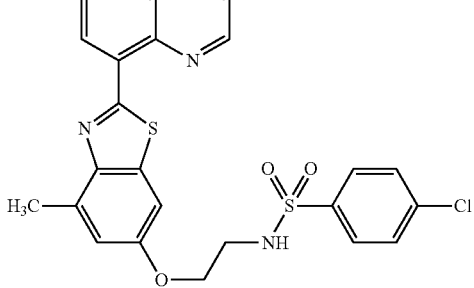
(86)

To a solution of Intermediate 26F (15 mg, 0.033 mmol) and DIEA (0.058 mL, 0.331 mmol) in DMF (1 mL) was added a solution of 4-chlorobenzene-1-sulfonyl chloride (10.49 mg, 0.050 mmol) in 0.2 ml of DCM. The mixture was stirred at room temperature for 1 h. LCMS indicated a completion of the reaction. Solvent was removed and the sample was purified via preparative LC/MS (method C, 60-100% B over 10 min., then a 5-min hold at 100% B). Fractions containing the desired product were combined and dried via centrifugal evaporation to Example 86 (4.9 mg, 8.29 μmol, 25.03% yield). $^1$H NMR (500 MHz, DMSO-$d_6$) δ 8.96 (s, 1H), 8.82-8.64 (m, 1H), 8.08-7.61 (m, 7H), 7.48-7.37 (m, 1H), 6.84-6.78 (m, 1H), 4.09-4.00 (m, 2H), 3.25-3.22 (m, 2H), 2.73 (s, 3H), 2.68 (s, 3H). LC-MS: method C, RT=2.53 min, MS (ESI) m/z: 591.1 (M+H)$^+$. Analytical HPLC purity (method B): 100%.

Example 87

N-(2-(2-(2-methoxy-7-methylquinoxalin-5-yl)-4-methylbenzo[d]thiazol-6-yloxy)ethyl)-4-methylbenzenesulfonamide

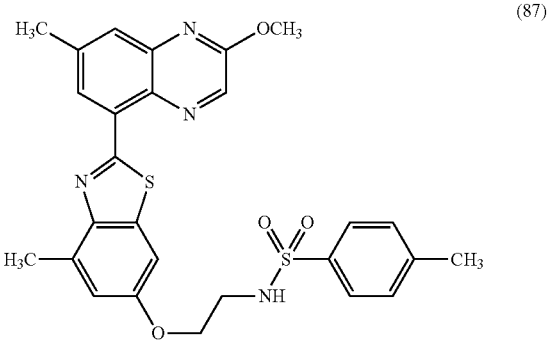
(87)

Intermediate 87A

N-(2-(2-(2-(difluoromethoxy)-7-methylquinoxalin-5-yl)-4-methylbenzo[d]thiazol-6-yloxy) ethyl)-4-methylbenzenesulfonamide

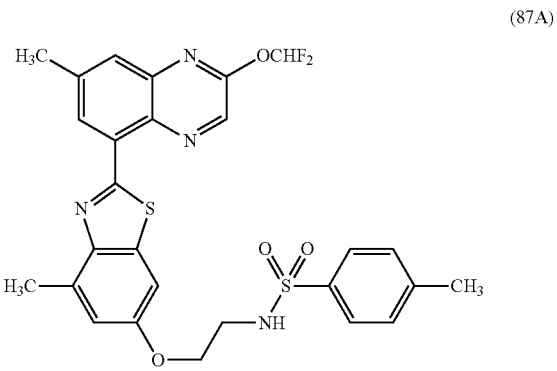
(87A)

To a solution of Intermediate 26F (15 mg, 0.033 mmol) and DIEA (0.058 mL, 0.331 mmol) in DMF (1 mL) was added a solution of 4-methylbenzene-1-sulfonyl chloride (9.47 mg, 0.050 mmol) in 0.2 ml of DCM. The mixture was stirred at room temperature for 1 h. LCMS indicated a completion of the reaction. Solvent was removed, the residual was purified via preparative LC/MS (method C, 55-95% B over 10 min., then a 5-min hold at 100% B). Fractions containing the desired product were combined and dried via centrifugal evaporation to give Intermediate 87A (5.5 mg, 9.64 μmol, 29% yield). $^1$H NMR (500 MHz, DMSO-$d_6$) δ 8.96 (s, 1H), 8.72 (d, J=1.7 Hz, 1H), 8.04-7.74 (m, 2H), 7.72 (d, J=8.3 Hz, 2H), 7.44 (d, J=2.2 Hz, 1H), 7.39 (d, J=8.0 Hz, 2H), 6.88 (d, J=1.4 Hz, 1H), 4.04 (t, J=5.4 Hz, 2H), 3.17 (t, J=5.4 Hz, 2H), 2.73 (s, 3H), 2.67 (s, 3H), 2.36 (s, 3H). LC-MS: method C, RT=2.50 min, MS (ESI) m/z: 571.2 (M+H)$^+$. Analytical HPLC purity (method B): 100%.

Example 87

To a solution of Intermediate 87A (3.32 mg, 5.82 μmol) in DMF (0.5 mL) was added sodium methoxide in MeOH (0.035 mL, 0.5M, 0.017 mmol). The mixture was stirred at room temperature for 2 h. LCMS indicated completion of the reaction. The reaction was quenched by water and was purified via preparative LC/MS (method C, 55-95% B over 10 min., then a 5-min hold at 100% B). Fractions containing the desired product were combined and dried via centrifugal evaporation to give Example 87 (2.7 mg, 5.05 μmol, 87% yield). $^1$H NMR (500 MHz, Methanol-$d_4$) δ 8.55 (d, J=1.9 Hz, 1H), 8.51 (s, 1H), 7.74 (d, J=8.3 Hz, 3H), 7.27 (d, J=8.3 Hz, 2H), 7.10 (d, J=2.5 Hz, 1H), 6.79 (d, J=1.4 Hz, 1H), 4.22 (br. s., 2H), 4.10 (s, 3H), 4.01 (t, J=5.5 Hz, 2H), 3.35-3.33 (m, 2H), 2.75 (s, 3H), 2.64 (s, 3H). LC-MS: method C, RT=2.55 min, MS (ESI) m/z: 535.3 (M+H)$^+$. Analytical HPLC purity (method B): 100%.

Example 89

4-fluoro N-(2-(2-(2-(methoxymethyl)-7-methylquinoxalin-5-yl)-4-methylbenzo[d]thiazol-6-yloxy)ethyl)benzenesulfonamide

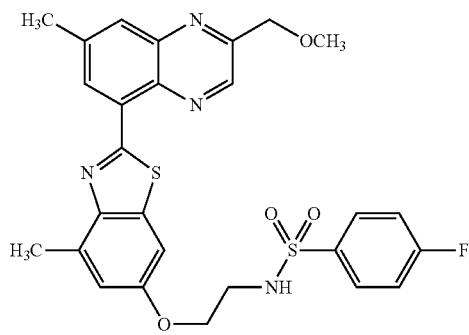
(89)

Intermediate 89A: 2-chloro-6-methoxy-4-methylbenzo[d]thiazole

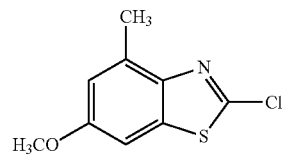
(89A)

To a solution of copper (II) chloride (1.661 g, 12.35 mmol) in acetonitrile (8 mL) at 40° C. was added tert-butyl nitrite (1.769 mL, 13.38 mmol), followed by Intermediate I-3A (2.2 g, 11.33 mmol) as a solid. The mixture was stirring at 40° C. for 2.0 h. HPLC and LCMS indicated a complete conversion of starting material. The mixture was diluted with EtOAc, washed with 0.5 HCl, saturated sodium bicarbonate and brine. After evaporation of solvent, Intermediate 89A (2.4 g, 11.23 mmol, 99% yield) was obtained as brown solid. $^1$H NMR (500 MHz, chloroform-d) δ 7.07 (d, J=2.5 Hz, 1H), 6.93-6.77 (m, 1H), 3.85 (s, 3H), 2.66 (s, 3H). LC-MS: method C, RT=2.08 min, MS (ESI) m/z: 213.9 (M+H)$^+$.

Intermediate 89B: 2-chloro-4-methylbenzo[d]thiazol-6-ol

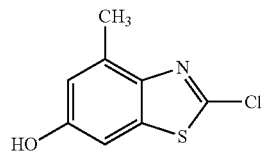
(89B)

Aluminum chloride (4.49 g, 33.7 mmol) was added to a solution of Intermediate 89A (2.4 g, 11.23 mmol) in toluene (50 mL). The mixture was heated at 110° C. for 1.5 h. TLC indicated a complete conversion of starting material. The reaction mixture was cooled to room temperature, quenched with ice-cold 1.0 N HCl (50 mL), stirred at room temperature for 30 min. The precipitate was collected by filtration, washed with water (3x), saturated sodium bicarbonate (3x), water (3x) and air-dried for 1.0 h under vacuum. It was further dried under high vacuum overnight to give Intermediate 89B as brown solid (2.2 g, 11.02 mmol, 98% yield).

Intermediate 89C: (6-(tert-butyldimethylsilyloxy)-2-chloro-4-methylbenzo[d]thiazole

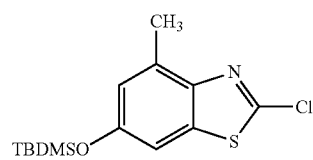
(89C)

To a stirred solution of Intermediate 89B (2.2 g, 11.02 mmol) in DMF (50 mL) was added TBDMS-Cl (2.325 g, 15.43 mmol) and imidazole (1.313 g, 19.28 mmol). The reaction mixture was left stirring at room temperature for 1.0 h. HPLC and TLC indicated a clean reaction. The mixture was partitioned between EtOAc/water. The organic layer was washed with brine, dried over sodium sulfate. After evaporation of solvent, the crude product was dissolved in a small amount of chloroform and charged to a 120 g ISCO column which was eluted with hexanes for 3 min., then a 30 min gradient from 0% to 50% EtOAc in hexanes. The desired fractions were combined and concentrated to give Intermediate 89C (1.57 g, 5.00 mmol, 45.4% yield) as a clear orange solid. $^1$H NMR (400 MHz, chloroform-d) δ 7.09-6.94 (m, 1H), 6.81 (dd, J=2.5, 0.8 Hz, 1H), 2.64 (s, 3H), 1.01 (s, 9H), 0.23 (s, 6H). LC-MS: method C, RT=2.74 min, MS (ESI) m/z: 314 (M+H)$^+$.

Intermediate 89D 6-(tert-butyldimethylsilyloxy)-2-(2-(methoxymethyl)-7-methylquinoxalin-5-yl)-4-methyl benzo[d]thiazole

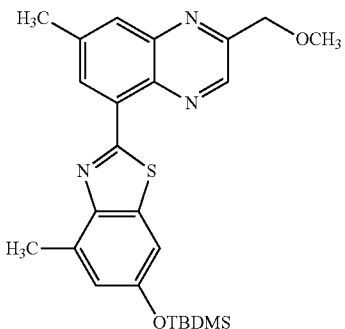
(89D)

To Intermediate I-2 (28 mg, 0.121 mmol), Intermediate 89C (37.9 mg, 0.121 mmol) and [1,1'-bis(diphenylphosphino)ferrocene]dichloropalladium (II) complex with dichloromethane (1:1) (4.93 mg, 6.03 µmol) was added toluene (0.75 mL), EtOH (0.25 mL) and sodium carbonate (0.121 mL, 2M, 0.241 mmol). The mixture was degassed with argon for 5 min. The reaction mixture was heated in a microwave reactor at 135° C. for 40 min. LCMS indicated a clean reaction. To the reaction mixture was added EtOAc/water/brine. The insoluble was removed by filtration with a pad of celite. The organic layers were collected, washed with brine, dried over sodium sulfate. After evaporation of solvent, the crude product was dissolved in a small amount of chloroform and charged to a 12 g ISCO column which was eluted with hexanes for 3 min., then a 20 min gradient from 0% to 75% dichloromethane in hexanes The desired fractions were combined and concentrated to give Intermediate 89D (48 mg, 0.103 mmol, 85% yield). LC-MS: method C, gradient time 1 min, RT=2.53 min, MS (ESI) m/z: 466.2 (M+H)$^+$.

Intermediate 89E 2-(2-(methoxymethyl)-7-methylquinoxalin-5-yl)-4-methylbenzo[d]thiazol-6-ol

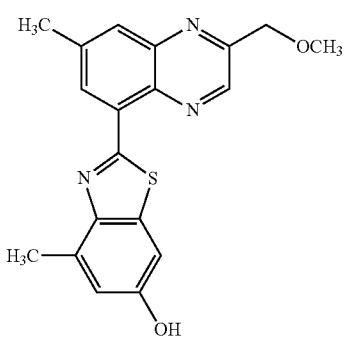
(89E)

To a solution of Intermediate 89D (48 mg, 0.103 mmol) in THF (5 mL) at room temperature was added acetic acid (0.013 mL, 0.227 mmol) followed by addition of 1.0 N TBAF in THF (0.124 mL, 0.124 mmol) dropwise. The mixture was stirred at room temperature for 30 min. LCMS indicated a completion of reaction. The mixture was diluted with EtOAc, washed with water, saturated sodium bicarbonate (2×), brine, and dried over sodium sulfate. After evaporation of the solvent, the crude product was purified with a 12 g ISCO column eluting with 0% to 80% EtOAc in hexanes for 15 min. The desired fraction was collected to give Intermediate 89E (36 mg, 0.102 mmol, 99% yield). $^1$H NMR (500 MHz, chloroform-d) δ 9.08 (s, 1H), 8.93-8.77 (m, 1H), 7.94 (s, 1H), 7.23 (d, J=2.2 Hz, 1H), 6.86 (d, J=1.7 Hz, 1H), 4.85 (s, 2H), 3.58 (s, 3H), 2.83 (s, 3H), 2.71 (s, 3H). LC-MS: method C, RT=2.21 min, MS (ESI) (m/z) 352 [M+H]$^+$

Intermediate 89F: tert-butyl 2-(2-(2-(methoxymethyl)-7-methylquinoxalin-5-yl)-4-methylbenzo[d]thiazol-6-yloxy)ethylcarbamate

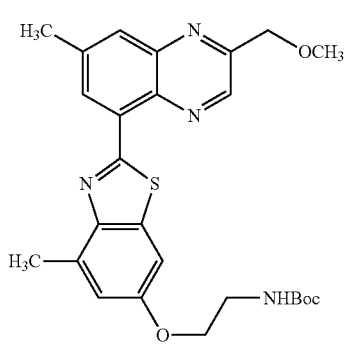
(89F)

A solution of DIAD (0.055 mL, 0.282 mmol) in 1 ml of toluene was added dropwise to a mixture of Intermediate 89E (33 mg, 0.094 mmol), tert-butyl (2-hydroxyethyl)carbamate (18.16 mg, 0.113 mmol) and triphenylphosphine (49.3 mg, 0.188 mmol) in toluene (1 mL) at 110° C. LCMS indicated a completion of the reaction. The mixture was concentrated and purified with a 40 g ISCO column eluted with 0-70% EtOAc in hexanes for 20 min. The desired fraction was collected and concentrated to give Intermediate 89F (45 mg, 0.091 mmol, 97% yield). $^1$H NMR (500 MHz, methanol-d$_4$) δ 9.05 (s, 1H), 8.79 (d, J=1.7 Hz, 1H), 7.90 (s, 1H), 7.28 (d, J=2.5 Hz, 1H), 6.93 (d, J=1.7 Hz, 1H), 4.81 (s, 2H), 4.09 (t, J=5.5 Hz, 2H), 3.56 (s, 3H), 3.50 (t, J=5.4 Hz, 2H), 2.78 (s, 3H), 2.69 (s, 3H), 1.44 (s, 9H). LC-MS: method C, RT=2.49 min, MS (ESI) (m/z) 495.1 [M+H]$^+$.

Intermediate 89G 2-(2-(2-(methoxymethyl)-7-methylquinoxalin-5-yl)-4-methylbenzo[d]thiazol-6-yloxy)ethanamine

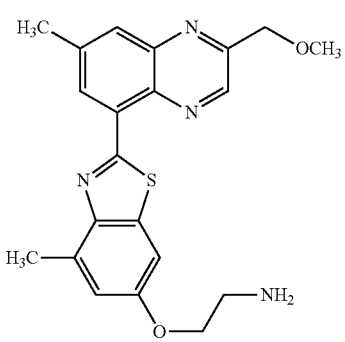
(89G)

To a solution of Intermediate 89F (40 mg, 0.081 mmol) in DCM (1 mL) was added TFA (1 mL, 12.98 mmol). The mixture was stirred at room temperature for 1 h. LCMS indicated a completion of the reaction. Solvent was removed. The crude sample was diluted with EtOAc and water, extracted with EtOAc, the combined organic layer was washed with saturated NaHCO$_3$ and brine, dried with MgSO$_4$ and concentrated to give Intermediate 89G (30 mg, 0.076 mmol, 94% yield). $^1$H NMR (500 MHz, Methanol-d$_4$) δ 9.05 (s, 1H), 8.81 (d, J=1.7 Hz, 1H), 7.91 (s, 1H), 7.29 (d, J=2.5 Hz, 1H), 6.95 (d, J=1.4 Hz, 1H), 4.80 (s, 2H), 4.26 (t, J=5.1 Hz, 2H), 3.54 (s, 3H), 3.35 (t, J=5.0 Hz, 2H), 2.79 (s, 3H), 2.68 (s, 3H). LC-MS: method C, RT=1.91 min, MS (ESI) m/z: 395 (M+H)$^+$.

Example 89

To a solution of Intermediate 89G (15 mg, 0.038 mmol) and 4-fluorobenzene-1-sulfonyl chloride (8.88 mg, 0.046 mmol) in DMF (1 mL) was added DIEA (0.066 mL, 0.380 mmol). The mixture was stirred at room temperature for 1 h. LCMS indicated a completion of the reaction. Solvent was removed, the residual was dissolved purified via preparative LC/MS (method D, 50-95% B over 10 min., then a 5-min hold at 100% B). Fractions containing the desired product were combined and dried via centrifugal evaporation to give Example 89 (0.9 mg, 1.629 μmol, 4.28% yield). $^1$H NMR (500 MHz, Methanol-d$_4$) δ 9.06 (s, 1H), 8.80 (d, J=1.9 Hz, 1H), 7.95-7.85 (m, 3H), 7.24-7.15 (m, 3H), 6.81 (dd, J=2.2, 0.8 Hz, 1H), 4.82 (s, 2H), 4.06 (t, J=5.5 Hz, 2H), 3.57 (s, 3H), 3.35 (t, J=5.5 Hz, 2H), 2.77 (s, 3H), 2.70 (s, 3H). LC-MS: method C, RT=2.50 min, MS (ESI) m/z: 553.2 (M+H)$^+$. Analytical HPLC purity (method B): 100%.

Example 90

4-fluoro N-(2-(2-(2-methoxy-7-methylquinoxalin-5-yl)-4-(trifluoromethyl)benzo[d]thiazol-6-yloxy)ethyl)benzenesulfonamide

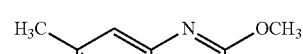
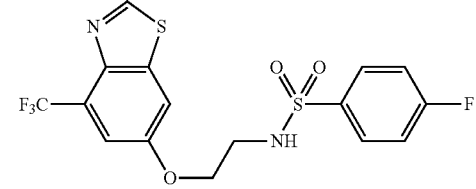
(90)

Intermediate 90A: tert-butyl 2-(4-nitro-3-(trifluoromethyl)phenoxy)ethylcarbamate

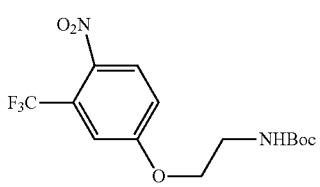
(90A)

DIAD (0.798 mL, 4.10 mmol) was added to a mixture of 4-nitro-3-(trifluoromethyl)phenol (0.34 g, 1.642 mmol) in THF (1.0 mL). Next, tert-butyl (2-hydroxyethyl)carbamate (0.529 g, 3.28 mmol) and triphenylphosphine (0.861 g, 3.28 mmol) in THF (10 mL) were added to the above mixture using syringe pump in 3 h. The reaction mixture was stirred at room temperature overnight. LCMS indicated a completion of the reaction. The mixture was concentrated and purified with a 40 g ISCO column eluted with 0-70% EtOAc in hexanes for 20 min. The desired fraction was collected and concentrated to give Intermediate 90A (1.1 g, 1.570 mmol, 96% yield) as brown oil. $^1$H NMR (400 MHz, chloroform-d) δ 8.01 (d, J=9.0 Hz, 1H), 7.30 (d, J=2.6 Hz, 1H), 7.13 (dd, J=9.0, 2.6 Hz, 1H), 4.18-4.13 (m, 2H), 3.58 (q, J=5.4 Hz, 2H), 1.45 (s, 9H). LC-MS: method C, RT=2.07 min, MS (ESI) m/z: 251 [M+1−Boc]$^+$.

Intermediate 90B: tert-butyl 2-(4-amino-3-(trifluoromethyl)phenoxy)ethylcarbamate

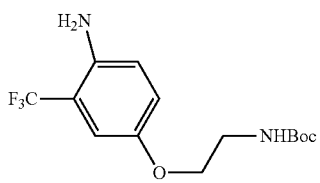
(90B)

To a solution of Intermediate 90A (574 mg, 1.64 mmol) in ethyl acetate (10 mL) under argon was added 10% Pd/C (100 mg, 1.640 mmol). The mixture was stirred under an atmosphere of hydrogen (balloon) at room temperature for 3.0 h. HPLC and TLC indicated a completion of reaction. Pd/C was removed by filtration. The filtrate was concentrated. The crude sample was purified with a 40 g ISCO column eluted with 0-100% EtOAc for 20 min. The desired fraction was collected and concentrated to give Intermediate 90B (670 mg, 1.569 mmol, 96% yield) as dark oil. $^1$H NMR (500 MHz, chloroform-d) δ 6.98 (d, J=2.8 Hz, 1H), 6.91 (dd, J=8.7, 2.9 Hz, 1H), 6.70 (d, J=8.8 Hz, 1H), 6.36 (br. s., 1H), 3.96 (t, J=5.1 Hz, 2H), 3.91 (br. s., 2H), 3.50 (d, J=5.0 Hz, 2H), 1.62 (s, 3H). LC-MS: method C, RT=1.83 min, MS (ESI) m/z: 221 (M+H−Boc)$^+$.

Intermediate 90C: tert-butyl 2-(2-amino-4-(trifluoromethyl)benzo[d]thiazol-6-yloxy) ethylcarbamate

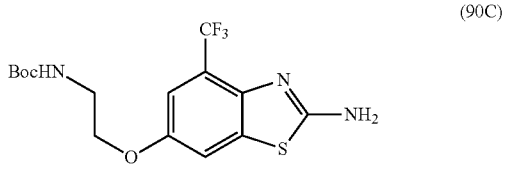 [SMILES: CC(C)(C)OC(=O)NCCOc1cc(C(F)(F)F)c2nc(N)sc2c1]

(90C)

To a solution of Intermediate 90B (180 mg, 0.562 mmol) in acetonitrile (5 mL) was added ammonium thiocyanate (128 mg, 1.686 mmol). The mixture was stirred at room temperature for 10 min. Benzyltrimethylammonium tribromide (219 mg, 0.562 mmol) in acetonitrile (2 mL) was added dropwise (5 min). The mixture was stirred at room temperature overnight. The mixture was diluted with EtOAc and NaHCO$_3$, extracted with EtOAc. The combined organic layer was washed with brine, dried with MgSO$_4$ and concentrated. The crude sample was purified with a 12 g ISCO column eluted with 0-100% EtOAc in hexanes for 15 min. The desired fraction was collected to give Intermediate 90C (100 mg, 0.265 mmol, 47.2% yield) as a white solid. $^1$H NMR (500 MHz, methanol-d$_4$) δ 7.48 (d, J=2.2 Hz, 1H), 7.14 (d, J=2.5 Hz, 1H), 4.05 (t, J=5.6 Hz, 2H), 3.43 (t, J=5.5 Hz, 2H), 1.44 (s, 9H). $^{19}$F NMR (471 MHz, methanol-d$_4$) δ −63.25 (s, 3F). LC-MS: method C, RT=1.85 min, MS (ESI) m/z: 378 (M+H)$^+$.

Intermediate 90D: tert-butyl (2-((2-bromo-4-(trifluoromethyl)benzo[d]thiazol-6-yl) oxy)ethyl)carbamate

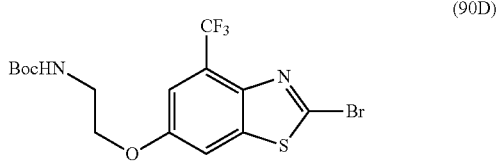 [SMILES: CC(C)(C)OC(=O)NCCOc1cc(C(F)(F)F)c2nc(Br)sc2c1]

(90D)

tert-Butyl nitrite (0.061 mL, 0.464 mmol) was added to copper (II) bromide (101 mg, 0.450 mmol) in dry acetonitrile (2 mL) under argon. The mixture was stirred at room temperature for 10 min. A suspension of Intermediate 90C (100 mg, 0.265 mmol) in dry acetonitrile (2 mL) was added dropwise. The reaction mixture was stirred at room temperature overnight. LCMS indicated a completion of the reaction. Acetonitrile was removed under vacuum, the reaction mixture was diluted with EtOAc, quenched with 1.0 N HCl. The organic layer was collected, washed with 0.5 N HCl (2×), saturated sodium bicarbonate, brine, dried over sodium sulfate. After evaporation of solvent, the crude sample was purified with a 40 g ISCO column eluted with 0-70% EtOAc in hexanes for 20 min. The desired fraction was collected and concentrated to give Intermediate 90D (92 mg, 0.208 mmol, 79% yield) as a white solid. LC-MS: method C, RT=2.20 min, MS (ESI) m/z: 547.2 (M+H)$^+$.

Intermediate 90E: tert-butyl 2-(2-(2-(difluoromethoxy)-7-methylquinoxalin-5-yl)-4-(trifluoromethyl)benzo[d]thiazol-6-yloxy)ethylcarbamate

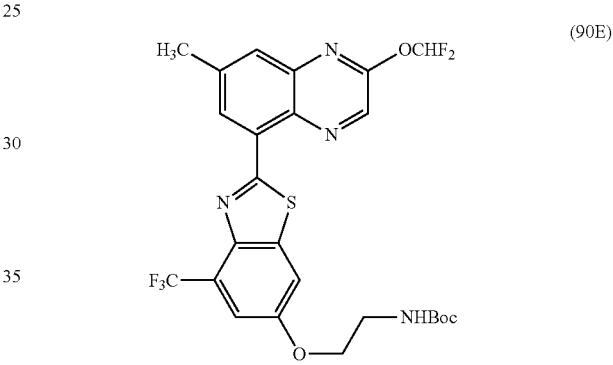

(90E)

To Intermediate I-1 (15.24 mg, 0.045 mmol), and Intermediate 90D (20 mg, 0.045 mmol) [1,1'-bis(diphenylphosphino)ferrocene]dichloropalladium (II) complex with dichloromethane (1:1) (1.851 mg, 2.266 μmol) was added toluene (0.75 mL), EtOH (0.25 mL) and sodium carbonate (0.045 mL, 2M, 0.091 mmol). The mixture was degassed with argon for 5 min. The reaction mixture was heated in a microwave reactor at 135° C. for 40 min. To the reaction mixture was added EtOAc/water/brine. The insoluble was removed by filtration with a pad of celite. The organic layers were collected, washed with brine, dried over sodium sulfate. After evaporation of solvent, the crude product was dissolved in a small amount of chloroform and charged to a 12 g ISCO column which was eluted with hexanes for 3 min., then a 20 min gradient from 0% to 75% dichloromethane in hexanes. The desired fractions were combined and concentrated to give Intermediate 90E (25.9 mg, 0.045 mmol, 100% yield) as a bright yellow solid. LC-MS: method C, gradient time 1 min, RT=1.67 min, MS (ESI) m/z: 571 (M+H)$^+$.

Intermediate 90F: tert-butyl 2-(2-(2-methoxy-7-methylquinoxalin-5-yl)-4-(trifluoromethyl)benzo[d]thiazol-6-yloxy)ethylcarbamate

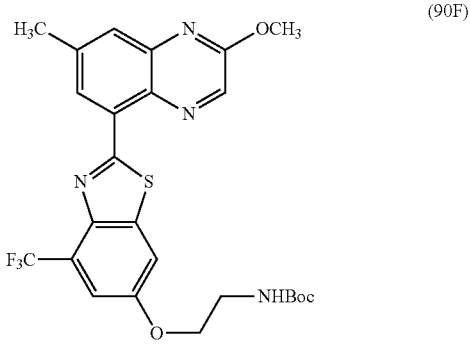

(90F)

To a solution of Intermediate 90E (25.7 mg, 0.045 mmol) in THF (1 mL) was added sodium methoxide (0.090 mL, 0.5M, 0.045 mmol) and the mixture was stirred at room temperature for 1 h. LCMS indicated a completion of the reaction. The mixture was diluted with DCM and water, extracted with DCM and the combined organic layer was washed with brine, dried over MgSO₄ and concentrated. The crude sample was purified with a 12 g ISCO column eluted with 0-70% EtOAc in hexanes for 15 min. The desired fraction was collected and concentrated to give Intermediate 90F (10 mg, 0.019 mmol, 41.6% yield) as a white solid. $^1$H NMR (500 MHz, Methanol-d₄) δ 8.63 (s, 1H), 8.51 (s, 1H), 7.75 (s, 1H), 7.65 (d, J=1.7 Hz, 1H), 7.39 (s, 1H), 4.14 (t, J=5.5 Hz, 2H), 4.11 (s, 3H), 3.52 (t, J=5.4 Hz, 2H), 2.64 (s, 3H), 1.44 (s, 9H). LC-MS: method C, R=2.66 min, MS (ESI) m/z: 535 (M+H)⁺.

Intermediate 90G: 2-(2-(2-methoxy-7-methylquinoxalin-5-yl)-4-(trifluoromethyl) benzo[d]thiazol-6-yloxy)ethanamine

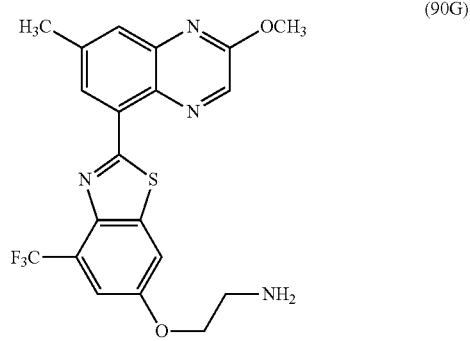 [SMILES: COc1cnc2c(-c3nc4c(C(F)(F)F)cc(OCCN)cc4s3)cc(C)cc2n1]

(90G)

To a solution of Intermediate 90F (7 mg, 0.013 mmol) in DCM (1 mL) was added TFA (0.020 mL, 0.262 mmol). The mixture was stirred at room temperature for 5 h. Solvent was removed and Intermediate 90G was used for next step without purification. LC-MS: method C, RT=2.15 min, MS (ESI) m/z: 435 (M+H)⁺.

Example 90

To a solution of Intermediate 90G (5.65 mg, 0.013 mmol) and 4-fluorobenzene-1-sulfonyl chloride (3.04 mg, 0.016 mmol) in DMF (1 mL) was added DIEA (0.023 mL, 0.130 mmol). The mixture was stirred at room temperature for 1 h. LCMS indicated a completion of the reaction. Solvent was removed, the residual was purified via preparative LC/MS (method D, 55-95% B over 10 min., then a 5-min hold at 100% B). Fractions containing the desired product were combined and dried via centrifugal evaporation to give Example 90 (4.4 mg, 7.43 μmol, 57.1% yield). $^1$H NMR (500 MHz, DMSO-d₆) δ 7.93 (s, 1H), 7.72 (d, J=1.7 Hz, 1H), 7.16 (d, J=2.5 Hz, 1H), 7.13-7.03 (m, 3H), 6.59-6.54 (m, 2H), 6.42 (d, J=2.2 Hz, 1H), 3.30 (t, J=5.2 Hz, 2H), 3.26 (s, 3H), 2.45 (br. s., 2H), 1.82 (s, 3H). LC-MS: method C, RT=2.54 min, MS (ESI) m/z: 593.1 (M+H)⁺. Analytical HPLC purity (method B): 100%.

Example 91

N-(2-(2-(2-cyclopropyl-7-methylquinoxalin-5-yl)-4-methylbenzo[d]thiazol-6-yloxy)ethyl)-4-fluorobenzenesulfonamide

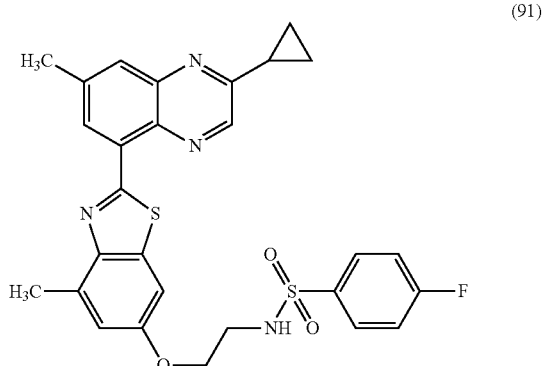

(91)

Intermediate 91A: tert-butyl (2-bromo-4-methyl-6-nitrophenyl)(2-cyclopropyl-2-oxoethyl)carbamate

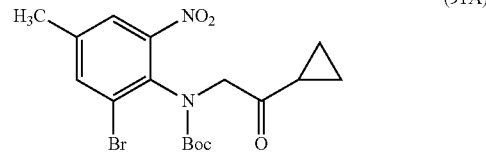

(91A)

To Intermediate I-1B (400 mg, 1.208 mmol) in DMF (5 mL) at room temperature was added Cs₂CO₃ (1181 mg, 3.62 mmol). The brown solution was stirred at room temperature for 5 min, followed by addition of 2-bromo-1-cyclopropylethanone (438 mg, 2.416 mmol) in acetonitrile (0.4 mL). The mixture was stirred at room temperature for 2 h. TLC and LCMS indicated a clean reaction. The mixture was diluted with EtOAc, washed with water, brine, dried over sodium sulfate and concentrated. The crude sample was purified with a 40 g ISCO column eluted with 0-100% EtOAc in hexanes for 20 min. The desired fraction was collected and concentrated to give Intermediate 91A (490 mg, 1.186 mmol, 98% yield) as yellow oil. LC-MS: method C, RT=2.03 min, MS (ESI) m/z: 356 and 358 [M+1−tBu]⁺.

Intermediate 91B:
5-bromo-2-cyclopropyl-7-methylquinoxaline

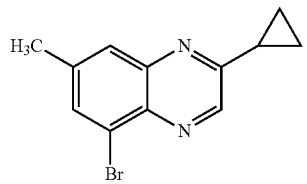

To Intermediate 91A (490 mg, 1.186 mmol) in DCM (4 mL) was added 4.0 N HCl in dioxane (3.56 mL, 14.23 mmol) and the mixture was stirred at room temperature for 1 h. TLC indicated a completion of the reaction. Solvent was removed to give the deprotected intermediate as yellow oil. The deprotected intermediate was dissolved in THF (4 mL). Tin(II) chloride dihydrate (883 mg, 3.91 mmol) was added followed by concentrated HCl (0.146 mL, 1.779 mmol). The mixture was placed and stirred in an oil bath pre-heated at 45° C. for 1.0 h. TLC and LCMS indicated a clean reaction. The reaction mixture was diluted with EtOAc/water and neutralized with saturated sodium bicarbonate. The mixture was stirred at room temperature for 15 min and extracted with EtOAc (5×). The precipitate (tin hydroxide) was removed by a separatory funnel. The organic layer was washed with saturated sodium bicarbonate, brine, dried over sodium sulfate and concentrated. The crude sample was purified with a 40 g ISCO column eluted with 0-60% EtOAc in hexanes for 15 min. The desired fraction was collected and concentrated to give Intermediate 91B (310 mg, 1.178 mmol, 99% yield) as a light yellow solid. $^1$H NMR (400 MHz, chloroform-d) δ 8.76 (s, 1H), 7.81 (d, J=1.8 Hz, 1H), 7.69 (dd, J=1.8, 0.9 Hz, 1H), 2.54 (s, 3H), 2.34-2.23 (m, 1H), 1.30-1.25 (m, 2H), 1.24-1.16 (m, 2H). LC-MS: method C, RT=2.07 min, MS (ESI) m/z: 263 and 265. $(M+H)^+$.

Intermediate 91C 2-cyclopropyl-7-methyl-5-(4,4,5,5-tetramethyl-1,3,2-dioxaborolan-2-yl)quinoxaline

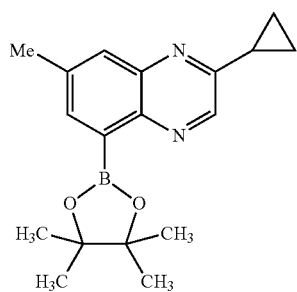

A mixture of Intermediate 91B (30 mg, 0.114 mmol), 4,4,4',4',5,5,5',5'-octamethyl-2,2'-bi(1,3,2-dioxaborolane) (50.7 mg, 0.200 mmol), potassium acetate (22.38 mg, 0.228 mmol) and [1,1'-bis(diphenylphosphino)ferrocene]dichloropalladium (II) complex with dichloromethane (1:1) (2.79 mg, 3.42 μmol) in dioxane (2 mL) was degassed with argon for 10 min. The reaction vial was heated in microwave reactor at 120° C. for 30 min. LCMS indicated complete conversion of starting material and a clean reaction. The mixture was diluted with EtOAc/water, insoluble material was removed by filtration. The filtrate was extracted with EtOAc, washed with brine, dried over sodium sulfate. After evaporation of solvent, the crude sample of Intermediate 91C was obtained and used for the next step without purification. LC-MS: method C, RT=2.03 min, MS (ESI) m/z: 229 $(M+H)^+$ (boronic acid).

Example 91

To Intermediate 91C (34.8 mg, 0.112 mmol), Intermediate I-5 (20 mg, 0.045 mmol) and [1,1'-bis(diphenylphosphino)ferrocene]dichloropalladium (II) complex with dichloromethane (1:1) (1.834 mg, 2.246 μmol) was added toluene (3 mL), EtOH (1 mL) and sodium carbonate (0.045 mL, 2M, 0.090 mmol). The mixture was degassed with argon for 5 min. The reaction mixture was heated in a microwave reactor at 130° C. for 40 min. To the reaction mixture was added EtOAc/water/brine. The insoluble was removed by filtration with a pad of celite. The organic layers were collected, washed with brine, dried over sodium sulfate. After evaporation of solvent, the crude product was purified via preparative LC/MS (method D, 60-100% B over 20 min., then a 5-min hold at 100% B). Fractions containing the desired product were combined and dried via centrifugal evaporation to give Example 91 (6.8 mg, 0.012 mmol, 27.6% yield). $^1$H NMR (500 MHz, DMSO-$d_6$) δ 9.03 (s, 1H), 8.67 (s, 1H), 8.03 (br. s., 1H), 7.95-7.81 (m, 3H), 7.48-7.37 (m, 3H), 6.85 (s, 1H), 4.05 (t, J=5.0 Hz, 2H), 3.22 (br. s., 2H), 2.72 (s, 3H), 2.64 (s, 3H), 1.29-1.13 (m, 5H). LC-MS: method C, RT=2.50 min, MS (ESI) m/z: 549.2 $(M+H)^+$. Analytical HPLC purity (method B): 99%.

Example 92

Benzyl 2-(2-(2-(methoxymethyl)-7-methylquinoxalin-5-yl)-4-methylbenzo[d]thiazol-6-yloxy)ethylcarbamate

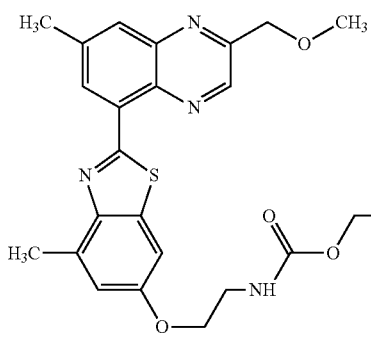

Intermediate 92A: tert-butyl 2-(3-methyl-4-nitrophenoxy)ethylcarbamate

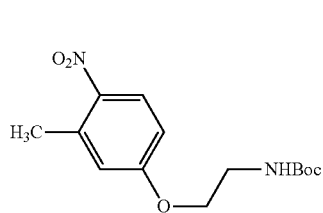

(92A)

A solution of DIAD (7.77 mL, 40.0 mmol) in 2 ml of toluene was added to a mixture of 3-methyl-4-nitrophenol (3.4 g, 22.20 mmol), tert-butyl (2-hydroxyethyl) carbamate (4.29 g, 26.6 mmol) and triphenylphosphine (6.99 g, 26.6 mmol) in toluene (50 mL) at 110° C. using syringe pump in 2 h. The reaction mixture was stirred at 110° C. for additional 30 min, then at room temperature overnight. The mixture was diluted with EtOAc and water, extracted with EtOAc, the combined organic layer was washed with NaHCO$_3$ and brine, dried with Na$_2$SO$_4$ and concentrated. The crude sample was purified with a 120 g ISCO column eluted with 0-70% EtOAc in hexanes for 40 min. The desired fraction was collected and concentrated to give Intermediate 92A (3.3 g, 11.14 mmol, 50.2% yield). $^1$H NMR (500 MHz, chloroform-d) δ 8.08 (d, J=8.8 Hz, 1H), 6.84-6.77 (m, 2H), 4.97 (br. s., 1H), 4.09 (t, J=5.1 Hz, 2H), 3.56 (q, J=5.0 Hz, 2H), 2.63 (s, 3H), 1.46 (s, 9H). LC-MS: method C, RT=2.03 min, MS (ESI) m/z: 197 (M+H−Boc)$^+$.

Intermediate 92B: tert-butyl 2-(4-amino-3-methylphenoxy)ethylcarbamate

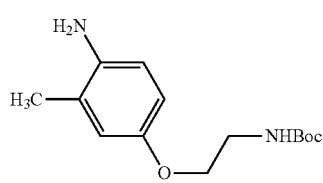

(92B)

To a solution of Intermediate 92A (3.5 g, 11.81 mmol) in ethyl acetate (10 mL) under argon was added 10% Pd/C (200 mg, 23.62 mmol). The mixture was stirred under an atmosphere of hydrogen (balloon) at room temperature overnight. Pd/C was removed by filtration. The filtrate was concentrated. The crude sample was purified with a 120 g ISCO column eluted with 0-100% EtOAc in hexanes for 45 min. The desire fraction was collected to give Intermediate 92B (2.5 g, 9.39 mmol, 79% yield) as a pink solid. $^1$H NMR (500 MHz, chloroform-d) δ 6.67 (s, 1H), 6.62 (d, J=1.7 Hz, 2H), 5.00 (br. s., 1H), 3.95 (t, J=5.1 Hz, 2H), 3.49 (d, J=5.0 Hz, 2H), 3.37 (br. s., 2H), 2.16 (d, J=0.6 Hz, 3H), 1.46 (s, 9H). LC-MS: method C, RT=1.34 min, MS (ESI) m/z: 167 [M+1−Boc]$^+$.

Intermediate 92C: tert-butyl 2-(2-amino-4-methyl-benzo[d]thiazol-6-yloxy)ethylcarbamate

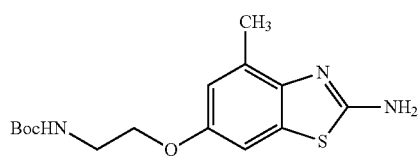

(92C)

To a solution of Intermediate 92B (2.5 g, 9.39 mmol) in acetonitrile (20 mL) was added ammonium thiocyanate (1.072 g, 14.08 mmol). The mixture was stirred at room temperature for 10 min. Benzyltrimethylammonium tribromide (3.66 g, 9.39 mmol) in acetonitrile (10 mL) was added dropwise (5 min). The mixture was stirred at room temperature overnight. LCMS indicated a clean reaction. The mixture was diluted with EtOAc/saturated sodium bicarbonate. The insoluble material was removed by filtration. The organic layer of the filtrate was collected, washed with brine, dried over sodium sulfate. After evaporation of solvent, the product was precipitated out from methanol, collected by filtration, washed with acetonitrile to give Intermediate 92C (2.8 g, 8.66 mmol, 92% yield) as a slightly yellow solid. $^1$H NMR (500 MHz, chloroform-d) δ 6.97 (d, J=2.2 Hz, 1H), 6.75 (d, J=1.9 Hz, 1H), 5.05 (s, 2H), 4.02 (t, J=5.0 Hz, 2H), 3.53 (d, J=4.7 Hz, 2H), 2.53 (s, 3H), 1.46 (s, 9H). LC-MS: method C, RT=2.57 min, MS (ESI) m/z: 324 (M+H)$^+$.

Intermediate 92D: tert-butyl 2-(2-chloro-4-methyl-benzo[d]thiazol-6-yloxy)ethylcarbamate

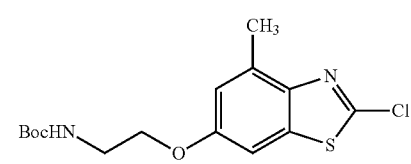

(92D)

To a stirred solution of Intermediate 92C (2.8 g, 8.66 mmol) and copper (II) chloride (1.029 g, 10.39 mmol) in acetonitrile (30 mL) was added tert-butyl nitrite (1.487 mL, 11.26 mmol). The mixture was stirred at room temperature for 2 h. Acetonitrile was removed under vacuum, the reaction mixture was diluted with EtOAc, quenched with 1.0 N HCl. The organic layer was collected, washed with 0.5 N HCl (2×), saturated sodium bicarbonate, brine, dried over sodium sulfate. After evaporation of solvent, the crude dark oil was purified with a 120 g ISCO column eluted with 0-70% EtOAc in hexanes for 40 min. The desired fraction was collected and concentrated to give Intermediate 92D (1.75 g, 5.10 mmol, 59.0% yield) as an off-white solid. $^1$H NMR (500 MHz, chloroform-d) δ 7.05 (d, J=2.5 Hz, 1H), 6.89 (dd, J=2.5, 0.8 Hz, 1H), 5.00 (br. s., 1H), 4.05 (t, J=5.1 Hz, 2H), 3.56 (d, J=5.0 Hz, 2H), 2.65 (s, 3H), 1.46 (s, 9H). LC-MS: method C, RT=2.21 min, MS (ESI) m/z: 343 (M+H)$^+$.

Intermediate 92E: 2-(2-chloro-4-methylbenzo[d]thiazol-6-yloxy)ethanamine

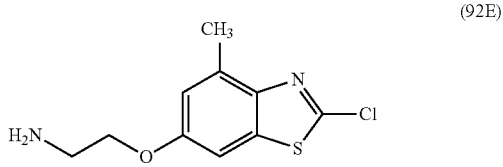

To a solution of Intermediate 92D (100 mg, 0.292 mmol) in DCM (1.5 mL) was added TFA (1.124 mL, 14.58 mmol). The mixture was stirred at room temperature for 1 h. LCMS indicated a completion of the reaction. The mixture was concentrated and the residual was diluted with EtOAc and saturated NaHCO$_3$, extracted with EtOAc. The combined organic layer was washed with brine, dried with MgSO$_4$ and concentrated to give Intermediate 92E (70 mg, 0.288 mmol, 99% yield) as an off-white solid. $^1$H NMR (400 MHz, Methanol-d$_4$) δ 7.29 (d, J=2.4 Hz, 1H), 7.06-6.84 (m, 1H), 4.19 (t, J=5.2 Hz, 2H), 3.28 (br. s., 2H), 2.58 (s, 3H). LC-MS: method C, RT=1.43 min, MS (ESI) m/z: 243 (M+H)$^+$.

Intermediate 92F: benzyl 2-(2-chloro-4-methyl-benzo[d]thiazol-6-yloxy)ethylcarbamate

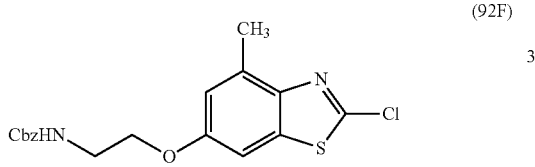

To a stirred solution of Intermediate 92E (70 mg, 0.288 mmol) in THF (1 mL) at room temperature was added sodium bicarbonate (1.154 mL, 2M, 2.307 mmol). CBz-Cl (0.049 mL, 0.346 mmol) was added dropwise. The mixture was stirred at room temperature for 1 h, LCMS indicated a completion of the reaction. The mixture was diluted with EtOAc and water, extracted with EtOAc. The combined organic layer was washed with brine, dried with MgSO$_4$ and concentrated. The crude sample was purified with a 12 g ISCO column eluted with 0-60% EtOAc in hexanes for 15 min. The desired product was collected and concentrated to give Intermediate 92F (100 mg, 0.265 mmol, 92% yield). $^1$H NMR (400 MHz, chloroform-d) δ 7.38-7.35 (m, 5H), 7.04 (d, J=2.2 Hz, 1H), 6.87 (d, J=1.3 Hz, 1H), 5.25 (br. s., 1H), 5.12 (s, 2H), 4.72 (s, 1H), 4.07 (t, J=5.1 Hz, 2H), 3.64 (q, J=5.3 Hz, 2H), 2.65 (s, 3H). LC-MS: method C, RT=2.22 min, MS (ESI) m/z: 377 (M+H)$^+$.

Example 92

To Intermediate I-2 (30 mg, 0.129 mmol), Intermediate 92F (58.5 mg, 0.155 mmol) and [1,1'-bis(diphenylphosphino)ferrocene]dichloropalladium (II) complex with dichloromethane (1:1) (5.28 mg, 6.46 µmol) was added toluene (3 mL), EtOH (1 mL) and sodium carbonate (0.129 mL, 2M, 0.259 mmol). The mixture was degassed with argon for 5 min. The reaction mixture was heated in a microwave reactor at 130° C. for 40 min. To the reaction mixture was added EtOAc/water/brine. The insoluble was removed by filtration with a pad of celite. The organic layers were collected, washed with brine, dried over sodium sulfate. After evaporation of solvent, the crude product was dissolved in a small amount of chloroform and charged to a 40 g ISCO column which was eluted with hexanes for 3 min., then a 20 min gradient from 0% to 100% EtOAc in hexanes The desired fractions were combined and concentrated. The sample was further purified via preparative LCMS (method D, 50-90% B over 10 min., then a 5-min hold at 100% B). Fractions containing the desired product were combined and dried via centrifugal evaporation to give Example 92 (42 mg, 0.079 mmol, 61.5% yield) as a yellow solid. $^1$H NMR (500 MHz, DMSO-d$_6$) δ 9.08 (s, 1H), 8.80 (s, 1H), 8.01 (s, 1H), 7.60-7.48 (m, 2H), 7.36 (d, J=4.4 Hz, 4H), 7.33-7.28 (m, 1H), 7.00 (br. s., 1H), 5.05 (s, 2H), 4.80 (s, 2H), 4.10 (t, J=5.5 Hz, 2H), 3.48-3.41 (m, 5H), 2.74 (s, 3H), 2.70 (s, 3H). LC-MS: method C, RT=2.50 min, MS (ESI) m/z: 529.2 (M+H)$^+$.

Example 93

4-chloro-6-methoxy-2-(2-(methoxymethyl)-7-methylquinoxalin-5-yl)benzo[d]thiazole

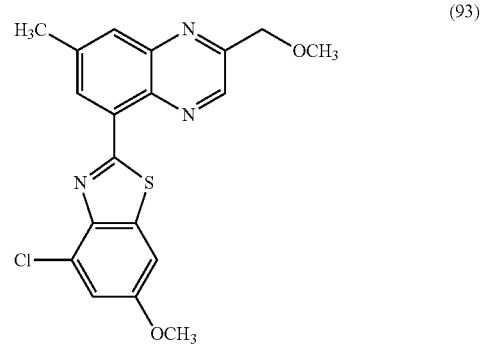

Intermediate 93A: 2-chloro-4-methoxy-1-nitrobenzene

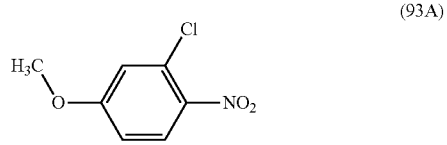

To a solution of 2-chloro-4-fluoro-1-nitrobenzene (220 mg, 1.253 mmol) in THF (2 mL) was added sodium methoxide (7.52 mL, 0.5, 3.76 mmol). The mixture was stirred at room temperature for 1.0 h. LCMS indicated a completion of the reaction The mixture was diluted with EtOAc, quenched with saturated ammonium chloride. The organic layer was washed with saturated sodium bicarbonate, brine, dried over sodium sulfate and concentrated. The crude product was purified with flash chromatography (loading in chloroform, 0% to 30% EtOAc in hexanes over 12 min using a 12 g silica gel cartridge). The desired fractions were combined and concentrated to give Intermediate 93A (230 mg, 1.226 mmol, 98% yield) as a yellow liquid. $^1$H NMR (400 MHz, chloroform-d) δ 8.02 (d, J=9.2 Hz, 1H), 7.03 (d, J=2.6 Hz, 1H), 6.89 (dd, J=9.2, 2.6 Hz, 1H), 3.90 (s, 3H). LC-MS: method C, RT=1.80 min, MS (ESI) m/z: 188 (M+H)$^+$.

Intermediate 93B: 2-chloro-4-methoxyaniline

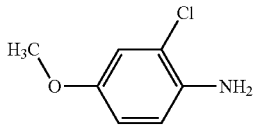

To a solution of Intermediate 93A (230 mg, 1.226 mmol) in MeOH (6.0 mL) was added ammonium chloride (1312 mg, 24.52 mmol) and zinc dust (802 mg, 12.26 mmol). The mixture was stirred at room temperature for 1 h. MeOH was removed under vacuum. The residue was diluted with EtOAc/saturated sodium bicarbonate and stirred at room temperature for 10 min. The mixture was filtered to remove insoluble material. The filtrate was collected, organic layer was washed with brine, dried over sodium sulfate and concentrated. The crude sample was purified with a 12 g ISCO column eluted with 0-100% EtOAc in hexanes for 15 min. The desired fraction was collected and concentrated to give Intermediate 93B (193 mg, 1.225 mmol, 100% yield) as oil. $^1$H NMR (400 MHz, chloroform-d) δ 6.86 (t, J=2.5 Hz, 1H), 6.76-6.64 (m, 2H), 3.74 (d, J=3.1 Hz, 3H). LC-MS: method C, RT=0.8 min, MS (ESI) m/z: 158 (M+H)$^+$.

Intermediate 93C: 4-chloro-6-methoxybenzo[d]thiazol-2-amine

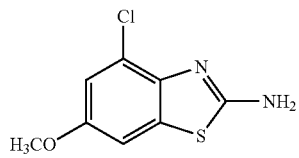

To a solution of Intermediate 93B (190 mg, 1.206 mmol) in acetonitrile (5.0 mL) was added ammonium thiocyanate (161 mg, 2.110 mmol). The mixture was stirred at room temperature for 10 min. Benzyltrimethylammonium tribromide (635 mg, 1.628 mmol) in acetonitrile (2.0 mL) was added dropwise (5 min). The mixture was stirred at room temperature overnight. Acetonitrile was removed under vacuum. The mixture was diluted with EtOAc, THF/saturated sodium bicarbonate. The insoluble material was removed by filtration. The organic layer of the filtrate was collected, washed with brine, dried over sodium sulfate and concentrated to give Intermediate 93C (250 mg, 1.165 mmol, 97% yield) as a yellow solid that was used for the next step without further purification. $^1$H NMR (400 MHz, methanol-d$_4$) δ 7.16 (d, J=2.4 Hz, 1H), 6.91 (d, J=2.4 Hz, 1H), 3.79 (s, 3H). LC-MS: method C, RT=1.38 min, MS (ESI) m/z: 215 (M+H)$^+$.

Intermediate 93D: 2-bromo-4-chloro-6-methoxybenzo[d]thiazole

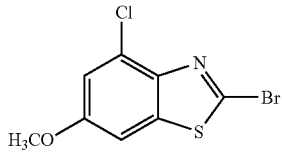

To a solution of copper (II) bromide (0.21 g, 1.51 mmol) in acetonitrile (8 mL) at 40° C. was added tert-butyl nitrite (0.200 mL, 1.514 mmol) followed by Intermediate 93C (250 mg, 1.165 mmol) as a solid. The mixture was stirring at 40° C. for 2.0 h. HPLC and LCMS indicated a complete conversion of starting material. The mixture was diluted with EtOAc, washed with 0.5 HCl, saturated sodium bicarbonate and brine. After evaporation of solvent, Intermediate 93D (215 mg, 0.772 mmol, 66.3% yield) was obtained as a yellow solid. $^1$H NMR (400 MHz, chloroform-d) δ 7.17 (d, J=2.4 Hz, 1H), 7.13 (d, J=2.4 Hz, 1H), 3.87 (s, 3H). LC-MS: method C, RT=2.08 min, MS (ESI) m/z: 279.9 (M+H)$^+$.

Example 93

To Intermediate I-2 (11 mg, 0.047 mmol), Intermediate 93D (15.85 mg, 0.057 mmol) and [1,1'-bis(diphenylphosphino)ferrocene]dichloropalladium (II) complex with dichloromethane (1:1) (1.936 mg, 2.370 μmol) was added toluene (3 mL), EtOH (1 mL) and sodium carbonate (0.047 mL, 2M, 0.095 mmol). The mixture was degassed with argon for 5 min. The reaction mixture was heated in a microwave reactor at 130° C. for 40 min. LCMS indicated a clean reaction. To the reaction mixture was added EtOAc/water/brine. The insoluble was removed by filtration with a pad of celite. The organic layers were collected, washed with brine, dried over sodium sulfate. After evaporation of solvent, the crude product was purified via preparative LC/MS (method D, 45-85% B over 20 min., then a 5-min hold at 100% B). Fractions containing the desired product were combined and dried via centrifugal evaporation to give Example 93 (3.3 mg, 8.47 μmol, 17.86% yield). $^1$H NMR (500 MHz, DMSO-d$_6$) δ 9.10 (s, 1H), 8.80 (d, J=1.7 Hz, 1H), 8.07 (s, 1H), 7.77 (d, J=2.5 Hz, 1H), 7.32 (d, J=2.2 Hz, 1H), 4.82 (s, 2H), 3.89 (s, 3H), 3.47 (s, 3H), 2.70 (s, 3H). LC-MS: method C, RT=2.50 min, MS (ESI) m/z: 386.1 (M+H)$^+$. Analytical HPLC purity (method B): 99%.

Example 94

5-(5-methoxybenzofuran-2-yl)-2-(methoxymethyl)-7-methylquinoxaline

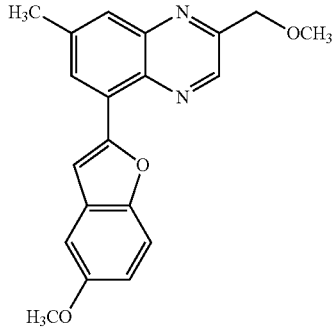

To Intermediate I-2E (5 mg, 0.019 mmol), (5-methoxybenzofuran-2-yl)boronic acid (4.31 mg, 0.022 mmol) and [1,1'-bis(diphenylphosphino)ferrocene] dichloropalladium (II) complex with dichloromethane (1:1) (0.764 mg, 0.936 μmol) was added toluene (0.75 mL), EtOH (0.25 mL) and sodium carbonate (0.019 mL, 2M, 0.037 mmol). The mixture was degassed with argon for 5 min. The reaction mixture was heated in a microwave reactor at 130° C. for 40 min. To the reaction mixture was added EtOAc/water/brine. The insoluble was removed by filtration with a pad of celite. The organic layers were collected, washed with brine, dried over sodium sulfate. After evaporation of solvent, the crude product was purified via preparative LC/MS (method D; 50-90% B over 10 min., then a 5-min hold at 100% B). Fractions containing the desired product were combined and dried via centrifugal evaporation to give Example 94 (5.1 mg, 0.014 mmol, 75.0% yield). $^1$H NMR (500 MHz, DMSO-$d_6$) δ 9.07 (s, 1H), 8.28 (d, J=1.7 Hz, 1H), 8.15 (s, 1H), 7.89 (s, 1H), 7.61-7.58 (m, 1H), 7.31 (d, J=2.5 Hz, 1H), 6.98-6.96 (m, 1H), 4.80 (s, 2H), 3.83 (s, 3H), 3.82 (s, 3H), 3.47 (s, 3H). LC-MS: method C, RT=2.36 min, MS (ESI) m/z: 335.10 (M+H)$^+$. Analytical HPLC purity (method B): 92%.

Example 95

N-(2-((2-(2-(methoxymethyl)-7-methylquinoxalin-5-yl)-4-methylbenzo[d]thiazol-6-yl) oxy)ethyl)benzenesulfonamide

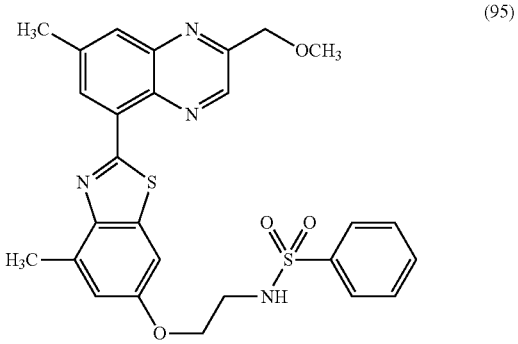 [SMILES: COCc1cnc2c(-c3nc4c(C)cc(OCCNS(=O)(=O)c5ccccc5)cc4s3)cc(C)cc2n1]

(95)

Intermediate 95A: tert-butyl 2-(2-(2-(methoxymethyl)-7-methylquinoxalin-5-yl)-4-methylbenzo[d]thiazol-6-yloxy)ethylcarbamate

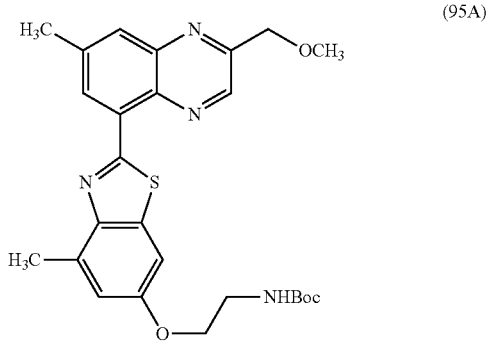 [SMILES: COCc1cnc2c(-c3nc4c(C)cc(OCCNC(=O)OC(C)(C)C)cc4s3)cc(C)cc2n1]

(95A)

To Intermediate I-2 (40 mg, 0.172 mmol), Intermediate 92D (59.1 mg, 0.172 mmol) and [1,1'-bis(diphenylphosphino)ferrocene]dichloropalladium (II) complex with dichloromethane (1:1) (7.04 mg, 8.62 μmol) was added toluene (0.75 mL), EtOH (0.25 mL) and sodium carbonate (0.172 mL, 2M, 0.345 mmol). The mixture was degassed with argon for 5 min. The reaction mixture was heated in a microwave reactor at 130° C. for 40 min. LCMS indicated a clean reaction. To the reaction mixture was added EtOAc/water/brine. The insoluble was removed by filtration with a pad of celite. The organic layers were collected, washed with brine, dried over sodium sulfate. After evaporation of solvent, the crude product was dissolved in a small amount of chloroform and charged to a 40 g ISCO column which was eluted with hexanes for 3 min., then a 20 min gradient from 0% to 100% EtOAc in hexanes. The desired fractions were combined and concentrated to give Intermediate 95A (80 mg, 0.162 mmol, 94% yield). $^1$H NMR (400 MHz, chloroform-d) δ 9.06 (d, J=3.5 Hz, 1H), 8.85 (d, J=3.3 Hz, 1H), 7.92 (br. s., 1H), 7.23 (t, J=2.6 Hz, 1H), 6.93 (br. s., 1H), 5.07 (br. s., 1H), 4.83 (d, J=2.4 Hz, 2H), 4.12-4.05 (m, 2H), 3.60-3.53 (m, 5H), 2.83 (s, 3H), 2.70 (d, J=2.0 Hz, 3H), 1.48 (s, 9H). LC-MS: method C, RT=2.50 min, MS (ESI) m/z: 495 (M+H)$^+$.

Intermediate 95B 2-(2-(2-(methoxymethyl)-7-methylquinoxalin-5-yl)-4-methylbenzo[d]thiazol-6-yloxy)ethanamine

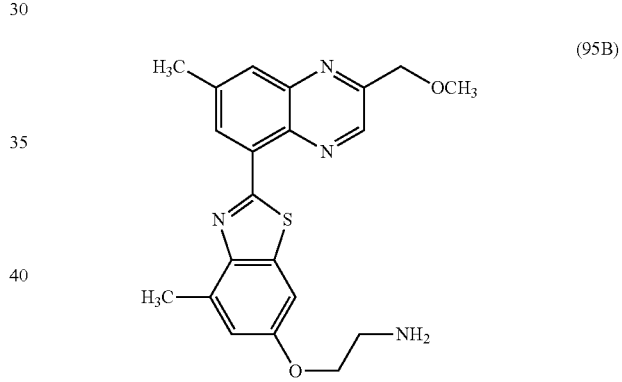

(95B)

To a solution of Intermediate 95A (18 mg, 0.036 mmol) in DCM (1 mL) was added 2,6-lutidine (16.95 μl, 0.146 mmol) followed by TMS-OTf (13.15 μl, 0.073 mmol) at room temperature. The mixture was stirred at room temperature overnight. Another portion of TMS-OTf (13.15 μl, 0.073 mmol) was added to the mixture, and the mixture was stirred at room temperature for 2 h. LCMS indicated a completion of the reaction. The mixture was diluted with EtOAc and NaHCO$_3$, extracted with EtOAc. The combined organic layer was washed with brine, dried with MgSO$_4$ and concentrated to give Intermediate 95B (14.2 mg, 0.036 mmol, 98% yield). The sample was used for next step without further purification. $^1$H NMR (400 MHz, Methanol-$d_4$) δ 9.06 (s, 1H), 8.82 (d, J=1.8 Hz, 1H), 7.93 (s, 1H), 7.36 (d, J=2.4 Hz, 1H), 6.99 (dd, J=2.4, 0.9 Hz, 1H), 4.82-4.81 (m, 2H), 4.15 (t, J=5.2 Hz, 2H), 3.15 (t, J=5.1 Hz, 2H), 2.79 (s, 3H), 2.70 (s, 3H). LC-MS: method C, RT=1.43 min, MS (ESI) m/z: 243 (M+H)$^+$.

Example 95

To a solution of Intermediate 95B (14.20 mg, 0.036 mmol) in DMF (1 mL) was added DIEA (0.063 mL, 0.360 mmol) and benzenesulfonyl chloride (5.57 μL, 0.043 mmol). The mixture was stirred at room temperature for 1 h. The reaction mixture was quenched with 0.2 ml of MeOH. Solvent was removed, the residual was purified via preparative LCMS (method D, 50-90% B over 12 min., then a 5-min hold at 100% B). Fractions containing the desired product were combined and dried via centrifugal evaporation to give Example 95 (3.3 mg, 6.05 mol, 16.80% yield). $^1$H NMR (500 MHz, methanol-$d_4$) δ 9.06 (s, 1H), 8.80 (d, J=1.5 Hz, 1H), 7.97-7.84 (m, 3H), 7.55 (d, J=7.4 Hz, 1H), 7.52-7.47 (m, 2H), 7.15 (d, J=2.0 Hz, 1H), 6.81 (d, J=1.5 Hz, 1H), 4.82 (s, 2H), 4.04 (t, J=5.4 Hz, 2H), 3.57 (s, 3H), 3.35 (t, J=5.7 Hz, 2H), 2.76 (s, 3H), 2.69 (s, 3H). LC-MS: method C, RT=2.43 min, MS (ESI) m/z: 535.15 (M+H)$^+$. Analytical HPLC purity (method B): 98%.

Example 96

2-fluoro N-(2-(2-(2-(methoxymethyl)-7-methylquinoxalin-5-yl)-4-methylbenzo[d]thiazol-6-yloxy)ethyl)benzenesulfonamide

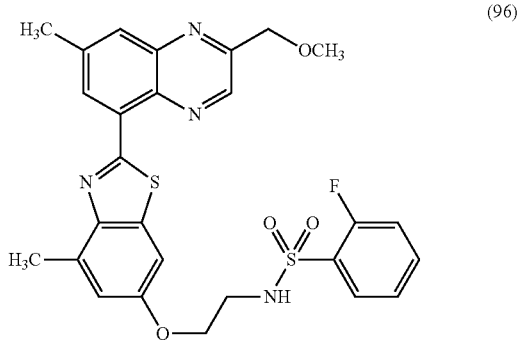 [SMILES: COCc1cnc2c(-c3nc4c(C)cc(OCCNS(=O)(=O)c5ccccc5F)cc4s3)cc(C)cc2n1]

(96)

To a solution of Intermediate 95B (8 mg, 0.020 mmol) in DMF (1 mL) was added DIEA (0.035 mL, 0.203 mmol) and 2-fluorobenzene-1-sulfonyl chloride (4.74 mg, 0.024 mmol). The mixture was stirred at room temperature for 1 h. LCMS indicated a completion of the reaction. Solvent was removed, the residual was purified via preparative LCMS (method D, 50-90% B over 10 min., then a 5-min hold at 100% B). Fractions containing the desired product were combined and dried via centrifugal evaporation to give Example 96 (4.2 mg, 7.60 mol, 37.5% yield). $^1$H NMR (500 MHz, DMSO-$d_6$) δ 9.08 (s, 1H), 8.78 (d, J=1.9 Hz, 1H), 8.01 (d, J=0.8 Hz, 1H), 7.84 (td, 1.7 Hz, 1H), 7.74-7.65 (m, 1H), 7.43-7.34 (m, 3H), 6.76 (d, J=1.4 Hz, 1H), 4.80 (s, 2H), 4.05 (t, J=5.4 Hz, 2H), 3.46 (s, 3H), 3.35-3.33 (m, 2H), 2.74-2.71 (m, 3H), 2.68 (s, 3H). LC-MS: method C, RT=2.38 min, MS (ESI) m/z: 553.1 (M+H)$^+$. Analytical HPLC purity (method B): 100%.

Example 97

3-fluoro N-(2-(2-(2-(methoxymethyl)-7-methylquinoxalin-5-yl)-4-methylbenzo[d]thiazol-6-yloxy)ethyl)benzenesulfonamide

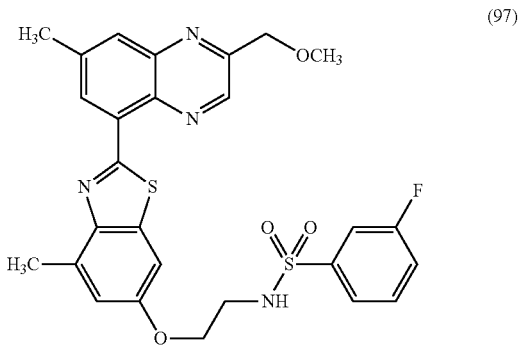 [SMILES: COCc1cnc2c(-c3nc4c(C)cc(OCCNS(=O)(=O)c5cccc(F)c5)cc4s3)cc(C)cc2n1]

(97)

To a solution of Intermediate 95B (8 mg, 0.020 mmol) in DMF (1 mL) was added DIEA (0.035 mL, 0.203 mmol) and 3-fluorobenzene-1-sulfonyl chloride (4.74 mg, 0.024 mmol). The mixture was stirred at room temperature for 1 h. LCMS indicated a completion of the reaction. Solvent was removed, the residual was purified via preparative LCMS (method D, 50-90% B over 10 min., then a 5-min hold at 100% B). Fractions containing the desired product were combined and dried via centrifugal evaporation to give Example 97 (4.1 mg, 7.34 mol, 36.2% yield). $^1$H NMR (500 MHz, DMSO-$d_6$) δ 9.08 (s, 1H), 8.80 (d, J=1.9 Hz, 1H), 8.14 (br. s., 1H), 8.02 (s, 1H), 7.73-7.61 (m, 3H), 7.50 (s, 1H), 7.45 (s, 1H), 6.86 (d, J=1.4 Hz, 1H), 4.81 (s, 2H), 4.06 (t, J=5.4 Hz, 2H), 3.47 (s, 3H), 3.26 (d, J=5.0 Hz, 2H), 2.74 (s, 3H), 2.69 (s, 3H). LC-MS: method C, RT=2.38 min, MS (ESI) m/z: 553.1 (M+H)$^+$. Analytical HPLC purity (method B): 99%.

Example 98

N-(2-(4-chloro-2-(2-(methoxymethyl)-7-methylquinoxalin-5-yl)benzo[d]thiazol-6-yloxy)ethyl)methanesulfonamide

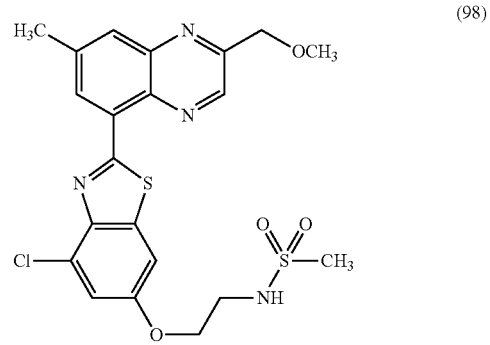 [SMILES: COCc1cnc2c(-c3nc4c(Cl)cc(OCCNS(C)(=O)=O)cc4s3)cc(C)cc2n1]

(98)

Intermediate 98A: tert-butyl 2-(3-chloro-4-nitrophenoxy)ethylcarbamate

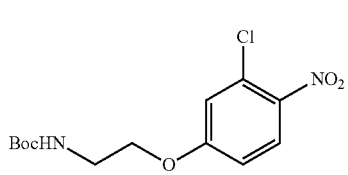
(98A)

To a solution of tert-butyl (2-hydroxyethyl)carbamate (3.67 g, 22.79 mmol) in THF (30 mL) was added 1 N sodium bis(trimethylsilyl)amide in THF (25.06 mL, 25.06 mmol). The mixture was stirred at room temperature for 10 min. 2-Chloro-4-fluoro-1-nitrobenzene (2 g, 11.39 mmol) was added and the reaction mixture was stirred at room temperature for 2 h. The mixture was diluted with EtOAc, quenched with saturated ammonium chloride. The organic layer was washed with saturated sodium bicarbonate, brine, dried over sodium sulfate and concentrated. The crude product was purified with flash chromatography (loading in chloroform, 0% to 45% EtOAc in hexanes over 15 min using a 120 g silica gel cartridge). The desired fractions were combined and concentrated to yield Intermediate 98A (3.6 g, 11.37 mmol, 100% yield) as a yellow liquid. $^1$H NMR (400 MHz, chloroform-d) δ 8.10-7.87 (m, 1H), 7.03 (d, J=2.4 Hz, 1H), 6.88 (dd, J=9.0, 2.6 Hz, 1H), 4.94 (br. s., 1H), 4.11-4.02 (m, 2H), 3.57 (q, J=5.4 Hz, 2H), 1.46 (s, 9H). LC-MS: method C, RT=2.04 min, MS (ESI) m/z: 217 [M+1−Boc]$^+$.

Intermediate 98B: tert-butyl 2-(4-amino-3-chlorophenoxy)ethylcarbamate

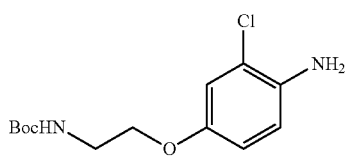
(98B)

To a solution of Intermediate 98A (3.6 g, 11.37 mmol) in MeOH (6.0 mL) was added ammonium chloride (7.30 g, 136 mmol) and zinc dust (4.46 g, 68.2 mmol). The mixture was stirred at room temperature overnight. MeOH was removed. The residue was diluted with EtOAc/saturated sodium bicarbonate and stirred at room temperature for 10 min. The mixture was filtered to remove insoluble material. The filtrate was collected, organic layer was washed with brine, dried over sodium sulfate and concentrated. The crude sample was purified with a 120 g ISCO column eluted with 0-100% EtOAc in hexanes for 40 min. The desired fraction was collected and concentrated to give Intermediate 98B (2.9 g, 10.11 mmol, 89% yield) as off-white solid. $^1$H NMR (400 MHz, chloroform-d) δ 6.86 (d, J=2.4 Hz, 1H), 6.80-6.65 (m, 2H), 3.94 (t, J=5.2 Hz, 2H), 3.49 (q, J=4.9 Hz, 2H), 1.46 (s, 9H). LC-MS: method C, RT=1.52 min, MS (ESI) m/z: 187 [M+1−Boc]$^+$.

Intermediate 98C: tert-butyl 2-(2-amino-4-chlorobenzo[d]thiazol-6-yloxy)ethylcarbamate

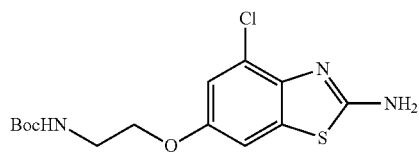
(98C)

To Intermediate 98B (2.9 g, 10.11 mmol) in acetonitrile (30 mL) was added ammonium thiocyanate (1.347 g, 17.70 mmol). The mixture was stirred at room temperature for 10 min. Benzyltrimethylammonium tribromide (5.32 g, 13.65 mmol) in acetonitrile (2.0 mL) was added dropwise (5 min). The mixture was stirred at room temperature overnight. Acetonitrile was removed. The residual was diluted with EtOAc and saturated sodium bicarbonate, extracted with EtOAc (3×). The combined organic layer was washed with brine, dried over sodium sulfate and concentrated to give Intermediate 98C (2.8 g, 8.14 mmol, 81% yield) as a yellow solid that was used for the next step without further purification. $^1$H NMR (400 MHz, Methanol-d$_4$) δ 7.02 (d, J=2.4 Hz, 1H), 6.90 (d, J=2.2 Hz, 1H), 3.97 (t, J=5.4 Hz, 2H), 3.48-3.39 (m, 2H), 1.41 (s, 9H). LC-MS: method C, RT=1.71 min, MS (ESI) m/z: 344 (M+H)$^+$.

Intermediate 98D: tert-butyl 2-(2-bromo-4-chlorobenzo[d]thiazol-6-yloxy) ethylcarbamate

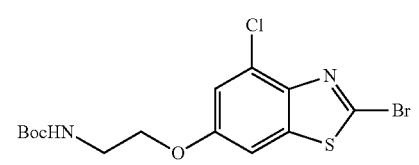
(98D)

To a solution of copper (II) bromide (1.402 g, 9.77 mmol) in acetonitrile (30 mL) at 40° C. was added tert-butyl nitrite (1.399 mL, 10.59 mmol) followed by Intermediate 98C (2.8 g, 8.14 mmol) as a solid. The mixture was stirring at 40° C. for 2.0 h and then room temperature overnight. The mixture was diluted with EtOAc, washed with 0.5 HCl, saturated sodium bicarbonate and brine. After evaporation of solvent, the crude sample was purified with a 40 g ISCO column eluted with 0-70% EtOAc in hexanes for 20 min. The desired fraction was collected and concentrated to give Intermediate 98D (240 mg, 0.589 mmol, 7.23% yield). $^1$H NMR (400 MHz, chloroform-d) δ 7.15 (d, J=2.4 Hz, 1H), 7.11 (d, J=2.4 Hz, 1H), 4.06 (t, J=5.2 Hz, 2H), 3.56 (q, J=5.3 Hz, 2H), 1.46 (s, 9H). LC-MS: method C, RT=2.21 min, MS (ESI) m/z: 406.9 and 408.9 (M+H)$^+$.

Intermediate 98E: tert-butyl 2-(4-chloro-2-(2-(methoxymethyl)-7-methylquinoxalin-5-yl)benzo[d]thiazol-6-yloxy)ethylcarbamate

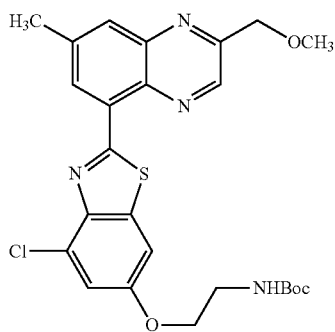

(98E)

To Intermediate I-2 (40 mg, 0.172 mmol), Intermediate 98D (70.3 mg, 0.172 mmol) and [1,1′-bis(diphenylphosphino)ferrocene]dichloropalladium (II) complex with dichloromethane (1:1) (7.04 mg, 8.62 μmol) was added toluene (1.5 mL), EtOH (0.5 mL) and sodium carbonate (0.172 mL, 2M, 0.345 mmol). The mixture was degassed with argon for 5 min. The reaction mixture was heated in a microwave reactor at 120° C. for 40 min. To the reaction mixture was added EtOAc/water/brine. The insoluble was removed by filtration with a pad of celite. The organic layers were collected, washed with brine, dried over sodium sulfate. After evaporation of solvent, the crude product was dissolved in a small amount of chloroform and charged to a 40 g ISCO column which was eluted with hexanes for 3 min., then a 20 min gradient from 0% to 100% EtOAc in hexanes. The desired fraction was collected and concentrated to give Intermediate 98E (85 mg, 0.165 mmol, 96% yields). $^1$H NMR (500 MHz, DMSO-$d_6$) δ 9.09 (s, 1H), 8.80 (d, J=1.7 Hz, 1H), 8.06 (s, 1H), 7.76 (d, J=2.2 Hz, 1H), 7.29 (d, J=2.2 Hz, 1H), 7.05 (br. s., 1H), 4.81 (s, 2H), 4.10 (t, J=5.6 Hz, 2H), 3.47 (s, 3H), 3.39-3.34 (m, 2H), 2.70 (s, 3H), 1.39 (s, 9H). LC-MS: method C, RT=2.54 min, MS (ESI) m/z: 515 (M+H)$^+$.

Intermediate 98F: 2-(4-chloro-2-(2-(methoxymethyl)-7-methylquinoxalin-5-yl) benzo[d]thiazol-6-yloxy)ethanamine

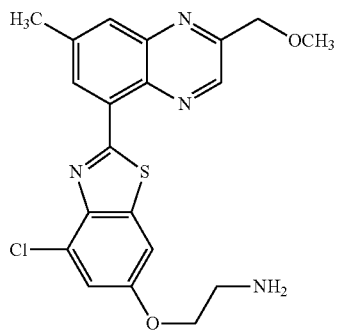

(98F)

To a solution of Intermediate 98E (85 mg, 0.165 mmol) in DCM (2 mL) was added 2,6-lutidine (0.058 mL, 0.495 mmol) followed by TMS-OTf (0.135 mL, 0.75 mmol) at 0° C. The mixture was stirred at room temperature for 2 h. LCMS indicated a completion of the reaction. The mixture was diluted with EtOAc and NaHCO$_3$, extracted with EtOAc. The combined organic layer was washed with brine and concentrated. The residual was added 1 ml of MeOH and stirred at room temperature for 15 min and concentrated to give Intermediate 98F (65 mg, 0.157 mmol, 95% yield) as a yellow solid. the crude sample was used for next step without purification. $^1$H NMR (400 MHz, Methanol-$d_4$) δ 9.04 (s, 1H), 8.90-8.82 (m, 1H), 7.92 (s, 1H), 7.38 (d, J=2.2 Hz, 1H), 7.19 (d, J=2.2 Hz, 1H), 4.81 (s, 2H), 4.10 (t, J=5.0 Hz, 2H), 3.56 (s, 3H), 3.10 (br. s., 2H), 2.69 (s, 3H). LC-MS: method C, RT=1.91 min, MS (ESI) m/z: 415 (M+H)$^+$.

Example 98

To a solution of Intermediate 98F (12.45 mg, 0.03 mmol) in DMF (1 mL) was added DIEA (0.052 mL, 0.300 mmol) and methanesulfonyl chloride (4.12 mg, 0.036 mmol). The mixture was stirred at room temperature for 15 min. The reaction was quenched with water, and the solvent was removed. The residual was purified via preparative LCMS (method D, 55-95% B over 10 min., then a 5-min hold at 100% B). Fractions containing the desired product were combined and dried via centrifugal evaporation to give Example 98 (6.2 mg, 0.013 mmol, 41.9% yield). $^1$H NMR (500 MHz, DMSO-$d_6$) δ 9.09 (s, 1H), 8.79 (d, J=1.9 Hz, 1H), 8.06 (d, J=0.6 Hz, 1H), 7.78 (d, J=2.2 Hz, 1H), 7.33 (s, 1H), 4.81 (s, 2H), 4.18 (t, J=5.5 Hz, 2H), 3.47 (s, 3H), 3.40 (d, J=5.0 Hz, 2H), 2.98 (s, 3H), 2.70 (s, 3H). LC-MS: method C, RT=2.10 min, MS (ESI) m/z: 493.10 (M+H)$^+$. Analytical HPLC purity (method B): 100%.

Example 99

N-(2-(4-chloro-2-(2-(methoxymethyl)-7-methylquinoxalin-5-yl)benzo[d]thiazol-6-yloxy) ethyl)benzenesulfonamide

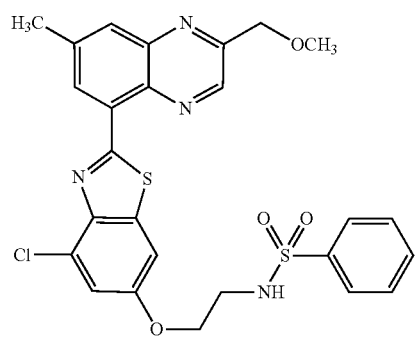

(99)

To a solution of Intermediate 98F (12.45 mg, 0.03 mmol) in DMF (1 mL) was added DIEA (0.052 mL, 0.300 mmol) and benzenesulfonyl chloride (6.36 mg, 0.036 mmol). The mixture was stirred at room temperature for 15 min. LCMS indicated a completion of the reaction. The reaction was quenched by water and solvent was removed. The residual was purified via preparative LC/MS (method D, 55-100% B over 11 min, then a 4-min hold at 100% B). Fractions containing the desired product were combined and dried via centrifugal evaporation to give Example 99 (7.0 mg, 0.012 mmol, 41.6% yield). $^1$H NMR (500 MHz, DMSO-$d_6$) δ 9.04 (s, 1H), 8.73 (d, J=1.4 Hz, 1H), 8.00 (s, 2H), 7.85 (d, J=7.2 Hz, 2H), 7.69-7.54 (m, 3H), 7.12 (d, J=2.2 Hz, 1H), 4.79 (s, 2H), 4.08 (t, J=5.2 Hz, 2H), 3.47 (s, 3H), 3.22 (t, J=5.0 Hz, 2H), 2.67 (s, 3H). LC-MS: method C, RT=2.38 min, MS (ESI) m/z: 555.2 (M+H)$^+$. Analytical HPLC purity (method B): 99%.

Example 100

N-(2-(4-chloro-2-(2-(methoxymethyl)-7-methylquinoxalin-5-yl)benzo[d]thiazol-6-yloxy) ethyl)-2-fluorobenzenesulfonamide

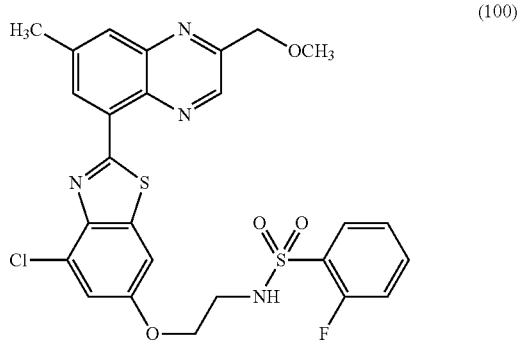 [SMILES: COCc1cnc2c(-c3nc4c(Cl)cc(OCCNS(=O)(=O)c5ccccc5F)cc4s3)cc(C)cc2n1]

(100)

To a solution of Intermediate 98F (12.45 mg, 0.03 mmol) in DMF (1 mL) was added DIEA (0.052 mL, 0.300 mmol) and 2-fluorobenzene-1-sulfonyl chloride (7.01 mg, 0.036 mmol). The mixture was stirred at room temperature for 15 min. LCMS indicated a completion of the reaction. The reaction was quenched by water and solvent was removed. The residual was purified via preparative LC/MS (method D, 55-100% B over 10 min., then a 5-min hold at 100% B). Fractions containing the desired product were combined and dried via centrifugal evaporation to give Example 100 (7.6 mg, 0.013 mmol, 44.2% yield). $^1$H NMR (500 MHz, DMSO-$d_6$) δ 9.08 (s, 1H), 8.78 (d, J=1.9 Hz, 1H), 8.05 (s, 1H), 7.84 (td, J=7.8, 1.5 Hz, 1H), 7.71-7.64 (m, 1H), 7.62 (d, J=2.2 Hz, 1H), 7.45-7.34 (m, 2H), 7.03 (d, J=2.5 Hz, 1H), 4.81 (s, 2H), 4.09 (t, J=5.2 Hz, 2H), 3.47 (s, 3H), 3.36 (t, J=5.2 Hz, 2H), 2.69 (s, 3H). LC-MS: method C, RT=2.38 min, MS (ESI) m/z: 573.1 (M+H)$^+$. Analytical HPLC purity (method B): 100%.

Example 101

N-(2-(4-chloro-2-(2-(methoxymethyl)-7-methylquinoxalin-5-yl)benzo[d]thiazol-6-yloxy) ethyl)-4-fluorobenzenesulfonamide

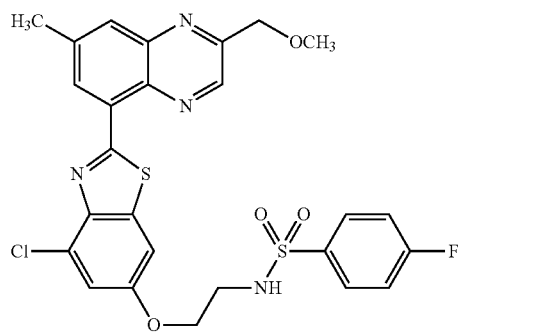

(101)

To a solution of Intermediate 98F (14.52 mg, 0.035 mmol) in DMF (1 mL) was added DIEA (0.061 mL, 0.350 mmol) and 4-fluorobenzene-1-sulfonyl chloride (8.17 mg, 0.042 mmol). The mixture was stirred at room temperature For 15 min. LCMS indicated a completion of the reaction. The reaction was quenched by water and solvent was removed. The residual was purified via preparative LC/MS (method D, 55-100% B over 10 min., then a 5-min hold at 100% B). Fractions containing the desired product were combined and dried via centrifugal evaporation to give Example 101 (11.3 mg, 0.020 mmol, 56.3% yield). $^1$H NMR (500 MHz, DMSO-$d_6$) δ 9.08 (s, 1H), 8.78 (d, J=1.7 Hz, 1H), 8.05 (s, 1H), 7.96-7.84 (m, 2H), 7.66 (d, J=2.5 Hz, 1H), 7.47-7.37 (m, 2H), 7.14 (d, J=2.2 Hz, 1H), 4.81 (s, 2H), 4.09 (t, J=5.2 Hz, 2H), 3.47 (s, 3H), 3.23 (t, J=5.2 Hz, 2H), 2.70 (s, 3H). LC-MS: method C, RT=2.38 min, MS (ESI) m/z: 573.1 (M+H)$^+$. Analytical HPLC purity (method B): 100%.

Example 102

N-(2-(4-chloro-2-(2-(methoxymethyl)-7-methylquinoxalin-5-yl)benzo[d]thiazol-6-yloxy) ethyl)-3-fluorobenzenesulfonamide

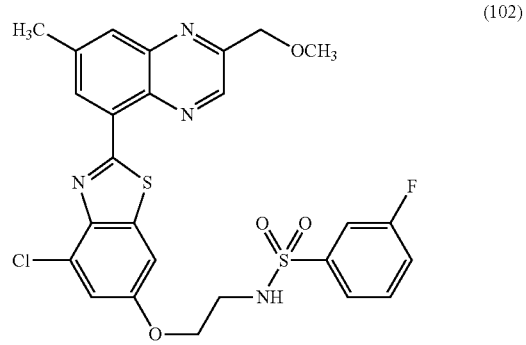 [SMILES: COCc1cnc2c(-c3nc4c(Cl)cc(OCCNS(=O)(=O)c5cccc(F)c5)cc4s3)cc(C)cc2n1]

(102)

To a solution of Intermediate 98F (12.45 mg, 0.03 mmol) in DMF (1 mL) was added DIEA (0.052 mL, 0.300 mmol) and 3-fluorobenzene-1-sulfonyl chloride (7.01 mg, 0.036 mmol). The mixture was stirred at room temperature for 15 min. LCMS indicated a completion of the reaction. The reaction was quenched by water and solvent was removed. The residual was purified via preparative LC/MS (method D, 55-100% B over 10 min., then a 5-min hold at 100% B). Fractions containing the desired product were combined and dried via centrifugal evaporation to give Example 102 (7.5 mg, 0.013 mmol, 42.8% yield). $^1$H NMR (500 MHz, DMSO-$d_6$) δ 9.08 (s, 1H), 8.78 (d, J=1.9 Hz, 1H), 8.05 (d, J=0.8 Hz, 1H), 7.75-7.59 (m, 4H), 7.52-7.42 (m, 1H), 7.13 (d, J=2.5 Hz, 1H), 4.81 (s, 2H), 4.09 (t, J=5.2 Hz, 2H), 3.47 (s, 3H), 3.27 (t, J=5.2 Hz, 2H), 2.69 (s, 3H). LC-MS: method C, RT=2.41 min, MS (ESI) m/z: 573.1 (M+H)$^+$. Analytical HPLC purity (method B): 98%.

Example 103

6-methoxy-2-(2-(methoxymethyl)-7-methylquinoxalin-5-yl)benzo[d]thiazole-4-carbonitrile

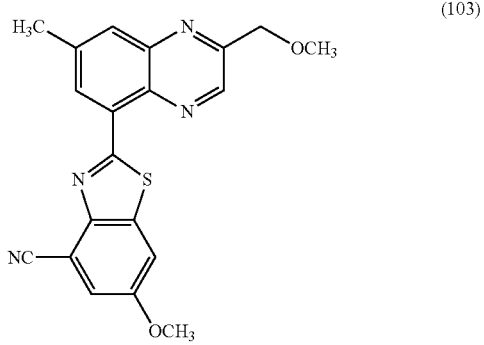 [SMILES: COCc1cnc2c(-c3nc4c(C#N)cc(OC)cc4s3)cc(C)cc2n1]

(103)

Intermediate 103A:
2-bromo-4-methoxy-1-nitrobenzene

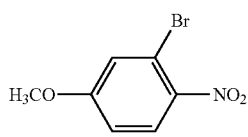

(103A)

To a solution of 2-bromo-4-fluoro-1-nitrobenzene (2 g, 9.09 mmol) in THF (30 mL) was added sodium methoxide (1.48 g, 27 mmol). The mixture was stirred at room temperature overnight. Solvent was removed under vacuum and the residual was diluted with EtOAc, quenched with saturated ammonium chloride. The organic layer was washed with saturated sodium bicarbonate, brine, dried over sodium sulfate and concentrated. The crude product was purified with flash chromatography (loading in chloroform, 0% to 50% EtOAc in hexanes over 40 min using a 120 g silica gel cartridge). The desired fractions were combined and concentrated to yield Intermediate 103A (1.7 g, 7.33 mmol, 81% yield) as an off-white solid. $^1$H NMR (400 MHz, chloroform-d) δ 8.00 (d, J=9.0 Hz, 1H), 7.23 (d, J=2.6 Hz, 1H), 6.93 (dd, J=9.0, 2.6 Hz, 1H), 3.90 (s, 3H). LC-MS: method C, RT=1.82 min, MS (ESI) m/z: 231.9 and 233.9 (M+H)$^+$.

Intermediate 103B: 2-bromo-4-methoxyaniline

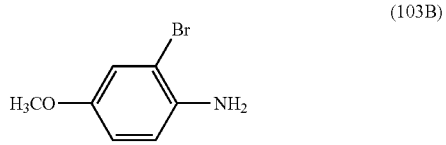 [SMILES: COc1ccc([N+](=O)[O-])c(Br)c1]

(103B)

To a solution of Intermediate 103A (1.7 g, 7.33 mmol) in MeOH (30 mL) was added ammonium chloride (7.84 g, 147 mmol) and zinc dust (4.79 g, 73.3 mmol). The mixture was stirred at room temperature for 1 h. LCMS indicated a clean reaction. MeOH was removed. The residue was diluted with EtOAc/saturated sodium bicarbonate and stirred at room temperature for 10 min. The mixture was filtered to remove insoluble material. The filtrate was collected, organic layer was washed with brine, dried over sodium sulfate, concentrated. The crude sample was purified with a 120 g ISCO column eluted with 0-100% EtOAc in hexanes for 40 min. The desired fraction was collected and concentrated to give Intermediate 103B (1.3 g, 6.43 mmol, 88% yield) as oil. $^1$H NMR (400 MHz, chloroform-d) δ 7.01 (d, J=2.0 Hz, 1H), 6.76-6.70 (m, 2H), 3.79 (br. s., 2H), 3.74 (s, 3H). LC-MS: method C, RT=0.80 min, MS (ESI) m/z: 202 and 204 (M+H)$^+$.

Intermediate 103C:
4-bromo-6-methoxybenzo[d]thiazol-2-amine

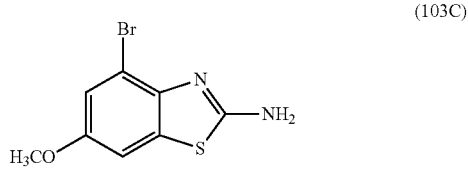

(103C)

To a mixture of Intermediate 103B (1.3 g, 6.43 mmol) in acetonitrile (15 mL) was added ammonium thiocyanate (0.857 g, 11.26 mmol). The mixture was stirred at room temperature for 10 min. Benzyltrimethylammonium tribromide (3.39 g, 8.69 mmol) in acetonitrile (10 mL) was added dropwise (5 min). The mixture was stirred at room temperature overnight. Acetonitrile was removed. The mixture was diluted with EtOAc, saturated sodium bicarbonate. The insoluble material was removed by filtration. The organic layer of the filtrate was collected, washed with brine, dried over sodium sulfate and concentrated to give Intermediate 103C (1.5 g, 5.79 mmol, 90% yield) as a yellow solid that was used for the next step without further purification. LC-MS: method C, RT=1.41 min, MS (ESI) m/z: 259 and 261 (M+H)$^+$.

Intermediate 103D: tert-butyl N-(4-bromo-6-methoxy-1,3-benzothiazol-2-yl)-N-[(tert-butoxy)carbonyl]carbamate

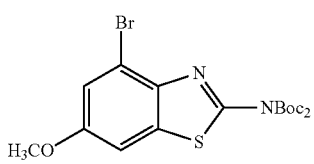

(103D)

To a solution of Intermediate 103C (1.2 g, 4.63 mmol) in DMF (20 mL) was added DMAP (566 mg, 4.63 mmol) and Boc$_2$O (3032 mg, 13.89 mmol). The mixture was stirred under argon over the weekend. The mixture was partitioned into water (300 mL) and extracted with ethyl acetate (2×200 mL). The organic layers were combined, washed with brine, dried over Na$_2$SO$_4$, filtered and concentrated. The residue was purified with a 40 g ISCO column eluted with 0-50% EtOAc/hexanes for 40 min. The desired fraction was collected and concentrated to give Intermediate 103D (400 mg, 0.871 mmol, 18.80% yield). LC-MS: method C, RT=2.40 min, MS (ESI) m/z: 302.9 and 304.9 (M+H−Boc)⁺.

Intermediate 103E: 2-amino-6-methoxybenzo[d]thiazole-4-carbonitrile

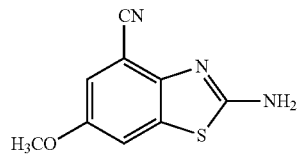

(103E)

A mixture of Intermediate 103D (100 mg, 0.218 mmol), zinc cyanide (25.6 mg, 0.218 mmol), palladium (II) trifluoroacetate (5.79 mg, 0.017 mmol), racemic-2-(di-t-butylphosphino)-1,1'-binaphthyl (13.88 mg, 0.035 mmol) and zinc dust (4.27 mg, 0.065 mmol) in DMA (1.5 mL) was degassed with argon for 5 min. The reaction mixture was heated in a microwave reactor at 100° C. for 20 min. It was diluted with EtOAc/saturated sodium bicarbonate. The organic layer was washed with brine, dried over sodium sulfate. After evaporation of solvent, the crude product was purified with a 12 g ISCO column eluted with 0-70% EtOAc in hexanes for 15 min. The desired fraction was collected to give di-boc protected intermediate (50 mg, 0.123 mmol, 56.6% yield) as colorless oil. The intermediate was redissolved in 1 ml of DCM and TFA (0.839 mL, 10.88 mmol) was added. The mixture was stirred at room temperature for 1 h. LCMS indicated a completion of the reaction. Solvent was removed and the residual was diluted EtOAc/saturated sodium bicarbonate. The organic layer was washed with brine, dried over sodium sulfate. After evaporation of solvent, the crude product was purified with a 12 g ISCO column eluted with 0-100% EtOAc in hexanes for 15 min. The desired fraction was collected and concentrated to give Intermediate 103E (24 mg, 0.117 mmol, 53.7% yield). ¹H NMR (400 MHz, methanol-d₄) δ 7.51 (d, J=2.6 Hz, 1H), 7.15 (d, J=2.6 Hz, 1H), 3.83 (s, 3H). LC-MS: method C, RT=1.42 min, MS (ESI) m/z: 206 (M+H)⁺.

Intermediate 103F: 2-bromo-6-methoxybenzo[d]thiazole-4-carbonitrile

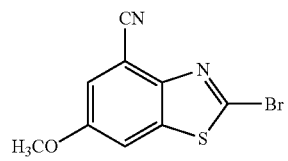

(103F)

To a stirred solution of copper (II) bromide (20.13 mg, 0.140 mmol) and Intermediate 103E (24 mg, 0.117 mmol) in acetonitrile (2 mL) was added tert-butyl nitrite (0.020 mL, 0.152 mmol). The mixture was stirred at 20° C. for 4.0 h. TLC and LCMS indicated a clean reaction. Acetonitrile was removed under vacuum, the reaction mixture was diluted with EtOAc, quenched with 1.0 N HCl. The organic layer was collected, washed with 0.5 N HCl (2×), saturated sodium bicarbonate, brine, dried over sodium sulfate. After evaporation of solvent, the crude was purified with a 12 g ISCO column eluted with 0-70% EtOAc in hexanes for 20 min. Intermediate 103F (15 mg, 0.056 mmol, 47.7% yield) was obtained as an off-white solid. ¹H NMR (400 MHz, chloroform-d) δ 7.49 (d, J=2.4 Hz, 1H), 7.38 (d, J=2.6 Hz, 1H), 3.92 (s, 3H). LC-MS: method C, RT=1.79 min, MS (ESI) m/z: 268.9 and 270.9 (M+H)⁺.

Example 103

To Intermediate I-2 (9.5 mg, 0.041 mmol), Intermediate 103F (11.02 mg, 0.041 mmol) and [1,1'-bis(diphenylphosphino)ferrocene]dichloropalladium (II) complex with dichloromethane (1:1) (1.672 mg, 2.047 μmol) was added toluene (0.75 mL), EtOH (0.25 mL) and sodium carbonate (0.041 mL, 2M, 0.082 mmol). The mixture was degassed with argon for 5 min. The reaction mixture was heated in a microwave reactor at 120° C. for 40 min. To the reaction mixture was added EtOAc/water/brine. The insoluble was removed by filtration with a pad of celite. The organic layers were collected, washed with brine, dried over sodium sulfate. After evaporation of solvent, the crude product was purified via preparative LC/MS (method D, 45-90% B over 20 min., then a 5-min hold at 100% B). Fractions containing the desired product were combined and dried via centrifugal evaporation to give Example 103 (1.7 mg, 4.34 μmol, 10.59% yield). ¹H NMR (500 MHz, DMSO-d₆) δ 9.10 (s, 1H), 8.82 (s, 1H), 8.16 (br. s., 1H), 8.09 (s, 1H), 7.75 (br. s., 1H), 4.82 (s, 2H), 3.93 (s, 3H), 3.48 (s, 3H), 2.72 (s, 3H). LC-MS: method C, RT=2.31 min, MS (ESI) m/z: 377.1 (M+H)⁺. Analytical HPLC purity (method B): 96%.

Example 104

N-(2-(4-cyclopropyl-2-(2-(methoxymethyl)-7-methylquinoxalin-5-yl)benzo[d]thiazol-6-yloxy)ethyl)benzenesulfonamide

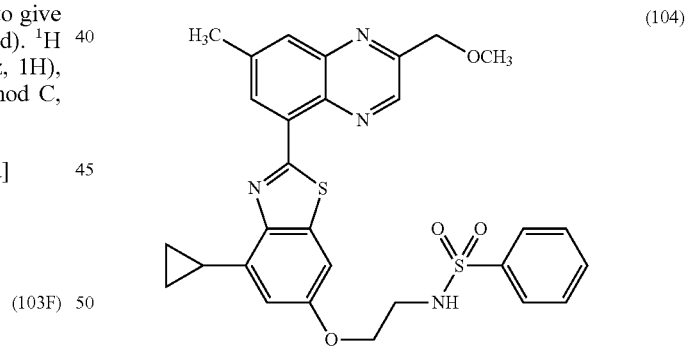

(104)

Intermediate 104A: tert-butyl 4-bromo-6-methoxybenzo[d]thiazol-2-ylcarbamate

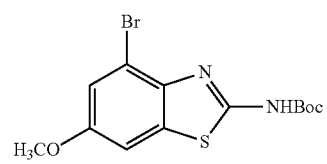

(104A)

To a solution of Intermediate 103D (300 mg, 0.653 mmol) in DCM (3 mL) was added TFA (0.101 mL, 1.306 mmol) and the mixture was stirred at room temperature overnight. The mixture was diluted with EtOAc and saturated NaHCO$_3$, extracted with EtOAc. The combined organic layer was washed with brine, dried with MgSO$_4$ and concentrated to give Intermediate 104A (235 mg, 0.654 mmol, 100% yield) as an off white solid which was used for next step without further purification. $^1$H NMR (400 MHz, chloroform-d) δ 7.24-7.20 (m, 2H), 3.86 (s, 3H), 1.56 (s, 9H). LC-MS: method C, RT=2.30 min, MS (ESI) m/z: 359 and 360.9 (M+H)$^+$.

Intermediate 104B: tert-butyl 4-cyclopropyl-6-methoxybenzo[d]thiazol-2-ylcarbamate

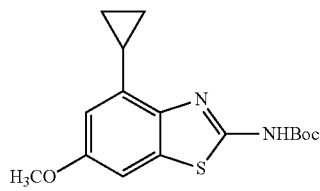

(104B)

A solution of Intermediate 104A (30 mg, 0.084 mmol) and [1,1'-bis(diphenylphosphino)ferrocene]dichloropalladium (II) complex with dichloromethane (1:1) (6.82 mg, 8.35 μmol) in THF (1 mL) was degassed for 2 min. To this solution was added cyclopropylzinc(II) bromide (0.835 mL, 0.5 M in THF, 0.418 mmol). The reaction tube was sealed and heated at 65° C. for 1 h. LCMS indicated a completion of the reaction. The reaction mixture was diluted with EtOAc/water. The organic phase was washed with brine, dried over sodium sulfate. The crude residue was purified with a 12 g ISCO column eluted with 0-70% EtOAc in hexanes for 15 min. Intermediate 104B (26 mg, 0.081 mmol, 97% yield) was obtained as colorless oil. LC-MS: method C, RT=2.33 min, MS (ESI) m/z: 321 (M+H)$^+$.

Intermediate 104C: 4-cyclopropyl-6-methoxybenzo[d]thiazol-2-amine

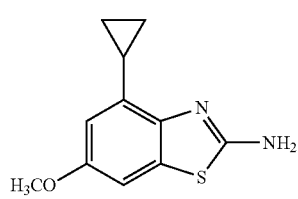

(104C)

To a solution of Intermediate 104B (125 mg, 0.390 mmol) in DCM (1 mL) was added TFA (3.01 mL, 39.0 mmol). The mixture was stirred at room temperature for 1 h. Solvent was removed under vacuum and the residual was diluted with EtOAc and saturated NaHCO$_3$, extracted with EtOAc. The combined organic layer was washed with brine, dried with MgSO$_4$ and concentrated to give Intermediate 104C (80 mg, 0.363 mmol, 93% yield) as an off-white solid. $^1$H NMR (400 MHz, chloroform-d) δ 6.94 (d, J=2.4 Hz, 1H), 6.41 (d, J=2.4 Hz, 1H), 5.19 (br. s., 2H), 3.80 (s, 3H), 2.57-2.43 (m, 1H), 1.14-0.99 (m, 2H), 0.86-0.74 (m, 2H). LC-MS: method C, RT=1.46 min, MS (ESI) m/z: 221 (M+H)$^+$.

Intermediate 104D: 2-bromo-4-cyclopropyl-6-methoxybenzo[d]thiazole

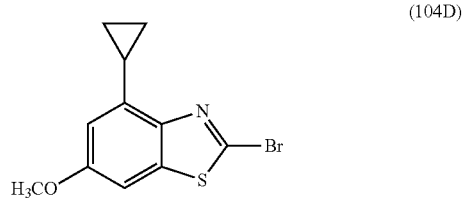 [SMILES: COc1cc(C2CC2)c2nc(Br)sc2c1]

(104D)

To a stirred solution of copper (II) bromide (188 mg, 1.307 mmol) and Intermediate 104C (240 mg, 1.089 mmol) in acetonitrile (3 mL) was added tert-butyl nitrite (0.187 mL, 1.416 mmol). The mixture was stirred at room temperature overnight. Acetonitrile was removed, the reaction mixture was diluted with EtOAc, quenched with 1.0 N HCl. The organic layer was collected, washed with 0.5 N HCl (2×), saturated sodium bicarbonate, brine, dried over sodium sulfate. After evaporation of solvent, the crude oil was purified with a 40 g ISCO column eluted with 0-70% EtOAc in hexanes for 20 min. The desired fraction was collected and concentrated to give Intermediate 104D (180 mg, 0.633 mmol, 58.1% yield) as yellow oil. $^1$H NMR (400 MHz, chloroform-d) δ 7.03 (d, J=2.4 Hz, 1H), 6.49 (d, J=2.4 Hz, 1H), 3.83 (s, 3H), 2.73 (s, 1H), 1.20-1.06 (m, 2H), 0.93-0.81 (m, 2H). LC-MS: method C, RT=2.26 min, MS (ESI) m/z: 283.9 and 285.9. (M+H)$^+$.

Intermediate 104E: 2-bromo-4-cyclopropylbenzo[d]thiazol-6-ol

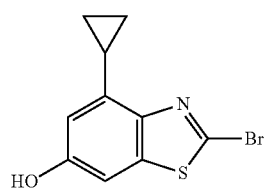

(104E)

To a solution of Intermediate 104D (150 mg, 0.528 mmol) in DCM (3 mL) was added boron tribromide (1.056 mL, 1.0 M in DCM, 1.056 mmol) at room temperature. The mixture was stirred at room temperature for 1 h. The mixture was diluted with EtOAc, quenched with ice and saturated NaHCO$_3$, extracted with EtOAc. The combined organic layer was washed with brine, dried with MgSO$_4$ and concentrated. The crude was purified with a 12 g ISCO column eluted with 0-100% EtOAc in hexanes for 20 min. The desired fraction was collected to give Intermediate 104E (100 mg, 0.37 mmol, 70.2% yield) as a white solid. $^1$H NMR (400 MHz, Methanol-d$_4$) δ 7.02 (d, J=2.4 Hz, 1H), 6.45 (d, J=2.2 Hz, 1H), 2.60 (tt, J=8.5, 5.2 Hz, 1H), 1.14-1.03 (m, 2H), 0.90-0.78 (m, 2H). LC-MS: method C, RT=2.01 min, MS (ESI) m/z: 269.9 and 271.9 (M+H)$^+$.

Intermediate 104F: tert-butyl 2-(2-bromo-4-cyclopropylbenzo[d]thiazol-6-yloxy) ethylcarbamate

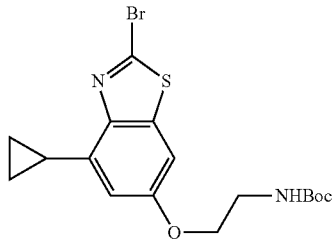
(104F)

A solution of DIAD (0.108 mL, 0.555 mmol) in toluene (1 ml) was added dropwise to a mixture of Intermediate 104E (50 mg, 0.185 mmol), tert-butyl (2-hydroxyethyl) carbamate (35.8 mg, 0.222 mmol) and triphenylphosphine (97 mg, 0.370 mmol) in toluene (1 mL) at 110° C. The mixture was stirred at 110° C. for 30 min. LCMS indicated a completion of the reaction. The mixture was concentrated and purified with a 12 g ISCO column eluted with 0-70% EtOAc in hexanes for 20 min. The desired fraction was collected and concentrated to give Intermediate 104F (70 mg, 0.169 mmol, 92% yield). $^1$H NMR (400 MHz, chloroform-d) δ 7.02 (d, J=2.4 Hz, 1H), 6.49 (d, J=2.4 Hz, 1H), 4.03 (t, J=5.2 Hz, 2H), 3.55 (q, J=5.2 Hz, 2H), 2.80-2.65 (m, 1H), 1.48-1.42 (m, 9H), 1.16-1.08 (m, 2H), 0.91-0.82 (m, 2H). LC-MS: method C, RT=2.35 min, MS (ESI) m/z: 412.9 and 414.9 (M+H)$^+$.

Intermediate 104G: tert-butyl 2-(4-cyclopropyl-2-(2-(methoxymethyl)-7-methylquinoxalin-5-yl)benzo[d]thiazol-6-yloxy)ethylcarbamate

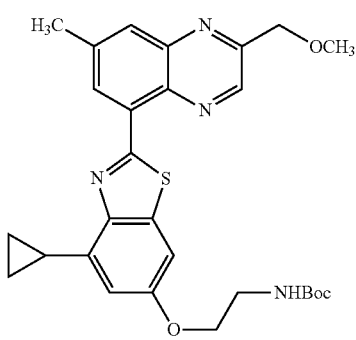
(104G)

To Intermediate I-2 (35 mg, 0.151 mmol), Intermediate 104F (62.3 mg, 0.151 mmol) and [1,1'-bis(diphenylphosphino)ferrocene]dichloropalladium (II) complex with dichloromethane (1:1) (6.16 mg, 2M, 7.54 µmol) was added toluene (0.75 mL), EtOH (0.25 mL) and sodium carbonate (0.151 mL, 0.302 mmol). The mixture was degassed with argon for 5 min. The reaction mixture was heated in a microwave reactor at 120° C. for 40 min. To the reaction mixture was added EtOAc/water/brine. The insoluble was removed by filtration with a pad of celite. The organic layers were collected, washed with brine, dried over sodium sulfate. After evaporation of solvent, the crude product was dissolved in a small amount of chloroform and charged to a 12 g ISCO column which was eluted with hexanes for 3 min., then a 20 min gradient from 0% to 100% EtOAc in hexanes The desired fractions were combined and concentrated to give Intermediate 104G (70 mg, 0.108 mmol, 71.3% yield). $^1$H NMR (500 MHz, DMSO-d$_6$) δ 9.09 (s, 1H), 8.82 (s, 1H), 8.02 (s, 1H), 7.49 (br. s., 1H), 7.02 (br. s., 1H), 6.58 (br. s., 1H), 4.81 (s, 2H), 4.04 (br. s., 2H), 3.47 (s, 3H), 3.33 (m., 2H), 3.01-2.88 (m, 1H), 2.69 (s, 3H), 1.39 (s, 9H), 1.17 (d, J=7.4 Hz, 2H), 1.00 (br. s., 2H). LC-MS: method C, RT=2.50 min, MS (ESI) m/z: 521 (M+H)$^+$.

Intermediate 104H 2-(4-cyclopropyl-2-(2-(methoxymethyl)-7-methylquinoxalin-5-yl)benzo[d]thiazol-6-yloxy) ethanamine

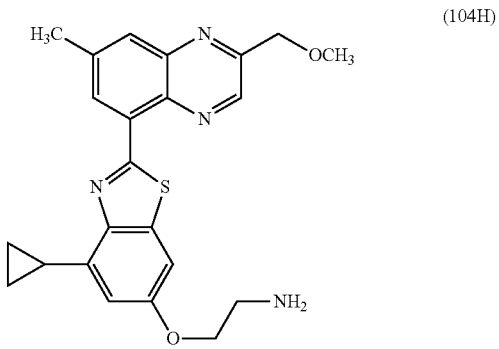 [SMILES: COCc1cnc2c(-c3nc4c(C5CC5)cc(OCCN)cc4s3)cc(C)cc2n1]
(104H)

To a solution of Intermediate 104G (65 mg, 0.125 mmol) in DCM (1 mL) was added 2,6-lutidine (43.6 µl, 0.375 mmol) followed by TMS-OTf (90 µL, 0.499 mmol) at room temperature. The mixture was stirred at room temperature for 1 h. The mixture was diluted with EtOAc and NaHCO$_3$, extracted with EtOAc. The combined organic layer was washed with brine, dried with MgSO$_4$ and concentrated to give Intermediate 104H (52.5 mg, 0.125 mmol, 100% yield). LC-MS: method C, RT=2.01 min, MS (ESI) m/z: 421 (M+H)$^+$.

Example 104

To a solution of Intermediate 104H (14 mg, 0.033 mmol) in DMF (1 mL) was added DIEA (0.058 mL, 0.333 mmol) and benzenesulfonyl chloride (5.15 µL, 0.040 mmol). The mixture was stirred at room temperature for 30 min. LCMS indicated a completion of the reaction. The reaction was quenched with 0.2 ml of MeOH. Solvent was removed. The residual was purified via preparative LC/MS (method D, 50-90% B over 20 min., then a 5-min hold at 100% B). Fractions containing the desired product were combined and dried via centrifugal evaporation to give Example 104 (4.8 mg, 8.56 µmol, 25.7% yield). $^1$H NMR (500 MHz, DMSO-d$_6$) δ 9.08 (s, 1H), 8.80 (s, 1H), 8.01 (s, 1H), 7.95 (br. s., 1H), 7.85 (d, J=7.2 Hz, 2H), 7.68-7.57 (m, 3H), 7.40 (s, 1H), 6.45 (s, 1H), 4.80 (s, 2H), 4.04 (br. s., 2H), 3.47 (s, 3H), 3.19 (br. s., 2H), 2.93 (br. s., 1H), 2.68 (s, 3H), 1.17 (d, J=8.0 Hz, 2H), 0.97 (d, J=3.3 Hz, 2H). LC-MS: method C, RT=2.53 min, MS (ESI) m/z: 561.20 (M+H)$^+$. Analytical HPLC purity (method B): 100%

Example 105

N-(2-(4-cyclopropyl-2-(2-(methoxymethyl)-7-methylquinoxalin-5-yl)benzo[d]thiazol-6-yloxy)ethyl)-4-fluorobenzenesulfonamide

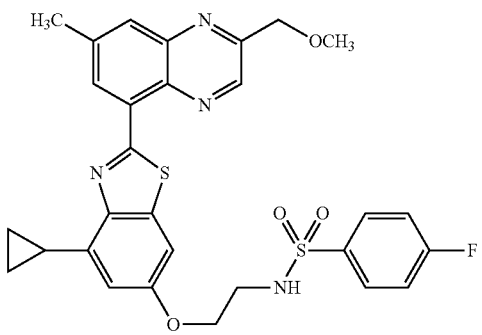
(105)

To a solution of Intermediate 104H (16 mg, 0.038 mmol) in DMF (1 mL) was added DIEA (0.066 mL, 0.380 mmol) and 4-fluorobenzene-1-sulfonyl chloride (8.89 mg, 0.046 mmol). The mixture was stirred at room temperature for 1 h. LCMS indicated a completion of the reaction. The reaction was quenched with 0.2 ml of MeOH. Solvent was removed, the residual was purified via preparative LCMS (method D, 50-90% B over 20 min., then a 5-min hold at 100% B). Fractions containing the desired product were combined and dried via centrifugal evaporation to give Example 105 (8.4 mg, 0.015 mmol, 38.2% yield). $^1$H NMR (500 MHz, DMSO-$d_6$) δ 9.08 (s, 1H), 8.81 (s, 1H), 8.02 (br. s., 2H), 7.92-7.86 (m, 2H), 7.49-7.37 (m, 3H), 6.44 (s, 1H), 4.81 (s, 2H), 4.04 (br. s., 2H), 3.47 (s, 3H), 3.21 (br. s., 2H), 2.92 (d, J=5.2 Hz, 1H), 2.70-2.66 (m, 3H), 1.17 (d, J=7.4 Hz, 2H), 0.97 (d, J=2.5 Hz, 2H). LC-MS: method C, RT=2.54 min, MS (ESI) m/z: 579.20 (M+H)$^+$. Analytical HPLC purity (method B): 100%.

Example 106

N-(2-(2-(2-(methoxymethyl)-7-methylquinoxalin-5-yl)benzo[d]thiazol-6-yloxy)ethyl)benzenesulfonamide

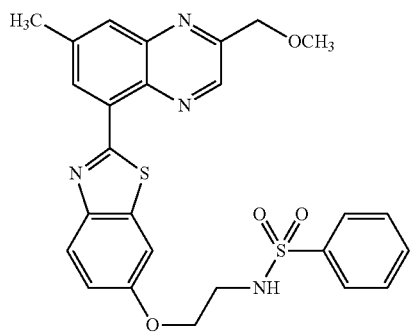
(106)

Intermediate 106A: 2-chlorobenzo[d]thiazol-6-ol

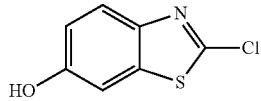
(106A)

Aluminum chloride (7.01 g, 52.6 mmol) was added to a solution of 2-chloro-6-methoxybenzo[d]thiazole (3.5 g, 17.53 mmol) in toluene (80 mL). The mixture was heated at 110° C. for 1.5 h. TLC indicated a complete conversion of starting material. The reaction mixture was cooled to room temperature, quenched with ice-cold 1.0 N HCl (50 mL), stirred at room temperature for 30 min. The precipitate was collected by filtration, washed with water (3×), saturated sodium bicarbonate (3×), water (3×) and air-dried for 1.0 h under vacuum. It was further dried under high vacuum overnight to give Intermediate 106A (2.9 g, 15.62 mmol, 89% yield) as a pale gray solid. The crude sample was used for the next step without purification. $^1$H NMR (400 MHz, methanol-$d_4$) δ 7.70 (d, J=8.8 Hz, 1H), 7.25 (d, J=2.4 Hz, 1H), 6.99 (dd, J=8.8, 2.4 Hz, 1H). LC-MS: method C, RT=1.65 min, MS (ESI) m/z: 185.8 (M+H)$^+$.

Intermediate 106B: tert-butyl 2-(2-chlorobenzo[d]thiazol-6-yloxy)ethylcarbamate

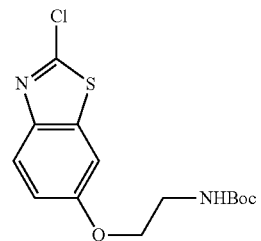
(106B)

A solution of DIAD (0.943 mL, 4.85 mmol) in toluene (4 mL) was added dropwise to a mixture of Intermediate 106A (300 mg, 1.616 mmol), tert-butyl (2-hydroxyethyl)carbamate (313 mg, 1.939 mmol) and triphenylphosphine (848 mg, 3.23 mmol) in toluene (10 mL) at 110° C. The mixture turned to a clean solution and was stirred at 110° C. for 30 min. LCMS indicated a completion of the reaction. The mixture was concentrated and purified with a 40 g ISCO column eluted with 0-70% EtOAc in hexanes for 20 min. The desired fraction was collected and concentrated to give Intermediate 106B (620 mg, 1.508 mmol, 93% yield). $^1$H NMR (400 MHz, chloroform-d) δ 7.83 (d, J=9.0 Hz, 1H), 7.23 (d, J=2.4 Hz, 1H), 7.07 (dd, J=8.9, 2.5 Hz, 1H), 5.12-4.94 (m, 2H), 4.11-4.05 (m, 2H), 3.57 (q, J=5.1 Hz, 2H), 1.51-1.42 (m, 9H). LC-MS: method C, RT=2.49 min, MS (ESI) m/z: 329 (M+H)$^+$.

431

Intermediate 106C: tert-butyl 2-(2-(2-(methoxymethyl)-7-methylquinoxalin-5-yl)benzo[d]thiazol-6-yloxy)ethylcarbamate

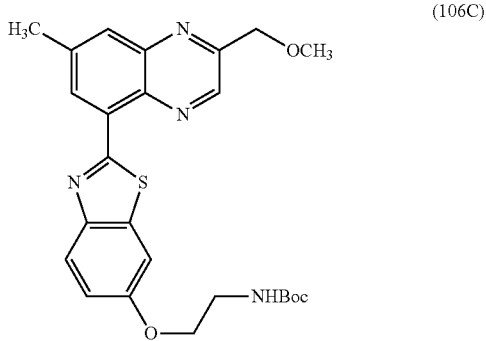 [SMILES: COCc1cnc2c(-c3nc4ccc(OCCNC(=O)OC(C)(C)C)cc4s3)cc(C)cc2n1]

(106C)

To Intermediate I-2 (35 mg, 0.151 mmol), Intermediate 106B (62.0 mg, 0.151 mmol) and [1,1'-bis(diphenylphosphino)ferrocene]dichloropalladium (II) complex with dichloromethane (1:1) (6.16 mg, 7.54 µmol) was added toluene (0.75 mL), EtOH (0.25 mL) and sodium carbonate (0.151 mL, 2M, 0.302 mmol). The mixture was degassed with argon for 5 min. The reaction mixture was heated in a microwave reactor at 120° C. for 30 min. To the reaction mixture was added EtOAc/water/brine. The insoluble was removed by filtration with a pad of celite. The organic layers were collected, washed with brine, dried over sodium sulfate. After evaporation of solvent, the crude product was dissolved in a small amount of chloroform and charged to a 40 g ISCO column which was eluted with hexanes for 3 min., then a 20 min gradient from 0% to 100% EtOAc in hexanes. The desired fractions were combined and concentrated to give Intermediate 106C (63 mg, 0.119 mmol, 79% yield) as a yellow solid. $^1$H NMR (500 MHz, DMSO-d$_6$) δ 9.09 (br. s., 1H), 8.80 (br. s., 1H), 8.05-7.99 (m, 2H), 7.74 (br. s., 1H), 7.16 (d, J=8.8 Hz, 1H), 7.05 (br. s., 1H), 4.81 (br. s., 2H), 4.08 (br. s., 2H), 3.47 (br. s., 3H), 3.36 (br. s., 2H), 2.68 (br. s., 3H), 1.39 (br. s., 9H). LC-MS: method C, RT=2.40 min, MS (ESI) m/z: 481 (M+H)$^+$.

Intermediate 106D 2-(2-(2-(methoxymethyl)-7-methylquinoxalin-5-yl)benzo[d]thiazol-6-yloxy)ethanamine

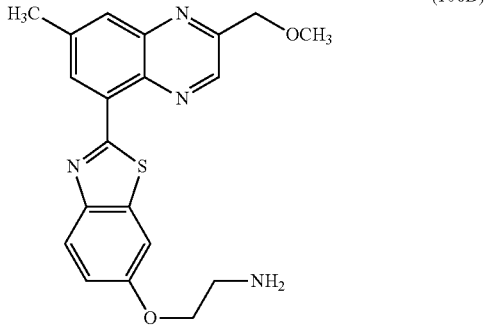

(106D)

To a mixture of Intermediate 106C (60 mg, 0.125 mmol) in DCM (2 ml) was added 2,6-lutidine (43.6 µl, 0.375 mmol) followed by TMS-OTf (90 µl, 0.499 mmol). The mixture was stirred at room temperature for 1 h. LCMS indicated a completion of the reaction. The mixture was diluted with EtOAc and NaHCO$_3$, extracted with EtOAc. The combined organic layer was washed with brine, dried with MgSO$_4$ and concentrated to give Intermediate 106D (45 mg, 0.118 mmol, 95% yield). $^1$H NMR (400 MHz, chloroform-d) δ 9.09 (s, 1H), 8.85 (d, J=1.8 Hz, 1H), 8.04 (d, J=8.8 Hz, 1H), 7.95 (s, 1H), 7.45 (d, J=2.4 Hz, 1H), 7.15 (dd, J=9.0, 2.4 Hz, 1H), 4.85 (s, 2H), 4.11 (t, J=4.8 Hz, 2H), 3.58 (s, 3H), 3.17 (br. s., 2H), 2.70 (s, 3H). LC-MS: method C, RT=1.74 min, MS (ESI) m/z: 381 (M+H)$^+$.

Example 106

To a solution of Intermediate 106D (14 mg, 0.037 mmol) in DMF (1 mL) was added DIEA (0.064 mL, 0.368 mmol) and benzenesulfonyl chloride (5.69 µl, 0.044 mmol). The mixture was stirred at room temperature for 30 min. LCMS indicated a completion of the reaction. The reaction mixture was quenched with 0.2 ml of MeOH. Solvent was removed, the residual was purified via preparative LC/MS (method D, 40-80% B over 10 min., then a 5-min hold at 100% B). Fractions containing the desired product were combined and dried via centrifugal evaporation to give Example 106 (10.7 mg, 0.021 mmol, 55.9% yield). $^1$H NMR (500 MHz, DMSO-d$_6$) δ 9.09 (br. s., 1H), 8.79 (br. s., 1H), 8.12-7.94 (m, 3H), 7.85 (d, J=6.9 Hz, 2H), 7.69-7.53 (m, 4H), 7.08 (d, J=8.5 Hz, 1H), 4.81 (br. s., 2H), 4.08 (br. s., 2H), 3.47 (br. s., 3H), 3.22 (br. s., 2H), 2.68 (br. s., 3H). LC-MS: method C, RT=2.25 min, MS (ESI) m/z: 521.15 (M+H)$^+$. Analytical HPLC purity (method B): 100%.

Example 107

4-fluoro N-(2-(2-(2-(methoxymethyl)-7-methylquinoxalin-5-yl)benzo[d]thiazol-6-yloxy)ethyl)benzenesulfonamide

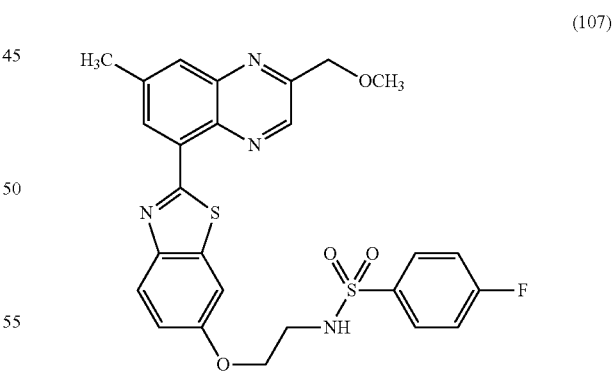

(107)

To a solution of Intermediate 106D (16 mg, 0.042 mmol) in DMF (1 mL) was added DIEA (0.073 mL, 0.421 mmol) and 4-fluorobenzene-1-sulfonyl chloride (9.82 mg, 0.050 mmol). The mixture was stirred at room temperature for 30 min. LCMS indicated a completion of the reaction. The reaction mixture was quenched with 0.2 ml of MeOH. Solvent was removed, the residual was purified via preparative LC/MS (method D, 40-80% B over 10 min., then a 5-min hold at 100% B). Fractions containing the desired product were combined and dried via centrifugal evaporation to give Example 107 (16.3 mg, 0.030 mmol, 70.5% yield). ¹H NMR (500 MHz, DMSO-d₆) δ 9.09 (br. s., 1H), 8.79 (br. s., 1H), 8.09-7.97 (m, 3H), 7.90 (br. s., 2H), 7.66 (br. s., 1H), 7.42 (t, J=8.4 Hz, 2H), 7.07 (d, J=9.1 Hz, 1H), 4.81 (br. s., 2H), 4.08 (br. s., 2H), 3.47 (m, 3H), 3.23 (br. s., 2H), 2.68 (br. s., 3H). LC-MS: method C, RT=2.25 min, MS (ESI) m/z: 539.15 (M+H)⁺. Analytical HPLC purity (method B): 98%.

Example 108

4-fluoro N-(2-(2-(2-(1 fluoroethyl)-7-methylquinoxalin-5-yl)-4-methylbenzo[d]thiazol-6-yloxy)ethyl)benzenesulfonamide

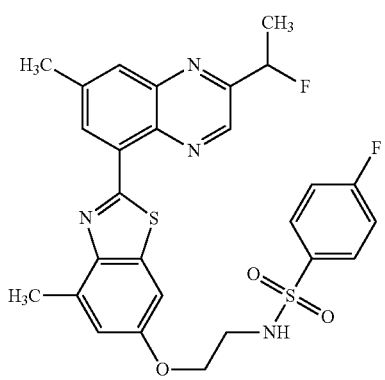
(108)

Intermediate 108A:
1-(5-bromo-7-methylquinoxalin-2-yl)ethanone

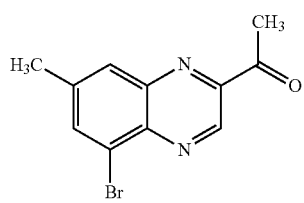
(108A)

To a suspension of methyl 5-bromo-7-methylquinoxaline-2-carboxylate (300 mg, 1.067 mmol) in toluene (5 mL) was added N1,N2-dimethylethane-1,2-diamine (DMEDA) (0.126 mL, 1.174 mmol) and trimethylaluminum (1.601 mL, 3.20 mmol) dropwise under argon at room temperature. The mixture was stirred at room temperature over the weekend. The mixture was diluted with EtOAc and water, extracted with EtOAc. The combined organic layer was washed with saturated NaHCO₃ and brine, dried with MgSO₄ and concentrated. The crude sample was purified with a 40 g ISCO column eluted with 0-80% EtOAc in hexanes for 20 min. The desired fraction was collected to give Intermediate 108A (250 mg, 0.943 mmol, 88% yield) as a yellow solid. ¹H NMR (400 MHz, chloroform-d) δ 9.50 (s, 1H), 8.07 (d, J=1.8 Hz, 1H), 7.96 (dd, J=1.7, 1.0 Hz, 1H), 2.85 (s, 3H), 2.63 (s, 3H). LC-MS: method C, RT=1.99 min, MS (ESI) m/z: 265 and 267 (M+H)⁺.

Intermediate 108B:
2-acetyl-7-methylquinoxalin-5-ylboronic acid

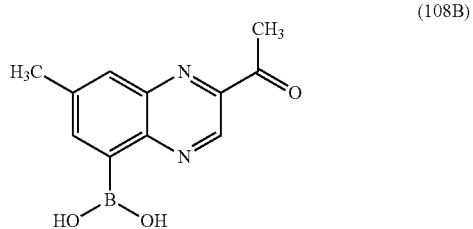 [SMILES: CC(=O)c1cnc2c(B(O)O)cc(C)cc2n1]
(108B)

A mixture of Intermediate 108A (80 mg, 0.302 mmol), 4,4,4',4',5,5,5',5'-octamethyl-2,2'-bi(1,3,2-dioxaborolane) (123 mg, 0.483 mmol), potassium acetate (59.2 mg, 0.604 mmol) and [1,1'-bis(diphenylphosphino)ferrocene]dichloropalladium (II) complex with dichloromethane (1:1) (9.86 mg, 0.012 mmol) in dioxane (1 ml) was degassed with argon for 10 min. The reaction mixture was heated in a microwave reactor at 130° C. for 30 min. The mixture was diluted with EtOAc/water, insoluble material was removed by filtration. The filtrate was extracted with EtOAc, washed with brine, dried over sodium sulfate, concentrated to give Intermediate 108B (69.0 mg, 0.3 mmol) which was used for next step without purification. LC-MS: method C, RT=1.94 min, MS (ESI) m/z: 231 (M+H)⁺ (boronic acid).

Intermediate 108C: N-(2-(2-(2-acetyl-7-methylquinoxalin-5-yl)-4-methylbenzo[d] thiazol-6-yloxy)ethyl)-4-fluorobenzenesulfonamide

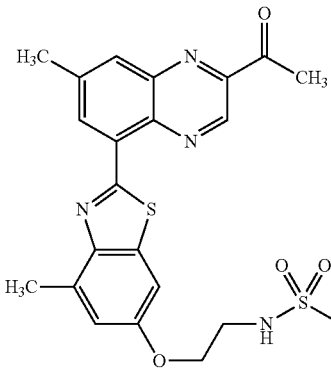
(108C)

To Intermediate 108B (69.0 mg, 0.3 mmol), Intermediate I-5 (111 mg, 0.250 mmol) and [1,1'-bis(diphenylphosphino)ferrocene]dichloropalladium (II) complex with dichloromethane (1:1) (10.21 mg, 0.013 mmol) was added toluene (1.5 mL), EtOH (0.5 mL) and sodium carbonate (0.250 mL, 2M, 0.500 mmol). The mixture was degassed with argon for 5 min. The reaction mixture was heated in a microwave reactor at 130° C. for 30 min. To the reaction mixture was added EtOAc/water/brine. The insoluble was removed by filtration with a pad of celite. The organic layers were collected, washed with brine, dried over sodium sulfate. After evaporation of solvent, the crude product was dissolved in a small amount of chloroform and charged to a 12 g ISCO column which was eluted with hexanes for 3 min., then a 15 min gradient from 0% to 100% EtOAc in hexanes. The desired fractions were combined and concentrated to give Intermediate 108C (20 mg, 0.036 mmol, 14.53% yield) as a yellow solid. $^1$H NMR (400 MHz, chloroform-d) δ 9.57 (s, 1H), 9.02 (d, J=1.8 Hz, 1H), 8.08 (dd, J=2.0, 0.9 Hz, 1H), 7.97-7.90 (m, 2H), 7.24-7.16 (m, 3H), 6.85 (d, J=1.5 Hz, 1H), 5.04-4.90 (m, 1H), 4.15-4.09 (m, 2H), 3.48-3.40 (m, 2H), 2.88 (s, 3H), 2.83 (s, 3H), 2.77 (s, 3H). LC-MS: method C, RT=2.50 min, MS (ESI) m/z: 551 (M+H)$^+$.

Intermediate 108D 4-fluoro N-(2-(2-(2-(1 hydroxyethyl)-7-methylquinoxalin-5-yl)-4-methylbenzo[d]thiazol-6-yloxy)ethyl)benzenesulfonamide

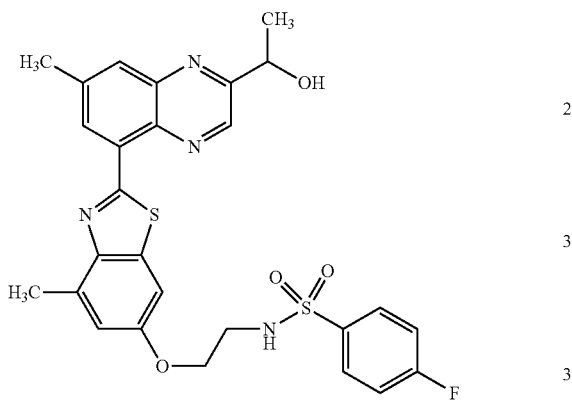

(108D)

To a solution of Intermediate 108C (20 mg, 0.036 mmol) in MeOH (1.5 ml) and THF (0.5 mL) was added CeCl$_3$ (13.53 mg, 0.036 mmol) and NaBH$_4$ (5.50 mg, 0.145 mmol) at 0° C. The reaction mixture was stirred at 0° C. for 1 h. TLC and LCMS indicated a completion of the reaction. The reaction mixture was diluted with saturated NH$_4$Cl solution and EtOAc. The combined organic layer was washed with brine, dried with sodium sulfate, and concentrated under reduced pressure to give Intermediate 108D (20 mg, 0.036 mmol, 100% yield). $^1$H NMR (500 MHz, DMSO-d$_6$) δ 9.21 (br. s., 1H), 8.78 (br. s., 1H), 8.06 (br. s., 1H), 8.02-7.94 (m, 1H), 7.90 (br. s., 2H), 7.45 (d, J=16.8 Hz, 3H), 6.86 (br. s., 1H), 5.86 (br. s., 1H), 5.03 (br. s., 1H), 4.05 (d, J=3.0 Hz, 2H), 3.21 (d, J=3.0 Hz, 2H), 2.73 (br. s., 3H), 2.68 (br. s., 3H). LC-MS: method C, RT=2.33 min, MS (ESI) m/z: 553 (M+H)$^+$.

Example 108

To a solution of Intermediate 108D (15 mg, 0.027 mmol) in DCM (1 ml) was added diethylaminosulfur trifluoride (7.17 μl, 0.054 mmol) dropwise at −78° C. The mixture was stirred from −78° C. to room temperature for 30 min. LCMS indicated a completion of the reaction. The reaction was quenched with water, extracted with EtOAc, the combined organic layer was washed with NaHCO$_3$, brine and concentrated. The crude sample was purified via preparative LC/MS (method D, 50-90% B over 20 min., then a 5-min hold at 100% B). Fractions containing the desired product were combined and dried via centrifugal evaporation to give Example 108 (5.3 mg, 9.46 μmol, 34.9% yield). $^1$H NMR (500 MHz, DMSO-d$_6$) δ 9.21 (br. s., 1H), 8.83 (br. s., 1H), 8.06 (br. s., 2H), 7.90 (br. s., 2H), 7.44 (d, J=13.5 Hz, 3H), 6.86 (br. s., 1H), 6.19-5.98 (m, 1H), 4.05 (br. s., 2H), 3.22 (br. s., 2H), 2.73 (br. s., 3H), 2.69 (br. s., 3H), 1.85-1.75 (m, 3H). LC-MS: method C, RT=2.70 min, MS (ESI) m/z: 555.10 (M+H)$^+$. Analytical HPLC purity (method B): 99%.

Example 109

N-(2-(4-cyano-2-(2-(methoxymethyl)-7-methylquinoxalin-5-yl)benzo[d]thiazol-6-yloxy)ethyl)-4-fluorobenzenesulfonamide

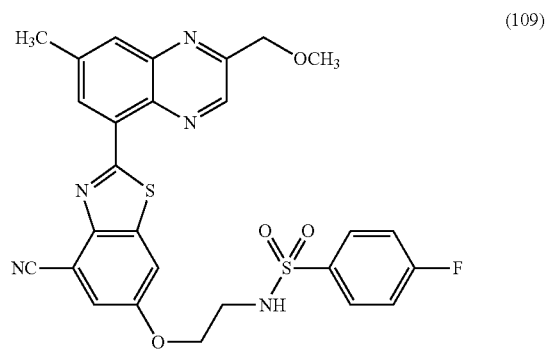 [SMILES: COCc1cnc2c(-c3nc4c(C#N)cc(OCCNS(=O)(=O)c5ccc(F)cc5)cc4s3)cc(C)cc2n1]

(109)

Intermediate 109A: tert-butyl 2-(4-cyano-2-(2-(methoxymethyl)-7-methylquinoxalin-5-yl)benzo[d]thiazol-6-yloxy)ethylcarbamate

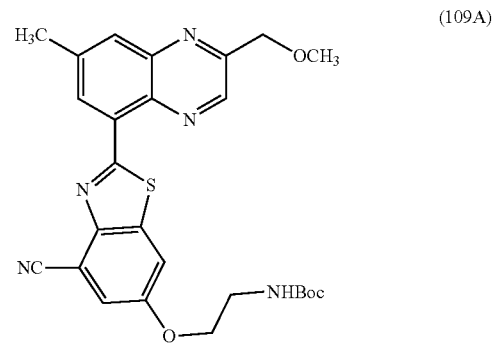 [SMILES: COCc1cnc2c(-c3nc4c(C#N)cc(OCCNC(=O)OC(C)(C)C)cc4s3)cc(C)cc2n1]

(109A)

A mixture of Intermediate 98E (60 mg, 0.116 mmol), zinc cyanide (27.36 mg, 0.232 mmol), palladium (II) trifluoroacetate (6.20 mg, 18.64 μmol), racemic-2-(di-t-butylphosphino)-1,1'-binaphthyl (14.86 mg, 0.019 mmol) and zinc dust (4.57 mg, 0.070 mmol) in DMA (2 mL) was degassed with argon for 5 min. The reaction mixture was heated in a microwave reactor at 130° C. for 1 h. The mixture was diluted with EtOAc/saturated sodium bicarbonate. The organic layer was washed with brine, dried over sodium sulfate. After evaporation of solvent, the crude product was purified with a 40 g ISCO column eluted with 0-100% EtOAc in hexanes for 20 min. The desired fraction was collected and concentrated to give Intermediate 109A (10 mg, 0.020 mmol, 16.98% yield). $^1$H NMR (400 MHz, chloroform-d) δ 9.09 (s, 1H), 9.04 (d, J=2.0 Hz, 1H), 7.95

(s, 1H), 7.66 (dd, J=4.2, 2.4 Hz, 1H), 7.43 (t, J=2.3 Hz, 1H), 4.86 (s, 2H), 4.19-4.14 (m, 2H), 3.62 (d, J=5.5 Hz, 2H), 3.59 (s, 3H), 2.73 (s, 3H), 1.48 (s, 9H). LC-MS: method C, RT=2.54 min, MS (ESI) m/z: 506 (M+H)+.

Intermediate 109B 6-(2-aminoethoxy)-2-(2-(methoxymethyl)-7-methylquinoxalin-5-yl)benzo[d]thiazole-4-carbonitrile

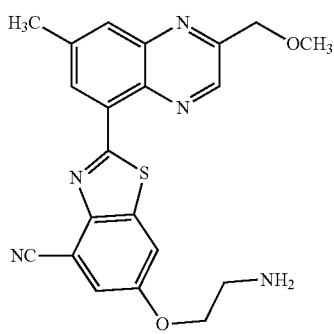

(109B)

To a mixture of Intermediate 109A (10 mg, 0.020 mmol) in DCM (1 mL) was added 2,6-lutidine (6.91 µl, 0.059 mmol) followed by TMS-OTf (14.30 µl, 0.079 mmol) at room temperature. The mixture was stirred at room temperature for 1 h. LCMS indicated a completion of the reaction. The mixture was diluted with EtOAc and saturated NaHCO3, extracted with EtOAc. The combined organic layer was washed with brine, dried with MgSO4 and concentrated to give Intermediate 109B which was used for next step without purification. LC-MS: method C, RT=1.83 min, MS (ESI) m/z: 406 (M+H)+.

Example 109

To a solution of Intermediate 109B in DMF (1 mL) was added DIEA (0.034 mL, 0.197 mmol) and 4-fluorobenzene-1-sulfonyl chloride (4.61 mg, 0.024 mmol). The mixture was stirred at room temperature for 30 min. LCMS indicated a completion of the reaction. The reaction was quenched with 0.2 ml of MeOH. Solvent was removed, the residual was purified via preparative LCMS (method D, 45-85% B over 18 min., then a 5-min hold at 100% B). Fractions containing the desired product were combined and dried via centrifugal evaporation to give Example 109 (0.7 mg, 0.621 µmol, 3.15% yield). $^1$H NMR (500 MHz, DMSO-$d_6$) δ 9.00 (s, 1H), 8.76 (d, J=1.7 Hz, 1H), 8.06 (d, J=2.5 Hz, 1H), 8.03 (d, J=0.5 Hz, 1H), 7.89 (dd, J=8.8, 5.2 Hz, 2H), 7.59 (dd, J=3.2, 2.6 Hz, 1H), 7.41 (t, J=8.8 Hz, 2H), 4.82 (s, 2H), 4.13 (td, J=5.1, 2.5 Hz, 2H), 3.47 (s, 3H), 3.24 (t, J=5.2 Hz, 2H), 2.78 (s, 3H). LC-MS: method C, RT=2.20 min, MS (ESI) m/z: 564.20 (M+H)+. Analytical HPLC purity (method B): 97%.

Example 110

2-(2-(2-methoxy-7-methylquinoxalin-5-yl)-4-methylbenzo[d]thiazol-6-yloxy)ethyl phenylcarbamate

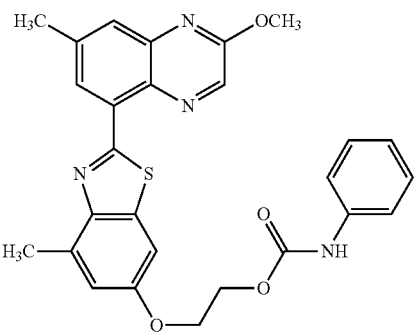

(110)

Intermediate 110A 2-(2-(2-methoxy-7-methylquinoxalin-5-yl)-4-methylbenzo[d]thiazol-6-yloxy)ethyl acetate

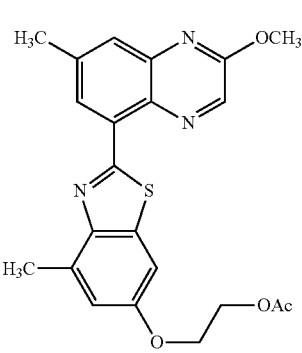

(110A)

To a solution of Intermediate 35B (125 mg, 0.370 mmol) in DMF (4 mL) was added cesium carbonate (362 mg, 1.111 mmol), then 2-bromoethyl acetate (0.049 mL, 0.445 mmol) was added dropwise. The reaction mixture was stirred at room temperature overnight. LCMS indicated a completion of the reaction. The reaction mixture was diluted with EtOAc and water, extracted with EtOAc, the combined organic layer was washed with brine, dried with MgSO4 and concentrated. The crude sample was purified with a 12 g ISCO column, eluted with 0-100% EtOAc in hexane for 15 min. The desired fraction was collected and concentrated to give Intermediate 110A (150 mg, 0.354 mmol, 96% yield) as a yellow solid. $^1$H NMR (400 MHz, chloroform-d) δ 8.65 (d, J=1.5 Hz, 1H), 8.54 (s, 1H), 7.73 (dd, J=1.8, 0.9 Hz, 1H), 7.25 (d, J=2.4 Hz, 1H), 6.95 (dd, 0.9 Hz, 1H), 4.53-4.43 (m, 2H), 4.30-4.21 (m, 2H), 4.12 (s, 3H), 2.19-2.09 (m, 3H). LC-MS: method C, RT=2.58 min, MS (ESI) m/z: 424 (M+H)+.

Intermediate 110B 2-(2-(2-methoxy-7-methylquinoxalin-5-yl)-4-methylbenzo[d]thiazol-6-yloxy)ethanol

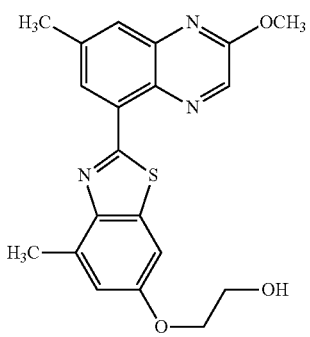
(110B)

To a suspension of Intermediate 110A (190 mg, 0.449 mmol) in THF (3 mL) and MeOH (1 mL) was added 1 N NaOH (1.346 mL, 1.346 mmol) at room temperature. The mixture was stirred at room temperature for 1 h. LCMS indicated a completion of the reaction. The mixture was diluted with EtOAc and 1N HCl, extracted with EtOAc, the combined organic layer was washed with water and brine, dried with MgSO$_4$ and concentrated to Intermediate 110B (155 mg, 0.394 mmol, 88% yield) as a yellow solid. $^1$H NMR (500 MHz, DMSO-d$_6$) δ 8.69 (s, 1H), 8.56 (s, 1H), 7.78 (s, 1H), 7.50 (s, 1H), 6.99 (s, 1H), 4.91 (br. s., 1H), 4.07 (m, 5H), 3.76 (d, J=4.1 Hz, 2H), 2.73 (s, 3H), 2.62 (s, 3H). LC-MS: method C, RT=2.41 min, MS (ESI) m/z: 382 (M+H)$^+$.

Intermediate 110C 2-(2-(2-methoxy-7-methylquinoxalin-5-yl)-4-methylbenzo[d]thiazol-6-yloxy)ethyl carbonochloridate

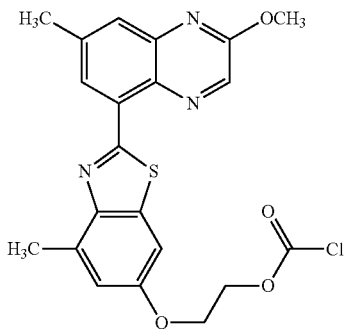
(110C)

To a solution of Intermediate 110B (150 mg, 0.393 mmol) in THF (5 mL) at room temperature was added 15% phosgene in toluene (1.387 mL, 1.966 mmol), and the mixture was stirred at room temperature for 5 h. LCMS indicated the reaction was complete. Solvent was removed and the sample was dried under vacuum overnight to give Intermediate 110C (175 mg, 0.394 mmol, 100% yield) as a yellow solid. It was used for the next step without any purification. LC-MS: method C, RT=2.73 min, MS (ESI) m/z: 444 (M+H)$^+$.

Example 110

To a solution of Intermediate 110C (20 mg, 0.045 mmol) in DCM (1 mL) and THF (0.5 mL) was added aniline (14.69 mg, 0.158 mmol), followed by DIEA (0.079 mL, 0.451 mmol). The mixture was stirred at room temperature for 0.5 h. LCMS indicated a completion of reaction. The reaction mixture was quenched by addition of a small amount of MeOH/water/0.1% TFA (HPLC solvent) and diluted with EtOAc and water, extracted with EtOAc. The combined organic layer was washed with brine, dried over MgSO$_4$ and concentrated. The crude sample was purified via preparative LC/MS (method D, 70-100% B over 10 min., then a 5-min hold at 100% B). Fractions containing the desired product were combined and dried via centrifugal evaporation to give Example 110 (8.6 mg, 0.017 mmol, 37.8% yield). $^1$H NMR (500 MHz, DMSO-d$_6$) δ 9.79 (br. s., 1H), 8.71 (s, 1H), 8.57 (s, 1H), 7.80 (s, 1H), 7.56 (s, 1H), 7.48 (d, J=8.0 Hz, 2H), 7.27 (t, J=7.6 Hz, 2H), 7.03 (s, 1H), 6.99 (t, J=7.4 Hz, 1H), 4.47 (br. s., 2H), 4.33 (br. s., 2H), 4.07 (s, 3H), 2.74 (s, 3H), 2.63 (s, 3H). LC-MS: method C, RT=2.80 min, MS (ESI) m/z: 501.20 (M+H)$^+$. Analytical HPLC purity (method B): 99%.

Example 111

2-(2-(2-methoxy-7-methylquinoxalin-5-yl)-4-methylbenzo[d]thiazol-6-yloxy)ethyl pyridin-3-ylcarbamate

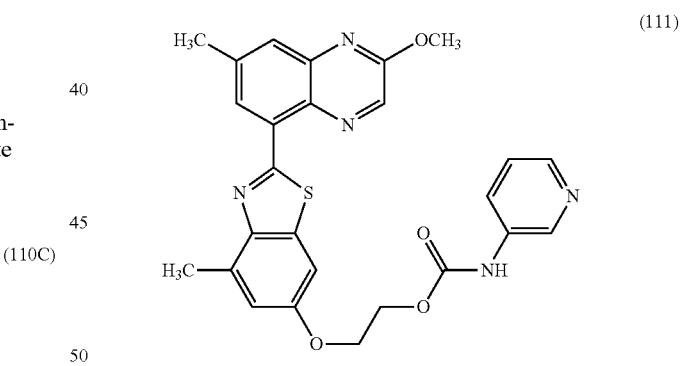
(111)

To a solution of Intermediate 110C (20 mg, 0.045 mmol) in DCM (1 mL) and THF (0.5 mL) was added pyridin-3-amine (14.84 mg, 0.158 mmol) followed by DIEA (0.079 mL, 0.451 mmol). The mixture was stirred at room temperature overnight. The reaction was quenched by addition of a small amount of MeOH/water/0.1% TFA (HPLC solvent). Solvent was removed under vacuum. The crude was purified via preparative LC/MS (method D, 55-100% B over 10 min., then a 5-min hold at 100% B). Fractions containing the desired product were combined and dried via centrifugal evaporation to give Example 111 (4.1 mg, 8.17 μmol, 18.14% yield). $^1$H NMR (500 MHz, DMSO-d$_6$) δ 10.05 (br. s., 1H), 8.65 (br. s., 1H), 8.58 (s, 1H), 8.22 (d, J=3.6 Hz, 1H), 7.91 (d, J=8.0 Hz, 1H), 7.80 (s, 1H), 7.57 (s, 1H), 7.42-7.29 (m, 1H), 7.03 (s, 1H), 4.50 (br. s., 2H), 4.34 (br. s., 2H), 4.08 (s, 3H), 2.78-2.69 (m, 3H), 2.63 (s, 3H). LC-MS: method C, RT=2.09 min, MS (ESI) m/z: 502.10 (M+H)⁺. Analytical HPLC purity (method B): 100%.

Example 112

2-(2-(2-methoxy-7-methylquinoxalin-5-yl)-4-methylbenzo[d]thiazol-6-yloxy)ethyl 6-methoxypyridin-3-ylcarbamate

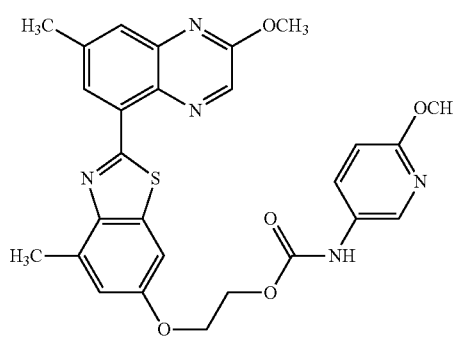

(112)

To a solution of Intermediate 110C (20 mg, 0.045 mmol) in DCM (1 mL) and THF (0.5 mL) was added 6-methoxypyridin-3-amine (19.58 mg, 0.158 mmol) followed by DIEA (0.079 mL, 0.451 mmol). The mixture was stirred at room temperature for 0.5 h. LCMS indicated a completion of reaction. The reaction was quenched by addition of a small amount of MeOH/water/0.1% TFA (HPLC solvent). Solvent was removed under vacuum. The crude sample was purified via preparative LC/MS (method D, 70-100% B over 10 min., then a 5-min hold at 100% B). Fractions containing the desired product were combined and dried via centrifugal evaporation to give Example 112 (8.6 mg, 0.016 mmol, 35.2% yield). $^1$H NMR (500 MHz, DMSO-$d_6$) δ 9.77 (br. s., 1H), 8.73 (s, 1H), 8.59 (s, 1H), 8.24 (br. s., 1H), 7.81 (s, 1H), 7.78 (d, J=7.7 Hz, 1H), 7.57 (s, 1H), 7.03 (s, 1H), 6.78 (d, J=8.8 Hz, 1H), 4.47 (br. s., 2H), 4.33 (br. s., 2H), 4.08 (s, 3H), 3.80 (s, 3H), 2.75 (s, 3H), 2.64 (s, 3H). LC-MS: method C, RT=2.52 min, MS (ESI) m/z: 532.25 (M+H)⁺. Analytical HPLC purity (method B): 98%.

Example 113

2-(2-(2-methoxy-7-methylquinoxalin-5-yl)-4-methylbenzo[d]thiazol-6-yloxy)ethyl pyridin-4-ylcarbamate

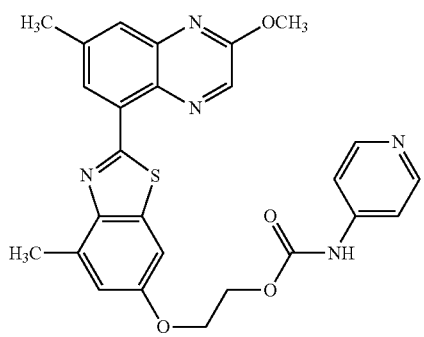

(113)

To a solution of Intermediate 110C (20 mg, 0.045 mmol) in DCM (1 mL) and THF (0.5 mL) was added pyridin-4-amine (14.84 mg, 0.158 mmol) followed by DIEA (0.079 mL, 0.451 mmol). The mixture was stirred at room temperature overnight. The reaction was quenched by addition of a small amount of MeOH/water/0.1% TFA (HPLC solvent). The reaction mixture was diluted with EtOAc and water, extracted with EtOAc. The combined organic layer was washed with brine, dried with MgSO₄ and concentrated. The crude sample was purified via preparative LC/MS (method D, 55-95% B over 15 min., then a 6-min hold at 100% B). Fractions containing the desired product were combined and dried via centrifugal evaporation to give Example 113 (2.6 mg, 4.98 μmol, 11.05% yield). $^1$H NMR (500 MHz, DMSO-$d_6$) δ 10.29 (s, 1H), 8.73 (s, 1H), 8.59 (s, 1H), 8.38 (d, J=4.7 Hz, 2H), 7.82 (s, 1H), 7.57 (s, 1H), 7.45 (d, J=5.0 Hz, 2H), 7.04 (s, 1H), 4.51 (br. s., 2H), 4.35 (br. s., 2H), 4.08 (s, 3H), 2.75 (s, 3H), 2.64 (s, 3H). LC-MS: method C, RT=2.11 min, MS (ESI) m/z: 502.15 (M+H)⁺. Analytical HPLC purity (method B): 96%.

Example 114

N-(2-(2-(2-((difluoromethoxy)methyl)-7-methylquinoxalin-5-yl)-4-methylbenzo[d]thiazol-6-yloxy)ethyl)-4-fluorobenzenesulfonamide

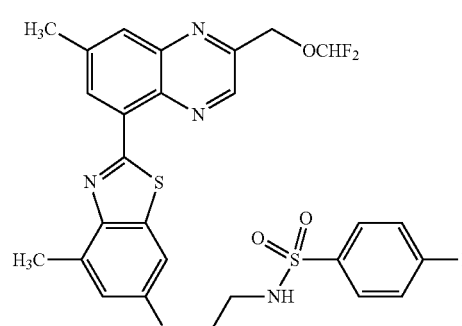

(114)

Intermediate 114A: methyl 7-methyl-5-(4,4,5,5-tetramethyl-1,3,2-dioxaborolan-2-yl)quinoxaline-2-carboxylate

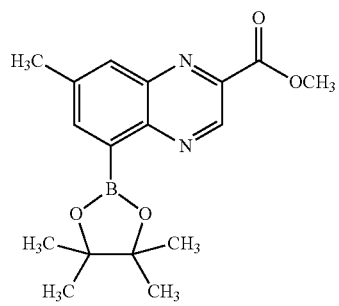

(114A)

A mixture of methyl 5-bromo-7-methylquinoxaline-2-carboxylate (225 mg, 0.800 mmol), 4,4,4',4',5,5,5',5'-octamethyl-2,2'-bi(1,3,2-dioxaborolane) (447 mg, 1.761 mmol), potassium acetate (196 mg, 2.001 mmol) and [1,1'-bis(diphenylphosphino)ferrocene] dichloropalladium (II) complex with dichloromethane (1:1) (26.1 mg, 0.032 mmol) in dioxane (3.0 mL) was degassed with argon for 10 min. The reaction mixture was heated in a microwave reactor at 120° C. for 30 min. LCMS indicated a complete conversion of starting material. The mixture was diluted with EtOAc/water, insoluble material was removed by filtration. The filtrate was extracted with EtOAc, washed with brine, dried over sodium sulfate. The crude product was purified with flash chromatography (loading in chloroform, 5% to 75% EtOAc in hexanes over 12 min using a 12 g silica gel cartridge). The desired fractions were combined and concentrated to yield Intermediate 114A (225 mg, 0.686 mmol, 86% yield) as brown solid. LC-MS: method C, RT=1.48 min, MS (ESI) m/z: 247 (M+H)+ (boronic acid).

Intermediate 114B: ethyl 5-(6-(2-(4-fluorophenylsulfonamido)ethoxy)-4-methylbenzo[d] thiazol-2-yl)-7-methylquinoxaline-2-carboxylate

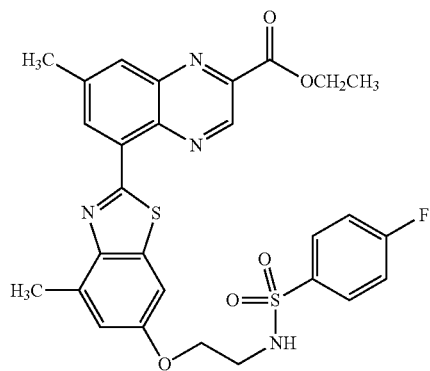

(114B)

To Intermediate 114A (89 mg, 0.271 mmol), Intermediate I-5 (115 mg, 0.258 mmol) and [1,1'-bis(diphenylphosphino)ferrocene]dichloropalladium (II) complex with dichloromethane (1:1) (10.54 mg, 0.013 mmol) was added toluene (3 mL), EtOH (1 mL) and sodium carbonate (0.258 mL, 2M, 0.516 mmol). The mixture was degassed with argon for 5 min. The reaction mixture was heated in a microwave reactor at 130° C. for 30 min. The mixture was diluted with EtOAc and water, extracted with EtOAc. The combined organic layer was washed with brine, dried with MgSO4 and concentrated. The crude sample was purified with a 12 g ISCO column eluted with EtOAc in hexanes for 15 min. The desired fraction was collected and concentrated to give Intermediate 114B (45 mg, 0.039 mmol, 15.01% yield) as a yellow solid [Note: Transesterification with the EtOH solvent occurred under these reaction conditions]. 1H NMR (400 MHz, chloroform-d) δ 9.62 (s, 1H), 9.02 (d, J=1.8 Hz, 1H), 8.84 (s, 1H), 8.17 (dd, J=1.8, 0.9 Hz, 1H), 8.00-7.76 (m, 2H), 7.23-7.07 (m, 2H), 6.84 (dd, J=2.4, 0.9 Hz 1H), 4.63 (q, J=7.3 Hz, 2H), 4.12-4.03 (m, 2H), 3.48-3.39 (m, 2H), 1.93 (s, 3H), 1.59 (s, 3H), 1.54 (t, J=7.2 Hz, 3H). LC-MS: method C, RT=2.44 min, MS (ESI) m/z: 581 (M+H)+.

Intermediate 114C 4-fluoro N-(2-(2-(2-(hydroxymethyl)-7-methylquinoxalin-5-yl)-4-methylbenzo[d]thiazol-6-yloxy)ethyl)benzenesulfonamide

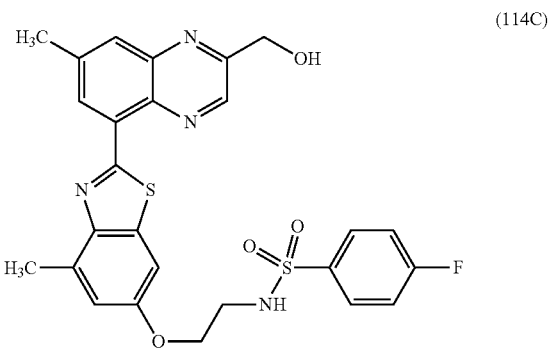 [SMILES: Cc1cc(-c2nc3c(C)cc(OCCNS(=O)(=O)c4ccc(F)cc4)cc3s2)c2ncc(CO)nc2c1]

(114C)

NaBH4 (2.93 mg, 0.077 mmol) and calcium chloride (4.30 mg, 0.039 mmol) was dissolved in THF (2 ml) and the mixture was stirred at room temperature for 1.5 h, followed by addition of a solution of Intermediate 114B (45 mg, 0.039 mmol) in THF (1 mL). The mixture was stirred at room temperature for 1.5 h. LCMS indicated a completion of the reaction. The mixture was diluted with water and EtOAc. The organic layer was washed with brine, dried with sodium sulfate, and concentrated. The crude sample was purified with a 40 g ISCO column eluted with 0-70% EtOAc in hexanes for 20 min. The desired fraction was collected and concentrated to give Intermediate 114C (20 mg, 0.037 mmol, 96% yield) as a yellow solid. LC-MS: method C, RT=2.23 min, MS (ESI) m/z: 539 (M+H)+.

Example 114

To a heated suspension of Intermediate 114C (20 mg, 0.037 mmol) and sodium sulfate (1.319 mg, 9.28 μmol) in acetonitrile (2.0 mL) at 65° C. was added 2,2-difluoro-2-(fluorosulfonyl)acetic acid (5.76 μl, 0.056 mmol) in acetonitrile (0.5 mL) dropwise over 40 min, The mixture was stirred at 65° C. for 0.5 h. After the mixture was cooled to room temperature, it was diluted with EtOAc and quenched with NaHCO3, extracted with EtOAc. The combined organic layer was washed with NaHCO3 and brine, dried over MgSO4 and concentrated. The crude sample was purified via preparative LC/MS (method D, 40-80% B over 10 min., then a 5-min hold at 100% B). Fractions containing the desired product were combined and dried via centrifugal evaporation to give Example 114 (0.4 mg, 0.584 μmol, 1.259% yield). LC-MS: method C, RT=2.48 min, MS (ESI) m/z: 589.20 (M+H)+. Analytical HPLC purity (method B): 86%.

Example 115

2-(2-(2-methoxy-7-methylquinoxalin-5-yl)benzo[d]thiazol-6-yloxy)ethyl 6-methoxypyridin-3-ylcarbamate

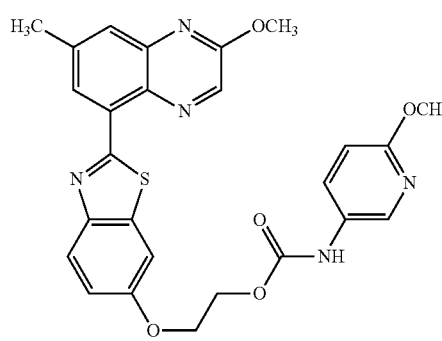
(115)

Intermediate 115A: 2-(2-chlorobenzo[d]thiazol-6-yloxy)ethanol

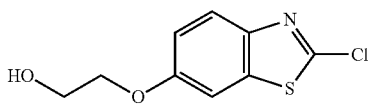
(115A)

To a solution of Intermediate I-4A (500 mg, 2.69 mmol) in DMF (10 mL) was added cesium carbonate (1755 mg, 5.39 mmol), then 2-bromoethyl acetate (0.356 mL, 3.23 mmol) was added dropwise. The reaction mixture was stirred at room temperature overnight, diluted with EtOAc and water, extracted with EtOAc. The combined organic layer was washed with brine, dried with MgSO$_4$ and concentrated. The crude sample was dissolved in 10 ml of THF followed by addition of NaOH (5.39 mL, 1M, 5.39 mmol). The mixture was stirred at room temperature for 1 h. LCMS indicated a completion of the reaction. The reaction mixture was diluted with EtOAc and water, extracted with EtOAc. The combined organic layer was washed with brine, dried with MgSO$_4$ and concentrated. The crude sample was purified with a 40 g ISCO column eluted with 0-100% EtOAc in hexanes for 20 min. The desired fraction was collected and concentrated to give Intermediate 115A (550 mg, 2.395 mmol, 89% yield) as off-white solid. $^1$H NMR (400 MHz, chloroform-d) δ 7.73 (d, J=8.8 Hz, 1H), 7.14 (d, J=2.4 Hz, 1H), 6.99 (dd, J=8.9, 2.5 Hz, 1H), 4.10-4.04 (m, 2H), 4.01-3.91 (m, 2H). LC-MS: method C, RT=1.64 min, MS (ESI) m/z: 230 (M+H)$^+$.

Intermediate 115B 2-(2-(2-(difluoromethoxy)-7-methylquinoxalin-5-yl)benzo[d]thiazol-6-yloxy)ethanol

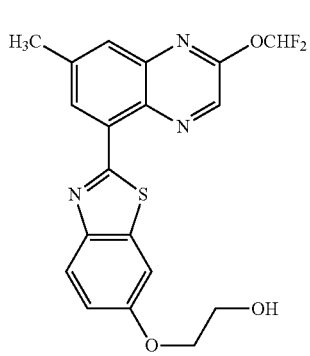
(115B)

To Intermediate I-1 (512 mg, 1.524 mmol), Intermediate 115A (350 mg, 1.524 mmol) and [1,1'-bis(diphenylphosphino)ferrocene]dichloropalladium (II) complex with dichloromethane (1:1) (49.8 mg, 0.061 mmol) was added toluene (3 mL) and EtOH (1). The mixture was sonicated for 1 min, and flushed with argon. To this was added sodium carbonate (1.524 mL, 2M, 3.05 mmol). The reaction mixture was heated in a microwave reactor at 130° C. for 30 min. The reaction mixture was diluted with EtOAc and water, extracted with EtOAc (3×). The combined organic layer was washed with brine, dried with MgSO$_4$ and concentrated. The residual was dissolved in 1 ml DMSO and DCM and was loaded to a 40 g ISCO column eluted with 0-100% EtOAc in hexanes for 20 min. The desired fractions were combined and concentrated to yield Intermediate 115B (550 mg, 1.363 mmol, 89% yield) as a brown-yellow solid. $^1$H NMR (400 MHz, chloroform-d) δ 8.75 (d, J=1.8 Hz, 1H), 8.67 (s, 1H), 8.03 (d, J=8.8 Hz, 1H), 7.77 (s, 1H), 7.86-7.46 (m, 1H), 7.43 (d, J=2.4 Hz, 1H), 7.15 (dd, J=9.0, 2.4 Hz, 1H), 4.23-4.16 (m, 2H), 4.04 (d, J=4.6 Hz, 2H), 2.67 (s, 3H). $^{19}$F NMR (376 MHz, chloroform-d) δ −89.73 (s, 2F). LC-MS: method C, RT=2.31 min, MS (ESI) m/z: 404 (M+H)$^+$.

Intermediate 115C 2-(2-(2-methoxy-7-methylquinoxalin-5-yl)benzo[d]thiazol-6-yloxy)ethanol

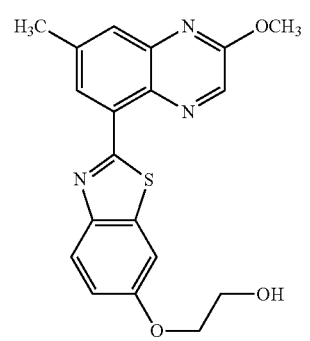
(115C)

To a solution of Intermediate 115B (550 mg, 1.363 mmol) in THF (10 mL) was added NaOMe in MeOH (4.3 M, 0.936 mL, 4.09 mmol). The mixture was stirred at room temperature for 1 h. LCMS indicated a completion of the reaction. The reaction was quenched by 1N HCl (12 ml) and extracted with DCM (3×). The combined organic layer was washed with brine, dried with MgSO₄ and concentrated to give Intermediate 115C (400 mg, 1.089 mmol, 80% yield) as a yellow solid. $^1$H NMR (400 MHz, chloroform-d) δ 8.63 (d, J=1.5 Hz, 1H), 8.57 (s, 1H), 8.04 (d, J=9.0 Hz, 1H), 7.76 (dd, J=2.0, 0.9 Hz, 1H), 7.45 (d, J=2.4 Hz, 1H), 7.16 (dd, 2.5 Hz, 1H), 4.27-4.18 (m, 2H), 4.14 (s, 3H), 4.08-4.01 (m, 2H), 2.66 (s, 3H). LC-MS: method C, RT=2.31 min, MS (ESI) m/z: 368 (M+H)⁺.

Intermediate 115D 2-(2-(2-methoxy-7-methylquinoxalin-5-yl)benzo[d]thiazol-6-yloxy)ethyl carbonochloridate

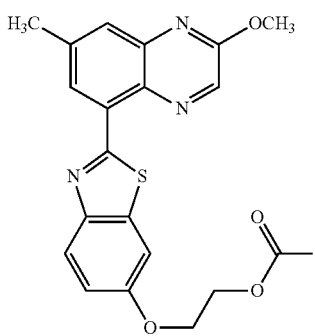
(115D)

To a suspension of Intermediate 115C (150 mg, 0.408 mmol) in THF (3 mL) at room temperature was added 15% phosgene in toluene (1.440 mL, 2.041 mmol). The mixture was stirred at room temperature overnight. Solvent was removed under vacuum and Intermediate 115D (175 mg, 0.407 mmol, 100% yield) was obtained as a yellow solid. It was used for the next step without any purification. LC-MS: method C, RT=2.56 min, MS (ESI) m/z: 430 (M+H)⁺.

Example 115

To a solution of 6-methoxypyridin-3-amine (15.16 mg, 0.122 mmol) in DCM (0.5 mL) was added Intermediate 115D (15 mg, 0.035 mmol) in THF (0.5 mL), followed by DIEA (0.061 mL, 0.349 mmol). The mixture was stirred at room temperature for 1 h. The reaction was quenched by addition of a small amount of MeOH/water/0.1% TFA (HPLC solvent) and concentrated. The residual was purified via preparative LC/MS (method D, 50-100% B over 12 min., then a 7-min hold at 100% B). Fractions containing the desired product were combined and dried via centrifugal evaporation to give Example 115 (5.0 mg, 9.56 μmol, 27.4% yield). $^1$H NMR (500 MHz, DMSO-d₆) δ 9.82 (br. s., 1H), 8.73 (s, 1H), 8.57 (d, J=1.4 Hz, 1H), 8.24 (br. s., 1H), 8.01 (d, J=9.1 Hz, 1H), 7.86-7.72 (m, 3H), 7.19 (dd, 2.5 Hz, 1H), 6.79 (d, J=8.8 Hz, 1H), 4.54-4.42 (m, 2H), 4.38-4.29 (m, 2H), 4.07 (s, 3H), 3.79 (s, 3H), 2.62 (s, 3H). LC-MS: method C, RT=2.23 min, MS (ESI) m/z: 518.20 (M+H)⁺. Analytical HPLC purity (method B): 99%.

Example 116

2-(2-(2-methoxy-7-methylquinoxalin-5-yl)-4-methylbenzo[d]thiazol-6-yloxy)ethyl 5-cyanopyridin-3-ylcarbamate

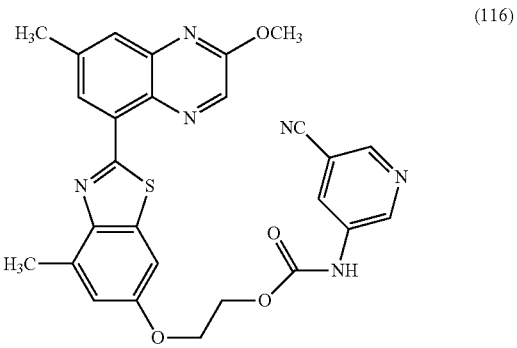 [SMILES: COc1cnc2c(-c3nc4c(C)cc(OCCOC(=O)Nc5cncc(C#N)c5)cc4s3)cc(C)cc2n1]
(116)

To a solution of Intermediate 110B in THF (0.5 mL) was added a suspension of (5-cyanopyridin-3-yl)carbamic chloride (21.42 mg, 0.118 mmol) (23.80 mg, 0.131 mmol) in DCM and toluene, followed by DIEA (0.046 ml, 0.262 mmol). The mixture was stirred at room temperature for 30 min. LCMS indicated a completion of the reaction. The mixture was quenched by 10% water/acetonitrile with 01% TFA. Solvent was removed and the crude was purified via preparative LC/MS (method D, 50-85% B over 20 min., then a 5-min hold at 100% B). Fractions containing the desired product were combined and dried via centrifugal evaporation to give Example 116 (9.0 mg, 0.016 mmol, 61.9% yield). $^1$H NMR (500 MHz, DMSO-d₆) δ 10.51 (br. s., 1H), 8.85 (d, J=2.5 Hz, 1H), 8.72 (s, 1H), 8.65 (d, J=1.7 Hz, 1H), 8.58 (d, J=1.7 Hz, 1H), 8.29 (s, 1H), 7.80 (s, 1H), 7.57 (d, J=2.2 Hz, 1H), 7.03 (d, J=1.7 Hz, 1H), 4.57-4.49 (m, 2H), 4.38-4.31 (m, 2H), 4.07 (s, 3H), 2.74 (s, 3H), 2.63 (s, 3H). LC-MS: method C, RT=2.52 min, MS (ESI) m/z: 527.15 (M+H)⁺. Analytical HPLC purity (method B): 95%.

Example 117

2-((2-(2-methoxy-7-methylquinoxalin-5-yl)-4-methylbenzo[d]thiazol-6-yl)oxy)ethyl (6-cyanopyridin-3-yl)carbamate

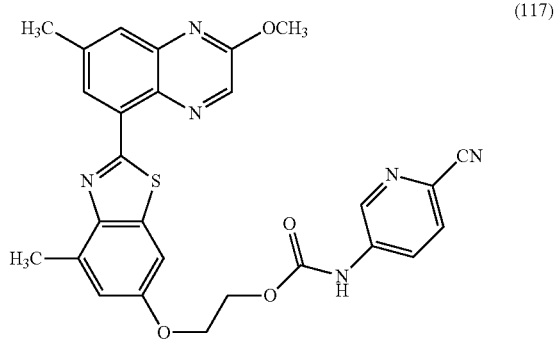 [SMILES: COc1cnc2c(-c3nc4c(C)cc(OCCOC(=O)Nc5ccc(C#N)nc5)cc4s3)cc(C)cc2n1]
(117)

To Intermediate 110B (15 mg, 0.039 mmol) in THF (0.5 mL) was added (6-cyanopyridin-3-yl)carbamic chloride (21.42 mg, 0.118 mmol) (21.42 mg, 0.118 mmol) in DCM (1 ml) followed by DIEA (0.069 ml, 0.393 mmol). The mixture was stirred at room temperature for 30 min. LCMS indicated a completion of the reaction. The mixture was quenched by 10% water/acetonitrile with 01% TFA. Solvent was removed, the residual was purified via preparative LC/MS (method D, 55-95% B over 10 min., then a 5-min hold at 100% B). Fractions containing the desired product were combined and dried via centrifugal evaporation to give Example 117 (13.1 mg, 0.025 mmol, 63.3% yield). LC-MS: method C, RT=2.55 min, MS (ESI) m/z: 527.20 (M+H)$^+$. Analytical HPLC purity (method B): 98%.

Example 118

2-((2-(2-methoxy-7-methylquinoxalin-5-yl)benzo[d]thiazol-6-yl)oxy)ethyl (3-cyanophenyl)carbamate

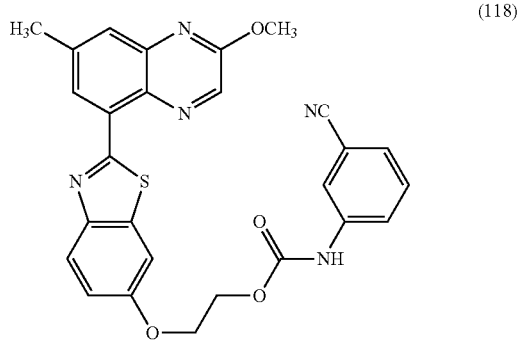 [SMILES: COc1cnc2c(-c3nc4ccc(OCCOC(=O)Nc5cccc(C#N)c5)cc4s3)cc(C)cc2n1]

(118)

To a solution of 3-aminobenzonitrile (14.43 mg, 0.122 mmol) in DCM (0.5 mL) was added Intermediate 115D (15 mg, 0.035 mmol) in THF (1 mL) followed by DIEA (0.061 mL, 0.349 mmol). The mixture was stirred at room temperature overnight. The reaction was quenched by addition of a small amount of MeOH/water/0.1% TFA (HPLC solvent) and concentrated. The residual was dissolved in DMSO and purified via preparative LC/MS (method D, 60-100% B over 20 min., then a 5-min hold at 100% B). Fractions containing the desired product were combined and dried via centrifugal evaporation to give Example 118 (2.1 mg, 3.94 mol, 11.29% yield). $^1$H NMR (500 MHz, DMSO-d$_6$) δ 10.26 (br. s., 1H), 8.74 (s, 1H), 8.58 (d, J=1.4 Hz, 1H), 8.02 (d, J=9.1 Hz, 1H), 7.90 (s, 1H), 7.82 (s, 1H), 7.78 (d, J=2.2 Hz, 1H), 7.75 (d, J=8.3 Hz, 1H), 7.54-7.48 (m, 1H), 7.48-7.44 (m, 1H), 7.20 (dd, J=8.8, 2.5 Hz, 1H), 4.52 (d, J=4.4 Hz, 2H), 4.37 (d, J=3.9 Hz, 2H), 4.08 (s, 3H), 2.63 (s, 3H). LC-MS: method C, RT=2.43 min, MS (ESI) m/z: 512.20 (M+H)$^+$. Analytical HPLC purity (method B): 96%.

Example 119

2-((2-(2-methoxy-7-methylquinoxalin-5-yl)-4-methylbenzo[d]thiazol-6-yl)oxy)ethyl (2-chloropyrimidin-5-yl)carbamate

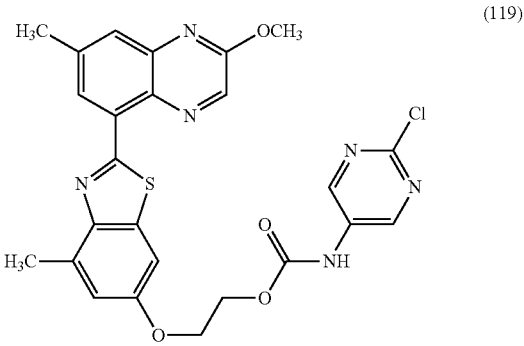 [SMILES: COc1cnc2c(-c3nc4c(C)cc(OCCOC(=O)Nc5cnc(Cl)nc5)cc4s3)cc(C)cc2n1]

(119)

To a solution of Intermediate 110B (15.5 mg, 0.041 mmol) in THF (1 mL) was added (2-chloropyrimidin-5-yl)carbamic chloride (39.0 mg, 0.203 mmol) in DCM (1 ml) followed by DIEA (0.071 ml, 0.406 mmol). The mixture was stirred at room temperature overnight, quenched by a drop of 10% water/acetonitrile with 0.1% TFA. Solvent was removed, the residual was dissolved in DMSO and purified via preparative LC/MS (method C, 55-100% B over 15 min., then a 5-min hold at 100% B). Fractions containing the desired product were combined and dried via centrifugal evaporation to give Example 119 (3.7 mg, 6.61 µmol, 16.28% yield). $^1$H NMR (500 MHz, DMSO-d$_6$) δ 8.82 (s, 2H), 8.73 (s, 1H), 8.59 (s, 1H), 7.82 (s, 1H), 7.57 (s, 1H), 7.03 (s, 1H), 4.53 (br. s., 2H), 4.35 (br. s., 2H), 4.07 (s, 3H), 2.74 (s, 3H), 2.64 (s, 3H). LC-MS: method C, RT=2.54 min, MS (ESI) m/z: 537.15 (M+H)$^+$. Analytical HPLC purity (method B): 96%.

Example 120

5-(6-fluoro-5-methoxybenzofuran-2-yl)-2-methoxy-7-methylquinoxaline

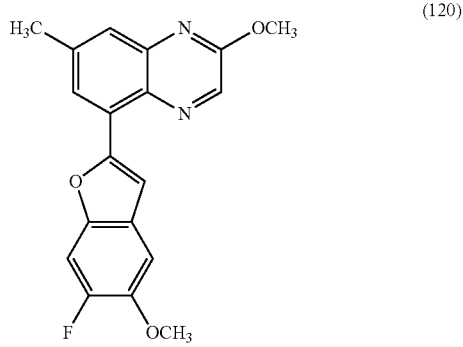 [SMILES: COc1cnc2c(-c3cc4cc(OC)c(F)cc4o3)cc(C)cc2n1]

(120)

Intermediate 120A: 4-fluoro-2-hydroxy-5-methoxybenzaldehyde

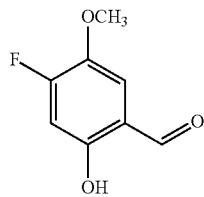
(120A)

To a solution of 3-fluoro-4-methoxyphenol (200 mg, 1.407 mmol) in THF (8 ml) was added magnesium chloride (260 mg, 2.81 mmol), triethylamine (0.981 mL, 7.04 mmol) and paraformaldehyde (211 mg, 7.04 mmol). The reaction mixture was heated to reflux at 80° C. under argon for 3.0 h. TLC and LCMS indicated a complete conversion of starting material. The reaction mixture was cooled to room temperature, diluted with EtOAc, quenched with 1.0 N HCl (8.0 mL)/water and stirred at room temperature for 15 min until the cloudy solution turned to a clear solution. The mixture was passed through a pad of wet celite. The organic layer was collected, washed with brine, dried over sodium sulfate and concentrated. The crude product was purified with flash chromatography (loading in chloroform, 0% to 30% EtOAc in hexanes over 15 min using a 12 g silica gel cartridge). The desired fractions were combined and concentrated to yield Intermediate 120A (235 mg, 1.381 mmol, 98% yield) as a white solid. $^{19}$F NMR (376 MHz, Chloroform-d) δ −117.87 (s, 1F). $^1$H NMR (400 MHz, chloroform-d) δ 11.09 (d, J=1.8 Hz, 1H), 9.81 (s, 1H), 7.09 (d, J=9.0 Hz, 1H), 6.75 (d, J=11.9 Hz, 1H), 3.91 (s, 3H). LC-MS: method C, RT=1.45 min, MS (ESI) m/z: No (M+H)$^+$.

Intermediate 120B: ethyl 6-fluoro-5-methoxybenzofuran-2-carboxylate

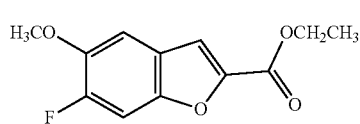
(120B)

To a mixture of Intermediate 120A (1.7 g, 9.99 mmol) and Cs$_2$CO$_3$ (3.91 g, 11.99 mmol) in acetonitrile (50 mL) was added ethyl bromoacetate (1.266 mL, 10.99 mmol). The mixture was stirred at room temperature over weekend. The mixture was filtered and the filter cake was rinse with EtOAc. The combined filtrate was concentrated to a white solid of ethyl 2-(5-fluoro-2-formyl-4-methoxyphenoxy)acetate. The crude sample was added to a solution of 2,8,9-trimethyl-2,5,8,9-tetraaza-1-phosphabicyclo[3.3.3]undecane (0.864 g, 4.00 mmol) in EtOH (10 mL). The mixture was heated at 70° C. for 2 h. TLC and LCMS indicated a completion of the reaction. The mixture was concentrated and the residual was purified with a 120 g ISCO column eluted with 0-100% EtOAc in hexanes for 40 min. The desired fraction was collected and concentrated to give Intermediate 120B (1.6 g, 6.72 mmol, 67.2% yield) as a white solid. $^1$H NMR (400 MHz, chloroform-d) δ 7.47 (d, J=0.9 Hz, 1H), 7.35 (dd, J=10.5, 0.8 Hz, 1H), 7.16 (d, J=8.1 Hz, 1H), 4.44 (q, J=7.0 Hz, 2H), 3.95 (s, 3H), 1.43 (t, J=7.2 Hz, 3H). $^{19}$F NMR (376 MHz, chloroform-d) δ −130.18 (s, 1F). LC-MS: method C, RT=1.93 min, MS (ESI) m/z: 239.1 (M+H)$^+$.

Intermediate 120C: 6-fluoro-5-methoxybenzofuran

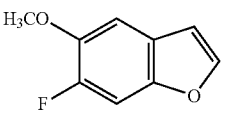
(120C)

To a solution of Intermediate 120B (1.6 g, 6.72 mmol) in THF (25 mL) and MeOH (5 mL) was added NaOH (0.806 g, 20.15 mmol) in water (10 mL). The mixture was stirred at room temperature for 1 h. LCMS indicated the reaction was complete. The mixture was diluted with EtOAc and 1N HCl (pH <2), extracted with EtOAc. The combined organic layer was washed with brine, dried over MgSO$_4$ and concentrated to 6-fluoro-5-methoxybenzofuran-2-carboxylic acid as a white solid. LC-MS: method C, RT=1.59 min, MS (ESI) m/z: 211 (M+H)$^+$. The crude acid was redissolved in DMSO (25 mL), then silver carbonate (0.740 g, 1.35 mmol) and AcOH (0.038 mL, 0.672 mmol) was added. The mixture was heated at 120° C. overnight. LCMS indicated a completion of the reaction. The mixture was filtered and the filter cake was washed with EtOAc. The filtrate was concentrated and purified with a 120 g ISCO column eluted with 0-50% EtOAc in hexanes for 40 min. The desired fraction was collected and concentrated to give Intermediate 120C (0.97 g, 5.84 mmol, 87% yield) as a yellow solid. $^1$H NMR (400 MHz, methanol-d$_4$) δ 7.71 (d, J=2.2 Hz, 1H), 7.30 (dd, J=10.9, 0.8 Hz, 1H), 7.27 (d, J=8.4 Hz, 1H), 6.79 (dd, J=2.2, 1.1 Hz, 1H). $^{19}$F NMR (376 MHz, methanol-d$_4$) δ −138.84 (s, 1F). LC-MS: method C, RT=1.74 min, MS (ESI) m/z: No (M+H)$^+$.

Intermediate 120D: 6-fluorobenzofuran-5-ol

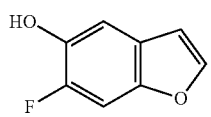
(120D)

To a mixture of Intermediate 120C (0.73 g, 4.39 mmol) and tetrabutylammonium iodide (1.704 g, 4.61 mmol) in DCM (4 ml) at −78° C. was added boron trichloride in heptane (10.33 ml, 1.0 M, 10.33 mmol) dropwise. The mixture was stirred at −78° C. for 45 min. The cooling bath was removed and the mixture was stirred at room temperature for 3.0 h. HPLC and TLC indicated a clean reaction. The mixture was poured into 1.5M K$_2$HPO$_4$ with ice, stirred for 20 min, extracted with EtOAc. The organic layers were collected, washed with 10% Na$_2$S$_2$O$_3$, water, brine, dried over sodium sulfate. After evaporation of solvent, the crude product was dissolved in a small amount of chloroform and charged to a 40 g ISCO column eluted with hexanes for 1 min., then a 15 min gradient from 0% to 50% EtOAc in hexanes. The desired fractions were combined and concentrated to give Intermediate 120D (650 mg, 4.27 mmol, 97% yield) as off-white solid. ¹⁹F NMR (376 MHz, chloroform-d) δ −142.05 (s, 1F). ¹H NMR (400 MHz, chloroform-d) δ 7.59 (d, J=2.2 Hz, 1H), 7.29-7.26 (d, Hz 1H), 7.17 (d, J=8.6 Hz, 1H), 6.73-6.64 (m, 1H), 5.00 (d, J=4.8 Hz, 1H). LC-MS: method C, RT=1.37 min, MS (ESI) m/z: No (M+H)⁺.

Intermediate 120E: tert-butyl(6-fluorobenzofuran-5-yloxy)dimethylsilane

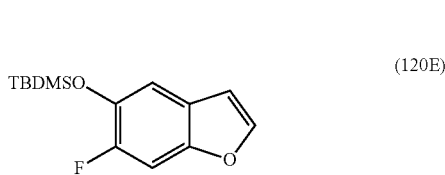 [SMILES: CC(C)(C)[Si](C)(C)Oc1cc2ccoc2cc1F]

(120E)

To a stirred solution of Intermediate 120D (0.65 g, 4.27 mmol) in DMF (15 mL) was added TBDMS-Cl (0.966 g, 6.41 mmol) and imidazole (0.524 g, 7.69 mmol). The reaction mixture was stirred at room temperature for 1.0 h. TLC and LCMS indicated a clean reaction. The mixture was partitioned between EtOAc/water. The organic layer was washed with water, brine, dried over sodium sulfate. After evaporation of solvent, the crude product was dissolved in a small amount of chloroform and charged to a 40 g silica gel cartridge which was eluted with hexanes for 3 min., then 15 min gradient from 0% to 15% EtOAc in hexanes. The desired fractions were combined and concentrated to give Intermediate 120E (1 g, 3.75 mmol, 88% yield) as clear oil. ¹H NMR (400 MHz, chloroform-d) δ 7.58 (d, J=2.2 Hz, 1H), 7.24 (dd, J=10.0, 0.8 Hz, 1H), 7.08 (d, J=8.4 Hz, 1H), 6.66 (dd, J=2.1, 1.0 Hz, 1H), 1.08-1.00 (m, 9H), 0.26-0.16 (m, 6H). ¹⁹F NMR (376 MHz, chloroform-d) δ −133.00 (s, 1F). LC-MS: method C, RT=2.53 min, MS (ESI) m/z: 267 (M+H)⁺.

Intermediate 120F: tert-butyl(6-fluoro-7-(trimethylsilyl)benzofuran-5-yloxy) dimethylsilane

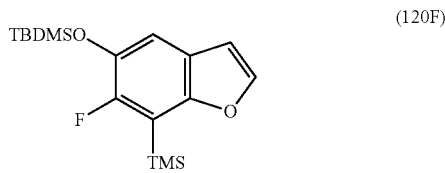 [SMILES: CC(C)(C)[Si](C)(C)Oc1cc2ccoc2c([Si](C)(C)C)c1F]

(120F)

To diisopropylamine (0.594 mL, 4.17 mmol) in THF (10 mL) at −78° C. was added 1.6 N n-BuLi in hexanes (2.083 mL, 3.33 mmol). The mixture was stirred at −78° C. for 0.5 h. Then Intermediate 120E (740 mg, 2.78 mmol) in THF (2 mL) was added, the mixture was stirred at −78° C. for 0.5 h. TMS-Cl in DCM (3.61 mL, 3.61 mmol) was added, and the reaction mixture was warmed up to room temperature over 0.5 h. The reaction mixture was diluted with EtOAc, quenched with saturated ammonium chloride. The organic layer was washed with Na₂CO₃, brine, dried over sodium sulfate. After evaporation of solvent, the crude was purified with a 40 g ISCO column eluted with 0-20% EtOAc in hexanes for 20 min. The desired fraction was collected and concentrated to give Intermediate 120F (840 mg, 2.481 mmol, 89% yield) as colorless oil. ¹⁹F NMR (376 MHz, chloroform-d) δ −121.09 (s, 1F). ¹H NMR (400 MHz, chloroform-d) δ 7.57 (d, J=2.2 Hz, 1H), 7.08 (d, J=8.8 Hz, 1H), 6.64 (d, J=2.2 Hz, 1H), 1.03 (s, 9H), 0.46 (d, J=1.1 Hz, 9H), 0.20 (d, J=1.1 Hz, 6H). LC-MS: method C, RT=2.24 min, MS (ESI) m/z: 339 (M+H)⁺.

Intermediate 120G tert-butyl(6-fluoro-2-iodo-7-(trimethylsilyl)benzofuran-5-yloxy)dimethylsilane

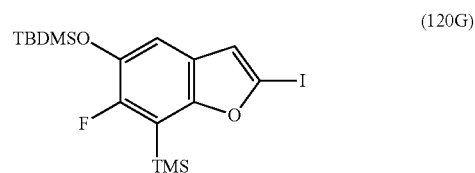 [SMILES: CC(C)(C)[Si](C)(C)Oc1cc2cc(I)oc2c([Si](C)(C)C)c1F]

(120G)

To a solution of Intermediate 120F (840 mg, 2.481 mmol) in THF (10 mL) at −78° C. was added 1.6 N n-BuLi in hexanes (2.016 mL, 3.23 mmol). The mixture was stirred at −78° C. for 0.5 h. Then iodine (945 mg, 3.72 mmol) in THF (2 mL) was added, the mixture was stirred at −78° C. for 0.5 h. LCMS indicated a completion of the reaction. The reaction mixture was diluted with EtOAc, quenched with saturated ammonium chloride. The organic layer was washed with Na₂S₂O₃ and brine, dried over sodium sulfate. After evaporation of solvent, the crude was purified with a 40 g ISCO column eluted with 0-20% EtOAc in hexanes for 20 min. The desired fraction was collected and concentrated to give Intermediate 120G (880 mg, 1.895 mmol, 76% yield) as colorless oil. ¹H NMR (400 MHz, chloroform-d) δ 7.00 (d, J=8.6 Hz, 1H), 6.81 (s, 1H), 1.03 (s, 9H), 0.45 (d, J=1.1 Hz, 9H), 0.18 (d, J=1.1 Hz, 6H). ¹⁹F NMR (376 MHz, chloroform-d) δ −120.92 (s, 1F). LC-MS: method C, RT=2.57 min, MS (ESI) m/z: 465 (M+H)⁺.

Intermediate 120H: 5-(5-(tert-butyldimethylsilyloxy)-6-fluoro-7-(trimethylsilyl) benzofuran-2-yl)-2-(difluoromethoxy)-7-methylquinoxaline

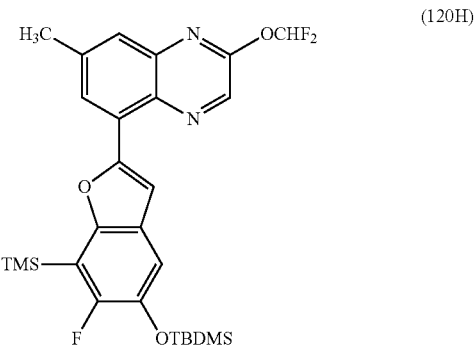 [SMILES: Cc1cc(-c2cc3cc(O[Si](C)(C)C(C)(C)C)c(F)c([Si](C)(C)C)c3o2)c2ncc(OC(F)F)nc2c1]

(120H)

To Intermediate I-1 (57.9 mg, 0.172 mmol), Intermediate 120G (80 mg, 0.172 mmol) and [1,1'-bis(diphenylphosphino)ferrocene]dichloropalladium (II) complex with dichloromethane (1:1) (7.03 mg, 8.61 μmol) was added toluene (0.75 mL) and EtOH (0.25 mL). The mixture was sonicated for 1 min, and flushed with argon. To the above mixture was added sodium carbonate (0.172 mL, 2M, 0.344 mmol). The reaction mixture was heated in a microwave reactor at 120° C. for 30 min. The crude reaction mixture was directly loaded onto a 40 g ISCO column, eluted with 0-20% EtOAc in hexanes for 20 min. The desired fractions were combined and concentrated to yield Intermediate 120H (100 mg, 0.128 mmol, 74.3% yield) as a yellow oil. $^1$H NMR (400 MHz, chloroform-d) δ 8.63 (s, 1H), 8.12 (d, J=1.8 Hz, 1H), 7.97 (s, 1H), 7.63 (dd, J=1.9, 1.0 Hz, 1H), 7.86-7.47 (m, 1H), 7.17 (d, J=8.6 Hz, 1H), 2.64 (s, 3H), 1.05 (s, 9H), 0.57 (d, J=1.1 Hz, 9H), 0.21 (d, J=0.9 Hz, 6H). $^{19}$F NMR (376 MHz, chloroform-d) δ −89.68 (s, 2F). LC-MS: method C, RT=4.63 min, MS (ESI) m/z: 547 (M+H)$^+$.

Intermediate 120I 6-fluoro-2-(2-methoxy-7-methylquinoxalin-5-yl)-7-(trimethylsilyl)benzofuran-5-ol

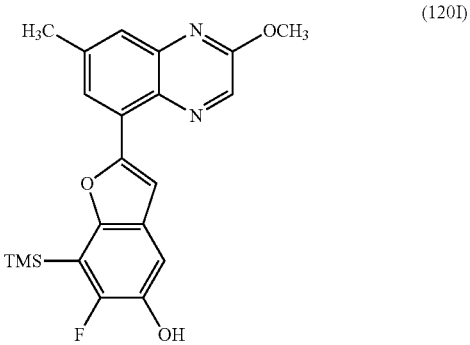 [SMILES: COc1cnc2c(-c3cc4cc(O)c(F)c([Si](C)(C)C)c4o3)cc(C)cc2n1]

(120I)

To solution of Intermediate 120H (100 mg, 0.128 mmol) in THF (3 mL) at room temperature was added sodium methoxide in MeOH (0.095 mL, 4.37M, 0.448 mmol). The reaction mixture was stirred at room temperature for 30 min. TLC and LCMS indicated a completion of the reaction. The reaction mixture was quenched with saturated NH$_4$Cl, diluted with EtOAc. The organic layer was washed with saturated sodium bicarbonate, brine, dried over MgSO$_4$ and concentrated. The crude was purified with a 12 g ISCO column eluted with 0-50% EtOAc in hexanes for 15 min. The desired fraction was collected and concentrated to give Intermediate 120I (69 mg, 0.122 mmol, 95% yield) as a yellow solid. $^1$H NMR (400 MHz, chloroform-d) δ 8.51 (s, 1H), 8.00 (d, J=1.8 Hz, 1H), 7.97 (s, 1H), 7.62 (dd, J=1.8, 0.9 Hz, 1H), 7.23 (d, J=9.2 Hz, 1H), 4.12 (s, 3H), 0.58 (s, 9H). LC-MS: method C, RT=2.77 min, MS (ESI) m/z: 397 (M+H)$^+$.

Intermediate 120J: 6-fluoro-2-(2-methoxy-7-methylquinoxalin-5-yl)benzofuran-5-ol

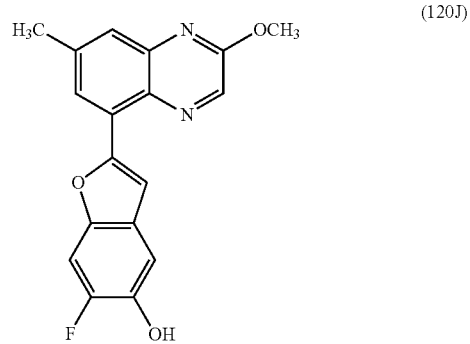 [SMILES: COc1cnc2c(-c3cc4cc(O)c(F)cc4o3)cc(C)cc2n1]

(120J)

To a solution of Intermediate 120I (69 mg, 0.122 mmol) in THF (2 mL) was added AcOH (0.021 mL, 0.365 mmol) followed by TBAF (0.488 mL, 0.488 mmol). The mixture was stirred at room temperature for 3 h. LCMS indicated a completion of the reaction. Solvent was removed and the residual was purified with a 12 g ISCO column eluted with 0-70% EtOAc/hexanes for 20 min. The desired fraction was collected and concentrated to give Intermediate 120J (30 mg, 0.093 mmol, 76% yield). $^1$H NMR (400 MHz, chloroform-d) δ 8.48 (s, 1H), 8.42-8.38 (m, 1H), 7.95 (s, 1H), 7.84 (s, 1H), 7.50 (s, 1H), 7.16 (d, J=10.6 Hz, 1H), 7.12-7.06 (m, 1H), 4.07-3.98 (m, 3H), 2.51 (s, 3H). $^{19}$F NMR (376 MHz, chloroform-d) δ −137.18 (s, 1F). LC-MS: method C, RT=2.42 min, MS (ESI) m/z: 325 (M+H)$^+$.

Example 120

To a solution of Intermediate 120J (15 mg, 0.046 mmol) in DMF (1 mL) was added Cs$_2$CO$_3$ (45.2 mg, 0.139 mmol) and MeI (0.014 mL, 0.231 mmol). The mixture was stirred at room temperature for 2 h. LCMS indicated a completion of the reaction. The mixture was filtered. The filtrate was purified via preparative LC/MS (method D, 65-100% B over 20 min., then a 5-min hold at 100% B). Fractions containing the desired product were combined and dried via centrifugal evaporation to give Example 120 (2.6 mg, 7.45 μmol, 16.12% yield). $^1$H NMR (500 MHz, chloroform-d) δ 8.51 (s, 1H), 8.08 (s, 1H), 8.02 (s, 1H), 7.62 (s, 1H), 7.33 (d, J=10.5 Hz, 1H), 7.19 (d, J=8.3 Hz, 1H), 4.12 (s, 3H), 3.96 (s, 3H), 2.62 (s, 3H). LC-MS: method C, RT=2.59 min, MS (ESI) m/z: 338.9 (M+H)$^+$. Analytical HPLC purity (method B): 97%.

Example 121

5-(7-chloro-6-fluoro-5-methoxybenzofuran-2-yl)-2-(methoxymethyl)-7-methylquinoxaline

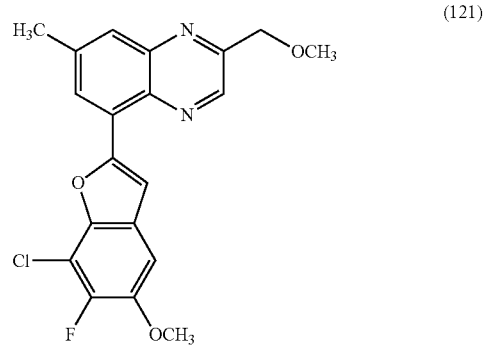 [SMILES: COCc1cnc2c(-c3cc4cc(OC)c(F)c(Cl)c4o3)cc(C)cc2n1]

(121)

Intermediate 121A:
7-chloro-6-fluoro-5-methoxybenzofuran

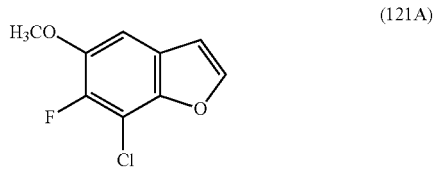 [SMILES: COc1cc2ccoc2c(Cl)c1F]

(121A)

To diisopropylamine (0.270 mL, 1.896 mmol) in THF (5 mL) at −78° C. was added 1.6 N n-BuLi in hexanes (0.948 mL, 1.517 mmol). The mixture was stirred at −78° C. for 0.5 h. Intermediate 120C (210 mg, 1.264 mmol) in THF (1 mL) was added, the mixture was stirred at −78° C. for 0.5 h. Hexachloroethane (449 mg, 1.896 mmol) in THF (1 mL) was added, and the reaction mixture was stirred at −78° C. for 0.5 h. The reaction mixture was diluted with EtOAc, quenched with saturated ammonium chloride. The organic layer was washed with Na$_2$SO$_3$, brine, dried over sodium sulfate and concentrated. The crude sample was purified with a 40 g ISCO column eluted with 0-70% EtOAc in hexanes for 20 min. The desired fraction was collected and concentrated to give Intermediate 121A (240 mg, 1.196 mmol, 95% yield) as a white solid. $^1$H NMR (400 MHz, chloroform-d) δ 7.67 (d, J=2.0 Hz, 1H), 7.05 (d, J=7.5 Hz, 1H), 6.76 (d, J=2.2 Hz, 1H), 3.94 (s, 3H). $^{19}$F NMR (376 MHz, chloroform-d) δ −140.56 (s, 1F). LC-MS: method C, RT=2.01 min, MS (ESI) m/z: No (M+H)$^+$.

Intermediate 121B:
7-chloro-6-fluoro-2-iodo-5-methoxybenzofuran

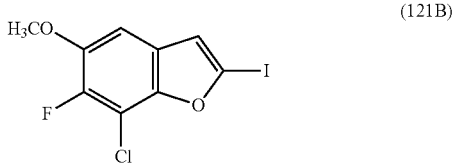 [SMILES: COc1cc2cc(I)oc2c(Cl)c1F]

(121B)

To a solution of Intermediate 121A (240 mg, 1.196 mmol) in THF (5 mL) at −78° C. was added 1.6 N n-BuLi in hexanes (0.972 mL, 1.555 mmol). The mixture was stirred at −78° C. for 0.5 h. Iodine (456 mg, 1.795 mmol) in THF (2 mL) was added, and the mixture was stirred at −78° C. for 0.5 h. The mixture was warmed up to room temperature and continued stirring for 1 h. The reaction mixture was diluted with EtOAc, quenched with saturated ammonium chloride. The organic layer was washed with Na$_2$S$_2$O$_3$, brine, dried over sodium sulfate. The crude sample was purified with a 12 g ISCO column eluted with 0-20% EtOAc in hexanes for 20 min. The desired fraction was collected and concentrated to give Intermediate 121B (280 mg, 0.686 mmol, 57.3% yield) as colorless oil. $^{19}$F NMR (376 MHz, chloroform-d) δ −140.34 (s, 1F). $^1$H NMR (400 MHz, chloroform-d) δ 6.96 (d, J=7.3 Hz, 1H), 6.92 (s, 1H), 3.93 (s, 3H). LC-MS: method C, RT=2.24 min, MS (ESI) m/z: No (M+H)$^+$.

Example 121

To Intermediate I-2 (11.37 mg, 0.049 mmol), Intermediate 121B (20 mg, 0.049 mmol) and [1,1'-bis(diphenylphosphino)ferrocene]dichloropalladium (II) complex with dichloromethane (1:1) (2.001 mg, 2.450 µmol) was added toluene (0.75 mL) and EtOH (0.25 mL). The mixture was sonicated for 1 min, and flushed with argon. To this mixture was added Na$_2$CO$_3$ (0.049 mL, 2M, 0.098 mmol). The reaction mixture was heated in a microwave reactor at 120° C. for 30 min. The crude reaction mixture was directly loaded onto a 12 g ISCO column, eluted with 0-50% EtOAc in hexanes for 20 min. The desired fractions were combined and concentrated. The sample was redissolved in DMSO and further purified via preparative LC/MS (method D, 65-100% B over 15 min., then a 5-min hold at 100% B). Fractions containing the desired product were combined and dried via centrifugal evaporation to give Example 121 (4.7 mg, 0.012 mmol, 24.55% yield). $^1$H NMR (500 MHz, DMSO-d$_6$) δ 9.05 (s, 1H), 8.24 (s, 1H), 8.21 (s, 1H), 7.90 (s, 1H), 7.56 (d, J=7.7 Hz, 1H), 4.79 (s, 2H), 3.93 (s, 3H), 3.46 (s, 3H), 2.66 (s, 3H). LC-MS: method C, RT=2.55 min, MS (ESI) m/z: 387.1(M+H)$^+$. Analytical HPLC purity (method B): 99%.

Example 122

5-(7-chloro-6-fluoro-5-methoxybenzofuran-2-yl)-2-methoxy-7-methylquinoxaline

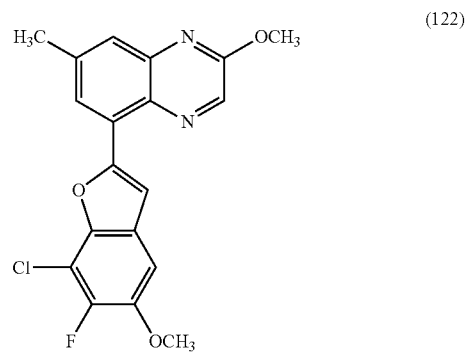 [SMILES: COc1cnc2c(-c3cc4cc(OC)c(F)c(Cl)c4o3)cc(C)cc2n1]

(122)

To Intermediate I-1 (16.47 mg, 0.049 mmol), Intermediate 121B (20 mg, 0.049 mmol) and [1,1'-bis(diphenylphosphino)ferrocene]dichloropalladium (II) complex with dichloromethane (1:1) (2.001 mg, 2.450 µmol) was added toluene (0.75 mL) and EtOH (0.25 mL). The mixture was sonicated for 1 min, and flushed with argon. To this was added sodium carbonate (0.049 mL, 2M, 0.098 mmol). The reaction mixture was heated in a microwave reactor at 120° C. for 30 min. The crude reaction mixture was directly loaded onto a 12 g ISCO column, eluted with 0-20% EtOAc in hexane for 20 min. The desired fractions were combined and concentrated to yield 5-(7-chloro-6-fluoro-5-methoxybenzofuran-2-yl)-2-(difluoromethoxy)-7-methylquinoxaline as a yellow oil. LC-MS: method C, RT=2.81 min, MS (ESI) m/z: 409 (M+H)$^+$. The above sample was dissolved in THF (1 ml) and sodium methoxide (0.036 mL, 4.37M, 0.172 mmol) was added. The mixture was stirred at room temperature for 30 min, quenched with a drop of 10% water/MeOH with 0.1% TFA (HPLC solvent) and concentrated. The crude was redissolved in DMSO and purified via preparative LC/MS (method C, 60-100% B over 20 min., then a 5-min hold at 100% B). Fractions containing the desired product were combined and dried via centrifugal evaporation to give Example 122 (0.8 mg, 2.146 µmol, 4.38% yield). $^1$H NMR (500 MHz, DMSO-d$_6$) δ 8.70 (s, 1H), 8.13 (s, 1H), 8.07 (s, 1H), 7.74 (s, 1H), 7.57 (d, J=7.7 Hz, 1H), 4.09 (s, 3H), 3.95 (s, 3H), 2.63 (s, 3H). LC-MS: method C, RT=2.76 min, MS (ESI) m/z: 373.05 (M+H)$^+$. Analytical HPLC purity (method B): 100%.

Example 123

2-((6-fluoro-2-(2-methoxy-7-methylquinoxalin-5-yl)benzofuran-5-yl)oxy)ethyl (2-methylpyridin-4-yl)carbamate

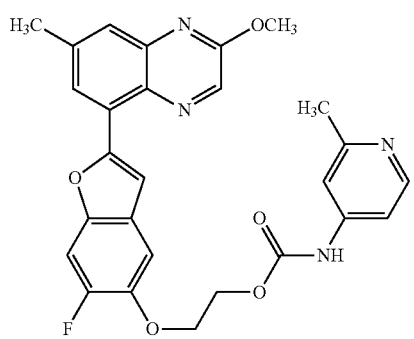
(123)

Intermediate 123A: 6-fluoro-2-iodobenzofuran-5-ol

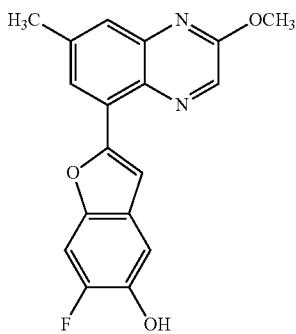
(123A)

To a solution of Intermediate 120G (64 mg, 0.138 mmol) in THF (1 mL) was added TBAF (0.413 mL, 0.413 mmol). The mixture was stirred at room temperature for 1 h. Solvent was removed under vacuum and the residual was purified with a 12 g ISCO column eluted with 0-70% EtOAc in hexanes for 15 min. The desired fraction was collected and concentrated to give Intermediate 123A (38 mg, 0.137 mmol, 99% yield) as white solid. $^{19}$F NMR (376 MHz, chloroform-d) δ −141.74 (s, 1F). $^1$H NMR (400 MHz, chloroform-d) δ 7.27-7.23 (m, 1H), 7.10 (d, J=8.6 Hz, 1H), 6.86 (d, J=0.9 Hz, 1H), 5.10-4.99 (m, 1H). LC-MS: method C, RT=1.84 min, MS (ESI) m/z: No (M+H)$^+$.

Intermediate 123B: 6-fluoro-2-(2-methoxy-7-methylquinoxalin-5-yl)benzofuran-5-ol

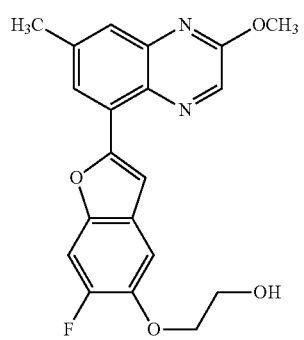
(123B)

To Intermediate I-1 (45.9 mg, 0.137 mmol), Intermediate 123A (38 mg, 0.137 mmol) and [1,1'-bis(diphenylphosphino)ferrocene]dichloropalladium (II) complex with dichloromethane (1:1) (5.58 mg, 6.83 μmol) was added toluene (0.75 mL) and EtOH (0.25 mL). The mixture was sonicated for 1 min, and flushed with argon. To this was added sodium carbonate (0.137 mL, 2M, 0.273 mmol). The reaction mixture was heated in a microwave reactor at 120° C. for 30 min. The crude reaction mixture was directly loaded onto a 12 g ISCO column, eluted with 0-50% EtOAc in hexanes for 15 min. The desired fractions were combined and concentrated to yield Intermediate 123B (78 mg, 0.130 mmol, 95% yield) as a yellow solid. $^1$H NMR (400 MHz, chloroform-d) δ 8.65 (s, 1H), 8.20 (s, 1H), 8.01 (s, 1H), 7.66 (s, 1H), 7.33 (d, J=10.1 Hz, 1H), 2.65 (s, 3H). $^{19}$F NMR (376 MHz, chloroform-d) δ −89.71 (s, 2F), −140.50 (s, 1F). LC-MS: method C, RT=2.37 min, MS (ESI) m/z: 361 (M+H)$^+$.

Intermediate 123C 2-(6-fluoro-2-(2-methoxy-7-methylquinoxalin-5-yl)benzofuran-5-yloxy)ethanol

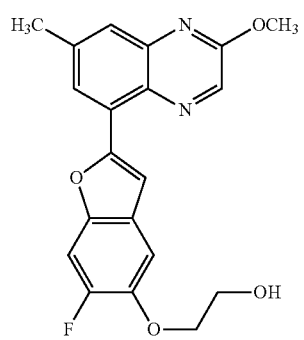
(123C)

To a solution of Intermediate 123B (49.4 mg, 0.137 mmol) in DMF (2 mL) was added Cs$_2$CO$_3$ (134 mg, 0.411 mmol) and 2-bromoethyl acetate (0.031 mL, 0.274 mmol). The mixture was stirred at room temperature for 1 h. LCMS indicated a completion of the reaction. The mixture was diluted with EtOAc and water, extracted with EtOAc. The combined organic layer was washed with brine, dried with MgSO$_4$ and concentrated. LC-MS: method C, RT=2.53 min, MS (ESI) m/z: 447 (M+H)$^+$. The crude sample was redissolved in THF (1 ml) and sodium methoxide (0.094 mL, 4.37M, 0.411 mmol) was added. The mixture was stirred at room temperature for 30 min, diluted with EtOAc and saturated NH$_4$Cl, extracted with EtOAc. The combined organic layer was washed with saturated NaHCO$_3$, brine, dried over MgSO$_4$ and concentrated. The crude sample was dissolved in DMF and load on a 40 g ISCO column, eluted with 0-100% EtOAc in hexanes for 20 min. The desired fraction was collected and concentrated to give Intermediate 123C (50 mg, 0.136 mmol, 99% yield) as a yellow solid. $^{19}$F NMR (376 MHz, methanol-d$_4$) δ −136.00 (s, 1F). $^1$H NMR (400 MHz, methanol-d$_4$) δ 8.51 (s, 1H), 8.07 (d, J=1.8 Hz, 1H), 8.02 (d, J=0.9 Hz, 1H), 7.62 (dd, J=1.8, 0.9 Hz, 1H), 7.38 (dd, J=10.8, 0.9 Hz, 1H), 7.34 (d, J=8.4 Hz, 1H), 4.19-4.16 (m, 2H), 4.11 (s, 3H), 3.97-3.92 (m, 2H), 2.61 (s, 3H). LC-MS: method C, RT=2.39 min, MS (ESI) m/z: 369 (M+H)$^+$.

Intermediate 123D 2-(6-fluoro-2-(2-methoxy-7-methylquinoxalin-5-yl)benzofuran-5-yloxy)ethyl carbonochloridate

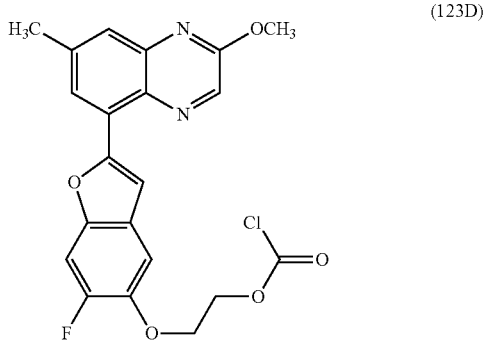 [SMILES: COc1cnc2c(-c3cc4cc(OCCOC(=O)Cl)c(F)cc4o3)cc(C)cc2n1]
(123D)

To a solution of Intermediate 123C (45 mg, 0.122 mmol) in THF (2 mL) was added 15% phosgene in toluene (0.431 mL, 0.611 mmol), and the mixture was stirred at room temperature overnight. Solvent was removed under vacuum to give Intermediate 123D as a yellow solid. It was used for the next step without any purification. LC-MS: method C, RT=2.63 min, MS (ESI) m/z: 431 (M+H)$^+$.

Example 123

To a solution of Intermediate 123D (10 mg, 0.023 mmol) in THF (1 mL) was added 2-methylpyridin-4-amine (7.53 mg, 0.070 mmol) in DCM (0.5 mL) followed by DIEA (0.041 mL, 0.232 mmol). The mixture was stirred at room temperature for 1 h. LCMS indicated a completion of the reaction. The reaction was quenched by addition of a small amount of 10% MeOH/water/0.1% TFA (HPLC solvent). Solvent was removed under vacuum. The residual was dissolved in DMSO and purified via preparative LC/MS (method C, 40-80% B over 20 min., then a 5-min hold at 100% B). Fractions containing the desired product were combined and dried via centrifugal evaporation to give Example 123 (2.7 mg, 5.37 µmol, 23.15% yield). $^1$H NMR (500 MHz, DMSO-d$_6$) δ 11.20 (br. s., 1H), 8.67 (s, 1H), 8.50 (d, J=6.6 Hz, 1H), 8.03 (s, 2H), 7.76-7.65 (m, 4H), 7.57 (d, J=8.5 Hz, 1H), 4.60 (br. s., 2H), 4.41 (br. s., 2H), 4.06 (s, 3H), 2.58 (br. s., 6H). LC-MS: method C, RT=1.99 min, MS (ESI) m/z: 503.15 (M+H)$^+$. Analytical HPLC purity (method B): 100%.

Example 124

(8-(7-chloro-6-fluoro-5-methoxybenzofuran-2-yl)-3-methoxyquinoxalin-6-yl)methanol

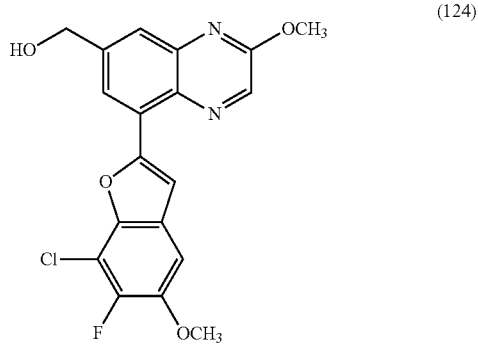 [SMILES: COc1cnc2c(-c3cc4cc(OC)c(F)c(Cl)c4o3)cc(CO)cc2n1]
(124)

To Intermediate I-27 (14.22 mg, 0.035 mmol), Intermediate 121B (14.22 mg, 0.035 mmol) and [1,1'-bis(diphenylphosphino)ferrocene]dichloropalladium (II) complex with dichloromethane (1:1) (1.423 mg, 1.742 µmol) was added toluene (0.75 mL) and EtOH (0.25 mL). The mixture was sonicated for 1 min, and flushed with argon. To this mixture was added sodium carbonate (0.035 mL, 2M, 0.070 mmol). The reaction mixture was heated in a microwave reactor at 120° C. for 30 min. The crude reaction mixture was directly loaded onto a 12 g ISCO column and eluted with 0-20% EtOAc in hexanes for 20 min. The desired fractions were combined and concentrated to yield 7-(((tert-butyldimethylsilyl)oxy)methyl)-5-(7-chloro-6-fluoro-5-methoxybenzofuran-2-yl)-2-methoxyquinoxaline as an off-white solid. The sample was dissolved in 2 ml of DCM and TFA (0.013 mL, 0.174 mmol) was added. The mixture was stirred at room temperature for 1 h. TLC indicated a small conversion. TBAF (0.070 mL, 0.070 mmol) was added to the mixture and stirred at room temperature overnight. LCMS indicate a completion of the reaction. Solvent was completely removed and the residual was purified via preparative LC/MS (method C, 45-90% B over 20 min., then a 5-min hold at 100% B). Fractions containing the desired product were combined and dried via centrifugal evaporation to give Example 124 (3.0 mg, 7.33 µmol, 21.04% yield). $^1$H NMR (500 MHz, DMSO-d$_6$) δ 8.69 (s, 1H), 8.17 (s, 1H), 8.09 (s, 1H), 7.79 (s, 1H), 7.52 (d, J=7.4 Hz, 1H), 5.60 (t, J=5.2 Hz, 1H), 4.80 (d, J=5.5 Hz, 2H), 4.07 (s, 3H), 3.93 (s, 3H). LC-MS: method C, RT=2.20 min, MS (ESI) m/z: 388.90 (M+H)$^+$. Analytical HPLC purity (method B): 95%.

Example 125

(8-(6-fluoro-5-methoxybenzofuran-2-yl)-3-methoxyquinoxalin-6-yl)methanol

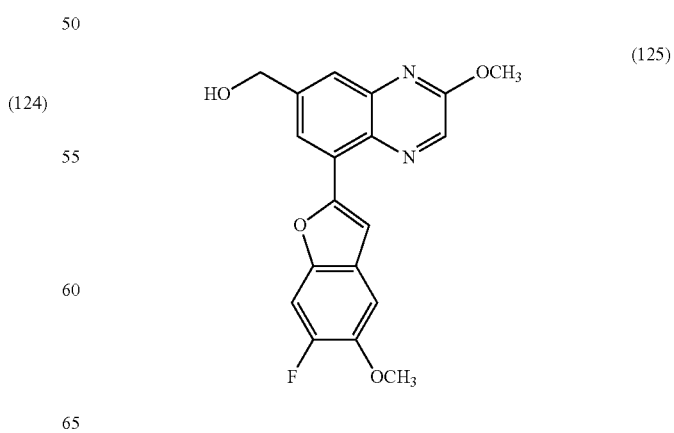
(125)

Intermediate 125A 2-(7-((tert-butyldimethylsilyloxy)methyl)-2-methoxyquinoxalin-5-yl)-6-fluorobenzofuran-5-ol

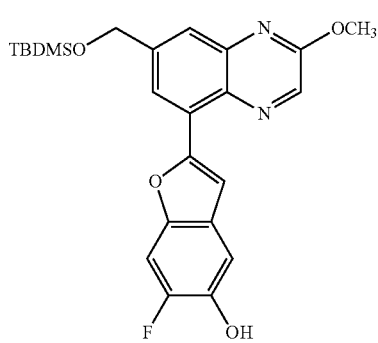

(125A)

To Intermediate I-27 (90 mg, 0.209 mmol), Intermediate 123A (58.1 mg, 0.209 mmol) and [1,1'-bis(diphenylphosphino)ferrocene]dichloropalladium (II) complex with dichloromethane (1:1) (8.54 mg, 10.45 μmol) was added toluene (0.75 mL) and EtOH (0.25 mL). The mixture was sonicated for 1 min, and flushed with argon. To this was added sodium carbonate (0.209 mL, 2M, 0.418 mmol). The reaction mixture was heated in a microwave reactor at 120° C. for 30 min. The crude reaction mixture was directly loaded onto a 40 g ISCO column which was eluted with 0-50% EtOAc in hexanes for 20 min. The desired fractions were combined and concentrated to yield Intermediate 125A (105 mg, 0.185 mmol, 88% yield) as a yellow oil. $^1$H NMR (400 MHz, chloroform-d) δ 8.55 (s, 1H), 8.18 (d, J=2.0 Hz, 1H), 8.00 (d, J=0.9 Hz, 1H), 7.82-7.77 (m, 1H), 7.31 (dd, J=10.0, 0.8 Hz, 1H), 7.25-7.22 (m, 1H), 5.00 (s, 2H), 4.14 (s, 3H), 1.02 (d, J=5.7 Hz, 9H), 0.19 (s, 6H). LC-MS: method C, RT=2.97 min, MS (ESI) m/z: 455 (M+H)$^+$.

Example 125

To a solution of Intermediate 125A (14 mg, 0.031 mmol) in DMF (1 mL) was added Cs$_2$CO$_3$ (30.1 mg, 0.092 mmol) and MeI (9.63 μL, 0.154 mmol). The mixture was stirred at room temperature for 2 h. LCMS indicated a completion of the reaction. The mixture was loaded to 12 g ISCO column which was eluted with 0-50% EtOAc in hexanes for 15 min. The desired fraction was combined and concentrated to give 7-(((tert-butyldimethylsilyl)oxy)methyl)-5-(6-fluoro-5-methoxybenzofuran-2-yl)-2-methoxyquinoxaline as a light yellow solid. The intermediate was dissolved in THF (2 ml), and TBAF (0.062 mL, 0.062 mmol) was added. The mixture was stirred at room temperature for 1 h. LCMS indicated a completion of the reaction. Solvent was removed, the residual was purified via preparative LC/MS (method D, 35-75% B over 15 min., then a 5-min hold at 100% B). Fractions containing the desired product were combined and dried via centrifugal evaporation to give Example 125 (3.3 mg, 9.13 μmol, 29.6% yield). $^1$H NMR (500 MHz, DMSO-d$_6$) δ 8.71 (s, 1H), 8.18 (d, J=1.7 Hz, 1H), 8.06 (d, J=0.8 Hz, 1H), 7.78 (d, J=1.7 Hz, 1H), 7.70 (d, J=11.0 Hz, 1H), 7.51 (d, J=8.8 Hz, 1H), 5.57 (t, J=5.8 Hz, 1H), 4.78 (d, J=5.5 Hz, 2H), 4.08 (s, 3H), 3.90 (s, 3H). LC-MS: method C, RT=1.95 min, MS (ESI) m/z: 355.15 (M+H)$^+$. Analytical HPLC purity (method B): 98%.

Example 126

2-((6-fluoro-2-(7-(hydroxymethyl)-2-methoxyquinoxalin-5-yl)benzofuran-5-yl)oxy)ethyl (2-methylpyridin-4-yl)carbamate

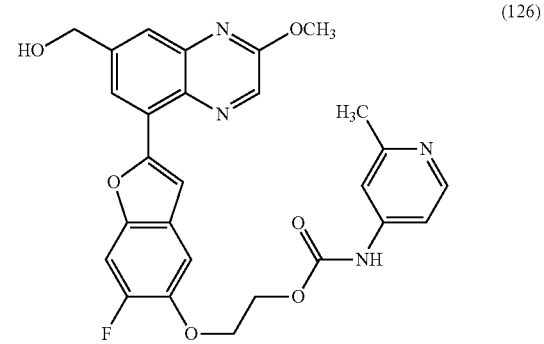 [SMILES: COc1cnc2c(-c3cc4cc(OCCOC(=O)Nc5ccnc(C)c5)c(F)cc4o3)cc(CO)cc2n1]

(126)

Intermediate 126A 2-(2-(7-((tert-butyldimethylsilyloxy)methyl)-2-methoxyquinoxalin-5-yl)-6-fluorobenzofuran-5-yloxy)ethanol

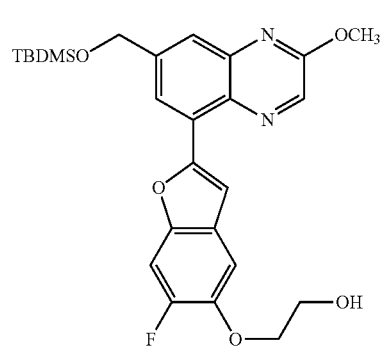

(126A)

To a solution of Intermediate 125A (90 mg, 0.158 mmol) in DMF (2 mL) was added Cs$_2$CO$_3$ (155 mg, 0.475 mmol) and 2-bromoethyl acetate (0.035 mL, 0.317 mmol). The mixture was stirred at room temperature overnight. LCMS indicated a completion of the reaction. The mixture was diluted with EtOAc and water, extracted with EtOAc. The combined organic layer was washed with brine, dried over MgSO$_4$ and concentrated. The crude sample was dissolved in THF (2 ml) and NaOMe (0.109 mL, 4.37M, 0.475 mmol) was added. The mixture was stirred at room temperature for 30 min. LCMS indicated a completion of the reaction. The mixture was diluted with EtOAc and saturate NH$_4$Cl, extracted with EtOAc. The combined organic layer was washed with NaHCO$_3$, brine, dried over MgSO$_4$ and concentrated. The crude sample was dissolved in a small amount of DMF, loaded on a 40 g ISCO column, eluted with 0-100% EtOAc in hexanes for 20 min. The desired fraction was collected and concentrated to give Intermediate 126A (47 mg, 0.075 mmol, 47.6% yield). $^1$H NMR (400 MHz, chloroform-d) δ 8.53 (s, 1H), 8.18 (d, J=1.8 Hz, 1H), 8.01 (d, J=0.7 Hz, 1H), 7.83-7.76 (m, 1H), 7.32 (dd, J=10.5, 0.8

Hz, 1H), 7.23 (d, J=8.4 Hz, 1H), 5.00 (s, 2H), 4.23-4.16 (m, 2H), 4.14 (s, 3H), 4.01 (dt, 4.3 Hz, 2H), 1.05-1.01 (m, 9H), 0.19 (s, 6H). LC-MS: method C, RT=2.98 min, MS (ESI) m/z: 499 (M+H)+.

Intermediate 126B 2-(2-(7-(((tert-butyldimethylsilyloxy)methyl)-2-methoxyquinoxalin-5-yl)-6-fluorobenzofuran-5-yloxy)ethyl carbonochloridate

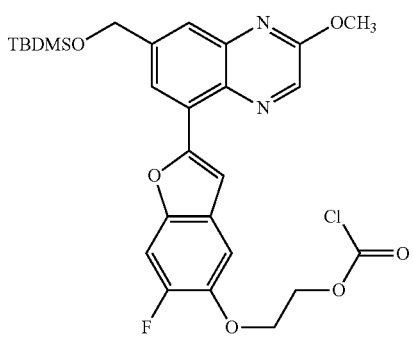

(126B)

To the solution of Intermediate 126A (47 mg, 0.075 mmol) and DIEA (0.066 ml, 0.377 mmol) in THF (1 mL) was added to 15% phosgene in toluene (0.160 ml, 0.226 mmol). The mixture was stirred at room temperature for 3 h. Solvent was removed under vacuum to give Intermediate 126B as a yellow solid. It was used for the next step without any purification. LC-MS: method C, RT=3.46 min, MS (ESI) m/z: 561 (M+H)+.

Example 126

To a solution of Intermediate 126B (10 mg, 0.018 mmol) in THF (1 mL) was added 2-methylpyridin-4-amine (5.78 mg, 0.053 mmol) in DCM (0.5 mL) followed by DIEA (0.031 mL, 0.178 mmol). The mixture was stirred at room temperature for 1 h. LCMS indicated a completion of the reaction. TBAF (0.071 mL, 0.071 mmol) was added, and the mixture was stirred at room temperature overnight. The reaction mixture was quenched by addition of a small amount of MeOH/water/0.1% TFA (HPLC solvent). Solvent was removed under vacuum. The residual was dissolved in DMSO and purified via preparative LC/MS (method D, 30-70% B over 20 min., then a 5-min hold at 100% B). Fractions containing the desired product were combined and dried via centrifugal evaporation to give Example 126 (2.3 mg, 4.26 mol, 23.89% yield). $^1$H NMR (500 MHz, DMSO-$d_6$) δ 10.35 (s, 1H), 8.70 (s, 1H), 8.28 (d, J=5.8 Hz, 1H), 8.18 (d, J=1.7 Hz, 1H), 8.05 (s, 1H), 7.78 (s, 1H), 7.73 (d, J=10.7 Hz, 1H), 7.56 (d, J=8.5 Hz, 1H), 7.37 (s, 1H), 7.33 (d, J=5.5 Hz, 1H), 5.57 (s, 1H), 4.78 (d, J=5.0 Hz, 2H), 4.57-4.45 (m, 2H), 4.42-4.32 (m, 2H), 4.07 (s, 3H), 2.41 (s, 3H). LC-MS: method C, RT=1.48 min, MS (ESI) m/z: 519.20 (M+H)+. Analytical HPLC purity (method B): 96%.

Example 127

3-methoxy-8-(6-methoxybenzo[d]thiazol-2-yl)qui-noxalin-6-yl)methanol

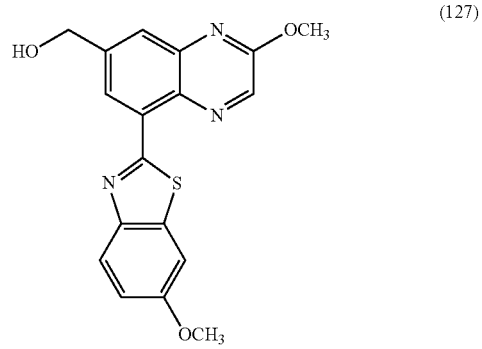 [SMILES: COc1ccc2nc(-c3cc(CO)cc4nc(OC)cnc34)sc2c1]

(127)

To Intermediate I-27 (10.6 mg, 0.025 mmol), 2-bromo-6-methoxybenzo[d] thiazole (6.01 mg, 0.025 mmol) and [1,1'-bis(diphenylphosphino)ferrocene] dichloropalladium (II) complex with dichloromethane (1:1) (1.006 mg, 1.231 μmol) was added toluene (0.75 mL) and EtOH (0.25 mL). The mixture was sonicated for 1 min, and flushed with argon. To this was added sodium carbonate (0.025 mL, 2M, 0.049 mmol). The reaction mixture was heated in a microwave reactor at 120° C. for 30 min. The crude reaction mixture was directly loaded on a 12 g ISCO column, eluted with 0-50% EtOAc in hexanes for 15 min. The desired fraction was collected and concentrated to yield 2-(7-(((tert-butyldimethylsilyl)oxy)methyl)-2-methoxyquinoxalin-5-yl)-6-methoxybenzo[d]thiazole. LC-MS: method C, RT=3.4 min, MS (ESI) m/z: 468 (M+H)+. The sample was redissolved in THF (1 ml) and TBAF (0.074 mL, 0.074 mmol) was added. The mixture was stirred at room temperature for 30 min. LCMS indicated a completion of the reaction. The mixture was concentrated and purified via preparative LC/MS (method C, 30-70% B over 20 min., then a 5-min hold at 100% B). Fractions containing the desired product were combined and dried via centrifugal evaporation to give Example 127 (1.4 mg, 3.80 μmol, 15.44% yield). $^1$H NMR (500 MHz, DMSO-$d_6$) δ 8.75 (s, 1H), 8.72 (s, 1H), 8.01 (d, J=8.9 Hz, 1H), 7.91 (s, 1H), 7.72 (d, J=2.4 Hz, 1H), 7.16 (dd, J=9.0, 2.3 Hz, 1H), 4.82 (d, J=5.5 Hz, 2H), 4.09 (s, 3H). LC-MS: method C, RT=1.82 min, MS (ESI) m/z: 345.10 (M+H)+. Analytical HPLC purity (method B): 100%.

Example 128

2-(2-(7-(hydroxymethyl)-2-methoxyquinoxalin-5-yl)-4-methylbenzo[d]thiazol-6-yloxy)ethyl 6-methylpyridin-3-ylcarbamate

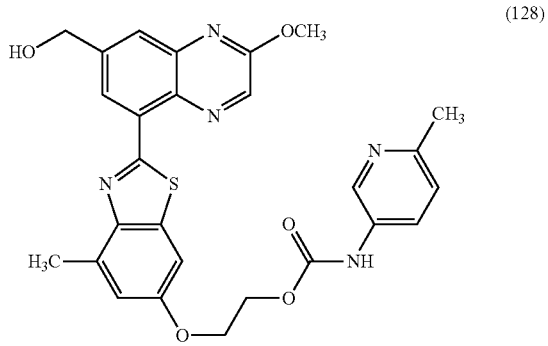 [SMILES: COc1cnc2c(-c3nc4c(C)cc(OCCOC(=O)Nc5ccc(C)nc5)cc4s3)cc(CO)cc2n1]

(128)

Intermediate 128A: 2-(2-chloro-4-methylbenzo[d]thiazol-6-yloxy)ethanol

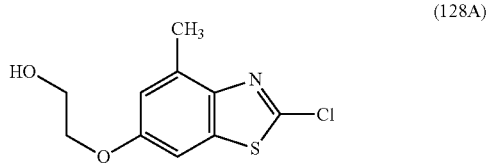
(128A)

To a suspension of Intermediate 89B (500 mg, 2.504 mmol) in DMF (10 mL) was added cesium carbonate (1.63 g, 5.01 mmol). Then 2-bromoethyl acetate (0.331 mL, 3.01 mmol) was added dropwise. The reaction mixture was stirred at room temperature overnight. LCMS indicated a completion of the reaction. NaOH (2.504 mL, 2M, 5.01 mmol) was added to the reaction mixture, followed by MeOH (1 ml). The mixture was stirred at room temperature for 1 h. LCMS indicated a completion of the reaction. The reaction mixture was diluted with EtOAc and water, extracted with EtOAc, the combined organic layer was washed with brine, dried with $MgSO_4$ and concentrated. The crude sample was purified with a 40 g ISCO column eluted with 0-100% EtOAc in hexane for 20 min. The desired fraction was collected and concentrated to give Intermediate 128A (600 mg, 2.462 mmol, 98% yield). $^1$H NMR (400 MHz, chloroform-d) δ 7.09 (d, J=2.2 Hz, 1H), 6.97-6.85 (m, 1H), 4.24-4.09 (m, 2H), 4.00 (d, J=3.7 Hz, 2H), 2.66 (s, 3H). LC-MS: method C, RT=1.82 min, MS (ESI) m/z: 244 (M+H)$^+$.

Intermediate 128B 2-(2-(7-((tert-butyldimethylsilyloxy)methyl)-2-methoxyquinoxalin-5-yl)-4-methylbenzo[d]thiazol-6-yloxy)ethanol

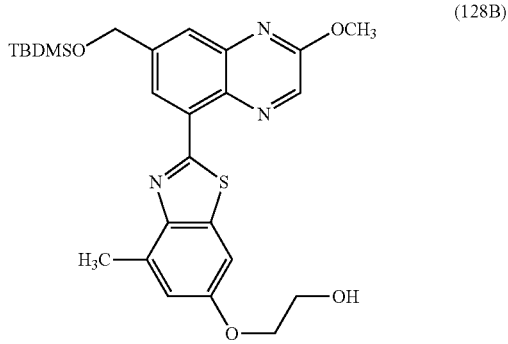 [SMILES: COc1cnc2c(-c3nc4c(C)cc(OCCO)cc4s3)cc(CO[Si](C)(C)C(C)(C)C)cc2n1]
(128B)

To Intermediate 124E (50 mg, 0.116 mmol), Intermediate 128A (28.3 mg, 0.116 mmol) and [1,1'-bis(diphenylphosphino)ferrocene]dichloropalladium (II) complex with dichloromethane (1:1) (4.74 mg, 5.81 µmol) was added toluene (1.5 mL) and EtOH (0.5 mL). The mixture was sonicated for 1 min, and flushed with argon. To this was added sodium carbonate (0.116 mL, 2M, 0.232 mmol). The reaction mixture was heated in a microwave reactor at 130° C. for 30 min. The crude reaction mixture was directly loaded to 12 g ISCO column eluted with 0% to 100% EtOAc in hexanes over 15 min. The desired fractions were combined and concentrated to yield Intermediate 128B (80 mg, 0.109 mmol, 94% yield) as a yellow solid. $^1$H NMR (400 MHz, chloroform-d) δ 8.80 (d, J=2.0 Hz, 1H), 8.58 (s, 1H), 7.94-7.90 (m, 1H), 7.27 (s, 1H), 6.96 (dd, J=2.4, 0.9 Hz, 1H), 5.05 (s, 2H), 4.20-4.16 (m, 2H), 4.15 (s, 3H), 4.05-3.98 (m, 2H), 2.82 (s, 3H), 1.04 (s, 9H), 0.21-0.20 (m, 6H). LC-MS: method C, RT=3.07 min, MS (ESI) m/z: 512 (M+H)$^+$.

Intermediate 128C 2-(2-(7-((tert-butyldimethylsilyloxy)methyl)-2-methoxyquinoxalin-5-yl)-4-methylbenzo[d]thiazol-6-yloxy)ethyl carbonochloridate

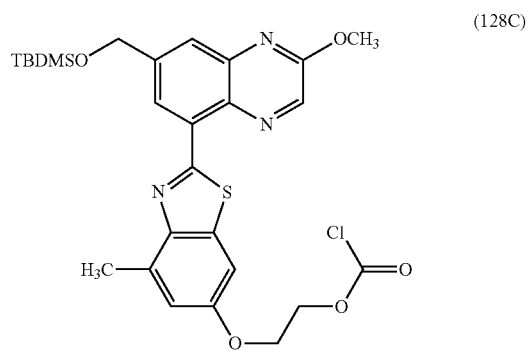 [SMILES: COc1cnc2c(-c3nc4c(C)cc(OCCOC(=O)Cl)cc4s3)cc(CO[Si](C)(C)C(C)(C)C)cc2n1]
(128C)

To a solution of Intermediate 128B (110 mg, 0.193 mmol) and DIEA (0.169 ml, 0.967 mmol) in THF (2 ml) was added 15% phosgene in toluene (0.409 ml, 0.580 mmol). The reaction mixture was stirred at room temperature overnight and then concentrated to give Intermediate 128C which was used for next step without purification. LC-MS: method C, RT=3.64 min, MS (ESI) m/z: 574 (M+H)$^+$.

Intermediate 128D 2-(2-(7-((tert-butyldimethylsilyloxy)methyl)-2-methoxyquinoxalin-5-yl)-4-methylbenzo[d]thiazol-6-yloxy)ethyl 6-methylpyridin-3-ylcarbamate

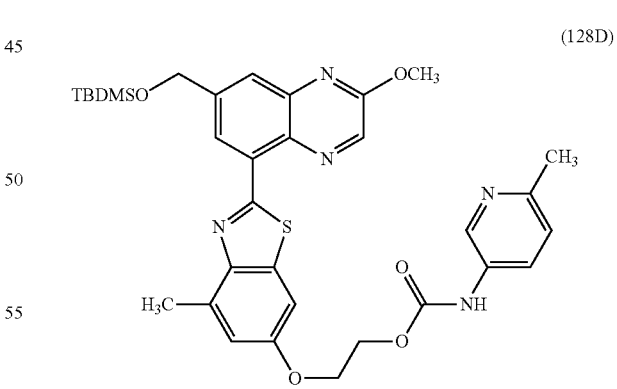
(128D)

To a solution of Intermediate 128C (16.5 mg, 0.029 mmol) in DCM (1 mL) was added 6-methylpyridin-3-amine (9.32 mg, 0.086 mmol) in DCM (0.5 mL) and DIEA (0.050 mL, 0.287 mmol). The mixture was stirred at room temperature for 1 h. The reaction mixture was loaded to a 12 g ISCO column, eluted with 0-100% EtOAc in hexane for 15 min. The desired fraction was collected and concentrated to give Intermediate 128D (18 mg, 0.028 mmol, 97% yield). $^1$H NMR (400 MHz, chloroform-d) δ 8.81 (d, J=2.0 Hz, 1H), 8.58 (s, 1H), 8.39 (d, J=2.4 Hz, 1H), 7.92-7.90 (m, 1H), 7.85 (br. s., 1H), 7.26 (s, 1H), 7.13 (d, J=8.4 Hz, 1H), 6.97 (dd, J=2.4, 0.9 Hz, 1H), 6.82-6.69 (m, 1H), 5.05 (s, 2H), 4.62-4.54 (m, 2H), 4.34-4.28 (m, 2H), 4.15 (s, 3H), 2.82 (s, 3H), 2.52 (s, 3H), 1.07-1.01 (m, 9H), 0.22-0.18 (m, 6H). LC-MS: method C, RT=2.48 min, MS (ESI) m/z: 646 (M+H)+.

Example 128

To a solution of Intermediate 128D (18 mg, 0.028 mmol) in DCM (1 mL) was added TBAF (0.139 mL, 0.139 mmol), the mixture was stirred at room temperature for 1 h. Solvent was removed, the residual was dissolved in DMSO and purified via preparative LC/MS (method D, 30-70% B over 20 min., then a 5-min hold at 100% B). Fractions containing the desired product were combined and dried via centrifugal evaporation to give Example 128 (3.0 mg, 5.53 mol, 19.84% yield). $^1$H NMR (500 MHz, DMSO-$d_6$) δ 10.05 (br. s., 1H), 8.73 (s, 1H), 8.71 (br. s., 1H), 8.55 (br. s., 1H), 7.92 (d, J=15.3 Hz, 1H), 7.86 (br. s., 1H), 7.55 (br. s., 1H), 7.32 (br. s., 1H), 7.02 (br. s., 1H), 4.81 (br. s., 2H), 4.48 (br. s., 2H), 4.33 (br. s., 2H), 4.08 (s, 3H), 2.88 (s, 3H), 2.43 (br. s., 3H). LC-MS: method C, RT=1.49 min, MS (ESI) m/z: 532.20 (M+H)+. Analytical HPLC purity (method B): 98%.

Example 129

2-(2-(7-(hydroxymethyl)-2-methoxyquinoxalin-5-yl)-4-methylbenzo[d]thiazol-6-yloxy)ethyl 2-methylpyridin-4-ylcarbamate (129)

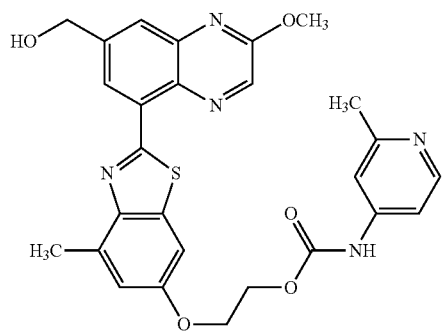

Intermediate 129A 2-(2-(7-((tert-butyldimethylsilyloxy)methyl)-2-methoxyquinoxalin-5-yl)-4-methylbenzo[d]thiazol-6-yloxy)ethyl 2-methylpyridin-4-ylcarbamate (129A)

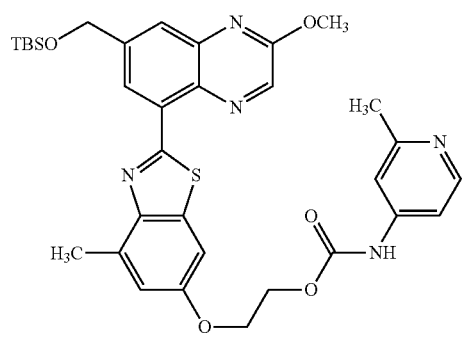

To a solution of Intermediate 128C (16.5 mg, 0.029 mmol) in DCM (1 mL) was added 2-methylpyridin-4-amine (9.32 mg, 0.086 mmol) in DCM (0.5 mL) and DIEA (0.050 mL, 0.287 mmol). The mixture was stirred at room temperature for 1 h. LCMS indicated a completion of reaction. The reaction mixture was loaded to a 12 g ISCO column, eluted with 0-100% EtOAc in hexanes for 15 min. The desired fraction was collected and concentrated to give Intermediate 129A (17 mg, 0.026 mmol, 92% yield). $^1$H NMR (400 MHz, chloroform-d) δ 8.81 (d, J=2.0 Hz, 1H), 8.59 (s, 1H), 8.37 (d, J=4.2 Hz, 1H), 7.94-7.90 (m, 1H), 7.29-7.22 (m, 1H), 7.14 (d, J=4.2 Hz, 1H), 6.97 (dd, 0.9 Hz, 1H), 6.87 (br. s., 1H), 5.05 (s, 2H), 4.64-4.56 (m, 2H), 4.35-4.29 (m, 2H), 4.15 (s, 3H), 2.82 (s, 3H), 2.53 (s, 3H), 1.06-1.01 (m, 10H), 0.23-0.18 (m, 6H). LC-MS: method C, RT=2.46 min, MS (ESI) m/z: 646 (M+H)+.

Example 129

To a solution of Intermediate 129A (17 mg, 0.026 mmol) in DCM (1 mL) was added TBAF (0.132 mL, 0.132 mmol), the mixture was stirred at room temperature for 1 h. Solvent was removed and the residual was dissolved in DMSO and purified via preparative LCMS (method D, 30-70% B over 25 min., then a 5-min hold at 100% B). Fractions containing the desired product were combined and dried via centrifugal evaporation to give Example 129 (2.9 mg, 5.40 mol, 20.52% yield). $^1$H NMR (500 MHz, DMSO-$d_6$) δ 8.70 (d, J=9.2 Hz, 2H), 8.25 (br. s., 1H), 7.88 (s, 1H), 7.53 (s, 1H), 7.31 (d, J=16.2 Hz, 2H), 7.01 (s, 1H), 4.81 (d, J=4.3 Hz, 2H), 4.50 (br. s., 2H), LC-MS: method C, RT=1.55 min, MS (ESI) m/z: 532.20 (M+H)+. Analytical HPLC purity (method B): 99%.

Example 130

5-(benzofuran-2-yl)-2-methoxy-7-methyl-1,6-naphthyridine (130)

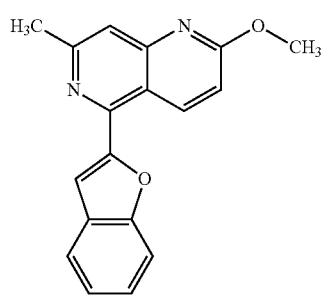

Intermediate 130A: (E)-2-(2-(dimethylamino)prop-1-en-1-yl)-6-methoxynicotinonitrile (130A)

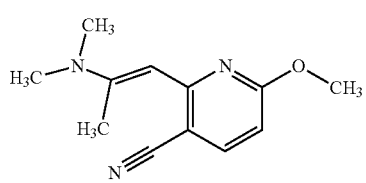

6-methoxy-2-methylnicotinonitrile (200 mg, 1.350 mmol) was dissolved in DMF (1350 μL) and N,N-dimethylacetamide dimethyl acetal (987 μL, 6.75 mmol) and heated to 150° C. for 24 hours. The reaction mixture was cooled to ambient temperature and concentrated in vacuo. The crude material was purified by column chromatography (ISCO, 12 g silica gel column, 17 minute gradient from 0 to 100% EtOAc in hexanes) to give Intermediate 130A (177.9 mg, 0.819 mmol, 60.7%) as a yellow solid: LC-MS: Ketone product mass observed, Method H, RT=0.72 min, MS (ESI) m/z: 191.2 (M+H)$^+$.

Intermediate 130B:
2-methoxy-7-methyl-1,6-naphthyridin-5-ol

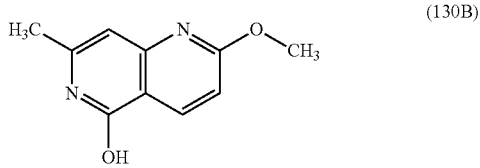

Intermediate 130A (178 mg, 0.819 mmol) was dissolved in CHCl$_3$ (6145 μL), AcOH (1024 μL), and HBr (1024 μL) and stirred for 18 hours. The reaction mixture was diluted with 1 N NaOH and extracted thrice with EtOAc. The combined organic layers were washed with brine, dried (Na$_2$SO$_4$), filtered, and concentrated in vacuo. The crude material was purified by column chromatography (ISCO, 24 g silica gel column, 19 minute gradient from 0 to 100% EtOAc in hexanes) to give Intermediate 130B (51.6 mg, 0.271, 33.1%) as a white solid: $^1$H NMR (400 MHz, METHANOL-d$_4$) δ 8.34 (d, J=8.8 Hz, 1H), 6.80 (d, J=8.8 Hz, 1H), 6.44 (br. s., 1H), 4.02 (d, J=2.8 Hz, 3H), 2.33 (s, 3H); LC-MS: Method H, RT=0.7 min, MS (ESI) m/z: 191.2 (M+H)$^+$.

Intermediate 130C: 2-methoxy-7-methyl-1,6-naphthyridin-5-yltrifluoromethanesulfonate

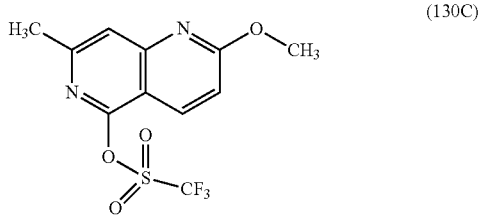

Intermediate 130B (0.0516 g, 0.271 mmol), pyridine (0.055 mL, 0.678 mmol), and DIEA (0.104 mL, 0.597 mmol) were dissolved in DCM (13.56 mL). Triflic anhydride (0.092 mL, 0.543 mmol) was added and the reaction mixture stirred for 1.5 hours. The reaction mixture was concentrated in vacuo. 2D TLC was used to determine if the triflate product was unstable to silica gel and there was a slight bit of decomposition observed. Therefore, the reaction mixture was filtered through a pad of silica gel in a fritted funnel with rapid DCM elution and concentrated in vacuo to give Intermediate 130C (77.5 mg, 0.240 mmol, 89%) as a red oil: $^1$H NMR (400 MHz, CHLOROFORM-d) δ 8.14 (d, J=9.0 Hz, 1H), 7.52 (s, 1H), 7.00 (d, J=9.0 Hz, 1H), 4.09 (s, 3H), 2.63 (s, 3H); LC-MS: Method H, RT=1.10 min, MS (ESI) m/z: 323.0 (M+H)$^+$.

Example 130

Intermediate 130C (30 mg, 0.093 mmol) and benzofuran-2-ylboronic acid (22.61 mg, 0.140 mmol) were dissolved in toluene (698 μL) and EtOH (233 μL). PdCl$_2$(dppf)-CH$_2$Cl$_2$ (4.56 mg, 5.59 μmol) was added and the reaction mixture was degassed by bubbling with argon for 15 minutes. Sodium carbonate (2 M, 55.9 μL, 0.112 mmol) was added and the reaction mixture was degassed for 5 minutes, then sealed and heated to 90° C. in the microwave for 30 minutes. The reaction mixture was purified by preparative HPLC (Method D, 30 to 80% B in 10 minutes) to give Example 130 (9.8 mg, 0.033 mmol, 35.2%): $^1$H NMR (500 MHz, METHANOL-d$_4$) δ 8.95 (d, J=9.4 Hz, 1H), 7.73 (d, J=7.7 Hz, 1H), 7.64 (d, J=8.3 Hz, 1H), 7.57 (s, 1H), 7.51 (s, 1H), 7.40 (t, J=7.3 Hz, 1H), 7.35-7.29 (m, 1H), 7.02 (d, J=9.4 Hz, 1H), 4.11 (s, 3H), 2.73 (s, 3H); LC-MS: Method H, RT=0.88 min, MS (ESI) m/z: 291.2 (M+H)$^+$. Analytical HPLC Method B: 97.2% purity.

Example 131

5-(benzofuran-2-yl)-7-methyl-2-vinylquinoxaline

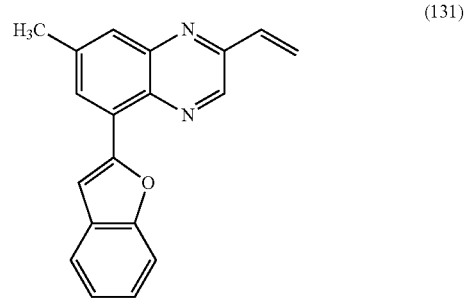 [SMILES: C=Cc1cnc2c(-c3cc4ccccc4o3)cc(C)cc2n1]

Intermediate 131A:
2-(benzyloxy)-5-iodo-7-methylquinoxaline

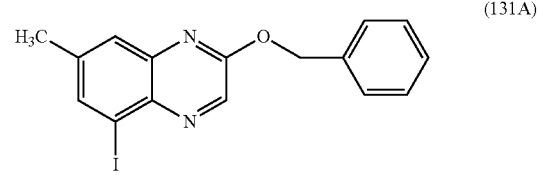 [SMILES: Cc1cc(I)c2ncc(OCc3ccccc3)nc2c1]

Intermediate I-14 (200 mg, 0.699 mmol) was suspended in toluene (4661 μL). Silver oxide (405 mg, 1.748 mmol) then benzyl bromide (83 μL, 0.699 mmol) were added and the reaction mixture was stirred for 1 week. The reaction mixture was filtered to remove the silver salts and concentrated in vacuo. The material was purified by column chromatography (ISCO, 12 g silica gel column, 15 minute gradient from 0 to 100% EtOAc in hexanes) to give Intermediate 131A (78.8 mg, 0.209 mmol, 30%) as an off-white solid: $^1$H NMR (400 MHz, CHLOROFORM-d) δ 8.47 (s, 1H), 8.01 (d, J=1.5 Hz, 1H), 7.64 (d, J=0.8 Hz, 1H), 7.52 (d, J=6.8 Hz, 2H), 7.45-7.32 (m, 3H), 5.54 (s, 2H), 2.52 (s, 3H); LC-MS: Method H, RT=1.22 min, MS (ESI) m/z: 377.0 (M+H)⁺.

Intermediate 131B: 5-(benzofuran-2-yl)-2-(benzyloxy)-7-methylquinoxaline

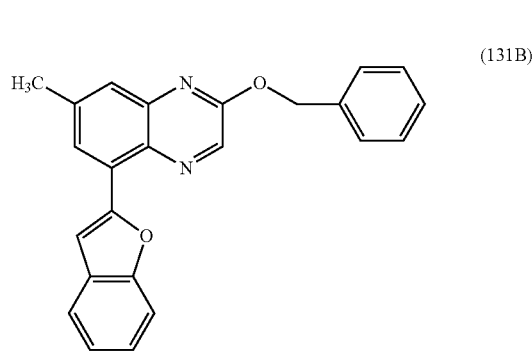 [SMILES: Cc1cc(-c2cc3ccccc3o2)c2ncc(OCc3ccccc3)nc2c1]

(131B)

Intermediate 131A (78.8 mg, 0.209 mmol) and benzofuran-2-ylboronic acid (50.9 mg, 0.314 mmol) were dissolved in toluene (1571 μL) and EtOH (524 μL). PdCl₂(dppf)-CH₂Cl₂ (10.26 mg, 0.013 mmol) was added and the reaction mixture was degassed by bubbling with argon for 15 minutes. Sodium carbonate (2 M, 126 μL, 0.251 mmol) was added and the reaction mixture was degassed for 5 minutes, then sealed and heated to 90° C. in the microwave for 30 minutes. The reaction mixture was diluted with EtOAc and filtered through a micron filter and concentrated in vacuo. The crude material was purified by column chromatography (ISCO, 12 g silica gel column, 17 minute gradient from 0 to 100% EtOAc in hexanes) to give Intermediate 131B (67.7 mg, 0.185 mmol, 88%) as a yellow solid: ¹H NMR (400 MHz, CHLOROFORM-d) δ 8.56 (s, 1H), 8.15 (d, J=2.0 Hz, 1H), 8.08 (d, J=0.8 Hz, 1H), 7.69-7.63 (m, 2H), 7.58-7.53 (m, 3H), 7.45-7.40 (m, 2H), 7.39-7.28 (m, 3H), 5.56 (s, 2H), 2.63 (s, 3H); LC-MS: Method H, compound did not ionize.

Intermediate 131C: 5-(benzofuran-2-yl)-7-methyl-3,4-dihydroquinoxalin-2(1H)-one

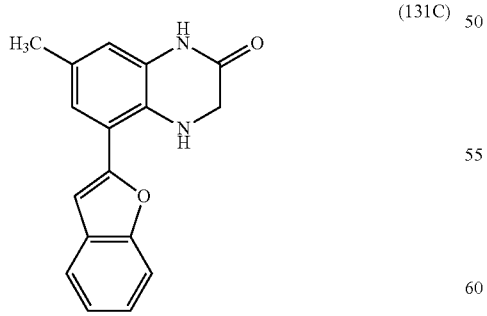

(131C)

Intermediate 131B (67.7 mg, 0.185 mmol) was partially dissolved in MeOH (1848 μL) and EtOAc (1848 μL). Palladium on carbon (19.66 mg, 0.018 mmol) was added. The reaction mixture was purged with hydrogen for 5 minutes and sealed under a hydrogen balloon for 2.5 hours. The reaction mixture was diluted with EtOAc, filtered through a micron filter, and concentrated in vacuo to give Intermediate 131C, which was used directly in the subsequent step: LC-MS: Method H, RT=0.97 min, MS (ESI) m/z: 279.1 (M+H)⁺.

Intermediate 131D: 5-(benzofuran-2-yl)-7-methylquinoxalin-2(1H)-one

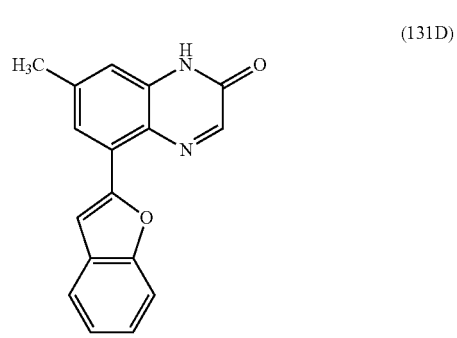 [SMILES: Cc1cc(-c2cc3ccccc3o2)c2ncc(=O)[nH]c2c1]

(131D)

Intermediate 131C (51 mg, 0.183 mmol) was suspended in MeOH (533 μL). NaOH (550 μL, 0.550 mmol) then H₂O₂ (96 μL, 1.100 mmol) were added and the reaction mixture was stirred for 18 hours. More H₂O₂ (96 μL, 1.100 mmol) was added and the reaction mixture was stirred for 24 hours. The reaction mixture was diluted with water and extracted with EtOAc. The organic layer was further washed with brine, dried (Na₂SO₄), filtered, and concentrated in vacuo to give Intermediate 131D (34.6 mg, 0.125 mmol, 68.3%) as a yellow solid: ¹H NMR (400 MHz, CHLOROFORM-d) δ 10.41 (br. s., 1H), 8.40 (s, 1H), 7.98 (d, J=1.0 Hz, 1H), 7.92 (d, J=1.3 Hz, 1H), 7.67 (d, J=7.5 Hz, 1H), 7.56 (d, J=8.3 Hz, 1H), 7.37-7.32 (m, 2H), 7.00 (s, 1H), 2.57 (s, 3H); LC-MS: Method H, RT=1.01 min, MS (ESI) m/z: 277.3 (M+H)⁺.

Intermediate 131E: 5-(benzofuran-2-yl)-7-methylquinoxalin-2-yl trifluoromethanesulfonate

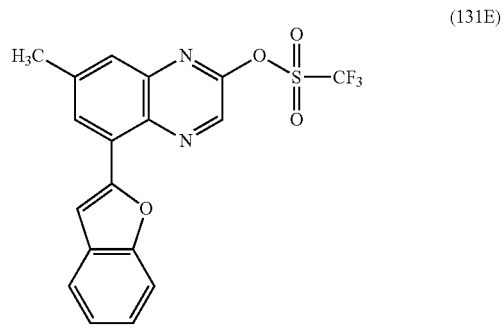 [SMILES: Cc1cc(-c2cc3ccccc3o2)c2ncc(OS(=O)(=O)C(F)(F)F)nc2c1]

(131E)

Intermediate 131D (26 mg, 0.094 mmol), pyridine (19.03 μL, 0.235 mmol), and DIEA (36.2 μL, 0.207 mmol) were dissolved in DCM (4705 Triflic anhydride (31.8 μL, 0.188 mmol) was added and the reaction mixture was stirred for 2 hours. The reaction mixture was concentrated in vacuo. The reaction mixture was filtered through a pad of silica gel in a fritted funnel with rapid DCM elution to give Intermediate 131E (24.8 mg, 0.061 mmol, 64.5%) as an orange solid: LC-MS: Method H, RT=1.28 min, MS (ESI) m/z: 409.0 (M+H)+.

Example 131

Intermediate 131E (24.8 mg, 0.061 mmol) and vinylboronic acid pinacol ester (21.09 μL, 0.121 mmol) were dissolved in toluene (455 μL) and EtOH (152 μL). PdCl$_2$(dppf)-CH$_2$Cl$_2$ (2.98 mg, 3.64 μmol) was added and the reaction mixture was degassed by bubbling with argon for 15 minutes. Sodium carbonate (2 M, 36.4 μL, 0.073 mmol) was added and the reaction mixture was degassed for 5 minutes, then sealed and heated to 90° C. in the microwave for 30 minutes. The reaction mixture was diluted with EtOAc and filtered through a micron filter and concentrated in vacuo. The crude material was purified by preparative HPLC (Method D, 45-75% B in 10 minutes) to give Example 131 (2.6 mg, 0.00874 mmol, 14%): $^1$H NMR (500 MHz, METHANOL-d$_4$) δ 9.11 (s, 1H), 8.28 (d, J=1.7 Hz, 1H), 8.11 (s, 1H), 7.77 (s, 1H), 7.67 (d, J=7.7 Hz, 1H), 7.56 (d, J=8.3 Hz, 1H), 7.33 (t, J=7.2 Hz, 1H), 7.27-7.21 (m, 1H), 7.05 (dd, J=17.9, 11.0 Hz, 1H), 6.51 (d, J=17.9 Hz, 1H), 5.85 (d, J=11.3 Hz, 1H), 2.66 (s, 3H); LC-MS: Method H, RT=1.24 min, MS (ESI) m/z: 287.2 (M+H)+. Analytical HPLC Method B: 97.3% purity.

Example 132

5-(benzofuran-2-yl)-2-ethyl-7-methylquinoxaline

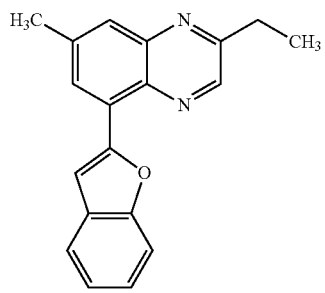

(132)

Example 131 (1.4 mg, 4.89 μmol) (92793-013-01) was dissolved in MeOH (244 μL). Palladium on carbon (0.520 mg, 0.489 μmol) was added and the reaction mixture was sealed under an atmosphere of hydrogen for 30 minutes. The reaction mixture was filtered and concentrated in vacuo. The crude material was purified by preparative HPLC (Method A, 30 to 100% B in 20 minutes; with a flow rate of 40 mL/min). The desired fractions were concentrated and lyophilized to give Example 132 (0.69 mg, 0.00235 mmol, 48.2% yield) as a yellow solid: $^1$H NMR (400 MHz, CHLOROFORM-d) δ 8.87 (s, 1H), 8.31 (d, J=1.8 Hz, 1H), 8.15 (d, J=0.8 Hz, 1H), 7.85 (d, J=0.8 Hz, 1H), 7.68 (d, J=7.8 Hz, 1H), 7.60-7.55 (m, 1H), 7.37-7.31 (m, 1H), 7.29-7.23 (m, 1H), 3.12 (q, J=7.7 Hz, 2H), 2.67 (s, 3H), 1.47 (t, J=7.7 Hz, 3H); LC-MS: Method H, RT=1.25 min, MS (ESI) m/z: 289.2 (M+H)+. Analytical HPLC Method A: 98.4% purity.

Example 133

5-(benzofuran-2-yl)-2-(difluoromethoxy)-8-methylquinoxaline

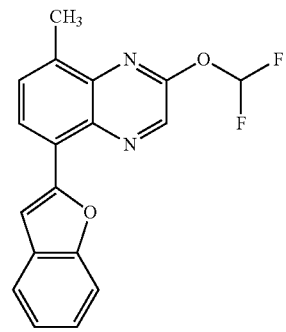

(133)

Intermediate 133A:
6-bromo-3-methyl-2-nitroaniline

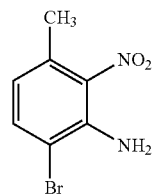

(133A)

3-Methyl-2-nitroaniline (250 mg, 1.643 mmol) and NBS (292 mg, 1.643 mmol) were dissolved in AcOH (8216 μL) and heated to 120° C. for 4 hours. The reaction mixture was cooled to ambient temperature and diluted with H$_2$O (50 mL). The material was extracted with EtOAc. The organic layer was washed twice with saturated NaHCO$_3$, then brine, dried (Na$_2$SO$_4$), filtered, and concentrated in vacuo. The crude material was purified by column chromatography (ISCO, 40 g silica gel column, 19 minute gradient from 0 to 100% EtOAc in hexanes) to give Intermediate 133A (302.8 mg, 1.311 mmol, 80%) as an orange solid: $^1$H NMR (400 MHz, CHLOROFORM-d) δ 7.43 (d, J=9.0 Hz, 1H), 6.59 (d, J=8.8 Hz, 1H), 4.77 (br. s., 2H), 2.47 (s, 3H); LC-MS: Method H, RT=0.94 min, MS (ESI) m/z: 231/233 (M+H)+.

Intermediate 133B:
3-bromo-6-methylbenzene-1,2-diamine

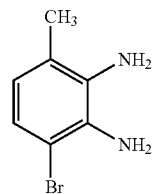

(133B)

Intermediate 133A (302.8 mg, 1.311 mmol) was dissolved in MeOH (8961 μL) and THF (1120 μL). Ammonium chloride (1402 mg, 26.2 mmol) and zinc (857 mg, 13.11 mmol) were added and the reaction mixture was heated to 40° C. for 1 hour. The reaction mixture was cooled to ambient temperature and concentrated in vacuo. The crude material was redissolved in EtOAc/saturated Sodium carbonate and allowed to stir vigorously for 15 minutes. The mixture was filtered through a sintered glass funnel. The organic layer was washed twice with water then brine, dried ($Na_2SO_4$), filtered, and concentrated in vacuo to give Intermediate 133B (257.8 mg, 1.282 mmol, 98%): $^1$H NMR (400 MHz, CHLOROFORM-d) δ 6.91 (d, J=8.2 Hz, 1H), 6.49 (d, J=8.8 Hz, 1H), 3.53 (br. s., 2H), 3.29 (br. s., 2H), 2.30 (s, 3H); LC-MS: Method H, RT=0.54 min, MS (ESI) m/z: 201/203 (M+H)$^+$.

Intermediate 133C:
3-(benzofuran-2-yl)-6-methylbenzene-1,2-diamine

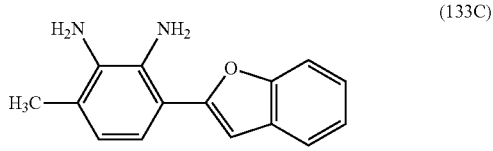 [SMILES: Cc1ccc(-c2cc3ccccc3o2)c(N)c1N]

(133C)

Intermediate 133B (257.8 mg, 1.282 mmol) and benzofuran-2-ylboronic acid (311 mg, 1.923 mmol) were dissolved in toluene (9616 μL) and EtOH (3205 μL). $PdCl_2$(dppf)-$CH_2Cl_2$ (62.8 mg, 0.077 mmol) was added and the reaction mixture was degassed by bubbling with argon for 15 minutes. Sodium carbonate (2 M, 769 μL, 1.539 mmol) was added and the reaction mixture was degassed for 5 minutes, then sealed and heated to 90° C. in the microwave for 60 minutes. The reaction mixture was diluted with EtOAc and filtered through a micron filter and concentrated in vacuo. The crude material was purified by column chromatography (ISCO, 40 g silica gel column, 19 minute gradient from 0 to 100% EtOAc in hexanes) to give Intermediate 133C (237.8 mg, 0.998 mmol, 78%) as a brown oil: $^1$H NMR (400 MHz, CHLOROFORM-d) δ 7.59-7.55 (m, 1H), 7.52-7.47 (m, 1H), 7.29-7.18 (m, 2H), 7.10 (d, J=8.3 Hz, 1H), 6.73-6.65 (m, 2H), 3.51 (br. s., 4H), 2.36 (s, 3H); LC-MS: Method H, The compound did not ionize.

Intermediate 133D: 5-(benzofuran-2-yl)-8-methylquinoxalin-2(1H)-one

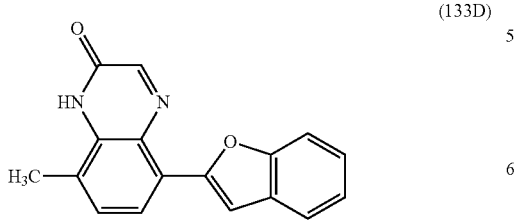

(133D)

Intermediate 133C (237.8 mg, 0.998 mmol) was dissolved in EtOH (2697 μL). Ethyl glyoxalate solution (50 wt %, 297 μL, 1.497 mmol) was added and the reaction mixture was heated to 80° C. and allowed to stir overnight. The reaction mixture was cooled to ambient temperature and filtered to collect the solid precipitate, which was washed with EtOH and collected to give Intermediate 133D (63.8 mg, 0.231 mmol, 23.1%) as an off-white solid mixture of regioisomers. The material was used as-is for the subsequent step: LC-MS: Method H, RT=0.94 min, MS (ESI) m/z: 277.1 (M+H)$^+$.

Example 133

Intermediate 133D (30 mg, 0.109 mmol) and $K_2CO_3$ (300 mg, 2.172 mmol) were dissolved in DMF (1086 μL) and heated to 100° C. for 5 min. Sodium 2-chloro-2,2-difluoroacetate (66.2 mg, 0.434 mmol) was added and the reaction mixture was heated for 2.5 hours. The reaction mixture was diluted with water and extracted thrice with DCM. The combined organic extracts were washed with brine, dried ($Na_2SO_4$), filtered, and concentrated in vacuo. The crude material was purified by preparative HPLC (Method D, 60 to 90% B in 25 minutes) then repurified by preparative HPLC (Method D, 55-80% B in 15 minutes) to give Example 133 (1.4 mg, 0.00417 mmol, 3.84%): $^1$H NMR (500 MHz, METHANOL-$d_4$) δ 8.62 (s, 1H), 8.24 (d, J=8.8 Hz, 1H), 8.02 (d, J=8.8 Hz, 1H), 7.91-7.59 (m, 3H), 7.36 (t, J=7.6 Hz, 1H), 7.32-7.27 (m, 1H), 7.19 (s, 1H), 2.97 (s, 3H); LC-MS: Method H, RT=1.17 min, MS (ESI) m/z: 327.1 (M+H)$^+$. Analytical HPLC Method B: 97.3% purity.

Example 134

8-(benzofuran-2-yl)-3-methoxy-6-methyl-1,7-naphthyridine\

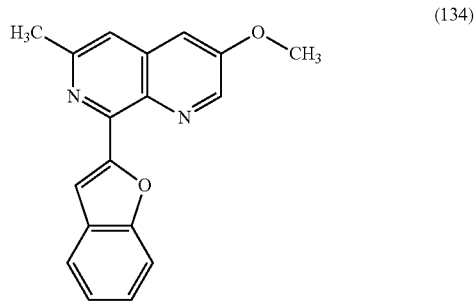

(134)

Intermediate 134A:
5-methoxy-3-methylpicolinonitrile

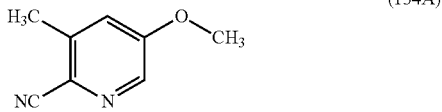

(134A)

5-Hydroxy-3-methylpicolinonitrile (0.25 g, 1.864 mmol) was suspended in DMF (12.43 mL). Cesium carbonate (1.518 g, 4.66 mmol) then iodomethane (0.146 mL, 2.330 mmol) were added and stirred for 3 hours. The reaction mixture was diluted with water and extracted with EtOAc. The organic layer was washed with brine, dried ($Na_2SO_4$), filtered, and concentrated in vacuo to give Intermediate 134A (252.7 mg, 1.706 mmol, 92%) as a light brown solid:

$^1$H NMR (400 MHz, CHLOROFORM-d) δ 8.21 (d, J=2.5 Hz, 1H), 7.07 (d, J=2.8 Hz, 1H), 3.91 (s, 3H), 2.54 (s, 3H); LC-MS: Method H, RT=0.71 min, MS (ESI) m/z: 149.2 (M+H)$^+$.

Intermediate 134B:
5-methoxy-3-(2-oxopropyl)picolinonitrile

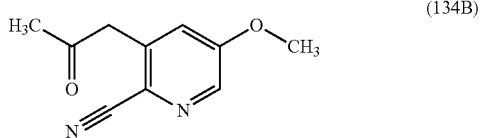
(134B)

Intermediate 134A (252.7 mg, 1.706 mmol) was dissolved in DMF (1706 μL) and N,N-dimethylacetamide dimethyl acetal (1247 μL, 8.53 mmol) and heated to 150° C. for 18 hours. More N,N-dimethylacetamide dimethylacetal (0.5 mL) was added and heating continued for 24 hours. The reaction mixture was cooled to ambient temperature and concentrated in vacuo. The crude material was purified by preparative HPLC (Method A, 20 to 100% B in 17 minutes) to give Intermediate 134B (81.8 mg, 0.430 mmol, 25.2%) as a brown oil: $^1$H NMR (400 MHz, CHLOROFORM-d) δ 8.30 (d, J=2.8 Hz, 1H), 7.11 (d, J=2.8 Hz, 1H), 3.98 (s, 2H), 3.92 (s, 3H), 2.35 (s, 3H); LC-MS: Method H, RT=0.64 min, MS (ESI) m/z: 191.2 (M+H)$^+$.

Intermediate 134C:
3-methoxy-6-methyl-1,7-naphthyridin-8-ol

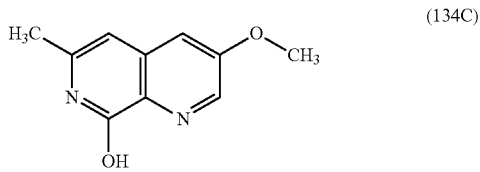
(134C)

Intermediate 134B (81.8 mg, 0.430 mmol) was dissolved in CHCl$_3$ (3226 μL), AcOH (538 μL), and HBr (538 μL) at and stirred overnight. The reaction mixture was diluted with 1 N NaOH and extracted thrice with EtOAc. The combined organic layers were washed with brine, dried (Na$_2$SO$_4$), filtered, and concentrated in vacuo. The crude material was purified by preparative HPLC (Method A, 20 to 100% B in 17 minutes) to give Intermediate 134C (7.6 mg, 0.040 mmol, 9.3%) as a brown solid: $^1$H NMR (400 MHz, METHANOL-d$_4$) δ 8.34 (d, J=8.8 Hz, 1H), 6.80 (d, J=8.8 Hz, 1H), 6.44 (br. s., 1H), 4.02 (d, J=2.8 Hz, 3H), 2.33 (s, 3H); LC-MS: Method H, RT=0.55 min, MS (ESI) m/z: 191.2 (M+H)$^+$.

Intermediate 134D:
3-methoxy-6-methyl-1,7-naphthyridin-8-yl trifluoromethanesulfonate

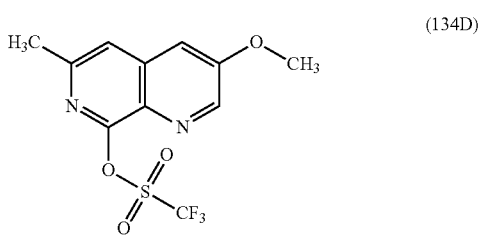
(134D)

Intermediate 134C (10.1 mg, 0.053 mmol), pyridine (21.47 μL, 0.266 mmol), and DIEA (20.40 μL, 0.117 mmol) were dissolved in DCM (2655 μL). Triflic anhydride (35.9 μL, 0.212 mmol) was added and the reaction mixture was stirred for 45 minutes. More triflic anhydride (35.9 μL, 0.212 mmol) was added and stirring continued for 30 minutes. The reaction mixture was filtered through a pad of silica gel in a fritted funnel with rapid DCM elution to give Intermediate 134D (11.8 mg, 0.037 mmol, 69%) as a red oil: LC-MS: Method H, RT=1.01 min, MS (ESI) m/z: 323.0 (M+H)$^+$.

Example 134

Intermediate 134D (11.8 mg, 0.037 mmol) and benzofuran-2-ylboronic acid (7.12 mg, 0.044 mmol) were dissolved in DMF (366 μL). PdCl$_2$(dppf)-CH$_2$Cl$_2$ (1.794 mg, 2.197 μmol) was added and the reaction mixture was degassed by bubbling with argon for 15 minutes. Sodium carbonate (2 M, 21.97 μL, 0.044 mmol) was added and the reaction mixture was degassed for 5 minutes, then sealed and heated to 90° C. in the microwave for 30 minutes. The reaction mixture was diluted with EtOAc and filtered through a micron filter and concentrated in vacuo. The crude material was purified by preparative HPLC (Method D, 0 to 40% B in 10 minutes) to give Example 134 (2.0 mg, 0.00675 mmol, 18.4%): $^1$H NMR (500 MHz, METHANOL-d$_4$) δ 8.82 (d, J=2.8 Hz, 1H), 8.57 (s, 1H), 7.79 (d, J=8.0 Hz, 1H), 7.69 (d, J=8.3 Hz, 1H), 7.64 (s, 1H), 7.54 (d, J=2.8 Hz, 1H), 7.47 (t, J=7.7 Hz, 1H), 7.37-7.30 (m, 1H), 4.07 (s, 3H), 2.82 (s, 3H); LC-MS: Method H, RT=0.78 min, MS (ESI) m/z: 291.1 (M+H)$^+$. Analytical HPLC Method B: 98% purity.

Example 135

5-(benzofuran-2-yl)-2-(furan-3-yl)-7-methylquinoxaline

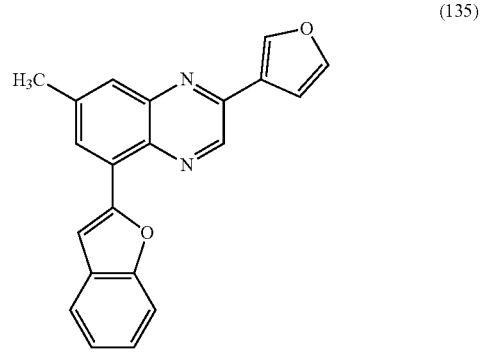 [SMILES: Cc1cc(-c2cc3ccccc3o2)c2ncc(-c3ccoc3)nc2c1]
(135)

Intermediate 135A:
5-bromo-7-methylquinoxalin-2-yl trifluoromethanesulfonate

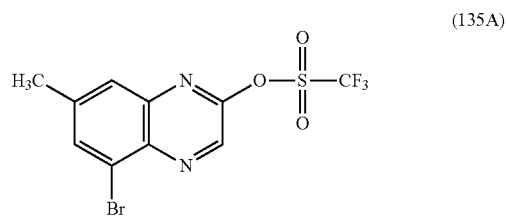 [SMILES: Cc1cc(Br)c2ncc(OS(=O)(=O)C(F)(F)F)nc2c1]
(135A)

Intermediate I-1F (0.2 g, 0.837 mmol), pyridine (0.338 mL, 4.18 mmol), and DIEA (0.321 mL, 1.840 mmol) were dissolved in DCM (41.8 mL). Triflic anhydride (0.565 mL, 3.35 mmol) was added and the reaction mixture was stirred for 1.5 hours. The reaction mixture was concentrated in vacuo. The reaction mixture was filtered through a pad of silica gel in a fritted funnel with rapid DCM elution to give Intermediate 135A (137.3 mg, 0.370 mmol, 44.2%) as a red oil: $^1$H NMR (400 MHz, CHLOROFORM-d) δ 8.78 (s, 1H), 8.04 (d, J=1.5 Hz, 1H), 7.83 (s, 1H), 2.62 (s, 3H); LC-MS: Method H, RT=1.10 min, The compound did not ionize.

Intermediate 135B:
5-bromo-2-(furan-3-yl)-7-methylquinoxaline

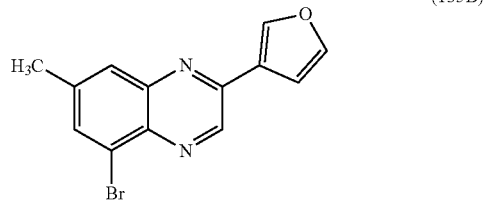

(135B)

Intermediate 135A (34.3 mg, 0.092 mmol) and furan-3-ylboronic acid (10.34 mg, 0.092 mmol) were dissolved in DMF (924 μL). PdCl$_2$(dppf)-CH$_2$Cl$_2$ (4.53 mg, 5.55 μmol) was added and the reaction mixture was degassed by bubbling with argon for 15 minutes. Sodium carbonate (2 M, 55.5 μL, 0.111 mmol) was added and the reaction mixture was degassed for 5 minutes, then sealed and heated to 90° C. in the microwave for 30 minutes. The reaction mixture was diluted with EtOAc and filtered through a micron filter and concentrated in vacuo. The crude material was purified by preparative HPLC (Method A, 20 to 100% B in 15 minutes), to give Intermediate 135B (2.9 mg, 0.010 mmol, 10.9%) as a brown solid: $^1$H NMR (400 MHz, CHLOROFORM-d) δ 9.07 (s, 1H), 8.24 (s, 1H), 7.87 (d, J=1.5 Hz, 1H), 7.83 (s, 1H), 7.59 (t, J=1.6 Hz, 1H), 7.15-7.11 (m, 1H), 2.58 (s, 3H); LC-MS: Method H, The compound did not ionize.

Example 135

Intermediate 135B (2.9 mg, 10.03 μmol) and benzofuran-2-ylboronic acid (2.437 mg, 0.015 mmol) were dissolved in toluene (752 μL) and EtOH (251 μL). PdCl$_2$(dppf)-CH$_2$Cl$_2$ (0.491 mg, 0.602 μmol) was added and the reaction mixture was degassed by bubbling with argon for 15 minutes. Sodium carbonate (2 M, 6.02 μL, 0.012 mmol) was added and the reaction mixture was degassed for 5 minutes, then sealed and heated to 90° C. in the microwave for 30 minutes. The reaction mixture was diluted with EtOAc and filtered through a micron filter and concentrated in vacuo. The crude material was purified by preparative HPLC (Method D, 55 to 90% B in 10 minutes) to give 135 (1.1 mg, 0.0032 mmol, 31.9%): $^1$H NMR (500 MHz, METHANOL-d$_4$) δ 9.19 (s, 1H), 8.38 (s, 1H), 8.28 (s, 1H), 8.13 (s, 1H), 7.82 (s, 1H), 7.71-7.64 (m, 2H), 7.57 (d, J=8.3 Hz, 1H), 7.33 (t, J=7.6 Hz, 1H), 7.28-7.23 (m, 1H), 7.20 (s, 1H), 2.67 (s, 3H); LC-MS: Method H, RT=1.28 min, MS (ESI) m/z: 327.1 (M+H)$^+$. Analytical HPLC Method B: 95% purity.

Example 136

2-(2-(difluoromethoxy)-7-methylquinoxalin-5-yl)-5,6-dihydro-4H-cyclopenta[d]thiazole

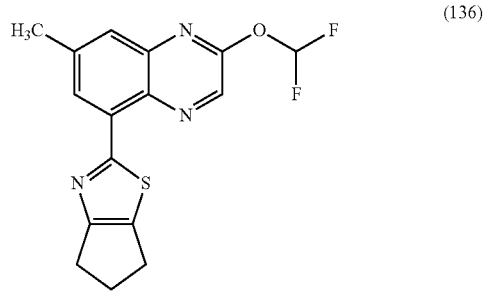 [SMILES: Cc1cc(-c2nc3c(s2)CCC3)c2ncc(OC(F)F)nc2c1]

(136)

Intermediate 136A: 2-bromo-5,6-dihydro-4H-cyclopenta[d]thiazole

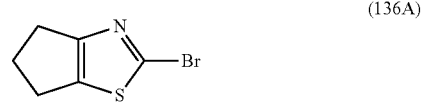

(136A)

5,6-Dihydro-4H-cyclopenta[d]thiazol-2-amine, HCl (50 mg, 0.283 mmol) and isoamyl nitrite (41.9 μL, 0.311 mmol) were dissolved in MeCN (1132 μL). Copper(II) bromide (60.9 mg, 0.425 mmol) was added portionwise over 1 hour. After an additional hour, the reaction mixture was diluted with water and extracted with DCM. The DCM layer was washed with brine, dried (Na$_2$SO$_4$), filtered, and concentrated in vacuo to give Intermediate 136A, which was volatile and was used as-is for the next reaction: LC-MS: Method H, RT=0.99 min, MS (ESI) m/z: 204/206 (M+H)$^+$.

Example 136

Intermediate I-1 (15 mg, 0.045 mmol) and Intermediate 136A (13.66 mg, 0.067 mmol) were dissolved in DMF (446 μL). PdCl$_2$(dppf)-CH$_2$Cl$_2$ (2.187 mg, 2.68 μmol) was added and the reaction mixture was degassed by bubbling with argon for 15 minutes. Sodium carbonate (2 M, 26.8 μL, 0.054 mmol) was added and the reaction mixture was degassed for 5 minutes, then sealed and heated to 100° C. in the microwave for 30 minutes. More PdCl$_2$(dppf)-CH$_2$Cl$_2$ (2.187 mg, 2.68 μmol) and Sodium carbonate (2 M, 26.8 μL, 0.054 mmol) were added and the reaction mixture was heated to 120° C. in the microwave for 30 minutes. The compound was diluted with DMF, filtered, and purified by preparative HPLC (Method D, 35 to 80% B in 10 minutes) then repurified by preparative HPLC (Method D, 45 to 80% B in 20 minutes) to give Example 136 (1.4 mg, 0.00403 mmol, 9.0%): $^1$H NMR (500 MHz, METHANOL-d$_4$) δ 8.64 (s, 1H), 8.42 (d, J=1.9 Hz, 1H), 7.83-7.51 (m, 2H), 3.03 (t, J=7.2 Hz, 2H), 2.95 (t, J=7.4 Hz, 2H), 2.63 (s, 3H), 2.62-2.53 (m, 2H); LC-MS: Method H, RT=1.21 min, MS (ESI) m/z: 333.9 (M+H)$^+$; Analytical HPLC Method B: 96% purity.

Example 137

2-(2-methoxy-7-methylquinoxalin-5-yl)-5,6,7,8-tetrahydro-4H-cyclohepta[d]thiazole

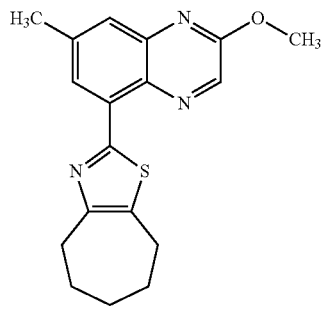

(137)

Intermediate I-12 (10 mg, 0.043 mmol) and 2-chlorocycloheptanone (6.28 mg, 0.043 mmol) were dissolved in dioxane (857 µL) and heated to 80° C. for 18 hours. More 2-chlorocycloheptanone (6.28 mg, 0.043 mmol) was added and the reaction mixture was heated to 110° C. for 24 hours. The reaction mixture was concentrated in vacuo, diluted with DMF, filtered, and purified by preparative HPLC (Method D, 55 to 95% B in 10 minutes) to give Example 137 (2.9 mg, 0.00873 mmol, 20.4%): $^1$H NMR (500 MHz, METHANOL-$d_4$) δ 8.48 (s, 1H), 8.26 (d, J=1.7 Hz, 1H), 7.66 (s, 1H), 4.11 (s, 3H), 3.08-3.01 (m, 2H), 2.95-2.89 (m, 2H), 2.60 (s, 3H), 1.98-1.87 (m, 2H), 1.83-1.71 (m, 4H); LC-MS: Method H, RT=1.13 min, MS (ESI) m/z: 326.1 (M+H)$^+$; Analytical HPLC Method B: 98% purity.

Example 138

2-(2-methoxy-7-methylquinoxalin-5-yl)-4,5,6,7-tetrahydrobenzo[d]thiazol-7-ol

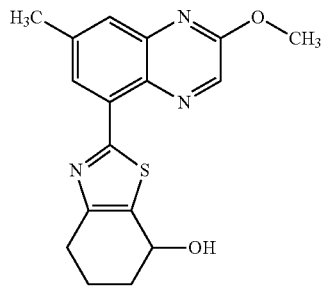

(138)

Intermediate 138A 2-(2-methoxy-7-methylquinoxalin-5-yl)-5,6-dihydrobenzo[d]thiazol-7(4H)-one

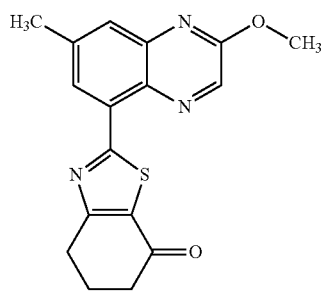

(138A)

Intermediate I-12 (15 mg, 0.064 mmol) and 2-chlorocyclohexane-1,3-dione (18.85 mg, 0.129 mmol) were dissolved in 1,4-dioxane (1286 µL) and heated to 100° C. for 18 hours. The reaction mixture was concentrated in vacuo, diluted with DMF, filtered, and purified by preparative HPLC (Method D, 35 to 75% B in 10 minutes) to give Intermediate 138A (4.6 mg, 0.014 mmol, 21.6%): $^1$H NMR (500 MHz, DMSO-$d_6$) δ 8.77 (s, 1H), 8.53 (s, 1H), 7.86 (s, 1H), 4.08 (s, 3H), 3.10 (t, J=6.1 Hz, 2H), 2.67-2.58 (m, 5H), 2.24-2.15 (m, 2H); LC-MS: Method H, RT=1.12 min, MS (ESI) m/z: 326.1 (M+H)$^+$; Analytical HPLC Method B: 98% purity.

Example 138

Intermediate 138A (3.68 mg, 0.011 mmol) was dissolved in MeOH (565 µL) and cooled to 0° C. Sodium borohydride (0.642 mg, 0.017 mmol) was added and the reaction mixture was allowed to slowly warm to ambient temperature and stir for 20 hours. The reaction mixture was diluted with water and extracted with EtOAc. The organic layer was washed with brine, dried ($Na_2SO_4$), filtered, and concentrated in vacuo. The crude material was diluted with DMF, filtered, and purified by preparative HPLC (Method D, 25 to 65% B in 10 minutes) to give Example 138 (2.3 mg, 0.00703 mmol, 62.1%): $^1$H NMR (500 MHz, METHANOL-$d_4$) δ 8.49 (s, 1H), 8.30 (d, J=1.7 Hz, 1H), 7.70 (d, J=0.8 Hz, 1H), 5.03 (br. s., 1H), 4.24 (br. s., 1H), 4.11 (s, 3H), 2.96-2.88 (m, 1H), 2.87-2.78 (m, 1H), 2.61 (s, 3H), 2.13 (d, J=9.9 Hz, 2H), 1.95-1.86 (m, 2H); LC-MS: Method H, RT=0.94 min, MS (ESI) m/z: 328.2 (M+H)$^+$; Analytical HPLC Method B: 100% purity.

Example 139

7-methoxy-2-(2-methoxy-7-methylquinoxalin-5-yl)-4,5,6,7-tetrahydrobenzo[d]thiazole

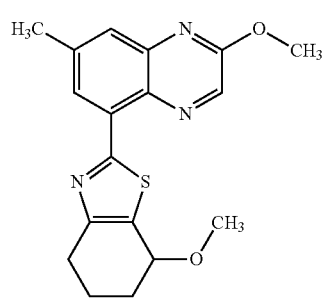

(139)

Example 138 (9.9 mg, 0.030 mmol) was dissolved in THF (605 Sodium hydride (1.330 mg, 0.033 mmol) was added and the reaction mixture was stirred for 30 minutes. Iodomethane (3.78 µL, 0.060 mmol) was added and the reaction mixture was stirred for 2 hours. The reaction mixture was diluted with EtOAc and washed with water, then brine, dried ($Na_2SO_4$), filtered, and concentrated in vacuo. The crude material was diluted with DMF, filtered, and purified by preparative HPLC (Method D, 40 to 80% B in 10 minutes) to give Example 139 (6.4 mg, 0.018 mmol, 60.8%): $^1$H NMR (500 MHz, METHANOL-$d_4$) δ 8.51 (s, 1H), 8.33 (d, J=1.7 Hz, 1H), 7.71 (dd, J=1.9, 0.8 Hz, 1H), 7.62 (dd, J=3.0, 1.7 Hz, 1H), 4.12 (s, 3H), 3.54 (s, 3H), 3.00-2.90 (m, 1H), 2.87-2.78 (m, 1H), 2.61 (s, 3H), 2.16-2.00 (m, 3H), 1.96-1.86 (m, 1H); LC-MS: Method H, RT=1.13 min, MS (ESI) m/z: 342.2 (M+H)+; Analytical HPLC Method B: 98% purity.

Example 140

6-methoxy-2-(2-methoxy-7-methylquinoxalin-5-yl)-4,5,6,7-tetrahydrobenzo[d]thiazole

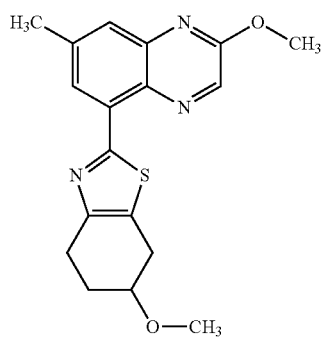

(140)

Intermediate 140A:
4-((tert-butyldimethylsilyl)oxy)cyclohexanone

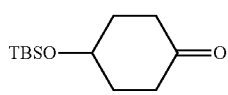

(140A)

4-hydroxycyclohexanone (500 mg, 4.38 mmol), TBS-Cl (792 mg, 5.26 mmol), and imidazole (447 mg, 6.57 mmol) were dissolved in DCM (8761 μL) for 3 hours. The reaction mixture was diluted with DCM, washed with water, 1 N HCl, saturated NaHCO₃, then brine, dried (Na₂SO₄), filtered, and concentrated in vacuo to give Intermediate 140A as a light yellow oil: ¹H NMR (400 MHz, CHLOROFORM-d) δ 4.09 (tt, J=5.1, 2.7 Hz, 1H), 2.69-2.56 (m, 2H), 2.24-2.14 (m, 2H), 1.99-1.77 (m, 4H), 0.88 (s, 9H), 0.06 (s, 6H).

Intermediate 140B 2-(2-methoxy-7-methylquinoxalin-5-yl)-4,5,6,7-tetrahydrobenzo[d]thiazol-6-ol

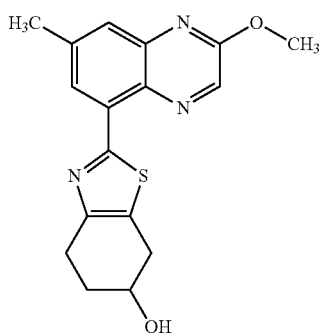

(140B)

Intermediate 140A (9.79 mg, 0.043 mmol), magnesium chloride (4.08 mg, 0.043 mmol), and NBS (7.63 mg, 0.043 mmol) were dissolved in dioxane (429 μL) and heated to 70° C. for 1 hour. Intermediate I-12 (10 mg, 0.043 mmol) was added and the reaction mixture was stirred for 18 hours. The reaction mixture was heated to 110° C. for 4 hours. The reaction mixture was diluted with EtOAc, washed with water, then brine, dried (Na₂SO₄), filtered, and concentrated in vacuo. The crude material was dissolved in 90:10:0.1 MeOH:H₂O:TFA (ca 1 mL) and allowed to stir overnight. The reaction mixture was concentrated in vacuo. The crude material was dissolved in DMF, filtered, and purified by preparative HPLC (Method D, 20 to 60% B in 10 minutes) to give Intermediate 140B (2.7 mg, 0.00825 mmol, 19.2%): ¹H NMR (500 MHz, METHANOL-d₄) δ 8.48 (s, 1H), 8.27 (d, J=1.9 Hz, 1H), 7.68 (d, J=0.8 Hz, 1H), 4.26-4.19 (m, 1H), 4.11 (s, 3H), 3.18 (dd, J=16.1, 4.8 Hz, 1H), 3.09-3.00 (m, 1H), 2.95-2.87 (m, 1H), 2.83 (dd, J=16.2, 7.2 Hz, 1H), 2.61 (s, 3H), 2.17-2.09 (m, 1H), 2.04-1.95 (m, 1H); LC-MS: Method H, RT=0.95 min, MS (ESI) m/z: 328.3 (M+H)+; Analytical HPLC Method B: 100% purity.

Example 140

Intermediate 140B (1.78 mg, 5.44 μmol) was dissolved in THF (109 Sodium hydride (0.239 mg, 5.98 μmol) was added and the reaction mixture was stirred for 30 minutes. Iodomethane (0.680 μL, 10.87 μmol) was added and the reaction mixture was stirred for 2 hours. The reaction mixture was diluted with EtOAc and washed with water, then brine, dried (Na₂SO₄), filtered, and concentrated in vacuo. The crude material was diluted with DMF, filtered, and purified by preparative HPLC (Method D, 45 to 90% B in 10 minutes) to give Example 140 (0.9 mg, 0.00264 mmol, 48.5%): ¹H NMR (500 MHz, METHANOL-d₄) δ 8.48 (s, 1H), 8.27 (d, J=1.9 Hz, 1H), 7.68 (d, J=0.8 Hz, 1H), 4.11 (s, 3H), 3.88-3.82 (m, 1H), 3.20 (dd, J=16.4, 5.4 Hz, 1H), 3.06-2.97 (m, 1H), 2.94-2.86 (m, 2H), 2.61 (s, 3H), 2.18-2.03 (m, 2H); LC-MS: Method H, RT=1.19 min, MS (ESI) m/z: 342.2 (M+H)+; Analytical HPLC Method B: 100% purity.

Example 141

2-(2-methoxy-7-methylquinoxalin-5-yl)-6,6-dimethyl-4,5,6,7-tetrahydrobenzo[d]thiazole

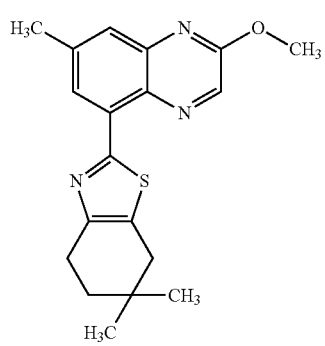

(141)

4,4-Dimethylcyclohexanone (6.49 mg, 0.051 mmol), magnesium chloride (4.08 mg, 0.043 mmol), and NBS (9.16 mg, 0.051 mmol) were dissolved in dioxane (429 μL) and heated to 70° C. for 1 hour. Intermediate I-12 (10 mg, 0.043 mmol) was added and the reaction mixture was heated to 110° C. for 18 hours. The reaction mixture was diluted with EtOAc, washed with water, then brine, dried (Na$_2$SO$_4$), filtered, and concentrated in vacuo. The crude material was dissolved in DMF, filtered, and purified by preparative HPLC (Method D, 55 to 100% B in 10 minutes) to give Example 141 (3.3 mg, 0.00943 mmol, 22%): $^1$H NMR (500 MHz, METHANOL-d$_4$) δ 8.48 (s, 1H), 8.27 (d, J=1.9 Hz, 1H), 7.68 (dd, J=1.9, 0.8 Hz, 1H), 4.11 (s, 3H), 2.88 (t, J=6.6 Hz, 2H), 2.66 (s, 2H), 2.61 (s, 3H), 1.72 (t, J=6.5 Hz, 2H), 1.08 (s, 6H); LC-MS: Method H, RT=1.24 min, MS (ESI) m/z: 340.0 (M+H)$^+$; Analytical HPLC Method B: 97% purity.

Example 142

2-(2-(2-methoxy-7-methylquinoxalin-5-yl)-5,6-dihydro-4H-cyclopenta[d]thiazol-5-yl) ethanol

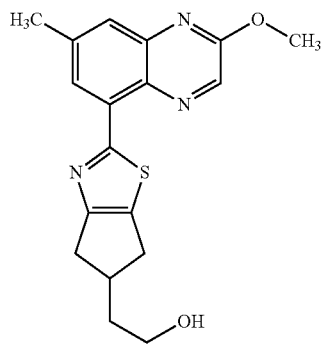

(142)

Intermediate 142A: 3-(2-((tert-butyldimethylsilyl)oxy)ethyl)cyclopentanone

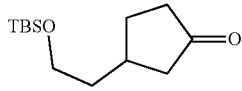

(142A)

3-(2-hydroxyethyl)cyclopentanone (500 mg, 3.90 mmol), TBS-Cl (706 mg, 4.68 mmol), and imidazole (398 mg, 5.85 mmol) were dissolved in DCM (7802 μL) for 3.5 hours. The reaction mixture was diluted with DCM, washed with water, 1 N HCl, saturated NaHCO$_3$, then brine, dried (Na$_2$SO$_4$), filtered, and concentrated in vacuo to give Intermediate 142A as a light yellow oil: $^1$H NMR (400 MHz, CHLOROFORM-d) δ 3.63-3.52 (m, 2H), 2.35-2.26 (m, 1H), 2.25-2.13 (m, 2H), 2.12-1.99 (m, 2H), 1.73 (ddd, J=17.9, 10.0, 1.3 Hz, 1H), 1.65-1.40 (m, 3H), 0.80 (s, 9H), −0.05 (s, 6H).

Example 142

Intermediate 142A (18.71 mg, 0.077 mmol), magnesium chloride (6.12 mg, 0.064 mmol), and NBS (13.73 mg, 0.077 mmol) were dissolved in dioxane (643 μL) and heated to 70° C. for 1 hour. 2-Methoxy-7-methylquinoxaline-5-carbothioamide (15 mg, 0.064 mmol) was added and the reaction mixture was heated to 110° C. for 18 hours. The reaction mixture was diluted with EtOAc, washed with water, then brine, dried (Na$_2$SO$_4$), filtered, and concentrated in vacuo. The crude material was dissolved in 90:10:0.1 MeOH:H$_2$O:TFA (ca 1 mL) for 18 hours. The reaction mixture was concentrated in vacuo. The crude material was dissolved in DMF, filtered, and purified by preparative HPLC (Method D, 35 to 80% B in 10 minutes) to give Example 142 (2.9 mg, 0.00790 mmol, 12.3%): LC-MS: Method H, RT=1.04 min, MS (ESI) m/z: 342.0 (M+H)$^+$; Analytical HPLC Method B: 93% purity.

Example 143

2-(2-(methoxymethyl)-7-methylquinoxalin-5-yl)-4,5,6,7-tetrahydrobenzo[d]thiazol-7-ol

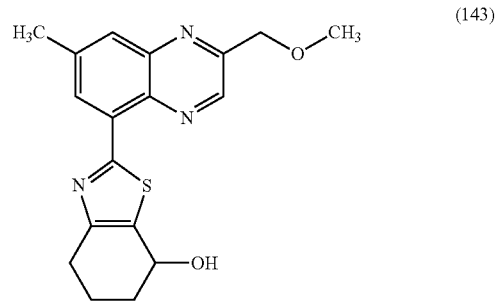

(143)

Intermediate 143A: 2-amino-5,6-dihydrobenzo[d]thiazol-7(4H)-one, HCl

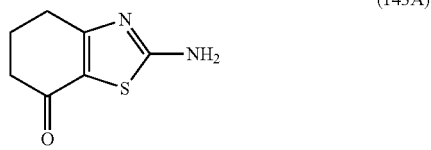

(143A)

2-chlorocyclohexane-1,3-dione (1 g, 6.82 mmol) and thiourea (0.519 g, 6.82 mmol) were dissolved in EtOH (13.65 mL) and heated to 80° C. for 3 days. The reaction mixture was cooled to ambient temperature and the solid collected by suction filtration, washing with EtOH to give Intermediate 143A (790 mg, 3.86 mmol, 56.6%) as a white solid: $^1$H NMR (400 MHz, METHANOL-d$_4$) δ 2.80 (t, J=6.2 Hz, 2H), 2.51 (dd, J=7.2, 5.8 Hz, 2H), 2.15 (quin, J=6.4 Hz, 2H); LC-MS: Method H, RT=0.63 min, MS (ESI) m/z: 169.0 (M+H)$^+$.

Intermediate 143B: 2-bromo-5,6-dihydrobenzo[d]thiazol-7(4H)-one

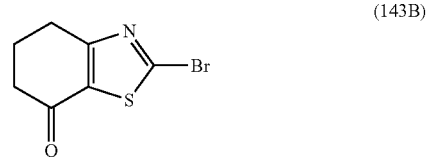 [SMILES: O=C1CCCc2nc(Br)sc21]

(143B)

Copper(II) bromide (1.466 g, 6.56 mmol) and t-butyl nitrite (0.780 mL, 6.56 mmol) were dissolved in MeCN (15.44 mL) and allowed to stir 10 minutes. Intermediate 143A (0.79 g, 3.86 mmol) was dissolved in MeCN (23.16 mL) and the copper solution was added and the reaction mixture was stirred for 1.5 hours. The reaction mixture was concentrated in vacuo. The residue was dissolved in EtOAc, washed twice with 1 N HCl, saturated NaHCO$_3$, then brine, dried (Na$_2$SO$_4$), filtered, and concentrated in vacuo to give Intermediate 143B (817.9 mg, 3.52 mmol, 91%) as an orange solid: $^1$H NMR (400 MHz, CHLOROFORM-d) δ 3.07 (t, J=6.2 Hz, 2H), 2.64 (dd, J=7.3, 5.7 Hz, 2H), 2.24 (quin, J=6.4 Hz, 2H); LC-MS: Method H, RT=0.98 min, MS (ESI) m/z: 232/234 (M+H)$^+$.

Intermediate 143C: 2-bromo-4,5,6,7-tetrahydrobenzo[d]thiazol-7-ol

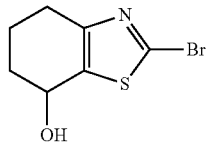

(143C)

Intermediate 143B (500 mg, 2.154 mmol) was dissolved in MeOH (10.8 mL) and cooled to 0° C. Sodium borohydride (163 mg, 4.31 mmol) was added and stirred for 1.5 hours. The reaction mixture was quenched with saturated ammonium chloride and extracted with EtOAc. The organic layer was washed with water, then brine, dried (Na$_2$SO$_4$), filtered, and concentrated in vacuo to give Intermediate 143C (488 mg, 2.084 mmol, 97%) as an orange oil: $^1$H NMR (400 MHz, CHLOROFORM-d) δ 4.93 (br. s., 1H), 2.89-2.79 (m, 1H), 2.79-2.69 (m, 1H), 2.17-2.07 (m, 1H), 2.06-1.98 (m, 1H), 1.92-1.80 (m, 2H); LC-MS: Method H, RT=0.88 min, MS (ESI) m/z: 234/236 (M+H)$^+$.

Example 143

Intermediate I-2 was purified by column chromatography (ISCO, 12 g silica gel column, 17 minute gradient from 0 to 20% MeOH in DCM) to give dimethyl (2-(methoxymethyl)-7-methylquinoxalin-5-yl)boronate (25 mg, 0.096 mmol), Intermediate 143C (27.0 mg, 0.115 mmol), and potassium phosphate tribasic (40.8 mg, 0.192 mmol) were dissolved in DMF (961 μL) and degassed by bubbling with argon for 15 minutes. Palladium tetrakistriphenylphosphine (11.11 mg, 9.61 μmol) was added and degassing continued for 5 minutes. The reaction mixture was heated to 85° C. at for 18 hours. The reaction mixture was diluted with DMF, filtered, and purified by preparative HPLC (Method D, 20 to 60% B in 20 minutes) to give Example 143 (5.4 mg, 0.015 mmol, 15.1%): $^1$H NMR (500 MHz, DMSO-d$_6$) δ 9.06 (s, 1H), 8.61 (s, 1H), 7.94 (s, 1H), 5.56 (d, J=6.3 Hz, 1H), 4.92 (br. s., 1H), 4.80 (s, 2H), 3.47 (s, 3H), 2.87-2.73 (m, 2H), 2.65 (s, 3H), 2.07-1.99 (m, 2H), 1.84-1.70 (m, 2H); LC-MS: Method H, RT=1.02 min, MS (ESI) m/z: 342.2 (M+H)$^+$; Analytical HPLC Method B: 92% purity.

Example 144

2-(2-(methoxymethyl)-7-methylquinoxalin-5-yl)-4,5,6,7-tetrahydrobenzo[d]thiazole

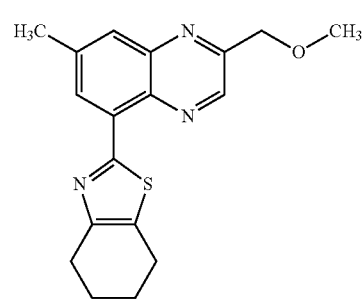

(144)

Intermediate 144A: 2-(tributylstannyl)-4,5,6,7-tetrahydrobenzo[d]thiazole

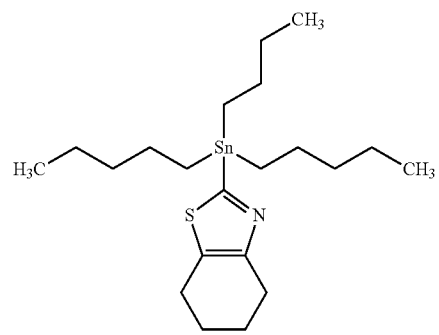

(144A)

2-Bromo-4,5,6,7-tetrahydrobenzo[d]thiazole (25 mg, 0.115 mmol) was dissolved in Et$_2$O (458 μL) and cooled to −78° C. BuLi (60.0 μL, 0.126 mmol) was added and the reaction mixture was stirred for 30 minutes. Tributylchlorostannane (31.1 μL, 0.115 mmol) was added and stirred for 40 minutes. The reaction mixture was warmed to ambient temperature and concentrated in vacuo. The crude material was suspended in hexanes and filtered through dry celite. The residue was concentrated in vacuo to give Intermediate 144A, which was used directly in the subsequent reaction.

Example 144

Intermediate I-2E (15 mg, 0.056 mmol), Intermediate 144A (30.1 mg, 0.070 mmol), and potassium acetate (11.02 mg, 0.112 mmol) were dissolved in dioxane (814 μL) and degassed by bubbling with argon for 15 minutes. Palladium tetrakistriphenylphosphine (3.24 mg, 2.81 μmol) was added and the reaction mixture was sealed and heated to 120° C. in the microwave for 2 hours. The reaction mixture was diluted with EtOAc, washed with water, 1 N HCl, then brine, dried (Na$_2$SO$_4$), filtered, and concentrated in vacuo. The crude material was diluted with DMF, filtered, and purified by preparative HPLC (Method D, 40 to 80% B in 20 minutes) and repurified by preparative HPLC (Method D, 50 to 85% B in 20 minutes) to give Example 144 (1.9 mg, 0.00584 mmol, 10.4%): $^1$H NMR (500 MHz, DMSO-d$_6$) δ

9.03 (s, 1H), 8.59 (s, 1H), 7.92 (s, 1H), 4.79 (s, 2H), 3.46 (s, 3H), 2.88 (br. s., 2H), 2.82 (br. s., 2H), 2.64 (s, 3H), 1.87 (br. s., 4H); LC-MS: Method H, RT=1.23 min, MS (ESI) m/z: 326.3 (M+H)+; Analytical HPLC Method B: 100% purity.

Example 145

2-(2-(methoxymethyl)-7-methylquinoxalin-5-yl)-6,6-dimethyl-4,5,6,7-tetrahydrobenzo[d]thiazol-7-ol

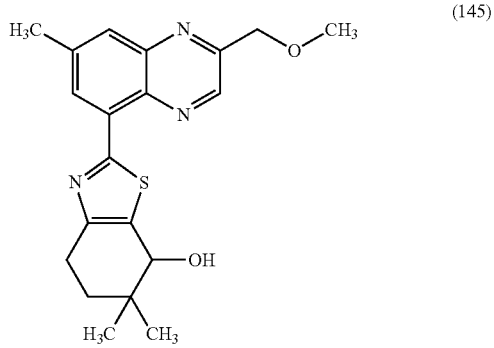

(145)

Intermediate 145A: 2-amino-6,6-dimethyl-5,6-dihydrobenzo[d]thiazol-7(4H)-one, HCl

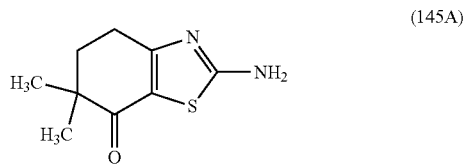

(145A)

2-bromo-4,4-dimethylcyclohexane-1,3-dione (0.5 g, 2.282 mmol) and thiourea (0.174 g, 2.282 mmol) were dissolved in EtOH (4.56 mL) and heated to 75° C. for 18 hours. The reaction mixture was cooled to ambient temperature then to 0° C. and the solid was collected by suction filtration, washing with cold EtOH to give Intermediate 145A (128.3 mg, 0.551 mmol, 24.2%) as an off-white solid: $^1$H NMR (400 MHz, METHANOL-d$_4$) δ 2.90 (t, J=6.2 Hz, 2H), 2.08 (t, J=6.2 Hz, 2H), 1.20 (s, 6H); LC-MS: Method H, RT=0.85 min, MS (ESI) m/z: 197.1 (M+H)+.

Intermediate 145B: 2-bromo-6,6-dimethyl-5,6-dihydrobenzo[d]thiazol-7(4H)-one

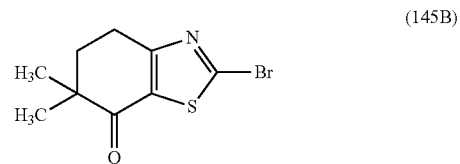

(145B)

Copper(II) bromide (248 mg, 1.111 mmol) and t-butyl nitrite (132 µL, 1.111 mmol) were dissolved in MeCN (2615 µL) and allowed to stir 10 minutes. Intermediate 145A (128.3 mg, 0.654 mmol) was dissolved in MeCN (3922 µL) and the copper solution was added and stirring continued for 1.5 hours. The reaction mixture was diluted with EtOAc, washed with 1 N HCl, saturated NaHCO$_3$, then brine, dried (Na$_2$SO$_4$), filtered, and concentrated in vacuo to give Intermediate 145B (110 mg, 0.423 mmol, 64.7%): $^1$H NMR (400 MHz, CHLOROFORM-d) δ 3.08 (t, J=6.2 Hz, 2H), 2.06 (t, J=6.2 Hz, 2H), 1.25 (s, 6H); LC-MS: Method H, RT=1.21 min, MS (ESI) m/z: 260/262 (M+H)+.

Intermediate 145C: 2-bromo-6,6-dimethyl-4,5,6,7-tetrahydrobenzo[d]thiazol-7-ol

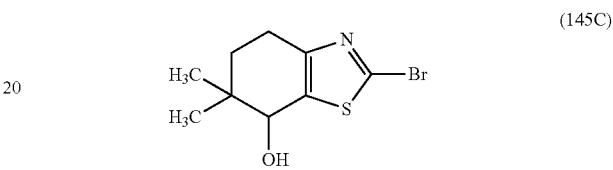

(145C)

Intermediate 145B (110 mg, 0.423 mmol) was dissolved in MeOH (2114 µL) and cooled to 0° C. Sodium borohydride (32.0 mg, 0.846 mmol) was added and the reaction mixture stirred for 40 minutes. The reaction mixture was quenched with saturated ammonium chloride and extracted with EtOAc. The organic layer was washed with water, then brine, dried (Na$_2$SO$_4$), filtered, and concentrated in vacuo to give Intermediate 145C (107 mg, 0.408 mmol, 97%) as a yellow oil: $^1$H NMR (400 MHz, CHLOROFORM-d) δ 4.45 (d, J=6.4 Hz, 1H), 2.88-2.68 (m, 2H), 1.93 (d, J=7.5 Hz, 1H), 1.82 (dt, J=13.8, 5.9 Hz, 1H), 1.70-1.63 (m, 1H), 1.07 (s, 3H), 1.02 (s, 3H); LC-MS: Method H, RT=1.12 min, MS (ESI) m/z: 263.9 (M+H)+.

Example 145

Intermediate I-2 was purified by column chromatography (ISCO, 12 g silica gel column, 17 minute gradient from 0 to 20% MeOH in DCM) to give dimethyl (2-(methoxymethyl)-7-methylquinoxalin-5-yl)boronate (20 mg, 0.077 mmol), Intermediate 145C (24.19 mg, 0.092 mmol), and potassium phosphate tribasic (32.6 mg, 0.154 mmol) were dissolved in DMF (769 µL) and degassed by bubbling with argon for 15 minutes. Palladium tetrakistriphenylphosphine (8.89 mg, 7.69 µmol) was added and degassing continued for 5 minutes. The reaction mixture was heated to 85° C. for 18 hours. The reaction mixture was diluted with DMF, filtered, and purified by preparative HPLC (Method D, 40 to 80% B in 20 minutes) to give Example 145 (5.6 mg, 0.015 mmol, 18.9%): $^1$H NMR (500 MHz, DMSO-d$_6$) δ 9.06 (s, 1H), 8.60 (d, J=1.4 Hz, 1H), 7.94 (s, 1H), 5.58 (d, J=6.9 Hz, 1H), 4.80 (s, 2H), 4.48 (d, J=6.3 Hz, 1H), 3.47 (s, 3H), 2.82-2.74 (m, 2H), 2.65 (s, 3H), 1.86-1.78 (m, 1H), 1.70-1.62 (m, 1H), 1.03 (s, 3H), 0.91 (s, 3H); LC-MS: Method H, RT=1.22 min, MS (ESI) m/z: 370.1 (M+H)+; Analytical HPLC Method B: 96% purity.

Example 146

2-(2-(methoxymethyl)-7-methylquinoxalin-5-yl)thiazolo[4,5-c]pyridine

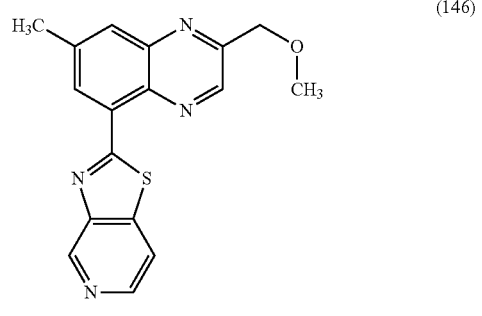

(146)

Intermediate 146A: 2-bromothiazolo[4,5-c]pyridine

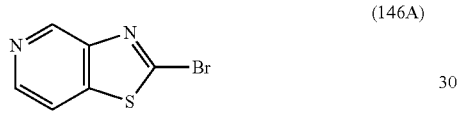

(146A)

Copper(II) bromide (71.6 mg, 0.320 mmol) and t-butyl nitrite (38.1 µL, 0.320 mmol) were dissolved in MeCN (754 µL) and allowed to stir 10 minutes. Thiazolo[4,5-c]pyridin-2-amine, TFA (50 mg, 0.189 mmol) was dissolved in MeCN (1131 µL) and the copper solution was added and the reaction mixture was stirred for 2 hours. The reaction mixture was diluted with EtOAc, washed with saturated NaHCO$_3$, water, then brine, dried (Na$_2$SO$_4$), filtered, and concentrated in vacuo to give Intermediate 146A (12.5 mg, 0.058 mmol, 30.8%) as a brown solid: LC-MS: Method H, RT=0.68 min, MS (ESI) m/z: 215/217 (M+H)$^+$.

Example 146

Intermediate I-2 (10 mg, 0.032 mmol) and Intermediate 146A (10.27 mg, 0.048 mmol) were dissolved in DMF (318 µL). PdCl$_2$(dppf)-CH$_2$Cl$_2$ (1.560 mg, 1.910 µmol) was added and the reaction mixture was degassed by bubbling with argon for 15 minutes. Sodium carbonate (2 M, 19.10 µL, 0.038 mmol) was added and the reaction mixture was degassed for 5 minutes, then sealed and heated to 100° C. in the microwave for 30 minutes. The reaction mixture was diluted with DMF, filtered, and purified by preparative HPLC (Method D, 25 to 65% B in 20 minutes) to give Example 146 (3.0 mg, 0.00893 mmol, 28.1%): $^1$H NMR (500 MHz, DMSO-d$_6$) δ 9.43 (br. s., 1H), 9.14 (br. s., 1H), 8.92 (br. s., 1H), 8.57 (br. s., 1H), 8.30 (br. s., 1H), 8.14 (br. s., 1H), 4.84 (br. s., 2H), 3.49 (br. s., 3H), 2.72 (br. s., 3H); LC-MS: Method H, RT=0.90 min, MS (ESI) m/z: 323.3 (M+H)$^+$; Analytical HPLC Method B: 96% purity.

Example 147

2-(2-(methoxymethyl)-7-methylquinoxalin-5-yl)thiazolo[5,4-b]pyridine

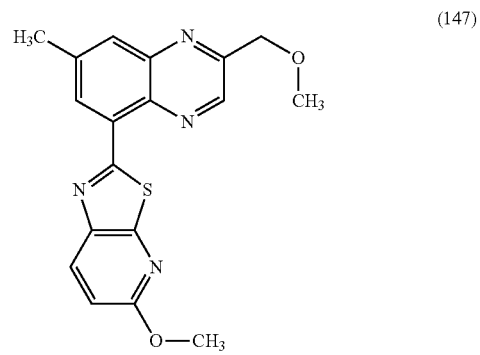

(147)

Intermediate 147A: 2-bromo-5-methoxythiazolo[5,4-b]pyridine

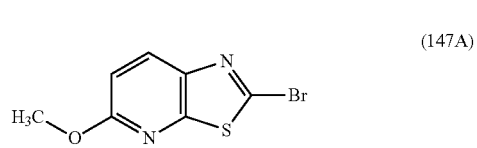

(147A)

Copper(II) bromide (64.3 mg, 0.288 mmol) and t-butyl nitrite (34.2 µL, 0.288 mmol) were dissolved in MeCN (677 µL) and allowed to stir 10 minutes. 5-methoxythiazolo[5,4-b]pyridin-2-amine, TFA (50 mg, 0.169 mmol) was dissolved in MeCN (1016 µL) and the copper solution was added and the reaction mixture was stirred for 1.5 hours. The reaction mixture was diluted with EtOAc, washed with saturated NaHCO$_3$, water, then brine, dried (Na$_2$SO$_4$), filtered, and concentrated in vacuo to give Intermediate 147A as a tan solid: $^1$H NMR (500 MHz, CHLOROFORM-d) δ 8.08 (d, J=8.8 Hz, 1H), 6.86 (d, J=8.8 Hz, 1H), 4.02 (s, 3H); LC-MS: Method H, RT=1.21 min, MS (ESI) m/z: 245/247 (M+H)$^+$.

Example 147

Intermediate I-2 (10 mg, 0.032 mmol) and Intermediate 147A (11.70 mg, 0.048 mmol) were dissolved in DMF (318 µL). PdCl$_2$(dppf)-CH$_2$Cl$_2$ (1.560 mg, 1.910 µmol) was added and the reaction mixture was degassed by bubbling with argon for 15 minutes. Sodium carbonate (2 M, 19.10 µL, 0.038 mmol) was added and the reaction mixture was degassed for 5 minutes, then sealed and heated to 100° C. in the microwave for 30 minutes. The reaction mixture was diluted with DMF, filtered, and purified by preparative HPLC (Method D, 45 to 85% B in 20 minutes) to give Example 147 (3.1 mg, 0.00862 mmol, 27.1%): $^1$H NMR (500 MHz, DMSO-d$_6$) δ 9.14 (br. s., 1H), 8.81 (br. s., 1H), 8.43 (d, J=8.0 Hz, 1H), 8.08 (br. s., 1H), 7.08 (d, J=8.8 Hz, 1H), 4.84 (br. s., 2H), 4.02 (br. s., 3H), 3.49 (br. s., 3H), 2.70 (br. s., 3H); LC-MS: Method H, RT=1.34 min, MS (ESI) m/z: 353.2 (M+H)$^+$; Analytical HPLC Method B: 98% purity.

Example 148

2-(2-(methoxymethyl)-7-methylquinoxalin-5-yl)thiazolo[5,4-b]pyridine

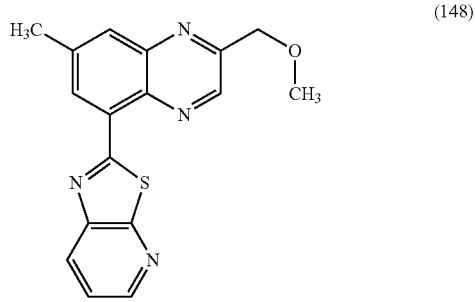
(148)

Intermediate I-2 (10 mg, 0.032 mmol) and 2-bromothiazolo[5,4-b]pyridine (10.27 mg, 0.048 mmol) (10.27 mg, 0.048 mmol) were dissolved in DMF (318 μL). PdCl$_2$(dppf)-CH$_2$Cl$_2$ (1.560 mg, 1.910 μmol) was added and the reaction mixture was degassed by bubbling with argon for 15 minutes. Sodium carbonate (2 M, 19.10 μL, 0.038 mmol) was added and the reaction mixture was degassed for 5 minutes, then sealed and heated to 100° C. in the microwave for 30 minutes. The reaction mixture was diluted with DMF, filtered, and purified by preparative HPLC (Method D, 30 to 70% B in 20 minutes) to give Example 148 (3.0 mg, 0.00893 mmol, 28.1%): $^1$H NMR (500 MHz, DMSO-d$_6$) δ 9.17 (br. s., 1H), 8.89 (br. s., 1H), 8.70 (br. s., 1H), 8.54 (d, J=8.3 Hz, 1H), 8.14 (br. s., 1H), 7.66 (br. s., 1H), 4.84 (br. s., 2H), 3.49 (br. s., 3H), 2.72 (br. s., 3H); LC-MS: Method H, RT=1.20 min, MS (ESI) m/z: 323.2 (M+H)$^+$; Analytical HPLC Method B: 96% purity.

Example 149

7-chloro-2-(2-(methoxymethyl)-7-methylquinoxalin-5-yl)thiazolo[5,4-c]pyridine

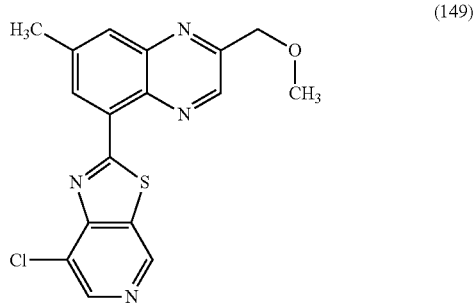 [SMILES: COCc1cnc2c(-c3nc4c(Cl)cncc4s3)cc(C)cc2n1]
(149)

Intermediate I-2 (10 mg, 0.032 mmol) and 2-bromo-7-chlorothiazolo[5,4-c]pyridine (11.91 mg, 0.048 mmol) were dissolved in DMF (318 μL). PdCl$_2$(dppf)-CH$_2$Cl$_2$ (1.560 mg, 1.910 μmol) was added and the reaction mixture was degassed by bubbling with argon for 15 minutes. Sodium carbonate (2 M, 19.10 μL, 0.038 mmol) was added and the reaction mixture was degassed for 5 minutes, then sealed and heated to 100° C. in the microwave for 30 minutes. The reaction mixture was diluted with DMF, filtered, and purified by preparative HPLC (Method D, 45 to 85% B in 12 minutes) to give Example 149 (3.1 mg, 0.00834 mmol, 26.2%): $^1$H NMR (500 MHz, DMSO-d$_6$) δ 9.46 (s, 1H), 9.17 (s, 1H), 8.96 (d, J=1.9 Hz, 1H), 8.75 (s, 1H), 8.21 (s, 1H), 4.86 (s, 2H), 3.49 (s, 3H), 2.75 (s, 3H); LC-MS: Method H, RT=1.28 min, MS (ESI) m/z: 357.1 (M+H)$^+$; Analytical HPLC Method B: 96% purity.

Example 150

5-methoxy-2-(2-methoxy-7-methylquinoxalin-5-yl)thiazolo[5,4-b]pyridine

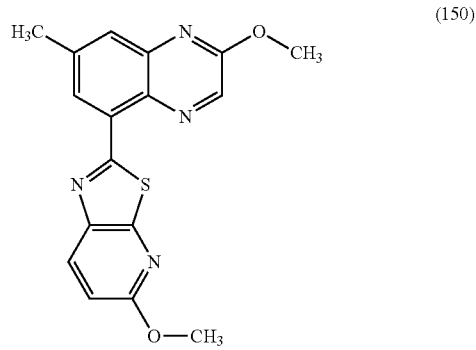
(150)

Intermediate I-9 (10 mg, 0.033 mmol), 2-bromo-5-methoxythiazolo[5,4-b] pyridine (9.80 mg, 0.040 mmol), and potassium phosphate tribasic (14.14 mg, 0.067 mmol) were dissolved in DMF (333 μL) and degassed by bubbling with argon for 15 minutes. Palladium tetrakistriphenylphosphine (3.85 mg, 3.33 μmol) was added and degassing continued for 5 minutes. The reaction mixture was heated to 85° C. for 18 hours. The reaction mixture was diluted with DMF, filtered, and purified by preparative HPLC (Method D, 60 to 100% B in 20 minutes) to give Example 150 (1.1 mg, 0.00325 mmol, 9.8%): LC-MS: Method H, RT=1.50 min, MS (ESI) m/z: 339.1 (M+H)$^+$; Analytical HPLC Method B: 100% purity.

Example 151

7-chloro-2-(2-methoxy-7-methylquinoxalin-5-yl)thiazolo[5,4-c]pyridine

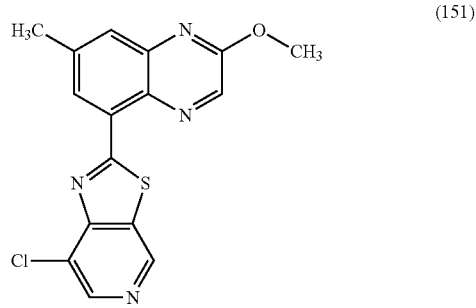 [SMILES: COc1cnc2c(-c3nc4c(Cl)cncc4s3)cc(C)cc2n1]
(151)

Intermediate I-9 (10 mg, 0.033 mmol), 2-bromo-7-chlorothiazolo[5,4-c]pyridine (9.98 mg, 0.040 mmol), and potassium phosphate tribasic (14.14 mg, 0.067 mmol) were dissolved in DMF (333 μL) and degassed by bubbling with argon for 15 minutes. Palladium tetrakistriphenylphosphine (3.85 mg, 3.33 μmol) was added and degassing continued for 5 minutes. The reaction mixture was heated to 85° C. for 24 hours. The reaction mixture was diluted with DMF, filtered, and purified by preparative HPLC (Method D, 50 to 100% B in 20 minutes) then repurified by preparative (Method D, 45 to 85% B in 20 minutes) to give Example 151 (0.9 mg, 0.00252 mmol, 7.6%): $^1$H NMR (500 MHz, CHLOROFORM-d) δ 9.17 (br. s., 1H), 8.88 (br. s., 1H), 8.68 (br. s., 1H), 8.62 (br. s., 1H), 7.89 (br. s., 1H), 4.18 (br. s., 3H), 2.73 (br. s., 3H); LC-MS: Method H, RT=1.40 min, MS (ESI) m/z: 343.1 (M+H)$^+$; Analytical HPLC Method B: 96% purity.

Example 152 methyl 6-methoxy-2-(2-methoxy-7-methylquinoxalin-5-yl)benzo[d]thiazole-4-carboxylate

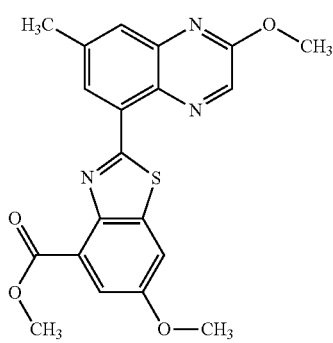

(152)

Intermediate I-9 (99 mg, 0.331 mmol), Intermediate I-20C (100 mg, 0.331 mmol), and potassium phosphate tribasic (141 mg, 0.662 mmol) were dissolved in DMF (3310 μL) and degassed by bubbling with argon for 15 minutes. Palladium tetrakistriphenylphosphine (38.2 mg, 0.033 mmol) was added and degassing continued for 5 minutes. The reaction mixture was heated to 85° C. for 18 hours. The reaction mixture was diluted with water and extracted thrice with EtOAc. The combined organic layers were washed with brine, dried (Na$_2$SO$_4$), filtered, and concentrated in vacuo. The crude material was diluted with DMF, filtered, and purified by preparative HPLC (Method D, 60 to 100% B in 15 minutes) to give Example 152 (2.7 mg, 0.00676 mmol, 2%) as a yellow solid: $^1$H NMR (500 MHz, DMSO-d$_6$) δ 8.77 (br. s., 1H), 8.61 (br. s., 1H), 8.04 (br. s., 1H), 7.87 (br. s., 1H), 7.57 (br. s., 1H), 4.10 (br. s., 3H), 4.01 (br. s., 3H), 3.93 (br. s., 3H), 2.67 (br. s., 3H); LC-MS: Method H, RT=1.40 min, MS (ESI) m/z: 396.1 (M+H)$^+$; Analytical HPLC Method B: 99% purity.

Example 153

6-methoxy-2-(3-(methoxymethyl)-6-methyl-1,7-naphthyridin-8-yl)-4-methylbenzo[d]thiazole

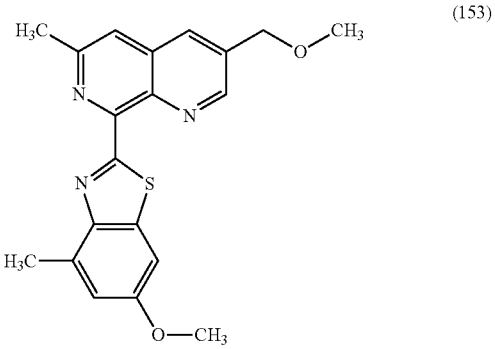

(153)

Intermediate 153A: 2-nitroacetamide

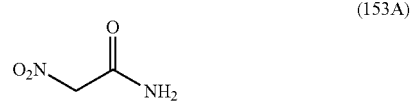

(153A)

Ethyl 2-nitroacetate (1 g, 7.51 mmol) was dissolved in NH$_3$ in MeOH (7 M, 16.10 mL, 113 mmol) and heated to 65° C. in a sealed tube at for 5 hours. The reaction mixture was cooled to ambient temperature and concentrated in vacuo to give Intermediate 153A, which was used directly in the subsequent reaction.

Intermediate 153B: ethyl 6-methyl-3-nitro-2-oxo-1,2-dihydropyridine-4-carboxylate

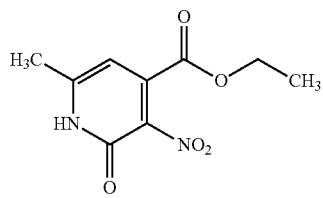

(153B)

Intermediate 153A (782 mg, 7.51 mmol), ethyl 2,4-dioxovalerate (1161 μL, 8.27 mmol), and piperidinium acetate (1091 mg, 7.51 mmol) were dissolved in water (37.6 mL) and stirred for 18 hours. The reaction mixture was concentrated in vacuo. The crude material was dissolved in DCM, filtered and purified by column chromatography (ISCO, 80 g silica gel column, 29 minute gradient from 0 to 20% MeOH in DCM) to give Intermediate 153B (890 mg, 3.93 mmol, 52.4%) as an orange solid: $^1$H NMR (400 MHz, CHLOROFORM-d) δ 6.49 (d, J=0.7 Hz, 1H), 4.40 (q, J=7.0 Hz, 2H), 2.49 (d, J=0.7 Hz, 3H), 1.38 (t, J=7.2 Hz, 3H); LC-MS: Method H, RT=0.90 min, MS (ESI) m/z: 227.2 (M+H)$^+$.

Intermediate 153C: ethyl 2-(benzyloxy)-6-methyl-3-nitroisonicotinate

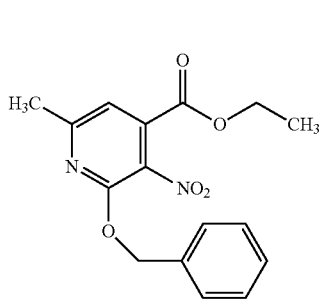
(153C)

Intermediate 153B (400 mg, 1.768 mmol) was suspended in toluene (11.8 mL). Silver oxide (1025 mg, 4.42 mmol) then benzyl bromide (210 µL, 1.768 mmol) were added and the reaction mixture was heated to 40° C. for 4 days. The reaction mixture was diluted with EtOAc and filtered through a micron filter. The residue was concentrated in vacuo. The crude material was purified by column chromatography (ISCO, 40 g silica gel column, 29 minute gradient from 0 to 100% EtOAc in hexanes) to give Intermediate 153C (260 mg, 0.822 mmol, 46.5%) as a white solid: $^1$H NMR (400 MHz, CHLOROFORM-d) δ 7.49-7.30 (m, 5H), 7.22 (d, J=0.4 Hz, 1H), 5.53 (s, 2H), 4.39 (q, J=7.0 Hz, 2H), 2.57 (d, J=0.4 Hz, 3H), 1.37 (t, J=7.2 Hz, 3H); LC-MS: Method H, RT=1.32 min, MS (ESI) m/z: 317.1 (M+H)$^+$.

Intermediate 153D: (2-(benzyloxy)-6-methyl-3-nitropyridin-4-yl)methanol

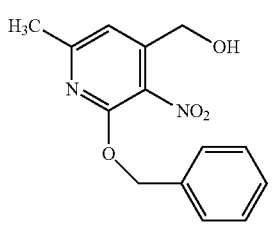
(153D)

Sodium borohydride (93 mg, 2.466 mmol) and calcium chloride (137 mg, 1.233 mmol) were dissolved in THF (3288 After 1 hour, a solution of Intermediate 153C (260 mg, 0.822 mmol) in THF (822 µL) was added dropwise. After 18 hours, the reaction mixture was diluted with EtOAc, washed with water, then brine, dried (Na$_2$SO$_4$), filtered, and concentrated in vacuo to give Intermediate 153D (169 mg, 0.616 mmol, 75%) as a yellow oil: $^1$H NMR (400 MHz, CHLOROFORM-d) δ 7.49-7.44 (m, 2H), 7.42-7.36 (m, 2H), 7.36-7.31 (m, 1H), 7.04 (s, 1H), 5.53 (s, 2H), 4.75 (s, 2H), 2.54 (s, 3H); LC-MS: Method H, RT=1.19 min, MS (ESI) m/z: 275.1 (M+H)$^+$.

Intermediate 153E: (3-amino-2-(benzyloxy)-6-methylpyridin-4-yl)methanol

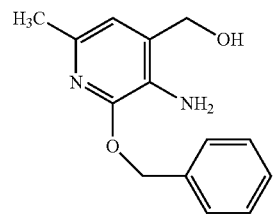
(153E)

Intermediate 153D (169 mg, 0.616 mmol) was dissolved in MeOH (4213 µL) and THF (527 µL). Ammonium chloride (659 mg, 12.32 mmol) and zinc (403 mg, 6.16 mmol) were added and the reaction mixture was heated to 40° C. for 1.5 hours. The reaction mixture was concentrated in vacuo. The crude material was redissolved in EtOAc/saturated sodium carbonate and allowed to stir vigorously for 15 minutes. The mixture was filtered through a sintered glass funnel. The organic layer was washed with water then brine, dried (Na$_2$SO$_4$), filtered, and concentrated in vacuo to give Intermediate 153E (146.7 mg, 0.601 mmol, 97%) as a yellow oil: $^1$H NMR (400 MHz, CHLOROFORM-d) δ 7.52-7.47 (m, 2H), 7.44-7.31 (m, 4H), 6.55 (s, 1H), 5.44 (s, 2H), 4.66 (s, 2H), 4.10 (br. s., 2H), 2.39 (d, J=0.4 Hz, 3H); LC-MS: Method H, RT=0.93 min, MS (ESI) m/z: 245.2 (M+H)$^+$.

Intermediate 153F: 3-amino-2-(benzyloxy)-6-methylisonicotinaldehyde

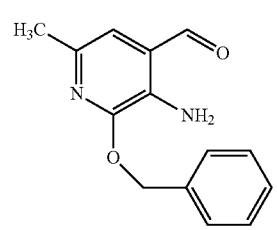
(153F)

Intermediate 153E (146 mg, 0.598 mmol) was dissolved in CHCl$_3$ (3984 µL). Manganese dioxide (312 mg, 3.59 mmol) was added. After 2.5 hours, the reaction mixture was filtered through celite and concentrated in vacuo to give Intermediate 153F (125.7 mg, 0.519 mmol, 87%) as an orange oil: $^1$H NMR (400 MHz, CHLOROFORM-d) δ 9.81 (s, 1H), 7.43-7.37 (m, 2H), 7.35-7.23 (m, 3H), 6.75 (s, 1H), 6.08 (br. s., 2H), 5.36 (s, 2H), 2.33 (d, J=0.7 Hz, 3H); LC-MS: Method H, RT=1.24 min, MS (ESI) m/z: 243.3 (M+H)$^+$.

Intermediate 153G: 8-(benzyloxy)-3-(methoxymethyl)-6-methyl-1,7-naphthyridine

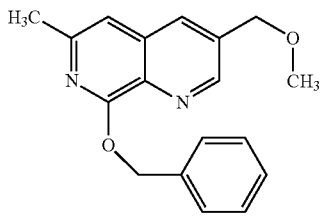
(153G)

Intermediate 153F (125 mg, 0.516 mmol), 3-methoxypropanal (50.0 mg, 0.568 mmol), and sodium methoxide (0.5 M, 1135 µL, 0.568 mmol) were dissolved in MeOH (5159 µL) and heated to reflux for 3.5 hours. The reaction mixture was diluted with saturated NH$_4$Cl and EtOAc. The layers were separated and the organic layer was washed with brine, dried (Na$_2$SO$_4$), filtered, and concentrated in vacuo. The crude material was purified by column chromatography (ISCO, 24 g silica gel column, 19 minute gradient from 0 to 100% EtOAc in hexanes) to give Intermediate 153G (47 mg, 0.160 mmol, 30.9%) as a yellow oil: $^1$H NMR (400 MHz, CHLOROFORM-d) δ 8.85 (d, J=2.0 Hz, 1H), 7.96-7.91 (m, 1H), 7.65-7.59 (m, 2H), 7.41-7.34 (m, 2H), 7.33-7.29 (m, 1H), 7.03 (d, J=0.7 Hz, 1H), 7.04-7.00 (m, 1H), 5.74 (s, 2H), 4.66 (d, J=0.7 Hz, 2H), 3.49 (s, 3H), 2.57 (d, J=0.7 Hz, 3H); LC-MS: Method H, RT=1.16 min, MS (ESI) m/z: 295.3 (M+H)$^+$.

Intermediate 153H: 3-(methoxymethyl)-6-methyl-1,7-naphthyridin-8-ol

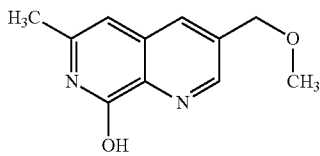
(153H)

Intermediate 153G (47 mg, 0.160 mmol) was dissolved in MeOH (1597 µL). Palladium on carbon (16.99 mg, 0.016 mmol) was added and the reaction mixture was sealed under a balloon of hydrogen for 30 minutes. The reaction mixture was filtered through a micron filter and concentrated in vacuo to give Intermediate 153H (29.6 mg, 0.145 mmol, 91%) as a yellow solid: LC-MS: Method H, RT=0.71 min, MS (ESI) m/z: 205.2 (M+H)$^+$.

Intermediate 153I: 8-chloro-3-(methoxymethyl)-6-methyl-1,7-naphthyridine

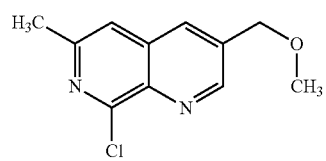
(153I)

Intermediate 153H (29.6 mg, 0.145 mmol) was dissolved in POCl$_3$ (675 µL, 7.25 mmol) and heated to 90° C. for 5 hours. The reaction mixture was diluted with EtOAc and quenched with water. The organic layer was washed with saturated NaHCO$_3$, brine, dried (Na$_2$SO$_4$), filtered, and concentrated in vacuo to give Intermediate 153I (24.3 mg, 0.109 mmol, 75%) as a brown solid: $^1$H NMR (400 MHz, CHLOROFORM-d) δ 8.99 (d, J=2.0 Hz, 1H), 8.09-8.04 (m, 1H), 7.44 (s, 1H), 4.72 (d, J=0.9 Hz, 2H), 3.53 (s, 3H), 2.72 (s, 3H); LC-MS: Method H, RT=0.83 min, MS (ESI) m/z: 223.2 (M+H)$^+$.

Intermediate 153J: 6-methoxy-4-methyl-2-(tributylstannyl)benzo[d]thiazole

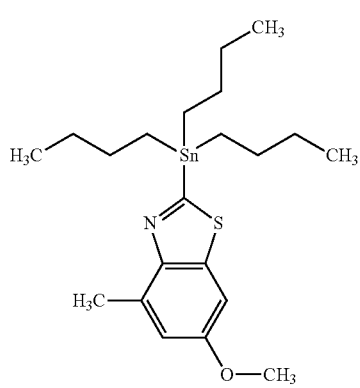
(153J)

Intermediate I-3 (20 mg, 0.077 mmol) was dissolved in Et$_2$O (310 µL) and cooled to −78° C. BuLi (2.5 M, 34.1 µL, 0.085 mmol) was added. After 30 minutes, tributylchlorostannane (21.02 µL, 0.077 mmol) was added. After 45 minutes, the reaction mixture was warmed to ambient temperature and concentrated in vacuo. The crude material was suspended in hexanes and filtered through dry celite. The residue was concentrated in vacuo to give Intermediate 153J, which was used directly in the next reaction.

Example 153

Intermediate 153I (10 mg, 0.045 mmol), Intermediate 153J (30.5 mg, 0.065 mmol), and potassium acetate (8.82 mg, 0.090 mmol) were dissolved in dioxane (449 µL) and degassed by bubbling with argon for 15 minutes. Palladium tetrakistriphenylphosphine (2.59 mg, 2.245 µmol) was added and the reaction mixture was sealed and heated to 120° C. in the microwave for 2 hours. The reaction mixture was diluted with EtOAc, washed with water, then brine, dried (Na$_2$SO$_4$), filtered, and concentrated in vacuo. The crude material was diluted with DMF, filtered, and purified by preparative HPLC (Method D, 20 to 60% B in 15 minutes) to give Example 153 (6 mg, 0.016 mmol, 35.8%): $^1$H NMR (500 MHz, DMSO-d$_6$) δ 9.06 (d, J=2.2 Hz, 1H), 8.39-8.34 (m, 1H), 7.91 (s, 1H), 7.57 (d, J=2.5 Hz, 1H), 7.07-6.99 (m, 1H), 4.75 (s, 2H), 3.88 (s, 3H), 3.44 (s, 3H), 2.78 (s, 3H), 2.76 (s, 3H); LC-MS: Method H, RT=1.07 min, MS (ESI) m/z: 366.1 (M+H)$^+$; Analytical HPLC Method B: 98% purity.

Example 154

(6-methoxy-2-(2-methoxy-7-methylquinoxalin-5-yl)benzo[d]thiazol-4-yl)methanol

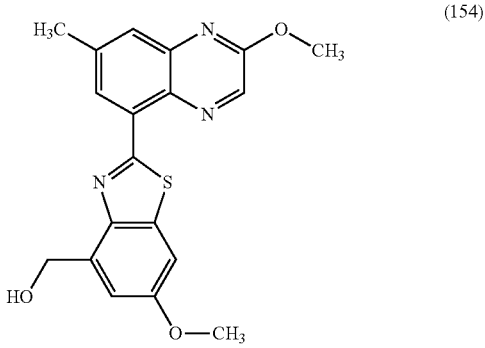 [SMILES: COc1cc(CO)c2nc(-c3cc(C)cc4nc(OC)cnc34)sc2c1]

(154)

Intermediate I-9 (12.77 mg, 0.043 mmol), Intermediate I-20D (14 mg, 0.051 mmol), and potassium phosphate tribasic (18.07 mg, 0.085 mmol) were dissolved in DMF (426 µL) and degassed by bubbling with argon for 15 minutes. Palladium tetrakistriphenylphosphine (4.92 mg, 4.26 µmol) was added and degassing continued for 5 minutes. The reaction mixture was heated to 85° C. for 18 hours. The reaction mixture was diluted with DMF, filtered, and purified by preparative HPLC (Method D, 45 to 90% B in 10 minutes) to give Example 154 (4.5 mg, 0.011 mmol, 26.5%): $^1$H NMR (500 MHz, DMSO-$d_6$) δ 8.73 (s, 1H), 8.59 (s, 1H), 7.82 (s, 1H), 7.59 (d, J=2.2 Hz, 1H), 7.22 (d, J=1.7 Hz, 1H), 5.38 (t, J=5.8 Hz, 1H), 5.13 (d, J=5.5 Hz, 2H), 4.09 (s, 3H), 3.89 (s, 3H), 2.65 (s, 3H); LC-MS: Method H, RT=1.26 min, MS (ESI) m/z: 368.2 (M+H)$^+$; Analytical HPLC Method B: 92% purity.

Example 155

(6-methoxy-2-(2-(methoxymethyl)-7-methylquinoxalin-5-yl)benzo[d]thiazol-4-yl) methanol

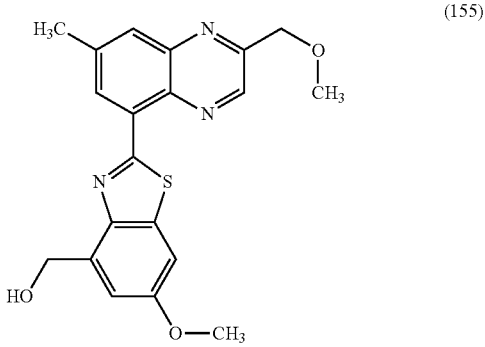 [SMILES: COCc1cnc2c(-c3nc4c(CO)cc(OC)cc4s3)cc(C)cc2n1]

(155)

Intermediate I-2 (13.37 mg, 0.043 mmol), Intermediate I-20D (14 mg, 0.051 mmol), and potassium phosphate tribasic (18.07 mg, 0.085 mmol) were dissolved in DMF (426 µL) and degassed by bubbling with argon for 15 minutes. Palladium tetrakistriphenylphosphine (4.92 mg, 4.26 µmol) was added and degassing continued for 5 minutes. The reaction mixture was heated to 85° C. for 18 hours. The reaction mixture was diluted with DMF, filtered, and purified by preparative HPLC (Method D, 30 to 70% B in 12 minutes) to give Example 155 (3.9 mg, 0.01012 mmol, 23.8%): $^1$H NMR (500 MHz, DMSO-$d_6$) δ 9.10 (s, 1H), 8.81 (s, 1H), 8.04 (s, 1H), 7.62 (d, J=2.2 Hz, 1H), 7.22 (d, J=1.4 Hz, 1H), 5.40 (t, J=5.6 Hz, 1H), 5.14 (d, J=5.5 Hz, 2H), 4.82 (s, 2H), 3.90 (s, 3H), 3.49 (s, 3H), 2.71 (s, 3H); LC-MS: Method H, RT=1.17 min, MS (ESI) m/z: 382.1 (M+H)$^+$; Analytical HPLC Method B: 99% purity.

Example 156

1-(6-methoxy-2-(2-(methoxymethyl)-7-methylquinoxalin-5-yl)benzo[d]thiazol-4-yl) ethanol

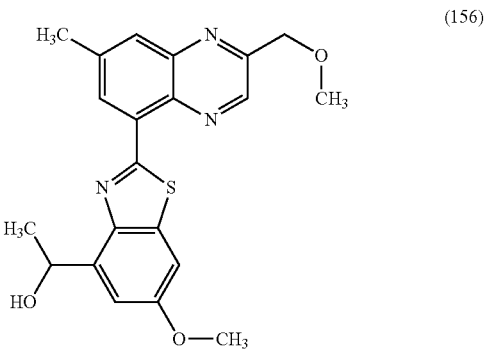 [SMILES: COCc1cnc2c(-c3nc4c(C(C)O)cc(OC)cc4s3)cc(C)cc2n1]

(156)

Intermediate 156A: 1-(2-bromo-6-methoxybenzo[d]thiazol-4-yl)ethanol

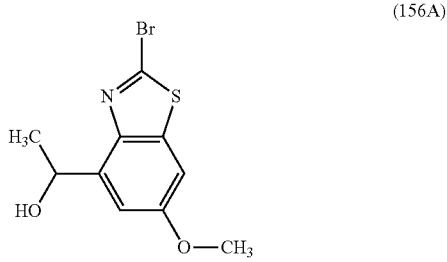

(156A)

Intermediate I-20 (40 mg, 0.147 mmol) was dissolved in THF (294 µL) and cooled to −78° C. Methylmagnesium bromide (61.2 µL, 0.184 mmol) was added. After 1 hour, the reaction mixture was warmed to 0° C. and stirred for 18 hours. The reaction mixture was quenched with saturated NH$_4$Cl and extracted with EtOAc. The organic layer was washed with water, then brine, dried (Na$_2$SO$_4$), filtered, and concentrated in vacuo. The crude material was purified by column chromatography (ISCO, 12 g silica gel column, 17 minute gradient from 0 to 100% EtOAc in hexanes) to give Intermediate 156A (26.8 mg, 0.093 mmol, 63.3%) as a clear oil: $^1$H NMR (400 MHz, CHLOROFORM-d) δ 7.17-7.11 (m, 1H), 7.08-7.04 (m, 1H), 5.41-5.31 (m, 1H), 3.87 (s, 3H), 3.44-3.34 (m, 1H), 1.66-1.60 (m, 3H); LC-MS: Method H, RT=1.06 min, MS (ESI) m/z: 288/290 (M+H)$^+$.

Example 156

Intermediate I-2 (12.18 mg, 0.039 mmol), Intermediate 156A (13.4 mg, 0.047 mmol), and potassium phosphate tribasic (16.45 mg, 0.078 mmol) were dissolved in DMF (388 μL) and degassed by bubbling with argon for 15 minutes. Palladium tetrakistriphenylphosphine (4.48 mg, 3.88 μmol) was added and degassing continued for 5 minutes. The reaction mixture was heated to 85° C. for 18 hours. The reaction mixture was diluted with DMF, filtered, and purified by preparative HPLC (Method D, 30 to 70% B in 20 minutes) to give Example 156 (5.1 mg, 0.012 mmol, 31.9%): $^1$H NMR (500 MHz, DMSO-$d_6$) δ 9.11 (br. s., 1H), 8.80 (br. s., 1H), 8.05 (br. s., 1H), 7.61 (br. s., 1H), 7.25 (br. s., 1H), 5.68 (d, J=4.7 Hz, 1H), 4.83 (br. s., 2H), 3.89 (br. s., 3H), 3.49 (br. s., 3H), 2.71 (br. s., 3H), 1.57 (d, J=5.0 Hz, 3H); LC-MS: Method H, RT=1.13 min, MS (ESI) m/z: 396.2 $(M+H)^+$; Analytical HPLC Method B: 96% purity.

Example 157

2-(6-methoxy-2-(2-(methoxymethyl)-7-methylquinoxalin-5-yl)benzo[d]thiazol-4-yl) propan-2-ol

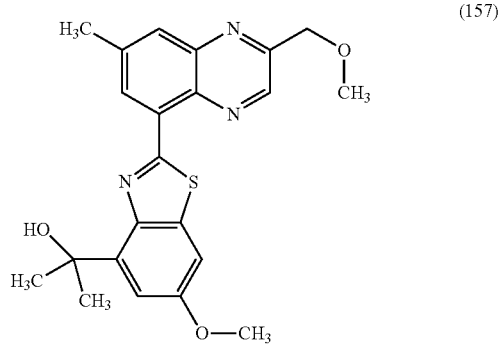 [SMILES: COCc1cnc2c(-c3nc4c(C(C)(C)O)cc(OC)cc4s3)cc(C)cc2n1]

(157)

Intermediate 157A: 2-(2-bromo-6-methoxybenzo[d]thiazol-4-yl)propan-2-ol

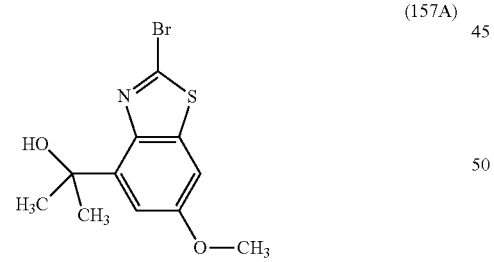

(157A)

Intermediate I-20C (50 mg, 0.165 mmol) was dissolved in THF (331 μL) and cooled to −78° C. Methylmagnesium bromide (124 μL, 0.372 mmol) was added and the reaction mixture warmed to 0° C. for 18 hours. The reaction mixture was quenched with saturated NH$_4$Cl and extracted with EtOAc. The organic layer was washed with water, then brine, dried (Na$_2$SO$_4$), filtered, and concentrated in vacuo. The crude material was purified by column chromatography (ISCO, 12 g silica gel column, 17 minute gradient from 0 to 100% EtOAc in hexanes) to give Intermediate 157A (13.6 mg, 0.045 mmol, 27.2%) as a clear oil: LC-MS: Method H, RT=1.00 min, MS (ESI) m/z: 302/304 $(M+H)^+$.

Example 157

Intermediate I-2 (11.78 mg, 0.038 mmol), Intermediate 157A (13.6 mg, 0.045 mmol), and potassium phosphate tribasic (15.92 mg, 0.075 mmol) were dissolved in DMF (375 μL) and degassed by bubbling with argon for 15 minutes. Palladium tetrakistriphenylphosphine (4.33 mg, 3.75 μmol) was added and degassing continued for 5 minutes. The reaction mixture was heated to 85° C. for 18 hours. The reaction mixture was diluted with DMF, filtered, and purified by preparative HPLC (Method D, 40 to 80% B in 15 minutes) to give Example 157 (8.1 mg, 0.020 mmol, 52.2%): $^1$H NMR (500 MHz, DMSO-$d_6$) δ 9.11 (s, 1H), 8.73 (d, J=1.9 Hz, 1H), 8.07-8.02 (m, 1H), 7.62 (d, J=2.5 Hz, 1H), 7.36 (d, J=2.8 Hz, 1H), 5.42 (s, 1H), 4.83 (s, 2H), 3.89 (s, 3H), 3.49 (s, 3H), 2.71 (s, 3H), 1.84 (s, 6H); LC-MS: Method H, RT=1.12 min, MS (ESI) m/z: 410.2 $(M+H)^+$; Analytical HPLC Method B: 99% purity.

Example 158

Cyclopropyl(6-methoxy-2-(2-(methoxymethyl)-7-methylquinoxalin-5-yl) benzo[d]thiazol-4-yl)methanol

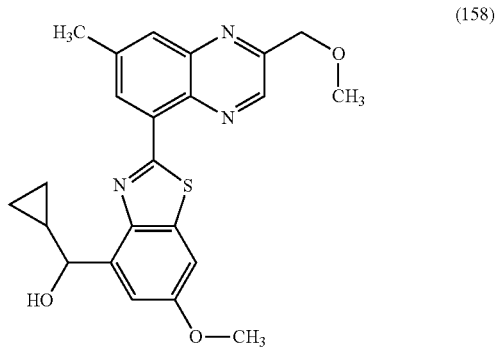 [SMILES: COCc1cnc2c(-c3nc4c(C(O)C5CC5)cc(OC)cc4s3)cc(C)cc2n1]

(158)

Intermediate 158A: (2-bromo-6-methoxybenzo[d]thiazol-4-yl)(cyclopropyl)methanol

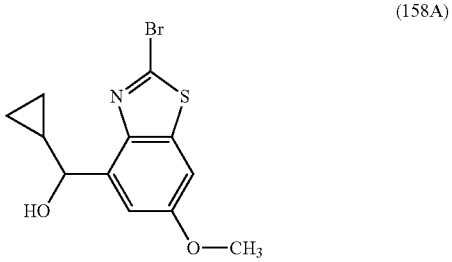 [SMILES: COc1cc(C(O)C2CC2)c2nc(Br)sc2c1]

(158A)

Intermediate I-20 (40 mg, 0.147 mmol) was dissolved in THF (294 μL) and cooled to −78° C. Cyclopropylmagnesium bromide (367 μL, 0.184 mmol) was added and the reaction mixture was warmed to 0° C. for 18 hours. The reaction mixture was quenched with saturated NH$_4$Cl and extracted with EtOAc. The organic layer was washed with water, then brine, dried (Na$_2$SO$_4$), filtered, and concentrated in vacuo. The crude material was purified by column chromatography (ISCO, 12 g silica gel column, 17 minute gradient from 0 to 100% EtOAc in hexanes) to give Intermediate 158A (24.5 mg, 0.078 mmol, 53%) as a yellow oil, which was used directly in the subsequent reaction.

Example 158

Intermediate I-2 (14.40 mg, 0.046 mmol), Intermediate 158A (12 mg, 0.038 mmol), and potassium phosphate tribasic (16.21 mg, 0.076 mmol) were dissolved in DMF (382 μL) and degassed by bubbling with argon for 15 minutes. Palladium tetrakistriphenylphosphine (4.41 mg, 3.82 μmol) was added and degassing continued for 5 minutes. The reaction mixture was heated to 85° C. for 18 hours. The reaction mixture was diluted with DMF, filtered, and purified by preparative HPLC (Method D, 35 to 75% B in 15 minutes) to give Example 158 (9.2 mg, 0.022 mmol, 57.1%): $^1$H NMR (500 MHz, DMSO-$d_6$) δ 9.11 (s, 1H), 8.78 (d, J=1.7 Hz, 1H), 8.05 (s, 1H), 7.63 (d, J=2.5 Hz, 1H), 7.25 (d, J=2.5 Hz, 1H), 5.35 (d, J=4.7 Hz, 1H), 5.14 (dd, J=6.5, 5.1 Hz, 1H), 4.83 (s, 2H), 3.89 (s, 3H), 3.48 (s, 3H), 2.71 (s, 3H), 1.36-1.27 (m, 1H), 0.62 (dt, J=9.1, 4.5 Hz, 1H), 0.54 (td, J=9.1, 5.1 Hz, 1H), 0.49-0.42 (m, 1H), 0.42-0.34 (m, 1H); LC-MS: Method H, RT=1.11 min, MS (ESI) m/z: 421.8 (M+H)$^+$; Analytical HPLC Method B: 100% purity.

Example 159

1-(6-methoxy-2-(2-(methoxymethyl)-7-methylquinoxalin-5-yl)benzo[d]thiazol-4-yl)-N,N-dimethylmethanamine (159)

Intermediate 159A: methyl 5-methoxy-2-nitrobenzoate (159A)

5-methoxy-2-nitrobenzoic acid (2 g, 10.14 mmol) was dissolved in MeOH (50.7 mL). SOCl$_2$ (2.96 mL, 40.6 mmol) was added and the reaction mixture was heated to reflux for 20 hours. The reaction mixture was concentrated in vacuo. The crude material was dissolved in EtOAc and washed with 1 N NaOH, then water, then brine, dried (Na$_2$SO$_4$), filtered, and concentrated in vacuo to give Intermediate 159A (1.7786 g, 8.42 mmol, 83%) as a brown oil: $^1$H NMR (400 MHz, CHLOROFORM-d) δ 8.04 (d, J=9.0 Hz, 1H), 7.07-6.99 (m, 2H), 3.94 (s, 3H), 3.92 (s, 3H); LC-MS: Method H, The compound did not ionize.

Intermediate 159B: (5-methoxy-2-nitrophenyl)methanol (159C)

Intermediate 159A (1.676 g, 7.94 mmol) was dissolved in toluene (52.9 mL) and THF (26.5 mL) and cooled to −78° C. DIBAL-H (17.46 mL, 17.46 mmol) was added for 30 minutes. The reaction mixture was warmed to ambient temperature for 2 hours. The reaction was quenched with 1 N HCl and stirred for 18 hours. The reaction mixture was diluted with EtOAc, filtered through celite, washed with water, then brine, dried (Na$_2$SO$_4$), filtered, and concentrated in vacuo. The crude material was purified by column chromatography (ISCO, 80 g silica gel column, 29 minute gradient from 0 to 100% EtOAc in hexanes) to give Intermediate 159B (1.21 g, 6.61 mmol, 83%) as a yellow solid: $^1$H NMR (400 MHz, CHLOROFORM-d) δ 8.18 (d, J=9.0 Hz, 1H), 7.22 (d, J=2.9 Hz, 1H), 6.90 (dd, J=9.0, 2.9 Hz, 1H), 5.00 (d, J=6.4 Hz, 2H), 3.92 (s, 3H), 2.55 (t, J=6.6 Hz, 1H); LC-MS: Method H, The compound did not ionize.

Intermediate 159C: 5-methoxy-2-nitrobenzyl methanesulfonate (159C)

Intermediate 159B (0.2 g, 1.092 mmol) and TEA (0.457 mL, 3.28 mmol) were dissolved in DCM (21.84 mL). Methanesulfonic anhydride (0.228 g, 1.310 mmol) was added for 45 minutes. The reaction mixture was diluted with DCM and washed with saturated NaHCO$_3$, dried (Na$_2$SO$_4$), filtered, and concentrated in vacuo to give Intermediate 159C. The material was used crude in the next step.

Intermediate 159D: 1-(5-methoxy-2-nitrophenyl)-N,N-dimethylmethanamine

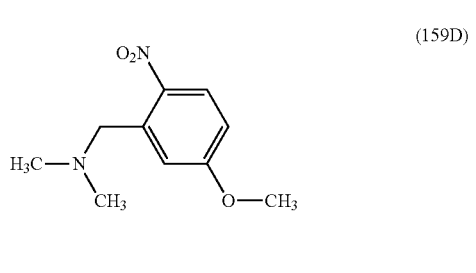

(159D)

Intermediate 159C (0.285 g, 1.091 mmol), DIEA (0.286 mL, 1.636 mmol), and dimethylamine (1.091 mL, 2.182 mmol) were dissolved in THF (10.91 mL) for 18 hours. The reaction mixture was concentrated in vacuo. The crude material was purified by column chromatography (ISCO, 40 g silica gel column, 19 minute gradient from 0 to 100% EtOAc in hexanes) to give Intermediate 159D (66.4 mg, 0.316 mmol, 29%) as a yellow oil: $^1$H NMR (400 MHz, CHLOROFORM-d) δ 7.99 (d, J=9.0 Hz, 1H), 7.24 (d, J=2.9 Hz, 1H), 6.83 (dd, J=9.0, 2.9 Hz, 1H), 3.90 (s, 3H), 3.77 (s, 2H), 2.27 (s, 6H); LC-MS: Method H, RT=0.54 min, MS (ESI) m/z: 211.2 (M+H)$^+$.

Intermediate 159E: 2-((dimethylamino)methyl)-4-methoxyaniline, TFA

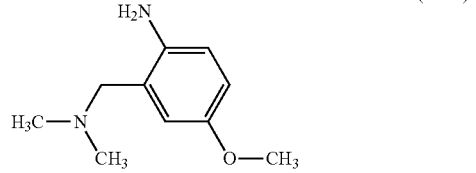

(159E)

Intermediate 159D (66 mg, 0.314 mmol) was dissolved in MeOH (2147 μL) and THF (268 μL). Ammonium chloride (336 mg, 6.28 mmol) and zinc (205 mg, 3.14 mmol) were added and the reaction mixture was heated to 40° C. for 4.5 hours. The reaction mixture was diluted with EtOAc and saturated sodium carbonate and allowed to stir vigorously for 15 minutes. The mixture was filtered through a sintered glass funnel. The organic layer was washed with water then brine, dried (Na$_2$SO$_4$), filtered, and concentrated in vacuo. The crude material was purified by preparative HPLC (Method A, 20 to 100% B in 12 minutes) to give Intermediate 159E (34.3 mg, 0.117 mmol, 37.1%) as a brown oil: $^1$H NMR (400 MHz, MeOH-d$_4$) δ 6.99-6.94 (m, 2H), 6.93-6.89 (m, 1H), 4.30 (s, 2H), 3.77 (s, 3H), 2.87 (s, 6H); LC-MS: Method H, RT=0.55 min, MS (ESI) m/z: 181.2 (M+H)$^+$.

Intermediate 159F: 4-((dimethylamino)methyl)-6-methoxybenzo[d]thiazol-2-amine

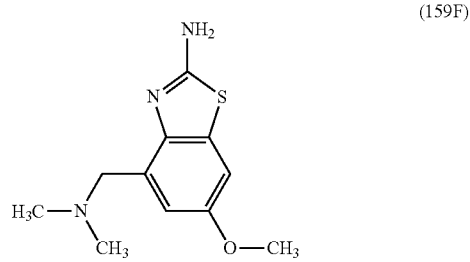

(159F)

Intermediate 159E (34.3 mg, 0.117 mmol) was dissolved in MeCN (583 μL). Ammonium thiocyanate (13.31 mg, 0.175 mmol) was added, followed by benzyltrimethylammonium tribromide (45.5 mg, 0.117 mmol) for 18 hours. The reaction mixture was diluted with EtOAc, washed with saturated NaHCO$_3$, then brine, dried (Na$_2$SO$_4$), filtered, and concentrated in vacuo to give Intermediate 159F (10.3 mg, 0.043 mmol, 37.2%) as a yellow oil: LC-MS: Method H, RT=1.01 min, MS (ESI) m/z: 238.1 (M+H)$^+$.

Intermediate 159G: 1-(2-bromo-6-methoxybenzo[d]thiazol-4-yl)-N,N-dimethylmethanamine

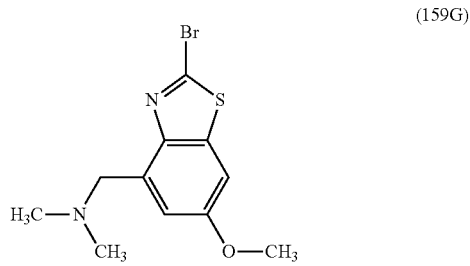

(159G)

Copper(II) bromide (16.00 mg, 0.072 mmol) and t-butyl nitrite (8.52 μL, 0.072 mmol) were dissolved in MeCN (169 μL) and allowed to stir 10 minutes. Intermediate 159F (10 mg, 0.042 mmol) was dissolved in MeCN (253 μL) and the copper solution was added at and the reaction mixture was stirred for 75 minutes. The reaction mixture was diluted with EtOAc, washed with 1 N HCl, saturated NaHCO$_3$, then brine, dried (Na$_2$SO$_4$), filtered, and concentrated in vacuo to give Intermediate 159G (9.8 mg, 0.033 mmol, 77%), which was used as-is for the subsequent step: LC-MS: Method H, RT=1.017 min, MS (ESI) m/z: 301/303 (M+H)$^+$.

Example 159

Intermediate I-2 (12.27 mg, 0.039 mmol), Intermediate 159G (9.8 mg, 0.033 mmol), and potassium phosphate tribasic (13.81 mg, 0.065 mmol) were dissolved in DMF (325 μL) and degassed by bubbling with argon for 15 minutes. Palladium tetrakistriphenylphosphine (3.76 mg, 3.25 μmol) was added and degassing continued for 5 minutes. The reaction mixture was heated to 85° C. for 18 hours. The reaction mixture was diluted with DMF, filtered, and purified by preparative HPLC (Method D, 20 to 60% B in 20 minutes) then repurified by preparative HPLC (Method D, 20 to 60% B in 15 minutes) to give Example 159 (2.8 mg, 0.00651 mmol, 20%): $^1$H NMR (500 MHz, DMSO-d$_6$) δ 9.11 (s, 1H), 8.90 (d, J=1.7 Hz, 1H), 8.08 (s, 1H), 7.82 (d, J=1.9 Hz, 1H), 7.32 (d, J=1.9 Hz, 1H), 4.82 (s, 2H), 4.59 (br. s., 2H), 3.91 (s, 3H), 3.48 (s, 3H), 2.72 (s, 6H) (1 methyl group buried under the water peak); LC-MS: Method H, RT=0.80 min, MS (ESI) m/z: 408.8 (M+H)$^+$; Analytical HPLC Method B: 95% purity.

Example 160

Cyclopropyl(6-methoxy-2-(2-methoxy-7-methylquinoxalin-5-yl)benzo[d]thiazol-4-yl) methanol

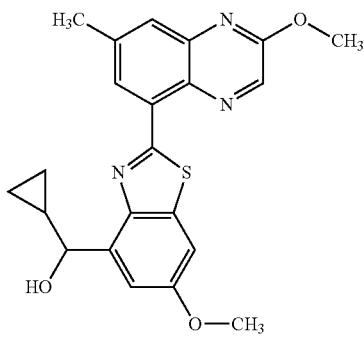

(160)

Intermediate I-9 (13.76 mg, 0.046 mmol), Intermediate 158A (12 mg, 0.038 mmol), and potassium phosphate tribasic (16.21 mg, 0.076 mmol) were dissolved in DMF (382 μL) and degassed by bubbling with argon for 15 minutes. Palladium tetrakistriphenylphosphine (4.41 mg, 3.82 μmol) was added and degassing continued for 5 minutes. The reaction mixture was heated to 85° C. for 18 hours. The reaction mixture was diluted with DMF, filtered, and purified by preparative HPLC (Method D, 45 to 85% B in 15 minutes) to give Example 160 (4.2 mg, 0.0103 mmol, 27%): $^1$H NMR (500 MHz, DMSO-d$_6$) δ 8.75 (s, 1H), 8.55 (d, J=1.7 Hz, 1H), 7.83 (s, 1H), 7.60 (d, J=2.5 Hz, 1H), 7.24 (d, J=2.5 Hz, 1H), 5.35 (d, J=5.0 Hz, 1H), 5.13 (dd, J=6.5, 5.1 Hz, 1H), 4.09 (s, 3H), 3.89 (s, 3H), 2.65 (s, 3H), 1.34-1.27 (m, 1H), 0.61 (dt, J=9.0, 4.4 Hz, 1H), 0.57-0.50 (m, 1H), 0.49-0.42 (m, 1H), 0.42-0.34 (m, 1H); LC-MS: Method H, RT=1.21 min, MS (ESI) m/z: 407.8 (M+H)$^+$; Analytical HPLC Method B: 98% purity.

Example 161

(6-methoxy-2-(2-(methoxymethyl)-7-methylquinoxalin-5-yl)benzo[d]thiazol-4-yl) (phenyl)methanol

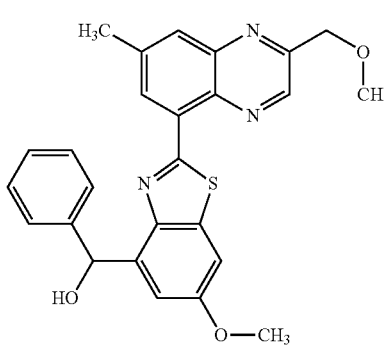

(161)

Intermediate 161A: (2-bromo-6-methoxybenzo[d]thiazol-4-yl)(phenyl)methanol

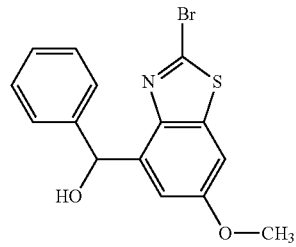

(161)

Intermediate I-20 (40 mg, 0.147 mmol) was dissolved in THF (294 μL) and cooled to −78° C. Phenylmagnesium bromide (61.2 μL, 0.184 mmol) was added and the reaction mixture was warmed to 0° C. for 18 hours. The reaction mixture was quenched with saturated NH$_4$Cl and extracted with EtOAc. The organic layer was washed with water, then brine, dried (Na$_2$SO$_4$), filtered, and concentrated in vacuo. The crude material was purified by column chromatography (ISCO, 12 g silica gel column, 17 minute gradient from 0 to 100% EtOAc in hexanes) to give Intermediate 161A (33.6 mg, 0.096 mmol, 65.3%) as a white solid: LC-MS: Method H, RT=1.01 min, MS (ESI) m/z: 350/352 (M+H)$^+$.

Example 161

Intermediate I-2 (14.80 mg, 0.047 mmol), Intermediate 161A (16.5 mg, 0.047 mmol), and potassium phosphate tribasic (20.00 mg, 0.094 mmol) were dissolved in DMF (471 μL) and degassed by bubbling with argon for 15 minutes. Palladium tetrakistriphenylphosphine (5.44 mg, 4.71 μmol) was added and degassing continued for 5 minutes. The reaction mixture was heated to 85° C. for 18 hours. The reaction mixture was diluted with DMF, filtered, and purified by preparative HPLC (Method D, 40 to 75% B in 15 minutes) to give Example 161 (11 mg, 0.024 mmol, 50%): $^1$H NMR (500 MHz, DMSO-d$_6$) δ 9.10 (s, 1H), 8.83 (d, J=1.7 Hz, 1H), 8.06 (d, J=0.6 Hz, 1H), 7.65-7.57 (m, 3H), 7.35-7.27 (m, 3H), 7.23-7.16 (m, 1H), 6.72 (d, J=4.1 Hz, 1H), 6.10 (d, J=4.4 Hz, 1H), 4.82 (s, 2H), 3.87 (s, 3H), 3.48 (s, 3H), 2.74 (s, 3H); LC-MS: Method H, RT=1.14 min, MS (ESI) m/z: 457.8 (M+H)$^+$; Analytical HPLC Method B: 98% purity.

Example 162

6-methoxy-2-(2-(methoxymethyl)-7-methylquinoxalin-5-yl)benzo[d]thiazole-4-carboxylic acid

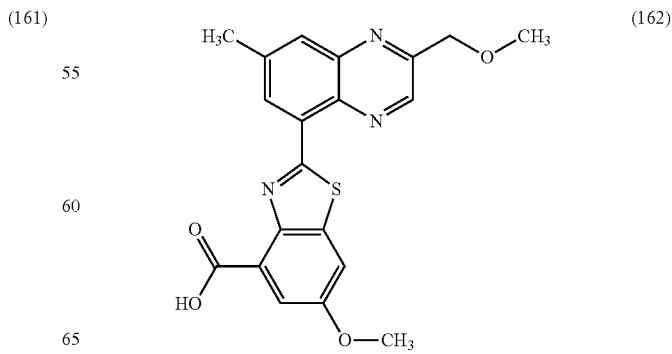

Intermediate 162A: 5-methoxy-2-nitrobenzoyl chloride

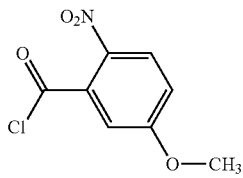

(162A)

5-Methoxy-2-nitrobenzoic acid (1 g, 5.07 mmol) was dissolved in DCM (50.7 mL). Oxalyl chloride (0.958 mL, 11.16 mmol) then DMF (0.039 mL, 0.507 mmol) was added at ambient temperature and the reaction mixture was stirred for 2.5 hours. The reaction mixture was concentrated in vacuo and stored on HIVAC to give Intermediate 162A, which was used directly in the subsequent reaction.

Intermediate 162B: tert-butyl 5-methoxy-2-nitrobenzoate

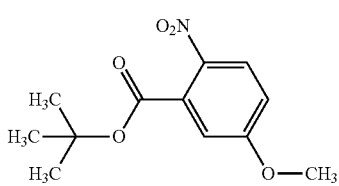

(162B)

Intermediate 162A (1.094 g, 5.07 mmol) was dissolved in THF (50.7 mL). Potassium tert-butoxide (0.854 g, 7.61 mmol) was added and the reaction mixture was stirred for 18 hours. The reaction mixture was diluted with EtOAc and washed with water, then brine, dried ($Na_2SO_4$), filtered, and concentrated in vacuo to give Intermediate 162B (910 mg, 3.59 mmol, 70.8%) as a brown oil: $^1$H NMR (400 MHz, CHLOROFORM-d) δ 7.98 (d, J=9.0 Hz, 1H), 7.03 (d, J=2.9 Hz, 1H), 6.98 (dd, J=9.0, 2.6 Hz, 1H), 3.91 (s, 3H), 1.58 (s, 9H); LC-MS: Method H, the compound did not ionize.

Intermediate 162C: tert-butyl 2-amino-5-methoxybenzoate

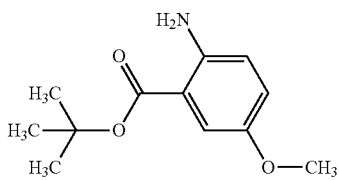

(162C)

Intermediate 162B (0.910 g, 3.59 mmol) was dissolved in EtOH (5.13 mL). Palladium on carbon (0.076 g, 0.072 mmol) then ammonium formate (1.133 g, 17.97 mmol) was added and the reaction mixture was heated to reflux for 1.5 hours. The reaction mixture was filtered through celite and concentrated in vacuo to give Intermediate 162C (795 mg, 3.56 mmol, 99%) as a brown oil: $^1$H NMR (400 MHz, CHLOROFORM-d) δ 7.33 (d, J=2.9 Hz, 1H), 6.92 (dd, J=8.8, 3.1 Hz, 1H), 6.61 (d, J=8.8 Hz, 1H), 5.36 (br. s., 2H), 3.76-3.74 (m, 3H), 1.59 (s, 9H); LC-MS: Method H, The compound did not ionize.

Intermediate 162D: tert-butyl 2-amino-6-methoxy-benzo[d]thiazole-4-carboxylate

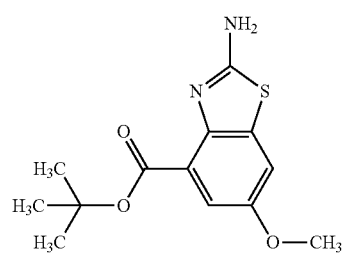

(162D)

Intermediate 162C (0.795 g, 3.56 mmol) was dissolved in MeCN (17.80 mL). Ammonium thiocyanate (0.407 g, 5.34 mmol) was added, followed by benzyltrimethylammonium tribromide (1.389 g, 3.56 mmol) for 18 hours. The reaction mixture was diluted with EtOAc, washed with saturated $NaHCO_3$, then brine, dried ($Na_2SO_4$), filtered, and concentrated in vacuo. The crude material was purified by column chromatography (ISCO, 80 g silica gel column, 29 minute gradient from 0 to 100% EtOAc in hexanes) to give Intermediate 162D (685.8 mg, 2.446 mmol, 68.7%) as a yellow solid: $^1$H NMR (400 MHz, chloroform-d) δ 7.46 (d, J=2.6 Hz, 1H), 7.29 (d, J=2.6 Hz, 1H), 5.71 (br. s., 2H), 3.85 (s, 3H), 1.63 (s, 9H); LC-MS: Method H, RT=1.32 min, MS (ESI) m/z: 282.1 (M+H)$^+$.

Intermediate 162E: tert-butyl 2-bromo-6-methoxy-benzo[d]thiazole-4-carboxylate

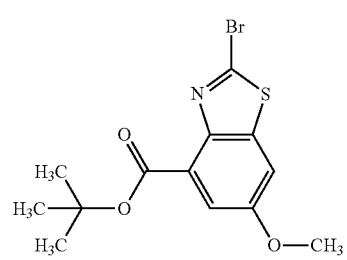

(162E)

Copper(II) bromide (0.928 g, 4.15 mmol) and t-butyl nitrite (0.494 mL, 4.15 mmol) were dissolved in MeCN (9.77 mL) and allowed to stir 10 minutes. Intermediate 162D (0.685 g, 2.443 mmol) was dissolved in MeCN (14.66 mL) and the copper solution was added for 2.5 hours. The reaction mixture was diluted with EtOAc, washed with 1 N HCl, saturated $NaHCO_3$, then brine, dried ($Na_2SO_4$), filtered, and concentrated in vacuo. The crude material was purified by column chromatography (ISCO, 80 g silica gel column, 29 minute gradient from 0 to 100% EtOAc in hexanes) to give Intermediate 162E (323.8 mg, 0.941 mmol, 38.5%) as a white solid: $^1$H NMR (400 MHz, CHLOROFORM-d) δ 7.59 (d, J=2.6 Hz, 1H), 7.40 (d, J=2.6 Hz, 1H), 3.90 (s, 3H), 1.65 (s, 9H); LC-MS: The compound did not ionize.

515

Intermediate 162F: tert-butyl 6-methoxy-2-(2-(methoxymethyl)-7-methylquinoxalin-5-yl)benzo[d]thiazole-4-carboxylate

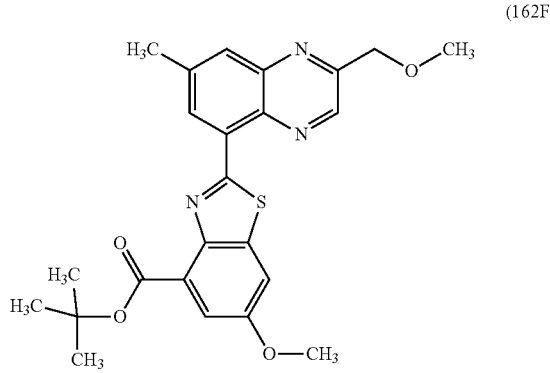 [SMILES: COCc1cnc2c(-c3nc4c(C(=O)OC(C)(C)C)cc(OC)cc4s3)cc(C)cc2n1]

(162F)

Intermediate I-2 (22.82 mg, 0.073 mmol), Intermediate 162E (25 mg, 0.073 mmol), and potassium phosphate tribasic (30.8 mg, 0.145 mmol) were dissolved in DMF (726 μL) and degassed by bubbling with argon for 15 minutes. Palladium tetrakistriphenylphosphine (8.39 mg, 7.26 μmol) was added and degassing continued for 5 minutes. The reaction mixture was heated to 85° C. for 18 hours. The reaction mixture was diluted with water and extracted thrice with EtOAc. The combined organic layers were washed with brine, dried ($Na_2SO_4$), filtered, and concentrated in vacuo. The crude material was purified by column chromatography (ISCO, 12 g silica gel column, 17 minute gradient from 0 to 100% EtOAc in hexanes) to give Intermediate 162F (14.7 mg, 0.033 mmol, 44.8%) as an orange solid: LC-MS: Method H, RT=1.22 min, MS (ESI) m/z: 452.2 (M+H)$^+$.

Example 162

Intermediate 162F (14.7 mg, 0.033 mmol) was dissolved in DCM (1085 μL) and cooled to 0° C. 2,6-Lutidine (11.38 μL, 0.098 mmol) and TMS-OTf (17.65 μL, 0.098 mmol) were added and the reaction mixture was warmed to ambient temperature for 45 minutes. The reaction mixture was diluted with water and extracted with DCM. The organic layer was washed with brine, dried ($Na_2SO_4$), filtered, and concentrated in vacuo. The crude material was dissolved in DMF, filtered, and purified by preparative HPLC (Method D, 20 to 60% B in 12 minutes) to give Example 162 (5.5 mg, 0.014 mmol, 42.3%): LC-MS: Method H, RT=1.07 min, MS (ESI) m/z: 396.1 (M+H)$^+$; Analytical HPLC Method B: 99% purity.

Example 163

(6-methoxy-2-(2-(methoxymethyl)-7-methylquinoxalin-5-yl)benzo[d]thiazol-4-yl)(phenyl)methanol

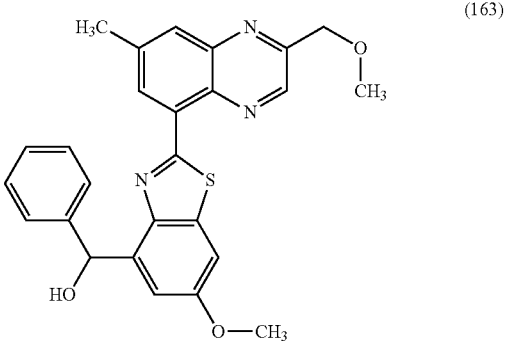

(163)

Example 161 (8 mg, 0.017 mmol) was purified by SFC chromatography (Berger Multigram II SFC, Chiralpak OJ-H, 21×250 mm, 5 micron, 25% MeOH/75% $CO_2$, 45 mL/min flow rate) to give Enantiomer 1 (1.54 mg, 0.0032 mmol, 19%) and Example 163 (Enantiomer 2, 3.4 mg, 0.00706 mmol, 40.4%) as a yellow solid: $^1$H NMR (400 MHz, CHLOROFORM-d) δ 9.08 (s, 1H), 8.75 (d, J=1.5 Hz, 1H), 7.96 (s, 1H), 7.57 (d, J=7.5 Hz, 2H), 7.39-7.33 (m, 2H), 7.32 (d, J=2.4 Hz, 1H), 7.28 (d, J=7.5 Hz, 1H), 6.86 (d, J=2.0 Hz, 1H), 6.40 (d, J=5.7 Hz, 1H), 5.78 (d, J=6.2 Hz, 1H), 4.84 (s, 2H), 3.86 (s, 3H), 3.58 (s, 3H), 2.70 (s, 3H); LC-MS: Method H, RT=1.11 min, MS (ESI) m/z: 458.3 (M+H)$^+$; 95% purity.

Example 164

1-(6-methoxy-2-(2-(methoxymethyl)-7-methylquinoxalin-5-yl)benzo[d]thiazol-4-yl)-2,2-dimethylpropan-1-ol

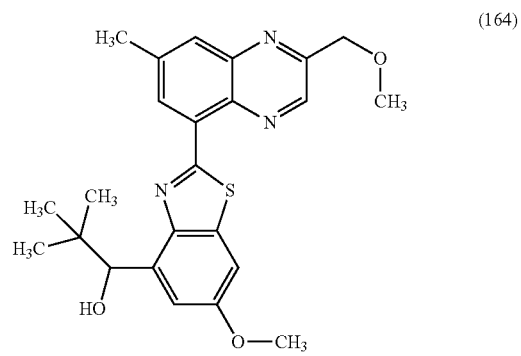 [SMILES: COCc1cnc2c(-c3nc4c(C(O)C(C)(C)C)cc(OC)cc4s3)cc(C)cc2n1]

(164)

Intermediate 164A: 1-(2-bromo-6-methoxybenzo[d]thiazol-4-yl)-2,2-dimethylpropan-1-ol

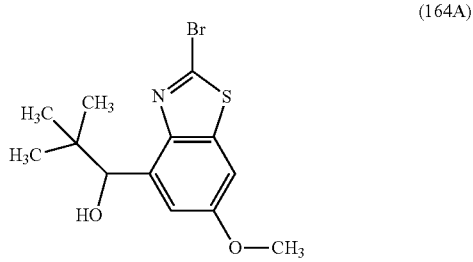 [SMILES: COc1cc(C(O)C(C)(C)C)c2nc(Br)sc2c1]
(164A)

Intermediate I-20 (100 mg, 0.367 mmol) was dissolved in THF (3675 μL) and cooled to −78° C. tert-Butylmagnesium chloride (1 M, 735 μL, 0.735 mmol) was added and warmed to 0° C. for 2 hours. The reaction was quenched with saturated $NH_4Cl$ and extracted with EtOAc. The organic layer was washed with water, then brine, dried ($Na_2SO_4$), filtered, and concentrated in vacuo. The crude material was purified by column chromatography (ISCO, 24 g silica gel column, 17 minute gradient from 0 to 100% EtOAc in hexanes) to give Intermediate 164A (74.2 mg, 0.225 mmol, 61.1%) as a yellow solid: LC-MS: Method H, RT=1.07 min, MS (ESI) m/z: 330/332 (M+H)+.

Intermediate 164B: 1-(6-methoxy-2-(2-(methoxymethyl)-7-methylquinoxalin-5-yl) benzo[d]thiazol-4-yl)-2,2-dimethylpropan-1-ol

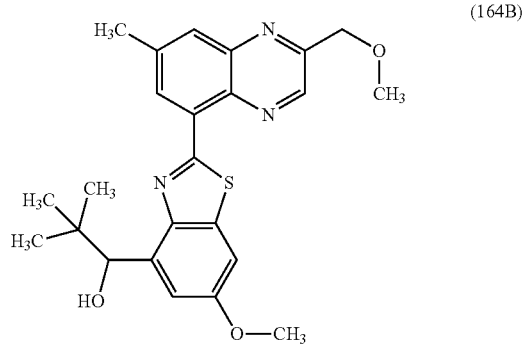 [SMILES: COCc1cnc2c(-c3nc4c(C(O)C(C)(C)C)cc(OC)cc4s3)cc(C)cc2n1]
(164B)

Intermediate I-2 (58.8 mg, 0.187 mmol) and Intermediate 164A (74.2 mg, 0.225 mmol) were dissolved in DMF (1872 μL). $PdCl_2(dppf)\text{-}CH_2Cl_2$ (9.17 mg, 0.011 mmol) was added and the reaction mixture was degassed by bubbling with argon for 15 minutes. Sodium carbonate (2 M, 112 μL, 0.225 mmol) was added and the reaction mixture was degassed for 5 minutes, then sealed and heated to 100° C. in the microwave for 30 minutes. The reaction mixture was diluted with EtOAc, washed with water, then brine, dried ($Na_2SO_4$), filtered, and concentrated in vacuo. The crude material was purified by column chromatography (ISCO, 24 g silica gel column, 19 minute gradient from 0 to 100% EtOAc in hexanes) to give Intermediate 164B (45 mg, 0.103 mmol, 54.9%) as a yellow solid: 1H NMR (500 MHz, DMSO-$d_6$) δ 9.11 (s, 1H), 8.77 (d, J=1.9 Hz, 1H), 8.05 (s, 1H), 7.65 (d, J=2.5 Hz, 1H), 7.16 (d, J=2.5 Hz, 1H), 5.45 (d, J=4.7 Hz, 1H), 5.34 (d, J=4.7 Hz, 1H), 4.83 (s, 2H), 3.89 (s, 3H), 3.48 (s, 3H), 2.72 (s, 3H), 0.97 (s, 9H); LC-MS: Method H, RT=1.19 min, MS (ESI) m/z: 438.2 (M+H)+.

Example 164

Intermediate 164B (62 mg, 0.017 mmol) was purified by SFC chromatography (Berger Multigram II SFC, Chiralpak OJ-H, 21×250 mm, 5 micron, 25% MeOH/75% $CO_2$, 45 mL/min flow rate) to give Enantiomer 1 (15.2 mg, 0.034 mmol, 24.3%) and Example 164 (Enantiomer 2, 18.3 mg, 0.040 mmol, 28%) as a yellow solid: 1H NMR (500 MHz, DMSO-$d_6$) δ 9.11 (s, 1H), 8.77 (d, J=1.9 Hz, 1H), 8.05 (s, 1H), 7.65 (d, J=2.5 Hz, 1H), 7.16 (d, J=2.5 Hz, 1H), 5.45 (d, J=4.7 Hz, 1H), 5.34 (d, J=4.7 Hz, 1H), 4.83 (s, 2H), 3.89 (s, 3H), 3.48 (s, 3H), 2.72 (s, 3H), 0.97 (s, 9H); LC-MS: Method H, RT=1.19 min, MS (ESI) m/z: 438.2 (M+H)+; 95% purity.

Example 165

Cyclohexyl(6-methoxy-2-(2-(methoxymethyl)-7-methylquinoxalin-5-yl)benzo[d]thiazol-4-yl)methanol

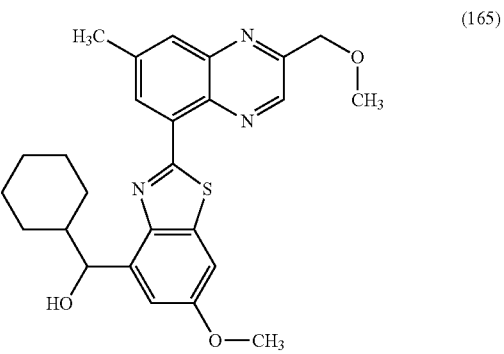 [SMILES: COCc1cnc2c(-c3nc4c(C(O)C5CCCCC5)cc(OC)cc4s3)cc(C)cc2n1]
(165)

Intermediate 165A: (2-bromo-6-methoxybenzo[d]thiazol-4-yl)(cyclohexyl)methanol

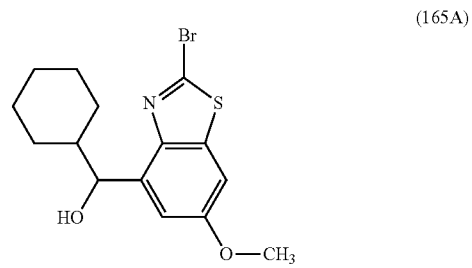 [SMILES: COc1cc(C(O)C2CCCCC2)c2nc(Br)sc2c1]
(165A)

Intermediate I-20 (20 mg, 0.073 mmol) was dissolved in THF (735 μL) and cooled to −78° C. Cyclohexylmagnesium bromide (1 M, 147 μL, 0.147 mmol) was added and the reaction mixture was warmed to 0° C. for 5 hours. The reaction was quenched with saturated $NH_4Cl$ and extracted with EtOAc. The organic layer was washed with water, then brine, dried ($Na_2SO_4$), filtered, and concentrated in vacuo. The crude material was purified by column chromatography (ISCO, 12 g silica gel column, 17 minute gradient from 0 to 100% EtOAc in hexanes) to give Intermediate 165A (5.3 mg, 0.015 mmol, 20.2%) as a clear oil: LC-MS: Method H, RT=1.13 min, MS (ESI) m/z: 356/358 (M+H)⁺.

Example 165

Intermediate I-2 (5.61 mg, 0.018 mmol) and Intermediate 165A (5.3 mg, 0.015 mmol) were dissolved in DMF (149 μL). PdCl₂(dppf)-CH₂Cl₂ (0.729 mg, 0.893 μmol) was added and the reaction mixture was degassed by bubbling with argon for 15 minutes. Sodium carbonate (2 M, 8.93 μL, 0.018 mmol) was added and the reaction mixture was degassed for 5 minutes, then sealed and heated to 100° C. in the microwave for 30 minutes. The reaction mixture was diluted with DMF, filtered, and purified by preparative HPLC (Method D, 70 to 100% B in 20 minutes) to give Example 165 (2.9 mg, 0.00626 mmol, 42.1%): ¹H NMR (500 MHz, DMSO-d₆) δ 9.10 (s, 1H), 8.75 (d, J=1.7 Hz, 1H), 8.04 (s, 1H), 7.61 (d, J=2.5 Hz, 1H), 7.16 (d, J=2.5 Hz, 1H), 5.37 (t, J=5.6 Hz, 1H), 5.22 (d, J=5.2 Hz, 1H), 4.82 (s, 2H), 3.88 (s, 3H), 3.48 (s, 3H), 2.71 (s, 3H), 1.89 (br. s., 1H), 1.81 (d, J=5.8 Hz, 1H), 1.70 (br. s., 1H), 1.66 (d, J=3.6 Hz, 1H), 1.59 (br. s., 1H), 1.44 (d, J=9.4 Hz, 1H), 1.21-1.09 (m, 5H); LC-MS: Method H, RT=1.24 min, MS (ESI) m/z: 464.3 (M+H)⁺; Analytical HPLC Method B: 100% purity.

Example 166

Cyclobutyl(6-methoxy-2-(2-(methoxymethyl)-7-methylquinoxalin-5-yl)benzo[d]thiazol-4-yl)methanol

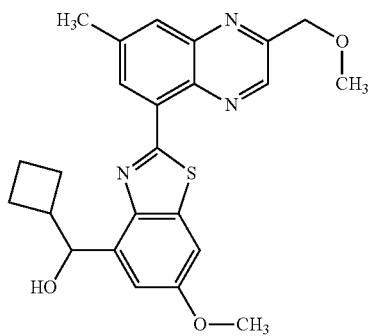

(166)

Intermediate 166A: (2-bromo-6-methoxybenzo[d]thiazol-4-yl)(cyclobutyl)methanol

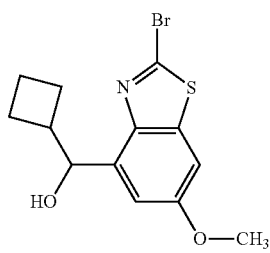

(166A)

Intermediate I-20 (20 mg, 0.073 mmol) was dissolved in THF (735 μL) and cooled to −78° C. Cyclobutylmagnesium bromide (0.25 M, 588 μL, 0.147 mmol) was added and the reaction mixture was warmed to 0° C. for 18 hours. The reaction was quenched with saturated NH₄Cl and extracted with EtOAc. The organic layer was washed with water, then brine, dried (Na₂SO₄), filtered, and concentrated in vacuo. The crude material was purified by column chromatography (ISCO, 12 g silica gel column, 17 minute gradient from 0 to 100% EtOAc in hexanes) to give Intermediate 166A (4 mg, 0.012 mmol, 16.6%): LC-MS: Method H, RT=0.82 min, MS (ESI) m/z: 328/330 (M+H)⁺.

Example 166

Intermediate I-2 (4.59 mg, 0.015 mmol) and Intermediate 166A (4 mg, 0.012 mmol) were dissolved in DMF (122 μL). PdCl₂(dppf)-CH₂Cl₂ (0.597 mg, 0.731 μmol) was added and the reaction mixture was degassed by bubbling with argon for 15 minutes. Sodium carbonate (2 M, 7.31 μL, 0.015 mmol) was added and the reaction mixture was degassed for 5 minutes, then sealed and heated to 100° C. in the microwave for 30 minutes. The reaction mixture was diluted with DMF, filtered, and purified by preparative HPLC (Method D, 50 to 100% B in 23 minutes) to give Example 166 (2.7 mg, 0.00595 mmol, 48.8%): ¹H NMR (500 MHz, CHLOROFORM-d) δ 9.01 (s, 1H), 8.67 (d, J=1.4 Hz, 1H), 7.89 (s, 1H), 7.25 (d, J=2.2 Hz, 1H), 6.87 (d, J=2.5 Hz, 1H), 4.95 (d, J=8.0 Hz, 1H), 4.77 (s, 2H), 3.87-3.82 (m, 3H), 3.51 (s, 3H), 2.92-2.84 (m, 1H), 2.65 (s, 3H), 2.18-2.06 (m, 2H), 1.91 (br. s., 1H), 1.86-1.75 (m, 3H); LC-MS: Method H, RT=1.15 min, MS (ESI) m/z: 436.2 (M+H)⁺; Analytical HPLC Method B: 96% purity.

Example 167

(6-methoxy-2-(2-(methoxymethyl)-7-methylquinoxalin-5-yl)benzo[d]thiazol-4-yl)(pyridin-2-yl)methanol

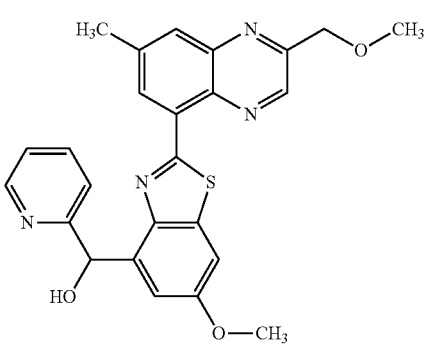

(167)

Intermediate 167A: (2-bromo-6-methoxybenzo[d]thiazol-4-yl)(pyridin-2-yl)methanol

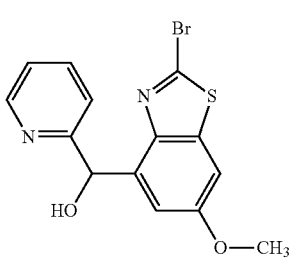

(167A)

Intermediate I-20 (20 mg, 0.073 mmol) was dissolved in THF (735 μL) and cooled to −78° C. Pyridin-2-ylmagnesium bromide (0.25 M, 588 μL, 0.147 mmol) was added and the reaction mixture was warmed to 0° C. for 18 hours. The reaction was quenched with saturated $NH_4Cl$ and extracted with EtOAc. The organic layer was washed with water, then brine, dried ($Na_2SO_4$), filtered, and concentrated in vacuo. The crude material was purified by column chromatography (ISCO, 12 g silica gel column, 17 minute gradient from 0 to 100% EtOAc in hexanes) to give Intermediate 167A (9.1 mg, 0.026 mmol, 35.3%) as a yellow oil: LC-MS: Method H, RT=0.66 min, MS (ESI) m/z: 351/353 (M+H)$^+$.

Example 167

Intermediate I-2 (9.77 mg, 0.031 mmol) and Intermediate 167A (9.1 mg, 0.026 mmol) were dissolved in DMF (259 μL). $PdCl_2(dppf)$-$CH_2Cl_2$ (1.270 mg, 1.555 μmol) was added and the reaction mixture was degassed by bubbling with argon for 15 minutes. Sodium carbonate (2 M, 15.55 μL, 0.031 mmol) was added and the reaction mixture was degassed for 5 minutes, then sealed and heated to 100° C. in the microwave for 30 minutes. The reaction mixture was diluted with DMF, filtered, and purified by preparative HPLC (Method D, 40 to 80% B in 20 minutes) to give Example 167 (2.7 mg, 0.00548 mmol, 21.1%): $^1$H NMR (500 MHz, DMSO-d$_6$) δ 9.10 (s, 1H), 8.72 (d, J=1.4 Hz, 1H), 8.48 (d, J=4.4 Hz, 1H), 8.04 (s, 1H), 7.90-7.80 (m, 1H), 7.76 (d, J=7.7 Hz, 1H), 7.65 (d, J=2.5 Hz, 1H), 7.31-7.22 (m, 1H), 7.14 (d, J=2.2 Hz, 1H), 6.72 (s, 1H), 6.22 (br. s., 1H), 4.82 (s, 2H), 3.86 (s, 3H), 3.48 (s, 3H), 2.71 (s, 3H); LC-MS: Method H, RT=0.80 min, MS (ESI) m/z: 459.2 (M+H)$^+$; Analytical HPLC Method B: 93% purity.

Example 168

(6-methoxy-2-(2-(methoxymethyl)-7-methylquinoxalin-5-yl)benzo[d]thiazol-4-yl) (pyridin-3-yl)methanol

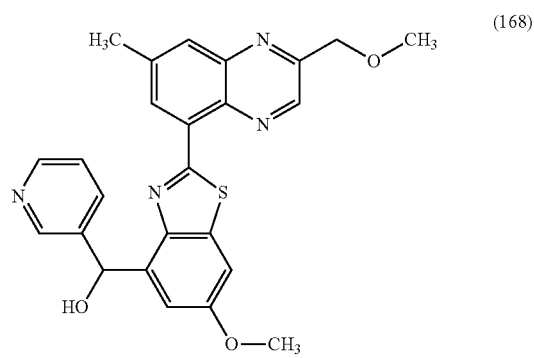 [SMILES: COCc1cnc2c(-c3nc4c(C(O)c5cccnc5)cc(OC)cc4s3)cc(C)cc2n1]

(168)

Intermediate 168A: (2-bromo-6-methoxybenzo[d]thiazol-4-yl)(pyridin-3-yl)methanol

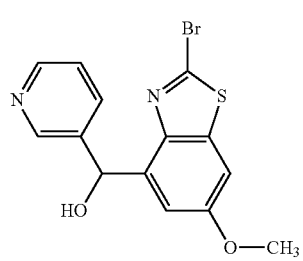

(168A)

Intermediate I-20 (20 mg, 0.073 mmol) was dissolved in THF (735 μL) and cooled to −78° C. Pyridin-3-ylmagnesium bromide (0.25 M, 588 μL, 0.147 mmol) was added and the reaction mixture was warmed to 0° C. for 18 hours. The reaction was quenched with saturated $NH_4Cl$ and extracted with EtOAc. The organic layer was washed with water, then brine, dried ($Na_2SO_4$), filtered, and concentrated in vacuo. The crude material was purified by column chromatography (ISCO, 12 g silica gel column, 17 minute gradient from 0 to 100% EtOAc in hexanes) to give Intermediate 168A (14.6 mg, 0.042 mmol, 56.6%) as a white solid: LC-MS: Method H, RT=0.65 min, MS (ESI) m/z: 351/353 (M+H)$^+$.

Example 168

Intermediate I-2 (15.67 mg, 0.050 mmol) and Intermediate 168A (14.6 mg, 0.042 mmol) were dissolved in DMF (416 μL). $PdCl_2(dppf)$-$CH_2Cl_2$ (2.037 mg, 2.494 μmol) was added and the reaction mixture was degassed by bubbling with argon for 15 minutes. Sodium carbonate (2 M, 24.94 μL, 0.050 mmol) was added and the reaction mixture was degassed for 5 minutes, then sealed and heated to 100° C. in the microwave for 30 minutes. The reaction mixture was diluted with DMF, filtered, and purified by preparative HPLC (Method D, 35 to 75% B in 20 minutes) to give Example 168 (10 mg, 0.022 mmol, 51.9%): $^1$H NMR (500 MHz, DMSO-d$_6$) δ 9.09 (s, 1H), 8.86 (s, 1H), 8.80 (s, 1H), 8.41 (d, J=4.4 Hz, 1H), 8.04 (s, 1H), 7.93 (d, J=8.0 Hz, 1H), 7.65 (d, J=2.5 Hz, 1H), 7.37 (d, J=2.5 Hz, 1H), 7.34 (dd, J=8.0, 4.7 Hz, 1H), 6.73 (d, J=4.1 Hz, 1H), 6.29 (d, J=4.4 Hz, 1H), 4.82 (s, 2H), 3.89 (s, 3H), 3.48 (s, 3H), 2.73 (s, 3H); LC-MS: Method H, RT=0.79 min, MS (ESI) m/z: 459.2 (M+H)$^+$; Analytical HPLC Method B: 99% purity.

Example 169

1-(6-methoxy-2-(2-(methoxymethyl)-7-methylquinoxalin-5-yl)benzo[d]thiazol-4-yl)-2,2-dimethylpropan-1-ol-1-d$_1$

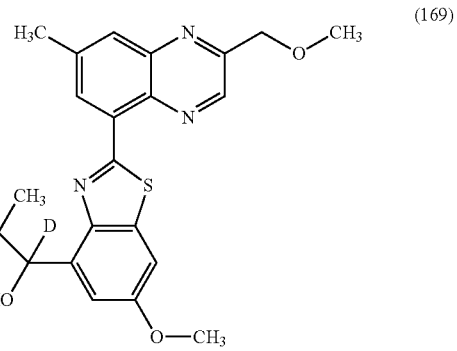

(169)

Intermediate 169A: (2-bromo-6-methoxybenzo[d]thiazol-4-yl)methanol-d$_2$

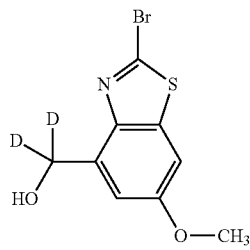

(169A)

Intermediate I-20C (370 mg, 1.225 mmol) was dissolved in toluene (8164 µL) and THF (4082 µL) and cooled to −78° C. DIBAL-D (3849 µL, 2.69 mmol) was added and the reaction mixture was stirred for 30 minutes. The reaction mixture was warmed to ambient temperature. After 1.5 hours, the reaction was quenched with 1 N HCl, stirred for 1 hour, and extracted with EtOAc. The organic layer was washed with saturated NaHCO$_3$, then brine, dried (Na$_2$SO$_4$), filtered, and concentrated in vacuo. The crude material was purified by column chromatography (ISCO, 40 g silica gel column, 19 minute gradient from 0 to 100% EtOAc in hexanes) to give Intermediate 169A (76.5 mg, 0.277 mmol, 22.5%) as a white solid: $^1$H NMR (400 MHz, CHLOROFORM-d) δ 7.17 (dd, J=7.7, 2.4 Hz, 1H), 7.05 (dd, 2.5 Hz, 1H), 3.87 (s, 3H), 2.95 (d, J=15.0 Hz, 1H); LC-MS: Method H, RT=0.83 min, MS (ESI) m/z: 276/278 (M+H)$^+$.

Intermediate 169B: 2-bromo-6-methoxybenzo[d]thiazole-4-carbaldehyde-d$_1$

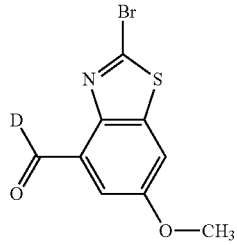

(169B)

Intermediate 169A (76 mg, 0.275 mmol) was dissolved in CHCl$_3$ (1835 µL). Manganese dioxide (144 mg, 1.651 mmol) was added and the reaction mixture was heated to 40° C. for 18 hours. More manganese dioxide (144 mg, 1.651 mmol) was added and heating continued for 36 hours. The reaction mixture was filtered through celite and concentrated in vacuo. The crude material was purified by column chromatography (ISCO, 24 g silica gel column, 17 minute gradient from 0 to 100% EtOAc in hexanes) to give Intermediate 169B (35.7 mg, 0.131 mmol, 47.5%) as a white solid: $^1$H NMR (400 MHz, CHLOROFORM-d) δ 7.62 (dd, J=5.1, 2.6 Hz, 1H), 7.54 (dd, J=8.1, 2.6 Hz, 1H), 3.93 (s, 3H); LC-MS: Method H, RT=0.95 min, MS (ESI) m/z: 275/277 (M+H)$^+$.

Intermediate 169C: 1-(2-bromo-6-methoxybenzo[d]thiazol-4-yl)-2,2-dimethylpropan-1-ol-1-d$_1$

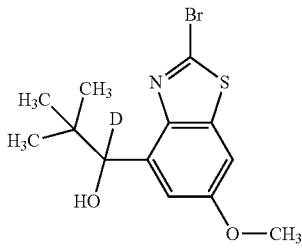

(169C)

Intermediate 169B (35 mg, 0.128 mmol) was dissolved in THF (1281 µL) and cooled to −78° C. tert-Butylmagnesium chloride (384 µL, 0.384 mmol) was added and the reaction mixture was warmed to 0° C. for 18 hours. The reaction was quenched with saturated NH$_4$Cl and extracted with EtOAc. The organic layer was washed with water, then brine, dried (Na$_2$SO$_4$), filtered, and concentrated in vacuo. The crude material was purified by column chromatography (ISCO, 12 g silica gel column, 17 minute gradient from 0 to 100% EtOAc in hexanes) to give Intermediate 169C (27.1 mg, 0.082 mmol, 63.8%) as a white solid: LC-MS: Method H, RT=1.06 min, MS (ESI) m/z: 331/333 (M+H)$^+$.

Intermediate 169D: 1-(6-methoxy-2-(2-(methoxymethyl)-7-methylquinoxalin-5-yl)benzo[d]thiazol-4-yl)-2,2-dimethylpropan-1-ol-1-d$_1$

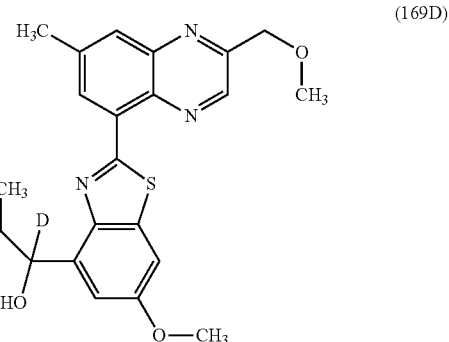

(169D)

Intermediate I-2 (30.8 mg, 0.098 mmol) and Intermediate 169C (27.1 mg, 0.082 mmol) were dissolved in DMF (818 µL). PdCl$_2$(dppf)-CH$_2$Cl$_2$ (4.01 mg, 4.91 µmol) was added and the reaction mixture was degassed by bubbling with argon for 15 minutes. Sodium carbonate (2 M, 49.1 µL, 0.098 mmol) was added and the reaction mixture was degassed for 5 minutes, then sealed and heated to 100° C. in the microwave for 30 minutes. The reaction mixture was diluted with EtOAc, washed with water, then brine, dried (Na$_2$SO$_4$), filtered, and concentrated in vacuo. The crude material was purified by column chromatography (ISCO, 12 g silica gel column, 19 minute gradient from 0 to 100% EtOAc in hexanes) to give Intermediate 169D (17.3 mg, 0.039 mmol, 48.2%) as a yellow solid: LC-MS: Method H, RT=1.18 min, MS (ESI) m/z: 439.3 (M+H)$^+$.

Example 169

Intermediate 169D (17.3 mg, 0.039 mmol) was purified by SFC chromatography (Berger Multigram II SFC, Chiralpak OJ-H, 21×250 mm, 5 micron, 25% MeOH/75% $CO_2$, 45 mL/min flow rate) to give Enantiomer 1 (6.5 mg, 0.014 mmol, 35.7%) and Example 169 (Enantiomer 2, 6.5 mg, 0.014 mmol, 35.7%) as a yellow solid: $^1$H NMR (400 MHz, CHLOROFORM-d) δ 9.08 (s, 1H), 8.69 (d, J=1.8 Hz, 1H), 7.96 (s, 1H), 7.34 (d, J=2.4 Hz, 1H), 6.93 (d, J=2.4 Hz, 1H), 5.71 (s, 1H), 4.85 (s, 2H), 3.92 (s, 3H), 3.58 (s, 3H), 2.72 (s, 3H), 1.05 (s, 9H); LC-MS: Method H, RT=1.18 min, MS (ESI) m/z: 439.3 (M+H)$^+$; 95% purity.

Example 170

1-(6-methoxy-2-(2-(methoxymethyl)-7-methylquinoxalin-5-yl)benzo[d]thiazol-4-yl)-2,2-dimethylpropan-1-ol-d$_5$

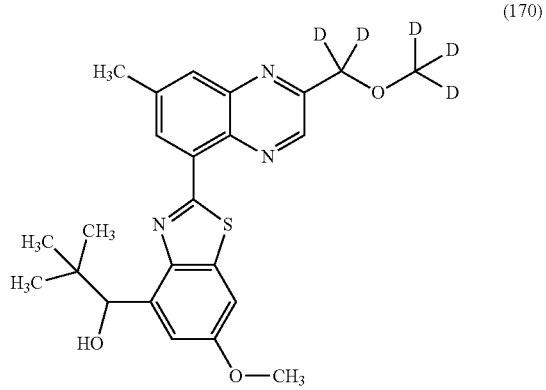 [SMILES: [2H]C([2H])([2H])OC([2H])([2H])c1cnc2c(-c3nc4c(C(O)C(C)(C)C)cc(OC)cc4s3)cc(C)cc2n1]

(170)

Intermediate 170A: 1-(6-methoxy-2-(2-(methoxymethyl)-7-methylquinoxalin-5-yl)benzo[d]thiazol-4-yl)-2,2-dimethylpropan-1-ol-d$_5$

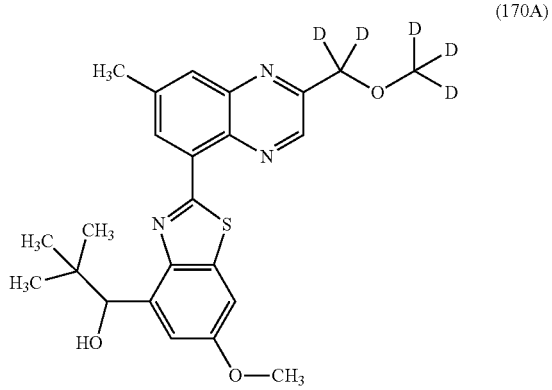 [SMILES: [2H]C([2H])([2H])OC([2H])([2H])c1cnc2c(-c3nc4c(C(O)C(C)(C)C)cc(OC)cc4s3)cc(C)cc2n1]

(170A)

Intermediate I-25 (39.6 mg, 0.124 mmol) and Intermediate 164A (41 mg, 0.124 mmol) were dissolved in DMF (1242 μL). PdCl$_2$(dppf)-CH$_2$Cl$_2$ (6.08 mg, 7.45 μmol) was added and the reaction mixture was degassed by bubbling with argon for 15 minutes. Sodium carbonate (2 M, 74.5 μL, 0.149 mmol) was added and the reaction mixture was degassed for 5 minutes, then sealed and heated to 100° C. in the microwave for 30 minutes. The reaction mixture was diluted with EtOAc, washed with water, then brine, dried (Na$_2$SO$_4$), filtered, and concentrated in vacuo. The crude material was purified by column chromatography (ISCO, 12 g silica gel column, 19 minute gradient from 0 to 100% EtOAc in hexanes) to give Intermediate 170A (17.8 mg, 0.040 mmol, 32.4%) as a yellow solid: LC-MS: Method H, RT=1.18 min, MS (ESI) m/z: 443.3 (M+H)$^+$.

Example 170

Intermediate 170A (19.8 mg, 0.045 mmol) was purified by SFC chromatography (Berger Multigram II SFC, Chiralpak OJ-H, 21×250 mm, 5 micron, 25% MeOH/75% $CO_2$, 45 mL/min flow rate) to give Enantiomer 1 (7.7 mg, 0.017 mmol, 36.9%) and Example 170 (Enantiomer 2, 7.8 mg, 0.017 mmol, 37.4%) as a yellow solid: $^1$H NMR (400 MHz, CHLOROFORM-d) δ 9.08 (s, 1H), 8.69 (d, J=1.8 Hz, 1H), 7.96 (s, 1H), 7.34 (d, J=2.4 Hz, 1H), 6.93 (d, J=2.4 Hz, 1H), 5.74 (br. s., 1H), 4.77 (br. s., 1H), 3.92 (s, 3H), 2.72 (s, 3H), 1.05 (s, 9H); LC-MS: Method H, RT=1.18 min, MS (ESI) m/z: 443.3 (M+H)$^+$; 95% purity.

Example 171

2,2,2-trifluoro-1-(6-methoxy-2-(2-(methoxymethyl)-7-methylquinoxalin-5-yl)benzo[d]thiazol-4-yl)ethanol

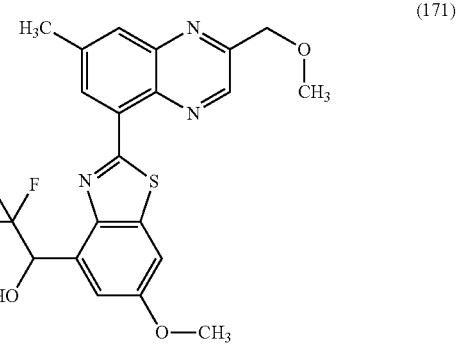

(171)

Intermediate 171A: 2-chloro-6-methoxybenzo[d]thiazole-4-carbaldehyde

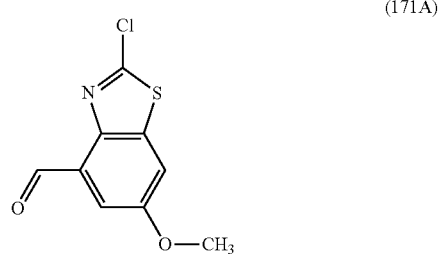

(171A)

Intermediate I-20 (250 mg, 0.919 mmol) was dissolved in THF (8352 μL) and concentrated HCl (835 μL) for 2.5 hours. The reaction mixture was diluted with EtOAc, washed with water, saturated NaHCO$_3$, then brine, dried (Na$_2$SO$_4$), filtered, and concentrated in vacuo to give Intermediate 171A (207 mg, 0.909 mmol, 99%) as an off-white solid: $^1$H NMR (400 MHz, CHLOROFORM-d) δ 10.85 (s, 1H), 7.62 (d, J=2.6 Hz, 1H), 7.53 (d, J=2.6 Hz, 1H), 3.93 (s, 3H); LC-MS: Method H, RT=1.02 min, MS (ESI) m/z: 242.1 (M+Na)$^+$.

Intermediate 171B: 1-(2-chloro-6-methoxybenzo[d]thiazol-4-yl)-2,2,2-trifluoroethanol

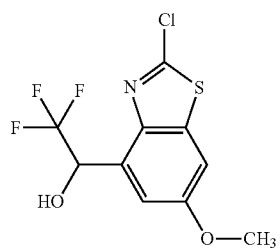

(171B)

Intermediate 171A (207 mg, 0.909 mmol) was dissolved in THF (18.2 mL). (Trifluoromethyl)trimethylsilane (161 µL, 1.091 mmol) then TBAF (1091 µL, 1.091 mmol) were added and the reaction mixture was stirred for 18 hours. The reaction mixture was diluted with EtOAc and washed with water, saturated NaHCO$_3$, then brine, dried (Na$_2$SO$_4$), filtered, and concentrated in vacuo. The crude material was purified by column chromatography (ISCO, 40 g silica gel column, 19 minute gradient from 0 to 100% EtOAc in hexanes) to give Intermediate 171B (70.8 mg, 0.238 mmol, 26.2%) as a white solid: LC-MS: Method H, RT=0.98 min, MS (ESI) m/z: 298.1 (M+H)$^+$.

Example 171

Intermediate I-2 (30.0 mg, 0.096 mmol) and Intermediate 171B (23.7 mg, 0.080 mmol) were dissolved in DMF (796 µL). PdCl$_2$(dppf)-CH$_2$Cl$_2$ (3.90 mg, 4.78 µmol) was added and the reaction mixture was degassed by bubbling with argon for 15 minutes. Sodium carbonate (2 M, 47.8 µL, 0.096 mmol) was added and the reaction mixture was degassed for 5 minutes, then sealed and heated to 100° C. in the microwave for 30 minutes. The reaction mixture was diluted with DMF, filtered, and purified by preparative HPLC (Method D, 45 to 95% B in 20 minutes) to give Example 171 (9.8 mg, 0.021 mmol, 26.6%): $^1$H NMR (500 MHz, DMSO-d$_6$) δ 9.12 (s, 1H), 8.83 (br. s., 1H), 8.07 (br. s., 1H), 7.84 (br. s., 1H), 7.33 (br. s., 1H), 7.07 (d, J=5.8 Hz, 1H), 6.22 (br. s., 1H), 4.83 (s, 2H), 3.92 (s, 3H), 3.49 (s, 3H), 2.72 (s, 3H); LC-MS: Method H, RT=1.08 min, MS (ESI) m/z: 450.2 (M+H)$^+$; Analytical HPLC Method B: 97% purity.

Example 172

(6-methoxy-2-(2-(methoxymethyl)-7-methylquinoxalin-5-yl)benzo[d]thiazol-4-yl)(pyridin-4-yl)methanol

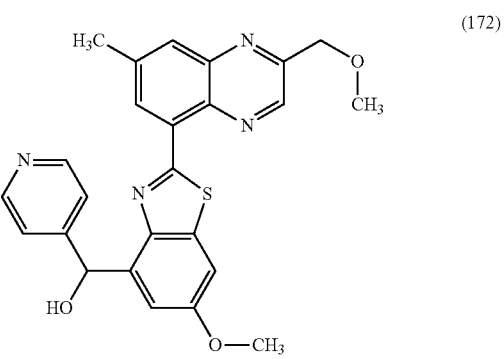 [SMILES: COCc1cnc2c(-c3nc4c(C(O)c5ccncc5)cc(OC)cc4s3)cc(C)cc2n1]

(172)

Intermediate 172A: (2-amino-6-methoxybenzo[d]thiazol-4-yl)(pyridin-4-yl)methanol

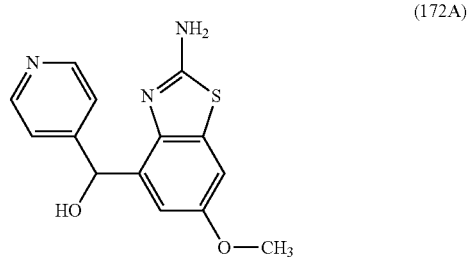

(172A)

Intermediate I-22 (50 mg, 0.193 mmol) was dissolved in THF (1930 Sodium hydride (8.49 mg, 0.212 mmol) was added and the reaction mixture was stirred for 10 minutes. The reaction mixture was cooled to −78° C. and BuLi (2.3 M, 101 µL, 0.232 mmol) was added, and the reaction mixture was stirred for 1 hour. Isonicotinaldehyde (41.3 mg, 0.386 mmol) was added and the reaction mixture was allowed to warm to ambient temperature. After 1 hour, the reaction mixture was diluted with EtOAc and washed with water, then brine, dried (Na$_2$SO$_4$), filtered, and concentrated in vacuo to give Intermediate 172A, which was used directly in the subsequent reaction: LC-MS: Method H, RT=0.47 min, MS (ESI) m/z: 288.2 (M+H)$^+$.

Intermediate 172B: (2-chloro-6-methoxybenzo[d]thiazol-4-yl)(pyridin-4-yl)methanol

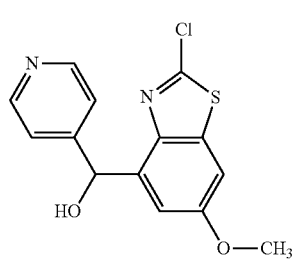

(172B)

Copper(II) chloride (36.0 mg, 0.268 mmol) and t-butyl nitrite (34.1 µL, 0.287 mmol) were dissolved in MeCN (766 µL) and allowed to stir 10 minutes. Intermediate 172A (55 mg, 0.191 mmol) was dissolved in MeCN (1148 µL) and the copper solution was added and the reaction mixture was heated to 60° C. for 2 hours. The reaction mixture was diluted with EtOAc, washed with saturated NaHCO$_3$, then brine, dried (Na$_2$SO$_4$), filtered, and concentrated in vacuo. The reaction mixture was purified by column chromatography (ISCO, 12 g silica gel column, 17 minute gradient from 0 to 20% MeOH in DCM) to give Intermediate 172B (11.5 mg, 0.037 mmol, 19.6%) as a yellow solid: LC-MS: Method H, RT=0.63 min, MS (ESI) m/z: 307.1 (M+H)$^+$.

Example 172

Intermediate I-2 (14.13 mg, 0.045 mmol) and Intermediate 172B (11.5 mg, 0.037 mmol) were dissolved in DMF (375 µL). PdCl$_2$(dppf)-CH$_2$Cl$_2$ (1.837 mg, 2.249 µmol) was added and the reaction mixture was degassed by bubbling with argon for 15 minutes. Sodium carbonate (2 M, 22.49 µL, 0.045 mmol) was added and the reaction mixture was degassed for 5 minutes, then sealed and heated to 100° C. in the microwave for 30 minutes. The reaction mixture was diluted with DMF, filtered, and purified by preparative HPLC (Method D, 35 to 75% B in 20 minutes) to give Example 172 (6 mg, 0.013 mmol, 34.9%): $^1$H NMR (500 MHz, DMSO-d$_6$) δ 9.10 (s, 1H), 8.83 (s, 1H), 8.57 (br. s., 2H), 8.06 (s, 1H), 7.70 (br. s., 2H), 7.67 (d, J=2.1 Hz, 1H), 7.26 (s, 2H), 6.75 (s, 1H), 4.83 (s, 2H), 3.88 (s, 3H), 2.74 (s, 3H); LC-MS: Method H, RT=0.78 min, MS (ESI) m/z: 459.3 (M+H)$^+$; Analytical HPLC Method B: 100% purity.

Example 173

3,3,3-trifluoro-1-(6-methoxy-2-(2-(methoxymethyl)-7-methylquinoxalin-5-yl)benzo[d]thiazol-4-yl)propan-1-ol

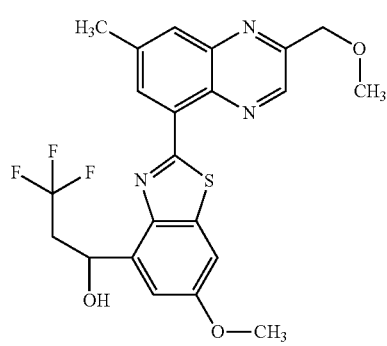

(173)

Intermediate 173A: 1-(2-amino-6-methoxybenzo[d]thiazol-4-yl)-3,3,3-trifluoropropan-1-ol

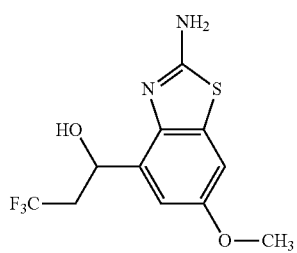

(173A)

Intermediate I-22 (50 mg, 0.193 mmol) was dissolved in THF (1930 Sodium hydride (8.49 mg, 0.212 mmol) was added and the reaction mixture was stirred for 15 minutes. The reaction mixture was cooled to −78° C. and BuLi (2.3 M, 101 µL, 0.232 mmol) was added and the reaction mixture was stirred for 30 minutes. 3,3,3-Trifluoropropanal (43.2 mg, 0.386 mmol) was added and the reaction mixture was allowed to warm to ambient temperature and stir for 1 hour. The reaction mixture was diluted with EtOAc and washed with water, then brine, dried (Na$_2$SO$_4$), filtered, and concentrated in vacuo to give Intermediate 173A, which was used directly in the subsequent step: LC-MS: Method H, RT=0.65 min, MS (ESI) m/z: 293.2 (M+H)$^+$.

Intermediate 173B: 1-(2-chloro-6-methoxybenzo[d]thiazol-4-yl)-3,3,3-trifluoropropan-1-ol

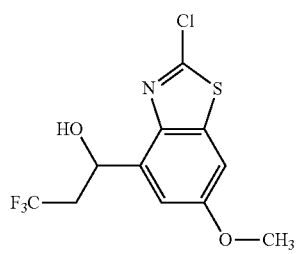

(173B)

Copper(II) chloride (36.3 mg, 0.270 mmol) and t-butyl nitrite (34.4 µL, 0.289 mmol) were dissolved in MeCN (772 µL) and allowed to stir 10 minutes. Intermediate 173A (56.4 mg, 0.193 mmol) was dissolved in MeCN (1158 µL) and the copper solution was added and the reaction mixture was heated to 60° C. After 3 hours, the reaction mixture was diluted with EtOAc, washed with 1 N HCl, saturated NaHCO$_3$, then brine, dried (Na$_2$SO$_4$), filtered, and concentrated in vacuo. The crude material was purified by column chromatography (ISCO, 12 g silica gel column, 17 minute gradient from 0 to 100% EtOAc in hexanes) to give Intermediate 173B (9.4 mg, 0.030 mmol, 15.6%) as a yellow oil: LC-MS: Method H, RT=0.98 min, MS (ESI) m/z: 312.1 (M+H)$^+$.

Example 173

Intermediate I-2 (11.37 mg, 0.036 mmol) and Intermediate 173B (9.4 mg, 0.030 mmol) were dissolved in DMF (302 µL). PdCl$_2$(dppf)-CH$_2$Cl$_2$ (1.478 mg, 1.809 µmol) was added and the reaction mixture was degassed by bubbling with argon for 15 minutes. Sodium carbonate (2 M, 18.09 µL, 0.036 mmol) was added and the reaction mixture was degassed for 5 minutes, then sealed and heated to 100° C. in the microwave for 30 minutes. More PdCl$_2$(dppf)-CH$_2$Cl$_2$ (1.478 mg, 1.809 µmol) was added and the reaction mixture was heated to 100° C. for 30 minutes in the microwave. The reaction mixture was diluted with DMF, filtered, and purified by preparative HPLC (Method D, 45 to 85% B in 25 minutes) to give Example 173 (2.5 mg, 0.00523 mmol, 17.4%): $^1$H NMR (500 MHz, DMSO-d$_6$) δ 9.10 (s, 1H), 8.75 (s, 1H), 8.05 (s, 1H), 7.68 (d, J=2.1 Hz, 1H), 7.30 (d, J=2.1 Hz, 1H), 5.93 (d, J=5.5 Hz, 1H), 5.85 (br. s., 1H), 4.82 (s, 2H), 3.91 (s, 3H), 3.02-2.90 (m, 1H), 2.84-2.73 (m, 1H), 2.69 (s, 3H) (1 methyl group under DMSO); LC-MS: Method H, RT=1.10 min, MS (ESI) m/z: 464.2 (M+H)$^+$; Analytical HPLC Method B: 97% purity.

Example 174

2,2,2-trifluoro-1-(6-methoxy-2-(2-methoxy-7-methylquinoxalin-5-yl)benzo[d]thiazol-4-yl)ethanol

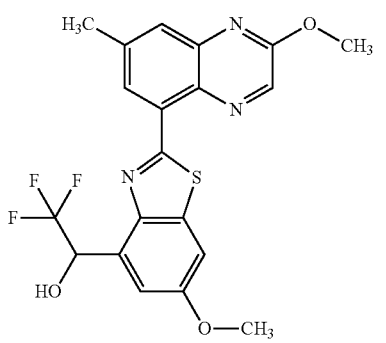

(174)

Intermediate I-9 (20.09 mg, 0.067 mmol) and Intermediate 171B (16.6 mg, 0.056 mmol) were dissolved in DMF (558 µL). PdCl$_2$(dppf)-CH$_2$Cl$_2$ (2.73 mg, 3.35 µmol) was added and the reaction mixture was degassed by bubbling with argon for 15 minutes. Sodium carbonate (2 M, 33.5 µL, 0.067 mmol) was added and the reaction mixture was degassed for 5 minutes, then sealed and heated to 100° C. in the microwave for 30 minutes. The reaction mixture was diluted with DMF, filtered, and purified by preparative HPLC (Method D, 40 to 80% B in 25 minutes) to give Example 174 (4.6 mg, 0.0104 mmol, 18.6%): $^1$H NMR (500 MHz, DMSO-d$_6$) δ 8.71 (s, 1H), 8.57 (s, 1H), 7.82 (s, 1H), 7.78 (s, 1H), 7.31 (s, 1H), 7.16 (d, J=6.1 Hz, 1H), 6.24-6.15 (m, 1H), 4.08 (s, 3H), 3.90 (s, 3H), 2.64 (s, 3H); LC-MS: Method H, RT=1.17 min, MS (ESI) m/z: 436.2 (M+H)$^+$; Analytical HPLC Method B: 98% purity.

Example 175

5-(benzofuran-2-yl)-2-methoxy-7-methylquinoxaline

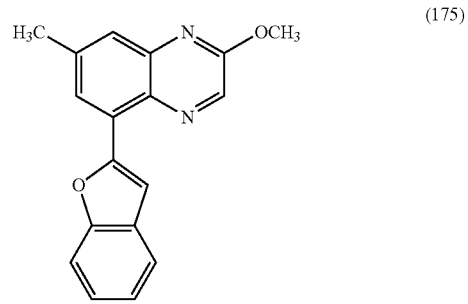 [SMILES: COc1cnc2c(-c3cc4ccccc4o3)cc(C)cc2n1]

(175)

Intermediate I-9A (0.053 g, 0.209 mmol) and benzofuran-2-ylboronic acid (0.051 g, 0.314 mmol) were dissolved in toluene (3.14 mL) and EtOH (1.047 mL). PdCl$_2$(dppf)-CH$_2$Cl$_2$ adduct (10.26 mg, 0.013 mmol) was added and the reaction mixture was degassed by bubbling with argon for 15 minutes. 2 M aqueous Na$_2$CO$_3$ (0.126 mL, 0.251 mmol) was added and the reaction mixture was degassed for 5 minutes, then sealed and heated to 120° C. in the microwave for 30 minutes. The reaction mixture was diluted with EtOAc, filtered through a micron filter, and concentrated in vacuo. The reaction mixture was purified on Prep HPLC using Method A to yield Example 175 (2.57 mg, 8.41 µmol, 4.02% yield). $^1$H NMR (400 MHz, CHLOROFORM-d) δ 8.52 (s, 1H), 8.14 (d, J=1.8 Hz, 1H), 8.08 (s, 1H), 7.67 (d, J=7.5 Hz, 1H), 7.63 (d, J=0.8 Hz, 1H), 7.56 (d, J=8.0 Hz, 1H), 7.32 (td, J=7.7, 1.3 Hz, 1H), 7.25-7.22 (m, 1H), 4.14-4.10 (m, 3H), 2.63 (s, 3H). LC-MS: method H, RT=1.27 min, MS (ESI) m/z: 291.1 (M+H)$^+$. Analytical HPLC: Method A, 94.5% purity.

Example 176

Methyl 5-(benzofuran-2-yl)-7-methylquinoxaline-2-carboxylate

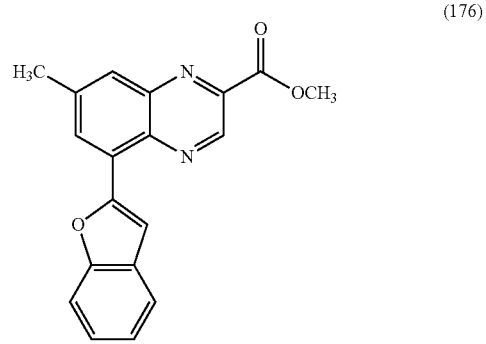 [SMILES: COC(=O)c1cnc2c(-c3cc4ccccc4o3)cc(C)cc2n1]

(176)

Intermediate 176A: ethyl 5-(benzofuran-2-yl)-7-methylquinoxaline-2-carboxylate

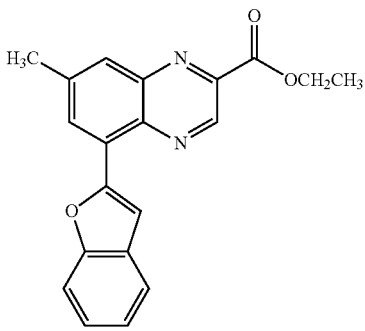

(176A)

Intermediate I-15B (0.250 g, 0.847 mmol) and benzofuran-2-ylboronic acid (0.137 g, 0.847 mmol) were dissolved in DMF (20 mL). PdCl$_2$(dppf)-CH$_2$Cl$_2$ adduct (0.042 g, 0.051 mmol) was added and the reaction mixture was degassed by bubbling with argon for 15 minutes. Na$_2$CO$_3$ (3 mL, 6.00 mmol) was added and the reaction mixture was degassed for 5 minutes, then sealed and heated to 90° C. in the microwave for 30 minutes. The reaction mixture was diluted with EtOAc and filtered through a micron filter and concentrated in vacuo. The reaction mixture was purified by ISCO to remove any Pd or ligand based impurities. 40 g column with a 0-100% gradient of EtOAc in hexanes was used. Fractions pooled and the residue was purified on Prep HPLC using Method A to yield Intermediate 176A (0.074 g, 0.223 mmol, 26.3% yield) LC-MS: method H, RT=1.20 min, MS (ESI) m/z: 333.0 (M+H)$^+$.

Intermediate 176B: 5-(benzofuran-2-yl)-7-methylquinoxaline-2-carboxylic acid

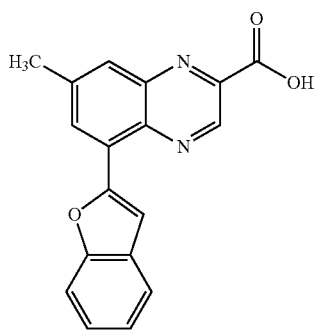

(176B)

Intermediate 176A (0.050 g, 0.150 mmol) was dissolved in THF (3 mL) and MeOH (0.300 mL). NaOH, 1 N in water (0.500 mL, 0.500 mmol) was added and the reaction mixture was allowed to stir at room temperature for 18 h. Diluted with 1 N HCl and EtOAc. The layers were separated and the aqueous layer was back extracted with EtOAc (×3). The organic layer was washed with brine, dried with sodium sulfate, and concentrated under reduced pressure to yield Intermediate 176B (0.046 g, 0.151 mmol, 100% yield) as a yellow solid. Used without further purification in the next step. $^1$H NMR (500 MHz, DMSO-d$_6$) δ 9.50 (s, 1H), 8.44 (s, 2H), 8.00 (s, 1H), 7.82 (d, J=7.4 Hz, 1H), 7.72 (dd, J=8.3, 0.8 Hz, 1H), 7.43 (td, J=7.7, 1.4 Hz, 1H), 7.36-7.30 (m, 1H), 2.71 (s, 3H). LC-MS: method H, RT=1.05 min, MS (ESI) m/z: 305.1 (M+H)$^+$.

Intermediate 176C: 5-(benzofuran-2-yl)-7-methylquinoxaline-2-carbonyl chloride

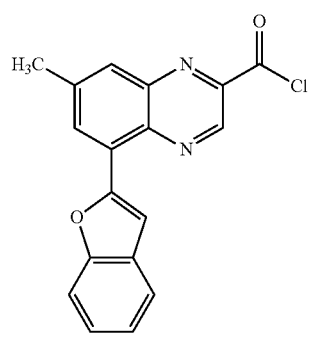

(176C)

Intermediate 176B (0.046 g, 0.151 mmol) was dissolved in DCM (3 mL) and oxalyl chloride (0.013 mL, 0.151 mmol) was added. DMF (1.170 µL, 0.015 mmol) was added and the reaction mixture was allowed to stir at room temperature for 30 min. The reaction mixture was concentrated and stored under vacuum for 1 h. Used without further purification in the next step. LC-MS: method H, RT=1.15 min, MS (ESI) m/z: 319.0 (M+H)$^+$. Methyl ester mass observed by LC/MS.

Example 176

Intermediate 176C (0.0125 g, 0.039 mmol) was dissolved in DCM (3 mL). DMAP (0.473 mg, 3.87 µmol), TEA (10.80 µL, 0.077 mmol), and methanol (1.241 mg, 0.039 mmol) were added and the reaction mixture was allowed to stir at room temperature over the weekend. The reaction mixture was concentrated. The reaction mixture was diluted with DMF, filtered, and purified by preparative HPLC (Method D, 50 to 90% B in 10 minutes) to give Example 176 (0.0057 g, 0.017 mmol, 44.8% yield): $^1$H NMR (500 MHz, METHANOL-d$_4$)) δ 9.53 (s, 1H), 8.44 (s, 1H), 8.17 (s, 1H), 7.97 (s, 1H), 7.68 (d, J=7.7 Hz, 1H), 7.56 (d, J=8.0 Hz, 1H), 7.35 (t, J=7.7 Hz, 1H), 7.29-7.22 (m, 1H), 3.37 (s, 3H), 2.69 (s, 3H). LC-MS: method H, RT=1.18 min, MS (ESI) m/z: 319.1(M+H)$^+$. Analytical HPLC Method B: 97.0% purity.

Example 177

8-(benzofuran-2-yl)-3-methoxy-6-methylquinoline

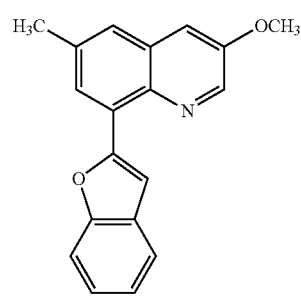

(177)

Intermediate 177A: (Z)-3((2-bromo-4-methylphenyl)amino)-2-nitroacrylaldehyde

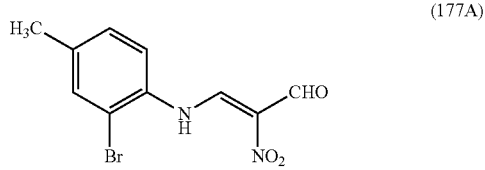 [SMILES: Cc1ccc(N/C=C(/C=O)[N+](=O)[O-])c(Br)c1]

2-Bromo-4-methylaniline (0.380 g, 2.044 mmol) was dissolved in hydrochloric acid, 2 N in water (1 mL) and sodium (Z)-2-nitro-3-oxoprop-1-en-1-olate hydrate (0.321 g, 2.044 mmol) in water (2.5 mL) was added to the reaction mixture. The reaction mixture was allowed to stir for 30 min and the solid was collected to yield Intermediate 177A (0.537 g, 1.884 mmol, 92%). Material carried on without further purification in the next step. $^1$H NMR (400 MHz, CHLOROFORM-d) δ 12.46 (br. s., 1H), 10.17 (s, 1H), 8.32 (d, J=14.6 Hz, 1H), 7.45 (s, 1H), 7.25-7.22 (m, 2H), 2.34 (s, 3H). LC-MS: method H, RT=0.96 min, MS (ESI) m/z: 285.0 (M+H)$^+$.

Intermediate 177B: 8-bromo-6-methyl-3-nitroquinoline

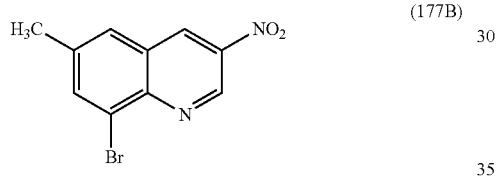

Intermediate 177A (0.537 g, 1.884 mmol) and 2-bromo-4-methylaniline hydrochloride (0.419 g, 1.884 mmol) were dissolved in acetic acid (3 mL) and allowed to reflux for 18 h. The reaction mixture was diluted with 1 N NaOH, until basic, and EtOAc. The layers were separated and the aqueous layer was back extracted with EtOAc (×3). The combined organic layer was washed with brine, dried with sodium sulfate, and concentrated under reduced pressure and was purified on ISCO, 40 g column 0-100% EtOAc in hexanes to yield Intermediate 177B (0.188 g, 0.704 mmol, 37.4% yield) as a yellow solid. LC-MS: method H, RT=0.99 min, MS (ESI) m/z: 267.0 (M+H)$^+$.

Intermediate 177C: 8-(benzofuran-2-yl)-6-methyl-3-nitroquinoline

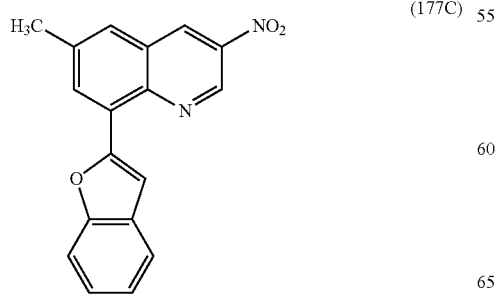

Intermediate 177B (0.070 g, 0.262 mmol) and benzofuran-2-ylboronic acid (0.042 g, 0.262 mmol) were dissolved in DMF (20 mL). PdCl$_2$(dppf)-CH$_2$Cl$_2$ adduct (0.013 g, 0.016 mmol) was added and the reaction mixture was degassed by bubbling with argon for 15 minutes. Na$_2$CO$_3$ (0.175 mL, 0.524 mmol) was added and the reaction mixture was degassed for 5 minutes, then sealed and heated to 90° C. in the microwave for 30 minutes. The reaction mixture was diluted with EtOAc and filtered through a micron filter and concentrated in vacuo. The reaction mixture was purified by ISCO 40 g column with a 0-100% gradient of EtOAc in hexanes was used. Combined impure fractions were diluted with DMF, filtered, and purified by preparative HPLC (Method D, 55 to 90% B in 10 minutes) to yield Intermediate 177C (0.0364 g, 0.120 mmol, 45.6% yield): $^1$H NMR (400 MHz, CHLOROFORM-d) δ 8.97 (d, J=2.5 Hz, 1H), 8.54 (d, J=1.8 Hz, 1H), 8.29 (d, J=0.8 Hz, 1H), 7.75 (s, 1H), 7.73-7.70 (m, 1H), 7.58 (dd, J=8.3, 0.8 Hz, 1H), 7.36 (td, J=7.7, 1.4 Hz, 1H), 7.30-7.27 (m, 1H), 2.69 (s, 3H). LC-MS: method H, RT=1.31 min, MS (ESI) m/z: 304.9 (M+H)$^+$. Analytical HPLC Method B: 100% purity.

Intermediate 177D: 8-(benzofuran-2-yl)-6-methylquinolin-3-amine

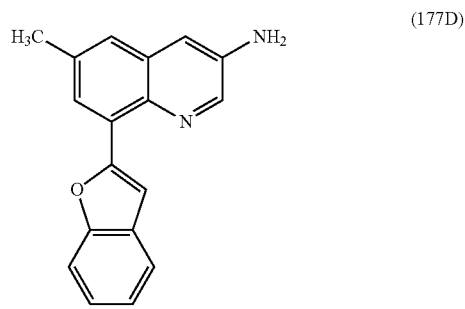 [SMILES: Cc1cc(-c2cc3ccccc3o2)c2ncc(N)cc2c1]

Intermediate 177C (0.031 g, 0.102 mmol) was dissolved in MeOH (5 mL) and Pd/C (1.084 mg, 10.19 μmol) was added. The reaction mixture was evacuated and back filled with argon (×3). The reaction mixture was then evacuated and back filled with hydrogen (0.205 mg, 0.102 mmol) (×3). The reaction mixture was allowed to stir at room temperature for 3 hours. The reaction mixture was filtered to remove the Pd/C and concentrated under reduced pressure to yield Intermediate 177D (0.022 g, 0.080 mmol, 79% yield). Used without further purification. $^1$H NMR (400 MHz, CHLOROFORM-d) δ 8.56 (d, J=2.8 Hz, 1H), 8.17 (d, J=0.8 Hz, 1H), 8.06 (d, J=1.8 Hz, 1H), 7.68-7.64 (m, 1H), 7.55 (dd, J=8.2, 0.6 Hz, 1H), 7.36 (s, 1H), 7.32-7.27 (m, 1H), 7.24 (dd, J=7.5, 1.0 Hz, 1H), 7.20 (d, J=2.8 Hz, 1H), 3.91 (s, 2H), 2.56 (s, 3H). LC-MS: method H, RT=0.95 min, MS (ESI) m/z: 275.3 (M+H)$^+$.

Intermediate 177E:
8-(benzofuran-2-yl)-6-methylquinolin-3-ol

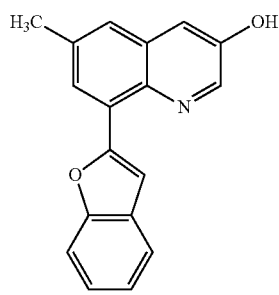

(177E)

Intermediate 177D (0.0178 g, 0.065 mmol) was dissolved in MeCN (0.468 mL) and cooled to 0° C. Tetrafluoroboric acid (9.84 μL, 0.071 mmol) was added and stirring continued for 10 minutes. After this time, a solution of tert-butyl nitrite (8.49 μL, 0.071 mmol) in MeCN (0.047 mL) was added dropwise and stirring continued for 10 minutes. After this time, the reaction mixture was cooled to −15° C. and water (0.936 mL) was added. This cooled solution was added into a solution of copper(II) nitrate, trihydrate (3.14 g, 12.98 mmol) and copper(I) oxide (0.418 g, 2.92 mmol) in water (9.36 mL), precooled to 0° C. Stirring was continued at the same temperature for 18 h. The reaction mixture was then extracted thrice with EtOAc. The combined organic extracts were washed with brine, dried with sodium sulfate, filtered through Celite, and concentrated in vacuo. The reaction mixture was purified on Prep HPLC Method A to yield Intermediate 177E 0.018 g, 0.065 mmol, 60%, 65% purity) Used in the next step without further purification. LC-MS: method H, RT=1.14 min, MS (ESI) m/z: 276.1(M+H)$^+$.

Example 177

Intermediate 177E (0.018 g, 0.065 mmol) was dissolved in acetone (3 mL) and K$_2$CO$_3$ (0.018 g, 0.131 mmol) was added. MeI (8.18 μl, 0.131 mmol) was added and the reaction mixture was allowed to stir at room temperature for 5 h. The reaction mixture was diluted with water and EtOAc. The layers were separated and the organic layer was washed with brine, dried with sodium sulfate, and concentrated under reduced pressure. The reaction mixture was diluted with DMF, filtered, and purified by preparative HPLC (Method D, 35 to 85% B in 10 minutes) to give Example 177 (0.0032 g, 10.95 μmol, 16.75% yield): $^1$H NMR (500 MHz, METHANOL-d$_4$) δ 8.68 (d, J=2.8 Hz, 1H), 8.12 (d, J=1.7 Hz, 1H), 8.08 (s, 1H), 7.65 (d, J=7.4 Hz, 1H), 7.56-7.53 (m, 2H), 7.46 (d, J=3.0 Hz, 1H), 7.32-7.27 (m, 1H), 7.26-7.19 (m, 1H), 3.98 (s, 3H), 2.59 (s, 3H)). LC-MS: method H, RT=1.31 min, MS (ESI) m/z: 290.2 (M+H)$^+$. Analytical HPLC Method B: 99% purity.

Example 178

2-(2-(difluoromethoxy)-7-methylquinoxalin-5-yl)-4,5,6,7-tetrahydrobenzo[d]thiazole

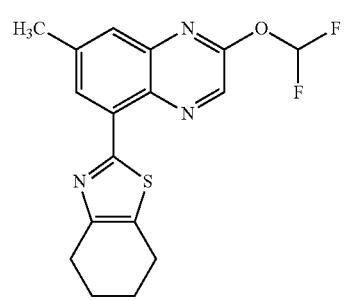

(178)

Intermediate I-1 (0.007 g, 0.028 mmol) and 2-bromo-4,5,6,7-tetrahydrobenzo[d]thiazole (6.01 mg, 0.028 mmol) were dissolved in DMF (3 mL). PdCl$_2$(dppf)-CH$_2$Cl$_2$ adduct (1.350 mg, 1.654 mmol) was added and the reaction mixture was degassed by bubbling with argon for 15 minutes. Na$_2$CO$_3$ (0.018 mL, 0.055 mmol) was added and the reaction mixture was degassed for 5 minutes, then sealed and heated to 90° C. in the microwave for 30 minutes. The reaction mixture was diluted with EtOAc and filtered through a micron filter and concentrated in vacuo. The reaction mixture was diluted with DMF, filtered, and purified by preparative HPLC (Method D, 50 to 85% B in 10 minutes) to yield Example 178 (0.0052 g, 0.015 mmol, 54.0% yield): $^1$H NMR (500 MHz, METHANOL-d$_4$) δ 8.64 (s, 1H), 8.43 (d, J=1.7 Hz, 1H), 7.84-7.53 (m, 2H), 2.89 (d, J=5.8 Hz, 4H), 2.64 (s, 3H), 2.00-1.87 (m, 4H). LC-MS: method H, RT=1.26 min, MS (ESI) m/z: 348.0 (M+H)$^+$. Analytical HPLC Method B: 99% purity.

Example 179

5-methoxy-2-(2-methoxy-7-methylquinoxalin-5-yl)-7-methylthiazolo[5,4-b]pyridine

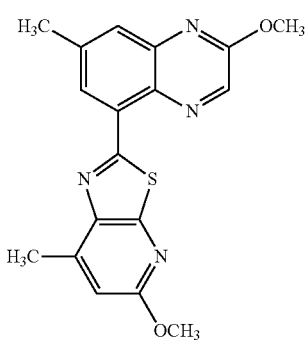

(179)

Intermediate I-9 (10 mg, 0.033 mmol), 2-bromo-5-methoxy-7-methylthiazolo[5,4-b]pyridine (10.36 mg, 0.040 mmol), and phosphoric acid, potassium salt (14.14 mg, 0.067 mmol) were dissolved in DMF (333 μl) and degassed by bubbling with argon for 15 minutes. Pd(Ph$_3$P)$_4$ (3.85 mg, 3.33 μmol) was added and degassing continued for 5 minutes. The reaction mixture was heated to 85° C. for 18 h. The reaction mixture was diluted with DMF, filtered, and purified by preparative HPLC (Method D, 60% to 100% B in 20 minutes) to yield Example 179 (0.0014 g, 3.89 µmol, 11.69% yield): $^1$H NMR (500 MHz, CHLOROFORM-d) δ 8.62 (br. s., 1H), 8.56 (br. s., 1H), 7.76 (br. s., 1H), 6.72 (br. s., 1H), 4.15 (br. s., 3H), 4.05 (br. s., 3H), 2.81 (br. s., 3H), 2.69 (br. s., 3H). LC-MS: method H, RT=1.57 min, MS (ESI) m/z: 353.0 (M+H)$^+$. Analytical HPLC Method B: 98% purity.

Example 180

6-fluoro-5-methoxy-2-(2-(methoxymethyl)-7-methylquinoxalin-5-yl)thiazolo[5,4-b] pyridine

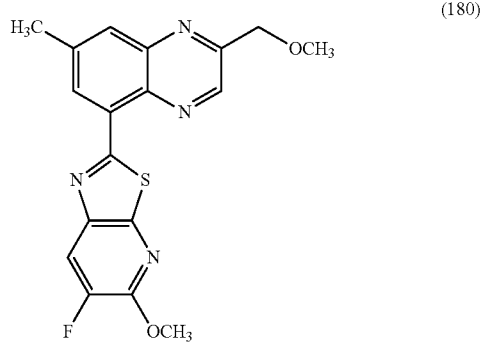

(180)

Intermediate I-2 (955 µl, 0.048 mmol), Intermediate I-17 (15.07 mg, 0.057 mmol), and phosphoric acid, potassium salt (20.27 mg, 0.095 mmol) were dissolved in DMF (477 µl) and degassed by bubbling with argon for 15 minutes. Pd(Ph$_3$)$_4$ (5.52 mg, 4.77 µmol) was added and degassing continued for 5 minutes. The reaction mixture was heated to 85° C. for 18 h. The reaction mixture was diluted with DMF, filtered, and purified by preparative HPLC (Method D, 45% to 75% B in 22 minutes) to yield Example 180 (2.0 mg, 4.91 µmol, 10.29% yield): $^1$H NMR (500 MHz, DMSO-d$_6$) δ 9.13 (s, 1H), 8.79 (s, 1H), 8.48 (d, J=10.7 Hz, 1H), 8.09 (s, 1H), 4.83 (s, 2H), 4.12 (s, 3H), 3.49 (s, 3H), 2.70 (s, 3H). LC-MS: method H, RT=1.39 min, MS (ESI) m/z: 371.1 (M+H)$^+$. Analytical HPLC Method B: 91% purity.

Example 181

5-methoxy-2-(2-(methoxymethyl)-7-methylquinoxalin-5-yl)-7-methylthiazolo[5,4-b] pyridine

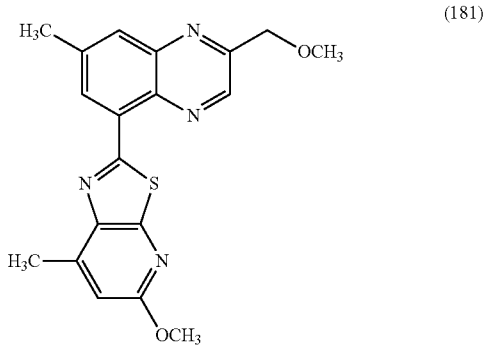 [SMILES: COCc1cnc2c(-c3nc4c(C)cc(OC)nc4s3)cc(C)cc2n1]

(181)

Intermediate I-2 (1273 µl, 0.064 mmol), Intermediate I-16 (19.79 mg, 0.076 mmol), and phosphoric acid, potassium salt (27.0 mg, 0.127 mmol) were dissolved in DMF (637 µl) and degassed by bubbling with argon for 15 minutes. Pd(PPh$_3$)$_4$ (7.36 mg, 6.37 µmol) was added and degassing continued for 5 minutes. The reaction mixture was heated to 85° C. for 18 h. The reaction mixture was diluted with DMF, filtered, and purified by preparative HPLC (Method D, 60% to 100% B in 20 minutes) to yield Example 181 (11 mg, 0.029 mmol, 45.7% yield): $^1$H NMR (500 MHz, CHLOROFORM-d) δ 9.06 (s, 1H), 8.82 (d, J=1.7 Hz, 1H), 7.94 (d, J=0.8 Hz, 1H), 6.71 (d, J=0.8 Hz, 1H), 4.84 (s, 2H), 4.03 (s, 3H), 3.58 (s, 3H), 2.79 (d, J=0.6 Hz, 3H), 2.71 (s, 3H) LC-MS: method H, RT=1.43 min, MS (ESI) m/z: 367.1 (M+H)$^+$. Analytical HPLC Method B: 97% purity.

Example 182

6-fluoro-5-methoxy-2-(2-methoxy-7-methylquinoxalin-5-yl)thiazolo[5,4-b]pyridine

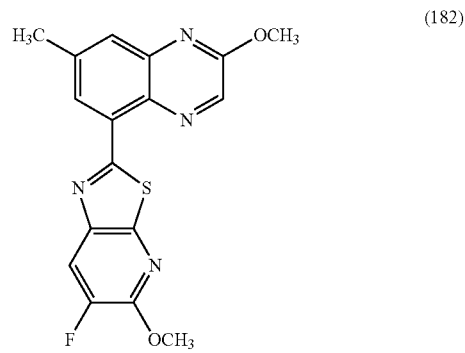 [SMILES: COc1cnc2c(-c3nc4cc(F)c(OC)nc4s3)cc(C)cc2n1]

(182)

Intermediate I-1 (0.020 g, 0.067 mmol) and Intermediate I-17 (0.018 g, 0.067 mmol) were dissolved in DMF (1 mL). PdCl$_2$(dppf)-CH$_2$Cl$_2$ adduct (3.26 mg, 4.00 µmol) was added and the reaction mixture was degassed by bubbling with argon for 15 minutes. Na$_2$CO$_3$, 3 M aqueous solution (0.100 mL, 0.300 mmol) was added and the reaction mixture was degassed for 5 minutes, then sealed and heated to 90° C. in the microwave for 30 minutes. The reaction mixture was filtered and the solid was collected. Recrystallized from DMSO to yield Example 182 (0.0024 g, 6.13 µmol, 9.20% yield) as a yellow solid: $^1$H NMR (400 MHz, CHLOROFORM-d) δ 8.57 (d, J=1.8 Hz, 1H), 8.54 (s, 1H), 7.98 (d, J=10.6 Hz, 1H), 7.77 (s, 1H), 4.15 (s, 3H), 4.13 (s, 3H), 2.65 (s, 3H). LC-MS: method H, RT=1.52 min, MS (ESI) m/z: 357.1 (M+H)$^+$. Analytical HPLC Method A: 91% purity.

Example 183

6-methoxy-2-(2-(methoxymethyl)-7-methylquinoxalin-5-yl)-4-methylbenzo[d]thiazole

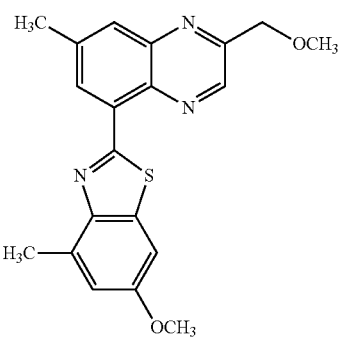

(183)

Intermediate I-2 (0.025 g, 0.080 mmol) and Intermediate I-3 (0.021 g, 0.080 mmol) were dissolved in DMF (3 mL). PdCl$_2$(dppf)-CH$_2$Cl$_2$ adduct (3.90 mg, 4.77 μmol) was added and the reaction mixture was degassed by bubbling with argon for 15 minutes. Na$_2$CO$_3$, 3 M aq. solution (0.100 mL, 0.300 mmol) was added and the reaction mixture was degassed for 5 minutes, then sealed and heated to 90° C. in the microwave for 30 minutes. The reaction mixture was diluted with EtOAc and water. The layers were separated and the organic layer was washed with brine, dried with sodium sulfate, and concentrated under reduced pressure. The reaction mixture was purified on Prep HPLC using Method A yield Example 183 (0.021 g, 0.057 mmol, 72.2% yield): $^1$H NMR (500 MHz, CHLOROFORM-d) δ 9.08 (s, 1H), 8.88 (s, 1H), 7.93 (s, 1H), 7.27-7.26 (m, 1H), 6.94 (s, 1H), 4.84 (s, 2H), 3.90 (s, 3H), 3.57 (d, J=0.6 Hz, 3H), 2.84 (s, 3H), 2.71 (s, 3H). LC-MS: method H, RT=1.40 min, MS (ESI) m/z: 366.2 (M+H)$^+$. Analytical HPLC: Method A, 92.3% purity.

Example 184

5-(benzofuran-2-yl)-2-(1-methoxyethyl)-7-methylquinoxaline

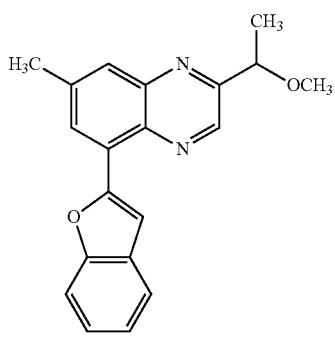

(184)

Intermediate 184A: ethyl 5-(benzofuran-2-yl)-7-methylquinoxaline-2-carboxylate

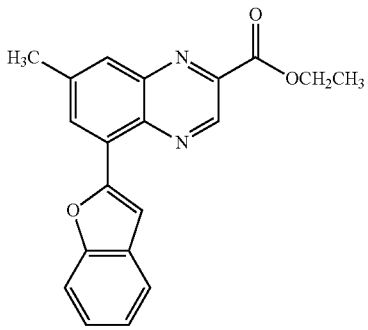

(184A)

Intermediate I-15 (0.650 g, 2.202 mmol) and benzofuran-2-ylboronic acid (0.357 g, 2.202 mmol) were dissolved in DMF (20 mL). PdCl$_2$(dppf)-CH$_2$Cl$_2$ adduct (0.108 g, 0.132 mmol) was added and the reaction mixture was degassed by bubbling with argon for 15 minutes. 3 M Na$_2$CO$_3$ (1.468 mL, 4.40 mmol) was added and the reaction mixture was degassed for 5 minutes, then sealed and heated to 90° C. in the microwave for 30 minutes. The reaction mixture was diluted with EtOAc and filtered through a micron filter and concentrated in vacuo. Purified by ISCO to remove any Pd or ligand based impurities using a 40 g column with a 0-100% gradient of EtOAc in hexanes. Fractions pooled and the residue was purified on Prep HPLC Method A to yield Intermediate 184A (0.117 g, 0.352 mmol, 15.98% yield). LC-MS: method H, RT=1.21 min, MS (ESI) m/z: 333.1 (M+H).

Intermediate 184B: 5-(benzofuran-2-yl)-7-methylquinoxaline-2-carboxylic acid

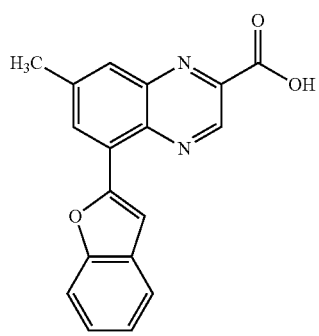

(184B)

Intermediate 184A (0.020 g, 0.060 mmol) was dissolved in THF (3 mL) and MeOH. NaOH, 1 N in water (0.500 mL, 0.500 mmol) was added and the reaction mixture was allowed to stir at room temperature for 18 h. Diluted with 1 N HCl and EtOAc. The layers were separated and the aqueous layer was back extracted with EtOAc (×3). The organic layer was washed with brine, dried with sodium sulfate, and concentrated under reduced pressure to yield Intermediate 184B (0.017 g, 0.060 mmol, 99% yield) as a yellow solid. Used without further purification in the next step. $^1$H NMR (500 MHz, DMSO-d$_6$) δ 9.49 (s, 1H), 8.42 (d, J=1.4 Hz, 1H), 8.23 (s, 1H), 8.03 (br. s., 1H), 7.81 (d, J=7.4 Hz, 1H), 7.71 (d, J=8.0 Hz, 1H), 7.41 (td, J=7.7, 1.4 Hz, 1H), 7.35-7.29 (m, 1H), 2.69 (s, 3H). LC-MS: method H, RT=1.05 min, MS (ESI) m/z: 305.0 (M+H)⁺.

Intermediate 184C: 5-(benzofuran-2-yl)-7-methylquinoxaline-2-carbonyl chloride

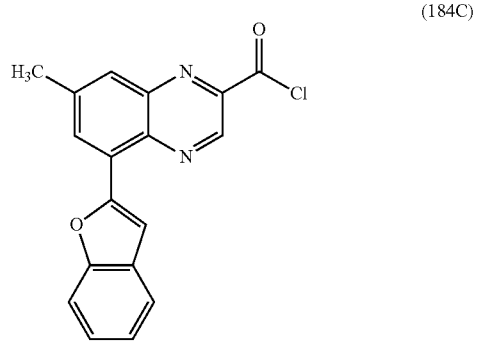 [SMILES: Cc1cc(-c2cc3ccccc3o2)c2ncc(C(=O)Cl)nc2c1]

Intermediate 184B (0.018 g, 0.059 mmol) was dissolved in DCM (3 mL) and oxalyl chloride (5.18 μl, 0.059 mmol) was added. DMF (0.458 μl, 5.92 μmol) was added and the reaction mixture was allowed to stir at room temperature for 30 min. The reaction was concentrated and stored under vacuum for 1 h to yield Intermediate 184C (0.019 g, 0.059 mmol, 100% yield). Used without further purification in the next step. LC-MS: method H, RT=1.16 min, MS (ESI) m/z: 319.1 (M+H)⁺. Observed mass of the methyl ether in the LC/MS.

Intermediate 184D: 5-(benzofuran-2-yl)-N-methoxy-N,7-dimethylquinoxaline-2-carboxamide

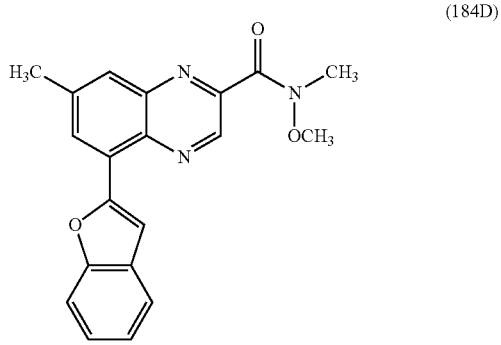

Intermediate 184C (0.019 g, 0.059 mmol) was dissolved in DCM (3 mL). DMAP (0.719 mg, 5.89 μmol), TEA (0.016 mL, 0.118 mmol), and N,O-dimethylhydroxylamine hydrochloride (5.74 mg, 0.059 mmol) were added and the reaction mixture was allowed to stir at room temperature for 18 h. The reaction mixture was diluted with water and EtOAc. The layers were extracted and the aqueous layer was back extracted with EtOAc (×3). The combined organic layer was washed with brine, dried with sodium sulfate, and concentrated under reduced pressure to yield Intermediate 184D (0.021 g, 0.060 mmol, 100% yield) as a yellow solid. Used without further purification in the next step. ¹H NMR (400 MHz, CHLOROFORM-d) δ 8.41 (d, J=1.8 Hz, 1H), 8.21 (s, 1H), 7.88 (s, 1H), 7.70 (d, J=7.5 Hz, 1H), 7.58 (d, J=8.3 Hz, 1H), 7.40-7.33 (m, 1H), 7.31-7.25 (m, 2H), 3.83 (br. s., 3H), 3.48 (d, J=15.6 Hz, 3H), 2.74-2.64 (m, 3H). LC-MS: method H, RT=1.13 min, MS (ESI) m/z: 348.1 (M+H)⁺.

Intermediate 184E: 5-(benzofuran-2-yl)-N-methoxy-N,7-dimethylquinoxaline-2-carboxamide

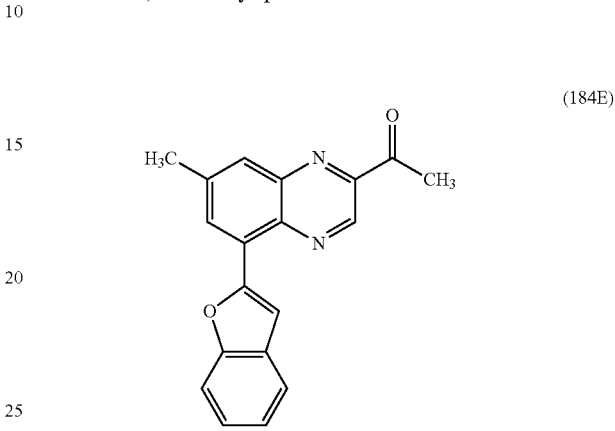

Intermediate 184D (0.0698 g, 0.201 mmol) was dissolved in THF (2.009 mL) and cooled to 0° C. methylmagnesium bromide (0.067 mL, 0.201 mmol) was added and the reaction mixture was allowed to slowly warm to room temperature over 3 h. The reaction mixture was diluted with EtOAc and 1 N aqueous HCl. The mixture was allowed to stir for 30 min. The layers were separated and the organic layer was washed with brine, dried with sodium sulfate, and concentrated under reduced pressure. The reaction mixture was purified on Prep HPLC using Method A to yield Intermediate 184E (0.0087 g, 0.029 mmol, 14.32% yield) as a yellow solid. ¹H NMR (400 MHz, CHLOROFORM-d) δ 9.54 (s, 1H), 8.46 (d, J=1.8 Hz, 1H), 8.23 (d, J=0.8 Hz, 1H), 7.94 (d, J=0.8 Hz, 1H), 7.71 (d, J=7.8 Hz, 1H), 7.58 (d, J=7.5 Hz, 1H), 7.35 (td, J=7.7, 1.3 Hz, 1H), 7.31-7.29 (m, 1H), 2.87 (s, 3H), 2.71 (s, 3H). LC-MS: method H, RT=1.25 min, MS (ESI) m/z: 303.1 (M+H)⁺.

Intermediate 184F: 1-(5-(benzofuran-2-yl)-7-methylquinoxalin-2-yl)ethanol

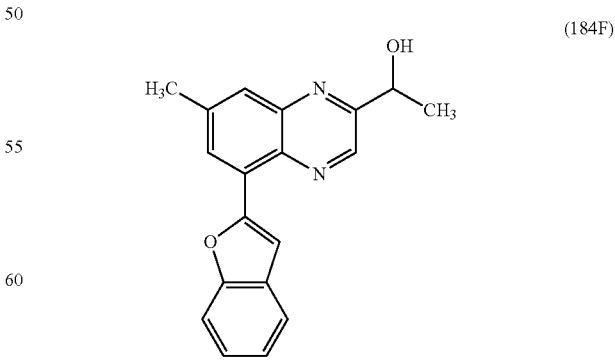

Intermediate 184E (0.010 g, 0.033 mmol) was dissolved in MeOH (1 mL) and cooled to 0° C. CeCl₃ (0.012 g, 0.033 mmol) was added to the reaction mixture followed by NaBH₄ (5.01 mg, 0.132 mmol). The reaction mixture was allowed to stir for 1 h. The reaction mixture was diluted with saturated NH₄Cl solution and EtOAc. The layers were separated and the aqueous layer was back extracted with EtOAc (x3). The combined organic layer was washed with brine, dried with sodium sulfate, and concentrated under reduced pressure to yield Intermediate 184F (0.009 g, 0.030 mmol, 89% yield). Will be used without further purification. LC-MS: method H, RT=1.23 min, MS (ESI) m/z: 305.1 (M+H)⁺.

Example 184

Intermediate 184F (0.0069 g, 0.023 mmol) was dissolved in DMF and NaH (0.907 mg, 0.023 mmol) was added. The reaction mixture was allowed to stir at room temperature for 10 min and MeI (1.418 µl, 0.023 mmol) was added. The reaction mixture was stirred at room temperature for 3 h. The reaction mixture was diluted with water and EtOAc. The layers were separated and the organic layer was washed with brine, dried with sodium sulfate and concentrated under reduced pressure to yield a yellow oil. The reaction mixture was diluted with DMF, filtered, and purified by preparative HPLC (Method D, 55% to 95% B in 10 minutes) to yield Example 184 (0.0005 g, 1.571 µmol, 6.93% yield): ¹H NMR (500 MHz, METHANOL-d₄) δ 9.07 (s, 1H), 8.34 (d, J=1.7 Hz, 1H), 8.16 (s, 1H), 7.82 (s, 1H), 7.68 (d, J=7.7 Hz, 1H), 7.57 (d, J=8.3 Hz, 1H), 7.36-7.31 (m, 1H), 7.27-7.23 (m, 1H), 4.69 (q, J=6.8 Hz, 1H), 3.42 (s, 3H), 2.68 (s, 3H), 1.62 (d, J=6.6 Hz, 3H). LC-MS: method H, RT=1.30 min, MS (ESI) m/z: 319.1 (M+H)⁺. Analytical HPLC Method B: 100% purity.

Example 185

6-methoxy-2-(3-(methoxymethyl)-6-methylquinolin-8-yl)-4-methylbenzo[d]thiazole

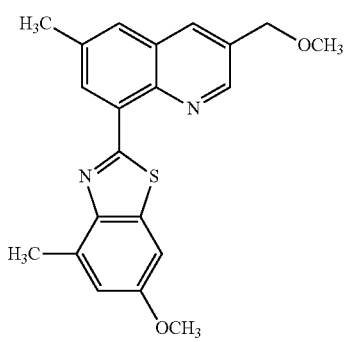
(185)

Intermediate 185A: methyl 8-bromo-6-methylquinoline-3-carboxylate

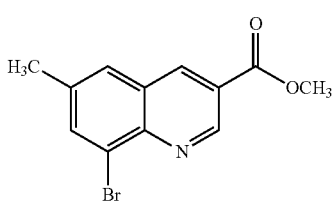
(185A)

8-bromo-6-methylquinoline-3-carboxylic acid (250 mg, 0.940 mmol) was dissolved in MeOH (3758 µl). Thionyl chloride (206 µl, 2.82 mmol) was added and the reaction mixture was heated to reflux for 4 h. The reaction mixture was cooled to ambient temperature and concentrated in vacuo to yield Intermediate 185A (0.263 g, 0.940 mmol, 100% yield): ¹H NMR (400 MHz, CHLOROFORM-d) δ 9.52 (d, J=2.0 Hz, 1H), 8.80 (d, J=1.8 Hz, 1H), 8.06 (d, J=1.5 Hz, 1H), 7.70 (s, 1H), 4.06 (s, 3H), 2.59 (s, 3H). LC-MS: method H, RT=1.14 min, MS (ESI) m/z: 280/282 (M+H)⁺.

Intermediate 185B: (8-bromo-6-methylquinolin-3-yl)methanol

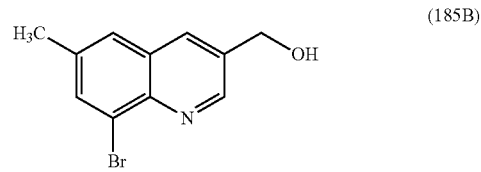
(185B)

NaBH₄ (70.2 mg, 1.856 mmol) and calcium chloride (103 mg, 0.928 mmol) were dissolved in THF (2750 µl). A solution of Intermediate 185A (260 mg, 0.928 mmol) in THF (688 µl) was added dropwise. The reaction mixture was allowed to stir for 18 h. The reaction mixture was diluted with EtOAc, washed with water, then brine, dried sodium sulfate, filtered, and concentrated in vacuo. The crude material was purified by column chromatography (ISCO, 40 g silica gel column, 19 minute gradient from 0 to 100% EtOAc in hexanes) to yield Intermediate 185B (0.146 g, 0.579 mmol, 62% yield): ¹H NMR (400 MHz, CHLOROFORM-d) δ 8.97 (d, J=1.8 Hz, 1H), 8.09 (s, 1H), 7.93 (s, 1H), 7.58 (s, 1H), 4.97 (d, J=5.5 Hz, 2H), 2.55 (s, 3H), 1.93 (t, J=5.7 Hz, 1H). LC-MS: method H, RT=0.85 min, MS (ESI) m/z: 252/254 (M+H)⁺.

Intermediate 185C: (8-bromo-6-methylquinolin-3-yl)methyl methanesulfonate

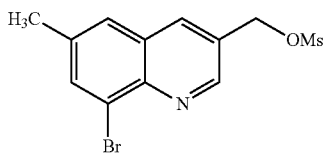
(185C)

Intermediate 185B (146 mg, 0.579 mmol) and TEA (242 µL, 1.737 mmol) were dissolved in DCM (16 mL). Methanesulfonic anhydride (121 mg, 0.695 mmol) was added and the reaction mixture was allowed to stir at room temperature for 3 h. The reaction mixture was diluted with DCM and washed with saturated NaHCO₃, dried sodium sulfate, filtered, and concentrated in vacuo to yield Intermediate 185C (0.191 g, 0.579 mmol, 100% yield). The material will be used crude in the next step. LC-MS: method H, RT=1.03 min, MS (ESI) m/z: 330.0 (M+H)⁺.

Intermediate 185D:
8-bromo-3-(methoxymethyl)-6-methylquinoline

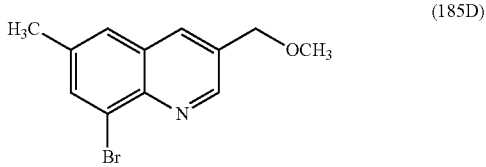

Intermediate 185C (190 mg, 0.575 mmol) was dissolved in THF (12 mL). 0.5 M sodium methoxide (2302 μl, 1.151 mmol) and the reaction mixture was allowed to stir for 18 h. The reaction mixture was concentrated in vacuo to remove the THF, diluted with EtOAc and washed with 0.5 N HCl, then brine, dried sodium sulfate, filtered, and concentrated in vacuo to yield Intermediate 185D (0.100 g, 0.376 mmol, 65% yield): $^1$H NMR (400 MHz, CHLOROFORM-d) δ 8.94 (d, J=2.0 Hz, 1H), 8.07-8.03 (m, 1H), 7.93 (d, J=1.8 Hz, 1H), 7.57 (s, 1H), 4.69 (s, 2H), 3.49 (s, 3H), 2.55 (s, 3H). LC-MS: method H, RT=1.00 min, MS (ESI) m/z: 266.0 (M+H)$^+$.

Intermediate 185E:
(3-(methoxymethyl)-6-methylquinolin-8-yl)boronic acid

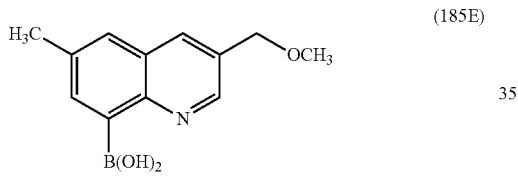

Intermediate 185D (100 mg, 0.376 mmol), bis(pinacolato) diboron (143 mg, 0.564 mmol), and potassium acetate (92 mg, 0.939 mmol) were dissolved in dioxane (2099 μl) and degassed for 5 minutes by bubbling with argon. PdCl$_2$(dppf)-CH$_2$Cl$_2$ adduct (24.55 mg, 0.030 mmol) was added and the reaction mixture was degassed for an additional 10 minutes. The reaction mixture was heated to 130° C. in the microwave for 45 minutes. The reaction mixture was then diluted with EtOAc and water. The reaction mixture was further extracted twice with EtOAc. The combined organic layers were washed with brine, dried sodium sulfate, filtered, and concentrated in vacuo. The crude material was purified by Prep LC (Axia Luna 5u C18 30×100 mm column, 12 minute gradient from 30 to 100% B in A, A=10:90:0.1 MeOH:H$_2$O:TFA, B=90:10:0.1 MeOH:H$_2$O:TFA) to yield Intermediate 185E (0.063 g, 0.240 mmol, 64% yield): LC-MS: method H, RT=0.75 min, MS (ESI) m/z: 232.1 (M+H)$^+$ (see mass of methyl boronic ester in the LC/MS).

Example 185

Intermediate 185E (0.025 g, 0.096 mmol) and Intermediate I-3 (0.025 g, 0.096 mmol) were dissolved in DMF (1 mL). PdCl$_2$(dppf)-CH$_2$Cl$_2$ adduct (4.73 mg, 5.79 μmol) was added and the reaction mixture was degassed by bubbling with argon for 15 minutes. Na$_2$CO$_3$, 3 M aq. solution (0.030 mL, 0.090 mmol) was added and the reaction mixture was degassed for 5 minutes, then sealed and heated to 90° C. in the microwave for 30 minutes. The reaction mixture was diluted with DMF, filtered, and purified by preparative HPLC (Method D, 30% to 70% B in 10 minutes) to yield Example 185 (0.0097 g, 0.026 mmol, 27.0% yield): $^1$H NMR (500 MHz, DMSO-d$_6$) δ 9.00 (d, J=1.9 Hz, 1H), 8.80 (d, J=1.4 Hz, 1H), 8.36 (s, 1H), 7.95 (s, 1H), 7.54 (d, J=2.2 Hz, 1H), 7.00 (d, J=1.4 Hz, 1H), 4.71 (s, 2H), 3.86 (s, 3H), 3.42 (s, 3H), 2.76 (s, 3H), 2.65 (s, 3H). LC-MS: method H, RT=1.22 min, MS (ESI) m/z: 365.3 (M+H)$^+$. Analytical HPLC Method B: 98% purity.

Example 186

2-(2-(difluoro(methoxy)methyl)-7-methylquinoxalin-5-yl)-6-methoxy-4-methylbenzo[d]thiazole

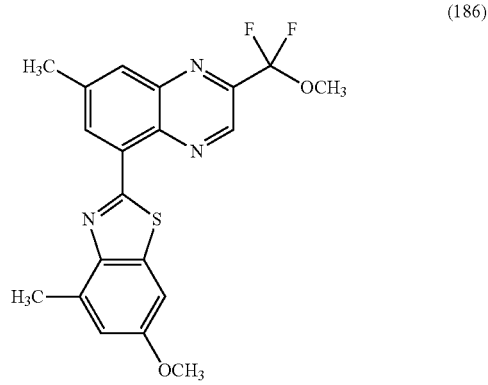 [SMILES: COc1cc(C)c2nc(-c3cc(C)cc4nc(C(F)(F)OC)cnc34)sc2c1]

Intermediate 186A: O-methyl
5-bromo-7-methylquinoxaline-2-carbothioate

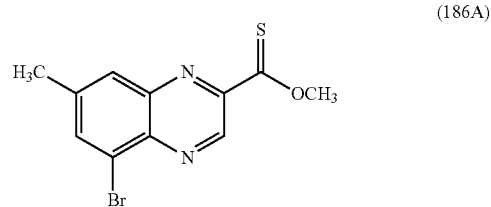 [SMILES: COC(=S)c1cnc2c(Br)cc(C)cc2n1]

Methyl 5-bromo-7-methylquinoxaline-2-carboxylate (0.200 g, 0.711 mmol) was dissolved in o-xylenes (2.85 mL) and Lawesson's Reagent (0.576 g, 1.423 mmol) was added. The reaction mixture was heated to reflux for 18 h. The reaction mixture was filtered and the filter cake washed with o-xylenes. o-Xylenes solution was loaded directly on the ISCO column. The reaction mixture was purified on ISCO 40 g column 0-50% EtOAc in hexanes gradient to yield Intermediate 186A (0.005 g, 0.017 mmol, 2.365% yield) as a yellow solid. $^1$H NMR (400 MHz, CHLOROFORM-d) δ 9.78 (s, 1H), 8.07 (d, J=1.8 Hz, 1H), 8.04 (d, J=0.9 Hz, 1H), 4.49 (s, 3H), 2.64 (s, 3H). LC-MS: method H, RT=1.27 min, MS (ESI) m/z: 296.9 (M+H)$^+$.

Intermediate 186B: 5-bromo-2-(difluoro(methoxy)methyl)-7-methylquinoxaline

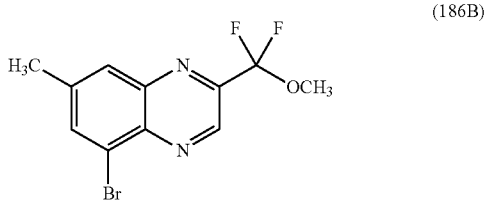
(186B)

Intermediate 186A (0.068 g, 0.229 mmol) was dissolved in CH$_2$Cl$_2$. Bis-(2-methoxyethyl)aminosulfur trifluoride (0.084 mL, 0.458 mmol) was added and the reaction mixture was allowed to stir at room temperature for 48 h. The reaction mixture was diluted with EtOAc and water. The organic layer was washed with sodium bicarbonate, washed with brine, dried with sodium sulfate, and concentrated under reduced pressure to yield Intermediate 186B (0.065 g, 0.214 mmol, 94% yield) a yellow oil. $^1$H NMR (400 MHz, CHLOROFORM-d) δ 9.21 (s, 1H), 8.08 (d, J=1.8 Hz, 1H), 8.01 (s, 1H), 3.91 (s, 3H), 2.64 (s, 3H). LC-MS: method H, RT=1.29 min, MS (ESI) m/z: 302.9 (M+H)$^+$.

Intermediate 186C: (2-(difluoro(methoxy)methyl)-7-methylquinoxalin-5-yl)boronic acid

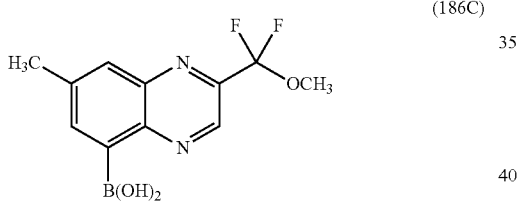
(186C)

A mixture of Intermediate 186B (0.070 g, 0.231 mmol), 4,4,4',4',5,5,5',5'-octamethyl-2,2'-bi(1,3,2-dioxaborolane) (0.088 g, 0.346 mmol), potassium acetate (0.057 g, 0.577 mmol) in dioxane (2.309 mL) were degassed by bubbling argon for 5 min. PdCl$_2$(dppf)-CH$_2$Cl$_2$ adduct (9.43 mg, 0.012 mmol) was added and the mixture was sealed and heated in microwave at 130° C. for 30 min. The reaction mixture was diluted with water and EtOAc. The layers were separated and the organic layer was washed with water, washed with brine, dried with sodium sulfate, and concentrated under reduced pressure. The reaction mixture was purified on Prep HPLC using Method A to yield Intermediate 186C (0.010 g, 0.037 mmol, 16.16% yield) as a brown solid. LC-MS: method H, RT=0.88 min, MS (ESI) m/z: 269.1 (M+H)$^+$.

Example 186

Intermediate 186C (0.010 g, 0.029 mmol) and Intermediate I-3 (7.37 mg, 0.029 mmol) were dissolved in DMF (1 mL). PdCl$_2$(dppf)-CH$_2$Cl$_2$ adduct (1.399 mg, 1.713 µmol) was added and the reaction mixture was degassed by bubbling with argon for 15 minutes. Na$_2$CO$_3$, 3 M aqueous solution (0.050 mL, 0.150 mmol) was added and the reaction mixture was degassed for 5 minutes, then sealed and heated to 90° C. in the microwave for 30 minutes. The reaction mixture was diluted with DMF, filtered, and purified by preparative HPLC (Method D, 55% to 100% B in 20 minutes) to yield Example 186 (0.0064 g, 0.016 mmol, 55.8% yield): $^1$H NMR (500 MHz, DMSO-d$_6$) δ 9.36 (s, 1H), 8.93 (s, 1H), 8.17 (s, 1H), 7.56 (d, J=2.2 Hz, 1H), 7.02 (d, J=1.1 Hz, 1H), 3.86 (s, 3H), 3.85 (s, 3H), 2.76 (s, 3H), 2.73 (s, 3H). LC-MS: method H, RT=1.50 min, M/S (ESI) m/z: 402.1 (M+H)$^+$. Analytical HPLC Method B: 100% purity.

Example 187

6-methoxy-4-methyl-2-(7-methyl-2-(phenoxymethyl)quinoxalin-5-yl)benzo[d]thiazole

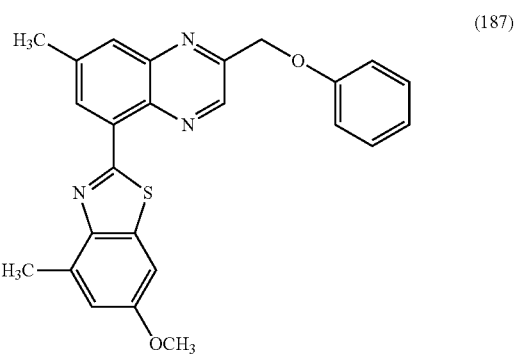 [SMILES: COc1cc(C)c2nc(-c3cc(C)cc4nc(COc5ccccc5)cnc34)sc2c1]
(187)

Intermediate 187A: 1-diazo-3-phenoxypropan-2-one

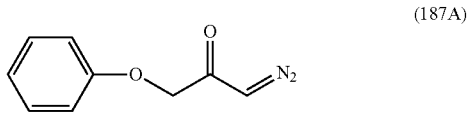
(187A)

To 2-phenoxyacetyl chloride (0.250 g, 1.465 mmol) in MeCN cooled with ice-bath was added (diazomethyl)trimethylsilane 2.0 M in diethyl ether (1.282 mL, 2.56 mmol). The mixture was allowed to stir at room temperature for 3 h. Solvent was removed under reduced pressure. The crude product was purified by flash chromatography (loading in chloroform, 0% to 50% EtOAc in hexane over 18 min using a 40 g silica gel cartridge). The desired fractions were combined and concentrated (bath temp below 35° C.) to yield Intermediate 187A (0.215 g, 1.220 mmol, 83% yield) as a pale yellow oil. $^1$H NMR (400 MHz, CHLOROFORM-d) δ 7.32 (t, J=8.0 Hz, 2H), 7.03 (t, J=7.4 Hz, 1H), 6.90 (d, J=8.4 Hz, 2H), 5.82 (s, 1H), 4.55 (s, 2H). LC-MS: method H, RT=1.27 min, MS (ESI) m/z: 177.1 (M+H)$^+$.

Intermediate 187B: 1-bromo-3-phenoxypropan-2-one

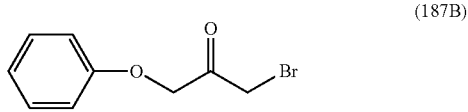 [SMILES: O=C(CBr)COc1ccccc1]
(187B)

Intermediate 187A (0.215 g, 1.220 mmol) was dissolved in Et$_2$O (4.88 mL) and the mixture was cooled to 0° C. and HBr (0.242 mL, 2.136 mmol) was added dropwise. After 5 min at 0° C., the reaction mixture was allowed to stir at room temperature for 10 min. The reaction mixture was diluted with ether, washed with saturated aqueous sodium bicarbonate, washed with brine, and dried over sodium sulfate. The organic layer was concentrated (kept bath below 30° C.) and the product was used immediately without further purification. Intermediate 187B (0.224 g, 0.978 mmol, 80% yield). $^1$H NMR (400 MHz, CHLOROFORM-d) δ 7.33 (t, J=7.9 Hz, 2H), 7.03 (t, J=7.4 Hz, 1H), 6.91 (d, J=8.1 Hz, 2H), 4.79 (s, 2H), 4.18 (s, 2H). LC-MS: method H, RT=1.09 min, Compound does not ionize well.

Intermediate 187C:
5-bromo-7-methyl-2-(phenoxymethyl)quinoxaline

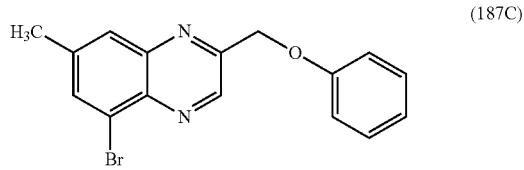 [SMILES: Cc1cc(Br)c2ncc(COc3ccccc3)nc2c1]

(187C)

To Intermediate I-1B (0.300 g, 0.906 mmol) in anhydrous DMF (30 mL) at 0° C. was added cesium carbonate (0.516 g, 1.585 mmol) in several portions. The brown solution was stirred at 0° C. for 10 min, followed by addition of Intermediate 187B (0.249 g, 1.087 mmol) in DMF (5.0 mL). The brown solution turned yellow. The mixture was stirred at room temperature for 18 h. The mixture was diluted with EtOAc, washed with water, brine, dried over sodium sulfate and concentrated. The residue was dissolved in ethyl acetate (8 mL) and 4.0 N HCl in dioxane (1.170 mL, 4.68 mmol) was added. The mixture was stirred at room temperature for 45 min. Solvent was removed under vacuum to give the deprotected intermediate as a yellow oil. The deprotected intermediate was dissolved in THF (20 mL). Tin(II) chloride dihydrate (0.290 g, 1.287 mmol) was added, followed by concentrated HCl (0.048 mL, 0.585 mmol). The mixture was placed and stirred in an oil bath pre-heated at 45° C. for 18 h. The reaction mixture was diluted with EtOAc/water and neutralized with saturated sodium bicarbonate. The mixture was stirred at room temperature for 15 min, the precipitate was removed by filtration. The organic layer was washed with saturated sodium bicarbonate, washed with brine, dried over sodium sulfate, and concentrated. The reaction mixture was purified on ISCO, 24 g column 0-100% EtOAc in hexanes to give Intermediate 187C (0.093 g, 0.254 mmol, 65.2% yield) as a light yellow solid. $^1$H NMR (400 MHz, CHLOROFORM-d) δ 9.13 (s, 1H), 7.95 (d, J=1.5 Hz, 1H), 7.83 (s, 1H), 7.36-7.28 (m, 2H), 7.06-6.95 (m, 3H), 5.44 (s, 2H), 2.60 (s, 3H). LC-MS: method H, RT=1.30 min, MS (ESI) m/z: 329.1 (M+H)$^+$.

Intermediate 187D: 7-methyl-2-(phenoxymethyl)-5-(4,4,5,5-tetramethyl-1,3,2-dioxaborolan-2-yl)quinoxaline

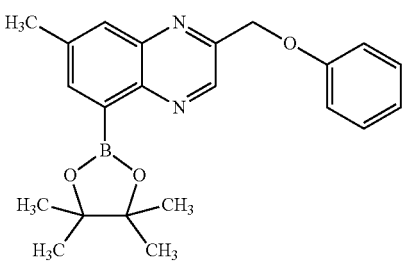

(187D)

A mixture of Intermediate 187C (0.093 g, 0.283 mmol), 4,4,4',4',5,5,5',5'-octamethyl-2,2'-bi(1,3,2-dioxaborolane) (0.108 g, 0.424 mmol), potassium acetate (0.069 g, 0.706 mmol) in dioxane (2.83 mL) were degassed by bubbling argon for 5 min. PdCl$_2$(dppf)-CH$_2$Cl$_2$ adduct (0.012 g, 0.014 mmol) was added and the mixture was sealed and heated in microwave at 130° C. for 30 min. The reaction mixture was diluted with water and EtOAc. The layers were separated and the organic layer was washed with water, washed with brine, dried with sodium sulfate, and concentrated under reduced pressure to yield Intermediate 187D (0.100 g, 0.266 mmol, 94% yield). Used without further purification. LC-MS: method H, RT=1.21 min. MS (ESI) m/z: 295.2 (M+H)$^+$ (Mass of the boronic acid was observed in LC/MS).

Example 187

Intermediate 187D (0.025 g, 0.066 mmol) and 2-bromo-6-methoxy-4-methylbenzo[d]thiazole (0.017 g, 0.066 mmol) were dissolved in DMF (1 mL). PdCl$_2$(dppf)-CH$_2$Cl$_2$ adduct (3.26 mg, 3.99 μmol) was added and the reaction mixture was degassed by bubbling with argon for 15 minutes. 3 M aqueous sodium bicarbonate solution (0.022 mL, 0.066 mmol) was added and the reaction mixture was degassed for 5 minutes, then sealed and heated to 90° C. in the microwave for 30 minutes. The reaction mixture was filtered and concentrated. The reaction mixture was diluted with DMF, filtered, and purified by preparative HPLC (Method D, 55% to 100% B in 20 minutes) to yield Example 187 (0.0084 g, 0.019 mmol, 28.7% yield): $^1$H NMR (500 MHz, CHLOROFORM-d) δ 9.22 (s, 1H), 8.93 (s, 1H), 7.97 (s, 1H), 7.36 (t, J=7.8 Hz, 2H), 7.28 (d, J=2.5 Hz, 1H), 7.10 (d, J=8.3 Hz, 2H), 7.05 (t, J=7.3 Hz, 1H), 6.97 (s, 1H), 5.49 (s, 2H), 3.93 (s, 3H), 2.87 (s, 3H), 2.76 (s, 3H). LC-MS: method H, RT=1.53 min, MS (ESI) m/z: 428.2 (M+H)$^+$. Analytical HPLC Method B: 97% purity.

Example 188

1-(5-(6-methoxy-4-methylbenzo[d]thiazol-2-yl)-7-methylquinoxalin-2-yl)-N,N-dimethylmethanamine

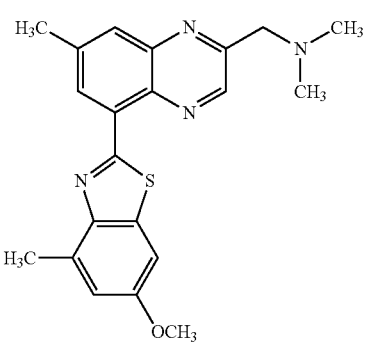

(188)

Intermediate 188A: Ethyl 5-(6-methoxy-4-methylbenzo[d]thiazol-2-yl)-7-methylquinoxaline-2-carboxylate

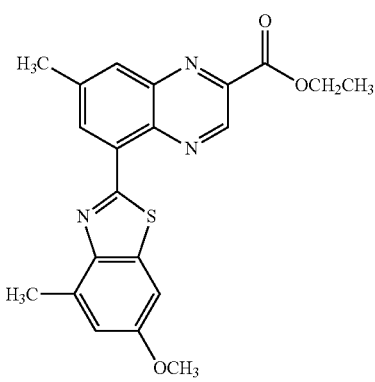

(188A)

Intermediate I-15 (0.030 g, 0.104 mmol) and Intermediate I-3 (0.027 g, 0.104 mmol) were dissolved in DMF (3 mL). PdCl$_2$(dppf)-CH$_2$Cl$_2$ adduct (5.10 mg, 6.25 µmol) was added and the reaction mixture was degassed by bubbling with argon for 15 minutes. Na$_2$CO$_3$, 3 M aqueous solution (0.100 mL, 0.300 mmol) was added and the reaction mixture was degassed for 5 minutes, then sealed and heated to 90° C. in the microwave for 30 minutes. The reaction mixture was diluted with water and EtOAc. The layers were separated and the organic layer was washed with brine, dried with sodium sulfate, and concentrated under reduced pressure to yield a black oil. The reaction mixture was purified on ISCO 12 g column 0-100% EtOAc in hexanes to yield Intermediate 188A (0.026 g, 0.066 mmol, 63.5% yield) as a yellow solid. $^1$H NMR (500 MHz, CHLOROFORM-d) δ 9.62 (s, 1H), 9.02 (s, 1H), 8.16 (s, 1H), 7.28-7.27 (m, 1H), 6.95 (s, 1H), 4.62 (q, J=7.2 Hz, 2H), 3.91 (s, 3H), 2.84 (s, 3H), 2.74 (s, 3H), 1.51 (br. s., 3H), 1.53-1.51 (m, 3H). LC-MS: method H, RT=1.41 min, MS (ESI) m/z: 394.1 (M+H)$^+$.

Intermediate 188B: (5-(6-methoxy-4-methylbenzo[d]thiazol-2-yl)-7-methylquinoxalin-2-yl)methanol

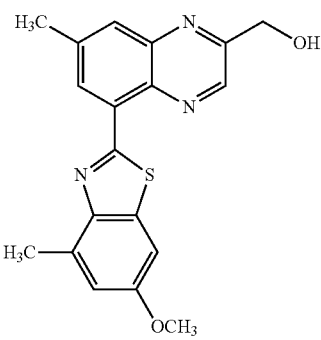

(188B)

Sodium borohydride (4.92 mg, 0.130 mmol) and calcium chloride (7.22 mg, 0.065 mmol) were dissolved in tetrahydrofuran (2 mL) and allowed to stir for 1 h. To this suspension was added Intermediate 188A (0.0256 g, 0.065 mmol) and the reaction mixture was allowed to stir at room temperature for 18 h. The reaction mixture diluted with water and EtOAc. The layer were separated and the organic layer was washed with brine, dried with sodium sulfate, and concentrated under reduced pressure to yield Intermediate 188B (0.025 g, 0.071 mmol, 109% yield) as a yellow oil. $^1$H NMR (400 MHz, CHLOROFORM-d) δ 8.94 (s, 1H), 8.91 (d, J=1.8 Hz, 1H), 7.98 (d, J=0.9 Hz, 1H), 7.31-7.30 (m, 1H), 6.97 (dd, J=2.5, 0.8 Hz, 1H), 5.10 (s, 2H), 3.93 (s, 3H), 2.87 (s, 3H), 2.75 (s, 3H). LC-MS: method H, RT=1.29 min, MS (ESI) m/z: 352.1 (M+H)$^+$.

Intermediate 188C: (5-(6-methoxy-4-methylbenzo[d]thiazol-2-yl)-7-methylquinoxalin-2-yl)methyl methanesulfonate

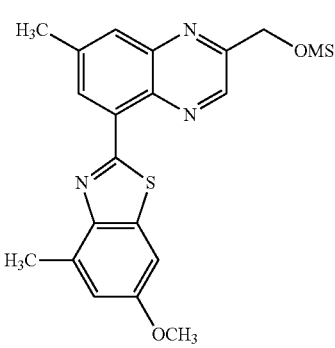

(188D)

Intermediate 188B (0.025 g, 0.071 mmol) was dissolved in DCM (3 mL) and treated with TEA (0.030 mL, 0.213 mmol). To this solution was added methanesulfonic anhydride (0.015 g, 0.085 mmol) and the reaction mixture was allowed to stir at room temperature for 1 h. The reaction mixture was diluted with EtOAc and saturated sodium bicarbonate. The layers were separated and the organic layer was washed with brine, dried with sodium sulfate and concentrated under reduced pressure to yield Intermediate 188C (0.027 g, 0.063 mmol, 88% yield). Used in next step to without further purification. LC-MS: method H, RT=1.34 min, MS (ESI) m/z: 430.1 (M+H)⁺.

Example 188

Intermediate 188C (0.0125 g, 0.029 mmol) was dissolved in tetrahydrofuran (0.291 mL) and DIEA (7.62 μl, 0.044 mmol) was added. To the stirred reaction mixture was added dimethylamine (7.37 μL, 0.146 mmol) and the reaction mixture was allowed to stir at room temperature for 18 h. The reaction mixture was diluted with DMF, filtered, and purified by preparative HPLC (Method D, 45% to 85% B in 18 minutes) to yield Example 188 (1.7 mg, 4.22 μmol, 14.51% yield): $^1$H NMR (500 MHz, DMSO-$d_6$) δ 9.09 (s, 1H), 8.79 (d, J=1.7 Hz, 1H), 8.02 (d, J=0.8 Hz, 1H), 7.56 (d, J=2.5 Hz, 1H), 7.01 (d, J=1.7 Hz, 1H), 3.86 (s, 3H), 3.35 (s, 2H), 2.76 (s, 3H), 2.69 (s, 3H), 2.33 (s, 6H). LC-MS: method H, RT=1.10 min, MS (ESI) m/z: 379.2 (M+H)⁺. Analytical HPLC Method B: 94% purity.

Example 189

2-(2-(ethoxymethyl)-7-methylquinoxalin-5-yl)-6-methoxy-4-methylbenzo[d]thiazole

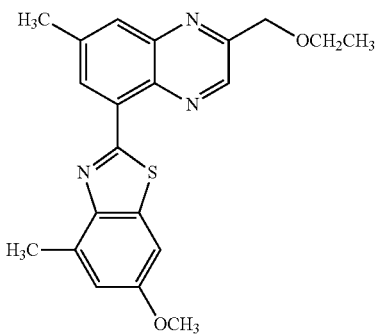
(189)

Intermediate 189A: 1-diazo-3-ethoxypropan-2-one

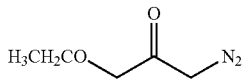
(189A)

To 2-ethoxyacetyl chloride (0.250 g, 2.040 mmol) in MeCN cooled with ice-bath was added (diazomethyl)trimethylsilane 2.0 M in diethyl ether (1.785 mL, 3.57 mmol). The mixture was allowed to stir at room temperature for 3 h. Solvent was removed under reduced pressure. The crude product was purified by flash chromatography (loading in chloroform, 0% to 50% EtOAc in hexane over 18 min using a 40 g silica gel cartridge). The desired fractions were combined and concentrated (bath temp below 35° C.) to yield Intermediate 189A (0.181 g, 1.413 mmol, 69.2% yield) as a pale yellow oil. $^1$H NMR (400 MHz, CHLOROFORM-d) δ 5.77 (s, 1H), 3.99 (s, 2H), 3.56 (q, J=6.9 Hz, 2H), 1.25 (t, J=7.0 Hz, 3H).

Intermediate 189B: 1-diazo-3-ethoxypropan-2-one

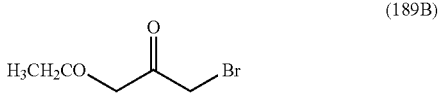
(189B)

Intermediate 189A (0.145 g, 1.132 mmol) was dissolved in Et₂O (4.53 mL) and cooled to 0° C. and HBr (0.224 mL, 1.980 mmol) was added dropwise. After 5 min at 0° C., the reaction mixture was allowed to stir at room temperature for 10 min. The reaction mixture was diluted with ether, washed with saturated sodium bicarbonate, washed with brine, and dried over sodium sulfate. The organic layer was concentrated (kept bath below 30° C.) and the product was used immediately without further purification. Intermediate 189B (0.148 g, 0.818 mmol, 72.2% yield). $^1$H NMR (400 MHz, CHLOROFORM-d) δ 4.26 (s, 2H), 4.07 (s, 2H), 3.59 (q, J=6.9 Hz, 2H), 1.27 (t, J=6.9 Hz, 3H).

Intermediate 189C: tert-butyl (2-bromo-4-methyl-6-nitrophenyl)(3-ethoxy-2-oxopropyl)carbamate

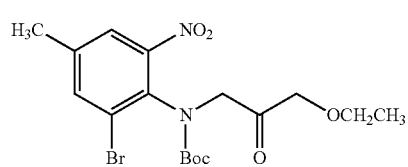
(189C)

To Intermediate I-1B (0.226 g, 0.681 mmol) in anhydrous DMF (30 mL) at 0° C. was added cesium carbonate (0.388 g, 1.192 mmol) in several parts. The brown solution was stirred at 0° C. for 10 min, followed by addition of Intermediate 189B (0.148 g, 0.818 mmol) in DMF (5.0 mL). The brown solution turned yellow. The mixture was stirred at room temperature for 18 h. The mixture was diluted with EtOAc, washed with water, brine, dried over sodium sulfate and concentrated. The crude product was purified by ISCO (40 g silica gel column, (0% to 60% EtOAc/Hexane over 18 min) to yield Intermediate 189C (0.197 g, 0.457 mmol, 67.0% yield) as a yellow solid. LC-MS: method H, RT=1.22 min, MS (ESI) m/z: 431.0 (M+H)⁺.

Intermediate 189D: 5-bromo-2-(ethoxymethyl)-7-methylquinoxaline

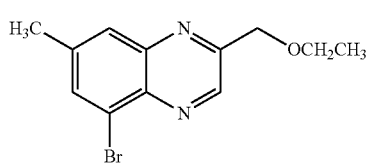
(189D)

To Intermediate 189C (0.187 g, 0.434 mmol) in Ethyl acetate (8 mL) was added 4.0 N HCl in dioxane (1.301 mL, 5.20 mmol) and the mixture was stirred at room temperature for 45 min. Solvent was removed under vacuum to give the deprotected intermediate as a yellow oil. The deprotected intermediate was dissolved in THF (20 mL). Tin(II) chloride dihydrate (0.323 g, 1.431 mmol) was added, followed by concentrated HCl (0.053 mL, 0.650 mmol). The mixture was placed and stirred in an oil bath pre-heated at 45° C. for 18 h. The reaction mixture was diluted with EtOAc/water and neutralized with saturated sodium bicarbonate. The mixture was stirred at room temperature for 15 min, the precipitate was removed by a separatory funnel. The organic layer was washed with saturated sodium bicarbonate, washed with brine, dried over sodium sulfate and concentrated. The reaction mixture was purified on ISCO 24 g column 0-100% EtOAc in hexanes to yield Intermediate 189D (0.056 g, 0.199 mmol, 45.9% yield): $^1$H NMR (400 MHz, CHLOROFORM-d) δ 9.05 (s, 1H), 7.93 (d, J=1.8 Hz, 1H), 7.81 (s, 1H), 4.86 (s, 2H), 3.68 (q, J=7.0 Hz, 2H), 2.58 (s, 3H), 1.31 (t, J=6.9 Hz, 3H). LC-MS: method H, RT=1.20 min, MS (ESI) m/z: 281.1 (M+H)$^+$.

Intermediate 189E: 2-(ethoxymethyl)-7-methyl-5-(4,4,5,5-tetramethyl-1,3,2-dioxaborolan-2-yl)quinoxaline

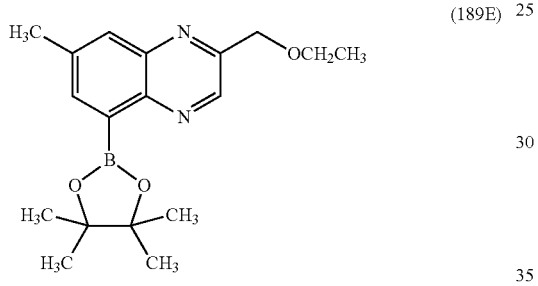

(189E)

A mixture of Intermediate 189D (0.056 g, 0.199 mmol), 4,4,4',4',5,5,5',5'-octamethyl-2,2'-bi(1,3,2-dioxaborolane) (0.076 g, 0.299 mmol), potassium acetate (0.049 g, 0.498 mmol) in dioxane (1.992 mL) were degassed by bubbling argon for 5 min. PdCl$_2$(dppf)-CH$_2$Cl$_2$ adduct (8.13 mg, 9.96 µmol) was added and the mixture was sealed and heated in microwave at 130° C. for 30 min. The reaction mixture was diluted with water and EtOAc. The layers were separated and the organic layer was washed with water, washed with brine, dried with sodium sulfate, and concentrated under reduced pressure to yield Intermediate 189E (0.050 g, 0.152 mmol, 76% yield) as a brown oil Used without further purification in the next step. LC-MS: method H, RT=1.06 min, MS (ESI) m/z: 247.2 (M+H)$^+$. Mass of the boronic acid seen in LC/MS.

Example 189

Intermediate 189E (0.025 g, 0.076 mmol) and Intermediate I-3 (0.020 g, 0.076 mmol) were dissolved in DMF (1 mL). PdCl$_2$(dppf)-CH$_2$Cl$_2$ adduct (3.73 mg, 4.57 µmol) was added and the reaction mixture was degassed by bubbling with argon for 15 minutes. 3 M sodium carbonate solution (0.025 mL, 0.076 mmol) was added and the reaction mixture was degassed for 5 minutes, then sealed and heated to 90° C. in the microwave for 30 minutes. The reaction mixture was filtered and concentrated. The reaction mixture was diluted with DMF, filtered, and purified by preparative HPLC (Method D, 55% to 100% B in 20 minutes) to yield Example 189 (0.0003 g, 0.759 µmol, 0.996% yield): $^1$H NMR (500 MHz, CHLOROFORM-d) δ 9.15 (s, 1H), 8.90 (d, J=1.4 Hz, 1H), 7.95 (s, 1H), 7.31-7.30 (m, 1H), 6.97 (s, 1H), 4.91 (s, 2H), 3.93 (s, 3H), 3.76 (q, J=6.9 Hz, 2H), 2.87 (s, 3H), 2.74 (s, 3H), 1.37 (t, J=6.9 Hz, 3H). LC-MS: method H, RT=1.49 min, MS (ESI) m/z: 380.2 (M+H)$^+$. Analytical HPLC Method B: 96% purity.

Example 190

6-methoxy-2-(4-methoxy-3-(methoxymethyl)-6-methylquinolin-8-yl)-4-methylbenzo[d]thiazole

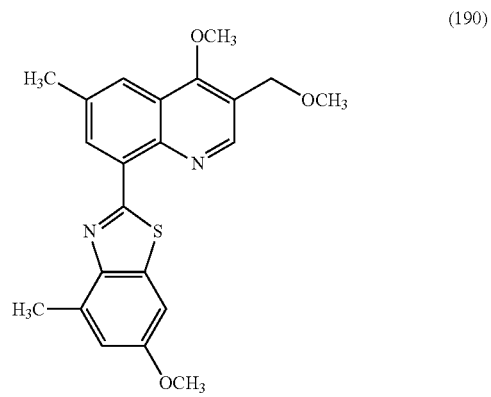 [SMILES: COCc1cnc2c(-c3nc4c(C)cc(OC)cc4s3)cc(C)cc2c1OC]

(190)

Intermediate 190A: diethyl 2-(((2-bromo-4-methylphenyl)amino)methylene)malonate

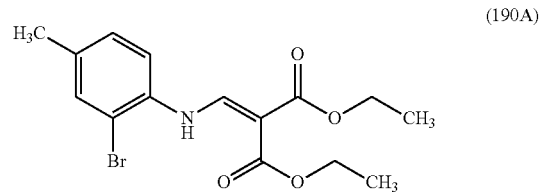 [SMILES: CCOC(=O)C(=CNc1ccc(C)cc1Br)C(=O)OCC]

(190A)

2-bromo-4-methylaniline (0.667 mL, 5.37 mmol) and diethyl 2-(ethoxy methylene)malonate (1.184 mL, 5.91 mmol) were heated to 100° C. under a stream of argon. The reaction mixture stirred for 2 h and was cooled to ambient temperature, diluted with hexanes, heated gently to break up the material, and the solid collected by suction filtration Intermediate 190A (1.80 g, 5.05 mmol, 94% yield): $^1$H NMR (400 MHz, CHLOROFORM-d) δ 11.22 (d, J=12.8 Hz, 1H), 8.48 (d, J=13.4 Hz, 1H), 7.42 (s, 1H), 7.21-7.11 (m, 2H), 4.35 (q, J=7.3 Hz, 2H), 4.26 (q, J=7.0 Hz, 2H), 1.39 (t, J=7.2 Hz, 3H), 1.33 (t, J=7.2 Hz, 3H).

Intermediate 190B: ethyl 8-bromo-4-hydroxy-6-methylquinoline-3-carboxylate

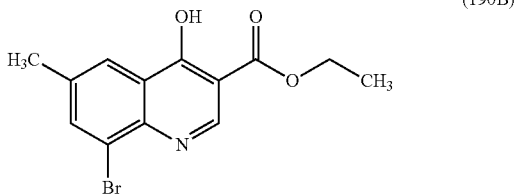

(190B)

Intermediate 190A (0.250 g, 0.702 mmol) was dissolved in biphenyl ether (12.5 mL) was added. The reaction mixture was stirred at 250° C. for 18 h. The reaction mixture was cooled to ambient temperature. The reaction mixture was filtered and washed with Et₂O to yield Intermediate 190B (0.187 g, 0.603 mmol, 86% yield) as a white solid. $^1$H NMR (400 MHz, CHLOROFORM-d) δ 12.33 (s, 1H), 9.19 (s, 1H), 8.09 (s, 1H), 7.99 (d, J=1.5 Hz, 1H), 4.52 (q, J=7.0 Hz, 2H), 2.54 (s, 3H), 1.48 (t, J=7.0 Hz, 3H). LC-MS: method H, RT=0.95 min, MS (ESI) m/z: 310.0 (M+H)⁺.

Intermediate 190C: ethyl 8-bromo-4-chloro-6-methylquinoline-3-carboxylate

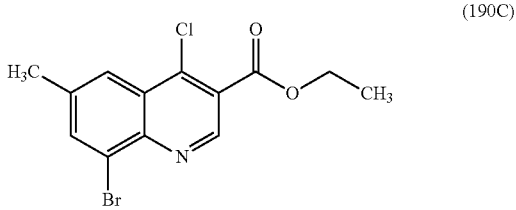 [SMILES: CCOC(=O)c1cnc2c(Br)cc(C)cc2c1Cl]

(190C)

Intermediate 190B (0.100 g, 0.322 mmol) was dissolved in POCl₃ (0.150 mL, 1.612 mmol) and heated to reflux for 3 h. The reaction mixture was carefully diluted with water and ice. The layers were separated and the organic layer was washed with aqueous saturated NaHCO₃, brine, dried with sodium sulfate, and concentrated under reduced pressure to yield Intermediate 190C (0.048 g, 0.146 mmol, 45.3% yield) as a pale yellow solid. Used without further purification in the next step. $^1$H NMR (400 MHz, CHLOROFORM-d) δ 9.61 (s, 1H), 8.44 (s, 1H), 8.33 (s, 1H), 4.60 (q, J=7.2 Hz, 2H), 2.75 (s, 3H), 1.51 (t, J=7.2 Hz, 3H). LC-MS: method H, RT=1.28 min, MS (ESI) m/z: 328.0 (M+H)⁺.

Intermediate 190D: methyl 8-bromo-4-methoxy-6-methylquinoline-3-carboxylate

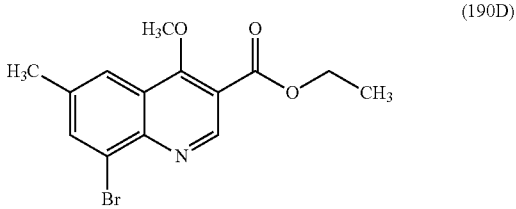 [SMILES: CCOC(=O)c1cnc2c(Br)cc(C)cc2c1OC]

(190D)

Intermediate 190C (0.480 g, 1.461 mmol) was dissolved in THF (10 mL) and sodium methoxide (8.76 mL, 4.38 mmol) was added. The reaction mixture was allowed to stir at room temperature for 30 min. The reaction mixture was diluted with water and EtOAc. The layers were separated and the organic layer was washed with brine, dried with sodium sulfate, and concentrated under reduced pressure to yield Intermediate 190D (0.454 g, 1.464 mmol, 100% yield) as a white solid: $^1$H NMR (400 MHz, CHLOROFORM-d) δ 9.21 (s, 1H), 8.02 (dd, J=1.8, 0.9 Hz, 1H), 7.98 (d, J=1.8 Hz, 1H), 4.14 (s, 3H), 4.01 (s, 3H), 2.55 (s, 3H). LC-MS: method H, RT=1.16 min, MS (ESI) m/z: 310.0 (M+H)⁺.

Intermediate 190E: (8-bromo-4-methoxy-6-methylquinolin-3-yl)methanol

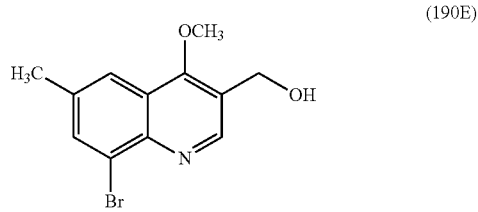 [SMILES: COc1c(CO)cnc2c(Br)cc(C)cc12]

(190E)

Calcium chloride (0.072 g, 0.645 mmol) and sodium borohydride (0.049 g, 1.290 mmol) were suspended in tetrahydrofuran and allowed to stir for 1 h. To the stirred reaction mixture was added Intermediate 190D (0.200 g, 0.645 mmol) in tetrahydrofuran (25 mL) and the reaction mixture was allowed to stir for 3 days. The reaction mixture was diluted with water and EtOAc. The layers were separated and the organic layer was washed with brine, dried with sodium sulfate, and concentrated under reduced pressure. The reaction mixture was purified by ISCO 24 g column 0-100% EtOAc in hexanes to yield Intermediate 190E (0.050 g, 0.177 mmol, 27.5% yield) as a white solid. $^1$H NMR (500 MHz, CHLOROFORM-d) δ 8.96 (s, 1H), 7.91 (d, J=1.4 Hz, 1H), 7.85 (d, J=0.8 Hz, 1H), 4.94 (d, J=5.8 Hz, 2H), 4.11 (d, J=0.8 Hz, 3H), 2.55 (s, 3H). LC-MS: method H, RT=0.84 min, MS (ESI) m/z: 282.1 (M+H)⁺.

Intermediate 190F: (8-bromo-4-methoxy-6-methylquinolin-3-yl)methyl methanesulfonate

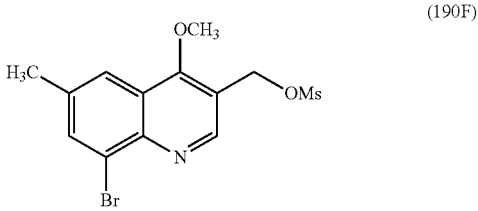

(190F)

Intermediate 190E (0.050 g, 0.177 mmol) was dissolved in DCM (3 mL) and treated with TEA (0.074 mL, 0.532 mmol). To this solution was added methanesulfonic acid (0.037 g, 0.213 mmol), and the reaction mixture was allowed to stir at room temperature for 1 h. The reaction mixture was diluted with EtOAc and saturated sodium bicarbonate. The layers were separated and the organic layer was washed with brine, dried with sodium sulfate and concentrated under reduced pressure to yield Intermediate 190F (0.027 g, 0.073 mmol, 53%). Used without further purification in the next step. LC-MS: method H, RT=0.96 min, MS (ESI) m/z: 296.1 (M+H)+ Observed the methyl ether in LC/MS.

Intermediate 190G: 8-bromo-4-methoxy-3-(methoxymethyl)-6-methylquinoline

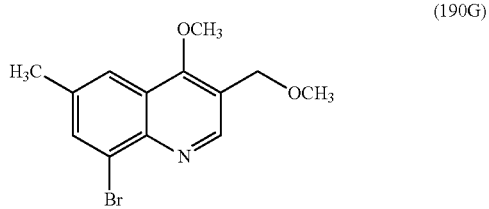 [SMILES: COCc1cnc2c(Br)cc(C)cc2c1OC]

(190G)

Intermediate 190F (0.180 g, 0.500 mmol) was dissolved in THF (5.00 ml) and DIPEA (0.131 ml, 0.750 mmol) was added. To the stirred reaction was added sodium methoxide (5.00 ml, 2.498 mmol), and the reaction was allowed to stir at room temperature overnight. The reaction was diluted with water and EtOAc. The layers were separated, and the organic layer was washed with brine, dried with sodium sulfate, and concentrated under reduced pressure to yield Intermediate 190G (0.068 g, 0.230 mmol, 46%) as a yellow solid. Used without further purification in the next step. LC-MS: method H, RT=0.97 min, MS (ESI) m/z: 298.1 (M+H)+.

Intermediate 190H: 4-methoxy-3-(methoxymethyl)-6-methyl-8-(4,4,5,5-tetramethyl-1,3,2-dioxaborolan-2-yl)quinoline

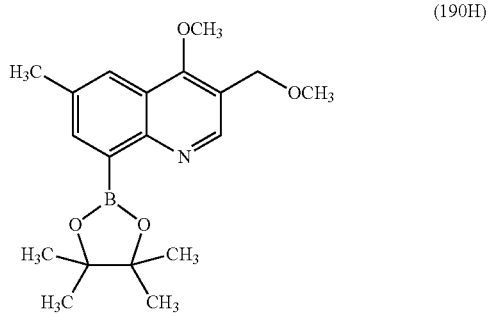 [SMILES: COCc1cnc2c(B3OC(C)(C)C(C)(C)O3)cc(C)cc2c1OC]

(190H)

A mixture of Intermediate 190G (0.027 g, 0.091 mmol), 4,4,4',4',5,5,5',5'-octamethyl-2,2'-bi(1,3,2-dioxaborolane) (0.035 g, 0.137 mmol), potassium acetate (0.022 g, 0.228 mmol) in dioxane (0.912 mL) were degassed by bubbling argon for 5 min. PdCl₂(dppf)-CH₂Cl₂ adduct (3.72 mg, 4.56 μmol) was added and the mixture was sealed and heated in microwave at 130° C. for 30 min. The reaction mixture was diluted with water and EtOAc. The layers were separated and the organic layer was washed with brine, dried with sodium sulfate, and concentrated under reduced pressure to yield Intermediate 190H (0.040, 0.058, 64%) as a brown oil. Used in the next step without further purification. LC-MS:

method H, RT=0.98 min, MS (ESI) m/z: 262.2 (M+H)+. Mass of the boronic acid was seen in LC/MS.

Example 190

Intermediate 190H (0.031 g, 0.090 mmol) and Intermediate I-3 (0.023 g, 0.090 mmol) were dissolved in DMF (3 mL). PdCl₂(dppf)-CH₂Cl₂ adduct (4.43 mg, 5.42 μmol) was added and the reaction mixture was degassed by bubbling with argon for 15 minutes. Na₂CO₃, 3 M aqueous solution (0.100 mL, 0.300 mmol) was added and the reaction mixture was degassed for 5 minutes, then sealed and heated to 90° C. in the microwave for 30 minutes. The reaction mixture was filtered and concentrated. The reaction mixture was diluted with DMF, filtered, and purified by preparative HPLC (Method D, 55% to 100% B in 22 minutes) to yield Example 190 (0.0036 g, 8.58 μmol, 9.50% yield): ¹H NMR (500 MHz, DMSO-d₆) δ 8.98 (s, 1H), 8.82 (s, 1H), 8.10 (s, 1H), 7.54 (d, J=1.9 Hz, 1H), 7.00 (s, 1H), 4.73 (s, 2H), 4.12 (s, 3H), 3.86 (s, 3H), 3.42 (s, 3H), 2.76 (s, 3H), 2.68 (s, 3H). LC-MS: method H, RT=1.10 min, MS (ESI) m/z: 395.2 (M+H)+. Analytical HPLC Method B: 94% purity.

Example 191

5-chloro-2-(2-(methoxymethyl)-7-methylquinoxalin-5-yl)-7-methylthiazolo[5,4-b] pyridine

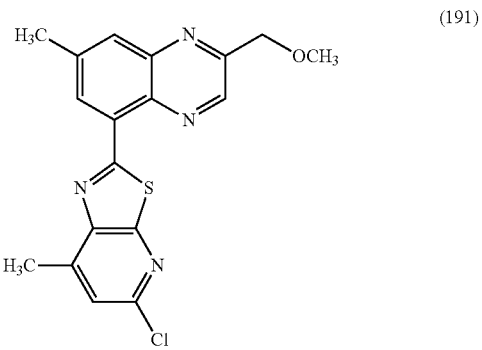 [SMILES: COCc1cnc2c(-c3nc4c(C)cc(Cl)nc4s3)cc(C)cc2n1]

(191)

Intermediate 191A: 5-chloro-7-methylthiazolo[5,4-b]pyridin-2-amine

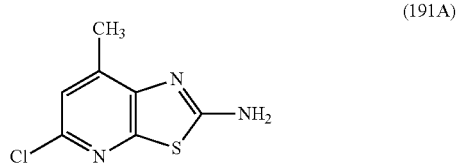

(191A)

Potassium thiocyanate (0.682 g, 7.01 mmol) was dissolved in acetic acid (10 mL) and cooled to 0° C. 6-chloro-4-methylpyridin-3-amine (1.00 g, 7.01 mmol) was dissolved in acetic acid (3.33 mL) and added dropwise. Bromine (0.361 mL, 7.01 mmol) was dissolved in acetic acid (3.33 mL) and added dropwise to the reaction mixture. The reaction mixture was allowed to warm to room temperature for 18 h. The reaction mixture was concentrated under reduced pressure. The resultant residue was diluted with water and neutralized with 1 N NaOH. The aqueous solution was extracted with EtOAc (×3). The combined organic layer was washed with brine, dried with sodium sulfate, and concentrated under reduced pressure. The reaction mixture was purified on Prep HPLC using Method A to yield Intermediate 191A (0.890 g, 4.46 mmol, 63.6% yield) as a white solid. $^1$H NMR (400 MHz, CHLOROFORM-d) δ 7.08 (d, J=0.7 Hz, 1H), 3.39 (dt, J=3.2, 1.6 Hz, 2H), 2.50 (d, J=0.7 Hz, 3H). LC-MS: method H, RT=0.92 min, MS (ESI) m/z: 200.1 (M+H)$^+$.

Intermediate 191B: 2-bromo-5-chloro-7-methylthiazolo[5,4-b]pyridine

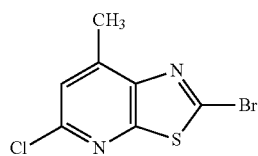

(191B)

Copper(II) bromide (0.295 g, 1.320 mmol) and t-butyl nitrite (0.157 mL, 1.320 mmol) were dissolved in MeCN (3.11 mL) and allowed to stir 10 minutes. Intermediate 191A (0.155 g, 0.776 mmol) was dissolved in MeCN (4.66 mL) and the copper solution was added. The reaction mixture was stirred for 30 min. The reaction mixture was diluted with EtOAc, washed with 1 N HCl, washed with saturated NaHCO$_3$, washed with brine, dried with sodium sulfate, filtered, and concentrated in vacuo to yield Intermediate 191B (0.163 g, 0.618 mmol, 80% yield). $^1$H NMR (400 MHz, METHANOL-d$_4$) δ 7.43 (d, J=0.9 Hz, 1H), 2.68 (d, J=0.9 Hz, 3H). LC-MS: method H, RT=1.30 min, MS (ESI) m/z: 263.0 (M+H)$^+$.

Example 191

Intermediate 191B (0.025 g, 0.095 mmol) was dissolved in Et$_2$O (0.379 mL) and cooled to −78° C. BuLi (0.042 mL, 0.104 mmol) was added and allowed to stir for 15 min. Tributylchlorostannane (0.026 mL, 0.095 mmol) was added and allowed to stir for 30 min. The reaction mixture was warmed to ambient temperature and concentrated in vacuo. The crude material was suspended in hexanes and filtered through dry celite. Used immediately without further purification. Intermediate I-2E (0.015 g, 0.056 mmol), stannane, and potassium acetate (0.011 g, 0.112 mmol) were dissolved in dioxane (0.562 mL) and degassed by bubbling with argon for 15 minutes. Pd(Ph$_3$P)$_4$ (3.24 mg, 2.81 µmol) was added and the reaction mixture was sealed and heated to 120° C. in the microwave for 2 hours. The reaction mixture was diluted with EtOAc and water. The layers were separated and the organic layer was washed with brine, dried with sodium sulfate, and concentrated under reduced pressure. The reaction mixture was diluted with DMF, filtered, and purified by preparative HPLC (Method D, 65% to 100% B in 12 minutes) to yield Example 191 (0.0023 g, 6.08 µmol, 10.82% yield): $^1$H NMR (500 MHz, DMSO-d$_6$) δ 9.17 (s, 1H), 8.88 (s, 1H), 8.14 (s, 1H), 7.62 (s, 1H), 4.84 (s, 2H), 3.49 (s, 3H), 2.84 (s, 3H), 2.73 (s, 3H). LC-MS: method H, RT=1.11 min, MS (ESI) m/z: 371.2 (M+H)$^+$. Analytical HPLC Method B: 98% purity.

Example 192

(5-methoxy-2-(2-(methoxymethyl)-7-methylquinoxalin-5-yl)thiazolo[5,4-b]pyridin-7-yl) methanol

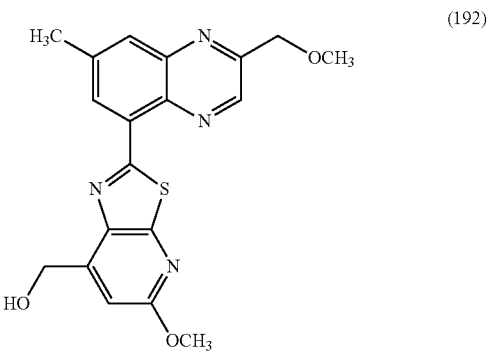 [SMILES: COCc1cnc2c(-c3nc4c(CO)cc(OC)nc4s3)cc(C)cc2n1]

(192)

Intermediate 192A: 2-methoxy-5-nitroisonicotinic acid

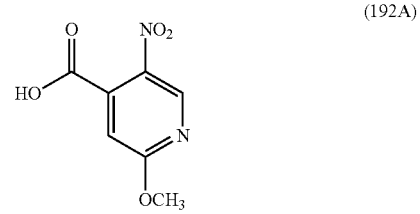 [SMILES: COc1cc(C(=O)O)c([N+](=O)[O-])cn1]

(192A)

2-chloro-5-nitroisonicotinic acid (0.100 g, 0.494 mmol) was dissolved in DCM (4.94 mL) and oxalyl chloride (0.043 mL, 0.494 mmol) was added. To the stirred reaction mixture was added 2 drops of DMF. The reaction mixture was stirred for 30 min and concentrated under reduced pressure. The compound was used without further purification in the next step. The residue was dissolved in tetrahydrofuran (4.98 mL) and sodium methoxide (3.98 mL, 1.991 mmol) was added. The reaction mixture was allowed to stir at room temperature for 18 h. The reaction mixture was diluted with water and EtOAc. 1 N HCl was added and the layers were separated. The organic layer was washed brine, dried with sodium sulfate, and concentrated under reduced pressure to yield Intermediate 192A (0.078 g, 0.394 mmol, 79% yield) as a white solid. $^1$H NMR (400 MHz, CHLOROFORM-d) δ 8.97 (s, 1H), 6.95 (s, 1H), 4.08 (s, 3H). LC-MS: method H, RT=0.82 min, MS (ESI) m/z: 198.9 (M+H)$^+$.

Intermediate 192B: methyl 2-methoxy-5-nitroisonicotinate

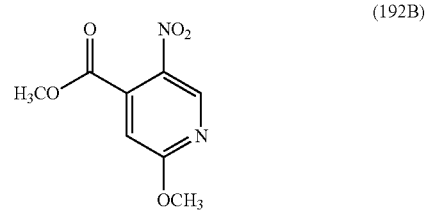 [SMILES: COC(=O)c1cc(OC)ncc1[N+](=O)[O-]]

(192B)

Intermediate 192A (0.085 g, 0.429 mmol) was dissolved in DCM (4.29 mL) and oxalyl chloride (0.038 mL, 0.429 mmol) was added. To the stirred reaction mixture was added 2 drops of DMF. The reaction mixture was stirred for 30 min and concentrated under reduced pressure. The compound was used without further purification in the next step. The residue dissolved in MeOH (4.16 mL) and sodium methoxide (0.831 mL, 0.416 mmol) was added. The reaction mixture was stirred at room temperature for 18 h. The reaction mixture was diluted with water and EtOAc. The layers were separated and the organic layer was washed with water, brine, dried with sodium sulfate, and concentrated under reduced pressure to yield Intermediate 192B (0.060 g, 0.283 mmol, 68.1% yield) as a white solid. $^1$H NMR (400 MHz, CHLOROFORM-d) δ 8.96 (s, 1H), 6.86 (s, 1H), 4.06 (s, 3H), 3.96 (s, 3H). LC-MS: method H, RT=0.83 min, MS (ESI) m/z: 213.1 (M+H)$^+$.

Intermediate 192C: methyl 5-amino-2-methoxyisonicotinate

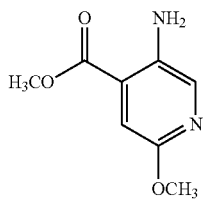

(192C)

Intermediate 192B (60 mg, 0.283 mmol) was dissolved in EtOH (1.131 mL). Pd/C (6.02 mg, 5.66 µmol) then ammonium formate (89 mg, 1.414 mmol) were added and the reaction mixture was heated to reflux for 1 h. The reaction mixture was filtered through celite and concentrated in vacuo to yield Intermediate 192C (47.5 mg, 0.261 mmol, 92% yield): $^1$H NMR (400 MHz, CHLOROFORM-d) δ 7.80 (s, 1H), 7.15 (s, 1H), 5.09 (br. s., 2H), 3.91 (s, 3H), 3.87 (s, 3H). LC-MS: method H, RT=0.67 min, MS (ESI) m/z: 183.1 (M+H)$^+$.

Intermediate 192D: methyl 2-amino-5-methoxythiazolo[5,4-b]pyridine-7-carboxylate, 2 AcOH

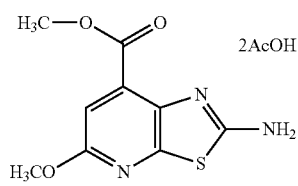

(192D)

Potassium thiocyanate (0.029 g, 0.299 mmol) was dissolved in acetic acid (10 mL) and cooled to 0° C. Intermediate 192C (0.0545 g, 0.299 mmol) was dissolved in acetic acid (3.33 mL) and added dropwise. Bromine (0.015 mL, 0.299 mmol) was dissolved in acetic acid (3.33 mL) and added dropwise to the reaction mixture. The reaction mixture was allowed to warm to room temperature and stir for 18 h. The reaction mixture was concentrated under reduced pressure. The resultant residue was diluted with water and neutralized with 1 N NaOH. The aqueous solution was extracted with EtOAc (×3). The combined organic layer was washed with brine, dried with sodium sulfate, and concentrated under reduced pressure to yield Intermediate 192D (0.100 g, 0.278 mmol, 93% yield). $^1$H NMR (400 MHz, METHANOL-d$_4$) δ 7.10 (s, 1H), 3.94 (s, 3H), 3.93 (s, 3H). LC-MS: method H, RT=0.67 min, MS (ESI) m/z: 240.1 (M+H)$^+$.

Intermediate 192E: methyl 2-bromo-5-methoxythiazolo[5,4-b]pyridine-7-carboxylate

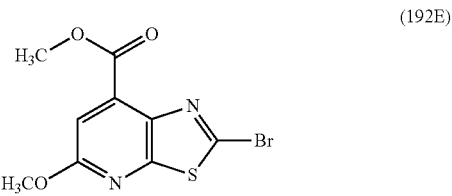 [SMILES: COC(=O)c1cc(OC)nc2sc(Br)nc12]

(192E)

Copper(II) bromide (0.106 g, 0.473 mmol) and t-butyl nitrite (0.056 mL, 0.473 mmol) were dissolved in MeCN (1.113 mL) and allowed to stir 10 minutes. Intermediate 192D (0.100 g, 0.278 mmol) was dissolved in MeCN (1.670 mL) and the copper solution was added. The reaction mixture was stirred for 1 h. The reaction mixture was diluted with EtOAc, washed with 1 N HCl, washed with saturated NaHCO$_3$, washed with brine, dried (Na$_2$SO$_4$), filtered, and concentrated in vacuo to yield Intermediate 192E (0.025 g, 0.082 mmol, 29.6% yield): $^1$H NMR (400 MHz, CHLOROFORM-d) δ 7.31 (s, 1H), 4.03 (s, 3H), 4.02 (s, 3H). LC-MS: method H, RT=0.96 min, MS (ESI) m/z:303.0 (M+H)$^+$.

Intermediate 192F: (2-bromo-5-methoxythiazolo[5,4-b]pyridin-7-yl)methanol

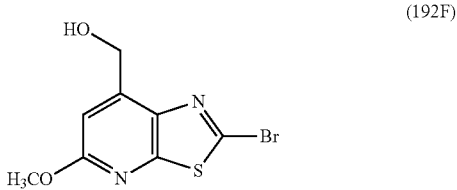 [SMILES: COc1cc(CO)c2nc(Br)sc2n1]

(192F)

Intermediate 192E (25 mg, 0.082 mmol) was dissolved in toluene (550 µl) and THF (275 µl) and cooled to −78° C. 1 M DIBAL-H (181 µl, 0.181 mmol) was added, and the reaction mixture was allowed to stir for 18 h. The reaction mixture was quenched with 1 N HCl (1 mL), diluted with EtOAc. The layers were separated and the organic layer was washed with brine, dried with sodium sulfate, and concentrated under reduced pressure to yield Intermediate 192F (0.02 g, 0.029 mmol, 35.3% yield). Used without further purification in the next step. LC-MS: method H, RT=0.96 min, MS (ESI) m/z: 275.0(M+H)$^+$.

Example 192

Intermediate I-2 (0.020 g, 0.064 mmol) and Intermediate 192E (0.018 g, 0.064 mmol) were dissolved in DMF (1 mL). PdCl$_2$(dppf)-CH$_2$Cl$_2$ adduct (3.12 mg, 3.82 µmol) was added and the reaction mixture was degassed by bubbling with argon for 15 minutes. Na$_2$CO$_3$, 3 M aqueous solution (0.100 mL, 0.300 mmol) was added and the reaction mixture was degassed for 5 minutes, then sealed and heated to 90° C. in the microwave for 30 minutes. The reaction mixture was diluted with DMF, filtered, and purified by preparative HPLC (Method D, 25% to 55% B in 20 minutes) to yield Example 192 (0.0012 g, 3.01 μmol, 4.73% yield): $^1$H NMR (500 MHz, DMSO-d$_6$) δ 9.13 (s, 1H), 8.78 (d, J=1.9 Hz, 1H), 8.07 (s, 1H), 7.05 (s, 1H), 5.64 (t, J=5.6 Hz, 1H), 5.13 (d, J=5.2 Hz, 2H), 4.83 (s, 2H), 4.01 (s, 3H), 3.49 (s, 3H), 2.71 (s, 3H). LC-MS: method H, RT=1.02 min, MS (ESI) m/z: 383.1 (M+H)$^+$. Analytical HPLC Method B: 98% purity.

Example 193

4-fluoro-N-(2-((2-(2-(methoxymethyl)-7-methylquinoxalin-5-yl)-7-methylthiazolo[5,4-b]pyridin-5-yl)oxy)ethyl)benzenesulfonamide

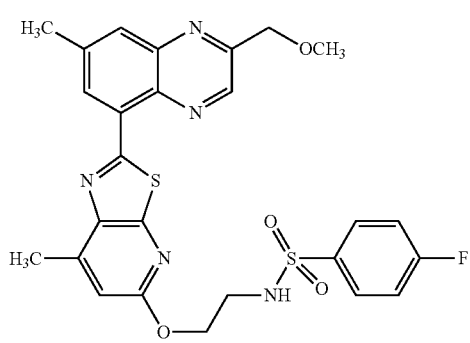

(193)

Intermediate 193A: 2-amino-7-methylthiazolo[5,4-b]pyridin-5-ol, 2 hydrobromide

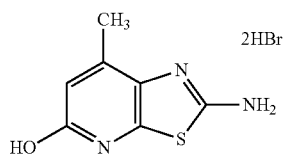

(193A)

Intermediate I-16 (0.750 g, 3.84 mmol) was dissolved HBr in acetic acid (2.61 mL, 23.05 mmol) and the reaction mixture was stirred at 130° C. for 3 h. The reaction mixture was concentrated under reduced pressure to yield Intermediate 193A (1.48 g, 4.31 mmol, 100%) as a tan solid. $^1$H NMR (400 MHz, METHANOL-d$_4$) δ 6.66 (d, J=0.9 Hz, 1H), 2.48 (d, J=0.7 Hz, 3H) LC-MS: method H, RT=0.47 min, MS (ESI) m/z: 182.1 (M+H)$^+$.

Intermediate 193B: tert-butyl (2-((2-amino-7-methylthiazolo[5,4-b]pyridin-5-yl)oxy)ethyl)carbamate

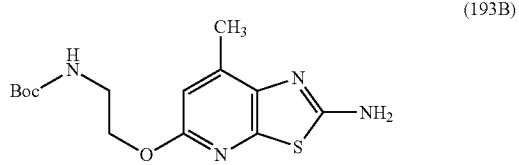 [SMILES: Cc1cc(OCCNC(=O)OC(C)(C)C)nc2sc(N)nc12]

(193B)

Intermediate 193A (0.100 g, 0.332 mmol) was dissolved in DMF (3.32 mL). t-Butyl (2-bromoethyl)carbamate (0.089 g, 0.398 mmol) and Cs$_2$CO$_3$ (0.541 g, 1.659 mmol) were added and the reaction mixture was stirred at 40° C. for 3 h. The reaction mixture was diluted with water and EtOAc. The layers were separated. The organic layer was washed with brine dried with sodium sulfate, and concentrated under reduced pressure. The reaction mixture was purified on ISCO using a 24 g column with a 0-100% gradient of EtOAc in hexanes to yield Intermediate 193B (0.038 g, 0.117 mmol, 35.3% yield) a brown solid. $^1$H NMR (400 MHz, CHLOROFORM-d) δ 6.53 (s, 1H), 5.14 (br. s., 2H), 4.33 (t, J=5.2 Hz, 2H), 3.71 (t, J=5.0 Hz, 1H), 3.52 (d, J=5.1 Hz, 2H), 2.49 (d, J=0.9 Hz, 3H). LC-MS: method H, RT=0.77 min, MS (ESI) m/z: 325.2 (M+H)$^+$.

Intermediate 193C: tert-butyl (2-((2-bromo-7-methylthiazolo[5,4-b]pyridin-5-yl)oxy)ethyl)carbamate

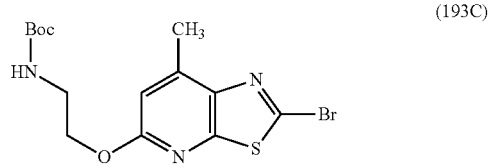 [SMILES: Cc1cc(OCCNC(=O)OC(C)(C)C)nc2sc(Br)nc12]

(193C)

Copper(II) bromide (0.044 g, 0.199 mmol) and t-butyl nitrite (0.024 mL, 0.199 mmol) were dissolved in MeCN (0.469 mL) and allowed to stir 10 minutes. Intermediate 193B (0.038 g, 0.117 mmol) was dissolved in MeCN (0.703 mL) and the copper solution was added. The reaction mixture was diluted with EtOAc, washed with 1 N HCl, washed with saturated NaHCO$_3$, washed with brine, dried with sodium sulfate, filtered, and concentrated in vacuo to yield Intermediate 193C (0.042 g, 0.108 mmol, 92% yield). LC-MS: method H, RT=1.12 min, MS (ESI) m/z: 390.0(M+H)$^+$.

Intermediate 193D: 2-((2-bromo-7-methylthiazolo[5,4-b]pyridin-5-yl)oxy)ethanamine

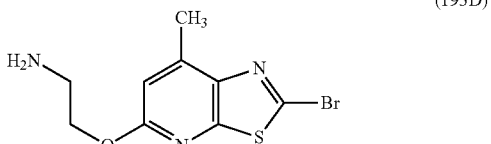

(193D)

To a mixture of Intermediate 193C (0.042 g, 0.108 mmol) in DCM (1) was added 2,6-lutidine (0.038 mL, 0.325 mmol) followed by TMS-OTf (0.078 mL, 0.433 mmol) at room temperature. The mixture was stirred at room temperature for 1 h. The mixture was diluted by EtOAc and NaHCO$_3$. The organic layer was washed by brine, dried by sodium sulfate and concentrated to Intermediate 193D (0.0185 g, 0.064 mmol, 59.4% yield). $^1$H NMR (400 MHz, CHLOROFORM-d) δ 6.68 (d, J=0.9 Hz, 1H), 4.37 (t, J=5.3 Hz, 2H), 3.11 (t, J=5.3 Hz, 2H), 2.63 (d, J=0.9 Hz, 3H), 2.53 (s, 1H). LC-MS: method H, RT=0.68 min, MS (ESI) m/z: 290.1 (M+H)$^+$.

Intermediate 193E: N-(2-((2-bromo-7-methylthiazolo[5,4-b]pyridin-5-yl)oxy)ethyl)-4-fluorobenzenesulfonamide

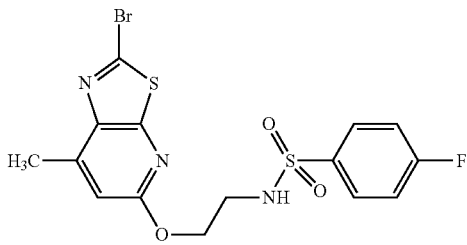

(193E)

To a solution of Intermediate 193D (0.018 g, 0.062 mmol) in DMF (1 mL) was added DIEA (0.109 mL, 0.625 mmol) and 4-fluorobenzene-1-sulfonyl chloride (0.015 g, 0.075 mmol). The mixture was stirred at room temperature for 1 h. The reaction mixture was diluted with water and EtOAc. The layers were separated and the organic layer was washed with brine, dried with sodium sulfate and concentrated under reduced pressure to yield Intermediate 193E (0.028 g, 0.063 mmol, 100% yield) as a yellow glass. $^1$H NMR (400 MHz, CHLOROFORM-d) δ 7.89-7.84 (m, 2H), 7.15 (t, J=8.7 Hz, 2H), 6.55 (d, J=0.9 Hz, 1H), 4.97 (br. s., 1H), 4.43-4.32 (m, 2H), 3.47-3.37 (m, 2H), 2.63 (d, J=0.9 Hz, 3H). LC-MS: method H, RT=1.09 min, MS (ESI) m/z: 446.0 (M+H)$^+$.

Example 193

Intermediate I-2 (0.010, 0.032 mmol) and Intermediate 193E (0.014 g, 0.032 mmol) were dissolved in DMF (1 mL). PdCl$_2$(dppf)-CH$_2$Cl$_2$ adduct (1.560 mg, 1.910 μmol) was added and the reaction mixture was degassed by bubbling with argon for 15 minutes. Na$_2$CO$_3$, 3 M aqueous solution (0.100 mL, 0.300 mmol) was added and the reaction mixture was degassed for 5 minutes, then sealed and heated to 90° C. in the microwave for 30 minutes. The reaction mixture was diluted with DMF, filtered, and purified by preparative HPLC (Method D, 45% to 90% B in 20 minutes) to yield Example 193 (0.0053 g, 9.48 μmol, 29.8% yield): $^1$H NMR (500 MHz, DMSO-d$_6$) δ 9.09 (s, 1H), 8.76 (d, J=1.7 Hz, 1H), 8.03 (s, 1H), 7.92-7.88 (m, 2H), 7.44-7.39 (m, 2H), 6.73 (s, 1H), 4.82 (s, 2H), 4.34 (t, J=5.5 Hz, 2H), 3.49 (s, 3H), 3.26 (q, J=5.6 Hz, 2H), 2.73 (s, 3H), 2.69 (s, 3H). LC-MS: method H, RT=1.15 min, MS (ESI) m/z: 554.1 (M+H)$^+$. Analytical HPLC Method B: 99% purity.

Example 194

4-fluoro-N-(2-((2-(2-methoxy-7-methylquinoxalin-5-yl)-7-methylthiazolo[5,4-b]pyridin-5-yl)oxy)ethyl)benzenesulfonamide

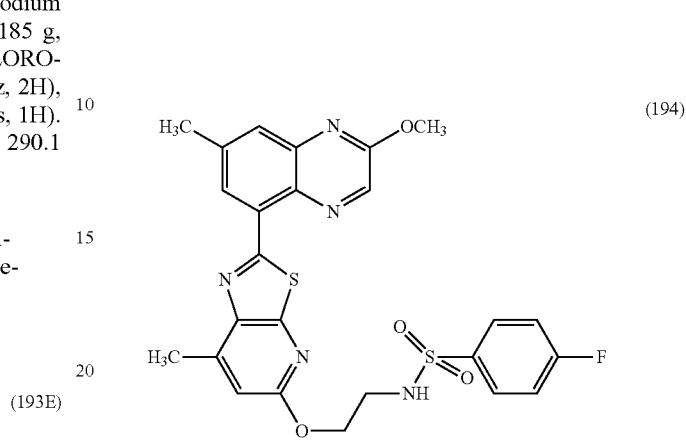

(194)

Intermediate I-2 (0.010, 0.032 mmol) and Example 193E (0.015 g, 0.032 mmol) were dissolved in DMF (1 mL). PdCl$_2$(dppf)-CH$_2$Cl$_2$ adduct (1.560 mg, 1.910 μmol) was added and the reaction mixture was degassed by bubbling with argon for 15 minutes. Na$_2$CO$_3$, 3 M aqueous solution (0.100 mL, 0.300 mmol) was added and the reaction mixture was degassed for 5 minutes, then sealed and heated to 90° C. in the microwave for 30 minutes. The reaction mixture was diluted with DMF, filtered, and purified by preparative HPLC (Method D, 60% to 90% B in 20 minutes) to yield Example 194 (0.0043 g, 7.65 μmol, 23% yield): $^1$H NMR (500 MHz, DMSO-d$_6$) δ 8.72 (s, 1H), 8.55 (d, J=1.4 Hz, 1H), 8.01 (t, J=5.8 Hz, 1H), 7.89 (dd, J=8.8, 5.2 Hz, 2H), 7.83 (s, 1H), 7.41 (t, J=8.8 Hz, 2H), 6.72 (s, 1H), 4.33 (t, J=5.5 Hz, 2H), 4.09 (s, 3H), 3.26 (d, J=5.8 Hz, 2H), 2.72 (s, 3H), 2.65 (s, 3H). LC-MS: method H, RT=1.15 min, MS (ESI) m/z: 540.1 (M+H)$^+$. Analytical HPLC Method B: 96% purity.

Example 195

5-(benzofuran-2-yl)-2-(methoxymethyl)-7-methylquinoxaline

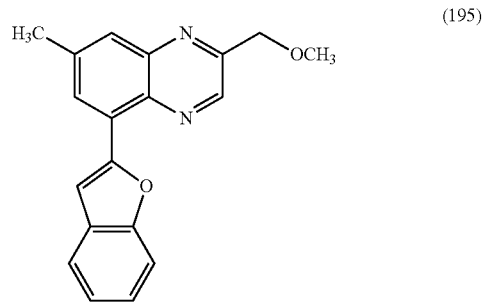 [SMILES: COCc1cnc2c(-c3cc4ccccc4o3)cc(C)cc2n1]

(195)

Intermediate 195A: ethyl 5-(benzofuran-2-yl)-7-methylquinoxaline-2-carboxylate

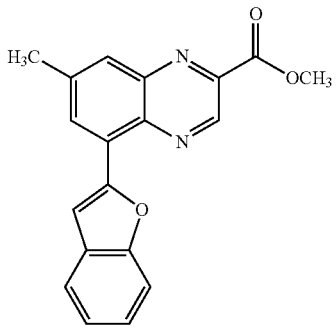
(195A)

Intermediate I-15 (0.250 g, 0.847 mmol) and benzofuran-2-ylboronic acid (0.137 g, 0.847 mmol) were dissolved in DMF (20 mL). PdCl$_2$(dppf)-CH$_2$Cl$_2$ adduct (0.042 g, 0.051 mmol) was added and the reaction mixture was degassed by bubbling with argon for 15 minutes. Na$_2$CO$_3$ (3 mL, 6.00 mmol) was added and the reaction mixture was degassed for 5 minutes, then sealed and heated to 90° C. in the microwave for 30 minutes. The reaction mixture was diluted with EtOAc and filtered through a micron filter and concentrated in vacuo. Purified by ISCO to remove any Pd or ligand based impurities. 40 g column with a 0-100% gradient of EtOAc in hexanes was used. Fractions pooled and the residue was purified on Prep HPLC using Method A to yield Intermediate 195A (0.074 g, 0.223 mmol, 26.3% yield) LC-MS: method H, RT=1.19 min, MS (ESI) m/z: 333.0 (M+H)$^+$.

Intermediate 195B: (5-(benzofuran-2-yl)-7-methylquinoxalin-2-yl)methanol

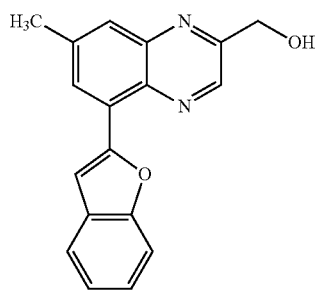
(195B)

Intermediate 195A (0.010 g, 0.030 mmol) was dissolved in THF (1 mL). LiBH$_4$ (1.311 mg, 0.060 mmol) was added and the reaction mixture was allowed to stir at room temperature for 18 h. The reaction mixture was diluted with water and EtOAc. The layers were separated and the organic layer was washed with brine, dried with sodium sulfate, and concentrated under reduced pressure to yield Intermediate 195B. LC-MS: method H, RT=1.07 min, MS (ESI) m/z: 291.1 (M+H)$^+$. Used without further purification in the next step.

Example 195

Intermediate 195B (0.0087 g, 0.030 mmol), Cs$_2$CO$_3$ (0.024 g, 0.075 mmol), and MeI (1.874 µl, 0.030 mmol) were dissolved in DMF (1 mL) and allowed to stir at 50° C. for over the weekend. The reaction mixture was diluted with water and EtOAc. The aqueous layer was back extracted with EtOAc and the combined organic layer was washed with brine, dried with sodium sulfate, and concentrated under reduced pressure. The reaction mixture was diluted with DMF, filtered, and purified by preparative HPLC (Method D, 45% to 80% B in 20 minutes) to yield Example 195 (0.0006 g, 1.932 µmol, 6.45% yield): $^1$H NMR (500 MHz, METHANOL-d$_4$) δ 9.05 (s, 1H), 8.34 (d, J=1.7 Hz, 1H), 8.15 (d, J=0.8 Hz, 1H), 7.80 (d, J=0.8 Hz, 1H), 7.68 (d, J=7.4 Hz, 1H), 7.58-7.55 (m, 1H), 7.33 (td, J=7.7, 1.1 Hz, 1H), 7.28-7.22 (m, 1H), 4.82 (s, 2H), 3.58 (s, 3H), 2.68 (s, 3H). LC-MS: method H, RT=1.17 min, MS (ESI) m/z: 305.3 (M+H)$^+$. Analytical HPLC Method B: 99% purity.

Example 196

2-((2-(2-methoxy-7-methylquinoxalin-5-yl)-7-methylthiazolo[5,4-b]pyridin-5-yl)oxy)ethyl pyridin-3-ylcarbamate

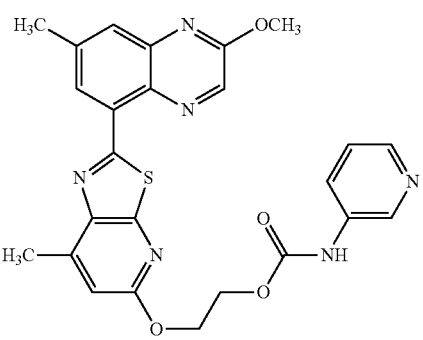
(196)

Intermediate 196A: 2-((2-amino-7-methylthiazolo[5,4-b]pyridin-5-yl)oxy)ethyl acetate

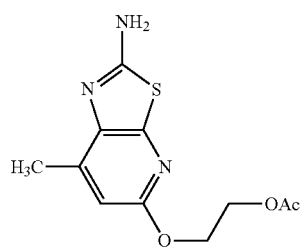
(195A)

Example 193A (0.050 g, 0.146 mmol) was dissolved in DMF. 2-Bromomethyl acetate (0.058 g, 0.350 mmol) and Cs$_2$CO$_3$ (0.237 g, 0.729 mmol) were added and the reaction mixture was stirred at 40° C. for 18 h. The reaction mixture was diluted with EtOAc and water. The layers were separated. The organic layer was washed with brine dried with sodium sulfate, and concentrated under reduced pressure. The reaction mixture was purified on ISCO using a 24 g column with a 0-100% EtOAc in hexanes gradient to yield Intermediate 196A (0.044 g, 0.165 mmol, 56.5% yield) as a pale yellow solid. $^1$H NMR (400 MHz, CHLOROFORM-d)

δ 6.53-6.53 (m, 1H), 5.01 (br. s., 2H), 4.52-4.48 (m, 2H), 4.44-4.39 (m, 2H), 2.49 (d, J=0.7 Hz, 3H), 2.09 (s, 3H). LC-MS: method H, RT=0.72 min, MS (ESI) m/z: 268.2 (M+H)+.

Intermediate 196B: 2-((2-bromo-7-methylthiazolo[5,4-b]pyridin-5-yl)oxy)ethyl acetate

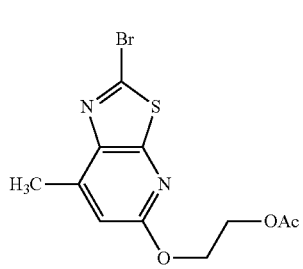

(195B)

Copper(II) bromide (0.063 g, 0.280 mmol) and t-butyl nitrite (0.033 mL, 0.280 mmol) were dissolved in MeCN (0.658 mL) and allowed to stir 10 minutes. Intermediate 196A (0.044 g, 0.165 mmol) was dissolved in MeCN (0.988 mL) and the copper solution was added. The reaction mixture was diluted with EtOAc, washed with 1 N HCl, saturated NaHCO₃, then brine, dried (Na₂SO₄), filtered, and concentrated in vacuo to yield Intermediate 196B (0.046 g, 0.139 mmol, 84% yield): ¹H NMR (400 MHz, CHLOROFORM-d) δ 6.69 (d, J=0.9 Hz, 1H), 4.57-4.53 (m, 2H), 4.44-4.41 (m, 2H), 2.63 (d, J=0.9 Hz, 3H), 2.09 (s, 3H). LC-MS: method H, RT=1.07 min, MS (ESI) m/z: 331.0 (M+H)+.

Intermediate 196C: 2-((2-(2-methoxy-7-methylquinoxalin-5-yl)-7-methylthiazolo[5,4-b] pyridin-5-yl)oxy)ethyl acetate

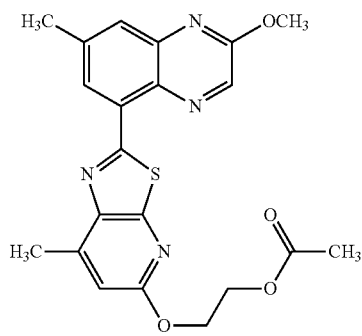

(196C)

Intermediate I-9 (0.042 g, 0.140 mmol) and Intermediate 196B (0.046 g, 0.140 mmol) were dissolved in DMF (1 mL). PdCl₂(dppf)-CH₂Cl₂ adduct (6.86 mg, 8.40 μmol) was added and the reaction mixture was degassed by bubbling with argon for 15 minutes. Na₂CO₃, 3 M aqueous solution (0.100 mL, 0.300 mmol) was added and the reaction mixture was degassed for 5 minutes, then sealed and heated to 90° C. in the microwave for 30 minutes. The reaction mixture was purified on ISCO using 24 g column with a 0-100% EtOAc in hexanes gradient to yield Intermediate 196C (0.021 g, 0.049 mmol, 35.4% yield) as an off white solid. ¹H NMR (400 MHz, CHLOROFORM-d) δ 8.60 (d, J=2.0 Hz, 1H), 8.54 (s, 1H), 7.75 (s, 1H), 6.74 (s, 1H), 4.63 (dd, J=5.8, 3.6 Hz, 2H), 4.51-4.43 (m, 2H), 4.13 (s, 3H), 2.79 (s, 3H), 2.66 (s, 3H), 2.11 (s, 3H). LC-MS: method H, RT=1.34 min, MS (ESI) m/z: 425.1 (M+H)+.

Intermediate 196D: 2-((2-(2-methoxy-7-methylquinoxalin-5-yl)-7-methylthiazolo[5,4-b] pyridin-5-yl)oxy)ethanol

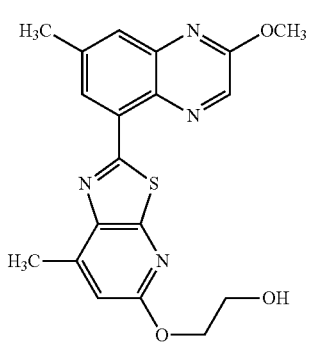

(196D)

To a suspension of Intermediate 196C (0.143 g, 0.337 mmol) in THF (3 mL) and MeOH (1 mL) was added NaOH (1.011 mL, 1.011 mmol) at room temperature. The mixture was stirred at room temperature for 1 h. The mixture was diluted by EtOAc and 1N HCl, extracted by EtOAc, the combined organic layer was washed by water and brine and dried by sodium sulfate, and concentrated to yield Intermediate 196D (0.120 g, 0.314 mmol, 93% yield) as a tan solid. ¹H NMR (400 MHz, METHANOL-d₄) δ 8.61 (s, 1H), 8.58 (s, 1H), 7.78 (s, 1H), 6.82 (s, 1H), 4.48-4.45 (m, 2H), 4.40-4.36 (m, 1H), 4.13 (s, 3H), 3.94-3.90 (m, 2H), 2.77 (s, 3H), 2.66 (s, 3H). LC-MS: method H, RT=1.15 min, MS (ESI) m/z: 383.9 (M+H)+.

Intermediate 196E: 2-((2-(2-methoxy-7-methylquinoxalin-5-yl)-7-methylthiazolo[5,4-b] pyridin-5-yl)oxy)ethyl carbonochloridate

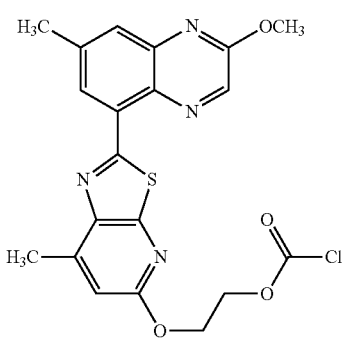

(196E)

To a solution of Intermediate 196D (0.025 g, 0.065 mmol) in THF (3 mL) at room temperature was added 15% phosgene in toluene (0.231 mL, 0.327 mmol) and the mixture was stirred at room temperature for 1 h. The reaction mixture was concentrated under vacuum to give Intermediate 196E (0.030 g, 0.067 mmol, 100% yield) as an yellow solid. It was used for the next step without any purification. LC-MS: method H, RT=1.35 min, MS (ESI) m/z: 444.7 (M+H)+.

Example 196

To a solution of Intermediate 196E (20 mg, 0.045 mmol) in DCM (1 mL) and THF (0.5 mL) was added pyridin-3-amine (14.81 mg, 0.157 mmol) followed by DIEA (0.079 mL, 0.450 mmol). The mixture was stirred at room temperature for 1 h. The reaction mixture was diluted with EtOAc and water. The combined organic layer was washed by brine and concentrated under vacuum. The reaction mixture was diluted with DMSO, filtered, and purified by preparative HPLC (Method D, 55% to 100% B in 20 minutes) to yield Example 196 (0.003 g, 5.61 μmol, 12.48% yield): $^1$H NMR (500 MHz, DMSO-$d_6$) δ 10.05 (br. s., 1H), 8.72 (s, 1H), 8.65 (s, 1H), 8.56 (d, J=1.4 Hz, 1H), 8.22 (d, J=4.7 Hz, 1H), 7.92 (d, J=8.0 Hz, 1H), 7.84 (s, 1H), 7.34 (dd, J=8.3, 4.7 Hz, 1H), 6.93 (s, 1H), 4.67-4.63 (m, 2H), 4.55-4.48 (m, 2H), 4.09 (s, 3H), 2.75 (s, 3H), 2.65 (s, 3H). LC-MS: method H, RT=1.15 min, MS (ESI) m/z: 503.9 (M+H)+. Analytical HPLC Method B: 94% purity.

Example 197

2-((2-(2-methoxy-7-methylquinoxalin-5-yl)-7-methylthiazolo[5,4-b]pyridin-5-yl)oxy)ethyl (6-cyanopyridin-3-yl)carbamate

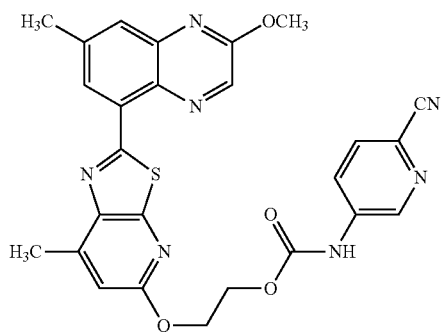

(197)

To a solution of Intermediate 196E (20 mg, 0.045 mmol) in DCM (1 mL) and THF (0.5 mL) was added 5-aminopicolinonitrile (18.74 mg, 0.157 mmol) followed by DIEA (0.079 mL, 0.450 mmol). The mixture was stirred at room temperature for 0.5 h. The reaction mixture was allowed to stir for 18 h at 40° C. The reaction mixture was diluted with EtOAc and water. The combined organic layer was washed by brine and concentrated under vacuum. The reaction mixture was diluted with DMSO, filtered, and purified by preparative HPLC (Method D, 50% to 85% B in 20 minutes) to yield Example 197 (3.2 mg, 5.88 μmol, 13% yield): $^1$H NMR (500 MHz, DMSO-$d_6$) δ 10.57 (s, 1H), 8.73 (d, J=2.2 Hz, 1H), 8.71 (s, 1H), 8.55 (s, 1H), 8.11 (dd, J=8.7, 2.3 Hz, 1H), 7.98 (d, J=8.5 Hz, 1H), 7.84 (s, 1H), 6.92 (s, 1H), 4.71-4.66 (m, 2H), 4.58-4.53 (m, 2H), 4.09 (s, 3H), 2.74 (s, 3H), 2.65 (s, 3H). LC-MS: method H, RT=1.24 min, MS (ESI) m/z: 527.8 (M+H)+. Analytical HPLC Method B: 97% purity.

Example 198

2-((6-fluoro-2-(2-methoxy-7-methylquinoxalin-5-yl)thiazolo[5,4-b]pyridin-5-yl)oxy)ethyl (6-cyanopyridin-3-yl)carbamate

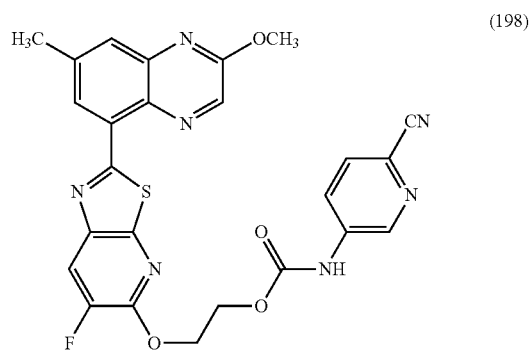 [SMILES: COc1cnc2c(-c3nc4cc(F)c(OCCOC(=O)Nc5ccc(C#N)nc5)nc4s3)cc(C)cc2n1]

(198)

Intermediate 198A: 2-amino-6-fluorothiazolo[5,4-b]pyridin-5-ol, 2 hydrobromide

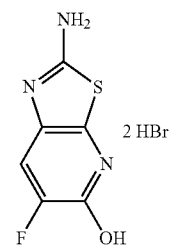

(198A)

Intermediate I-17 (0.500 g, 2.510 mmol) was dissolved HBr in acetic acid (1.704 mL, 15.06 mmol), and the reaction was stirred at 130° C. for 3 h. The reaction was concentrated under reduced pressure to yield Intermediate 198A (0.422 g, 1.216 mmol, 48.5% yield) as a tan solid. $^1$H NMR (400 MHz, METHANOL-$d_4$) δ 7.67 (d, J=9.7 Hz, 1H). LC-MS: method H, RT=0.44 min, MS (ESI) m/z: 186.1 (M+H)+.

Intermediate 198B: 2-((2-amino-6-fluorothiazolo[5,4-b]pyridin-5-yl)oxy)ethyl acetate

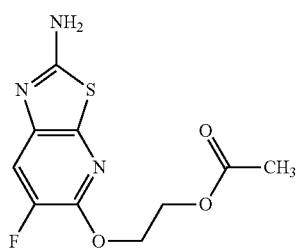

(198B)

Intermediate 198A (0.100 g, 0.288 mmol) was dissolved in DMF (2.88 ml) and Cs$_2$CO$_3$ (0.376 g, 1.153 mmol) was added followed by 2-bromoethyl acetate (0.058 g, 0.346 mmol). The reaction was stirred at room temperature for 3 h. Reaction was diluted with water and EtOAc. The layers were separated, and the aqueous layer was washed with EtOAc thrice. The combined organic layer was washed with brine, dried with sodium sulfate, and concentrated under reduced pressure to yield Intermediate 198B (0.079 g, 0.291 mmol, 101% yield) as a brown solid. Will be used without further purification in the next step. (0.079 g, 0.291 mmol, 100% yield): $^1$H NMR (400 MHz, CHLOROFORM-d$_6$) δ 7.46 (d, J=10.6 Hz, 1H), 4.65-4.54 (m, 2H), 4.49-4.43 (m, 2H), 2.10 (s, 4H). LC-MS: method H, RT=0.67 min, MS (ESI) m/z: 272.1 (M+H)$^+$.

Intermediate 198C: 2-((2-bromo-6-fluorothiazolo[5,4-b]pyridin-5-yl)oxy)ethyl acetate

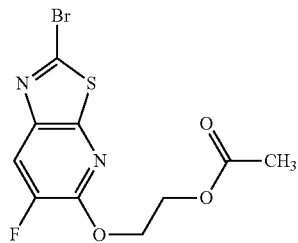

(198C)

Copper(II) bromide (0.078 g, 0.347 mmol) and t-butyl nitrite (0.041 ml, 0.347 mmol) were dissolved in MeCN (0.818 ml) and allowed to stir for 10 minutes. Intermediate 198B (0.080 g, 0.204 mmol) was dissolved in MeCN (1.226 ml), and the copper solution was added. The reaction was stirred for 1 h. The reaction was diluted with EtOAc, washed with 1 N HCl, washed with saturated NaHCO$_3$, washed with brine, dried (Na$_2$SO$_4$), filtered, and concentrated in vacuo to yield Intermediate 198C (0.069 g, 0.206 mmol, 100%). $^1$H NMR (400 MHz, CHLOROFORM-d) δ 7.89 (d, J=9.7 Hz, 1H), 4.69-4.65 (m, 2H), 4.51-4.46 (m, 2H), 2.10 (s, 3H). LC-MS: method H, RT=0.96 min, MS (ESI) m/z: 335.0 (M+H)$^+$.

Intermediate 198D: 2-((6-fluoro-2-(2-methoxy-7-methylquinoxalin-5-yl)thiazolo[5,4-b]pyridin-5-yl)oxy)ethyl acetate

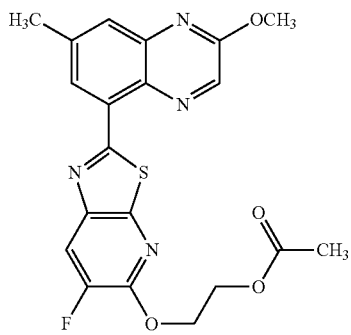

(198D)

Intermediate I-9 (0.062 g, 0.206 mmol) and Intermediate 198C (0.069 g, 0.206 mmol) were dissolved in DMF (1 ml). PdCl$_2$(dppf)-CH$_2$Cl$_2$ adduct (10.09 mg, 0.012 mmol) was added, and the reaction was degassed by bubbling with argon for 15 minutes. A 3 M aqueous solution of Na$_2$CO$_3$ (0.100 ml, 0.300 mmol) was added, and the reaction was degassed for 5 minutes. The reaction vessel was sealed and heated to 90° C. in the microwave for 30 minutes. The reaction was filtered and purified on ISCO using 24 g column with a 0-100% EtOAc in hexanes gradient to yield Intermediate 198D (0.069 g, 0.161 mmol, 78% yield) as an off white solid. LC-MS: method H, RT=0.55 min, MS (ESI) m/z: 429.1 (M+H)$^+$.

Intermediate 198E: 2-((6-fluoro-2-(2-methoxy-7-methylquinoxalin-5-yl)thiazolo[5,4-b]pyridin-5-yl)oxy)ethanol

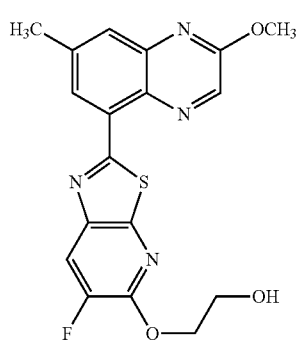

(198E)

To a suspension of Intermediate 198D (0.021 g, 0.049 mmol) in THF (1 mL) and MeOH (0.333 mL) was added NaOH (0.147 mL, 0.147 mmol) at room temperature. The mixture was stirred for 1 h. The mixture was diluted with EtOAc and 1N HCl. The layers were separated, and the aqueous layer was back extracted with EtOAc. The combined organic layer was washed with water, washed with brine, dried with Na$_2$SO$_4$, and concentrated under reduced pressure to yield Intermediate 198E (0.020 g, 0.052 mmol, 106% yield) as a white solid. Will be used without further purification in the next step. $^1$H NMR (400 MHz, CHLOROFORM-d) δ 8.58 (d, J=2.0 Hz, 1H), 8.54 (s, 1H), 8.01 (d, J=10.1 Hz, 1H), 7.79-7.77 (m, 1H), 4.71-4.63 (m, 2H), 4.13 (s, 3H), 4.08 (d, J=7.5 Hz, 2H), 2.65 (s, 3H). LC-MS: method H, RT=1.09 min, MS (ESI) m/z: 387.1 (M+H)$^+$.

Intermediate 198F: 2-((6-fluoro-2-(2-methoxy-7-methylquinoxalin-5-yl)thiazolo[5,4-b]pyridin-5-yl)oxy)ethyl carbonochloridate

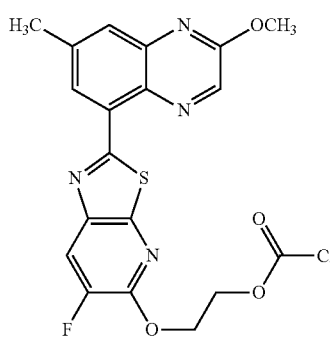

(198F)

To a solution of Intermediate 198E (0.025 g, 0.065 mmol) in THF (3 mL) at room temperature was added 15% phosgene in toluene (0.228 mL, 0.323 mmol), and the mixture was stirred at room temperature for 2 h. Solvent was completely removed and the sample was under vacuum overnight to yield Intermediate 198F (0.029 g, 0.065 mmol, 100% yield) as a yellow solid. LC-MS: method H, RT=1.30 min, MS (ESI) m/z: 448.6 (M+H)$^+$.

Example 198

To a solution of Intermediate 198F (15 mg, 0.033 mmol) in DCM (1 mL) and THF (0.5 mL) was added 5-aminopicolinonitrile (13.93 mg, 0.117 mmol) followed by DIEA (0.058 mL, 0.334 mmol). The mixture was stirred at room temperature for 1 h. The reaction mixture was quenched with 0.2 mL of MeOH. The reaction mixture was concentrated. The reaction mixture was diluted with DMSO, filtered, and purified by preparative HPLC (Method D, 55% to 85% B in 20 minutes) to yield Example 198 (4.6 mg, 8.22 µmol, 24.60% yield): $^1$H NMR (500 MHz, DMSO-d$_6$) δ 10.56 (br. s., 1H), 8.72 (d, J=8.8 Hz, 2H), 8.56 (br. s., 1H), 8.50 (d, J=11.3 Hz, 1H), 8.11 (d, J=8.0 Hz, 1H), 7.96-7.94 (m, 1H), 7.88 (br. s., 1H), 4.82 (br. s., 2H), 4.61 (br. s., 2H), 4.10 (br. s., 3H), 2.65 (br. s., 3H). LC-MS: method H, RT=1.16 min, MS (ESI) m/z: 532.1 (M+H)$^+$. Analytical HPLC Method B: 95% purity.

Example 199

N-(2-((2-(7-chloro-2-methoxyquinoxalin-5-yl)-4-methylbenzo[d]thiazol-6-yl)oxy)ethyl)-4-fluorobenzenesulfonamide In a vial charged with a stirring bar, Intermediate I-28 (130 mg, 0.406 mmol) and Intermediate I-5 (235 mg, 0.527 mmol) were dissolved in 1,4-dioxane (8 mL). Na$_2$CO$_3$ (6 mL, 12.00 mmol) was added, followed by PdCl$_2$(dppf)-CH$_2$Cl$_2$ adduct (16.56 mg, 0.020 mmol). The mixture was stirred at 100° C. for 1 hour. After cooling to room temperature, the reaction mixture was diluted by adding 30 mL of EtOAc and 20 mL of water. After separation, the aqueous layer was extracted with 20 mL of EtOAc. Then organic phases were combined, washed with brine, dried over Na$_2$SO$_4$ and concentrated. The crude product was purified by flash chromatography (40 g silica gel column, 0-100% EtOAc/Hexane) to give Example 199 as a yellow solid (203 mg, 90%). $^1$H NMR (500 MHz, DMSO-d$_6$) δ 8.75 (s, 1H), 8.59 (d, J=2.2 Hz, 1H), 8.03 (br s, 1H), 7.99 (d, J=2.2 Hz, 1H), 7.90 (dd, J=8.8, 5.2 Hz, 2H), 7.48-7.39 (m, 3H), 6.85 (d, J=1.4 Hz, 1H), 4.07 (s, 3H), 4.04 (s, 2H), 3.22 (br s, 2H), 2.70 (s, 3H); LC-MS: method J, RT=1.27 min, MS (ESI) m/z: 559.1 (M+H)$^+$.

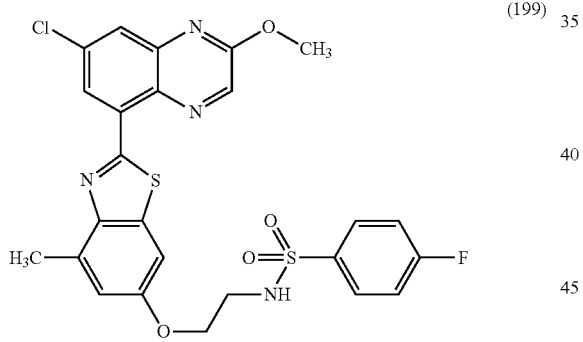

(199)

Examples 200 to 225

The following additional examples have been prepared, isolated and characterized using the methods described for Example 199 and the examples above.

| Ex. No. | Structure | LCMS [M + H]$^+$ m/z | LCMS RT(Min)/ Method | NMR |
|---|---|---|---|---|
| 200 | 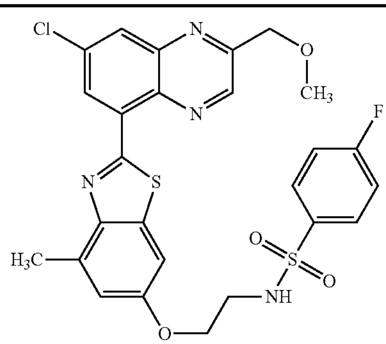 | 573.2 | 1.15/J | $^1$H NMR (500 MHz, chloroform-d) δ 9.14 (s, 1H), 9.01 (d, J = 2.5 Hz, 1H), 8.14 (d, J = 2.2 Hz, 1H), 7.97-7.90 (m, 2H), 7.20 (t, J = 8.5 Hz, 2H), 7.16 (d, J = 2.5 Hz, 1H), 6.86 (d, J = 1.4 Hz, 1H), 4.98 (t, J = 6.3 Hz, 1H), 4.86 (s, 2H), 4.11 (t, J = 5.2 Hz, 2H), 3.60 (s, 3H), 3.45 (d, J = 5.5 Hz, 2H), 2.83 (s, 3H). |

-continued

| Ex. No. | Structure | LCMS [M + H]+ m/z | LCMS RT(Min)/ Method | NMR |
|---|---|---|---|---|
| 201 | 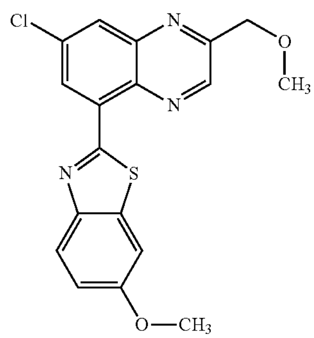 [SMILES: COCc1cnc2c(-c3nc4ccc(OC)cc4s3)cc(Cl)cc2n1] | 386.1 | 1.29/H | ¹H NMR (500 MHz, DMSO-d₆) δ 9.18 (s, 1H), 8.84 (s, 1H), 8.32 (s, 1H), 8.05 (d, J = 9.1 Hz, 1H), 7.77 (br s, 1H), 7.19 (d, J = 8.8 Hz, 1H), 4.83 (s, 2H), 3.89 (s, 3H), 3.48 (s, 3H). |
| 202 | 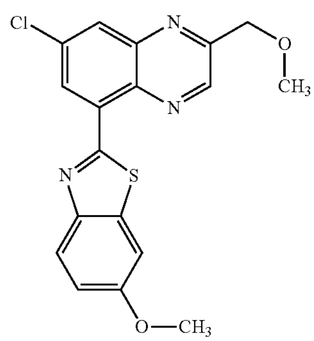 [SMILES: COCc1cnc2c(-c3nc4ccc(OC)cc4s3)cc(Cl)cc2n1] | 372.10 | 2.19/L | ¹H NMR (500 MHz, DMSO-d₆) δ 9.18 (s, 1H), 8.84 (s, 1H), 8.32 (s, 1H), 8.05 (d, J = 9.1 Hz, 1H), 7.77 (br s, 1H), 7.19 (d, J = 8.8 Hz, 1H), 4.83 (s, 2H), 3.89 (s, 3H), 3.48 (s, 3H). |
| 203 | 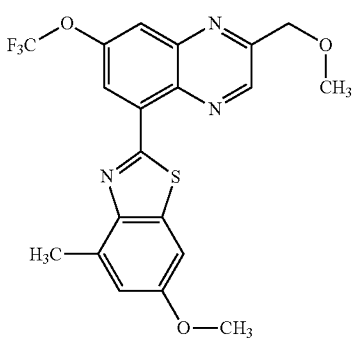 [SMILES: COCc1cnc2c(-c3nc4c(C)cc(OC)cc4s3)cc(OC(F)(F)F)cc2n1] | 436.15 | 2.882/L | ¹H NMR (500 MHz, DMSO-d₆) δ 9.22 (s, 1H), 8.82 (br s, 1H), 8.20 (br s, 1H), 7.59 (br s, 1H), 7.04 (br s, 1H), 4.86 (s, 2H), 3.87 (d, J = 1.1 Hz, 3H), 3.50 (s, 3H), 2.76 (s, 3H). |
| 204 | 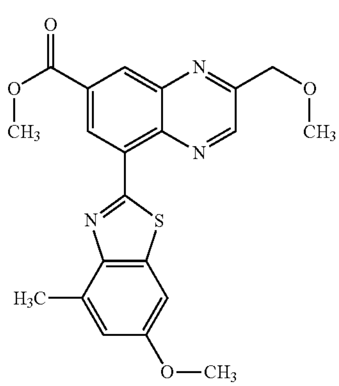 [SMILES: COCc1cnc2c(-c3nc4c(C)cc(OC)cc4s3)cc(C(=O)OC)cc2n1] | 410.2 | 2.434/L | ¹H NMR (500 MHz, DMSO-d₆) δ 9.38 (d, J = 1.9 Hz, 1H), 9.26 (s, 1H), 8.68 (d, J = 1.9 Hz, 1H), 7.57 (d, J = 2.2 Hz, 1H), 7.03 (s, 1H), 4.86 (s, 2H), 4.02 (s, 3H), 3.86 (s, 3H), 3.50 (s, 3H), 2.76 (s, 3H). |

| Ex. No. | Structure | LCMS [M + H]+ m/z | LCMS RT(Min)/ Method | NMR |
|---|---|---|---|---|
| 205 | 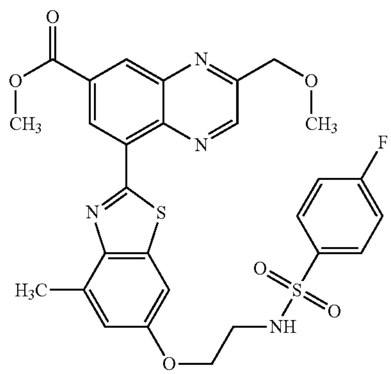 [SMILES: COCc1cnc2c(-c3nc4c(C)cc(OCCNS(=O)(=O)c5ccc(F)cc5)cc4s3)cc(C(=O)OC)cc2n1] | 597.15 | 2.323/L | ¹H NMR (500 MHz, DMSO-d₆) δ 9.34 (d, J = 1.7 Hz, 1H), 9.23 (s, 1H), 8.65 (d, J = 1.9 Hz, 1H), 8.04 (br s, 1H), 7.94-7.85 (m, 2H), 7.50-7.38 (m, 3H), 6.88 (s, 1H), 4.85 (s, 2H), 4.06 (t, J = 5.1 Hz, 2H), 4.02 (s, 3H), 3.49 (s, 3H), 3.23 (t, J = 5.0 Hz, 2H), 2.74 (s, 3H). |
| 206 | 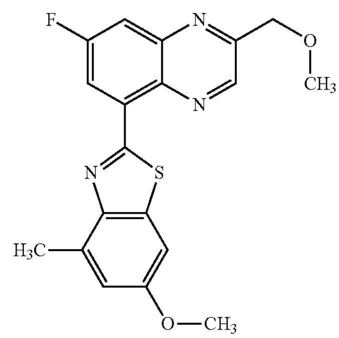 | 370.2 | 1.23/J | ¹H NMR (400 MHz, chloroform-d) δ 9.12 (s, 1H), 8.85 (dd, J = 9.9, 2.9 Hz, 1H), 7.78 (dd, J = 8.6, 2.9 Hz, 1H), 6.96 (d, J = 1.3 Hz, 1H), 4.86 (s, 2H), 3.91 (s, 3H), 3.60 (s, 3H), 2.83 (s, 3H). |
| 207 | 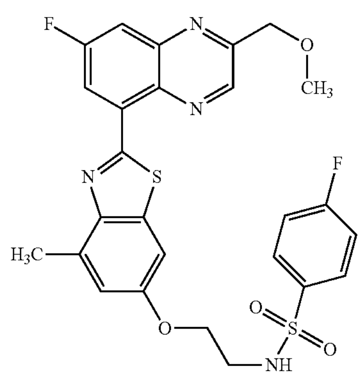 [SMILES: COCc1cnc2c(-c3nc4c(C)cc(OCCNS(=O)(=O)c5ccc(F)cc5)cc4s3)cc(F)cc2n1] | 557.2 | 1.12/J | ¹H NMR (400 MHz, chloroform-d) δ 9.12 (s, 1H), 8.85 (dd, J = 9.7, 2.9 Hz, 1H), 7.99-7.88 (m, 2H), 7.79 (dd, J = 8.4, 2.9 Hz, 1H), 7.24-7.15 (m, 3H), 6.86 (s, 1H), 4.99 (t, J = 5.8 Hz, 1H), 4.86 (s, 2H), 4.11 (t, J = 5.0 Hz, 2H), 3.60 (s, 3H), 3.45 (q, J = 5.5 Hz, 2H), 2.85-2.79 (m, 3H). |
| 208 | 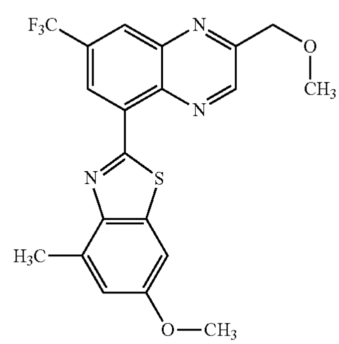 | 420.05 | 2.74/L | ¹H NMR (500 MHz, METHANOL-d₄) δ 9.22 (s, 1H), 9.13 (d, J = 1.5 Hz, 1H), 8.39 (s, 1H), 7.27 (d, J = 2.5 Hz, 1H), 6.92 (s, 1H), 4.86 (s, 2H), 3.88 (s, 3H), 3.59 (s, 3H), 2.78 (s, 3H). |

-continued

| Ex. No. | Structure | LCMS [M + H]+ m/z | LCMS RT(Min)/ Method | NMR |
|---|---|---|---|---|
| 209 | 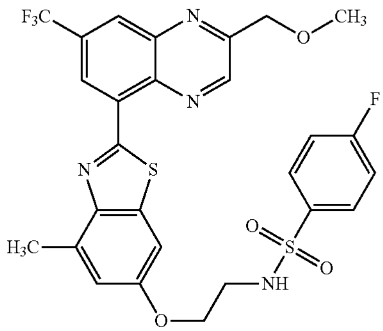 [SMILES: COCc1cnc2c(-c3nc4c(C)cc(OCCNS(=O)(=O)c5ccc(F)cc5)cc4s3)cc(C(F)(F)F)cc2n1] | 629.05 (M + Na)+ | 2.65/L | ¹H NMR (500 MHz, METHANOL-d$_4$) δ 9.23 (s, 1H), 9.13 (d, J = 1.5 Hz, 1H), 8.40 (s, 1H), 7.94-7.87 (m, 2H), 7.26-7.09 (m, 3H), 6.82 (s, 1H), 4.87 (s, 2H), 4.06 (t, J = 5.4 Hz, 2H), 3.59 (s, 3H), 3.35 (t, J = 5.4 Hz, 2H), 2.77 (s, 3H). |
| 210 | 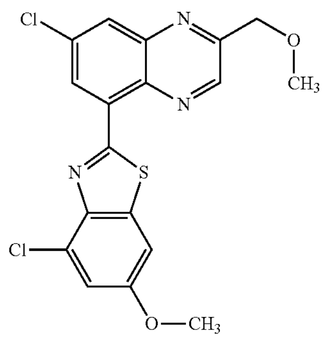 [SMILES: COCc1cnc2c(-c3nc4c(Cl)cc(OC)cc4s3)cc(Cl)cc2n1] | 406.1 | 1.23/H | ¹H NMR (400 MHz, chloroform-d) δ 9.14 (s, 1H), 9.08 (d, J = 2.4 Hz, 1H), 8.17 (d, J = 2.4 Hz, 1H), 7.35 (d, J = 2.4 Hz, 1H), 7.21 (d, J = 2.4 Hz, 1H), 4.86 (s, 2H), 3.93 (s, 3H), 3.60 (s, 3H). |
| 211 | 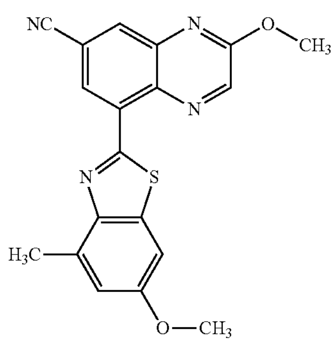 | 363.0 | 2.633/L | ¹H NMR (500 MHz, DMSO-d$_6$) δ 8.97 (br s, 1H), 8.94 (s, 1H), 8.54 (br s, 1H), 7.58 (br s, 1H), 7.05 (br s, 1H), 4.14 (br s, 3H), 3.87 (br s, 3H), 2.78 (br s, 3H). |
| 212 | 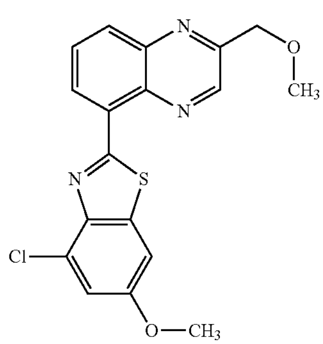 [SMILES: COCc1cnc2c(-c3nc4c(Cl)cc(OC)cc4s3)cccc2n1] | 372.0 | 1.06/J | ¹H NMR (400 MHz, chloroform-d) δ 9.17 (s, 1H), 9.14 (dd, J = 7.5, 1.3 Hz, 1H), 8.20 (dd, J = 8.1, 1.3 Hz, 1H), 7.95 (t, J = 7.9 Hz, 1H), 7.35 (d, J = 2.2 Hz, 1H), 7.20 (d, J = 2.2 Hz, 1H), 4.88 (s, 2H), 3.93 (s, 3H), 3.60 (s, 3H). |

| Ex. No. | Structure | LCMS [M + H]+ m/z | LCMS RT(Min)/ Method | NMR |
|---|---|---|---|---|
| 213 | 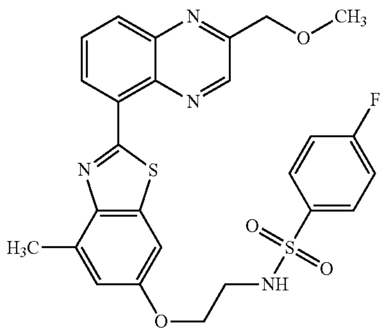 [SMILES: COCc1cnc2c(-c3nc4c(C)cc(OCCNS(=O)(=O)c5ccc(F)cc5)cc4s3)cccc2n1] | 539.20 | 2.542/L | ¹H NMR (500 MHz, DMSO-d₆) δ 9.16 (br s, 1H), 9.01-8.94 (m, 1H), 8.23 (d, J = 8.0 Hz, 1H), 8.06 (br s, 2H), 7.90 (br s, 2H), 7.49-7.38 (m, 3H), 6.86 (br s, 1H), 4.83 (br s, 2H), 4.05 (br s, 2H), 3.47 (br s, 3H), 3.22 (br s, 2H), 2.73 (br s, 3H). |
| 214 | 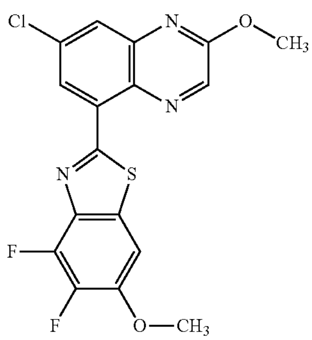 [SMILES: COc1cnc2c(-c3nc4c(F)c(F)c(OC)cc4s3)cc(Cl)cc2n1] | 393.6 | 1.23/J | ¹H NMR (400 MHz, chloroform-d) δ 8.86 (d, J = 2.2 Hz, 1H), 8.59 (s, 1H), 7.96 (d, J = 2.4 Hz, 1H), 7.24 (dd, J = 6.7, 1.9 Hz, 1H), 4.15 (s, 3H), 4.02 (s, 3H); ¹⁹F NMR (376 MHz, chloroform-d) δ −146.29 (d, J = 18.3 Hz, 1F), −160.18 (dd, J = 18.3, 6.9 Hz, 1F). |
| 215 | 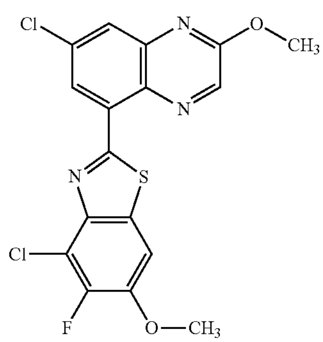 [SMILES: COc1cnc2c(-c3nc4c(Cl)c(F)c(OC)cc4s3)cc(Cl)cc2n1] | 410.0 | 1.45/J | ¹H NMR (400 MHz, Dioxane) δ 8.85 (d, J = 2.4 Hz, 1H), 8.63 (s, 1H), 8.04 (d, J = 2.4 Hz, 1H), 7.54 (d, J = 7.5 Hz, 1H), 4.11 (s, 3H), 3.97 (s, 3H); ¹⁹F NMR (376 MHz, dioxane) δ −136.60 (s, 1F). |
| 216 | 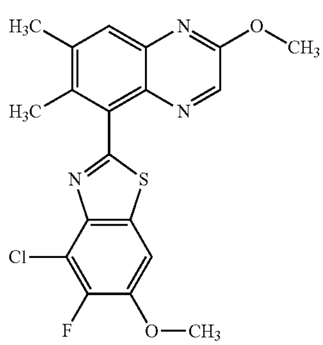 [SMILES: COc1cnc2c(-c3nc4c(Cl)c(F)c(OC)cc4s3)c(C)c(C)cc2n1] | 404.05 | 2.289/L | ¹H NMR (500 MHz, DMSO-d₆) δ 8.47 (s, 1H), 8.03 (d, J = 7.4 Hz, 1H), 7.90 (s, 1H), 4.05 (s, 3H), 3.98 (s, 3H), 2.54 (s, 3H), 2.29 (s, 3H). |

| Ex. No. | Structure | LCMS [M + H]+ m/z | LCMS RT(Min)/ Method | NMR |
|---|---|---|---|---|
| 217 | 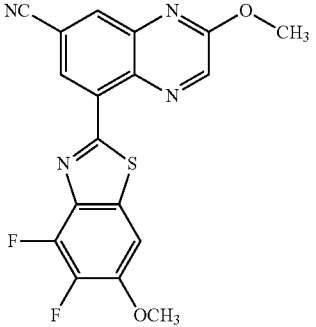 [SMILES: COc1cnc2c(-c3nc4c(F)c(F)c(OC)cc4s3)cc(C#N)cc2n1] | 385.10 | 2.341/K | ¹H NMR (500 MHz, DMSO-d₆) δ 9.08 (s, 1H), 8.99 (s, 1H), 8.59 (s, 1H), 6.86 (d, J = 7.7 Hz, 1H), 3.99 (s, 3H), 3.25 (br s, 3H). |
| 218 | 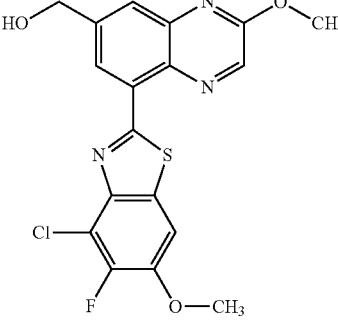 | 406.05 | 2.049/L | ¹H NMR (500 MHz, DMSO-d₆) δ 8.74 (br s, 2H), 8.01-7.89 (m, 2H), 5.66 (br s, 1H), 4.83 (br s, 2H), 4.09 (br s, 3H), 3.97 (br s, 3H). |
| 219 | 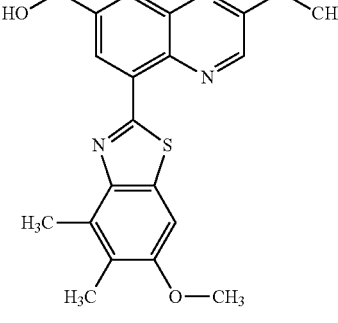 | 382.15 | 2.228/L | ¹H NMR (500 MHz, DMSO-d₆) δ 8.76 (br s, 2H), 7.91 (br s, 1H), 7.55 (br s, 1H), 5.63 (d, J = 3.9 Hz, 1H), 4.85 (br s, 2H), 4.11 (br s, 3H), 3.91 (br s, 3H), 2.76 (br s, 3H), 2.26 (br s, 3H). |
| 220 | 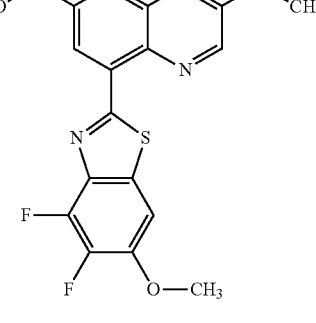 | 390.15 | 1.957/L | ¹H NMR (500 MHz, DMSO-d₆) δ 8.70 (br s, 2H), 7.90 (br s, 1H), 7.76 (br s, 1H), 5.66 (br s, 1H), 4.83 (br s, 2H), 4.10 (br s, 3H), 3.98 (br s, 3H). |

| Ex. No. | Structure | LCMS [M + H]+ m/z | LCMS RT(Min)/ Method | NMR |
|---|---|---|---|---|
| 221 | 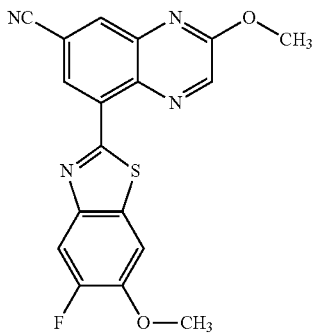 [SMILES: COc1cnc2c(-c3nc4cc(F)c(OC)cc4s3)cc(C#N)cc2n1] | 367.10 | 2.234/L | 1H NMR (500 MHz, DMSO-d6) δ 8.98 (s, 1H), 8.88 (d, J = 1.9 Hz, 1H), 8.55 (d, J = 1.9 Hz, 1H), 8.05-7.98 (m, 2H), 4.13 (s, 3H), 3.97 (s, 3H). |
| 222 | 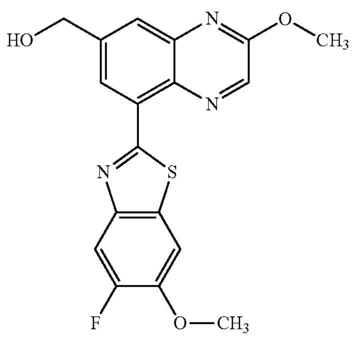 [SMILES: COc1cnc2c(-c3nc4cc(F)c(OC)cc4s3)cc(CO)cc2n1] | 372.10 | 1.851/L | 1H NMR (500 MHz, DMSO-d6) δ 8.77 (s, 1H), 8.73 (d, J = 1.7 Hz, 1H), 8.01-7.88 (m, 3H), 5.62 (t, J = 5.8 Hz, 1H), 4.82 (d, J = 5.8 Hz, 2H), 4.09 (s, 3H), 3.96 (s, 3H). |
| 223 | 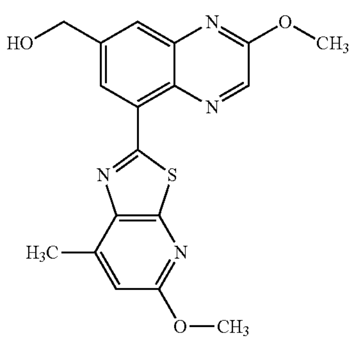 [SMILES: COc1cnc2c(-c3nc4c(C)cc(OC)nc4s3)cc(CO)cc2n1] | 369.15 | 2.010/L | 1H NMR (500 MHz, DMSO-d6) δ 8.74 (s, 1H), 8.68 (s, 1H), 7.91 (s, 1H), 6.87 (s, 1H), 5.62 (t, J = 5.8 Hz, 1H), 4.82 (d, J = 5.5 Hz, 2H), 4.09 (s, 3H), 3.95 (s, 3H), 2.72 (s, 3H). |
| 224 | 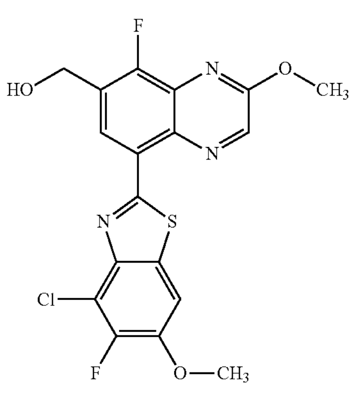 [SMILES: COc1cnc2c(-c3nc4c(Cl)c(F)c(OC)cc4s3)cc(CO)c(F)c2n1] | 424.15 | 2.106/L | 1H NMR (500 MHz, DMSO-d6) δ 8.87 (s, 1H), 8.61 (s, 1H), 6.21 (s, 1H), 4.87 (d, J = 5.8 Hz, 2H), 4.12 (s, 3H), 3.98 (s, 3H). |

Example 225

8-(6-(2-(4-fluorophenylsulfonamido)ethoxy)-4-methylbenzo[d]thiazol-2-yl)-3-(methoxymethyl)quinoxaline-6-carboxamide

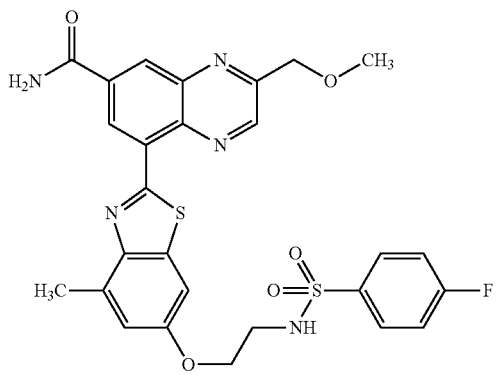

(225)

Intermediate 225A: 8-(6-(2-(4-fluorophenylsulfonamido)ethoxy)-4-methylbenzo[d]thiazol-2-yl)-3-(methoxymethyl)quinoxaline-6-carboxylic acid

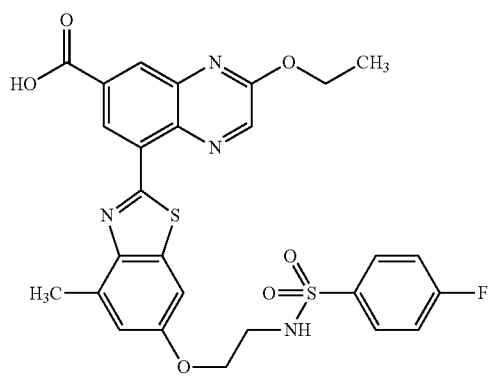

(225A)

Example 205 (223 mg, 0.374 mmol) was dissolved in THF (10 mL) and water (10 mL). The mixture was treated with LiOH·H$_2$O (31.4 mg, 0.748 mmol) at 40° C. for 1 hour. After cooling to room temperature, the reaction mixture was diluted by adding 30 mL of EtOAc and 10 ml of water, followed by 2 mL of 1N HCl (aq.). After shaking and separation, the organic phase was washed with 10 mL of brine and dried over Na$_2$SO$_4$. Concentration gave the desired product as a white solid (145 mg, 63.9%). $^1$H NMR (500 MHz, DMSO-d$_6$) δ 9.40 (s, 1H), 9.21 (s, 1H), 8.63 (s, 1H), 8.04 (t, J=5.4 Hz, 1H), 7.90 (dd, 5.4 Hz, 2H), 7.51-7.35 (m, 3H), 6.86 (s, 1H), 4.85 (s, 2H), 4.05 (t, J=5.0 Hz, 2H), 3.48 (br s, 3H), 3.22 (d, J=5.0 Hz, 2H), 2.74 (s, 3H); LC-MS: method L, RT=1.939 min, MS (ESI) m/z: 583.15 (M+H)$^+$.

Intermediate 225A (30 mg, 0.051 mmol) was dissolved in DMF (1 mL). NH$_4$Cl (8.26 mg, 0.154 mmol) was added, followed by HATU (23.49 mg, 0.062 mmol) and DIEA (0.027 mL, 0.154 mmol). The mixture was stirred at room temperature for 3 h. LCMS showed starting material remained. Another 3 equivalents of DIEA and NH$_4$Cl and 1 equivalents of HATU were added. The reaction mixture was stirred at room temperature for an additional 2 h. The crude material was purified via preparative LC with condition D and dried via centrifugal evaporation to yield the desired product (5.5 mg, 0.0095 mmol, 18.4%). $^1$H NMR (500 MHz, DMSO-d$_6$) δ 9.38 (d, J=1.4 Hz, 1H), 9.22 (s, 1H), 8.74 (d, J=1.7 Hz, 1H), 8.50 (br s, 1H), 8.02 (br s, 1H), 7.90 (dd, J=8.5, 5.2 Hz, 2H), 7.82 (br s, 1H), 7.47 (s, 1H), 7.43 (t, J=8.8 Hz, 2H), 6.88 (s, 1H), 4.86 (s, 2H), 4.06 (t, J=5.2 Hz, 2H), 3.49 (s, 3H), 3.27-3.16 (m, 2H), 2.76 (s, 3H); LC-MS: method L, RT=1.80 min, MS (ESI) m/z: 582.15 (M+H)$^+$.

Examples 226 to 228

The following additional examples were prepared, isolated and characterized using the methods described above for Example 225.

Example 226

8-(6-(2-(4-fluorophenylsulfonamido)ethoxy)-4-methylbenzo[d]thiazol-2-yl)-3-(methoxymethyl)-N,N-dimethylquinoxaline-6-carboxamide

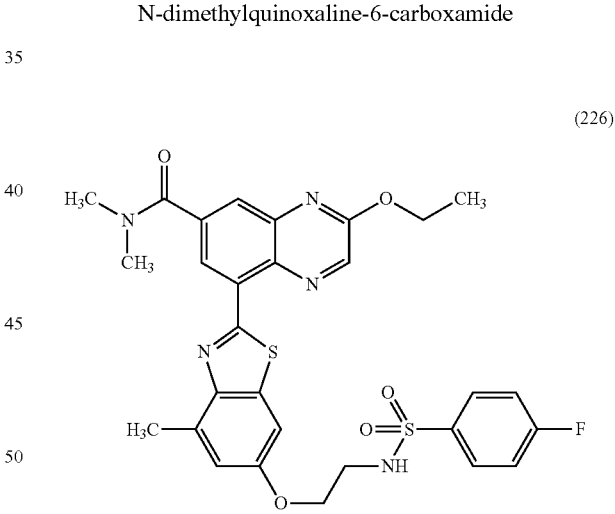

(226)

$^1$H NMR (500 MHz, DMSO-d$_6$) δ 9.38 (d, J=1.4 Hz, 1H), 9.22 (s, 1H), 8.74 (d, J=1.7 Hz, 1H), 8.50 (br s, 1H), 8.02 (br s, 1H), 7.90 (dd, 5.2 Hz, 2H), 7.82 (br s, 1H), 7.47 (s, 1H), 7.43 (t, J=8.8 Hz, 2H), 6.88 (s, 1H), 4.86 (s, 2H), 4.06 (t, J=5.2 Hz, 2H), 3.49 (s, 3H), 3.27-3.16 (m, 2H), 2.76 (s, 3H); LC-MS: method L, RT=1.80 min, MS (ESI) m/z: 582.15 (M+H)$^+$.

Example 227

4-fluoro-N-(2-((2-(2-(methoxymethyl)-7-(piperidine-1-carbonyl)quinoxalin-5-yl)-4-methylbenzo[d]thiazol-6-yl)oxy)ethyl)benzenesulfonamide

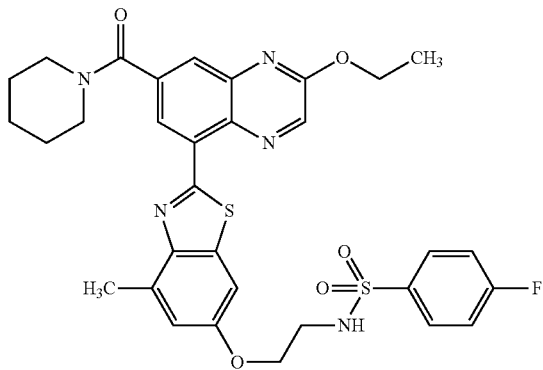

(227)

¹H NMR (500 MHz, DMSO-d₆) δ 9.19 (s, 1H), 8.88 (d, J=1.4 Hz, 1H), 8.16 (d, J=1.4 Hz, 1H), 8.03 (br s, 1H), 7.90 (dd, 5.2 Hz, 2H), 7.47 (s, 1H), 7.43 (t, J=8.8 Hz, 2H), 6.87 (s, 1H), 4.84 (s, 2H), 4.10-4.02 (m, 2H), 3.71 (br s, 2H), 3.48 (s, 3H), 3.42 (br s, 2H), 3.22 (br s, 2H), 2.72 (br s, 3H), 1.66 (br s, 4H), 1.54 (br s, 2H); LC-MS: method L, RT=2.27 min, MS (ESI) m/z: 650.25 (M+H)⁺.

Example 228

8-(6-(2-(4-fluorophenylsulfonamido)ethoxy)-4-methylbenzo[d]thiazol-2-yl)-N-(2-methoxyethyl)-3-(methoxymethyl)quinoxaline-6-carboxamide

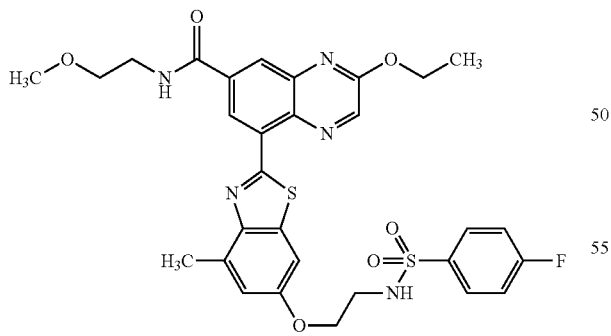

(288)

¹H NMR (500 MHz, DMSO-d₆) δ 9.34 (d, J=1.7 Hz, 1H), 9.22 (s, 1H), 9.08 (br s, 1H), 8.71 (d, J=1.7 Hz, 1H), 8.03 (br s, 1H), 7.93-7.87 (m, 2H), 7.48 (s, 1H), 7.42 (t, J=8.8 Hz, 2H), 6.88 (s, 1H), 4.86 (s, 2H), 4.06 (t, J=5.0 Hz, 2H), 3.55 (br s, 5H), 3.49 (s, 3H), 3.31 (s, 2H), 3.26-3.19 (m, 2H), 2.76 (s, 3H); LC-MS: method L, RT=1.92 min, MS (ESI) m/z: 640.20 (M+H)⁺.

Example 229

4-fluoro-N-(2-((2-(2-methoxy-7-vinylquinoxalin-5-yl)-4-methylbenzo[d]thiazol-6-yl) oxy)ethyl)benzenesulfonamide

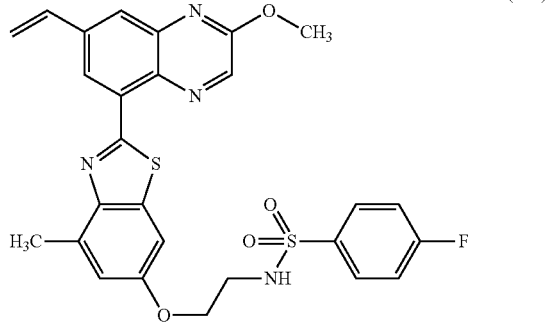

(229)

To a vial charged with a stirring bar was added Example 199 (20 mg, 0.036 mmol), potassium vinyl trifluoroborate (9.58 mg, 0.072 mmol), Cs₂CO₃ (35.0 mg, 0.107 mmol), (S)-BINAP (4.46 mg, 7.16 μmol) and Pd₀Ac₂ (0.803 mg, 3.58 μmol). DMF (1 mL) was added. After degassing with bubbling N₂ for 10 minutes, the vial was sealed and was heated at 120° C. for 1 hour. After cooling to room temperature, the reaction mixture was diluted by adding 10 mL of EtOAc and 10 mL of water. After separation, the organic phase was passed through anhydrous Na₂SO₄ and concentrated on a rotary evaporator. The crude material was purified via preparative LC/MS (method C) and dried via centrifugal evaporation to yield the Example 229 (1.9 mg, 0.0034 mmol, 9.6%). ¹H NMR (500 MHz, DMSO-d₆) δ 8.82 (d, J=1.7 Hz, 1H), 8.74 (s, 1H), 8.05 (d, J=1.7 Hz, 1H), 8.03 (br s, 1H), 7.97-7.83 (m, 2H), 7.49-7.38 (m, 3H), 7.08 (dd, J=17.6, 11.0 Hz, 1H), 6.86 (d, J=1.4 Hz, 1H), 6.19 (d, J=17.9 Hz, 1H), 5.57 (d, J=11.0 Hz, 1H), 4.09 (s, 3H), 4.05 (t, J=5.4 Hz, 2H), 3.22 (br s, 2H), 2.74 (s, 3H);); LC-MS: method K, RT=2.59 min, MS (ESI) m/z: 559.1 (M+H)⁺.

Example 230

N-(2-((2-(7-ethynyl-2-methoxyquinoxalin-5-yl)-4-methylbenzo[d]thiazol-6-yl)oxy)ethyl)-4-fluorobenzenesulfonamide

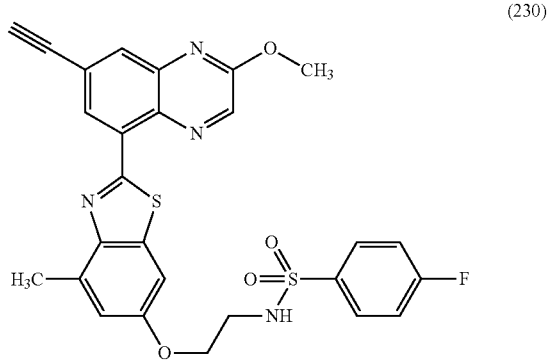 [SMILES: C#Cc1cc(-c2nc3c(C)cc(OCCNS(=O)(=O)c4ccc(F)cc4)cc3s2)c2ncc(OC)nc2c1]

(230)

Intermediate 230A: 4-fluoro-N-(2-((2-(2-methoxy-7-((trimethylsilyl)ethynyl)quinoxalin-5-yl)-4-methylbenzo[d]thiazol-6-yl)oxy)ethyl)benzenesulfonamide

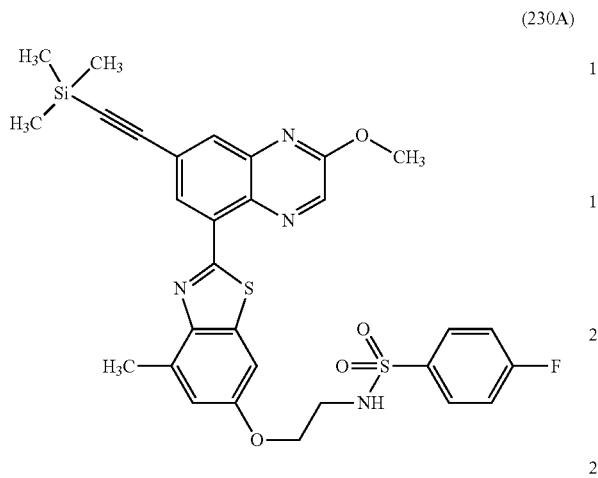

(230A)

Example 230

Intermediate 230A (10 mg, 0.016 mmol) was dissolved in MeOH (0.5 mL)/DCM (0.5 mL) and was treated with $K_2CO_3$ (1.113 mg, 8.05 µmol) for 1 hour. The solid was filtered and solvent was removed on a rotary evaporator. The crude material was purified via preparative LC/MS (method C) and dried via centrifugal evaporation to yield the title compound (1.4 mg, 0.0025 mmol, 16%). $^1$H NMR (500 MHz, DMSO-$d_6$) δ 8.80 (s, 1H), 8.70 (d, J=1.7 Hz, 1H), 8.02 (d, J=1.7 Hz, 2H), 7.90 (dd, 5.4 Hz, 2H), 7.47-7.38 (m, 3H), 6.86 (s, 1H), 4.58 (s, 1H), 4.09 (s, 3H), 4.05 (t, J=5.2 Hz, 2H), 3.22 (d, J=5.2 Hz, 2H), 2.72 (s, 3H); LC-MS: method L, RT=2.58 min, MS (ESI) m/z: 549.15 (M+H)$^+$.

In a microwave vial charged with a stirring bar, a solution of Example 199 (20 mg, 0.036 mmol), $PdCl_2(CH_3CN)_2$ (1.856 mg, 7.16 µmol), 2-(Dicyclohexylphosphino)-2',4',6'-triisopropylbiphenyl (6.82 mg, 0.014 mmol) and $Cs_2CO_3$ (29.1 mg, 0.089 mmol) in acetonitrile (1 mL)) was stirred for 0.5 h at room temperature under $N_2$ atmosphere. To the mixture was added ethynyltrimethylsilane (35.1 mg, 0.358 mmol), and the resultant mixture was stirred for 1 hour at 90° C. in the microwave. The reaction mixture was concentrated under reduced pressure, and the resulting residue was purified by flash chromatography (24 g silica gel column, 0-50% EtOAc/Hexane gradient) to give Intermediate 230A as a yellow solid (13.6 mg, 61.2%). LC-MS: method B, RT=3.0 min, MS (ESI) m/z: 621.1 (M+H)$^+$.

Example 231

N-(2-((2-(7-cyano-2-methoxyquinoxalin-5-yl)-4-methylbenzo[d]thiazol-6-yl)oxy)ethyl)-4-fluorobenzenesulfonamide

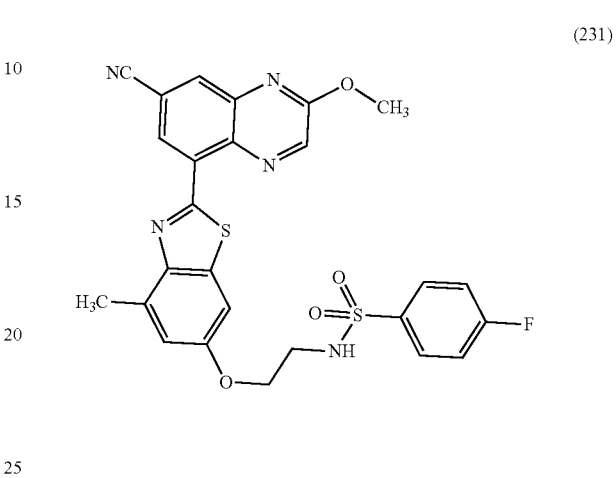

(231)

Example 199 (40 mg, 0.072 mmol), $Pd_2(dba)_3$ (19.66 mg, 0.021 mmol), DPPF (23.80 mg, 0.043 mmol), dicyanozinc (8.40 mg, 0.072 mmol) and zinc (7.02 mg, 0.107 mmol) were mixed in NMP (1 mL) in a microwave vial that was flushed with $N_2$ for 10 minutes. The resulting mixture was heated at 120° C. with vigorous stirring until LCMS showed the disappearance of starting material (3 h). The mixture was cooled to room temperature, diluted with ethyl acetate (50 ml), and then washed with water and brine. After drying over $Na_2SO_4$, the ethyl acetate solution was concentrated by rotary evaporation. The crude material was purified via preparative LC/MS-HPLC, method D and dried via centrifugal evaporation to give Example 231 (7.4 mg, 0.013 mmol, 18.8%). $^1$H NMR (500 MHz, DMSO-$d_6$) δ 8.92 (s, 1H), 8.87 (d, J=1.7 Hz, 1H), 8.48 (d, J=1.7 Hz, 1H), 7.90 (dd, J=8.5, 5.5 Hz, 3H), 7.45-7.39 (m, 3H), 6.87 (s, 1H), 4.11 (s, 3H), 4.05 (t, J=5.1 Hz, 2H), 3.22 (t, J=5.2 Hz, 2H), 2.72 (s, 3H); LC-MS: method L, RT=2.205 min, MS (ESI) m/z: 550.10 (M+H)$^+$.

Examples 232 and 233

Examples 232 and 233 were prepared, isolated and characterized using the methods described in Example 231 above.

Example 232

N-(2-((2-(7-cyano-2-(methoxymethyl)quinoxalin-5-yl)-4-methylbenzo[d]thiazol-6-yl) oxy)ethyl)-4-fluorobenzenesulfonamide

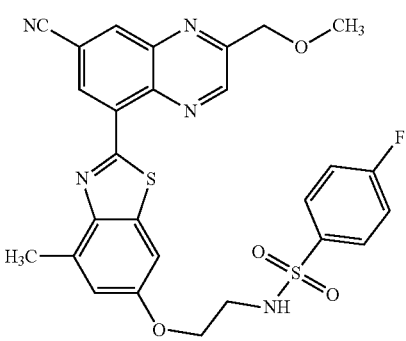

(232)

Example 232 was made from Example 200. $^1$H NMR (500 MHz, DMSO-$d_6$) δ 9.24 (s, 1H), 9.02 (d, J=1.7 Hz, 1H), 8.77 (d, J=1.7 Hz, 1H), 7.90 (dd, J=8.8, 5.2 Hz, 3H), 7.44 (d, J=9.1 Hz, 2H), 6.86 (d, J=1.1 Hz, 1H), 4.84 (s, 2H), 4.05 (t, J=5.2 Hz, 2H), 3.49 (s, 3H), 3.23 (t, J=5.1 Hz, 2H), 2.72 (s, 3H); LC-MS: method L, RT=2.074 min, MS (ESI) m/z: 564.15 (M+H)$^+$.

Example 233

8-(6-methoxy-4-methylbenzo[d]thiazol-2-yl)-3-(methoxymethyl)quinoxaline-6-carbonitrile

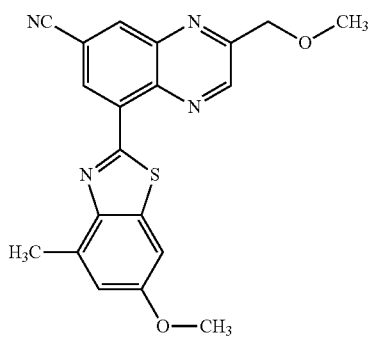

(233)

Example 233 was made from Example 201. $^1$H NMR (400 MHz, chloroform-d) δ 9.28 (s, 1H), 9.25 (d, J=2.0 Hz, 1H), 8.48 (d, J=1.8 Hz, 1H), 7.28-7.27 (m, 1H), 6.99 (dd, J=2.6, 0.9 Hz, 1H), 4.90 (s, 2H), 3.93 (s, 3H), 3.63 (s, 3H), 2.04 (s, 3H); LC-MS: method J, RT=1.08 min, MS (ESI) m/z: 377.1 (M+H)$^+$.

Example 234

4-fluoro-N-(2-((2-(2-(methoxymethyl)-7-vinylquinoxalin-5-yl)-4-methylbenzo[d]thiazol-6-yl)oxy)ethyl)benzenesulfonamide

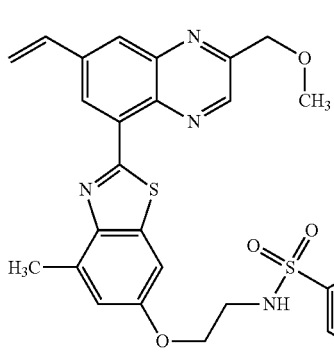

(234)

To a vial charged with a stirring bar was added Example 200 (40 mg, 0.070 mmol), potassium vinyl trifluoroborate (18.70 mg, 0.140 mmol), Cs$_2$CO$_3$ (68.2 mg, 0.209 mmol), (S)-BINAP (17.39 mg, 0.028 mmol) and PdOAc$_2$ (3.13 mg, 0.014 mmol). DMF (1 mL) was added. After degassing with bubbling N$_2$ for 10 minutes, the vial was sealed and was heated at 120° C. for 1 hour. After cooling to room temperature, the reaction mixture was diluted by adding 10 mL of EtOAc and 10 mL of water. After separation, the organic phase was passed through Na$_2$SO$_4$ and concentrated on a rotary evaporator. The crude material was purified via preparative LC/MS with condition D and dried via centrifugal evaporation to yield Example 234 (10.6 mg, 0.018 mmol, 25.5%). $^1$H NMR (500 MHz, DMSO-$d_6$) δ 9.09 (s, 1H), 9.04 (d, J=1.7 Hz, 1H), 8.26 (d, J=1.4 Hz, 1H), 8.04 (br s, 1H), 7.90 (dd, J=8.8, 5.2 Hz, 2H), 7.48-7.39 (m, 3H), 7.13 (dd, J=17.6, 11.0 Hz, 1H), 6.86 (s, 1H), 6.23 (d, J=17.3 Hz, 1H), 5.62 (d, J=11.0 Hz, 1H), 4.81 (s, 2H), 4.06 (t, J=5.1 Hz, 2H), 3.47 (s, 3H), 3.22 (t, J=5.2 Hz, 2H), 2.75 (s, 3H); LC-MS: method L, RT=2.203 min, MS (ESI) m/z: 565.15 (M+H)$^+$.

Example 235

4-fluoro-N-(2-((2-(7-(hydroxymethyl)-2-methoxyquinoxalin-5-yl)-4-methylbenzo[d]thiazol-6-yl)oxy)ethyl)benzenesulfonamide

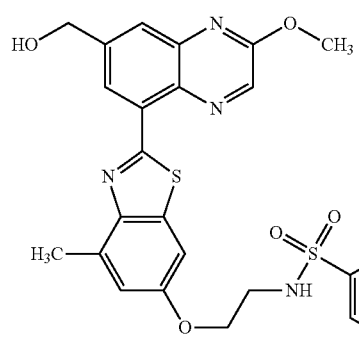

(235)

Intermediate 235A: 4-fluoro-N-(2-((2-(7-formyl-2-methoxyquinoxalin-5-yl)-4-methylbenzo[d]thiazol-6-yl)oxy)ethyl)benzenesulfonamide (235A)

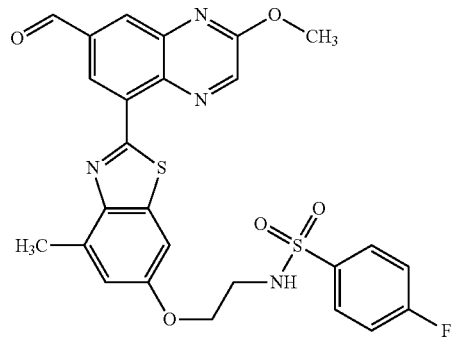

Sodium periodate (0.424 g, 1.983 mmol) was added to a solution of Example 229 (0.364 g, 0.661 mmol) and osmium (VIII) oxide (0.084 mL, 0.013 mmol) in THF (10 mL) and water (3 mL). After 6 h, 20 mL of water and 30 mL of EtOAc was added. Phases were separated, and the aqueous phase was extracted with ethyl acetate (20 mL) and then the combined organic phases were washed with sodium thiosulfate solution and brine, dried over sodium sulfate, filtered and concentrated to give Intermediate 235A (0.319 g, 0.576 mmol, 87.2% yield) as a yellow solid. LC-MS: method J, RT=1.30 min, MS (ESI) m/z: 553.1 (M+H)+.

Example 235

Intermediate 235A (16 mg, 0.029 mmol) was dissolved in 1,4-dioxane (1 mL)/MeOH (1 mL) and was treated with NaBH$_4$ (2.191 mg, 0.058 mmol) at room temperature for 30 minutes. Several drops of saturated NH$_4$Cl (aq.) were added to quench the reaction. The reaction mixture was diluted by adding 15 mL of EtOAc and 10 mL of water. After separation, the organic phase was washed with brine, dried over Na$_2$SO$_4$, filtered, and solvent was removed to give crude product. The crude material was purified via preparative LC/MS with the condition C and dried via centrifugal evaporation to yield Example 235 (6.3 mg, 0.011 mmol, 39%). $^1$H NMR (500 MHz, DMSO-d$_6$) δ 8.76 (s, 1H), 8.73 (s, 1H), 8.03 (t, J=5.8 Hz, 1H), 7.94-7.87 (m, 3H), 7.46-7.39 (m, 3H), 6.86 (s, 1H), 5.61 (t, J=5.8 Hz, 1H), 4.83 (d, J=5.5 Hz, 2H), 4.09 (s, 3H), 4.05 (t, J=5.4 Hz, 2H), 3.22 (q, J=5.4 Hz, 2H), 2.73 (s, 3H); LC-MS: method L, RT=2.046 min, MS (ESI) m/z: 555.15 (M+H)+.

Example 236

N-(2-((2-(7-(1,2-dihydroxyethyl)-2-methoxyquinoxalin-5-yl)-4-methylbenzo[d]thiazol-6-yl)oxy)ethyl)-4-fluorobenzenesulfonamide (236)

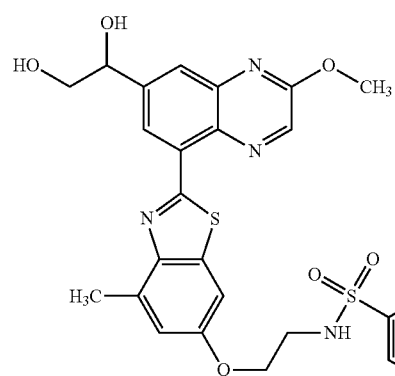

Example 229 (7 mg, 0.013 mmol) was suspended in acetone (1 mL)/water (0.3 mL). 4-Methylmorpholine N-oxide (1.787 mg, 0.015 mmol) was added, followed by OsO$_4$ (1.616 μl, 0.254 μmol). The mixture was stirred at room temperature overnight. On the next day, solvent was removed on a rotary evaporator and the residue was dissolved in 5 mL of EtOAc and was washed with 5 mL of water, dried over Na$_2$SO$_4$, filtered and concentrated to give the crude product. The crude material was purified via preparative LC/MS with the condition D and dried via centrifugal evaporation to afford Example 236 (3.9 mg, 0.0064 mmol, 50%). $^1$H NMR (500 MHz, DMSO-d$_6$) δ 8.78 (d, J=1.9 Hz, 1H), 8.76 (s, 1H), 8.03 (br s, 1H), 7.93 (d, J=1.7 Hz, 1H), 7.92-7.87 (m, 2H), 7.46-7.39 (m, 3H), 6.86 (d, J=1.7 Hz, 1H), 5.68 (d, J=3.3 Hz, 1H), 4.87 (br s, 2H), 4.09 (s, 3H), 4.05 (t, J=5.2 Hz, 2H), 3.69-3.56 (m, 2H), 3.22 (t, J=5.2 Hz, 2H), 2.73 (s, 3H); LC-MS: method L, RT=1.833 min, MS (ESI) m/z: 585.20 (M+H)+.

Example 237

4-fluoro-N-(2-((2-(7-(2-hydroxyethyl)-2-methoxyquinoxalin-5-yl)-4-methylbenzo[d]thiazol-6-yl)oxy)ethyl)benzenesulfonamide (237)

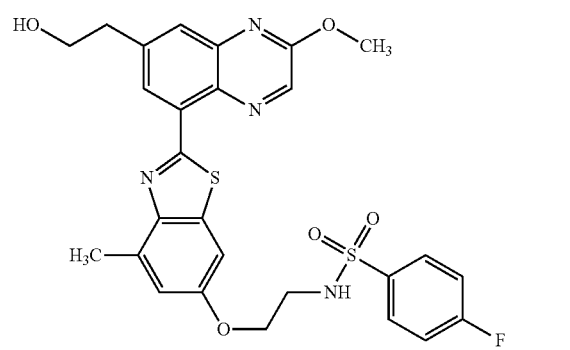

To a solution of Example 229 (20 mg, 0.036 mmol) in THF (1 mL) under N$_2$ at 0° C. was added BH$_3$·THF (0.036 mL, 0.036 mmol) slowly. The reaction mixture was allowed to warm to room temperature and stir at room temperature for 3 h. The reaction mixture was cooled in an ice bath, and NaOH (2.91 mg, 0.073 mmol) in EtOH/H$_2$O (2:1, 0.6 mL) was added, followed by H$_2$O$_2$ (0.011 mL, 0.109 mmol) dropwise. The mixture was warmed to room temperature and stirred at room temperature for 18 h. On the next day, a small amount of saturated NH$_4$Cl (aq.) was added to quench the reaction. The reaction mixture was diluted by adding 15 mL EtOAc and 10 mL of water. After separation, the aqueous layer was passed through anhydrous Na$_2$SO$_4$ and solvent was removed on a rotary evaporator. The crude product was purified by prep-HPLC with method B and dried on a lyophilizer to give Example 237 (1.32 mg, 0.002 mmol, 5.9%). $^1$H NMR (400 MHz, DMSO-d$_6$) δ 8.76 (s, 1H), 8.64 (d, J=2.0 Hz, 1H), 8.04 (br s, 1H), 7.95-7.86 (m, 3H), 7.48-7.40 (m, 3H), 6.87 (d, J=1.5 Hz, 1H), 4.77 (t, J=5.3 Hz, 1H), 4.10 (s, 3H), 4.06 (t, J=5.3 Hz, 2H), 3.85-3.78 (m, 2H), 3.23 (br s, 2H), 3.07 (t, J=6.6 Hz, 2H), 2.74 (s, 3H); LC-MS: method J, RT=0.83 min, MS (ESI) m/z: 569.1 (M+H)$^+$.

Example 238

N-(2-((2-(7-(aminomethyl)-2-methoxyquinoxalin-5-yl)-4-methylbenzo[d]thiazol-6-yl)oxy)ethyl)-4-fluorobenzenesulfonamide

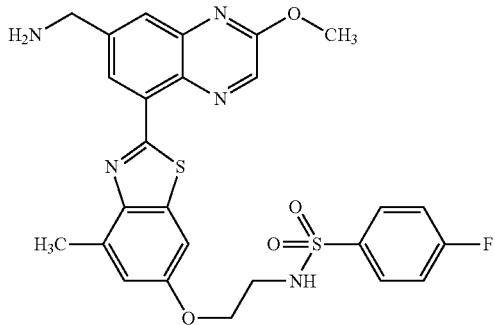

(238)

Intermediate 238A: N-(2-((2-(7-(((2,4-dimethoxybenzyl)amino)methyl)-2-methoxyquinoxalin-5-yl)-4-methylbenzo[d]thiazol-6-yl)oxy)ethyl)-4-fluorobenzenesulfonamide

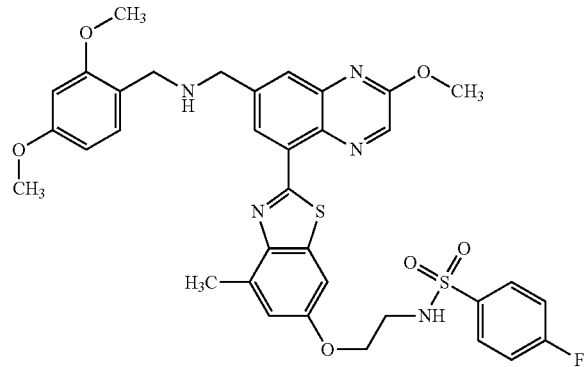

(238A)

Intermediate 235A (110 mg, 0.199 mmol) was dissolved in THF (2 mL) and mixed with (2,4-dimethoxy phenyl) methanamine (133 mg, 0.796 mmol). Acetic acid (0.114 mL, 1.991 mmol) was added and the reaction mixture was stirred at room temperature for 30 minutes. Sodium Triacetoxyborohydride (93 mg, 0.438 mmol) was added. The mixture was stirred at room temperature for 6 h. The reaction mixture was diluted by adding 30 mL of EtOAc and was washed with saturated NaHCO$_3$(aq.) and brine, and concentrated on a rotary evaporator to give crude product that was purified by flash chromatography (24 g, 30-100% EtOAc/Hexane in 20 minutes) to give the title compound (79 mg, 0.092 mmol, 46.2% yield) as a yellow solid. $^1$H NMR (400 MHz, chloroform-d) δ 8.78 (s, 1H), 8.59 (s, 1H), 7.99 (s, 1H), 7.93 (dd, J=8.1, 5.1 Hz, 2H), 7.23-7.17 (m, 3H), 7.15 (s, 1H), 6.82 (s, 1H), 6.49-6.44 (m, 2H), 4.96 (br s, 1H), 4.14 (s, 3H), 4.12-4.05 (m, 5H), 3.87-3.83 (m, 5H), 3.82 (s, 3H), 3.44 (br s, 2H), 2.83 (s, 3H); LC-MS: method H, RT=1.13 min, MS (ESI) m/z: 704.2 (M+H)$^+$.

Example 238

Intermediate 238A (76 mg, 0.108 mmol) was dissolved in DCM (1 mL) and was treated with TFA (1 ml, 12.98 mmol) at room temperature for 18 h. No product was shown on LCMS. Then mixture was transferred to a microwave vial and was irradiated at 100° C. for 2 h. Then solvent was removed on a rotary evaporator, residue was dissolved in small amount of DCM/MeOH and evaporated. The crude product was purified on prep-HPLC condition D and dried via centrifugal evaporation to afford Example 238 (24 mg, 0.043 mmol, 40%). $^1$H NMR (500 MHz, DMSO-d$_6$) δ 8.73 (d, J=9.9 Hz, 1H), 7.99 (s, 1H), 7.96-7.86 (m, 2H), 7.48-7.38 (m, 3H), 6.86 (br s, 1H), 4.09 (br s, 3H), 4.06 (d, J=4.4 Hz, 2H), 3.36-3.29 (m, 2H), 3.23 (d, J=4.4 Hz, 2H), 2.74 (s, 2H), 2.52 (br s, 3H); LC-MS: method L, RT=1.617 min, MS (ESI) m/z: 554.20 (M+H)$^+$.

Example 239

4-fluoro-N-(2-((2-(7-(1-hydroxyethyl)-2-methoxyquinoxalin-5-yl)-4-methylbenzo[d]thiazol-6-yl)oxy)ethyl)benzenesulfonamide

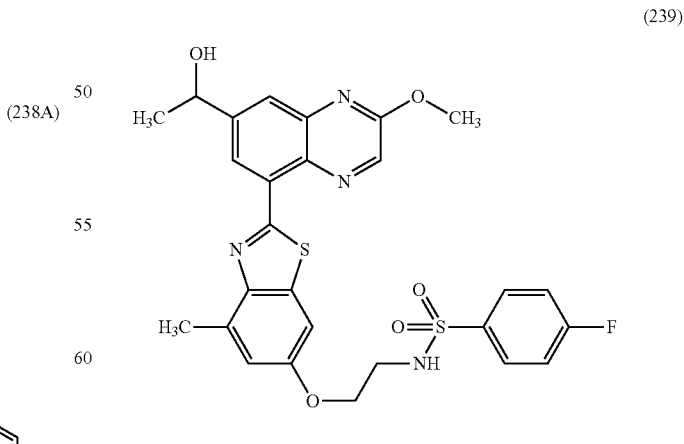

(239)

Intermediate 235A (15 mg, 0.027 mmol) was dissolved in THF (2 mL) and was treated with CH$_3$MgBr in ether (0.018 mL, 0.054 mmol) at −78° C. After addition, the mixture was warmed to room temperature slowly, and a small amount of NH₄Cl (sat., aq.) was added to quench the reaction. 10 mL of EtOAc and 5 mL of water was added to dilute the reaction mixture. After separation, the organic phase was passed through Na₂SO₄ and solvent was removed on a rotary evaporator. The crude material was purified via preparative LC/MS and dried via centrifugal evaporation to yield Example 239 (1.6 mg, 0.0027 mmol, 10%). ¹H NMR (500 MHz, DMSO-d₆) δ 8.78 (d, J=1.9 Hz, 1H), 8.76 (s, 1H), 8.03 (br s, 1H), 7.94-7.87 (m, 3H), 7.46-7.41 (m, 3H), 6.86 (d, J=1.7 Hz, 1H), 5.58 (d, J=4.1 Hz, 1H), 5.09-5.02 (m, 1H), 4.09 (s, 3H), 4.05 (t, J=5.4 Hz, 2H), 3.22 (t, J=5.4 Hz, 2H), 2.73 (s, 3H), 1.49 (d, J=6.6 Hz, 3H); LC-MS: method K, RT=2.119 min, MS (ESI) m/z: 569.2 (M+H)⁺.

Example 240

4-fluoro-N-(2-((2-(7-(hydroxy(phenyl)methyl)-2-methoxyquinoxalin-5-yl)-4-methylbenzo[d]thiazol-6-yl)oxy)ethyl)benzenesulfonamide (240)

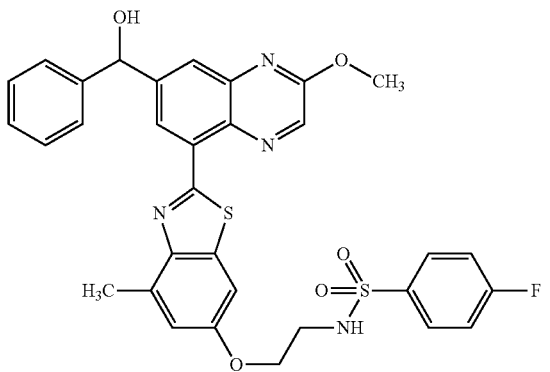

Example 240 was made by following the procedure of Example 239. ¹H NMR (500 MHz, chloroform-d) δ 8.83 (d, J=1.9 Hz, 1H), 8.58 (s, 1H), 7.99 (d, J=1.4 Hz, 1H), 7.94-7.89 (m, 2H), 7.51 (d, J=7.4 Hz, 2H), 7.41-7.35 (m, 2H), 7.31 (d, J=7.4 Hz, 1H), 7.19 (t, J=8.5 Hz, 2H), 7.12 (d, J=2.2 Hz, 1H), 6.81 (d, J=1.7 Hz, 1H), 6.14 (d, J=3.3 Hz, 1H), 4.97 (s, 1H), 4.12 (s, 3H), 4.08 (t, J=5.1 Hz, 2H), 3.46-3.40 (m, 2H), 2.79 (s, 3H), 2.51 (d, J=3.6 Hz, 1H); LC-MS: method L, RT=2.380 min, MS (ESI) m/z: 631.2 (M+H)⁺.

Example 241

4-fluoro-N-(2-((2-(2-methoxy-7-(prop-1-en-2-yl)quinoxalin-5-yl)-4-methylbenzo[d]thiazol-6-yl)oxy)ethyl)benzenesulfonamide (241)

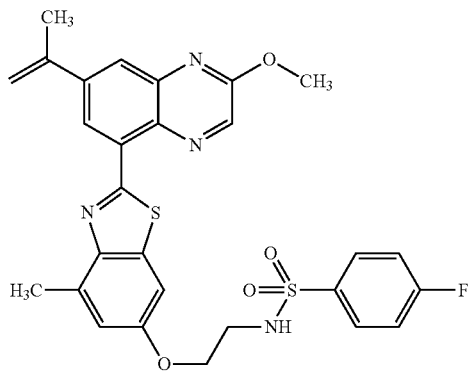

Example 199 (42.5 mg, 0.076 mmol) was dissolved in 1,4-dioxane (1.5 mL) and mixed with 4,4,5,5-tetramethyl-2-(prop-1-en-2-yl)-1,3,2-dioxaborolane (25.6 mg, 0.152 mmol). Na₂CO₃ (1 mL, 2.000 mmol) was added, followed by PdCl₂(dppf)-CH₂Cl₂ adduct (6.21 mg, 7.60 μmol). The mixture was stirred in a microwave at 120° C. for 1 hour. After it cooled to room temperature, the reaction mixture was diluted by adding 15 mL of EtOAc and 10 mL of water. After separation, the organic phase was washed with brine and dried over Na₂SO₄. Removing solvent on a rotary evaporator gave crude product that was purified by flash chromatography (4 g silica column, 0-50% EtOAc/Hexane gradient) to give Example 241 (22 mg, 0.035 mmol, 46.6% yield) as a yellow solid. ¹H NMR (400 MHz, chloroform-d) δ 8.98 (d, J=2.0 Hz, 1H), 8.56 (s, 1H), 8.00-7.90 (m, 3H), 7.24-7.16 (m, 2H), 7.13 (d, J=2.2 Hz, 1H), 6.82 (d, J=1.5 Hz, 1H), 5.75 (s, 1H), 5.36 (s, 1H), 5.03 (t, J=6.1 Hz, 1H), 4.15 (s, 3H), 4.09 (t, J=5.0 Hz, 2H), 3.44 (q, J=5.5 Hz, 2H), 2.82 (s, 3H), 2.35 (s, 3H); LC-MS: method H, RT=1.17 min, MS (ESI) m/z: 565.1 (M+H)⁺.

Example 242

4-fluoro-N-(2-((2-(7-(2-hydroxypropan-2-yl)-2-methoxyquinoxalin-5-yl)-4-methylbenzo[d]thiazol-6-yl)oxy)ethyl)benzenesulfonamide (242)

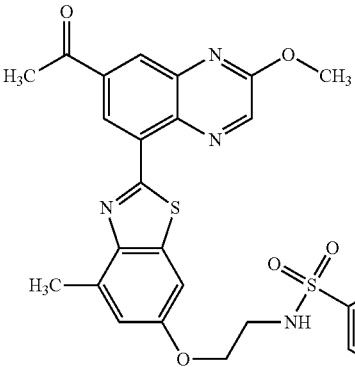

Intermediate 242A: N-(2-((2-(7-acetyl-2-methoxy-quinoxalin-5-yl)-4-methylbenzo[d]thiazol-6-yl)oxy)ethyl)-4-fluorobenzenesulfonamide (242A)

Sodium periodate (22.73 mg, 0.106 mmol) was added into a solution of Example 241 (20 mg, 0.035 mmol), Osmium tetroxide (5.56 μl, 0.708 μmol) in THF (1 ml) and water (0.3 mL), and stirred for 6 h. 10 mL of water and 20 mL of EtOAc was added. After separation, the aqueous layer was extracted with ethyl acetate (10 mL) and then the combined organic phases were washed with sodium thiosulfate solution and brine, dried over sodium sulfate, filtered and concentrated to give Intermediate 242A (20.07 mg, 0.035 mmol, 100% yield) as product. LC-MS: method H, RT=1.14 min, MS (ESI) m/z: 566.8 (M+H)$^+$.

Example 242

Intermediate 242A (20 mg, 0.035 mmol) was dissolved in THF (2 mL) under $N_2$ and was cooled to −78° C. $CH_3MgBr$ (0.047 mL, 0.141 mmol) was added into the reaction mixture slowly. The mixture was warmed to room temperature slowly, and a small amount of $NH_4Cl$ (saturated aq.) was added to quench the reaction. The reaction mixture was diluted by adding 10 mL of EtOAc and 10 mL of water. After separation, the organic phase was concentrated, purified via preparative LC/MS with condition D, and dried via centrifugal evaporation to yield Example 242 (2.4 mg, 0.0038 mmol, 11%). $^1$H NMR (500 MHz, DMSO-$d_6$) δ 8.96 (d, J=1.9 Hz, 1H), 8.76 (s, 1H), 8.06 (br s, 1H), 8.00 (d, J=1.9 Hz, 1H), 7.90 (dd, J=8.8, 5.2 Hz, 2H), 7.45-7.40 (m, 3H), 6.85 (d, J=1.7 Hz, 1H), 5.51 (s, 1H), 4.09 (s, 3H), 4.04 (t, J=5.4 Hz, 2H), 3.21 (t, J=5.1 Hz, 2H), 2.73 (s, 3H), 1.60 (s, 6H); LC-MS: method L, RT=2.183 min, MS (ESI) m/z: 583.2 (M+H)$^+$.

Example 243

(8-(5-fluoro-6-methoxy-4-methylbenzo[d]thiazol-2-yl)-3-methoxyquinoxalin-6-yl) methanol

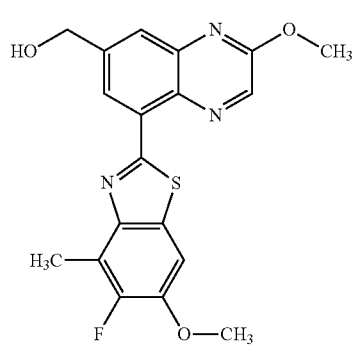

(243)

Intermediate 243A: 5-fluoro-6-methoxy-2-(2-methoxy-7-vinylquinoxalin-5-yl)-4-methylbenzo[d]thiazole

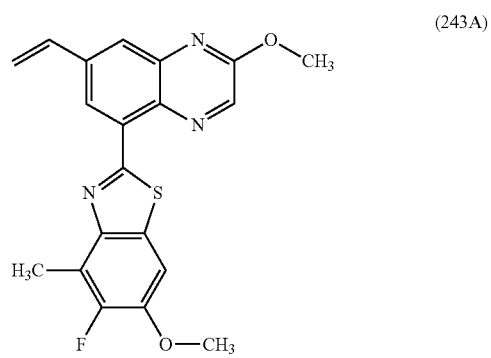 [SMILES: C=Cc1cc(-c2nc3c(C)c(F)c(OC)cc3s2)c2ncc(OC)nc2c1]

(243A)

Intermediate 243A was made by following the procedure in Example 234. LC-MS: method J, RT=1.05 min, MS (ESI) m/z: 382.1 (M+H)$^+$.

Intermediate 243B: 8-(5-fluoro-6-methoxy-4-methylbenzo[d]thiazol-2-yl)-3-methoxyquinoxaline-6-carbaldehyde

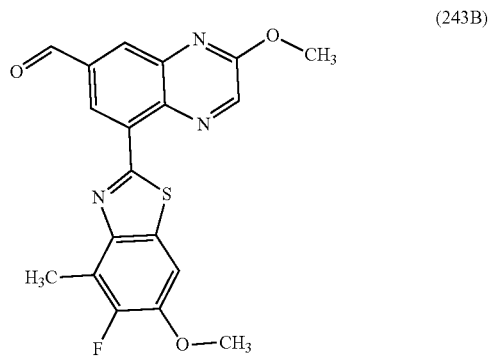 [SMILES: COc1cnc2c(-c3nc4c(C)c(F)c(OC)cc4s3)cc(C=O)cc2n1]

(243B)

Intermediate 243B was made by following the procedure in Intermediate 235A. LC-MS: method J, RT=0.86 min, MS (ESI) m/z: 384.1 (M+H)$^+$.

Example 243

Example 243 was made by following the procedure in Example 235. $^1$H NMR (500 MHz, chloroform-d) δ 8.81 (s, 1H), 8.60 (s, 1H), 7.97 (s, 1H), 7.30 (d, J=7.7 Hz, 1H), 5.02 (d, J=3.0 Hz, 2H), 4.14 (s, 3H), 3.99 (s, 3H), 2.78 (s, 3H), 2.01 (br s, 1H); LC-MS: method L, RT=2.059 min, MS (ESI) m/z: 386.15 (M+H)$^+$.

Examples 244 to 246

Examples 244 to 246 were made by following the general procedure described in Example 239.

Example 244

1-(8-(5-fluoro-6-methoxy-4-methylbenzo[d]thiazol-2-yl)-3-methoxyquinoxalin-6-yl) ethanol

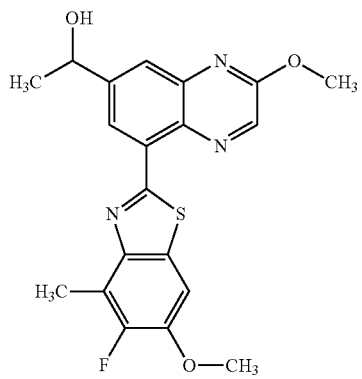

(244)

¹H NMR (500 MHz, DMSO-d₆) δ 8.80 (s, 1H), 8.76 (s, 1H), 7.93 (s, 1H), 7.76 (d, J=7.7 Hz, 1H), 5.61 (br s, 1H), 5.06 (br s, 1H), 4.09 (s, 3H), 3.93 (s, 3H), 2.69 (br s, 3H), 1.49 (d, J=5.8 Hz, 3H); LC-MS: method L, RT=2.234 min, MS (ESI) m/z: 400.15 (M+H)⁺.

Example 245

(8-(5-fluoro-6-methoxy-4-methylbenzo[d]thiazol-2-yl)-3-methoxyquinoxalin-6-yl) (phenyl)methanol

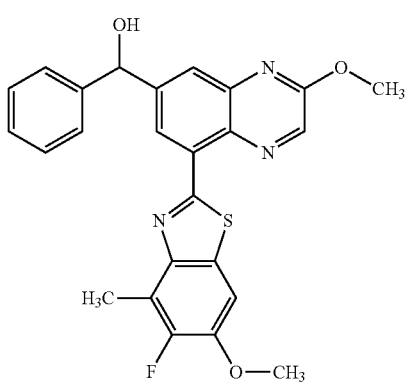

(245)

¹H NMR (500 MHz, DMSO-d₆) δ 8.81 (s, 1H), 8.73 (s, 1H), 7.94 (s, 1H), 7.73 (d, J=8.0 Hz, 1H), 7.51 (d, J=7.4 Hz, 2H), 7.36 (t, J=7.4 Hz, 2H), 7.28-7.22 (m, 1H), 6.35 (br s, 1H), 6.06 (br s, 1H), 4.07 (s, 3H), 3.92 (s, 3H), 2.66 (s, 3H); LC-MS: method L, RT=2.428 min, MS (ESI) m/z: 462.20 (M+H)⁺.

Example 246

Cyclopropyl(8-(5-fluoro-6-methoxy-4-methylbenzo[d]thiazol-2-yl)-3-methoxyquinoxalin-6-yl)methanol

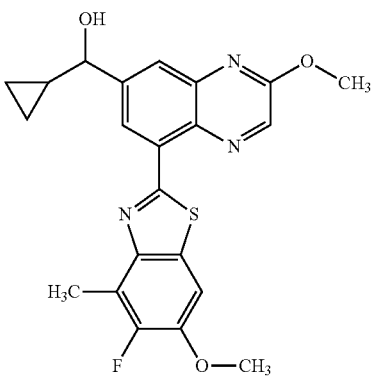

(246)

¹H NMR (500 MHz, DMSO-d₆) δ 8.88 (s, 1H), 8.77 (s, 1H), 7.97 (s, 1H), 7.77 (d, J=8.0 Hz, 1H), 5.62 (br s, 1H), 4.31 (br s, 1H), 4.09 (s, 3H), 3.94 (s, 3H), 2.69 (br s, 3H), 1.28-1.11 (m, 1H), 0.59-0.43 (m, 4H); LC-MS: method L, RT=2.324 min, MS (ESI) m/z: 426.15 (M+H)⁺.

Example 247

4-fluoro-N-(2-((2-(7-fluoro-2-methylquinoxalin-5-yl)-4-methylbenzo[d]thiazol-6-yl) oxy)ethyl)benzenesulfonamide

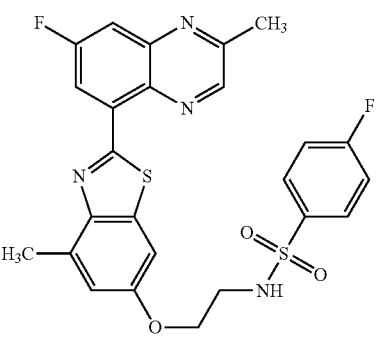

(247)

Example 247 was a side product isolated from the synthesis of Example 207. ¹H NMR (400 MHz, chloroform-d) δ 8.86 (s, 1H), 8.80 (dd, J=9.8, 3.0 Hz, 1H), 7.99-7.90 (m, 2H), 7.73 (dd, J=8.5, 3.0 Hz, 1H), 7.21 (t, J=8.6 Hz, 2H), 7.16 (d, J=2.4 Hz, 1H), 6.85 (s, 1H), 5.03-4.96 (m, 1H), 4.11 (t, J=5.0 Hz, 2H), 3.45 (q, J=5.6 Hz, 2H), 2.84 (s, 3H), 2.82 (s, 3H); LC-MS: method J, RT=1.15 min, MS (ESI) m/z: 527.1 (M+H)⁺.

Example 248

(8-(5-fluoro-6-isopropoxybenzo[d]thiazol-2-yl)-3-methoxyquinoxalin-6-yl)methanol

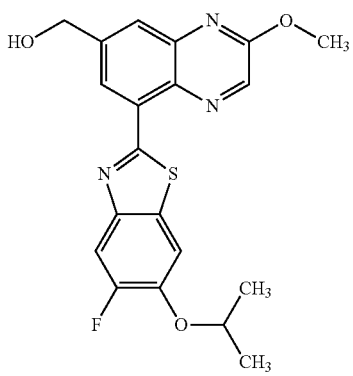

(248)

Example 248 was prepared from Intermediate I-35 by following the procedure described in Example 199. ¹H NMR (500 MHz, DMSO-$d_6$) δ 8.69 (s, 1H), 8.67 (s, 1H), 7.92 (d, J=3.7 Hz, 1H), 7.90 (s, 1H), 7.87 (s, 1H), 4.80 (d, J=5.8 Hz, 2H), 4.72 (dt, J=12.1, 6.0 Hz, 1H), 4.06 (s, 3H), 1.35 (d, J=6.1 Hz, 6H); LC-MS: method L, RT=2.16 min, MS (ESI) m/z: 399.95 (M+H)⁺.

Example 249

N-(2-((2-(7-chloro-2-methoxyquinoxalin-5-yl)-4-methylbenzo[d]thiazol-6-yl)oxy) ethyl)pyridine-3-sulfonamide

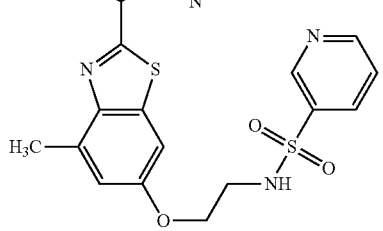

(249)

Intermediate 249A: tert-butyl (2-((2-(7-chloro-2-methoxyquinoxalin-5-yl)-4-methylbenzo[d]thiazol-6-yl)oxy)ethyl)carbamate

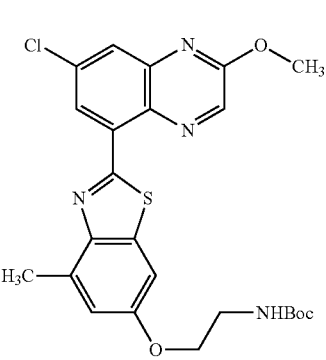

(249A)

Intermediate 249A was made from Intermediate I-28 and Intermediate I-5D by following the procedure described in Example 199. LC-MS: method J, RT=1.28 min, MS (ESI) m/z: 501.1 (M+H)⁺.

Intermediate 249B: 2-((2-(7-chloro-2-methoxyquinoxalin-5-yl)-4-methylbenzo[d]thiazol-6-yl)oxy)ethanamine, TFA Salt

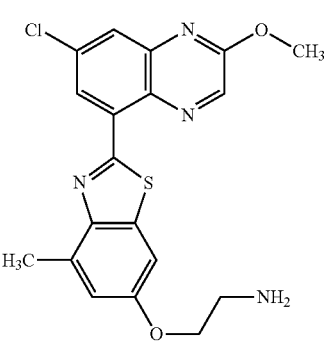

(249B)

Intermediate 249A (237 mg, 0.473 mmol) was dissolved in DCM (2 mL) and was treated with TFA (1 mL, 12.98 mmol) at room temperature for 1 hour. After 1 hour, the solvent was removed on a rotary evaporator and the residue coevaporated with DCM (3×). The residue was dried in vacuo and the crude product was used in the next step without further purification. LC-MS: method H, RT=1.04 min, MS (ESI) m/z: 400.7 (M+H)⁺.

Example 249

Intermediate 249B (20 mg, 0.050 mmol) was suspended in DCM (4 mL). Pyridine-3-sulfonyl chloride hydrochloride (16.02 mg, 0.075 mmol) was added, followed by DIEA (0.035 mL, 0.200 mmol) and the mixture was stirred at room temperature for 30 minutes. Solvent was removed and the crude material was purified via preparative LC/MS with condition C to yield Example 249 (3.5 mg, 0.0064, 13%). ¹H NMR (500 MHz, DMSO-$d_6$) δ 9.00 (d, J=1.9 Hz, 1H), 8.81 (dd, J=4.8, 1.2 Hz, 1H), 8.77 (s, 1H), 8.61 (d, J=2.2 Hz, 1H), 8.26 (t, J=5.8 Hz, 1H), 8.22 (dt, J=8.3, 1.8 Hz, 1H), 8.01 (d, J=2.5 Hz, 1H), 7.63 (dd, J=7.8, 4.8 Hz, 1H), 7.41 (d, J=2.5 Hz, 1H), 6.82 (d, J=1.4 Hz, 1H), 4.08 (s, 3H), 4.06 (t, J=5.2 Hz, 2H), 3.29 (m, 2H), 2.70 (s, 3H); LC-MS: method L, RT=2.554 min, MS (ESI) m/z: 542.15 (M+H)+.

Example 250

Ethyl 2-((2-(7-chloro-2-methoxyquinoxalin-5-yl)-4-methylbenzo[d]thiazol-6-yl)oxy) acetate

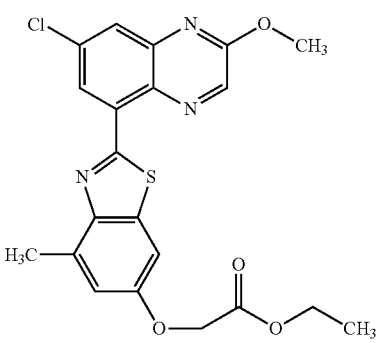

(250)

Example 250 was prepared from Intermediate I-28 and Intermediate I-39 by following the procedure described in Example 199. ¹H NMR (400 MHz, chloroform-d) δ 8.81 (d, J=2.4 Hz, 1H), 8.60 (s, 1H), 7.93 (d, J=2.4 Hz, 1H), 7.23 (d, J=2.2 Hz, 1H), 7.01 (dd, J=2.4, 0.9 Hz, 1H), 4.71 (s, 2H), 4.31 (q, J=7.3 Hz, 2H), 4.14 (s, 3H), 2.84 (s, 3H), 1.33 (t, J=7.2 Hz, 3H); LC-MS: method L, RT=2.834 min, MS (ESI) m/z: 444.10 (M+H)+.

Example 251

2-((2-(7-chloro-2-methoxyquinoxalin-5-yl)-4-methylbenzo[d]thiazol-6-yl)oxy)acetic acid

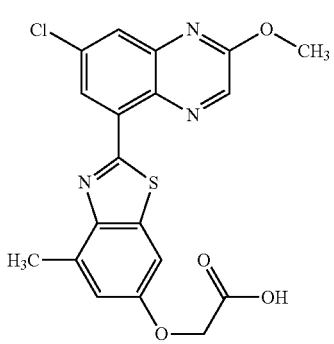

(251)

Example 251 was another product isolated during purification of 250. ¹H NMR (500 MHz, chloroform-d) δ 8.81 (d, J=2.2 Hz, 1H), 8.60 (s, 1H), 7.94 (d, J=1.9 Hz, 1H), 7.27 (s, 1H), 7.02 (s, 1H), 4.77 (s, 2H), 4.14 (s, 3H), 2.85 (s, 3H); LC-MS: method L, RT=2.398 min, MS (ESI) m/z: 416.05 (M+H)+.

Example 252

2-((2-(7-(hydroxymethyl)-2-methoxyquinoxalin-5-yl)-4-methylbenzo[d]thiazol-6-yl)oxy)ethyl (6-methoxypyridin-3-yl)carbamate

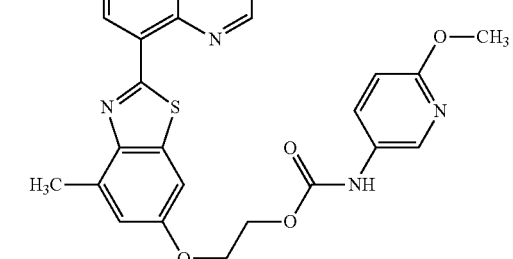

(252)

Intermediate 252A: 2-((2-(7-chloro-2-methoxyquinoxalin-5-yl)-4-methylbenzo[d]thiazol-6-yl)oxy)ethanol

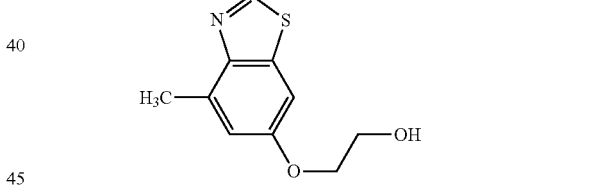

(252A)

Example 250 (230 mg, 0.518 mmol) was dissolved in 1,4-dioxane (5 mL) and was cooled to 0° C. under N₂. The mixture was treated with LiBH₄ (16.93 mg, 0.777 mmol) at room temperature for 18 h. On the next morning, a small amount of saturated NH₄Cl (aq.) was added to quench the reaction. The reaction mixture was diluted by adding 50 mL of EtOAc and 20 mL of water. After shaking and separation, 30 mL of EtOAc was used to extract the aqueous phase. The combined organic phases were dried over Na₂SO₄, filtered, and concentrated to give Intermediate 252A, which was used without purification. LC-MS: method H, RT=0.93 min, MS (ESI) m/z: 402.1 (M+H)+.

Intermediate 252B: 2-((2-(2-methoxy-7-vinylqui-noxalin-5-yl)-4-methylbenzo[d]thiazol-6-yl)oxy)ethanol

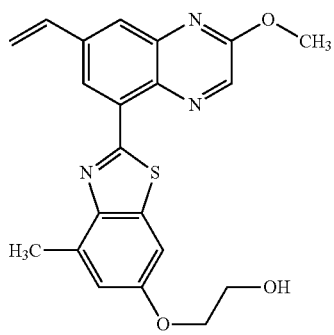

(252B)

Intermediate 252B was prepared from Intermediate 252A by following procedure described in Example 229. LC-MS: method J, RT=0.81 min, MS (ESI) m/z: 394.1 (M+H)+.

Intermediate 252C: 2-((2-(2-methoxy-7-vinylqui-noxalin-5-yl)-4-methylbenzo[d]thiazol-6-yl)oxy)ethyl carbonochloridate

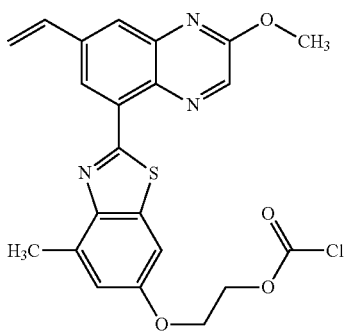

(252C)

Phosgene in toluene (0.922 mL, 1.398 mmol) was added dropwise to Intermediate 252B (110 mg, 0.280 mmol) dissolved in anhydrous THF (10 mL). The mixture was stirred at room temperature for 4 hours. Solvent was removed by rotary evaporator and the residue was used in the next step without purification. LC-MS: method J, RT=1.10 min, MS (ESI) m/z: 456.1 (M+H)+.

Intermediate 252D: 2-((2-(2-methoxy-7-vinylqui-noxalin-5-yl)-4-methylbenzo[d]thiazol-6-yl)oxy)ethyl (6-methoxypyridin-3-yl)carbamate

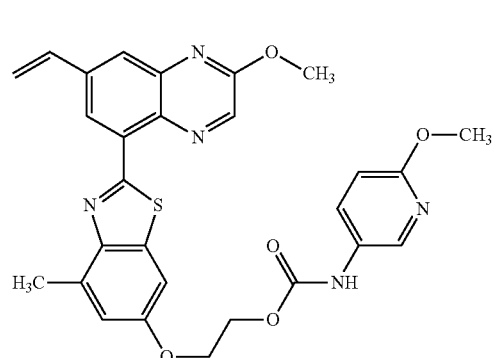

(252D)

Intermediate 252C (30 mg, 0.066 mmol) was mixed with DIEA (0.046 mL, 0.263 mmol) in DCM (1 mL) and 6-methoxypyridin-3-amine (24.51 mg, 0.197 mmol) was added. The mixture was stirred at room temperature for 18 hours. On the next day, the reaction mixture was purified by flash chromatography (12 g silica column, 0-100% EtOAc/Hexane gradient), and the product was purified again by preparative HPLC with method B and dried on a lyophilizer to give Intermediate 252D (5.6 mg, 10.30 μmol, 15.66% yield) as a yellow solid. LC-MS: method H, RT=1.21 min, MS (ESI) m/z: 544.1 (M+H)+.

Intermediate 252E: 2-((2-(7-formyl-2-methoxyqui-noxalin-5-yl)-4-methylbenzo[d]thiazol-6-yl)oxy)ethyl (6-methoxypyridin-3-yl)carbamate (252E)

Intermediate 252E was prepared from Intermediate 252D by following the procedure described in Intermediate 235A. LC-MS: method H, RT=1.11 min, MS (ESI) m/z: 545.8 (M+H)+.

Example 252

Example 252 was prepared from Intermediate 252E by following the procedure described in Example 235. ¹H NMR (500 MHz, DMSO-d₆) δ 9.77 (br s, 1H), 8.75 (s, 1H), 8.72 (d, J=1.7 Hz, 1H), 8.24 (br s, 1H), 7.91 (d, J=0.8 Hz, 1H), 7.78 (d, J=7.4 Hz, 1H), 7.57 (d, J=2.2 Hz, 1H), 7.03 (d, J=1.7 Hz, 1H), 6.78 (d, J=8.8 Hz, 1H), 5.61 (t, J=5.8 Hz, 1H), 4.83 (d, J=5.8 Hz, 2H), 4.54-4.41 (m, 2H), 4.40-4.27 (m, 2H), 4.09 (s, 3H), 3.80 (s, 3H), 2.75 (s, 3H); LC-MS: method L, RT=1.955 min, MS (ESI) m/z: 548.2 (M+H)+.

Example 253

6-methoxy-2-(2-(methoxymethyl)-7-methylquinoxalin-5-yl)benzo[d]thiazole

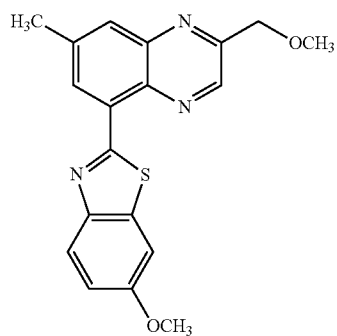

(253)

Intermediate 253A:
2-bromo-6-methoxybenzo[d]thiazole

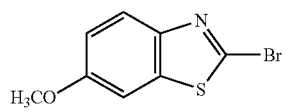

(253A)

To a black solution of Copper (II) bromide (149 mg, 0.666 mmol) in Acetonitrile (1 mL) was added t-Butyl nitrite (0.095 mL, 0.721 mmol) at room temperature followed by 6-methoxybenzo[d]thiazol-2-amine (100 mg, 0.555 mmol). Immediate bubbling and a mild exotherm was observed upon benzothiazole addition. After 3 hours, the reaction mixture was diluted with EtOAc and washed with 1.0 M HCl, saturated NaHCO₃, and then Brine. The organic phase was dried over MgSO₄, filtered and concentrated to a reddish-brown solid. The crude material was purified by ISCO flash chromatography (0-15% EtOAc/Hex over 20 min, 12 g silica gel cartridge, Product at 5%). The desired fractions were combined and concentrated to yield Intermediate 253A (84 mg, 0.344 mmol, 62.0% yield) as an off-white solid. LC-MS: Method H, RT=1.12 min, MS (ESI) m/z: 244.0, 246.0 (M+H)+. ¹H NMR (400 MHz, CHLOROFORM-d) δ 7.89 (d, J=9.0 Hz, 1H), 7.28 (1H under CDCl₃), 7.09 (dd, J=9.0, 2.6 Hz, 1H), 3.90 (s, 3H)

Example 253

Intermediate I-2 (19.2 mg, 0.061 mmol) and Intermediate 253A (15.78 mg, 0.065 mmol) were solvated in DMF (1 mL). PdCl₂(dppf)-CH₂Cl₂ adduct (2.82 mg, 3.45 μmol) was added and the solution was degassed by sparging with argon for 10 min. Sodium carbonate (9.14 mg, 0.086 mmol) was then added, followed by water (0.100 mL), and the solution was further degassed for an additional 5 min. The vial was sealed and heated to 100° C. in the microwave for 30 min. The crude solution was filtered and purified by preparative HPLC (Method D, 40-80% over 20 minutes) to yield Example 253 (6.7 mg, 0.019 mmol, 43.8% yield). LC-MS: Method H, RT=1.31 min, MS (ESI) m/z: 353.2 (M+H)+. ¹H NMR (400 MHz, CHLOROFORM-d) δ 7.89 (d, J=9.0 Hz, 1H), 7.28 (1H Under CDCl₃), 7.09 (dd, J=9.0, 2.6 Hz, 1H), 3.90 (s, 3H).

Example 254

4-fluoro-6-methoxy-2-(2-(methoxymethyl)-7-methylquinoxalin-5-yl)benzo[d]thiazole

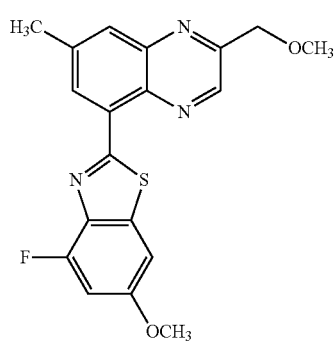

(254)

Intermediate 254A: 4-fluoro-6-methoxybenzo[d]thiazol-2-amine

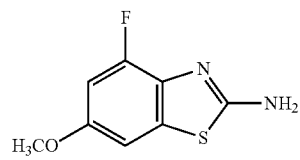

(254A)

To a solution of 2-fluoro-4-methoxyaniline (150 mg, 1.063 mmol) in Acetonitrile (5.314 mL) was added ammonium thiocyanate (121 mg, 1.594 mmol). The mixture was stirred at room temperature for 5 min until fully solvated. Benzyltrimethylammonium tribromide (414 mg, 1.063 mmol) was then added at room temperature causing the solution to take on a bright yellow color with solids precipitating. The mixture was allowed to stir at room temperature overnight, at which point LCMS indicated complete conversion. The mixture was diluted with EtOAc and washed with saturated sodium bicarbonate. The organic layer was collected, washed with brine, dried over magnesium sulfate, filtered and concentrated. The crude material was purified by ISCO (0-10% DCM/MeOH over 20 min using a 24 g silica gel cartridge) to give Intermediate 254A (101 mg, 0.510 mmol, 47.9% yield). LC-MS: Method H, RT=0.77 min, MS (ESI) m/z: 199.1 (M+H)+. ¹H NMR (400 MHz, METHANOL-d₄) δ 7.01 (d, J=2.0 Hz, 1H), 6.67 (dd, J=12.4, 2.3 Hz, 1H), 3.78 (s, 3H), 3.33-3.28 (m, 2H).

619

Intermediate 254B: 4-fluoro-6-methoxybenzo[d]thiazol-2-amine

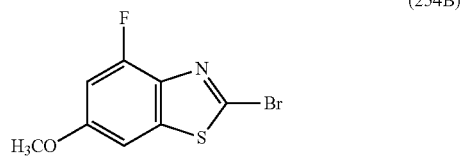

(254B)

To a dark green solution of Copper (II) bromide (125 mg, 0.560 mmol) and Intermediate 254A (101 mg, 0.510 mmol) solvated in acetonitrile (1 mL) and THF (2 mL) was added t-butyl nitrite (0.088 mL, 0.662 mmol). After stirring for 4 h at room temperature, the mixture was dilute with EtOAc and washed with 1.0 M HCl followed by Brine. The organic phase was concentrated and purified by ISCO flash chromatography (0-10% EtOAc/Hex over 20 min, 24 g silica gel cartridge-product at 5%) to afford Intermediate 254B (63 mg, 0.240 mmol, 47.2% yield) as a white solid. LC-MS: Method H, RT=1.17 min, MS (ESI) m/z: 262.0, 264.0 (M+H)$^+$. $^1$H NMR (400 MHz, CHLOROFORM-d) δ 7.05 (dd, J=2.2, 0.9 Hz, 1H), 6.83 (dd, J=11.6, 2.3 Hz, 1H), 3.87 (s, 3H).

Example 254

Intermediate I-2 (19.2 mg, 0.061 mmol) and Intermediate 254B (14.68 mg, 0.056 mmol) were solvated in DMF (1 mL). PdCl$_2$(dppf)-CH$_2$Cl$_2$ adduct (2.82 mg, 3.45 μmol) was added and the solution was degassed by bubbling argon for 10 min. Sodium Carbonate (2.0 M in H$_2$O) (100 μL, 0.200 mmol) was then added, and the solution was further degassed for an additional 5 min. The microwave vial was sealed and heated to 100° C. in the microwave for 30 min. The crude reaction mixture was diluted with Et$_2$O and washed with water followed by brine. The organic phase was concentrated and purified by ISCO (24 g, 0-50% EtOAc/Hex, 18 min—recovered SM at 10%, Product at 20%). Example 254 (2.2 mg, 5.78 μmol, 13.40% yield) was isolated as a bright yellow solid. LC-MS: Method H, RT=1.37 min, MS (ESI) m/z: 370.1 (M+H)$^+$. $^1$H NMR (400 MHz, CHLOROFORM-d) δ 9.09 (s, 1H), 8.94 (s, 1H), 7.97 (s, 1H), 7.29-7.21 (m, 2H under CDCl$_3$), 6.88 (dd, J=11.8, 2.3 Hz, 1H), 4.86 (s, 2H), 3.93 (s, 3H), 3.59 (s, 3H), 2.71 (s, 3H).

Example 255

6-ethoxy-2-(2-(methoxymethyl)-7-methylquinoxalin-5-yl)benzo[d]thiazole

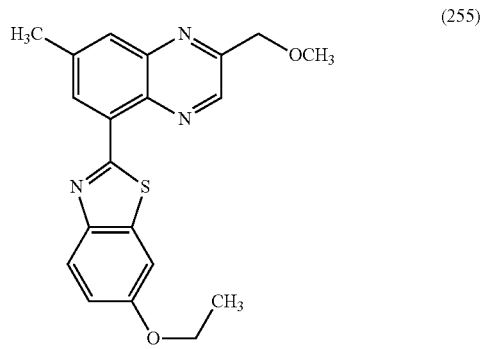 [SMILES: CCOc1ccc2nc(-c3cc(C)cc4nc(COC)cnc34)sc2c1]

(255)

620

Intermediate 255A: 2-bromo-6-ethoxybenzo[d]thiazole

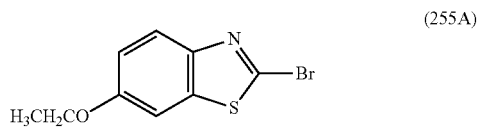

(255A)

To a solution of Copper (II) bromide (138 mg, 0.618 mmol) in acetonitrile (1 mL) was added t-butyl nitrite (0.088 mL, 0.669 mmol) at room temperature followed by 6-ethoxybenzo[d]thiazol-2-amine (100 mg, 0.515 mmol). The reaction mixture was heated to 50° C. for 45 min. The mixture was cooled to room temperature, diluted with EtOAc and washed with 1.0 M HCl followed by brine. The organic phase was dried over MgSO$_4$, filtered and concentrated. The crude material was purified by ISCO (24 g, 0-15% EtOAc/Hex). Example 255A (62 mg, 0.240 mmol, 46.7% yield) was isolated as a light brown solid. LC-MS: Method H, RT=1.19 min, MS (ESI) m/z: 258.2, 260.2 (M+H)$^+$. $^1$H NMR (400 MHz, CHLOROFORM-d) δ 7.86 (d, J=9.0 Hz, 1H), 7.24 (d, J=2.4 Hz, 1H), 7.06 (dd, J=8.9, 2.3 Hz, 1H), 4.09 (q, J=7.0 Hz, 2H), 1.46 (t, J=6.9 Hz, 3H).

Example 255

Intermediate I-2 (19.2 mg, 0.061 mmol) and Intermediate 255A (16.69 mg, 0.065 mmol) were solvated in DMF (1 mL). PdCl$_2$(dppf)-CH$_2$Cl$_2$ adduct (2.82 mg, 3.45 μmol) was added and the solution was degassed by bubbling argon for 10 min. Sodium Carbonate (2.0 M in H$_2$O) (100 μL, 0.200 mmol) was then added, and the solution was further degassed for an additional 5 min. The vial was sealed and heated to 100° C. in the microwave for 30 min in the microwave. The crude solution was filtered and purified by preparative HPLC (Method D, 50-90% over 10 minutes) to yield Example 255 (5.4 mg, 0.015 mmol, 34.3% yield). LC-MS: Method H, RT=1.38 min, MS (ESI) m/z: 366.2 (M+H)$^+$. $^1$H NMR (400 MHz, CHLOROFORM-d) δ 7.89 (d, J=9.0 Hz, 1H), 7.28 (1H Under CDCl$_3$), 7.09 (dd, J=9.0, 2.6 Hz, 1H), 3.90 (s, 3H).

Example 256

2-(2-(methoxymethyl)-7-methylquinoxalin-5-yl)benzo[d]thiazole

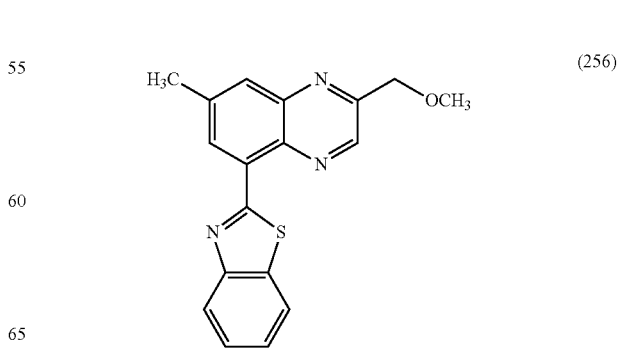

(256)

Intermediate 256A:
2-bromo-6-ethoxybenzo[d]thiazole

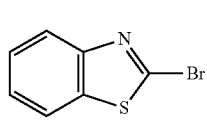

(256A)

To a solution of copper (II) bromide (134 mg, 0.600 mmol) in Acetonitrile (1 mL) was added benzo[d]thiazol-2-amine (100 mg, 0.666 mmol) at room temperature. t-Butyl nitrite (0.106 mL, 0.800 mmol) was then added. Bubbling immediately observed. After 30 min, diluted with EtOAc and washed with 1.0 M HCl followed by brine. The organic phase was concentrated and purified by ISCO flash chromatography (0-5% EtOAc/Hex over 20 min, 24 g silica gel cartridge—product at 2.5%) to afford Intermediate 256A (80 mg, 0.374 mmol, 56.1% yield) as a pink oil. LC-MS: Method H, RT=1.16 min, MS (ESI) m/z: 214.0, 216.0 (M+H)$^+$. $^1$H NMR (400 MHz, CHLOROFORM-d) δ 8.00 (d, J=8.1 Hz, 1H), 7.82 (d, J=7.9 Hz, 1H), 7.53-7.37 (m, 2H).

Example 256

Intermediate I-2 (19.2 mg, 0.061 mmol) and Intermediate 256A (10.0 mg, 0.047 mmol) were solvated in DMF (1 mL). PdCl$_2$(dppf)-CH$_2$Cl$_2$ adduct (3.05 mg, 3.74 μmol) was added and the solution was degassed by bubbling argon for 10 min. Sodium Carbonate (2.0 M in H$_2$O) (100 μL, 0.200 mmol) was then added, and the solution was further degassed for an additional 5 min. The vial was sealed and heated to 100° C. in the microwave for 30 min. The crude solution was filtered and purified by preparative HPLC (Method D, 45-90% over 10 minutes) to yield 256 (3.2 mg, 0.008 mmol, 34.3% yield). LC-MS: Method H, RT=1.37 min, MS (ESI) m/z: 322.0 (M+H)$^+$. $^1$H NMR (500 MHz, DMSO-d$_6$) δ 9.11 (s, 1H), 8.87 (s, 1H), 8.21 (d, J=8.0 Hz, 1H), 8.14 (d, J=8.0 Hz, 1H), 8.07 (s, 1H), 7.58 (t, J=7.7 Hz, 1H), 7.52-7.46 (m, 1H), 4.82 (s, 2H), 3.47 (s, 3H), 2.70 (s, 3H).

Example 257

4,6-difluoro-2-(2-(methoxymethyl)-7-methylquinoxalin-5-yl)benzo[d]thiazole

Intermediate 257A:
2-bromo-4,6-difluorobenzo[d]thiazole

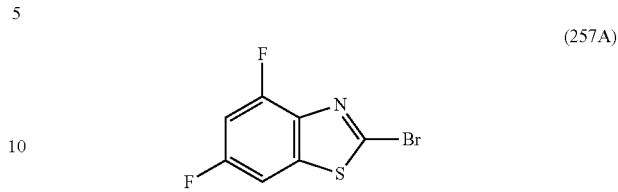

(257A)

To a black solution of copper (II) bromide (144 mg, 0.645 mmol) in Acetonitrile (1 mL) was added t-Butyl nitrite (0.092 mL, 0.698 mmol) followed by 4,6-difluorobenzo[d]thiazol-2-amine (100 mg, 0.537 mmol). The reaction mixture was heated to 50° C. After 40 min, the reaction mixture was cooled to room temperature, diluted with EtOAc and washed with 1.0 M HCl followed by brine. The crude material was concentrated and purified by flash chromatography (0-15% EtOAc/Hex over 18 min, 12 g silica gel cartridge). The desired fractions were combined and concentrated to yield Intermediate 257A (126 mg, 0.504 mmol, 94% yield) as a white solid. LC-MS: Method H, RT=1.14 min, MS (ESI) m/z: None (M+H)$^+$. $^1$H NMR (400 MHz, CHLOROFORM-d) δ 7.35 (d, J=7.5 Hz, 1H), 7.03 (td, J=9.6, 2.2 Hz, 1H). $^{19}$F NMR (CHLOROFORM-d) δ −85.7, −91.7

Example 257

Intermediate I-2 (15.1 mg, 0.048 mmol), PdCl$_2$(dppf)-CH$_2$Cl$_2$ adduct (2.61 mg, 3.20 μmol) and Intermediate 257A (10 mg, 0.040 mmol) were solvated in DMF (1 mL). Sodium carbonate (2.0 M in H$_2$O) (100 μL, 0.200 mmol) was added, and the solution was degassed with argon for 10 min. The vial was then sealed and heated to 100° C. in the microwave for 30 min. The crude solution was filtered and purified by preparative HPLC (Method D, 45-85% over 10 minutes) to yield Example 257 (8.3 mg, 0.021 mmol, 52.3% yield). LC-MS: Method H, RT=1.41 min, MS (ESI) m/z: 358.0 (M+H)$^+$. $^1$H NMR (500 MHz, DMSO-d$_6$) δ 9.10 (s, 1H), 8.84 (s, 1H), 8.09 (s, 1H), 8.03-7.97 (m, 1H), 7.51 (t, J=9.4 Hz, 1H), 4.82 (s, 2H), 3.47 (s, 3H), 2.70 (s, 3H).

Example 258

4,6-dimethoxy-2-(2-(methoxymethyl)-7-methylquinoxalin-5-yl)benzo[d]thiazole

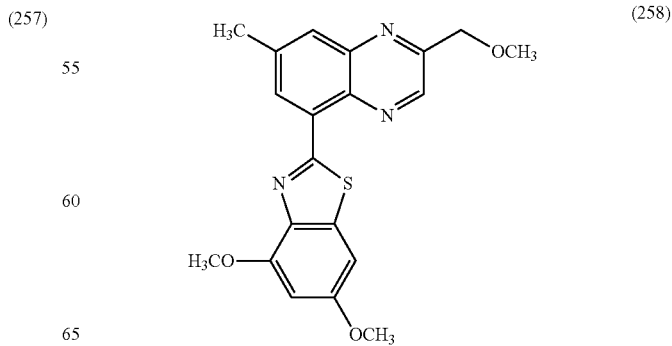

(258)

Intermediate 258A:
2-bromo-4,6-dimethoxybenzo[d]thiazole

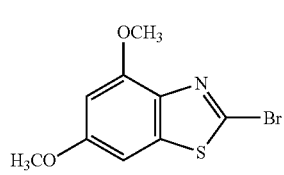
(258A)

To a solution of copper (II) bromide (127 mg, 0.571 mmol) in acetonitrile (1 mL) was added 4,6-dimethoxybenzo[d]thiazol-2-amine (100 mg, 0.476 mmol) at room temperature. t-Butyl nitrite (0.082 mL, 0.618 mmol) was then added dropwise at room temperature causing immediate bubbling. After 1 hr, the reaction mixture was diluted with EtOAc and washed with 1.0 M HCl. The organic phase was dried over MgSO$_4$, filtered and concentrated. The crude material was purified by ISCO flash chromatography (0-30% EtOAc/Hex over 35 min, 12 g silica gel cartridge). Intermediate 258A (56 mg, 0.204 mmol, 43% yield) as a white solid. LC-MS: Method H, RT=1.13 min, MS (ESI) m/z: 274.0, 276.0 (M+H)$^+$. $^1$H NMR (400 MHz, CHLOROFORM-d) δ 6.81 (d, J=2.0 Hz, 1H), 6.52 (d, J=2.2 Hz, 1H), 3.99 (s, 3H), 3.86 (s, 3H).

Example 258

Intermediate I-2 (13.8 mg, 0.044 mmol), PdCl$_2$(dppf)-CH$_2$Cl$_2$ adduct (2.38 mg, 2.92 μmol) and Intermediate 258A (10 mg, 0.036 mmol) were solvated in DMF (1 mL). Sodium carbonate (2.0 M in H$_2$O) (100 μL, 0.200 mmol) was added, and the solution was degassed with argon for 10 min. The vial was then sealed and heated to 100° C. in the microwave for 30 min. The crude solution was filtered and purified by preparative HPLC (Method D, 45-85% over 10 minutes) to yield Example 258 (6.4 mg, 0.015 mmol, 41.9% yield). LC-MS: Method H, RT=1.29 min, MS (ESI) m/z: 382.0 (M+H)$^+$. $^1$H NMR (500 MHz, DMSO-d$_6$) δ 9.09 (s, 1H), 8.77 (s, 1H), 8.02 (s, 1H), 7.29 (s, 1H), 6.68 (s, 1H), 4.81 (s, 2H), 4.00 (s, 3H), 3.87 (s, 3H), 3.47 (s, 3H), 2.69 (s, 3H).

Example 259

4-methoxy-2-(2-(methoxymethyl)-7-methylquinoxalin-5-yl)benzo[d]thiazole

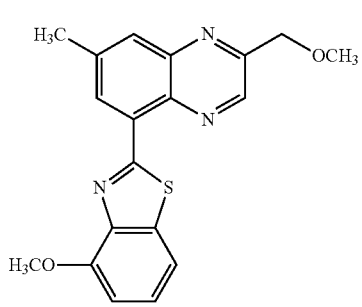
(259)

Intermediate 259A:
2-bromo-4-methoxybenzo[d]thiazole

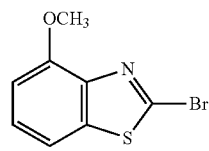
(259A)

Copper (II) bromide (112 mg, 0.499 mmol) and 4-methoxybenzo[d]thiazol-2-amine (100 mg, 0.555 mmol) were solvated in Acetonitrile (1 mL) t-Butyl nitrite (0.081 mL, 0.610 mmol) was added at room temperature. After 30 min, the reaction mixture was dilute with EtOAc and washed with 1.0 M HCl followed by brine. The crude material was concentrated and purified by ISCO flash chromatography (0-10% EtOAc/Hex over 20 min, 24 g silica gel cartridge) to afford Intermediate 259A (68 mg, 0.279 mmol, 50.2% yield). LC-MS: Method H, RT=1.12 min, MS (ESI) m/z: 242.0. 244.0 (M+H)$^+$. $^1$H NMR (400 MHz, CHLOROFORM-d) δ 7.39-7.36 (m, 2H), 6.92 (dd, J=6.2, 2.9 Hz, 1H), 4.05 (s, 3H).

Example 259

Intermediate I-2 (15.4 mg, 0.049 mmol), PdCl$_2$(dppf)-CH$_2$Cl$_2$ adduct (2.68 mg, 3.28 μmol) and Intermediate 259A (10 mg, 0.041 mmol) were solvated in DMF (1 mL). Sodium Carbonate (2.0 M in H$_2$O) (100 μL, 0.200 mmol) was added, and the solution was degassed with argon for 10 min. The vial was then sealed and heated to 100° C. in the microwave for 30 min. The crude solution was filtered and purified by preparative HPLC (Method D, 45-85% over 10 minutes) to yield Example 259 (4.1 mg, 0.012 mmol, 28.5% yield). LC-MS: Method H, RT=1.30 min, MS (ESI) m/z: 352.1 (M+H)$^+$. $^1$H NMR (500 MHz, DMSO-d$_6$) δ 9.10 (s, 1H), 8.84 (s, 1H), 8.06 (s, 1H), 7.73 (d, J=8.0 Hz, 1H), 7.43 (t, J=8.0 Hz, 1H), 7.09 (d, J=8.0 Hz, 1H), 4.82 (s, 2H), 4.03 (s, 3H), 3.47 (s, 3H), 2.71 (s, 3H).

Example 260

4-chloro-2-(2-(methoxymethyl)-7-methylquinoxalin-5-yl)benzo[d]thiazole

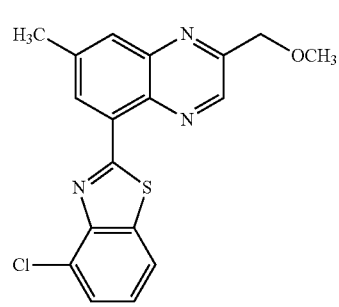
(260)

Intermediate 260A:
2-bromo-4-chlorobenzo[d]thiazole

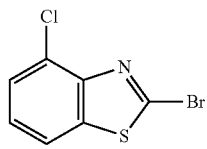
(260A)

Copper (II) bromide (134 mg, 0.600 mmol) and 4-chlorobenzo[d]thiazol-2-amine (100 mg, 0.542 mmol) were solvated in acetonitrile (1 mL) and THF (1 mL). t-Butyl nitrite (0.086 mL, 0.650 mmol) was then added at room temperature. After 30 min, the reaction mixture was dilute with EtOAc and washed with 1.0 M HCl followed by brine. The crude material was concentrated and purified by ISCO flash chromatography (0-5% EtOAc/Hex over 20 min, 24 g silica gel cartridge, product at 2.5%) to afford Intermediate 260A (88 mg, 0.279 mmol, 65.4% yield). LC-MS: Method H, RT=1.20 min, MS (ESI) m/z: 248.0. 250.0, 252.1 (M+H)$^+$. $^1$H NMR (400 MHz, CHLOROFORM-d) δ 7.72 (d, J=7.9 Hz, 1H), 7.52 (d, J=7.9 Hz, 1H), 7.41-7.33 (m, 1H).

Example 260

Intermediate I-2 (15.1 mg, 0.048 mmol), PdCl$_2$(dppf)-CH$_2$Cl$_2$ adduct (2.63 mg, 3.22 µmol) and Intermediate 260A (10 mg, 0.040 mmol) were solvated in DMF (1 mL). Sodium Carbonate (2.0 M in H$_2$O) (100 µL, 0.200 mmol) was added, and the solution was degassed with argon for 10 min. The vial was then sealed and heated to 100° C. in the microwave for 30 min. The crude solution was filtered and purified by preparative HPLC (Method D, 45-85% over 10 minutes) to yield Example 260 (4.6 mg, 0.012 mmol, 30.5% yield). LC-MS: Method H, RT=1.44 min, MS (ESI) m/z: 356.0, 358.0 (M+H)$^+$. $^1$H NMR (500 MHz, DMSO-d$_6$) δ 9.12 (s, 1H), 8.88 (s, 1H), 8.19 (d, J=7.7 Hz, 1H), 8.11 (s, 1H), 7.67 (d, J=7.7 Hz, 1H), 7.48 (t, J=7.7 Hz, 1H), 4.83 (s, 2H), 3.47 (s, 3H), 2.72 (s, 3H).

Example 261

2-(2-(methoxymethyl)-7-methylquinoxalin-5-yl)-4-methylbenzo[d]thiazole

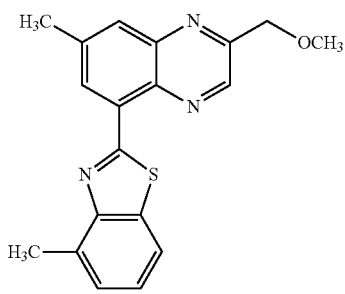
(261)

Intermediate 261A:
2-bromo-4-methylbenzo[d]thiazole

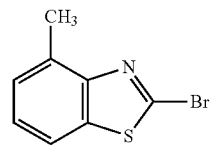
(261A)

Copper (II) bromide (122 mg, 0.546 mmol) and 2-bromo-4-methylbenzo[d] thiazole (100 mg, 0.609 mmol) were solvated in acetonitrile (1 mL) and THF (1 mL). t-Butyl nitrite (0.096 mL, 0.728 mmol) was then added at room temperature. After 30 min, the reaction mixture was dilute with EtOAc and washed with 1.0 M HCl followed by brine. The crude material was concentrated and purified by ISCO flash chromatography (0-5% EtOAc/Hex over 20 min, 24 g silica gel cartridge, product at 2.5%) to afford Intermediate 261A (88 mg, 0.386 mmol, 63.6% yield). LC-MS: Method H, RT=1.25 min, MS (ESI) m/z: 227.9, 229.9 (M+H)$^+$. $^1$H NMR (400 MHz, CHLOROFORM-d) δ 7.64 (dt, J=7.7, 0.8 Hz, 1H), 7.34-7.27 (m, 2H), 2.72 (s, 3H).

Example 261

Intermediate I-2 (16.7 mg, 0.053 mmol), PdCl$_2$(dppf)-CH$_2$Cl$_2$ adduct (2.53 mg, 3.10 µmol) and Intermediate 261A (10 mg, 0.044 mmol) were solvated in DMF (1 mL). Sodium Carbonate (2.0 M in H$_2$O) (100 µL, 0.200 mmol) was added, and the solution was degassed with argon for 10 min. The vial was then sealed and heated to 100° C. in the microwave for 30 min. The crude solution was filtered and purified by preparative HPLC (Method D, 55-85% over 10 minutes) to yield Example 261 (4.5 mg, 0.013 mmol, 29.1% yield). LC-MS: Method H, RT=1.52 min, MS (ESI) m/z: 336.1 (M+H)$^+$. $^1$H NMR (500 MHz, DMSO-d$_6$) δ 9.10 (s, 1H), 8.88 (s, 1H), 8.07 (s, 1H), 8.02-7.97 (m, 1H), 7.38 (d, J=3.9 Hz, 2H), 4.82 (s, 2H), 3.47 (s, 3H), 2.81 (s, 3H), 2.71 (s, 3H).

Example 262

2-(2-(methoxymethyl)-7-methylquinoxalin-5-yl)-4-methyl-6-(trifluoromethoxy)benzo[d]thiazole

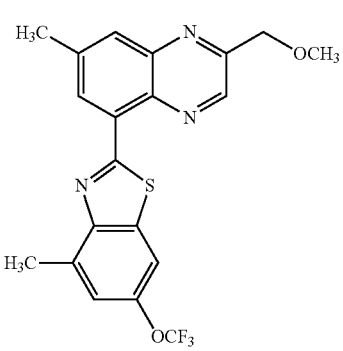
(262)

Intermediate 262A: 4-methyl-6-(trifluoromethoxy)benzo[d]thiazol-2-amine

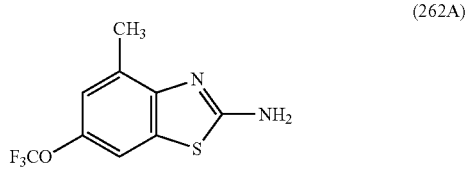 [SMILES: Cc1cc(OC(F)(F)F)cc2sc(N)nc12]

To a solution of 2-methyl-4-(trifluoromethoxy)aniline (150 mg, 0.785 mmol) in acetonitrile (3.924 mL) was added ammonium thiocyanate (90 mg, 1.177 mmol) followed by benzyltrimethylammonium tribromide (306 mg, 0.785 mmol) causing the reaction mixture to become a bright yellow, heterogeneous suspension. The reaction mixture was allowed to stir at room temperature overnight. After 13 h, the reaction mixture was diluted with EtOAc and washed with saturated NaHCO$_3$ followed by brine. The bright yellow organic phase was dried over MgSO$_4$, filtered and concentrated. The resulting crude mixture was purified by ISCO (24 g Column, 0-70% EtOAc/Hex, 18 min. Product at 37%) to give Intermediate 262A (112 mg, 0.451 mmol, 57.5% yield) as a white powder. LC-MS: Method H, RT=1.03 min, MS (ESI) m/z: 249.1 (M+H)$^+$. $^1$H NMR (400 MHz, CHLOROFORM-d) δ 7.32 (s, 1H), 7.02 (s, 1H), 5.24 (br. s., 2H), 2.57 (s, 3H). $^{19}$F NMR (376 MHz, CHLOROFORM-d) δ −58.12 (s, 1F).

Intermediate 262B: 2-bromo-4-methyl-6-(trifluoromethoxy)benzo[d]thiazole

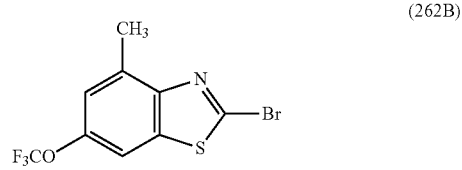 [SMILES: Cc1cc(OC(F)(F)F)cc2sc(Br)nc12]

Copper (II) bromide (100 mg, 0.479 mmol) and Intermediate 262A (108 mg, 0.435 mmol) were solvated in acetonitrile (2 mL). t-Butyl nitrite (0.075 mL, 0.566 mmol) was then added at room temperature. After 30 min, the reaction mixture was dilute with EtOAc and washed with 1.0 M HCl followed by brine. The crude material was concentrated and purified by ISCO flash chromatography (0-5% EtOAc/Hex over 20 min, 24 g silica gel cartridge, product at 2.5%) to afford Intermediate 262B (124 mg, 0.386 mmol, 91% yield). LC-MS: Method H, RT=1.42 min, MS (ESI) m/z: 312.0, 314.0 (M+H)$^+$. $^1$H NMR (400 MHz, CHLOROFORM-d) δ 7.51 (s, 1H), 7.17 (s, 1H), 2.73 (s, 3H). $^{19}$F NMR (376 MHz, CHLOROFORM-d) δ −57.93 (s, 1F).

Example 262

Intermediate I-2 (15.7 mg, 0.050 mmol), PdCl$_2$(dppf)-CH$_2$Cl$_2$ adduct (2.72 mg, 3.33 μmol) and Intermediate 262B (13 mg, 0.042 mmol) were solvated in DMF (1 mL). Sodium carbonate (2.0 M in H$_2$O) (100 μL, 0.200 mmol) was added, and the solution was degassed with argon for 10 min. The vial was then sealed and heated to 100° C. in the microwave for 30 min. The crude solution was filtered and purified by preparative HPLC (Method D, 55-100% over 20 minutes) to yield Example 262 (5.9 mg, 0.014 mmol, 33.4% yield). LC-MS: Method H, RT=1.56 min, MS (ESI) m/z: 420.0 (M+H)$^+$. $^1$H NMR (500 MHz, METHANOL-d$_4$) δ 9.10 (s, 1H), 8.91 (d, J=1.5 Hz, 1H), 7.98 (s, 1H), 7.71 (s, 1H), 7.21 (s, 1H), 4.86 (s, 2H), 3.61 (s, 3H), 2.88 (s, 3H), 2.74 (s, 3H).

Preparation of 2-Aminobenzothiazoles

The following 2-aminobenzothiazoles were made according to the following general procedure, which is analogous to the examples described above:

The appropriately substituted aniline (1.0 equiv) was solvated in acetonitrile (0.2 M). To this mixture was added ammonium thiocyanate (1.3 equiv) followed by benzyltrimethylammonium tribromide (1.0 equiv). After being allowed to stir at room temperature for the designated amount of time, the reaction mixture was diluted with CH$_2$Cl$_2$ and washed with saturated NaHCO$_3$ followed by brine. The organic phase was dried over MgSO$_4$, filtered and concentrated before being purified by silica gel chromatography to provide the desired material.

| Intermediate | Structure | Time | Yield | LCMS [M + H]$^+$ m/z | LCMS Retention Time (Min) Method H | NMR |
|---|---|---|---|---|---|---|
| 263A | ![structure] | 3 d | 80% | 231.1 | 0.95 | $^1$H NMR (400 MHz, CHLOROFORM-d) δ 7.26 (s, 1H), 6.95 (s, 1H), 6.90 (t, J = 74.8 Hz, 1H), 5.39 (br. s., 2H), 2.40 (s, 3H). $^{19}$F NMR (376 MHz, CHLOROFORM-d) δ −81.04 (s, 1F). |

-continued

| Intermediate | Structure | Time | Yield | LCMS [M + H]+ m/z | LCMS Retention Time (Min) Method H | NMR |
|---|---|---|---|---|---|---|
| 265A | 2-amino-4-chloro-7-fluoro-6-methoxybenzothiazole | 7 d | 24% | 233.3, 235.1 | 1.04 | ¹H NMR (400 MHz, CD₃OD-d) δ 7.11 (d, J = 7.5 Hz, 1H), 3.87 (s, 3H). |
| 266A | 2-amino-4-chloro-6-fluorobenzothiazole | 16 h | 72% | 203.0 205.0 | 0.94 | ¹H NMR (400 MHz, METHANOL-d₄) δ 7.37 (dd, J = 8.0, 2.5 Hz, 1H), 7.13 (dd, J = 9.1, 2.5 Hz, 1H). |
| 269A | 2-amino-4-methoxy-5,6-difluorobenzothiazole | 16 h | 77% | 217.1 | 0.89 | ¹H NMR (400 MHz, METHANOL-d₄) δ 7.24 (dd, J = 9.6, 6.9 Hz, 1H), 4.06 (d, J = 1.1 Hz, 3H). |
| 270A | 2-amino-4-methyl-6-fluorobenzothiazole | 16 h | 64% | 199.1 | 0.74 | ¹H NMR (400 MHz, METHANOL-d₄) δ 6.96 (dd, J = 8.1, 2.4 Hz, 1H), 6.70 (dd, J = 11.2, 2.4 Hz, 1H), 3.91 (s, 3H). |
| 271A | 2-amino-4-methyl-5-fluoro-6-methoxybenzothiazole | 16 h | 73% | 229.1 | 0.79 | ¹H NMR (400 MHz, METHANOL-d₄) δ 7.08 (d, J = 7.3 Hz, 1H), 4.01 (d, J = 1.1 Hz, 3H), 3.85 (s, 3H). |
| 276A | 2-amino-5-methyl-6-methoxybenzothiazole | 16 h | 67% | 195.2 | 0.66 | ¹H NMR (400 MHz, CHLOROFORM-d) δ 7.33 (d, J = 0.7 Hz, 1H), 7.04 (s, 1H), 4.97 (br. s., 2H), 3.84 (s, 3H), 2.27 (s, 3H). |

| Intermediate | Structure | Time | Yield | LCMS [M + H]+ m/z | LCMS Retention Time (Min) Method | H NMR |
|---|---|---|---|---|---|---|
| 277A | 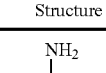 | 4 d | 49% | 199.1 | 0.56 | 1H NMR (400 MHz, METHANOL-d4) δ 7.34 (d, J = 8.4 Hz, 1H), 7.10 (d, J = 11.9 Hz, 1H), 3.86 (s, 3H). |

Preparation of 2-Bromobenzothiazoles

The following 2-bromobenzothiazoles were made according to the following general procedure, which is analogous to the examples described above:

The appropriately substituted 2-aminobenzothiazole (1.0 equiv) was suspended in acetonitrile (0.2 M). To this mixture was added copper (II) bromide (1.0 equiv) followed by t-butyl nitrite (1.3 equiv). After being allowed to stir at room temperature for 30 min, the reaction mixture was diluted with EtOAc and washed with 1.0 M HCl followed by brine. The organic phase was dried over MgSO4, filtered and concentrated before being purified by silica gel chromatography to provide the desired material.

| Intermediate | Structure | Yield | LCMS [M + H]+ m/z | LCMS Retention Time (Min) Method | H NMR |
|---|---|---|---|---|---|
| 263B | 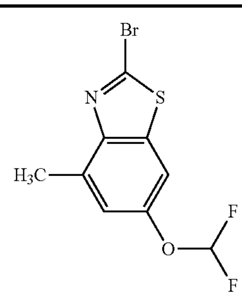 | 64% | 294.1, 296.1 | 1.24 | 1H NMR (400 MHz, CHLOROFORM-d) δ 7.45 (s, 1H), 7.10 (s, 1H), 7.04 (t, J = 74.4 Hz, 1H), 2.48 (s, 3H). |
| 264A | 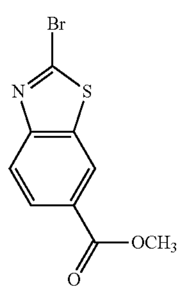 [SMILES: COC(=O)c1ccc2nc(Br)sc2c1] | 45% | 272.1, 274.1 | 1.22 | 1H NMR (400 MHz, CHLOROFORM-d) δ 8.56 (d, J = 1.3 Hz, 1H), 8.16 (dd, J = 8.6, 1.5 Hz, 1H), 8.04 (d, J = 8.1 Hz, 1H), 3.98 (s, 3H). |
| 265B | 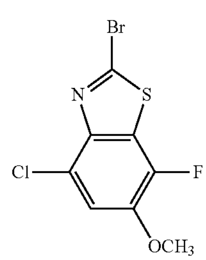 [SMILES: COc1cc(Cl)c2nc(Br)sc2c1F] | 28% | 295.9, 297.9, 298.9 | 1.32 | 1H NMR (400 MHz, CHLOROFORM-d) δ 7.22 (d, J = 7.3 Hz, 1H), 3.99 (s, 3H). |

-continued

| Intermediate | Structure | Yield | LCMS [M + H]+ m/z | LCMS Retention Time (Min) Method H | NMR |
|---|---|---|---|---|---|
| 266B | 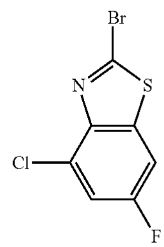 [SMILES: Fc1cc(Cl)c2nc(Br)sc2c1] | 62% | 265.9, 267.9, 270.0 | 1.22 | ¹H NMR (400 MHz, CHLOROFORM-d) δ 7.49-7.42 (m, 1H), 7.37-7.30 (m, 1H). |
| 268A | 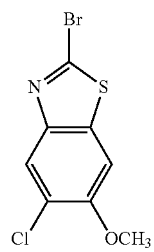 [SMILES: COc1cc2sc(Br)nc2cc1Cl] | 44% | 278.0, 280.0, 282.0 | 1.22 | ¹H NMR (400 MHz, CHLOROFORM-d) δ 8.00 (s, 1H), 7.30 (s, 1H), 3.98 (s, 4H). |
| 269B | 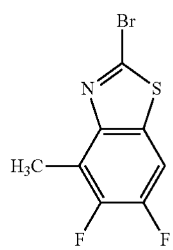 | 60% | 278.1, 280.1 | 1.21 | ¹H NMR (400 MHz, CHLOROFORM-d) δ 7.27 (dd, J = 6.4, 2.6 Hz, 1H), 4.33 (d, J = 2.0 Hz, 3H). |
| 270B | 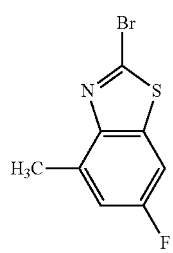 | 49% | 262.1, 264.1 | 1.11 | ¹H NMR (400 MHz, CHLOROFORM-d) δ 7.09 (dd, J = 7.7, 2.2 Hz, 1H), 6.70 (dd, J = 10.9, 2.3 Hz, 1H), 4.03 (s, 3H). |
| 271B | 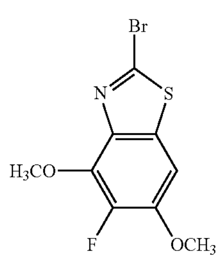 [SMILES: COc1cc2sc(Br)nc2c(OC)c1F] | 53% | 292.1, 294.1 | 1.14 | ¹H NMR (400 MHz, CHLOROFORM-d) δ 7.00 (d, J = 7.0 Hz, 1H), 4.28 (d, J = 2.0 Hz, 3H), 3.95 (s, 3H). |
| 272A | 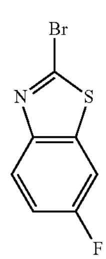 [SMILES: Fc1ccc2nc(Br)sc2c1] | 88% | 232.0, 234.0 | 1.17 | ¹H NMR (400 MHz, CHLOROFORM-d) δ 7.95 (dd, J = 9.0, 4.8 Hz, 1H), 7.51 (dd, J = 7.9, 2.4 Hz, 1H), 7.23 (appar. td, J = 8.9, 2.6 Hz, 1H). |

| Intermediate | Structure | Yield | LCMS [M + H]+ m/z | LCMS Retention Time (Min) Method H | NMR |
|---|---|---|---|---|---|
| 273A | 2-bromo-4-fluorobenzothiazole | 91% | 232.0, 234.0 | 1.17 | ¹H NMR (400 MHz, CHLOROFORM-d) δ 7.59 (d, J = 8.1 Hz, 1H), 7.40 (appar. td, J = 8.1, 4.6 Hz, 1H), 7.20 (dd, J = 9.6, 8.7 Hz, 1H). |
| 274A | 2-bromo-6-chlorobenzothiazole | 73% | 248.0, 250.1, 252.1 | 1.25 | ¹H NMR (400 MHz, CHLOROFORM-d) δ 7.91 (d, J = 8.6 Hz, 1H), 7.82-7.79 (m, 1H), 7.45 (dd, J = 8.7, 2.1 Hz, 1H). |
| 275A | 2-bromo-4,6-dichlorobenzothiazole | 73% | 281.9, 283.9 | 1.32 | ¹H NMR (400 MHz, CHLOROFORM-d) δ 7.71 (d, J = 1.8 Hz, 1H), 7.53 (d, J = 2.0 Hz, 1H). |
| 276B | 2-bromo-6-methoxy-5-methylbenzothiazole | 74% | 258.1, 260.1 | 1.05 | ¹H NMR (400 MHz, CHLOROFORM-d) δ 7.71 (d, J = 0.7 Hz, 1H), 7.16 (s, 1H), 3.89 (s, 3H), 2.32 (d, J = 0.7 Hz, 3H). |
| 277B | 2-bromo-5-fluoro-6-methoxybenzothiazole | 45% | 262.0, 264.0 | 0.96 | ¹H NMR (400 MHz, CHLOROFORM-d) δ 7.69 (d, J = 11.0 Hz, 1H), 7.31 (d, J = 7.7 Hz, 1H), 3.96 (s, 3H). |

Preparation of Quinoxaline-Benzothiazole Examples

The following Quinoxaline-Benzothiazole adducts were made according to the following general procedure, which is analogous to the examples described above:

The appropriately substituted 2-bromobenzothiazole (1.0 equiv), PdCl$_2$(dppf)-CH$_2$Cl$_2$ adduct (0.08 equiv), and the appropriate boronic acid or ester (1.0 equiv) were solvated in DMF (0.05 M). A 2.0 M solution of aqueous sodium carbonate (4.0 equiv) was then added, and the mixture was degassed by bubbling argon through the solution for 10 min. The vial was then sealed and heated to 100° C. in the microwave for 30 min. The crude solution was filtered and purified by preparative HPLC to yield the desired example.

| Ex | Structure | B(OR)₂ | Br-Bzt | LCMS [M + H]⁺ m/z | LCMS RT (Min) Method H | HPLC Prep Method D | NMR |
|---|---|---|---|---|---|---|---|
| 263 | 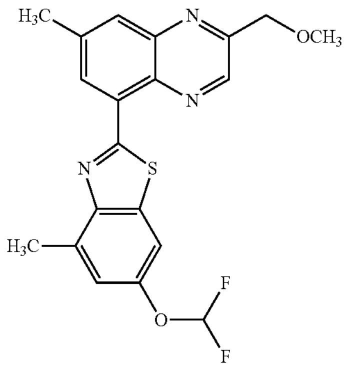 [SMILES: COCc1cnc2c(-c3nc4c(C)cc(OC(F)F)cc4s3)cc(C)cc2n1] | I-2 | 263B | 402.2 | 1.43 | 50-90% 20 min | ¹H NMR (500 MHz, DMSO-d₆) δ 9.11 (s, 1H), 8.85 (d, J = 1.7 Hz, 1H), 8.08 (s, 1H), 7.87 (s, 1H), 7.68 (t, J = 74.3 Hz, 1H), 7.21 (s, 1H), 4.82 (s, 2H), 3.47 (s, 3H), 2.71 (s, 3H) [another (s, 3H) was buried under DMSO at 2.5 ppm]. |
| 264 | 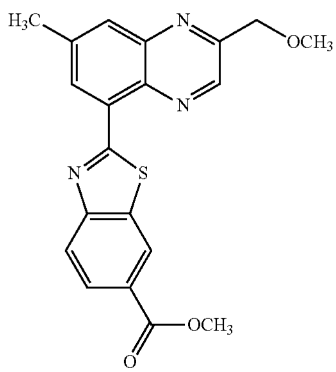 [SMILES: COCc1cnc2c(-c3nc4ccc(C(=O)OC)cc4s3)cc(C)cc2n1] | I-2 | 264A | 380.2 | 1.35 | 55-100% 11 min | ¹H NMR (500 MHz, DMSO-d₆) δ 9.14 (s, 1H), 8.92 (d, J = 1.7 Hz, 1H), 8.87 (d, J = 1.7 Hz, 1H), 8.23 (d, J = 8.8 Hz, 1H), 8.15-8.10 (m, 2H), 4.83 (s, 2H), 3.93 (s, 3H), 3.48 (s, 3H), 2.71 (s, 3H). |
| 265 | 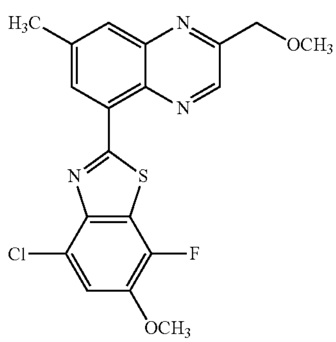 [SMILES: COCc1cnc2c(-c3nc4c(Cl)cc(OC)c(F)c4s3)cc(C)cc2n1] | I-2 | 265B | 404.1 406.1 | 1.43 | 70-100% 10 min | ¹H NMR (400 MHz, CHLOROFORM-d) δ 9.10 (s, 1H), 8.97 (d, J = 1.5 Hz, 1H), 8.00 (s, 1H), 7.30-7.27 (m, 1H-under CDCl₃), 4.86 (s, 2H), 4.02 (s, 3H), 3.59 (s, 3H), 2.73 (s, 3H). |
| 266 | 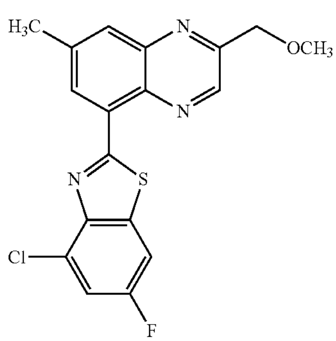 [SMILES: COCc1cnc2c(-c3nc4c(Cl)cc(F)cc4s3)cc(C)cc2n1] | I-2 | 266B | 374.1, 376.1 | 1.45 | 55-100% 20 min | ¹H NMR (500 MHz, DMSO-d₆) δ 9.11 (s, 1H), 8.84 (s, 1H), 8.14 (d, J = 8.3 Hz, 1H), 8.11 (s, 1H), 7.72 (d, J = 8.8 Hz, 1H), 4.84 (s, 2H), 3.49 (s, 3H), 2.72 (s, 3H). |

-continued

| Ex | Structure | B(OR)$_2$ | Br-Bzt | LCMS [M + H]$^+$ m/z | LCMS RT (Min) Method H | HPLC Prep Method D | NMR |
|---|---|---|---|---|---|---|---|
| 267 | 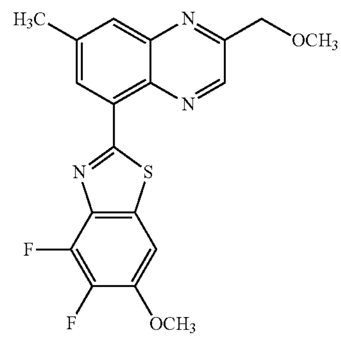 [SMILES: COCc1cnc2c(-c3nc4c(F)c(F)c(OC)cc4s3)cc(C)cc2n1] | I-2 | I-41 | 388.2 | 1.34 | 50-90% 20 min | $^1$H NMR (500 MHz, DMSO-d$_6$) δ 9.10 (br. s., 1H), 8.81 (br. s., 1H), 8.06 (br. s., 1H), 7.86 (d, J = 5.8 Hz, 1H), 4.83 (br. s., 2H), 4.00 (br. s., 3H), 3.49 (br. s., 3H), 2.70 (br. s., 3H). |
| 268 | 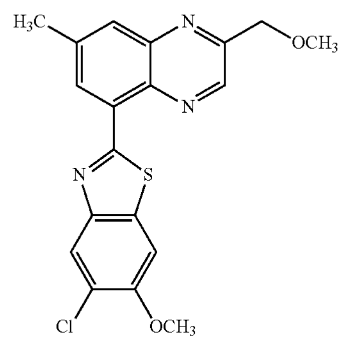 [SMILES: COCc1cnc2c(-c3nc4cc(Cl)c(OC)cc4s3)cc(C)cc2n1] | I-2 | 268A | 385.5, 387.5 | 1.32 | 50-90% 20 min | $^1$H NMR (500 MHz, DMSO-d$_6$) δ 9.11 (br. s., 1H), 8.79 (br. s., 1H), 8.20 (br. s., 1H), 8.06 (br. s., 1H), 7.99 (br. s., 1H), 4.83 (br. s., 2H), 3.99 (br. s., 3H), 3.49 (br. s., 3H), 2.69 (br. s., 3H). |
| 269 | 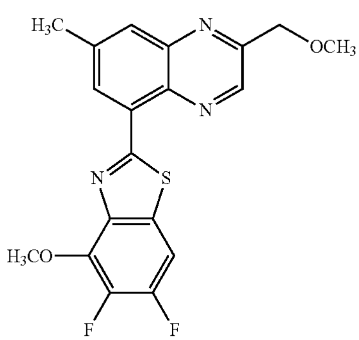 [SMILES: COCc1cnc2c(-c3nc4c(OC)c(F)c(F)cc4s3)cc(C)cc2n1] | I-2 | 269B | 388.1 | 1.40 | 55-90% 25 min | $^1$H NMR (500 MHz, DMSO-d$_6$) δ 9.11 (br. s., 1H), 8.86 (br. s., 1H), 8.11 (br. s., 1H), 8.03 (br. s., 1H), 4.83 (br. s., 2H), 4.44 (br. s., 3H), 3.48 (br. s., 3H), 2.72 (br. s., 3H). |
| 270 | 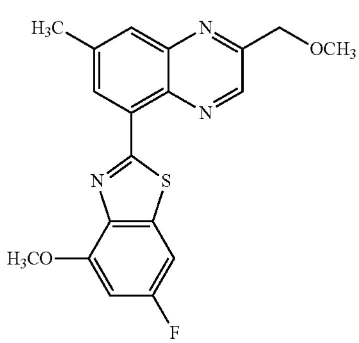 [SMILES: COCc1cnc2c(-c3nc4c(OC)cc(F)cc4s3)cc(C)cc2n1] | I-2 | 270B | 370.2 | 1.30 | 45-85% 20 min | $^1$H NMR (500 MHz, DMSO-d$_6$) δ 9.08 (s, 1H), 8.79 (s, 1H), 8.05 (s, 1H), 7.62 (d, J = 8.1 Hz, 1H), 7.05 (d, J = 9.6 Hz, 1H), 4.81 (s, 2H), 4.04 (s, 3H), 3.46 (s, 3H), 2.69 (s, 3H). |

-continued

| Ex | Structure | B(OR)$_2$ | Br-Bzt | LCMS [M + H]$^+$ m/z | LCMS RT (Min) Method H | HPLC Prep Method D | NMR |
|---|---|---|---|---|---|---|---|
| 271 | 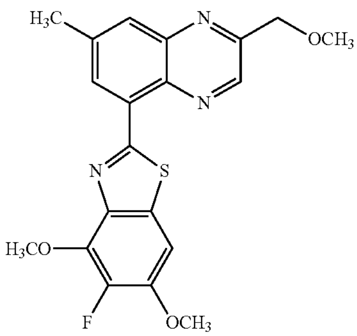 [SMILES: COCc1cnc2c(-c3nc4c(OC)c(F)c(OC)cc4s3)cc(C)cc2n1] | I-2 | 271B | 400.2 | 1.30 | 45-85% 10 min | $^1$H NMR (500 MHz, DMSO-d$_6$) δ 9.09 (s, 1H), 8.80 (d, J = 1.7 Hz, 1H), 8.04 (s, 1H), 7.67 (d, J = 7.4 Hz, 1H), 4.81 (s, 2H), 4.34 (s, 3H), 3.94 (s, 3H), 3.47 (s, 3H), 2.69 (s, 3H). |
| 272 | 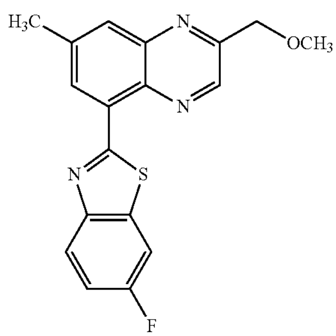 [SMILES: COCc1cnc2c(-c3nc4ccc(F)cc4s3)cc(C)cc2n1] | I-2 | 272A | 340.1 | 1.38 | 35-75% 20 min | $^1$H NMR (500 MHz, DMSO-d$_6$) δ 9.11 (s, 1H), 8.85 (s, 1H), 8.17 (dd, J = 8.9, 4.8 Hz, 1H), 8.13 (d, J = 8.5 Hz, 1H), 8.09 (s, 1H), 7.46 (td, J = 8.9, 2.1 Hz, 1H), 4.83 (s, 2H), 3.48 (s, 3H), 2.70 (s, 3H). |
| 273 | 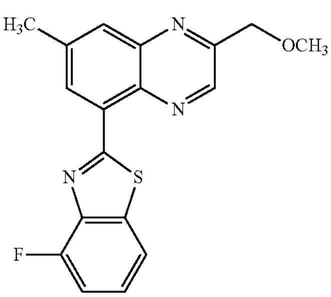 [SMILES: COCc1cnc2c(-c3nc4c(F)cccc4s3)cc(C)cc2n1] | I-2 | 273A | 340.1 | 1.37 | 40-80% 20 min | $^1$H NMR (500 MHz, DMSO-d$_6$) δ 9.13 (s., 1H), 8.90 (s., 1H), 8.12 (s, 1H), 8.06 (d, J = 7.2 Hz, 1H), 7.52 (s., 1H), 7.47-7.39 (m, J = 9.6 Hz, 1H), 4.84 (s., 2H), 3.49 (s., 3H), 2.72 (s., 3H). |
| 274 | 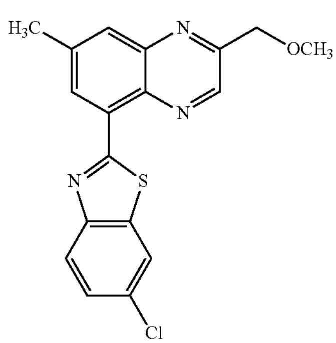 [SMILES: COCc1cnc2c(-c3nc4ccc(Cl)cc4s3)cc(C)cc2n1] | I-2 | 274A | 356.3, 358.2 | 1.47 | 60-100% 10 min | $^1$H NMR (500 MHz, DMSO-d$_6$) δ 9.13 (s, 1H), 8.89 (d, J = 1.9 Hz, 1H), 8.39 (d, J = 2.2 Hz, 1H), 8.15 (d, J = 8.8 Hz, 1H), 8.11 (s, 1H), 7.62 (dd, J = 8.5, 2.2 Hz, 1H), 4.84 (s, 2H), 3.48 (s, 3H), 2.71 (s, 3H). |

-continued

| Ex | Structure | B(OR)₂ | Br-Bzt | LCMS [M + H]⁺ m/z | LCMS RT (Min) Method H | HPLC Prep Method D | NMR |
|---|---|---|---|---|---|---|---|
| 275 | (structure) | I-2 | 275A | 390.1, 392.0, 394.1 | 1.57 | 60-100% 20 min | ¹H NMR (500 MHz, DMSO-d₆) δ 9.14 (s, 1H), 8.88 (s, 1H), 8.39 (s, 1H), 8.15 (s, 1H), 7.84 (s, 1H), 4.84 (s, 2H), 2.73 (s, 2H) [another (s, 3H) was buried under H₂O at 3.5 ppm]. |
| 276 | (structure) | I-2 | 276B | 438.2 | 1.16 | 45-85% 20 min | ¹H NMR (500 MHz, DMSO-d₆) δ 9.10 (s, 1H), 8.79 (s, 1H), 8.02 (br. s., 1H), 7.91 (s, 1H), 7.71 (s, 1H), 4.82 (s, 2H), 3.93 (s, 3H), 3.49 (s, 3H), 2.69 (s, 3H), 2.34 (s, 3H). |
| 277 | (structure) | I-2 | 277B | 370.2 | 1.13 | 45-95% 15 min | ¹H NMR (500 MHz, DMSO-d₆) δ 9.11 (br. s., 1H), 8.81 (br. s., 1H), 8.06 (br. s., 1H), 7.99 (d, J = 9.6 Hz, 2H), 4.83 (br. s., 2H), 3.98 (br. s., 3H), 3.49 (br. s., 3H), 2.70 (br. s., 3H). |
| 278 | (structure) | I-9 | I-41 | 374.1 | 1.49 | 55-95% 15 min | ¹H NMR (500 MHz, DMSO-d₆) δ 8.74 (br. s., 1H), 8.59 (br. s., 1H), 7.92-7.76 (m, 2H), 4.09 (br. s., 3H), 3.99 (br. s., 3H), 2.65 (br. s., 3H). |

-continued

| Ex | Structure | B(OR)₂ | Br-Bzt | LCMS [M + H]⁺ m/z | LCMS RT (Min) Method H | HPLC Prep Method D | NMR |
|---|---|---|---|---|---|---|---|
| 279 | 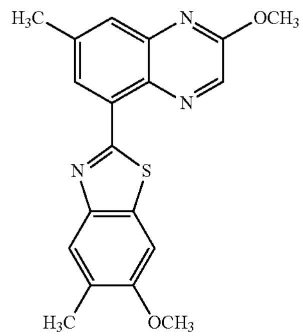 [SMILES: COc1cnc2c(-c3nc4cc(C)c(OC)cc4s3)cc(C)cc2n1] | I-9 | 276B | 438.2 | 1.16 | 45-80% 10 min | ¹H NMR (500 MHz, DMSO-d₆) δ 8.75 (s, 1H), 8.59 (d, J = 1.9 Hz, 1H), 7.90 (s, 1H), 7.83 (d, J = 0.8 Hz, 1H), 7.70 (s, 1H), 4.10 (s, 3H), 3.93 (s, 3H), 2.65 (s, 3H), 2.33 (s, 3H). |
| 280 | 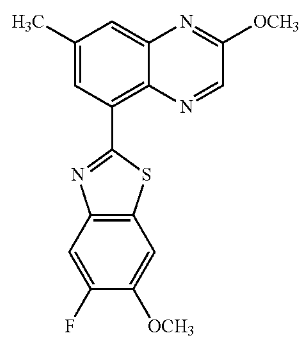 [SMILES: COc1cnc2c(-c3nc4cc(F)c(OC)cc4s3)cc(C)cc2n1] | I-9 | 277B | 356.2 | 1.22 | 60-100% 20 min | ¹H NMR (500 MHz, DMSO-d₆) δ 8.76 (s, 1H), 8.60 (d, J = 1.7 Hz, 1H), 7.99 (d, J = 6.6 Hz, 1H), 7.97 (d, J = 3.0 Hz, 1H), 7.85 (s, 1H), 4.10 (s, 3H), 3.97 (s, 3H), 2.65 (s, 3H). |
| 281 | 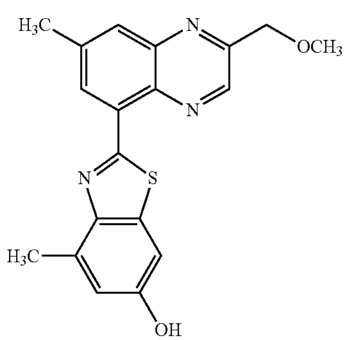 [SMILES: COCc1cnc2c(-c3nc4c(C)cc(O)cc4s3)cc(C)cc2n1] | I-2 | I-40 | 352.3 | 1.24 | 40-80% 10 min | ¹H NMR (500 MHz, DMSO-d₆) δ 9.76 (br. s., 1H), 9.08 (s, 1H), 8.79 (d, J = 1.7 Hz, 1H), 8.02 (s, 1H), 7.28 (d, J = 2.2 Hz, 1H), 6.87 (d, J = 1.4 Hz, 1H), 4.82 (s, 2H), 3.48 (s, 3H), 2.73 (s, 3H), 2.70 (s, 3H). |
| 282 | 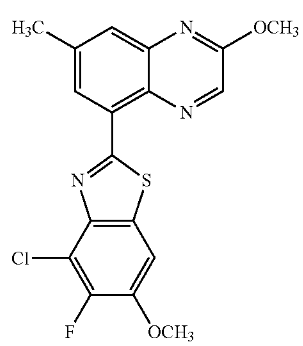 [SMILES: COc1cnc2c(-c3nc4c(Cl)c(F)c(OC)cc4s3)cc(C)cc2n1] | I-9 | I-43 | 390.0, 392.0 | 1.52 | 70-100% 15 min | ¹H NMR (500 MHz, DMSO-d₆) δ 8.78 (br. s., 1H), 8.63 (br. s., 1H), 7.97 (br. s, 1H), 7.89 (br. s., 1H), 4.10 (br. s., 3H), 3.99 (br. s., 3H), 2.67 (br. s., 3H). |

| Ex | Structure | B(OR)$_2$ | Br-Bzt | LCMS [M + H]$^+$ m/z | LCMS RT (Min) Method H | HPLC Prep Method D | NMR |
|---|---|---|---|---|---|---|---|
| 283 | 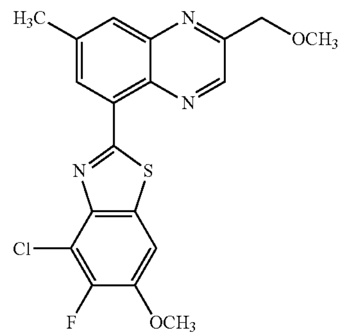 | I-2 | I-43 | 404.1, 406.1 | 1.16 | 45-80% 20 min | $^1$H NMR (500 MHz, DMSO-d$_6$) δ 9.13 (s, 1H), 8.84 (s, 1H), 8.10 (s, 1H), 8.04 (d, J = 7.7 Hz, 1H), 4.84 (s, 2H), 4.01 (s, 3H), 3.49 (s, 3H), 2.72 (s, 3H). |
| 284 | 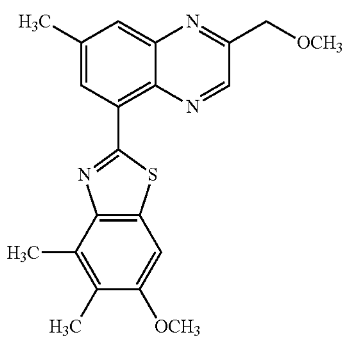 [SMILES: COCc1cnc2c(-c3nc4c(C)c(C)c(OC)cc4s3)cc(C)cc2n1] | I-2 | I-47 | 380.2 | 1.48 | 70-100% 20 min | $^1$H NMR (500 MHz, DMSO-d$_6$) δ 9.10 (s, 1H), 8.84 (d, J = 1.9 Hz, 1H), 8.03 (d, J = 0.8 Hz, 1H), 7.58 (s, 1H), 4.83 (s, 2H), 3.91 (s, 3H), 3.49 (s, 3H), 2.77 (s, 3H), 2.71 (s, 3H), 2.27 (s, 3H). |
| 285 | 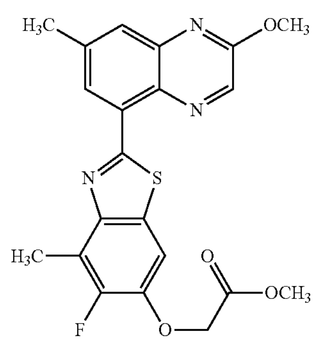 [SMILES: COC(=O)COc1cc2sc(-c3cc(C)cc4nc(OC)cnc34)nc2c(C)c1F] | I-9 | I-52 | 428.1 | 1.20 | 60-100% 10 min | $^1$H NMR (500 MHz, DMSO-d$_6$) δ 8.75 (s, 1H), 7.97 (s, 1H), 7.86 (s, 1H), 7.75 (d, J = 7.7 Hz, 1H), 4.10 (s, 3H), 3.75 (s, 3H), 2.90 (s, 3H), 2.75 (s, 3H). |
| 286 | 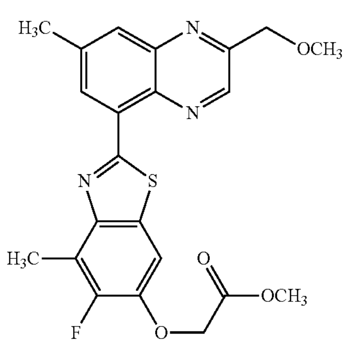 [SMILES: COCc1cnc2c(-c3nc4c(C)c(F)c(OCC(=O)OC)cc4s3)cc(C)cc2n1] | I-2 | I-52 | 442.2 | 1.04 | 45-85% 15 min | $^1$H NMR (500 MHz, DMSO-d$_6$) δ 9.09 (s, 1H), 8.83 (d, J = 1.4 Hz, 1H), 8.04 (s, 1H), 7.77 (d, J = 8.3 Hz, 1H), 5.00 (s, 2H), 4.82 (s, 2H), 3.76 (s, 3H), 3.48 (s, 3H), 2.72 (d, J = 1.4 Hz, 3H), 2.70 (s, 3H). |

| Ex | Structure | B(OR)$_2$ | Br-Bzt | LCMS [M + H]$^+$ m/z | LCMS RT (Min) Method H | HPLC Prep Method D | NMR |
|---|---|---|---|---|---|---|---|
| 287 | 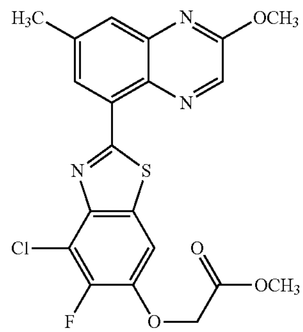 [SMILES: COC(=O)COc1cc2sc(-c3cc(C)cc4nc(OC)cnc34)nc2c(Cl)c1F] | I-9 | I-57 | 448.1, 450.1 | 1.18 | 60-100% 15 min | $^1$H NMR (500 MHz, DMSO-d$_6$) δ 9.09 (s, 1H), 8.83 (d, J = 1.4 Hz, 1H), 8.04 (s, 1H), 7.77 (d, J = 8.3 Hz, 1H), 4.82 (s, 2H), 3.76 (s, 3H), 3.48 (s, 3H), 2.72 (d, J = 1.4 Hz, 3H), 2.70 (s, 3H). |
| 288 | 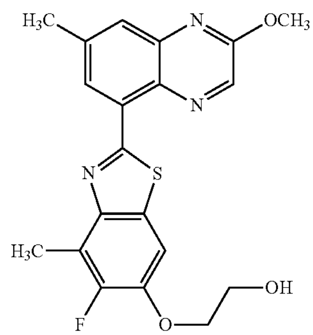 [SMILES: COc1cnc2c(-c3nc4c(C)c(F)c(OCCO)cc4s3)cc(C)cc2n1] | I-9 | I-53 | 400.2 | 1.08 | 45-80% 10 min | $^1$H NMR (500 MHz, DMSO-d$_6$) δ 8.74 (s, 1H), 8.61 (s, 1H), 7.83 (s, 1H), 7.77 (d, J = 8.0 Hz, 1H), 4.96 (t, J = 5.4 Hz, 1H), 4.17 (t, J = 4.8 Hz, 2H), 4.09 (s, 3H), 3.82 (q, J = 4.8 Hz, 2H), 2.70 (s, 3H), 2.65 (s, 3H). |
| 289 | 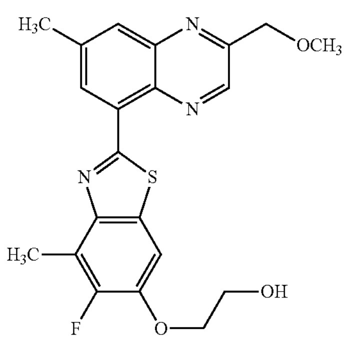 [SMILES: COCc1cnc2c(-c3nc4c(C)c(F)c(OCCO)cc4s3)cc(C)cc2n1] | I-2 | I-53 | 414.2 | 0.89 | 30-70% 10 min | $^1$H NMR (500 MHz, DMSO-d$_6$) δ 9.09 (s, 1H), 8.82 (s, 1H), 8.03 (s, 1H), 7.79 (d, J = 8.0 Hz, 1H), 4.96 (t, J = 5.4 Hz, 1H), 4.82 (s, 2H), 4.17 (t, J = 5.0 Hz, 2H), 3.82 (q, J = 5.1 Hz, 2H), 3.49 (s, 3H), 2.70 (s, 6H). |
| 290 | 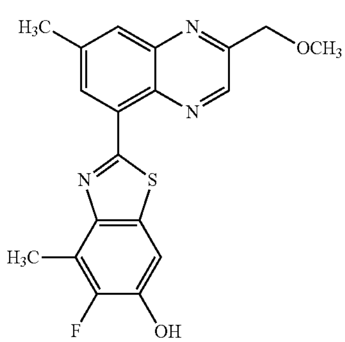 [SMILES: COCc1cnc2c(-c3nc4c(C)c(F)c(O)cc4s3)cc(C)cc2n1] | I-2 | I-46 | 370.1 | 0.93 | 45-85% 10 min | $^1$H NMR (500 MHz, DMSO-d$_6$) δ 9.07 (s, 1H), 8.81 (d, J = 1.1 Hz, 1H), 8.02 (s, 1H), 7.45 (d, J = 8.3 Hz, 1H), 4.82 (s, 2H), 3.48 (s, 3H), 2.70 (s, 3H), 2.69 (d, J = 1.1 Hz, 3H). |

-continued

| Ex | Structure | B(OR)$_2$ | Br-Bzt | LCMS [M + H]$^+$ m/z | LCMS RT (Min) Method H | HPLC Prep Method D | NMR |
|---|---|---|---|---|---|---|---|
| 291 | 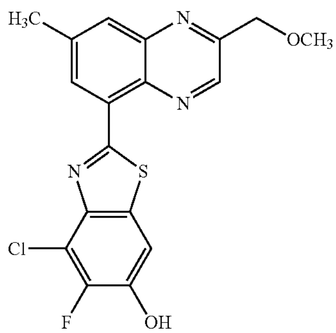 [SMILES: COCc1cnc2c(-c3nc4c(Cl)c(F)c(O)cc4s3)cc(C)cc2n1] | I-2 | I-44 | 390.1, 392.0 | 1.27 | 30-70% 10 min | $^1$H NMR (500 MHz, DMSO-d$_6$) δ 9.07 (s, 1H), 8.79 (d, J = 1.4 Hz, 1H), 8.04 (s, 1H), 7.63 (d, J = 7.7 Hz, 1H), 4.82 (s, 2H), 3.48 (s, 3H), 2.70 (s, 3H). |
| 292 | 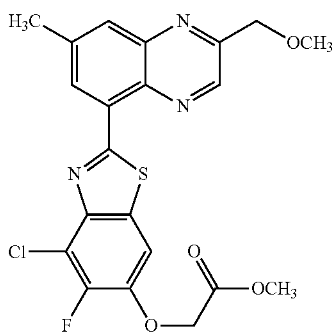 [SMILES: COCc1cnc2c(-c3nc4c(Cl)c(F)c(OCC(=O)OC)cc4s3)cc(C)cc2n1] | I-2 | I-57 | 462.1, 464.1 | 1.04 | 30-65% 10 min, 100% 5 min | $^1$H NMR (500 MHz, DMSO-d$_6$) δ 9.12 (s, 1H), 8.84 (s, 1H), 8.10 (s, 1H), 8.03 (d, J = 7.7 Hz, 1H), 5.07 (s, 2H), 4.84 (s, 2H), 3.77 (s, 3H), 3.49 (s, 3H), 2.72 (s, 3H). |
| 293 | 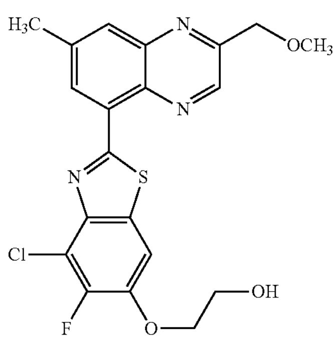 [SMILES: COCc1cnc2c(-c3nc4c(Cl)c(F)c(OCCO)cc4s3)cc(C)cc2n1] | I-2 | I-59 | 434.1, 436.1 | 0.89 | 35-70% 10 min, 100% 5 min | $^1$H NMR (500 MHz, DMSO-d$_6$) δ 9.09 (s, 1H), 8.79 (s, 1H), 8.05 (s, 1H), 8.00 (d, J = 7.7 Hz, 1H), 5.00 (t, J = 5.4 Hz, 1H), 4.82 (s, 2H), 4.22 (t, J = 4.8 Hz, 2H), 3.83 (q, J = 5.0 Hz, 2H), 3.49 (s, 3H), 2.70 (s, 3H). |
| 294 | 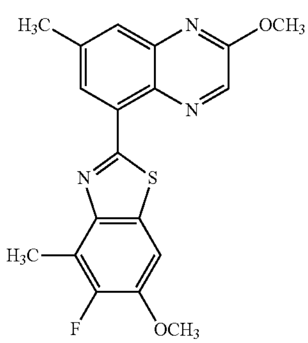 [SMILES: COc1cnc2c(-c3nc4c(C)c(F)c(OC)cc4s3)cc(C)cc2n1] | I-9 | I-45 | 370.2 | 1.30 | 55-95% 10 min, 100% 7 min | $^1$H NMR (500 MHz, DMSO-d$_6$) δ 8.76 (s, 1H), 8.64 (s, 1H), 7.85 (s, 1H), 7.79 (d, J = 8.0 Hz, 1H), 4.10 (s, 3H), 3.95 (s, 3H), 2.71 (s, 3H), 2.66 (s, 3H). |

| Ex | Structure | B(OR)₂ | Br-Bzt | LCMS [M + H]⁺ m/z | LCMS RT (Min) Method H | HPLC Prep Method D | NMR |
|---|---|---|---|---|---|---|---|
| 295 | (structure) | I-2 | I-45 | 384.1 | 1.17 | 50-85% 10 min, 100% 5 min | ¹H NMR (500 MHz, DMSO-d₆) δ 9.12 (s, 1H), 8.86 (s, 1H), 8.06 (s, 1H), 7.82 (d, J = 8.3 Hz, 1H), 4.83 (s, 2H), 3.96 (s, 3H), 3.49 (s, 3H), 2.72 (s, 6H). |
| 296 | (structure) | I-2 | I-49 | 438.1 | 1.14 | 60-100% 15 min | ¹H NMR (500 MHz, DMSO-d₆) δ 9.09 (s, 1H), 8.84 (s, 1H), 8.03 (s, 1H), 7.54 (s, 1H), 4.94 (s, 2H), 4.82 (s, 2H), 3.76 (s, 3H), 3.49 (s, 3H), 2.78 (s, 3H), 2.71 (s, 3H), 2.33 (s, 3H). |
| 297 | (structure) | I-2 | I-51 | 410..2 | 1.30 | 45-90% 12 min, 100% 5 min | ¹H NMR (500 MHz, DMSO-d₆) δ 9.09 (s, 1H), 8.83 (s, 1H), 8.01 (s, 1H), 7.56 (s, 1H), 4.90 (t, J = 5.4 Hz, 1H), 4.82 (s, 2H), 4.11 (br. s., 2H), 3.82 (d, J = 4.7 Hz, 2H), 3.48 (s, 3H), 2.76 (s, 3H), 2.70 (s, 3H), 2.29 (s, 3H). |
| 298 | (structure) | I-2 | I-56 | 400.1, 402.1 | 1.41 | 70-100% 10 min | ¹H NMR (500 MHz, DMSO-d₆) δ 9.12 (s, 1H), 8.83 (s, 1H), 8.07 (s, 1H), 7.80 (s, 1H), 4.84 (s, 2H), 3.96 (s, 3H), 3.49 (s, 3H), 2.72 (s, 3H), 2.41 (s, 3H). |

| Ex | Structure | B(OR)$_2$ | Br-Bzt | LCMS [M + H]$^+$ m/z | LCMS RT (Min) Method H | HPLC Prep Method D | NMR |
|---|---|---|---|---|---|---|---|
| 299 | 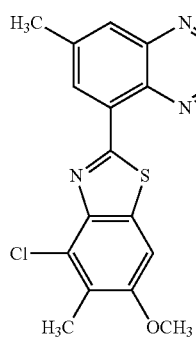 | I-9 | I-56 | 386.1, 388.1 | 1.50 | 70-100% 15 min | $^1$H NMR (500 MHz, DMSO-d$_6$) δ 8.77 (s, 1H), 8.61 (d, J = 1.7 Hz, 1H), 7.86 (s, 1H), 7.76 (s, 1H), 4.10 (s, 3H), 3.95 (s, 3H), 2.67 (s, 3H), 2.40 (s, 3H). |
| 300 | 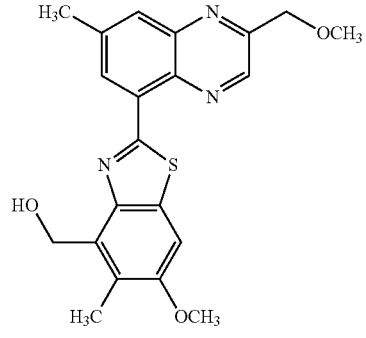 [SMILES: COCc1cnc2c(-c3nc4c(CO)c(C)c(OC)cc4s3)cc(C)cc2n1] | I-2 | I-54 | 395.8 | 1.06 | 55-100% 15 min | $^1$H NMR (500 MHz, DMSO-d$_6$) δ 9.11 (s, 1H), 8.85 (br. s., 1H), 8.03 (br. s., 1H), 7.69 (s, 1H), 5.20 (br. s., 2H), 5.10-5.04 (m, 1H), 4.82 (s, 2H), 3.92 (s, 3H), 3.48 (s, 3H), 2.71 (s, 3H), 2.37 (s, 3H). |
| 301 | 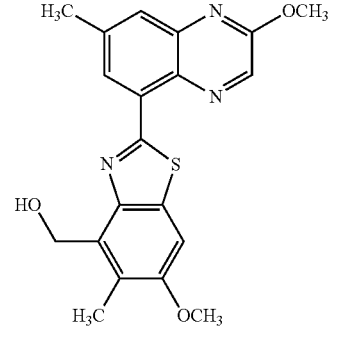 [SMILES: COc1cnc2c(-c3nc4c(CO)c(C)c(OC)cc4s3)cc(C)cc2n1] | I-9 | I-54 | 381.8 | 1.16 | 50-100% 20 min | $^1$H NMR (500 MHz, DMSO-d$_6$) δ 8.73 (s, 1H), 8.62 (d, J = 1.7 Hz, 1H), 7.81 (s, 1H), 7.65 (s, 1H), 5.18 (d, J = 5.2 Hz, 2H), 5.09-5.02 (m, 1H), 4.08 (s, 3H), 3.91 (s, 3H), 2.65 (s, 3H), 2.36 (s, 3H). |
| 302 | 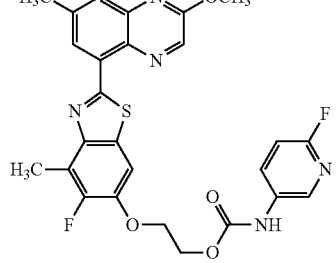 | I-9 | I-62 | 538.1 | 1.21 | 60-100% 13 min | $^1$H NMR (500 MHz, DMSO-d$_6$) δ 10.15 (br. s., 1H), 8.75 (s, 1H), 8.62 (s, 1H), 8.30 (br. s., 1H), 8.04 (d, J = 7.4 Hz, 1H), 7.97 (s, 1H), 7.84 (s, 1H), 7.19-7.12 (m, 1H), 4.55 (br. s., 2H), 4.43 (br. s., 2H), 4.10 (s, 3H), 2.70 (s, 3H), 2.66 (s, 3H). |

-continued

| Ex | Structure | B(OR)₂ | Br-Bzt | LCMS [M + H]⁺ m/z | LCMS RT (Min) Method H | HPLC Prep Method D | NMR |
|---|---|---|---|---|---|---|---|
| 303 | 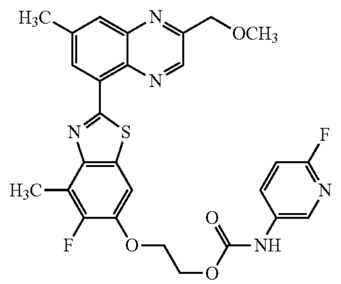 [SMILES: COCc1cnc2c(-c3nc4c(C)c(F)c(OCCOC(=O)Nc5ccc(F)nc5)cc4s3)cc(C)cc2n1] | I-2 | I-62 | 552.1 | 1.04 | 45-100% 10 min | ¹H NMR (500 MHz, DMSO-d₆) δ 10.15 (br. s., 1H), 9.11 (s, 1H), 8.84 (s, 1H), 8.30 (br. s., 1H), 8.05 (br. s., 1H), 7.97 (s, 1H), 7.86 (d, J = 8.0 Hz, 1H), 7.16 (dd, J = 8.8, 3.0 Hz, 1H), 4.83 (s, 2H), 4.55 (d, J = 4.4 Hz, 2H), 4.45 (d, J = 3.6 Hz, 2H), 3.49 (s, 3H), 2.90 (s, 3H), 2.75 (s, 3H). |
| 304 | 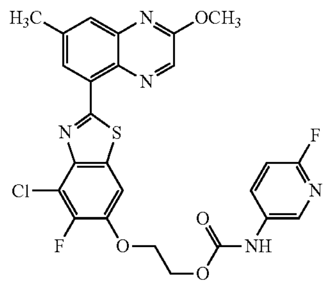 [SMILES: COc1cnc2c(-c3nc4c(Cl)c(F)c(OCCOC(=O)Nc5ccc(F)nc5)cc4s3)cc(C)cc2n1] | I-9 | I-63 | 558.1, 560.1 | 1.18 | 70-100% 12 min | ¹H NMR (400 MHz, THF) δ 8.83 (d, J = 1.5 Hz, 1H), 8.61 (s, 1H), 8.24 (s, 1H), 8.18-8.08 (m, 1H), 7.84 (s, 1H), 7.77 (d, J = 7.3 Hz, 1H), 6.95 (dd, J = 8.8, 3.5 Hz, 1H), 4.64-4.58 (m, 2H), 4.52-4.46 (m, 2H), 4.15 (s, 3H), 2.70 (s, 3H). |
| 305 | 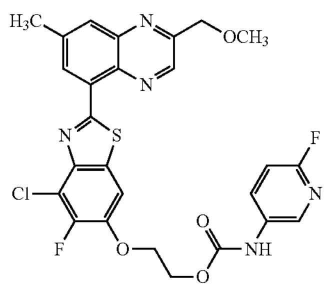 [SMILES: COCc1cnc2c(-c3nc4c(Cl)c(F)c(OCCOC(=O)Nc5ccc(F)nc5)cc4s3)cc(C)cc2n1] | I-2 | I-63 | 572.1, 574.1 | 1.03 | 50-100% 10 min | ¹H NMR (500 MHz, CHLOROFORM-d) δ 9.11 (s, 1H), 9.00 (s, 1H), 8.18 (br. s., 1H), 8.05 (s, 3H), 6.96 (dd, J = 8.8, 3.0 Hz, 1H), 4.88 (s, 2H), 4.69-4.64 (m, 2H), 4.48-4.41 (m, 2H), 3.62 (s, 3H), 2.76 (s, 3H). |

Example 306

2-(2-(methoxymethyl)-7-methylquinoxalin-5-yl)-4-methylbenzo[d]thiazol-6-ol

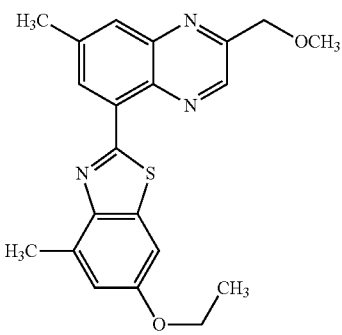

(306)

Intermediate 306A: 2-bromo-6-ethoxy-4-methyl-benzo[d]thiazole

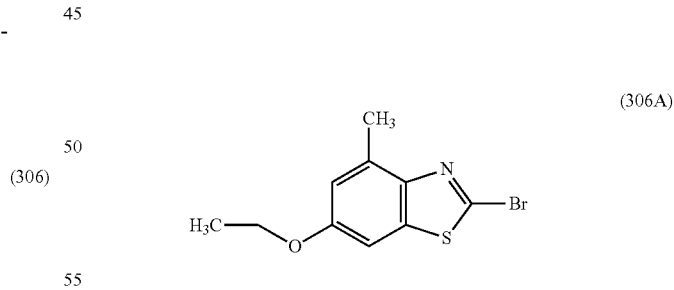

(306A)

To a solution of Intermediate I-40 (18 mg, 0.074 mmol) solvated in DMF (1 mL) was added potassium carbonate (51.0 mg, 0.369 mmol) followed by iodoethane (0.018 mL, 0.221 mmol). The reaction mixture was allowed to stir at room temperature overnight. After 15 hours, the reaction mixture was diluted with hexanes and extracted with water. The organic phase was concentrated in vacuo to provide Intermediate 306A (18 mg, 0.066 mmol, 90% yield) which was used without further purification. LC-MS: Method H, RT=1.31 min, MS (ESI) m/z: 272.1, 274.1 (M+H)⁺. ¹H NMR (400 MHz, CHLOROFORM-d) δ 7.07 (d, J=2.4 Hz, 1H), 6.87 (dd, J=2.4, 0.7 Hz, 1H), 4.06 (q, J=7.0 Hz, 2H), 2.66 (s, 3H), 1.45 (t, J=7.0 Hz, 3H).

Example 306

This example was prepared according to the general procedure for quinoxaline-benzothiazoles described in the table above. Thus, reaction of Intermediate 306A with Intermediate I-2 afforded Example 306 in 43% yield following purification by preparative HPLC (Method D, 60-100% over 10 min). LC-MS: Method H, RT=1.49 min, MS (ESI) m/z: 380.3 (M+H)$^+$. $^1$H NMR (500 MHz, DMSO-$d_6$) δ 9.09 (s, 1H), 8.80 (d, J=1.9 Hz, 1H), 8.03 (s, 1H), 7.53 (d, J=2.2 Hz, 1H), 7.00 (s, 1H), 4.81 (s, 2H), 4.12 (q, J=6.9 Hz, 2H), 3.47 (s, 3H), 2.75 (s, 3H), 2.69 (s, 3H), 1.38 (t, J=7.0 Hz, 3H).

Example 307

6-(benzyloxy)-2-(2-(methoxymethyl)-7-methylquinoxalin-5-yl)-4-methylbenzo[d]thiazole

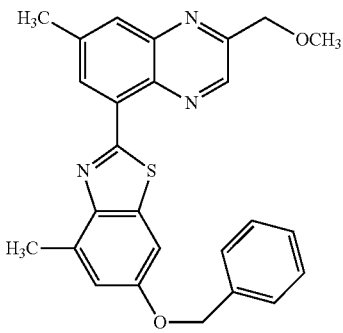

(307)

Intermediate 307A: 6-(benzyloxy)-2-bromo-4-methylbenzo[d]thiazole

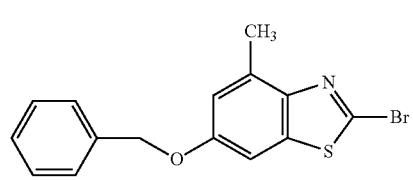

(307A)

To a solution of Intermediate I-40 (18 mg, 0.074 mmol) solvated in DMF (1 mL) was added potassium carbonate (51.0 mg, 0.369 mmol) followed by benzyl bromide (0.013 mL, 0.111 mmol). The reaction mixture was allowed to stir at room temperature overnight. After 15 hours, the reaction mixture was diluted with hexanes and extracted with water. The organic phase was concentrated in vacuo to provide Intermediate 307A (23 mg, 0.066 mmol, 91% yield) which was used without further purification. LC-MS: Method H, RT=1.37 min, MS (ESI) m/z: 334.1, 336.1 (M+H)$^+$. $^1$H NMR (400 MHz, CHLOROFORM-d) δ 7.44-7.20 (m, 5H), 7.06 (d, J=2.2 Hz, 1H), 6.89 (s, 1H), 5.02 (s, 2H), 2.59 (s, 3H).

Example 307

This example was prepared according to the general procedure for quinoxaline-benzothiazoles described in the table above. Thus, reaction of Intermediate 307A with Intermediate I-2 afforded Example 307 in 48% yield following purification by preparative HPLC (Method D, 55-100% over 10 min). LC-MS: Method H, RT=1.48 min, MS (ESI) m/z: 442.3 (M+H)$^+$. $^1$H NMR (500 MHz, DMSO-$d_6$) δ 9.08 (s, 1H), 8.80 (s, 1H), 8.02 (s, 1H), 7.63 (d, J=2.2 Hz, 1H), 7.51 (d, J=7.4 Hz, 2H), 7.42 (t, J=7.6 Hz, 2H), 7.38-7.32 (m, 1H), 7.09 (s, 1H), 5.20 (s, 2H), 4.81 (s, 2H), 3.46 (s, 3H), 2.75 (s, 3H), 2.69 (s, 3H).

Example 308

(2-(2-(methoxymethyl)-7-methylquinoxalin-5-yl)benzo[d]thiazol-6-yl)methanol

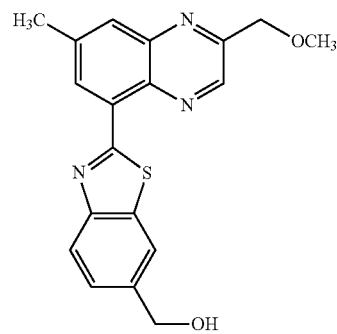

(308)

Intermediate 308A: ethyl 2-bromobenzo[d]thiazole-6-carboxylate

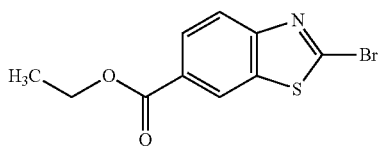

(308A)

This example was prepared according to the general procedure for 2-aminobenzothiazoles described in the table above. Thus, reaction of ethyl 2-aminobenzo[d]thiazole-6-carboxylate afforded Intermediate 308A in 98% yield. LC-MS: Method A, RT=2.06 min, MS (ESI) m/z: 286.0, 288.0 (M+H)$^+$. $^1$H NMR (500 MHz, CHLOROFORM-d) δ 8.56 (d, J=1.4 Hz, 1H), 8.18 (dd, J=8.5, 1.7 Hz, 1H), 8.04 (d, J=8.5 Hz, 1H), 4.45 (q, J=7.2 Hz, 2H), 1.45 (t, J=7.2 Hz, 3H).

Intermediate 308B:
(2-bromobenzo[d]thiazol-6-yl)methanol

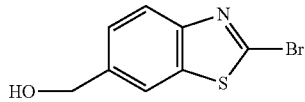
(308B)

Intermediate 308A (0.85 g, 2.97 mmol) was dissolved in THF (20 mL) and cooled to 0° C. 1.0 M Super-Hydride in THF (6.54 mL, 6.54 mmol) was added dropwise to this cooled solution. After stirring at 0° C. for 1 h, the reaction was quenched with saturated ammonium chloride and then diluted with EtOAc. The organic layer was washed with brine, dried over sodium sulfate, filtered and concentrated. The crude product was purified by silica gel chromatography (24 g, 5-60% EtOAc/Hexanes, 18 min) to give Intermediate 308B (0.5 g, 2.048 mmol, 69.0% yield) as a white solid. LC-MS: Method A, RT=1.54 min, MS (ESI) m/z: 244.0 and 246.0 (M+H)+. 1H NMR (500 MHz, CHLOROFORM-d) δ 7.93 (d, J=8.5 Hz, 1H), 7.70 (d, J=0.8 Hz, 1H), 7.39 (dd, 1.5 Hz, 1H), 5.08 (s, 2H).

Example 308

This example was prepared according to the general procedure for quinoxaline-benzothiazoles described in the table above. Thus, reaction of Intermediate 308B with Intermediate I-2 afforded Example 308 in 19% yield following purification by preparative HPLC (Method D, 20-60% over 10 min). LC-MS: Method H, RT=1.15 min, MS (ESI) m/z: 352.2 (M+H)+. 1H NMR (500 MHz, DMSO-d6) δ 9.13 (s, 1H), 8.88 (d, J=1.7 Hz, 1H), 8.13 (s, 1H), 8.10 (d, J=8.3 Hz, 1H), 8.08 (s, 1H), 7.54 (dd, J=8.5, 1.4 Hz, 1H), 5.38 (t, J=5.8 Hz, 1H), 4.83 (s, 2H), 4.69 (d, J=5.8 Hz, 2H), 3.49 (s, 3H), 2.71 (s, 3H).

Example 309

6-(methoxymethyl)-2-(2-(methoxymethyl)-7-methylquinoxalin-5-yl)benzo[d]thiazole

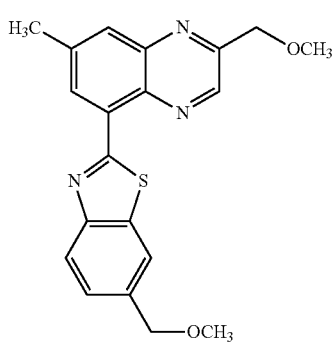
(309)

Intermediate 309A: 2-bromo-6-(methoxymethyl)benzo[d]thiazole

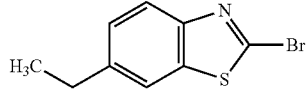
(309A)

Intermediate 308B (52 mg, 0.213 mmol) was solvated in THF (2.1 mL) and cooled to 0° C. Sodium Hydride (42.6 mg, 1.065 mmol) was added, causing effervescence. After 5 minutes, methyl iodide (0.067 mL, 1.065 mmol) was added. The mixture was then allowed to warm to room temperature and stirred for 10 minutes until all of the bubbling subsided. The reaction was quenched with saturated NH4Cl and diluted with EtOAc. The organic phase was extracted, washed with brine, dried over MgSO4 and concentrated. The crude material was purified by ISCO (12 g, 0-20% EtOAc/Hexanes, 18 min. Product at 8%) to afford Intermediate 309A (10 mg, 0.039 mmol, 18% yield). LC-MS: Method H, RT=1.19 min, MS (ESI) m/z: 258.1, 260.1 (M+H)+. 1H NMR (400 MHz, CHLOROFORM-d) δ 7.96 (d, J=8.4 Hz, 1H), 7.81 (d, J=0.7 Hz, 1H), 7.43 (dd, J=8.4, 1.5 Hz, 1H), 4.58 (s, 2H), 3.44 (s, 3H).

Example 309

This example was prepared according to the general procedure for quinoxaline-benzothiazoles described in the table above. Thus, reaction of Intermediate 309A with Intermediate I-2 afforded Example 309 in 27% yield following purification by preparative HPLC (Method D, 45-85% over 10 min). LC-MS: Method H, RT=1.33 min, MS (ESI) m/z: 366.3 (M+H)+. 1H NMR (500 MHz, DMSO-d6) δ 9.13 (s, 1H), 8.88 (d, J=1.4 Hz, 1H), 8.15 (s, 1H), 8.12 (d, J=8.3 Hz, 1H), 8.09 (s, 1H), 7.54 (d, J=8.3 Hz, 1H), 4.84 (s, 2H), 4.61 (s, 2H), 3.49 (s, 3H), 3.37 (s, 3H), 2.71 (s, 3H).

Example 310

6-methoxy-2-(2-(methoxymethyl)-7-methylquinoxalin-5-yl)benzo[d]thiazol-5-ol

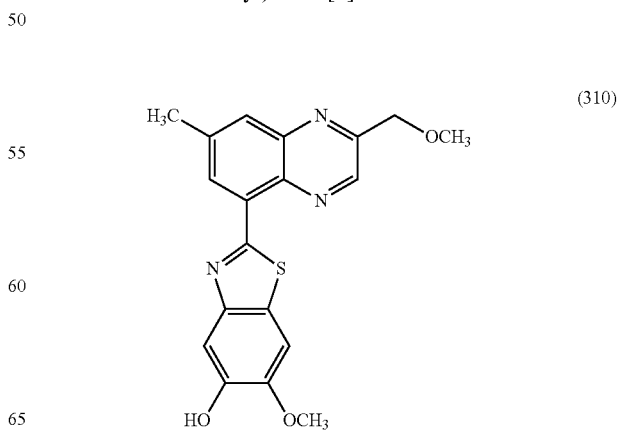
(310)

Intermediate 310A: 3-((tert-butyldimethylsilyl)oxy)-4-methoxyaniline

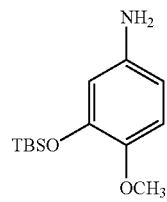
(310A)

5-amino-2-methoxyphenol (500 mg, 3.59 mmol) was solvated in DMF (3.00 mL) and DCM (15.000 mL). To this solution was added TBDMS-Cl (596 mg, 3.95 mmol) followed by imidazole (269 mg, 3.95 mmol) at room temperature. After 2 h, the reaction was quenched with saturated NaHCO$_3$ and extracted 2× with DCM. The organic phase was concentrated and purified by ISCO (80 g, 0-100% EtOAc/Hexanes, 33 min. Product at 35%) to give Intermediate 310A (576 mg, 1.591 mmol, 44.3% yield). LC-MS: Method H, RT=0.99 min, MS (ESI) m/z: 254.2 (M+H)$^+$. $^1$H NMR (400 MHz, CHLOROFORM-d) δ 6.69 (d, J=8.4 Hz, 1H), 6.31-6.24 (m, 2H), 3.73 (s, 3H), 3.38 (br. s., 2H), 1.00 (s, 9H), 0.16 (s, 6H).

Intermediate 310B: 5-((tert-butyldimethylsilyl)oxy)-6-methoxybenzo[d]thiazol-2-amine

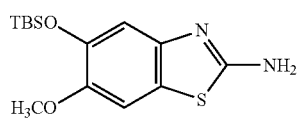
(310B)

This example was prepared according to the general procedure for the synthesis of 2-aminobenzothiazoles described in the table above. Thus, Intermediate 310A was reacted to afford Intermediate 310B as a viscous brown oil (36% Yield). LC-MS: Method H, RT=1.16 min, MS (ESI) m/z: 311.2 (M+H)$^+$. $^1$H NMR (400 MHz, CHLOROFORM-d) δ 7.11 (s, 1H), 7.07 (s, 1H), 4.93 (br. s., 2H), 3.83 (s, 3H), 1.02 (s, 9H), 0.18 (s, 6H).

Intermediate 310C: 2-bromo-5-((tert-butyldimethylsilyl)oxy)-6-methoxybenzo[d]thiazole

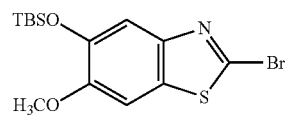
(310C)

This intermediate was prepared according to the general procedure for the synthesis of 2-bromobenzothiazoles described in the table above. Thus, Intermediate 310B was reacted to afford Intermediate 310C as a purple oil (53% yield). LC-MS: Method H, RT=1.50 min, MS (ESI) m/z: 374.0, 376.0 (M+H)$^+$. $^1$H NMR (400 MHz, CHLOROFORM-d) δ 7.08 (s, 1H), 6.99 (s, 1H), 3.69 (s, 3H), 0.84 (s, 9H), 0.00 (s, 6H).

Intermediate 310D: 2-bromo-6-methoxybenzo[d]thiazol-5-ol

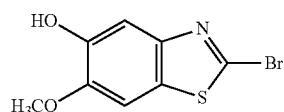
(310D)

To a solution of Intermediate 310C (76 mg, 0.203 mmol) in THF (2030 μl) was added TBAF (1.0 M in THF) (264 μl, 0.264 mmol) at room temperature. After 10 min, the reaction mixture was diluted with EtOAc and washed with brine. The organic phase was concentrated and purified by ISCO (12 g, 0-70% EtOAc/Hexanes, 18 min. Product at 28%) to give Intermediate 310D (28 mg, 0.108 mmol, 53.0% yield) as a white solid. LC-MS: Method H, RT=1.05 min, MS (ESI) m/z: 260.0, 262.0 (M+H)$^+$. $^1$H NMR (400 MHz, CHLOROFORM-d) δ 7.53 (s, 1H), 7.21 (s, 1H), 5.80 (s, 1H), 3.99 (s, 3H).

Example 310

This example was prepared according to the general procedure for quinoxaline-benzothiazoles described in the table above. Thus, reaction of Intermediate 310D with Intermediate I-2 afforded Example 310 in 36% yield following purification by preparative HPLC (Method D, 15-55% over 20 min). LC-MS: Method H, RT=1.17 min, MS (ESI) m/z: 368.1 (M+H)$^+$. $^1$H NMR (500 MHz, DMSO-d$_6$) δ 9.46 (br. s., 1H), 9.09 (s, 1H), 8.79 (s, 1H), 8.01 (s, 1H), 7.69 (s, 1H), 7.47 (s, 1H), 4.82 (s, 2H), 3.91 (s, 3H), 3.48 (s, 3H), 2.68 (s, 3H).

Example 311

5,6-dimethoxy-2-(2-(methoxymethyl)-7-methylquinoxalin-5-yl)benzo[d]thiazole

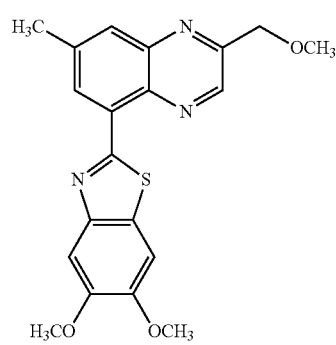
(311)

Intermediate 311A:
2-bromo-5,6-dimethoxybenzo[d]thiazole

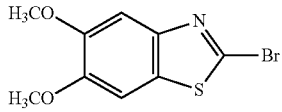

To a solution of Intermediate 310D (14 mg, 0.054 mmol) solvated in DMF (1 mL) was added potassium carbonate (37.2 mg, 0.269 mmol) followed by iodomethane (10.10 μl, 0.161 mmol). The reaction mixture was allowed to stir at room temperature overnight. After 14 h, the reaction mixture was diluted with hexanes and washed with water followed by brine. The organic phase was dried over MgSO$_4$, filtered and concentrated to provide Intermediate 311A (11 mg, 0.040 mmol, 75% yield) as a white solid, which was taken on without further purification. LC-MS: Method H, RT=1.13 min, MS (ESI) m/z: 274.0, 276.0 (M+H)$^+$. $^1$H NMR (400 MHz, CHLOROFORM-d) δ 7.46 (s, 1H), 7.22 (s, 1H), 3.97 (s, 3H), 3.96 (s, 3H.)

Example 311

This example was prepared according to the general procedure for quinoxaline-benzothiazoles described in the table above. Thus, reaction of Intermediate 311A with Intermediate I-2 afforded Example 311 in 30% yield following purification by preparative HPLC (Method D, 30-70% over 10 min). LC-MS: Method H, RT=1.27 min, MS (ESI) m/z: 382.1 (M+H)$^+$. $^1$H NMR (500 MHz, DMSO-d$_6$) δ 9.11 (s, 1H), 8.80 (s, 1H), 8.03 (s, 1H), 7.75 (s, 1H), 7.67 (s, 1H), 4.82 (s, 2H), 3.91 (s, 3H), 3.90 (s, 3H), 3.48 (s, 3H), 2.69 (s, 3H).

Example 312

(6-methoxy-2-(2-(methoxymethyl)-7-methylquinoxalin-5-yl)benzo[d]thiazol-5-yl) methanol

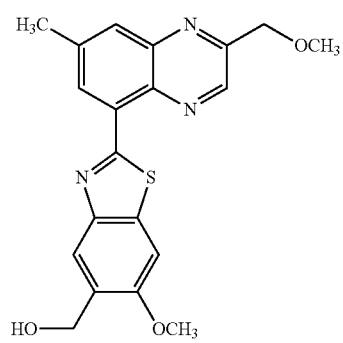

Intermediate 312A: 2-methoxy-5-nitrobenzonitrile

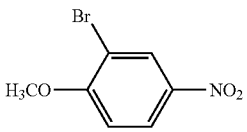

To a vessel charged with 2-bromo-1-methoxy-4-nitrobenzene (1 g, 4.31 mmol), zinc cyanide (0.506 g, 4.31 mmol), zinc (0.028 g, 0.431 mmol) and palladium tetrakis (0.174 g, 0.151 mmol) was added DMF (14.37 ml), and the mixture was sparged with argon for 20 min. The vial was sealed and heated to 90° C. overnight. After 22 h, the black solution was diluted with water and EtOAc. The organic phase was extracted, washed with brine, concentrated and purified by ISCO (80 g, 0-100% EtOAc/Hexanes, 28 min. Product at 50%) to provide Intermediate 312A (520 mg, 2.92 mmol, 67.7% yield) as an off-white solid. LC-MS: Method H, RT=0.78 min, MS (ESI) m/z: None Observed (M+H)$^+$. $^1$H NMR (400 MHz, CHLOROFORM-d) δ 8.49 (d, J=2.6 Hz, 1H), 8.48-8.43 (m, 1H), 7.10 (d, J=9.2 Hz, 1H), 4.08 (s, 3H).

Intermediate 312B: 2-methoxy-5-nitrobenzaldehyde

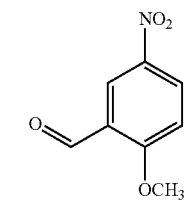

A solution of Intermediate 312A (520 mg, 2.92 mmol) in Et$_2$O (23.400 mL) was cooled to 0° C. under an atmosphere of N$_2$. A solution of DIBAl—H (1.0 M in Toluene) (4.38 mL, 4.38 mmol) was then added dropwise causing bubbling to occur. After 5 min of stirring, the reaction mixture was allowed to thaw to room temperature. After an additional 3 h, the orange solution was poured into a mixture of ice and 10 mL of glacial acetic acid. This mixture was stirred while the ice melted, diluted with EtOAc and DI water and then extracted. The organic phase was concentrated and purified by ISCO (80 g, 0-100% EtOAc/Hexanes, 28 min. Product at 55%) to afford Intermediate 312B (410 mg, 1.811 mmol, 62.0% yield) as a light orange solid. LC-MS: Method H, RT=0.77 min, MS (ESI) m/z: 182.1 (M+H)$^+$. $^1$H NMR (400 MHz, CHLOROFORM-d) δ 10.46 (s, 1H), 8.71 (d, J=2.9 Hz, 1H), 8.45 (dd, J=9.2, 2.9 Hz, 1H), 7.12 (d, J=9.2 Hz, 1H), 4.08 (s, 3H).

Intermediate 312C: (2-methoxy-5-nitrophenyl)methanol

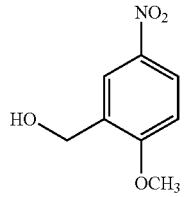

(312C)

A solution of Intermediate 312B (410 mg, 2.263 mmol) in Toluene (11.500 mL) and THF (11.50 mL) was cooled to −78° C. under an atmosphere of $N_2$. DIBAL-H (1.0 M in Toluene) (3.40 mL, 3.40 mmol) was then added to the cooled solution dropwise. After the initial bubbling had subsided, the reaction mixture was allowed to thaw to room temperature. After 1 h, the reaction mixture was cooled to 0° C. and quenched with 1.0 M HCl. The resulting suspension was stirred vigorously for 45 min to fully cleave the aluminate complex. The mixture was then diluted with EtOAc and extracted. The organic phase was washed with brine, dried over $MgSO_4$, filtered and concentrated. The resulting crude product was purified by ISCO (80 g, 0-100% EtOAc/Hexanes, 33 min. Product at 50%) to give Intermediate 312C (370 mg, 1.717 mmol, 76% yield) as a light yellow solid. LC-MS: Method H, RT=0.68 min, MS (ESI) m/z: 184.0 $(M+H)^+$. $^1$H NMR (400 MHz, CHLOROFORM-d) δ 8.29 (d, J=2.9 Hz, 1H), 8.21 (dd, J=9.0, 2.6 Hz, 1H), 6.94 (d, J=9.0 Hz, 1H), 4.75 (d, J=6.4 Hz, 2H), 3.97 (s, 3H), 2.07 (t, J=6.4 Hz, 1H).

Intermediate 312D: tert-butyl((2-methoxy-5-nitrobenzyl)oxy)dimethylsilane

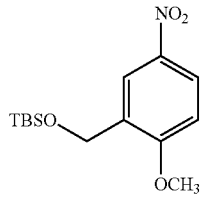

(312D)

To a solution of Intermediate 312C (370 mg, 1.717 mmol) and triethylamine (0.479 mL, 3.43 mmol) in DCM (17.200 mL) was added TBS-Cl (336 mg, 2.232 mmol) followed by DMAP (42.0 mg, 0.343 mmol). After 2 h, the reaction mixture was concentrated and the crude material was purified by ISCO (80 g, 0-20% EtOAc/Hexanes, 28 min. Product at 15%) to give Intermediate 312D (490 mg, 1.647 mmol, 96% yield) as a yellow oil. LC-MS: Method H, RT=1.24 min, MS (ESI) m/z: None Observed $(M+H)^+$. $^1$H NMR (400 MHz, CHLOROFORM-d) δ 8.45-8.35 (m, 1H), 8.17 (dd, 2.6 Hz, 1H), 6.88 (d, J=8.8 Hz, 1H), 4.75 (s, 2H), 3.94 (s, 3H), 0.99 (s, 9H), 0.15 (s, 6H).

Intermediate 312E: 3-(((tert-butyldimethylsilyl)oxy)methyl)-4-methoxyaniline

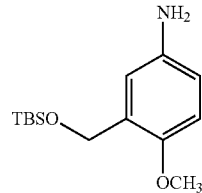

(312E)

Degussa grade Pd/C (175 mg, 0.165 mmol) was added to a 250 mL round bottom flask containing Intermediate 312D (490 mg, 1.647 mmol). The mixture was carefully wet with a few mL of MeOH before adding the total volume of solvent (14.0 mL). The head space of the flask was evacuated until the solvent began to slightly bubble and then back-filled with $N_2$. A hydrogen balloon was attached to the flask, and the solution was sparged with $H_2$ for about 5 minutes through a vent needle. The vent was removed and the reaction mixture was stirred vigorously under the $H_2$ atmosphere for 1 h before being filtered over celite to remove the Pd/C. The celite was rinsed with EtOAc, and the filtrate was concentrated to afford Intermediate 312E (430 mg, 1.608 mmol, 98% yield) as a brown oil. LC-MS: Method H, RT=0.81 min, MS (ESI) m/z: 268.3 $(M+H)^+$. $^1$H NMR (400 MHz, CHLOROFORM-d) δ 6.88 (d, J=2.9 Hz, 1H), 6.66 (d, J=8.4 Hz, 1H), 6.55 (dd, J=8.4, 2.9 Hz, 1H), 4.72 (s, 2H), 3.75 (s, 3H), 3.43 (br. s., 2H), 0.97 (s, 9H).

Intermediate 312F: 5-(((tert-butyldimethylsilyl)oxy)methyl)-6-methoxybenzo[d]thiazol-2-amine

Intermediate 312G: (2-amino-6-methoxybenzo[d]thiazol-5-yl)methanol

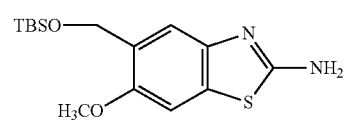

(312F)

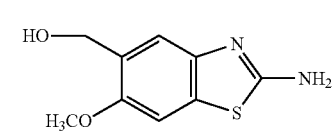

(312G)

To a solution of Intermediate 312E (430 mg, 1.608 mmol) in acetonitrile (13.700 mL) was added ammonium thiocyanate (159 mg, 2.090 mmol). The mixture was stirred at room temperature for 10 min followed by the addition of benzyltrimethylammonium tribromide (627 mg, 1.608 mmol). After 3 days the reaction mixture was diluted with saturated $NaHCO_3$ and extract with EtOAc 3×. The organic phase was dried over $MgSO_4$, filtered, concentrated and purified by ISCO (40 g, 0-100% EtOAc/Hexanes, 19 min. Product at 50%) to give Intermediate 312F (219 mg, 0.675 mmol, 42.0% yield) as a brown oil. LC-MS: Method H, RT=0.89 min, MS (ESI) m/z: 325.3 $(M+H)^+$. $^1$H NMR (400 MHz, CHLOROFORM-d) δ 7.69 (s, 1H), 7.06 (s, 1H), 4.97 (br. s., 2H), 4.80 (d, J=0.9 Hz, 2H), 3.84 (s, 3H), 0.98 (s, 9H), 0.13

(s, 6H). The silica gel column was further flushed (0-20% DCM/MeOH, 19 min. Product at 12%) to afford Intermediate 312G (166 mg, 0.790 mmol, 49.1% yield) as a tan solid. LC-MS: Method H, RT=0.47 min, MS (ESI) m/z: 211.2 (M+H)+. 1H NMR (400 MHz, METHANOL-d4) δ 7.41 (s, 1H), 7.21 (s, 1H), 4.64 (s, 2H), 3.83 (s, 3H).

Intermediate 312H: (2-bromo-6-methoxybenzo[d]thiazol-5-yl)methanol

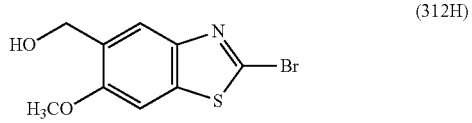 [SMILES: COc1cc2sc(Br)nc2cc1CO]

(312H)

To a suspension of Intermediate 312G (160 mg, 0.761 mmol) in acetonitrile (7610 µl) was added copper (II) bromide (170 mg, 0.761 mmol) followed by t-Butyl nitrite (131 µl, 0.989 mmol). After 1 h of stirring, the reaction mixture was diluted with EtOAc, and poured into a 1.0 M HCl solution. The organic phase was dried over MgSO4, filtered, concentrated and purified by ISCO (40 g, 0-70% EtOAc/Hexanes, 19 min. Product at 35%) to afford Intermediate 312H (119 mg, 0.434 mmol, 57.0% yield) as an off-white solid. LC-MS: Method H, RT=0.81 min, MS (ESI) m/z: 274.1, 276.1 (M+H)+. 1H NMR (400 MHz, METHANOL-d4) δ 7.93 (s, 1H), 7.50 (s, 1H), 4.71 (d, J=0.7 Hz, 2H), 3.91 (s, 3H).

Example 312

This example was prepared according to the general procedure for quinoxaline-benzothiazoles described in the table above. Thus, reaction of Intermediate 312H with Intermediate I-2 afforded Example 312 in 47% yield following purification by preparative HPLC (Method D, 30-70% over 20 min). LC-MS: Method H, RT=0.96 min, MS (ESI) m/z: 382.2 (M+H)+. 1H NMR (500 MHz, DMSO-d6) δ 9.11 (br. s., 1H), 8.82 (br. s., 1H), 8.08 (br. s., 1H), 8.04 (br. s., 1H), 7.74 (br. s., 1H), 4.83 (br. s., 2H), 4.65 (br. s., 2H), 3.92 (br. s., 3H), 3.49 (br. s., 3H), 2.70 (br. s., 3H).

Example 313

6-chloro-5-fluoro-4-methoxy-2-(2-(methoxymethyl)-7-methylquinoxalin-5-yl) benzo[d]thiazole

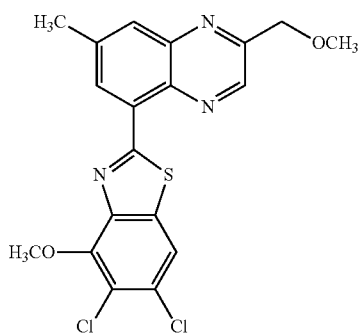

(313)

Intermediate 313A: 1-chloro-2-fluoro-3-methoxy-4-nitrobenzene

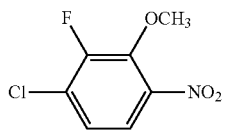

(313A)

To a 0° C. solution of 1-chloro-2-fluoro-3-methoxybenzene (1.606 g, 10 mmol) in acetic acid (5.00 ml) was added fuming nitric acid (0.933 ml, 20.00 mmol) followed by the dropwise addition of sulfuric acid (2.132 ml, 40.0 mmol). After 30 min, the reaction mixture was poured into water and diluted with ethyl acetate. The organic phase was separated and washed 2× with saturated NaHCO3 followed by a final brine wash. The organic solution was then dried over MgSO4, filtered, concentrated and purify by ISCO (120 g, 10-50% EtOAc/Hexanes, 25 min. Desired regioisomer eluted first) affording Intermediate 313A (900 mg, 4.38 mmol, 44% yield) as a yellow solid. LC-MS: Method H, RT=1.15 min, MS (ESI) m/z: None Observed (M+H)+. 1H NMR (400 MHz, CHLOROFORM-d) δ 7.60 (dd, J=9.0, 2.2 Hz, 1H), 7.24 (dd, J=9.0, 6.6 Hz, 1H), 4.11 (d, J=1.8 Hz, 3H). Regiochemistry confirmed through NMR analysis of both regioisomeric products.

Intermediate 313B: 4-chloro-3-fluoro-2-methoxyaniline

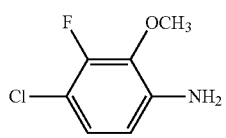

(313B)

A solution of Intermediate 313A (700 mg, 3.41 mmol) in MeOH (17.000 mL, 0.2 M) was added NH4Cl (3643 mg, 68.1 mmol) and zinc dust (2226 mg, 34.1 mmol) was heated to reflux for 1 h. The resulting mixture was allowed to cool to room temperature and the solvent was removed in vacuo. The resulting residue was diluted with EtOAc and saturated sodium bicarbonate (0.2 M of each) and stirred vigorously for an additional 1 hr. The mixture was filtered over celite, the organic layer was separated, washed with brine, dried over MgSO4, filtered and concentrated to give Intermediate 313B (466 mg, 2.66 mmol, 78% yield) as a dark brown solid. This material was taken on without further purification. LC-MS: Method H, RT=1.05 min, MS (ESI) m/z: 176.1, 178.1 (M+H)+. 1I-NMR (400 MHz, CHLOROFORM-d) δ 6.87 (dd, 7.5 Hz, 1H), 6.43 (dd, J=8.7, 1.9 Hz, 1H), 3.92 (d, J=1.5 Hz, 3H), 3.49 (s, 2H).

Intermediate 313C: 6-chloro-5-fluoro-4-methoxy-benzo[d]thiazol-2-amine

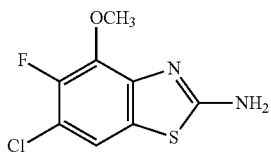
(313C)

This example was prepared according to the general procedure for 2-aminobenzothiazoles described in the table above. Thus, reaction of Intermediate 313B afforded Intermediate 313C in 21% yield. LC-MS: Method H, RT=0.99 min, MS (ESI) m/z: 233.1, 235.0 (M+H)$^+$. $^1$H NMR (400 MHz, CHLOROFORM-d) δ 7.30 (d, J=6.2 Hz, 1H), 5.38 (br. s., 2H), 4.15 (d, J=1.8 Hz, 3H).

Intermediate 313D: 6-chloro-5-fluoro-4-methoxy-benzo[d]thiazol-2-amine

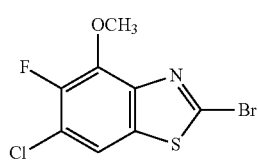
(313D)

Intermediate 313D was prepared according to the general procedure for 2-bromobenzothiazoles described in the table above. Thus, reaction of Intermediate 313C afforded Intermediate 313D in 58% yield. LC-MS: Method H, RT=1.29 min, MS (ESI) m/z: 296.0, 298.0, 299.9 (M+H)$^+$. $^1$H NMR (400 MHz, CHLOROFORM-d) δ 7.50 (d, J=5.7 Hz, 1H), 4.30 (d, J=1.8 Hz, 3H).

Example 313

This example was prepared according to the general procedure for quinoxaline-benzothiazoles described in the table above. Thus, reaction of Intermediate 313D with Intermediate I-2 afforded Example 313 in 8% yield following purification by preparative HPLC (Method D, 60-100% over 20 min). LC-MS: Method H, RT=1.49 min, MS (ESI) m/z: 404.1, 406.1 (M+H)$^+$. $^1$H NMR (500 MHz, DMSO-d$_6$) δ 9.13 (s, 1H), 8.89 (s, 1H), 8.20 (d, J=6.1 Hz, 1H), 8.13 (br. s., 1H), 4.84 (s, 2H), 4.41 (s, 3H), 3.48 (s, 3H), 2.73 (s, 3H).

Example 314

4-cyclopropyl-5-fluoro-6-methoxy-2-(2-(methoxymethyl)-7-methylquinoxalin-5-yl)benzo[d]thiazole

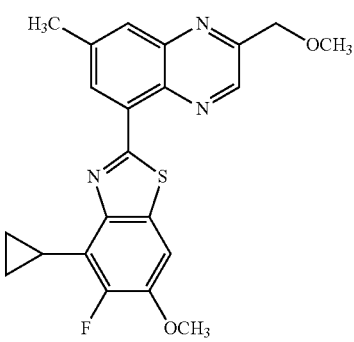
(314)

Example 283 (19 mg, 0.047 mmol) was solvated in a solution of cyclopropylzinc(II) bromide (0.5 M in THF, 1411 μl, 0.706 mmol) and transferred to a microwave vial containing Pd(dppf)$_2$Cl$_2$—CH$_2$Cl$_2$ adduct (3.84 mg, 4.70 μmol). The solution was sparged with argon for 5 min, sealed and then heated to 100° C. in the microwave. The crude reaction mixture was then concentrated, retaken in DMF, filtered and purified by preparatory HPLC (Method D, 60-100% over 20 min) to afford Example 314 (1.1 mg, 2.69 μmol, 6% yield). LC-MS: Method H, RT=1.47 min, MS (ESI) m/z: 410.1, (M+H)$^+$. $^1$H NMR (500 MHz, DMSO-d$_6$) δ 9.10 (s, 1H), 8.73 (d, J=1.7 Hz, 1H), 8.05 (s, 1H), 7.75 (d, J=7.7 Hz, 1H), 4.86-4.78 (m, 2H), 3.94 (s, 3H), 3.49 (s, 3H), 2.70 (s, 3H), 2.66-2.58 (m, 1H), 1.18-1.13 (m, 2H), 0.87 (t, J=6.9 Hz, 2H).

Example 315

6-ethoxy-4,5-difluoro-2-(2-methoxy-7-methylquinoxalin-5-yl)benzo[d]thiazole

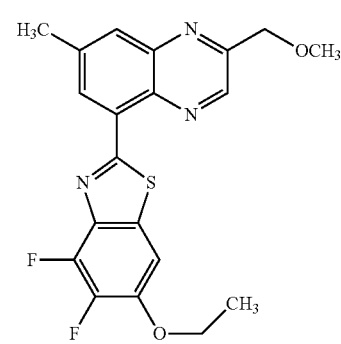
(315)

Intermediate 315A: 2-bromo-6-ethoxy-4,5-difluorobenzo[d]thiazole

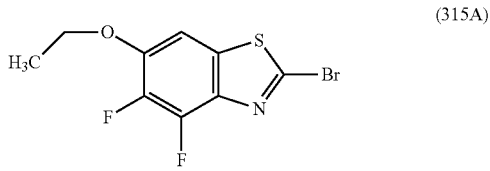
(315A)

To a vial charged with Intermediate I-42 (13 mg, 0.049 mmol) and Cs$_2$CO$_3$ (80 mg, 0.244 mmol) was added DMF (1 mL). The resulting mixture was vigorously stirred for 5 min before the addition of iodoethane (0.012 mL, 0.147 mmol). After 16 h of stirring at room temperature, the reaction mixture was diluted with hexanes and extracted with water. The organic phase was dried over MgSO$_4$, filtered, concentrated and purified by ISCO (12 g, 0-20% EtOAc/Hexanes, 16 min. Product at 8%) to afford Intermediate 315A (9 mg, 0.031 mmol, 62.6% yield) as a white solid. LC-MS: Method H, RT=1.27 min, MS (ESI) m/z: 294.0, 296.0 (M+H)$^+$. $^1$H NMR (400 MHz, CHLOROFORM-d) δ 7.08 (dd, J=6.6, 2.0 Hz, 1H), 4.16 (q, J=6.9 Hz, 2H), 1.51 (t, J=7.0 Hz, 3H).

Example 315

This example was prepared according to the general procedure for quinoxaline-benzothiazoles described in the table above. Thus, reaction of Intermediate 315A with Intermediate I-2 afforded Example 315 in 22% yield following purification by preparative HPLC (Method D, 60-100% over 20 min). LC-MS: Method H, RT=1.48 min, MS (ESI) m/z: 388.1 (M+H)$^+$. $^1$H NMR (500 MHz, DMSO-d$_6$) δ 8.76 (s, 1H), 8.62 (s, 1H), 7.87 (s, 1H), 7.83 (d, J=6.9 Hz, 1H), 4.26 (q, J=6.9 Hz, 2H), 4.10 (s, 3H), 2.66 (s, 3H), 1.45 (t, J=7.0 Hz, 3H).

Example 316

N-(2-((4,5-difluoro-2-(2-methoxy-7-methylquinoxalin-5-yl)benzo[d]thiazol-6-yl) oxy)ethyl)-3-fluorobenzenesulfonamide

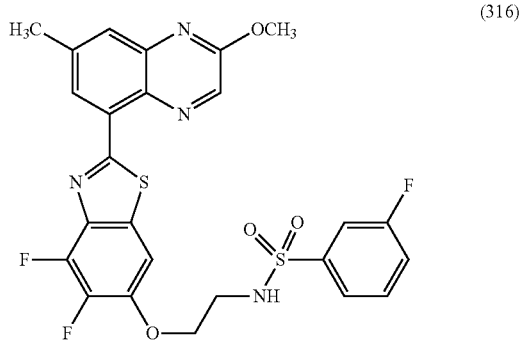 [SMILES: COc1cnc2c(-c3nc4c(F)c(F)c(OCCNS(=O)(=O)c5cccc(F)c5)cc4s3)cc(C)cc2n1]
(316)

Intermediate 316A: tert-butyl (2-((2-bromo-4,5-difluorobenzo[d]thiazol-6-yl)oxy)ethyl)carbamate

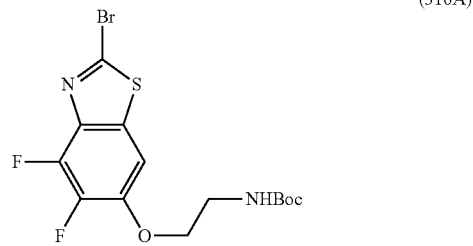
(316A)

A solution of Intermediate I-42 (100 mg, 0.376 mmol) and triphenylphosphine (197 mg, 0.752 mmol) in THF (2 mL) was heated to reflux. To this refluxing mixture was added a pre-mixed solution of DIAD (0.219 mL, 1.128 mmol) and tert-butyl (2-hydroxyethyl)carbamate (182 mg, 1.128 mmol) in THF (2 mL) over the course of 2 h via syringe pump. The crude reaction mixture was concentrated and purified by ISCO (40 g, 0-30% DCM/EtOAc, 22 min, Product at 8%) to afford Intermediate 316A (53 mg, 0.130 mmol, 34.5% yield) as a yellow amorphous solid. LC-MS: Method H, RT=1.25 min, MS (ESI) m/z: 409.0, 411.0 (M+H)$^+$. $^1$H NMR (400 MHz, CHLOROFORM-d) d 7.11 (dd, J=6.5, 1.9 Hz, 1H), 5.03 (br. s., 1H), 4.14 (t, J=5.2 Hz, 2H), 3.60 (q, J=5.4 Hz, 2H), 1.45 (s, 9H).

Intermediate 316B: 2-((2-bromo-4,5-difluorobenzo[d]thiazol-6-yl)oxy)ethanamine HCl

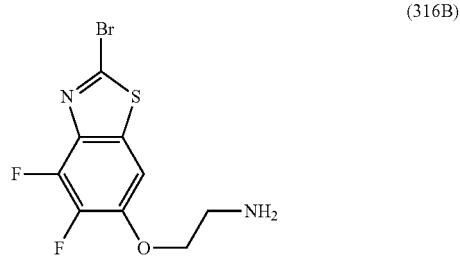 [SMILES: NCCOc1cc2sc(Br)nc2c(F)c1F]
(316B)

To a flask charged with Intermediate 316A (53 mg, 0.130 mmol) was added 4.0 N HCl in dioxane (2.43 mL, 9.71 mmol) causing a white slurry to immediately form. After 1 h, the solution was concentrated in vacuo to afford Intermediate 316B as an HCl salt. LC-MS: Method H, RT=0.83 min, MS (ESI) m/z: 265.1, 267.1 (M+H—CH$_2$CH$_2$NH$_2$)$^+$. $^1$H NMR (400 MHz, METHANOL-d$_4$) δ 7.59 (dd, J=6.9, 2.1 Hz, 1H), 4.42-4.36 (m, 2H), 3.46 (t, J=4.8 Hz, 2H).

Intermediate 316C: N-(2-((2-bromo-4,5-difluorobenzo[d]thiazol-6-yl)oxy)ethyl)-3-fluorobenzenesulfonamide

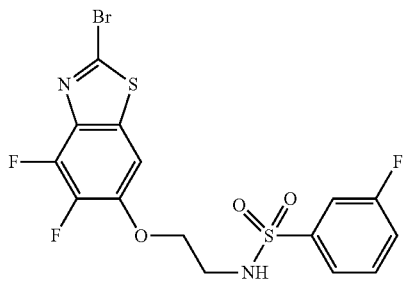

(316C)

To a solution of Intermediate 316B (44 mg, 0.127 mmol) in THF (1.5 mL) was added DIEA (0.067 mL, 0.382 mmol) and 3-fluorobenzene-1-sulfonyl chloride (37.2 mg, 0.191 mmol). The white slurry was stirred for 1 hr before being quenched with water and extracted with EtOAc. The organic phase was further washed with brine, concentrated, and purified by ISCO (12 g, 0-50% EtOAc/Hexanes, 20 min. Product at 38%) to afford Intermediate 316C (53 mg, 0.113 mmol, 89% yield) as a pale yellow, amorphous solid. LC-MS: Method H, RT=1.21 min, MS (ESI) m/z: 467.0, 469.0 (M+H)$^+$. $^1$H NMR (400 MHz, CHLOROFORM-d) δ 7.72-7.67 (m, 1H), 7.63-7.56 (m, 1H), 7.51 (td, 5.3 Hz, 1H), 7.31-7.24 (m, 1H), 7.03 (dd, J=6.6, 2.0 Hz, 1H), 5.16 (t, J=6.2 Hz, 1H), 4.16 (t, J=5.1 Hz, 2H), 3.53-3.46 (m, 2H).

Example 316

This example was prepared according to the general procedure for quinoxaline-benzothiazoles described in the table above. Thus, reaction of Intermediate 316C with Intermediate I-9 afforded Example 316 in 43% yield following purification by preparative HPLC (Method D, 50-100% over 20 min). LC-MS: Method H, RT=1.36 min, MS (ESI) m/z: 561.1 (M+H)$^+$. $^1$H NMR (500 MHz, DMSO-d$_6$) δ 8.67 (s, 1H), 8.53 (d, J=1.1 Hz, 1H), 8.23 (br. s., 1H), 7.79 (s, 1H), 7.72-7.67 (m, 2H), 7.67-7.61 (m, 2H), 7.48 (td, J=8.5, 1.9 Hz, 1H), 4.18 (t, J=5.1 Hz, 2H), 4.08 (s, 3H), 3.36-3.30 (m, 2H-buried under DMSO), 2.62 (s, 3H).

Example 317

N-(2-((4,5-difluoro-2-(2-(methoxymethyl)-7-methylquinoxalin-5-yl)benzo[d]thiazol-6-yl)oxy)ethyl)-3-fluorobenzenesulfonamide

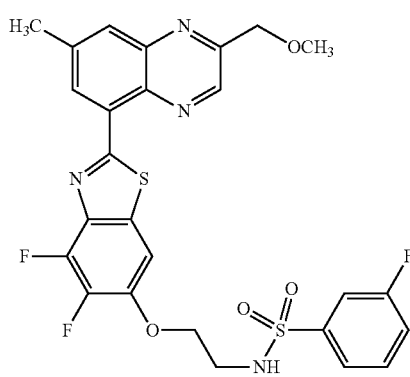

(317)

This example was prepared according to the general procedure for quinoxaline-benzothiazoles described in the table above. Thus, reaction of Intermediate 316C with Intermediate I-2 afforded Example 317 in 6% yield following purification by preparative HPLC (Method D, 45-90% over 20 min). LC-MS: Method H, RT=1.30 min, MS (ESI) m/z: 575.1 (M+H)$^+$. $^1$H NMR (500 MHz, DMSO-d$_6$) δ 9.25-9.04 (m, 1H), 8.83 (br. s., 1H), 8.25 (br. s., 1H), 8.08 (br. s., 1H), 7.79 (d, J=6.1 Hz, 1H), 7.69 (d, J=7.7 Hz, 1H), 7.63 (d, J=7.7 Hz, 1H), 7.46 (br. s., 1H), 4.82 (br. s., 2H), 4.20 (d, J=4.4 Hz, 2H), 3.49 (d, J=5.0 Hz, 3H), 3.36-3.30 (m, 2H-buried under DMSO) 2.70 (br. s., 3H).

Example 318

2-((4-chloro-5-fluoro-2-(2-methoxy-7-methylquinoxalin-5-yl)benzo[d]thiazol-6-yl)oxy)ethanol

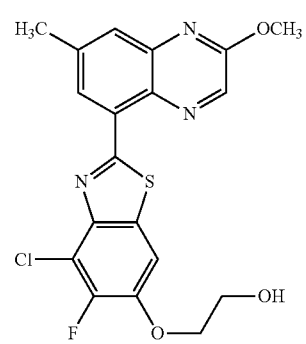

(318)

Intermediate 318A: 2-((4-chloro-2-(2-(difluoromethoxy)-7-methylquinoxalin-5-yl)-5-fluorobenzo[d]thiazol-6-yl)oxy)ethanol

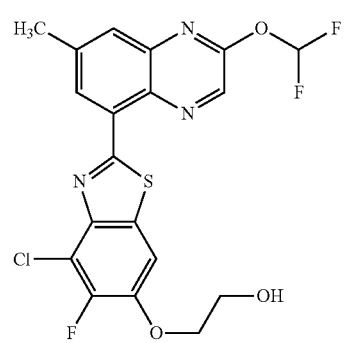

(318A)

A 20 mL microwave vial was charged with Intermediate I-1 (623 mg, 1.853 mmol), Intermediate I-59 (605 mg, 1.853 mmol) and [1,1'-bis(diphenylphosphino) ferrocene]dichloropalladium (II) complex with dichloromethane (1:1) (76 mg, 0.093 mmol). These solids were suspended in a combination of Toluene (11.600 mL), EtOH (3.87 mL) and a 2.0 M solution of Na$_2$CO$_3$ (1.389 mL, 2.78 mmol). The resulting mixture was sparged with argon for 10 min, sealed and then heated in a microwave at 130° C. for 30 min. The crude reaction mixture was diluted with 100 mL EtOAc and filtered over celite. The organic solution was concentrated onto celite and purified by ISCO (80 g, 0-100% EtOAc/Hexanes, 36 min. Product dragged from 50%-100%) to afford Intermediate 318A (630 mg, 1.382 mmol, 74.6% yield) as a bright yellow solid. LC-MS: Method H, RT=1.13 min, MS (ESI) m/z: 456.0, 458.1 (M+H)+. $^1$H NMR (400 MHz, DMSO-d$_6$) δ 9.00 (s, 1H), 8.76 (d, J=1.8 Hz, 1H), 8.03 (d, J=7.7 Hz, 1H), 7.96 (d, J=0.9 Hz, 1H), 7.90 (t, J=71.1 Hz, 1H), 4.99 (t, J=5.5 Hz, 1H), 4.22 (t, J=4.8 Hz, 2H), 3.82 (q, J=5.2 Hz, 2H), 2.70 (s, 3H).

Example 318

To a solution of Intermediate 318A (630 mg, 1.382 mmol) in THF (27.600 mL) was added a 0.5 M solution of NaOMe in MeOH (27.6 mL, 13.82 mmol). After 1 h of stirring, the reaction mixture was quenched with 1.0 N HCl (27.6 mL) and diluted with EtOAc. The organic phase was washed with brine, and concentrated in vacuo to afford Example 318 (650 mg, 1.393 mmol, 91% yield). The majority of this crude material was taken on without further purification, but a small portion was further purified by preparative HPLC for characterization (Method D, 45-80% over 13 min, 100% for 5 min). LC-MS: Method H, RT=1.05 min, MS (ESI) m/z: 420.1, 422.1 (M+H)+. $^1$H NMR (400 MHz, DMSO-d$_6$) δ 8.76 (s, 1H), 8.61 (d, J=1.8 Hz, 1H), 8.00 (d, J=7.7 Hz, 1H), 7.87 (s, 1H), 4.99 (t, J=5.4 Hz, 1H), 4.22 (t, J=5.0 Hz, 2H), 4.10 (s, 3H), 3.82 (q, J=5.2 Hz, 2H), 2.67 (s, 3H).

Example 319

1-((2-(2-(methoxymethyl)-7-methylquinoxalin-5-yl)-4,5-dimethylbenzo[d]thiazol-6-yl)oxy)-2-methylpropan-2-ol A solution of Intermediate I-49 (16 mg, 0.048 mmol) in THF (1 mL) was cooled to −78° C. To this cold solution was added MeMgBr (3.0 M in Et$_2$O) (0.162 mL, 0.485 mmol) dropwise. The resulting mixture was allowed to warm to 0° C. Once at 0° C. the reaction was quenched with 1 mL of 1 M HCl. This mixture was then concentrated and purified by ISCO (12 g, 0-50% EtOAc/Hexanes, 16 min. Product at 25%,) to afford Intermediate 319A (5 mg, 0.015 mmol, 31.2% yield) as a colorless oil. LC-MS: Method H, RT=1.29 min, MS (ESI) m/z: 330.1, 332.1 (M+H)+. $^1$H NMR (400 MHz, CHLOROFORM-d) δ 7.06 (s, 1H), 3.83 (s, 2H), 2.65 (s, 3H), 2.30 (s, 3H), 2.14 (s, 1H), 1.40 (s, 6H).

Example 319

This example was prepared according to the general procedure for quinoxaline-benzothiazoles described in the table above. Thus, reaction of Intermediate 319A with Intermediate I-2 afforded Example 319 in 67% yield following purification by preparative HPLC (Method D, 70-100% over 10 min). LC-MS: Method H, RT=1.16 min, MS (ESI) m/z: 438.2 (M+H)+. $^1$H NMR (500 MHz, DMSO-d$_6$) δ 9.10 (s, 1H), 8.83 (s, 1H), 8.01 (s, 1H), 7.53 (s, 1H), 4.82 (s, 2H), 4.71 (s, 1H), 3.83 (s, 2H), 3.49 (s, 3H), 2.77 (s, 3H), 2.70 (s, 3H), 2.31 (s, 3H), 1.30 (s, 6H).

Example 320

2-((2-(2-(methoxymethyl)-7-methylquinoxalin-5-yl)-4,5-dimethylbenzo[d]thiazol-6-yl) oxy)ethyl methyl carbonate

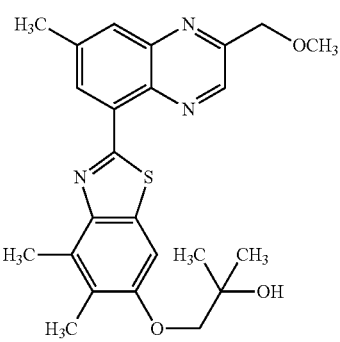

(319)

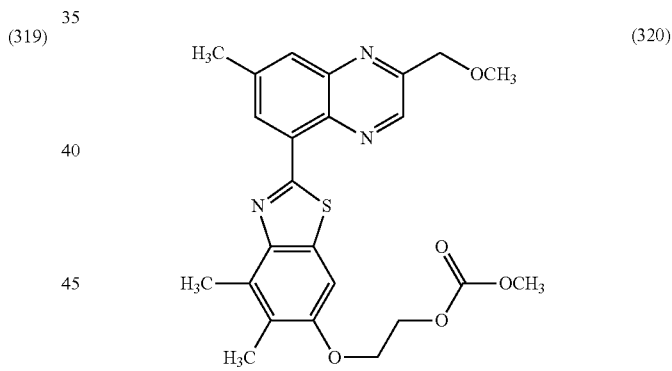

(320)

Intermediate 319A: 1-((2-bromo-4,5-dimethylbenzo[d]thiazol-6-yl)oxy)-2-methylpropan-2-ol Intermediate 320A: 2-((2-chloro-4,5-dimethylbenzo[d]thiazol-6-yl)oxy)ethyl methyl carbonate

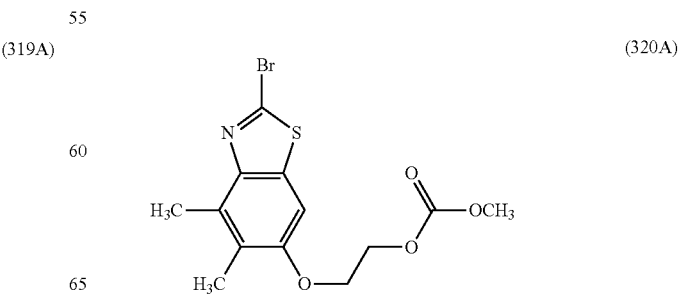

(319A)

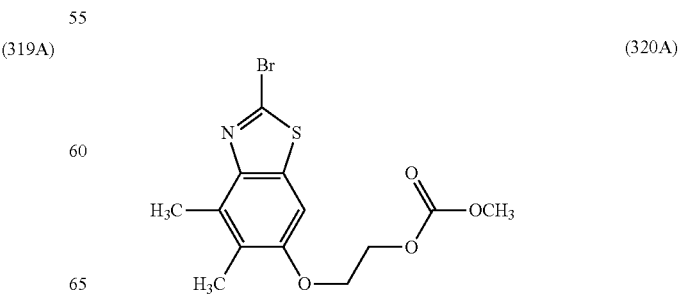

(320A)

To a solution of Intermediate I-51 (30 mg, 0.099 mmol) in THF (1 mL) was added Hunig's Base (0.087 mL, 0.496 mmol) followed by a solution of phosgene (15% by wt in toluene) (0.210 mL, 0.298 mmol). After 15 min of stirring, 1 mL of MeOH was added and the reaction mixture was concentrated. The crude residue was purified by ISCO (12 g, 0-30% EtOAc/Hexanes, 16 min. Product at 15%) to afford Intermediate 320A (12 mg, 0.038 mmol, 38.3% yield) as a white solid. LC-MS: Method H, RT=0.95 min, MS (ESI) m/z: 316.1, 318.1 (M+H)+. $^1$H NMR (400 MHz, CHLOROFORM-d) δ 7.02 (d, J=8.4 Hz, 1H), 4.59-4.53 (m, 2H), 4.25-4.18 (m, 2H), 3.82 (s, 3H), 2.63 (d, J=5.1 Hz, 3H), 2.26 (s, 3H).

Example 320

This example was prepared according to the general procedure for quinoxaline-benzothiazoles described in the table above. Thus, reaction of Intermediate 320A with Intermediate I-2 afforded Example 320 in 50% yield following purification by preparative HPLC (Method D, 60-100% over 15 min). LC-MS: Method H, RT=1.17 min, MS (ESI) m/z: 468.2 (M+H)+. $^1$H NMR (500 MHz, DMSO-$d_6$) δ 9.09 (s, 1H), 8.82 (s, 1H), 8.01 (s, 1H), 7.59 (s, 1H), 4.82 (s, 2H), 4.54 (br. s., 2H), 4.32 (br. s., 2H), 3.76 (s, 3H), 3.49 (s, 3H), 2.76 (s, 3H), 2.70 (s, 3H), 2.25 (s, 3H).

Example 321

2-((2-(2-(methoxymethyl)-7-methylquinoxalin-5-yl)-4,5-dimethylbenzo[d]thiazol-6-yl)oxy)propan-1-ol (racemate)

This example was prepared in a manner analogous to Intermediate I-51. Thus, Intermediate I-50 (rac) was reacted to afford Intermediate 321A (rac) (91% yield) as an off-white, amorphous solid. LC-MS: Method H, RT=1.26 min, MS (ESI) m/z: 314.0, 316.0 (M+H)+. $^1$H NMR (400 MHz, CHLOROFORM-d) δ 7.14 (s, 1H), 4.57-4.46 (m, 1H), 3.80 (d, J=5.3 Hz, 2H), 2.64 (s, 3H), 2.26 (s, 3H), 1.30 (d, J=6.4 Hz, 3H), 1.26 (br. s, 1H).

Example 321

This example was prepared according to the general procedure for quinoxaline-benzothiazoles described in the table above. Thus, reaction of Intermediate 321A (rac) with Intermediate I-2 afforded Example 321 (rac) in 66% yield following purification by preparative HPLC (Method D, 40-75% over 10 min, 100% for 5 min). LC-MS: Method H, RT=0.90 min, MS (ESI) m/z: 423.9 (M+H)+. $^1$H NMR (500 MHz, DMSO-$d_6$) δ 9.09 (s, 1H), 8.83 (s, 1H), 8.01 (s, 1H), 7.62 (s, 1H), 4.88 (t, J=5.5 Hz, 1H), 4.82 (s, 2H), 4.60-4.48 (m, 1H), 3.66 (dt, J=11.1, 5.3 Hz, 1H), 3.60-3.52 (m, 1H), 3.49 (s, 3H), 2.76 (s, 3H), 2.70 (s, 3H), 2.27 (s, 3H), 1.30 (d, J=5.8 Hz, 3H).

Example 322

1-((2-(2-(methoxymethyl)-7-methylquinoxalin-5-yl)-4,5-dimethylbenzo[d]thiazol-6-yl) oxy)propan-2-ol (racemate)

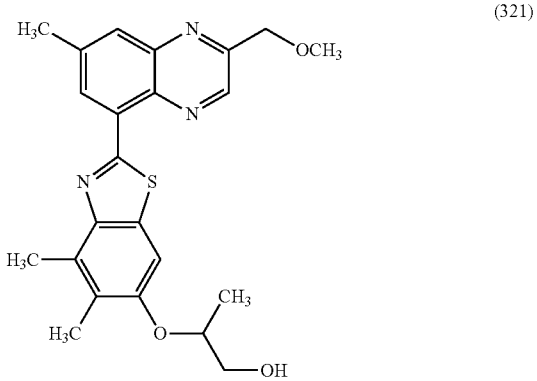 [SMILES: COCc1cnc2c(-c3nc4c(C)c(C)c(OC(C)CO)cc4s3)cc(C)cc2n1]

(321)

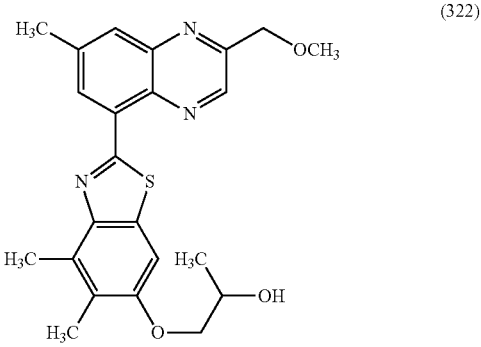 [SMILES: COCc1cnc2c(-c3nc4c(C)c(C)c(OCC(C)O)cc4s3)cc(C)cc2n1]

(322)

Intermediate 321A: 2-((2-bromo-4,5-dimethylbenzo[d]thiazol-6-yl)oxy)propan-1-ol

Intermediate 322A: 2-((2-bromo-4,5-dimethylbenzo[d]thiazol-6-yl)oxy)acetaldehyde

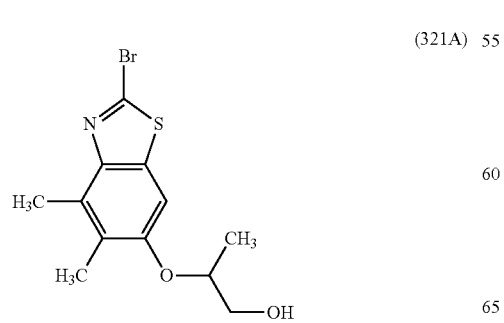

(321A)

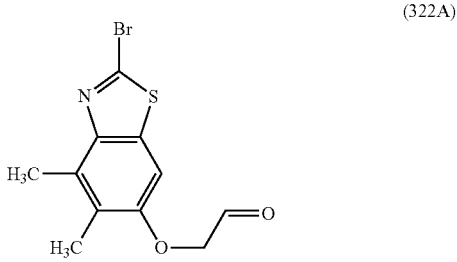 [SMILES: Cc1c(OCC=O)cc2sc(Br)nc2c1C]

(322A)

A solution of Intermediate I-51 (20 mg, 0.066 mmol) in DCM (1 mL) was cooled to 0° C. To this cooled mixture was added Dess-Martin Periodinane (84 mg, 0.199 mmol). After 1 h, the solution was allowed to thaw to room temperature and stirred vigorously for an additional 5 h. The reaction mixture was then concentrated and the residue was purified by ISCO (12 g, 0-50% EtOAc/Hexanes, 16 min. Product at 25%) to afford Intermediate 322A (11 mg, 0.037 mmol, 55.4% yield) as a white solid. LC-MS: Method H, RT=1.09 min, MS (ESI) m/z: 317.7, 319.7 (M+H+H$_2$O)$^+$. $^1$H NMR (400 MHz, CHLOROFORM-d) δ 9.90 (t, J=1.1 Hz, 1H), 6.93 (s, 1H), 4.62 (d, J=1.1 Hz, 2H), 2.69-2.63 (m, 3H), 2.35 (s, 3H).

Intermediate 322B: 1-((2-bromo-4,5-dimethylbenzo[d]thiazol-6-yl)oxy)propan-2-ol (Racemate)

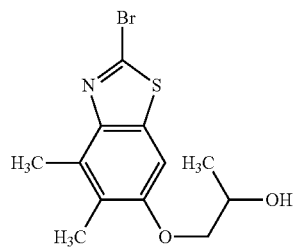
(322B)

A solution of Intermediate 322A (11 mg, 0.037 mmol) in THF (2 mL) was cooled to −78° C. MeMgBr (3.0 M in Et$_2$O) (0.122 mL, 0.366 mmol) was then added dropwise to this cold solution. After 1 h of vigorous stirring, the reaction mixture was quenched with saturated NH$_4$Cl and then allowed to thaw to room temperature. Once at room temperature, the mixture was diluted with EtOAc, the organic phase was extracted, dried over MgSO$_4$, filtered, concentrated, and purified by ISCO (12 g, 0-50% EtOAc/Hexanes, 16 min. Product at 28%) to afford Intermediate 322B (rac) (6 mg, 0.013 mmol, 36.2% yield). LC-MS: Method H, RT=1.57 min, MS (ESI) m/z: 315.9, 317.9 (M+H)$^+$. $^1$H NMR (400 MHz, CHLOROFORM-d) δ 7.06 (s, 1H), 4.62 (d, J=1.1 Hz, 1H), 4.27 (ddd, J=10.1, 6.8, 3.2 Hz, 1H), 4.01-3.94 (m, 1H), 3.85 (dd, J=9.1, 7.4 Hz, 1H), 2.64 (s, 3H), 2.28 (s, 3H), 1.33 (d, J=6.6 Hz, 3H)

Example 322

This example was prepared according to the general procedure for quinoxaline-benzothiazoles described in the table above. Thus, reaction of Intermediate 322B with Intermediate I-2 afforded Example 322 (rac) in 46% yield following purification by preparative HPLC (Method D, 45-90% over 10 min, 100% for 5 min). LC-MS: Method H, RT=0.98 min, MS (ESI) m/z: 424.2 (M+H)$^+$. $^1$H NMR (500 MHz, DMSO-d$_6$) δ 9.10 (s, 1H), 8.83 (s, 1H), 8.02 (s, 1H), 7.55 (s, 1H), 4.92 (d, J=3.9 Hz, 1H), 4.82 (s, 2H), 4.11-4.03 (m, 1H), 4.01-3.93 (m, 1H), 3.92-3.85 (m, 1H), 3.49 (s, 3H), 2.77 (s, 3H), 2.71 (s, 3H), 2.29 (s, 3H), 1.25 (d, J=6.1 Hz, 3H).

Example 323

3-((2-(2-(methoxymethyl)-7-methylquinoxalin-5-yl)-4,5-dimethylbenzo[d]thiazol-6-yl)oxy)butan-2-ol (Diastereomeric Mixture)

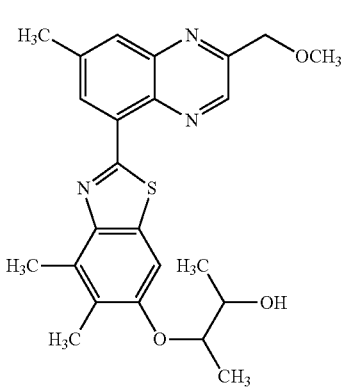
(323)

Intermediate 323A: 2-((2-bromo-4,5-dimethylbenzo[d]thiazol-6-yl)oxy)propanal (Racemate)

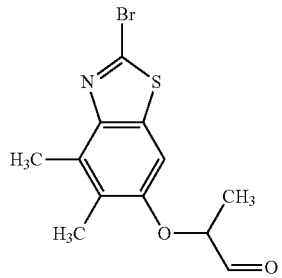
(323A)

This example was prepared in a manner analogous to Intermediate 322A. Thus, Intermediate 321A (rac) was reacted to afford Intermediate 323A (rac) (71% yield). LC-MS: Method H, RT=1.37 min, MS (ESI) m/z: 214.0, 216.0 (M+H)$^+$. $^1$H NMR (400 MHz, CHLOROFORM-d) δ 9.72 (d, J=2.0 Hz, 1H), 6.93 (s, 1H), 4.64 (qd, 2.0 Hz, 1H), 2.66 (s, 3H), 2.33 (s, 3H), 1.55 (d, J=6.8 Hz, 3H).

Intermediate 323B: 3-((2-bromo-4,5-dimethylbenzo[d]thiazol-6-yl)oxy)butan-2-ol (Diastereomeric Mixture)

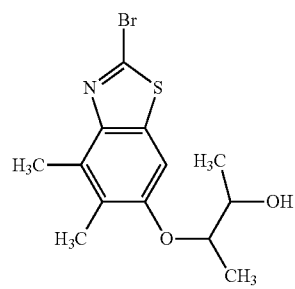
(323B)

This example was prepared in a manner analogous to Intermediate 322B. Thus, Intermediate 323A (rac) was reacted to afford Intermediate 323B (diastereomeric mixture) (57% yield). LC-MS: Method H, RT=1.40 min, MS (ESI) m/z: 330.0, 332.0 (M+H)+. ¹H NMR (400 MHz, CHLOROFORM-d) δ 7.10 (s, 1H), 4.36 (qd, J=6.3, 3.4 Hz, 1H), 4.06 (br. s., 1H), 2.64 (s, 3H), 2.27 (s, 3H), 1.95 (br. s., 1H), 1.30 (d, J=6.4 Hz, 3H), 1.30-1.25 (m, 3H) [Major Diastereomer]. ¹H NMR (400 MHz, CHLOROFORM-d) δ 7.13 (s, 1H), 4.20 (quin, J=6.3 Hz, 1H), 3.97-3.88 (m, 1H), 2.64 (s, 3H), 2.42 (br. s., 1H), 2.27 (s, 3H), 1.30 (d, J=6.4 Hz, 3H), 1.30-1.24 (m, 3H) [Minor Diastereomer].

Example 323

This example was prepared according to the general procedure for quinoxaline-benzothiazoles described in the table above. Thus, reaction of Intermediate 323B (diastereomeric mixture) with Intermediate I-2 afforded Example 323 (diastereomeric mixture) in 62% yield following purification by preparative HPLC (Method D, 50-100% over 40 min). LC-MS: Method H, RT=1.13 min, MS (ESI) m/z: 438.2 (M+H)+. ¹H NMR (500 MHz, DMSO-d₆) δ 9.10 (s, 1H), 8.84 (s, 1H), 8.02 (s, 1H), 7.59 (s, 1H), 7.23-6.95 (m, 1H), 4.82 (s, 2H), 4.36 (d, J=5.8 Hz, 1H), 3.81 (d, J=4.4 Hz, 1H), 3.49 (s, H), 2.76 (s, 3H), 2.71 (s, 3H), 2.27 (s, 3H), 1.30 (d, J=5.8 Hz, 3H), 1.21 (d, J=6.1 Hz, 3H) [Major Diastereomer]. ¹H NMR (500 MHz, DMSO-d₆) δ 9.10 (s, 1H), 8.84 (s, 1H), 8.02 (s, 1H), 7.60 (br. s., 1H), 7.24-6.96 (m, 1H), 4.82 (s, 2H), 4.45 (br. s., 1H), 3.88 (d, J=3.6 Hz, 1H), 3.49 (s, 3H), 2.76 (s, 3H), 2.71 (s, 3H), 2.27 (s, 3H), 1.26 (d, J=5.5 Hz, 3H), 1.17 (d, J=6.1 Hz, 3H) [Minor Diastereomer].

Example 324

2-((4-chloro-5-fluoro-2-(2-methoxy-7-methylquinoxalin-5-yl)benzo[d]thiazol-6-yl)oxy)-1-morpholinoethanone

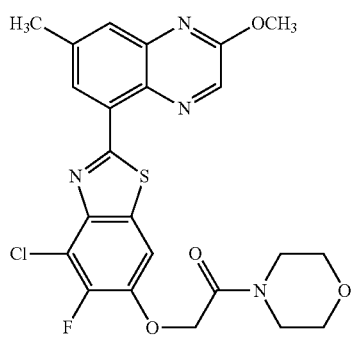

(324)

Intermediate 324A: 2-((4-chloro-5-fluoro-2-(2-methoxy-7-methylquinoxalin-5-yl) benzo[d]thiazol-6-yl)oxy)acetic acid

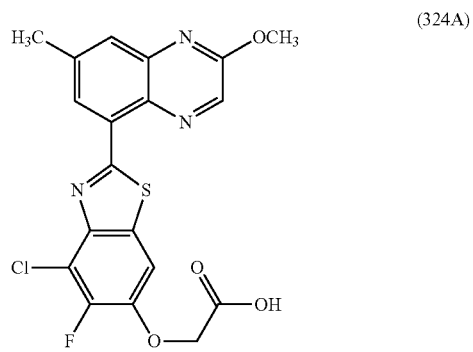 [SMILES: COc1cnc2c(-c3nc4c(Cl)c(F)c(OCC(=O)O)cc4s3)cc(C)cc2n1]

(324A)

This example was prepared according to the general procedure for quinoxaline-benzothiazoles described in the table above. Thus, reaction of Intermediate I-58 with Intermediate I-9 afforded Intermediate 324A in 52% yield. LC-MS: Method H, RT=0.79 min, MS (ESI) m/z: 434.0, 436.0 (M+H)+. ¹H NMR (400 MHz, DMSO-d₆) δ 8.75 (s, 1H), 8.60 (s, 1H), 7.86 (s, 1H), 7.64 (d, J=7.3 Hz, 1H), 4.38 (br. s., 2H), 4.09 (s, 3H), 2.66 (s, 3H).

Example 324

To a suspension of Intermediate 324A (10 mg, 0.023 mmol) in DMF (1 mL) was added N-ethyl-N-isopropylpropan-2-amine (0.024 mL, 0.138 mmol) followed by 2,4,6-tripropyl-1,3,5,2,4,6-trioxatriphosphinane 2,4,6-trioxide (50% solution in DMF) (0.041 mL, 0.069 mmol). The reaction mixture was stirred at room temperature for 2 min until all of starting material had solvated, then morpholine (5.96 μl, 0.069 mmol) was added. After 15 min, the reaction mixture was filtered and purified by preparative HPLC (Method D, 45-85% over 20 min, 100% for 5 min) to afford Example 324 (3.0 mg, 5.96 μmol, 26% yield). LC-MS: Method H, RT=1.14 min, MS (ESI) m/z: 503.1, 505.1 (M+H)+. ¹H NMR (500 MHz, DMSO-d₆) δ 8.74 (s, 1H), 8.62 (s, 1H), 7.91 (d, J=7.7 Hz, 1H), 7.88 (s, 1H), 5.13 (s, 2H), 4.10 (s, 3H), 3.69 (br. s., 2H), 3.62 (br. s., 2H), 3.49 (br. s., 4H), 2.67 (s, 3H).

Example 325

(6-methoxy-2-(2-methoxy-7-methylquinoxalin-5-yl)-5-methylbenzo[d]thiazol-4-yl) methanol (bis-Deuterated)

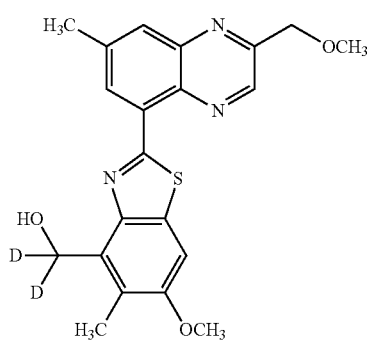

(325)

Example 326

1-(6-methoxy-2-(2-(methoxymethyl)-7-methylquinoxalin-5-yl)-5-methylbenzo[d]thiazol-4-yl)ethanol

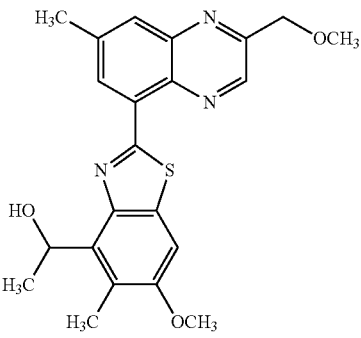

(326)

Intermediate 325A: (2-bromo-6-methoxy-5-methylbenzo[d]thiazol-4-yl)methanol (bis-Deuterated)

(325A)

Intermediate 326A: 1-(2-bromo-6-methoxy-5-methylbenzo[d]thiazol-4-yl)ethanol

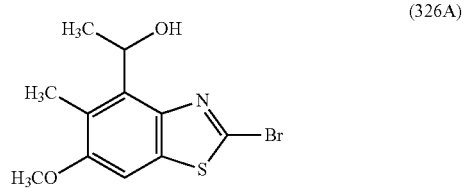

(326A)

A solution of Intermediate I-54D (50 mg, 0.158 mmol) in toluene (791 μl) and THF (791 μl) was cooled to −78° C. under an atmosphere of $N_2$. To this mixture was added DIBAL-D (0.7 M in toluene) (904 μl, 0.633 mmol). After 30 min of stirring, the solution was allowed to thaw to room temperature before being quenched with 3 mL 1 M HCl. The resulting mixture was stirred vigorously for 30 min before being dilute with EtOAc. The organic phase was then extracted, washed with brine, dried over $MgSO_4$, filtered, concentrated and purified by ISCO (12 g, 0-100% EtOAc/Hexanes, 16 min. Product at 38%) to afford Intermediate 325A (5 mg, 0.017 mmol, 10.90% yield) as a white solid. LC-MS: Method H, RT=0.88 min, MS (ESI) m/z: 289.7, 291.7 (M+H)$^+$. $^1$H NMR (400 MHz, CHLOROFORM-d) δ 7.14 (s, 1H), 3.88 (s, 3H), 3.35 (s, 1H), 2.33 (s, 3H)

Example 325

This example was prepared according to the general procedure for quinoxaline-benzothiazoles described in the table above. Thus, reaction of Intermediate 325A with Intermediate I-2 afforded Example 325 in 61% yield following purification by preparative HPLC (Method D, 30-65% over 15 min, 100% for 5 min). LC-MS: Method H, RT=1.06 min, MS (ESI) m/z: 397.8 (M+H)$^+$. $^1$H NMR (500 MHz, DMSO-$d_6$) δ 9.10 (s, 1H), 8.85 (d, J=1.7 Hz, 1H), 8.03 (s, 1H), 7.69 (s, 1H), 5.02 (s, 1H), 4.82 (s, 2H), 3.92 (s, 3H), 3.48 (s, 3H), 2.71 (s, 3H), 2.37 (s, 3H).

A solution of Intermediate I-55 (40 mg, 0.140 mmol) in THF (1398 μl) was cooled to −78° C. MeMgBr (3.0 M in $Et_2O$) (466 μl, 1.398 mmol) was added dropwise to this cold mixture. After 30 min, the reaction was quenched with saturated $NH_4Cl$ and the resulting mixture was allowed to thaw to room temperature. Once at room temperature, the mixture was diluted with EtOAc and washed with saturated $NH_4Cl$ followed by brine. The organic phase was dried over $MgSO_4$, filtered, concentrated and purified by ISCO (12 g, 0-70% EtOAc/Hexanes, 16 min. Product at 20%) to afford Intermediate 326A (12 mg, 0.040 mmol, 28.4% yield). LC-MS: Method H, RT=1.00 min, MS (ESI) m/z: 302.0, 304.0 (M+H)$^+$. $^1$H NMR (400 MHz, CHLOROFORM-d) δ 7.10 (s, 1H), 5.33-5.29 (m, 1H), 3.87 (s, 3H), 2.26 (s, 3H), 1.62-1.58 (m, 3H).

Example 326

This example was prepared according to the general procedure for quinoxaline-benzothiazoles described in the table above. Thus, reaction of Intermediate 326A with Intermediate I-2 afforded Example 326 in 54% yield following purification by preparative HPLC (Method D, 45-80% over 20 min, 100% for 5 min). LC-MS: Method H, RT=1.11 min, MS (ESI) m/z: 410.2 (M+H)$^+$. $^1$H NMR (500 MHz, CHLOROFORM-d) δ 9.09 (s, 1H), 8.71 (s, 1H), 7.95 (s, 1H), 7.29 (s, 1H), 6.72 (d, J=10.7 Hz, 1H), 5.49-5.39 (m, 1H), 4.85 (s, 2H), 3.94 (s, 3H), 3.74 (s, 1H), 3.58 (s, 3H), 2.71 (s, 3H), 2.32 (s, 3H), 1.72 (d, J=6.6 Hz, 3H).

Example 327

2-((4-chloro-2-(2-(methoxymethyl)-7-methylquinoxalin-5-yl)-5-methylbenzo[d]thiazol-6-yl)oxy)ethanol

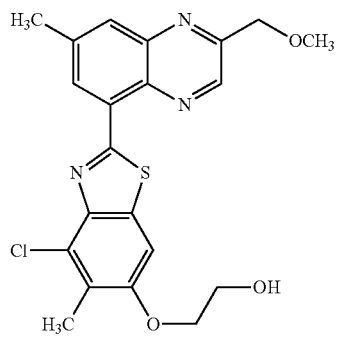
(327)

Intermediate 327A: 2-bromo-4-chloro-5-methylbenzo[d]thiazol-6-ol

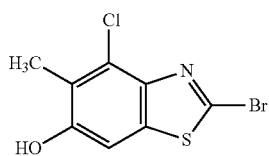
(327A)

This example was prepared in a manner analogous to Intermediate I-44. Thus, Intermediate I-56 was reacted to afford Intermediate 327A (36% yield) as a light pink solid. LC-MS: Method H, RT=0.94 min, MS (ESI) m/z: 277.7, 279.7, 281.6 (M+H)⁺. ¹H NMR (400 MHz, METHANOL-d₄) δ 7.19 (s, 1H), 2.37 (s, 3H).

Intermediate 327B: methyl 2-((2-bromo-4-chloro-5-methylbenzo[d]thiazol-6-yl)oxy) acetate

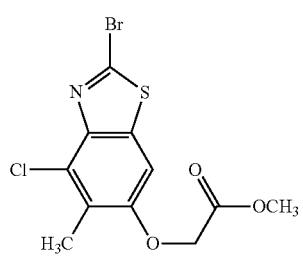
(327B)

This example was prepared in a manner analogous to Intermediate I-49. Thus, Intermediate 327A was reacted to afford Intermediate 327B (79% yield) as an off-white solid. LC-MS: Method H, RT=1.02 min, MS (ESI) m/z: 350.0, 352.0, 353.9 (M+H)⁺. ¹H NMR (400 MHz, CHLOROFORM-d) δ 7.01 (s, 1H), 4.71 (s, 2H), 3.82 (s, 3H), 2.48 (s, 3H).

Intermediate 327C: 2-((2-bromo-4-chloro-5-methylbenzo[d]thiazol-6-yl)oxy)ethanol

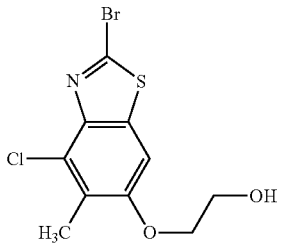
(327C)

This intermediate was prepared in a manner analogous to Intermediate I-51. Thus, Intermediate 327B was reacted to afford Intermediate 327C (82% yield) as an off-white, amorphous solid. LC-MS: Method H, RT=0.93 min, MS (ESI) m/z: 321.9, 324.0, 325.9 (M+H)⁺. ¹H NMR (400 MHz, CHLOROFORM-d) δ 7.13 (s, 1H), 4.17-4.12 (m, 2H), 4.05 (q, J=4.9 Hz, 2H), 2.43 (s, 3H), 1.99 (t, J=6.1 Hz, 1H)

Example 327

This example was prepared according to the general procedure for quinoxaline-benzothiazoles described in the table above. Thus, reaction of Intermediate 327C with Intermediate I-2 afforded Example 327 in 49% yield following purification by preparative HPLC (Method D, 45-90% over 20 min, 100% for 5 min). LC-MS: Method H, RT=1.10 min, MS (ESI) m/z: 430.1, 432.1 (M+H)⁺. ¹H NMR (500 MHz, CHLOROFORM-d) δ 9.07 (s, 1H), 8.95 (s, 1H), 7.95 (s, 1H), 7.31 (s, 1H), 4.84 (s, 2H), 4.21 (t, J=4.3 Hz, 2H), 4.08 (d, J=3.9 Hz, 2H), 3.58 (s, 3H), 2.71 (s, 3H), 2.49 (s, 3H), 2.08-1.98 (m, 1H).

Example 328

1-(6-methoxy-2-(2-(methoxymethyl)-7-methylquinoxalin-5-yl)-5-methylbenzo[d]thiazol-4-yl)-2,2-dimethylpropan-1-ol (Racemate)

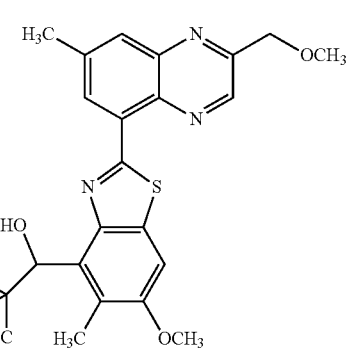
(328)

Intermediate 328A: 1-(2-bromo-6-methoxy-5-methylbenzo[d]thiazol-4-yl)-2,2-dimethylpropan-1-ol (Racemate)

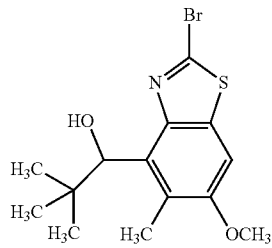
(328A)

A solution of Intermediate I-55 (20 mg, 0.070 mmol) in THF (1 mL) was cooled to −78° C. tert-butylmagnesium chloride (0.091 mL, 0.091 mmol) was added. After 30 min, the reaction mixture was warmed to −10° C. and then quenched with saturated NH₄Cl. The resulting mixture was then diluted with EtOAc, and the organic phase was extracted, dried over MgSO₄, filtered, concentrated and purified by ISCO (12 g, 0-100% EtOAc/Hexanes, 16 min. Product at 16%) to afford Intermediate 328A (rac) (8.5 mg, 0.025 mmol, 35.3% yield). LC-MS: Method H, RT=1.16 min, MS (ESI) m/z: 344.0, 346.0 (M+H)⁺. ¹H NMR (400 MHz, CHLOROFORM-d) δ 7.12 (s, 1H), 4.96 (d, J=11.4 Hz, 1H), 3.88 (s, 3H), 2.28 (s, 3H), 0.96 (s, 9H).

Example 328

This example was prepared according to the general procedure for quinoxaline-benzothiazoles described in the table above. Thus, reaction of Intermediate 328A (rac) with Intermediate I-2 afforded Example 328 (rac) in 18% yield following purification by preparative HPLC (Method D, 65-100% over 15 min). LC-MS: Method H, RT=1.23 min, MS (ESI) m/z: 452.2 (M+H)⁺. ¹H NMR (500 MHz, DMSO-d₆) δ 9.12 (s, 1H), 8.64 (s, 1H), 8.07 (s, 1H), 7.73 (s, 1H), 6.34 (d, J=10.7 Hz, 1H), 5.00 (d, J=10.7 Hz, 1H), 4.83 (br. s., 2H), 3.94 (s, 3H), 3.49 (s, 3H), 2.72 (br. s., 3H), 2.30 (s, 3H), 1.00 (br. s., 9H).

Example 329

5-fluoro-6-isopropoxy-2-(2-(methoxymethyl)-7-methylquinoxalin-5-yl)benzo[d]thiazole

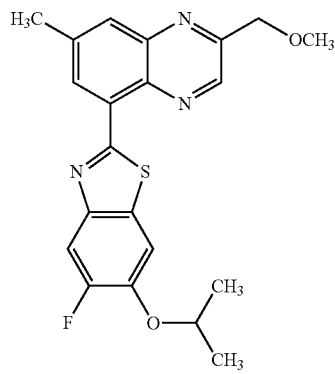
(329)

Intermediate 329A: 2-bromo-5-fluoro-6-isopropoxybenzo[d]thiazole

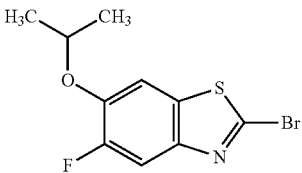
(329A)

To a solution of Intermediate I-60 (34 mg, 0.137 mmol) in DMF (685 μl) was added 2-iodopropane (68.5 μl, 0.685 mmol) followed by K₂CO₃ (47.4 mg, 0.343 mmol). After 3 h of vigorous stirring, the reaction mixture was diluted with EtOAc, filtered over celite, concentrated and purified by ISCO (12 g, 0-10% EtOAc/Hexanes, 16 min. Product at 3%) to afford Intermediate 329A (38 mg, 0.131 mmol, 96% yield) as a white solid. LC-MS: Method H, RT=1.07 min, MS (ESI) m/z: 290.1, 292.1 (M+H)⁺. ¹H NMR (400 MHz, CHLOROFORM-d) δ 7.68 (d, J=11.0 Hz, 1H), 7.33 (d, J=7.5 Hz, 1H), 4.57 (spt, J=6.1 Hz, 1H), 1.41 (d, J=5.9 Hz, 6H).

Example 329

This example was prepared according to the general procedure for quinoxaline-benzothiazoles described in the table above. Thus, reaction of Intermediate 329A with Intermediate I-2 afforded Example 329 in 32% yield following purification by preparative HPLC (Method D, 55-100% over 20 min). LC-MS: Method H, RT=1.20 min, MS (ESI) m/z: 398.3 (M+H)⁺. ¹H NMR (500 MHz, DMSO-d₆) δ 9.10 (s, 1H), 8.80 (s, 1H), 8.05 (s, 1H), 8.01 (d, J=8.0 Hz, 1H), 7.97 (d, J=11.6 Hz, 1H), 4.83 (s, 2H), 4.81-4.73 (m, 1H), 3.49 (s, 3H), 2.69 (s, 3H), 1.39 (d, J=6.1 Hz, 6H).

Example 330

N-(2-((4-chloro-5-fluoro-2-(2-methoxy-7-methylquinoxalin-5-yl)benzo[d]thiazol-6-yl)oxy)ethyl)benzenesulfonamide

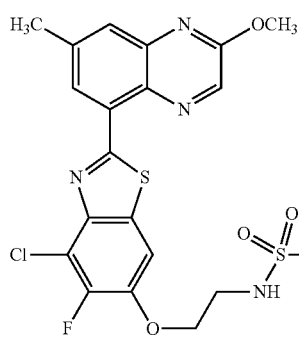
(330)

Intermediate 330A: 2-((4-chloro-5-fluoro-2-(2-methoxy-7-methylquinoxalin-5-yl) benzo[d]thiazol-6-yl)oxy)ethyl methanesulfonate

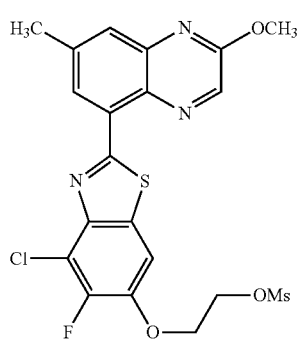

(330A)

To a solution of Example 318 (18 mg, 0.043 mmol) in DCM (1 mL) was added triethylamine (0.012 mL, 0.086 mmol) followed by methanesulfonic anhydride (9.71 mg, 0.056 mmol). After 30 min, the reaction mixture was further diluted with DCM and washed with saturated NaHCO₃ followed by brine. The organic phase was dried over MgSO₄, filtered and concentrated in vacuo to afford Intermediate 330A (18 mg, 0.036 mmol, 84% yield) as an amorphous yellow solid. This material was taken forward without further purification. LC-MS: Method H, RT=1.18 min, MS (ES) m/z: 498.1, 500.1 (M+H)⁺. ¹H NMR (400 MHz, THF) δ 8.68 (d, J=1.5 Hz, 1H), 8.46 (s, 1H), 7.69 (dd, J=2.0, 0.9 Hz, 1H), 7.62 (d, J=7.5 Hz, 1H), 4.55-4.47 (m, 2H), 4.39-4.33 (m, 2H), 4.00 (s, 3H), 3.01 (s, 3H), 2.55 (s, 3H).

Example 330

To a solution of Intermediate 330A (8 mg, 0.016 mmol) in DMF (1 mL) was added benzenesulfonamide (7.58 mg, 0.048 mmol) followed by K₂CO₃ (11.10 mg, 0.080 mmol). The reaction vial was sealed and heated to 100° C. in the microwave for 30 min. The crude reaction mixture was filtered and purified by preparative HPLC (Method D, 60-100% over 20 min) to afford Example 330 (1.6 mg, 2.78 µl, 17% yield). LC-MS: Method H, RT=1.22 min, MS (ESI) m/z: 559.1, 561.2 (M+H)⁺. ¹H NMR (500 MHz, CHLOROFORM-d) δ 8.73 (br. s., 1H), 8.54 (br. s., 1H), 7.91 (br. s., 2H), 7.77 (br. s., 1H), 7.60-7.47 (m, 3H), 7.25 (br. s., 1H), 5.12 (br. s., 1H), 4.19-4.09 (m, 5H), 3.49 (br. s., 2H), 2.67 (br. s., 3H).

Example 331

2-((4-chloro-5-fluoro-2-(2-methoxy-7-methylquinoxalin-5-yl)benzo[d]thiazol-6-yl) oxy)ethyl pyridin-3-ylcarbamate

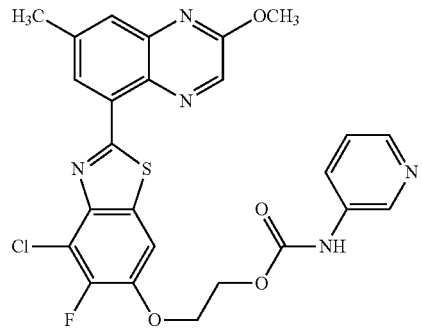

(331)

To a suspension of Example 318 (75 mg, 0.179 mmol) in THF (3.6 mL) was added a solution of phosgene (15% by wt. in toluene) (1.2 mL, 1.790 mmol). After 30 min, the resulting chlorofomate intermediate was concentrated down to a yellow residue. This residue was retaken in THF (3.6 mL) and pyridin-3-amine (50.4 mg, 0.537 mmol) was added followed by Hunig's Base (313 µl, 1.79 mmol). After an additional 5 min, the reaction mixture was concentrated, retaken in DMF, filtered and purified by preparative HPLC (Method D, 50-100% over 10 min) to afford Example 331 (17.9 mg, 0.032 mmol, 18.19% yield) as a yellow solid. LC-MS: Method H, RT=0.98 min, MS (ESI) m/z: 540.2, 542.2 (M+H)⁺. ¹H NMR (400 MHz, DMSO-d₆) δ 9.99 (br. s., 1H), 8.68 (s, 1H), 8.53 (d, J=1.8 Hz, 1H), 8.19 (br. s., 1H), 7.98 (d, J=7.7 Hz, 1H), 7.84 (d, J=8.1 Hz, 1H), 7.80 (s, 1H), 7.29 (br. s., 1H), 4.48 (d, J=4.2 Hz, 2H), 4.41 (d, J=4.4 Hz, 2H), 4.02 (s, 3H), 2.59 (s, 3H). ¹⁹F NMR (376 MHz, DMSO-d₆) δ -135.91.

Preparation of Carbamate Examples

The following carbamates were prepared according to the following general procedure, which is analogous to Example 331 described above:

To a solution of the appropriately substituted Quinoxaline-Benzothiazole Alcohol (1.0 equiv) in THF (0.05 M) was added a solution of phosgene (15% by wt. in toluene, 10 equiv). The combined solution was stirred at room temperature for the designated amount of time before the intermediate chloroformate was concentrated in vacuo. This intermediate was retaken in THF (0.05 M) and the appropriately substituted amino-pyridine, aniline or amine (3.0 equiv) was added. After a minute of vigorous stirring, an excess of diisopropylethylamine (10 equiv) or pyridine (10 equiv) was added. After an additional 5 min of stirring, the resulting mixture was concentrated, retaken in DMF, filtered and purified by preparative HPLC to yield the desired example.

| Ex | Structure | R—OH | Time | LCMS [M + H]+ m/z | LCMS RT (Min) Method H | HPLC Prep Method D | NMR |
|---|---|---|---|---|---|---|---|
| 332 | 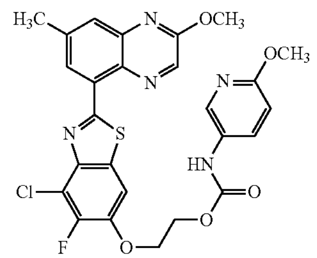 [SMILES: COc1ccc(NC(=O)OCCOc2cc3sc(-c4cc(C)cc5nc(OC)cnc45)nc3c(Cl)c2F)cn1] | 318 | 1 h | 570.1, 572.1 | 1.20 | 65-100% 20 min | ¹H NMR (500 MHz, DMSO-d₆) δ 8.76 (br. s., 1H), 8.61 (br. s., 1H), 8.24 (br. s., 1H), 7.97 (br. s., 2H), 7.88 (br. s., 1H), 6.79 (br. s., 1H), 6.59 (br. s., 1H), 4.62-4.43 (m, 2H), 4.33 (br. s., 2H), 4.10 (br. s., 3H), 3.80 (br. s., 3H), 2.75 (br. s., 3H). |
| 333 | 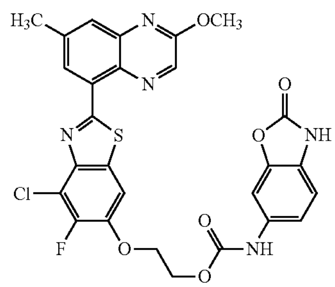 [SMILES: COc1cnc2c(-c3nc4c(Cl)c(F)c(OCCOC(=O)Nc5ccc6[nH]c(=O)oc6c5)cc4s3)cc(C)cc2n1] | 318 | 1 h | 596.2, 598.2 | 0.87 | 55-100% 23 min | ¹H NMR (500 MHz, DMSO-d₆) δ 11.50 (br. s., 1H), 9.87 (br. s., 1H), 8.75 (br. s., 1H), 8.60 (br. s., 1H), 8.05 (br. s., 1H), 7.87 (br. s., 1H), 7.51 (br. s., 1H), 7.17 (br. s., 1H), 7.01 (d, J = 7.7 Hz, 1H), 4.54 (br. s., 2H), 4.48 (br. s., 2H), 4.10 (br. s., 3H), 2.67 (br. s., 3H). |
| 334 | 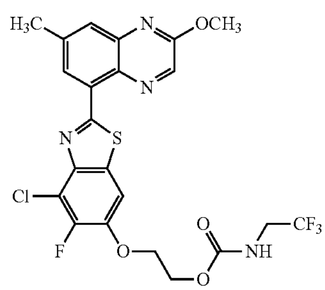 [SMILES: COc1cnc2c(-c3nc4c(Cl)c(F)c(OCCOC(=O)NCC(F)(F)F)cc4s3)cc(C)cc2n1] | 318 | 1 h | 545.1, 547.1 | 1.21 | 55-100% 23 min | ¹H NMR (500 MHz, DMSO-d₆) δ 8.70 (s, 1H), 8.56 (br. s., 1H), 8.14 (br. s., 1H), 7.97 (d, J = 7.2 Hz, 2H), 7.82 (br. s., 1H), 4.56-4.36 (m, 2H), 4.08 (br. s., 2H), 3.83 (br. s, 3H), 2.65 (br. s., 3H). |
| 335 | 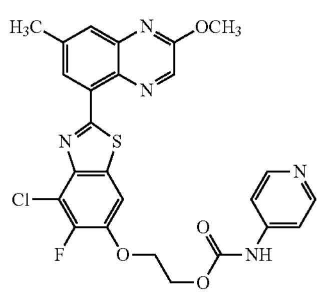 [SMILES: COc1cnc2c(-c3nc4c(Cl)c(F)c(OCCOC(=O)Nc5ccncc5)cc4s3)cc(C)cc2n1] | 318 | 1 h | 540.2, 542.2 | 1.19 | 55-95% 20 min, 100% 5 min | ¹H NMR (400 MHz, DMSO-d₆) δ 10.32 (s, 1H), 8.78 (s, 1H), 8.62 (s, 1H), 8.39 (d, J = 6.6 Hz, 2H), 8.07 (d, J = 7.3 Hz, 1H), 7.89 (s, 1H), 7.46 (d, J = 6.6 Hz, 2H), 4.58 (br. s., 2H), 4.48 (br. s., 2H), 4.15-4.05 (m, 4H), 2.66 (s, 3H). |
| 336 | 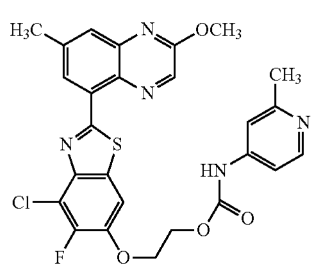 [SMILES: COc1cnc2c(-c3nc4c(Cl)c(F)c(OCCOC(=O)Nc5ccnc(C)c5)cc4s3)cc(C)cc2n1] | 318 | 1 h | 554.2, 556.2 | 1.14 | 40-80% 20 min, 100% 5 min | ¹H NMR (500 MHz, DMSO-d₆) δ 10.23 (br. s., 1H), 8.72 (s, 1H), 8.57 (s, 1H), 8.25 (d, J = 4.9 Hz, 1H), 8.01 (d, J = 6.7 Hz, 1H), 7.84 (br. s., 1H), 7.31 (br. s., 1H), 7.28 (d, J = 4.9 Hz, 1H), 4.56 (br. s., 2H), 4.47 (br. s., 2H), 4.17-4.10 (m, 2H), 4.08 (s, 3H), 2.65 (s, 3H), 2.38 (s, 3H). |

-continued

| Ex | Structure | R—OH | Time | LCMS [M + H]+ m/z | LCMS RT (Min) Method H | HPLC Prep Method D | NMR |
|---|---|---|---|---|---|---|---|
| 337 | 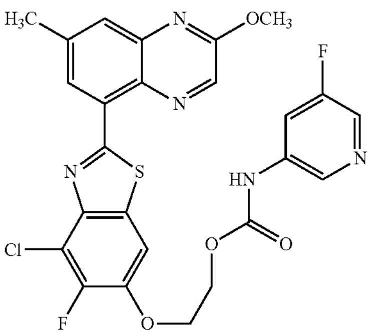 [SMILES: COc1cnc2c(-c3nc4c(Cl)c(F)c(OCCOC(=O)Nc5cncc(F)c5)cc4s3)cc(C)cc2n1] | 318 | 1 h | 558.2, 600.2 | 1.17 | 50-90% 15 min, 100% 5 min | ¹H NMR (500 MHz, DMSO-d₆) δ 10.38 (br. s., 1H), 8.76 (s, 1H), 8.61 (s, 1H), 8.49 (s, 1H), 8.23 (s, 1H), 8.06 (d, J = 7.0 Hz, 1H), 7.91-7.81 (m, 2H), 4.58 (br. s., 2H), 4.49 (br. s., 2H), 4.10 (s, 3H), 2.66 (s, 3H). |
| 338 | 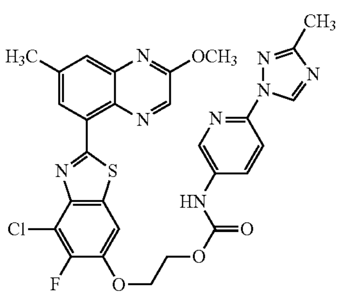 [SMILES: COc1cnc2c(-c3nc4c(Cl)c(F)c(OCCOC(=O)Nc5ccc(-n6cnc(C)n6)nc5)cc4s3)cc(C)cc2n1] | 318 | 1 h | 622.1, 624.1 | 1.16 | 50-90% 15 min, 100% 5 min | |
| 339 | 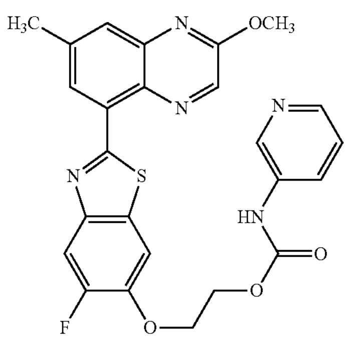 [SMILES: COc1cnc2c(-c3nc4cc(F)c(OCCOC(=O)Nc5cccnc5)cc4s3)cc(C)cc2n1] | I-66 | 1 h | 506.2 | 0.93 | 40-90% 20 min, 100% 5 min | ¹H NMR (500 MHz, DMSO-d₆) δ 10.07 (br. s., 1H), 8.76 (s, 1H), 8.66 (br. s., 1H), 8.59 (d, J = 1.9 Hz, 1H), 8.23 (d, J = 4.1 Hz, 1H), 8.02 (d, J = 8.3 Hz, 1H), 8.00 (d, J = 11.6 Hz, 1H), 7.91 (d, J = 8.3 Hz, 1H), 7.85 (s, 1H), 7.34 (dd, J = 8.4, 4.5 Hz, 1H), 4.58-4.53 (m, 2H), 4.48-4.40 (m, 2H), 4.09 (s, 3H), 2.64 (s, 3H). |
| 340 | 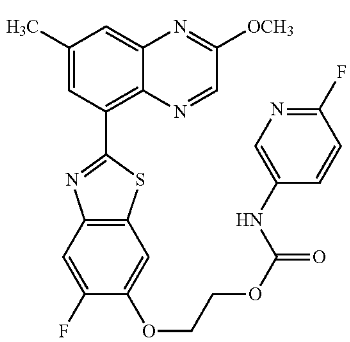 [SMILES: COc1cnc2c(-c3nc4cc(F)c(OCCOC(=O)Nc5ccc(F)nc5)cc4s3)cc(C)cc2n1] | I-66 | 1 h | 524.2 | 1.16 | 50-85% 20 min, 100% 5 min | ¹H NMR (500 MHz, DMSO-d₆) δ 10.13 (br. s., 1H), 8.73 (s, 1H), 8.56 (s, 1H), 8.29 (br. s., 1H), 8.04 (br. s., 1H), 8.02-7.96 (m, 2H), 7.82 (s, 1H), 7.15 (dd, J = 8.9, 3.2 Hz, 1H), 4.54 (d, J = 4.1 Hz, 2H), 4.45 (d, J = 4.1 Hz, 2H), 4.08 (s, 3H), 2.63 (s, 3H). |

-continued

| Ex | Structure | R—OH | Time | LCMS [M + H]+ m/z | LCMS RT (Min) Method H | HPLC Prep Method D | NMR |
|---|---|---|---|---|---|---|---|
| 341 | 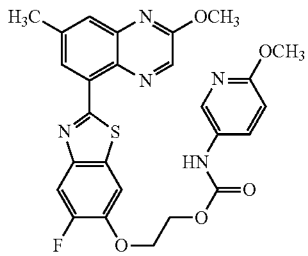 [SMILES: COc1ccc(NC(=O)OCCOc2cc3sc(-c4cc(C)cc5nc(OC)cnc45)nc3cc2F)cn1] | I-66 | 1 h | 536.2 | 1.15 | 50-85% 20 min, 100% 5 min | ¹H NMR (500 MHz, DMSO-d₆) δ 8.76 (s, 1H), 8.59 (d, J = 1.7 Hz, 1H), 8.24 (br. s., 1H), 8.06-7.96 (m, 3H), 7.85 (s, 1H), 7.78 (br. s., 1H), 6.79 (d, J = 8.8 Hz, 1H), 4.51 (d, J = 4.7 Hz, 2H), 4.44 (d, J = 4.4 Hz, 2H), 4.09 (s, 3H), 3.80 (s, 3H), 2.64 (s, 3H). |
| 342 | 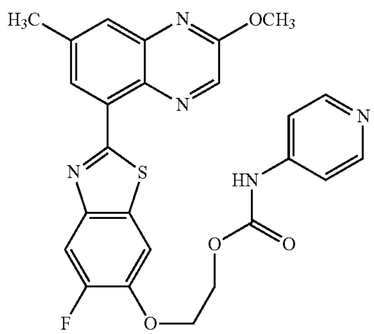 [SMILES: COc1cnc2c(-c3nc4cc(F)c(OCCOC(=O)Nc5ccncc5)cc4s3)cc(C)cc2n1] | I-66 | 1 h | 506.2 | 0.95 | 40-80% 20 min, 100% 5 min | ¹H NMR (500 MHz, DMSO-d₆) δ 10.31 (s, 1H), 8.75 (s, 1H), 8.58 (d, J = 1.7 Hz, 1H), 8.39 (d, J = 6.1 Hz, 2H), 8.02 (d, J = 8.3 Hz, 1H), 7.99 (d, J = 11.6 Hz, 1H), 7.84 (d, J = 0.8 Hz, 1H), 7.48-7.44 (m, 2H), 4.59-4.53 (m, 2H), 4.46 (d, J = 4.1 Hz, 2H), 4.09 (s, 3H), 2.64 (s, 3H). |
| 343 | 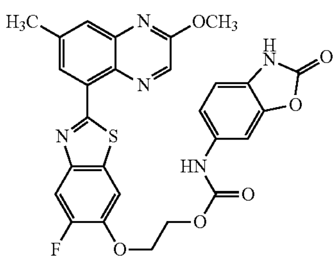 [SMILES: COc1cnc2c(-c3nc4cc(F)c(OCCOC(=O)Nc5ccc6[nH]c(=O)oc6c5)cc4s3)cc(C)cc2n1] | I-66 | 1 h | 562.2 | 1.10 | 45-80% 20 min, 100% 5 min | ¹H NMR (500 MHz, DMSO-d₆) δ 9.87 (br. s., 1H), 8.74 (s, 1H), 8.58 (d, J = 1.7 Hz, 1H), 8.04-7.95 (m, 2H), 7.87-7.81 (m, 1H), 7.50 (br. s., 1H), 7.17 (d, J = 8.0 Hz, 1H), 7.00 (d, J = 8.5 Hz, 1H), 4.56-4.49 (m, 2H), 4.47-4.39 (m, 2H), 4.09 (s, 3H), 2.63 (s, 3H). |
| 344 | 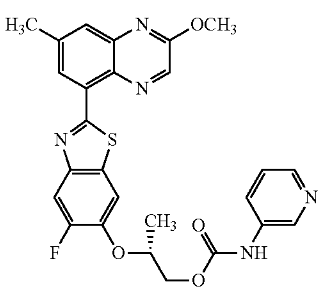 [SMILES: COc1cnc2c(-c3nc4cc(F)c(O[C@H](C)COC(=O)Nc5cccnc5)cc4s3)cc(C)cc2n1] | I-71 | 16 h | 520.2 | 0.97 | 35-75% 20 min, 100% 5 min | ¹H NMR (500 MHz, DMSO-d₆) δ 10.20 (br. s., 1H), 8.76-8.70 (m, 2H), 8.57 (d, J = 1.7 Hz, 1H), 8.30 (d, J = 4.4 Hz, 1H), 8.06 (d, J = 8.3 Hz, 1H), 8.02 (d, J = 8.0 Hz, 1H), 7.97 (d, J = 11.6 Hz, 1H), 7.84 (d, J = 0.8 Hz, 1H), 7.49 (dd, J = 8.5, 5.0 Hz, 1H), 4.91 (td, J = 6.1, 3.2 Hz, 1H), 4.46-4.41 (m, 1H), 4.40-4.34 (m, 1H), 4.09 (s, 3H), 2.63 (s, 3H), 1.42 (d, J = 6.3 Hz, 3H). |
| 345 | 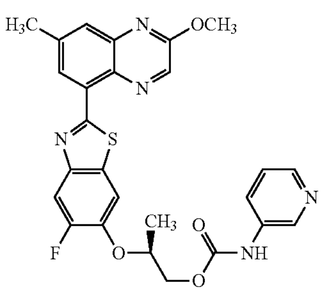 [SMILES: COc1cnc2c(-c3nc4cc(F)c(O[C@@H](C)COC(=O)Nc5cccnc5)cc4s3)cc(C)cc2n1] | I-70 | 16 h | 520.2 | 0.97 | 50-90% 20 min, 100% 6 min | ¹H NMR (500 MHz, DMSO-d₆) δ 10.20 (br. s., 1H), 8.76-8.70 (m, 2H), 8.57 (d, J = 1.7 Hz, 1H), 8.30 (d, J = 4.4 Hz, 1H), 8.06 (d, J = 8.3 Hz, 1H), 8.02 (d, J = 8.0 Hz, 1H), 7.97 (d, J = 11.6 Hz, 1H), 7.84 (d, J = 0.8 Hz, 1H), 7.49 (dd, J = 8.5, 5.0 Hz, 1H), 4.91 (td, J = 6.1, 3.2 Hz, 1H), 4.46-4.41 (m, 1H), 4.40-4.34 (m, 1H), 4.09 (s, 3H), 2.63 (s, 3H), 1.42 (d, J = 6.3 Hz, 3H). |

| Ex | Structure | R—OH | Time | LCMS [M + H]+ m/z | LCMS RT (Min) Method H | HPLC Prep Method D | NMR |
|---|---|---|---|---|---|---|---|
| 346 | 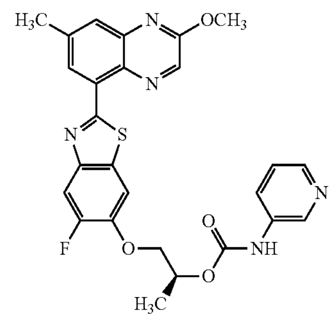 [SMILES: COc1cnc2c(-c3nc4cc(F)c(OC[C@H](C)OC(=O)Nc5cccnc5)cc4s3)cc(C)cc2n1] | I-68 | 24 h | 520.2 | 0.98 | 45-100% 20 min, 100% 5 min | 1H NMR (500 MHz, DMSO-d6) δ 9.98 (br. s., 1H), 8.74 (s, 1H), 8.65 (s, 1H), 8.57 (d, J = 1.7 Hz, 1H), 8.24-8.18 (m, 1H), 8.01 (d, J = 8.3 Hz, 1H), 7.97 (d, J = 11.8 Hz, 1H), 7.91 (d, J = 8 0 Hz, 1H), 7.83 (d, J = 0.8 Hz 1H), 7.32 (dd, J = 8.3, 4.7 Hz, 1H), 5.27 (td, J = 6.3, 3.2 Hz, 1H), 4.40-4.33 (m, 1H), 4.31-4.25 (m, 1H), 4.08 (s, 3H), 2.63 (s, 3H), 1.43 (d, J = 6.3 Hz, 3H). |
| 347 | 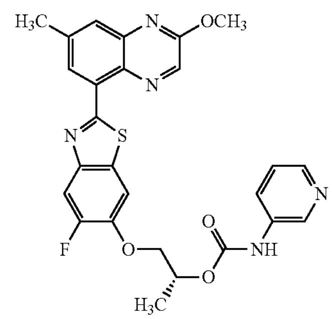 [SMILES: COc1cnc2c(-c3nc4cc(F)c(OC[C@@H](C)OC(=O)Nc5cccnc5)cc4s3)cc(C)cc2n1] | I-67 | 24 h | 520.2 | 0.98 | 45-100% 20 min, 100% 5 min | 1H NMR (500 MHz, DMSO-d6) δ 9.98 (br. s., 1H), 8.74 (s, 1H), 8.65 (s, 1H), 8.57 (d, J = 1.7 Hz, 1H), 8.24-8.18 (m, 1H), 8.01 (d, J = 8.3 Hz, 1H), 7.97 (d, J = 11.8 Hz, 1H), 7.91 (d, J = 8.0 Hz, 1H), 7.83 (d, J = 0.8 Hz, 1H), 7.32 (dd, J = 8.3, 4.7 Hz, 1H), 5.27 (td, J = 6.3, 3.2 Hz, 1H), 4.40-4.33 (m, 1H), 4.31-4.25 (m, 1H), 4.08 (s, 3H), 2.63 (s, 3H), 1.43 (d, J = 6.3 Hz, 3H). |
| 348 | 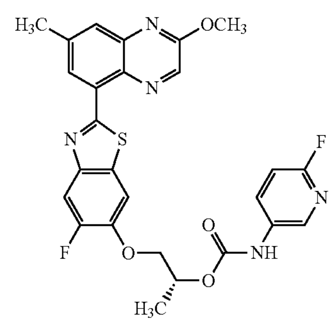 [SMILES: COc1cnc2c(-c3nc4cc(F)c(OC[C@@H](C)OC(=O)Nc5ccc(F)nc5)cc4s3)cc(C)cc2n1] | I-67 | 24 h | 538.2 | 1.18 | 50-100% 20 min, 100% 5 min | 1H NMR (500 MHz, DMSO-d6) δ 8.73 (s, 1H), 8.56 (d, J = 1.7 Hz, 1H), 8.29 (br. s., 1H), 8.03 (br. s., 1H), 8.02-7.93 (m, 3H), 7.82 (s, 1H), 7.18-7.10 (m, 1H), 5.26 (td, J = 6.3, 3.3 Hz, 1H), 4.40-4.32 (m, 1H), 4.31-4.24 (m, 1H), 4.08 (s, 3H), 2.63 (s, 3H), 1.43 (d, J = 6.6 Hz, 3H). |
| 349 | 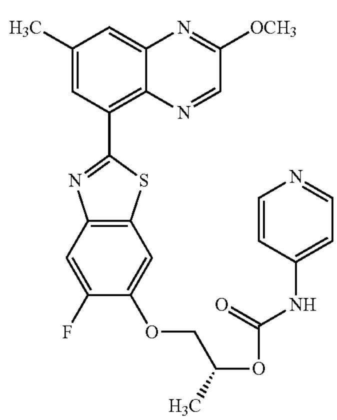 [SMILES: COc1cnc2c(-c3nc4cc(F)c(OC[C@@H](C)OC(=O)Nc5ccncc5)cc4s3)cc(C)cc2n1] | I-67 | 24 h | 520.2 | 0.94 | 55-95% 22 min, 100% 5 min | 1H NMR (500 MHz, DMSO-d6) δ 8.62 (s, 1H), 8.46 (br. s., 3H), 7.94-7.87 (m, 2H), 7.73 (s, 1H), 7.62 (br. s., 2H), 5.75-5.75 (m, 1H), 5.32 (d, J = 2.7 Hz, 1H), 4.37 (d, J = 8.2 Hz, 1H), 4.32-4.24 (m, 1H), 4.05 (s, 3H), 2.58 (s, 3H), 1.46 (d, J = 6.4 Hz, 3H). |

| Ex | Structure | R—OH | Time | LCMS [M + H]+ m/z | LCMS RT (Min) Method H | HPLC Prep Method D | NMR |
|---|---|---|---|---|---|---|---|
| 350 | 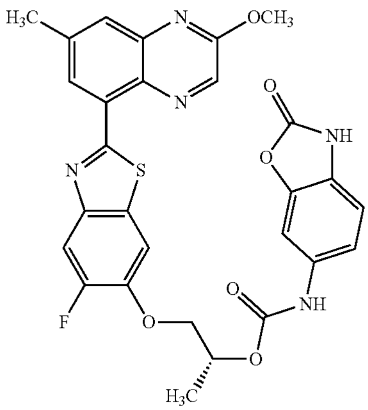 [SMILES: COc1cnc2c(-c3nc4cc(F)c(OC[C@@H](C)OC(=O)Nc5ccc6[nH]c(=O)oc6c5)cc4s3)cc(C)cc2n1] | I-67 | 24 h | 576.2 | 1.13 | 45-90% 20 min, 100% 5 min | ¹H NMR (500 MHz, DMSO-d₆) δ 11.47 (s, 1H), 8.73 (s, 1H), 8.56 (d, J = 1.7 Hz, 1H), 8.00 (d, J = 8.3 Hz, 1H), 7.97 (d, J = 11.6 Hz, 1H), 7.82 (s, 1H), 7.53-7.46 (m, 1H), 7.17 (d, J = 8.5 Hz, 1H), 6.99 (d, J = 8.3 Hz, 1H), 5.24 (td, J = 6.3, 3.4 Hz, 1H), 4.40-4.32 (m, 1H), 4.32-4.25 (m, 1H), 4.08 (s, 3H), 2.63 (s, 3H), 1.42 (d, J = 6.6 Hz, 3H). |
| 351 | 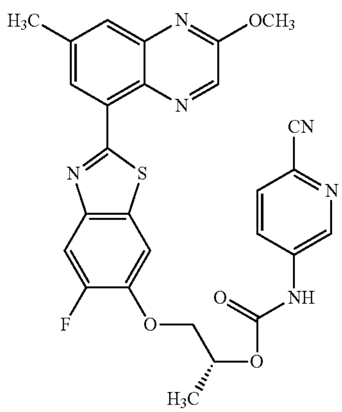 | I-67 | 24 h | 545.2 | 1.21 | 45-100% 25 min, 100% 10 min | ¹H NMR (500 MHz, DMSO-d₆) δ 8.77-8.72 (m, 2H), 8.58 (d, J = 1.9 Hz, 1H), 8.10 (dd, J = 8.5, 2.5 Hz, 1H), 8.01 (d, J = 8.3 Hz, 1H), 7.98 (d, J = 11.6 Hz, 1H), 7.94 (d, J = 8.8 Hz, 1H), 7.84 (dd, J = 1.8, 1.0 Hz, 1H), 5.29 (td, J = 6.3, 3.2 Hz, 1H), 4.43-4.35 (m, 1H), 4.33-4.26 (m, 1H), 4.09 (s, 3H), 2.64 (s, 3H), 1.44 (d, J = 6.3 Hz, 3H). |
| 352 | 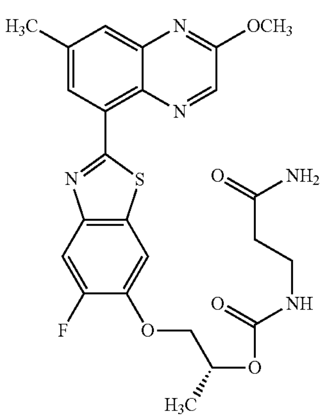 [SMILES: COc1cnc2c(-c3nc4cc(F)c(OC[C@@H](C)OC(=O)NCCC(N)=O)cc4s3)cc(C)cc2n1] | I-67 | 24 h | 514.2 | 1.06 | 35-75% 20 min, 75% 10 min | ¹H NMR (500 MHz, DMSO-d₆) δ 8.66 (s, 1H), 8.50 (s, 1H), 7.94-7.87 (m, 2H), 7.76 (s, 1H), 7.33 (br. s., 1H), 7.15 (br. s., 1H), 6.80 (br. s., 1H), 5.06 (br. s., 1H), 4.19 (br. s., 2H), 4.05 (s, 3H), 3.17 (d, J = 5.8 Hz, 2H), 2.59 (s, 3H), 2.24 (t, J = 6.9 Hz, 2H), 1.30 (d, J = 6.1 Hz, 3H). |

| Ex | Structure | R—OH | Time | LCMS [M + H]+ m/z | LCMS RT (Min) Method H | HPLC Prep Method D | NMR |
|---|---|---|---|---|---|---|---|
| 353 | 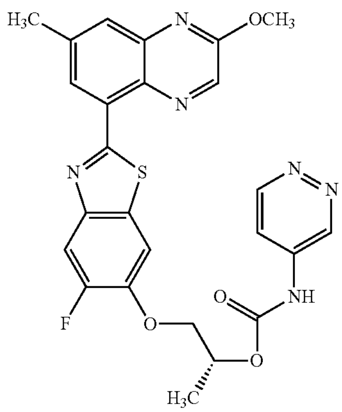 [SMILES: COc1cnc2c(-c3nc4cc(F)c(OC[C@@H](C)OC(=O)Nc5ccnnc5)cc4s3)cc(C)cc2n1] | I-67 | 24 h | 521.2 | 1.00 | 40-80% 20 min, 100% 5 min | ¹H NMR (500 MHz, DMSO-d₆) δ 10.53 (s, 1H), 9.21 (d, J = 2.2 Hz, 1H), 8.98 (d, J = 6.1 Hz, 1H), 8.59 (d, J = 1.7 Hz, 1H), 8.02 (d, J = 8.5 Hz, 1H), 7.99 (d, J = 11.6 Hz, 1H), 7.85 (s, 1H), 7.76 (dd, J = 5.8, 2.8 Hz, 1H), 5.31 (td, J = 6.3, 3.0 Hz, 1H), 4.43-4.37 (m, 1H), 4.30 (dd, J = 11.0, 6.1 Hz, 1H), 4.09 (s, 3H), 2.64 (s, 3H), 1.45 (d, J = 6.3 Hz, 3H). |
| 354 | 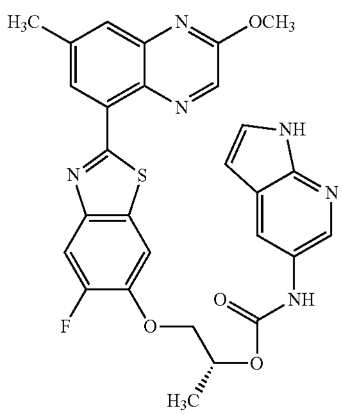 [SMILES: COc1cnc2c(-c3nc4cc(F)c(OC[C@@H](C)OC(=O)Nc5cnc6[nH]ccc6c5)cc4s3)cc(C)cc2n1] | I-67 | 24 h | 559.2 | 1.07 | 20-100% 10 min, 100% 5 min | |
| 355 | 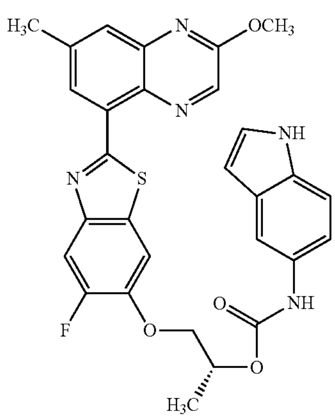 [SMILES: COc1cnc2c(-c3nc4cc(F)c(OC[C@@H](C)OC(=O)Nc5ccc6[nH]ccc6c5)cc4s3)cc(C)cc2n1] | I-67 | 24 h | 558.2 | 1.21 | 20-100% 10 min, 100% 5 min | ¹H NMR (500 MHz, DMSO-d₆) δ 9.46 (br. s., 1H), 8.65 (s, 1H), 8.49 (s, 1H), 7.95-7.89 (m, 2H), 7.75 (s, 1H), 7.68 (br. s., 1H), 7.28 (d, J = 3.0 Hz, 2H), 7.16 (d, J = 7.7 Hz, 1H), 6.34 (br. s., 1H), 5.24 (d, J = 3.4 Hz, 1H), 4.40-4.20 (m, 2H), 4.05 (s, 3H), 2.59 (s, 3H), 1.42 (d, J = 6.4 Hz, 3H). |

-continued

| Ex | Structure | R—OH | Time | LCMS [M + H]+ m/z | LCMS RT (Min) Method H | HPLC Prep Method D | NMR |
|---|---|---|---|---|---|---|---|
| 356 | 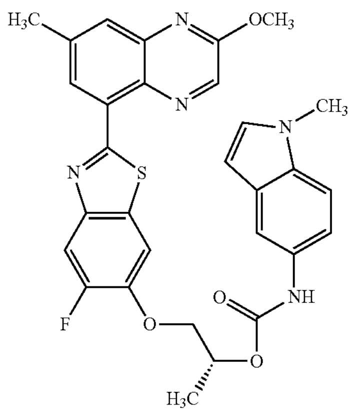 [SMILES: COc1cnc2c(-c3nc4cc(F)c(OC[C@@H](C)OC(=O)Nc5ccc6c(ccn6C)c5)cc4s3)cc(C)cc2n1] | I-67 | 24 h | 572.2 | 1.25 | 20-100% 10 min, 100% 5 min | ¹H NMR (500 MHz, DMSO-d₆) δ 9.49 (br. s., 1H), 8.65 (s, 1H), 8.50 (s, 1H), 7.98-7.88 (m, 2H), 7.76 (s, 1H), 7.68 (br. s., 1H), 7.32 (d, J = 8.8 Hz, 1H), 7.25 (d, J = 2.4 Hz, 1H), 7.22 (br. s., 1H), 6.33 (br. s., 1H), 5.24 (d, J = 3.0 Hz, 1H), 4.38-4.19 (m, 2H), 4.05 (s, 3H), 3.74 (s, 2H), 2.59 (s, 3H), 1.42 (d, J = 6.4 Hz, 3H). |
| 357 | 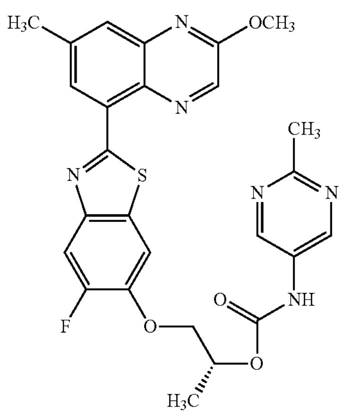 [SMILES: COc1cnc2c(-c3nc4cc(F)c(OC[C@@H](C)OC(=O)Nc5cnc(C)nc5)cc4s3)cc(C)cc2n1] | I-67 | 24 h | 535.2 | 1.14 | 40-80% 20 min, 100% 5 min | ¹H NMR (500 MHz, DMSO-d₆) δ 10.03 (br. s., 1H), 8.73 (br. s., 2H), 8.59 (s, 1H), 8.43 (br. s., 1H), 7.86 (d, J = 10.4 Hz, 2H), 7.71 (s, 1H), 5.25 (br. s., 1H), 4.33 (d, J = 8.4 Hz, 1H), 4.24 (dd, J = 10.6, 6.2 Hz, 1H), 4.03 (s, 3H), 3.68 (br. s., 3H), 2.56 (s, 3H), 1.40 (d, J = 6.4 Hz, 3H). |
| 358 | 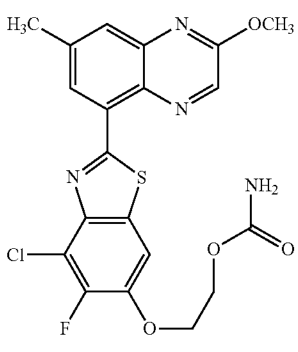 [SMILES: COc1cnc2c(-c3nc4c(Cl)c(F)c(OCCOC(N)=O)cc4s3)cc(C)cc2n1] | 318 | 1 h | 463.1, 465.1 | 1.15 | 45-90% 20 min, 100% 5 min | ¹H NMR (500 MHz, DMSO-d₆) δ 8.73 (s, 1H), 8.59 (s, 1H), 7.97 (d, J = 7.9 Hz, 1H), 7.86 (br. s., 1H), 6.57 (br. s., 2H), 4.36 (d, J = 7.3 Hz, 4H), 4.09 (s, 3H), 2.66 (s, 3H). |
| 359 | 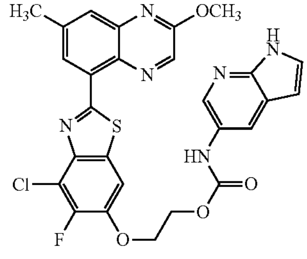 [SMILES: COc1cnc2c(-c3nc4c(Cl)c(F)c(OCCOC(=O)Nc5cnc6[nH]ccc6c5)cc4s3)cc(C)cc2n1] | 318 | 1 h | 579.2, 581.2 | 1.09 | 50-100% 20 min, 100% 5 min | ¹H NMR (500 MHz, DMSO-d₆) δ 9.80 (br. s., 1H), 8.73 (s, 1H), 8.59 (s, 1H), 8.29 (br. s., 1H), 8.12 (br. s., 1H), 8.02 (d, J = 7.0 Hz, 1H), 7.86 (s, 1H), 7.49 (br. s., 1H), 6.46 (br. s., 1H), 4.60 (br. s., 2H), 4.52 (br. s., 2H), 4.14 (s, 3H), 2.70 (s, 3H). |

-continued

| Ex | Structure | R—OH | Time | LCMS [M + H]+ m/z | LCMS RT (Min) Method H | HPLC Prep Method D | NMR |
|---|---|---|---|---|---|---|---|
| 360 | 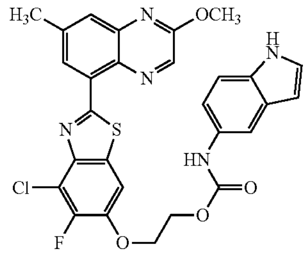 [SMILES: COc1cnc2c(-c3nc4c(Cl)c(F)c(OCCOC(=O)Nc5ccc6[nH]ccc6c5)cc4s3)cc(C)cc2n1] | 318 | 1 h | 578.2, 580.2 | 1.22 | 50-100% 20 min, 100% 5 min | ¹H NMR (500 MHz, DMSO-d₆) δ 9.57 (br. s., 1H), 8.63 (s, 1H), 8.50 (br. s., 1H), 7.92 (d, J = 7.0 Hz, 1H), 7.78 (br. s., 1H), 7.73 (br. s., 1H), 7.40-7.31 (m, 2H), 7.21 (br. s., 1H), 6.41 (br. s., 1H), 4.57 (br. s., 2H), 4.48 (br. s., 2H), 4.11 (s, 3H), 2.66 (br. s., 3H). |
| 361 | 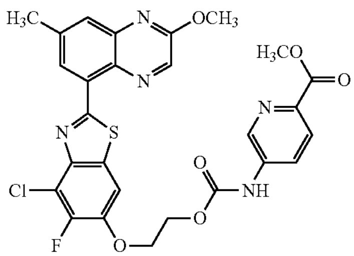 [SMILES: COC(=O)c1ccc(NC(=O)OCCOc2cc3sc(-c4cc(C)cc5nc(OC)cnc45)nc3c(Cl)c2F)cn1] | 318 | 1 h | 598.2, 600.2 | 1.18 | 65-95% 25 min, 95% 10 min | ¹H NMR (500 MHz, CHLOROFORM-d) δ 8.67 (s, 1H), 8.52 (s, 1H), 8.47 (s, 1H), 7.71 (s, 1H), 8.08-8.03 (m, 1H), 7.35 (d, J = 7.2 Hz, 1H), 6.95 (br. s., 1H), 4.59 (br. s., 2H), 4.34 (br. s., 2H), 4.06 (s, 3H), 3.92 (s, 3H), 2.60 (s, 3H). |
| 362 | 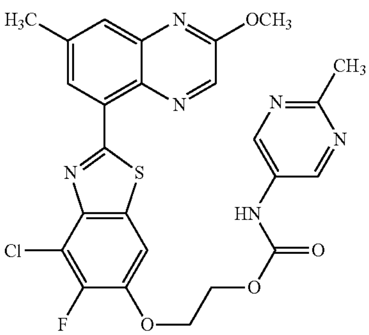 [SMILES: COc1cnc2c(-c3nc4c(Cl)c(F)c(OCCOC(=O)Nc5cnc(C)nc5)cc4s3)cc(C)cc2n1] | 318 | 1 h | 555.2, 557.2 | 1.16 | 50-100% 20 min 100% 5 min | ¹H NMR (500 MHz, CHLOROFORM-d) δ 8.74-8.61 (m, 3H), 8.47 (s, 1H), 7.71 (s, 1H), 7.34 (d, J = 7.2 Hz, 1H), 6.66 (br. s., 1H), 4.61-4.52 (m, 2H), 4.35-4.31 (m, 2H), 4.06 (s, 3H), 2.63 (s, 3H), 2.60 (s, 3H). |
| 363 | 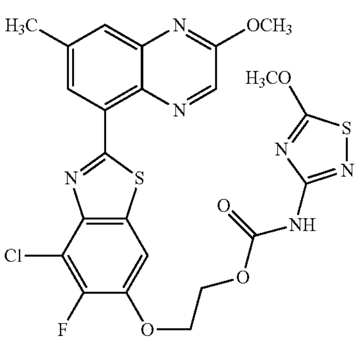 [SMILES: COc1cnc2c(-c3nc4c(Cl)c(F)c(OCCOC(=O)Nc5nsc(OC)n5)cc4s3)cc(C)cc2n1] | 318 | 1 h | 577.2, 579.2 | 1.19 | 50-100% 20 min, 100% 5 min | ¹H NMR (500 MHz, CHLOROFORM-d) δ 8.76 (br. s., 1H), 8.57 (br. s., 1H), 7.80 (br. s., 1H), 7.63 (br. s., 1H), 7.44 (br. s., 1H), 4.67 (br. s., 2H), 4.43 (br. s., 2H), 4.16 (br. s., 6H), 2.69 (br. s., 3H). |
| 364 | 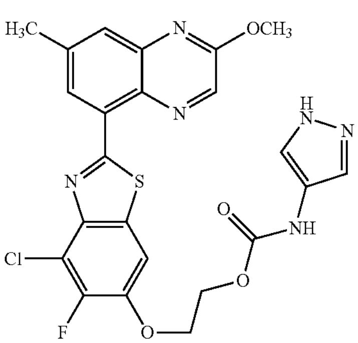 [SMILES: COc1cnc2c(-c3nc4c(Cl)c(F)c(OCCOC(=O)Nc5cn[nH]c5)cc4s3)cc(C)cc2n1] | 318 | 1 h | 529.2, 531.2 | 1.16 | 50-80% 25 min, 100% 7 min | ¹H NMR (500 MHz, DMSO-d₆) δ 9.61 (s, 1H), 8.65 (s, 1H), 8.52 (s, 1H), 7.92 (d, J = 7.6 Hz, 1H), 7.80 (s, 1H), 7.60 (br. s., 2H), 4.55 (br. s., 2H), 4.46 (br. s., 2H), 4.11 (s, 3H), 2.67 (s, 3H). |

| Ex | Structure | R—OH | Time | LCMS [M + H]+ m/z | LCMS RT (Min) Method H | HPLC Prep Method D | NMR |
|---|---|---|---|---|---|---|---|
| 365 | 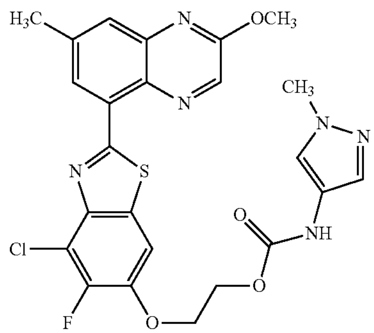 [SMILES: COc1cnc2c(-c3nc4c(Cl)c(F)c(OCCOC(=O)Nc5cnn(C)c5)cc4s3)cc(C)cc2n1] | 318 | 1 h | 543.2, 545.2 | 1.21 | 50-90% 25 min, 100% 10 min | ¹H NMR (500 MHz, CD₂Cl₂) δ 8.65 (br. s., 1H), 8.46 (br. s., 1H), 7.70 (br. s., 1H), 7.51 (br. s., 1H), 7.36 (d, J = 5.8 Hz, 1H), 7.27 (br. s., 1H), 6.49 (br. s., 1H), 4.50 (br. s., 2H), 4.30 (br. s., 2H), 4.05 (br. s., 3H), 3.76 (br. s., 3H), 2.59 (br. s., 3H). |
| 366 | 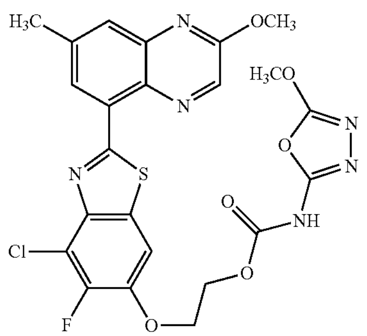 [SMILES: COc1cnc2c(-c3nc4c(Cl)c(F)c(OCCOC(=O)Nc5nnc(OC)o5)cc4s3)cc(C)cc2n1] | 318 | 1 h | 545.1, 547.1 | 1.12 | 60-90% 22 min, 100% 7 min | ¹H NMR (500 MHz, DMSO-d₆) δ 8.62 (s, 1H), 8.49 (br. s., 1H), 7.92 (s, 1H), 7.86 (d, J = 7.9 Hz, 1H), 7.77 (br. s., 1H), 4.49 (br. s., 2H), 4.38 (br. s., 2H), 4.04 (s, 3H), 2.88 (s, 3H), 2.72 (s, 3H). |
| 367 | 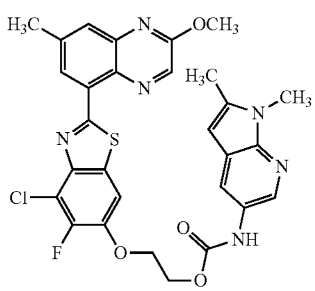 [SMILES: COc1cnc2c(-c3nc4c(Cl)c(F)c(OCCOC(=O)Nc5cnc6c(c5)cc(C)n6C)cc4s3)cc(C)cc2n1] | 318 | 1 h | 607.2, 609.2 | 1.19 | 60-100% 20 min, 100% 5 min | ¹H NMR (500 MHz, DMSO-d₆) δ 9.67 (br. s., 1H), 8.60 (s, 1H), 8.47 (br. s., 1H), 8.15 (br. s., 1H), 7.90 (br. s., 2H), 7.75 (br. s., 1H), 6.15 (br. s., 1H), 4.51 (br. s., 2H), 4.43 (br. s., 2H), 4.04 (s, 3H), 3.51 (s, 3H), 2.60 (s, 3H), 2.38 (br. s., 3H). |
| 368 | 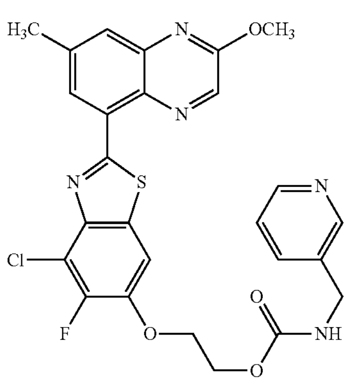 [SMILES: COc1cnc2c(-c3nc4c(Cl)c(F)c(OCCOC(=O)NCc5cccnc5)cc4s3)cc(C)cc2n1] | 318 | 1 h | 554.2, 556.2 | 1.02 | 50-95% 20 min, 100% 5 min | ¹H NMR (500 MHz, DMSO-d₆) δ 8.69 (s, 1H), 8.55 (s, 1H), 8.46 (br. s., 1H), 8.43 (br. s., 1H), 7.93 (br. s., 2H), 7.82 (s, 1H), 7.64 (br. s., 1H), 7.33 (br. s., 1H), 4.38 (d, J = 9.8 Hz, 4H), 4.22 (d, J = 5.8 Hz, 2H), 4.06 (s, 3H), 2.63 (s, 3H). |

-continued

| Ex | Structure | R—OH | Time | LCMS [M + H]+ m/z | LCMS RT (Min) Method H | HPLC Prep Method D | NMR |
|---|---|---|---|---|---|---|---|
| 369 | 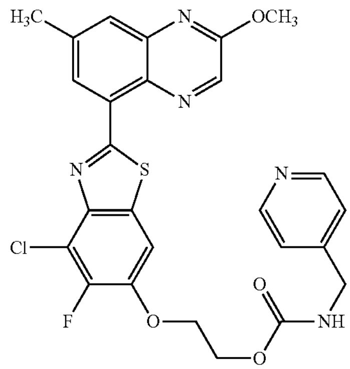 [SMILES: COc1cnc2c(-c3nc4c(Cl)c(F)c(OCCOC(=O)NCc5ccncc5)cc4s3)cc(C)cc2n1] | 318 | 1 h | 554.2, 556.2 | 1.01 | 50-100% 20 min, 100% 5 min | 1H NMR (500 MHz, DMSO-d6) δ 8.72 (br. s., 1H), 8.60-8.51 (m, 3H), 8.11-7.88 (m, 2H), 7.85 (br. s., 1H), 7.32 (d, J = 4.6 Hz, 2H), 4.47 (d, J = 15.9 Hz, 4H), 4.30 (d, J = 6.1 Hz, 2H), 4.13 (s, 3H), 2.69 (s, 3H). |
| 370 | 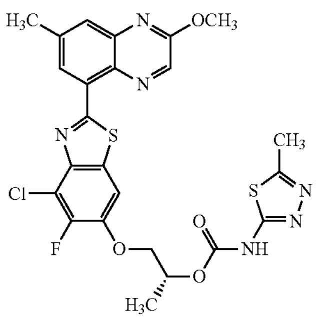 [SMILES: COc1cnc2c(-c3nc4c(Cl)c(F)c(OC[C@@H](C)OC(=O)Nc5nnc(C)s5)cc4s3)cc(C)cc2n1] | I-69 | 24 h | 575.4, 577.4 | 1.19 | 60-100% 20 min, 100% 5 min | 1H NMR (500 MHz, DMSO-d6) δ 8.71 (br. s., 1H), 8.56 (br. s., 1H), 7.99 (d, J = 7.02 Hz, 1H), 7.83 (br. s., 1H), 5.33 (br. s., 1H), 4.41 (d, J = 10.68 Hz, 1H), 4.30 (br. s., 1H), 4.09 (br. s., 3H), 1.43 (d, J = 5.49 Hz, 3H). |
| 371 | 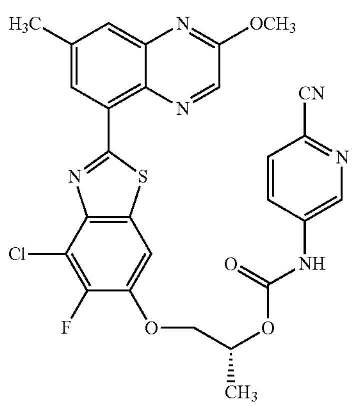 [SMILES: COc1cnc2c(-c3nc4c(Cl)c(F)c(OC[C@@H](C)OC(=O)Nc5ccc(C#N)nc5)cc4s3)cc(C)cc2n1] | I-69 | 24 h | 579.4, 581.4 | 1.22 | 70-100% 20 min, 100% 5 min | 1H NMR (500 MHz, DMSO-d6) δ 8.73 (br. s., 1H), 8.63 (br. s., 1H), 8.48 (br. s., 1H), 8.08 (d, J = 8.55 Hz, 1H), 7.86-8.00 (m, 3H), 7.76 (br. s., 1H), 5.30 (br. s., 1H), 4.22-4.46 (m, 2H), 4.06 (br. s., 3H), 2.62 (br. s., 3H), 1.44 (d, J = 4.88 Hz, 3H). |
| 372 | 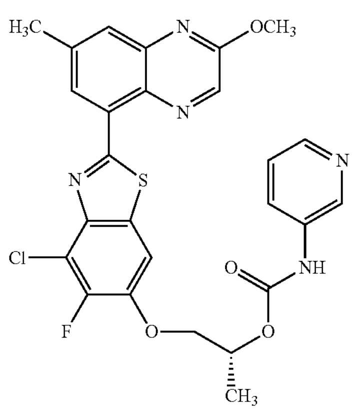 [SMILES: COc1cnc2c(-c3nc4c(Cl)c(F)c(OC[C@@H](C)OC(=O)Nc5cccnc5)cc4s3)cc(C)cc2n1] | I-69 | 24 h | 554.1, 556.1 | 1.24 | 60-100% 13 min, 100% 5 min | 1H NMR (500 MHz, DMSO-d6) δ 9.97 (br. s., 1H), 8.65 (br. s., 2H), 8.50 (br. s., 1H), 8.21 (br. s., 1H), 7.86-8.00 (m, 2H), 7.78 (br. s., 1H), 7.33 (br. s., 1H), 5.28 (br. s., 1H), 4.24-4.45 (m, 2H), 4.07 (s, 3H), 2.62 (s, 3H), 1.43 (d, J = 5.80 Hz, 3H). |

-continued

| Ex | Structure | R—OH | Time | LCMS [M + H]+ m/z | LCMS RT (Min) Method H | HPLC Prep Method D | NMR |
|---|---|---|---|---|---|---|---|
| 373 | 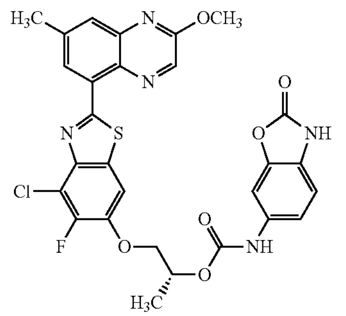 [SMILES: COc1cnc2c(-c3nc4c(Cl)c(F)c(OC[C@@H](C)OC(=O)Nc5ccc6[nH]c(=O)oc6c5)cc4s3)cc(C)cc2n1] | I-69 | 24 h | 611.1, 613.1 | 1.20 | 65-100% 13 min, 100% 5 min | ¹H NMR (500 MHz, DMSO-d₆) δ 9.63-9.76 (m, 1H), 8.74 (s, 1H), 8.59 (s, 1H), 7.98-8.05 (m, 1H), 7.85 (s, 1H), 7.71-7.79 (m, 1H), 7.36-7.49 (m, 1H), 7.05-7.17 (m, 1H), 6.89-6.97 (m, 1H), 4.99-5.34 (m, 1H), 4.23-4.43 (m, 2H), 4.08 (s, 3H), 3.08-3.19 (m, 1H), 2.64 (s, 3H), 1.40 (d, J = 6.10 Hz, 3H). |
| 374 | 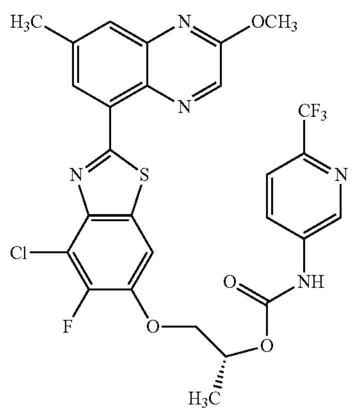 [SMILES: COc1cnc2c(-c3nc4c(Cl)c(F)c(OC[C@@H](C)OC(=O)Nc5ccc(C(F)(F)F)nc5)cc4s3)cc(C)cc2n1] | I-69 | 24 h | 622.2, 624.2 | 1.36 | 60-100% 20 min, 100% 5 min | ¹H NMR (500 MHz, DMSO-d₆) δ 10.39 (br. s., 1H), 8.76 (s, 1H), 8.68 (s, 1H), 8.54 (s, 1H), 8.12 (d, J = 8.55 Hz, 1H), 7.98 (d, J = 7.63 Hz, 1H), 7.74-7.87 (m, 2H), 5.29 (br. s., 1H), 4.22-4.47 (m, 2H), 4.07 (s, 3H), 2.62 (s, 3H), 1.43 (d, J = 6.41 Hz, 3H). |
| 375 | 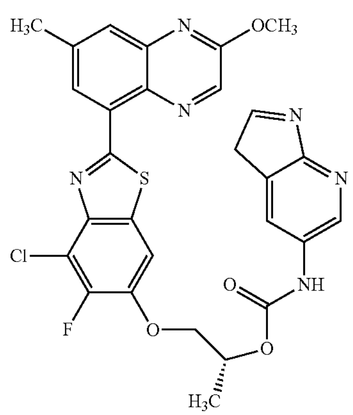 [SMILES: COc1cnc2c(-c3nc4c(Cl)c(F)c(OC[C@@H](C)OC(=O)Nc5cnc6c(c5)CC=N6)cc4s3)cc(C)cc2n1] | I-69 | 24 h | 593.2, 595.2 | 1.15 | 55-85% 16 min, 100% 7 min | ¹H NMR (500 MHz, DMSO-d₆) δ 11.43 (br. s., 1H), 9.42-9.72 (m, 1H), 8.59 (s, 1H), 8.46 (s, 1H), 8.19 (br. s., 1H), 8.02 (br. s., 1H), 7.84-7.94 (m, 1H), 7.74 (s, 1H), 7.39 (br. s., 1H), 6.37 (br. s., 1H), 5.24 (d, J = 3.36 Hz, 1H), 4.19-4.40 (m, 2H), 4.04 (s, 3H), 2.59 (s, 3H), 1.40 (d, J = 6.41 Hz, 3H). |
| 376 | 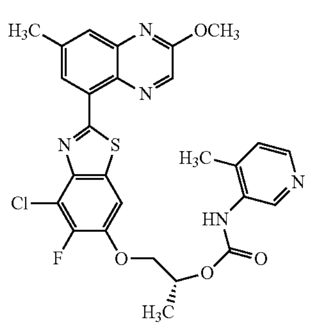 [SMILES: COc1cnc2c(-c3nc4c(Cl)c(F)c(OC[C@@H](C)OC(=O)Nc5cnccc5C)cc4s3)cc(C)cc2n1] | I-69 | 24 h | 568.2, 570.2 | 1.06 | 40-100% 20 min, 100% 5 min | ¹H NMR (500 MHz, DMSO-d₆) δ 9.46 (br. s., 1H), 8.66 (br. s., 1H), 8.54 (s, 1H), 8.40 (s, 1H), 8.30 (d, J = 4.58 Hz, 1H), 7.84 (d, J = 7.63 Hz, 1H), 7.68 (s, 1H), 7.48 (d, J = 5.19 Hz, 1H), 5.22 (dd, J = 3.05, 6.10 Hz, 1H), 4.14-4.41 (m, 2H), 3.99 (s, 3H), 2.54 (s, 3H), 2.13-2.33 (m, 3H), 1.37 (d, J = 6.41 Hz, 3H). |

-continued

| Ex | Structure | R—OH | Time | LCMS [M + H]+ m/z | LCMS RT (Min) Method H | HPLC Prep Method D | NMR |
|---|---|---|---|---|---|---|---|
| 377 | 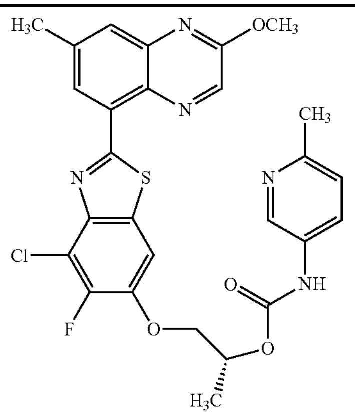 | I-69 | 24 h | 568.2, 570.2 | 1.07 | 60-100% 20 min, 100% 5 min | ¹H NMR (500 MHz, DMSO-d₆) δ 9.80 (br. s., 1H), 8.11-8.68 (m, 3H), 7.59-7.89 (m, 3H), 7.15 (d, J = 8.24 Hz, 1H), 5.23 (br. s., 1H), 4.20-4.48 (m, 2H), 4.02 (s, 3H), 2.57 (s, 3H), 2.36 (s, 3H), 1.40 (d, J = 6.41 Hz, 3H). |
| 378 | 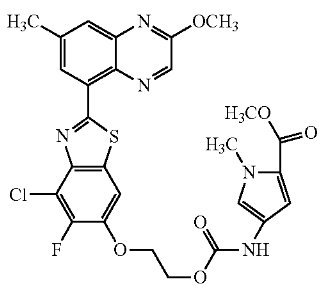 [SMILES: COC(=O)c1cc(NC(=O)OCCOc2cc3sc(-c4cc(C)cc5nc(OC)cnc45)nc3c(Cl)c2F)cn1C] | 318 | 1 h | 600.2, 602.2 | 1.28 | 50-85% 20 min, 100% 7 min | ¹H NMR (500 MHz, DMSO-d₆) δ 9.48-9.57 (m, 1H), 8.67 (s, 1H), 8.53 (s, 1H), 7.90-8.00 (m, 1H), 7.80 (s, 1H), 6.95-7.11 (m, 1H), 6.52-6.68 (m, 1H), 4.25-4.47 (m, 4H), 4.03 (s, 3H), 3.64 (br. s., 2H), 3.34-3.45 (m, 6H), 2.59 (s, 3H). |

Example 379

1-((5-fluoro-2-(2-methoxy-7-methylquinoxalin-5-yl)benzo[d]thiazol-6-yl)oxy)-3-isobutoxypropan-2-yl pyridin-3-ylcarbamate

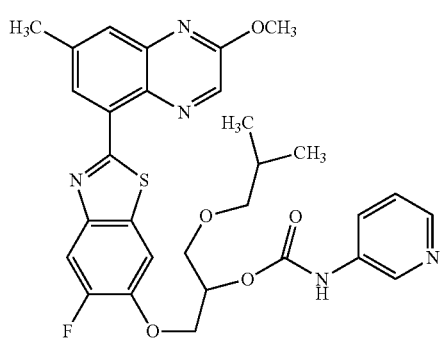

(379)

Intermediate 379A: 1-((5-fluoro-2-(2-methoxy-7-methylquinoxalin-5-yl)benzo[d]thiazol-6-yl)oxy)-3-isobutoxypropan-2-ol

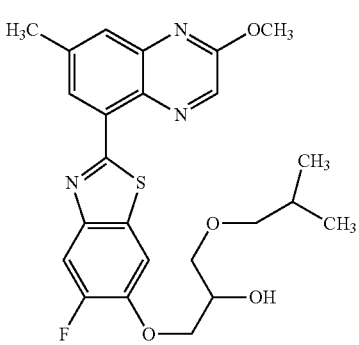

(379A)

To a suspension of Intermediate I-64 (15 mg, 0.044 mmol) in THF (1 mL) was added tetrabutylammonium bromide (28.3 mg, 0.088 mmol) followed by a 0.33 M solution of KOH (0.20 mL, 0.066 mmol). 2-(isobutoxymethyl)oxirane (0.1 mL) was then added, and the resulting mixture was heated to 65° C. in a sealed tube. After 16 h, the reaction was quenched with saturated NH₄Cl and diluted with EtOAc. The organic phase was washed with brine, dried over MgSO₄, filtered, concentrated and purified by ISCO (4 g, 0-60% EtOAc/Hexanes, 16 min. Product at 25%) to afford Intermediate 379A (14 mg, 0.024 mmol, 54.1% yield) as a yellow solid. LC-MS: Method H, RT=1.23 min, MS (ESI) m/z: 472.2 (M+H)⁺. ¹H NMR (400 MHz, CHLOROFORM-d) δ 8.60 (d, J=1.8 Hz, 1H), 8.54 (s, 1H), 7.81 (d, J=11.4 Hz, 1H), 7.75 (d, J=0.9 Hz, 1H), 7.50 (d, J=7.9 Hz, 1H), 4.30-4.22 (m, 1H), 4.22-4.15 (m, 2H), 4.13 (s, 3H), 3.70-3.61 (m, 2H), 3.32-3.25 (m, 2H), 2.65 (s, 3H), 2.62 (d, J=4.8 Hz, 1H), 1.97-1.80 (m, 1H), 0.92 (d, J=6.8 Hz, 6H).

Example 379

This example was prepared according to the general procedure for carbamates described in the table above. Thus, reaction of Intermediate 379A with 3-aminopyridine afforded Example 379 in 77% yield following purification by preparative HPLC (Method D, 45-100% over 15 min). LC-MS: Method H, RT=1.03 min, MS (ESI) m/z: 592.3 (M+H)⁺. ¹H NMR (500 MHz, DMSO-d₆) δ 10.37 (br. s., 1H), 8.79 (br. s., 1H), 8.72 (s, 1H), 8.56 (s, 1H), 8.36 (d, J=4.3 Hz, 1H), 8.10 (d, J=7.6 Hz, 1H), 8.02 (d, J=8.2 Hz, 1H), 7.97 (d, J=11.6 Hz, 1H), 7.82 (s, 1H), 7.61-7.53 (m, 1H), 5.42-5.32 (m, 1H), 4.53-4.45 (m, 1H), 4.45-4.37 (m, 1H), 4.09 (s, 3H), 3.80 (d, J=5.2 Hz, 2H), 3.37-3.29 (m, 1H), 3.28-3.22 (m, 1H), 2.63 (s, 3H), 1.84 (dt, J=13.2, 6.7 Hz, 1H), 0.93-0.81 (m, 6H).

Example 380

1-(benzyloxy)-3-((5-fluoro-2-(2-methoxy-7-methylquinoxalin-5-yl)benzo[d]thiazol-6-yl)oxy)propan-2-yl pyridin-3-ylcarbamate

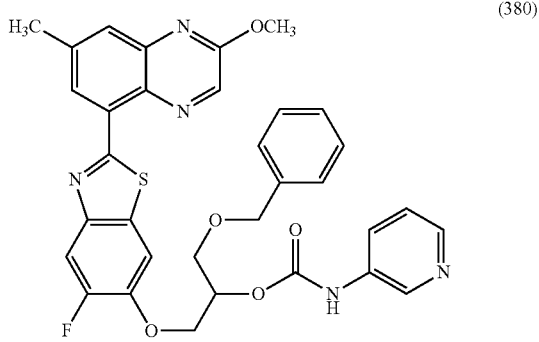 [SMILES: COc1cnc2c(-c3nc4cc(F)c(OCC(COCc5ccccc5)OC(=O)Nc5cccnc5)cc4s3)cc(C)cc2n1]

(380)

Intermediate 380A: 1-(benzyloxy)-3-((5-fluoro-2-(2-methoxy-7-methylquinoxalin-5-yl) benzo[d]thiazol-6-yl)oxy)propan-2-ol

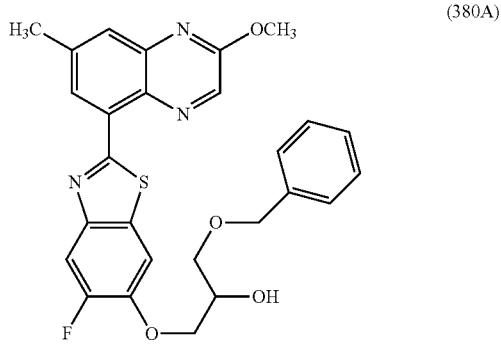 [SMILES: COc1cnc2c(-c3nc4cc(F)c(OCC(O)COCc5ccccc5)cc4s3)cc(C)cc2n1]

(380A)

To a suspension of Intermediate I-64 (15 mg, 0.044 mmol) in THF (1 mL) was added tetrabutylammonium bromide (28.3 mg, 0.088 mmol) followed by a 0.33 M solution of KOH (0.20 mL, 0.066 mmol). 2-((benzyloxy)methyl)oxirane (72.2 mg, 0.439 mmol) was then added, and the resulting mixture was heated to 65° C. in a sealed tube. After 16 h, the reaction was quenched with saturated NH₄Cl and diluted with EtOAc. The organic phase was washed with brine, dried over MgSO₄, filtered, concentrated and purified by ISCO (4 g, 0-60% EtOAc/Hexanes, 16 min. Product at 35%) to afford Intermediate 380A (16 mg, 0.032 mmol, 72.0% yield) as a yellow solid. LC-MS: Method H, RT=1.21 min, MS (ESI) m/z: 506.2 (M+H)⁺. ¹H NMR (400 MHz, CHLOROFORM-d) δ 8.60 (d, J=2.0 Hz, 1H), 8.53 (s, 1H), 7.80 (d, J=11.2 Hz, 1H), 7.74 (dd, J=1.8, 0.9 Hz, 1H), 7.46 (d, J=7.7 Hz, 1H), 7.38-7.27 (m, 5H), 4.61 (s, 2H), 4.33-4.24 (m, 1H), 4.23-4.17 (m, 2H), 4.12 (s, 3H), 3.77-3.68 (m, 2H), 2.66-2.62 (m, 4H).

Example 380

Example 380 was prepared according to the general procedure for carbamates described in the table above. Thus, reaction of Intermediate 380A with 3-aminopyridine afforded Example 380 in 34% yield following purification by preparative HPLC (Method D, 45-100% over 18 min). LC-MS: Method H, RT=1.02 min, MS (ESI) m/z: 626.3 (M+H)⁺. ¹H NMR (500 MHz, DMSO-d₆) δ 10.28 (br. s., 1H), 8.74 (br. s., 2H), 8.58 (br. s., 1H), 8.31 (br. s., 1H), 8.07-7.95 (m, 3H), 7.85 (br. s., 1H), 7.50 (br. s., 1H), 7.39-7.27 (m, 5H), 5.41 (br. s., 1H), 4.60 (d, J=7.3 Hz, 2H), 4.47 (d, J=17.4 Hz, 2H), 4.09 (br. s., 3H), 3.86 (br. s., 2H), 2.64 (br. s., 3H).

Example 381

2-((4-chloro-5-fluoro-2-(2-methoxy-7-methylquinoxalin-5-yl)benzo[d]thiazol-6-yl)oxy)propyl (6-methoxypyridin-3-yl)carbamate (racemate)

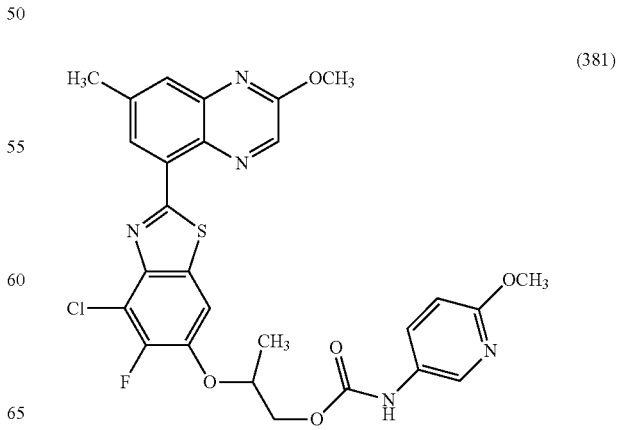

(381)

Intermediate 381A: methyl 2-((2-bromo-4-chloro-5-fluorobenzo[d]thiazol-6-yl)oxy) propanoate (Racemate)

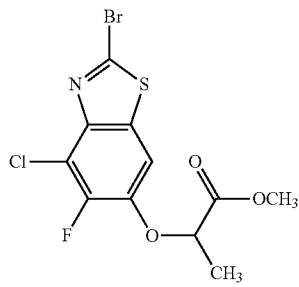

(381A)

Intermediate 381A was prepared in a manner analogous to Intermediate I-50. Thus, Intermediate I-44 was reacted to afford Intermediate 381A (rac) (46% yield) as a white solid. LC-MS: Method H, RT=1.12 min, MS (ESI) m/z: 368.0, 370.0, 372.0 (M+H)$^+$. $^1$H NMR (400 MHz, CHLOROFORM-d) δ 7.23 (d, J=6.8 Hz, 1H), 4.81 (q, J=6.8 Hz, 1H), 3.78 (s, 3H), 1.71 (d, J=6.8 Hz, 3H).

Intermediate 381B: 2-((2-bromo-4-chloro-5-fluorobenzo[d]thiazol-6-yl)oxy)propan-1-ol (Racemate)

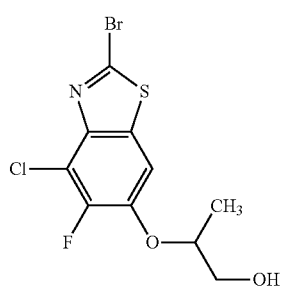

(381B)

Intermediate 381B was prepared in a manner analogous to Intermediate I-51. Thus, Intermediate 381A (rac) was reacted to afford Intermediate 381B (rac) (75% yield) as an off-white, amorphous solid. LC-MS: Method H, RT=1.05 min, MS (ESI) m/z: 339.9, 341.9, 343.9 (M+H)$^+$. $^1$H NMR (400 MHz, METHANOL-d$_4$) δ 7.71 (d, J=7.3 Hz, 1H), 4.64-4.52 (m, 1H), 3.79-3.67 (m, 2H), 1.34 (d, J=6.2 Hz, 3H)

Intermediate 381C: 2-((2-bromo-4-chloro-5-fluorobenzo[d]thiazol-6-yl)oxy)propyl (6-methoxypyridin-3-yl)carbamate (Racemate)

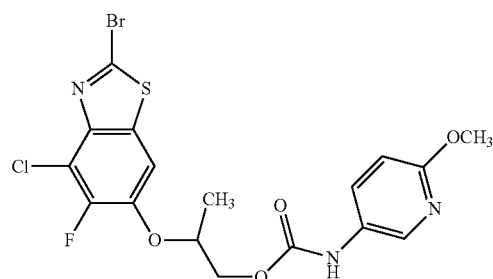

(381C)

Intermediate 381C was prepared according to the general procedure for carbamates described in the table above. Thus, reaction of Intermediate 381B (rac) with 3-amino-6-methoxypyridine afforded Intermediate 381C (rac) in 90% yield. LC-MS: Method H, RT=1.11 min, MS (ESI) m/z: 489.9, 491.9, 493.9 (M+H)$^+$. $^1$H NMR (400 MHz, CHLOROFORM-d) δ 8.05 (br. s., 1H), 7.73 (br. s., 1H), 7.35 (d, J=7.3 Hz, 1H), 6.72 (d, J=8.8 Hz, 1H), 6.53 (br. s., 1H), 4.76-4.59 (m, 1H), 4.36 (d, J=5.3 Hz, 2H), 3.91 (s, 3H), 1.43 (d, J=6.4 Hz, 3H).

Example 381

Example 381 was prepared according to the general procedure for quinoxaline-benzothiazoles described in the table above. Thus, reaction of Intermediate 381C (rac) with Intermediate I-9 afforded Example 381 (rac) in 23% yield following purification by preparative HPLC (Method D, 55-95% over 30 min). LC-MS: Method H, RT=1.31 min, MS (ESI) m/z: 584.1, 586,1 (M+H)$^+$. $^1$H NMR (500 MHz, DMSO-d$_6$) δ 9.71 (br. s., 1H), 8.73 (s, 1H), 8.58 (d, J=1.4 Hz, 1H), 8.21 (br. s., 1H), 8.07 (d, J=7.4 Hz, 1H), 7.85 (s, 1H), 7.77 (br. s., 1H), 6.77 (d, J=8.3 Hz, 1H), 4.92 (td, J=6.2, 3.3 Hz, 1H), 4.46-4.27 (m, 2H), 4.10 (s, 3H), 3.78 (s, 3H), 2.66 (s, 3H), 1.43 (d, J=6.3 Hz, 3H)

Example 382

(S)-2-((4-chloro-5-fluoro-2-(2-methoxy-7-methylquinoxalin-5-yl)benzo[d]thiazol-6-yl)oxy)propyl (6-methoxypyridin-3-yl)carbamate

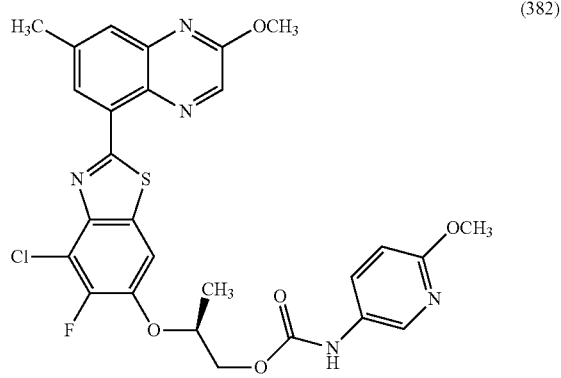 [SMILES: COc1ccc(NC(=O)OC[C@H](C)Oc2cc3sc(-c4cc(C)cc5nc(OC)cnc45)nc3c(Cl)c2F)cn1]

(382)

This example was prepared by subjecting Example 381 (rac) to chiral, super-critical fluid chromatography conditions (Berger Multigram II SFC, Chiralpak OJ, 21×250 mm, 5 micron, 45% EtOH/-0.1% DEA/55% CO$_2$, 40 mL/min flow rate) to give Example 382 as the second eluting enantiomer. The absolute stereochemistry of this example was assigned by analogy to other biologically active enantiomers in the same series. LC-MS: Method H, RT=1.31 min, MS (ESI) m/z: 584.1, 586.1 (M+H)$^+$. $^1$H NMR (500 MHz, DMSO-d$_6$) δ 9.71 (br. s., 1H), 8.73 (s, 1H), 8.58 (d, J=1.4 Hz, 1H), 8.21 (br. s., 1H), 8.07 (d, J=7.4 Hz, 1H), 7.85 (s, 1H), 7.77 (br. s., 1H), 6.77 (d, J=8.3 Hz, 1H), 4.92 (td, J=6.2, 3.3 Hz, 1H), 4.46-4.27 (m, 2H), 4.10 (s, 3H), 3.78 (s, 3H), 2.66 (s, 3H), 1.43 (d, J=6.3 Hz, 3H).

Example 383

2-((4-chloro-5-fluoro-2-(2-methoxy-7-methylquinoxalin-5-yl)benzo[d]thiazol-6-yl)oxy)ethyl (2-chlorothiazol-4-yl)carbamate

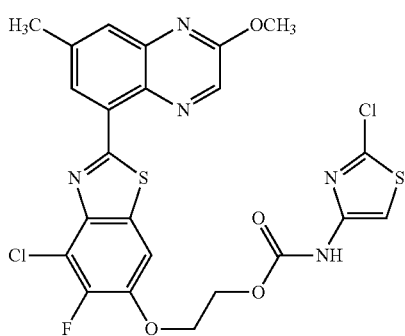
(383)

To a suspension of Example 318 (12 mg, 0.029 mmol) and 2-chlorothiazole-4-carboxylic acid (9.35 mg, 0.057 mmol) in Toluene (1 mL) was added triethylamine (7.97 μl, 0.057 mmol) followed by diphenylphosphoryl azide (15.73 mg, 0.057 mmol). The reaction vessel was then sealed and heated to 110° C. for 3 hours. The resulting mixture was cooled to room temperature, concentrated and purified by preparative HPLC (Method D, 60-100% over 20 min, hold at 100% for 10 min) to afford Example 383 in 20% yield. LC-MS: Method H, RT=1.35 min, MS (ESI) m/z: 580.1 (M+H)$^+$. $^1$H NMR (500 MHz, DMSO-d$_6$) δ 9.71 (br. s., 1H), 8.73 (s, 1H), 8.58 (d, J=1.4 Hz, 1H), 8.21 (br. s., 1H), 8.07 (d, J=7.4 Hz, 1H), 7.85 (s, 1H), 7.77 (br. s., 1H), 6.77 (d, J=8.3 Hz, 1H), 4.92 (td, J=6.2, 3.3 Hz, 1H), 4.46-4.27 (m, 2H), 4.10 (s, 3H), 3.78 (s, 3H), 2.66 (s, 3H), 1.43 (d, J=6.3 Hz, 3H).

Example 384

2-((4-chloro-5-fluoro-2-(2-methoxy-7-methylquinoxalin-5-yl)benzo[d]thiazol-6-yl)oxy)ethyl thiazol-5-ylcarbamate

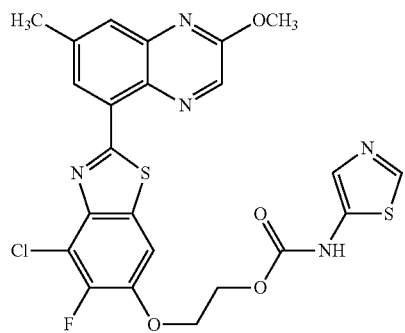
(384)

Example 384 was prepared in a manner analogous to Example 383. Thus, Example 318 was reacted with thiazole-5-carboxylic acid to afford Example 384 (3% yield) following purification by preparative HPLC (Method D, 40-80% over 20 min, hold at 100% for 5 min). LC-MS: Method H, RT=1.21 min, MS (ESI) m/z: 546.1, 548.1 (M+H)$^+$. $^1$H NMR (500 MHz, CHLOROFORM-d) δ 8.66-8.85 (m, 1H), 8.53-8.62 (m, 1H), 8.38-8.51 (m, 1H), 7.71-7.85 (m, 1H), 7.53-7.64 (m, 1H), 7.36-7.45 (m, 1H), 7.28-7.33 (m, 1H), 4.67 (br. s., 2H), 4.41 (br. s., 2H), 4.14 (br. s., 3H), 2.68 (br. s., 3H).

Example 385

(R)-1-((4-chloro-5-fluoro-2-(2-methoxy-7-methylquinoxalin-5-yl)benzo[d]thiazol-6-yl)oxy)propan-2-yl (6-(hydroxymethyl)pyridin-3-yl)carbamate

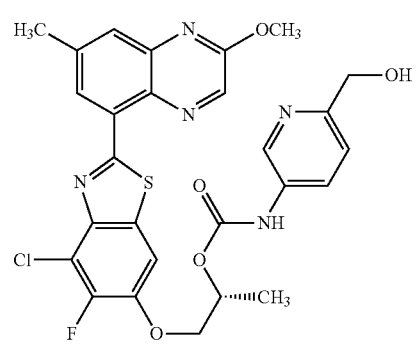
(385)

Intermediate 385A: (5-aminopyridin-2-yl)methanol

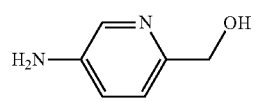
(385A)

To a suspension of methyl 5-aminopicolinate (70 mg, 0.460 mmol) in THF (3 mL) was added a solution of LAH (1 M in THF) (0.920 mL, 0.920 mmol) at 0° C. The mixture was allowed to warm to room temperature and stirred overnight. After 16 h, the reaction was quenched with water (0.1 mL) at 0° C. A solution of sodium hydroxide (2 N, 0.1 mL) was subsequently added followed by an additional quantity of water (0.3 mL). Magnesium sulfate was added and the mixture was stirred for 1 hour before being filtered over a pad of celite and washed with THF. The filtrate was concentrated in vacuo to afford Intermediate 385A (35 mg, 0.282 mmol, 61.3% yield) as a yellow solid. This material was taken on without further purification. LC-MS: Method H, RT=0.44 min, MS (ESI) m/z: 125.1 (M+H)$^+$. $^1$H NMR (400 MHz, DMSO-d$_6$) δ 7.80-7.88 (m, 1H), 7.05-7.16 (m, 1H), 6.83-6.96 (m, 1H), 4.88-5.04 (m, 1H), 4.27-4.41 (m, 2H).

Intermediate 385B: 6-(((tert-butyldimethylsilyl)oxy)methyl)pyridin-3-amine

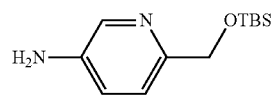
(385B)

To a stirred solution of crude Intermediate 385A (225 mg, 1.812 mmol) in DMF (5 mL) was added TBDMS-Cl (410 mg, 2.72 mmol) followed by imidazole (222 mg, 3.26 mmol). The reaction mixture was stirred for 1 h at room temperature before being concentrated and purified by ISCO (24 g, 0-100% EtOAc/Hexanes, 15 min. Product at 65%) to afford Intermediate 385B (132 mg, 0.554 mmol, 30.5% yield), as a yellow solid. LC-MS: Method H, RT=0.81 min, MS (ESI) m/z: 239.4 (M+H)+. 1H NMR (400 MHz, DMSO-d6) δ 7.79 (d, J=2.64 Hz, 1H), 7.00 (s, 1H), 6.77-6.91 (m, 1H), 5.13 (s, 2H), 4.50 (s, 2H), 0.84 (s, 9H), 0.00 (s, 6H).

Intermediate 385C: (R)-1-((4-chloro-5-fluoro-2-(2-methoxy-7-methylquinoxalin-5-yl) benzo[d]thiazol-6-yl)oxy)propan-2-yl (6-(((tert-butyldimethylsilyl) oxy)methyl)pyridin-3-yl)carbamate

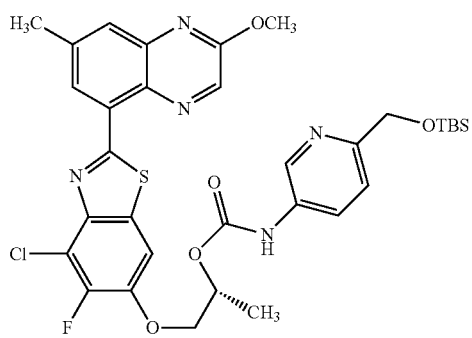

(385C)

This intermediate was prepared according to the general procedure for carbamates described in the table above. Thus, reaction of Intermediate I-69 with Intermediate 385B afforded Intermediate 385C, which was telescoped into the subsequent silyl-deprotection reaction. LC-MS: Method H, RT=1.26 min, MS (ESI) m/z: 698.5, 700.5 (M+H)+.

Example 385

Intermediate 385C was concentrated and redissolved in 10 mL mixture of MeOH (9.5 mL) and 12 M HCl (0.5 mL). The resulting solution was stirred for 10 minutes before being concentrated down and purified by preparative HPLC (Method D, 50-100% over 10 min, hold at 100% for 10 min) to afford Example 385 in 9% overall yield as a yellow solid. LC-MS: Method H, RT=1.07 min, MS (ESI) m/z: 584.3, 586.3 (M+H)+. 1H NMR (400 MHz, DMSO-d6) δ 9.69-9.99 (m, 1H), 8.77 (s, 1H), 8.60-8.65 (m, 1H), 8.53-8.57 (m, 1H), 8.02-8.10 (m, 1H), 7.82-7.93 (m, 2H), 7.33-7.42 (m, 1H), 5.21-5.37 (m, 2H), 4.46-4.52 (m, 2H), 4.38-4.45 (m, 1H), 4.24-4.35 (m, 1H), 2.67 (s, 4H), 1.43 (d, J=6.38 Hz, 3H).

Example 386

(2R,3S)-3-((5-fluoro-2-(2-methoxy-7-methylquinoxalin-5-yl)benzo[d]thiazol-6-yl)oxy)butan-2-yl (2-methylpyrimidin-5-yl)carbamate

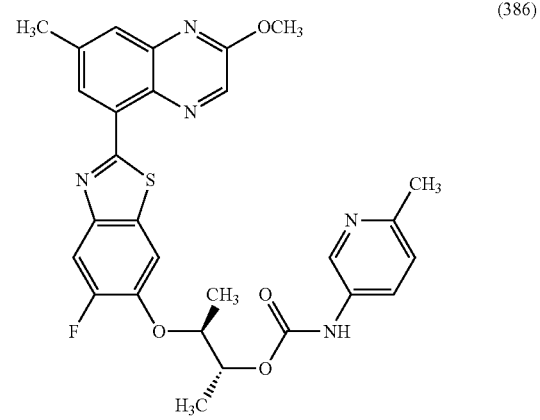

(386)

Example 386 was prepared according to the general procedure for carbamates described in the table above. Thus, reaction of Intermediate I-72 with 2-methylpyrimidin-5-amine and pyridine afforded Example 386 in 46% yield following purification by Prep HPLC (Method D, 50-100% over 10 min, hold 100% for 8 min). LC-MS: Method H, RT=1.20 min, MS (ESI) m/z: 549.2 (M+H)+. 1H NMR (400 MHz, CHLOROFORM-d) δ 8.74 (s, 2H), 8.63 (d, J=1.5 Hz, 1H), 8.57 (s, 1H), 7.85 (d, J=11.4 Hz, 1H), 7.79 (s, 1H), 7.58-7.52 (m, 1H), 6.51 (br. s., 1H), 5.18 (dd, J=6.5, 3.0 Hz, 1H), 4.69-4.59 (m, 1H), 4.16 (s, 3H), 2.70 (s, 3H), 2.68 (s, 3H), 1.50 (d, J=6.6 Hz, 3H), 1.46 (d, J=6.4 Hz, 3H).

Example 387

(2R,3S)-3-((5-fluoro-2-(2-methoxy-7-methylquinoxalin-5-yl)benzo[d]thiazol-6-yl)oxy)butan-2-yl (6-(2-hydroxyethyl)pyridin-3-yl)carbamate

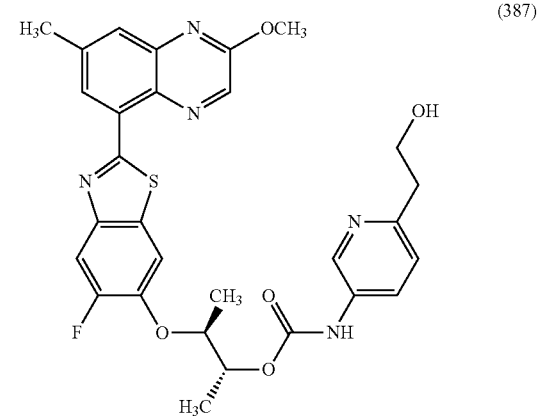 [SMILES: COc1cnc2c(-c3nc4cc(F)c(O[C@@H](C)[C@@H](C)OC(=O)Nc5ccc(CCO)nc5)cc4s3)cc(C)cc2n1]

(387)

Example 387 was prepared according to the general procedure for carbamates described in the table above. Thus, reaction of Intermediate I-72 with 6-(2-((tert-butyldimethylsilyl)oxy)ethyl)pyridin-3-amine afforded the TBS-protected intermediate of the desired product. The crude reaction mixture was concentrated and retaken in a 20:1 mixture of MeOH/concentrated HCl to affect the desired silyl deprotection and afford Example 387 in 46% yield following purification by Prep HPLC (Method D, 50-100% over 10 min, hold 100% for 8 min). LC-MS: Method H, RT=0.98 min, MS (ESI) m/z: 578.2 (M+H)+. $^1$H NMR (400 MHz, CHLOROFORM-d) δ 9.79 (br. s., 1H), 8.73 (s, 1H), 8.58 (d, J=1.8 Hz, 1H), 8.53 (br. s., 1H), 8.04 (d, J=8.4 Hz, 1H), 7.96 (d, J=11.7 Hz, 1H), 7.83 (s, 1H), 7.78 (d, J=7.0 Hz, 1H), 7.20 (d, J=8.4 Hz, 1H), 5.10 (qd, J=6.5, 2.9 Hz, 1H), 4.82-4.73 (m, 1H), 4.08 (s, 3H), 3.67 (t, J=6.9 Hz, 2H), 2.79 (t, J=6.8 Hz, 2H), 2.63 (s, 3H), 1.39 (m, 6H)

Example 388

(2R,3S)-3-((5-fluoro-2-(2-methoxy-7-methylquinoxalin-5-yl)benzo[d]thiazol-6-yl)oxy)butan-2-yl (2-(2-hydroxyethoxy)pyridin-4-yl)carbamate

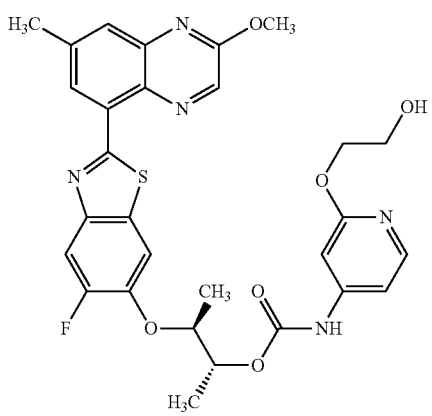

(388)

Example 388 was prepared according to the general procedure for carbamates described in the table above. Thus, reaction of Intermediate I-72 with 2-(2-((tert-butyldimethylsilyl)oxy)ethoxy)pyridin-4-amine afforded the TBS-protected intermediate of the desired product. Excess TBAF (10 equiv, 1 M in THF) was added to the crude reaction mixture to afford Example 388 in 26% yield following purification by Prep HPLC (Method D, 50-100% over 10 min, hold 100% for 8 min). LC-MS: Method H, RT=1.06 min, MS (ESI) m/z: 594.2 (M+H)+. $^1$H NMR (400 MHz, CHLOROFORM-d) δ 9.99 (s, 1H), 8.67 (s, 1H), 8.51 (d, J=1.8 Hz, 1H), 7.97 (d, J=8.1 Hz, 1H), 7.89 (d, J=11.7 Hz, 1H), 7.86 (d, J=5.9 Hz, 1H), 7.77 (s, 1H), 6.96 (dd, J=5.7, 1.8 Hz, 1H), 6.83 (d, J=1.3 Hz, 1H), 5.10-5.00 (m, 1H), 4.76-4.67 (m, 2H), 4.12 (t, J=5.1 Hz, 2H), 4.01 (s, 3H), 3.58 (q, J=5.4 Hz, 2H), 2.56 (s, 3H), 1.32 (m, 6H).

Example 389

(2R,3S)-3-((2-(2-ethoxy-7-methylquinoxalin-5-yl)-5-fluorobenzo[d]thiazol-6-yl)oxy)butan-2-yl (2-methylpyrimidin-5-yl)carbamate

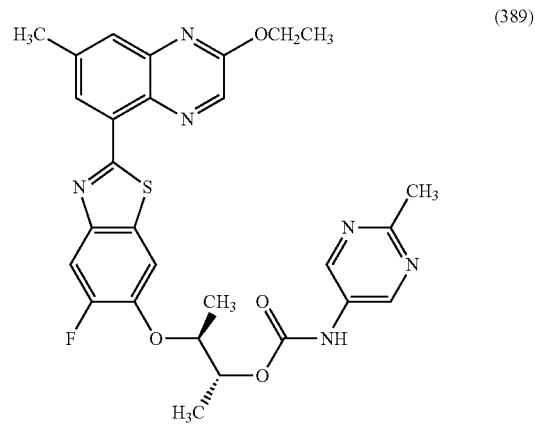

(389)

To a solution of Intermediate I-73 (30 mg, 0.051 mmol) in THF (1.5 mL) was added ethanol (0.5 mL, 8.56 mmol) followed by sodium hydride (20.53 mg, 0.513 mmol, 60% suspension in mineral oil). The reaction mixture was stirred for 10 min at room temperature before being quenched with saturated NH$_4$Cl (~0.15 mL). The resulting mixture was diluted with EtOAc, filtered over celite, concentrated, retaken in DMF, filtered and purified by Prep HPLC (Method D, 50-100% over 10 min, hold 100% for 8 min) to afford Example 389 (17.7 mg, 0.030 mmol, 58% yield) as a yellow solid. LC-MS: Method H, RT=1.25 min, MS (ESI) m/z: 563.2 (M+H)+. $^1$H NMR (500 MHz, DMSO-d$_6$) δ 9.96 (br. s., 1H), 8.71 (br. s., 2H), 8.63 (s, 1H), 8.50 (s, 1H), 8.00 (d, J=8.2 Hz, 1H), 7.91 (d, J=11.3 Hz, 1H), 7.75 (s, 1H), 5.10 (dd, J=6.7, 2.4 Hz, 1H), 4.78 (d, J=4.0 Hz, 1H), 4.49 (q, J=7.0 Hz, 2H), 2.59 (s, 3H), 2.50 (s, 3H-buried under d-DMSO), 1.42 (t, J=7.2 Hz, 3H), 1.38 (m, 6H).

Example 390

(2R,3S)-3-((5-fluoro-2-(7-methyl-2-(methylamino)quinoxalin-5-yl)benzo[d]thiazol-6-yl)oxy)butan-2-yl (2-methylpyrimidin-5-yl)carbamate

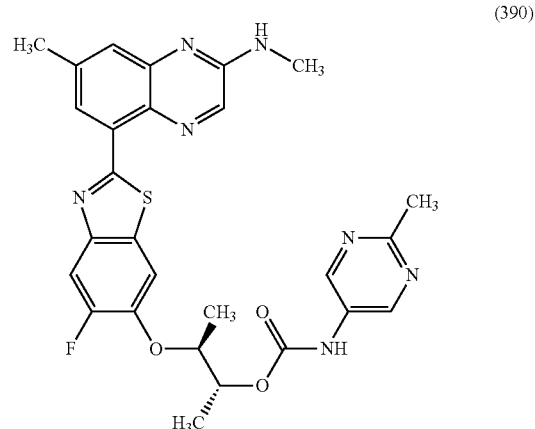

(390)

To a vial charged with Intermediate I-73 (10 mg, 0.017 mmol) was added methanamine (33% solution in EtOH) (1 mL, 8.00 mmol). The mixture was stirred at room temperature for 16 h before being concentrated and purified by Prep HPLC (Method D, 50-100% over 10 min, hold 100% for 8 min) to afford Example 390 (17.7 mg, 0.030 mmol, 58% yield) as a yellow solid. LC-MS: Method H, RT=0.92 min, MS (ESI) m/z: 548.1 (M+H)+. $^1$H NMR (500 MHz, DMSO-$d_6$) δ 9.97 (br. s., 1H), 8.72 (br. s., 2H), 8.42 (s, 1H), 8.27 (s, 1H), 8.00 (d, J=8.2 Hz, 1H), 7.92 (d, J=11.3 Hz, 1H), 7.56 (s, 1H), 5.10 (d, J=4.9 Hz, 1H), 4.79 (d, J=4.0 Hz, 1H), 2.96 (s, 3H), 2.50 (s, 3H-buried under d-DMSO), 1.38 (m, 6H).

Example 391

(2R,3S)-3-((5-fluoro-2-(2-methoxy-7-methylquinoxalin-5-yl)benzo[d]thiazol-6-yl)oxy)butan-2-yl (6-carbamoylpyridin-3-yl)carbamate

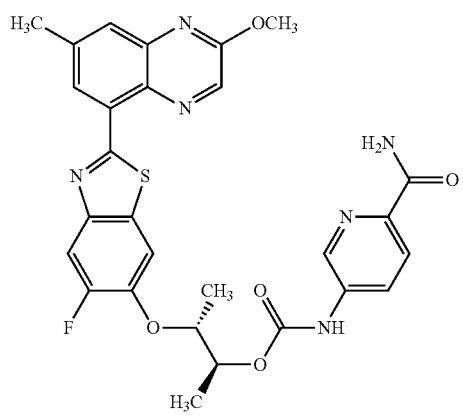

(391)

To a vial charged with Intermediate I-74 (20 mg, 0.034 mmol) was added ammonia (7M solution in MeOH) (1 mL, 14.00 mmol). The mixture was sealed and heated to 65° C. for 24 h before being concentrated and purified by Prep HPLC (Method D, 50-100% over 10 min, hold 100% for 8 min) to afford Example 391 (8 mg, 0.013 mmol, 38% yield) as a yellow solid. LC-MS: Method H, RT=1.21 min, MS (ESI) m/z: 577.2 (M+H)+. $^1$H NMR (500 MHz, DMSO-$d_6$) δ 10.18 (br. s., 1H), 8.71-8.61 (m, 2H), 8.52 (s, 1H), 8.01 (d, J=8.2 Hz, 2H), 7.98-7.89 (m, 3H), 7.79 (s, 1H), 7.45 (br. s., 1H), 5.12 (d, J=5.8 Hz, 1H), 4.80 (d, J=6.1 Hz, 1H), 4.05 (s, 3H), 2.60 (s, 3H), 1.39 (m, 6H).

Example 392

(2R,3S)-3-((5-fluoro-2-(2-methoxy-7-methylquinoxalin-5-yl)benzo[d]thiazol-6-yl)oxy)butan-2-yl (6-((2-hydroxyethyl)carbamoyl)pyridin-3-yl)carbamate

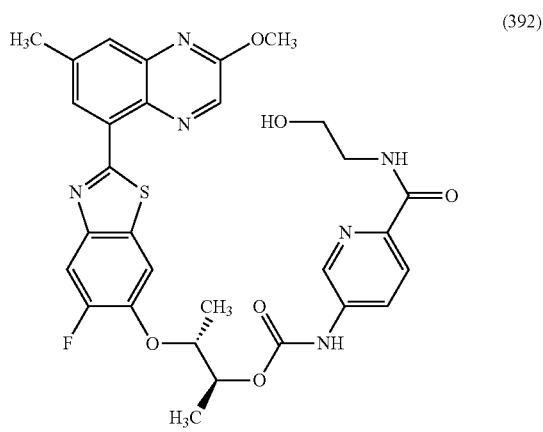 [SMILES: COc1cnc2c(-c3nc4cc(F)c(O[C@H](C)[C@H](C)OC(=O)Nc5ccc(C(=O)NCCO)nc5)cc4s3)cc(C)cc2n1]

(392)

To a solution of Intermediate I-74 (10 mg, 0.017 mmol) in THF (1 mL) was added ethanolamine (0.1 mL). The reaction mixture was allowed to stir at room temperature for 16 h before being concentrated and purified by Prep HPLC (Method D, 50-100% over 10 min, hold 100% for 8 min) to afford Example 392 (8.7 mg, 0.014 mmol, 81% yield) as a yellow solid. LC-MS: Method H, RT=1.15 min, MS (ESI) m/z: 621.1 (M+H)+. $^1$H NMR (500 MHz, DMSO-$d_6$) δ 10.15 (br. s., 1H), 8.63 (d, J=5.8 Hz, 2H), 8.53-8.43 (m, 2H), 7.97 (d, J=8.5 Hz, 2H), 7.94-7.86 (m, 2H), 7.76 (s, 1H), 5.11 (d, J=5.8 Hz, 1H), 4.89-4.84 (m, 1H), 4.81 (br. s., 1H), 4.04 (s, 3H), 3.48 (d, J=5.5 Hz, 2H), 3.32 (d, J=5.5 Hz, 2H), 2.58 (s, 3H), 1.38 (m, 6H).

Example 393

(2R,3S)-3-((5-fluoro-2-(7-methyl-2-(methylcarbamoyl)quinoxalin-5-yl)benzo[d]thiazol-6-yl)oxy)butan-2-yl (2-methylpyrimidin-5-yl)carbamate

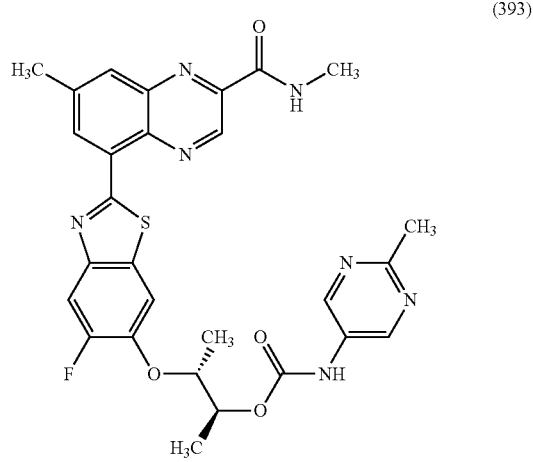

(393)

To a solution of Intermediate I-75 (13 mg, 0.022 mmol) in THF (1 mL) was added methanamine (33% solution in EtOH) (0.2 mL, 1.60 mmol). The reaction mixture was allowed to stir at room temperature for 16 h before being concentrated and purified by Prep HPLC (Method D, 50-100% over 10 min, hold 100% for 8 min) to afford Example 393 (5 mg, 0.008 mmol, 37% yield) as a yellow solid. LC-MS: Method H, RT=0.99 min, MS (ESI) m/z: 576.2 (M+H)+. $^1$H NMR (500 MHz, DMSO-d$_6$) δ 9.48 (s, 1H), 9.07 (d, J=4.9 Hz, 1H), 8.83 (s, 1H), 8.73 (br. s., 2H), 8.11-8.01 (m, 2H), 7.94 (d, J=11.6 Hz, 1H), 5.12 (d, J=6.4 Hz, 1H), 4.83 (d, J=4.3 Hz, 1H), 2.98-2.90 (m, 3H), 2.70 (s, 3H), 2.52 (br. s., 3H), 1.40 (m, 6H).

Preparation of Carbamate Examples

The Carbamates in the table below were prepared according to the following general procedure, which is analogous to Intermediate I-82 described above:

To a solution of the appropriately substituted quinoxaline-benzothiazole alcohol (1.0 equiv) in THF (0.05 M) was added a solution of phosgene (15% by wt. in toluene, 10 equiv). This solution was stirred at room temperature overnight, and the intermediate chloroformate was concentrated in vacuo. This crude chloroformate was then retaken in THF (0.05 M) and added dropwise to a pre-mixed solution of pyridine (10 equiv) and the appropriately substituted amino-heterocycle or amine (3.0 equiv) in either THF (0.05 M) or DCM (0.05) (whichever gave the best reagent solubility). After 10 min of stirring, the combined mixture was concentrated and purified by preparative HPLC to yield the desired example.

| Ex. No. | Structure | R—OH | LCMS [M + H]+ m/z | LCMS RT (Min) Method H | HPLC Prep Method D | NMR |
|---|---|---|---|---|---|---|
| 394 | 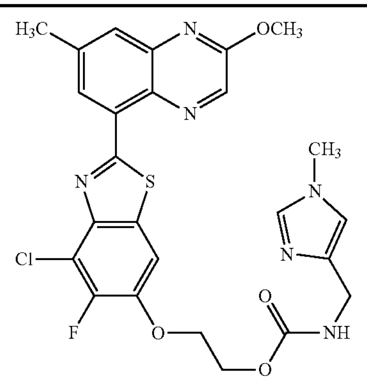 | I-67 | 568.3 | 1.13 | 30-65% 20 min, 100% 5 min | $^1$H NMR (500 MHz, DMSO-d$_6$) δ 8.74 (s, 1H), 8.58 (d, J = 1.7 Hz, 1H), 7.99-7.94 (m, 2H), 7.83 (s, 1H), 7.14 (t, J = 5.5 Hz, 1H), 5.13-5.04 (m, 1H), 4.27-4.16 (m, 2H), 4.09 (s, 3H), 3.31-3.16 (m, 6H), 2.63 (s, 3H), 2.39 (t, J = 7.2 Hz, 2H), 1.88-1.78 (m, 2H), 1.73 (quin, J = 6.7 Hz, 2H), 1.32 (d, J = 6.6 Hz, 3H) |
| 395 | 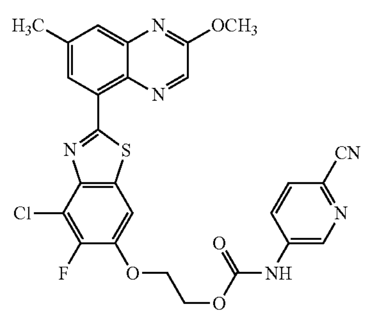 [SMILES: COc1cnc2c(-c3nc4c(Cl)c(F)c(OCCOC(=O)Nc5ccc(C#N)nc5)cc4s3)cc(C)cc2n1] | 318 | 565.2, 567.3 | 1.22 | 60-100% 20 min, 100% 8 min | — |
| 396 | 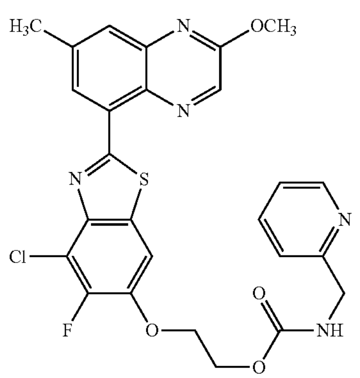 [SMILES: COc1cnc2c(-c3nc4c(Cl)c(F)c(OCCOC(=O)NCc5ccccn5)cc4s3)cc(C)cc2n1] | 318 | 545.2, 556.2 | 1.02 | 50-100% 20 min, 100% 5 min | $^1$H NMR (500 MHz, DMSO-d$_6$) δ 8.67 (s, 1H), 8.53 (br. s., 1H), 8.46 (br. s., 1H), 7.92 (br. s., 1H), 7.88 (d, J = 6.4 Hz, 1H), 7.81 (br. s., 1H), 7.73 (t, J = 7.2 Hz, 1H), 7.38-7.30 (m, 1H), 7.29-7.21 (m, 1H), 4.39 (d, J = 7.6 Hz, 4H), 4.28 (d, J = 5.8 Hz, 2H), 4.05 (s, 3H), 2.62 (s, 3H) |

| Ex. No. | Structure | R—OH | LCMS [M + H]+ m/z | LCMS RT (Min) Method H | HPLC Prep Method D | NMR |
|---|---|---|---|---|---|---|
| 397 | 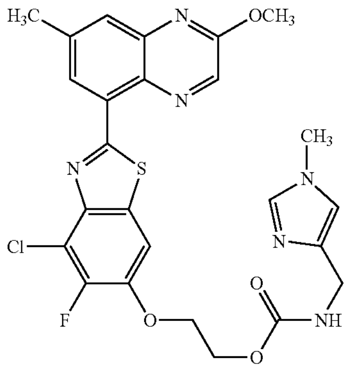 [SMILES: COc1cnc2c(-c3nc4c(Cl)c(F)c(OCCOC(=O)NCc5cn(C)cn5)cc4s3)cc(C)cc2n1] | 318 | 557.2, 559.3 | 1.21 | 45-90% 30 min, 100% 5 min | ¹H NMR (500 MHz, DMSO-d₆) δ 8.59 (s, 1H), 8.45 (br. s., 1H), 7.85-7.81 (m, 1H), 7.72 (br. s., 1H), 7.51 (br. s., 1H), 7.40 (s, 1H), 6.82 (s, 1H), 4.31 (d, J = 8.2 Hz, 4H), 4.00 (m, 5H), 3.47 (br. s., 3H), 2.56 (s, 3H) |
| 398 | 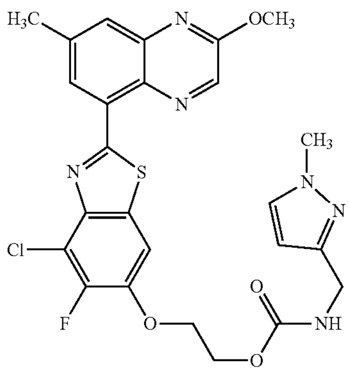 [SMILES: COc1cnc2c(-c3nc4c(Cl)c(F)c(OCCOC(=O)NCc5ccn(C)n5)cc4s3)cc(C)cc2n1] | 318 | 557.2, 559.2 | 1.21 | 45-100% 20 min, 100% 5 min | ¹H NMR (500 MHz, CDCl₃) δ 8.67 (s, 1H), 8.47 (s, 1H), 7.70 (s, 1H), 7.33 (d, J = 6.9 Hz, 1H), 7.20 (br. s., 1H), 6.10 (s, 1H), 5.19 (br. s., 1H), 4.46 (br. s., 2H), 4.32 (d, J = 5.5 Hz, 2H), 4.27 (br. s., 2H), 4.06 (s, 3H), 3.78 (s, 3H), 2.60 (s, 3H) |
| 399 | 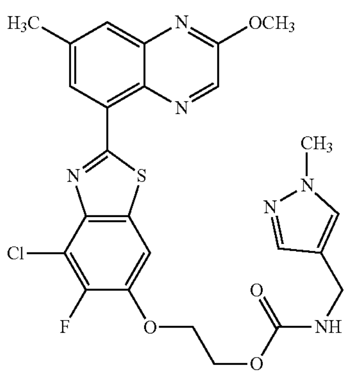 [SMILES: COc1cnc2c(-c3nc4c(Cl)c(F)c(OCCOC(=O)NCc5cnn(C)c5)cc4s3)cc(C)cc2n1] | 318 | 557.2, 559.2 | 1.18 | 45-80% 20 min, 100% 7 min | ¹H NMR (500 MHz, DMSO-d₆) δ 8.61 (s, 1H), 8.47 (s, 1H), 7.85 (d, J = 7.3 Hz, 1H), 7.74 (s, 1H), 7.58 (br. s., 1H), 7.47 (s, H), 7.24 (s, H), 4.31 (d, J = 8.2 Hz, 4H), 4.01 (s, 3H), 3.97 (d, J = 5.8 Hz, 2H), 3.71 (s, 3H), 2.57 (s, 3H) |
| 400 | 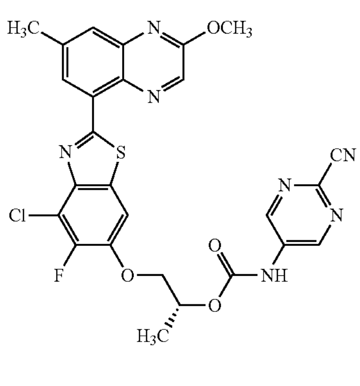 [SMILES: COc1cnc2c(-c3nc4c(Cl)c(F)c(OC[C@@H](C)OC(=O)Nc5cnc(C#N)nc5)cc4s3)cc(C)cc2n1] | I-69 | 580.2, 582.2 | 1.30 | 50-100% 20 min, 100% 5 min | ¹H NMR (500 MHz, DMSO-d₆) δ 9.04 (s, 2H), 8.73 (s, 1H), 8.58 (s, 1H), 8.03 (d, J = 7.6 Hz, 1H), 7.86 (s, 1H), 5.36 (br. s., 1H), 4.53-4.45 (m, 1H), 4.38 (dd, J = 10.8, 6.0 Hz, 1H), 4.13 (s, 3H), 2.69 (s, 3H), 1.51 (d, J = 6.4 Hz, 3H) |

-continued

| Ex. No. | Structure | R—OH | LCMS [M + H]+ m/z | LCMS RT (Min) Method H | HPLC Prep Method D | NMR |
|---|---|---|---|---|---|---|
| 401 | (structure) | I-69 | 590.2, 592.2 | 1.34 | 50-100% 20 min, 100% 5 min | ¹H NMR (500 MHz, DMSO-d₆) δ 8.80 (s, 2H), 8.74 (s, 1H), 8.59 (d, J = 1.7 Hz, 1H), 8.04 (d, J = 7.7 Hz, 1H), 7.86 (s, 1H), 5.27 (td, J = 6.3, 3.0 Hz, 1H), 4.44-4.39 (m, 1H), 4.32 (dd, J = 10.9, 5.9 Hz, 1H), 4.09 (s, 3H), 2.65 (s, 3H), 1.43 (d, J = 6.6 Hz, 3H) |
| 402 | (structure) | I-69 | 586.1, 588.1 | 1.35 | 50-100% 20 min, 100% 5 min | ¹H NMR (500 MHz, DMSO-d₆) δ 8.69 (s, 1H), 8.54 (s, 1H), 8.13 (br. s., 1H), 7.98 (d, J = 7.3 Hz, 1H), 7.91 (br. s., 1H), 7.81 (s, 1H), 5.31 (br. s., 1H), 4.47-4.39 (m, 1H), 4.34 (dd, J = 10.4, 6.1 Hz, 1H), 4.12 (s, 3H), 2.67 (s, 3H), 2.25 (s, 3H), 1.48 (d, J = 6.4 Hz, 3H) |
| 403 | (structure) | I-69 | 632.0, 634.0, 636.0 | 1.30 | 60-90% 20 min, 100% 5 min | ¹H NMR (400 MHz, THF) δ 9.25 (br. s., 1H), 8.82 (d, J = 2.0 Hz, 1H), 8.60 (s, 1H), 8.41 (d, J = 2.6 Hz, 1H), 7.95 (dd, J = 8.7, 2.8 Hz, 1H), 7.83 (dd, J = 1.8, 0.9 Hz, 1H), 7.76 (d, J = 7.5 Hz, 1H), 7.44 (d, J = 8.8 Hz, 1H), 5.42-5.26 (m, 1H), 4.44-4.27 (m, 2H), 4.15 (s, 3H), 2.70 (s, 3H), 1.55-1.49 (m, 3H) |
| 404 | (structure) | I-81 | 568.2, 570.2 | 1.10 | 40-80% 20 min, 100% 5 min | ¹H NMR (500 MHz, DMSO-d₆) δ 10.07 (br. s., 1H), 8.67 (br. s., 1H), 8.62 (s, 1H), 8.48 (s, 1H), 8.24 (br. s., 1H), 7.98 (d, J = 6.7 Hz, 2H), 7.75 (s, 1H), 7.45 (br. s., 1H), 5.08 (d, J = 6.7 Hz, 1H), 4.76 (br. s., 1H), 4.01 (s, 3H), 2.57 (s, 3H), 1.36 (d, J = 6.1 Hz, 3H), 1.33 (d, J = 6.4 Hz, 3H) |

| Ex. No. | Structure | R—OH | LCMS [M + H]+ m/z | LCMS RT (Min) Method H | HPLC Prep Method D | NMR |
|---|---|---|---|---|---|---|
| 405 | 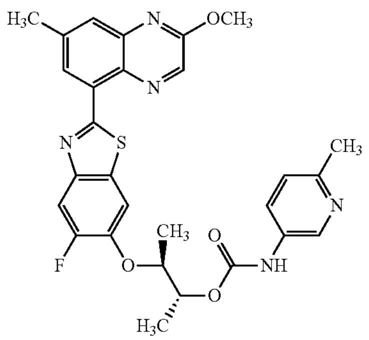 | I-72 | 548.1 | 1.05 | 15-100% 15 min, 100% 5 min | $^1$H NMR (500 MHz, DMSO-d$_6$) δ 9.81 (br. s., 1H), 8.71 (s, 1H), 8.55 (s, 1H), 8.49 (br. s., 1H), 8.02 (d, J = 8.2 Hz, 1H), 7.94 (d, J = 11.6 Hz, 1H), 7.82 (s, 1H), 7.77 (br. s., 1H), 7.19 (d, J = 7.9 Hz, 1H), 5.09 (d, J = 4.6 Hz, 1H), 4.77 (br. s., 1H), 4.07 (s, 3H), 2.61 (s, 3H), 2.37 (s, 3H), 1.38 (m, 6H) |
| 406 | 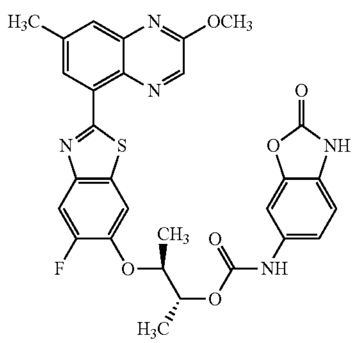 [SMILES: COc1cnc2c(-c3nc4cc(F)c(O[C@@H](C)[C@@H](C)OC(=O)Nc5ccc6[nH]c(=O)oc6c5)cc4s3)cc(C)cc2n1] | I-72 | 590.1 | 1.22 | 25-100% 20 min, 100% 5 min | $^1$H NMR (500 MHz, DMSO-d$_6$) δ 11.47 (s, 1H), 9.67 (br. s., 1H), 8.69 (s, 1H), 8.54 (s, 1H), 8.01 (d, J = 8.2 Hz, 1H), 7.94 (d, J = 11.3 Hz, 1H), 7.81 (s, 1H), 7.45 (br. s., 1H), 7.12 (br. s., 1H), 6.96 (d, J = 8.2 Hz, 1H), 5.07 (d, J = 6.4 Hz, 1H), 4.77 (br. s., 1H), 4.06 (s, 3H), 2.61 (s, 3H), 1.38 (d, J = 6.4 Hz, 3H), 1.36 (d, J = 6.7 Hz, 3H) |
| 407 | 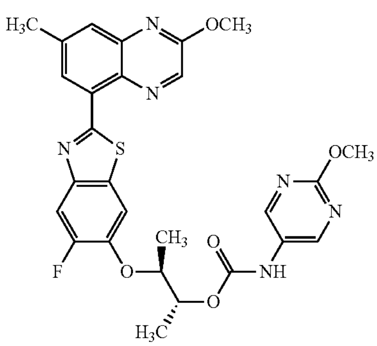 [SMILES: COc1cnc2c(-c3nc4cc(F)c(O[C@@H](C)[C@@H](C)OC(=O)Nc5cnc(OC)nc5)cc4s3)cc(C)cc2n1] | I-72 | 565.1 | 1.26 | 50-100% 15 min, 100% 5 min | $^1$H NMR (500 MHz, DMSO-d$_6$) δ 9.88 (br. s., 1H), 8.77 (s, 1H), 8.68 (br. s., 2H), 8.62 (s, 1H), 8.09 (d, J = 7.9 Hz, 1H), 8.01 (d, J = 11.6 Hz, 1H), 7.88 (s, 1H), 5.15 (d, J = 6.4 Hz, 1H), 4.87 (d, J = 6.4 Hz, 1H), 4.14 (s, 3H), 3.90 (s, 3H), 2.68 (s, 3H), 1.48-1.40 (m, 6H) |
| 408 | 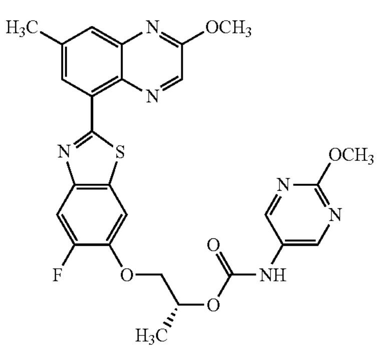 [SMILES: COc1cnc2c(-c3nc4cc(F)c(OC[C@@H](C)OC(=O)Nc5cnc(OC)nc5)cc4s3)cc(C)cc2n1] | I-67 | 551.1 | 1.22 | 50-100% 12 min, 100% 5 min | $^1$H NMR (500 MHz, DMSO-d$_6$) δ 9.91 (br. s., 1H), 8.69 (s, 1H), 8.63 (br. s., 2H), 8.52 (s, 1H), 7.99-7.90 (m, 2H), 7.78 (s, 1H), 5.23 (br. s., 1H), 4.38-4.31 (m, 1H), 4.29-4.21 (m, 1H), 4.06 (s, 3H), 3.85 (s, 3H), 2.60 (s, 3H), 1.40 (d, J = 6.4 Hz, 3H) |

| Ex. No. | Structure | R—OH | LCMS [M + H]+ m/z | LCMS RT (Min) Method H | HPLC Prep Method D | NMR |
|---|---|---|---|---|---|---|
| 409 | 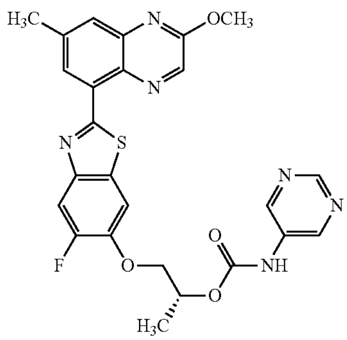 [SMILES: COc1cnc2c(-c3nc4cc(F)c(OC[C@@H](C)OC(=O)Nc5cncnc5)cc4s3)cc(C)cc2n1] | I-67 | 521.1 | 1.22 | 45-78% 25 min, 100% 7 min | ¹H NMR (400 MHz, DMSO-d₆) δ 10.20 (br. s., 1H), 8.89 (s, 2H), 8.84 (s, 1H), 8.73 (s, 1H), 8.56 (d, J = 2.0 Hz, 1H), 8.00 (d, J = 8.4 Hz, 1H), 7.97 (d, J = 11.7 Hz, 1H), 7.82 (dd, J = 2.0, 0.9 Hz, 1H), 5.35-5.22 (m, 1H), 4.43-4.35 (m, 1H), 4.33-4.25 (m, 1H), 4.08 (s, 3H), 2.63 (s, 3H), 1.44 (d, J = 6.6 Hz, 3H) |
| 410 | 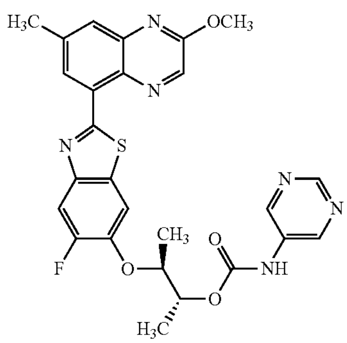 [SMILES: COc1cnc2c(-c3nc4cc(F)c(O[C@@H](C)[C@@H](C)OC(=O)Nc5cncnc5)cc4s3)cc(C)cc2n1] | I-72 | 535.1 | 1.25 | 45-90% 20 min, 100% 5 min | ¹H NMR (400 MHz, DMSO-d₆) δ 10.13 (br. s., 1H), 8.87 (s, 2H), 8.82 (s, 1H), 8.73 (s, 1H), 8.58 (d, J = 1.8 Hz, 1H), 8.06 (d, J = 8.1 Hz, 1H), 7.97 (d, J = 11.7 Hz, 1H), 7.84 (dd, J = 2.0, 0.9 Hz, 1H), 5.14 (qd, J = 6.4, 2.8 Hz, 1H), 4.87-4.77 (m, 1H), 4.09 (s, 3H), 2.64 (s, 3H), 1.44-1.38 (m, 6H) |
| 411 | 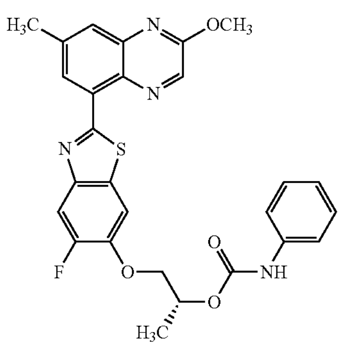 [SMILES: COc1cnc2c(-c3nc4cc(F)c(OC[C@@H](C)OC(=O)Nc5ccccc5)cc4s3)cc(C)cc2n1] | I-67 | 519.2 | 1.27 | 45-90% 20 min, 100% 5 min | ¹H NMR (500 MHz, DMSO-d₆) δ 9.73 (br. s., 1H), 8.69 (s, 1H), 8.53 (s, 1H), 7.99-7.91 (m, 2H), 7.80 (s, 1H), 7.48 (d, J = 7.3 Hz, 2H), 7.28 (t, J = 7.5 Hz, 2H), 7.00 (t, J = 7.3 Hz, 1H), 5.25 (br. s., 1H), 4.38-4.31 (m, 1H), 4.30-4.22 (m, 1H), 4.07 (s, 3H), 2.61 (s, 3H), 1.42 (d, J = 6.1 Hz, 3H) |
| 412 | 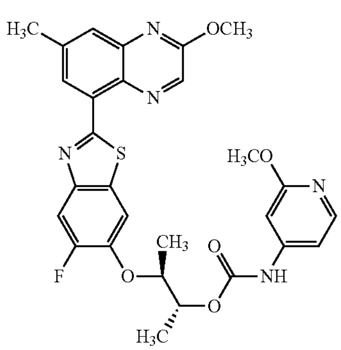 [SMILES: COc1cc(NC(=O)O[C@H](C)[C@H](C)Oc2cc3sc(-c4cc(C)cc5nc(OC)cnc45)nc3cc2F)ccn1] | I-72 | 564.1 | 1.12 | 70-100% 20 min, 100% 7 min | ¹H NMR (500 MHz, DMSO-d₆) δ 10.09 (s, 1H), 8.68 (s, 1H), 8.52 (s, 1H), 8.01 (d, J = 8.4 Hz, 1H), 7.97-7.91 (m, 2H), 7.78 (s, 1H), 7.01 (d, J = 5.4 Hz, 1H), 6.91 (s, 1H), 5.12 (dd, J = 6.4, 2.4 Hz, 1H), 4.79 (d, J = 3.7 Hz, 1H), 4.06 (s, 3H), 3.77 (s, 3H), 2.60 (s, 3H), 1.39 (m, 6H) |

| Ex. No. | Structure | R—OH | LCMS [M + H]+ m/z | LCMS RT (Min) Method H | HPLC Prep Method D | NMR |
|---|---|---|---|---|---|---|
| 413 | 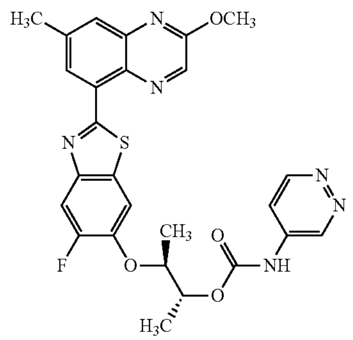 [SMILES: COc1cnc2c(-c3nc4cc(F)c(O[C@@H](C)[C@@H](C)OC(=O)Nc5ccnnc5)cc4s3)cc(C)cc2n1] | I-72 | 535.1 | 1.06 | 40-95% 21 min, 100% 6 min | $^1$H NMR (500 MHz, DMSO-d$_6$) δ 10.54 (br. s., 1H), 9.19 (br. s., 1H), 9.00 (br. s., 1H), 8.68 (s, 1H), 8.53 (s, 1H), 8.01 (d, J = 7.9 Hz, 1H), 7.94 (d, J = 11.6 Hz, 1H), 7.81 (br. s., 2H), 5.16 (br. s., 1H), 4.81 (br. s., 1H), 4.07 (s, 3H), 2.62 (s, 3H), 1.41 (d, J = 5.8 Hz, 6H) |
| 414 | 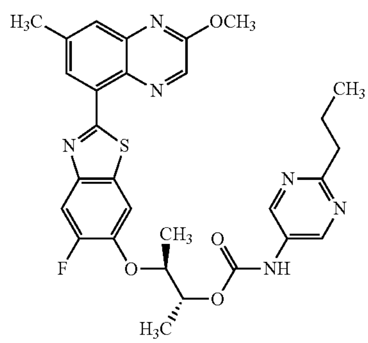 [SMILES: CCCc1ncc(NC(=O)O[C@H](C)[C@H](C)Oc2cc3sc(-c4cc(C)cc5nc(OC)cnc45)nc3cc2F)cn1] | I-72 | 577.2 | 1.27 | 45-100% 10 min, 100% 5 min | $^1$H NMR (500 MHz, DMSO-d$_6$) δ 9.90 (br. s., 1H), 8.72 (br. s., 2H), 8.66 (s, 1H), 8.51 (s, 1H), 7.99 (d, J = 8.2 Hz, 1H), 7.91 (d, J = 11.3 Hz, 1H), 7.78 (s, 1H), 5.09 (d, J = 4.3 Hz, 1H), 4.80 (d, J = 3.7 Hz, 1H), 4.05 (s, 3H), 2.71 (t, J = 7.3 Hz, 2H), 2.59 (s, 3H), 1.66 (sxt, J = 7.3 Hz, 2H), 1.38 (t, J = 5.8 Hz, 6H), 0.83 (t, J = 7.3 Hz, 3H) |
| 415 | 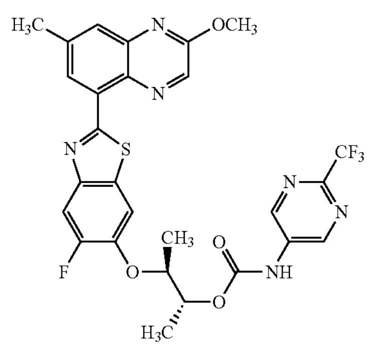 [SMILES: COc1cnc2c(-c3nc4cc(F)c(O[C@@H](C)[C@@H](C)OC(=O)Nc5cnc(C(F)(F)F)nc5)cc4s3)cc(C)cc2n1] | I-72 | 603.1 | 1.31 | 60-100% 22 min, 100% 5 min | $^1$H NMR (500 MHz, DMSO-d$_6$) δ 10.51 (br. s., 1H), 9.01 (s, 2H), 8.64 (s, 1H), 8.49 (s, 1H), 7.99 (d, J = 8.1 Hz, 1H), 7.91 (d, J = 11.4 Hz, 1H), 7.77 (s, 1H), 5.14 (dd, J = 6.6, 2.2 Hz, 1H), 4.84 (d, J = 4.0 Hz, 1H), 4.05 (s, 3H), 2.59 (s, 3H), 1.40 (d, J = 5.7 Hz, 6H) |
| 416 | 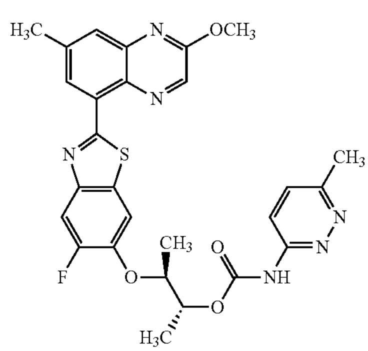 | I-72 | 549.2 | 1.11 | 55-95% 20 min, 100% 5 min | $^1$H NMR (500 MHz, DMSO-d$_6$) δ 10.64 (s, 1H), 8.72 (s, 1H), 8.56 (s, 1H), 8.03 (d, J = 8.2 Hz, 1H), 7.94 (d, J = 10.4 Hz, 2H), 7.83 (s, 1H), 7.52 (d, J = 9.2 Hz, 1H), 5.13 (d, J = 6.7 Hz, 1H), 4.76 (d, J = 5.8 Hz, 1H), 4.08 (s, 3H), 2.63 (s, 3H), 2.50 (s, 3H-buried under d-DMSO), 1.41 (d, J = 6.4 Hz, 3H), 1.38 (d, J = 6.4 Hz, 3H) |

| Ex. No. | Structure | R—OH | LCMS [M + H]+ m/z | LCMS RT (Min) Method H | HPLC Prep Method D | NMR |
|---|---|---|---|---|---|---|
| 417 | 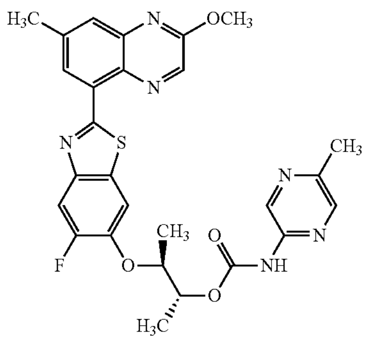 | I-72 | 549.2 | 1.27 | 60-100% 20 min, 100% 5 min | ¹H NMR (500 MHz, DMSO-d₆) δ 10.38 (s, 1H), 8.96 (s, 1H), 8.72 (br. s., 1H), 8.57 (br. s., 1H), 8.25 (s, 1H), 8.06 (d, J = 7.9 Hz, 1H), 7.97 (d, J = 11.3 Hz, 1H), 7.84 (br. s., 1H), 5.19 (dd, J = 6.4, 2.7 Hz, 1H), 4.82 (d, J = 3.4 Hz, 1H), 4.12 (s, 3H), 2.66 (s, 3H), 2.46 (s, 3H), 1.47 (d, J = 6.4 Hz, 3H), 1.44 (d, J = 6.7 Hz, 3H) |
| 418 | 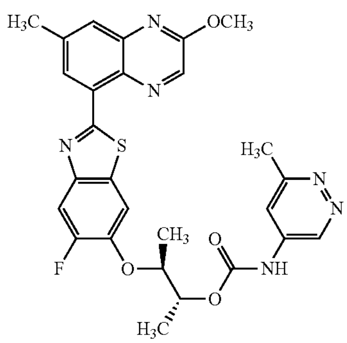 [SMILES: COc1cnc2c(-c3nc4cc(F)c(O[C@@H](C)[C@@H](C)OC(=O)Nc5cnnc(C)c5)cc4s3)cc(C)cc2n1] | I-72 | 549.1 | 1.15 | 50-100% 19 min, 100% 5 min | ¹H NMR (500 MHz, DMSO-d₆) δ 10.35 (s, 1H), 9.04 (br. s., 1H), 8.72 (s, 1H), 8.56 (d, J = 1.5 Hz, 1H), 8.04 (d, J = 8.2 Hz, 1H), 7.96 (d, J = 11.6 Hz, 1H), 7.83 (s, 1H), 7.60 (s, 1H), 5.20-5.09 (m, 1H), 4.82 (dd, J = 6.4, 2.7 Hz, 1H), 4.08 (s, 3H), 2.63 (s, 3H), 2.51 (br. s., 3H-Buried under d-DMSO signal), 1.41 (d, J = 6.4 Hz, 6H) |
| 419 | 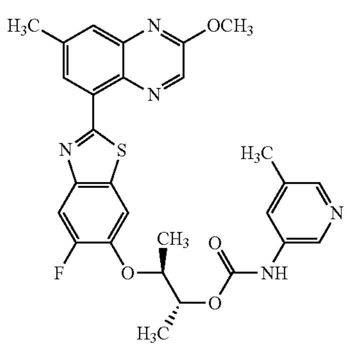 [SMILES: COc1cnc2c(-c3nc4cc(F)c(O[C@@H](C)[C@@H](C)OC(=O)Nc5cncc(C)c5)cc4s3)cc(C)cc2n1] | I-72 | 548.2 | 1.26 | 25-100% 15 min, 100% 5 min | ¹H NMR (500 MHz, DMSO-d₆) δ 10.19 (br. s., 1H), 8.73 (s, 1H), 8.61 (br. s., 1H), 8.57 (s, 1H), 8.23 (s, 1H), 8.05 (d, J = 8.2 Hz, 1H), 7.99-7.91 (m, 2H), 7.84 (s, 1H), 5.13 (d, J = 6.4 Hz, 1H), 4.82 (d, J = 5.8 Hz, 1H), 4.09 (s, 3H), 2.63 (s, 3H), 2.32 (s, 3H), 1.41 (d, J = 4.6 Hz, 6H) |
| 420 | 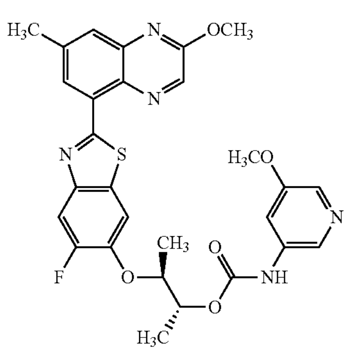 [SMILES: COc1cncc(NC(=O)O[C@H](C)[C@H](C)Oc2cc3sc(-c4cc(C)cc5nc(OC)cnc45)nc3cc2F)c1] | I-72 | 564.2 | 1.28 | 30-100% 15 min, 100% 5 min (Meth C) | ¹H NMR (500 MHz, DMSO-d₆) δ 10.06 (br. s., 1H), 8.72 (s, 1H), 8.57 (s, 1H), 8.31 (br. s., 1H), 8.08-8.00 (m, 2H), 7.96 (d, J = 11.3 Hz, 1H), 7.83 (s, 1H), 7.64 (br. s., 1H), 5.12 (d, J = 6.4 Hz, 1H), 4.81 (d, J = 6.1 Hz, 1H), 4.08 (s, 3H), 3.81 (s, 2H), 2.63 (s, 3H), 1.40 (t, J = 5.3 Hz, 6H) |

| Ex. No. | Structure | R—OH | LCMS [M + H]+ m/z | LCMS RT (Min) Method H | HPLC Prep Method D | NMR |
|---|---|---|---|---|---|---|
| 421 | 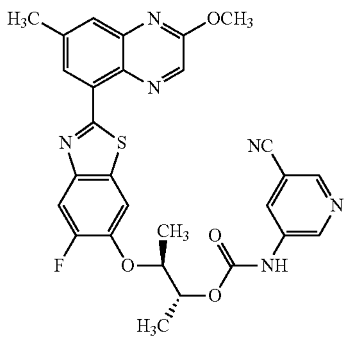 [SMILES: COc1cnc2c(-c3nc4cc(F)c(O[C@@H](C)[C@@H](C)OC(=O)Nc5cncc(C#N)c5)cc4s3)cc(C)cc2n1] | I-72 | 559.3 | 1.49 | 50-100% 10 min, 100% 10 min (Meth C) | $^1$H NMR (500 MHz, DMSO-d$_6$) δ 10.27 (br. s., 1H), 8.83 (br. s., 1H), 8.71 (s, 1H), 8.61 (s, 1H), 8.56 (s, 1H), 8.25 (br. s., 1H), 8.04 (d, J = 7.9 Hz, 1H), 7.95 (d, J = 11.3 Hz, 1H), 7.82 (s, 1H), 5.13 (d, J = 6.4 Hz, 1H), 4.83 (d, J = 6.1 Hz, 1H), 4.08 (s, 3H), 2.63 (s, 3H), 1.41 (d, J = 6.1 Hz, 6H) |
| 422 | 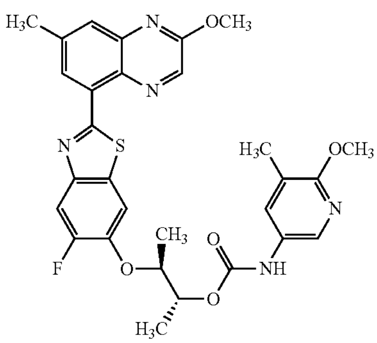 [SMILES: COc1cnc2c(-c3nc4cc(F)c(O[C@@H](C)[C@@H](C)OC(=O)Nc5cnc(OC)c(C)c5)cc4s3)cc(C)cc2n1] | I-72 | 578.2 | 1.45 | 60-100% 10 min, 100% 10 min | $^1$H NMR (500 MHz, DMSO-d$_6$) δ 9.50 (br. s., 1H), 8.72 (s, 1H), 8.57 (s, 1H), 8.02 (d, J = 7.9 Hz, 2H), 7.95 (d, J = 11.3 Hz, 1H), 7.82 (s, 1H), 7.59 (br. s., 1H), 5.06 (d, J = 5.2 Hz, 1H), 4.79 (d, J = 5.8 Hz, 1H), 4.08 (s, 3H), 3.80 (s, 3H), 2.63 (s, 3H), 2.08 (s, 3H), 1.38 (t, J = 7.6 Hz, 6H) |
| 423 | 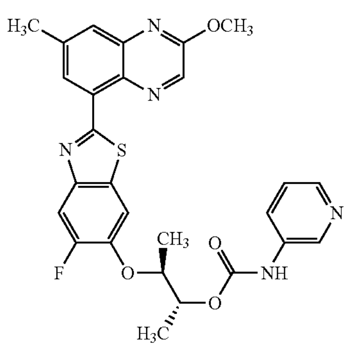 [SMILES: COc1cnc2c(-c3nc4cc(F)c(O[C@@H](C)[C@@H](C)OC(=O)Nc5cccnc5)cc4s3)cc(C)cc2n1] | I-72 | 534.0 | 1.00 | 60-100% 20 min, 100% 10 min | $^1$H NMR (500 MHz, DMSO-d$_6$) δ 9.93 (br. s., 1H), 8.72 (s, 1H), 8.66 (br. s., 1H), 8.56 (s, 1H), 8.22 (d, J = 4.3 Hz, 1H), 8.04 (d, J = 8.2 Hz, 1H), 7.96 (d, J = 11.6 Hz, 1H), 7.91 (br. s., 1H), 7.83 (s, 1H), 7.35 (dd, J = 8.1, 4.7 Hz, 1H), 5.13 (d, J = 6.4 Hz, 1H), 4.80 (d, J = 3.7 Hz, 1H), 4.09 (s, 3H), 2.63 (s, 3H), 1.41 (t, J = 6.3 Hz, 6H) |
| 424 | 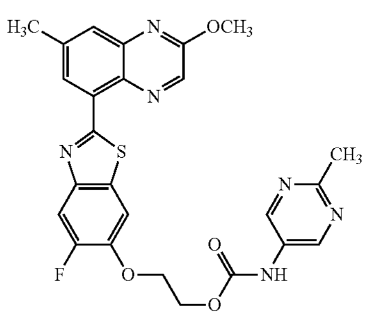 | I-66 | 520.9 | 1.10 | 45-90% 20 min, 100% 5 min | $^1$H NMR (500 MHz, DMSO-d$_6$) δ 10.16 (br. s., 1H), 8.77 (d, J = 4.3 Hz, 3H), 8.59 (s, 1H), 8.06-7.97 (m, 2H), 7.86 (s, 1H), 4.57 (br. s., 2H), 4.46 (br. s., 2H), 4.10 (s, 3H), 2.65 (s, 3H), 2.56 (s, 3H) |

| Ex. No. | Structure | R—OH | LCMS [M + H]+ m/z | LCMS RT (Min) Method H | HPLC Prep Method D | NMR |
|---|---|---|---|---|---|---|
| 425 | (structure shown) | I-81 | 582.9, 584.9 | 1.26 | 60-100% 20 min, 100% 7 min (Meth C) | ¹H NMR (500 MHz, DMSO-d₆) δ 9.95 (br. s., 1H), 8.78-8.67 (m, 3H), 8.57 (s, 1H), 8.06 (d, J = 7.6 Hz, 1H), 7.84 (s, 1H), 5.13 (dd, J = 6.6, 2.3 Hz, 1H), 4.85 (d, J = 6.4 Hz, 1H), 4.09 (s, 3H), 2.65 (s, 3H), 2.56 (s, 3H), 1.42 (d, J = 6.4 Hz, 3H), 1.40 (d, J = 6.7 Hz, 3H) |

Example 426

(2R,3S)-3-((5-fluoro-2-(2-methoxy-7-methylquinoxalin-5-yl)benzo[d]thiazol-6-yl)oxy)butan-2-yl (6-(morpholine-4-carbonyl)pyridin-3-yl)carbamate (426)

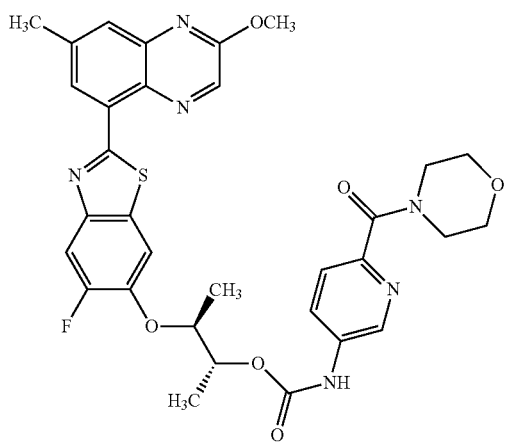

To a vial charged with Intermediate I-74 (10 mg, 0.017 mmol) was added DCM (1 mL). To this solution was added magnesium chloride (16.09 mg, 0.169 mmol) followed by morpholine (0.1 mL, 1.148 mmol). The resulting mixture was sealed, stirred vigorously and heated to 65° C. overnight before being diluted with EtOAc, filtered over Celite, concentrated, and purified by Prep HPLC (Method C, 25-100% over 15 min, hold 100% for 5 min) to afford Example 426 (9.6 mg, 0.015 mmol, 86% yield). LC-MS: Method H, RT=1.20 min, MS (ESI) m/z: 647.2 (M+H)⁺. ¹H NMR (500 MHz, DMSO-d₆) δ 10.12 (br. s., 1H), 8.64 (s, 1H), 8.59 (br. s., 1H), 8.49 (s, 1H), 7.98 (d, J=7.9 Hz, 2H), 7.91 (d, J=11.6 Hz, 1H), 7.76 (s, 1H), 7.57 (d, J=8.5 Hz, 1H), 5.12 (d, J=4.6 Hz, 1H), 4.80 (d, J=5.8 Hz, 1H), 4.05 (s, 3H), 3.62 (d, J=15.9 Hz, 2H), 3.49 (d, J=17.1 Hz, 2H), 2.59 (s, 3H), 2.52 (br. s., 4H), 1.39 (m, 6H).

Preparation of Amide Examples

The amides in the accompanying table were prepared according to the following three general procedures, which are analogous to the ones used to synthesize Examples 391-392 and 426 described above.

Primary Amides: To a vial charged with the appropriately substituted hetero-aryl ester (1.0 equiv) was added ammonia (7M solution in MeOH) (0.02 M). The resulting mixture was sealed and heated to 65° C. overnight before being concentrated and purified by Prep HPLC (Method D unless otherwise indicated) to afford the desired example.

Secondary Amides: To a solution of the appropriately substituted hetero-aryl ester (1.0 equiv) in THF (0.02 M) was added the desired amine (100 equiv). The resulting mixture was sealed and heated to 65° C. overnight before being concentrated and purified by Prep HPLC (Method D unless otherwise indicated) to afford the desired example.

Tertiary Amides: To a solution of the appropriately substituted hetero-aryl ester (1.0 equiv) in DCM (0.02 M) was added MgCl₂ (10 equiv) followed by the desired amine (100 equiv). The resulting mixture was sealed, stirred vigorously and heated to 65° C. overnight before being diluted with EtOAc, filtered over Celite, concentrated and purified by Prep HPLC (Method D unless otherwise indicated) to afford the desired example.

| Ex. No. | Structure | Ester | LCMS [M + H]+ m/z | LCMS RT (Min) Method H | HPLC Prep Method D | NMR |
|---|---|---|---|---|---|---|
| 427 | 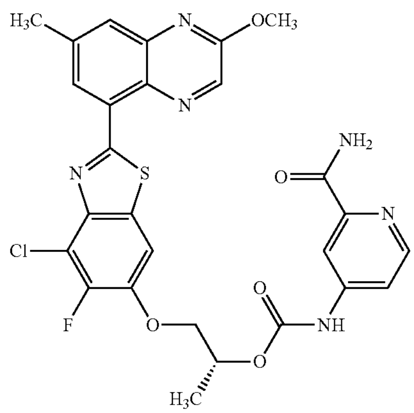 [SMILES: COc1cnc2c(-c3nc4c(Cl)c(F)c(OC[C@@H](C)OC(=O)Nc5ccnc(C(N)=O)c5)cc4s3)cc(C)cc2n1] | I-87 | 597.1, 599.2 | 1.16 | 45-95% 20 min, 100% 5 min | ¹H NMR (500 MHz, DMSO-d₆) δ 10.44 (s, 1H), 8.71 (s, 1H), 8.56 (s, 1H), 8.42 (d, J = 5.2 Hz, 1H), 8.15 (s, 1H), 8.01 (d, J = 7.9 Hz, 2H), 7.83 (s, 1H), 7.63 (br. s., 1H), 7.57 (br. s., 1H), 5.30 (br. s., 1H), 4.46-4.37 (m, 1H), 4.31 (d, J = 5.8 Hz, 1H), 4.07 (s, 3H), 2.64 (s, 3H), 1.44 (d, J = 6.1 Hz, 3H) |
| 428 | 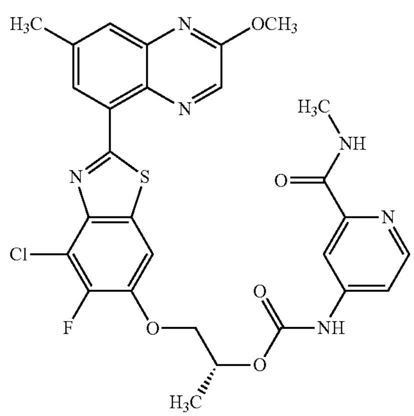 [SMILES: CNC(=O)c1cc(NC(=O)O[C@H](C)COc2cc3sc(-c4cc(C)cc5nc(OC)cnc45)nc3c(Cl)c2F)ccn1] | I-87 | 611.1, 613.1 | 1.17 | 45-95% 20 min, 100% 5 min | ¹H NMR (500 MHz, DMSO-d₆) δ 10.42 (s, 1H), 8.71-8.63 (m, 2H), 8.54 (s, 1H), 8.42 (d, J = 5.5 Hz, 1H), 8.13 (s, 1H), 7.99 (d, J = 7.6 Hz, 1H), 7.81 (s, 1H), 7.62 (d, J = 4.9 Hz, 1H), 5.29 (br. s., 1H), 4.40 (d, J = 8.5 Hz, 1H), 4.30 (dd, J = 10.5, 6.3 Hz, 1H), 4.07 (s, 3H), 2.78 (d, J = 4.9 Hz, 3H), 2.63 (s, 3H), 1.43 (d, J = 6.4 Hz, 3H) |
| 429 | 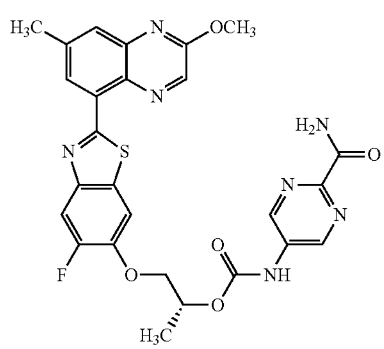 [SMILES: COc1cnc2c(-c3nc4cc(F)c(OC[C@@H](C)OC(=O)Nc5cnc(C(N)=O)nc5)cc4s3)cc(C)cc2n1] | I-84 | 564.1 | 1.10 | 60-100% 13 min, 100% 5 min | ¹H NMR (500 MHz, DMSO-d₆) δ 8.94 (s, 2H), 8.65 (s, 1H), 8.48 (s, 1H), 8.05 (br. s., 1H), 7.94 (d, J = 8.2 Hz, 1H), 7.91 (d, J = 11.6 Hz, 1H), 7.75 (s, 1H), 7.63 (br. s., 1H), 5.32-5.17 (m, 1H), 4.39-4.30 (m, 1H), 4.29-4.21 (m, 1H), 4.02 (s, 3H), 2.56 (s, 3H), 1.41 (d, J = 6.4 Hz, 3H) |
| 430 | 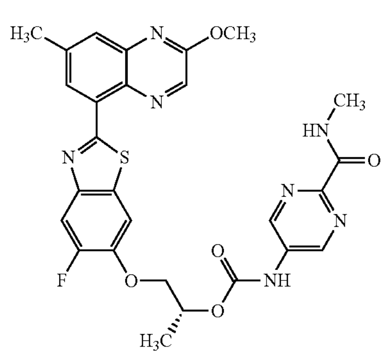 [SMILES: CNC(=O)c1ncc(NC(=O)O[C@H](C)COc2cc3sc(-c4cc(C)cc5nc(OC)cnc45)nc3cc2F)cn1] | I-84 | 578.1 | 1.12 | 50-100% 10 min, 100% 5 min | ¹H NMR (500 MHz, DMSO-d₆) δ 8.97 (s, 2H), 8.77-8.69 (m, 2H), 8.55 (s, 1H), 8.00 (d, J = 8.2 Hz, 1H), 7.97 (d, J = 11.6 Hz, 1H), 7.82 (s, 1H), 5.29 (br. s., 1H), 4.40 (d, J = 8.2 Hz, 1H), 4.29 (dd, J = 10.7, 6.1 Hz, 1H), 4.07 (s, 3H), 2.78 (d, J = 4.6 Hz, 3H), 2.62 (s, 3H), 1.44 (d, J = 6.4 Hz, 3H) |

| Ex. No. | Structure | Ester | LCMS [M + H]+ m/z | LCMS RT (Min) Method H | HPLC Prep Method D | NMR |
|---|---|---|---|---|---|---|
| 431 | 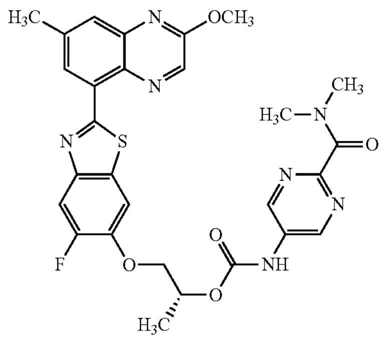 [SMILES: COc1cnc2c(-c3nc4cc(F)c(OC[C@@H](C)OC(=O)Nc5cnc(C(=O)N(C)C)nc5)cc4s3)cc(C)cc2n1] | I-84 | 592.2 | 1.15 | 60-100% 13 min, 100% 5 min | ¹H NMR (500 MHz, DMSO-d₆) δ 10.39 (br. s., 1H), 8.92 (s, 2H), 8.71 (s, 1H), 8.54 (s, 1H), 7.99 (d, J = 8.2 Hz, 1H), 7.96 (d, J = 11.6 Hz, 1H), 7.80 (s, 1H), 5.29 (d, J = 2.7 Hz, 1H), 4.42-4.35 (m, 1H), 4.32-4.25 (m, 1H), 4.06 (s, 3H), 2.98 (s, 3H), 2.77 (s, 3H), 2.61 (s, 3H), 1.44 (d, J = 6.4 Hz, 3H) |
| 432 | 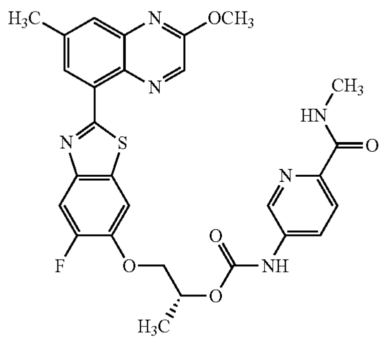 [SMILES: CNC(=O)c1ccc(NC(=O)O[C@H](C)COc2cc3sc(-c4cc(C)cc5nc(OC)cnc45)nc3cc2F)cn1] | I-82 | 577.2 | 1.17 | 15-100% 20 min, 100% 7 min | ¹H NMR (500 MHz, DMSO-d₆) δ 10.26 (br. s., 1H), 8.68 (s, 2H), 8.59 (d, J = 4.6 Hz, 1H), 8.52 (s, 1H), 8.02 (d, J = 8.9 Hz, 1H), 7.99-7.90 (m, 3H), 7.79 (s, 1H), 5.27 (d, J = 3.1 Hz, 1H), 4.37 (dt, J = 7.9 Hz, 1H), 4.31-4.23 (m, 1H), 4.06 (s, 3H), 2.77 (d, J = 4.6 Hz, 3H), 2.60 (s, 3H), 1.42 (d, J = 6.4 Hz, 3H) |
| 433 | 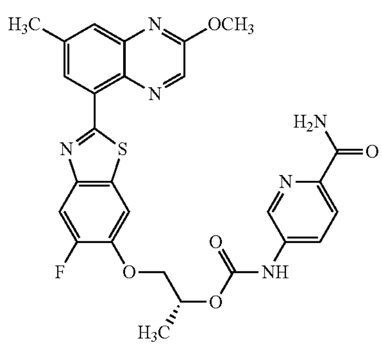 [SMILES: COc1cnc2c(-c3nc4cc(F)c(OC[C@@H](C)OC(=O)Nc5ccc(C(N)=O)nc5)cc4s3)cc(C)cc2n1] | I-82 | 563.1 | 1.15 | 25-65% 20 min, 100% 9 min | ¹H NMR (500 MHz, DMSO-d₆) δ 10.24 (br. s., 1H), 8.64 (s, 1H), 8.62 (s, 1H), 8.46 (s, 1H), 8.03-7.97 (m, 1H), 7.95-7.85 (m, 4H), 7.72 (s, 1H), 7.43 (br. s., 1H), 5.27-5.19 (m, 1H), 4.36-4.29 (m, 1H), 4.26-4.19 (m, 1H), 4.01 (s, 3H), 2.55 (s, 3H), 1.39 (d, J = 6.4 Hz, 3H) |
| 434 | 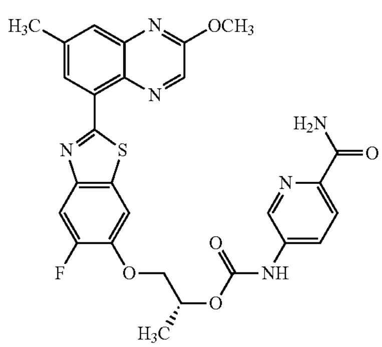 [SMILES: COc1cnc2c(-c3nc4cc(F)c(OC[C@@H](C)OC(=O)Nc5ccc(C(N)=O)nc5)cc4s3)cc(C)cc2n1] | I-82 | 591.1 | 1.16 | 10-100% 20 min, 100% 5 min | ¹H NMR (500 MHz, DMSO-d₆) δ 10.19 (br. s., 1H), 8.67 (s, 1H), 8.62 (s, 1H), 8.51 (s, 1H), 8.02-7.89 (m, 3H), 7.77 (s, 1H), 7.53 (d, J = 8.5 Hz, 1H), 5.27 (d, J = 3.1 Hz, 1H), 4.36 (d, J = 7.9 Hz, 1H), 4.31-4.23 (m, 1H), 4.05 (s, 3H), 2.97 (s, 3H), 2.96 (s, 3H), 2.59 (s, 3H), 1.42 (d, J = 6.7 Hz, 3H) |

-continued

| Ex. No. | Structure | Ester | LCMS [M + H]+ m/z | LCMS RT (Min) Method H | HPLC Prep Method D | NMR |
|---|---|---|---|---|---|---|
| 435 | 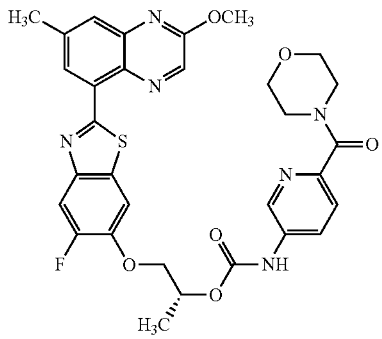 [SMILES: COc1cnc2c(-c3nc4cc(F)c(OC[C@@H](C)OC(=O)Nc5ccc(C(=O)N6CCOCC6)nc5)cc4s3)cc(C)cc2n1] | I-82 | 633.1 | 1.17 | 10-100% 20 min, 100% 5 min | ¹H NMR (500 MHz, DMSO-d₆) δ 10.22 (br. s., 1H), 8.67 (s, 1H), 8.62 (s, 1H), 8.50 (s, 1H), 8.01 (d, J = 8.2 Hz, 1H), 7.98-7.90 (m, 2H), 7.77 (s, 1H), 7.59 (d, J = 8.5 Hz, 1H), 5.27 (d, J = 2.7 Hz, 1H), 4.36 (d, J = 7.9 Hz, 1H), 4.27 (dd, J = 10.7, 6.1 Hz, 1H), 4.05 (s, 3H), 3.62 (m, 4H), 3.52 (m, 4H), 2.59 (s, 3H), 1.42 (d, J = 6.4 Hz, 3H) |
| 436 | 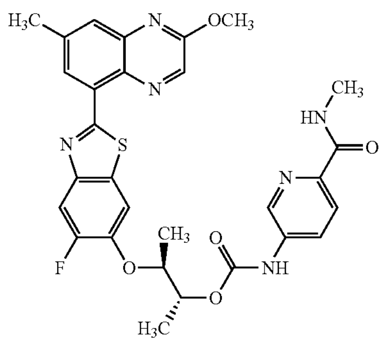 [SMILES: CNC(=O)c1ccc(NC(=O)O[C@H](C)[C@H](C)Oc2cc3sc(-c4cc(C)cc5nc(OC)cnc45)nc3cc2F)cn1] | I-74 | 591.1 | 1.18 | 25-100% 20 min, 100% 5 min | ¹H NMR (500 MHz, DMSO-d₆) δ 10.13 (br. s., 1H), 8.67 (s, 1H), 8.64 (br. s., 1H), 8.55 (d, J = 4.6 Hz, 1H), 8.52 (s, 1H), 8.04-7.96 (m, 2H), 7.95-7.88 (m, 2H), 7.79 (s, 1H), 5.11 (dd, J = 6.4, 2.4 Hz, 1H), 4.82 (d, J = 4.0 Hz, 1H), 4.06 (s, 3H), 2.76 (d, J = 4.6 Hz, 3H), 2.60 (s, 3H), 1.39 (m, 6H) |
| 437 | 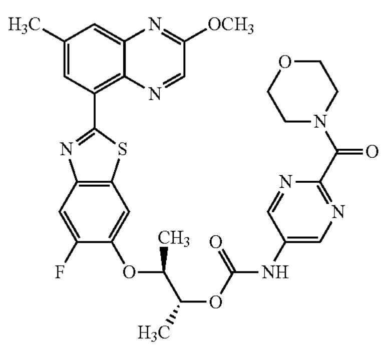 [SMILES: COc1cnc2c(-c3nc4cc(F)c(O[C@@H](C)[C@@H](C)OC(=O)Nc5cnc(C(=O)N6CCOCC6)nc5)cc4s3)cc(C)cc2n1] | I-86 | 648.2 | 1.18 | 20-100% 20 min, 100% 5 min | ¹H NMR (500 MHz, DMSO-d₆) δ 10.25 (br. s., 1H), 8.85 (s, 2H), 8.63 (s, 1H), 8.47 (s, 1H), 7.97 (d, J = 7.9 Hz, 1H), 7.88 (d, J = 11.6 Hz, 1H), 7.74 (s, 1H), 5.08 (dd, J = 6.6, 2.6 Hz, 1H), 4.75 (m, 1H), 4.00 (s, 3H), 3.57 (m, 4H), 3.40 (br. s., 2H), 3.17-3.08 (br. s., 2H), 2.55 (s, 3H), 1.34 (m, 6H) |
| 438 | 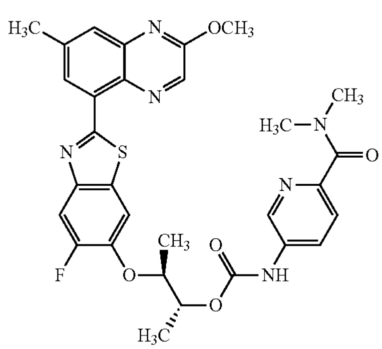 [SMILES: COc1cnc2c(-c3nc4cc(F)c(O[C@@H](C)[C@@H](C)OC(=O)Nc5ccc(C(=O)N(C)C)nc5)cc4s3)cc(C)cc2n1] | I-74 | 605.2 | 1.19 | 40-80% 20 min, 100% 10 min | ¹H NMR (500 MHz, DMSO-d₆) δ 10.07 (br. s., 1H), 8.65 (s, 1H), 8.58 (br. s., 1H), 8.50 (s, 1H), 7.98 (d, J = 8.2 Hz, 1H), 7.95 (d, J = 7.6 Hz, 1H), 7.91 (d, J = 11.6 Hz, 1H), 7.77 (s, 1H), 7.50 (d, J = 8.5 Hz, 1H), 5.11 (d, J = 4.3 Hz, 1H), 4.79 (d, J = 4.6 Hz, 1H), 4.04 (s, 3H), 2.95 (s, 3H), 2.91 (s, 3H), 2.58 (s, 3H), 1.38 (m, 6H) |

| Ex. No. | Structure | Ester | LCMS [M + H]+ m/z | LCMS RT (Min) Method H | HPLC Prep Method D | NMR |
|---|---|---|---|---|---|---|
| 439 | 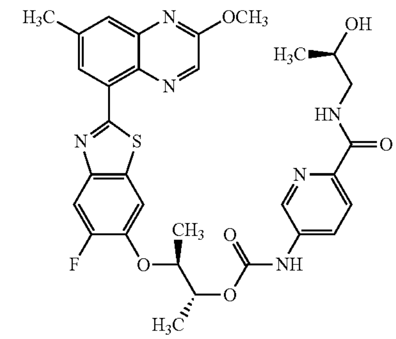 [SMILES: COc1cnc2c(-c3nc4cc(F)c(O[C@@H](C)[C@@H](C)OC(=O)Nc5ccc(C(=O)NC[C@@H](C)O)nc5)cc4s3)cc(C)cc2n1] | I-74 | 635.2 | 1.18 | 25-100% 15 min, 100% 5 min | ¹H NMR (500 MHz, DMSO-d₆) δ 10.19 (br. s., 1H), 8.71-8.64 (m, 2H), 8.53 (s, 1H), 8.41 (t, J = 6.0 Hz, 1H), 8.02 (d, J = 8.2 Hz, 2H), 7.94 (d, J = 11.0 Hz, 2H), 7.80 (s, 1H), 5.12 (dd, J = 6.6, 2.3 Hz, 1H), 4.87-4.77 (m, 2H), 4.06 (s, 3H), 3.75 (dt, J = 11.7, 5.6 Hz, 1H), 3.34 (br. s., 1H), 3.19-3.09 (m, 1H), 2.61 (s, 3H), 1.40 (m, 6H), 1.04 (d, J = 6.4 Hz, 3H) |
| 440 | 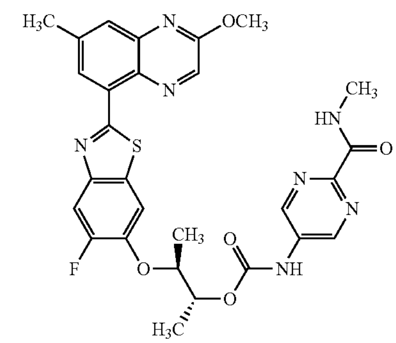 [SMILES: CNC(=O)c1ncc(NC(=O)O[C@H](C)[C@H](C)Oc2cc3sc(-c4cc(C)cc5nc(OC)cnc45)nc3cc2F)cn1] | I-86 | 592.1 | 1.15 | 30-80% 18 min, 100% 5 min | ¹H NMR (500 MHz, DMSO-d₆) δ 8.93 (s, 2H), 8.71 (d, J = 4.9 Hz, 1H), 8.68 (s, 1H), 8.53 (s, 1H), 8.02 (d, J = 8.2 Hz, 1H), 7.94 (d, J = 11.3 Hz, 1H), 7.79 (s, 1H), 5.13 (d, J = 4.3 Hz, 1H), 4.84 (d, J = 4.0 Hz, 1H), 4.06 (s, 3H), 2.76 (d, J = 4.9 Hz, 3H), 2.60 (s, 3H), 1.40 (d, J = 6.4 Hz, 6H) |
| 441 | 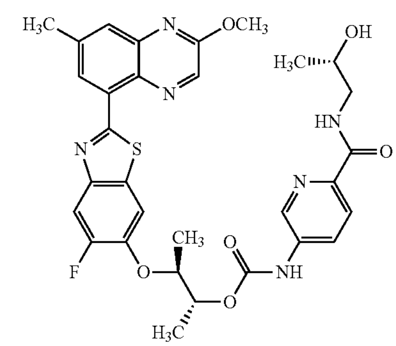 [SMILES: COc1cnc2c(-c3nc4cc(F)c(O[C@@H](C)[C@@H](C)OC(=O)Nc5ccc(C(=O)NC[C@H](C)O)nc5)cc4s3)cc(C)cc2n1] | I-74 | 635.2 | 1.19 | 45-90% 22 min, 100% 5 min | ¹H NMR (500 MHz, DMSO-d₆) δ 10.18 (br. s., 1H), 8.66 (s, 2H), 8.52 (s, 1H), 8.41 (t, J = 5.8 Hz, 1H), 8.00 (m, 2H), 7.94 (s, 1H), 7.92 (d, J = 4.6 Hz, 1H), 7.78 (s, 1H), 5.12 (d, J = 6.4 Hz, 1H), 4.86 (d, J = 4.6 Hz, 1H), 4.81 (d, J = 6.1 Hz, 1H), 4.05 (s, 3H), 3.75 (dt, J = 11.3, 5.6 Hz, 1H), 3.29 (dt, J = 12.4, 6.1 Hz, 1H), 3.16-3.07 (m, 1H), 2.59 (s, 3H), 1.39 (t, J = 5.3 Hz, 6H), 1.04 (d, J = 6.1 Hz, 3H) |
| 442 | 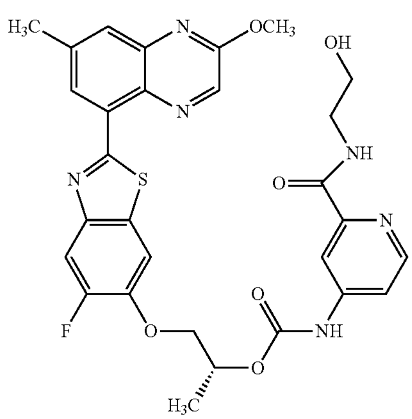 [SMILES: COc1cnc2c(-c3nc4cc(F)c(OC[C@@H](C)OC(=O)Nc5ccnc(C(=O)NCCO)c5)cc4s3)cc(C)cc2n1] | I-83 | 607.1 | 1.08 | 45-90% 20 min, 100% 8 min | ¹H NMR (500 MHz, DMSO-d₆) δ 8.77 (s, 1H), 8.69 (t, J = 5.8 Hz, 1H), 8.60 (s, 1H), 8.50 (d, J = 5.5 Hz, 1H), 8.22 (s, 1H), 8.05 (d, J = 8.2 Hz, 1H), 8.02 (d, J = 11.6 Hz, 1H), 7.86 (s, 1H), 7.72 (dd, J = 5.5, 1.8 Hz, 1H), 5.36 (d, J = 3.1 Hz, 1H), 4.44 (d, J = 7.9 Hz, 1H), 4.38-4.31 (m, 1H), 4.13 (s, 3H), 3.57 (q, J = 5.6 Hz, 2H), 2.67 (s, 3H), 1.50 (d, J = 6.4 Hz, 3H) |

| Ex. No. | Structure | Ester | LCMS [M + H]+ m/z | LCMS RT (Min) Method H | HPLC Prep Method D | NMR |
|---|---|---|---|---|---|---|
| 443 | 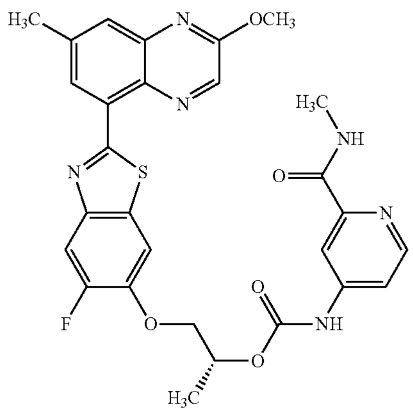 [SMILES: CNC(=O)c1cc(NC(=O)O[C@H](C)COc2cc3sc(-c4cc(C)cc5nc(OC)cnc45)nc3cc2F)ccn1] | I-83 | 577.1 | 1.12 | 50-100% 20 min, 100% 8 min | $^1$H NMR (500 MHz, DMSO-d$_6$) δ 10.52 (s, 1H), 8.77 (d, J = 4.9 Hz, 1H), 8.74 (s, 1H), 8.58 (s, 1H), 8.49 (d, J = 5.5 Hz, 1H), 8.20 (s, 1H), 8.02 (d, J = 8.5 Hz, 1H), 8.00 (d, J = 11.6 Hz, 1H), 7.84 (s, 1H), 7.70 (dd, J = 5.3, 2.0 Hz, 1H), 5.36 (d, J = 2.7 Hz, 1H), 4.48-4.41 (m, 1H), 4.38-4.31 (m, 1H), 4.12 (s, 3H), 2.86 (d, J = 4.9 Hz, 3H), 2.66 (s, 3H), 1.50 (d, J = 6.4 Hz, 3H) |
| 444 | 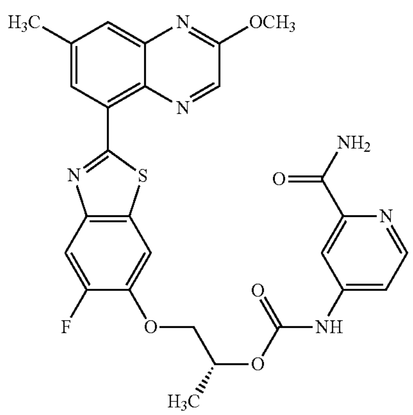 [SMILES: COc1cnc2c(-c3nc4cc(F)c(OC[C@@H](C)OC(=O)Nc5ccnc(C(N)=O)c5)cc4s3)cc(C)cc2n1] | I-83 | 563.1 | 1.11 | 25-100% 20 min, 100% 5 min | $^1$H NMR (500 MHz, DMSO-d$_6$) δ 10.47 (s, 1H), 8.69 (s, 1H), 8.53 (s, 1H), 8.42 (d, J = 5.2 Hz, 1H), 8.15 (s, 1H), 8.05 (br. s., 1H), 7.98 (d, J = 7.9 Hz, 1H), 7.94 (d, J = 11.6 Hz, 1H), 7.79 (s, 1H), 7.64 (d, J = 5.5 Hz, 1H), 7.60 (br. s., 1H), 5.29 (br. s., 1H), 4.40-4.34 (m, 1H), 4.31-4.24 (m, 1H), 4.06 (s, 3H), 2.60 (s, 3H), 1.44 (d, J = 6.4 Hz, 3H) |
| 445 | 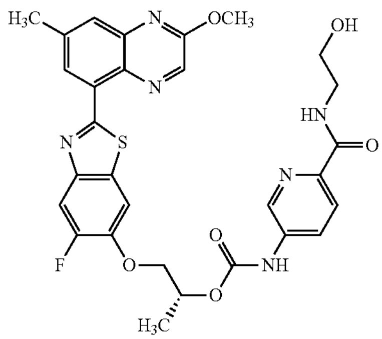 [SMILES: COc1cnc2c(-c3nc4cc(F)c(OC[C@@H](C)OC(=O)Nc5ccc(C(=O)NCCO)nc5)cc4s3)cc(C)cc2n1] | I-82 | 607.0 | 1.22 | 30-70% 20 min, 100% 5 min | $^1$H NMR (500 MHz, DMSO-d$_6$) δ 10.29 (br. s., 1H), 8.70 (br. s., 1H), 8.65 (s, 1H), 8.57-8.51 (m, 1H), 8.50 (s, 1H), 8.05 (d, J = 8.2 Hz, 1H), 8.00-7.89 (m, 3H), 7.77 (s, 1H), 5.29 (br. s., 1H), 4.89 (t, J = 4.9 Hz, 1H), 4.42-4.34 (m, 1H), 4.32-4.24 (m, 1H), 4.06 (s, 3H), 3.53-3.48 (m, 2H), 3.36 (d, J = 5.8 Hz, 2H), 2.60 (s, 3H), 1.44 (d, J = 6.1 Hz, 3H) |
| 446 | 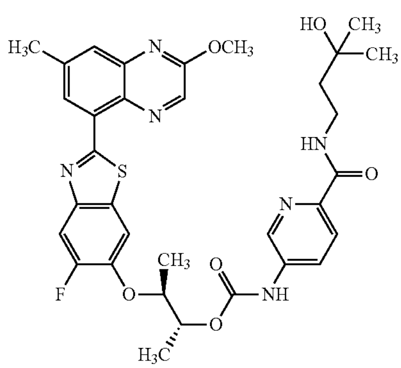 [SMILES: COc1cnc2c(-c3nc4cc(F)c(O[C@@H](C)[C@@H](C)OC(=O)Nc5ccc(C(=O)NCCC(C)(C)O)nc5)cc4s3)cc(C)cc2n1] | I-74 | 663.1 | 1.28 | 50-100% 20 min, 100% 5 min | $^1$H NMR (500 MHz, DMSO-d$_6$) δ 10.15 (br. s., 1H), 8.70-8.59 (m, 3H), 8.50 (s, 1H), 8.04-7.97 (m, J = 8.2 Hz, 2H), 7.94-7.88 (m, 2H), 7.77 (s, 1H), 5.13 (d, J = 6.1 Hz, 1H), 4.83 (d, J = 5.8 Hz, 1H), 4.06 (s, 3H), 3.35 (m, 2H), 2.60 (s, 3H), 1.61 (t, J = 7.2 Hz, 2H), 1.41 (t, J = 6.3 Hz, 6H), 1.14 (s, 6H) |

| Ex. No. | Structure | Ester | LCMS [M + H]+ m/z | LCMS RT (Min) Method H | HPLC Prep Method D | NMR |
|---|---|---|---|---|---|---|
| 447 | 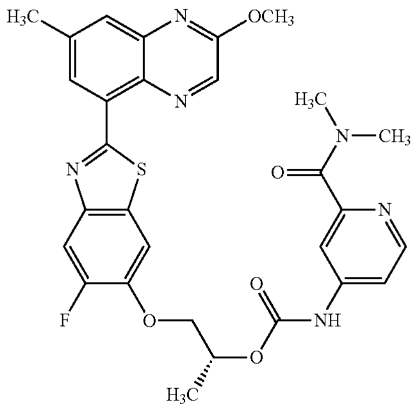 [SMILES: COc1cnc2c(-c3nc4cc(F)c(OC[C@@H](C)OC(=O)Nc5ccnc(C(=O)N(C)C)c5)cc4s3)cc(C)cc2n1] | I-83 | 591.0 | 1.14 | 45-90% 20 min, 100% 5 min | ¹H NMR (500 MHz, DMSO-d₆) δ 10.41 (s, 1H), 8.65 (s, 1H), 8.49 (s, 1H), 8.38 (d, J = 5.5 Hz, 1H), 7.96-7.89 (m, 2H), 7.76 (s, 1H), 7.59 (s, 1H), 7.51 (d, J = 5.5 Hz, 1H), 5.29 (br. s., 1H), 4.37 (d, J = 9.8 Hz, 1H), 4.27 (dd, J = 10.5, 6.0 Hz, 1H), 4.06 (s, 3H), 2.98 (s, 3H), 2.89 (s, 3H), 2.59 (s, 3H), 1.44 (d, J = 6.4 Hz, 3H) |
| 448 | 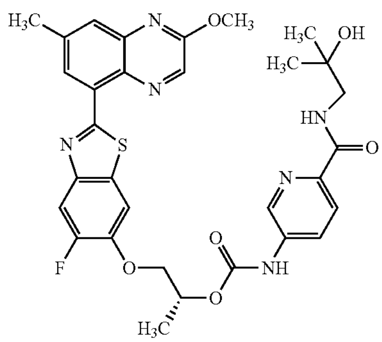 [SMILES: COc1cnc2c(-c3nc4cc(F)c(OC[C@@H](C)OC(=O)Nc5ccc(C(=O)NCC(C)(C)O)nc5)cc4s3)cc(C)cc2n1] | I-82 | 635.1 | 1.24 | 45-90% 20 min, 100% 5 min | ¹H NMR (500 MHz, DMSO-d₆) δ 10.30 (br. s., 1H), 8.70 (br. s., 1H), 8.64 (s, 1H), 8.48 (s, 1H), 8.37-8.29 (m, 1H), 8.08 (d, J = 8.5 Hz, 1H), 7.99 (d, J = 8.5 Hz, 1H), 7.95-7.89 (m, 2H), 7.75 (s, 1H), 5.29 (br. s., 1H), 4.80 (s, 1H), 4.41-4.34 (m, 1H), 4.31-4.24 (m, 1H), 4.05 (s, 3H), 3.26 (d, J = 5.8 Hz, 2H), 2.59 (s, 3H), 1.44 (d, J = 6.4 Hz, 3H), 1.10 (s, 6H) |
| 449 | 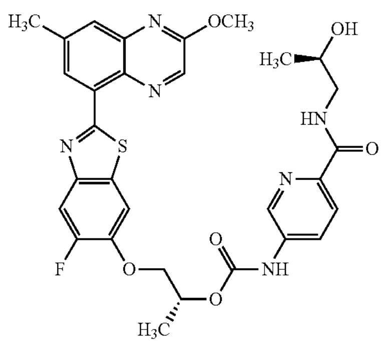 [SMILES: COc1cnc2c(-c3nc4cc(F)c(OC[C@@H](C)OC(=O)Nc5ccc(C(=O)NC[C@@H](C)O)nc5)cc4s3)cc(C)cc2n1] | I-82 | 621.2 | 1.18 | 45-90% 25 min, 100% 5 min | ¹H NMR (500 MHz, DMSO-d₆) δ 10.22 (br. s., 1H), 8.70-8.61 (m, 2H), 8.50 (s, 1H), 8.49-8.45 (m, 1H), 8.01 (br. s., 1H), 7.96-7.89 (m, 3H), 7.80 (s, 1H), 5.34-5.22 (m, J = 8.1 Hz, 1H), 4.37 (d, J = 8.8 Hz, 1H), 4.30-4.22 (m, 1H), 4.05 (s, 3H), 3.80 (m, 1H), 3.28 (d, J = 5.4 Hz, 1H), 3.20-3.07 (m, 1H), 2.60 (s, 3H), 1.40 (d, J = 6.4 Hz, 3H), 1.04 (d, J = 6.4 Hz, 3H) |
| 450 | 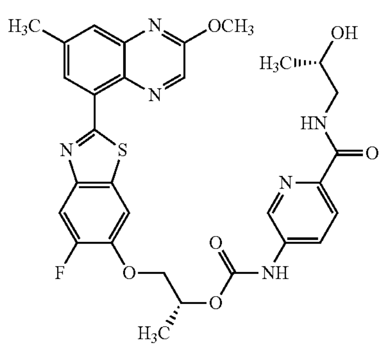 [SMILES: COc1cnc2c(-c3nc4cc(F)c(OC[C@@H](C)OC(=O)Nc5ccc(C(=O)NC[C@H](C)O)nc5)cc4s3)cc(C)cc2n1] | I-82 | 621.2 | 1.18 | 45-90% 25 min, 100% 8 min | ¹H NMR (500 MHz, DMSO-d₆) δ 8.76 (s, 1H), 8.73 (s, 1H), 8.60 (s, 1H), 8.44 (br. s., 1H), 8.11-7.96 (m, 4H), 7.86 (s, 1H), 5.31 (br. s., 1H), 4.84 (d, J = 4.9 Hz, 1H), 4.41 (d, J = 8.5 Hz, 1H), 4.34-4.28 (m, 1H), 4.10 (s, 3H), 3.79 (br. s., 1H), 3.39-3.28 (m, 1H), 3.21-3.12 (m, 1H), 2.65 (s, 3H), 1.45 (d, J = 6.4 Hz, 3H), 1.07 (d, J = 6.1 Hz, 3H) |

| Ex. No. | Structure | Ester | LCMS [M + H]+ m/z | LCMS RT (Min) Method H | HPLC Prep Method D | NMR |
|---|---|---|---|---|---|---|
| 451 | 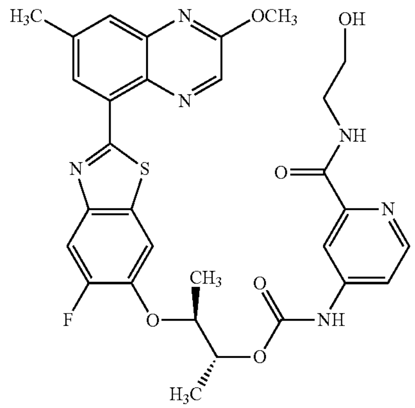 [SMILES: COc1cnc2c(-c3nc4cc(F)c(O[C@@H](C)[C@@H](C)OC(=O)Nc5ccnc(C(=O)NCCO)c5)cc4s3)cc(C)cc2n1] | I-85 | 621.3 | 1.08 | 60-95% 20 min, 100% 7 min | ¹H NMR (500 MHz, DMSO-d₆) δ 10.39 (s, 1H), 8.68 (s, 1H), 8.62 (t, J = 5.7 Hz, 1H), 8.53 (s, 1H), 8.42 (d, J = 5.7 Hz, 1H), 8.15 (s, 1H), 8.03 (d, J = 8.1 Hz, 1H), 7.94 (d, J = 11.8 Hz, 1H), 7.79 (s, 1H), 7.63 (d, J = 3.7 Hz, 1H), 5.15 (dd, J = 6.4, 2.4 Hz, 1H), 4.86-4.78 (m, 2H), 4.07 (s, 3H), 3.51 (q, J = 5.8 Hz, 2H), 3.40-3.31 (m, 2H), 2.61 (s, 3H), 1.41 (d, J = 4.7 Hz, 6H) |
| 452 | 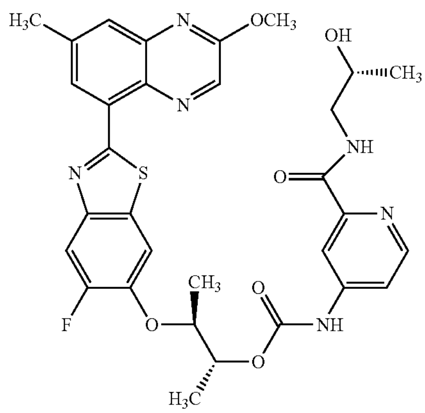 [SMILES: COc1cnc2c(-c3nc4cc(F)c(O[C@@H](C)[C@@H](C)OC(=O)Nc5ccnc(C(=O)NC[C@@H](C)O)c5)cc4s3)cc(C)cc2n1] | I-85 | 653.3 | 1.11 | 60-100% 20 min, 100% 5 min | ¹H NMR (500 MHz, DMSO-d₆) δ 10.39 (s, 1H), 8.69 (s, 1H), 8.60-8.51 (m, 2H), 8.43 (d, J = 5.7 Hz, 1H), 8.16 (s, 1H), 8.04 (d, J = 8.1 Hz, 1H), 7.94 (d, J = 11.4 Hz, 1H), 7.80 (s, 1H), 7.63 (d, J = 4.0 Hz, 1H), 5.15 (dd, J = 6.4, 2.4 Hz, 1H), 4.81 (dd, J = 6.4, 2.4 Hz, 1H), 4.07 (s, 3H), 3.82-3.71 (m, 1H), 3.43-3.27 (m, 1H), 3.22-3.10 (m, 1H), 2.61 (s, 3H), 1.41 (m, 6H), 1.06 (d, J = 6.1 Hz, 3H) |
| 453 | 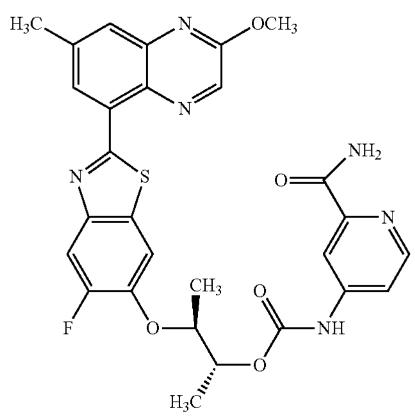 [SMILES: COc1cnc2c(-c3nc4cc(F)c(O[C@@H](C)[C@@H](C)OC(=O)Nc5ccnc(C(N)=O)c5)cc4s3)cc(C)cc2n1] | I-85 | 577.2 | 1.10 | 60-100% 18 min, 100% 7 min | ¹H NMR (500 MHz, DMSO-d₆) δ 10.38 (s, 1H), 8.70 (s, 1H), 8.54 (s, 1H), 8.42 (d, J = 5.7 Hz, 1H), 8.16 (s, 1H), 8.08-8.01 (m, 2H), 7.95 (d, J = 11.4 Hz, 1H), 7.80 (s, 1H), 7.66-7.56 (m, 2H), 5.15 (d, J = 4.4 Hz, 1H), 4.81 (d, J = 4.0 Hz, 1H), 4.07 (s, 3H), 2.62 (s, 3H), 1.41 (m, 6H) |
| 454 | 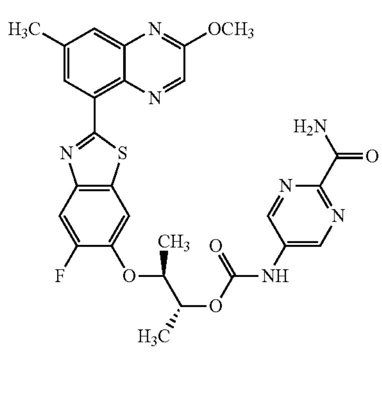 [SMILES: COc1cnc2c(-c3nc4cc(F)c(O[C@@H](C)[C@@H](C)OC(=O)Nc5cnc(C(N)=O)nc5)cc4s3)cc(C)cc2n1] | I-86 | 578.2 | 1.12 | 45-90% 20 min, 100% 7 min | ¹H NMR (500 MHz, DMSO-d₆) δ 10.39 (br. s., 1H), 8.97 (s, 2H), 8.71 (s, 1H), 8.55 (s, 1H), 8.09 (br. s., 1H), 8.05 (d, J = 8.1 Hz, 1H), 7.96 (d, J = 11.4 Hz, 1H), 7.81 (s, 1H), 7.67 (br. s., 1H), 5.21-5.11 (m, 1H), 4.83 (d, J = 4.0 Hz, 1H), 4.08 (s, 3H), 2.62 (s, 3H), 1.42 (m, 6H) |

| Ex. No. | Structure | Ester | LCMS [M + H]+ m/z | LCMS RT (Min) Method H | HPLC Prep Method D | NMR |
|---|---|---|---|---|---|---|
| 455 | 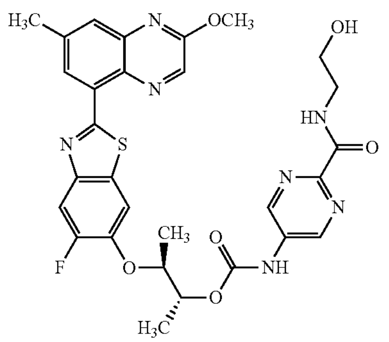 [SMILES: COc1cnc2c(-c3nc4cc(F)c(O[C@@H](C)[C@@H](C)OC(=O)Nc5cnc(C(=O)NCCO)nc5)cc4s3)cc(C)cc2n1] | I-86 | 622.3 | 1.09 | 45-90% 20 min, 100% 5 min | ¹H NMR (500 MHz, DMSO-d₆) δ 10.38 (br. s., 1H), 8.96 (s, 2H), 8.70 (s, 1H), 8.64 (t, J = 5.9 Hz, 1H), 8.55 (s, 1H), 8.04 (d, J = 8.1 Hz, 1H), 7.95 (d, J = 11.4 Hz, 1H), 7.81 (s, 1H), 5.15 (d, J = 6.7 Hz, 1H), 4.88-4.83 (m, 1H), 4.81 (t, J = 5.6 Hz, 1H), 4.07 (s, 3H), 3.51 (q, J = 6.1 Hz, 2H), 3.34 (m, 2H), 2.62 (s, 3H), 1.42 (m, 6H) |
| 456 | 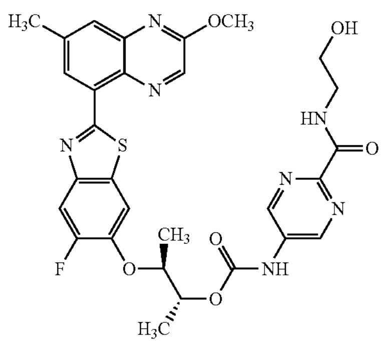 [SMILES: COc1cnc2c(-c3nc4cc(F)c(O[C@@H](C)[C@@H](C)OC(=O)Nc5cnc(C(=O)NCCO)nc5)cc4s3)cc(C)cc2n1] | I-86 | 636.3 | 1.11 | 45-90% 20 min, 100% 5 min | ¹H NMR (500 MHz, DMSO-d₆) δ 10.39 (br. s., 1H), 8.97 (br. s., 2H), 8.69 (s, 1H), 8.59-8.50 (m, 2H), 8.04 (d, J = 8.1 Hz, 1H), 7.95 (d, J = 11.1 Hz, 1H), 7.80 (s, 1H), 5.15 (d, J = 6.4 Hz, 1H), 4.85 (d, J = 4.7 Hz, 2H), 4.07 (s, 3H), 3.83-3.71 (m, 1H), 3.28 (dt, J = 12.4, 6.1 Hz, 1H), 3.16 (dt, J = 12.9, 6.2 Hz, 1H), 2.62 (s, 3H), 1.42 (m, 6H), 1.06 (d, J = 6.1 Hz, 3H) |
| 457 | 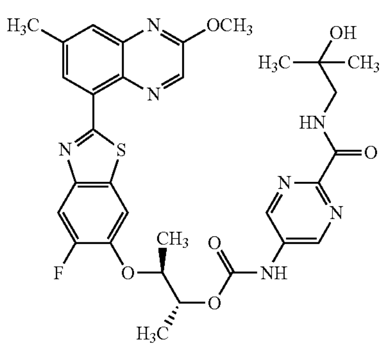 [SMILES: COc1cnc2c(-c3nc4cc(F)c(O[C@@H](C)[C@@H](C)OC(=O)Nc5cnc(C(=O)NCC(C)(C)O)nc5)cc4s3)cc(C)cc2n1] | I-86 | 650.3 | 1.13 | 45-90% 20 min, 100% 5 min | ¹H NMR (500 MHz, DMSO-d₆) δ 10.40 (br. s., 1H), 8.98 (s, 2H), 8.69 (s, 1H), 8.54 (s, 1H), 8.39 (t, J = 6.1 Hz, 1H), 8.04 (d, J = 8.1 Hz, 1H), 7.95 (d, J = 11.1 Hz, 1H), 7.81 (s, 1H), 5.15 (d, J = 4.4 Hz, 1H), 4.85 (d, J = 4.0 Hz, 1H), 4.71 (s, 1H), 4.07 (s, 3H), 3.25 (d, J = 6.4 Hz, 2H), 2.62 (s, 3H), 1.42 (m, 6H), 1.10 (s, 6H) |
| 458 | 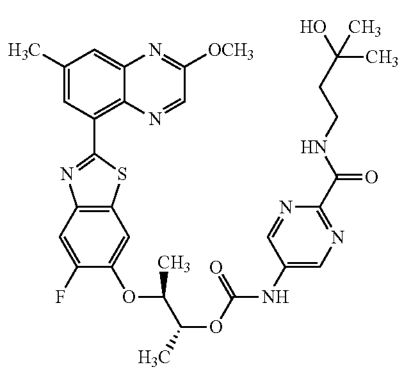 [SMILES: COc1cnc2c(-c3nc4cc(F)c(O[C@@H](C)[C@@H](C)OC(=O)Nc5cnc(C(=O)NCCC(C)(C)O)nc5)cc4s3)cc(C)cc2n1] | I-86 | 664.2 | 1.14 | 45-90% 20 min, 100% 5 min | ¹H NMR (500 MHz, DMSO-d₆) δ 10.35 (br. s., 1H), 8.94 (s, 2H), 8.79 (t, J = 5.6 Hz, 1H), 8.68 (s, 1H), 8.53 (s, 1H), 8.03 (d, J = 8.4 Hz, 1H), 7.94 (d, J = 11.8 Hz, 1H), 7.79 (s, 1H), 5.20-5.09 (m, 1H), 4.85 (d, J = 4.0 Hz, 1H), 4.47 (s, 1H), 4.07 (s, 3H), 3.38-3.30 (m, 2H), 2.61 (s, 3H), 1.62 (t, J = 7.4 Hz, 2H), 1.41 (m, 6H), 1.14 (s, 6H) |

| Ex. No. | Structure | Ester | LCMS [M + H]+ m/z | LCMS RT (Min) Method H | HPLC Prep Method D | NMR |
|---|---|---|---|---|---|---|
| 459 | 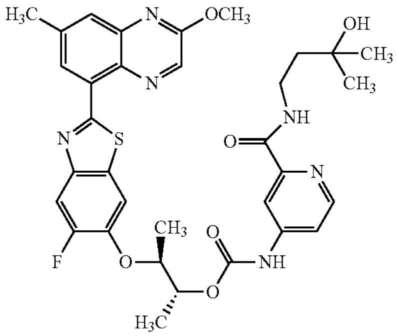 [SMILES: COc1cnc2c(-c3nc4cc(F)c(O[C@@H](C)[C@@H](C)OC(=O)Nc5ccnc(C(=O)NCCC(C)(C)O)c5)cc4s3)cc(C)cc2n1] | I-85 | 664.2 | 1.14 | 45-90% 20 min, 100% 5 min | ¹H NMR (500 MHz, DMSO-d₆) δ 10.35 (br. s., 1H), 8.94 (s, 2H), 8.79 (t, J = 5.6 Hz, 1H), 8.68 (s, 1H), 8.53 (s, 1H), 8.03 (d, J = 8.4 Hz, 1H), 7.94 (d, J = 11.8 Hz, 1H), 7.79 (s, 1H), 5.20-5.09 (m, 1H), 4.85 (d, J = 4.0 Hz, 1H), 4.47 (s, 1H), 4.07 (s, 3H), 3.38-3.30 (m, 2H), 2.61 (s, 3H), 1.62 (t, J = 7.4 Hz, 2H), 1.41 (m, 6H), 1.14 (s, 6H) |
| 460 | 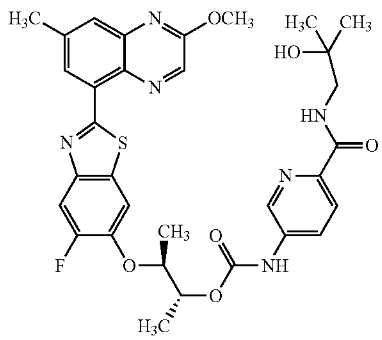 [SMILES: COc1cnc2c(-c3nc4cc(F)c(O[C@@H](C)[C@@H](C)OC(=O)Nc5ccc(C(=O)NCC(C)(C)O)nc5)cc4s3)cc(C)cc2n1] | I-74 | 649.3 | 1.19 | 55-95% 20 min, 100% 5 min | ¹H NMR (500 MHz, DMSO-d₆) δ 10.21 (br. s., 1H), 8.68 (s, 2H), 8.53 (s, 1H), 8.30 (t, J = 6.1 Hz, 1H), 8.09-8.00 (m, 2H), 7.99-7.90 (m, 2H), 7.80 (s, 1H), 5.14 (dd, J = 6.4, 2.4 Hz, 1H), 4.83 (d, J = 3.7 Hz, 1H), 4.07 (s, 3H), 3.24 (d, J = 6.4 Hz, 2H), 2.61 (s, 3H), 1.45-1.37 (m, 6H), 1.09 (s, 6H) |
| 461 | 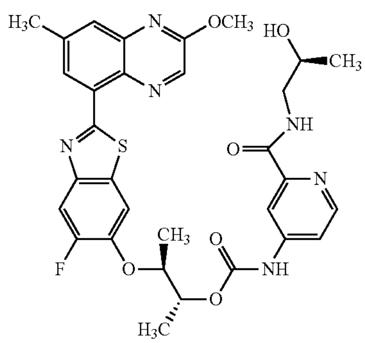 [SMILES: COc1cnc2c(-c3nc4cc(F)c(O[C@@H](C)[C@@H](C)OC(=O)Nc5ccnc(C(=O)NC[C@H](C)O)c5)cc4s3)cc(C)cc2n1] | I-85 | 635.2 | 1.11 | 60-100% 18 min, 100% 5 min | ¹H NMR (500 MHz, DMSO-d₆) δ 10.39 (s, 1H), 8.68 (s, 1H), 8.60-8.50 (m, 2H), 8.42 (d, J = 5.7 Hz, 1H), 8.15 (s, 1H), 8.03 (d, J = 8.1 Hz, 1H), 7.94 (d, J = 11.8 Hz, 1H), 7.79 (s, 1H), 7.63 (d, J = 3.7 Hz, 1H), 5.15 (dd, J = 6.6, 2.5 Hz, 1H), 4.88 (d, J = 4.7 Hz, 1H), 4.81 (dd, J = 6.2, 2.5 Hz, 1H), 4.06 (s, 3H), 3.77 (dt, J = 11.4, 5.6 Hz, 1H), 3.36-3.27 (m, 1H), 3.20-3.10 (m, 1H), 2.61 (s, 3H), 1.47-1.35 (m, 6H), 1.05 (d, J = 6.1 Hz, 3H) |
| 462 | 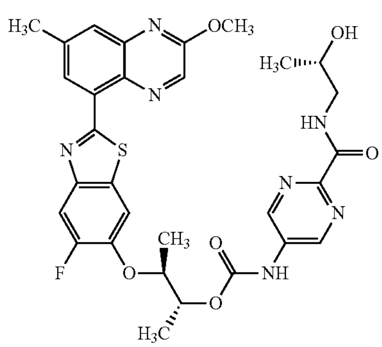 [SMILES: COc1cnc2c(-c3nc4cc(F)c(O[C@@H](C)[C@@H](C)OC(=O)Nc5cnc(C(=O)NC[C@H](C)O)nc5)cc4s3)cc(C)cc2n1] | I-86 | 636.3 | 1.11 | 45-90% 20 min, 100% 5 min | ¹H NMR (500 MHz, DMSO-d₆) δ 10.38 (br. s., 1H), 8.96 (br. s., 2H), 8.67 (s, 1H), 8.56 (t, J = 5.7 Hz, 1H), 8.52 (s, 1H), 8.03 (d, J = 8.1 Hz, 1H), 7.94 (d, J = 11.4 Hz, 1H), 7.79 (s, 1H), 5.15 (dd, J = 6.6, 2.2 Hz, 1H), 4.90-4.79 (m, 2H), 4.07 (s, 3H), 3.78 (dt, J = 11.3, 5.8 Hz, 1H), 3.29 (dt, J = 12.2, 6.2 Hz, 1H), 3.20-3.10 (m, 1H), 2.61 (s, 3H), 1.41 (m, 6H), 1.06 (d, J = 6.1 Hz, 3H) |

-continued

| Ex. No. | Structure | Ester | LCMS [M + H]+ m/z | LCMS RT (Min) Method H | HPLC Prep Method D | NMR |
|---|---|---|---|---|---|---|
| 463 | 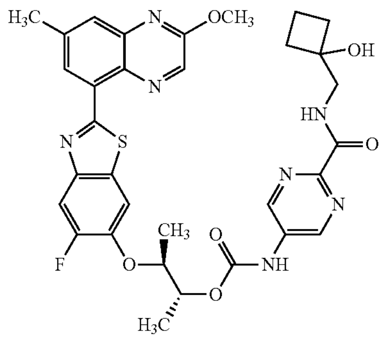 [SMILES: COc1cnc2c(-c3nc4cc(F)c(O[C@@H](C)[C@@H](C)OC(=O)Nc5cnc(C(=O)NCC6(O)CCC6)nc5)cc4s3)cc(C)cc2n1] | I-86 | 662.3 | 1.15 | 50-100% 22 min, 100% 7 min | ¹H NMR (500 MHz, DMSO-d₆) δ 10.41 (br. s., 1H), 8.97 (s, 2H), 8.70 (s, 1H), 8.55 (s, 1H), 8.36 (t, J = 5.9 Hz, 1H), 8.04 (d, J = 8.1 Hz, 1H), 7.95 (d, J = 11.8 Hz, 1H), 7.81 (s, 1H), 5.40 (s, 1H), 5.20-5.09 (m, 1H), 4.85 (d, J = 6.1 Hz, 1H), 4.08 (s, 3H), 2.62 (s, 3H), 2.01-1.87 (m, 4H), 1.70-1.57 (m, 1H), 1.56-1.43 (m, 1H), 1.42 (m, 6H) |
| 464 | 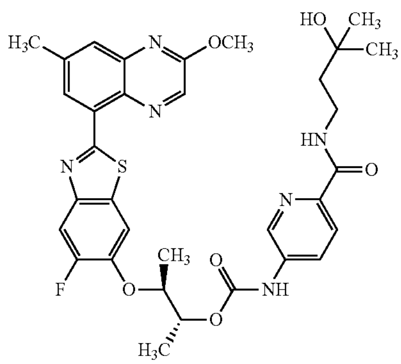 [SMILES: COc1cnc2c(-c3nc4cc(F)c(O[C@@H](C)[C@@H](C)OC(=O)Nc5ccc(C(=O)NCCC(C)(C)O)nc5)cc4s3)cc(C)cc2n1] | I-82 | 649.2 | 1.21 | 45-90% 19 min, 100% 10 min | ¹H NMR (500 MHz, DMSO-d₆) δ 8.81 (s, 1H), 8.75 (br. s., 2H), 8.65 (br. s., 1H), 8.18-7.99 (m, 4H), 7.91 (br. s., 1H), 5.37 (br. s., 1H), 4.46 (br. s., 1H), 4.38 (br. s., 1H), 4.16 (s, 43), 3.46 (m, 2H), 2.71 (s, 3H), 1.70 (m, 2H), 1.51 (d, J = 6.4 Hz, 3H), 1.22 (s, 6H) |
| 465 | 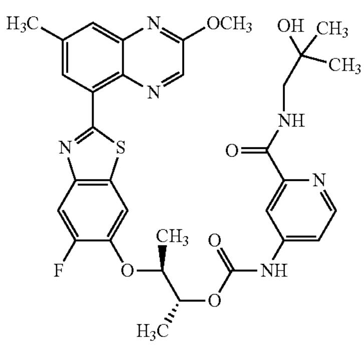 [SMILES: COc1cnc2c(-c3nc4cc(F)c(O[C@@H](C)[C@@H](C)OC(=O)Nc5ccnc(C(=O)NCC(C)(C)O)c5)cc4s3)cc(C)cc2n1] | I-85 | 649.3 | 1.14 | 40-80% 20 min, 100% 5 min | ¹H NMR (500 MHz, DMSO-d₆) δ 10.37 (s, 1H), 8.70 (s, 1H), 8.55 (s, 1H), 8.44 (d, J = 5.2 Hz, 2H), 8.17 (s, 1H), 8.03 (d, J = 8.2 Hz, 1H), 7.94 (d, J = 11.6 Hz, 1H), 7.81 (s, 1H), 7.66-7.60 (m, 1H), 5.15 (dd, J = 6.7, 2.4 Hz, 1H), 4.81 (dd, J = 6.1, 2.4 Hz, 1H), 4.74 (s, 1H), 4.08 (s, 3H), 3.26 (d, J = 6.1 Hz, 2H), 2.62 (s, 3H), 1.41 (m, 6H), 1.10 (s, 6H) |
| 466 | 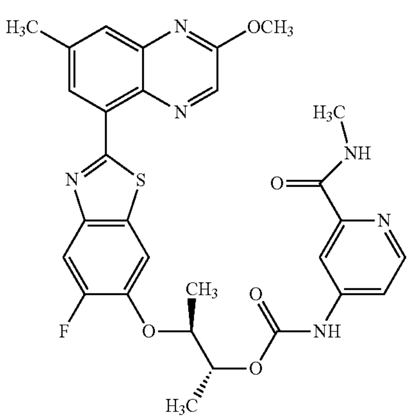 [SMILES: CNC(=O)c1cc(NC(=O)O[C@H](C)[C@H](C)Oc2cc3sc(-c4cc(C)cc5nc(OC)cnc45)nc3cc2F)ccn1] | I-85 | 591.1 | 1.15 | 45-90% 25 min, 100% 7 min | ¹H NMR (500 MHz, DMSO-d₆) δ 10.34 (s, 1H), 8.73-8.62 (m, 2H), 8.54 (s, 1H), 8.41 (d, J = 4.9 Hz, 1H), 8.13 (br. s., 1H), 8.02 (d, J = 8.2 Hz, 1H), 7.93 (d, J = 11.6 Hz, 1H), 7.80 (s, 1H), 7.62 (br. s., 1H), 5.15 (dd, J = 6.4, 2.7 Hz, 1H), 4.81 (dd, J = 6.3, 2.6 Hz, 1H), 4.07 (s, 3H), 2.79 (d, J = 4.6 Hz, 3H), 2.62 (s, 3H), 1.41 (m, 6H) |

-continued

| Ex. No. | Structure | Ester | LCMS [M + H]+ m/z | LCMS RT (Min) Method H | HPLC Prep Method D | NMR |
|---|---|---|---|---|---|---|
| 467 | 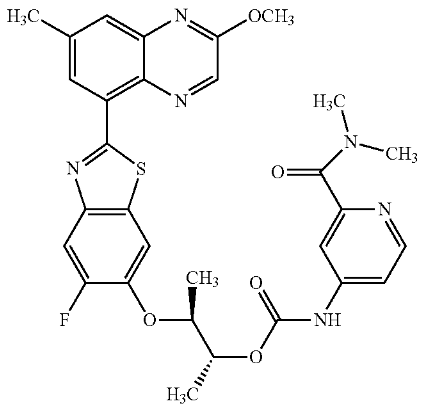 [SMILES: COc1cnc2c(-c3nc4cc(F)c(O[C@@H](C)[C@@H](C)OC(=O)Nc5ccnc(C(=O)N(C)C)c5)cc4s3)cc(C)cc2n1] | I-85 | 605.1 | 1.08 | 40-75% 25 min, 100% 7 min | ¹H NMR (500 MHz, DMSO-d₆) δ 10.30 (s, 1H), 8.68 (s, 1H), 8.53 (s, 1H), 8.36 (d, J = 5.5 Hz, 1H), 8.02 (d, J = 8.2 Hz, 1H), 7.94 (d, J = 11.6 Hz, 1H), 7.80 (s, 1H), 7.58 (s, 1H), 7.51-7.43 (m, 1H), 5.14 (dd, J = 6.6, 2.6 Hz, 1H), 4.81 (dd, J = 6.3, 2.6 Hz, 1H), 4.07 (s, 3H), 2.98 (s, 3H), 2.89 (s, 3H), 2.61 (s, 3H), 1.41 (m, 6H) |
| 468 | 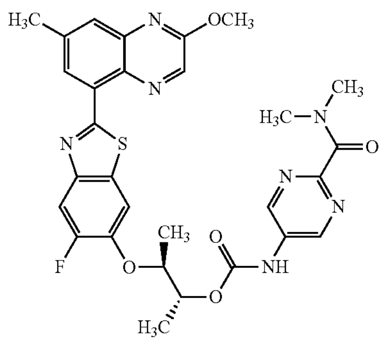 [SMILES: COc1cnc2c(-c3nc4cc(F)c(O[C@@H](C)[C@@H](C)OC(=O)Nc5cnc(C(=O)N(C)C)nc5)cc4s3)cc(C)cc2n1] | I-86 | 606.2 | 1.19 | 45-90% 22 min, 100% 7 min | ¹H NMR (500 MHz, DMSO-d₆) δ 10.27 (br. s., 1H), 8.91 (s, 2H), 8.69 (s, 1H), 8.53 (s, 1H), 8.03 (d, J = 7.9 Hz, 1H), 7.94 (d, J = 11.6 Hz, 1H), 7.80 (s, 1H), 5.15 (dd, J = 6.6, 2.6 Hz, 1H), 4.87-4.76 (m, 1H), 4.07 (s, 3H), 2.99 (s, 3H), 2.76 (s, 3H), 2.62 (s, 3H), 1.45-1.37 (m, 6H) |
| 469 | 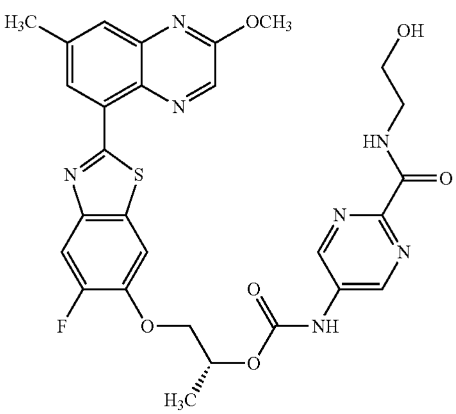 [SMILES: COc1cnc2c(-c3nc4cc(F)c(OC[C@@H](C)OC(=O)Nc5cnc(C(=O)NCCO)nc5)cc4s3)cc(C)cc2n1] | I-82 | 607.9 | 1.06 | 45-80% 25 min, 80% 4 min | ¹H NMR (500 MHz, DMSO-d₆) δ 8.97 (s, 2H), 8.67 (t, J = 5.8 Hz, 1H), 8.64 (s, 1H), 8.48 (s, 1H), 7.95-7.87 (m, 2H), 7.75 (s, 1H), 5.35-5.23 (m, 1H), 4.94-4.88 (m, 1H), 4.38 (d, J = 8.2 Hz, 1H), 4.28 (dd, J = 10.7, 6.1 Hz, 1H), 4.05 (s, 3H), 3.55-3.49 (m, 2H), 3.36 (q, J = 6.0 Hz, 2H), 2.59 (s, 3H), 1.44 (d, J = 6.4 Hz, 3H) |

Preparation of Hindered Amide Examples

The sterically hindered amides in the accompanying table were prepared according to the following two-step procedure.

Saponification: To a solution of the appropriately substituted hetero-aryl ester (1.0 equiv) in THF (0.05 M) was added a 1 M solution of LiOH (5 equiv). The resulting mixture was stirred vigorously at for 3 h before being quenched with a 1 M solution of HCl (10 equiv). The solution was concentrated to a crude residue in vacuo and taken on to the subsequent HATU coupling without purification.

HATU Coupling: The crude saponified residue above (1.0 equiv) was retaken in DMF (0.1 M) and stirred at room temperature. To this solution was added diisopropylethylamine (10 equiv) and the appropriate amine substrate (1.5 equiv) followed by HATU (1.5 equiv). The resulting mixture was stirred for 10 min before being quenched with methanol (100 equiv), concentrated, and purified by Prep HPLC (Method D, unless otherwise indicated) to afford the desired example.

| Ex. No. | Structure | Ester | LCMS [M+H]+ m/z | LCMS RT (Min) Method H | HPLC Prep Method D | NMR |
|---|---|---|---|---|---|---|
| 470 | 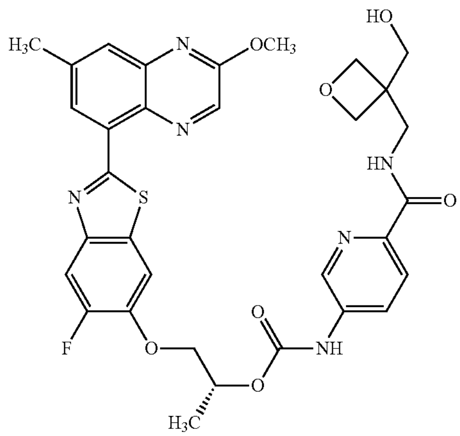 [SMILES: COc1cnc2c(-c3nc4cc(F)c(OC[C@@H](C)OC(=O)Nc5ccc(C(=O)NCC6(CO)COC6)nc5)cc4s3)cc(C)cc2n1] | I-82 | 663.1 | 1.13 | 45-90% 20 min, 100% 6 min | ¹H NMR (500 MHz, DMSO-d₆) δ 10.29 (br. s., 1H), 8.87 (t, J = 6.3 Hz, 1H), 8.72 (s, 1H), 8.69 (s, 1H), 8.53 (s, 1H), 8.07 (d, J = 8.5 Hz, 1H), 8.02-7.91 (m, 3H), 7.79 (s, 1H), 5.30 (d, J = 3.1 Hz, 1H), 5.05 (t, J = 5.5 Hz, 1H), 4.39 (d, J = 6.1 Hz, 3H), 4.33-4.23 (m, 3H), 4.07 (s, 3H), 3.64-3.54 (m, 4H), 2.61 (s, 3H), 1.44 (d, J = 6.4 Hz, 3H) |
| 471 | 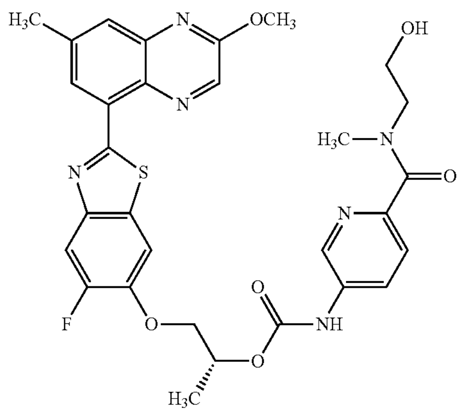 [SMILES: COc1cnc2c(-c3nc4cc(F)c(OC[C@@H](C)OC(=O)Nc5ccc(C(=O)N(C)CCO)nc5)cc4s3)cc(C)cc2n1] | I-82 | 621.2 | 1.10 | 30-100% 20 min, 100% 5 min | ¹H NMR (500 MHz, DMSO-d₆) δ 10.22 (br. s., 1H), 8.73 (s, 1H), 8.71-8.64 (m, 1H), 8.57 (s, 1H), 8.06 (d, J = 8.5 Hz, 1H), 8.03-7.96 (m, 2H), 7.85 (s, 1H), 7.59 (d, J = 8.5 Hz, 1H), 5.35 (br. s., 1H), 4.43 (d, J = 8.5 Hz, 1H), 4.38-4.30 (m, 1H), 4.13 (s, 3H), 3.56 (br. s., 3H), 3.47 (br. s., 1H), 3.06 (br. s., 3H), 2.67 (s, 3H), 1.49 (d, J = 6.1 Hz, 3H) |
| 472 | 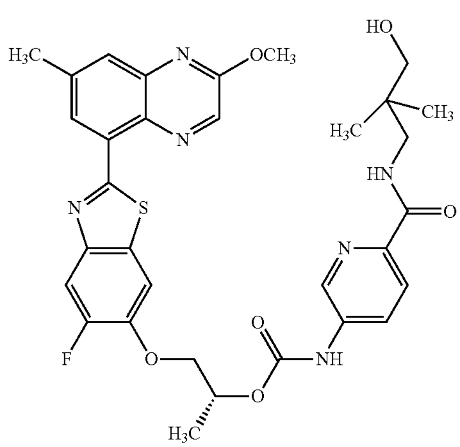 [SMILES: COc1cnc2c(-c3nc4cc(F)c(OC[C@@H](C)OC(=O)Nc5ccc(C(=O)NCC(C)(C)CO)nc5)cc4s3)cc(C)cc2n1] | I-82 | 649.2 | 1.22 | 35-100% 20 min, 100% 10 min | ¹H NMR (500 MHz, DMSO-d₆) δ 10.32 (br. s., 1H), 8.79 (s, 1H), 8.76 (br. s., 1H), 8.68 (br. s., 1H), 8.63 (s, 1H), 8.13 (d, J = 7.9 Hz, 1H), 8.08-8.01 (m, 3H), 7.90 (s, 1H), 5.37 (br. s., 1H), 4.47 (d, J = 8.5 Hz, 1H), 4.38 (br. s., 1H), 4.16 (s, 3H), 3.28-3.21 (m, 5H), 2.70 (s, 3H), 1.51 (d, J = 6.1 Hz, 3H), 0.89 (s, 6H) |

| Ex. No. | Structure | Ester | LCMS [M + H]+ m/z | LCMS RT (Min) Method H | HPLC Prep Method D | NMR |
|---|---|---|---|---|---|---|
| 473 | 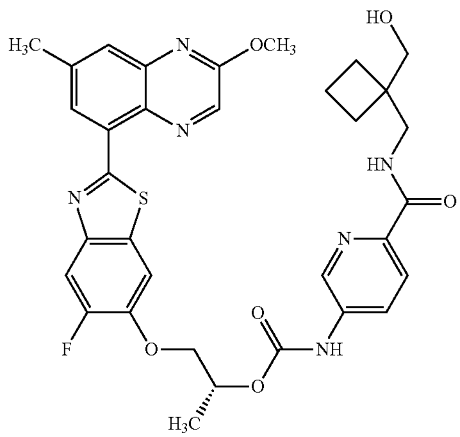 | I-82 | 661.3 | 1.19 | 50-100% 20 min, 100% 5 min | ¹H NMR (500 MHz, DMSO-d₆) δ 10.25 (br. s., 1H), 8.72 (s, 1H), 8.66 (d, J = 12.2 Hz, 2H), 8.56 (s, 1H), 8.06 (d, J = 10.4 Hz, 1H), 8.01-7.93 (m, 3H), 7.84 (s, 1H), 5.29 (br. s., 1H), 4.43-4.37 (m, 1H), 4.33-4.25 (m, 1H), 4.09 (s, 3H), 3.40 (br. s., 4H), 2.63 (s, 3H), 1.86-1.65 (m, 6H), 1.43 (d, J = 6.4 Hz, 3H) |
| 474 | 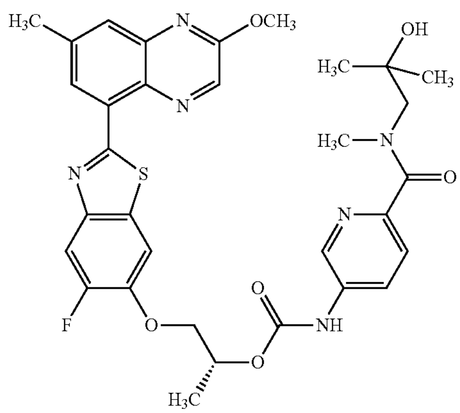 [SMILES: COc1cnc2c(-c3nc4cc(F)c(OC[C@@H](C)OC(=O)Nc5ccc(C(=O)N(C)CC(C)(C)O)nc5)cc4s3)cc(C)cc2n1] | I-82 | 649.2 | 1.15 | 45-100% 11 min, 100% 6 min | ¹H NMR (500 MHz, DMSO-d₆) δ 10.16 (d, J = 12.2 Hz, 1H), 8.65 (s, 1H), 8.64-8.57 (m, 1H), 8.49 (s, 1H), 7.99 (br. s., 1H), 7.95-7.88 (m, 2H), 7.77 (s, 1H), 7.56-7.46 (m, 1H), 5.28 (br. s., 1H), 4.36 (d, J = 10.1 Hz, 1H), 4.31-4.24 (m, 1H), 4.06 (s, 3H), 3.58 (s, 2H), 3.10-3.00 (m, 3H), 2.60 (s, 3H), 1.43 (d, J = 6.4 Hz, 3H), 1.15 (s, 3H), 0.91 (s, 3H) |
| 475 | 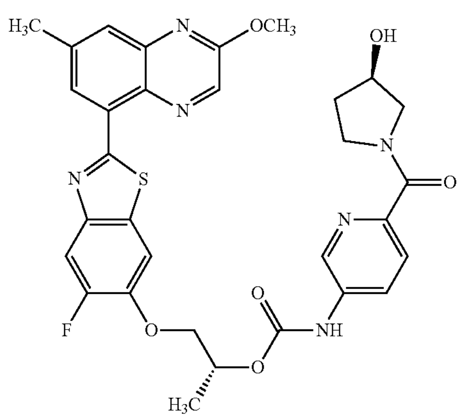 | I-82 | 633.2 | 1.10 | 45-100% 20 min, 100% 5 min | ¹H NMR (500 MHz, DMSO-d₆) δ 10.19 (d, J = 6.1 Hz, 1H), 8.64 (s, 2H), 8.49 (s, 1H), 8.01 (d, J = 8.5 Hz, 1H), 7.96-7.85 (m, 2H), 7.79-7.67 (m, 2H), 5.28 (br. s., 1H), 4.41-4.33 (m, 1H), 4.33-4.23 (m, 2H), 4.06 (s, 3H), 3.81-3.59 (m, 2H), 3.54-3.37 (m, 2H), 2.59 (s, 3H), 1.96-1.85 (m, 1H), 1.80 (br. s., 1H), 1.43 (d, J = 6.4 Hz, 3H) |

| Ex. No. | Structure | Ester | LCMS [M+H]+ m/z | LCMS RT (Min) Method H | HPLC Prep Method D | NMR |
|---|---|---|---|---|---|---|
| 476 | 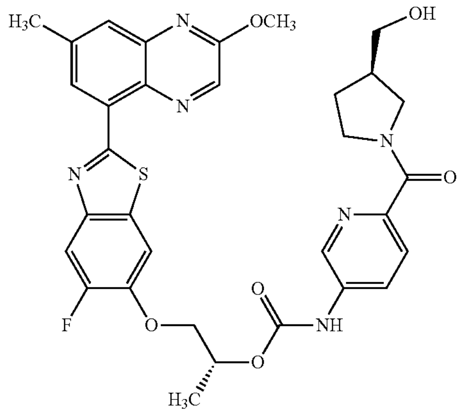 [SMILES: COc1cnc2c(-c3nc4cc(F)c(OC[C@@H](C)OC(=O)Nc5ccc(C(=O)N6CC[C@@H](CO)C6)nc5)cc4s3)cc(C)cc2n1] | I-82 | 647.2 | 1.10 | 35-75% 20 min, 100% 5 min | ¹H NMR (500 MHz, DMSO-d₆) δ 10.18 (br. s., 1H), 8.68-8.59 (m, 2H), 8.50 (s, 1H), 8.00 (br. s., 1H), 7.96-7.88 (m, 2H), 7.77 (s, 1H), 7.71 (d, J = 8.2 Hz, 1H), 5.28 (br. s., 1H), 4.41-4.34 (m, 1H), 4.28 (dd, J = 10.7, 6.1 Hz, 1H), 4.06 (s, 3H), 3.79-3.66 (m, 1H), 3.49-3.35 (m, 3H), 3.34-3.28 (m, 1H), 3.27-3.20 (m, 1H), 2.60 (s, 3H), 2.34-2.24 (m, 1H), 1.96-1.85 (m, 1H), 1.67-1.55 (m, 1H), 1.43 (d, J = 6.4 Hz, 3H) |
| 477 | 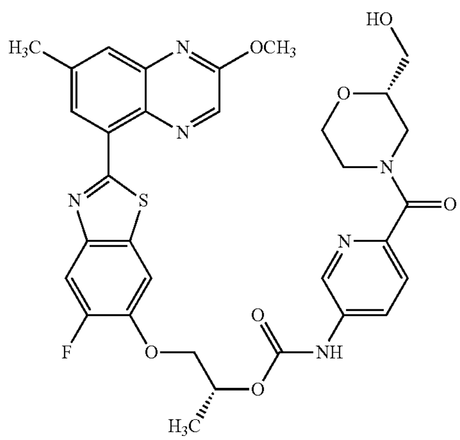 [SMILES: COc1cnc2c(-c3nc4cc(F)c(OC[C@@H](C)OC(=O)Nc5ccc(C(=O)N6CCO[C@H](CO)C6)nc5)cc4s3)cc(C)cc2n1] | I-82 | 663.3 | 1.10 | 40-85% 16 min, 100% 5 min | ¹H NMR (500 MHz, DMSO-d₆) δ 10.20 (br. s., 1H), 8.67 (s, 1H), 8.63 (br. s., 1H), 8.51 (s, 1H), 8.02 (d, J = 8.5 Hz, 1H), 7.97-7.89 (m, 2H), 7.78 (s, 1H), 7.59 (d, J = 8.5 Hz, 1H), 5.28 (br. s., 1H), 4.46-4.33 (m, 2H), 4.28 (dd, J = 10.5, 6.0 Hz, 1H), 4.06 (s, 3H), 3.97-3.84 (m, 1H), 3.77 (br. s., 1H), 3.51-3.33 (m, 3H), 3.31-3.11 (m, 1H), 3.02-2.88 (m, 1H), 2.67 (d, J = 10.1 Hz, 1H), 2.60 (s, 3H), 1.43 (d, J = 6.4 Hz, 3H) |
| 478 | 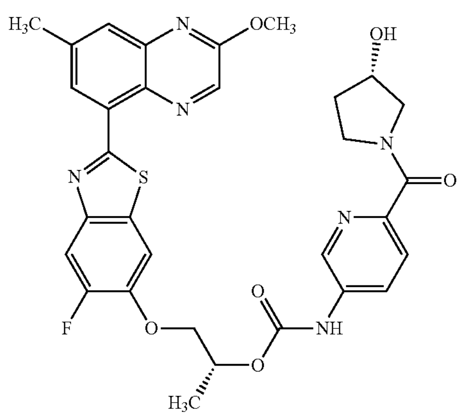 [SMILES: COc1cnc2c(-c3nc4cc(F)c(OC[C@@H](C)OC(=O)Nc5ccc(C(=O)N6CC[C@H](O)C6)nc5)cc4s3)cc(C)cc2n1] | I-82 | 633.2 | 1.10 | 35-95% 20 min, 100% 5 min | ¹H NMR (500 MHz, DMSO-d₆) δ 10.18 (br. s., 1H), 8.67-8.59 (m, 2H), 8.49 (s, 1H), 8.01 (br. s., 1H), 7.95-7.87 (m, 2H), 7.76 (s, 1H), 7.72 (dd, J = 12.5, 8.5 Hz, 1H), 5.28 (d, J = 3.1 Hz, 1H), 4.37 (d, J = 9.5 Hz, 1H), 4.27 (dd, J = 10.5, 6.0 Hz, 2H), 4.05 (s, 3H), 3.78-3.69 (m, 1H), 3.59 (s, 2H), 3.52 (d, J = 11.6 Hz, 1H), 3.42 (d, J = 13.1 Hz, 1H), 2.59 (s, 3H), 1.90 (dd, J = 8.9, 4.0 Hz, 1H), 1.80 (br. s., 1H), 1.43 (d, J = 6.4 Hz, 3H) |

| Ex. No. | Structure | Ester | LCMS [M + H]+ m/z | LCMS RT (Min) Method H | HPLC Prep Method D | NMR |
|---|---|---|---|---|---|---|
| 479 | 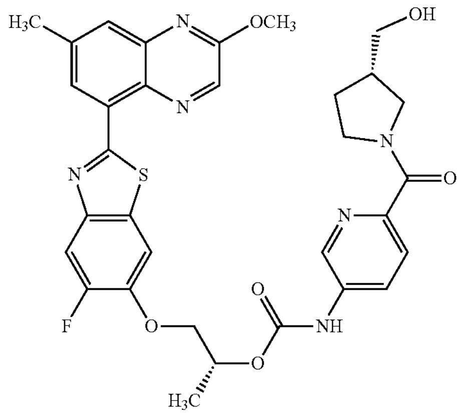 [SMILES: COc1cnc2c(-c3nc4cc(F)c(OC[C@@H](C)OC(=O)Nc5ccc(C(=O)N6CC[C@H](CO)C6)nc5)cc4s3)cc(C)cc2n1] | I-82 | 647.2 | 1.10 | 45-90% 19 min, 100% 5 min | ¹H NMR (500 MHz, DMSO-d₆) δ 10.18 (br. s., 1H), 8.65 (s, 1H), 8.62 (br. s., 1H), 8.50 (s, 1H), 8.01 (t, J = 7.3 Hz, 1H), 7.95-7.88 (m, 2H), 7.77 (s, 1H), 7.73-7.68 (m, 1H), 6.62 (d, J = 8.5 Hz, 1H), 5.28 (br. s., 1H), 4.37 (d, J = 8.2 Hz, 1H), 4.28 (dd, J = 10.8, 6.3 Hz, 1H), 4.06 (s, 3H), 3.78-3.66 (m, 1H), 3.48-3.35 (m, 3H), 3.34-3.27 (m, 1H), 3.24 (dd, J = 12.4, 7.2 Hz, 1H), 2.60 (s, 3H), 2.35-2.23 (m, 1H), 1.96-1.84 (m, 1H), 1.67-1.54 (m, 1H), 1.43 (d, J = 6.7 Hz, 3H) |
| 480 | 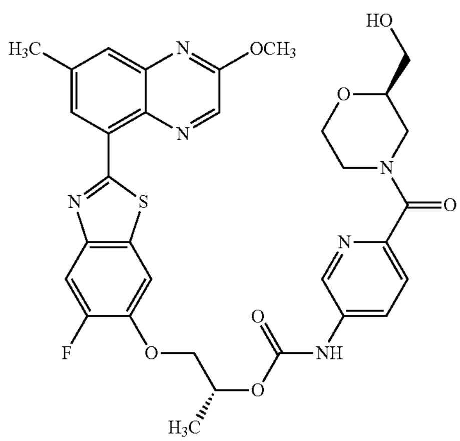 [SMILES: COc1cnc2c(-c3nc4cc(F)c(OC[C@@H](C)OC(=O)Nc5ccc(C(=O)N6CCO[C@@H](CO)C6)nc5)cc4s3)cc(C)cc2n1] | I-82 | 663.3 | 1.10 | 40-85% 15 min, 100% 5 min | ¹H NMR (500 MHz, DMSO-d₆) δ 10.20 (br. s., 1H), 8.67 (s, 1H), 8.63 (br. s., 1H), 8.51 (s, 1H), 8.02 (d, J = 8.5 Hz, 1H), 7.97-7.87 (m, 2H), 7.78 (s, 1H), 7.59 (d, J = 5.2 Hz, 1H), 5.29 (br. s., 1H), 4.48-4.23 (m, 3H), 4.06 (s, 3H), 3.96-3.84 (m, 1H), 3.82-3.72 (m, 1H), 3.51-3.06 (m, 4H), 3.00-2.89 (m, 1H), 2.67 (d, J = 9.8 Hz, 1H), 2.60 (s, 3H), 1.43 (d, J = 6.4 Hz, 3H) |
| 481 | 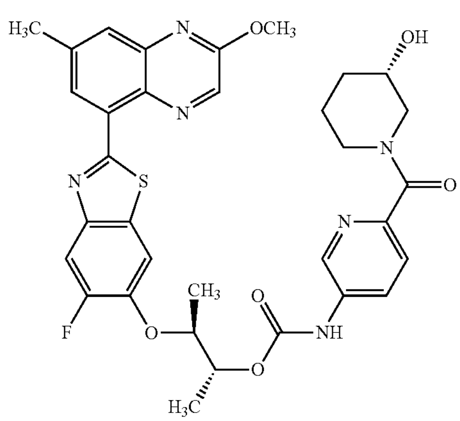 [SMILES: COc1cnc2c(-c3nc4cc(F)c(O[C@@H](C)[C@@H](C)OC(=O)Nc5ccc(C(=O)N6CCC[C@H](O)C6)nc5)cc4s3)cc(C)cc2n1] | I-74 | 661.2 | 1.20 | 45-90% 25 min, 100% 6 min | — |

| Ex. No. | Structure | Ester | LCMS [M+H]+ m/z | LCMS RT (Min) Method H | HPLC Prep Method D | NMR |
|---|---|---|---|---|---|---|
| 482 | 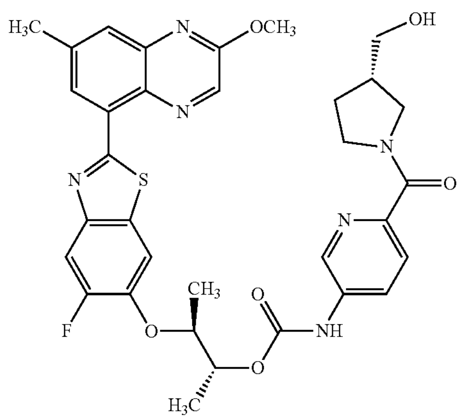 [SMILES: COc1cnc2c(-c3nc4cc(F)c(O[C@@H](C)[C@@H](C)OC(=O)Nc5ccc(C(=O)N6CC[C@H](CO)C6)nc5)cc4s3)cc(C)cc2n1] | I-74 | 661.2 | 1.17 | 45-90% 25 min, 100% 6 min | ¹H NMR (500 MHz, DMSO-d₆) δ 10.09 (br. s., 1H), 8.70-8.65 (m, 1H), 8.60 (d, J = 6.7 Hz, 1H), 8.53 (s, 1H), 8.07-7.90 (m, 3H), 7.79 (s, 1H), 7.70 (d, J = 8.5 Hz, 1H), 5.13 (br. s., 1H), 4.83 (br. s., 1H), 4.78-4.65 (m, 1H), 4.12-4.02 (m, 3H), 3.73 (dd, J = 19.1, 11.7 Hz, 1H), 3.66-3.51 (m, 1H), 3.46-3.35 (m, 3H), 3.35-3.17 (m, 1H), 2.66-2.59 (m, 3H), 2.35-2.21 (m, 1H), 1.89 (br. s., 1H), 1.60 (d, J = 7.9 Hz, 1H), 1.41 (t, J = 5.0 Hz, 6H) |
| 483 | 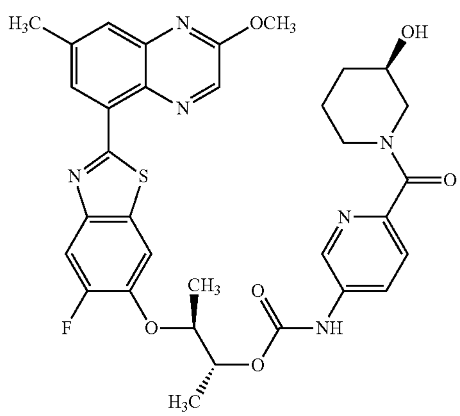 [SMILES: COc1cnc2c(-c3nc4cc(F)c(O[C@@H](C)[C@@H](C)OC(=O)Nc5ccc(C(=O)N6CCC[C@@H](O)C6)nc5)cc4s3)cc(C)cc2n1] | I-74 | 661.2 | 1.20 | 45-90% 25 min, 100% 6 min | — |
| 484 | 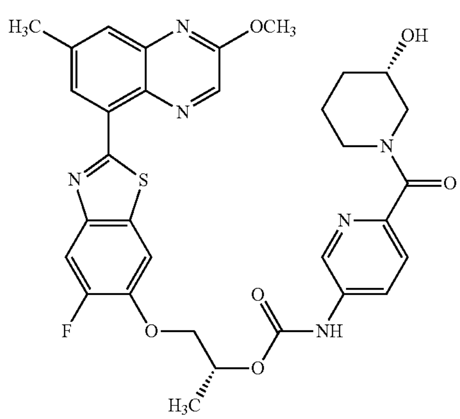 [SMILES: COc1cnc2c(-c3nc4cc(F)c(OC[C@@H](C)OC(=O)Nc5ccc(C(=O)N6CCC[C@H](O)C6)nc5)cc4s3)cc(C)cc2n1] | I-82 | 647.3 | 1.22 | 45-90% 15 min, 100% 5 min | ¹H NMR (500 MHz, DMSO-d₆) δ 10.19 (br. s., 1H), 8.69 (s, 1H), 8.64 (br. s., 1H), 8.53 (s, 1H), 8.07-7.91 (m, 3H), 7.79 (s, 1H), 7.58-7.46 (m, 1H), 5.29 (br. s., 1H), 4.38 (d, J = 8.9 Hz, 1H), 4.33-4.26 (m, 1H), 4.23 (d, J = 11.3 Hz, 1H), 4.07 (s, 3H), 3.87 (d, J = 13.1 Hz, 1H), 3.67-3.38 (m, 2H), 3.16 (br. s., 1H), 3.06-2.94 (m, 1H), 2.83-2.71 (m, 1H), 2.61 (s, 3H), 1.94-1.81 (m, 1H), 1.76 (br. s., 1H), 1.62 (br. s., 1H), 1.44 (d, J = 6.1 Hz, 4H), 1.38 (d, J = 9.5 Hz, 1H) |

| Ex. No. | Structure | Ester | LCMS [M+H]+ m/z | LCMS RT (Min) Method H | HPLC Prep Method D | NMR |
|---|---|---|---|---|---|---|
| 485 | 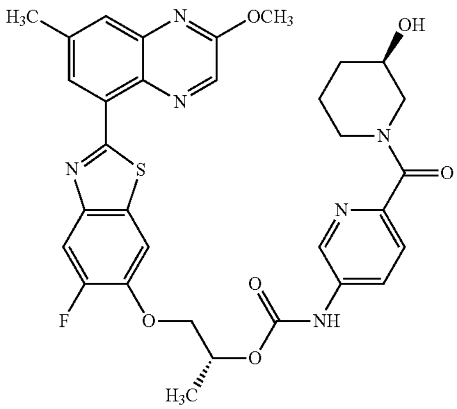 [SMILES: COc1cnc2c(-c3nc4cc(F)c(OC[C@@H](C)OC(=O)Nc5ccc(C(=O)N6CCC[C@@H](O)C6)nc5)cc4s3)cc(C)cc2n1] | I-82 | 647.3 | 1.22 | 45-90% 15 min, 100% 5 min | ¹H NMR (500 MHz, DMSO-d₆) δ 10.19 (br. s., 1H), 8.69 (s, 1H), 8.63 (br. s., 1H), 8.53 (s, 1H), 8.07-7.90 (m, 3H), 7.79 (s, 1H), 7.59-7.46 (m, 1H), 5.29 (br. s., 1H), 4.38 (d, J = 8.9 Hz, 1H), 4.33-4.17 (m, 1H), 4.12-4.01 (m, 3H), 3.88 (br. s., 1H), 3.68-3.53 (m, 1H), 3.16 (br. s., 1H), 3.01 (d, J = 7.6 Hz, 1H), 2.77 (t, J = 10.5 Hz, 1H), 2.61 (s, 3H), 1.96-1.80 (m, 1H), 1.76 (br. s., 1H), 1.62 (br. s., 1H), 1.51-1.30 (m, 5H) |
| 486 | 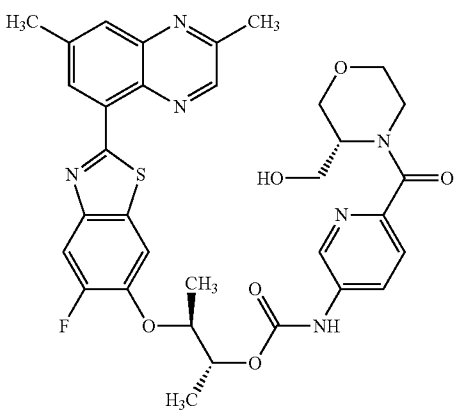 [SMILES: Cc1cc(-c2nc3cc(F)c(O[C@@H](C)[C@@H](C)OC(=O)Nc4ccc(C(=O)N5CCOC[C@H]5CO)nc4)cc3s2)c2ncc(C)nc2c1] | I-74 | 677.2 | 1.21 | 40-90% 19 min, 100% 5 min | — |
| 487 | 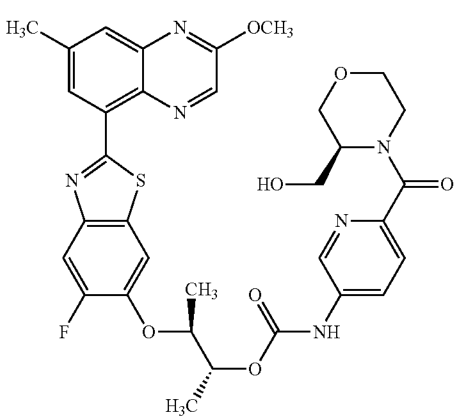 [SMILES: COc1cnc2c(-c3nc4cc(F)c(O[C@@H](C)[C@@H](C)OC(=O)Nc5ccc(C(=O)N6CCOC[C@@H]6CO)nc5)cc4s3)cc(C)cc2n1] | I-74 | 677.2 | 1.20 | 45-90% 20 min, 100% 5 min | ¹H NMR (500 MHz, DMSO-d₆) δ 10.11 (br. s., 1H), 8.72 (s, 1H), 8.61 (br. s., 1H), 8.57 (d, J = 1.2 Hz, 1H), 8.05 (d, J = 8.2 Hz, 1H), 7.99 (d, J = 8.5 Hz), 7.96 (d, J = 11.6 Hz, 1H), 7.83 (s, 1H), 7.56 (d, J = 8.5 Hz, 1H), 5.14 (dd, J = 6.4, 2.4 Hz, 1H), 4.81 (dd, J = 6.3, 2.6 Hz, 1H), 4.32 (br. s., 1H), 4.16-3.98 (m, 4H), 3.97-3.85 (m, 1H), 3.82-3.40 (m, 3H), 2.63 (s, 3H), 1.41 (dd, J = 6.3, 4.1 Hz, 6H). |

-continued

| Ex. No. | Structure | Ester | LCMS [M + H]+ m/z | LCMS RT (Min) Method H | HPLC Prep Method D | NMR |
|---|---|---|---|---|---|---|
| 488 | (structure) | I-82 | 663.3 | 1.21 | 40-100% 15 min, 100% 5 min | ¹H NMR (500 MHz, DMSO-d₆) δ 10.21 (br. s., 1H), 8.73 (s, 1H), 8.62 (br. s., 1H), 8.56 (s, 1H), 8.05-7.99 (m, 2H), 7.97 (d, J = 11.6 Hz, 1H), 7.82 (s, 1H), 7.57 (d, J = 8.5 Hz, 1H), 5.28 (dd, J = 8.9, 6.1 Hz, 1H), 4.88 (br. s., 1H), 4.42-4.36 (m, 1H), 4.35-4.25 (m, 1H), 4.08 (s, 3H), 4.02 (d, J = 11.3 Hz, 1H), 3.97-3.85 (m, 1H), 3.78 (d, J = 11.6 Hz, 1H), 3.70 (d, J = 6.7 Hz, 1H), 3.57 (br. s., 1H), 3.50 (d, J = 13.4 Hz, 1H), 2.63 (s, 3H), 1.44 (d, J = 6.4 Hz, 3H) |
| 489 | (structure) | I-82 | 663.3 | 1.21 | 40-100% 15 min, 100% 5 min | ¹H NMR (500 MHz, DMSO-d₆) δ 10.21 (br. s., 1H), 8.74 (s, 1H), 8.62 (br. s., 1H), 8.57 (s, 1H), 8.05-7.94 (m, 3H), 7.83 (s, 1H), 7.57 (d, J = 8.5 Hz, 1H), 5.29 (dd, J = 9.2, 6.1 Hz, 1H), 5.00-4.78 (m, 1H), 4.43-4.36 (m, 1H), 4.35-4.24 (m, 1H), 4.16-3.99 (m, 4H), 3.98-3.85 (m, 1H), 3.82-3.66 (m, 1H), 3.66-3.42 (m, 2H), 2.63 (s, 3H), 1.44 (d, J = 6.4 Hz, 3H) |

Example 490

(2R,3S)-3-((2-(2-(difluoromethoxy)-7-methylquinoxalin-5-yl)-5-fluorobenzo[d]thiazol-6-yl)oxy)butan-2-yl (2-methylpyrimidin-5-yl)carbamate

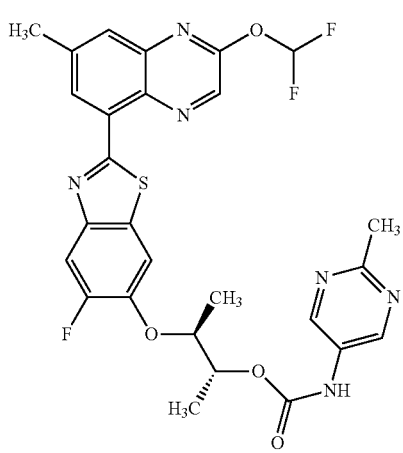

(490)

To a solution Intermediate I-72B (150 mg, 0.334 mmol) in THF (6.5 mL) was added a 15% phosgene solution in toluene (2354 μl, 3.34 mmol). The resulting slurry was allowed to stir overnight before concentrated down to a crude yellow residue. This intermediate chloroformate was retaken in THF (6.5 mL) and added dropwise to a premixed solution of 2-methylpyrimidin-5-amine (39.9 mg, 0.365 mmol) and pyridine (0.134 mL, 1.660 mmol) in THF (6.5 mL). After 10 min of stirring, the reaction mixture was concentrated and loaded directly onto an ISCO cartridge for purification (40 g, 0-100% EtOAc/DCM, product at 85%) to afford Example 490 (182 mg, 0.331 mmol, 94% yield) as a yellow solid. A small amount of material was purified by Prep HPLC for final characterization (Method D, 50-100% over 10 min, hold 100% for 5 min). LC-MS: Method H, RT=1.17 min, MS (ESI) m/z: 585.2 (M+H)+. ¹H NMR (400 MHz, CDCl₃) δ 8.76 (d, J=2.0 Hz, 1H), 8.72 (br. s., 2H), 8.69 (s, 1H), 7.86-7.78 (m, 2H), 7.66 (t, J=71.8 Hz, 1H), 7.53 (d, J=7.9 Hz, 1H), 6.49 (br. s., 1H), 5.21-5.12 (m, 1H), 4.63 (dd, J=6.4, 3.3 Hz, 1H), 2.69 (s, 3H), 2.68 (s, 3H), 1.47 (d, J=6.6 Hz, 3H), 1.44 (d, J=6.4 Hz, 3H). ¹⁹F NMR (376 MHz, CDCl₃) δ -89.78 (s, 3F), -132.17 (s, 1F).

Preparation of Substituted Quinoxalines

The substituted quinoxalines in the accompanying table were prepared according to the following general procedure, which is analogous to the procedure used to synthesize Example 389.

To a solution of THF (0.05 M) and the appropriate alcohol (100 equiv) was added sodium hydride (60% by wt., 10 equiv). After the bubbling subsided, a solution of Example 490 (1.0 equiv) in THF (0.05 M) was added dropwise. After 20 min of vigorous stirring at RT, the reaction mixture was quenched with a few drops of saturated $NH_4Cl$, diluted with EtOAc, filtered over Celite, concentrated and purified by Prep HPLC (Method D, unless otherwise indicated) to afford the desired example.

| Ex. No. | Structure | Quinoxaline | LCMS [M + H]$^+$ m/z | LCMS RT (Min) Method H | HPLC Prep Method D | NMR |
|---|---|---|---|---|---|---|
| 491 | 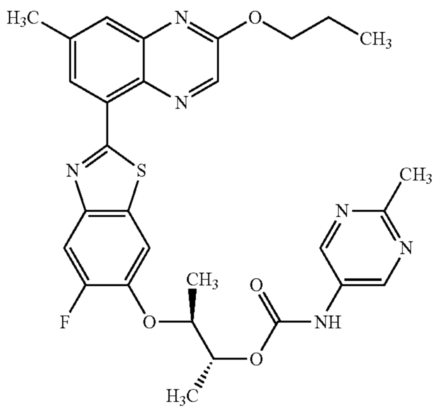 | 490 | 577.2 | 1.31 | 75-100% 15 min, 100% 10 min | $^1$H NMR (500 MHz, DMSO-d$_6$) δ 9.95 (br. s., 1H), 8.71 (br. s., 2H), 8.64 (s, 1H), 8.49 (s, 1H), 8.00 (d, J = 7.9 Hz, 1H), 7.91 (d, J = 11.3 Hz, 1H), 7.73 (s, 1H), 5.09 (d, J = 6.4 Hz, 1H), 4.78 (d, J = 4.3 Hz, 1H), 4.39 (t, J = 6.6 Hz, 2H), 2.58 (s, 3H), 2.50 (s, 3H-Buried under d-DMSO), 1.82 (sxt, J = 7.0 Hz, 2H), 1.38 (m, 6H), 1.02 (t, J = 7.3 Hz, 3H) |
| 492 | 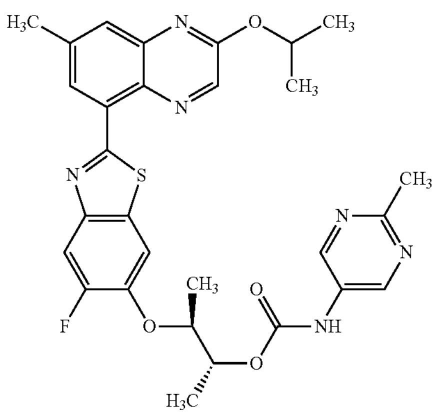 | 490 | 577.2 | 1.30 | 75-100% 15 min, 100% 10 min | $^1$H NMR (500 MHz, DMSO-d$_6$) δ 9.95 (br. s., 1H), 8.71 (br. s., 2H), 8.59 (s, 1H), 8.50 (s, 1H), 8.01 (d, J = 8.2 Hz, 1H), 7.91 (d, J = 11.6 Hz, 1H), 7.75 (s, 1H), 5.45 (dt, J = 12.2, 6.1 Hz, 1H), 5.09 (d, J = 6.4 Hz, 1H), 4.78 (d, J = 4.3 Hz, 1H), 2.59 (s, 3H), 2.50 (s, 3H-Buried under d-DMSO), 1.41 (d, J = 6.1 Hz, 6H), 1.38 (m, 6H) |
| 493 | 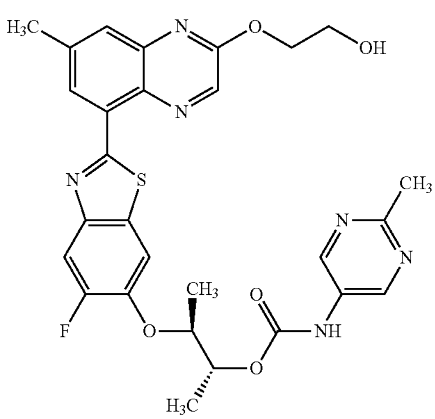 | 490 | 579.2 | 1.07 | 20-60% 20 min, 100% 10 min | $^1$H NMR (500 MHz, DMSO-d$_6$) δ 8.67 (br. s., 2H), 8.63 (s, 1H), 8.47 (s, 1H), 7.97 (d, J = 7.9 Hz, 1H), 7.88 (d, J = 11.3 Hz, 1H), 7.71 (s, 1H), 5.04 (d, J = 6.1 Hz, 1H), 4.73 (d, J = 4.3 Hz, 1H), 4.43 (d, J = 4.3 Hz, 2H), 3.77 (br. s., 2H), 2.55 (s, 3H), 2.50 (s, 3H-Buried under d-DMSO), 1.33 (m, 6H) |

Preparation of Alcohol Examples

The Alcohols in the accompanying table were prepared according to the following two general procedures.

Primary Alcohols: A solution of the appropriately substituted hetero-aryl ester (1.0 equiv) in THF (0.2 M) was cooled to −78° C. To this cooled reaction mixture was added DIBAl—H (1 M solution in toluene, 3.0 equiv) and the reaction mixture was to stirred at −78° C. for 1 hour. The reaction mixture was then quenched with saturated Rochelle's salt and allowed to stir for 2 h at room temperature. The resulting mixture was diluted with water and extracted with EtOAc. The organic layer was washed with brine, dried with magnesium sulfate, filtered over a pad of silica gel and concentrated. [Note: If crude NMR analysis of the isolated residue showed a substantial amount of the intermediate aldehyde remaining, then the material was resubjected to the DIBAl—H conditions described above in order to achieve complete reduction.] The crude material was purified by Prep HPLC (Method D, unless otherwise indicated) to afford the desired example.

Tertiary Alcohols: A solution of the appropriately substituted hetero-aryl ester (1.0 equiv) in THF (0.05 M) was cooled to −78° C. To this cooled reaction mixture was added methyl magnesium bromide (3.0 M solution in ether, 10 equiv). The reaction mixture was allowed to warm to room temperature and stirred for 30 minutes at ambient temperature. The reaction mixture was then quenched with saturated ammonium chloride, diluted with water and extracted with EtOAc. The organic layer was washed with brine, dried with magnesium sulfate, filtered over Celite and concentrated. The resulting residue was purified by Prep HPLC (Method D, unless otherwise indicated) to afford the desired example.

| Ex. No. | Structure | Ester | LCMS [M + H]+ m/z | LCMS RT (Min) Method H | HPLC Prep Method D | NMR |
|---|---|---|---|---|---|---|
| 494 | (structure) | I-87 | 584.1, 586.1 | 1.05 | 70-95% 20 min, 100% 7 min | $^1$H NMR (500 MHz, DMSO-$d_6$) δ 10.27 (s, 1H), 8.76 (s, 1H), 8.61 (s, 1H), 8.33 (d, J = 5.5 Hz, 1H), 8.05 (d, J = 7.3 Hz, 1H), 7.88 (s, 1H), 7.67 (s, 1H), 7.38 (br. s., 1H), 5.35 (br. s., 1H), 4.54 (d, J = 5.2 Hz, 2H), 4.49-4.41 (m, 1H), 4.39-4.32 (m, 1H), 4.14 (s, 3H), 2.70 (s, 3H), 1.49 (d, J = 6.1 Hz, 3H) |
| 495 | (structure) | I-83 | 550.2 | 0.99 | 40-80% 25 min, 100% 5 min | $^1$H NMR (500 MHz, DMSO-$d_6$) δ 10.93 (br. s., 1H), 8.72 (s, 1H), 8.55 (s, 1H), 8.43 (d, J = 6.1 Hz, 1H), 8.03-7.92 (m, 2H), 7.82 (s, 2H), 7.61 (d, J = 5.2 Hz, 1H), 5.32 (br. s., 1H), 4.66 (s, 2H), 4.40 (d, J = 9.2 Hz, 1H), 4.29 (dd, J = 10.8, 6.3 Hz, 1H), 4.07 (s, 3H), 3.90 (s, 1H), 2.62 (s, 3H), 1.45 (d, J = 6.4 Hz, 3H) |

-continued

| Ex. No. | Structure | Ester | LCMS [M + H]+ m/z | LCMS RT (Min) Method H | HPLC Prep Method D | NMR |
|---|---|---|---|---|---|---|
| 496 | (structure) | I-84 | 551.2 | 1.11 | 45-90% 25 min, 100% 10 min | ¹H NMR (500 MHz, DMSO-d₆) δ 8.91 (br. s., 2H), 8.77 (s, 1H), 8.60 (s, 1H), 8.09-7.98 (m, 2H), 7.87 (s, 1H), 5.34 (d, J = 3.1 Hz, 1H), 4.60 (d, J = 4.9 Hz, 2H), 4.49-4.40 (m, 1H), 4.34 (dd, J = 10.8, 6.0 Hz, 1H), 4.13 (s, 3H), 2.68 (s, 3H), 1.50 (d, J = 6.4 Hz, 3H) |
| 497 | (structure) | I-84 | 579.2 | 1.20 | 40-75% 20 min, 100% 5 min | ¹H NMR (500 MHz, DMSO-d₆) δ 8.85 (br. s., 2H), 8.66 (s, 1H), 8.50 (s, 1H), 7.95 (d, J = 8.5 Hz, 1H), 7.92 (d, J = 11.6 Hz, 1H), 7.76 (s, 1H), 5.33-5.21 (m, 1H), 4.36 (dd, J = 10.7, 2.7 Hz, 1H), 4.30-4.23 (m, 1H), 4.05 (s, 3H), 2.59 (s, 3H), 1.45 (s, 6H), 1.43 (d, J = 6.7 Hz, 3H) |
| 498 | (structure) | I-82 | 578.2 | 1.03 | 70-100% 20 min, 100% 10 min | ¹H NMR (500 MHz, DMSO-d₆) δ 9.90 (br. s., 1H), 8.68 (s, 1H), 8.55-8.49 (m, 2H), 7.94 (t, J = 11.0 Hz, 2H), 7.85 (d, J = 8.5 Hz, 1H), 7.77 (s, 1H), 7.56 (d, J = 8.5 Hz, 1H), 5.25 (d, J = 3.4 Hz, 1H), 4.36-4.31 (m, 1H), 4.29-4.22 (m, 1H), 4.05 (s, 3H), 2.59 (s, 3H), 1.41 (d, J = 6.4 Hz, 3H), 1.39 (s, 6H) |

| Ex. No. | Structure | Ester | LCMS [M + H]+ m/z | LCMS RT (Min) Method H | HPLC Prep Method D | NMR |
|---|---|---|---|---|---|---|
| 499 | (structure) | I-74 | 564.1 | 1.03 | 30-90% 25 min, 100% 5 min | ¹H NMR (500 MHz, DMSO-d₆) δ 9.83 (br. s., 1H), 8.68 (s, 1H), 8.53 (br. s., 2H), 8.01 (d, J = 8.2 Hz, 1H), 7.93 (d, J = 11.6 Hz, 1H), 7.84 (br. s., 1H), 7.79 (s, 1H), 7.36 (d, J = 8.5 Hz, 1H), 5.09 (dd, J = 6.6, 2.6 Hz, 1H), 4.77 (d, J = 3.7 Hz, 1H), 4.46 (s, 2H), 4.06 (s, 3H), 2.60 (s, 3H), 1.38 (m, 6H) |
| 500 | (structure) | I-74 | 592.1 | 1.14 | 45-95% 12 min, 100% 5 min | ¹H NMR (500 MHz, DMSO-d₆) δ 9.82 (br. s., 1H), 8.69 (s, 1H), 8.56-8.48 (m, 2H), 8.02 (d, J = 8.2 Hz, 1H), 7.94 (d, J = 11.6 Hz, 1H), 7.83 (br. s., 1H), 7.79 (s, 1H), 7.55 (d, J = 8.5 Hz, 1H), 5.11 (d, J = 5.5 Hz, 1H), 4.79 (d, J = 6.1 Hz, 1H), 4.07 (s, 3H), 2.61 (s, 3H), 1.43-1.37 (m, 12H) |
| 501 | (structure) | I-86 | 593.2 | 1.27 | 40-90% 15 min, 100% 5 min | ¹H NMR (500 MHz, DMSO-d₆) δ 10.06 (br. s., 1H), 8.83 (br. s., 2H), 8.69 (s, 1H), 8.54 (s, 1H), 8.03 (d, J = 7.9 Hz, 1H), 7.94 (d, J = 11.6 Hz, 1H), 7.80 (s, 1H), 5.13 (d, J = 4.3 Hz, 1H), 4.82 (d, J = 4.0 Hz, 1H), 4.07 (s, 3H), 2.61 (s, 3H), 1.44 (s, 6H), 1.41 (m, 6H) |

-continued

| Ex. No. | Structure | Ester | LCMS [M + H]+ m/z | LCMS RT (Min) Method H | HPLC Prep Method D | NMR |
|---|---|---|---|---|---|---|
| 502 | (structure) | I-86 | 565.0 | 1.23 | 30-70% 20 min, 100% 5 min | ¹H NMR (500 MHz, DMSO-d₆) δ 10.08 (br. s., 1H), 8.83 (br. s., 2H), 8.74 (s, 1H), 8.58 (s, 1H), 8.05 (d, J = 8.2 Hz, 1H), 7.97 (d, J = 11.6 Hz, 1H), 7.85 (s, 1H), 5.29 (t, J = 6.1 Hz, 1H), 5.13 (d, J = 5.8 Hz, 1H), 4.82 (br. s., 1H), 4.52 (d, J = 6.1 Hz, 2H), 4.09 (s, 3H), 3.47 (br. s., 2H), 2.64 (s, 3H), 1.40 (m, 6H) |

Preparation of Quinoxaline Examples

The quinoxalines in the accompanying table were prepared according to the following general procedure, which is analogous to the procedure described for Example 263. Thus, the appropriately substituted 2-bromobenzothiazole (1.0 equiv), PdCl₂(dppf)-CH₂Cl₂ adduct (0.08 equiv), and Intermediate I-9 (1.1 equiv) were solvated in a 3:1 mixture of toluene and ethanol (0.05 M). A 2.0 M solution of aqueous sodium carbonate (9 equiv) was then added, and the mixture was degassed by bubbling argon through the solution for 10 min. The vial was then sealed under an atmosphere of argon and heated to 105° C. thermally for 1 h. The resulting crude solution was diluted with EtOAc, filtered over Celite, concentrated, and purified by preparative HPLC (Method D, unless otherwise indicated) to yield the desired example.

| Ex. No. | Structure | Br—Bzt | LCMS [M + H]+ m/z | LCMS RT (Min) Method H | HPLC Prep Method D | NMR |
|---|---|---|---|---|---|---|
| 503 | (structure) | 260A | 341.9, 343.9 | 1.38 | 75-100% 25 min, 100% 4 min | 1H NMR (500 MHz, DMSO-d₆) δ 8.78 (s, 1H), 8.68 (s, 1H), 8.19 (d, J = 7.6 Hz, 1H), 7.92 (s, 1H), 7.68 (d, J = 7.6 Hz, 1H), 7.53-7.45 (m, 1H), 4.11 (s, 3H), 2.69 (s, 3H) |
| 504 | (structure) | 256A | 308.0 | 1.30 | 60-100% 18 min, 100% 10 min | 1H NMR (500 MHz, DMSO-d₆) δ 8.76 (s, 1H), 8.67 (s, 1H), 8.20 (d, J = 7.9 Hz, 1H), 8.14 (d, J = 8.2 Hz, 1H), 7.88 (s, 1H), 7.59 (t, J = 7.3 Hz, 1H), 7.53-7.47 (m, 1H), 4.10 (s, 3H), 2.66 (s, 3H) |

-continued

| Ex. No. | Structure | Br—Bzt | LCMS [M + H]+ m/z | LCMS RT (Min) Method H | HPLC Prep Method D | NMR |
|---|---|---|---|---|---|---|
| 505 | 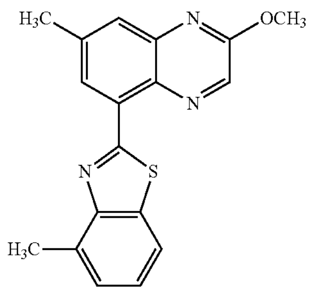 [SMILES: COc1cnc2c(-c3nc4c(C)cccc4s3)cc(C)cc2n1] | 261A | 322.0 | 1.40 | 80-100% 25 min, 100% 5 min | 1H NMR (500 MHz, DMSO-d6) δ 8.76 (s, 1H), 8.67 (s, 1H), 7.99 (d, J = 3.7 Hz, 1H), 7.88 (s, 1H), 7.42-7.34 (m, 2H), 4.10 (s, 3H), 2.81 (s, 3H), 2.67 (s, 3H) |
| 506 | 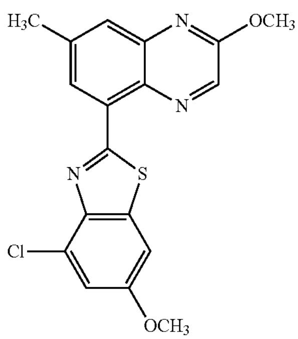 [SMILES: COc1cc(Cl)c2nc(-c3cc(C)cc4nc(OC)cnc34)sc2c1] | 93D | 371.9, 373.9 | 1.37 | 60-100% 18 min, 100% 15 min | 1H NMR (500 MHz, DMSO-d6) δ 8.75 (s, 1H), 8.59 (s, 1H), 7.86 (s, 1H), 7.75 (d, J = 2.4 Hz, 1H), 7.32 (d, J = 2.1 Hz, 1H), 4.10 (s, 3H), 3.90 (s, 3H), 2.66 (s, 3H) |
| 507 | 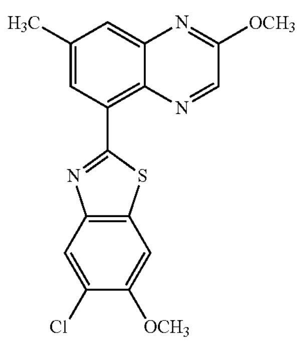 [SMILES: COc1cnc2c(-c3nc4cc(Cl)c(OC)cc4s3)cc(C)cc2n1] | 268A | 371.9, 373.9 | 1.37 | 60-100% 18 min, 100% 15 min | 1H NMR (500 MHz, DMSO-d6) δ 8.76 (s, 1H), 8.59 (s, 1H), 8.20 (s, 1H), 7.96 (s, 1H), 7.86 (br. s., 2H), 4.10 (s, 3H), 3.98 (s, 3H), 2.65 (s, 3H) |
| 509 | 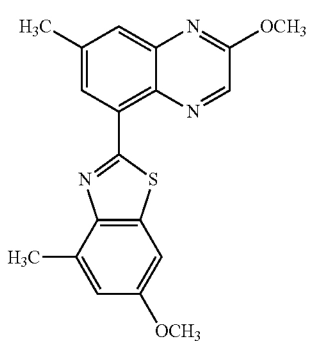 [SMILES: COc1cc(C)c2nc(-c3cc(C)cc4nc(OC)cnc34)sc2c1] | I-3 | 351.9 | 1.37 | 60-100% 18 min, 100% 15 min | 1H NMR (500 MHz, DMSO-d6) δ 8.74 (s, 1H), 8.60 (s, 1H), 7.83 (s, 1H), 7.53 (s, 1H), 7.01 (s, 1H), 4.10 (s, 3H), 3.86 (s, 3H), 2.76 (s, 3H), 2.66 (s, 3H) |

| Ex. No. | Structure | Br—Bzt | LCMS [M + H]+ m/z | LCMS RT (Min) Method H | HPLC Prep Method D | NMR |
|---|---|---|---|---|---|---|
| 510 | (structure) | 273A | 326.0 | 1.32 | 65-100% 25 min, 100% 4 min | 1H NMR (500 MHz, DMSO-d6) δ 8.78 (s, 1H), 8.68 (s, 1H), 8.03 (d, J = 7.9 Hz, 1H), 7.91 (s, 1H), 7.55-7.48 (m, 1H), 7.45-7.38 (m, 1H), 4.11 (s, 3H), 2.67 (s, 3H) |

Preparation of Quinoline Examples

The Quinolines in the accompanying table were prepared according to the following general procedure, which is analogous to the procedure described for Example 263. Thus, Intermediate I-88 (1.0 equiv), PdCl$_2$(dppf)-CH$_2$Cl$_2$ adduct (0.08 equiv), and the appropriately substituted quinoline (1.1 equiv) were solvated in a 3:1 mixture of toluene and ethanol (0.05 M). A 2.0 M solution of aqueous sodium carbonate (9 equiv) was added, and the mixture was degassed by bubbling argon through the solution for 10 min. The vial was then sealed then sealed under an atmosphere of argon and thermally heated to 105° C. 1 h. The crude solution was diluted with EtOAc, filtered over Celite, concentrated and purified by preparative HPLC (Method D, unless otherwise indicated) to yield the desired example.

| Ex. No. | Structure | Quin | LCMS [M + H]+ m/z | LCMS RT (Min) Method H | HPLC Prep Method D | NMR |
|---|---|---|---|---|---|---|
| 512 | (structure) | I-121 | 614.0, 616.1 | 1.14 | 40-90% 20 min, 100% 5 min | $^1$H NMR (500 MHz, DMSO-d$_6$) δ 9.76 (br. s., 1H), 8.58 (d, J = 2.4 Hz, 3H), 8.34 (d, J = 1.8 Hz, 1H), 7.91 (s, 1H), 7.83 (d, J = 7.9 Hz, 1H), 7.74 (d, J = 11.6 Hz, 1H), 7.66 (d, J = 2.1 Hz, 1H), 5.13-5.03 (m, 1H), 4.74 (d, J = 3.7 Hz, 1H), 4.21 (t, J = 4.6 Hz, 2H), 3.88 (s, 2H), 1.43-1.31 (m, 6H) |
| 513 | (structure) | I-126 | 628.0, 629.9 | 1.19 | 50-100% 25 min, 100% 5 min | $^1$H NMR (500 MHz, DMSO-d$_6$) δ 9.80 (br. s., 1H), 8.83 (d, J = 2.4 Hz, 1H), 8.61 (br. s., 3H), 8.16 (s, 1H), 8.04 (d, J = 8.2 Hz, 1H), 7.96 (d, J = 11.3 Hz, 1H), 7.90 (br. s., 1H), 5.10 (d, J = 6.4 Hz, 1H), 4.81 (d, J = 6.1 Hz, 1H), 4.32-4.17 (m, 4H), 3.68 (d, J = 4.6 Hz, 2H), 1.46 (t, J = 6.9 Hz, 3H), 1.43-1.32 (m, 6H) |

-continued

| Ex. No. | Structure | Quin | LCMS [M + H]+ m/z | LCMS RT (Min) Method H | HPLC Prep Method D | NMR |
|---|---|---|---|---|---|---|
| 514 | (structure) | I-124 | 594.1 | 1.03 | 40-100% 20 min, 100% 5 min | 1H NMR (500 MHz, DMSO-d6) δ 9.81 (br. s., 1H), 8.79 (d, J = 2.4 Hz, 1H), 8.60 (br. s., 3H), 8.02 (d, J = 8.2 Hz, 1H), 7.94 (d, J = 11.3 Hz, 1H), 7.87 (d, J = 6.1 Hz, 2H), 5.09 (d, J = 6.4 Hz, 1H), 4.80 (d, J = 3.4 Hz, 1H), 4.23 (d, J = 4.6 Hz, 2H), 3.99 (s, 3H), 3.69 (d, J = 4.3 Hz, 2H), 2.61 (s, 3H), 1.39 (d, J = 6.1 Hz, 6H) |
| 515 | (structure) | I-124 | 650., 652.0 | 1.14 | 50-90% 23 min, 100% 5 min | 1H NMR (500 MHz, DMSO-d6) δ 9.81 (br. s., 1H), 9.06 (d, J = 1.8 Hz, 1H), 8.77 (s, 1H), 8.61 (br. s., 2H), 8.35 (d, J = 5.2 Hz, 2H), 8.07 (d, J = 7.9 Hz, 1H), 7.98 (d, J = 11.6 Hz, 1H), 7.51 (t, J = 74.2 Hz, 1H), 5.11 (d, J = 6.1 Hz, 1H), 4.83 (d, J = 4.3 Hz, 1H), 4.24 (t, J = 4.9 Hz, 2H), 3.69 (d, J = 4.9 Hz, 2H), 1.45-1.36 (m, 6H) |

Example 516

1-((5-fluoro-2-(2-methoxy-7-methylquinoxalin-5-yl)benzo[d]thiazol-6-yl)oxy)-3-methoxypropan-2-yl pyridin-3-ylcarbamate (rac)

Intermediate 516A: 1-((5-fluoro-2-(2-methoxy-7-methylquinoxalin-5-yl)benzo[d]thiazol-6-yl)oxy)-3-methoxypropan-2-ol

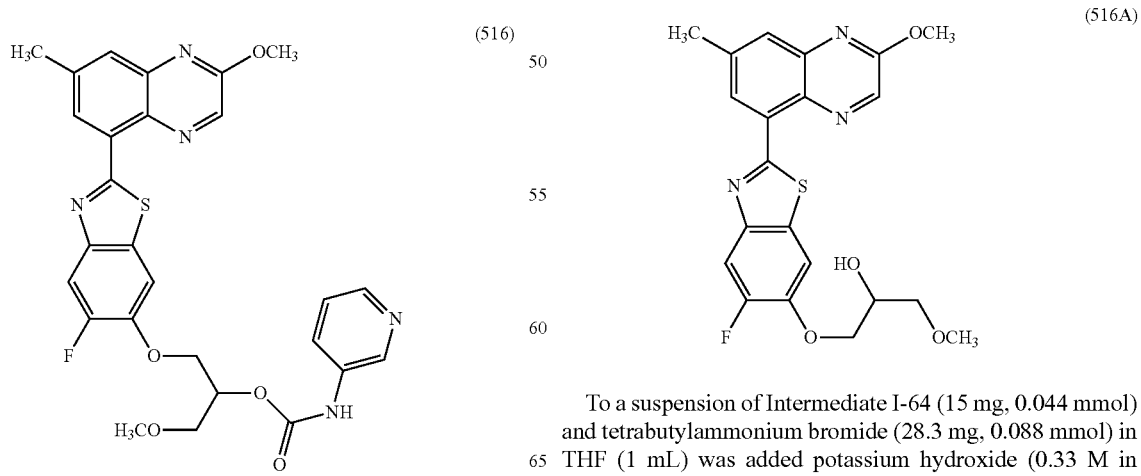

To a suspension of Intermediate I-64 (15 mg, 0.044 mmol) and tetrabutylammonium bromide (28.3 mg, 0.088 mmol) in THF (1 mL) was added potassium hydroxide (0.33 M in H2O) (0.200 mL, 0.066 mmol) followed by racemic 2-(methoxymethyl)oxirane (38.7 mg, 0.439 mmol). The mixture was then sealed and heated to 65° C. overnight. After 15 h, the reaction was quenched with saturated NaHCO$_3$ and diluted with EtOAc. The organic phase was washed with brine, dried over MgSO$_4$, filtered over Celite, concentrated and purified by ISCO (4 g, 0-60% EtOAc/Hexanes, 16 min. Product at 40%) to afford Intermediate 516A (11 mg, 0.026 mmol, 58.3% yield) as a yellow solid. LC-MS: Method H, RT=1.09 min, MS (ESI) m/z: 430.2 (M+H)$^+$. $^1$H NMR (400 MHz, CDCl$_3$) δ 8.59 (d, J=1.8 Hz, 1H), 8.53 (s, 1H), 7.80 (d, J=11.2 Hz, 1H), 7.74 (d, J=0.9 Hz, 1H), 7.48 (d, J=7.9 Hz, 1H), 4.26 (quin, J=5.2 Hz, 1H), 4.21-4.16 (m, 2H), 4.12 (s, 3H), 3.69-3.57 (m, 2H), 3.45 (s, 3H), 3.43 (d, J=6.6 Hz, 1H), 2.64 (s, 3H).

Example 516 (rac)

To a solution of Intermediate 516A (10 mg, 0.023 mmol) in THF (1 mL) was added 15% phosgene in toluene (0.164 mL, 0.233 mmol) at room temperature. The reaction mixture was allowed to stir overnight. After 16 h, the reaction mixture was concentrated to afford the desired chloroformate intermediate as a crude yellow residue. This crude material was retaken in THF (1 mL) and added dropwise to a pre-mixed solution of pyridin-3-amine (4.38 mg, 0.047 mmol) and pyridine (0.019 mL, 0.232 mmol) After 5 min of stirring, the reaction mixture was concentrated and purified by prep HPLC (Method C, 20-60% over 20 min, hold 100% for 5 min) to afford Example 516 (10.5 mg, 0.023 mmol, 78% yield) as a yellow solid. LC-MS: Method H, RT=0.94 min, MS (ESI) m/z: 550.2 (M+H)$^+$. $^1$H NMR (500 MHz, DMSO-d$_6$) δ 10.41 (br. s., 1H), 8.81 (br. s., 1H), 8.67 (s, 1H), 8.51 (s, 1H), 8.37 (d, J=4.4 Hz, 1H), 8.12 (d, J=7.9 Hz, 1H), 7.97 (d, J=8.2 Hz, 1H), 7.93 (d, J=11.5 Hz, 1H), 7.77 (s, 1H), 7.60 (dd, J=8.4, 5.0 Hz, 1H), 5.37 (d, J=4.6 Hz, 1H), 4.50-4.43 (m, 1H), 4.43-4.36 (m, 1H), 4.07 (s, 3H), 3.82-3.72 (m, 2H), 3.37 (s, 3H), 2.61 (s, 3H).

Example 517

(R)-1-((5-fluoro-2-(2-methoxy-7-methylquinoxalin-5-yl)benzo[d]thiazol-6-yl)oxy)butan-2-yl pyridin-3-ylcarbamate

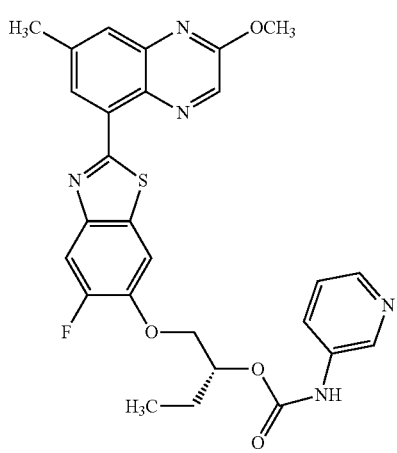

(517)

Intermediate 517A: (R)-1-((5-fluoro-2-(2-methoxy-7-methylquinoxalin-5-yl)benzo[d]thiazol-6-yl)oxy)butan-2-ol

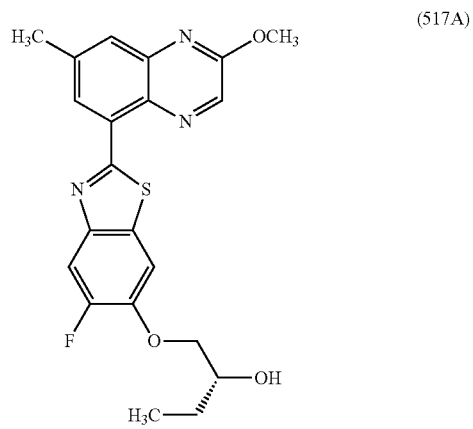 [SMILES: CC[C@@H](O)COc1cc2sc(-c3cc(C)cc4nc(OC)cnc34)nc2cc1F]

(517A)

This intermediate was prepared in a manner analogous to Intermediate 516A. Thus, Intermediate I-64 was reacted with (R)-2-ethyloxirane to afford Intermediate 517A (77% yield) as a yellow solid. LC-MS: Method H, RT=1.14 min, MS (ESI) m/z: 414.2 (M+H)$^+$. $^1$H NMR (400 MHz, CDCl$_3$) δ 8.59 (d, J=2.0 Hz, 1H), 8.53 (s, 1H), 7.81 (d, J=11.4 Hz, 1H), 7.74 (s, 1H), 7.45 (d, J=7.9 Hz, 1H), 4.16-4.09 (m, 4H), 4.08-3.95 (m, 2H), 2.64 (s, 3H), 2.44 (d, J=3.7 Hz, 1H), 1.74-1.63 (m, 2H), 1.07 (t, J=7.5 Hz, 3H).

Example 517

This intermediate was prepared in a manner analogous to Example 516. Thus, Intermediate 517A was reacted with phosgene followed by pyridin-3-amine. The crude reaction residue was purified by Prep HPLC (Method D, 55-100% over 20 min, hold 100% for 5 min) to afford Example 517 (68% yield) as a yellow solid. LC-MS: Method H, RT=0.97 min, MS (ESI) m/z: 534.2 (M+H)$^+$. $^1$H NMR (400 MHz, CDCl$_3$) δ 8.59 (d, J=2.0 Hz, 1H), 8.53 (s, 1H), 7.81 (d, J=11.4 Hz, 1H), 7.74 (s, 1H), 7.45 (d, J=7.9 Hz, 1H), 4.16-4.09 (m, 4H), 4.08-3.95 (m, 2H), 2.64 (s, 3H), 2.44 (d, J=3.7 Hz, 1H), 1.74-1.63 (m, 2H), 1.07 (t, J=7.5 Hz, 3H).

Example 518

4-((4-chloro-5-fluoro-2-(2-methoxy-7-methylquinoxalin-5-yl)benzo[d]thiazol-6-yl)oxy)-N-(pyridin-3-yl)butanamide

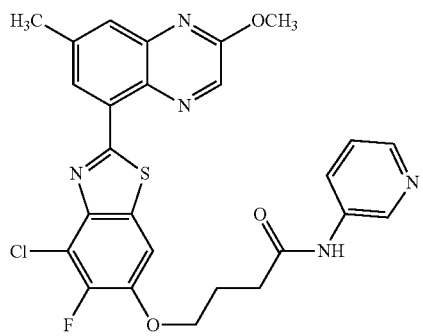

(518)

Intermediate 518A: tert-butyl 4-((4-chloro-5-fluoro-2-(2-methoxy-7-methylquinoxalin-5-yl)benzo[d]thiazol-6-yl)oxy)butanoate

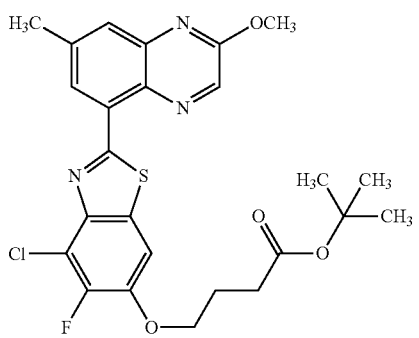

(518A)

To a solution of Intermediate I-65 (100 mg, 0.266 mmol) in DMF (1330 µl) was added tert-butyl 4-bromobutanoate (89 mg, 0.399 mmol) followed by potassium carbonate (73.6 mg, 0.532 mmol). The reaction vessel was sealed and the red colored solution was heated to 65° C. After 2 h, the reaction mixture was cooled to room temperature and quenched with a few drops of AcOH. The resulting mixture was diluted with EtOAc, filtered over Celite and concentrate in vacuo to afford crude Intermediate 518A, which was telescoped into the next reaction without purification. LC-MS: Method H, RT=1.43 min, MS (ESI) m/z: [Not observed] (M+H)⁺. $^1$H NMR (400 MHz, CDCl$_3$) δ 8.66 (s, 1H), 8.44 (s, 1H), 7.69 (br. s., 1H), 7.29 (d, J=7.5 Hz, 1H), 4.19-4.04 (m, 5H), 2.63 (s, 3H), 2.58-2.44 (m, 2H), 2.15 (dq, J=12.8, 6.4 Hz, 2H), 1.45 (s, 9H).

Intermediate 518B: 4-((4-chloro-5-fluoro-2-(2-methoxy-7-methylquinoxalin-5-yl) benzo[d]thiazol-6-yl)oxy)butanoic acid

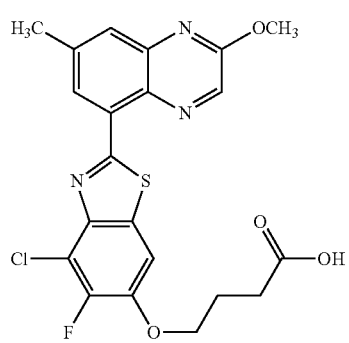

(518B)

To a solution of crude Intermediate 518A (138 mg, 0.266 mmol) in DCM (2664 µl) was added TFA (2664 µl). The resulting solution immediately became dark red in color. After stirring at room temperature for 30 min, the reaction mixture was concentrated in vacuo to afford crude Intermediate 518B, which was telescoped into the next reaction without purification. LC-MS: Method H, RT=1.25 min, MS (ESI) m/z: 462.1, 464.1 (M+H)⁺. $^1$H NMR (400 MHz, CDCl$_3$) δ 8.69 (d, J=1.8 Hz, 1H), 8.49 (s, 1H), 7.75-7.70 (m, 1H), 7.33 (d, J=7.3 Hz, 1H), 4.16-4.10 (m, 5H), 2.65 (s, 3H), 2.47 (t, J=7.4 Hz, 2H), 2.04-1.93 (m, 2H).

Example 518

To a brown suspension crude Intermediate 518B (15 mg, 0.032 mmol) in DMF (1 mL) was added N-ethyl-N-isopropylpropan-2-amine (0.034 mL, 0.195 mmol) followed by 2,4,6-tripropyl-1,3,5,2,4,6-trioxatriphosphinane 2,4,6-trioxide (50% in DMF) (0.058 mL, 0.097 mmol). The reaction mixture was stirred at room temperature for 2, then pyridin-3-amine (9.17 mg, 0.097 mmol) was added. After an additional 10 min of stirring, the reaction mixture was concentrated and purified by prep HPLC (Method D, 50-100% over 15 min, hold 100% for 7 min) to afford Example 518 (3.3 mg, 0.006 mmol, 18% yield) as a yellow solid over the three step sequence. LC-MS: Method H, RT=1.06 min, MS (ESI) m/z: 538.2, 540.2 (M+H)⁺. $^1$H NMR (500 MHz, DMSO-d$_6$) δ 10.27 (s, 1H), 8.79 (br. s., 1H), 8.74 (s, 1H), 8.59 (s, 1H), 8.27 (d, J=4.3 Hz, 1H), 8.08 (d, J=7.9 Hz, 1H), 7.99 (d, J=7.3 Hz, 1H), 7.85 (s, 1H), 7.39 (dd, J=8.2, 4.6 Hz, 1H), 4.26 (t, J=6.1 Hz, 2H), 4.08 (s, 3H), 2.65 (s, 3H), 2.60 (t, J=7.3 Hz, 2H), 2.15 (t, J=6.6 Hz, 2H).

Example 519

1-(2-((4-chloro-5-fluoro-2-(2-methoxy-7-methylquinoxalin-5-yl)benzo[d]thiazol-6-yl)oxy)ethyl)-3-(pyridin-3-yl)urea

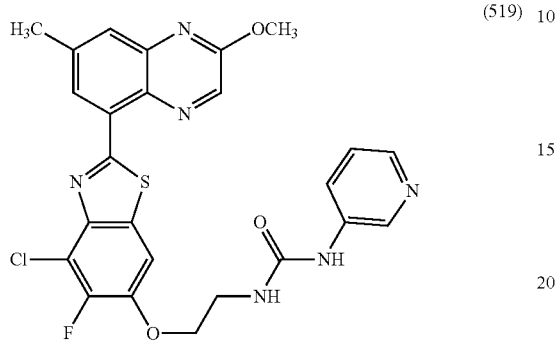

(519)

Intermediate 519A: tert-butyl (2-((4-chloro-5-fluoro-2-(2-methoxy-7-methylquinoxalin-5-yl)benzo[d]thiazol-6-yl)oxy)ethyl)carbamate

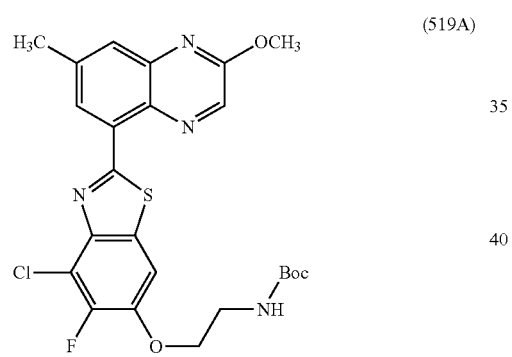

(519A)

To a dark red solution of Intermediate I-65 (85 mg, 0.226 mmol) and cesium carbonate (221 mg, 0.679 mmol) in DMF (2262 μl) was added tert-butyl (2-bromoethyl)carbamate (76 mg, 0.339 mmol) as a cold solid from the freezer [Note: did not allow reagent to melt]. The reaction mixture was sealed and heated to 65° C. After 1 h of heating, the reaction was quenched with 0.3 mL AcOH, diluted with EtOAc, filtered over Celite and concentrated to a dark yellow solid. The crude material was purified by ISCO (12 g, 0-20% EtOAc/DCM, 16 min.) to afford Intermediate 519A (81 mg, 0.156 mmol, 69.0% yield) as a yellow solid. LC-MS: Method H, RT=1.31 min, MS (ESI) m/z: 519.2, 521.2 (M+H)$^+$. $^1$H NMR (400 MHz, CDCl$_3$) δ 8.65 (d, J=1.8 Hz, 1H), 8.43 (s, 1H), 7.69 (dd, J=2.0, 0.9 Hz, 1H), 7.26 (d, J=6.4 Hz, 1H), 5.17 (br. s., 1H), 4.17-4.15 (m, 2H), 4.10 (s, 3H), 3.63 (d, J=5.3 Hz, 2H), 2.63 (s, 3H), 1.48 (s, 9H).

Intermediate 519B: 2-((4-chloro-5-fluoro-2-(2-methoxy-7-methylquinoxalin-5-yl)benzo[d]thiazol-6-yl)oxy)ethanamine, TFA

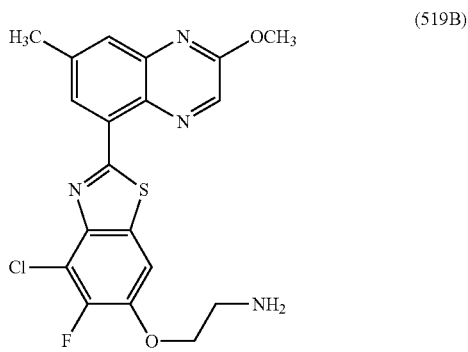 [SMILES: COc1cnc2c(-c3nc4c(Cl)c(F)c(OCCN)cc4s3)cc(C)cc2n1]

(519B)

To a suspension of Intermediate 519A (40 mg, 0.077 mmol) in DCM (2 mL) was added TFA (1.0 mL). The resulting solution immediately became bright red in color. After stirring at room temperature for 15 min, the reaction mixture was concentrated in vacuo to afford crude Intermediate 519B (41.1 mg, 0.077 mmol, 100% yield). This material was telescoped into subsequent reactions without further purification. LC-MS: Method H, RT=0.95 min, MS (ESI) m/z: 419.4, 421.4 (M+H)$^+$.

Example 519

To a solution of Intermediate 519B (20 mg, 0.038 mmol) in THF (2 mL) was added diisopropylethylamine (0.13 mL, 0.75 mmol) followed by 3-isocyanatopyridine (13.52 mg, 0.113 mmol) at room temperature. After 15 h, the reaction mixture was concentrated and purified by prep HPLC (Method D, 45-95% over 15 min, hold 100% for 5 min) to afford Example 519 (1.2 mg, 0.002 mmol, 6% yield) as a yellow solid over the two step sequence. LC-MS: Method H, RT=0.98 min, MS (ESI) m/z: 539.1, 541.1 (M+H)$^+$. $^1$H NMR (500 MHz, DMSO-d$_6$) δ 8.84 (s, 1H), 8.71 (s, 1H), 8.56 (s, 1H), 8.54 (s, 1H), 8.11 (d, J=4.6 Hz, 1H), 7.98 (d, J=7.6 Hz, 1H), 7.88 (d, J=8.5 Hz, 1H), 7.83 (s, 1H), 7.26 (dd, J=8.4, 4.7 Hz, 1H), 6.64-6.56 (m, 1H), 4.24 (t, J=5.0 Hz, 2H), 4.07 (s, 3H), 3.59 (d, J=5.5 Hz, 2H), 2.63 (s, 3H).

Example 520

1-(2-((4-chloro-5-fluoro-2-(2-methoxy-7-methylquinoxalin-5-yl)benzo[d]thiazol-6-yl)oxy)ethyl)-1-methyl-3-(2-methylpyrimidin-5-yl)urea

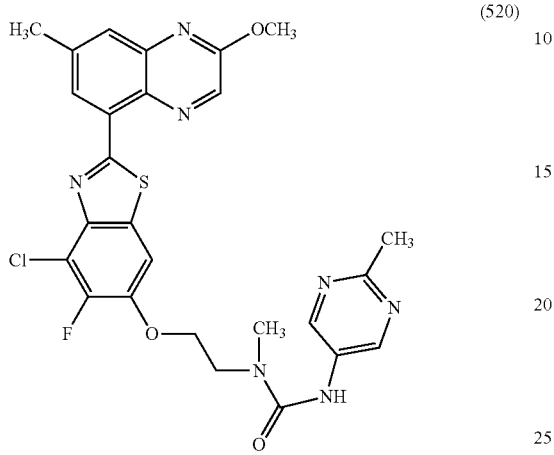

(520)

Intermediate 520A: tert-butyl (2-((4-chloro-5-fluoro-2-(2-methoxy-7-methylquinoxalin-5-yl)benzo[d]thiazol-6-yl)oxy)ethyl)(methyl)carbamate (520A)

To a suspension of Intermediate 519A (43 mg, 0.083 mmol) in THF (1 mL) was added sodium hydride (9.94 mg, 0.249 mmol). The bright red solution was stirred at room temperature for 5 min before methyl iodide (2.0 M in MTBE) (0.207 mL, 0.414 mmol) was added. The reaction was then allowed to stir overnight before being quenched with AcOH, concentrated, and loaded directly onto an ISCO cartridge for purification (12 g, 0-50% EtOAc/Hexanes, 16 min. Product at 25%) to afford Intermediate 520A (24 mg, 0.045 mmol, 54.3% yield) as a yellow solid. LC-MS: Method H, RT=1.37 min, MS (ESI) m/z: 533.1, 535.1 (M+H)$^+$. $^1$H NMR (400 MHz, CDCl$_3$) δ 8.73 (d, J=1.8 Hz, 1H), 8.54 (s, 1H), 7.77 (d, J=0.7 Hz, 1H), 7.37 (d, J=7.0 Hz, 1H), 4.25 (d, J=17.6 Hz, 2H), 4.13 (s, 3H), 3.74-3.66 (m, 2H), 3.05 (s, 3H), 2.66 (s, 3H), 1.48 (s, 9H).

Intermediate 520B: 2-((4-chloro-5-fluoro-2-(2-methoxy-7-methylquinoxalin-5-yl)benzo[d]thiazol-6-yl)oxy)-N-methylethanamine, TFA

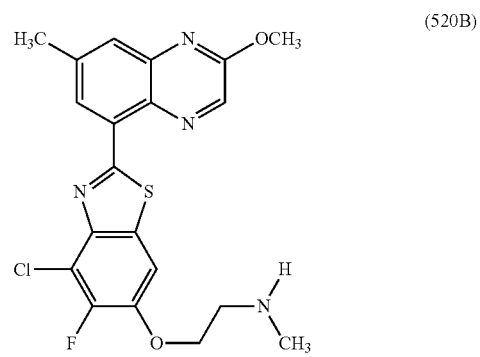 [SMILES: CNCCOc1cc2sc(-c3cc(C)cc4nc(OC)cnc34)nc2c(Cl)c1F]

(520B)

To a suspension of Intermediate 520A (24 mg, 0.045 mmol) in DCM (2 mL) was added TFA (1.0 mL). The resulting solution immediately became bright red in color. After stirring for 20 min at room temperature, the reaction mixture was concentrated in vacuo to afford crude Intermediate 520B (24.63 mg, 0.045 mmol, 100% yield). This material was telescoped into the subsequent reactions without further purification. LC-MS: Method H, RT=0.92 min, MS (ESI) m/z: 433.0, 435.0 (M+H)$^+$.

Example 520

To a mixture of crude Intermediate 520B (12 mg, 0.022 mmol) and DIPEA (0.057 mL, 0.329 mmol) in THF (1 mL) was added 15% phosgene in toluene (0.108 mL, 0.154 mmol) at room temperature. The solution immediately became smoky and deposited white salts. After 10 min, 2-methylpyrimidin-5-amine (7.18 mg, 0.066 mmol) and silver nitrate (18.64 mg, 0.110 mmol) were added. The reaction mixture was then sealed and heated to 65° C. for 1 h. The resulting reaction mixture was cooled to room temperature, diluted with EtOAc, filtered over Celite, concentrated and purified by prep HPLC (Method D, 40-75% over 25 min, hold 100% for 7 min) to afford Example 520 (1.1 mg, 0.002 mmol, 8% yield) as a yellow solid over the two step sequence. LC-MS: Method H, RT=1.15 min, MS (ESI) m/z: 568.3, 570.2 (M+H)$^+$. $^1$H NMR (500 MHz, DMSO-d$_6$) δ 8.76 (s, 2H), 8.69 (s, 1H), 8.55 (s, 1H), 7.95 (d, J=7.3 Hz, 1H), 7.81 (s, 1H), 4.34 (br. s., 2H), 4.07 (s, 3H), 3.81 (br. s., 2H), 3.11 (s, 3H), 2.63 (s, 3H), 2.52 (s, 3H).

Example 521

(2R,3S)-3-((5-fluoro-2-(2-methoxy-7-methylquinoxalin-5-yl)benzo[d]thiazol-6-yl)oxy) butan-2-yl (6-(morpholinomethyl)pyridin-3-yl)carbamate

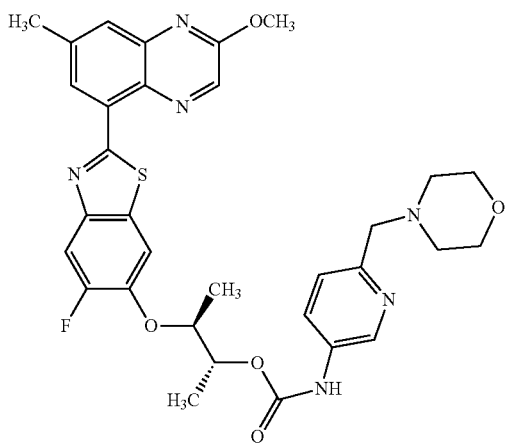

(521)

To a solution of Example 426 (9 mg, 0.014 mmol) in THF (1 mL) was added diacetoxyzinc (5.11 mg, 0.028 mmol) followed by triethoxysilane (0.026 mL, 0.139 mmol). The resulting mixture was sealed and heated to 65° C. overnight. The resulting reaction mixture was diluted with EtOAc, washed with brine, dried over MgSO$_4$, filtered and purified by prep HPLC (Method D, 45-100% over 20 min, hold 100% for 6 min) to afford Example 521 (1.4 mg, 0.002 mmol, 14% yield) as a yellow solid. LC-MS: Method H, RT=1.07 min, MS (ESI) m/z: 633.2 (M+H)$^+$. $^1$H NMR (500 MHz, DMSO-d$_6$) δ 9.94-9.68 (m, 1H), 8.67 (s, 1H), 8.51 (s, 2H), 7.98 (d, J=8.2 Hz, 1H), 7.90 (d, J=11.6 Hz, 1H), 7.78 (s, 2H), 7.29 (br. s., 1H), 5.04 (d, J=5.8 Hz, 1H), 4.73 (br. s., 1H), 4.01 (s, 3H), 3.52 (br. s., 2H) [note: morpholine protons appear to under-integrate], 2.56 (s, 3H), 1.32 (m, 6H).

Example 522

(2R,3S)-3-((2-(2-(dimethylamino)-7-methylquinoxalin-5-yl)-5-fluorobenzo[d]thiazol-6-yl)oxy)butan-2-yl (2-methylpyrimidin-5-yl)carbamate

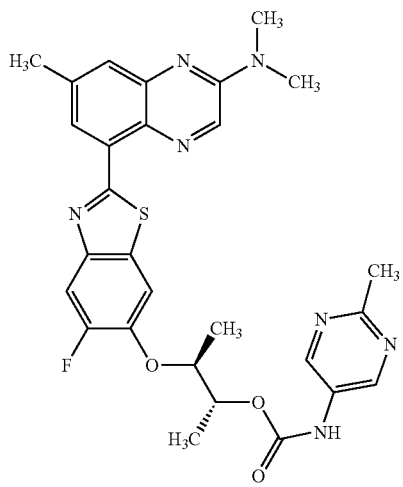

(522)

To a vial containing Intermediate I-73 (10 mg, 0.017 mmol) was added dimethylamine (2 M in THF) (1 mL, 2.000 mmol) followed by 2-propanol (1 mL). The vial was sealed and heated to 65° C. After 6 h of heating the reaction mixture was concentrated, and purified by prep HPLC (Method D, 40-80% over 20 min, hold 100% for 5 min) to afford Example 522 (7.8 mg, 0.014 mmol, 80% yield) as a yellow solid. LC-MS: Method H, RT=1.07 min, MS (ESI) m/z: 562.2 (M+H)$^+$. $^1$H NMR (500 MHz, DMSO-d$_6$) δ 9.98 (br. s., 1H), 8.76 (s, 1H), 8.74 (br. s., 2H), 8.30 (s, 1H), 8.01 (d, J=8.2 Hz, 1H), 7.94 (d, J=11.3 Hz, 1H), 7.57 (s, 1H), 5.11 (d, J=6.1 Hz, 1H), 4.83 (d, J=6.4 Hz, 1H), 3.27 (br. s., 6H), 2.55 (br. s., 3H), 1.40 (br. s., 6H).

Example 523

5-(((((2R,3S)-3-((5-fluoro-2-(2-methoxy-7-methylquinoxalin-5-yl)benzo[d]thiazol-6-yl)oxy)butan-2-yl)oxy)carbonyl)amino)picolinic acid, TFA

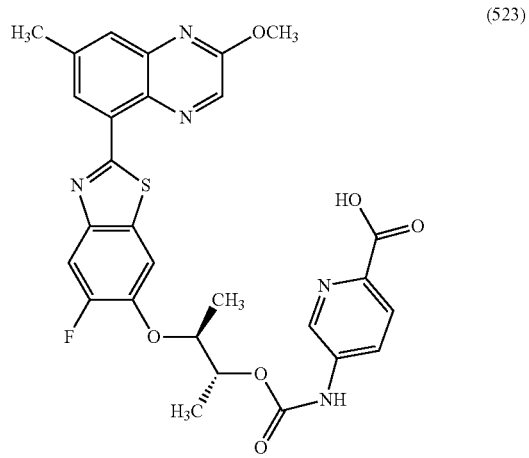 [SMILES: COc1cnc2c(-c3nc4cc(F)c(O[C@@H](C)[C@@H](C)OC(=O)Nc5ccc(C(=O)O)nc5)cc4s3)cc(C)cc2n1]

(523)

To a solution of Intermediate I-74 (8.5 mg, 0.015 mmol) in THF (1 mL) was added lithium hydroxide (1 M) (0.2 mL, 0.200 mmol). The reaction mixture was sealed and heated to 65° C. After 1 h, the reaction mixture was quenched with 1 M HCl, diluted with EtOAc, extracted, concentrated, and purified by prep HPLC (Method C, 30-100% over 20 min, hold 100% for 5 min) to afford Example 523 (4.6 mg, 0.008, 54% yield) as a yellow solid. LC-MS: Method H, RT=1.17 min, MS (ESI) m/z: 578.1 (M+H)$^+$. $^1$H NMR (500 MHz, DMSO-d$_6$) δ 8.77 (br. s., 1H), 8.72 (s, 1H), 8.57 (s, 1H), 8.11-8.01 (m, 3H), 7.98 (d, J=11.6 Hz, 1H), 7.84 (s, 1H), 5.20 (d, J=6.4 Hz, 1H), 4.87 (d, J=4.3 Hz, 1H), 4.13 (s, 3H), 2.66 (s, 3H), 1.47 (t, J=6.3 Hz, 6H).

Example 524

(2R,3S)-3-((5-fluoro-2-(2-methoxy-7-methylquinoxalin-5-yl)benzo[d]thiazol-6-yl)oxy)butan-2-yl carbamate

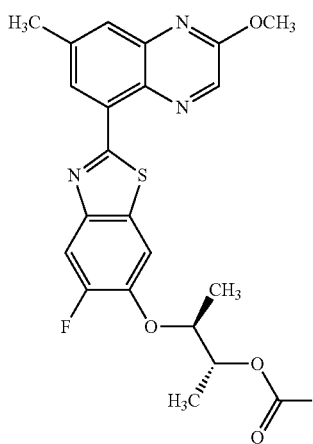

(524)

To a solution Intermediate I-72 (85 mg, 0.206 mmol) in THF (4112 µl) was added 15% phosgene in toluene (1450 µl, 2.056 mmol). The resulting slurry was allowed to stir overnight before being concentrated down to a crude yellow residue. This chloroformate intermediate was retaken in THF (1 mL) and added dropwise to a separate vial containing a solution of ammonia (0.5 M in dioxane) (0.420 mL, 0.210 mmol). After 5 min of stirring at RT, the reaction mixture was concentrated and purified by prep HPLC (Method D, 45-80% over 30 min, hold 100% for 8 min) to afford Example 524 (5.7 mg, 0.012 mmol, 59% yield) as a yellow solid. LC-MS: Method H, RT=1.10 min, MS (ESI) m/z: 457.3 (M+H)+. $^1$H NMR (500 MHz, DMSO-$d_6$) δ 8.74 (s, 1H), 8.59 (s, 1H), 8.02 (d, J=7.9 Hz, 1H), 7.98 (d, J=11.3 Hz, 1H), 7.85 (s, 1H), 6.63 (br. s., 2H), 4.95 (dd, J=6.3, 3.2 Hz, 1H), 4.71 (dd, J=6.1, 3.4 Hz, 1H), 4.13 (s, 3H), 2.67 (s, 3H), 1.40 (d, J=6.4 Hz, 3H), 1.34 (d, J=6.4 Hz, 3H).

Example 525

1-((5-fluoro-2-(2-methoxy-7-methylquinoxalin-5-yl)benzo[d]thiazol-6-yl)oxy)-3-isobutoxypropan-2-yl (2-methylpyrimidin-5-yl)carbamate (rac)

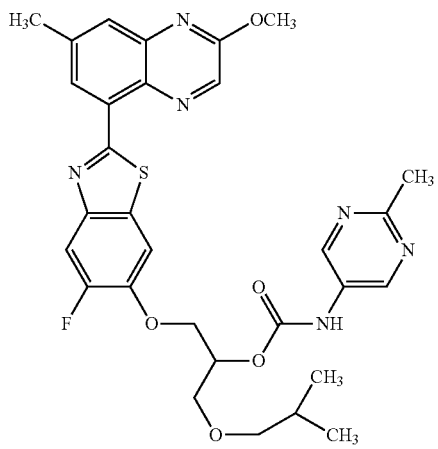

(525)

This example was prepared in a manner analogous to Example 379 above. Thus, reaction of Intermediate 379A with 2-methylpyrimidin-5-amine afforded Example 525 (rac) in 76% yield following purification by preparative HPLC (Method C, 60-95% over 25 min, hold at 100% for 10 min). LC-MS: Method H, RT=1.24 min, MS (ESI) m/z: 607.1 (M+H)+. $^1$H NMR (500 MHz, DMSO-$d_6$) δ 10.17 (br. s., 1H), 8.76 (br. s., 2H), 8.72 (s, 1H), 8.56 (s, 1H), 8.00 (d, J=8.2 Hz, 1H), 7.97 (d, J=11.6 Hz, 1H), 7.82 (s, 1H), 5.33 (br. s., 1H), 4.50-4.43 (m, 1H), 4.43-4.36 (m, 1H), 4.09 (s, 3H), 3.78 (d, J=5.2 Hz, 2H), 3.42-3.20 (m, 2H), 2.63 (s, 3H), 1.82 (dt, J=13.4, 6.7 Hz, 1H), 0.86 (d, J=6.4 Hz, 6H).

Example 526

(2R,3S)-3-((2-(2-ethoxy-7-methylquinoxalin-5-yl)-5-fluorobenzo[d]thiazol-6-yl)oxy)butan-2-yl (6-(2-hydroxyethyl)pyridin-3-yl)carbamate

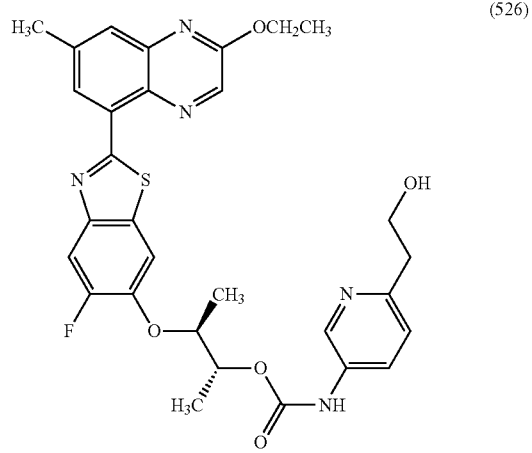 [SMILES: CCOc1cnc2c(-c3nc4cc(F)c(O[C@@H](C)[C@@H](C)OC(=O)Nc5ccc(CCO)nc5)cc4s3)cc(C)cc2n1]

(526)

To a solution of Intermediate I-80 (300 mg, 0.702 mmol) in THF (1.4 mL, 0.05 M) was added 15% phosgene in toluene (4949 µl, 7.02 mmol). The resulting slurry was allowed to stir overnight. After 16 h, the reaction mixture was concentrated down to a yellow residue. This crude chloroformate intermediate was retaken in THF (2 mL) and slowly added to a premixed solution of Intermediate I-109 (33.5 mg, 0.133 mmol) and pyridine (0.083 mL, 1.021 mmol) in THF (2 mL). After 5 min of stirring at room temperature, the reaction mixture was concentrated to remove excess pyridine and then retaken in THF (2 mL). To this mixture was added TBAF (1 M in THF) (0.306 mL, 0.306 mmol), and the resulting solution was stirred at room temperature for 6 h. The resulting mixture was concentrated and purified by prep HPLC (Method D, 50-100% over 20 min, hold 100% for 5 min) to afford Example 526 (31.4 mg, 0.051 mmol, 50% yield) as a yellow solid. LC-MS: Method H, RT=1.06 min, MS (ESI) m/z: 592.2 (M+H)+. $^1$H NMR (500 MHz, DMSO-$d_6$) δ 9.81 (br. s., 1H), 8.73 (s, 1H), 8.60 (s, 1H), 8.58 (br. s., 1H), 8.09 (d, J=8.2 Hz, 1H), 8.00 (d, J=11.6 Hz, 1H), 7.87-7.78 (m, 1H), 7.23 (d, J=8.5 Hz, 1H), 5.16 (d, J=6.4 Hz, 1H), 4.83 (d, J=4.0 Hz, 1H), 4.67 (t, J=5.0 Hz, 1H), 4.58 (q, J=7.0 Hz, 2H), 3.74 (q, J=6.2 Hz, 2H), 2.85 (t, J=6.9 Hz, 2H), 2.67 (s, 3H), 1.50 (t, J=7.0 Hz, 3H), 1.45 (t, J=7.5 Hz, 6H).

Example 527

(2R,3S)-3-((2-(2-ethoxy-7-methylquinoxalin-5-yl)-5-fluorobenzo[d]thiazol-6-yl)oxy)butan-2-yl (6-((2-hydroxy-2-methylpropyl)carbamoyl)pyridin-3-yl) carbamate

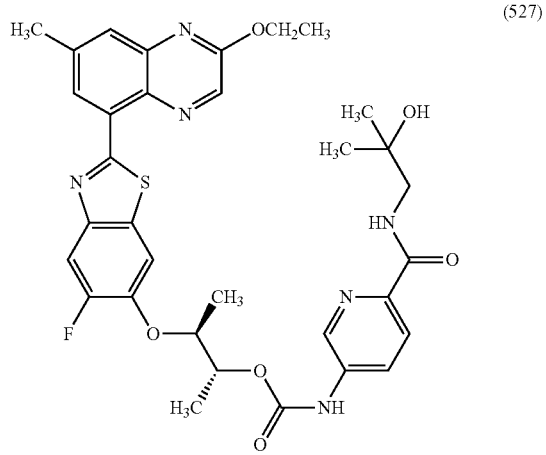 [SMILES: CCOc1cnc2c(-c3nc4cc(F)c(O[C@@H](C)[C@@H](C)OC(=O)Nc5ccc(C(=O)NCC(C)(C)O)nc5)cc4s3)cc(C)cc2n1]

(527)

The following example was prepared in a manner analogous to the general hindered amide procedure described in the table above. Thus, Intermediate I-89 was reacted with 1-amino-2-methylpropan-2-ol (100 equiv) and magnesium chloride (10 equiv) to afford Example 527 in 36% yield following purification by preparative HPLC (Method D, 45-90% over 20 min, hold at 100% for 8 min). LC-MS: Method H, RT=1.27 min, MS (ESI) m/z: 663.2 (M+H)$^+$. $^1$H NMR (500 MHz, DMSO-d$_6$) δ 10.23 (br. s., 1H), 8.73 (s, 1H), 8.71 (s, 1H), 8.59 (s, 1H), 8.35 (t, J=6.1 Hz, 1H), 8.12-8.05 (m, 2H), 8.04-7.98 (m, 2H), 7.84 (s, 1H), 5.19 (dd, J=6.6, 2.6 Hz, 1H), 4.92-4.85 (m, 1H), 4.81 (s, 1H), 4.59 (q, J=7.0 Hz, 2H), 3.33-3.27 (m, 2H), 2.68 (s, 3H), 1.50 (t, J=7.2 Hz, 3H), 1.47 (t, J=5.8 Hz, 6H), 1.15 (s, 6H).

Example 528

(2R,3S)-3-((5-fluoro-2-(2-methoxy-7-methylquinoxalin-5-yl)benzo[d]thiazol-6-yl)oxy)butan-2-yl (2-(hydroxymethyl)pyrimidin-5-yl)carbamate

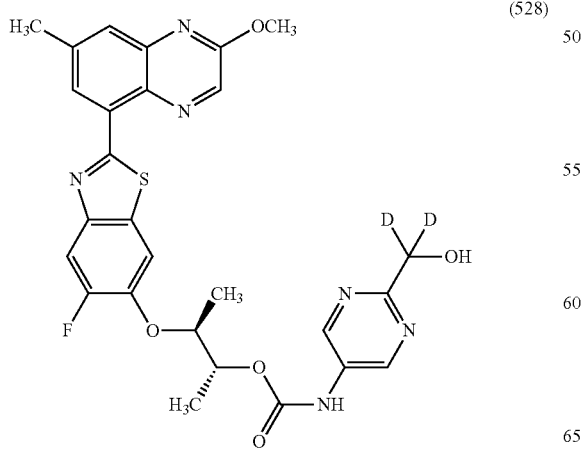

(528)

Intermediate I-86 (55 mg, 0.093 mmol) was solvated in THF (1 mL) and cooled to −78° C. To this mixture was added DIBAl-D (0.7 M in toluene) (0.398 mL, 0.278 mmol). After 1 h of stirring at −78° C., the reaction mixture was quenched with 1 mL of a 1 M HCl solution at −78° C. The resulting mixture was allowed to thaw to room temperature and stirred for a total of 30 min until the solution became fluid and bright yellow. The reaction mixture was then diluted with EtOAc and washed with saturated NH$_4$Cl before being dried over MgSO$_4$ and filtered over a pad of SiO$_2$ gel to remove aluminates. The resulting filtrate was concentrated and resubjected to the reduction conditions above to push any remaining deutero-aldehyde intermediate to the desired deutero-alcohol product. Following a repeat of the previous work-up procedure, the crude product was purified by prep HPLC (Method D, 35-100% over 20 min, hold 100% for 5 min) to afford Example 528 (16.3 mg, 0.028 mmol, 30% yield) as a yellow solid. LC-MS: Method H, RT=1.11 min, MS (ESI) m/z: 567.1 (M+H)$^+$. $^1$H NMR (500 MHz, DMSO-d$_6$) δ 8.80 (br. s., 2H), 8.68 (s, 1H), 8.53 (s, 1H), 8.00 (d, J=8.2 Hz, 1H), 7.92 (d, J=11.6 Hz, 1H), 7.80 (s, 1H), 5.16-5.04 (m, 1H), 4.80 (d, J=3.4 Hz, 1H), 4.48 (d, J=5.5 Hz, 1H), 4.06 (s, 3H), 2.60 (s, 3H), 1.38 (t, J=5.8 Hz, 6H).

Example 529

(2R,3S)-3-((2-(2-ethoxy-7-methylquinoxalin-5-yl)-5-fluorobenzo[d]thiazol-6-yl)oxy)butan-2-yl (2-(hydroxymethyl)pyrimidin-5-yl)carbamate

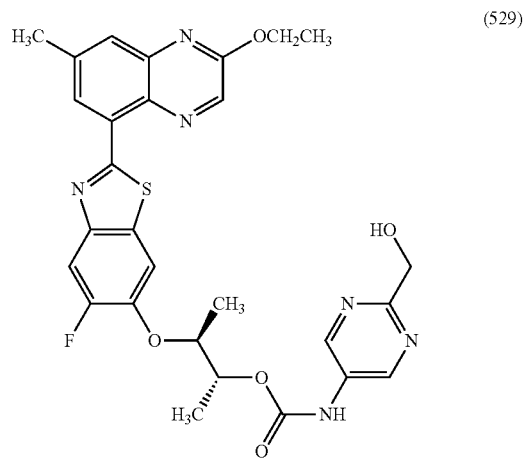 [SMILES: CCOc1cnc2c(-c3nc4cc(F)c(O[C@@H](C)[C@@H](C)OC(=O)Nc5cnc(CO)nc5)cc4s3)cc(C)cc2n1]

(529)

The following example was made in a manner analogous to the primary alcohol procedure described in the table above. Thus, Intermediate I-90 was reacted with DIBAl—H to afford Example 529 in 53% yield following purification by preparative HPLC (Method D, 50-100% over 21 min, hold at 100% for 6 min). LC-MS: Method H, RT=1.20 min, MS (ESI) m/z: 579.2 (M+H)$^+$. $^1$H NMR (500 MHz, DMSO-d$_6$) δ 8.82 (br. s., 2H), 8.69 (s, 1H), 8.55 (s, 1H), 8.03 (d, J=8.2 Hz, 1H), 7.95 (d, J=11.6 Hz, 1H), 7.81 (s, 1H), 5.13 (d, J=4.0 Hz, 1H), 4.81 (d, J=4.0 Hz, 1H), 4.59-4.47 (m, 4H), 2.63 (s, 3H), 1.45 (t, J=7.0 Hz, 3H), 1.40 (t, J=5.5 Hz, 6H).

Example 530

(R)-1-((5-fluoro-2-(2-methoxy-7-methylquinoxalin-5-yl)benzo[d]thiazol-6-yl)oxy) propan-2-yl (6-((2-methyl-2-(phosphonooxy)propyl)carbamoyl)pyridin-3-yl)carbamate, TFA

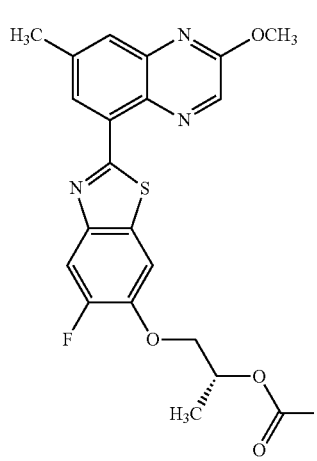
(530)

Intermediate 530A: (R)-1-((5-fluoro-2-(2-methoxy-7-methylquinoxalin-5-yl)benzo[d] thiazol-6-yl)oxy) propan-2-yl (6-((2-hydroxy-2-methylpropyl)carbamoyl)pyridin-3-yl)(Boc)carbamate

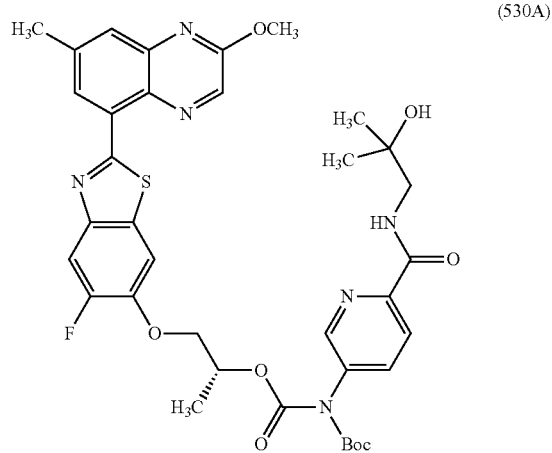 [SMILES: COc1cnc2c(-c3nc4cc(F)c(OC[C@@H](C)OC(=O)N(C(=O)OC(C)(C)C)c5ccc(C(=O)NCC(C)(C)O)nc5)cc4s3)cc(C)cc2n1]
(530A)

To a solution of Example 448 (55 mg, 0.087 mmol) in THF (5 mL) was added DMAP (26.5 mg, 0.217 mmol) followed by BOC-Anhydride (0.024 mL, 0.104 mmol). After 30 min of stirring at room temperature, the reaction was quenched with methanol, concentrated and purified by ISCO (12 g, 0-100% EtOAc/Hex, Product at 75%) to afford Intermediate 530A (52 mg, 0.071 mmol, 82% yield) as a yellow foaming solid. LC-MS: Method H, RT=1.22 min, MS (ESI) m/z: 735.3 (M+H)+. 1H NMR (400 MHz, CDCl3) δ 8.61 (d, J=1.8 Hz, 1H), 8.54 (s, 1H), 8.39 (d, J=2.0 Hz, 1H), 8.24 (t, J=6.2 Hz, 1H), 8.17 (d, J=8.1 Hz, 1H), 7.83 (d, J=11.4 Hz, 1H), 7.75 (dd, J=1.8, 0.9 Hz, 1H), 7.65 (dd, J=8.1, 2.4 Hz, 1H), 7.35 (d, J=7.7 Hz, 1H), 5.42-5.31 (m, 1H), 4.16-4.08 (m, 5H), 3.99 (dd, J=10.3, 6.8 Hz, 1H), 3.48-3.40 (m, 1H), 3.37-3.29 (m, 1H), 2.64 (s, 3H), 2.04 (s, 1H), 1.42 (s, 9H), 1.38 (d, J=6.4 Hz, 3H), 1.24 (s, 3H), 1.21 (s, 3H).

Intermediate 530B: (R)-1-((5-fluoro-2-(2-methoxy-7-methylquinoxalin-5-yl)benzo[d] thiazol-6-yl)oxy) propan-2-yl (6-((2-((bis(2-(trimethylsilyl)ethoxy) phosphoryl)oxy)-2-methylpropyl)carbamoyl)pyridin-3-yl)(Boc)carbamate

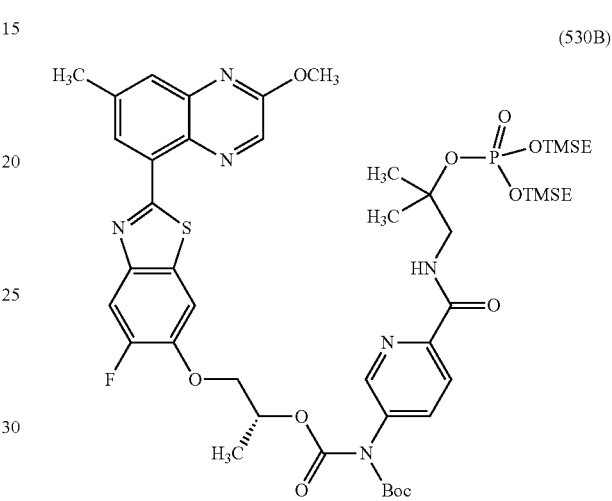
(530B)

To a solution of Intermediate 530A (20 mg, 0.027 mmol) and 1H-tetrazole (9.53 mg, 0.136 mmol) in DCM (1 mL) was added bis(2-(trimethylsilyl)ethyl) diisopropylphosphoramidite (49.8 mg, 0.136 mmol). The reaction mixture was sealed and heated to 50° C. for 30 min. After the desired phosphite intermediate was formed (monitored by TLC), the resulting solution was cooled to room temperature and hydrogen peroxide (35% wt. in H2O) (0.119 mL, 1.361 mmol) was added. After 20 min of additional stirring, the crude phosphate was diluted with EtOAc, and washed with saturated Na2S2O3. The organic phase was dried over MgSO4, filtered over Celite and concentrated to give Intermediate 530B (27.6 mg, 0.027 mmol, 100% yield) as a yellow oil. Quantitative yield was assumed and the crude intermediate was telescoped into the next reaction without further purification. LC-MS: Method H, RT=1.55 min, MS (ESI) m/z: 1015.4 (M+H)+.

Example 530

To a solution of crude Intermediate 530B (28 mg, 0.028 mmol) in DCM (2 mL) was added TFA (1.0 mL) at room temperature. After 10 min of stirring, the reaction mixture was concentrated and purified by Prep HPLC (Method C, 50-100% over 10 min, hold 100% for 5 min) to afford Example 530 (7.4 mg, 0.009 mmol, 31% yield) as a yellow TFA salt over the three step sequence. LC-MS: Method H, RT=1.09 min, MS (ESI) m/z: 715.1 (M+H)+. 1H NMR (400 MHz, DMSO-d6) δ 10.27 (s, 1H), 8.69 (s, 1H), 8.67-8.59 (m, 2H), 8.52 (d, J=1.5 Hz, 1H), 8.07-8.00 (m, 1H), 7.98-7.88 (m, 3H), 7.78 (d, J=0.9 Hz, 1H), 5.22 (td, J=6.2, 3.2 Hz, 1H), 4.37-4.29 (m, 1H), 4.27-4.17 (m, 1H), 4.02 (s, 3H), 3.49 (d, J=5.1 Hz, 2H), 2.56 (s, 3H), 1.37 (d, J=6.6 Hz, 3H), 1.27 (s, 6H). ¹⁹F NMR (376 MHz, DMSO-d₆) δ −73.51, −134.32.

Example 531

(2R,3S)-3-((2-(2-ethoxy-7-methylquinoxalin-5-yl)-5-fluorobenzo[d]thiazol-6-yl)oxy)butan-2-yl (6-(((S)-2-hydroxypropyl)carbamoyl)pyridin-3-yl)carbamate, TFA

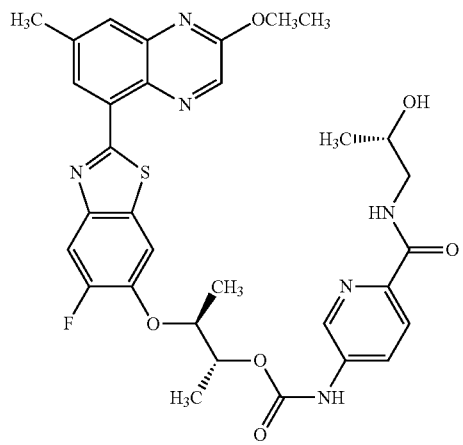
(531)

Intermediate I-89 (70 mg, 0.116 mmol) was solvated in THF (1.156 mL) and (S)-1-aminopropan-2-ol (0.12 mL, 1.524 mmol) was added to the solution. The reaction vial was sealed and heated to 65° C. After 18 h of heating, the reaction mixture was concentrated and purified by prep HPLC (Method C, 50-100% over 19 min, hold 100% for 10 min) to afford Example 531 (55 mg, 0.070 mmol, 61% yield) as a yellow solid. LC-MS: Method H, RT=1.27 min, MS (ESI) m/z: 649.2 (M+H)⁺. ¹H NMR (500 MHz, DMSO-d₆) δ 10.16 (br. s., 1H), 8.67 (s, 1H), 8.63 (s, 1H), 8.52 (s, 1H), 8.42 (t, J=5.8 Hz, 1H), 8.07-7.98 (m, 2H), 7.98-7.89 (m, 2H), 7.76 (s, 1H), 5.13 (d, J=4.0 Hz, 1H), 4.82 (d, J=5.2 Hz, 1H), 4.52 (q, J=7.0 Hz, 2H), 3.82-3.72 (m, 1H), 3.48 (br. s., 1H), 3.37-3.26 (m, 1H), 3.18-3.08 (m, 1H), 2.61 (s, 3H), 1.47-1.42 (m, 3H), 1.41 (t, J=5.8 Hz, 6H), 1.05 (d, J=6.1 Hz, 3H).

Example 532

(2R,3S)-3-((2-(2-ethoxy-7-methylquinoxalin-5-yl)-5-fluorobenzo[d]thiazol-6-yl)oxy)butan-2-yl (2-((phosphonooxy)methyl)pyrimidin-5-yl)carbamate

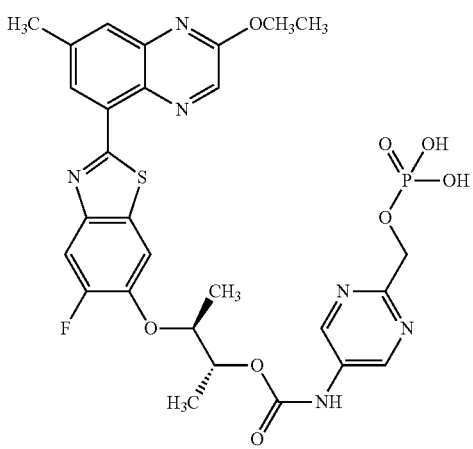
(532)

Intermediate 532A: (2R,3S)-3-((2-(2-ethoxy-7-methylquinoxalin-5-yl)-5-fluorobenzo[d]thiazol-6-yl)oxy)butan-2-yl (2-(((bis(2-(trimethylsilyl)ethoxy)phosphoryl)oxy)methyl)pyrimidin-5-yl)carbamate

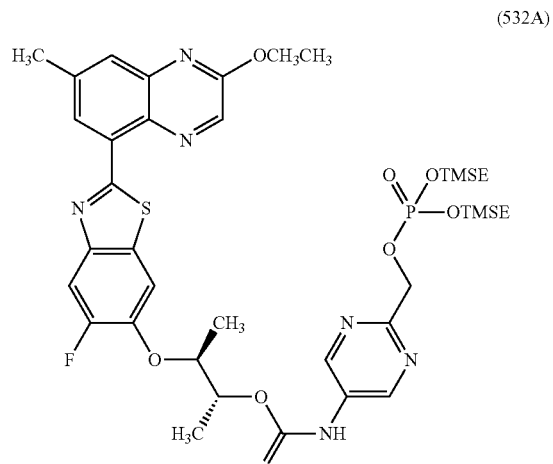
(532A)

To a solution of Example 529 (20 mg, 0.035 mmol) and 1H-tetrazole (24.21 mg, 0.346 mmol) in DCM (3457 µl) was added bis(2-(trimethylsilyl)ethyl) diisopropylphosphoramidite (126 mg, 0.346 mmol) at room temperature. After 1 h, the reaction mixture was cooled to 0° C. and hydrogen peroxide (35% wt. in H₂O) (90.8 µl, 1.037 mmol) was added. The resulting mixture was allowed to thaw to room temperature and stirred vigorously for 30 min. The reaction mixture was then diluted with EtOAc and washed with saturated Na₂S₂O₃. The organic phase was dried over MgSO₄, filtered over Celite and concentrated to give Intermediate 532A (29.7 mg, 0.035 mmol, 100% yield) as a yellow oil mixed with excess phosphate reagent. Quantitative yield was assumed, and the crude intermediate was telescoped into the next reaction without further purification. LC-MS: Method H, RT=1.52 min, MS (ESI) m/z: 859.5 (M+H)⁺.

Example 532

Crude Intermediate 532A (29 mg, 0.034 mmol) was solvated in DCM (2 mL). TFA (0.500 mL) was added causing the solution to turn dark yellow and bubble vigorously. After 10 min, the reaction mixture was concentrated and purified by Prep HPLC (Method C, 50-100% over 10 min, hold 100% for 5 min) to afford Example 532 (12.2 mg, 0.018, 54% yield) as a yellow solid over the three step sequence. LC-MS: Method H, RT=1.13 min, MS (ESI) m/z: 659.1 (M+H)⁺. ¹H NMR (400 MHz, DMSO-d₆) δ 10.08 (br. s., 1H), 8.78 (s, 2H), 8.62 (s, 1H), 8.48 (s, 1H), 7.98 (d, J=8.1 Hz, 1H), 7.88 (d, J=11.7 Hz, 1H), 7.72 (s, 1H), 5.06 (dd, J=6.4, 2.6 Hz, 1H), 4.83-4.74 (m, 2H), 4.74-4.64 (m, 1H), 4.46 (q, J=7.0 Hz, 2H), 2.55 (s, 3H), 1.37 (t, J=7.0 Hz, 3H), 1.33 (d, J=6.6 Hz, 6H). ¹⁹F NMR (376 MHz, DMSO-d₆) δ −133.47 (s, 1F). ³¹P NMR (162 MHz, DMSO-d₆) δ 24.2 (s, 1P)

Example 533

(2R,3S)-3-((5-fluoro-2-(2-methoxy-7-methylquinoxalin-5-yl)benzo[d]thiazol-6-yl)oxy)butan-2-yl (5-hydroxypyridin-3-yl)carbamate

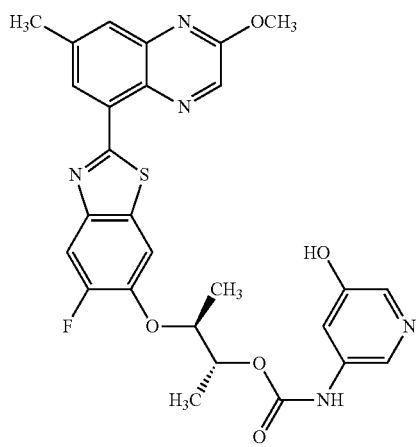
(533)

Intermediate 533A:
5-((tert-butyldimethylsilyl)oxy)pyridin-3-amine

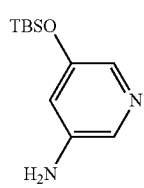
(533A)

To a vial containing 5-aminopyridin-3-ol (75 mg, 0.681 mmol) was added DCM (6986 μl) and THF (3493 μl) followed by Et₃N (285 μl, 2.043 mmol). TBS-Cl (123 mg, 0.817 mmol) was then added to the solution at room temperature. After 1 h of stirring, MeOH (5510, 13.62 mmol) was added to quench the remaining TBS-Cl. The reaction mixture was then diluted with EtOAc and washed with brine. The resulting organic phase was dried over MgSO₄, filtered over Celite, concentrated and co-evaporated with toluene to afford Intermediate 533A (150 mg, 0.669 mmol, 98% yield) as a brown oil. LC-MS: Method H, RT=0.77 min, MS (ESI) m/z: 225.2 (M+H)⁺. ¹H NMR (400 MHz, CDCl₃) δ 7.73 (d, J=2.4 Hz, 1H), 7.66 (d, J=2.2 Hz, 1H), 6.49 (t, J=2.3 Hz, 1H), 3.65 (br. s., 2H), 0.98 (s, 9H), 0.21 (s, 6H).

Intermediate 533B: (2R,3S)-3-((5-fluoro-2-(2-methoxy-7-methylquinoxalin-5-yl) benzo[d]thiazol-6-yl)oxy)butan-2-yl (5-(((tert-butyldimethylsilyl)oxy) pyridin-3-yl) carbamate

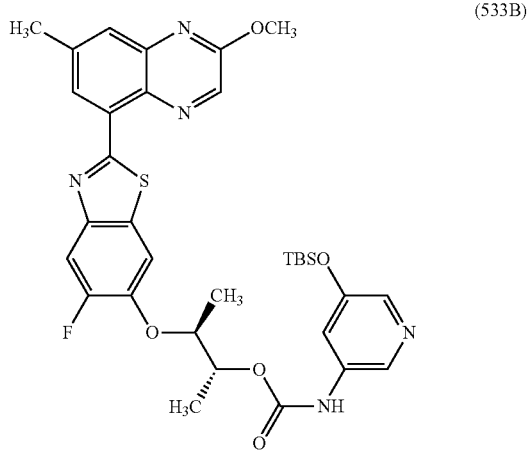 [SMILES: COc1cnc2c(-c3nc4cc(F)c(O[C@@H](C)[C@@H](C)OC(=O)Nc5cncc(O[Si](C)(C)C(C)(C)C)c5)cc4s3)cc(C)cc2n1]
(533B)

To a solution Intermediate I-72 (95 mg, 0.230 mmol) in THF (4595 μl) was added 15% phosgene in toluene (1620 μl, 2.298 mmol). The resulting slurry was allowed to stir at room temperature overnight. After 16 h, the reaction mixture was concentrated to remove excess phosgene. The resulting crude chloroformate was retaken in DCM (2290 μl) and slowly added to a pre-mixed suspension of Intermediate 533A and pyridine (185 μl, 2.290 mmol) in DCM (2290 μl). After 10 min, the reaction mixture was concentrated and purified by ISCO (24 g, 0-80% DCM/EtOAc, Product at 33%) to afford Intermediate 533B (110 mg, 0.133 mmol, 57.9% yield) as a yellow solid. LC-MS: Method H, RT=1.22 min, MS (ESI) m/z: 664.1 (M+H)⁺. ¹H NMR (400 MHz, CDCl₃) δ 8.60 (d, J=2.0 Hz, 1H), 8.55 (s, 1H), 8.03 (d, J=2.2 Hz, 1H), 7.92 (d, J=2.4 Hz, 1H), 7.82 (d, J=11.2 Hz, 1H), 7.77 (dd, J=1.8, 0.9 Hz, 1H), 7.60 (br. s., 1H), 7.53 (d, J=7.7 Hz, 1H), 6.67 (br. s., 1H), 5.21-5.12 (m, 1H), 4.60 (qd, J=6.2, 3.3 Hz, 1H), 4.13 (s, 3H), 2.65 (s, 3H), 1.47 (d, J=6.4 Hz, 3H), 1.43 (d, J=6.4 Hz, 3H), 0.23 (s, 6H), 0.00 (s, 9H).

Example 533

To a solution of Intermediate 533B (25 mg, 0.030 mmol) in THF (1 mL) was added acetic acid (0.017 mL, 0.301 mmol) followed by TBAF (1 M in THF) (0.090 mL, 0.090 mmol) (10:35 am). The resulting mixture was stirred at room temperature for 20 min, before being concentrated and purified by Prep HPLC (Method D, 45-90% over 22 min, hold at 100% for 5 min) to afford Example 533 (9.3 mg, 0.016 mmol, 54% yield). LC-MS: Method H, RT=1.00 min, MS (ESI) m/z: 550.1 (M+H)⁺. ¹H NMR (500 MHz, DMSO-d₆) δ 9.82 (br. s., 1H), 8.66 (s, 1H), 8.51 (s, 1H), 8.10 (br. s., 1H), 7.99 (d, J=7.9 Hz, 1H), 7.92 (d, J=11.6 Hz, 1H), 7.77 (s, 2H), 7.45 (br. s., 1H), 5.11 (dd, J=6.6, 2.6 Hz, 1H), 4.77 (dd, J=6.4, 2.7 Hz, 1H), 4.06 (s, 3H), 2.60 (s, 3H), 1.39 (dd, J=10.7, 6.4 Hz, 6H).

Example 534

(2R,3S)-3-((5-fluoro-2-(2-methoxy-7-methylquinoxalin-5-yl)benzo[d]thiazol-6-yl)oxy) butan-2-yl (5-(2-hydroxyethoxy)pyridin-3-yl)carbamate

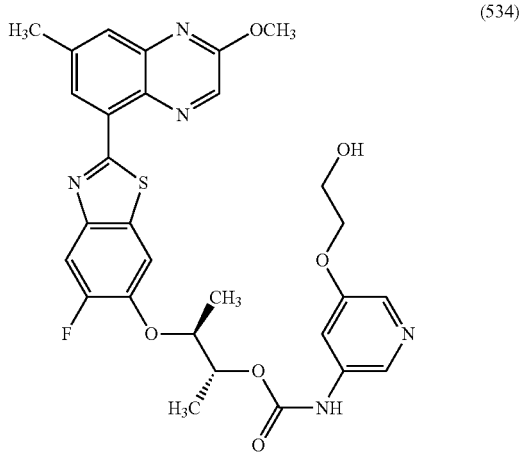 [SMILES: COc1cnc2c(-c3nc4cc(F)c(O[C@@H](C)[C@@H](C)OC(=O)Nc5cncc(OCCO)c5)cc4s3)cc(C)cc2n1]

(534)

Intermediate 534A: methyl 2-((5-(((((2R,3S)-3-((5-fluoro-2-(2-methoxy-7-methylquinoxalin-5-yl)benzo[d]thiazol-6-yl)oxy)butan-2-yl)oxy)carbonyl)amino)pyridin-3-yl)oxy)acetate

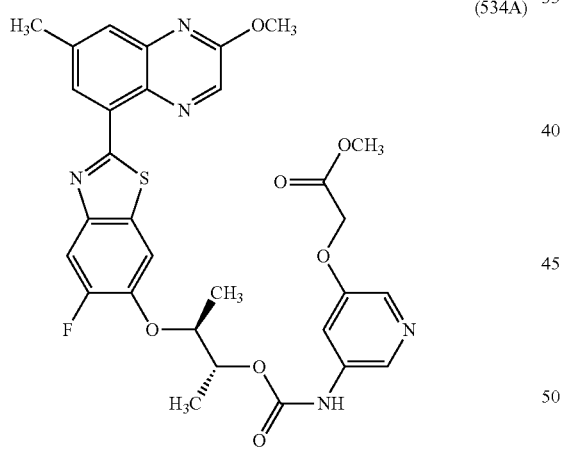

(534A)

To a solution of Example 533 (25 mg, 0.045 mmol) in DMF (1 mL) was added cesium carbonate (22.23 mg, 0.068 mmol) followed by methyl bromoacetate (5.03 μl, 0.055 mmol). After 1.5 h of vigorous stirring and room temperature, the reaction mixture was diluted with EtOAc and filtered over a short pad of SiO$_2$ gel. The resulting organic phase was concentrated to remove residual DMF, retaken in EtOAc, washed with brine, dried over MgSO$_4$, filtered and concentrated to afford Intermediate 534A (22 mg, 0.035 mmol, 78% yield) as a thick yellow oil. LC-MS: Method H, RT=1.07 min, MS (ESI) m/z: 622.1 (M+H)$^+$. $^1$H NMR (400 MHz, CDCl$_3$) δ 8.59 (d, J=1.8 Hz, 1H), 8.53 (s, 1H), 8.07 (d, J=1.8 Hz, 1H), 8.03 (d, J=2.4 Hz, 1H), 7.81 (d, J=11.2 Hz, 1H), 7.75 (s, 1H), 7.70 (br. s., 1H), 7.51 (d, J=7.9 Hz, 1H), 6.92 (br. s., 1H), 5.20-5.09 (m, 1H), 4.67 (s, 2H), 4.64-4.54 (m, 1H), 4.12 (s, 3H), 3.81 (s, 3H), 2.64 (s, 3H), 1.46 (d, J=6.6 Hz, 3H), 1.44-1.41 (m, 3H).

Example 534

A solution of Intermediate 534A (11 mg, 0.018 mmol) in THF (1 mL) was cooled to −78° C. To this mixture was added DIBAL-H (1 M in toluene) (0.088 mL, 0.088 mmol). Following the reagent addition, the reaction mixture was allowed to thaw to room temperature. After 30 min of vigorous stirring, the reaction mixture was quenched with 1 M HCl, concentrated, and purified by Prep HPLC (Method D, 45-90% over 20 min, hold 100% for 5 min) to afford Example 534 (1.8 mg, 0.002 mmol, 16% yield) as a yellow solid. LC-MS: Method H, RT=0.91 min, MS (ESI) m/z: 594.2 (M+H)$^+$. $^1$H NMR (500 MHz, DMSO-d$_6$) δ 9.87 (br. s., 1H), 8.66 (s, 1H), 8.51 (s, 1H), 8.22 (br. s., 1H), 7.98 (d, J=7.9 Hz, 1H), 7.91 (d, J=11.3 Hz, 2H), 7.78 (s, 1H), 7.51 (br. s., 1H), 5.10 (d, J=6.4 Hz, 1H), 4.79 (d, J=4.0 Hz, 1H), 4.06 (s, 3H), 3.99 (t, J=4.6 Hz, 2H), 3.72-3.59 (m, 2H), 2.60 (s, 3H), 1.38 (dd, J=9.6, 6.6 Hz, 6H).

Example 535

(2R,3S)-3-((2-(2-ethoxy-7-methylquinoxalin-5-yl)-5-fluorobenzo[d]thiazol-6-yl)oxy)butan-2-yl (2-((S)-1-hydroxyethyl)pyrimidin-5-yl)carbamate

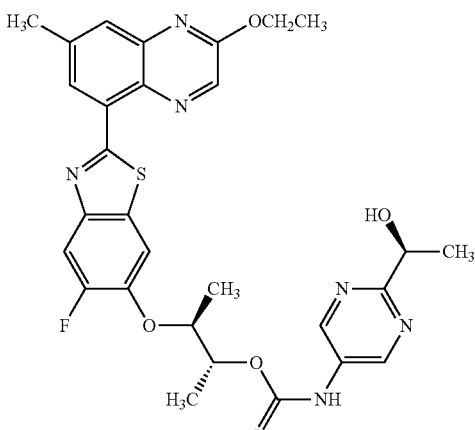

(535)

A solution of Intermediate I-90 (50 mg, 0.085 mmol) in THF (1693 μl) was cooled to −78° C. To this cooled mixture was added DIBAl—H (1 M in toluene) (425 μl, 0.425 mmol), which caused the solution to take on a reddish hue. After 1 h, the reaction mixture was quenched cold with 1.7 mL of Rochelle's Salt, allowed to thaw to room temperature, and stirred vigorously overnight. After 16 h, the reaction mixture was diluted with EtOAc and extracted. The organic phase was dried over MgSO$_4$, filtered over Celite and concentrated. The crude residue was purified by ISCO (12 g, 0-100% EtOAc/DCM, Pdt at 50%) to afford Example 535 (44 mg, 0.074 mmol, 88% yield) as a diastereomeric mixture. This material was further purified by chiral HPLC (Chiracel OD, Semi-prep-80% Heptane/20% EtOH/MeOH (1:1) isocratic eluent with a 16 mL/min flow rate. Diastereomer retention time 60-75 min) to afford homochiral Example 535 (16.4 mg, 0.027 mmol, 37% yield). LC-MS: Method H, RT=1.20 min, MS (ESI) m/z: 593.0 (M+H)+. 1H NMR (400 MHz, DMSO-d6) δ 9.95 (br. s., 1H), 8.75 (s, 2H), 8.64 (s, 1H), 8.50 (d, J=1.8 Hz, 1H), 7.98 (d, J=8.1 Hz, 1H), 7.89 (d, J=11.7 Hz, 1H), 7.75 (dd, J=1.8, 0.9 Hz, 1H), 5.11-4.98 (m, 2H), 4.77-4.69 (m, 1H), 4.68-4.59 (m, 1H), 4.47 (q, J=7.0 Hz, 2H), 2.56 (s, 3H), 1.38 (t, J=7.0 Hz, 3H), 1.33 (dd, J=6.5, 2.5 Hz, 6H), 1.28 (d, J=6.4 Hz, 3H).

Example 536

(2R,3S)-3-((2-(2-ethoxy-7-methylquinoxalin-5-yl)-5-fluorobenzo[d]thiazol-6-yl)oxy) butan-2-yl (2-((R)-1-hydroxyethyl)pyrimidin-5-yl)carbamate

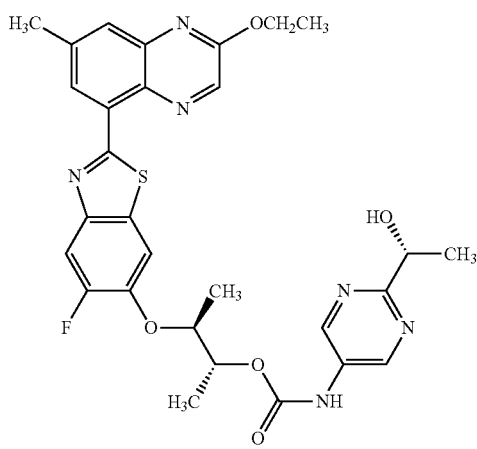

(536)

Example 536 was synthesized concurrently with Example 535 above. Thus, the above diastereomeric mixture was purified by chiral HPLC (Chiracel OD, Semi-prep-80% Heptane/20% EtOH/MeOH (1:1) isocratic eluent with a 16 mL/min flow rate. Diastereomer retention time 85-100 min) to afford homochiral Example 536 (17.2 mg, 0.028 mmol, 37% yield). LC-MS: Method H, RT=1.20 min, MS (ESI) m/z: 593.0 (M+H)+. 1H NMR (400 MHz, DMSO-d6) δ 9.95 (br. s., 1H), 8.75 (s, 2H), 8.64 (s, 1H), 8.50 (d, J=2.0 Hz, 1H), 7.98 (d, J=8.1 Hz, 1H), 7.89 (d, J=11.7 Hz, 1H), 7.75 (s, 1H), 5.10-4.99 (m, 2H), 4.74 (dd, J=6.3, 2.8 Hz, 1H), 4.68-4.60 (m, 1H), 4.47 (q, J=7.0 Hz, 2H), 2.56 (s, 3H), 1.38 (t, J=7.0 Hz, 3H), 1.33 (dd, J=6.3, 2.5 Hz, 6H), 1.28 (d, J=6.6 Hz, 3H).

Example 537

2-((5-fluoro-2-(2-methoxy-7-methylquinoxalin-5-yl)benzo[d]thiazol-6-yl)oxy)ethyl (2-(2-hydroxyethyl)pyrimidin-5-yl)carbamate

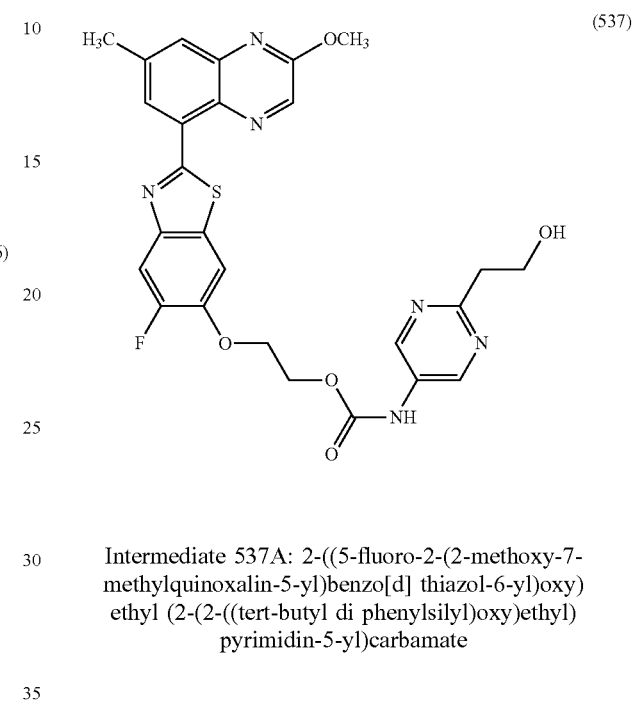

(537)

Intermediate 537A: 2-((5-fluoro-2-(2-methoxy-7-methylquinoxalin-5-yl)benzo[d] thiazol-6-yl)oxy) ethyl (2-(2-((tert-butyl di phenylsilyl)oxy)ethyl) pyrimidin-5-yl)carbamate

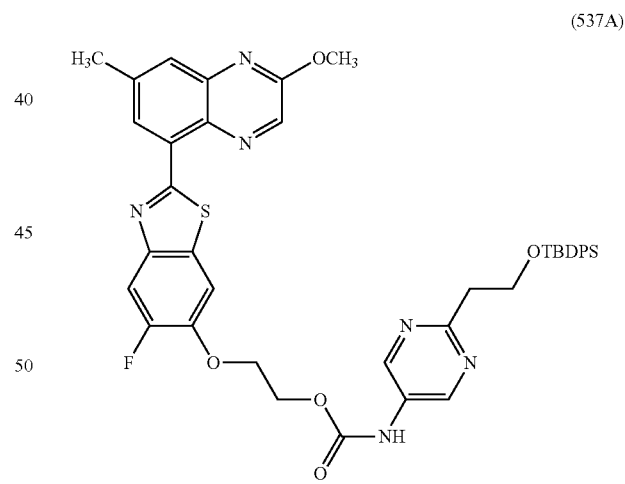

(537A)

To a solution Intermediate I-66 (15 mg, 0.039 mmol) in THF (1 mL) was added 15% phosgene in toluene (0.274 mL, 0.389 mmol). The resulting slurry was allowed to stir overnight. After 16 h the reaction mixture was concentrated to a crude yellow residue. The resulting chloroformate intermediate was retaken in THF (1 mL) and added dropwise to a pre-mixed solution of Intermediate I-98 (13.49 mg, 0.036 mmol) and pyridine (0.014 mL, 0.179 mmol) in THF (1 mL). After 10 min of stirring at room temperature, the reaction mixture was concentrated in vacuo to remove excess pyridine, and Intermediate 537A was telescoped into the subsequent deprotection step without further purification. LC-MS: Method H, RT=1.46 min, MS (ESI) m/z: 789.0 (M+H)+.

Example 537

To a crude solution of Intermediate 537A (14 mg, 0.018 mmol) in THF (0.75 mL) and MeOH (0.75 mL) was added (R)-(−)-camphorsulfonic acid (12.37 mg, 0.053 mmol). The reaction vial was sealed and heated to 65° C. After 1.5 h of heating, the reaction mixture was cooled to room temperature and quenched with triethylamine (0.025 mL, 0.177 mmol). The resulting mixture was concentrated, and purified by Prep HPLC (Method D, 40-80% over 22 min, hold at 100% for 5 min) to afford Example 537 (5.2 mg, 0.009 mmol, 52% yield) as a yellow solid over the three step sequence. LC-MS: Method H, RT=1.04 min, MS (ESI) m/z: 550.9 (M+H)+. $^1$H NMR (500 MHz, DMSO-$d_6$) δ 10.16 (br. s., 1H), 8.79 (s, 2H), 8.72 (s, 1H), 8.55 (s, 1H), 8.03-7.94 (m, 2H), 7.82 (s, 1H), 4.57 (br. s., 2H), 4.45 (br. s., 2H), 4.08 (s, 3H), 3.82 (q, J=6.4 Hz, 2H), 2.97 (t, J=6.7 Hz, 2H), 2.63 (s, 3H).

Example 538

(2R,3S)-3-((4-chloro-5-fluoro-2-(2-methoxy-7-methylquinoxalin-5-yl)benzo[d]thiazol-6-yl)oxy)butan-2-yl (2-(2-hydroxyethyl)pyrimidin-5-yl)carbamate

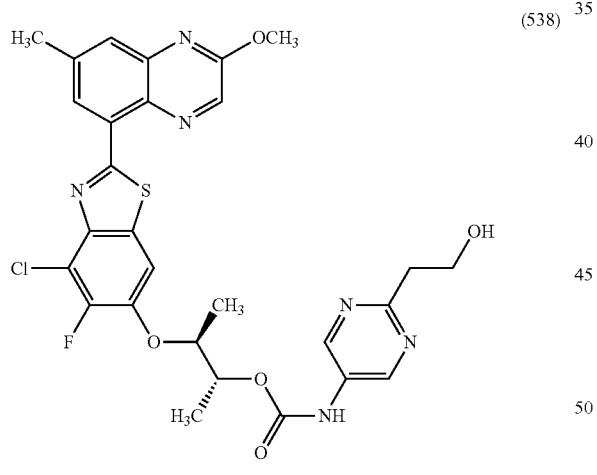

(538)

Example 538 was prepared in a manner analogous to Example 536 above. Thus, Intermediate I-81 was reacted with phosgene, followed by Intermediate I-98, followed by CSA to afford Example 538 (66% yield over the three step sequence) after purification by Prep HPLC (Method D, 55-90% over 25 min, hold at 90% for 4 min). LC-MS: Method H, RT=1.18 min, MS (ESI) m/z: 612.9, 614.9 (M+H)+. $^1$H NMR (500 MHz, DMSO-$d_6$) δ 9.97 (br. s., 1H), 8.76 (br. s., 2H), 8.70 (s, 1H), 8.56 (s, 1H), 8.06 (d, J=7.6 Hz, 1H), 7.83 (s, 1H), 5.14 (dd, J=6.6, 2.6 Hz, 1H), 4.85 (d, J=6.4 Hz, 1H), 4.09 (s, 3H), 3.84-3.74 (m, 2H), 3.34 (br. s., 1H), 2.94 (t, J=6.7 Hz, 2H), 2.65 (s, 3H), 1.43 (d, J=6.4 Hz, 3H), 1.40 (d, J=6.4 Hz, 3H).

Example 539

(2R,3S)-3-((2-(6-chloro-3-methoxyquinolin-8-yl)-5-fluorobenzo[d]thiazol-6-yl)oxy)butan-2-yl (2-(hydroxymethyl)pyrimidin-5-yl)carbamate

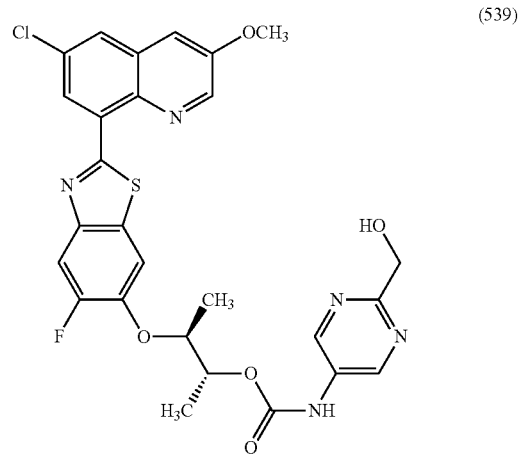 [SMILES: COc1cnc2c(-c3nc4cc(F)c(O[C@@H](C)[C@@H](C)OC(=O)Nc5cnc(CO)nc5)cc4s3)cc(Cl)cc2c1]

(539)

Intermediate 539A: methyl 5-(((((2R,3S)-3-((2-(6-chloro-3-methoxyquinolin-8-yl)-5-fluorobenzo[d]thiazol-6-yl)oxy)butan-2-yl)oxy)carbonyl)amino)pyrimidine-2-carboxylate

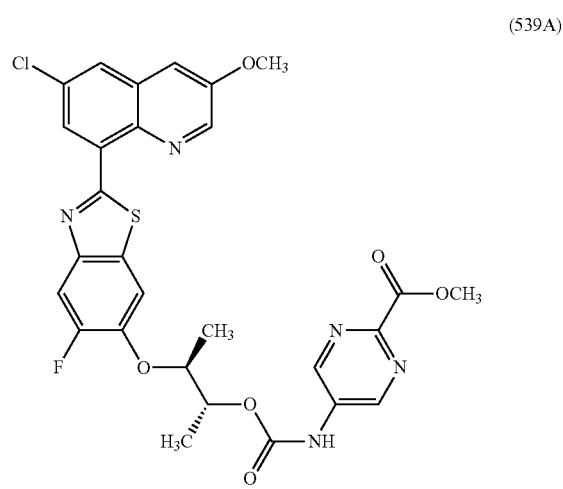 [SMILES: COC(=O)c1ncc(NC(=O)O[C@H](C)[C@H](C)Oc2cc3sc(-c4cc(Cl)cc5cc(OC)cnc45)nc3cc2F)cn1]

(539A)

To a solution Intermediate I-91 (30 mg, 0.069 mmol) in THF (1386 µl) was added 15% phosgene in toluene (489 µl, 0.693 mmol). The resulting slurry was allowed to stir overnight. After 16 h, the mixture was concentrated to remove the excess phosgene. The resulting chloroformate was retaken in DCM (7.00 mL) and slowly added to a pre-mixed solution of Intermediate I-107 (39.6 mg, 0.209 mmol) and pyridine (0.084 mL, 1.044 mmol) in DCM (1.4 mL). After 30 min, the reaction mixture was concentrated and purified by ISCO (12 g, 0-100% EtOAC/DCM) to afford Intermediate 539A (24 mg, 0.029 mmol, 42.3% yield). LC-MS: Method H, RT=1.14 min, MS (ESI) m/z: 612.2, 614.1 (M+H)+. $^1$H NMR (400 MHz, CDCl$_3$) δ 9.04 (s, 2H), 8.75 (d, J=3.1 Hz, 1H), 8.69 (d, J=2.4 Hz, 1H), 7.84-7.75 (m, 2H), 7.54 (d, J=7.9 Hz, 1H), 7.38 (d, J=2.9 Hz, 1H), 5.23-5.10 (m, 1H), 4.70-4.60 (m, 1H), 4.02 (s, 3H), 3.99 (s, 3H), 1.48 (d, J=6.4 Hz, 3H), 1.45 (d, J=6.4 Hz, 4H).

Example 539

Example 539 was prepared in a manner analogous to the primary alcohols described in the table above. Thus, Intermediate 539A was reacted with DIBAl—H to afford Example 539 (10% yield) following purification by Prep HPLC (Method D, 45-90% over 22 min, hold at 100% for 5 min). LC-MS: Method H, RT=1.09 min, MS (ESI) m/z: 584.2, 586.1 (M+H)$^+$. $^1$H NMR (500 MHz, DMSO-d$_6$) δ 10.04 (br. s., 1H), 8.88 (br. s., 1H), 8.83 (br. s., 2H), 8.64 (br. s., 1H), 8.21 (br. s., 1H), 8.06 (d, J=7.6 Hz, 1H), 8.01-7.91 (m, 2H), 5.14 (br. s., 1H), 4.82 (br. s., 1H), 4.51 (br. s., 2H), 4.00 (br. s., 3H), 1.41 (br. s., 6H).

Example 540

(2R,3S)-3-((2-(6-chloro-3-methoxyquinolin-8-yl)-5-fluorobenzo[d]thiazol-6-yl)oxy)butan-2-yl (2-((R)-2-hydroxypropoxy)pyrimidin-5-yl)carbamate

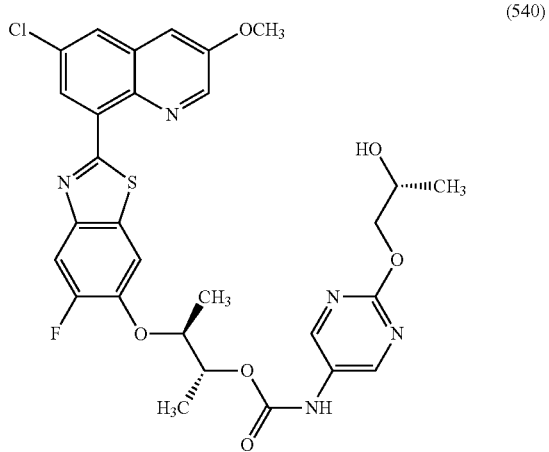 [SMILES: COc1cnc2c(-c3nc4cc(F)c(O[C@@H](C)[C@@H](C)OC(=O)Nc5cnc(OC[C@@H](C)O)nc5)cc4s3)cc(Cl)cc2c1]
(540)

Intermediate 540A: (2R,3S)-3-((2-(6-chloro-3-methoxyquinolin-8-yl)-5-fluorobenzo[d] thiazol-6-yl)oxy)butan-2-yl (2-((R)-2-((tert-butyldimethylsilyl)oxy)propoxy)pyrimidin-5-yl)carbamate

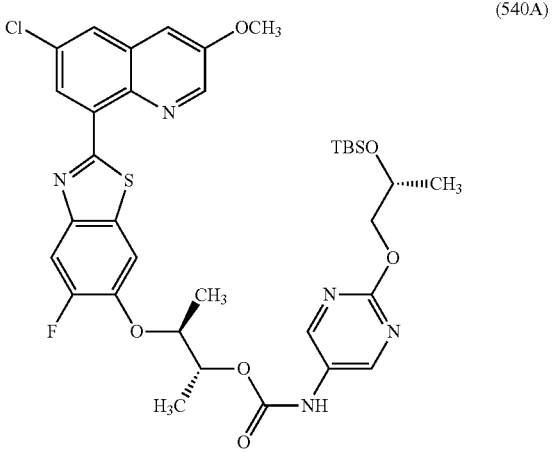 [SMILES: COc1cnc2c(-c3nc4cc(F)c(O[C@@H](C)[C@@H](C)OC(=O)Nc5cnc(OC[C@@H](C)O[Si](C)(C)C(C)(C)C)nc5)cc4s3)cc(Cl)cc2c1]
(540A)

To a solution of Intermediate I-91 (40 mg, 0.092 mmol) in THF (1848 μl) was added 15% phosgene in toluene (652 μl, 0.924 mmol). The resulting slurry was allowed to stir overnight. After 16 h, the mixture was concentrated to remove the excess phosgene. The resulting chloroformate was retaken in THF (1.0 mL) and added dropwise to a pre-mixed solution of Intermediate I-104 (19.19 mg, 0.068 mmol) and pyridine (0.036 mL, 0.451 mmol) in THF (1 mL). After 10 min, the reaction mixture was concentrated to remove excess pyridine and telescoped into the TBS deprotection without further purification. LC-MS: Method H, RT=1.48 min, MS (ESI) m/z: 742.0, 744.0 (M+H)$^+$.

Example 540

To a crude solution of Intermediate 540A (33 mg, 0.044 mmol) in THF (0.75 mL) and MeOH (0.750 mL) was added R(-(−)-camphor sulfonic acid (31.0 mg, 0.133 mmol). The reaction vial was sealed and heated to 65° C. After 30 min of heating, the mixture was cooled to room temperature and triethylamine (0.062 mL, 0.445 mmol) was added to quench the reaction. The reaction mixture was concentrated and purified by Prep HPLC (Method D, 55-100% over 20 min, hold at 100% for 7 min) to afford Example 540 (17.6, 0.027 mmol, 62% yield) as a yellow solid. LC-MS: Method H, RT=1.17 min, MS (ESI) m/z: 628.0, 629.9 (M+H)$^+$. $^1$H NMR (500 MHz, DMSO-d$_6$) δ 9.80 (br. S., 1H), 8.86 (br. S., 1H), 8.62 (br. S., 3H), 8.19 (s, 1H), 8.04 (d, J=7.6 Hz, 1H), 7.97 (d, J=11.3 Hz, 1H), 7.94 (br. S., 1H), 5.10 (d, J=6.4 Hz, 1H), 4.82 (br. S., 1H), 4.12-4.06 (m, 1H), 4.03-3.97 (m, 4H), 3.92 (d, J=10.7 Hz, 1H), 1.40 (t, J=6.3 Hz, 6H), 1.12 (d, J=6.1 Hz, 3H).

Example 541

(2R,3S)-3-((2-(6-chloro-3-methoxyquinolin-8-yl)-5-fluorobenzo[d]thiazol-6-yl)oxy)butan-2-yl (2-((S)-2-hydroxypropoxy)pyrimidin-5-yl)carbamate

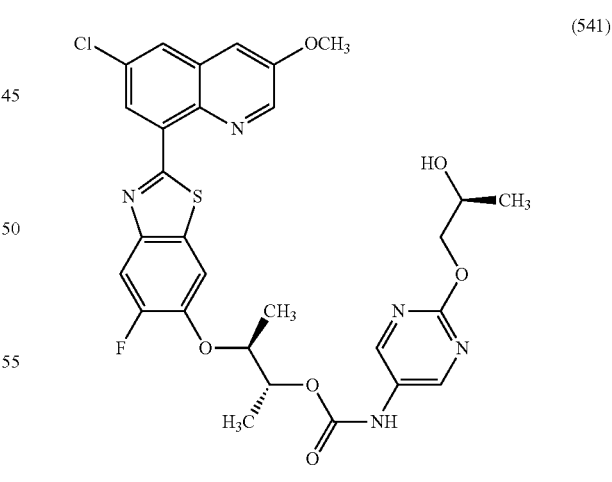
(541)

Example 541 was prepared in a manner analogous Example 540 described above. Thus, Intermediate I-91 was reacted with phosgene, followed by Intermediate I-103, followed by CSA to afford Example 541 (72% yield over the three step sequence) after purification by Prep HPLC (Method D, 60-100% over 20 min, hold at 100% for 6 min). LC-MS: Method H, RT=1.17 min, MS (ESI) m/z: 628.0, 629.9 (M+H)⁺. $^1$H NMR (500 MHz, DMSO-$d_6$) δ 9.80 (br. s., 1H), 8.84 (d, J=2.1 Hz, 1H), 8.60 (br. s., 3H), 8.17 (s, 1H), 8.03 (d, J=7.9 Hz, 1H), 7.95 (d, J=11.3 Hz, 1H), 7.92 (d, J=2.4 Hz, 1H), 5.10 (d, J=6.4 Hz, 1H), 4.89 (d, J=4.9 Hz, 1H), 4.82 (d, J=4.0 Hz, 1H), 4.12-4.05 (m, 1H), 4.05-4.00 (m, 1H), 3.99 (s, 3H), 3.93 (dt, J=11.4, 5.6 Hz, 1H), 1.44-1.34 (m, 6H), 1.11 (d, J=6.4 Hz, 3H).

Preparation of Carbamate Examples

To a solution of the appropriately substituted quinoxaline-benzothiazole alcohol (1.0 equiv) in THF (0.05 M) was added a solution of phosgene (15% by wt. in toluene, 10 equiv). This solution was stirred at room temperature overnight before the intermediate chloroformate was concentrated in vacuo. This crude chloroformate was retaken in THF (0.05 M) and added dropwise to a pre-mixed solution of pyridine (10 equiv) and the appropriately substituted amino-heterocycle (1.1-3.0 equiv) in either THF (0.05 M) or DCM (0.05), whichever gave the best reagent solubility. After 30 min of stirring, the combined mixture was concentrated, retaken in DMF, filtered and purified by preparative HPLC to yield the desired example.

If the reactant amino-heterocycle contained a silyl protecting group, the silyl group was removed according to Procedure J before final purification. If the reactant amino-heterocycle contained an acetonide protecting group, the ketal was removed according to Procedure K before final purification.

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 542 | 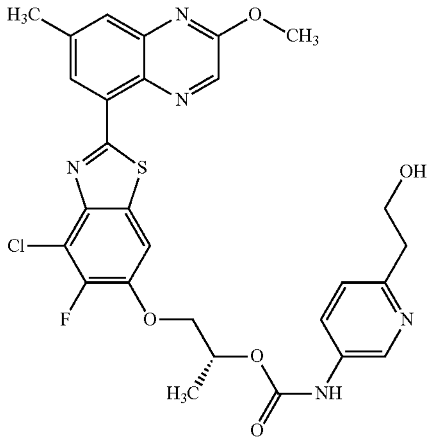 [SMILES: COc1cnc2c(-c3nc4c(Cl)c(F)c(OC[C@@H](C)OC(=O)Nc5ccc(CCO)nc5)cc4s3)cc(C)cc2n1] | I-69 | I-109 | 598.1 | Orthogonal HPLC method B Injection 2, 2.136 | 45-90% 20 min, 100% 5 min | ¹H NMR (500 MHz, DMSO-d₆) δ 9.90 (br. s., 1H), 8.40-8.75 (m, 3H), 7.70-7.99 (m, 3H), 7.26 (d, J = 8.24 Hz, 1H), 5.32 (br. s., 1H), 4.27-4.49 (m, 2H), 4.11 (s, 3H), 3.75 (br. s., 2H), 2.81-2.91 (m, 2H), 2.66 (s, 3H), 1.48 (d, J = 6.10 Hz, 3H). |
| 543 | 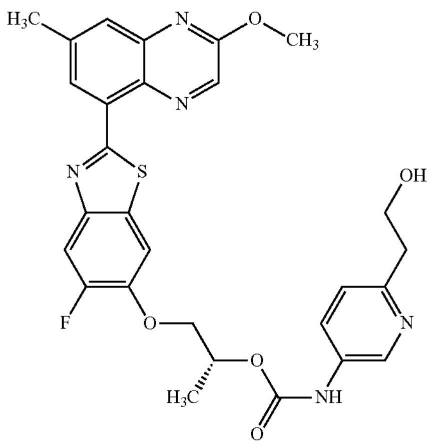 [SMILES: COc1cnc2c(-c3nc4cc(F)c(OC[C@@H](C)OC(=O)Nc5ccc(CCO)nc5)cc4s3)cc(C)cc2n1] | I-67 | I-109 | 564.2 | Orthogonal HPLC method B Injection 2, 1.962 | 40-80% 5 min, 100% 20 min | ¹H NMR (500 MHz, DMSO-d₆) δ 9.96-9.57 (m, 1H), 8.75 (s, 1H), 8.62-8.49 (m, 2H), 8.10-7.94 (m, 2H), 7.84 (s, 1H), 7.81-7.74 (m, 1H), 7.19 (d, J = 8.5 Hz, 1H), 5.32-5.15 (m, 1H), 4.67-4.53 (m, 1H), 4.41-4.23 (m, 2H), 4.13-4.05 (m, 3H), 3.69 (t, J = 6.9 Hz, 2H), 2.80 (t, J = 7.0 Hz, 2H), 2.66-2.59 (m, 3H), 1.42 (d, J = 6.6 Hz, 3H). |

-continued

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 544 | 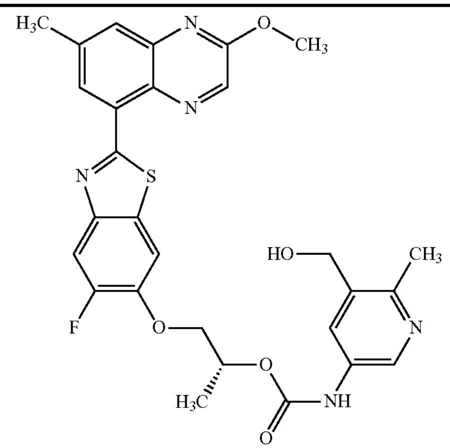 | I-67 | I-112 | 564.1 | Orthogonal HPLC method B Injection 2, 1.961 | 40-80% 20 min, 100% 6 min | ¹H NMR (500 MHz, DMSO-d₆) δ 9.81 (br. s., 1H), 8.63 (s, 1H), 8.46 (s, 1H), 8.34 (br. s., 1H), 7.95-7.81 (m, 3H), 7.72 (s, 1H), 5.19 (d, J = 3.1 Hz, 1H), 4.40 (br. s., 2H), 4.32-4.11 (m, 2H), 2.54 (s, 3H), 2.44 (br. s., 3H), 2.26 (s, 3H), 1.36 (d, J = 6.4 Hz, 3H). |
| 545 | 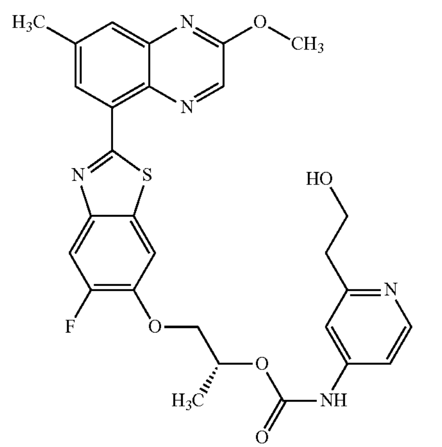 [SMILES: COc1cnc2c(-c3nc4cc(F)c(OC[C@@H](C)OC(=O)Nc5ccnc(CCO)c5)cc4s3)cc(C)cc2n1] | I-67 | I-94 | 564.15 | Orthogonal HPLC method B Injection 2, 1.960 | 50-100% 15 min, 100% 5 min | ¹H NMR (500 MHz, DMSO-d₆) δ 10.11 (s, 1H), 8.64 (s, 1H), 8.48 (s, 1H), 8.21 (d, J = 5.5 Hz, 1H), 7.98-7.84 (m, 2H), 7.74 (s, 1H), 7.29 (s, 1H), 7.23 (d, J = 5.2 Hz, 1H), 5.20 (d, J = 3.1 Hz, 1H), 4.33-4.26 (m, 1H), 4.26-4.16 (m, 1H), 4.00 (s, 3H), 3.63 (t, J = 6.9 Hz, 2H), 2.71 (t, J = 6.7 Hz, 2H), 2.55 (s, 3H), 1.36 (d, J = 6.4 Hz, 3H). |

| Ex. No. | Structure | R—OH | R—NH₂ | LCMS [M+H]⁺ m/z | LCMS RT (Min) | HPLC Prep Method D | NMR |
|---|---|---|---|---|---|---|---|
| 546 | 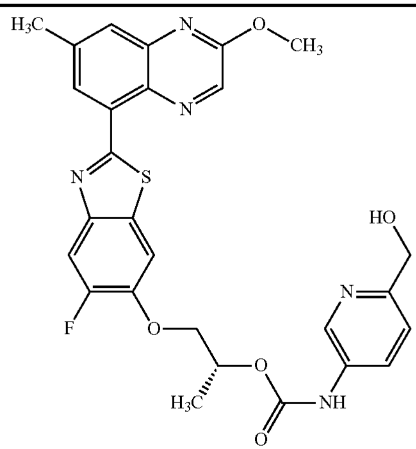 | I-67 | I-385B | 550.2 | Orthogonal HPLC method B Injection 2, 1.995 | 15-100% 15 min, 100% 5 min | ¹H NMR (500 MHz, DMSO-d₆) δ 9.96 (br. s., 1H), 8.70 (s, 1H), 8.62-8.45 (m, 2H), 8.06-7.84 (m, 3H), 7.80 (s, 1H), 7.40 (d, J = 8.2 Hz, 1H), 5.25 (d, J = 3.1 Hz, 1H), 4.50-4.46 (m, 2H), 4.39-4.18 (m, 2H), 4.06 (s, 3H), 2.60 (s, 3H), 1.50-1.20 (m, 3H). |
| 547 | 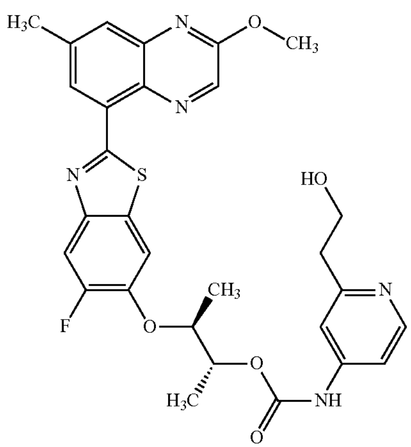 [SMILES: COc1cnc2c(-c3nc4cc(F)c(O[C@@H](C)[C@@H](C)OC(=O)Nc5ccnc(CCO)c5)cc4s3)cc(C)cc2n1] | I-72 | I-94 | 578.19. | Orthogonal HPLC method B Injection 2, 2.058 | 30-80% 15 min, 100% 5 min | ¹H NMR (500 MHz, DMSO-d₆) δ 10.13 (s, 1H), 8.76 (s, 1H), 8.60 (s, 1H), 8.31 (d, J = 5.5 Hz, 1H), 8.08 (d, J = 7.9 Hz, 1H), 8.00 (d, J = 11.3 Hz, 1H), 7.87 (s, 1H), 7.46-7.28 (m, 2H), 5.18 (d, J = 4.6 Hz, 1H), 4.84 (br. s., 1H), 4.13 (s, 3H), 3.75 (t, J = 6.7 Hz, 2H), 3.57-3.43 (m, 1H), 2.89-2.76 (m, 2H), 2.67 (s, 3H), 1.46 (t, J = 6.4 Hz, 6H). |

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 549 | 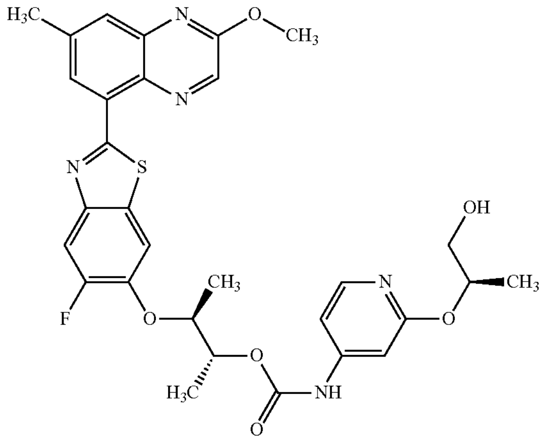 [SMILES: COc1cnc2c(-c3nc4cc(F)c(O[C@@H](C)[C@@H](C)OC(=O)Nc5ccnc(O[C@H](C)CO)c5)cc4s3)cc(C)cc2n1] | I-72 | I-111 | 608.20 | Orthogonal HPLC method B Injection 2, 2.178 | 30-80% 22 min, 100% 7 min | ¹H NMR (500 MHz, DMSO-d₆) δ 10.08 (s, 1H), 8.72 (s, 1H), 8.56 (s, 1H), 8.04 (d, J = 8.1 Hz, 1H), 7.99-7.89 (m, 2H), 7.82 (s, 1H), 7.01 (d, J = 5.4 Hz, 1H), 6.85 (s, 1H), 5.19-5.01 (m, 2H), 4.89-4.74 (m, J = 3.7 Hz, 1H), 4.08 (s, 3H), 3.56-3.34 (m, 2H), 2.63 (s, 3H), 1.40 (t, J = 6.1 Hz, 6H), 1.17 (d, J = 6.1 Hz, 3H). |
| 550 | 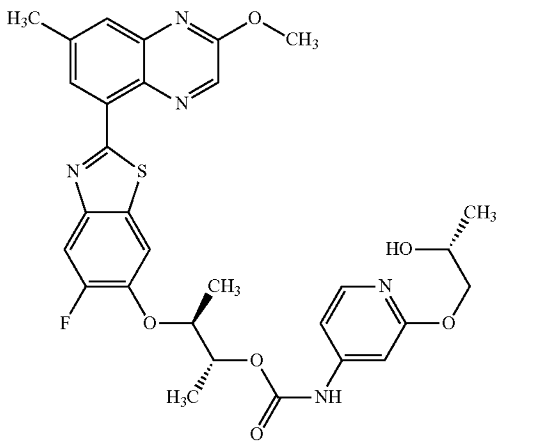 [SMILES: COc1cnc2c(-c3nc4cc(F)c(O[C@@H](C)[C@@H](C)OC(=O)Nc5ccnc(OC[C@@H](C)O)c5)cc4s3)cc(C)cc2n1] | I-72 | I-111 | 608.20 | Orthogonal HPLC method B Injection 2, 2.167 | 30-80% 22 min, 100% 7 min | ¹H NMR (500 MHz, DMSO-d₆) δ 10.10 (s, 1H), 8.70 (s, 1H), 8.54 (s, 1H), 8.05-7.89 (m, 3H), 7.80 (s, 1H), 7.02 (d, J = 4.7 Hz, 1H), 6.91 (s, 1H), 5.12 (d, J = 4.0 Hz, 1H), 4.79 (br. s., 1H), 4.04-3.85 (m, 3H), 2.62 (s, 3H), 1.40 (t, J = 5.6 Hz, 6H), 1.09 (d, J = 6.4 Hz, 3H). |

-continued

| Ex. No. | Structure | R—OH | R—NH$_2$ | LCMS [M + H]$^+$ m/z | LCMS RT (Min) | HPLC Prep Method D | NMR |
|---|---|---|---|---|---|---|---|
| 552 | 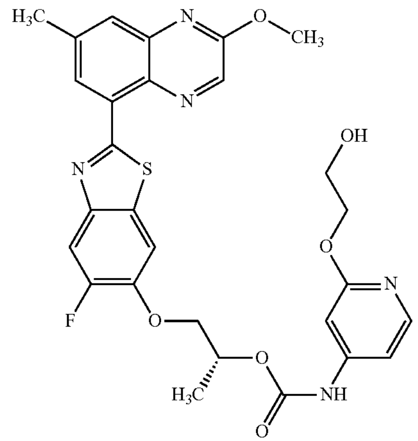 [SMILES: COc1cnc2c(-c3nc4cc(F)c(OC[C@@H](C)OC(=O)Nc5ccnc(OCCO)c5)cc4s3)cc(C)cc2n1] | I-67 | I-110 | 580.1 | Orthogonal HPLC method B Injection 2, 2.003 | 30-100% 20 min, 100% 5 min | $^1$H NMR (500 MHz, DMSO-d$_6$) δ 10.17 (s, 1H), 8.70 (s, 1H), 8.59-8.49 (m, 1H), J = 1.5 Hz, 1H), 8.03-7.89 (m, 3H), 7.80 (s, 1H), 7.06 (dd, J = 5.6, 1.7 Hz, 1H), 6.93 (s, 1H), 5.35-5.21 (m, 1H), 4.43-4.24 (m, 2H), 4.24-4.16 (m, J = 5.0, 5.0 Hz, 2H), 4.07 (s, 3H), 3.68 (q, J = 5.5 Hz, 2H), 3.43 (br. s., 2H), 2.62 (s, 3H), 1.43 (d, J = 6.4 Hz, 3H). |
| 553 | 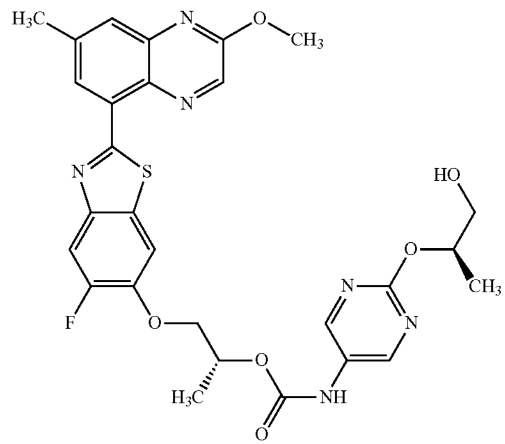 [SMILES: COc1cnc2c(-c3nc4cc(F)c(OC[C@@H](C)OC(=O)Nc5cnc(O[C@H](C)CO)nc5)cc4s3)cc(C)cc2n1] | I-67 | I-106 | 595.15. | Orthogonal HPLC method B Injection 2, 2.265 | 45-100% 20 min, 100% 5 min | $^1$H NMR (500 MHz, DMSO-d$_6$) δ 9.85 (br. s., 1H), 8.65 (s, 1H), 8.60 (br. s., 2H), 8.50 (s, 1H), 7.97-7.87 (m, 2H), 7.77 (s, 1H), 5.29-5.19 (m, 1H), 5.10-4.97 (m, 1H), 4.42-4.20 (m, 2H), 4.06 (s, 3H), 3.60-3.55 (m, 2H), 2.60 (s, 3H), 1.41 (d, J = 6.4 Hz, 3H). |

-continued
| Ex. No. | Structure | R—OH | R—NH$_2$ | LCMS [M + H]$^+$ m/z | LCMS RT (Min) | HPLC Prep Method D | NMR |
|---|---|---|---|---|---|---|---|
| 554 | 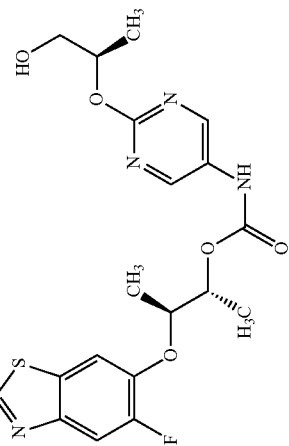 | I-72 | I-106 | 609.19 | Orthogonal HPLC method B Injection 2, 2.348 | 50-100% 20 min, 100% 5 min | $^1$H NMR (500 MHz, DMSO-d$_6$) δ 9.89-9.70 (m, 1H), 8.68 (s, 1H), 8.59 (br. s., 2H), 8.53 (s, 1H), 8.01 (d, J = 8.2 Hz, 1H), 7.93 (d, J = 11.6 Hz, 1H), 7.80 (s, 1H), 5.20-4.53 (m, 3H), 4.07 (s, 3H), 3.60-3.47 (m, 1H), 2.61 (s, 3H), 1.44-1.31 (m, 6H), 1.21 (d, J = 6.1 Hz, 3H). |
| 555 | 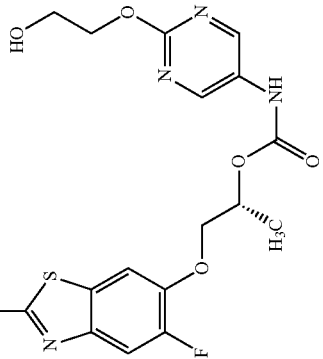 | I-67 | I-97 | 581.1. | LCMS Method H, 1.11 | 50-100% 10 min, 100% 5 min | $^1$H NMR (400 MHz, DMSO-d$_6$) δ 8.76 (s, 1H), 8.68-8.54 (m, 3H), 8.12-7.94 (m, 2H), 7.85 (s, 1H), 5.34-5.14 (m, 1H), 4.99-4.75 (m, 1H), 4.44-4.32 (m, 1H), 4.32-4.17 (m, J = 5.0, 5.0 Hz, 3H), 4.09 (s, 3H), 3.75-3.61 (m, 2H), 2.64 (s, 3H), 1.42 (d, J = 6.6 Hz, 3H). |

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 556 | 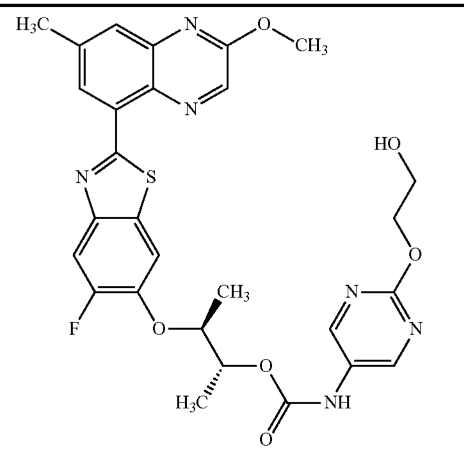 | I-72 | I-97 | 595.2 | LCMS Method H, 1.16 | 50-100% 10 min, 100% 8 min | ¹H NMR (400 MHz, DMSO-d₆) δ 9.72 (br. s., 1H), 8.67 (s, 1H), 8.53 (br. s., 2H), 8.51 (d, J = 1.8 Hz, 1H), 7.97 (d, J = 8.1 Hz, 1H), 7.89 (d, J = 11.7 Hz, 1H), 7.77 (d, J = 0.7 Hz, 1H), 5.02 (qd, J = 6.5, 2.8 Hz, 1H), 4.80-4.68 (m, 2H), 4.16 (t, J = 5.1 Hz, 2H), 4.02 (s, 3H), 3.60 (q, J = 5.4 Hz, 2H), 2.56 (s, 3H), 1.31 (m, 6H). |
| 557 | 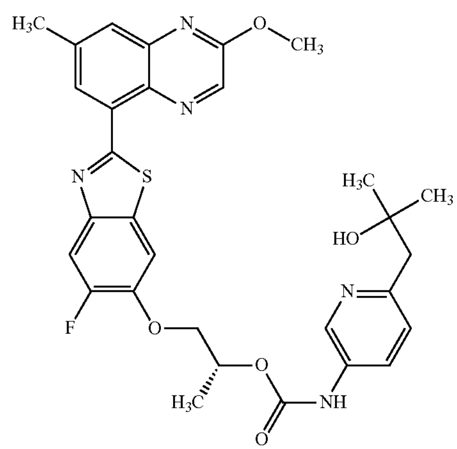 [SMILES: COc1cnc2c(-c3nc4cc(F)c(OC[C@@H](C)OC(=O)Nc5ccc(CC(C)(C)O)nc5)cc4s3)cc(C)cc2n1] | I-67 | I-92 | 592.36 | Orthogonal HPLC method B Injection 2, 2.052 | 40-100% 10 min, 100% 5 min | ¹H NMR (500 MHz, DMSO-d₆) δ 9.86 (br. s., 1H), 8.67 (s, 1H), 8.57-8.45 (m, 2H), 8.05-7.89 (m, 2H), 7.84-7.71 (m, 2H), 7.23 (d, J = 8.2 Hz, 1H), 5.30-5.16 (m, J = 6.3, 3.2 Hz, 1H), 4.40-4.19 (m, 2H), 4.06 (s, 3H), 2.60 (s, 3H), 1.42 (d, J = 6.4 Hz, 3H), 1.06 (s, 6H). |

-continued

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 558 | 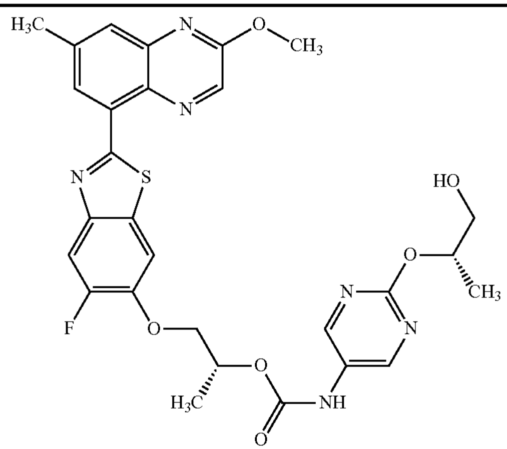 | I-67 | I-105 | 595.20 | Orthogonal HPLC method B Injection 2, 2.270 | 45-100% 20 min, 100% 5 min | ¹H NMR (500 MHz, DMSO-d₆) δ 8.74 (s, 1H), 8.67 (br. s., 2H), 8.58 (s, 1H), 8.05-7.93 (m, 2H), 7.85 (s, 1H), 5.40-5.25 (m, 1H), 5.15-4.91 (m, 1H), 4.46-4.27 (m, 2H), 3.57 (s, 3H), 2.62 (s, 2H), 1.48 (d, J = 6.4 Hz, 3H), 1.28 (d, J = 6.1 Hz, 3H). |
| 559 | 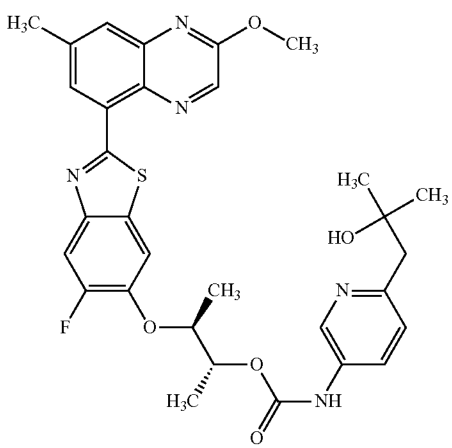 [SMILES: COc1cnc2c(-c3nc4cc(F)c(O[C@@H](C)[C@@H](C)OC(=O)Nc5ccc(CC(C)(C)O)nc5)cc4s3)cc(C)cc2n1] | I-72 | I-92 | 606.35 | Orthogonal HPLC method B Injection 2, 2.138 | 40-100% 12 min, 100% 5 min | ¹H NMR (500 MHz, DMSO-d₆) δ 9.83-9.57 (m, 1H), 8.62 (s, 1H), 8.52-8.42 (m, 2H), 7.96 (d, J = 8.2 Hz, 1H), 7.89 (d, J = 11.6 Hz, 1H), 7.75 (s, 2H), 7.19 (d, J = 8.5 Hz, 1H), 5.09 (dd, J = 6.4, 2.7 Hz, 1H), 4.77 (dd, J = 6.3, 2.6 Hz, 1H), 4.05 (s, 3H), 1.38 (dd, J = 11.1, 6.3 Hz, 7H), 1.03 (s, 6H). |

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 560 | 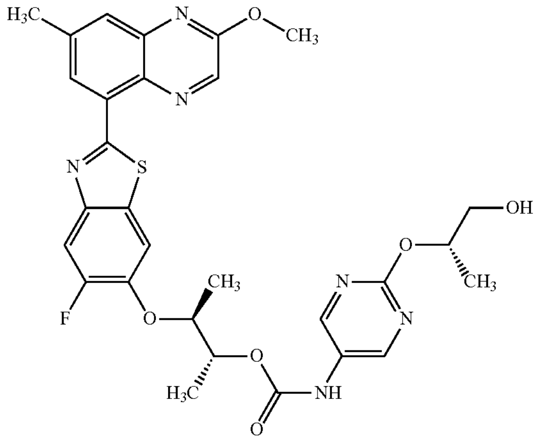 [SMILES: COc1cnc2c(-c3nc4cc(F)c(O[C@@H](C)[C@@H](C)OC(=O)Nc5cnc(O[C@@H](C)CO)nc5)cc4s3)cc(C)cc2n1] | I-72 | I-105 | 609.20 | Orthogonal HPLC method B Injection 2, 2.362 | 35-75% 20 min, 100% 5 min | ¹H NMR (500 MHz, DMSO-d₆) δ 9.73 (br. s., 1H), 8.76-8.34 (m, 4H), 8.02-7.85 (m, 3H), 7.75 (s, 1H), 5.16-4.91 (m, 2H), 4.79 (br. s., 1H), 4.09-3.97 (m, 4H), 3.72-3.65 (m, 3H), 2.58 (s, 3H), 1.43-1.33 (m, 6H), 1.18 (d, J = 6.4 Hz, 3H). |
| 561 | 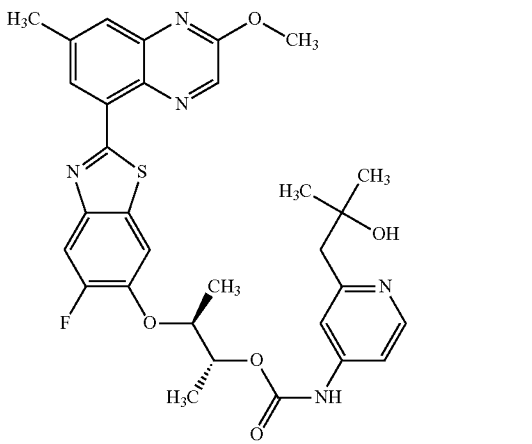 [SMILES: COc1cnc2c(-c3nc4cc(F)c(O[C@@H](C)[C@@H](C)OC(=O)Nc5ccnc(CC(C)(C)O)c5)cc4s3)cc(C)cc2n1] | I-72 | I-95 | 606.22 | Orthogonal HPLC method B Injection 2, 2.253 | 15-100% 19 min, 100% 5 min | ¹H NMR (500 MHz, DMSO-d₆) δ 8.72 (s, 1H), 8.57 (s, 1H), 8.04-7.86 (m, 3H), 7.83 (s, 1H), 6.44-6.31 (m, 2H), 6.13 (br. s., 1H), 4.95 (dd, J = 6.4, 3.1 Hz, 1H), 4.73 (dd, J = 6.1, 3.1 Hz, 1H), 4.09 (s, 3H), 3.10-3.02 (m, 1H), 2.99-2.92 (m, 1H), 2.63 (s, 3H), 1.41 (s, 3H), 1.40 (s, 3H), 1.37-1.29 (m, J = 5.8, 5.8 Hz, 7H). |

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 562 | 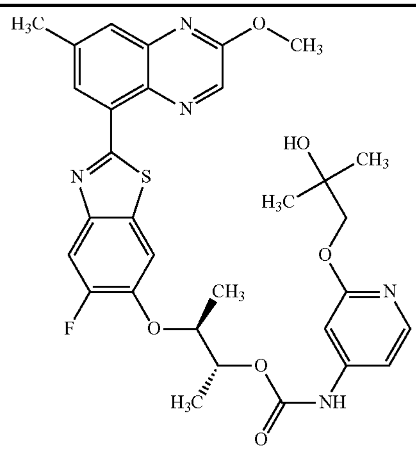 | I-72 | I-96 | 622.21 | Orthogonal HPLC method B Injection 2, 2.199 | 50-100% 20 min, 100% 5 min | ¹H NMR (500 MHz, DMSO-d₆) δ 10.13 (s, 1H), 8.75 (s, 1H), 8.60 (d, J = 1.5 Hz, 1H), 8.16-7.80 (m, 4H), 7.12-6.86 (m, 2H), 5.30-5.11 (m, J = 6.4, 2.7 Hz, 1H), 4.97-4.81 (m, J = 6.4, 2.7 Hz, 1H), 4.13 (s, 3H), 4.02 (s, 2H), 2.67 (s, 3H), 1.45 (t, J = 6.1 Hz, 6H), 1.20 (s, 6H). |
| 563 | 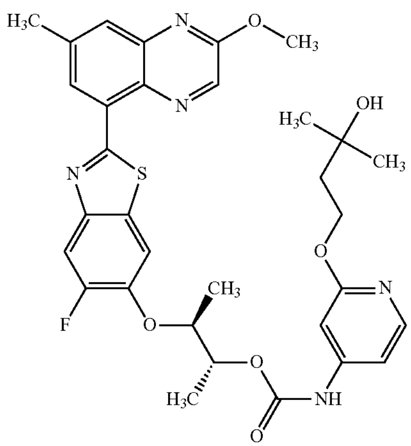 [SMILES: COc1cnc2c(-c3nc4cc(F)c(O[C@@H](C)[C@@H](C)OC(=O)Nc5ccnc(OCCC(C)(C)O)c5)cc4s3)cc(C)cc2n1] | I-72 | I-108 | 636.26 | Orthogonal HPLC method B Injection 2, 2.190 | 50-100% 20 min, 100% 5 min | ¹H NMR (500 MHz, DMSO-d₆) δ 9.97 (s, 1H), 8.62 (s, 1H), 8.47 (s, 1H), 7.94 (d, J = 8.2 Hz, 1H), 7.89-7.81 (m, 2H), 7.73 (s, 1H), 6.92 (d, J = 4.3 Hz, 1H), 6.80 (s, 1H), 5.09-4.99 (m, J = 6.7, 2.7 Hz, 1H), 4.78-4.67 (m, J = 6.3, 2.6 Hz, 1H), 4.21 (t, J = 7.2 Hz, 2H), 4.00 (s, 3H), 2.55 (s, 3H), 1.71 (t, J = 7.3 Hz, 2H), 1.32 (t, J = 6.6 Hz, 6H), 1.06 (s, 6H). |

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 564 | 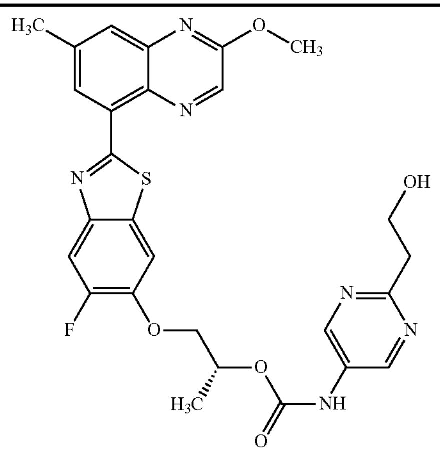 | I-67 | I-98 | 565.15 | Orthogonal HPLC method B Injection 2, 2.111 | 45-85% 25 min, 100% 6 min | ¹H NMR (500 MHz, DMSO-d₆) δ 8.80-8.62 (m, 3H), 8.50 (s, 1H), 7.99-7.88 (m, 2H), 7.78 (s, 1H), 5.27 (d, J = 2.7 Hz, 1H), 4.40-4.32 (m, J = 8.2 Hz, 1H), 4.31-4.20 (m, J = 10.8, 6.3 Hz, 1H), 4.06 (s, 3H), 3.81 (q, J = 6.4 Hz, 2H), 2.95 (t, J = 6.7 Hz, 2H), 2.60 (s, 3H), 1.42 (d, J = 6.4 Hz, 3H). |
| 565 | 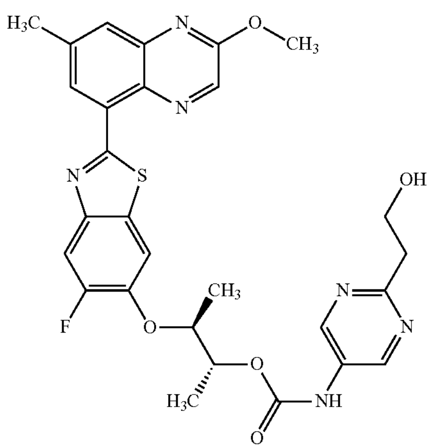 [SMILES: COc1cnc2c(-c3nc4cc(F)c(O[C@@H](C)[C@@H](C)OC(=O)Nc5cnc(CCO)nc5)cc4s3)cc(C)cc2n1] | I-72 | I-98 | 579.18 | Orthogonal HPLC method B Injection 2, 2.298 | 45-90% 25 min, 100% 6 min | ¹H NMR (500 MHz, DMSO-d₆) δ 8.78-8.67 (m, 3H), 8.55 (s, 1H), 8.04-7.89 (m, 2H), 7.83 (s, 1H), 5.19-5.05 (m, 1H), 4.85-4.77 (m, 1H), 3.79 (d, J = 5.8 Hz, 2H), 2.93 (t, J = 6.7 Hz, 2H), 1.39 (t, J = 6.9 Hz, 6H). |

-continued

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 566 | 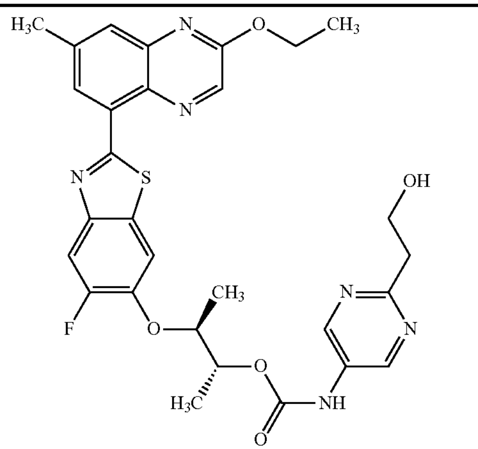 | I-80 | I-98 | 593.24 | Orthogonal HPLC method B Injection 2, 2.359 | 50-100% 20 min, 100% 10 min | ¹H NMR (500 MHz, DMSO-d₆) δ 9.95 (br. s., 1H), 8.75 (br. s., 2H), 8.63 (s, 1H), 8.51 (s, 1H), 8.00 (d, J = 7.9 Hz, 1H), 7.92 (d, J = 11.3 Hz, 1H), 7.76 (s, 1H), 5.12 (dd, J = 6.6, 2.6 Hz, 1H), 4.79 (d, J = 4.0 Hz, 1H), 4.66 (t, J = 5.5 Hz, 1H), 4.51 (q, J = 7.0 Hz, 2H), 3.87-3.62 (m, 2H), 2.94 (t, J = 6.7 Hz, 2H), 2.56 (s, 3H), 1.54-1.28 (m, 9H). |
| 567 | 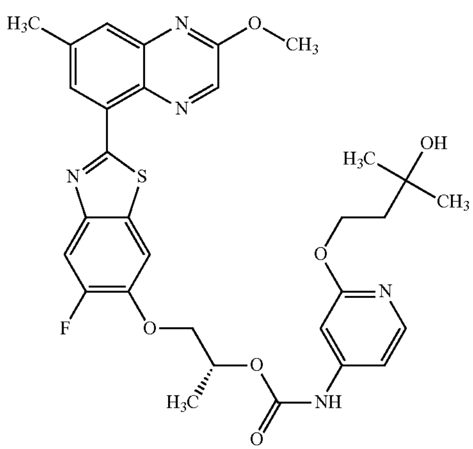 [SMILES: COc1cnc2c(-c3nc4cc(F)c(OC[C@@H](C)OC(=O)Nc5ccnc(OCCC(C)(C)O)c5)cc4s3)cc(C)cc2n1] | I-67 | I-108 | 622.2 | Orthogonal HPLC method B Injection 2, 2.087 | 50-100% 20 min, 100% 7 min | ¹H NMR (500 MHz, DMSO-d₆) δ 10.13 (s, 1H), 8.70 (s, 1H), 8.54 (s, 1H), 8.09-7.91 (m, 3H), 7.81 (s, 1H), 7.01 (d, J = 5.8 Hz, 1H), 6.90 (s, 1H), 5.26 (br. s., 1H), 4.45-4.14 (m, 4H), 4.08 (s, 3H), 2.62 (s, 3H), 1.79 (t, J = 7.2 Hz, 2H), 1.42 (d, J = 6.4 Hz, 3H), 1.14 (s, 6H). |

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 568 | 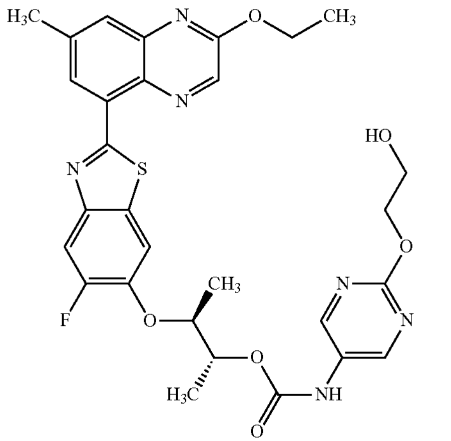 [SMILES: CCOc1cnc2c(-c3nc4cc(F)c(O[C@@H](C)[C@@H](C)OC(=O)Nc5cnc(OCCO)nc5)cc4s3)cc(C)cc2n1] | I-80 | I-97 | 609.19 | Orthogonal HPLC method B Injection 2, 2.408 | 30-100% 15 min, 100% 10 min | ¹H NMR (500 MHz, DMSO-d₆) δ 8.70 (s, 1H), 8.57 (s, 3H), 8.06-7.92 (m, 2H), 7.82 (s, 1H), 5.14-5.03 (m, 1H), 4.94-4.89 (m, 1H), 4.85-4.75 (m, 1H), 4.55 (d, J = 7.0 Hz, 2H), 4.23 (br. s., 2H), 3.74-3.63 (m, J = 4.9 Hz, 2H), 2.63 (s, 3H), 1.45 (t, J = 7.0 Hz, 3H), 1.42-1.31 (m, 6H). |
| 569 | 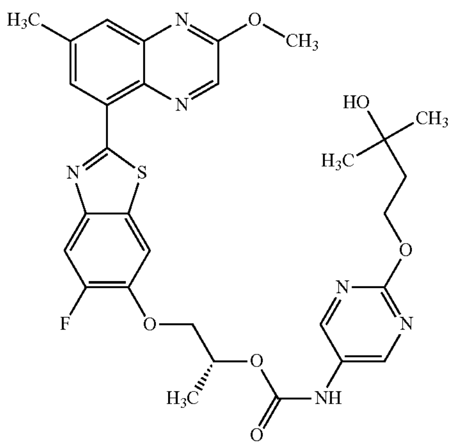 [SMILES: COc1cnc2c(-c3nc4cc(F)c(OC[C@@H](C)OC(=O)Nc5cnc(OCCC(C)(C)O)nc5)cc4s3)cc(C)cc2n1] | I-67 | I-100 | 623.15 | Orthogonal HPLC method B Injection 2, 2.345 | 45-100% 21 min, 100% 5 min | ¹H NMR (500 MHz, DMSO-d₆) δ 9.88 (br. s., 1H), 8.71-8.56 (m, 3H), 8.50 (s, 1H), 8.02-7.86 (m, 2H), 7.76 (s, 1H), 5.24 (br. s., 1H), 4.41-4.18 (m, 4H), 3.97 (s, 3H), 2.59 (s, 3H), 1.81 (br. s., 2H), 1.41 (d, J = 6.1 Hz, 3H), 1.14 (br. s., 6H). |

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 570 | 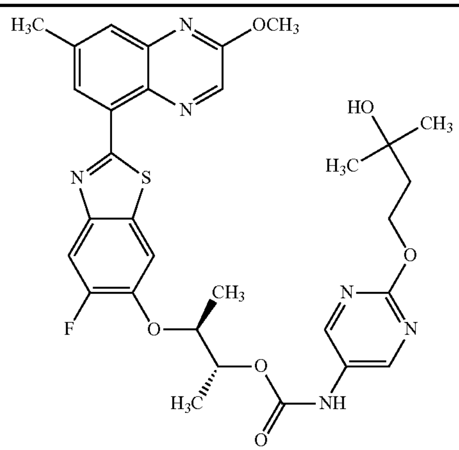 | I-72 | I-100 | 637.2 | Orthogonal HPLC method B Injection 2, 2.436 | 50-100% 6 min, 100% 22 min | ¹H NMR (500 MHz, DMSO-d₆) δ 9.77 (br. s., 1H), 8.70-8.42 (m, 4H), 8.09-7.86 (m, 2H), 7.77 (s, 1H), 5.16-5.03 (m, 1H), 4.91-4.72 (m, J = 6.4 Hz, 1H), 4.28 (t, J = 6.6 Hz, 2H), 4.05 (s, 3H), 2.59 (s, 3H), 1.79 (t, J = 7.1 Hz, 2H), 1.45-1.31 (m, J = 6.7 Hz, 6H), 1.19-1.01 (m, 6H). |
| 571 | 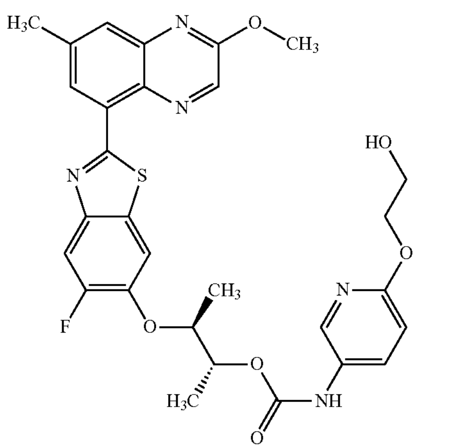 [SMILES: COc1cnc2c(-c3nc4cc(F)c(O[C@@H](C)[C@@H](C)OC(=O)Nc5ccc(OCCO)nc5)cc4s3)cc(C)cc2n1] | I-72 | I-93 | 594.15 | Orthogonal HPLC method B Injection 2, 2.303 | 35-100% 15 min, 100% 10 min | ¹H NMR (500 MHz, DMSO-d₆) δ 9.57 (br. s., 1H), 8.65 (s, 1H), 8.50 (s, 1H), 8.16 (br. s., 1H), 8.01-7.86 (m, 2H), 7.77 (s, 2H), 6.75 (d, J = 8.2 Hz, 1H), 5.07 (d, J = 6.1 Hz, 1H), 4.77 (d, J = 6.1 Hz, 1H), 4.17 (t, J = 4.9 Hz, 2H), 4.06 (s, 3H), 3.67 (d, J = 4.9 Hz, 1H), 3.59-3.55 (m, 2H), 2.60 (s, 3H), 1.38 (dd, J = 12.1, 6.3 Hz, 6H). |

-continued

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 572 | 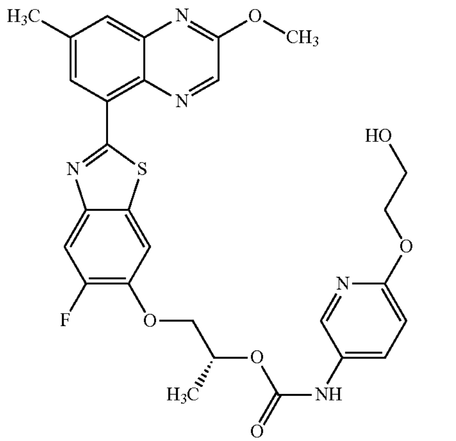 [SMILES: COc1cnc2c(-c3nc4cc(F)c(OC[C@@H](C)OC(=O)Nc5ccc(OCCO)nc5)cc4s3)cc(C)cc2n1] | I-67 | I-93 | 580.17 | Orthogonal HPLC method B Injection 2, 2.215 | 35-100% 10 min, 100% 10 min | ¹H NMR (500 MHz, DMSO-d₆) δ 9.80-9.39 (m, 1H), 8.66 (s, 1H), 8.51 (s, 1H), 8.19 (br. s., 1H), 7.97-7.87 (m, 2H), 7.78 (br. s., 2H), 6.77 (d, J = 8.5 Hz, 1H), 5.23 (br. s., 1H), 4.36-4.23 (m, 2H), 4.19 (d, J = 4.9 Hz, 2H), 4.06 (s, 3H), 3.68 (d, J = 4.9 Hz, 1H), 3.59 (br. s., 1H), 2.60 (s, 3H), 1.40 (d, J = 6.4 Hz, 3H). |
| 573 | 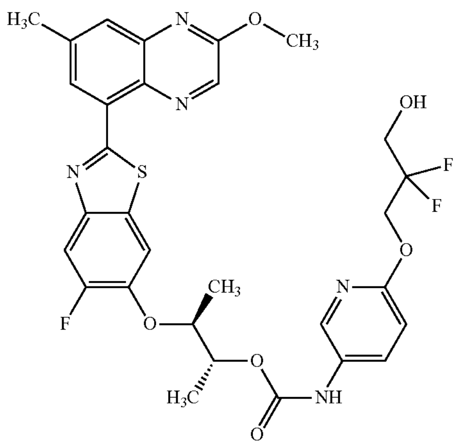 [SMILES: COc1cnc2c(-c3nc4cc(F)c(O[C@@H](C)[C@@H](C)OC(=O)Nc5ccc(OCC(F)(F)CO)nc5)cc4s3)cc(C)cc2n1] | I-72 | I-99 | 644.18 | Orthogonal HPLC method B Injection 2, 2.541 | 45-100% 15 min, 100% 10 min | ¹H NMR (500 MHz, DMSO-d₆) δ 9.65 (br. s., 1H), 8.67 (s, 1H), 8.52 (s, 1H), 8.20 (br. s., 1H), 8.02-7.88 (m, 2H), 7.79 (br. s., 2H), 6.86 (d, J = 8.2 Hz, 1H), 5.08 (d, J = 4.0 Hz, 1H), 4.78 (d, J = 4.0 Hz, 1H), 4.51 (t, J = 13.4 Hz, 2H), 4.06 (s, 3H), 3.78-3.65 (m, 2H), 2.61 (s, 3H), 1.38 (dd, J = 11.0, 6.4 Hz, 6H). |

| Ex. No. | Structure | R—OH | R—NH$_2$ | LCMS [M + H]$^+$ m/z | LCMS RT (Min) | HPLC Prep Method D | NMR |
|---|---|---|---|---|---|---|---|
| 574 | 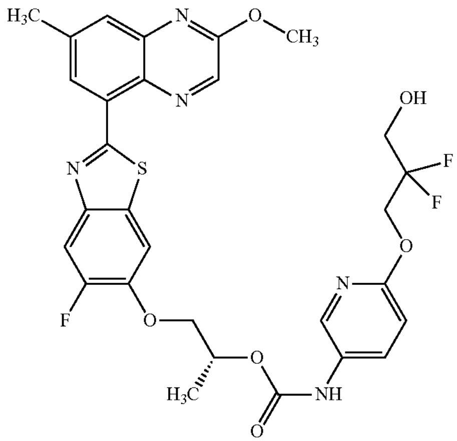 [SMILES: COc1cnc2c(-c3nc4cc(F)c(OC[C@@H](C)OC(=O)Nc5ccc(OCC(F)(F)CO)nc5)cc4s3)cc(C)cc2n1] | I-67 | I-99 | 630.16 | Orthogonal HPLC method B Injection 2, 2.460 | 35-100% 15 min, 100% 10 min | $^1$H NMR (500 MHz, DMSO-d$_6$) δ 9.85-9.51 (m, 1H), 8.61 (s, 1H), 8.46 (s, 1H), 8.20 (br. s., 1H), 7.93-7.68 (m, 4H), 6.86 (d, J = 8.9 Hz, 1H), 5.22 (br. s., 1H), 4.51 (t, J = 13.4 Hz, 2H), 4.37-4.18 (m, 2H), 4.04 (s, 3H), 3.75-3.73 (m, 2H), 2.56 (s, 3H), 1.39 (d, J = 6.4 Hz, 3H). |
| 575 | 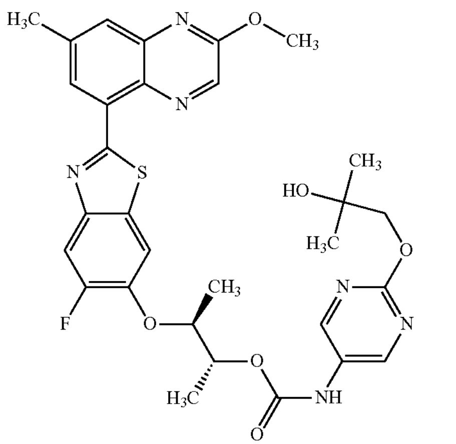 [SMILES: COc1cnc2c(-c3nc4cc(F)c(O[C@@H](C)[C@@H](C)OC(=O)Nc5cnc(OCC(C)(C)O)nc5)cc4s3)cc(C)cc2n1] | I-72 | I-101 | 623.2 | Orthogonal HPLC method B Injection 2, 2.418 | 40-80% 30 min, 100% 6 min | $^1$H NMR (500 MHz, DMSO-d$_6$) δ 9.72 (br. s., 1H), 8.61 (s, 1H), 8.53 (br. s., 2H), 8.46 (s, 1H), 7.94 (d, J = 8.2 Hz, 1H), 7.86 (d, J = 11.3 Hz, 1H), 7.73 (s, 1H), 5.02 (d, J = 6.4 Hz, 1H), 4.73 (d, J = 4.0 Hz, 1H), 4.63 (s, 1H), 4.00 (s, 3H), 3.95-3.89 (m, 2H), 2.54 (s, 3H), 1.38-1.26 (m, 6H), 1.10 (s, 6H). |

-continued

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 576 | 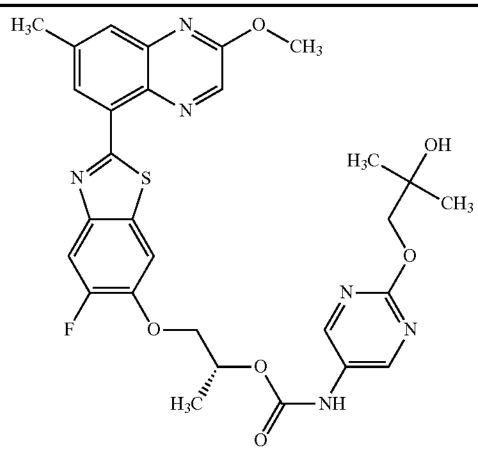 | I-67 | I-101 | 609.19 | Orthogonal HPLC method B Injection 2, 2.340 | 50-83% 20 min, 100% 5 min | ¹H NMR (500 MHz, DMSO-d₆) δ 8.68 (s, 1H), 8.62 (br. s., 2H), 8.52 (s, 1H), 8.00-7.90 (m, 2H), 7.79 (s, 1H), 5.35-5.03 (m, 1H), 4.44-4.22 (m, 2H), 4.07 (s, 3H), 2.61 (s, 3H), 1.42 (d, J = 6.4 Hz, 3H), 1.18 (s, 6H). |
| 577 | 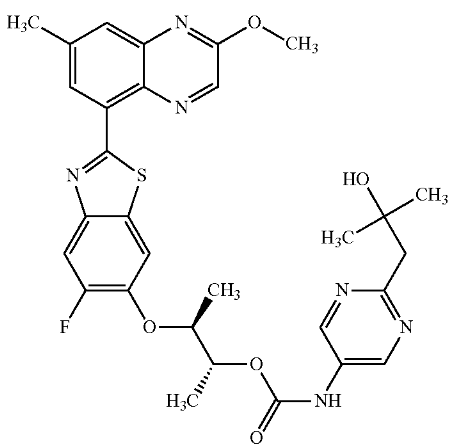 [SMILES: COc1cnc2c(-c3nc4cc(F)c(O[C@@H](C)[C@@H](C)OC(=O)Nc5cnc(CC(C)(C)O)nc5)cc4s3)cc(C)cc2n1] | I-72 | I-102 | 607.21 | Orthogonal HPLC method B Injection 2, 2.366 | 40-80% 25 min, 100% 6 min | ¹H NMR (500 MHz, DMSO-d₆) δ 10.14-9.80 (m, 1H), 8.84-8.76 (m, 2H), 8.75-8.71 (m, 1H), 8.61-8.55 (m, 1H), 8.08-8.03 (m, 1H), 7.99-7.93 (m, 1H), 7.87-7.83 (m, 1H), 5.19-5.03 (m, 1H), 4.91-4.73 (m, 1H), 4.13-4.06 (m, 3H), 2.66-2.59 (m, 3H), 1.45-1.32 (m, 6H), 1.11-1.04 (m, 6H). |

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 578 | 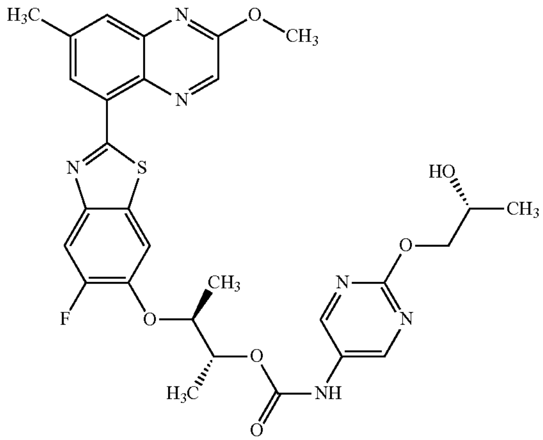 [SMILES: COc1cnc2c(-c3nc4cc(F)c(O[C@@H](C)[C@@H](C)OC(=O)Nc5cnc(OC[C@@H](C)O)nc5)cc4s3)cc(C)cc2n1] | I-72 | I-103 | 609.19 | Orthogonal HPLC method B Injection 2, 2.333 | 35-100% 20 min, 100% 5 min | ¹H NMR (500 MHz, DMSO-d₆) δ 9.85-9.67 (m, 1H), 8.70 (d, J = 2.1 Hz, 1H), 8.62-8.51 (m, 3H), 8.06-7.90 (m, 2H), 7.81 (s, 1H), 5.16-5.04 (m, J = 6.7 Hz, 1H), 4.90 (br. s., 1H), 4.84-4.73 (m, J = 6.1, 2.4 Hz, 1H), 4.07 (s, 4H), 4.04-3.83 (m, 2H), 3.44-3.34 (m, 3H), 2.62 (s, 3H), 1.38 (t, J = 6.1 Hz, 6H), 1.10 (d, J = 6.4 Hz, 3H). |
| 579 | 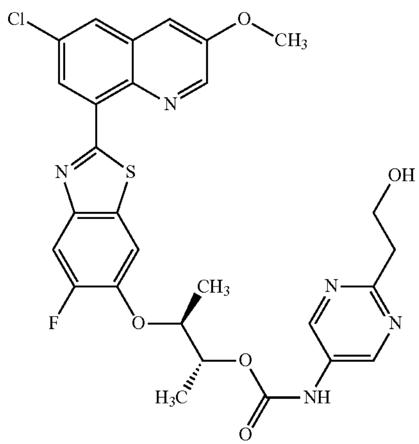 [SMILES: COc1cnc2c(-c3nc4cc(F)c(O[C@@H](C)[C@@H](C)OC(=O)Nc5cnc(CCO)nc5)cc4s3)cc(Cl)cc2c1] | I-91 | I-98 | 598.13 | Orthogonal HPLC method B Injection 2, 2.232 | 45-90% 20 min, 100% 7 min | ¹H NMR (500 MHz, DMSO-d₆) δ 10.11-9.73 (m, 1H), 8.88 (br. s., 1H), 8.76 (br. s., 2H), 8.64 (br. s., 1H), 8.20 (br. s., 1H), 8.06 (d, J = 7.3 Hz, 1H), 8.01-7.90 (m, 2H), 5.20-5.04 (m, 1H), 4.87-4.73 (m, 1H), 4.00 (br. s., 3H), 3.83-3.65 (m, 2H), 2.97-2.84 (m, 2H), 1.47-1.35 (m, 6H). |

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 580 | 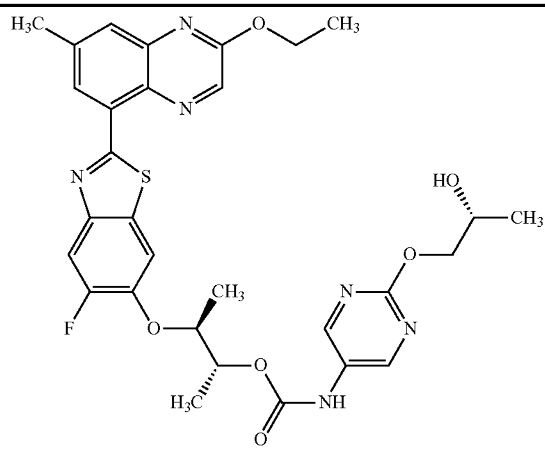 | I-80 | I-103 | 623.21 | Orthogonal HPLC method B Injection 2, 2.466 | 50-100% 10 min, 100% 5 min | ¹H NMR (500 MHz, DMSO-d₆) δ 9.79 (br. s., 1H), 8.76-8.32 (m, 4H), 8.05-7.88 (m, 2H), 7.78 (s, 1H), 5.18-5.03 (m, 1H), 4.87-4.73 (m, 1H), 4.52 (q, J = 7.0 Hz, 2H), 4.14-3.76 (m, 3H), 2.61 (s, 3H), 1.52-1.33 (m, 10H), 1.11 (d, J = 6.1 Hz, 3H). |
| 581 | 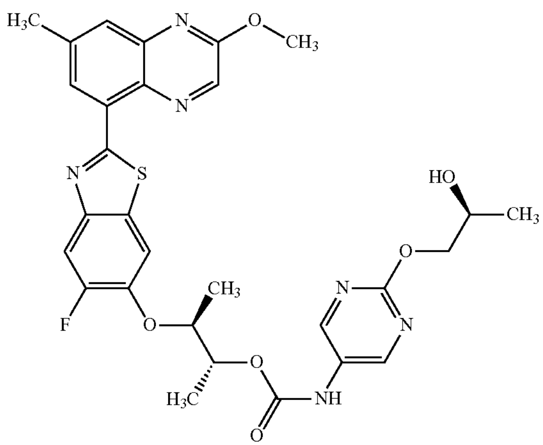 [SMILES: COc1cnc2c(-c3nc4cc(F)c(O[C@@H](C)[C@@H](C)OC(=O)Nc5cnc(OC[C@H](C)O)nc5)cc4s3)cc(C)cc2n1] | I-72 | I-104 | 609.1 | Orthogonal HPLC method B Injection 2, 2.35 | 50-100% 22 min, 100% 5 min | ¹H NMR (500 MHz, DMSO-d₆) δ 9.79 (br. s., 1H), 8.76-8.45 (m, 4H), 8.03 (d, J = 8.2 Hz, 1H), 7.95 (d, J = 11.3 Hz, 1H), 7.82 (s, 1H), 5.17-5.06 (m, 1H), 4.86-4.74 (m, J = 3.4 Hz, 1H), 4.17-4.05 (m, 4H), 4.04-3.86 (m, 2H), 2.63 (s, 3H), 1.45-1.35 (m, 6H), 1.12 (d, J = 6.1 Hz, 3H). |

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 582 | 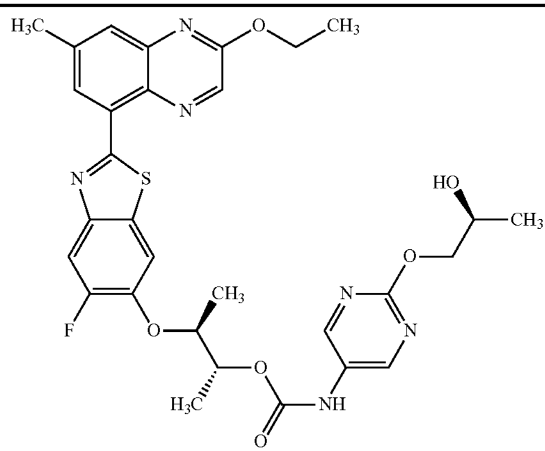 | I-80 | I-104 | 623.0 | Orthogonal HPLC method B Injection 2, 2.51 | 45-90% 22 min, 100% 5 min | ¹H NMR (500 MHz, DMSO-d₆) δ 9.80 (br. s., 1H), 8.74-8.43 (m, 4H), 8.03 (d, J = 8.2 Hz, 1H), 7.95 (d, J = 11.3 Hz, 1H), 7.79 (s, 1H), 5.17-5.05 (m, J = 6.1 Hz, 1H), 4.88-4.73 (m, 1H), 4.54 (q, J = 6.9 Hz, 2H), 4.18-3.86 (m, 3H), 2.62 (s, 3H), 1.45 (t, J = 7.0 Hz, 3H), 1.40-1.36 (m, J = 6.7 Hz, 6H), 1.12 (d, J = 6.1 Hz, 3H). |
| 583 | 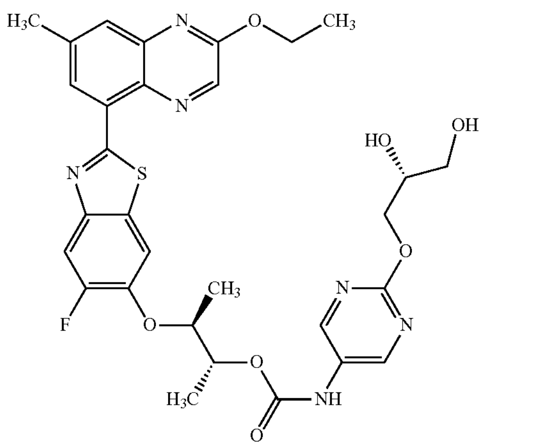 [SMILES: CCOc1cnc2c(-c3nc4cc(F)c(O[C@@H](C)[C@@H](C)OC(=O)Nc5cnc(OC[C@H](O)CO)nc5)cc4s3)cc(C)cc2n1] | I-80 | I-114 | 639.2 | Orthogonal HPLC method B Injection 2, 2.402 | 45-90% 22 min, 100% 5 min | ¹H NMR (500 MHz, DMSO-d₆) δ 9.93-9.60 (m, 1H), 8.68 (s, 1H), 8.62 (br. s., 2H), 8.55 (s, 1H), 8.04 (d, J = 8.2 Hz, 1H), 7.95 (d, J = 11.3 Hz, 1H), 7.79 (s, 1H), 5.10 (dd, J = 6.6, 2.6 Hz, 1H), 4.80 (dd, J = 6.4, 2.7 Hz, 1H), 4.66 (s, 1H), 4.53 (q, J = 7.0 Hz, 2H), 4.26 (dd, J = 11.0, 4.3 Hz, 1H), 4.13 (dd, J = 10.8, 6.6 Hz, 1H), 3.79 (d, J = 4.9 Hz, 1H), 3.43 (t, J = 5.6 Hz, 1H), 3.39-3.28 (m, 1H), 2.62 (s, 3H), 1.45 (t, J = 7.0 Hz, 3H), 1.42-1.36 (m, 6H). |

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 584 | 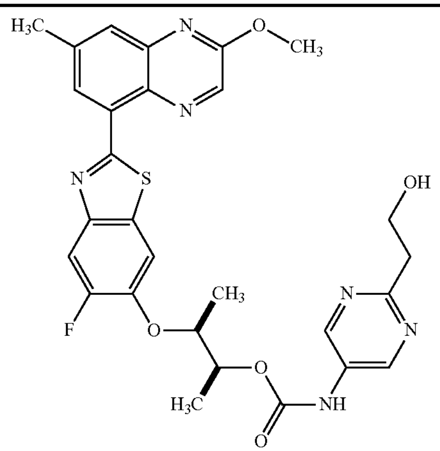 | 612 | I-98 | 579.2 | Orthogonal HPLC method B Injection 2, 2.24 | 45-90% 22 min, 100% 5 min | ¹H NMR (500 MHz, DMSO-d₆) δ 10.03 (br. s., 1H), 8.79 (br. s., 2H), 8.73 (s, 1H), 8.57 (s, 1H), 8.05 (d, J = 8.2 Hz, 1H), 7.95 (d, J = 11.6 Hz, 1H), 7.70 (dd, J = 6.9, 2.3 Hz, 2H), 5.19-5.05 (m, 1H), 4.79-4.68 (m, 1H), 4.61 (t, J = 5.5 Hz, 1H), 4.09 (s, 3H), 3.81 (q, J = 6.2 Hz, 2H), 2.96 (t, J = 6.7 Hz, 2H), 2.63 (s, 3H), 1.45-1.45 (m, 1H), 1.39 (dd, J = 11.9, 6.4 Hz, 6H). |
| 585 | 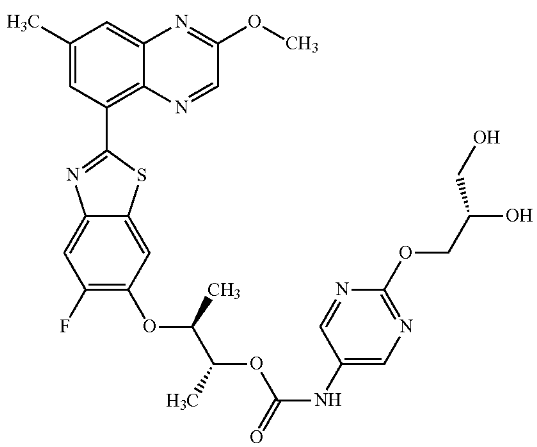 [SMILES: COc1cnc2c(-c3nc4cc(F)c(O[C@@H](C)[C@@H](C)OC(=O)Nc5cnc(OC[C@@H](O)CO)nc5)cc4s3)cc(C)cc2n1] | I-72 | I-113 | 625.3 | Orthogonal HPLC method B Injection 2, 2.25 | 45-90% 18 min, 100% 5 min | ¹H NMR (500 MHz, DMSO-d₆) δ 9.82 (br. s., 1H), 8.71 (s, 1H), 8.62 (br. s., 2H), 8.56 (s, 1H), 8.03 (d, J = 8.2 Hz, 1H), 7.95 (d, J = 11.6 Hz, 1H), 7.82 (s, 1H), 5.11 (dd, J = 6.4, 2.7 Hz, 1H), 4.81 (dd, J = 6.1, 2.7 Hz, 1H), 4.29-4.23 (m, 1H), 4.14 (ddd, J = 10.5, 6.6, 3.7 Hz, 1H), 4.08 (s, 3H), 3.84-3.71 (m, 1H), 3.46-3.40 (m, 1H), 3.52-3.13 (m, 2H), 2.63 (s, 3H), 1.46-1.21 (m, 6H). |

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 586 | 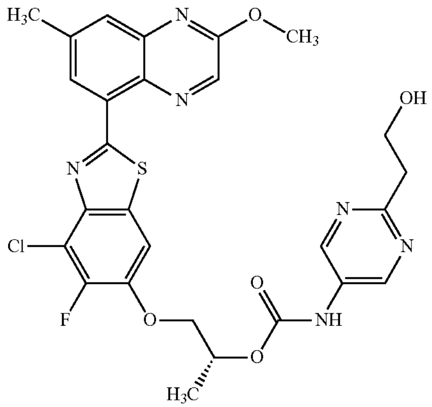 [SMILES: COc1cnc2c(-c3nc4c(Cl)c(F)c(OC[C@@H](C)OC(=O)Nc5cnc(CCO)nc5)cc4s3)cc(C)cc2n1] | I-69 | I-98 | 600.1 | Orthogonal HPLC method B Injection 2, 2.24 | 50-100% 20 min, 100% 5 min | ¹H NMR (500 MHz, DMSO-d₆) δ 10.07 (br. s., 1H), 8.78 (br. s., 2H), 8.67 (s, 1H), 8.52 (s, 1H), 7.96 (d, J = 7.6 Hz, 1H), 7.79 (s, 1H), 5.36-5.17 (m, J = 2.7 Hz, 1H), 4.44-4.36 (m, 1H), 4.33-4.27 (m, J = 10.8, 6.0 Hz, 1H), 4.08 (s, 3H), 3.87-3.74 (m, 2H), 2.96 (t, J = 6.9 Hz, 2H), 2.63 (s, 3H), 1.44 (d, J = 6.4 Hz, 3H). |
| 587 | 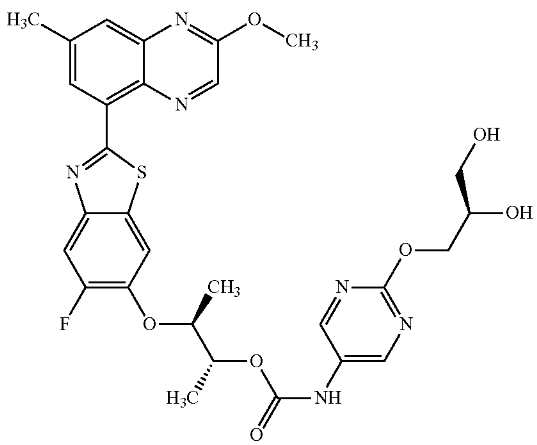 [SMILES: COc1cnc2c(-c3nc4cc(F)c(O[C@@H](C)[C@@H](C)OC(=O)Nc5cnc(OC[C@H](O)CO)nc5)cc4s3)cc(C)cc2n1] | I-72 | I-114 | 625.0 | Orthogonal HPLC method B Injection 2, 2.17 | 45-90% 18 min, 100% 5 min | ¹H NMR (500 MHz, DMSO-d₆) δ 9.81 (br. s., 1H), 8.71 (s, 1H), 8.62 (br. s., 2H), 8.55 (s, 1H), 8.03 (d, J = 8.2 Hz, 1H), 7.95 (d, J = 11.3 Hz, 1H), 7.81 (s, 1H), 5.10 (dd, J = 6.4, 2.4 Hz, 1H), 4.96 (d, J = 5.2 Hz, 1H), 4.85-4.74 (m, 1H), 4.68 (t, J = 5.5 Hz, 1H), 4.26 (dd, J = 11.0, 4.0 Hz, 1H), 4.13 (dd, J = 10.8, 6.6 Hz, 1H), 3.84-3.74 (m, 1H), 3.68-3.54 (m, 1H), 3.46-3.31 (m, 1H), 2.63 (s, 3H), 1.46-1.17 (m, 6H). |

| Ex. No. | Structure | R—OH | R—NH₂ | LCMS [M + H]⁺ m/z | LCMS Orthogonal HPLC RT (Min) | HPLC Prep Method D | NMR |
|---|---|---|---|---|---|---|---|
| 588 | 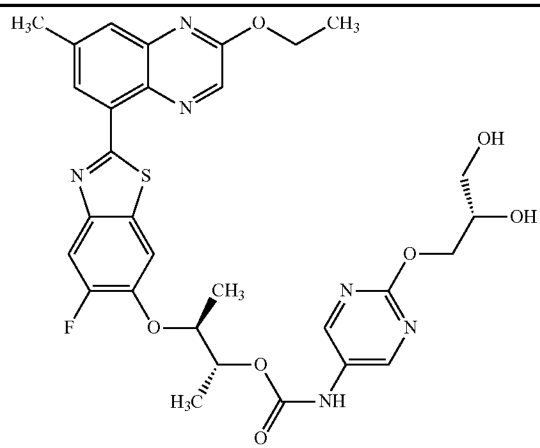 | I-80 | I-113 | 639.1 | Orthogonal HPLC method B Injection 2, 2.337 | 55-90% 25 min, 100% 4 min | ¹H NMR (500 MHz, DMSO-d₆) δ 9.82 (br. s., 1H), 8.70 (s, 1H), 8.62 (br. s., 2H), 8.57 (s, 1H), 8.05 (d, J = 7.9 Hz, 1H), 7.96 (d, J = 11.6 Hz, 1H), 7.81 (s, 1H), 5.10 (d, J = 6.7 Hz, 1H), 4.95 (d, J = 5.2 Hz, 1H), 4.80 (br. s., 1H), 4.66 (t, J = 5.6 Hz, 1H), 4.54 (q, J = 7.0 Hz, 2H), 4.32-4.23 (m, 1H), 4.19-4.10 (m, 1H), 3.83-3.68 (m, 1H), 3.43 (t, J = 5.6 Hz, 1H), 3.39-3.31 (m, 1H), 2.63 (s, 3H), 1.46 (t, J = 7.0 Hz, 3H), 1.42-1.36 (m, 6H). |
| 589 | 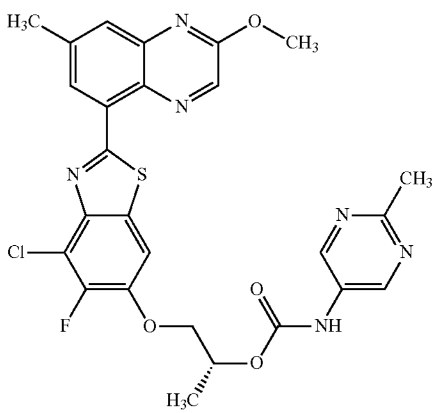 [SMILES: COc1cnc2c(-c3nc4c(Cl)c(F)c(OC[C@@H](C)OC(=O)Nc5cnc(C)nc5)cc4s3)cc(C)cc2n1] | I-69 | — | 569.05 | Orthogonal HPLC method B Injection 2, 2.218 | 45-85% 22 min, 100% 7 min | ¹H NMR (500 MHz, DMSO-d₆) δ 8.74 (br. s., 2H), 8.66 (s, 1H), 8.51 (s, 1H), 7.95 (d, J = 7.32 Hz, 1H), 7.78 (s, 1H), 5.25 (br. s., 1H), 4.35-4.46 (m, 1H), 4.22-4.32 (m, 1H), 4.06 (s, 3H), 2.62 (s, 3H), 2.52 (s, 3H), 1.42 (d, J = 6.41 Hz, 3H). |

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 590 | 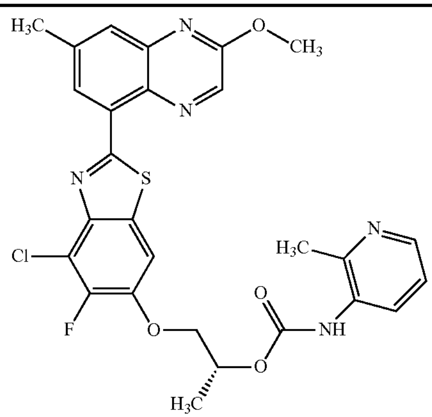 | I-69 | — | 569.05 | Orthogonal HPLC method B Injection 2, 2.229 | 40-100% 20 min, 100% 5 min | ¹H NMR (500 MHz, DMSO-d₆) δ 9.15 (br. s., 1H), 8.69 (s, 1H), 8.54 (s, 1H), 8.20 (d, J = 4.27 Hz, 1H), 7.97 (d, J = 7.32 Hz, 1H), 7.81 (s, 1H), 7.71 (d, J = 7.93 Hz, 1H), 6.98-7.25 (m, 1H), 5.24 (br. s., 1H), 4.36 (br. s., 1H), 4.27 (br. s., 1H), 4.06 (s, 3H), 2.63 (s, 3H), 2.37 (s, 3H), 1.39 (d, J = 6.41 Hz, 3H. |
| 591 | 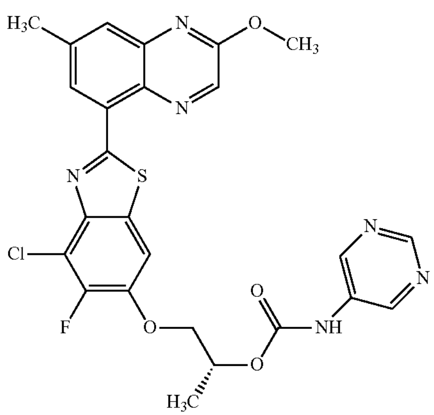 [SMILES: COc1cnc2c(-c3nc4c(Cl)c(F)c(OC[C@@H](C)OC(=O)Nc5cncnc5)cc4s3)cc(C)cc2n1] | I-69 | — | 555.10 | Orthogonal HPLC method B Injection 2, 2.452 | 30-90% 21 min, 100% 5 min | ¹H NMR (500 MHz, DMSO-d₆) δ 10.05-10.37 (m, 1H), 8.88 (s, 2H), 8.84 (s, 1H), 8.72 (s, 1H), 8.56 (d, J = 1.38 Hz, 1H), 8.01 (d, J = 7.70 Hz, 1H), 7.83 (s, 1H), 5.29 (dd, J = 3.03, 6.33 Hz, 1H), 4.41 (dd, J = 3.03, 10.73 Hz, 1H), 4.31 (dd, J = 5.91, 10.87 Hz, 1H), 4.07-4.11 (m, 3H), 2.64 (s, 4H), 1.44 (d, J = 6.60 Hz, 4H). |

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 592 | 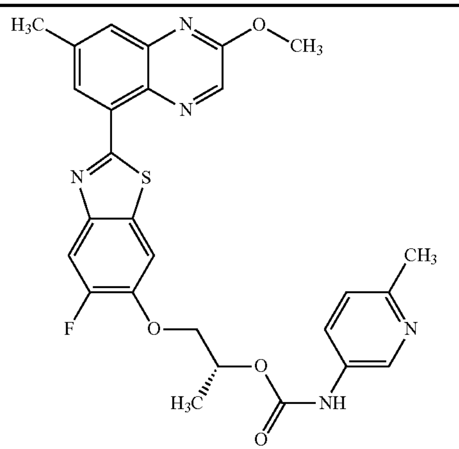 | I-67 | — | 534.2 | Orthogonal HPLC method B Injection 2, 2.063 | 40-80% 22 min, 100% 10 min | ¹H NMR (500 MHz, DMSO-d₆) δ 9.84 (br. s., 1H), 8.70 (s, 1H), 8.55-8.42 (m, 2H), 8.01-7.91 (m, 2H), 7.82-7.67 (m, 2H), 7.16 (d, J = 8.2 Hz, 1H), 5.36-5.02 (m, 1H), 4.41-4.17 (m, 2H), 4.06 (s, 3H), 2.60 (s, 3H), 2.40-2.23 (m, 3H), 1.40 (d, J = 6.4 Hz, 3H). |
| 593 | 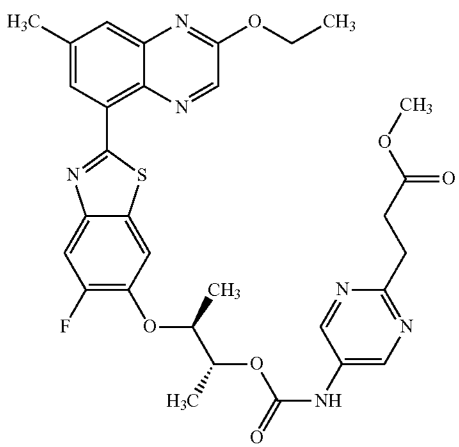 [SMILES: CCOc1cnc2c(-c3nc4cc(F)c(O[C@@H](C)[C@@H](C)OC(=O)Nc5cnc(CCC(=O)OC)nc5)cc4s3)cc(C)cc2n1] | I-80 | I-117 | 634.9 | Orthogonal HPLC method B Injection 2, 2.63 | 60-100% 15 min, 100% 10 min | ¹H NMR (500 MHz, DMSO-d₆) δ 9.92 (br. s., 1H), 8.70 (br. s., 2H), 8.61 (s, 1H), 8.49 (s, 1H), 7.96 (d, J = 8.2 Hz, 1H), 7.90 (d, J = 11.6 Hz, 1H), 7.75 (s, 1H), 5.18-5.02 (m, J = 6.6, 2.6 Hz, 1H), 4.87-4.71 (m, J = 4.0 Hz, 1H), 4.50 (q, J = 7.0 Hz, 2H), 3.54 (s, 2H), 3.03 (t, J = 7.0 Hz, 2H), 2.72 (t, J = 7.0 Hz, 2H), 2.56 (s, 3H), 1.53-1.12 (m, 9H). |

-continued

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 594 | 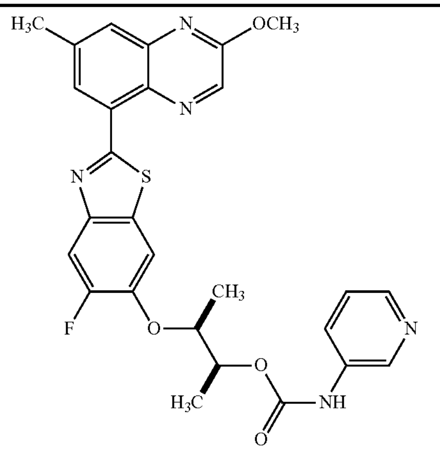 | 612 | — | 533.9 | Orthogonal HPLC method B Injection 2, 2.15 | 45-90% 22 min, 100% 5 min | ¹H NMR (500 MHz, DMSO-d₆) δ 10.03 (br. s., 1H), 8.75 (s, 1H), 8.69 (br. s., 1H), 8.59 (s, 1H), 8.26 (d, J = 4.0 Hz, 1H), 8.07 (d, J = 8.2 Hz, 1H), 7.97 (d, J = 11.6 Hz, 2H), 7.84 (s, 1H), 7.44-7.33 (m, 1H), 5.18-4.96 (m, 1H), 4.79-4.64 (m, 1H), 4.10 (s, 3H), 2.56 (s, 3H), 1.39 (dd, J = 12.8, 6.4 Hz, 6H). |
| 595 | 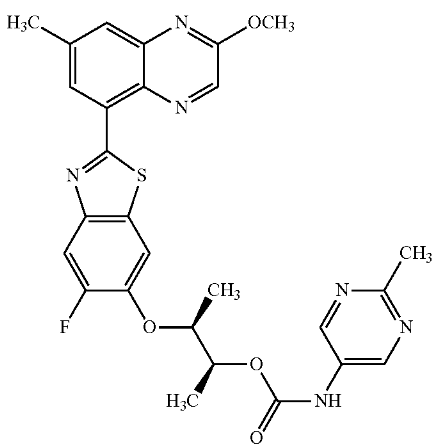 | 612 | — | 549.0 | Orthogonal HPLC method B Injection 2, 2.40 | 50-100% 20 min, 100% 5 min | ¹H NMR (500 MHz, DMSO-d₆) δ 10.02 (br. s, 1H), 8.90-8.68 (m, 3H), 8.56 (s, 1H), 8.05 (d, J = 8.2 Hz, 1H), 7.95 (d, J = 11.6 Hz, 1H), 7.82 (s, 1H), 5.27-4.96 (m, 1H), 4.81-4.55 (m, 1H), 4.09 (s, 3H), 2.63 (s, 3H), 2.56 (s, 3H), 1.39 (dd, J = 11.9, 6.4 Hz, 6H). |

-continued

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 596 | 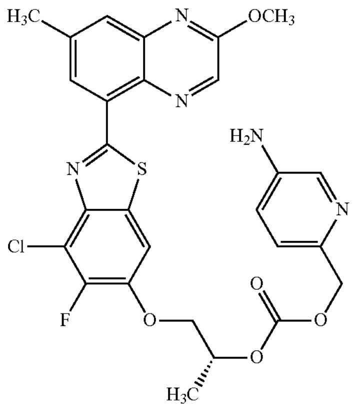 [SMILES: COc1cnc2c(-c3nc4c(Cl)c(F)c(OC[C@@H](C)OC(=O)OCc5ccc(N)cn5)cc4s3)cc(C)cc2n1] | I-69 | I-385A | 584.1 | Orthogonal HPLC method B Injection 2, 2.13 | 35-68% 25 min, 100% 7 min | ¹H NMR (500 MHz, DMSO-d₆) δ 9.88 (br. s., 1H), 8.34-8.65 (m, 3H), 7.82-7.98 (m, 2H), 7.73 (s, 1H), 7.37 (d, J = 8.54 Hz, 1H), 5.16-5.33 (m, 1H), 4.47 (br. s., 2H), 4.20-4.38 (m, 2H), 4.04 (s, 3H), 2.59 (s, 3H), 1.41 (d, J = 6.71 Hz, 3H). |
| 597 | 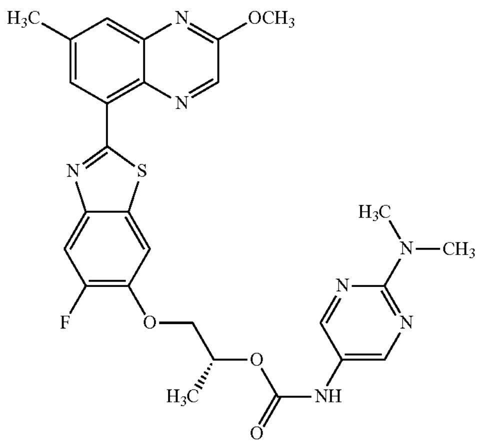 | I-67 | I-115 | 564.2 | Orthogonal HPLC method B Injection 2, 2.25 | 25-100% 20 min, 100% 5 min | ¹H NMR (500 MHz, DMSO-d₆) δ 9.44 (br. s., 1H), 8.72 (s, 1H), 8.56 (s, 1H), 8.37 (br. s., 1H), 7.96 (d, J = 11.0 Hz, 2H), 7.82 (s, 1H), 5.29-5.07 (m, 1H), 4.32 (br. s., 2H), 4.07 (s, 3H), 3.05 (br. s., 6H), 2.62 (s, 3H), 1.38 (d, J = 5.8 Hz, 3H). |

-continued

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 598 | 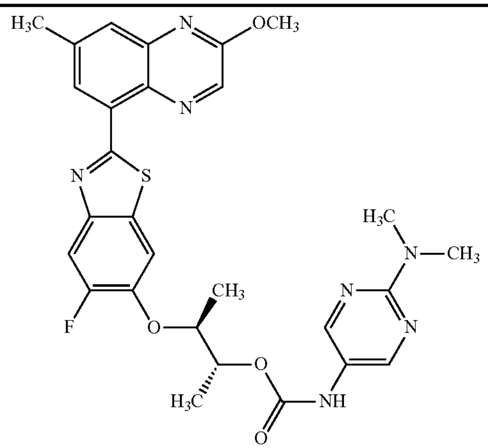 | I-72 | I-115 | 578.2 | Orthogonal HPLC method B Injection 2, 2.308 | 40-80% 15 min, 100% 5 min | ¹H NMR (500 MHz, DMSO-d₆) δ 9.34 (br. s., 1H), 8.67 (s, 1H), 8.52 (s, 1H), 8.33 (br. s., 2H), 8.07-7.87 (m, 2H), 7.78 (s, 1H), 5.03 (d, J = 4.3 Hz, 1H), 4.76 (br. s., 1H), 4.05 (s, 3H), 3.02 (s, 6H), 2.59 (s, 3H), 1.43-1.27 (m, 6H). |
| 599 | 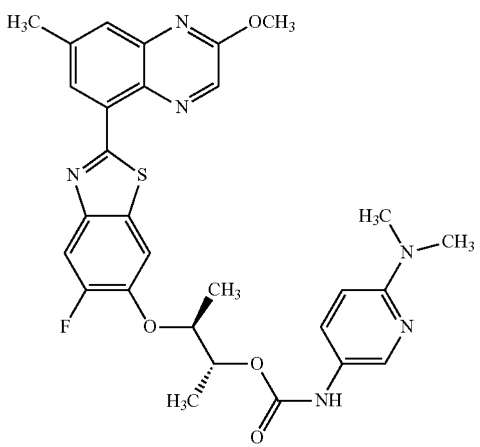 | I-72 | — | 577.20 | Orthogonal HPLC method B Injection 2, 2.762 | 70-100% 12 min, 100% 5 min | ¹H NMR (500 MHz, DMSO-d₆) δ 9.32 (br. s., 1H), 8.69 (s, 1H), 8.53 (s, 1H), 8.11 (br. s., 1H), 8.01 (d, J = 7.9 Hz, 1H), 7.93 (d, J = 11.6 Hz, 1H), 7.79 (s, 1H), 7.57 (br. s., 1H), 6.58 (d, J = 8.5 Hz, 1H), 5.04 (d, J = 4.3 Hz, 1H), 4.75 (br. s., 1H), 4.06 (s, 3H), 2.93 (s, 6H), 2.60 (s, 3H), 1.36 (dd, J = 13.4, 5.8 Hz, 6H). |

-continued

| Ex. No. | Structure | R—OH | R—NH$_2$ | LCMS [M + H]$^+$ m/z | LCMS RT (Min) | HPLC Prep Method D | NMR |
|---|---|---|---|---|---|---|---|
| 600 | 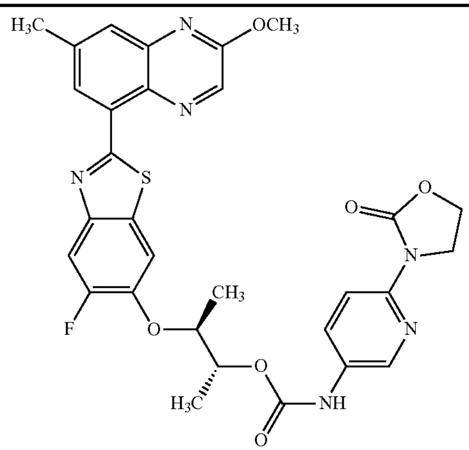 | I-72 | — | 619.15 | Orthogonal HPLC method B Injection 2, 2.41 | 50-100% 10 min, 100% 5 min | $^1$H NMR (500 MHz, DMSO-d$_6$) δ 9.78 (br. s., 1H), 8.68 (s, 1H), 8.53 (s, 1H), 8.37 (br. s., 1H), 8.06-7.83 (m, 4H), 7.79 (s, 1H), 5.08 (dd, J = 6.6, 2.6 Hz, 1H), 4.80 (dd, J = 6.3, 2.6 Hz, 1H), 4.51-4.30 (m, 2H), 4.12-3.97 (m, 5H), 2.60 (s, 3H), 1.38 (t, J = 6.9 Hz, 6H). |
| 601 | 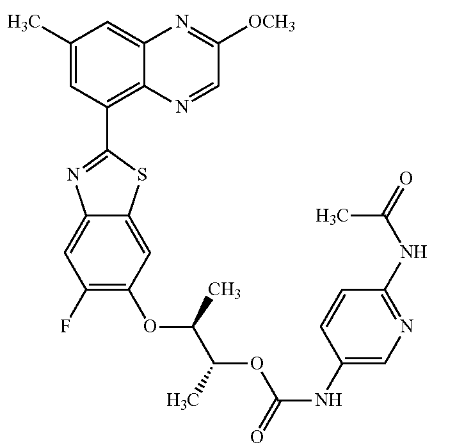 [SMILES: COc1cnc2c(-c3nc4cc(F)c(O[C@@H](C)[C@@H](C)OC(=O)Nc5ccc(NC(C)=O)nc5)cc4s3)cc(C)cc2n1] | I-72 | — | 591.20 | Orthogonal HPLC method B Injection 2, 2.104 | 50-100% 12 min, 100% 5 min | $^1$H NMR (500 MHz, DMSO-d$_6$) δ 10.35 (s, 1H), 9.75 (br. s., 1H), 8.67 (s, 1H), 8.53 (s, 1H), 8.35 (br. s., 1H), 8.09-7.89 (m, 2H), 7.79 (s, 1H), 5.08 (dd, J = 6.4, 2.4 Hz, 1H), 4.79 (dd, J = 6.1, 2.7 Hz, 1H), 4.06 (q, 3H), 2.60 (s, 3H), 2.03 (s, 3H), 1.38 (t, J = 6.6 Hz, 6H). |

| Ex. No. | Structure | R—OH | R—NH$_2$ | LCMS [M + H]$^+$ m/z | LCMS RT (Min) | HPLC Prep Method D | NMR |
|---|---|---|---|---|---|---|---|
| 602 | 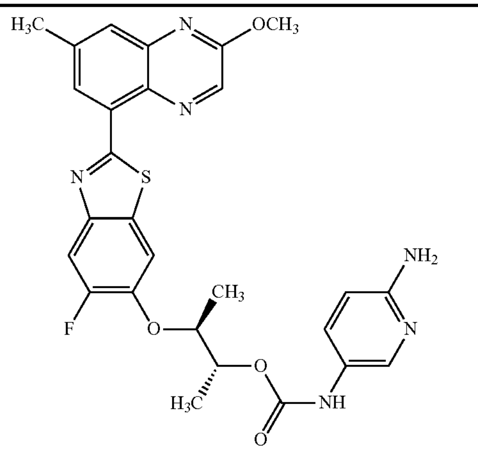 | I-72 | — | 549.20 | Orthogonal HPLC method B Injection 2, 2.034 | 45-90% 25 min, 100% 5 min | $^1$H NMR (500 MHz, DMSO-d$_6$) δ 9.25 (br. s., 1H), 8.70 (s, 1H), 8.54 (s, 1H), 8.01 (d, J = 7.9 Hz, 1H), 7.94 (d, J = 11.3 Hz, 2H), 7.80 (s, 1H), 7.43 (br. s., 1H), 6.40 (d, J = 8.5 Hz, 1H), 5.03 (d, J = 4.0 Hz, 1H), 4.73 (br. s., 1H), 4.06 (s, 3H), 2.61 (s, 3H), 1.44-1.30 (m, 6H). |
| 603 | 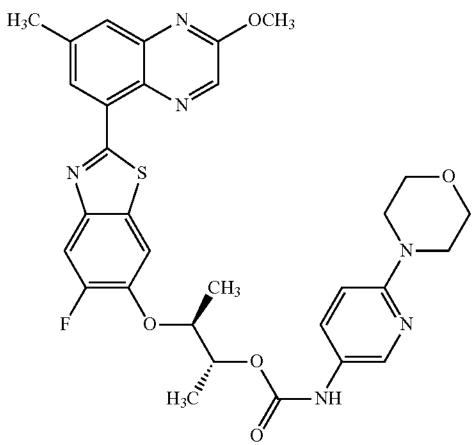 [SMILES: COc1cnc2c(-c3nc4cc(F)c(O[C@@H](C)[C@@H](C)OC(=O)Nc5ccc(N6CCOCC6)nc5)cc4s3)cc(C)cc2n1] | I-72 | — | 619.21 | Orthogonal HPLC method B Injection 2, 2.267 | 30-100% 15 min, 100% 5 min | $^1$H NMR (500 MHz, DMSO-d$_6$) δ 9.51-9.30 (m, 1H), 8.77-8.72 (m, 1H), 8.63-8.52 (m, 1H), 8.25-8.13 (m, 1H), 8.07-8.01 (m, 1H), 8.00-7.93 (m, 1H), 7.88-7.82 (m, 1H), 7.73-7.58 (m, 1H), 6.90-6.70 (m, 1H), 5.13-4.99 (m, 1H), 4.86-4.59 (m, 1H), 4.09 (s, 3H), 3.75-3.61 (m, 8H), 2.64 (s, 3H), 1.42-1.31 (m, 6H). |

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 604 | 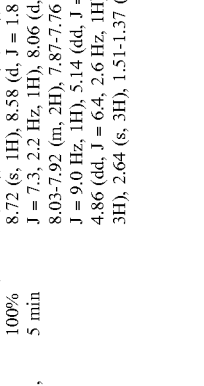 | I-72 | — | 706.05 | Orthogonal HPLC method B Injection 2, 2.525 | 30-70% 20 min, 100% 5 min | ¹H NMR (400 MHz, DMSO-d₆) δ 11.06 (br. s., 1H), 10.12-9.78 (m, 1H), 8.79 (br. s., 2H), 8.72 (s, 1H), 8.58 (d, J = 1.8 Hz, 1H), 8.19 (dd, J = 7.3, 2.2 Hz, 1H), 8.06 (d, J = 8.1 Hz, 1H), 8.03-7.92 (m, 2H), 7.87-7.76 (m, 1H), 7.57 (t, J = 9.0 Hz, 1H), 5.14 (dd, J = 6.6, 2.6 Hz, 1H), 4.86 (dd, J = 6.4, 2.6 Hz, 1H), 4.15-4.02 (m, 3H), 2.64 (s, 3H), 1.51-1.37 (m, 6H). |
| 605 | 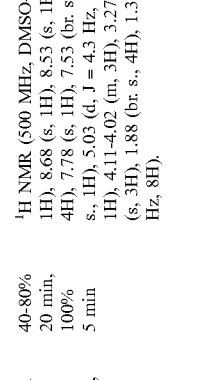 | I-72 | — | 602.55 | Orthogonal HPLC method B Injection 2, 2.196 | 40-80% 20 min, 100% 5 min | ¹H NMR (500 MHz, DMSO-d₆) δ 9.25 (br. s., 1H), 8.68 (s, 1H), 8.53 (s, 1H), 8.11-7.88 (m, 4H), 7.78 (s, 1H), 7.53 (br. s., 1H), 6.35 (br. s., 1H), 5.03 (d, J = 4.3 Hz, 1H), 4.75 (br. s., 1H), 4.11-4.02 (m, 3H), 3.27 (br. s., 2H), 2.60 (s, 3H), 1.88 (br. s., 4H), 1.36 (dd, J = 14.5, 5.3 Hz, 8H). |

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 606 | 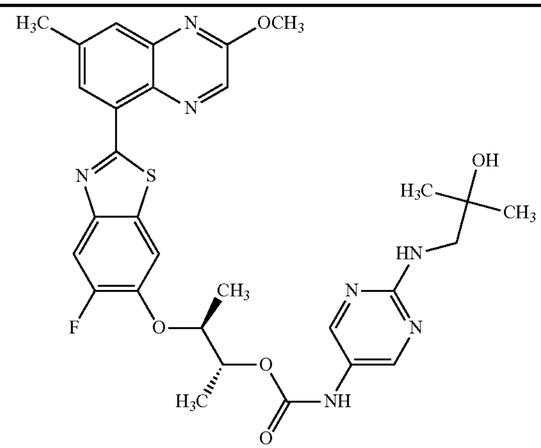 | I-72 | — | 622.0 | Orthogonal HPLC method B Injection 2, 2.219 | 30-70% 20 min, 100% 5 min | ¹H NMR (500 MHz, DMSO-d₆) δ 9.33 (br. s., 1H), 8.67 (s, 1H), 8.52 (s, 1H), 8.27 (br. s., 2H), 8.03-7.88 (m, 2H), 7.78 (s, 1H), 5.03 (d, J = 6.4 Hz, 1H), 4.75 (br. s., 1H), 4.05 (s, 3H), 3.22 (d, J = 5.8 Hz, 2H), 2.60 (s, 3H), 1.47-1.24 (m, 6H), 1.06 (s, 6H). |
| 607 | 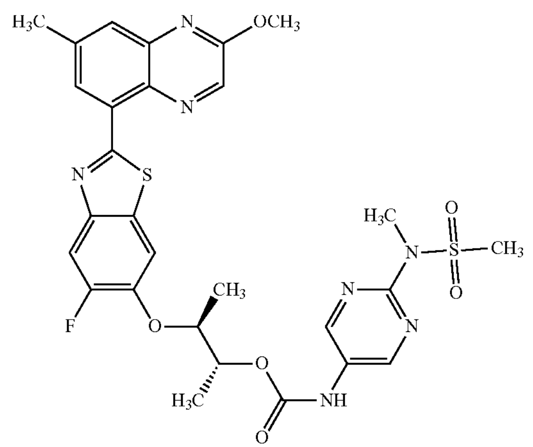 | I-72 | I-116 | 642.16 | Orthogonal HPLC method B Injection 2, 2.517 | 30-70% 20 min, 100% 5 min | ¹H NMR (400 MHz, MeOH-d₄) δ 8.76-8.61 (m, 2H), 8.56-8.45 (m, 2H), 7.79-7.68 (m, 3H), 5.18-5.05 (m, 1H), 4.12 (s, 3H), 3.36 (d, J = 1.5 Hz, 6H), 2.63 (s, 3H), 1.45 (d, J = 6.4 Hz, 6H). |

| Ex. No. | Structure | R—OH | R—NH$_2$ | LCMS [M + H]$^+$ m/z | LCMS RT (Min) | HPLC Prep Method D | NMR |
|---|---|---|---|---|---|---|---|
| 608 | 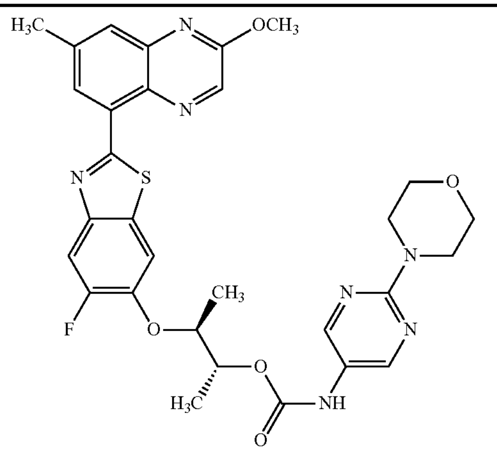 | I-72 | — | 620.12 | Orthogonal HPLC method B Injection 2, 2.438 | 40-80% 20 min, 100% 5 min | $^1$H NMR (500 MHz, DMSO-d$_6$) δ 9.46 (br. s., 1H), 8.69 (s, 1H), 8.54 (s, 1H), 8.40 (br. s., 2H), 8.07-7.89 (m, 2H), 7.80 (s, 1H), 5.04 (d, J = 4.9 Hz, 1H), 4.79 (br. s., 1H), 4.06 (s, 4H), 3.68-3.50 (m, 8H), 2.61 (s, 3H), 1.75-1.75 (m, 1H), 1.35 (d, J = 6.4 Hz, 6H). |
| 609 | 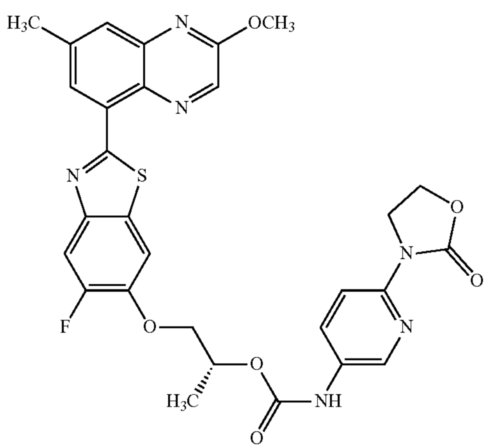 [SMILES: COc1cnc2c(-c3nc4cc(F)c(OC[C@@H](C)OC(=O)Nc5ccc(N6CCOC6=O)nc5)cc4s3)cc(C)cc2n1] | I-67 | — | 605.16 | Orthogonal HPLC method B Injection 2, 2.362 | 20-100% 15 min, 100% 5 min | $^1$H NMR (500 MHz, DMSO-d$_6$) δ 9.88 (br. s., 1H), 8.67 (s, 1H), 8.51 (s, 1H), 8.41 (br. s., 1H), 8.01-7.86 (m, 4H), 7.78 (s, 1H), 5.25 (br. s., 1H), 4.55-4.19 (m, 4H), 4.16-3.99 (m, 5H), 3.62-3.52 (m, 3H), 2.60 (s, 3H), 1.42 (d, J = 6.1 Hz, 3H). |

| Ex. No. | Structure | R—OH | R—NH₂ | LCMS [M + H]⁺ m/z | LCMS RT (Min) | HPLC Prep Method D | NMR |
|---|---|---|---|---|---|---|---|
| 610 | 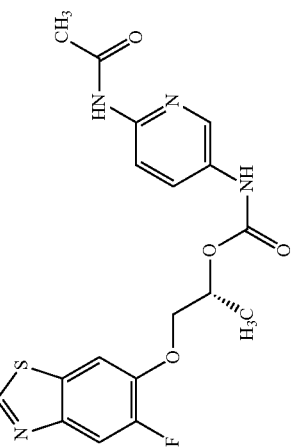 | I-67 | — | 577.17 | Orthogonal HPLC method B Injection 2, 2.056 | 20-100% 20 min, 100% 5 min | ¹H NMR (500 MHz, DMSO-d₆) δ 10.36 (s, 1H), 8.72 (s, 1H), 8.56 (d, J = 1.7 Hz, 1H), 8.38 (br. s., 1H), 8.06-7.91 (m, 3H), 7.87-7.78 (m, 2H), 5.24 (td, J = 6.3, 3.4 Hz, 1H), 4.43-4.22 (m, 2H), 4.08 (s, 3H), 3.90 (s, 3H), 1.42 (d, J = 6.3 Hz, 3H). |
| 611 | 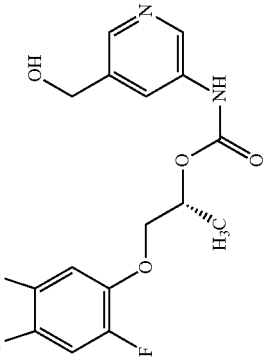 | I-67 | I-119 | 550.20 | 2.155 | 45-95% 13 min, 100% 6 min | ¹H NMR (500 MHz, DMSO-d₆) δ 9.96-9.57 (m, 1H), 8.75 (s, 1H), 8.62-8.49 (m, 2H), 8.10-7.94 (m, 2H), 7.84 (s, 1H), 7.81-7.74 (m, 1H), 7.19 (d, J = 8.5 Hz, 1H), 5.32-5.15 (m, 1H), 4.67-4.53 (m, 1H), 4.41-4.23 (m, 2H), 4.13-4.05 (m, 3H), 3.69 (t, J = 6.9 Hz, 2H), 2.80 (t, J = 7.0 Hz, 2H), 2.66-2.59 (m, 3H), 1.42 (d, J = 6.6 Hz, 3H). |

Example 612

(2S,3S)-3-((5-fluoro-2-(2-methoxy-7-methylquinoxalin-5-yl)benzo[d]thiazol-6-yl)oxy)butan-2-ol

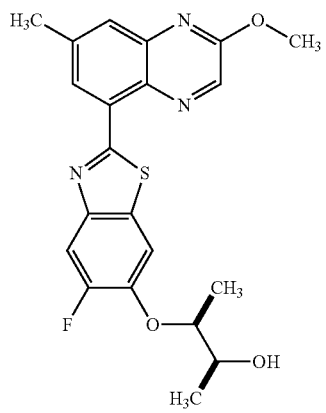
(612)

This intermediate was prepared from (2R,3S)-butane-2,3-diol using the same synthetic sequence as described for Intermediate I-72. LC-MS: Method H, RT=1.21 min, MS (ESI) m/z: 414.0 (M+H)+. $^1$H NMR (400 MHz, CDCl$_3$) δ 8.70-8.62 (m, 1H), 8.58 (s, 1H), 7.90-7.83 (m, 1H), 7.82-7.77 (m, 1H), 7.60-7.45 (m, 1H), 4.36-4.19 (m, 1H), 4.16 (s, 3H), 4.05-3.87 (m, 1H), 2.68 (s, 3H), 2.65-2.58 (m, 1H), 1.38 (d, J=6.4 Hz, 3H), 1.34 (d, J=6.4 Hz, 3H).

Example 613

(2R,3S)-3-((2-(2-carbamoyl-7-methylquinoxalin-5-yl)-5-fluorobenzo[d]thiazol-6-yl)oxy)butan-2-yl (2-methylpyrimidin-5-yl)carbamate

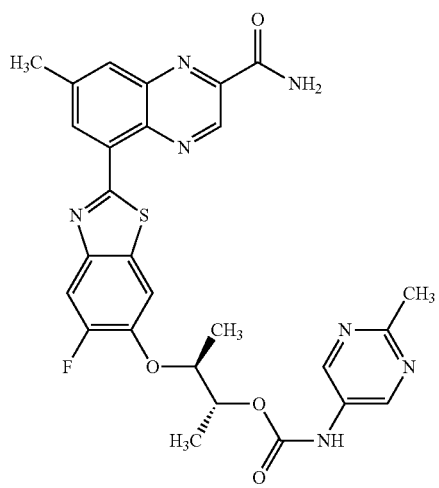
(613)

Intermediate I-75 was dissolved in a 7 M ammonia solution in MeOH (2 mL, 92 mmol) and the resulting mixture stirred for 12 h at 65° C. The reaction mixture was then concentrated and purified by reverse phase HPLC (Method D, 30-70% 20 min, 100% 5 min) to yield Example 613 (8.4 mg, 0.014 mmol, 74% yield). LC-MS: Method H, RT=0.99 min, MS (ESI) m/z: 562.20 (M+H)+. $^1$H NMR (500 MHz, DMSO-d$_6$) δ 9.52 (s, 1H), 8.87 (s, 1H), 8.73 (br. s., 2H), 8.44 (s, 1H), 8.19-7.73 (m, 4H), 5.12 (dd, J=6.4, 2.4 Hz, 1H), 4.83 (dd, J=6.3, 2.6 Hz, 1H), 3.48-3.26 (m, 2H), 2.71 (s, 3H), 1.41 (t, J=6.4 Hz, 7H).

Example 614

(2R,3S)-3-((5-fluoro-2-(7-methyl-2-(methylcarbamoyl)quinoxalin-5-yl)benzo[d]thiazol-6-yl)oxy)butan-2-yl (2-methylpyrimidin-5-yl)carbamate

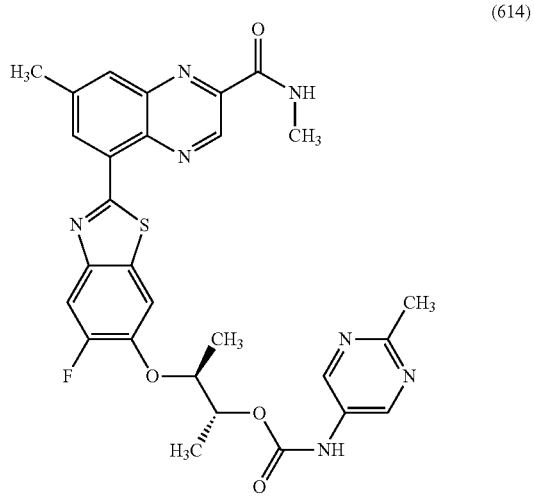
(614)

Example 614 was prepared from methylamine (33% in EtOH) using the method described for Example 613. LC-MS: Method H, RT=0.99 min, MS (ESI) m/z: 576.18 (M+H)+. $^1$H NMR (500 MHz, DMSO-d$_6$) δ 9.48 (s, 1H), 9.07 (d, J=4.9 Hz, 1H), 8.83 (s, 1H), 8.73 (br. s., 2H), 8.11-8.01 (m, 2H), 7.94 (d, J=11.6 Hz, 1H), 5.12 (d, J=6.4 Hz, 1H), 4.83 (d, J=4.3 Hz, 1H), 2.98-2.90 (m, 3H), 2.70 (s, 3H), 2.52 (br. s., 3H), 1.40 (t, J=6.9 Hz, 6H).

Example 615

(2R,3S)-3-((2-(2-(dimethylcarbamoyl)-7-methylquinoxalin-5-yl)-5-fluorobenzo[d]thiazol-6-yl)oxy)butan-2-yl (2-methylpyrimidin-5-yl)carbamate

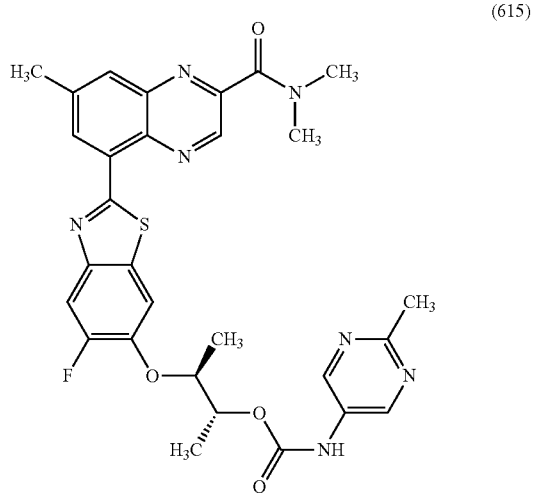
(615)

Example 615 was prepared from dimethylamine (2M in THF) using the method as described for Example 613. LC-MS: Method H, RT=0.99 min, MS (ESI) m/z: 590.20 (M+H)+. 1H NMR (500 MHz, DMSO-d6) δ 9.96 (br. s., 1H), 9.19 (s, 1H), 8.84 (s, 1H), 8.72 (br. s., 2H), 8.09-8.03 (m, 2H), 7.96 (d, J=11.3 Hz, 1H), 5.12 (d, J=6.1 Hz, 1H), 4.82 (d, J=5.5 Hz, 1H), 3.26-3.07 (m, 6H), 2.69 (s, 3H), 1.40 (t, J=6.4 Hz, 6H).

Example 616

(2R,3S)-3-((5-fluoro-2-(2-((2-hydroxyethyl)carbamoyl)-7-methylquinoxalin-5-yl)benzo[d]thiazol-6-yl)oxy)butan-2-yl (2-methylpyrimidin-5-yl)carbamate

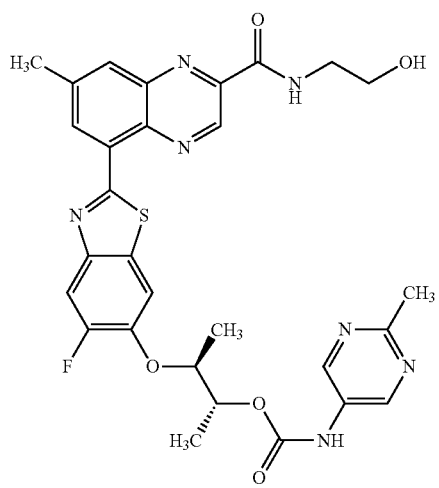

(616)

Example 616 was prepared from 2-aminoethanol using the same method as described for Example 613. LC-MS: Method H, RT=1.09 min, MS (ESI) m/z: 606.0 (M+H)+.

Preparation of Alcohol Examples

The alcohols in the accompanying table were prepared according to the following three general procedures.

Primary Alcohols: The appropriately substituted hetero-aryl ester was subjected to conditions described in Procedure G. Purification by Prep HPLC (Method D) afforded the desired example.

Secondary Alcohols: The appropriately substituted hetero-aryl aldehyde was subjected to conditions described in Procedure H. Purification by Prep HPLC (Method D) afforded the desired example.

Tertiary Alcohols: The appropriately substituted hetero-aryl ester was subjected to conditions described in Procedure H. Purification by Prep HPLC (Method D) afforded the desired example.

| Ex. No. | Structure | Ester/Aldehyde | LCMS [M + H]+ m/z | Orthogonal HPLC method B Injection 2 | HPLC Prep Method D | NMR |
|---|---|---|---|---|---|---|
| 617 | 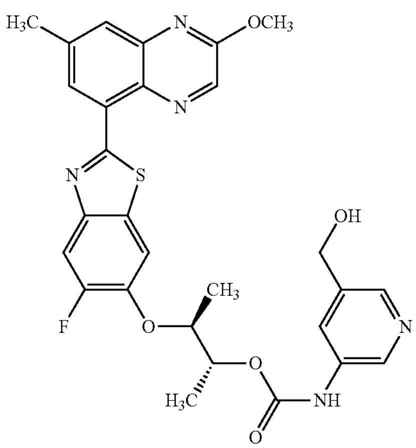 [SMILES: COc1cnc2c(-c3nc4cc(F)c(O[C@@H](C)[C@@H](C)OC(=O)Nc5cncc(CO)c5)cc4s3)cc(C)cc2n1] | I-118 | 564.0 | 2.037 | 45-90% 20 min, 100% 7 min | 1H NMR (500 MHz, DMSO-d6) δ 9.89 (br. s., 1H), 8.72 (s, 1H), 8.56 (s, 1H), 8.51 (br. s., 1H), 8.15 (s, 1H), 8.04 (d, J = 8.2 Hz, 1H), 7.96 (d, J = 11.6 Hz, 1H), 7.89 (br. s., 1H), 7.82 (s, 1H), 5.33 (t, J = 5.6 Hz, 1H), 5.19-5.03 (m, J = 6.6, 2.6 Hz, 1H), 4.83-4.73 (m, 1H), 4.49 (d, J = 5.5 Hz, 2H), 4.09 (s, 3H), 2.63 (s, 3H), 1.41 (t, J = 6.3 Hz, 6H) |

-continued

| Ex. No. | Structure | Ester/ Aldehyde | LCMS [M + H]+ m/z | Orthogonal HPLC method B Injection 2 | HPLC Prep Method D | NMR |
|---|---|---|---|---|---|---|
| 618 | 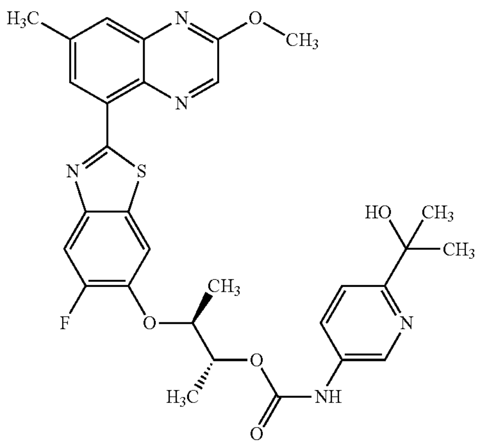 [SMILES: COc1cnc2c(-c3nc4cc(F)c(O[C@@H](C)[C@@H](C)OC(=O)Nc5ccc(C(C)(C)O)nc5)cc4s3)cc(C)cc2n1] | I-74 | 592.1 | 2.126 | 45-90% 12 min, 100% 5 min | ¹H NMR (500 MHz, DMSO-d₆) δ 9.82 (br. s., 1H), 8.69 (s, 1H), 8.56-8.48 (m, 2H), 8.02 (d, J = 8.2 Hz, 1H), 7.94 (d, J = 11.6 Hz, 1H), 7.83 (br. s., 1H), 7.79 (s, 1H), 7.55 (d, J = 8.5 Hz, 1H), 5.11 (d, J = 5.5 Hz, 1H), 4.79 (d, J = 6.1 Hz, 1H), 4.07 (s, 3H), 2.61 (s, 3H), 1.43-1.37 (m, 12H) |
| 619 | 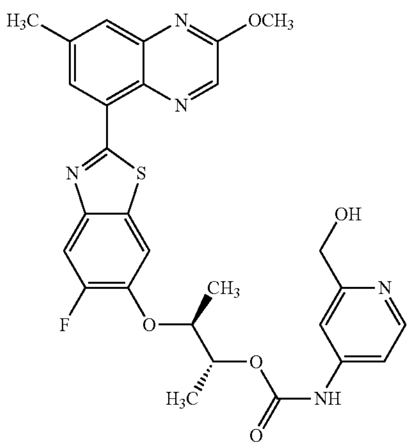 [SMILES: COc1cnc2c(-c3nc4cc(F)c(O[C@@H](C)[C@@H](C)OC(=O)Nc5ccnc(CO)c5)cc4s3)cc(C)cc2n1] | I-85 | 564.1 | 2.092 | 55-85% 25 min, 85% 4 min | ¹H NMR (500 MHz, DMSO-d₆) δ 10.18 (s, 1H), 8.71 (s, 1H), 8.56 (s, 1H), 8.27 (d, J = 5.5 Hz, 1H), 8.04 (d, J = 8.2 Hz, 1H), 7.96 (d, J = 11.6 Hz, 1H), 7.82 (s, 1H), 7.62 (s, 1H), 7.34 (d, J = 4.0 Hz, 1H), 5.14 (dd, J = 6.4, 2.7 Hz, 1H), 4.80 (dd, J = 6.4, 2.7 Hz, 1H), 4.49 (d, J = 4.6 Hz, 2H), 4.08 (s, 3H), 2.63 (s, 3H), 1.41 (t, J = 6.0 Hz, 6H) |
| 620 | 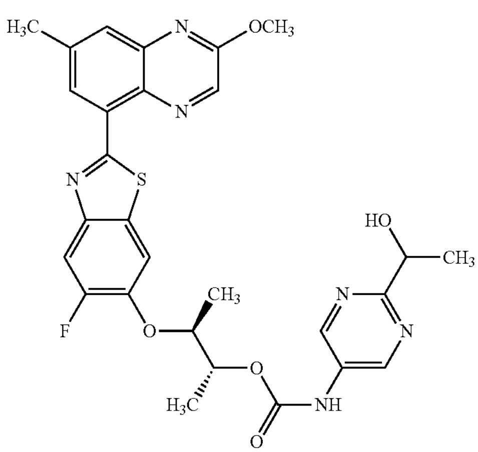 [SMILES: COc1cnc2c(-c3nc4cc(F)c(O[C@@H](C)[C@@H](C)OC(=O)Nc5cnc(C(C)O)nc5)cc4s3)cc(C)cc2n1] | I-120 | 579.2 | 2.384 | 45-90% 20 min, 100% 7 min | ¹H NMR (500 MHz, DMSO-d₆) δ 10.04 (br. s., 1H), 8.83 (br. s., 2H), 8.72 (s, 1H), 8.56 (s, 1H), 8.04 (d, J = 8.2 Hz, 1H), 7.96 (d, J = 11.6 Hz, 1H), 7.82 (s, 1H), 5.14 (d, J = 5.2 Hz, 1H), 4.82 (d, J = 3.7 Hz, 1H), 4.76-4.66 (m, 1H), 4.09 (s, 3H), 3.40-3.37 (m, 1H), 2.63 (s, 3H), 1.41 (dd, J = 6.0, 4.1 Hz, 6H), 1.36 (d, J = 6.4 Hz, 3H) |

Example 621

2-((4-chloro-5-fluoro-2-(2-methoxy-7-methylquinoxalin-5-yl)benzo[d]thiazol-6-yl)oxy)ethyl isothiazol-5-ylcarbamate

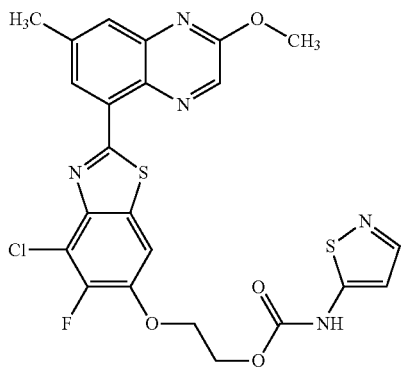

(621)

Example 318 (12 mg, 0.029 mmol), isothiazole-5-carboxylic acid (7.38 mg, 0.057 mmol) and triethylamine (7.97 µL, 0.057 mmol) were suspended in toluene (1 mL) in a pressure rated 1 dram vial. Diphenylphosphoryl azide (15.73 mg, 0.057 mmol) was added to the mixture which was heated to 110° C. for 3 hours. The crude reaction mixture was purified by reverse phase HPLC (Method D, 65-100% 20 min, 100% 5 min) to yield Example 621 (1.3 mg, 2.38 mmol, 8% yield). LC-MS: Method H, RT=1.25 min, MS (ESI) m/z: 546.10 (M+H)$^+$. $^1$H NMR (500 MHz, DMSO-d$_6$) δ 8.77 (s, 1H), 8.62 (s, 1H), 8.21 (s, 1H), 8.02-8.12 (m, 1H), 7.88 (s, 1H), 6.81 (s, 1H), 4.61-4.69 (m, 2H), 4.46-4.56 (m, 2H), 4.10 (s, 3H), 3.19 (s, 3H).

Example 622

(R)-5-(((4-chloro-5-fluoro-2-(2-methoxy-7-methylquinoxalin-5-yl)benzo[d]thiazol-6-yl)oxy)methyl)oxazolidin-2-one

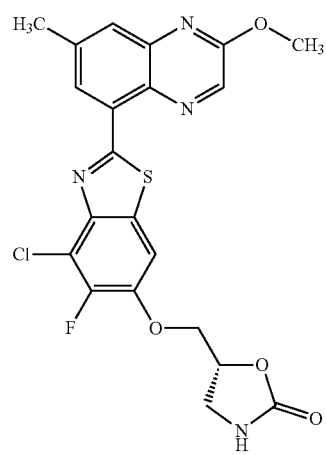

(622)

Intermediate 622A:
(R)-5-(chloromethyl)oxazolidin-2-one

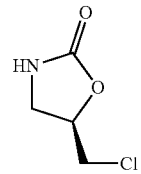

(622A)

(R)-2-(chloromethyl)oxirane (285 mg, 3.08 mmol), potassium cyanate (500 mg, 6.16 mmol) and magnesium sulfate (742 mg, 6.16 mmol) were dissolved in water (10 mL) and the mixture was heated to 100° C. under a reflux condenser for 18 h. The reaction mixture was then diluted with water and extracted with EtOAc (3x). The combined organic layer was washed with brine, dried with sodium sulfate, filtered and concentrated to yield Intermediate 622A (210 mg, 1.549 mmol, 50.3% yield). The product was brought forward without further purification. $^1$H NMR (400 MHz, CDCl$_3$) δ 5.81 (br. s., 1H), 4.98-4.75 (m, 1H), 3.84-3.65 (m, 3H), 3.57 (ddd, J=9.0, 5.9, 1.0 Hz, 1H).

Example 622

Intermediate I-65 (30 mg, 0.080 mmol) was dissolved in DMF (2 mL) along with potassium carbonate (33.1 mg, 0.239 mmol), Intermediate 622A (21.64 mg, 0.160 mmol) and potassium iodide (13.25 mg, 0.080 mmol). The reaction mixture was then stirred at 80° C. for 18 h before being diluted with EtOAc. The organic layer was washed with 10% aq. LiCl (3x), brine, dried with sodium sulfate, filtered, and concentrated. The crude residue was purified by reverse phase HPLC (Method D, 30-75% 30 min, 100% 5 min) to yield Example 622 (4 mg, 8.00 µmol, 10.02% yield). LC-MS: Method H, RT=1.17 min, MS (ESI) m/z: 475.05 (M+H)$^+$. $^1$H NMR (500 MHz, DMSO-d$_6$) δ 8.75 (s, 1H), 8.60 (s, 1H), 7.99-8.08 (m, 1H), 7.87 (s, 1H), 7.59-7.69 (m, 1H), 4.93-5.09 (m, 1H), 4.27-4.49 (m, 2H), 4.09 (s, 3H), 3.48-3.72 (m, 1H), 3.36-3.45 (m, 1H), 2.65 (s, 3H).

Example 623

4-(((4-chloro-5-fluoro-2-(2-methoxy-7-methylquinoxalin-5-yl)benzo[d]thiazol-6-yl)oxy)methyl)oxazol-2-amine

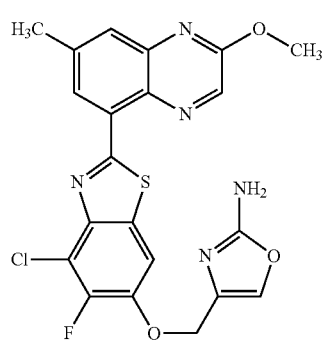

(623)

905

Intermediate 623A: 1-bromo-3-((tert-butyldimethyl-silyl)oxy)propan-2-one

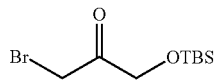

(623A)

1-bromo-3-((tert-butyldimethylsilyl)oxy)propan-2-ol (500 mg, 1.857 mmol) was dissolved in DCM (10 mL). Dess-Martin Periodinane (1181 mg, 2.79 mmol) was added to the reaction mixture which stirred at room temperature for 2 hours. The reaction mixture was concentrated and the resulting residue was dissolved in a small amount of methylene chloride before being charged to a 12 g silica gel cartridge which was eluted with a 15 min gradient from 0-100% EtOAc in hexane. Fractions containing the desired product were collected and concentrated to yield Intermediate 623A (300 mg, 1.123 mmol, 60.5% yield) as a clear oil. $^1$H NMR (400 MHz, CDCl$_3$) δ 4.25 (s, 2H), 3.94-4.05 (m, 2H), 0.75-0.89 (m, 9H), −0.10-0.09 (m, 6H).

Example 623

Intermediate 623A (20 mg, 0.053 mmol) was dissolved in DMF (2 mL). Potassium carbonate (22.07 mg, 0.160 mmol) was added to the mixture followed by I-65 (20 mg, 0.053 mmol). The reaction mixture was stirred for 1 h at room temperature after which additional Intermediate 623A (20 mg, 0.053 mmol) was added to the mixture. The reaction mixture was allowed to stir for 2 hours at room temperature and then quenched with a few drops of AcOH. The mixture was diluted with EtOAc and the organic layer was washed with 10% aq. LiCl (3×), brine, dried with sodium sulfate, filtered and concentrated. The resulting residue was dissolved in THF (5 mL)/water (0.500 mL)/acetic acid (0.500 mL). 1M TBAF in THF (0.064 mL, 0.064 mmol) was added to the mixture which was allowed to stir for 1 hour at room temperature after which additional 1M TBAF in THF (0.064 mL, 0.064 mmol) was added. The mixture was then diluted 1.5 M dipotassium phosphate solution and extracted with EtOAc (3×). The combined organic layer was washed with brine, dried with sodium sulfate, filtered and concentrated. The resulting residue was dissolved in THF (1 mL) along with cyanamide (21.59 mg, 0.514 mmol), 1N aqueous sodium acetate (0.051 mL, 0.051 mmol), tetrabutylammonium hydroxide (13.33 mg, 0.051 mmol) and 1M aq. NaOH (0.051 mL, 0.051 mmol). The reaction mixture was allowed to stir at room temperature for 3 h then a few drops of AcOH added and the reaction mixture was concentrated and purified by reverse phase HPLC (Method D, 40-73% 22 min, 100% 7 min) to yield Example 623 (0.6 mg, 0.001 mmol, 2% yield) over the three step sequence. LC-MS: Method H, RT=1.05 min, MS (ESI) m/z: 472.10 (M+H)$^+$. $^1$H NMR (500 MHz, DMSO-d$_6$) δ 8.76 (s, 1H), 8.61 (s, 1H), 8.10-8.14 (m, 1H), 7.81-7.90 (m, 1H), 7.56 (s, 1H), 6.66 (s, 2H), 5.02 (s, 2H), 4.10 (s, 3H), 2.66 (s, 3H).

906

Example 624

(2R,3S)-3-((2-(2-ethoxy-7-methylquinoxalin-5-yl)-5-fluorobenzo[d]thiazol-6-yl)oxy)butan-2-yl (2-(2-(phosphonooxy)ethyl)pyrimidin-5-yl)carbamate

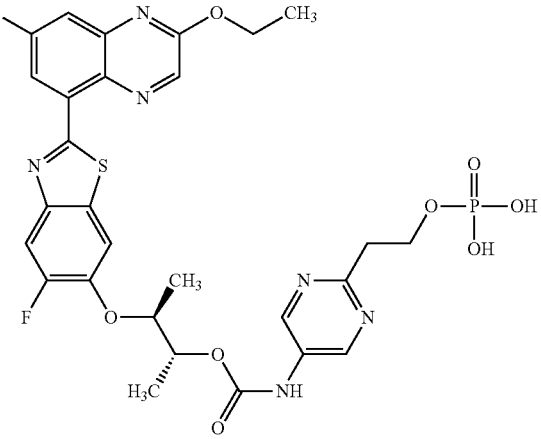

(624)

Intermediate 624A: (2R,3S)-3-((2-(2-ethoxy-7-methylquinoxalin-5-yl)-5-fluorobenzo[d] thiazol-6-yl)oxy)butan-2-yl (2-(2-((bis(2-(trimethylsilyl)ethoxy)phosphoryl)oxy)ethyl) pyrimidin-5-yl) carbamate

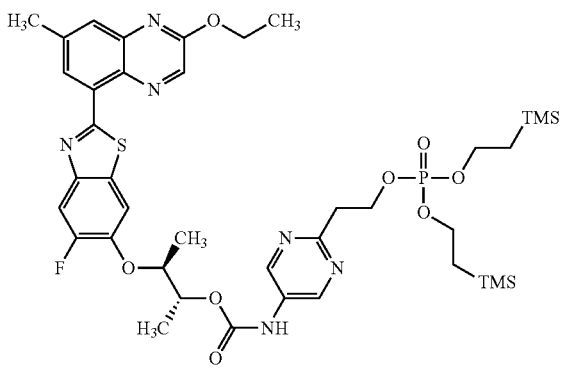

(624A)

To a suspension of Example 566 (313 mg, 0.528 mmol) in DCM (40 mL) was added bis(2-(trimethylsilyl)ethyl) diisopropylphosphoramidite (0.7 mL, 1.704 mmol) followed by 1H-tetrazole (137 mg, 1.956 mmol) and the resulting mixture was stirred for 30 minutes at room temperature. The reaction mixture was then cooled to 0° C. and hydrogen peroxide (35% wt. in H$_2$O) (0.3 mL, 3.43 mmol) was added dropwise over 2 minutes. After stirring for 30 minutes at rt, the reaction mixture was diluted with 30 mL of DCM and the organic layer was washed with saturated aqueous sodium sulfite (2×), brine (1×), dried with sodium sulfate, filtered and concentrated. The resulting residue was dissolved in a small amount of DCM and purified by silica gel chromatography (gradient of 0-100% EtOAc/DCM). The fractions containing desired product were concentrated to yield Intermediate 624A (349 mg, 0.4 mmol, 76% yield). LC-MS: Method H, MS (ESI) m/z: 873.2 (M+H)+. ¹H NMR (400 MHz, CDCl₃) δ 8.79 (br. s., 2H), 8.53 (d, J=2.0 Hz, 1H), 8.46 (s, 1H), 7.77 (d, J=11.4 Hz, 1H), 7.69 (dd, J=2.0, 0.9 Hz, 1H), 7.49 (d, J=7.7 Hz, 1H), 7.39-7.30 (m, 1H), 5.21-4.99 (m, 1H), 4.60-4.44 (m, 5H), 4.16-3.98 (m, 4H), 3.28 (t, J=6.8 Hz, 2H), 1.48 (t, J=7.0 Hz, 3H), 1.42 (dd, J=16.3, 6.4 Hz, 6H), 1.10-0.98 (m, J=8.6, 8.6, 0.7 Hz, 4H), 0.03-0.04 (m, 18H).

Example 624

Intermediate 624A (226 mg, 0.259 mmol) was dissolved in DCM (10 mL). TFA (0.140 mL, 1.812 mmol) and water (0.033 mL, 1.812 mmol) were added to the solution which was stirred at room temperature. After 5 minutes of stirring, additional TFA (0.140 mL, 1.812 mmol) was added dropwise and the reaction mixture was allowed to stir for 50 minutes at room temperature. Concentration of the reaction mixture followed by trituration from ether yielded a particulate solid. The mother liquor was removed by filtration, and the remaining solid was redissolved in dioxane and concentrated to afford 624 in quantitative yield. LC-MS: Method H, RT=1.10 min, MS (ESI) m/z: 673.2 (M+H)+. ¹H NMR (400 MHz, DMSO-d₆) δ 10.03 (br. s., 1H), 8.78 (br. s., 2H), 8.68 (s, 1H), 8.54 (d, J=1.8 Hz, 1H), 8.04 (d, J=8.4 Hz, 1H), 7.94 (d, J=11.7 Hz, 1H), 7.78 (dd, J=2.0, 0.9 Hz, 1H), 5.11 (dd, J=6.6, 2.6 Hz, 1H), 4.78 (dd, J=6.4, 2.9 Hz, 1H), 4.51 (q, J=7.0 Hz, 2H), 4.23 (q, J=6.8 Hz, 2H), 3.10 (t, J=6.7 Hz, 2H), 2.60 (s, 3H), 1.46-1.29 (m, 9H).

Example 625

2-(6-chloro-3-(methoxymethyl)quinolin-8-yl)-6-methoxy-4-methylbenzo[d]thiazole

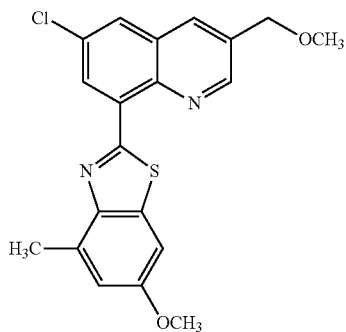

(625)

Intermediate 625A: 8-bromo-6-chloro-3-(methoxymethyl)quinoline

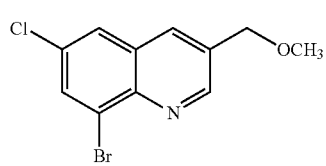

(625A)

Intermediate I-123 (33.5 mg, 0.143 mmol), 3-methoxypropanal (13.8 mg, 0.157 mmol), and sodium methoxide (0.5 M in MeOH, 314 μL, 0.157 mmol) were dissolved in MeOH (1.43 mL) and heated to reflux. After 3 hours, the reaction mixture was diluted with saturated NH₄Cl and EtOAc. The layers were separated and the organic layer was washed with brine, dried (Na₂SO₄), filtered, and concentrated in vacuo. The crude material was purified by column chromatography (ISCO, 24 g silica gel column, 19 minute gradient from 0 to 100% EtOAc in hexanes) to give Intermediate 625A (23.5 mg, 0.082 mmol, 57%) as a yellow solid: ¹H NMR (400 MHz, CDCl₃) δ 8.99 (d, J=2.2 Hz, 1H), 8.09-8.07 (m, 1H), 8.04 (d, J=2.2 Hz, 1H), 7.82 (d, J=2.2 Hz, 1H), 4.71 (s, 2H), 3.51 (s, 3H); LC-MS: Method H, RT=1.19 min, MS (ESI) m/z: 286/288 (M+H)+.

Intermediate 625B: (6-chloro-3-(methoxymethyl)quinolin-8-yl)boronic acid

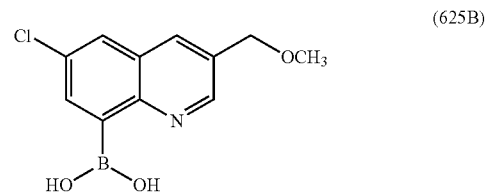 [SMILES: COCc1cnc2c(B(O)O)cc(Cl)cc2c1]

(625B)

Intermediate 625A (73.2 mg, 0.255 mmol), bispinacolatodiboron (97 mg, 0.383 mmol), and potassium acetate (62.7 mg, 0.639 mmol) were dissolved in 1,4-dioxane (2.56 mL) and degassed for 5 minutes by bubbling with argon. PdCl₂(dppf)-CH₂Cl₂Adduct (16.7 mg, 0.020 mmol) was added and the reaction degassed for an additional 10 minutes. The reaction mixture was heated to 130° C. in the microwave for 45 minutes. The reaction mixture was diluted with EtOAc and water. The aqueous layer was further extracted twice with EtOAc. The combined organic layers were washed with brine, dried (Na₂SO₄), filtered, and concentrated in vacuo. The crude material was purified by preparative HPLC (Method A, 30-100% B in 15 minutes) to give Intermediate 625B (31.4 mg, 0.125 mmol, 49%) was a brown solid: LC-MS: Method H, RT=0.97 min, MS (ESI) m/z: 252.1 (M+H)+.

Example 625

Intermediate 625B (10 mg, 0.040 mmol), Intermediate I-3 (12.32 mg, 0.048 mmol), and PdCl₂(dppf)-CH₂Cl₂ adduct (1.95 mg, 2.39 μmol) were dissolved in 1,4-dioxane (306 μL) and Na₂CO₃ (2 M, 179 μL, 0.358 mmol) and heated to 100° C. After 1 hour, the reaction mixture was cooled to ambient temperature, diluted with EtOAc, washed with water, then brine, dried (Na₂SO₄), filtered, and concentrated in vacuo. The crude material was purified by preparative HPLC (Method D, 60-100% B in 20 minutes) to give Example 625 (7.0 mg, 0.018 mmol, 46%): ¹H NMR (500 MHz, DMSO-d₆) δ 9.09 (br. s., 1H), 8.84 (br. s., 1H), 8.45 (br. s., 1H), 8.33 (br. s., 1H), 7.56 (br. s., 1H), 7.02 (br. s., 1H), 4.74 (s, 2H), 3.87 (s, 3H), 3.44 (s, 3H), 2.76 (s, 3H); LC-MS: Method H, RT=1.44 min, MS (ESI) m/z: 385.1 (M+H)+; Analytical HPLC Method B, 100% purity.

Example 626

2-(6-chloro-3-methoxyquinolin-8-yl)-6-methoxy-4-methylbenzo[d]thiazole

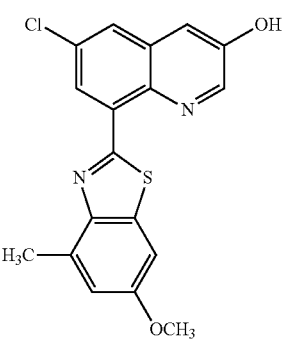

(626)

Intermediate 626A: 6-methoxy-4-methyl-2-(tributyl-stannyl)benzo[d]thiazole

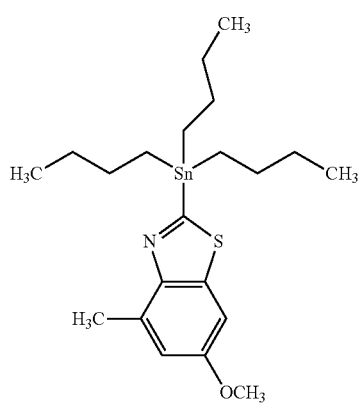

(626A)

Intermediate I-3 (300 mg, 1.162 mmol) was dissolved in Et$_2$O (4.65 mL) and cooled to −78° C. BuLi (2.5 M in hexanes, 511 µL, 1.278 mmol) was then added. After 45 minutes, tributylchlorostannane (315 µL, 1.16 mmol) was added. After 15 minutes, the reaction mixture was warmed to ambient temperature and concentrated in vacuo. The crude material was suspended in hexanes and filtered through dry celite. The residue was concentrated in vacuo to give Intermediate 626A, which was used directly in the subsequent step.

Intermediate 626B: 2-(3-(benzyloxy)-6-chloroquinolin-8-yl)-6-methoxy-4-methylbenzo[d]thiazole

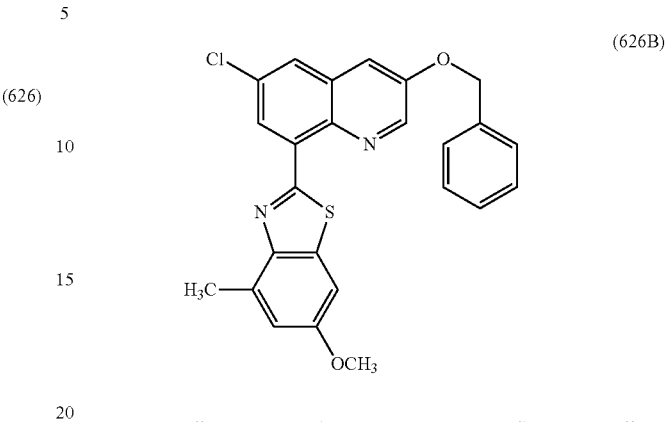

(626B)

Intermediate I-122A (270 mg, 0.774 mmol), Intermediate 626A (526 mg, 1.12 mmol), and potassium acetate (152 mg, 1.55 mmol) were dissolved in 1,4-dioxane (7.74 mL) and degassed by bubbling with argon for 15 minutes. Palladium tetrakistriphenylphosphine (44.7 mg, 0.039 mmol) was added and the reaction vessel was sealed and heated to 120° C. in the microwave for 2 hours. The reaction mixture was diluted with EtOAc, washed with water, then brine, dried (Na$_2$SO$_4$), filtered, and concentrated in vacuo. The crude material was purified by column chromatography (ISCO, 40 g silica gel column, 19 minute gradient from 0 to 100% EtOAc in hexanes) then repurified by column chromatography (ISCO, 40 g silica gel column, 19 minute gradient from 0 to 100% DCM in hexanes) to give Intermediate 626B (201 mg, 0.45 mmol, 58%) as a yellow solid: $^1$H NMR (400 MHz, CDCl$_3$) δ 8.90 (d, J=2.9 Hz, 1H), 8.86 (d, J=2.4 Hz, 1H), 7.77 (d, J=2.2 Hz, 1H), 7.56-7.38 (m, 6H), 7.28 (s, 1H), 6.96 (dd, J=2.6, 0.9 Hz, 1H), 5.27 (s, 2H), 3.92 (s, 3H), 2.85 (s, 3H); LC-MS: Method H, RT=1.58 min, MS (ESI) m/z: 447.1 (M+H)$^+$.

Intermediate 626C: 6-chloro-8-(6-methoxy-4-methylbenzo[d]thiazol-2-yl)quinolin-3-ol

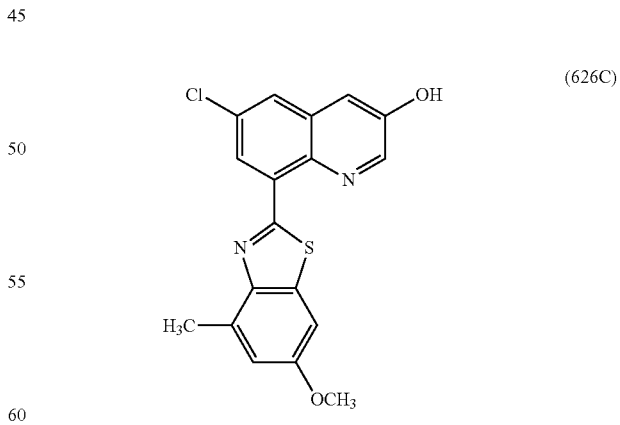

(626C)

Intermediate 626B (25 mg, 0.056 mmol) and pentamethylbenzene (58.0 mg, 0.392 mmol) were dissolved in DCM (2.8 mL) and cooled to −78° C. Boron trichloride (1 M in heptane, 145 µL, 0.145 mmol) was added and the reaction mixture was allowed to slowly warm to ambient temperature. After stirring overnight, the reaction was quenched with 1 N HCl and extracted thrice with EtOAc. The combined organic layers were washed with brine, dried ($Na_2SO_4$), filtered, and concentrated in vacuo. The crude material was purified by column chromatography (ISCO, 4 g silica gel column, 15 minute gradient from 0 to 100% EtOAc in hexanes) to give Intermediate 626C (17.1 mg, 0.048 mmol, 86%) as a yellow solid: $^1$H NMR (400 MHz, $CDCl_3$) δ 8.87 (d, J=2.4 Hz, 1H), 8.82 (d, J=2.9 Hz, 1H), 7.77 (d, J=2.2 Hz, 1H), 7.48 (d, J=2.9 Hz, 1H), 6.96 (dd, J=2.6, 0.9 Hz, 1H), 3.92 (s, 3H), 2.86 (s, 3H); LC-MS: Method H, RT=1.39 min, MS (ESI) m/z: 357.1 (M+H)$^+$.

Example 626

Intermediate 626C (17 mg, 0.048 mmol), $K_2CO_3$ (13.2 mg, 0.095 mmol), and MeI (11.9 μL, 0.191 mmol) were dissolved in acetone (1.91 mL). After stirring overnight, the reaction mixture was concentrated in vacuo and purified by preparative HPLC (Method D, 55-95% B in 10 minutes) to give Example 626 (5.5 mg, 0.015 mmol, 31%): $^1$H NMR (500 MHz, DMSO-$d_6$) δ 8.89 (br. s., 1H), 8.67 (s, 1H), 8.18 (s, 1H), 7.95 (br. s., 1H), 7.54 (s, 1H), 7.01 (br. s., 1H), 4.00 (s, 3H), 3.86 (s, 3H), 2.75 (s, 3H); LC-MS: Method H, RT=1.51 min, MS (ESI) m/z: 371.1 (M+H)$^+$; Analytical HPLC Method B, 100% purity.

Example 627

2-(6-methoxy-2-(2-methoxy-7-methylquinoxalin-5-yl)benzo[d]thiazol-4-yl)propan-2-ol

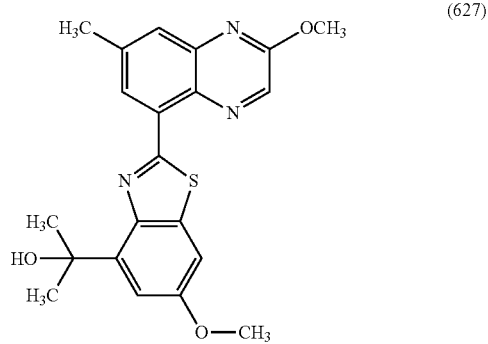 [SMILES: COc1cc(C(C)(C)O)c2nc(-c3cc(C)cc4nc(OC)cnc34)sc2c1]
(627)

Intermediate 627A: 2-(2-bromo-6-methoxybenzo[d]thiazol-4-yl)propan-2-ol

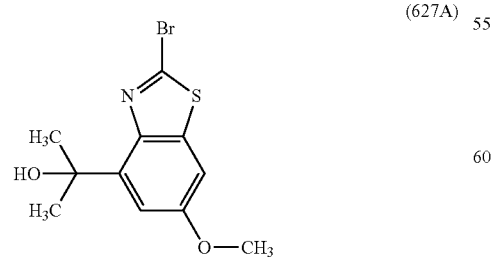
(627A)

Intermediate I-20C (50 mg, 0.165 mmol) was dissolved in THF (331 μL) and cooled to −78° C. Methylmagnesium bromide (3 M in $Et_2O$, 124 μL, 0.372 mmol) was added and the reaction mixture was allowed to slowly warm to 0° C. in the freezer. After stirring overnight, the reaction was quenched with saturated $NH_4Cl$ and extracted with EtOAc. The organic layer was washed with water, then brine, dried ($Na_2SO_4$), filtered, and concentrated in vacuo. The crude material was purified by column chromatography (ISCO, 12 g silica gel column, 17 minute gradient from 0 to 100% EtOAc in hexanes) to give Intermediate 627A (13.6 mg, 0.045 mmol, 27%) as a clear oil: LC-MS: Method H, RT=1.00 min, MS (ESI) m/z: 302/304 (M+H)$^+$.

Example 627

Intermediate I-9 (11.6 mg, 0.039 mmol), Intermediate 627A (14 mg, 0.046 mmol), and potassium phosphate, tribasic (16.4 mg, 0.077 mmol) were dissolved in DMF (386 μL) and degassed by bubbling with argon for 15 minutes. Palladium tetrakistriphenylphosphine (4.46 mg, 3.86 μmol) was added and degassing continued for 5 minutes. The reaction was then sealed and heated to 85° C. After stirring overnight, the crude material was purified by preparative HPLC (Method D, 50-100% B in 14 minutes) to give Example 627 (6.6 mg, 0.016 mmol, 42%): $^1$H NMR (500 MHz, DMSO-$d_6$) δ 8.75 (s, 1H), 8.51 (d, J=1.7 Hz, 1H), 7.84 (dd, J=1.8, 1.0 Hz, 1H), 7.59 (d, J=2.5 Hz, 1H), 7.35 (d, J=2.5 Hz, 1H), 5.42 (s, 1H), 4.10 (s, 3H), 3.88 (s, 3H), 2.66 (s, 3H), 1.83 (s, 6H); LC-MS: Method H, RT=1.27 min, MS (ESI) m/z: 396.2 (M+H)$^+$; Analytical HPLC Method B, 97% purity.

Example 628

1-(6-methoxy-2-(2-(methoxymethyl)-7-methylquinoxalin-5-yl)benzo[d]thiazol-4-yl)-2,2-dimethylpropan-1-ol

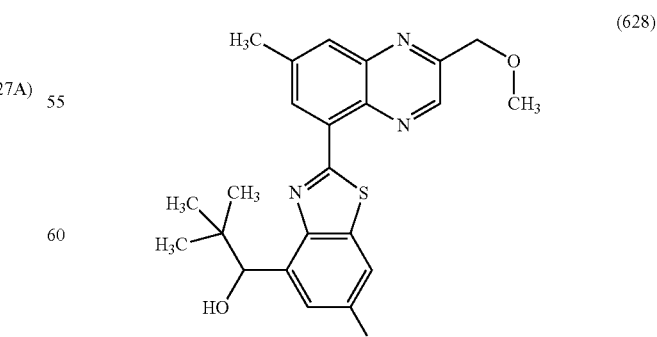
(628)

Intermediate 628A: 1-(2-bromo-6-methoxybenzo[d]thiazol-4-yl)-2,2-dimethylpropan-1-ol

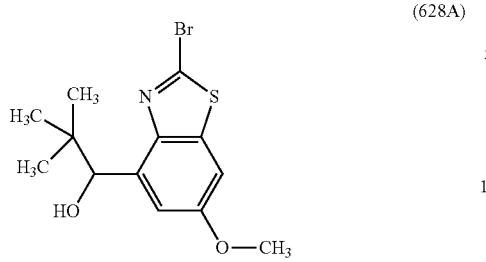

(628A)

Intermediate I-20 (40 mg, 0.147 mmol) was dissolved in THF (294 µL) and cooled to −78° C. tert-Butylmagnesium chloride (1 M in THF, 184 µL, 0.184 mmol) was then added and the reaction mixture was allowed to slowly warm to 0° C. in the freezer. After stirring overnight, the reaction was quenched with saturated NH$_4$Cl and extracted with EtOAc. The organic layer was washed with water, then brine, dried (Na$_2$SO$_4$), filtered, and concentrated in vacuo. The crude material was purified by column chromatography (ISCO, 12 g silica gel column, 17 minute gradient from 0 to 100% EtOAc in hexanes) to give Intermediate 628A (29 mg, 0.088 mmol, 60%) as a white solid: LC-MS: Method H, RT=1.10 min, MS (ESI) m/z: 330/332 (M+H)$^+$.

Example 628

Intermediate I-2 (16.6 mg, 0.053 mmol), Intermediate 628A (14.5 mg, 0.044 mmol), and potassium phosphate, tribasic (18.6 mg, 0.088 mmol) were dissolved in DMF (439 µL) and degassed by bubbling with argon for 15 minutes. Palladium tetrakistriphenylphosphine (5.07 mg, 4.39 µmol) was added and degassing continued for 5 minutes. The reaction vessel was then sealed and heated to 85° C. After heating overnight, the crude material was purified by preparative HPLC (Method D, 45-85% B in 20 minutes) to give Example 628 (6.4 mg, 0.015 mmol, 33%): $^1$H NMR (500 MHz, DMSO-d$_6$) δ 9.11 (s, 1H), 8.77 (d, J=1.9 Hz, 1H), 8.05 (s, 1H), 7.65 (d, J=2.5 Hz, 1H), 7.16 (d, J=2.5 Hz, 1H), 5.45 (d, J=4.7 Hz, 1H), 5.34 (d, J=4.7 Hz, 1H), 4.83 (s, 2H), 3.89 (s, 3H), 3.48 (s, 3H), 2.72 (s, 3H), 0.97 (s, 9H); LC-MS: Method H, RT=1.24 min, MS (ESI) m/z: 437.8 (M+H)$^+$; Analytical HPLC Method B, 98% purity.

Example 629

(6-methoxy-2-(2-methoxy-7-methylquinoxalin-5-yl)benzo[d]thiazol-4-yl) (phenyl)methanol

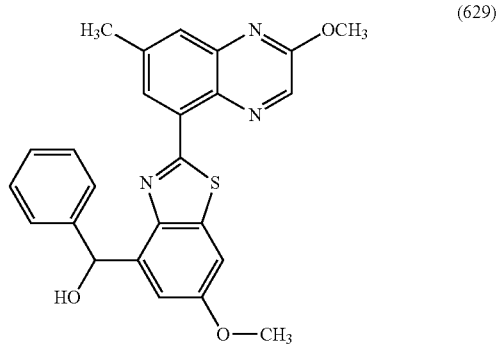 [SMILES: COc1cc(C(O)c2ccccc2)c2nc(-c3cc(C)cc4nc(OC)cnc34)sc2c1]

(629)

Intermediate 629A: (2-bromo-6-methoxybenzo[d]thiazol-4-yl)(phenyl)methanol

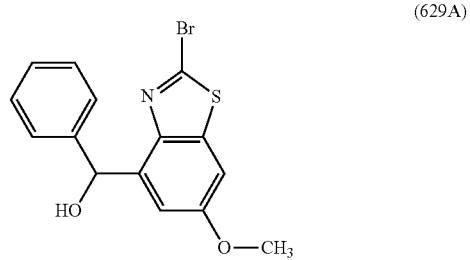 [SMILES: COc1cc(C(O)c2ccccc2)c2nc(Br)sc2c1]

(629A)

Intermediate I-20 (40 mg, 0.147 mmol) was dissolved in THF (294 µL) and cooled to −78° C. Phenylmagnesium bromide (3 M in Et$_2$O, 61.2 µL, 0.184 mmol) was added and the reaction mixture was allowed to slowly warm to 0° C. in the freezer. After stirring overnight, the reaction was quenched with saturated NH$_4$Cl and extracted with EtOAc. The organic layer was washed with water, then brine, dried (Na$_2$SO$_4$), filtered, and concentrated in vacuo. The crude material was purified by column chromatography (ISCO, 12 g silica gel column, 17 minute gradient from 0 to 100% EtOAc in hexanes) to give Intermediate 629A (33.6 mg, 0.096 mmol, 65%) as a white solid: LC-MS: Method H, RT=1.01 min, MS (ESI) m/z: 350/352 (M+H)$^+$.

Example 629

Intermediate I-9 (14.1 mg, 0.047 mmol), Intermediate 629A (16.5 mg, 0.047 mmol), and potassium phosphate, tribasic (20 mg, 0.094 mmol) were dissolved in DMF (471 µL) and degassed by bubbling with argon for 15 minutes. Palladium tetrakistriphenylphosphine (5.44 mg, 4.71 µmol) was added and degassing continued for 5 minutes. The reaction vessel was then sealed and heated to 85° C. After heating overnight, the crude material was purified by preparative HPLC (Method D, 40-75% B in 15 minutes) then repurified by preparative HPLC (Method D, 60-100% B in 12 minutes) to give Example 629 (7.4 mg, 0.017 mmol, 35%): $^1$H NMR (500 MHz, DMSO-d$_6$) δ 8.74 (s, 1H), 8.61 (d, J=1.7 Hz, 1H), 7.83 (s, 1H), 7.62-7.55 (m, 3H), 7.35-7.26 (m, 3H), 7.23-7.15 (m, 1H), 6.70 (d, J=4.4 Hz, 1H), 6.10 (d, J=4.1 Hz, 1H), 4.09 (s, 3H), 3.86 (s, 3H), 2.67 (s, 3H); LC-MS: Method H, RT=1.24 min, MS (ESI) m/z: 443.8 (M+H)$^+$; Analytical HPLC Method B, 99% purity.

Example 630

1-(6-methoxy-2-(2-methoxy-7-methylquinoxalin-5-yl)benzo[d]thiazol-4-yl)-2,2-dimethylpropan-1-ol

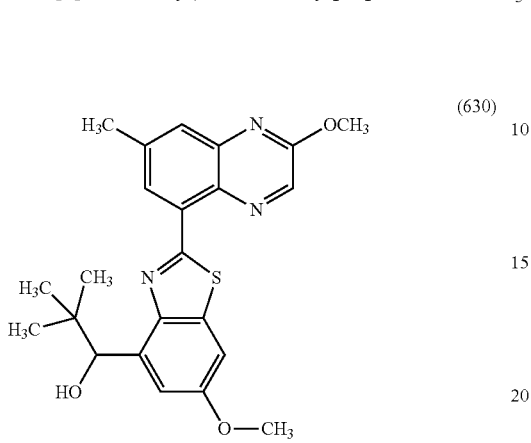

(630)

Intermediate I-9 (15.8 mg, 0.053 mmol), Intermediate 628A (14.5 mg, 0.044 mmol), and potassium phosphate, tribasic (18.6 mg, 0.088 mmol) were dissolved in DMF (439 µL) and degassed by bubbling with argon for 15 minutes. Palladium tetrakistriphenylphosphine (5.07 mg, 4.39 µmol) was added and degassing continued for 5 minutes. The reaction vessel was then sealed and heated to 85° C. After heating overnight, the crude material was purified by preparative HPLC (Method D, 50-85% B in 15 minutes) then repurified by preparative HPLC (Method D, 60-100% B in 20 minutes) to give Example 630 (3.8 mg, 0.0087 mmol, 20%): $^1$H NMR (500 MHz, DMSO-$d_6$) δ 8.75 (s, 1H), 8.55 (d, J=1.7 Hz, 1H), 7.83 (s, 1H), 7.61 (d, J=2.5 Hz, 1H), 7.15 (d, J=2.5 Hz, 1H), 5.43 (s, 1H), 5.34 (br. s., 1H), 4.09 (s, 3H), 3.88 (s, 3H), 2.66 (s, 3H), 0.96 (s, 9H); LC-MS: Method H, RT=1.32 min, MS (ESI) m/z: 423.8 (M+H)$^+$; Analytical HPLC Method B, 97% purity.

Example 631

1-(6-methoxy-2-(2-methoxy-7-methylquinoxalin-5-yl)benzo[d]thiazol-4-yl)-2-phenylethanol

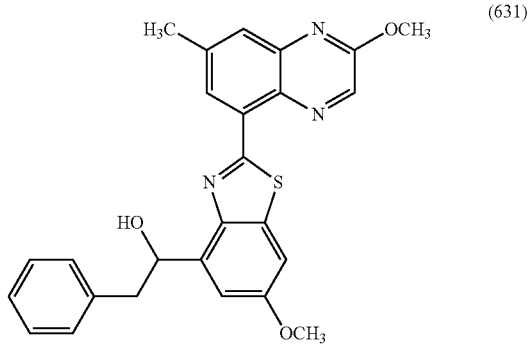 [SMILES: COc1cc(C(O)Cc2ccccc2)c2nc(-c3cc(C)cc4nc(OC)cnc34)sc2c1]

(631)

Intermediate 631A: 1-(2-bromo-6-methoxybenzo[d]thiazol-4-yl)-2-phenylethanol

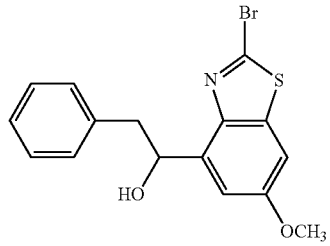

(631A)

Intermediate I-20 (40 mg, 0.147 mmol) was dissolved in THF (294 µL) and cooled to −78° C. Benzylmagnesium chloride (2 M in Et$_2$O, 92 µL, 0.184 mmol) was added and the reaction mixture was allowed to slowly warm to 0° C. in the freezer. After stirring overnight, the reaction was quenched with saturated NH$_4$Cl and extracted with EtOAc. The organic layer was washed with water, then brine, dried (Na$_2$SO$_4$), filtered, and concentrated in vacuo. The crude material was purified by column chromatography (ISCO, 12 g silica gel column, 17 minute gradient from 0 to 100% EtOAc in hexanes) to give Intermediate 631A (18.9 mg, 0.052 mmol, 35%) as a yellow oil: LC-MS: Method H, RT=1.07 min, MS (ESI) m/z: 364/366 (M+H)$^+$.

Example 631

Intermediate I-9 (9.39 mg, 0.031 mmol), Intermediate 631A (9.5 mg, 0.026 mmol), and potassium phosphate, tribasic (11.1 mg, 0.052 mmol) were dissolved in DMF (261 µL) and degassed by bubbling with argon for 15 minutes. Palladium tetrakistriphenylphosphine (3.01 mg, 2.61 µmol) was added and degassing continued for 5 minutes. The reaction was then sealed and heated to 85° C. After heating overnight, the crude material was purified by preparative HPLC (Method D, 45-80% B in 20 minutes) then repurified by preparative HPLC (Method D, 70-100% B in 15 minutes) to give Example 631 (1.2 mg, 0.0026 mmol, 10%): $^1$H NMR (500 MHz, DMSO-$d_6$) δ 8.76 (s, 1H), 8.61 (d, J=1.4 Hz, 1H), 7.85 (s, 1H), 7.60 (d, J=2.5 Hz, 1H), 7.38-7.33 (m, 2H), 7.33-7.27 (m, 2H), 7.23-7.16 (m, 2H), 5.71 (dt, J=8.3, 4.4 Hz, 1H), 5.49 (d, J=5.2 Hz, 1H), 4.10 (s, 3H), 3.87 (s, 3H), 3.29 (dd, J=13.5, 3.6 Hz, 1H), 2.97 (dd, J=13.6, 8.4 Hz, 1H), 2.69 (s, 3H); LC-MS: Method H, RT=1.27 min, MS (ESI) m/z: 457.8 (M+H)$^+$; Analytical HPLC Method B, 100% purity.

Example 632

1-(5-fluoro-6-methoxy-2-(2-methoxy-7-methylquinoxalin-5-yl)benzo[d]thiazol-4-yl)-2,2-dimethylpropan-1-ol

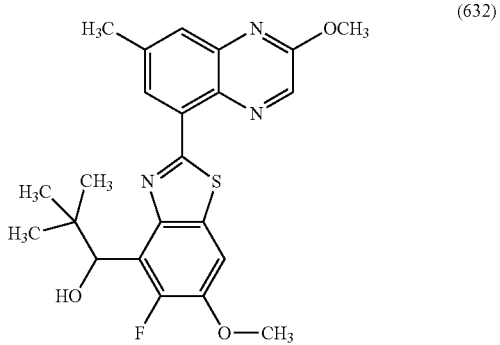 [SMILES: COc1cnc2c(-c3nc4c(C(O)C(C)(C)C)c(F)c(OC)cc4s3)cc(C)cc2n1]

Intermediate 632A: 1-(2-amino-5-fluoro-6-methoxybenzo[d]thiazol-4-yl)-2,2-dimethylpropan-1-ol

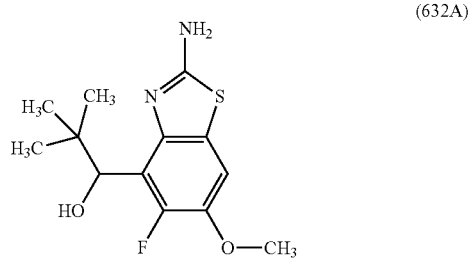 [SMILES: COc1cc2sc(N)nc2c(C(O)C(C)(C)C)c1F]

Intermediate I-43C (100 mg, 0.430 mmol) was dissolved in THF (4.3 mL). Sodium hydride (18.9 mg, 0.473 mmol) was then added. After 30 minutes, the reaction mixture was cooled to −78° C. and tert-butyllithium (1 M, 430 μL, 0.516 mmol) was added. After 45 minutes, pivalaldehyde (96 μL, 0.86 mmol) was added and the reaction mixture was allowed to warm to ambient temperature. After the reaction mixture achieved ambient temperature, it was diluted with EtOAc and washed with water, then brine, dried (Na$_2$SO$_4$), filtered, and concentrated in vacuo to give Intermediate 632A, which was used immediately in the subsequent reaction: LC-MS: Method H, RT=0.74 min, MS (ESI) m/z: 285.2 (M+H)$^+$.

Intermediate 632B: 1-(2-chloro-5-fluoro-6-methoxybenzo[d]thiazol-4-yl)-2,2-dimethylpropan-1-ol

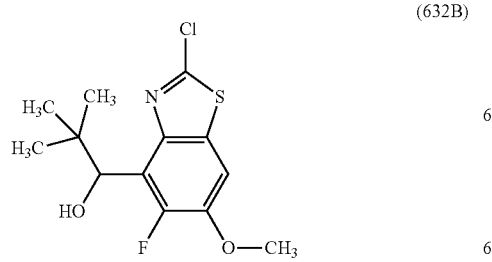

Copper(II) chloride (81 mg, 0.601 mmol) and t-butyl nitrite (77 μL, 0.644 mmol) were dissolved in MeCN (1.72 mL) and allowed to stir 10 minutes. Intermediate 632A (122 mg, 0.429 mmol) was dissolved in MeCN (2.57 mL) and the copper solution was added and heated to 60° C. After 1.5 hours, the reaction mixture was diluted with EtOAc, washed with 1 N HCl, saturated NaHCO$_3$, then brine, dried (Na$_2$SO$_4$), filtered, and concentrated in vacuo. The crude material was purified by column chromatography (ISCO, 12 g silica gel column, 17 minute gradient from 0 to 100% EtOAc in hexanes) to give Intermediate 632B (21 mg, 0.021 mmol, 4.8%) as a brown solid: LC-MS: Method H, RT=1.14 min, MS (ESI) m/z: 304.1 (M+H)$^+$.

Example 632

Intermediate I-9 (24.9 mg, 0.083 mmol) and Intermediate 632B (21 mg, 0.069 mmol) were dissolved in DMF (691 μL). PdCl$_2$(dppf)-CH$_2$Cl$_2$ adduct (3.39 mg, 4.15 μmol) was added and the reaction mixture was degassed by bubbling with argon for 15 minutes. Sodium carbonate (2 M, 41.5 μl, 0.083 mmol) was added and the reaction mixture was degassed for 5 minutes, then sealed and heated to 100° C. in the microwave for 30 minutes. The material was heated in the microwave for an additional 30 minutes at 120° C. The crude material was purified by preparative HPLC (Method D, 70-100% B in 20 minutes) then repurified by preparative HPLC (Method D, 60-100% B in 20 minutes) to give Example 632 (0.7 mg, 0.0015 mmol, 2.2%): $^1$H NMR (500 MHz, DMSO-d$_6$) δ 8.72 (s, 1H), 8.50 (d, J=1.7 Hz, 1H), 7.85 (d, J=7.7 Hz, 1H), 7.83-7.80 (m, 1H), 5.57 (br. s., 1H), 5.25 (br. s., 1H), 4.08 (s, 3H), 3.94 (s, 3H), 2.64 (s, 3H), 1.00 (s, 9H); LC-MS: Method H, RT=1.34 min, MS (ESI) m/z: 442.2 (M+H)$^+$; Analytical HPLC Method B, 97% purity.

Example 633

2,2,2-trifluoro-1-(6-methoxy-2-(2-methoxy-7-methylquinoxalin-5-yl)benzo[d]thiazol-4-yl)ethanol

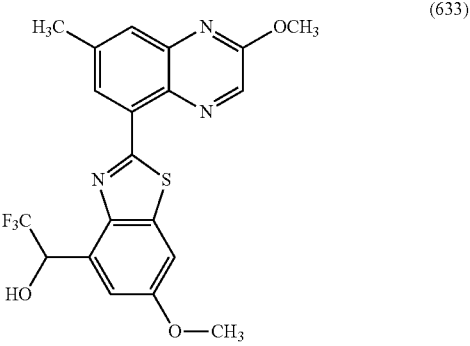 [SMILES: COc1cc(C(O)C(F)(F)F)c2nc(-c3cc(C)cc4nc(OC)cnc34)sc2c1]

Intermediate 633A: 1-(2-chloro-6-methoxybenzo[d]thiazol-4-yl)-2,2,2-trifluoroethanol

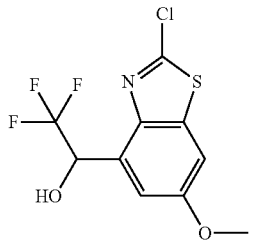
(633A)

Intermediate I-21 (207 mg, 0.909 mmol) was dissolved in THF (18.2 mL). (Trifluoromethyl)trimethylsilane (161 µL, 1.09 mmol) then TBAF (1 M in THF, 1.09 mL, 1.09 mmol) were added to the reaction. After stirring overnight, the reaction mixture was diluted with EtOAc and washed with water, saturated NaHCO$_3$, then brine, dried (Na$_2$SO$_4$), filtered, and concentrated in vacuo. The crude material was purified by column chromatography (ISCO, 40 g silica gel column, 19 minute gradient from 0 to 100% EtOAc in hexanes) to give Intermediate 633A (70.8 mg, 0.238 mmol, 26%) as a white solid: LC-MS: Method H, RT=0.98 min, MS (ESI) m/z: 298.1 (M+H)$^+$.

Intermediate 633B: 2,2,2-trifluoro-1-(6-methoxy-2-(2-methoxy-7-methylquinoxalin-5-yl)benzo[d]thiazol-4-yl)ethanol (Racemic)

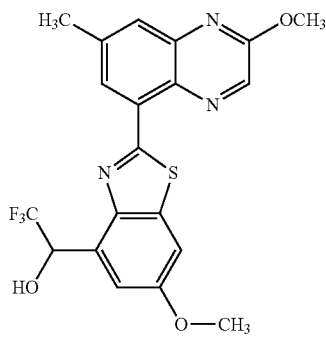
(633B)

Intermediate I-9 (70.6 mg, 0.235 mmol) and Intermediate 633A (70 mg, 0.235 mmol) were dissolved in DMF (2.35 mL). PdCl$_2$(dppf)-CH$_2$Cl$_2$ adduct (11.5 mg, 0.014 mmol) was added and the reaction degassed by bubbling with argon for 15 minutes. Sodium carbonate (2 M, 141 µL, 0.282 mmol) was added and the reaction degassed for 5 minutes, then sealed and heated to 100° C. in the microwave for 30 minutes. The reaction mixture was diluted with water and extracted thrice with EtOAc. The combined organic layers were washed with brine, dried (Na$_2$SO$_4$), filtered, and concentrated in vacuo. The crude material was purified by column chromatography (ISCO, 24 g silica gel column, 19 minute gradient from 0 to 100% EtOAc in hexanes) to give Intermediate 633B (racemic) (49.9 mg, 0.115 mmol, 49%) as a yellow solid: $^1$H NMR (400 MHz, CDCl$_3$) δ 8.55 (s, 1H), 8.48 (d, J=1.8 Hz, 1H), 7.78 (d, J=0.9 Hz, 1H), 7.43 (d, J=2.4 Hz, 1H), 7.35 (d, J=9.9 Hz, 1H), 7.06 (s, 1H), 5.35 (dd, J=9.8, 7.4 Hz, 1H), 4.13 (s, 3H), 3.93 (s, 3H), 2.66 (s, 3H); LC-MS: Method H, RT=1.21 min, MS (ESI) m/z: 436.1 (M+H)$^+$.

Example 633

Intermediate 633B (49.9 mg, 0.115 mmol) was purified by chiral SFC (Chiralpak OJ-H, 21×250 mm, 5 micron, 25% IPA/75% CO$_2$, 2 mL/min) to give Example 633 (Peak 2, Enantiomer 2, 20.4 mg, 0.044 mmol, 38%, >99% ee) as a yellow solid: $^1$H NMR (400 MHz, CDCl$_3$) δ 8.55 (s, 1H), 8.48 (d, J=1.5 Hz, 1H), 7.78 (dd, J=1.9, 1.0 Hz, 1H), 7.43 (d, J=2.4 Hz, 1H), 7.35 (d, J=9.9 Hz, 1H), 7.06 (d, J=2.2 Hz, 1H), 5.40-5.30 (m, 1H), 4.13 (s, 3H), 3.93 (s, 3H), 2.66 (s, 3H); LC-MS: Method H, RT=1.21 min, MS (ESI) m/z: 436.1 (M+H)$^+$.

Example 634

4-(1-fluoro-2,2-dimethylpropyl)-6-methoxy-2-(2-methoxy-7-methylquinoxalin-5-yl)benzo[d]thiazole

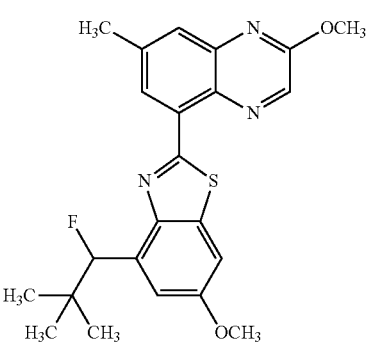
(634)

Intermediate 634A: 2-bromo-4-(1-fluoro-2,2-dimethylpropyl)-6-methoxybenzo[d]thiazole

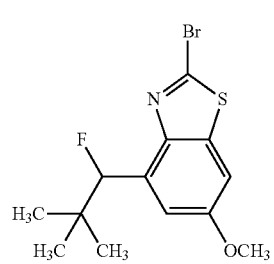
(634A)

Intermediate 628A (20 mg, 0.061 mmol) and Deoxofluor (14 µL, 0.076 mmol) were dissolved in DCM (606 µL). After 1 hour, the reaction mixture was diluted with EtOAc and washed with saturated NaHCO$_3$, water, then brine, dried (Na$_2$SO$_4$), filtered, and concentrated in vacuo to give Intermediate 634A (24 mg, 0.072 mmol, 100%), which was used immediately in the subsequent reaction: LC-MS: Method H, RT=1.29 min, MS (ESI) m/z: 332/334 (M+H)$^+$.

Example 634

Intermediate I-9 (10.8 mg, 0.036 mmol) and Intermediate 634A (10 mg, 0.030 mmol) were dissolved in DMF (301

μL). PdCl$_2$(dppf)-CH$_2$Cl$_2$ adduct (1.48 mg, 1.81 μmol) was added and the reaction degassed by bubbling with argon for 15 minutes. Sodium carbonate (18.1 μL, 0.036 mmol) was added and the reaction degassed for 5 minutes, then sealed and heated to 100° C. in the microwave for 30 minutes. The crude material was purified by preparative HPLC (Method D, 80-100% B in 15 minutes) to give Example 634 (3.5 mg, 0.0079 mmol, 26%): $^1$H NMR (500 MHz, CDCl$_3$) δ 8.50 (s, 1H), 8.48 (s, 1H), 7.67 (s, 1H), 7.30 (d, J=2.2 Hz, 1H), 7.11 (d, J=2.2 Hz, 1H), 6.37-6.25 (m, 1H), 4.06 (s, 3H), 3.85 (s, 3H), 2.60 (s, 3H), 1.03 (s, 9H); LC-MS: Method H, RT=1.47 min, MS (ESI) m/z: 426.2 (M+H)$^+$; Analytical HPLC Method B, 96% purity.

Example 635

4-(benzyloxy)-6-methoxy-2-(2-(methoxymethyl)-7-methylquinoxalin-5-yl)benzo[d]thiazole

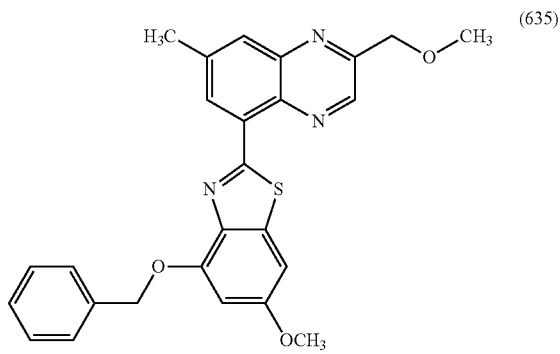 [SMILES: COCc1cnc2c(-c3nc4c(OCc5ccccc5)cc(OC)cc4s3)cc(C)cc2n1]

(635)

Intermediate 635A:
2-(benzyloxy)-4-methoxy-1-nitrobenzene

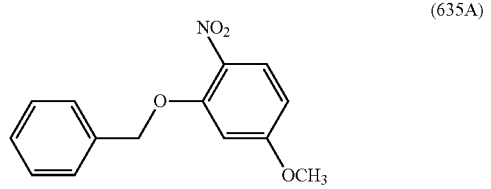 [SMILES: COc1ccc([N+](=O)[O-])c(OCc2ccccc2)c1]

(635A)

5-Methoxy-2-nitrophenol (1 g, 5.91 mmol), potassium carbonate (2.45 g, 17.7 mmol), and benzyl bromide (1.06 ml, 8.87 mmol) were dissolved in DMF (11.8 mL). After stirring overnight, the reaction mixture was diluted with water and extracted twice with EtOAc. The combined organic layers were washed with water, then brine, dried (Na$_2$SO$_4$), filtered, and concentrated in vacuo. The crude material was purified by column chromatography (ISCO, 120 g silica gel column, 29 minute gradient from 0 to 100% EtOAc in hexanes) to give Intermediate 635A (1.51 g, 5.81 mmol, 98%) as a light yellow oil: $^1$H NMR (400 MHz, CDCl$_3$) δ 8.01 (d, J=9.0 Hz, 1H), 7.52-7.46 (m, 2H), 7.43-7.37 (m, 2H), 7.36-7.30 (m, 1H), 6.57 (d, J=2.4 Hz, 1H), 6.52 (dd, J=9.1, 2.5 Hz, 1H), 5.22 (s, 2H), 3.84 (s, 3H); LC-MS: Method H, The compound did not ionize.

Intermediate 635B: 2-(benzyloxy)-4-methoxyaniline

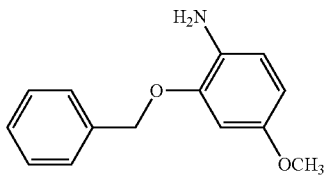

(635B)

Intermediate 635A (1.51 g, 5.81 mmol) was dissolved in MeOH (39.7 mL) and THF (4.96 mL). Ammonium chloride (6.21 g, 116 mmol) and zinc (3.80 g, 58.1 mmol) were added and the reaction mixture was heated to 40° C. After 3.5 hours, the reaction mixture was concentrated in vacuo. The crude material was redissolved in EtOAc/saturated Na$_2$CO$_3$ and allowed to stir vigorously for 15 minutes. The mixture was filtered through a sintered glass funnel. The organic layer was washed with water then brine, dried (Na$_2$SO$_4$), filtered, and concentrated in vacuo. The crude material was purified by column chromatography (ISCO, 80 g silica gel column, 29 minute gradient from 0 to 100% EtOAc in hexanes) to give Intermediate 635B (511 mg, 2.23 mmol, 38%) as a brown oil: $^1$H NMR (400 MHz, CDCl$_3$) δ 7.46-7.31 (m, 5H), 6.68 (d, J=8.4 Hz, 1H), 6.53 (d, J=2.6 Hz, 1H), 6.38 (dd, J=8.6, 2.6 Hz, 1H), 5.06 (s, 2H), 3.74 (s, 3H), 3.56 (br. s., 2H); LC-MS: Method H, RT=0.69 min, MS (ESI) m/z: 230.2 (M+H)$^+$.

Intermediate 635C: 4-(benzyloxy)-6-methoxybenzo[d]thiazol-2-amine (635C)

Intermediate 635B (0.5 g, 2.18 mmol) was dissolved in MeCN (10.9 mL). Ammonium thiocyanate (0.249 g, 3.27 mmol) was added, followed by benzyltrimethylammonium tribromide (0.850 g, 2.18 mmol). After stirring for 2 days, the reaction mixture was diluted with saturated NaHCO$_3$ and the solid collected by suction filtration and washed with water to give Intermediate 635C (574 mg, 2 mmol, 92%) as a purple solid: LC-MS: Method H, RT=0.77 min, MS (ESI) m/z: 287.2 (M+H)$^+$.

Intermediate 635D: 4-(benzyloxy)-2-chloro-6-methoxybenzo[d]thiazole

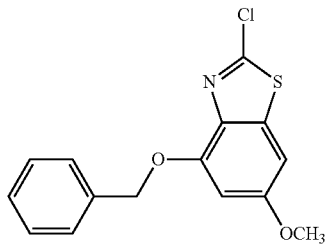

(635D)

Copper(II) chloride (0.377 g, 2.80 mmol) and t-butyl nitrite (0.357 mL, 3.00 mmol) were dissolved in MeCN (8 mL) and allowed to stir 10 minutes. Intermediate 635C (0.573 g, 2.001 mmol) was dissolved in MeCN (12 mL) and the copper solution was added and the reaction mixture was heated to 60° C. After 2 hours, the reaction mixture was concentrated in vacuo to remove the majority of the MeCN. The reaction was then diluted with EtOAc, washed twice with 1 N HCl, water, then brine, dried ($Na_2SO_4$), filtered, and concentrated in vacuo. The crude material was purified by column chromatography (ISCO, 80 g silica gel column, 29 minute gradient from 0 to 100% EtOAc in hexanes) to give Intermediate 635D (147 mg, 0.481 mmol, 24%) as a white solid: $^1$H NMR (400 MHz, $CDCl_3$) δ 7.48 (d, J=7.3 Hz, 2H), 7.40-7.34 (m, 2H), 7.32 (d, J=7.3 Hz, 1H), 6.79 (d, J=2.4 Hz, 1H), 6.54 (d, J=2.2 Hz, 1H), 5.32 (s, 2H), 3.80 (s, 3H); LC-MS: Method H, RT=1.17 min, MS (ESI) m/z: 306.1 (M+H)$^+$.

Example 635

Intermediate I-2 (13.2 mg, 0.042 mmol) and Intermediate 635D (10 mg, 0.035 mmol) were dissolved in DMF (350 μL). $PdCl_2(dppf)$-$CH_2Cl_2$ adduct (1.72 mg, 2.1 μmol) was added and the reaction degassed by bubbling with argon for 15 minutes. Sodium carbonate (2 M, 21 μL, 0.042 mmol) was added and the reaction degassed for 5 minutes, then sealed and heated to 100° C. in the microwave for 30 minutes. The crude material was purified by preparative HPLC (Method D, 40-80% B in 22 minutes) to give Example 635 (7.6 mg, 0.015 mmol, 44%): $^1$H NMR (500 MHz, $CDCl_3$) δ 9.00 (s, 1H), 8.85 (br. s., 1H), 7.85 (br. s., 1H), 7.50 (d, J=6.9 Hz, 2H), 7.39-7.22 (m, 3H), 6.95 (br. s., 1H), 6.52 (br. s., 1H), 5.38 (s, 2H), 4.77 (s, 2H), 3.79 (s, 3H), 3.50 (d, J=1.4 Hz, 3H), 2.61 (br. s., 3H); LC-MS: Method H, RT=1.29 min, MS (ESI) m/z: 458.2 (M+H)$^+$; Analytical HPLC Method B, 93% purity.

Example 636

1-(2-(7-chloro-2-methoxyquinoxalin-5-yl)-6-methoxybenzo[d]thiazol-4-yl)-2,2-dimethylpropan-1-ol

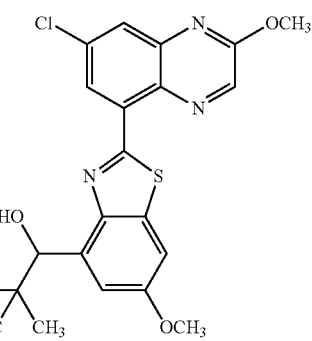

(636)

Intermediate I-28 (10.4 mg, 0.044 mmol) and Intermediate 628A (12 mg, 0.036 mmol) were dissolved in DMF (363 μL). $PdCl_2(dppf)$-$CH_2Cl_2$ adduct (1.78 mg, 2.18 μmol) was added and the reaction degassed by bubbling with argon for 15 minutes. Sodium carbonate (2 M, 21.8 μL, 0.044 mmol) was added and the reaction degassed for 5 minutes, then sealed and heated to 100° C. in the microwave for 30 minutes. The crude material was purified by preparative HPLC (Method D, 40-100% B in 15 minutes) then repurified by preparative HPLC (Method D, 45-85% B in 22 minutes) to give Example 636 (1.2 mg, 0.0025 mmol, 6.8%): $^1$H NMR (500 MHz, DMSO-$d_6$) δ 8.82 (s, 1H), 8.60 (d, J=2.2 Hz, 1H), 8.05 (d, J=2.2 Hz, 1H), 7.62 (d, J=2.2 Hz, 1H), 7.16 (d, J=2.2 Hz, 1H), 5.41 (br. s., 1H), 5.32 (br. s., 1H), 4.10 (s, 3H), 3.88 (s, 3H), 0.95 (s, 9H); LC-MS: Method H, RT=1.43 min, MS (ESI) m/z: 444.2 (M+H)$^+$; Analytical HPLC Method B, 91% purity.

Example 637

1-(6-methoxy-2-(2-methoxy-7-methylquinoxalin-5-yl)benzo[d]thiazol-4-yl)-2,2-dimethylpropan-1-ol

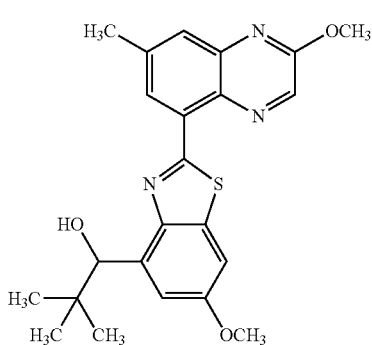

(637)

Intermediate 637A: 1-(2-bromo-6-methoxybenzo[d]thiazol-4-yl)-2,2-dimethylpropan-1-ol

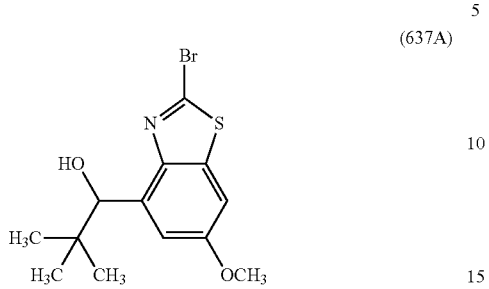
(637A)

Intermediate 628A (110 mg, 0.333 mmol) was purified by chiral preparative HPLC (Chiralpak AD, 90% heptane/10% EtOH:MeOH (50:50)) to give Intermediate 637A (33.8 mg, 0.102 mmol, 31%) as a clear oil: $^1$H NMR (400 MHz, CDCl$_3$) δ 7.16 (d, J=2.6 Hz, 1H), 6.98-6.91 (m, 1H), 4.84 (d, J=8.4 Hz, 1H), 4.02 (d, J=8.4 Hz, 1H), 3.86 (s, 3H), 0.96 (s, 9H); LC-MS: Method H, RT=1.14 min, MS (ESI) m/z: 330/332 (M+H)$^+$.

Example 637

Intermediate I-9 (5.45 mg, 0.018 mmol) and Intermediate 637A (5 mg, 0.015 mmol) were dissolved in DMF (151 μL). PdCl$_2$(dppf)-CH$_2$Cl$_2$ adduct (0.742 mg, 0.908 μmol) was added and the reaction degassed by bubbling with argon for 15 minutes. Sodium carbonate (2 M, 9.08 μL, 0.018 mmol) was added and the reaction degassed for 5 minutes, then sealed and heated to 100° C. in the microwave for 30 minutes. The crude material was purified by preparative HPLC (Method D, 70-100% B in 15 minutes) to give Example 637 (4.6 mg, 0.011 mmol, 70%): $^1$H NMR (500 MHz, DMSO-d$_6$) δ 8.78 (s, 1H), 8.59 (s, 1H), 7.87 (s, 1H), 7.65 (s, 1H), 7.20 (s, 1H), 5.48 (d, J=4.6 Hz, 1H), 5.38 (d, J=4.6 Hz, 1H), 4.14 (s, 3H), 3.93 (s, 3H), 2.70 (s, 3H), 1.01 (s, 9H); LC-MS: Method H, RT=1.36 min, MS (ESI) m/z: 424.1 (M+H)$^+$; Analytical HPLC Method B, 97% purity.

Example 638

2-((4-(1-hydroxy-2,2-dimethylpropyl)-2-(2-methoxy-7-methylquinoxalin-5-yl)benzo[d]thiazol-6-yl)oxy)ethyl (5-cyanopyridin-3-yl)carbamate

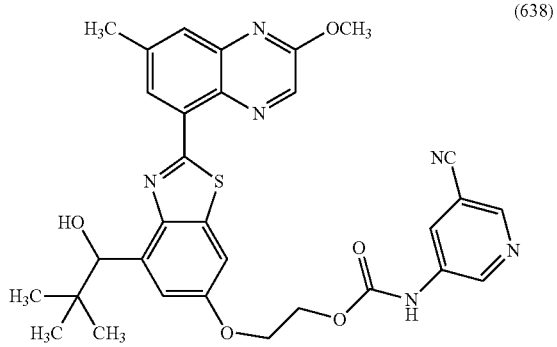 [SMILES: COc1cnc2c(-c3nc4c(C(O)C(C)(C)C)cc(OCCOC(=O)Nc5cncc(C#N)c5)cc4s3)cc(C)cc2n1]
(638)

Intermediate 638A: 1-(2-amino-6-methoxybenzo[d]thiazol-4-yl)-2,2-dimethylpropan-1-one

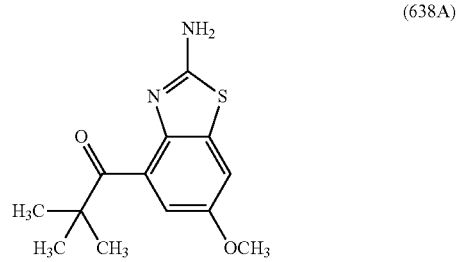
(638A)

Intermediate I-22 (0.5 g, 1.93 mmol) was dissolved in THF (19.3 mL). Sodium hydride (0.085 g, 2.12 mmol) was added. After 30 minutes, the reaction mixture was cooled to −78° C. and BuLi (1.68 ml, 3.86 mmol) was added. After 1 hour, methyl pivalate (0.77 mL, 5.79 mmol) was added and the reaction mixture was allowed to warm to ambient temperature. After achieving ambient temperature, the reaction mixture was diluted with EtOAc and washed with water, then brine, dried (Na$_2$SO$_4$), filtered, and concentrated in vacuo. The crude material was purified by column chromatography (ISCO, 24 g silica gel column, 19 minute gradient from 0 to 20% MeOH in DCM) to give Intermediate 638A (382 mg, 1.45 mmol, 75%) as a brown solid: $^1$H NMR (400 MHz, CDCl$_3$) δ 7.14 (d, J=2.4 Hz, 1H), 6.73 (d, J=2.6 Hz, 1H), 5.09 (br. s., 2H), 3.82 (s, 3H), 1.29 (s, 9H); LC-MS: Method H, RT=0.76 min, MS (ESI) m/z: 265.2 (M+H)$^+$.

Intermediate 638B: 1-(2-amino-6-hydroxybenzo[d]thiazol-4-yl)-2,2-dimethylpropan-1-one

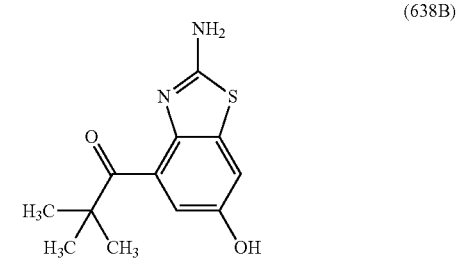 [SMILES: CC(C)(C)C(=O)c1cc(O)cc2sc(N)nc12]
(638B)

Intermediate 638A (380 mg, 1.44 mmol) was dissolved in AcOH (5.75 mL) and HBr (976 μL, 8.63 mmol) and heated to reflux. After heating for 2 days, the reaction mixture was concentrated in vacuo to give Intermediate 638B, which was used directly in the subsequent reaction: LC-MS: Method H, RT=0.64 min, MS (ESI) m/z: 251.1 (M+H)$^+$.

Intermediate 638C: 2-((2-amino-4-pivaloylbenzo[d]thiazol-6-yl)oxy)ethyl acetate

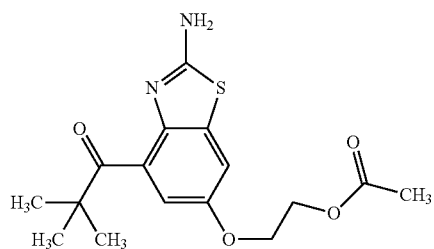
(638C)

Intermediate 638B (360 mg, 1.44 mmol), Cs₂CO₃ (2.81 g, 8.63 mmol), and 2-bromoethyl acetate (397 μL, 3.60 mmol) were dissolved in DMF (5.75 mL). After stirring overnight, the reaction mixture was diluted with water and extracted thrice with EtOAc. The combined organic layers were washed with brine, dried (Na₂SO₄), filtered, and concentrated in vacuo. The crude material was purified by preparative HPLC (Method A, 30-100% B in 12 minutes) to give Intermediate 638C (139 mg, 0.412 mmol, 29%) as a white solid: LC-MS: Method H, RT=0.76 min, MS (ESI) m/z: 337.2 (M+H)⁺.

Intermediate 638D: 2-((2-chloro-4-pivaloylbenzo[d]thiazol-6-yl)oxy)ethyl acetate

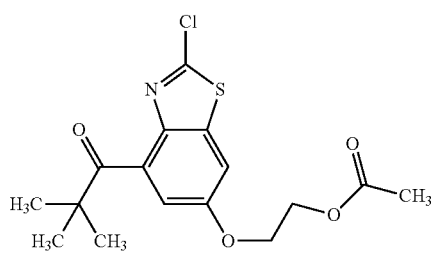
(638D)

Copper(II) chloride (78 mg, 0.577 mmol) and t-butyl nitrite (73.5 μL, 0.618 mmol) were dissolved in MeCN (1.65 mL) and allowed to stir 10 minutes. Intermediate 638C (139 mg, 0.412 mmol) was dissolved in MeCN (2.47 mL) and the copper solution was added and the reaction mixture was heated to 60° C. After 2.5 hours, the reaction mixture was concentrated in vacuo to remove the majority of the MeCN. The reaction was then diluted with EtOAc, washed twice with 1 N HCl, water, then brine, dried (Na₂SO₄), filtered, and concentrated in vacuo to give Intermediate 638D (134 mg, 0.377 mmol, 91%) as an orange oil: LC-MS: Method H, RT=1.11 min, MS (ESI) m/z: 356.1 (M+H)⁺.

Intermediate 638E: 1-(2-chloro-6-(2-hydroxy-ethoxy)benzo[d]thiazol-4-yl)-2,2-dimethylpropan-1-ol

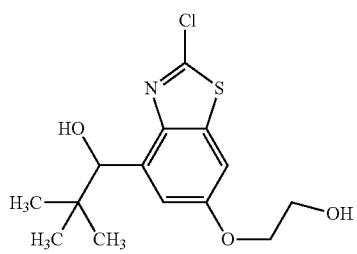
(638E)

Intermediate 638D (134 mg, 0.377 mmol) was dissolved in toluene (2.51 mL) and THF (1.26 mL) and cooled to −78° C. DIBAL-H (1 M in toluene, 1.13 mL, 1.13 mmol) was added and the reaction was warmed to ambient temperature. After 5 hours, more DIBAL-H (1130 μL, 1.130 mmol) was added. After 45 minutes, the reaction was quenched with a saturated solution of Rochelle's salt. After stirring overnight, the reaction mixture was extracted with EtOAc. The organic layer was further washed with brine, dried (Na₂SO₄), filtered, and concentrated in vacuo. The crude material was purified by column chromatography (ISCO, 12 g silica gel column, 17 minute gradient from 0 to 100% EtOAc in hexanes). The resulting product was purified by chiral preparative HPLC (Chiralpak AD, 16% MeOH/EtOH (50/50) in heptane) to give Intermediate 638E (7.2 mg, 0.023 mmol, 6.1%) as a clear oil: LC-MS: Method H, RT=0.97 min, MS (ESI) m/z: 316.1 (M+H)⁺.

Intermediate 638F: 2-((2-chloro-4-(1-hydroxy-2,2-dimethylpropyl)benzo[d]thiazol-6-yl)oxy)ethyl carbonochloridate

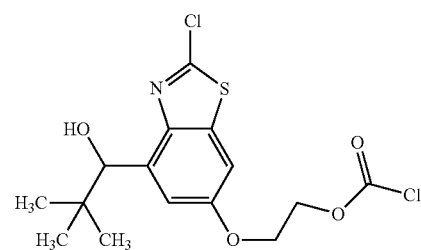
(638F)

Intermediate 638E (7.2 mg, 0.023 mmol) and phosgene solution (15% in toluene, 0.114 mmol) were dissolved in THF (228 After 1.5 hours, the reaction mixture was concentrated in vacuo to give Intermediate 638F, which was used directly in the subsequent reaction.

Intermediate 638G: 2-((2-chloro-4-(1-hydroxy-2,2-dimethylpropyl)benzo[d]thiazol-6-yl)oxy)ethyl (5-cyanopyridin-3-yl)carbamate

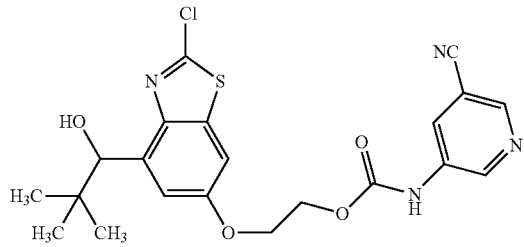

(638G)

Intermediate 638F (8.6 mg, 0.023 mmol), 5-aminonicotinonitrile (9.48 mg, 0.080 mmol), and pyridine (18.4 µL, 0.227 mmol) were dissolved in DCM (455 After 45 minutes, the reaction mixture was concentrated in vacuo to give Intermediate 638G, which was used directly in the subsequent reaction: LC-MS: Method H, RT=1.07 min, MS (ESI) m/z: 461.1 (M+H)$^+$.

Example 638

Intermediate I-9 (8.21 mg, 0.027 mmol) and Intermediate 638G (10.5 mg, 0.023 mmol) were dissolved in DMF (228 µL). PdCl$_2$(dppf)-CH$_2$Cl$_2$ adduct (1.12 mg, 1.37 µmol) was added and the reaction degassed by bubbling with argon for 15 minutes. Sodium carbonate (2 M, 13.7 µL, 0.027 mmol) was added and the reaction degassed for 5 minutes, then sealed and heated to 100° C. in the microwave for 30 minutes. The crude material was purified by preparative HPLC (Method D, 65-100% B in 20 minutes) to give Example 638 (2.0 mg, 0.0033 mmol, 15%): $^1$H NMR (500 MHz, DMSO-d$_6$) δ 8.79 (br. s., 1H), 8.66 (s, 1H), 8.59 (s, 1H), 8.46 (s, 1H), 8.23 (br. s., 1H), 7.89 (s, 1H), 7.75 (s, 1H), 7.58 (br. s., 1H), 7.09 (br. s., 1H), 5.35 (d, J=4.9 Hz, 1H), 5.24 (d, J=4.6 Hz, 1H), 4.49 (br. s., 2H), 4.30 (d, J=11.3 Hz, 2H), 4.01 (s, 3H), 2.58 (s, 3H), 0.88 (s, 9H); LC-MS: Method H, RT=1.27 min, MS (ESI) m/z: 599.2 (M+H)$^+$; Analytical HPLC Method B, 100% purity.

Example 639

8-(4-(1-hydroxy-2,2-dimethylpropyl)-6-methoxybenzo[d]thiazol-2-yl)-3-methoxyquinoxaline-6-carbonitrile

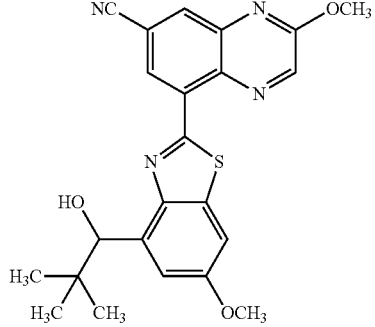

(639)

Intermediate I-38 (4.16 mg, 0.018 mmol) and Intermediate 637A (5 mg, 0.015 mmol) were dissolved in DMF (151 µL). PdCl$_2$(dppf)-CH$_2$Cl$_2$ adduct (0.742 mg, 0.908 µmol) was added and the reaction degassed by bubbling with argon for 15 minutes. Sodium carbonate (2 M, 9.08 µL, 0.018 mmol) was added and the reaction degassed for 5 minutes, then sealed and heated to 100° C. in the microwave for 30 minutes. The crude material was purified by preparative HPLC (Method D, 45-90% B in 20 minutes) to give Example 639 (2.1 mg, 0.0046 mmol, 30%): $^1$H NMR (500 MHz, DMSO-d$_6$) δ 9.02 (s, 1H), 8.93 (s, 1H), 8.59 (s, 1H), 7.69 (br. s., 1H), 7.23 (br. s., 1H), 5.49 (br. s., 1H), 5.38 (d, J=4.0 Hz, 1H), 4.19 (s, 3H), 3.94 (s, 3H), 1.02 (s, 9H); LC-MS: Method H, RT=1.25 min, MS (ESI) m/z: 435.2 (M+H)$^+$; Analytical HPLC Method B, 95% purity.

Example 640

1-(6-ethoxy-2-(2-methoxy-7-methylquinoxalin-5-yl)benzo[d]thiazol-4-yl)-2,2-dimethylpropan-1-ol

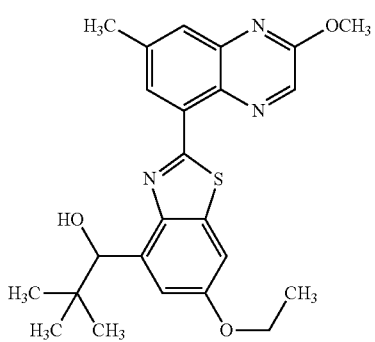

(640)

Intermediate 640A: 1-(2-chloro-6-methoxybenzo[d]thiazol-4-yl)-2,2-dimethylpropan-1-one

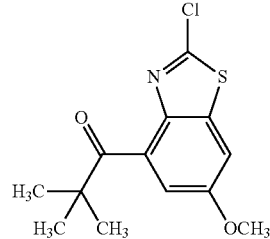

(640A)

Copper(II) chloride (0.363 g, 2.70 mmol) and t-butyl nitrite (0.344 mL, 2.89 mmol) were dissolved in MeCN (7.72 mL) and allowed to stir 10 minutes. Intermediate 638A (0.51 g, 1.93 mmol) was dissolved in MeCN (11.6 mL) and the copper solution was added and the reaction mixture was heated to 60° C. After 2 hours, the reaction mixture was diluted with EtOAc, washed with 1 N HCl, saturated NaHCO$_3$, then brine, dried (Na$_2$SO$_4$), filtered, and concentrated in vacuo. The crude material was purified by column chromatography (ISCO, 40 g silica gel column, 17 minute gradient from 0 to 100% EtOAc in hexanes) to give Intermediate 640A (211 mg, 0.743 mmol, 39%) as a brown oil:

¹H NMR (400 MHz, CDCl₃) δ 7.23 (d, J=2.6 Hz, 1H), 6.87 (d, J=2.4 Hz, 1H), 3.87 (s, 3H), 1.30 (s, 9H); LC-MS: Method H, RT=1.15 min, MS (ESI) m/z: 284.2 (M+H)⁺.

Intermediate 640B: 1-(2-chloro-6-hydroxybenzo[d]thiazol-4-yl)-2,2-dimethylpropan-1-one

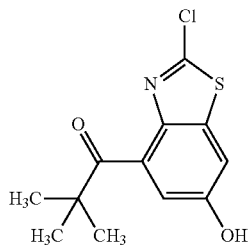

(640B)

Intermediate 640A (190 mg, 0.670 mmol) and borontribromide (1 M in THF, 2.01 mL, 2.01 mmol) were dissolved in DCM (6.7 mL). After 2 hours, the reaction mixture was diluted with DCM, washed with 1 N HCl, then brine, dried (Na₂SO₄), filtered, and concentrated in vacuo to give Intermediate 640B, which was used directly in the subsequent step: LC-MS: Method H, RT=1.01 min, MS (ESI) m/z: 270.1 (M+H)⁺.

Intermediate 640C: 1-(2-(2-(difluoromethoxy)-7-methylquinoxalin-5-yl)-6-hydroxybenzo[d]thiazol-4-yl)-2,2-dimethylpropan-1-one

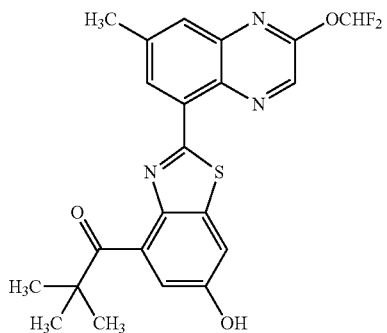

(640C)

Intermediate I-1 (221 mg, 0.872 mmol) and Intermediate 640B (196 mg, 0.727 mmol) were dissolved in DMF (7.27 mL). PdCl₂(dppf)-CH₂Cl₂ adduct (35.6 mg, 0.044 mmol) was added and the reaction degassed by bubbling with argon for 15 minutes. Sodium carbonate (2M, 436 µL, 0.872 mmol) was added and the reaction mixture was degassed for 5 minutes, then sealed and heated to 100° C. in the microwave for 40 minutes. More PdCl₂(dppf)-CH₂Cl₂Adduct (35.6 mg, 0.044 mmol) was added and the reaction mixture was heated for an additional 30 minutes in the microwave at 100° C. The reaction mixture was diluted with water and extracted thrice with EtOAc. The combined organic layers were washed with brine, dried (Na₂SO₄), filtered, and concentrated in vacuo. The crude material was purified by column chromatography (ISCO, 40 g silica gel column, 19 minute gradient from 0 to 100% EtOAc in hexanes) to give Intermediate 640C (182 mg, 0.411 mmol, 57%) as a yellow solid: ¹H NMR (400 MHz, CDCl₃) δ 8.68 (d, J=1.8 Hz, 1H), 8.66 (s, 1H), 7.77 (dd, J=1.8, 0.9 Hz, 1H), 7.85-7.44 (m, 1H), 7.38 (d, J=2.4 Hz, 1H), 6.84 (d, J=2.6 Hz, 1H), 5.18 (s, 1H), 2.66 (s, 3H), 1.39 (s, 9H); LC-MS: Method H, RT=1.21 min, MS (ESI) m/z: 444.2 (M+H)⁺.

Intermediate 640D: 1-(6-hydroxy-2-(2-methoxy-7-methylquinoxalin-5-yl) benzo[d]thiazol-4-yl)-2,2-dimethylpropan-1-one

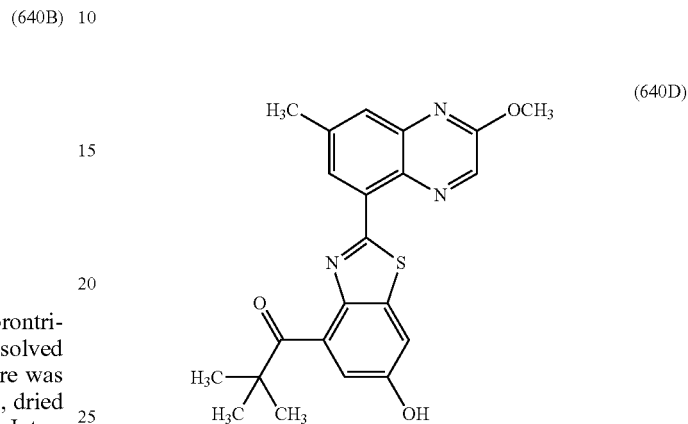

(640D)

Intermediate 640C (180 mg, 0.406 mmol) was azeotroped with toluene and stored on HIVAC overnight. The starting material was dissolved in THF (8.12 mL). Sodium methoxide (0.5 M in MeOH, 554 µL, 2.03 mmol) was then added. After 1 hour, the reaction mixture was diluted with 1 N HCl and extracted thrice with EtOAc. The combined organic layers were washed with brine, dried (Na₂SO₄), filtered, and concentrated in vacuo to give Intermediate 640D (167 mg, 0.411 mmol, 100%) as an off-white solid: ¹H NMR (400 MHz, CDCl₃) δ 8.55 (d, J=1.8 Hz, 1H), 8.53 (s, 1H), 7.74 (dd, J=1.8, 0.9 Hz, 1H), 7.38 (d, J=2.4 Hz, 1H), 6.82 (d, J=2.4 Hz, 1H), 5.08 (s, 1H), 4.12 (s, 3H), 2.62 (s, 3H), 1.39 (s, 9H); LC-MS: Method H, RT=1.25 min, MS (ESI) m/z: 408.2 (M+H)⁺.

Intermediate 640E: 1-(6-ethoxy-2-(2-methoxy-7-methylquinoxalin-5-yl)benzo[d]thiazol-4-yl)-2,2-dimethylpropan-1-one

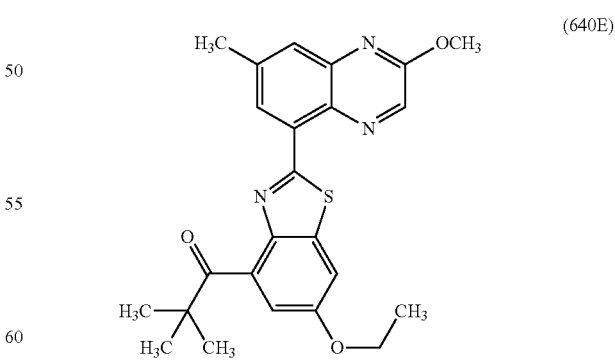

(640E)

Intermediate 640D (20 mg, 0.049 mmol) was dissolved in THF (982 µL). Cesium carbonate (16 mg, 0.049 mmol) then ethyl iodide (5.95 µL, 0.074 mmol) were added. After stirring overnight, the reaction mixture was diluted with EtOAc, washed with water, then brine, dried (Na₂SO₄), filtered, and concentrated in vacuo to give Intermediate 640E, which was used directly in the subsequent reaction: LC-MS: Method H, RT=1.43 min, MS (ESI) m/z: 436.2 (M+H)+.

Example 640

Intermediate 640E (21 mg, 0.048 mmol) was dissolved in MeOH (964 µL) and cooled to 0° C. Sodium borohydride (5.47 mg, 0.145 mmol) was then added. After 1.5 hours, the reaction was warmed to ambient temperature. After 1.5 hours, the reaction mixture was diluted with EtOAc, washed with water then brine, dried ($Na_2SO_4$), filtered, and concentrated in vacuo. The crude material was purified by preparative HPLC (Method D, 60-100% B in 30 minutes) to give Example 640 (5.7 mg, 0.013 mmol, 27%): $^1$H NMR (500 MHz, DMSO-$d_6$) δ 8.79 (s, 1H), 8.59 (s, 1H), 7.88 (s, 1H), 7.63 (br. s., 1H), 7.19 (br. s., 1H), 5.47 (br. s., 1H), 5.38 (br. s., 1H), 4.23-4.16 (m, 2H), 4.15 (s, 3H), 2.71 (s, 3H), 1.46 (t, J=6.7 Hz, 3H), 1.01 (s, 9H); LC-MS: Method H, RT=1.40 min, MS (ESI) m/z: 438.2 (M+H)+; Analytical HPLC Method B, 100% purity.

Example 641

2-(6-methoxy-2-(2-methoxy-7-methylquinoxalin-5-yl)benzo[d]thiazol-4-yl)ethanol

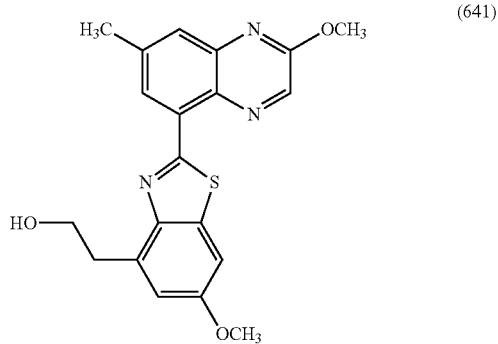 [SMILES: COc1cc(CCO)c2nc(-c3cc(C)cc4nc(OC)cnc34)sc2c1]

(641)

Intermediate 641A: ethyl 2-(5-methoxy-2-nitrophenyl)acetate

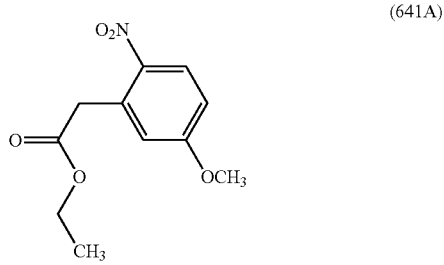 [SMILES: CCOC(=O)Cc1cc(OC)ccc1[N+](=O)[O-]]

(641A)

Ethyl 2-(5-hydroxy-2-nitrophenyl)acetate (100 mg, 0.444 mmol), potassium carbonate (123 mg, 0.888 mmol), and iodomethane (41.6 µL, 0.666 mmol) were dissolved in acetone (4.44 mL). After stirring overnight, the reaction mixture was concentrated in vacuo, diluted with EtOAc, washed with aqueous HCl, water, then brine, dried ($Na_2SO_4$), filtered, and concentrated in vacuo to give Intermediate 641A (102 mg, 0.427 mmol, 96%) as a brown oil: $^1$H NMR (400 MHz, CDCl$_3$) δ 8.22 (d, J=9.0 Hz, 1H), 6.93 (dd, J=9.1, 2.8 Hz, 1H), 6.82 (d, J=2.6 Hz, 1H), 4.21 (q, J=7.1 Hz, 2H), 4.02 (s, 2H), 3.92 (s, 3H), 1.29 (t, J=7.0 Hz, 3H); LC-MS: Method H, RT=0.93 min, MS (ESI) m/z: 240.0 (M+H)+.

Intermediate 641B: 2-(5-methoxy-2-nitrophenyl)ethanol

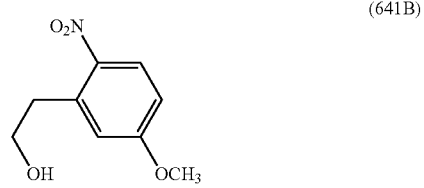

(641B)

Intermediate 641A (100 mg, 0.418 mmol) was dissolved in toluene (2.79 mL) and THF (1.39 mL) and cooled to −78° C. DIBAL-H (1 M in toluene, 920 µL, 0.920 mmol) was added and the reaction mixture was allowed to warm slowly to ambient temperature. After 1.5 hours, the reaction was quenched with saturated Rochelle's salt. After stirring overnight, the reaction mixture was extracted with EtOAc, washed with water, then brine, dried ($Na_2SO_4$), filtered, and concentrated in vacuo. The crude material was purified by column chromatography (ISCO, 12 g silica gel column, 17 minute gradient from 0 to 100% EtOAc in hexanes) to give Intermediate 641B (65 mg, 0.33 mmol, 79%) as a yellow oil: $^1$H NMR (400 MHz, CDCl$_3$) δ 8.09 (d, J=9.0 Hz, 1H), 6.91-6.84 (m, 2H), 3.99 (t, J=6.3 Hz, 2H), 3.91 (s, 3H), 3.25 (t, J=6.3 Hz, 2H); LC-MS: Method H, Did not ionize well.

Intermediate 641C: 2-(2-amino-5-methoxyphenyl)ethanol

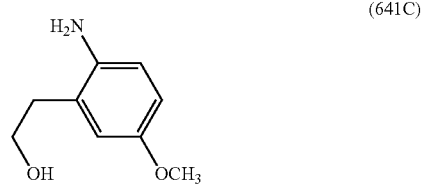 [SMILES: COc1ccc([N+](=O)[O-])c(CCO)c1]

(641C)

Intermediate 641B (65 mg, 0.330 mmol) was dissolved in EtOH (471 Palladium on carbon (7.02 mg, 6.59 µmol) then ammonium formate (104 mg, 1.65 mmol) were added and the reaction mixture was heated to reflux. After 1 hour, the reaction mixture was filtered through celite and concentrated in vacuo to give Intermediate 641C (54.8 mg, 0.328 mmol, 99%) as a brown oil: $^1$H NMR (400 MHz, CDCl$_3$) δ 7.29 (s, 1H), 6.69 (s, 2H), 3.94 (t, J=6.1 Hz, 2H), 3.77 (s, 3H), 2.82 (t, J=6.2 Hz, 2H); LC-MS: Method H, RT=0.51 min, MS (ESI) m/z: 168.0 (M+H)+.

Intermediate 641D: 2-(2-amino-6-methoxybenzo[d]thiazol-4-yl)ethanol

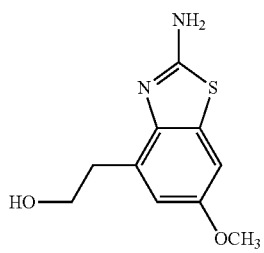

Intermediate 641C (55 mg, 0.329 mmol) was dissolved in MeCN (1.64 mL). Ammonium thiocyanate (37.6 mg, 0.493 mmol) was added, followed by benzyltrimethylammonium tribromide (128 mg, 0.329 mmol). After stirring for 5 days, the reaction mixture was diluted with saturated NaHCO$_3$. The reaction mixture was extracted thrice with EtOAc. The combined organic layers were washed with brine, dried (Na$_2$SO$_4$), filtered, and concentrated in vacuo to give Intermediate 641D (59.9 mg, 0.267 mmol, 81%) as a brown solid: LC-MS: Method H, RT=0.59 min, MS (ESI) m/z: 225.0 (M+H)$^+$.

Intermediate 641E: 2-(2-chloro-6-methoxybenzo[d]thiazol-4-yl)ethanol

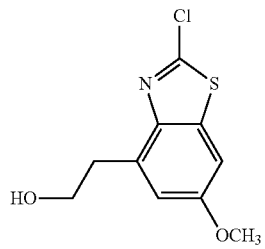

Copper(II) chloride (50.4 mg, 0.375 mmol) and t-butyl nitrite (47.7 μL, 0.401 mmol) were dissolved in MeCN (1.07 mL) and allowed to stir 10 minutes. Intermediate 641D (60 mg, 0.268 mmol) was dissolved in MeCN (1.6 mL) and the copper solution was added and the reaction mixture was heated to 60° C. After 1.5 hours, the reaction mixture was diluted with EtOAc, washed with 1 N HCl, saturated NaHCO$_3$, then brine, dried (Na$_2$SO$_4$), filtered, and concentrated in vacuo to give Intermediate 641E (51.6 mg, 0.212 mmol, 79%) as a red oil: $^1$H NMR (400 MHz, CDCl$_3$) δ 7.14 (d, J=2.4 Hz, 1H), 6.96 (d, J=2.4 Hz, 1H), 4.02 (br. s., 2H), 3.88 (s, 3H), 3.29 (t, J=6.1 Hz, 2H), 2.34 (br. s., 1H); LC-MS: Method H, RT=0.90 min, MS (ESI) m/z: 244.0 (M+H)$^+$.

Example 641

Intermediate I-9 (14.8 mg, 0.049 mmol) and Intermediate 641E (10 mg, 0.041 mmol) were dissolved in DMF (410 μL). PdCl$_2$(dppf)-CH$_2$Cl$_2$ adduct (2.01 mg, 2.46 μmol) was added and the reaction degassed by bubbling with argon for 15 minutes. Sodium carbonate (2 M, 24.6 μL, 0.049 mmol) was added and the reaction degassed for 5 minutes, then sealed and heated to 100° C. in the microwave for 30 minutes. The crude material was purified by preparative HPLC (Method D, 40-90% B in 15 minutes) to give Example 641 (6.4 mg, 0.016 mmol, 40%): $^1$H NMR (500 MHz, DMSO-d$_6$) δ 8.69 (s, 1H), 8.53 (s, 1H), 7.78 (s, 1H), 7.52 (s, 1H), 7.00 (s, 1H), 4.81 (t, J=5.2 Hz, 1H), 4.06 (s, 3H), 3.88-3.73 (m, 5H), 3.30 (t, J=7.0 Hz, 2H), 2.62 (s, 3H); LC-MS: Method H, RT=1.19 min, MS (ESI) m/z: 382.1 (M+H)$^+$; Analytical HPLC Method B, 97% purity.

Example 642

(6-methoxy-2-(2-methoxy-7-methylquinoxalin-5-yl)benzo[d]thiazol-4-yl)(3-(trifluoromethyl)phenyl)methanol

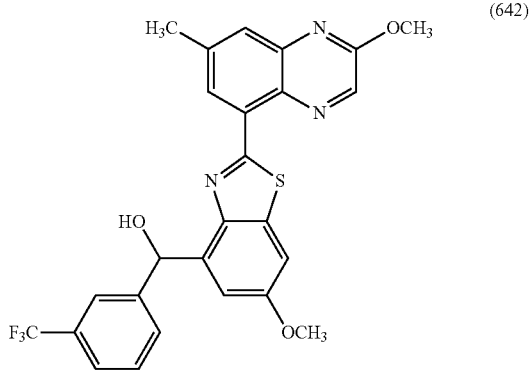 [SMILES: COc1cc(C(O)c2cccc(C(F)(F)F)c2)c2nc(-c3cc(C)cc4nc(OC)cnc34)sc2c1]

Intermediate 642A: (2-amino-6-methoxybenzo[d]thiazol-4-yl)(3-(trifluoromethyl) phenyl)methanol

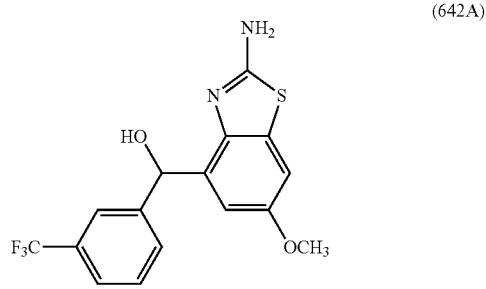 [SMILES: COc1cc(C(O)c2cccc(C(F)(F)F)c2)c2nc(N)sc2c1]

Intermediate I-22 (50 mg, 0.193 mmol) was dissolved in THF (1.93 mL). Sodium hydride (17 mg, 0.425 mmol) was added. After 30 minutes, the reaction mixture was cooled to −78° C. and BuLi (2.5 M in hexanes, 101 μL, 0.232 mmol) was added. After 30 minutes, 3-(trifluromethyl)benzaldehyde (50.4 mg, 0.289 mmol) was added and the reaction mixture was allowed to warm to ambient temperature. After achieving ambient temperature, the reaction mixture was diluted with EtOAc, washed with water, then brine, dried (Na$_2$SO$_4$), filtered, and concentrated in vacuo to give Intermediate 642A, which was used directly in the subsequent reaction: LC-MS: Method H, RT=0.83 min, MS (ESI) m/z: 355.0 (M+H)$^+$.

Intermediate 642B: (2-chloro-6-methoxybenzo[d]thiazol-4-yl)(3-(trifluoromethyl)phenyl)methanol

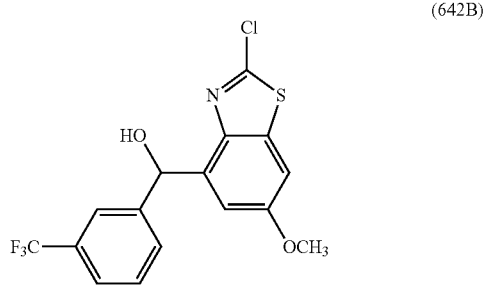 [SMILES: COc1cc(C(O)c2cccc(C(F)(F)F)c2)c2nc(Cl)sc2c1]

(642B)

Intermediate 642A (68 mg, 0.192 mmol), lithium chloride (8.14 mg, 0.192 mmol), copper(II) chloride (25.8 mg, 0.192 mmol), and tert-butyl nitrite (22.9 µL, 0.192 mmol) were dissolved in MeCN (1.92 mL). After 2 hours, the reaction mixture was diluted with EtOAc, washed with 1 N HCl, saturated NaHCO$_3$, then brine, dried (Na$_2$SO$_4$), filtered, and concentrated in vacuo to give Intermediate 642B (73.5 mg, 0.197 mmol, 100%) as a red oil: LC-MS: Method H, RT=1.10 min, MS (ESI) m/z: 374.0 (M+H)$^+$.

Example 642

Intermediate I-9 (15 mg, 0.050 mmol) and Intermediate 642B (22.4 mg, 0.060 mmol) were dissolved in DMF (250 µL). PdCl$_2$(dppf)-CH$_2$Cl$_2$ adduct (2.45 mg, 3.00 µmol) was added and the reaction degassed by bubbling with argon for 15 minutes. Sodium carbonate (2 M, 30.0 µL, 0.060 mmol) was added and the reaction degassed for 5 minutes, then sealed and heated to 100° C. in the microwave for 30 minutes. The crude material was purified by preparative HPLC (Method D, 45-90% B in 20 minutes) then repurified by preparative HPLC (Method D, 60-100% B in 15 minutes) to give Example 642 (7.5 mg, 0.015 mmol, 29%): $^1$H NMR (500 MHz, DMSO-d$_6$) δ 8.78 (s, 1H), 8.65 (s, 1H), 8.17 (s, 1H), 7.90 (s, 1H), 7.87 (d, J=7.6 Hz, 1H), 7.67 (d, J=2.4 Hz, 1H), 7.64-7.55 (m, 2H), 7.41 (d, J=2.1 Hz, 1H), 6.76 (d, J=4.3 Hz, 1H), 6.44 (d, J=4.3 Hz, 1H), 4.14 (s, 3H), 3.94 (s, 3H), 2.72 (s, 3H); LC-MS: Method H, RT=1.34 min, MS (ESI) m/z: 512.1 (M+H)$^+$; Analytical HPLC Method B, 100% purity.

Example 643

(2-isopropylphenyl)(6-methoxy-2-(2-methoxy-7-methylquinoxalin-5-yl)benzo[d]thiazol-4-yl)methanol

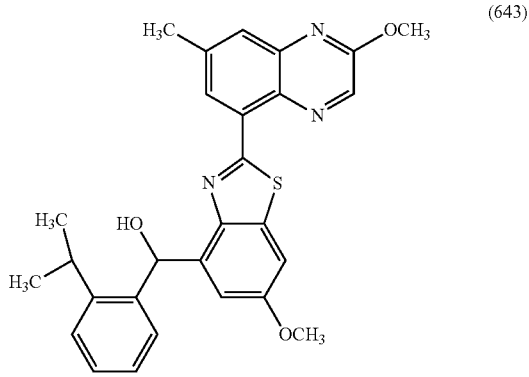 [SMILES: COc1cc(C(O)c2ccccc2C(C)C)c2nc(-c3cc(C)cc4nc(OC)cnc34)sc2c1]

(643)

Intermediate 643A: (2-amino-6-methoxybenzo[d]thiazol-4-yl)(2-isopropylphenyl)methanol

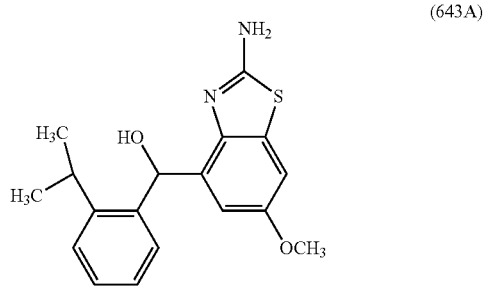 [SMILES: COc1cc(C(O)c2ccccc2C(C)C)c2nc(N)sc2c1]

(643A)

Intermediate I-22 (50 mg, 0.193 mmol) was dissolved in THF (1.93 mL). Sodium hydride (17 mg, 0.425 mmol) was then added. After 30 minutes, the reaction mixture was cooled to −78° C. and BuLi (2.5 M in hexanes, 101 µL, 0.232 mmol) was added. After 30 minutes, 2-isopropylbenzaldehyde (42.9 mg, 0.289 mmol) was added and the reaction mixture was allowed to warm to ambient temperature. After achieving ambient temperature, the reaction mixture was diluted with EtOAc, washed with water, then brine, dried (Na$_2$SO$_4$), filtered, and concentrated in vacuo to give Intermediate 643A, which was used directly in the subsequent reaction: LC-MS: Method H, RT=0.87 min, MS (ESI) m/z: 329.1 (M+H)$^+$.

Intermediate 643B: (2-chloro-6-methoxybenzo[d]thiazol-4-yl)(2-isopropylphenyl)methanol

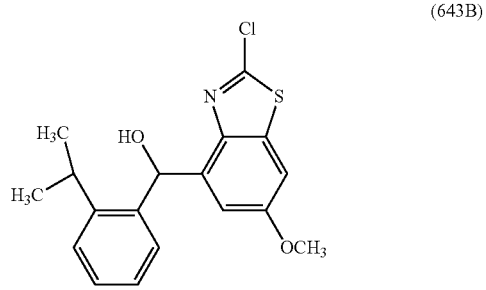 [SMILES: COc1cc(C(O)c2ccccc2C(C)C)c2nc(Cl)sc2c1]

(643B)

Intermediate 643A (63 mg, 0.192 mmol), lithium chloride (8.13 mg, 0.192 mmol), copper(II) chloride (25.8 mg, 0.192 mmol), and tert-butyl nitrite (22.9 µL, 0.192 mmol) were dissolved in MeCN (1.92 mL). After 2 hours, the reaction mixture was diluted with EtOAc, washed with 1 N HCl, saturated NaHCO$_3$, then brine, dried (Na$_2$SO$_4$), filtered, and concentrated in vacuo to give Intermediate 643B, which was used directly in the subsequent reaction: LC-MS: Method H, RT=1.18 min, MS (ESI) m/z: 348 (M+H)$^+$.

Example 643

Intermediate I-9 (15 mg, 0.050 mmol) and Intermediate 643B (20.9 mg, 0.060 mmol) were dissolved in DMF (250 µL). PdCl$_2$(dppf)-CH$_2$Cl$_2$ adduct (2.45 mg, 3.00 µmol) was added and the reaction degassed by bubbling with argon for 15 minutes. Sodium carbonate (2 M, 30.0 µL, 0.060 mmol) was added and the reaction degassed for 5 minutes, then sealed and heated to 100° C. in the microwave for 30 minutes. The crude material was purified by preparative HPLC (Method D, 50-100% B in 20 minutes) then repurified by preparative HPLC (Method D, 60-100% B in 20 minutes) to give Example 643 (1.7 mg, 0.0034 mmol, 6.7%): $^1$H NMR (500 MHz, DMSO-$d_6$) δ 8.71 (s, 1H), 8.45 (s, 1H), 7.80 (s, 1H), 7.61 (d, J=2.4 Hz, 1H), 7.36-7.26 (m, 3H), 7.20 (t, J=7.6 Hz, 1H), 7.14-7.08 (m, 1H), 6.98 (d, J=4.9 Hz, 1H), 5.92 (d, J=5.2 Hz, 1H), 4.07 (s, 3H), 3.96-3.85 (m, 4H), 2.60 (s, 3H), 1.32 (d, J=7.0 Hz, 3H), 1.21 (d, J=6.7 Hz, 3H); LC-MS: Method H, RT=1.37 min, MS (ESI) m/z: 486.1 (M+H)$^+$; Analytical HPLC Method B, 96% purity.

Example 644

Ethyl 1-(hydroxy(6-methoxy-2-(2-methoxy-7-methylquinoxalin-5-yl)benzo[d]thiazol-4-yl)methyl)cyclobutanecarboxylate

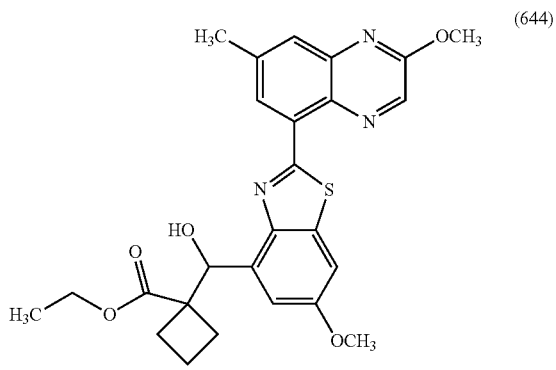 [SMILES: CCOC(=O)C1(C(O)c2cc(OC)cc3sc(-c4cc(C)cc5nc(OC)cnc45)nc23)CCC1]

(644)

Intermediate 644A: Ethyl 1-(2-amino-6-methoxybenzo[d]thiazole-4-carbonyl)cyclobutanecarboxylate

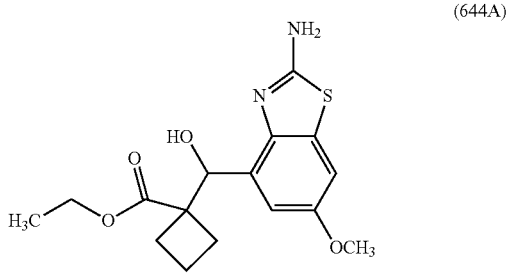 [SMILES: CCOC(=O)C1(C(O)c2cc(OC)cc3sc(N)nc23)CCC1]

(644A)

Intermediate I-22 (50 mg, 0.193 mmol) was dissolved in THF (1.93 mL). Sodium hydride (17 mg, 0.425 mmol) was then added. After 15 minutes, the reaction mixture was cooled to −78° C. and BuLi (2.5 M in hexanes, 101 μL, 0.232 mmol) was added. After 30 minutes, diethyl cyclobutane-1,1-dicarboxylate (58.0 mg, 0.289 mmol) was added and the reaction mixture was allowed to warm to ambient temperature. After achieving ambient temperature, the reaction mixture was diluted with EtOAc, washed with water, then brine, dried (Na$_2$SO$_4$), filtered, and concentrated in vacuo to give Intermediate 644A, which was used directly in the subsequent reaction: LC-MS: Method H, RT=0.77 min, MS (ESI) m/z: 335.0 (M+H)$^+$.

Intermediate 644B: Ethyl 1-(2-chloro-6-methoxybenzo[d]thiazole-4-carbonyl) cyclobutane-1-carboxylate

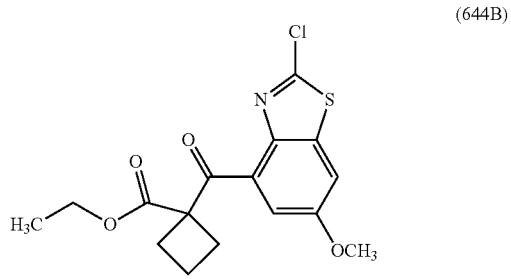 [SMILES: CCOC(=O)C1(C(=O)c2cc(OC)cc3sc(Cl)nc23)CCC1]

(644B)

Intermediate 644A (64.5 mg, 0.193 mmol), lithium chloride (8.18 mg, 0.193 mmol), copper(II) chloride (25.9 mg, 0.193 mmol), and tert-butyl nitrite (23 μL, 0.193 mmol) were dissolved in MeCN (1.93 mL). After 2 hours, the reaction mixture was diluted with EtOAc, washed with 1 N HCl, saturated NaHCO$_3$, then brine, dried (Na$_2$SO$_4$), filtered, and concentrated in vacuo. The crude material was purified by column chromatography (ISCO, 12 g silica gel column, 17 minute gradient from 0 to 100% EtOAc in hexanes) to give Intermediate 644B (12 mg, 0.034 mmol, 18%) as a white solid: LC-MS: Method H, RT=1.16 min, MS (ESI) m/z: 354.1 (M+H)$^+$.

Intermediate 644C: Ethyl 1-((2-chloro-6-methoxybenzo[d]thiazol-4-yl)(hydroxy)methyl) cyclobutane-1-carboxylate

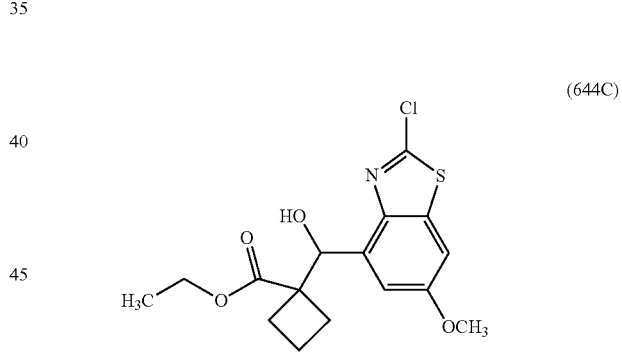

(644C)

Intermediate 644B (12 mg, 0.034 mmol) was dissolved in MeOH (339 μL) at 0° C. Sodium borohydride (2.57 mg, 0.068 mmol). After 45 minutes, the reaction mixture was diluted with EtOAc, washed with water then brine, dried (Na$_2$SO$_4$), filtered, and concentrated in vacuo to give Intermediate 644C, which was used directly in the subsequent reaction: LC-MS: Method H, RT=1.07 min, MS (ESI) m/z: 356.0 (M+H)$^+$.

Example 644

Intermediate I-9 (12.2 mg, 0.040 mmol) and Intermediate 644C (12 mg, 0.034 mmol) were dissolved in DMF (169 μL). PdCl$_2$(dppf)-CH$_2$Cl$_2$ adduct (1.65 mg, 2.02 μmol) was added and the reaction degassed by bubbling with argon for 15 minutes. Sodium carbonate (20.2 μL, 0.040 mmol) was added and the reaction degassed for 5 minutes, then sealed and heated to 100° C. in the microwave for 30 minutes. The crude material was purified by preparative HPLC (Method D, 60-100% B in 22 minutes) to give Example 644 (3.1 mg, 0.0062 mmol, 18%): $^1$H NMR (500 MHz, DMSO-d$_6$) δ 8.65 (s, 1H), 8.47 (s, 1H), 7.75 (s, 1H), 7.55 (s, 1H), 7.08 (d, J=1.7 Hz, 1H), 5.83 (d, J=5.4 Hz, 1H), 5.78 (d, J=5.7 Hz, 1H), 4.01 (s, 3H), 3.88-3.78 (m, 3H), 3.76 (dd, J=7.1, 4.4 Hz, 2H), 2.57 (s, 3H), 2.53-2.35 (m, 2H), 2.19 (br. s., 1H), 2.08 (br. s., 1H), 1.67-1.58 (m, 1H), 1.54 (br. s., 1H), 0.87 (t, J=7.1 Hz, 3H); LC-MS: Method H, RT=1.31 min, MS (ESI) m/z: 494.1 (M+H)$^+$; Analytical HPLC Method B, 99% purity.

Example 645

(2R,3S)-3-((2-(6-chloro-3-methoxyquinolin-8-yl)-5-fluorobenzo[d]thiazol-6-yl)oxy)butan-2-yl (2-methylpyrimidin-5-yl)carbamate

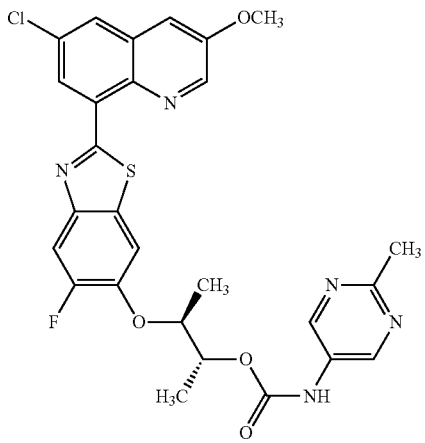

(645)

Intermediate I-121 (12 mg, 0.038 mmol), Intermediate I-130 (18.5 mg, 0.045 mmol) and PdCl$_2$(dppf) (1.65 mg, 2.25 μmol) were dissolved in 1,4-dioxane (375 μL) and Na$_2$CO$_3$ (2 M, 169 μL, 0.338 mmol) and heated to 100° C. After 1 hour, the reaction mixture was cooled to ambient temperature, diluted with EtOAc, washed with water, then brine, dried (Na$_2$SO$_4$), filtered, and concentrated in vacuo. The crude material was purified by preparative HPLC (Method D, 50-100% B in 20 minutes) to give Example 645 (6.6 mg, 0.011 mmol, 30%): $^1$H NMR (500 MHz, DMSO-d$_6$) δ 9.92 (br. s., 1H), 8.82 (br. s., 1H), 8.71 (br. s., 2H), 8.58 (s, 1H), 8.15 (s, 1H), 8.00 (d, J=8.2 Hz, 1H), 7.93 (d, J=11.9 Hz, 1H), 7.90 (br. s., 1H), 5.11 (d, J=6.1 Hz, 1H), 4.82 (d, J=6.1 Hz, 1H), 3.98 (s, 3H), 2.50 (s, 3H), 1.39 (t, J=6.7 Hz, 6H); LC-MS: Method H, RT=1.21 min, MS (ESI) m/z: 568.1 (M+H)$^+$; Analytical HPLC Method B, 96% purity.

Example 646

(1-(hydroxymethyl)cyclobutyl)(6-methoxy-2-(2-methoxy-7-methylquinoxalin-5-yl) benzo[d]thiazol-4-yl)methanol

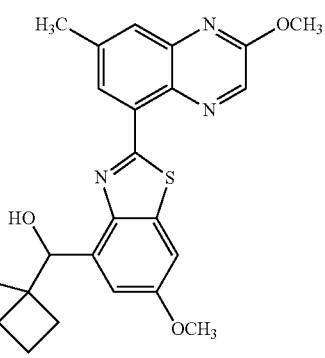

(646)

Intermediate 646A: Methyl 1-(2-amino-6-methoxy-benzo[d]thiazole-4-carbonyl)cyclobutanecarboxylate

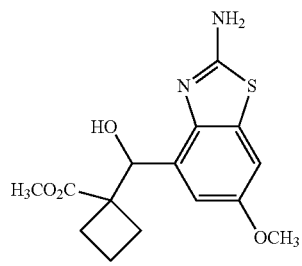

(646A)

Intermediate I-22 (1 g, 3.86 mmol) was dissolved in THF (38.6 mL). Sodium hydride (0.340 g, 8.49 mmol) was then added. After 15 minutes, the reaction mixture was cooled to −78° C. and BuLi (2.5 M in hexanes, 2.01 mL, 4.63 mmol) was added. After 45 minutes, dimethyl cyclobutane-1,1-dicarboxylate (0.892 mL, 5.79 mmol) was added and the reaction mixture was allowed to warm to ambient temperature. After the reaction reached ambient temperature, it was diluted with EtOAc, washed with water, then brine, dried (Na$_2$SO$_4$), filtered, and concentrated in vacuo to give Intermediate 646A, which was used directly in the subsequent step: LC-MS: Method H, RT=0.75 min, MS (ESI) m/z: 321.1 (M+H)$^+$.

Intermediate 646B: Methyl 1-(2-chloro-6-methoxy-benzo[d]thiazole-4-carbonyl)cyclobutanecarboxylate

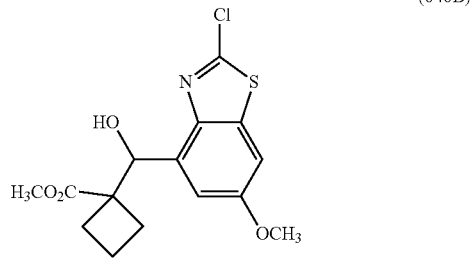

(646B)

Intermediate 646A (1.24 g, 3.86 mmol), lithium chloride (0.164 g, 3.86 mmol), copper(II) chloride (0.519 g, 3.86 mmol), and tert-butyl nitrite (0.460 mL, 3.86 mmol) were dissolved in MeCN (38.6 mL). After 2 hours, the reaction mixture was diluted with EtOAc, washed with 1 N HCl, saturated NaHCO$_3$, then brine, dried (Na$_2$SO$_4$), filtered, and concentrated in vacuo. The crude material was purified by column chromatography (ISCO, 12 g silica gel column, 17 minute gradient from 0 to 100% EtOAc in hexanes) to give Intermediate 646B (124 mg, 0.365 mmol, 9.5% over 2 steps) as a yellow solid: $^1$H NMR (400 MHz, CDCl$_3$) δ 7.76 (d, J=2.6 Hz, 1H), 7.43 (d, J=2.6 Hz, 1H), 3.92 (s, 3H), 3.68 (s, 3H), 2.80-2.65 (m, 2H), 2.64-2.50 (m, 2H), 2.25-2.11 (m, 1H), 1.94-1.80 (m, 1H); LC-MS: Method H, RT=1.14 min, MS (ESI) m/z: 340.1 (M+H)$^+$.

Intermediate 646C: (2-chloro-6-methoxybenzo[d]thiazol-4-yl)(1-(hydroxymethyl) cyclobutyl)methanol

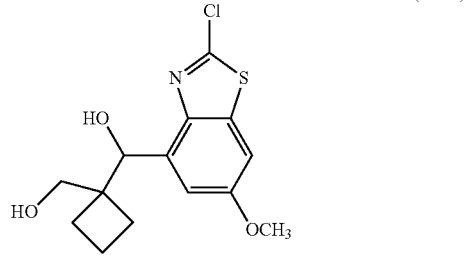

(646C)

Intermediate 646B (124 mg, 0.365 mmol) and NaBH$_4$ (13.8 mg, 0.365 mmol) were dissolved in MeOH (1.82 mL) at 0° C. After 4 hours, the reaction mixture was diluted with EtOAc, washed with water then brine, dried (Na$_2$SO$_4$), filtered, and concentrated in vacuo. The crude material was purified by column chromatography (ISCO, 12 g silica gel column, 17 minute gradient from 0 to 100% EtOAc in hexanes) to give Intermediate 646C (23.8 mg, 0.076 mmol, 21%) as a clear oil: $^1$H NMR (500 MHz, CDCl$_3$) δ 7.19 (d, J=2.5 Hz, 1H), 7.16 (d, J=2.5 Hz, 1H), 5.41 (d, J=5.8 Hz, 1H), 3.88 (s, 3H), 3.74-3.67 (m, 1H), 3.46-3.36 (m, 2H), 3.26 (d, J=5.8 Hz, 1H), 2.38-2.22 (m, 2H), 1.89 (dd, J=9.2, 3.2 Hz, 1H), 1.82-1.72 (m, 2H), 1.53-1.49 (m, 1H); LC-MS: Method H, RT=0.95 min, MS (ESI) m/z: 314.1 (M+H)$^+$.

Example 646

Intermediate I-9 (20.1 mg, 0.067 mmol) and Intermediate 646C (20 mg, 0.064 mmol) were dissolved in DMF (319 µL). PdCl$_2$(dppf)-CH$_2$Cl$_2$ adduct (3.12 mg, 3.82 µmol) was added and the reaction degassed by bubbling with argon for 15 minutes. Sodium carbonate (2 M, 38.2 µL, 0.076 mmol) was added and the reaction degassed for 5 minutes, then sealed and heated to 100° C. in the microwave for 30 minutes. More PdCl$_2$(dppf)-CH$_2$Cl$_2$ adduct (3.12 mg, 3.82 µmol) was added and the reaction mixture was heated in the microwave for an additional 30 minutes at 100° C. The crude material was purified by preparative HPLC (Method D, 45-95% B in 20 minutes) to give Example 646 (12.4 mg, 0.026 mmol, 41%): $^1$H NMR (500 MHz, DMSO-d$_6$) δ 8.71 (s, 1H), 8.47 (br. s., 1H), 7.82 (br. s., 1H), 7.60 (br. s., 1H), 7.20 (br. s., 1H), 5.64 (br. s., 1H), 5.51 (br. s., 1H), 4.80 (br. s., 1H), 4.08 (s, 3H), 3.47 (br. s., 1H), 3.26 (d, J=5.5 Hz, 1H), 2.63 (br. s., 3H), 2.35 (br. s., 1H), 2.17 (br. s., 1H), 1.79-1.55 (m, 4H); LC-MS: Method H, RT=1.22 min, MS (ESI) m/z: 452.1 (M+H)$^+$; Analytical HPLC Method B, 96% purity.

Example 647

(2R,3S)-3-((2-(6-chloro-3-ethylquinolin-8-yl)-5-fluorobenzo[d]thiazol-6-yl)oxy)butan-2-yl(2-methylpyrimidin-5-yl)carbamate

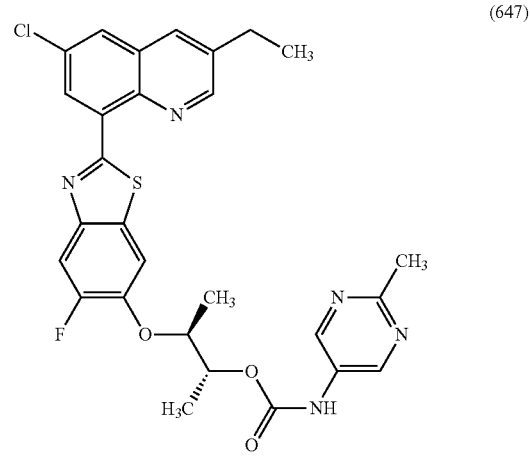 [SMILES: CCc1cnc2c(-c3nc4cc(F)c(O[C@@H](C)[C@@H](C)OC(=O)Nc5cnc(C)nc5)cc4s3)cc(Cl)cc2c1]

(647)

Intermediate 647A: 8-bromo-6-chloro-3-ethylquinoline

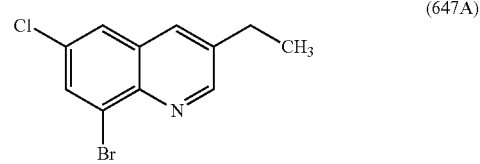

(647A)

Intermediate I-123 (185 mg, 0.789 mmol), butyraldehyde (71.1 µL, 0.789 mmol), and sodium methoxide (0.5 M in MeOH, 1.74 mL, 0.868 mmol) were dissolved in MeOH (1.58 mL) and heated to reflux. After heating overnight, the reaction mixture was diluted with saturated NH$_4$Cl, partially concentrated in vacuo and diluted with EtOAc. The layers were separated and the organic layer was washed with brine, dried (Na$_2$SO$_4$), filtered, and concentrated in vacuo. The crude material was purified by column chromatography (ISCO, 24 g silica gel column, 19 minute gradient from 0 to 50% EtOAc in hexanes) to give Intermediate 647A (192 mg, 0.710 mmol, 90%) as a yellow solid: $^1$H NMR (400 MHz, CDCl$_3$) δ 8.90 (d, J=2.2 Hz, 1H), 7.97 (d, J=2.2 Hz, 1H), 7.87-7.82 (m, 1H), 7.74 (d, J=2.2 Hz, 1H), 2.88 (q, J=7.5 Hz, 2H), 1.36 (t, J=7.6 Hz, 3H); LC-MS: Method H, RT=1.20 min, MS (ESI) m/z: 270/272 (M+H)$^+$.

Intermediate 647B: 6-chloro-3-ethyl-8-(4,4,5,5-tetramethyl-1,3,2-dioxaborolan-2-yl) quinoline

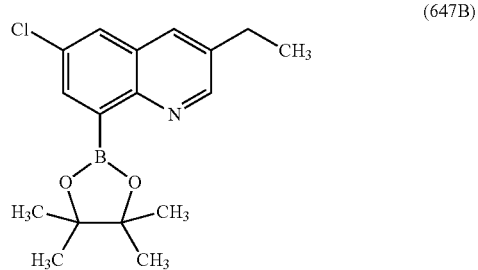 [SMILES: CCc1cnc2c(B3OC(C)(C)C(C)(C)O3)cc(Cl)cc2c1]

(647B)

Intermediate 647A (192 mg, 0.710 mmol), bispinacolatodiboron (216 mg, 0.852 mmol), and potassium acetate (174 mg, 1.78 mmol) were dissolved in 1,4-dioxane (7.1 mL) and degassed for 5 minutes by bubbling with argon. PdCl$_2$(dppf)-CH$_2$Cl$_2$ adduct (46.4 mg, 0.057 mmol) was added and the reaction degassed for an additional 10 minutes. The reaction mixture was heated to 130° C. in the microwave for 2 hours. The reaction mixture was diluted with EtOAc and water. The reaction was further extracted twice with EtOAc. The combined organic layers were washed with brine, dried (Na$_2$SO$_4$), filtered, and concentrated in vacuo to give Intermediate 647B, which was used directly in the subsequent reaction: LC-MS: Method H, RT=0.93 min, MS (ESI) m/z: 236.1 (boronic acid mass observed, M+H)$^+$.

Example 647

Intermediate 647B (15 mg, 0.047 mmol), I-130 (19.4 mg, 0.047 mmol) and PdCl$_2$(dppf) (2.07 mg, 2.83 μmol) were dissolved in 1,4-dioxane (472 μL) and Na$_2$CO$_3$ (2 M, 213 μL, 0.425 mmol) and heated to 100° C. After 1 hour, the reaction mixture was cooled to ambient temperature, diluted with EtOAc, washed with water, then brine, dried (Na$_2$SO$_4$), filtered, and concentrated in vacuo. The crude material was purified by preparative HPLC (Method D, 65-100% B in 25 minutes) to give Example 647 (4.3 mg, 0.0074 mmol, 15%): $^1$H NMR (500 MHz, DMSO-d$_6$) δ 9.93 (br. s., 1H), 9.06 (d, J=2.1 Hz, 1H), 8.77 (d, J=2.1 Hz, 1H), 8.73 (br. s., 2H), 8.34 (s, 1H), 8.28 (d, J=2.4 Hz, 1H), 8.07 (d, J=8.2 Hz, 1H), 7.99 (d, J=11.6 Hz, 1H), 5.11 (dd, J=6.6, 2.6 Hz, 1H), 4.84 (dd, J=6.4, 2.7 Hz, 1H), 2.92 (q, J=7.4 Hz, 2H), 2.55 (s, 3H), 1.40 (dd, J=6.3, 4.4 Hz, 6H), 1.35 (t, J=7.6 Hz, 3H); LC-MS: Method H, RT=1.30 min, MS (ESI) m/z: 566.1 (M+H)$^+$; Analytical HPLC Method B, 98% purity.

Example 648

(2R,3S)-3-((5-fluoro-2-(3-methoxy-6-methylquinolin-8-yl)benzo[d]thiazol-6-yl)oxy)butan-2-yl (2-methylpyrimidin-5-yl)carbamate

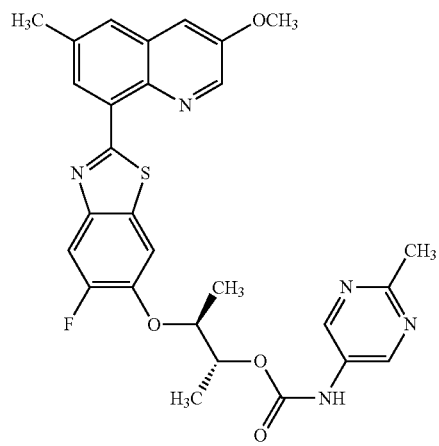

(648)

Intermediate I-124 (15 mg, 0.050 mmol), Intermediate I-130 (20.6 mg, 0.050 mmol) and PdCl$_2$(dppf) (2.2 mg, 3.01 μmol) were dissolved in 1,4-dioxane (501 μL) and Na$_2$CO$_3$ (2 M, 226 μL, 0.451 mmol) and heated to 100° C. After 1 hour, the reaction mixture was cooled to ambient temperature and concentrated in vacuo. The crude material was purified by preparative HPLC (Method D, 45-100% B in 15 minutes) to give Example 648 (8.4 mg, 0.015 mmol, 30%): $^1$H NMR (500 MHz, DMSO-d$_6$) δ 9.95 (br. s., 1H), 8.79 (d, J=2.7 Hz, 1H), 8.74 (br. s., 2H), 8.61 (d, J=1.5 Hz, 1H), 8.03 (d, J=8.2 Hz, 1H), 7.94 (d, J=11.6 Hz, 1H), 7.89-7.82 (m, 2H), 5.16-5.05 (m, 1H), 4.80 (dd, J=6.1, 2.7 Hz, 1H), 3.99 (s, 3H), 2.61 (s, 3H), 1.40 (dd, J=6.4, 2.4 Hz, 6H) (1 methyl group under solvent); LC-MS: Method H, RT=1.14 min, MS (ESI) m/z: 548.1 (M+H)$^+$; Analytical HPLC Method B, 99% purity.

Example 649

(2R,3S)-3-((2-(6-chloro-3-ethoxyquinolin-8-yl)-5-fluorobenzo[d]thiazol-6-yl)oxy)butan-2-yl (2-methylpyrimidin-5-yl)carbamate

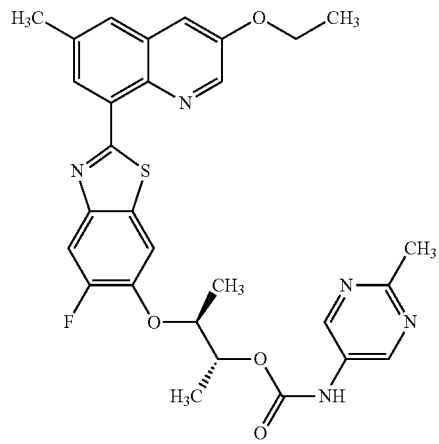

(649)

Intermediate I-126 (15 mg, 0.045 mmol), Intermediate I-130 (18.5 mg, 0.045 mmol) and PdCl$_2$(dppf) (1.97 mg, 2.70 μmol) were dissolved in 1,4-dioxane (450 μL) and Na$_2$CO$_3$ (2 M, 202 μL, 0.405 mmol) and heated to 100° C. After 1 hour, the reaction mixture was cooled to ambient temperature. The reaction mixture was concentrated in vacuo. The crude material was purified by preparative HPLC (Method D, 50-100% B in 20 minutes) then repurified by preparative HPLC (Method D, 50-100% B in 20 minutes) to give Example 649 (2.5 mg, 0.0041 mmol, 9.2%): $^1$H NMR (500 MHz, DMSO-d$_6$) δ 9.94 (br. s., 1H), 8.85 (d, J=2.7 Hz, 1H), 8.73 (br. s., 2H), 8.62 (d, J=2.1 Hz, 1H), 8.18 (d, J=2.1 Hz, 1H), 8.05 (d, J=8.2 Hz, 1H), 7.97 (d, J=11.6 Hz, 1H), 7.93 (d, J=2.7 Hz, 1H), 5.11 (dd, J=6.6, 2.6 Hz, 1H), 4.82 (dd, J=6.4, 2.4 Hz, 1H), 4.27 (q, J=7.0 Hz, 2H), 2.55 (s, 3H), 1.46 (t, J=6.9 Hz, 3H), 1.40 (t, J=5.5 Hz, 6H); LC-MS: Method H, RT=1.30 min, MS (ESI) m/z: 582.1 (M+H)$^+$; Analytical HPLC Method B, 96% purity.

Example 650

(2R,3S)-3-((2-(6-chloro-3-(difluoromethoxy)quinolin-8-yl)-5-fluorobenzo[d]thiazol-6-yl)oxy)butan-2-yl (2-methylpyrimidin-5-yl)carbamate

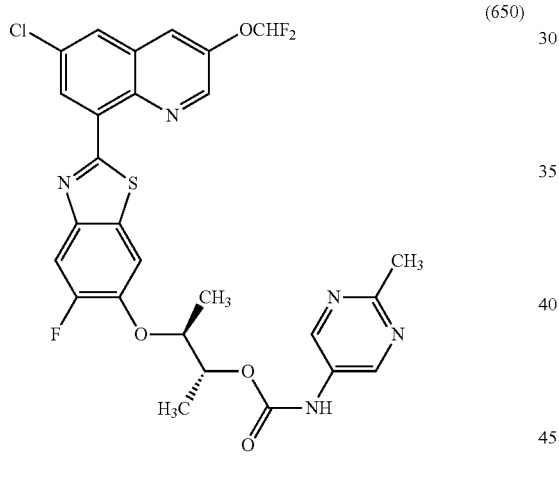

(650)

Intermediate I-127 (22 mg, 0.062 mmol), Intermediate I-130 (25.4 mg, 0.062 mmol) and PdCl$_2$(dppf) (2.72 mg, 3.71 μmol) were dissolved in 1,4-dioxane (619 μL) and Na$_2$CO$_3$ (2 M, 278 μL, 0.557 mmol) and heated to 100° C. After 1 hour, the reaction mixture was cooled to ambient temperature and concentrated in vacuo. The crude material was purified by preparative HPLC (Method D, 45-90% B in 20 minutes) to give Example 650 (3.9 mg, 0.0063 mmol, 10%): $^1$H NMR (500 MHz, DMSO-d$_6$) δ 9.93 (br. s., 1H), 9.06 (d, J=2.4 Hz, 1H), 8.78 (s, 1H), 8.72 (br. s., 2H), 8.36 (br. s., 2H), 8.07 (d, J=7.9 Hz, 1H), 7.99 (d, J=11.3 Hz, 1H), 7.67-7.34 (m, 1H), 5.11 (dd, J=6.4, 2.1 Hz, 1H), 4.88-4.79 (m, 1H), 2.55 (s, 3H), 1.40 (t, J=5.8 Hz, 6H); LC-MS: Method H, RT=1.37 min, MS (ESI) m/z: 604.1 (M+H)$^+$; Analytical HPLC Method B, 98% purity.

Example 651

(2R,3S)-3-((2-(6-chloro-3-(2,2-difluoroethoxy)quinolin-8-yl)-5-fluorobenzo[d]thiazol-6-yl)oxy)butan-2-yl (2-methylpyrimidin-5-yl)carbamate

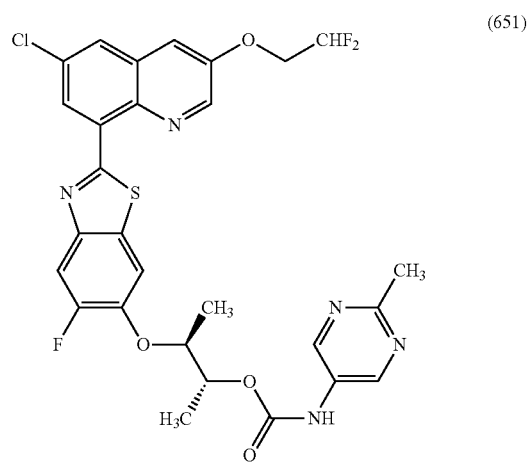 [SMILES: Cc1ncc(NC(=O)O[C@H](C)[C@H](C)Oc2cc3sc(-c4cc(Cl)cc5cc(OCC(F)F)cnc45)nc3cc2F)cn1]

(651)

Intermediate 651A:
8-bromo-6-chloro-3-(2,2-difluoroethoxy)quinoline

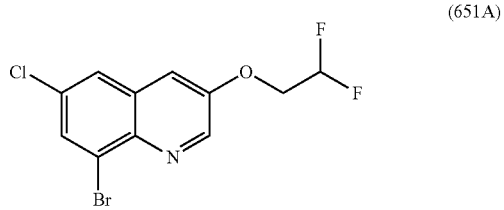 [SMILES: FC(F)COc1cnc2c(Br)cc(Cl)cc2c1]

(651A)

Intermediate I-122 (82 mg, 0.317 mmol), K$_2$CO$_3$ (132 mg, 0.952 mmol), and 2-bromo-1,1-difluoroethane (92 mg, 0.634 mmol) were dissolved in Acetone (3.17 mL) and heated to 50° C. in a sealed tube. After heating overnight, the reaction mixture was diluted with EtOAc, washed with water, then brine, dried (Na$_2$SO$_4$), filtered, and concentrated in vacuo to give Intermediate 651A (60.4 mg, 0.187 mmol, 59%) as an orange solid: $^1$H NMR (400 MHz, CDCl$_3$) δ 8.80 (d, J=2.9 Hz, 1H), 7.91 (d, J=2.2 Hz, 1H), 7.71 (d, J=2.2 Hz, 1H), 7.33 (d, J=2.9 Hz, 1H), 6.36-6.02 (m, 1H), 4.34 (td, J=12.8, 4.0 Hz, 2H); LC-MS: Method H, RT=1.19 min, MS (ESI) m/z: 322/324 (M+H)$^+$.

Intermediate 651B: 6-chloro-3-(2,2-difluoroethoxy)-8-(4,4,5,5-tetramethyl-1,3,2-dioxaborolan-2-yl)quinoline

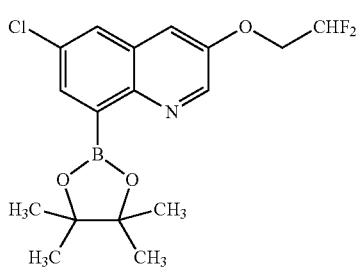

(651B)

Intermediate 651A (60.4 mg, 0.187 mmol), bispinacolatodiboron (57.1 mg, 0.225 mmol), and potassium acetate (45.9 mg, 0.468 mmol) were dissolved in 1,4-dioxane (1.87 mL) and degassed for 5 minutes by bubbling with argon. PdCl$_2$(dppf)-CH$_2$Cl$_2$ adduct (12.2 mg, 0.015 mmol) was added and the reaction degassed for an additional 10 minutes. The reaction mixture was heated to 130° C. in the microwave for 2 hours. The reaction mixture was diluted with EtOAc and water. The reaction was further extracted twice with EtOAc. The combined organic layers were washed with brine, dried (Na$_2$SO$_4$), filtered, and concentrated in vacuo to give Intermediate 651B, which was used directly in the subsequent reaction: LC-MS: Method H, RT=1.14 min, MS (ESI) m/z: 287.9 (M+H)$^+$.

Example 651

Intermediate 651B (17 mg, 0.046 mmol), Intermediate I-130 (18.9 mg, 0.046 mmol) and PdCl$_2$(dppf) (2.02 mg, 2.76 µmol) were dissolved in 1,4-dioxane (460 µL) and Na$_2$CO$_3$ (2 M, 207 µL, 0.414 mmol) and heated to 100° C. After 1 hour, the reaction mixture was cooled to ambient temperature and concentrated in vacuo. The crude material was purified by preparative HPLC (Method D, 50-100% B in 20 minutes) then repurified by preparative HPLC (Method D, 45-90% in 20 minutes) to give Example 651 (3.6 mg, 0.0058 mmol, 13%): $^1$H NMR (500 MHz, DMSO-d$_6$) δ 9.94 (br. s., 1H), 8.95 (br. s., 1H), 8.73 (br. s., 2H), 8.67 (s, 1H), 8.18 (s, 1H), 8.11-8.03 (m, 2H), 7.98 (d, J=11.3 Hz, 1H), 6.67-6.42 (m, 1H), 5.11 (d, J=6.4 Hz, 1H), 4.82 (d, J=6.1 Hz, 1H), 4.60 (t, J=13.6 Hz, 2H), 2.55 (s, 3H), 1.40 (t, J=5.3 Hz, 6H); LC-MS: Method H, RT=1.37 min, MS (ESI) m/z: 604.1 (M+H)$^+$; Analytical HPLC Method B, 100% purity.

Example 652

(2R,3S)-3-((2-(6-chloro-3-(methylamino)quinolin-8-yl)-5-fluorobenzo[d]thiazol-6-yl)oxy)butan-2-yl (2-methylpyrimidin-5-yl)carbamate

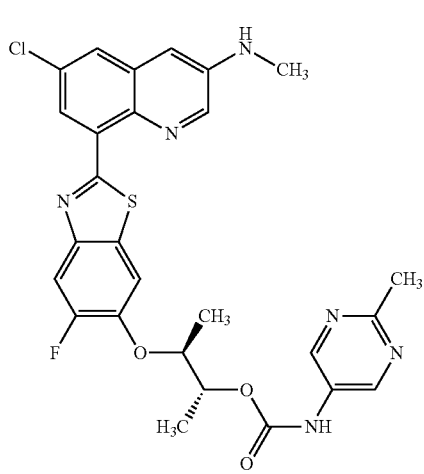

(652)

Intermediate 652A: tert-butyl (8-bromo-6-chloroquinolin-3-yl)(methyl)carbamate (652A)

Intermediate I-123 (100 mg, 0.426 mmol), tert-butyl methyl(2-oxoethyl) carbamate (73.9 mg, 0.426 mmol), and sodium methoxide (0.5 M in MeOH, 938 µL, 0.469 mmol) were dissolved in MeOH (1.71 mL) and heated to reflux. After heating overnight, the reaction mixture was diluted with saturated NH$_4$Cl, partially concentrated in vacuo and diluted with EtOAc. The layers were separated and the organic layer was washed with brine, dried (Na$_2$SO$_4$), filtered, and concentrated in vacuo. The crude material was purified by column chromatography (ISCO, 24 g silica gel column, 21 minute gradient from 0 to 50% EtOAc in hexanes) to give Intermediate 652A (64 mg, 0.172 mmol, 40%) as an orange oil: $^1$H NMR (500 MHz, CDCl$_3$) δ 9.02 (d, J=2.5 Hz, 1H), 7.99 (d, J=2.2 Hz, 1H), 7.90 (d, J=2.2 Hz, 1H), 7.76 (d, J=2.2 Hz, 1H), 3.42 (s, 3H), 1.51 (s, 9H); LC-MS: Method H, RT=1.39 min, MS (ESI) m/z: 371/373 (M+H)$^+$.

Intermediate 652B:
8-bromo-6-chloro-N-methylquinolin-3-amine

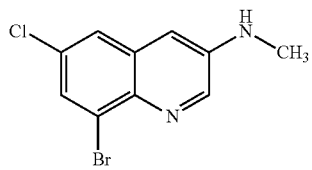
(652B)

Intermediate 652A (64 mg, 0.172 mmol) was dissolved in DCM (1.72 mL) and TFA (66.3 μL, 0.861 mmol). After stirring for 4 days, the reaction mixture was diluted with DCM, washed with 1N NaOH, water, then brine, dried (Na$_2$SO$_4$), filtered, and concentrated in vacuo to give Intermediate 652B (43.4 mg, 0.160 mmol, 93%) as an off-white solid: $^1$H NMR (400 MHz, CDCl$_3$) δ 8.49 (d, J=2.9 Hz, 1H), 7.68 (d, J=2.2 Hz, 1H), 7.58 (d, J=2.0 Hz, 1H), 6.85 (d, J=2.9 Hz, 1H), 4.27 (br. s., 1H), 2.96 (d, J=5.1 Hz, 3H); LC-MS: Method H, RT=1.31 min, MS (ESI) m/z: 271/273 (M+H)$^+$.

Intermediate 652C: 6-chloro-N-methyl-8-(4,4,5,5-tetramethyl-1,3,2-dioxaborolan-2-yl) quinolin-3-amine

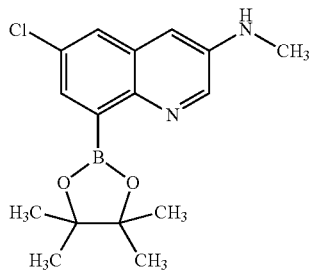
(652C)

Intermediate 652B (20 mg, 0.074 mmol), bispinacolatodiboron (37.4 mg, 0.147 mmol), potassium acetate (18.1 mg, 0.184 mmol), and PdCl$_2$(dppf)-CH$_2$Cl$_2$ adduct (4.81 mg, 5.89 μmol) were stored on HIVAC for 15 minutes then were dissolved in dry 1,4-dioxane (368 μL) and degassed for 15 minutes by bubbling with argon. The reaction mixture was heated to 130° C. in the microwave for 40 minutes. The reaction mixture was diluted with EtOAc and washed with water then brine, dried (Na$_2$SO$_4$), filtered, and concentrated in vacuo to give Intermediate 652C, which was used directly in the subsequent reaction: LC-MS: Method H, RT=0.98 min, MS (ESI) m/z: 237.0 (boronic acid mass observed, M+H)$^+$.

Example 652

Intermediate 652C (8 mg, 0.025 mmol), Intermediate I-130 (10.3 mg, 0.025 mmol) and PdCl$_2$(dppf) (1.1 mg, 1.51 μmol) were dissolved in 1,4-dioxane (251 μL) and Na$_2$CO$_3$ (2 M, 113 μL, 0.226 mmol) and heated to 100° C. After 1 hour, the reaction mixture was cooled to ambient temperature and concentrated in vacuo. The crude material was purified by preparative HPLC (Method D, 40-80% in 20 minutes) to give Example 652 (3.3 mg, 0.0057 mmol, 23%): $^1$H NMR (500 MHz, DMSO-d$_6$) δ 9.94 (br. s., 1H), 8.73 (br. s., 2H), 8.67 (br. s., 1H), 8.39 (s, 1H), 8.03 (d, J=7.6 Hz, 1H), 7.99-7.91 (m, 2H), 7.64-7.48 (m, 1H), 7.14 (br. s., 1H), 5.11 (d, J=6.1 Hz, 1H), 4.81 (d, J=6.1 Hz, 1H), 2.85 (br. s., 3H), 2.55 (s, 3H), 1.40 (d, J=6.1 Hz, 6H); LC-MS: Method H, compound did not ionize; Analytical HPLC Method B, 98% purity.

Example 653

(2R,3S)-3-((2-(6-(difluoromethyl)-3-methoxyquinolin-8-yl)-5-fluorobenzo[d]thiazol-6-yl)oxy)butan-2-yl (2-methylpyrimidin-5-yl)carbamate

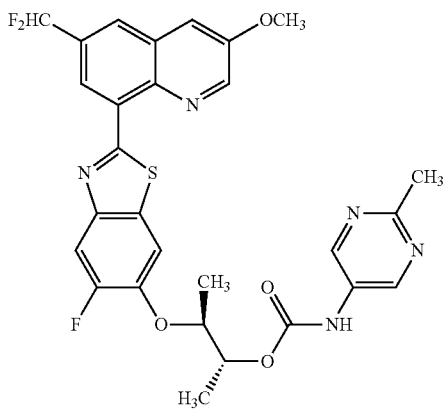
(653)

Intermediate I-128 (15 mg, 0.045 mmol), Intermediate I-130 (18.4 mg, 0.045 mmol) and PdCl$_2$(dppf) (1.96 mg, 2.69 μmol) were dissolved in 1,4-dioxane (448 μL) and Na$_2$CO$_3$ (2 M, 201 μL, 0.403 mmol) and heated to 100° C. After 1 hour, the reaction mixture was cooled to ambient temperature and concentrated in vacuo. The crude material was purified by preparative HPLC (Method D, 45-90% B in 22 minutes) to give Example 653 (5.1 mg, 0.0087 mmol, 19%): $^1$H NMR (500 MHz, DMSO-d$_6$) δ 9.91 (br. s., 1H), 8.90 (d, J=2.4 Hz, 1H), 8.82 (s, 1H), 8.70 (br. s., 2H), 8.30 (s, 1H), 8.04 (d, J=2.4 Hz, 1H), 7.99 (d, J=8.2 Hz, 1H), 7.95 (d, J=11.6 Hz, 1H), 7.33 (t, J=44 Hz, 1H), 5.15-5.06 (m, 1H), 4.81 (d, J=4.0 Hz, 1H), 3.99 (s, 3H), 2.49 (s, 3H), 1.38 (t, J=7.2 Hz, 6H); LC-MS: Method H, RT=1.11 min, MS (ESI) m/z: 584.1 (M+H)$^+$; Analytical HPLC Method B, 99% purity.

Example 654

(2R,3S)-3-((5-fluoro-2-(6-(fluoromethyl)-3-methoxyquinolin-8-yl)benzo[d]thiazol-6-yl) oxy)butan-2-yl (2-methylpyrimidin-5-yl)carbamate

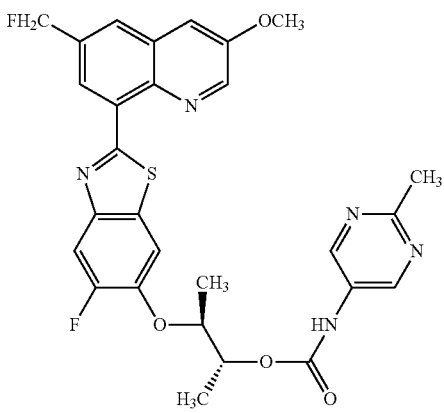

(654)

Intermediate I-129 (15 mg, 0.047 mmol), Intermediate I-130 (19.4 mg, 0.047 mmol) and PdCl$_2$(dppf) (2.08 mg, 2.84 µmol) were dissolved in 1,4-dioxane (473 µL) and Na$_2$CO$_3$ (2 M, 213 µL, 0.426 mmol) and heated to 100° C. After 1 hour, the reaction mixture was cooled to ambient temperature and concentrated in vacuo. The crude material was purified by preparative HPLC (Method D, 45-90% B in 20 minutes) to give Example 654 (2.5 mg, 0.0043 mmol, 9.1%): $^1$H NMR (500 MHz, DMSO-d$_6$) δ 9.96 (br. s., 1H), 8.89 (d, J=2.7 Hz, 1H), 8.75 (d, J=14.0 Hz, 3H), 8.13 (s, 1H), 8.07-8.00 (m, 2H), 7.96 (d, J=11.6 Hz, 1H), 5.76 (d, J=20 Hz, 2H), 5.12 (dd, J=6.4, 2.7 Hz, 1H), 4.82 (d, J=3.7 Hz, 1H), 4.01 (s, 3H), 3.45 (s, 3H), 1.46-1.34 (m, 6H); LC-MS: Method H, RT=1.07 min, MS (ESI) m/z: 566.1 (M+H)$^+$; Analytical HPLC Method B, 97% purity.

Example 655

(2R,3S)-3-((2-(6-cyano-3-methoxyquinolin-8-yl)-5-fluorobenzo[d]thiazol-6-yl)oxy)butan-2-yl (2-methylpyrimidin-5-yl)carbamate

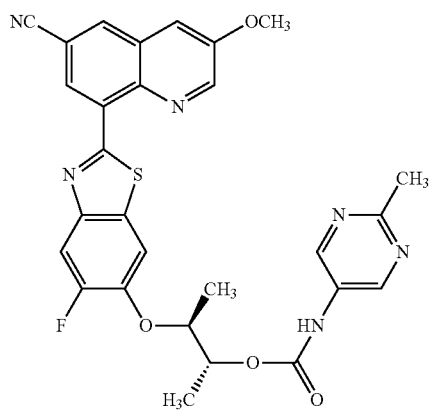

(655)

Intermediate 655A: methyl 2-amino-3-bromo-5-cyanobenzoate

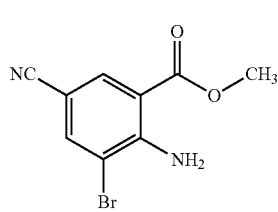

(655A)

Methyl 2-amino-5-cyanobenzoate (0.25 g, 1.42 mmol) and NBS (0.253 g, 1.42 mmol) were dissolved in AcOH (2.84 mL) and heated to 120° C. After 2 hours, the reaction mixture was cooled to ambient temperature and diluted with EtOAc. The reaction was then quenched with vigorous stirring with saturated NaHCO$_3$. The layers were separated and the organic layer further washed with brine, dried (Na$_2$SO$_4$), filtered, and concentrated in vacuo to give Intermediate 655A (356 mg, 1.4 mmol, 98%) as a white solid: $^1$H NMR (400 MHz, CDCl$_3$) δ 8.22 (d, J=1.8 Hz, 1H), 7.82 (d, J=1.8 Hz, 1H), 3.95 (s, 3H); LC-MS: Method H, compound did not ionize

Intermediate 655B: 4-amino-3-bromo-5-(hydroxymethyl)benzonitrile

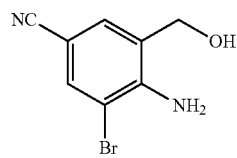

(655B)

Intermediate 655A (356 mg, 1.4 mmol) was dissolved in THF (4.65 mL). Lithium borohydride (60.8 mg, 2.79 mmol) was added and the reaction mixture was heated to 50° C. After 1 hour, the reaction mixture was diluted with water. The reaction mixture was then extracted thrice with EtOAc. The combined organic layers were washed with brine, dried (Na$_2$SO$_4$), filtered, and concentrated in vacuo. The crude material was purified by column chromatography (ISCO, dry load, 40 g silica gel column, 19 minute gradient from 0 to 100% EtOAc in hexanes, polar weighted) to give Intermediate 655B (106 mg, 0.465 mmol, 33%) as a white solid: $^1$H NMR (400 MHz, CDCl$_3$) δ 7.71 (d, J=1.8 Hz, 1H), 7.32 (d, J=1.8 Hz, 1H), 5.35 (br. s., 2H), 4.73 (s, 2H), 1.79 (br. s., 1H); LC-MS: Method H, compound did not ionize

Intermediate 655C: 4-amino-3-bromo-5-formylbenzonitrile

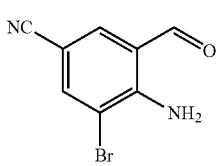

(655C)

Intermediate 655B (106 mg, 0.465 mmol) was dissolved in CHCl$_3$ (3.1 mL). Manganese dioxide (243 mg, 2.79 mmol) was added and the reaction mixture was heated to 40° C. After heating overnight, the reaction mixture was filtered through celite and concentrated in vacuo to give Intermediate 655C (88.3 mg, 0.392 mmol, 84%) as a white solid: $^1$H NMR (400 MHz, CDCl$_3$) δ 9.85 (s, 1H), 7.88-7.86 (m, 1H), 7.86-7.83 (m, 1H); LC-MS: Method H, compound did not ionize.

Intermediate 655D:
3-(benzyloxy)-8-bromoquinoline-6-carbonitrile

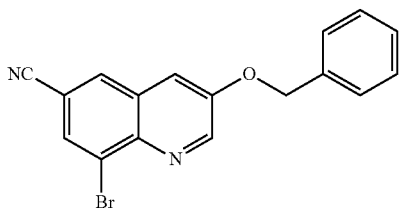

(655D)

Intermediate 655C (88.3 mg, 0.392 mmol), 2-(benzyloxy) acetaldehyde (58.9 mg, 0.392 mmol), and sodium methoxide (0.5 M, 863 μL, 0.432 mmol) were dissolved in MeOH (1.57 mL) and heated to reflux. After heating overnight, the reaction mixture was diluted with saturated NH$_4$Cl, partially concentrated in vacuo and diluted with EtOAc. The layers were separated and the organic layer was washed with brine, dried (Na$_2$SO$_4$), filtered, and concentrated in vacuo. The crude material was purified by column chromatography (ISCO, 40 g silica gel column, 19 minute gradient from 0 to 100% EtOAc in hexanes) to give Intermediate 655D (59.5 mg, 0.175 mmol, 45%) as a yellow solid: LC-MS: Method H, RT=1.11 min, MS (ESI) m/z: 339/341 (M+H)$^+$.

Intermediate 655E:
8-bromo-3-hydroxyquinoline-6-carbonitrile, HCl

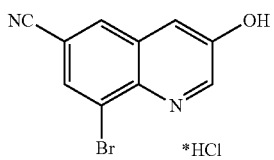

(655E)

Intermediate 655D (59 mg, 0.174 mmol) and pentamethylbenzene (181 mg, 1.218 mmol) were dissolved in DCM (3.48 mL) and cooled to −78° C. Boron trichloride (1 M in heptane, 452 μL, 0.452 mmol) was added and the reaction mixture was allowed to slowly warm to ambient temperature. After stirring overnight, the reaction mixture was diluted with hexanes and 1 N HCl and allowed to stir for 1 hour. The solid was collected by suction filtration to give Intermediate 655E (24.5 mg, 0.086 mmol, 49%) as a white solid: $^1$H NMR (400 MHz, MeOH$_4$) δ 8.73 (d, J=2.9 Hz, 1H), 8.27 (d, J=1.8 Hz, 1H), 8.06 (d, J=1.8 Hz, 1H), 7.59 (d, J=2.6 Hz, 1H); LC-MS: Method H, RT=0.80 min, MS (ESI) m/z: 249/251 (M+H)$^+$.

Intermediate 655F:
8-bromo-3-methoxyquinoline-6-carbonitrile

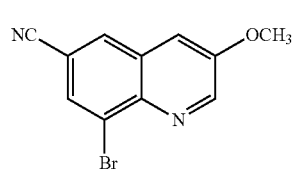

(655F)

Intermediate 655E (24.5 mg, 0.086 mmol), K$_2$CO$_3$ (35.6 mg, 0.257 mmol), and methyl iodide (10.7 μL, 0.172 mmol) were dissolved in acetone (858 μL) and heated to 50° C. in a sealed tube. After heating overnight, the reaction mixture was diluted with EtOAc, washed with water, then brine, dried (Na$_2$SO$_4$), filtered, and concentrated in vacuo to give Intermediate 655F (21.5 mg, 0.082 mmol, 95%) as a white solid: $^1$H NMR (400 MHz, CDCl$_3$) δ 8.92 (d, J=2.9 Hz, 1H), 8.12 (d, J=1.8 Hz, 1H), 8.07 (d, J=1.5 Hz, 1H), 7.43 (d, J=2.9 Hz, 1H), 4.03 (s, 3H); LC-MS: Method H, RT=0.93 min, MS (ESI) m/z: 263/265 (M+H)$^+$.

Intermediate 655G: 3-methoxy-8-(4,4,5,5-tetramethyl-1,3,2-dioxaborolan-2-yl) quinoline-6-carbonitrile

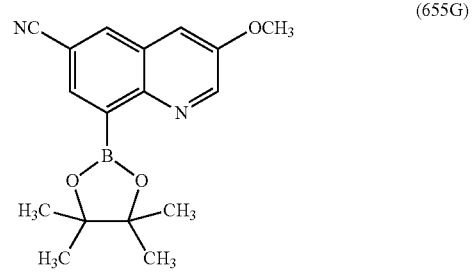 [SMILES: COc1cnc2c(B3OC(C)(C)C(C)(C)O3)cc(C#N)cc2c1]

(655G)

Intermediate 655F (21 mg, 0.080 mmol), bispinacolatodiboron (40.5 mg, 0.160 mmol), potassium acetate (19.6 mg, 0.200 mmol), and PdCl$_2$(dppf)-CH$_2$Cl$_2$ adduct (5.21 mg, 6.39 μmol) were stored on HIVAC for 15 minutes then were dissolved in 1,4-dioxane (399 μL) and degassed for 15 minutes by bubbling with argon. The reaction mixture was heated to 130° C. in the microwave for 40 minutes. The reaction mixture was diluted with EtOAc and washed with water then brine, dried (Na$_2$SO$_4$), filtered, and concentrated in vacuo to give Intermediate 655G, which was used directly in the subsequent reaction.

Example 655

Intermediate 655G (20 mg, 0.064 mmol), Intermediate I-130 (26.5 mg, 0.064 mmol) and PdCl$_2$(dppf) (2.83 mg, 3.87 μmol) were dissolved in 1,4-dioxane (645 μL) and Na$_2$CO$_3$ (2 M, 290 μL, 0.580 mmol) and heated to 100° C. After 1 hour, the reaction mixture was cooled to ambient temperature and concentrated in vacuo. The crude material was purified by preparative HPLC (Method D, 45-90% B in 20 minutes) then repurified by preparative HPLC (Method D, 40-80% B in 20 minutes) to give Example 655 (1.3 mg, 0.0023 mmol, 3.6%): $^1$H NMR (500 MHz, DMSO-d$_6$) δ

9.95 (br. s., 1H), 8.95 (d, J=2.4 Hz, 1H), 8.80-8.69 (m, 3H), 8.60 (s, 1H), 8.05-7.98 (m, 2H), 7.93 (d, J=11.6 Hz, 1H), 5.12 (d, J=6.4 Hz, 1H), 4.82 (d, J=4.0 Hz, 1H), 4.01 (s, 3H), 3.41 (br. s., 3H), 1.41 (t, J=6.6 Hz, 6H); LC-MS: Method H, compound did not ionize; Analytical HPLC Method B, 100% purity.

Example 656

(2-(6-chloro-3-methoxyquinolin-8-yl)-6-methoxy-benzo[d]thiazol-4-yl)(1-(trifluoromethyl)cyclobutyl)methanol

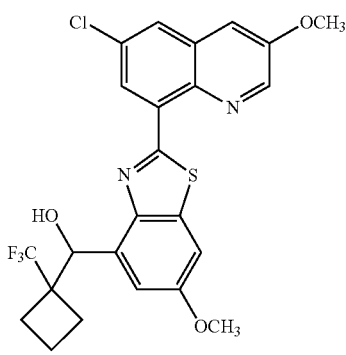

(656)

Intermediate 656A: (2-amino-6-methoxybenzo[d]thiazol-4-yl)(1-(trifluoromethyl) cyclobutyl)methanone

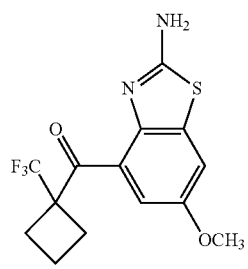

(656A)

Intermediate I-22 (1 g, 3.86 mmol) was dissolved in THF (38.6 mL). NaH (0.170 g, 4.25 mmol) was added. After 15 minutes, the reaction mixture was cooled to −78° C. and BuLi (1.93 mL, 4.82 mmol) was added. After 30 minutes, ethyl 1-(trifluoromethyl) cyclobutanecarboxylate (2.27 g, 11.6 mmol) was added and the reaction mixture was allowed to warm to ambient temperature. After achieving ambient temperature, the reaction mixture was diluted with EtOAc and washed with water, then brine, dried (Na$_2$SO$_4$), filtered, and concentrated in vacuo to give Intermediate 656A, which was used directly in the subsequent step: LC-MS: Method H, RT=0.79 min, MS (ESI) m/z: 331.1 (M+H)$^+$.

Intermediate 656B: (2-chloro-6-methoxybenzo[d]thiazol-4-yl)(1-(trifluoromethyl) cyclobutyl)methanone

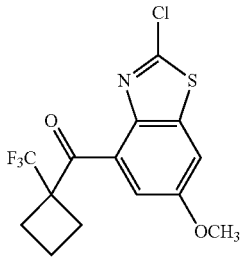

(656B)

Intermediate 656A (1.28 g, 3.86 mmol), lithium chloride (0.164 g, 3.86 mmol), copper(II) chloride (0.519 g, 3.86 mmol), and tert-butyl nitrite (0.461 mL, 3.86 mmol) were dissolved in MeCN (38.6 mL). After 3 hours, the reaction mixture was diluted with EtOAc, washed with 1 N HCl, saturated NaHCO$_3$, then brine, dried (Na$_2$SO$_4$), filtered, and concentrated in vacuo. The crude material was purified by column chromatography (ISCO, 40 g silica gel column, 19 minute gradient from 0 to 100% EtOAc in hexanes) to give Intermediate 656B (386 mg, 1.1 mmol, 29% over 2 steps): $^1$H NMR (400 MHz, CDCl$_3$) δ 7.36 (d, J=2.4 Hz, 1H), 7.12 (d, J=2.4 Hz, 1H), 3.91 (s, 3H), 3.01-2.89 (m, 2H), 2.66-2.56 (m, 2H), 2.23-2.09 (m, 1H), 2.06-1.92 (m, 1H); LC-MS: Method H, RT=1.18 min, MS (ESI) m/z: 350.1 (M+H)$^+$.

Intermediate 656C: (2-chloro-6-methoxybenzo[d]thiazol-4-yl)(1-(trifluoromethyl) cyclobutyl)methanol

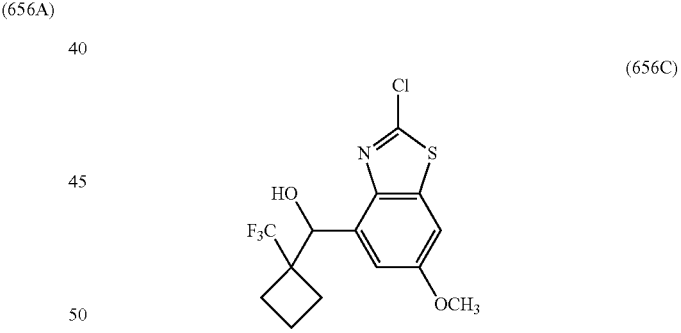

(656C)

Intermediate 656B (386 mg, 1.104 mmol) was suspended in MeOH (5.52 mL) and cooled to 0° C. Sodium borohydride (84 mg, 2.21 mmol) was then added. After 45 minutes, the reaction mixture was diluted with water and extracted with EtOAc. The organic layer was washed with brine, dried (Na$_2$SO$_4$), filtered, and concentrated in vacuo. The crude material was purified by column chromatography (ISCO, 40 g silica gel column, 19 minute gradient from 0 to 100% EtOAc in hexanes) to give Intermediate 656C (314 mg, 0.891 mmol, 81%) as a yellow oil: $^1$H NMR (400 MHz, CDCl$_3$) δ 7.21 (d, J=2.4 Hz, 1H), 7.10 (d, J=2.4 Hz, 1H), 5.31 (d, J=8.6 Hz, 1H), 4.28 (d, J=8.6 Hz, 1H), 3.90 (s, 3H), 2.69-2.59 (m, 1H), 2.39-2.25 (m, 2H), 2.24-2.14 (m, 1H), 1.99-1.86 (m, 1H), 1.69-1.59 (m, 1H); LC-MS: Method H, RT=1.13 min, MS (ESI) m/z: 352.1 (M+H)$^+$.

Intermediate 656D: (2-chloro-6-methoxybenzo[d]thiazol-4-yl)(1-(trifluoromethyl) cyclobutyl)methanol

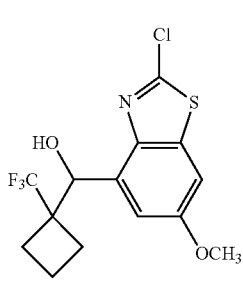
(656D)

Intermediate 656C (314 mg, 0.891 mmol) was purified by chiral SFC (Chiralpak OJ-H, 30×250 mm, 5 micron, 5% MeOH/95% CO$_2$, 70 mL/min, 150 bar, 40° C.) to give Intermediate 656D (136 mg, 0.386 mmol, 43%, 87.8% ee): $^1$H NMR and LCMS data was identical to Intermediate 656C.

Example 656

Intermediate I-121 (20 mg, 0.063 mmol), Intermediate 656D (22 mg, 0.063 mmol) and PdCl$_2$(dppf) (2.75 mg, 3.75 μmol) were dissolved in 1,4-dioxane (626 μL) and Na$_2$CO$_3$ (2 M, 282 μL, 0.563 mmol) and heated to 100° C. After 2 hours, the reaction mixture was cooled to ambient temperature and concentrated in vacuo. The crude material was purified by preparative HPLC (Method D, 60-100% B in 20 minutes) to give Example 656 (6.7 mg, 0.013 mmol, 21%): $^1$H NMR (500 MHz, DMSO-d$_6$) δ 8.88 (d, J=2.4 Hz, 1H), 8.58 (s, 1H), 8.18 (s, 1H), 7.93 (d, J=2.1 Hz, 1H), 7.69 (s, 1H), 7.33 (s, 1H), 5.94 (s, 1H), 4.00 (s, 3H), 3.90 (s, 3H), 3.42-3.36 (m, 1H), 2.70 (d, J=8.5 Hz, 1H), 2.21-2.12 (m, 2H), 2.09 (d, J=5.8 Hz, 1H), 1.83 (d, J=9.8 Hz, 1H), 1.56 (dd, J=10.5, 5.3 Hz, 1H); LC-MS: Method H, RT=1.32 min, MS (ESI) m/z: 509.0 (M+H)$^+$; Analytical HPLC Method B, 100% purity.

Example 657

(2R,3S)-3-((2-(3,6-dimethoxyquinolin-8-yl)-5-fluorobenzo[d]thiazol-6-yl)oxy)butan-2-yl (2-methylpyrimidin-5-yl)carbamate

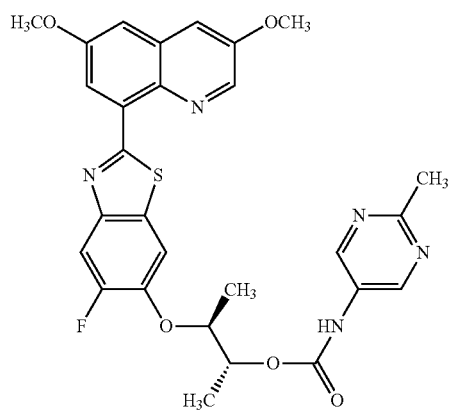
(657)

Intermediate 657A: 5-methoxy-2-nitrobenzoyl chloride

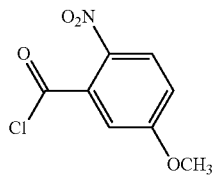
(657A)

5-methoxy-2-nitrobenzoic acid (3.9 g, 19.78 mmol) was dissolved in DCM (39.6 mL). Oxalyl chloride (13.8 mL, 27.7 mmol) and then DMF (0.153 mL, 1.98 mmol) were added at ambient temperature. After 1.5 hours, the reaction mixture was concentrated in vacuo to give Intermediate 657A, which was used directly in the subsequent step.

Intermediate 657B: ethyl 5-methoxy-2-nitrobenzoate

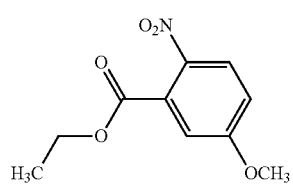
(657B)

Intermediate 657A (4.26 g, 19.8 mmol) was dissolved in sodium methoxide (0.5 M in MeOH, 59.3 mL, 29.6 mmol). THF (60 mL) was added to aid solubility. After stirring overnight, the reaction mixture was concentrated in vacuo, diluted with EtOAc and washed with water, then brine, dried (Na$_2$SO$_4$), filtered, and concentrated in vacuo to give Intermediate 657B (3.43 g, 15.2 mmol, 77%) as a yellow oil (Note, final extraction solution was allowed to sit overnight and the methyl ester swapped to the ethyl ester at that point): $^1$H NMR (400 MHz, CDCl$_3$) δ 8.04 (d, J=9.0 Hz, 1H), 7.06-7.04 (m, 1H), 7.04-6.99 (m, 1H), 4.41 (q, J=7.0 Hz, 2H), 3.92 (s, 3H), 1.37 (t, J=7.2 Hz, 3H)

Intermediate 657C: Ethyl 2-amino-5-methoxybenzoate

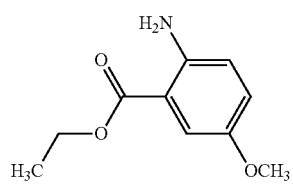
(657C)

Intermediate 657B (3.43 g, 15.2 mmol) was dissolved in EtOH (21.8 mL). Palladium on carbon (0.324 g, 0.305 mmol) and then ammonium formate (4.80 g, 76 mmol) were added and the reaction mixture was heated to reflux. After 3 hours, the reaction mixture was filtered through celite and concentrated in vacuo to give Intermediate 657C (2.85 g, 14.6 mmol, 96%) as an orange oil: $^1$H NMR (400 MHz, CDCl$_3$) δ 7.37 (d, J=3.1 Hz, 1H), 6.95 (dd, J=8.9, 3.0 Hz, 1H), 6.63 (d, J=8.8 Hz, 1H), 5.40 (br. s., 2H), 4.34 (q, J=7.3 Hz, 2H), 3.77 (s, 3H), 1.39 (t, J=7.2 Hz, 3H); LC-MS: Method H, RT=0.76 min, MS (ESI) m/z: 196 (M+H)$^+$.

Intermediate 657D: ethyl 2-amino-3-bromo-5-methoxybenzoate

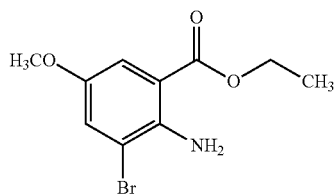

(657D)

Intermediate 657C (0.5 g, 2.56 mmol) and NBS (0.456 g, 2.56 mmol) were dissolved in AcOH (5.12 mL). After 3 hours, the reaction was quenched with vigorous stirring with saturated NaHCO$_3$. The layers were separated and the organic layer was further washed with water, then brine, dried (Na$_2$SO$_4$), filtered, and concentrated in vacuo. The crude material was purified by column chromatography (ISCO, 40 g silica gel column, 27 minute gradient from 0 to 100% EtOAc in hexanes) to give Intermediate 657D (236 mg, 0.861 mmol, 34%) as a yellow oil: $^1$H NMR (500 MHz, CDCl$_3$) δ 7.46 (d, J=2.8 Hz, 1H), 7.30 (d, J=3.0 Hz, 1H), 5.98 (br. s., 2H), 4.38 (q, J=7.1 Hz, 2H), 3.78 (s, 3H), 1.41 (t, J=7.2 Hz, 3H); LC-MS: Method H, RT=1.05 min, MS (ESI) m/z: 274/276 (M+H)$^+$.

Intermediate 657E: (2-amino-3-bromo-5-methoxyphenyl)methanol

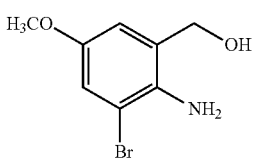

(657E)

Intermediate 657D (236 mg, 0.861 mmol) was dissolved in THF (2.87 mL). Lithium borohydride (37.5 mg, 1.72 mmol) was added and the reaction mixture was heated to 50° C. After 2 hours, the reaction mixture was diluted with water and stirred for 30 minutes. All of the lithium borohydride had not dissolved, so concentrated HCl was added carefully to speed up the quenching process. The reaction mixture was then extracted three times with EtOAc. The combined organic layers were washed with brine, dried (Na$_2$SO$_4$), filtered, and concentrated in vacuo to give Intermediate 657E (188 mg, 0.808 mmol, 94%) as an orange solid: $^1$H NMR (400 MHz, CDCl$_3$) δ 7.03 (d, J=2.9 Hz, 1H), 6.71 (d, J=2.9 Hz, 1H), 4.68 (s, 2H), 4.35 (br. s., 2H), 3.76 (s, 3H), 1.72 (br. s., 1H); LC-MS: Method H, RT=0.68 min, MS (ESI) m/z: 232/234 (M+H)$^+$.

Intermediate 657F: 2-amino-3-bromo-5-methoxybenzaldehyde

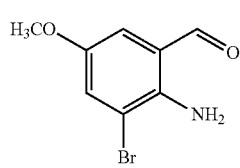

(657F)

Intermediate 657E (186 mg, 0.801 mmol) was dissolved in CHCl$_3$ (5.34 mL). Manganese dioxide (418 mg, 4.81 mmol) was added and the reaction mixture was heated to 40° C. After heating overnight, the reaction mixture was filtered through celite and concentrated in vacuo to give Intermediate 657F (167 mg, 0.724 mmol, 90%) as a red solid: $^1$H NMR (400 MHz, CDCl$_3$) δ 9.82 (s, 1H), 7.36 (d, J=2.9 Hz, 1H), 7.04 (d, J=2.9 Hz, 1H), 6.35 (br. s., 2H), 3.82 (s, 3H); LC-MS: Method H, RT=0.90 min, MS (ESI) m/z: 230/232 (M+H)$^+$.

Intermediate 657G: 3-(benzyloxy)-8-bromo-6-methoxyquinoline

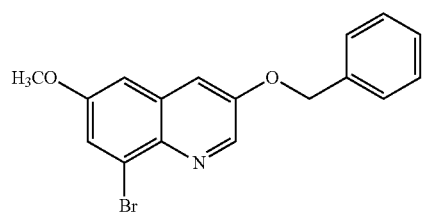

(657G)

Intermediate 657F (165 mg, 0.717 mmol), 2-(benzyloxy) acetaldehyde (108 mg, 0.717 mmol), and sodium methoxide (0.5 M in MeOH, 1.58 mL, 0.789 mmol) were dissolved in MeOH (2.87 mL) and heated to reflux. After heating overnight, the reaction mixture was diluted with saturated NH$_4$Cl, partially concentrated in vacuo and diluted with EtOAc. The layers were separated and the organic layer was washed with brine, dried (Na$_2$SO$_4$), filtered, and concentrated in vacuo. The crude material was purified by column chromatography (ISCO, 24 g silica gel column, 19 minute gradient from 0 to 100% EtOAc in hexanes) to give Intermediate 657G (210 mg, 0.610 mmol, 85%): LC-MS: Method H, RT=1.10 min, MS (ESI) m/z: 344/346 (M+H)$^+$.

Intermediate 657H: 8-bromo-6-methoxyquinolin-3-ol, HCl

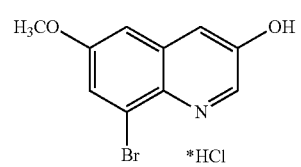

(657H)

Intermediate 657G (210 mg, 0.610 mmol) and pentamethylbenzene (633 mg, 4.27 mmol) were dissolved in DCM (12.2 mL) and cooled to −78° C. Boron trichloride (1 M in heptane, 1.59 mL, 1.59 mmol) was then added and the reaction mixture was allowed to warm slowly to ambient temperature. After stirring overnight, the reaction mixture was diluted with hexanes and 1 N HCl and allowed to stir for 1 hour. The solid was collected by suction filtration to give Intermediate 657H (38.9 mg, 0.134 mmol, 22%) as a brown solid: $^1$H NMR (400 MHz, MeOH$_4$) δ 8.54 (d, J=2.6 Hz, 1H), 8.01 (d, J=2.4 Hz, 1H), 7.77 (d, J=2.4 Hz, 1H), 7.39 (d, J=2.4 Hz, 1H), 3.97 (s, 3H); LC-MS: Method H, RT=0.77 min, MS (ESI) m/z: 254/256 (M+H)$^+$.

Intermediate 657I: 8-bromo-3,6-dimethoxyquinoline

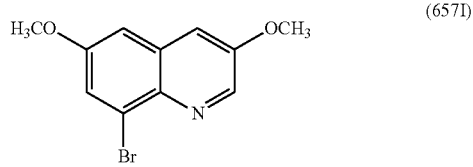 [SMILES: COc1cnc2c(Br)cc(OC)cc2c1]

(657I)

Intermediate 657H (38.9 mg, 0.134 mmol), K$_2$CO$_3$ (55.5 mg, 0.402 mmol), and methyl iodide (16.7 μL, 0.268 mmol) were dissolved in acetone (1.34 mL) and heated to 50° C. in a sealed tube. After heating overnight, the reaction mixture was diluted with EtOAc, washed with water, then brine, dried (Na$_2$SO$_4$), filtered, and concentrated in vacuo to give Intermediate 657I (32 mg, 0.119 mmol, 89%) as a tan solid: $^1$H NMR (400 MHz, CDCl$_3$) δ 8.55 (d, J=2.6 Hz, 1H), 7.51 (d, J=2.6 Hz, 1H), 7.22 (d, J=2.9 Hz, 1H), 6.93 (d, J=2.6 Hz, 1H), 3.88 (s, 3H), 3.84 (s, 3H); LC-MS: Method H, RT=0.93 min, MS (ESI) m/z: 268/270 (M+H)$^+$.

Intermediate 657J: 3,6-dimethoxy-8-(4,4,5,5-tetramethyl-1,3,2-dioxaborolan-2-yl) quinoline

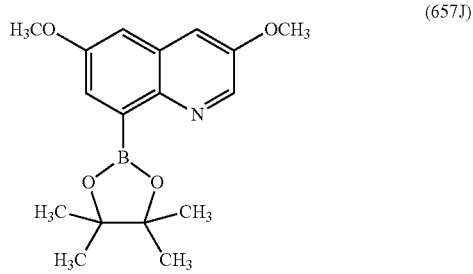 [SMILES: COc1cnc2c(B3OC(C)(C)C(C)(C)O3)cc(OC)cc2c1]

(657J)

Intermediate 657I (32 mg, 0.119 mmol), bispinacolatodiboron (60.6 mg, 0.239 mmol), potassium acetate (29.3 mg, 0.298 mmol), and PdCl$_2$(dppf)-CH$_2$Cl$_2$ adduct (7.80 mg, 9.55 μmol) were stored on HIVAC for 15 minutes, then were dissolved in 1,4-dioxane (597 μL), and degassed for 15 minutes by bubbling with argon. The reaction mixture was heated to 130° C. in the microwave for 40 minutes. The reaction mixture was diluted with EtOAc and washed with water then brine, dried (Na$_2$SO$_4$), filtered, and concentrated in vacuo to give Intermediate 657J, which was used directly in the subsequent reaction: LC-MS: Method H, RT=0.66 min, MS (ESI) m/z: 234.2 (boronic acid mass observed, M+H)$^+$.

Example 657

Intermediate 657J (18 mg, 0.057 mmol), Intermediate I-130 (23.5 mg, 0.057 mmol) and PdCl$_2$(dppf) (2.51 mg, 3.43 μmol) were dissolved in 1,4-dioxane (571 μL) and Na$_2$CO$_3$ (2 M, 257 μL, 0.514 mmol) and heated to 100° C. After 2 hours, the reaction mixture was cooled to ambient temperature. The reaction mixture was concentrated in vacuo. The crude material was purified by preparative HPLC (Method D, 45-90% B in 20 minutes) to give Example 657 (6.2 mg, 0.011 mmol, 19%): $^1$H NMR (500 MHz, DMSO-d$_6$) δ 9.96 (br. s., 1H), 8.82-8.64 (m, 3H), 8.33 (br. s., 1H), 8.04 (d, J=7.9 Hz, 1H), 7.96 (d, J=11.6 Hz, 1H), 7.87 (br. s., 1H), 7.55 (br. s., 1H), 5.12 (d, J=4.9 Hz, 1H), 4.81 (br. s., 1H), 3.99 (s, 6H), 2.56 (s, 3H), 1.40 (d, J=5.8 Hz, 6H); LC-MS: Method H, RT=1.12 min, MS (ESI) m/z: 565.9 (M+H)$^+$; Analytical HPLC Method B, 100% purity.

Example 658

2-((4-(1-hydroxy-2,2-dimethylpropyl)-2-(2-methoxy-7-methylquinoxalin-5-yl)benzo[d]thiazol-6-yl)oxy)ethyl pyridin-4-ylcarbamate

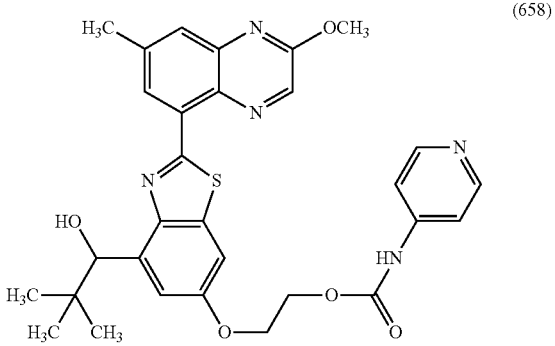 [SMILES: COc1cnc2c(-c3nc4c(C(O)C(C)(C)C)cc(OCCOC(=O)Nc5ccncc5)cc4s3)cc(C)cc2n1]

(658)

Intermediate 658A: 1-(2-chloro-6-(2-hydroxyethoxy)benzo[d]thiazol-4-yl)-2,2-dimethylpropan-1-ol

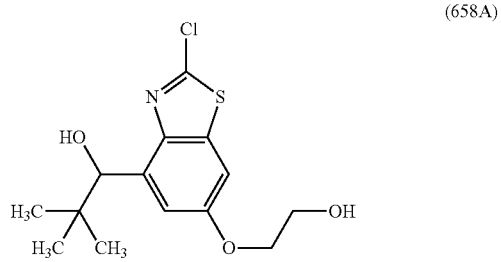 [SMILES: CC(C)(C)C(O)c1cc(OCCO)cc2sc(Cl)nc12]

(658A)

Intermediate 638D (19.4 mg, 0.055 mmol) was dissolved in toluene (363 μL) and THF (182 μL) and cooled to −78° C. DIBAL-H (1 M in toluene, 164 μL, 0.164 mmol) was then added and the reaction mixture was allowed to warm slowly to ambient temperature. After stirring overnight, another 50 μL of DIBAL was then added. After 2.5 hours, the reaction was quenched with a saturated solution of Rochelle's salt. The reaction mixture was extracted with EtOAc. The organic layer was further washed with brine, dried (Na₂SO₄), filtered, and concentrated in vacuo to give Intermediate 658A (28.3 mg, 0.090 mmol, 100%) as an orange oil, which was used directly in the subsequent reaction: LC-MS: Method H, RT=0.97 min, MS (ESI) m/z: 316.2 (M+H)⁺.

Intermediate 658B: 2-((2-chloro-4-(1-hydroxy-2,2-dimethylpropyl)benzo[d]thiazol-6-yl) oxy)ethyl carbonochloridate

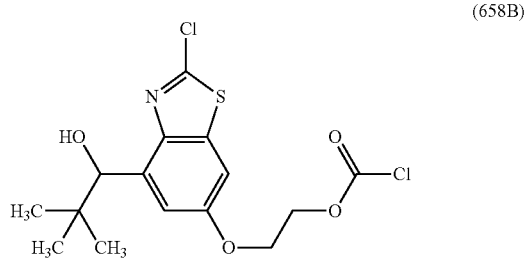 [SMILES: CC(C)(C)C(O)c1cc(OCCOC(=O)Cl)cc2sc(Cl)nc12]

(658B)

Intermediate 658A (24 mg, 0.076 mmol) and phosgene solution (15% in toluene, 268 μL, 0.380 mmol) were dissolved in THF (760 μL). After 30 minutes, the reaction mixture was concentrated in vacuo to give Intermediate 658B, which was used directly in the subsequent reaction: LC-MS: Method H, RT=1.17 min, MS (ESI) m/z: 378.0 (M+H)⁺.

Intermediate 658C: 2-((2-chloro-4-(1-hydroxy-2,2-dimethylpropyl)benzo[d]thiazol-6-yl) oxy)ethyl pyridin-4-ylcarbamate

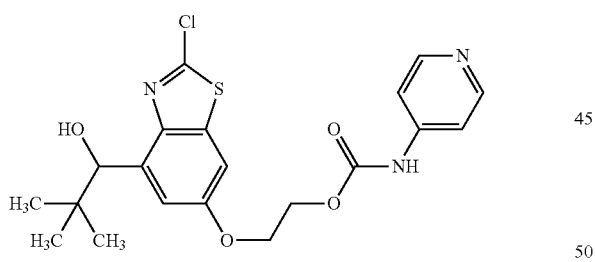

(658C)

Intermediate 658B (14 mg, 0.037 mmol), pyridin-4-amine (12.2 mg, 0.130 mmol), and diisopropylethylamine (64.6 μL, 0.370 mmol) were dissolved in DCM (740 μL). After 30 minutes, the reaction mixture was concentrated in vacuo to give Intermediate 658C, which was used directly in the subsequent step: LC-MS: Method H, RT=0.87 min, MS (ESI) m/z: 436.1 (M+H)⁺.

Example 658

Intermediate I-9 (13.2 mg, 0.044 mmol) and Intermediate 658C (16 mg, 0.037 mmol) were dissolved in DMF (367 μL). PdCl₂(dppf)-CH₂Cl₂ adduct (1.8 mg, 2.2 μmol) was added and the reaction mixture was degassed by bubbling with argon for 15 minutes. Sodium carbonate (2 M, 22 μL, 0.044 mmol) was added and the reaction mixture was degassed for 5 minutes, then sealed and heated to 100° C. in the microwave for 30 minutes. The crude material was purified by preparative HPLC (Method D, 55-100% B in 20 minutes) to give Example 658 (3.3 mg, 0.0057 mmol, 16%): ¹H NMR (500 MHz, DMSO-d₆) δ 10.29 (s, 1H), 8.72 (s, 1H), 8.52 (s, 1H), 8.38 (d, J=5.8 Hz, 2H), 7.81 (s, 1H), 7.64 (d, J=2.1 Hz, 1H), 7.45 (d, J=6.1 Hz, 2H), 7.15 (d, J=2.1 Hz, 1H), 5.42 (d, J=4.6 Hz, 1H), 5.31 (d, J=4.9 Hz, 1H), 4.53 (br. s., 2H), 4.42-4.23 (m, 2H), 4.07 (s, 3H), 3.35 (s, 1H), 2.64 (s, 3H), 0.94 (s, 9H); LC-MS: Method H, RT=1.08 min, MS (ESI) m/z: 574.2 (M+H)⁺; Analytical HPLC Method B, 99% purity.

Example 659

(2R,3S)-3-((2-(3-(difluoromethoxy)-6-methylquinolin-8-yl)-5-fluorobenzo[d]thiazol-6-yl)oxy)butan-2-yl (2-methylpyrimidin-5-yl)carbamate

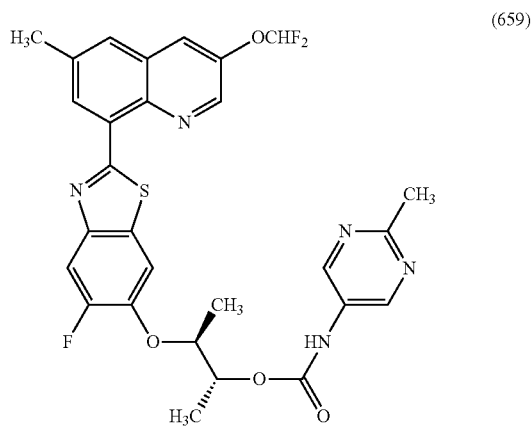

(659)

Intermediate 659A: 8-bromo-3-(difluoromethoxy)-6-methylquinoline

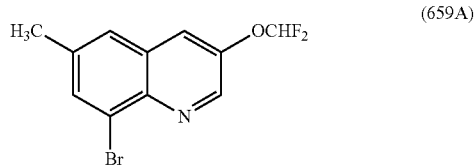 [SMILES: Cc1cc(Br)c2ncc(OC(F)F)cc2c1]

(659A)

Intermediate I-125E (100 mg, 0.42 mmol) and K₂CO₃ (290 mg, 2.1 mmol) were suspended in DMF (4.2 mL) and heated to 100° C. Sodium 2-chloro-2,2-difluoroacetate (256 mg, 1.68 mmol) was then added. After 1.5 hours, the reaction mixture was cooled to ambient temperature, diluted with water, and thrice extracted with EtOAc. The combined organic extracts were washed with brine, dried (Na₂SO₄), filtered, and concentrated in vacuo. The crude material was purified by column chromatography (ISCO, 24 g silica gel column, 19 minute gradient from 0 to 50% EtOAc in hexanes) to give Intermediate 659A (58 mg, 0.201 mmol, 48%): ¹H NMR (500 MHz, CDCl₃) δ 8.85 (d, J=2.5 Hz, 1H), 7.93 (d, J=1.7 Hz, 1H), 7.81 (d, J=2.5 Hz, 1H), 7.56 (s, 1H), 6.88-6.47 (m, 1H), 2.56 (s, 3H); LC-MS: Method H, RT=1.08 min, MS (ESI) m/z: 288/290 (M+H)⁺.

Intermediate 659B: 3-(difluoromethoxy)-6-methyl-8-(4,4,5,5-tetramethyl-1,3,2-dioxaborolan-2-yl)quinoline

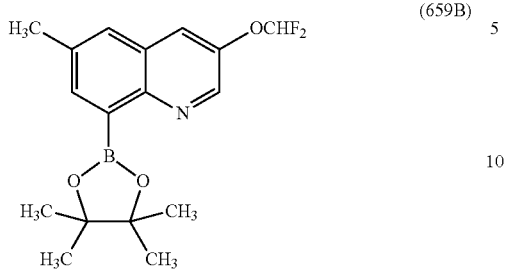

(659B)

Intermediate 659A (58 mg, 0.201 mmol), bispinacolatodiboron (102 mg, 0.403 mmol), potassium acetate (49.4 mg, 0.503 mmol), and PdCl$_2$(dppf)-CH$_2$Cl$_2$ adduct (13.2 mg, 0.016 mmol) were stored on HIVAC for 15 minutes then were dissolved in dry 1,4-dioxane (1.01 mL) and degassed for 15 minutes by bubbling with argon. The reaction mixture was heated to 130° C. in the microwave for 40 minutes. The reaction mixture was diluted with EtOAc and washed with water then brine, dried (Na$_2$SO$_4$), filtered, and concentrated in vacuo to give Intermediate 659B, which was used directly in the subsequent reaction: LC-MS: Method H, RT=0.82 min, MS (ESI) m/z: 254.0 (boronic acid mass observed, M+H)$^+$.

Example 659

Intermediate 659B (15 mg, 0.045 mmol), Intermediate I-130 (18.4 mg, 0.045 mmol) and PdCl$_2$(dppf) (1.96 mg, 2.69 μmol) were dissolved in 1,4-dioxane (448 μL) and Na$_2$CO$_3$ (2 M, 201 μL, 0.403 mmol) and heated to 100° C. After 1 hour, the reaction mixture was cooled to ambient temperature and concentrated in vacuo. The crude material was purified by preparative HPLC (Method D, 45-90% B in 20 minutes) to give Example 659 (8.7 mg, 0.015 mmol, 33%): $^1$H NMR (500 MHz, DMSO-d$_6$) δ 9.95 (br. s., 1H), 8.98 (br. s., 1H), 8.77 (br. s., 1H), 8.74 (br. s., 2H), 8.29 (br. s., 1H), 8.06 (d, J=7.6 Hz, 1H), 8.00 (br. s., 1H), 7.96 (d, J=11.3 Hz, 1H), 7.66-7.32 (m, 1H), 5.12 (d, J=6.4 Hz, 1H), 4.82 (d, J=5.8 Hz, 1H), 2.64 (s, 3H), 2.55 (s, 3H), 1.40 (br. s., 6H); LC-MS: Method H, compound did not ionize; Analytical HPLC Method B, 100% purity.

Example 660

(2R,3S)-3-((2-(3-ethoxy-6-methylquinolin-8-yl)-5-fluorobenzo[d]thiazol-6-yl)oxy)butan-2-yl (2-methylpyrimidin-5-yl)carbamate

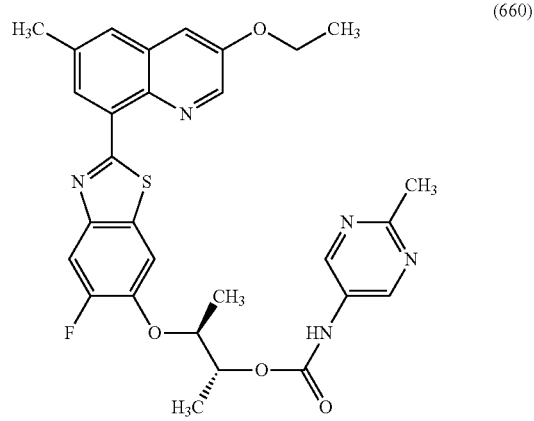

(660)

Intermediate 660A:
8-bromo-3-ethoxy-6-methylquinoline

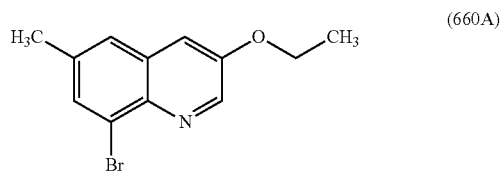

(660A)

Intermediate I-125E (100 mg, 0.364 mmol), K$_2$CO$_3$ (151 mg, 1.09 mmol), and iodoethane (114 mg, 0.728 mmol) were dissolved in acetone (3.64 mL) and heated to 50° C. in a sealed tube. After heating overnight, the reaction mixture was diluted with EtOAc, washed with water, then brine, dried (Na$_2$SO$_4$), filtered, and concentrated in vacuo to give Intermediate 660A (105 mg, 0.394 mmol, 100%) as a yellow solid: $^1$H NMR (400 MHz, CDCl$_3$) δ 8.73 (d, J=2.9 Hz, 1H), 7.76 (d, J=1.5 Hz, 1H), 7.46 (s, 1H), 7.30 (d, J=2.9 Hz, 1H), 4.19 (q, J=7.0 Hz, 2H), 2.52 (s, 3H), 1.54 (t, J=6.9 Hz, 3H); LC-MS: Method H, RT=1.14 min, MS (ESI) m/z: 266/268 (M+H)$^+$.

Intermediate 660B: 3-ethoxy-6-methyl-8-(4,4,5,5-tetramethyl-1,3,2-dioxaborolan-2-yl) quinoline

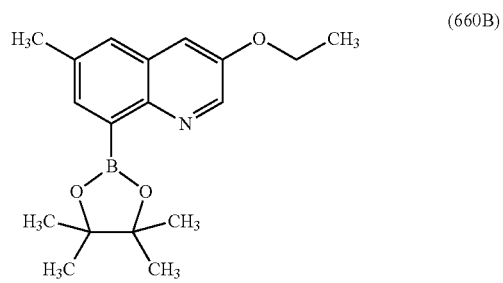 [SMILES: CCOc1cnc2c(B3OC(C)(C)C(C)(C)O3)cc(C)cc2c1]

(660B)

Intermediate 660A (100 mg, 0.376 mmol), bispinacolatodiboron (191 mg, 0.752 mmol), potassium acetate (92 mg, 0.939 mmol), and PdCl$_2$(dppf)-CH$_2$Cl$_2$ adduct (24.6 mg, 0.030 mmol) were stored on HIVAC for 15 minutes then were dissolved in dry 1,4-dioxane (1.88 mL) and degassed for 15 minutes by bubbling with argon. The reaction mixture was heated to 130° C. in the microwave for 40 minutes. The reaction mixture was diluted with EtOAc and washed with water then brine, dried (Na$_2$SO$_4$), filtered, and concentrated in vacuo to give Intermediate 660B, which was used directly in the subsequent reaction: LC-MS: Method H, RT=0.70 min, MS (ESI) m/z: 232.0 (boronic acid mass observed, M+H)$^+$.

Example 660

Intermediate 660B (15 mg, 0.048 mmol), Intermediate I-130 (19.7 mg, 0.048 mmol) and PdCl$_2$(dppf) (2.1 mg, 2.87 μmol) were dissolved in 1,4-dioxane (479 μL) and Na$_2$CO$_3$ (2 M, 216 μL, 0.431 mmol) and heated to 100° C. After 1 hour, the reaction mixture was cooled to ambient temperature and concentrated in vacuo. The crude material was purified by preparative HPLC (Method D, 50-100% B in 15 minutes) to give Example 660 (7.2 mg, 0.013 mmol, 27%):

¹H NMR (500 MHz, DMSO-d₆) δ 9.95 (br. s., 1H), 8.77 (br. s., 1H), 8.74 (br. s., 2H), 8.60 (br. s., 1H), 8.04 (d, J=7.9 Hz, 1H), 7.94 (d, J=11.6 Hz, 1H), 7.85 (br. s., 2H), 5.11 (d, J=6.1 Hz, 1H), 4.80 (d, J=5.5 Hz, 1H), 4.33-4.20 (m, 2H), 2.61 (s, 3H), 2.55 (s, 3H), 1.46 (t, J=6.6 Hz, 3H), 1.40 (d, J=5.5 Hz, 6H); LC-MS: Method H, RT=1.04 min, MS (ESI) m/z: 562.2 (M+H)⁺; Analytical HPLC Method B, 100% purity.

Example 661

5-(benzofuran-2-yl)-2-ethoxy-7-methylquinoxaline

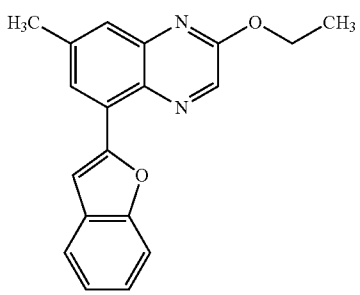

(661)

Intermediate 661A: tert-butyl N-(2-bromo-4-methyl-6-nitrophenyl)-N-[(tert-butoxy)carbonyl] carbamate

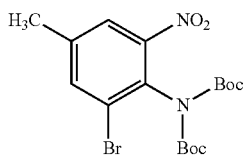

(661A)

2-Bromo-4-methyl-6-nitroaniline (3 g, 12.98 mmol), DMAP (0.159 g, 1.298 mmol), and Boc₂O (7.54 ml, 32.5 mmol) were dissolved in THF (21.64 ml) and allowed to stir overnight. The reaction mixture was diluted with water and extracted with EtOAc. The organic layer was washed with brine, dried (Na₂SO₄), filtered, and concentrated in vacuo. The crude material was purified by column chromatography (ISCO, 80 g silica gel column, 29 minute gradient from 0 to 50% EtOAc in hexanes) to yield Intermediate 661A (5.41 g, 12.54 mmol, 97% yield) as a yellow solid. ¹H NMR (400 MHz, MeOH₄) δ 7.90 (s, 2H), 2.47 (s, 3H), 1.36 (s, 18H). LC-MS: method H, RT=1.10 min, compound does not ionize.

Intermediate 661B: methyl 2-((2-bromo-4-methyl-6-nitrophenyl)(tert-butoxycarbonyl)amino)acetate

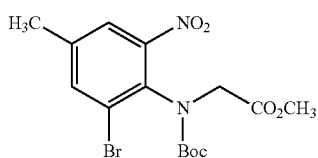

(661B)

Intermediate 661A (5.41 g, 12.54 mmol) was dissolved in DCM (20.91 ml) and TFA (1.933 ml, 25.09 mmol) was added. The reaction mixture was stirred at room temperature for 45 min. The reaction mixture was diluted with DCM, quenched with saturated NaHCO₃, washed with brine, dried (Na₂SO₄), filtered, and concentrated in vacuo. The crude material was redissolved in DMF (20.91 ml). Cs₂CO₃ (10.22 g, 31.4 mmol) was added and stirred for 15 minutes. Methyl bromoacetate (1.387 ml, 15.05 mmol) was added and stirred for an additional 15 min. The reaction mixture was diluted with EtOAc, washed with water, then brine, dried (Na₂SO₄), filtered, and concentrated in vacuo. The crude material was purified by column chromatography (ISCO, 120 g silica gel column, 29 minute gradient from 0 to 50% EtOAc in hexanes) to yield Intermediate 661B (4.58 g, 11.36 mmol, 91% yield) as a yellow oil. ¹H NMR (400 MHz, CDCl₃) δ 7.79-7.54 (m, 2H), 4.55 (d, J=17.3 Hz, 1H), 4.00 (s, 1H), 3.68 (s, 3H), 2.43 (s, 3H), 1.56-1.53 (m, 3H), 1.42-1.33 (m, 9H). LC-MS: method H, RT=1.02 min, compound does not ionize.

Intermediate 661C: methyl 2-((2-bromo-4-methyl-6-nitrophenyl)amino)acetate

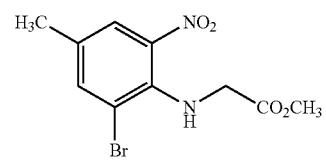

(661C)

Intermediate 661B (4.58 g, 11.36 mmol) was dissolved in HCl in dioxanes (14.20 ml, 56.8 mmol) and stirred at room temperature for 5 h. The reaction mixture was concentrated to yield Intermediate 661C (3.55 g, 11.71 mmol, 100% yield) as a yellow solid. Used without further purification. ¹H NMR (400 MHz, CDCl₃) δ 7.72 (d, J=2.8 Hz, 2H), 4.56 (d, J=17.3 Hz, 1H), 4.05 (d, J=17.6 Hz, 1H), 3.69 (s, 3H), 2.43 (s, 3H). LC-MS: method H, RT=0.97 min, MS (ESI) m/z: 303.1 (M+H)⁺.

Intermediate 661D: 5-bromo-7-methyl-3,4-dihydroquinoxalin-2(1H)-one

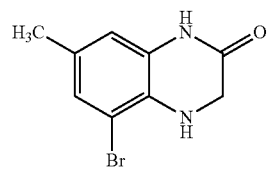

(661D)

Intermediate 661C (3.55 g, 11.71 mmol) was dissolved in MeOH (42.6 ml). Concentrated HCl (3.90 ml, 46.8 mmol) then tin(II) chloride dihydrate (10.57 g, 46.8 mmol) were added and the reaction heated to 65° C. for 2.5 h. The reaction mixture was cooled to ambient temperature, neutralized with 10 N NaOH and diluted with brine and EtOAc. The mixture was filtered through celite and the layers separated. The organic layer was washed with saturated NaHCO₃, then brine, dried (Na₂SO₄), filtered, and concentrated in vacuo to yield Intermediate 661D (2.30 g, 9.54 mmol, 81%). $^1$H NMR (400 MHz, CDCl$_3$) δ 8.75 (br. s., 1H), 6.95 (s, 1H), 6.52 (s, 1H), 4.29 (br. s., 1H), 4.04 (d, J=1.3 Hz, 2H), 2.22 (s, 3H). LC-MS: method H, RT=0.78 min, MS (ESI) m/z: 241.1 (M+H)$^+$.

Intermediate 661E:
5-bromo-7-methylquinoxalin-2(1H)-one

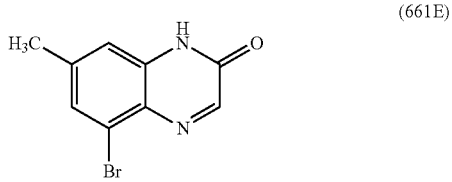

(661E)

Intermediate 661D (2.30 g, 9.54 mmol) was suspended in MeOH (27.7 ml). NaOH (28.6 ml, 28.6 mmol) then H$_2$O$_2$ (5.01 ml, 57.2 mmol) were added and the reaction mixture was allowed to stir at room temperature for 48 h. The reaction was quenched with saturated Na$_2$SO$_3$. The reaction was then diluted with saturated NaHCO$_3$ and extracted thrice with EtOAc. The combined organic layers were filtered through celite, washed with brine, dried (Na$_2$SO$_4$), filtered, and concentrated in vacuo. Compound was then triturated with EtOAc to yield Intermediate 661E (1.32 g, 5.52 mmol, 57.9% yield) as an off white solid. $^1$H NMR (400 MHz, DMSO-d$_6$) δ 8.16 (s, 1H), 7.49 (s, 1H), 7.09 (s, 1H), 2.40 (s, 3H). LC-MS: method H, RT=0.75 min, MS (ESI) m/z: 239.0 (M+H)$^+$.

Intermediate 661F:
5-bromo-2-ethoxy-7-methylquinoxaline

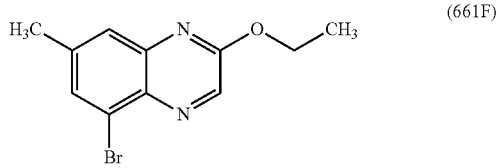

(661F)

Intermediate 661E (0.050 g, 0.209 mmol) was dissolved in DMF (1 mL). To this solution was added Cs$_2$CO$_3$ (0.341 g, 1.046 mmol), and the reaction mixture was allowed to stir for 5 min. Iodoethane (0.017 mL, 0.209 mmol) was then added, and the reaction mixture was allowed to room temperature for 48 hours. The reaction mixture was diluted with water and EtOAc. The layers were separated and the organic layer was washed with brine, dried with sodium sulfate and concentrated under reduced pressure. Purified on Prep HPLC using Solvent A: 10% MeOH/90% H$_2$O/0.1% TFA and Solvent B 90% MeOH/10% H$_2$O/0.1% TFA on Phenomenex AXIA C18 30×100 mm with a 10 min gradient and 5 min hold time with a flow rate of 40 mL/min to yield Intermediate 661F (0.012 g, 0.045 mmol, 21.48% yield) as a yellow solid. $^1$H NMR (400 MHz, CDCl$_3$) δ 8.32 (s, 1H), 7.52-7.47 (m, 1H), 7.11 (s, 1H), 4.30 (q, J=7.2 Hz, 2H), 2.51 (s, 3H), 1.38 (t, J=7.2 Hz, 3H). LC-MS: method H, RT=0.87 min, MS (ESI) m/z: 267.0 (M+H)$^+$.

Example 661

Intermediate 661F (0.012 g, 0.045 mmol) and benzofuran-2-ylboronic acid (10.91 mg, 0.067 mmol) were dissolved in toluene (0.674 ml) and EtOH (0.225 ml). PdCl$_2$(dppf)-CH$_2$Cl$_2$ adduct (2.201 mg, 2.70 µmol) was added and the reaction degassed by bubbling with argon for 15 minutes. Na$_2$CO$_3$ (0.027 ml, 0.054 mmol) was added and the reaction degassed for 5 minutes, then sealed and heated to 120° C. in the microwave for 30 minutes. The reaction mixture was diluted with EtOAc, filtered through a micron filter, and concentrated in vacuo. The crude material was purified by Prep LC (Axia Luna 5u C18 30×100 mm column, 10 minute gradient from 20 to 100% B in A, A=10:90:0.1 MeOH:H$_2$O:TFA, B=90:10:0.1 MeOH:H$_2$O:TFA) to yield Example 661 (0.88 mg, 2.75 µmol, 6.11% yield) as a tan solid. $^1$H NMR (400 MHz, CDCl$_3$) δ 8.50 (s, 1H), 8.13 (d, J=2.0 Hz, 1H), 8.07 (d, J=0.8 Hz, 1H), 7.67 (d, J=7.5 Hz, 1H), 7.60 (d, J=1.0 Hz, 1H), 7.56 (d, J=8.8 Hz, 1H), 7.35-7.29 (m, 1H), 7.28-7.22 (m, 1H), 4.56 (q, J=7.0 Hz, 2H), 2.62 (s, 3H), 1.50 (t, J=7.2 Hz, 3H). LC-MS: method H, RT=1.31 min, MS (ESI) m/z: 305.1 (M+H)$^+$.

Example 662

4-methoxyphenyl (2-((2-(2-methoxy-7-methylquinoxalin-5-yl)-7-methylthiazolo[5,4-b]pyridin-5-yl)oxy)ethyl)carbamate

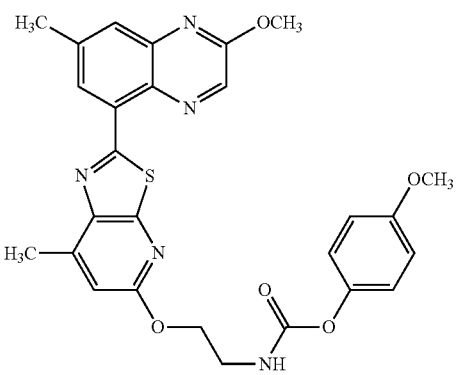

(662)

Intermediate 662A: tert-butyl (2-((2-amino-7-methylthiazolo[5,4-b]pyridin-5-yl)oxy)ethyl)carbamate

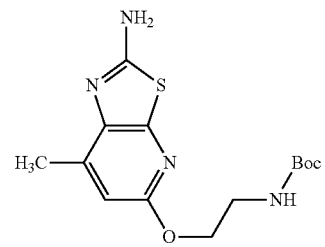

(662A)

Intermediate I-138A (0.250 g, 0.729 mmol) was dissolved in DMF (7.29 ml). tert-Butyl (2-bromoethyl)carbamate (0.196 g, 0.875 mmol) and Cs$_2$CO$_3$ (1.187 g, 3.64 mmol) were added and the reaction mixture was stirred at 40° C. overnight. The reaction mixture was diluted with EtOAc and water and the layers were separated. The organic layer was washed with brine, dried with sodium sulfate, and concentrated under reduced pressure. The reaction was purified on ISCO using a 40 g column with a 0-100% EtOAc in hexanes gradient to yield Intermediate 662A (0.074 g, 0.228 mmol, 31.3% yield) as a pale yellow solid. $^1$H NMR (400 MHz, CDCl$_3$) δ 6.54 (s, 1H), 5.01 (br. s., 2H), 4.33 (t, J=5.2 Hz, 2H), 3.52 (d, J=4.8 Hz, 2H), 2.49 (d, J=0.7 Hz, 3H), 1.45 (s, 9H), 1.28-1.24 (m, 1H). LC-MS: method H, RT=0.83 min, MS (ESI) m/z: 325.2 (M+H)$^+$.

Intermediate 662B: tert-butyl (2-((2-bromo-7-methylthiazolo[5,4-b]pyridin-5-yl)oxy)ethyl)carbamate

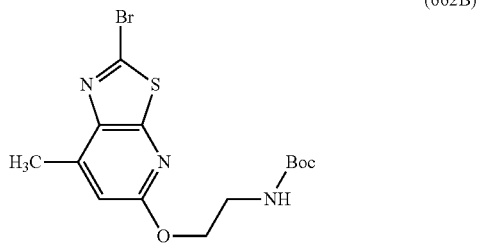

(662B)

Copper(II) bromide (0.087 g, 0.388 mmol) and t-butyl nitrite (0.046 ml, 0.388 mmol) were dissolved in MeCN (0.912 ml) and allowed to stir 10 minutes. Intermediate 662A (0.074 g, 0.228 mmol) was dissolved in MeCN (1.369 ml) and the copper solution was added. The reaction mixture was diluted with EtOAc, washed with 1 N HCl, saturated NaHCO$_3$, then brine, dried (Na+SO$_4$), filtered, and concentrated in vacuo to yield Intermediate 662B (0.080 g, 0.206 mmol, 90% yield). $^1$H NMR (400 MHz, CDCl$_3$) δ 6.66 (d, J=0.9 Hz, 1H), 4.39 (t, J=5.3 Hz, 2H), 3.54 (d, J=5.1 Hz, 2H), 2.63 (d, J=0.9 Hz, 3H), 1.45 (s, 9H). LC-MS: method H, RT=1.13 min, MS (ESI) m/z: 388.1 (M+H)$^+$.

Intermediate 662C: tert-butyl (2-((2-(2-methoxy-7-methylquinoxalin-5-yl)-7-methylthiazolo[5,4-b]pyridin-5-yl)oxy)ethyl)carbamate

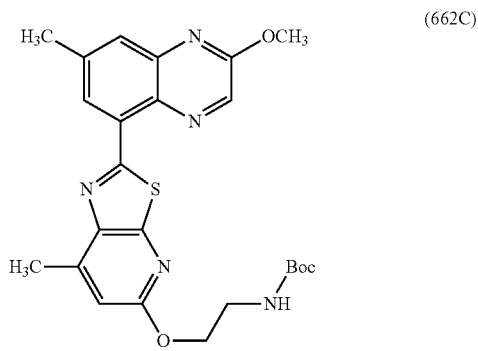 [SMILES: COc1cnc2c(-c3nc4c(C)cc(OCCNC(=O)OC(C)(C)C)nc4s3)cc(C)cc2n1]

(662C)

Intermediate I-9 (0.062 g, 0.206 mmol) and Intermediate 662B (0.080 g, 0.206 mmol) were dissolved in DMF (1 ml). PdCl$_2$(dppf)-CH$_2$Cl$_2$ adduct (10.10 mg, 0.012 mmol) was added and the reaction degassed by bubbling with argon for 15 minutes. Na$_2$CO$_3$, 3 M aqueous solution (0.100 ml, 0.300 mmol) was added and the reaction degassed for 5 minutes, then sealed and heated to 90° C. in the microwave for 30 minutes. The reaction mixture was filtered and purified on 24 g ISCO column with 0-100% EtOAc in hexanes gradient to yield Intermediate 662C (0.048 g, 0.100 mmol, 48.4% yield) as a pale yellow solid. $^1$H NMR (400 MHz, CDCl$_3$) δ 8.60 (d, J=2.0 Hz, 1H), 8.54 (s, 1H), 7.77-7.72 (m, 1H), 6.70 (d, J=0.7 Hz, 1H), 4.47 (t, J=5.2 Hz, 2H), 4.12 (s, 3H), 3.58 (d, J=4.8 Hz, 2H), 2.79 (d, J=0.7 Hz, 3H), 2.66 (s, 3H), 1.53 (s, 9H). LC-MS: method H, RT=1.36 min, MS (ESI) m/z: 482.1 (M+H)$^+$.

Intermediate 662D: 2-((2-(2-methoxy-7-methylquinoxalin-5-yl)-7-methylthiazolo[5,4-b] pyridin-5-yl)oxy)ethanamine

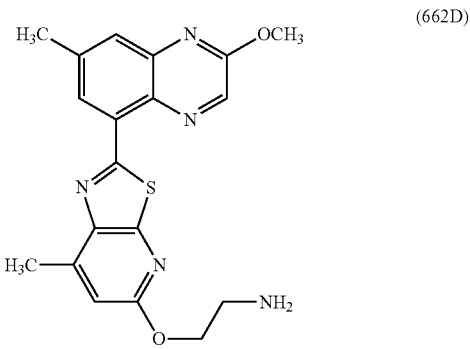

(662D)

To a mixture of Intermediate 662C (0.048 g, 0.100 mmol) in DCM (1) was added 2,6-lutidine (0.035 ml, 0.299 mmol) followed by TMS-OTf (0.072 ml, 0.399 mmol) at room temperature. The mixture was stirred at room temperature for 1 h. The mixture was diluted with NaHCO$_3$ and extracted by EtOAc. The combined organic layer was washed by brine, dried by sodium sulfate and concentrated to yield Intermediate 662D (0.036 g, 0.094 mmol, 95% yield). $^1$H NMR (400 MHz, CDCl$_3$) δ 8.60 (d, J=1.5 Hz, 1H), 8.53 (s, 1H), 7.74 (d, J=0.9 Hz, 1H), 6.72 (d, J=0.9 Hz, 1H), 4.44 (t, J=5.3 Hz, 2H), 4.12 (s, 3H), 3.12 (t, J=5.3 Hz, 2H), 2.79 (d, J=0.9 Hz, 3H), 2.66 (s, 3H). LC-MS: method H, RT=1.08 min, MS (ESI) m/z: 382.1 (M+H)$^+$.

Example 662

Intermediate 662D (0.020 g, 0.052 mmol) was dissolved in DCM (0.350 ml) and THF (0.175 ml). To the solution was added 4-methoxyphenyl carbonochloridate (0.029 g, 0.157 mmol) followed by DIEA (0.092 ml, 0.524 mmol). The solution was allowed to stir at room temperature overnight. The reaction mixture was concentrated and suspended in 2 mL of hot DMSO, filtered, and purified by preparative HPLC (Method D, 70% to 100% B in 20 minutes) to yield Example 662 (0.0027 g, 5.08 μmol, 9.69% yield): MS (ESI) m/z: 532.2 (M+H)$^+$. $^1$H NMR (500 MHz, DMSO-d$_6$) δ 8.76 (br. s., 1H), 8.59 (br. s., 1H), 7.94-7.85 (m, 2H), 7.03 (d, J=8.0 Hz, 2H), 6.79-6.67 (m, 2H), 4.47 (br. s., 2H), 4.11 (br. s., 3H), 3.76 (br. s., 4H), 3.67 (br. s., 2H), 2.77 (br. s., 3H), 2.67 (br. s., 3H). LC-MS: method H, RT=1.45 min, MS (ESI) m/z: 532.1 (M+H)$^+$. Analytical HPLC Method B: 100% purity.

Example 663

(6-methoxy-2-(2-methoxy-7-methylquinoxalin-5-yl)benzo[d]thiazol-4-yl)(tetrahydro-2H-pyran-4-yl)methanol

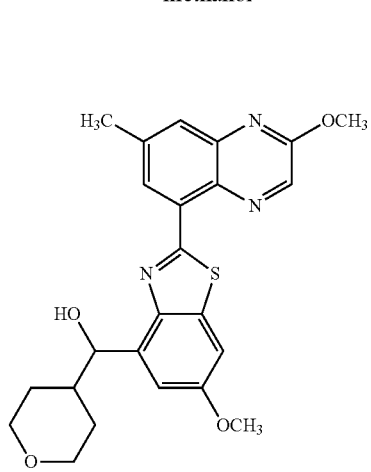

(663)

Intermediate 663A: (2-amino-6-methoxybenzo[d]thiazol-4-yl)(tetrahydro-2H-pyran-4-yl) methanol

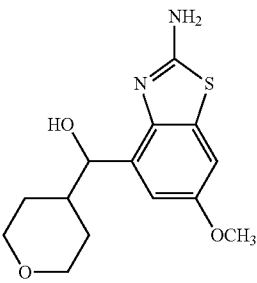

(663A)

Intermediate I-22 (50 mg, 0.193 mmol) was dissolved in THF (1930 µl). NaH (8.49 mg, 0.212 mmol) was added and the reaction mixture was stirred for 5 min. The reaction mixture was cooled to −78° C. and BuLi (101 µL, 0.232 mmol) was added and allowed to stir for 30 min. Tetrahydro-2H-pyran-4-carbaldehyde (44.0 mg, 0.386 mmol) was added and the reaction mixture was allowed to warm to ambient temperature. The reaction mixture was diluted with EtOAc and washed with water, then brine, dried ($Na_2SO_4$), filtered, and concentrated in vacuo to yield Intermediate 663A (0.05 g, 0.170 mmol, 88%). Used without further purification. LC-MS: method H, RT=0.56 min, MS (ESI) m/z: 295.2 (M+H)$^+$.

Intermediate 663B: (2-chloro-6-methoxybenzo[d]thiazol-4-yl)(tetrahydro-2H-pyran-4-yl)methanol

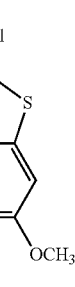

(663B)

Copper(II) chloride (0.044 g, 0.329 mmol) and t-butyl nitrite (0.039 ml, 0.329 mmol) were dissolved in MeCN (0.775 ml) and allowed to stir 10 minutes. Intermediate 663A (0.057 g, 0.194 mmol) was dissolved in MeCN (1.162 ml) and the copper solution was added. The reaction mixture was stirred for 2.5 h at 60° C. The reaction mixture was diluted with EtOAc, washed with 1 N HCl, saturated $NaHCO_3$, then brine, dried ($Na_2SO_4$), filtered, and concentrated in vacuo. Purified on ISCO using 0-100% EtOAc in hexanes gradient on a 24 g column to yield Intermediate 663B (0.020 g, 0.064 mmol, 32.9% yield). $^1$H NMR (400 MHz, $CDCl_3$) δ 7.15 (d, J=2.4 Hz, 1H), 6.95 (d, J=2.4 Hz, 1H), 4.72 (t, J=7.6 Hz, 1H), 3.97 (d, J=6.6 Hz, 2H), 3.87 (s, 3H), 3.46-3.34 (m, 3H), 3.27 (td, J=11.8, 2.2 Hz, 1H), 1.28-1.23 (m, 2H), 0.94-0.81 (m, 2H). LC-MS: method H, RT=0.56 min, MS (ESI) m/z: 314.1 (M+H)$^+$.

Example 663

Intermediate I-9 (9.57 mg, 0.032 mmol) and Intermediate 663B (0.010, 0.032 mmol) were dissolved in DMF (1 ml). $PdCl_2$(dppf)-$CH_2Cl_2$ adduct (1.561 mg, 1.912 µmol) was added and the reaction degassed by bubbling with argon for 15 minutes. $Na_2CO_3$, 3 M aqueous solution (0.100 ml, 0.300 mmol) was added and the reaction degassed for 5 minutes, then sealed and heated to 90° C. in the microwave for 30 minutes. The reaction mixture was concentrated and suspended in 2 mL of hot DMSO, filtered, and purified by preparative HPLC (Method D, 30% to 70% B in 25 minutes) to yield Example 663 (0.0044 g, 9.45 µmol, 29.7% yield): $^1$H NMR (500 MHz, DMSO-$d_6$) δ 8.73 (br. s., 1H), 8.54 (br. s., 1H), 7.82 (br. s., 1H), 7.59 (br. s., 1H), 7.16 (br. s., 1H), 5.48-5.31 (m, 2H), 4.08 (br. s., 3H), 3.88-3.86 (m, 3H), 3.78 (d, J=9.8 Hz, 1H), 3.27-3.16 (m, 2H), 2.64 (br. s., 3H), 2.00 (br. s., 1H), 1.71 (d, J=11.8 Hz, 1H), 1.45 (t, J=12.6 Hz, 3H), 1.19 (d, J=12.5 Hz, 2H). LC-MS: method H, RT=1.45 min, MS (ESI) m/z: 452.2 (M+H)$^+$. Analytical HPLC Method B: 97% purity.

Example 664

(6-methoxy-2-(2-methoxy-7-methylquinoxalin-5-yl)benzo[d]thiazol-4-yl)(tetrahydro-2H-pyran-4-yl)methanol

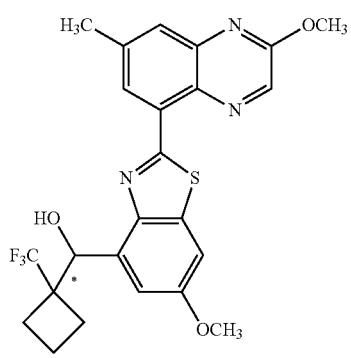

(664)

Intermediate 664A: (2-amino-6-methoxybenzo[d]thiazol-4-yl)(1-(trifluoromethyl)cyclobutyl)methanone

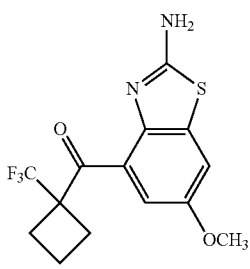

(664A)

Intermediate I-22 (50 mg, 0.193 mmol) was dissolved in THF (1930 µl). NaH (8.49 mg, 0.212 mmol) was added and the reaction mixture was stirred for 30 min. The reaction mixture was cooled to −78° C. and BuLi (101 µl, 0.232 mmol) was added and the reaction mixture was allowed to stir for 30 min. Methyl 1-(trifluoromethyl) cyclobutanecarboxylate (35.1 mg, 0.193 mmol) was added and the reaction mixture was allowed to warm to ambient temperature. The reaction mixture was stirred for 10 min and diluted with water and EtOAc. The layers were separated and the aqueous layer was back extracted with EtOAc. The combined organic layer was washed with water, dried with sodium sulfate, and concentrated under reduced pressure to yield Intermediate 664A (0.023 g, 0.191 mmol, 33%). LC-MS: method H, RT=0.77 min, MS (ESI) m/z: 331.2 (M+H)⁺.

Intermediate 664B: (2-chloro-6-methoxybenzo[d]thiazol-4-yl)(1-(trifluoromethyl) cyclobutyl)methanone

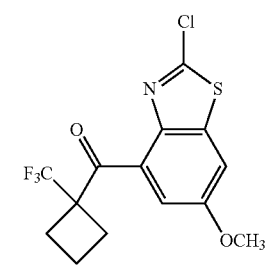

(664B)

Copper(II) chloride (0.042 g, 0.309 mmol) and t-butyl nitrite (0.037 ml, 0.309 mmol) were dissolved in MeCN (0.727 ml) and allowed to stir 10 minutes. Intermediate 664A (0.060 g, 0.182 mmol) was dissolved in MeCN (1.090 ml) and the copper solution was added. The reaction mixture was stirred for 2.5 h at 60° C. The reaction mixture was diluted with EtOAc, washed with 1 N HCl, saturated NaHCO₃, then brine, dried (Na₂SO₄), filtered, and concentrated in vacuo. Purified on ISCO using a 12 g column with 0-100% gradient of EtOAc in hexanes to yield Intermediate 664B (0.025 g, 0.036 mmol, 19.68% yield). LC-MS: method H, RT=1.12 min, MS (ESI) m/z: 350.1 (M+H)⁺.

Intermediate 664C: (2-chloro-6-methoxybenzo[d]thiazol-4-yl)(1-(trifluoromethyl) cyclobutyl)methanol (664C)

Intermediate 664B (0.035 g, 0.100 mmol) was dissolved in MeOH (1.00 ml) and cooled to 0° C. Sodium borohydride (3.79 mg, 0.100 mmol) was added to the flask, and the reaction mixture was allowed to stir for 2 h. The reaction mixture was diluted with water and EtOAc. The layers were separated, and the aqueous layer was back extracted with EtOAc×3. The combined organic layer was washed with water, dried with sodium sulfate, and concentrated under reduced pressure to yield Intermediate 664C (0.030 g, 0.085 mmol, 85% yield) as a white solid. Used without further purification. LC-MS: method H, RT=1.12 min, MS (ESI) m/z: 352.1 (M+H)⁺.

Example 664

Intermediate I-9 (0.065 g, 0.216 mmol) and Intermediate 664B (0.076 g, 0.216 mmol) were dissolved in DMF (2.160 ml). PdCl₂(dppf)-CH₂Cl₂ adduct (10.59 mg, 0.013 mmol)

was added and the reaction degassed by bubbling with argon for 15 minutes. Na₂CO₃, 3 M aqueous solution (0.100 ml, 0.300 mmol) was added and the reaction degassed for 5 minutes, then sealed and heated to 90° C. in the microwave for 30 minutes. Enantiomers were separated using Lux 5u Cellulose-4, 21×250 mm, 5 micron column with 35% EtOH/ 65% CO₂, UV 220 nm to afford Example 664 (10.7 mg, 0.021 mmol, 9.61% yield) as a single enantiomer (99% enantiomeric excess). ¹H NMR (400 MHz, CDCl₃) δ 8.56 (s, 1H), 8.48 (d, J=2.0 Hz, 1H), 7.77 (s, 1H), 7.37 (d, J=2.4 Hz, 1H), 7.03 (d, J=2.2 Hz, 1H), 5.81 (d, J=9.2 Hz, 1H), 5.34 (d, J=9.2 Hz, 1H), 4.13 (s, 3H), 3.92 (s, 3H), 2.73 (s, 2H), 2.65 (s, 3H), 2.35 (s, 4H), 1.88 (s, 1H). LC-MS: method H, RT=1.34 min, MS (ESI) m/z: 490.1 (M+H)⁺. Analytical HPLC Method B: 97% purity Examples 665 to 677

The following additional examples have been prepared, isolated and characterized using the methods described for Example 663 or Example 664 and the examples above.

| Ex. No. | Structure | LCMS [M + H]⁺ m/z | LCMS RT(Min)/ Method | NMR |
|---|---|---|---|---|
| 665 | 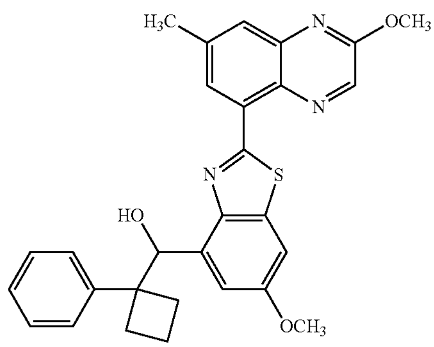 [SMILES: COc1cc(C(O)C2(c3ccccc3)CCC2)c2nc(-c3cc(C)cc4nc(OC)cnc34)sc2c1] | 498.2 | 1.37/H | ¹H NMR (500 MHz, DMSO-d₆) δ 8.67 (s, 1H), 8.41 (s, 1H), 7.78 (s, 1H), 7.46 (s, 1H), 7.11-7.07 (m, 2H), 6.99-6.94 (m, 1H), 6.90 (d, J = 7.3 Hz, 2H), 6.48 (s, 1H), 5.94 (d, J = 4.9 Hz, 1H), 5.59 (d, J = 4.9 Hz, 1H), 4.06 (s, 3H), 3.66 (s, 3H), 2.75 (d, J = 7.3 Hz, 1H), 2.65 (s, 4H), 2.25 (d, J = 9.2 Hz, 1H), 2.18-2.03 (m, 2H), 1.75 (br. s., 1H). |
| 666 | 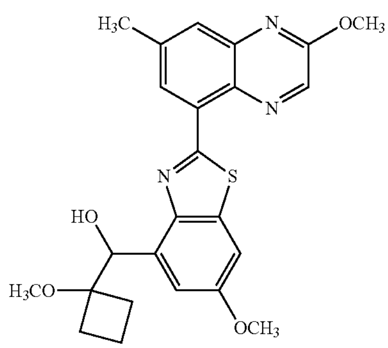 [SMILES: COc1cc(C(O)C2(OC)CCC2)c2nc(-c3cc(C)cc4nc(OC)cnc34)sc2c1] | 466.2 | 1.35/H | ¹H NMR (500 MHz, DMSO-d₆) δ 8.72 (br. s., 1H), 8.56 (br. s., 1H), 7.81 (br. s., 1H), 7.59 (br. s., 1H), 7.15 (br. s., 1H), 5.67 (br. s., 1H), 5.36 (br. s., 1H), 4.07 (br. s., 3H), 3.86 (br. s., 3H), 3.43-3.38 (m, 2H), 3.17 (br. s., 3H), 2.63 (br. s., 3H), 2.35 (br. s., 1H), 2.23-2.13 (m, 1H), 1.74 (br. s., 4H). |
| 667 | 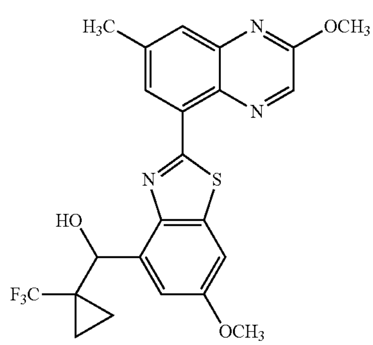 [SMILES: COc1cc(C(O)C2(C(F)(F)F)CC2)c2nc(-c3cc(C)cc4nc(OC)cnc34)sc2c1] | 476.1 | 1.29/H | ¹H NMR (500 MHz, DMSO-d₆) δ 8.70 (s, 1H), 8.53 (s, 1H), 7.79 (s, 1H), 7.62 (s, 1H), 7.19 (s, 1H), 5.93-5.90 (m, 1H), 5.89-5.86 (m, 1H), 4.06 (s, 3H), 3.86 (s, 3H), 2.60 (s, 3H), 1.22 (br. s., 1H), 0.92 (br. s., 2H), 0.49 (d, J = 9.5 Hz, 1H). |

-continued

| Ex. No. | Structure | LCMS [M + H]+ m/z | LCMS RT(Min)/ Method | NMR |
|---|---|---|---|---|
| 668 | 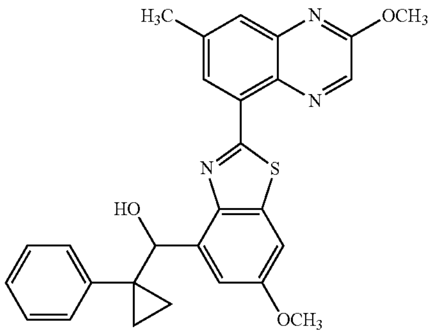 [SMILES: COc1cc(C(O)C2(c3ccccc3)CC2)c2nc(-c3cc(C)cc4nc(OC)cnc34)sc2c1] | 484.2 | 1.27/H | ¹H NMR (500 MHz, DMSO-d₆) δ 8.68 (s, 1H), 8.46 (s, 1H), 7.78 (s, 1H), 7.48 (d, J = 1.7 Hz, 1H), 7.20-7.00 (m, 5H), 6.73 (s, 1H), 5.58 (d, J = 4.4 Hz, 1H), 5.51 (d, J = 4.0 Hz, 1H), 4.06 (s, 3H), 3.71 (s, 3H), 2.65 (s, 3H), 1.37 (d, J = 4.4 Hz, 1H), 1.00 (d, J = 4.0 Hz, 1H), 0.78-0.65 (m, 2H). |
| 669 | 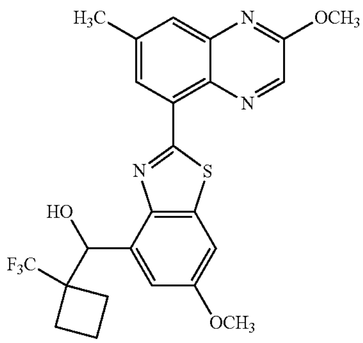 [SMILES: COc1cc(C(O)C2(C(F)(F)F)CCC2)c2nc(-c3cc(C)cc4nc(OC)cnc34)sc2c1] | 490.1 | 1.34/H | ¹H NMR (500 MHz, DMSO-d₆) δ 8.67 (s, 1H), 8.45 (s, 1H), 7.78 (s, 1H), 7.63 (d, J = 2.1 Hz, 1H), 7.29 (d, J = 2.1 Hz, 1H), 5.98 (d, J = 5.2 Hz, 1H), 5.92 (d, J = 5.2 Hz, 1H), 4.05 (s, 3H), 3.86 (s, 3H), 2.58 (s, 3H), 2.21-2.01 (m, 2H), 1.80 (d, J = 10.4 Hz, 1H), 1.67-1.53 (m, 1H), 1.20 (br. s., 1H), 0.80 (br. s., 1H). |
| 671 | 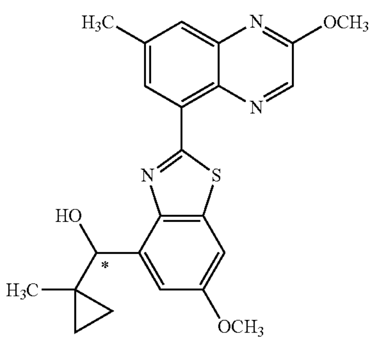 [SMILES: COc1cc(C(O)C2(C)CC2)c2nc(-c3cc(C)cc4nc(OC)cnc34)sc2c1] | 476.1 | 1.29/H | ¹H NMR (400 MHz, CDCl₃) δ 8.55 (s, 1H), 8.49 (s, 1H), 7.77 (s, 1H), 7.34 (d, J = 2.4 Hz, 1H), 7.01 (d, J = 2.4 Hz, 1H), 5.72-5.64 (m, 1H), 5.53 (s, 1H), 4.13 (s, 3H), 3.92 (s, 3H), 2.66 (s, 3H), 1.17 (br. s., 1H), 1.02 (dt, J = 18.2, 5.7 Hz, 2H), 0.58 (d, J = 8.8 Hz, 1H) |
| 672 | 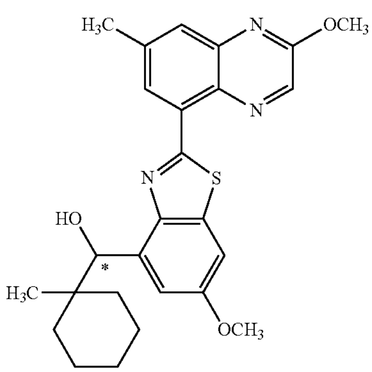 [SMILES: COc1cc(C(O)C2(C)CCCCC2)c2nc(-c3cc(C)cc4nc(OC)cnc34)sc2c1] | 464.2 | 1.43 | ¹H NMR (400 MHz, CDCl₃) δ 8.55 (s, 1H), 8.47 (d, J = 1.5 Hz, 1H), 7.75 (dd, J = 1.8, 0.9 Hz, 1H), 7.31 (d, J = 2.4 Hz, 1H), 6.91 (d, J = 2.4 Hz, 1H), 5.84 (d, J = 9.7 Hz, 1H), 4.79 (d, J = 9.5 Hz, 1H), 4.13 (s, 3H), 3.91 (s, 3H), 2.66 (s, 3H), 1.61 (br. s., 10H), 0.96 (s, 3H). |

| Ex. No. | Structure | LCMS [M + H]+ m/z | LCMS RT(Min)/ Method | NMR |
|---|---|---|---|---|
| 673 | 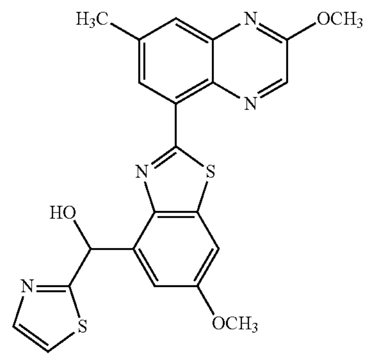 [SMILES: COc1cc(C(O)c2nccs2)c2nc(-c3cc(C)cc4nc(OC)cnc34)sc2c1] | 451.0 | 1.15/H | ¹H NMR (500 MHz, DMSO-d₆) δ 8.68 (s, 1H), 8.50 (s, 1H), 7.78 (s, 1H), 7.70-7.60 (m, 3H), 7.13 (s, 1H), 6.96 (br. s., 1H), 6.91 (br. s., 1H), 4.06 (s, 3H), 3.84 (s, 3H), 2.61 (s, 3H). |
| 674 | 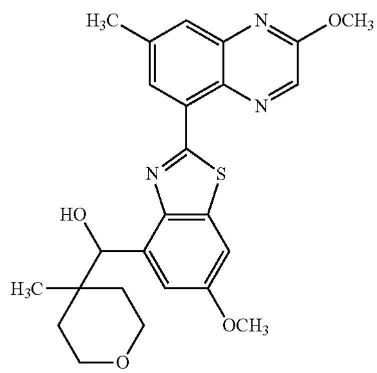 [SMILES: COc1cc(C(O)C2(C)CCOCC2)c2nc(-c3cc(C)cc4nc(OC)cnc34)sc2c1] | 466.2 | 1.23/H | ¹H NMR (500 MHz, DMSO-d₆) δ 8.67 (s, 1H), 8.49 (s, 1H), 7.78 (s, 1H), 7.58 (s, 1H), 7.13 (s, 1H), 5.58-5.42 (m, 2H), 4.05 (s, 3H), 3.85 (s, 3H), 3.77-3.59 (m, 3H), 3.42 (br. s., 1H), 2.61 (s, 3H), 1.93-1.73 (m, 2H), 1.44 (br. s., 1H), 0.98 (s, 3H), 0.89-0.82 (m, 1H). |
| 675 | 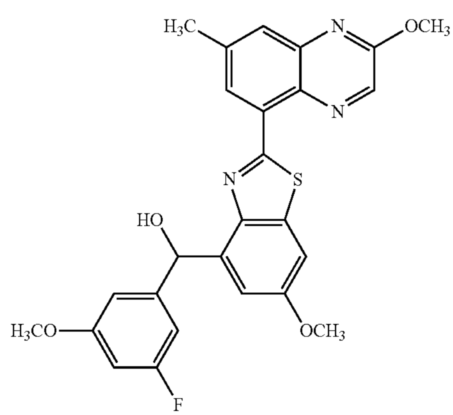 [SMILES: COc1cc(F)cc(C(O)c2cc(OC)cc3sc(-c4cc(C)cc5nc(OC)cnc45)nc23)c1] | 492.1 | 1.29/H | ¹H NMR (500 MHz, DMSO-d₆) δ 8.73 (s, 1H), 8.66 (s, 1H), 7.84 (s, 1H), 7.61 (d, J = 2.1 Hz, 1H), 7.32 (s, 1H), 7.14 (s, 1H), 7.01 (d, J = 9.8 Hz, 1H), 6.72-6.64 (m, 2H), 6.32 (d, J = 4.3 Hz, 1H), 4.12 (s, 3H), 3.91 (s, 3H), 3.78 (s, 3H), 2.68 (s, 3H). |
| 676 | 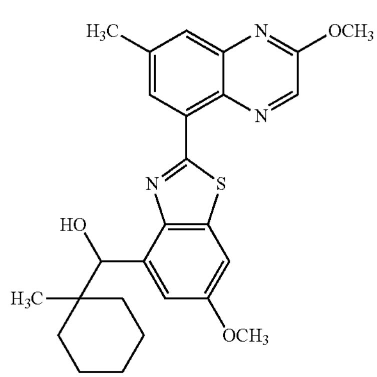 [SMILES: COc1cc(C(O)C2(C)CCCCC2)c2nc(-c3cc(C)cc4nc(OC)cnc34)sc2c1] | 464.2 | 1.39/H | ¹H NMR (500 MHz, DMSO-d₆) δ 8.71 (s, 1H), 8.52 (s, 1H), 7.80 (s, 1H), 7.58 (br. s., 1H), 7.14 (br. s., 1H), 5.46 (br. s., 1H), 5.32 (d, J = 4.0 Hz, 1H), 4.08 (s, 3H), 3.87 (s, 3H), 3.48 (br. s., 3H), 2.63 (s, 3H), 1.69-1.49 (m, 6H), 1.43-1.29 (m, 2H), 1.24-1.13 (m, 1H), 1.05 (d, J = 12.5 Hz, 1H). |

-continued

| Ex. No. | Structure | LCMS [M + H]+ m/z | LCMS RT(Min)/ Method | NMR |
|---|---|---|---|---|
| 677 | 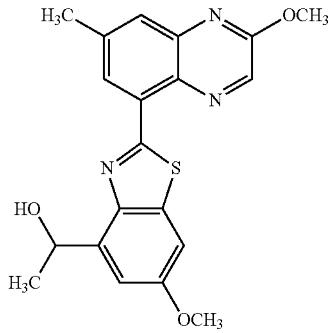 [SMILES: COc1cc(C(C)O)c2nc(-c3cc(C)cc4nc(OC)cnc34)sc2c1] | 382.1 | 1.19/H | $^1$H NMR (500 MHz, DMSO-d$_6$) δ 8.71 (s, 1H), 8.55 (s, 1H), 7.80 (s, 1H), 7.57 (d, J = 2.4 Hz, 1H), 7.23 (d, J = 2.1 Hz, 1H), 5.72-5.59 (m, 1H), 4.08 (s, 3H), 3.88 (s, 3H), 3.39 (br. s., 1H), 2.64 (s, 3H), 2.56 (s, 3H). |

Example 678

(R)-1-((6-fluoro-2-(2-methoxy-7-methylquinoxalin-5-yl)thiazolo[5,4-b]pyridin-5-yl)oxy)propan-2-yl (2-methylpyrimidin-5-yl)carbamate

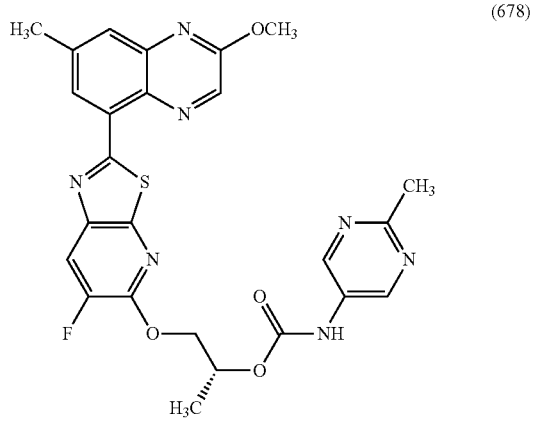

(678)

To a solution of Intermediate I-132 (17 mg, 0.037 mmol) in DCM (1 mL) and THF (0.5 mL) was added 2-methylpyrimidin-5-amine (8.02 mg, 0.073 mmol) followed by pyridine (0.030 mL, 0.367 mmol). The mixture was stirred at room temperature for 1 hour. The reaction was quenched with 0.2 mL of MeOH. The reaction mixture was concentrated and redissolved in DMF, filtered, and purified by preparative HPLC (Method D, 25 to 100% B in 20 minutes) to yield Example 678 (5.9 mg, 10.58 µmol, 28.8% yield): $^1$H NMR (500 MHz, DMSO-d$_6$) δ 9.97 (br. s., 1H), 8.71 (br. s., 2H), 8.63-8.59 (m, 1H), 8.44 (s, 1H), 8.37 (d, J=10.7 Hz, 1H), 7.77 (s, 1H), 5.26 (br. s., 1H), 4.79 (d, J=10.7 Hz, 1H), 4.57-4.44 (m, 1H), 4.05 (s, 3H), 3.44 (br. s., 3H), 2.58 (s, 3H), 1.40 (d, J=6.4 Hz, 3H). LC-MS: method H, RT=1.45 min, MS (ESI) m/z: 536.2 (M+H)$^+$. Analytical HPLC Method B: 96% purity.

Examples 679 to 702

The following additional examples have been prepared, isolated and characterized using the methods described for Example 678 and the examples above. If necessary, removal of silyl protecting groups was accomplished by treatment of the protected compound with a solution of 90% MeOH, 9.9% water, and 0.1% TFA or MeOH/HCl (20/1) solution to afford the desired compound.

| Ex. No. | Structure | Amine | LCMS [M + H]+ m/z | LCMS RT (Min) Method H | NMR |
|---|---|---|---|---|---|
| 679 | 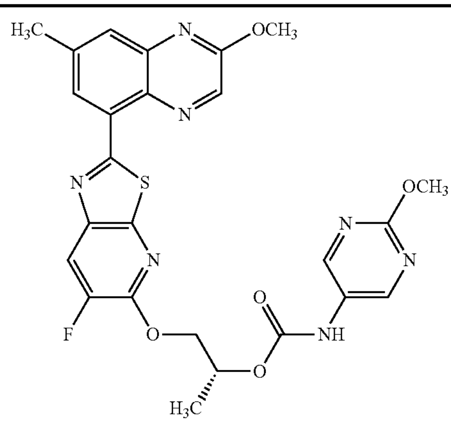 | | 552.1 | 1.27 | $^1$H NMR (500 MHz, DMSO-d$_6$) δ 9.82 (br. s., 1H), 8.62-8.54 (m, 2H), 8.40 (br. s., 1H), 8.34 (d, J = 10.7 Hz, 1H), 7.73 (s, 1H), 5.24 (br. s., 1H), 4.79 (d, J = 11.3 Hz, 1H), 4.48 (t, J = 11.6 Hz, 1H), 4.04 (s, 3H), 3.45 (br. s., 1H), 2.57 (s, 3H), 2.54 (s, 3H), 1.46-1.37 (m, 3H). |

| Ex. No. | Structure | Amine | LCMS [M + H]+ m/z | LCMS RT (Min) Method H | NMR |
|---|---|---|---|---|---|
| 680 | 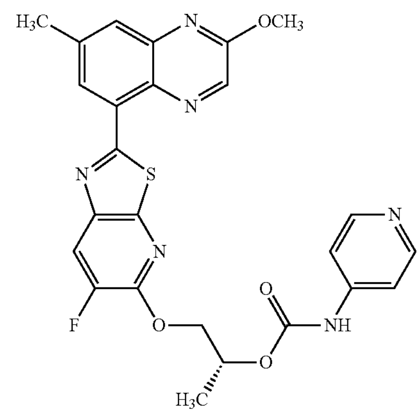 [SMILES: COc1cnc2c(-c3nc4cc(F)c(OC[C@@H](C)OC(=O)Nc5ccncc5)nc4s3)cc(C)cc2n1] | | 521.1 | 1.07 | ¹H NMR (500 MHz, DMSO-d₆) δ 8.60-8.56 (m, 1H), 8.42 (s, 1H), 8.35 (d, J = 9.5 Hz, 3H), 7.75 (s, 1H), 7.43 (d, J = 5.2 Hz, 2H), 5.28 (br. s., 1H), 4.78 (d, J = 10.1 Hz, 1H), 4.56-4.47 (m, 1H), 4.04 (s, 3H), 2.57 (s, 3H), 1.54-1.31 (m, 3H). |
| 681 | 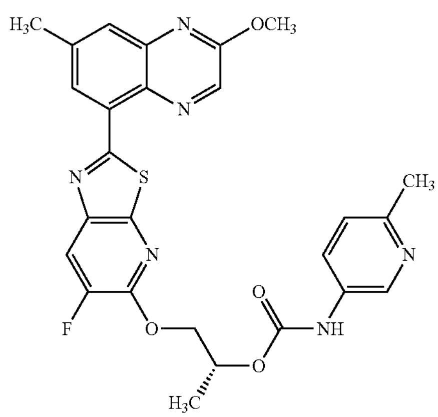 | | 535.1 | 1.06 | ¹H NMR (500 MHz, DMSO-d₆) δ 9.80 (br. s., 1H), 8.62 (s, 1H), 8.45 (br. s., 2H), 8.37 (d, J = 10.7 Hz, 1H), 7.77 (s, 2H), 7.16 (d, J = 7.9 Hz, 1H), 5.26 (br. s., 1H), 4.75 (d, J = 9.5 Hz, 1H), 4.50 (dd, J = 11.7, 6.0 Hz, 1H), 4.05 (s, 3H), 2.59 (s, 3H), 2.35 (s, 3H), 1.39 (d, J = 6.4 Hz, 3H). |
| 682 | 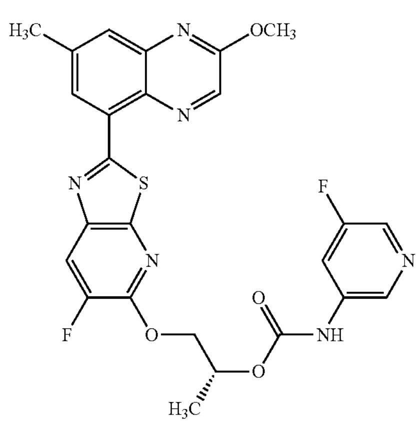 [SMILES: COc1cnc2c(-c3nc4cc(F)c(OC[C@@H](C)OC(=O)Nc5cncc(F)c5)nc4s3)cc(C)cc2n1] | | 539.1 | 1.27 | ¹H NMR (500 MHz, DMSO-d₆) δ 10.21 (br. s., 1H), 8.60 (s, 1H), 8.46-8.34 (m, 3H), 8.17 (s, 1H), 7.94 (s, 1H), 7.76 (s, 1H), 5.28 (br. s., 1H), 4.78 (d, J = 10.4 Hz, 1H), 4.51 (dd, J = 11.7, 5.6 Hz, 1H), 4.05 (s, 3H), 3.42 (br. s., 3H), 2.58 (s, 3H), 1.41 (d, J = 6.4 Hz, 3H). |

-continued

| Ex. No. | Structure | Amine | LCMS [M + H]+ m/z | LCMS RT (Min) Method H | NMR |
|---|---|---|---|---|---|
| 683 | 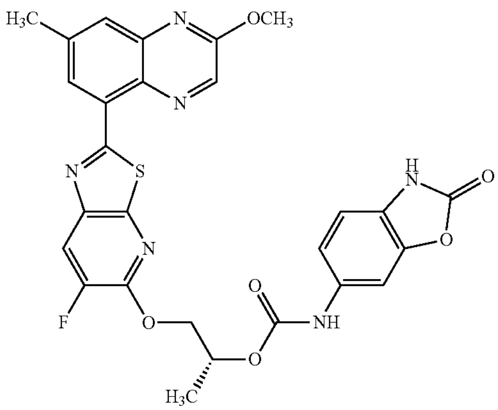 [SMILES: COc1cnc2c(-c3nc4cc(F)c(OC[C@@H](C)OC(=O)Nc5ccc6[nH]c(=O)oc6c5)nc4s3)cc(C)cc2n1] | | 577.1 | 1.23 | ¹H NMR (500 MHz, DMSO-d₆) δ 8.67 (s, 1H), 8.51 (d, J = 1.7 Hz, 1H), 8.43 (d, J = 10.7 Hz, 1H), 7.82 (s, 1H), 7.39-7.33 (m, 1H), 7.09-7.04 (m, 1H), 6.88 (d, J = 8.5 Hz, 1H), 5.26 (td, J = 6.3, 3.0 Hz, 1H), 4.74 (dd, J = 11.7, 2.9 Hz, 1H), 4.54 (dd, J = 11.7, 6.2 Hz, 1H), 4.08 (s, 3H), 2.62 (s, 3H), 1.40 (d, J = 6.6 Hz, 3H). |
| 684 | 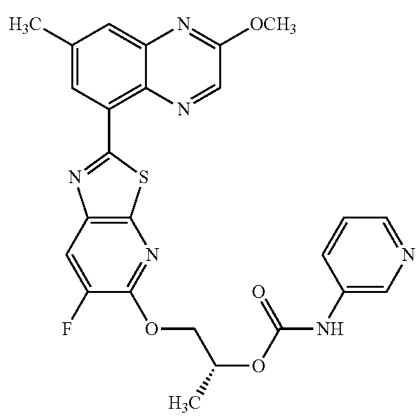 [SMILES: COc1cnc2c(-c3nc4cc(F)c(OC[C@@H](C)OC(=O)Nc5cccnc5)nc4s3)cc(C)cc2n1] | | 521.2 | 1.07 | ¹H NMR (500 MHz, DMSO-d₆) δ 8.61 (s, 2H), 8.44 (s, 1H), 8.37 (d, J = 10.7 Hz, 1H), 8.19 (br. s., 1H), 7.89 (br. s., 1H), 7.76 (s, 1H), 7.32 (br. s., 1H), 5.28 (br. s., 1H), 4.75 (d, J = 9.8 Hz, 1H), 4.52 (dd, J = 11.4, 6.0 Hz, 1H), 4.05 (s, 3H), 2.58 (s, 3H), 1.41 (d, J = 6.4 Hz, 3H). |
| 685 | 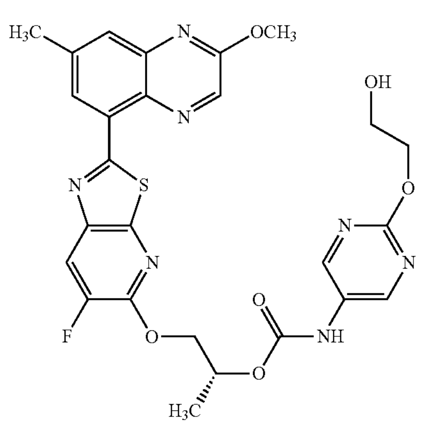 [SMILES: COc1cnc2c(-c3nc4cc(F)c(OC[C@@H](C)OC(=O)Nc5cnc(OCCO)nc5)nc4s3)cc(C)cc2n1] | I-97 | 582.2 | 1.15 | ¹H NMR (400 MHz, CDCl₃) δ 8.73-8.51 (m, 4H), 8.01 (d, J = 9.7 Hz, 1H), 7.79 (br. s., 1H), 6.64 (br. s., 1H), 5.80 (br. s., 1H), 5.41 (br. s., 1H), 4.83 (br. s., 1H), 4.50 (br. s., 2H), 4.15 (s, 3H), 4.00 (br. s., 2H), 2.67 (s, 3H), 1.52 (t, J = 6.1 Hz, 3H). |

-continued
| Ex. No. | Structure | Amine | LCMS [M + H]⁺ m/z | LCMS RT (Min) Method H | NMR |
|---|---|---|---|---|---|
| 686 | 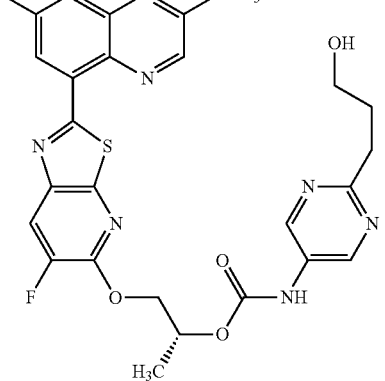 | I-98 | 566.2 | 1.13 | ¹H NMR (500 MHz, DMSO-d₆) δ 9.96 (br. s., 1H), 8.76-8.65 (m, 3H), 8.51 (s, 2H), 8.42 (d, J = 10.7 Hz, 2H), 7.83 (s, 2H), 5.75-5.64 (m, 1H), 5.27 (br. s., 1H), 4.81 (d, J = 11.6 Hz, 1H), 4.58-4.46 (m, 1H), 4.07 (s, 3H), 3.77 (br. s., 2H), 2.91 (d, J = 6.7 Hz, 2H), 2.61 (s, 3H), 1.40 (d, J = 6.4 Hz, 3H). |
| 687 | 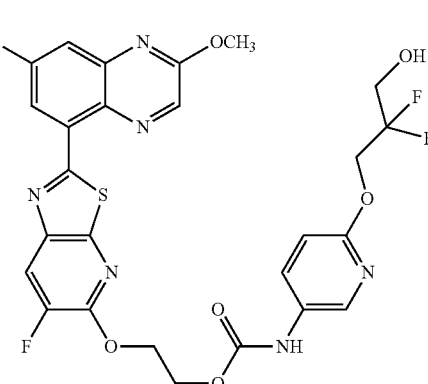 | I-99 | 631.2 | 1.27 | ¹H NMR (500 MHz, DMSO-d₆) δ 9.69 (br. s., 1H), 8.58 (s, 1H), 8.42 (s, 1H), 8.33 (d, J = 10.7 Hz, 1H), 8.20 (br. s., 1H), 7.85-7.78 (m, 1H), 7.74 (s, 1H), 6.87 (d, J = 8.5 Hz, 1H), 5.72-5.59 (m, 1H), 5.26 (br. s., 1H), 4.75 (d, J = 9.8 Hz, 1H), 4.56-4.43 (m, 3H), 4.05 (s, 3H), 3.82-3.65 (m, 2H), 2.58 (s, 3H), 1.41 (d, J = 6.4 Hz, 3H). |
| 688 | 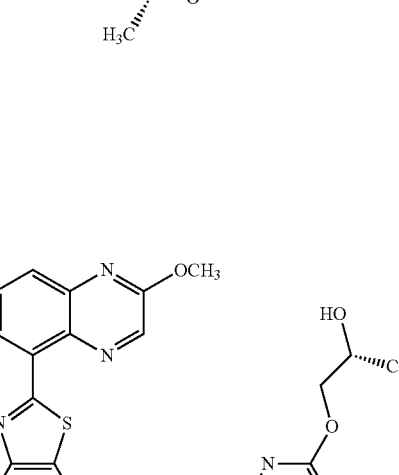 | I-103 | 596.1 | 1.26 | ¹H NMR (500 MHz, DMSO-d₆) δ 9.87-9.76 (m, 1H), 8.65 (s, 1H), 8.60 (br. s., 2H), 8.48 (s, 1H), 8.41 (d, J = 10.7 Hz, 1H), 7.80 (s, 1H), 5.69 (d, J = 6.4 Hz, 1H), 5.31-5.23 (m, 1H), 4.86-4.76 (m, 1H), 4.53 (dd, J = 11.6, 6.1 Hz, 1H), 4.07 (s, 3H), 4.05-3.99 (m, 1H), 3.93 (br. s., 1H), 3.54 (d, J = 4.9 Hz, 1H), 2.61 (s, 3H), 1.41 (d, J = 6.4 Hz, 3H), 1.12 (d, J = 6.1 Hz, 3H). |

| Ex. No. | Structure | Amine | LCMS [M + H]+ m/z | LCMS RT (Min) Method H | NMR |
|---|---|---|---|---|---|
| 689 | 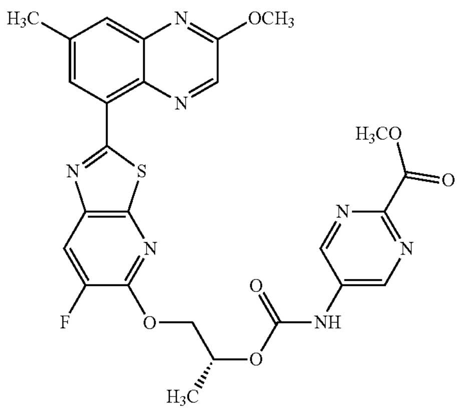 [SMILES: COC(=O)c1ncc(NC(=O)O[C@H](C)COc2nc3sc(-c4cc(C)cc5nc(OC)cnc45)nc3cc2F)cn1] | I-107 | 580.2 | 1.20 | ¹H NMR (500 MHz, DMSO-d₆) δ 9.39 (br. s., 1H), 8.23 (br. s., 1H), 7.97-7.84 (m, 3H), 7.63 (d, J = 7.6 Hz, 2H), 7.34-7.05 (m, 2H), 6.57 (d, J = 9.5 Hz, 1H), 5.75 (d, J = 6.1 Hz, 1H), 2.54 (s, 3H), 2.50 (br. s., 3H), 2.13 (br. s., 3H), 1.54 (d, J = 4.9 Hz, 3H). |
| 690 | 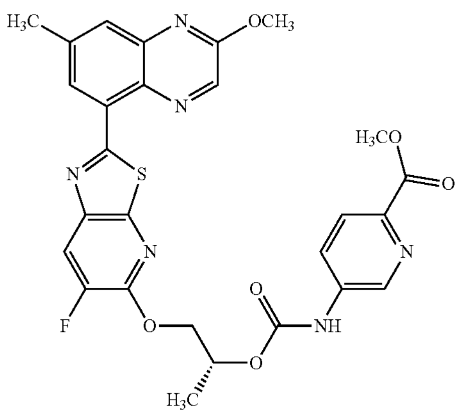 [SMILES: COC(=O)c1ccc(NC(=O)O[C@H](C)COc2nc3sc(-c4cc(C)cc5nc(OC)cnc45)nc3cc2F)cn1] | | 579.2 | 1.23 | ¹H NMR (500 MHz, DMSO-d₆) δ 8.65 (br. s., 2H), 8.54 (s, 1H), 8.46 (d, J = 10.7 Hz, 1H), 8.05 (br. s., 1H), 8.00 (s, 1H), 7.86 (s, 1H), 5.29 (br. s., 1H), 4.96 (d, J = 11.9 Hz, 1H), 4.53 (dd, J = 11.6, 5.2 Hz, 1H), 4.09 (s, 3H), 2.64 (s, 3H), 1.44 (d, J = 6.4 Hz, 3H). |
| 691 | 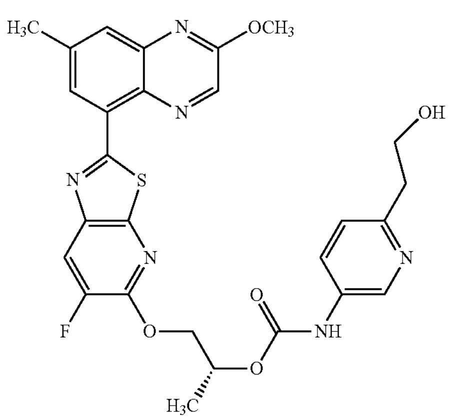 [SMILES: COc1cnc2c(-c3nc4cc(F)c(OC[C@@H](C)OC(=O)Nc5ccc(CCO)nc5)nc4s3)cc(C)cc2n1] | I-109 | 565.1 | 1.00 | ¹H NMR (500 MHz, DMSO-d₆) δ 9.78 (br. s., 1H), 8.65 (s, 1H), 8.57-8.47 (m, 2H), 8.39 (d, J = 10.7 Hz, 1H), 7.90-7.68 (m, 2H), 7.18 (d, J = 8.5 Hz, 1H), 5.66 (br. s., 1H), 5.28 (dt, J = 6.3, 3.3 Hz, 1H), 4.76 (dd, J = 11.7, 2.9 Hz, 1H), 4.53 (dd, J = 11.7, 6.3 Hz, 1H), 4.07 (s, 3H), 3.68 (d, J = 5.2 Hz, 2H), 2.79 (t, J = 6.7 Hz, 2H), 2.61 (s, 3H), 1.42 (d, J = 6.7 Hz, 3H). |

| Ex. No. | Structure | Amine | LCMS [M + H]+ m/z | LCMS RT (Min) Method H | NMR |
|---|---|---|---|---|---|
| 692 | 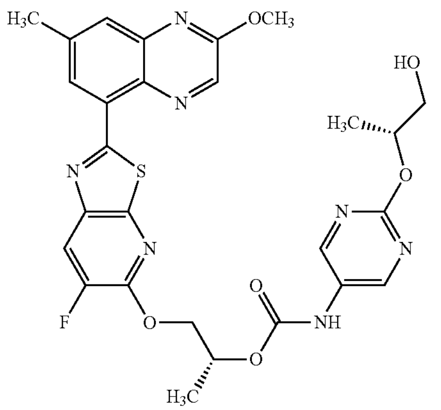 [SMILES: COc1cnc2c(-c3nc4cc(F)c(OC[C@@H](C)OC(=O)Nc5cnc(O[C@H](C)CO)nc5)nc4s3)cc(C)cc2n1] | I-106 | 596.1 | 1.20 | ¹H NMR (500 MHz, DMSO-d₆) δ 9.80 (br. s., 1H), 8.64-8.62 (m, 1H), 8.60 (br. s., 2H), 8.47 (s, 1H), 8.39 (d, J = 10.7 Hz, 1H), 7.79 (s, 1H), 5.68 (br. s., 1H), 5.31-5.23 (m, 1H), 5.01 (d, J = 5.2 Hz, 1H), 4.89-4.84 (m, 1H), 4.82-4.76 (m, 1H), 4.53 (dd, J = 11.7, 6.0 Hz, 2H), 4.07 (s, 3H), 2.60 (s, 3H), 1.48-1.39 (m, 3H), 1.25-1.18 (m, 3H). |
| 693 | 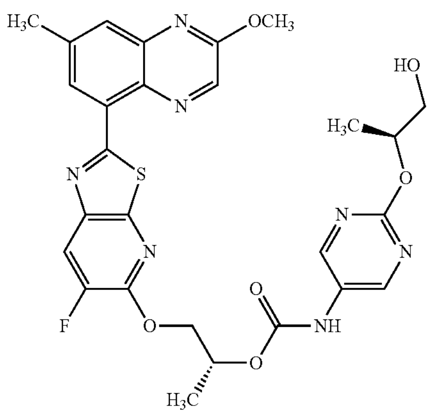 [SMILES: COc1cnc2c(-c3nc4cc(F)c(OC[C@@H](C)OC(=O)Nc5cnc(O[C@@H](C)CO)nc5)nc4s3)cc(C)cc2n1] | I-105 | 596.2 | 1.20 | ¹H NMR (500 MHz, DMSO-d₆) δ 9.80 (br. s., 1H), 8.67-8.54 (m, 2H), 8.45 (s, 2H), 8.37 (d, J = 10.7 Hz, 1H), 7.77 (s, 1H), 5.68 (br. s., 1H), 5.27 (br. s., 2H), 5.00 (d, J = 5.2 Hz, 2H), 4.91-4.85 (m, 1H), 4.80 (d, J = 9.5 Hz, 1H), 4.52 (dd, J = 11.6, 5.8 Hz, 2H), 4.07 (s, 3H), 2.60 (s, 3H), 1.42 (d, J = 6.4 Hz, 3H), 1.20 (d, J = 6.4 Hz, 3H). |
| 694 | 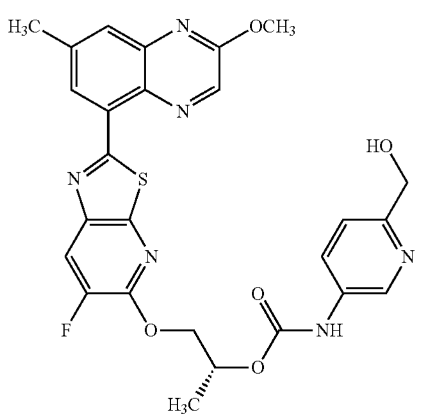 [SMILES: COc1cnc2c(-c3nc4cc(F)c(OC[C@@H](C)OC(=O)Nc5ccc(CO)nc5)nc4s3)cc(C)cc2n1] | 385B | 551.1 | 1.01 | ¹H NMR (500 MHz, DMSO-d₆) δ 9.87 (br. s., 1H), 8.65-8.60 (m, 1H), 8.55-8.49 (m, 1H), 8.46 (d, J = 1.5 Hz, 1H), 8.37 (d, J = 10.7 Hz, 1H), 7.89 (d, J = 8.2 Hz, 1H), 7.77 (s, 1H), 7.39 (d, J = 8.5 Hz, 1H), 5.67 (br. s., 1H), 5.29 (dt, J = 6.4, 3.2 Hz, 1H), 4.76 (dd, J = 11.6, 2.7 Hz, 1H), 4.54 (dd, J = 11.9, 6.1 Hz, 1H), 4.49 (s, 1H), 4.07 (s, 3H), 2.60 (s, 3H), 1.51-1.35 (m, 3H). |

| Ex. No. | Structure | Amine | LCMS [M + H]+ m/z | LCMS RT (Min) Method H | NMR |
|---|---|---|---|---|---|
| 695 | 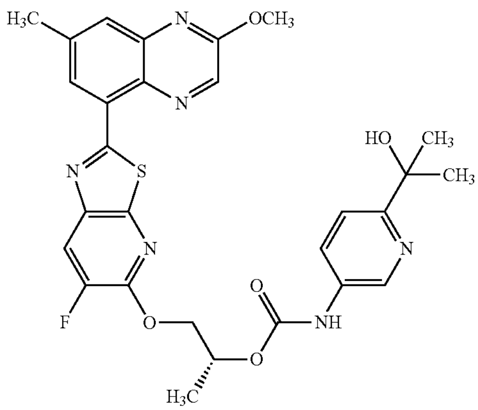 [SMILES: COc1cnc2c(-c3nc4cc(F)c(OC[C@@H](C)OC(=O)Nc5ccc(C(C)(C)O)nc5)nc4s3)cc(C)cc2n1] | I-92 | 593.2 | 1.03 | ¹H NMR (500 MHz, DMSO-d₆) δ 9.72 (br. s., 1H), 8.55 (s, 1H), 8.42 (br. s., 1H), 8.37 (s, 1H), 8.29 (d, J = 10.7 Hz, 1H), 7.69 (s, 2H), 7.12 (d, J = 8.5 Hz, 1H), 5.25-5.15 (m, 1H), 4.68 (dd, J = 11.6, 2.4 Hz, 1H), 4.59 (s, 1H), 4.46 (dd, J = 11.7, 6.3 Hz, 1H), 3.99 (s, 3H), 2.52 (s, 3H), 1.35 (d, J = 6.4 Hz, 3H), 0.97 (d, J = 2.4 Hz, 6H). |
| 696 | 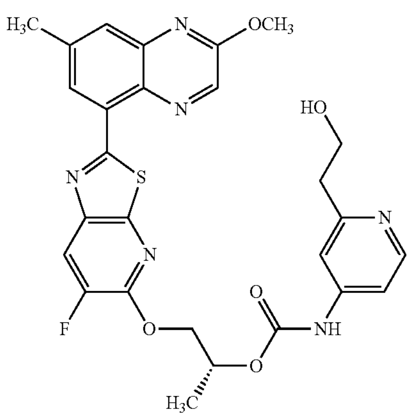 [SMILES: COc1cnc2c(-c3nc4cc(F)c(OC[C@@H](C)OC(=O)Nc5ccnc(CCO)c5)nc4s3)cc(C)cc2n1] | I-94 | 565.2 | 1.02 | ¹H NMR (500 MHz, DMSO-d₆) δ 8.63-8.58 (m, 1H), 8.45 (s, 1H), 8.39-8.34 (m, 1H), 8.28-8.22 (m, 1H), 7.77 (s, 1H), 7.32 (s, 1H), 7.28 (d, J = 3.7 Hz, 2H), 5.72-5.61 (m, 1H), 5.33-5.26 (m, 1H), 4.78 (d, J = 9.2 Hz, 1H), 4.53 (dd, J = 11.7, 6.3 Hz, 1H), 4.07 (s, 3H), 3.68 (br. s., 2H), 2.79-2.70 (m, 2H), 2.60 (s, 3H), 1.49-1.39 (m, 3H). |
| 697 | 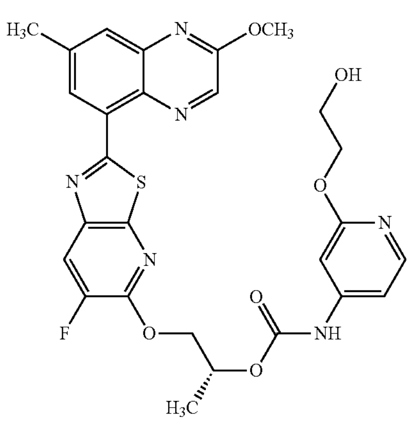 [SMILES: COc1cnc2c(-c3nc4cc(F)c(OC[C@@H](C)OC(=O)Nc5ccnc(OCCO)c5)nc4s3)cc(C)cc2n1] | I-110 | 581.1 | 1.03 | ¹H NMR (500 MHz, DMSO-d₆) δ 10.09 (br. s., 1H), 8.61 (s, 1H), 8.47 (s, 1H), 8.38 (d, J = 11.0 Hz, 1H), 7.93 (d, J = 5.8 Hz, 1H), 7.79 (s, 1H), 7.04 (d, J = 5.8 Hz, 1H), 6.88 (s, 1H), 5.29 (br. s., 1H), 4.80 (d, J = 11.9 Hz, 1H), 4.55-4.50 (m, 2H), 4.22-4.14 (m, 4H), 4.07 (s, 3H), 2.61 (s, 3H), 1.42 (d, J = 6.7 Hz, 3H). |

| Ex. No. | Structure | Amine | LCMS [M + H]+ m/z | LCMS RT (Min) Method H | NMR |
|---|---|---|---|---|---|
| 698 | 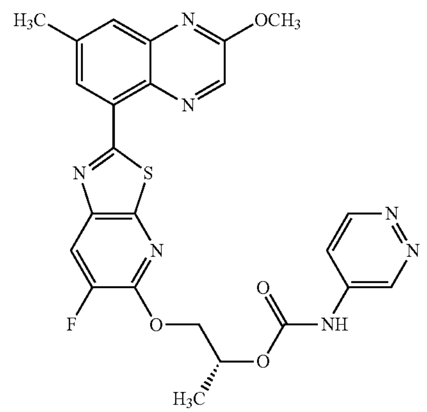 [SMILES: COc1cnc2c(-c3nc4cc(F)c(OC[C@@H](C)OC(=O)Nc5ccnnc5)nc4s3)cc(C)cc2n1] | | 522.1 | 1.03 | ¹H NMR (500 MHz, DMSO-d₆) δ 10.43 (br. s., 1H), 9.16-9.11 (m, 1H), 8.98 (d, J = 5.8 Hz, 1H), 8.68-8.63 (m, 1H), 8.52 (br. s., 1H), 8.47-8.39 (m, 1H), 7.85 (br. s., 1H), 7.76 (br. s., 1H), 5.37-5.24 (m, 1H), 4.98-4.88 (m, 1H), 4.54 (s, 1H), 4.39-4.28 (m, 1H), 4.09 (s, 3H), 2.63 (s, 3H), 1.53-1.41 (m, 3H). |
| 699 | 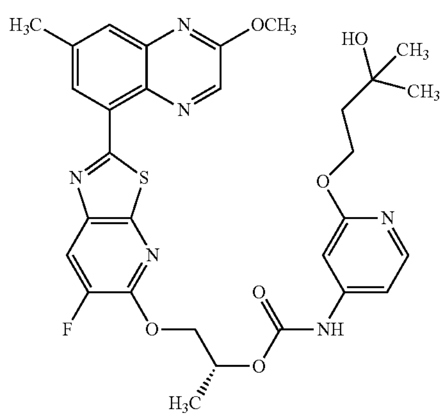 [SMILES: COc1cnc2c(-c3nc4cc(F)c(OC[C@@H](C)OC(=O)Nc5ccnc(OCCC(C)(C)O)c5)nc4s3)cc(C)cc2n1] | I-108 | 623.2 | 1.10 | ¹H NMR (500 MHz, DMSO-d₆) δ 10.07 (s, 1H), 8.57 (s, 1H), 8.43 (s, 1H), 8.34 (d, J = 10.7 Hz, 1H), 7.94 (d, J = 5.8 Hz, 1H), 7.75 (s, 1H), 7.01 (d, J = 5.8 Hz, 1H), 6.85 (s, 1H), 5.28 (br. s., 1H), 4.80 (d, J = 9.8 Hz, 1H), 4.50 (dd, J = 11.7, 5.6 Hz, 1H), 4.34-4.19 (m, 2H), 4.06 (s, 3H), 3.46 (br. s., 2H), 2.59 (s, 3H), 1.76 (t, J = 7.3 Hz, 2H), 1.42 (d, J = 6.4 Hz, 3H), 1.14-1.08 (m, 6H). |
| 700 | 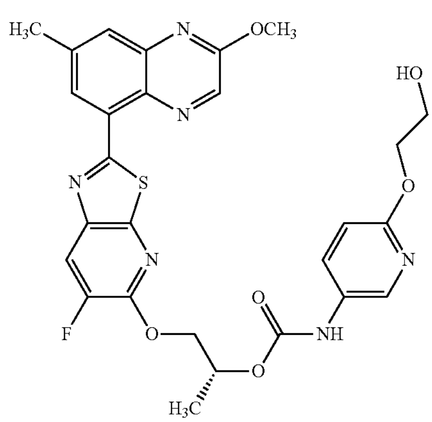 [SMILES: COc1cnc2c(-c3nc4cc(F)c(OC[C@@H](C)OC(=O)Nc5ccc(OCCO)nc5)nc4s3)cc(C)cc2n1] | I-93 | 581.1 | 1.18 | ¹H NMR (500 MHz, DMSO-d₆) δ 9.60 (br. s., 1H), 8.59 (s, 1H), 8.43 (br. s., 1H), 8.34 (d, J = 10.7 Hz, 1H), 8.16 (br. s., 1H), 7.75 (br. s., 2H), 6.75 (d, J = 8.9 Hz, 1H), 5.74-5.59 (m, 1H), 5.25 (br. s., 1H), 4.76 (d, J = 10.1 Hz, 1H), 4.57-4.44 (m, 1H), 4.16 (d, J = 4.3 Hz, 2H), 4.06 (s, 3H), 3.67 (br. s., 2H), 2.59 (s, 3H), 1.51-1.37 (m, 3H). |

| Ex. No. | Structure | Amine | LCMS [M + H]+ m/z | LCMS RT (Min) Method H | NMR |
|---|---|---|---|---|---|
| 701 | 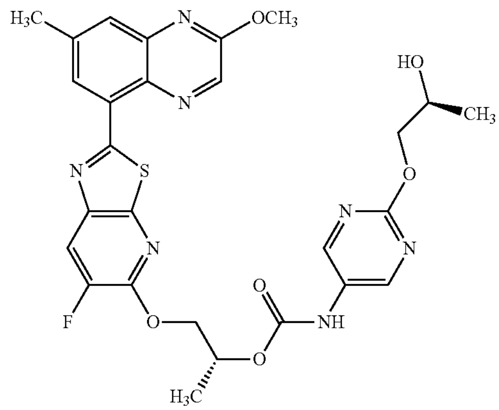 [SMILES: COc1cnc2c(-c3nc4cc(F)c(OC[C@@H](C)OC(=O)Nc5cnc(OC[C@H](C)O)nc5)nc4s3)cc(C)cc2n1] | I-104 | 596.1 | 1.26 | ¹H NMR (500 MHz, DMSO-d₆) δ 9.82 (br. s., 1H), 8.70-8.65 (m, 1H), 8.63-8.55 (m, 2H), 8.51 (s, 1H), 8.43 (d, J = 11.0 Hz, 1H), 7.82 (s, 1H), 5.70 (br. s., 1H), 5.27 (t, J = 6.1 Hz, 1H), 4.89-4.77 (m, 2H), 4.53 (dd, J = 11.6, 5.8 Hz, 1H), 4.08 (s, 3H), 4.03-3.89 (m, 1H), 3.58-3.34 (m, 1H), 2.62 (s, 3H), 1.41 (d, J = 6.4 Hz, 3H), 1.11 (d, J = 5.8 Hz, 3H). |
| 702 | 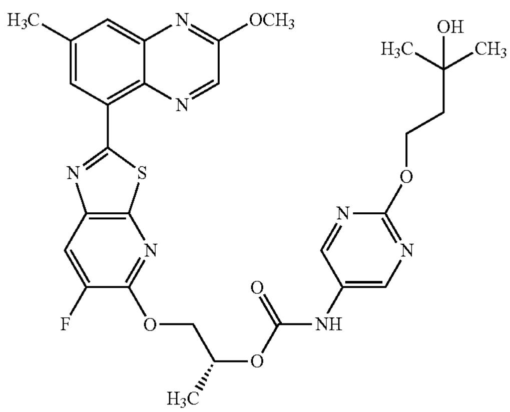 [SMILES: COc1cnc2c(-c3nc4cc(F)c(OC[C@@H](C)OC(=O)Nc5cnc(OCCC(C)(C)O)nc5)nc4s3)cc(C)cc2n1] | I-100 | 624.2 | 1.30 | ¹H NMR (500 MHz, DMSO-d₆) δ 9.79 (br. s., 1H), 8.69 (s, 1H), 8.59 (br. s., 2H), 8.53 (s, 1H), 8.44 (d, J = 10.7 Hz, 1H), 7.84 (s, 1H), 5.25 (br. s., 1H), 4.85 (br. s., 1H), 4.58-4.48 (m, 1H), 4.38 (s, 1H), 4.30 (d, J = 7.6 Hz, 2H), 4.09 (s, 3H), 3.43-3.33 (m, 2H), 2.63 (s, 3H), 1.41 (d, J = 6.7 Hz, 3H), 1.14 (s, 6H). |

Example 708

(2R,3S)-3-((6-fluoro-2-(2-methoxy-7-methylquinoxalin-5-yl)thiazolo[5,4-b]pyridin-5-yl)oxy)butan-2-yl (2-oxo-2,3-dihydrobenzo[d]oxazol-6-yl)carbamate (708)

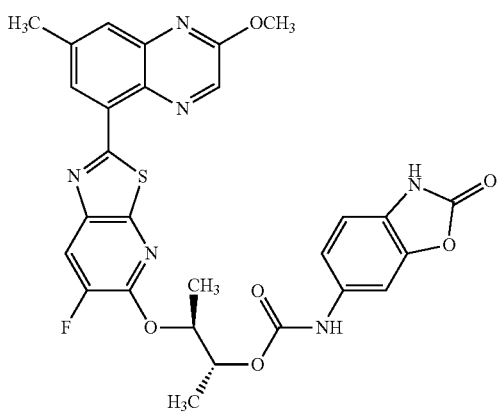

To a solution of Intermediate I-134 (17 mg, 0.036 mmol) in DCM (1 mL) and THF (0.5 mL), was added 6-aminobenzo[d]oxazol-2(3H)-one (10.70 mg, 0.071 mmol) followed by pyridine (0.029 mL, 0.356 mmol). The mixture was stirred at room temperature for 1 hour. The reaction was quenched with 0.2 mL of MeOH. The reaction mixture was concentrated and redissolved in DMF, filtered, and purified by preparative HPLC (Method D, 40 to 80% B in 20 minutes) to yield Example 708 (6 mg, 9.96 μmol, 27.9% yield): ¹H NMR (500 MHz, DMSO-d₆) δ 9.56 (br. s., 1H), 8.53 (s, 1H), 8.44 (s, 1H), 8.35 (d, J=10.4 Hz, 1H), 7.75 (s, 1H), 7.39 (br. s., 1H), 7.09 (br. s., 1H), 6.91 (d, J=7.6 Hz, 1H), 5.64 (d, J=6.4 Hz, 1H), 5.13 (d, J=6.4 Hz, 1H), 4.06 (s, 3H), 3.54-3.38 (m, 1H), 2.59 (s, 3H), 1.45 (d, J=6.4 Hz, 3H), 1.40-1.35 (m, 3H). LC-MS: method H, RT=1.28 min, MS (ESI) m/z: 591.1 (M+H)+. Analytical HPLC Method B: 98% purity.

Examples 709 to 731

The following additional examples have been prepared, isolated and characterized using the methods described for Example 708 and the examples above. If necessary, removal of silyl protecting groups was accomplished by treatment of the protected compound with a solution of 90% MeOH, 9.9% water, and 0.1% TFA or MeOH/HCl (20/1) solution to afford the desired compound.

| Ex. No. | Structure | Amine | LCMS [M + H]+ m/z | LCMS RT (Min) Method H | NMR |
|---|---|---|---|---|---|
| 709 | 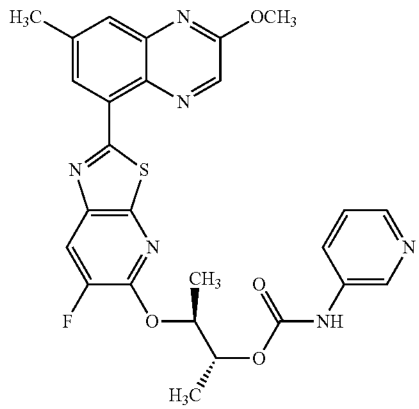 [SMILES: COc1cnc2c(-c3nc4cc(F)c(O[C@@H](C)[C@@H](C)OC(=O)Nc5cccnc5)nc4s3)cc(C)cc2n1] | | 535.2 | 1.01 | $^1$H NMR (500 MHz, DMSO-d$_6$) δ 9.81 (br. s., 1H), 8.61-8.50 (m, 2H), 8.39 (br. s., 1H), 8.31 (d, J = 10.7 Hz, 1H), 8.16 (br. s., 1H), 7.87 (br. s., 1H), 7.72 (br. s., 1H), 7.30 (br. s., 1H), 5.62 (d, J = 5.2 Hz, 1H), 5.16 (d, J = 6.1 Hz, 1H), 4.05 (s, 3H), 3.56 (br. s., 3H), 1.45 (d, J = 5.8 Hz, 3H), 1.39 (d, J = 5.8 Hz, 3H). |
| 710 | 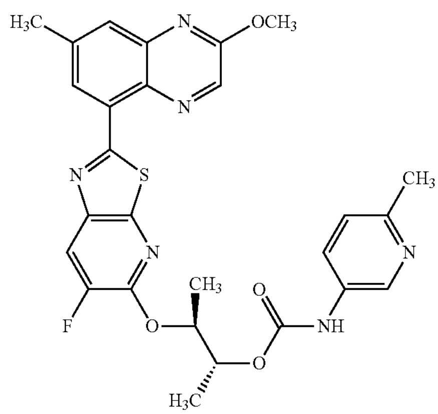 | | 549.1 | 1.11 | $^1$H NMR (500 MHz, DMSO-d$_6$) δ 9.76 (br. s., 1H), 8.60 (s, 1H), 8.46 (br. s., 2H), 8.38 (d, J = 10.7 Hz, 1H), 7.78 (br. s., 2H), 7.21 (br. s., 1H), 5.66 (d, J = 6.7 Hz, 1H), 5.14 (d, J = 6.1 Hz, 1H), 4.07 (s, 3H), 2.60 (s, 3H), 2.35 (s, 3H), 1.45 (d, J = 6.4 Hz, 3H), 1.39 (d, J = 6.4 Hz, 3H). |
| 711 | 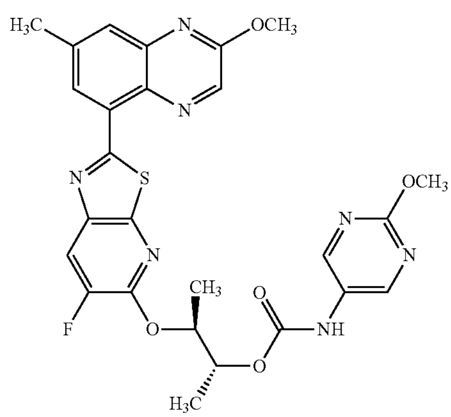 [SMILES: COc1cnc2c(-c3nc4cc(F)c(O[C@@H](C)[C@@H](C)OC(=O)Nc5cnc(OC)nc5)nc4s3)cc(C)cc2n1] | | 566.0 | 1.31 | $^1$H NMR (500 MHz, DMSO-d$_6$) δ 9.70 (br. s., 1H), 8.60 (d, J = 9.2 Hz, 3H), 8.48 (s, 1H), 8.40 (d, J = 10.4 Hz, 1H), 7.80 (s, 1H), 5.73 (d, J = 5.2 Hz, 1H), 5.11 (d, J = 6.4 Hz, 1H), 4.08 (s, 3H), 3.79 (s, 3H), 2.61 (s, 3H), 1.44 (d, J = 6.4 Hz, 3H), 1.38 (d, J = 6.7 Hz, 3H). |

| Ex. No. | Structure | Amine | LCMS [M + H]+ m/z | LCMS RT (Min) Method H | NMR |
|---|---|---|---|---|---|
| 712 | 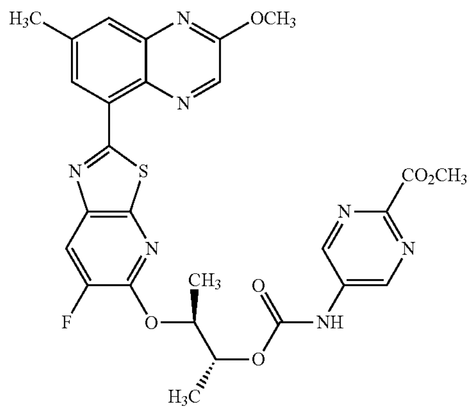 [SMILES: COC(=O)c1ncc(NC(=O)O[C@H](C)[C@H](C)Oc2nc3sc(-c4cc(C)cc5nc(OC)cnc45)nc3cc2F)cn1] | I-107 | 594.2 | 1.18 | ¹H NMR (500 MHz, DMSO-d₆) δ 10.28 (s, 1H), 8.91 (br. s., 2H), 8.49-8.41 (m, 2H), 8.37 (d, J = 11.0 Hz, 1H), 7.75 (s, 1H), 5.82 (d, J = 6.7 Hz, 1H), 5.14 (d, J = 5.2 Hz, 1H), 4.07 (s, 3H), 3.83 (s, 3H), 2.58 (s, 3H), 1.45 (d, J = 6.7 Hz, 3H), 1.40 (d, J = 6.4 Hz, 3H). |
| 713 | 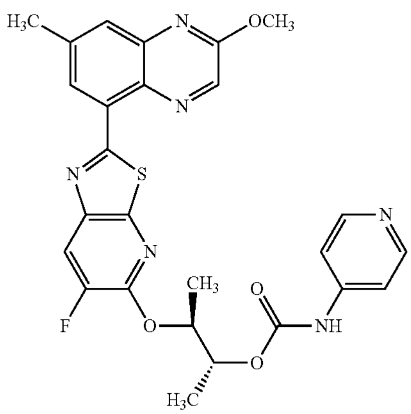 [SMILES: COc1cnc2c(-c3nc4cc(F)c(O[C@@H](C)[C@@H](C)OC(=O)Nc5ccncc5)nc4s3)cc(C)cc2n1] | | 535.2 | 1.01 | ¹H NMR (500 MHz, DMSO-d₆) δ 10.04 (s, 1H), 8.50 (s, 1H), 8.39 (s, 1H), 8.34-8.29 (m, 3H), 7.72 (s, 1H), 7.39 (d, J = 5.2 Hz, 2H), 5.66 (d, J = 6.7 Hz, 1H), 5.16 (d, J = 6.7 Hz, 1H), 4.05 (s, 3H), 2.56 (s, 3H), 1.45 (d, J = 6.4 Hz, 3H), 1.39 (d, J = 6.4 Hz, 3H). |
| 714 | 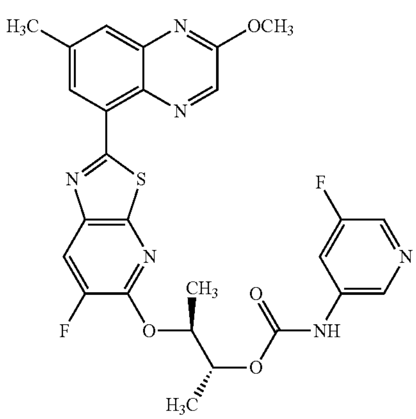 [SMILES: COc1cnc2c(-c3nc4cc(F)c(O[C@@H](C)[C@@H](C)OC(=O)Nc5cncc(F)c5)nc4s3)cc(C)cc2n1] | | 553.2 | 1.25 | ¹H NMR (500 MHz, DMSO-d₆) δ 10.07 (br. s., 1H), 8.51 (s, 1H), 8.40 (s, 1H), 8.36 (br. s., 1H), 8.32 (d, J = 10.7 Hz, 1H), 8.13 (br. s., 1H), 7.83-7.76 (m, 1H), 7.72 (s, 1H), 5.67 (d, J = 6.4 Hz, 1H), 5.15 (d, J = 6.4 Hz, 1H), 4.05 (s, 3H), 2.58-2.56 (m, 3H), 1.44 (d, J = 6.1 Hz, 3H), 1.39 (d, J = 6.4 Hz, 3H). |

| Ex. No. | Structure | Amine | LCMS [M + H]+ m/z | LCMS RT (Min) Method H | NMR |
|---|---|---|---|---|---|
| 715 | 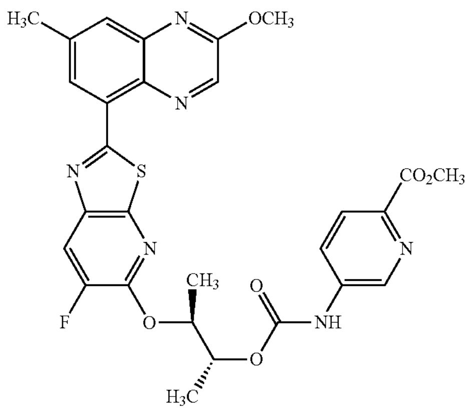 [SMILES: COC(=O)c1ccc(NC(=O)O[C@H](C)[C@H](C)Oc2nc3sc(-c4cc(C)cc5nc(OC)cnc45)nc3cc2F)cn1] | CO₂CH₃ on pyridine with NH₂ | 593.2 | 1.21 | ¹H NMR (500 MHz, DMSO-d₆) δ 10.06 (s, 1H), 8.54 (br. s., 1H), 8.44 (s, 1H), 8.41 (s, 1H), 8.33 (d, J = 10.7 Hz, 1H), 8.00 (br. s., 1H), 7.93 (d, J = 8.5 Hz, 1H), 7.74 (s, 1H), 5.81 (d, J = 6.4 Hz, 1H), 5.11 (d, J = 6.4 Hz, 1H), 4.06 (s, 3H), 3.77 (s, 3H), 2.58 (br. s., 3H), 1.44 (d, J = 6.4 Hz, 3H), 1.38 (d, J = 6.4 Hz, 3H). |
| 716 | 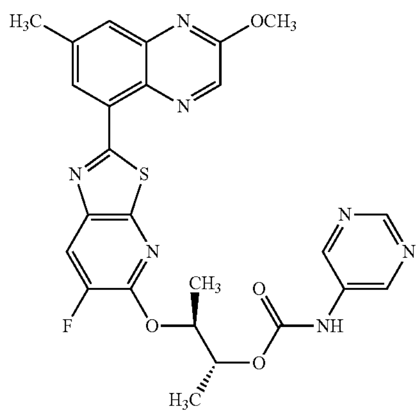 [SMILES: COc1cnc2c(-c3nc4cc(F)c(O[C@@H](C)[C@@H](C)OC(=O)Nc5cncnc5)nc4s3)cc(C)cc2n1] | 5-aminopyrimidine | 536.3 | 1.23 | ¹H NMR (500 MHz, DMSO-d₆) δ 10.12-9.93 (m, 1H), 8.83 (br. s., 2H), 8.79 (s, 1H), 8.67 (s, 1H), 8.54 (d, J = 1.9 Hz, 1H), 8.44 (d, J = 10.7 Hz, 1H), 7.85 (s, 1H), 5.70 (dd, J = 6.7, 2.6 Hz, 1H), 5.16 (dd, J = 6.6, 2.5 Hz, 1H), 4.09 (s, 3H), 2.63 (s, 3H), 1.45 (d, J = 6.6 Hz, 3H), 1.40 (d, J = 6.6 Hz, 3H). |
| 717 | 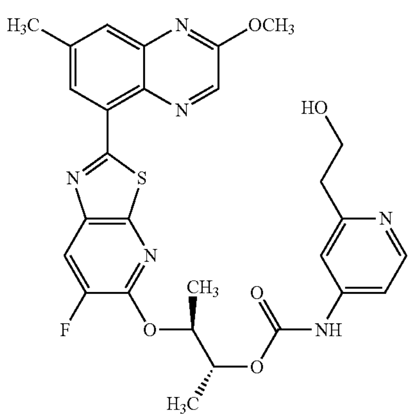 [SMILES: COc1cnc2c(-c3nc4cc(F)c(O[C@@H](C)[C@@H](C)OC(=O)Nc5ccnc(CCO)c5)nc4s3)cc(C)cc2n1] | I-94 | 579.3 | 1.00 | 1H NMR (500 MHz, DMSO-d₆) δ 10.00 (s, 1H), 8.60 (s, 1H), 8.49 (s, 1H), 8.40 (d, J = 11.0 Hz, 1H), 8.24 (d, J = 5.5 Hz, 1H), 7.80 (s, 1H), 7.29 (br. s., 2H), 5.67 (d, J = 6.4 Hz, 1H), 5.16 (d, J = 6.7 Hz, 1H), 4.08 (s, 3H), 3.64 (t, J = 6.6 Hz, 2H), 2.72 (t, J = 6.7 Hz, 2H), 2.61 (s, 3H), 1.46 (d, J = 6.4 Hz, 3H), 1.40 (d, J = 6.4 Hz, 3H). |

-continued

| Ex. No. | Structure | Amine | LCMS [M + H]+ m/z | LCMS RT (Min) Method H | NMR |
|---|---|---|---|---|---|
| 718 | 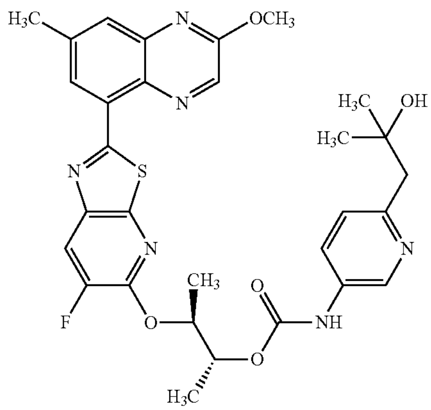 [SMILES: COc1cnc2c(-c3nc4cc(F)c(O[C@@H](C)[C@@H](C)OC(=O)Nc5ccc(CC(C)(C)O)nc5)nc4s3)cc(C)cc2n1] | I-92 | 607.2 | 1.06 | ¹H NMR (500 MHz, DMSO-d₆) δ 9.64 (br. s., 1H), 8.54 (s, 1H), 8.40 (s, 2H), 8.29 (d, J = 10.7 Hz, 1H), 7.74 (s, 2H), 7.22-7.13 (m, 1H), 5.65 (dd, J = 6.7, 2.4 Hz, 1H), 5.12 (dd, J = 6.7, 2.4 Hz, 1H), 4.05 (s, 3H), 3.71-3.70 (m, 1H), 2.67 (d, J = 9.2 Hz, 2H), 2.57 (s, 3H), 1.43 (d, J = 6.7 Hz, 3H), 1.36 (d, J = 6.4 Hz, 3H), 0.97 (d, J = 8.9 Hz, 6H). |
| 719 | 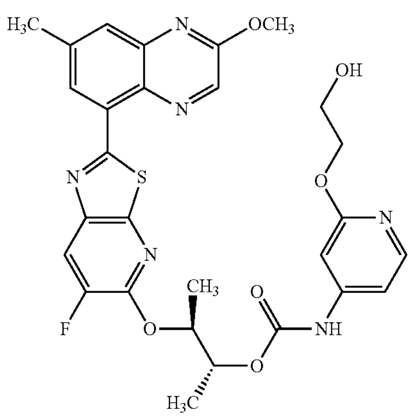 [SMILES: COc1cnc2c(-c3nc4cc(F)c(O[C@@H](C)[C@@H](C)OC(=O)Nc5ccnc(OCCO)c5)nc4s3)cc(C)cc2n1] | I-110 | 595.1 | 1.07 | ¹H NMR (500 MHz, DMSO-d₆) δ 9.93 (s, 1H), 8.55 (s, 1H), 8.46 (s, 1H), 8.36 (d, J = 10.7 Hz, 1H), 7.89 (d, J = 5.5 Hz, 1H), 7.77 (s, 1H), 7.00 (d, J = 5.5 Hz, 1H), 6.81 (s, 1H), 5.68 (dd, J = 6.6, 2.3 Hz, 1H), 5.14 (dd, J = 6.7, 2.1 Hz, 1H), 4.19-4.09 (m, 3H), 4.07 (s, 3H), 3.65-3.58 (m, 1H), 3.46 (br. s., 1H), 2.60 (s, 3H), 1.44 (d, J = 6.4 Hz, 3H), 1.38 (d, J = 6.7 Hz, 3H). |
| 720 | 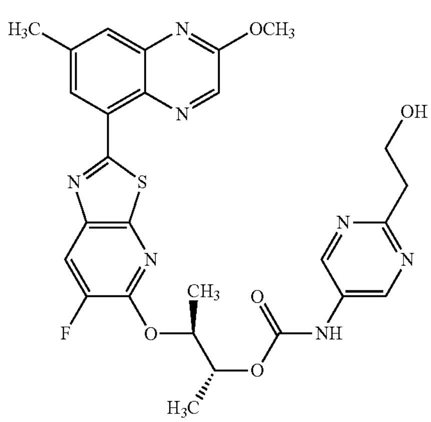 [SMILES: COc1cnc2c(-c3nc4cc(F)c(O[C@@H](C)[C@@H](C)OC(=O)Nc5cnc(CCO)nc5)nc4s3)cc(C)cc2n1] | I-109 | 579.1 | 1.04 | MS (ESI) m/z: 579.1 (M + H)+. ¹H NMR (500 MHz, DMSO-d₆) δ 9.67 (br. s., 1H), 8.58 (s, 1H), 8.44 (s, 2H), 8.33 (d, J = 10.7 Hz, 1H), 7.76 (s, 2H), 7.16 (d, J = 7.9 Hz, 1H), 5.62 (dd, J = 6.4, 2.4 Hz, 1H), 5.14 (dd, J = 6.4, 2.4 Hz, 1H), 4.06 (s, 3H), 3.65 (t, J = 6.9 Hz, 1H), 3.48 (br. s., 1H), 2.76 (d, J = 4.0 Hz, 2H), 2.59 (s, 3H), 1.44 (d, J = 6.4 Hz, 3H), 1.38 (d, J = 6.7 Hz, 3H). |

| Ex. No. | Structure | Amine | LCMS [M + H]+ m/z | LCMS RT (Min) Method H | NMR |
|---|---|---|---|---|---|
| 721 | 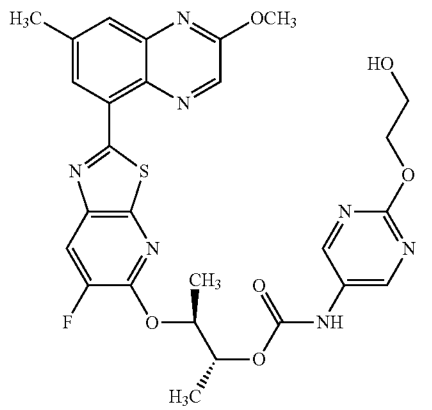 [SMILES: COc1cnc2c(-c3nc4cc(F)c(O[C@@H](C)[C@@H](C)OC(=O)Nc5cnc(OCCO)nc5)nc4s3)cc(C)cc2n1] | I-97 | 596.1 | 1.21 | ¹H NMR (500 MHz, DMSO-d₆) δ 9.71 (br. s., 1H), 8.62 (br. s., 1H), 8.50 (s, 1H), 8.40 (d, J = 10.7 Hz, 1H), 7.82 (s, 1H), 5.75 (d, J = 6.4 Hz, 1H), 5.17 (d, J = 6.7 Hz, 1H), 4.96 (t, J = 5.5 Hz, 1H), 4.28-4.16 (m, 2H), 4.12 (s, 3H), 3.72 (d, J = 5.2 Hz, 2H), 2.65 (s, 3H), 1.49 (d, J = 6.4 Hz, 3H), 1.43 (d, J = 6.7 Hz, 3H). |
| 722 | 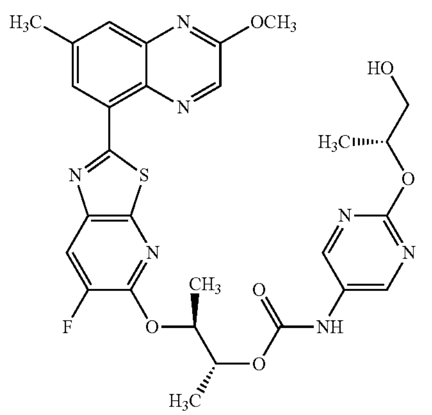 [SMILES: COc1cnc2c(-c3nc4cc(F)c(O[C@@H](C)[C@@H](C)OC(=O)Nc5cnc(O[C@H](C)CO)nc5)nc4s3)cc(C)cc2n1] | I-106 | 610.1 | 1.24 | ¹H NMR (500 MHz, DMSO-d₆) δ 9.78-9.71 (m, 1H), 8.70-8.60 (m, 2H), 8.52 (s, 1H), 8.43 (d, J = 10.4 Hz, 1H), 7.84 (s, 1H), 5.73 (dd, J = 6.4, 2.4 Hz, 1H), 5.18 (dd, J = 6.6, 2.3 Hz, 1H), 5.02 (br. s., 1H), 4.93-4.86 (m, 1H), 4.13 (s, 3H), 3.65-3.38 (m, 3H), 2.66 (s, 3H), 1.49 (d, J = 6.1 Hz, 3H), 1.43 (d, J = 6.7 Hz, 3H). |
| 723 | 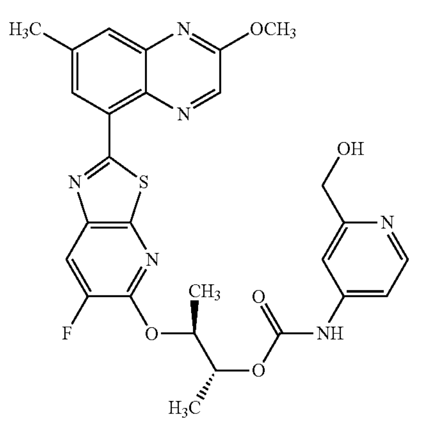 [SMILES: COc1cnc2c(-c3nc4cc(F)c(O[C@@H](C)[C@@H](C)OC(=O)Nc5ccnc(CO)c5)nc4s3)cc(C)cc2n1] | I-94 | 565.1 | 1.05 | ¹H NMR (500 MHz, DMSO-d₆) δ 9.82-9.74 (m, 1H), 8.63 (s, 1H), 8.48 (s, 1H), 8.53-8.46 (m, 2H), 8.39 (d, J = 11.0 Hz, 1H), 7.92-7.83 (m, 1H), 7.80 (s, 1H), 7.38 (d, J = 8.5 Hz, 1H), 5.64 (dd, J = 6.6, 2.6 Hz, 1H), 5.16 (dd, J = 6.6, 2.3 Hz, 1H), 4.47 (s, 2H), 4.08 (s, 3H), 2.61 (s, 3H), 1.46 (d, J = 6.4 Hz, 3H), 1.40 (d, J = 6.7 Hz, 3H). |

-continued

| Ex. No. | Structure | Amine | LCMS [M + H]+ m/z | LCMS RT (Min) Method H | NMR |
|---|---|---|---|---|---|
| 724 | 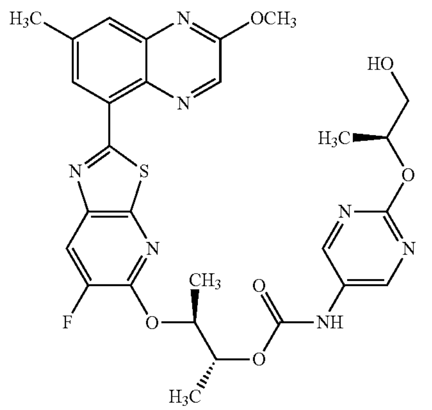 [SMILES: COc1cnc2c(-c3nc4cc(F)c(O[C@@H](C)[C@@H](C)OC(=O)Nc5cnc(O[C@@H](C)CO)nc5)nc4s3)cc(C)cc2n1] | I-105 | 610.1 | 1.23 | $^1$H NMR (500 MHz, DMSO-d$_6$) δ 9.68-9.57 (m, 1H), 8.57 (s, 1H), 8.52 (br. s., 1H), 8.43 (s, 1H), 8.34 (d, J = 10.7 Hz, 1H), 7.75 (s, 1H), 5.65 (dd, J = 6.7, 2.4 Hz, 1H), 5.08 (d, J = 4.0 Hz, 1H), 4.91 (d, J = 5.5 Hz, 1H), 4.80 (t, J = 5.6 Hz, 1H), 4.03 (s, 3H), 3.54-3.38 (m, 3H), 2.56 (s, 3H), 1.39 (d, J = 6.4 Hz, 3H), 1.33 (d, J = 6.7 Hz, 3H), 1.10 (d, J = 6.1 Hz, 3H). |
| 725 | 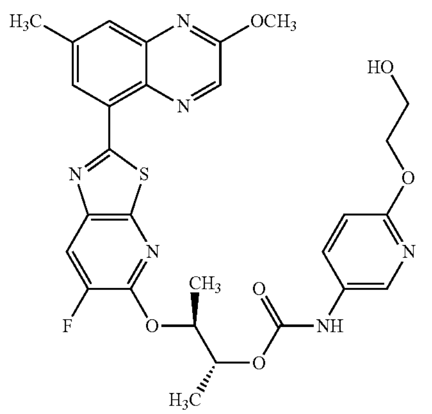 [SMILES: COc1cnc2c(-c3nc4cc(F)c(O[C@@H](C)[C@@H](C)OC(=O)Nc5ccc(OCCO)nc5)nc4s3)cc(C)cc2n1] | I-93 | 595.2 | 1.22 | $^1$H NMR (500 MHz, DMSO-d$_6$) δ 9.42 (br. s., 1H), 8.52 (br. s., 1H), 8.40 (br. s., 1H), 8.34-8.24 (m, 1H), 8.14-8.01 (m, 1H), 7.73 (br. s., 2H), 6.80-6.59 (m, 1H), 5.66 (br. s., 1H), 5.09 (d, J = 6.1 Hz, 1H), 4.92 (s, 1H), 4.15-4.08 (m, 1H), 4.05 (s, 3H), 3.72-3.57 (m, 4H), 2.59-2.55 (m, 3H), 1.42 (d, J = 6.1 Hz, 3H), 1.35 (d, J = 6.4 Hz, 3H). |
| 726 | 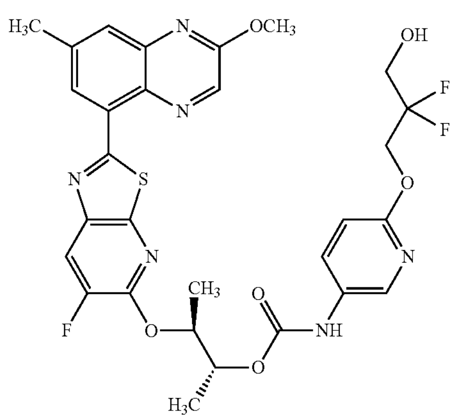 [SMILES: COc1cnc2c(-c3nc4cc(F)c(O[C@@H](C)[C@@H](C)OC(=O)Nc5ccc(OCC(F)(F)CO)nc5)nc4s3)cc(C)cc2n1] | I-99 | 645.2 | 1.30 | $^1$H NMR (500 MHz, DMSO-d$_6$) δ 9.57 (br. s., 1H), 8.54 (s, 1H), 8.42 (s, 1H), 8.31 (d, J = 10.4 Hz, 1H), 8.17 (br. s., 1H), 7.85 (br. s., 1H), 7.75 (s, 1H), 6.88 (br. s., 1H), 5.79 (t, J = 6.1 Hz, 1H), 5.71 (d, J = 5.8 Hz, 1H), 5.17 (d, J = 5.8 Hz, 1H), 4.60-4.39 (m, 2H), 4.10 (s, 3H), 3.77 (br. s., 2H), 2.61 (s, 3H), 1.49 (d, J = 6.4 Hz, 3H), 1.42 (d, J = 6.4 Hz, 3H). |

-continued

| Ex. No. | Structure | Amine | LCMS [M + H]+ m/z | LCMS RT (Min) Method H | NMR |
|---|---|---|---|---|---|
| 727 | 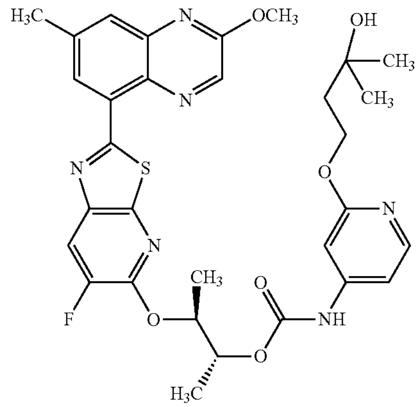 [SMILES: COc1cnc2c(-c3nc4cc(F)c(O[C@@H](C)[C@@H](C)OC(=O)Nc5ccnc(OCCC(C)(C)O)c5)nc4s3)cc(C)cc2n1] | I-108 | 637.2 | 1.13 | ¹H NMR (500 MHz, DMSO-d₆) δ 9.90 (s, 1H), 8.54 (s, 1H), 8.45 (s, 1H), 8.34 (d, J = 10.7 Hz, 1H), 7.90 (d, J = 5.2 Hz, 1H), 7.77 (s, 1H), 6.99 (d, J = 5.2 Hz, 1H), 6.76 (s, 1H), 5.70 (d, J = 4.9 Hz, 1H), 5.13 (d, J = 6.4 Hz, 1H), 4.27-4.13 (m, 2H), 4.06 (s, 3H), 3.48 (s, 1H), 2.59 (s, 3H), 2.52 (br. s., 6H), 1.72 (t, J = 6.4 Hz, 2H), 1.44 (d, J = 6.4 Hz, 3H), 1.38 (d, J = 6.4 Hz, 3H). |
| 728 | 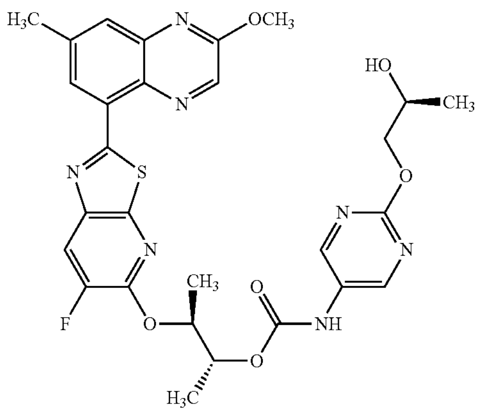 [SMILES: COc1cnc2c(-c3nc4cc(F)c(O[C@@H](C)[C@@H](C)OC(=O)Nc5cnc(OC[C@H](C)O)nc5)nc4s3)cc(C)cc2n1] | I-103 | 610.2 | 1.29 | ¹H NMR (500 MHz, DMSO-d₆) δ 9.72-9.62 (m, 1H), 8.63 (br. s., 1H), 8.57 (br. s., 2H), 8.50 (s, 1H), 8.41 (d, J = 10.4 Hz, 1H), 7.81 (s, 1H), 5.71 (d, J = 6.7 Hz, 1H), 5.12 (dd, J = 6.4, 2.1 Hz, 1H), 4.97 (d, J = 5.5 Hz, 1H), 4.84 (d, J = 4.9 Hz, 1H), 4.08 (s, 3H), 4.06-3.96 (m, 1H), 3.94-3.89 (m, 2H), 2.62 (s, 3H), 1.44 (d, J = 6.4 Hz, 3H), 1.38 (d, J = 6.7 Hz, 3H), 1.10 (t, J = 5.8 Hz, 3H). |
| 729 | 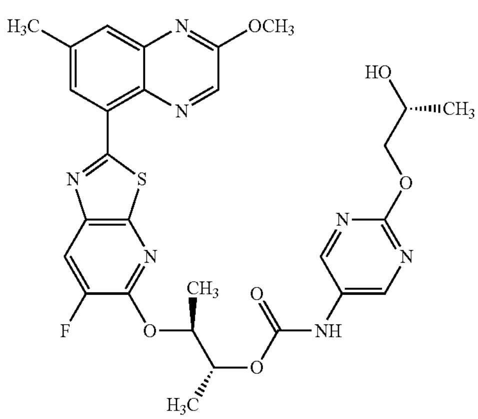 [SMILES: COc1cnc2c(-c3nc4cc(F)c(O[C@@H](C)[C@@H](C)OC(=O)Nc5cnc(OC[C@@H](C)O)nc5)nc4s3)cc(C)cc2n1] | I-104 | 610.2 | 1.29 | ¹H NMR (500 MHz, DMSO-d₆) δ 9.72-9.65 (m, 1H), 8.64 (br. s., 1H), 8.57 (br. s., 2H), 8.51 (s, 1H), 8.41 (d, J = 10.7 Hz, 1H), 7.82 (s, 1H), 5.71 (d, J = 6.4 Hz, 1H), 5.16-5.09 (m, 1H), 4.84 (d, J = 4.9 Hz, 1H), 4.08 (s, 3H), 4.06-3.97 (m, 1H), 3.91 (s, 2H), 2.62 (s, 3H), 1.44 (d, J = 6.1 Hz, 3H), 1.38 (d, J = 6.7 Hz, 3H), 1.10 (s, 3H). |

-continued

| Ex. No. | Structure | Amine | LCMS [M + H]+ m/z | LCMS RT (Min) Method H | NMR |
|---|---|---|---|---|---|
| 730 | 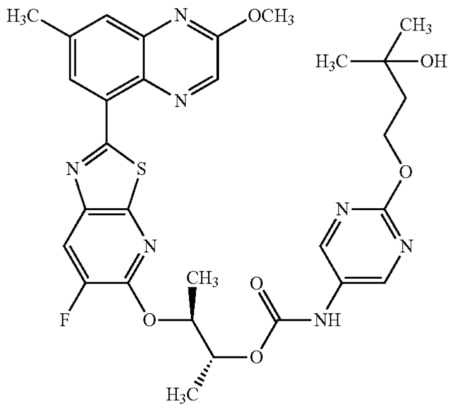 [SMILES: COc1cnc2c(-c3nc4cc(F)c(O[C@@H](C)[C@@H](C)OC(=O)Nc5cnc(OCCC(C)(C)O)nc5)nc4s3)cc(C)cc2n1] | I-100 | 638.2 | 1.32 | ¹H NMR (500 MHz, DMSO-d₆) δ 8.62 (s, 1H), 8.56 (br. s., 2H), 8.50 (s, 1H), 8.40 (d, J = 10.7 Hz, 1H), 7.81 (s, 1H), 5.73 (d, J = 4.9 Hz, 1H), 5.11 (dd, J = 6.4, 1.8 Hz, 1H), 4.34-4.16 (m, 2H), 4.08 (s, 3H), 2.61 (s, 3H), 1.78 (t, J = 7.3 Hz, 2H), 1.43 (d, J = 6.4 Hz, 3H), 1.38 (d, J = 6.7 Hz, 3H), 1.13 (d, J = 2.7 Hz, 6H). |
| 731 | 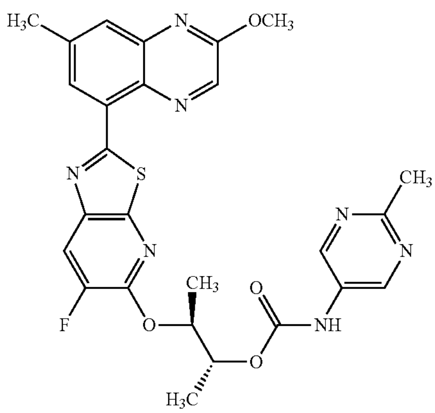 | | 550.2 | 1.23 | ¹H NMR (500 MHz, DMSO-d₆) δ 8.68 (br. s., 2H), 8.62 (s, 1H), 8.49 (s, 1H), 8.40 (d, J = 11.0 Hz, 1H), 7.81 (s, 1H), 5.69 (d, J = 6.4 Hz, 1H), 5.12 (d, J = 6.4 Hz, 1H), 4.07 (s, 3H), 2.60 (s, 3H), 2.46 (s, 3H), 1.43 (d, J = 6.4 Hz, 3H), 1.37 (d, J = 6.4 Hz, 3H). |

Example 733

(R)-1-((2-(2-methoxy-7-methylquinoxalin-5-yl)-7-methylthiazolo[5,4-b]pyridin-5-yl)oxy)propan-2-yl pyridin-3-ylcarbamate

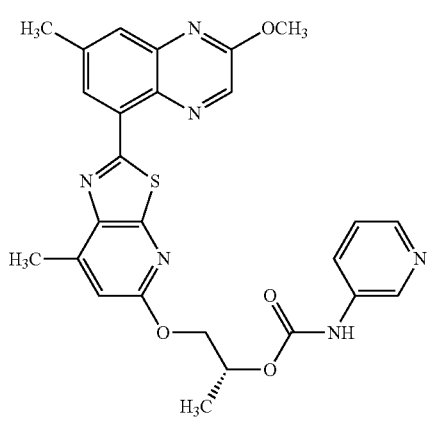

(733)

To a solution of Intermediate I-138 (10 mg, 0.022 mmol) in DCM (1 mL) and THF (0.5 mL) was added pyridin-3-amine (7.18 mg, 0.076 mmol) followed by DIEA (0.038 mL, 0.218 mmol). The mixture was stirred at room temperature for 1 h. The reaction was quenched with 0.2 mL of MeOH. The reaction mixture was concentrated, redissolved in DMF, filtered, and purified by preparative HPLC (Method D, 25 to 100% B in 15 minutes) to yield Example 733 (3.5 mg, 6.57 μmol, 30.2% yield): ¹H NMR (500 MHz, DMSO-d₆) δ 8.70 (s, 1H), 8.62 (br. s., 1H), 8.54 (s, 1H), 8.19 (br. s., 1H), 7.89 (br. s., 1H), 7.82 (s, 1H), 7.30 (d, J=7.9 Hz, 1H), 6.90 (s, 1H), 5.24 (br. s., 1H), 4.65-4.41 (m, 2H), 4.08 (s, 3H), 2.72 (s, 3H), 2.63 (s, 3H), 1.39 (d, J=6.4 Hz, 3H). LC-MS: method H, RT=1.07 min, MS (ESI) m/z: 517.2 (M+H)⁺. Analytical HPLC Method B: 97% purity.

Examples 734 to 740

The following additional examples have been prepared, isolated and characterized using the methods described for Example 733 and the examples above

| Ex. No. | Structure | Amine | LCMS [M + H]+ m/z | LCMS RT (Min) Method H | NMR |
|---|---|---|---|---|---|
| 734 | 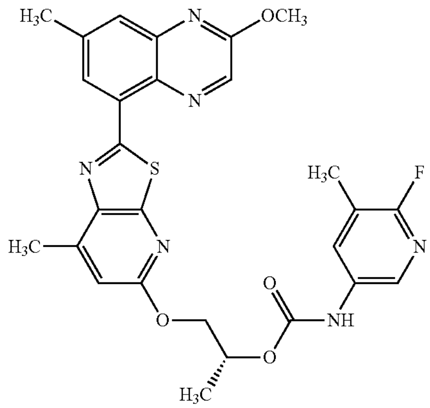 [SMILES: COc1cnc2c(-c3nc4c(C)cc(OC[C@@H](C)OC(=O)Nc5cnc(F)c(C)c5)nc4s3)cc(C)cc2n1] | | 549.2 | 1.36 | ¹H NMR (500 MHz, DMSO-d$_6$) δ 9.88 (br. s., 1H), 8.68 (s, 1H), 8.53 (s, 1H), 8.05 (br. s., 1H), 7.81 (s, 1H), 6.90 (s, 1H), 5.22 (br. s., 1H), 4.68-4.38 (m, 2H), 4.08 (s, 3H), 2.72 (s, 3H), 2.63 (s, 3H), 2.18 (s, 3H), 1.38 (d, J = 6.1 Hz, 4H). |
| 735 | 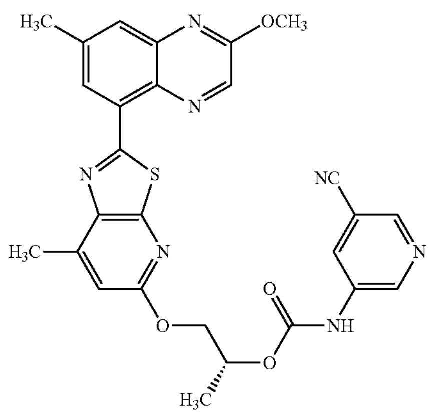 [SMILES: COc1cnc2c(-c3nc4c(C)cc(OC[C@@H](C)OC(=O)Nc5cncc(C#N)c5)nc4s3)cc(C)cc2n1] | | 542.2 | 1.30 | ¹H NMR (500 MHz, DMSO-d$_6$) δ 10.30 (br. s., 1H), 8.81 (br. s., 1H), 8.66 (s, 1H), 8.61 (s, 1H), 8.51 (s, 1H), 8.26 (br. s., 1H), 7.80 (s, 1H), 6.89 (s, 1H), 5.26 (br. s., 1H), 4.74-4.34 (m, 2H), 4.07 (s, 3H), 2.71 (s, 3H), 2.62 (s, 3H), 1.40 (d, J = 6.4 Hz, 3H). |
| 736 | 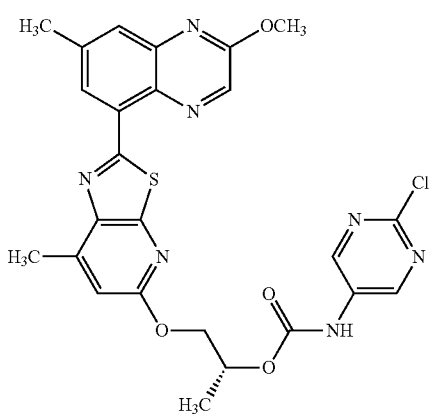 [SMILES: COc1cnc2c(-c3nc4c(C)cc(OC[C@@H](C)OC(=O)Nc5cnc(Cl)nc5)nc4s3)cc(C)cc2n1] | | 553.1 | 1.35 | ¹H NMR (500 MHz, DMSO-d$_6$) δ 8.77 (br. s., 2H), 8.59 (s, 1H), 8.44 (s, 1H), 7.73 (s, 1H), 6.85 (s, 1H), 5.22 (br. s., 1H), 4.68 (d, J = 9.5 Hz, 1H), 4.38 (dd, J = 11.9, 6.1 Hz, 1H), 4.04 (s, 3H), 2.67 (s, 3H), 2.58 (s, 3H), 1.39 (d, J = 6.7 Hz, 3H). |

-continued

| Ex. No. | Structure | Amine | LCMS [M + H]+ m/z | LCMS RT (Min) Method H | NMR |
|---|---|---|---|---|---|
| 737 | 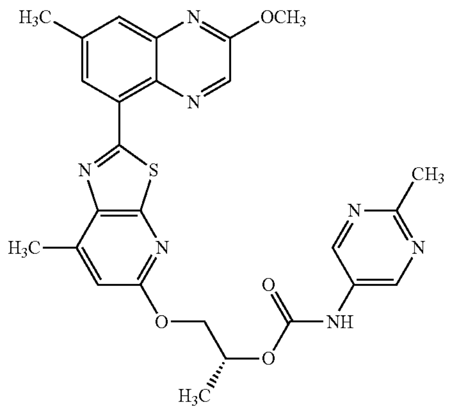 | | 532.2 | 1.25 | ¹H NMR (500 MHz, DMSO-d₆) δ 8.73 (br. s., 2H), 8.59 (s, 1H), 8.43 (s, 1H), 7.73 (s, 1H), 6.84 (s, 1H), 5.22 (dd, J = 6.4, 3.4 Hz, 1H), 4.61 (dd, J = 11.7, 2.6 Hz, 1H), 4.39 (dd, J = 11.7, 6.3 Hz, 1H), 4.04 (s, 3H), 2.66 (s, 3H), 2.58 (s, 3H), 2.51 (br. s., 3H), 1.38 (d, J = 6.4 Hz, 3H). |
| 738 | 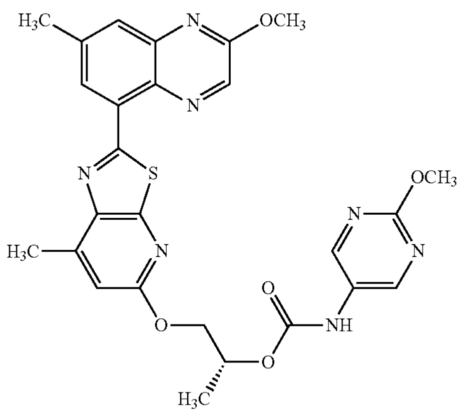 [SMILES: COc1cnc2c(-c3nc4c(C)cc(OC[C@@H](C)OC(=O)Nc5cnc(OC)nc5)nc4s3)cc(C)cc2n1] | | 548.2 | 1.30 | ¹H NMR (500 MHz, DMSO-d₆) δ 8.67 (s, 1H), 8.61 (br. s., 2H), 8.52 (s, 1H), 7.80 (s, 1H), 6.89 (s, 1H), 5.19 (br. s., 1H), 4.66 (d, J = 9.5 Hz, 1H), 4.39 (dd, J = 11.7, 6.0 Hz, 1H), 4.06 (s, 3H), 3.86-3.79 (m, 3H), 2.70 (s, 3H), 2.62 (s, 3H), 1.37 (d, J = 6.4 Hz, 3H). |
| 740 | 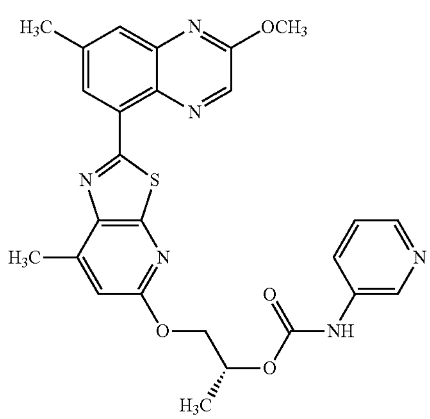 [SMILES: COc1cnc2c(-c3nc4c(C)cc(OC[C@@H](C)OC(=O)Nc5cccnc5)nc4s3)cc(C)cc2n1] | | 530.2 | 1.12 | ¹H NMR (500 MHz, DMSO-d₆) δ 9.80 (br. s., 1H), 8.62-8.57 (m, 1H), 8.55 (s, 1H), 8.42 (s, 1H), 8.18 (br. s., 1H), 7.88 (br. s., 1H), 7.72 (s, 1H), 7.38-7.22 (m, 1H), 6.80 (s, 1H), 5.56-5.46 (m, 1H), 5.10 (dd, J = 6.4, 2.4 Hz, 1H), 4.04 (s, 3H), 2.66 (s, 3H), 2.58 (s, 3H), 1.37 (dd, J = 11.6, 6.4 Hz, 6H). |

Example 741

(R)-1-((6-fluoro-2-(2-methoxy-7-methylquinoxalin-5-yl)thiazolo[5,4-b]pyridin-5-yl)oxy) propan-2-yl (6-((2-hydroxy-2-methylpropyl)carbamoyl)pyridin-3-yl)carbamate

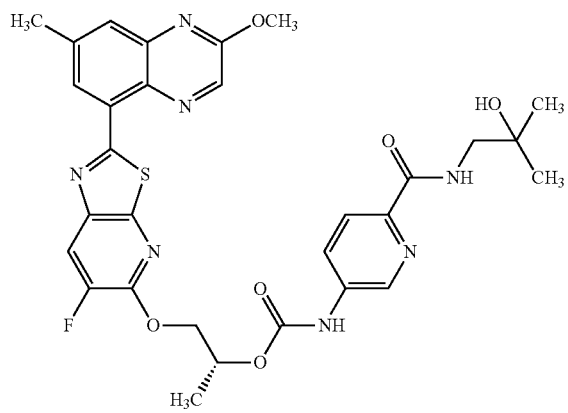

(741)

To a suspension of Example 689 (0.012 g, 0.021 mmol) in THF (0.207 ml) was added 1-amino-2-methylpropan-2-ol (0.029 ml, 0.622 mmol) followed by magnesium chloride (0.020 g, 0.207 mmol). The reaction vial was sealed and heated to 65° C. overnight. The reaction mixture was diluted with EtOAc and filtered through Celite. The reaction mixture was concentrated, redissolved in DMF, filtered, and purified by preparative HPLC (Method D, 50 to 100% B in 21 minutes) to yield Example 741 (0.0011 g, 1.713 µmol, 8.26% yield): $^1$H NMR (500 MHz, DMSO-$d_6$) δ 10.15 (br. s., 1H), 8.60 (br. s., 1H), 8.55 (s, 1H), 8.45 (s, 1H), 8.35 (d, J=11.0 Hz, 1H), 8.26 (br. s., 1H), 8.04 (d, J=7.9 Hz, 1H), 7.95 (d, J=8.5 Hz, 1H), 7.78 (s, 1H), 5.28 (br. s., 1H), 4.89 (d, J=10.1 Hz, 1H), 4.50 (dd, J=11.7, 5.6 Hz, 1H), 4.06 (s, 3H), 3.23 (dd, J=11.1, 6.3 Hz, 2H), 2.59 (s, 3H), 1.43 (d, J=6.4 Hz, 3H), 1.08 (d, J=5.8 Hz, 6H). LC-MS: method H, RT=1.23 min, MS (ESI) m/z: 636.2 (M+H)$^+$. Analytical HPLC Method B: 99% purity.

Examples 742 to 749

The following additional examples have been prepared, isolated and characterized using the methods described for Example 741 and the examples above.

| Ex. No. | Structure | ester | LCMS [M + H]$^+$ m/z | LCMS RT (Min)/ Method | NMR |
|---|---|---|---|---|---|
| 742 | 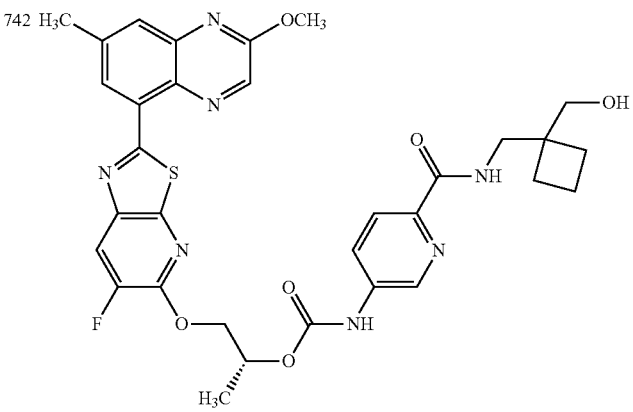 | 689 | 632.2 | 2.17/B | $^1$H NMR (500 MHz, DMSO-$d_6$) δ 10.16 (br. s., 2H), 8.61 (br. s., 2H), 8.50 (br. s., 1H), 8.41 (d, J = 9.8 Hz, 1H), 8.03 (br. s., 1H), 7.95 (d, J = 8.5 Hz, 1H), 7.82 (br. s., 1H), 5.83-5.67 (m, 1H), 5.29 (br. s., 2H), 4.95-4.83 (m, 3H), 4.53 (br. s., 2H), 4.08 (br. s., 3H), 3.38 (br. s., 3H), 2.62 (br. s., 3H), 1.85-1.66 (m, 6H). |
| 743 | 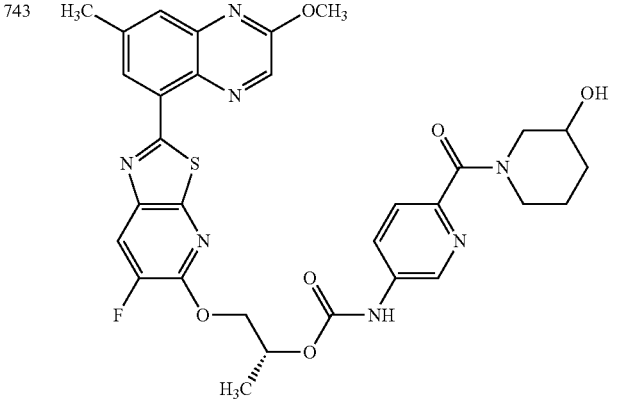 | 689 | 648.2 | 2.25/B | $^1$H NMR (500 MHz, DMSO-$d_6$) δ 10.11 (d, J = 12.2 Hz, 1H), 8.58 (br. s., 2H), 8.42 (br. s., 1H), 8.33 (d, J = 10.1 Hz, 1H), 7.99 (br. s., 1H), 7.74 (br. s, 1H), 7.51 (t, J = 10.2 Hz, 1H), 5.31 (br. s., 1H), 5.06 (br. s, 1H), 4.78 (d, J = 10.1 Hz, 2H), 4.06 (s, 3H), 3.51 (s, 2H), 3.14 (br. s., 2H), 3.01-2.91 (m, 2H), 2.58 (s, 3H), 1.92-1.72 (m, 3H), 1.43 (d, J = 6.4 Hz, 3H). |

| Ex. No. | Structure | LCMS ester | LCMS [M + H]+ m/z | LCMS RT (Min)/ Method | NMR |
|---|---|---|---|---|---|
| 744 | 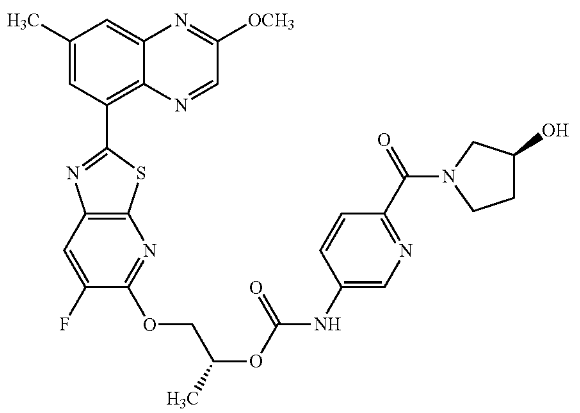 [SMILES: COc1cnc2c(-c3nc4cc(F)c(OC[C@@H](C)OC(=O)Nc5ccc(C(=O)N6CC[C@H](O)C6)nc5)nc4s3)cc(C)cc2n1] | 689 | 634.2 | 2.20/B | ¹H NMR (500 MHz, DMSO-d₆) δ 10.15-10.04 (m, 1H), 8.56 (d, J = 10.1 Hz, 2H), 8.42 (br. s., 1H), 8.33 (d, J = 10.4 Hz, 1H), 8.02 (br. s., 1H), 7.75 (br. s., 2H), 5.30 (br. s., 1H), 5.09-4.97 (m, 1H), 4.92-4.74 (m, 1H), 4.52 (br. s., 1H), 4.28 (br. s., 1H), 4.05 (s, 3H), 3.80-3.67 (m, 1H), 3.52-3.36 (m, 2H), 2.58 (br. s., 3H), 1.95-1.84 (m, 1H), 1.77 (br. s., 2H), 1.43 (d, J = 6.1 Hz, 3H). |
| 745 | 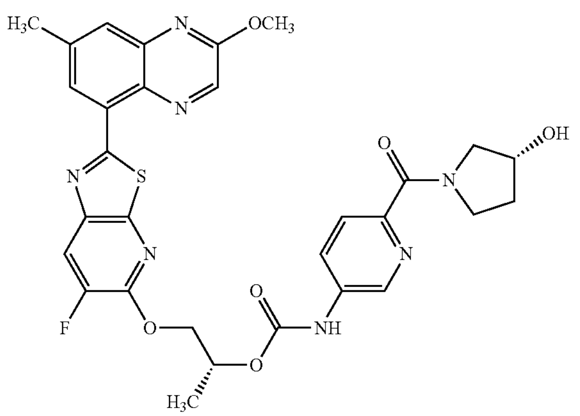 [SMILES: COc1cnc2c(-c3nc4cc(F)c(OC[C@@H](C)OC(=O)Nc5ccc(C(=O)N6CC[C@@H](O)C6)nc5)nc4s3)cc(C)cc2n1] | 689 | 634.2 | 2.20/B | ¹H NMR (500 MHz, DMSO-d₆) δ 10.15-10.04 (m, 1H), 8.56 (d, J = 10.1 Hz, 2H), 8.42 (br. s., 1H), 8.33 (d, J = 10.4 Hz, 1H), 8.02 (br. s., 1H), 7.75 (br. s., 2H), 5.30 (br. s., 1H), 5.09-4.97 (m, 1H), 4.92-4.74 (m, 1H), 4.52 (br. s., 1H), 4.28 (br. s., 1H), 4.05 (s, 3H), 3.80-3.67 (m, 1H), 3.52-3.36 (m, 2H), 2.58 (br. s, 3H), 1.95-1.84 (m, 1H), 1.77 (br. s., 2H), 1.43 (d, J = 6.1 Hz, 3H). |
| 746 | 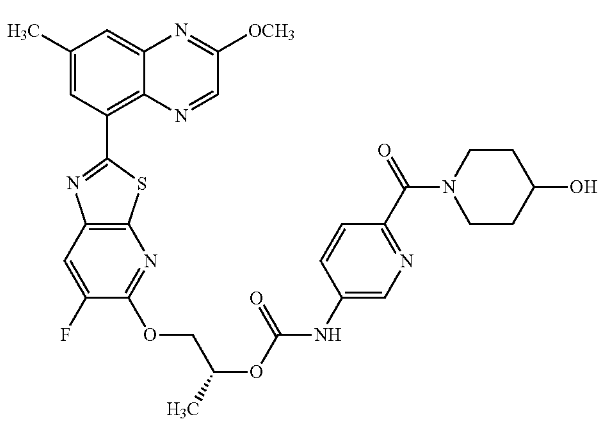 [SMILES: COc1cnc2c(-c3nc4cc(F)c(OC[C@@H](C)OC(=O)Nc5ccc(C(=O)N6CCC(O)CC6)nc5)nc4s3)cc(C)cc2n1] | 689 | 648.2 | 2.19/B | ¹H NMR (500 MHz, DMSO-d₆) δ 10.11 (br. s., 1H), 8.63-8.53 (m, 2H), 8.45 (s, 1H), 8.36 (d, J = 10.7 Hz, 1H), 7.98 (br. s., 1H), 7.77 (s, 1H), 7.52 (d, J = 8.5 Hz, 1H), 5.31 (br. s., 1H), 4.87-4.75 (m, 2H), 4.61-4.48 (m, 1H), 4.06 (s, 3H), 4.01 (br. s., 1H), 3.72 (br. s., 1H), 3.60 (br. s., 1H), 3.22-3.10 (m, 2H), 2.60 (s, 3H), 1.79 (br. s., 1H), 1.67 (br. s., 1H), 1.43 (d, J = 6.1 Hz, 3H), 1.40-1.24 (m, 2H). |

-continued

| Ex. No. | Structure | LCMS ester | LCMS [M + H]+ m/z | LCMS RT (Min)/ Method | NMR |
|---|---|---|---|---|---|
| 747 | 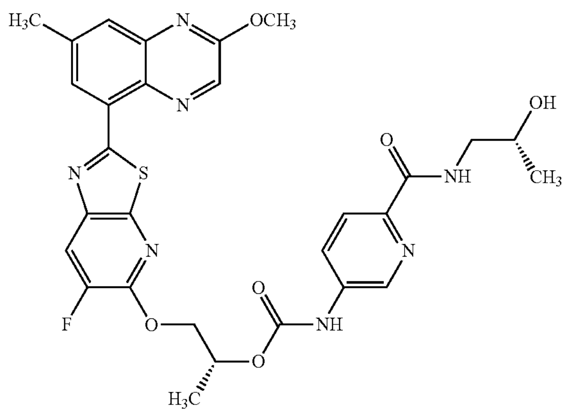 [SMILES: COc1cnc2c(-c3nc4cc(F)c(OC[C@@H](C)OC(=O)Nc5ccc(C(=O)NC[C@@H](C)O)nc5)nc4s3)cc(C)cc2n1] | 689 | 622.1 | 1.17/H | ¹H NMR (500 MHz, DMSO-d₆) δ 10.16 (br. s., 1H), 8.62 (br. s., 1H), 8.58 (s, 1H), 8.47 (s, 1H), 8.41-8.34 (m, 2H), 8.03 (br. s., 1H), 7.95 (d, J = 8.5 Hz, 1H), 7.79 (s, 1H), 5.29 (br. s., 1H), 4.89 (d, J = 10.1 Hz, 1H), 4.52 (dd, J = 11.7, 5.3 Hz, 1H), 4.07 (s, 3H), 3.75 (br. s., 1H), 3.53 (s, 1H), 3.32-3.25 (m, 1H), 3.18-3.10 (m, 1H), 2.61 (s, 3H), 1.43 (d, J = 6.4 Hz, 3H), 1.10-0.99 (m, 3H). |
| 748 | 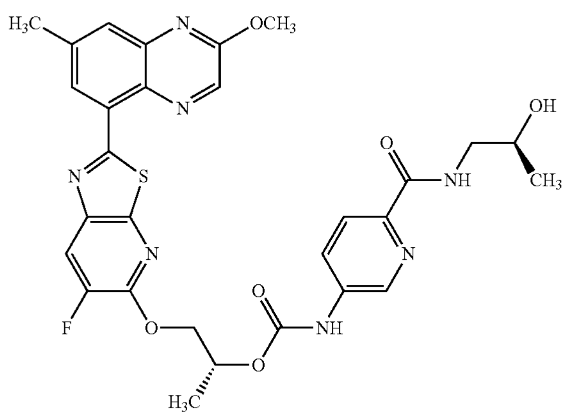 [SMILES: COc1cnc2c(-c3nc4cc(F)c(OC[C@@H](C)OC(=O)Nc5ccc(C(=O)NC[C@H](C)O)nc5)nc4s3)cc(C)cc2n1] | 689 | 622.2 | 1.17/H | ¹H NMR (500 MHz, DMSO-d₆) δ 10.17 (br. s., 1H), 8.63 (br. s., 1H), 8.58 (s, 1H), 8.48 (s, 1H), 8.43-8.33 (m, 2H), 8.03 (br. s., 1H), 7.94 (d, J = 8.5 Hz, 1H), 7.79 (s, 1H), 5.29 (br. s., 1H), 4.88 (d, J = 10.1 Hz, 1H), 4.52 (dd, J = 11.3, 5.5 Hz, 1H), 4.07 (s, 3H), 3.77 (br. s., 1H), 3.50-3.44 (m, 1H), 3.30 (br. s., 1H), 3.13 (d, J = 7.0 Hz, 1H), 2.61 (s, 3H), 1.44 (d, J = 6.4 Hz, 3H), 1.05 (d, J = 5.8 Hz, 3H). |
| 749 | 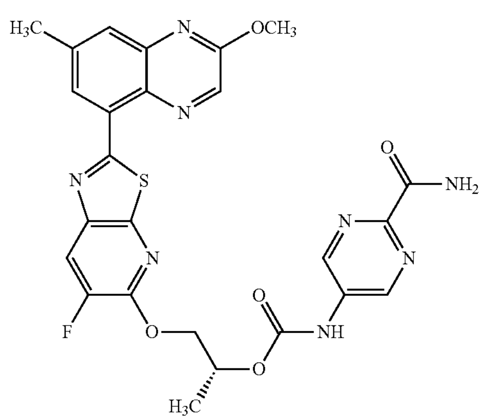 [SMILES: COc1cnc2c(-c3nc4cc(F)c(OC[C@@H](C)OC(=O)Nc5cnc(C(N)=O)nc5)nc4s3)cc(C)cc2n1] | 690 | 565.1 | 1.10/H | ¹H NMR (500 MHz, DMSO-d₆) δ 8.95 (br. s., 2H), 8.58 (s, 1H), 8.43 (s, 1H), 8.36 (d, J = 10.8 Hz, 1H), 8.19-8.01 (m, 2H), 7.75 (s, 1H), 7.65 (br. s., 1H), 5.35-5.26 (m, 1H), 4.84 (d, J = 9.8 Hz, 1H), 4.59-4.48 (m, 1H), 4.05 (s, 3H), 2.58 (s, 3H), 1.44 (d, J = 6.4 Hz, 3H). |

Example 750

(2R,3S)-3-((6-fluoro-2-(2-methoxy-7-methylquinoxalin-5-yl)thiazolo[5,4-b]pyridin-5-yl)oxy)butan-2-yl (6-(((S)-2-hydroxypropyl)carbamoyl)pyridin-3-yl)carbamate

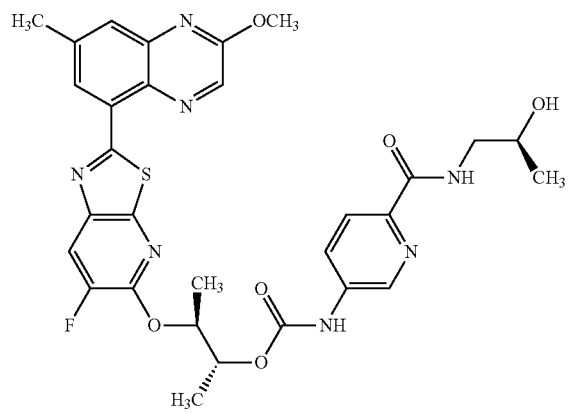

(750)

To a suspension of Example 715 (0.030 g, 0.051 mmol) in THF (0.506 ml) was added (S)-1-aminopropan-2-ol (0.114 g, 1.519 mmol) followed by magnesium chloride (0.047 g, 0.510 mmol). The reaction vial was sealed and heated to 65° C. overnight. The reaction mixture was diluted with EtOAc and filtered through Celite. The reaction mixture was concentrated, redissolved in DMF, filtered, and purified by preparative HPLC (Method D, 35 to 100% B in 20 minutes) to yield Example 750 (0.0129 g, 0.020 mmol, 40.1% yield $^1$H NMR (500 MHz, DMSO-$d_6$) δ 9.95 (br. s., 1H), 8.51 (d, J=8.2 Hz, 1H), 8.41 (s, 2H), 8.31 (d, J=10.7 Hz, 2H), 7.99 (br. s., 1H), 7.89 (t, J=7.3 Hz, 1H), 7.73 (s, 1H), 5.77 (d, J=6.7 Hz, 1H), 5.12 (d, J=6.4 Hz, 1H), 4.91 (s, 1H), 4.05 (s, 3H), 3.77-3.69 (m, 1H), 3.38-2.96 (m, 2H), 2.57 (s, 3H), 1.44 (d, J=6.4 Hz, 3H), 1.38 (d, J=6.4 Hz, 3H), 1.08-0.98 (m, 3H). LC-MS: method H, RT=1.23 min): MS (ESI) m/z: 636.1 (M+H)$^+$. Analytical HPLC Method B: 100% purity.

Examples 751 to 761

The following additional examples have been prepared, isolated and characterized using the methods described for Example 741 and the examples above.

| Ex. No. | Structure | ester | LCMS [M + H]$^+$ m/z | LCMS RT (Min)/ Method | NMR |
|---|---|---|---|---|---|
| 751 | 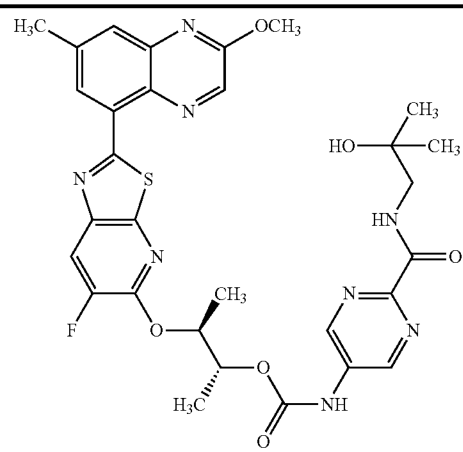 | 712 | 650.2 | 2.37/B | $^1$H NMR (500 MHz, DMSO-$d_6$) δ 10.23-10.17 (m, 1H), 8.90 (br. s., 2H), 8.48 (s, 1H), 8.43 (s, 1H), 8.37-8.30 (m, 2H), 7.75 (s, 1H), 5.78 (dd, J = 6.6, 2.3 Hz, 1H), 5.22-5.08 (m, 1H), 4.72 (s, 1H), 4.05 (s, 3H), 3.51-3.45 (m, 2H), 3.30-3.14 (m, 2H), 2.58 (s, 3H), 1.45 (d, J = 6.7 Hz, 3H), 1.40 (d, J = 6.4 Hz, 3H), 1.08 (d, J = 10.4 Hz, 6H). |
| 752 | 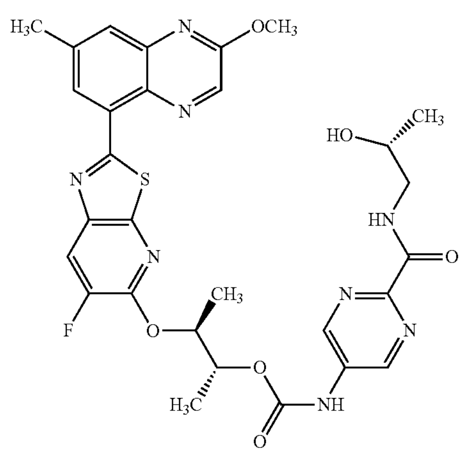 [SMILES: COc1cnc2c(-c3nc4cc(F)c(O[C@@H](C)[C@@H](C)OC(=O)Nc5cnc(C(=O)NC[C@@H](C)O)nc5)nc4s3)cc(C)cc2n1] | 712 | 637.2 | 1.14/H | $^1$H NMR (500 MHz, DMSO-$d_6$) δ 10.16 (br. s., 1H), 8.87 (br. s., 2H), 8.47 (s, 2H), 8.43 (s, 1H), 8.34 (d, J = 11.0 Hz, 1H), 7.75 (s, 1H), 5.78 (d, J = 6.7 Hz, 1H), 5.13 (d, J = 6.7 Hz, 1H), 4.86 (d, J = 4.9 Hz, 1H), 4.04 (s, 3H), 3.81-3.71 (m, 1H), 3.47 (s, 3H), 3.31-3.22 (m, 1H), 3.16-3.06 (m, 1H), 2.57 (s, 3H), 1.43 (d, J = 6.4 Hz, 2H), 1.38 (d, J = 6.4 Hz, 2H), 1.03 (d, J = 6.1 Hz, 3H). |

-continued

| Ex. No. | Structure | ester | LCMS [M + H]+ m/z | LCMS RT (Min)/ Method | NMR |
|---|---|---|---|---|---|
| 753 | 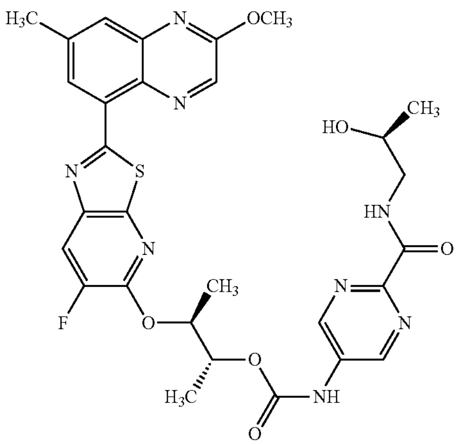 [SMILES: COc1cnc2c(-c3nc4cc(F)c(O[C@@H](C)[C@@H](C)OC(=O)Nc5cnc(C(=O)NC[C@H](C)O)nc5)nc4s3)cc(C)cc2n1] | 712 | 637.2 | 1.14/H | ¹H NMR (500 MHz, DMSO-d₆) δ 10.16 (br. s., 1H), 8.87 (br. s., 2H), 8.47 (s, 2H), 8.43 (s, 1H), 8.34 (d, J = 11.0 Hz, 1H), 7.75 (s, 1H), 5.78 (d, J = 6.7 Hz, 1H), 5.13 (d, J = 6.7 Hz, 1H), 4.86 (d, J = 4.9 Hz, 1H), 4.04 (s, 3H), 3.81-3.71 (m, 1H), 3.47 (s, 3H), 3.31-3.22 (m, 1H), 3.16-3.06 (m, 1H), 2.57 (s, 3H), 1.43 (d, J = 6.4 Hz, 2H), 1.38 (d, J = 6.4 Hz, 2H), 1.03 (d, J = 6.1 Hz, 3H). |
| 754 | 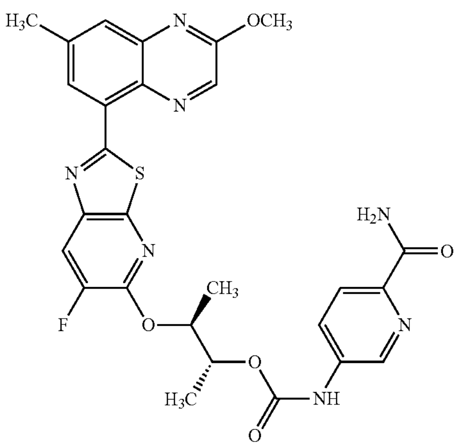 [SMILES: COc1cnc2c(-c3nc4cc(F)c(O[C@@H](C)[C@@H](C)OC(=O)Nc5ccc(C(N)=O)nc5)nc4s3)cc(C)cc2n1] | 715 | 578.2 | 1.23/H | ¹H NMR (500 MHz, DMSO-d₆) δ 10.07 (s, 1H), 8.60 (br. s., 1H), 8.53 (s, 1H), 8.45 (s, 1H), 8.38 (d, J = 10.8 Hz, 1H), 8.02-7.97 (m, 1H), 7.95-7.88 (m, 2H), 7.76 (s, 1H), 7.42 (br. s., 1H), 5.69 (dd, J = 6.4, 2.4 Hz, 1H), 5.20-5.11 (m, 1H), 4.06 (s, 3H), 2.59 (s, 3H), 1.45 (d, J = 6.4 Hz, 3H), 1.40 (d, J = 6.4 Hz, 3H). |
| 755 | 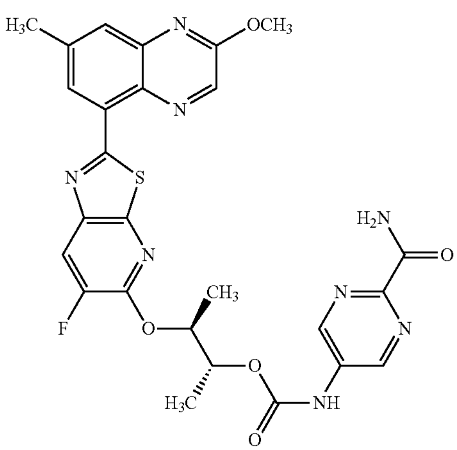 [SMILES: COc1cnc2c(-c3nc4cc(F)c(O[C@@H](C)[C@@H](C)OC(=O)Nc5cnc(C(N)=O)nc5)nc4s3)cc(C)cc2n1] | 712 | 579.0 | 1.14/H | ¹H NMR (500 MHz, DMSO-d₆) δ 10.27 (br. s., 1H), 8.92 (br. s., 2H), 8.59 (s, 1H), 8.48 (s, 1H), 8.41 (d, J = 10.8 Hz, 1H), 8.06 (br. s., 1H), 7.79 (s, 1H), 7.64 (br. s., 1H), 5.73 (d, J = 6.4 Hz, 1H), 5.18 (d, J = 4.4 Hz, 1H), 4.07 (s, 3H), 2.60 (s, 3H), 1.46 (d, J = 6.7 Hz, 3H), 1.41 (d, J = 6.7 Hz, 3H). |

| Ex. No. | Structure | ester | LCMS [M + H]+ m/z | LCMS RT (Min)/ Method | NMR |
|---|---|---|---|---|---|
| 756 | 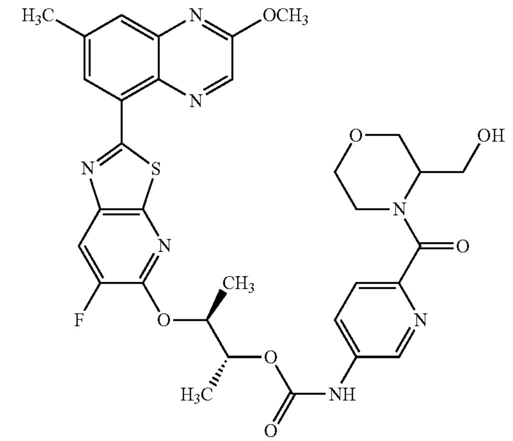 [SMILES: COc1cnc2c(-c3nc4cc(F)c(O[C@@H](C)[C@@H](C)OC(=O)Nc5ccc(C(=O)N6CCOCC6CO)nc5)nc4s3)cc(C)cc2n1] | 715 | 678.2 | 2.56/B | ¹H NMR (500 MHz, DMSO-d₆) δ 10.01 (br. s., 1H), 8.64 (s, 1H), 8.59-8.53 (m, 1H), 8.51 (s, 1H), 8.41 (d, J = 11.0 Hz, 1H), 8.05-7.93 (m, 1H), 7.82 (s, 1H), 7.59-7.52 (m, 1H), 5.67 (br. s., 1H), 5.17 (d, J = 6.1 Hz, 1H), 4.36-4.15 (m, 1H), 4.08 (s, 3H), 4.05-3.99 (m, 1H), 3.91 (s, 2H), 3.75 (br. s., 2H), 3.66-3.31 (m, 3H), 3.33-2.97 (m, 1H), 2.62 (s, 3H), 1.45 (d, J = 6.7 Hz, 3H), 1.40 (d, J = 6.4 Hz, 3H). |
| 757 | 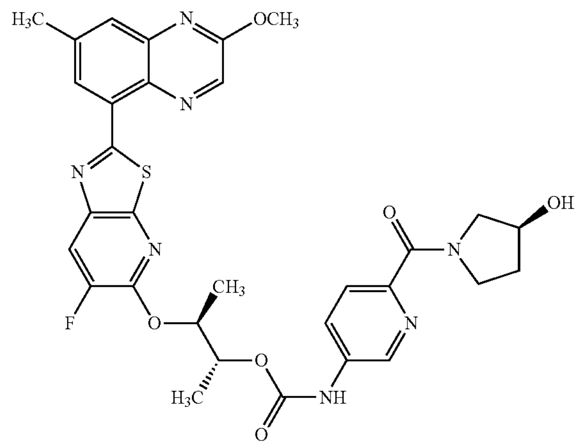 [SMILES: COc1cnc2c(-c3nc4cc(F)c(O[C@@H](C)[C@@H](C)OC(=O)Nc5ccc(C(=O)N6CC[C@H](O)C6)nc5)nc4s3)cc(C)cc2n1] | 715 | 648.2 | 2.41/B | ¹H NMR (500 MHz, DMSO-d₆) δ 9.99-9.88 (m, 1H), 8.52-8.48 (m, 1H), 8.42 (br. s., 1H), 8.38-8.28 (m, 2H), 8.12-7.87 (m, 1H), 7.74 (br. s., 1H), 7.69 (d, J = 7.9 Hz, 1H), 5.81-5.65 (m, 1H), 5.14 (br. s., 1H), 5.05-4.92 (m, 1H), 4.24 (br. s., 1H), 4.05 (s, 3H), 3.58 (d, J = 5.8 Hz, 3H), 3.51-3.32 (m, 1H), 2.58 (s, 3H), 1.93-1.65 (m, 2H), 1.45 (br. s., 3H), 1.39 (d, J = 6.1 Hz, 3H). |
| 758 | 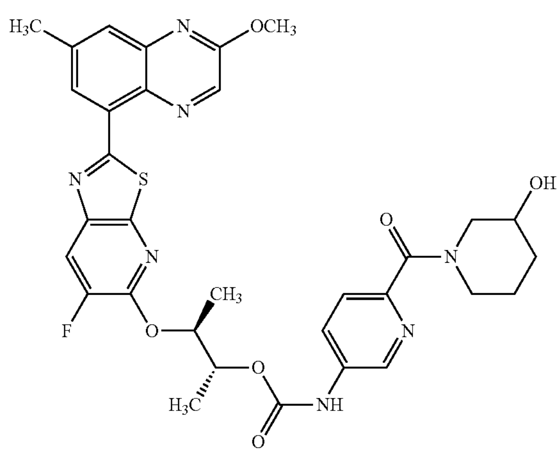 [SMILES: COc1cnc2c(-c3nc4cc(F)c(O[C@@H](C)[C@@H](C)OC(=O)Nc5ccc(C(=O)N6CCCC(O)C6)nc5)nc4s3)cc(C)cc2n1] | 715 | 662.2 | 2.47/B | ¹H NMR (500 MHz, DMSO-d₆) δ 9.96 (d, J = 18.9 Hz, 1H), 8.54 (br. s., 2H), 8.41 (br. s., 1H), 8.32 (d, J = 10.7 Hz, 1H), 7.96 (br. s., 1H), 7.74 (s, 1H), 7.50 (d, J = 8.9 Hz, 1H), 5.67 (br. s., 2H), 5.18-5.09 (m, 2H), 4.90 (d, J = 4.9 Hz, 1H), 4.05 (s, 3H), 3.84 (br. s., 1H), 3.47 (br. s., 1H), 3.14 (br. s., 1H), 2.90 (s, 1H), 2.82-2.64 (m, 1H), 2.56 (s, 3H), 1.90-1.70 (m, 2H), 1.45 (d, J = 6.4 Hz, 3H), 1.39 (d, J = 6.4 Hz, 3H). |

| Ex. No. | Structure | ester | LCMS [M + H]+ m/z | LCMS RT (Min)/ Method | NMR |
|---|---|---|---|---|---|
| 759 | 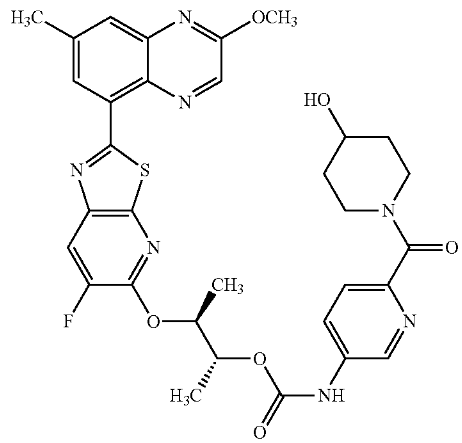 [SMILES: COc1cnc2c(-c3nc4cc(F)c(O[C@@H](C)[C@@H](C)OC(=O)Nc5ccc(C(=O)N6CCC(O)CC6)nc5)nc4s3)cc(C)cc2n1] | 715 | 662.0 | 2.97/B | ¹H NMR (500 MHz, DMSO-d₆) δ 9.95 (br. s., 1H), 8.53 (s, 2H), 8.40 (s, 1H), 8.30 (d, J = 10.7 Hz, 1H), 8.04-7.90 (m, 1H), 7.72 (s, 1H), 7.49 (br. s., 1H), 5.67 (br. s., 1H), 5.15 (d, J = 6.4 Hz, 1H), 4.90 (br. s., 1H), 4.04 (s, 3H), 3.74-3.55 (m, 4H), 3.24-2.95 (m, 2H), 2.57 (br. s., 3H), 1.78 (br. s., 1H), 1.68-1.54 (m, 1H), 1.44 (d, J = 6.1 Hz, 3H), 1.39 (d, J = 6.1 Hz, 3H), 1.27 (br. s., 1H). |
| 760 | 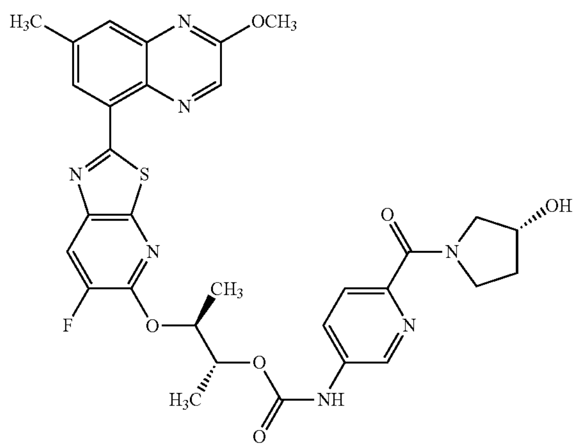 [SMILES: COc1cnc2c(-c3nc4cc(F)c(O[C@@H](C)[C@@H](C)OC(=O)Nc5ccc(C(=O)N6CC[C@@H](O)C6)nc5)nc4s3)cc(C)cc2n1] | 715 | 648.0 | 2.98/B | ¹H NMR (500 MHz, DMSO-d₆) δ 9.99-9.88 (m, 1H), 8.52-8.48 (m, 1H), 8.42 (br. s., 1H), 8.38-8.28 (m, 2H), 8.12-7.87 (m, 1H), 7.74 (br. s., 1H), 7.69 (d, J = 7.9 Hz, 1H), 5.81-5.65 (m, 1H), 5.14 (br. s., 1H), 5.05-4.92 (m, 1H), 4.24 (br. s., 1H), 4.05 (s, 3H), 3.58 (d, J = 5.8 Hz, 3H), 3.51-3.32 (m, 1H), 2.58 (s, 3H), 1.93-1.65 (m, 2H), 1.45 (br. s., 3H), 1.39 (d, J = 6.1 Hz, 3H). |
| 761 | 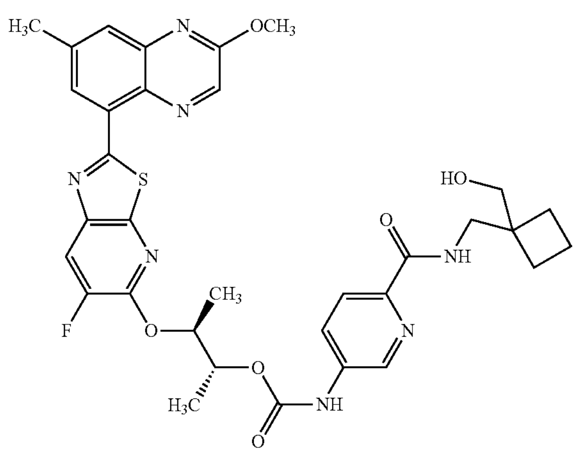 [SMILES: COc1cnc2c(-c3nc4cc(F)c(O[C@@H](C)[C@@H](C)OC(=O)Nc5ccc(C(=O)NCC6(CO)CCC6)nc5)nc4s3)cc(C)cc2n1] | 712 | 676.0 | 3.43/B | ¹H NMR (500 MHz, DMSO-d₆) δ 9.98 (br. s., 1H), 8.51 (d, J = 7.0 Hz, 2H), 8.45 (d, J = 11.6 Hz, 2H), 8.33 (d, J = 10.7 Hz, 1H), 7.99 (br. s., 1H), 7.90 (d, J = 7.9 Hz, 1H), 7.75 (s, 1H), 5.76 (d, J = 6.4 Hz, 1H), 5.14 (br. s., 1H), 4.83 (br. s., 1H), 4.06 (s, 3H), 3.36 (d, J = 4.9 Hz, 2H), 2.58 (s, 3H), 1.83-1.62 (m, 8H), 1.45 (d, J = 6.1 Hz, 3H), 1.39 (d, J = 6.4 Hz, 3H). |

Example 762

N-(2-((2-(2-methoxy-7-methylquinoxalin-5-yl)-7-methylthiazolo[5,4-b]pyridin-5-yl)oxy)ethyl)-4-methylbenzenesulfonamide

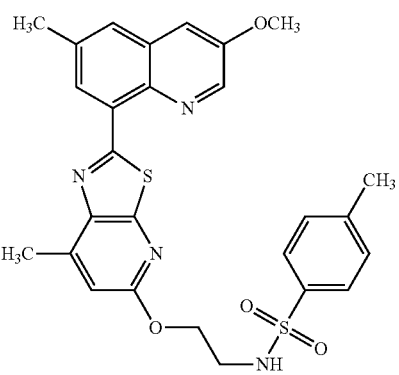
(762)

To a solution of Intermediate 662D (15 mg, 0.039 mmol) in DMF (1 mL) was added DIEA (0.069 mL, 0.393 mmol) and 4-methylbenzene-1-sulfonyl chloride (9.00 mg, 0.047 mmol). The mixture was stirred at room temperature for 1 hour. The reaction was quenched by 0.2 ml of MeOH. The reaction mixture was concentrated, redissolved in DMF, filtered, and purified by preparative HPLC (Method D, 65 to 100% B in 22 minutes) to yield Example 762 (7.52 mg, 0.014 mmol, 35.7% yield): $^1$H NMR (500 MHz, DMSO-d$_6$) δ 8.70 (s, 1H), 8.52 (s, 1H), 7.89 (t, J=5.4 Hz, 1H), 7.80 (s, 1H), 7.71 (d, J=8.0 Hz, 2H), 7.37 (d, J=8.0 Hz, 2H), 6.72 (s, 1H), 4.31 (t, J=5.5 Hz, 2H), 4.08 (s, 3H), 3.21 (d, J=5.5 Hz, 2H), 2.71 (s, 3H), 2.63 (s, 3H), 2.35 (s, 3H). LC-MS: method H, RT=1.23 min): MS (ESI) m/z: 536.1 (M+H)$^+$. Analytical HPLC Method B: 100% purity.

Example 763

6-fluoro-5-methoxy-2-(2-(methoxymethyl)-7-methylquinoxalin-5-yl)-7-methylthiazolo[5,4-b]pyridine

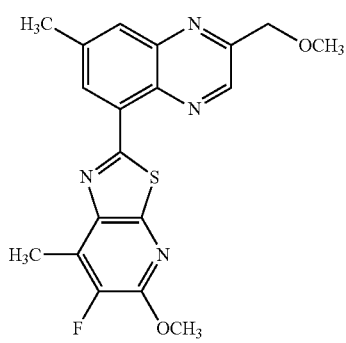
(763)

Intermediate 763A:
5-bromo-3-fluoro-2-methoxy-4-methylpyridine

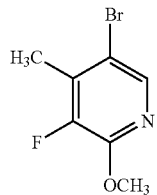
(763A)

3-fluoro-2-methoxy-4-methylpyridine (0.500 g, 3.54 mmol) was dissolved in AcOH (17.71 ml). Next, bromine (0.219 ml, 4.25 mmol) and sodium acetate (0.581 g, 7.09 mmol) were added, and the reaction mixture was heated to 80° C. overnight. The reaction was carefully quenched with saturated NaHCO$_3$ and extracted with EtOAc. The organic layer was washed with 1 N NaOH, water, then brine, then dried (Na$_2$SO$_4$), filtered, and concentrated in vacuo to yield Intermediate 763A (0.450 g, 2.045 mmol, 57.7% yield) as a white solid. LC-MS: Method H, RT=1.02 min, MS (ESI) m/z: 220.1 (M+H)$^+$.

Intermediate 763B: N-benzyl-5-fluoro-6-methoxy-4-methylpyridin-3-amine

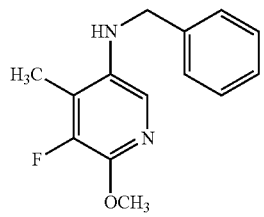
(763B)

Intermediate 763A (0.450 g, 2.045 mmol), copper(I) iodide (0.078 g, 0.409 mmol), potassium carbonate (0.424 g, 3.07 mmol), and L-proline (0.094 g, 0.818 mmol) was added. The reaction mixture was placed under vacuum and backfilled with argon. The solids were dissolved in DMSO (20.45 ml) and stirred for 5 min. To the reaction was added benzylamine (0.268 ml, 2.454 mmol) and the reaction mixture was heated to 80° C. overnight. The reaction mixture was diluted with water and EtOAc. The layers were separated and the organic layer was washed with water, washed with brine, dried with sodium sulfate, and concentrated under reduced pressure. Purified on ISCO using a 40 g column with 0-100% EtOAc in hexanes gradient to yield Intermediate 763B (0.123 g, 0.499 mmol, 24.42% yield): $^1$H NMR (400 MHz, CDCl$_3$) δ 7.39-7.27 (m, 6H), 4.33 (d, J=5.1 Hz, 2H), 3.93 (s, 3H), 3.48 (br. s., 1H), 2.12 (d, J=2.2 Hz, 3H). LC-MS: method H, RT=0.99 min, MS (ESI) m/z: 247.2 (M+H)$^+$.

Intermediate 763C: 5-fluoro-6-methoxy-4-methylpyridin-3-amine

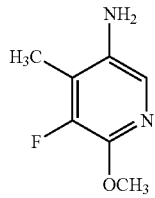

(763C)

Intermediate 763B (0.150 g, 0.609 mmol) was dissolved in MeOH (6.09 ml) and palladium on carbon (0.130 g, 0.122 mmol) was added. The reaction mixture was placed under vacuum and back filled with argon three times. The reaction mixture was placed under vacuum and back filled with hydrogen (1.228 mg, 0.609 mmol) three times. The reaction mixture was allowed to stir at room temperature for 3 h. The reaction mixture was filtered and concentrated to yield Intermediate 763C (0.074 g, 0.474 mmol, 78% yield) as a yellow solid. $^1$H NMR (400 MHz, CDCl$_3$) δ 7.41 (s, 1H), 3.94 (s, 3H), 3.33 (br. s., 1H), 2.13 (d, J=2.0 Hz, 3H). LC-MS: method H, RT=0.55 min, MS (ESI) m/z: MS (ESI) m/z: 157.0 (M+H)$^+$.

Intermediate 763D: 6-fluoro-5-methoxy-7-methyl-thiazolo[5,4-b]pyridin-2-amine

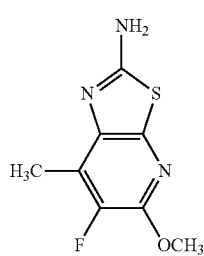

(763D)

Potassium thiocyanate (0.046 g, 0.474 mmol) was dissolved in acetic acid (1.137 ml) and cooled to 0° C. Intermediate 763C (0.074 g, 0.474 mmol) was dissolved in acetic acid (0.379 ml) and added dropwise. Bromine (0.049 ml, 0.948 mmol) was dissolved in acetic acid (0.379 ml) and added dropwise to the reaction mixture. The reaction mixture was allowed to warm to room temperature and stir overnight. The reaction mixture was concentrated under reduced pressure. The resultant residue was diluted with water and neutralized with 1 N NaOH. The aqueous solution was extracted with EtOAc×3. The combined organic layer was washed with brine, dried with sodium sulfate, and concentrated under reduced pressure to yield Intermediate 763D (0.099 g, 0.464 mmol, 98% yield). LC-MS: Method H, RT=0.71 min, MS (ESI) m/z: MS (ESI) m/z: 214.1 (M+H)$^+$.

Intermediate 763E: 2-bromo-6-fluoro-5-methoxy-7-methylthiazolo[5,4-b]pyridine

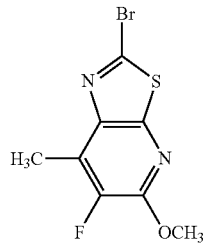

(763E)

Copper(II)bromide (0.178 g, 0.797 mmol) and t-butyl nitrite (0.095 ml, 0.797 mmol) were dissolved in MeCN (1.876 ml) and allowed to stir 10 minutes. Intermediate 763D (0.100 g, 0.469 mmol) was dissolved in MeCN (2.81 ml) and the copper solution was added. The reaction mixture was stirred for 2.5 h at 60° C. The reaction mixture was diluted with EtOAc, washed with 1 N HCl, saturated NaHCO$_3$, then brine, dried (Na$_2$SO$_4$), filtered, and concentrated in vacuo. Purified on ISCO using a 12 g column with 0-100% gradient of EtOAc in hexanes to yield Intermediate 763E (0.098 g, 0.354 mmol, 75% yield). $^1$H NMR (400 MHz, CDCl$_3$) δ 4.06 (s, 1H), 2.60 (d, J=2.2 Hz, 1H). LC-MS: method H, RT=1.13 min, MS (ESI) m/z: MS (ESI) m/z: 277.1 (M+H)$^+$.

Example 763

Intermediate I-2 (0.017 g, 0.054 mmol) and Intermediate 763E (0.015 g, 0.054 mmol) were dissolved in DMF (1 ml). PdCl$_2$(dppf)-CH$_2$Cl$_2$ adduct (2.65 mg, 3.25 µmol) was added and the reaction mixture was degassed by bubbling with argon for 15 minutes. Next, Na$_2$CO$_3$, 3 M aqueous solution (0.100 ml, 0.300 mmol) was added and the reaction mixture was degassed for 5 minutes, then sealed and heated to 90° C. in a microwave for 30 minutes. The reaction mixture was concentrated, redissolved in DMF, filtered, and purified by preparative HPLC (Method D, 60 to 100% B in 20 minutes) to yield Example 763 (0.0008 g, 1.831 µmol, 3.38% yield): LC-MS: method H, RT=1.30 min, MS (ESI) m/z: 385.2 (M+H)$^+$. Analytical HPLC Method B: 88% purity.

Example 764

(2R,3S)-3-((6-fluoro-2-(2-methoxy-7-methylquinoxalin-5-yl)thiazolo[5,4-b]pyridin-5-yl)oxy)butan-2-yl (2-(hydroxymethyl)pyrimidin-5-yl)carbamate

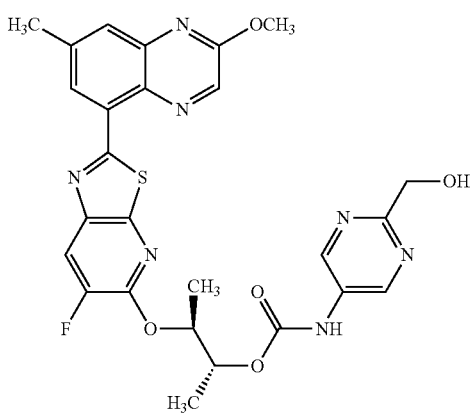

(764)

Example 712 (50 mg, 0.084 mmol) was solvated in THF (1 mL) and cooled to −78° C. To this mixture was added diisobutylaluminum hydride (1 M in toluene) (0.253 mL, 0.253 mmol) and the reaction mixture was stirred for 30 min. The reaction was quenched with 1 mL of a 1 M HCl solution at −78° C. The reaction mixture was allowed to thaw to room temperature and stirred for a total of 30 min. The mixture was diluted with EtOAc and washed with saturated NH₄Cl before being dried over MgSO₄ and filtered over a pad of SiO₂ gel. The filtrate was concentrated and resubjected to identical reaction conditions. The reaction mixture was diluted with sat'd Rochelle's salt and allowed to stir overnight. The reaction mixture was diluted with EtOAc and the layers were separated. The aqueous layer was back extracted with EtOAc x3 and the combined organic layer was washed with brine, dried with sodium sulfate, and concentrated under reduced pressure to yield Example 764 (24.2 mg, 0.042 mmol, 49.8% yield): $^1$H NMR (400 MHz, CDCl₃) δ 8.91-8.84 (m, 2H), 8.58 (d, J=1.8 Hz, 1H), 8.55 (s, 1H), 8.01 (d, J=10.3 Hz, 1H), 7.85-7.74 (m, 1H), 6.69-6.53 (m, 1H), 5.75 (dd, 2.5 Hz, 1H), 5.27 (dd, 2.6 Hz, 1H), 4.82 (d, J=4.8 Hz, 2H), 4.16 (s, 3H), 3.49 (s, 1H), 2.67 (s, 3H), 1.50 (t, J=6.9 Hz, 6H). LC-MS: method H, RT=1.23 min): MS (ESI) m/z: 566.2 (M+H)⁺. Analytical HPLC Method B: 95% purity.

Example 765

(2R,3S)-3-((6-fluoro-2-(2-methoxy-7-methylquinoxalin-5-yl)thiazolo[5,4-b]pyridin-5-yl) oxy)butan-2-yl (6-(2-hydroxypropan-2-yl)pyridin-3-yl)carbamate

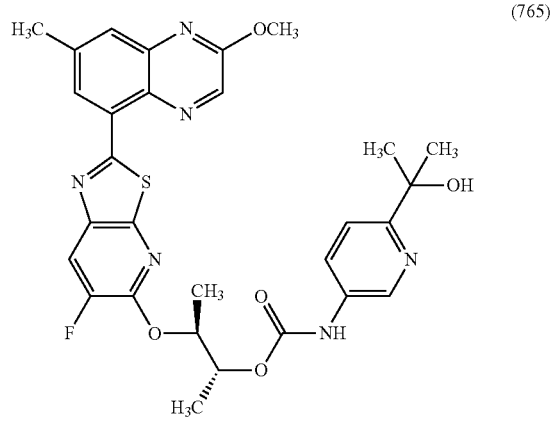 [SMILES: COc1cnc2c(-c3nc4cc(F)c(O[C@@H](C)[C@@H](C)OC(=O)Nc5ccc(C(C)(C)O)nc5)nc4s3)cc(C)cc2n1]

(765)

A solution of Example 715 (0.045 g, 0.076 mmol) in THF (1 mL) was cooled to −78° C. Methylmagnesium bromide (0.101 mL, 0.304 mmol) was added and the mixture was allowed to warm to room temperature. The mixture was stirred for 1 h. The reaction mixture was diluted with water and EtOAc. The layers were separated and the organic layer was washed with brine, dried with sodium sulfate, and concentrated under reduced pressure. Purified by ISCO using a 24 g column eluting with 0-70% EtOAc in DCM to yield Example 765 (0.015 g, 0.025 mmol, 33.3% yield). $^1$H NMR (400 MHz, CDCl₃) δ 8.56 (d, J=1.8 Hz, 2H), 8.37 (s, 1H), 7.98 (d, J=10.3 Hz, 1H), 7.77 (s, 1H), 7.31 (s, 2H), 6.59 (br. s., 1H), 5.66 (br. s., 1H), 5.23 (dd, J=6.5, 3.0 Hz, 1H), 4.13 (s, 3H), 2.65 (s, 3H), 1.48 (d, J=6.6 Hz, 3H), 1.46 (d, J=6.6 Hz, 3H), 1.25 (s, 6H). LC-MS: method H, RT=1.08 min, MS (ESI) m/z: 593.2 (M+H)⁺.

The methyl ketone (2R,3S)-3-((6-fluoro-2-(2-methoxy-7-methylquinoxalin-5-yl) thiazolo[5,4-b]pyridin-5-yl)oxy)butan-2-yl (6-acetylpyridin-3-yl)carbamate was also isolated from the reaction as Intermediate 765A (0.020 g, 0.035 mmol 35% yield), which will be used below. LC-MS: method H, RT=1.31 min, MS (ESI) m/z: 577.2 (M+H)⁺. Analytical HPLC Method B: 99% purity.

Example 766

(2R,3S)-3 #6-fluoro-2-(2-methoxy-7-methylquinoxalin-5-yl)thiazolo[5,4-b]pyridin-5-yl)oxy)butan-2-yl (6-(1-hydroxyethyl)pyridin-3-yl)carbamate

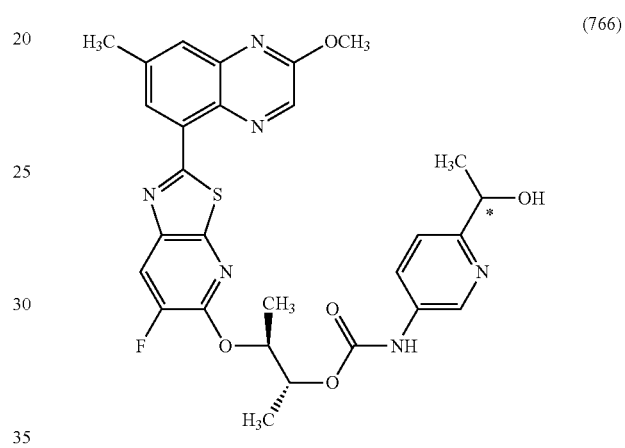

(766)

Intermediate 765A (0.020 g, 0.035 mmol) was dissolved in THF (0.347 ml) and cooled to −78° C. To the cooled reaction mixture was added DIBAL-H in toluene (0.087 ml, 0.087 mmol), and the reaction mixture was allowed to stir for 1 h. The reaction mixture was allowed to warm to room temperature and saturated solution of Rochelle's salt was added. The resulting mixture was allowed to stir overnight. The reaction mixture was diluted with EtOAc and water. The layers were separated and the organic layer was washed with brine, dried with sodium sulfate and concentrated under reduced pressure. The reaction mixture was concentrated, redissolved in DMF, filtered, and purified by preparative HPLC (Method D, 60 to 100% B in 15 minutes, then a 6 minute hold time) to yield the racemic product. The reaction was further purified 35% EtOH/65% CO₂ in a 15 min run, Lux 5u Cellulose-4, 21×250 mm, 5 micron column, flow rate 45 mL/min, 150 Bar, 40° C. and UV detection was set to 220 nm to yield Example 766 (3.3 mg, 5.48 μmol, 15.78% yield) as the first eluting isomer: $^1$H NMR (500 MHz, DMSO-d₆) δ 9.79 (br. s., 1H), 8.63 (br. s., 1H), 8.48 (s, 2H), 8.37 (d, J=10.7 Hz, 1H), 7.80 (s, 2H), 5.64 (d, J=4.9 Hz, 1H), 5.15 (d, J=5.8 Hz, 1H), 4.07 (s, 3H), 3.56-3.48 (m, 3H), 2.61 (s, 3H), 1.44 (d, J=6.4 Hz, 3H), 1.38 (d, J=6.4 Hz, 3H). LC-MS: method H, RT=1.08 min, MS (ESI) m/z: 579.2 (M+H)⁺. Analytical HPLC Method B: 99% purity.

Example 767

(2R,3S)-3-((6-fluoro-2-(2-methoxy-7-methylquinoxalin-5-yl)thiazolo[5,4-b]pyridin-5-yl)oxy)butan-2-yl (6-(1-hydroxyethyl)pyridin-3-yl)carbamate

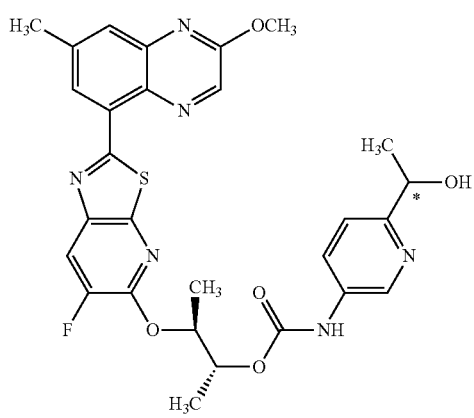

(767)

Example 768

(R)-1-((6-fluoro-2-(2-methoxy-7-methylquinoxalin-5-yl)thiazolo[5,4-b]pyridin-5-yl)oxy)propan-2-yl (2-(hydroxymethyl)pyrimidin-5-yl)carbamate

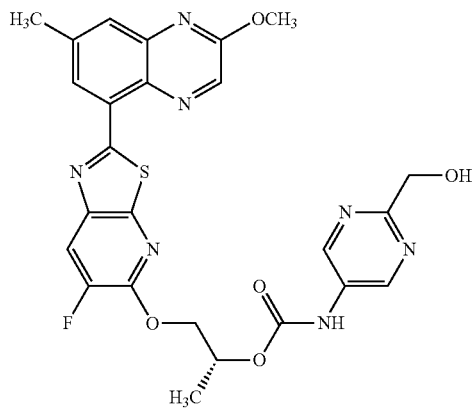

(768)

Intermediate 765A (0.020 g, 0.035 mmol) was dissolved in THF (0.347 ml) and cooled to −78° C. To the cooled reaction, was added DIBAL-H in toluene (0.087 ml, 0.087 mmol), and the reaction mixture was allowed to stir for 1 h. The reaction mixture was allowed to warm to room temperature and sat'd solution of Rochelle's salt was added. The reaction mixture was allowed to stir overnight. The reaction mixture was diluted with EtOAc and water. The layers were separated and the organic layer was washed with brine, dried with sodium sulfate and concentrated under reduced pressure. The reaction mixture was concentrated, redissolved in DMF, filtered, and purified by preparative HPLC (Method D, 60 to 100% B in 15 minutes, then a 6 minute hold time) to yield the racemic product. The reaction was further purified as above 35% EtOH/65% $CO_2$ in a 15 min run, Lux 5u Cellulose-4, 21×250 mm, 5 micron column, flow rate 45 mL/min, 150 Bar, 40° C. and UV detection was set to 220 nm to yield Example 767 (2.9 mg, 4.66 μmol, 13.4% yield) as the second eluting isomer: $^1$H NMR (500 MHz, DMSO-$d_6$) δ 9.80-9.64 (m, 1H), 8.63 (s, 1H), 8.48 (s, 2H), 8.37 (d, J=10.7 Hz, 1H), 7.80 (s, 2H), 7.43-7.35 (m, 1H), 5.69-5.60 (m, 1H), 5.22-5.10 (m, 1H), 4.64 (d, J=6.4 Hz, 1H), 4.07 (s, 3H), 3.55 (br. s., 4H), 2.61 (s, 3H), 1.45 (d, J=6.7 Hz, 3H), 1.38 (d, J=6.7 Hz, 3H). LC-MS: method H, RT=1.08 min, MS (ESI) m/z: 579.2 (M+H)$^+$. Analytical HPLC Method B: 99% purity.

Example 689 (50 mg, 0.086 mmol) was solvated in THF (1 mL) and cooled to −78° C. To this mixture was added diisobutylaluminum hydride (1 M in toluene) (0.259 mL, 0.259 mmol) and stirred for 30 min. The reaction was quenched with 1 mL of a 1 M HCl solution at −78° C. The reaction mixture was allowed to thaw to room temperature and stirred for a total of 30 min. The mixture was diluted with EtOAc and washed with saturated $NH_4Cl$ before being dried over $MgSO_4$ and filtered over a pad of $SiO_2$ gel to remove aluminates. The filtrate was concentrated and resubjected to identical reaction conditions. The reaction mixture was diluted with sat'd Rochelle's salt and allowed to stir overnight. The reaction mixture was diluted with EtOAc and the layers were separated. The aqueous layer was back extracted with EtOAc x3 and the combined organic layer was washed with brine, dried with sodium sulfate, and concentrated under reduced pressure. The reaction was purified on ISCO using a 12 g column eluting with 0-100% EtOAc in hexanes to yield Example 768 (19.60 mg, 0.034 mmol, 39.1% yield) as a yellow solid. $^1$H NMR (400 MHz, CDCl$_3$) δ 8.88 (br. s., 2H), 8.59 (s, 1H), 8.57 (s, 1H), 8.03 (d, J=10.3 Hz, 1H), 7.81 (s, 1H), 6.67 (br. s., 1H), 5.44 (dt, J=6.3, 3.0 Hz, 1H), 4.89-4.78 (m, 3H), 4.57 (d, J=6.2 Hz, 1H), 4.16 (s, 3H), 3.50 (br. s., 1H), 2.68 (s, 3H), 1.53 (d, J=6.4 Hz, 3H). MS (ESI) m/z: 552.1 (M+H)$^+$. LC-MS: method H, RT=1.12 min, MS (ESI) m/z: 552.1 (M+H)$^+$. Analytical HPLC Method B: 95% purity.

Example 769

(2R,3S)-3-((2-(6-chloro-3-methoxyquinolin-8-yl)-6-fluorothiazolo[5,4-b]pyridin-5-yl)oxy)butan-2-yl (2-methylpyrimidin-5-yl)carbamate

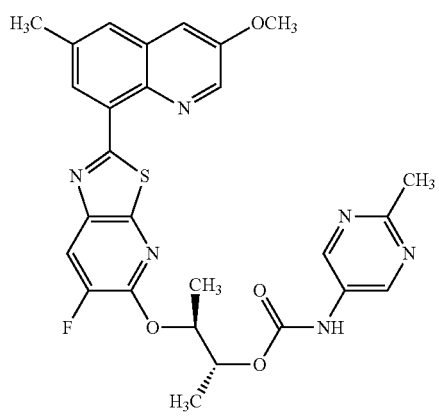

(769)

Intermediate I-121 (15 mg, 0.047 mmol), Intermediate I-135 (21.26 mg, 0.052 mmol) and PdCl$_2$(dppf) (2.061 mg, 2.82 μmol) were dissolved in dioxane (469 μl) and Na$_2$CO$_3$ (211 μl, 0.422 mmol) and heated to 100° C. in an oil bath for 2 hours. The reaction mixture was cooled to ambient temperature, diluted with EtOAc, washed with water, then brine, dried (Na$_2$SO$_4$), filtered, and concentrated in vacuo. The reaction mixture was concentrated, redissolved in DMF, filtered, and purified by preparative HPLC (Method D, 25 to 100% B in 15 minutes) to yield Example 769 (7.2, 12.65 mmol, 2.70E+04% yield): $^1$H NMR (500 MHz, DMSO-d$_6$) δ 9.81 (br. s., 1H), 8.77 (br. s., 1H), 8.68 (br. s., 2H), 8.55 (s, 1H), 8.41 (d, J=10.7 Hz, 1H), 8.19 (s, 1H), 7.93 (br. s., 1H), 5.73 (d, J=6.4 Hz, 1H), 5.13 (d, J=6.1 Hz, 1H), 4.00 (s, 3H), 2.46 (s, 3H), 1.44 (d, J=6.4 Hz, 3H), 1.38 (d, J=6.4 Hz, 3H). LC-MS: method H, RT=1.42, MS (ESI) m/z: 569.1 (M+H)$^+$. Analytical HPLC Method B: 100%

Examples 770 to 775

The following additional examples have been prepared, isolated and characterized using the methods described for Example 769 and the examples above. If necessary, removal of silyl protecting groups was accomplished by treatment of the protected compound with a solution of 90% MeOH, 9.9% water, and 0.1% TFA or MeOH/HCl (20/1) solution to afford the desired compound.

| Ex. No. | Structure | Boronic acid | Chloride | LCMS [M + H]$^+$ m/z | LCMS RT (Min) Method H | NMR |
|---|---|---|---|---|---|---|
| 770 | 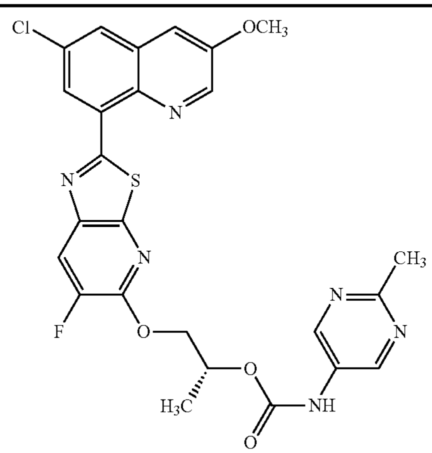 | I-121 | I-139 | 555.1 | 1.40 | $^1$H NMR (500 MHz, DMSO-d$_6$) δ 10.03-9.92 (m, 1H), 8.82 (br. s., 1H), 8.73 (br. s., 2H), 8.56 (s, 1H), 8.44 (d, J = 10.7 Hz, 1H), 8.19 (s, 1H), 7.93 (br. s., 1H), 5.28 (br. s., 1H), 4.84 (d, J = 11.6 Hz, 1H), 4.55 (dd, J = 11.7, 6.3 Hz, 1H), 4.00 (s, 3H), 2.50-2.50 (m, 3H), 1.43 (d, J = 6.4 Hz, 3H). |
| 771 | 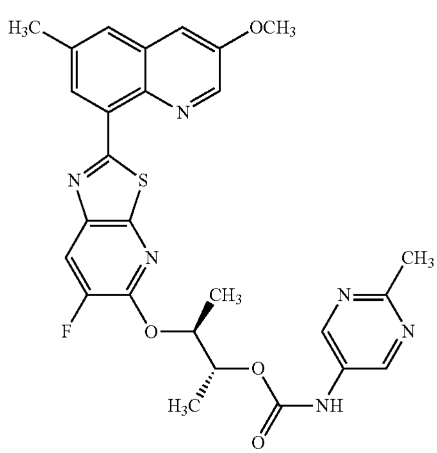 | I-124 | I-139 | 535.2 | 1.03 | $^1$H NMR (500 MHz, DMSO-d$_6$) δ 8.73 (br. s., 2H), 8.58 (br. s., 1H), 8.47-8.38 (m, 1H), 7.89 (d, J = 9.8 Hz, 1H), 7.21-6.97 (m, 2H), 5.28 (br. s., 1H), 4.84 (d, J = 11.6 Hz, 1H), 4.62-4.50 (m, 1H), 4.00 (s, 3H), 2.61 (s, 3H), 1.48-1.40 (m, 3H). |

-continued

| Ex. No. | Structure | Boronic acid | Chloride | LCMS [M + H]+ m/z | LCMS RT (Min) Method H | NMR |
|---|---|---|---|---|---|---|
| 772 | 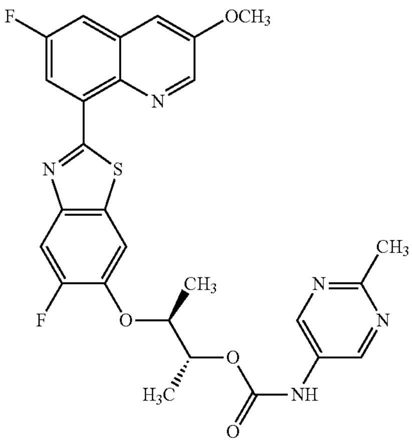 [SMILES: COc1cnc2c(-c3nc4cc(F)c(O[C@@H](C)[C@@H](C)OC(=O)Nc5cnc(C)nc5)cc4s3)cc(F)cc2c1] | I-136 | I-130 | 552.2 | 1.09 | 1H NMR (500 MHz, DMSO-d6) δ 8.77 (br. s., 1H), 8.66 (br. s., 2H), 8.41 (d, J = 9.5 Hz, 1H), 7.99 (d, J = 7.9 Hz, 1H), 7.93-7.82 (m, 3H), 5.04 (d, J = 6.4 Hz, 1H), 4.75 (d, J = 6.1 Hz, 1H), 3.93 (s, 3H), 2.48 (br. s., 3H), 1.33 (br. s., 6H). |
| 773 | 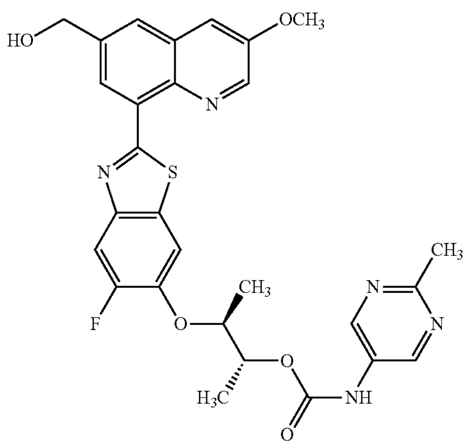 [SMILES: COc1cnc2c(-c3nc4cc(F)c(O[C@@H](C)[C@@H](C)OC(=O)Nc5cnc(C)nc5)cc4s3)cc(CO)cc2c1] | I-140 | I-130 | 564.3 | 0.92 | 1H NMR (500 MHz, DMSO-d6) δ 9.96 (br. s., 1H), 8.83 (br. s., 1H), 8.75 (br. s., 2H), 8.06-7.99 (m, 2H), 7.98-7.93 (m, 2H), 5.22-5.05 (m, 1H), 4.81 (br. s., 2H), 4.00 (br. s., 3H), 2.55 (br. s., 5H), 1.40 (br. s., 6H). |
| 774 | 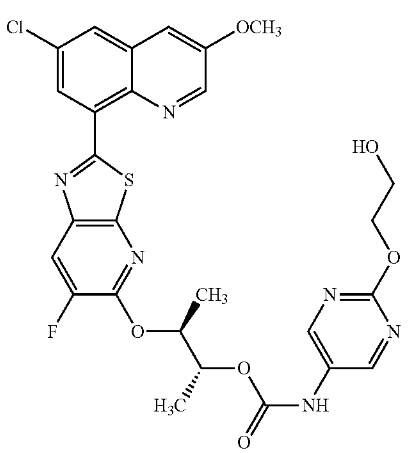 [SMILES: COc1cnc2c(-c3nc4cc(F)c(O[C@@H](C)[C@@H](C)OC(=O)Nc5cnc(OCCO)nc5)nc4s3)cc(Cl)cc2c1] | I-121 | I-137 | 615.1 | 1.18 | 1H NMR (500 MHz, DMSO-d6) δ 9.66 (br. s., 1H), 8.76 (br. s., 1H), 8.59-8.56 (m, 2H), 8.54 (d, J = 2.1 Hz, 1H), 8.40 (d, J = 10.7 Hz, 1H), 8.17 (d, J = 2.1 Hz, 1H), 7.91 (d, J = 2.7 Hz, 1H), 5.72 (dd, J = 6.6, 2.3 Hz, 1H), 5.11 (dd, J = 6.4, 2.1 Hz, 1H), 4.87 (s, 1H), 4.22-4.10 (m, 2H), 3.99 (s, 3H), 3.66 (d, J = 5.5 Hz, 2H), 1.43 (d, J = 6.4 Hz, 3H), 1.37 (d, J = 6.7 Hz, 3H). |

| Ex. No. | Structure | Boronic acid | Chloride | LCMS [M + H]⁺ m/z | LCMS RT (Min) Method H | NMR |
|---|---|---|---|---|---|---|
| 775 | 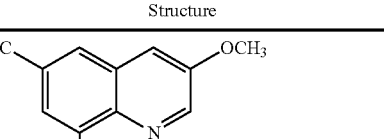 | I-124 | I-137 | 595.0 | 1.08 | ¹H NMR (500 MHz, DMSO-d$_6$) δ 9.71-9.54 (m, 1H), 8.65 (d, J = 2.1 Hz, 1H), 8.56-8.46 (m, 3H), 8.33 (d, J = 10.7 Hz, 1H), 7.83-7.72 (m, 2H), 5.63 (dd, J = 6.6, 2.3 Hz, 1H), 5.14-4.99 (m, 1H), 4.76 (s, 1H), 4.19-4.03 (m, 2H), 3.92 (s, 3H), 3.60 (d, J = 5.5 Hz, 2H), 2.53 (s, 3H), 1.36 (d, J = 6.4 Hz, 3H), 1.31 (d, J = 6.7 Hz, 3H). |

Example 776

(2R,3S)-3-((2-(6-chloro-3-methoxyquinolin-8-yl)-6-fluorothiazolo[5,4-b]pyridin-5-yl) oxy)butan-2-yl (5-fluoropyridin-3-yl)carbamate Intermediate 776A: (2R,3S)-3-((2-(6-chloro-3-methoxyquinolin-8-yl)-6-fluorothiazolo[5,4-b]pyridin-5-yl)oxy)butan-2-ol

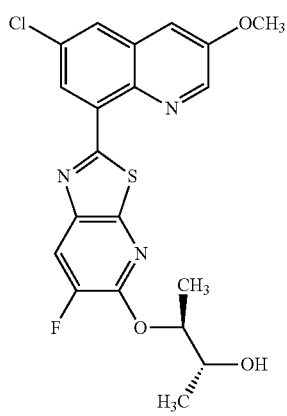

(776A)

(776)

Intermediate I-121 (75 mg, 0.235 mmol), Intermediate I-133 (64.7 mg, 0.235 mmol) and PdCl$_2$(dppf) (10.30 mg, 0.014 mmol) were dissolved in dioxane (2347 μl) and Na$_2$CO$_3$ (1056 μl, 2.112 mmol) and heated to 100° C. in an oil bath for 2 hours. The reaction mixture was cooled to ambient temperature, diluted with EtOAc, washed with water, then brine, dried (Na$_2$SO$_4$), filtered, and concentrated in vacuo. Purified on ISCO using 0-100% EtOAc in DCM on a 24 g column to yield Intermediate 776A (0.054 g, 0.124 mmol, 53.0% yield) as a yellow solid. ¹H NMR (400 MHz, CDCl$_3$) δ 8.80 (dd, J=16.2, 2.5 Hz, 2H), 8.02 (d, J=10.3 Hz, 1H), 7.85 (d, J=2.4 Hz, 1H), 7.41 (d, J=2.9 Hz, 1H), 5.48-5.35 (m, 1H), 4.22-4.10 (m, 1H), 4.03 (s, 3H), 2.56-2.47 (m, 1H), 1.46 (d, J=6.4 Hz, 3H), 1.33 (d, J=6.6 Hz, 3H). LC-MS: method H, RT=1.23 min, MS (ESI) m/z: 433.9 (M+H)⁺.

Intermediate 776B: (2R,3S)-3-((2-(6-chloro-3-methoxyquinolin-8-yl)-6-fluorothiazolo[5,4-b]pyridin-5-yl)oxy)butan-2-yl carbonochloridate

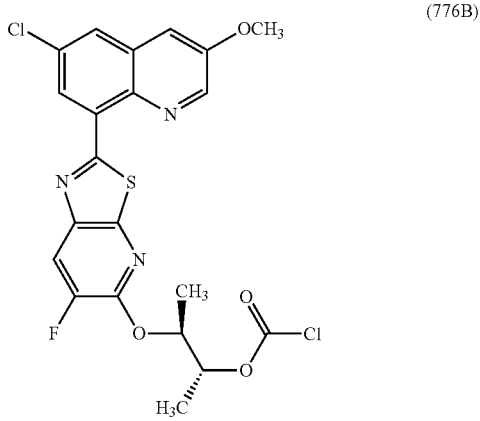 [SMILES: COc1cnc2c(-c3nc4cc(F)c(O[C@@H](C)[C@@H](C)OC(=O)Cl)nc4s3)cc(Cl)cc2c1]
(776B)

To a solution of Intermediate 776A (0.054 g, 0.124 mmol) in THF (5 mL) at room temperature was added 15% phosgene in toluene (0.439 mL, 0.622 mmol), and the mixture was stirred at room temperature overnight. Solvent was completely removed to give Intermediate 776B (0.062 g, 0.112 mmol, 90% yield) as a yellow solid. LC-MS: method H, RT=1.39 min MS (ESI) m/z: 495.9 (M+H)$^+$.

Example 776

5-fluoropyridin-3-amine (3.39 mg, 0.030 mmol) and pyridine (0.016 mL, 0.201 mmol) were dissolved in DCM (2 mL). To this solution was added Intermediate 776B (0.010 g, 0.020 mmol) as a solution in DCM (1 mL). The reaction mixture was allowed to stir for 1 h. The reaction mixture was concentrated under reduced pressure, redissolved in DMF, filtered, and purified by preparative HPLC (Method D, 25 to 100% B in 15 minutes) to yield Example 776 (0.0072 g, 0.013 mmol, 62.5% yield): $^1$H NMR (500 MHz, DMSO-d$_6$) δ 10.07 (br. s., 1H), 8.76 (s, 1H), 8.54 (s, 1H), 8.44-8.37 (m, 2H), 8.18 (s, 1H), 8.14 (s, 1H), 7.92 (d, J=2.4 Hz, 1H), 7.81 (br. s., 1H), 5.71 (d, J=6.1 Hz, 1H), 5.17 (d, J=5.2 Hz, 1H), 4.00 (s, 3H), 1.46 (d, J=6.4 Hz, 3H), 1.41 (d, J=6.4 Hz, 3H). LC-MS: method H, RT=1.28 min, MS (ESI) m/z: 572.0 (M+H)$^+$. Analytical HPLC Method B: 100% purity.

Examples 777 to 791

The following additional examples have been prepared, isolated and characterized using the methods described for Example 776 and the examples above. If necessary, removal of silyl protecting groups was accomplished by treatment of the protected compound with a solution of 90% MeOH, 9.9% water, and 0.1% TFA or MeOH/HCl (20/1) solution to afford the desired compound.

| Ex. No. | Structure | Amine | LCMS [M + H]$^+$ m/z | LCMS RT (Min) Method H | NMR |
|---|---|---|---|---|---|
| 777 | 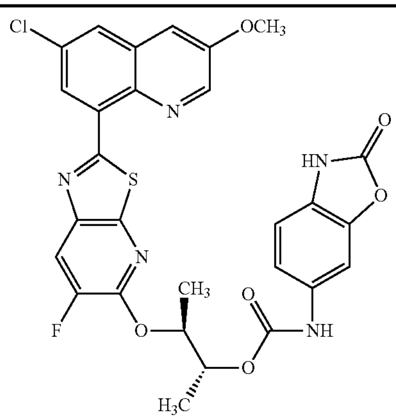 | | 610.0 | 1.50 | $^1$H NMR (500 MHz, DMSO-d$_6$) δ 11.39 (s, 1H), 9.53 (br. s., 1H), 8.70 (br. s., 1H), 8.52 (s, 1H), 8.37 (d, J = 11.0 Hz, 1H), 8.14 (s, 1H), 7.88 (d, J = 2.4 Hz, 1H), 7.37 (br. s., 1H), 7.09 (br. s., 1H), 6.90 (d, J = 8.2 Hz, 1H), 5.66 (d, J = 4.6 Hz, 1H), 5.13 (d, J = 4.3 Hz, 1H), 3.98 (s, 3H), 1.45 (d, J = 6.4 Hz, 3H), 1.38 (d, J = 6.4 Hz, 3H). |
| 778 | 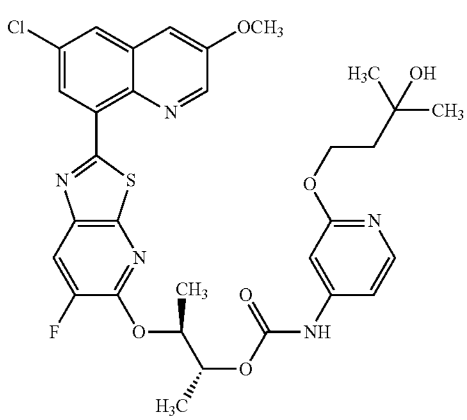 [SMILES: COc1cnc2c(-c3nc4cc(F)c(O[C@@H](C)[C@@H](C)OC(=O)Nc5ccnc(OCCC(C)(C)O)c5)nc4s3)cc(Cl)cc2c1] | | 656.0 | 1.08 | $^1$H NMR (500 MHz, DMSO-d$_6$) δ 9.90 (s, 1H), 8.69 (d, J = 2.4 Hz, 1H), 8.50 (s, 1H), 8.35 (d, J = 10.7 Hz, 1H), 8.13 (s, 1H), 7.94-7.84 (m, 2H), 7.00-6.95 (m, 1H), 6.76 (br. s., 1H), 5.77-5.64 (m, 1H), 5.23-5.09 (m, 1H), 4.19 (dt, J = 19.8, 7.4 Hz, 2H), 3.97 (s, 3H), 3.49 (s, 1H), 1.74-1.68 (m, 2H), 1.44 (d, J = 6.4 Hz, 3H), 1.38 (d, J = 6.4 Hz, 3H), 1.10 (s, 6H). |

-continued

| Ex. No. | Structure | Amine | LCMS [M + H]+ m/z | LCMS RT (Min) Method H | 1H NMR |
|---|---|---|---|---|---|
| 779 | 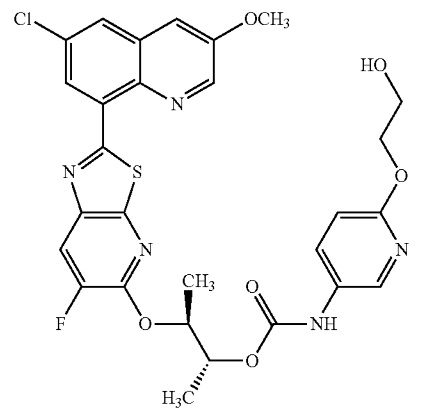 [SMILES: COc1cnc2c(-c3nc4cc(F)c(O[C@@H](C)[C@@H](C)OC(=O)Nc5ccc(OCCO)nc5)nc4s3)cc(Cl)cc2c1] | | 614.1 | 1.06 | 1H NMR (500 MHz, DMSO-d6) δ 9.49 (br. s., 1H), 8.79 (br. s., 1H), 8.56 (s, 1H), 8.42 (d, J = 10.7 Hz, 1H), 8.19 (s, 1H), 8.12 (br. s., 1H), 7.93 (br. s., 1H), 7.76 (br. s., 1H), 6.72 (br. s., 1H), 5.68 (d, J = 6.7 Hz, 1H), 5.12 (d, J = 6.7 Hz, 1H), 4.18-4.06 (m, 2H), 4.00 (s, 3H), 3.65 (t, J = 4.9 Hz, 2H), 3.36 (br. s., 1H), 1.45 (d, J = 6.4 Hz, 3H), 1.38 (d, J = 6.7 Hz, 3H). |
| 780 | 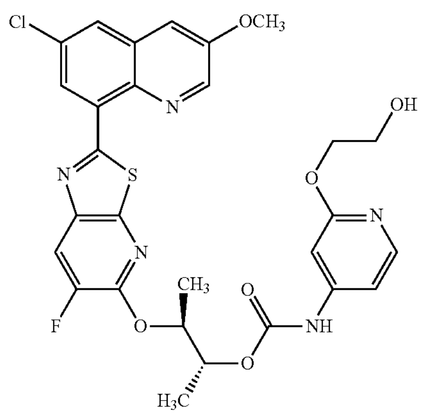 [SMILES: COc1cnc2c(-c3nc4cc(F)c(O[C@@H](C)[C@@H](C)OC(=O)Nc5ccnc(OCCO)c5)nc4s3)cc(Cl)cc2c1] | | 614.1 | 1.06 | 1H NMR (500 MHz, DMSO-d6) δ 9.95 (s, 1H), 8.74 (d, J = 2.7 Hz, 1H), 8.55 (d, J = 2.1 Hz, 1H), 8.41 (d, J = 11.0 Hz, 1H), 8.18 (d, J = 1.8 Hz, 1H), 7.94-7.88 (m, 2H), 7.02 (d, J = 5.5 Hz, 1H), 6.82 (s, 1H), 5.70 (d, J = 6.7 Hz, 1H), 5.16 (d, J = 6.7 Hz, 1H), 4.14 (dq, J = 19.5, 5.5 Hz, 2H), 4.00 (s, 3H), 3.61 (d, J = 4.0 Hz, 2H), 3.39 (s, 1H), 1.45 (d, J = 6.4 Hz, 3H), 1.39 (d, J = 6.4 Hz, 3H). |
| 781 | 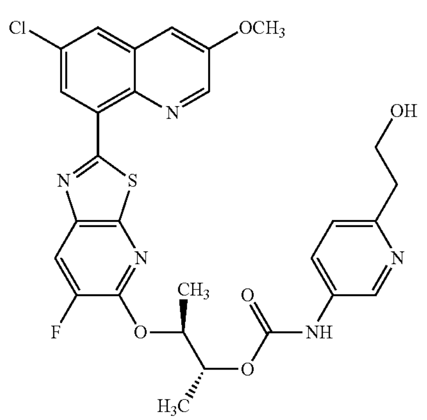 [SMILES: COc1cnc2c(-c3nc4cc(F)c(O[C@@H](C)[C@@H](C)OC(=O)Nc5ccc(CCO)nc5)nc4s3)cc(Cl)cc2c1] | | 598.1 | 1.06 | 1H NMR (500 MHz, DMSO-d6) δ 9.74 (br. s., 1H), 8.80 (d, J = 2.4 Hz, 1H), 8.56 (s, 1H), 8.49 (br. s., 1H), 8.42 (d, J = 11.0 Hz, 1H), 8.19 (s, 1H), 7.93 (d, J = 2.4 Hz, 1H), 7.79 (br. s., 1H), 7.26-7.18 (m, 1H), 5.66 (d, J = 6.4 Hz, 1H), 5.16 (d, J = 7.3 Hz, 1H), 4.00 (s, 3H), 3.66 (t, J = 6.9 Hz, 2H), 3.38 (br. s., 1H), 2.77 (q, J = 6.1 Hz, 2H), 1.46 (d, J = 6.4 Hz, 3H), 1.39 (d, J = 6.4 Hz, 3H). |

| Ex. No. | Structure | Amine | LCMS [M + H]+ m/z | LCMS RT (Min) Method H | 1H NMR |
|---|---|---|---|---|---|
| 782 | 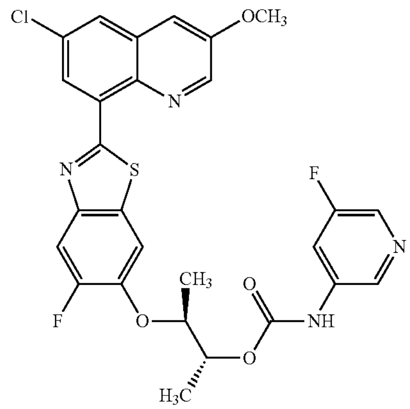 [SMILES: COc1cnc2c(-c3nc4cc(F)c(O[C@@H](C)[C@@H](C)OC(=O)Nc5cncc(F)c5)cc4s3)cc(Cl)cc2c1] | | 570.9 | 1.25 | 1H NMR (500 MHz, DMSO-d6) δ 10.21-10.16 (m, 1H), 8.87 (d, J = 2.7 Hz, 1H), 8.63 (s, 1H), 8.47 (br. s., 1H), 8.20 (br. s., 2H), 8.06 (d, J = 8.2 Hz, 1H), 7.98 (d, J = 11.3 Hz, 1H), 7.95 (d, J = 2.4 Hz, 1H), 7.83 (d, J = 12.2 Hz, 1H), 5.13 (br. s., 1H), 4.82 (br. s., 1H), 4.00 (s, 3H), 1.49-1.34 (m, 6H). |
| 783 | 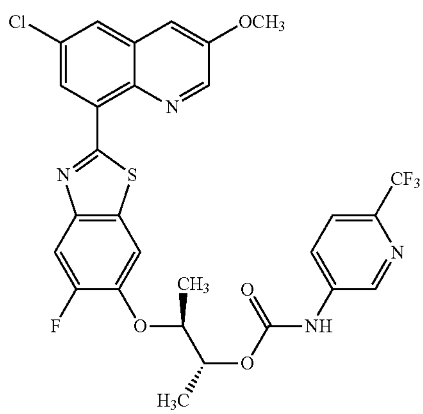 [SMILES: COc1cnc2c(-c3nc4cc(F)c(O[C@@H](C)[C@@H](C)OC(=O)Nc5ccc(C(F)(F)F)nc5)cc4s3)cc(Cl)cc2c1] | | 622.9 | 1.31 | 1H NMR (500 MHz, DMSO-d6) δ 10.32 (s, 1H), 8.83 (d, J = 2.7 Hz, 1H), 8.77 (s, 1H), 8.60 (d, J = 1.8 Hz, 1H), 8.17 (d, J = 1.8 Hz, 1H), 8.14-8.10 (m, 1H), 8.04 (d, J = 8.2 Hz, 1H), 7.95 (d, J = 11.6 Hz, 1H), 7.92 (d, J = 2.4 Hz, 1H), 7.81 (d, J = 8.9 Hz, 1H), 5.15 (dd, J = 6.6, 2.3 Hz, 1H), 4.84 (d, J = 4.0 Hz, 1H), 3.99 (s, 3H), 1.42 (dd, J = 6.0, 3.8 Hz, 6H). |
| 784 | 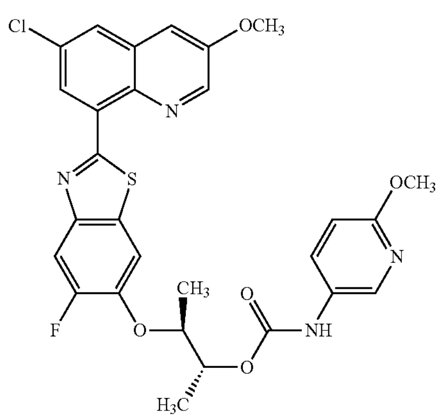 [SMILES: COc1cnc2c(-c3nc4cc(F)c(O[C@@H](C)[C@@H](C)OC(=O)Nc5ccc(OC)nc5)cc4s3)cc(Cl)cc2c1] | | 582.9 | 1.26 | 1H NMR (500 MHz, DMSO-d6) δ 9.65-9.57 (m, 1H), 8.85 (d, J = 2.1 Hz, 1H), 8.61 (s, 1H), 8.23-8.20 (m, 1H), 8.18 (s, 1H), 8.03 (d, J = 7.9 Hz, 1H), 7.96 (d, J = 11.6 Hz, 1H), 7.93 (br. s., 1H), 7.82-7.73 (m, 1H), 6.76 (d, J = 8.2 Hz, 1H), 5.09 (d, J = 4.6 Hz, 1H), 4.80 (d, J = 5.5 Hz, 1H), 3.99 (s, 3H), 3.78 (s, 3H), 1.39 (dd, J = 9.9, 6.6 Hz, 6H). |

| Ex. No. | Structure | Amine | LCMS [M + H]+ m/z | LCMS RT (Min) Method H | NMR |
|---|---|---|---|---|---|
| 785 | 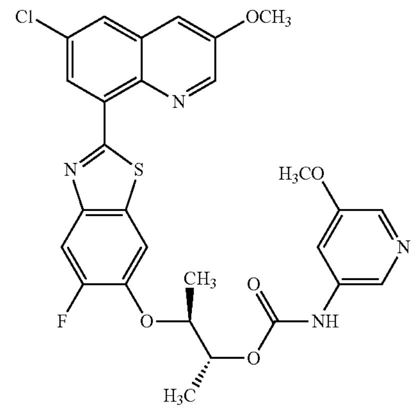 [SMILES: COc1cncc(NC(=O)O[C@H](C)[C@H](C)Oc2cc3sc(-c4cc(Cl)cc5cc(OC)cnc45)nc3cc2F)c1] | | 583.0 | 1.05 | ¹H NMR (500 MHz, DMSO-$d_6$) d 9.91 (br. s., 1H), 8.85 (d, J = 2.4 Hz, 1H), 8.61 (s, 1H), 8.24 (br. s., 1H), 8.18 (s, 1H), 8.04 (d, J = 8.2 Hz, 1H), 7.99-7.91 (m, 3H), 7.55 (br. s., 1H), 5.12 (d, J = 4.6 Hz, 1H), 4.81 (d, J = 4.0 Hz, 1H), 3.99 (s, 3H), 3.78 (s, 3H), 1.41 (t, J = 6.6 Hz, 6H). |
| 786 | 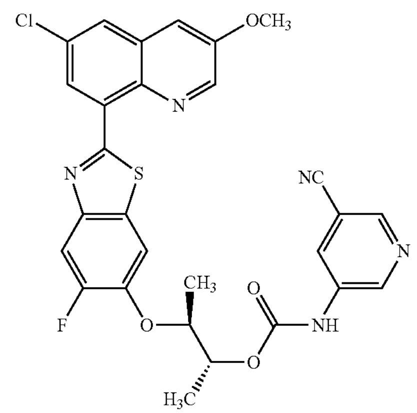 [SMILES: COc1cnc2c(-c3nc4cc(F)c(O[C@@H](C)[C@@H](C)OC(=O)Nc5cncc(C#N)c5)cc4s3)cc(Cl)cc2c1] | | 577.9 | 1.25 | ¹H NMR (500 MHz, DMSO-$d_6$) d 10.28 (br. s., 1H), 8.87-8.81 (m, 2H), 8.60 (s, 2H), 8.25 (br. s., 1H), 8.18 (s, 1H), 8.04 (d, J = 8.2 Hz, 1H), 7.96 (d, J = 11.3 Hz, 1H), 7.92 (d, J = 2.1 Hz, 1H), 5.14 (d, J = 4.3 Hz, 1H), 4.85 (d, J = 4.0 Hz, 1H), 3.99 (s, 3H), 1.42 (d, J = 4.9 Hz, 6H). |
| 787 | 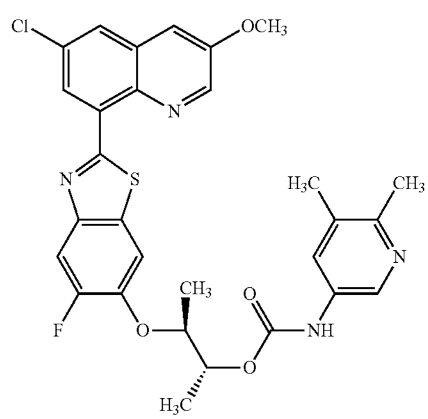 [SMILES: COc1cnc2c(-c3nc4cc(F)c(O[C@@H](C)[C@@H](C)OC(=O)Nc5cnc(C)c(C)c5)cc4s3)cc(Cl)cc2c1] | | 582.8 | 1.02 | ¹H NMR (500 MHz, DMSO-$d_6$) d 9.71 (br. s., 1H), 8.86 (d, J = 2.4 Hz, 1H), 8.62 (s, 1H), 8.33 (br. s., 1H), 8.18 (s, 1H), 8.04 (d, J = 8.2 Hz, 1H), 7.96 (d, J = 11.6 Hz, 1H), 7.93 (br. s., 1H), 7.63 (br. s., 1H), 5.10 (d, J = 4.0 Hz, 1H), 4.81 (d, J = 4.3 Hz, 1H), 4.00 (s, 3H), 2.33 (s, 3H), 2.18 (s, 3H), 1.40 (t, J = 7.3 Hz, 6H). |

-continued

| Ex. No. | Structure | Amine | LCMS [M + H]+ m/z | LCMS RT (Min) Method H | NMR |
|---|---|---|---|---|---|
| 788 | 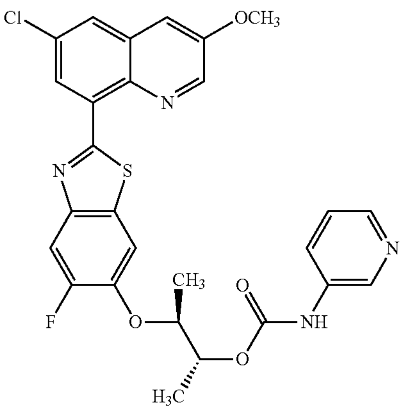 [SMILES: COc1cnc2c(-c3nc4cc(F)c(O[C@@H](C)[C@@H](C)OC(=O)Nc5cccnc5)cc4s3)cc(Cl)cc2c1] | | 552.9 | 1.02 | 1H NMR (500 MHz, DMSO-d6) δ 9.91 (br. s., 1H), 8.86 (d, J = 2.7 Hz, 1H), 8.65 (br. s., 1H), 8.62 (d, J = 2.1 Hz, 1H), 8.21 (d, J = 4.3 Hz, 1H), 8.18 (s, 1H), 8.05 (d, J = 8.2 Hz, 1H), 7.97 (d, J = 11.6 Hz, 1H), 7.93 (d, J = 2.7 Hz, 1H), 7.92-7.88 (m, 1H), 7.33 (dd, J = 8.2, 4.6 Hz, 1H), 5.22-5.08 (m, 1H), 4.81 (d, J = 3.7 Hz, 1H), 4.00 (s, 3H), 1.41 (t, J = 6.7 Hz, 6H). |
| 789 | 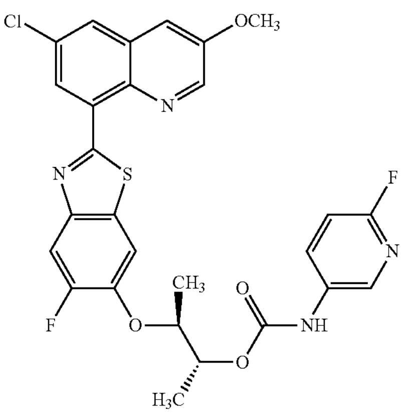 [SMILES: COc1cnc2c(-c3nc4cc(F)c(O[C@@H](C)[C@@H](C)OC(=O)Nc5ccc(F)nc5)cc4s3)cc(Cl)cc2c1] | | 571.0 | 1.27 | 1H NMR (500 MHz, DMSO-d6) d 10.01-9.90 (m, 1H), 8.85 (d, J = 2.4 Hz, 1H), 8.61 (d, J = 2.1 Hz, 1H), 8.27 (br. s., 1H), 8.18 (d, J = 1.8 Hz, 1H), 8.04 (d, J = 8.2 Hz, 2H), 7.97 (d, J = 11.6 Hz, 1H), 7.93 (d, J = 2.4 Hz, 1H), 7.12 (d, J = 6.4 Hz, 1H), 5.12 (dd, J = 6.6, 2.6 Hz, 1H), 4.81 (d, J = 3.7 Hz, 1H), 4.00 (s, 3H), 1.41 (t, J = 6.4 Hz, 6H). |
| 790 | 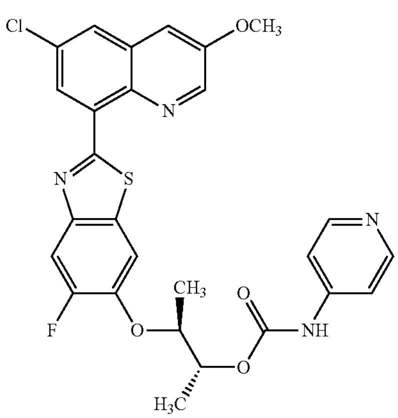 [SMILES: COc1cnc2c(-c3nc4cc(F)c(O[C@@H](C)[C@@H](C)OC(=O)Nc5ccncc5)cc4s3)cc(Cl)cc2c1] | | 552.9 | 1.02 | 1H NMR (500 MHz, DMSO-d6) δ 10.31 (s, 1H), 8.86 (d, J = 2.7 Hz, 1H), 8.62 (d, J = 1.8 Hz, 1H), 8.41 (d, J = 5.5 Hz, 2H), 8.19 (d, J = 1.8 Hz, 1H), 8.05 (d, J = 8.2 Hz, 1H), 7.97 (d, J = 11.3 Hz, 1H), 7.94 (d, J = 2.4 Hz, 1H), 7.52 (d, J = 5.8 Hz, 2H), 5.16 (d, J = 4.0 Hz, 1H), 4.82 (d, J = 3.7 Hz, 1H), 4.00 (s, 3H), 1.48-1.36 (m, 6H). |

| Ex. No. | Structure | Amine | LCMS [M + H]+ m/z | LCMS RT (Min) Method H | NMR |
|---|---|---|---|---|---|
| 791 | (structure shown) | (structure shown) | 549.2 | 1.06 | 1H NMR (500 MHz, DMSO-d6) δ 9.76 (br. s., 1H), 8.65 (br. s., 2H), 8.49 (s, 1H), 8.34 (d, J = 10.7 Hz, 1H), 7.80 (d, J = 9.8 Hz, 2H), 7.61-7.33 (m, 1H), 7.18-6.88 (m, 1H), 5.65 (d, J = 6.4 Hz, 1H), 5.06 (d, J = 6.4 Hz, 1H), 3.92 (s, 3H), 2.54 (s, 3H), 2.41 (s, 3H), 1.37 (d, J = 6.1 Hz, 3H), 1.32 (d, J = 6.4 Hz, 3H). |

Example 792

(2R,3S)-3-(((6-fluoro-2-(3-methoxy-6-methylquinolin-8-yl)thiazolo[5,4-b]pyridin-5-yl)oxy)butan-2-yl (2-(hydroxymethyl)pyrimidin-5-yl)carbamate

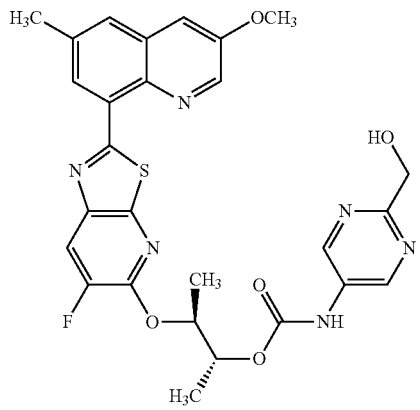

(792)

Intermediate 792A: methyl 5-(((((2R,3S)-3-((6-fluoro-2-(3-methoxy-6-methylquinolin-8-yl)thiazolo[5,4-b]pyridin-5-yl)oxy)butan-2-yl)oxy)carbonyl)amino)pyrimidine-2-carboxylate

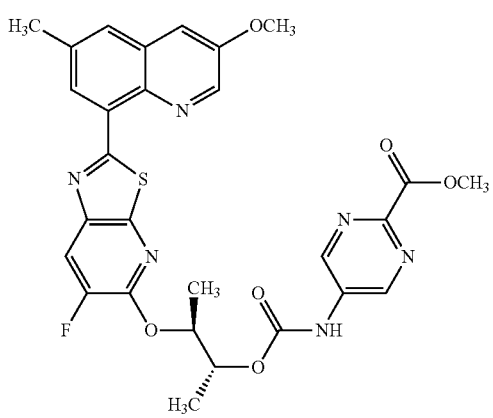

(792A)

Intermediate I-124 (6.56 mg, 0.022 mmol), Intermediate I-141 (10 mg, 0.022 mmol), and PdCl2(dppf) (0.963 mg, 1.316 μmol) were dissolved in dioxane (219 μl) and 3 M aqueous Na2CO3 (99 μL, 0.197 mmol) was added. The reaction mixture was heated to 100° C. in an oil bath for 2 hours. The reaction mixture was cooled to ambient temperature, diluted with EtOAc, washed with water, washed with brine, dried (Na2SO4), filtered, and concentrated in vacuo. The reaction material was dissolved in DCM and filtered. Purified on ISCO using 0-100% EtOAc in DCM on a 4 g column to yield Intermediate 792A (7.5 mg, 0.013 mmol, 57.7% yield) as a yellow solid. LC-MS: method H, RT=1.23 min, MS (ESI) m/z: 593.1 (M+H)+.

Example 792

Intermediate 792A (7.5 mg, 0.013 mmol) was dissolved in THF (127 μl) and lithium borohydride (0.276 mg, 0.013 mmol) was added in one portion. The reaction mixture was allowed to stir at room temperature for 3 h. Residue was dissolved in THF and air was bubbled through the reaction until the solvent was evaporated. The reaction material was dissolved in DMF, filtered, and purified by preparative HPLC (Method D, 45 to 90% B in 15 minutes) to yield Example 792 (1.7 mg, 2.95 μmol, 23.32% yield): 1H NMR (500 MHz, DMSO-d6) δ 9.96 (br. s., 1H), 8.80 (br. s., 2H), 8.74 (br. s., 1H), 8.57 (br. s., 1H), 8.41 (d, J=10.7 Hz, 1H), 7.88 (d, J=10.4 Hz, 2H), 5.70 (br. s., 1H), 5.17 (br. s., 1H), 4.49 (br. s., 2H), 4.00 (br. s., 3H), 3.84-3.34 (m, 1H), 2.61 (br. s., 3H), 1.54-1.34 (m, 6H). LC-MS: method H, RT=1.28 min, MS (ESI) m/z: 565.2 (M+H)+. Analytical HPLC Method B: 98% purity.

Example 793

(2R,3S)-3-((2-(6-chloro-3-methoxyquinolin-8-yl)-6-fluorothiazolo[5,4-b]pyridin-5-yl)oxy)butan-2-yl (2-(hydroxymethyl)pyrimidin-5-yl)carbamate

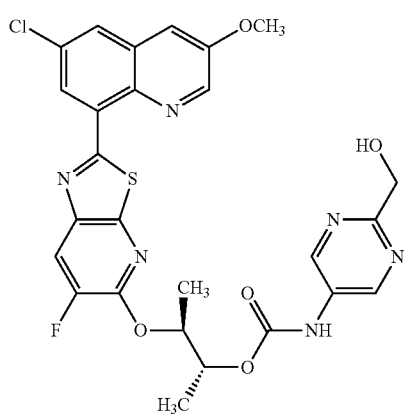

(793)

Intermediate 793A: methyl 5-(((((2R,3S)-3-((2-(6-chloro-3-methoxyquinolin-8-yl)-6-fluorothiazolo[5,4-b]pyridin-5-yl)oxy)butan-2-yl)oxy)carbonyl)amino)pyrimidine-2-carboxylate

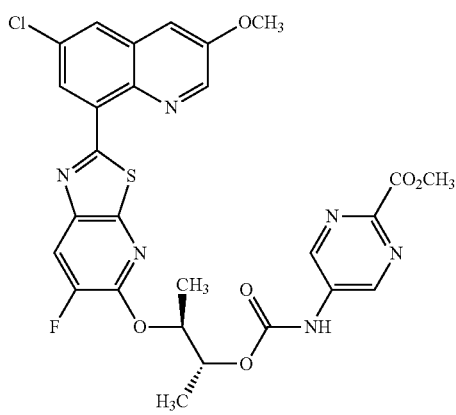

(793A)

Intermediate I-121 (7.01 mg, 0.022 mmol), Intermediate I-141 (10 mg, 0.022 mmol), and PdCl$_2$(dppf) (0.963 mg, 1.316 µmol) were dissolved in dioxane (2190) and 3 M aqueous Na$_2$CO$_3$ (99 µL, 0.197 mmol) was added. The reaction mixture was heated to 100° C. in an oil bath for 2 hours. The reaction mixture was cooled to ambient temperature, diluted with EtOAc, washed with water, washed with brine, dried (Na$_2$SO$_4$), filtered, and concentrated in vacuo. The reaction material was dissolved in DCM and filtered. Purified on ISCO using 0-100% EtOAc in DCM on a 4 g column to yield Intermediate 793A (5.9 mg, 0.0096 mmol, 44% yield) as a yellow solid. LC-MS: method H, RT=1.23 min, MS (ESI) m/z: 613.1 (M+H)$^+$.

Example 793

Intermediate 793A (5.9 mg, 0.009 mmol) was dissolved in THF (1270) and lithium borohydride (0.276 mg, 0.013 mmol) was added in one portion. The reaction mixture was allowed to stir at room temperature for 3 h. Residue was dissolved in THF and air was bubbled through the reaction until the solvent was evaporated. The reaction material was dissolved in DMF, filtered, and purified by preparative HPLC (Method D, 45 to 90% B in 15 minutes) to yield Example 793 (1.1 mg, 1.79 µmol, 19% yield): $^1$H NMR (500 MHz, DMSO-d$_6$) δ 9.94 (br. s., 1H), 8.91-8.71 (m, 2H), 8.58 (br. s., 1H), 8.45 (d, J=10.1 Hz, 1H), 8.21 (br. s., 1H), 7.95 (br. s., 1H), 7.70 (d, J=14.3 Hz, 1H), 5.71 (br. s., 1H), 5.17 (br. s., 1H), 4.48 (br. s., 2H), 4.00 (br. s., 3H), 3.43-3.28 (m, 1H), 1.52-1.36 (m, 6H). LC-MS: method H, RT=0.95 min, MS (ESI) m/z: 585.1 (M+H)$^+$. Analytical HPLC Method B: 95% purity.

Example 794

(R)-1-((2-(6-chloro-3-methoxyquinolin-8-yl)-6-fluorothiazolo[5,4-b] pyridin-5-yl)oxy)propan-2-yl (2-(hydroxymethyl)pyrimidin-5-yl)carbamate

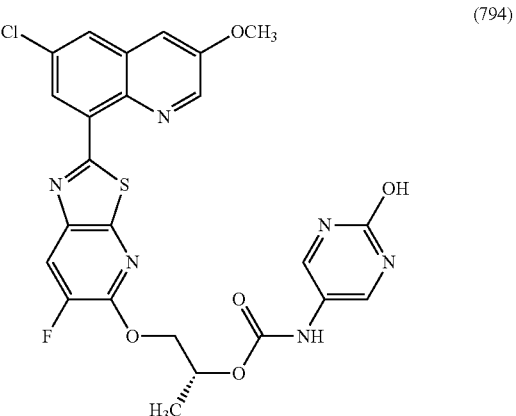

(794)

Intermediate 794A: (R)-methyl 5-((((1-((2-(6-chloro-3-methoxyquinolin-8-yl)-6-fluorothiazolo[5,4-b]pyridin-5-yl)oxy)propan-2-yl)oxy)carbonyl)amino)pyrimidine-2-carboxylate

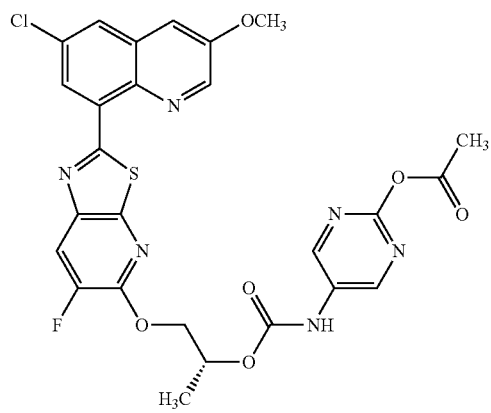

(794A)

Example 795

(2R,3S)-3-((4-chloro-2-(6-chloro-3-methoxyquinolin-8-yl)-5-fluorobenzo[d]thiazol-6-yl)oxy)butan-2-yl (2-(2-hydroxyethoxy)pyrimidin-5-yl)carbamate

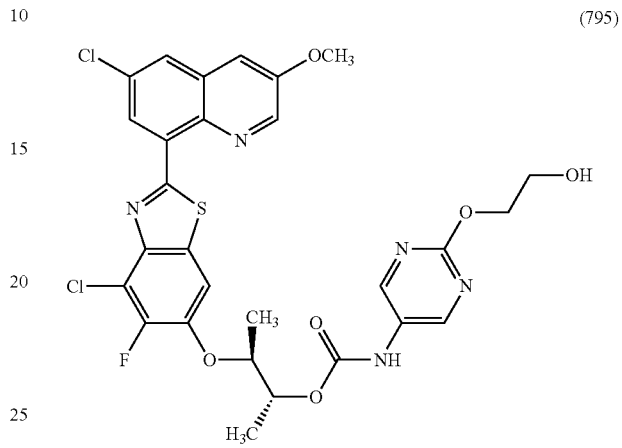

(795)

Intermediate I-121 (7.23 mg, 0.022 mmol), Intermediate I-142 (10 mg, 0.022 mmol) and PdCl$_2$(dppf) (0.963 mg, 1.316 μmol) were dissolved in dioxane (219 μl) and 3M aqueous Na$_2$CO$_3$ (99 μl, 0.197 mmol) was added. The reaction mixture was heated to 100° C. in an oil bath for 2 hours. The reaction mixture was cooled to ambient temperature, diluted with EtOAc, washed with water, washed with brine, dried (Na$_2$SO$_4$), filtered, and concentrated in vacuo. The material was dissolved in DCM and filtered. Purified on ISCO using 0-100% EtOAc in DCM on a 4 g column to yield Intermediate 792A (4.5 mg, 0.0075 mmol, 33% yield) as a yellow solid. LC-MS: method H, RT=1.23 min, MS (ESI) m/z: 599.1 (M+H)$^+$.

Example 794

Intermediate 794A (4.5 mg, 0.008 mmol) was dissolved in THF (127 μl) and lithium borohydride (0.276 mg, 0.013 mmol) was added in one portion. The reaction mixture was allowed to stir at room temperature for 3 h. Residue was dissolved in THF and air was bubbled through the reaction mixture until the solvent was evaporated. The mixture was dissolved in DMF, filtered, and purified by preparative HPLC (Method D, 45 to 90% B in 15 minutes) to yield Example 794 (0.8 mg, 1.33 μmol, 18% yield). $^1$H NMR (500 MHz, DMSO-d$_6$) δ 10.08 (br. s., 1H), 8.84 (d, J=18.0 Hz, 3H), 8.59 (br. s., 1H), 8.48 (d, J=9.8 Hz, 1H), 8.22 (br. s., 1H), 7.96 (br. s., 1H), 5.30 (br. s., 1H), 4.84 (d, J=11.9 Hz, 1H), 4.60-4.54 (m, 1H), 4.51 (br. s., 2H), 4.01 (br. s., 3H), 3.41-3.23 (m, 1H), 1.43 (br. s., 3H). LC-MS: method H, RT=0.96 min, MS (ESI) m/z: 571.1 (M+H)$^+$. Analytical HPLC Method B: 95% purity.

Intermediate I-97 (10.83 mg, 0.035 mmol) and pyridine (0.019 mL, 0.236 mmol) were dissolved in DCM (2 mL). To this solution was added Intermediate I-143 (0.0125 g, 0.024 mmol) as a solution in DCM (1 mL). The reaction mixture was allowed to stir for 30 min. The reaction mixture was concentrated under reduced pressure and dissolved in 2 mL of 1:1 THF:MeOH solution and CSA (5.48 mg, 0.024 mmol) was added. The reaction mixture was allowed to stir at room temperature for 2 h. TEA (0.033 mL, 0.236 mmol) was added to quench the CSA, and the reaction mixture was concentrated and dissolved in 2 mL of DMF, filtered, and purified by preparative HPLC (Method D, 50 to 100% B in 20 minutes) to yield Example 795 (0.0075 g, 0.012 mmol, 49.0% yield): $^1$H NMR (500 MHz, DMSO-d$_6$) δ 9.80 (br. s., 1H), 8.82 (d, J=2.1 Hz, 1H), 8.59 (br. s., 3H), 8.18 (s, 1H), 8.05 (d, J=7.3 Hz, 1H), 7.92 (br. s., 1H), 5.11 (d, J=4.9 Hz, 1H), 4.86 (br. s., 1H), 4.23 (br. s., 2H), 3.99 (s, 3H), 3.68 (d, J=4.9 Hz, 2H), 3.34 (br. s., 1H), 1.41 (dd, J=15.3, 6.1 Hz, 6H). LC-MS: method H, RT=1.23 min, MS (ESI) m/z: 647.9 (M+H)$^+$. Analytical HPLC Method B: 100% purity.

Examples 796 to 804

The following additional examples have been prepared, isolated and characterized using the methods described for Example 795 and the examples above.

| Ex. No. | Structure | Amine | LCMS [M + H]+ m/z | LCMS RT (Min) Method H | NMR |
|---|---|---|---|---|---|
| 796 | 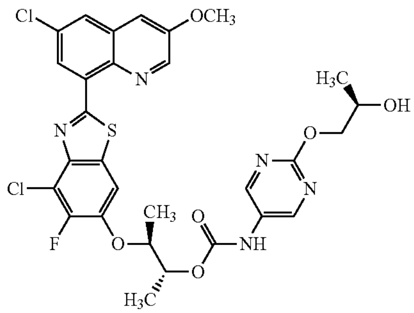 [SMILES: COc1cnc2c(-c3nc4c(Cl)c(F)c(O[C@@H](C)[C@@H](C)OC(=O)Nc5cnc(OC[C@@H](C)O)nc5)cc4s3)cc(Cl)cc2c1] | | 663.9 | 1.26 | ¹H NMR (500 MHz, DMSO-d₆) δ 9.80 (br. s., 1H), 8.80 (br. s., 1H), 8.63-8.54 (m, 3H), 8.16 (s, 1H), 8.04 (d, J = 7.3 Hz, 1H), 7.90 (br. s., 1H), 5.11 (d, J = 7.0 Hz, 1H), 4.85 (d, J = 7.0 Hz, 1H), 4.07 (d, J = 6.4 Hz, 1H), 4.02 (br. s., 1H), 3.99 (s, 3H), 3.96-3.89 (m, 1H), 3.36 (d, J = 4.6 Hz, 1H), 1.41 (dd, J = 15.6, 6.1 Hz, 6H), 1.11 (d, J = 6.1 Hz, 3H). |
| 797 | 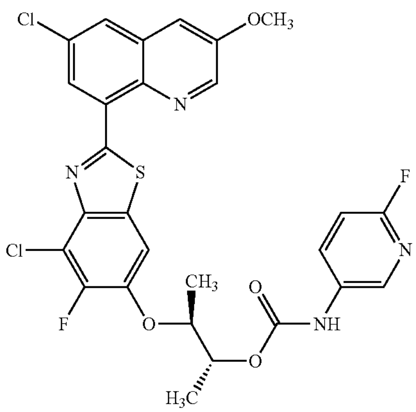 [SMILES: COc1cnc2c(-c3nc4c(Cl)c(F)c(O[C@@H](C)[C@@H](C)OC(=O)Nc5ccc(F)nc5)cc4s3)cc(Cl)cc2c1] | | 605.1 | 1.33 | ¹H NMR (500 MHz, DMSO-d₆) δ 9.94 (br. s., 1H), 8.78 (d, J = 2.7 Hz, 1H), 8.55 (d, J = 2.1 Hz, 1H), 8.30-8.24 (m, 1H), 8.14 (d, J = 2.1 Hz, 1H), 8.02 (d, J = 7.3 Hz, 2H), 7.88 (d, J = 2.7 Hz, 1H), 7.11 (d, J = 7.0 Hz, 1H), 5.13 (dd, J = 6.4, 2.4 Hz, 1H), 4.84 (d, J = 4.0 Hz, 1H), 3.98 (s, 3H), 1.42 (dd, J = 16.2, 6.4 Hz, 6H). |
| 798 | 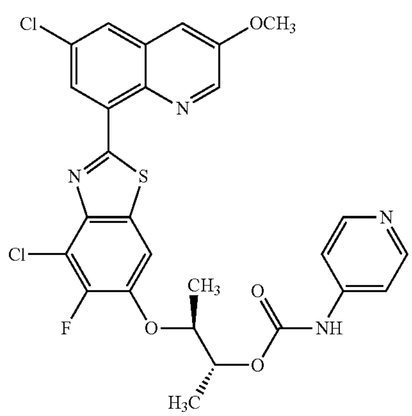 [SMILES: COc1cnc2c(-c3nc4c(Cl)c(F)c(O[C@@H](C)[C@@H](C)OC(=O)Nc5ccncc5)cc4s3)cc(Cl)cc2c1] | | 588.8 | 1.10 | ¹H NMR (500 MHz, DMSO-d₆) δ 11.00 (s, 1H), 8.82 (d, J = 2.7 Hz, 1H), 8.59 (d, J = 2.4 Hz, 3H), 8.18 (d, J = 2.1 Hz, 1H), 8.07 (d, J = 7.6 Hz, 1H), 7.92 (d, J = 2.7 Hz, 1H), 7.79 (d, J = 6.4 Hz, 2H), 5.22 (dd, J = 6.7, 2.4 Hz, 1H), 4.95-4.77 (m, 1H), 3.99 (s, 3H), 1.44 (t, J = 7.0 Hz, 6H). |
| 799 | 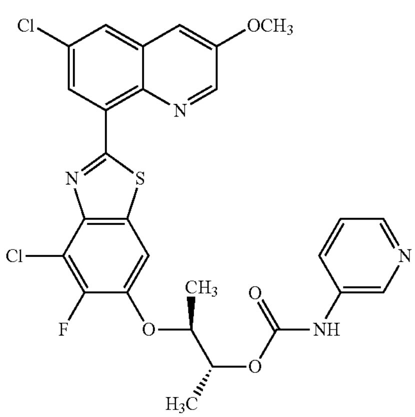 [SMILES: COc1cnc2c(-c3nc4c(Cl)c(F)c(O[C@@H](C)[C@@H](C)OC(=O)Nc5cccnc5)cc4s3)cc(Cl)cc2c1] | | 588.8 | 1.11 | ¹H NMR (500 MHz, DMSO-d₆) δ 9.91 (br. s., 1H), 8.83 (d, J = 3.1 Hz, 1H), 8.65 (br. s., 1H), 8.61 (d, J = 2.1 Hz, 1H), 8.23-8.17 (m, 2H), 8.07 (d, J = 7.6 Hz, 1H), 7.93 (d, J = 2.7 Hz, 2H), 7.33 (dd, J = 8.1, 4.7 Hz, 1H), 5.15 (dd, J = 6.4, 2.7 Hz, 1H), 4.92-4.77 (m, 1H), 4.00 (s, 3H), 1.42 (dd, J = 15.3, 6.4 Hz, 6H). |

-continued

| Ex. No. | Structure | Amine | LCMS [M + H]+ m/z | LCMS RT (Min) Method H | NMR |
|---|---|---|---|---|---|
| 800 | 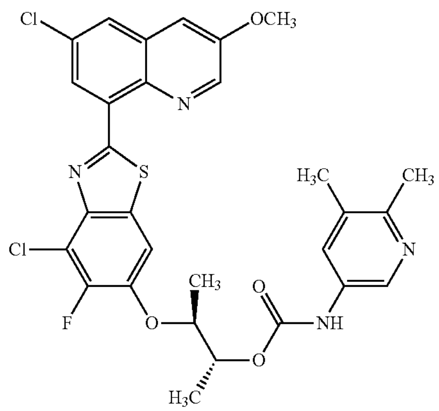 [SMILES: COc1cnc2c(-c3nc4c(Cl)c(F)c(O[C@@H](C)[C@@H](C)OC(=O)Nc5cnc(C)c(C)c5)cc4s3)cc(Cl)cc2c1] | | 616.8 | 1.12 | ¹H NMR (500 MHz, DMSO-$d_6$) δ 10.15 (br. s., 1H), 8.83 (d, J = 2.7 Hz, 1H), 8.61 (d, J = 2.1 Hz, 1H), 8.50 (br. s., 1H), 8.20 (d, J = 2.1 Hz, 1H), 8.06 (d, J = 7.6 Hz, 1H), 7.97-7.85 (m, 2H), 5.14 (d, J = 6.4 Hz, 1H), 4.87 (d, J = 4.0 Hz, 1H), 4.00 (s, 3H), 2.42 (s, 3H), 2.26 (s, 3H), 1.42 (dd, J = 14.2, 6.6 Hz, 6H). |
| 801 | 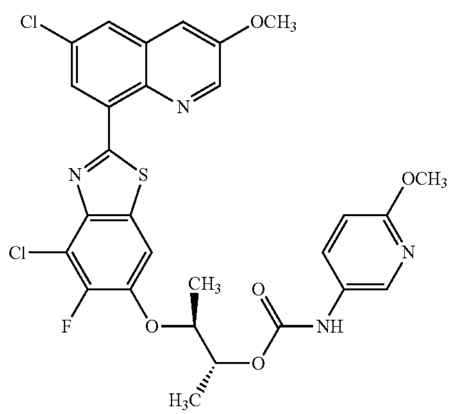 [SMILES: COc1cnc2c(-c3nc4c(Cl)c(F)c(O[C@@H](C)[C@@H](C)OC(=O)Nc5ccc(OC)nc5)cc4s3)cc(Cl)cc2c1] | | 618.8 | 1.33 | ¹H NMR (500 MHz, DMSO-$d_6$) δ 9.60 (br. s., 1H), 8.82 (d, J = 2.7 Hz, 1H), 8.60 (d, J = 2.1 Hz, 1H), 8.18 (d, J = 2.1 Hz, 2H), 8.04 (d, J = 7.3 Hz, 1H), 7.92 (d, J = 2.7 Hz, 1H), 7.76 (br. s., 1H), 6.75 (d, J = 7.9 Hz, 1H), 5.10 (dd, J = 6.6, 2.6 Hz, 1H), 4.83 (dd, J = 6.4, 2.7 Hz, 1H), 3.99 (s, 3H), 3.77 (s, 3H), 1.42 (d, J = 6.1 Hz, 3H), 1.39 (d, J = 6.4 Hz, 3H). |
| 802 | 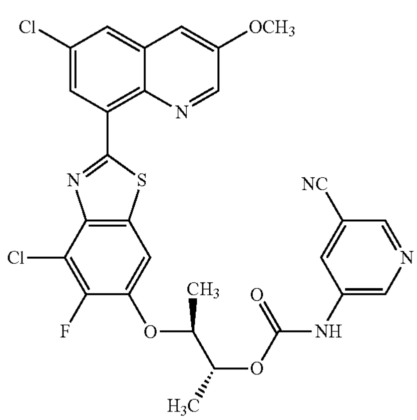 [SMILES: COc1cnc2c(-c3nc4c(Cl)c(F)c(O[C@@H](C)[C@@H](C)OC(=O)Nc5cncc(C#N)c5)cc4s3)cc(Cl)cc2c1] | | 613.8 | 1.32 | ¹H NMR (500 MHz, DMSO-$d_6$) δ 10.27 (br. s., 1H), 8.81 (d, J = 2.7 Hz, 2H), 8.62-8.56 (m, 2H), 8.25 (br. s., 1H), 8.17 (d, J = 1.8 Hz, 1H), 8.05 (d, J = 7.6 Hz, 1H), 7.91 (d, J = 2.4 Hz, 1H), 5.15 (dd, J = 6.6, 2.3 Hz, 1H), 4.88 (d, J = 4.0 Hz, 1H), 3.99 (s, 3H), 1.43 (dd, J = 12.2, 6.4 Hz, 6H). |

| Ex. No. | Structure | Amine | LCMS [M+H]+ m/z | LCMS RT (Min) Method H | NMR |
|---|---|---|---|---|---|
| 803 | (structure shown) | (structure shown) | 618.9 | 1.13 | ¹H NMR (500 MHz, DMSO-d₆) δ 9.86 (br. s., 1H), 8.76 (d, J = 2.7 Hz, 1H), 8.53 (d, J = 2.1 Hz, 1H), 8.19 (br. s., 1H), 8.12 (d, J = 2.4 Hz, 1H), 8.00 (d, J = 7.6 Hz, 1H), 7.89 (s, 1H), 7.85 (d, J = 2.7 Hz, 1H), 7.50 (br. s., 1H), 5.09 (dd, J = 6.6, 2.6 Hz, 1H), 4.89-4.68 (m, 1H), 3.94 (s, 3H), 3.73 (s, 3H), 1.38 (d, J = 6.4 Hz, 3H), 1.35 (d, J = 6.7 Hz, 3H). |
| 804 | (structure shown) | (structure shown) | 605.1 | 1.32 | ¹H NMR (500 MHz, DMSO-d₆) δ 10.18 (br. s., 1H), 8.79 (d, J = 2.7 Hz, 1H), 8.56 (d, J = 2.4 Hz, 1H), 8.46 (br. s., 1H), 8.19 (d, J = 2.4 Hz, 1H), 8.15 (d, J = 2.1 Hz, 1H), 8.04 (d, J = 7.3 Hz, 1H), 7.89 (d, J = 2.7 Hz, 1H), 7.82 (d, J = 10.4 Hz, 1H), 5.15 (dd, J = 6.6, 2.6 Hz, 1H), 4.85 (d, J = 3.7 Hz, 1H), 3.98 (s, 3H), 1.42 (dd, J = 14.2, 6.6 Hz, 6H). |

Example 806

1-(6-fluoro-2-(2-methoxy-7-methylquinoxalin-5-yl)benzo[d]thiazol-4-yl)-2,2-dimethylpropan-1-ol (806)

Intermediate 806A:
4-bromo-6-fluorobenzo[d]thiazol-2-amine (806A)

2-Bromo-4-fluoroaniline (0.54 g, 2.84 mmol) was dissolved in MeCN (14.21 ml). Ammonium thiocyanate (0.324 g, 4.26 mmol) was added to the reaction mixture followed by benzyltrimethylammonium tribromide (1.108 g, 2.84 mmol), and the reaction mixture was allowed to stir for 12 hours. The reaction mixture was diluted with saturated aqueous NaHCO₃, and the solids were collected by suction filtration and washed with water to yield Intermediate 806A (0.700 g, 2.84 mmol, 100%). ¹H NMR (400 MHz, MeOH₄) δ 7.41 (dd, J=8.0, 2.5 Hz, 1H), 7.26 (dd, 2.5 Hz, 1H). LC-MS: method H, RT=0.81 min, MS (ESI) m/z: 247/249 (M+H)⁺.

Intermediate 806B: 1-(2-amino-6-fluorobenzo[d]thiazol-4-yl)-2,2-dimethylpropan-1-ol

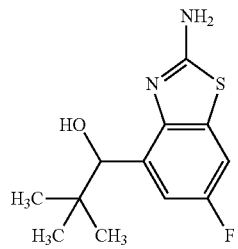
(806B)

Intermediate 806A (50 mg, 0.202 mmol) was dissolved in THF (2024 µl). NaH (8.90 mg, 0.223 mmol) was added and the reaction mixture was stirred for 30 min. The reaction mixture was cooled to −78° C. and BuLi (106 µl, 0.243 mmol) was added. The reaction mixture was allowed to stir for 30 min. Pivalaldehyde (17.43 mg, 0.202 mmol) was added, and the reaction mixture was allowed to warm to ambient temperature. The reaction mixture was stirred for 10 min then diluted with water and EtOAc. The layers were separated and the aqueous layer was back extracted with EtOAc. The combined organic layer was washed with water, dried with sodium sulfate, and concentrated under reduced pressure to yield Intermediate 806B (0.064 g, 0.151 mmol, 75% yield). Used without further purification as a 60% pure mixture. LC-MS: method H, RT=0.56 min, MS (ESI) m/z: 255.2 (M+H)+.

Intermediate 806C: 1-(2-chloro-6-fluorobenzo[d]thiazol-4-yl)-2,2-dimethylpropan-1-ol

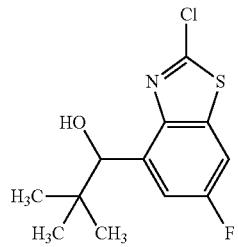
(806C)

Copper(II) chloride (0.058 g, 0.434 mmol) and t-butyl nitrite (0.052 ml, 0.434 mmol) were dissolved in MeCN (1.022 ml) and allowed to stir 10 minutes. Intermediate 806B (0.065 g, 0.256 mmol) was dissolved in MeCN (1.533 ml), and the copper solution was added. The reaction mixture was stirred for 2.5 h at 60° C. The reaction mixture was diluted with EtOAc and water. The layers were separated, and the organic layer was washed with 1 N HCl, washed with saturated aqueous NaHCO3, washed with brine, dried (Na2SO4), filtered, and concentrated in vacuo. The crude material was purified on ISCO using a 12 g column with 0-100% gradient of EtOAc in hexanes to yield Intermediate 806C (0.008 g, 0.029 mmol, 11.43% yield) as a white solid. LC-MS: method H, RT=1.14 min, MS (ESI) m/z: 274.1 (M+H)+.

Example 806

Intermediate I-9 (8.77 mg, 0.029 mmol) and Intermediate 806C (0.008 g, 0.029 mmol) were dissolved in DMF (0.292 ml). PdCl2(dppf)-CH2Cl2 adduct (1.432 mg, 1.753 µmol) was added, and the reaction mixture was degassed by bubbling with argon for 15 minutes. Na2CO3, 3 M aqueous solution (0.100 ml, 0.300 mmol) was added, and the reaction mixture was degassed for 5 minutes, then sealed and heated to 90° C. in the microwave for 30 minutes. The reaction mixture was filtered and purified by preparative HPLC (Method D, 20 to 100% B in 20 minutes) to yield Example 806 (0.0032 g, 0.007 mmol, 24%  % yield): $^1$H NMR (500 MHz, DMSO-d$_6$) δ 8.72 (s, 1H), 8.55 (s, 1H), 7.92 (d, J=7.9 Hz, 1H), 7.84 (s, 1H), 7.32 (d, J=10.4 Hz, 1H), 5.46 (br. s., 1H), 4.07 (s, 3H), 2.64 (s, 3H), 0.95 (s, 9H). LC-MS: method H, RT=1.39 min, MS (ESI) m/z: 412.2 (M+H)+. Analytical HPLC Method B: 92% purity.

Example 807

1-(5-methoxy-2-(2-methoxy-7-methylquinoxalin-5-yl)thiazolo[5,4-b]pyridin-7-yl)-2,2-dimethylpropan-1-ol

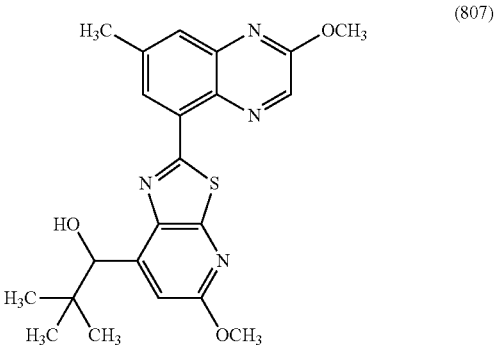 [SMILES: COc1cnc2c(-c3nc4c(C(O)C(C)(C)C)cc(OC)nc4s3)cc(C)cc2n1]
(807)

Intermediate 807A: 2-bromo-7-(dibromomethyl)-5-methoxythiazolo[5,4-b]pyridine

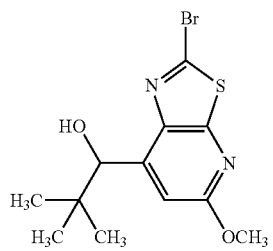
(807A)

Intermediate I-16 (0.250 g, 0.965 mmol) was dissolved in CCl$_4$ (3 mL) and NBS (0.859 g, 4.82 mmol) was added followed by AIBN (0.048 g, 0.289 mmol). The reaction mixture was allowed to stir at reflux for 12 hours. The reaction mixture was cooled and diluted with water and EtOAc. The layers were separated and the organic layer was washed with 1 N HCl, washed with brine, dried with sodium sulfate, and concentrated under reduced pressure to yield Intermediate 807A (0.125 g, 0.300 mmol, 31%) which was used without purification. LC-MS: method H, RT=1.14 min, MS (ESI) m/z: 416.9 (M+H)+.

Intermediate 807B: 1-(2-bromo-5-methoxythiazolo[5,4-b]pyridin-7-yl)-2,2-dimethylpropan-1-ol

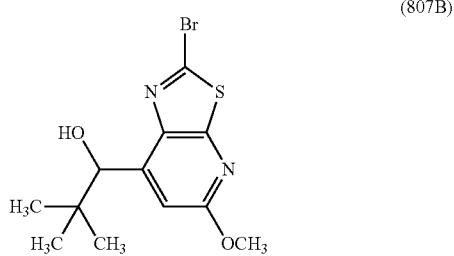 [SMILES: COc1cc(C(O)C(C)(C)C)c2nc(Br)sc2n1]
(807B)

Intermediate 807A (0.125 g, 0.458 mmol) was dissolved in THF (4.58 ml) and t-butyl magnesium chloride (0.267 g, 2.288 mmol) was added at −78° C. The reaction mixture was allowed to slowly warm to room temperature. The reaction was quenched with saturated aqueous NH$_4$Cl and the reaction mixture was diluted with EtOAc. The layers were separated, and the organic layer was washed with brine, dried with sodium sulfate, and concentrated under reduced pressure to yield Intermediate 807B (0.034 g, 0.103 mmol, 22.43% yield): $^1$H NMR (400 MHz, CDCl$_3$) δ 6.72 (s, 1H), 4.78 (d, J=8.1 Hz, 1H), 3.98 (s, 3H), 3.79 (d, J=8.4 Hz, 1H), 0.96 (s, 9H). LC-MS: method H, RT=1.18 min, MS (ESI) m/z: 331.0 (M+H)$^+$.

Example 807

Intermediate I-9 (0.034 g, 0.115 mmol) and Intermediate 806B (0.038 g, 0.115 mmol) were dissolved in DMF (1.147 ml). PdCl$_2$(dppf)-CH$_2$Cl$_2$ adduct (5.62 mg, 6.88 μmol) was added, and the reaction mixture was degassed by bubbling with argon for 15 minutes. Na$_2$CO$_3$, 3 M aqueous solution (0.100 ml, 0.300 mmol) was added and the reaction mixture was degassed for 5 minutes, then sealed and heated to 90° C. in the microwave for 30 minutes. The reaction mixture was filtered and purified by preparative HPLC (Method D, 60 to 100% B in 17 minutes) to yield Example 807 (13.7 mg, 0.032 mmol, 27.8% yield): $^1$H NMR (500 MHz, DMSO-d$_6$) δ 8.73 (s, 1H), 8.52 (s, 1H), 7.84 (s, 1H), 6.95 (s, 1H), 5.53 (d, J=4.6 Hz, 1H), 5.32 (d, J=4.6 Hz, 1H), 4.09 (s, 3H), 3.99 (s, 3H), 2.65 (s, 3H), 0.97 (s, 9H). LC-MS: method H, RT=1.23 min, MS (ESI) m/z: 425.1 (M+H)$^+$. Analytical HPLC Method B: 99% purity.

Example 808

6-methoxy-2-(2-methoxy-7-methylquinoxalin-5-yl)-4-(methoxymethyl)benzo[d]thiazole

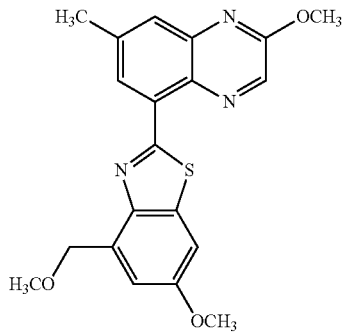
(808)

Intermediate 808A: 2-bromo-6-methoxy-4-(methoxymethyl)benzo[d]thiazole

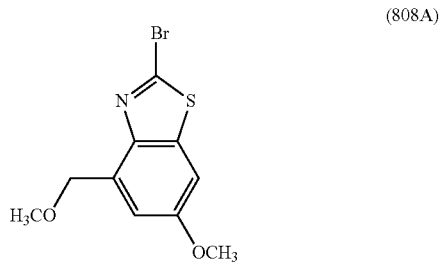 [SMILES: COCc1cc(OC)cc2sc(Br)nc12]
(808A)

Intermediate I-20D (0.100 g, 0.365 mmol) was dissolved in THF (3.65 ml) and sodium hydride (0.022 g, 0.547 mmol) was added. The reaction mixture was allowed to stir for 10 min and MeI (0.034 ml, 0.547 mmol) was added. The reaction mixture was allowed to stir at room temperature for 3 h. The reaction mixture was diluted with water and EtOAc. The layers were separated, and the organic layer was washed with brine, dried with sodium sulfate, and concentrated under reduced pressure. The crude reaction mixture was purified on ISCO using a 12 g column eluting with 0-100% EtOAc in hexanes to yield Intermediate 808A (0.037 g, 0.129 mmol, 35.5% yield) as a white solid. $^1$H NMR (400 MHz, CDCl$_3$) δ 7.20 (s, 2H), 4.96 (s, 2H), 3.90 (s, 3H), 3.53 (s, 3H). LC-MS: method H, RT=1.28 min, MS (ESI) m/z: 287.9(M+H)$^+$.

Example 808

Intermediate I-9 (10 mg, 0.033 mmol) and Intermediate 808A (8.12 mg, 0.033 mmol) were dissolved in DMF (0.333 ml). PdCl$_2$(dppf)-CH$_2$Cl$_2$ adduct (1.632 mg, 1.999 μmol) was added, and the reaction mixture was degassed by bubbling with argon for 15 minutes. Na$_2$CO$_3$, 3 M aqueous solution (0.100 ml, 0.300 mmol) was added, and the reaction mixture was degassed for 5 minutes, then sealed and heated to 90° C. in the microwave for 30 minutes. The reaction mixture was filtered and purified by preparative HPLC (Method D, 70 to 100% B in 25 minutes) to yield Example 808 (0.0046 g, 0.012 mmol, 36% yield): $^1$H NMR (500 MHz, DMSO-d$_6$) δ 8.74 (s, 1H), 8.58 (s, 1H), 7.83 (s, 1H), 7.65 (d, J=2.4 Hz, 1H), 7.14 (s, 1H), 5.04 (s, 2H), 4.09 (s, 3H), 3.89 (s, 3H), 2.65 (s, 3H), 2.56 (s, 3H). LC-MS: method H, RT=1.31 min, MS (ESI) m/z: 382.12 (M+H)$^+$. Analytical HPLC Method B: 100% purity.

Example 809

2-(2-methoxy-7-methylquinoxalin-5-yl)thiazolo[4,5-c]pyridine

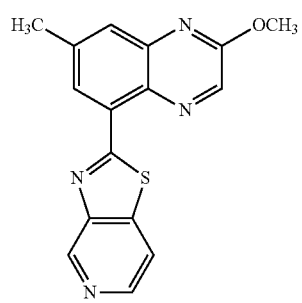
(809)

Intermediate 809A: 2-chlorothiazolo[4,5-c]pyridine

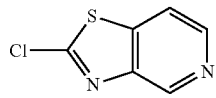
(809A)

Copper(II) chloride (0.445 g, 3.31 mmol) and t-butyl nitrite (0.669 ml, 5.62 mmol) were dissolved in MeCN (13.23 ml) and allowed to stir 10 minutes. Thiazolo[4,5-c]pyridin-2-amine (0.500 g, 3.31 mmol) was dissolved in MeCN (19.84 ml) and the copper solution was added. The reaction mixture was stirred for 1.5 h at 60° C. The reaction mixture was diluted with EtOAc and water. The layers were separated, and the organic layer was washed with brine, dried ($Na_2SO_4$), filtered, and concentrated in vacuo. Purified on ISCO using a 40 g column with 0-100% gradient of EtOAc in hexanes to yield Intermediate 809A (0.125 g, 0.733 mmol, 22.15% yield). LC-MS: method H, RT=0.51 min, MS (ESI) m/z: 170.9 $(M+H)^+$.

Example 809

Intermediate I-9 (17.59 mg, 0.059 mmol) and Intermediate 809A (10 mg, 0.059 mmol) were dissolved in DMF (0.586 ml). $PdCl_2$(dppf)-$CH_2Cl_2$ adduct (2.87 mg, 3.52 μmol) was added, and the reaction mixture was degassed by bubbling with argon for 15 minutes. $Na_2CO_3$, 3 M aqueous solution (0.100 ml, 0.300 mmol) was added, and the reaction mixture was degassed for 5 minutes, then sealed and heated to 90° C. in the microwave for 30 minutes. The reaction mixture was filtered and purified by preparative HPLC (Method D, 20 to 25% B in 25 minutes) to yield Example 809 (1.3 mg, 4.22 μmol, 7.19% yield): $^1$H NMR (500 MHz, DMSO-$d_6$) δ 9.51 (br. s., 1H), 8.77 (s, 1H), 8.69 (s, 1H), 8.61 (br. s., 1H), 8.41 (br. s., 1H), 7.95 (s, 1H), 4.10 (s, 3H), 2.67 (s, 3H). LC-MS: method H, RT=0.86 min, MS (ESI) m/z: 309.1 $(M+H)^+$. Analytical HPLC Method B: 100% purity.

Example 810

2-((6-fluoro-2-(2-methoxy-7-methylquinoxalin-5-yl)thiazolo[5,4-b]pyridin-5-yl)oxy)ethyl pyridin-3-ylcarbamate

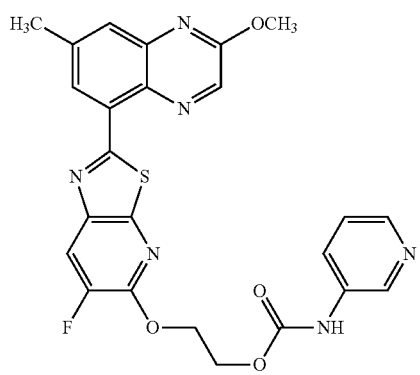
(810)

Intermediate 810A: 2-((2-amino-6-fluorothiazolo[5,4-b]pyridin-5-yl)oxy)ethyl acetate

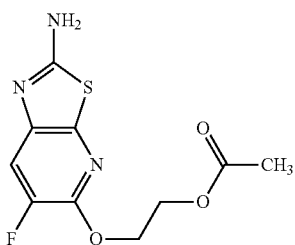
(810A)

Intermediate I-131A (1.394 g, 4.02 mmol) was dissolved in DMF (40.2 ml) and $Cs_2CO_3$ (7.85 g, 24.10 mmol) was added followed by 2-bromoethyl acetate (0.805 g, 4.82 mmol). The reaction mixture was stirred at room temperature for 3 hours. The reaction mixture was then heated to 40° C. and allow to stir for 12 hours. The reaction mixture was diluted with water and EtOAc. The layers were separated, and the organic layer was washed with brine, dried with sodium sulfate, and concentrated under reduced pressure to yield Intermediate 810A (0.540 g, 1.991 mmol, 49.6% yield). $^1$H NMR (400 MHz, $CDCl_3$) δ 7.51 (d, J=10.6 Hz, 1H), 5.16 (br. s., 2H), 4.64-4.57 (m, 2H), 4.50-4.42 (m, 2H), 2.09 (s, 3H). LC-MS: method H, RT=0.69 min, MS (ESI) m/z: 272.1 $(M+H)^+$.

Intermediate 810B: 2-((2-chloro-6-fluorothiazolo[5,4-b]pyridin-5-yl)oxy)ethyl acetate

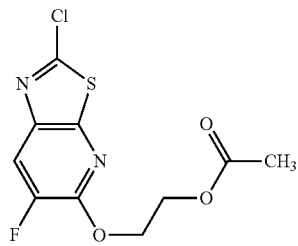

(810B)

Copper(II) chloride (0.455 g, 3.38 mmol) and t-butyl nitrite (0.403 ml, 3.38 mmol) were dissolved in MeCN (7.96 ml) and the mixture was allowed to stir for 10 minutes. Intermediate 810A (0.540 g, 1.991 mmol) was dissolved in MeCN (11.94 ml), and the copper solution was added. The reaction mixture was stirred for 2.5 hours at 60° C. The reaction mixture was diluted with EtOAc and water. The layers were separated, and the organic layer was washed with 1 N HCl, washed with saturated aqueous NaHCO$_3$, washed with brine, dried (Na$_2$SO$_4$), filtered, and concentrated in vacuo. Purified on ISCO using a 12 g column with 0-100% gradient of EtOAc in hexanes to yield Intermediate 810B (0.306 g, 1.053 mmol, 52.9% yield) as a yellow solid. $^1$H NMR (400 MHz, CDCl$_3$) δ 7.86 (d, J=9.7 Hz, 1H), 4.71-4.64 (m, 2H), 4.52-4.45 (m, 2H), 2.10 (s, 3H). LC-MS: method H, RT=1.01 min, MS (ESI) m/z: 291.0 (M+H)$^+$.

Intermediate 810C: 2-((6-fluoro-2-(2-methoxy-7-methylquinoxalin-5-yl)thiazolo[5,4-b] pyridin-5-yl)oxy)ethyl acetate

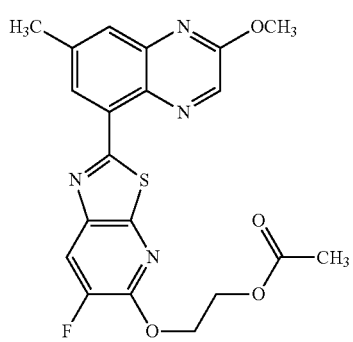

(810C)

Intermediate I-9 (20.65 mg, 0.069 mmol) and Intermediate 810B (20 mg, 0.069 mmol) were dissolved in DMF (0.688 ml). PdCl$_2$(dppf)-CH$_2$Cl$_2$ adduct (3.37 mg, 4.13 µmol) was added, and the reaction mixture was degassed by bubbling with argon for 15 minutes. Na$_2$CO$_3$, 3 M aqueous solution (0.100 ml, 0.300 mmol) was added, and the reaction mixture was degassed for 5 minutes, then sealed and heated to 90° C. in the microwave for 30 minutes. Purified on ISCO using a 12 g column eluting with 0-100% EtOAc in DCM to yield Intermediate 810C (0.039 g, 0.055 mmol, 79% yield) as a yellow solid. LC-MS: method H, RT=1.28 min, MS (ESI) m/z: 428.9 (M+H)$^+$.

Intermediate 810D: 2-((6-fluoro-2-(2-methoxy-7-methylquinoxalin-5-yl)thiazolo[5,4-b]pyridin-5-yl)oxy)ethanol

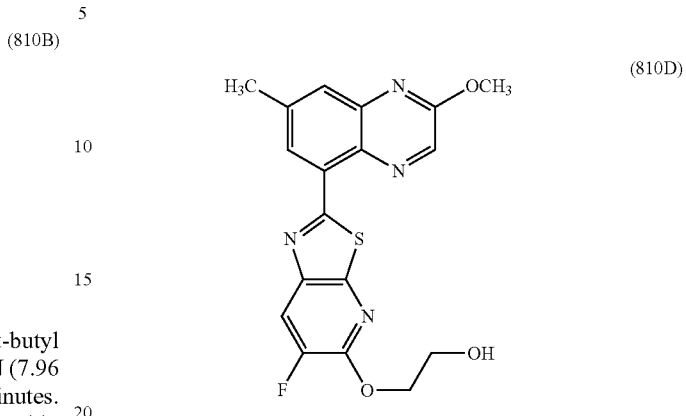

(810D)

To a suspension of Intermediate 810C (0.039 g, 0.091 mmol) in THF (1 mL) and MeOH (0.333 mL) was added NaOH (0.273 mL, 0.273 mmol) at room temperature. The mixture was stirred at room temperature for 1 hour. The mixture was diluted by EtOAc and 1N HCl. The layers were separated, and the organic layer was washed with water, washed with brine, dried with sodium sulfate, and concentrated to yield Intermediate 810D (0.050 g, 0.129 mmol, 100% yield) as a white solid. Used without further purification in the next step. LC-MS: method H, RT=1.14 min, MS (ESI) m/z: 386.9 (M+H)$^+$.

Intermediate 810E: 2-((6-fluoro-2-(2-methoxy-7-methylquinoxalin-5-yl)thiazolo[5,4-b] pyridin-5-yl)oxy)ethyl carbonochloridate

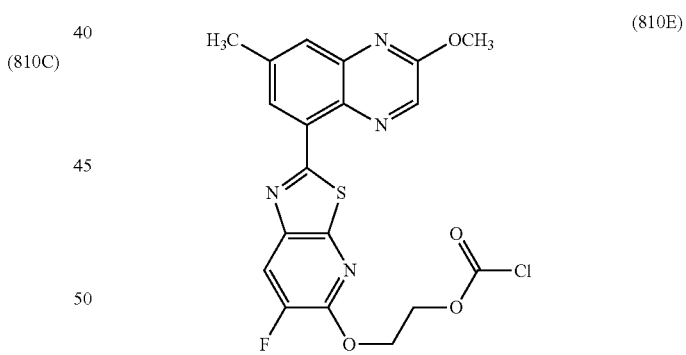

(810E)

To a solution of Intermediate 810D (0.050 g, 0.129 mmol) in THF (5 mL) at room temperature was added 15% phosgene in toluene (0.456 mL, 0.647 mmol), and the mixture was stirred for 3 h. Solvent was completely removed to yield Intermediate 810E (0.058 g, 0.129 mmol, 100% yield) as a yellow solid. The material was used immediately in the next step without purification. LC-MS: method H, RT=1.30 min, MS (ESI) m/z: 448.8 (M+H)$^+$.

Example 810

Pyridin-3-amine (0.012 g, 0.129 mmol) and pyridine (0.105 mL, 1.292 mmol) were dissolved in DCM (2 mL). Intermediate 810E (0.058 g, 0.129 mmol) was added as a

Example 811

2-((6-fluoro-2-(2-methoxy-7-methylquinoxalin-5-yl)thiazolo[5,4-b]pyridin-5-yl)oxy) ethyl (6-fluoro-5-methylpyridin-3-yl)carbamate

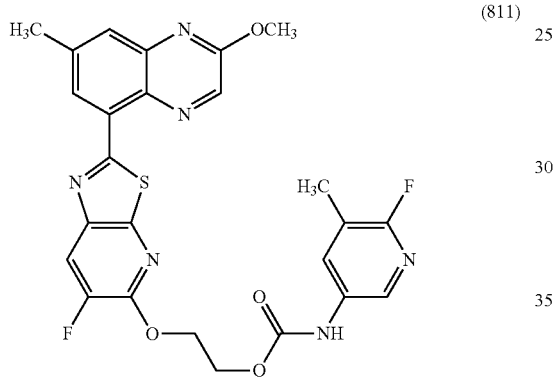

(811)

To a solution of Intermediate 810E (7.5 mg, 0.017 mmol) in DCM (1 mL) and THF (0.5 mL) was added 6-fluoro-5-methylpyridin-3-amine (7.38 mg, 0.058 mmol) followed by DIPEA (0.029 mL, 0.167 mmol). The mixture was stirred at room temperature for 1 hour. The reaction was quenched with 0.2 mL of MeOH. The reaction mixture was concentrated, dissolved in DMF, and filtered. The reaction was purified by preparative HPLC (Method D, 50 to 100% B in 20 minutes, 5 min hold time at 100%) to yield Example 811 (0.0052 g, 9.37 μmol, 56.1% yield): LC-MS: method H, RT=1.22 min, MS (ESI) m/z: 539.2 (M+H)$^+$. Analytical HPLC Method B: 97% purity.

solution in DCM (1 mL). The reaction mixture was allowed to stir for 30 min. The reaction mixture was concentrated under reduced pressure and purified on ISCO using 0-100% EtOAc in hexanes on a 12 g column. The reaction mixture was further purified by preparative HPLC (Method D, 35 to 75% B in 25 minutes, 4 min hold time at 75%) to yield Example 810 (0.0052 g, 10.06 μmol, 7.79% yield) as a pale yellow solid. $^1$H NMR (500 MHz, DMSO-$d_6$) δ 10.00 (s, 1H), 8.73 (s, 1H), 8.62 (br. s., 1H), 8.56 (s, 1H), 8.46 (s, 1H), 8.20 (br. s., 1H), 7.88 (br. s., 2H), 7.33 (br. s., 1H), 4.79 (br. s., 2H), 4.57 (br. s., 2H), 4.10 (s, 3H), 2.64 (br. s., 3H). LC-MS: method H, RT=0.98 min, MS (ESI) m/z: 507.1 (M+H)$^+$. Analytical HPLC Method B: 98% purity.

Example 812

2-((2-(2-methoxy-7-methylquinoxalin-5-yl)-7-methylthiazolo[5,4-b]pyridin-5-yl)oxy) ethyl (6-(thiophen-2-yl)pyridin-3-yl)carbamate

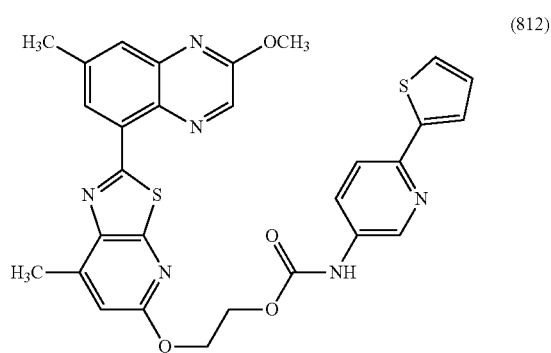 [SMILES: COc1cnc2c(-c3nc4c(C)cc(OCCOC(=O)Nc5ccc(-c6cccs6)nc5)nc4s3)cc(C)cc2n1]

(812)

Intermediate 812A: 2-((2-amino-7-methylthiazolo[5,4-b]pyridin-5-yl)oxy)ethyl acetate

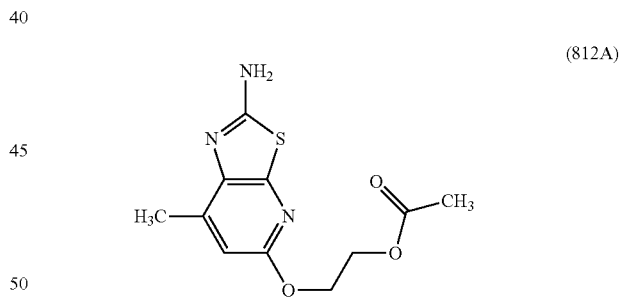

(812A)

2-((2-amino-7-methylthiazolo[5,4-b]pyridin-5-yl)oxy) ethyl acetate (0.050 g, 0.146 mmol) was dissolved in DMF. 2-Bromomethyl acetate (0.058 g, 0.350 mmol) and Cs$_2$CO$_3$ (0.237 g, 0.729 mmol) were added and the reaction mixture was stirred at 40° C. for 18 h. The reaction mixture was diluted with EtOAc and water. The layers were separated. The organic layer was washed with brine dried with sodium sulfate, and concentrated under reduced pressure. The reaction mixture was purified on ISCO using a 24 g column with a 0-100% EtOAc in hexanes gradient to yield Intermediate 812A (0.044 g, 0.165 mmol, 56.5% yield) as a pale yellow solid. $^1$H NMR (400 MHz, CDCl$_3$) δ 6.53-6.53 (m, 1H), 5.01 (br. s., 2H), 4.52-4.48 (m, 2H), 4.44-4.39 (m, 2H), 2.49 (d, J=0.7 Hz, 3H), 2.09 (s, 3H). LC-MS: method H, RT=0.72 min, MS (ESI) m/z: 268.2 (M+H)$^+$.

Intermediate 812B: 2-((2-bromo-7-methylthiazolo[5,4-b]pyridin-5-yl)oxy)ethyl acetate

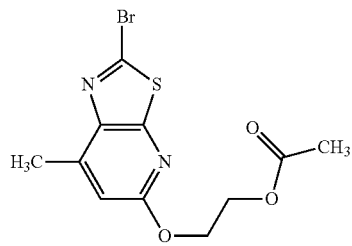
(812B)

Copper(II) bromide (0.063 g, 0.280 mmol) and t-butyl nitrite (0.033 mL, 0.280 mmol) were dissolved in MeCN (0.658 mL) and allowed to stir 10 minutes. Intermediate 812A (0.044 g, 0.165 mmol) was dissolved in MeCN (0.988 mL) and the copper solution was added. The reaction mixture was diluted with EtOAc and water. The organic layer was washed with 1 N HCl, washed with saturated aqueous NaHCO$_3$, washed with brine, dried (Na$_2$SO$_4$), filtered, and concentrated in vacuo to yield Intermediate 812B (0.046 g, 0.139 mmol, 84% yield): $^1$H NMR (400 MHz, CHLOROFORM-d) δ 6.69 (d, J=0.9 Hz, 1H), 4.57-4.53 (m, 2H), 4.44-4.41 (m, 2H), 2.63 (d, J=0.9 Hz, 3H), 2.09 (s, 3H). LC-MS: method H, RT=1.07 min, MS (ESI) m/z: 331.0 (M+H)$^+$.

Intermediate 812C: 2-((2-(2-methoxy-7-methylquinoxalin-5-yl)-7-methylthiazolo[5,4-b] pyridin-5-yl)oxy)ethyl acetate

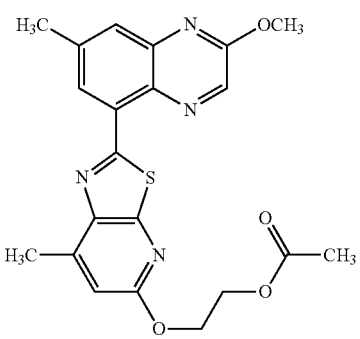
(812C)

Intermediate I-9 (0.042 g, 0.140 mmol) and Intermediate 812B (0.046 g, 0.140 mmol) were dissolved in DMF (1 mL). PdCl$_2$(dppf)-CH$_2$Cl$_2$Adduct (6.86 mg, 8.40 μmol) was added and the reaction mixture was degassed by bubbling with argon for 15 minutes. Na$_2$CO$_3$, 3 M aqueous solution (0.100 mL, 0.300 mmol) was added and the reaction mixture was degassed for 5 minutes, then sealed and heated to 90° C. in the microwave for 30 minutes. The reaction was purified on ISCO using 24 g column with a 0-100% EtOAc in hexanes gradient to yield Intermediate 812C (0.021 g, 0.049 mmol, 35.4% yield) as an off white solid. $^1$H NMR (400 MHz, CDCl$_3$) δ 8.60 (d, J=2.0 Hz, 1H), 8.54 (s, 1H), 7.75 (s, 1H), 6.74 (s, 1H), 4.63 (dd, J=5.8, 3.6 Hz, 2H), 4.51-4.43 (m, 2H), 4.13 (s, 3H), 2.79 (s, 3H), 2.66 (s, 3H), 2.11 (s, 3H). LC-MS: method H, RT=1.34 min, MS (ESI) m/z: 425.1 (M+H)$^+$.

Intermediate 812D: 2-((2-(2-methoxy-7-methylquinoxalin-5-yl)-7-methylthiazolo[5,4-b] pyridin-5-yl)oxy)ethanol

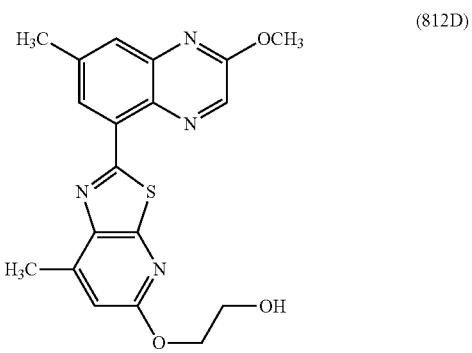
(812D)

To a suspension of Intermediate 812C (0.143 g, 0.337 mmol) in THF (3 mL) and MeOH (1 mL) was added NaOH (1.011 mL, 1.011 mmol) at room temperature. The mixture was stirred at room temperature for 1 hour. The mixture was diluted with EtOAc and 1N HCl. The organic layer was washed with water, washed with brine, dried with sodium sulfate, and concentrated to yield Intermediate 812D (0.120 g, 0.314 mmol, 93% yield) as a tan solid. $^1$H NMR (400 MHz, MeOH-d$_4$) δ 8.61 (s, 1H), 8.58 (s, 1H), 7.78 (s, 1H), 6.82 (s, 1H), 4.48-4.45 (m, 2H), 4.40-4.36 (m, 1H), 4.13 (s, 3H), 3.94-3.90 (m, 2H), 2.77 (s, 3H), 2.66 (s, 3H). LC-MS: method H, RT=1.15 min, MS (ESI) m/z: 383.9 (M+H)$^+$.

Intermediate 812E: 2-((2-(2-methoxy-7-methylquinoxalin-5-yl)-7-methylthiazolo[5,4-b] pyridin-5-yl)oxy)ethyl carbonochloridate

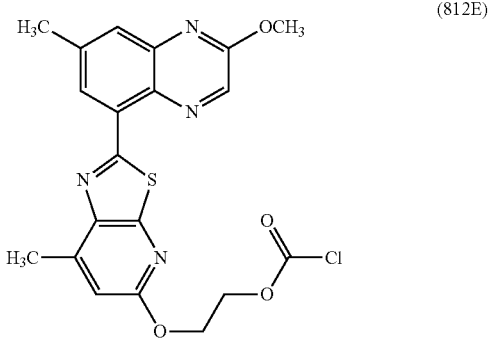
(812E)

To a solution of Intermediate 812D (0.025 g, 0.065 mmol) in THF (3 mL) at was added 15% phosgene in toluene (0.231 mL, 0.327 mmol) and the mixture was stirred at for 1 h. The reaction mixture was concentrated under vacuum to give Intermediate 812E (0.030 g, 0.067 mmol, 100% yield) as a yellow solid. It was used for the next step without any purification. LC-MS: method H, RT=1.35 min, MS (ESI) m/z: 444.7 (M+H)$^+$.

Example 812

To a solution of Intermediate 812E (20 mg, 0.045 mmol) in DCM (1 mL) and THF (0.5 mL) was added 6-(thiophen-2-yl)pyridin-3-amine (14.81 mg, 0.157 mmol) followed by DIEA (0.079 mL, 0.450 mmol). The mixture was stirred at for 1 hour. The reaction mixture was diluted with EtOAc and water. The combined organic layer was washed with brine and concentrated under vacuum. The reaction mixture was diluted with DMSO, filtered, and purified by preparative HPLC (Method D, 55% to 100% B in 20 minutes) to yield Example 812 (0.0057 g, 5.61 μmol, 12.48% yield): $^1$H NMR (500 MHz, DMSO-$d_6$) δ 10.05 (br. s., 1H), 8.63 (s, 1H), 8.56 (br. s., 1H), 8.50 (s, 1H), 7.92 (br. s., 1H), 7.83 (d, J=8.8 Hz, 1H), 7.78 (s, 1H), 7.63 (d, J=3.3 Hz, 1H), 7.55 (d, J=4.8 Hz, 1H), 7.12 (t, J=3.9 Hz, 1H), 6.90 (s, 1H), 4.66 (br. s., 2H), 4.52 (br. s., 2H), 4.06 (s, 3H), 2.72 (s, 3H), 2.62 (s, 3H). LC-MS: method H, RT=1.21 min, MS (ESI) m/z: 585.5 (M+H)$^+$. Analytical HPLC Method B: 97% purity.

Example 813

(R)-1-((2-(2-ethoxy-7-methylquinoxalin-5-yl)-6-fluorothiazolo[5,4-b]pyridin-5-yl)oxy)propan-2-yl (2-methylpyrimidin-5-yl)carbamate

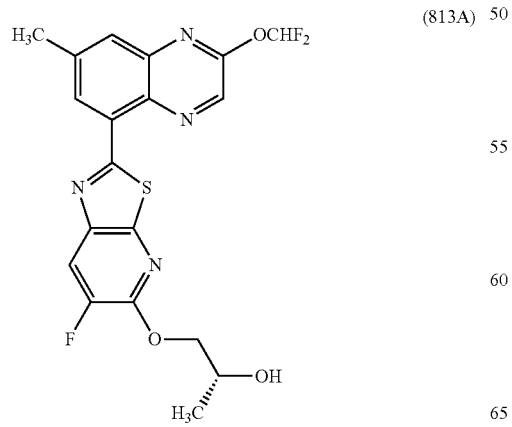

(813)

Intermediate 813A: (R)-1-((2-(2-(difluoromethoxy)-7-methylquinoxalin-5-yl)-6-fluorothiazolo[5,4-b]pyridin-5-yl)oxy)propan-2-ol

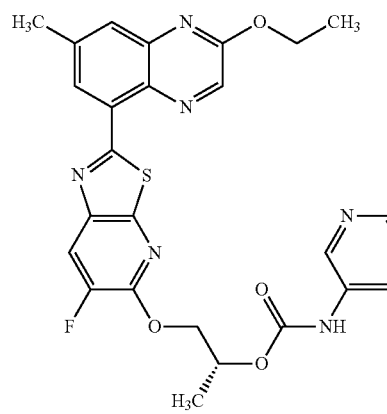

(813A)

Intermediate I-1 (0.483 g, 1.903 mmol) and Intermediate I-131 (0.500 g, 1.903 mmol) were dissolved in DMF (19.03 ml). PdCl$_2$(dppf)-CH$_2$Cl$_2$ adduct (0.093 g, 0.114 mmol) was added, and the reaction mixture was degassed by bubbling with argon for 15 minutes. Na$_2$CO$_3$, 3 M aqueous solution (0.100 ml, 0.300 mmol) was added, and the reaction mixture was degassed for 5 minutes, then sealed and heated to 90° C. in the microwave for 30 minutes. The reaction mixture was diluted with water and EtOAc. The layers were separated and the organic layer was washed with brine, dried with sodium sulfate, and concentrated under reduced pressure to yield a brown oil. Purified by ISCO using 0-70% gradient of EtOAc in hexanes on a 120 g column over 15 min to yield Intermediate 813A (0.591 g, 1.354 mmol, 71.1% yield): $^1$H NMR (500 MHz, CDCl$_3$) δ 8.74 (d, J=1.7 Hz, 1H), 8.71 (s, 1H), 8.04 (d, J=10.2 Hz, 1H), 7.84 (dd, J=1.8, 1.0 Hz, 1H), 7.83-7.53 (m, 1H), 4.58 (dd, J=10.7, 2.8 Hz, 1H), 4.47-4.37 (m, 1H), 4.34 (br. s., 1H), 2.71 (s, 3H), 1.61-1.53 (m, 1H), 1.38 (d, J=6.3 Hz, 3H). LC-MS: method H, RT=1.24 min, MS (ESI) m/z: 437.1 (M+H)$^+$.

Intermediate 813B: (R)-1-((2-(2-ethoxy-7-methylquinoxalin-5-yl)-6-fluorothiazolo[5,4-b]pyridin-5-yl)oxy)propan-2-ol

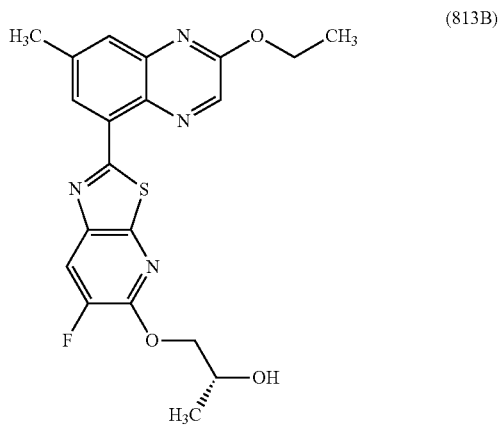 [SMILES: CCOc1cnc2c(-c3nc4cc(F)c(OC[C@@H](C)O)nc4s3)cc(C)cc2n1]

(813B)

Intermediate 813A (0.035 g, 0.080 mmol) was dissolved in THF (2 ml) and sodiummethoxide (0.040 ml, 0.080 mmol, 2 M in EtOH) was added. The reaction mixture was allowed to stir at for 2 hours. The reaction mixture was diluted with water and EtOAc. The layers were separated, and the organic layer was washed with brine, dried with sodium sulfate, and concentrated under reduced pressure to yield Intermediate 813B (0.030 g, 0.058 mmol, 80% yield). Used without further purification in the next step. LC-MS: method H, RT=1.30 min, MS (ESI) m/z: 415.1 (M+H)$^+$.

Intermediate 813C: (R)-1-((2-(2-ethoxy-7-methylquinoxalin-5-yl)-6-fluorothiazolo[5,4-b]pyridin-5-yl)oxy)propan-2-yl carbonochloridate

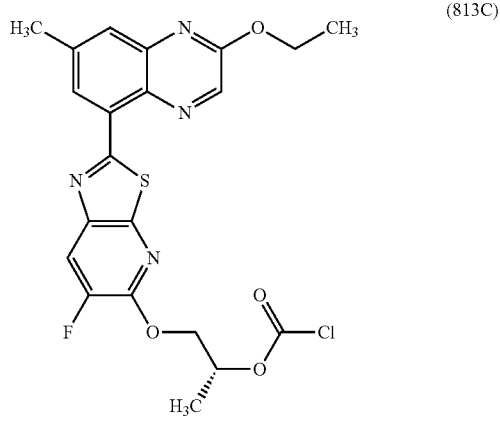 [SMILES: CCOc1cnc2c(-c3nc4cc(F)c(OC[C@@H](C)OC(=O)Cl)nc4s3)cc(C)cc2n1]

(813C)

Example 814

(R)-1-((2-(2-ethoxy-7-methylquinoxalin-5-yl)-6-fluorothiazolo[5,4-b]pyridin-5-yl)oxy)propan-2-yl (2-(2-hydroxyethoxy)pyrimidin-5-yl)carbamate

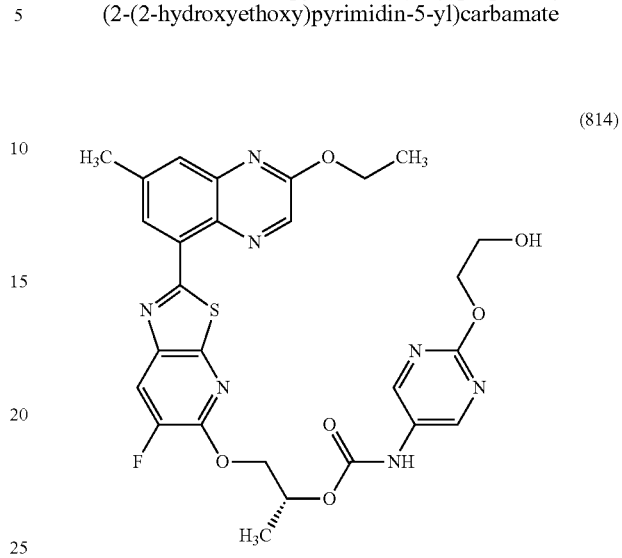

(814)

Intermediate 814A: (R)-1-((2-(2-ethoxy-7-methylquinoxalin-5-yl)-6-fluorothiazolo[5,4-b]pyridin-5-yl)oxy)propan-2-yl (2-(2-hydroxyethoxy)pyrimidin-5-yl)carbamate

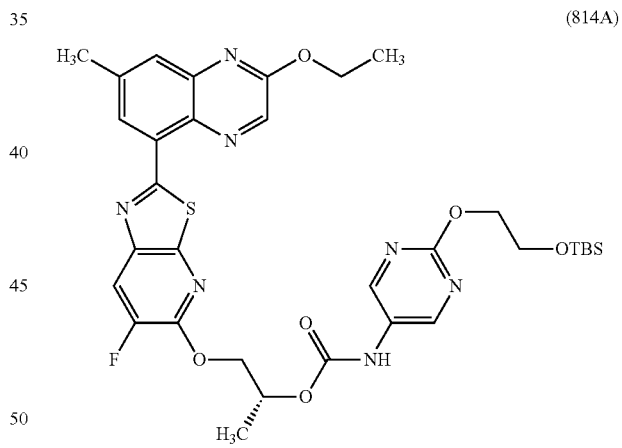

(814A)

To a solution of Intermediate 813B (0.030 g, 0.058 mmol) in THF (3 mL) at was added 15% phosgene in toluene (0.511 mL, 0.724 mmol), and the mixture was stirred at for 12 hours. Solvent was completely removed, and the sample was stored under vacuum overnight to yield Intermediate 813C (0.035 g, 0.066 mmol, 91% yield) as a yellow solid. LC-MS: method H, RT=1.42 min, MS (ESI) m/z: 477.1 (M+H)$^+$.

Example 813

2-Methylpyrimidin-5-amine (13.73 mg, 0.126 mmol) and pyridine (0.068 mL, 0.839 mmol) were dissolved in DCM (3 mL). Intermediate 813C (40 mg, 0.084 mmol) was added as a solution in DCM (1 mL). The reaction mixture was allowed to stir for 1 hour. The reaction mixture was concentrated under reduced pressure and purified by ISCO using a 12 g column with a 0-100% EtOAc in hexanes gradient to yield Example 813 (0.0203 g, 0.035 mmol, 41.8% yield) as a yellow solid. $^1$H NMR (400 MHz, CDCl$_3$) δ 8.74 (br. s., 2H), 8.55 (t, J=2.3 Hz, 1H), 8.50 (d, J=2.6 Hz, 1H), 8.01 (s, 1H), 7.98 (d, J=0.9 Hz, 1H), 7.74 (s, 1H), 6.55 (br. s., 1H), 5.75 (dd, J=6.5, 3.4 Hz, 1H), 5.39 (dd, J=6.5, 3.4 Hz, 1H), 4.57 (d, J=7.0 Hz, 3H), 2.64 (s, 3H), 1.52 (d, J=1.5 Hz, 3H), 1.50 (s, 3H), 1.48 (d, J=1.5 Hz, 3H). LC-MS: method H, RT=1.27 min, MS (ESI) m/z: 550.1 (M+H)$^+$. Analytical HPLC Method B: 95% purity.

Intermediate I-97 (16.95 mg, 0.063 mmol) and pyridine (0.034 mL, 0.419 mmol) were dissolved in DCM (3 mL). Intermediate 813C (20 mg, 0.042 mmol) was added as a solution in DCM (1 mL). The reaction mixture was allowed to stir for 1 hour. The reaction mixture was concentrated under reduced pressure. Used without further purification in the next step. LC-MS: method H, RT=1.56 min, MS (ESI) m/z: 710.3 (M+H)$^+$.

Example 814

Intermediate 814A (0.009 g, 0.013 mmol) was dissolved in THF (2 mL) and 2 mL of 90% MeOH, 10% water, 0.1% TFA was added. The reaction mixture was allowed to stir for 12 hours. The reaction mixture was concentrated, dissolved in DMF, filtered, and purified by preparative HPLC (Method D, 50% to 100% B in 19 minutes, 6 min hold time) to yield Example 814 (7.7 mg, 0.013 mmol, 100% yield): $^1$H NMR (500 MHz, DMSO-$d_6$) δ 9.81-9.74 (m, 1H), 8.61-8.52 (m, 3H), 8.41 (br. s., 1H), 8.33 (d, J=10.7 Hz, 1H), 7.71 (s, 1H), 5.67 (br. s., 1H), 5.24 (br. s., 1H), 4.93-4.87 (m, 1H), 4.80 (d, J=9.8 Hz, 1H), 4.48 (q, J=6.8 Hz, 5H), 4.20 (d, J=5.2 Hz, 3H), 2.57 (s, 3H), 1.45-1.38 (m, 6H). LC-MS: method H, RT=1.20 min, MS (ESI) m/z: 596.2 (M+H)$^+$. Analytical HPLC Method B: 100% purity.

Example 815

(R)-1-((2-(2-ethoxy-7-methylquinoxalin-5-yl)-6-fluorothiazolo[5,4-b]pyridin-5-yl)oxy) propan-2-yl (2-((R)-2-hydroxypropoxy)pyrimidin-5-yl)carbamate

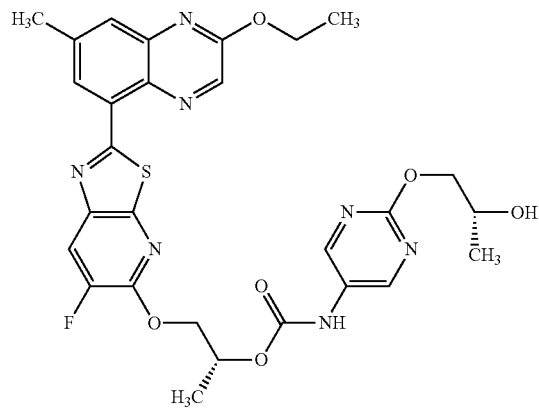

(815)

Intermediate 815A: (R)-1-((2-(2-ethoxy-7-methylquinoxalin-5-yl)-6-fluorothiazolo [5,4-b]pyridin-5-yl)oxy)propan-2-yl (2-((R)-2-((tert-butyldimethylsilyl)oxy)propoxy) pyrimidin-5-yl)carbamate

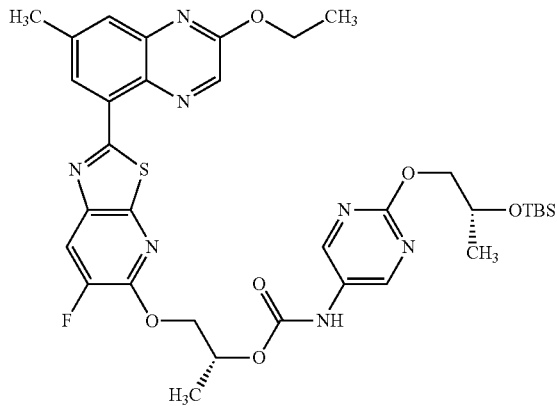

(815A)

Intermediate I-103 (0.020 g, 0.069 mmol) and pyridine (0.051 mL, 0.629 mmol) were dissolved in DCM (2 mL) Intermediate 813C (0.030 g, 0.063 mmol) was added as a solution in DCM (1 mL). The reaction mixture was allowed to stir for 1 hour. The reaction mixture was concentrated under reduced pressure and purified on ISCO using 24 g column eluting with 0-100% EtOAc in hexanes over 15 min to yield Intermediate 815A (28.3 mg, 0.039 mmol, 62.1% yield) as a pale yellow solid. $^1$H NMR (400 MHz, CDCl$_3$) δ 9.08-9.05 (m, 2H), 8.56 (d, J=2.0 Hz, 1H), 8.52 (s, 1H), 8.01 (d, J=10.3 Hz, 1H), 7.77 (s, 1H), 6.80 (s, 1H), 5.87-5.73 (m, 1H), 5.28 (dd, J=6.6, 2.9 Hz, 1H), 4.68-4.54 (m, 1H), 4.09 (s, 2H), 2.67 (s, 3H), 1.54-1.48 (m, 9H). LC-MS: method H, RT=1.58 min, MS (ESI) m/z: 724.0 (M+H)$^+$.

Example 815

Intermediate 815A (0.0283 g, 0.039 mmol) was dissolved in THF (1 mL) and EtOH (1 mL). To the solution was added 4 M HCl in dioxane (1 mL, 110 mmol), and the reaction mixture was allowed to stir at room temperature for 3 hours. The reaction mixture was concentrated under reduced pressure, dissolved in DMF, filtered, and purified by preparative HPLC (Method D, 50% to 100% B in 20 minutes, 10 min hold time) to yield Example 815 (0.0145 g, 0.024 mmol, 60.8% yield): $^1$H NMR (500 MHz, DMSO-$d_6$) δ 9.86-9.73 (m, 1H), 8.62-8.53 (m, 3H), 8.44 (br. s., 1H), 8.36 (d, J=10.7 Hz, 1H), 7.74 (s, 1H), 5.69 (br. s., 1H), 5.26 (br. s., 2H), 4.83 (d, J=10.1 Hz, 1H), 4.50 (q, J=7.0 Hz, 4H), 4.29 (d, J=7.6 Hz, 1H), 4.04 (d, J=12.8 Hz, 1H), 3.93 (br. s., 1H), 3.52-3.46 (m, 3H), 2.59 (s, 3H), 1.47-1.40 (m, 6H). LC-MS: method H, RT=1.23 min, MS (ESI) m/z: 610.1 (M+H)$^+$. Analytical HPLC Method B: 100% purity.

Example 816

(2R,3S)-3-((2-(2-ethoxy-7-methylquinoxalin-5-yl)-6-fluorothiazolo[5,4-b]pyridin-5-yl)oxy)butan-yl)oxy)butan-2-yl (2-(hydroxymethyl)pyrimidin-5-yl)carbamate

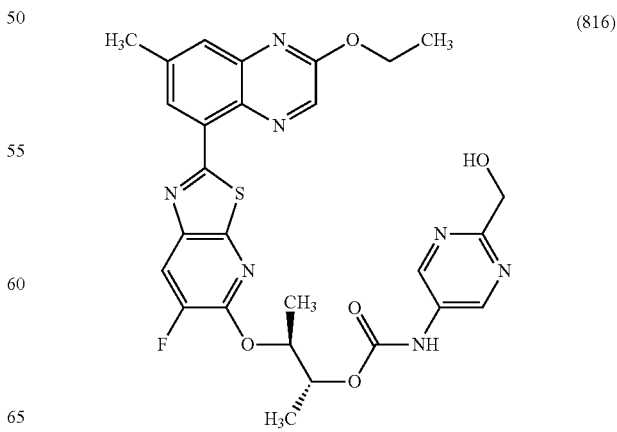

(816)

Intermediate 816A: (2R,3S)-3-((2-(2-(difluoromethoxy)-7-methylquinoxalin-5-yl)-6-fluorothiazolo[5,4-b]pyridin-5-yl)oxy)butan-2-ol

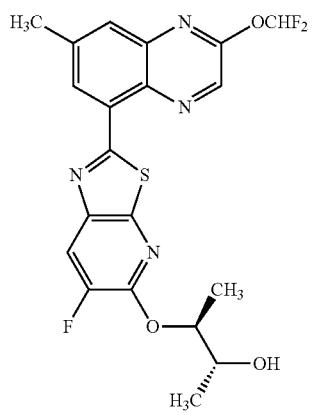
(816A)

Intermediate I-1 (0.075 g, 0.285 mmol) and Intermediate I-133 (0.082 g, 0.285 mmol) were dissolved in DMF (2.95 ml). PdCl$_2$(dppf)-CH$_2$Cl$_2$ adduct (0.012 g, 0.018 mmol) was added, and the reaction mixture was degassed by bubbling with argon for 15 minutes. Na$_2$CO$_3$, 3 M aqueous solution (0.100 ml, 0.300 mmol) was added, and the reaction mixture was degassed for 5 minutes, then sealed and heated to 90° C. in the microwave for 30 minutes. The reaction mixture was diluted with water and EtOAc. The layers were separated and the organic layer was washed with brine, dried with sodium sulfate, and concentrated under reduced pressure to yield a brown oil. Purified by ISCO using 0-100% gradient of EtOAc in hexanes on a 24 g column over 15 min to yield Intermediate 816A (0.050 g, 0.111 mmol, 37.6% yield): $^1$H NMR (400 MHz, CDCl$_3$) δ 8.74 (d, J=1.8 Hz, 1H), 8.71 (s, 1H), 8.03 (d, J=10.1 Hz, 1H), 7.89-7.49 (m, 2H), 5.41 (dd, J=6.5, 3.0 Hz, 1H), 4.26-4.08 (m, 1H), 2.49 (d, J=4.6 Hz, 1H), 1.46 (d, J=6.4 Hz, 3H), 1.33 (d, J=6.4 Hz, 3H). LC-MS: method H, RT=1.27 min, MS (ESI) m/z: 451.1 (M+H)$^+$.

Intermediate 816B: (2R,3S)-3-((2-(2-ethoxy-7-methylquinoxalin-5-yl)-6-fluorothiazolo[5,4-b]pyridin-5-yl)oxy)butan-2-ol

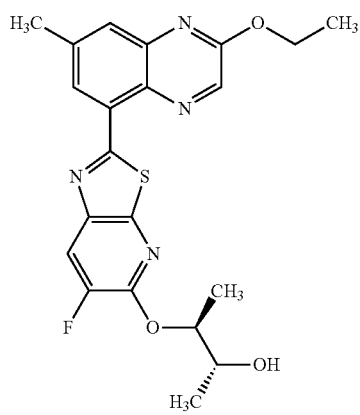
(816B)

Intermediate 816A (0.100 g, 0.222 mmol) was dissolved in THF (2 ml) and sodiumethoxide (0.111 ml, 0.222 mmol, 2 M in EtOH) was added. The reaction mixture was allowed to stir at room temperature for 2 hours. The reaction mixture was diluted with water and EtOAc. The layers were separated, and the organic layer was washed with brine, dried with sodium sulfate, and concentrated under reduced pressure to yield Intermediate 816B (0.090 g, 0.210 mmol, 95% yield). Used without further purification in the next step. LC-MS: method H, RT=1.25 min, MS (ESI) m/z: 429.1 (M+H)$^+$.

Intermediate 816C: (2R,3S)-3-((2-(2-ethoxy-7-methylquinoxalin-5-yl)-6-fluorothiazolo[5,4-b]pyridin-5-yl)oxy)butan-2-yl carbonochloridate

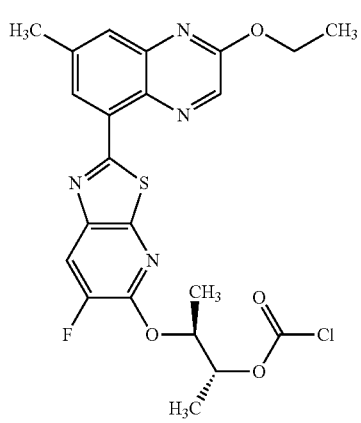
(816C)

To a solution of Intermediate 816B (0.025 g, 0.058 mmol) in THF (5 mL) at room temperature was added 15% phosgene in toluene (0.206 mL, 0.292 mmol), and the mixture was stirred at room temperature for 12 hours. Solvent was completely removed, and the sample was stored under vacuum overnight to yield Intermediate 816C (0.029 g, 0.053 mmol, 90% yield) as a yellow solid. LC-MS: method H, RT=1.43 min, MS (ESI) m/z: 490.0 (M+H)$^+$.

Intermediate 816D: methyl 5-(((((2R,3S)-3-((2-(2-ethoxy-7-methylquinoxalin-5-yl)-6-fluorothiazolo[5,4-b]pyridin-5-yl)oxy)butan-2-yl)oxy)carbonyl)amino)pyrimidine-2-carboxylate

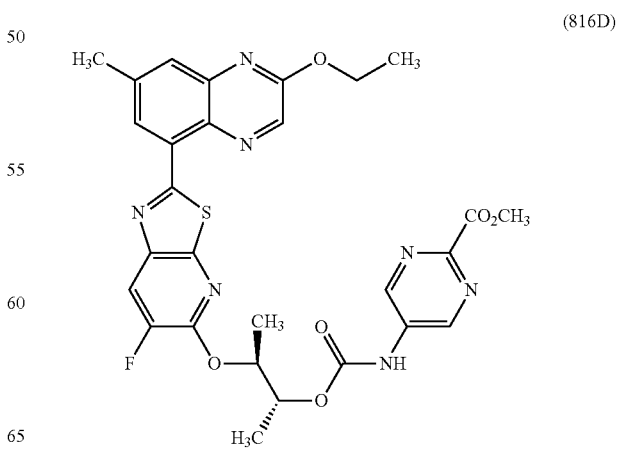
(816D)

Methyl 5-aminopyrimidine-2-carboxylate (10.29 mg, 0.067 mmol) and pyridine (0.049 mL, 0.611 mmol) were dissolved in DCM (2 mL) Intermediate 816C (0.030 g, 0.061 mmol) was added as a solution in DCM (1 mL). The reaction mixture was allowed to stir for 1 hour. The reaction mixture was concentrated under reduced pressure and purified on ISCO using 24 g column eluting with 0-100% EtOAc over 15 min to yield Intermediate 816D (24.6 mg, 0.040 mmol, 66.3% yield) as a pale yellow solid. $^1$H NMR (400 MHz, CDCl$_3$) δ 8.47 (d, J=1.8 Hz, 3H), 8.44 (s, 1H), 7.91 (d, J=10.3 Hz, 1H), 7.66 (s, 1H), 7.13 (s, 1H), 5.70-5.60 (m, 1H), 5.31 (br. s., 1H), 2.56 (s, 3H), 1.41 (d, J=6.8 Hz, 5H), 1.17 (s, 3H), 0.07-0.11 (m, 6H). LC-MS: method H, RT=1.27 min, MS (ESI) m/z: 608.0 (M+H)$^+$.

Example 816

Intermediate 816D (39 mg, 0.064 mmol) was solvated in THF (1 mL) and cooled to −78° C. Diisobutylaluminum hydride (1 M in toluene) (0.193 mL, 0.193 mmol) was added to the cooled mixture, and the reaction mixture was stirred for 30 min. The reaction mixture was quenched with 1 mL of a 1 M HCl solution at −78° C. The resulting thick, orange sludge was allowed to thaw to room temperature and stirred for a total of 30 min until the solution became fluid and bright yellow. The mixture was diluted with EtOAc and washed with saturated NH$_4$Cl before being dried over sodium sulfate and filtered over a pad of SiO$_2$ gel to remove aluminates. The filtrate was concentrated and resubjected to identical reaction conditions to those described above. This second reaction mixture was quenched with saturated Rochelle's salt and allowed to stir at room temperature for 1 hour. The resulting mixture was diluted with EtOAc and the layers were separated. The aqueous layer was back extracted with EtOAc 3×, and the combined organic layer was washed with brine, dried with sodium sulfate, and concentrated under reduced pressure. The crude material was dissolved in DMF, filtered, and purified by preparative HPLC (Method D, 50% to 100% B in 22 minutes, 5 min hold time) to yield Example 816 (0.0078 g, 0.013 mmol, 20.97% yield): $^1$H NMR (500 MHz, DMSO-d$_6$) δ 9.95 (br. s., 1H), 8.79 (br. s., 2H), 8.61 (s, 1H), 8.49 (s, 1H), 8.41 (d, J=10.7 Hz, 1H), 7.79 (s, 1H), 5.68 (d, J=6.4 Hz, 1H), 5.17 (d, J=5.2 Hz, 1H), 4.53 (q, J=7.0 Hz, 2H), 4.49 (s, 2H), 2.61 (s, 3H), 1.47-1.43 (m, 6H), 1.40 (d, J=6.4 Hz, 3H). LC-MS: method H, RT=0.98 min, MS (ESI) m/z: 580.0 (M+H)$^+$. Analytical HPLC Method B: 100% purity.

Example 817

1-(2-(2-ethoxy-7-methylquinoxalin-5-yl)-6-methoxybenzo[d]thiazol-4-yl)-2,2-dimethylpropan-1-ol

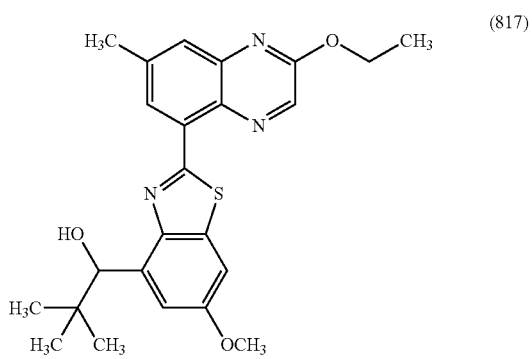 [SMILES: CCOc1cnc2c(-c3nc4c(C(O)C(C)(C)C)cc(OC)cc4s3)cc(C)cc2n1]

(817)

Intermediate 817A: 2-ethoxy-7-methyl-5-(4,4,5,5-tetramethyl-1,3,2-dioxaborolan-2-yl) quinoxaline

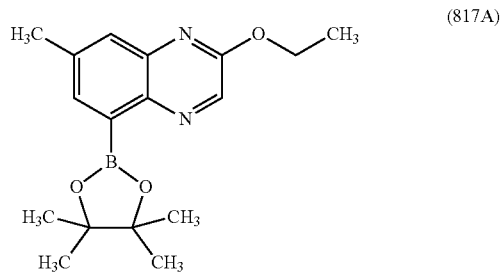 [SMILES: CCOc1cnc2c(B3OC(C)(C)C(C)(C)O3)cc(C)cc2n1]

(817A)

In a sealed tube, Intermediate 661F (290 mg, 1.086 mmol), 4,4,4',4',5,5,5',5'-octamethyl-2,2'-bi(1,3,2-dioxaborolane) (551 mg, 2.171 mmol), and potassium acetate (213 mg, 2.171 mmol) were mixed in 1,4-dioxane (5 mL). After degassing with bubbling argon for 10 minutes, Pd(dppf)Cl$_2$·CH$_2$Cl$_2$ (44.3 mg, 0.054 mmol) was added. The vial was sealed and heated at 120° C. for 60 minutes in the microwave. The reaction mixture was cooled to room temperature, loaded on celite and was purified on ISCO (40 g column, 0-50% EtOAc/Hexane in 18 minutes) to yield Intermediate 817A (0.311 g, 0.990 mmol, 91% yield): $^1$H NMR (400 MHz, DMSO-d$_6$) δ 8.53 (s, 1H), 7.91 (s, 1H), 7.68 (s, 1H), 4.47 (q, J=7.2 Hz, 2H), 3.26 (br. s., 3H), 1.41 (t, J=7.0 Hz, 3H), 1.34 (s, 12H). LC-MS: method H, RT=0.94 min, MS (ESI) m/z: 233.0 (M+H)$^+$ (mass of the boronic acid).

Example 817

Intermediate 817A (10 mg, 0.032 mmol) and Intermediate 628A (9.10 mg, 0.032 mmol) were dissolved in DMF (1 ml). PdCl$_2$(dppf)-CH$_2$Cl$_2$ adduct (1.560 mg, 1.910 μmol) was added, and the reaction mixture was degassed by bubbling with argon for 15 minutes. Na$_2$CO$_3$, 3 M aqueous solution (0.100 ml, 0.300 mmol) was added, and the reaction mixture was degassed for 5 minutes, then sealed and heated to 90°

C. in the microwave for 30 minutes. The reaction mixture was filtered and purified by preparative HPLC (Method D, 45% to 80% B in 25 minutes, 7 min hold time) to yield Example 817 (4.5 mg, 9.87 μmol, 31.0% yield): $^1$H NMR (500 MHz, DMSO-$d_6$) δ 8.68 (s, 1H), 8.51 (s, 1H), 7.78 (s, 1H), 7.58 (s, 1H), 7.13 (s, 1H), 5.41 (d, J=4.6 Hz, 1H), 5.36 (br. s., 1H), 4.53 (q, J=7.0 Hz, 2H), 3.86 (s, 3H), 2.63 (s, 3H), 1.44 (t, J=7.0 Hz, 3H), 0.94 (s, 9H). LC-MS: method H, RT=1.39 min, MS (ESI) m/z: 438.2 (M+H)$^+$. Analytical HPLC Method B: 96% purity.

Example 818

(R)-1-((2-(7-cyano-2-methoxyquinoxalin-5-yl)-5-fluorobenzo[d]thiazol-6-yl)oxy)propan-2-yl (6-cyanopyridin-3-yl)carbamate

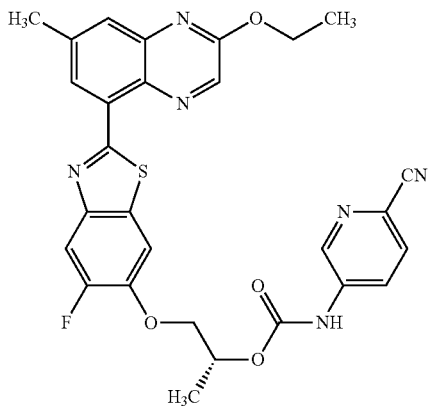

(818)

Intermediate 818A (R)-1-((2-bromo-5-fluorobenzo[d]thiazol-6-yl)oxy)propan-2-ol

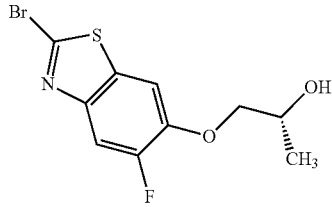

(818A)

In a flask charged with a stirring bar, Intermediate I-60 (215 mg, 0.867 mmol) was suspended in (R)-2-methyloxirane (1 mL, 0.867 mmol). Potassium carbonate (144 mg, 1.040 mmol) was added, followed by tetrabutylammonium bromide (335 mg, 1.040 mmol). The mixture was allowed to stir at 60° C. for 18 hours. On the next day, the reaction mixture was diluted by adding 20 mL of DCM and silica gel was added. The solvent was removed on the rotavapor and sample was dry loaded on ISCO (24 g silica gel column, 0-60% EtOAc/Hexane). Collection of the desired fraction and removal of solvent gave Intermediate 818A (245.4 mg, 0.802 mmol, 92% yield) as colorless oil. $^1$H NMR (400 MHz, DMSO-$d_6$) δ 7.93 (d, J=1.3 Hz, 1H), 7.97-7.89 (m, 1H), 4.96 (d, J=4.8 Hz, 1H), 4.07-3.98 (m, 1H), 3.98-3.89 (m, 2H), 1.18 (d, J=6.2 Hz, 3H); $^{19}$F NMR (376 MHz, DMSO-$d_6$) δ −133.79 (s, 1F); LC-MS: method E, RT=0.85 min, MS (ESI) m/z: 306.0, 308.0 (M+H)$^+$.

Intermediate 818B: (R)-1-((2-bromo-5-fluorobenzo[d]thiazol-6-yl)oxy)propan-2-yl carbonochloridate

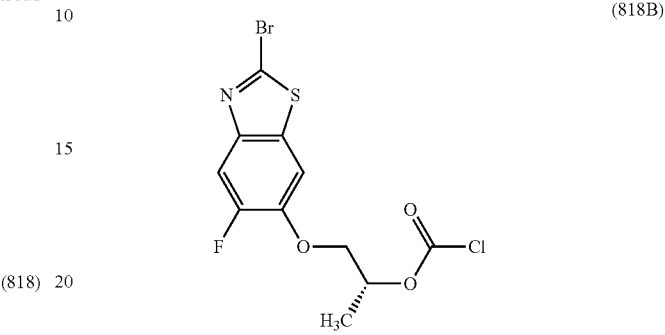

(818B)

Intermediate 818A (110 mg, 0.359 mmol) was dissolved in THF (5 mL) under $N_2$. Phosgene (2.56 mL, 3.59 mmol, 15% by wt.) in toluene solution was added. The resulting mixture was stirred at room temperature for 5 hours, then the solvent was removed on rotavapor and residue was dried on HVAC for 30 minutes. The crude product was used in the next step without purification. LC-MS: method E, RT=1.08 min, MS (ESI) m/z: 365.0, 366.9 (M+H)$^+$.

Intermediate 818C: (R)-1-((2-chloro-5-fluorobenzo[d]thiazol-6-yl)oxy)propan-2-yl (6-cyanopyridin-3-yl)carbamate

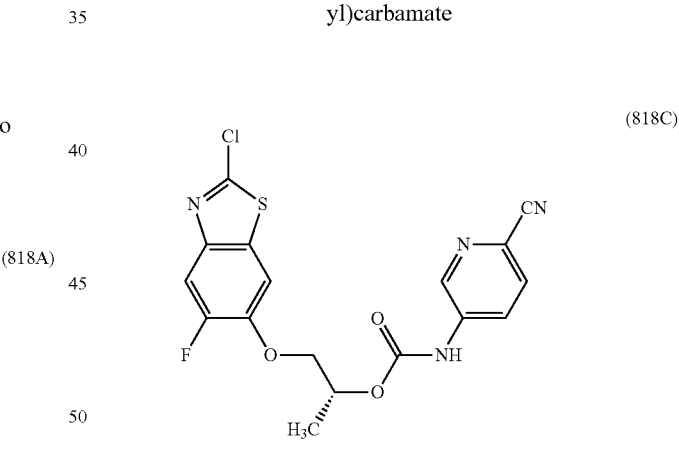

(818C)

Intermediate 818B (66 mg, 0.179 mmol) was dissolved in DCM (3 mL) and mixed with 5-aminopicolinonitrile (85 mg, 0.716 mmol). Anhydrous pyridine (0.072 mL, 0.895 mmol) was added. The mixture was allowed to stir at room temperature for 2 hours. The solvent was removed on rotavapor and the residue was purified on ISCO column (24 g silica gel, 0-100% EtOAc/Hexane). The desired fractions were collected and removing solvent gave Intermediate 818C (59 mg, 0.145 mmol, 81% yield) as a white solid. $^1$H NMR (400 MHz, DMSO-$d_6$) δ 10.51 (s, 1H), 8.75 (d, J=2.6 Hz, 1H), 8.08 (dd, 2.5 Hz, 1H), 8.01-7.87 (m, 3H), 5.26 (td, J=6.4, 3.1 Hz, 1H), 4.37-4.32 (m, 1H), 4.23 (dd, J=11.0, 6.2 Hz, 1H), 1.41 (d, J=6.6 Hz, 3H); $^{19}$F NMR (376 MHz, DMSO-$d_6$) δ −133.72 (s, 1F); LC-MS: method E, RT=0.97 min, MS (ESI) m/z: 407.0 (M+H)$^+$.

Example 818

In a vial charged with a stirring bar, Intermediate 818C (14 mg, 0.034 mmol) was mixed with Intermediate I-38 (12.7 mg, 0.041 mmol) in 1,4-dioxane (1 mL). PdCl₂(dppf)-DCM (2.81 mg, 3.44 µmol) was added, followed by Na₂CO₃ (0.5 ml, 1.0 mmol). The reaction mixture was allowed to stir at 100° C. for 30 minutes. After cooling down to room temperature, the layers were separated and the aqueous layer was extracted by EtOAc (2 mL×2). Then organic phases were combined and concentrated on Rotavapor. The residue was dissolved in DMF and purified by prep-HPLC, Method B to afford Example 818 (3.8 mg, 0.007 mmol, 20% yield) as the title compound. ¹H NMR (500 MHz, DMSO-d₆) δ 8.92 (s, 1H), 8.81 (s, 1H), 8.74 (s, 1H), 8.51 (s, 1H), 8.08 (d, J=8.2 Hz, 1H), 8.03-7.90 (m, 3H), 5.29 (br. s., 1H), 4.40 (d, J=8.5 Hz, 1H), 4.29 (dd, J=10.7, 5.8 Hz, 1H), 4.11 (s, 3H), 3.35 (s, 1H), 1.44 (d, J=6.4 Hz, 3H); LC-MS: method L, RT=2.26 min, MS (ESI) m/z: 556.15 (M+H)⁺.

Example 819

(R)-1-((2-(7-cyano-2-methoxyquinoxalin-5-yl)-5-fluorobenzo[d]thiazol-6-yl)oxy)propan-2-yl (2-methylpyrimidin-5-yl)carbamate

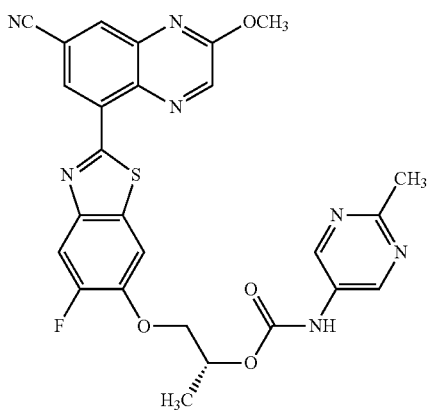

(819)

Intermediate 819A: (R)-1-((2-chloro-5-fluorobenzo[d]thiazol-6-yl)oxy)propan-2-yl (2-methylpyrimidin-5-yl)carbamate

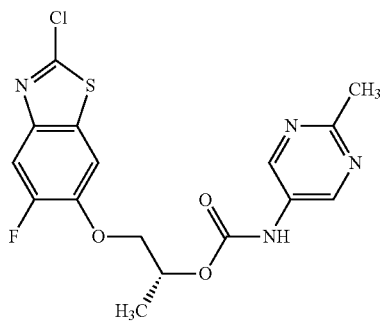

(819A)

Intermediate 819A was synthesized by the method described in Intermediate 818C, using 2-methylpyrimidin-5-amine instead of 5-aminopicolinonitrile. LC-MS: method E, RT=0.86 min, MS (ESI) m/z: 397.1 (M+H)⁺.

Example 819

Example 819 (2.2 mg, 0.004 mmol, 16% yield) was made from Intermediate 819A (9.0 mg, 0.023 mmol) by the method described for Example 818. LC-MS: method L, RT=2.03 min, MS (ESI) m/z: 546.10 (M+H)⁺.

Example 820

(2R,3S)-3-((2-(7-chloro-2-methoxyquinoxalin-5-yl)-5-fluorobenzo[d]thiazol-6-yl)oxy)butan-2-yl (2-methoxypyrimidin-5-yl)carbamate

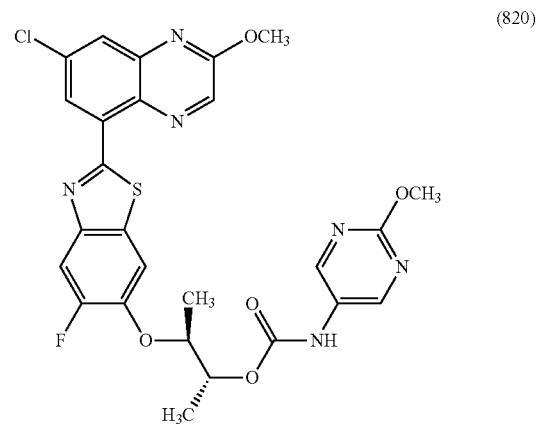 [SMILES: COc1cnc2c(-c3nc4cc(F)c(O[C@@H](C)[C@@H](C)OC(=O)Nc5cnc(OC)nc5)cc4s3)cc(Cl)cc2n1]

(820)

Intermediate 820A: (2R,3S)-3-((2-(7-chloro-2-methoxyquinoxalin-5-yl)-5-fluorobenzo[d]thiazol-6-yl)oxy)butan-2-ol

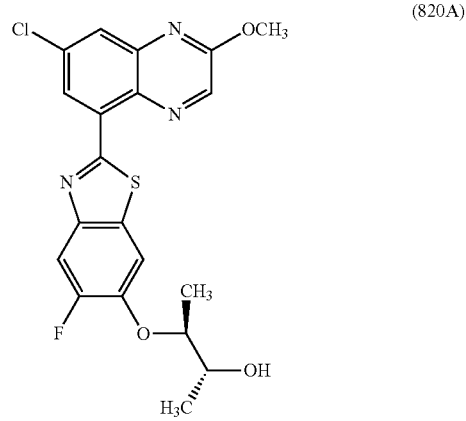 [SMILES: COc1cnc2c(-c3nc4cc(F)c(O[C@@H](C)[C@@H](C)O)cc4s3)cc(Cl)cc2n1]

(820A)

In a vial charged with a stirring bar, Intermediate I-72A (228 mg, 0.713 mmol) was mixed with Intermediate I-28 (170 mg, 0.713 mmol) in 1,4-dioxane (5 mL). Na₂CO₃ (2 mL, 4.00 mmol) was added, followed by Pd(dppf)Cl₂-DCM (29.1 mg, 0.036 mmol). The mixture was stirred at 100° C.

for 30 min. After cooling down to room temperature, the reaction mixture was diluted by adding 30 mL of EtOAc and 20 mL of water. After separation, the aqueous layer was extracted by EtOAc (20 mL×2). Then the organic phases were combined and washed with brine, dried over Na$_2$SO$_4$, filtered and concentrated. The crude product was purified on CombiFlash (40 g silica gel column, 0-100% EtOAc/Hexane). Removing solvent gave Intermediate 820A (296 mg, 0.682 mmol, 96% yield) as a yellow solid. LC-MS: method E, RT=1.09 min, MS (ESI) m/z: 434.1 (M+H)$^+$.

Intermediate 820B: (2R,3S)-3-((2-(7-chloro-2-methoxyquinoxalin-5-yl)-5-fluorobenzo[d]thiazol-6-yl)oxy)butan-2-yl carbonochloridate

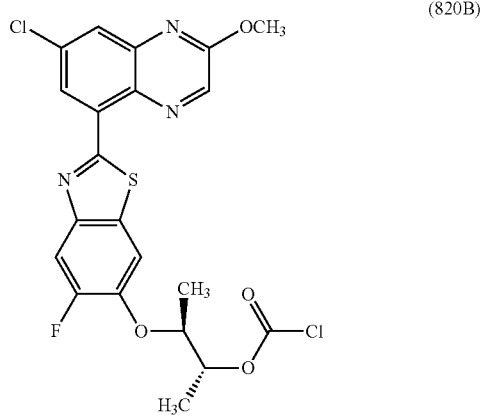 [SMILES: COc1cnc2c(-c3nc4cc(F)c(O[C@@H](C)[C@@H](C)OC(=O)Cl)cc4s3)cc(Cl)cc2n1]

(820B)

Intermediate 820A (0.290 g, 0.668 mmol) was dissolved in anhydrous THF (7 mL) and was treated with phosgene (4.77 mL, 6.68 mmol, 15% by wt. in toluene) at room temperature overnight. On the next day, LCMS showed a clean reaction. Then solvent was removed on the rotavapor and the residue was dried on high vacuum for 1 hour. The crude product was used in the next step as is. LC-MS: method E, RT=1.34 min, MS (ESI) m/z: 496.1 (M+H)$^+$.

Example 820

In a round bottom flask charged with a stirring bar, Intermediate 820B (60 mg, 0.121 mmol) was dissolved in DCM (2 mL) and mixed with 2-methoxypyrimidin-5-amine (60.5 mg, 0.484 mmol). Pyridine (0.049 mL, 0.604 mmol) was added and the mixture was stirred at room temperature for 4 hours. Solvent was removed on a rotavapor and the residue was loaded on silica gel and purified by CC (40 g silica gel, 0-100% EtOAc/Hexane gradient). The desired fractions were removed and freeze-dried to give Example 820 (55.8 mg, 0.093 mmol, 77% yield) as a yellow solid. $^1$H NMR (400 MHz, DMSO-d$_6$) δ ppm 9.69-9.87 (1H, m), 8.82 (1H, s), 8.63 (1H, d, J=2.42 Hz), 8.61 (1H, br. s.), 8.08 (1H, d, J=2.42 Hz), 8.06 (1H, d, J=8.14 Hz), 8.00 (1H, d, J=11.44 Hz), 5.09 (1H, dd, J=6.60, 2.64 Hz), 4.82 (1H, dd, J=6.38, 2.86 Hz), 4.10 (3H, s), 3.83 (3H, s), 3.57 (1H, s), 1.36-1.42 (6H, m); $^{19}$F NMR (376 MHz, DMSO-d$_6$) δ ppm −132.98 (1F, s); LC-MS: method G, RT=1.14 min, MS (ESI) m/z: 585.1 (M+H)$^+$.

Examples 821 to 830

The following additional examples have been prepared, isolated and characterized using the methods described for Example 820 and the examples above, from corresponded quinoxaline boronic acids and aniline intermediates.

| Ex. No. | Structure | LCMS [M + H]$^+$ m/z | LCMS RT(Min)/Method | NMR |
|---|---|---|---|---|
| 821 | 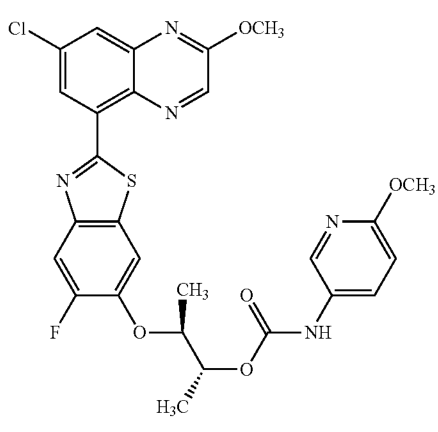 [SMILES: COc1ccc(NC(=O)O[C@H](C)[C@H](C)Oc2cc3sc(-c4cc(Cl)cc5nc(OC)cnc45)nc3cc2F)cn1] | 584.15 | 2.66/L | $^1$H NMR (500 MHz, DMSO-d$_6$) δ ppm 9.61 (1 H, br. s.), 8.79 (1 H, s), 8.58 (1 H, d, J = 1.83 Hz), 8.19 (1 H, br. s.), 8.01-8.06 (2 H, m), 7.97 (1 H, d, J = 11.29 Hz), 7.74 (1 H, br. s.), 6.74 (1 H, d, J = 7.63 Hz), 5.07 (1 H, d, J = 4.27 Hz), 4.79 (1 H, d, J = 3.97 Hz), 4.08 (3 H, s), 3.76 (3 H, s), 1.38 (6 H, dd, J = 11.14, 6.26 Hz) |

-continued

| Ex. No. | Structure | LCMS [M + H]+ m/z | LCMS RT(Min)/ Method | NMR |
|---|---|---|---|---|
| 822 | 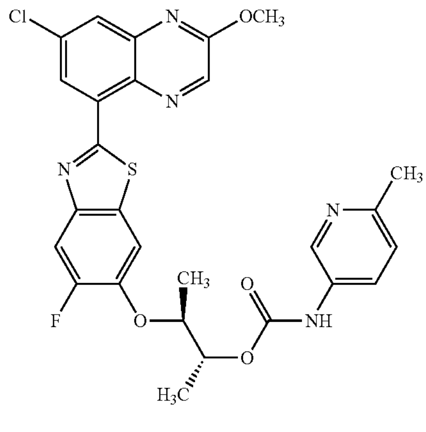 [SMILES: COc1cnc2c(-c3nc4cc(F)c(O[C@@H](C)[C@@H](C)OC(=O)Nc5ccc(C)nc5)cc4s3)cc(Cl)cc2n1] | 568.15 | 2.22/L | ¹H NMR (500 MHz, DMSO-d₆) δ ppm 9.82 (1 H, br. s.), 8.82 (1 H, s), 8.62 (1 H, d, J = 2.44 Hz), 8.50 (1 H, br. s.), 8.04-8.10 (2 H, m), 8.00 (1 H, d, J = 11.29 Hz), 7.77 (1 H, br. s.), 7.20 (1 H, br. s.), 5.09 (1 H, d, J = 6.71 Hz), 4.80 (1 H, br. s.), 4.10 (3 H, s), 2.37 (3 H, s), 1.33-1.46 (6 H, m) |
| 823 | 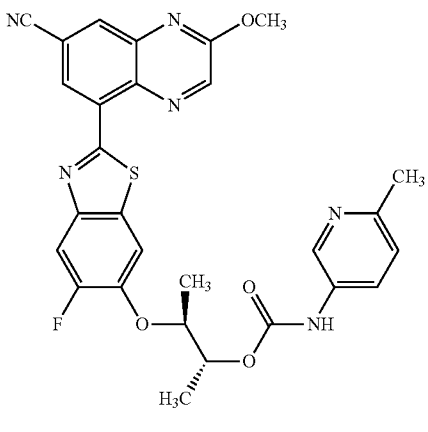 [SMILES: COc1cnc2c(-c3nc4cc(F)c(O[C@@H](C)[C@@H](C)OC(=O)Nc5ccc(C)nc5)cc4s3)cc(C#N)cc2n1] | 559.2 | 1.90/L | ¹H NMR (500 MHz, DMSO-d₆) δ ppm 9.78 (1 H, br. s.), 8.85 (1 H, s), 8.73 (1 H, s), 8.48 (1 H, br. s.), 8.45 (1 H, s), 8.02 (1 H, d, J = 7.93 Hz), 7.92 (1 H, d, J = 11.29 Hz), 7.75 (1 H, br. s.), 7.15 (1 H, d, J = 8.24 Hz), 5.10 (1 H, d, J = 6.41 Hz), 4.79 (1 H, d, J = 3.97 Hz), 4.09 (3 H, s), 2.36 (3 H, s), 1.39 (6 H, dd, J = 11.29, 6.41 Hz) |
| 824 | 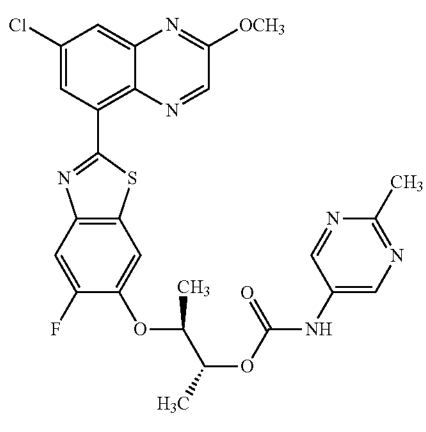 [SMILES: COc1cnc2c(-c3nc4cc(F)c(O[C@@H](C)[C@@H](C)OC(=O)Nc5cnc(C)nc5)cc4s3)cc(Cl)cc2n1] | 569.0 | 1.26/E | ¹H NMR (400 MHz, DMSO-d₆) δ ppm 9.93 (1 H, br. s.), 8.84 (1 H, s), 8.72 (2 H, br. s.), 8.64 (1 H, d, J = 2.42 Hz), 8.09 (1 H, d, J = 2.42 Hz), 8.07 (1 H, d, J = 8.36 Hz), 8.01 (1 H, d, J = 11.44 Hz), 5.11 (1 H, dd, J = 6.49, 2.75 Hz), 4.77-4.93 (1 H, m), 4.10 (3 H, s), 2.51-2.52 (3 H, m), 1.39 (6 H, dd, J = 6.49, 3.41 Hz). ¹⁹F NMR (376 MHz, DMSO-d₆) δ ppm −132.97 (1 F, s) |

-continued

| Ex. No. | Structure | LCMS [M + H]+ m/z | LCMS RT(Min)/ Method | NMR |
|---|---|---|---|---|
| 825 | 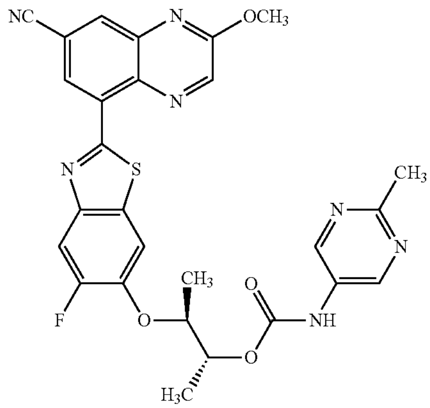 [SMILES: COc1cnc2c(-c3nc4cc(F)c(O[C@@H](C)[C@@H](C)OC(=O)Nc5cnc(C)nc5)cc4s3)cc(C#N)cc2n1] | 560.2 | 2.11/L | ¹H NMR (500 MHz, DMSO-$d_6$) δ ppm 9.95 (1 H, br. s.), 8.94 (1 H, s), 8.84 (1 H, s), 8.71 (2 H, br. s.), 8.53 (1 H, s), 8.06 (1 H, d, J = 8.24 Hz), 7.99 (1 H, d, J = 11.60 Hz), 5.10 (1 H, d, J = 6.41 Hz), 4.83 (1 H, d, J = 5.19 Hz), 4.11 (3 H, s), 2.50 (3 H, s), 1.39 (6 H, t, J = 6.26 Hz) |
| 826 | 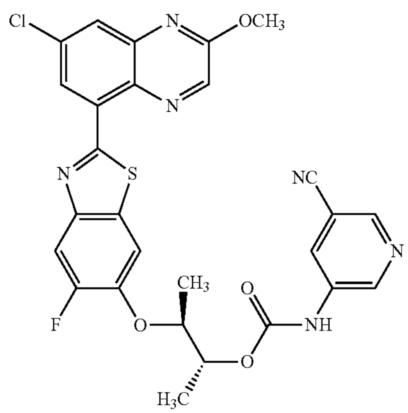 [SMILES: COc1cnc2c(-c3nc4cc(F)c(O[C@@H](C)[C@@H](C)OC(=O)Nc5cncc(C#N)c5)cc4s3)cc(Cl)cc2n1] | 579.1 | 1.15/E | ¹H NMR (400 MHz, DMSO-$d_6$) δ ppm 10.26 (1 H, s), 8.83 (1 H, s), 8.81 (1 H, s), 8.64 (1 H, d, J = 2.20 Hz), 8.60 (1 H, s), 8.23 (1 H, br. s.), 8.06-8.12 (2 H, m), 8.01 (1 H, d, J = 11.44 Hz), 5.12 (1 H, d, J = 6.82 Hz), 4.85 (1 H, s), 4.11 (3 H, s), 1.40 (6 H, d, J = 6.60 Hz) ¹⁹F NMR (376 MHz, DMSO-$d_6$) δ ppm −132.95 (1 F, s) |
| 827 | 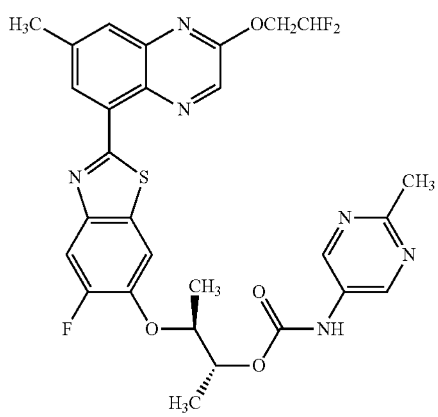 | 599.1 | 0.90/J | ¹H NMR (500 MHz, DMSO-$d_6$) δ ppm 9.85-10.06 (1 H, m), 8.80 (1 H, s), 8.72 (2 H, br. s.), 8.57 (1 H, s), 8.02 (1 H, d, J = 8.24 Hz), 7.93 (1 H, d, J = 11.29 Hz), 7.81 (1 H, s), 6.39-6.65 (1 H, m), 5.10 (1 H, dd, J = 6.56, 2.29 Hz), 4.68-4.89 (3 H, m), 2.61 (3 H, s), 2.54 (3 H, s), 1.38 (6 H, t, J = 5.65 Hz) |

-continued

| Ex. No. | Structure | LCMS [M + H]+ m/z | LCMS RT(Min)/ Method | NMR |
|---|---|---|---|---|
| 828 | 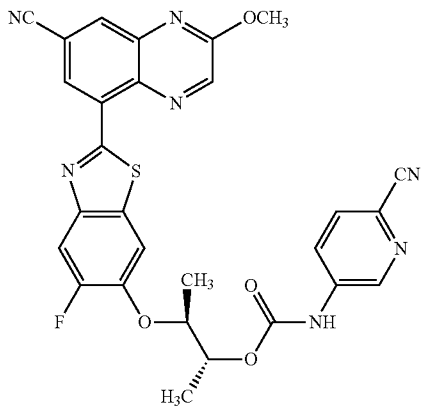 [SMILES: COc1cnc2c(-c3nc4cc(F)c(O[C@@H](C)[C@@H](C)OC(=O)Nc5ccc(C#N)nc5)cc4s3)cc(C#N)cc2n1] | 570.20 | 2.36/L | ¹H NMR (500 MHz, DMSO-$d_6$) δ ppm 8.85 (1 H, s), 8.73 (1 H, s), 8.66 (1 H, br. s.), 8.45 (1 H, s), 8.00 (2 H, d, J = 7.93 Hz), 7.82-7.95 (2 H, m), 5.09 (1 H, d, J = 6.41 Hz), 4.81 (1 H, d, J = 4.27 Hz), 4.06 (3 H, s), 1.37 (7 H, t, J = 5.34 Hz) |
| 829 | 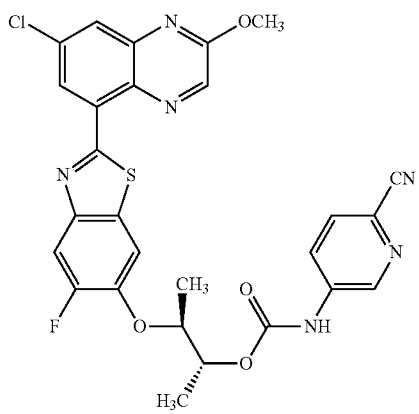 [SMILES: COc1cnc2c(-c3nc4cc(F)c(O[C@@H](C)[C@@H](C)OC(=O)Nc5ccc(C#N)nc5)cc4s3)cc(Cl)cc2n1] | 579.15 | 2.69/M | ¹H NMR (500 MHz, DMSO-$d_6$) δ ppm 10.40 (1 H, s), 8.66-8.77 (2 H, m), 8.51 (1 H, d, J = 2.14 Hz), 7.85-8.12 (5 H, m), 5.13 (1 H, dd, J = 6.41, 2.14 Hz), 4.84 (1 H, d, J = 3.97 Hz), 4.06 (3 H, s), 1.35-1.45 (6 H, m) |
| 830 | 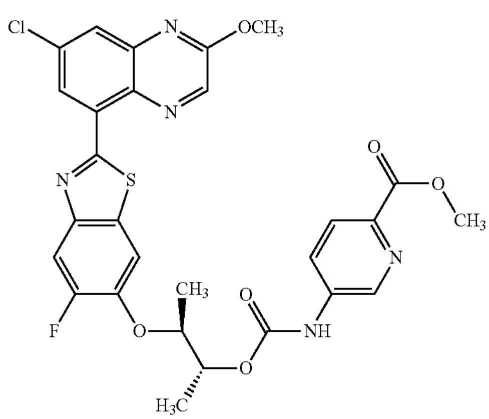 [SMILES: COC(=O)c1ccc(NC(=O)O[C@H](C)[C@H](C)Oc2cc3sc(-c4cc(Cl)cc5nc(OC)cnc45)nc3cc2F)cn1] | 612.2 | 2.69/G | ¹H NMR (400 MHz, DMSO-$d_6$) δ 10.24 (s, 1H), 8.82 (s, 1H), 8.70 (d, J = 2.0 Hz, 1H), 8.62 (d, J = 1.3 Hz, 1H), 8.16-7.83 (m, 5H), 5.12 (dd, J = 6.6, 2.6 Hz, 1H), 4.86 (d, J = 6.6 Hz, 1H), 4.10 (s, 3H), 3.80 (s, 3H), 1.41 (dd, J = 6.5, 2.8 Hz, 6H) |

Example 831

(2R,3S)-3-((2-(7-chloro-2-methoxyquinoxalin-5-yl)-5-fluorobenzo[d]thiazol-6-yl)oxy)butan-2-yl (6-(hydroxymethyl)pyridin-3-yl)carbamate

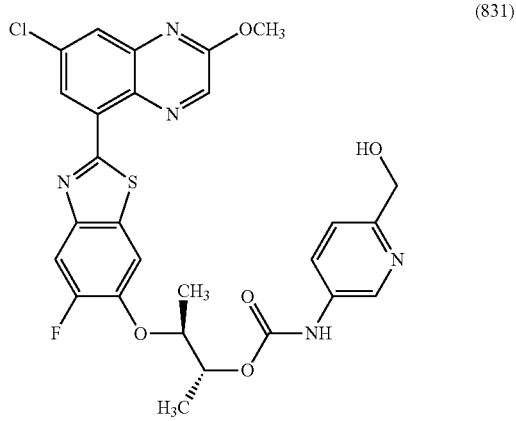 [SMILES: COc1cnc2c(-c3nc4cc(F)c(O[C@@H](C)[C@@H](C)OC(=O)Nc5ccc(CO)nc5)cc4s3)cc(Cl)cc2n1]

(831)

Example 830 (10 mg, 0.016 mmol) was dissolved in anhydrous THF (1 mL) and cooled to −78° C. under an atmosphere of $N_2$. DIBAL-H (0.082 mL, 0.082 mmol) was then added drop wise. After 2 min of stirring at −78° C., the reddish solution was allowed to thaw to room temperature. Next, 1 mL of saturated Rochelle's Salt solution was added to quench the reaction, causing the solution to return to a yellow color. The reaction mixture was stirred vigorously for 3 h before being diluted with EtOAc and washed with saturated $NH_4Cl$ (aq.). The organic phase was dried over $Na_2SO_4$, filtered, concentrated. The crude product was purified by prep-HPLC, Method D to afford Example 831 (2.4 mg, 0.004 mmol, 24% yield) as the title compound. $^1$H NMR (500 MHz, DMSO-$d_6$) δ ppm 9.81 (1H, br. s.), 8.64 (1H, s), 8.50 (1H, br. s.), 8.44 (1H, s), 7.77-8.03 (4H, m), 7.34(1H, d, J=8.54 Hz), 5.36-5.45 (1H, m), 5.10 (1H, d, J=5.19 Hz), 4.76(1H, br. s.), 4.45 (2H, d, J=5.19 Hz), 4.03 (3H, s), 1.38 (6H, dd, J=12.36, 6.26 Hz); $^{19}$F NMR (471 MHz, DMSO-$d_6$) δ ppm −132.94 (1F, s.); LC-MS: method L, RT=2.24 min, MS (ESI) m/z: 584.25 (M+H)$^+$.

Example 832

(2R,3S)-3-((2-(7-chloro-2-methoxyquinoxalin-5-yl)-5-fluorobenzo[d]thiazol-6-yl)oxy)butan-2-yl (6-(methylcarbamoyl)pyridin-3-yl)carbamate

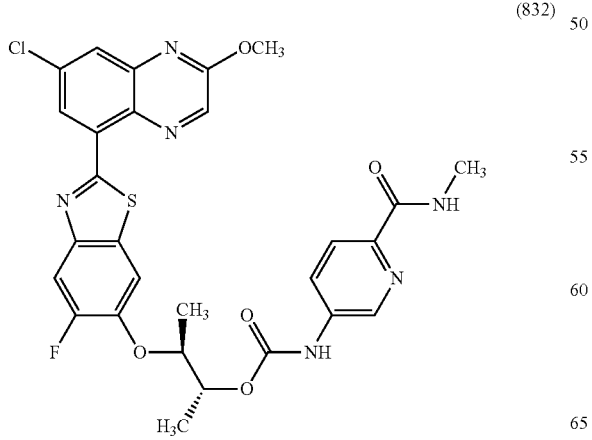

(832)

To a vial charged with Example 830 (8 mg, 0.013 mmol) were added THF (0.4 mL), followed by methylamine (0.6 mL, 0.013 mmol). The reaction mixture was sealed and heated at 60° C. for 30 minutes. The solvent was removed and the residue was redissolved in DMF, before being purified by prep-HPLC, Method D to afford Example 832 (4.9 mg, 0.008 mmol, 59% yield) as the title compound. $^1$H NMR (500 MHz, DMSO-$d_6$) δ ppm 10.11 (1H, br. s.), 8.61 (1H, br. s.), 8.54 (1H, d, J=4.58 Hz), 8.43 (1H, s), 7.61-8.11 (6H, m), 5.11 (1H, d, J=6.10 Hz), 4.83 (1H, d, J=6.10 Hz), 4.03 (3H, s), 2.75 (3H, d, J=4.58 Hz), 1.40 (6H, dd, J=8.85, 7.02 Hz); $^{19}$F NMR (471 MHz, DMSO-$d_6$) δ ppm −132.95 (1F, br. s.); LC-MS: method L, RT=2.57 min, MS (ESI) m/z: 611.15 (M+H)$^+$.

Example 833

(2R,3S)-3-((2-(7-chloro-2-methoxyquinoxalin-5-yl)-5-fluorobenzo[d]thiazol-6-yl)oxy) butan-2-yl (6-carbamoylpyridin-3-yl)carbamate

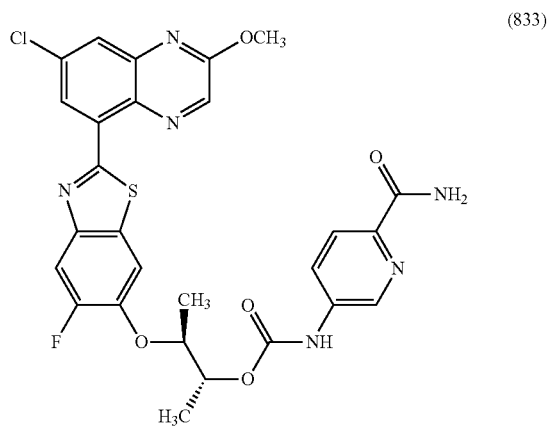 [SMILES: COc1cnc2c(-c3nc4cc(F)c(O[C@@H](C)[C@@H](C)OC(=O)Nc5ccc(C(N)=O)nc5)cc4s3)cc(Cl)cc2n1]

(833)

Example 830 (8 mg, 0.013 mmol) was dissolved in THF (0.5 mL). $NH_3$ (2 mL, 14.00 mmol) in methanol (7N) was added. The reaction mixture was sealed and heated at 60° C. for 20 hours. On the next day, solvent was removed and the residue was purified by prep-HPLC, Method D to afford Example 833 (4.5 mg, 0.007 mmol, 55% yield) as the title compound. $^1$H NMR (500 MHz, DMSO-$d_6$) δ ppm 10.16 (1H, br. s.), 8.50-8.70 (2H, m), 8.39 (1H, br. s.), 7.75-8.09 (6H, m), 7.43 (1H, br. s.), 5.12 (1H, d, J=6.10 Hz), 4.78 (1H, d, J=4.58 Hz), 4.01 (3H, s), 1.33-1.46 (6H, m); $^{19}$F NMR (471 MHz, DMSO-$d_6$) δ ppm −132.98 (1F, br. s.); LC-MS: method L, RT=2.50 min, MS (ESI) m/z: 597.10 (M+H)$^+$.

Example 834

(2R,3S)-3-((2-(7-chloro-2-methoxyquinoxalin-5-yl)-5-fluorobenzo[d]thiazol-6-yl)oxy)butan-2-yl (6-(dimethylcarbamoyl)pyridin-3-yl)carbamate (834)

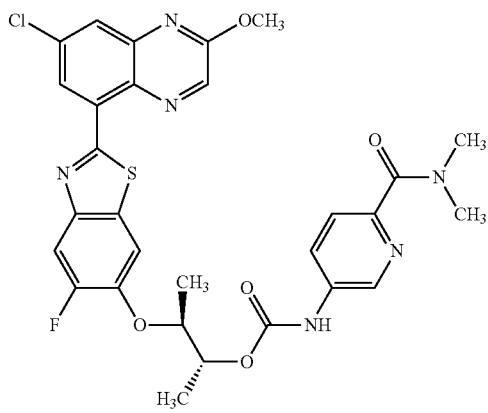

To a vial charged with Example 830 (8 mg, 0.013 mmol) was added THF (0.5 mL). The resulting solution was cooled to 0° C. and magnesium chloride (6.22 mg, 0.065 mmol) was added. The mixture was allowed to stir for 30 min before dimethylamine (0.196 mL, 0.392 mmol) was added. The ice bath was allowed to expire and the reaction mixture was stirred at 60° C. for 2 hours. After cooling down to room temperature, solvent was removed and the residue was dissolved in DMF. The remaining solids were removed by filtration and the resulting solution was purified by prep-HPLC, Method D to afford Example 834 (0.8 mg, 0.001 mmol, 10% yield) as the title compound. $^1$H NMR (500 MHz, DMSO-d$_6$) δ ppm 10.07 (1H, br. s.), 8.80 (1H, s), 8.60 (2H, d, J=2.48 Hz), 8.03-8.10 (2H, m), 7.92-8.02 (2H, m), 7.52 (1H, d, J=8.53 Hz), 5.13 (1H, dd, J=6.60, 2.75 Hz), 4.83 (1H, dd, J=6.33, 2.75 Hz), 4.09 (3H, s), 2.96 (6H, d, J=6.33 Hz), 1.40 (6H, dd, J=6.33, 5.23 Hz); $^{19}$F NMR (471 MHz, DMSO-d$_6$) δ ppm -138.05 (1F, br. s.); LC-MS: method L, RT=2.52 min, MS (ESI) m/z: 625.15 (M+H)$^+$.

Example 835

(2R,3S)-3-((2-(7-chloro-2-methoxyquinoxalin-5-yl)-5-fluorobenzo[d]thiazol-6-yl)oxy)butan-2-yl (6-(2-hydroxy-2-methylpropyl)pyridin-3-yl)carbamate (835)

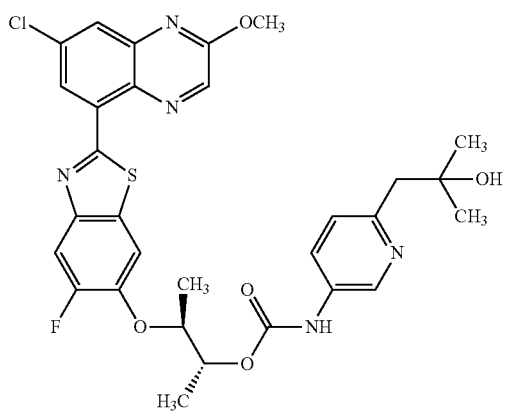

1-(5-aminopyridin-2-yl)-2-methylpropan-2-ol (2.95 mg, 0.018 mmol) was dissolved in DCM (0.5 mL) and pyridine (1.955 μL, 0.024 mmol) was added. A solution of Intermediate 820B (8 mg, 0.016 mmol) in DCM (0.5 mL) was added dropwise to the reaction mixture. The mixture was stirred at room temperature overnight. On the next day, solvent was removed and the residue was purified by prep-HPLC, Method D to afford Example 835 (6.8 mg, 0.010 mmol, 63% yield). $^1$H NMR (500 MHz, DMSO-d$_6$) δ ppm 9.76 (1H, br. s.), 8.65 (1H, s), 8.49 (1H, br. s.), 8.46 (1H, d, J=2.14 Hz), 7.94 (1H, d, J=8.24 Hz), 7.92 (1H, d, J=2.14 Hz), 7.87 (1H, d, J=11.60 Hz), 7.75 (1H, br. s.), 7.19(1H, d, J=8.24 Hz), 5.09(1H, dd, J=6.41, 2.75 Hz), 4.77 (1H, dd, J=6.26, 2.59 Hz), 4.04 (3H, s), 3.53 (1H, s), 2.72 (2H, s), 1.38 (6H, dd, J=12.66, 6.56 Hz), 1.02 (6H, s); $^{19}$F NMR (471 MHz, DMSO-d$_6$) δ ppm -132.92 (1F, br. s.); LC-MS: method L, RT=2.29 min, MS (ESI) m/z: 626.15 (M+H)$^+$.

Example 836

(2R,3S)-3-((2-(7-chloro-2-methoxyquinoxalin-5-yl)-5-fluorobenzo[d]thiazol-6-yl)oxy)butan-2-yl (6-(2-hydroxyethyl)pyridin-3-yl)carbamate

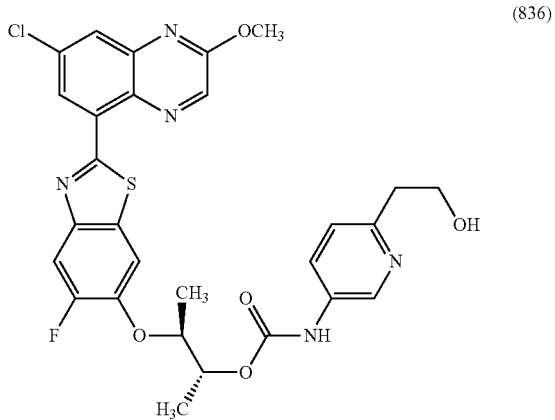 [SMILES: COc1cnc2c(-c3nc4cc(F)c(O[C@@H](C)[C@@H](C)OC(=O)Nc5ccc(CCO)nc5)cc4s3)cc(Cl)cc2n1]

(836)

Intermediate I-93 (7.83 mg, 0.031 mmol) was dissolved in DCM (0.5 mL) and pyridine (3.42 μl, 0.042 mmol) was added. Then Intermediate 820B (14 mg, 0.028 mmol) in DCM (0.5 mL) was added dropwise to the reaction mixture. The mixture was stirred at room temperature overnight. On the next day, TBAF (0.282 mL, 0.282 mmol) solution was added. After stirring for 3 hours, HCl (0.071 mL, 0.282 mmol) was added. The reaction mixture was stirred at room temperature for an additional 30 minutes. Then solvent was removed on the rotavapor and the residue was purified by prep-HPLC, Method D to afford Example 836 (4.8 mg, 0.008 mmol, 27% yield). $^1$H NMR (500 MHz, DMSO-d$_6$) δ ppm 9.75 (1H, br. s.), 8.64 (1H, s), 8.49 (1H, br. s.), 8.45 (1H, s), 7.93 (1H, d,J=8.24 Hz), 7.91(1H, s), 7.85(1H, d,J=11.60 Hz), 7.71-7.79 (1H, m), 7.18(1H, d, J=8.54 Hz), 5.09 (1H, d, J=6.41 Hz), 4.76 (1H, d, J=5.80 Hz), 4.03 (3H, s), 3.66 (1H, t, J=6.71 Hz), 3.56 (1H, d, J=2.75 Hz), 2.77 (2H, t, J=6.71 Hz), 1.37 (7H, dd, J=13.43, 6.41 Hz); $^{19}$F NMR (471 MHz, DMSO-d$_6$) δ ppm -132.95 (1F, br. s.); LC-MS: method L, RT=2.19 min, MS (ESI) m/z: 598.15 (M+H)$^+$.

Example 837

2-(7-chloro-2-methoxyquinoxalin-5-yl)-6-methoxy-4-methylbenzo[d]thiazole

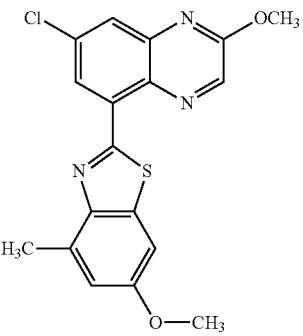

(837)

In a vial charged with a stirring bar, Intermediate I-28 (17 mg, 0.053 mmol) was dissolved in 1,4-dioxane (1 mL), mixed with 2-bromo-6-methoxy-4-methylbenzo [d]thiazole (17.80 mg, 0.069 mmol). $Na_2CO_3$ (1 mL, 2.0 mmol) was added, followed by $PdCl_2(dppf)$-DCM (4.33 mg, 5.30 μmol). The reaction mixture was stirred at 100° C. for 1 hour. After cooling down to room temperature, the reaction mixture was diluted by adding 20 ml of EtOAc and 20 mL of water. After shaking and separation, the organic phase was passed through $Na_2SO_4$ and concentrated on rotavapor. The residue was purified by prep-HPLC, Method D to afford Example 837 (2.0 mg, 0.005 mmol, 10% yield). $^1H$ NMR (500 MHz, $CDCl_3$-d) δ 8.80 (d, J=2.5 Hz, 1H), 8.59 (s, 1H), 7.92 (d, J=2.5 Hz, 1H), 7.24 (d, J=2.5 Hz, 1H), 6.95 (s, 1H), 4.14 (s, 3H), 3.90 (s, 3H), 2.83 (s, 3H); LC-MS: method L, RT=2.934 min, MS (ESI) m/z: 372.10 $(M+H)^+$.

What is claimed is:
1. A compound of Formula (I) to (IV):

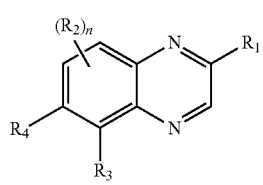

(I)

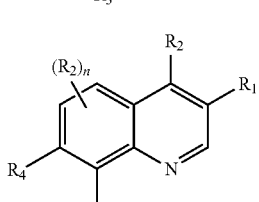

(II)

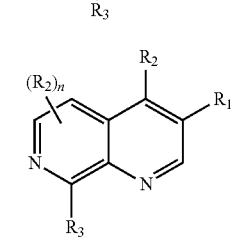

(III)

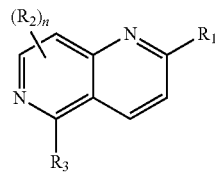

(IV)

or a salt thereof, wherein:

$R_1$ is F, Cl, —OH, $C_{1-4}$ alkyl, $C_{1-4}$ fluoroalkyl, $C_{2-4}$ alkenyl, $C_{2-4}$ alkynyl, $C_{3-7}$ cycloalkyl, $C_{3-7}$ fluorocycloalkyl, $C_{1-4}$ alkoxy, $C_{1-4}$ fluoroalkoxy, $C_{2-4}$ hydroxyalkoxy, $C_{3-6}$ cycloalkoxy, $(C_{1-3}$ alkoxy)-$(C_{1-3}$ alkylene), $(C_{1-3}$ alkoxy)-$(C_{1-3}$ fluoroalkylene), $(C_{1-3}$ deuteroalkoxy)-$(C_{1-3}$ deuteroalkylene), $(C_{1-3}$ fluoroalkoxy)-$(C_{1-3}$ alkylene), $(C_{1-3}$ fluoroalkoxy)-$(C_{1-3}$ fluoroalkylene), —$(CH_2)_{1-3}O$(phenyl), —$(CH_2)_{1-3}NR_aR_a$, —$C(O)O(C_{1-6}$ alkyl), —$C(O)NR_aR_a$, —$C(O)NR_bR_b$, —$NH_2$, —$NH(C_{1-6}$ alkyl), —$N(C_{1-6}$ alkyl)$_2$, —NH($C_{1-6}$ hydroxyalkyl), azetidinyl, pyrrolidinyl, furanyl, pyranyl, piperidinyl, morpholinyl, piperazinyl, —$S(O)_2(C_{1-3}$ alkyl), —$S(O)_2NR_aR_a$, $C_{1-3}$ alkylthio, or $C_{1-3}$ fluoroalkylthio;

$R_2$, at each occurrence, is independently H, F, Cl, Br, —OH, —CN, $C_{1-4}$ alkyl, $C_{1-4}$ fluoroalkyl, $C_{1-4}$ hydroxyalkyl, $C_{1-3}$ aminoalkyl, $C_{2-4}$ alkenyl, $C_{2-4}$ alkynyl, $C_{3-7}$ cycloalkyl, $C_{3-7}$ fluorocycloalkyl, $C_{1-6}$ alkoxy, $C_{1-3}$ fluoroalkoxy, $C_{1-3}$ alkylthio, $C_{1-3}$ fluoroalkylthio, $(C_{1-3}$ alkoxy)-$(C_{1-3}$ alkylene), $(C_{1-3}$ fluoroalkoxy)-$(C_{1-3}$ alkylene), —$C(O)NH_2$, —$C(O)NH(C_{1-6}$ alkyl), —$C(O)N(C_{1-6}$ alkyl)$_2$, —$C(O)O(C_{1-6}$ alkyl), —$C(O)NH(CH_2CH_2O(C_{1-3}$ alkyl)), —$C(O)NR_bR_b$, —$C(O)$(piperidinyl), —$CH(OH)(C_{3-6}$ cycloalkyl), —$CH(OH)$(phenyl), —$CH(OH)$(pyridyl), —$S(O)_2(C_{1-3}$ alkyl), —$S(O)_2NR_aR_a$, or a cyclic group selected from phenyl, 5- to 6-membered heteroaryl, and 5- to 7-membered heterocyclyl, wherein said cyclic group is substituted with zero to 5 substituents independently selected from F, Cl, hydroxy, $C_{1-3}$ alkyl, $C_{1-3}$ alkoxy, cyclopropyl, and —CN;

$R_3$ is a bicyclic group selected from indolyl, benzofuranyl, benzo[b]thiophenyl, benzo[d]imidazolyl, benzo[d]oxazolyl, benzo[d]thiazolyl, imidazol[1,2-a]pyridinyl, thiazolo[4,5-b]pyridinyl, thiazolo[4,5-c]pyridinyl, thiazolo[5,4-b]pyridinyl, thiazolo[5,4-c]pyridinyl, 4,5,6,7-tetrahydrobenzo[d]thiazolyl, 4,5,6,7-tetrahydrobenzofuranyl, 4,5,6,7-tetrahydrothiazolo[5,4-c]pyridinyl, 5,6,7,8-tetrahydro-4H-cyclohepta[d]thiazolyl, 5,6-dihydro-4H-cyclopenta[d]thiazolyl, indolizinyl, pyrrolo[1,2-a]pyrimidinyl, 6,7-dihydrothiazolo[5,4-c]pyridinyl, 6,7-dihydro-5H-imidazo[2,1-b][1,3]oxazinyl, 4,5,6,7-tetrahydrobenzothiophenyl, furo[3,2-b]pyridinyl, and furo[2,3-b]pyridinyl, each bicyclic group substituted with zero to 3 $R_{3a}$;

$R_{3a}$, at each occurrence, is independently:
(i) F, Cl, —CN, —OH, $C_{1-3}$ alkyl, $C_{1-6}$ fluoroalkyl, $C_{1-6}$ hydroxyalkyl, $C_{1-6}$ hydroxy-deuteroalkyl, $C_{1-6}$ hydroxy-fluoroalkyl, $C_{1-6}$ alkoxy, $C_{1-3}$ fluoroalkoxy, $C_{3-6}$ cycloalkyl, $C_{3-6}$ fluorocycloalkyl, 4- to 7-membered heterocyclyl, —CH(OH)$R_y$, wherein $R_y$ is $C_{3-6}$ cycloalkyl, aryl, heteroaryl, or 4- to 7-membered heterocyclyl; $(C_{1-3}$ alkoxy)-$(C_{1-3}$ alkylene), —$(CH_2)_{1-3}NR_aR_a$, —$(CH_2)_{1-3}NHS(O)_2$(aryl), —$O(CH_2)_{1-3}$(aryl), —$O(CH_2)_{1-3}$(thiazolyl), —$O(CH_2)_{1-3}$(oxazolidinonyl), —$O(CH_2)_{1-3}$(amino isoxazolyl), —$O(CH_2)_{1-3}$(imidazolyl substituted with phenyl), $C_{1-6}$ hydroxyalkoxy, $(C_{1-3}$ alkoxy)—(C$_{1-6}$ alkoxy), —O(CH$_2$)$_{1-4}$O(aryl), —O(CH$_2$)$_{1-4}$O(CH$_2$)$_{1-3}$(aryl), —O(CH$_2$)$_{1-4}$NR$_a$R$_a$, —O(CH$_2$)$_{1-3}$CHR$_a$NR$_a$(methoxy pyrimidinyl), —O(CH$_2$)$_{1-4}$NHS(O)$_2$(C$_{1-3}$alkyl), —O(CH$_2$)$_{1-4}$NHS(O)$_2$(aryl), —O(CH$_2$)$_{1-4}$C(O)OH, —O(CH$_2$)$_{1-4}$C(O)O(C$_{1-6}$ alkyl), —O(CH$_2$)$_{1-4}$C(O)NR$_a$(CH$_2$)$_{0-3}$(aryl), —O(CH$_2$)$_{1-4}$C(O)NR$_a$(CH$_2$)$_{0-3}$(heteroaryl), —O(CH$_2$)$_{1-4}$C(O)(morpholinyl), —O(CH$_2$)$_{1-4}$OC(O)O(C$_{1-3}$ alkyl), —O(CH$_2$)$_{1-3}$CHR$_a$OC(O)NR$_a$(CH$_2$)$_{1-4}$C(O)NR$_a$R$_a$, —CH$_2$CHR$_a$OC(O)NR$_a$(heteroaryl), —O(CH$_2$)$_{1-4}$OC(O)NR$_a$(heteroaryl), —O(imidazolyl substituted with aryl), —C(O)OH, —C(O)O(C$_{1-6}$ alkyl), —NR$_a$C(O)(furanyl), —NR$_a$C(O)(pyranyl), —NR$_a$C(O)O(C$_{1-6}$ alkyl), —NR$_a$C(O)O(C$_{1-4}$(aryl), —O(CH$_2$)$_{1-4}$NR$_a$C(O)O(C$_{1-6}$ alkyl), —O(CH$_2$)$_{1-4}$NR$_a$C(O)O(CH$_2$)$_{0-4}$(tetrahydropyranyl), —O(CH$_2$)$_{1-4}$NR$_a$C(O)O(CH$_2$)$_{0-4}$(aryl), —O(CH$_2$)$_{1-4}$NR$_a$C(O)O(CH$_2$)$_{0-4}$(heteroaryl), or —O(CH$_2$)$_{1-4}$NR$_a$C(O)O(CH$_2$)$_{0-4}$(tetrahydrofuranyl), wherein each of said aryl, heteroaryl, and 3- to 6-membered heterocyclyl is substituted with zero to 5 substituents independently selected from F, Cl, —CN, C$_{1-3}$ alkyl, C$_{1-3}$ fluoroalkyl, C$_{1-4}$ hydroxyalkyl, C$_{1-3}$ alkoxy, —OCF$_3$, —OCHF$_2$, —NH$_2$, —NH(C$_{1-6}$ alkyl), —N(C$_{1-6}$ alkyl)$_2$, —C(O)O(C$_{1-3}$ alkyl), C$_{1-3}$ hydroxyalkoxy, phenyl, —CONR$_c$R$_c$, and —S(O)$_2$NR$_c$R$_c$;

(ii) —CH(OH)CR$_h$R$_i$R$_j$ wherein R$_h$ and R$_i$ are independently H, F, C$_{1-4}$ alkyl, C$_{1-4}$ fluoroalkyl, C$_{1-3}$ alkoxy, C$_{1-3}$ fluoroalkoxy, or taken together with the carbon atom to which they are attached, form C$_{3-8}$ cycloalkyl or 4- to 7-membered heterocyclyl ring; and R$_j$ is H, C$_{1-6}$ alkyl, C$_{1-5}$ fluoroalkyl, (C$_{1-3}$ alkoxy)—(C$_{1-3}$ alkylene), C$_{3-8}$ cycloalkyl, C$_{3-8}$ heterocyclyl, aryl, or heteroaryl;

(iii) —O(CH$_2$)$_{1-4}$NR$_a$S(O)$_2$(C$_{1-4}$ alkyl) or —O(CH$_2$)$_{1-4}$NR$_a$S(O)$_2$R$_w$, wherein R$_w$ is aryl or heteroaryl, each substituted with zero to 2 substituents independently selected from F, Cl, cyano, C$_{1-3}$ alkyl, C$_{1-3}$ alkoxy, —OCF$_3$, —OCHF$_2$, and C$_{1-3}$ fluoroalkyl; or (iv) —O(CH$_2$)$_{1-4}$OC(O)NR$_a$R$_x$, —OCH(R$_d$)(CH$_2$)$_{1-3}$OC(O)NR$_a$R$_x$, —OCR$_a$R$_d$(CH$_2$)$_{1-30}$C(O)NR$_a$R$_x$, —O(CH$_2$)$_{1-3}$CH(R$_d$)OC(O)NR$_a$R$_x$, —O(CH$_2$)$_{1-3}$CR$_d$R$_d$OC(O)NR$_a$R$_x$, —OCH(R$_d$)CH(R$_d$)(CH$_2$)$_{0-2}$OC(O)NR$_a$R$_x$, or —OCR$_d$R$_d$CR$_d$R$_d$(CH$_2$)$_{0-2}$OC(O)NR$_a$R$_x$, wherein R$_x$ is selected from H, C$_{1-4}$ alkyl, C$_{1-4}$ fluoroalkyl, aryl, heteroaryl, and —CH$_2$(heteroaryl), each aryl and heteroaryl substituted with zero to 2 substituents independently selected from F, Cl, Br, —CN, —OH, C$_{1-3}$ alkyl, C$_{1-3}$ fluoroalkyl, C$_{1-6}$ hydroxyalkyl, C$_{1-6}$ hydroxy-deuteroalkyl, C$_{1-6}$ hydroxyalkoxy, C$_{1-6}$ hydroxy-fluoroalkoxy, C$_{1-3}$ alkoxy, —C(O)OH, —(CH$_2$)$_{0-3}$C(O)O(C$_{1-3}$ alkyl), —(CH$_2$)$_{1-3}$OP(O)(OH)$_2$, —CH$_2$(morpholinyl), —C(O)NH$_2$, —C(O)NH(C$_{1-6}$ alkyl), —C(O)N(C$_{1-6}$ alkyl)$_2$, —C(O)NR$_a$(C$_{1-6}$ hydroxyalkyl), —C(O)NR$_b$R$_b$, —S(O)$_2$NR$_a$R$_a$, —NH$_2$, —NH(C$_{1-6}$ alkyl), —NR$_a$(C$_{1-6}$ hydroxyalkyl), —N(C$_{1-6}$ alkyl)$_2$, —NR$_a$C(O)(C$_{1-6}$ alkyl), —NR$_a$C(O)(chloro, fluorophenyl), —NR$_a$S(O)$_2$(C$_{1-3}$ alkyl), —C(O)NR$_a$(CH$_2$)$_{0-1}$(hydroxymethyloxetanyl), —C(O)NR$_a$(CH$_2$)$_{0-1}$ (hydroxymethyl C$_{3-6}$ cycloalkyl), —C(O)NR$_a$(CH$_2$)$_{0-1}$ (hydroxy C$_{3-6}$ cycloalkyl), —C(O)NHCH$_2$C(CH$_3$)$_2$OP(O)(OH)$_2$, —C(O)(hydroxypiperidinyl), —C(O)(hydroxypyrrolidinyl), —C(O)(hydroxymethylpyrrolidinyl), —C(O)(morpholinyl), —C(O)(hydroxymethylmorpholinyl), pyrrolidinyl, morpholinyl, thiophenyl, methyl triazolyl, and oxazolidinonyl;

R$_4$ is H, F, Cl, or —CH$_3$;

R$_a$, at each occurrence, is independently H, C$_{1-4}$alkyl, or C$_{1-4}$fluoroalkyl;

two R$_b$ along with the nitrogen atom to which they are attached form a 4- to 7-membered heterocyclo ring having 1 to 2 nitrogen atoms and 0-1 oxygen or sulfur atoms;

R$_c$, at each occurrence, is independently C$_{1-3}$ alkyl or C$_{1-3}$ hydroxyalkyl, or two R$_c$ along with the nitrogen atom to which they are attached form a heterocyclyl or bicyclic heterocyclyl;

R$_d$, at each occurrence, is independently C$_{1-6}$ alkyl, C$_{1-4}$ fluoroalkyl, C$_{1-6}$ hydroxyalkyl, (C$_{1-4}$ alkoxy)—(C$_{1-3}$ alkylene), (C$_{1-2}$ fluoroalkoxy)—(C$_{1-2}$ alkylene), (C$_{3-6}$ cycloalkyl)—(C$_{0-2}$ alkylene), aryl-(C$_{1-2}$ alkylene), heteroaryl-(C$_{1-2}$ alkylene), aryloxy-(C$_{1-2}$ alkylene), aryl-CH$_2$O-(C$_{1-2}$ alkylene), or heteroaryloxy-(C$_{1-2}$ alkylene); and n is zero, 1, or 2.

2. The compound according to claim 1 or a salt thereof; wherein:

R$_1$ is —OH, C$_{1-2}$ alkyl, —CHFCH$_3$, —CH═CH$_2$, C$_{1-3}$ alkoxy, C$_{1-2}$ fluoroalkoxy, —OCH$_2$CH$_2$OH, —CH$_2$O(C$_{1-2}$ alkyl), —CD$_2$OCD$_3$, —CH$_2$OCHF$_2$, —CF$_2$OCH$_3$, —CH$_2$O(phenyl), § -CH(CH$_3$)OCH$_3$, —NH(CH$_3$), —N(CH$_3$)$_2$, —CH$_2$N(CH$_3$)$_2$, —C(O)NH$_2$, —C(O)NH(CH$_3$), —C(O)N(CH$_3$)$_2$, —C(O)NH(CH$_2$CH$_2$OH), —C(O)OCH$_3$, —CH(CH$_3$)OCH$_3$, cyclopropyl, furanyl, or —O(cyclopropyl);

R$_2$, at each occurrence, is independently H, F, Cl, —CN, —CH$_3$, —CH$_2$F, —CHF$_2$, —CF$_3$, —OCH$_3$, —OCF$_3$, —CH$_2$OH, —CH$_2$CH$_2$OH, —CH(CH$_3$)OH, —C(CH$_3$)$_2$OH, —CH(OH)CH$_2$OH, —CH$_2$NH$_2$, —C(O)NH$_2$, —C(O)N(CH$_3$)$_2$, —C(O)(piperidinyl), —C(O)OCH$_3$, —C(O)NH(CH$_2$CH$_2$OCH$_3$), —CH(OH)(cyclopropyl), —CH(OH)(phenyl), —CH═CH$_2$, —C(CH$_3$)═CH$_2$, or —C≡CH;

R$_3$ is:

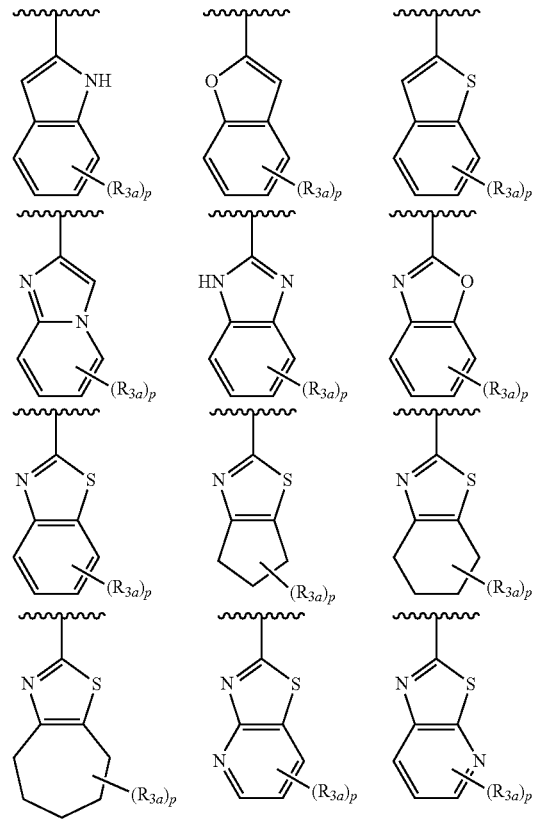

-continued

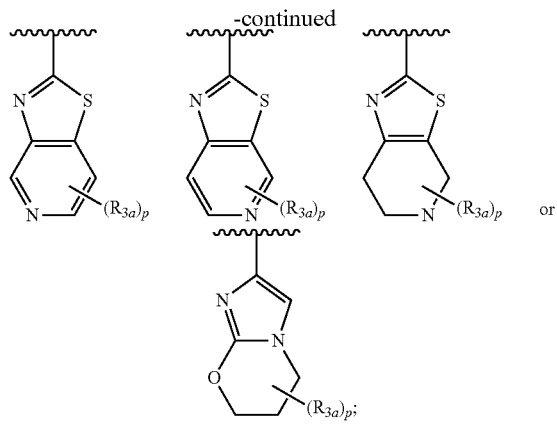

$R_{3a}$, at each occurrence, is independently:

(i) F, Cl, —CN, —OH, —CH$_3$, —CF$_3$, —CHFC(CH$_3$)$_3$, cyclopropyl, —CH$_2$OH, —CD$_2$OH, —CH$_2$CH$_2$OH, —CH(OH)CH$_3$, —C(CH$_3$)$_2$OH, —CH(OH)C(CH$_3$)$_3$, —CD(OH)C(CH$_3$)$_3$, —CH(OH)CF$_3$, —CH(OH)CH$_2$CF$_3$, —CH(OH)(cyclopropyl), —CH(OH)(methylcyclopropyl), —CH(OH)(trifluoromethylcyclopropyl), —CH(OH)(cyclopropyl substituted with phenyl), —CH(OH)(cyclobutyl), —CH(OH)(methoxycyclobutyl), —CH(OH)(ethoxycarbonylcyclobutyl), —CH(OH)(trifluoromethylcyclobutyl), —CH(OH)(hydroxymethylcyclobutyl), —CH(OH)(cyclobutyl substituted with phenyl), —CH(OH)(cyclohexyl), —CH(OH)(methylcyclohexyl), —CH(OH)(phenyl), —CH(OH)(isopropylphenyl), —CH(OH)(trifluoromethylphenyl), —CH(OH)(fluoro, methoxyphenyl), —CH(OH)(pyridinyl), —CH(OH)(thiazolyl), —CH(OH)(tetrahydropyranyl), —CH(OH)(methyltetrahydropyranyl), —CH$_2$OCH$_3$, —CH$_2$N(CH$_3$)$_2$, —CH$_2$NHS(O)$_2$(phenyl), or —CH(OH)CH$_2$(phenyl);

(ii) —OCH$_3$, —OCH$_2$CH$_3$, —OCH(CH$_3$)$_2$, —OCF$_3$, —OCHF$_2$, —OCH$_2$(phenyl), —OCH$_2$(thiazolyl), —OCH$_2$(oxazolidinonyl), —OCH$_2$(amino isoxazolyl), —OCH$_2$(imidazolyl substituted with phenyl), —OCH$_2$CH$_2$OH, —OCH$_2$CH(CH$_3$)OH, —OCH$_2$CH$_2$OCH$_3$, —OCH(CH$_3$)CH$_2$OH, —OCH$_2$CH(OH)CH$_3$, —OCH(CH$_3$)CH(OH)CH$_3$, —OCH$_2$C(CH$_3$)$_2$OH, —OCH$_2$CH$_2$O(phenyl), —OCH$_2$CH$_2$OCH$_2$(phenyl), —OCH$_2$CH$_2$NH(CH$_3$), —OCH$_2$CH(CH$_3$)NH(methoxy pyrimidinyl), —OCH$_2$C(O)OH, —OCH$_2$C(O)OCH$_3$, —OCH$_2$C(O)OCH$_2$CH$_3$, —OCH$_2$C(O)OC(CH$_3$)$_3$, —OCH$_2$C(O)NH(phenyl), —OCH$_2$C(O)NHCH$_2$(phenyl), —OCH$_2$C(O)(morpholinyl), —OCH$_2$CH$_2$CH$_2$C(O)NH(pyridinyl), —OCH$_2$CH$_2$OC(O)OCH$_3$, —OCH$_2$CH(CH$_3$)OC(O)NHCH$_2$CH$_2$C(O)NH$_2$, —OCH$_2$CH(CH$_2$CH$_3$)OC(O)NH(pyridinyl), —OCH$_2$CH(CH$_2$OCH$_3$)OC(O)NH(pyridinyl), —OCH$_2$CH(CH$_2$OC(CH$_3$)$_3$)OC(O)NH(pyridinyl), —OCH$_2$CH(CH$_2$OCH$_2$CH(CH$_3$)$_2$)OC(O)NH(pyridinyl), —OCH$_2$CH(CH$_2$OCH$_2$(phenyl))OC(O)NH(pyridinyl), —OCH$_2$CH(CH$_2$OCH$_2$CH(CH$_3$)$_2$)OC(O)NH(pyrimidinyl), or —OCH$_2$CH(CH$_2$OCH$_2$CH(CH$_3$)$_2$)OC(O)NH(methyl pyrimidinyl);

(iii) —C(O)OH, —C(O)OCH$_3$, or —C(O)OC(CH$_3$)$_3$;
(iv) —NHC(O)OCH$_3$, —NHC(O)OC(CH$_3$)$_3$, —NHC(O)OCH$_2$(phenyl), —NHC(O)OCH$_2$(tetrahydrofuranyl), or —NHC(O)O(tetrahydropyranyl);
(v) —OCH$_2$CH$_2$NHC(O)OCH$_3$, —OCH$_2$CH$_2$NHC(O)O(tetrahydropyranyl), —OCH$_2$CH$_2$NHC(O)OCH$_2$(phenyl), —OCH$_2$CH$_2$NHC(O)O(methoxyphenyl), —OCH$_2$CH$_2$NHC(O)O(tetrahydrofuranyl), —OCH$_2$CH$_2$NHC(O)OCH$_2$(tetrahydrofuranyl), —OCH$_2$CH$_2$NHC(O)NH(pyridinyl), —OCH$_2$CH$_2$N(CH$_3$)C(O)NH(methylpyrimidinyl), or —OCH$_2$CH(CH$_3$)OC(O)OCH$_2$(aminopyridinyl);
(vi) —OCH$_2$CH$_2$NHS(O)$_2$CH$_3$ or —OCH$_2$CH$_2$NHS(O)$_2$R$_w$ wherein R$_w$ is phenyl or pyridinyl, each substituted with zero to 2 substituents independently selected from F, Cl, and —CH$_3$; or
(vii) —OCH$_2$CH$_2$OC(O)NHR$_z$, —OCH(CH$_3$)CH$_2$OC(O)NHR$_z$, —OCH$_2$CH(CH$_3$)OC(O)NHR$_z$, —OCH(CH$_3$)CH(CH$_3$)OC(O)NHR$_z$, —OCH$_2$CH(CH$_2$O(isobutyl))OC(O)NHR$_z$, —OCH$_2$CH(CH$_2$CH$_3$)OC(O)NHR$_z$, —OCH$_2$CH(CH$_2$OCH$_3$)OC(O)NHR$_z$, or —OCH$_2$CH(CH$_2$OCH$_2$CH(CH$_3$)$_2$)OC(O)NHR$_z$ wherein R$_z$ is H, —CH$_2$CF$_3$, phenyl, pyrrolyl, pyrazolyl, thiazolyl, isothiazolyl, pyridinyl, pyridazinyl, pyrimidinyl, pyrazinyl, oxadiazolyl, thiadiazolyl, indolyl, pyrrolo[2,3-b]pyridinyl, benzo[d]oxazolonyl, —CH$_2$(pyrazolyl), —CH$_2$(imidazolyl), or —CH$_2$(pyridinyl), each substituted with zero to 2 substituents independently selected from F, Cl, Br, —CN, —OH, —CH$_3$, —CH$_2$CH$_2$CH$_3$, —CF$_3$, —CH$_2$OH, —CD$_2$OH, —CH(CH$_3$)OH, —CH$_2$CH$_2$OH, —CH$_2$CH$_2$CH$_2$OH, —C(CH$_3$)$_2$OH, —CH$_2$CH(CH$_3$)OH, —CH$_2$C(CH$_3$)$_2$OH, —CH$_2$CH$_2$C(O)OCH$_3$, —CH$_2$OP(O)(OH)$_2$, —CH$_2$CH$_2$OP(O)(OH)$_2$, —CH$_2$(morpholinyl), —OCH$_3$, —OCH$_2$CH$_2$OH, —OCH$_2$CH(CH$_3$)OH, —OCH$_2$C(CH$_3$)$_2$OH, —OCH$_2$CH$_2$C(CH$_3$)$_2$OH, —OCH(CH$_3$)CH$_2$OH, —OCH$_2$CH(OH)CH$_2$OH, —OCH$_2$CF$_2$OH, —OCH$_2$CF$_2$CH$_2$OH, —C(O)OH, —C(O)OCH$_3$, —C(O)NH$_2$, —C(O)NH(CH$_3$), —C(O)N(CH$_3$)$_2$, —C(O)NH(CH$_2$CH$_2$OH), —C(O)NH(CH$_2$CH(CH$_3$)OH), —C(O)NH(CH$_2$C(CH$_3$)$_2$OH), —C(O)NH(CH$_2$CH$_2$C(CH$_3$)$_2$OH), —C(O)N(CH$_3$)CH$_2$CH$_2$OH, —C(O)N(CH$_3$)CH$_2$C(CH$_3$)$_2$OH, —C(O)NHCH$_2$(hydroxymethyloxetanyl), —C(O)NH(hydroxymethylcyclobutyl), —C(O)NHCH$_2$(hydroxycyclobutyl), —C(O)NHCH$_2$(hydroxymethylcyclobutyl), —C(O)NHCH$_2$C(CH$_3$)$_2$OP(O)(OH)$_2$, —C(O)(hydroxypiperidinyl), —C(O)(hydroxypyrrolidinyl), —C(O)(hydroxymethylpyrrolidinyl), —C(O)(morpholinyl), —C(O)(hydroxymethylmorpholinyl), —NH$_2$, —N(CH$_3$)$_2$, —NHC(O)CH$_3$, —NHC(O)(chloro, fluorophenyl), —NH(CH$_2$C(CH$_3$)$_2$OH), —N(CH$_3$)S(O)$_2$CH$_3$, pyrrolidinyl, morpholinyl, thiophenyl, methyl triazolyl, and oxazolidinonyl;

R$_4$ is H, F, or —CH$_3$; and
p is zero, 1, 2, or 3.

3. The compound according to claim 1 or a salt thereof, wherein:
R$_3$ is:

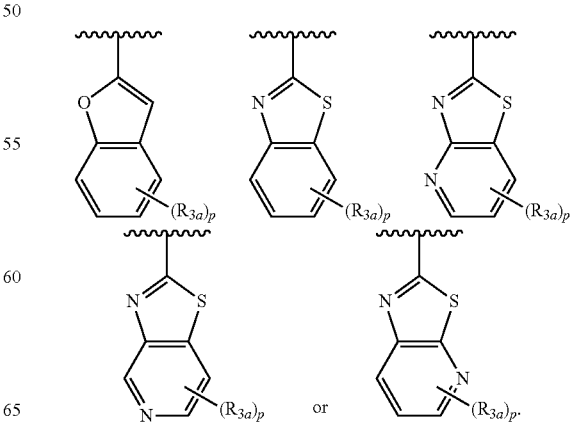

4. The compound according to claim 1 having the structure of Formula (I):

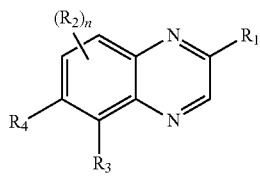

or a salt thereof.

5. The compound according to claim 4 or a salt thereof, wherein:
$R_1$ is —OCH$_3$, —OCHF$_2$, —OCH$_2$CH$_3$, or —CH$_2$OCH$_3$;
$R_2$, at each occurrence, is independently H, F, Cl, —CN, —CH$_3$, —OCH$_3$, or —CH$_2$OH; and
$R_3$ is:

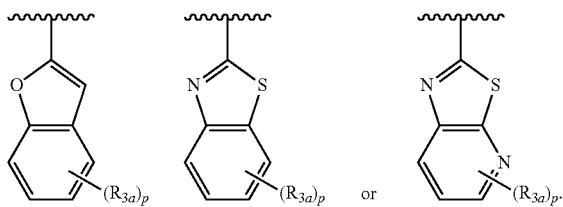

6. The compound according to claim 1 or a salt thereof, wherein said compound is selected from:
5-(benzofuran-2-yl)-2-(difluoromethoxy)-7-methylquinoxaline (1);
2-(difluoromethoxy)-5-(5-methoxybenzofuran-2-yl)-7-methylquinoxaline (2);
2-(2-(difluoromethoxy)-7-methylquinoxalin-5-yl)benzo[d]oxazole (3);
2-(2-(difluoromethoxy)-7-methylquinoxalin-5-yl)benzo[d]thiazole (4);
2-(difluoromethoxy)-5-(1H-indol-2-yl)-7-methylquinoxaline (5);
2-(difluoromethoxy)-5-(4,5-dimethoxybenzofuran-2-yl)-7-methylquinoxaline (6);
6-(benzyloxy)-2-(2-(difluoromethoxy)-7-methylquinoxalin-5-yl)benzo[d]thiazole (7);
4-chloro-2-(2-(difluoromethoxy)-7-methylquinoxalin-5-yl)benzo[d]thiazole (8);
2-(2-(difluoromethoxy)-7-methylquinoxalin-5-yl)thiazolo[4,5-b]pyridine (9);
2-(2-(difluoromethoxy)-7-methylquinoxalin-5-yl)-6-methoxy-4-methylbenzo[d]thiazole (10);
tert-butyl 2-(2-(difluoromethoxy)-7-methylquinoxalin-5-yl)-6,7-dihydrothiazolo[5,4-c]pyridine-5(4H)-carboxylate (11);
2-(2-(difluoromethoxy)-7-methylquinoxalin-5-yl)-7-methoxy-4-methylbenzo[d]thiazole (12);
2-(2-(difluoromethoxy)-7-methylquinoxalin-5-yl)-4,6-difluoro-7-methoxybenzo[d]thiazole (13);
tert-butyl (2-(2-(difluoromethoxy)-7-methylquinoxalin-5-yl)benzo[d]thiazol-7-yl) carbamate (14);
2-(2-(difluoromethoxy)-7-methylquinoxalin-5-yl)-7-(thiazol-4-ylmethoxy)benzo[d]thiazole (15);
tetrahydrofuran-3-yl (2-((2-(2-(difluoromethoxy)-7-methylquinoxalin-5-yl)benzo[d]thiazol-6-yl)oxy)ethyl)carbamate (16);
2-(2-(difluoromethoxy)-7-methylquinoxalin-5-yl)-7-(2-phenoxyethoxy)benzo[d]thiazole (17);
7-(2-(benzyloxy)ethoxy)-2-(2-(difluoromethoxy)-7-methylquinoxalin-5-yl)benzo[d] thiazole (18);
(tetrahydrofuran-2-yl)methyl (2-((2-(2-(difluoromethoxy)-7-methylquinoxalin-5-yl) benzo[d]thiazol-6-yl)oxy)ethyl)carbamate (19);
tetrahydro-2H-pyran-4-yl (2-((2-(2-(difluoromethoxy)-7-methylquinoxalin-5-yl) benzo[d]thiazol-6-yl) oxy)ethyl)carbamate (20);
tetrahydro-2H-pyran-4-yl (2-(2-(difluoromethoxy)-7-methylquinoxalin-5-yl) benzo[d]thiazol-7-yl)carbamate (21);
(tetrahydrofuran-2-yl) methyl (2-(2-(difluoromethoxy)-7-methylquinoxalin-5-yl) benzo[d]thiazol-7-yl)carbamate (22);
2-(2-(difluoromethoxy)-7-methylquinoxalin-5-yl)-5-methoxythiazolo[5,4-b]pyridine (23);
2-(2-(difluoromethoxy)-7-methylquinoxalin-5-yl)-7-methoxythiazolo[4,5-c]pyridine (24);
tert-butyl (2-(2-(difluoromethoxy)-7-methylquinoxalin-5-yl)-4,5,6,7-tetrahydrobenzofuran-4-yl) carbamate (25);
4-fluoro-N-(2-((2-(2-methoxy-7-methylquinoxalin-5-yl)-4-methylbenzo[d]thiazol-6-yl)oxy)ethyl)benzenesulfonamide (26);
N-(2-((4-chloro-2-(2-methoxy-7-methylquinoxalin-5-yl) benzo[d]thiazol-6-yl)oxy)ethyl) benzenesulfonamide (27);
N-(2-((4-chloro-2-(2-methoxy-7-methylquinoxalin-5-yl) benzo[d]thiazol-6-yl)oxy)ethyl)-4-fluorobenzenesulfonamide (28);
4-fluoro-N-(2-((2-(2-(methoxymethyl)-7-methylquinoxalin-5-yl)-4-methylbenzo[d]thiazol-6-yl)oxy) ethyl) benzenesulfonamide (29);
N-(2-((2-(2-ethoxy-7-methylquinoxalin-5-yl)-4-methyl-benzo [d]thiazol-6-yl)oxy) ethyl)-4-fluorobenzenesulfonamide (30);
N-(2-((2-(2-ethyl-7-methylquinoxalin-5-yl)-4-methyl-benzo[d]thiazol-6-yl)oxy)ethyl)-4-fluorobenzenesulfonamide (31);
methyl 5-(6-(2-(4-fluorophenylsulfonamido)ethoxy)-4-methylbenzo[d]thiazol-2-yl)-7-methylquinoxaline-2-carboxylate (32);
N-(2-((2-(2-cyclopropoxy-7-methylquinoxalin-5-yl)-4-methylbenzo[d]thiazol-6-yl)oxy)ethyl)-4-fluorobenzenesulfonamide (33);
4-fluoro-N-(2-((2-(2-(fluoromethoxy)-7-methylquinoxalin-5-yl)-4-methylbenzo[d]thiazol-6-yl) oxy)ethyl)benzenesulfonamide (34);
2-(2-methoxy-7-methylquinoxalin-5-yl)-4-methyl-6-((2-phenyl-1H-imidazol-5-yl)methoxy)benzo[d]thiazole (35);
N-benzyl-2-((2-(2-methoxy-7-methylquinoxalin-5-yl)-4-methylbenzo[d]thiazol-6-yl) oxy)acetamide (36);
5-(7-chlorobenzofuran-2-yl)-2-methoxy-7-methylquinoxaline (37);
2-((7-chloro-2-(2-methoxy-7-methylquinoxalin-5-yl)benzofuran-5-yl)oxy)ethyl (2-methylpyridin-4-yl)carbamate (38);
N-(2-((7-chloro-2-(2-methoxy-7-methylquinoxalin-5-yl) benzofuran-5-yl)oxy)ethyl)benzenesulfonamide (39);
5-(benzo[b]thiophen-2-yl)-2-(difluoromethoxy)-7-methylquinoxaline (40);
N-(2-((7-chloro-2-(2-methoxy-7-methylquinoxalin-5-yl) benzofuran-5-yl)oxy)ethyl)benzenesulfonamide (39);

2-(difluoromethoxy)-5-(7-methoxybenzofuran-2-yl)-7-methylquinoxaline (41);
2-(difluoromethoxy)-5-(4-methoxybenzofuran-2-yl)-7-methylquinoxaline (42);
5-(4-(benzyloxy)benzofuran-2-yl)-2-methoxy-7-methylquinoxaline (43);
5-(5-(benzyloxy) benzofuran-2-yl)-2-(difluoromethoxy)-7-methylquinoxaline (44);
2-(difluoromethoxy)-5-(imidazo[1,2-a]pyridin-2-yl)-7-methylquinoxaline (45);
methyl 2-(2-(2-(difluoromethoxy)-7-methylquinoxalin-5-yl)benzofuran-5-yloxy)ethylcarbamate (46);
5-(1H-benzo[d]imidazol-2-yl)-2-(difluoromethoxy)-7-methylquinoxaline (47);
2-(2-(difluoromethoxy)-7-methylquinoxalin-5-yl)-6-methoxybenzo[d]thiazole (48);
tert-butyl 2-(2-(2-(difluoromethoxy)-7-methylquinoxalin-5-yl)benzofuran-5-yloxy) acetate (49);
2-(difluoromethoxy)-5-(5-methoxy-1H-benzo[d]imidazol-2-yl)-7-methylquinoxaline (50);
2-(2-(difluoromethoxy)-7-methylquinoxalin-5-yl)-4-methoxybenzo[d]thiazole (51);
2-(2-(difluoromethoxy)-7-methylquinoxalin-5-yl)-4-methylbenzo[d]thiazole (52);
2-(2-(difluoromethoxy)-7-methylquinoxalin-5-yl)-4-fluorobenzo[d]thiazole (53);
2-(2-(2-(difluoromethoxy)-7-methylquinoxalin-5-yl)benzofuran-5-yloxy)—N-methylethanamine (54);
2-(2-(difluoromethoxy)-7-methylquinoxalin-5-yl)-4,6-dimethoxybenzo[d]thiazole (55);
2-methoxy-5-(5-methoxybenzofuran-2-yl)-7-methylquinoxaline (56);
2-(2-(difluoromethoxy)-7-methylquinoxalin-5-yl)-7-methoxybenzo[d]thiazole (58);
2-(2-(difluoromethoxy)-7-methylquinoxalin-5-yl)-4-fluoro-6-methoxybenzo[d]thiazole (59);
2-(2-(difluoromethoxy)-7-methylquinoxalin-5-yl)-5-fluorobenzo[d]thiazole (60);
methyl 2-(2-(difluoromethoxy)-7-methylquinoxalin-5-yl) benzo[d]thiazole-7-carboxylate (61);
2-(2-(difluoromethoxy)-7-methylquinoxalin-5-yl)-6,7-dihydrothiazolo[5,4-c]pyridine-5(4H)-carboxylate (62);
N-(2-(2-(2-(difluoromethoxy)-7-methylquinoxalin-5-yl)benzo[d]thiazol-6-yloxy)ethyl) benzenesulfonamide (63);
(2-(2-(difluoromethoxy)-7-methylquinoxalin-5-yl)benzo[d] thiazol-7-yl)methanol (64);
2-(2-(difluoromethoxy)-7-methylquinoxalin-5-yl)-7-(methoxymethyl)benzo[d]thiazole (65);
N-((2-(2-(difluoromethoxy)-7-methylquinoxalin-5-yl)benzo[d]thiazol-7-yl)methyl)benzenesulfonamide (66);
N-(2-(2-(2-(difluoromethoxy)-7-methylquinoxalin-5-yl)-4-fluorobenzo[d]thiazol-6-yloxy)ethyl) benzenesulfonamide (67);
2-(2-(difluoromethoxy)-7-methylquinoxalin-5-yl)-5-methylbenzo[d]thiazole (68);
methyl 2-(2-(2-(difluoromethoxy)-7-methylquinoxalin-5-yl)benzo[d]thiazol-7-yloxy)ethylcarbamate (69);
methyl 2-(2-(2-(difluoromethoxy)-7-methylquinoxalin-5-yl)-4-methylbenzo[d]thiazol-7-yloxy)ethylcarbamate (70);
2-(2-(difluoromethoxy)-7-methylquinoxalin-5-yl)-6-(thiazol-4-ylmethoxy)benzo[d]thiazole (71);
N-(2-(2-(2-methoxy-7-methylquinoxalin-5-yl)benzo[d]thiazol-6-yloxy)ethyl) benzenesulfonamide (72);
N-(2-(2-(2-(difluoromethoxy)-7-methylquinoxalin-5-yl)-4-methylbenzo[d]thiazol-6-yloxy)ethyl)benzenesulfonamide (73);
2-(2-(2-(difluoromethoxy)-7-methylquinoxalin-5-yl) benzo[d]thiazol-7-yloxy)ethanol (74);
2-(2-(difluoromethoxy)-7-methylquinoxalin-5-yl)-7-(2-methoxyethoxy)benzo[d]thiazole (75);
benzyl 2-(2-(difluoromethoxy)-7-methylquinoxalin-5-yl) benzo[d]thiazol-7-ylcarbamate (76);
2-(2-methoxy-7-methylquinoxalin-5-yl)-6-(2-methoxyethoxy)benzo[d]thiazole (77);
2-(2-methoxy-7-methylquinoxalin-5-yl)-7-(2-methoxyethoxy)benzo[d]thiazole (78);
N-(2-(2-(2-methoxy-7-methylquinoxalin-5-yl)-4-methylbenzo[d]thiazol-6-yloxy)ethyl) benzenesulfonamide (79);
methyl 2-(2-(difluoromethoxy)-7-methylquinoxalin-5-yl) benzo[d]thiazol-7-ylcarbamate (80);
N-(2-(2-(2-(difluoromethoxy)-7-methylquinoxalin-5-yl)-4-methylbenzo[d]thiazol-6-yloxy)ethyl)-4-fluorobenzenesulfonamide (81);
2-(2-(2-(difluoromethoxy)-7-methylquinoxalin-5-yl) benzo[d]thiazol-7-yloxy)—N-phenylacetamide (82);
N-(2-(2-(2-(difluoromethoxy)-7-methylquinoxalin-5-yl)-4-methylbenzo[d]thiazol-6-yloxy)ethyl)-4-(trifluoromethyl) benzenesulfonamide (83);
N-(2-(2-(2-(difluoromethoxy)-7-methylquinoxalin-5-yl)-4-methylbenzo[d]thiazol-6-yloxy)ethyl)-2,4-difluorobenzenesulfonamide (84);
N-(2-(2-(2-(difluoromethoxy)-7-methylquinoxalin-5-yl)-4-methylbenzo[d]thiazol-6-yloxy)ethyl)-3,4-difluorobenzenesulfonamide (85);
4-chloro-N-(2-(2-(2-(difluoromethoxy)-7-methylquinoxalin-5-yl)-4-methylbenzo[d]thiazol-6-yloxy) ethyl) benzenesulfonamide (86);
N-(2-(2-(2-methoxy-7-methylquinoxalin-5-yl)-4-methylbenzo[d]thiazol-6-yloxy) ethyl)-4-methylbenzenesulfonamide (87);
4-fluoro-N-(2-(2-(2-(methoxymethyl)-7-methylquinoxalin-5-yl)-4-methylbenzo[d]thiazol-6-yloxy)ethyl)benzenesulfonamide (89);
4-fluoro-N-(2-(2-(2-methoxy-7-methylquinoxalin-5-yl)-4-(trifluoromethyl)benzo[d]thiazol-6-yloxy) ethyl) benzenesulfonamide (90);
N-(2-(2-(2-cyclopropyl-7-methylquinoxalin-5-yl)-4-methylbenzo[d]thiazol-6-yloxy)ethyl)-4-fluorobenzenesulfonamide (91);
benzyl 2-(2-(2-(methoxymethyl)-7-methylquinoxalin-5-yl)-4-methylbenzo[d]thiazol-6-yloxy) ethylcarbamate (92);
4-chloro-6-methoxy-2-(2-(methoxymethyl)-7-methylquinoxalin-5-yl)benzo[d]thiazole (93);
5-(5-methoxybenzofuran-2-yl)-2-(methoxymethyl)-7-methylquinoxaline (94);
N-(2-(4-methoxy-2-(2-(methoxymethyl)-7-methylquinoxalin-5-yl)benzo[d]thiazol-6-yloxy)ethyl)benzenesulfonamide (95);
2-fluoro-N-(2-(2-(2-(methoxymethyl)-7-methylquinoxalin-5-yl)-4-methylbenzo[d]thiazol-6-yloxy)ethyl) benzenesulfonamide (96);
3-fluoro-N-(2-(2-(2-(methoxymethyl)-7-methylquinoxalin-5-yl)-4-methylbenzo[d]thiazol-6-yloxy)ethyl)benzenesulfonamide (97);
N-(2-(4-chloro-2-(2-(methoxymethyl)-7-methylquinoxalin-5-yl)benzo[d]thiazol-6-yloxy)ethyl) methanesulfonamide (98);

N-(2-(4-chloro-2-(2-(methoxymethyl)-7-methylquinoxalin-5-yl)benzo[d]thiazol-6-yloxy)ethyl)benzenesulfonamide (99);

N-(2-(4-chloro-2-(2-(methoxymethyl)-7-methylquinoxalin-5-yl)benzo[d]thiazol-6-yloxy)ethyl)-2-fluorobenzenesulfonamide (100);

N-(2-(4-chloro-2-(2-(methoxymethyl)-7-methylquinoxalin-5-yl)benzo[d]thiazol-6-yloxy)ethyl)-4-fluorobenzenesulfonamide (101);

N-(2-(4-chloro-2-(2-(methoxymethyl)-7-methylquinoxalin-5-yl)benzo[d]thiazol-6-yloxy)ethyl)-3-fluorobenzenesulfonamide (102);

6-methoxy-2-(2-(methoxymethyl)-7-methylquinoxalin-5-yl)benzo[d]thiazole-4-carbonitrile (103);

N-(2-(4-cyclopropyl-2-(2-(methoxymethyl)-7-methylquinoxalin-5-yl)benzo[d]thiazol-6-yloxy)ethyl) benzenesulfonamide (104);

N-(2-(4-cyclopropyl-2-(2-(methoxymethyl)-7-methylquinoxalin-5-yl)benzo[d]thiazol-6-yloxy)ethyl)-4-fluorobenzenesulfonamide (105);

N-(2-(2-(2-(methoxymethyl)-7-methylquinoxalin-5-yl)benzo[d]thiazol-6-yloxy) ethyl)benzenesulfonamide (106);

4-fluoro-N-(2-(2-(2-(methoxymethyl)-7-methylquinoxalin-5-yl)benzo[d]thiazol-6-yloxy)ethyl)benzenesulfonamide (107);

4-fluoro-N-(2-(2-(2-(1-fluoroethyl)-7-methylquinoxalin-5-yl)-4-methylbenzo[d]thiazol-6-yloxy)ethyl)benzenesulfonamide (108);

N-(2-(4-cyano-2-(2-(methoxymethyl)-7-methylquinoxalin-5-yl)benzo[d]thiazol-6-yloxy)ethyl)-4-fluorobenzenesulfonamide (109);

2-(2-(2-methoxy-7-methylquinoxalin-5-yl)-4-methylbenzo[d]thiazol-6-yloxy)ethyl phenylcarbamate (110);

2-(2-(2-methoxy-7-methylquinoxalin-5-yl)-4-methylbenzo[d] thiazol-6-yloxy)ethyl pyridin-3-ylcarbamate (111);

2-(2-(2-methoxy-7-methylquinoxalin-5-yl)-4-methylbenzo[d]thiazol-6-yloxy)ethyl 6-methoxypyridin-3-ylcarbamate (112);

2-(2-(2-methoxy-7-methylquinoxalin-5-yl)-4-methylbenzo[d]thiazol-6-yloxy)ethyl pyridin-4-ylcarbamate (113);

N-(2-(2-(2-((difluoromethoxy)methyl)-7-methylquinoxalin-5-yl)-4-methylbenzo[d]thiazol-6-yloxy)ethyl)-4-fluorobenzenesulfonamide (114);

2-(2-(2-methoxy-7-methylquinoxalin-5-yl)benzo[d]thiazol-6-yloxy)ethyl 6-methoxypyridin-3-ylcarbamate (115);

2-(2-(2-methoxy-7-methylquinoxalin-5-yl)-4-methylbenzo[d]thiazol-6-yloxy)ethyl 5-cyanopyridin-3-ylcarbamate (116);

2-((2-(2-methoxy-7-methylquinoxalin-5-yl)-4-methylbenzo[d]thiazol-6-yl)oxy)ethyl (6-cyanopyridin-3-yl) carbamate (117);

2-((2-(2-methoxy-7-methylquinoxalin-5-yl)benzo[d]thiazol-6-yl)oxy) ethyl (3-cyanophenyl)carbamate (118);

2-((2-(2-methoxy-7-methylquinoxalin-5-yl)-4-methylbenzo[d]thiazol-6-yl)oxy)ethyl (2-chloropyrimidin-5-yl)carbamate (119);

5-(6-fluoro-5-methoxybenzofuran-2-yl)-2-methoxy-7-methylquinoxaline (120);

5-(7-chloro-6-fluoro-5-methoxybenzofuran-2-yl)-2-(methoxymethyl)-7-methylquinoxaline (121);

5-(7-chloro-6-fluoro-5-methoxybenzofuran-2-yl)-2-methoxy-7-methylquinoxaline (122);

2-((6-fluoro-2-(2-methoxy-7-methylquinoxalin-5-yl)benzofuran-5-yl)oxy)ethyl (2-methylpyridin-4-yl)carbamate (123);

(8-(7-chloro-6-fluoro-5-methoxybenzofuran-2-yl)-3-methoxyquinoxalin-6-yl)methanol (124);

(8-(6-fluoro-5-methoxybenzofuran-2-yl)-3-methoxyquinoxalin-6-yl)methanol (125);

2-((6-fluoro-2-(7-(hydroxymethyl)-2-methoxyquinoxalin-5-yl)benzofuran-5-yl)oxy)ethyl (2-methylpyridin-4-yl)carbamate (126);

3-methoxy-8-(6-methoxybenzo[d]thiazol-2-yl)quinoxalin-6-yl)methanol (127);

2-(2-(7-(hydroxymethyl)-2-methoxyquinoxalin-5-yl)-4-methylbenzo[d]thiazol-6-yloxy)ethyl 6-methylpyridin-3-ylcarbamate (128);

2-(2-(7-(hydroxymethyl)-2-methoxyquinoxalin-5-yl)-4-methylbenzo[d]thiazol-6-yloxy)ethyl 2-methylpyridin-4-ylcarbamate (129);

2-((6-fluoro-2-(7-(hydroxymethyl)-2-methoxyquinoxalin-5-yl)benzofuran-5-yl)oxy)ethyl (2-methylpyridin-4-yl)carbamate (126);

5-(benzofuran-2-yl)-7-methyl-2-vinylquinoxaline (131);

5-(benzofuran-2-yl)-2-ethyl-7-methylquinoxaline (132);

5-(benzofuran-2-yl)-2-(difluoromethoxy)-8-methylquinoxaline (133);

5-(benzofuran-2-yl)-2-(furan-3-yl)-7-methylquinoxaline (135);

2-(2-(difluoromethoxy)-7-methylquinoxalin-5-yl)-5,6-dihydro-4H-cyclopenta[d]thiazole (136);

2-(2-methoxy-7-methylquinoxalin-5-yl)-5,6,7,8-tetrahydro-4H-cyclohepta[d]thiazole (137);

2-(2-methoxy-7-methylquinoxalin-5-yl)-4,5,6,7-tetrahydrobenzo[d]thiazol-7-ol (138);

7-methoxy-2-(2-methoxy-7-methylquinoxalin-5-yl)-4,5,6,7-tetrahydrobenzo[d]thiazole (139);

6-methoxy-2-(2-methoxy-7-methylquinoxalin-5-yl)-4,5,6,7-tetrahydrobenzo[d]thiazole (140);

2-(2-methoxy-7-methylquinoxalin-5-yl)-6,6-dimethyl-4,5,6,7-tetrahydrobenzo[d]thiazole (141);

2-(2-(difluoromethoxy)-7-methylquinoxalin-5-yl)-5,6-dihydro-4H-cyclopenta[d]thiazole (136);

2-(2-(2-methoxy-7-methylquinoxalin-5-yl)-5,6-dihydro-4H-cyclopenta[d] thiazol-5-yl) ethanol (142);

2-(2-(methoxymethyl)-7-methylquinoxalin-5-yl)-4,5,6,7-tetrahydrobenzo[d] thiazol-7-ol (143);

2-(2-(methoxymethyl)-7-methylquinoxalin-5-yl)-4,5,6,7-tetrahydrobenzo[d]thiazole (144);

2-(2-(methoxymethyl)-7-methylquinoxalin-5-yl)-6,6-dimethyl-4,5,6,7-tetrahydrobenzo[d]thiazol-7-ol (145);

2-(2-(methoxymethyl)-7-methylquinoxalin-5-yl)thiazolo[4,5-c]pyridine (146);

2-(2-(methoxymethyl)-7-methylquinoxalin-5-yl)thiazolo[5,4-b]pyridine (147);

2-(2-(methoxymethyl)-7-methylquinoxalin-5-yl)thiazolo[5,4-b]pyridine (148);

7-chloro-2-(2-(methoxymethyl)-7-methylquinoxalin-5-yl)thiazolo[5,4-c]pyridine (149);

5-methoxy-2-(2-methoxy-7-methylquinoxalin-5-yl)thiazolo[5,4-b]pyridine (150);

7-chloro-2-(2-methoxy-7-methylquinoxalin-5-yl)thiazolo[5,4-c]pyridine (151);

6-methoxy-2-(2-methoxy-7-methylquinoxalin-5-yl)benzo[d]thiazole-4-carboxylate (152);

(6-methoxy-2-(2-methoxy-7-methylquinoxalin-5-yl)benzo[d]thiazol-4-yl)methanol (154);

(6-methoxy-2-(2-(methoxymethyl)-7-methylquinoxalin-5-yl)benzo[d]thiazol-4-yl) methanol (155);

1-(6-methoxy-2-(2-(methoxymethyl)-7-methylquinoxalin-5-yl)benzo[d] thiazol-4-yl) ethanol (156);
2-(6-methoxy-2-(2-(methoxymethyl)-7-methylquinoxalin-5-yl)benzo[d]thiazol-4-yl) propan-2-ol (157);
cyclopropyl(6-methoxy-2-(2-(methoxymethyl)-7-methylquinoxalin-5-yl) benzo[d]thiazol-4-yl)methanol (158);
1-(6-methoxy-2-(2-(methoxymethyl)-7-methylquinoxalin-5-yl)benzo[d]thiazol-4-yl)—N,N-dimethyl methanamine (159);
cyclopropyl(6-methoxy-2-(2-methoxy-7-methylquinoxalin-5-yl)benzo[d]thiazol-4-yl) methanol (160);
(6-methoxy-2-(2-(methoxymethyl)-7-methylquinoxalin-5-yl)benzo[d]thiazol-4-yl) (phenyl)methanol (161);
6-methoxy-2-(2-(methoxymethyl)-7-methylquinoxalin-5-yl)benzo[d]thiazole-4-carboxylic acid (162);
(6-methoxy-2-(2-(methoxymethyl)-7-methylquinoxalin-5-yl)benzo[d]thiazol-4-yl)(phenyl) methanol (163);
1-(6-methoxy-2-(2-(methoxymethyl)-7-methylquinoxalin-5-yl)benzo[d]thiazol-4-yl)-2,2-dimethylpropan-1-ol (164);
cyclohexyl(6-methoxy-2-(2-(methoxymethyl)-7-methylquinoxalin-5-yl)benzo[d]thiazol-4-yl)methanol (165);
cyclobutyl(6-methoxy-2-(2-(methoxymethyl)-7-methylquinoxalin-5-yl)benzo[d]thiazol-4-yl)methanol (166);
(6-methoxy-2-(2-(methoxymethyl)-7-methylquinoxalin-5-yl)benzo [d]thiazol-4-yl)(pyridin-2-yl)methanol (167);
(6-methoxy-2-(2-(methoxymethyl)-7-methylquinoxalin-5-yl)benzo[d]thiazol-4-yl) (pyridin-3-yl)methanol (168);
1-(6-methoxy-2-(2-(methoxymethyl)-7-methylquinoxalin-5-yl)benzo[d]thiazol-4-yl)-2,2-dimethylpropan-1-ol-1-$d_1$ (169);
1-(6-methoxy-2-(2-(methoxymethyl)-7-methylquinoxalin-5-yl)benzo[d]thiazol-4-yl)-2,2-dimethylpropan-1-ol-$d_5$ (170);
2,2,2-trifluoro-1-(6-methoxy-2-(2-(methoxymethyl)-7-methylquinoxalin-5-yl)benzo[d]thiazol-4-yl)ethanol (171);
(6-methoxy-2-(2-(methoxymethyl)-7-methylquinoxalin-5-yl)benzo[d]thiazol-4-yl)(pyridin-4-yl)methanol (172);
3,3,3-trifluoro-1-(6-methoxy-2-(2-(methoxymethyl)-7-methylquinoxalin-5-yl)benzo[d]thiazol-4-yl)propan-1-ol (173);
2,2,2-trifluoro-1-(6-methoxy-2-(2-methoxy-7-methylquinoxalin-5-yl)benzo[d]thiazol-4-yl) ethanol (174);
5-(benzofuran-2-yl)-2-methoxy-7-methylquinoxaline (175);
methyl 5-(benzofuran-2-yl)-7-methylquinoxaline-2-carboxylate (176);
8-(benzofuran-2-yl)-3-methoxy-6-methylquinoline (177);
2-(2-(difluoromethoxy)-7-methylquinoxalin-5-yl)-4,5,6,7-tetrahydrobenzo[d]thiazole (178);
5-methoxy-2-(2-methoxy-7-methylquinoxalin-5-yl)-7-methylthiazolo[5,4-b]pyridine (179);
6-fluoro-5-methoxy-2-(2-(methoxymethyl)-7-methylquinoxalin-5-yl)thiazolo[5,4-b] pyridine (180);
5-methoxy-2-(2-(methoxymethyl)-7-methylquinoxalin-5-yl)-7-methylthiazolo[5,4-b] pyridine (181);
6-fluoro-5-methoxy-2-(2-methoxy-7-methylquinoxalin-5-yl)thiazolo[5,4-b]pyridine (182);
6-methoxy-2-(2-(methoxymethyl)-7-methylquinoxalin-5-yl)-4-methylbenzo[d]thiazole (183);
5-(benzofuran-2-yl)-2-(1-methoxyethyl)-7-methylquinoxaline (184);
2-(2-(difluoro(methoxy)methyl)-7-methylquinoxalin-5-yl)-6-methoxy-4-methylbenzo[d]thiazole (186);
6-methoxy-4-methyl-2-(7-methyl-2-(phenoxymethyl)quinoxalin-5-yl)benzo[d]thiazole (187);
1-(5-(6-methoxy-4-methylbenzo[d]thiazol-2-yl)-7-methylquinoxalin-2-yl)—N,N-dimethylmethanamine (188);
2-(2-(ethoxymethyl)-7-methylquinoxalin-5-yl)-6-methoxy-4-methylbenzo[d]thiazole (189);
5-chloro-2-(2-(methoxymethyl)-7-methylquinoxalin-5-yl)-7-methylthiazolo[5,4-b] pyridine (191);
(5-methoxy-2-(2-(methoxymethyl)-7-methylquinoxalin-5-yl)thiazolo[5,4-b]pyridin-7-yl) methanol (192);
4-fluoro-N-(2-((2-(2-(methoxymethyl)-7-methylquinoxalin-5-yl)-7-methylthiazolo[5,4-b]pyridine-5-yl)oxy)ethyl) benzenesulfonamide (193);
4-fluoro-N-(2-((2-(2-methoxy-7-methylquinoxalin-5-yl)-7-methylthiazolo[5,4-b]pyridine-5-yl)oxy)ethyl)benzenesulfonamide (194);
5-(benzofuran-2-yl)-2-(methoxymethyl)-7-methylquinoxaline (195);
2-((2-(2-methoxy-7-methylquinoxalin-5-yl)-7-methylthiazolo[5,4-b]pyridin-5-yl)oxy)ethyl pyridin-3-ylcarbamate (196);
2-((2-(2-methoxy-7-methylquinoxalin-5-yl)-7-methylthiazolo[5,4-b]pyridin-5-yl)oxy)ethyl (6-cyanopyridin-3-yl)carbamate (197);
2-((6-fluoro-2-(2-methoxy-7-methylquinoxalin-5-yl)thiazolo[5,4-b]pyridin-5-yl)oxy)ethyl (6-cyanopyridin-3-yl)carbamate (198);
N-(2-((2-(7-chloro-2-methoxyquinoxalin-5-yl)-4-methylbenzo[d]thiazol-6-yl)oxy) ethyl)-4-fluorobenzenesulfonamide (199);
N-(2-((2-(7-chloro-2-(methoxymethyl) quinoxalin-5-yl)-4-methylbenzo[d]thiazol-6-yl)oxy)ethyl)-4-fluorobenzenesulfonamide (200);
2-(7-chloro-2-(methoxymethyl)quinoxalin-5-yl)-6-methoxybenzo[d]thiazole (201);
2-(7-chloro-2-(methoxymethyl)quinoxalin-5-yl)-6-methoxybenzo[d]thiazole (202);
6-methoxy-2-(2-(methoxymethyl)-7-(trifluoromethoxy)quinoxalin-5-yl)-4-methylbenzo[d] thiazole (203);
methyl 8-(6-methoxy-4-methylbenzo[d]thiazol-2-yl)-3-(methoxymethyl) quinoxaline-6-carboxylate (204);
methyl 8-(6-(2-(4-fluorophenylsulfonamido)ethoxy)-4-methylbenzo[d]thiazol-2-yl)-3-(methoxymethyl)quinoxaline-6-carboxylate (205);
2-(7-fluoro-2-(methoxymethyl)quinoxalin-5-yl)-6-methoxy-4-methylbenzo[d]thiazole (206);
4-fluoro-N-(2-((2-(7-fluoro-2-(methoxymethyl)quinoxalin-5-yl)-4-methylbenzo[d]thiazol-6-yl)oxy)ethyl)benzenesulfonamide (207);
6-methoxy-2-(2-(methoxymethyl)-7-(trifluoromethyl)quinoxalin-5-yl)-4-methylbenzo[d]thiazole (208);
4-fluoro-N-(2-((2-(2-(methoxymethyl)-7-(trifluoromethyl)quinoxalin-5-yl)-4-methylbenzo[d]thiazol-6-yl)oxy) ethyl)benzenesulfonamide (209);
4-chloro-2-(7-chloro-2-(methoxymethyl) quinoxalin-5-yl)-6-methoxybenzo[d]thiazole (210);
3-methoxy-8-(6-methoxy-4-methylbenzo[d] thiazol-2-yl)quinoxaline-6-carbonitrile (211);
4-chloro-6-methoxy-2-(2-(methoxymethyl) quinoxalin-5-yl)benzo[d]thiazole (212);
4-fluoro-N-(2-((2-(2-(methoxymethyl) quinoxalin-5-yl)-4-methylbenzo[d]thiazol-6-yl)oxy)ethyl) benzenesulfonamide (213);

2-(7-chloro-2-methoxyquinoxalin-5-yl)-4,5-difluoro-6-methoxybenzo[d]thiazole (214);

4-chloro-2-(7-chloro-2-methoxyquinoxalin-5-yl)-5-fluoro-6-methoxybenzo[d]thiazole (215);

4-chloro-5-fluoro-6-methoxy-2-(2-methoxy-6,7-dimethylquinoxalin-5-yl)benzo[d] thiazole (216);

8-(4,5-difluoro-6-methoxybenzo[d] thiazol-2-yl)-3-methoxyquinoxaline-6-carbonitrile (217);

(8-(4-chloro-5-fluoro-6-methoxybenzo[d]thiazol-2-yl)-3-methoxyquinoxalin-6-yl)methanol (218);

(3-methoxy-8-(6-methoxy-4,5-dimethylbenzo [d]thiazol-2-yl)quinoxalin-6-yl)methanol (219);

(8-(4,5-difluoro-6-methoxybenzo[d] thiazol-2-yl)-3-methoxyquinoxalin-6-yl)methanol (220);

8-(5-fluoro-6-methoxybenzo[d] thiazol-2-yl)-3-methoxyquinoxaline-6-carbonitrile (221);

(8-(5-fluoro-6-methoxybenzo [d]thiazol-2-yl)-3-methoxyquinoxalin-6-yl)methanol (222);

(3-methoxy-8-(5-methoxy-7-methylthiazolo[5,4-b]pyridin-2-yl)quinoxalin-6-yl)methanol (223);

(8-(4-chloro-5-fluoro-6-methoxybenzo[d]thiazol-2-yl)-5-fluoro-3-methoxyquinoxalin-6-yl)methanol (224);

8-(6-(2-(4-fluorophenylsulfonamido)ethoxy)-4-methylbenzo[d]thiazol-2-yl)-3-(methoxymethyl)quinoxaline-6-carboxamide (225);

8-(6-(2-(4-fluorophenylsulfonamido) ethoxy)-4-methylbenzo[d]thiazol-2-yl)-3-(methoxymethyl)—N,N-dimethylquinoxaline-6-carb oxamide (226);

4-fluoro-N-(2-((2-(2-(methoxymethyl)-7-(piperidine-1-carbonyl) quinoxalin-5-yl)-4-methylbenzo[d]thiazol-6-yl)oxy)ethyl)benzenesulfonamide (227);

8-(6-(2-(4-fluorophenylsulfonamido)ethoxy)-4-methylbenzo[d]thiazol-2-yl)—N-(2-methoxyethyl)-3-(methoxymethyl)quinoxaline-6-carboxamide (228);

4-fluoro-N-(2-((2-(2-methoxy-7-vinylquinoxalin-5-yl)-4-methylbenzo[d]thiazol-6-yl)oxy)ethyl) benzenesulfonamide (229);

N-(2-((2-(7-ethynyl-2-methoxyquinoxalin-5-yl)-4-methylbenzo[d]thiazol-6-yl)oxy)ethyl)-4-fluorobenzenesulfonamide (230);

N-(2-((2-(7-cyano-2-methoxyquinoxalin-5-yl)-4-methylbenzo[d]thiazol-6-yl)oxy)ethyl)-4-fluorobenzenesulfonamide (231);

N-(2-((2-(7-cyano-2-(methoxymethyl)quinoxalin-5-yl)-4-methylbenzo[d]thiazol-6-yl) oxy)ethyl)-4-fluorobenzenesulfonamide (232);

8-(6-methoxy-4-methylbenzo[d]thiazol-2-yl)-3-(methoxymethyl)quinoxaline-6-carbonitrile (233);

4-fluoro-N-(2-((2-(2-(methoxymethyl)-7-vinylquinoxalin-5-yl)-4-methylbenzo[d]thiazol-6-yl)oxy)ethyl) benzenesulfonamide (234);

4-fluoro-N-(2-((2-(7-(hydroxymethyl)-2-methoxyquinoxalin-5-yl)-4-methylbenzo[d]thiazol-6-yl)oxy)ethyl) benzenesulfonamide (235);

N-(2-((2-(7-(1,2-dihydroxyethyl)-2-methoxyquinoxalin-5-yl)-4-methylbenzo[d]thiazol-6-yl)oxy) ethyl)-4-fluorobenzenesulfonamide (236);

4-fluoro-N-(2-((2-(7-(2-hydroxyethyl)-2-methoxyquinoxalin-5-yl)-4-methylbenzo[d]thiazol-6-yl)oxy)ethyl) benzenesulfonamide (237);

N-(2-((2-(7-(aminomethyl)-2-methoxyquinoxalin-5-yl)-4-methylbenzo[d]thiazol-6-yl)oxy)ethyl)-4-fluorobenzenesulfonamide (238);

4-fluoro-N-(2-((2-(7-(1-hydroxyethyl)-2-methoxyquinoxalin-5-yl)-4-methylbenzo[d]thiazol-6-yl)oxy)ethyl)benzenesulfonamide (239);

4-fluoro-N-(2-((2-(7-(hydroxy(phenyl)methyl)-2-methoxyquinoxalin-5-yl)-4-methylbenzo[d]thiazol-6-yl)oxy)ethyl)benzenesulfonamide (240);

4-fluoro-N-(2-((2-(2-methoxy-7-(prop-1-en-2-yl)quinoxalin-5-yl)-4-methylbenzo [d]thiazol-6-yl)oxy) ethyl) benzenesulfonamide (241);

4-fluoro-N-(2-((2-(7-(2-hydroxypropan-2-yl)-2-methoxyquinoxalin-5-yl)-4-methylbenzo[d]thiazol-6-yl)oxy) ethyl)benzenesulfonamide (242);

(8-(5-fluoro-6-methoxy-4-methylbenzo[d]thiazol-2-yl)-3-methoxyquinoxalin-6-yl) methanol (243);

1-(8-(5-fluoro-6-methoxy-4-methylbenzo[d] thiazol-2-yl)-3-methoxyquinoxalin-6-yl) ethanol (244);

(8-(5-fluoro-6-methoxy-4-methylbenzo[d] thiazol-2-yl)-3-methoxyquinoxalin-6-yl) (phenyl)methanol (245);

cyclopropyl(8-(5-fluoro-6-methoxy-4-methylbenzo[d] thiazol-2-yl)-3-methoxyquinoxalin-6-yl)methanol (246);

4-fluoro-N-(2-((2-(7-fluoro-2-methylquinoxalin-5-yl)-4-methylbenzo[d]thiazol-6-yl) oxy)ethyl)benzenesulfonamide (247);

(8-(5-fluoro-6-isopropoxybenzo[d]thiazol-2-yl)-3-methoxyquinoxalin-6-yl)methanol (248);

N-(2-((2-(7-chloro-2-methoxyquinoxalin-5-yl)-4-methylbenzo[d]thiazol-6-yl)oxy) ethyl)pyridine-3-sulfonamide (249);

ethyl 2-((2-(7-chloro-2-methoxyquinoxalin-5-yl)-4-methylbenzo[d] thiazol-6-yl)oxy) acetate (250);

2-((2-(7-chloro-2-methoxyquinoxalin-5-yl)-4-methylbenzo[d]thiazol-6-yl)oxy)acetic acid (251);

2-((2-(7-(hydroxymethyl)-2-methoxyquinoxalin-5-yl)-4-methylbenzo[d]thiazol-6-yl)oxy)ethyl (6-methoxypyridin-3-yl)carbamate (252);

6-methoxy-2-(2-(methoxymethyl)-7-methylquinoxalin-5yl)benzo[d] thiazole (253);

4-fluoro-6-methoxy-2-(2-(methoxymethyl)-7-methylquinoxalin-5-yl) benzo[d]thiazole (254);

6-ethoxy-2-(2-(methoxymethyl)-7-methylquinoxalin-5-yl)benzo [d]thiazole (255);

2-(2-(methoxymethyl)-7-methylquinoxalin-5-yl)benzo[d] thiazole (256);

4,6-difluoro-2-(2-(methoxymethyl)-7-methylquinoxalin-5-yl)benzo[d]thiazole (257);

4,6-dimethoxy-2-(2-(methoxymethyl)-7-methylquinoxalin-5-yl)benzo[d]thiazole (258);

4-methoxy-2-(2-(methoxymethyl)-7-methylquinoxalin-5-yl)benzo[d]thiazole (259);

4-chloro-2-(2-(methoxymethyl)-7-methylquinoxalin-5-yl)benzo[d]thiazole (260);

2-(2-(methoxymethyl)-7-methylquinoxalin-5-yl)-4-methylbenzo[d]thiazole (261);

2-(2-(methoxymethyl)-7-methylquinoxalin-5-yl)-4-methyl-6-(trifluoromethoxy)benzo[d] thiazole (262);

6-(difluoromethoxy)-2-(2-(methoxymethyl)-7-methylquinoxalin-5-yl)-4-methylbenzo[d]thiazole (263);

methyl 2-(2-(methoxymethyl)-7-methylquinoxalin-5-yl)-4-methylbenzo[d]thiazole-6-carboxylate (264);

4-chloro-7-fluoro-6-methoxy-2-(2-(methoxymethyl)-7-methylquinoxalin-5-yl)benzo[d]thiazole (265);

4-chloro-6-fluoro-2-(2-(methoxymethyl)-7-methylquinoxalin-5-yl)benzo[d]thiazole (266);

4,5-difluoro-6-methoxy-2-(2-(methoxymethyl)-7-methylquinoxalin-5-yl)benzo[d]thiazole (267);

5-chloro-6-methoxy-2-(2-(methoxymethyl)-7-methylquinoxalin-5-yl)benzo[d]thiazole (268);

5,6-difluoro-4-methoxy-2-(2-(methoxymethyl)-7-methylquinoxalin-5-yl)benzo [d]thiazole (269);

6-fluoro-4-methoxy-2-(2-(methoxymethyl)-7-methylquinoxalin-5-yl)benzo[d]thiazole (270);
5-fluoro-4,6-dimethoxy-2-(2-(methoxymethyl)-7-methylquinoxalin-5-yl)benzo[d]thiazole (271);
6-fluoro-2-(2-(methoxymethyl)-7-methylquinoxalin-5-yl)benzo[d]thiazole (272);
4-fluoro-2-(2-(methoxymethyl)-7-methylquinoxalin-5-yl)benzo[d]thiazole (273);
6-chloro-2-(2-(methoxymethyl)-7-methylquinoxalin-5-yl)benzo[d]thiazole (274);
4,6-dichloro-2-(2-(methoxymethyl)-7-methylquinoxalin-5-yl)benzo[d]thiazole (275);
6-methoxy-2-(2-(methoxymethyl)-7-methylquinoxalin-5-yl)-5-methylbenzo[d]thiazole (276);
5-fluoro-6-methoxy-2-(2-(methoxymethyl)-7-methylquinoxalin-5-yl)benzo[d]thiazole (277);
4,5-difluoro-6-methoxy-2-(2-methoxy-7-methylquinoxalin-5-yl)benzo[d]thiazole (278);
6-methoxy-2-(2-methoxy-7-methylquinoxalin-5-yl)-5-methylbenzo[d]thiazole (279);
5-fluoro-6-methoxy-2-(2-methoxy-7-methylquinoxalin-5-yl)benzo[d]thiazole (280);
2-(2-(methoxymethyl)-7-methylquinoxalin-5-yl)-4-methylbenzo[d]thiazol-6-ol (281);
4-chloro-5-fluoro-6-methoxy-2-(2-methoxy-7-methylquinoxalin-5-yl)benzo[d]thiazole (282);
4-chloro-5-fluoro-6-methoxy-2-(2-(methoxymethyl)-7-methylquinoxalin-5-yl)benzo[d]thiazole (283);
6-methoxy-2-(2-(methoxymethyl)-7-methylquinoxalin-5-yl)-4,5-dimethylbenzo[d]thiazole (284);
methyl 2-((5-fluoro-2-(2-methoxy-7-methylquinoxalin-5-yl)-4-methylbenzo[d]thiazol-6-yl)oxy)acetate (285);
methyl 2-((5-fluoro-2-(2-(methoxymethyl)-7-methylquinoxalin-5-yl)-4-methylbenzo[d]thiazol-6-yl) oxy)acetate (286);
methyl 2-((4-chloro-5-fluoro-2-(2-methoxy-7-methylquinoxalin-5-yl) benzo[d]thiazol-6-yl)oxy)acetate (287);
2-((5-fluoro-2-(2-methoxy-7-methylquinoxalin-5-yl)-4-methylbenzo[d]thiazol-6-yl)oxy)ethanol (288);
2-((5-fluoro-2-(2-(methoxymethyl)-7-methylquinoxalin-5-yl)-4-methylbenzo[d]thiazol-6-yl)oxy)ethanol (289);
5-fluoro-2-(2-(methoxymethyl)-7-methylquinoxalin-5-yl)-4-methylbenzo[d] thiazol-6-ol (290);
4-chloro-5-fluoro-2-(2-(methoxymethyl)-7-methylquinoxalin-5-yl) benzo[d]thiazol-6-ol (291);
methyl 2-((4-chloro-5-fluoro-2-(2-(methoxymethyl)-7-methylquinoxalin-5-yl)benzo[d]thiazol-6-yl)oxy)acetate (292);
2-((4-chloro-5-fluoro-2-(2-(methoxymethyl)-7-methylquinoxalin-5-yl)benzo[d]thiazol-6-yl)oxy)ethanol (293);
5-fluoro-6-methoxy-2-(2-methoxy-7-methylquinoxalin-5-yl)-4-methylbenzo[d]thiazole (294);
5-fluoro-6-methoxy-2-(2-(methoxymethyl)-7-methylquinoxalin-5-yl)-4-methylbenzo[d]thiazole (295);
methyl 2-((2-(2-(methoxymethyl)-7-methylquinoxalin-5-yl)-4,5-dimethylbenzo[d]thiazol-6-yl)oxy)acetate (296);
2-((2-(2-(methoxymethyl)-7-methylquinoxalin-5-yl)-4,5-dimethylbenzo[d]thiazol-6-yl)oxy)ethanol (297);
4-chloro-6-methoxy-2-(2-(methoxymethyl)-7-methylquinoxalin-5-yl)-5-methylbenzo[d]thiazole (298);
4-chloro-6-methoxy-2-(2-methoxy-7-methylquinoxalin-5-yl)-5-methylbenzo[d] thiazole (299);
(6-methoxy-2-(2-(methoxymethyl)-7-methylquinoxalin-5-yl)-5-methylbenzo[d]thiazol-4-yl)methanol (300);
(6-methoxy-2-(2-(methoxymethyl)-7-methylquinoxalin-5-yl)-5-methylbenzo[d]thiazol-4-yl)methanol (301);
2-((5-fluoro-2-(2-methoxy-7-methylquinoxalin-5-yl)-4-methylbenzo[d]thiazol-6-yl)oxy)ethyl (6-fluoropyridin-3-yl)carbamate (302);
2-((5-fluoro-2-(2-(methoxymethyl)-7-methylquinoxalin-5-yl)-4-methylbenzo[d]thiazol-6-yl)oxy)ethyl (6-fluoropyridin-3-yl) carbamate (303);
2-((4-chloro-5-fluoro-2-(2-methoxy-7-methylquinoxalin-5-yl)benzo[d] thiazol-6-yl)oxy)ethyl (6-fluoropyridin-3-yl)carbamate (304);
2-((4-chloro-5-fluoro-2-(2-(methoxymethyl)-7-methylquinoxalin-5-yl)benzo[d]thiazol-6-yl)oxy)ethyl(6-fluoropyridin-3-yl)carbamate (305);
2-(2-(methoxymethyl)-7-methylquinoxalin-5-yl)-4-methylbenzo[d]thiazol-6-ol (306);
6-(benzyloxy)-2-(2-(methoxymethyl)-7-methylquinoxalin-5-yl)-4-methylbenzo[d]thiazole (307);
(2-(2-(methoxymethyl)-7-methylquinoxalin-5-yl)benzo[d]thiazol-6-yl)methanol (308);
6-(methoxymethyl)-2-(2-(methoxymethyl)-7-methylquinoxalin-5-yl)benzo[d]thiazole (309);
6-methoxy-2-(2-(methoxymethyl)-7-methylquinoxalin-5-yl)benzo[d]thiazol-5-ol (310);
5,6-dimethoxy-2-(2-(methoxymethyl)-7-methylquinoxalin-5-yl)benzo[d]thiazole (311);
(6-methoxy-2-(2-(methoxymethyl)-7-methylquinoxalin-5-yl)benzo[d]thiazol-5-yl) methanol (312);
6-chloro-5-fluoro-4-methoxy-2-(2-(methoxymethyl)-7-methylquinoxalin-5-yl) benzo[d] thiazole (313);
4-cyclopropyl-5-fluoro-6-methoxy-2-(2-(methoxymethyl)-7-methylquinoxalin-5-yl)benzo[d]thiazole (314);
6-ethoxy-4,5-difluoro-2-(2-methoxy-7-methylquinoxalin-5-yl)benzo[d]thiazole (315);
N-(2-((4,5-difluoro-2-(2-methoxy-7-methylquinoxalin-5-yl)benzo[d]thiazol-6-yl) oxy)ethyl)-3-fluorobenzenesulfonamide (316);
N-(2-((4,5-difluoro-2-(2-(methoxymethyl)-7-methylquinoxalin-5-yl)benzo[d]thiazol-6-yl)oxy)ethyl)-3-fluorobenzenesulfonamide (317);
2-((4-chloro-5-fluoro-2-(2-methoxy-7-methylquinoxalin-5-yl)benzo[d]thiazol-6-yl)oxy)ethanol (318);
1-((2-(2-(methoxymethyl)-7-methylquinoxalin-5-yl)-4,5-dimethylbenzo[d]thiazol-6-yl)oxy)-2-methylpropan-2-ol (319);
2-((2-(2-(methoxymethyl)-7-methylquinoxalin-5-yl)-4,5-dimethylbenzo[d]thiazol-6-yl) oxy)ethyl methyl carbonate (320);
2-((2-(2-(methoxymethyl)-7-methylquinoxalin-5-yl)-4,5-dimethylbenzo[d]thiazol-6-yl)oxy) propan-1-ol (racemate) (321);
1-((2-(2-(methoxymethyl)-7-methylquinoxalin-5-yl)-4,5-dimethylbenzo[d]thiazol-6-yl) oxy)propan-2-ol (racemate) (322);
3-((2-(2-(methoxymethyl)-7-methylquinoxalin-5-yl)-4,5-dimethylbenzo[d]thiazol-6-yl)oxy)butan-2-ol (diastereomeric) (323);
2-((4-chloro-5-fluoro-2-(2-methoxy-7-methylquinoxalin-5-yl)benzo[d]thiazol-6-yl)oxy)-1-morpholinoethanone (324);
(6-methoxy-2-(2-methoxy-7-methylquinoxalin-5-yl)-5-methylbenzo[d]thiazol-4-yl) methanol (bis-deuterated) (325);
1-(6-methoxy-2-(2-(methoxymethyl)-7-methylquinoxalin-5-yl)-5-methylbenzo[d]thiazol-4-yl)ethanol (326);

2-((4-chloro-2-(2-(methoxymethyl)-7-methylquinoxalin-5-yl)-5-methylbenzo[d]thiazol-6-yl)oxy)ethanol (327);

1-(6-methoxy-2-(2-(methoxymethyl)-7-methylquinoxalin-5-yl)-5-methylbenzo[d]thiazol-4-yl)-2,2-dimethylpropan-1-ol (racemate) (328);

5-fluoro-6-isopropoxy-2-(2-(methoxymethyl)-7-methylquinoxalin-5-yl) benzo[d]thiazole (329);

N-(2-((4-chloro-5-fluoro-2-(2-methoxy-7-methylquinoxalin-5-yl) benzo[d]thiazol-6-yl)oxy)ethyl)benzenesulfonamide (330);

2-((4-chloro-5-fluoro-2-(2-methoxy-7-methylquinoxalin-5-yl)benzo[d]thiazol-6-yl) oxy)ethyl pyridin-3-ylcarbamate (331);

2-((4-chloro-5-fluoro-2-(2-methoxy-7-methylquinoxalin-5-yl)benzo[d]thiazol-6-yl)oxy)ethyl (6-methoxypyridin-3-yl)carbamate (332);

2-((4-chloro-5-fluoro-2-(2-methoxy-7-methylquinoxalin-5-yl)benzo[d]thiazol-6-yl)oxy)ethyl (2-oxo-2,3-dihydrobenzo[d]oxazol-6-yl)carbamate (333);

2-((4-chloro-5-fluoro-2-(2-methoxy-7-methylquinoxalin-5-yl)benzo[d]thiazol-6-yl)oxy)ethyl (2,2,2-trifluoroethyl)carbamate (334);

2-((4-chloro-5-fluoro-2-(2-methoxy-7-methylquinoxalin-5-yl)benzo[d]thiazol-6-yl)oxy)ethyl pyridin-4-ylcarbamate (335);

2-((4-chloro-5-fluoro-2-(2-methoxy-7-methylquinoxalin-5-yl)benzo[d]thiazol-6-yl)oxy)ethyl (2-methylpyridin-4-yl)carbamate (336);

2-((4-chloro-5-fluoro-2-(2-methoxy-7-methylquinoxalin-5-yl)benzo[d]thiazol-6-yl)oxy)ethyl (5-fluoropyridin-3-yl)carbamate (337);

2-((4-chloro-5-fluoro-2-(2-methoxy-7-methylquinoxalin-5-yl)benzo[d]thiazol-6-yl)oxy)ethyl (6-(3-methyl-1H-1,2,4-triazol-1-yl)pyridin-3-yl)carbamate (338);

2-((5-fluoro-2-(2-methoxy-7-methylquinoxalin-5-yl) benzo[d]thiazol-6-yl)oxy)ethyl pyridin-3-ylcarbamate (339);

2-((5-fluoro-2-(2-methoxy-7-methylquinoxalin-5-yl) benzo[d]thiazol-6-yl)oxy)ethyl (6-fluoropyridin-3-yl) carbamate (340);

2-((5-fluoro-2-(2-methoxy-7-methylquinoxalin-5-yl) benzo[d]thiazol-6-yl)oxy) ethyl (6-methoxypyridin-3-yl)carbamate (341);

2-((5-fluoro-2-(2-methoxy-7-methylquinoxalin-5-yl) benzo[d]thiazol-6-yl)oxy)ethyl pyridin-4-ylcarbamate (342);

2-((5-fluoro-2-(2-methoxy-7-methylquinoxalin-5-yl) benzo[d]thiazol-6-yl)oxy)ethyl (2-oxo-2,3-dihydrobenzo[d]oxazol-6-yl)carbamate (343);

(R)-2-((5-fluoro-2-(2-methoxy-7-methylquinoxalin-5-yl) benzo[d]thiazol-6-yl)oxy)propyl pyridin-3-ylcarbamate (344);

(S)-2-((5-fluoro-2-(2-methoxy-7-methylquinoxalin-5-yl) benzo[d]thiazol-6-yl)oxy)propyl pyridin-3-ylcarbamate (345);

(S)-1-((5-fluoro-2-(2-methoxy-7-methylquinoxalin-5-yl) benzo[d]thiazol-6-yl)oxy)propan-2-yl pyridin-3-ylcarbamate (346);

(R)-1-((5-fluoro-2-(2-methoxy-7-methylquinoxalin-5-yl) benzo[d]thiazol-6-yl)oxy)propan-2-yl pyridin-3-ylcarbamate (347);

(R)-1-((5-fluoro-2-(2-methoxy-7-methylquinoxalin-5-yl) benzo[d] thiazol-6-yl)oxy)propan-2-yl (6-fluoropyridin-3-yl)carbamate (348);

(R)-1-((5-fluoro-2-(2-methoxy-7-methylquinoxalin-5-yl) benzo[d]thiazol-6-yl)oxy)propan-2-yl pyridin-4-ylcarbamate (349);

(R)-1-((5-fluoro-2-(2-methoxy-7-methylquinoxalin-5-yl) benzo[d] thiazol-6-yl)oxy)propan-2-yl (2-oxo-2,3-dihydrobenzo[d]oxazol-6-yl)carbamate (350);

(R)-1-((5-fluoro-2-(2-methoxy-7-methylquinoxalin-5-yl) benzo[d]thiazol-6-yl)oxy) propan-2-yl (6-cyanopyridin-3-yl)carbamate (351);

(R)-1-((5-fluoro-2-(2-methoxy-7-methylquinoxalin-5-yl) benzo[d]thiazol-6-yl)oxy)propan-2-yl (3-amino-3-oxopropyl) carbamate (352);

(R)-1-((5-fluoro-2-(2-methoxy-7-methylquinoxalin-5-yl) benzo[d] thiazol-6-yl)oxy)propan-2-yl pyridazin-4-ylcarbamate (353);

(R)-1-((5-fluoro-2-(2-methoxy-7-methylquinoxalin-5-yl) benzo[d]thiazol-6-yl)oxy)propan-2-yl 1H-pyrrolo[2,3-b]pyridin-5-ylcarbamate (354);

(R)-1-((5-fluoro-2-(2-methoxy-7-methylquinoxalin-5-yl) benzo[d]thiazol-6-yl)oxy)propan-2-yl 1H-indol-5-ylcarbamate (355);

(R)-1-((5-fluoro-2-(2-methoxy-7-methylquinoxalin-5-yl) benzo[d]thiazol-6-yl)oxy)propan-2-yl (1-methyl-1H-indol-5-yl)carbamate (356);

(R)-1-((5-fluoro-2-(2-methoxy-7-methylquinoxalin-5-yl) benzo[d]thiazol-6-yl)oxy)propan-2-yl (2-methylpyrimidin-5-yl)carbamate (357);

2-((4-chloro-5-fluoro-2-(2-methoxy-7-methylquinoxalin-5-yl)benzo[d]thiazol-6-yl)oxy) ethyl carbamate (358);

2-((4-chloro-5-fluoro-2-(2-methoxy-7-methylquinoxalin-5-yl) benzo[d]thiazol-6-yl)oxy)ethyl 1H-pyrrolo[2,3-b]pyridin-5-ylcarbamate (359);

2-((4-chloro-5-fluoro-2-(2-methoxy-7-methylquinoxalin-5-yl)benzo[d]thiazol-6-yl)oxy)ethyl 1H-indol-5-ylcarbamate (360);

methyl 5-(((2-((4-chloro-5-fluoro-2-(2-methoxy-7-methylquinoxalin-5-yl)benzo[d]thiazol-6-yl)oxy)ethoxy) carbonyl)amino)picolinate (361);

2-((4-chloro-5-fluoro-2-(2-methoxy-7-methylquinoxalin-5-yl)benzo[d]thiazol-6-yl)oxy)ethyl (2-methylpyrimidin-5-yl)carbamate (362);

2-((4-chloro-5-fluoro-2-(2-methoxy-7-methylquinoxalin-5-yl)benzo[d]thiazol-6-yl)oxy)ethyl (5-methoxy-1,2,4-thiadiazol-3-yl)carbamate (363);

2-((4-chloro-5-fluoro-2-(2-methoxy-7-methylquinoxalin-5-yl)benzo[d]thiazol-6-yl)oxy)ethyl 1H-pyrazol-4-ylcarbamate (364);

2-((4-chloro-5-fluoro-2-(2-methoxy-7-methylquinoxalin-5-yl)benzo[d]thiazol-6-yl)oxy) ethyl (1-methyl-1H-pyrazol-4-yl)carbamate (365);

2-((4-chloro-5-fluoro-2-(2-methoxy-7-methylquinoxalin-5-yl)benzo[d]thiazol-6-yl)oxy)ethyl (5-methyl-1,3,4-oxadiazol-2-yl) carbamate (366);

2-((4-chloro-5-fluoro-2-(2-methoxy-7-methylquinoxalin-5-yl)benzo[d] thiazol-6-yl)oxy)ethyl (1,2-dimethyl-1H-pyrrolo[2,3-b]pyridin-5-yl)carbamate (367);

2-((4-chloro-5-fluoro-2-(2-methoxy-7-methylquinoxalin-5-yl)benzo[d]thiazol-6-yl)oxy) ethyl (pyridin-3-ylmethyl)carbamate (368);

2-((4-chloro-5-fluoro-2-(2-methoxy-7-methylquinoxalin-5-yl)benzo[d]thiazol-6-yl)oxy)ethyl (pyridin-4-ylmethyl)carbamate (369);

(R)-1-((4-chloro-5-fluoro-2-(2-methoxy-7-methylquinoxalin-5-yl)benzo[d]thiazol-6-yl)oxy)propan-2-yl (5-methyl-1,3,4-thiadiazol-2-yl)carbamate (370);

(R)-1-((4-chloro-5-fluoro-2-(2-methoxy-7-methylquinoxalin-5-yl)benzo[d]thiazol-6-yl)oxy)propan-2-yl (6-cyanopyridin-3-yl)carbamate (371);

(R)-1-((4-chloro-5-fluoro-2-(2-methoxy-7-methylquinoxalin-5-yl)benzo[d]thiazol-6-yl)oxy)propan-2-yl pyridin-3-ylcarbamate (372);
(R)-1-((4-chloro-5-fluoro-2-(2-methoxy-7-methylquinoxalin-5-yl)benzo[d]thiazol-6-yl)oxy)propan-2-yl (2-oxo-2,3-dihydrobenzo[d]oxazol-6-yl)carbamate (373);
(R)-1-((4-chloro-5-fluoro-2-(2-methoxy-7-methylquinoxalin-5-yl)benzo[d]thiazol-6-yl)oxy)propan-2-yl (6-(trifluoromethyl)pyridin-3-yl)carbamate (374);
(R)-1-((4-chloro-5-fluoro-2-(2-methoxy-7-methylquinoxalin-5-yl)benzo[d]thiazol-6-yl)oxy)propan-2-yl 3H-pyrrolo [2,3-b]pyridin-5-ylcarbamate (375);
(R)-1-((4-chloro-5-fluoro-2-(2-methoxy-7-methylquinoxalin-5-yl)benzo[d]thiazol-6-yl)oxy)propan-2-yl (4-methylpyridin-3-yl) carbamate (376);
(R)-1-((4-chloro-5-fluoro-2-(2-methoxy-7-methylquinoxalin-5-yl) benzo[d]thiazol-6-yl)oxy)propan-2-yl (6-methylpyridin-3-yl)carbamate (377);
methyl 4-(((2-((4-chloro-5-fluoro-2-(2-methoxy-7-methylquinoxalin-5-yl)benzo[d]thiazol-6-yl) oxy)ethoxy)carbonyl)amino)-1-methyl-1H-pyrrole-2-carboxylate (378);
1-((5-fluoro-2-(2-methoxy-7-methylquinoxalin-5-yl) benzo[d]thiazol-6-yl)oxy)-3-isobutoxypropan-2-yl pyridin-3-ylcarbamate (379);
1-(benzyloxy)-3-((5-fluoro-2-(2-methoxy-7-methylquinoxalin-5-yl)benzo[d]thiazol-6-yl)oxy)propan-2-yl pyridin-3-ylcarbamate (380);
2-((4-chloro-5-fluoro-2-(2-methoxy-7-methylquinoxalin-5-yl)benzo[d]thiazol-6-yl)oxy)propyl (6-methoxypyridin-3-yl)carbamate (racemate) (381);
(S)-2-((4-chloro-5-fluoro-2-(2-methoxy-7-methylquinoxalin-5-yl)benzo[d]thiazol-6-yl)oxy)propyl (6-methoxypyridin-3-yl)carbamate (382);
2-((4-chloro-5-fluoro-2-(2-methoxy-7-methylquinoxalin-5-yl)benzo[d]thiazol-6-yl)oxy)ethyl (2-chlorothiazol-4-yl)carbamate (383);
2-((4-chloro-5-fluoro-2-(2-methoxy-7-methylquinoxalin-5-yl)benzo[d]thiazol-6-yl)oxy)ethyl thiazol-5-ylcarbamate (384);
(R)-1-((4-chloro-5-fluoro-2-(2-methoxy-7-methylquinoxalin-5-yl)benzo[d]thiazol-6-yl)oxy)propan-2-yl (6-(hydroxymethyl)pyridin-3-yl)carbamate (385);
(2R,3S)-3-((5-fluoro-2-(2-methoxy-7-methylquinoxalin-5-yl)benzo [d]thiazol-6-yl)oxy)butan-2-yl (2-methylpyrimidin-5-yl)carbamate (386);
(2R,3S)-3-((5-fluoro-2-(2-methoxy-7-methylquinoxalin-5-yl)benzo[d]thiazol-6-yl)oxy)butan-2-yl (6-(2-hydroxyethyl)pyridin-3-yl)carbamate (387);
(2R,3S)-3-((5-fluoro-2-(2-methoxy-7-methylquinoxalin-5-yl)benzo[d]thiazol-6-yl)oxy)butan-2-yl (2-(2-hydroxyethoxy) pyridin-4-yl)carbamate (388);
(2R,3S)-3-((2-(2-ethoxy-7-methylquinoxalin-5-yl)-5-fluorobenzo[d]thiazol-6-yl)oxy)butan-2-yl (2-methylpyrimidin-5-yl)carbamate (389);
(2R,3S)-3-((5-fluoro-2-(7-methyl-2-(methylamino)quinoxalin-5-yl)benzo[d]thiazol-6-yl)oxy)butan-2-yl (2-methylpyrimidin-5-yl)carbamate (390);
(2R,3S)-3-((5-fluoro-2-(2-methoxy-7-methylquinoxalin-5-yl)benzo[d]thiazol-6-yl)oxy)butan-2-yl (6-carbamoylpyridin-3-yl)carbamate (391);
(2R,3S)-3-((5-fluoro-2-(2-methoxy-7-methylquinoxalin-5-yl)benzo[d]thiazol-6-yl)oxy)butan-2-yl (6-((2-hydroxyethyl) carbamoyl)pyridin-3-yl)carbamate (392);
(2R,3S)-3-((5-fluoro-2-(7-methyl-2-(methylcarbamoyl) quinoxalin-5-yl)benzo[d]thiazol-6-yl)oxy)butan-2-yl (2-methylpyrimidin-5-yl)carbamate (393);
2-((4-chloro-5-fluoro-2-(2-methoxy-7-methylquinoxalin-5-yl)benzo[d]thiazol-6-yl)oxy)ethyl ((1-methyl-1H-imidazol-4-yl)methyl)carbamate (394);
2-((4-chloro-5-fluoro-2-(2-methoxy-7-methylquinoxalin-5-yl)benzo[d]thiazol-6-yl)oxy)ethyl (6-cyanopyridin-3-yl)carbamate (395);
2-((4-chloro-5-fluoro-2-(2-methoxy-7-methylquinoxalin-5-yl)benzo[d]thiazol-6-yl)oxy)ethyl (pyridin-2-ylmethyl)carbamate (396);
2-((4-chloro-5-fluoro-2-(2-methoxy-7-methylquinoxalin-5-yl)benzo[d]thiazol-6-yl)oxy)ethyl ((1-methyl-1H-imidazol-4-yl)methyl)carbamate (397);
2-((4-chloro-5-fluoro-2-(2-methoxy-7-methylquinoxalin-5-yl)benzo[d]thiazol-6-yl)oxy)ethyl ((1-methyl-1H-pyrazol-3-yl)methyl)carbamate (398);
2-((4-chloro-5-fluoro-2-(2-methoxy-7-methylquinoxalin-5-yl)benzo[d]thiazol-6-yl)oxy)ethyl ((1-methyl-1H-pyrazol-4-yl)methyl)carbamate (399);
(R)-1-((4-chloro-5-fluoro-2-(2-methoxy-7-methylquinoxalin-5-yl)benzo[d]thiazol-6-yl)oxy)propan-2-yl (2-cyanopyrimidin-5-yl)carbamate (400);
(R)-1-((4-chloro-5-fluoro-2-(2-methoxy-7-methylquinoxalin-5-yl)benzo[d]thiazol-6-yl)oxy)propan-2-yl (2-chloropyrimidin-5-yl)carbamate (401);
(R)-1-((4-chloro-5-fluoro-2-(2-methoxy-7-methylquinoxalin-5-yl)benzo[d]thiazol-6-yl)oxy)propan-2-yl (6-fluoro-5-methylpyridin-3-yl)carbamate (402);
(R)-1-((4-chloro-5-fluoro-2-(2-methoxy-7-methylquinoxalin-5-yl)benzo[d]thiazol-6-yl)oxy)propan-2-yl (6-bromopyridin-3-yl)carbamate (403);
(2R,3S)-3-((4-chloro-5-fluoro-2-(2-methoxy-7-methylquinoxalin-5-yl)benzo[d]thiazol-6-yl)oxy)butan-2-yl pyridin-3-ylcarbamate (404);
(2R,3S)-3-((5-fluoro-2-(2-methoxy-7-methylquinoxalin-5-yl)benzo[d]thiazol-6-yl)oxy)butan-2-yl (6-methylpyridin-3-yl)carbamate (405);
(2R,3S)-3-((5-fluoro-2-(2-methoxy-7-methylquinoxalin-5-yl)benzo[d]thiazol-6-yl)oxy)butan-2-yl (2-oxo-2,3-dihydrobenzo[d]oxazol-6-yl)carbamate (406);
(2R,3S)-3-((5-fluoro-2-(2-methoxy-7-methylquinoxalin-5-yl)benzo[d]thiazol-6-yl)oxy)butan-2-yl (2-methoxypyrimidin-5-yl)carbamate (407);
(R)-1-((5-fluoro-2-(2-methoxy-7-methylquinoxalin-5-yl) benzo[d]thiazol-6-yl)oxy)propan-2-yl (2-methoxypyrimidin-5-yl)carbamate (408);
(R)-1-((5-fluoro-2-(2-methoxy-7-methylquinoxalin-5-yl) benzo[d]thiazol-6-yl)oxy)propan-2-yl pyrimidin-5-ylcarbamate (409);
(2R,3S)-3-((5-fluoro-2-(2-methoxy-7-methylquinoxalin-5-yl)benzo[d]thiazol-6-yl)oxy)butan-2-yl pyrimidin-5-ylcarbamate (410);
(R)-1-((5-fluoro-2-(2-methoxy-7-methylquinoxalin-5-yl) benzo[d]thiazol-6-yl)oxy)propan-2-yl phenylcarbamate (411);
(2R,3S)-3-((5-fluoro-2-(2-methoxy-7-methylquinoxalin-5-yl)benzo[d]thiazol-6-yl)oxy)butan-2-yl (2-methoxypyridin-4-yl)carbamate (412);
(2R,3S)-3-((5-fluoro-2-(2-methoxy-7-methylquinoxalin-5-yl)benzo[d]thiazol-6-yl)oxy)butan-2-yl pyridazin-4-ylcarbamate (413);
(2R,3S)-3-((5-fluoro-2-(2-methoxy-7-methylquinoxalin-5-yl)benzo[d]thiazol-6-yl)oxy)butan-2-yl (2-propylpyrimidin-5-yl)carbamate (414);

(2R,3S)-3-((5-fluoro-2-(2-methoxy-7-methylquinoxalin-5-yl)benzo[d]thiazol-6-yl)oxy)butan-2-yl (2-(trifluoromethyl)pyrimidin-5-yl)carbamate (415);

(2R,3S)-3-((5-fluoro-2-(2-methoxy-7-methylquinoxalin-5-yl)benzo[d]thiazol-6-yl)oxy)butan-2-yl (6-methylpyridazin-3-yl)carbamate (416);

(2R,3S)-3-((5-fluoro-2-(2-methoxy-7-methylquinoxalin-5-yl)benzo[d]thiazol-6-yl)oxy)butan-2-yl (5-methylpyrazin-2-yl)carbamate (417);

(2R,3S)-3-((5-fluoro-2-(2-methoxy-7-methylquinoxalin-5-yl)benzo[d]thiazol-6-yl)oxy)butan-2-yl (6-methylpyridazin-4-yl)carbamate (418);

(2R,3S)-3-((5-fluoro-2-(2-methoxy-7-methylquinoxalin-5-yl)benzo[d]thiazol-6-yl)oxy)butan-2-yl (5-methylpyridin-3-yl)carbamate (419);

(2R,3S)-3-((5-fluoro-2-(2-methoxy-7-methylquinoxalin-5-yl)benzo[d]thiazol-6-yl)oxy)butan-2-yl (5-methoxypyridin-3-yl)carbamate (420);

(2R,3S)-3-((5-fluoro-2-(2-methoxy-7-methylquinoxalin-5-yl)benzo[d]thiazol-6-yl)oxy)butan-2-yl (5-cyanopyridin-3-yl)carbamate (421);

(2R,3S)-3-((5-fluoro-2-(2-methoxy-7-methylquinoxalin-5-yl)benzo[d]thiazol-6-yl)oxy)butan-2-yl (6-methoxy-5-methylpyridin-3-yl)carbamate (422);

(2R,3S)-3-((5-fluoro-2-(2-methoxy-7-methylquinoxalin-5-yl)benzo[d]thiazol-6-yl)oxy)butan-2-yl pyridin-3-ylcarbamate (423);

2-((5-fluoro-2-(2-methoxy-7-methylquinoxalin-5-yl)benzo[d]thiazol-6-yl)oxy)ethyl (2-methylpyrimidin-5-yl)carbamate (424);

(2R,3S)-3-((4-chloro-5-fluoro-2-(2-methoxy-7-methylquinoxalin-5-yl)benzo[d]thiazol-6-yl)oxy)butan-2-yl (2-methylpyrimidin-5-yl)carbamate (425);

(2R,3S)-3-((5-fluoro-2-(2-methoxy-7-methylquinoxalin-5-yl)benzo[d]thiazol-6-yl)oxy)butan-2-yl (6-(morpholine-4-carbonyl)pyridin-3-yl)carbamate (426);

(R)-1-((4-chloro-5-fluoro-2-(2-methoxy-7-methylquinoxalin-5-yl)benzo[d]thiazol-6-yl)oxy)propan-2-yl (2-carbamoylpyridin-4-yl)carbamate (427);

(R)-1-((4-chloro-5-fluoro-2-(2-methoxy-7-methylquinoxalin-5-yl)benzo[d]thiazol-6-yl)oxy)propan-2-yl (2-(methylcarbamoyl)pyridin-4-yl)carbamate (428);

(R)-1-((5-fluoro-2-(2-methoxy-7-methylquinoxalin-5-yl)benzo[d]thiazol-6-yl)oxy)propan-2-yl (2-carbamoylpyrimidin-5-yl)carbamate (429);

(R)-1-((5-fluoro-2-(2-methoxy-7-methylquinoxalin-5-yl)benzo[d]thiazol-6-yl)oxy)propan-2-yl (2-(methylcarbamoyl)pyrimidin-5-yl)carbamate (430);

(R)-1-((5-fluoro-2-(2-methoxy-7-methylquinoxalin-5-yl)benzo[d]thiazol-6-yl)oxy)propan-2-yl (2-(dimethylcarbamoyl)pyrimidin-5-yl)carbamate (431);

(R)-1-((5-fluoro-2-(2-methoxy-7-methylquinoxalin-5-yl)benzo[d]thiazol-6-yl)oxy)propan-2-yl (6-(methylcarbamoyl)pyridin-3-yl)carbamate (432);

(R)-1-((5-fluoro-2-(2-methoxy-7-methylquinoxalin-5-yl)benzo[d]thiazol-6-yl)oxy)propan-2-yl (6-carbamoylpyridin-3-yl)carbamate (433);

(R)-1-((5-fluoro-2-(2-methoxy-7-methylquinoxalin-5-yl)benzo[d]thiazol-6-yl)oxy)propan-2-yl (6-carbamoylpyridin-3-yl)carbamate (434);

(R)-1-((5-fluoro-2-(2-methoxy-7-methylquinoxalin-5-yl)benzo[d]thiazol-6-yl)oxy)propan-2-yl (6-(morpholine-4-carbonyl)pyridin-3-yl)carbamate (435);

(2R,3S)-3-((5-fluoro-2-(2-methoxy-7-methylquinoxalin-5-yl)benzo[d]thiazol-6-yl)oxy)butan-2-yl (6-(methylcarbamoyl)pyridin-3-yl)carbamate (436);

(2R,3S)-3-((5-fluoro-2-(2-methoxy-7-methylquinoxalin-5-yl)benzo[d]thiazol-6-yl)oxy)butan-2-yl (2-(morpholine-4-carbonyl)pyrimidin-5-yl)carbamate (437);

(2R,3S)-3-((5-fluoro-2-(2-methoxy-7-methylquinoxalin-5-yl)benzo[d]thiazol-6-yl)oxy)butan-2-yl (6-(dimethylcarbamoyl)pyridin-3-yl)carbamate (438);

(2R,3S)-3-((5-fluoro-2-(2-methoxy-7-methylquinoxalin-5-yl)benzo[d]thiazol-6-yl)oxy)butan-2-yl (6-(((R)-2-hydroxypropyl)carbamoyl)pyridin-3-yl)carbamate (439);

(2R,3S)-3-((5-fluoro-2-(2-methoxy-7-methylquinoxalin-5-yl)benzo[d]thiazol-6-yl)oxy)butan-2-yl (2-(methylcarbamoyl)pyrimidin-5-yl)carbamate (440);

(2R,3S)-3-((5-fluoro-2-(2-methoxy-7-methylquinoxalin-5-yl)benzo[d]thiazol-6-yl)oxy)butan-2-yl (6-(((S)-2-hydroxypropyl)carbamoyl)pyridin-3-yl)carbamate (441);

(R)-1-((5-fluoro-2-(2-methoxy-7-methylquinoxalin-5-yl)benzo[d]thiazol-6-yl)oxy)propan-2-yl (2-((2-hydroxyethyl)carbamoyl)pyridin-4-yl)carbamate (442);

(R)-1-((5-fluoro-2-(2-methoxy-7-methylquinoxalin-5-yl)benzo[d]thiazol-6-yl)oxy)propan-2-yl (2-(methylcarbamoyl)pyridin-4-yl)carbamate (443);

(R)-1-((5-fluoro-2-(2-methoxy-7-methylquinoxalin-5-yl)benzo[d]thiazol-6-yl)oxy)propan-2-yl (2-carbamoylpyridin-4-yl)carbamate (444);

(R)-1-((5-fluoro-2-(2-methoxy-7-methylquinoxalin-5-yl)benzo[d]thiazol-6-yl)oxy)propan-2-yl (6-((2-hydroxyethyl)carbamoyl)pyridin-3-yl)carbamate (445);

(2R,3S)-3-((5-fluoro-2-(2-methoxy-7-methylquinoxalin-5-yl)benzo[d]thiazol-6-yl)oxy)butan-2-yl (6-((3-hydroxy-3-methylbutyl)carbamoyl)pyridin-3-yl)carbamate (446);

(R)-1-((5-fluoro-2-(2-methoxy-7-methylquinoxalin-5-yl)benzo[d]thiazol-6-yl)oxy)propan-2-yl (2-(dimethylcarbamoyl)pyridin-4-yl)carbamate (447);

(R)-1-((5-fluoro-2-(2-methoxy-7-methylquinoxalin-5-yl)benzo[d]thiazol-6-yl)oxy)propan-2-yl (6-((2-hydroxy-2-methylpropyl)carbamoyl)pyridin-3-yl)carbamate (448);

(R)-1-((5-fluoro-2-(2-methoxy-7-methylquinoxalin-5-yl)benzo[d]thiazol-6-yl)oxy)propan-2-yl (6-(((R)-2-hydroxypropyl)carbamoyl)pyridin-3-yl)carbamate (449);

(R)-1-((5-fluoro-2-(2-methoxy-7-methylquinoxalin-5-yl)benzo[d]thiazol-6-yl)oxy)propan-2-yl (6-(((S)-2-hydroxypropyl)carbamoyl)pyridin-3-yl)carbamate (450);

(2R,3S)-3-((5-fluoro-2-(2-methoxy-7-methylquinoxalin-5-yl)benzo[d]thiazol-6-yl)oxy)butan-2-yl (2-((2-hydroxyethyl)carbamoyl)pyridin-4-yl)carbamate (451);

(2R,3S)-3-((5-fluoro-2-(2-methoxy-7-methylquinoxalin-5-yl)benzo[d]thiazol-6-yl)oxy)butan-2-yl (2-(((R)-2-hydroxypropyl)carbamoyl)pyridin-4-yl)carbamate (452);

(2R,3S)-3-((5-fluoro-2-(2-methoxy-7-methylquinoxalin-5-yl)benzo[d]thiazol-6-yl)oxy)butan-2-yl (2-carbamoylpyridin-4-yl)carbamate (453);

(2R,3S)-3-((5-fluoro-2-(2-methoxy-7-methylquinoxalin-5-yl)benzo[d]thiazol-6-yl)oxy)butan-2-yl (2-carbamoylpyrimidin-5-yl)carbamate (454);

(2R,3S)-3-((5-fluoro-2-(2-methoxy-7-methylquinoxalin-5-yl)benzo[d]thiazol-6-yl)oxy)butan-2-yl (2-((2-hydroxyethyl)carbamoyl)pyrimidin-5-yl)carbamate (455);

(2R,3S)-3-((5-fluoro-2-(2-methoxy-7-methylquinoxalin-5-yl)benzo[d]thiazol-6-yl)oxy)butan-2-yl (2-((2-hydroxyethyl)carbamoyl)pyrimidin-5-yl)carbamate (456);

(2R,3S)-3-((5-fluoro-2-(2-methoxy-7-methylquinoxalin-5-yl)benzo[d]thiazol-6-yl)oxy)butan-2-yl (2-((2-hydroxy-2-methylpropyl)carbamoyl)pyrimidin-5-yl)carbamate (457);

(2R,3S)-3-((5-fluoro-2-(2-methoxy-7-methylquinoxalin-5-yl)benzo[d]thiazol-6-yl)oxy)butan-2-yl (2-((3-hydroxy-3-methylbutyl)carbamoyl)pyrimidin-5-yl)carbamate (458);

(2R,3S)-3-((5-fluoro-2-(2-methoxy-7-methylquinoxalin-5-yl)benzo[d]thiazol-6-yl)oxy)butan-2-yl (2-((3-hydroxy-3-methylbutyl)carbamoyl)pyridin-4-yl)carbamate (459);

(2R,3S)-3-((5-fluoro-2-(2-methoxy-7-methylquinoxalin-5-yl)benzo[d]thiazol-6-yl)oxy)butan-2-yl (6-((2-hydroxy-2-methylpropyl)carbamoyl)pyridin-3-yl)carbamate (460);

(2R,3S)-3-((5-fluoro-2-(2-methoxy-7-methylquinoxalin-5-yl)benzo[d]thiazol-6-yl)oxy)butan-2-yl (2-(((S)-2-hydroxypropyl)carbamoyl)pyridin-4-yl)carbamate (461);

(2R,3S)-3-((5-fluoro-2-(2-methoxy-7-methylquinoxalin-5-yl)benzo[d]thiazol-6-yl)oxy)butan-2-yl (2-(((S)-2-hydroxypropyl)carbamoyl)pyrimidin-5-yl)carbamate (462);

(2R,3S)-3-((5-fluoro-2-(2-methoxy-7-methylquinoxalin-5-yl)benzo[d]thiazol-6-yl)oxy)butan-2-yl (2-(((1-hydroxycyclobutyl)methyl)carbamoyl)pyrimidin-5-yl)carbamate (463);

(2R,3S)-3-((5-fluoro-2-(2-methoxy-7-methylquinoxalin-5-yl)benzo[d]thiazol-6-yl)oxy)butan-2-yl (6-((3-hydroxy-3-methylbutyl)carbamoyl)pyridin-3-yl)carbamate (464);

(2R,3S)-3-((5-fluoro-2-(2-methoxy-7-methylquinoxalin-5-yl)benzo[d]thiazol-6-yl)oxy)butan-2-yl (2-((2-hydroxy-2-methylpropyl)carbamoyl)pyridin-4-yl)carbamate (465);

(2R,3S)-3-((5-fluoro-2-(2-methoxy-7-methylquinoxalin-5-yl)benzo[d]thiazol-6-yl)oxy)butan-2-yl (2-(methylcarbamoyl)pyridin-4-yl)carbamate (466);

(2R,3S)-3-((5-fluoro-2-(2-methoxy-7-methylquinoxalin-5-yl)benzo[d]thiazol-6-yl)oxy)butan-2-yl (2-(dimethylcarbamoyl)pyridin-4-yl)carbamate (467);

(2R,3S)-3-((5-fluoro-2-(2-methoxy-7-methylquinoxalin-5-yl)benzo[d]thiazol-6-yl)oxy)butan-2-yl (2-(dimethylcarbamoyl)pyrimidin-5-yl)carbamate (468);

(R)-1-((5-fluoro-2-(2-methoxy-7-methylquinoxalin-5-yl)benzo[d]thiazol-6-yl)oxy)propan-2-yl (2-((2-hydroxyethyl)carbamoyl)pyrimidin-5-yl)carbamate (469);

(R)-1-((5-fluoro-2-(2-methoxy-7-methylquinoxalin-5-yl)benzo[d]thiazol-6-yl)oxy)propan-2-yl (6-(((3-(hydroxymethyl)oxetan-3-yl)methyl)carbamoyl)pyridin-3-yl)carbamate (470);

(R)-1-((5-fluoro-2-(2-methoxy-7-methylquinoxalin-5-yl)benzo[d]thiazol-6-yl)oxy)propan-2-yl (6-((2-hydroxyethyl)(methyl)carbamoyl)pyridin-3-yl)carbamate (471);

(R)-1-((5-fluoro-2-(2-methoxy-7-methylquinoxalin-5-yl)benzo[d]thiazol-6-yl)oxy)propan-2-yl (6-((3-hydroxy-2,2-dimethylpropyl)carbamoyl)pyridin-3-yl)carbamate (472);

(R)-1-((5-fluoro-2-(2-methoxy-7-methylquinoxalin-5-yl)benzo[d]thiazol-6-yl)oxy)propan-2-yl (6-(((1-(hydroxymethyl)cyclobutyl)methyl)carbamoyl)pyridin-3-yl)carbamate (473);

(R)-1-((5-fluoro-2-(2-methoxy-7-methylquinoxalin-5-yl)benzo[d]thiazol-6-yl)oxy)propan-2-yl (6-((2-hydroxy-2-methylpropyl)(methyl)carbamoyl)pyridin-3-yl)carbamate (474);

R)-1-((5-fluoro-2-(2-methoxy-7-methylquinoxalin-5-yl)benzo[d]thiazol-6-yl)oxy)propan-2-yl (6-((R)-3-hydroxypyrrolidine-1-carbonyl)pyridin-3-yl)carbamate (475);

(R)-1-((5-fluoro-2-(2-methoxy-7-methylquinoxalin-5-yl)benzo[d]thiazol-6-yl)oxy)propan-2-yl (6-((R)-3-(hydroxymethyl)pyrrolidine-1-carbonyl)pyridin-3-yl)carbamate (476);

(R)-1-((5-fluoro-2-(2-methoxy-7-methylquinoxalin-5-yl)benzo[d]thiazol-6-yl)oxy)propan-2-yl (6-((S)-2-(hydroxymethyl)morpholine-4-carbonyl)pyridin-3-yl)carbamate (477);

(R)-1-((5-fluoro-2-(2-methoxy-7-methylquinoxalin-5-yl)benzo[d]thiazol-6-yl)oxy)propan-2-yl (6-((S)-3-hydroxypyrrolidine-1-carbonyl)pyridin-3-yl)carbamate (478);

(R)-1-((5-fluoro-2-(2-methoxy-7-methylquinoxalin-5-yl)benzo[d]thiazol-6-yl)oxy)propan-2-yl (6-((S)-3-(hydroxymethyl)pyrrolidine-1-carbonyl)pyridin-3-yl)carbamate (479);

(R)-1-((5-fluoro-2-(2-methoxy-7-methylquinoxalin-5-yl)benzo[d]thiazol-6-yl)oxy)propan-2-yl (6-((R)-2-(hydroxymethyl)morpholine-4-carbonyl)pyridin-3-yl)carbamate (480);

(2R,3S)-3-((5-fluoro-2-(2-methoxy-7-methylquinoxalin-5-yl)benzo[d]thiazol-6-yl)oxy)butan-2-yl (6-((S)-3-hydroxypiperidine-1-carbonyl)pyridin-3-yl)carbamate (481);

(2R,3S)-3-((5-fluoro-2-(2-methoxy-7-methylquinoxalin-5-yl)benzo[d]thiazol-6-yl)oxy)butan-2-yl (6-((S)-3-(hydroxymethyl)pyrrolidine-1-carbonyl)pyridin-3-yl)carbamate (482);

(2R,3S)-3-((5-fluoro-2-(2-methoxy-7-methylquinoxalin-5-yl)benzo[d]thiazol-6-yl)oxy)butan-2-yl (6-((R)-3-hydroxypiperidine-1-carbonyl)pyridin-3-yl)carbamate (483);

(R)-1-((5-fluoro-2-(2-methoxy-7-methylquinoxalin-5-yl)benzo[d]thiazol-6-yl)oxy)propan-2-yl (6-((S)-3-hydroxypiperidine-1-carbonyl)pyridin-3-yl)carbamate (484);

(R)-1-((5-fluoro-2-(2-methoxy-7-methylquinoxalin-5-yl)benzo[d]thiazol-6-yl)oxy)propan-2-yl (6-((R)-3-hydroxypiperidine-1-carbonyl)pyridin-3-yl)carbamate (485);

(2R,3S)-3-((2-(2,7-dimethylquinoxalin-5-yl)-5-fluorobenzo[d]thiazol-6-yl)oxy)butan-2-yl (6-((R)-3-(hydroxymethyl)morpholine-4-carbonyl)pyridin-3-yl)carbamate (486);

(2R,3S)-3-((5-fluoro-2-(2-methoxy-7-methylquinoxalin-5-yl)benzo[d]thiazol-6-yl)oxy)butan-2-yl (6-((S)-3-(hydroxymethyl)morpholine-4-carbonyl)pyridin-3-yl)carbamate (487);

(R)-1-((5-fluoro-2-(2-methoxy-7-methylquinoxalin-5-yl)benzo[d]thiazol-6-yl)oxy)propan-2-yl (6-((R)-3-(hydroxymethyl)morpholine-4-carbonyl)pyridin-3-yl)carbamate (488);

(R)-1-((5-fluoro-2-(2-methoxy-7-methylquinoxalin-5-yl)benzo[d]thiazol-6-yl)oxy)propan-2-yl (6-((S)-3-(hydroxymethyl)morpholine-4-carbonyl)pyridin-3-yl)carbamate (489);

(2R,3S)-3-((2-(2-(difluoromethoxy)-7-methylquinoxalin-5-yl)-5-fluorobenzo[d]thiazol-6-yl)oxy)butan-2-yl (2-methylpyrimidin-5-yl)carbamate (490);

(2R,3S)-3-((5-fluoro-2-(7-methyl-2-propoxyquinoxalin-5-yl)benzo[d]thiazol-6-yl)oxy)butan-2-yl (2-methylpyrimidin-5-yl)carbamate (491);

(2R,3S)-3-((5-fluoro-2-(2-isopropoxy-7-methylquinoxalin-5-yl)benzo[d]thiazol-6-yl)oxy)butan-2-yl (2-methylpyrimidin-5-yl)carbamate (492);

(2R,3S)-3-((5-fluoro-2-(2-(2-hydroxyethoxy)-7-methylquinoxalin-5-yl)benzo[d]thiazol-6-yl)oxy)butan-2-yl (2-methylpyrimidin-5-yl)carbamate (493);

(R)-1-((4-chloro-5-fluoro-2-(2-methoxy-7-methylquinoxalin-5-yl)benzo[d]thiazol-6-yl)oxy)propan-2-yl (2-(hydroxymethyl)pyridin-4-yl)carbamate (494);

(R)-1-((5-fluoro-2-(2-methoxy-7-methylquinoxalin-5-yl)benzo[d]thiazol-6-yl)oxy)propan-2-yl (2-(hydroxymethyl)pyridin-4-yl)carbamate (495);

(R)-1-((5-fluoro-2-(2-methoxy-7-methylquinoxalin-5-yl)benzo[d]thiazol-6-yl)oxy)propan-2-yl (2-(hydroxymethyl)pyrimidin-5-yl)carbamate (496);

(R)-1-((5-fluoro-2-(2-methoxy-7-methylquinoxalin-5-yl)benzo[d]thiazol-6-yl)oxy)propan-2-yl (2-(2-hydroxypropan-2-yl)pyrimidin-5-yl)carbamate (497);

(R)-1-((5-fluoro-2-(2-methoxy-7-methylquinoxalin-5-yl)benzo[d]thiazol-6-yl)oxy)propan-2-yl (6-(2-hydroxypropan-2-yl)pyridin-3-yl)carbamate (498);

(2R,3S)-3-((5-fluoro-2-(2-methoxy-7-methylquinoxalin-5-yl)benzo[d]thiazol-6-yl)oxy)butan-2-yl (6-(hydroxymethyl)pyridin-3-yl)carbamate (499);

(2R,3S)-3-((5-fluoro-2-(2-methoxy-7-methylquinoxalin-5-yl)benzo[d]thiazol-6-yl)oxy)butan-2-yl (6-(2-hydroxypropan-2-yl)pyridin-3-yl)carbamate (500);

(2R,3S)-3-((5-fluoro-2-(2-methoxy-7-methylquinoxalin-5-yl)benzo[d]thiazol-6-yl)oxy)butan-2-yl (2-(2-hydroxypropan-2-yl)pyrimidin-5-yl)carbamate (501);

(2R,3S)-3-((5-fluoro-2-(2-methoxy-7-methylquinoxalin-5-yl)benzo[d]thiazol-6-yl)oxy)butan-2-yl (2-(hydroxymethyl)pyrimidin-5-yl)carbamate (502);

4-chloro-2-(2-methoxy-7-methylquinoxalin-5-yl)benzo[d]thiazole (503);

2-(2-methoxy-7-methylquinoxalin-5-yl)benzo[d]thiazole (504);

2-(2-methoxy-7-methylquinoxalin-5-yl)-4-methylbenzo[d]thiazole (505);

4-chloro-6-methoxy-2-(2-methoxy-7-methylquinoxalin-5-yl)benzo[d]thiazole (506);

5-chloro-6-methoxy-2-(2-methoxy-7-methylquinoxalin-5-yl)benzo[d]thiazole (507);

6-methoxy-2-(2-methoxy-7-methylquinoxalin-5-yl)-4-methylbenzo[d]thiazole (509);

6-methoxy-2-(2-methoxy-7-methylquinoxalin-5-yl)-4-methylbenzo[d]thiazole (510);

1-((5-fluoro-2-(2-methoxy-7-methylquinoxalin-5-yl)benzo[d]thiazol-6-yl)oxy)-3-methoxypropan-2-yl pyridin-3-ylcarbamate (516);

(R)-1-((5-fluoro-2-(2-methoxy-7-methylquinoxalin-5-yl)benzo[d]thiazol-6-yl)oxy)butan-2-yl pyridin-3-ylcarbamate (517);

4-((4-chloro-5-fluoro-2-(2-methoxy-7-methylquinoxalin-5-yl)benzo[d]thiazol-6-yl)oxy)—N-(pyridin-3-yl)butanamide (518);

1-(2-((4-chloro-5-fluoro-2-(2-methoxy-7-methylquinoxalin-5-yl)benzo[d]thiazol-6-yl)oxy)ethyl)-3-(pyridin-3-yl)urea (519);

1-(2-((4-chloro-5-fluoro-2-(2-methoxy-7-methylquinoxalin-5-yl)benzo[d]thiazol-6-yl)oxy)ethyl)-1-methyl-3-(2-methylpyrimidin-5-yl)urea (520);

(2R,3S)-3-((5-fluoro-2-(2-methoxy-7-methylquinoxalin-5-yl)benzo[d]thiazol-6-yl)oxy) butan-2-yl (6-(morpholinomethyl)pyridin-3-yl)carbamate (521);

(2R,3S)-3-((2-(2-(dimethylamino)-7-methylquinoxalin-5-yl)-5-fluorobenzo[d]thiazol-6-yl)oxy)butan-2-yl (2-methylpyrimidin-5-yl)carbamate (522);

5-(((((2R,3S)-3-((5-fluoro-2-(2-methoxy-7-methylquinoxalin-5-yl)benzo[d]thiazol-6-yl)oxy)butan-2-yl)oxy)carbonyl)amino)picolinic acid, (523);

(2R,3S)-3-((5-fluoro-2-(2-methoxy-7-methylquinoxalin-5-yl)benzo[d]thiazol-6-yl)oxy) butan-2-yl carbamate (524);

1-((5-fluoro-2-(2-methoxy-7-methylquinoxalin-5-yl)benzo[d]thiazol-6-yl)oxy)-3-isobutoxypropan-2-yl (2-methylpyrimidin-5-yl)carbamate (525);

(2R,3S)-3-((2-(2-ethoxy-7-methylquinoxalin-5-yl)-5-fluorobenzo[d]thiazol-6-yl)oxy)butan-2-yl (6-(2-hydroxyethyl)pyridin-3-yl)carbamate (526);

(2R,3S)-3-((2-(2-ethoxy-7-methylquinoxalin-5-yl)-5-fluorobenzo[d]thiazol-6-yl)oxy)butan-2-yl (6-((2-hydroxy-2-methylpropyl)carbamoyl)pyridin-3-yl)carbamate (527);

(2R,3S)-3-((5-fluoro-2-(2-methoxy-7-methylquinoxalin-5-yl)benzo[d]thiazol-6-yl)oxy)butan-2-yl (2-(hydroxymethyl)pyrimidin-5-yl)carbamate (528);

(2R,3S)-3-((2-(2-ethoxy-7-methylquinoxalin-5-yl)-5-fluorobenzo[d]thiazol-6-yl)oxy)butan-2-yl (2-(hydroxymethyl)pyrimidin-5-yl)carbamate (529);

(R)-1-((5-fluoro-2-(2-methoxy-7-methylquinoxalin-5-yl)benzo[d]thiazol-6-yl)oxy) propan-2-yl (6-((2-methyl-2-(phosphonooxy)propyl)carbamoyl)pyridin-3-yl)carbamate, (530);

(2R,3S)-3-((2-(2-ethoxy-7-methylquinoxalin-5-yl)-5-fluorobenzo[d]thiazol-6-yl)oxy)butan-2-yl (6-(((S)-2-hydroxypropyl)carbamoyl)pyridin-3-yl)carbamate, (531);

(2R,3S)-3-((2-(2-ethoxy-7-methylquinoxalin-5-yl)-5-fluorobenzo[d]thiazol-6-yl)oxy)butan-2-yl (2-((phosphonooxy)methyl)pyrimidin-5-yl)carbamate (532);

(2R,3S)-3-((5-fluoro-2-(2-methoxy-7-methylquinoxalin-5-yl)benzo[d]thiazol-6-yl)oxy)butan-2-yl (5-hydroxypyridin-3-yl)carbamate (533);

(2R,3S)-3-((5-fluoro-2-(2-methoxy-7-methylquinoxalin-5-yl)benzo[d]thiazol-6-yl)oxy) butan-2-yl (5-(2-hydroxyethoxy)pyridin-3-yl)carbamate (534);

(2R,3S)-3-((2-(2-ethoxy-7-methylquinoxalin-5-yl)-5-fluorobenzo[d]thiazol-6-yl)oxy)butan-2-yl (2-((S)-1-hydroxyethyl)pyrimidin-5-yl)carbamate (535);

(2R,3S)-3-((2-(2-ethoxy-7-methylquinoxalin-5-yl)-5-fluorobenzo[d]thiazol-6-yl)oxy) butan-2-yl (2-((R)-1-hydroxyethyl)pyrimidin-5-yl)carbamate (536);

2-((5-fluoro-2-(2-methoxy-7-methylquinoxalin-5-yl)benzo[d]thiazol-6-yl)oxy)ethyl (2-(2-hydroxyethyl)pyrimidin-5-yl)carbamate (537);

(2R,3S)-3-((4-chloro-5-fluoro-2-(2-methoxy-7-methylquinoxalin-5-yl)benzo[d]thiazol-6-yl)oxy)butan-2-yl (2-(2-hydroxyethyl)pyrimidin-5-yl)carbamate (538);

(2R,3S)-3-((2-(6-chloro-3-methoxyquinolin-8-yl)-5-fluorobenzo[d]thiazol-6-yl)oxy)butan-2-yl (2-(hydroxymethyl)pyrimidin-5-yl)carbamate (539);

(2R,3S)-3-((2-(6-chloro-3-methoxyquinolin-8-yl)-5-fluorobenzo[d]thiazol-6-yl)oxy)butan-2-yl (2-((R)-2-hydroxypropoxy)pyrimidin-5-yl)carbamate (540);

(2R,3S)-3-((2-(6-chloro-3-methoxyquinolin-8-yl)-5-fluorobenzo[d]thiazol-6-yl)oxy)butan-2-yl (2-((S)-2-hydroxypropoxy)pyrimidin-5-yl)carbamate (541);

(R)-1-((4-chloro-5-fluoro-2-(2-methoxy-7-methylquinoxalin-5-yl)benzo[d]thiazol-6-yl)oxy)propan-2-yl (6-(2-hydroxyethyl)pyridin-3-yl)carbamate (542);

(R)-1-((5-fluoro-2-(2-methoxy-7-methylquinoxalin-5-yl)benzo[d]thiazol-6-yl)oxy)propan-2-yl (6-(2-hydroxyethyl)pyridin-3-yl)carbamate (543);

(R)-1-((5-fluoro-2-(2-methoxy-7-methylquinoxalin-5-yl)benzo[d]thiazol-6-yl)oxy)propan-2-yl (5-(hydroxymethyl)-6-methylpyridin-3-yl)carbamate (544);

(R)-1-((5-fluoro-2-(2-methoxy-7-methylquinoxalin-5-yl)benzo[d]thiazol-6-yl)oxy)propan-2-yl (2-(2-hydroxyethyl)pyridin-4-yl)carbamate (545);

(R)-1-((5-fluoro-2-(2-methoxy-7-methylquinoxalin-5-yl)benzo[d]thiazol-6-yl)oxy)propan-2-yl (6-(hydroxymethyl)pyridin-3-yl)carbamate (546);

(2R,3S)-3-((5-fluoro-2-(2-methoxy-7-methylquinoxalin-5-yl)benzo[d]thiazol-6-yl)oxy)butan-2-yl (2-(2-hydroxyethyl)pyridin-4-yl)carbamate (547);

(2R,3S)-3-((5-fluoro-2-(2-methoxy-7-methylquinoxalin-5-yl)benzo[d]thiazol-6-yl)oxy)butan-2-yl (2-(((R)-1-hydroxypropan-2-yl)oxy)pyridin-4-yl)carbamate (549);

(2R,3S)-3-((5-fluoro-2-(2-methoxy-7-methylquinoxalin-5-yl)benzo[d]thiazol-6-yl)oxy)butan-2-yl (2-((R)-2-hydroxypropoxy)pyridin-4-yl)carbamate (550);

(R)-1-((5-fluoro-2-(2-methoxy-7-methylquinoxalin-5-yl)benzo[d]thiazol-6-yl)oxy)propan-2-yl (2-(2-hydroxyethoxy)pyridin-4-yl)carbamate (552);

(R)-1-((5-fluoro-2-(2-methoxy-7-methylquinoxalin-5-yl)benzo[d]thiazol-6-yl)oxy)propan-2-yl (2-(((R)-1-hydroxypropan-2-yl)oxy)pyrimidin-5-yl)carbamate (553);

(2R,3S)-3-((5-fluoro-2-(2-methoxy-7-methylquinoxalin-5-yl)benzo[d]thiazol-6-yl)oxy)butan-2-yl (2-(((R)-1-hydroxypropan-2-yl)oxy)pyrimidin-5-yl)carbamate (554);

(R)-1-((5-fluoro-2-(2-methoxy-7-methylquinoxalin-5-yl)benzo[d]thiazol-6-yl)oxy)propan-2-yl (2-(2-hydroxyethoxy)pyrimidin-5-yl)carbamate (555);

(2R,3S)-3-((5-fluoro-2-(2-methoxy-7-methylquinoxalin-5-yl)benzo[d]thiazol-6-yl)oxy)butan-2-yl (2-(2-hydroxyethoxy)pyrimidin-5-yl)carbamate (556);

(R)-1-((5-fluoro-2-(2-methoxy-7-methylquinoxalin-5-yl)benzo[d]thiazol-6-yl)oxy)propan-2-yl (6-(2-hydroxy-2-methylpropyl)pyridin-3-yl)carbamate (557);

(R)-1-((5-fluoro-2-(2-methoxy-7-methylquinoxalin-5-yl)benzo[d]thiazol-6-yl)oxy)propan-2-yl (2-(((S)-1-hydroxypropan-2-yl)oxy)pyrimidin-5-yl)carbamate (558);

(2R,3S)-3-((5-fluoro-2-(2-methoxy-7-methylquinoxalin-5-yl)benzo[d]thiazol-6-yl)oxy)butan-2-yl (6-(2-hydroxy-2-methylpropyl)pyridin-3-yl)carbamate (559);

(2R,3S)-3-((5-fluoro-2-(2-methoxy-7-methylquinoxalin-5-yl)benzo[d]thiazol-6-yl)oxy)butan-2-yl (2-(((S)-1-hydroxypropan-2-yl)oxy)pyrimidin-5-yl)carbamate (560);

(2R,3S)-3-((5-fluoro-2-(2-methoxy-7-methylquinoxalin-5-yl)benzo[d]thiazol-6-yl)oxy)butan-2-yl (2-(2-hydroxy-2-methylpropyl)pyridin-4-yl)carbamate (561);

(2R,3S)-3-((5-fluoro-2-(2-methoxy-7-methylquinoxalin-5-yl)benzo[d]thiazol-6-yl)oxy)butan-2-yl (2-(2-hydroxy-2-methylpropoxy)pyridin-4-yl)carbamate (562);

(2R,3S)-3-((5-fluoro-2-(2-methoxy-7-methylquinoxalin-5-yl)benzo[d]thiazol-6-yl)oxy)butan-2-yl (2-(3-hydroxy-3-methylbutoxy)pyridin-4-yl)carbamate (563);

(R)-1-((5-fluoro-2-(2-methoxy-7-methylquinoxalin-5-yl)benzo[d]thiazol-6-yl)oxy)propan-2-yl (2-(2-hydroxyethyl)pyrimidin-5-yl)carbamate (564);

(2R,3S)-3-((5-fluoro-2-(2-methoxy-7-methylquinoxalin-5-yl)benzo[d]thiazol-6-yl)oxy)butan-2-yl (2-(2-hydroxyethyl)pyrimidin-5-yl)carbamate (565);

(2R,3S)-3-((2-(2-ethoxy-7-methylquinoxalin-5-yl)-5-fluorobenzo[d]thiazol-6-yl)oxy)butan-2-yl (2-(2-hydroxyethyl)pyrimidin-5-yl)carbamate (566);

(R)-1-((5-fluoro-2-(2-methoxy-7-methylquinoxalin-5-yl)benzo[d]thiazol-6-yl)oxy)propan-2-yl (2-(3-hydroxy-3-methylbutoxy)pyridin-4-yl)carbamate (567);

(2R,3S)-3-((2-(2-ethoxy-7-methylquinoxalin-5-yl)-5-fluorobenzo[d]thiazol-6-yl)oxy)butan-2-yl (2-(2-hydroxyethoxy)pyrimidin-5-yl)carbamate (568);

(R)-1-((5-fluoro-2-(2-methoxy-7-methylquinoxalin-5-yl)benzo[d]thiazol-6-yl)oxy)propan-2-yl (2-(3-hydroxy-3-methylbutoxy)pyrimidin-5-yl)carbamate (569);

(2R,3S)-3-((5-fluoro-2-(2-methoxy-7-methylquinoxalin-5-yl)benzo[d]thiazol-6-yl)oxy)butan-2-yl (2-(3-hydroxy-3-methylbutoxy)pyrimidin-5-yl)carbamate (570);

(2R,3S)-3-((5-fluoro-2-(2-methoxy-7-methylquinoxalin-5-yl)benzo[d]thiazol-6-yl)oxy)butan-2-yl (6-(2-hydroxyethoxy)pyridin-3-yl)carbamate (571);

(R)-1-((5-fluoro-2-(2-methoxy-7-methylquinoxalin-5-yl)benzo[d]thiazol-6-yl)oxy)propan-2-yl (6-(2-hydroxyethoxy)pyridin-3-yl)carbamate (572);

(2R,3S)-3-((5-fluoro-2-(2-methoxy-7-methylquinoxalin-5-yl)benzo[d]thiazol-6-yl)oxy)butan-2-yl (6-(2,2-difluoro-3-hydroxypropoxy)pyridin-3-yl)carbamate (573);

(R)-1-((5-fluoro-2-(2-methoxy-7-methylquinoxalin-5-yl)benzo[d]thiazol-6-yl)oxy)propan-2-yl (6-(2,2-difluoro-3-hydroxypropoxy)pyridin-3-yl)carbamate (574);

(2R,3S)-3-((5-fluoro-2-(2-methoxy-7-methylquinoxalin-5-yl)benzo[d]thiazol-6-yl)oxy)butan-2-yl (2-(2-hydroxy-2-methylpropoxy)pyrimidin-5-yl)carbamate (575);

(R)-1-((5-fluoro-2-(2-methoxy-7-methylquinoxalin-5-yl)benzo[d]thiazol-6-yl)oxy)propan-2-yl (2-(2-hydroxy-2-methylpropoxy)pyrimidin-5-yl)carbamate (576);

(2R,3S)-3-((5-fluoro-2-(2-methoxy-7-methylquinoxalin-5-yl)benzo[d]thiazol-6-yl)oxy)butan-2-yl (2-(2-hydroxy-2-methylpropyl)pyrimidin-5-yl)carbamate (577);

(2R,3S)-3-((5-fluoro-2-(2-methoxy-7-methylquinoxalin-5-yl)benzo[d]thiazol-6-yl)oxy)butan-2-yl (2-((R)-2-hydroxypropoxy)pyrimidin-5-yl)carbamate (578);

(2R,3S)-3-((2-(6-chloro-3-methoxyquinolin-8-yl)-5-fluorobenzo[d]thiazol-6-yl)oxy)butan-2-yl (2-(2-hydroxyethyl)pyrimidin-5-yl)carbamate (579);

(2R,3S)-3-((2-(2-ethoxy-7-methylquinoxalin-5-yl)-5-fluorobenzo[d]thiazol-6-yl)oxy)butan-2-yl (2-((R)-2-hydroxypropoxy)pyrimidin-5-yl)carbamate (580);

(2R,3S)-3-((5-fluoro-2-(2-methoxy-7-methylquinoxalin-5-yl)benzo[d]thiazol-6-yl)oxy)butan-2-yl (2-((S)-2-hydroxypropoxy)pyrimidin-5-yl)carbamate (581);

(2R,3S)-3-((2-(2-ethoxy-7-methylquinoxalin-5-yl)-5-fluorobenzo[d]thiazol-6-yl)oxy)butan-2-yl (2-((S)-2-hydroxypropoxy)pyrimidin-5-yl)carbamate (582);

(2R,3S)-3-((2-(2-ethoxy-7-methylquinoxalin-5-yl)-5-fluorobenzo[d]thiazol-6-yl)oxy)butan-2-yl (2-((R)-2,3-dihydroxypropoxy)pyrimidin-5-yl)carbamate (583);

(2S,3S)-3-((5-fluoro-2-(2-methoxy-7-methylquinoxalin-5-yl)benzo[d]thiazol-6-yl)oxy)butan-2-yl (2-(2-hydroxyethyl)pyrimidin-5-yl)carbamate (584);

(2R,3S)-3-((5-fluoro-2-(2-methoxy-7-methylquinoxalin-5-yl)benzo[d]thiazol-6-yl)oxy)butan-2-yl (2-((S)-2,3-dihydroxypropoxy)pyrimidin-5-yl)carbamate (585);

(R)-1-((4-chloro-5-fluoro-2-(2-methoxy-7-methylquinoxalin-5-yl)benzo[d]thiazol-6-yl)oxy)propan-2-yl (2-(2-hydroxyethyl)pyrimidin-5-yl)carbamate (586);

(2R,3S)-3-((5-fluoro-2-(2-methoxy-7-methylquinoxalin-5-yl)benzo[d]thiazol-6-yl)oxy)butan-2-yl (2-((R)-2,3-dihydroxypropoxy)pyrimidin-5-yl)carbamate (587);

(2R,3S)-3-((2-(2-ethoxy-7-methylquinoxalin-5-yl)-5-fluorobenzo[d]thiazol-6-yl)oxy)butan-2-yl (2-((S)-2,3-dihydroxypropoxy)pyrimidin-5-yl)carbamate (588);

(R)-1-((4-chloro-5-fluoro-2-(2-methoxy-7-methylquinoxalin-5-yl)benzo[d]thiazol-6-yl)oxy)propan-2-yl (2-methylpyrimidin-5-yl)carbamate (589);

(R)-1-((4-chloro-5-fluoro-2-(2-methoxy-7-methylquinoxalin-5-yl)benzo[d]thiazol-6-yl)oxy)propan-2-yl (2-methylpyridin-3-yl)carbamate (590);

(R)-1-((4-chloro-5-fluoro-2-(2-methoxy-7-methylquinoxalin-5-yl)benzo[d]thiazol-6-yl)oxy)propan-2-yl pyrimidin-5-ylcarbamate (591);

(R)-1-((5-fluoro-2-(2-methoxy-7-methylquinoxalin-5-yl)benzo[d]thiazol-6-yl)oxy)propan-2-yl (6-methylpyridin-3-yl)carbamate (592);

methyl 3-(5-(((((2R,3S)-3-((2-(2-ethoxy-7-methylquinoxalin-5-yl)-5-fluorobenzo[d]thiazol-6-yl)oxy)butan-2-yl)oxy)carbonyl)amino)pyrimidin-2-yl)propanoate (593);

(2S,3S)-3-((5-fluoro-2-(2-methoxy-7-methylquinoxalin-5-yl)benzo[d]thiazol-6-yl)oxy)butan-2-yl pyridin-3-ylcarbamate (594);

(2S,3S)-3-((5-fluoro-2-(2-methoxy-7-methylquinoxalin-5-yl)benzo[d]thiazol-6-yl)oxy)butan-2-yl (2-methylpyrimidin-5-yl)carbamate (595);

(R)-(5-aminopyridin-2-yl)methyl (1-((4-chloro-5-fluoro-2-(2-methoxy-7-methylquinoxalin-5-yl)benzo[d]thiazol-6-yl)oxy)propan-2-yl) carbonate (596);

(R)-1-((5-fluoro-2-(2-methoxy-7-methylquinoxalin-5-yl)benzo[d]thiazol-6-yl)oxy)propan-2-yl (2-(dimethylamino)pyrimidin-5-yl)carbamate (597);

(2R,3S)-3-((5-fluoro-2-(2-methoxy-7-methylquinoxalin-5-yl)benzo[d]thiazol-6-yl)oxy)butan-2-yl (2-(dimethylamino)pyrimidin-5-yl)carbamate (598);

(2R,3S)-3-((5-fluoro-2-(2-methoxy-7-methylquinoxalin-5-yl)benzo[d]thiazol-6-yl)oxy)butan-2-yl (6-(dimethylamino)pyridin-3-yl)carbamate (599);

(2R,3S)-3-((5-fluoro-2-(2-methoxy-7-methylquinoxalin-5-yl)benzo[d]thiazol-6-yl)oxy)butan-2-yl (6-(2-oxooxazolidin-3-yl)pyridin-3-yl)carbamate (600);

(2R,3S)-3-((5-fluoro-2-(2-methoxy-7-methylquinoxalin-5-yl)benzo[d]thiazol-6-yl)oxy)butan-2-yl (6-acetamidopyridin-3-yl)carbamate (601);

(2R,3S)-3-((5-fluoro-2-(2-methoxy-7-methylquinoxalin-5-yl)benzo[d]thiazol-6-yl)oxy)butan-2-yl (6-aminopyridin-3-yl)carbamate (602);

(2R,3S)-3-((5-fluoro-2-(2-methoxy-7-methylquinoxalin-5-yl)benzo[d]thiazol-6-yl)oxy)butan-2-yl (6-morpholinopyridin-3-yl)carbamate (603);

(2R,3S)-3-((5-fluoro-2-(2-methoxy-7-methylquinoxalin-5-yl)benzo[d]thiazol-6-yl)oxy)butan-2-yl (2-(3-chloro-4-fluorobenzamido)pyrimidin-5-yl)carbamate (604);

(2R,3S)-3-((5-fluoro-2-(2-methoxy-7-methylquinoxalin-5-yl)benzo[d]thiazol-6-yl)oxy)butan-2-yl (6-(pyrrolidin-1-yl)pyridin-3-yl)carbamate (605);

(2R,3S)-3-((5-fluoro-2-(2-methoxy-7-methylquinoxalin-5-yl)benzo[d]thiazol-6-yl)oxy)butan-2-yl (2-((2-hydroxy-2-methylpropyl)amino)pyrimidin-5-yl)carbamate (606);

(2R,3S)-3-((5-fluoro-2-(2-methoxy-7-methylquinoxalin-5-yl)benzo[d]thiazol-6-yl)oxy)butan-2-yl (2-(N-methylmethylsulfonamido)pyrimidin-5-yl)carbamate (607);

(2R,3S)-3-((5-fluoro-2-(2-methoxy-7-methylquinoxalin-5-yl)benzo[d]thiazol-6-yl)oxy)butan-2-yl (2-morpholinopyrimidin-5-yl)carbamate (608);

(R)-1-((5-fluoro-2-(2-methoxy-7-methylquinoxalin-5-yl)benzo[d]thiazol-6-yl)oxy)propan-2-yl (6-(2-oxooxazolidin-3-yl)pyridin-3-yl)carbamate (609);

(R)-1-((5-fluoro-2-(2-methoxy-7-methylquinoxalin-5-yl)benzo[d]thiazol-6-yl)oxy)propan-2-yl (6-acetamidopyridin-3-yl)carbamate (610);

(R)-1-((5-fluoro-2-(2-methoxy-7-methylquinoxalin-5-yl)benzo[d]thiazol-6-yl)oxy)propan-2-yl (5-(hydroxymethyl)pyridin-3-yl)carbamate (611);

(2S,3S)-3-((5-fluoro-2-(2-methoxy-7-methylquinoxalin-5-yl)benzo[d]thiazol-6-yl)oxy)butan-2-ol (612);

(2R,3S)-3-((2-(2-carbamoyl-7-methylquinoxalin-5-yl)-5-fluorobenzo[d]thiazol-6-yl)oxy)butan-2-yl (2-methylpyrimidin-5-yl)carbamate (613);

(2R,3S)-3-((5-fluoro-2-(7-methyl-2-(methylcarbamoyl)quinoxalin-5-yl)benzo[d]thiazol-6-yl)oxy)butan-2-yl (2-methylpyrimidin-5-yl)carbamate (614);

(2R,3S)-3-((2-(2-(dimethylcarbamoyl)-7-methylquinoxalin-5-yl)-5-fluorobenzo[d]thiazol-6-yl)oxy)butan-2-yl (2-methylpyrimidin-5-yl)carbamate (615);

(2R,3S)-3-((5-fluoro-2-(2-((2-hydroxyethyl)carbamoyl)-7-methylquinoxalin-5-yl)benzo[d]thiazol-6-yl)oxy)butan-2-yl (2-methylpyrimidin-5-yl)carbamate (616);

(2R,3S)-3-((5-fluoro-2-(2-methoxy-7-methylquinoxalin-5-yl)benzo[d]thiazol-6-yl)oxy)butan-2-yl (5-(hydroxymethyl)pyridin-3-yl)carbamate (617);

(2R,3S)-3-((5-fluoro-2-(2-methoxy-7-methylquinoxalin-5-yl)benzo[d]thiazol-6-yl)oxy)butan-2-yl (6-(2-hydroxypropan-2-yl)pyridin-3-yl)carbamate (618);

(2R,3S)-3-((5-fluoro-2-(2-methoxy-7-methylquinoxalin-5-yl)benzo[d]thiazol-6-yl)oxy)butan-2-yl (2-(hydroxymethyl)pyridin-4-yl)carbamate (619);

(2R,3S)-3-((5-fluoro-2-(2-methoxy-7-methylquinoxalin-5-yl)benzo[d]thiazol-6-yl)oxy)butan-2-yl (2-(1-hydroxyethyl)pyrimidin-5-yl)carbamate (620);

2-((4-chloro-5-fluoro-2-(2-methoxy-7-methylquinoxalin-5-yl)benzo[d]thiazol-6-yl)oxy)ethyl isothiazol-5-ylcarbamate (621);

(R)-5-(((4-chloro-5-fluoro-2-(2-methoxy-7-methylquinoxalin-5-yl)benzo[d]thiazol-6-yl)oxy)methyl) oxazolidin-2-one (622);

4-(((4-chloro-5-fluoro-2-(2-methoxy-7-methylquinoxalin-5-yl)benzo[d]thiazol-6-yl)oxy)methyl)oxazol-2-amine (623);

(2R,3S)-3-((2-(2-ethoxy-7-methylquinoxalin-5-yl)-5-fluorobenzo[d]thiazol-6-yl)oxy)butan-2-yl (2-(2-(phosphonooxy)ethyl)pyrimidin-5-yl)carbamate (624);

2-(6-methoxy-2-(2-methoxy-7-methylquinoxalin-5-yl)benzo[d]thiazol-4-yl)propan-2-ol (627);

1-(6-methoxy-2-(2-(methoxymethyl)-7-methylquinoxalin-5-yl)benzo[d]thiazol-4-yl)-2,2-dimethylpropan-1-ol (628);

(6-methoxy-2-(2-methoxy-7-methylquinoxalin-5-yl)benzo[d]thiazol-4-yl) (phenyl)methanol (629);

1-(6-methoxy-2-(2-methoxy-7-methylquinoxalin-5-yl)benzo[d]thiazol-4-yl)-2,2-dimethylpropan-1-ol (630);

1-(6-methoxy-2-(2-methoxy-7-methylquinoxalin-5-yl) benzo[d]thiazol-4-yl)-2-phenylethanol (631);
1-(5-fluoro-6-methoxy-2-(2-methoxy-7-methylquinoxalin-5-yl)benzo[d]thiazol-4-yl)-2,2-dimethylpropan-1-ol (632);
2,2,2-trifluoro-1-(6-methoxy-2-(2-methoxy-7-methylquinoxalin-5-yl)benzo[d]thiazol-4-yl)ethanol (633);
4-(1-fluoro-2,2-dimethylpropyl)-6-methoxy-2-(2-methoxy-7-methylquinoxalin-5-yl)benzo[d]thiazole (634);
4-(benzyloxy)-6-methoxy-2-(2-(methoxymethyl)-7-methylquinoxalin-5-yl)benzo[d]thiazole (635);
1-(2-(7-chloro-2-methoxyquinoxalin-5-yl)-6-methoxybenzo[d]thiazol-4-yl)-2,2-dimethylpropan-1-ol (636);
1-(6-methoxy-2-(2-methoxy-7-methylquinoxalin-5-yl) benzo[d]thiazol-4-yl)-2,2-dimethylpropan-1-ol (637);
2-((4-(1-hydroxy-2,2-dimethylpropyl)-2-(2-methoxy-7-methylquinoxalin-5-yl)benzo[d]thiazol-6-yl) oxy)ethyl (5-cyanopyridin-3-yl)carbamate (638);
8-(4-(1-hydroxy-2,2-dimethylpropyl)-6-methoxybenzo[d]thiazol-2-yl)-3-methoxyquinoxaline-6-carbonitrile (639);
1-(6-ethoxy-2-(2-methoxy-7-methylquinoxalin-5-yl) benzo[d]thiazol-4-yl)-2,2-dimethylpropan-1-ol (640);
2-(6-methoxy-2-(2-methoxy-7-methylquinoxalin-5-yl) benzo[d]thiazol-4-yl)ethanol (641);
(6-methoxy-2-(2-methoxy-7-methylquinoxalin-5-yl) benzo[d]thiazol-4-yl)(3-(trifluoromethyl)phenyl) methanol (642);
(2-isopropylphenyl)(6-methoxy-2-(2-methoxy-7-methylquinoxalin-5-yl)benzo[d]thiazol-4-yl)methanol (643);
ethyl 1-(hydroxy(6-methoxy-2-(2-methoxy-7-methylquinoxalin-5-yl)benzo[d]thiazol-4-yl)methyl) cyclobutanecarboxylate (644);
(2R,3S)-3-((2-(6-chloro-3-methoxyquinolin-8-yl)-5-fluorobenzo[d]thiazol-6-yl)oxy)butan-2-yl (2-methylpyrimidin-5-yl)carbamate (645);
(1-(hydroxymethyl)cyclobutyl)(6-methoxy-2-(2-methoxy-7-methylquinoxalin-5-yl) benzo[d]thiazol-4-yl)methanol (646);
(2R,3S)-3-((2-(6-chloro-3-ethylquinolin-8-yl)-5-fluorobenzo[d]thiazol-6-yl)oxy)butan-2-yl (2-methylpyrimidin-5-yl)carbamate (647);
2-((4-(1-hydroxy-2,2-dimethylpropyl)-2-(2-methoxy-7-methylquinoxalin-5-yl)benzo[d]thiazol-6-yl) oxy)ethyl pyridin-4-ylcarbamate (658);
5-(benzofuran-2-yl)-2-ethoxy-7-methylquinoxaline (661);
4-methoxyphenyl (2-((2-(2-methoxy-7-methylquinoxalin-5-yl)-7-methylthiazolo[5,4-b]pyridin-5-yl)oxy) ethyl) carbamate (662);
(6-methoxy-2-(2-methoxy-7-methylquinoxalin-5-yl) benzo[d]thiazol-4-yl)(tetrahydro-2H-pyran-4-yl) methanol (663);
(6-methoxy-2-(2-methoxy-7-methylquinoxalin-5-yl) benzo[d]thiazol-4-yl)(tetrahydro-2H-pyran-4-yl) methanol (664);
(6-methoxy-2-(2-methoxy-7-methylquinoxalin-5-yl) benzo[d]thiazol-4-yl)(1-phenylcyclobutyl)methanol (665);
(6-methoxy-2-(2-methoxy-7-methylquinoxalin-5-yl) benzo[d]thiazol-4-yl)(1-methoxycyclobutyl)methanol (666);
(6-methoxy-2-(2-methoxy-7-methylquinoxalin-5-yl) benzo[d]thiazol-4-yl)(1-(trifluoromethyl)cyclopropyl) methanol (667);
(6-methoxy-2-(2-methoxy-7-methylquinoxalin-5-yl) benzo[d]thiazol-4-yl)(1-phenylcyclopropyl)methanol (668);
(6-methoxy-2-(2-methoxy-7-methylquinoxalin-5-yl) benzo[d]thiazol-4-yl)(1-(trifluoromethyl)cyclobutyl) methanol (669);
(6-methoxy-2-(2-methoxy-7-methylquinoxalin-5-yl) benzo[d]thiazol-4-yl)(1-methylcyclopropyl)methanol (671);
(6-methoxy-2-(2-methoxy-7-methylquinoxalin-5-yl) benzo[d]thiazol-4-yl)(1-methylcyclohexyl)methanol (672);
(6-methoxy-2-(2-methoxy-7-methylquinoxalin-5-yl) benzo[d]thiazol-4-yl)(thiazol-2-yl)methanol (673);
(6-methoxy-2-(2-methoxy-7-methylquinoxalin-5-yl) benzo[d]thiazol-4-yl)(4-methyltetrahydro-2H-pyran-4-yl)methanol (674);
(3-fluoro-5-methoxyphenyl)(6-methoxy-2-(2-methoxy-7-methylquinoxalin-5-yl)benzo[d]thiazol-4-yl)methanol (675);
(6-methoxy-2-(2-methoxy-7-methylquinoxalin-5-yl) benzo[d]thiazol-4-yl)(1-methylcyclohexyl)methanol (676);
1-(6-methoxy-2-(2-methoxy-7-methylquinoxalin-5-yl) benzo[d]thiazol-4-yl)ethan-1-ol (677);
(R)-1-((6-fluoro-2-(2-methoxy-7-methylquinoxalin-5-yl) thiazolo[5,4-b]pyridin-5-yl)oxy)propan-2-yl (2-methylpyrimidin-5-yl)carbamate (678);
(R)-1-((6-fluoro-2-(2-methoxy-7-methylquinoxalin-5-yl) thiazolo[5,4-b]pyridin-5-yl)oxy)propan-2-yl (2-methoxypyrimidin-5-yl)carbamate (679);
(R)-1-((6-fluoro-2-(2-methoxy-7-methylquinoxalin-5-yl) thiazolo[5,4-b]pyridin-5-yl)oxy)propan-2-yl pyridin-4-ylcarbamate (680);
(R)-1-((6-fluoro-2-(2-methoxy-7-methylquinoxalin-5-yl) thiazolo[5,4-b]pyridin-5-yl)oxy)propan-2-yl (6-methylpyridin-3-yl)carbamate (681);
(R)-1-((6-fluoro-2-(2-methoxy-7-methylquinoxalin-5-yl) thiazolo[5,4-b]pyridin-5-yl)oxy)propan-2-yl (5-fluoropyridin-3-yl)carbamate (682);
(R)-1-((6-fluoro-2-(2-methoxy-7-methylquinoxalin-5-yl) thiazolo[5,4-b]pyridin-5-yl)oxy)propan-2-yl (2-oxo-2,3-dihydrobenzo[d]oxazol-6-yl)carbamate (683);
(R)-1-((6-fluoro-2-(2-methoxy-7-methylquinoxalin-5-yl) thiazolo[5,4-b]pyridin-5-yl)oxy)propan-2-yl pyridin-3-ylcarbamate (684);
(R)-1-((6-fluoro-2-(2-methoxy-7-methylquinoxalin-5-yl) thiazolo[5,4-b]pyridin-5-yl)oxy)propan-2-yl (2-(2-hydroxyethoxy)pyrimidin-5-yl)carbamate (685);
(R)-1-((6-fluoro-2-(2-methoxy-7-methylquinoxalin-5-yl) thiazolo[5,4-b]pyridin-5-yl)oxy)propan-2-yl (2-(3-hydroxypropyl)pyrimidin-5-yl)carbamate (686);
(R)-1-((6-fluoro-2-(2-methoxy-7-methylquinoxalin-5-yl) thiazolo[5,4-b]pyridin-5-yl)oxy)propan-2-yl (6-(2,2-difluoro-3-hydroxypropoxy)pyridin-3-yl)carbamate (687);
(R)-1-((6-fluoro-2-(2-methoxy-7-methylquinoxalin-5-yl) thiazolo[5,4-b]pyridin-5-yl)oxy)propan-2-yl (2-((R)-2-hydroxypropoxy)pyrimidin-5-yl)carbamate (688);
methyl (R)-5-(((((1-((6-fluoro-2-(2-methoxy-7-methylquinoxalin-5-yl)thiazolo[5,4-b]pyridine-5-yl)oxy)propan-2-yl)oxy)carbonyl)amino)pyrimidine-2-carboxylate (689);
methyl (R)-5-(((((1-((6-fluoro-2-(2-methoxy-7-methylquinoxalin-5-yl)thiazolo[5,4-b]pyridine-5-yl)oxy)propan-2-yl)oxy)carbonyl)amino)picolinate (690);

(R)-1-((6-fluoro-2-(2-methoxy-7-methylquinoxalin-5-yl) thiazolo[5,4-b]pyridin-5-yl)oxy)propan-2-yl (6-(2-hydroxyethyl)pyridin-3-yl)carbamate (691);

(R)-1-((6-fluoro-2-(2-methoxy-7-methylquinoxalin-5-yl) thiazolo[5,4-b]pyridin-5-yl)oxy)propan-2-yl (2-(((R)-1-hydroxypropan-2-yl)oxy)pyrimidin-5-yl)carbamate (692);

(R)-1-((6-fluoro-2-(2-methoxy-7-methylquinoxalin-5-yl) thiazolo[5,4-b]pyridin-5-yl)oxy)propan-2-yl (2-(((S)-1-hydroxypropan-2-yl)oxy)pyrimidin-5-yl)carbamate (693);

(R)-1-((6-fluoro-2-(2-methoxy-7-methylquinoxalin-5-yl) thiazolo[5,4-b]pyridin-5-yl)oxy)propan-2-yl (6-(hydroxymethyl)pyridin-3-yl)carbamate (694);

(R)-1-((6-fluoro-2-(2-methoxy-7-methylquinoxalin-5-yl) thiazolo[5,4-b]pyridin-5-yl)oxy)propan-2-yl (6-(2-hydroxypropan-2-yl)pyridin-3-yl)carbamate (695);

(R)-1-((6-fluoro-2-(2-methoxy-7-methylquinoxalin-5-yl) thiazolo[5,4-b]pyridin-5-yl)oxy)propan-2-yl (2-(2-hydroxyethyl)pyridin-4-yl)carbamate (696);

(R)-1-((6-fluoro-2-(2-methoxy-7-methylquinoxalin-5-yl) thiazolo[5,4-b]pyridin-5-yl)oxy)propan-2-yl (2-(2-hydroxyethoxy)pyridin-4-yl)carbamate (697);

(R)-1-((6-fluoro-2-(2-methoxy-7-methylquinoxalin-5-yl) thiazolo[5,4-b]pyridin-5-yl)oxy)propan-2-yl pyridazin-4-ylcarbamate (698);

(R)-1-((6-fluoro-2-(2-methoxy-7-methylquinoxalin-5-yl) thiazolo[5,4-b]pyridin-5-yl)oxy)propan-2-yl (2-(3-hydroxy-3-methylbutoxy)pyridin-4-yl)carbamate (699);

(R)-1-((6-fluoro-2-(2-methoxy-7-methylquinoxalin-5-yl) thiazolo[5,4-b]pyridin-5-yl)oxy)propan-2-yl (6-(2-hydroxyethoxy)pyridin-3-yl)carbamate (700);

(R)-1-((6-fluoro-2-(2-methoxy-7-methylquinoxalin-5-yl) thiazolo[5,4-b]pyridin-5-yl)oxy)propan-2-yl (2-((S)-2-hydroxypropoxy)pyrimidin-5-yl)carbamate (701);

(R)-1-((6-fluoro-2-(2-methoxy-7-methylquinoxalin-5-yl) thiazolo[5,4-b]pyridin-5-yl)oxy)propan-2-yl (2-(3-hydroxy-3-methylbutoxy)pyrimidin-5-yl)carbamate (702);

(2R,3S)-3-((6-fluoro-2-(2-methoxy-7-methylquinoxalin-5-yl)thiazolo[5,4-b]pyridin-5-yl)oxy)butan-2-yl (2-oxo-2,3-dihydrobenzo[d]oxazol-6-yl)carbamate (708);

(2R,3S)-3-((6-fluoro-2-(2-methoxy-7-methquinoxalin-5-yl)thiazolo[5,4-b]pyridine-5-yl)oxy)butan-2-yl pyridin-3-ylcarbamate (709);

(2R,3S)-3-((6-fluoro-2-(2-methoxy-7-methylquinoxalin-5-yl)thiazolo[5,4-b]pyridine-5-yl)oxy)butan-2-yl (6-methylpyridin-3-yl)carbamate (710);

(2R,3S)-3-((6-fluoro-2-(2-methoxy-7-methylquinoxalin-5-yl)thiazolo[5,4-b]pyridine-5-yl)oxy)butan-2-yl (2-methoxypyrimidin-5-yl)carbamate (711);

methyl 5-(((((2R,3S)-3-((6-fluoro-2-(2-methoxy-7-methylquinoxalin-5-yl)thiazolo[5,4-b]pyridine-5-yl)oxy) butan-2-yl)oxy)carbonyl)amino)pyrimidine-2-carboxylate (712);

(2R,3S)-3-((6-fluoro-2-(2-methoxy-7-methylquinoxalin-5-yl)thiazolo[5,4-b]pyridine-5-yl)oxy)butan-2-yl pyridin-4-ylcarbamate (713);

(2R,3S)-3-((6-fluoro-2-(2-methoxy-7-methylquinoxalin-5-yl)thiazolo[5,4-b]pyridine-5-yl)oxy)butan-2-yl (5-fluoropyridin-3-yl)carbamate (714);

methyl 5-(((((2R,3S)-3-((6-fluoro-2-(2-methoxy-7-methylquinoxalin-5-yl)thiazolo[5,4-b]pyridine-5-yl)oxy) butan-2-yl)oxy)carbonyl)amino)picolinate (715);

(2R,3S)-3-((6-fluoro-2-(2-methoxy-7-methylquinoxalin-5-yl)thiazolo[5,4-b]pyridine-5-yl)oxy)butan-2-yl pyrimidin-5-ylcarbamate (716);

(2R,3S)-3-((6-fluoro-2-(2-methoxy-7-methylquinoxalin-5-yl)thiazolo[5,4-b]pyridine-5-yl)oxy)butan-2-yl (2-(2-hydroxyethyl)pyridin-4-yl)carbamate (717);

(2R,3S)-3-((6-fluoro-2-(2-methoxy-7-methylquinoxalin-5-yl)thiazolo[5,4-b]pyridine-5-yl)oxy)butan-2-yl (6-(2-hydroxy-2-methylpropyl)pyridin-3-yl)carbamate (718);

(2R,3S)-3-((6-fluoro-2-(2-methoxy-7-methylquinoxalin-5-yl)thiazolo[5,4-b]pyridine-5-yl)oxy)butan-2-yl (2-(2-hydroxyethoxy)pyridin-4-yl)carbamate (719);

(2R,3S)-3-((6-fluoro-2-(2-methoxy-7-methylquinoxalin-5-yl)thiazolo[5,4-b]pyridine-5-yl)oxy)butan-2-yl (2-(2-hydroxyethyl)pyrimidin-5-yl)carbamate (720);

(2R,3S)-3-((6-fluoro-2-(2-methoxy-7-methylquinoxalin-5-yl)thiazolo[5,4-b]pyridine-5-yl)oxy)butan-2-yl (2-(2-hydroxyethoxy)pyrimidin-5-yl)carbamate (721);

(2R,3S)-3-((6-fluoro-2-(2-methoxy-7-methylquinoxalin-5-yl)thiazolo[5,4-b]pyridine-5-yl)oxy)butan-2-yl (2-(((R)-1-hydroxypropan-2-yl)oxy)pyrimidin-5-yl)carbamate (722);

(2R,3S)-3-((6-fluoro-2-(2-methoxy-7-methylquinoxalin-5-yl)thiazolo[5,4-b]pyridine-5-yl)oxy)butan-2-yl (2-(hydroxymethyl)pyridin-4-yl)carbamate (723);

(2R,3S)-3-((6-fluoro-2-(2-methoxy-7-methylquinoxalin-5-yl)thiazolo[5,4-b]pyridine-5-yl)oxy)butan-2-yl (2-(((S)-1-hydroxypropan-2-yl)oxy)pyrimidin-5-yl)carbamate (724);

(2R,3S)-3-((6-fluoro-2-(2-methoxy-7-methylquinoxalin-5-yl)thiazolo[5,4-b]pyridine-5-yl)oxy)butan-2-yl (6-(2-hydroxyethoxy)pyridin-3-yl)carbamate (725);

(2R,3S)-3-((6-fluoro-2-(2-methoxy-7-methylquinoxalin-5-yl)thiazolo[5,4-b]pyridine-5-yl)oxy)butan-2-yl (6-(2,2-difluoro-3-hydroxypropoxy)pyridin-3-yl)carbamate (726);

(2R,3S)-3-((6-fluoro-2-(2-methoxy-7-methylquinoxalin-5-yl)thiazolo[5,4-b]pyridine-5-yl)oxy)butan-2-yl (2-(3-hydroxy-3-methylbutoxy)pyridin-4-yl)carbamate (727);

(2R,3S)-3-((6-fluoro-2-(2-methoxy-7-methylquinoxalin-5-yl)thiazolo[5,4-b]pyridine-5-yl)oxy)butan-2-yl (2-((S)-2-hydroxypropoxy)pyrimidin-5-yl)carbamate (728);

(2R,3S)-3-((6-fluoro-2-(2-methoxy-7-methylquinoxalin-5-yl)thiazolo[5,4-b]pyridine-5-yl)oxy)butan-2-yl (2-((R)-2-hydroxypropoxy)pyrimidin-5-yl)carbamate (729);

(2R,3S)-3-((6-fluoro-2-(2-methoxy-7-methylquinoxalin-5-yl)thiazolo[5,4-b]pyridine-5-yl)oxy)butan-2-yl (2-(3-hydroxy-3-methylbutoxy)pyrimidin-5-yl)carbamate (730);

(2R,3S)-3-((6-fluoro-2-(2-methoxy-7-methylquinoxalin-5-yl)thiazolo[5,4-b]pyridine-5-yl)oxy)butan-2-yl (2-methylpyrimidin-5-yl)carbamate (731);

R)-1-((2-(2-methoxy-7-methylquinoxalin-5-yl)-7-methylthiazolo[5,4-b]pyridin-5-yl)oxy)propan-2-yl pyridin-3-ylcarbamate (733);

(R)-1-((2-(2-methoxy-7-methylquinoxalin-5-yl)-7-methylthiazolo[5,4-b]pyridin-5-yl)oxy)propan-2-yl (6-fluoro-5-methylpyridin-3-yl)carbamate (734);

(R)-1-((2-(2-methoxy-7-methylquinoxalin-5-yl)-7-methylthiazolo[5,4-b]pyridin-5-yl)oxy)propan-2-yl (5-cyanopyridin-3-yl)carbamate (735);

(R)-1-((2-(2-methoxy-7-methylquinoxalin-5-yl)-7-methylthiazolo[5,4-b]pyridin-5-yl)oxy)propan-2-yl (2-chloropyrimidin-5-yl)carbamate (736);

(R)-1-((2-(2-methoxy-7-methylquinoxalin-5-yl)-7-methylthiazolo[5,4-b]pyridin-5-yl)oxy)propan-2-yl (2-methylpyrimidin-5-yl)carbamate (737);

(R)-1-((2-(2-methoxy-7-methylquinoxalin-5-yl)-7-methylthiazolo[5,4-b]pyridin-5-yl)oxy)propan-2-yl (2-methoxypyrimidin-5-yl)carbamate (738);

(R)-1-((2-(2-methoxy-7-methylquinoxalin-5-yl)-7-methylthiazolo[5,4-b]pyridin-5-yl)oxy)propan-2-yl pyridin-3-ylcarbamate (740);

(R)-1-((6-fluoro-2-(2-methoxy-7-methylquinoxalin-5-yl)thiazolo[5,4-b]pyridin-5-yl)oxy) propan-2-yl (6-((2-hydroxy-2-methylpropyl)carbamoyl)pyridin-3-yl)carbamate (741);

(R)-1-((6-fluoro-2-(2-methoxy-7-methylquinoxalin-5-yl)thiazolo[5,4-b]pyridin-5-yl)oxy)propan-2-yl (6-(((1-(hydroxymethyl)cyclobutyl)methyl)carbamoyl)pyridin-3-yl)carbamate (742);

(R)-1-((6-fluoro-2-(2-methoxy-7-methylquinoxalin-5-yl)thiazolo[5,4-b]pyridin-5-yl)oxy)propan-2-yl (6-(3-hydroxypiperidine-1-carbonyl)pyridin-3-yl)carbamate (743);

(R)-1-((6-fluoro-2-(2-methoxy-7-methylquinoxalin-5-yl)thiazolo[5,4-b]pyridin-5-yl)oxy)propan-2-yl (6-((S)-3-hydroxypyrrolidine-1-carbonyl)pyridin-3-yl)carbamate (744);

(R)-1-((6-fluoro-2-(2-methoxy-7-methylquinoxalin-5-yl)thiazolo[5,4-b]pyridin-5-yl)oxy)propan-2-yl (6-((R)-3-hydroxypyrrolidine-1-carbonyl)pyridin-3-yl)carbamate (745);

(R)-1-((6-fluoro-2-(2-methoxy-7-methylquinoxalin-5-yl)thiazolo[5,4-b]pyridin-5-yl)oxy)propan-2-yl (6-(4-hydroxypiperidine-1-carbonyl)pyridin-3-yl)carbamate (746);

(R)-1-((6-fluoro-2-(2-methoxy-7-methylquinoxalin-5-yl)thiazolo[5,4-b]pyridin-5-yl)oxy)propan-2-yl (6-(((R)-2-hydroxypropyl)carbamoyl)pyridin-3-yl)carbamate (747);

(R)-1-((6-fluoro-2-(2-methoxy-7-methylquinoxalin-5-yl)thiazolo[5,4-b]pyridin-5-yl)oxy)propan-2-yl (6-(((S)-2-hydroxypropyl)carbamoyl)pyridin-3-yl)carbamate (748);

(R)-1-((6-fluoro-2-(2-methoxy-7-methylquinoxalin-5-yl)thiazolo[5,4-b]pyridin-5-yl)oxy)propan-2-yl (2-carbamoylpyrimidin-5-yl)carbamate (749);

(2R,3S)-3-((6-fluoro-2-(2-methoxy-7-methylquinoxalin-5-yl)thiazolo[5,4-b]pyridin-5-yl) oxy)butan-2-yl (6-(((S)-2-hydroxypropyl)carbamoyl)pyridin-3-yl)carbamate (750);

(2R,3S)-3-((6-fluoro-2-(2-methoxy-7-methylquinoxalin-5-yl)thiazolo[5,4-b]pyridine-5-yl)oxy)butan-2-yl (2-((2-hydroxy-2-methylpropyl)carbamoyl)pyrimidin-5-yl)carbamate (751);

(2R,3S)-3-((6-fluoro-2-(2-methoxy-7-methylquinoxalin-5-yl)thiazolo[5,4-b]pyridine-5-yl)oxy)butan-2-yl (2-(((R)-2-hydroxypropyl)carbamoyl)pyrimidin-5-yl)carbamate (752);

(2R,3S)-3-((6-fluoro-2-(2-methoxy-7-methylquinoxalin-5-yl)thiazolo[5,4-b]pyridine-5-yl)oxy)butan-2-yl (2-(((S)-2-hydroxypropyl)carbamoyl)pyrimidin-5-yl)carbamate (753);

(2R,3S)-3-((6-fluoro-2-(2-methoxy-7-methylquinoxalin-5-yl)thiazolo[5,4-b]pyridine-5-yl)oxy)butan-2-yl (6-carbamoylpyridin-3-yl)carbamate (754);

(2R,3S)-3-((6-fluoro-2-(2-methoxy-7-methylquinoxalin-5-yl)thiazolo[5,4-b]pyridine-5-yl)oxy)butan-2-yl (2-carbamoylpyrimidin-5-yl)carbamate (755);

(2R,3S)-3-((6-fluoro-2-(2-methoxy-7-methylquinoxalin-5-yl)thiazolo[5,4-b]pyridine-5-yl)oxy)butan-2-yl (6-(3-(hydroxymethyl)morpholine-4-carbonyl)pyridin-3-yl)carbamate (756);

(2R,3S)-3-((6-fluoro-2-(2-methoxy-7-methylquinoxalin-5-yl)thiazolo[5,4-b]pyridine-5-yl)oxy)butan-2-yl (6-((S)-3-hydroxypyrrolidine-1-carbonyl)pyridin-3-yl)carbamate (757);

(2R,3S)-3-((6-fluoro-2-(2-methoxy-7-methylquinoxalin-5-yl)thiazolo[5,4-b]pyridine-5-yl)oxy)butan-2-yl (6-(3-hydroxypiperidine-1-carbonyl)pyridin-3-yl)carbamate (758);

(2R,3S)-3-((6-fluoro-2-(2-methoxy-7-methylquinoxalin-5-yl)thiazolo[5,4-b]pyridine-5-yl)oxy)butan-2-yl (6-(4-hydroxypiperidine-1-carbonyl)pyridin-3-yl)carbamate (759);

(2R,3S)-3-((6-fluoro-2-(2-methoxy-7-methylquinoxalin-5-yl)thiazolo[5,4-b]pyridine-5-yl)oxy)butan-2-yl (6-((R)-3-hydroxypyrrolidine-1-carbonyl)pyridin-3-yl)carbamate (760);

(2R,3S)-3-((6-fluoro-2-(2-methoxy-7-methylquinoxalin-5-yl)thiazolo[5,4-b]pyridine-5-yl)oxy)butan-2-yl (6-(((1-(hydroxymethyl)cyclobutyl)methyl)carbamoyl)pyridin-3-yl)carbamate (761);

N-(2-((2-(2-methoxy-7-methylquinoxalin-5-yl)-7-methylthiazolo[5,4-b]pyridin-5-yl)oxy)ethyl)-4-methylbenzenesulfonamide (762);

6-fluoro-5-methoxy-2-(2-(methoxymethyl)-7-methylquinoxalin-5-yl)-7-methylthiazolo[5,4-b]pyridine (763);

(2R,3S)-3-((6-fluoro-2-(2-methoxy-7-methylquinoxalin-5-yl)thiazolo[5,4-b]pyridin-5-yl)oxy)butan-2-yl (2-(hydroxymethyl)pyrimidin-5-yl)carbamate (764);

(2R,3S)-3-((6-fluoro-2-(2-methoxy-7-methylquinoxalin-5-yl)thiazolo[5,4-b]pyridin-5-yl) oxy)butan-2-yl (6-(2-hydroxypropan-2-yl)pyridin-3-yl)carbamate (765);

(2R,3S)-3-((6-fluoro-2-(2-methoxy-7-methylquinoxalin-5-yl)thiazolo[5,4-b]pyridin-5-yl)oxy)butan-2-yl (6-(1-hydroxyethyl)pyridin-3-yl)carbamate (766);

(2R,3S)-3-((6-fluoro-2-(2-methoxy-7-methylquinoxalin-5-yl)thiazolo[5,4-b]pyridin-5-yl)oxy)butan-2-yl (6-(1-hydroxyethyl)pyridin-3-yl)carbamate (767);

(R)-1-((6-fluoro-2-(2-methoxy-7-methylquinoxalin-5-yl)thiazolo[5,4-b]pyridin-5-yl)oxy)propan-2-yl (2-(hydroxymethyl)pyrimidin-5-yl)carbamate (768);

1-(6-fluoro-2-(2-methoxy-7-methylquinoxalin-5-yl)benzo[d]thiazol-4-yl)-2,2-dimethylpropan-1-ol (806);

1-(5-methoxy-2-(2-methoxy-7-methylquinoxalin-5-yl)thiazolo[5,4-b]pyridin-7-yl)-2,2-dimethylpropan-1-ol (807);

6-methoxy-2-(2-methoxy-7-methylquinoxalin-5-yl)-4-(methoxymethyl)benzo[d]thiazole (808);

2-(2-methoxy-7-methylquinoxalin-5-yl)thiazolo[4,5-c]pyridine (809);

2-((6-fluoro-2-(2-methoxy-7-methylquinoxalin-5-yl)thiazolo[5,4-b]pyridin-5-yl)oxy)ethyl pyridin-3-ylcarbamate (810);

2-((6-fluoro-2-(2-methoxy-7-methylquinoxalin-5-yl)thiazolo[5,4-b]pyridin-5-yl)oxy) ethyl (6-fluoro-5-methylpyridin-3-yl)carbamate (811);

2-((2-(2-methoxy-7-methylquinoxalin-5-yl)-7-methylthiazolo[5,4-b]pyridin-5-yl)oxy) ethyl (6-(thiophen-2-yl)pyridin-3-yl)carbamate (812);

(R)-1-((2-(2-ethoxy-7-methylquinoxalin-5-yl)-6-fluoro-thiazolo[5,4-b]pyridin-5-yl)oxy)propan-2-yl (2-methylpyrimidin-5-yl)carbamate (813);

(R)-1-((2-(2-ethoxy-7-methylquinoxalin-5-yl)-6-fluoro-thiazolo[5,4-b]pyridin-5-yl)oxy)propan-2-yl (2-(2-hydroxyethoxy)pyrimidin-5-yl)carbamate (814);

(R)-1-((2-(2-ethoxy-7-methylquinoxalin-5-yl)-6-fluoro-thiazolo[5,4-b]pyridin-5-yl)oxy) propan-2-yl (2-((R)-2-hydroxypropoxy)pyrimidin-5-yl)carbamate (815);

(2R,3S)-3-((2-(2-ethoxy-7-methylquinoxalin-5-yl)-6-fluorothiazolo[5,4-b]pyridin-5-yl)oxy)butan-2-yl (2-(hydroxymethyl)pyrimidin-5-yl)carbamate (816);

1-(2-(2-ethoxy-7-methylquinoxalin-5-yl)-6-methoxy-benzo[d]thiazol-4-yl)-2,2-dimethylpropan-1-ol (817);

(R)-1-((2-(7-cyano-2-methoxyquinoxalin-5-yl)-5-fluoro-benzo[d]thiazol-6-yl)oxy)propan-2-yl (6-cyanopyridin-3-yl)carbamate (818);

(R)-1-((2-(7-cyano-2-methoxyquinoxalin-5-yl)-5-fluoro-benzo[d]thiazol-6-yl)oxy)propan-2-yl (2-methylpyrimidin-5-yl)carbamate (819);

(2R,3S)-3-((2-(7-chloro-2-methoxyquinoxalin-5-yl)-5-fluorobenzo[d]thiazol-6-yl)oxy)butan-2-yl (2-methoxypyrimidin-5-yl)carbamate (820);

(2R,3S)-3-((2-(7-chloro-2-methoxyquinoxalin-5-yl)-5-fluorobenzo[d]thiazol-6-yl)oxy)butan-2-yl (6-methoxypyridin-3-yl)carbamate (821);

(2R,3S)-3-((2-(7-chloro-2-methoxyquinoxalin-5-yl)-5-fluorobenzo[d]thiazol-6-yl)oxy)butan-2-yl (6-methylpyridin-3-yl)carbamate (822);

(2R,3S)-3-((2-(7-cyano-2-methoxyquinoxalin-5-yl)-5-fluorobenzo[d]thiazol-6-yl)oxy)butan-2-yl (6-methylpyridin-3-yl)carbamate (823);

(2R,3S)-3-((2-(7-chloro-2-methoxyquinoxalin-5-yl)-5-fluorobenzo[d]thiazol-6-yl)oxy)butan-2-yl (2-methylpyrimidin-5-yl)carbamate (824);

(2R,3S)-3-((2-(7-cyano-2-methoxyquinoxalin-5-yl)-5-fluorobenzo[d]thiazol-6-yl)oxy)butan-2-yl (2-methylpyrimidin-5-yl)carbamate (825);

(2R,3S)-3-((2-(7-chloro-2-methoxyquinoxalin-5-yl)-5-fluorobenzo[d]thiazol-6-yl)oxy)butan-2-yl (5-cyano-pyridin-3-yl)carbamate (826);

(2R,3S)-3-((2-(2-(2,2-difluoroethoxy)-7-methylquinoxalin-5-yl)-5-fluorobenzo[d]thiazol-6-yl)oxy)butan-2-yl (2-methylpyrimidin-5-yl)carbamate (827);

(2R,3S)-3-((2-(7-cyano-2-methoxyquinoxalin-5-yl)-5-fluorobenzo[d]thiazol-6-yl)oxy)butan-2-yl (6-cyano-pyridin-3-yl)carbamate (828);

(2R,3S)-3-((2-(7-chloro-2-methoxyquinoxalin-5-yl)-5-fluorobenzo[d]thiazol-6-yl)oxy)butan-2-yl (6-cyano-pyridin-3-yl)carbamate (829);

methyl 5-(((((2R,3S)-3-((2-(7-chloro-2-methoxyquinoxalin-5-yl)-5-fluorobenzo[d]thiazol-6-yl)oxy)butan-2-yl)oxy)carbonyl)amino)picolinate (830);

(2R,3S)-3-((2-(7-chloro-2-methoxyquinoxalin-5-yl)-5-fluorobenzo[d]thiazol-6-yl)oxy)butan-2-yl (6-(hydroxymethyl)pyridin-3-yl)carbamate (831);

(2R,3S)-3-((2-(7-chloro-2-methoxyquinoxalin-5-yl)-5-fluorobenzo[d]thiazol-6-yl)oxy)butan-2-yl (6-(methylcarbamoyl)pyridin-3-yl)carbamate (832);

(2R,3S)-3-((2-(7-chloro-2-methoxyquinoxalin-5-yl)-5-fluorobenzo[d]thiazol-6-yl)oxy) butan-2-yl (6-carbamoylpyridin-3-yl)carbamate (833);

(2R,3S)-3-((2-(7-chloro-2-methoxyquinoxalin-5-yl)-5-fluorobenzo[d]thiazol-6-yl)oxy)butan-2-yl (6-(dimethylcarbamoyl)pyridin-3-yl)carbamate (834);

(2R,3S)-3-((2-(7-chloro-2-methoxyquinoxalin-5-yl)-5-fluorobenzo[d]thiazol-6-yl)oxy)butan-2-yl (6-(2-hydroxy-2-methylpropyl)pyridin-3-yl)carbamate (835);

(2R,3S)-3-((2-(7-chloro-2-methoxyquinoxalin-5-yl)-5-fluorobenzo[d]thiazol-6-yl)oxy)butan-2-yl (6-(2-hydroxyethyl)pyridin-3-yl)carbamate (836); and and 2-(7-chloro-2-methoxyquinoxalin-5-yl)-6-methoxy-4-methylbenzo[d]thiazole (837).

7. The compound according to claim 1 having the structure of Formula (II):

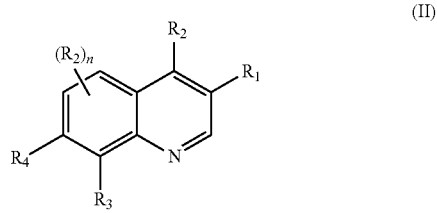

or a salt thereof.

8. The compound according to claim 7 or a salt thereof, wherein:

$R_1$ is —OH, —OCH$_3$, —OCH$_2$CH$_3$, —OCHF$_2$, —OCH$_2$CHF$_2$, —CH$_2$OCH$_3$, or —NH(CH$_3$);

$R_2$, at each occurrence, is independently F, Cl, —CN, —CH$_3$, —CH$_2$OH, —CH$_2$F, —CHF$_2$, or —OCH$_3$;

$R_3$ is:

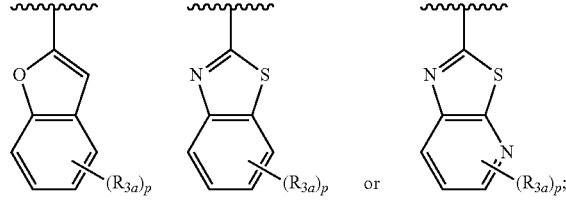

and $R_{3a}$, at each occurrence, is independently F, Cl, —CH$_3$, —OCH$_3$, —CH(OH)(trifluoromethylcyclobutyl), —OCH$_2$CH(CH$_3$)OC(O)NHR$_z$, or —OCH(CH$_3$)CH(CH$_3$)OC(O)NHR$_z$, wherein R$_z$ is pyridinyl, pyrimidinyl, or benzo[d]oxazolonyl, each substituted with zero to 2 substituents independently selected from F, —OH, —CN, —CH$_3$, —CF$_3$, —CH$_2$OH, —CH$_2$CH$_2$OH, —OCH$_2$CH$_2$OH, —OCH$_3$, —CH$_2$CH(CH$_3$)OH, and —OCH$_2$CH$_2$C(CH$_3$)$_2$OH.

9. The compound according to claim 1 or a salt thereof, wherein said compound is selected from:

8-(benzofuran-2-yl)-3-methoxy-6-methylquinoline (177);

6-methoxy-2-(3-(methoxymethyl)-6-methylquinolin-8-yl)-4-methylbenzo[d]thiazole (185);

6-methoxy-2-(4-methoxy-3-(methoxymethyl)-6-methylquinolin-8-yl)-4-methylbenzo[d]thiazole (190);

(2R,3S)-3-((2-(6-chloro-3-methoxyquinolin-8-yl)-5-fluorobenzo[d]thiazol-6-yl)oxy)butan-2-yl (2-(2-hydroxyethoxy)pyrimidin-5-yl)carbamate (512);

(2R,3S)-3-((2-(6-chloro-3-ethoxyquinolin-8-yl)-5-fluorobenzo[d]thiazol-6-yl)oxy)butan-2-yl (2-(2-hydroxyethoxy)pyrimidin-5-yl)carbamate (513);

(2R,3S)-3-((5-fluoro-2-(3-methoxy-6-methylquinolin-8-yl)benzo[d]thiazol-6-yl)oxy)butan-2-yl (2-(2-hydroxyethoxy)pyrimidin-5-yl)carbamate (514);

(2R,3S)-3-((2-(6-chloro-3-(difluoromethoxy)quinolin-8-yl)-5-fluorobenzo[d]thiazol-6-yl)oxy)butan-2-yl (2-(2-hydroxyethoxy)pyrimidin-5-yl)carbamate (515);

2-(6-chloro-3-(methoxymethyl)quinolin-8-yl)-6-methoxy-4-methylbenzo[d]thiazole (625);

2-(6-chloro-3-methoxyquinolin-8-yl)-6-methoxy-4-methylbenzo[d]thiazole (626);

(2R,3S)-3-((5-fluoro-2-(3-methoxy-6-methylquinolin-8-yl)benzo[d]thiazol-6-yl)oxy)butan-2-yl (2-methylpyrimidin-5-yl)carbamate (648);

(2R,3S)-3-((2-(6-chloro-3-ethoxyquinolin-8-yl)-5-fluorobenzo[d]thiazol-6-yl)oxy)butan-2-yl (2-methylpyrimidin-5-yl)carbamate (649);

(2R,3S)-3-((2-(6-chloro-3-(difluoromethoxy)quinolin-8-yl)-5-fluorobenzo[d]thiazol-6-yl)oxy)butan-2-yl (2-methylpyrimidin-5-yl)carbamate (650);

(2R,3S)-3-((2-(6-chloro-3-(2,2-difluoroethoxy)quinolin-8-yl)-5-fluorobenzo[d]thiazol-6-yl)oxy)butan-2-yl (2-methylpyrimidin-5-yl)carbamate (651);

(2R,3S)-3-((2-(6-chloro-3-(methylamino)quinolin-8-yl)-5-fluorobenzo[d]thiazol-6-yl)oxy)butan-2-yl (2-methylpyrimidin-5-yl)carbamate (652);

(2R,3S)-3-((2-(6-(difluoromethyl)-3-methoxyquinolin-8-yl)-5-fluorobenzo[d]thiazol-6-yl)oxy)butan-2-yl (2-methylpyrimidin-5-yl)carbamate (653);

(2R,3S)-3-((5-fluoro-2-(6-(fluoromethyl)-3-methoxyquinolin-8-yl)benzo[d]thiazol-6-yl) oxy)butan-2-yl (2-methylpyrimidin-5-yl)carbamate (654);

(2R,3S)-3-((2-(6-cyano-3-methoxyquinolin-8-yl)-5-fluorobenzo[d]thiazol-6-yl)oxy)butan-2-yl (2-methylpyrimidin-5-yl)carbamate (655);

(2-(6-chloro-3-methoxyquinolin-8-yl)-6-methoxybenzo[d]thiazol-4-yl)(1-(trifluoromethyl)cyclobutyl)methanol (656);

(2R,3S)-3-((2-(3,6-dimethoxyquinolin-8-yl)-5-fluorobenzo[d]thiazol-6-yl)oxy)butan-2-yl (2-methylpyrimidin-5-yl)carbamate (657);

(2R,3S)-3-((2-(3-(difluoromethoxy)-6-methylquinolin-8-yl)-5-fluorobenzo[d]thiazol-6-yl)oxy)butan-2-yl (2-methylpyrimidin-5-yl)carbamate (659);

(2R,3S)-3-((2-(3-ethoxy-6-methylquinolin-8-yl)-5-fluorobenzo[d]thiazol-6-yl)oxy)butan-2-yl (2-methylpyrimidin-5-yl)carbamate (660);

(2R,3S)-3-((2-(6-chloro-3-methoxyquinolin-8-yl)-6-fluorothiazolo[5,4-b]pyridin-5-yl)oxy)butan-2-yl (2-methylpyrimidin-5-yl)carbamate (769);

(R)-1-((2-(6-chloro-3-methoxyquinolin-8-yl)-6-fluorothiazolo[5,4-b]pyridin-5-yl)oxy)propan-2-yl (2-methylpyrimidin-5-yl)carbamate (770);

(2R,3S)-3-((6-fluoro-2-(3-methoxy-6-methylquinolin-8-yl)thiazolo[5,4-b]pyridin-5-yl)oxy)butan-2-yl (2-methylpyrimidin-5-yl)carbamate (771);

(2R,3S)-3-((5-fluoro-2-(6-fluoro-3-methoxyquinolin-8-yl)benzo[d]thiazol-6-yl)oxy)butan-2-yl (2-methylpyrimidin-5-yl)carbamate (772);

(2R,3S)-3-((5-fluoro-2-(6-(hydroxymethyl)-3-methoxyquinolin-8-yl)benzo[d]thiazol-6-yl)oxy)butan-2-yl (2-methylpyrimidin-5-yl)carbamate (773);

(2R,3S)-3-((2-(6-chloro-3-methoxyquinolin-8-yl)-6-fluorothiazolo[5,4-b]pyridin-5-yl)oxy)butan-2-yl (2-(2-hydroxyethoxy)pyrimidin-5-yl)carbamate (774);

(2R,3S)-3-((6-fluoro-2-(3-methoxy-6-methylquinolin-8-yl)thiazolo[5,4-b]pyridin-5-yl)oxy)butan-2-yl (2-(2-hydroxyethoxy)pyrimidin-5-yl)carbamate (775);

(2R,3S)-3-((2-(6-chloro-3-methoxyquinolin-8-yl)-6-fluorothiazolo[5,4-b]pyridin-5-yl) oxy)butan-2-yl (5-fluoropyridin-3-yl)carbamate (776);

(2R,3S)-3-((2-(6-chloro-3-methoxyquinolin-8-yl)-6-fluorothiazolo[5,4-b]pyridin-5-yl)oxy)butan-2-yl (2-oxo-2,3-dihydrobenzo[d]oxazol-6-yl)carbamate (777);

(2R,3S)-3-((2-(6-chloro-3-methoxyquinolin-8-yl)-6-fluorothiazolo[5,4-b]pyridin-5-yl)oxy)butan-2-yl (2-(3-hydroxy-3-methylbutoxy)pyridin-4-yl)carbamate (778);

(2R,3S)-3-((2-(6-chloro-3-methoxyquinolin-8-yl)-6-fluorothiazolo[5,4-b]pyridin-5-yl)oxy)butan-2-yl (6-(2-hydroxyethoxy)pyridin-3-yl)carbamate (779);

(2R,3S)-3-((2-(6-chloro-3-methoxyquinolin-8-yl)-6-fluorothiazolo[5,4-b]pyridin-5-yl)oxy)butan-2-yl (2-(2-hydroxyethoxy)pyridin-4-yl)carbamate (780);

(2R,3S)-3-((2-(6-chloro-3-methoxyquinolin-8-yl)-6-fluorothiazolo[5,4-b]pyridin-5-yl)oxy)butan-2-yl (6-(2-hydroxyethyl)pyridin-3-yl)carbamate (781);

(2R,3S)-3-((2-(6-chloro-3-methoxyquinolin-8-yl)-5-fluorobenzo[d]thiazol-6-yl)oxy)butan-2-yl (5-fluoropyridin-3-yl)carbamate (782);

(2R,3S)-3-((2-(6-chloro-3-methoxyquinolin-8-yl)-5-fluorobenzo[d]thiazol-6-yl)oxy)butan-2-yl (6-(trifluoromethyl)pyridin-3-yl)carbamate (783);

(2R,3S)-3-((2-(6-chloro-3-methoxyquinolin-8-yl)-5-fluorobenzo[d]thiazol-6-yl)oxy)butan-2-yl (6-methoxypyridin-3-yl)carbamate (784);

(2R,3S)-3-((2-(6-chloro-3-methoxyquinolin-8-yl)-5-fluorobenzo[d]thiazol-6-yl)oxy)butan-2-yl (5-methoxypyridin-3-yl)carbamate (785);

(2R,3S)-3-((2-(6-chloro-3-methoxyquinolin-8-yl)-5-fluorobenzo[d]thiazol-6-yl)oxy)butan-2-yl (5-cyanopyridin-3-yl)carbamate (786);

(2R,3S)-3-((2-(6-chloro-3-methoxyquinolin-8-yl)-5-fluorobenzo[d]thiazol-6-yl)oxy)butan-2-yl (5,6-dimethylpyridin-3-yl)carbamate (787);

(2R,3S)-3-((2-(6-chloro-3-methoxyquinolin-8-yl)-5-fluorobenzo[d]thiazol-6-yl)oxy)butan-2-yl pyridin-3-ylcarbamate (788);

(2R,3S)-3-((2-(6-chloro-3-methoxyquinolin-8-yl)-5-fluorobenzo[d]thiazol-6-yl)oxy)butan-2-yl (6-fluoropyridin-3-yl)carbamate (789);

(2R,3S)-3-((2-(6-chloro-3-methoxyquinolin-8-yl)-5-fluorobenzo[d]thiazol-6-yl)oxy)butan-2-yl pyridin-4-ylcarbamate (790);

(2R,3S)-3-((6-fluoro-2-(3-methoxy-6-methylquinolin-8-yl)thiazolo[5,4-b]pyridin-5-yl)oxy)butan-2-yl (2-methylpyrimidin-5-yl)carbamate (791);

(2R,3S)-3-((6-fluoro-2-(3-methoxy-6-methylquinolin-8-yl)thiazolo[5,4-b]pyridin-5-yl)oxy)butan-2-yl (2-(hydroxymethyl)pyrimidin-5-yl)carbamate (792);

(2R,3S)-3-((2-(6-chloro-3-methoxyquinolin-8-yl)-6-fluorothiazolo[5,4-b]pyridin-5-yl)oxy)butan-2-yl (2-(hydroxymethyl)pyrimidin-5-yl)carbamate (793);

(R)-1-((2-(6-chloro-3-methoxyquinolin-8-yl)-6-fluorothiazolo[5,4-b]pyridin-5-yl)oxy)propan-2-yl (2-(hydroxymethyl)pyrimidin-5-yl)carbamate (794);

(2R,3S)-3-((4-chloro-2-(6-chloro-3-methoxyquinolin-8-yl)-5-fluorobenzo[d]thiazol-6-yl)oxy)butan-2-yl (2-(2-hydroxyethoxy)pyrimidin-5-yl)carbamate (795);

(2R,3S)-3-((4-chloro-2-(6-chloro-3-methoxyquinolin-8-yl)-5-fluorobenzo[d]thiazol-6-yl)oxy)butan-2-yl (2-((R)-2-hydroxypropoxy)pyrimidin-5-yl)carbamate (796);

(2R,3S)-3-((4-chloro-2-(6-chloro-3-methoxyquinolin-8-yl)-5-fluorobenzo[d]thiazol-6-yl)oxy)butan-2-yl (6-fluoropyridin-3-yl)carbamate (797);

(2R,3S)-3-((4-chloro-2-(6-chloro-3-methoxyquinolin-8-yl)-5-fluorobenzo[d]thiazol-6-yl)oxy)butan-2-yl pyridin-4-ylcarbamate (798);

(2R,3S)-3-((4-chloro-2-(6-chloro-3-methoxyquinolin-8-yl)-5-fluorobenzo[d]thiazol-6-yl)oxy)butan-2-yl pyridin-3-ylcarbamate (799);
(2R,3S)-3-((4-chloro-2-(6-chloro-3-methoxyquinolin-8-yl)-5-fluorobenzo[d]thiazol-6-yl)oxy)butan-2-yl (5,6-dimethylpyridin-3-yl)carbamate (800);
(2R,3S)-3-((4-chloro-2-(6-chloro-3-methoxyquinolin-8-yl)-5-fluorobenzo[d]thiazol-6-yl)oxy)butan-2-yl (6-methoxypyridin-3-yl)carbamate (801);
(2R,3S)-3-((4-chloro-2-(6-chloro-3-methoxyquinolin-8-yl)-5-fluorobenzo[d]thiazol-6-yl)oxy)butan-2-yl (5-cyanopyridin-3-yl)carbamate (802);
(2R,3S)-3-((4-chloro-2-(6-chloro-3-methoxyquinolin-8-yl)-5-fluorobenzo[d]thiazol-6-yl)oxy)butan-2-yl (5-methoxypyridin-3-yl)carbamate (803); and
(2R,3S)-3-((4-chloro-5-fluoro-2-(3-methoxy-6-methylquinolin-8-yl)benzo[d]thiazol-6-yl)oxy)butan-2-yl (5-fluoropyridin-3-yl)carbamate (804).

10. A pharmaceutical composition, which comprises a pharmaceutically acceptable carrier and a compound according to claim 1 or a pharmaceutically acceptable salt thereof, alone or in combination with another therapeutic agent.

11. A method for the treatment of a thromboembolic disorder, which comprises the steps of administering to a patient in need thereof a therapeutically effective amount of a compound according to claim 1 or a pharmaceutically acceptable salt thereof, wherein the thromboembolic disorder is selected from the group consisting of arterial cardiovascular thromboembolic disorders, venous cardiovascular thromboembolic disorders, and thromboembolic disorders in the chambers of the heart or in the peripheral circulation.

12. The method according to claim 7 wherein the thromboembolic disorder is selected from the group consisting of unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, and procedures in which blood is exposed to an artificial surface that promotes thrombosis.

13. A method of inhibiting or preventing platelet aggregation, which comprises the step of administering to a subject in need thereof a therapeutically effective amount of a compound according to claim 1 or a salt thereof.

14. A compound, wherein the compound is

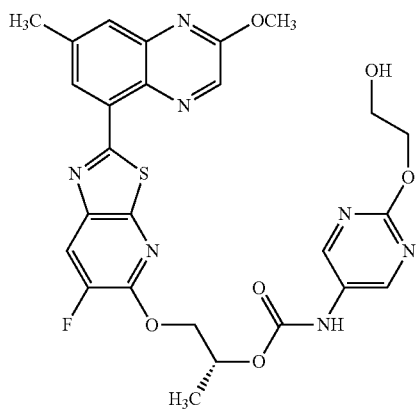 [SMILES: COc1cnc2c(-c3nc4cc(F)c(OC[C@@H](C)OC(=O)Nc5cnc(OCCO)nc5)nc4s3)cc(C)cc2n1]

or salt thereof.

15. A pharmaceutical composition, which comprises a pharmaceutically acceptable carrier and a compound according to claim 14 or a pharmaceutically acceptable salt thereof, alone or in combination with another therapeutic agent.

16. A method for the treatment of a thromboembolic disorder, which comprises the steps of administering to a patient in need thereof a therapeutically effective amount of a compound according to claim 14 or a pharmaceutically acceptable salt thereof, wherein the thromboembolic disorder is selected from the group consisting of arterial cardiovascular thromboembolic disorders, venous cardiovascular thromboembolic disorders, and thromboembolic disorders in the chambers of the heart or in the peripheral circulation.

17. The method according to claim 16 wherein the thromboembolic disorder is selected from the group consisting of unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, and procedures in which blood is exposed to an artificial surface that promotes thrombosis.

18. A compound, wherein the compound is

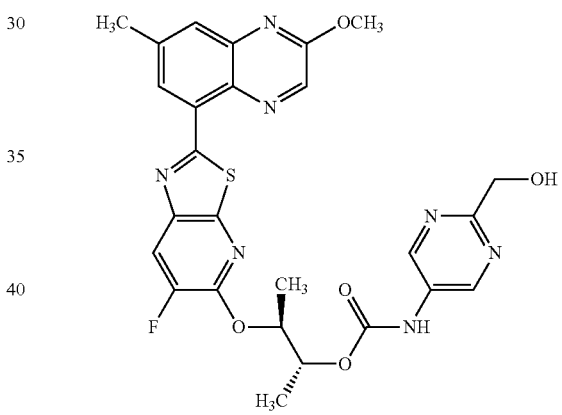

or salt thereof.

19. A pharmaceutical composition, which comprises a pharmaceutically acceptable carrier and a compound according to claim 18 or a pharmaceutically acceptable salt thereof, alone or in combination with another therapeutic agent.

20. A method for the treatment of a thromboembolic disorder, which comprises the steps of administering to a patient in need thereof a therapeutically effective amount of a compound according to claim 19 or a pharmaceutically acceptable salt thereof, wherein the thromboembolic disorder is selected from the group consisting of arterial cardiovascular thromboembolic disorders, venous cardiovascular thromboembolic disorders, and thromboembolic disorders in the chambers of the heart or in the peripheral circulation.

21. The method according to claim 20 wherein the thromboembolic disorder is selected from the group consisting of unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, and procedures in which blood is exposed to an artificial surface that promotes thrombosis.

22. A compound, wherein the compound is

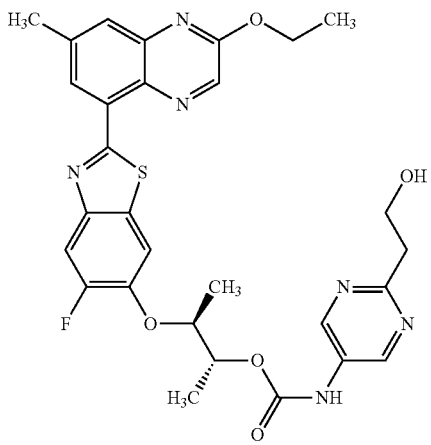 [SMILES: CCOc1cnc2c(-c3nc4cc(F)c(O[C@@H](C)[C@@H](C)OC(=O)Nc5cnc(CCO)nc5)cc4s3)cc(C)cc2n1]

or salt thereof.

23. A pharmaceutical composition, which comprises a pharmaceutically acceptable carrier and a compound according to claim 22 or a pharmaceutically acceptable salt thereof, alone or in combination with another therapeutic agent.

24. A method for the treatment of a thromboembolic disorder, which comprises the steps of administering to a patient in need thereof a therapeutically effective amount of a compound according to claim 22 or a pharmaceutically acceptable salt thereof, wherein the thromboembolic disorder is selected from the group consisting of arterial cardiovascular thromboembolic disorders, venous cardiovascular thromboembolic disorders, and thromboembolic disorders in the chambers of the heart or in the peripheral circulation.

25. The method according to claim 24 wherein the thromboembolic disorder is selected from the group consisting of unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, and procedures in which blood is exposed to an artificial surface that promotes thrombosis.

26. A compound, wherein the compound is

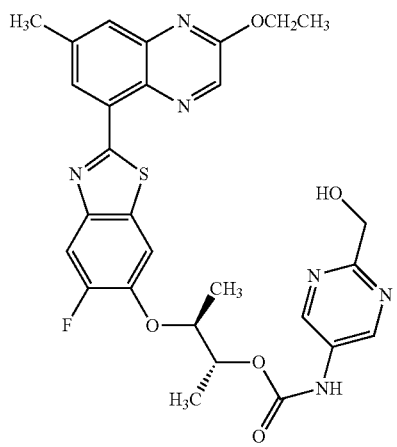 [SMILES: CCOc1cnc2c(-c3nc4cc(F)c(O[C@@H](C)[C@@H](C)OC(=O)Nc5cnc(CO)nc5)cc4s3)cc(C)cc2n1]

or salt thereof.

27. A pharmaceutical composition, which comprises a pharmaceutically acceptable carrier and a compound according to claim 26 for a pharmaceutically acceptable salt thereof, alone or in combination with another therapeutic agent.

28. A method for the treatment of a thromboembolic disorder, which comprises the steps of administering to a patient in need thereof a therapeutically effective amount of a compound according to claim 26 or a pharmaceutically acceptable salt thereof, wherein the thromboembolic disorder is selected from the group consisting of arterial cardiovascular thromboembolic disorders, venous cardiovascular thromboembolic disorders, and thromboembolic disorders in the chambers of the heart or in the peripheral circulation.

29. The method according to claim 28 wherein the thromboembolic disorder is selected from the group consisting of unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, and procedures in which blood is exposed to an artificial surface that promotes thrombosis.

30. A compound, wherein the compound is

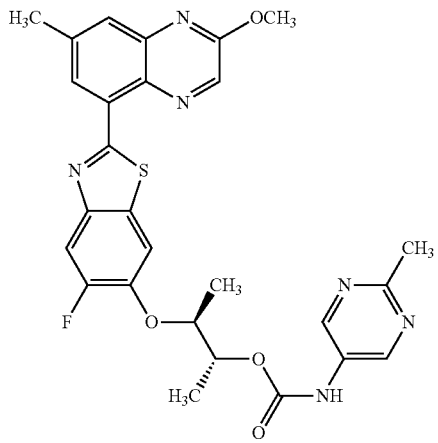

or salt thereof.

31. A pharmaceutical composition, which comprises a pharmaceutically acceptable carrier and a compound according to claim 30 or a pharmaceutically acceptable salt thereof, alone or in combination with another therapeutic agent.

32. A method for the treatment of a thromboembolic disorder, which comprises the steps of administering to a patient in need thereof a therapeutically effective amount of a compound according to claim 30 or a pharmaceutically acceptable salt thereof, wherein the thromboembolic disorder is selected from the group consisting of arterial cardiovascular thromboembolic disorders, venous cardiovascular thromboembolic disorders, and thromboembolic disorders in the chambers of the heart or in the peripheral circulation.

33. The method according to claim 32 wherein the thromboembolic disorder is selected from the group consisting of unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, and procedures in which blood is exposed to an artificial surface that promotes thrombosis.

\* \* \* \* \*